(12) United States Patent
Beck et al.

(10) Patent No.: US 9,175,313 B2
(45) Date of Patent: Nov. 3, 2015

(54) THREE-DIMENSIONAL STRUCTURE OF ISOPRENE SYNTHASE AND ITS USE THEREOF FOR GENERATING VARIANTS

(71) Applicants: Danisco US Inc., Palo Alto, CA (US); The Goodyear Tire & Rubber Company, Akron, OH (US)

(72) Inventors: Zachary Q. Beck, Palo Alto, CA (US); Richard R. Bott, Burlingame, CA (US); Jeffrey V. Miller, Menlo Park, CA (US); Christopher L. Rife, Redwood City, CA (US); Derek H. Wells, Palo Alto, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 13/888,265

(22) Filed: May 6, 2013

(65) Prior Publication Data
US 2013/0252303 A1 Sep. 26, 2013

Related U.S. Application Data

(62) Division of application No. 12/765,825, filed on Apr. 22, 2010, now Pat. No. 8,518,686.

(60) Provisional application No. 61/172,199, filed on Apr. 23, 2009, provisional application No. 61/255,831, filed on Oct. 28, 2009.

(51) Int. Cl.
| | | |
|---|---|---|
| *C12N 1/20* | (2006.01) | |
| *C12N 1/00* | (2006.01) | |
| *C12N 15/00* | (2006.01) | |
| *C12P 7/04* | (2006.01) | |
| *C12P 5/02* | (2006.01) | |
| *C12P 5/00* | (2006.01) | |
| *C07H 21/04* | (2006.01) | |
| *C12N 9/88* | (2006.01) | |

(52) U.S. Cl.
CPC . *C12P 5/007* (2013.01); *C12N 9/88* (2013.01); *C12Y 402/03027* (2013.01); *C07K 2299/00* (2013.01)

(58) Field of Classification Search
None
See application file for complete search history.

(56) References Cited

U.S. PATENT DOCUMENTS

| | | |
|---|---|---|
| 1,344,713 A | 6/1920 | Peters |
| 3,686,349 A | 8/1972 | Schliebs et al. |
| 4,570,029 A | 2/1986 | Kulprathipanja et al. |
| 4,647,344 A | 3/1987 | Lindner et al. |
| 4,683,195 A | 7/1987 | Mullis et al. |
| 4,683,202 A | 7/1987 | Mullis |
| 4,703,007 A | 10/1987 | Mulholland et al. |
| 4,846,872 A | 7/1989 | Kamuro et al. |
| 4,965,188 A | 10/1990 | Mullis et al. |
| 5,322,770 A | 6/1994 | Gelfand |
| 5,349,126 A | 9/1994 | Chappell et al. |
| 5,380,831 A | 1/1995 | Adang et al. |
| 5,436,391 A | 7/1995 | Fujimoto et al. |
| 5,545,816 A | 8/1996 | Ausich et al. |
| 5,849,970 A | 12/1998 | Fall et al. |
| 5,874,276 A | 2/1999 | Fowler et al. |
| 6,022,725 A | 2/2000 | Fowler et al. |
| 6,106,888 A | 8/2000 | Dale et al. |
| 6,176,176 B1 | 1/2001 | Dale et al. |
| 6,268,328 B1 | 7/2001 | Mitchinson et al. |
| 6,270,739 B1 | 8/2001 | Barnicki et al. |
| 6,294,653 B1 | 9/2001 | Mayfield |
| 6,582,914 B1 | 6/2003 | Caldwell et al. |
| 6,806,076 B1 | 10/2004 | Miyake et al. |
| 6,989,257 B2 | 1/2006 | Berry et al. |
| 6,998,471 B2 | 2/2006 | Hallahan et al. |
| 7,129,392 B2 | 10/2006 | Hahn et al. |
| 7,132,268 B2 | 11/2006 | Miyake et al. |
| 7,132,527 B2 | 11/2006 | Payne et al. |
| 7,172,886 B2 | 2/2007 | Keasling et al. |
| 7,183,089 B2 | 2/2007 | Keasling et al. |
| 7,208,298 B2 | 4/2007 | Miyake et al. |
| 7,241,587 B2 | 7/2007 | Dodge et al. |
| 7,262,041 B2 | 8/2007 | Baldwin et al. |
| 7,364,885 B2 | 4/2008 | Miyake et al. |
| 7,371,558 B2 | 5/2008 | Cervin et al. |
| 7,531,333 B2 | 5/2009 | Miyake et al. |

(Continued)

FOREIGN PATENT DOCUMENTS

| | | |
|---|---|---|
| DE | 196 29 568 C1 | 1/1998 |
| EP | 0 215 594 A2 | 3/1987 |

(Continued)

OTHER PUBLICATIONS

Albrecht, M. et al. (Aug. 2000). "Novel Hydroxycarotenoids with Improved Antioxidative Properties Produced by Gene Combination in *Escherichia coli*," *Nature Biotechnology* 18:843-846.

(Continued)

*Primary Examiner* — Iqbal H Chowdhury
(74) *Attorney, Agent, or Firm* — Mintz Levin Cohn Ferris Glovsky and Popeo, P.C.

(57) ABSTRACT

The present invention provides a three-dimensional structures of *P. tremuloides* isoprene synthase and *P. alba* isoprene synthase. The invention also provides methods of using the three-dimensional structure to design isoprene synthases with improved activity for increased isoprene production in microbial host cells. Biosynthetically produced isoprene of the present invention finds use in the manufacture of rubber and elastomers.

18 Claims, 92 Drawing Sheets

(56) References Cited

U.S. PATENT DOCUMENTS

| | | | |
|---|---|---|---|
| 8,173,410 | B2 | 5/2012 | Bott et al. |
| 8,288,148 | B2 | 10/2012 | Cervin et al. |
| 8,420,759 | B2 | 4/2013 | Feher et al. |
| 8,518,686 | B2 | 8/2013 | Beck et al. |
| 8,709,785 | B2 | 4/2014 | Cervin et al. |
| 2002/0095818 | A1 | 7/2002 | Jain et al. |
| 2003/0033626 | A1 | 2/2003 | Hahn et al. |
| 2004/0005678 | A1 | 1/2004 | Kleasling et al. |
| 2004/0219629 | A1 | 11/2004 | Cheng et al. |
| 2005/0287655 | A1 | 12/2005 | Tabata et al. |
| 2006/0009647 | A1 | 1/2006 | Yeates et al. |
| 2006/0020095 | A1 | 1/2006 | Gandon-Pain |
| 2008/0038805 | A1 | 2/2008 | Melis |
| 2008/0178354 | A1 | 7/2008 | Chappell |
| 2009/0155874 | A1 | 6/2009 | Clark et al. |
| 2010/0003716 | A1* | 1/2010 | Cervin et al. ............ 435/40.5 |
| 2010/0048964 | A1 | 2/2010 | Calabria et al. |
| 2010/0086978 | A1 | 4/2010 | Beck et al. |
| 2010/0113846 | A1 | 5/2010 | McAuliffe et al. |
| 2010/0196982 | A1 | 8/2010 | Anderson |
| 2010/0285549 | A1 | 11/2010 | Muramatsu et al. |
| 2011/0045563 | A1 | 2/2011 | Melis |
| 2013/0045891 | A1 | 2/2013 | Beck et al. |
| 2013/0078699 | A1 | 3/2013 | Cervin et al. |
| 2013/0260432 | A1 | 10/2013 | Bott et al. |

FOREIGN PATENT DOCUMENTS

| | | |
|---|---|---|
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 1 118 855 A2 | 7/2001 |
| EP | 1 118 855 A3 | 7/2001 |
| JP | 2006-271379 A | 10/2006 |
| JP | 2008-035831 A | 2/2008 |
| JP | 2008-061506 A | 3/2008 |
| JP | 2008-182950 A | 8/2008 |
| JP | 2009-207402 A | 9/2009 |
| KR | 2001-0084864 A | 9/2001 |
| RU | 2 197 461 C2 | 1/2003 |
| WO | WO-95/04134 A1 | 2/1995 |
| WO | WO-95/11913 A1 | 5/1995 |
| WO | WO-96/35796 A1 | 11/1996 |
| WO | WO-98/02550 A2 | 1/1998 |
| WO | WO-98/02550 A3 | 1/1998 |
| WO | WO-00/17327 A2 | 3/2000 |
| WO | WO-00/17327 A3 | 3/2000 |
| WO | WO-00/17327 A9 | 3/2000 |
| WO | WO-01/58839 A1 | 8/2001 |
| WO | WO-02/076189 A1 | 10/2002 |
| WO | WO-02/099095 A2 | 12/2002 |
| WO | WO-02/099095 A3 | 12/2002 |
| WO | WO-2004/033646 A2 | 4/2004 |
| WO | WO-2004/033646 A3 | 4/2004 |
| WO | WO-2004/111214 A1 | 12/2004 |
| WO | WO-2005/001036 A2 | 1/2005 |
| WO | WO-2005/001036 C1 | 1/2005 |
| WO | WO-2005/007682 A2 | 1/2005 |
| WO | WO-2005/007682 A3 | 1/2005 |
| WO | WO-2005/078074 A2 | 8/2005 |
| WO | WO-2005/078074 A3 | 8/2005 |
| WO | WO-2006/063752 A1 | 6/2006 |
| WO | WO-2006/085899 A2 | 8/2006 |
| WO | WO-2006/085899 A3 | 8/2006 |
| WO | WO-2007/018062 A1 | 2/2007 |
| WO | WO-2007/136847 A2 | 11/2007 |
| WO | WO-2007/136847 A3 | 11/2007 |
| WO | WO-2007/140339 A2 | 12/2007 |
| WO | WO-2007/140339 A3 | 12/2007 |
| WO | WO-2007/140339 A8 | 12/2007 |
| WO | WO-2008/002472 A2 | 1/2008 |
| WO | WO-2008/002472 A3 | 1/2008 |
| WO | WO-2008/003078 A2 | 1/2008 |
| WO | WO-2008/003078 A3 | 1/2008 |
| WO | WO-2008/003078 A8 | 1/2008 |
| WO | WO-2008/137092 A2 | 11/2008 |
| WO | WO-2008/137092 A3 | 11/2008 |
| WO | WO-2008/153925 A2 | 12/2008 |
| WO | WO-2008/153925 A3 | 12/2008 |
| WO | WO-2008/153925 A9 | 12/2008 |
| WO | WO-2008/153934 A2 | 12/2008 |
| WO | WO-2008/153934 A3 | 12/2008 |
| WO | WO-2008/153935 A2 | 12/2008 |
| WO | WO-2008/153935 A3 | 12/2008 |
| WO | WO-2009/036067 A2 | 3/2009 |
| WO | WO-2009/036067 A3 | 3/2009 |
| WO | WO-2009/064910 A2 | 5/2009 |
| WO | WO-2009/064910 A3 | 5/2009 |
| WO | WO-2009/076676 A2 | 6/2009 |
| WO | WO-2009/076676 A3 | 6/2009 |
| WO | WO-2009/100231 A2 | 8/2009 |
| WO | WO-2009/100231 A3 | 8/2009 |
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/003007 A3 | 1/2010 |
| WO | WO-2010/005525 A1 | 1/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/148150 A1 | 12/2010 |
| WO | WO-2011/000026 A1 | 1/2011 |

OTHER PUBLICATIONS

Allison, R. et al. (1986). "The Nucleotide Sequence of the Coding Region of Tobacco Etch Virus Genomic RNA: Evidence for the Synthesis of a Single Polyprotein," *Virology* 154:9-20.

Alper, H. et al. (2008). "Uncovering the Gene Knockout Landscape for Improved Lycopene Production in *E. coli*," *Appl. Microbiol. Biotechnol.* 10 pages.

Alterthum, F. et al. (Aug. 1989). "Efficient Ethanol Production from Glucose, Lactose, and Xylose by Recombinant *Escherichia coli*," *Applied Environmental Microbiology* 55(8):1943-1948.

Altschul, S.F. et al. (1990). "Basic Local Alignment Search Tool," *J Mol. Biol.* 215:403-410.

Altschul, S.F. et al. (1996). "Local Alignment Statistics," Chapter 27 in *Multiple Alignment and Phylogenetic Trees*, American Press, Inc. 266:460-480.

Altschul, S.F. et al. (1997). "Gapped BLAST and PSI-BLAST: A New Generation of Protein Database Search Programs," *Nucleic Acids Research* 25(17):3389-3402.

Alves, R. et al. (Nov. 2000). "Effect of Overall Feedback Inhibition in Unbranched Biosynthetic Pathways," *Biophysical Journal* 79(5):2290-2304.

Anderson, M.S. et al. (Nov. 15, 1989). "Isopentenyl Diphosphate: Dimethylallyl Diphosphate Isomerase. An Improved Purification of the Enzyme and Isolation of the Gene from *Saccharomyces cerevisiae*," *J. Biol. Chem.* 264(32):19169-19175.

Andreassi, J.L. et al. (2004, e-pub. Dec. 4, 2004). "*Streptococcus pneumoniae* Isoprenoid Biosynthesis Is Downregulated by Diphosphomevalonate: An Antimicrobial Target," *Biochemistry* 43(51):16461-16466.

Andreassi, J.L. et al. (2007, e-pub. Mar. 30, 2007). "Crystal Structure of the *Streptococcus pneumoniae* Mevalonate Kinase in Complex with Diphosphomevalonate," *Protein Science* 16:983-989.

(56) References Cited

OTHER PUBLICATIONS

Aon, J.C. et al. (Feb. 2008, e-pub. Dec. 14, 2007). "Suppressing Posttranslational Gluconoylation of Heterologous Proteins by Metabolic Engineering of *Escherichia coli*," *Applied and Environmental Microbiology* 74(4):950-958.
Arai, Y. et al. (2004). "Production of Polyhydroxybutyrate by Polycistronic Expression of Bacterial Genes in Tobacco Plastid," *Plant Cell Physiol*. 45(9):1176-1184.
Ashby, M.N. et al. (Aug. 5, 1990). "Elucidation of the Deficiency in Two Yeast Coenzyme Q Mutants: Characterization of the Structural Gene Encoding Hexaprenyl Pyrophosphate Synthetase," *The Journal of Biological Chemistry* 265(22):13157-13164.
Ausubel, F. M. et al. eds. (1987). "Introduction of DNA into Mammalian Cells," Chapter 9 in *Current Protocols in Molecular Biology*.
Baba, T. et al. (Feb. 21, 2006). "Construction of *Escherichia coli* K-12 In-Frame, Single-Gene Knockout Mutants: The Keio Collection," *Molecular Systems Biology* pp. 1-11.
Ballas, N. et al. (1989). "Efficient Functioning of Plant Promoters and Poly(A) Sites in *Xenopus oocytes*," *Nucleic Acids Research* 17(19):7891-7903.
Barkovich, R. et al. (2001, e-pub. Dec. 1, 2000). "Metabolic Engineering of Isoprenoids," *Metabolic Engineering* 3:27-39.
Beaucage, S.L. et al. (1981). "Deoxynucleoside Phosphoramidites—A New Class of Key Intermediates for Deoxypolynucleotide Synthesis," *Tetrahedron Letters* 22(20):1859-1862.
Bellion, E. et al. (1993). "Methylamine Utilization in Yeast and Bacteria: Studies Using in vivo NMR," Chapter 32 in *Microbial Growth on $C_1$ Compounds*, Murrell, J.C. et al. eds, Intercept Ltd: Andover, UK, pp. 415-432.
Berman, H. et al. (2007, e-pub. Nov. 16, 2006). "The Worldwide Protein Data Bank (wwPDB): Ensuring a Single, Uniform Archive of PDB Data," *Nucleic Acids Research* 35:D301-D303.
Beytia, E. et al. (Oct. 25, 1970). "Purification and Mechanism of Action of Hog Liver Mevalonic Kinase," *The Journal of Biological Chemistry* 245(20):5450-5458.
Bock, R. et al. (2000). "Extranuclear Inheritance: Plastid Genetics: Manipulation of Plastid Genomes and Biotechnological Applications," *Progress in Botany* 61:76-90.
Bock, R. (2001). "Transgenic Plastids in Basic Research and Plant Biotechnology," *J. Mol. Biol*. 312:425-438.
Bock, R. (Jun. 2004). "Taming Plastids for a Green Future," *Trends in Biotechnology* 22(6):311-318.
Boel, E. et al. (1984). "Two Different Types of Intervening Sequences in the Glucoamylase Gene from *Aspergillus niger*," *The EMBO Journal* 3(7):1581-1585.
Bouvier, F. et al. (2005). "Biogenesis, Molecular Regulation and Function of Plant Isoprenoids," *Progress in Lipid Research* 44:357-429.
Boynton, J.E. et al. (1993). "Chloroplast Transformation in *Chlamydomonas*," *Methods in Enzymology* 217(37):510-536.
Broun, P. et al. (Nov. 13, 1998). "Catalytic Plasticity of Fatty Acid Modification Enzymes Underlying Chemical Diversity of Plant Lipids," *Science* 282:1315-1317.
Brünger, A.T. et al. (1998). "Crystallography & NMR System: A New Software Suite for Macromolecular Structure Determination," *Acta Cryst*. D54:905-921.
Bubunenko, M. et al. (Apr. 2007). "Essentiality of Ribosomal and Transcription Antitermination Proteins Analyzed by Systematic Gene Replacement in *Escherichia coli*," *Journal of Bacteriology* 189(7):2844-2853.
Campbell, E.I. et al. (1989). "Improved Transformation Efficiency of *Aspergillus niger* Using the Homologous *nia*D Gene for Nitrate Reductase," *Curr. Genet*. 16:53-56.
Campbell, J.W. et al. (Oct. 2001). "*Escherichia coli* FadR Positively Regulates Transcription of the *fabB* Fatty Acid Biosynthetic Gene," *J. Bacteriol*. 183(20):5982-5990.
Campos, N. et al. (2001). "*Escherichia coli* Engineering to Synthesize Isopentenyl Diphosphate and Dimethylallyl Diphosphate from Mevalonate: A Novel System for the Genetic Analysis of the 2-C-Methyl-D-Erythritol 4-Phospate Pathway for Isoprenoid Biosynthesis," *Biochem. J*. 353:59-67.
Cao, Q.-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.
Chamberlin, M. et al. (Oct. 17, 1970). "New RNA Polymerase from *Escherichia coli* Infected with Bacteriophage T7," *Nature* 228:227-231.
Champenoy, S. et al. (1998). "Expression of the Yeast Mevalonate Kinase Gene in Transgenic Tobacco," *Molecular Breeding* 4:291-300.
Chan, W. et al. (2007, e-pub. Apr. 10, 2007). "A Recombineering Based Approach for High-Throughput Conditional Knockout Targeting Vector Construction," *Nucleic Acids Research* 35(8):e64, 13 pages.
Chappell, J. et al. (1995). "Is the Reaction Catalyzed by 3-Hydroxy-3-Methylglutaryl—Coenzyme A Reductase a Rate-Limiting Step for Isoprenoid Biosynthesis in Plants?" *Plant Physiology* 109:1337-1343.
Chemler, J.A. et al. (May 23, 2006). "Biosynthesis of Isoprenoids, Polyunsaturated Fatty Acids and Flavonoids in *Saccharomyces cerevisiae*," *Microbial Cell Factories* 5:20, 9 pages.
Cherepanov, P.P. et al. (1995). "Gene Disruption in *Escherichia coli*: $Tc^H$ and $Km^H$ Cassettes with the Option of Flp-Catalyzed Excision of the Antibiotic-Resistance Determinant," *Gene* 158(1):9-14.
Chica, R.A. et al. (2005). "Semi-Rational Approaches to Engineering Enzyme Activity: Combining the Benefits of Directed Evolution and Rational Design," *Current Opinion in Biotechnology* 16:378-384.
Cho, H.-J. et al. (1995). "Expression Pattern of Bacterial Polycistronic Genes in Tobacco Cells," *Journal of Fermentation and Bioengineering* 80(2):111-117.
Clarke, S. (1992). "Protein Isoprenylation and Methylation at Carboxyl-Terminal Cysteine Residues," *Annu. Rev. Biochem*. 61:355-386.
Clough, S.J. et al. (1998). "Floral Dip: A Simplified Method for *Agrobacterium*-Mediated Transformation of *Arabidopsis thaliana*," *The Plant Journal* 16(6):735-743.
Collaborative Computational Project, No. 4. (1994). "The *CCP4* Suite: Programs for Protein Crystallography," *Acta Cryst*. D50:760-763.
Cordier, H. et al. (1999). "Heterologous Expression in *Saccharomyces cerevisiae* of an *Arabidopsis thaliana* cDNA Encoding Mevalonate Diphosphate Decarboxylase," *Plant Molecular Biology* 39:953-967.
Cunningham, F.X. et al. (1998). "Genes and Enzymes of Carotenoid Biosynthesis in Plants," *Ann. Rev. Plant Physiol. Plant Mol. Biol*. 49:557-583.
Cunningham, F.X. et al. (Oct. 2000). "Evidence of a Role for LytB in the Nonmevalonate Pathway of Isoprenoid Biosynthesis," *Journal of Bacteriology* 182(20):5841-5848.
Dale, P.J. (1992). "Spread of Engineered Genes to Wild Relatives," *Plant Physiol*. 100:13-15.
Dale, G.E. et al. (2003). "The Protein as a Variable in Protein Crystallization," *Journal of Structural Biology* 142:88-97.
Daniell, H. (1997). "Transformation and Foreign Gene Expression in Plants Mediated by Microprojectile Bombardment," Chapter 35 in *Methods in Molecular Biology, Recombinant Gene Expression Protocols*, Tuan, R. ed., Human Press, Inc., Totowa, NJ, 62:463-489.
Daniell, H. et al. (Apr. 1998) "Containment of Herbicide Resistance Through Genetic Engineering of the Chloroplast Genome," *Nature Biotechnology* 16:345-348.
Datsenko, K.A. et al. (Jun. 6, 2000). "One-Step Inactivation of Chromosomal Genes in *Escherichia coli* K-12 Using PCR Products," *PNAS* 97(12):6640-6645.
Datta, S. et al. (2006). "A Set of Recombineering Plasmids for Gram-Negative Bacteria," *Gene* 379:109-115.
Datukishvili, N.T. et al. (2001). "Isolation and Purification of Protein Responsible for the Conversion of Dimethylallylpyrophosphate from Poplar Leaves into Isoprene," *Russian Journal of Plant Physiology* 48(2):222-225.
Davidson, S. (Oct.-Dec. 2003). "Light Factories," located at <http://www.publish.csiro.au/?act=view_file&file_id=EC117p10.pdf>, last visited on Oct. 2, 2008.

(56) References Cited

OTHER PUBLICATIONS

Davis, I.W. et al. (2007). "MolProbity: All-Atom Contacts and Structure Validation for Proteins and Nucleic Acids," *Nucleic Acids Research* 35:W375-W383.
De Cosa, B. et al. (Jan. 2001). "Overexpression of the *Bt cry*2Aa2operon in Chloroplasts Leads to Formation of Insecticidal Crystals," *Nature Biotechnology* 19:71-74.
Del Campo, E. M. et al. (1997). "Plastid *ndhD* Gene of Barley, Sequence and Transcript Editing (Accesion No. Y12258) (PGR 97-090)," *Plant Physiol.* 114:747-749.
Della-Cioppa, G. et al. (1987). "Protein Trafficking in Plant Cells," *Plant Physiol.* 84:965-968.
Deppenmeier, U. et al. (2002). "The Genome of *Methanosarcina mazei*: Evidence for Lateral Gene Transfer Between Bacteria and Archaea," *J. Mol. Microbiol. Biotechnol.* 4(4):453-461.
Deroles, S.C. et al. (1988). "Expression and Inheritance of Kanamycin Resistance in a Large Number of Transgenic Petunias Generated by *Agrobacterium*-Mediated Transformation," *Plant Molecular Biology* 11:355-364.
Dettmer, K. et al. (2000). "Stability of Reactive Low Boiling Hydrocarbons on Carbon Based Adsorbents Typically Used for Adsorptive Enrichment and Thermal Desorption," *Fresenius J. Anal. Chem.* 366:70-78.
Devereux, J. et al. (1984). "A Comprehensive Set of Sequence Analysis Programs for the VAX," *Nucleic Acids Research* 12(1):387-395.
Devos, D. et al. (2000). "Practical Limits of Function Prediction," *Proteins: Structure, Function, and Genetics* 41:98-107.
Dewick, P.M. et al. (2002, e-pub. Jan. 22, 2002). "The Biosynthesis of $C_5$—$C_{25}$ Terpenoid Compounds," *Nat. Prod. Rep.* 19:181-222.
Dhe-Paganon, S. et al. (1994). "Mechanism of Mevalonate Pyrophosphate Decarboxylase: Evidence for a Carbocationic Transition State," *Biochemistry* 33(45):13355-13362.
Dorsey, J.K. et al. (Sep. 25, 1968). "The Inhibition of Mevalonic Kinase by Geranyl and Farnesyl Pyrophosphates," *The Journal of Biological Chemistry* 243(18):4667-4670.
Doumith, M. et al. (2000, e-pub. Aug. 25, 2000). "Analysis of Genes Involved in 6-Deoxyhexose Biosynthesis and Transfer in *Saccharopolyspora erythraea*," *Mol. Gen Genet.* 264:477-485.
Dynan, W.S. et al. (Aug. 29, 1985). "Control of Eukaryotic Messenger RNA Synthesis by Sequence-Specific DNA-Binding Proteins," *Nature* 316:774-778.
Eisenreich, W. et al. (Sep. 1998). "The Deoxyxylulose Phosphate Pathway of Terpenoid Biosynthesis in Plants and Microorganisms," *Chemistry and Biology* 5(9):R221-R233.
Eisenreich, W. et al, (Feb. 2001). "Deoxyxylulose Phosphate Pathway to Terpenoids," *Trends in Plant Science* 6(2):78-84.
Elroy-Stein, O. et al. (Aug. 1989). "Cap-Independent Translation of mRNA Conferred by Encephalomyocarditis Virus 5' Sequence Improves the Performance of the Vaccinia Virus/Bacteriophage T7 Hybrid Expression System," *PNAS USA* 86:6126-6130.
EMBL-EBI Accession No. A0PFK2, last updated on Mar. 2, 2010, located at <http://srs.ebi.ac.uk/srsbin/cgi-bin/wgetz?-e+[UNIPROT:A0PFK2_POPNI]+-newId>, last visited on Jun. 2, 2010, 2 pages.
EMBL-EBI Accession No. A9PGR5, last updated on Mar. 2, 2010, located at <http://srs.ebi.ac.uk/srsbin/cgi-bin/wgetz?-e+[UNIPROT:A9PGR5_POPTR]+-newId>, last visited on Jun. 2, 2010, 2 pages.
EMBL-EBI Accession No. AB198180, last updated May 10, 2005, located at <http://www.ebi.ac.uk/cgi-bin/dbfetch?db=embl&id=ab198180&Subm . . . >, last visited on Jul. 8, 2009, 2 pages.
EMBL-EBI Accession No. AY341431, last updated Apr. 16, 2005, located at <http://www.ebi.ac.uk/cgi-bin/dbfetch?db=embl&id=AY341431∈ . . . >, last visited on Nov. 26, 2009, 2 pages.
Emsley, P. et al. (2004). "*Coot*: Model-Building Tools for Molecular Graphics," *Acta Crystallographica* D60:2126-2132.
Emsley, P. et al. (2010). "Features and Development of *Coot*," *Acta Crystallographica* D66:486-501.
Extended European Search Report mailed on Jun. 14, 2011, for EP Patent Application No. 08860589.4, filed on Dec. 15, 2008, 10 pages.
Fall, R. (Sep. 12, 2003). "Final Technical Report: DE-FG03-97ER20274, Microbial Production of Isoprene. Dates Covered: Jun. 15, 2000 to Jun. 14, 2003," located at <http://www.osti.gov/scitech/servlets/purl/814920>, last visited on Nov. 11, 2013, 4 pages.
Farmer, W.R. et al. (May 2000). "Improving Lycopene Production in *Escherichia coli* by Engineering Metabolic Control," *Nature Biotechnology* 18:533-537.
Feng, D.-F. et al. (1987). "Progressive Sequence Alignment as a Prerequisite to Correct Phylogenetic Trees," *Journal of Molecular Evolution* 25:351-360.
Finkelstein, D.B. (1992). "Transformation," Chapter 6 in *Biotechnology of Filamentous Fungi*, Butterworth-Heinemann: Boston, MA, pp. 113-156.
Flores, S. et al. (Aug. 20, 2004, e-pub. Jul. 23, 2004). "Growth-Rate Recovery of *Escherichia coli* Cultures Carrying a Multicopy Plasmid, by Engineering of the Pentose-Phosphate Pathway," *Biotechnology and Bioengineering* 87(4):485-494.
Fu, Z. et al. (2008, e-pub. Feb. 27, 2008). "Biochemical and Structural Basis for Feedback Inhibition of Mevalonate Kinase and Isoprenoid Metabolism," *Biochemistry* 47:3715-3724.
Gallie, D.R. et al. (1989). "Eukaryotic Viral 5'-Leader Sequences Act as Translational Enhancers in Eukaryotes and Prokaryotes," in *Molecular Biology of RNA*, Cech, T.R. ed., Alan R. Liss, Inc: New York, NY, pp. 237-256.
Garret, T.A. et al. (May 15, 1998). "Accumulation of a Lipid a Precursor Lacking the 4'-Phosphate Following Inactivation of the *Escherichia coli IpxK* Gene," *The Journal of Biological Chemistry* 273(20):12457-12465.
GenBank Accession No. AB198180, last updated on May 10, 2005, located at <http://www.ncbi.nlm.nih.gov/nuccore/63108309>, last visited on Jun. 2, 2010, 2 pages.
GenBank Accession No. AJ294819.1, last updated Apr. 15, 2005, located at <http://www.ncbi.nlm.nih.gov/nuccore/AJ294819.1>, last visited on Dec. 7, 2011, 2 pages.
GenBank Accession No. AJ457070, last updated on Apr. 15, 2005, located at <http://www.ncbi.nlm.nih.gov/nuccore/38092202>, last visited on Jun. 2, 2010, 2 pages.
GenBank Accession No. AM410988.1, last updated Aug. 14, 2008, located at <http://www.ncbi.nlm.nih.gov/nuccore/AM410988.1>, last visited on Dec. 7, 2011, 2 pages.
GenBank Accession No. AY182241, last updated on May 4, 2004, located at <http://www.ncbi.nlm.nih.gov/nuccore/32265057>, last visited on Jun. 2, 2010, 2 pages.
GenBank Accession No. AY279379, last updated on Mar. 11, 2005, located at <http://www.ncbi.nlm.nih.gov/nuccore/30984014>, last visited on Jun. 2, 2010, 2 pages.
GenBank Accession No. AY316691, last updated on Feb. 15, 2005, located at <http://www.ncbi.nlm.nih.gov/nuccore/35187003>, last visited on Jun. 2, 2010, 2 pages.
GenBank Accession No. AY341431, last updated on Feb. 15, 2005, located at <http://www.ncbi.nlm.nih.gov/nuccore/33358228>, last visited on Jun. 2, 2010, 3 pages.
GenBank Accession No. EF147555.1, last updated Mar. 24, 2009, located at <http://www.ncbi.nlm.nih.gov/nuccore/EF147555.1>, last visited on Dec. 7, 2011, 2 pages.
GenBank Accession No. EF638224.1, last updated May 3, 2010, located at <http://www.ncbi.nlm.nih.gov/nuccore/EF638224.1>, last visited on Dec. 7, 2011, 2 pages.
GenBank Accession No. EU693027, last updated on May 27, 2008, located at <http://www.ncbi.nlm.nih.gov/nuccore/189017053>, last visited on Jun. 2, 2010, 2 pages.
GenBank Accession No. CAC35696, last updated Apr. 15, 2005, located at <http://www.ncbi.nlm.nih.gov/protein/CAC35696>, last visited on Nov. 1, 2011, 1 page.
Geneseq Database Accession No. AFB74822, "Monoterpene synthetase protein SEQ ID No. 4." Retrieved from EBI accession No. GSP:AFB74822 (Apr. 19, 2007), located at http://ibis/exam/dbfetch.jsp?id=GSP:AFB74822, last visited on Apr. 17, 2012, 2 pages.
Goedegebuur, F. et al. (2002, e-pub. May 7, 2002). "Cloning and Relational Analysis of 15 Novel Fungal Endoglucanases from Family 12 Glycosyl Hydrolase," *Curr. Genet.* 41:89-98.
Goldschmidt-Clermont, M. (1991). "Transgenic Expression of Aminoglycoside Adenine Transferase in the Chloroplast: A Select-

(56) References Cited

OTHER PUBLICATIONS able Marker for Site-Directed Transformation of Chlamydomonas," *Nucleic Acids Res.* 19(15):4083-4089.

Goodwin, T.W. (1971). "Biosynthesis of Carotenoids and Plant Triterpenes: The Fifth CIBA Medal Lecture," *Biochem. J.* 123(3):293-329.

Gräwert, T. et al. (2004, e-pub. Sep. 21, 2004). "IspH Protein of *Escherichia coli*: Studies on Iron—Sulfur Cluster Implementation and Catalysis," *Journal American Chemistry Society* 126:12847-12855.

Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.

Grochowski, L.L. et al. (May 2006). "*Methanocaldococcus jannaschii* Uses a Modified Mevalonate Pathway for Biosynthesis of Isopentenyl Diphosphate," *Journal of Bacteriology* 188(9):3192-3198.

Guda, C. et al. (2000). "Stable Expression for a Biodegradable Protein-Based Polymer in Tobacco Chloroplasts," *Plant Cell Reports* 19:257-262.

Guerineau, F. et al. (1991). "Effect of Deletions in the Cauliflower Mosaic Virus Polyadenylation Sequence on the Choice of the Polyadenylation Sites in Tobacco Protoplasts," *Mol. Gen. Genet.* 226:141-144.

Guo, D.-A. et al. (1995). "Developmental Regulation of Sterol Biosynthesis in *Zea mays*," *Lipids* 30(3):203-219.

Hahn, F.M. et al. (May 12, 1995). "Isolation of *Schizosaccharomyces pombe* Isopentenyl Diphosphate Isomerase in cDNA Clones by Complementation and Synthesis of the Enzyme in *Escherichia coli*," *The Journal of Biological Chemistry* 270(19):11298-11303.

Hahn, F.M. et al. (Feb. 1996). "Open Reading Frame 176 in the Photosynthesis Gene Cluster of *Rhodobacter capsulatus* Encodes *idi*, a Gene for Isopentenyl Diphosphate Isomerase," *Journal of Bacteriology* 178(3):619-624.

Hahn, F.M. et al. (Aug. 1999). "*Escherichia coli* Open Reading Frame 696 Is *idi*, a Nonessential Gene Encoding Isopentenyl Diphosphate Isomerase," *Journal of Bacteriology* 181(15):4499-4504.

Hahn, F.M. et al. (Jan. 2001). "1-Deoxy D-Xylulose 5-Phosphate Synthase, the Gene Product of Open Reading Frame (ORF) 2816 and ORF 2895 in *Rhodobacter capsulatus*," *Journal of Bacteriology* 183(1):1-11.

Hamano, Y. et al. (2001). "Cloning of a Gene Cluster Encoding Enzymes Responsible for the Mevalonate Pathway from a Terpenoid-Antibiotic-Producing *Streptomyces* Strain," *Biosci. Biotechnol. Biochem.* 65(7):1627-1635.

Hamilton, C.M. et al. (Sep. 1989). "New Method for Generating Deletions and Gene Replacements in *Escherichia coli*," *Journal of Bacteriology* 171(9):4617-4622.

Hanai, T. et al. (Dec. 2007). "Engineered Synthetic Pathway for Isopropanol Production in *Escherichia coli*," *Applied and Environmental Microbiology* 73(24):7814-7818.

Harker, M. et al. (1999). "Expression of Prokaryotic 1-Deoxy-D-Xylulose-5-Phosphatases in *Escherichia coli* Increases Carotenoid and Ubiquinone Biosynthesis," *FEBS Letters* 448:115-119.

Harkki, A. et al. (Jun. 1989). "A Novel Fungal Expression System: Secretion of Active Calf Chymosin from the Filamentous Fungus *Trichoderma reesei*," *Bio/Technology* 7:596-603.

Hedl, M. et al. (Apr. 2002). "*Enterococcus faecalis* Acetoacetyl-Coenzyme A Thiolase/3-Hydroxy-3-Methylglutaryl-Coenzyme A Reductase, a Dual-Function Protein of Isopentenyl Diphosphate Biosynthesis," *Journal of Bacteriology* 184(8):2116-2122.

Hedl, M. et al. (Apr. 2004). "Class II 3-Hydroxy-3-Methylglutaryl Coenzyme A Reductases," *Journal of Bacteriology* 186(7):1927-1932.

Hellman, U. et al. (1995). "Improvement of an "In-Gel" Digestion Procedure for the Micropreparation of Internal Protein Fragments for Amino Acid Fragments for Amino Acid Sequencing," *Analytical Biochemistry* 224:451-455.

Henikoff, S. (Nov. 1992). "Amino Acid Substitution Matrices from Protein Blocks," *Proc. Natl. Acad. Sci. USA* 89:10915-10919.

Herbers, K. et al. (Jun. 1996). "Manipulating Metabolic Partitioning in Transgenic Plants", *TIBTECH* 14:198-205.

Herz, S. et al. (Mar. 14, 2000). "Biosynthesis of Terpenoids: YgbB Protein Converts 4-Diphosphocytidyl-2C-Methyl-D-Erythritol 2-Phosphate to 2C-Methyl-D-Erythritol 2,4-Cyclodiphosphate," *PNAS* 97(6):2486-2490.

Higgins, D.G. et al. (1989). "Fast and Sensitive Multiple Sequence Alignments on a Microcomputer," *Cabios Communications* 5(2):151-153.

Hinson, D.D. et al. (1997). "Post-Translation Regulation of Mevalonate Kinase by Intermediates of the Cholesterol and Nonsterol Isoprene Biosynthetic Pathways," *Journal of Lipid Research* 38:2216-2223.

Hoeffler, J-F. et al. (2002). "Isoprenoid Biosynthesis via the Methylerythritol Phosphate Pathway. Mechanistic Investigations of the 1-Deoxy-D-Xylulose 5-Phosphate Reductoisomerase," *Eur. J. Biochem.* 269:4446-4457.

Huang, K.-X. et al. (1999). "Overexpression, Purification, and Characterization of the Thermostable Mevalonate Kinase from *Methanococcus jannaschii*," *Protein Expression and Purification* 17:33-40.

Hunter, B.K. (1985). "Formaldehyde Metabolism by *Escherichia coli*. Carbon and Solvent Deuterium Incorporation into Glycerol, 1,2-Propanediol, and 1,3-Propanediol," *Biochemistry* 24(15):4148-4155.

Hyatt, D.C. et al. (Mar. 27, 2007). "Structure of Limonene Synthase, A Simple Model for Terpenoid Cyclase Catalysis," *PNAS* 104(13):5360-5365.

Ilmén, M. et al. (Apr. 1997). "Regulation of Cellulase Gene Expression in the Filamentous Fungus *Trichoderma reesei*," *Appl. Environ. Microbiol.* 63(4):1298-1306.

Innis, M.A. et al. (Apr. 5, 1985). "Expression, Glycosylation, and Secretion of an *Aspergillus* Glucoamylase by *Saccharomyces cerevisiae*," *Science* 228:21-26.

Jenkins, L.S. et al. (Jan. 1987). "Genetic and Molecular Characterization of the Genes Involved in Short-Chain Fatty Acid Degradation in *Escherichia coli*: The *ato* System," *Journal of Bacteriology* 169(1):42-52.

Jeong, S-W. et al. (2004, e-pub. Jan. 21, 2004). "Dicistronic Expression of the Green Fluorescent Protein and Antibiotic Resistance Genes in the Plastid for Selection and Tracking of Plastid-Transformed Cells in Tobacco," *Plant Cell Rep* 22:747-751.

Jeong, D-W. et al. (2007). "Cloning and Characterization of a Gene Encoding Phosphoketolase in a *Lactobacillus paraplantarum* Isolated from *Kimchi*," *Journal of Microbiology and Biotechnology* 17(5):822-829.

Jobling, S.A. et al. (Feb. 12, 1987). "Enhanced Translation of Chimaeric Messenger RNAs Containing a Plant Viral Untranslated Leader Sequence," *Nature* 235:622-625.

Jones, K.L. et al. (2000). "Low-Copy Plasmids Can Perform as Well as or Better Than High-Copy Plasmids for Metabolic Engineering of Bacteria," *Metabolic Engineering* 2:238-338.

Jones, E.Y. et al. (1991). "Methodology Employed for the Structure Determination of Tumour Necrosis Factor, a Case of High Non-Crystallographic Symmetry," *Acta Cryst* A47:753-770.

Joshi, C.P. (1987). "Putative Polyadenylation Signals in Nuclear Genes of Higher Plants: A Compilation and Analysis," *Nucleic Acids Research* 15(23):9627-9640.

Julsing, M.K. et al. (Jul. 2007, e-pub. Apr. 26, 2007). "Functional Analysis of Genes Involved in the Biosynthesis of Isoprene in *Bacillus subtilis*," *Applied Microbiol. Biotechnol.* 75(6):1377-1384.

Kacian, D.L. et al. (Oct. 1972). "A Replicating RNA Molecule Suitable for a Detailed Analysis of Extracellular Evolution and Replication," *Proc. Natl. Acad. Sci. USA* 69(10):3038-3042.

Kajiwara, S. et al. (1997). "Expression of an Exogenous Isopentenyl Diphosphate Isomerase Gene Enhances Isoprenoid Biosynthesis in *Escherichia coli*," *Biochem. J.* 324:421-426.

Kampranis, S.C. et al. (Jun. 2007). "Rational Conversion of Substrate and Product Specificity in a *Salvia* Monoterpene Synthase: Structural Insights into the Evolution of Terpene Synthase Function," *The Plant Cell* 19:1994-2005.

(56) References Cited

OTHER PUBLICATIONS

Kaneda, K. et al. (Jan. 30, 2001). "An Unusual Isopentenyl Diphosphate Isomerase Found in the Mevalonate Pathway Gene Cluster from *Streptomyces* sp. Strain CL190," *PNAS* 98(3):932-937.

Karl, T. et al. (2003). "Dynamic Measurements of Partition Coefficients Using Proton-Transfer-Reaction Mass Spectrometry (PTR-MS)," *International Journal of Mass Spectrometry* 223-224:383-395.

Karlin, S. (Jun. 1993). "Applications and Statistics for Multiple High-Scoring Segments in Molecular Sequences," *Proc. Natl. Acad. Sci. USA* 90:5873-5787.

Kavanagh, T.A. et al. (Jul. 1999). "Homeologous Plastid DNA Transformation in Tobacco Is Mediated by Multiple Recombination Events," *Genetics* 152(3):1111-1122.

Keasling, J.D. (Mar. 29, 2004). "Genetic Tools for Metabolic Enzyme Production in *Escherichia Coli*," presented at NIGMS 2004 PSI Protein Production & Crystallization Workshop, Bethesda, MD, Mar. 29-31, 2004, located at <http://www-nmr.cabm.rutgers.edu/labdocuments/workshops/psi_ppcw_32904/ppcw_32904.html>, last visited on Jun. 4, 2010, 66 pages.

Keasling, J.D. (May 7, 2005). "Drugs from Bugs: Engineering Microorganisms to Produce New Drugs," presented at Engineering a Better World: *Our Environment, Our Health*, Berkeley, CA, May 7, 2005, 62 pages.

Keasling, J.D. (Sep. 23, 2007). "Engineering Microbes for Production of Low-Cost, Effective, Anti-Malarial Drugs," *presented at Enzyme Engineering XIX*, Harrison Hot Springs, British Columbia, Canada, Sep. 23-28, 2007, 152 pages.

Keegan, R.M. et al. (2007). "Automated Search-Model Discovery and Preparation for Structure Solution by Molecular Replacement," *Acta Crystallographica* D63:447-457.

Keeler, K.H. et al. (1996). "Movement of Crop Transgenes into Wild Plants," Chapter 20 in *Herbicide Resistant Crops: Agricultural, Environmental, Economic, Regulatory, and Technical Aspects*, Duke, S.O. ed., Lewis Publishers: Boca Raton, FL., pp. 303-330.

Kelly, J.M. et al. (1985). "Transformation of *Aspergillus niger* by the *amd*S Gene of *Aspergillus nidulans*," *The EMBO Journal* 4(2):475-479.

Khan, M.S. et al. (Sep. 1999). "Fluorescent Antibiotic Resistance Marker for Tracking Plastid Transformation in Higher Plants," *Nature Biotechnology* 17:910-914.

Kieser, T. eds. et al. (Jul. 2000). "Introduction of DNA into *Streptomyces*," Chapter 10 in *Practical Streptomyces Genetics*, pp. 229-252.

Kisselev, L. (Jan. 2002). "Polypeptide Release Factors in Prokaryotes and Eukaryotes: Same Function, Different Structure," *Structure* 10:8-9.

Klein-Marcuschamer, D. et al. (2007, e-pub. Aug. 2, 2007). "Engineering Microbial Cell Factories for Biosynthesis of Isoprenoid Molecules: Beyond Lycopene," *TRENDS in Biotechnology* 25(9):417-424.

Klein-Marcuschamer, D. et al. (Feb. 19, 2008). "Assessing the Potential of Mutational Strategies to Elicit New Phenotypes in Industrial Strains," *PNAS* 105(7):2319-2324.

Koga, Y. et al. (Mar. 2007). "Biosynthesis of Ether-Type Polar Lipids in Archaea and Evolutionary Considerations," *Microbiology and Molecular Biology Reviews* 71(1):97-120.

Köksal, M. et al. (2010, e-pub. Jul. 17, 2010). "Structure of Isoprene Synthase Illuminates the Chemical Mechanism of Teragram Atmospheric Carbon Emission," *J. Mol. Biol.* pp. 1-11.

Kooter, J. M., et al. (Sep. 1999). "Listening to the Silent Genes: Transgene Silencing, Gene Regulation and Pathogen Control," *Trends in Plant Science* 4(9):340-347.

Kota, M. et al. (Mar. 1999). "Overexpression of the *Bacillus thuringiensis* (Bt) Cry2Aa2 Protein in Chloroplasts Confers Resistance to Plants Against Susceptible and Bt-Resistant Insects," *Proc. Natl. Acad. Sci. USA* 96:1840-1845.

Kozak, M. (Oct. 25, 1991). "Structural Features in Eukaryotic mRNAs That Modulate the Initiation of Translation," *The Journal of Biological Chemistry* 266(30):19867-19870.

Kozak, M. (1999). "Initiation of Translation in Prokaryotes and Eukaryotes," *Gene* 234:187-208.

Kunkel, T. A. (Jan. 1985). "Rapid and Efficient Site-Specific Mutagenesis without Phenotypic Selection," *Proc. Natl. Acad. Sci. USA* 82:488-492.

Kuzma, J. et al. (1995). "Bacteria Produce the Volatile Hydrocarbon Isoprene," *Current Microbiology* 30:97-103.

Kuzuyama, T. et al. (1998). "Direct Formation of 2-*C* Methyl-D-Erythritol 4-Phosphate from 1-Deoxy-D-Xylulose 5-Phosphate by 1-Deoxy-D-Xylulose 5-Phosphate Reductoisomerase, a New Enzyme in the Non-Mevalonate Pathway to Isopentenyl Diphosphate," *Tetrahedron Letters* 39:4509-4512.

Kuzuyama, T. et al. (1998). "Fosmidomycin, a Specific Inhibitor of 1-Deoxy-D-Xylulose 5-Phosphate Reductoisomerase in the Nonmevalonate Pathway for Terpenoid Biosynthesis," *Tetrahedron Letters* 39:7913-7916.

Lange, B.M. et al. (Nov. 23, 1999). "Isopentenyl Diphosphate Biosynthesis via a Mevalonate-Independent Pathway: Isopentenyl Monophosphate Kinase Catalyzes the Terminal Enzymatic Step," *PNAS* 96(24):13714-13719.

Lange, B.M. et al. (Sep. 2001). "Isoprenoid Biosynthesis. Metabolite Profiling of Peppermint Oil Gland Secretory Cells and Application to Herbicide Target Analysis," *Plant Physiology* 127:305-314.

Law, C.K. (1984). "Heat and Mass Transfer in Combustion: Fundamental Concepts and Analytical Techniques," *Progress in Energy and Combustion Science* 10:295-318.

Lehning, A. et al. (1999). "Isoprene Synthase Activity and Its Relation to Isoprene Emission in *Quercus robur* L. Leaves," *Plant, Cell and Environment* 22:495-504.

Lerner, C.G. et al. (1990). "Low Copy Number Plasmids for Regulated Low-Level Expression of Cloned Genes in *Escherichia coli* with Blue/White Insert Screening Capability," *Nucleic Acids Research* 18(15):4631.

Li, W. et al. (2010, e-pub. Nov. 1, 2009). "Non-Redundant Patent Sequence Databases with Value-Added Annotations at Two Levels," *Nucleic Acids Research* 38:D52-D56.

Lichtenthaler, H.K. et al. (1997). "Biosynthesis of Isoprenoids in Higher Plant Chloroplasts Proceeds via a Mevalonate-Independent Pathway," *FEBS Letters* 400:271-274.

Lichtenthaler, H.K. (1999). "The 1-Deoxy-D-Xylulose-5-Phosphate Pathway of Isoprenoid Biosynthesis in Plants," *Annu. Rev. Plant Physiol. Plant Mol. Biol.* 50:47-65.

Lin, X.-M. et al. (2008, e-pub. Apr. 26, 2008). "Proteomic Analysis of Nalidixic Acid Resistance in *Escherichia coli*: Identification and Functional Characterization of OM Proteins," *Journal of Proteome Research* pp. A-G.

Lluch, M.A. et al. (2000). "Molecular Cloning and Expression Analysis of the Mevalonate Kinase Gene from *Arabidopsis thaliana*," *Plant Molecular Biology* 42:365-376.

Lois, L.M. et al. (Mar. 1998). "Cloning and Characterization of a Gene from *Escherichia coli* Encoding a Transketolase-Like Enzyme that Catalyzes the Synthesis of D-1-Deoxyxylulose 5-Phosphate, a Common Precursor for Isoprenoid, Thiamin, and Pyridoxol Biosynthesis," *Proc. Natl. Acad. Sci. USA* 95:2105-2110.

Loivamäki, M. et al. (Jun. 2007). "Arabidopsis, A Model to Study Biological Functions of Isoprene Emission?" *Plant Physiology* 144:1066-1078.

Lommel, S.A. et al. (1991). "Identification of the Maize Chlorotic Mottle Virus Capsid Protein Cistron and Characterization of its Subgenomic Messenger RNA," *Virology* 181:382-385.

Lücker, J. et al. (2002). "Monoterpene Biosynthesis in Lemon (*Citrus Limon*). cDNA Isolation and Functional Analysis of Four Monoterpene Synthases," *European Journal of Biochemistry* 269:3160-3171.

Luli, G.W. et al. (Apr. 1990). "Comparison of Growth, Acetate Production, and Acetate Inhibition of *Escherichia coli* in Batch and Fed-Batch Fermentations," *Applied and Environmental Microbiology* 56(4):1004-1011.

Lüttgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-D-Erythritol," *PNAS* 97(3):1062-1067.

(56) References Cited

OTHER PUBLICATIONS

Macejak, D.G. et al. (Sep. 5, 1991). "Internal Initiation of Translation Mediated by the 5' Leader of a Cellular mRNA," *Nature* 353:90-94.
Mahmoud, S.S. et al. (Jul. 17, 2001). "Metabolic Engineering of Essential Oil Yield and Composition in Mint by Altering Expression of Deoxyxylulose Phosphate Reductoisomerase and Menthofuran Synthase," *PNAS* 98(15):8915-8920.
Maldonado-Mendoza, I.E. et al. (Jul. 1997). "Molecular Characterization of Three Differentially Expressed Members of the *Camptotheca acuminata* 3-Hydroxy-3-Methylglutaryl CoA Reductase (HMGR) Gene Family," *Plant Molecular Biology* 34(5):781-790.
Mann, V. et al. (Aug. 2000). "Metabolic Engineering of Astaxanthin Production in Tobacco Flowers," *Nature Biotechnology* 18:888-892.
Martin, V.J.J. et al. (Dec. 5, 2001). "The In Vivo Synthesis of Plant Sesquiterpenes by *Escherichia coli*," *Biotechnology and Bioengineering* 75(5):497-503.
Martin, V.J.J. et al. (Jul. 2003). "Engineering a Mevalonate Pathway in *Escherichia coli* for Production of Terpenoids," *Nature Biotechnology* 21(7):796-802.
Martin, W. et al. (May 14, 1998). "Gene Transfer to the Nucleus and the Evolution of Chloroplasts," *Nature* 393:162-165.
Mashego, M.R. et al. (2007, e-pub. Nov. 8, 2006). "Microbial Metabolomics: Past, Present and Future Methodologies," *Biotechnol. Lett.* 29:1-16.
Matsuoka, S. et al. (Feb. 25, 1991). "Variable Product Specificity of Microsomal Dehydrodolichyl Diphosphate Synthase from Rat Liver," *The Journal of Biological Chemistry* 266(6):3464-3468.
Matteucci, M.D. et al. (1981). "Synthesis of Deoxyoligonucleotides on a Polymer Support," *J. American Chemical Society* 103(11):3185-3191.
Matthews, P.D. et al. (2000). "Metabolic Engineering of Carotenoid Accumulation in *Escherichia coli* by Modulation of the Isoprenoid Precursor Pool with Expression of Deoxyxylulose Phosphate Synthase," *Appl. Microbiol. Biotechnol.* 53:396-400.
Maury, J. et al. (2005, e-pub. Jul. 5, 2005). "Microbial Isoprenoid Production: An Example of Green Chemistry through Metabolic Engineering," *Adv. Biochem. Engin/Biotechnol.* 100:19-51.
McPherson, A. (2004). "Introduction to Protein Crystallization," *Methods* 34:254-265.
Meile, L. et al. (May 2001). "Characterization of the D-Xylulose 5-Phosphate/D-Fructose 6-Phosphate Phosphoketolase Gene (*xfp*) from *Bifidobacterium lactis*," *Journal of Bacteriology* 183(9):2929-2936.
Meinkoth, J. et al. (1984). "Hybridization of Nucleic Acids Immobilized on Solid Supports," *Analytical Biochemistry* 138:267-284.
Meyer, P. et al. (1996). "Homology-Dependent Gene Silencing in Plants," *Ann. Rev. Plant Physiol. Plant Mol. Biol.* 47:23-48.
Miao, L. et al. (2006, e-pub. Mar. 15, 2006). "Effect of Culture Conditions on Mycelial Growth, Antibacterial Activity, and Metabolite Profiles of the Marine-derived Fungus *Arthrinium c.f. saccharicola*," *Appl. Microbiol. Biotechnol.* 72:1063-1073.
Millen, R.S. et al. (Mar. 2001). "Many Parallel Losses of *infA* from Chloroplast DNA During Angiosperm Evolution with Multiple Independent Transfers to the Nucleus," *The Plant Cell* 13:645-658.
Miller, B. (2001). "Erstmalige Isolierung Eines Isoprenysthase-Gens und Heterologe Expression Des Aus Der Pappel Stammenden Gens Sowie Charakterisierung der Eingangsgene des Mevalonat-unabhängigen Isoprenoidbiosyntheseweges aus dem Cyanobakterium Synechococcus leopoliensis," located at <http://kups.ub.uni-koeln.de/883/>, last visited on Jun. 23, 2011, English Translation included, 2 pages.
Miller, B. et al. (2001, e-pub. May 10, 2001). "First Isolation of an Isoprene Synthase Gene from Poplar and Successful Expression of the Gene in *Escherichia coli*," *Planta* 213:483-487
Miller, J. "High-Throughput Screening for Protein Engineering of Industrial Enzymes," published by Genencor on Jun. 5, 2009, Online document—retrieved on Apr. 17, 2012, XP002673697, 29 pages.

Milne, P.J. et al. (1995). "Measurement of Vertical Distribution of Isoprene in Surface Seawater, its Chemical Fate, and its Emission from Several Phytoplankton Monocultures," *Marine Chemistry* 48:237-244.
Mo, H. et al. (2004). "Studies of the Isoprenoid-Mediated Inhibition of Mevalonate Synthesis Applied to Cancer Chemotherapy and Chemoprevention," *Exp. Biol. Med.* 229:567-585.
Mogen, B.D. et al. (Dec. 1990). "Upstream Sequences Other than AAUAAA are Required for Efficient Messenger RNA 3'-End Formation in Plants," *The Plant Cell* 2:1261-1272.
Monson, R.K. et al. (1992). "Relationships Among Isoprene Emission Rate, Photosynthesis, and Isoprene Synthase Activity as Influenced by Temperature," *Plant Physiol.* 98:1175-1180.
Munroe, D. et al. (1990). "Tales of Poly(A): a Review," *Gene* 91:151-158.
Murray, E.E. et al. (1989). "Codon Usage in Plant Genes," *Nucleic Acids Research* 17(2):477-498.
Nakamura, C.E. et al. (2003). "Metabolic Engineering for the Microbial Production of 1,3-Propanediol," *Current Opinion in Biotechnology* 14:454-459.
Nanchen, A. et al. (Apr. 2008, e-pub. Jan. 25, 2008). "Cyclic AMP-Dependent Catabolite Repression Is the Dominant Control Mechanism of Metabolic Fluxes Under Glucose Limitation in *Escherichia coli*," *Journal of Bacteriology* 190(7):2323-2330.
Nawrath, C. et al. (Dec. 1994). "Targeting of the Polyhydroxybutyrate Biosynthetic Pathway to the Plastids of *Arabidopsis thaliana* Results in High Levels of Polymer Accumulation," *Proc. Natl. Acad. Sci. USA* 91:12760-12764.
Needleman, S. B. et al. (1970). "A General Method Applicable to the Search for Similarities in the Amino Acid Sequence of Two Proteins," *J. Mol. Biol.* 48:443-453.
Neidhardt, F.C. et al. (Sep. 1974). "Culture Medium for Enterobacteria," *Journal of Bacteriology* 119(3):736-747.
Neidhardt, F.C. et al. (1990). "Table 1. Overall Macromolecular Composition of an Average *E. coli* B/r Cell*a*," Chapter 1 in *Physiology of the Bacterial Cell: A Molecular Approach*, Sinauer Associates, Inc., Sunderland, MA, pp. 4.
Nevalainen, K.M.H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc., New York, NY, pp. 129-148.
Newman, J.D. et al. (Nov. 5, 2006, e-pub. Jul. 28, 2006). "High-Level Production of Amorpha-4,11-Diene in a Two-Phase Partitioning Bioreactor of Metabolically Engineered *Escherichia coli*," *Biotechnology and Bioengineering* 95(4):684-691.
Newman, T. et al. (1994). "Genes Galore: A Summary of Methods for Accessing Results from Large-Scale Partial Sequencing of Anonymous *Arabidopsis* cDNA Clones," *Plant Physiology* 106:1241-1255.
Nielsen, K.M. et al. (1997). "Analysis and Developmental Profile of Carotenoid Pigments in Petals of Three Yellow Petunia Cultivars," *Scientia Horticulturae* 71:257-266.
Niinemets, Ü. et al. (Nov. 2002). "Stomatal Constraints May Affect Emission of Oxygenated Monoterpenoids from the Foliage of *Pinus pinea*," *Plant Physiology* 130:1371-1385.
Noronha, S.B. et al. (May 5, 2000). "Investigation of the TCA Cycle and the Glyoxylate Shunt in *Escherichia coli* BL21 and JM109 Using $^{13}$C-NMR/MS," *Biotechnology and Bioengineering* 68(3):316-327.
Nunberg, J.H. et al. (Nov. 1984). "Molecular Cloning and Characterization of the Glucoamylase Gene of *Aspergillus awamori*," *Mol. Cell. Biol.* 4(11):2306-2315.
Oh, M.-K. et al. (Apr. 12, 2002). "Global Expression Profiling of Acetate-Grown *Escherichia coli*," *The Journal of Biological Chemistry* 277(15):13175-13183.
Okamura, E. et al. (Jun. 22, 2010). "Unprecedented Acetoacetyl-coenzyme a Synthesizing Enzyme of the Thiolase Superfamily Involved in the Mevalonate Pathway," *PNAS* 107(25):11265-11270.
Ondrey, G. et al. (Oct. 2008). "Bio-Based Isoprene," *Chemical Engineering, Access Intelligence Association*, Rockville, MA, 115(1):14.
Oulmouden, A. et al. (1991). "Nucleotide Sequence of the *ERG12* Gene of *Saccharomyces cerevisiae* Encoding Mevalonate Kinase," *Curr. Genet.* 19:9-14.

(56) References Cited

OTHER PUBLICATIONS

Pachuk, C.J. et al. (2000). "Chain Reaction Cloning: A One-Step Method for Directional Ligation of Multiple DNA Fragments," *Gene* 243:19-25.

Pearson, W.R. et al. (Apr. 1988). "Improved Tools for Biological Sequence Comparison," *Proc. Natl. Acad. Sci. USA* 85:2444-2448.

Pegg, S.C.-H. et al. (2006). "Leveraging Enzyme Structure-Function Relationships for Functional Inference and Experimental Design: The Structure-Function Linkage Database," *Biochemistry* 45:2545-2555.

Penttila, M. et al. (1987). "A Versatile Transformation System for the Cellulolytic Filamentous Fungus *Trichoderma reesei*," *Gene* 61:155-164.

Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., American Society for Microbiology: Washington, D.C., pp. 615-624.

Phan, R.M. et al. (2001, e-pub. Sep. 13, 2001). "Synthesis of (S)-Isoprenoid Thiodiphosphates as Substrates and Inhibitors," *J. Org. Chem.* 66(20):6705-6710.

Phillips, T.A. et al. (Jul. 1984). "Ion Gene Product of *Escherichia coli* is a Heat-Shock Protein," *Journal of Bacteriology* 159(1):283-287.

Phue, J.-N. et al. (2004). "Transcription Levels of Key Metabolic Genes are the Cause for Different Glucose Utilization Pathways in *E. coli* B (BL21) and *E. coli* K (JM109)," *Journal of Biotechnology* 109:21-30.

Phue, J.-N. et al. (2005, e-pub. Aug. 11, 2005). "Impact of Dissolved Oxygen Concentration on Acetate Accumulation and Physiology of *E. coli* BL21, Evaluating Transcription Levels of Key Genes at Different Dissolved Oxygen Conditions," *Metabolic Engineering* 7:353-363.

Pilloff, D. et al. (Feb. 14, 2003). "The Kinetic Mechanism of Phosphomevalonate Kinase," *The Journal of Biological Chemistry* 278(7):4510-4515.

Pitera, D.J. et al. (2007, e-pub. Nov. 23, 2006). "Balancing a Heterologous Mevalonate Pathway for Improved Isoprenoid Production in *Escherichia coli*," *Metabolic Engineering* 9:193-207.

Pommer, H. et al. (1975). "Industrial Synthesis of Terpene Compounds," *Pure and Applied Chemistry* 43(3-4):527-551.

Potter, D. et al. (Oct. 10, 1997). "Identification of Catalytic Residues in Human Mevalonate Kinase," *The Journal of Biological Chemistry* 272(41):25449-25454.

Pourquié, J. et al. (1988). "Scale Up of Cellulase Production and Utilization," in *Biochemistry and Genetics of Cellulose Degradation*, Aubert, J.-P. et al. eds., Academic Press: San Diego, CA, pp. 71-86.

Proudfoot, N. (Feb. 22, 1991). "Poly(A) Signals," *Cell* 64:671-674.

Ramos-Valdivia, A.C. et al. (1997). "Isopentenyl Diphosphate Isomerase: A Core Enzyme in Isoprenoid Biosynthesis: A Review of its Biochemistry and Function," *Natural Product Reports* 6:591-603.

Raschke, M. et al. (2004, e-pub. Oct. 28, 2004). "A High-Performance Liquid Chromatography Methods for the Analysis of Intermediates of the Deoxyxylulose Phosphate Pathway," *Analytical Biochemistry* 335:235-243.

Re, E.B. et al. (1995). "Co-Expression of Native and Introduced Genes Reveals Cryptic Regulation of HMG CoA Reductase Expression in *Arabidopsis*," *The Plant Journal* 7(5):771-784.

Reiling, K.K. et al. (Jul. 20, 2004, e-pub. Jun. 18, 2004). "Mono and Diterpene Production in *Escherichia coli*," *Biotechnology and Bioengineering* 87(2):200-212.

Rodríguez-Concepción, M. et al. (2000). "Genetic Evidence of Branching in the Isoprenoid Pathway for the Production of Isopentenyl Diphosphate and Dimethylallyl Diphosphate in *Escherichia coli*," *FEBS Letters* 473:328-332.

Rodríguez-Concepción, M. et al. (Nov. 2002). "Elucidation of the Methylerythritol Phosphate Pathway for Isoprenoid Biosynthesis in Bacteria and Plastids. A Metabolic Milestone Achieved Through Genomics," *Plant Physiology* 130:1079-1089.

Rodríguez-Villalón, A. et al. (2008). "Carotenoid Accumulation in Bacteria with Enhanced Supply of Isoprenoid Precursors by Upregulation of Exogenous or Endogenous Pathways," *Journal of Biotechnology* 135:78-84.

Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-C-Methylerythritol," *PNAS* 96(21):11758-11763.

Rohdich, F. et al. (Jun. 6, 2000). "Biosynthesis of Terpenoids: 4-Diphosphocytidyl-2C-Methyl-D-Erythritol Synthase of *Arabidopsis thaliana*," *PNAS* 97(12):6451-6456.

Rohmer, M. (1998). "Isoprenoid Biosynthesis via the Mevalonate-Independent Route, a Novel Target for Antibacterial Drugs?" *Progress in Drug Research* 50:137-154.

Röhrich, R.C. et al. (2005, e-pub. Nov. 2, 2005). "Reconstitution of an Apicoplast-Localised Electron Transfer Pathway Involved in the Isoprenoid Biosynthesis of *Plasmodium falciparum*," *FEBS Letters* 579:6433-6438.

Rondon, M.R. et al. (May 1999). "Toward Functional Genomics in Bacteria: Analysis of Gene Expression in *Escherichia coli* from a Bacterial Artificial Chromosome Library of *Bacillus cereus*," *Proc. Natl. Acad. Sci. USA* 96:6451-6455.

Rosenfeld, J. et al. (1992). "In-Gel Digestion of Proteins for Internal Sequence Analysis After One- or Two-Dimensional Gel Electrophoresis," *Analytical Biochemistry* 203:173-179.

Rost, B. et al. (2004). "The PredictProtein Server," *Nucleic Acids Research* 32:W321-W326.

Sánchez, C. et al. (Apr. 2002). "The Biosynthetic Gene Cluster for the Antitumor Rebeccamycin: Characterization and Generation of Indolocarbazole Derivatives," *Chemistry and Biology* 9(4):519-531.

Sander, R. (Apr. 8, 1999). *Compilation of Henry's Law Constants for Inorganic and Organic Species of Potential Importance in Environmental Chemistry*, 3:1-107.

Sanfaçon, H. et al. (1991). "A Dissection of the Cauliflower Mosaic Virus Polyadenylation Signal," *Genes & Development* 5:141-149.

Sasaki, K. et al. (2005, e-pub. Apr. 7, 2005). "Gene Expression and Characterization of Isoprene Synthase from *Populus alba*," *FEBS Letters* 579:2514-2518.

Schneider, D. et al. (Jul. 9, 2002). "Genomic Comparisons Among *Escherichia coli* Strains B, K-12, and OI57:H7 Using IS Elements as Molecular Markers," *BMC Microbiology* 2:18, 8 pages.

Schnitzler, J.-P. et al. (2005, e-pub. Jul. 29, 2005). "Biochemical Properties of Isoprene Synthase in Poplar (*Populus x canescens*)," *Planta* 222(5):777-786.

Schöller, C. et al. (1997). "Volatile Metabolites from Some Gram-Negative Bacteria," *Chemosphere* 35(7):1487-1495.

Scott, E. et al. (2007, e-pub. Mar. 27, 2007). "Biomass in the Manufacture of Industrial Products—The Use of Proteins and Amino Acids," *Appl. Microbiol. Biotechnol.* 75:751-762.

Sen, S. et al. (2007). "Developments in Directed Evolution for Improving Enzyme Functions," *Appl. Biochem. Biotechnol.* 143:212-223.

Serino, G. et al. (1997). "A Negative Selection Scheme Based on the Expression of Cytosine Deaminase in Plastids," *The Plant Journal* 12(3):697-701.

Sharkey, T.D. et al. (Feb. 1, 2005). "Supplemental data for: Evolution of the Isoprene Biosynthetic Pathway in Kudzu," *Plant Physiology* 137(2):700-712.

Sharkey, T.D. et al. (Feb. 2005). "Evolution of the Isoprene Biosynthetic Pathway in Kudzu," *Plant Physiology* 137:700-712.

Sheir-Neiss, G. et al. (Jul. 1984). "Characterization of the Secreted Cellulases of *Trichoderma reesei* Wild Type and Mutants During Controlled Fermentations," *Appl. Microbiol. Biotechnol.* 20(1):46-53.

Shelton, D. et al. (2004, e-pub. Nov. 26, 2004). "Isolation and Partial Characterization of a Putative Monoterpene Synthase from *Melaleuca alternifolia*," *Plant Physiology and Biochemistry* 42:875-882.

Shinozaki, K. et al. (1986). "The Complete Nucleotide Sequence of the Tobacco Chloroplast Genome: its Gene Organization and Expression," *The EMBO Journal* 5(9):2043-2049.

(56) References Cited

OTHER PUBLICATIONS

Shirk, M.C. et al. (2002, e-pub. Jul. 27, 2002). "Isoprene Formation in *Bacillus subtilis*: A Barometer of Central Carbon Assimilation in a Bioreactor?" *Biotechnol. Prog.* 18(5):1109-1115.
Silver, G.M. et al. (1991). "Enzymatic Synthesis of Isoprene from Dimethylallyl Diphosphate in Aspen Leaf Extracts," *Plant Physiol.* 97:1588-1591.
Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.
Sivy, T.L. et al. (2002). "Isoprene Synthase Activity Parallels Fluctuations of Isoprene Release During Growth of *Bacillus subtilis*," *Biochemical and Biophysical Research Communications* 294:71-75.
Siwko, M.E. et al. (2007, e-pub. Oct. 4, 2006). "Does Isoprene Protect Plant Membranes from Thermal Shock? A Molecular Dynamics Study," *Biochimica et Biophysica Acta* 1768:198-206.
Slabinski, L. et al. (2007). "The Challenge of Protein Structure Determination—Lessons from Structural Genomics," *Protein Science* 16:2472-2482.
Slater, S. et al. (Apr. 1992). "Production of Poly-(3-Hydroxybutyrate-Co-3-Hydroxyvalerate) in a Recombinant *Escherichia coli* Strain," *Applied and Environmental Microbiology* 58(4):1089-1094.
Slater, S. et al. (Oct. 1999). "Metabolic Engineering of *Arabidopsis* and *Brassica* for Poly(3-Hydroxybutyrate-*co*-3-Hydroxyvalerate) Copolymer Production," *Nature Biotechnology* 17:1011-1016.
Smit, A. et al. (2000). "Biosynthesis of Isoprenoids via Mevalonate in Archaea: The Lost Pathway," *Genome Research* 10:1468-1484.
Smith, T.F. et al. (1981). "Comparison of Biosequences," *Advances in Applied Mathematics* 2:482-489.
Sprenger, G.A. et al. (Nov. 1997). "Identification of a Thiamin-Dependent Synthase in *Escherichia coli* Required for the Formation of the 1-Deoxy-D-Xylulose 5-Phosphate Precursor to Isoprenoids, Thiamin, and Pyridoxol,"*Proc. Natl. Acad. Sci. USA* 94:12857-12862.
Starks, C.M. et al. (Sep. 19, 1997). "Structural Basis for Cyclic Terpene Biosynthesis by Tobacco 5-Epi-Aristolochene Synthase," *Science* 277:1815-1820.
Staub, J. M. et al. (1995). "Expression of a Chimeric *uidA* Gene Indicates that Polycistronic mRNAs are Efficiently Translated in Tobacco Plastids," *The Plant Journal* 7(5):845-848.
Staub, J. M. et al. (Mar. 2000). "High-Yield Production of a Human Therapeutic Protein in Tobacco Chloroplast," *Nature Biotechnology* 18:333-338.
Steinbüchel, A. (2003). "Production of Rubber-Like Polymers by Microorganisms," *Current Opinion in Microbiology* 6:261-270.
Steller, I. et al. (1997). "An Algorithm for Automatic Indexing of Oscillation Images using Fourier Analysis," *Journal of Applied Crystallography* 30:1036.1040.
Stermer, B.A. et al. (1994). "Regulation of HMG-CoA Reductase Activity in Plants," *Journal of Lipid Research* 35:1133-1140.
Stevens, D.R. et al. (1997). "Genetic Engineering of Eukaryotic Algae: Progress and Prospects," *J. Phycol.* 33:713-722.
Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.
Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *Journal of Bacteriology* 184(15):4065-4070.
Takagi, M. et al. (Aug. 2000). "A Gene Cluster for the Mevalonate Pathway from *Streptomyces* sp. Strain CL190," *Journal of Bacteriology* 182(15):4153-4157.
Takahashi, S. et al. (Feb. 1999). "Purification, Characterization, and Cloning of a Eubacterial 3-Hydroxy-3-Methylglutaryl Coenzyme A Reductase, a Key Enzyme Involved in Biosynthesis of Terpenoids," *Journal of Bacteriology* 181(4):1256-1263.
Takara Bio Inc. (Feb. 2008). "Chaperon Plasmid Set," Cat. # 3340, pp. 1-8.
Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.
Thomas, F. et al. (1988). "Expression of the *rp123*, *rp12* and *rps19* Genes in Spinach Chloroplasts," *Nucleic Acids Research* 16(6):2461-2472.
Thomason, L.C. et al. (2007, e-pub. Apr. 16, 2007). "Multicopy Plasmid Modification with Phage λ Red Recombineering," *Plasmid* 58:148-158.
Thouvenot, B. et al. (2004). "The Strong Efficiency of the *Escherichia coli gapA* P1 Promoter Depends on a Complex Combination of Functional Determinants," *Biochem. J.* 383:371-382.
Timberlake, W.E. (1991). "Cloning and Analysis of Fungal Genes," Chapter 3 in *More Gene Manipulations in Fungi*, Bennett, J.W. et al. eds., Academic Press, San Diego, CA, pp. 70-76.
Tokuriki, N. et al. (2009, e-pub. Sep. 16, 2009). "Stability Effects of Mutations and Protein Evolvability," *Current Opinion in Structural Biology* 19(5):596-604.
Toriyama, K. et al. (1985). "Cell Suspension and Protoplast Culture in Rice," *Plant Science* 41:179-183.
Tsay, Y.H. et al. (Feb. 1991). "Cloning and Characterization of *ERG8*, an Essential Gene of *Saccharomyces cerevisiae* That Encodes Phosphomevalonate Kinase," *Molecular and Cellular Biology* 11(2):620-631.
Tsudsuki, T. (Apr. 27, 1998) "Direct submission, bases 1-155939", *Data Processing Center*, Submitted Feb. 27, 1998, Aichi-Gakuin University, Aichi, Japan, 12 pages.
UniProt Database Accession No. A2XGY9, last updated Jul. 27, 2011, located at <http://www.uniprot.org/jobs/201109112CDIG8GYZL.txt>, last visited on Sep. 11, 2011, 2 pages.
UniProt Database Accession No. A5AR04, last updated Jul. 27, 2011, located at <http://www.uniprot.org/jobs/20110911315BAWWKZ7.txt>, last visited on Sep. 11, 2011, 1 page.
UniProt Database Accession No. A5AV19, last updated on Oct. 16, 2013, located at http://www.uniprot.org/uniprot/A5AV19, last visited on Oct. 29, 2013, 3 pages.
UniProt Database Accession No. A5B7V4, last updated Jul. 27, 2011, located at <http://www.uniprot.org/jobs/2011091150O6CWCI3L.txt>, last visited on Sep. 11, 2011, 1 page.
UniProt Database Accession No. A5BKK1, last updated Jul. 27, 2011, located at <http://www.uniprot.org/jobs/20110911315BB1QWK6.txt>, last visited on Sep. 11, 2011, 1 page.
UniProt Database Accession No. A5BLS5, last updated Jul. 27, 2011, located at <http://www.uniprot.org/jobs/201109112CDIFUU28L.txt>, last visited on Sep. 11, 2011, 1 page.
UniProt Database Accession No. A7IZZ1, last updated on Oct. 16, 2013, located at http://www.uniprot.org/uniprot/A7IZZ1, last visited on Oct. 29, 2013, 5 pages.
UniProt Database Accession No. A9PGR5, last updated Jul. 27, 2011, located at <http://www.uniprot.org/jobs/201109112CDIFT06PL.txt>, last visited on Sep. 11, 2011, 1 page.
UniProt Database Accession No. A9Q7C9, last updated on Oct. 16, 2013, located at http://www.uniprot.org/uniprot/A9Q7C9, last visited on Oct. 29, 2013, 3 pages.
UniProt Database Accession No. B1P189, last updated Jul. 27, 2011, located at <http://www.uniprot.org/jobs/201109112CDIFXI7BK.txt>, last visited on Sep. 11, 2011, 1 page.
UniProt Database Accession No. B3GEM8, last updated Jul. 27, 2011, located at <http://www.uniprot.org/jobs/20110911315BAG9N17.txt>, last visited on Sep. 11, 2011, 1 page.
UniProt Database Accession No. B3TPQ7, "SubName: Full=Alpha-terpineol synthase." Retrieved from EBI accession No. UNIPROT:B3TPQ7 (Sep. 2, 2008), last updated on May 16, 2012, located at http://www.uniprot.org/uniprot/B3TPQ7, last visited on Jul. 23, 2012, 5 pages, (XP-002674045, XP-002674053).
UniProt Database Accession No. B6F137, last updated on Oct. 16, 2013, located at http://www.uniprot.org/uniprot/B6F137, last visited on Oct. 29, 2013, 3 pages.

(56) References Cited

OTHER PUBLICATIONS

UniProt Database Accession No. B7FLI6, last updated Jul. 27, 2011, located at <http://www.uniprot.org/jobs/20110911315BAXCRQU.txt>, last visited on Sep. 11, 2011, 1 page.
UniProt Database Accession No. B9HE95, last updated Jul. 27, 2011, located at <http://www.uniprot.org/jobs/201109112CDIFY9X6U.txt>, last visited on Sep. 11, 2011, 2 pages.
UniProt Database Accession No. B9MXU1, last updated Jul. 27, 2011, located at <http://www.uniprot.org/jobs/201109112CDIFV8DIC.txt>, last visited on Sep. 11, 2011, 2 pages.
UniProt Database Accession No. B9PAP5, last updated Jul. 27, 2011, located at <http://www.uniprot.org/jobs/201109112CDIG1HNFH.txt>, last visited on Sep. 11, 2011, 2 pages.
UniProt Database Accession No. B9RPM0, "SubName: Full=(R)-limonene synthase." Retrieved from EBI accession No. UNIPROT:B9RPM0 (Mar. 24, 2009), last updated on May 16, 2012, located at http://www.uniprot.org/uniprot/B9RPM0, last visited on Jul. 23, 2012, 3 pages.
UniProt Database Accession No. B9T537, last updated Nov. 30, 2010, located at <http://www.uniprot.org/jobs/20110911315BB065GR.txt>, last visited on Sep. 11, 2011, 1 page.
UniProt Database Accession No. B9T825, last updated Jul. 27, 2011, located at <http://www.uniprot.org/jobs/20110911315BALANC9.txt>, last visited on Sep. 11, 2011, 1 page.
UniProt Database Accession No. D7LHH0, last updated Oct. 16, 2013, located at http://www.uniprot.org/uniprot/D7LHH0, last visited on Oct. 29, 2013, 4 pages.
UniProt Database Accession No. G1JUH1, last updated Oct. 16, 2013, located at http://www.uniprot.org/uniprot/G1JUH1, last visited on Oct. 29, 2013, 5 pages.
UniProt Database Accession No. Q0PCI3, last updated Jul. 27, 2011, located at <http://www.uniprot.org/jobs/20110911315BAPL92C.txt>, last visited on Sep. 11, 2011, 1 page.
UniProt Database Accession No. Q0PCI4, last updated Jul. 27, 2011, located at <http://www.uniprot.org/jobs/20110911315BAQURQ8.txt>, last visited on Sep. 11, 2011, 1 page.
UniProt Database Accession No. Q50L36, last updated May 31, 2011, located at <http://www.uniprot.org/jobs/201109112CDIGBF1M4.txt>, last visited on Sep. 11, 2011, 2 pages.
UniProt Database Accession No. Q5SBP1, last updated Apr. 5 2011, located at <http://www.uniprot.org/jobs/201109112CDIGFFR1Q.txt>, last visited on Sep. 11, 2011, 2 pages.
UniProt Database Accession No. Q5SBP2, last updated Apr. 5, 2011, located at <http://www.uniprot.org/jobs/201109112CDIG4W1U8.txt>, last visited on Sep. 11, 2011, 2 pages.
UniProt Database Accession No. Q5SBP4, last updated Jul. 27, 2011, located at <http://www.uniprot.org/jobs/20110914OO0OYGHJF.txt>, last visited on Sep. 11, 2011, 2 pages.
UniProt Database Accession No. Q5UB07, last updated Jul. 27, 2011, located at <http://www.uniprot.org/jobs/201109112CDIFZCWUC.txt>, last visited on Sep. 11, 2011, 1 page.
UniProt Database Accession No. Q672F7, last updated Jul. 27, 2011, located at <http://www.uniprot.org/jobs/201109112CDIFWBP6O.txt >, last visited on Sep. 11, 2011, 1 page.
UniProt Database Accession No. Q6EJ97, last updated Apr. 5, 2011, located at <http://www.uniprot.org/jobs/20110911315BARZM8D.txt>, last visited on Sep. 11, 2011, 2 pages.
UniProt Database Accession No. Q6PWU1, "SubName: Full=(−)-a-terpineol synthase." Retrieved from EBI accession No. UNIPROT:Q6PWU1 (Jul. 5, 2004), last updated on Jul. 11, 2012, located at http://www.uniprot.org/uniprot/Q6PWU1, last visited on Jul. 23, 2012, 4 pages.
UniProt Database Accession No. Q7Y1V1, last updated Jul. 27, 2011, located at <http://www.uniprot.org/jobs/201109112CDIGOLK2O.txt>, last visited on Sep. 11, 2011, 1 page.
UniProt Database Accession No. Q8L5K1, last updated Oct. 16, 2013, located at http://www.uniprot.org/uniprot/Q8L5K1, last visited on Oct. 29, 2013, 3 pages.

UniProt Database Accession No. Q93X23, last updated on Oct. 16, 2013, located at http://www.uniprot.org/uniprot/Q93X23, last visited on Oct. 29, 2013, 5 pages.
UniProt Database Accession No. Q941H1, last updated Jul. 27, 2011, located at <http://www.uniprot.org/jobs/201109112CDIG6PW6Y.txt>, last visited on Sep. 11, 2011, 1 page.
UniProt Database Accession No. Q9AR86, last updated May 31, 2011, located at <http://www.uniprot.org/jobs/20110914OO0P1KMN7.txt>, last visited on Sep. 11, 2011, 2 pages.
UniProt Database Accession No. Q9LIA1; Q84UU7, last updated Jul. 27, 2011, located at <http://www.uniprotorg/jobs/20110911315BB4RI8G.txt>, last visited on Sep. 11, 2011, 3 pages.
UniProt Database Accession No. Q9LRZ6, "RecName: Full=Beta-myrcene/(E)-beta-ocimene synthase 2, chloroplastic; EC=4.2.3.15; AltName: Full=Terpenoid synthase 24; Short=AtTpS24; Flags: Precursor." Retrieved from EBI accession No. UNIPROT:Q9LRZ6 (Oct. 1, 2000); last updated on Jul. 11, 2012, located at http://www.uniprot.org/uniprot/Q9LRZ6, last visited on Jul. 23, 2012, 8 pages.
UniProt Database Accession No. Q7XAS7, last updated Apr. 5, 2011, located at <http://www.uniprot.org/jobs/201109112CDIGCK99G.txt>, last visited on Sep. 11, 2011, 2 pages.
UniProt Database Accession No. Q9FQ26, last updated Jul. 27, 2011, located at <http://www.uniprot.org/jobs/20110911315BB3SH2Y.txt>, last visited on Sep. 11, 2011, 1 page.
Vadali, R.V. et al. (2005, e-pub. Sep. 2, 2005). "Enhanced Lycopene Productivity by Manipulation of Carbon Flow to Isopentenyl Diphosphate in *Escherichia coli*," *Biotechnol. Prog.* 21(5):1558-1561.
Vagin, A. et al. (1997). "*MOLREP*: An Automated Program for Molecular Replacement," *Journal of Applied Crystallography* 30:1022-1025.
Vandamme, E.J. et al. (2002, e-pub. 2002). "Bioflavours and Fragrances via Fermentation and Biocatalysis," *Journal of Chemical Technology and Biotechnology* 77:1323-1332.
Van Den Hondel, C.A.M.J.J. et al. (1991). "Heterologous Gene Expression in Filamentous Fungi," Chapter 18 in *More Gene Manipulations in Fungi*, Bennett, J.W. et al. eds., Academic Press, Inc.: San Diego, CA, pp. 396-428.
Van De Walle, M. et al. (Jan. 5, 1998). "Proposed Mechanism of Acetate Accumulation in Two Recombinant *Escherichia coli* Strains During High Density Fermentation," *Biotechnology and Bioengineering* 57(1):71-78.
Van Hylckama, J.E.T. et al. (Apr. 2000). "Characterization of the Gene Cluster Involved in Isoprene Metabolism in *Rhodococcus* sp. Strain AD45," *Journal of Bacteriology* 182(7):1956-1963.
Vane, L.M. (2005, e-pub. Apr. 21, 2005). "A Review of Pervaporation for Product Recovery from Biomass Fermentation Processes," *Journal of Chemical Technology and Biotechnology* 80:603-629.
Velikova, V. et al. (2005). "Consequences of Inhibition of Isoprene Synthesis in *Phragmites australis* Leaves Exposed to Elevated Temperatures," *Agriculture, Ecosystems & Environment* 106:209-217.
Vidal, M. et al. (2006, e-pub. Nov. 23, 2005). "Evaluation of Lower Flammability Limits of Fuel-Air-Diluent Mixtures Using Calculated Adiabatic Flame Temperatures," *Journal of Hazardous Materials* 130:21-27.
Voss, S. et al. (1997). "Mutagenesis of a Flexible Loop in Streptavidin Leads to Higher Affinity for the *Strep*-tag II Peptide and Improved Performance in Recombinant Protein Purification," *Protein Engineering* 10(8):975-982.
Voynova, N.E. et al. (Jan. 2004). "*Staphylococcus aureus* Mevalonate Kinase: Isolation and Characterization of an Enzyme of the Isoprenoid Biosynthetic Pathway," *Journal of Bacteriology* 186(1):61-67.
Wagner, W.P. et al. (Aug. 1999). "Three Distinct Phases of Isoprene Formation During Growth and Sporulation of *Bacillus subtilis*," *Journal of Bacteriology* 181(15):4700-4703.
Wagner, W.P. et al. (Jan. 2000, e-pub. Nov. 18, 1999). "Isoprene Biosynthesis in *Bacillus subtilis* via the Methylerythritol Phosphate Pathway," *J. Nat. Prod.* 63(1):37-40.
Wang, C.-W. et al. (Jan. 20, 1999). "Engineered Isoprenoid Pathway Enhances Astaxanthin Production in *Escherichia coli*," *Biotechnology and Bioengineering* 62(2):235-241.

(56) References Cited

OTHER PUBLICATIONS

Ward, M. et al. (Aug. 1993). "Use of *Aspergillus* Overproducing Mutants, Cured for Integrated Plasmid, to Overproduce Heterologous Proteins," *Appl. Microbiol. Biotechnol.* 39(6):738-743.

Weissermel, K. et al. (2003). *Industrial Organic Chemistry, 4th, Completely Revised Edition*, translated by Lindley, C.R. et al., Wiley-VCH GmbH & Co. KGaA, Weinheim, Germany, pp. 117-222.

Whisstock, J.C. et al. (2003). "Prediction of Protein Function from Protein Sequence and Structure," *Quarterly Reviews of Biophysics* 36(3):307-340.

Whittington, D.A. et al. (Nov. 26, 2002). "Bornyl Diphosphate Synthase: Structure and Strategy for Carbocation Manipulation by a Terpenoid Cyclase," *PNAS* 99(24):15375-15380.

Wilde, R.J. et al. (1986). "Transcript Analysis of the Citrate Synthase and Succinate Dehydrogenase Genes of *Escherichia coli* K12," *Journal of General Microbiology* 132:3239-3251.

Wildermuth, M.C. et al. (1998). "Biochemical Characterization of Stromal and Thylakoid-Bound Isoforms of Isoprene Synthase in Willow Leaves," *Plant Physiology* 116:1111-1123.

Wilding, E.I. et al. (Aug. 2000). "Identification, Evolution, and Essentiality of the Mevalonate Pathway for Isopentenyl Diphosphate Biosynthesis in Gram-Positive Cocci," *Journal of Bacteriology* 182(15):4319-4327.

Wilkins, K. (1996). "Volatile Metabolites from Actinomycetes," *Chemosphere* 32(7):1427-1434.

Williams, D.C. et al. (1998). "Truncation of Limonene Synthase Preprotein Provides a Fully Active 'Pseudomature' Form of This Monoterpene Cyclase and Reveals the Function of the Amino-Terminal Arginine Pair," *Biochemistry* 37(35):12213-12220.

Wishart, M.J. et al. (Nov. 10, 1995). "A Single Mutation Converts a Novel Phosphotyrosine Binding Domain into a Dual-Specificity Phosphatase," *The Journal of Biological Chemistry* 270(45):26782-26785.

Withers, S.T. et al. (Oct. 2007, e-pub. Aug. 10, 2007). "Identification of Isopentenol Biosynthetic Genes from *Bacillus subtilis* by a Screening Method Based on Isoprenoid Precursor Toxicity," *Applied and Environmental Microbiology* 73(19):6277-6283.

Witkowski, A. et al. (1999, e-pub. Aug. 18, 1999). "Conversion of β-Ketoacyl Synthase to a Malonyl Decarboxylase by Replacement of the Active-Site Cysteine with Glutamine," *Biochemistry* 38(36):11643-11650.

Wolfertz, M. et al. (2003). "Biochemical Regulation of Isoprene Emission," *Plant, Cell and Environment* 26:1357-1364.

Wolfertz, M. et al. (Aug. 2004). "Rapid Regulation of the Methylerythritol 4-Phosphate Pathway During Isoprene Synthesis," *Plant Physiology* 135:1939-1945.

Wu, D.Y. et al. (1989). "The Ligation Amplification Reaction (LAR)-Amplification of Specific DNA Sequences Using Sequential Rounds of Template-Dependent Ligation," *Genomics* 4:560-569.

Xia, X.-X. et al. (2008). "Comparison of the Extracellular Proteomes of *Escherichia coli* B and K-12 Strains During High Cell Density Cultivation," *Proteomics* 8:1-15.

Yamada, K. et al. (1989). "Production of Glycerol from Methanol by a Mutant Strain of *Candida boidinii* No. 2201," *Agric. Biol. Chem.* 53(2):541-543.

Yang, D. et al. (Mar. 15, 2002, published ahead of print Dec. 19, 2001). "Structure of the *Methanococcus jannaschii* Mevalonate Kinase, a Member of the GHMP Kinase Superfamily," *The Journal of Biological Chemistry* 277(11):9462-9467.

Ye, X. et al. (Jan. 14, 2000). "Engineering the Provitamin A (β-Carotene) Biosynthetic Pathway into (Carotenoid-Free) Rice Endosperm," *Science* 287:303-305.

Yelton, M.M. et al. (Mar. 1984). "Transformation of *Aspergillus nidulans* by Using a *trpC* Plasmid," *Proc. Natl. Acad. Sci. USA* 81:1470-1474.

Yoon, S.-H. et al. (2007, e-pub. May 15, 2007). "Increased β-Carotene Production in Recombinant *Escherichia coli* Harboring an Engineered Isoprenoid Precursor Pathway with Mevalonate Addition," *Biotechnol. Prog.* 23(3):599-605.

Yoon, S.-H. et al. (2009). "Combinatorial Expression of Bacterial Whole Mevalonate Pathway for the Production of β-Carotene in *E. coli*," *Journal of Biotechnology* 140:218-226.

Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.

International Search Report mailed on Jun. 18, 2009, for PCT Patent Application No. PCT/US08/86869, filed on Dec. 15, 2008, one page.

International Search Report mailed on Dec. 8, 2009, for PCT Application No. PCT/US2009/041581, filed on Apr. 23, 2009, nine pages.

International Search Report mailed on Dec. 30, 2010, for PCT Application No. PCT/US2010/032134, filed on Apr. 22, 2010, 15 pages.

International Search Report mailed on Jul. 24, 2012, for PCT Patent Application No. PCT/US2011/058188, filed on Oct. 27, 2011, ten pages.

* cited by examiner

Figure 3A (Seq. ID 1: Sequence of p9795)

tagaaaaactcatcgagcatcaaatgaaactgcaatttattcatatcaggattatcaat
accatattttgaaaagccgtttctgtaatgaaggagaaaactcaccgaggcagttcc
ataggatggcaagatcctggtatcggtctgcgattccgactcgtccaacatcaatacaa
cctattaatttccctcgtcaaaaataaggttatcaagtgagaaatcaccatgagtgac
gactgaatccggtgagaatggcaaaagtttatgcatttctttccagacttgttcaacag
gccagccattacgctcgtcatcaaaatcactcgcatcaaccaaaccgttattcattcgt
gattgcgcctgagcgaggcgaaatacgcgatcgctgttaaaaggacaattacaaacagg
aatcgagtgcaaccggcgcaggaacactgccagcgcatcaacaatattttcacctgaat
caggatattcttctaatacctggaacgctgttttccggggatcgcagtggtgagtaac
catgcatcatcaggagtacggataaaatgcttgatggtcggaagtggcataaattccgt
cagccagtttagtctgaccatctcatctgtaacatcattggcaacgctacctttgccat
gtttcagaaacaactctggcgcatcggcttcccatacaagcgatagattgtcgcacct
gattgcccgacattatcgcgagcccatttatacccatataaatcagcatccatgttgga
atttaatcgcggcctcgacgtttccgttgaatatggctcatattcttccttttcaat
attattgaagcatttatcaggttattgtctcatgagcggatacatatttgaatgtatt
tagaaaaataaacaaataggggtcagtgttacaaccaattaaccaattctgaacattat
cgcgagcccatttatacctgaatatggctcataacacccttgtttgcctggcggcagt
agcgcggtggtcccacctgaccccatgccgaactcagaagtgaaacgccgtagcgccga
tggtagtgtggggactcccatgcgagagtagggaactgccaggcatcaaataaaacga
aaggctcagtcgaaagactgggcctttcgcccgggctaattaggggtgtcgcctttc
gattgacgctgcagttagacatacatcagctggttaatcgggaagggtcaatcagcag
cagtttgatgcggttttcagtcgcgtagtctgggcgacccagaccatcgccatactggt
aggtgcagtgggaaacacgtgccatgttaactgcgatttccatgaacgctttaggcagc
agggtggagtcgctaacgcgttcacgattcatcttttccattcggcgtcgatcagttt
acgcagttcttcgcgggcctgttcctcgctggtaccatcgttttcgtgcatgtagctaa
tgatagaattggtagtctcgccacgttccagctccgccgcagaggtggccagatcgttg
cacaggcggaagataacgcagctagaacgcaccagaccatggaagtcggtcagggaacg
cagcgcgtggtcggagatgtcttcctgctgctggcatacggaaaagtaagacggcgcca
gcagcgctacaccggaggaggaaacgctggcgttttccaggtacttggagaaagccggg
ataatttgttgttggaccatttcgcctcttgcagaaaggctttgcacagttcacgcca
gcttttcgtcagataggacaggttgttatgacctttctctttcagaatagaataggacg
tgtcgttaacggtgttgtacagtgccaggaaacacagtttcatatagtccggcagggtg
ttaatagcgttaacgtcccagcgctctacagcatcggtgaacagttgcagttcgtccag
agtgccataaacgtcatacacgtcatcgatgatcgtcaccagaccaaacattttagtaa
cagctttgcgacattcaccaaactgcgggtctggcgccatacccagtgcccagaaataa
acttccatcaggcggtcgcgtacaaaatccagtttgctagccaggcccatctcggtcca
ccagcgggacagatcttgcagctctttctggtgcagggtctgtaccatgttaaaatcca
gcttcgccagctccagcagcagctggtgatgcggttcttcggttcgtatttatccagg
aaccaacgtgcctccagacggtgcagacgctggtgatatggcagttccagggcgtggct
cacttgttctgcaaccttggtattaatgccttcttcaggttgttcttcaggtgggtga
tggaaaaggtacgcgcctcctccagcaggttctcaccctcgaaacccaggtaagacgct
tcatacaggctcagcaggccttggacgtcacctttcagttcaccgctgaaaccaccttc
tttatccttgaaacgctcaaaaacatcctgagaaacctcgaaaccgtgctgacgcagca
gacggaaagacagagcggttgcgtgcaggtcagatttgttctttttgttttcgtccagc
agtacgatgttttccagggctttaatgatgtcttttcaaatttgtaggtcagacccag Figure 3B (Seq. ID 1: Sequence of p9795)

```
gcgctgcacatcgtcgatcagctccagcagggacagcggctgggtgtctacacggttga
tcatgcagcgaacttcttcctccagtttggtcgcttctcctccagcttttccacttc
aggtcgttctccagggattgcaggaattcgaattccacaggtttggctgatagtttgc
ggaacgacgggaattatgctcggtaatctgagtaaattgagaagaggtcgcacacatgt
tcagcgacaagggcgacacaaaatttattctaaatgcataataaatactgataacatct
tatagtttgtattatattttgtattatcgttgacatgtataattttgatatcaaaaact
gattttcccttattattttcgagatttatttcttaattctctttaacaaactagaaa
tattgtatatacaaaaaatcataataatagatgaatagtttaattataggtgttcatc
aatcgaaaagcaacgtatcttatttaaagtgcgttgcttttctcatttataaggtt
aaataattctcatatatcaagcaaagtgacaggcgcccttaaatattctgacaaatgct
ctttccctaaactcccccataaaaaaaccgccgaagcgggttttacgttatttgcg
gattaacgattactcgttatcagaaccgcccagggggcccgagcttaagactggccgtc
gttttacaacacagaaagagtttgtagaaacgcaaaaggccatccgtcagggccttc
tgcttagtttgatgcctggcagttccctactctcgccttccgcttcctcgctcactgac
tcgctgcgctcggtcgttcggctgcggcgagcggtatcagctcactcaaaggcggtaat
acggttatccacagaatcaggggataacgcaggaaagaacatgtgagcaaaaggccagc
aaaaggccaggaaccgtaaaaaggccgcgttgctggcgttttccataggctccgccc
cctgacgagcatcacaaaaatcgacgctcaagtcagaggtggcgaaacccgacaggact
ataaagataccaggcgtttccccctggaagctccctcgtgcgctctcctgttccgaccc
tgccgcttaccggatacctgtccgcctttctcccttcgggaagcgtggcgctttctcat
agctcacgctgtaggtatctcagttcggtgtaggtcgttcgctccaagctgggctgtgt
gcacgaaccccccgttcagcccgaccgctgcgccttatccggtaactatcgtcttgagt
ccaacccggtaagacacgacttatcgccactggcagcagccactggtaacaggattagc
agagcgaggtatgtaggcggtgctacagagttcttgaagtggtgggctaactacggcta
cactagaagaacagtatttggtatctgcgctctgctgaagccagttaccttcggaaaaa
gagttggtagctcttgatccggcaaacaaaccaccgctggtagcggtggtttttttgtt
tgcaagcagcagattacgcgcagaaaaaaggatctcaagaagatcctttgatcttttc
tacggggtctgacgctcagtggaacgacgcgcgtaactcacgttaagggattttggt
catgagcttgcgccgtcccgtcaagtcagcgtaatgctctgcttt
```

Figure 5A (Seq. ID 2: Sequence of pTrcKudzu)

```
gtttgacagcttatcatcgactgcacggtgcaccaatgcttctggcgtcaggcagccat
cggaagctgtggtatggctgtgcaggtcgtaaatcactgcataattcgtgtcgctcaag
gcgcactccgttctggataatgttttttgcgccgacatcataacggttctggcaaata
ttctgaaatgagctgttgacaattaatcatccggctcgtataatgtgtggaattgtgag
cggataacaatttcacacaggaaacagcgccgctgagaaaaagcgaagcggcactgctc
tttaacaatttatcagacaatctgtgtgggcactcgaccggaattatcgattaacttta
ttattaaaaattaaagaggtatatattaatgtatcgattaaataaggaggaataaacca
tgtgtgcgacctcttctcaatttactcagattaccgagcataattcccgtcgttccgca
aactatcagccaaacctgtggaatttcgaattcctgcaatccctggagaacgacctgaa
agtggaaaagctggaggagaaagcgaccaaactggaggaagaagttcgctgcatgatca
accgtgtagacacccagccgctgtcctgctggagctgatcgacgatgtgcagcgcctg
ggtctgacctacaaatttgaaaagacatcattaaagccctggaaaacatcgtactgct
ggacgaaaacaaaagaacaaatctgacctgcacgcaaccgctctgtctttccgtctgc
tgcgtcagcacggtttcgaggttctcaggatgttttgagcgtttcaaggataaagaa
ggtggttttcagcggtgaactgaaaggtgacgtccaaggcctgctgagcctgtatgaagc
gtcttacctgggtttcgagggtgagaacctgctggaggaggcgcgtaccttttccatca
cccacctgaagaacaacctgaaagaaggcattaataccaaggttgcagaacaagtgagc
cacgccctggaactgccatatcaccagcgtctgcaccgtctggaggcacgttggttcct
ggataaatacgaaccgaagaaccgcatcaccagctgctgctggagctggcgaagctgg
attttaacatggtacagaccctgcaccagaaagagctgcaagatctgtcccgctggtgg
accgagatgggcctggctagcaaactggattttgtacgcgaccgcctgatggaagttta
tttctgggcactgggtatggcgccagacccgcagtttggtgaatgtcgcaaagctgtta
ctaaaatgtttggtctggtgacgatcatcgatgacgtgtatgacgtttatggcactctg
gacgaactgcaactgttcaccgatgctgtagagcgctgggacgttaacgctattaacac
cctgccggactatatgaaactgtgtttcctggcactgtacaacaccgttaacgacacgt
cctattctattctgaaagagaaaggtcataacaacctgtcctatctgacgaaaagctgg
cgtgaactgtgcaaagcctttctgcaagaggcgaaatggtccaacaacaaaattatccc
ggctttctccaagtacctggaaaacgccagcgtttcctcctccggtgtagcgctgctgg
cgccgtcttacttttccgtatgccagcagcaggaagacatctccgaccacgcgctgcgt
tccctgaccgacttccatggtctggtgcgttctagctgcgttatcttccgcctgtgcaa
cgatctggccacctctgcggcggagctggaacgtggcgagactaccaattctatcatta
gctacatgcacgaaaacgatggtaccagcgaggaacaggcccgcgaagaactgcgtaaa
ctgatcgacgccgaatggaaaaagatgaatcgtgaacgcgttagcgactccaccctgct
gcctaaagcgttcatggaaatcgcagttaacatggcacgtgtttcccactgcacctacc
agtatggcgatggtctggtcgccagactacgcgactgaaaaccgcatcaaactgctg
ctgattgacccttttccgattaaccagctgatgtatgtctaactgcagctggtaccata
tgggaattcgaagctttctagaacaaaaactcatctcagaagaggatctgaatagcgcc
gtcgaccatcatcatcatcatcattgagtttaaacggtctccagcttggctgttttggc
ggatgagagaagattttcagcctgatacagattaaatcagaacgcagaagcggtctgat
aaaacagaatttgcctggcggcagtagcgcggtggtcccacctgacccatgccgaact
cagaagtgaaacgccgtagcgccgatggtagtgtggggtctccccatgcgagagtaggg
aactgccaggcatcaaataaaacgaaaggctcagtcgaaagactgggcctttcgttta
tctgttgtttgtcggtgaacgctctcctgagtaggacaaatccgccgggagcggatttg
aacgttgcgaagcaacggcccggagggtggcgggcaggacgcccgccataaactgccag
gcatcaaattaagcagaaggccatcctgacggatggcctttttgcgtttctacaaactc
```

Figure 5B (Seq. ID 2: Sequence of pTrcKudzu)

```
tttttgtttattttctaaatacattcaaatatgtatccgctcatgagacaataaccct
gataaatgcttcaataatattgaaaaggaagagtatgagtattcaacatttccgtgtc
gcccttattccttttttgcggcattttgccttcctgtttttgctcacccagaaacgct
ggtgaaagtaaaagatgctgaagatcagttgggtgcacgagtgggttacatcgaactgg
atctcaacagcggtaagatccttgagagttttcgccccgaagaacgttttccaatgatg
agcacttttaaagttctgctatgtggcgcggtattatcccgtgttgacgccgggcaaga
gcaactcggtcgccgcatacactattctcagaatgacttggttgagtactcaccagtca
cagaaaagcatcttacggatggcatgacagtaagagaattatgcagtgctgccataacc
atgagtgataacactgcggccaacttacttctgacaacgatcggaggaccgaaggagct
aaccgcttttttgcacaacatgggggatcatgtaactcgccttgatcgttgggaaccgg
agctgaatgaagccataccaaacgacgagcgtgacaccacgatgcctgtagcaatggca
acaacgttgcgcaaactattaactggcgaactacttactctagcttcccggcaacaatt
aatagactggatggaggcggataaagttgcaggaccacttctgcgctcggcccttccgg
ctggctggtttattgctgataaatctggagccggtgagcgtgggtctcgcggtatcatt
gcagcactggggccagatggtaagccctcccgtatcgtagttatctacacgacggggag
tcaggcaactatggatgaacgaaatagacagatcgctgagataggtgcctcactgatta
agcattggtaactgtcagaccaagtttactcatatactttagattgatttaaaactt
catttttaatttaaaaggatctaggtgaagatcctttttgataatctcatgaccaaaat
cccttaacgtgagttttcgttccactgagcgtcagaccccgtagaaaagatcaaggat
cttcttgagatcctttttttctgcgcgtaatctgctgcttgcaaacaaaaaaaccaccg
ctaccagcggtggtttgtttgccggatcaagagctaccaactctttttccgaaggtaac
tggcttcagcagagcgcagataccaaatactgtccttctagtgtagccgtagttaggcc
accacttcaagaactctgtagcaccgcctacatacctcgctctgctaatcctgttacca
gtggctgctgccagtggcgataagtcgtgtcttaccgggttggactcaagacgatagtt
accggataaggcgcagcggtcgggctgaacggggggttcgtgcacacagcccagcttgg
agcgaacgacctacaccgaactgagatacctacagcgtgagctatgagaaagcgccacg
cttcccgaagggagaaaggcggacaggtatccggtaagcggcagggtcggaacaggaga
gcgcacgagggagcttccaggggaaacgcctggtatctttatagtcctgtcgggtttc
gccacctctgacttgagcgtcgatttttgtgatgctcgtcaggggcggagcctatgg
aaaaacgccagcaacgcggcctttttacggttcctggccttttgctggccttttgctca
catgttctttcctgcgttatcccctgattctgtggataaccgtattaccgcctttgagt
gagctgataccgctcgccgcagccgaacgaccgagcgcagcgagtcagtgagcgagga
agcggaagagcgcctgatgcggtattttctccttacgcatctgtgcggtattcacaccg
catatggtgcactctcagtacaatctgctctgatgccgcatagttaagccagtatacac
tccgctatcgctacgtgactgggtcatggctgcgccccgacacccgccaacacccgctg
acgcgccctgacgggcttgtctgctcccggcatccgcttacagacaagctgtgaccgtc
tccgggagctgcatgtgtcagaggttttcaccgtcatcaccgaaacgcgcgaggcagca
gatcaattcgcgcgcgaaggcgaagcggcatgcatttacgttgacaccatcgaatggtg
caaaacctttcgcggtatggcatgatagcgcccggaagagagtcaattcagggtggtga
atgtgaaaccagtaacgttatacgatgtcgcagagtatgccggtgtctcttatcagacc
gtttcccgcgtggtgaaccaggccagccacgtttctgcgaaaacgcgggaaaaagtgga
agcggcgatggcggagctgaattacattcccaaccgcgtggcacaacaactggcgggca
aacagtcgttgctgattggcgttgccacctccagtctggccctgcacgcgccgtcgcaa
attgtcgcggcgattaaatctcgcgccgatcaactgggtgccagcgtggtggtgtcgat
ggtagaacgaagcggcgtcgaagcctgtaaagcggcggtgcacaatcttctcgcgcaac
```

Figure 5C (Seq. ID 2: Sequence of pTrcKudzu)

```
gcgtcagtgggctgatcattaactatccgctggatgaccaggatgccattgctgtggaa
gctgcctgcactaatgttccggcgttatttcttgatgtctctgaccagacacccatcaa
cagtattattttctcccatgaagacggtacgcgactgggcgtggagcatctggtcgcat
tgggtcaccagcaaatcgcgctgttagcgggcccattaagttctgtctcggcgcgtctg
cgtctggctggctggcataaatatctcactcgcaatcaaattcagccgatagcggaacg
ggaaggcgactggagtgccatgtccggttttcaacaaaccatgcaaatgctgaatgagg
gcatcgttccactgcgatgctggttgccaacgatcagatggcgctgggcgcaatgcgc
gccattaccgagtccgggctgcgcgttggtgcggatatctcggtagtgggatacgacga
taccgaagacagctcatgttatatccgccgtcaaccaccatcaaacaggattttcgcc
tgctggggcaaaccagcgtggaccgcttgctgcaactctctcagggccaggcggtgaag
ggcaatcagctgttgcccgtctcactggtgaaaagaaaaaccaccctggcgcccaatac
gcaaaccgcctctcccgcgcgttggccgattcattaatgcagctggcacgacaggttt
cccgactggaaagcgggcagtgagcgcaacgcaattaatgtgagttagcgcgaattgat
ctg
```

Figure 7A (Seq ID 3: Sequence of pMAL-C4X)

```
ccgacaccatcgaatggtgcaaaacctttcgcggtatggcatgatagcgcccggaagag
agtcaattcaggqtggtgaatgtgaaaccagtaacgttatacgatgtcgcagagtatgc
cggtgtctcttatcagaccgtttccgcgtggtgaaccaggccagccacgtttctgcga
aaacgcgggaaaaagtggaagcggcgatggcggagctgaattacattcccaaccgcgtg
gcacaacaactggcgggcaaacagtcgttgctgattggcgttgccacctccagtctggc
cctgcacgcgccgtcgcaaattgtcgcggcgattaaatctcgcgccgatcaactgggtg
ccagcgtggtggtgtcgatggtagaacgaagcggcgtcgaagcctgtaaagcggcgtg
cacaatcttctcgcgcaacgcgtcagtggctgatcattaactatcgctggatgacca
ggatgccattgctgtggaagctgcctgcactaatgttccggcgttatttcttgatgtct
ctgaccagacacccatcaacagtattattttctcccatgaagacggtacgcgactgggc
gtggagcatctggtcgcattgggtcaccagcaaatcgcgctgttagcgggcccattaag
ttctgtctcggcgcgtctgcgtctggctggctggcataaatatctcactcgcaatcaaa
ttcagccgatagcggaacgggaaggcgactggagtgccatgtccggttttcaacaaacc
atgcaaatgctgaatgagggcatcgttcccactgcgatgctggttgccaacgatcagat
ggcgctgggcgcaatgcgcgccattaccgagtccgggctgcgcgttggtgcggatatct
cggtagtgggatacgacgataccgaagacagctcatgttatatcccgccgttaaccacc
atcaaacaggattttcgcctgctggggcaaaccagcgtggaccgcttgctgcaactctc
tcagggccaggcggtgaagggcaatcagctgttgcccgtctcactggtgaaaagaaaaa
ccaccctggcgcccaatacgcaaaccgcctctccccgcgcgttggccgattcattaatg
cagctggcacgacaggtttcccgactggaaagcgggcagtgagcgcaacgcaattaatg
taagttagctcactcattaggcacaattctcatgtttgacagcttatcatcgactgcac
ggtgcaccaatgcttctggcgtcaggcagccatcggaagctgtggtatggctgtgcagg
tcgtaaatcactgcataattcgtgtcgctcaaggcgcactccgttctggataatgttt
tttgcgccgacatcataacggttctggcaaatattctgaaatgagctgttgacaattaa
tcatcggctcgtataatgtgtggaattgtgagcggataacaatttcacacaggaaacag
ccagtccgtttaggtgttttcacgagcacttcaccaacaaggaccatagcatatgaaaa
tcgaagaaggtaaactggtaatctggattaacggcgataaaggctataacggtctcgct
gaagtcggtaagaaattcgagaagataccggaattaaagtcaccgttgagcatccgga
taaactggaagagaaattcccacaggttgcggcaactggcgatggccctgacattatct
tctgggcacacgaccgctttggtggctacgctcaatctggcctgttggctgaaatcacc
ccggacaaagcgttccaggacaagctgtatccgtttacctgggatgccgtacgttacaa
cggcaagctgattgcttaccgatcgctgttgaagcgttatcgctgatttataacaaag
atctgctgccgaacccgccaaaaacctgggaagagatcccggcgctggataaagaactg
aaagcgaaaggtaagagcgcgctgatgttcaacctgcaagaaccgtacttcacctggcc
gctgattgctgctgacggggttatgcgttcaagtatgaaaacggcaagtacgacatta
agacgtgggcgtggataacgctggcgcgaaagcgggtctgaccttcctggttgacctg
attaaaaacaaacacatgaatgcagacaccgattactccatcgcagaagctgcctttaa
taaaggcgaaacagcgatgaccatcaacggcccgtgggcatggtccaacatcgacacca
gcaaagtgaattatggtgtaacggtactgccgaccttcaagggtcaaccatccaaaccg
ttcgttggcgtgctgagcgcaggtattaacgccgccagtccgaacaaagagctggcaaa
agagttcctcgaaaactatctgctgactgatgaaggtctggaagcggttaataaagaca
aaccgctgggtgccgtagcgctgaagtcttacgaggaagagttggtgaaagatccgcgg
attgccgccactatggaaaacgcccagaaaggtgaaatcatgccgaacatcccgcagat
gtccgctttctggtatgccgtgcgtactgcggtgatcaacgccgccagcggtcgtcaga
ctgtcgatgaagccctgaaagacgcgcagactaattcgagctcgaacaacaacaacaat
```

Figure 7B (Seq ID 3: Sequence of pMAL-C4X)

```
aacaataacaacaacctcgggatcgagggaaggatttcagaattcggatcctctagagt
cgacctgcaggcaagcttggcactggccgtcgttttacaacgtcgtgactgggaaaacc
ctggcgttacccaacttaatcgccttgcagcacatccccctttcgccagctggcgtaat
agcgaagaggcccgcaccgatcgcccttcccaacagttgcgcagcctgaatggcgaatg
gcagcttggctgttttggcggatgagataagattttcagcctgatacagattaaatcag
aacgcagaagcggtctgataaaacagaatttgcctggcggcagtagcgcggtggtccca
cctgaccccatgccgaactcagaagtgaaacgccgtagcgccgatggtagtgtggggtc
tccccatgcgagagtagggaactgccaggcatcaaataaaacgaaaggctcagtcgaaa
gactgggcctttcgttttatctgttgtttgtcggtgaacgctctcctgagtaggacaaa
tccgccgggagcggatttgaacgttgcgaagcaacggcccggagggtggcgggcaggac
gcccgccataaactgccaggcatcaaattaagcagaaggccatcctgacggatggcctt
tttgcgtttctacaaactcttttgtttattttctaaatacattcaaatatgtatccg
ctcatgagacaataaccctgataaatgcttcaataatattgaaaaaggaagagtatgag
tattcaacatttccgtgtcgcccttattccctttttttgcggcatttttgccttcctgttt
ttgctcacccagaaacgctggtgaaagtaaaagatgctgaagatcagttgggtgcacga
gtgggttacatcgaactggatctcaacagcggtaagatccttgagagttttcgccccga
agaacgttctccaatgatgagcacttttaaagttctgctatgtggcgcggtattatccc
gtgttgacgccgggcaagagcaactcggtcgccgcatacactattctcagaatgacttg
gttgagtactcaccagtcacagaaaagcatcttacggatggcatgacagtaagagaatt
atgcagtgctgccataaccatgagtgataacactgcggccaacttacttctgacaacga
tcggaggaccgaaggagctaaccgcttttttgcacaacatggggatcatgtaactcgc
cttgatcgttgggaaccggagctgaatgaagccataccaaacgacgagcgtgacaccac
gatgcctgtagcaatggcaacaacgttgcgcaaactattaactggcgaactacttactc
tagcttcccggcaacaattaatagactggatggaggcggataaagttgcaggaccactt
ctgcgctcggcccttccggctggctggtttattgctgataaatctggagccggtgagcg
tgggtctcgcggtatcattgcagcactggggccagatggtaagccctcccgtatcgtag
ttatctacacgacggggagtcaggcaactatggatgaacgaaatagacagatcgctgag
ataggtgcctcactgattaagcattggtaactgtcagaccaagtttactcatatatact
ttagattgatttaccccggttgataatcagaaaagccccaaaaacaggaagattgtata
agcaaatatttaaattgtaaacgttaatattttgttaaaattcgcgttaaattttgtt
aaatcagctcattttttaaccaataggccgaaatcggcaaaatcccttataaatcaaaa
gaatagaccgagatagggttgagtgttgttccagtttggaacaagagtccactattaaa
gaacgtggactccaacgtcaaagggcgaaaaaccgtctatcagggcgatggcccactac
gtgaaccatcacccaaatcaagttttttggggtcgaggtgccgtaaagcactaaatcgg
aaccctaaagggagcccccgatttagagcttgacggggaaagccggcgaacgtggcgag
aaaggaagggaagaaagcgaaaggagcgggcgctagggcgctggcaagtgtagcggtca
cgctgcgcgtaaccaccacacccgccgcgcttaatgcgccgctacagggcgcgtaaaag
gatctaggtgaagatcctttttgataatctcatgaccaaaatcccttaacgtgagtttt
cgttccactgagcgtcagacccgtagaaaagatcaaaggatcttcttgagatccttt
tttctgcgcgtaatctgctgcttgcaaacaaaaaaaccaccgctaccagcggtggtttg
tttgccggatcaagagctaccaactctttttccgaaggtaactggcttcagcagagcgc
agataccaaatactgtccttctagtgtagccgtagttaggccaccacttcaagaactct
gtagcaccgcctacatacctcgctctgctaatcctgttaccagtggctgctgccagtgg
cgataagtcgtgtcttaccgggttggactcaagacgatagttaccggataaggcgcagc
ggtcgggctgaacggggggttcgtgcacacagcccagcttggagcgaacgacctacacc
```

Figure 7C (Seq ID 3: Sequence of pMAL-C4X)

gaactgagatacctacagcgtgagctatgagaaagcgccacgcttcccgaagggagaaa
ggcggacaggtatccggtaagcggcagggtcggaacaggagagcgcacgagggagcttc
caggggggaaacgcctggtatctttatagtcctgtcgggtttcgccacctctgacttgag
cgtcgattttgtgatgctcgtcagggggcggagcctatggaaaaacgccagcaacgc
ggccttttacggttcctggccttttgctggccttttgctcacatgttctttcctgcgt
tatcccctgattctgtggataaccgtattaccgcctttgagtgagctgataccgctcgc
cgcagccgaacgaccgagcgcagcgagtcagtgagcgaggaagcggaagagcgcctgat
gcggtattttctccttacgcatctgtgcggtatttcacaccgcatatatggtgcactct
cagtacaatctgctctgatgccgcatagttaagccagtatacactccgctatcgctacg
tgactgggtcatggctgcgcccgacacccgccaacacccgctgacgcgcctgacggg
cttgtctgctcccggcatccgcttacagacaagctgtgaccgtctccgggagctgcatg
tgtcagaggttttcaccgtcatcaccgaaacgcgcgaggcagctgcggtaaagctcatc
agcgtggtcgtgcagcgattcacagatgtctgctgttcatccgcgtccagctcgttga
gtttctccagaagcgttaatgtctggcttctgataaagcgggccatgttaagggcggtt
ttttcctgtttggtcactgatgcctccgtgtaaggggggatttctgttcatggggtaat
gataccgatgaaacgagagaggatgctcacgatacgggttactgatgatgaacatgccc
ggttactggaacgttgtgagggtaaacaactggcggtatggatgcggcgggaccagaga
aaaatcactcagggtcaatgccagcgcttcgttaatacagatgtaggtgttccacaggg
tagccagcagcatcctgcgatgcagatccggaacataatggtgcagggcgctgacttcc
gcgtttccagactttacgaaacacggaaaccgaagaccattcatgttgttgctcaggtc
gcagacgttttgcagcagcagtcgcttcacgttcgctcgcgtatcggtgattcattctg
ctaaccagtaaggcaacccgccagcctagccgggtcctcaacgacaggagcacgatca
tgcgcacccgtggccaggaccaacgctgcccgaaatt Figure 9A (Seq ID 4: Sequence of pMAL-C4X Kudzu)

```
ccgacaccatcgaatggtgcaaaacctttcgcggtatggcatgatagcgcccggaagag
agtcaattcagggtggtgaatgtgaaaccagtaacgttatacgatgtcgcagagtatgc
cggtgtctcttatcagaccgtttcccgcgtggtgaaccaggccagccacgtttctgcga
aaacgcgggaaaaagtggaagcggcgatggcggagctgaattacattcccaaccgcgtg
gcacaacaactggcgggcaaacagtcgttgctgattggcgttgccacctccagtctggc
cctgcacgcgccgtcgcaaattgtcgcggcgattaaatctcgcgccgatcaactgggtg
ccagcgtggtggtgtcgatggtagaacgaagcggcgtcgaagcctgtaaagcggcggtg
cacaatcttctcgcgcaacgcgtcagtgggctgatcattaactatccgctggatgacca
ggatgccattgctgtggaagctgcctgcactaatgttccggcgttatttcttgatgtct
ctgaccagacacccatcaacagtattattttctcccatgaagacggtacgcgactgggc
gtggagcatctggtcgcattgggtcaccagcaaatcgcgctgttagcgggcccattaag
ttctgtctcggcgcgtctgcgtctggctggctggcataaatatctcactcgcaatcaaa
ttcagccgatagcggaacgggaaggcgactggagtgccatgtccggttttcaacaaacc
atgcaaatgctgaatgagggcatcgttcccactgcgatgctggttgccaacgatcagat
ggcgctgggcgcaatgcgcgccattaccgagtccgggctgcgcgttggtgcggatatct
cggtagtgggatacgacgataccgaagacagctcatgttatatccgccgttaaccacc
atcaaacaggattttcgcctgctggggcaaaccagcgtggaccgcttgctgcaactctc
tcagggccaggcggtgaagggcaatcagctgttgcccgtctcactggtgaaaagaaaaa
ccaccctggcgcccaatacgcaaaccgcctctccccgcgcgttggccgattcattaatg
cagctggcacgacaggtttcccgactggaaagcgggcagtgagcgcaacgcaattaatg
taagttagctcactcattaggcacaattctcatgtttgacagcttatcatcgactgcac
ggtgcaccaatgcttctggcgtcaggcagccatcggaagctgtggtatggctgtgcagg
tcgtaaatcactgcataattcgtgtcgctcaaggcgcactccgttctggataatgttt
tttgcgccgacatcataacggttctggcaaatattctgaaatgagctgttgacaattaa
tcatcggctcgtataatgtgtggaattgtgagcggataacaatttcacacaggaaacag
ccagtccgtttaggtgttttcacgagcacttcaccaacaaggaccatagcatatgaaaa
tcgaagaaggtaaactggtaatctggattaacggcgataaaggctataacggtctcgct
gaagtcggtaagaaattcgagaaagataccggaattaaagtcaccgttgagcatccgga
taaactggaagagaaattcccacaggttgcggcaactggcgatggccctgacattatct
tctgggcacacgaccgctttggtggctacgctcaatctggcctgttggctgaaatcacc
ccggacaaagcgttccaggacaagctgtatccgtttacctgggatgccgtacgttacaa
cggcaagctgattgcttacccgatcgctgttgaagcgttatcgctgatttataacaaag
atctgctgccgaacccgccaaaaacctgggaagagatcccggcgctggataaagaactg
aaagcgaaaggtaagagcgcgctgatgttcaacctgcaagaaccgtacttcacctggcc
gctgattgctgctgacggggggttatgcgttcaagtatgaaaacggcaagtacgacatta
aagacgtgggcgtggataacgctggcgcgaaagcgggtctgaccttcctggttgacctg
attaaaaacaaacacatgaatgcagacaccgattactccatcgcagaagctgcctttaa
taaaggcgaaacagcgatgaccatcaacggcccgtgggcatggtccaacatcgacacca
gcaaagtgaattatggtgtaacggactgccgaccttcaagggtcaaccatccaaaccg
ttcgttggcgtgctgagcgcaggtattaacgccgccagtccgaacaaagagctggcaaa
agagttcctcgaaaactatctgctgactgatgaaggtctggaagcggttaataaagaca
aaccgctgggtgccgtagcgctgaagtcttacgaggaagagttggtgaaagatccgcgg
attgccgccactatggaaaacgcccagaaaggtgaaatcatgccgaacatcccgcagat
gtccgctttctggtatgccgtgcgtactgcggtgatcaacgccgccagcggtcgtcaga
ctgtcgatgaagccctgaaagacgcgcagactaattcgagctcgaacaacaacaacaat
```

Figure 9B (Seq ID 4: Sequence of pMAL-C4X Kudzu)

```
aacaataacaacaacctcgggatcgagggaaggatttcagaattctgtgcgacctcttc
tcaatttactcagattaccgagcataattcccgtcgttccgcaaactatcagccaaacc
tgtggaatttcgaattcctgcaatccctggagaacgacctgaaagtggaaaagctggag
gagaaagcgaccaaactggaggaagaagttcgctgcatgatcaaccgtgtagacaccca
gccgctgtccctgctggagctgatcgacgatgtgcagcgcctgggtctgacctacaaat
ttgaaaagacatcattaaagccctggaaacatcgtactgctggacgaaaacaaaaag
aacaaatctgacctgcacgcaaccgctctgtctttccgtctgctgcgtcagcacggttt
cgaggtttctcaggatgttttgagcgtttcaaggataaagaaggtggtttcagcggtg
aactgaaaggtgacgtccaaggcctgctgagcctgtatgagcgtcttacctgggtttc
gagggtgagaacctgctggaggaggcgcgtaccttttccatcacccacctgaagaacaa
cctgaaagaaggcattaataccaaggttgcagaacaagtgagccacgccctggaactgc
catatcaccagcgtctgcaccgtctggaggcacgttggttcctggataaatacgaaccg
aaagaaccgcatcaccagctgctgctggagctggcgaagctggattttaacatggtaca
gaccctgcaccagaaagagctgcaagatctgtcccgctggtggaccgagatgggcctgg
ctagcaaactggattttgtacgcgaccgcctgatggaagtttatttctgggcactgggt
atggcgccagacccgcagtttggtgaatgtcgcaaagctgttactaaaatgtttggtct
ggtgacgatcatcgatgacgtgtatgacgtttatggcactctggacgaactgcaactgt
tcaccgatgctgtagagcgctgggacgttaacgctattaacaccctgccggactatatg
aaactgtgtttcctggcactgtacaacaccgttaacgacacgtcctattctattctgaa
agagaaaggtcataacaacctgtcctatctgacgaaaagctggcgtgaactgtgcaaag
cctttctgcaagaggcgaaatggtccaacaacaaaattatcccggctttctccaagtac
ctggaaaacgccagcgtttcctcctccggtgtagcgctgctggcgcgtcttactttc
cgtatgccagcagcaggaagacatctccgaccacgcgctgcgttccctgaccgacttcc
atggtctggtgcgttctagctgcgttatcttccgcctgtgcaacgatctggccacctct
gcggcggagctggaacgtggcgagactaccaattctatcattagctacatgcacgaaaa
cgatggtaccagcgaggaacaggcccgcgaagaactgcgtaaactgatcgacgccgaat
ggaaaaagatgaatcgtgaacgcgttagcgactccaccctgctgcctaaagcgttcatg
gaaatcgcagttaacatggcacgtgtttcccactgcacctaccagtatggcgatggtct
gggtcgcccagactacgcgactgaaaaccgcatcaaactgctgctgattgaccctttcc
cgattaaccagctgatgtatgtctaagcttggcactggccgtcgttttacaacgtcgtg
actgggaaaaccctggcgttacccaacttaatcgccttgcagcacatcccctttcgcc
agctggcgtaatagcgaagaggcccgcaccgatcgcccttcccaacagttgcgcagcct
gaatggcgaatggcagcttggctgttttggcggatgagataagatttcagcctgatac
agattaaatcagaacgcagaagcggtctgataaaacagaatttgcctggcggcagtagc
gcggtggtcccacctgacccatgccgaactcagaagtgaaacgccgtagcgccgatgg
tagtgtggggtctcccatgcgagagtagggaactgccaggcatcaaataaaacgaaag
gctcagtcgaagactgggcctttcgttttatctgttgtttgtcggtgaacgctctcct
gagtaggacaaatccgccgggagcggatttgaacgttgcgaagcaacggcccggagggt
ggcgggcaggacgcccgccataaactgccaggcatcaaattaagcagaaggccatcctg
acggatggcctttttgcgtttctacaaactcttttgtttatttttctaaatacattca
aatatgtatccgctcatgagacaataaccctgataaatgcttcaataatattgaaaaag
gaagagtatgagtattcaacatttccgtgtcgcccttattccttttttgcggcatttt
gccttcctgtttttgctcacccagaaacgctggtgaaagtaaaagatgctgaagatcag
ttgggtgcacgagtgggttacatcgaactggatctcaacagcggtaagatccttgagag
ttttcgccccgaagaacgttctccaatgatgagcacttttaaagttctgctatgtggcg
```

Figure 9C (Seq ID 4: Sequence of pMAL-C4X Kudzu)

```
cggtattatcccgtgttgacgccgggcaagagcaactcggtcgccgcatacactattct
cagaatgacttggttgagtactcaccagtcacagaaaagcatcttacggatggcatgac
agtaagagaattatgcagtgctgccataaccatgagtgataacactgcggccaacttac
ttctgacaacgatcggaggaccgaaggagctaaccgcttttttgcacaacatgggggat
catgtaactcgccttgatcgttgggaaccggagctgaatgaagccataccaaacgacga
gcgtgacaccacgatgcctgtagcaatggcaacaacgttgcgcaaactattaactggcg
aactacttactctagcttcccggcaacaattaatagactggatggaggcggataaagtt
gcaggaccacttctgcgctcggcccttccggctggctggtttattgctgataaatctgg
agccggtgagcgtgggtctcgcggtatcattgcagcactggggccagatggtaagccct
cccgtatcgtagttatctacacgacggggagtcaggcaactatggatgaacgaaataga
cagatcgctgagataggtgcctcactgattaagcattggtaactgtcagaccaagttta
ctcatatactttagattgatttaccccggttgataatcagaaaagccccaaaaacag
gaagattgtataagcaaatatttaaattgtaaacgttaatatttgttaaaattcgcgt
taaattttgttaaatcagctcatttttaaccaataggccgaaatcggcaaaatccct
tataaatcaaaagaatagaccgagatagggttgagtgttgttccagtttggaacaagag
tccactattaaagaacgtggactccaacgtcaaagggcgaaaaaccgtctatcagggcg
atggcccactacgtgaaccatcacccaaatcaagttttttggggtcgaggtgccgtaaa
gcactaaatcggaaccctaaaggagccccgatttagagcttgacggggaaagccggc
gaacgtggcgagaaaggaagggaagaaagcgaaaggagcgggcgctagggcgctggcaa
gtgtagcggtcacgctgcgcgtaaccaccacccgccgcgcttaatgcgccgctacag
ggcgcgtaaaaggatctaggtgaagatccttttgataatctcatgaccaaaatccctt
aacgtgagttttcgttccactgagcgtcagacccgtagaaaagatcaaaggatcttct
tgagatccttttttctgcgcgtaatctgctgcttgcaaacaaaaaaaccaccgctacc
agcggtggtttgtttgccggatcaagagctaccaactcttttccgaaggtaactggct
tcagcagagcgcagataccaaatactgtccttctagtgtagccgtagttaggccaccac
ttcaagaactctgtagcaccgcctacatacctcgctctgctaatcctgttaccagtggc
tgctgccagtggcgataagtcgtgtcttaccgggttggactcaagacgatagttaccgg
ataaggcgcagcggtcgggctgaacggggggttcgtgcacacagcccagcttggagcga
acgacctacaccgaactgagatacctacagcgtgagctatgagaaagcgccacgcttcc
cgaagggagaaaggcggacaggtatccggtaagcggcagggtcggaacaggagagcgca
cgagggagcttccaggggaaacgcctggtatctttatagtcctgtcgggtttcgccac
ctctgacttgagcgtcgatttttgtgatgctcgtcaggggggcggagcctatggaaaaa
cgccagcaacgcggcctttttacggttcctggccttttgctggccttttgctcacatgt
tctttcctgcgttatcccctgattctgtggataaccgtattaccgcctttgagtgagct
gataccgctcgccgcagccgaacgaccgagcgcagcgagtcagtgagcgaggaagcgga
agagcgcctgatgcggtattttctccttacgcatctgtgcggtatttcacaccgcatat
atggtgcactctcagtacaatctgctctgatgccgcatagttaagccagtatacactcc
gctatcgctacgtgactgggtcatggctgcgccccgacacccgccaacacccgctgacg
cgccctgacgggcttgtctgctcccggcatccgcttacagacaagctgtgaccgtctcc
gggagctgcatgtgtcagaggttttcaccgtcatcaccgaaacgcgcgaggcagctgcg
gtaaagctcatcagcgtggtcgtgcagcgattcacagatgtctgcctgttcatccgcgt
ccagctcgttgagtttctccagaagcgttaatgtctggcttctgataaagcgggccatg
ttaagggcggttttttcctgtttggtcactgatgcctccgtgtaaggggattctgtt
catgggggtaatgataccgatgaaacgagagaggatgctcacgatacgggttactgatg
atgaacatgcccggttactggaacgttgtgagggtaaacaactggcggtatggatgcgg
```

Figure 9D (Seq ID 4: Sequence of pMAL-C4X Kudzu)

```
cgggaccagagaaaaatcactcagggtcaatgccagcgcttcgttaatacagatgtagg
tgttccacagggtagccagcagcatcctgcgatgcagatccggaacataatggtgcagg
gcgctgacttccgcgtttccagactttacgaaacacggaaaccgaagaccattcatgtt
gttgctcaggtcgcagacgttttgcagcagcagtcgcttcacgttcgctcgcgtatcgg
tgattcattctgctaaccagtaaggcaacccgccagcctagccgggtcctcaacgaca
ggagcacgatcatgcgcacccgtggccaggacccaacgctgcccgaatt
```

Figure 10
A.
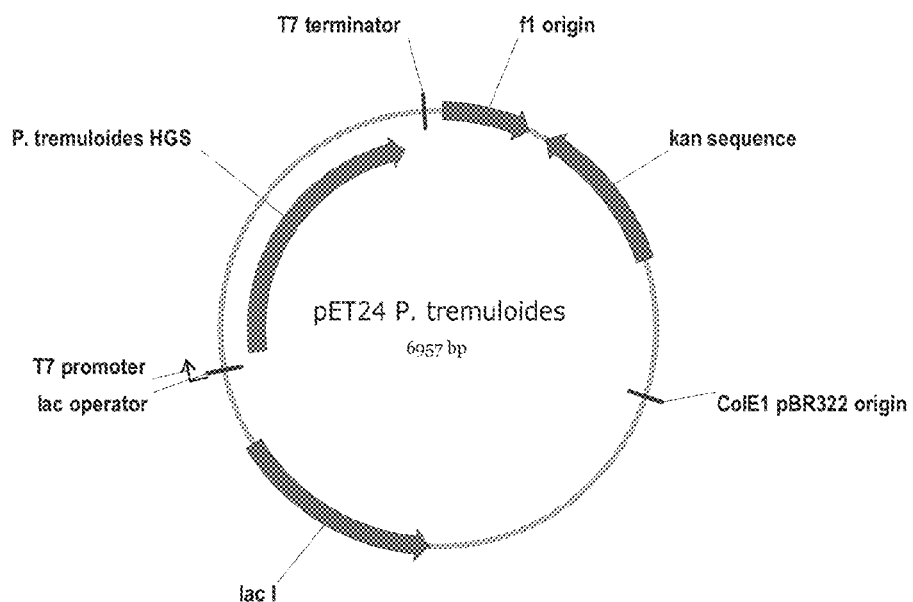
B.
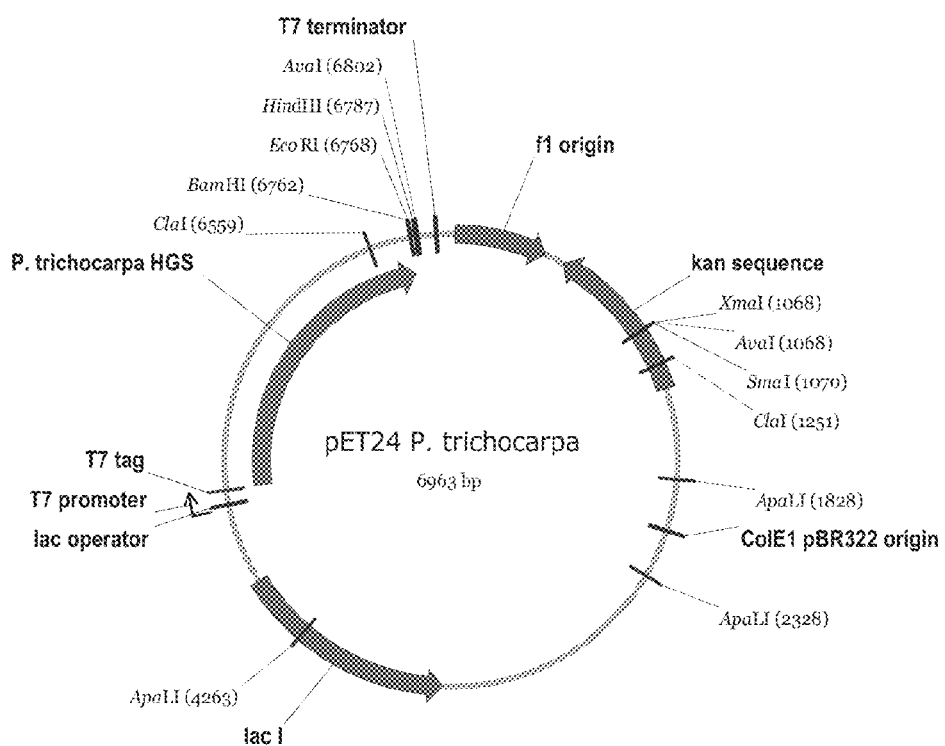

Figure 11 (Amino Acid Sequence of P. tremuloides IspS (in P. tremuloides pET24a))

MRCSVSTENVSFSETETETRRSANYEPNSWDYDYLLSSDTDESIEVHKDKAKKLEAEVR
REINNEKAEFLTLLELIDNVQRLGLGYRFESDIRRALDRFVSSGGFDGVTKTSLHGTAL
SFRLLRQHGFEVSQEAFSGFKDQNGNFLENLKEDIKAILSLYEASFLALEGENILDEAK
VFAISHLKELSEEKIGKELAEQVSHALELPLHRRTQRLEAVWSIEAYRKKEDANQVLLE
LAILDYNMIQSVYQRDLRETSRWWRVGLATKLHFARDRLIESFYWAVGVAFEPQYSDC
RNSVAKMFSFVTIIDDIYDVYGTLDELELFTDAVERWDVNAINDLPDYMKLCFLALYNT
INEIAYDNLKDKGENILPYLTKAWADLCNAFLQEAKWLYNKSTPTFDDYFGNAWKSSSG
PLQLIFAYFAVVQNIKKEEIENLQKYHDIISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFER

Figure 12A (DNA Sequence of P. tremuloides pET24a)

```
tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctccctt
agggttccgatttagtgctttacggcacctcgaccccaaaaaacttgattagggtgatg
gttcacgtagtgggccatcgccctgatagacggtttttcgccctttgacgttggagtcc
acgttctttaatagtggactcttgttccaaactggaacaacactcaaccctatctcggt
ctattcttttgatttataagggattttgccgatttcggcctattggttaaaaaatgagc
tgatttaacaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatattttgaaaaagccgtttctgtaa
tgaaggagaaaactcaccgaggcagttccataggatggcaagatcctggtatcggtctg
cgattccgactcgtccaacatcaatacaacctattaatttccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttccggggatcgcagtggtgagtaaccatgcatcatcaggagtacggataaaatgc
ttgatggtcggaagaggcataaattccgtcagccagtttagtctgaccatctcatctgt
aacatcattggcaacgctaccttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagtttta
ttgttcatgaccaaaatcccttaacgtgagttttcgttccactgagcgtcagacccgt
agaaaagatcaaaggatcttcttgagatcctttttttctgcgcgtaatctgctgcttgc
aaacaaaaaaaccaccgctaccagcggtggtttgtttgccggatcaagagctaccaact
cttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccaggggaaacgcctggtatcttta
tagtcctgtcgggtttcgccacctctgacttgagcgtcgatttttgtgatgctcgtcag
ggggcggagcctatggaaaaacgccagcaacgcggcctttttacggttcctggcctt
tgctggccttttgctcacatgttctttcctgcgttatccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgcccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag
atgtctgcctgttcatccgcgtccagctcgttgagtttctccagaagcgttaatgtctg
```

Figure 12B (DNA Sequence of P. tremuloides pET24a)

```
gcttctgataaagcgggccatgttaagggcggttttttcctgtttggtcactgatgcct
ccgtgtaaggggg atttctgttcatggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaacccgccag
cctagccgggtcctcaacgacaggagcacgatcatgcgcaccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgccacc
ggaaggagctgactggggttgaaggctctcaagggcatcggtcgagatccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggttttttcttttcaccagtgagacgggcaacagctgattgccctt
caccgcctggccctgagagagttgcagcaagcggtccacgctggtttgcccagcaggc
gaaaatcctgtttgatggtggttaacggcgggataacatgagctgtcttcggtatcg
tcgtatccactaccgagatatccgcaccaacgcgcagcccggactcggtaatggcgcg
cattgcgccagcgccatctgatcgttggcaaccagcatcgcagtgggaacgatgccct
cattcagcatttgcatggtttgttgaaaaccggacatggcactccagtcgccttccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
acttttccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactctgcattaggaagc
agcccagtagtaggttgaggccgttgagcaccgccgccgcaaggaatggtgcatgcaag
gagatggcgcccaacagtccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactatagggaattgtgagcg
gataacaattcccctctagaaataattttgtttaactttaagaaggagatatacatatg
cgttgtagcgtgtccaccgaaaatgtgtctttctctgaaactgaaaccgaaacgcgtcg
ttctgcgaactacgaacctaacagctgggactatgattacctgctgtcctccgacacgg
acgagtccatcgaagtacacaaagacaaagcgaaaaagctggaagccgaagttcgtcgc
gagattaataacgaaaaagcagaatttctgaccctgctggaactgattgacaacgtcca
```

Figure 12C (DNA Sequence of P. tremuloides pET24a)

gcgcctgggcctgggttaccgtttcgagtctgatatccgtcgtgcgctggatcgcttcg
tttcctccggcggcttcgatggcgtaaccaagacttccctgcacggtacggcactgtct
ttccgtctgctgcgtcaacacggttttgaggtttctcaggaagcgttcagcggcttcaa
agaccaaaacggcaacttcctggagaacctgaaggaagatatcaaagctatcctgagcc
tgtacgaggccagcttcctggctctggaaggcgaaaacatcctggacgaggcgaaggtt
ttcgcaatctctcatctgaaagaactgtctgaagaaagatcggtaaagagctggcaga
acaggtgtcccatgcactggaactgccactgcatcgccgtactcagcgtctggaagcag
tatggtctatcgaggcctaccgtaaaaaggaggacgcgaaccaggttctgctggagctg
gcaattctggattacaacatgatccagtctgtataccagcgtgatctgcgtgaaacgtc
ccgttggtggcgtcgtgtgggtctggcgaccaaactgcactttgctcgtgaccgcctga
ttgagagcttctactgggccgtgggtgtagcattcgaaccgcaatactccgactgccgt
aactccgtcgcaaaaatgttttctttcgtaaccattatcgacgatatctacgatgtata
cggcaccctggacgaactggagctgtttactgatgcagttgagcgttgggacgtaaacg
ccatcaacgacctgccggattacatgaaactgtgctttctggctctgtataacactatt
aacgaaatcgcctacgacaacctgaaagataaaggtgagaacatcctgccgtatctgac
caaagcctgggctgacctgtgcaacgcttcctgcaagaagccaagtggctgtacaaca
atctactccgacctttgacgactacttcggcaacgcatggaaatcctcttctggcccg
ctgcaactgatcttcgcttacttcgctgtcgtgcagaacattaaaaaggaagagatcga
aaacctgcaaaaataccatgacatcatctctcgtccttcccatatcttccgtctgtgca
atgacctggctagcgcgtctgcggaaattgcgcgtggtgaaaccgcaaatagcgtttct
tgttacatgcgcactaaaggtatctccgaagaactggctaccgaaagcgtgatgaatct
gatcgatgaaacctggaaaagatgaacaaggaaaaactgggtggtagcctgttcgcga
aaccgttcgtggaaaccgcgatcaacctggcacgtcaatctcactgcacttatcataac
ggcgacgcgcatacctctccggatgagctgacccgcaaacgcgttctgtctgtaatcac
tgaaccgattctgccgtttgaacgctaaggatccgaattcgagctccgtcgacaagctt
gcggccgcactcgagcaccaccaccaccaccactgagatccggctgctaacaaagcccg
aaaggaagctgagttggctgctgccaccgctgagcaataactagcataaccccttgggg
cctctaaacgggtcttgaggggttttttgctgaaaggaggaactatatccggat Figure 13 (Amino Acid Sequence of P. trichocharpa IspS (in P. trichocharpa pET24a))

MRCSVSTENVSFTETETETRRSANYEPNSWDYDYLLSSDTDESIEVYKDKAKKLEAEVR
REINNEKAEFLTLLELIDNVQRLGLGYRFESDIRRALDRFVSSGGFDAVTKTSLHATAL
SFRLLRQHGFEVSQEAFSGFKDQNGNFLENLKEDIKAILSLYEASFLALEGENILDEAK
VFAISHLKELSEEKIGKDLAEQVNHALELPLHRRTQRLEAVLSIEAYRKKEDADQVLLE
LAILDYNMIQSVYQRDLRETSRWWRRVGLATKLHFARDRLIESFYWAVGVAFEPQYSDC
RNSVAKMFSFVTIIDDIYDVYGTLDELELFTNAVERWDVNAIDDLPDYMKLCFLALYNT
INEIAYDNLKEKGENILPYLTKAWADLCNAFLQEAKWLYNKSTPTFDEYFGNAWKSSSG
PLQLVFAYFAVVQNIKKEEIENLQKYHDIISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFER

Figure 14A (DNA sequence of P. trichocharpa pET24a)

```
tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctccctt
agggttccgatttagtgctttacggcacctcgaccccaaaaaacttgattagggtgatg
gttcacgtagtgggccatcgcctgatagacggttttcgccttgacgttggagtcc
acgttctttaatagtggactcttgttccaactggaacaacactcaaccctatctcggt
ctattcttttgatttataagggatttgccgatttcggcctattggttaaaaaatgagc
tgatttaacaaaaatttaacgcgaattttaacaaaatattaacgtttacaattttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatatttttgaaaaagccgtttctgtaa
tgaaggagaaaactcaccgaggcagttccataggatggcaagatcctggtatcggtctg
cgattccgactcgtccaacatcaatacaacctattaatttccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatatttcacctgaatcaggatattcttctaataccggaatgctg
ttttccggggatcgcagtggtgagtaaccatgcatcatcaggagtacggataaaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagttta
ttgttcatgaccaaaatcccttaacgtgagttttcgttccactgagcgtcagacccgt
agaaaagatcaaaggatcttcttgagatccttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccggggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccaggggggaaacgcctggtatcttta
tagtcctgtcgggtttcgccacctctgacttgagcgtcgatttttgtgatgctcgtcag
ggggcggagcctatggaaaaacgccagcaacgcggcctttttacggttcctggcctttt
gctggccttttgctcacatgttctttcctgcgttatccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatggtgcactctcagtacaatctgctctgatgccgca
tagttaagccagtatacactccgctatcgctacgtgactgggtcatggctgcgcccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag
atgtctgcctgttcatccgcgtccagctcgttgagtttctccagaagcgttaatgtctg
```

Figure 14B (DNA sequence of P. trichocharpa pET24a)

```
gcttctgataaagcgggccatgttaagggcggttttttcctgtttggtcactgatgcct
ccgtgtaaggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgaagcgacaggccgatcatcgtcgcgctc
cagcgaaagcggtcctcgccgaaaatgacccagagcgctgccggcacctgtcctacgag
ttgcatgataagaagacagtcataagtgcggcgacgatagtcatgccccgcgcccacc
ggaaggagctgactgggttgaaggctctcaagggcatcggtcgagatccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggtttttcttttcaccagtgagacgggcaacagctgattgccctt
caccgcctggccctgagagagttgcagcaagcggtccacgctggtttgccccagcaggc
gaaaatcctgtttgatggtggttaacggcgggataatcatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
acttttttccccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactcctgcattaggaagc
agcccagtagtaggttgaggccgttgagcaccgccgccgcaaggaatggtgcatgcaag
gagatggcgcccaacagtccccggccacggggcctgccaccatacccacgccgaaaca
agcgctcatgagcccgaagtggcgagccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactatagggaattgtgagcg
gataacaattcccctctagaaataattttgtttaactttaagaaggagatatacatatg
catatgcgttgtagcgtgtccaccgaaaatgtgtctttcaccgaaactgaaaccgaaac
gcgtcgttctgcgaactacgaacctaacagctgggactatgattacctgctgtcctccg
acacggacgagtccatcgaagtatacaaagacaaagcgaaaaagctggaagccgaagtt
cgtcgcgagattaataacgaaaaagcagaatttctgaccctgctggaactgattgacaa
```

Figure 14C (DNA sequence of P. trichocharpa pET24a)

cgtccagcgcctgggcctgggttaccgtttcgagtctgatatccgtcgtgcgctggatc
gcttcgtttcctccggcggcttcgatgcggtaaccaagacttccctgcacgcgacggca
ctgtctttccgtctgctgcgtcaacacggttttgaggtttctcaggaagcgttcagcgg
cttcaaagaccaaaacggcaacttcctggagaacctgaaggaagatatcaaagctatcc
tgagcctgtacgaggccagcttcctggctctggaaggcgaaaacatcctggacgaggcg
aaggttttcgcaatctctcatctgaaagaactgtctgaagaaaagatcggtaaagatct
ggcagaacaggtgaaccatgcactggaactgccactgcatcgccgtactcagcgtctgg
aagcagtactgtctatcgaggcctaccgtaaaaggaggacgcggatcaggttctgctg
gagctggcaattctggattacaacatgatccagtctgtataccagcgtgatctgcgtga
aacgtccgttggtggcgtcgtgtgggtctggcgaccaaactgcactttgctcgtgacc
gctgattgagagcttctactgggccgtgggtgtagcattcgaaccgcaatactccgac
tgccgtaactccgtcgcaaaaatgttttctttcgtaaccattatcgacgatatctacga
tgtatacggcaccctggacgaactggagctgtttactaacgcagttgagcgttgggacg
taaacgccatcgacgatctgccggattacatgaaactgtgctttctggctctgtataac
actattaacgaaatcgcctacgacaacctgaaagaaaaggtgagaacatcctgccgta
tctgaccaaagcctgggctgacctgtgcaacgctttcctgcaagaagccaagtggctgt
acaacaaatctactccgacctttgacgaatacttcggcaacgcatggaaatcctcttct
ggcccgctgcaactggtgttcgcttacttcgctgtcgtgcagaacattaaaaaggaaga
gatcgaaaacctgcaaaaataccatgacatcatctctcgtccttcccatatcttccgtc
tgtgcaatgacctggctagcgcgtctgcggaaattgcgcgtggtgaaaccgcaaatagc
gtttcttgttacatgcgcactaaaggtatctccgaagaactggctaccgaaagcgtgat
gaatctgatcgatgaaacctggaaaaagatgaacaaggaaaaactgggtggtagcctgt
tcgcgaaaccgttcgtggaaccgcgatcaacctggcacgtcaatctcactgcacttat
cataacggcgacgcgcataccctctccggatgagctgacccgcaaacgcgttctgtctgt
aatcactgaaccgattctgccgtttgaacgctaaggatccgaattcgagctccgtcgac
aagcttgcggccgcactcgagcaccaccaccaccaccactgagatccggctgctaacaa
agcccgaaaggaagctgagttggctgctgccaccgctgagcaataactagcataacccc
ttggggcctctaaacgggtcttgaggggttttttgctgaaaggaggaactatatccgga
t Figure 15
A.
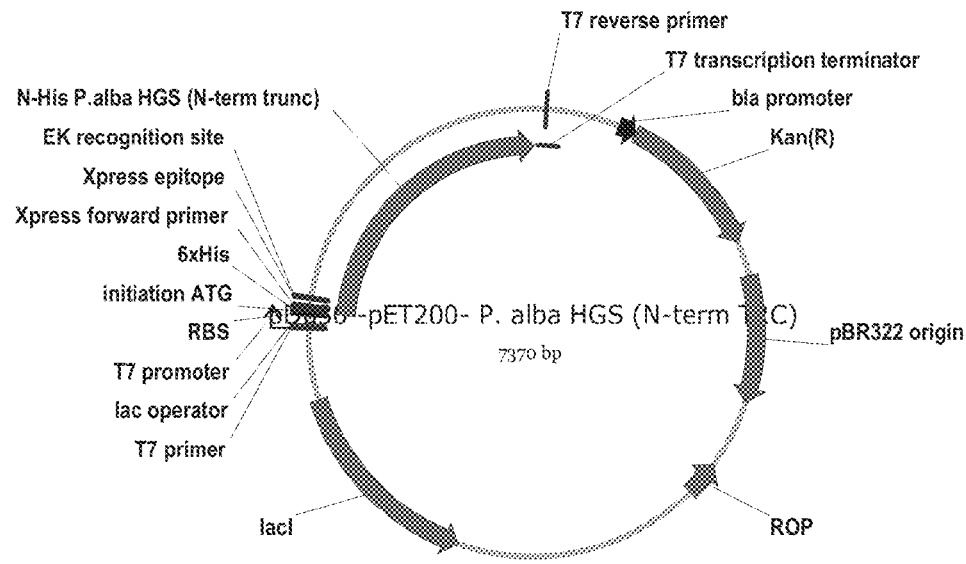
B.
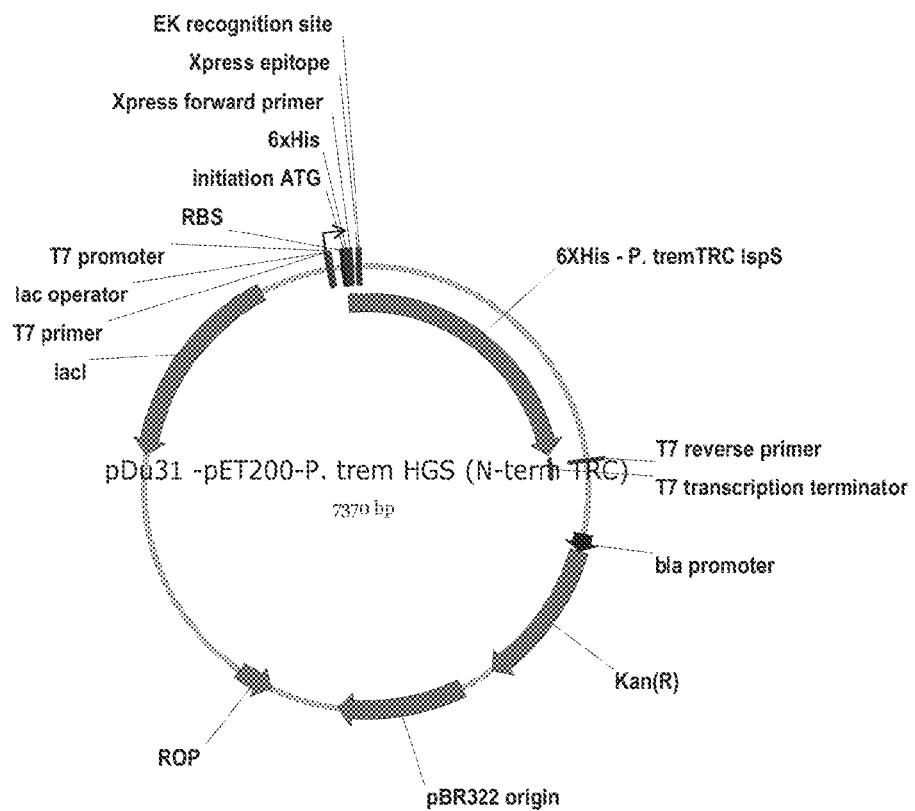

Figure 16 (Amino Acid Sequence of IspS variant P. albaTRC-pET200 (in pDu30))

MRGSHHHHHHGMASMTGGQQMGRDLYDDDDKDHPFTMRRSANYEPNSWDYDYLLSSDTD
ESIEVYKDKAKKLEAEVRREINNEKAEFLTLLELIDNVQRLGLGYRFESDIRGALDRFV
SSGGFDAVTKTSLHGTALSFRLLRQHGFEVSQEAFSGFKDQNGNFLENLKEDIKAILSL
YEASFLALEGENILDEAKVFAISHLKELSEEKIGKELAEQVNHALELPLHRRTQRLEAV
WSIEAYRKKEDANQVLLELAILDYNMIQSVYQRDLRETSRWWRRVGLATKLHFARDRLI
ESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNK
STPTFDDYFGNAWKSSSGPLQLVFAYFAVVQNIKKEEIENLQKYHDTISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER

Figure 17A (DNA Sequence of pDu30)

aagggcgagctcaacgatccggctgctaacaaagcccgaaaggaagctgagttggctgc
tgccaccgctgagcaataactagcataaccccttggggcctctaaacgggtcttgagga
gttttttgctgaaaggaggaactatatccggatatcccgcaagaggcccggcagtaccg
gcataaccaagcctatgcctacagcatccagggtgacggtgccgaggatgacgatgagc
gcattgttagatttcatacacggtgcctgactgcgttagcaatttaactgtgataaact
accgcattaaagcttatcgatgataagctgtcaaacatgagaattaattcttgaagacg
aaagggcctcgtgatacgcctatttttataggttaatgtcatgataataatggtttctt
agacgtcaggtggcacttttcggggaaatgtgcgcggaacccctatttgtttattttc
taaatacattcaaatatgtatccgctcatgagacaataaccctgataaatgcttcaata
atattgaaaaaggaagagtatgattgaacaagatggattgcacgcaggttctccggccg
cttgggtggagaggctattcggctatgactgggcacaactgacaatcggctgctctgat
gccgccgtgttccggctgtcagcgcaggggcgcccggttcttttgtcaagaccgacct
gtccggtgccctgaatgaactgcaggacgaggcagcgcggctatcgtggctggccacga
cgggcgttcttgcgcagctgtgctcgacgttgtcactgaagcgggaagggactggctg
ctattgggcgaagtgccggggcaggatctcctgtcatctcaccttgctcctgccgagaa
agtatccatcatggctgatgcaatgcggcggctgcatacgcttgatccggctacctgcc
cattcgaccaccaagcgaaacatcgcatcgagcgggcacgtactcggatggaagccggt
cttgtcgatcaggatgatctggacgaagagcatcaggggctcgcgccagccgaactgtt
cgccaggctcaaggcgcgcatgcccgacggcgaggatctcgtcgtgacacatggcgatg
cctgcttgccgaatatcatggtggaaaatggccgcttttctggattcatcgactgtggc
cggctgggtgtggcggaccgctatcaggacatagcgttggctacccgtgatattgctga
agagcttggcggcgaatgggctgaccgcttcctcgtgctttacggtatcgccgctcccg
attcgcagcgcatcgccttctatcgccttcttgacgagttcttctgagcgggactctgg
ggttcgaaatgaccgaccaagcgacgcctaactgtcagaccaagtttactcatatatac
tttagattgatttaaaacttcattttttaatttaaaaggatctaggtgaagatcctttt
gataatctcatgaccaaaatcccttaacgtgagttttcgttccactgagcgtcagaccc
cgtagaaaagatcaaaggatcttcttgagatcctttttttctgcgcgtaatctgctgct
tgcaaacaaaaaaaccaccgctaccagcggtggtttgtttgccggatcaagagctacca
actcttttccgaaggtaactggcttcagcagagcgcagataccaaatactgtccttct
agtgtagccgtagttaggccaccacttcaagaactctgtagcaccgcctacatacctcg
ctctgctaatcctgttaccagtggctgctgccagtggcgataagtcgtgtcttaccggg
ttggactcaagacgatagttaccggataaggcgcagcggtcgggctgaacggggggttc
gtgcacacagcccagcttggagcgaacgacctacaccgaactgagatacctacagcgtg
agctatgagaaagcgccacgcttcccgaagggagaaaggcggacaggtatccggtaagc
ggcagggtcggaacaggagagcgcacgagggagcttccaggggaaacgcctggtatct
ttatagtcctgtcgggtttcgccacctctgacttgagcgtcgatttttgtgatgctcgt
caggggggcggagcctatggaaaaacgccagcaacgcggcctttttacggttcctggcc
ttttgctggccttttgctcacatgttctttcctgcgttatcccctgattctgtggataa
ccgtattaccgcctttgagtgagctgataccgctcgccgcagccgaacgaccgagcgca
gcgagtcagtgagcgaggaagcggaagagcgcctgatgcggtattttctccttacgcat
ctgtgcggtatttcacaccgcaatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag Figure 17B (DNA Sequence of pDu30)

```
atgtctgcctgttcatccgcgtccagctcgttgagtttctccagaagcgttaatgtctg
gcttctgataaagcgggccatgttaagggcggttttttcctgtttggtcactgatgcct
ccgtgtaagggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaacccgccag
cctagccgggtcctcaacgacaggagcacgatcatgcgcacccgtggccaggacccaac
gctgcccgagatgcgccgcgtgcggctgctggagatggcggacgcgatggatatgttct
gccaagggttggtttgcgcattcacagttctccgcaagaattgattggctccaattctt
ggagtggtgaatccgttagcgaggtgccgccggcttccattcaggtcgaggtggcccgg
ctccatgcaccgcgacgcaacgcggggaggcagacaaggtatagggcggcgcctacaat
ccatgccaaccgttccatgtgctcgccgaggcggcataaatcgccgtgacgatcagcg
gtccaatgatcgaagttaggctggtaagagccgcgagcgatccttgaagctgtccctga
tggtcgtcatctacctgcctggacagcatggcctgcaacgcgggcatcccgatgccgcc
ggaagcgagaagaatcataatggggaaggccatccagcctcgcgtcgcgaacgccagca
agacgtagcccagcgcgtcggccgccatgccggcgataatggcctgcttctcgccgaaa
cgtttggtggcgggaccagtgacgaaggcttgagcgagggcgtgcaagattccgaatac
cgcaagcgacaggccgatcatcgtcgcgctccagcgaaagcggtcctcgccgaaaatga
cccagagcgctgccggcacctgtcctacgagttgcatgataaagaagacagtcataagt
gcggcgacgatagtcatgccccgcgcccaccggaaggagctgactgggttgaaggctct
caagggcatcggtcgagatcccggtgcctaatgagtgagctaacttacattaattgcgt
tgcgctcactgcccgctttccagtcgggaaacctgtcgtgccagctgcattaatgaatc
ggccaacgcgcggggagaggcggtttgcgtattgggcgccagggtggttttcttttca
ccagtgagacgggcaacagctgattgcccttcaccgctggccctgagagagttgcagc
aagcggtccacgctggttttgcccagcaggcgaaaatcctgtttgatggtggttaacgg
cgggatataacatgagctgtcttcggtatcgtcgtatcccactaccgagatatccgcac
caacgcgcagcccggactcggtaatggcgcgcattgcgcccagcgccatctgatcgttg
gcaaccagcatcgcagtgggaacgatgccctcattcagcatttgcatggtttgttgaaa
accggacatggcactccagtcgccttcccgttccgctatcggctgaatttgattgcgag
tgagatatttatgccagccagccagacgcagacgcgccgagacagaacttaatgggccc
gctaacagcgcgatttgctggtgacccaatgcgaccagatgctccacgccagtcgcgt
accgtcttcatgggagaaaataatactgttgatgggtgtctggtcagagacatcaagaa
ataacgccggaacattagtgcaggcagcttccacagcaatggcatcctggtcatccagc
ggatagttaatgatcagcccactgacgcgttgcgcgagaagattgtgcaccgccgcttt
acaggcttcgacgccgcttcgttctaccatcgacaccaccacgctggcacccagttgat
cggcgcgagatttaatcgccgcgacaatttgcgacggcgcgtgcagggccagactggag
gtggcaacgccaatcagcaacgactgtttgccgccagttgttgtgccacgcggttggg
aatgtaattcagctccgccatcgccgcttccacttttcccgcgttttcgcagaaacgt
ggctggcctggttcaccacgcgggaaacggtctgataagagacaccggcatactctgcg
acatcgtataacgttactggtttcacattcaccaccctgaattgactctcttccgggcg
ctatcatgccataccgcgaaaggttttcgccattcgatggtgtccgggatctcgacgc
tctcccttatgcgactcctgcattaggaagcagcccagtagtaggttgaggccgttgag
```

Figure 17C (DNA Sequence of pDu30)

```
caccgccgccgcaaggaatggtgcatgcaaggagatggcgcccaacagtcccccggcca
cggggcctgccaccatacccacgccgaaacaagcgctcatgagcccgaagtggcgagcc
cgatcttccccatcggtgatgtcggcgatataggcgccagcaaccgcacctgtggcgcc
ggtgatgccggccacgatgcgtccggcgtagaggatcgagatctcgatcccgcgaaatt
aatacgactcactatagggaattgtgagcggataacaattcccctctagaaataattt
tgtttaactttaagaaggagatatacatatgcggggttctcatcatcatcatcatcatg
gtatggctagcatgactggtggacagcaaatgggtcgggatctgtacgacgatgacgat
aaggatcatcccttcaccatgcgtcgttctgcgaactacgaacctaacagctgggacta
tgattacctgctgtcctccgacacggacgagtccatcgaagtatacaaagacaaagcga
aaaagctggaagccgaagttcgtcgcgagattaataacgaaaaagcagaatttctgacc
ctgctggaactgattgacaacgtccagcgcctgggcctgggttaccgtttcgagtctga
tatccgtggtgcgctggatcgcttcgttcctccggcggcttcgatgcggtaaccaaga
cttccctgcacggtacggcactgtctttccgtctgctgcgtcaacacggttttgaggtt
tctcaggaagcgttcagcggcttcaaagaccaaaacggcaacttcctggagaacctgaa
ggaagatatcaaagctatcctgagcctgtacgaggccagcttcctggctctggaaggcg
aaaacatcctggacgaggcgaaggttttcgcaatctctcatctgaaagaactgtctgaa
gaaaagatcggtaaagagctggcagaacaggtgaaccatgcactggaactgccactgca
tcgccgtactcagcgtctggaagcagtatggtctatcgaggcctaccgtaaaaaggagg
acgcgaatcaggttctgctggagctggcaattctggattacaacatgatccagtctgta
taccagcgtgatctgcgtgaaacgtcccgttggtggcgtcgtgtgggtctggcgaccaa
actgcactttgctcgtgaccgcctgattgagagcttctactgggccgtgggtgtagcat
tcgaaccgcaatactccgactgccgtaactccgtcgcaaaaatgttttctttcgtaacc
attatcgacgatatctacgatgtatacggcaccctggacgaactggagctgtttactga
tgcagttgagcgttgggacgtaaacgccatcaacgacctgccggattacatgaaactgt
gctttctggctctgtataacactattaacgaaatcgcctacgacaacctgaaagataaa
ggtgagaacatcctgccgtatctgaccaaagcctgggctgacctgtgcaacgcttcct
gcaagaagccaagtggctgtacaacaaatctactccgacctttgacgactacttcggca
acgcatggaaatcctcttctggcccgctgcaactggtgttcgcttacttcgctgtcgtg
cagaacattaaaaaggaagagatcgaaaacctgcaaaaataccatgacaccatctctcg
tccttcccatatcttccgtctgtgcaatgacctggctagcgcgtctgcggaaattgcgc
gtggtgaaaccgcaaatagcgtttcttgttacatgcgcactaaaggtatctccgaagaa
ctggctaccgaaagcgtgatgaatctgatcgatgaaacctggaaaagatgaacaagga
aaaactgggtggtagcctgttcgcgaaaccgttcgtggaaaccgcgatcaacctggcac
gtcaatctcactgcacttatcataacggcgacgcgcatacctctccggatgagctgacc
cgcaaacgcgttctgtctgtaatcactgaaccgattctgccgtttgaacgctaa
```

Figure 18 (Amino Acid Sequence of IspS variant P.tremTRC-pET200 (in pDu31))

MRGSHHHHHHGMASMTGGQQMGRDLYDDDDKDHPFTMRRSANYEPNSWDYDYLLSSDTD
ESIEVHKDKAKKLEAEVRREINNEKAEFLTLLELIDNVQRLGLGYRFESDIRRALDRFV
SSGGFDGVTKTSLHGTALSFRLLRQHGFEVSQEAFSGFKDQNGNFLENLKEDIKAILSL
YEASFLALEGENILDEAKVFAISHLKELSEEKIGKELAEQVSHALELPLHRRTQRLEAV
WSIEAYRKKEDANQVLLELAILDYNMIQSVYQRDLRETSRWWRRVGLATKLHFARDRLI
ESFYWAVGVAFEPQYSDCRNSVAKMFSFVTIIDDIYDVYGTLDELELFTDAVERWDVNA
INDLPDYMKLCFLALYNTINEIAYDNLKDKGENILPYLTKAWADLCNAFLQEAKWLYNK
STPTFDDYFGNAWKSSSGPLQLIFAYFAVVQNIKKEEIENLQKYHDIISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER

Figure 19A (DNA Sequence of pDu31)

```
cgtcgttctgcgaactacgaacctaacagctgggactatgattacctgctgtcctcga
cacggacgagtccatcgaagtacacaagacaaagcgaaaaagctggaagccgaagttc
gtcgcgagattaataacgaaaaagcagaatttctgaccctgctggaactgattgacaac
gtccagcgcctgggcctgggttaccgtttcgagtctgatatccgtcgtgcgctggatcg
cttcgtttctccggcggcttcgatggcgtaaccaagacttcctgcacggtacggcac
tgtctttccgtctgctgcgtcaacacggttttgaggtttctcaggaagcgttcagcgc
ttcaaagaccaaaacggcaacttctggagaacctgaaggaagatatcaaagctatcct
gagcctgtacgaggccagcttcctggctctggaaggcgaaaacatcctggacgaggcga
aggttttcgcaatctctcatctgaaagaactgtctgaagaaaagatcggtaaagagctg
gcagaacaggtgtcccatgcactggaactgccactgcatcgccgtactcagcgtctgga
agcagtatggtctatcgaggcctaccgtaaaaaggaggacgcgaaccaggttctgctgg
agctggcaattctggattacaacatgatccagtctgtataccagcgtgatctgcgtgaa
acgtcccgttggtggcgtcgtgtgggtctggcgaccaaactgcactttgctcgtgaccg
cctgattgagagcttctactgggccgtgggtgtagcattcgaaccgcaatactccgact
gccgtaactccgtcgcaaaaatgttttctttcgtaaccattatcgacgatatctacgat
gtatacggcaccctggacgaactggagctgtttactgatgcagttgagcgttgggacgt
aaacgccatcaacgacctgccggattacatgaaactgtgctttctggctctgtataaca
ctattaacgaaatcgcctacgacaacctgaaagataaaggtgagaacatcctgccgtat
ctgaccaaagcctggctgacctgtcaacgctttcctgcaagaagccaagtggctgta
caacaaatctactccgacctttgacgactacttcggcaacgcatggaaatcctcttctg
gcccgctgcaactgatcttcgcttacttcgctgtcgtgcagaacattaaaaaggaagag
atcgaaaacctgcaaaaataccatgacatcatctctcgtccttccatatcttccgtct
gtgcaatgacctggctagcgcgtctgcggaaattgcgcgtggtgaaaccgcaaatagcg
tttcttgttacatgcgcactaaaggtatctccgaagaactggctaccgaaagcgtgatg
aatctgatcgatgaaacctggaaaaagatgaacaaggaaaaactgggtggtagcctgtt
cgcgaaaccgttcgtggaaaccgcgatcaacctggcacgtcaatctcactgcacttatc
ataacggcgacgcgcatacctctccggatgagctgacccgcaaacgcgttctgtctgta
atcactgaaccgattctgccgtttgaacgctaaaagggcgagctcaacgatccggctgc
taacaaagcccgaaaggaagctgagttggctgctgccaccgctgagcaataactagcat
aaccccttggggcctctaaacgggtcttgaggagttttttgctgaaaggaggaactata
tccggatatcccgcaagaggccggcagtaccggcataaccaagcctatgcctacagca
tccagggtgacggtgccgaggatgacgatgagcgcattgttagatttcatacacggtgc
ctgactgcgttagcaatttaactgtgataaactaccgcattaaagcttatcgatgataa
gctgtcaaacatgagaattaattcttgaagacgaaagggcctcgtgatacgcctatttt
tataggttaatgtcatgataataatggtttcttagacgtcaggtggcacttttcggga
aatgtgcgcggaacccctatttgtttatttttctaaatacattcaaatatgtatccgct
catgagacaataaccctgataaatgcttcaataatattgaaaaaggaagagtatgattg
aacaagatggattgcacgcaggttctccggccgcttgggtggagaggctattcggctat
gactgggcacaactgacaatcggctgctctgatgccgccgtgttccggctgtcagcgca
gggcgcccggttcttttgtcaagaccgacctgtccggtgccctgaatgaactgcagg
acgaggcagcgcggctatcgtggctggccacgacgggcgttccttgcgcagctgtgctc
gacgttgtcactgaagcgggaagggactggctgctattgggcgaagtgccggggcagga
tctcctgtcatctcaccttgctcctgccgagaaagtatccatcatggctgatgcaatgc
ggcggctgcatacgcttgatccggctacctgcccattcgaccaccaagcgaaacatcgc
atcgagcgggcacgtactcggatggaagccggtcttgtcgatcaggatgatctggacga
```

Figure 19B (DNA Sequence of pDu31)

agagcatcaggggctcgcgccagccgaactgttcgccaggctcaaggcgcgcatgcccg
acggcgaggatctcgtcgtgacacatggcgatgcctgcttgccgaatatcatggtggaa
aatggccgcttttctggattcatcgactgtggccggctgggtgtggcggaccgctatca
ggacatagcgttggctacccgtgatattgctgaagagcttggcggcgaatgggctgacc
gcttcctcgtgctttacggtatcgccgctcccgattcgcagcgcatcgccttctatcgc
cttcttgacgagttcttctgagcgggactctggggttcgaaatgaccgaccaagcgacg
cctaactgtcagaccaagttactcatatactttagattgatttaaaacttcatttt
taatttaaaaggatctaggtgaagatcctttttgataatctcatgaccaaaatcccta
acgtgagttttcgttccactgagcgtcagaccccgtagaaaagatcaaaggatcttctt
gagatcctttttttctgcgcgtaatctgctgcttgcaaacaaaaaaaccaccgctacca
gcggtggtttgtttgccggatcaagagctaccaactcttttccgaaggtaactggctt
cagcagagcgcagataccaaatactgtccttctagtgtagccgtagttaggccaccact
tcaagaactctgtagcaccgcctacatacctcgctctgctaatcctgttaccagtggct
gctgccagtggcgataagtcgtgtcttaccgggttggactcaagacgatagttaccgga
taaggcgcagcggtcgggctgaacggggggttcgtgcacacagcccagcttggagcgaa
cgacctacaccgaactgagatacctacagcgtgagctatgagaaagcgccacgcttccc
gaagggagaaaggcggacaggtatccggtaagcggcagggtcggaacaggagagcgcac
gagggagcttccaggggggaaacgcctggtatctttatagtcctgtcgggtttcgccacc
tctgacttgagcgtcgatttttgtgatgctcgtcaggggggcggagcctatggaaaaac
gccagcaacgcggcctttttacggttcctggccttttgctggccttttgctcacatgtt
ctttcctgcgttatcccctgattctgtggataaccgtattaccgcctttgagtgagctg
ataccgctcgccgcagccgaacgaccgagcgcagcgagtcagtgagcgaggaagcggaa
gagcgcctgatgcggtattttctccttacgcatctgtgcggtatttcacaccgcaatgg
tgcactctcagtacaatctgctctgatgccgcatagttaagccagtatacactccgcta
tcgctacgtgactgggtcatggctgcgccccgacacccgccaacacccgctgacgcgcc
ctgacgggcttgtctgctcccggcatccgcttacagacaagctgtgaccgtctccggga
gctgcatgtgtcagaggttttcaccgtcatcaccgaaacgcgcgaggcagctgcggtaa
agctcatcagcgtggtcgtgaagcgattcacagatgtctgcctgttcatccgcgtccag
ctcgttgagtttctccagaagcgttaatgtctggcttctgataaagcgggccatgttaa
gggcggttttttcctgtttggtcactgatgcctccgtgtaaggggatttctgttcatg
gggtaatgataccgatgaaacgagagaggatgctcacgatacgggttactgatgatga
acatgcccggttactggaacgttgtgagggtaaacaactggcggtatggatgcggcggg
accagagaaaaatcactcagggtcaatgccagcgcttcgttaatacagatgtaggtgtt
ccacagggtagccagcagcatcctgcgatgcagatccggaacataatggtgcagggcgc
tgacttccgcgtttccagactttacgaaacacggaaaccgaagaccattcatgttgttg
ctcaggtcgcagacgttttgcagcagcagtcgcttcacgttcgctcgcgtatcggtgat
tcattctgctaaccagtaaggcaacccgccagcctagccgggtcctcaacgacaggag
cacgatcatgcgcacccgtggccaggacccaacgctgcccgagatgcgccgcgtgcggc
tgctggagatggcggacgcgatggatatgttctgccaagggttggtttgcgcattcaca
gttctccgcaagaattgattggctccaattcttggagtggtgaatccgttagcgaggtg
ccgccggcttccattcaggtcgaggtggcccggctccatgcaccgcgacgcaacgcggg
gaggcagacaaggtatagggcggcgcctacaatccatgccaacccgttccatgtgctcg
ccgaggcggcataaatcgccgtgacgatcagcggtccaatgatcgaagttaggctggta
agagccgcgagcgatccttgaagctgtccctgatggtcgtcatctacctgcctggacag
catggcctgcaacgcgggcatcccgatgccgccggaagcgagaagaatcataatgggga Figure 19C (DNA Sequence of pDu31)

```
aggccatccagcctcgcgtcgcgaacgccagcaagacgtagcccagcgcgtcggccgcc
atgccggcgataatggcctgcttctcgccgaaacgtttggtggcgggaccagtgacgaa
ggcttgagcgagggcgtgcaagattccgaataccgcaagcgacaggccgatcatcgtcg
cgctccagcgaaagcggtcctcgccgaaaatgacccagagcgctgccggcacctgtcct
acgagttgcatgataaagaagacagtcataagtgcggcgacgatagtcatgccccgcgc
ccaccggaaggagctgactgggttgaaggctctcaagggcatcggtcgagatcccggtg
cctaatgagtgagctaacttacattaattgcgttgcgctcactgcccgctttccagtcg
ggaaacctgtcgtgccagctgcattaatgaatcggccaacgcgcggggagaggcggttt
gcgtattgggcgccagggtggttttcttttcaccagtgagacgggcaacagctgattg
cccttcaccgcctggccctgagagagttgcagcaagcggtccacgctggtttgcccag
caggcgaaaatcctgtttgatggtggttaacggcgggatataacatgagctgtcttcgg
tatcgtcgtatcccactaccgagatatccgccaccaacgcgcagcccggactcggtaatg
gcgcgcattgcgcccagcgccatctgatcgttggcaaccagcatcgcagtgggaacgat
gccctcattcagcatttgcatggtttgttgaaaaccggacatggcactccagtcgcctt
cccgttccgctatcggctgaatttgattgcgagtgagatatttatgccagccagccaga
cgcagacgcgccgagacagaacttaatgggccgctaacagcgcgatttgctggtgacc
caatgcgaccagatgctccacgcccagtcgcgtaccgtcttcatgggagaaaataatac
tgttgatgggtgtctggtcagagacatcaagaaataacgccggaacattagtgcaggca
gcttccacagcaatggcatcctggtcatccagcggatagttaatgatcagcccactgac
gcgttgcgcgagaagattgtgcaccgccgctttacaggcttcgacgccgcttcgttcta
ccatcgacaccaccacgctggcacccagttgatcggcgcgagatttaatcgccgcgaca
atttgcgacggcgcgtgcagggccagactggaggtggcaacgccaatcagcaacgactg
tttgcccgccagttgttgtgccacgcggttgggaatgtaattcagctccgccatcgccg
cttccacttttttcccgcgttttcgcagaaacgtggctggcctggttcaccacgcgggaa
acggtctgataagagacaccggcatactctgcgacatcgtataacgttactggtttcac
attcaccaccctgaattgactctcttccgggcgctatcatgccataccgcgaaaggttt
tgcgccattcgatggtgtccgggatctcgacgctctcccttatgcgactcctgcattag
gaagcagcccagtagtaggttgaggccgttgagcaccgccgcgcaaggaatggtgcat
gcaaggagatggcgcccaacagtccccggccacgggcctgccaccatacccacgccg
aaacaagcgctcatgagcccgaagtggcgagcccgatcttccccatcggtgatgtcggc
gatataggcgccagcaaccgcacctgtggcgccggtgatgccggccacgatgcgtccgg
cgtagaggatcgagatctcgatcccgcgaaattaatacgactcactatagggaattgt
gagcggataacaattcccctctagaaataattttgtttaactttaagaaggagatatac
atatgcggggttctcatcatcatcatcatcatggtatggctagcatgactggtggacag
caaatgggtcgggatctgtacgacgatgacgataaggatcatcccttcaccatg
```

Figure 20 (Amino Acid Sequence of IspS variant P.trichTRC-pET200 (in pDu32))

MRGSHHHHHHGMASMTGGQQMGRDLYDDDDKDHPFTMRRSANYEPNSWDYDYLLSSDTD
ESIEVYKDKAKKLEAEVRREINNEKAEFLTLLELIDNVQRLGLGYRFESDIRRALDRFV
SSGGFDAVTKTSLHATALSFRLLRQHGFEVSQEAFSGFKDQNGNFLENLKEDIKAILSL
YEASFLALEGENILDEAKVFAISHLKELSEEKIGKDLAEQVNHALELPLHRRTQRLEAV
LSIEAYRKKEDADQVLLELAILDYNMIQSVYQRDLRETSRWWRRVGLATKLHFARDRLI
ESFYWAVGVAFEPQYSDCRNSVAKMFSFVTIIDDIYDVYGTLDELELFTNAVERWDVNA
IDDLPDYMKLCFLALYNTINEIAYDNLKEKGENILPYLTKAWADLCNAFLQEAKWLYNK
STPTFDEYFGNAWKSSSGPLQLVFAYFAVVQNIKKEEIENLQKYHDIISRPSHIFRLCN
DLASASAEIARGETANSVSCYMRTKGISEELATESVMNLIDETWKKMNKEKLGGSLFAK
PFVETAINLARQSHCTYHNGDAHTSPDELTRKRVLSVITEPILPFER

Figure 21A (DNA Sequence of pDu32)

cgtcgttctgcgaactacgaacctaacagctgggactatgattacctgctgtcctccga
cacggacgagtccatcgaagtatacaaagacaaagcgaaaaagctggaagccgaagttc
gtcgcgagattaataacgaaaaagcagaatttctgaccctgctggaactgattgacaac
gtccagcgcctgggcctgggttaccgtttcgagtctgatatccgtcgtgcgctggatcg
cttcgtttcctccggcggcttcgatgcggtaaccaagacttccctgcacgcgacggcac
tgtctttccgtctgctgcgtcaacacggttttgaggtttctcaggaagcgttcagcggc
ttcaaagaccaaaacggcaacttcctggagaacctgaaggaagatatcaaagctatcct
gagcctgtacgaggccagcttcctggctctggaaggcgaaaacatcctggacgaggcga
aggttttcgcaatctctcatctgaaagaactgtctgaagaaagatcggtaaagatctg
gcagaacaggtgaaccatgcactggaactgccactgcatcgccgtactcagcgtctgga
agcagtactgtctatcgaggcctaccgtaaaaaggaggacgcggatcaggttctgctgg
agctggcaattctggattacaacatgatccagtctgtataccagcgtgatctgcgtgaa
acgtcccgttggtggcgtcgtgtgggtctggcgaccaaactgcactttgctcgtgaccg
cctgattgagagcttctactgggccgtggggtgtagcattcgaaccgcaatactccgact
gccgtaactccgtcgcaaaaatgttttctttcgtaaccattatcgacgatatctacgat
gtatacggcaccctggacgaactggagctgtttactaacgcagttgagcgttgggacgt
aaacgccatcgacgatctgccggattacatgaaactgtgctttctggctctgtataaca
ctattaacgaaatcgcctacgacaacctgaaagaaaaaggtgagaacatcctgccgtat
ctgaccaaagcctgggctgacctgtgcaacgcttcctgcaagaagccaagtggctgta
caacaaatctactccgaccttgacgaatacttcggcaacgcatggaaatcctcttctg
gcccgctgcaactggtgttcgcttacttcgctgtcgtgcagaacattaaaaaggaagag
atcgaaaacctgcaaaaataccatgacatcatctctcgtccttcccatatcttccgtct
gtgcaatgacctggctagcgcgtctgcggaaattgcgcgtggtgaaaccgcaaatagcg
tttcttgttacatgcgcactaaaggtatctccgaagaactggctaccgaaagcgtgatg
aatctgatcgatgaaacctggaaaaagatgaacaaggaaaaactgggtggtagcctgtt
cgcgaaaccgttcgtggaaaccgcgatcaacctggcacgtcaatctcactgcacttatc
ataacggcgacgcgcataccctctccggatgagctgacccgcaaacgcgttctgtctgta
atcactgaaccgattctgccgtttgaacgctaaaagggcgagctcaacgatccggctgc
taacaaagcccgaaaggaagctgagttggctgctgccaccgctgagcaataactagcat
aacccctcggggcctctaaacgggtcttgaggagttttttgctgaaaggaggaactata
tccggatatcccgcaagaggcccggcagtaccggcataaccaagcctatgcctacagca
tccagggtgacggtgccgaggatgacgatgagcgcattgttagatttcatacacggtgc
ctgactgcgttagcaatttaactgtgataaactaccgcattaaagcttatcgatgataa
gctgtcaaacatgagaattaattcttgaagacgaaagggcctcgtgatacgcctatttt
tataggttaatgtcatgataataatggtttcttagacgtcaggtggcacttttcgggga
aatgtgcgcggaacccctatttgtttatttttctaaatacattcaaatatgtatccgct
catgagacaataaccctgataaatgcttcaataatattgaaaaaggaagagtatgattg
aacaagatggattgcacgcaggttctccggccgcttgggtggagaggctattcggctat
gactgggcacaactgacaatcggctgctctgatgccgccgtgttccggctgtcagcgca
gggcgcccggttcttttttgtcaagaccgacctgtccggtgccctgaatgaactgcagg
acgaggcagcgcggctatcgtggctggccacgacgggcgttccttgcgcagctgtgctc
gacgttgtcactgaagcgggaagggactggctgctattgggcgaagtgccggggcagga
tctcctgtcatctcaccttgctcctgccgagaaagtatccatcatggctgatgcaatgc
ggcggctgcatacgcttgatccggctacctgcccattcgaccaccaagcgaaacatcgc
atcgagcgggcacgtactcggatggaagccggtcttgtcgatcaggatgatctggacga Figure 21B (DNA Sequence of pDu32)

```
agagcatcaggggctcgcgccagccgaactgttcgccaggctcaaggcgcgcatgcccg
acggcgaggatctcgtcgtgacacatggcgatgcctgcttgccgaatatcatggtggaa
atggccgcttttctggattcatcgactgtggccggctgggtgtggcggaccgctatca
ggacatagcgttggctaccgtgatattgctgaagagcttggcggcgaatgggctgacc
gcttcctcgtgctttacggtatcgccgctcccgattcgcagcgcatcgccttctatcgc
cttcttgacgagttcttctgagcgggactctggggttcgaaatgaccgaccaagcgacg
cctaactgtcagaccaagtttactcatatactttagattgatttaaaacttcattt
taatttaaaaggatctaggtgaagatccttttgataatctcatgaccaaaatcccta
acgtgagttttcgttccactgagcgtcagacccgtagaaaagatcaaaggatcttctt
gagatcctttttttctgcgcgtaatctgctgcttgcaaacaaaaaaaccaccgctacca
gcggtggtttgtttgccggatcaagagctaccaactcttttccgaaggtaactggctt
cagcagagcgcagataccaaatactgtccttctagtgtagccgtagttaggccaccact
tcaagaactctgtagcaccgcctacatacctcgctctgctaatcctgttaccagtggct
gctgccagtggcgataagtcgtgtcttaccgggttggactcaagacgatagttaccgga
taaggcgcagcggtcgggctgaacggggggttcgtgcacacagcccagcttggagcgaa
cgacctacaccgaactgagatacctacagcgtgagctatgagaaagcgccacgcttccc
gaagggagaaaggcggacaggtatccggtaagcggcagggtcggaacaggagagcgcac
gagggagcttccaggggggaaacgcctggtatctttatagtcctgtcgggtttcgccacc
tctgacttgagcgtcgatttttgtgatgctcgtcaggggggcggagcctatggaaaaac
gccagcaacgcggcctttttacggttcctggccttttgctggccttttgctcacatgtt
ctttcctgcgttatcccctgattctgtggataaccgtattaccgcctttgagtgagctg
ataccgctcgccgcagccgaacgaccgagcgcagcgagtcagtgagcgaggaagcggaa
gagcgcctgatgcggtattttctccttacgcatctgtgcggtatttcacaccgcaatgg
tgcactctcagtacaatctgctctgatgccgcatagttaagccagtatacactccgcta
tcgctacgtgactgggtcatggctgcgccccgacaccgccaacaccgctgacgcgcc
ctgacgggcttgtctgctcccggcatccgcttacagacaagctgtgaccgtctccgga
gctgcatgtgtcagaggttttcaccgtcatcaccgaaacgcgcgaggcagctgcggtaa
agctcatcagcgtggtcgtgaagcgattcacagatgtctgctgttcatccgcgtccag
ctcgttgagtttctccagaagcgttaatgtctggcttctgataaagcgggccatgttaa
gggcggttttttcctgtttggtcactgatgcctccgtgtaaggggatttctgttcatg
ggggtaatgataccgatgaaacgagagaggatgctcacgatacgggttactgatgatga
acatgcccggttactggaacgttgtgagggtaaacaactggcggtatggatgcggcggg
accagagaaaaatcactcagggtcaatgccagcgcttcgttaatacagatgtaggtgtt
ccacagggtagccagcagcatcctgcgatgcagatccggaacataatggtgcagggcgc
tgacttccgcgtttccagactttacgaaacacggaaaccgaagaccattcatgttgttg
ctcaggtcgcagacgttttgcagcagcagtcgcttcacgttcgctcgcgtatcggtgat
tcattctgctaaccagtaaggcaacccgccagcctagccgggtcctcaacgacaggag
cacgatcatgcgcacccgtggccaggacccaacgctgcccgagatgcgccgcgtgcggc
tgctggagatggcggacgcgatggatatgttctgccaagggttggtttgcgcattcaca
gttctccgcaagaattgattggctccaattcttggagtggtgaatccgttagcgaggtg
ccgccggcttccattcaggtcgaggtggcccggctccatgcaccgcgacgcaacgcggg
gaggcagacaaggtataggcggcgcctacaatccatgccaacccgttccatgtgctcg
ccgaggcggcataaatcgccgtgacgatcagcggtccaatgatcgaagttaggctggta
agagccgcgagcgatccttgaagctgtccctgatggtcgtcatctacctgcctggacag
catggcctgcaacgcgggcatcccgatgccgccggaagcgagaagaatcataatgggga
```

Figure 21C (DNA Sequence of pDu32)

```
aggccatccagcctcgcgtcgcgaacgccagcaagacgtagcccagcgcgtcggccgcc
atgccggcgataatggcctgcttctcgccgaaacgtttggtggcgggaccagtgacgaa
ggcttgagcgagggcgtgcaagattccgaataccgcaagcgacaggccgatcatcgtcg
cgctccagcgaaagcggtcctcgccgaaaatgacccagagcgctgccggcacctgtcct
acgagttgcatgataaagaagacagtcataagtgcggcgacgatagtcatgccccgcgc
ccaccggaaggagctgactgggttgaaggctctcaagggcatcggtcgagatcccggtg
cctaatgagtgagctaacttacattaattgcgttgcgctcactgcccgctttccagtcg
ggaaacctgtcgtgccagctgcattaatgaatcggccaacgcgcggggagaggcggttt
gcgtattgggcgccagggtggttttcttttcaccagtgagacgggcaacagctgattg
cccttcaccgcctggccctgagagagttgcagcaagcggtccacgctggtttgcccag
caggcgaaaatcctgtttgatggtggttaacggcgggatataacatgagctgtcttcgg
tatcgtcgtatccactaccgagatatccgcaccaacgcgcagcccggactcggtaatg
gcgcgcattgcgccagcgccatctgatcgttggcaaccagcatcgcagtgggaacgat
gccctcattcagcatttgcatggttttgttgaaaaccggacatggcactccagtcgcctt
cccgttccgctatcggctgaatttgattgcgagtgagatatttatgccagccagccaga
cgcagacgcgccgagacagaacttaatgggccgctaacagcgcgatttgctggtgacc
caatgcgaccagatgctccacgccagtcgcgtaccgtcttcatgggagaaaataatac
tgttgatgggtgtctggtcagagacatcaagaaataacgccggaacattagtgcaggca
gcttccacagcaatggcatcctggtcatccagcggatagttaatgatcagcccactgac
gcgttgcgcgagaagattgtgcaccgccgctttacaggcttcgacgccgcttcgttcta
ccatcgacaccaccacgctggcacccagttgatcggcgcgagatttaatcgccgcgaca
atttgcgacggcgcgtgcagggccagactggaggtggcaacgccaatcagcaacgactg
tttgcccgccagttgttgtgccacgcggttgggaatgtaattcagctccgccatcgccg
cttccacttttttccgcgtttttcgcagaaacgtggctggcctggttcaccacgcgggaa
acggtctgataagagacaccggcatactctgcgacatcgtataacgttactggtttcac
attcaccaccctgaattgactctcttccgggcgctatcatgccataccgcgaaaggttt
tgcgccattcgatggtgtccgggatctcgacgctctcccttatgcgactcctgcattag
gaagcagcccagtagtaggttgaggccgttgagcaccgccgccgcaaggaatggtgcat
gcaaggagatggcgcccaacagtccccggccacggggcctgccaccataccacgccg
aaacaagcgctcatgagcccgaagtggcgagcccgatcttccccatcggtgatgtcggc
gatataggcgccagcaaccgcacctgtggcgccggtgatgccggccacgatgcgtccgg
cgtagaggatcgagatctcgatcccgcgaaattaatacgactcactatagggaattgt
gagcggataacaattcccctctagaaataattttgtttaactttaagaaggagatatac
atatgcggggttctcatcatcatcatcatcatggtatggctagcatgactggtggacag
caaatgggtcgggatctgtacgacgatgacgataaggatcatcccttcaccatg
```

Figure 22A (DNA sequence of pDu27)

aagggcgagctcaacgatccggctgctaacaaagcccgaaaggaagctgagttggctgc
tgccaccgctgagcaataactagcataaccccttggggcctctaaacgggtcttgagga
gttttttgctgaaaggaggaactatatccggatatcccgcaagaggcccggcagtaccg
gcataaccaagcctatgcctacagcatccaggdgtgacggtgccgaggatgacgatgagc
gcattgttagatttcatacacggtgcctgactgcgttagcaatttaactgtgataaact
accgcattaaagcttatcgatgataagctgtcaaacatgagaattaattcttgaagacg
aaagggcctcgtgatacgcctatttttataggttaatgtcatgataataatggtttctt
agacgtcaggtggcacttttcggggaaatgtgcgcggaacccctatttgtttatttttc
taaatacattcaaatatgtatccgctcatgagacaataaccctgataaatgcttcaata
atattgaaaaaggaagagtatgattgaacaagatggattgcacgcaggttctccggccg
cttgggtggagaggctattcggctatgactgggcacaactgacaatcggctgctctgat
gccgccgtgttccggctgtcagcgcaggggcgcccggttcttttttgtcaagaccgacct
gtccggtgccctgaatgaactgcaggacgaggcagcgcggctatcgtggctggccacga
cgggcgttccttgcgcagctgtgctcgacgttgtcactgaagcgggaagggactggctg
ctattgggcgaagtgccggggcaggatctcctgtcatctcaccttgctcctgccgagaa
agtatccatcatggctgatgcaatgcggcggctgcatacgcttgatccggctacctgcc
cattcgaccaccaagcgaaacatcgcatcgagcgggcacgtactcggatggaagccggt
cttgtcgatcaggatgatctggacgaagagcatcaggggctcgcgccagccgaactgtt
cgccaggctcaaggcgcgcatgcccgacggcgaggatctcgtcgtgacacatggcgatg
cctgcttgccgaatatcatggtggaaaatggccgcttttctggattcatcgactgtggc
cggctgggtgtggcggaccgctatcaggacatagcgttggctacccgtgatattgctga
agagcttggcggcgaatgggctgaccgcttcctcgtgctttacggtatcgccgctcccg
attcgcagcgcatcgccttctatcgccttcttgacgagttcttctgagcgggactctgg
ggttcgaaatgaccgaccaagcgacgcctaactgtcagaccaagtttactcatatatac
tttagattgatttaaaacttcattttaattaaaaggatctaggtgaagatcctttt
gataatctcatgaccaaaatcccttaacgtgagttttcgttccactgagcgtcagaccc
cgtagaaaagatcaaaggatcttcttgagatcctttttttctgcgcgtaatctgctgct
tgcaaacaaaaaaaccaccgctaccagcggtggtttgtttgccggatcaagagctacca
actctttttccgaaggtaactggcttcagcagagcgcagataccaaatactgtccttct
agtgtagccgtagttaggccaccacttcaagaactctgtagcaccgcctacatacctcg
ctctgctaatcctgttaccagtggctgctgccagtggcgataagtcgtgtcttaccggg
ttggactcaagacgatagttaccggataaggcgcagcggtcgggctgaacggggggttc
gtgcacacagcccagcttggagcgaacgacctacaccgaactgagatacctacagcgtg
agctatgagaaagcgccacgcttcccgaagggagaaaggcggacaggtatccggtaagc
ggcagggtcggaacaggagagcgcacgagggagcttccaggggaaacgcctggtatct
ttatagtcctgtcgggtttcgccacctctgacttgagcgtcgatttttgtgatgctcgt
caggggggcggagcctatggaaaaacgccagcaacgcggcctttttacggttcctggcc
ttttgctggccttttgctcacatgttctttcctgcgttatcccctgattctgtggataa
ccgtattaccgcctttgagtgagctgataccgctcgccgcagccgaacgaccgagcgca
gcgagtcagtgagcgaggaagcggaagagcgcctgatgcggtatttctccttacgcat
ctgtgcggtatttcacaccgcaatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag Figure 22B (DNA sequence of pDu27)

```
atgtctgcctgttcatccgcgtccagctcgttgagtttctccagaagcgttaatgtctg
gcttctgataaagcgggccatgttaagggcggttttttctgtttggtcactgatgcct
ccgtgtaaggggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcaccgtggccaggacccaac
gctgcccgagatgcgccgcgtgcggctgctggagatggcggacgcgatggatatgttct
gccaagggttggtttgcgcattcacagttctccgcaagaattgattggctccaattctt
ggagtggtgaatccgttagcgaggtgccgccggcttccattcaggtcgaggtggcccgg
ctccatgcaccgcgacgcaacgcggggaggcagacaaggtatagggcggcgcctacaat
ccatgccaacccgttccatgtgctcgccgaggcggcataaatcgccgtgacgatcagcg
gtccaatgatcgaagttaggctggtaagagccgcgagcgatccttgaagctgtccctga
tggtcgtcatctacctgcctggacagcatggcctgcaacgcgggcatcccgatgccgcc
ggaagcgagaagaatcataatggggaaggccatccagcctcgcgtcgcgaacgccagca
agacgtagcccagcgcgtcggccgccatgccggcgataatggcctgcttctcgccgaaa
cgtttggtggcgggaccagtgacgaaggcttgagcgagggcgtgcaagattccgaatac
cgcaagcgacaggccgatcatcgtcgcgctccagcgaaagcggtcctcgccgaaaatga
cccagagcgctgccggcacctgtcctacgagttgcatgataaagaagacagtcataagt
gcggcgacgatagtcatgcccgcgccaccggaaggagctgactggttgaaggctct
caagggcatcggtcgagatcccggtgcctaatgagtgagctaacttacattaattgcgt
tgcgctcactgcccgctttccagtcgggaaacctgtcgtgccagctgcattaatgaatc
ggccaacgcgcggggagaggcggtttgcgtattgggcgccagggtggttttttcttttca
ccagtgagacgggcaacagctgattgcccttcaccgcctggccctgagagagttgcagc
aagcggtccacgctggtttgccccagcaggcgaaaatcctgtttgatggtggttaacgg
cgggatataacatgagctgtcttcggtatcgtcgtatcccactaccgagatatccgcac
caacgcgcagcccggactcggtaatggcgcgcattgcgcccagcgccatctgatcgttg
gcaaccagcatcgcagtgggaacgatgccctcattcagcatttgcatggtttgttgaaa
accggacatggcactccagtcgccttcccgttccgctatcggctgaatttgattgcgag
tgagatatttatgccagccagccagacgcagacgcgccgagacagaacttaatgggccc
gctaacagcgcgatttgctggtgacccaatgcgaccagatgctccacgcccagtcgcgt
accgtcttcatgggagaaaataatactgttgatgggtgtctggtcagagacatcaagaa
ataacgccggaacattagtgcaggcagcttccacagcaatggcatcctggtcatccagc
ggatagttaatgatcagcccactgacgcgttgcgcgagaagattgtgcaccgccgcttt
acaggcttcgacgccgcttcgttctaccatcgacaccaccgctggcacccagttgat
cggcgcgagatttaatcgccgcgacaatttgcgacggcgcgtgcagggccagactggag
gtggcaacgccaatcagcaacgactgtttgccgccagttgttgtgccacgcggttggg
aatgtaattcagctccgccatcgccgcttccactttttcccgcgttttcgcagaaacgt
ggctggcctggttcaccacgcgggaaacggtctgataagagacaccggcatactctgcg
acatcgtataacgttactggtttcacattcaccaccctgaattgactctcttccgggcg
ctatcatgccataccgcgaaaggttttgcgccattcgatggtgtccgggatctcgacgc
tctcccttatgcgactcctgcattaggaagcagccagtagtaggttgaggccgttgag
```

Figure 22C (DNA sequence of pDu27)

```
caccgccgccgcaaggaatggtgcatgcaaggagatggcgcccaacagtccccggcca
cggggcctgccaccatacccacgccgaaacaagcgctcatgagcccgaagtggcgagcc
cgatcttccccatcggtgatgtcggcgatataggcgccagcaaccgcacctgtggcgcc
ggtgatgccggccacgatgcgtccggcgtagaggatcgagatctcgatcccgcgaaatt
aatacgactcactatagggaattgtgagcggataacaattcccctctagaaataattt
tgtttaactttaagaaggagatatacatatgcggggttctcatcatcatcatcatcatg
gtatggctagcatgactggtggacagcaaatgggtcgggatctgtacgacgatgacgat
aaggatcatcccttcaccatgcgttgtagcgtgtccaccgaaaatgtgtctttcaccga
aactgaaaccgaagctcgtcgttctgcgaactacgaacctaacagctgggactatgatt
acctgctgtcctccgacacggacgagtccatcgaagtatacaaagacaaagcgaaaaag
ctggaagccgaagttcgtcgcgagattaataacgaaaaagcagaatttctgaccctgct
ggaactgattgacaacgtccagcgcctgggcctgggttaccgtttcgagtctgatatcc
gtggtgcgctggatcgcttcgtttcctccggcggcttcgatgcggtaaccaagacttcc
ctgcacggtacggcactgtctttccgtctgctgcgtcaacacggttttgaggtttctca
ggaagcgttcagcggcttcaaagaccaaaacggcaacttcctggagaacctgaaggaag
atatcaaagctatcctgagcctgtacgaggccagcttcctggctctggaaggcgaaaac
atcctggacgaggcgaaggttttcgcaatctctcatctgaaagaactgtctgaagaaaa
gatcggtaaagagctggcagaacaggtgaaccatgcactggaactgccactgcatcgcc
gtactcagcgtctggaagcagtatggtctatcgaggcctaccgtaaaaaggaggacgcg
aatcaggttctgctggagctggcaattctggattacaacatgatccagtctgtatacca
gcgtgatctgcgtgaaacgtcccgttggtggcgtcgtgtgggtctggcgaccaaactgc
actttgctcgtgaccgcctgattgagagcttctactgggccgtgggtgtagcattcgaa
ccgcaatactccgactgccgtaactccgtcgcaaaaatgtttctttcgtaaccattat
cgacgatatctacgatgtatacggcaccctggacgaactggagctgtttactgatgcag
ttgagcgttgggacgtaaacgccatcaacgacctgccggattacatgaaactgtgcttt
ctggctctgtataacactattaacgaaatcgcctacgacaacctgaaagataaaggtga
gaacatcctgccgtatctgaccaaagcctgggctgacctgtcaacgctttcctgcaag
aagccaagtggctgtacaacaaatctactccgacctttgacgactacttcggcaacgca
tggaaatcctcttctggcccgctgcaactggtgttcgcttacttcgctgtcgtgcagaa
cattaaaaaggaagagatcgaaaacctgcaaaaataccatgacaccatctctcgtcctt
cccatatcttccgtctgtgcaatgacctggctagcgcgtctgcggaaattgcgcgtggt
gaaaccgcaaatagcgtttcttgttacatgcgcactaaaggtatctccgaagaactggc
taccgaaagcgtgatgaatctgatcgatgaaacctggaaaaagatgaacaaggaaaaac
tgggtggtagcctgttcgcgaaaccgttcgtggaaaccgcgatcaacctggcacgtcaa
tctcactgcacttatcataacggcgacgcgcataccctctccggatgagctgacccgcaa
acgcgttctgtctgtaatcactgaaccgattctgccgtttgaacgctaa
```

Figure 23 (Amino Acid Sequence of Full Length P. alba IspS (in P. alba pET24a))

MRCSVSTENVSFTETETEARRSANYEPNSWDYDYLLSSDTDESIEVYKDKAKKLEAEVR
REINNEKAEFLTLLELIDNVQRLGLGYRFESDIRGALDRFVSSGGFDAVTKTSLHGTAL
SFRLLRQHGFEVSQEAFSGFKDQNGNFLENLKEDIKAILSLYEASFLALEGENILDEAK
VFAISHLKELSEEKIGKELAEQVNHALELPLHRRTQRLEAVWSIEAYRKKEDANQVLLE
LAILDYNMIQSVYQRDLRETSRWWRRVGLATKLHFARDRLIESFYWAVGVAFEPQYSDC
RNSVAKMFSFVTIIDDIYDVYGTLDELELFTDAVERWDVNAINDLPDYMKLCFLALYNT
INEIAYDNLKDKGENILPYLTKAWADLCNAFLQEAKWLYNKSTPTFDDYFGNAWKSSSG
PLQLVFAYFAVVQNIKKEEIENLQKYHDTISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFER

Figure 24A (DNA sequence of P. alba pET24a)

```
tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctccctt
agggttccgatttagtgctttacggcacctcgaccccaaaaaacttgattagggtgatg
gttcacgtagtgggccatcgccctgatagacggtttttcgccctttgacgttggagtcc
acgttctttaatagtggactcttgttccaaactggaacaacactcaacctatctcggt
ctattcttttgatttataaggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatattttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
taccatataaatcagcatccatgttggaatttaatcgcggcctagagcaagacgtttc
ccgttgaatatggctcataacacccctttgtattactgtttatgtaagcagacagtttta
ttgttcatgaccaaaatcccttaacgtgagttttcgttccactgagcgtcagaccccgt
agaaaagatcaaaggatcttcttgagatcctttttttctgcgcgtaatctgctgcttgc
aaacaaaaaaaccaccgctaccagcggtggtttgtttgccggatcaagagctaccaact
ctttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttccgaagggagaaaggcggacaggtatccggtaagcggc
agggtcggaacaggagagcgcacgagggagcttccaggggaaacgcctggtatcttta
tagtcctgtcgggtttcgccacctctgacttgagcgtcgatttttgtgatgctcgtcag
ggggcggagcctatggaaaaacgccagcaacgcggcctttttacggttcctggccttt
tgctggccttttgctcacatgttctttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag
atgtctgcctgttcatccgcgtccagctcgttgagtttctccagaagcgttaatgtctg
```

Figure 24B (DNA sequence of P. alba pET24a)

gcttctgataaagcgggccatgttaagggcggttttttcctgtttggtcactgatgcct
ccgtgtaagggggatttctgttcatggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagacttacgaaacacg
gaaaccgaagaccattcatgttgttgctcaggtcgcagacgttttgcagcagcagtcgc
ttcacgttcgctcgcgtatcggtgattcattctgctaaccagtaaggcaaccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggttttcttttcaccagtgagacgggcaacagctgattgccctt
caccgcctggccctgagagagttgcagcaagcggtccacgctggtttgcccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
acttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactcctgcattaggaagc
agcccagtagtaggttgaggccgttgagcaccgccgccgcaaggaatggtgcatgcaag
gagatggcgcccaacagtccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactatagggaattgtgagcg
gataacaattcccctctagaaataattttgtttaactttaagaaggagatatacatatg
cgttgtagcgtgtccaccgaaaatgtgtctttcaccgaaactgaaaccgaagctcgtcg
ttctgcgaactacgaacctaacagctgggactatgattacctgctgtcctccgacacgg
acgagtccatcgaagtatacaaagacaaagcgaaaaagctggaagccgaagttcgtcgc
gagattaataacgaaaaagcagaatttctgaccctgctggaactgattgacaacgtcca Figure 24C (DNA sequence of P. alba pET24a)

```
gcgcctgggcctgggttaccgtttcgagtctgatatccgtggtgcgctggatcgcttcg
tttcctccggcggcttcgatgcggtaaccaagacttccctgcacggtacggcactgtct
ttccgtctgctgcgtcaacacggttttgaggtttctcaggaagcgttcagcggcttcaa
agaccaaaacggcaacttcctggagaacctgaaggaagatatcaaagctatcctgagcc
tgtacgaggccagcttcctggctctggaaggcgaaaacatcctggacgaggcgaaggtt
ttcgcaatctctcatctgaaagaactgtctgaagaaaagatcggtaaagagctggcaga
acaggtgaaccatgcactggaactgccactgcatcgccgtactcagcgtctggaagcag
tatggtctatcgaggcctaccgtaaaaaggaggacgcgaatcaggttctgctggagctg
gcaattctggattacaacatgatccagtctgtataccagcgtgatctgcgtgaaacgtc
ccgttggtggcgtcgtgtgggtctggcgaccaaactgcactttgctcgtgaccgcctga
ttgagagcttctactgggccgtgggtgtagcattcgaaccgcaatactccgactgccgt
aactccgtcgcaaaaatgttttctttcgtaaccattatcgacgatatctacgatgtata
cggcaccctggacgaactggagctgtttactgatgcagttgagcgttgggacgtaaacg
ccatcaacgacctgccggattacatgaaactgtgctttctggctctgtataacactatt
aacgaaatcgcctacgacaacctgaaagataaaggtgagaacatcctgccgtatctgac
caaagctgggctgacctgtgcaacgcttttcctgcaagaagccaagtggctgtacaaca
aatctactccgacctttgacgactacttcggcaacgcatggaaatcctcttctggcccg
ctgcaactggtgttcgcttacttcgctgtcgtgcagaacattaaaaaggaagagatcga
aaacctgcaaaaataccatgacaccatctctcgtccttccatatcttccgtctgtgca
atgacctggctagcgcgtctgcggaaattgcgcgtggtgaaaccgcaaatagcgtttct
tgttacatgcgcactaaaggtatctccgaagaactggctaccgaaagcgtgatgaatct
gatcgatgaaacctggaaaaagatgaacaaggaaaaactgggtggtagcctgttcgcga
accgttcgtggaaaccgcgatcaacctggcacgtcaatctcactgcacttatcataac
ggcgacgcgcatacctctccggatgagctgacccgcaaacgcgttctgtctgtaatcac
tgaaccgattctgccgtttgaacgctaaggatccgaattcgagctccgtcgacaagctt
gcggccgcactcgagcaccaccaccaccaccactgagatccggctgctaacaaagcccg
aaaggaagctgagttggctgctgccaccgctgagcaataactagcataaccccttgggg
cctctaaacgggtcttgaggggttttttgctgaaaggaggaactatatccggat
```

Figure 25
A.
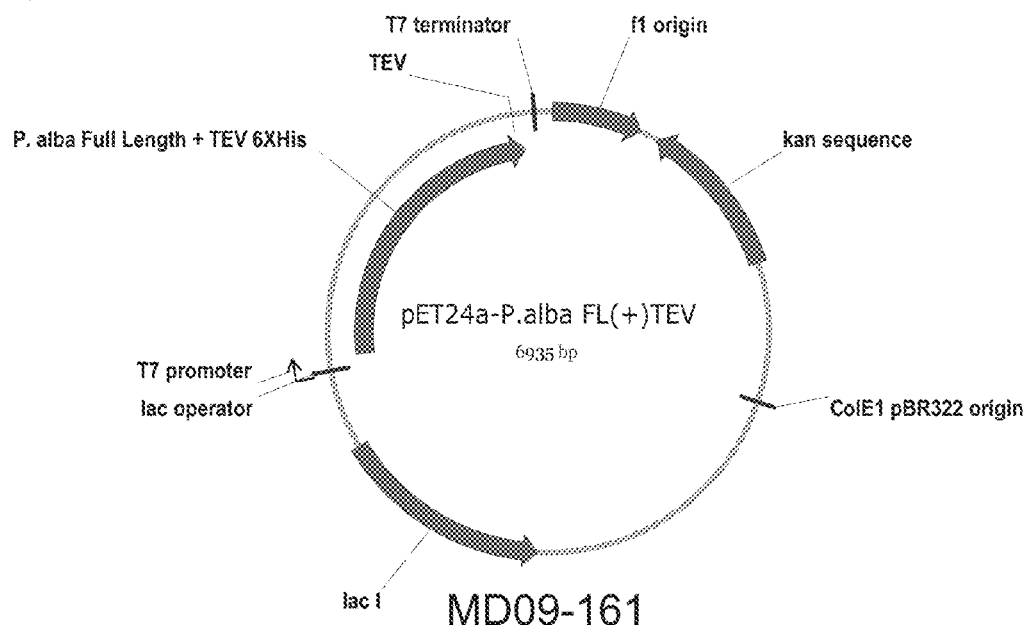
B.
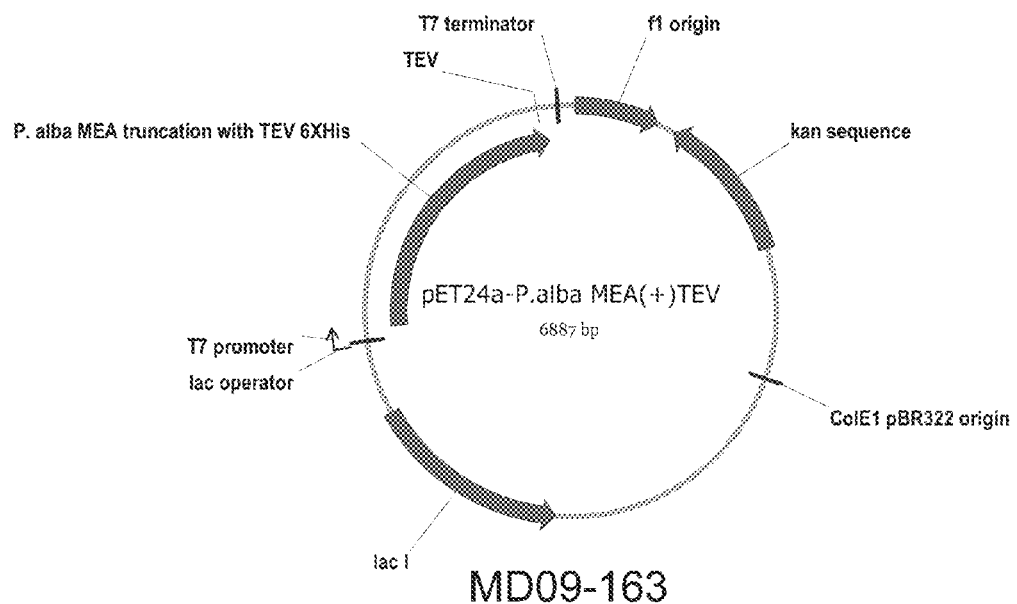

Figure 26 (Amino Acid Sequence of P. alba MEA(+)TEV (in MD09-163))

MEARRSANYEPNSWDYDYLLSSDTDESIEVYKDKAKKLEAEVRREINNEKAEFLTLLEL
IDNVQRLGLGYRFESDIRGALDRFVSSGGFDAVTKTSLHGTALSFRLLRQHGFEVSQEA
FSGFKDQNGNFLENLKEDIKAILSLYEASFLALEGENILDEAKVFAISHLKELSEEKIG
KELAEQVNHALELPLHRRTQRLEAVWSIEAYRKKEDANQVLLELAILDYNMIQSVYQRD
LRETSRWWRRVGLATKLHFARDRLIESFYWAVGVAFEPQYSDCRNSVAKMFSFVTIIDD
IYDVYGTLDELELFTDAVERWDVNAINDLPDYMKLCFLALYNTINEIAYDNLKDKGENI
LPYLTKAWADLCNAFLQEAKWLYNKSTPTFDDYFGNAWKSSSGPLQLVFAYFAVVQNIK
KEEIENLQKYHDTISRPSHIFRLCNDLASASAEIARGETANSVSCYMRTKGISEELATE
SVMNLIDETWKKMNKEKLGGSLFAKPFVETAINLARQSHCTYHNGDAHTSPDELTRKRV
LSVITEPILPFERENLYFQGLEHHHHHH

Figure 27A (DNA sequence of MD09-163 = pET24a-P. alba MEA(+)TEV)

(CDS is underlined, TEV protease site is bold) (Figure 6 shows plasmid map)

tggcgaatgggacgcgccctgtagcggcgcattaagcgcggcgggtgtggtggttacgc
gcagcgtgaccgctacacttgccagcgccctagcgcccgctcctttcgctttcttccct
cctttctcgccacgttcgccggctttccccgtcaagctctaaatcggggggctccctttt
agggttccgatttagtgctttacggcacctcgaccccaaaaaacttgattagggtgatg
gttcacgtagtgggccatcgccctgatagacggttttccgcctttgacgttggagtcc
acgttctttaatagtggactcttgttccaaactggaacaacactcaaccctatctcggt
ctattcttttgatttataagggatttttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatattttgaaaaagccgtttctgtaa
tgaaggagaaaactcaccgaggcagttccataggatggcaagatcctggtatcggtctg
cgattccgactcgtccaacatcaatacaacctattaatttccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttcccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagttttta
ttgttcatgaccaaaatcccttaacgtgagttttcgttccactgagcgtcagacccgt
agaaaagatcaaaggatcttcttgagatcctttttttctgcgcgtaatctgctgcttgc
aaacaaaaaaaccaccgctaccagcggtggtttgtttgccggatcaagagctaccaact
cttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccaggggaaacgcctggtatcttta
tagtcctgtcgggtttcgccacctctgacttgagcgtcgatttttgtgatgctcgtcag
gggggcggagcctatggaaaaacgccagcaacgcggcctttttacggttcctggccttt
tgctggccttttgctcacatgttctttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac Figure 27B (DNA sequence of MD09-163 = pET24a-P. alba MEA(+)TEV)

```
cgaaacgcgcgaggcagctgcggtaaagctcatcagcgtggtcgtgaagcgattcacag
atgtctgcctgttcatccgcgtccagctcgttgagtttctccagaagcgttaatgtctg
gcttctgataaagcgggccatgttaagggcggttttttcctgtttggtcactgatgcct
ccgtgtaaggggatttctgttcatggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaacccccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgaagcgacaggcgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgcccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggttttttcttttcaccagtgagacgggcaacagctgattgccctt
caccgcctggccctgagagagttgcagcaagcggtccacgctggtttgcccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgcgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
acttttccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctcccttatgcgactcctgcattaggaagc
agcccagtagtaggttgaggccgttgagcaccgccgccgcaaggaatggtgcatgcaag
gagatggcgcccaacagtcccccggccacggggcctgccaccatacccacgccgaaaca
agcgctcatgagcccgaagtggcgagcccgatctcccatcggtgatgtcggcgatat
aggcgccagcaaccgcacctgtggcgccggtgatgccggccacgatgcgtccggcgtag
aggatcgagatctcgatcccgcgaaattaatacgactcactataggggaattgtgagcg
gataacaattcccctctagaaataattttgtttaactttaagaaggagatatacatatg
gaagctcgtcgttctgcgaactacgaacctaacagctgggactatgattacctgctgtc
ctccgacacggacgagtccatcgaagtatacaaagacaaagcgaaaaagctggaagccg
```

Figure 27C (DNA sequence of MD09-163 = pET24a-P. alba MEA(+)TEV)

```
aagttcgtcgcgagattaataacgaaaaagcagaatttctgaccctgctggaactgatt
gacaacgtccagcgcctgggcctgggttaccgtttcgagtctgatatccgtggtgcgct
ggatcgcttcgtttcctccggcggcttcgatgcggtaaccaagacttccctgcacggta
cggcactgtctttccgtctgctgcgtcaacacggttttgaggtttctcaggaagcgttc
agcggcttcaaagaccaaaacggcaacttcctggagaacctgaaggaagatatcaaagc
tatcctgagcctgtacgaggccagcttcctggctctggaaggcgaaaacatcctggacg
aggcgaaggttttcgcaatctctcatctgaaagaactgtctgaagaaagatcggtaaa
gagctggcagaacaggtgaaccatgcactggaactgccactgcatcgccgtactcagcg
tctggaagcagtatggtctatcgaggcctaccgtaaaaaggaggacgcgaatcaggttc
tgctggagctggcaattctggattacaacatgatccagtctgtataccagcgtgatctg
cgtgaaacgtcccgttggtggcgtcgtgtgggtctggcgaccaaactgcactttgctcg
tgaccgcctgattgagagcttctactgggccgtgggtgtagcattcgaaccgcaatact
ccgactgccgtaactccgtcgcaaaaatgttttctttcgtaaccattatcgacgatatc
tacgatgtatacggcaccctggacgaactggagctgtttactgatgcagttgagcgttg
ggacgtaaacgccatcaacgacctgccggattacatgaaactgtgctttctggctctgt
ataacactattaacgaaatcgcctacgacaacctgaaagataaaggtgagaacatcctg
ccgtatctgaccaaagcctgggctgacctgtgcaacgctttcctgcaagaagccaagtg
gctgtacaacaaatctactccgacctttgacgactacttcggcaacgcatggaaatcct
cttctggcccgctgcaactggtgttcgcttacttcgctgtcgtgcagaacattaaaaag
gaagagatcgaaaacctgcaaaaataccatgacaccatctctcgtccttcccatatctt
ccgtctgtgcaatgacctggctagcgcgtctgcggaaattgcgcgtggtgaaaccgcaa
atagcgtttcttgttacatgcgcactaaaggtatctccgaagaactggctaccgaaagc
gtgatgaatctgatcgatgaaacctggaaaagatgaacaaggaaaaactgggtggtag
cctgttcgcgaaaccgttcgtggaaccgcgatcaacctggcacgtcaatctcactgca
cttatcataacggcgacgcgcatacctctccggatgagctgaccgcaaacgcgttctg
tctgtaatcactgaaccgattctgccgtttgaacgcgaaaacctgtatttttcagggcct
cgagcaccaccaccaccaccactgagatccggctgctaacaaagcccgaaaggaagctg
agttggctgctgccaccgctgagcaataactagcataacccttggggcctctaaacgg
gtcttgaggggttttttgctgaaaggaggaactatatccggat
```

Figure 28 (Amino Acid Sequence of P. alba FL (+) TEV (in MD09-161))

MRCSVSTENVSFTETETEARRSANYEPNSWDYDYLLSSDTDESIEVYKDKAKKLEAEVR
REINNEKAEFLTLLELIDNVQRLGLGYRFESDIRGALDRFVSSGGFDAVTKTSLHGTAL
SFRLLRQHGFEVSQEAFSGFKDQNGNFLENLKEDIKAILSLYEASFLALEGENILDEAK
VFAISHLKELSEEKIGKELAEQVNHALELPLHRRTQRLEAVWSIEAYRKKEDANQVLLE
LAILDYNMIQSVYQRDLRETSRWWRRVGLATKLHFARDRLIESFYWAVGVAFEPQYSDC
RNSVAKMFSFVTIIDDIYDVYGTLDELELFTDAVERWDVNAINDLPDYMKLCFLALYNT
INEIAYDNLKDKGENILPYLTKAWADLCNAFLQEAKWLYNKSTPTFDDYFGNAWKSSSG
PLQLVFAYFAVVQNIKKEEIENLQKYHDTISRPSHIFRLCNDLASASAEIARGETANSV
SCYMRTKGISEELATESVMNLIDETWKKMNKEKLGGSLFAKPFVETAINLARQSHCTYH
NGDAHTSPDELTRKRVLSVITEPILPFERENLYFQGLEHHHHHH

Figure 29A (DNA sequence of MD09-161 = pET24a-P. alba FL(+)TEV)

(CDS is underlined, TEV protease site is bold) (Figure 6 shows plasmid map)

tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctcccttt
agggttccgatttagtgctttacggcacctcgaccccaaaaaacttgattagggtgatg
gttcacgtagtgggccatcgccctgatagacggttttttcgccctttgacgttggagtcc
acgttctttaatagtggactcttgttccaaactggaacaacactcaaccctatctcggt
ctattcttttgatttataaggggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatattttgaaaaagccgtttctgtaa
tgaaggagaaaactcaccgaggcagttccataggatggcaagatcctggtatcggtctg
cgattccgactcgtccaacatcaatacaacctattaatttcccctcgtcaaaaataagg
ttatcaagtgagaaatcaccatgagtgacgactgaatccggtgagaatggcaaaagttt
atgcatttctttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttccccggggatcgcagtggtgagtaaccatgcatcatcaggagtacggataaaatgc
ttgatggtcggaagaggcataaattccgtcagccagtttagtctgaccatctcatctgt
aacatcattggcaacgctaccttgccatgtttcagaaacaactctggcgcatcgggct
tcccatacaatcgatagattgtcgcacctgattgcccgacattatcgcgagcccattta
tacccatataatcagcatccatgttggaatttaatcgcggcctagagcaagacgtttc
ccgttgaatatggctcataacacccccttgtattactgtttatgtaagcagacagtttta
ttgttcatgaccaaaatcccttaacgtgagttttcgttccactgagcgtcagaccccgt
agaaaagatcaaaggatcttcttgagatccttttttctgcgcgtaatctgctgcttgc
aaacaaaaaaaccaccgctaccagcggtggtttgtttgccggatcaagagctaccaact
cttttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccaggggaaacgcctggtatcttta
tagtcctgtcgggtttcgccacctctgacttgagcgtcgatttttgtgatgctcgtcag
ggggcggagcctatggaaaaacgccagcaacgcggcctttttacggttcctggccttt
tgctggccttttgctcacatgttctttcctgcgttatcccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatgtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac Figure 29B (DNA sequence of MD09-161 = pET24a-P. alba FL(+)TEV)

```
cgaaacgcgcgaggcagctgcggtaaagctcatcagcgtggtcgtgaagcgattcacag
atgtctgcctgttcatccgcgtccagctcgttgagtttctccagaagcgttaatgtctg
gcttctgataaagcgggccatgttaagggcggttttttcctgtttggtcactgatgcct
ccgtgtaaggggggatttctgttcatgggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaacccgccag
cctagccgggtcctcaacgacaggagcacgatcatgcgcacccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgccccgcgcccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccaggttggttttttcttttcaccagtgagacgggcaacagctgattgccctt
caccgcctggccctgagagagttgcagcaagcggtccacgctggtttgcccagcaggc
gaaaatcctgtttgatggtggttaacggcgggatataacatgagctgtcttcggtatcg
tcgtatcccactaccgagatatccgcaccaacgcgcagcccggactcggtaatggcgcg
cattgcgcccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
acttttcccgcgttttcgcagaaacgtggctggcctggttcaccacgcgggaaacggt
ctgataagagacaccggcatactctgcgacatcgtataacgttactggtttcacattca
ccaccctgaattgactctcttccggcgctatcatgccataccgcgaaaggttttgcgc
catcgatggtgtccgggatctcgacgctctcccttatgcgactctgcattaggaagc
agcccagtagtaggttgaggccgttgagcaccgccgccgcaaggaatggtgcatgcaag
gagatggcgcccaacagtcccccggccacggggcctgccaccatacccacgccgaaaca
agcgctcatgagcccgaagtggcgagcccgatcttccccatcggtgatgtcggcgatat
aggcgccagcaaccgcacctgtggcgccggtgatgccggccacgatgcgtccggcgtag
aggatcgagatctcgatcccgcgaaattaatacgactcactatagggaattgtgagcg
gataacaattcccctctagaaataattttgtttaactttaagaaggagatatacatatg
cgttgtagcgtgtccaccgaaaatgtgtctttcaccgaaactgaaaccgaagctcgtcg
ttctgcgaactacgaacctaacagctgggactatgattacctgctgtcctccgacacgg
```

Figure 29C (DNA sequence of MD09-161 = pET24a-P. alba FL(+)TEV)

acgagtccatcgaagtatacaaagacaaagcgaaaaagctggaagccgaagttcgtcgc
gagattaataacgaaaaagcagaatttctgaccctgctggaactgattgacaacgtcca
gcgcctgggcctgggttaccgtttcgagtctgatatccgtggtgcgctggatcgcttcg
tttcctccggcggcttcgatgcggtaaccaagacttccctgcacggtacggcactgtct
ttccgtctgctgcgtcaacacggttttgaggtttctcaggaagcgttcagcggcttcaa
agaccaaaacggcaacttcctggagaacctgaaggaagatatcaaagctatcctgagcc
tgtacgaggccagcttcctggctctggaaggcgaaaacatcctggacgaggcgaaggtt
ttcgcaatctctcatctgaaagaactgtctgaagaaagatcggtaaagagctggcaga
acaggtgaaccatgcactggaactgccactgcatcgccgtactcagcgtctggaagcag
tatggtctatcgaggcctaccgtaaaaaggaggacgcgaatcaggttctgctggagctg
gcaattctggattacaacatgatccagtctgtataccagcgtgatctgcgtgaaacgtc
ccgttggtggcgtcgtgtgggtctggcgaccaaactgcactttgctcgtgaccgcctga
ttgagagcttctactgggccgtgggtgtagcattcgaaccgcaatactccgactgccgt
aactccgtcgcaaaaatgttttctttcgtaaccattatcgacgatatctacgatgtata
cggcaccctggacgaactggagctgtttactgatgcagttgagcgttgggacgtaaacg
ccatcaacgacctgccggattacatgaaactgtgctttctggctctgtataacactatt
aacgaaatcgcctacgacaacctgaaagataaaggtgagaacatcctgccgtatctgac
caaagcctgggctgacctgtgcaacgctttcctgcaagaagccaagtggctgtacaaca
atctactccgacctttgacgactacttcggcaacgcatggaaatcctcttctggcccg
ctgcaactggtgttcgcttacttcgctgtcgtgcagaacattaaaaaggaagagatcga
aaacctgcaaaaataccatgacaccatctctcgtccttcccatatcttccgtctgtgca
atgacctggctagcgcgtctgcggaaattgcgcgtggtgaaaccgcaaatagcgtttct
tgttacatgcgcactaaaggtatctccgaagaactggctaccgaaagcgtgatgaatct
gatcgatgaaacctggaaaagatgaacaaggaaaaactgggtggtagcctgttcgcga
aaccgttcgtggaaaccgcgatcaacctggcacgtcaatctcactgcacttatcataac
ggcgacgcgcatacctctccggatgagctgaccgcaaacgcgttctgtctgtaatcac
tgaaccgattctgccgtttgaacgcgaaaacctgtatttcagggcctcgagcaccacc
accaccaccactgagatccggctgctaacaaagcccgaaaggaagctgagttggctgct
gccaccgctgagcaataactagcataaccccttggggcctctaaacgggtcttgagggg
ttttttgctgaaaggaggaactatatccggat

Figure 37

Kudzu IspS protein (SEQ ID NO:42)

MCATSSQFTQITEHNSRRSANYQPNLWNFEFLQSLENDLKVEKLEEKATK
LEEEVRCMINRVDTQPLSLLELIDDVQRLGLTYKFEKDIIKALENIVLLD
ENKKNKSDLHATALSFRLLRQHGFEVSQDVFERFKDKEGGFSGELKGDVQ
GLLSLYEASYLGFEGENLLEEARTFSITHLKNNLKEGINTKVAEQVSHAL
ELPYHQRLHRLEARWFLDKYEPKEPHHQLLLELAKLDFNMVQTLHQKELQ
DLSRWWTEMGLASKLDFVRDRLMEVYFWALGMAPDPQFGECRKAVTKMFG
LVTIIDDVYDVYGTLDELQLFTDAVERWDVNAINTLPDYMKLCFLALYNT
VNDTSYSILKEKGHNNLSYLTKSWRELCKAFLQEAKWSNNKIIPAFSKYL
ENASVSSSGVALLAPSYFSVCQQQEDISDHALRSLTDFHGLVRSSCVIFR
LCNDLATSAAELERGETTNSIISYMHENDGTSEEQAREELRKLIDAEWKK
MNRERVSDSTLLPKAFMEIAVNMARVSHCTYQYGDGLGRPDYATENRIKL
LLIDPFPINQLMYV

Figure 38

*Populus [alba v tremuloides] IspS protein* (SEQ ID NO:43)

MCSVSTENVSFTETETEARRSANYEPNSWDYDFLLSSDTDESIEVYKDKAKKLEAEVRRE
INNEKAEFLTLLELIDNVQRLGLGYRFESDIRRALDRFVSSGGFDGVTKTSLHATALSFR
LLRQHGFEVSQEAFSGFKDQNGNFLENLKEDTKAILSLYEASFLALEGENILDEARVFAI
SHLKELSEEKIGKELAEQVNHALELPLHRRTQRLEAVWSIEAYRKKEDANQVLLELAILD
YNMIQSVYQRDLRETSRWWRRVGLATKLHFAKDRLIESFYWAVGVAFEPQYSDCRNSVAK
MFSFVTIIDDIYDVYGTLDELELFTDAVERWDVNAINDLPDYMKLCFLALYNTINEIAYD
NLKDKGENILPYLTKAWADLCNAFLQEAKWLYNKSTPTFDDYFGNAWKSSSGPLQLIFAY
FAVVQNIKKEEIENLQKYHDIISRPSHIFRLCNDLASASAEIARGETANSVSCYMRTKGI
SEELATESVMNLIDETCKKMNKEKLGGSLFAKPFVETAINLARQSHCTYHNGDAHTSPDE
LTRKRVLSVITEPILPFER

Figure 40A  DNA sequence of pCL201 (IspS CDS is underlined):

```
tggcgaatgggacgcgccctgtagcggcgcattaagcgcggcgggtgtggtggttacgc
gcagcgtgaccgctacacttgccagcgccctagcgcccgctcctttcgctttcttccct
tcctttctcgccacgttcgccggctttccccgtcaagctctaaatcgggggctccctt
agggttccgatttagtgctttacggcacctcgaccccaaaaaacttgattagggtgatg
gttcacgtagtgggccatcgccctgatagacggttttttcgccttttgacgttggagtcc
acgttctttaatagtggactcttgttccaaactggaacaacactcaaccctatctcggt
ctattcttttgatttataagggattttgccgatttcggcctattggttaaaaaatgagc
tgatttaacaaaaatttaacgcgaattttaacaaaatattaacgtttacaatttcaggt
ggcacttttcggggaaatgtgcgcggaacccctatttgtttatttttctaaatacattc
aaatatgtatccgctcatgaattaattcttagaaaaactcatcgagcatcaaatgaaac
tgcaatttattcatatcaggattatcaataccatattttgaaaaagccgtttctgtaa
tgaaggagaaaactcaccgaggcagttccataggatggcaagatcctggtatcggtctg
cgattccgactcgtccaacatcaatacaacctattaatttccctcgtcaaaaataagg
ttatcaagtgagaaatcaccatgagtgacgactgaatccggtgagaatggcaaaagttt
atgcatttcttccagacttgttcaacaggccagccattacgctcgtcatcaaaatcac
tcgcatcaaccaaaccgttattcattcgtgattgcgcctgagcgagacgaaatacgcga
tcgctgttaaaaggacaattacaaacaggaatcgaatgcaaccggcgcaggaacactgc
cagcgcatcaacaatattttcacctgaatcaggatattcttctaatacctggaatgctg
ttttccggggatcgcagtggtgagtaaccatgcatcatcaggagtacggataaaatgc
ttgatggtcggaagaggcataaattccgtcagccagtttagtctgaccatctcatctgt
aacatcattggcaacgctacctttgccatgtttcagaaacaactctggcgcatcgggct
tcccatacaatcgatagattgtcgcacctgattgcccgacattatcgcgagcccattta
tacccatataaatcagcatccatgttggaatttaatcgcggcctagagcaagacgtttc
ccgttgaatatggctcataacaccccttgtattactgtttatgtaagcagacagtttta
ttgttcatgaccaaaatcccttaacgtgagttttcgttccactgagcgtcagaccccgt
agaaaagatcaaaggatcttcttgagatcctttttttctgcgcgtaatctgctgcttgc
aaacaaaaaaaccaccgctaccagcggtggtttgtttgccggatcaagagctaccaact
cttttccgaaggtaactggcttcagcagagcgcagataccaaatactgtccttctagt
gtagccgtagttaggccaccacttcaagaactctgtagcaccgcctacatacctcgctc
tgctaatcctgttaccagtggctgctgccagtggcgataagtcgtgtcttaccgggttg
gactcaagacgatagttaccggataaggcgcagcggtcgggctgaacggggggttcgtg
cacacagcccagcttggagcgaacgacctacaccgaactgagatacctacagcgtgagc
tatgagaaagcgccacgcttcccgaagggagaaaggcggacaggtatccggtaagcggc
agggtcggaacaggagagcgcacgagggagcttccaggggaaacgcctggtatcttta
tagtcctgtcgggtttcgccacctctgacttgagcgtcgatttttgtgatgctcgtcag
gggggcggagcctatggaaaaacgccagcaacgcggcctttttacggttcctggccttt
tgctggccttttgctcacatgttctttcctgcgttatccctgattctgtggataaccg
tattaccgcctttgagtgagctgataccgctcgccgcagccgaacgaccgagcgcagcg
agtcagtgagcgaggaagcggaagagcgcctgatgcggtattttctccttacgcatctg
tgcggtatttcacaccgcatatatggtgcactctcagtacaatctgctctgatgccgca
tagttaagccagtatacactccgctatcgctacgtgactgggtcatggctgcgccccga
cacccgccaacacccgctgacgcgccctgacgggcttgtctgctcccggcatccgctta
cagacaagctgtgaccgtctccgggagctgcatgtgtcagaggttttcaccgtcatcac
cgaaacgcgcgaggcagctgcggtaaagctcatcagcgtggtcgtgaagcgattcacag
```

Figure 40B

```
atgtctgcctgttcatccgcgtccagctcgttgagtttctccagaagcgttaatgtctg
gcttctgataaagcgggccatgttaagggcggttttttcctgtttggtcactgatgcct
ccgtgtaaggggatttctgttcatggggtaatgataccgatgaaacgagagaggatg
ctcacgatacgggttactgatgatgaacatgcccggttactggaacgttgtgagggtaa
acaactggcggtatggatgcggcgggaccagagaaaaatcactcagggtcaatgccagc
gcttcgttaatacagatgtaggtgttccacagggtagccagcagcatcctgcgatgcag
atccggaacataatggtgcagggcgctgacttccgcgtttccagactttacgaaacacg
gaaaccgaagaccattcatgttgttgctcaggtcgcagacgttttgcagcagcagtcgc
ttcacgttcgctcgcgtatcggtgattcattctgctaaccagtaaggcaacccgccag
cctagccgggtcctcaacgacaggagcacgatcatgcgcaccgtggggccgccatgcc
ggcgataatggcctgcttctcgccgaaacgtttggtggcgggaccagtgacgaaggctt
gagcgagggcgtgcaagattccgaataccgcaagcgacaggccgatcatcgtcgcgctc
cagcgaaagcggtcctcgccgaaaatgacccagagcgctgccggcacctgtcctacgag
ttgcatgataaagaagacagtcataagtgcggcgacgatagtcatgcccgcgccacc
ggaaggagctgactgggttgaaggctctcaagggcatcggtcgagatcccggtgcctaa
tgagtgagctaacttacattaattgcgttgcgctcactgcccgctttccagtcgggaaa
cctgtcgtgccagctgcattaatgaatcggccaacgcgcggggagaggcggtttgcgta
ttgggcgccagggtggttttcttttcaccagtgagacgggcaacagctgattgccctt
caccgcctggccctgagagagttgcagcaagcggtccacgctggtttgcccagcaggc
gaaaatcctgtttgatggtggttaacggcgggatataacatgagctgtcttcggtatcg
tcgtatcccactaccgagatatccgcaccaacgcgcagccggactcggtaatggcgcg
cattgcgccagcgccatctgatcgttggcaaccagcatcgcagtgggaacgatgccct
cattcagcatttgcatggtttgttgaaaaccggacatggcactccagtcgccttcccgt
tccgctatcggctgaatttgattgcgagtgagatatttatgccagccagccagacgcag
acgcgccgagacagaacttaatgggcccgctaacagcgcgatttgctggtgacccaatg
cgaccagatgctccacgcccagtcgcgtaccgtcttcatgggagaaaataatactgttg
atgggtgtctggtcagagacatcaagaaataacgccggaacattagtgcaggcagcttc
cacagcaatggcatcctggtcatccagcggatagttaatgatcagcccactgacgcgtt
gcgcgagaagattgtgcaccgccgctttacaggcttcgacgccgcttcgttctaccatc
gacaccaccacgctggcacccagttgatcggcgcgagatttaatcgccgcgacaatttg
cgacggcgcgtgcagggccagactggaggtggcaacgccaatcagcaacgactgtttgc
ccgccagttgttgtgccacgcggttgggaatgtaattcagctccgccatcgccgcttcc
acttttcccgcgttttcgcagaaacgtggctggcctggttcaccacgcgggaaacggt
ctgataagagacaccggcatactctgcgacatcgtataacgttactggtttcacattca
ccaccctgaattgactctcttccgggcgctatcatgccataccgcgaaaggttttgcgc
cattcgatggtgtccgggatctcgacgctctccttatgcgactcctgcattaggaagc
agcccagtagtaggttgaggccgttgagcaccgccgccgcaaggaatggtgcatgcaag
gagatggcgccaacagtccccggccacggggcctgccaccatacccacgccgaaaca
agcgctcatgagcccgaagtggcgagcccgatcttcccatcggtgatgtcggcgatat
aggcgccagcaaccgcacctgtggcgccggtgatgccggccacgatgcgtccggcgtag
aggatcgagatctcgatcccgcgaaattaatacgactcactataggggaattgtgagcg
gataacaattcccctctagaaataattttgtttaactttaagaaggagatatacatatg
gaagcacgtcgctctgcgaactacgaacctaacagctgggactatgattacctgctgtc
ctccgacacggacgagtccatcgaagtatacaaagacaaagcgaaaaagctggaagccg
aagttcgtcgcgagattaataacgaaaaagcagaatttctgaccctgctggaactgatt
```

Figure 40C

```
gacaacgtccagcgcctgggcctgggttaccgtttcgagtctgatatccgtggtgcgct
ggatcgcttcgtttcctccggcggcttcgatgcggtaaccaagacttcctgcacggta
cggcactgtctttccgtctgctgcgtcaacacggttttgaggtttctcaggaagcgttc
agcggcttcaaagaccaaaacggcaacttcctggagaacctgaaggaagatatcaaagc
tatcctgagcctgtacgaggccagcttcctggctctggaaggcgaaaacatcctggacg
aggcgaaggttttcgcaatctctcatctgaaagaactgtctgaagaaagatcggtaaa
gagctggcagaacaggtgaaccatgcactggaactgccactgcatcgccgtactcagcg
tctggaagcagtatggtctatcgaggcctaccgtaaaaaggaggacgcgaatcaggttc
tgctggagctggcaattctggattacaacatgatccagtctgtataccagcgtgatctg
cgtgaaacgtcccgttggtggcgtcgtgtgggtctggcgaccaaactgcactttgctcg
tgaccgcctgattgagagcttctactgggccgtgggtgtagcattcgaaccgcaatact
ccgactgccgtaactccgtcgcaaaaatgttttctttcgtaaccattatcgacgatatc
tacgatgtatacggcaccctggacgaactggagctgttactgatgcagttgagcgttg
ggacgtaaacgccatcaacgacctgccggattacatgaaactgtgctttctggctctgt
ataacactattaacgaaatcgcctacgacaacctgaaagataaaggtgagaacatcctg
ccgtatctgaccaaagcctgggctgacctgtgcaacgctttcctgcaagaagccaagtg
gctgtacaacaaatctactccgacctttgacgactacttcggcaacgcatggaaatcct
cttctggccgctgcaactggtgttcgcttacttcgctgtcgtgcagaacattaaaaag
gaagagatcgaaaacctgcaaaaataccatgacaccatctctcgtccttcccatatctt
ccgtctgtgcaatgacctggctagcgcgtctgcggaaattgcgcgtggtgaaaccgcaa
atagcgtttcttgttacatgcgcactaaaggtatctccgaagaactggctaccgaaagc
gtgatgaatctgatcgatgaaacctggaaaaagatgaacaaggaaaaactgggtggtag
cctgttcgcgaaaccgttcgtggaaccgcgatcaacctggcacgtcaatctcactgca
cttatcataacggcgacgcgcataccctccggatgagctgaccgcaaacgcgttctg
tctgtaatcactgaaccgattctgccgtttgaacgctaaggatccgaattcgagctccg
tcgacaagcttgcggccgcactcgagcaccaccaccaccaccactgagatccggctgct
aacaaagcccgaaaggaagctgagttggctgctgccaccgctgagcaataactagcata
accccttggggcctctaaacgggtcttgaggggttttttgctgaaggaggaactatat
ccggat
```

Figure 41. Amino Acid Sequence of P. alba IspS (residues 1 through 544):

MEARRSANYEPNSWDYDYLLSSDTDESIEVYKDKAKKLEAEVRREINNEKAEFLTLLELI
DNVQRLGLGYRFESDIRGALDRFVSSGGFDAVTKTSLHGTALSFRLLRQHGFEVSQEAFS
GFKDQNGNFLENLKEDIKAILSLYEASFLALEGENILDEAKVFAISHLKELSEEKIGKEL
AEQVNHALELPLHRRTQRLEAVWSIEAYRKKEDANQVLLELAILDYNMIQSVYQRDLRET
SRWWRRVGLATKLHFARDRLIESFYWAVGVAFEPQYSDCRNSVAKMFSFVTIIDDIYDVY
GTLDELELFTDAVERWDVNAINDLPDYMKLCFLALYNTINEIAYDNLKDKGENILPYLTK
AWADLCNAFLQEAKWLYNKSTPTFDDYFGNAWKSSSGPLQLVFAYFAVVQNIKKEEIENL
QKYHDTISRPSHIFRLCNDLASASAEIARGETANSVSCYMRTKGISEELATESVMNLIDE
TWKKMNKEKLGGSLFAKPFVETAINLARQSHCTYHNGDAHTSPDELTRKRVLSVITEPIL
PFER

Figure 45

|   | 1 | 2 | 3 | 4 | 5 | 6 | 7 | 8 | 9 | 10 | 11 | 12 |
|---|---|---|---|---|---|---|---|---|---|----|----|----|
| A | A | C | D | E | F | G | H | I | K | L | 1 wt | Vector only |
| B | M | N | P | Q | R | S | T | V | W | Y | 1 wt | Vector only |
| C | A | C | D | E | F | G | H | I | K | L | 2 wt | Vector only |
| D | M | N | P | Q | R | S | T | V | W | Y | 2 wt | Vector only |
| E | A | C | D | E | F | G | H | I | K | L | 3 wt | Vector only |
| F | M | N | P | Q | R | S | T | V | W | Y | 3 wt | Vector only |
| G | A | C | D | E | F | G | H | I | K | L | 4 wt | Vector only |
| H | M | N | P | Q | R | S | T | V | W | Y | 4 wt | Vector only |

Position 1
Position 2
Position 3
Position 4

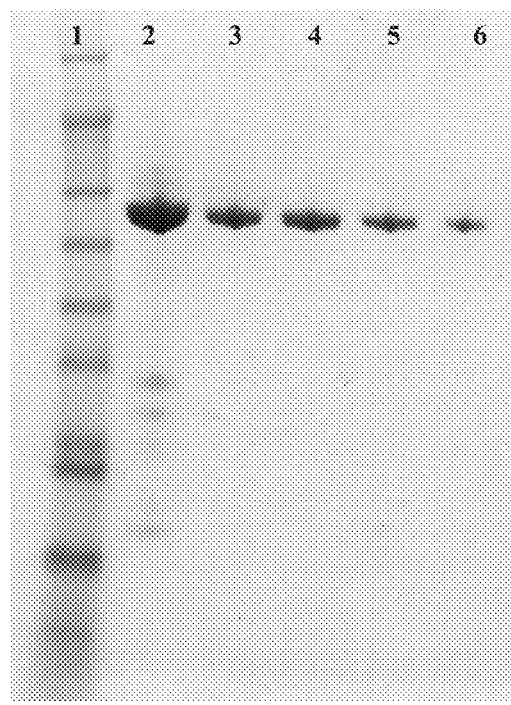
Figure 51. SDS-PAGE gel showing IspS-L494P at different stages of the purification. Lane 1- molecular weight standard; Lane 2- IspS-L494P prior to treatment with TurboTEV; Lane 3- IspS-L494P treated with TurboTEV; Lanes 4-6- IspS-L494P after final buffer exchange at different dilution levels.

Figure 52: $2F_O-2F_C$ electron density map at residue 494 contoured at 1-sigma. Panel A shows 494L, Panel B shows 494P.
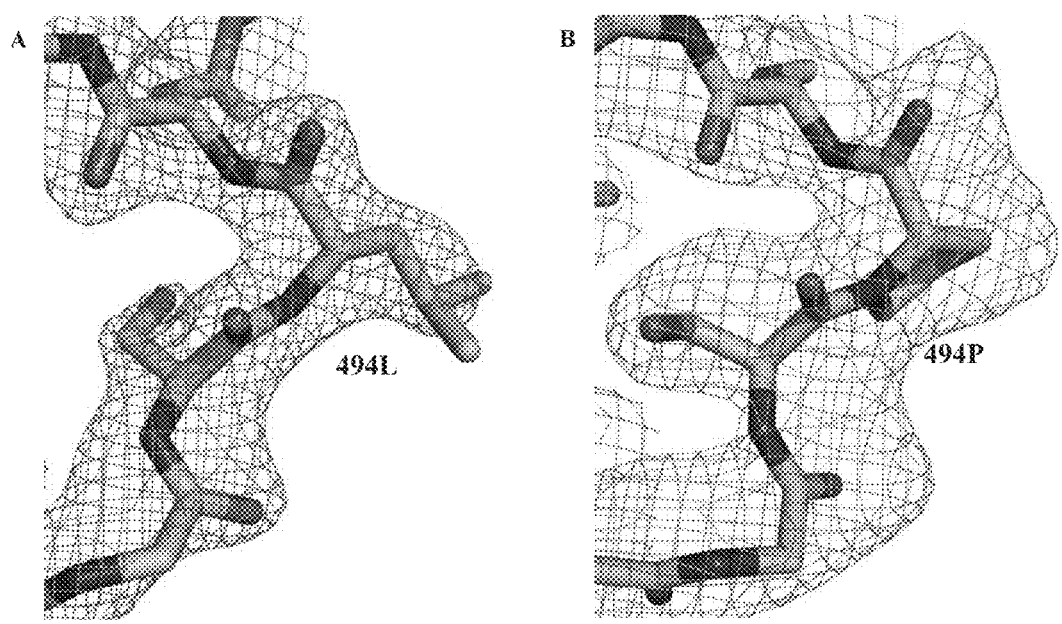

Figure 53: Alignment of the loop containing residue 494. Wild type IspS is light grey and IspS-L494P is dark grey. The L494P mutation results in an alternate loop structure.
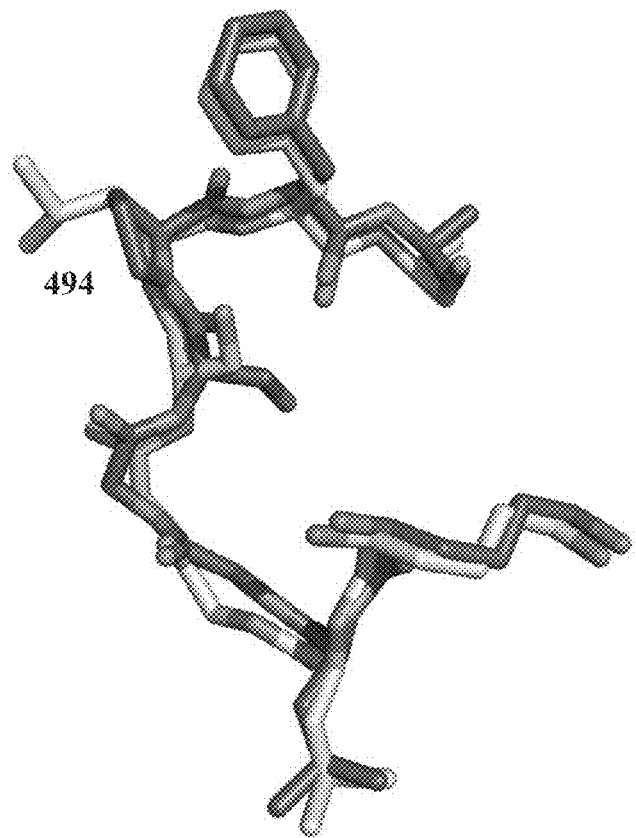

Figure 54: SDS-PAGE gel showing purified IspS-T536F at different dilutions (lanes 2-4) and molecular weight standard (lane 1).
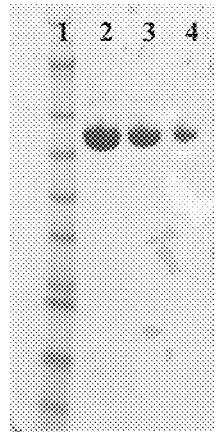
Figure 55: SDS-PAGE gel showing total cell lysate (lanes 2, 5, 8), supernatant (lanes 3, 6, 9), and purified protein (lanes 4, 7, 10) for wild type IspS, IspS-L494P and IspS-T536F, respectively. A molecular weight marker is in lane 1.
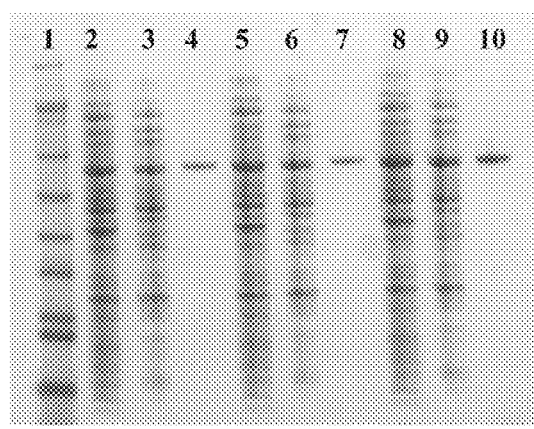

Figure 56: Thermal unfolding curves for wild type IspS, IspS-L494P, and IspS-T536F incubated with buffer only. $T_M$ values are indicated for each variant.
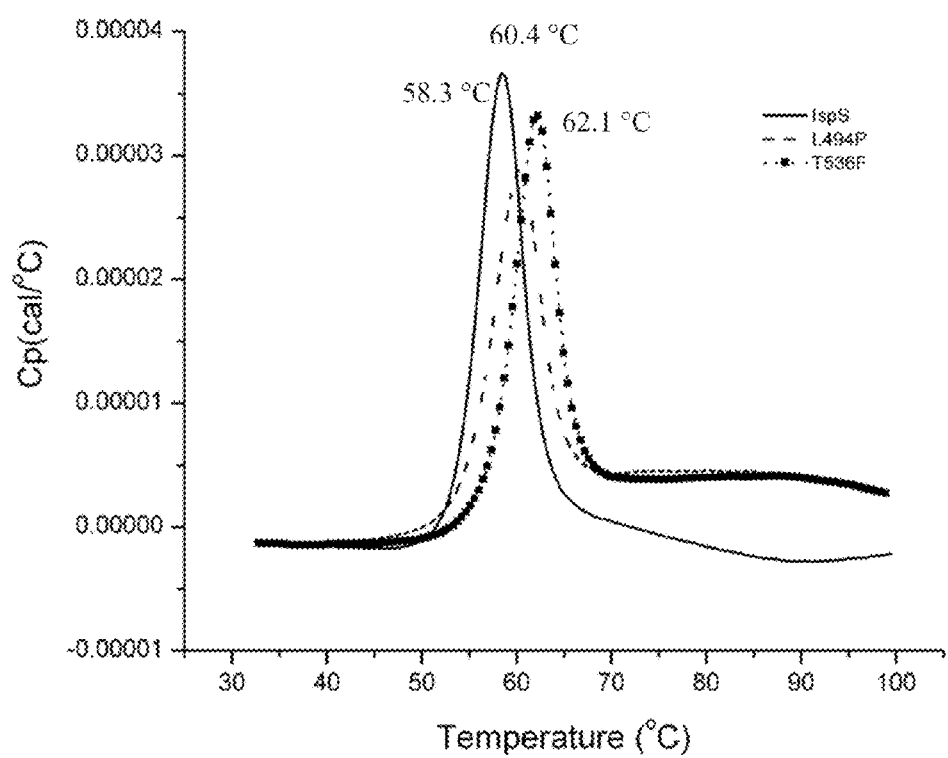

Figure 57: Thermal unfolding curves for wild type IspS, IspS-L494P, and IspS-T536F incubated with 5 mM sodium pyrophosphate. $T_M$ values are indicated for each variant.
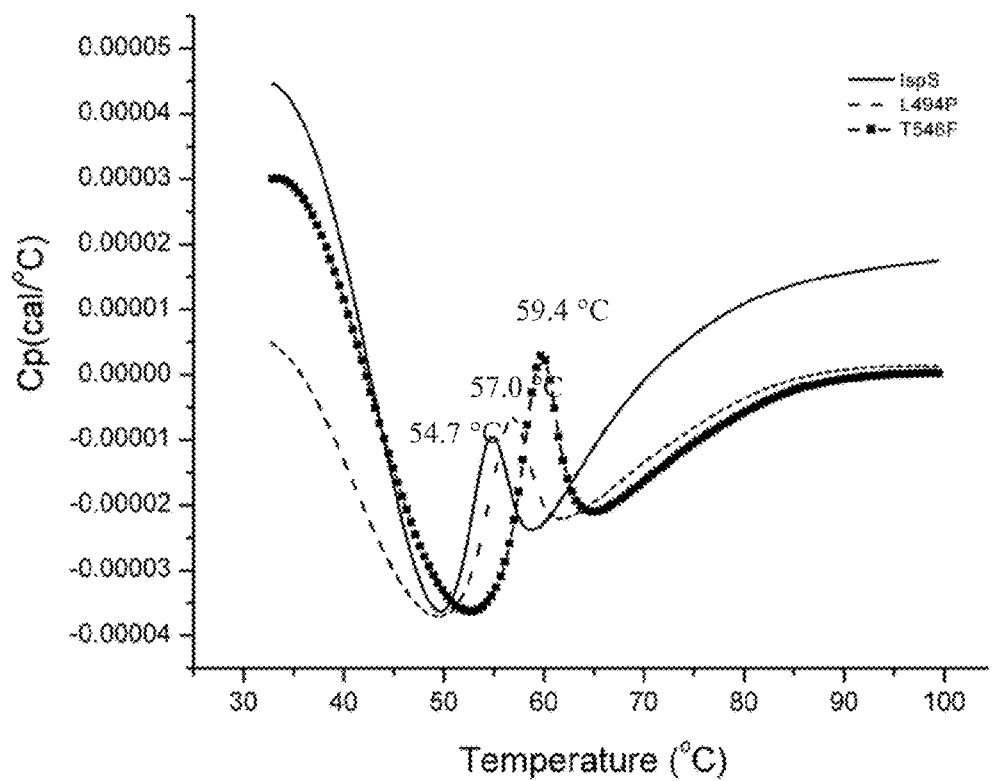

Figure 58: Temperature activity ration curves for wild type IspS (WT), IspS-L494P (LP), and IspS-T536F (TF). Data are plotted as a ratio of the specific activity (nmol/mg/min) of the protein at a given temperature divided by the specific activity at 35 °C.
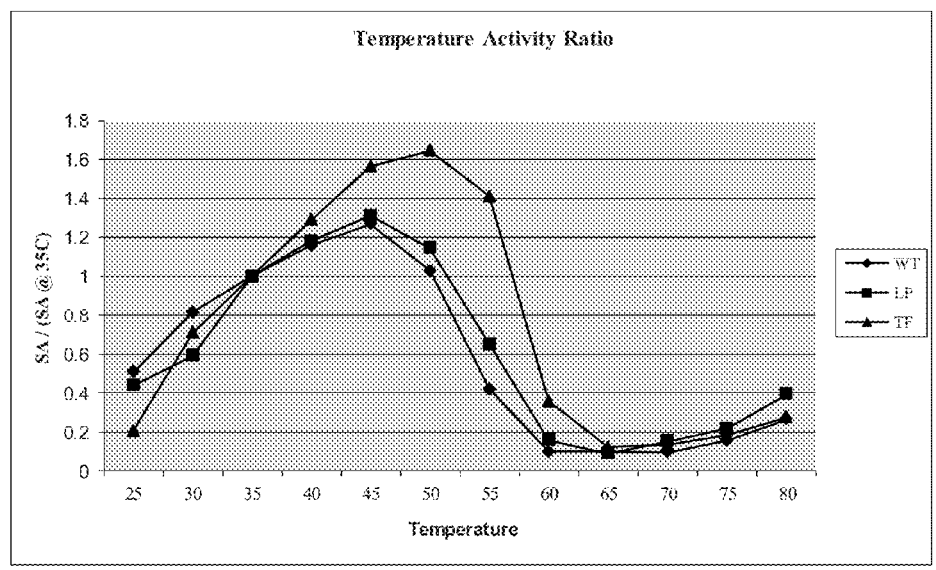

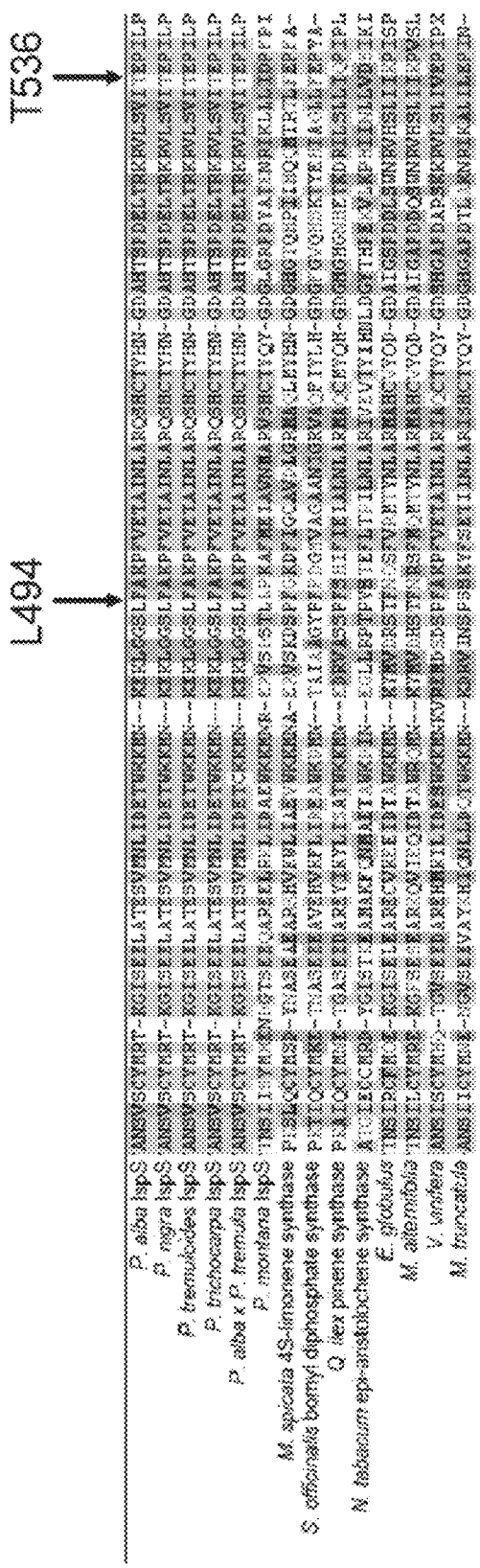
Figure 59: Local alignment of P. alba isoprene synthase and related terpene synthase enzymes Figure 60: Map of plasmid MD09-163 with A453N, G491S, L494P, and T536C/F Mutations
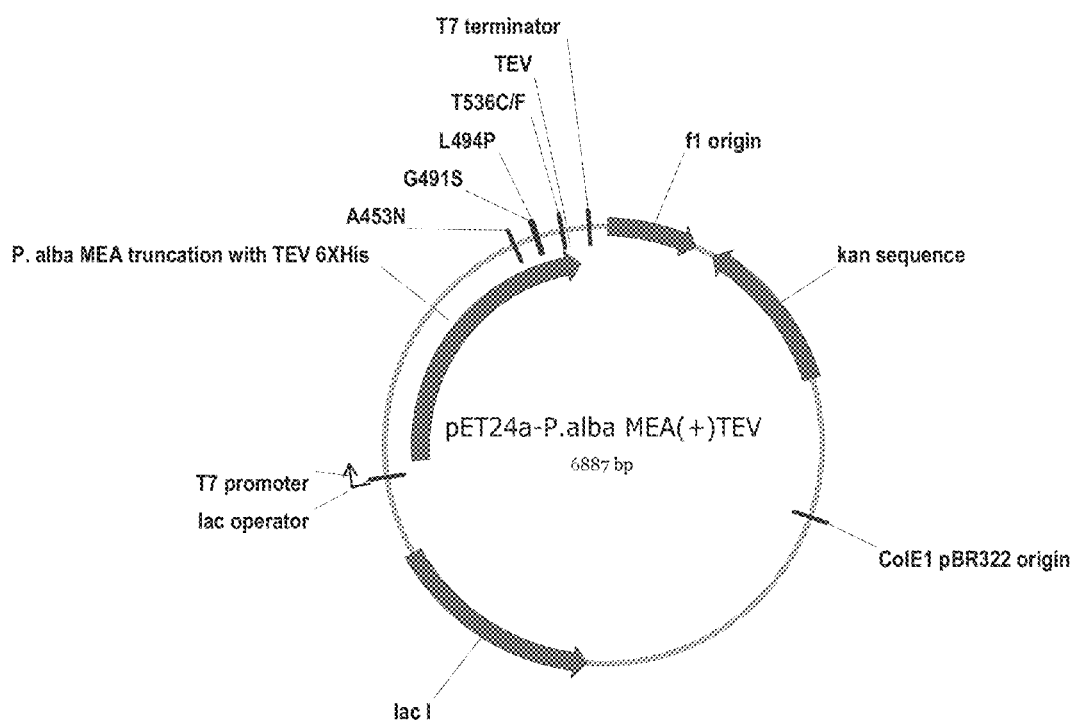

Figure 61: Dilution Series of Isoprene Synthases Assayed for Rate vs. [DMAPP]
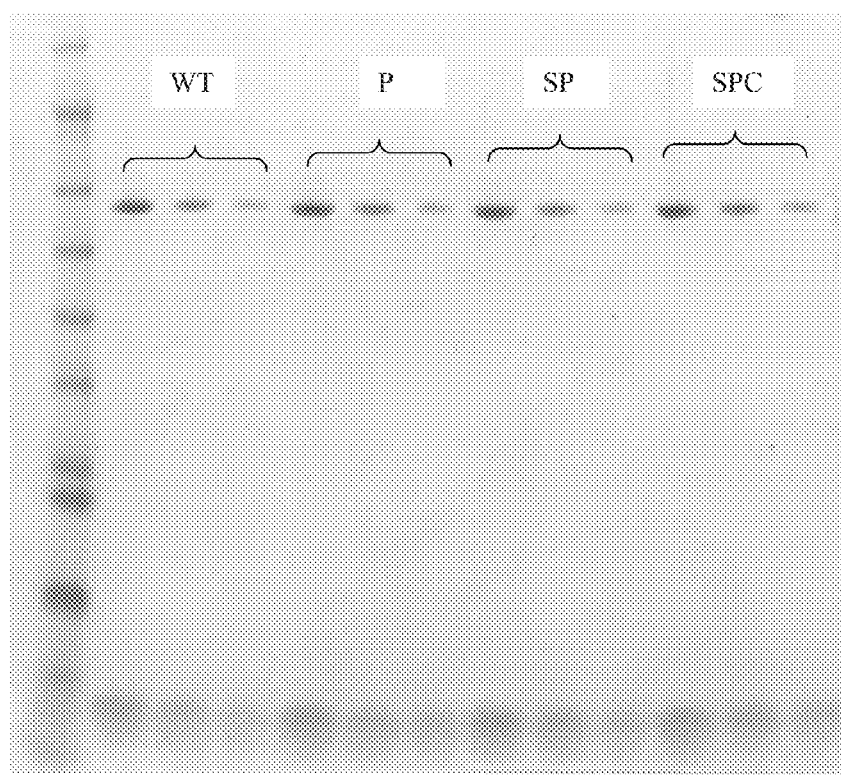

Figure 62: Specific activity of each variant with 4 mM DMAPP assayed at 30°C. The black bar indicates the specific activity of the WT isoprene synthase.
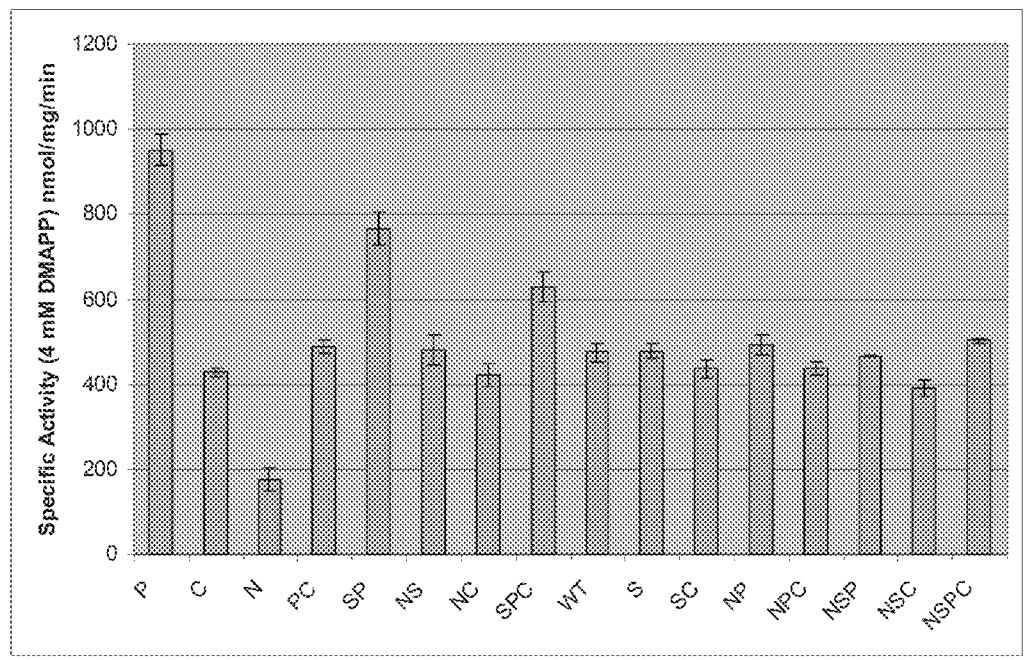

Figure 63: Rate vs. [DMAPP] for the P, SP and SPC variants of isoprene synthase and WT isoprene synthase. Each data point on the graph is the average of three independently performed kinetic assays. Error bars are reported as one standard deviation above and below the data point.
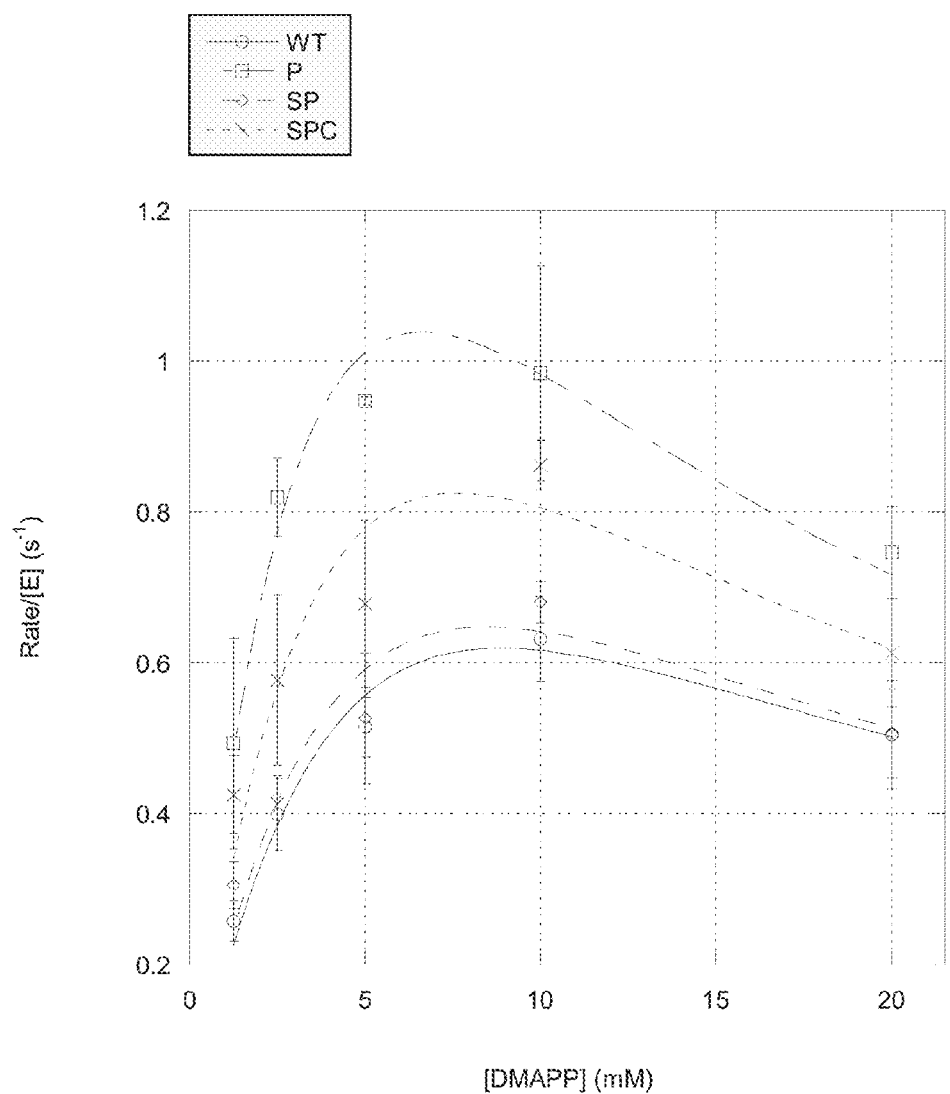

Figure 64: Alignment of the *P. tremuloides* (black) and *P. alba* structures (grey) showing high level of structural homology.
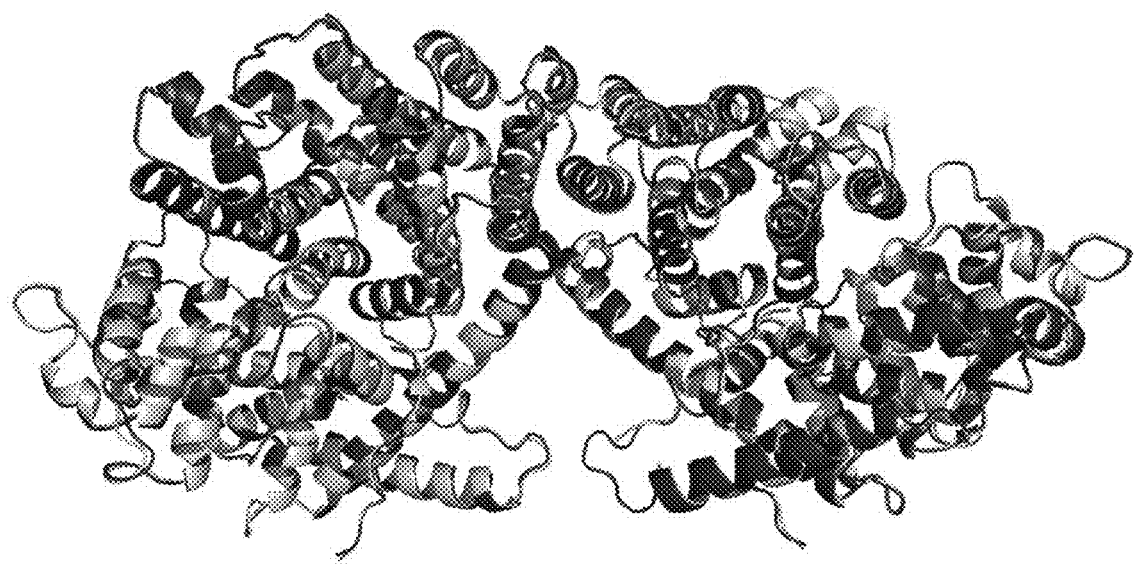

SEQUENCE LISTING

<160> NUMBER OF SEQ ID NOS: 112

<210> SEQ ID NO 1
<211> LENGTH: 4352
<212> TYPE: DNA
<213> ORGANISM: Artificial Sequence
<220> FEATURE:
<223> OTHER INFORMATION: Synthetic Construct

<400> SEQUENCE: 1

```
tagaaaaact catcgagcat caaatgaaac tgcaatttat tcatatcagg attatcaata      60
ccatatttt gaaaaagccg tttctgtaat gaaggagaaa actcaccgag gcagttccat      120
aggatggcaa gatcctggta tcggtctgcg attccgactc gtccaacatc aatacaacct     180
attaatttcc cctcgtcaaa aataaggtta tcaagtgaga atcaccatg agtgacgact      240
gaatccggtg agaatggcaa aagtttatgc atttcttcc agacttgttc aacaggccag      300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgtttttccg gggatcgcag tggtgagtaa ccatgcatca     540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
ttatcgcgag cccatttata cccatataaa tcagcatcca tgttggaatt taatcgcggc     780
ctcgacgttt cccgttgaat atggctcata ttcttccttt ttcaatatta ttgaagcatt     840
tatcagggtt attgtctcat gagcggatac atatttgaat gtatttagaa aaataaacaa     900
ataggggtca gtgttacaac caattaacca attctgaaca ttatcgcgag cccatttata    960
cctgaatatg gctcataaca cccttgttt gcctggcggc agtagcgcgg tggtcccacc     1020
tgacccatg ccgaactcag aagtgaaacg ccgtagcgcc gatggtagtg tggggactcc     1080
ccatgcgaga gtagggaact gccaggcatc aaataaaacg aaaggctcag tcgaaagact     1140
gggcctttcg cccgggctaa ttaggggtg tcgcccttc gattgacgct gcagttagac      1200
atacatcagc tggttaatcg ggaaagggtc aatcagcagc agtttgatgc ggttttcagt    1260
cgcgtagtct gggcgaccca gaccatcgcc atactggtag gtgcagtggg aaacacgtgc    1320
catgttaact gcgatttcca tgaacgcttt aggcagcagg gtggagtcgc taacgcgttc    1380
acgattcatc ttttccatt cggcgtcgat cagtttacgc agttcttcgc gggcctgttc     1440
ctcgctggta ccatcgtttt cgtgcatgta gctaatgata gaattggtag tctcgccacg    1500
ttccagctcc gccgcagagg tggccagatc gttgcacagg cggaagataa cgcagctaga    1560
acgcaccaga ccatggaagt cggtcaggga acgcagcgcg tggtcggaga tgtcttcctg    1620
ctgctggcat acggaaaagt aagacggcgc cagcagcgct acaccggagg aggaaacgct    1680
ggcgttttcc aggtacttgg agaaagccgg gataattttg ttgttggacc atttcgcctc    1740
ttgcagaaag gctttgcaca gttcacgcca gcttttcgtc agataggaca ggttgttatg    1800
accttctct ttcagaatag aataggacgt gtcgttaacg gtgttgtaca gtgccaggaa     1860
acacagttc atatagtccg gcagggtgtt aatagcgtta acgtcccagc gctctacagc     1920
atcggtgaac agttgcagtt cgtccagagt gccataaacg tcatacacgt catcgatgat    1980
cgtcaccaga ccaaacattt tagtaacagc tttgcgacat tcaccaaact gcgggtctgg    2040
cgccataccc agtgcccaga ataaacttc catcaggcgg tcgcgtacaa aatccagttt     2100
gctagccagg cccatctcgg tccaccagcg ggacagatct tgcagctctt tctggtgcag    2160
ggtctgtacc atgttaaaat ccagcttcgc cagctccagc agcagctggt gatgcggttc     2220
tttcggttcg tatttatcca ggaaccaacg tgcctccaga cggtgcagac gctggtgata    2280
tggcagttcc agggcgtggc tcacttgttc tgcaaccttg gtattaatgc cttctttcag    2340
gttgttcttc aggtgggtga tggaaaaggt acgcgcctcc tccagcaggt tctcaccctc    2400
```

```
gaaacccagg taagacgctt catacaggct cagcaggcct tggacgtcac ctttcagttc    2460
accgctgaaa ccaccttctt tatccttgaa acgctcaaaa acatcctgag aaacctcgaa    2520
accgtgctga cgcagcagac ggaaagacag agcggttgcg tgcaggtcag atttgttctt    2580
tttgttttcg tccagcagta cgatgttttc cagggcttta atgatgtctt tttcaaattt    2640
gtaggtcaga cccaggcgct gcacatcgtc gatcagctcc agcagggaca gcggctgggt    2700
gtctacacgg ttgatcatgc agcgaacttc ttcctccagt ttggtcgctt tctcctccag    2760
cttttccact ttcaggtcgt tctccaggga ttgcaggaat tcgaaattcc acaggtttgg    2820
ctgatagttt gcggaacgac gggaattatg ctcggtaatc tgagtaaatt gagaagaggt    2880
cgcacacatg ttcagcgaca agggcgacac aaaatttatt ctaaatgcat aataaatact    2940
gataacatct tatagtttgt attatatttt gtattatcgt tgacatgtat aattttgata    3000
tcaaaaactg attttcccct tattattttc gagatttatt ttcttaattc tctttaacaa    3060
actagaaata ttgtatatac aaaaaatcat aaataataga tgaatagttt aattataggt    3120
gttcatcaat cgaaaaagca acgtatctta tttaaagtgc gttgcttttt tctcatttat    3180
aaggttaaat aattctcata tatcaagcaa agtgacaggc gcccttaaat attctgacaa    3240
atgctctttc cctaaactcc ccccataaaa aaacccgccg aagcgggttt ttacgttatt    3300
tgcggattaa cgattactcg ttatcagaac cgcccagggg gcccgagctt aagactggcc    3360
gtcgttttac aacacagaaa gagtttgtag aaacgcaaaa aggccatccg tcagggcct    3420 tctgcttagt ttgatgcctg gcagttccct actctcgcct tccgcttcct cgctcactga    3480
ctcgctgcgc tcggtcgttc ggctgcggcg agcggtatca gctcactcaa aggcggtaat    3540
acggttatcc acagaatcag gggataacgc aggaaagaac atgtgagcaa aaggccagca    3600
aaaggccagg aaccgtaaaa aggccgcgtt gctggcgttt ttccataggc tccgcccccc    3660
tgacgagcat cacaaaaatc gacgctcaag tcagaggtgg cgaaacccga caggactata    3720
aagataccag gcgtttcccc ctggaagctc cctcgtgcgc tctcctgttc cgaccctgcc    3780
gcttaccgga tacctgtccg cctttctccc ttcgggaagc gtggcgcttt ctcatagctc    3840
acgctgtagg tatctcagtt cggtgtaggt cgttcgctcc aagctgggct gtgtgcacga    3900
accccccgtt cagcccgacc gctgcgcctt atccggtaac tatcgtcttg agtccaaccc    3960
ggtaagacac gacttatcgc cactggcagc agccactggt aacaggatta gcagagcgag    4020
gtatgtaggc ggtgctacag agttcttgaa gtggtggcct aactacggct acactagaag    4080
aacagtattt ggtatctgcg ctctgctgaa gccagttacc ttcggaaaaa gagttggtag    4140
ctcttgatcc ggcaaacaaa ccaccgctgg tagcggtggt ttttttgttt gcaagcagca    4200
gattacgcgc agaaaaaaag gatctcaaga agatcctttg atcttttcta cggggtctga    4260
cgctcagtgg aacgacgcgc gcgtaactca cgttaaggga ttttggtcat gagcttgcgc    4320
cgtcccgtca gtcagcgta atgctctgct tt    4352
```

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2

```
gtttgacagc ttatcatcga ctgcacggtg caccaatgct tctggcgtca ggcagccatc    60
```

-continued

| | |
|---|---|
| ggaagctgtg gtatggctgt gcaggtcgta aatcactgca taattcgtgt cgctcaaggc | 120 |
| gcactcccgt tctggataat gtttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatgtgtgc | 420 |
| gacctcttct caatttactc agattaccga gcataattcc cgtcgttccg caaactatca | 480 |
| gccaaacctg tggaatttcg aattcctgca atccctggag aacgacctga agtggaaaa | 540 |
| gctggaggag aaagcgacca aactggagga agaagttcgc tgcatgatca accgtgtaga | 600 |
| cacccagccg ctgtccctgc tggagctgat cgacgatgtg cagcgcctgg gtctgaccta | 660 |
| caaatttgaa aaagacatca ttaaagccct ggaaaacatc gtactgctgg acgaaaacaa | 720 |
| aaagaacaaa tctgacctgc acgcaaccgc tctgtctttc cgtctgctgc gtcagcacgg | 780 |
| tttcgaggtt tctcaggatg ttttttgagcg tttcaaggat aaagaaggtg gtttcagcgg | 840 |
| tgaactgaaa ggtgacgtcc aaggcctgct gagcctgtat gaagcgtctt acctgggttt | 900 |
| cgagggtgag aacctgctgg aggaggcgcg taccttttcc atcacccacc tgaagaacaa | 960 |
| cctgaaagaa ggcattaata ccaaggttgc agaacaagtg agccacgccc tggaactgcc | 1020 |
| atatcaccag cgtctgcacc gtctggaggc acgttggttc ctggataaat acgaaccgaa | 1080 |
| agaaccgcat caccagctgc tgctggagct ggcgaagctg gattttaaca tggtacagac | 1140 |
| cctgcaccag aaagagctgc aagatctgtc ccgctggtgg accagatggg gcctggctag | 1200 |
| caaactggat tttgtacgcg accgcctgat ggaagtttat ttctgggcac tgggtatggc | 1260 |
| gccagacccg cagtttggtg aatgtcgcaa agctgttact aaaatgtttg gtctggtgac | 1320 |
| gatcatcgat gacgtgtatg acgtttatgg cactctggac gaactgcaac tgttcaccga | 1380 |
| tgctgtagag cgctgggacg ttaacgctat taacaccctg ccggactata tgaaactgtg | 1440 |
| tttcctggca ctgtacaaca ccgttaacga cacgtcctat tctattctga agagaaagg | 1500 |
| tcataacaac ctgtcctatc tgacgaaaag ctggcgtgaa ctgtgcaaag cctttctgca | 1560 |
| agaggcgaaa tggtccaaca acaaaattat cccggctttc tccaagtacc tggaaaacgc | 1620 |
| cagcgttttcc tcctccggtg tagcgctgct ggcgccgtct tacttttccg tatgccagca | 1680 |
| gcaggaagac atctccgacc acgcgctgcg ttccctgacc gacttccatg gtctggtgcg | 1740 |
| ttctagctgc gttatcttcc gcctgtgcaa cgatctggcc acctctgcgg cggagctgga | 1800 |
| acgtggcgag actaccaatt ctatcattag ctacatgcac gaaaacgatg gtaccagcga | 1860 |
| ggaacaggcc cgcgaagaac tgcgtaaact gatcgacgcc gaatggaaaa agatgaatcg | 1920 |
| tgaacgcgtt agcgactcca ccctgctgcc taaagcgttc atggaaatcg cagttaacat | 1980 |
| ggcacgtgtt tcccactgca cctaccagta tggcgatggt ctgggtcgcc cagactacgc | 2040 |
| gactgaaaac cgcatcaaac tgctgctgat tgacccttc ccgattaacc agctgatgta | 2100 |
| tgtctaactg cagctggtac catatgggaa ttcgaagctt tctagaacaa aaactcatct | 2160 |
| cagaagagga tctgaatagc gccgtcgacc atcatcatca tcatcattga gtttaaacgg | 2220 |
| tctccagctt ggctgttttg gcggatgaga gaagattttc agcctgatac agattaaatc | 2280 |
| agaacgcaga agcggtctga taaaacagaa tttgcctggc ggcagtagcg cggtggtccc | 2340 |
| acctgacccc atgccgaact cagaagtgaa acgccgtagc gccgatggta gtgtggggtc | 2400 |
| tccccatgcg agagtaggga actgccaggc atcaaataaa acgaaaggct cagtcgaaag | 2460 |

-continued

```
actgggcctt tcgttttatc tgttgtttgt cggtgaacgc tctcctgagt aggacaaatc    2520
cgccgggagc ggatttgaac gttgcgaagc aacggcccgg agggtggcgg gcaggacgcc    2580
cgccataaac tgccaggcat caaattaagc agaaggccat cctgacggat ggccttttg     2640
cgtttctaca aactcttttt gtttattttt ctaaatacat tcaaatatgt atccgctcat    2700
gagacaataa ccctgataaa tgcttcaata atattgaaaa aggaagagta tgagtattca    2760
acatttccgt gtcgccctta ttccctttt tgcggcattt tgccttcctg ttttgctca     2820
cccagaaacg ctggtgaaag taaaagatgc tgaagatcag ttgggtgcac gagtgggtta    2880
catcgaactg gatctcaaca gcggtaagat ccttgagagt tttcgccccg aagaacgttt    2940
tccaatgatg agcacttta aagttctgct atgtggcgcg gtattatccc gtgttgacgc     3000
cgggcaagag caactcggtc gccgcataca ctattctcag aatgacttgg ttgagtactc    3060
accagtcaca gaaaagcatc ttacggatgg catgacagta agagaattat gcagtgctgc    3120
cataaccatg agtgataaca ctgcggccaa cttacttctg acaacgatcg gaggaccgaa    3180
ggagctaacc gctttttgc acaacatggg ggatcatgta actcgccttg atcgttggga    3240
accggagctg aatgaagcca taccaaacga cgagcgtgac accacgatgc ctgtagcaat    3300
ggcaacaacg ttgcgcaaac tattaactgg cgaactactt actctagctt cccggcaaca    3360
attaatagac tggatggagg cggataaagt tgcaggacca cttctgcgct cggcccttcc    3420
ggctggctgg tttattgctg ataaatctgg agccggtgag cgtgggtctc gcggtatcat    3480
tgcagcactg gggccagatg gtaagccctc ccgtatcgta gttatctaca cgacggggag    3540
tcaggcaact atggatgaac gaaatagaca gatcgctgag ataggtgcct cactgattaa    3600
gcattggtaa ctgtcagacc aagtttactc atatatactt tagattgatt taaaacttca    3660
tttttaattt aaaaggatct aggtgaagat ccttttgat aatctcatga ccaaaatccc    3720
ttaacgtgag ttttcgttcc actgagcgtc agacccgta gaaaagatca aaggatcttc    3780
ttgagatcct ttttttctgc gcgtaatctg ctgcttgcaa acaaaaaaac caccgctacc    3840
agcggtggtt tgtttgccgg atcaagagct accaactctt tttccgaagg taactggctt    3900
cagcagagcg cagataccaa atactgtcct tctagtgtag ccgtagttag gccaccactt    3960
caagaactct gtagcaccgc ctacatacct cgctctgcta atcctgttac cagtggctgc    4020
tgccagtggc gataagtcgt gtcttaccgg gttggactca agacgatagt taccggataa    4080
ggcgcagcgg tcgggctgaa cggggggttc gtgcacacag cccagcttgg agcgaacgac    4140
ctacaccgaa ctgagatacc tacagcgtga gctatgagaa agcgccacgc ttcccgaagg    4200
gagaaaggcg gacaggtatc cggtaagcgg cagggtcgga acaggagagc gcacgaggga    4260
gcttccaggg ggaaacgcct ggtatcttta tagtcctgtc gggtttcgcc acctctgact    4320
tgagcgtcga ttttgtgat gctcgtcagg ggggcggagc ctatggaaaa acgccagcaa    4380
cgcggccttt ttacggttcc tggccttttg ctggcctttt gctcacatgt tctttcctgc    4440
gttatcccct gattctgtgg ataaccgtat taccgccttt gagtgagctg ataccgctcg    4500
ccgcagccga acgaccgagc gcagcgagtc agtgagcgag gaagcggaag agcgcctgat    4560
gcggtatttt ctccttacgc atctgtgcgg tatttcacac cgcatatggt gcactctcag    4620
tacaatctgc tctgatgccg catagttaag ccagtataca ctccgctatc gctacgtgac    4680
tgggtcatgg ctgcgccccg acacccgcca acacccgctg acgcgccctg acgggcttgt    4740
ctgctcccgg catccgctta cagacaagct gtgaccgtct ccgggagctg catgtgtcag    4800
```

| aggttttcac cgtcatcacc gaaacgcgcg aggcagcaga tcaattcgcg cgcgaaggcg | 4860 |
| aagcggcatg catttacgtt gacaccatcg aatggtgcaa aacctttcgc ggtatggcat | 4920 |
| gatagcgccc ggaagagagt caattcaggg tggtgaatgt gaaaccagta acgttatacg | 4980 |
| atgtcgcaga gtatgccggt gtctcttatc agaccgtttc ccgcgtggtg aaccaggcca | 5040 |
| gccacgtttc tgcgaaaacg cgggaaaaag tggaagcggc gatggcggag ctgaattaca | 5100 |
| ttcccaaccg cgtggcacaa caactggcgg gcaaacagtc gttgctgatt ggcgttgcca | 5160 |
| cctccagtct ggccctgcac gcgccgtcgc aaattgtcgc ggcgattaaa tctcgcgccg | 5220 |
| atcaactggg tgccagcgtg gtggtgtcga tggtagaacg aagcggcgtc gaagcctgta | 5280 |
| aagcggcggt gcacaatctt ctcgcgcaac gcgtcagtgg gctgatcatt aactatccgc | 5340 |
| tggatgacca ggatgccatt gctgtggaag ctgcctgcac taatgttccg gcgttatttc | 5400 |
| ttgatgtctc tgaccagaca cccatcaaca gtattatttt ctcccatgaa gacggtacgc | 5460 |
| gactgggcgt ggagcatctg gtcgcattgg gtcaccagca atcgcgctg ttagcgggcc | 5520 |
| cattaagttc tgtctcggcg cgtctgcgtc tggctggctg gcataaatat ctcactcgca | 5580 |
| atcaaattca gccgatagcg gaacgggaag gcgactggag tgccatgtcc ggttttcaac | 5640 |
| aaaccatgca aatgctgaat gagggcatcg ttcccactgc gatgctggtt gccaacgatc | 5700 |
| agatggcgct gggcgcaatg cgcgccatta ccgagtccgg gctgcgcgtt ggtgcggata | 5760 |
| tctcggtagt gggatacgac gataccgaag acagctcatg ttatatcccg ccgtcaacca | 5820 |
| ccatcaaaca ggattttcgc ctgctggggc aaaccagcgt ggaccgcttg ctgcaactct | 5880 |
| ctcagggcca ggcggtgaag gcaatcagc tgttgcccgt ctcactggtg aaaagaaaaa | 5940 |
| ccaccctggc gcccaatacg caaaccgcct ctccccgcgc gttggccgat tcattaatgc | 6000 |
| agctggcacg acaggtttcc cgactggaaa gcgggcagtg agcgcaacgc aattaatgtg | 6060 |
| agttagcgcg aattgatctg | 6080 |

<210> SEQ ID NO 3
<211> LENGTH: 6646
<212> TYPE: DNA
<213> ORGANISM: Artificial Sequence
<220> FEATURE:
<223> OTHER INFORMATION: Synthetic Construct

<400> SEQUENCE: 3

| ccgacaccat cgaatggtgc aaaacctttc gcggtatggc atgatagcgc cggaagagag | 60 |
| gtcaattcag ggtggtgaat gtgaaaccag taacgttata cgatgtcgca gagtatgccg | 120 |
| gtgtctctta tcagaccgtt tcccgcgtgg tgaaccaggc cagccacgtt tctgcgaaaa | 180 |
| cgcgggaaaa agtggaagcg gcgatggcgg agctgaatta cattcccaac cgcgtggcac | 240 |
| aacaactggc gggcaaacag tcgttgctga ttggcgttgc cacctccagt ctggccctgc | 300 |
| acgcgccgtc gcaaattgtc gcggcgatta atctcgcgc cgatcaactg ggtgccagcg | 360 |
| tggtggtgtc gatggtagaa cgaagcggcg tcgaagcctg taaagcggcg gtgcacaatc | 420 |
| ttctcgcgca acgcgtcagt gggctgatca ttaactatcc gctggatgac caggatgcca | 480 |
| ttgctgtgga agctgcctgc actaatgttc cggcgttatt tcttgatgtc tctgaccaga | 540 |
| cacccatcaa cagtattatt ttctcccatg aagacggtac gcgactgggc gtggagcatc | 600 |
| tggtcgcatt gggtcaccag caaatcgcgc tgttagcggg cccattaagt tctgtctcgg | 660 |
| cgcgtctgcg tctggctggc tggcataaat atctcactcg caatcaaatt cagccgatag | 720 |
| cggaacggga aggcgactgg agtgccatgt ccggttttca acaaaccatg caaatgctga | 780 |

```
atgagggcat cgttcccact gcgatgctgg ttgccaacga tcagatggcg ctgggcgcaa      840
tgcgcgccat taccgagtcc gggctgcgcg ttggtgcgga tatctcggta gtgggatacg      900
acgataccga agacagctca tgttatatcc cgccgttaac caccatcaaa caggattttc      960
gcctgctggg gcaaaccagc gtggaccgct tgctgcaact ctctcagggc caggcggtga     1020
agggcaatca gctgttgccc gtctcactgg tgaaagaaa aaccaccctg cgcccaata       1080
cgcaaaccgc ctctccccgc gcgttggccg attcattaat gcagctggca cgacaggttt     1140
cccgactgga aagcgggcag tgagcgcaac gcaattaatg taagttagct cactcattag     1200
gcacaattct catgtttgac agcttatcat cgactcacg gtgcaccaat gcttctggcg     1260
tcaggcagcc atcggaagct gtggtatggc tgtgcaggtc gtaaatcact gcataattcg     1320
tgtcgctcaa ggcgcactcc cgttctggat aatgttttt gcgccgacat cataacggtt      1380
ctggcaaata ttctgaaatg agctgttgac aattaatcat cggctcgtat aatgtgtgga     1440
attgtgagcg gataacaatt tcacacagga acagccagt ccgtttaggt gttttcacga      1500
gcacttcacc aacaaggacc atagcatatg aaaatcgaag aaggtaaact ggtaatctgg     1560
attaacggcg ataaaggcta taacggtctc gctgaagtcg gtaagaaatt cgagaaagat     1620
accggaatta aagtcaccgt tgagcatccg gataaactgg aagagaaatt cccacaggtt     1680
gcggcaactg cgatggccc tgacattatc ttctgggcac acgaccgctt tggtggctac      1740
gctcaatctg gcctgttggc tgaaatcacc ccggacaaag cgttccagga caagctgtat     1800
ccgtttacct gggatgccgt acgttacaac ggcaagctga ttgcttaccc gatcgctgtt     1860
gaagcgttat cgctgattta aacaaagat ctgctgccga acccgccaaa aacctgggaa      1920
gagatcccgg cgctggataa agaactgaaa gcgaaaggta gagcgcgct gatgttcaac      1980
ctgcaagaac cgtacttcac ctggccgctg attgctgctg acggggtta tgcgttcaag      2040
tatgaaaacg gcaagtacga cattaaagac gtgggcgtgg ataacgctgg cgcgaaagcg     2100
ggtctgacct tcctggttga cctgattaaa aacaaacaca tgaatgcaga caccgattac     2160
tccatcgcag aagctgcctt taataaaggc gaaacagcga tgaccatcaa cggcccgtgg     2220
gcatggtcca acatcgacac cagcaaagtg aattatggtg taacggtact gccgaccttc     2280
aagggtcaac catccaaacc gttcgttggc gtgctgagcg caggtattaa cgccgccagt     2340
ccgaacaaag agctggcaaa agagttcctc gaaaactatc tgctgactga tgaaggtctg     2400
gaagcggtta taaagacaa accgctgggt gccgtagcgc tgaagtctta cgaggaagag     2460
ttggtgaaag atccgcggat tgccgccact atggaaaacg cccagaaagg tgaaatcatg     2520
ccgaacatcc cgcagatgtc cgctttctgg tatgccgtgc gtactgcggt gatcaacgcc     2580
gccagcggtc gtcagactgt cgatgaagcc ctgaaagacg cgcagactaa ttcgagctcg     2640
aacaacaaca caataacaa taacaacaac ctcgggatcg agggaaggat ttcagaattc       2700
ggatcctcta gagtcgacct gcaggcaagc ttggcactgg ccgtcgtttt acaacgtcgt     2760
gactgggaaa accctggcgt tacccaactt aatcgccttg cagcacatcc ccctttcgcc     2820
agctggcgta atagcgaaga ggcccgcacc gatcgccctt cccaacagtt gcgcagcctg     2880
aatggcgaat ggcagcttgg ctgttttggc ggatgagata agattttcag cctgatacag     2940
attaaatcag aacgcagaag cggtctgata aaacagaatt tgcctggcgg cagtagcgcg     3000
gtggtcccac ctgaccccat gccgaactca gaagtgaaac gccgtagcgc cgatggtagt     3060
gtggggtctc cccatgcgag agtagggaac tgccaggcat caaataaaac gaaaggctca     3120
```

```
gtcgaaagac tgggcctttc gttttatctg ttgtttgtcg gtgaacgctc tcctgagtag      3180
gacaaatccg ccgggagcgg atttgaacgt tgcgaagcaa cggcccggag ggtggcgggc      3240
aggacgcccg ccataaactg ccaggcatca aattaagcag aaggccatcc tgacggatgg      3300 ccttttttgcg tttctacaaa ctcttttttgt ttatttttct aaatacattc aaatatgtat      3360
ccgctcatga gacaataacc ctgataaatg cttcaataat attgaaaaag gaagagtatg      3420
agtattcaac atttccgtgt cgcccttatt ccctttttttg cggcattttg ccttcctgtt      3480
tttgctcacc cagaaacgct ggtgaaagta aaagatgctg aagatcagtt gggtgcacga      3540
gtgggttaca tcgaactgga tctcaacagc ggtaagatcc ttgagagttt cgccccgaa      3600 gaacgttctc caatgatgag cacttttaaa gttctgctat gtggcgcggt attatcccgt      3660
gttgacgccg ggcaagagca actcggtcgc cgcatacact attctcagaa tgacttggtt      3720
gagtactcac cagtcacaga aaagcatctt acgatggca tgacagtaag agaattatgc      3780
agtgctgcca taaccatgag tgataacact gcggccaact tacttctgac aacgatcgga      3840
ggaccgaagg agctaaccgc ttttttgcac aacatggggg atcatgtaac tcgccttgat      3900
cgttgggaac cggagctgaa tgaagccata ccaaacgacg agcgtgacac cacgatgcct      3960
gtagcaatgg caacaacgtt gcgcaaacta ttaactggcg aactacttac tctagcttcc      4020
cggcaacaat taatagactg gatggaggcg gataaagttg caggaccact tctgcgctcg      4080
gcccttccgg ctggctggtt tattgctgat aaatctggag ccggtgagcg tgggtctcgc      4140
ggtatcattg cagcactggg gccagatggt aagccctccc gtatcgtagt tatctacacg      4200
acggggagtc aggcaactat ggatgaacga atagacaga tcgctgagat aggtgcctca      4260
ctgattaagc attggtaact gtcagaccaa gtttactcat atatacttta gattgattta      4320
ccccggttga taatcagaaa agccccaaaa acaggaagat tgtataagca aatatttaaa      4380
ttgtaaacgt taatattttg ttaaaattcg cgttaaattt ttgttaaatc agctcatttt      4440
ttaaccaata ggccgaaatc ggcaaaatcc cttataaatc aaaagaatag accgagatag      4500
ggttgagtgt tgttccagtt tggaacaaga gtccactatt aaagaacgtg gactccaacg      4560
tcaaagggcg aaaaaccgtc tatcagggcg atggcccact acgtgaacca tcacccaaat      4620
caagtttttt ggggtcgagg tgccgtaaag cactaaatcg aaccctaaa gggagccccc      4680 gatttagagc ttgacgggga agccggcga acgtggcgag aaaggaaggg aagaaagcga      4740
aaggagcggg cgctagggcg ctggcaagtg tagcggtcac gctgcgcgta accaccacac      4800
ccgccgcgct taatgcgccg ctacaggcg cgtaaaagga tctaggtgaa gatcctttt      4860 gataatctca tgaccaaaat cccttaacgt gagttttcgt tccactgagc gtcagacccc      4920
gtagaaaaga tcaaaggatc ttcttgagat ccttttttttc tgcgcgtaat ctgctgcttg      4980
caaacaaaaa aaccaccgct accagcggtg gtttgtttgc cggatcaaga gctaccaact      5040 cttttttccga aggtaactgg cttcagcaga gcgcagatac caaatactgt ccttctagtg      5100
tagccgtagt taggccacca cttcaagaac tctgtagcac cgcctacata cctcgctctg      5160
ctaatcctgt taccagtggc tgctgccagt ggcgataagt cgtgtcttac cgggttggac      5220
tcaagacgat agttaccgga taaggcgcag cggtcgggct gaacgggggg ttcgtgcaca      5280
cagcccagct tggagcgaac gacctacacc gaactgagat acctacagcg tgagctatga      5340
gaaagcgcca cgcttcccga agggagaaag gcggacaggt atccggtaag cggcagggtc      5400
ggaacaggag agcgcacgag ggagcttcca ggggaaacg cctggtatct ttatagtcct      5460
gtcgggtttc gccacctctg acttgagcgt cgatttttgt gatgctcgtc agggggggcgg      5520
```

```
agcctatgga aaaacgccag caacgcggcc tttttacggt tcctggcctt ttgctggcct   5580
tttgctcaca tgttctttcc tgcgttatcc cctgattctg tggataaccg tattaccgcc   5640
tttgagtgag ctgataccgc tcgccgcagc cgaacgaccg agcgcagcga gtcagtgagc   5700
gaggaagcgg aagagcgcct gatgcggtat tttctcctta cgcatctgtg cggtatttca   5760
caccgcatat atggtgcact ctcagtacaa tctgctctga tgccgcatag ttaagccagt   5820
atacactccg ctatcgctac gtgactgggt catggctgcg ccccgacacc cgccaacacc   5880
cgctgacgcg ccctgacggg cttgtctgct cccggcatcc gcttacagac aagctgtgac   5940
cgtctccggg agctgcatgt gtcagaggtt ttcaccgtca tcaccgaaac gcgcgaggca   6000
gctgcggtaa agctcatcag cgtggtcgtg cagcgattca cagatgtctg cctgttcatc   6060
cgcgtccagc tcgttgagtt tctccagaag cgttaatgtc tggcttctga taaagcgggc   6120
catgttaagg gcggtttttt cctgtttggt cactgatgcc tccgtgtaag ggggatttct   6180
gttcatgggg gtaatgatac cgatgaaacg agagaggatg ctcacgatac gggttactga   6240
tgatgaacat gcccggttac tggaacgttg tgagggtaaa caactggcgg tatggatgcg   6300
gcgggaccag agaaaaatca ctcagggtca atgccagcgc ttcgttaata cagatgtagg   6360
tgttccacag ggtagccagc agcatcctgc gatgcagatc cggaacataa tggtgcaggg   6420
cgctgacttc cgcgttttcca gactttacga aacacgaaaa ccgaagacca ttcatgttgt   6480
tgctcaggtc gcagacgttt tgcagcagca gtcgcttcac gttcgctcgc gtatcggtga   6540
ttcattctgc taaccagtaa ggcaaccccg ccagcctagc cgggtcctca acgacaggag   6600
cacgatcatg cgcacccgtg gccaggaccc aacgctgccc gaaatt               6646

<210> SEQ ID NO 4
<211> LENGTH: 8310
<212> TYPE: DNA
<213> ORGANISM: Artificial Sequence
<220> FEATURE:
<223> OTHER INFORMATION: Synthetic Construct

<400> SEQUENCE: 4
ccgacaccat cgaatggtgc aaaacctttc gcggtatggc atgatagcgc ccggaagaga     60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
```

```
acgataccga agacagctca tgttatatcc cgccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg gcgcccaata   1080
cgcaaaccgc ctctcccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactcacg gtgcaccaat gcttctggcg    1260
tcaggcagcc atcggaagct gtggtatggc tgtgcaggtc gtaaatcact gcataattcg   1320
tgtcgctcaa ggcgcactcc cgttctggat aatgttttt cgccgacat cataacggtt     1380
ctggcaaata ttctgaaatg agctgttgac aattaatcat cggctcgtat aatgtgtgga   1440
attgtgagcg gataacaatt tcacacagga acagccagt ccgtttaggt gttttcacga    1500
gcacttcacc aacaaggacc atagcatatg aaaatcgaag aaggtaaact ggtaatctgg   1560
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt tggtggctac   1740
gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta aacaaagat ctgctgccga cccgccaaa aacctgggaa     1920
gagatcccgg cgctggataa agaactgaaa gcgaaggta agagcgcgct gatgttcaac   1980
ctgcaagaac cgtacttcac ctggccgctg attgctgctg acggggtta tgcgttcaag    2040
tatgaaaacg gcaagtacga cattaaagac gtgggcgtgg ataacgctgg cgcgaaagcg   2100
ggtctgacct tcctggttga cctgattaaa aacaaacaca tgaatgcaga caccgattac   2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggtgaaaa atccgcggat tgccgccact atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgaagcc ctgaaagacg cgcagactaa ttcgagctcg   2640
aacaacaaca acaataacaa taacaacaac ctcgggatcg agggaaggat ttcagaattc   2700
tgtgcgacct cttctcaatt tactcagatt accgagcata attcccgtcg ttccgcaaac   2760
tatcagccaa acctgtggaa tttcgaattc ctgcaatccc tggagaacga cctgaaagtg   2820
gaaaagctgg aggagaaagc gaccaaactg gaggaagaag ttcgctgcat gatcaaccgt   2880
gtagacaccc agccgctgtc cctgctggag ctgatcgacg atgtgcagcg cctgggtctg   2940
acctacaaat ttgaaaaaga catcattaaa gccctggaaa acatcgtact gctggacgaa   3000
aacaaaaaga caaatctga cctgcacgca accgctctgt cttttccgtct gctgcgtcag    3060
cacggtttcg aggtttctca ggatgtttt gagcgtttca aggataaaga aggtggtttc    3120
agcggtgaac tgaaaggtga cgtccaaggc ctgctgagcc tgtatgaagc gtcttacctg   3180
ggtttcgagg gtgagaacct gctggaggag gcgcgtacct tttccatcac ccacctgaag   3240
aacaacctga aagaaggcat taataccaag gttgcagaac aagtgagcca cgccctggaa   3300
```

```
ctgccatatc accagcgtct gcaccgtctg gaggcacgtt ggttcctgga taaatacgaa    3360
ccgaaagaac cgcatcacca gctgctgctg gagctggcga agctggattt taacatggta    3420
cagaccctgc accagaaaga gctgcaagat ctgtcccgct ggtggaccga gatgggcctg    3480
gctagcaaac tggattttgt acgcgaccgc ctgatggaag tttatttctg ggcactgggt    3540
atggcgccag acccgcagtt tggtgaatgt cgcaaagctg ttactaaaat gtttggtctg    3600
gtgacgatca tcgatgacgt gtatgacgtt tatggcactc tggacgaact gcaactgttc    3660
accgatgctg tagagcgctg ggacgttaac gctattaaca ccctgccgga ctatatgaaa    3720
ctgtgtttcc tggcactgta caacaccgtt aacgacacgt cctattctat tctgaaagag    3780
aaaggtcata caacctgtc ctatctgacg aaaagctggc gtgaactgtg caaagccttt    3840
ctgcaagagg cgaaatggtc caacaacaaa attatcccgg cttctccaa gtacctggaa    3900 aacgccagcg tttcctcctc cggtgtagcg ctgctggcgc cgtcttactt tccgtatgc    3960 cagcagcagg aagacatctc cgaccacgcg ctgcgttccc tgaccgactt ccatggtctg    4020
gtgcgttcta gctgcgttat cttccgcctg tgcaacgatc tggccacctc tgcggcggag    4080
ctggaacgtg gcgagactac caattctatc attagctaca tgcacgaaaa cgatggtacc    4140
agcgaggaac aggcccgcga agaactgcgt aaactgatcg acgccgaatg gaaaaagatg    4200
aatcgtgaac gcgttagcga ctccaccctg ctgcctaaag cgttcatgga atcgcagtt    4260 aacatggcac gtgtttccca ctgcacctac cagtatggcg atggtctggg tcgcccagac    4320
tacgcgactg aaaaccgcat caaactgctg ctgattgacc cttteccgat taaccagctg    4380 atgtatgtct aagcttggca ctggccgtcg ttttacaacg tcgtgactgg gaaaaccctg    4440
gcgttaccca acttaatcgc cttgcagcac atccccttt cgccagctgg cgtaatagcg    4500
aagaggcccg caccgatcgc ccttcccaac agttgcgcag cctgaatggc gaatggcagc    4560
ttggctgttt tggcggatga gataagattt tcagcctgat acagattaaa tcagaacgca    4620
gaagcggtct gataaaacag aatttgcctg gcggcagtag cgcggtggtc ccacctgacc    4680
ccatgccgaa ctcagaagtg aaacgccgta gcgccgatgg tagtgtgggg tctccccatg    4740
cgagagtagg gaactgccag gcatcaaata aaacgaaagg ctcagtcgaa agactgggcc    4800
tttcgtttta tctgttgttt gtcggtgaac gctctcctga gtaggacaaa tccgccggga    4860
gcggatttga acgttgcgaa gcaacggccc ggagggtggc gggcaggacg cccgccataa    4920
actgccaggc atcaaattaa gcagaaggcc atcctgacgg atggcctttt tgcgtttcta    4980
caaactcttt ttgtttattt ttctaaatac attcaaatat gtatccgctc atgagacaat    5040
aaccctgata aatgcttcaa taatattgaa aaggaagag tatgagtatt caacatttcc    5100
gtgtcgccct tattccctt tttgcggcat tttgccttcc tgtttttgct cacccagaaa    5160
cgctggtgaa agtaaaagat gctgaagatc agttgggtgc acgagtgggt tacatcgaac    5220
tggatctcaa cagcggtaag atccttgaga gttttcgccc cgaagaacgt tctccaatga    5280
tgagcacttt taaagttctg ctatgtggcg cggtattatc ccgtgttgac gccgggcaag    5340
agcaactcgg tcgccgcata cactattctc agaatgactt ggttgagtac tcaccagtca    5400
cagaaaagca tcttacggat ggcatgacag taagagaatt atgcagtgct gccataacca    5460
tgagtgataa cactgcggcc aacttacttc tgacaacgat cggaggaccg aaggagctaa    5520
ccgctttttt gcacaacatg ggggatcatg taactcgcct tgatcgttgg gaaccggagc    5580
tgaatgaagc cataccaaac gacgagcgtg acaccacgat gcctgtagca atggcaacaa    5640
```

```
cgttgcgcaa actattaact ggcgaactac ttactctagc ttcccggcaa caattaatag      5700
actggatgga ggcggataaa gttgcaggac cacttctgcg ctcggccctt ccggctggct      5760
ggtttattgc tgataaatct ggagccggtg agcgtgggtc tcgcggtatc attgcagcac      5820
tggggccaga tggtaagccc tcccgtatcg tagttatcta cacgacgggg agtcaggcaa      5880
ctatggatga acgaaataga cagatcgctg agataggtgc ctcactgatt aagcattggt      5940
aactgtcaga ccaagtttac tcatatatac tttagattga tttacccggg ttgataatca      6000
gaaaagcccc aaaaacagga agattgtata agcaaatatt taaattgtaa acgttaatat      6060
tttgttaaaa ttcgcgttaa attttttgtta aatcagctca ttttttaacc aataggccga      6120
aatcggcaaa atcccttata aatcaaaaga atagaccgag atagggttga gtgttgttcc      6180
agtttggaac aagagtccac tattaaagaa cgtggactcc aacgtcaaag ggcgaaaaac      6240
cgtctatcag ggcgatggcc cactacgtga accatcaccc aaatcaagtt ttttggggtc      6300
gaggtgccgt aaagcactaa atcggaaccc taaagggagc ccccgattta gagcttgacg      6360
gggaaagccg gcgaacgtgg cgagaaagga agggaagaaa gcgaaaggag cgggcgctag      6420
ggcgctggca agtgtagcgg tcacgctgcg cgtaaccacc acacccgccg cgcttaatgc      6480
gccgctacag ggcgcgtaaa aggatctagg tgaagatcct tttttgataat ctcatgacca      6540 aaatccctta acgtgagttt tcgttccact gagcgtcaga ccccgtagaa aagatcaaag      6600
gatcttcttg agatcctttt tttctgcgcg taatctgctg cttgcaaaca aaaaaaccac      6660
cgctaccagc ggtggtttgt ttgccggatc aagagctacc aactcttttt ccgaaggtaa      6720
ctggcttcag cagagcgcag ataccaaata ctgtccttct agtgtagccg tagttaggcc      6780
accacttcaa gaactctgta gcaccgccta catacctcgc tctgctaatc ctgttaccag      6840
tggctgctgc cagtggcgat aagtcgtgtc ttaccgggtt ggactcaaga cgatagttac      6900
cggataaggc gcagcggtcg ggctgaacgg ggggttcgtg cacacagccc agcttggagc      6960
gaacgaccta caccgaactg agatacctac agcgtgagct atgagaaagc gccacgcttc      7020
ccgaagggag aaaggcggac aggtatccgg taagcggcag ggtcggaaca ggagagcgca      7080
cgagggagct tccaggggga aacgcctggt atctttatag tcctgtcggg tttcgccacc      7140
tctgacttga gcgtcgattt ttgtgatgct cgtcaggggg gcggagccta tggaaaaacg      7200
ccagcaacgc ggcctttttta cggttcctgg ccttttgctg ccttttgct cacatgttct      7260 ttcctgcgtt atcccctgat tctgtggata accgtattac cgcctttgag tgagctgata      7320
ccgctcgccg cagccgaacg accgagcgca gcgagtcagt gagcgaggaa gcggaagagc      7380
gcctgatgcg gtattttctc cttacgcatc tgtgcggtat ttcacaccgc atatatggtg      7440
cactctcagt acaatctgct ctgatgccgc atagttaagc cagtatacac tccgctatcg      7500
ctacgtgact gggtcatggc tgcgccccga cacccgccaa cacccgctga cgcgccctga      7560
cgggcttgtc tgctcccggc atccgcttac agacaagctg tgaccgtctc cgggagctgc      7620
atgtgtcaga ggttttcacc gtcatcaccg aaacgcgcga ggcagctgcg gtaaagctca      7680
tcagcgtggt cgtgcagcga ttcacagatg tctgcctgtt catccgcgtc cagctcgttg      7740
agtttctcca gaagcgttaa tgtctggctt ctgataaagc gggccatgtt aagggcggtt      7800
ttttcctgtt tggtcactga tgcctccgtg taagggggat ttctgttcat gggggtaatg      7860
ataccgatga aacgagagag gatgctcacg atacgggtta ctgatgatga acatgcccgg      7920
ttactggaac gttgtgaggg taaacaactg gcggtatgga tgcggcggga ccagagaaaa      7980
atcactcagg gtcaatgcca gcgcttcgtt aatacagatg taggtgttcc acagggtagc      8040
```

```
cagcagcatc ctgcgatgca gatccggaac ataatggtgc agggcgctga cttccgcgtt    8100
tccagacttt acgaaacacg gaaaccgaag accattcatg ttgttgctca ggtcgcagac    8160
gttttgcagc agcagtcgct tcacgttcgc tcgcgtatcg gtgattcatt ctgctaacca    8220
gtaaggcaac cccgccagcc tagccgggtc ctcaacgaca ggagcacgat catgcgcacc    8280
cgtggccagg acccaacgct gcccgaaatt                                     8310
```

<210> SEQ ID NO 5
<211> LENGTH: 560
<212> TYPE: PRT
<213> ORGANISM: Populus tremuloides

<400> SEQUENCE: 5

```
Met Arg Cys Ser Val Ser Thr Glu Asn Val Ser Phe Ser Glu Thr Glu
 1               5                   10                  15

Thr Glu Thr Arg Arg Ser Ala Asn Tyr Glu Pro Asn Ser Trp Asp Tyr
             20                  25                  30

Asp Tyr Leu Leu Ser Ser Asp Thr Asp Glu Ser Ile Glu Val His Lys
         35                  40                  45

Asp Lys Ala Lys Lys Leu Glu Ala Glu Val Arg Glu Ile Asn Asn
     50                  55                  60

Glu Lys Ala Glu Phe Leu Thr Leu Leu Glu Leu Ile Asp Asn Val Gln
 65                  70                  75                  80

Arg Leu Gly Leu Gly Tyr Arg Phe Glu Ser Asp Ile Arg Arg Ala Leu
                 85                  90                  95

Asp Arg Phe Val Ser Ser Gly Gly Phe Asp Gly Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Ser His Ala Leu Glu Leu Pro Leu
        195                 200                 205

His Arg Arg Thr Gln Arg Leu Glu Ala Val Trp Ser Ile Glu Ala Tyr
    210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
    290                 295                 300

Phe Val Thr Ile Ile Asp Asp Ile Tyr Asp Val Tyr Gly Thr Leu Asp
305                 310                 315                 320
```

```
Glu Leu Glu Leu Phe Thr Asp Ala Val Glu Arg Trp Asp Val Asn Ala
            325                 330                 335

Ile Asn Asp Leu Pro Asp Tyr Met Lys Leu Cys Phe Leu Ala Leu Tyr
        340                 345                 350

Asn Thr Ile Asn Glu Ile Ala Tyr Asp Asn Leu Lys Asp Lys Gly Glu
    355                 360                 365

Asn Ile Leu Pro Tyr Leu Thr Lys Ala Trp Ala Asp Leu Cys Asn Ala
370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
                405                 410                 415

Leu Ile Phe Ala Tyr Phe Ala Val Val Gln Asn Ile Lys Lys Glu Glu
                420                 425                 430

Ile Glu Asn Leu Gln Lys Tyr His Asp Ile Ile Ser Arg Pro Ser His
            435                 440                 445

Ile Phe Arg Leu Cys Asn Asp Leu Ala Ser Ala Ser Ala Glu Ile Ala
    450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
                500                 505                 510

Lys Pro Phe Val Glu Thr Ala Ile Asn Leu Ala Arg Gln Ser His Cys
            515                 520                 525

Thr Tyr His Asn Gly Asp Ala His Thr Ser Pro Asp Glu Leu Thr Arg
    530                 535                 540

Lys Arg Val Leu Ser Val Ile Thr Glu Pro Ile Leu Pro Phe Glu Arg
545                 550                 555                 560

<210> SEQ ID NO 6
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 6
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaagccg tttctgtaat gaaggagaaa      660
actcaccgag gcagttccat aggatggcaa gatcctggta tcggtctgcg attccgactc     720
```

```
gtccaacatc aataacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg caacgctac    1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
```

| | |
|---|---|
| ccgccagcct agccgggtcc tcaacgacag gagcacgatc atgcgcaccc gtggggccgc | 3180 |
| catgccggcg ataatggcct gcttctcgcc gaaacgtttg gtggcgggac cagtgacgaa | 3240 |
| ggcttgagcg agggcgtgca agattccgaa taccgcaagc gacaggccga tcatcgtcgc | 3300 |
| gctccagcga aagcggtcct cgccgaaaat gacccagagc gctgccggca cctgtcctac | 3360 |
| gagttgcatg ataaagaaga cagtcataag tgcggcgacg atagtcatgc cccgcgccca | 3420 |
| ccggaaggag ctgactgggt tgaaggctct caagggcatc ggtcgagatc ccggtgccta | 3480 |
| atgagtgagc taacttacat taattgcgtt gcgctcactg cccgctttcc agtcgggaaa | 3540 |
| cctgtcgtgc cagctgcatt aatgaatcgg ccaacgcgcg gggagaggcg gtttgcgtat | 3600 |
| tgggcgccag ggtggttttt cttttcacca gtgagacggg caacagctga ttgcccttca | 3660 |
| ccgcctggcc ctgagagagt tgcagcaagc ggtccacgct ggtttgcccc agcaggcgaa | 3720 |
| aatcctgttt gatggtggtt aacggcggga tataacatga gctgtcttcg gtatcgtcgt | 3780 |
| atcccactac cgagatatcc gcaccaacgc gcagcccgga ctcggtaatg gcgcgcattg | 3840 |
| cgcccagcgc catctgatcg ttggcaacca gcatcgcagt gggaacgatg ccctcattca | 3900 |
| gcatttgcat ggtttgttga aaaccggaca tggcactcca gtcgccttcc cgttccgcta | 3960 |
| tcggctgaat ttgattgcga gtgagatatt tatgccagcc agccagacgc agacgcgccg | 4020 |
| agacagaact taatgggccc gctaacagcg cgatttgctg gtgacccaat gcgaccagat | 4080 |
| gctccacgcc cagtcgcgta ccgtcttcat gggagaaaat aatactgttg atgggtgtct | 4140 |
| ggtcagagac atcaagaaat aacgccgaaa cattagtgca ggcagcttcc acagcaatgg | 4200 |
| catcctggtc atccagcgga tagttaatga tcagcccact gacgcgttgc gcgagaagat | 4260 |
| tgtgcaccgc cgctttacag gcttcgacgc cgcttcgttc taccatcgac accaccacgc | 4320 |
| tggcacccag ttgatcggcg cgagatttaa tcgccgcgac aatttgcgac ggcgcgtgca | 4380 |
| gggccagact ggaggtggca acgccaatca gcaacgactg tttgcccgcc agttgttgtg | 4440 |
| ccacgcggtt gggaatgtaa ttcagctccg ccatcgccgc ttccactttt tcccgcgttt | 4500 |
| tcgcagaaac gtggctggcc tggttcacca cgcgggaaac ggtctgataa gagacaccgg | 4560 |
| catactctgc gacatcgtat aacgttactg gtttcacatt caccaccctg aattgactct | 4620 |
| cttccgggcg ctatcatgcc ataccgcgaa aggttttgcg ccattcgatg gtgtccggga | 4680 |
| tctcgacgct ctcccttatg cgactcctgc attaggaagc agcccagtag taggttgagg | 4740 |
| ccgttgagca ccgccgccgc aaggaatggt gcatgcaagg agatggcgcc caacagtccc | 4800 |
| ccggccacgg ggcctgccac catacccacg ccgaaacaag cgctcatgag cccgaagtgg | 4860 |
| cgagcccgat cttccccatc ggtgatgtcg gcgatatagg cgccagcaac cgcacctgtg | 4920 |
| gcgccggtga tgccggccac gatgcgtccg gcgtagagga tcgagatctc gatcccgcga | 4980 |
| aattaatacg actcactata ggggaattgt gagcggataa caattcccct ctagaaataa | 5040 |
| ttttgtttaa ctttaagaag gagatataca tatgcgttgt agcgtgtcca ccgaaaatgt | 5100 |
| gtctttctct gaaactgaaa ccgaaacgcg tcgttctgcg aactacgaac ctaacagctg | 5160 |
| ggactatgat tacctgctgt cctccgacac ggacgagtcc atcgaagtac acaaagacaa | 5220 |
| agcgaaaaag ctggaagccg aagttcgtcg cgagattaat aacgaaaaag cagaatttct | 5280 |
| gaccctgctg gaactgattg acaacgtcca gcgcctgggc ctgggttacc gtttcgagtc | 5340 |
| tgatatccgt cgtgcgctgg atcgcttcgt ttcctccggc ggcttcgatg gcgtaaccaa | 5400 |
| gacttccctg cacggtacgg cactgtcttt ccgtctgctg cgtcaacacg gttttgaggt | 5460 |

-continued

| | | | | |
|---|---|---|---|---|
| ttctcaggaa | gcgttcagcg | gcttcaaaga | ccaaaacggc | aacttcctgg agaacctgaa | 5520 |
| ggaagatatc | aaagctatcc | tgagcctgta | cgaggccagc | ttcctggctc tggaaggcga | 5580 |
| aaacatcctg | gacgaggcga | aggttttcgc | aatctctcat | ctgaaagaac tgtctgaaga | 5640 |
| aaagatcggt | aaagagctgg | cagaacaggt | gtcccatgca | ctggaactgc cactgcatcg | 5700 |
| ccgtactcag | cgtctggaag | cagtatggtc | tatcgaggcc | taccgtaaaa aggaggacgc | 5760 |
| gaaccaggtt | ctgctggagc | tggcaattct | ggattacaac | atgatccagt ctgtatacca | 5820 |
| gcgtgatctg | cgtgaaacgt | cccgttggtg | gcgtcgtgtg | ggtctggcga ccaaactgca | 5880 |
| ctttgctcgt | gaccgcctga | ttgagagctt | ctactgggcc | gtgggtgtag cattcgaacc | 5940 |
| gcaatactcc | gactgccgta | actccgtcgc | aaaaatgttt | tctttcgtaa ccattatcga | 6000 |
| cgatatctac | gatgtatacg | gcaccctgga | cgaactggag | ctgtttactg atgcagttga | 6060 |
| gcgttgggac | gtaaacgcca | tcaacgacct | gccggattac | atgaaactgt gctttctggc | 6120 |
| tctgtataac | actattaacg | aaatcgccta | cgacaacctg | aaagataaag gtgagaacat | 6180 |
| cctgccgtat | ctgaccaaag | cctgggctga | cctgtgcaac | gctttcctgc aagaagccaa | 6240 |
| gtggctgtac | aacaaatcta | ctccgacctt | tgacgactac | ttcggcaacg catggaaatc | 6300 |
| ctcttctggc | ccgctgcaac | tgatcttcgc | ttacttcgct | gtcgtgcaga acattaaaaa | 6360 |
| ggaagagatc | gaaaacctgc | aaaaatacca | tgacatcatc | tctcgtcctt cccatatctt | 6420 |
| ccgtctgtgc | aatgacctgg | ctagcgcgtc | tgcggaaatt | gcgcgtggtg aaaccgcaaa | 6480 |
| tagcgtttct | tgttacatgc | gcactaaagg | tatctccgaa | gaactggcta ccgaaagcgt | 6540 |
| gatgaatctg | atcgatgaaa | cctggaaaaa | gatgaacaag | gaaaaactgg gtggtagcct | 6600 |
| gttcgcgaaa | ccgttcgtgg | aaaccgcgat | caacctggca | cgtcaatctc actgcactta | 6660 |
| tcataacggc | gacgcgcata | cctctccgga | tgagctgacc | cgcaaacgcg ttctgtctgt | 6720 |
| aatcactgaa | ccgattctgc | cgtttgaacg | ctaaggatcc | gaattcgagc tccgtcgaca | 6780 |
| agcttgcggc | cgcactcgag | caccaccacc | accaccactg | agatccggct gctaacaaag | 6840 |
| cccgaaagga | agctgagttg | gctgctgcca | ccgctgagca | ataactagca taacccttg | 6900 |
| gggcctctaa | acgggtcttg | aggggttttt | tgctgaaagg | aggaactata tccggat | 6957 |

<210> SEQ ID NO 7
<211> LENGTH: 560
<212> TYPE: PRT
<213> ORGANISM: Populus trichocarpa

<400> SEQUENCE: 7

```
Met Arg Cys Ser Val Ser Thr Glu Asn Val Ser Phe Thr Glu Thr Glu
 1               5                  10                  15

Thr Glu Thr Arg Arg Ser Ala Asn Tyr Glu Pro Asn Ser Trp Asp Tyr
             20                  25                  30

Asp Tyr Leu Leu Ser Ser Asp Thr Asp Glu Ser Ile Glu Val Tyr Lys
         35                  40                  45

Asp Lys Ala Lys Lys Leu Glu Ala Glu Val Arg Arg Glu Ile Asn Asn
     50                  55                  60

Glu Lys Ala Glu Phe Leu Thr Leu Leu Glu Leu Ile Asp Asn Val Gln
 65                  70                  75                  80

Arg Leu Gly Leu Gly Tyr Arg Phe Glu Ser Asp Ile Arg Arg Ala Leu
                 85                  90                  95

Asp Arg Phe Val Ser Ser Gly Gly Phe Asp Ala Val Thr Lys Thr Ser
            100                 105                 110
```

```
Leu His Ala Thr Ala Leu Ser Phe Arg Leu Leu Arg Gln His Gly Phe
            115                 120                 125

Glu Val Ser Gln Glu Ala Phe Ser Gly Phe Lys Asp Gln Asn Gly Asn
        130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Asp Leu Ala Glu Gln Val Asn His Ala Leu Glu Leu Pro Leu
        195                 200                 205

His Arg Arg Thr Gln Arg Leu Glu Ala Val Leu Ser Ile Glu Ala Tyr
210                 215                 220

Arg Lys Lys Glu Asp Ala Asp Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
290                 295                 300

Phe Val Thr Ile Ile Asp Asp Ile Tyr Asp Val Tyr Gly Thr Leu Asp
305                 310                 315                 320

Glu Leu Glu Leu Phe Thr Asn Ala Val Glu Arg Trp Asp Val Asn Ala
                325                 330                 335

Ile Asp Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Glu Lys Gly Glu
        355                 360                 365

Asn Ile Leu Pro Tyr Leu Thr Lys Ala Trp Ala Asp Leu Cys Asn Ala
370                 375                 380

Phe Leu Gln Glu Ala Lys Trp Leu Tyr Asn Lys Ser Thr Pro Thr Phe
385                 390                 395                 400

Asp Glu Tyr Phe Gly Asn Ala Trp Lys Ser Ser Gly Pro Leu Gln
                405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Ile Ile Ser Arg Pro Ser His
        435                 440                 445

Ile Phe Arg Leu Cys Asn Asp Leu Ala Ser Ala Ser Ala Glu Ile Ala
450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
        515                 520                 525

Thr Tyr His Asn Gly Asp Ala His Thr Ser Pro Asp Glu Leu Thr Arg
```

|   |   | 530 |   |   | 535 |   |   | 540 |   |   |
|---|---|---|---|---|---|---|---|---|---|---|

Lys Arg Val Leu Ser Val Ile Thr Glu Pro Ile Leu Pro Phe Glu Arg
545             550             555             560

<210> SEQ ID NO 8
<211> LENGTH: 6963
<212> TYPE: DNA
<213> ORGANISM: Artificial Sequence
<220> FEATURE:
<223> OTHER INFORMATION: Synthetic Construct

<400> SEQUENCE: 8

| tggcgaatgg gacgcgccct gtagcggcgc attaagcgcg gcgggtgtgg tggttacgcg | 60 |
|---|---|
| cagcgtgacc gctacacttg ccagcgccct agcgcccgct cctttcgctt tcttcccttc | 120 |
| ctttctcgcc acgttcgccg gctttccccg tcaagctcta atcgggggc tcccttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta tagggatttt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa ccccatttg tttattttc taaatacatt caaatatgta | 540 |
| tccgctcatg aattaattct tagaaaaact catcgagcat caaatgaaac tgcaatttat | 600 |
| tcatatcagg attatcaata ccatattttt gaaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga acgaaatac gcgatcgctg ttaaaaggac | 960 |
| aattacaaac aggaatcgaa tgcaaccggc gcaggaacac tgccagcgca tcaacaatat | 1020 |
| tttcacctga atcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa aatcccttaa | 1440 |
| cgtgagtttt cgttccactg agcgtcagac cccgtagaaa agatcaaagg atcttcttga | 1500 |
| gatccttttt ttctgcgcgt aatctgctgc ttgcaaacaa aaaaaccacc gctaccagcg | 1560 |
| gtggtttgtt tgccggatca agagctacca actcttttc cgaaggtaac tggcttcagc | 1620 |
| agagcgcaga taccaaatac tgtccttcta gtgtagccgt agttaggcca ccacttcaag | 1680 |
| aactctgtag caccgcctac atacctcgct ctgctaatcc tgttaccagt ggctgctgcc | 1740 |
| agtggcgata gtcgtgtct taccgggttg gactcaagac gatagttacc ggataaggcg | 1800 |
| cagcggtcgg gctgaacggg gggttcgtgc acacagccca gcttggagcg aacgacctac | 1860 |
| accgaactga gatacctaca gcgtgagcta tgagaaagcg ccacgcttcc cgaagggaga | 1920 |

-continued

```
aaggcggaca ggtatccggt aagcggcagg gtcggaacag gagagcgcac gagggagctt    1980
ccagggggaa acgcctggta tcttttatagt cctgtcgggt ttcgccacct ctgacttgag   2040
cgtcgatttt tgtgatgctc gtcagggggg cggagcctat ggaaaaacgc cagcaacgcg   2100
gccttttttac ggttcctggc cttttgctgg ccttttgctc acatgttctt tcctgcgtta  2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aaggggggatt tctgttcatg gggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacgcgc gatttgctgg tgacccaat gcgaccagat    4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
```

```
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccacttt tcccgcgttt    4500 tcgcagaaac gtggctggcc tggttcacca cgcgggaaac ggtctgataa agacaccgg    4560 catactctgc gacatcgtat aacgttactg gtttcacatt caccaccctg aattgactct   4620
cttccgggcg ctatcatgcc ataccgcgaa aggttttgcg ccattcgatg tgtccggga    4680 tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcatatg cgttgtagcg tgtccaccga   5100
aaatgtgtct ttcaccgaaa ctgaaaccga aacgcgtcgt tctgcgaact acgaacctaa   5160
cagctgggac tatgattacc tgctgtcctc cgacacggac gagtccatcg aagtatacaa   5220
agacaaagcg aaaaagctgg aagccgaagt tcgtcgcgag attaataacg aaaaagcaga   5280
atttctgacc ctgctggaac tgattgacaa cgtccagcgc ctgggcctgg gttaccgttt   5340
cgagtctgat atccgtcgtg cgctggatcg cttcgtttcc tccggcgggct tcgatgcggt   5400 aaccaagact tccctgcacg cgacggcact gtctttccgt ctgctgcgtc aacacggttt   5460
tgaggtttct caggaagcgt tcagcggctt caaagaccaa aacggcaact tcctggagaa   5520
cctgaaggaa gatatcaaag ctatcctgag cctgtacgag gccagcttcc tggctctgga   5580
aggcgaaaac atcctggacg aggcgaaggt tttcgcaatc tctcatctga agaactgtc    5640 tgaagaaaag atcggtaaag atctggcaga acaggtgaac catgcactgg aactgccact   5700
gcatcgccgt actcagcgtc tggaagcagt actgtctatc gaggcctacc gtaaaaagga   5760
ggacgcggat caggttctgc tggagctggc aattctggat tacaacatga tccagtctgt   5820
ataccagcgt gatctgcgtg aaacgtcccg ttggtggcgt cgtgtgggtc tggcgaccaa   5880
actgcacttt gctcgtgacc gcctgattga gagcttctac tgggcgtgg gtgtagcatt    5940 cgaaccgcaa tactccgact gccgtaactc cgtcgcaaaa atgttttctt tcgtaaccat   6000
tatcgacgat atctacgatg tatacggcac cctggacgaa ctggagctgt ttactaacgc   6060
agttgagcgt tgggacgtaa acgccatcga cgatctgccg gattacatga aactgtgctt   6120
tctggctctg tataacacta ttaacgaaat cgcctacgac aacctgaaag aaaaaggtga   6180
gaacatcctg ccgtatctga ccaaagcctg ggctgacctg tgcaacgctt tcctgcaaga   6240
agccaagtgg ctgtacaaca atctactcc gacctttgac gaatacttcg caacgcatg     6300 gaaatcctct tctggcccgc tgcaactggt gttcgcttac ttcgctgtcg tgcagaacat   6360 taaaaggaa gagatcgaaa acctgcaaaa ataccatgac atcatctctc gtccttccca    6420
tatcttccgt ctgtgcaatg acctggctag cgcgtctgcg gaaattgcgc gtggtgaaac   6480
cgcaaatagc gtttcttgtt acatgcgcac taaaggtatc tccgaagaac tggctaccga   6540
aagcgtgatg aatctgatcg atgaaacctg gaaaagatg aacaaggaaa aactgggtgg    6600
tagcctgttc gcgaaaccgt tcgtggaaac cgcgatcaac ctggcacgtc aatctcactg   6660
```

-continued

```
cacttatcat aacggcgacg cgcataccto tccggatgag ctgacccgca aacgcgttct   6720
gtctgtaatc actgaaccga ttctgccgtt tgaacgctaa ggatccgaat tcgagctccg   6780
tcgacaagct tgcggccgca ctcgagcacc accaccacca ccactgagat ccggctgcta   6840
acaaagcccg aaaggaagct gagttggctg ctgccaccgc tgagcaataa ctagcataac   6900
cccttggggc ctctaaacgg gtcttgaggg gttttttgct gaaaggagga actatatccg   6960
gat                                                                 6963
```

<210> SEQ ID NO 9
<211> LENGTH: 578
<212> TYPE: PRT
<213> ORGANISM: Artificial Sequence
<220> FEATURE:
<223> OTHER INFORMATION: Synthetic Construct

<400> SEQUENCE: 9

```
Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
             20                  25                  30

His Pro Phe Thr Met Arg Arg Ser Ala Asn Tyr Glu Pro Asn Ser Trp
         35                  40                  45

Asp Tyr Asp Tyr Leu Leu Ser Ser Asp Thr Asp Glu Ser Ile Glu Val
 50                  55                  60

Tyr Lys Asp Lys Ala Lys Lys Leu Glu Ala Glu Val Arg Arg Glu Ile
 65                  70                  75                  80

Asn Asn Glu Lys Ala Glu Phe Leu Thr Leu Leu Glu Leu Ile Asp Asn
                 85                  90                  95

Val Gln Arg Leu Gly Leu Gly Tyr Arg Phe Glu Ser Asp Ile Arg Gly
            100                 105                 110

Ala Leu Asp Arg Phe Val Ser Ser Gly Gly Phe Asp Ala Val Thr Lys
        115                 120                 125

Thr Ser Leu His Gly Thr Ala Leu Ser Phe Arg Leu Leu Arg Gln His
130                 135                 140

Gly Phe Glu Val Ser Gln Glu Ala Phe Ser Gly Phe Lys Asp Gln Asn
145                 150                 155                 160

Gly Asn Phe Leu Glu Asn Leu Lys Glu Asp Ile Lys Ala Ile Leu Ser
                165                 170                 175

Leu Tyr Glu Ala Ser Phe Leu Ala Leu Glu Gly Glu Asn Ile Leu Asp
            180                 185                 190

Glu Ala Lys Val Phe Ala Ile Ser His Leu Lys Glu Leu Ser Glu Glu
        195                 200                 205

Lys Ile Gly Lys Glu Leu Ala Glu Gln Val Asn His Ala Leu Glu Leu
    210                 215                 220

Pro Leu His Arg Arg Thr Gln Arg Leu Glu Ala Val Trp Ser Ile Glu
225                 230                 235                 240

Ala Tyr Arg Lys Lys Glu Asp Ala Asn Gln Val Leu Leu Glu Leu Ala
                245                 250                 255

Ile Leu Asp Tyr Asn Met Ile Gln Ser Val Tyr Gln Arg Asp Leu Arg
            260                 265                 270

Glu Thr Ser Arg Trp Trp Arg Arg Val Gly Leu Ala Thr Lys Leu His
        275                 280                 285

Phe Ala Arg Asp Arg Leu Ile Glu Ser Phe Tyr Trp Ala Val Gly Val
    290                 295                 300
```

Ala Phe Glu Pro Gln Tyr Ser Asp Cys Arg Asn Ser Val Ala Lys Met
305                 310                 315                 320

Phe Ser Phe Val Thr Ile Ile Asp Asp Ile Tyr Asp Val Tyr Gly Thr
                325                 330                 335

Leu Asp Glu Leu Glu Leu Phe Thr Asp Ala Val Glu Arg Trp Asp Val
            340                 345                 350

Asn Ala Ile Asn Asp Leu Pro Asp Tyr Met Lys Leu Cys Phe Leu Ala
                355                 360                 365

Leu Tyr Asn Thr Ile Asn Glu Ile Ala Tyr Asp Asn Leu Lys Asp Lys
370                 375                 380

Gly Glu Asn Ile Leu Pro Tyr Leu Thr Lys Ala Trp Ala Asp Leu Cys
385                 390                 395                 400

Asn Ala Phe Leu Gln Glu Ala Lys Trp Leu Tyr Asn Lys Ser Thr Pro
                405                 410                 415

Thr Phe Asp Asp Tyr Phe Gly Asn Ala Trp Lys Ser Ser Gly Pro
                420                 425                 430

Leu Gln Leu Val Phe Ala Tyr Phe Ala Val Val Gln Asn Ile Lys Lys
                435                 440                 445

Glu Glu Ile Glu Asn Leu Gln Lys Tyr His Asp Thr Ile Ser Arg Pro
450                 455                 460

Ser His Ile Phe Arg Leu Cys Asn Asp Leu Ala Ser Ala Ser Ala Glu
465                 470                 475                 480

Ile Ala Arg Gly Glu Thr Ala Asn Ser Val Ser Cys Tyr Met Arg Thr
                485                 490                 495

Lys Gly Ile Ser Glu Glu Leu Ala Thr Glu Ser Val Met Asn Leu Ile
                500                 505                 510

Asp Glu Thr Trp Lys Lys Met Asn Lys Glu Lys Leu Gly Gly Ser Leu
                515                 520                 525

Phe Ala Lys Pro Phe Val Glu Thr Ala Ile Asn Leu Ala Arg Gln Ser
530                 535                 540

His Cys Thr Tyr His Asn Gly Asp Ala His Thr Ser Pro Asp Glu Leu
545                 550                 555                 560

Thr Arg Lys Arg Val Leu Ser Val Ile Thr Glu Pro Ile Leu Pro Phe
                565                 570                 575

Glu Arg

<210> SEQ ID NO 10
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 10
aagggcgagc tcaacgatcc ggctgctaac aaagcccgaa aggaagctga gttggctgct      60
gccaccgctg agcaataact agcataaccc cttggggcct ctaaacgggt cttgaggagt     120 ttttttgctga aggaggaac tatatccgga tatcccgcaa gaggcccggc agtaccggca     180
taaccaagcc tatgcctaca gcatccaggg tgacggtgcc gaggatgacg atgagcgcat     240
tgttagattt catacacggt gcctgactgc gttagcaatt taactgtgat aaactaccgc     300
attaaagctt atcgatgata agctgtcaaa catgagaatt aattcttgaa gacgaaaggg     360
cctcgtgata cgcctatttt tataggttaa tgtcatgata taatggtttc ttagacgtc      420 aggtggcact tttcggggaa atgtgcgcgg aaccctatt tgtttatttt tctaaataca     480

```
ttcaaatatg tatccgctca tgagacaata accctgataa atgcttcaat aatattgaaa      540
aaggaagagt atgattgaac aagatggatt gcacgcaggt tctccggccg cttgggtgga      600
gaggctattc ggctatgact gggcacaact gacaatcggc tgctctgatg ccgccgtgtt      660
ccggctgtca gcgcagggc gcccggttct ttttgtcaag accgacctgt ccggtgccct       720
gaatgaactg caggacgagg cagcgcggct atcgtggctg gccacgacgg gcgttccttg      780
cgcagctgtg ctcgacgttg tcactgaagc gggaagggac tggctgctat tgggcgaagt      840
gccggggcag gatctcctgt catctcacct tgctcctgcc gagaaagtat ccatcatggc      900
tgatgcaatg cggcggctgc atacgcttga tccggctacc tgcccattcg accaccaagc      960
gaaacatcgc atcgagcggg cacgtactcg gatggaagcc ggtcttgtcg atcaggatga      1020
tctggacgaa gagcatcagg ggctcgcgcc agccgaactg ttcgccaggc tcaaggcgcg      1080
catgcccgac ggcgaggatc tcgtcgtgac acatggcgat gcctgcttgc cgaatatcat      1140
ggtggaaaat ggccgctttt ctggattcat cgactgtggc cggctgggtg tggcggaccg      1200
ctatcaggac atagcgttgg ctacccgtga tattgctgaa gagcttggcg gcgaatgggc      1260
tgaccgcttc ctcgtgcttt acggtatcgc cgctcccgat tcgcagcgca tcgccttcta      1320
tcgccttctt gacgagttct tctgagcggg actctggggt tcgaaatgac cgaccaagcg      1380
acgcctaact gtcagaccaa gtttactcat atatacttta gattgattta aaacttcatt      1440
tttaatttaa aaggatctag gtgaagatcc ttttttgataa tctcatgacc aaaatccctt      1500
aacgtgagtt ttcgttccac tgagcgtcag accccgtaga aaagatcaaa ggatcttctt      1560
gagatccttt ttttctgcgc gtaatctgct gcttgcaaac aaaaaaacca ccgctaccag      1620
cggtggtttg tttgccggat caagagctac caactctttt tccgaaggta actggcttca      1680
gcagagcgca gataccaaat actgtccttc tagtgtagcc gtagttaggc caccacttca      1740
agaactctgt agcaccgcct acatacctcg ctctgctaat cctgttacca gtggctgctg      1800
ccagtggcga taagtcgtgt cttaccgggt tggactcaag acgatagtta ccggataagg      1860
cgcagcggtc gggctgaacg gggggttcgt gcacacagcc cagcttggag cgaacgacct      1920
acaccgaact gagatacctac agcgtgagc tatgagaaag cgccacgctt cccgaaggga      1980
gaaaggcgga caggtatccg gtaagcggca gggtcggaac aggagagcgc acgagggagc      2040 ttccagggg aaacgcctgg tatctttata gtcctgtcgg gtttcgccac ctctgacttg      2100
agcgtcgatt tttgtgatgc tcgtcagggg gcggagcct atggaaaaac gccagcaacg      2160
cggccttttt acgttcctg ccttttgct ggccttttgc tcacatgttc tttcctgcgt      2220
tatcccctga ttctgtggat aaccgtatta ccgcctttga gtgagctgat accgctcgcc      2280
gcagccgaac gaccgagcgc agcgagtcag tgagcgagga agcggaagag cgcctgatgc      2340
ggtattttct ccttacgcat ctgtgcggta tttcacaccg caatggtgca ctctcagtac      2400
aatctgctct gatgccgcat agttaagcca gtatacactc cgctatcgct acgtgactgg      2460
gtcatggctg cgccccgaca cccgccaaca cccgctgacg cgccctgacg gcttgtctg      2520 ctcccggcat ccgcttacag acaagctgtg accgtctccg ggagctgcat gtgtcagagg      2580
ttttcaccgt catcaccgaa acgcgcgagg cagctgcggt aaagctcatc agcgtggtcg      2640
tgaagcgatt cacagatgtc tgcctgttca tccgcgtcca gctcgttgag tttctccaga      2700
agcgttaatg tctggcttct gataaagcgg ccatgttaa gggcggtttt ttcctgtttg      2760
gtcactgatg cctccgtgta aggggatttc tgttcatgg gggtaatgat accgatgaaa      2820
cgagagagga tgctcacgat acgggttact gatgatgaac atgcccggtt actggaacgt      2880
```

```
tgtgaggta  aacaactggc  ggtatggatg  cggcgggacc  agagaaaaat  cactcagggt   2940
caatgccagc  gcttcgttaa  tacagatgta  ggtgttccac  agggtagcca  gcagcatcct   3000
gcgatgcaga  tccggaacat  aatggtgcag  ggcgctgact  tccgcgtttc  cagactttac   3060
gaaacacgga  aaccgaagac  cattcatgtt  gttgctcagg  tcgcagacgt  tttgcagcag   3120
cagtcgcttc  acgttcgctc  gcgtatcggt  gattcattct  gctaaccagt  aaggcaaccc   3180
cgccagccta  gccgggtcct  caacgacagg  agcacgatca  tgcgcacccg  tggccaggac   3240
ccaacgctgc  ccgagatgcg  ccgcgtgcgg  ctgctggaga  tggcggacgc  gatggatatg   3300
ttctgccaag  ggttggtttg  cgcattcaca  gttctccgca  agaattgatt  ggctccaatt   3360
cttggagtgg  tgaatccgtt  agcgaggtgc  cgccggcttc  cattcaggtc  gaggtggccc   3420
ggctccatgc  accgcgacgc  aacgcgggga  ggcagacaag  gtatagggcg  cgcctacaa    3480
tccatgccaa  cccgttccat  gtgctcgccg  aggcggcata  aatcgccgtg  acgatcagcg   3540
gtccaatgat  cgaagttagg  ctggtaagag  ccgcgagcga  tccttgaagc  tgtccctgat   3600
ggtcgtcatc  tacctgcctg  acagcatgg   cctgcaacgc  gggcatcccg  atgccgccgg   3660
aagcgagaag  aatcataatg  gggaaggcca  tccagcctcg  cgtcgcgaac  gccagcaaga   3720
cgtagcccag  cgcgtcggcc  gccatgccgg  cgataatggc  ctgcttctcg  ccgaaacgtt   3780
tggtggcggg  accagtgacg  aaggcttgag  cgagggcgtg  caagattccg  aataccgcaa   3840
gcgacaggcc  gatcatcgtc  gcgctccagc  gaaagcggtc  ctcgccgaaa  atgacccaga   3900
gcgctgccgg  cacctgtcct  acgagttgca  tgataaagaa  gacagtcata  agtgcggcga   3960
cgatagtcat  gccccgcgcc  caccggaagg  agctgactgg  gttgaaggct  ctcaagggca   4020
tcggtcgaga  tccccggtgcc  taatgagtga  gctaacttac  attaattgcg  ttgcgctcac   4080
tgcccgcttt  ccagtcggga  aacctgtcgt  gccagctgca  ttaatgaatc  ggccaacgcg   4140
cggggagagg  cggtttgcgt  attgggcgcc  agggtggttt  ttcttttcac  cagtgagacg   4200
ggcaacagct  gattgccctt  caccgcctgg  ccctgagaga  gttgcagcaa  gcggtccacg   4260
ctggtttgcc  ccagcaggcg  aaaatcctgt  ttgatggtgg  ttaacggcgg  atataacat    4320
gagctgtctt  cggtatcgtc  gtatcccact  accgagatat  ccgcaccaac  gcgcagcccg   4380
gactcggtaa  tggcgcgcat  tgcgcccagc  gccatctgat  cgttggcaac  cagcatcgca   4440
gtgggaacga  tgccctcatt  cagcatttgc  atggtttgtt  gaaaaccgga  catggcactc   4500
cagtcgcctt  cccgttccgc  tatcggctga  atttgattgc  gagtgagata  tttatgccag   4560
ccagccagac  gcagacgcgc  cgagacagaa  cttaatgggc  ccgctaacag  cgcgatttgc   4620
tggtgaccca  atgcgaccag  atgctccacg  cccagtcgcg  taccgtcttc  atgggagaaa   4680
ataatactgt  tgatgggtgt  ctggtcagag  acatcaagaa  ataacgccgg  aacattagtg   4740
caggcagctt  ccacagcaat  ggcatcctgg  tcatccagcg  gatagttaat  gatcagccca   4800
ctgacgcgtt  gcgcgagaag  attgtgcacc  gccgctttac  aggcttcgac  gccgcttcgt   4860
tctaccatcg  acaccaccac  gctggcaccc  agttgatcgg  cgcgagattt  aatcgccgcg   4920
acaatttgcg  acggcgcgtg  cagggccaga  ctggaggtgg  caacgccaat  cagcaacgac   4980
tgtttgcccg  ccagttgttg  tgccacgcgg  ttgggaatgt  aattcagctc  cgccatcgcc   5040
gcttccactt  tttcccgcgt  tttcgcagaa  acgtggctgg  cctggttcac  cacgcgggaa   5100
acggtctgat  aagagacacc  ggcatactct  gcgacatcgt  ataacgttac  tggtttcaca   5160
ttcaccaccc  tgaattgact  ctcttccggg  cgctatcatg  ccataccgcg  aaaggttttg   5220
```

| | | | | |
|---|---|---|---|---|
| cgccattcga | tggtgtccgg | gatctcgacg | ctctccctta | tgcgactcct | gcattaggaa | 5280 |
| gcagcccagt | agtaggttga | ggccgttgag | caccgccgcc | gcaaggaatg | gtgcatgcaa | 5340 |
| ggagatggcg | cccaacagtc | ccccggccac | ggggcctgcc | accataccca | cgccgaaaca | 5400 |
| agcgctcatg | agcccgaagt | ggcgagcccg | atcttcccca | tcggtgatgt | cggcgatata | 5460 |
| ggcgccagca | accgcacctg | tggcgccggt | gatgccggcc | acgatgcgtc | cggcgtagag | 5520 |
| gatcgagatc | tcgatcccgc | gaaattaata | cgactcacta | tagggaatt | gtgagcggat | 5580 |
| aacaattccc | ctctagaaat | aattttgttt | aactttaaga | aggagatata | catatgcggg | 5640 |
| gttctcatca | tcatcatcat | catggtatgg | ctagcatgac | tggtggacag | caaatgggtc | 5700 |
| gggatctgta | cgacgatgac | gataaggatc | atcccttcac | catgcgtcgt | tctgcgaact | 5760 |
| acgaacctaa | cagctgggac | tatgattacc | tgctgtcctc | cgacacggac | gagtccatcg | 5820 |
| aagtatacaa | agacaaagcg | aaaaagctgg | aagccgaagt | tcgtcgcgag | attaataacg | 5880 |
| aaaaagcaga | atttctgacc | ctgctggaac | tgattgacaa | cgtccagcgc | ctgggcctgg | 5940 |
| gttaccgttt | cgagtctgat | atccgtggtg | cgctggatcg | cttcgtttcc | tccggcggct | 6000 |
| tcgatgcggt | aaccaagact | tccctgcacg | gtacggcact | gtctttccgt | ctgctgcgtc | 6060 |
| aacacggttt | tgaggtttct | caggaagcgt | tcagcggctt | caaagaccaa | aacggcaact | 6120 |
| tcctggagaa | cctgaaggaa | gatatcaaag | ctatcctgag | cctgtacgag | gccagcttcc | 6180 |
| tggctctgga | aggcgaaaac | atcctggacg | aggcgaaggt | tttcgcaatc | tctcatctga | 6240 |
| aagaactgtc | tgaagaaaag | atcggtaaag | agctggcaga | acaggtgaac | catgcactgg | 6300 |
| aactgccact | gcatcgccgt | actcagcgtc | tggaagcagt | atggtctatc | gaggcctacc | 6360 |
| gtaaaaagga | ggacgcgaat | caggttctgc | tggagctggc | aattctggat | tacaacatga | 6420 |
| tccagtctgt | ataccagcgt | gatctgcgtg | aaacgtcccg | ttggtggcgt | cgtgtgggtc | 6480 |
| tggcgaccaa | actgcacttt | gctcgtgacc | gcctgattga | gagcttctac | tgggccgtgg | 6540 |
| gtgtagcatt | cgaaccgcaa | tactccgact | gccgtaactc | cgtcgcaaaa | atgttttctt | 6600 |
| tcgtaaccat | tatcgacgat | atctacgatg | tatacggcac | cctggacgaa | ctggagctgt | 6660 |
| ttactgatgc | agttgagcgt | tgggacgtaa | acgccatcaa | cgacctgccg | gattacatga | 6720 |
| aactgtgctt | tctggctctg | tataacacta | ttaacgaaat | cgcctacgac | aacctgaaag | 6780 |
| ataaaggtga | gaacatcctg | ccgtatctga | ccaaagcctg | ggctgacctg | tgcaacgctt | 6840 |
| tcctgcaaga | agccaagtgg | ctgtacaaca | aatctactcc | gaccttttgac | gactacttcg | 6900 |
| gcaacgcatg | gaaatcctct | tctggcccgc | tgcaactggt | gttcgcttac | ttcgctgtcg | 6960 |
| tgcagaacat | taaaaaggaa | gagatcgaaa | acctgcaaaa | ataccatgac | accatctctc | 7020 |
| gtccttccca | tatcttccgt | ctgtgcaatg | acctggctag | cgcgtctgcg | gaaattgcgc | 7080 |
| gtggtgaaac | cgcaaatagc | gtttcttgtt | acatgcgcac | taaaggtatc | tccgaagaac | 7140 |
| tggctaccga | aagcgtgatg | aatctgatcg | atgaaacctg | gaaaagatg | aacaaggaaa | 7200 |
| aactgggtgg | tagcctgttc | gcgaaaccgt | tcgtggaaac | cgcgatcaac | ctggcacgtc | 7260 |
| aatctcactg | cacttatcat | aacggcgacg | cgcataccac | tccggatgag | ctgacccgca | 7320 |
| aacgcgttct | gtctgtaatc | actgaaccga | ttctgccgtt | tgaacgctaa | | 7370 |

<210> SEQ ID NO 11
<211> LENGTH: 578
<212> TYPE: PRT
<213> ORGANISM: Populus tremuloides

<400> SEQUENCE: 11

-continued

```
Met Arg Gly Ser His His His His His His Gly Met Ala Ser Met Thr
 1               5                          10                 15
Gly Gly Gln Gln Met Gly Arg Asp Leu Tyr Asp Asp Asp Lys Asp
             20                  25                  30
His Pro Phe Thr Met Arg Arg Ser Ala Asn Tyr Glu Pro Asn Ser Trp
             35                  40                  45
Asp Tyr Asp Tyr Leu Leu Ser Ser Asp Thr Asp Glu Ser Ile Glu Val
         50                  55                  60
His Lys Asp Lys Ala Lys Lys Leu Glu Ala Glu Val Arg Arg Glu Ile
 65                  70                  75                  80
Asn Asn Glu Lys Ala Glu Phe Leu Thr Leu Leu Glu Leu Ile Asp Asn
                 85                  90                  95
Val Gln Arg Leu Gly Leu Gly Tyr Arg Phe Glu Ser Asp Ile Arg Arg
             100                 105                 110
Ala Leu Asp Arg Phe Val Ser Ser Gly Gly Phe Asp Gly Val Thr Lys
             115                 120                 125
Thr Ser Leu His Gly Thr Ala Leu Ser Phe Arg Leu Leu Arg Gln His
130                 135                 140
Gly Phe Glu Val Ser Gln Glu Ala Phe Ser Gly Phe Lys Asp Gln Asn
145                 150                 155                 160
Gly Asn Phe Leu Glu Asn Leu Lys Glu Asp Ile Lys Ala Ile Leu Ser
                 165                 170                 175
Leu Tyr Glu Ala Ser Phe Leu Ala Leu Glu Gly Glu Asn Ile Leu Asp
             180                 185                 190
Glu Ala Lys Val Phe Ala Ile Ser His Leu Lys Glu Leu Ser Glu Glu
             195                 200                 205
Lys Ile Gly Lys Glu Leu Ala Glu Gln Val Ser His Ala Leu Glu Leu
210                 215                 220
Pro Leu His Arg Arg Thr Gln Arg Leu Glu Ala Val Trp Ser Ile Glu
225                 230                 235                 240
Ala Tyr Arg Lys Lys Glu Asp Ala Asn Gln Val Leu Leu Glu Leu Ala
             245                 250                 255
Ile Leu Asp Tyr Asn Met Ile Gln Ser Val Tyr Gln Arg Asp Leu Arg
             260                 265                 270
Glu Thr Ser Arg Trp Trp Arg Arg Val Gly Leu Ala Thr Lys Leu His
             275                 280                 285
Phe Ala Arg Asp Arg Leu Ile Glu Ser Phe Tyr Trp Ala Val Gly Val
             290                 295                 300
Ala Phe Glu Pro Gln Tyr Ser Asp Cys Arg Asn Ser Val Ala Lys Met
305                 310                 315                 320
Phe Ser Phe Val Thr Ile Ile Asp Asp Ile Tyr Asp Val Tyr Gly Thr
                 325                 330                 335
Leu Asp Glu Leu Glu Leu Phe Thr Asp Ala Val Glu Arg Trp Asp Val
             340                 345                 350
Asn Ala Ile Asn Asp Leu Pro Asp Tyr Met Lys Leu Cys Phe Leu Ala
             355                 360                 365
Leu Tyr Asn Thr Ile Asn Glu Ile Ala Tyr Asp Asn Leu Lys Asp Lys
             370                 375                 380
Gly Glu Asn Ile Leu Pro Tyr Leu Thr Lys Ala Trp Ala Asp Leu Cys
385                 390                 395                 400
Asn Ala Phe Leu Gln Glu Ala Lys Trp Leu Tyr Asn Lys Ser Thr Pro
                 405                 410                 415
```

Thr Phe Asp Asp Tyr Phe Gly Asn Ala Trp Lys Ser Ser Gly Pro
                420                 425                 430

Leu Gln Leu Ile Phe Ala Tyr Phe Ala Val Val Gln Asn Ile Lys Lys
            435                 440                 445

Glu Glu Ile Glu Asn Leu Gln Lys Tyr His Asp Ile Ile Ser Arg Pro
        450                 455                 460

Ser His Ile Phe Arg Leu Cys Asn Asp Leu Ala Ser Ala Ser Ala Glu
465                 470                 475                 480

Ile Ala Arg Gly Glu Thr Ala Asn Ser Val Ser Cys Tyr Met Arg Thr
                485                 490                 495

Lys Gly Ile Ser Glu Glu Leu Ala Thr Glu Ser Val Met Asn Leu Ile
            500                 505                 510

Asp Glu Thr Trp Lys Lys Met Asn Lys Glu Lys Leu Gly Gly Ser Leu
        515                 520                 525

Phe Ala Lys Pro Phe Val Glu Thr Ala Ile Asn Leu Ala Arg Gln Ser
    530                 535                 540

His Cys Thr Tyr His Asn Gly Asp Ala His Thr Ser Pro Asp Glu Leu
545                 550                 555                 560

Thr Arg Lys Arg Val Leu Ser Val Ile Thr Glu Pro Ile Leu Pro Phe
                565                 570                 575

Glu Arg

<210> SEQ ID NO 12
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 12
cgtcgttctg cgaactacga acctaacagc tgggactatg attacctgct gtcctccgac      60
acggacgagt ccatcgaagt acacaaagac aaagcgaaaa agctggaagc cgaagttcgt     120
cgcgagatta ataacgaaaa agcagaattt ctgaccctgc tggaactgat tgacaacgtc     180
cagcgcctgg gcctgggtta ccgtttcgag tctgatatcc gtcgtgcgct ggatcgcttc     240
gtttcctccg gcggcttcga tggcgtaacc aagacttccc tgcacggtac ggcactgtct     300
ttccgtctgc tgcgtcaaca cggttttgag gtttctcagg aagcgttcag cggcttcaaa     360
gaccaaaacg gcaacttcct ggagaacctg aaggaagata tcaaagctat cctgagcctg     420
tacgaggcca gcttcctggc tctggaaggc gaaacatcc tggacgaggc gaaggttttc      480
gcaatctctc atctgaaaga actgtctgaa gaaaagatcg gtaaagagct ggcagaacag     540
gtgtcccatg cactggaact gccactgcat cgccgtactc agcgtctgga agcagtatgg     600
tctatcgagg cctaccgtaa aaaggaggac gcgaaccagg ttctgctgga gctggcaatt     660
ctggattaca acatgatcca gtctgtatac cagcgtgatc tgcgtgaaac gtcccgttgg     720
tggcgtcgtg tgggtctggc gaccaaactg cactttgctc gtgaccgcct gattgagagc     780
ttctactggg ccgtgggtgt agcattcgaa ccgcaatact ccgactgccg taactccgtc     840
gcaaaaatgt ttctttcgt aaccattatc gacgatatct cgatgtata cggcaccctg      900
gacgaactgg agctgtttac tgatgcagtt gagcgttggg acgtaaacgc catcaacgac     960
ctgccggatt acatgaaact gtgctttctg ctctgtata acactattaa cgaaatcgcc    1020
tacgacaacc tgaaagataa aggtgagaac atcctgccgt atctgaccaa agcctgggct    1080
gacctgtgca acgctttcct gcaagaagcc aagtggctgt acaacaaatc tactccgacc    1140

-continued

```
tttgacgact acttcggcaa cgcatggaaa tcctcttctg gcccgctgca actgatcttc      1200
gcttacttcg ctgtcgtgca gaacattaaa aaggaagaga tcgaaaacct gcaaaaatac      1260
catgacatca tctctcgtcc ttcccatatc ttccgtctgt gcaatgacct ggctagcgcg      1320
tctgcggaaa ttgcgcgtgg tgaaaccgca aatagcgttt cttgttacat gcgcactaaa      1380
ggtatctccg aagaactggc taccgaaagc gtgatgaatc tgatcgatga acctggaaa       1440 aagatgaaca aggaaaaact gggtggtagc ctgttcgcga aaccgttcgt ggaaaccgcg      1500
atcaacctgg cacgtcaatc tcactgcact tatcataacg gcgacgcgca tacctctccg      1560
gatgagctga cccgcaaacg cgttctgtct gtaatcactg aaccgattct gccgtttgaa      1620
cgctaaaagg gcgagctcaa cgatccggct gctaacaaag cccgaaagga agctgagttg      1680
gctgctgcca ccgctgagca ataactagca taaccccttg gggcctctaa acgggtcttg      1740
aggagttttt tgctgaaagg aggaactata tccggatatc ccgcaagagg cccggcagta      1800
ccggcataac caagcctatg cctacagcat ccagggtgac ggtgccgagg atgacgatga      1860
gcgcattgtt agatttcata cacggtgcct gactgcgtta gcaatttaac tgtgataaac      1920
taccgcatta agcttatcg atgataagct gtcaaacatg agaattaatt cttgaagacg       1980
aaagggcctc gtgatacgcc tatttttata ggttaatgtc atgataataa tggtttctta      2040
gacgtcaggt ggcacttttc ggggaaatgt gcgcggaacc ctatttgtt tattttcta        2100 aatacattca aatatgtatc cgctcatgag acaataaccc tgataaatgc ttcaataata      2160
ttgaaaaagg aagagtatga ttgaacaaga tggattgcac gcaggttctc cggccgcttg      2220
ggtggagagg ctattcggct atgactgggc acaactgaca atcggctgct ctgatgccgc      2280
cgtgttccgg ctgtcagcgc aggggcgccc ggttcttttt gtcaagaccg acctgtccgg      2340
tgccctgaat gaactgcagg acgaggcagc gcggctatcg tggctggcca cgacgggcgt      2400
tccttgcgca gctgtgctcg acgttgtcac tgaagcggga agggactggc tgctattggg      2460
cgaagtgccg gggcaggatc tcctgtcatc tcaccttgct cctgccgaga agtatccat       2520 catggctgat gcaatgcggc ggctgcatac gcttgatccg gctacctgcc cattcgacca      2580
ccaagcgaaa catcgcatcg agcgggcacg tactcggatg gaagccggtc ttgtcgatca      2640
ggatgatctg gacgaagagc atcagggct cgcgccagcc gaactgttcg ccaggctcaa       2700
ggcgcgcatg cccgacggcg aggatctcgt cgtgacacat ggcgatgcct gcttgccgaa      2760
tatcatggtg gaaaatggcc gcttttctgg attcatcgac tgtggccggc tgggtgtggc      2820
ggaccgctat caggacatag cgttggctac ccgtgatatt gctgaagagc ttggcggcga      2880
atgggctgac cgcttcctcg tgctttacgg tatcgccgct cccgattcgc agcgcatcgc      2940
cttctatcgc cttcttgacg agttcttctg agcgggactc tggggttcga atgaccgac       3000 caagcgacgc ctaactgtca gaccaagttt actcatatat actttagatt gatttaaaac      3060 ttcatttta atttaaaagg atctaggtga agatccttt tgataatctc atgaccaaaa        3120 tccc tt aacg tgagttttcg ttccactgag cgtcagaccc cgtagaaaag atcaaaggat    3180
cttcttgaga tcctttttt ctgcgcgtaa tctgctgctt gcaaacaaaa aaaccaccgc       3240
taccagcggt ggtttgtttg ccggatcaag agctaccaac tctttttccg aaggtaactg      3300
gcttcagcag agcgcagata ccaaatactg tccttctagt gtagccgtag ttaggccacc      3360
acttcaagaa ctctgtagca ccgcctacat acctcgctct gctaatcctg ttaccagtgg      3420
ctgctgccag tggcgataag tcgtgtctta ccgggttgga ctcaagacga tagttaccgg      3480
```

```
ataaggcgca gcggtcgggc tgaacggggg gttcgtgcac acagcccagc ttggagcgaa    3540
cgacctacac cgaactgaga tacctacagc gtgagctatg agaaagcgcc acgcttcccg    3600
aagggagaaa ggcggacagg tatccggtaa gcggcagggt cggaacagga gagcgcacga    3660
gggagcttcc aggggaaac gcctggtatc tttatagtcc tgtcgggttt cgccacctct     3720
gacttgagcg tcgattttg tgatgctcgt caggggggcg gagcctatgg aaaaacgcca     3780
gcaacgcggc cttttacgg ttcctggcct ttttgctggcc ttttgctcac atgttctttc   3840
ctgcgttatc ccctgattct gtggataacc gtattaccgc ctttgagtga gctgataccg    3900
ctcgccgcag ccgaacgacc gagcgcagcg agtcagtgag cgaggaagcg gaagagcgcc    3960
tgatgcggta ttttctcctt acgcatctgt gcggtatttc acaccgcaat ggtgcactct    4020
cagtacaatc tgctctgatg ccgcatagtt aagccagtat acactccgct atcgctacgt    4080
gactgggtca tggctgcgcc ccgacacccg ccaacacccg ctgacgcgcc ctgacgggct    4140
tgtctgctcc cggcatccgc ttacagacaa gctgtgaccg tctccgggag ctgcatgtgt    4200
cagaggtttt caccgtcatc accgaaaacgc gcgaggcagc tgcggtaaag ctcatcagcg    4260
tggtcgtgaa gcgattcaca gatgtctgcc tgttcatccg cgtccagctc gttgagtttc    4320
tccagaagcg ttaatgtctg gcttctgata aagcgggcca tgttaagggc ggttttttcc    4380
tgtttggtca ctgatgcctc cgtgtaaggg ggatttctgt tcatgggggt aatgataccg    4440
atgaaacgag agaggatgct cacgatacgg gttactgatg atgaacatgc ccggttactg    4500
gaacgttgtg agggtaaaca actggcggta tggatgcggc gggaccagag aaaaatcact    4560
cagggtcaat gccagcgctt cgttaataca gatgtaggtg ttccacaggg tagccagcag    4620
catcctgcga tgcagatccg gaacataatg gtgcagggcg ctgacttccg cgtttccaga    4680
ctttacgaaa cacggaaacc gaagaccatt catgttgttg ctcaggtcgc agacgttttg    4740
cagcagcagt cgcttcacgt tcgctcgcgt atcggtgatt cattctgcta accagtaagg    4800
caaccccgcc agcctagccg ggtcctcaac gacaggagca cgatcatgcg cacccgtggc    4860
caggacccaa cgctgcccga tgcgccgc gtgcggctgc tggagatggc ggacgcgatg    4920
gatatgttct gccaagggtt ggtttgcgca ttcacagttc tccgcaagaa ttgattggct    4980
ccaattcttg gagtggtgaa tccgttagcg aggtgccgcc ggcttccatt caggtcgagg    5040
tggcccggct ccatgcaccg cgacgcaacg cggggaggca gacaaggtat agggcggcgc    5100
ctacaatcca tgccaacccg ttccatgtgc tcgccgaggc ggcataaatc gccgtgacga    5160
tcagcggtcc aatgatcgaa gttaggctgg taagagccgc gagcgatcct tgaagctgtc    5220
cctgatggtc gtcatctacc tgcctggaca gcatggcctg caacgcgggc atcccgatgc    5280
cgccggaagc gagaagaatc ataatgggga aggccatcca gcctcgcgtc gcgaacgcca    5340
gcaagacgta gcccagcgcg tcggccgcca tgccggcgat aatggcctgc ttctcgccga    5400
aacgtttggt ggcgggacca gtgacgaagg cttgagcgag ggcgtgcaag attccgaata    5460
ccgcaagcga caggccgatc atcgtcgcgc tccagcgaaa gcggtcctcg ccgaaaatga    5520
cccagagcgc tgccggcacc tgtcctacga gttgcatgat aaagaagaca gtcataagtg    5580
cggcgacgat agtcatgccc gcgcccacc ggaaggagct gactggggttg aaggctctca    5640
agggcatcgg tcgagatccc ggtgcctaat gagtgagcta acttacatta attgcgttgc    5700
gctcactgcc cgctttccag tcgggaaacc tgtcgtgcca gctgcattaa tgaatcggcc    5760
aacgcgcggg gagaggcggt ttgcgtattg gcgccaggtg gttttttcct tttcaccagt    5820
gagacgggca acagctgatt gcccttcacc gcctggccct gagagagttg cagcaagcgg    5880
```

```
tccacgctgg tttgccccag caggcgaaaa tcctgtttga tggtggttaa cggcgggata    5940
taacatgagc tgtcttcggt atcgtcgtat cccactaccg agatatccgc accaacgcgc    6000
agcccggact cggtaatggc gcgcattgcg cccagcgcca tctgatcgtt ggcaaccagc    6060
atcgcagtgg gaacgatgcc ctcattcagc atttgcatgg tttgttgaaa accggacatg    6120
gcactccagt cgccttcccg ttccgctatc ggctgaattt gattgcgagt gagatattta    6180
tgccagccag ccagacgcag acgcgccgag acagaactta atgggcccgc taacagcgcg    6240
atttgctggt gacccaatgc gaccagatgc tccacgccca gtcgcgtacc gtcttcatgg    6300
gagaaaataa tactgttgat gggtgtctgg tcagagacat caagaaataa cgccggaaca    6360
ttagtgcagg cagcttccac agcaatggca tcctggtcat ccagcggata gttaatgatc    6420
agcccactga cgcgttgcgc gagaagattg tgcaccgccg ctttacaggc ttcgacgccg    6480
cttcgttcta ccatcgacac caccacgctg cacccagtt gatcggcgcg agatttaatc    6540
gccgcgacaa tttgcgacgg cgcgtgcagg gccagactgg aggtggcaac gccaatcagc    6600
aacgactgtt tgcccgccag ttgttgtgcc acgcggttgg gaatgtaatt cagctccgcc    6660
atcgccgctt ccacttttc ccgcgttttc gcagaaacgt ggctggcctg gttcaccacg    6720
cgggaaacgg tctgataaga gacaccggca tactctgcga catcgtataa cgttactggt    6780
ttcacattca ccaccctgaa ttgactctct tccgggcgct atcatgccat accgcgaaag    6840
gttttgcgcc attcgatggt gtccgggatc tcgacgctct cccttatgcg actcctgcat    6900
taggaagcag cccagtagta ggttgaggcc gttgagcacc gccgccgcaa ggaatggtgc    6960
atgcaaggag atggcgccca acagtccccc ggccacgggg cctgccacca tacccacgcc    7020
gaaacaagcg ctcatgagcc cgaagtggcg agcccgatct tccccatcgg tgatgtcggc    7080
gatataggcg ccagcaaccg cacctgtggc gccggtgatg ccggccacga tgcgtccggc    7140
gtagaggatc gagatctcga tcccgcgaaa ttaatacgac tcactatagg gaattgtga    7200
gcggataaca attcccctct agaaataatt ttgtttaact ttaagaagga gatatacata    7260
tgcggggttc tcatcatcat catcatcatg gtatggctag catgactggt ggacagcaaa    7320
tgggtcggga tctgtacgac gatgacgata aggatcatcc cttcaccatg                7370
```

<210> SEQ ID NO 13
<211> LENGTH: 578
<212> TYPE: PRT
<213> ORGANISM: Artificial Sequence
<220> FEATURE:
<223> OTHER INFORMATION: Synthetic Construct

<400> SEQUENCE: 13

```
Met Arg Gly Ser His His His His His Gly Met Ala Ser Met Thr
 1               5                  10                  15

Gly Gly Gln Gln Met Gly Arg Asp Leu Tyr Asp Asp Asp Lys Asp
             20                  25                  30

His Pro Phe Thr Met Arg Arg Ser Ala Asn Tyr Glu Pro Asn Ser Trp
         35                  40                  45

Asp Tyr Asp Tyr Leu Leu Ser Ser Asp Thr Asp Glu Ser Ile Glu Val
 50                  55                  60

Tyr Lys Asp Lys Ala Lys Lys Leu Glu Ala Glu Val Arg Arg Glu Ile
 65                  70                  75                  80

Asn Asn Glu Lys Ala Glu Phe Leu Thr Leu Leu Glu Leu Ile Asp Asn
                 85                  90                  95
```

-continued

```
Val Gln Arg Leu Gly Leu Gly Tyr Arg Phe Glu Ser Asp Ile Arg Arg
                100                 105                 110

Ala Leu Asp Arg Phe Val Ser Ser Gly Gly Phe Asp Ala Val Thr Lys
            115                 120                 125

Thr Ser Leu His Ala Thr Ala Leu Ser Phe Arg Leu Leu Arg Gln His
        130                 135                 140

Gly Phe Glu Val Ser Gln Glu Ala Phe Ser Gly Phe Lys Asp Gln Asn
145                 150                 155                 160

Gly Asn Phe Leu Glu Asn Leu Lys Glu Asp Ile Lys Ala Ile Leu Ser
                165                 170                 175

Leu Tyr Glu Ala Ser Phe Leu Ala Leu Glu Gly Glu Asn Ile Leu Asp
            180                 185                 190

Glu Ala Lys Val Phe Ala Ile Ser His Leu Lys Glu Leu Ser Glu Glu
        195                 200                 205

Lys Ile Gly Lys Asp Leu Ala Glu Gln Val Asn His Ala Leu Glu Leu
210                 215                 220

Pro Leu His Arg Arg Thr Gln Arg Leu Glu Ala Val Leu Ser Ile Glu
225                 230                 235                 240

Ala Tyr Arg Lys Lys Glu Asp Ala Asp Gln Val Leu Leu Glu Leu Ala
            245                 250                 255

Ile Leu Asp Tyr Asn Met Ile Gln Ser Val Tyr Gln Arg Asp Leu Arg
        260                 265                 270

Glu Thr Ser Arg Trp Trp Arg Arg Val Gly Leu Ala Thr Lys Leu His
    275                 280                 285

Phe Ala Arg Asp Arg Leu Ile Glu Ser Phe Tyr Trp Ala Val Gly Val
290                 295                 300

Ala Phe Glu Pro Gln Tyr Ser Asp Cys Arg Asn Ser Val Ala Lys Met
305                 310                 315                 320

Phe Ser Phe Val Thr Ile Asp Asp Ile Tyr Asp Val Tyr Gly Thr
            325                 330                 335

Leu Asp Glu Leu Glu Leu Phe Thr Asn Ala Val Glu Arg Trp Asp Val
        340                 345                 350

Asn Ala Ile Asp Asp Leu Pro Asp Tyr Met Lys Leu Cys Phe Leu Ala
    355                 360                 365

Leu Tyr Asn Thr Ile Asn Glu Ile Ala Tyr Asp Asn Leu Lys Glu Lys
370                 375                 380

Gly Glu Asn Ile Leu Pro Tyr Leu Thr Lys Ala Trp Ala Asp Leu Cys
385                 390                 395                 400

Asn Ala Phe Leu Gln Glu Ala Lys Trp Leu Tyr Asn Lys Ser Thr Pro
            405                 410                 415

Thr Phe Asp Glu Tyr Phe Gly Asn Ala Trp Lys Ser Ser Gly Pro
        420                 425                 430

Leu Gln Leu Val Phe Ala Tyr Phe Ala Val Val Gln Asn Ile Lys Lys
    435                 440                 445

Glu Glu Ile Glu Asn Leu Gln Lys Tyr His Asp Ile Ile Ser Arg Pro
450                 455                 460

Ser His Ile Phe Arg Leu Cys Asn Asp Leu Ala Ser Ala Ser Ala Glu
465                 470                 475                 480

Ile Ala Arg Gly Glu Thr Ala Asn Ser Val Ser Cys Tyr Met Arg Thr
            485                 490                 495

Lys Gly Ile Ser Glu Glu Leu Ala Thr Glu Ser Val Met Asn Leu Ile
        500                 505                 510

Asp Glu Thr Trp Lys Lys Met Asn Lys Glu Lys Leu Gly Gly Ser Leu
```

```
                515                 520                 525
Phe Ala Lys Pro Phe Val Glu Thr Ala Ile Asn Leu Ala Arg Gln Ser
            530                 535                 540

His Cys Thr Tyr His Asn Gly Asp Ala His Thr Ser Pro Asp Glu Leu
545                 550                 555                 560

Thr Arg Lys Arg Val Leu Ser Val Ile Thr Glu Pro Ile Leu Pro Phe
                565                 570                 575

Glu Arg

<210> SEQ ID NO 14
<211> LENGTH: 7370
<212> TYPE: DNA
<213> ORGANISM: Artificial Sequence
<220> FEATURE:
<223> OTHER INFORMATION: Synthetic Construct

<400> SEQUENCE: 14
```

| | | | | | |
|---|---|---|---|---|---|
| cgtcgttctg | cgaactacga | acctaacagc | tgggactatg | attacctgct | gtcctccgac | 60 |
| acggacgagt | ccatcgaagt | atacaaagac | aaagcgaaaa | agctggaagc | cgaagttcgt | 120 |
| cgcgagatta | taacgaaaaa | agcagaattt | ctgaccctgc | tggaactgat | tgacaacgtc | 180 |
| cagcgcctgg | gcctgggtta | ccgtttcgag | tctgatatcc | gtcgtgcgct | ggatcgcttc | 240 |
| gtttcctccg | gcggcttcga | tgcggtaacc | aagacttccc | tgcacgcgac | ggcactgtct | 300 |
| ttccgtctgc | tgcgtcaaca | cggttttgag | gtttctcagg | aagcgttcag | cggcttcaaa | 360 |
| gaccaaaacg | gcaacttcct | ggagaacctg | aaggaagata | tcaaagctat | cctgagcctg | 420 |
| tacgaggcca | gcttcctggc | tctggaaggc | gaaaacatcc | tggacgaggc | gaaggttttc | 480 |
| gcaatctctc | atctgaaaga | actgtctgaa | gaaaagatcg | gtaaagatct | ggcagaacag | 540 |
| gtgaaccatg | cactggaact | gccactgcat | cgccgtactc | agcgtctgga | agcagtactg | 600 |
| tctatcgagg | cctaccgtaa | aaaggaggac | gcggatcagg | ttctgctgga | gctggcaatt | 660 |
| ctggattaca | acatgatcca | gtctgtatac | cagcgtgatc | tgcgtgaaac | gtcccgttgg | 720 |
| tggcgtcgtg | tgggtctggc | gaccaaactg | cactttgctc | gtgaccgcct | gattgagagc | 780 |
| ttctactggg | ccgtgggtgt | agcattcgaa | ccgcaatact | ccgactgccg | taactccgtc | 840 |
| gcaaaaatgt | tttctttcgt | aaccattatc | gacgatatct | acgatgtata | cggcaccctg | 900 |
| gacgaactgg | agctgtttac | taacgcagtt | gagcgttggg | acgtaaacgc | catcgacgat | 960 |
| ctgccggatt | acatgaaact | gtgctttctg | gctctgtata | acactattaa | cgaaatcgcc | 1020 |
| tacgacaacc | tgaaagaaaa | aggtgagaac | atcctgccgt | atctgaccaa | agcctgggct | 1080 |
| gacctgtgca | acgcttttcc | tcaagaagcc | aagtggctgt | acaacaaatc | tactccgacc | 1140 |
| tttgacgaat | acttcggcaa | cgcatggaaa | tcctcttctg | gcccgctgca | actggtgttc | 1200 |
| gcttacttcg | ctgtcgtgca | gaacattaaa | aaggaagaga | tcgaaaacct | gcaaaaatac | 1260 |
| catgacatca | tctctcgtcc | ttcccatatc | ttccgtctgt | gcaatgacct | ggctagcgcg | 1320 |
| tctgcggaaa | ttgcgcgtgg | tgaaaccgca | aatagcgttt | cttgttacat | gcgcactaaa | 1380 |
| ggtatctccg | aagaactggc | taccgaaagc | gtgatgaatc | tgatcgatga | aacctggaaa | 1440 |
| aagatgaaca | aggaaaaact | gggtggtagc | ctgttcgcga | accgttcgt | ggaaccgcg | 1500 |
| atcaacctgg | cacgtcaatc | tcactgcact | tatcataacg | gcgacgcgca | tacctctccg | 1560 |
| gatgagctga | cccgcaaacg | cgttctgtct | gtaatcactg | aaccgattct | gccgtttgaa | 1620 |
| cgctaaaagg | gcgagctcaa | cgatccggct | gctaacaaag | cccgaaagga | agctgagttg | 1680 |

-continued

```
gctgctgcca ccgctgagca ataactagca taaccccttg gggcctctaa acgggtcttg    1740
aggagttttt tgctgaaagg aggaactata tccggatatc ccgcaagagg cccggcagta    1800
ccggcataac caagcctatg cctacagcat ccagggtgac ggtgccgagg atgacgatga    1860
gcgcattgtt agatttcata cacggtgcct gactgcgtta gcaatttaac tgtgataaac    1920
taccgcatta agcttatcg atgataagct gtcaaacatg agaattaatt cttgaagacg    1980
aaagggcctc gtgatacgcc tatttttata ggttaatgtc atgataataa tggtttctta    2040
gacgtcaggt ggcacttttc ggggaaatgt gcgcggaacc cctatttgtt tattttccta    2100
aatacattca aatatgtatc cgctcatgag acaataaccc tgataaatgc ttcaataata    2160
ttgaaaaagg aagagtatga ttaacaaga tggattgcac gcaggttctc cggccgcttg    2220
ggtggagagg ctattcggct atgactggc acaactgaca atcggctgct ctgatgccgc     2280
cgtgttccgg ctgtcagcgc aggggcgccc ggttcttttt gtcaagaccg acctgtccgg    2340
tgccctgaat gaactgcagg acgaggcagc gcggctatcg tggctggcca cgacgggcgt    2400
tccttgcgca gctgtgctcg acgttgtcac tgaagcggga agggactggc tgctattggg    2460
cgaagtgccg gggcaggatc tcctgtcatc tcaccttgct cctgccgaga agtatccat     2520
catggctgat gcaatgcggc ggctgcatac gcttgatccg gctacctgcc cattcgacca    2580
ccaagcgaaa catcgcatcg agcgggcacg tactcggatg aagccggtc ttgtcgatca     2640
ggatgatctg gacgaagagc atcagggct cgcgccagcc gaactgttcg ccaggctcaa     2700
ggcgcgcatg cccgacggcg aggatctcgt cgtgacacat ggcgatgcct gcttgccgaa    2760
tatcatggtg gaaaatggcc gcttttctgg attcatcgac tgtggccggc tgggtgtggc    2820
ggaccgctat caggacatag cgttggctac ccgtgatatt gctgaagagc ttggcggcga    2880
atgggctgac cgcttcctcg tgctttacgg tatcgccgct cccgattcgc agcgcatcgc    2940
cttctatcgc cttcttgacg agttcttctg agcgggactc tggggttcga aatgaccgac    3000
caagcgacgc ctaactgtca gaccaagttt actcatatat actttagatt gatttaaaac    3060
ttcatttta atttaaaagg atctaggtga agatcctttt tgataatctc atgaccaaaa    3120
tcccttaacg tgagttttcg ttccactgag cgtcagaccc cgtagaaaag atcaaaggat    3180
cttcttgaga tccttttttt ctgcgcgtaa tctgctgctt gcaaacaaaa aaaccaccgc    3240
taccagcggt ggtttgtttg ccggatcaag agctaccaac tctttttccg aaggtaactg    3300
gcttcagcag agcgcagata ccaaatactg tccttctagt gtagccgtag ttaggccacc    3360
acttcaagaa ctctgtagca ccgcctacat acctcgctct gctaatcctg ttaccagtgg    3420
ctgctgccag tggcgataag tcgtgtctta ccgggttgga ctcaagacga tagttaccgg    3480
ataaggcgca gcggtcgggc tgaacggggg gttcgtgcac acagcccagc ttggagcgaa    3540
cgacctacac cgaactgaga tacctacagc gtgagctatg agaaagcgcc acgcttcccg    3600
aagggagaaa ggcggacagg tatccggtaa gcggcagggt cggaacagga gagcgcacga    3660
gggagcttcc agggggaaac gcctggtatc tttatagtcc tgtcgggttt cgccacctct    3720
gacttgagcg tcgatttttg tgatgctcgt caggggggcg gagcctatgg aaaaacgcca    3780
gcaacgcggc cttttacgg ttcctggcct tttgctggcc ttttgctcac atgttctttc     3840
ctgcgttatc ccctgattct gtggataacc gtattaccgc ctttgagtga gctgataccg    3900
ctcgccgcag ccgaacgacc gagcgcagcg agtcagtgag cgaggaagcg gaagagcgcc    3960
tgatgcggta ttttctcctt acgcatctgt gcggtatttc acaccgcaat ggtgcactct    4020
cagtacaatc tgctctgatg ccgcatagtt aagccagtat acactccgct atcgctacgt    4080
```

```
gactgggtca tggctgcgcc ccgacacccg ccaacacccg ctgacgcgcc ctgacgggct    4140
tgtctgctcc cggcatccgc ttacagacaa gctgtgaccg tctccgggag ctgcatgtgt    4200
cagaggtttt caccgtcatc accgaaacgc gcgaggcagc tgcggtaaag ctcatcagcg    4260
tggtcgtgaa gcgattcaca gatgtctgcc tgttcatccg cgtccagctc gttgagtttc    4320
tccagaagcg ttaatgtctg gcttctgata aagcgggcca tgttaagggc ggttttttcc    4380
tgtttggtca ctgatgcctc cgtgtaaggg ggatttctgt tcatgggggt aatgataccg    4440
atgaaacgag agaggatgct cacgatacgg gttactgatg atgaacatgc ccggttactg    4500
gaacgttgtg agggtaaaca actggcggta tggatgcggc gggaccagag aaaaatcact    4560
cagggtcaat gccagcgctt cgttaataca gatgtaggtg ttccacaggg tagccagcag    4620
catcctgcga tgcagatccg gaacataatg gtgcagggcg ctgacttccg cgttccaga     4680 ctttacgaaa cacggaaacc gaagaccatt catgttgttg ctcaggtcgc agacgttttg    4740
cagcagcagt cgcttcacgt tcgctcgcgt atcggtgatt cattctgcta accagtaagg    4800
caaccccgcc agcctagccg ggtcctcaac gacaggagca cgatcatgcg cacccgtggc    4860
caggacccaa cgctgcccga gatgcgccgc gtgcggctgc tggagatggc ggacgcgatg    4920
gatatgttct gccaagggtt ggtttgcgca ttcacagttc tccgcaagaa ttgattggct    4980
ccaattcttg gagtggtgaa tccgttagcg aggtgccgcc ggcttccatt caggtcgagg    5040
tggcccggct ccatgcaccg cgacgcaacg cggggaggca gacaaggtat agggcggcgc    5100
ctacaatcca tgccaacccg ttccatgtgc tcgccgaggc ggcataaatc gccgtgacga    5160
tcagcggtcc aatgatcgaa gttaggctgg taagagccgc gagcgatcct tgaagctgtc    5220
cctgatggtc gtcatctacc tgcctggaca gcatggcctg caacgcgggc atcccgatgc    5280
cgccggaagc gagaagaatc ataatgggga aggccatcca gcctcgcgtc gcgaacgcca    5340
gcaagacgta gcccagcgcg tcggccgcca tgccggcgat aatggcctgc ttctcgccga    5400
aacgtttggt ggcgggacca gtgacgaagg cttgagcgag ggcgtgcaag attccgaata    5460
ccgcaagcga caggccgatc atcgtcgcgc tccagcgaaa gcggtcctcg ccgaaaatga    5520
cccagagcgc tgccggcacc tgtcctacga gttgcatgat aaagaagaca gtcataagtg    5580
cggcgacgat agtcatgccc cgcgcccacc ggaaggagct gactgggttg aaggctctca    5640
agggcatcgg tcgagatccc ggtgcctaat gagtgagcta acttacatta attgcgttgc    5700
gctcactgcc cgctttccag tcgggaaacc tgtcgtgcca gctgcattaa tgaatcggcc    5760
aacgcgcggg gagaggcggt ttgcgtattg ggcgccaggg tggtttttct tttcaccagt    5820
gagacgggca acagctgatt gcccttcacc gcctggccct gagagagttg cagcaagcgg    5880
tccacgctgg tttgccccag caggcgaaaa tcctgtttga tggtggttaa cggcgggata    5940
taacatgagc tgtcttcggt atcgtcgtat cccactaccg agatatccgc accaacgcgc    6000
agcccggact cggtaatggc gcgcattgcg cccagcgcca tctgatcgtt ggcaaccagc    6060
atcgcagtgg gaacgatgcc ctcattcagc atttgcatgg tttgttgaaa accggacatg    6120
gcactccagt cgccttcccg ttccgctatc ggctgaattt gattgcgagt gagatattta    6180
tgccagccag ccagacgcag acgcgccgag acagaactta atgggcccgc taacagcgcg    6240
atttgctggt gacccaatgc gaccagatgc tccacgccca gtcgcgtacc gtcttcatgg    6300
gagaaaataa tactgttgat gggtgtctgg tcagagacat caagaaataa cgccggaaca    6360
ttagtgcagg cagcttccac agcaatggca tcctggtcat ccagcggata gttaatgatc    6420
```

| | |
|---|---|
| agcccactga cgcgttgcgc gagaagattg tgcaccgccg ctttacaggc ttcgacgccg | 6480 |
| cttcgttcta ccatcgacac caccacgctg gcacccagtt gatcggcgcg agatttaatc | 6540 |
| gccgcgacaa tttgcgacgg cgcgtgcagg gccagactgg aggtggcaac gccaatcagc | 6600 |
| aacgactgtt tgcccgccag ttgttgtgcc acgcggttgg gaatgtaatt cagctccgcc | 6660 |
| atcgccgctt ccactttttc ccgcgttttc gcagaaacgt ggctggcctg gttcaccacg | 6720 |
| cgggaaacgg tctgataaga gacaccggca tactctgcga catcgtataa cgttactggt | 6780 |
| ttcacattca ccaccctgaa ttgactctct tccgggcgct atcatgccat accgcgaaag | 6840 |
| gttttgcgcc attcgatggt gtccgggatc tcgacgctct cccttatgcg actcctgcat | 6900 |
| taggaagcag cccagtagta ggttgaggcc gttgagcacc ccgccgcaa ggaatggtgc | 6960 |
| atgcaaggag atggcgccca acagtccccc ggccacgggg cctgccacca tacccacgcc | 7020 |
| gaaacaagcg ctcatgagcc cgaagtggcg agcccgatct tccccatcgg tgatgtcggc | 7080 |
| gatataggcg ccagcaaccg cacctgtggc gccggtgatg ccggcacga tgcgtccggc | 7140 |
| gtagaggatc gagatctcga tcccgcgaaa ttaatacgac tcactatagg ggaattgtga | 7200 |
| gcggataaca attcccctct agaaataatt ttgtttaact ttaagaagga gatatacata | 7260 |
| tgcggggttc tcatcatcat catcatcatg gtatggctag catgactggt ggacagcaaa | 7320 |
| tgggtcggga tctgtacgac gatgacgata aggatcatcc cttcaccatg | 7370 |

<210> SEQ ID NO 15
<211> LENGTH: 7424
<212> TYPE: DNA
<213> ORGANISM: Artificial Sequence
<220> FEATURE:
<223> OTHER INFORMATION: Synthetic Construct

<400> SEQUENCE: 15

| | |
|---|---|
| aagggcgagc tcaacgatcc ggctgctaac aaagcccgaa aggaagctga gttggctgct | 60 |
| gccaccgctg agcaataact agcataaccc cttggggcct ctaaacgggt cttgaggagt | 120 |
| tttttgctga aaggaggaac tatatccgga tatcccgcaa gaggcccggc agtaccggca | 180 |
| taaccaagcc tatgcctaca gcatccaggg tgacggtgcc gaggatgacg atgagcgcat | 240 |
| tgttagattt catacacggt gcctgactgc gttagcaatt taactgtgat aaactaccgc | 300 |
| attaaagctt atcgatgata agctgtcaaa catgagaatt aattcttgaa gacgaaaggg | 360 |
| cctcgtgata cgcctatttt tataggttaa tgtcatgata ataatggttt cttagacgtc | 420 |
| aggtggcact tttcggggaa atgtgcgcgg aaccccatt tgtttatttt tctaaataca | 480 |
| ttcaaatatg tatccgctca tgagacaata accctgataa atgcttcaat aatattgaaa | 540 |
| aaggaagagt atgattgaac aagatggatt gcacgcaggt tctccggccg cttgggtgga | 600 |
| gaggctattc ggctatgact gggcacaact dcaatcggc tgctctgatg ccgccgtgtt | 660 |
| ccggctgtca gcgcagggc gcccggttct ttttgtcaag accgacctgt ccggtgccct | 720 |
| gaatgaactg caggacgagg cagcgcggct atcgtggctg gccacgacgg gcgttccttg | 780 |
| cgcagctgtg ctcgacgttg tcactgaagc gggaagggac tggctgctat gggcgaagt | 840 |
| gccggggcag gatctcctgt catctcacct tgctcctgcc gagaaagtat ccatcatggc | 900 |
| tgatgcaatg cggcggctgc atacgcttga tccggctacc tgcccattcg accaccaagc | 960 |
| gaaacatcgc atcgagcggg cacgtactcg gatggaagcc ggtcttgtcg atcaggatga | 1020 |
| tctggacgaa gagcatcagg ggctcgcgcc agccgaactg ttcgccaggc tcaaggcgcg | 1080 |
| catgcccgac ggcgaggatc tcgtcgtgac acatggcgat gcctgcttgc cgaatatcat | 1140 |

-continued

```
ggtggaaaat ggccgctttt ctggattcat cgactgtggc cggctgggtg tggcggaccg    1200
ctatcaggac atagcgttgg ctacccgtga tattgctgaa gagcttggcg gcgaatgggc    1260
tgaccgcttc ctcgtgcttt acggtatcgc cgctcccgat tcgcagcgca tcgccttcta    1320
tcgccttctt gacgagttct tctgagcggg actctgggt tcgaaatgac cgaccaagcg     1380
acgcctaact gtcagaccaa gtttactcat atatacttta gattgattta aaacttcatt    1440
tttaatttaa aaggatctag gtgaagatcc ttttgataa tctcatgacc aaaatcccctt    1500 aacgtgagtt tcgttccac tgagcgtcag accccgtaga aaagatcaaa ggatcttctt     1560
gagatccttt ttttctgcgc gtaatctgct gcttgcaaac aaaaaaacca ccgctaccag    1620
cggtggtttg tttgccggat caagagctac caactctttt tccgaaggta actggcttca    1680
gcagagcgca gataccaaat actgtccttc tagtgtagcc gtagttaggc caccacttca    1740
agaactctgt agcaccgcct acatacctcg ctctgctaat cctgttacca gtggctgctg    1800
ccagtggcga taagtcgtgt cttaccgggt tggactcaag acgatagtta ccggataagg    1860
cgcagcggtc gggctgaacg gggggttcgt gcacacagcc cagcttggag cgaacgacct    1920
acaccgaact gagataccta cagcgtgagc tatgagaaag cgccacgctt cccgaaggga    1980
gaaaggcgga caggtatccg gtaagcggca gggtcggaac aggagagcgc acgagggagc    2040
ttccaggggg aaacgcctgg tatctttata gtcctgtcgg gtttcgccac ctctgacttg    2100
agcgtcgatt tttgtgatgc tcgtcagggg gcggagcct atggaaaaac gccagcaacg     2160
cggccttttt acgttcctg gccttttgct ggcctttgc tcacatgttc tttcctgcgt       2220
tatcccctga ttctgtggat aaccgtatta ccgcctttga gtgagctgat accgctcgcc    2280
gcagccgaac gaccgagcgc agcgagtcag tgagcgagga gcggaagag cgcctgatgc     2340 ggtattttct ccttacgcat ctgtgcggta tttcacaccg caatggtgca ctctcagtac    2400
aatctgctct gatgccgcat agttaagcca gtatacactc cgctatcgct acgtgactgg    2460
gtcatggctg cgccccgaca cccgccaaca cccgctgacg cgccctgacg ggcttgtctg    2520
ctcccggcat ccgcttacag acaagctgtg accgtctccg ggagctgcat gtgtcagagg    2580
ttttcaccgt catcaccgaa acgcgcgagg cagctgcggt aaagctcatc agcgtggtcg    2640
tgaagcgatt cacagatgtc tgcctgttca tccgcgtcca gctcgttgag tttctccaga    2700
agcgttaatg tctggcttct gataaagcgg ccatgttaa gggcggtttt ttcctgtttg     2760
gtcactgatg cctccgtgta aggggatt ctgttcatgg gggtaatgat accgatgaaa      2820
cgagagagga tgctcacgat acgggttact gatgatgaac atgcccggtt actgaacgt     2880 tgtgagggta aacaactggc ggtatggatg cggcgggacc agagaaaaat cactcagggt    2940
caatgccagc gcttcgttaa tacagatgta ggtgttccac agggtagcca gcagcatcct    3000
gcgatgcaga tccggaacat aatggtgcag gcgctgact tccgcgtttc cagactttac     3060
gaaacacgga aaccgaagac cattcatgtt gttgctcagg tcgcagacgt tttgcagcag    3120
cagtcgcttc acgttcgctc gcgtatcggt gattcattct gctaaccagt aaggcaaccc    3180
cgccagccta gccgggtcct caacgacagg agcacgatca tgcgcacccg tggccaggac    3240
ccaacgctgc ccgagatgcg ccgcgtgcgg ctgctggaga tggcggacgc gatggatatg    3300
ttctgccaag ggttggttg cgcattcaca gttctccgca agaattgatt ggctccaatt    3360
cttggagtgg tgaatccgtt agcgaggtgc cgccggcttc cattcaggtc gaggtggccc   3420
ggctccatgc accgcgacgc aacgcgggga ggcagacaag gtatagggcg cgcctacaa    3480
```

-continued

```
tccatgccaa cccgttccat gtgctcgccg aggcggcata atcgccgtg acgatcagcg      3540
gtccaatgat cgaagttagg ctggtaagag ccgcgagcga tccttgaagc tgtccctgat     3600
ggtcgtcatc tacctgcctg acagcatgg cctgcaacgc gggcatcccg atgccgccgg      3660
aagcgagaag aatcataatg gggaaggcca tccagcctcg cgtcgcgaac gccagcaaga     3720
cgtagcccag cgcgtcggcc gccatgccgg cgataatggc ctgcttctcg ccgaaacgtt     3780
tggtggcggg accagtgacg aaggcttgag cgagggcgtg caagattccg aataccgcaa     3840
gcgacaggcc gatcatcgtc gcgctccagc gaaagcggtc ctcgccgaaa atgacccaga     3900
gcgctgccgg cacctgtcct acgagttgca tgataaagaa gacagtcata agtgcgcga     3960
cgatagtcat gccccgcgcc caccggaagg agctgactgg gttgaaggct ctcaagggca     4020
tcggtcgaga tcccggtgcc taatgagtga gctaacttac attaattgcg ttgcgctcac     4080
tgcccgcttt ccagtcggga aacctgtcgt gccagctgca ttaatgaatc ggccaacgcg     4140
cggggagagg cggtttgcgt attgggcgcc agggtggttt ttcttttcac cagtgagacg     4200
ggcaacagct gattgccctt caccgcctgg ccctgagaga gttgcagcaa gcggtccacg     4260
ctggtttgcc ccagcaggcg aaaatcctgt ttgatggtgg ttaacggcgg gatataacat     4320
gagctgtctt cggtatcgtc gtatcccact accgagatat ccgccaccaac gcgcagcccg    4380
gactcggtaa tggcgcgcat tgcgcccagc gccatctgat cgttggcaac cagcatcgca    4440
gtgggaacga tgccctcatt cagcatttgc atggtttgtt gaaaaccgga catggcactc    4500
cagtcgcctt cccgttccgc tatcggctga atttgattgc gagtgagata tttatgccag    4560
ccagccagac gcagacgcgc cgagacagaa cttaatgggc ccgctaacag cgcgatttgc    4620
tggtgaccca atgcgaccag atgctccacg cccagtcgcg taccgtcttc atgggagaaa    4680
ataatactgt tgatgggtgt ctggtcagag acatcaagaa ataacgccgg aacattagtg    4740
caggcagctt ccacagcaat ggcatcctgg tcatccagcg gatagttaat gatcagccca    4800
ctgacgcgtt gcgcgagaag attgtgcacc gccgctttac aggcttcgac gccgcttcgt    4860
tctaccatcg acaccaccac gctggcaccc agttgatcgg cgcgagattt aatcgccgcg    4920
acaatttgcg acgcgcgtg cagggccaga ctggaggtgg caacgccaat cagcaacgac     4980
tgtttgcccg ccagttgttg tgccacgcgg ttgggaatgt aattcagctc cgccatcgcc    5040
gcttccactt tttcccgcgt tttcgcagaa acgtggctgg cctggttcac cacgcgggaa    5100
acggtctgat aagagacacc ggcatactct gcgacatcgt ataacgttac tggtttcaca    5160
ttcaccaccc tgaattgact ctcttccggg cgctatcatg ccataccgcg aaaggttttg    5220
cgccattcga tggtgtccgg gatctcgacg ctctccctta tgcgactcct gcattaggaa    5280
gcagcccagt agtaggttga ggccgttgag caccgccgcc gcaaggaatg gtgcatgcaa    5340
ggagatggcg cccaacagtc cccggccac ggggcctgcc accataccca cgccgaaaca     5400
agcgctcatg agcccgaagt ggcgagcccg atcttcccca tcggtgatgt cggcgatata    5460
ggcgccagca accgcacctg tggcgccggt gatgccggcc acgatgcgtc cggcgtagag    5520
gatcgagatc tcgatcccgc gaaattaata cgactcacta tagggaatt gtgagcggat    5580
aacaattccc ctctagaaat aattttgttt aactttaaga aggagatata catatgcggg    5640
gttctcatca tcatcatcat catggtatgg ctagcatgac tggtggacag caaatgggtc    5700
gggatctgta cgacgatgac gataaggatc atcccttcac catgcgttgt agcgtgtcca    5760
ccgaaaatgt gtctttcacc gaaactgaaa ccgaagctcg tcgttctgcg aactacgaac    5820
ctaacagctg ggactatgat tacctgctgt cctccgacac ggacgagtcc atcgaagtat    5880
```

-continued

```
acaaagacaa agcgaaaaag ctggaagccg aagttcgtcg cgagattaat aacgaaaaag    5940
cagaatttct gaccctgctg gaactgattg acaacgtcca gcgcctgggc ctgggttacc    6000
gtttcgagtc tgatatccgt ggtgcgctgg atcgcttcgt ttcctccggc ggcttcgatg    6060
cggtaaccaa gacttccctg cacggtacgg cactgtcttt ccgtctgctg cgtcaacacg    6120
gttttgaggt ttctcaggaa gcgttcagcg gcttcaaaga ccaaaacggc aacttcctgg    6180
agaacctgaa ggaagatatc aaagctatcc tgagcctgta cgaggccagc ttcctggctc    6240
tggaaggcga aaacatcctg gacgaggcga aggttttcgc aatctctcat ctgaaagaac    6300
tgtctgaaga aaagatcggt aaagagctgg cagaacaggt gaaccatgca ctggaactgc    6360
cactgcatcg ccgtactcag cgtctggaag cagtatggtc tatcgaggcc taccgtaaaa    6420
aggaggacgc gaatcaggtt ctgctggagc tggcaattct ggattacaac atgatccagt    6480
ctgtatacca gcgtgatctg cgtgaaacgt cccgttggtg gcgtcgtgtg ggtctggcga    6540
ccaaactgca ctttgctcgt gaccgcctga ttgagagctt ctactgggcc gtgggtgtag    6600
cattcgaacc gcaatactcc gactgccgta actccgtcgc aaaaatgttt tctttcgtaa    6660
ccattatcga cgatatctac gatgtatacg gcaccctgga cgaactggag ctgtttactg    6720
atgcagttga gcgttgggac gtaaacgcca tcaacgacct gccggattac atgaaactgt    6780
gctttctggc tctgtataac actattaacg aaatcgccta cgacaacctg aaagataaag    6840
gtgagaacat cctgccgtat ctgaccaaag cctgggctga cctgtgcaac gctttcctgc    6900
aagaagccaa gtggctgtac aacaaatcta ctccgacctt tgacgactac ttcggcaacg    6960
catggaaatc ctcttctggc ccgctgcaac tggtgttcgc ttacttcgct gtcgtgcaga    7020
acattaaaaa ggaagagatc gaaaacctgc aaaaatacca tgacaccatc tctcgtcctt    7080
cccatatctt ccgtctgtgc aatgacctgg ctagcgcgtc tgcggaaatt gcgcgtggtg    7140
aaaccgcaaa tagcgtttct tgttacatgc gcactaaagg tatctccgaa gaactggcta    7200
ccgaaagcgt gatgaatctg atcgatgaaa cctggaaaaa gatgaacaag gaaaaactgg    7260
gtggtagcct gttcgcgaaa ccgttcgtgg aaaccgcgat caacctggca cgtcaatctc    7320
actgcactta tcataacggc gacgcgcata cctctccgga tgagctgacc cgcaaacgcg    7380
ttctgtctgt aatcactgaa ccgattctgc gtttgaacg ctaa                      7424
```

<210> SEQ ID NO 16
<211> LENGTH: 560
<212> TYPE: PRT
<213> ORGANISM: Populus alba

<400> SEQUENCE: 16

```
Met Arg Cys Ser Val Ser Thr Glu Asn Val Ser Phe Thr Glu Thr Glu
 1               5                  10                  15

Thr Glu Ala Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val Tyr Lys
        35                  40                  45

Asp Lys Ala Lys Lys Leu Glu Ala Glu Val Arg Arg Glu Ile Asn Asn
    50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95
```

```
Asp Arg Phe Val Ser Ser Gly Gly Phe Asp Ala Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Asn His Ala Leu Glu Leu Pro Leu
        195                 200                 205

His Arg Arg Thr Gln Arg Leu Glu Ala Val Trp Ser Ile Glu Ala Tyr
    210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
    290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Asp Lys Gly Glu
        355                 360                 365

Asn Ile Leu Pro Tyr Leu Thr Lys Ala Trp Ala Asp Leu Cys Asn Ala
    370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
                405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Thr Ile Ser Arg Pro Ser His
        435                 440                 445

Ile Phe Arg Leu Cys Asn Asp Leu Ala Ser Ala Ser Ala Glu Ile Ala
    450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
```

```
                515                 520                 525
Thr Tyr His Asn Gly Asp Ala His Thr Ser Pro Asp Glu Leu Thr Arg
        530                 535                 540

Lys Arg Val Leu Ser Val Ile Thr Glu Pro Ile Leu Pro Phe Glu Arg
545                 550                 555                 560
```

<210> SEQ ID NO 17
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 17

| | | | | |
|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttattttc | taaatacatt | caaatatgta | 540 |
| tccgctcatg | aattaattct | tagaaaaact | catcgagcat | caaatgaaac | tgcaattat | 600 |
| tcatatcagg | attatcaata | ccatattttt | gaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaattcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgtttccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatcctttt | ttctgcgcgt | aatctgctgc | ttgcaaacaa | aaaaaccacc | gctaccagcg | 1560 |
| gtggtttgtt | tgccggatca | agagctacca | actcttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |
| cagcggtcgg | gctgaacggg | gggttcgtgc | acacagccca | gcttggagcg | aacgacctac | 1860 |

```
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100 gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
```

-continued

```
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatataca tatgcgttgt agcgtgtcca ccgaaaatgt     5100
gtctttcacc gaaactgaaa ccgaagctcg tcgttctgcg aactacgaac ctaacagctg    5160
ggactatgat tacctgctgt cctccgacac ggacgagtcc atcgaagtat acaaagacaa    5220
agcgaaaaag ctggaagccg aagttcgtcg cgagattaat aacgaaaaag cagaatttct    5280
gaccctgctg gaactgattg acaacgtcca gcgcctgggc ctgggttacc gtttcgagtc    5340
tgatatccgt ggtgcgctgg atcgcttcgt ttcctccggc ggcttcgatg cggtaaccaa    5400
gacttccctg cacggtacgg cactgtcttt ccgtctgctg cgtcaacacg gttttgaggt    5460
ttctcaggaa gcgttcagcg gcttcaaaga ccaaaacggc aacttcctgg agaacctgaa    5520
ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagagctgg cagaacaggt gaaccatgca ctggaactgc cactgcatcg    5700
ccgtactcag cgtctggaag cagtatggtc tatcgaggcc taccgtaaaa aggaggacgc    5760
gaatcaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880
ctttgctcgt gaccgcctga ttgagagctt ctactgggcc gtgggtgtag cattcgaacc    5940
gcaatactcc gactgccgta actccgtcgc aaaaatgttt tctttcgtaa ccattatcga    6000
cgatatctac gatgtatacg gcaccctgga cgaactggag ctgtttactg atgcagttga    6060
gcgttgggac gtaaacgcca tcaacgacct gccggattac atgaaactgt gctttctggc    6120
tctgtataac actattaacg aaatcgccta cgacaacctg aaagataaag gtgagaacat    6180
cctgccgtat ctgaccaaag cctgggctga cctgtgcaac gctttcctgc aagaagccaa    6240
gtggctgtac aacaaatcta ctccgacctt tgacgactac ttcggcaacg catggaaatc    6300
ctcttctggc ccgctgcaac tggtgttcgc ttacttcgct gtcgtgcaga acattaaaaa    6360
ggaagagatc gaaaacctgc aaaaatacca tgacaccatc tctcgtcctt cccatatctt    6420
ccgtctgtgc aatgacctgg ctagcgcgtc tgcggaaatt gcgcgtggtg aaaccgcaaa    6480
tagcgttctc tgttacatgc gcactaaagg tatctccgaa gaactggcta ccgaaagcgt    6540
gatgaatctg atcgatgaaa cctggaaaaa gatgaacaag gaaaaactgg gtggtagcct    6600
```

```
gttcgcgaaa ccgttcgtgg aaaccgcgat caacctggca cgtcaatctc actgcactta   6660
tcataacggc gacgcgcata cctctccgga tgagctgacc cgcaaacgcg ttctgtctgt   6720
aatcactgaa ccgattctgc cgtttgaacg ctaaggatcc gaattcgagc tccgtcgaca   6780
agcttgcggc cgcactcgag caccaccacc accaccactg agatccggct gctaacaaag   6840
cccgaaagga agctgagttg gctgctgcca ccgctgagca ataactagca taaccccttg   6900
gggcctctaa acgggtcttg agggttttt tgctgaaagg aggaactata tccggat      6957
```

<210> SEQ ID NO 18
<211> LENGTH: 559
<212> TYPE: PRT
<213> ORGANISM: Artificial Sequence
<220> FEATURE:
<223> OTHER INFORMATION: Synthetic Construct

<400> SEQUENCE: 18

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300
```

```
Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
            325                 330                 335

Asn Thr Ile Asn Glu Ile Ala Tyr Asp Asn Leu Lys Asp Lys Gly Glu
        340                 345                 350

Asn Ile Leu Pro Tyr Leu Thr Lys Ala Trp Ala Asp Leu Cys Asn Ala
    355                 360                 365

Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
            435                 440                 445

Arg Gly Glu Thr Ala Asn Ser Val Ser Cys Tyr Met Arg Thr Lys Gly
450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
            515                 520                 525

Lys Arg Val Leu Ser Val Ile Thr Glu Pro Ile Leu Pro Phe Glu Arg
530                 535                 540

Glu Asn Leu Tyr Phe Gln Gly Leu Glu His His His His His His
545                 550                 555
```

<210> SEQ ID NO 19
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 19

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcggggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taggatttt tgccgatttc ggcctattgg ttaaaaatg agctgattta     420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
```

```
tcatatcagg attatcaata ccatatttt gaaaaagccg tttctgtaat gaaggagaaa    660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga gacgaaatac gcgatcgctg ttaaaaggac   960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
tggtgagtaa ccatgcatca tcaggagtac ggataaaatg cttgatggtc ggaagaggca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataacac  1380
cccttgtatt actgtttatg taagcagaca gttttattgt tcatgaccaa aatcccttaa  1440
cgtgagtttt cgttccactg agcgtcagac cccgtagaaa agatcaaagg atcttcttga  1500
gatccttttt ttctgcgcgt aatctgctgc ttgcaaacaa aaaaaccacc gctaccagcg  1560
gtggtttgtt tgccggatca agagctacca actctttttc cgaaggtaac tggcttcagc  1620
agagcgcaga taccaaatac tgtccttcta gtgtagccgt agttaggcca ccacttcaag  1680
aactctgtag caccgcctac atacctcgct ctgctaatcc tgttaccagt ggctgctgcc  1740
agtggcgata agtcgtgtct taccgggttg gactcaagac gatagttacc ggataaggcg  1800
cagcggtcgg gctgaacggg gggttcgtgc acacagccca gcttggagcg aacgacctac  1860
accgaactga gatacctaca gcgtgagcta tgagaaagcg ccacgcttcc cgaagggaga  1920
aaggcggaca ggtatccggt aagcggcagg gtcggaacag gagagcgcac gagggagctt  1980
ccagggggaa acgcctggta tctttatagt cctgtcgggt ttcgccacct ctgacttgag  2040
cgtcgatttt tgtgatgctc gtcagggggg cggagcctat ggaaaaacgc cagcaacgcg  2100
gcctttttac ggttcctggc cttttgctgg ccttttgctc acatgttctt tcctgcgtta  2160
tcccctgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
ggtcatggct gcgccccgac acccgccaac acccgctgac gcgccctgac gggcttgtct  2460
gctcccggca tccgcttaca gacaagctgt gaccgtctcc gggagctgca tgtgtcagag  2520
gttttcaccg tcatcaccga aacgcgcgag gcagctgcgg taaagctcat cagcgtggtc  2580
gtgaagcgat tcacagatgt ctgcctgttc atccgcgtcc agctcgttga gtttctccag  2640
aagcgttaat gtctggcttc tgataaagcg ggccatgtta agggcggttt tttcctgttt  2700
ggtcactgat gcctccgtgt aagggggatt tctgttcatg gggtaatga  taccgatgaa  2760
acgagagagg atgctcacga tacgggttac tgatgatgaa catgcccggt tactggaacg  2820
ttgtgagggt aaacaactgg cggtatggat gcggcgggac cagagaaaaa tcactcaggg  2880
tcaatgccag cgcttcgtta atacagatgt aggtgttcca cagggtagcc agcagcatcc  2940
tgcgatgcag atccggaaca taatggtgca gggcgctgac ttccgcgttt ccagacttta  3000
```

```
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg cgcgcattg    3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgcggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
```

-continued

| | |
|---|---|
| tgcggtaacc aagacttccc tgcacggtac ggcactgtct ttccgtctgc tgcgtcaaca | 5400 |
| cggttttgag gtttctcagg aagcgttcag cggcttcaaa gaccaaaacg gcaacttcct | 5460 |
| ggagaacctg aaggaagata tcaaagctat cctgagcctg tacgaggcca gcttcctggc | 5520 |
| tctggaaggc gaaaacatcc tggacgaggc gaaggttttc gcaatctctc atctgaaaga | 5580 |
| actgtctgaa gaaaagatcg gtaaagagct ggcagaacag gtgaaccatg cactggaact | 5640 |
| gccactgcat cgccgtactc agcgtctgga agcagtatgg tctatcgagg cctaccgtaa | 5700 |
| aaaggaggac gcgaatcagg ttctgctgga gctggcaatt ctggattaca acatgatcca | 5760 |
| gtctgtatac cagcgtgatc tgcgtgaaac gtcccgttgg tggcgtcgtg tgggtctggc | 5820 |
| gaccaaactg cactttgctc gtgaccgcct gattgagagc ttctactggg ccgtgggtgt | 5880 |
| agcattcgaa ccgcaatact ccgactgccg taactccgtc gcaaaaatgt tttctttcgt | 5940 |
| aaccattatc gacgatatct acgatgtata cggcaccctg gacgaactgg agctgtttac | 6000 |
| tgatgcagtt gagcgttggg acgtaaacgc catcaacgac ctgccggatt acatgaaact | 6060 |
| gtgctttctg gctctgtata acactattaa cgaaatcgcc tacgacaacc tgaaagataa | 6120 |
| aggtgagaac atcctgccgt atctgaccaa agcctgggct gacctgtgca acgctttcct | 6180 |
| gcaagaagcc aagtggctgt acaacaaatc tactccgacc tttgacgact acttcggcaa | 6240 |
| cgcatggaaa tcctcttctg gcccgctgca actggtgttc gcttacttcg ctgtcgtgca | 6300 |
| gaacattaaa aaggaagaga tcgaaaacct gcaaaaatac catgacacca tctctcgtcc | 6360 |
| ttcccatatc ttccgtctgt gcaatgacct ggctagcgcg tctgcggaaa ttgcgcgtgg | 6420 |
| tgaaaccgca aatagcgttt cttgttacat gcgcactaaa ggtatctccg aagaactggc | 6480 |
| taccgaaagc gtgatgaatc tgatcgatga acctggaaaa agatgaaca aggaaaaact | 6540 |
| gggtggtagc ctgttcgcga aaccgttcgt ggaaaccgcg atcaacctgg cacgtcaatc | 6600 |
| tcactgcact tatcataacg gcgacgcgca tacctctccg gatgagctga cccgcaaacg | 6660 |
| cgttctgtct gtaatcactg aaccgattct gccgtttgaa cgcgaaaacc tgtattttca | 6720 |
| gggcctcgag caccaccacc accaccactg agatccggct gctaacaaag cccgaaagga | 6780 |
| agctgagttg gctgctgcca ccgctgagca ataactagca taaccccttg gggcctctaa | 6840 |
| acgggtcttg aggggttttt tgctgaaagg aggaactata tccggat | 6887 |

<210> SEQ ID NO 20
<211> LENGTH: 575
<212> TYPE: PRT
<213> ORGANISM: Artificial Sequence
<220> FEATURE:
<223> OTHER INFORMATION: Synthetic Construct

<400> SEQUENCE: 20

Met Arg Cys Ser Val Ser Thr Glu Asn Val Ser Phe Thr Glu Thr
1               5                   10                  15

Thr Glu Ala Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val Tyr Lys
        35                  40                  45

Asp Lys Ala Lys Lys Leu Glu Ala Glu Val Arg Glu Ile Asn Asn
    50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95

-continued

```
Asp Arg Phe Val Ser Ser Gly Phe Asp Ala Val Thr Lys Thr Ser
            100                 105                 110
Leu His Gly Thr Ala Leu Ser Phe Arg Leu Leu Arg Gln His Gly Phe
        115                 120                 125
Glu Val Ser Gln Glu Ala Phe Ser Gly Phe Lys Asp Gln Asn Gly Asn
    130                 135                 140
Phe Leu Glu Asn Leu Lys Glu Asp Ile Lys Ala Ile Leu Ser Leu Tyr
145                 150                 155                 160
Glu Ala Ser Phe Leu Ala Leu Glu Gly Glu Asn Ile Leu Asp Glu Ala
                165                 170                 175
Lys Val Phe Ala Ile Ser His Leu Lys Glu Leu Ser Glu Glu Lys Ile
            180                 185                 190
Gly Lys Glu Leu Ala Glu Gln Val Asn His Ala Leu Glu Leu Pro Leu
        195                 200                 205
His Arg Arg Thr Gln Arg Leu Glu Ala Val Trp Ser Ile Glu Ala Tyr
    210                 215                 220
Arg Lys Lys Glu Asp Ala Asn Gln Val Leu Leu Glu Leu Ala Ile Leu
225                 230                 235                 240
Asp Tyr Asn Met Ile Gln Ser Val Tyr Gln Arg Asp Leu Arg Glu Thr
                245                 250                 255
Ser Arg Trp Trp Arg Arg Val Gly Leu Ala Thr Lys Leu His Phe Ala
            260                 265                 270
Arg Asp Arg Leu Ile Glu Ser Phe Tyr Trp Ala Val Gly Val Ala Phe
        275                 280                 285
Glu Pro Gln Tyr Ser Asp Cys Arg Asn Ser Val Ala Lys Met Phe Ser
    290                 295                 300
Phe Val Thr Ile Ile Asp Asp Ile Tyr Asp Val Tyr Gly Thr Leu Asp
305                 310                 315                 320
Glu Leu Glu Leu Phe Thr Asp Ala Val Glu Arg Trp Asp Val Asn Ala
                325                 330                 335
Ile Asn Asp Leu Pro Asp Tyr Met Lys Leu Cys Phe Leu Ala Leu Tyr
            340                 345                 350
Asn Thr Ile Asn Glu Ile Ala Tyr Asp Asn Leu Lys Asp Lys Gly Glu
        355                 360                 365
Asn Ile Leu Pro Tyr Leu Thr Lys Ala Trp Ala Asp Leu Cys Asn Ala
    370                 375                 380
Phe Leu Gln Glu Ala Lys Trp Leu Tyr Asn Lys Ser Thr Pro Thr Phe
385                 390                 395                 400
Asp Asp Tyr Phe Gly Asn Ala Trp Lys Ser Ser Gly Pro Leu Gln
                405                 410                 415
Leu Val Phe Ala Tyr Phe Ala Val Gln Asn Ile Lys Lys Glu Glu
            420                 425                 430
Ile Glu Asn Leu Gln Lys Tyr His Asp Thr Ile Ser Arg Pro Ser His
        435                 440                 445
Ile Phe Arg Leu Cys Asn Asp Leu Ala Ser Ala Ser Ala Glu Ile Ala
    450                 455                 460
Arg Gly Glu Thr Ala Asn Ser Val Ser Cys Tyr Met Arg Thr Lys Gly
465                 470                 475                 480
Ile Ser Glu Glu Leu Ala Thr Glu Ser Val Met Asn Leu Ile Asp Glu
                485                 490                 495
Thr Trp Lys Lys Met Asn Lys Glu Lys Leu Gly Gly Ser Leu Phe Ala
            500                 505                 510
```

```
Lys Pro Phe Val Glu Thr Ala Ile Asn Leu Ala Arg Gln Ser His Cys
            515                 520                 525

Thr Tyr His Asn Gly Asp Ala His Thr Ser Pro Asp Glu Leu Thr Arg
        530                 535                 540

Lys Arg Val Leu Ser Val Ile Thr Glu Pro Ile Leu Pro Phe Glu Arg
545                 550                 555                 560

Glu Asn Leu Tyr Phe Gln Gly Leu Glu His His His His His His
                565                 570                 575

<210> SEQ ID NO 21
<211> LENGTH: 6935
<212> TYPE: DNA
<213> ORGANISM: Artificial Sequence
<220> FEATURE:
<223> OTHER INFORMATION: Synthetic Construct

<400> SEQUENCE: 21
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg     180 gttccgattt agtgctttac ggcacctcga ccccaaaaaa cttgattagg gtgatggttc     240
acgtagtggg ccatcgccct gatagacggt ttttcgccct tgacgttgg agtccacgtt     300 ctttaatagt ggactcttgt tccaaactgg aacaacactc aaccctatct cggtctattc     360
ttttgattta agggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg aattaattct tagaaaaact catcgagcat caaatgaaac tgcaatttat     600
tcatatcagg attatcaata ccatatttt gaaaagccg tttctgtaat aaggagaaa     660 actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa agtttatgc atttctttcc     840 agacttgttc aacaggccag ccattacgct cgtcatcaaa atcactcgca tcaaccaaac     900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440 cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
```

```
agtggcgata agtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccaggggaaa acgcctggta tctttatagt cctgtcgggt ttcgccacct ctgacttgag    2040
cgtcgatttt tgtgatgctc gtcaggggg cggagcctat ggaaaaacgc cagcaacgcg    2100
gccttttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
```

```
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcgttgt agcgtgtcca ccgaaaatgt    5100
gtctttcacc gaaactgaaa ccgaagctcg tcgttctgcg aactacgaac ctaacagctg    5160
ggactatgat tacctgctgt cctccgacac ggacgagtcc atcgaagtat acaaagacaa    5220
agcgaaaaag ctggaagccg aagttcgtcg cgagattaat aacgaaaaag cagaatttct    5280 gacccctgctg gaactgattg acaacgtcca gcgcctgggc ctgggttacc gtttcgagtc    5340
tgatatccgt ggtgcgctgg atcgcttcgt ttcctccggc ggcttcgatg cggtaaccaa    5400
gacttccctg cacggtacgg cactgtcttt ccgtctgctg cgtcaacacg gttttgaggt    5460
ttctcaggaa gcgttcagcg gcttcaaaga ccaaaacggc aacttcctgg agaacctgaa    5520
ggaagatatc aaagctatcc tgagcctgta cgaggccagc ttcctggctc tggaaggcga    5580
aaacatcctg gacgaggcga aggttttcgc aatctctcat ctgaaagaac tgtctgaaga    5640
aaagatcggt aaagagctgg cagaacaggt gaaccatgca ctggaactgc cactgcatcg    5700
ccgtactcag cgtctggaag cagtatggtc tatcgaggcc taccgtaaaa aggaggacgc    5760
gaatcaggtt ctgctggagc tggcaattct ggattacaac atgatccagt ctgtatacca    5820
gcgtgatctg cgtgaaacgt cccgttggtg gcgtcgtgtg ggtctggcga ccaaactgca    5880
ctttgctcgt gaccgcctga ttgagagctt ctactgggcc gtgggtgtag cattcgaacc    5940
gcaatactcc gactgccgta actccgtcgc aaaaatgttt tctttcgtaa ccattatcga    6000
cgatatctac gatgtatacg gcaccctgga cgaactggag ctgtttactg atgcagttga    6060
gcgttgggac gtaaacgcca tcaacgacct gccggattac atgaaactgt gctttctggc    6120
tctgtataac actattaacg aaatcgccta cgacaacctg aaagataaag gtgagaacat    6180
cctgccgtat ctgaccaaag cctgggctga cctgtgcaac gctttcctgc aagaagccaa    6240
gtggctgtac aacaaatcta ctccgaccct tgacgactac ttcggcaacg catggaaatc    6300
ctcttctggc ccgctgcaac tggtgttcgc ttacttcgct gtcgtgcaga acattaaaaa    6360
ggaagagatc gaaaacctgc aaaaatacca tgacaccatc tctcgtcctt cccatatctt    6420
ccgtctgtgc aatgacctgg ctagcgcgtc tgcggaaatt gcgcgtggtg aaaccgcaaa    6480
```

```
tagcgtttct tgttacatgc gcactaaagg tatctccgaa gaactggcta ccgaaagcgt    6540
gatgaatctg atcgatgaaa cctggaaaaa gatgaacaag gaaaaactgg gtggtagcct    6600
gttcgcgaaa ccgttcgtgg aaaccgcgat caacctggca cgtcaatctc actgcactta    6660
tcataacggc gacgcgcata cctctccgga tgagctgacc cgcaaacgcg ttctgtctgt    6720
aatcactgaa ccgattctgc cgtttgaacg cgaaaacctg tattttcagg gcctcgagca    6780
ccaccaccac caccactgag atccggctgc taacaaagcc cgaaggaag ctgagttggc     6840 tgctgccacc gctgagcaat aactagcata accccttggg gcctctaaac gggtcttgag    6900
gggttttttg ctgaaaggag gaactatatc cggat                                6935
```

<210> SEQ ID NO 22
<211> LENGTH: 23
<212> TYPE: DNA
<213> ORGANISM: Artificial Sequence
<220> FEATURE:
<223> OTHER INFORMATION: Synthetic Construct

<400> SEQUENCE: 22
cggtgaactg aaaggtgacg tcc                                             23

<210> SEQ ID NO 23
<211> LENGTH: 25
<212> TYPE: DNA
<213> ORGANISM: Artificial Sequence
<220> FEATURE:
<223> OTHER INFORMATION: Synthetic Construct

<400> SEQUENCE: 23
ggacgttaac gctattaaca ccctg                                           25

<210> SEQ ID NO 24
<211> LENGTH: 22
<212> TYPE: DNA
<213> ORGANISM: Artificial Sequence
<220> FEATURE:
<223> OTHER INFORMATION: Synthetic Construct

<400> SEQUENCE: 24
cacatcgtcg atcagctcca gc                                              22

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25
ggtcgtcaga ctgtcgatga agcc                                            24

<210> SEQ ID NO 26
<211> LENGTH: 39
<212> TYPE: DNA
<213> ORGANISM: Artificial Sequence
<220> FEATURE:
<223> OTHER INFORMATION: Synthetic Construct

<400> SEQUENCE: 26
gcttatgaat tctgtgcgac ctcttctcaa tttactcag                            39

<210> SEQ ID NO 27

-continued

```
<211> LENGTH: 38
<212> TYPE: DNA
<213> ORGANISM: Artificial Sequence
<220> FEATURE:
<223> OTHER INFORMATION: Synthetic Construct

<400> SEQUENCE: 27
gcttataagc ttagacatac atcagctggt taatcggg                              38

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
ctcctccagc aggttctcac c                                                21

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct

<400> SEQUENCE: 29
caccatgcgt tgtagcgtgt cca                                              23

<210> SEQ ID NO 30
<211> LENGTH: 52
<212> TYPE: DNA
<213> ORGANISM: Artificial Sequence
<220> FEATURE:
<223> OTHER INFORMATION: Synthetic Construct

<400> SEQUENCE: 30
gggcccgttt aaactttaac tagactctgc agttagcgtt caaacggcag aa              52

<210> SEQ ID NO 31
<211> LENGTH: 25
<212> TYPE: DNA
<213> ORGANISM: Artificial Sequence
<220> FEATURE:
<223> OTHER INFORMATION: Synthetic Construct

<400> SEQUENCE: 31
caccatgcgt cgttctgcga actac                                            25

<210> SEQ ID NO 32
<211> LENGTH: 26
<212> TYPE: DNA
<213> ORGANISM: Artificial Sequence
<220> FEATURE:
<223> OTHER INFORMATION: Synthetic Construct

<400> SEQUENCE: 32
gcaccatgcg tcgttctgcg aactac                                           26

<210> SEQ ID NO 33
<211> LENGTH: 37
<212> TYPE: DNA
<213> ORGANISM: Artificial Sequence
<220> FEATURE:
<223> OTHER INFORMATION: Synthetic Construct

<400> SEQUENCE: 33
```

```
gatcgaaggg cgatcgtgtc acagtctggc gaaaccg                                    37
```

<210> SEQ ID NO 34
<211> LENGTH: 43
<212> TYPE: DNA
<213> ORGANISM: Artificial Sequence
<220> FEATURE:
<223> OTHER INFORMATION: Synthetic Construct

<400> SEQUENCE: 34

```
ctgaattctg cagatatctg tttttccact cttcgttcac ttt                             43
```

<210> SEQ ID NO 35
<211> LENGTH: 33
<212> TYPE: DNA
<213> ORGANISM: Artificial Sequence
<220> FEATURE:
<223> OTHER INFORMATION: Synthetic Construct

<400> SEQUENCE: 35

```
tctagagggc ccaagaaaaa tgccccgctt acg                                        33
```

<210> SEQ ID NO 36
<211> LENGTH: 111
<212> TYPE: DNA
<213> ORGANISM: Artificial Sequence
<220> FEATURE:
<223> OTHER INFORMATION: Synthetic Construct

<400> SEQUENCE: 36

```
gatcgcggcc gcgcccttga cgatgccaca tcctgagcaa ataattcaac cactaattgt           60
gagcggataa cacaaggagg aaacagctat gtcattaccg ttcttaactt c                   111
```

<210> SEQ ID NO 37
<211> LENGTH: 75
<212> TYPE: DNA
<213> ORGANISM: Artificial Sequence
<220> FEATURE:
<223> OTHER INFORMATION: Synthetic Construct

<400> SEQUENCE: 37

```
gatcgggccc caagaaaaaa ggcacgtcat ctgacgtgcc ttttttattt gtagacgcgt           60
tgttatagca ttcta                                                           75
```

<210> SEQ ID NO 38
<211> LENGTH: 81
<212> TYPE: DNA
<213> ORGANISM: Artificial Sequence
<220> FEATURE:
<223> OTHER INFORMATION: Synthetic Construct

<400> SEQUENCE: 38

```
aaagtagccg aagatgacgg tttgtcacat ggagttggca ggatgtttga ttaaaagcaa           60
ttaaccctca ctaaagggcg g                                                    81
```

<210> SEQ ID NO 39
<211> LENGTH: 160
<212> TYPE: DNA
<213> ORGANISM: Artificial Sequence
<220> FEATURE:
<223> OTHER INFORMATION: Synthetic Construct

<400> SEQUENCE: 39

```
agagtgttca ccaaaaataa taacctttcc cggtgcagaa gttaagaacg gtaatgacat      60
agctgtttcc tccttgtgtt atccgctcac aattagtggt tgaattatttt gctcaggatg     120 tggcatcgtc aagggctaat acgactcact atagggctcg                            160
```

```
<210> SEQ ID NO 40
<211> LENGTH: 14
<212> TYPE: PRT
<213> ORGANISM: Artificial Sequence
<220> FEATURE:
<223> OTHER INFORMATION: Synthetic Construct

<400> SEQUENCE: 40

Ser Ala Ser Ala Glu Ile Ala Arg Gly Glu Thr Ala Asn Ser
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic Construct

<400> SEQUENCE: 41

Tyr His Asn Gly Asp Ala His Thr Ser Pro Asp Glu Leu
1               5                   10

<210> SEQ ID NO 42
<211> LENGTH: 564
<212> TYPE: PRT
<213> ORGANISM: Peuraria lobata

<400> SEQUENCE: 42

Met Cys Ala Thr Ser Ser Gln Phe Thr Gln Ile Thr Glu His Asn Ser
1               5                   10                  15

Arg Arg Ser Ala Asn Tyr Gln Pro Asn Leu Trp Asn Phe Glu Phe Leu
            20                  25                  30

Gln Ser Leu Glu Asn Asp Leu Lys Val Glu Lys Leu Glu Glu Lys Ala
        35                  40                  45

Thr Lys Leu Glu Glu Glu Val Arg Cys Met Ile Asn Arg Val Asp Thr
    50                  55                  60

Gln Pro Leu Ser Leu Leu Glu Leu Ile Asp Asp Val Gln Arg Leu Gly
65                  70                  75                  80

Leu Thr Tyr Lys Phe Glu Lys Asp Ile Ile Lys Ala Leu Glu Asn Ile
                85                  90                  95

Val Leu Leu Asp Glu Asn Lys Lys Asn Lys Ser Asp Leu His Ala Thr
            100                 105                 110

Ala Leu Ser Phe Arg Leu Leu Arg Gln His Gly Phe Gly Val Ser Gln
        115                 120                 125

Asp Val Phe Glu Arg Phe Lys Asp Lys Glu Gly Gly Phe Ser Gly Glu
    130                 135                 140

Leu Lys Gly Asp Val Gln Gly Leu Leu Ser Leu Tyr Glu Ala Ser Tyr
145                 150                 155                 160

Leu Gly Phe Glu Gly Glu Asn Leu Leu Glu Glu Ala Arg Thr Phe Ser
                165                 170                 175

Ile Thr His Leu Lys Asn Asn Leu Lys Glu Gly Ile Asn Thr Lys Val
            180                 185                 190

Ala Glu Gln Val Ser His Ala Leu Glu Leu Pro Tyr His Gln Arg Leu
        195                 200                 205
```

```
His Arg Leu Glu Ala Arg Trp Phe Leu Asp Lys Tyr Glu Pro Lys Glu
    210                 215                 220

Pro His His Gln Leu Leu Leu Glu Leu Ala Lys Leu Asp Phe Asn Met
225                 230                 235                 240

Val Gln Thr Leu His Gln Lys Glu Leu Gln Asp Leu Ser Arg Trp Trp
                245                 250                 255

Thr Glu Met Gly Leu Ala Ser Lys Leu Asp Phe Val Arg Asp Arg Leu
            260                 265                 270

Met Glu Val Tyr Phe Trp Ala Leu Gly Met Ala Pro Asp Pro Gln Phe
        275                 280                 285

Gly Glu Cys Arg Lys Ala Val Thr Lys Met Phe Gly Leu Val Thr Ile
    290                 295                 300

Ile Asp Asp Val Tyr Asp Val Tyr Gly Thr Leu Asp Glu Leu Gln Leu
305                 310                 315                 320

Phe Thr Asp Ala Val Glu Arg Trp Asp Val Asn Ala Ile Asn Thr Leu
                325                 330                 335

Pro Asp Tyr Met Lys Leu Cys Phe Leu Ala Leu Tyr Asn Thr Val Asn
            340                 345                 350

Asp Thr Ser Tyr Ser Ile Leu Lys Glu Lys Gly His Asn Asn Leu Ser
        355                 360                 365

Tyr Leu Thr Lys Ser Trp Arg Glu Leu Cys Lys Ala Phe Leu Gln Glu
    370                 375                 380

Ala Lys Trp Ser Asn Asn Lys Ile Ile Pro Ala Phe Ser Lys Tyr Leu
385                 390                 395                 400

Glu Asn Ala Ser Val Ser Ser Gly Val Ala Leu Leu Ala Pro Ser
                405                 410                 415

Tyr Phe Ser Val Cys Gln Gln Gln Glu Asp Ile Ser Asp His Ala Leu
            420                 425                 430

Arg Ser Leu Thr Asp Phe His Gly Leu Val Arg Ser Ser Cys Val Ile
        435                 440                 445

Phe Arg Leu Cys Asn Asp Leu Ala Thr Ser Ala Ala Glu Leu Glu Arg
    450                 455                 460

Gly Glu Thr Thr Asn Ser Ile Ile Ser Tyr Met His Glu Asn Asp Gly
465                 470                 475                 480

Thr Ser Glu Glu Gln Ala Arg Glu Glu Leu Arg Lys Leu Ile Asp Ala
                485                 490                 495

Glu Trp Lys Lys Met Asn Arg Glu Arg Val Ser Asp Ser Thr Leu Leu
            500                 505                 510

Pro Lys Ala Phe Met Glu Ile Ala Val Asn Met Ala Arg Val Ser His
        515                 520                 525

Cys Thr Tyr Gln Tyr Gly Asp Gly Leu Gly Arg Pro Asp Tyr Ala Thr
    530                 535                 540

Glu Asn Arg Ile Lys Leu Leu Ile Asp Pro Phe Pro Ile Asn Gln
545                 550                 555                 560

Leu Met Tyr Val

<210> SEQ ID NO 43
<211> LENGTH: 559
<212> TYPE: PRT
<213> ORGANISM: Populus alba x tremuloides

<400> SEQUENCE: 43

Met Cys Ser Val Ser Thr Glu Asn Val Ser Phe Thr Glu Thr Glu Thr
 1                5                  10                 15
```

Glu Ala Arg Arg Ser Ala Asn Tyr Glu Pro Asn Ser Trp Asp Tyr Asp
            20                  25                  30

Phe Leu Leu Ser Ser Asp Thr Asp Gly Ser Ile Glu Val Tyr Lys Asp
        35                  40                  45

Lys Ala Lys Lys Leu Glu Ala Glu Val Arg Arg Glu Ile Asn Asn Glu
 50                  55                  60

Lys Ala Glu Phe Leu Thr Leu Leu Glu Leu Ile Asp Asn Val Gln Arg
 65                  70                  75                  80

Leu Gly Leu Gly Tyr Arg Phe Glu Ser Asp Ile Arg Arg Ala Leu Asp
                85                  90                  95

Arg Phe Val Ser Ser Gly Gly Phe Asp Gly Val Thr Lys Thr Ser Leu
            100                 105                 110

His Ala Thr Ala Leu Ser Phe Arg Leu Leu Arg Gln His Gly Phe Glu
            115                 120                 125

Val Ser Gln Glu Ala Phe Ser Gly Phe Lys Asp Gln Asn Gly Asn Phe
            130                 135                 140

Leu Glu Asn Leu Lys Glu Asp Thr Lys Ala Ile Leu Ser Leu Tyr Glu
145                 150                 155                 160

Ala Ser Phe Leu Ala Leu Glu Gly Glu Asn Ile Leu Asp Glu Ala Arg
                165                 170                 175

Val Phe Ala Ile Ser His Leu Lys Glu Leu Ser Glu Glu Lys Ile Gly
            180                 185                 190

Lys Glu Leu Ala Glu Gln Val Asn His Ala Leu Glu Leu Pro Leu His
            195                 200                 205

Arg Arg Thr Gln Arg Leu Glu Ala Val Trp Ser Ile Glu Ala Tyr Arg
210                 215                 220

Lys Lys Glu Asp Ala Asn Gln Val Leu Leu Glu Leu Ala Ile Leu Asp
225                 230                 235                 240

Tyr Asn Met Ile Gln Ser Val Tyr Gln Arg Asp Leu Arg Glu Thr Ser
                245                 250                 255

Arg Trp Trp Arg Arg Val Gly Leu Ala Thr Lys Leu His Phe Ala Lys
            260                 265                 270

Asp Arg Leu Ile Glu Ser Phe Tyr Trp Ala Val Gly Val Ala Phe Glu
            275                 280                 285

Pro Gln Tyr Ser Asp Cys Arg Asn Ser Val Ala Lys Met Phe Ser Phe
            290                 295                 300

Val Thr Ile Ile Asp Asp Ile Tyr Asp Val Tyr Gly Thr Leu Asp Glu
305                 310                 315                 320

Leu Glu Leu Phe Thr Asp Ala Val Glu Arg Trp Asp Val Asn Ala Ile
                325                 330                 335

Asn Asp Leu Pro Asp Tyr Met Lys Leu Cys Phe Leu Ala Leu Tyr Asn
            340                 345                 350

Thr Ile Asn Glu Ile Ala Tyr Asp Asn Leu Lys Asp Lys Gly Glu Asn
            355                 360                 365

Ile Leu Pro Tyr Leu Thr Lys Ala Trp Ala Asp Leu Cys Asn Ala Phe
            370                 375                 380

Leu Gln Glu Ala Lys Trp Leu Tyr Asn Lys Ser Thr Pro Thr Phe Asp
385                 390                 395                 400

Asp Tyr Phe Gly Asn Ala Trp Lys Ser Ser Gly Pro Leu Gln Leu
                405                 410                 415

Ile Phe Ala Tyr Phe Ala Val Val Gln Asn Ile Lys Lys Glu Glu Ile
            420                 425                 430

Glu Asn Leu Gln Lys Tyr His Asp Ile Ile Ser Arg Pro Ser His Ile

```
                435                 440                 445
Phe Arg Leu Cys Asn Asp Leu Ala Ser Ala Ser Ala Glu Ile Ala Arg
    450                 455                 460

Gly Glu Thr Ala Asn Ser Val Ser Cys Tyr Met Arg Thr Lys Gly Ile
465                 470                 475                 480

Ser Glu Glu Leu Ala Thr Glu Ser Val Met Asn Leu Ile Asp Glu Thr
                485                 490                 495

Cys Lys Lys Met Asn Lys Glu Lys Leu Gly Gly Ser Leu Phe Ala Lys
            500                 505                 510

Pro Phe Val Glu Thr Ala Ile Asn Leu Ala Arg Gln Ser His Cys Thr
        515                 520                 525

Tyr His Asn Gly Asp Ala His Thr Ser Pro Asp Glu Leu Thr Arg Lys
    530                 535                 540

Arg Val Leu Ser Val Ile Thr Glu Pro Ile Leu Pro Phe Glu Arg
545                 550                 555
```

<210> SEQ ID NO 44
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 44

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatatttt gaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgcgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
```

-continued

```
cccttgtatt actgtttatg taagcagaca gtttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccaggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100
gccttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca acaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg gccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggtttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
```

```
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagca cgtcgctctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagactttcc cgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
```

```
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccgca aatagcgttt cttgttacat gcgcactaaa ggtatctccg aagaactggc   6480
taccgaaagc gtgatgaatc tgatcgatga aacctggaaa aagatgaaca aggaaaaact   6540
gggtggtagc ctgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatcactg aaccgattct gccgtttgaa cgctaaggat ccgaattcga   6720
gctccgtcga caagcttgcg gccgcactcg agcaccacca ccaccaccac tgagatccgg   6780
ctgctaacaa agcccgaaag gaagctgagt tggctgctgc caccgctgag caataactag   6840
cataacccct ggggcctcta aacgggtctt gaggggtttt tttgctgaaa ggaggaacta   6900
tatccggat                                                          6909
```

<210> SEQ ID NO 45
<211> LENGTH: 544
<212> TYPE: PRT
<213> ORGANISM: Populus alba

<400> SEQUENCE: 45

Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr

```
            225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
                260                 265                 270

Glu Pro Gln Tyr Ser Asp Cys Arg Asn Ser Val Ala Lys Met Phe Ser
                275                 280                 285

Phe Val Thr Ile Ile Asp Asp Ile Tyr Asp Val Tyr Gly Thr Leu Asp
                290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
                340                 345                 350

Asn Ile Leu Pro Tyr Leu Thr Lys Ala Trp Ala Asp Leu Cys Asn Ala
                355                 360                 365

Phe Leu Gln Glu Ala Lys Trp Leu Tyr Asn Lys Ser Thr Pro Thr Phe
                370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
                420                 425                 430

Ile Phe Arg Leu Cys Asn Asp Leu Ala Ser Ala Ser Ala Glu Ile Ala
                435                 440                 445

Arg Gly Glu Thr Ala Asn Ser Val Ser Cys Tyr Met Arg Thr Lys Gly
                450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
                515                 520                 525

Lys Arg Val Leu Ser Val Ile Thr Glu Pro Ile Leu Pro Phe Glu Arg
530                 535                 540

<210> SEQ ID NO 46
<211> LENGTH: 47
<212> TYPE: DNA
<213> ORGANISM: Artificial Sequence
<220> FEATURE:
<223> OTHER INFORMATION: Synthetic Construct

<400> SEQUENCE: 46
ggagatatac atatggaagc acgtcgctct gcgaactacg aacctaa         47

<210> SEQ ID NO 47
<211> LENGTH: 47
<212> TYPE: DNA
<213> ORGANISM: Artificial Sequence
<220> FEATURE:
<223> OTHER INFORMATION: Synthetic Construct
```

```
<400> SEQUENCE: 47
ttaggttcgt agttcgcaga gcgacgtgct tccatatgta tatctcc        47

<210> SEQ ID NO 48
<211> LENGTH: 20
<212> TYPE: DNA
<213> ORGANISM: Artificial Sequence
<220> FEATURE:
<223> OTHER INFORMATION: Synthetic Construct

<400> SEQUENCE: 48
taatacgact cactataggg                                      20

<210> SEQ ID NO 49
<211> LENGTH: 19
<212> TYPE: DNA
<213> ORGANISM: Artificial Sequence
<220> FEATURE:
<223> OTHER INFORMATION: Synthetic Construct

<400> SEQUENCE: 49
gctagttatt gctcagcgg                                       19

<210> SEQ ID NO 50
<211> LENGTH: 22
<212> TYPE: DNA
<213> ORGANISM: Artificial Sequence
<220> FEATURE:
<223> OTHER INFORMATION: Synthetic Construct

<400> SEQUENCE: 50
gcactgtctt tccgtctgct gc                                   22

<210> SEQ ID NO 51
<211> LENGTH: 20
<212> TYPE: DNA
<213> ORGANISM: Artificial Sequence
<220> FEATURE:
<223> OTHER INFORMATION: Synthetic Construct

<400> SEQUENCE: 51
cttcggcaac gcatggaaat                                      20

<210> SEQ ID NO 52
<211> LENGTH: 20
<212> TYPE: DNA
<213> ORGANISM: Artificial Sequence
<220> FEATURE:
<223> OTHER INFORMATION: Synthetic Construct

<400> SEQUENCE: 52
ctcgtacagg ctcaggatag                                      20

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct

<400> SEQUENCE: 53
ttacgtccca acgctcaact                                      20

<210> SEQ ID NO 54
<211> LENGTH: 36
```

<212> TYPE: DNA
<213> ORGANISM: Artificial Sequence
<220> FEATURE:
<223> OTHER INFORMATION: Synthetic Construct

<400> SEQUENCE: 54
gcgcgtggtg aaaccaacaa tagcgtttct tgttac                                    36

<210> SEQ ID NO 55
<211> LENGTH: 41
<212> TYPE: DNA
<213> ORGANISM: Artificial Sequence
<220> FEATURE:
<223> OTHER INFORMATION: Synthetic Construct

<400> SEQUENCE: 55
agatgaacaa ggaaaaactg agtggtagcc tgttcgcgaa a                              41

<210> SEQ ID NO 56
<211> LENGTH: 37
<212> TYPE: DNA
<213> ORGANISM: Artificial Sequence
<220> FEATURE:
<223> OTHER INFORMATION: Synthetic Construct

<400> SEQUENCE: 56
gaaaaactgg gtggtagccc gttcgcgaaa ccgttcg                                   37

<210> SEQ ID NO 57
<211> LENGTH: 37
<212> TYPE: DNA
<213> ORGANISM: Artificial Sequence
<220> FEATURE:
<223> OTHER INFORMATION: Synthetic Construct

<400> SEQUENCE: 57
gttctgtctg taatctgcga accgattctg ccgtttg                                   37

<210> SEQ ID NO 58
<211> LENGTH: 44
<212> TYPE: DNA
<213> ORGANISM: Artificial Sequence
<220> FEATURE:
<223> OTHER INFORMATION: Synthetic Construct

<400> SEQUENCE: 58
gaacaaggaa aaactgagtg gtagcccgtt cgcgaaaccg ttcg                           44

<210> SEQ ID NO 59
<211> LENGTH: 31
<212> TYPE: DNA
<213> ORGANISM: Artificial Sequence
<220> FEATURE:
<223> OTHER INFORMATION: Synthetic Construct

<400> SEQUENCE: 59
gaaaaactga gtggtagcct gttcgcgaaa c                                         31

<210> SEQ ID NO 60
<211> LENGTH: 31
<212> TYPE: DNA
<213> ORGANISM: Artificial Sequence
<220> FEATURE:
<223> OTHER INFORMATION: Synthetic Construct

<400> SEQUENCE: 60

```
aggctaccac tcagttttc cttgttcatc t                                            31
```

<210> SEQ ID NO 61
<211> LENGTH: 37
<212> TYPE: DNA
<213> ORGANISM: Artificial Sequence
<220> FEATURE:
<223> OTHER INFORMATION: Synthetic Construct

<400> SEQUENCE: 61

```
gttctgtctg taatctttga accgattctg ccgtttg                                     37
```

<210> SEQ ID NO 62
<211> LENGTH: 29
<212> TYPE: DNA
<213> ORGANISM: Artificial Sequence
<220> FEATURE:
<223> OTHER INFORMATION: Synthetic Construct

<400> SEQUENCE: 62

```
cggttcaaag attacagaca gaacgcgtt                                              29
```

<210> SEQ ID NO 63
<211> LENGTH: 559
<212> TYPE: PRT
<213> ORGANISM: Artificial Sequence
<220> FEATURE:
<223> OTHER INFORMATION: Synthetic Construct

<400> SEQUENCE: 63

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
```

```
            225                 230                 235                 240
        Ser Arg Trp Trp Arg Arg Val Gly Leu Ala Thr Lys Leu His Phe Ala
                        245                 250                 255
        Arg Asp Arg Leu Ile Glu Ser Phe Tyr Trp Ala Val Gly Val Ala Phe
                        260                 265                 270
        Glu Pro Gln Tyr Ser Asp Cys Arg Asn Ser Val Ala Lys Met Phe Ser
                        275                 280                 285
        Phe Val Thr Ile Ile Asp Asp Ile Tyr Asp Val Tyr Gly Thr Leu Asp
                        290                 295                 300
        Glu Leu Glu Leu Phe Thr Asp Ala Val Glu Arg Trp Asp Val Asn Ala
        305                 310                 315                 320
        Ile Asn Asp Leu Pro Asp Tyr Met Lys Leu Cys Phe Leu Ala Leu Tyr
                        325                 330                 335
        Asn Thr Ile Asn Glu Ile Ala Tyr Asp Asn Leu Lys Asp Lys Gly Glu
                        340                 345                 350
        Asn Ile Leu Pro Tyr Leu Thr Lys Ala Trp Ala Asp Leu Cys Asn Ala
                        355                 360                 365
        Phe Leu Gln Glu Ala Lys Trp Leu Tyr Asn Lys Ser Thr Pro Thr Phe
                        370                 375                 380
        Asp Asp Tyr Phe Gly Asn Ala Trp Lys Ser Ser Ser Gly Pro Leu Gln
        385                 390                 395                 400
        Leu Val Phe Ala Tyr Phe Ala Val Val Gln Asn Ile Lys Lys Glu Glu
                        405                 410                 415
        Ile Glu Asn Leu Gln Lys Tyr His Asp Thr Ile Ser Arg Pro Ser His
                        420                 425                 430
        Ile Phe Arg Leu Cys Asn Asp Leu Ala Ser Ser Ala Glu Ile Ala
                        435                 440                 445
        Arg Gly Glu Thr Ala Asn Ser Val Ser Cys Tyr Met Arg Thr Lys Gly
                        450                 455                 460
        Ile Ser Glu Glu Leu Ala Thr Glu Ser Val Met Asn Leu Ile Asp Glu
        465                 470                 475                 480
        Thr Trp Lys Lys Met Asn Lys Glu Lys Leu Gly Gly Ser Leu Phe Ala
                        485                 490                 495
        Lys Pro Phe Val Glu Thr Ala Ile Asn Leu Ala Arg Gln Ser His Cys
                        500                 505                 510
        Thr Tyr His Asn Gly Asp Ala His Thr Ser Pro Asp Glu Leu Thr Arg
                        515                 520                 525
        Lys Arg Val Leu Ser Val Ile Thr Glu Pro Ile Leu Pro Phe Glu Arg
                        530                 535                 540
        Glu Asn Leu Tyr Phe Gln Gly Leu Glu His His His His His
        545                 550                 555

<210> SEQ ID NO 64
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 64
tggcgaatgg gacgcgccct gtagcggcgc attaagcgcg gcgggtgtgg tggttacgcg        60
cagcgtgacc gctacacttg ccagcgccct agcgcccgct cctttcgctt tcttcccttc       120
ctttctcgcc acgttcgccg gctttccccg tcaagctcta atcgggggc tcccttttagg       180 gttccgattt agtgctttac ggcacctcga ccccaaaaaa cttgattagg gtgatggttc       240
```

```
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taagggatttt tgccgatttc ggcctattgg ttaaaaaatg agctgattta    420
acaaaatttt aacgcgaatt ttaacaaaat attaacgttt acaatttcag gtggcacttt     480
tcggggaaat gtgcgcggaa cccctatttg tttattttc taaatacatt caaatatgta     540
tccgctcatg aattaattct tagaaaaact catcgagcat caaatgaaac tgcaatttat     600
tcatatcagg attatcaata ccatatttt gaaaaagccg tttctgtaat aaggagaaa      660
actcaccgag gcagttccat aggatggcaa gatcctggta tcggtctgcg attccgactc    720
gtccaacatc aatacaacct attaatttcc cctcgtcaaa aataaggtta tcaagtgaga   780
aatcaccatg agtgacgact gaatccggtg agaatggcaa aagtttatgc atttcttcc     840
agacttgttc aacaggccag ccattacgct cgtcatcaaa atcactcgca tcaaccaaac    900
cgttattcat tcgtgattgc gcctgagcga acgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccattatata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc gaagggaga     1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg cctttgctc acatgttctt tcctgcgtta     2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
```

```
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagactttα    3000 cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgccggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccatc ggtgatgtcg gcgatatagg cgccagcaac cgcacctgtg    4920
gcgccggtga tgccggccac gatgcgtccg gcgtagagga tcgagatctc gatcccgcga    4980
```

```
aattaatacg actcactata ggggaattgt gagcggataa caattcccct ctagaaataa      5040
ttttgtttaa ctttaagaag gagatataca tatggaagct cgtcgttctg cgaactacga      5100
acctaacagc tgggactatg attacctgct gtcctccgac acggacgagt ccatcgaagt      5160
atacaaagac aaagcgaaaa agctggaagc cgaagttcgt cgcgagatta ataacgaaaa      5220
agcagaattt ctgaccctgc tggaactgat tgacaacgtc cagcgcctgg gcctgggtta      5280
ccgtttcgag tctgatatcc gtggtgcgct ggatcgcttc gtttcctccg cgggcttcga      5340
tgcggtaacc aagacttccc tgcacggtac ggcactgtct ttccgtctgc tgcgtcaaca      5400
cggttttgag gtttctcagg aagcgttcag cggcttcaaa gaccaaaacg caacttcct       5460 ggagaacctg aaggaagata tcaaagctat cctgagcctg tacgaggcca gcttcctggc      5520
tctggaaggc gaaaacatcc tggacgaggc gaaggttttc gcaatctctc atctgaaaga      5580
actgtctgaa gaaaagatcg gtaaagagct ggcagaacag gtgaaccatg cactggaact      5640
gccactgcat cgccgtactc agcgtctgga agcagtatgg tctatcgagg cctaccgtaa      5700
aaaggaggac gcgaatcagg ttctgctgga gctggcaatt ctggattaca acatgatcca      5760
gtctgtatac cagcgtgatc tgcgtgaaac gtcccgttgg tggcgtcgtg tgggtctggc      5820
gaccaaactg cactttgctc gtgaccgcct gattgagagc ttctactggg ccgtgggtgt      5880
agcattcgaa ccgcaatact ccgactgccg taactccgtc gcaaaaatgt tttctttcgt      5940
aaccattatc gacgatatct acgatgtata cggcaccctg gacgaactgg agctgtttac      6000
tgatgcagtt gagcgttggg acgtaaacgc catcaacgac ctgccggatt acatgaaact      6060
gtgctttctg gctctgtata acactattaa cgaaatcgcc tacgacaacc tgaaagataa      6120
aggtgagaac atcctgccgt atctgaccaa agcctgggct gacctgtgca acgctttcct      6180
gcaagaagcc aagtggctgt acaacaaatc tactccgacc tttgacgact acttcggcaa      6240
cgcatggaaa tcctcttctg gcccgctgca actggtgttc gcttacttcg ctgtcgtgca      6300
gaacattaaa aaggaagaga tcgaaaacct gcaaaaatac catgacacca tctctcgtcc      6360
ttcccatatc ttccgtctgt gcaatgacct ggctagcgcg tctgcggaaa ttgcgcgtgg      6420
tgaaaccgca aatagcgttt cttgttacat gcgcactaaa ggtatctccg aagaactggc      6480
taccgaaagc gtgatgaatc tgatcgatga aacctggaaa aagatgaaca aggaaaaact      6540
gggtggtagc ctgttcgcga aaccgttcgt ggaaaccgcg atcaacctgg cacgtcaatc      6600
tcactgcact tatcataacg gcgacgcgca tacctctccg gatgagctga cccgcaaacg      6660
cgttctgtct gtaatcactg aaccgattct gccgtttgaa cgcgaaaacc tgtattttca      6720
gggcctcgag caccaccacc accaccactg agatccggct gctaacaaag cccgaaagga      6780
agctgagttg gctgctgcca ccgctgagca ataactagca taaccccttg ggcctctaa      6840 acgggtcttg aggggttttt tgctgaaagg aggaactata tccggat                   6887
```

<210> SEQ ID NO 65
<211> LENGTH: 559
<212> TYPE: PRT
<213> ORGANISM: Artificial Sequence
<220> FEATURE:
<223> OTHER INFORMATION: Synthetic Construct

<400> SEQUENCE: 65

Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys

-continued

```
                20                  25                  30
Asp Lys Ala Lys Lys Leu Glu Ala Glu Val Arg Arg Glu Ile Asn Asn
             35                  40                  45
Glu Lys Ala Glu Phe Leu Thr Leu Leu Glu Leu Ile Asp Asn Val Gln
 50                  55                  60
Arg Leu Gly Leu Gly Tyr Arg Phe Glu Ser Asp Ile Arg Gly Ala Leu
 65                  70                  75                  80
Asp Arg Phe Val Ser Ser Gly Gly Phe Asp Ala Val Thr Lys Thr Ser
                 85                  90                  95
Leu His Gly Thr Ala Leu Ser Phe Arg Leu Leu Arg Gln His Gly Phe
            100                 105                 110
Glu Val Ser Gln Glu Ala Phe Ser Gly Phe Lys Asp Gln Asn Gly Asn
            115                 120                 125
Phe Leu Glu Asn Leu Lys Glu Asp Ile Lys Ala Ile Leu Ser Leu Tyr
            130                 135                 140
Glu Ala Ser Phe Leu Ala Leu Glu Gly Glu Asn Ile Leu Asp Glu Ala
145                 150                 155                 160
Lys Val Phe Ala Ile Ser His Leu Lys Glu Leu Ser Glu Glu Lys Ile
                165                 170                 175
Gly Lys Glu Leu Ala Glu Gln Val Asn His Ala Leu Glu Leu Pro Leu
            180                 185                 190
His Arg Arg Thr Gln Arg Leu Glu Ala Val Trp Ser Ile Glu Ala Tyr
            195                 200                 205
Arg Lys Lys Glu Asp Ala Asn Gln Val Leu Leu Glu Leu Ala Ile Leu
            210                 215                 220
Asp Tyr Asn Met Ile Gln Ser Val Tyr Gln Arg Asp Leu Arg Glu Thr
225                 230                 235                 240
Ser Arg Trp Trp Arg Arg Val Gly Leu Ala Thr Lys Leu His Phe Ala
                245                 250                 255
Arg Asp Arg Leu Ile Glu Ser Phe Tyr Trp Ala Val Gly Val Ala Phe
            260                 265                 270
Glu Pro Gln Tyr Ser Asp Cys Arg Asn Ser Val Ala Lys Met Phe Ser
            275                 280                 285
Phe Val Thr Ile Ile Asp Asp Ile Tyr Asp Val Tyr Gly Thr Leu Asp
            290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                325                 330                 335
Asn Thr Ile Asn Glu Ile Ala Tyr Asp Asn Leu Lys Asp Lys Gly Glu
            340                 345                 350
Asn Ile Leu Pro Tyr Leu Thr Lys Ala Trp Ala Asp Leu Cys Asn Ala
            355                 360                 365
Phe Leu Gln Glu Ala Lys Trp Leu Tyr Asn Lys Ser Thr Pro Thr Phe
            370                 375                 380
Asp Asp Tyr Phe Gly Asn Ala Trp Lys Ser Ser Gly Pro Leu Gln
385                 390                 395                 400
Leu Val Phe Ala Tyr Phe Ala Val Val Gln Asn Ile Lys Lys Glu Glu
                405                 410                 415
Ile Glu Asn Leu Gln Lys Tyr His Asp Thr Ile Ser Arg Pro Ser His
            420                 425                 430
Ile Phe Arg Leu Cys Asn Asp Leu Ala Ser Ala Ser Ala Glu Ile Ala
            435                 440                 445
```

```
Arg Gly Glu Thr Asn Asn Ser Val Ser Cys Tyr Met Arg Thr Lys Gly
            450                 455                 460

Ile Ser Glu Glu Leu Ala Thr Glu Ser Val Met Asn Leu Ile Asp Glu
465                 470                 475                 480

Thr Trp Lys Lys Met Asn Lys Lys Leu Gly Gly Ser Leu Phe Ala
                485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
            515                 520                 525

Lys Arg Val Leu Ser Val Ile Thr Glu Pro Ile Leu Pro Phe Glu Arg
            530                 535                 540

Glu Asn Leu Tyr Phe Gln Gly Leu Glu His His His His His
545                 550                 555
```

<210> SEQ ID NO 66
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 66

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tcccttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttatttttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttcttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |

```
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc  cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccaggggaa  acgcctggta tctttatagt cctgtcgggt ttcgccacct ctgacttgag   2040
cgtcgatttt tgtgatgctc gtcaggggg  cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
```

-continued

```
atcccactac cgagatatcc gcaccaacgc gcagcccgga ctcggtaatg gcgcgcattg      3840
cgcccagcgc catctgatcg ttggcaacca gcatcgcagt gggaacgatg ccctcattca      3900
gcatttgcat ggtttgttga aaaccggaca tggcactcca gtcgccttcc cgttccgcta      3960
tcggctgaat ttgattgcga gtgagatatt tatgccagcc agccgacgcg agacgcgccg      4020
agacagaact taatgggccc gctaacagcg cgatttgctg gtgacccaat gcgaccagat      4080
gctccacgcc cagtcgcgta ccgtcttcat gggagaaaat aatactgttg atgggtgtct      4140
ggtcagagac atcaagaaat aacgccggaa cattagtgca ggcagcttcc acagcaatgg      4200
catcctggtc atccagcgga tagttaatga tcagcccact gacgcgttgc gcgagaagat      4260
tgtgcaccgc cgctttacag gcttcgacgc cgcttcgttc taccatcgac accaccacgc      4320
tggcacccag ttgatcggcg cgagatttaa tcgccgcgac aatttgcgac ggcgcgtgca      4380
gggccagact ggaggtggca acgccaatca gcaacgactg tttgcccgcc agttgttgtg      4440
ccacgcggtt gggaatgtaa ttcagctccg ccatcgccgc ttccactttt tcccgcgttt      4500
tcgcagaaac gtggctggcc tggttcacca cgcgggaaac ggtctgataa gagacaccgg      4560
catactctgc gacatcgtat aacgttactg gtttcacatt caccaccctg aattgactct      4620
cttccgggcg ctatcatgcc ataccgcgaa aggttttgcg ccattcgatg gtgtccggga      4680
tctcgacgct ctcccttatg cgactcctgc attaggaagc agcccagtag taggttgagg      4740
ccgttgagca ccgccgccgc aaggaatggt gcatgcaagg agatggcgcc caacagtccc      4800
ccggccacgg ggcctgccac catacccacg ccgaaacaag cgctcatgag cccgaagtgg      4860
cgagcccgat cttccccatc ggtgatgtcg gcgatatagg cgccagcaac cgcacctgtg      4920
gcgccggtga tgccggccac gatgcgtccg gcgtagagga tcgagatctc gatcccgcga      4980
aattaatacg actcactata ggggaattgt gagcggataa caattcccct ctagaaataa      5040
ttttgtttaa ctttaagaag gagatataca tatggaagct cgtcgttctg cgaactacga      5100
acctaacagc tgggactatg attacctgct gtcctccgac acggacgagt ccatcgaagt      5160
atacaaagac aaagcgaaaa agctggaagc cgaagttcgt cgcgagatta ataacgaaaa      5220
agcagaattt ctgaccctgc tggaactgat tgacaacgtc cagcgcctgg gcctgggtta      5280
ccgtttcgag tctgatatcc gtggtgcgct ggatcgcttc gtttcctccg gcggcttcga      5340
tgcggtaacc aagacttccc tgcacggtac ggcactgtct ttccgtctgc tgcgtcaaca      5400
cggttttgag gtttctcagg aagcgttcag cggcttcaaa gaccaaaacg gcaacttcct      5460
ggagaacctg aaggaagata tcaaagctat cctgagcctg tacgaggcca gcttcctggc      5520
tctggaaggc gaaaacatcc tggacgaggc gaaggttttc gcaatctctc atctgaaaga      5580
actgtctgaa gaaagatcg gtaaagagct ggcagaacag gtgaaccatg cactggaact      5640
gccactgcat cgccgtactc agcgtctgga agcagtatgg tctatcgagg cctaccgtaa      5700
aaaggaggac gcgaatcagg ttctgctgga gctggcaatt ctggattaca acatgatcca      5760
gtctgtatac cagcgtgatc tgcgtgaaac gtcccgttgg tggcgtcgtg tgggtctggc      5820
gaccaaactg cactttgctc gtgaccgcct gattgagagc ttctactggg ccgtgggtgt      5880
agcattcgaa ccgcaatact ccgactgccg taactccgtc gcaaaatgt tttctttcgt      5940 aaccattatc gacgatatct acgatgtata cggcaccctg gacgaactgg agctgtttac      6000
tgatgcagtt gagcgttggg acgtaaacgc catcaacgac ctgccggatt acatgaaact      6060
gtgctttctg gctctgtata acactattaa cgaaatcgcc tacgacaacc tgaaagataa      6120
aggtgagaac atcctgccgt atctgaccaa agcctgggct gacctgtgca acgctttcct      6180
```

-continued

```
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccaac aatagcgttt cttgttacat gcgcactaaa ggtatctccg aagaactggc    6480
taccgaaagc gtgatgaatc tgatcgatga acctggaaa aagatgaaca aggaaaaact    6540
gggtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg ggcctctaa    6840 acgggtcttg aggggttttt tgctgaaagg aggaactata tccggat    6887
```

<210> SEQ ID NO 67
<211> LENGTH: 559
<212> TYPE: PRT
<213> ORGANISM: Artificial Sequence
<220> FEATURE:
<223> OTHER INFORMATION: Synthetic Construct

<400> SEQUENCE: 67

```
Met Glu Ala Arg Arg Ser Ala Asn Tyr Glu Pro Asn Ser Trp Asp Tyr
  1               5                  10                  15

Asp Tyr Leu Leu Ser Ser Asp Thr Asp Glu Ser Ile Glu Val Tyr Lys
             20                  25                  30

Asp Lys Ala Lys Lys Leu Glu Ala Glu Val Arg Arg Glu Ile Asn Asn
         35                  40                  45

Glu Lys Ala Glu Phe Leu Thr Leu Leu Glu Leu Ile Asp Asn Val Gln
     50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                 85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240
```

Ser Arg Trp Trp Arg Arg Val Gly Leu Ala Thr Lys Leu His Phe Ala
            245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
            275                 280                 285

Phe Val Thr Ile Ile Asp Asp Ile Tyr Asp Val Tyr Gly Thr Leu Asp
            290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
            325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
            355                 360                 365

Phe Leu Gln Glu Ala Lys Trp Leu Tyr Asn Lys Ser Thr Pro Thr Phe
            370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
            405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
            435                 440                 445

Arg Gly Glu Thr Ala Asn Ser Val Ser Cys Tyr Met Arg Thr Lys Gly
            450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Ser Gly Ser Leu Phe Ala
            485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
            515                 520                 525

Lys Arg Val Leu Ser Val Ile Thr Glu Pro Ile Leu Pro Phe Glu Arg
            530                 535                 540

Glu Asn Leu Tyr Phe Gln Gly Leu Glu His His His His His His
545                 550                 555

<210> SEQ ID NO 68
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 68
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tccctttagg      180 gttccgattt agtgctttac ggcacctcga ccccaaaaaa cttgattagg gtgatggttc     240

-continued

```
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttcttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatcctttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcaggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
```

```
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccatc ggtgatgtcg gcgatatagg cgccagcaac cgcacctgtg    4920
gcgccggtga tgccggccac gatgcgtccg gcgtagagga tcgagatctc gatcccgcga    4980
```

```
aattaatacg actcactata ggggaattgt gagcggataa caattcccct ctagaaataa    5040
ttttgtttaa ctttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgacccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca cgctttcct     6180 gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga acctggaaaa aagatgaaca aggaaaaact    6540
gagtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg ggcctctaa     6840 acgggtcttg aggggttttt tgctgaaagg aggaactata tccggat                  6887
```

<210> SEQ ID NO 69
<211> LENGTH: 559
<212> TYPE: PRT
<213> ORGANISM: Artificial Sequence
<220> FEATURE:
<223> OTHER INFORMATION: Synthetic Construct

<400> SEQUENCE: 69

Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

```
Asp Lys Ala Lys Lys Leu Glu Ala Glu Val Arg Arg Glu Ile Asn Asn
         35                  40                  45

Glu Lys Ala Glu Phe Leu Thr Leu Leu Glu Leu Ile Asp Asn Val Gln
 50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                 85                  90                  95

Leu His Gly Thr Ala Leu Ser Phe Arg Leu Leu Arg Gln His Gly Phe
                100                 105                 110

Glu Val Ser Gln Glu Ala Phe Ser Gly Phe Lys Asp Gln Asn Gly Asn
            115                 120                 125

Phe Leu Glu Asn Leu Lys Glu Asp Ile Lys Ala Ile Leu Ser Leu Tyr
        130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
210                 215                 220

Asp Tyr Asn Met Ile Gln Ser Val Tyr Gln Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
        290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445
```

```
Arg Gly Glu Thr Ala Asn Ser Val Ser Cys Tyr Met Arg Thr Lys Gly
        450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Pro Phe Ala
                485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
            515                 520                 525

Lys Arg Val Leu Ser Val Ile Thr Glu Pro Ile Leu Pro Phe Glu Arg
530                 535                 540

Glu Asn Leu Tyr Phe Gln Gly Leu Glu His His His His His His
545                 550                 555

<210> SEQ ID NO 70
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 70
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta      420 acaaaattt aacgcgaatt ttaacaaaat attaacgttt acaatttcag gtggcacttt      480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa ataaggtta tcaagtgaga     780 aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgaaatac gcgatcgctg ttaaaaggac      960
aattacaaac aggaatcgaa tgcaaccggc gcaggaacac tgccagcgca tcaacaatat    1020
tttcacctga tcaggatat tcttctaata cctggaatgc tgttttcccg gggatcgcag     1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
```

-continued

```
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
```

-continued

```
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccacttttt tcccgcgttt   4500 tcgcagaaac gtggctggcc tggttcacca cgcgggaaac ggtctgataa agacaccgg    4560 catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
```

-continued

```
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ccgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg gggcctctaa    6840
acgggtcttg aggggttttt tgctgaaagg aggaactata tccggat                  6887
```

<210> SEQ ID NO 71
<211> LENGTH: 559
<212> TYPE: PRT
<213> ORGANISM: Artificial Sequence
<220> FEATURE:
<223> OTHER INFORMATION: Synthetic Construct

<400> SEQUENCE: 71

| Met | Glu | Ala | Arg | Arg | Ser | Ala | Asn | Tyr | Glu | Pro | Asn | Ser | Trp | Asp | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Tyr | Leu | Leu | Ser | Ser | Asp | Thr | Asp | Glu | Ser | Ile | Glu | Val | Tyr | Lys |
|     |     |     | 20  |     |     |     |     | 25  |     |     |     |     | 30  |     |     |

| Asp | Lys | Ala | Lys | Lys | Leu | Glu | Ala | Glu | Val | Arg | Arg | Glu | Ile | Asn | Asn |
|     |     |     | 35  |     |     |     |     | 40  |     |     |     |     | 45  |     |     |

| Glu | Lys | Ala | Glu | Phe | Leu | Thr | Leu | Leu | Glu | Leu | Ile | Asp | Asn | Val | Gln |
|     | 50  |     |     |     |     | 55  |     |     |     |     | 60  |     |     |     |     |

| Arg | Leu | Gly | Leu | Gly | Tyr | Arg | Phe | Glu | Ser | Asp | Ile | Arg | Gly | Ala | Leu |
| 65  |     |     |     |     | 70  |     |     |     |     | 75  |     |     |     |     | 80  |

| Asp | Arg | Phe | Val | Ser | Ser | Gly | Gly | Phe | Asp | Ala | Val | Thr | Lys | Thr | Ser |
|     |     |     |     | 85  |     |     |     |     | 90  |     |     |     |     | 95  |     |

| Leu | His | Gly | Thr | Ala | Leu | Ser | Phe | Arg | Leu | Leu | Arg | Gln | His | Gly | Phe |
|     |     |     |     | 100 |     |     |     |     | 105 |     |     |     |     | 110 |     |

| Glu | Val | Ser | Gln | Glu | Ala | Phe | Ser | Gly | Phe | Lys | Asp | Gln | Asn | Gly | Asn |
|     |     |     | 115 |     |     |     |     | 120 |     |     |     |     | 125 |     |     |

| Phe | Leu | Glu | Asn | Leu | Lys | Glu | Asp | Ile | Lys | Ala | Ile | Leu | Ser | Leu | Tyr |
|     | 130 |     |     |     |     | 135 |     |     |     |     | 140 |     |     |     |     |

| Glu | Ala | Ser | Phe | Leu | Ala | Leu | Glu | Gly | Glu | Asn | Ile | Leu | Asp | Glu | Ala |
| 145 |     |     |     |     | 150 |     |     |     |     | 155 |     |     |     |     | 160 |

| Lys | Val | Phe | Ala | Ile | Ser | His | Leu | Lys | Glu | Leu | Ser | Glu | Glu | Lys | Ile |
|     |     |     |     | 165 |     |     |     |     | 170 |     |     |     |     | 175 |     |

| Gly | Lys | Glu | Leu | Ala | Glu | Gln | Val | Asn | His | Ala | Leu | Glu | Leu | Pro | Leu |
|     |     |     | 180 |     |     |     |     | 185 |     |     |     |     | 190 |     |     |

| His | Arg | Arg | Thr | Gln | Arg | Leu | Glu | Ala | Val | Trp | Ser | Ile | Glu | Ala | Tyr |
|     |     |     | 195 |     |     |     |     | 200 |     |     |     |     | 205 |     |     |

| Arg | Lys | Lys | Glu | Asp | Ala | Asn | Gln | Val | Leu | Leu | Glu | Leu | Ala | Ile | Leu |
|     | 210 |     |     |     |     | 215 |     |     |     |     | 220 |     |     |     |     |

| Asp | Tyr | Asn | Met | Ile | Gln | Ser | Val | Tyr | Gln | Arg | Asp | Leu | Arg | Glu | Thr |
| 225 |     |     |     |     | 230 |     |     |     |     | 235 |     |     |     |     | 240 |

Ser Arg Trp Trp Arg Arg Val Gly Leu Ala Thr Lys Leu His Phe Ala
            245                 250                 255

Arg Asp Arg Leu Ile Glu Ser Phe Tyr Trp Ala Val Gly Val Ala Phe
        260                 265                 270

Glu Pro Gln Tyr Ser Asp Cys Arg Asn Ser Val Ala Lys Met Phe Ser
    275                 280                 285

Phe Val Thr Ile Ile Asp Asp Ile Tyr Asp Val Tyr Gly Thr Leu Asp
290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
    530                 535                 540

Glu Asn Leu Tyr Phe Gln Gly Leu Glu His His His His His His
545                 550                 555

<210> SEQ ID NO 72
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 72
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcggggc tcccttttagg    180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300

-continued

```
ctttaatagt ggactcttgt tccaaactgg aacaacactc aaccctatct cggtctattc    360
ttttgattta aagggatttt tgccgatttc ggcctattgg ttaaaaatg agctgattta     420 acaaaaattt aacgcgaatt ttaacaaaat attaacgttt acaatttcag gtggcacttt   480
tcggggaaat gtgcgcggaa cccctatttg tttattttc taaatacatt caaatatgta    540
tccgctcatg aattaattct tagaaaaact catcgagcat caaatgaaac tgcaatttat   600
tcatatcagg attatcaata ccatatttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga   780
aatcaccatg agtgacgact gaatccggtg agaatggcaa aagtttatgc atttctttcc    840
agacttgttc aacaggccag ccattacgct cgtcatcaaa atcactcgca tcaaccaaac   900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca    1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa    1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggggg cggagcctat ggaaaaacgc cagcaacgcg   2100
gcctttttac ggttcctggc cttttgctgg cttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg   2280 tatttctcc ttacgcatct gtgcggtatt tcacaccgca tatatggtgc actctcagta    2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
```

```
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
```

```
tttgtttaa ctttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaacatcc tggacgaggc gaaggttttc gcaatctctc atctgaaaga    5580
actgtctgaa gaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940 aaccattatc gacgatatct acgatgtata cggcaccctg gacgaactgg agctgtttac    6000
tgatgcagtt gagcgttggg acgtaaacgc catcaacgac ctgccggatt acatgaaact    6060 gtgcttctg gctctgtata acactattaa cgaaatcgcc tacgacaacc tgaaagataa    6120
aggtgagaac atcctgccgt atctgaccaa agcctgggct gacctgtgca cgctttcct    6180 gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga acctggaaa aagatgaaca aggaaaaact    6540
gggtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatctgcg aaccgattct gccgtttgaa cgcgaaaacc tgtattttca    6720
gggcctcgag caccaccacc accaccactg agatccggct gctaacaaag cccgaaagga    6780
agctgagttg ctgctgccaa ccgctgagca ataactagca taaccccttg ggcctctaa    6840 acgggtcttg aggggttttt tgctgaaagg aggaactata tccggat            6887
```

<210> SEQ ID NO 73
<211> LENGTH: 559
<212> TYPE: PRT
<213> ORGANISM: Artificial Sequence
<220> FEATURE:
<223> OTHER INFORMATION: Synthetic Construct

<400> SEQUENCE: 73

Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

-continued

```
Asp Lys Ala Lys Lys Leu Glu Ala Glu Val Arg Arg Glu Ile Asn Asn
         35                  40                  45
Glu Lys Ala Glu Phe Leu Thr Leu Leu Glu Leu Ile Asp Asn Val Gln
 50                  55                  60
Arg Leu Gly Leu Gly Tyr Arg Phe Glu Ser Asp Ile Arg Gly Ala Leu
 65                  70                  75                  80
Asp Arg Phe Val Ser Ser Gly Phe Asp Ala Val Thr Lys Thr Ser
                     85                  90                  95
Leu His Gly Thr Ala Leu Ser Phe Arg Leu Leu Arg Gln His Gly Phe
                100                 105                 110
Glu Val Ser Gln Glu Ala Phe Ser Gly Phe Lys Asp Gln Asn Gly Asn
            115                 120                 125
Phe Leu Glu Asn Leu Lys Glu Asp Ile Lys Ala Ile Leu Ser Leu Tyr
    130                 135                 140
Glu Ala Ser Phe Leu Ala Leu Glu Gly Glu Asn Ile Leu Asp Glu Ala
145                 150                 155                 160
Lys Val Phe Ala Ile Ser His Leu Lys Glu Leu Ser Glu Glu Lys Ile
                165                 170                 175
Gly Lys Glu Leu Ala Glu Gln Val Asn His Ala Leu Glu Leu Pro Leu
            180                 185                 190
His Arg Arg Thr Gln Arg Leu Glu Ala Val Trp Ser Ile Glu Ala Tyr
    195                 200                 205
Arg Lys Lys Glu Asp Ala Asn Gln Val Leu Leu Glu Leu Ala Ile Leu
210                 215                 220
Asp Tyr Asn Met Ile Gln Ser Val Tyr Gln Arg Asp Leu Arg Glu Thr
225                 230                 235                 240
Ser Arg Trp Trp Arg Arg Val Gly Leu Ala Thr Lys Leu His Phe Ala
                245                 250                 255
Arg Asp Arg Leu Ile Glu Ser Phe Tyr Trp Ala Val Gly Val Ala Phe
            260                 265                 270
Glu Pro Gln Tyr Ser Asp Cys Arg Asn Ser Val Ala Lys Met Phe Ser
    275                 280                 285
Phe Val Thr Ile Ile Asp Asp Ile Tyr Asp Val Tyr Gly Thr Leu Asp
290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                325                 330                 335
Asn Thr Ile Asn Glu Ile Ala Tyr Asp Asn Leu Lys Asp Lys Gly Glu
            340                 345                 350
Asn Ile Leu Pro Tyr Leu Thr Lys Ala Trp Ala Asp Leu Cys Asn Ala
    355                 360                 365
Phe Leu Gln Glu Ala Lys Trp Leu Tyr Asn Lys Ser Thr Pro Thr Phe
370                 375                 380
Asp Asp Tyr Phe Gly Asn Ala Trp Lys Ser Ser Gly Pro Leu Gln
385                 390                 395                 400
Leu Val Phe Ala Tyr Phe Ala Val Gln Asn Ile Lys Lys Glu Glu
                405                 410                 415
Ile Glu Asn Leu Gln Lys Tyr His Asp Thr Ile Ser Arg Pro Ser His
            420                 425                 430
Ile Phe Arg Leu Cys Asn Asp Leu Ala Ser Ala Ser Ala Glu Ile Ala
    435                 440                 445
Arg Gly Glu Thr Asn Asn Ser Val Ser Cys Tyr Met Arg Thr Lys Gly
```

```
                450              455             460
Ile Ser Glu Glu Leu Ala Thr Glu Ser Val Met Asn Leu Ile Asp Glu
465                 470                  475                 480

Thr Trp Lys Lys Met Asn Lys Glu Lys Leu Ser Gly Ser Leu Phe Ala
                485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
            515                 520                 525

Lys Arg Val Leu Ser Val Ile Thr Glu Pro Ile Leu Pro Phe Glu Arg
530                 535                 540

Glu Asn Leu Tyr Phe Gln Gly Leu Glu His His His His His
545                 550                 555
```

<210> SEQ ID NO 74
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 74

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcgggggc tccctttagg    180
gttccgattt agtgctttac ggcacctcga ccccaaaaaa cttgattagg gtgatggttc    240
acgtagtggg ccatcgccct gatagacggt ttttcgccct tgacgttgg agtccacgtt    300
ctttaatagt ggactcttgt tccaaactgg aacaacactc aaccctatct cggtctattc    360
ttttgattta agggattt tgccgatttc ggcctattgg ttaaaaaatg agctgattta     420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa agtttatgc atttcttttcc   840
agacttgttc aacaggccag ccattacgct cgtcatcaaa atcactcgca tcaaccaaac    900
cgttattcat tcgtgattgc gcctgagcga cgaaatac gcgatcgctg ttaaaaggac      960
aattacaaac aggaatcgaa tgcaaccggc gcaggaacac tgccagcgca tcaacaatat   1020
tttcacctga tcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa atcccttaa    1440
cgtgagtttt cgttccactg agcgtcagac cccgtagaaa agatcaaagg atcttcttga   1500
```

```
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
```

```
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg tgtccggga    4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgccggtaacc aagacttccc tgcacggtac ggcactgtct ttccgtctgc tgcgtcaaca   5400
cggttttgag gtttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgcttcctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
```

-continued

```
cgcatggaaa tcctcttctg gcccgctgca actggtgttc gcttacttcg ctgtcgtgca   6300
gaacattaaa aaggaagaga tcgaaaacct gcaaaaatac catgcaccca tctctcgtcc   6360
ttcccatatc ttccgtctgt gcaatgacct ggctagcgcg tctgcggaaa ttgcgcgtgg   6420
tgaaaccaac aatagcgttt cttgttacat gcgcactaaa ggtatctccg aagaactggc   6480
taccgaaagc gtgatgaatc tgatcgatga aacctggaaa aagatgaaca aggaaaaact   6540
gagtggtagc ctgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatcactg aaccgattct gccgtttgaa cgcgaaaacc tgtattttca   6720
gggcctcgag caccaccacc accaccactg agatccggct gctaacaaag cccgaaagga   6780
agctgagttg gctgctgcca ccgctgagca ataactagca taaccccttg ggcctctaa    6840 acgggtcttg aggggttttt tgctgaaagg aggaactata tccggat                 6887
```

<210> SEQ ID NO 75
<211> LENGTH: 559
<212> TYPE: PRT
<213> ORGANISM: Artificial Sequence
<220> FEATURE:
<223> OTHER INFORMATION: Synthetic Construct

<400> SEQUENCE: 75

```
Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
```

```
                    245                 250                 255
Arg Asp Arg Leu Ile Glu Ser Phe Tyr Trp Ala Val Gly Val Ala Phe
            260                 265                 270
Glu Pro Gln Tyr Ser Asp Cys Arg Asn Ser Val Ala Lys Met Phe Ser
        275                 280                 285
Phe Val Thr Ile Ile Asp Ile Tyr Asp Val Tyr Gly Thr Leu Asp
    290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                325                 330                 335
Asn Thr Ile Asn Glu Ile Ala Tyr Asp Asn Leu Lys Asp Lys Gly Glu
            340                 345                 350
Asn Ile Leu Pro Tyr Leu Thr Lys Ala Trp Ala Asp Leu Cys Asn Ala
        355                 360                 365
Phe Leu Gln Glu Ala Lys Trp Leu Tyr Asn Lys Ser Thr Pro Thr Phe
    370                 375                 380
Asp Asp Tyr Phe Gly Asn Ala Trp Lys Ser Ser Gly Pro Leu Gln
385                 390                 395                 400
Leu Val Phe Ala Tyr Phe Ala Val Val Gln Asn Ile Lys Lys Glu Glu
                405                 410                 415
Ile Glu Asn Leu Gln Lys Tyr His Asp Thr Ile Ser Arg Pro Ser His
            420                 425                 430
Ile Phe Arg Leu Cys Asn Asp Leu Ala Ser Ala Ser Ala Glu Ile Ala
        435                 440                 445
Arg Gly Glu Thr Asn Asn Ser Val Ser Cys Tyr Met Arg Thr Lys Gly
    450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Leu Gly Gly Ser Pro Phe Ala
                485                 490                 495
Lys Pro Phe Val Glu Thr Ala Ile Asn Leu Ala Arg Gln Ser His Cys
            500                 505                 510
Thr Tyr His Asn Gly Asp Ala His Thr Ser Pro Asp Glu Leu Thr Arg
        515                 520                 525
Lys Arg Val Leu Ser Val Ile Thr Glu Pro Ile Leu Pro Phe Glu Arg
    530                 535                 540
Glu Asn Leu Tyr Phe Gln Gly Leu Glu His His His His His
545                 550                 555

<210> SEQ ID NO 76
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 76
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcgggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
```

```
ctttaatagt ggactcttgt tccaaactgg aacaacactc aaccctatct cggtctattc    360
ttttgattta taagggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatatttt gaaaaagccg tttctgtaat gaaggagaaa    660
actcaccgag gcagttccat aggatggcaa gatcctggta tcggtctgcg attccgactc    720
gtccaacatc aatacaacct attaattcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gtttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccggggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggggaa acgcctggta tctttatagt cctgtcgggt ttcgccacct ctgacttgag   2040
cgtcgatttt tgtgatgctc gtcaggggggg cggagcctat ggaaaaacgc cagcaacgcg   2100
gcctttttac ggttcctggc cttttgctgg cctttgctc acatgttctt tcctgcgtta   2160 tccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
```

-continued

```
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt cccgcgtttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
```

-continued

```
ttttgtttaa ctttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940
aaccattatc gacgatatct acgatgtata cggcacccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccaac aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ccgttcgcga aaccgttcgt ggaaaccgcg atcaacctgg cacgtcaatc    6600
tcactgcact tatcataacg cgacgcgca tacctctccg gatgagctga cccgcaaacg    6660
cgttctgtct gtaatcactg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg gggcctctaa    6840
acgggtcttg aggggttttt tgctgaaagg aggaactata tccggat                 6887
```

<210> SEQ ID NO 77
<211> LENGTH: 559
<212> TYPE: PRT
<213> ORGANISM: Artificial Sequence
<220> FEATURE:
<223> OTHER INFORMATION: Synthetic Construct

<400> SEQUENCE: 77

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
```

-continued

```
                35                  40                  45
Glu Lys Ala Glu Phe Leu Thr Leu Leu Glu Leu Ile Asp Asn Val Gln
 50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                 85                  90                  95

Leu His Gly Thr Ala Leu Ser Phe Arg Leu Leu Arg Gln His Gly Phe
                100                 105                 110

Glu Val Ser Gln Glu Ala Phe Ser Gly Phe Lys Asp Gln Asn Gly Asn
            115                 120                 125

Phe Leu Glu Asn Leu Lys Glu Asp Ile Lys Ala Ile Leu Ser Leu Tyr
            130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
            195                 200                 205

Arg Lys Lys Glu Asp Ala Asn Gln Val Leu Leu Glu Leu Ala Ile Leu
210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
            275                 280                 285

Phe Val Thr Ile Ile Asp Asp Ile Tyr Asp Val Tyr Gly Thr Leu Asp
            290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
                340                 345                 350

Asn Ile Leu Pro Tyr Leu Thr Lys Ala Trp Ala Asp Leu Cys Asn Ala
            355                 360                 365

Phe Leu Gln Glu Ala Lys Trp Leu Tyr Asn Lys Ser Thr Pro Thr Phe
            370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ser Ala Glu Ile Ala
            435                 440                 445

Arg Gly Glu Thr Asn Asn Ser Val Ser Cys Tyr Met Arg Thr Lys Gly
450                 455                 460
```

```
Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
530                 535                 540

Glu Asn Leu Tyr Phe Gln Gly Leu Glu His His His His His His
545                 550                 555

<210> SEQ ID NO 78
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 78
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta       420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa agtttatgc atttctttcc     840 agacttgttc aacaggccag ccattacgct cgtcatcaaa atcactcgca tcaaccaaac     900
cgttattcat tcgtgattgc gcctgagcga cgaaatac gcgatcgctg ttaaaaggac      960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa     1440 cgtgagtttt cgttccactg agcgtcagac cccgtagaaa agatcaaagg atcttcttga    1500
```

```
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca gggtagcc agcagcatcc    2940 tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
```

```
gcatttgcat ggtttgttga aaaccggaca tggcactcca gtcgccttcc cgttccgcta    3960
tcggctgaat ttgattgcga gtgagatatt tatgccagcc agccgacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccacttttt tcccgcgttt    4500
tcgcagaaac gtggctggcc tggttcacca cgcgggaaac ggtctgataa agacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagct cgtcgttctg cgaactacga    5100
acctaacagc tgggactatg attacctgct gtcctccgac acgacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgcttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
```

```
cgcatggaaa tcctcttctg gcccgctgca actggtgttc gcttacttcg ctgtcgtgca    6300
gaacattaaa aaggaagaga tcgaaaacct gcaaaatac catgacacca tctctcgtcc     6360
ttcccatatc ttccgtctgt gcaatgacct ggctagcgcg tctgcggaaa ttgcgcgtgg    6420
tgaaaccaac aatagcgttt cttgttacat gcgcactaaa ggtatctccg aagaactggc    6480
taccgaaagc gtgatgaatc tgatcgatga acctggaaa aagatgaaca aggaaaaact     6540
gggtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatctgcg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg gggcctctaa    6840
acgggtcttg aggggttttt tgctgaaagg aggaactata tccggat                  6887
```

<210> SEQ ID NO 79
<211> LENGTH: 559
<212> TYPE: PRT
<213> ORGANISM: Artificial Sequence
<220> FEATURE:
<223> OTHER INFORMATION: Synthetic Construct

<400> SEQUENCE: 79

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255
```

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
            275                 280                 285

Phe Val Thr Ile Ile Asp Asp Ile Tyr Asp Val Tyr Gly Thr Leu Asp
        290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ser Ala Glu Ile Ala
        435                 440                 445

Arg Gly Glu Thr Asn Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Ser Gly Ser Pro Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Phe Glu Arg
    530                 535                 540

Glu Asn Leu Tyr Phe Gln Gly Leu Glu His His His His His His
545                 550                 555

<210> SEQ ID NO 80
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 80
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360

-continued

```
ttttgattta taagggattt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttattttc taaatacatt caaatatgta      540
tccgctcatg aattaattct tagaaaaact catcgagcat caaatgaaac tgcaatttat      600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa aataaggtta tcaagtgaga      780
aatcaccatg agtgacgact gaatccggtg agaatggcaa agtttatgc atttctttcc      840 agacttgttc aacaggccag ccattacgct cgtcatcaaa atcactcgca tcaaccaaac      900
cgttattcat tcgtgattgc gcctgagcga acgaaatac gcgatcgctg ttaaaaggac      960
aattacaaac aggaatcgaa tgcaaccggc gcaggaacac tgccagcgca tcaacaatat     1020
tttcacctga atcaggatat tcttctaata cctggaatgc tgttttcccg gggatcgcag     1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200
ctttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500
gatccttttt ttctgcgcgt aatctgctgc ttgcaaacaa aaaaaccacc gctaccagcg     1560
gtggtttgtt tgccggatca agagctacca actctttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata gtcgtgtct taccggggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc cgaagggaga     1920
aaggcggaca ggtatccggt aagcggcagg gtcggaacag gagagcgcac gagggagctt     1980 ccaggggaa acgcctggta tctttatagt cctgtcgggt ttcgccacct ctgacttgag     2040
cgtcgatttt tgtgatgctc gtcaggggg cggagcctat ggaaaaacgc cagcaacgcg     2100
gcctttttac ggttcctggc cttttgctgg cctttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac cccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt tttcctgttt     2700
```

-continued

```
ggtcactgat gcctccgtgt aagggggatt tctgttcatg ggggtaatga taccgatgaa      2760
acgagagagg atgctcacga tacgggttac tgatgatgaa catgcccggt tactggaacg      2820
ttgtgagggt aaacaactgg cggtatggat gcggcgggac cagagaaaaa tcactcaggg      2880
tcaatgccag cgcttcgtta atacagatgt aggtgttcca cagggtagcc agcagcatcc      2940
tgcgatgcag atccggaaca taatggtgca gggcgctgac ttccgcgttt ccagacttta      3000
cgaaacacgg aaaccgaaga ccattcatgt tgttgctcag gtcgcagacg ttttgcagca      3060
gcagtcgctt cacgttcgct cgcgtatcgg tgattcattc tgctaaccag taaggcaacc      3120
ccgccagcct agccgggtcc tcaacgacag gagcacgatc atgcgcaccc gtggggccgc      3180
catgccggcg ataatggcct gcttctcgcc gaaacgtttg gtggcgggac cagtgacgaa      3240
ggcttgagcg agggcgtgca agattccgaa taccgcaagc gacaggccga tcatcgtcgc      3300
gctccagcga aagcggtcct cgccgaaaat gacccagagc gctgccggca cctgtcctac      3360
gagttgcatg ataaagaaga cagtcataag tgccggcgacg atagtcatgc cccgcgccca      3420
ccggaaggag ctgactgggt tgaaggctct caagggcatc ggtcgagatc ccggtgccta      3480
atgagtgagc taacttacat taattgcgtt gcgctcactg cccgctttcc agtcgggaaa      3540
cctgtcgtgc cagctgcatt aatgaatcgg ccaacgcgcg gggagaggcg gtttgcgtat      3600
tgggcgccag ggtggttttt cttttcacca gtgagacggg caacagctga ttgcccttca      3660
ccgcctggcc ctgagagagt tgcagcaagc ggtccacgct ggtttgcccc agcaggcgaa      3720
aatcctgttt gatggtggtt aacggcggga tataacatga gctgtcttcg gtatcgtcgt      3780
atcccactac cgagatatcc gcaccaacgc gcagcccgga ctcggtaatg gcgcgcattg      3840
cgcccagcgc catctgatcg ttggcaacca gcatcgcagt gggaacgatg ccctcattca      3900
gcatttgcat ggtttgttga aaaccggaca tggcactcca gtcgccttcc cgttccgcta      3960
tcggctgaat ttgattgcga gtgagatatt tatgccagcc agccagacgc agacgcgccg      4020
agacagaact taatgggccc gctaacagcg cgatttgctg gtgacccaat gcgaccagat      4080
gctccacgcc cagtcgcgta ccgtcttcat gggagaaaat aatactgttg atgggtgtct      4140
ggtcagagac atcaagaaat aacgccggaa cattagtgca ggcagcttcc acagcaatgg      4200
catcctggtc atccagcgga tagttaatga tcagcccact gacgcgttgc gcgagaagat      4260
tgtgcaccgc cgctttacag gcttcgacgc cgcttcgttc taccatcgac accaccacgc      4320
tggcacccag ttgatcggcg cgagatttaa tcgccgcgac aatttgcgac ggcgcgtgca      4380
gggccagact ggaggtggca acgccaatca gcaacgactg tttgcccgcc agttgttgtg      4440
ccacgcggtt gggaatgtaa ttcagctccg ccatcgccgc ttccactttt tcccgcgttt      4500
tcgcagaaac gtggctggcc tggttcacca cgcgggaaac ggtctgataa gagacaccgg      4560
catactctgc gacatcgtat aacgttactg gtttcacatt caccaccctg aattgactct      4620
cttccgggcg ctatcatgcc ataccgcgaa aggttttgcg ccattcgatg gtgtccggga      4680
tctcgacgct ctcccttatg cgactcctgc attaggaagc agcccagtag taggttgagg      4740
ccgttgagca ccgccgccgc aaggaatggt gcatgcaagg agatggcgcc caacagtccc      4800
ccggccacgg gcctgccac cataccccacg ccgaaacaag cgctcatgag cccgaagtgg      4860
cgagcccgat cttccccatc ggtgatgtcg gcgatatagg cgccagcaac cgcacctgtg      4920
gcgccggtga tgccggccac gatgcgtccg gcgtagagga tcgagatctc gatcccgcga      4980
aattaatacg actcactata ggggaattgt gagcggataa caattcccct ctagaaataa      5040
ttttgtttaa ctttaagaag gagatataca tatggaagct cgtcgttctg cgaactacga      5100
```

```
acctaacagc tgggactatg attacctgct gtcctccgac acggacgagt ccatcgaagt   5160
atacaaagac aaagcgaaaa agctggaagc cgaagttcgt cgcgagatta taacgaaaa    5220 agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gtttctcagg aagcgttcag cggcttcaaa gaccaaaacg caacttcct   5460 ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt tttctttcgt   5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgctttctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
cgcatggaaa tcctcttctg gcccgctgca actggtgttc gcttacttcg ctgtcgtgca   6300
gaacattaaa aaggaagaga tcgaaaacct gcaaaaatac catgacacca tctctcgtcc   6360
ttcccatatc ttccgtctgt gcaatgacct ggctagcgcg tctgcggaaa ttgcgcgtgg   6420
tgaaaccaac aatagcgttt cttgttacat gcgcactaaa ggtatctccg aagaactggc   6480
taccgaaagc gtgatgaatc tgatcgatga acctggaaa aagatgaaca aggaaaaact   6540
gagtggtagc ccgttcgcga aaccgttcgt ggaaaccgcg atcaacctgg cacgtcaatc   6600
tcactgcact tatcataacg gcgacgcgca tacctctccg gatgagctga cccgcaaacg   6660
cgttctgtct gtaatcactg aaccgattct gccgtttgaa cgcgaaaacc tgtattttca   6720
gggcctcgag caccaccacc accaccactg agatccggct gctaacaaag cccgaaagga   6780
agctgagttg gctgctgcca ccgctgagca ataactagca taaccccttg ggcctctaa    6840 acgggtcttg aggggttttt tgctgaaagg aggaactata tccggat                  6887
```

<210> SEQ ID NO 81
<211> LENGTH: 559
<212> TYPE: PRT
<213> ORGANISM: Artificial Sequence
<220> FEATURE:
<223> OTHER INFORMATION: Synthetic Construct

<400> SEQUENCE: 81

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45
```

```
Glu Lys Ala Glu Phe Leu Thr Leu Leu Glu Leu Ile Asp Asn Val Gln
 50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                 85                  90                  95

Leu His Gly Thr Ala Leu Ser Phe Arg Leu Leu Arg Gln His Gly Phe
                100                 105                 110

Glu Val Ser Gln Glu Ala Phe Ser Gly Phe Lys Asp Gln Asn Gly Asn
                115                 120                 125

Phe Leu Glu Asn Leu Lys Glu Asp Ile Lys Ala Ile Leu Ser Leu Tyr
130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
                180                 185                 190

His Arg Arg Thr Gln Arg Leu Glu Ala Val Trp Ser Ile Glu Ala Tyr
                195                 200                 205

Arg Lys Lys Glu Asp Ala Asn Gln Val Leu Leu Glu Leu Ala Ile Leu
210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
                260                 265                 270

Glu Pro Gln Tyr Ser Asp Cys Arg Asn Ser Val Ala Lys Met Phe Ser
                275                 280                 285

Phe Val Thr Ile Ile Asp Asp Ile Tyr Asp Val Tyr Gly Thr Leu Asp
                290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
                340                 345                 350

Asn Ile Leu Pro Tyr Leu Thr Lys Ala Trp Ala Asp Leu Cys Asn Ala
                355                 360                 365

Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
                420                 425                 430

Ile Phe Arg Leu Cys Asn Asp Leu Ala Ser Ala Ser Ala Glu Ile Ala
                435                 440                 445

Arg Gly Glu Thr Asn Asn Ser Val Ser Cys Tyr Met Arg Thr Lys Gly
450                 455                 460
```

```
Ile Ser Glu Glu Leu Ala Thr Glu Ser Val Met Asn Leu Ile Asp Glu
465                 470                 475                 480

Thr Trp Lys Lys Met Asn Lys Gly Lys Leu Ser Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
    530                 535                 540

Glu Asn Leu Tyr Phe Gln Gly Leu Glu His His His His His His
545                 550                 555
```

<210> SEQ ID NO 82
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 82

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggggc tcccttttagg  180
gttccgattt agtgctttac ggcacctcga ccccaaaaaa cttgattagg gtgatggttc   240
acgtagtggg ccatcgccct gatagacggt ttttcgccct tgacgttgg agtccacgtt   300
ctttaatagt ggactcttgt tccaaactgg aacaacactc aaccctatct cggtctattc   360
ttttgattta agggatttt tgccgatttc ggcctattgg ttaaaaaatg agctgattta   420
acaaaaattt aacgcgaatt ttaacaaaat attaacgttt acaatttcag gtggcacttt   480
tcggggaaat gtgcgcggaa cccctatttg tttatttttc taaatacatt caaatatgta   540
tccgctcatg aattaattct tagaaaaact catcgagcat caaatgaaac tgcaatttat   600
tcatatcagg attatcaata ccatatttt gaaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa ataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga gacgaaatac gcgatcgctg ttaaaaggac   960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
tggtgagtaa ccatgcatca tcaggagtac ggataaaatg cttgatggtc ggaagaggca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataacac  1380
cccttgtatt actgtttatg taagcagaca gttttattgt tcatgaccaa atcccttaa   1440
cgtgagtttt cgttccactg agcgtcagac cccgtagaaa agatcaaagg atcttcttga  1500
gatccttttt ttctgcgcgt aatctgctgc ttgcaaacaa aaaaaccacc gctaccagcg  1560
```

```
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa acgcctggta tctttatagt cctgtcgggt ttcgccacct ctgacttgag     2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
```

-continued

```
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agagacaccgg   4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg caacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
```

```
gaacattaaa aaggaagaga tcgaaaacct gcaaaatac catgacacca tctctcgtcc      6360
ttcccatatc ttccgtctgt gcaatgacct ggctagcgcg tctgcggaaa ttgcgcgtgg      6420
tgaaaccaac aatagcgttt cttgttacat gcgcactaaa ggtatctccg aagaactggc      6480
taccgaaagc gtgatgaatc tgatcgatga acctggaaaa aagatgaaca aggaaaaact      6540
gagtggtagc ctgttcgcga aaccgttcgt ggaaaccgcg atcaacctgg cacgtcaatc      6600
tcactgcact tatcataacg gcgacgcgca tacctctccg gatgagctga cccgcaaacg      6660
cgttctgtct gtaatctgcg aaccgattct gccgtttgaa cgcgaaaacc tgtatttcca      6720
gggcctcgag caccaccacc accaccactg agatccggct gctaacaaag cccgaaagga      6780
agctgagttg gctgctgcca ccgctgagca ataactagca taaccccttg gggcctctaa      6840
acgggtcttg aggggttttt tgctgaaagg aggaactata tccggat                   6887
```

<210> SEQ ID NO 83
<211> LENGTH: 559
<212> TYPE: PRT
<213> ORGANISM: Artificial Sequence
<220> FEATURE:
<223> OTHER INFORMATION: Synthetic Construct

<400> SEQUENCE: 83

```
Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255
```

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
        290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Asn Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Pro Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Cys Glu Pro Ile Leu Pro Phe Glu Arg
    530                 535                 540

Glu Asn Leu Tyr Phe Gln Gly Leu Glu His His His His His His
545                 550                 555

<210> SEQ ID NO 84
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 84
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcggggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aacccatctc ggtctattc     360

```
ttttgattta aagggatttt tgccgatttc ggcctattgg ttaaaaaatg agctgattta      420
acaaaaattt aacgcgaatt ttaacaaaat attaacgttt acaatttcag gtggcactttt    480 tcggggaaat gtgcgcggaa ccccta tttg tttattttc taaatacatt caaatatgta     540
tccgctcatg aattaattct tagaaaaact catcgagcat caaatgaaac tgcaattta      600 tcatatcagg attatcaata ccatatttt gaaaaagccg tttctgtaat gaaggagaaa      660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttcttttcc  840 agacttgttc aacaggccag ccattacgct cgtcatcaaa atcactcgca tcaaccaaac    900
cgttattcat tcgtgattgc gcctgagcga acgaaatac gcgatcgctg ttaaaaggac     960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200 cttttgccatg tttcagaaac aactctggcg catcgggctt cccatacaat cgatagattg  1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380 ccttgtatt actgtttatg taagcagaca gttttattgt tcatgaccaa aatcccttaa    1440
cgtgagtttt cgttccactg agcgtcagac cccgtagaaa agatcaaagg atcttcttga   1500 gatcctttttt ttctgcgcgt aatctgctgc ttgcaaacaa aaaaaccacc gctaccagcg  1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
```

-continued

```
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc ccgcgccca    3420 ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagct cgtcgttctg cgaactacga    5100
```

-continued

```
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgccggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggtttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca cgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgcaccca tctctcgtcc    6360
ttcccatatc ttccgtctgt gcaatgacct ggctagcgcg tctgcggaaa ttgcgcgtgg    6420
tgaaaccaac aatagcgttt cttgttacat gcgcactaaa ggtatctccg aagaactggc    6480
taccgaaagc gtgatgaatc tgatcgatga acctggaaa aagatgaaca aggaaaaact    6540
gggtggtagc ccgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatctgcg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg gggcctctaa    6840
acgggtcttg aggggttttt tgctgaaagg aggaactata tccggat    6887
```

<210> SEQ ID NO 85
<211> LENGTH: 559
<212> TYPE: PRT
<213> ORGANISM: Artificial Sequence
<220> FEATURE:
<223> OTHER INFORMATION: Synthetic Construct

<400> SEQUENCE: 85

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
                20                  25                  30

Asp Lys Ala Lys Lys Leu Glu Ala Glu Val Arg Arg Glu Ile Asn Asn
            35                  40                  45
```

```
Glu Lys Ala Glu Phe Leu Thr Leu Leu Glu Leu Ile Asp Asn Val Gln
     50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                     85                  90                  95

Leu His Gly Thr Ala Leu Ser Phe Arg Leu Leu Arg Gln His Gly Phe
             100                 105                 110

Glu Val Ser Gln Glu Ala Phe Ser Gly Phe Lys Asp Gln Asn Gly Asn
             115                 120                 125

Phe Leu Glu Asn Leu Lys Glu Asp Ile Lys Ala Ile Leu Ser Leu Tyr
130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                 165                 170                 175

Gly Lys Glu Leu Ala Glu Gln Val Asn His Ala Leu Glu Leu Pro Leu
             180                 185                 190

His Arg Arg Thr Gln Arg Leu Glu Ala Val Trp Ser Ile Glu Ala Tyr
             195                 200                 205

Arg Lys Lys Glu Asp Ala Asn Gln Val Leu Leu Glu Leu Ala Ile Leu
210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                 245                 250                 255

Arg Asp Arg Leu Ile Glu Ser Phe Tyr Trp Ala Val Gly Val Ala Phe
             260                 265                 270

Glu Pro Gln Tyr Ser Asp Cys Arg Asn Ser Val Ala Lys Met Phe Ser
             275                 280                 285

Phe Val Thr Ile Ile Asp Asp Ile Tyr Asp Val Tyr Gly Thr Leu Asp
290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                 325                 330                 335

Asn Thr Ile Asn Glu Ile Ala Tyr Asp Asn Leu Lys Asp Lys Gly Glu
             340                 345                 350

Asn Ile Leu Pro Tyr Leu Thr Lys Ala Trp Ala Asp Leu Cys Asn Ala
             355                 360                 365

Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                 405                 410                 415

Ile Glu Asn Leu Gln Lys Tyr His Asp Thr Ile Ser Arg Pro Ser His
             420                 425                 430

Ile Phe Arg Leu Cys Asn Asp Leu Ala Ser Ala Ser Ala Glu Ile Ala
             435                 440                 445

Arg Gly Glu Thr Asn Asn Ser Val Ser Cys Tyr Met Arg Thr Lys Gly
450                 455                 460

Ile Ser Glu Glu Leu Ala Thr Glu Ser Val Met Asn Leu Ile Asp Glu
```

```
                465                 470                 475                 480
Thr Trp Lys Lys Met Asn Lys Glu Lys Leu Ser Gly Ser Pro Phe Ala
                    485                 490                 495
Lys Pro Phe Val Glu Thr Ala Ile Asn Leu Ala Arg Gln Ser His Cys
                500                 505                 510
Thr Tyr His Asn Gly Asp Ala His Thr Ser Pro Asp Glu Leu Thr Arg
                515                 520                 525
Lys Arg Val Leu Ser Val Ile Cys Glu Pro Ile Leu Pro Phe Glu Arg
            530                 535                 540
Glu Asn Leu Tyr Phe Gln Gly Leu Glu His His His His His His
545                 550                 555
```

<210> SEQ ID NO 86
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 86

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcgggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttatttttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgtttttccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatcctttt | ttctgcgcgt | aatctgctgc | ttgcaaacaa | aaaaaccacc | gctaccagcg | 1560 |

-continued

```
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccaccct ctgacttgag    2040 cgtcgatttt tgtgatgctc gtcaggggggg cggagcctat ggaaaaacgc cagcaacgcg    2100
gcctttttac ggttcctggc cttttgctgg cctttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
```

-continued

```
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
```

-continued

```
gaacattaaa aaggaagaga tcgaaaacct gcaaaaatac catgacacca tctctcgtcc      6360
ttcccatatc ttccgtctgt gcaatgacct ggctagcgcg tctgcggaaa ttgcgcgtgg      6420
tgaaaccaac aatagcgttt cttgttacat gcgcactaaa ggtatctccg aagaactggc      6480
taccgaaagc gtgatgaatc tgatcgatga aacctggaaa aagatgaaca aggaaaaact      6540
gagtggtagc ccgttcgcga aaccgttcgt ggaaaccgcg atcaacctgg cacgtcaatc      6600
tcactgcact tatcataacg gcgacgcgca tacctctccg gatgagctga cccgcaaacg      6660
cgttctgtct gtaatctgcg aaccgattct gccgtttgaa cgcgaaaacc tgtattttca      6720
gggcctcgag caccaccacc accaccactg agatccggct gctaacaaag cccgaaagga      6780
agctgagttg gctgctgcca ccgctgagca ataactagca taaccccttg gggcctctaa      6840
acgggtcttg aggggttttt tgctgaaagg aggaactata tccggat                   6887
```

<210> SEQ ID NO 87
<211> LENGTH: 559
<212> TYPE: PRT
<213> ORGANISM: Artificial Sequence
<220> FEATURE:
<223> OTHER INFORMATION: Synthetic Construct

<400> SEQUENCE: 87

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
```

```
                    260                 265                 270
Glu Pro Gln Tyr Ser Asp Cys Arg Asn Ser Val Ala Lys Met Phe Ser
                275                 280                 285

Phe Val Thr Ile Ile Asp Asp Ile Tyr Asp Val Tyr Gly Thr Leu Asp
            290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
                340                 345                 350

Asn Ile Leu Pro Tyr Leu Thr Lys Ala Trp Ala Asp Leu Cys Asn Ala
                355                 360                 365

Phe Leu Gln Glu Ala Lys Trp Leu Tyr Asn Lys Ser Thr Pro Thr Phe
                370                 375                 380

Asp Asp Tyr Phe Gly Asn Ala Trp Lys Ser Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
                420                 425                 430

Ile Phe Arg Leu Cys Asn Asp Leu Ala Ser Ala Ser Ala Glu Ile Ala
                435                 440                 445

Arg Gly Glu Thr Ala Asn Ser Val Ser Cys Tyr Met Arg Thr Lys Gly
            450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Ser Gly Ser Pro Phe Ala
                485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
                515                 520                 525

Lys Arg Val Leu Ser Val Ile Thr Glu Pro Ile Leu Pro Phe Glu Arg
                530                 535                 540

Glu Asn Leu Tyr Phe Gln Gly Leu Glu His His His His His His
545                 550                 555
```

<210> SEQ ID NO 88
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 88

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aacccatatct cggtctattc     360 ttttgattta agggattt tgccgatttc ggcctattgg ttaaaaaatg agctgattta     420
```

-continued

```
acaaaaattt aacgcgaatt ttaacaaaat attaacgttt acaatttcag gtggcacttt     480
tcggggaaat gtgcgcggaa ccccctatttg tttatttttc taaatacatt caaatatgta    540
tccgctcatg aattaattct tagaaaaact catcgagcat caaatgaaac tgcaatttat     600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa agtttatgc atttctttcc     840 agacttgttc aacaggccag ccattacgct cgtcatcaaa atcactcgca tcaaccaaac    900
cgttattcat tcgtgattgc gcctgagcga gacgaaatac gcgatcgctg ttaaaggac     960 aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200 cttttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
```

```
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccgagcg ctgccggca cctgtcctac    3360 gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga ctgtcttcg gtatcgtcgt    3780 atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagct cgtcgttctg cgaactacga    5100
acctaacagc tgggactatg attacctgct gtcctccgac acggacgagt ccatcgaagt    5160
```

```
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940 aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga acctggaaaa aagatgaaca aggaaaaact    6540
gagtggtagc ccgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgcgaaaacc tgtattttca    6720
gggcctcgag caccaccacc accaccactg agatccggct gctaacaaag cccgaaagga    6780
agctgagttg ctgctgccac cgctgagcaa taactagca taaccccttg ggcctctaa    6840 acgggtcttg aggggttttt tgctgaaagg aggaactata tccggat              6887
```

<210> SEQ ID NO 89
<211> LENGTH: 559
<212> TYPE: PRT
<213> ORGANISM: Artificial Sequence
<220> FEATURE:
<223> OTHER INFORMATION: Synthetic Construct

<400> SEQUENCE: 89

Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln

```
            50                  55                  60
Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                     85                  90                  95

Leu His Gly Thr Ala Leu Ser Phe Arg Leu Leu Arg Gln His Gly Phe
                    100                 105                 110

Glu Val Ser Gln Glu Ala Phe Ser Gly Phe Lys Asp Gln Asn Gly Asn
                115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                    165                 170                 175

Gly Lys Glu Leu Ala Glu Gln Val Asn His Ala Leu Glu Leu Pro Leu
                180                 185                 190

His Arg Arg Thr Gln Arg Leu Glu Ala Val Trp Ser Ile Glu Ala Tyr
                195                 200                 205

Arg Lys Lys Glu Asp Ala Asn Gln Val Leu Leu Glu Leu Ala Ile Leu
210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
                260                 265                 270

Glu Pro Gln Tyr Ser Asp Cys Arg Asn Ser Val Ala Lys Met Phe Ser
                275                 280                 285

Phe Val Thr Ile Ile Asp Asp Ile Tyr Asp Val Tyr Gly Thr Leu Asp
                290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
                340                 345                 350

Asn Ile Leu Pro Tyr Leu Thr Lys Ala Trp Ala Asp Leu Cys Asn Ala
                355                 360                 365

Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
                420                 425                 430

Ile Phe Arg Leu Cys Asn Asp Leu Ala Ser Ala Ser Ala Glu Ile Ala
                435                 440                 445

Arg Gly Glu Thr Ala Asn Ser Val Ser Cys Tyr Met Arg Thr Lys Gly
450                 455                 460

Ile Ser Glu Glu Leu Ala Thr Glu Ser Val Met Asn Leu Ile Asp Glu
465                 470                 475                 480
```

```
Thr Trp Lys Lys Met Asn Lys Glu Lys Leu Ser Gly Ser Leu Phe Ala
            485                 490                 495
Lys Pro Phe Val Glu Thr Ala Ile Asn Leu Ala Arg Gln Ser His Cys
            500                 505                 510
Thr Tyr His Asn Gly Asp Ala His Thr Ser Pro Asp Glu Leu Thr Arg
            515                 520                 525
Lys Arg Val Leu Ser Val Ile Cys Glu Pro Ile Leu Pro Phe Glu Arg
            530                 535                 540
Glu Asn Leu Tyr Phe Gln Gly Leu Glu His His His His His His
545                 550                 555

<210> SEQ ID NO 90
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 90
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct tgacgttgga gtccacgtt     300
ctttaatagt ggactcttgt tccaaactgg aacaacactc aaccctatct cggtctattc     360
ttttgattta agggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga tcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
```

```
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
```

-continued

```
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg cctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
```

```
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gagtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatctgcg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg gggcctctaa    6840
acgggtcttg aggggttttt tgctgaaagg aggaactata tccggat                 6887
```

<210> SEQ ID NO 91
<211> LENGTH: 559
<212> TYPE: PRT
<213> ORGANISM: Artificial Sequence
<220> FEATURE:
<223> OTHER INFORMATION: Synthetic Construct

<400> SEQUENCE: 91

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270
```

```
Glu Pro Gln Tyr Ser Asp Cys Arg Asn Ser Val Ala Lys Met Phe Ser
        275                 280                 285
Phe Val Thr Ile Ile Asp Asp Ile Tyr Asp Val Tyr Gly Thr Leu Asp
        290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                325                 330                 335
Asn Thr Ile Asn Glu Ile Ala Tyr Asp Asn Leu Lys Asp Lys Gly Glu
            340                 345                 350
Asn Ile Leu Pro Tyr Leu Thr Lys Ala Trp Ala Asp Leu Cys Asn Ala
        355                 360                 365
Phe Leu Gln Glu Ala Lys Trp Leu Tyr Asn Lys Ser Thr Pro Thr Phe
    370                 375                 380
Asp Asp Tyr Phe Gly Asn Ala Trp Lys Ser Ser Gly Pro Leu Gln
385                 390                 395                 400
Leu Val Phe Ala Tyr Phe Ala Val Val Gln Asn Ile Lys Lys Glu Glu
                405                 410                 415
Ile Glu Asn Leu Gln Lys Tyr His Asp Thr Ile Ser Arg Pro Ser His
            420                 425                 430
Ile Phe Arg Leu Cys Asn Asp Leu Ala Ser Ala Ser Ala Glu Ile Ala
        435                 440                 445
Arg Gly Glu Thr Ala Asn Ser Val Ser Cys Tyr Met Arg Thr Lys Gly
    450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Leu Ser Gly Ser Pro Phe Ala
                485                 490                 495
Lys Pro Phe Val Glu Thr Ala Ile Asn Leu Ala Arg Gln Ser His Cys
            500                 505                 510
Thr Tyr His Asn Gly Asp Ala His Thr Ser Pro Asp Glu Leu Thr Arg
        515                 520                 525
Lys Arg Val Leu Ser Val Ile Cys Glu Pro Ile Leu Pro Phe Glu Arg
    530                 535                 540
Glu Asn Leu Tyr Phe Gln Gly Leu Glu His His His His His His
545                 550                 555

<210> SEQ ID NO 92
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 92
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta     420
```

```
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa ataaggttat caagtgaga    780 aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200 cttttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500 gatcctttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttac ggttcctggc cttttgctgg ccttttgctc acatgttctt tcctgcgtta   2160 tccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280 tatttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgcccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
```

```
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc cggtgccta    3480 atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgcggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagct cgtcgttctg cgaactacga    5100
acctaacagc tgggactatg attacctgct gtcctccgac acggacgagt ccatcgaagt    5160
```

```
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940
aaccattatc gacgatatct acgatgtata cggcacccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca cgctttcct    6180
gcaagaagcc aagtggctgt acaacaaatc tactccgacc tttgacgact acttcggcaa    6240
cgcatggaaa tcctcttctg ccccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga acctggaaaa aagatgaaca aggaaaaact    6540
gagtggtagc ccgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatctgcg aaccgattct gccgttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg ggcctctaa    6840
acgggtcttg aggggttttt tgctgaaagg aggaactata tccggat               6887
```

<210> SEQ ID NO 93
<211> LENGTH: 559
<212> TYPE: PRT
<213> ORGANISM: Artificial Sequence
<220> FEATURE:
<223> OTHER INFORMATION: Synthetic Construct

<400> SEQUENCE: 93

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
             20                  25                  30

Asp Lys Ala Lys Lys Leu Glu Ala Glu Val Arg Arg Glu Ile Asn Asn
         35                  40                  45

Glu Lys Ala Glu Phe Leu Thr Leu Leu Glu Leu Ile Asp Asn Val Gln
     50                  55                  60
```

-continued

Arg Leu Gly Leu Gly Tyr Arg Phe Glu Ser Asp Ile Arg Gly Ala Leu
65                  70                  75                  80

Asp Arg Phe Val Ser Gly Gly Phe Asp Ala Val Thr Lys Thr Ser
            85                  90                  95

Leu His Gly Thr Ala Leu Ser Phe Arg Leu Arg Gln His Gly Phe
                100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

```
Thr Trp Lys Lys Met Asn Lys Glu Lys Leu Gly Gly Ser Pro Phe Ala
            485                 490                 495

Lys Pro Phe Val Glu Thr Ala Ile Asn Leu Ala Arg Gln Ser His Cys
        500                 505                 510

Thr Tyr His Asn Gly Asp Ala His Thr Ser Pro Asp Glu Leu Thr Arg
    515                 520                 525

Lys Arg Val Leu Ser Val Ile Cys Glu Pro Ile Leu Pro Phe Glu Arg
530                 535                 540

Glu Asn Leu Tyr Phe Gln Gly Leu Glu His His His His His His
545                 550                 555
```

<210> SEQ ID NO 94
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 94

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcgggggc tccctttagg    180
gttccgattt agtgctttac ggcacctcga ccccaaaaaa cttgattagg gtgatggttc   240
acgtagtggg ccatcgccct gatagacggt ttttcgccct tgacgttgg agtccacgtt    300
ctttaatagt ggactcttgt tccaaactgg aacaacactc aacctatct cggtctattc    360
ttttgattta agggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaattta    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa ataaggttta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga cgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa atcccttaa    1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
```

-continued

```
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcaggggggg cggagcctat ggaaaaacgc cagcaacgcg   2100 gccttttttac ggttcctggc cttttgctgg ccttttgctc acatgttctt tcctgcgtta   2160 tccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacgcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
```

-continued

```
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagct cgtcgttctg cgaactacga    5100
acctaacagc tgggactatg attacctgct gtcctccgac acgacgagt ccatcgaagt    5160 atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaaatac catgacacca tctctcgtcc    6360
```

```
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga acctggaaaa agatgaaca aggaaaaact    6540 gggtggtagc ccgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatctgcg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg gggcctctaa    6840
acgggtcttg aggggttttt tgctgaaagg aggaactata tccggat                  6887
```

<210> SEQ ID NO 95
<211> LENGTH: 559
<212> TYPE: PRT
<213> ORGANISM: Artificial Sequence
<220> FEATURE:
<223> OTHER INFORMATION: Synthetic Construct

<400> SEQUENCE: 95

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270
```

```
Glu Pro Gln Tyr Ser Asp Cys Arg Asn Ser Val Ala Lys Met Phe Ser
            275                 280                 285
Phe Val Thr Ile Ile Asp Asp Ile Tyr Asp Val Tyr Gly Thr Leu Asp
        290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                325                 330                 335
Asn Thr Ile Asn Glu Ile Ala Tyr Asp Asn Leu Lys Asp Lys Gly Glu
            340                 345                 350
Asn Ile Leu Pro Tyr Leu Thr Lys Ala Trp Ala Asp Leu Cys Asn Ala
        355                 360                 365
Phe Leu Gln Glu Ala Lys Trp Leu Tyr Asn Lys Ser Thr Pro Thr Phe
    370                 375                 380
Asp Asp Tyr Phe Gly Asn Ala Trp Lys Ser Ser Gly Pro Leu Gln
385                 390                 395                 400
Leu Val Phe Ala Tyr Phe Ala Val Val Gln Asn Ile Lys Lys Glu Glu
                405                 410                 415
Ile Glu Asn Leu Gln Lys Tyr His Asp Thr Ile Ser Arg Pro Ser His
            420                 425                 430
Ile Phe Arg Leu Cys Asn Asp Leu Ala Ser Ala Ser Ala Glu Ile Ala
        435                 440                 445
Arg Gly Glu Thr Ala Asn Ser Val Ser Cys Tyr Met Arg Thr Lys Gly
    450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Leu Gly Gly Ser Leu Phe Ala
                485                 490                 495
Lys Pro Phe Val Glu Thr Ala Ile Asn Leu Ala Arg Gln Ser His Cys
            500                 505                 510
Thr Tyr His Asn Gly Asp Ala His Thr Ser Pro Asp Glu Leu Thr Arg
        515                 520                 525
Lys Arg Val Leu Ser Val Ile Phe Glu Pro Ile Leu Pro Phe Glu Arg
    530                 535                 540
Glu Asn Leu Tyr Phe Gln Gly Leu Glu His His His His His His
545                 550                 555

<210> SEQ ID NO 96
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 96
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggatttt tgccgatttc ggcctattgg ttaaaaaatg agctgattta     420
acaaaaattt aacgcgaatt ttaacaaaat attaacgttt acaatttcag gtggcacttt     480
```

-continued

```
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatatttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa agtttatgc atttctttcc    840 agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccattata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggga acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg cctttgctc acatgttctt cctgcgtta    2160 tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac ccgctgacg cgccctgac gggcttgtct   2460 gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
```

```
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccgaaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgcggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
```

```
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatctttg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg ggcctctaa     6840 acgggtcttg aggggttttt tgctgaaagg aggaactata tccggat                  6887
```

<210> SEQ ID NO 97  
<211> LENGTH: 559  
<212> TYPE: PRT  
<213> ORGANISM: Artificial Sequence  
<220> FEATURE:  
<223> OTHER INFORMATION: Synthetic Construct

<400> SEQUENCE: 97

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60
```

-continued

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
            85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
            115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Pro Phe Ala

```
                485                 490                 495
Lys Pro Phe Val Glu Thr Ala Ile Asn Leu Ala Arg Gln Ser His Cys
        500                 505                 510

Thr Tyr His Asn Gly Asp Ala His Thr Ser Pro Asp Glu Leu Thr Arg
        515                 520                 525

Lys Arg Val Leu Ser Val Ile Phe Glu Pro Ile Leu Pro Phe Glu Arg
        530                 535                 540

Glu Asn Leu Tyr Phe Gln Gly Leu Glu His His His His His His
545                 550                 555

<210> SEQ ID NO 98
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 98
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggcc tccctttagg      180 gttccgattt agtgctttac ggcacctcga ccccaaaaaa cttgattagg gtgatggttc     240
acgtagtggg ccatcgccct gatagacggt ttttcgccct tgacgttgg agtccacgtt      300 ctttaatagt ggactcttgt tccaaactgg aacaacactc aaccctatct cggtctattc     360
ttttgattta agggattt tgccgatttc ggcctattgg ttaaaaatg agctgattta        420 acaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga cgaaatac gcgatcgctg ttaaaaggac      960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa atcccttaa    1440 cgtgagtttt cgttccactg agcgtcagac cccgtagaaa agatcaaagg atcttcttga   1500
gatccttttt tctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
```

```
aactctgtag caccgcctac atacctcgct ctgctaatcc tgttaccagt ggctgctgcc   1740
agtggcgata agtcgtgtct taccggttg gactcaagac gatagttacc ggataaggcg    1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac accgctgac gcgcctgac gggcttgtct     2460 gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataagaaga cagtcataag tgcggcgacg atagtcatgc cccgcgccca    3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
```

-continued

```
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttctttcgt    5940
aaccattatc gacgatatct acgatgtata cggcacctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
```

-continued

```
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ccgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatctttg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg gggcctctaa    6840
acgggtcttg aggggttttt tgctgaaagg aggaactata tccggat                  6887
```

<210> SEQ ID NO 99
<211> LENGTH: 89
<212> TYPE: PRT
<213> ORGANISM: Artificial Sequence
<220> FEATURE:
<223> OTHER INFORMATION: Synthetic Construct

<400> SEQUENCE: 99

```
Ala Asn Ser Val Ser Cys Tyr Met Arg Thr Lys Gly Ile Ser Glu Glu
  1               5                  10                  15

Leu Ala Thr Glu Ser Val Met Asn Leu Ile Asp Glu Thr Trp Lys Lys
             20                  25                  30

Met Asn Lys Glu Lys Leu Gly Gly Ser Leu Phe Ala Lys Pro Phe Val
         35                  40                  45

Glu Thr Ala Ile Asn Leu Ala Arg Gln Ser His Cys Thr Tyr His Asn
     50                  55                  60

Gly Asp Ala His Thr Ser Pro Asp Glu Leu Thr Arg Lys Arg Val Leu
 65                  70                  75                  80

Ser Val Ile Thr Glu Pro Ile Leu Pro
                 85
```

<210> SEQ ID NO 100
<211> LENGTH: 89
<212> TYPE: PRT
<213> ORGANISM: Artificial Sequence
<220> FEATURE:
<223> OTHER INFORMATION: Synthetic Construct

<400> SEQUENCE: 100

```
Ala Asn Ser Val Ser Cys Tyr Met Arg Thr Lys Gly Ile Ser Glu Glu
  1               5                  10                  15

Leu Ala Thr Glu Ser Val Met Asn Leu Ile Asp Glu Thr Trp Lys Lys
             20                  25                  30

Met Asn Lys Glu Lys Leu Gly Gly Ser Leu Phe Ala Lys Pro Phe Val
         35                  40                  45

Glu Thr Ala Ile Asn Leu Ala Arg Gln Ser His Cys Thr Tyr His Asn
     50                  55                  60

Gly Asp Ala His Thr Ser Pro Asp Glu Leu Thr Arg Lys Arg Val Leu
 65                  70                  75                  80

Ser Val Ile Thr Glu Pro Ile Leu Pro
                 85
```

<210> SEQ ID NO 101
<211> LENGTH: 89
<212> TYPE: PRT
<213> ORGANISM: Artificial Sequence
<220> FEATURE:

<223> OTHER INFORMATION: Synthetic Construct

<400> SEQUENCE: 101

Ala Asn Ser Val Ser Cys Tyr Met Arg Thr Lys Gly Ile Ser Glu Glu
1               5                   10                  15

Leu Ala Thr Glu Ser Val Met Asn Leu Ile Asp Glu Thr Trp Lys Lys
            20                  25                  30

Met Asn Lys Glu Lys Leu Gly Gly Ser Leu Phe Ala Lys Pro Phe Val
        35                  40                  45

Glu Thr Ala Ile Asn Leu Ala Arg Gln Ser His Cys Thr Tyr His Asn
    50                  55                  60

Gly Asp Ala His Thr Ser Pro Asp Glu Leu Thr Arg Lys Arg Val Leu
65                  70                  75                  80

Ser Val Ile Thr Glu Pro Ile Leu Pro
                85

<210> SEQ ID NO 102
<211> LENGTH: 89
<212> TYPE: PRT
<213> ORGANISM: Artificial Sequence
<220> FEATURE:
<223> OTHER INFORMATION: Synthetic Construct

<400> SEQUENCE: 102

Ala Asn Ser Val Ser Cys Tyr Met Arg Thr Lys Gly Ile Ser Glu Glu
1               5                   10                  15

Leu Ala Thr Glu Ser Val Met Asn Leu Ile Asp Glu Thr Trp Lys Lys
            20                  25                  30

Met Asn Lys Glu Lys Leu Gly Gly Ser Leu Phe Ala Lys Pro Phe Val
        35                  40                  45

Glu Thr Ala Ile Asn Leu Ala Arg Gln Ser His Cys Thr Tyr His Asn
    50                  55                  60

Gly Asp Ala His Thr Ser Pro Asp Glu Leu Thr Arg Lys Arg Val Leu
65                  70                  75                  80

Ser Val Ile Thr Glu Pro Ile Leu Pro
                85

<210> SEQ ID NO 103
<211> LENGTH: 89
<212> TYPE: PRT
<213> ORGANISM: Artificial Sequence
<220> FEATURE:
<223> OTHER INFORMATION: Synthetic Construct

<400> SEQUENCE: 103

Ala Asn Ser Val Ser Cys Tyr Met Arg Thr Lys Gly Ile Ser Glu Glu
1               5                   10                  15

Leu Ala Thr Glu Ser Val Met Asn Leu Ile Asp Glu Thr Cys Lys Lys
            20                  25                  30

Met Asn Lys Glu Lys Leu Gly Gly Ser Leu Phe Ala Lys Pro Phe Val
        35                  40                  45

Glu Thr Ala Ile Asn Leu Ala Arg Gln Ser His Cys Thr Tyr His Asn
    50                  55                  60

Gly Asp Ala His Thr Ser Pro Asp Glu Leu Thr Arg Lys Arg Val Leu
65                  70                  75                  80

Ser Val Ile Thr Glu Pro Ile Leu Pro
                85

```
<210> SEQ ID NO 104
<211> LENGTH: 91
<212> TYPE: PRT
<213> ORGANISM: Artificial Sequence
<220> FEATURE:
<223> OTHER INFORMATION: Synthetic Construct

<400> SEQUENCE: 104

Thr Asn Ser Ile Ile Ser Tyr Met His Glu Asn Asp Gly Thr Ser Glu
 1               5                  10                  15

Glu Gln Ala Arg Glu Glu Leu Arg Lys Leu Ile Asp Ala Glu Trp Lys
             20                  25                  30

Lys Met Asn Arg Glu Arg Val Ser Asp Ser Thr Leu Leu Pro Lys Ala
         35                  40                  45

Phe Met Glu Ile Ala Val Asn Met Ala Arg Val Ser His Cys Thr Tyr
     50                  55                  60

Gln Tyr Gly Asp Gly Leu Gly Arg Pro Asp Tyr Ala Thr Glu Asn Arg
 65                  70                  75                  80

Ile Lys Leu Leu Leu Ile Asp Pro Phe Pro Ile
                 85                  90

<210> SEQ ID NO 105
<211> LENGTH: 89
<212> TYPE: PRT
<213> ORGANISM: Artificial Sequence
<220> FEATURE:
<223> OTHER INFORMATION: Synthetic Construct

<400> SEQUENCE: 105

Pro Lys Ser Leu Gln Cys Tyr Met Ser Asp Tyr Asn Ala Ser Glu Ala
 1               5                  10                  15

Glu Ala Arg Lys His Val Lys Trp Leu Ile Ala Glu Val Trp Lys Lys
             20                  25                  30

Met Asn Ala Glu Arg Val Ser Lys Asp Ser Pro Phe Gly Lys Asp Phe
         35                  40                  45

Ile Gly Cys Ala Val Asp Leu Gly Arg Met Ala Gln Leu Met Tyr His
     50                  55                  60

Asn Gly Asp Gly His Gly Thr Gln His Pro Ile Ile His Gln Gln Met
 65                  70                  75                  80

Thr Arg Thr Leu Phe Glu Pro Phe Ala
                 85

<210> SEQ ID NO 106
<211> LENGTH: 88
<212> TYPE: PRT
<213> ORGANISM: Artificial Sequence
<220> FEATURE:
<223> OTHER INFORMATION: Synthetic Construct

<400> SEQUENCE: 106

Pro Lys Thr Ile Gln Cys Tyr Met Lys Glu Thr Asn Ala Ser Glu Glu
 1               5                  10                  15

Glu Ala Val Glu His Val Lys Phe Leu Ile Arg Glu Ala Trp Lys Asp
             20                  25                  30

Met Asn Thr Ala Ile Ala Ala Gly Tyr Pro Phe Pro Asp Gly Met Val
         35                  40                  45

Ala Gly Ala Ala Asn Ile Gly Arg Val Ala Gln Phe Ile Tyr Leu His
     50                  55                  60

Gly Asp Gly Phe Gly Val Gln His Ser Lys Thr Tyr Glu His Ile Ala
 65                  70                  75                  80
```

```
Gly Leu Leu Phe Glu Pro Tyr Ala
                85

<210> SEQ ID NO 107
<211> LENGTH: 89
<212> TYPE: PRT
<213> ORGANISM: Artificial Sequence
<220> FEATURE:
<223> OTHER INFORMATION: Synthetic Construct

<400> SEQUENCE: 107

Pro Lys Ala Ile Gln Cys Tyr Met Asn Glu Thr Gly Ala Ser Glu Glu
1               5                   10                  15

Asp Ala Arg Glu Tyr Ile Lys Tyr Leu Ile Ser Ala Thr Trp Lys Lys
                20                  25                  30

Met Asn Glu Asp Arg Val Ala Ser Ser Pro Phe Ser His Ile Phe Ile
            35                  40                  45

Glu Ile Ala Leu Asn Leu Ala Arg Met Ala Gln Cys Met Tyr Gln His
    50                  55                  60

Gly Asp Gly His Gly His Gly Asn His Glu Thr Lys Asp Arg Ile Leu
65                  70                  75                  80

Ser Leu Leu Ile Gln Pro Ile Pro Leu
                85

<210> SEQ ID NO 108
<211> LENGTH: 90
<212> TYPE: PRT
<213> ORGANISM: Artificial Sequence
<220> FEATURE:
<223> OTHER INFORMATION: Synthetic Construct

<400> SEQUENCE: 108

Ala Thr Gly Ile Glu Cys Cys Met Arg Asp Tyr Gly Ile Ser Thr Lys
1               5                   10                  15

Glu Ala Met Ala Lys Phe Gln Asn Met Ala Glu Thr Ala Trp Lys Asp
                20                  25                  30

Ile Asn Glu Gly Leu Leu Arg Pro Thr Pro Val Ser Thr Glu Phe Leu
            35                  40                  45

Thr Pro Ile Leu Asn Leu Ala Arg Ile Val Glu Val Thr Tyr Ile His
    50                  55                  60

Asn Leu Asp Gly Tyr Thr His Pro Glu Lys Val Leu Lys Pro His Ile
65                  70                  75                  80

Ile Asn Leu Leu Val Asp Ser Ile Lys Ile
                85                  90

<210> SEQ ID NO 109
<211> LENGTH: 86
<212> TYPE: PRT
<213> ORGANISM: Artificial Sequence
<220> FEATURE:
<223> OTHER INFORMATION: Synthetic Construct

<400> SEQUENCE: 109

Thr Asn Ser Ile Arg Cys Phe Met Glu Lys Gly Ile Ser Glu Leu Glu
1               5                   10                  15

Ala Arg Glu Cys Val Lys Glu Glu Ile Asp Thr Ala Trp Lys Lys Met
                20                  25                  30

Asn Lys Tyr Met Val Asp Arg Ser Thr Phe Asn Ser Phe Val Arg Met
            35                  40                  45
```

```
Thr Tyr Asn Leu Ala Arg Met Ala His Cys Val Tyr Asp Gly Asp Ala
 50                  55                  60

Ile Gly Ser Pro Asp Asp Leu Ser Trp Asn Arg Val His Ser Leu Ile
 65                  70                  75                  80

Ile Lys Pro Ile Ser Pro
                 85

<210> SEQ ID NO 110
<211> LENGTH: 89
<212> TYPE: PRT
<213> ORGANISM: Artificial Sequence
<220> FEATURE:
<223> OTHER INFORMATION: Synthetic Construct

<400> SEQUENCE: 110

Thr Asn Ser Ile Leu Cys Tyr Met Arg Glu Lys Gly Phe Ser Glu Ser
 1               5                  10                  15

Glu Ala Arg Lys Gln Val Ile Glu Gln Ile Asp Thr Ala Trp Arg Gln
                20                  25                  30

Met Asn Lys Tyr Met Val Asp His Ser Thr Phe Asn Arg Ser Phe Met
             35                  40                  45

Gln Met Thr Tyr Asn Leu Ala Arg Met Ala His Cys Val Tyr Gln Asp
 50                  55                  60

Gly Asp Ala Ile Gly Ala Pro Asp Asp Gln Ser Trp Asn Arg Val His
 65                  70                  75                  80

Ser Leu Ile Ile Lys Pro Val Ser Leu
                 85

<210> SEQ ID NO 111
<211> LENGTH: 91
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 91
<223> OTHER INFORMATION: x=unknown

<400> SEQUENCE: 111

Ala Asn Ser Ile Ser Cys Tyr Met Gly Gln Thr Gly Val Ser Glu Glu
 1               5                  10                  15

Asp Ala Arg Glu His Met Lys Ile Leu Ile Asp Glu Ser Trp Lys Lys
                20                  25                  30

Met Asn Lys Val Arg Glu Met Asp Ser Asp Ser Pro Phe Ala Lys Pro
             35                  40                  45

Phe Val Glu Thr Ala Ile Asn Leu Ala Arg Ile Ala Gln Cys Thr Tyr
 50                  55                  60

Gln Thr Gly Asp Ser His Gly Ala Pro Asp Ala Arg Ser Lys Lys Arg
 65                  70                  75                  80

Val Leu Ser Leu Ile Val Glu Pro Ile Pro Xaa
                 85                  90

<210> SEQ ID NO 112
<211> LENGTH: 88
<212> TYPE: PRT
<213> ORGANISM: Artificial Sequence
<220> FEATURE:
<223> OTHER INFORMATION: Synthetic Construct

<400> SEQUENCE: 112
```

-continued

```
Ala Asn Ser Ile Ile Cys Tyr Met Asn Glu Asn Gly Val Ser Glu Glu
 1               5                  10                  15

Val Ala Tyr Lys His Ile Gln Asn Leu Leu Asp Gln Thr Trp Lys Lys
            20                  25                  30

Met Asn Lys Asp Arg Val Ile Asn Ser Pro Ser Ser Lys Tyr Phe Ser
        35                  40                  45

Glu Thr Ile Ile Asn Leu Ala Arg Ile Ser His Cys Thr Tyr Gln Tyr
    50                  55                  60

Gly Asp Gly His Gly Ala Pro Asp Thr Leu Ala Lys Asn Arg Ile Lys
65                  70                  75                  80

Ala Leu Ile Leu Glu Pro Ile Asn
                85
```

THREE-DIMENSIONAL STRUCTURE OF ISOPRENE SYNTHASE AND ITS USE THEREOF FOR GENERATING VARIANTS

CROSS-REFERENCE TO RELATED APPLICATIONS

This application is a divisional patent application of U.S. patent application Ser. No. 12/765,825, filed Apr. 22, 2010, which claims the benefit of U.S. Provisional patent application 61/172,199, filed on Apr. 23, 2009, and U.S. Provisional patent application 61/255,831, filed on Oct. 28, 2009, the disclosures of which are herein incorporated by reference in their entirety.

FIELD OF INVENTION

The present invention is related to the crystallization and three-dimensional structure determination of *Populus tremuloides* isoprene synthase and *Populus alba* isoprene synthase. The invention also provides methods of producing variants of isoprene synthase for increased isoprene production in microbial host cells.

BACKGROUND OF THE INVENTION

Isoprenoids are isoprene polymers that find use in pharmaceuticals, neutraceuticals, flavors, fragrances, and rubber products. Natural isoprenoid supplies, however, are limited due to ecological concerns. For this reason, and to provide isoprenoid compositions having fewer impurities and greater uniformity, isoprenoids such as rubber are often produced synthetically.

Isoprene (2-methyl-1,3-butadiene) is a volatile hydrocarbon that is insoluble in water and soluble in alcohol. Commercially viable quantities of isoprene can be obtained by direct isolation from petroleum C5 cracking fractions or by dehydration of C5 isoalkanes or isoalkenes (Weissermel and Arpe, Industrial Organic Chemistry, 4th ed., Wiley-VCH, pp. 117-122, 2003). The C5 skeleton can also be synthesized from smaller subunits. It would be desirable, however, to have a commercially viable method of producing isoprene that was independent of nonrenewable resources.

Biosynthetic production of isoprene occurs by two distinct metabolic pathways (Julsing et al., Appl Microbiol Biotechnol, 75:1377-1384, 2007). In eukaryotes and archae, isoprene is formed via the mevalonate (MVA) pathway, while some eubacteria and higher plants produce isoprene via the methylerythritol phosphate (MEP) pathway. Isoprene emissions from plants are light and temperature-dependent with increases linked to leaf development. An isoprene-producing enzyme, isoprene synthase, has been identified in Aspen trees (Silver and Fall, Plant Physiol, 97:1588-1591, 1991; and Silver and Fall, J Biol Chem, 270:13010-13016, 1995) and is believed to be responsible for the in vivo production of isoprene from whole leaves. Bacterial production of isoprene has also been described (Kuzma et al., Curr Microbiol, 30:97-103, 1995; and Wilkins, Chemosphere, 32:1427-1434, 1996), and varies in amount with the phase of bacterial growth and the nutrient content of the culture medium (U.S. Pat. No. 5,849,970 to Fall et al.; and Wagner et al., J Bacteriol, 181: 4700-4703, 1999, both herein incorporated by reference in their entirety). The levels of isoprene obtainable through bacterial systems of the prior art, however, are insufficient for commercial uses.

Polypeptides, e.g. isoprene synthase, have a three-dimensional structure determined by the primary amino acid sequence and the environment surrounding the polypeptide. This three-dimensional structure establishes the polypeptide's activity, stability, binding affinity, binding specificity, and other biochemical attributes. Thus, knowledge of a protein's three-dimensional structure can provide much guidance in designing improvements to its biological activity, for example, greater catalytic activity, dimerization and/or solubility.

The three-dimensional structure of a polypeptide can be determined in a number of ways. Many of the most precise methods employ X-ray crystallography (See, e.g., Van Holde, (1971) Physical Biochemistry, Prentice-Hall, New Jersey, pp. 221-39). This technique relies on the ability of crystalline lattices to diffract X-rays or other forms of radiation. Diffraction experiments suitable for determining the three-dimensional structure of macromolecules typically require high-quality crystals. The crystallization properties of a polypeptide vary greatly (Dale, et al., J. Struct. Biol. 142:88-97, 2003; MacPherson, A., Methods 34:254-265, 2004; and Slabinski, L et al., Protein Science 16:2472-2482, 2007). In some cases polypeptides crystallize readily whereas in other cases polypeptides have proven extremely difficult to obtain. There is no comprehensive theory to guide efforts to crystallize macromolecules and as a result, most efforts macromolecular crystal growth is empirical in nature (MacPherson, 2004).

Previous efforts to utilize the structure of isoprene synthase in order to improve production of isoprene have relied on the structures of other terpene synthases in which three-dimensional structures are available including bornyl diphosphate synthase and 5-epi-aristolochene synthase (See e.g., U.S. patent application Ser. No. 12/429,143 and WO 2008/137092). What is needed is a three-dimensional structure of isoprene synthase to aid in the design of variants of isoprene synthase to allow commercial scale biological production of isoprenoids.

A three-dimensional structure of isoprene synthase is found to have a structurally homologous fold with previously determined synthetases, e.g. bornyl diphosphate synthase and limonene synthase, including conservation in the region involved with the coordinates of required metal ion cofactors, the active and substrate binding sites. The structure has provided insight in the conformational changes that are necessary for these enzyme to bind substrate and catalyze a coordinated series of reactions. Specifically the structure has identified flexible regions that are likely to be shared by all structurally homologous synthetase and that modification of the amino acids found in these regions and the neighboring regions would be expected to effect improved performance of these enzymes. A three-dimensional structure of isoprene synthase may provide a three-dimensional configuration of points, or reaction coordinates, representing the active site of isoprene synthase for the conversion of dimethylallyl diphosphate (DMAPP) into isoprene. Such a configuration of points can aid in the design of synthetic agents for the conversion of DMAPP into isoprene.

BRIEF SUMMARY OF THE INVENTION

The invention provides methods and compositions for generating variants of isoprene synthase with improved activity, expression or stability by utilizing three dimensional structure of isoprene synthase. In one aspect, the invention provides a) using a three dimensional structure of isoprene synthase to identify at least one location in the isoprene synthase for amino acid substitutions that is capable of increasing the activity, expression or stability of isoprene synthase; and b)

modifying the isoprene synthase at the location(s) to generate an isoprene synthase variant with improved activity, expression or stability. In one embodiment, the location is selected from the group consisting of: flexible loop, disphosphate/metal binding site, active site, isoprenyl binding site, surface region, negatively charged region, hinge region, and electrostatic patch region.

In another aspect, the invention provides for methods of generating a variant of an isoprene synthase with improved activity, expression or stability; the method comprising; a) identifying hydrophobic amino acid residues on the surface of isoprene synthase based on the three dimensional structure of P. alba isoprene synthase; b) introducing one or more amino acid substitutions in the surface amino acids of isoprene synthase; c) identifying variants with substitutions that improve activity, expression or stability of the isoprene synthase compared to the P. alba isoprene synthase amino acid sequence of SEQ ID NO:45. In some embodiments, the hydrophobic surface amino acid is selected from the group consisting of I28, V30, L130, G153, L303, L469 and L494.

In other aspects, the invention provides for an isoprene synthase variant produced any of the methods disclosed herein. In some aspects, the isoprene synthase variant is isolated.

In other aspects, the isoprene synthase variant comprises one or more substitution(s) selected from the group consisting of I28W, I28T, I28R, I28Y, V30K, L130W, L130K, L130S, L130Y, L130R, L130V, L130I, L130E, L130D, G153K, G153H, G153L, G153W, L303I, L469A, L469Q, L494P, L494C, L494I, L494V, L494S, L494G, and L494D.

In other aspects, the invention provides for isoprene synthase variant, wherein the variant comprises one or more substitution(s) of a hydrophobic surface amino acid selected from the group consisting of I28, V30, L130, G153, L303, L469 and L494. In some aspects, the mutation is selected from the group consisting of I28W, I28T, I28R, I28Y, V30K, L130W, L130K, L130S, L130Y, L130R, L130V, L130I, L130E, L130D, G153K, G153H, G153L, G153W, L303I, L469A, L469Q, L494P, L494C, L494I, L494V, L494S, L494G, and L494D.

In other aspects, the invention provides for any host cell comprising the nucleic acid encoding for any of the isoprene synthase variants disclosed herein. The invention also provides for host cells that express or are capable of expressing any of the isoprene synthase variants disclosed herein.

In other aspects, the invention provides for methods of generating a variant of an isoprene synthase with improved activity, expression or stability; the method comprising; a) identifying residues in the hinge region of isoprene synthase based on the three dimensional structure of P. alba isoprene synthase; b) introducing one or more amino acid substitutions in the hinge region amino acids of isoprene synthase; c) identifying variants with substitutions that improve activity, expression or stability of the isoprene synthase compared to the P. alba isoprene synthase amino acid sequence of SEQ ID NO:45. In some embodiments, the hinge region amino acid is selected from the group consisting of R198, I229 and L260.

In other aspects, the invention provides for an isolated isoprene synthase variant, wherein the variant comprises one or more substitution(s) in a hinge region amino acid selected from the group consisting of R198, I229 and L260. In other aspects, the invention provides for variants comprising one or more substitution(s) selected from the group consisting of I229V, I229L, I229C, I229T, I229P, I229N, L260N, L260M, and L260I.

In other aspects, the invention provides for methods of generating a variant of an isoprene synthase with improved activity, expression or stability; the method comprising; a) identifying amino acid residues in the negatively charged area of isoprene synthase based on the three dimensional structure of P. alba isoprene synthase; b) introducing one or more amino acid substitutions in the negatively charged area amino acids of isoprene synthase; c) identifying variants with substitutions that improve activity, expression or stability of the isoprene synthase compared to the P. alba isoprene synthase amino acid sequence of SEQ ID NO:45. In some embodiments, the negatively charged area amino acid is selected from the group consisting of D311 and D323. In some embodiments, the variant comprises one or more substitution(s) selected from the group consisting of D311M, D311F, D311L, D311G, D311I, D311A, D311T, D311R, D311V, D311E, D323M, D323W, D323Y, D323F, D323I, D323S, D323V, D323A, D323G, and D323Q.

In other aspects, the invention provides for an isoprene synthase variant, wherein the wherein the variant comprises one or more substitution(s) in a negatively charged area amino acid selected from the group consisting of D311 and D323.

In other aspects, the invention provides for methods of generating a variant of an isoprene synthase with improved activity, expression or stability; the method comprising; a) identifying amino acid residues in the flexible loops of isoprene synthase based on the three dimensional structure of P. alba isoprene synthase; b) introducing one or more amino acid substitutions in the flexible loop amino acids of isoprene synthase; and c) identifying variants with substitutions that improve activity, expression or stability of the isoprene synthase compared to the P. alba isoprene synthase amino acid sequence of SEQ ID NO:45. In some embodiments, the flexible loop amino acid is selected from the group consisting of A443, A453, N454, H515 and A519. In other embodiments, the variant comprises one or more substitution(s) selected from the group consisting of A443S, A443G, A443R, A443Q, A453L, A453N, A453I, A453V, H515M, H515Q, A519H, A519S, A519G, A519W and A519T.

In other aspects, the invention provides for an isoprene synthase variant, wherein the variant comprises one or more substitution(s) in a flexible loop amino acid selected from the group consisting of A443, A453, N454, H515 and A519. In some embodiments, the variant is substituted at amino acid T536. In other embodiments, the variant comprises one or more substitution(s) selected from the group consisting of T536F, T536Y, T536V, T536I, T536M, T536H, T536C, T536L, T536K, T536A, T536S and T536G.

In other aspects, the invention provides for methods of generating a variant of an isoprene synthase with improved activity, expression or stability; the method comprising; a) identifying amino acid residues in the diphosphate/metal binding site of isoprene synthase based on the three dimensional structure of P. alba isoprene synthase; b) introducing one or more amino acid substitutions in the diphosphate/metal binding site amino acids of isoprene synthase; and c) identifying variants with substitutions that improve activity, expression or stability of the isoprene synthase compared to the P. alba isoprene synthase amino acid sequence of SEQ ID NO:45.

In other aspects, the invention provides for isoprene synthase variants, wherein the variant comprises one or more substitution(s) in a diphosphate/metal binding site amino acid.

In other aspects, the invention provides for methods of generating a variant of an isoprene synthase with improved activity, expression or stability; the method comprising; a) identifying amino acid residues in the isoprenyl binding site of isoprene synthase based on the three dimensional structure of *P. alba* isoprene synthase; b) introducing one or more amino acid substitutions in the isoprenyl binding site amino acids of isoprene synthase; and c) identifying variants with substitutions that improve activity, expression or stability of the isoprene synthase compared to the *P. alba* isoprene synthase amino acid sequence of SEQ ID NO:45).

In other aspects, the invention provides for isoprene synthase variants, wherein the variant comprises one or more substitution(s) in a isoprenyl binding site amino acid.

In other aspects, the invention provides for methods of producing isoprene, comprising: (a) providing a host cell of any one of claims 9, 15, 21, 27, 30, 34, and 38; and (b) culturing the host cell under conditions suitable for producing isoprene.

The invention provides methods of generating a variant of an isoprene synthase with improved activity, expression or stability comprising; a) identifying amino acid residues on the surface of isoprene synthase based on the three dimensional structure of *P. alba* isoprene synthase; b) introducing one or more amino acid substitutions in the surface amino acids of isoprene synthase; c) identifying mutations that improve activity, expression or stability of the isoprene synthase compared to the *P. alba* isoprene synthase comprising the amino acid sequence of SEQ ID NO: 18. In some embodiments, the amino acid substitutions include one or more of the following: hydrophobic to positively charged, positively charged to hydrophobic, hydrophobic to negatively charged, negatively charged to hydrophobic, hydrophobic to neutral polar, neutral polar to hydrophobic, neutral polar to positively charged, positively charged to neutral polar, neutral polar to negatively charged, negatively charged to neutral polar, positively charged to negatively charged, and negatively charged to positively charged.

The invention provides methods for generating a variant of an isoprene synthase with improved activity comprising a) identifying amino acid residues in or near the diphosphate/metal binding site in the three dimensional structure of *P. tremuloides* isoprene synthase; b) introducing one or more amino acid substitutions in or near the diphosphate/metal binding site of isoprene synthase; c) identifying mutations that improve the activity of the isoprene synthase compared to the *P. tremuloides* isoprene synthase comprising the amino acid sequence of SEQ ID NO:11. In some embodiments the invention provides an isolated isoprene synthase variant produced by these methods. In some embodiments, the amino acids in the diphosphate/metal binding site are selected from the group consisting of D293, Y385, S392 and D437.

The invention provides methods of generating a variant of an isoprene synthase with improved activity comprising a) identifying amino acid residues in the isoprenyl binding site in the three dimensional structure of *P. tremuloides* isoprene synthase; b) introducing one or more amino acid substitutions in the isoprenyl binding site of isoprene synthase; c) identifying mutations that improve the activity of the isoprene synthase compared to the *P. tremuloides* isoprene synthase comprising the amino acid sequence of SEQ ID NO:11. In some embodiments the invention provides an isolated isoprene synthase variant produced by this method. In some embodiments, the amino acids in the isoprenyl binding site are selected from the group consisting of S261, W264, F285, T289, S393, S394, F432 and Y512.

The invention provides methods of generating a variant of an isoprene synthase with improved activity comprising a) identifying amino acid residues in the substrate access loop in the three dimensional structure of *P. tremuloides* isoprene synthase; b) introducing one or more amino acid substitutions in the substrate access loop of isoprene synthase; c) identifying mutations that improve the activity of the isoprene synthase compared to the *P. tremuloides* isoprene synthase comprising the amino acid sequence of SEQ ID NO:11. In some embodiments the invention provides an isolated isoprene synthase variant produced by these methods. In some embodiments the amino acids in the substrate access loop are selected from the group consisting of S440, A441, S442, A443, E444, I445, A446, R447, G448, E449, T450, A451, N452, S453, Y512, H513, N514, G515, D516, A517, H518, T519, S520, P521, D522, E523, and L524.

The invention provides a variant of a parent synthase that is structurally homologous to isoprene synthase and having modified residues corresponding to or analogous to the following residues of the flexible N-terminus and/or adjacent residues; 1-28, 239, 243, 253-257, 259, 260, 293, 295-300, 303, 325, 374 of an isoprene synthase. In some embodiments, the synthase is an isoprene synthase. In some embodiments, the invention provides a variant of a parent synthase that is structurally homologous to isoprene synthase and having modified residues corresponding to or analogous to the following residues of the flexible loop I and/or adjacent residues; 438-453, 293, 295, 297, 370, 371, 373, 374, 378-380, 382, 385, 386, 433-437, 454-458, 469, 472, 476, 512 of isoprene synthase. In some embodiments, the synthase is an isoprene synthase. In some embodiments, the invention provides a variant of a parent synthase that is structurally homologous to isoprene synthase and having modified residues corresponding to or analogous to the following residues of the flexible loop II and/or adjacent residues; 512-526, 187, 188, 255, 257, 270, 271, 273, 274, 285, 288, 439, 440, 442, 508-512, and 528-532 of isoprene synthase the synthase is an isoprene synthase.

The invention provides methods of generating a variant of a parent terpene synthase or terpene synthase structural homolog with improved activity comprising a) identifying amino acid residues in or near one or more substrate access loops in the three dimensional structure of the terpene synthase or terpene synthase structural homolog, b) introducing one or more amino acid substitutions in or near the one or more substrate access loops of the terpene synthase or terpene synthase structural homolog, c) identifying substitutions that improve the activity of the terpene synthase or terpene synthase structural homolog variant compared to the parent terpene synthase or terpene synthase structural homolog. In some embodiments, the terpene synthase or terpene synthase structural homolog is an isoprene synthase. In some embodiments, the isoprene synthase is *P. tremuloides* isoprene synthase comprising SEQ ID NO:11. In some embodiments, the isoprene synthase is *P. alba* isoprene synthase comprising SEQ ID NO: 18. In some embodiments, the variant comprises a substitution of one or more of the following amino acid residues L17, L18, S19, S20, S239, R243, F253, A254, R255, D256, R257, I259, E260, D293, Y295, D296, V297, Y298, G299, T300, E303, Y325, L374, Y375, V529, L530, T534, D293, Y295, V297, E370, A371, W373, L374, S378, T379, P380, F382, Y385, F386, R433, L434 C435, N436, D437, V454, S455, C456, Y457, M458, T469, V472, I476, Y512, E187, L188, R255, R257, F270, E271, Q273, Y274, F285, V288, A439, S440, S442, S508, H509, C510, T511, Y512, R528, V529, L530, S531, and V532.

The invention provides methods of generating a variant of isoprene synthase by a) obtaining a crystal comprising an isoprene synthase; b) obtaining the atomic coordinates of the crystal; c) correlating the atomic coordinate data with one or more molecular modeling techniques; d) identifying at least one modification predicted to effect the activity, expression or stability of isoprene synthase; and e) modifying the isoprene synthase based on the prediction. In some embodiments, the isoprene synthase is *P. tremuloides* isoprene synthase. In some embodiments, the isoprene synthase is a *P. alba* isoprene synthase.

In some aspects, the invention provides methods of generating a variant of an isoprene synthase comprising a) correlating the atomic coordinate data for *P. tremuloides* isoprene synthesis of Table 3-7 with one of more molecular modeling techniques b) identifying at least one modification predicted to effect the activity, expression or stability of isoprene synthase; and c) modifying the isoprene synthase based on the prediction obtained in b).

In some aspects, the invention provides methods of generating a variant of an isoprene synthase comprising a) correlating the atomic coordinate data for *P. alba* isoprene synthesis of Table 4-2 with one of more molecular modeling techniques b) identifying at least one modification predicted to effect the activity, expression or stability of isoprene synthase; and c) modifying the isoprene synthase based on the prediction obtained in b).

In other aspects, the invention provides methods of identifying a candidate variant of an isoprene synthase comprising: a) comparing the atomic structure of the isoprene synthase without a bound ligand to the atomic structure of the isoprene synthase with a bound ligand, and b) computationally identifying candidate variants of the isoprene synthesis for the ability to bind the ligand.

The invention provides methods of generating a variant of an isoprene synthase with improved activity, expression or stability comprising; a) identifying amino acid residues on the surface of isoprene synthase based on the three dimensional structure of *P. tremuloides* isoprene synthase; b) introducing one or more amino acid substitutions in the surface amino acids of isoprene synthase; c) identifying mutations that improve activity, expression or stability of the isoprene synthase compared to the *P. tremuloides* isoprene synthase comprising the amino acid sequence of SEQ ID NO: 11. In some embodiments, the amino acid substitutions include one or more of the following: hydrophobic to positively charged, positively charged to hydrophobic, hydrophobic to negatively charged, negatively charged to hydrophobic, hydrophobic to neutral polar, neutral polar to hydrophobic, neutral polar to positively charged, positively charged to neutral polar, neutral polar to negatively charged, negatively charged to neutral polar, positively charged to negatively charged, and negatively charged to positively charged.

The invention provides methods of generating variants of an isoprene synthase with improved activity, expression or stability by a) identifying hydrophobic amino acid residues on the surface of isoprene synthase based on the three dimensional structure of *P. alba* isoprene synthase; b) introducing one or more amino acid substitutions in the surface amino acids of isoprene synthase; c) identifying mutations that improve activity, expression or stability of the isoprene synthase compared to the parent *P. alba* isoprene synthase.

The invention provides isolated *P. alba* isoprene synthase variants comprising a mutation of a hydrophobic surface amino acid at one or more of the following residues: I28, V30, L130, G153, L303, L469 and L494. In some embodiments, the variant comprises one or more of the following mutations: I28W, I28T, I28R, I28Y, V30K, L130W, L130K, L1305, L130Y, L130R, L130V, L130I, L130E, L130D, G153K, G153H, G153L, G153W, L303I, L469A, L469Q, L494P, L494C, L494I, L494V, L494S, L494G, and L494D.

The invention provides methods of generating variants of a parent isoprene synthase with improved activity, expression or stability by a) identifying residues in the hinge region of isoprene synthase based on the three dimensional structure of *P. alba* isoprene synthase; b) introducing one or more amino acid substitutions in the hinge region amino acids of isoprene synthase; c) identifying mutations that improve activity, expression or stability of the isoprene synthase compared to the parent *P. alba* isoprene synthase.

In some aspects, the invention provides isolated *P. alba* isoprene synthase variants comprising a mutation in or near a hinge region wherein the variant comprises a mutation at one or more of the following residues R198, I229 and L260. In some embodiments, the variant comprises one or more of the following mutations: I229V, I229L, I229C, I229T, I229P, I229N, L260N, L260M, and L260I.

The invention provides methods of generating variants of an isoprene synthase with improved activity, expression or stability by a) identifying amino acid residues in the electrostatic patch of isoprene synthase based on the three dimensional structure of *P. alba* isoprene synthase; b) introducing one or more amino acid substitutions in the electrostatic patch amino acids of isoprene synthase; c) identifying mutations that improve activity, expression or stability of the isoprene synthase compared to the parent *P. alba* isoprene synthase.

In some aspects, the invention provides isolated *P. alba* isoprene synthase variants, wherein the wherein the variant comprises a mutation in an electrostatic patch amino acid including, but not limited to residues D311 and D323. In some embodiments, the variant comprises one or more of the following mutations: D311M, D311F, D311L, D311G, D311I, D311A, D311T, D311R, D311V, D311E, D323M, D323W, D323Y, D323F, D323I, D323S, D323V, D323A, D323G, and D323Q.

The invention provides methods of generating variants of an isoprene synthase with improved activity, expression or stability by a) identifying amino acid residues in the flexible loops of isoprene synthase based on the three dimensional structure of *P. alba* isoprene synthase; b) introducing one or more amino acid substitutions in the flexible loop amino acids of isoprene synthase; c) identifying mutations that improve activity, expression or stability of the isoprene synthase compared to the parent *P. alba* isoprene synthase.

The invention provides isolated *P. alba* isoprene synthase variants comprises a mutation in a flexible loop at one or more of the following residues: A443, A453, N454, H515, A519 and E525. In some embodiments, the variant comprises one or more of the following mutations: A443S, A443G, A443R, A443Q, A453L, A453N, A453I, A453V, H515M, H515Q, A519H, A519S, A519G, A519W and A519T.

In some aspects, the invention provides isolated *P. alba* isoprene synthase variants mutated at amino acid T536. In some embodiments, the variant comprises one of the following mutations: T536F, T536Y, T536V, T536I, T536M, T536H, T536C, T536L, T536K, T536A, T536S and T536G.

The invention provides methods of generating variants of an isoprene synthase with improved activity, expression or stability; the method comprising; a) identifying amino acid residues in the diphosphate/metal binding site of isoprene synthase based on the three dimensional structure of *P. alba* isoprene synthase; b) introducing one or more amino acid substitutions in the diphosphate/metal binding site amino acids of isoprene synthase; c) identifying mutations that improve activity, expression or stability of the isoprene synthase compared to the parent *P. alba* isoprene synthase. In some aspects, the invention provides isolated isoprene synthase variants, comprising a mutation in a diphosphate/metal binding site residue of *P. alba* isoprene synthase.

The invention provides methods of generating variants of an isoprene synthase with improved activity, expression or stability; the method comprising a) identifying amino acid residues in the isoprenyl binding site of isoprene synthase based on the three dimensional structure of *P. alba* isoprene synthase; b) introducing one or more amino acid substitutions in the isoprenyl binding site amino acids of isoprene synthase; c) identifying mutations that improve activity, expression or stability of the isoprene synthase compared to the parent *P. alba* isoprene synthase. In some aspects, the invention provides isolated *P. alba* isoprene synthase variants comprises a mutation in a isoprenyl binding site amino acid.

In another aspect, the invention provides a crystalline form of an isoprene synthase. In particular, the invention provides methods of improving the activity of a terpene synthase based on the crystalline form of isoprene synthase. In some embodiments, the crystalline form of the isoprene synthase further comprises a ligand, for example dimethylallyl pyrophosphate (DMAPP).

In some aspects, a crystalline form of *P. tremuloides* isoprene synthase comprises a structure characterized by tetragonal space group symmetry P4$_3$2$_1$2 and unit cell dimensions of a=154.2 angstroms, b=154.2 angstroms and c=142.7 angstroms and wherein the alpha=beta=gamma=90 degrees. In some embodiments, the unit cell dimensions are a=146.5 to 161.9 angstroms, b=146.5 to 161.9 angstroms and c=135.6 to 149.8 angstroms and wherein the alpha=beta=gamma=90 degrees.

In some aspects, a crystalline form of *P. alba* isoprene synthase comprises a structure characterized by tetragonal space group symmetry P4$_3$2$_1$2 and unit cell dimensions of a=156.8 angstroms, b=156.8 angstroms and c=142.5 angstroms and wherein the alpha=beta=gamma=90 degrees. In some embodiments, the unit cell dimensions are a=148.96 to 164.6 angstroms, b=148.96 to 164.6 angstroms and c=135.4 to 149.6 angstroms and wherein alpha=beta=gamma=90 degrees.

The invention provides a crystalline form of a polypeptide comprising a structure defined by one or more structure coordinates of *P. tremuloides* isoprene synthase amino acids Arg 255, Asp 292, Asp 296, Glu 370, Arg 433 and Asn436, Ser261, Trp264, Phe285, Thr289, Ser393, Phe432 and Tyr512 according to Table 3-7, or similar structural coordinates for said residues comprising a root mean square deviation of less than about 1.5 Å when superimposed on the non-hydrogen atom positions of the corresponding atomic coordinates of Table 3-7. In some embodiments, the root mean square deviation is less than about 0.75 Å when superimposed on the non-hydrogen atom positions of the corresponding atomic coordinates of Table 3-7. In some embodiments, the root mean square deviation is less than about 0.35 Å when superimposed on the non-hydrogen atom positions of the corresponding atomic coordinates of Table 3-7.

In some embodiments of the invention, the invention provides a crystalline form of a *P. tremuloides* isoprene synthase wherein amino acid residues Arg 255, Asp 292, Asp 296, Glu 370, Arg 433 and Asn 436 comprise the diphosphate/metal binding sites of the isoprene synthase. In some embodiments, amino acid residues Ser 261, Trp 264, Phe 285, Thr 289, Ser 393, Ser 394, Phe 432, and Try 512 comprise the isoprenyl binding site of the isoprene synthase. In some embodiments, amino acid residues 438-453 having the sequence SASAEIARGETANS (SEQ ID NO:40) and residues 512-526 having the sequence YHNGDAHTSPDEL (SEQ ID NO:41) comprise the substrate access loops of the isoprene synthase. In some embodiments, amino acids 1-16 and 17-28 comprise N-terminal loops designated N-terminal loop I and N-terminal loop II.

The invention provides a crystalline form of a polypeptide that comprises an amino acid sequence having at least 75% identity to SEQ ID NO:11. In some embodiments, the polypeptide comprises an amino acid sequence having at least 85% identity to SEQ ID NO:11. In other embodiments, the polypeptide comprises an amino acid sequence having at least 90% identity to SEQ ID NO:11.

The invention provides a crystalline form of a polypeptide that comprises an amino acid sequence having at least 75% identity to SEQ ID NO:18. In some embodiments, the polypeptide comprises an amino acid sequence having at least 85% identity to SEQ ID NO:18. In other embodiments, the polypeptide comprises an amino acid sequence having at least 90% identity to SEQ ID NO:11.

The invention provides a scalable three-dimensional configuration of points, at least a portion of said points derived from structure coordinates of at least a portion of a *P. tremuloides* isoprene synthase molecule or molecular complex listed in Table 3-7 and having a root mean square deviation of less than about 1.5 Å from said structure coordinates. In some embodiments, at least a portion of the points derived from the *P. tremuloides* isoprene synthase structure coordinates are derived from structure coordinates representing the locations of at least the backbone atoms of a plurality of the amino acids defining at least one *P. tremuloides* isoprene synthase or *P. tremuloides* isoprene synthase-like diphosphate/metal binding site comprising amino acids Arg 255, Asp 292, Asp 296, Glu 370, Arg 433 and Asn436. In some embodiments, at least a portion of the points derived from the *P. tremuloides* isoprene synthase structure coordinates are derived from structure coordinates representing the locations of at least the backbone atoms of a plurality of the amino acids defining at least one *P. tremuloides* isoprene synthase or *P. tremuloides* isoprene synthase-like isoprenyl binding site, the isoprenyl binding site comprising amino acids Ser 261, Trp 264, Phe 285, Thr 289, Ser 393, Ser 394, Phe 432, and Tyr 512. In other embodiments, at least a portion of the points derived from structure coordinates representing the locations of at least the backbone atoms of a plurality of the amino acids defining at least one *P. tremuloides* isoprene synthase or *P. tremuloides* isoprene synthase-like flexible loop including but not limited to Loop I amino acid residues 438-453 including the sequence SASAEIARGETANS (SEQ ID NO:40), residues 512-526 having the sequence YHNGDAHTSPDEL (SEQ ID NO:41), amino acids 1-16 forming N-terminal loop I amino acids 17-28 forming N-terminal loop II. In some embodiments, at least a portion of the points derived from the *P. tremuloides* isoprene synthase structure coordinates are derived from structure coordinates representing the locations of at least the backbone atoms of a plurality of the amino acids defining at least one *P. tremuloides* isoprene synthase or *P. tremuloides* isoprene synthase-like diphosphate/metal binding site, the diphosphate/metal binding site comprising amino acids Arg 255, Asp 292, Asp 296, Glu 370, Arg 433 and Asn436; and at least a portion of the points derived from the *P. tremuloides* isoprene synthase structure coordinates are derived from structure coordinates representing the locations of at least the backbone atoms of a plurality of the amino acids defining at least one *P. tremuloides* isoprene synthase or *P. tremuloides* isoprene synthase-like isoprenyl binding site, the isoprenyl binding site comprising amino acids Ser 261, Trp 264, Phe 285, Thr 289, Ser 393, Ser 394, Phe 432, and Try 512.

The invention provides a machine-readable medium embedded with information that corresponds to a three-dimensional structural representation of a crystalline form of a *P. tremuloides* isoprene synthase or of a *P. alba* isoprene synthase. Additionally, the invention provides a computer system comprising a database containing information on the three dimensional structure of a crystalline form of a *P. tremuloides* isoprene synthase or a *P. alba* isoprene synthase and a user interface to view the information. A figure showing the high structural homology between the two coordinate sets included is shown as a stereodisgram in FIG. 64.

The invention provides agents characterized by a three-dimensional configuration of points derived from structure coordinates of at least a portion of a *P. tremuloides* isoprene synthase molecule or molecular complex listed in Table 3-7 and having a root mean square deviation of less than about 1.5 Å from said structure coordinates. In some embodiments, agents are characterized by a three-dimensional configuration of points derived from structure coordinates representing the locations of at least the backbone atoms of a plurality of the amino acids defining at least one *P. tremuloides* isoprene synthase or *P. tremuloides* isoprene synthase-like diphosphate/metal binding site comprising amino acids Arg 255, Asp 292, Asp 296, Glu 370, Arg 433 and Asn436. In some embodiments, agents are characterized by at least a portion of the points derived from the *P. tremuloides* isoprene synthase structure coordinates are derived from structure coordinates representing the locations of at least the backbone atoms of a plurality of the amino acids defining at least one *P. tremuloides* isoprene synthase or *P. tremuloides* isoprene synthase-like isoprenyl binding site, the isoprenyl binding site comprising amino acids Ser 261, Trp 264, Phe 285, Thr 289, Ser 393, Ser 394, Phe 432, and Try 512. In other embodiments, agents are characterized by at least a portion of the points derived from structure coordinates representing the locations of at least the backbone atoms of a plurality of the amino acids defining at least one *P. tremuloides* isoprene synthase or *P. tremuloides* isoprene synthase-like flexible loop including but not limited to Loop I amino acid residues 438-453 including the sequence SASAEIARGETANS (SEQ ID NO:40), residues 512-526 having the sequence YHNGDAHTSPDEL (SEQ ID NO:41), amino acids 1-16 forming N-terminal loop I amino acids 17-28 forming N-terminal loop II.

The invention provides a scalable three-dimensional configuration of points, at least a portion of the points derived from structure coordinates of a *P. alba* isoprene synthase molecule or a molecular complex listed in Table 4-2 and having a root mean square deviation of less than about 1.5 Å from said structure coordinates. In some embodiments, at lease a portion of the points derived from the *P. alba* isoprene synthase structure coordinates are derived from structure coordinates representing the locations of at least the backbone atoms of a plurality of the amino acids defining at least one *P. alba* isoprene synthase or *P. alba* isoprene synthase-like sites, including but not limited to, a diphosphate/metal binding site, a isoprenyl binding site, a flexible loop, an electrostatic patch and a hinge region.

The invention provides agents characterized by a three-dimensional configuration of points derived from the structure coordinates of at lease a portion of a *P. alba* isoprene synthase molecule or molecular complex listed in Table 4-2 and having a root mean square deviation of less than about 1.5 Å from said structure coordinates. In some embodiments, agents are characterized by a three-dimensional configuration of points derived from the structural reaction coordinates representing the locations of at least the backbone atoms of a plurality of the amino acids defining at least one *P. alba* isoprene synthase or *P. alba* isoprene synthase-like of diphosphate/metal binding site, a flexible loop, an electrostatic patch and a hinge region.

The invention provides methods of producing isoprene by (a) providing a host cell comprising a *P. alba* isoprene synthase variant and (b) culturing the host cell under conditions suitable for producing isoprene.

BRIEF DESCRIPTION OF THE DRAWINGS

FIG. 3 (3A, B) provides the nucleotide sequence (SEQ ID NO:1) of plasmid p9795.

FIG. 5 (5A, B, C) provides the nucleotide sequence (SEQ ID NO:2) of plasmid pTrcKudzu.

FIG. 7 (7A, B, C) provides the nucleotide sequence (SEQ ID NO:3) of plasmid pMAL-C4X.

FIG. 9 (9A, B, C, D) provide the nucleotide sequence (SEQ ID NO:4) of pMAL-C4X-Kudzu.

FIG. 10 provides maps of pET24 *P. tremuloides* (A) and pET24 *P. trichocarpa* (B).

FIG. 11 provides the amino acid Sequence (SEQ ID NO:5) of *P. tremuloides* IspS in *P. tremuloides* pET24a.

FIG. 12 (12A, B, C) provides the nucleotide sequence (SEQ ID NO:6) of plasmid *P. tremuloides* pET24.

FIG. 13 provides the amino acid sequence (SEQ ID NO:7) of *P. trichocarpa* IspS in *P. trichocarpa* pET24a.

FIG. 14 (14A, B, C) provides the nucleotide sequence (SEQ ID NO:8) of plasmid *P. trichocarpa* pET24.

FIG. 15A provides the map of plasmids pDu30.

FIG. 15B provides the map of plasmids pDu31.

FIG. 16 provides the amino acid sequence (SEQ ID NO:9) of the *P. alba* IspS variant in pDu30.

FIG. 17 (17A, B, C) provides the nucleotide sequence (SEQ ID NO:10) of plasmid pDu30.

FIG. 18 provides the amino acid sequence (SEQ ID NO:11) of the *P. tremuloides* IspS variant in pDu31. The numbering convention for purposes of describing the three-dimensional structure of isoprene synthase is such that the first number of the complete sequence containing the tag is −35, with the first three residues of IspS being MRR (underlined).

FIG. 19 (19A, B, C) provides the nucleotide sequence (SEQ ID NO:12) of plasmid pDu31.

FIG. 20 provides the amino acid sequence (SEQ ID NO:13) of the *P. trichocarpa* IspS variant in pDu32.

FIG. 21 (21A, B, C) provides the nucleotide sequence (SEQ ID NO:14) of plasmid pDu32.

FIG. 22 (22A, B, C) provides the nucleotide sequence (SEQ ID NO:15) of plasmid pDu27.

FIG. 23 provides the amino acid sequence (SEQ ID NO:16) of full length *P. alba* IspS in *P. alba* pET24a.

FIG. 24 (24A, B, C) provides the nucleotide sequence of sequence (SEQ ID NO:17) of *P. alba* pET24a.

FIG. 25 provides the maps of plasmids MD09-161 (A) and MD09-163 (B).

FIG. 26 provides amino acid sequence (SEQ ID NO:18) of *P. alba* MEA(+)TEV in MD09-163.

FIG. 27 (A, B, C) provides the nucleotide sequence (SEQ ID NO:19) of plasmid MD09-163. The CDS is underlined and the TEV protease site is bold.

FIG. 28 provides the amino acid sequence (SEQ ID NO:20) of *P. alba* FL (+) TEV in MD09-161.

FIG. 29 (29A, B, C) provides the nucleotide sequence (SEQ ID NO:21) of MD09-161. The CDS is underlined and the TEV protease site is bold.

FIG. 37 provides the amino acid sequence (SEQ ID NO:42) of a kudzu isoprene synthase.

FIG. 38 provides the amino acid sequence of a *Populus [alba×tremuloides]* isoprene synthase (SEQ ID NO:43).

FIG. 40 (40A, B, C) provides the nucleotide sequence (SEQ ID NO:44) of pCL201. The IspS CDS is underlined.

FIG. 41 provides the amino acid sequence of *P. alba* IspS residues 1 through 544 (SEQ ID NO:45).

FIG. 45 shows the layout of a typical 96-well plate containing four complete libraries to be screened for isoprene production and protein concentration.

FIG. 51 shows an SDS-PAGE gel showing IspS-L494P at different stages of the purification. Lane 1-molecular weight standard; Lane 2-IspS-L494P prior to treatment with TurboTEV; Lane 3-IspS-L494P treated with TurboTEV; Lanes 4-6-IspS-L494P after final buffer exchange at different dilution levels.

FIG. 52 shows $2F_O$-$2F_C$ electron density map at residue 494 contoured at 1-sigma. Panel A shows 494L, Panel B shows 494P.

FIG. 53 depicts the alignment of the loop containing residue 494. Wild type IspS is light grey and IspS-L494P is dark grey. The L494P mutation results in an alternate loop structure.

FIG. 54 depicts a SDS-PAGE gel showing purified IspS-T536F at different dilutions (lanes 2-4) and molecular weight standard (lane 1).

FIG. 55 depicts a SDS-PAGE gel showing total cell lysate (lanes 2, 5, 8), supernatant (lanes 3, 6, 9), and purified protein (lanes 4, 7, 10) for wild type IspS, IspS-L494P and IspS-T536F, respectively. A molecular weight marker is in lane 1.

FIG. 56 depicts thermal unfolding curves for wild type IspS, IspS-L494P, and IspS-T536F incubated with buffer only. $T_M$ values are indicated for each variant.

FIG. 57 depicts thermal unfolding curves for wild type IspS, IspS-L494P, and IspS-T536F incubated with 5 mM sodium pyrophosphate. $T_M$ values are indicated for each variant.

FIG. 58 depicts temperature activity ration curves for wild type IspS (WT), IspS-L494P (LP), and IspS-T536F (TF). Data are plotted as a ratio of the specific activity (nmol/mg/min) of the protein at a given temperature divided by the specific activity at 35° C.

FIG. 59 depicts local alignment of *P. alba* isoprene synthase and related terpene synthase enzymes (SEQ IDS NOs: 99-112).

FIG. 60 depicts a map of plasmid MD09-163 with A453N, G491S, L494P, and T536C/F mutations.

FIG. 61 depicts a gel showing a dilution series of Isoprene Synthases assayed for rate vs. [DMAPP].

FIG. 62 depicts a graph showing the specific activity of each variant with 4 mM DMAPP assayed at 30° C. The black bar indicates the specific activity of the WT isoprene synthase.

FIG. 63 depicts a graph showing rate vs. [DMAPP] for the P, SP and SPC variants of isoprene synthase and WT isoprene synthase. Each data point on the graph is the average of three independently performed kinetic assays. Error bars are reported as one standard deviation above and below the data point.

FIG. 64 depicts an alignment of the P. tremuloides (black) and P. alba structures (grey) showing high level of structural homology.

DETAILED DESCRIPTION OF THE INVENTION

Figure 1:
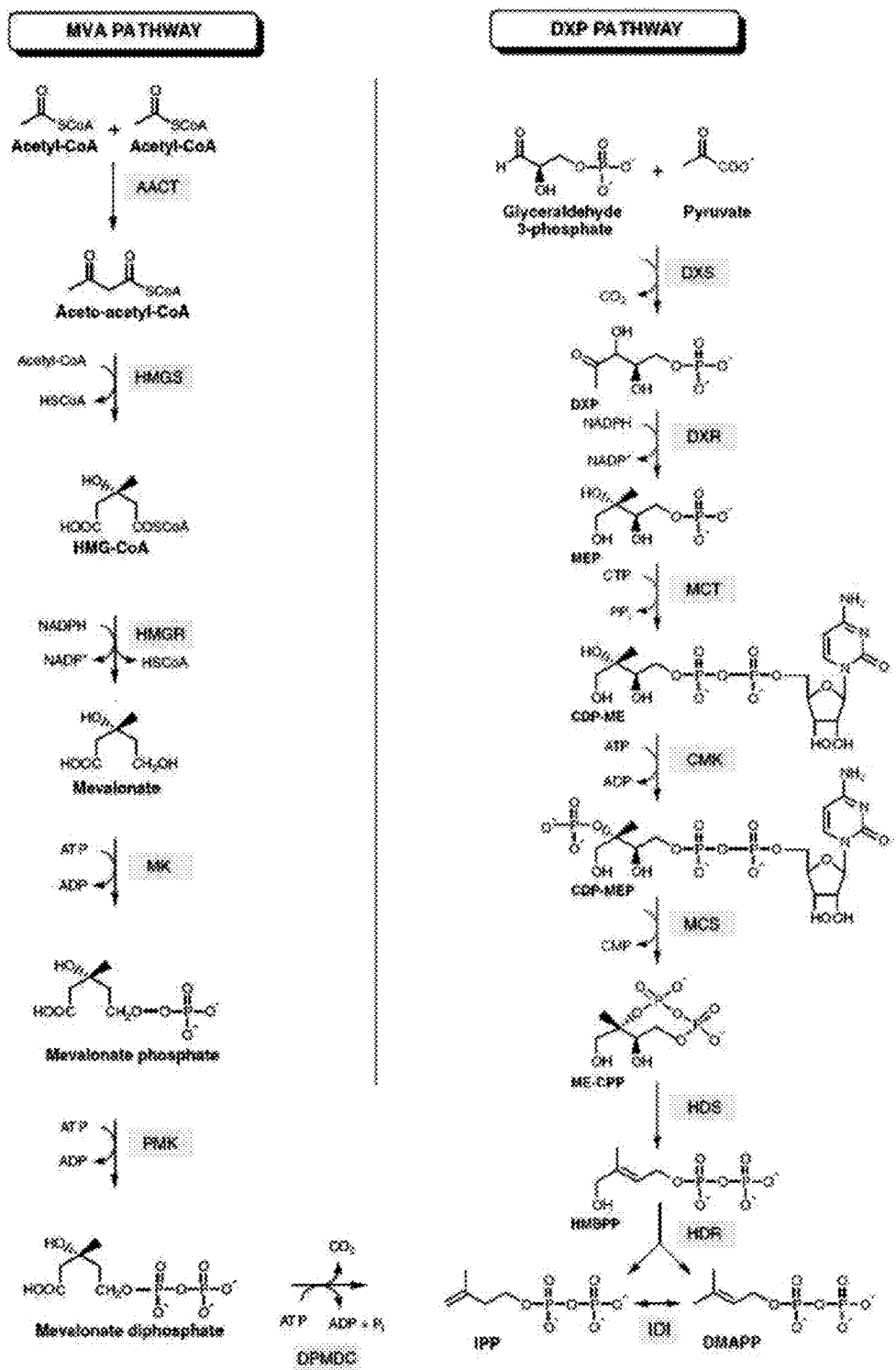
FIG. 1 shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet. 19:9-14, 1991. PMK; Phosphomevalonate kinase, ERGS, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

The present invention provides methods and compositions comprising at least one synthase enzyme with improved activity (e.g., catalytic activity) and/or solubility, variants of synthase and agents characterized by modifications of the amino acid residues in two flexible loops and/or N-terminus and/or their adjacent regions. In particular, the present invention provides for the selective modification of these segments in a three-dimensional structure of an isoprene synthase. Isoprene synthase contemplated by the invention include, but are not limited to plant isoprene synthases; e.g., poplar isoprene synthase, kudzu isoprene synthase, oak isoprene synthase and the like. Poplar isoprene synthase include, but are not limited to, isoprene synthases from P. tremuloides, P. alba, P. alba v. tremuloides, P. trichocharpa, and the like. Variant isoprene synthases for increased isoprene production in microbial host cells are derived based on the three-dimensional structure. Agents which can increase isoprene production can also be modeled using the three-dimensional structure of an isoprene synthase provided herein. Biosynthetically produced isoprene of the present invention finds use in the manufacture of rubber and elastomers.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual," Third Edition, Cold Spring Harbor, 2001; and Ausubel et al., "Current Protocols in Molecular Biology," 1987). All patents, patent applications, articles and publications mentioned herein, both supra and infra, are hereby expressly incorporated herein by reference.

Definitions

As used herein, the term isoprene refers to 2-methyl-1,3-butadiene (CAS #78-79-5). Isoprene can be produced as the direct and final volatile C5 hydrocarbon product from the elimination of pyrophosphate from 3,3-dimethylallyl pyrophosphate (DMAPP), and does not involve the linking or polymerization of (an) IPP molecule(s) to (a) DMAPP molecule(s).

As used herein, the terms "isoprene synthase," and "IspS," refer to the enzymes that catalyze the elimination or pyrophosphate from diemethylallyl diphosphate (DMAPP) to form isoprene. In some preferred embodiments, the IspS is an enzyme obtained from plants such as kudzu, poplar or red oak. In some embodiments, the term "IspS" refers to a naturally occurring mature enzyme or portion thereof.

As used herein, the term "variant proteins" refers to proteins that differ from a parent protein (e.g., kudzu IspS set forth as SEQ ID NO:42 and P. alba IspS set forth in SEQ ID NO:16 or FIG. 23) and from one another by a small number of amino acid residues. The number of differing amino acid residues may be one or more, preferably 1, 2, 3, 4, 5, 6, 7, 8, 9, 10, 11, 12, 13, 14, 15, 20, 30, 40, 50, or more amino acid residues. In some preferred embodiments, the number of different amino acids between variants is between 1 and 10. In some particularly preferred embodiments, related proteins and particularly variant proteins have at least 35%, 40%, 45%, 50%, 55%, 60%, 65%, 70%, 75%, 80%, 85%, 90%, 95%, 97%, 98%, or 99% amino acid sequence identity. Related (and derivative) proteins can comprise "variant proteins." Additionally, a related protein or a variant protein as used herein refers to a protein that differs from another related protein or a parent protein in the number of prominent regions. For example, in some embodiments, variant proteins have 1, 2, 3, 4, 5, or 10 corresponding prominent regions that differ from the parent protein.

As discussed in greater detail herein, several methods are known in the art that are suitable for generating variants of the enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

As used herein, the singular form "a", "an", and "the" includes plural references unless indicated otherwise.

As used herein, the term "agent" can refer to any type of composition of matter, including but not limited to, polypeptides, nucleotides, small molecules, and synthetic compounds.

As used herein, the term "gene" refers to a polynucleotide (e.g., a DNA segment) that encodes a polypeptide and includes regions preceding and following the coding regions as well as intervening sequences (introns) between individual coding segments (exons).

As used herein, the terms "starting gene" and "parent gene" refer to a gene of interest that encodes a protein of interest that is to be improved and/or changed using the present invention. Likewise, the terms "starting protein" and "parent protein" refer to a protein of interest that is to be improved and/or changed using the present invention.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one.

As used herein, "homology" refers to sequence similarity or identity, with identity being preferred. This homology is determined using standard techniques known in the art (See e.g., Smith and Waterman, Adv Appl Math, 2:482, 1981; Needleman and Wunsch, J Mol Biol, 48:443, 1970; Pearson and Lipman, Proc Natl Acad Sci USA, 85:2444, 1988; programs such as GAP, BESTFIT, FASTA, and TFASTA in the Wisconsin Genetics Software Package, Genetics Computer Group, Madison, Wis.; and Devereux et al., Nucl Acid Res, 12:387-395, 1984).

As used herein, an "analogous sequence" on an isoprene synthase is one wherein the function of the gene is essentially the same as the gene based on the kudzu isoprene synthase. Additionally, analogous genes include at least 45%, 50%, 55%, 60%, 65%, 70%, 75%, 80%, 85%, 90%, 95%, 97%, 98%, 99% or 100% sequence identity with the sequence of the kudzu isoprene synthase. In additional embodiments more than one of the above properties applies to the sequence. Analogous sequences are determined by known methods of sequence alignment. A commonly used alignment method is BLAST, although as indicated above and below, there are other methods that also find use in aligning sequences.

"Percent sequence identity," "percent amino acid sequence identity," "percent gene sequence identity," and/or "percent nucleic acid/polynucleotide sequence identity," with respect to two amino acids, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "crystal lattice" means the array of points defined by the vertices of packed unit cells.

As used herein, the term "unit cell" means a basic parallelipiped shaped block. The entire volume of a crystal can be constructed by regular assembly of such blocks. Each unit cell comprises a complete representation of the unit of pattern, the repetition of which builds up the crystal. Thus, the term "unit cell" means the fundamental portion of a crystal structure that is repeated infinitely by translation in three dimensions. A unit cell is characterized by three vectors a, b, and c, not located in one plane, which form the edges of a parallelepiped. Angles α, β, and γ define the angles between the vectors: angle α is the angle between vectors b and c; angle β is the angle between vectors a and c; and angle γ is the angle between vectors a and b. The entire volume of a crystal can be constructed by regular assembly of unit cells; each unit cell comprises a complete representation of the unit of pattern, the repetition of which builds up the crystal.

The term "structure coordinates" refers to Cartesian coordinates derived from mathematical equations related to the patterns obtained on diffraction of a monochromatic beam of x-rays by the atoms (scattering centers) of an isoprene synthase complex in crystal form. The diffraction data are used to calculate an electron density map of the repeating unit of the crystal. The electron density maps are then used to establish the positions of the individual atoms of the isoprene synthase protein or protein/ligand complex.

As used herein, the terms "active site," "binding site" or "binding pocket" refer to a region of a polypeptide or a molecular complex comprising the polypeptide that, as a result of the primary amino acid sequence of the polypeptide and/or its three-dimensional shape, favorably associates with another chemical entity or compound including ligands or inhibitors. Thus, an active site may include or consist of features such as interfaces between domains. Chemical entities or compounds that may associate with an active site include, but are not limited to, compounds, ligands, cofactors, substrates, inhibitors, agonists, antagonists, etc.

"Structural reaction residues" refers to a three-dimensional collection of atoms involved in an enzymatic reaction. For example, these would include those forming the active site, those coordinating metal ions and those forming the substrate bind region. In particular, those forming the flexible loops and N-terminus and the adjacent residues that stabilize the flexible segments when substrate is bound.

Structurally equivalent synthases refer to those synthases for which a crystallographic structure has been determined, whose atomic coordinates can be aligned by a publically available software package, such as PYMOL (DeLano Scientific LLC) such that a preponderance of the main chain alpha carbon atoms can be aligned within a rms deviation of 0.2 nm. For this purpose, a preponderance would be defined as either 50%, 60% or 70% of the total alpha carbons of the isoprene synthase structure.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of a *P. tremuloides* isoprene synthase, a *P. alba* isoprene synthase, or an active site portion thereof, as defined by the structure coordinates described herein.

"Having substantially the same three-dimensional structure" refers to a polypeptide that is characterized by a set of atomic structure coordinates that have a root mean square deviation (r.m.s.d.) of less than or equal to about 1.5 Å when superimposed onto the atomic structure coordinates of an isoprene synthase, e.g. the atomic structure coordinates of Table 3-7 or Table 4-2 when at least about 50% to 100% of the Cα atoms of the coordinates are included in the superposition.

As used herein, "homologous segment" refers to a segment of an enzyme having a root mean square deviation of less than about 1.5 Å in models of related enzymes. For example the model of the *P. tremuloides* isoprene synthase molecule or molecular complex listed in Table 3-7 can be used to identify homologous segments having a root mean square deviation of less than about 1.5 Å in models of related isoprene synthases.

Slight variations in structure coordinates can be generated by mathematically manipulating the isoprene synthase structure coordinates provided herein. For example, the structure coordinates set forth in Table 3-7 or Table 4-2 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Thus, for the purpose of the structures provided herein, any active site, binding site or binding pocket defined by a set of structure coordinates for a polypeptide or for a homolog of a polypeptide from any source having a root mean square deviation of non-hydrogen atoms of less than about 1.5 Å when superimposed on the non-hydrogen atom positions of the corresponding atomic coordinates of Table 3-7 or Table 4-2, are considered substantially identical or homologous.

As used herein, "equivalent or homologous residues" refers to proteins that share particular amino acid residues. Equivalent residues may be identified by determining homology at the level of tertiary structure for a terpene synthase (e.g., isoprene synthase) whose tertiary structure has been determined by x-ray crystallography. Equivalent residues are defined as those for which the atomic coordinates of two (2) or more of the main chain atoms of a particular amino acid residue of the terpene synthase having putative equivalent residues and the substrate of interest (e.g., N on N, CA on CA, C on C and O on O) are within 0.2 nm and preferably 0.15 nm after alignment. Alignment is achieved after the best model has been oriented and positioned to give the maximum overlap of atomic coordinates of non-hydrogen protein atoms of the terpene synthases and substrates analyzed. The preferred model is the crystallographic model giving the lowest R factor for experimental diffraction data at the highest resolution available, determined using methods known to those skilled in the art of crystallography and protein characterization/analysis. For example, equivalent residues which are functionally analogous to a specific residue of isoprene synthase are defined as those amino acids at a structurally homologous synthase which may adopt a conformation such that they either alter, modify, or contribute to protein structure, substrate binding or catalysis in a manner defined or attributed to a specific residue of isoprene synthase.

Isoprene Synthase

Isoprene monomer is employed in the manufacture of polyisoprene and various copolymers (with isobutylene, butadiene, styrene, or other monomers). To build a strain (prokaryotic or eukaryotic) capable of producing commercially viable levels of isoprene requires optimization of the entire pathway, either MVA to isoprene or DXP to isoprene. A key enzyme in the pathway is isoprene synthase (IspS), which converts the precursor DMAPP to isoprene. The only isoprene synthases (IspS) identified to date are those from plants such as poplar, English oak and kudzu vine. Although some bacteria, such as *Bacillus subtilis*, also produce isoprene, a prokaryotic IspS has yet to be identified and the native IspS activity in *Bacillus* is not sufficient for a commercial process. The plant IspS enzymes identified to date have been partially characterized in part by expression in *E. coli* and some of the kinetic parameters of these enzymes have been determined in vitro with purified protein. However, the kinetic parameters ($K_m$, rate, etc.) of the native IspS enzymes are insufficient for commercial production of isoprene in a biological host.

To solve this problem as described herein, an isoprene synthase is expressed in a bacterial host. In addition, the isoprene synthase is engineered for a change in a property of interest. The invention provides a three-dimensional structure which can aid in the design of variants of isoprene synthase and agents with similar three-dimensional structure and/or reaction coordinates to the three-dimensional structure provided herein. These variants and agents are useful for the commercial production of isoprene in a biological host.

Characterization of wild-type and mutant isoprene synthase is accomplished via any means or "test" suitable and is preferably based on the assessment of properties of interest. Properties of interest include but are not limited to: pH optima, temperature stability (e.g., $T_m$ value), intracellular and extracellular solubility, $K_m$ value, $k_{cat}$ value, or specific activity, as well as sensitivity to potential inhibitors including substrate or product inhibition. Oxidative and proteolytic stability are also of interest. Furthermore, activation or inhibition due to metal ion effects and ionic strength is of interest. These properties and parameters can be assessed by the conversion of DMAPP to isoprene in vitro with purified or partially purified isoprene synthase or in vivo in the context of a host organism such as *E. coli* expressing the DXP pathway, the MVA pathway, or both. It is contemplated that enzymes having various degrees of stability, solubility, activity, and/or expression level in one or more of test conditions will find use in the present invention for the production of isoprene in a diversity of hosts.

The invention features compositions and methods for the production of increased amounts of isoprene. In particular, these compositions and methods increase the rate of isoprene production and increase the total amount of isoprene that is produced. The biosynthetic processes for isoprene production described herein are a desirable alternative to using natural rubber. As discussed further below, the amount of isoprene produced by cells can be greatly increased by introducing a heterologous nucleic acid encoding an isoprene synthase (IspS) polypeptide into the cells. Isoprene synthase polypeptides convert dimethylallyl diphosphate (DMAPP) into isoprene.

Additionally isoprene production by cells containing a heterologous isoprene synthase nucleic acid can be enhanced by increasing the amount of a 1-deoxy-D-xylulose-5-phosphate synthase (DXS) polypeptide, and/or an isopentenyl diphosphate isomerase (IDI) polypeptide, expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

The encoded DXS and IDI polypeptides are part of the DXP pathway for the biosynthesis of isoprene (FIG. 1). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount of IPP that is converted into DMAPP, which in turn is converted into isoprene.

In some embodiments, the production of isoprene by cells containing a heterologous isoprene synthase nucleic acid can be augmented by increasing expression of one or more MVA polypeptide(s) in the cells (FIG. 1). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity.

In one embodiment, DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 µl of 1M $MgCl_2$, 1 mM (250 µg/ml) DMAPP, 65 µl of Plant Extract Buffer (PEB) (50 mM Tris-HCl, pH 8.0, 20 mM $MgCl_2$, 5% glycerol, and 2 mM DTT) is added to 25 µl of cell extract in a 20 ml Headspace vial with a metal screw cap and teflon coated silicon septum (Agilent Technologies) and cultured at 37° C. for 15 minutes with shaking. The reaction is quenched by adding 200 µl of 250 mM EDTA or by heat inactivation, and isoprene is quantified by GC/MS.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as variant polypeptides and nucleic acids derived from any of the source organisms described herein.

In some embodiments, the isoprene synthase polypeptide or nucleic acid is from the family Fabaceae, the family Salicaceae, or the family Fagaceae. In some embodiments, the isoprene synthase polypeptide or nucleic acid is a naturally-occurring polypeptide or nucleic acid from *Pueraria montana* (kudzu) (Sharkey et al., Plant Physiology 137: 700-712, 2005), poplar (such as *Populus alba×tremula* CAC35696, Miller et al., Planta 213: 483-487, 2001) or *Populus alba*, aspen (such as *Populus tremuloides*) Silver et al., JBC 270 (22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by GenBank Accession Nos. AY341431, AY316691, AB198180, AJ294819.1, EU693027.1, EF638224.1, AM410988.1, EF147555.1, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is not a naturally-occurring polypeptide or nucleic acid from poplar (such as *Populus alba×tremula* CAC35696).

Three Dimensional Structure and/or Crystallization

Polypeptides, e.g. isoprene synthase, have a three-dimensional structure determined by the primary amino acid sequence and the environment surrounding the polypeptide. This three-dimensional structure establishes the polypeptide's activity, stability, binding affinity, binding specificity, and other biochemical attributes. Thus, knowledge of a protein's three-dimensional structure can provide much guidance in designing improvements to its biological activity; for example, greater catalytic activity and/or solubility.

The three-dimensional structure of a polypeptide can be determined in a number of ways. Many of the most precise methods employ X-ray crystallography (See, e.g., Van Holde, (1971) Physical Biochemistry, Prentice-Hall, New Jersey, pp. 221-39). This technique relies on the ability of crystalline lattices to diffract X-rays or other forms of radiation. Diffraction experiments suitable for determining the three-dimensional structure of macromolecules typically require high-quality crystals. The crystallization properties of a polypeptide vary greatly (Dale, et al., *J. Struct. Biol.* 142:88-97, 2003; MacPherson, A., *Methods* 34:254-265, 2004; and Slabinski, L et al., *Protein Science* 16:2472-2482, 2007). In some cases, polypeptides crystallize readily whereas in other cases, polypeptides have proven extremely difficult to obtain. There is no comprehensive theory to guide efforts to crystallize macromolecules and as a result, most efforts macromolecular crystal growth is empirical in nature (MacPherson, 2004). Factors which can influence the production of crystals including physical, chemical and biochemical factors. These factors include purity of the polypeptide, pH, salt, and concentrations of other precipitants.

Another key variable in the generation of crystals of a polypeptide is the polypeptide itself. Some polypeptides crystallize rather easily while homologous proteins prove to be very difficult to crystallize (Dale et al. 2003). It is generally recognized that rigid, stable proteins are much more likely to crystallize than proteins that are internally flexible or have dynamic surfaces. Solubility is another factor that impacts macromolecular crystallization. Insoluble polypeptides do not readily form crystals because they tend to aggregate. Highly soluble polypeptides, on the other hand, do not readily form crystals because of difficulties in obtaining a supersaturated state. Glycoslyated polypeptides also do not readily form crystals because they tend to be highly soluble. As such, posttranslational modifications can have a large impact on the crystallization of a polypeptide.

Another hurdle in the development of a three-dimensional structure of a polypeptide is the "phase problem." A crystal behaves like a three-dimensional diffraction grating, which gives rise to both constructive and destructive interference effects in the diffraction pattern, such that it appears on the detector as a series of discrete spots which are known as reflections. Each reflection contains information on all atoms in the structure and conversely each atom contributes to the intensity of each reflection. As with all forms of electromagnetic radiation, X-rays have wave properties, in other words, they have both an amplitude and a phase. In order to recombine a diffraction pattern, both of these parameters are required for each reflection. Unfortunately, only the amplitudes can be recorded experimentally and as such, all phase information is lost. One method to solve the "phase problem" is to compare the molecular coordinates with the coordinates of a similar protein by a process called Molecular Replacement.

"Molecular Replacement" refers to the method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the polypeptides comprising the new crystal (Jones et al., 1991, Acta Crystallogr. 47:753-70; Brunger et al., 1998, Acta Crystallogr. D. Biol. Crystallogr. 54:905-21).

The isoprene synthases of plants are expected to be homologous to terpene synthases. Previous efforts to utilize the structure of isoprene synthase in order to improve production of isoprene have relied on the structures of other terpene synthases in which three-dimensional structures are available including bornyl diphosphate synthase and 5-epi-aristolochene synthase (see e.g., U.S. Provisional patent application Ser. No. 12/429,143 and WO 2008/137092).

A set of coordinates determined by X-ray crystallography is not without standard error. In general, the error in the coordinates tends to be reduced as the resolution is increased, since more experimental diffraction data is available for the model fitting and refinement. Thus, for example, more diffraction data can be collected from a crystal that diffracts to a resolution of 3.0 angstroms than from a crystal that diffracts to a lower resolution, such as 3.5 angstroms. Consequently, the refined structural coordinates will usually be more accurate when fitted and refined using data from a crystal that diffracts to higher resolution. If the coordinates are not sufficiently accurate, then the design process will be ineffective. In most cases, it is very difficult or impossible to collect sufficient diffraction data to define atomic coordinates precisely when the crystals diffract to a resolution of only 3.5 angstroms or poorer. Thus, in most cases, it is difficult to use X-ray structures in structure-based ligand design when the X-ray structures are based on crystals that diffract to a resolution of only 3.5 angstroms or poorer. However, common experience has shown that crystals diffracting to 3.0 angstroms or better can yield X-ray structures with sufficient accuracy to greatly facilitate structure-based drug design. Further improvement in the resolution can further facilitate structure-based design, but the coordinates obtained at 3.0 angstroms resolution are generally adequate for most purposes. The three-dimensional structure of isoprene synthase provided by the present invention was resolved to 3.05 angstroms (see Example 3).

Three Dimensional Structure and/or Crystallization of IspS

A number of different constructs expressing different isoprene synthases were generated in order to obtain a three-dimensional structure of the enzyme. One construct contained the kudzu isoprene synthase linked to a fragment of the maltose binding protein (MBP) to facilitate purification. The purified MBD-Kudzu isoprene synthase was subjected to commercially available crystallization screens including Crystal Screen (Hampton Research) and JCSG+ Suite (Qiagen). No fewer than 1536 different conditions were surveyed, including ranges of pH, protein concentration and crystallization reagents. In the majority of cases, the MBP-Kudzu isoprene synthase fusion protein precipitated out of solution and no crystals were obtained.

A second attempt to crystallize isoprene synthase focused on isoprene synthase from *P. alba*. Here the protein was linked to a histidine tag for ease of purification. Over 288 conditions were screened and the nine best crystals were prepared for data collection but the crystals either did not defract or were salt crystals. Likewise, crystals derived from a full-length, untagged *P. alba* isoprene synthase and an N-terminally truncated *P. trichocharpa* isoprene synthase did not diffract.

Crystals were obtained from a construct containing a 19 residue N-terminal truncation of *P. alba* isoprene synthase and linked to a histidine tag. Resolution of the crystal structure was improved from 16 Å to 5 Å. As discussed above, it is preferred that three-dimensional structures are determined in cases where crystal resolution is 3.5 Å or finer. Crystals were obtained from a second N-terminally truncated *P. alba* isoprene synthase following a screen of 528 variations of pH, precipitating agents, concentrations and inhibitors. In order to improve diffraction, various crystal freezing conditions were tested but the diffraction limits only improved from 10 Å to 6.5 Å. Crystallization conditions were further optimized and a crystal resolution of 2.7 Å was obtained.

An isoprene synthase from *P. tremuloides* was generated with an N-terminal truncation and a histidine tag and used in commercially available screens. Rod and plate-like crystals were observed and an additional 120 experiments were performed by varying pH, concentration and crystallization reagents. Here, the best crystal has a resolution of 5 Å. Modification of the freezing conditions resulted in a crystal that diffracted at 3.3 Å and ultimately to 3.05 Å using beamline 11-1 of the Stanford Synchroton Radiation Laboratory.

The phasing problem was resolved by molecular replacement using a monomer of limonene synthase as the starting model. Like isoprene synthase, limonene synthase is terpene synthase which has 41.4% sequence identity to *P. tremuloides* isoprene synthase.

The invention provides a crystalline form of isoprene synthase. In some aspects, the invention provides a crystalline from of *P. tremuloides* isoprene synthase. The crystals belong to the tetragonal space group $P4_32_12$, and have unit cell dimensions a is about 154.2 Å, b is about 154.2 Å, c is about 142.7 Å where $\alpha=\beta=\gamma=90°$. Unit cells dimensions may vary; for example, by 5%. In some aspects, the invention provides a crystalline from of *P. alba* isoprene synthase. The crystals belong to the tetragonal space group $P4_32_12$, and have unit cell dimensions a is about 156.8 Å, b is about 156.8 Å, c is about 142.5 Å where $\alpha=\beta=\gamma=90°$.

The structure is found to be structurally homologous to other known synthase structures specifically bornyl diphosphate synthase, 5-epi-aritolochene synthase and 4S-limonene synthase. All share a common overall tertiary fold, as measured by a lower than 2.0 Angstrom (0.2 nm) standard deviation for a preponderance of the main chain alpha carbon atoms following alignment. Isoprene synthase has 541 amino acid residues, each with one alpha carbon atom: 433 of these can be aligned with those of limonene synthase with a root mean squared deviation (rms) of 0.12 nm; 418 of these can be aligned with those of bornyl diphosphate synthase with an rms of 0.12 nm; and 395 of these can be aligned with those of 5-epi-aristolochene synthase with an rms of 0.14 nm.

The invention provides the three-dimensional structure of the active site of isoprene synthase. The metal ion and phosphate recognition region comprises amino acid residues Arg 255, Asp 292, Asp 296, Glu 370, Arg 433 and Asn436 of the *P. tremuloides* isoprene synthase. As such, the invention provides the site where dimethylallyl pyrophosphate may bind and react with the isoprene synthase to produce isoprene. Side chains of amino acid residues in the *P. tremuloides* IspS that are found in proximity to the metal and diphosphate binding side chains include Asp 293, Tyr 385, Ser 392, and Asp 437.

The invention provides the substrate access loops of isoprene synthase. The substrate access loops of *P. tremuloides* IspS are in regions that deviate from the bornyl diphosphate synthase (BdpS) structure. In the BdpS structure, the residues create a cover over the active site. Upon substrate binding, the structure of *P. tremuloides* IspS may form a similar structure. In the *P. tremuloides* IspS enzyme, residues 440-453, which have the sequence SASAEIARGETANS (SEQ ID NO:40), and residues 512-526, which have the sequence YHNGDAHTSPDEL (SEQ ID NO:41), form the substrate access loops.

The invention provides the three-dimensional structure of the isoprenyl binding site of isoprene synthase. These are residues in the *P. tremuloides* IspS structure that may bind to the product, isoprene. These residues include Ser 261, Trp 264, Phe 285, Thr 289, Ser 393, Ser 394, Phe 432, and Tyr 512.

In some aspects the invention provides the three-dimensional structure of isoprene synthase which further comprises a ligand; for example, dimethylallyl pyrophosphate. In some cases, the three-dimensional structure of isoprene synthase without a ligand is compared to the three-dimensional structure of isoprene synthase with bound ligand. Such comparisons in the three-dimensional structures of isoprene synthase with or without a ligand may reveal structural perturbations in the enzyme following substrate binding. Molecular modeling may provide clues for designing variants of isoprene synthase for improved activity.

The invention provides structurally equivalent agents that mimic the structure of isoprene synthase or a portion thereof. A structurally equivalent agent is related in terms of its three-dimensional structure. In some cases, the structurally equivalent agent mimics the activity (e.g. catalytic activity) of the isoprene synthase or a structurally equivalent portion of the isoprene synthase. For example, a structurally equivalent agent may be structurally analogous to the active site of an isoprene synthase.

Use of Three-Dimensional Structure of Isoprene Synthase

Structure information, typically in the form of the atomic structure coordinates, can be used in a variety of computational or computer-based methods to, for example, design, screen for and/or identify variants of isoprene synthase for improved activity, expression or stability. Three-dimensional modeling may be performed using the experimentally determined coordinates derived from X-ray diffraction patterns, such as those in Table 3-7 and Table 4-2, for example, wherein such modeling includes, but is not limited to, drawing pictures of the actual structures, building physical models of the actual structures, and determining the structures of related subunits and/ligand and subunit/ligand complexes using the coordinates. Such molecular modeling can utilize known X-ray diffraction molecular modeling algorithms or molecular modeling software to generate atomic coordinates corresponding to the three-dimensional structure of an isoprene synthase.

The structure coordinates generated for *P. tremuloides* isoprene synthase or one of its active sites shown in Table 3-7, *P. alba* isoprene synthase or one of its active sites shown in Table 4-2 or the structure coordinates generated by *P. tremuloides* or *P. alba* isoprene synthase/ligand complex define a unique configuration of points in space. Those of skill in the art understand that a set of structure coordinates for protein or an protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

The invention provides methods for increasing the production of isoprene in a host cell by increasing the activity, expression or stability of an isoprene synthase in the host cell. Based on the three-dimensional structure of isoprene synthase, one of skill in the art can use computational methods to modify properties of the isoprene synthase including but not limited to pH optima, $K_M$ value, $k_{cat}$ value, and specific activity of the enzyme. In other aspects of the invention, the three-dimensional structure of isoprene synthase or agents with similar three-dimensional structures may be used as a guide to improve oxidative and/or proteolytic stability of isoprene synthase. The three-dimensional structure of isoprene synthase may be used to evaluate inhibitors of its enzymatic activity including, but not limited to, substrate and product inhibition. In other aspects of the invention, the three dimensional structure may be used to design isoprene synthase variants agents with similar three-dimensional structures for increased expression; for example, by making amino acid substitutions in the isoprene synthase protein which do not alter the three dimensional structure of the protein but allow more favorable expression for a given host cell.

In some aspects of the invention, a portion of the three dimensional structure of isoprene synthase may be used as a guide to design isoprene synthase variants or to design agents that mimic at least a portion of the isoprene synthase. As such, the invention provides a three dimensional configuration of points of a portion of the points shown in Table 3-7 or Table 4-2 or Table 8-2. Examples of portions of isoprene synthase include, but are not limited to, an active site, a diphosphate/metal binding site, an isoprenyl binding site, a flexible loop, a hinge region, and an electrostatic patch region.

In some aspects, the invention provides a three dimensional configuration of points that are analogous to the three dimensional configuration of points shown in Table 3-7 or Table 4-2 or Table 8-2 or a portion thereof. Analogous three dimensional configuration of points are at least 50%, 55%, 60%, 65%, 70%, 75%, 80%, 85%, 90%, 95%, or 100% identical to the three dimensional configuration of points shown in Table 3-7 or Table 4-2 or a portion thereof, such as an active site, a diphosphate/metal binding site, an isoprenyl binding site, a flexible loop, a hinge region or an electrostatic patch region.

The three-dimensional structures of *P. tremuloides* IspS provide the identification of sites in the *P. tremuloides* IspS and other poplar isoprene synthases (e.g. *P. alba* IspS) that are candidates for mutagenesis to produce variant isoprene synthase enzymes with improved performance. The present invention provides sites isoprene synthase that might alter the interaction of the metal binding, diphosphate recognition, DMAPP chain binding, isoprenyl binding and/or the approach to the active site. Variants of isoprene synthase are designed for greater production of isoprene in host cells.

In some aspects, the invention provides methods of developing variants of isoprene synthase with improved enzyme kinetics. Improved enzyme kinetics can be determined by enzymatic assays. An increase in $k_{cat}$ and/or a decrease in $K_i$ or $K_M$ compared to wild type isoprene synthase indicated an increase in the specific activity of the variant.

It is to be understood the disclosure herein for generating variants using three dimensional structure of isoprene synthase are equally applicable to other enzymes having substantially the same three-dimensional structure. This can refers to a polypeptide that is characterized by a set of atomic structure coordinates that have a root mean square deviation (r.m.s.d.) of less than or equal to about 1.5 Å when superimposed onto the atomic structure coordinates of an isoprene synthase, e.g. the atomic structure coordinates of Table 3-7 or Table 4-2 or Table 8-2 when at least about 50% to 100% of the Cα atoms of the coordinates are included in the superposition.

The invention also contemplates generating variants using homologous segments to the three dimensional structure of the isoprene synthases disclosed herein. This can refer to a segment of an enzyme having a root mean square deviation of less than about 1.5 Å in models of related enzymes. For example the model of the *P. tremuloides* isoprene synthase molecule or molecular complex listed in Table 3-7, Table 4-2 or Table 8-2 can be used to identify homologous segments having a root mean square deviation of less than about 1.5 Å in models of related isoprene synthases.

Slight variations in structure coordinates can be generated by mathematically manipulating the isoprene synthase structure coordinates provided herein. For example, the structure coordinates set forth in Table 3-7 or Table 4-2 or Table 8-2 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Thus, for the purpose of the structures provided herein, any active site, binding site or binding pocket defined by a set of structure coordinates for a polypeptide or for a homolog of a polypeptide from any source having a root mean square deviation of non-hydrogen atoms of less than about 1.5 Å when superimposed on the non-hydrogen atom positions of the corresponding atomic coordinates of Table 3-7 or Table 4-2 or Table 8-2, are considered substantially identical or homologous. As such, all variants with equivalent or homologous residues are contemplated within the scope of this invention, regardless if it is has the same amino acid(s) or a different amino acid(s).

As described above, the present invention provides the three-dimensional structure of the active site (diphosphate/metal binding site) of isoprene synthase. The active site includes amino acid residues Arg 255, Asp 292, Asp 296, Glu 370, Arg 433 and Asn436 if *P. tremuloides* isoprene synthase. In addition, based on the three-dimensional structure of *P. tremuloides* isoprene synthase, the side chains of amino acid residues found in proximity to the diphosphate/metal binding site were identified. These residues include, but are not limited to, Asp 293, Tyr 385, Ser 392, and Asp 437 of *P. tremuloides* isoprene synthase. Engineering of these sites may result in increased enzyme activity. In some cases, mutation in an active site residue may decrease or completely abolish the activity of the isoprene synthase.

The three-dimensional structure of isoprene synthase may also be used to identify residues that bind the substrate of isoprene synthase, e.g. DMAPP. The residues may be used as a basis to generate isoprene synthase variants that may be used modulate substrate specificity and/or reaction rates (altered on and off rates of substrate and product). These residues include, but are not limited to, Ser 261, Trp 264, Phe 285, Thr 289, Ser 393, Ser 394, Phe 432, and Try 512 of *P. tremuloides* isoprene synthase.

The three dimensional structure of isoprene synthase has revealed that several loops forming the active site are flexible. One may exploit the flexibility to enhance enzyme performance by making substitutions in the amino aids forming these segments to facilitate the transitions the enzyme must undergo in the steps of binding substrate and allowing rearrangement of substrate in different kinetic steps that are postulated to occur during enzymatic de-phosphorylation and for electron transfer to convert DMAPP to isoprene. Three segments have been identified that form a considerable portion of the substrate binding pocket, notably the truncated N-terminus, along with two loops comprised of residues 438-453 (Loop I) and residues 512-527 (Loop II) (FIGS. 33-36). These loops may be present in at least two conformations: the "open" form in the absence of substrate and a "closed," or active form when the substrate is bound. These residues provide targets for the generation of isoprene synthase variants with improved activity. For example, the residues in these loops of *P. tremuloides* isoprene synthase, including residues 440-453 (SASAEIARGETANS (SEQ ID NO:40)) and 512-524 (YHNGDAHTSPDEL (SEQ ID NO:41)), may be in a position to alter the activity of the isoprene synthase.

The flexible loop residues of isoprene synthase can be targets for Site Evaluation Library analysis. A library can be generated such that a particular amino acid residue(s) are mutated to different amino acid substitutions and then tested for activity (e.g. DMAPP activity) in an appropriate host cell. As exemplified in Example 5 below, residues A443, A453, N545, H515, A519 and E525 of the P. alba IspS (SEQ ID NO:41) were mutated and analyzed for DMAPP activity. P. alba IspS variants with improved activity identified by this analysis include, but are not limited to, A453N, H515M, A453I and A443S. Thus, other mutations in the flexible loop or mutations that affect the flexible loop can be found that increase isoprene synthase activity in the manner described herein. For example, conservative substitutions can be made that result in an increase in isoprene synthase activity.

The three-dimensional structure of isoprene synthase has revealed amino acids on the surface of the enzyme. For example, surface hydrophobic residues may affect protein folding, solubility or activity. In order to enhance the solubility of isoprene synthase, hydrophobic surface residues may be mutated to reduce the tendency of the enzyme to aggregate. In some cases, hydrophobic surface residues may be mutated to neutral of hydrophilic residues to increase the solubility and/or decrease the aggregation of isoprene synthase molecules. One skilled in the art would recognize hydrophobic residues, neutral residues and hydrophilic residues. Examples of surface hydrophobic residues include but are not limited to I28, V30, L130, G153, V299, L303, L469 and L494 of the P. alba IspS (SEQ ID NO:41). P. alba IspS variants with improved activity include, but are not limited to, L494P, L494C, L494V, L494G, L494I and L469A. Thus, other mutations in the surface hydrophobic residues can be found that increase isoprene synthase activity in the manner described herein. For example, conservative substitutions can be made that result in an increase in isoprene synthase activity. It is to be understood that all descriptions of mutations and/or substitutions herein refer to one mutation by itself or a combination (e.g., 2, 3, 4, 5, or more) of mutations. For example, an isoprene synthase variant with L494P is contemplated as well as an isoprene synthase variant with L494P and T536F.

The three dimensional structure of isoprene synthase has a "hinge region" located in a helix that spans the N-terminus and the C-terminus. In one aspect, the three dimensional structure of isoprene synthase has a "hinge region" located in a helix that spans the N-terminus and the C-terminus of the protein monomer. Without being bound by theory, the hinge region may dictate how these two halves of the enzyme may interact with each other. The hinge region includes residues 216-244. Examples of amino acid residues in the hinge region or that may interact with the hinge region include, but are not limited to, R198, I229 and L260 of the P. alba IspS (SEQ ID NO:41). Variants in the hinge region with improved activity include, but are not limited to, I229C, I229T, I229P, I229N, L260N, L260M, and L260I. Thus, other mutations in the hinge residues can be found that increase isoprene synthase activity in the manner described herein. For example, conservative substitutions can be made that result in an increase in isoprene synthase activity.

An electrostatic patch was identified by the three dimensional structure of isoprene synthase by the presence of a high density of acidic residues. Residues in the electrostatic patch include D304, E307, D311, E314 and D323. Without being bound by theory, this region may regulate activity of isoprene synthase. Examples of amino acid residues in the electrostatic patch include but are not limited to D311 and D323 of the P. alba IspS (SEQ ID NO:41). Variants with improved activity include, but are not limited to, D311M, D311F, D311L, D311G, D311I, D311A, D311T, D311R, D311V, D311E, D323W, D323Y, D323F, D323I, D323S, D323V, D323A, D323G, and D323Q. Thus, other mutations in the electrostatic patch residues or that affect the electrostatic patch can be found that increase isoprene synthase activity in the manner described herein. For example, conservative substitutions can be made that result in an increase in isoprene synthase activity.

Analysis of the three dimensional structure of isoprene synthase revealed other regions for targeting variants. For example, variants may be targeted to loop regions of the protein which can absorb structural perturbations to a greater extent than helices. As described in Example 5, residues D345, R528 and T536 of P. alba IspS (SEQ ID NO:41) were targets for SEL analysis. Without being bound by theory, D345 may be involved in dimerization of isoprene synthase. R528 adjacent to the flexible loop described above. Residue T536 is located at the C-terminal residue of the last helix on the C-terminal end of isoprene synthase. Variants with improved isoprene synthase activity include, but are not limited to, T536C, T536I, T536F, T536Y, T536A, T536K, T536L, T536R, T536V and T536M.

In some aspects of the invention, the variant isoprene synthase does not contain mutations at homologous residues corresponding to one or more of the following residues in kudzu isoprene synthase: A20, N21, Y22, Q23, P24, N25, L26, E30, F31, Q33, L35, E36, N37, L39, K40, V41, K43, L44, C57, R61, V62, D63, Q65, K87, E94, N95, L99, D100, N105, K137, E138, G143, E144, N182, L184, K185, G187, N189, T190, P225, H226, K247, T257, E258, M259, D266, R271, W278, C291, F299, V302, Y309, D310, N334, D353, S357, I3581, E361, L377, F381, E384, N389, I392, I393, K398, Y399, E401, N402, A403, S406, S407, S408, G409, A411, L413, C421, Q423, Q424, E425, D426, H430, L432, R433, S434, D437, R443, C446, F449, A456, T457, S458, A459, A460, E461, L462, E463, R464, G465, E466, T467, T468, N469, H476, N478, D479, Q485, D508, P513, A515, M523, S527, Y531, Q532, Y533, L537, G538, R539, Y542, A543, and P557 (based on FIG. 37; SEQ ID NO:42).

In other aspects of the invention, the variant isoprene synthase does not contain mutations at homologous residues corresponding to one or more of the following residues in P. alba v tremuloides isoprene synthase: K272, R274, W281, F302, V305, Y312, D313, L380, F384, E387, Y402, N404, A406, S409, S410, S411, G412, L414, Q415, L416, F449, N453, L454, A455, S456, A457, S4548, A459, E460, I461, A462, R463, G464, E465, T466, N469, C497, L521, S525, S537, E540, and residues 22 to 27 (based on FIG. 38; SEQ ID NO:43).

In other aspects of the invention, the variant isoprene synthase does not contain mutations at homologous residues corresponding to one or more of the following mutations in P. alba isoprene synthase: V10M, F125, T15A, E18G, V58I, V58F, L70Q, L70V, L70T, T71P, V79L, E89D, G94A, S119F, F120L, G127R, E175V, T212I, S257A, R262G, A266G, F280L, N297K, F305L, L319M, E323K, A328T, D342E, A359T, K366N, E368D, L374M, S396T, V4185, K438N, H440R, T442I, T442A, I449V, A469S, K500R, K505Q, G507S, S509N, F511Y, and N532K (based on SEQ ID NO:16).

In some aspects of the invention, the variant isoprene synthase does not contain combinations of mutations at homologous residues corresponding to one or more of the following combination mutations in a single P. alba isoprene synthase: G127R/F511Y, L70Q/G94A/R262G/F305L, F12S/T15A/E18G/N297K, S396T/T442I, V10M/E323K, F120L/A266G, K438N/K500R, V79L/S509N, E175V/S257A/E368D/

A469S, T71P/L374M, F280L/H440R, E89D/H440R, V58F/A328T/N532K, S119F/D342E/I449V, and K366N/G507S (based on SEQ ID NO:16).

It has been shown that mutating amino-acid residues on the surface of protease enzymes can improve their activity, expression, and stability (WO2008/153925, WO2008/153934, WO2008/153935). Surprisingly, we have found that mutating amino-acid residues on the surface of a completely different enzyme, isoprene synthase, can enhance its expression, solubility, and activity. L70R is an example of such a beneficial surface mutation.

Elucidation of the three-dimensional structure of an enzyme is essential for accurately identifying amino-acid residues on its surface. Homology modeling using structures with sequences approximately 40% identical to isoprene synthase (e.g., bornyl synthase and limonene synthase, the enzymes of known structure with closest identity to isoprene synthase) can reveal gross aspects of the modeled enzyme structure, but is insufficient to precisely identify surface-exposed residues and quantify their degree of surface exposure. Surface exposure of an amino-acid residue is quantified by the percentage of solvent-accessible surface area of its side chain.

The following classes of mutations in isoprene synthase may improve solubility of the enzyme by targeting amino-acid residues that are about >50% solvent-exposed, in some cases about >65% solvent-exposed, and in other cases >85% solvent-exposed:

Hydrophobic→positively charged, and vice versa
Hydrophobic→negatively charged, and vice versa
Hydrophobic→neutral polar, and vice versa
Neutral polar→positively charged, and vice versa
Neutral polar→negatively charged, and vice versa
Positively charged→negatively charged, and vice versa These classes of mutations may also be used to improve the activity, substrate stability, dimerization of isoprene synthase.

The three-dimensional structure of isoprene synthase reveals the structural reaction coordinates of isoprene synthesis. As such, the invention provides a three-dimensional configuration of atoms involved in the catalytic conversion of DMAPP to isoprene. In some aspects, the invention provides an agent comprising a three-dimensional configuration of atoms for the catalytic conversion of DMAPP to isoprene. Example of agents include, but are not limited to, synthetic molecules including synthetic polypeptides as well as re-engineered polypeptides. For example, other members of the terpene synthase family may be altered to comprise the three-dimensional configuration of atoms for the catalytic conversion of DMAPP to isoprene.

Machine Readable Storage Media

Transformation of the structure coordinates for all or a portion of *P. tremuloides* isoprene synthase or an isoprene synthase/ligand complex or one of its active sites, for structurally homologous molecules, or for the structural equivalents of any of these molecules or molecular complexes as defined above, into three-dimensional graphical representations of the molecule or complex can be conveniently achieved through the use of commercially-available software.

The invention thus further provides a machine-readable storage medium including a data storage material encoded with machine readable data which, when using a machine programmed with instructions for using said data, displays a graphical three-dimensional representation of any of the molecule or molecular complexes of this invention that have been described above. In a preferred embodiment, the machine-readable data storage medium includes a data storage material encoded with machine readable data which, when using a machine programmed with instructions for using said data, displays a graphical three-dimensional representation of a molecule or molecular complex including all or any parts of a *P. tremuloides* isoprene synthase active site or a *P. tremuloides*-like active site; for example from a poplar isoprene synthase including but not limited to *P. alba* isoprene synthase, as defined above. In another aspect, the machine-readable data storage medium displays a graphical three-dimensional representation of a molecule or molecular complex defined by the structure coordinates of all of the amino acids in Table 3-7, ± a root mean square deviation from the backbone atoms of said amino acids of not more than 1.5 Å. In another aspect, the machine-readable data storage medium displays a graphical three-dimensional representation of a molecule or molecular complex defined by the structure coordinates of all of the amino acids in Table 4-2, ± a root mean square deviation from the backbone atoms of said amino acids of not more than 1.5 Å.

In an alternative aspect of the invention, the machine-readable data storage medium includes a data storage material encoded with a first set of machine readable data which includes the Fourier transform of the structure coordinates set forth in Table 3-7 or 4-2, and which, when using a machine programmed with instructions for using said data, can be combined with a second set of machine readable data including the x-ray diffraction pattern of a molecule or molecular complex to determine at least a portion of the structure coordinates corresponding to the second set of machine readable data.

For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

Isoprene Synthase Variants, Agents with Similar 3-D Structures, and their Use

Compositions and methods to make and use variants derived from the three-dimensional structure of isoprene synthase and agents with similar three-dimensional structure to isoprene synthase are provided herein.

The invention provides methods to generate and test candidate variants of isoprene synthesis based on an evaluation of the three-dimensional structure of the protein. Candidate residues for alteration are derived by a computational analysis of the three-dimensional structure with regard to one or more desired characteristics of the variant; for example, increased specific activity, increased stability, increased expression and the like. Candidate variants may then be generated using standard molecular biology techniques. Variants can be assessed based on the desired outcome. For example, a variant isoprene synthase engineered for increased specific activity can be tested for the conversion of DMAPP to isoprene in vitro with purified or partially purified variant isoprene synthase or in vivo in the context of a host organism such as *E. coli*. In some cases, the *E. coli* may also express the DXP pathway, the MVA pathway, or both. Improved activity is assessed in comparison with other isoprene synthases; for example, a wild type isoprene synthase. It is contemplated that enzymes having various degrees of stability, solubility, activity, and/or expression level in one or more of test conditions will find use in the present invention for the production of isoprene in a diversity of hosts. High throughput methods may provide an investigation of these properties in an economical manner.

The invention provides compositions and methods for the production of increased amounts of isoprene. In particular, these compositions and methods increase the rate of isoprene production and increase the total amount of isoprene that is produced. In some aspects of the invention, the amount of isoprene produced by cells may be increased by introducing a heterologous nucleic acid encoding a variant isoprene synthase polypeptide into the cells.

Exemplary Polypeptides and Nucleic Acids

Various isoprene synthase polypeptides and nucleic acids can be used in the compositions and methods of the invention. As used herein, "polypeptides" includes polypeptides, proteins, peptides, fragments of polypeptides, and fusion polypeptides that include part or all of a first polypeptide (e.g., an isoprene synthase) and part or all of a second polypeptide (e.g., a peptide that facilitates purification or detection of the fusion polypeptide, such as a His-tag). In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, 100% or greater than 100% of an activity of a corresponding full-length polypeptide. In particular embodiments, the polypeptide includes a segment of or the entire amino acid sequence of any naturally-occurring isoprene synthase. In some embodiments, the polypeptide has one or more mutations compared to the sequence of a wild-type (i.e., a sequence occurring in nature) isoprene synthase.

In some embodiments, the polypeptide is a heterologous polypeptide. By "heterologous polypeptide" is meant a polypeptide whose amino acid sequence is not identical to that of another polypeptide naturally expressed in the same host cell.

In various embodiments, the nucleic acid is a recombinant nucleic acid. For instance, in some embodiments, an isoprene synthase nucleic acid is operably linked to another nucleic acid encoding all or a portion of another polypeptide such that the recombinant nucleic acid encodes a fusion polypeptide that includes an isoprene synthase and all or part of another polypeptide (e.g., a peptide that facilitates purification or detection of the fusion polypeptide, such as a His-tag). In some embodiments, part or all of a recombinant nucleic acid is chemically synthesized. In some aspects, the nucleic acid is a heterologous nucleic acid. By "heterologous nucleic acid" is meant a nucleic acid whose nucleic acid sequence is not identical to that of another nucleic acid naturally found in the same host cell.

In particular embodiments the nucleic acid includes a segment of or the entire nucleic acid sequence of any naturally-occurring isoprene synthase nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid. In some aspects, the nucleic acid has one or more mutations compared to the sequence of a wild-type (i.e., a sequence occurring in nature) isoprene synthase nucleic acid. In some embodiments, the nucleic acid has one or more mutations (e.g., a silent mutation) that increase the transcription or translation of isoprene synthase nucleic acid. In some embodiments, the nucleic acid is a degenerate variant of any nucleic acid encoding an isoprene synthase polypeptide.

An isoprene synthase nucleic acid can be incorporated into a vector, such as an expression vector, using standard techniques (Sambrook et al., Molecular Cloning: A Laboratory Manual, Cold Spring Harbor, 2001, which is hereby incorporated by reference in its entirety, particularly with respect to the screening of appropriate DNA sequences and the construction of vectors). Methods used to ligate the DNA construct comprising a nucleic acid of interest such as isoprene synthase, a promoter, a terminator, and other sequences and to insert them into a suitable vector are well known in the art. Additionally, vectors can be constructed using known recombination techniques (e.g., Invitrogen Life Technologies, Gateway Technology).

In some embodiments, it may be desirable to over-express isoprene synthase nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, 2nd ed., Cold Spring Harbor, 2001, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990; and Ausubel et al., Eds. Current Protocols in Molecular Biology, 1994, which are each hereby incorporated by reference in their entireties, particularly with respect to molecular biology and cloning techniques.

Exemplary Host Cells

A variety of host cells can be used to express isoprene synthase and to produce isoprene in the methods of the claimed invention. The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Other exemplary host cells that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Transformation Methods

Isoprene synthase, DXS, IDI, and/or MVA pathway nucleic acids or vectors containing them can be inserted into a host cell (e.g., a bacterial cell) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, 3rd ed., Cold Spring Harbor, 2001; and Campbell et al., Curr Genet, 16:53-56, 1989, which are each hereby incorporated by reference in their entireties, particularly with respect to transformation methods). The introduced nucleic acids may be integrated into chromosomal DNA or maintained as extrachromosomal replicating sequences.

Other exemplary transformation methods that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Cell Culture Media

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharides), invert sugar (e.g., enzymatically treated sucrose syrup), glycerol, glycerine (e.g., a glycerine byproduct of a biodiesel or soap-making process), dihydroxyacetone, one-carbon source, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source; beet sugar or cane sugar molasses), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria.

In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary fatty acids include compounds of the formula R—COOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more C12-C22 fatty acids, such as a C12 saturated fatty acid, a C14 saturated fatty acid, a C16 saturated fatty acid, a C18 saturated fatty acid, a C20 saturated fatty acid, or a C22 saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, fatty acid, monoglyceride, diglyceride, or triglyceride that is added before and/or during the culturing of the host cells. In some embodiments, the carbon source includes both (i) a lipid, fatty acid, monoglyceride, diglyceride, or triglyceride and (ii) a carbohydrate, such as glucose. In some embodiments, the ratio of the lipid, fatty acid, monoglyceride, diglyceride, or triglyceride to the carbohydrate is about 1:1 on a carbon basis (i.e., one carbon in the lipid, fatty acid, monoglyceride, diglyceride, or triglyceride per carbohydrate carbon). In particular embodiments, the amount of the lipid, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., Bioresource Technology 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., Bioresource Technology 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry-to-dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., Agric. Biol. Chem., 53(2) 541-543, 1989, which is hereby incorporated by reference in its entirety, particularly with respect to carbon sources) and in bacteria (Hunter et. al., Biochemistry, 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, Bacterial Metabolism, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth $C_1$-Compd., Int. Symp., 7th ed., 415-32. Editors: Murrell et al., Publisher: Intercept, Andover, UK, 1993, which is hereby incorporated by reference in its entirety, particularly with respect to carbon sources). Similarly, various species of Candida metabolize alanine or oleic acid (Sulter et al., Arch. Microbiol. 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988; and Ilmen et al., Appl. Environ. Microbiol. 63:1298-1306, 1997, hereby incorporated by reference, particularly with respect to cell media). Exemplary growth media are common commercially prepared media such as Luria Bertani (LB) broth, Sabouraud Dextrose (SD) broth, or Yeast medium (YM) broth. One skilled in the art of microbiology or fermentation science would know other defined or synthetic growth media that may also be used, and the appropriate medium for growth of particular host cells.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect to cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Other exemplary cell culture media that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Production of Isoprene

In some embodiments, the cells are cultured in a culture medium under conditions permitting the production of isoprene by the cells. In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/gwcm/hr). In some embodiments, the amount of isoprene is between about 2 to about 5,000 nmole/gwcm/hr, such as between about 2 to about 100 nmole/gwcm/hr, about 100 to about 500 nmole/gwcm/hr, about 150 to about 500 nmole/gwcm/hr, about 500 to about 1,000 nmole/gwcm/hr, about 1,000 to about 2,000 nmole/gwcm/hr, or about 2,000 to about 5,000 nmole/gwcm/hr. The amount of isoprene in units of nmole/gwcm/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, e.g., Greenberg et al, Atmos. Environ. 27A: 2689-2692, 1993; Silver et al., Plant Physiol. 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/gwcm/h). In some embodiments, the amount of isoprene is between about 2 to about 5,000 ng/gwcm/h, such as between about 2 to about 100 ng/gwcm/h, about 100 to about 500 ng/gwcm/h, about 500 to about 1,000 ng/gwcm/h, about 1,000 to about 2,000 ng/gwcm/h, or about 2,000 to about 5,000 ng/gwcm/h. The amount of isoprene in ng/gwcm/h can be calculated by multiplying the value for isoprene production in the units of nmole/gwcm/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/L broth, wherein the volume of broth includes the volume of the cells and the cell medium). In some embodiments, the amount of isoprene is between about 2 to about 5,000 mg/L broth, such as between about 2 to about 100 mg/L broth, about 100 to about 500 mg/L broth, about 500 to about 1,000 mg/L broth, about 1,000 to about 2,000 mg/L broth, or about 2,000 to about 5,000 mg/L broth. The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace. If the $OD_{600}$ value is not 1.0, then the measurement can be normalized to an $OD_{600}$ value of 1.0 by dividing by the $OD_{600}$ value. The value of mg isoprene/L headspace can be converted to mg/Lbroth/hr/$OD_{600}$ of culture broth by multiplying by a factor of 38. The value in units of mg/Lbroth/hr/$OD_{600}$ can be multiplied by the number of hours and the $OD_{600}$ value to obtain the cumulative titer in units of mg of isoprene/L of broth.

The instantaneous isoprene production rate in mg/L broth/hr in a fermentor can be measured by taking a sample of the fermentor off-gas, analyzing it for the amount of isoprene (in units such as mg of isoprene per L of gas), and multiplying this value by the rate at which off-gas is passed though each liter of broth (e.g., at 1 vvm (volume of air/volume of broth/minute) this is 60 Lgas per hour). Thus, an off-gas level of 1 mg/Lgas corresponds to an instantaneous production rate of 60 mg/Lbroth/hr at air flow of 1 vvm. If desired, the value in the units mg/Lbroth/hr can be divided by the $OD_{600}$ value to obtain the specific rate in units of mg/Lbroth/hr/OD. The average value of mg isoprene/Lgas can be converted to the total product productivity (grams of isoprene per liter of fermentation broth, mg/Lbroth) by multiplying this average off-gas isoprene concentration by the total amount of off-gas sparged per liter of fermentation broth during the fermentation. Thus, an average off-gas isoprene concentration of 0.5 mg/Lbroth/hr over 10 hours at 1 vvm corresponds to a total product concentration of 300 mg isoprene/Lbroth.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, or 1.6% of the carbon in the cell culture medium into isoprene. In some embodiments, the percent conversion of carbon into isoprene is between about 0.002 to about 1.6%, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

% Carbon Yield=(moles carbon in isoprene produced)/(moles carbon in carbon source)*100  Equation 1

For this calculation, yeast extract can be assumed to contain 50% w/w carbon.

% Carbon Yield=(39.1 g isoprene*1/68.1 mol/g*5 C/mol)/[(181221 g glucose*1/180 mol/g*6 C/mol)+(17780 g yeast extract*0.5*1/12 mol/g)]*100=0.042%  Equation 2

One skilled in the art can readily convert the rates of isoprene production or amount of isoprene produced into any other units. Exemplary equations are listed below for interconverting between units.

Units for Rate of Isoprene Production (Total and Specific)

1 g isoprene/$L_{broth}$/hr=14.7 mmol isoprene/$L_{broth}$/hr (total volumetric rate)  Equation 3

1 nmol isoprene/$g_{wcm}$/hr=1 nmol isoprene/$L_{broth}$/hr/$OD_{600}$(This conversion assumes that one liter of broth with an $OD_{600}$ value of 1 has a wet cell weight of 1 gram.)  Equation 4

1 nmol isoprene/$g_{wcm}$/hr=68.1 ng isoprene/$g_{wcm}$/hr (given the molecular weight of isoprene)  Equation 5

1 nmol isoprene/$L_{gas}O_2$/hr=90 nmol isoprene/$L_{broth}$/hr (at an $O_2$ flow rate of 90 L/hr per L of culture broth)  Equation 6

1 µg isoprene/$L_{gas}$ isoprene in off-gas=60 µg isoprene/$L_{broth}$/hr at a flow rate of 60 $L_{gas}$ per $L_{broth}$ (1 vvm)  Equation 7

Units for Titer (Total and Specific)

1 nmol isoprene/mg cell protein=150 nmol isoprene/$L_{broth}$/$OD_{600}$(This conversion assumes that one liter of broth with an $OD_{600}$ value of 1 has a total cell protein of approximately 150 mg)(specific productivity)  Equation 8

1 g isoprene/$L_{broth}$=14.7 mmol isoprene/$L_{broth}$(total titer)  Equation 9

If desired, Equation 10 can be used to convert any of the units that include the wet weight of the cells into the corresponding units that include the dry weight of the cells.

Dry weight of cells=(wet weight of cells)/3.3  Equation 10

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques, such as gas stripping, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. See, e.g. U.S. Patent Application Publication No. 2009/0203102, PCT publication WO 2009/076676 and U.S. patent application Ser. No. 12/496,573. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. It is also to be understood that one, some, or all of the properties of the various embodiments described herein may be combined to form other embodiments of the present invention. These and other aspects of the invention will become apparent to one of skill in the art.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Construction of MBD Kudzu IspS

This example describes construction of a vector expressing a maltose-binding protein-kudzu isoprene synthase fusion molecule.

I. Construction of pTrcKudzu

Figure 2:
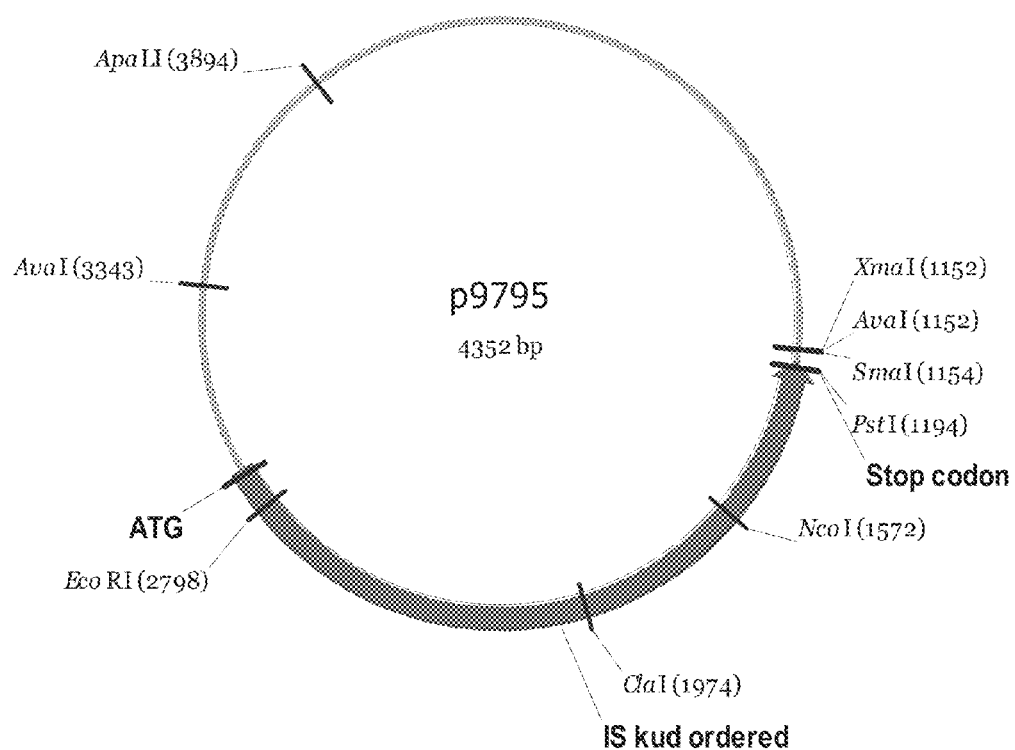
FIG. 2 provides a map of plasmid p9795.
Figure 4:
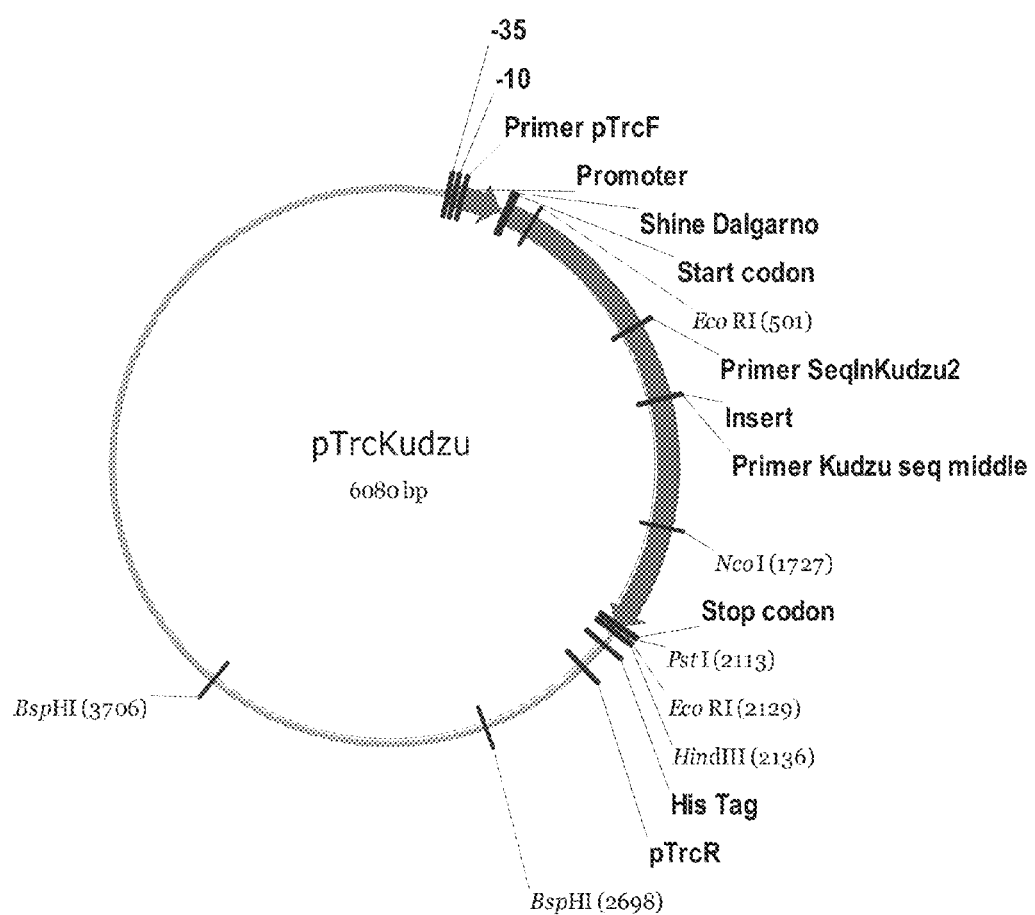
FIG. 4 provides a map of plasmid pTrcKudzu.

A synthetic gene, coding for isoprene synthase (IspS) of the kudzu vine (*Pueraria lobata*) and codon-optimized for *E. coli*, was purchased from DNA2.0 (Menlo Park, Calif.) and provided as plasmid p9795 (FIGS. 2 and 3). The Insert was been removed by digestion with BspLU11I/PstI, gel-purified, and religated into NcoI/PstI-digested pTrcHis2B (Invitrogen, Carlsbad, Calif.). The resulting plasmid was named pTrcKudzu (FIGS. 4 and 5). The stop codon in the insert is before the PstI site, which results in a construct in which the His-Tag is not attached to the IspS protein.

II. Construction of Plasmid pMAL-C4X Kudzu

A PCR reaction was performed to amplify the *E. coli* codon-optimized kudzu gene using plasmid pTrcKudzu as the DNA template, primers EL-959 and EL-960 Table 1-1, 10 mM dNTP (Roche, Indianapolis, Ind.), and Pfu Ultra II Fusion DNA polymerase (Stratagene, La Jolla, Calif.) according to manufacturer's protocol. PCR conditions were as follows: 95° C. for 2 min (first cycle only), 95° C. for 25 sec, 60° C. for 25 sec, 72° C. for 30 sec, and repeat for 28 cycles, with final extension at 72° C. for 1 min. The PCR product was then purified using the QIAquick PCR Purification Kit (Qiagen Inc, Valencia, Calif.).

Figure 6:
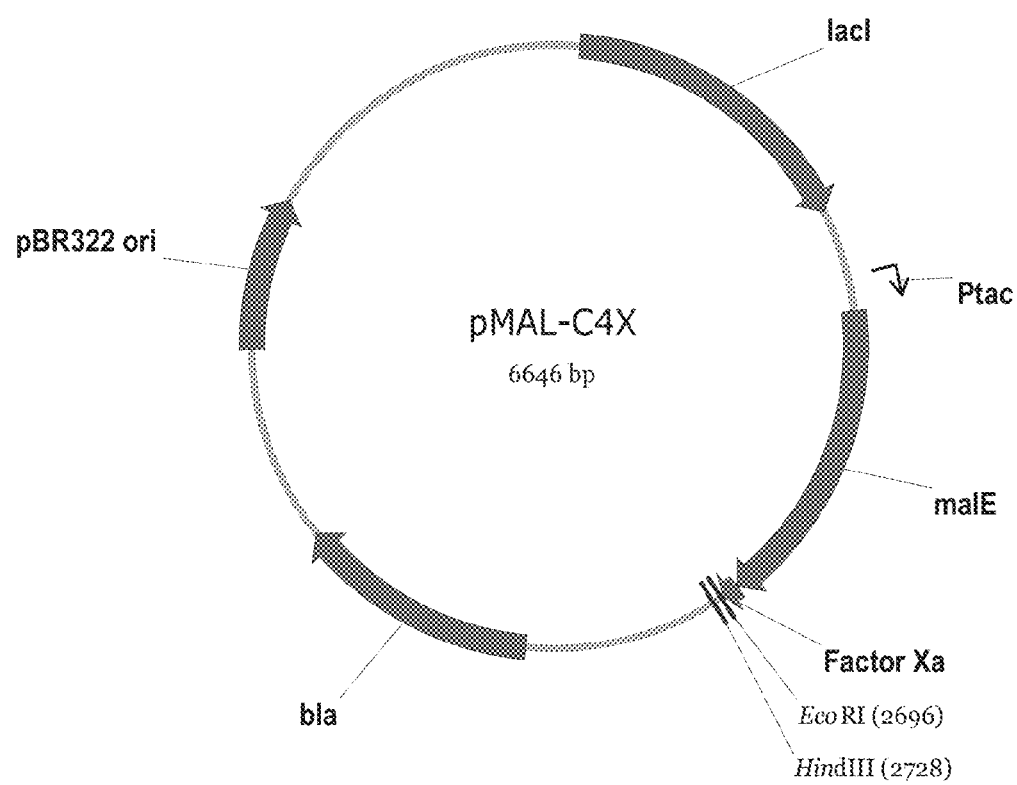
FIG. 6 provides a map of plasmid pMAL-C4X.

The kudzu PCR product (1 µg) was digested using EcoRI and HindIII restriction endonucleases (Roche) according to manufacturer's protocol. The digest was incubated 37° C. for 30 minutes to minimize digestion of the internal EcoRI site that is present in the kudzu gene. The digested PCR fragment was then purified using the QIAquick PCR Purification Kit. The vector pMAL-C4X (0.5 µg) (New England Biolabs, Ipswich, Mass.; FIGS. 6 and 7) was digested using EcoRI and HindIII restriction endonucleases (Roche) according to manufacturer's protocol. The digested vector was then gel purified using the QIAquick Gel Extraction Kit (Qiagen Inc). A DNA ligation reaction was performed using T4 DNA ligase (New England Biolabs) with a 5:1 ratio of digested kudzu PCR product to digested pMAL-C4X vector according to manufacturer's protocol. An aliquot of the ligation reaction was then transformed into TOP10 chemically competent cells (Invitrogen Corp). Transformants were selected on LA+50 μg/μl carbenicillin plates.

Figure 8:
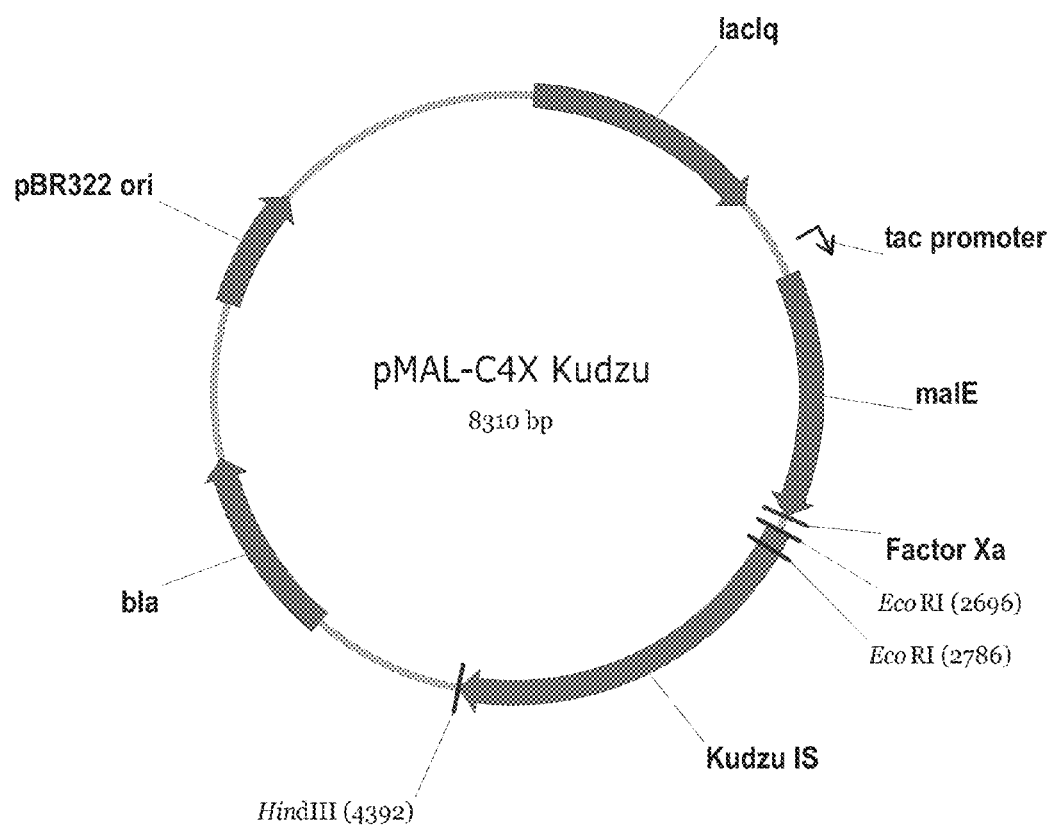
FIG. 8 provides a map of plasmid pMAL-C4X-Kudzu.
Figure 15C:
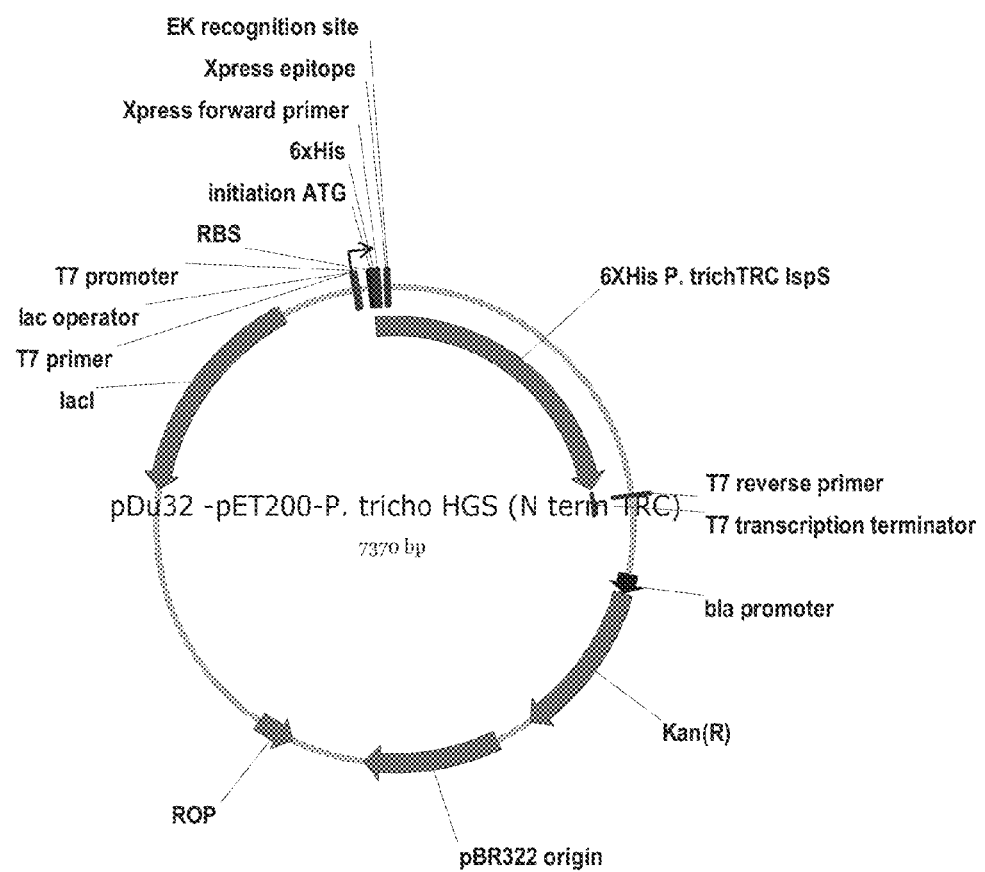
FIG. 15C provides the map of plasmids pDu32.

Screening of transformants containing the kudzu gene was performed by picking colonies and performing PCR with primers EL-957 and EL-966 using PuReTaq Ready-To-Go PCR beads (GE Healthcare, Piscataway, N.J.) according to manufacturer's protocol. PCR conditions were as follows: 95° C. for 2 min (first cycle only), 95° C. for 30 sec, 50° C. for 30 sec, 72° C. for 40 sec, and repeat for 28 cycles, with final extension at 72° C. for 1 min. PCR products were analyzed on a 2% E-gel (Invitrogen Corp) looking for a 600 bp fragment. Colonies containing the correct sized PCR product insert were submitted for DNA sequencing using primers EL-950, EL-951, EL-953, and EL-957. DNA sequencing confirmed the construction of plasmid pMAL-C4X Kudzu (FIGS. 8 and 9).

The reaction was incubated for 5 minutes at room temperature, and the 6 μl topoisomerase mixture was then transformed into E. coli Top10 chemically competent cells (Invitrogen) according to the manufacturer's protocol. Transformants were selected for on LB Kan50, and incubated at 37° C. overnight. Five colonies per construct were chosen and screened using PuReTaq Ready-To-Go PCR Beads (Amersham) using the T7 Forward and MCM 182 primers (Table 2-1). Clones harboring inserts of the correct size were further verified by plasmid miniprep using the QIAPrep Spin Miniprep kit (Qiagen) followed by sequencing using the T7 Forward and T7 Reverse primers (Quintara Biosciences). One fully sequenced construct for each IspS variant (FIGS. 10-14), was chosen for further study. 1 μl of each plasmid was transformed into BL21(λDE3) pLysS (Invitrogen) according to the manufacturer's protocol. Transformants were selected for on LB medium with Kan50+Cm35 and incubated at 37°

TABLE 1-1

Primer sequences

| Primer name | Primer sequence | |
|---|---|---|
| EL-950 | CGGTGAACTGAAAGGTGACGTCC | (SEQ ID NO: 22) |
| EL-951 | GGACGTTAACGCTATTAACACCCTG | (SEQ ID NO: 23) |
| EL-953 | CACATCGTCGATCAGCTCCAGC | (SEQ ID NO: 24) |
| EL-957 | GGTCGTCAGACTGTCGATGAAGCC | (SEQ ID NO: 25) |
| EL-959 | GCTTATGAATTCTGTGCGACCTCTTCTCAATTTACTCAG | (SEQ ID NO: 26) |
| EL-960 | GCTTATAAGCTTAGACATACATCAGCTGGTTAATCGGG | (SEQ ID NO: 27) |
| EL-966 | CTCCTCCAGCAGGTTCTCACC | (SEQ ID NO: 28) |

III. Expression Strain MBP-Kudzu

Plasmid pMAL-C4X Kudzu was transformed into One-Shot BL21(λDE3) chemically competent cells (Invitrogen Corp). Expression strain transformants were selected on LA+50 mg/ml carbenicillin plates.

Example 2

IspS Variants for Crystal Structure Trials

This example describes methods to generate affinity tagged isoprene synthase (IspS) enzymes for expression, purification and crystallization.

I. Strain Construction

For constructs in the pET200D-TOPO vector (Invitrogen), PCR products of the IspS enzymes from P. alba, P. tremuloides, and P. trichocharpa were gel extracted and purified (Qiagen), using 0.8% E-gel (Invitrogen), according to the manufacturer's recommended protocol. PCR reactions for pET200 constructs are as follows: Reaction mixture was 1 μl (Templates)-pET24a-P. alba, 5 μl 10× PfuUltraII Fusion buffer, 1 μl dNTP's (10 mM), 1 μl primer (50 uM) primer F-(MCM219 or 218), 1 μl primer (50 uM) primer R-(MCM182), 41 μl diH2O and 1 μl of PfuUltra II Fusion DNA Polymerase from Stratagene; Cycle Parameter were 95° C. 1 min., 95° C. 1 min, 55° C. 20 sec., 72° C. 27 sec. for 29 cycles followed by 72° C. for 3 min and then 4° C. until cool, using an Eppendorf Mastercycler. Similar reactions were performed for P. tremuloides, P. trichocarpa, and kudzu. 3 μl of purified product was then ligated to the pET200D/TOPO vector (Invitrogen), according to the manufacturer's protocol.

C. overnight. The resulting strains were used for expression and purification of various IspS enzymes for crystallography studies.

Construction of an N-terminally 6×His-tagged IspS (in pDu27, see FIG. 22) for protein purification was prepared as follows. The following PCR Reaction mixture was used: 1 μl (Template)-P. alba pET24a, 5 μl 10× PfuUltraII Fusion buffer, 1 μl dNTP's (10 mM), 1 μl primer (50 uM) primer F-(MCM219), 1 μl primer (50 uM) primer R-(MCM182) (Table 2-1), 41 μl diH2O and 1 μl of PfuUltra II Fusion DNA Polymerase (Stratagene). PCR Cycling Parameters were as follows: 95° C. 1 min., 95° C. 1 min, 55° C. 20 sec., 72° C. 27 sec. for 29 cycles followed by 72° C. for 3 min and 4° C. until cool, using an Eppendorf Mastercycler. The PCR product of the full length P. alba IspS (from the template P. alba pET24a, FIG. 24) was gel extracted and purified, using 0.8% E-gel (Invitrogen) and Qiagen QIAquick Gel Extraction and QIAprep Spin Miniprep kits, according to the manufacturer's recommended protocol. A 3 μl aliquot of purified product was ligated to the pET200D/TOPO vector (Invitrogen), according to the manufacturer's protocol. The reaction was incubated for 5 minutes at room temperature, and the 6 μl topoisomerase mixture was then transformed into E. coli Top10 chemically competent cells (Invitrogen) according to the manufacturer's protocol. Transformants were selected for on LB plates containing kanamycin (50 ug/ml) (Kan50), and incubated at 37° C. overnight. Five colonies were picked and screened using PuReTaq Ready-To-Go PCR Beads (Amersham) using the T7 Forward and MCM182 primers (Table 2-1). Clones harboring inserts of the correct size were further verified by sequencing using the T7 Forward and T7 Reverse primers (Quintara Biosciences). One construct, pDu27 (see FIG. 22), was chosen for further study. A 1 µl aliquot of the plasmid preparation was transformed into BL21(λDE3)pLysS (Invitrogen) according to the manufacturer's protocol. Transformants were selected for on LB plates containing Kan50+ and chloramphenicol (35 µg/ml) (Cm35) and incubated at 37° C. overnight. The resulting strain was used for expression and purification of N-terminally 6×His-tagged P. alba IspS.

Constructs with affinity (6×His) and proteolysis (TEV, Tobacco Etch Virus) tags were generated using P. alba pET24a as a template for PCR reactions. PCR reaction mixtures were prepared as follows: 1 ul (P. alba pET24a), 5 ul 10×PfuUltraII Fusion buffer, 1 ul dNTP's (10 mM), 1 ul primer (50 uM) Alba FL-NdeI-For or Alba TRC (MEA)-NdeI-F, 1 ul primer (50 uM) Alba FLTRC (+) TEV-R, 41 ul diH2O and 1 ul of PfuUltra II Fusion DNA Polymerase from Stratagene. PCR cycling parameters were as follows: 95° C. 1 min., 95° C. 30 sec., 55° C. 20 sec., 72° C. 25 sec. for one cycle and then repeating 95° C. 30 sec., 55° C. 20 sec., 72° C. 25 sec. for an additional 28 cycles, followed by 72° C. 3 min and then 4° C. After amplification and verification of the correct molecular weight of the product by visualization on 0.8% E-gel (Invitrogen), PCR products were digested with restriction enzymes NdeI and XhoI (Roche) for 2 hours at 37° C., and then gel purified using the Qiaquick Gel Purification system (Qiagen) according to the manufacturer's recommended protocol. 3 ul of purified product was ligated to pET-24a (Invitrogen) that was digested with NdeI and XhoI (Roche), gel purified and dephosphorylated (using SAP, shrimp alkaline phosphatase) (Promega) according to the manufacturer's recommended protocols. T4 ligase (NEB) was used for the ligation reaction, which was incubated overnight at 16° C. The ligation reaction was dialyzed into water for 30 min., and 2 µl of the reaction was used to electroporate MCM331 (see below) competent cells. Cells were allowed to recover at 30° C. for 2 hours, and then selected on Kan50 with 5 mM (R)-(−)-Mevalonolactone (MVA) (Sigma) spread onto the plate. Positive transformants were inoculated into 3 ml of liquid LB Kan50, and plasmids were isolated using the QIAPrep Spin miniprep kit (Qiagen). Inserts were verified by restriction digestion using NdeI and XhoI (Roche) and positive clones were sequenced (Quintara Biosciences) with T7 promoter and T7 terminator sequencing primers. 1 µl of each plasmid (see Table 2-3 for plasmid description; FIGS. 15-29) was transformed into chemically competent E. coli BL21 (λDE3) pLysS (Invitrogen) according to the manufacturer's recommended protocol. Transformants were selected on LB Kan50+Cm35 (Chloramphenicol 35 ug/ml) plates and incubated at 37° C. See Table 2-4 for a description of all expression strains.

Preparation of Strain MCM331

Strain MCM331 was prepared as follows. A synthetic operon containing mevalonate kinase, mevalonate phosphate kinase, mevalonate pyrophosphate decarboxylase, and the IPP isomerase was integrated into the chromosome of E. coli. If desired, expression may be altered by integrating different promoters 5' of the operon.

i) Target Vector Construction

The attTn7 site was selected for integration. Regions of homology upstream (attTn7 up) (primers MCM78 and MCM79; Table 2-2) and downstream (attTn7 down) (primers MCM88 and MCM89) were amplified by PCR from MG1655 cells. A 50 µL reaction with 1 µL 10 µM primers, 3 µL ddH2O, 45 µL Invitrogen Platinum PCR Supermix High Fidelity, and a scraped colony of MG1655 was denatured for 2:00 at 94° C., cycled 25 times (2:00 at 94° C., 0:30 at 50° C., and 1:00 at 68° C.), extended for 7:00 at 72° C., and cooled to 4° C. This resulting DNA was cloned into pCR2.1 (Invitrogen) according to the manufacturer's instructions, resulting in plasmids MCM278 (attTn7 up) and MCM252 (attTn7 down). The 832 bp ApaI-PvuI fragment digested and gel purified from MCM252 was cloned into ApaI-PvuI digested and gel purified plasmid pR6K, creating plasmid MCM276. The 825 bp PstI-NotI fragment digested and gel purified from MCM278 was cloned into PstI-NotI digested and gel purified MCM276, creating plasmid MCM281.

ii) Cloning of Lower Pathway and Promoter

MVK-PMK-MVD-IDI genes were amplified from pTrcK-KDyIkIS with primers MCM104 and MCM105 using Roche Expand Long PCR System according to the manufacturer's instructions. This product was digested with NotI and ApaI and cloned into MCM281 which had been digested with NotI and ApaI and gel purified. Primers MCM120 and MCM127 were used to amplify CMR cassette from the GeneBridges FRT-gb2-Cm-FRT template DNA using Stratagene Pfu Ultra II. A PCR program of denaturing at 95° C. for 4:00, 5 cycles of 95° C. for 0:20, 55° C. for 0:20, 72° C. for 2:00, 25 cycles of 95° C. for 0:20, 58° C. for 0:20, 72° C. for 2:00, 72° C. for 10:00, and then cooling to 4° C. was used with four 50 µL PCR reactions containing 1 uL~10 ng/µL template, 1 µL each primer, 1.25 µL 10 mM dNTPs, 5 µL 10× buffer, 1 µL enzyme, and 39.75 µL ddH20. Reactions were pooled, purified on a Qiagen PCR cleanup column, and used to electroporate water-washed Pir1 cells containing plasmid MCM296. Electroporation was carried out in 2 mM cuvettes at 2.5V and 200 ohms. Electroporation reactions were recovered in LB for 3 hr at 30° C. Transformant MCM330 was selected on LA with CMPS, Kan50.

iii) Integration into E. coli Chromosome

Miniprepped DNA (Qiaquick Spin kit) from MCM330 was digested with SnaBI and used to electroporate BL21(DE3) (Novagen) or MG1655 containing GeneBridges plasmid pRedET Carb. Cells were grown at 30° C. to ~OD1 then induced with 0.4% L-arabinose at 37° C. for 1.5 hours. These cells were washed three times in 4 C ddH2O before electroporation with 2 µL of DNA. Integrants were selected on L agar with containing chloramphenicol (5 µg/ml) and subsequently confirmed not to grow on L agar+Kanamycin (50 µg/ml). BL21 integrant MCM331 and MG1655 integrant MCM333 were frozen.

TABLE 2-1

Primers

| | | |
|---|---|---|
| MCM219 | caccatgcgttgtagcgtgtcca | (SEQ ID NO: 29) |
| MCM182 | gggcccgtttaaactttaactagactctgcagttagcgttcaaacggcagaa | (SEQ ID NO: 30) |
| MCM218 | caccatgcgtcgttctgcgaactac | (SEQ ID NO: 31) |

TABLE 2-2

Primers of construction of MCM331

| | | |
|---|---|---|
| MCM78 | attTn7 up rev for integration construct | gcatgctcgagcggccgcTTTTAATCAAACATCCTGCCAACTC (SEQ ID NO: 32) |
| MCM79 | attTn7 down rev for integration construct | gatcgaagggcgatcgTGTCACAGTCTGGCGAAACCG (SEQ ID NO: 33) |
| MCM88 | attTn7 up forw for integration construct | ctgaattctgcagatatcTGTTTTTCCACTCTTCGTTCACTTT (SEQ ID NO: 34) |
| MCM89 | attTn7 down forw for integration construct | tctagagggcccAAGAAAAATGCCCCGCTTACG (SEQ ID NO: 35) |
| MCM104 | GI1.2 promoter - MVK | Gatcgcggccgcgcccttgacgatgccacatcctgagcaa Ataattcaaccactaattgtgagcggataacacaaggagg Aaacagctatgtcattaccgttcttaacttc (SEQ ID NO: 36) |
| MCM105 | aspA terminator - yIDI | Gatcgggccccaagaaaaaaggcacgtcatctgacgtgcc Tttttttatttgtagacgcgttgttatagcattcta (SEQ ID NO: 37) |
| MCM120 | Forward of attTn7: attTn7 homology, GB marker homology | aaagtagccgaagatgacggtttgtcacatggagtt ggcaggatgtttgattaaaagcAATTAACCCTCACTA AAGGGCGG (SEQ ID NO: 38) |
| MCM127 | Rev complement of 1.2 GI: GB marker homology(extra long), promoter, RBS, ATG | AGAGTGTTCACCAAAAATAATAACCTTTCCCGGTGCAgaa Gttaagaacggtaatgacatagctgtttcctccttgtgtt Atccgctcacaattagtggttgaattatttgctcaggatg tggcatcgtcaagggcTAATACGACTCACTATAGGGCTCG (SEQ ID NO: 39) |

TABLE 2-3

Plasmids

| | |
|---|---|
| P. alba pET24a | pET24a with "full length" IspS from P. alba |
| P. trichocharpa pET24a | pET24a with "full length" IspS from P. trichocharpa |
| P. tremuloides pET24a | pET24a with "full length" IspS from P. tremuloides |
| MBP-Kudzu | |
| pDu27 | P. albaFL-pET200/Top 10 |
| pDu30 | P. albaTRC-pET200/Top10 |
| pDu31 | P. tremTRC-pET200/Top 10 |
| pDu32 | P. trichTRC-pET200/Top10 |
| MD09-161 | pET24a-P.alba FL C-Term (+) TEV, His tag/MCM331 |
| MD09-163 | pET24a-P.alba TRC (MEA) C-Term (+) TEV, His tag/MCM331 |

TABLE 2-4

Strains

| | |
|---|---|
| MBP-Kudzu | |
| MD08-99 | BL21 DE3 pLys + pDu27 |
| MD08-100 | BL21 DE3 pLys + pDu30 |
| MD08-102 | BL21 DE3 pLys + pDu31 |
| MD08-104 | BL21 DE3 pLys + pDu32 |
| MD09-165 | BL21(DE3)pLysS, pET24a-P.alba FL C-Term (+) TEV, His tag |
| MD09-167 | BL21(DE3) pLysS, pET24a-P.alba TRC (MEA) C-Term (+) TEV, His tag |

II. Purification of 6×His-Tagged IspS
Expression of 6×His-Tagged IspS

N-terminally 6×His-tagged IspS was expressed and purified from strain MD08-99. The growth procedure is suitable for histidine tagged enzymes expressed in BL21(λDE3) pLysS cells. A 10 ml of overnight culture was prepared for each 1L of planned growth. The appropriate antibiotics (50 mg/ml kanamycin, 50 mg/ml chloramphenicol, and/or 50 mg/ml Carbenecillin) was added to 10 ml of LB medium in a 25 ml flask and was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1L Day culture was inoculated with 10 ml of overnight culture and grown at 30-37° C. with shaking at ~220 rpm until the $OD_{600}$ reached ~0.4-0.6. Day cultures were then induced with 400 μM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process. Purification of 6×His-Tagged IspS For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 40-50 ml of lysis buffer was used per 1L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 μl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 μl).

The clarified lysate was run over HisTrap HP columns (GE Healthcare) using a gradient from 0-100% Ni buffer B. Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a HiPrep 26/10 Desalting column (GE healthcare) packed with Sephadex G25 resin. The G-25 buffer consisted of 50 mM HEPES, 50 mM NaCl, and 1 mM DTT, pH 7.4. The desired sample was then purified over a HiTrap Q HP column (GE) using a gradient elution from 0% Q seph buffer A to 100% Q seph buffer B (Q seph buffer A: 50 mM Tris, 0.05 M NaCl, 1 mM DTT, pH 7.6 and Q seph buffer B: 50 mM Tris, 1.0 M NaCl, 1 mM DTT, pH 7.6). Fractions containing the desired protein were analyzed and concentrated. Sample buffer was then exchanged into 50 mM HEPES, 50 mM NaCL, pH 7.4 with 1 mM DTT by passing the sample over a Hi Prep 26/10 Desalting column (GE healthcare) packed with Sephadex G25 resin. A final polishing step of Gel filtration was used when necessary. The sample was passed through a Hi Load 26/60 Superdex 200 prep grade (GE) in gel filtration buffer: (50 mM HEPES, 150 mM NaCl, 1 mM DTT, pH 7.4). Fractions were then analyzed and concentrated. The samples were then stored at −80° C. For preparation for analysis of the band, the sample is run on an SDS-PAGE gel (4-12% NUPAGE gel, Invitrogen), stained and the desired band excised and processed as described below.

III. Digestion of TEV (Tobacco Etch Virus) or EK (Enterokinase)-Tagged Enzymes

TEV Cleavage (IspS from Strains MD09-165 and MD09-167)

For digestion, enzymes were purified through a Ni charged sepharose (GE Healthcare) and desalted into 50 mM HEPES, 50 mM NaCl pH 7.4 buffer containing 1 mM DTT. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (that is also tagged) and impurities. The Ni column pass though and washes were analyzed using SDS-PAGE gel (NUPAGE, Invitrogen) and DMAPP activity assays. Samples containing pure enzyme were pooled and desalted into 50 mM NaCl pH 7.4 buffer containing 1 mM DTT and stored at −80° C.

EK Cleavage (IspS from Strains MD08-102 and MD08-104)

For digestion enzymes were purified through a Ni charges sepharose (GE Healthcare) and desalted into 50 mM HEPES, 50 mM NaCl pH 7.4 buffer containing 1 mM DTT.

Digestion was performed with EKMax (E180-02) (Invitrogen) using 1 unit of EKMax per 20 ug of purified protein at 4° C. overnight. Samples were passed over EK Away resin (Invitrogen) to remove excess enterokinase. Samples were batched onto Ni charged sepharose resin (equilibrated in the Ni was buffer) and incubated for 30 min at 4° C., with occasional inverting. This removed uncleaved enzyme, tag, and impurities. The Ni column pass though and washes were analyzed using SDS-PAGE gel (4-12% NUPAGE, Invitrogen) and DMAPP activity assays. Samples containing pure enzyme were pooled and desalted into 50 mM NaCl pH 7.4 buffer containing 1 mM DTT. Stored at −80° C.

IV. Purification of MBP-IspS

Construction of pMAL-C4X Kudzu for the expression of MBP-Kudzu isoprene synthase is described in Example 1. MBP-Kudzu isoprene synthase production from E. coli grown in batch culture at the 15-L scale.

Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

Citric Acids*$H_2O$ 40 g, $MnSO_4*H_2O$ 30 g, NaCl 10 g, FeSO4*$7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$, pH to 3.0 with HCl/NaOH, then q.s. to volume and filter sterilized with 0.22 micron filter.

Fermentation was performed in a 15-L bioreactor with BL21 (DE3) E. coli cells containing the pMAL-C4X plasmid expressing a maltose binding protein (MBP)-Kudzu isoprene synthase fusion molecule. This experiment was carried out to produce isoprene synthase at the desired fermentation pH 7.0 and temperature 30° C. A frozen vial of the E. coli strain was thawed and inoculated into tryptone-yeast extract medium. After the inoculum grew to OD 1.0, measured at 550 nm ($OD_{550}$), 120 mL was used to inoculate a 15-L bioreactor bringing the initial volume to 9-L.

Expression of the desired molecule was achieved by adding isopropyl-beta-D-1-thiogalactopyranoside (IPTG). The IPTG concentration was brought to 1 mM when the $OD_{550}$ reached a value of 10. Cells containing the desired product were harvested 3 hrs after IPTG addition.

MBP-IspS Purification

The broth was centrifuged for 15 min at 10000×g. The pellet was collected and frozen at −80° C. until further purification. Cells were resuspended in MBP-Bind Buffer (5% glycerol, 20 mM Tris pH 7.4, 200 mM NaCl, 2 mM DTT, 1 mg/ml lysozyme) and passed through the french press three times at 20000 psi. The lysate was then ultracentrifuged at 100000×g for 1 hour to yield a relatively clear solution. The supernatant was pipetted from the top of the tube without disturbing the gelatinous material on the bottom of the centrifuge tube. Gel filtration was performed on the supernatant using a Superdex-200 26/60 column (GE healthcare). The column was developed using MBP-Bind buffer at a flow rate of 3 mL/min at 23° C. Fractions were tested for DMAPP activity as described below. Active fractions were pooled and loaded onto 25 mL amylose resin (New England Biolabs). The column was washed with 10 column volumes MBP-Bind buffer and the protein was then eluted with 2 column volumes of MBP-Bind buffer containing 10 mM maltose to yield >90% pure MBP-IspS.

V. DMAPP Assay

The following reaction mixture was used for the DMAPP assay: 25 μL lysate mixture, 5 μL MgCl2 (1 M), 5 μL DMAPP (100 mM), and 65 μL 100 mM Tris pH 8, 100 mM NaCl for a total volume of 100 μL. The reaction is performed at 30° C. for 15 minutes in a gas tight 1.8 mL GC tube. Reactions are terminated by the addition of 100 μL 500 mM EDTA (pH 8). The amount of isoprene produced was measured by GC/MS.

The analysis was performed (for the 2 mL and 96-well plate methods) using an Agilent 6890 GC/MS system interfaced with a 5973 MS Leap CTC CombiPAL autosampler operating in headspace mode. An Agilent HP-5 (5% Phenyl Methyl Siloxane (15 m×0.25 mm×0.25 uM)) column was used for separation of analytes. The sampler was set up to inject 100 μL of headspace gas. The GC/MS method utilized helium as the carrier gas at a flow of 1 ml/min. The injection port was held at 250° C. with a split ratio of 50:1. The oven temperature was held at 37° C. for the 2 min duration of the analysis. The Agilent 5793N mass selective detector was run in single ion monitoring (SIM) mode on mass 67. The detector was switched off from 0.00 to 0.44 minutes to allow the elution of permanent gases and on 0.44 mins to 0.60 mins. Under these conditions isoprene (2-methyl-1,3-butadiene) was observed to elute at 0.49 minutes. A calibration table was used to quantify the absolute amount of isoprene and was found to be linear from 0 μg/L to 5600 mg/L (using calibration gas).

Example 3

Three-Dimensional Structure of IspS

Seven constructs of plant isoprene synthase (IspS) were prepared in the hope that one or more would yield crystals suitable for x-ray diffraction. These were: a construct containing N-terminal histidine-tagged maltose binding protein and kudzu IspS (MBP-kudzu), full-length *P. alba* IspS with N-terminal histidine-tag (MD08-99), *P. alba* IspS with the first nineteen N-terminal residues removed (MD08-100), this construct also had the N-terminal his-tag removed after purification. Full-length, untagged *P. alba* IspS (strain RM11608-2). A truncated *P. alba* IspS construct featuring two additional residues before the twin-arginine motif was generated (MD09-167). *P. tricharpa* IspS was generated, which contains both an N-terminal his-tag and N-terminal truncation (MD08-104), and another construct composed of IspS from *P. tremuloides* was generated with an N-terminal his-tag and N-terminal truncation (MD08-102). Construction of strains expressing various isoprene synthases are described above.

Protein from each construct was purified and a concentrated protein solution was then prepared for surveying possible crystallization conditions. Each protein was purified independently and surveyed as described below. All in-house crystallization screens were set up using the hanging drop vapor diffusion method. At a minimum, each protein was surveyed using the following commercial screens: the Crystal Screen from Hampton Research (Aliso Viejo, Calif.) and the JCSG+ Suite from Qiagen (Valencia, Calif.).

Purified MBP-kudzu using was set up using the following commercial screens: the Crystal Screen from Hampton Research and the JCSG+ Suite from. Additionally, purified MBP-kudzu was sent to the Hauptman-Woodward Institute (Buffalo, N.Y.) for high-throughput screening, where no fewer than 1536 conditions were surveyed. The purified MBP-kudzu fusion precipitated out of solution in the majority of conditions, and no protein crystals were observed.

The next construct used for crystallization screening was MD08-99 (full-length *P. alba* IspS with N-terminal histidine-tag). MD08-99 was purified and the histidine-tag was removed. The same three initial crystallization screens were performed as for MBP-kudzu. The Hampton Research Crystal Screen and Qiagen JCSG+ Suite were each performed at multiple protein concentrations. Small needle-like crystals were observed in some Hampton Research Crystal Screen conditions. Further attempts to improve the crystals involved co-crystallization with the IspS inhibitor sodium ibandronate (Sigma-Aldrich, St Louis, Mo.). Taken together, an additional 288 crystallization conditions were attempted with variations of pH, concentration, and crystallization reagents. The nine best crystals were then prepared for data collection and tested in-house on a Rigaku RU200 rotating anode generator and R-AXIS IV++, and they either did not diffract x-rays or were salt crystals.

The first nineteen N-terminal residues of *P. alba* IspS were removed to produce construct MD08-100. This construct had the N-terminal histidine-tag removed after purification. In house crystallization screens were performed using the Hampton Research Crystal Screen and Qiagen JCSG+ Suite, each with multiple protein concentrations. Initial crystal hits included hexagonal plates that diffracted to 16 Å resolution, and small rods that diffracted to 5 Å resolution using the in-house x-ray generator. In an attempt to improve the crystals, MD08-100 was co-crystallized with either sodium ibandronate or sodium pyrophosphate (Sigma-Aldrich, St Louis, Mo.), both of which are inhibitors of the IspS activity. Neither inhibitor resulted in improved crystals or improved diffraction. An additional 168 crystallization conditions were attempted with variations of pH, concentration, and crystallization reagents. The twenty-one most promising MD08-100 crystals were screened for diffraction, with the best resolution obtained being 5 Å.

Full-length, untagged *P. alba* IspS (strain RM11608-2) from a fermentation run was purified. An initial screen was set up using the Hampton Research Crystal Screen, and crystals were observed in four different conditions. All four crystals were tested for diffraction in-house, with three being salt crystals and one not diffracting.

A truncated *P. alba* IspS construct featuring two additional residues before the twin-arginine motif was generated (MD09-167). This construct contains a C-terminal histidine-tag, and crystallization experiments were set up with the tag either cleaved or not cleaved, at varying protein concentrations, and with or without sodium pyrophosphate. Initial crystallization screens were done as per MBP-kudzu. Crystals from this construct were observed in numerous conditions; optimization included 528 variations of pH, precipitating agents, concentrations, and inhibitors. From the optimization experiments, fifteen different MD09-167 crystals were screened in-house for diffraction. In an effort to improve the resolution, various crystal freezing conditions were tested, with the effect of improving the diffraction limits from 10 Å to 6.5 Å.

A new construct containing *P. tricharpa* IspS was generated, which contains both an N-terminal histidine-tag and an N-terminal truncation (MD08-104). Purified MD08-104 with cleaved histidine-tag was surveyed using the Hampton Research Crystal Screen and the Qiagen JCSG+ suite. This construct generated heavier precipitate than the *P. alba* IspS constructs. Very small needles were observed, with none of the crystals being suitable for diffraction.

Another construct composed of IspS from *P. tremuloides* was generated with an N-terminal histidine-tag and an N-terminal truncation (MD08-102; SEQ ID NO:11). Purified MD08-102 with and without cleaved histidine-tag was set up using the Hampton Research Crystal Screen and the Qiagen JCSG+ Suite at varying protein concentrations. Rod and plate-like crystals were observed in some conditions and an additional 120 experiments were performed to improve the crystals by varying pH, concentration, and crystallization reagents. From the optimization experiments, ten crystals were tested in-house, with the initial best diffraction reaching 5 Å. Upon further modification of the freezing conditions of the crystals, a crystal was found that diffracted to 3.3 Å from the uncleaved histidine-tagged protein. This crystal was grown by mixing 2 μL of protein (10 mg/ml, with 30 mM $MgCl_2$) with 2 μL of precipitant solution [10% (wt/vol) polyethylene glycol 8000, 0.1 M HEPES, pH 7.5, 8% ethylene glycol] and equilibrated against 500 μL of precipitant. A cluster of rod-shaped crystals appeared after three weeks. The crystals belong to the tetragonal space group P43212, and have unit cell dimensions a=154.2, b=154.2, c=142.7.

In-house x-ray diffraction data were collected under a nitrogen stream at 100 K using a Rigaku RU200 generator and R-AXIS IV++ detector. Before flash-freezing the crystal in liquid nitrogen, it was cryoprotected by swiping it through a solution containing 10% (wt/vol) polyethylene glycol 8000, 0.1 M HEPES, pH 7.5, and 25% ethylene glycol. Data were integrated using Mosflm (Leslie, A. (1998) J. of Appl. Crystallography 30, 1036-1040) and scaled using SCALA (Collaborative Computational Project, N. (1994) Acta Crystallographica Section D 50, 760-763). The data were then phased by molecular replacement using MrBUMP (Keegan, R. M., and Winn, M. D. (2007) Acta Crystallographica Section D 63, 447-457; Vagin, A., and Teplyakov, A. (1997) J. of Appl. Crystallography 30, 1022-1025), with a monomer of limonene synthase (Protein Data Bank ID 2ONH) (Berman, H., et al. (2007) Nucl. Acids Res. 35, D301-303) as the starting model. The crystal contains one dimer in the asymmetric unit with a solvent content of 66%.

A 3.05 Å data set from the same crystal was then collected using beamline 11-1 of the Stanford Synchrotron Radiation Laboratory. These data were also processed using Mosflm and SCALA. Data collection and refinement statistics are given in Table 3-1.

Refinement with Refmac5 (Collaborative Computational Project, N. (1994) Acta Crystallographica Section D 50, 760-763) was used with iterative manual rebuilding steps using the visualization program Coot (Emsley, P., and Cowtan, K. (2004) Acta Crystallographica Section D 60, 2126-2132). During refinement, the geometry of the protein was checked using Molprobity (Davis, I. W., et al. (2007) Nucl. Acids Res., gkm216).

Figure 30:
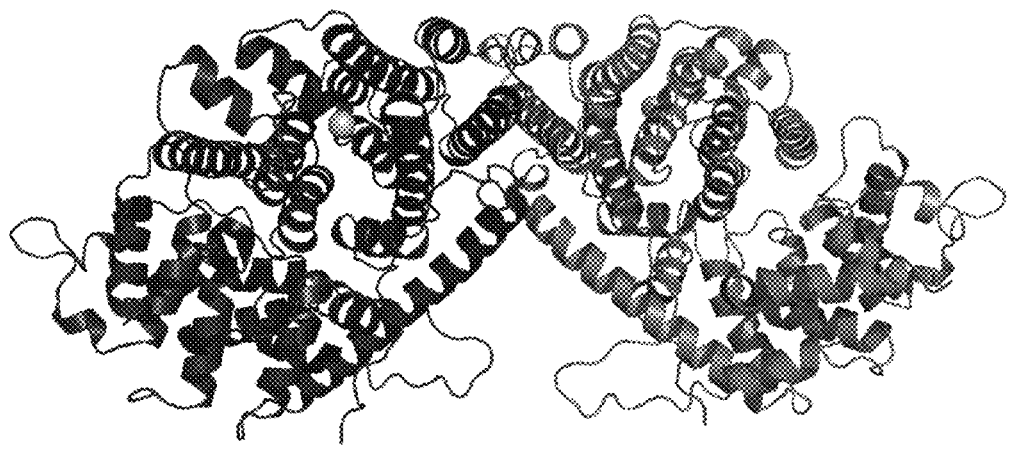
FIG. 30 provides the three-dimensional structure of *P. tremuloides* IspS shown as a dimer. Chain A is in dark gray, chain B is in medium gray and the single magnesium ion found in each active site is light gray.
Figure 31:
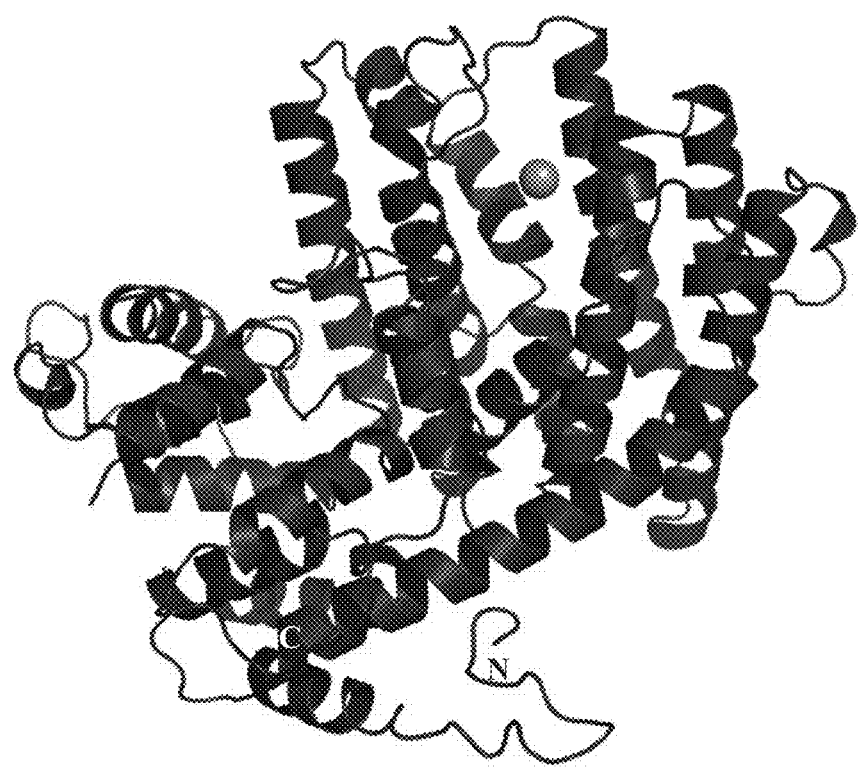
FIG. 31 provides a monomer view of the structure of *P. tremuloides* IspS. The magnesium is shown as a light gray sphere and the N- and C-terminals are indicated.

The fold of P. tremuloides IspS is similar to bornyl diphosphate synthase (Whittington, D. A., et al. (2002) Proc. Natl. Acad. Sci. USA 99, 15375-15380), limonene synthase (Hyatt, D. C., et al. (2007) Proc. Natl. Acad. Sci. USA 104, 5360-5365), and tobacco 5-epi-aristolochene synthase (Starks, C. M., et al. (1997) Science 277, 1815-1820). The structure consists of two helical domains, a C-terminal domain containing the active site and N-terminal domain with unknown function (FIGS. 30 and 31). Coordinates are provided in Table 3-7.

TABLE 3-1

Data Collection and Refinement Statistics

| Data Collection | |
|---|---|
| Space Group | $P4_32_12$ |
| Cell dimensions | |
| A, b, c (Å) | 154.2, 154.2, 142.7 |
| α, β, γ, (°) | 90.0, 90.0, 90.0 |
| Resolution (Å) | 37.8-3.05 |
| $R_{merge}$ | 16.4 (72.9)$^a$ |
| <I/σI> | 10.3 (2.6) |
| Completeness (%) | 99.8 (100) |
| Redundancy | 7.3 (7.4) |
| Refinement | |
| Resolution (Å) | 37.8-3.05 |
| No. measured reflections | 248741 |
| No. Unique reflections | 34201 |
| $R_{work}$ | 21.1 |
| $R_{free}$ | 27.1 |
| rmsd bonds, (Å) | 0.011 |
| rmsd angles, (°) | 1.28 |
| No. of Atoms | |
| Protein, ions$^b$ | 8331 |
| Water | 18 |

Flexible Loops

Figure 32:
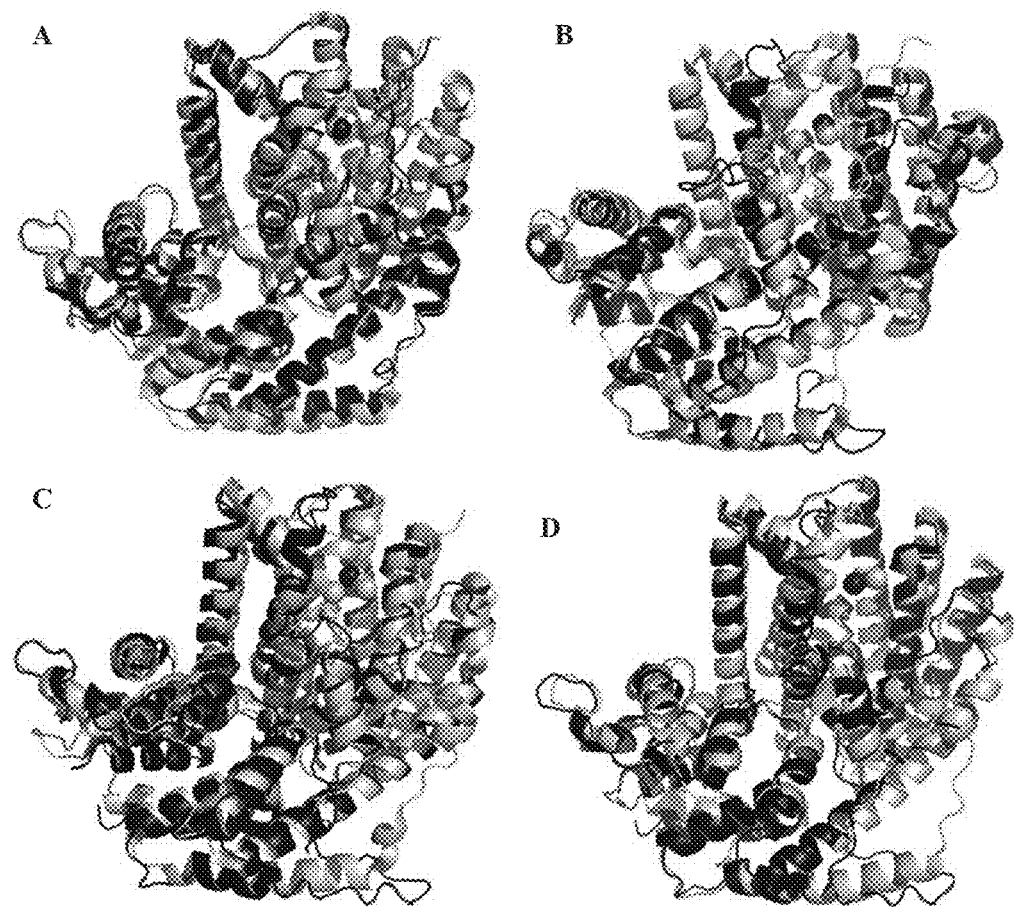
FIG. 32 shows the structural alignments between (A) BdpS and LS, (B) BdpS and *P. tremuloides* IspS, (C) LS and *P. tremuloides* IspS, and (D) TEAS and *P. tremuloides* IspS. In each case the first structure is in light gray and the second is in dark gray. Divalent cations are shown as spheres.
Figure 33:
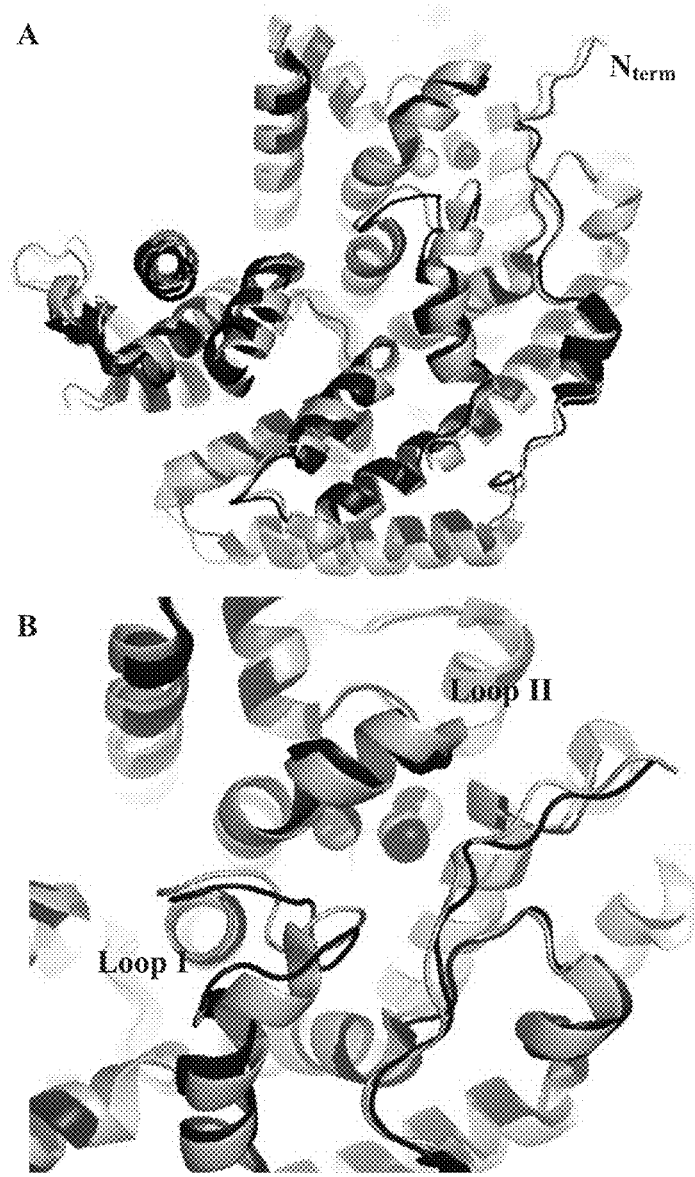
FIG. 33 shows the three dimensional structure of loops in BdpS and LS. Panel A shows the N-terminal loop of Ls in light gray and the N-terminal loop of BdpS in dark gray. Panel B shows that Loop I and Loop II are structurally homologous.
Figure 34:
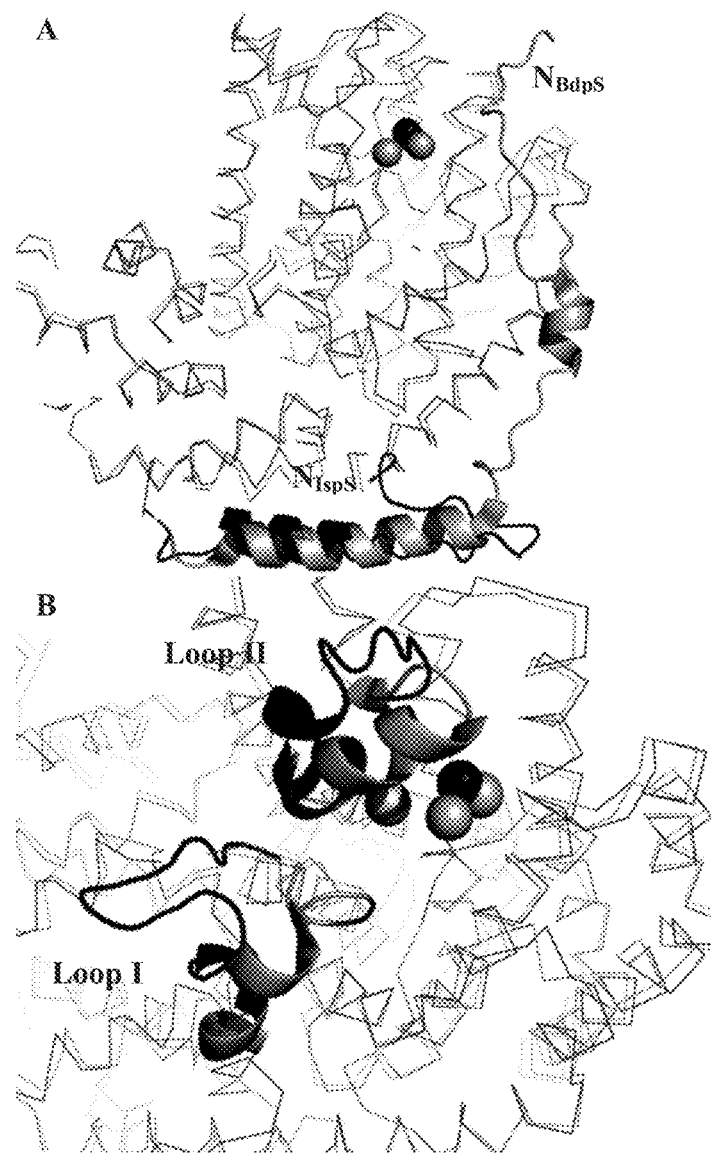
FIG. 34 shows the N-terminal loop of BdpS (dark gray) and *P. tremuloides* IspS (light gray) are structurally divergent. Panel A shows the N-terminal loop and panel B shows Loop I and Loop II.
Figure 35:
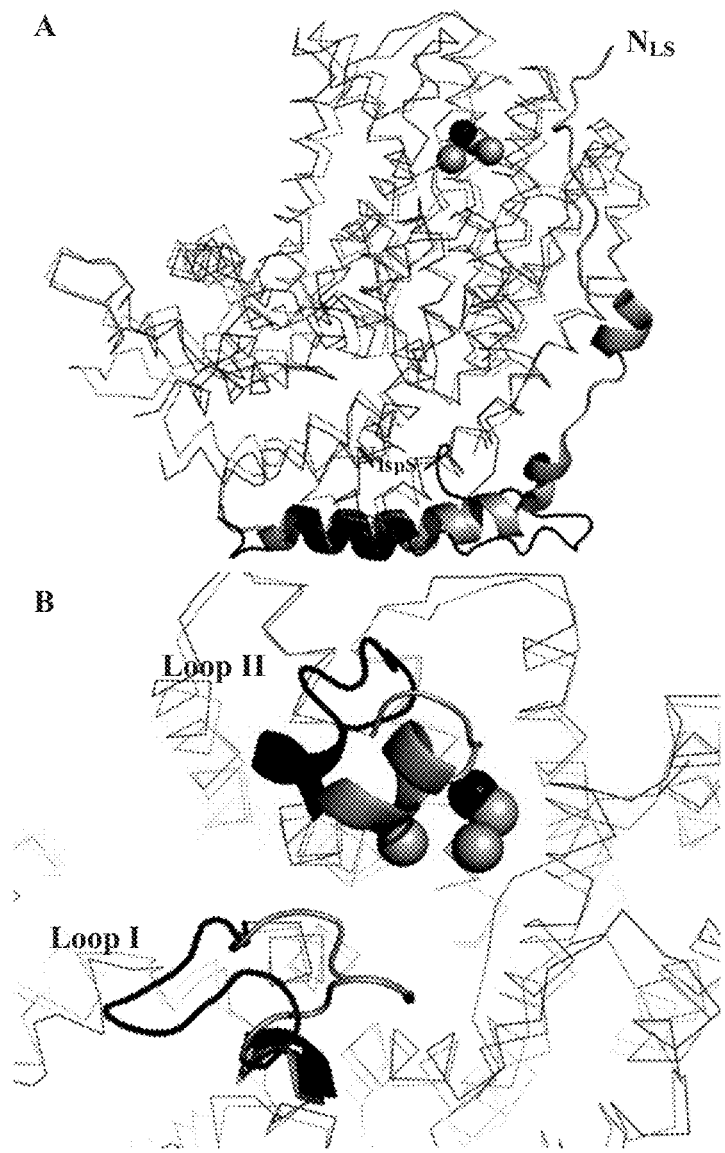
FIG. 35 shows the N-terminal loop of LS (light gray) and *P. tremuloides* IspS (dark gray) are structurally divergent. Panel A shows the N-terminal loop and panel B shows Loop I and Loop II.
Figure 36:
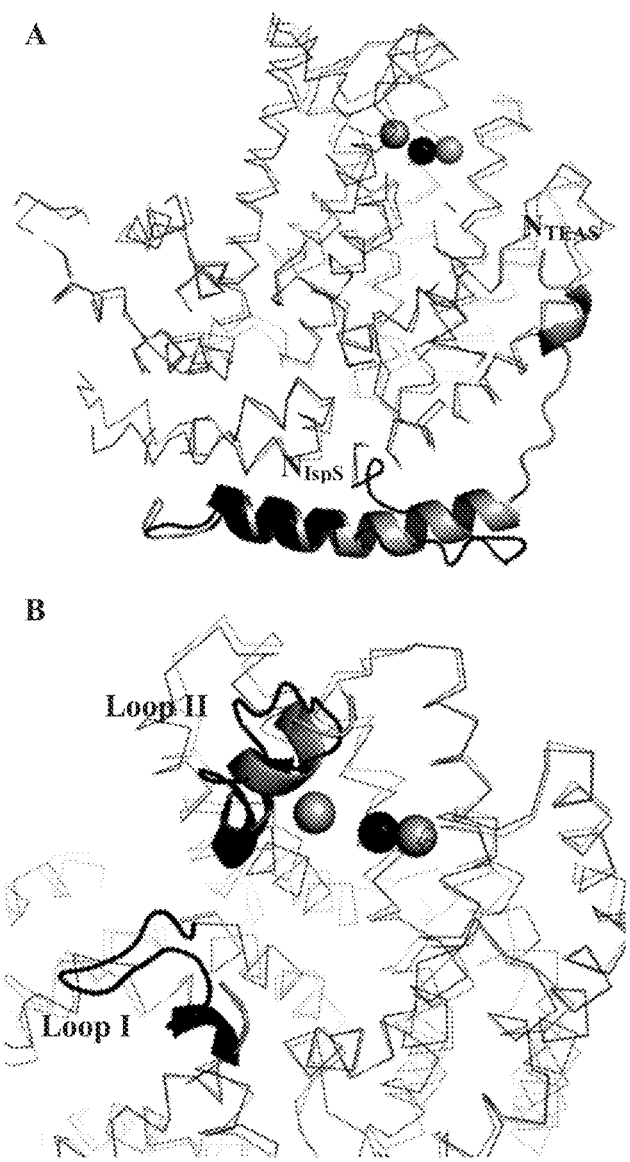
FIG. 36 shows the N-terminal loop of TEAS (light gray) and *P. tremuloides* IspS (dark gray) are structurally divergent. Panel A shows the N-terminal loop and panel B shows Loop I and Loop II. Loop I is disordered in TEAS.

The unique and unexpected discovery coming from the determination of the three-dimensional structure of isoprene synthase is that several crucial loops forming the active site are flexible. The discovery can be immediately seen when the known structure of other terpene synthases are compared with the structure of isoprene synthase (FIG. 32). Overall, the structures are highly conserved in the conformation of secondary structure and connectivity loops. (In this example of the P. tremuloides IspS from construct P.tremTRC-pET200, the numbering convention is such that the first number of the complete sequence containing the tag is −35, with the first residue of IspS being 1.) However, three segments, forming a considerable portion of the substrate binding pocket, notably the truncated N-terminus, along with two loops comprised of residues 438-453 (Loop I) and residues 512-527 (Loop II) are seen to diverge (FIGS. 33 to 36). This has been attributed to the absence of substrate complexed with the enzyme in our structure determination.

In comparing the enzyme with BdpS, for example, we find that the loops corresponding to residues 498-513 and 573-587 are composed of the same number of residues and have a homologous, but not identical amino sequence in these regions. We expect that the related terpene synthases will be found to display similar flexibility in the segments as these structures become more thoroughly studied. The residues in terpene synthases corresponding to these variable loop regions are enumerated in Table 3-2.

TABLE 3-2

Residues corresponding to variable loops in terpene synthases.

| | P. tremuloides IspS | LS | BdpS | TEAS |
|---|---|---|---|---|
| N-term I | Met 1 | Met 57 | Ile 54 | Val 14 |
| | Arg 2 | Arg 58 | Arg 55 | Arg 15 |
| | Arg 3 | Arg 59 | Arg 56 | Pro 16 |
| | Ser 4 | Ser 60 | Ser 57 | Val 17 |
| | Ala 5 | Gly 61 | Gly 58 | Ala 18 |
| | Asn 6 | Asn 62 | Asn 59 | Asp 19 |
| | Tyr 7 | Tyr 63 | Tyr 60 | Phe 20 |
| | Glu 8 | Asn 64 | Gln 61 | Ser 21 |
| | Pro 9 | Pro 65 | Pro 62 | Pro 22 |
| | Asn 10 | Ser 66 | Ala 63 | Ser 23 |
| | Ser 11 | Arg 67 | Leu 64 | Leu 24 |
| | Trp 12 | Trp 68 | Trp 65 | Trp 25 |
| | Asp 13 | Asp 69 | Asp 66 | Gly 26 |
| | Tyr 14 | Val 70 | Ser 67 | Asp 27 |
| | Asp 15 | Asn 71 | Asn 68 | Gln 28 |
| | Tyr 16 | Phe 72 | Tyr 69 | Phe 29 |
| N-term II | Leu 17 | Ile 73 | Ile 70 | Leu 30 |
| | Leu 18 | Gln 74 | Gln 71 | Ser 31 |
| | Ser 19 | Ser 75 | Ser 72 | Phe 32 |
| | Ser 20 | Leu 76 | Leu 73 | Ser 34 |
| | Asp 21 | Leu 77 | Asn 74 | Ile 35 |
| | Thr 22 | Ser 78 | Thr 75 | Asp 36 |
| | Asp 23 | Asp 79 | Pro 76 | Asn 37 |
| | Glu 24 | Tyr 80 | Tyr 77 | Gln 38 |
| | Ser 25 | Lys 81 | Thr 78 | Val 39 |
| | Ile 26 | Glu 82 | Glu 79 | Ala 40 |
| | Glu 27 | Asp 83 | Glu 80 | Glu 41 |
| | Val 28 | Lys 84 | Arg 81 | Lys 42 |
| Loop I | Leu 438 | Leu 498 | Leu 498 | Thr 446 |
| | Ala 439 | Gly 499 | Gly 499 | Ala 447 |
| | Ser 440 | Thr 500 | Thr 500 | The 448 |
| | Ala 441 | Ser 501 | Ser 502 | Tyr 449 |
| | Ser 442 | Val 502 | Tyr 503 | Glu 450 |
| | Ala 443 | Glu 503 | Phe 504 | Val 451 |
| | Glu 444 | Glu 504 | Glu 505 | Glu 452 |
| | Ile 445 | Val 505 | Leu 506 | Lys 453 |
| | Ala 446 | Ser 506 | Ala 507 | Ser 454 |
| | Arg 447 | Arg 507 | Arg 508 | Arg 455 |
| | Gly 448 | Gly 508 | Gly 509 | Gly 456 |
| | Glu 449 | Asp 509 | Asp 510 | Gln 457 |
| | Thr 450 | Val 510 | Val 511 | Ile 458 |
| | Ala 451 | Pro 511 | Pro 512 | Ala 459 |
| | Asn 452 | Lys 512 | Lys 513 | Thr 460 |
| | Ser 453 | Ser 513 | Thr 514 | Gly 461 |

TABLE 3-2-continued

Residues corresponding to variable loops in terpene synthases.

| | P. tremuloides IspS | LS | BdpS | TEAS |
|---|---|---|---|---|
| Loop II | Tyr 512 | Tyr 576 | Tyr 573 | Tyr 520 Ile 521 |
| | His 513 | His 577 | Leu 574 | His 522 |
| | Asn 514 | Asn 578 | His 575 | Asn 523 |
| | Gly 515 | Gly 579 | Gly 576 | Leu 524 |
| | Asp 516 | Asp 580 | Asp 577 | Asp 525 |
| | Ala 517 | Gly 581 | Gly 578 | Gly 526 |
| | His 518 | His 582 | Phe 579 | Tyr 527 |
| | Thr 519 | Gly 583 | Gly 580 | The 528 |
| | Ser 520 | Thr 584 | Val 581 | His 529 |
| | Pro 521 | Gln 585 | Gln 582 | Pro 530 |
| | Asp 522 | His 585 | His 583 | Glu 531 |
| | Glu 523 | Pro 586 | Ser 584 | Lys 532 |
| | Leu 524 | Ile 587 | Lys 585 | Val 533 |
| | Thr 525 | Ile 588 | Thr 586 | Lue 534 |
| | Arg 526 | His 589 | Tyr 587 | Lys 535 |

This important finding can be exploited for the engineering of improved isoprene synthase in a straightforward manner. It would be desirable to exploit the flexibility to enhance enzyme performance by making substitutions in the amino acids forming these segments to facilitate the transitions the enzyme must undergo in the steps of binding substrate and allowing rearrangement of substrate in different kinetic steps that are postulated to occur during enzymatic de-phosphorylation and for electron transfer to convert DMAPP to isoprene.

The structure provides the new insight that these loops can be present in at least two conformations: the "open" form in the absence of substrate, as we have see in the uncomplexed structure of the isoprene synthase, and a "closed," or active form when the substrate is bound. It would therefore also be beneficial to modify residues coming in contact with the loops in the active form as described in Table 3-3.

TABLE 3-3

Residues coming within 5 angstroms of flexible elements

| | P trem IspS | 1N1B | 2ONG | 5EAS[e] |
|---|---|---|---|---|
| N-term neighbors | L17, L18, S19, S20, S239, R243, F253, A254, R255, D256, R257, I259, E260, D293, Y295, D296, V297, Y298, G299, T300, E303, Y325, L374, Y375, elements of loop I, elements of loop II, V529, L530, T534 | 70I, 71Q, 72S, 73L, 298S, 302S, 312F, 313V, 314R, 315D, 316R, 318V, 319E, 352D, 354Y, 355D, 356V, 357Y, 358G, 359T, 362E, 384Y, 433Y, 434H, elements of loop I, elements of loop II, 589I, 590A, 594F | I73, Q74, S75, L76, F299, R303, F313, A314, R315, A316, R317, V319, E320, D353, Y355, D356, V357, Y358, G359, T360, E363, Y385, F434, Y435, elements of loop I, elements of loop II, M590, T591, F595 | L30, S31, F32, S33, S248, K252, Y262, A263, R264, D265, R266, V268, D269, D302, F304, D305, A306, Y307, G308, T309, E312, Y334, F383, I384, elements of loop I, elements of loop II, I538, I538, V543 |
| Loop I neighbors | Elements of N-term, D293, Y295, V297, E370, A371, W373, L374, S378, T379, P380, F382, Y385, F386, R433, L434 C435, N436, D437, V454, S455, C456, Y457, M458, T469, V472, I476, Y512, elements of loop II | Elements of N-term, 352D, 354Y, 356V, 429E, 430A, 432W, 433Y, 437Y, 438T, 439P, 441L, 444Y, 445L, 493R, 494L, 495P, 496D, 497D, 514I, 515Q, 516C, 517Y, 518M, 529V, 532V, 536I, 572Y, elements of loop II | Elements of N-term, D353, Y355, V357, E430, A431, W433, F434, H438, K439, P440, L442, Y445, L446, R493, L494, A495, D496, D497, L514, Q515, C516, Y517, M518, R529, V532, I536, Y573, elements of loop II | Elements of N-term, D304, F304, A306, E379, S380, W382, F383, Y387, T388, P389, V391, Y394, L395, R441, V442, I443, D444, D445, I462, E463, C464, C465, M466, M477, F480, A484, Y520, elements of loop II |
| Loop II neighbors | Elements of N-terminus, E187, L188, R255, R257, F270, E271, Q273, Y274, F285, V288, A439, S440, S442, S508, H509, C510, T511, Y512, R528, V529, L530, S531, V532 | Elements of N-terminus, 246D, 247L, 314R, 316R, 329E, 330S, 332F, 333W, 344I, 348I, 499G, 500T, 503Y, 568A, 569Q, 570F, 571I, 572Y, 588H, 589I, 590A, 591G, 592L | Elements of N-terminus, D247, I248, R315, R317, E330, P331, Q333, H334, N345, I347, G499, T500, V502, A569, Q570, L571, M572, Y573, Q589, M590, T591, R592, T593 | Elements of N-terminus, E195, Q196, R264, R266, F279, E280, Q282, Y283, I294, I297, A447, T448, E450, V516, E517, V518, T519, Y520, H537, I538, I539, N540, L541 |

Selection of Sites for Improvement of Plant Isoprene Synthase

The isoprene synthases of plants were expected to be homologous to the terpene synthases. The three-dimensional structures of three homologous terpene synthases have been determined: Salvia officinalis bornyl diphosphate synthase (BdpS; pdb entry 1N1B), Mentha spicata limonene synthase (LS; pdb entry 2ONG), and tobacco 5-epi-aristolochene synthase (TEAS; pdb entry 5EAS). These enzymes share only 33% homology but their tertiary structure is conserved. Sequence identity is shown in Table 3-4, and structural homology between the structures is shown in Table 3-5. In addition, the structures of intermediate complexes with all three related enzymes have shown that not only tertiary folding, but also detailed interactions in the active sites of these enzymes are highly conserved.

TABLE 3-4

Percent Identity of Terpene Cyclases.

| | P trem IspS | 1N1B | 2ONG | 5EAS[e] |
|---|---|---|---|---|
| P alba IspS[a] | 98.6 | 40.7 | 41.3 | 33.2 |
| P trem IspS[b] | | 41.0 | 41.4 | 33.2 |

TABLE 3-4-continued

Percent Identity of Terpene Cyclases.

| | P trem IspS | 1N1B | 2ONG | 5EAS[e] |
|---|---|---|---|---|
| 1N1B[c] | | | 51.4 | 33.8 |
| 2ONG[d] | | | | 33.3 |

[a]Polar alba isoprene synthase
[b]Polar tremuloides isoprene synthase
[c]bornyl diphosphate synthase
[d]limonene synthase
[e]5-epi-aristolochene synthase

TABLE 3-5

Structural Alignment of Terpene Synthases.

| | 1N1B[b] | 2ONG[c] | 5EAS[d] |
|---|---|---|---|
| P trem IspS[a] | 1.40 (465)[e] | 1.29 (468) | 1.62 (458) |
| 1N1B | | 1.27 (520) | 1.97 (476) |
| 2ONG | | | 1.83 (477) |

[a]Polar tremuloides isoprene synthase
[b]bornyl diphosphate synthase
[c]limonene synthase
[d]5-epi-aristolochene synthase
[e]Root mean square deviation in Å for Cα atoms, with the number of aligned residues in parenthesis In this example of the *P. tremuloides* IspS from construct P.tremTRC-pET200, the numbering convention is such that the first number of the complete sequence containing the tag is −35, with the first residue of IspS being 1.

A comparison of the active site from the structure of BdpS and the structure of IspS indicates that the active site involved in metal ion binding and phosphate recognition is conserved. In particular, Arg 255, Asp 292, Asp 296, Glu 370, Arg 433 and Asn 436 of *P. tremuloides* IspS were observed to overlap equivalent residues in BdpS. The positioning of an intermediate of the BdpS was also compared with the IspS structure. Based on this it was possible to identify the analogous binding region and the approach direction that dimethylallyl pyrophosphate would require in order to bind and react with the IspS enzyme.

Based on the structure of IspS, sites in the IspS were identified as candidates for mutagenesis to produce variant IspS enzymes with improved performance. Briefly, sites were selected in the IspS that might alter the interaction of the metal binding, diphosphate recognition, DMAPP chain binding and/or the approach to the active site.

I. Diphosphate/Metal Binding Sites

The side chains of amino acid residues in the IspS that are found in proximity to the metal and diphosphate binding side chains were identified. These residues include Asp 293, Tyr 385, Ser 392, and Asp 437 of *P. tremuloides* IspS. Engineering of these sites may result in increased enzyme activity.

II. Substrate Access Loops

The substrate access loops of IspS are in regions that deviate from the BdpS structure. In the BdpS structure the residues create a cover over the active site. It is likely that upon substrate binding the structure of IspS will form a similar structure. As such the residues in these loops, including residues 440-453 and 512-524, may be in a position to alter the activity of the IspS. In the *P. tremuloides* IspS enzyme, residues 440-453 have the sequence SASAEIARGETANS (SEQ ID NO:40) and residues 512-526 have the sequence YHNGDAHTSPDEL (SEQ ID NO:41).

III. Isoprenyl Binding Site

The complex of BdpS and the product of the reaction, bornyl diphosphate (PDB entry 1N24), was used to identify residues in the IspS structure that with protein engineering may be used modulate substrate specificity and/or reaction rate (altered on and off rates of substrate and product). These residues include Ser 261, Trp 264, Phe 285, Thr 289, Ser 393, Ser 394, Phe 432, and Try 512 *P. tremuloides* IspS.

TABLE 3-6

Candidate Mutagenesis Sites

| | P. tremuloides IspS |
|---|---|
| DPP/Metal Binding Sites | Asp 293 |
| | Tyr 385 |
| | Ser 392 |
| | Asp 437 |
| Substrate Access Loop I | Ser 440 |
| | Ala 441 |
| | Ser 442 |
| | Ala 443 |
| | Glu 444 |
| | Ile 445 |
| | Ala 446 |
| | Arg 447 |
| | Gly 448 |
| | Glu 449 |
| | Thr 450 |
| | Ala 451 |
| | Asn 452 |
| | Ser 453 |
| Substate Access Loop II | Tyr 512 |
| | His 513 |
| | Asn 514 |
| | Gly 515 |
| | Asp 516 |
| | Ala 517 |
| | His 518 |
| | Thr 519 |
| | Ser 520 |
| | Pro 521 |
| | Asp 522 |
| | Glu 523 |
| | Leu 524 |
| Isoprenyl Binding Site | Ser 261 |
| | Trp 264 |
| | Phe 285 |
| | Thr 289 |
| | Ser 393 |
| | Ser 394 |
| | Phe 432 |
| | Tyr 512 |

TABLE 3-7

Coordinates of *P. tremuloides* IspS

```
HEADER    --- XX-XXX-XX xxxx
COMPND    ---
REMARK  3
REMARK  3  REFINEMENT.
REMARK  3    PROGRAM: REFMAC 5.5.0088
REMARK  3    AUTHORS: MURSHUDOV, VAGIN, DODSON
REMARK  3
```

TABLE 3-7-continued

Coordinates of *P. tremuloides* IspS

| | | |
|---|---|---|
| REMARK 3 | | REFINEMENT TARGET: MAXIMUM LIKELIHOOD |
| REMARK 3 | | |
| REMARK 3 | | DATA USED IN REFINEMENT. |
| REMARK 3 | | RESOLUTION RANGE HIGH (ANGSTROMS): 3.05 |
| REMARK 3 | | RESOLUTION RANGE LOW (ANGSTROMS): 110.17 |
| REMARK 3 | | DATA CUTOFF (SIGMA(F)): NONE |
| REMARK 3 | | COMPLETENESS FOR RANGE (%): 99.67 |
| REMARK 3 | | NUMBER OF REFLECTIONS: 32446 |
| REMARK 3 | | |
| REMARK 3 | | FIT TO DATA USED IN REFINEMENT. |
| REMARK 3 | | CROSS-VALIDATION METHOD: THROUGHOUT |
| REMARK 3 | | FREE R VALUE TEST SET SELECTION: RANDOM |
| REMARK 3 | | R VALUE (WORKING + TEST SET): .21396 |
| REMARK 3 | | R VALUE (WORKING SET): .21092 |
| REMARK 3 | | FREE R VALUE: .27112 |
| REMARK 3 | | FREE R VALUE TEST SET SIZE (%): 5.1 |
| REMARK 3 | | FREE R VALUE TEST SET COUNT: 1727 |
| REMARK 3 | | |
| REMARK 3 | | FIT IN THE HIGHEST RESOLUTION BIN. |
| REMARK 3 | | TOTAL NUMBER OF BINS USED: 20 |
| REMARK 3 | | BIN RESOLUTION RANGE HIGH: 3.050 |
| REMARK 3 | | BIN RESOLUTION RANGE LOW: 3.129 |
| REMARK 3 | | REFLECTION IN BIN (WORKING SET): 2359 |
| REMARK 3 | | BIN COMPLETENESS (WORKING + TEST) (%): 100.00 |
| REMARK 3 | | BIN R VALUE (WORKING SET): .288 |
| REMARK 3 | | BIN FREE R VALUE SET COUNT: 127 |
| REMARK 3 | | BIN FREE R VALUE: .352 |
| REMARK 3 | | |
| REMARK 3 | | NUMBER OF NON-HYDROGEN ATOMS USED IN REFINEMENT. |
| REMARK 3 | | ALL ATOMS: 8349 |
| REMARK 3 | | |
| REMARK 3 | | B VALUES. |
| REMARK 3 | | FROM WILSON PLOT (A**2): NULL |
| REMARK 3 | | MEAN B VALUE (OVERALL, A**2): 24.592 |
| REMARK 3 | | OVERALL ANISOTROPIC B VALUE. |
| REMARK 3 | | B11 (A**2): .41 |
| REMARK 3 | | B22 (A**2): .41 |
| REMARK 3 | | B33 (A**2): −.81 |
| REMARK 3 | | B12 (A**2): .00 |
| REMARK 3 | | B13 (A**2): .00 |
| REMARK 3 | | B23 (A**2): .00 |
| REMARK 3 | | |
| REMARK 3 | | ESTIMATED OVERALL COORDINATE ERROR. |
| REMARK 3 | | ESU BASED ON R VALUE (A): NULL |
| REMARK 3 | | ESU BASED ON FREE R VALUE (A): .427 |
| REMARK 3 | | ESU BASED ON MAXIMUM LIKELIHOOD (A): .327 |
| REMARK 3 | | ESU FOR B VALUES BASED ON MAXIMUM LIKELIHOOD (A**2): 39.836 |
| REMARK 3 | | |
| REMARK 3 | | CORRELATION COEFFICIENTS. |
| REMARK 3 | | CORRELATION COEFFICIENT FO-FC: .916 |
| REMARK 3 | | CORRELATION COEFFICIENT FO-FC FREE: .868 |
| REMARK 3 | | |
| REMARK 3 | | RMS DEVIATIONS FROM IDEAL VALUES COUNT RMS WEIGHT |
| REMARK 3 | | BOND LENGTHS REFINED ATOMS (A): 8495; .011; .022 |
| REMARK 3 | | BOND LENGTHS OTHERS (A): 5804; .001; .020 |
| REMARK 3 | | BOND ANGLES REFINED ATOMS (DEGREES): 11476; 1.279; 1.953 |
| REMARK 3 | | BOND ANGLES OTHERS (DEGREES): 14093; .882; 3.000 |
| REMARK 3 | | TORSION ANGLES, PERIOD 1 (DEGREES): 1020; 7.002; 5.000 |
| REMARK 3 | | TORSION ANGLES, PERIOD 2 (DEGREES): 435; 35.412; 24.299 |
| REMARK 3 | | TORSION ANGLES, PERIOD 3 (DEGREES): 1525; 18.250; 15.000 |
| REMARK 3 | | TORSION ANGLES, PERIOD 4 (DEGREES): 58; 16.811; 15.000 |
| REMARK 3 | | CHIRAL-CENTER RESTRAINTS (A**3): 1266; .070; .200 |
| REMARK 3 | | GENERAL PLANES REFINED ATOMS (A): 9416; .005; .020 |
| REMARK 3 | | GENERAL PLANES OTHERS (A): 1780; .001; .020 |
| REMARK 3 | | |
| REMARK 3 | | ISOTROPIC THERMAL FACTOR RESTRAINTS. COUNT RMS WEIGHT |
| REMARK 3 | | MAIN-CHAIN BOND REFINED ATOMS (A**2): 5104; .514; 1.500 |
| REMARK 3 | | MAIN-CHAIN BOND OTHER ATOMS (A**2): 2068; .059; 1.500 |
| REMARK 3 | | MAIN-CHAIN ANGLE REFINED ATOMS (A**2): 8204; 1.000; 2.000 |
| REMARK 3 | | SIDE-CHAIN BOND REFINED ATOMS (A**2): 3391; 1.218; 3.000 |
| REMARK 3 | | SIDE-CHAIN ANGLE REFINED ATOMS (A**2): 3272; 2.157; 4.500 |
| REMARK 3 | | |
| REMARK 3 | | NCS RESTRAINTS STATISTICS |
| REMARK 3 | | NUMBER OF DIFFERENT NCS GROUPS: F 1 |
| REMARK 3 | | |
| REMARK 3 | | NCS GROUP NUMBER: 1 |

TABLE 3-7-continued

Coordinates of *P. tremuloides* IspS

| | |
|---|---|
| REMARK 3 | CHAIN NAMES: A B |
| REMARK 3 | NUMBER OF COMPONENTS NCS GROUP: 1 |
| REMARK 3 | COMPONENT C SSSEQI TO C SSSEQI CODE |
| REMARK 3 | 1 A 17 A 541 6 |
| REMARK 3 | 1 B 17 B 541 6 |
| REMARK 3 | GROUP CHAIN COUNT RMS WEIGHT |
| REMARK 3 | LOOSE POSITIONAL 1 1 (A): 7038; .37; 5.00 |
| REMARK 3 | LOOSE THERMAL 1 1 (A**2): 7038; 1.09; 10.00 |
| REMARK 3 | |
| REMARK 3 | TWIN DETAILS |
| REMARK 3 | NUMBER OF TWIN DOMAINS: NULL |
| REMARK 3 | |
| REMARK 3 | |
| REMARK 3 | TLS DETAILS |
| REMARK 3 | NUMBER OF TLS GROUPS: 8 |
| REMARK 3 | ATOM RECORD CONTAINS RESIDUAL B FACTORS ONLY |
| REMARK 3 | |
| REMARK 3 | TLS GROUP: 1 |
| REMARK 3 | NUMBER OF COMPONENTS GROUP: 1 |
| REMARK 3 | COMPONENTS C SSSEQI TO C SSSEQI |
| REMARK 3 | RESIDUE RANGE: A 17 A 219 |
| REMARK 3 | ORIGIN FOR THE GROUP (A): −64.7667 37.6643 −.0896 |
| REMARK 3 | T TENSOR |
| REMARK 3 | T11: .0648 T22: .0357 |
| REMARK 3 | T33: .0787 T12: .0200 |
| REMARK 3 | T13: .0129 T23: −.0089 |
| REMARK 3 | L TENSOR |
| REMARK 3 | L11: 3.7204 L22: 1.5111 |
| REMARK 3 | L33: 2.6701 L12: .5715 |
| REMARK 3 | L13: .6692 L23: −.9699 |
| REMARK 3 | S TENSOR |
| REMARK 3 | S11: .0562 S12: .0478 S13: −.1976 |
| REMARK 3 | S21: −.1702 S22: −.0055 S23: .1376 |
| REMARK 3 | S31: .0900 S32: −.2188 S33: −.0507 |
| REMARK 3 | |
| REMARK 3 | TLS GROUP: 2 |
| REMARK 3 | NUMBER OF COMPONENTS GROUP: 1 |
| REMARK 3 | COMPONENTS C SSSEQI TO C SSSEQI |
| REMARK 3 | RESIDUE RANGE: A 220 A 287 |
| REMARK 3 | ORIGIN FOR THE GROUP (A): −59.5787 8.4529 −.7693 |
| REMARK 3 | T TENSOR |
| REMARK 3 | T11: .1615 T22: .0645 |
| REMARK 3 | T33: .1539 T12: −.0314 |
| REMARK 3 | T13: −.0461 T23: .0198 |
| REMARK 3 | L TENSOR |
| REMARK 3 | L11: 2.4192 L22: 4.6709 |
| REMARK 3 | L33: .7709 L12: −3.2943 |
| REMARK 3 | L13: −.1814 L23: −.0705 |
| REMARK 3 | S TENSOR |
| REMARK 3 | S11: .0055 S12: −.0699 S13: −.2073 |
| REMARK 3 | S21: −.1805 S22: .0996 S23: .3781 |
| REMARK 3 | S31: .2596 S32: .0887 S33: −.1051 |
| REMARK 3 | |
| REMARK 3 | TLS GROUP: 3 |
| REMARK 3 | NUMBER OF COMPONENTS GROUP: 1 |
| REMARK 3 | COMPONENTS C SSSEQI TO C SSSEQI |
| REMARK 3 | RESIDUE RANGE: A 288 A 374 |
| REMARK 3 | ORIGIN FOR THE GROUP (A): −40.1866 1.6932 .5805 |
| REMARK 3 | T TENSOR |
| REMARK 3 | T11: .1149 T22: .1003 |
| REMARK 3 | T33: .1629 T12: .0153 |
| REMARK 3 | T13: .0224 T23: .0164 |
| REMARK 3 | L TENSOR |
| REMARK 3 | L11: .2271 L22: .7399 |
| REMARK 3 | L33: 4.8529 L12: .3413 |
| REMARK 3 | L13: .4755 L23: −.1746 |
| REMARK 3 | S TENSOR |
| REMARK 3 | S11: −.0449 S12: −.0288 S13: −.1131 |
| REMARK 3 | S21: −.1346 S22: −.0665 S23: −.2749 |
| REMARK 3 | S31: −.0040 S32: .1558 S33: .1114 |
| REMARK 3 | |
| REMARK 3 | TLS GROUP: 4 |
| REMARK 3 | NUMBER OF COMPONENTS GROUP: 1 |
| REMARK 3 | COMPONENTS C SSSEQI TO C SSSEQI |
| REMARK 3 | RESIDUE RANGE: A 375 A 541 |
| REMARK 3 | ORIGIN FOR THE GROUP (A): −47.2220 21.5399 6.9217 |
| REMARK 3 | T TENSOR |

TABLE 3-7-continued

Coordinates of *P. tremuloides* IspS

```
REMARK  3    T11:  .1551 T22:  .1194
REMARK  3    T33:  .1485 T12: -.0666
REMARK  3    T13:  .0275 T23:  .0272
REMARK  3    L TENSOR
REMARK  3    L11: 2.2352 L22: 2.1698
REMARK  3    L33: 2.3370 L12: -.4501
REMARK  3    L13: 2.2662 L23: -.1852
REMARK  3    S TENSOR
REMARK  3    S11:  .0233 S12: -.3041 S13: -.0323
REMARK  3    S21:  .3375 S22:  .0236 S23:  .0121
REMARK  3    S31:  .0592 S32: -.2979 S33: -.0469
REMARK  3
REMARK  3    TLS GROUP:  5
REMARK  3    NUMBER OF COMPONENTS GROUP:  1
REMARK  3    COMPONENTS C SSSEQI TO C SSSEQI
REMARK  3    RESIDUE RANGE:   B 17 B 219
REMARK  3    ORIGIN FOR THE GROUP (A): -73.9834 -39.9016 -18.5783
REMARK  3    T TENSOR
REMARK  3    T11:  .0658 T22:  .1153
REMARK  3    T33:  .1251 T12: -.0621
REMARK  3    T13: -.0164 T23: -.0098
REMARK  3    L TENSOR
REMARK  3    L11: 4.6230 L22: 1.7260
REMARK  3    L33: 3.8816 L12: -.4202
REMARK  3    L13: -1.8646 L23: -.9046
REMARK  3    S TENSOR
REMARK  3    S11: -.0685 S12:  .0375 S13: -.0003
REMARK  3    S21:  .1931 S22:  .0510 S23: -.0097
REMARK  3    S31:  .0317 S32: -.2047 S33:  .0175
REMARK  3
REMARK  3    TLS GROUP:  6
REMARK  3    NUMBER OF COMPONENTS GROUP:  1
REMARK  3    COMPONENTS   C SSSEQI TO   C SSSEQI
REMARK  3    RESIDUE RANGE:   B   220   B   287
REMARK  3    ORIGIN FOR THE GROUP (A): -62.1586 -12.7634 -18.1912
REMARK  3    T TENSOR
REMARK  3    T11:  .1825 T22:  .0804
REMARK  3    T33:  .1512 T12:  .0549
REMARK  3    T13:  .0773 T23:  .0208
REMARK  3    L TENSOR
REMARK  3    L11: 5.4421 L22: 4.0606
REMARK  3    L33: 1.5369 L12: 4.6706
REMARK  3    L13: -2.0058 L23: -1.5537
REMARK  3    S TENSOR
REMARK  3    S11:  .1622 S12:  .0431 S13:  .3257
REMARK  3    S21:  .1755 S22:  .0292 S23:  .2977
REMARK  3    S31: -.1910 S32: -.0506 S33: -.1914
REMARK  3
REMARK  3    TLS GROUP:  7
REMARK  3    NUMBER OF COMPONENTS GROUP:  1
REMARK  3    COMPONENTS   C SSSEQI TO   C SSSEQI
REMARK  3    RESIDUE RANGE: B   288   B   374
REMARK  3    ORIGIN FOR THE GROUP (A): -41.6930 -10.8250 -19.6636
REMARK  3    T TENSOR
REMARK  3    T11:  .1424 T22:  .0604
REMARK  3    T33:  .1153 T12:  .0184
REMARK  3    T13:  .0146 T23:  .0276
REMARK  3    L TENSOR
REMARK  3    L11:  .6426 L22:  .8163
REMARK  3    L33: 2.3437 L12: -.1831
REMARK  3    L13: -.5246 L23:  .4917
REMARK  3    S TENSOR
REMARK  3    S11:  .0592 S12: -.0206 S13:  .0071
REMARK  3    S21:  .0906 S22: -.0229 S23: -.1585
REMARK  3    S31: -.0355 S32:  .0262 S33: -.0363
REMARK  3
REMARK  3    TLS GROUP:  8
REMARK  3    NUMBER OF COMPONENTS GROUP:  1
REMARK  3    COMPONENTS   C SSSEQI TO   C SSSEQI
REMARK  3    RESIDUE RANGE:   B   375   B   541
REMARK  3    ORIGIN FOR THE GROUP (A): -53.4886 -28.3212 -26.0670
REMARK  3    T TENSOR
REMARK  3    T11:  .1107 T22:  .1220
REMARK  3    T33:  .1514 T12:  .0692
REMARK  3    T13: -.0073 T23:  .0518
REMARK  3    L TENSOR
REMARK  3    L11: 2.6766 L22:  1.8433
REMARK  3    L33: 2.6389 L12:  .1130
```

TABLE 3-7-continued

Coordinates of *P. tremuloides* IspS

| REMARK | 3 | L13: −2.4696 L23: .6986 |
|---|---|---|
| REMARK | 3 | S TENSOR |
| REMARK | 3 | S11: .1115 S12: .3882 S13: .0569 |
| REMARK | 3 | S21: −.0725 S22: −.0724 S23: .1450 |
| REMARK | 3 | S31: −.1453 S32: −.4044 S33: −.0392 |
| REMARK | 3 | |
| REMARK | 3 | |
| REMARK | 3 | BULK SOLVENT MODELLING. |
| REMARK | 3 | METHOD USED: MASK |
| REMARK | 3 | PARAMETERS FOR MASK CALCULATION |
| REMARK | 3 | VDW PROBE RADIUS: 1.40 |
| REMARK | 3 | ION PROBE RADIUS: .80 |
| REMARK | 3 | SHRINKAGE RADIUS: .80 |
| REMARK | 3 | |
| REMARK | 3 | OTHER REFINEMENT REMARKS: |
| REMARK | 3 | HYDROGENS HAVE BEEN ADDED IN THE RIDING POSITIONS |
| REMARK | 3 | U VALUES: RESIDUAL ONLY |
| REMARK | 3 | |
| CISPEP | 1 | ALA A 446 ARG A 447 .00 |
| CISPEP | 2 | GLY A 515 ASP A 516 .00 |
| CISPEP | 3 | THR B 22 ASP B 23 .00 |
| CISPEP | 4 | ALA B 446 ARG B 447 .00 |
| CISPEP | 5 | GLY B 515 ASP B 516 .00 |
| CRYST1 | | 155.800 155.800 143.690 90.00 90.00 90.00 P 43 21 2 |
| SCALE1 | | .006418 .000000 .000000 .00000 |
| SCALE2 | | .000000 .006418 .000000 .00000 |
| SCALE3 | | .000000 .000000 .006959 .00000 |
| ATOM | 1 | N | LEU | A | 17 | −63.930 | 24.416 | −19.202 | 1.00 | 30.90 | N |
| ATOM | 2 | CA | LEU | A | 17 | −64.132 | 23.019 | −19.731 | 1.00 | 31.43 | C |
| ATOM | 4 | CB | LEU | A | 17 | −63.308 | 22.800 | −21.021 | 1.00 | 31.35 | C |
| ATOM | 7 | CG | LEU | A | 17 | −64.002 | 23.016 | −22.386 | 1.00 | 31.95 | C |
| ATOM | 9 | CD1 | LEU | A | 17 | −62.989 | 23.068 | −23.550 | 1.00 | 31.88 | C |
| ATOM | 13 | CD2 | LEU | A | 17 | −65.052 | 21.915 | −22.676 | 1.00 | 31.95 | C |
| ATOM | 17 | C | LEU | A | 17 | −63.783 | 21.952 | −18.660 | 1.00 | 31.39 | C |
| ATOM | 18 | O | LEU | A | 17 | −63.142 | 22.291 | −17.651 | 1.00 | 31.61 | O |
| ATOM | 22 | N | LEU | A | 18 | −64.216 | 20.693 | −18.877 | 1.00 | 31.11 | N |
| ATOM | 23 | CA | LEU | A | 18 | −63.986 | 19.529 | −17.957 | 1.00 | 30.78 | C |
| ATOM | 25 | CB | LEU | A | 18 | −62.503 | 19.072 | −17.935 | 1.00 | 30.97 | C |
| ATOM | 28 | CG | LEU | A | 18 | −61.303 | 19.949 | −17.496 | 1.00 | 31.10 | C |
| ATOM | 30 | CD1 | LEU | A | 18 | −61.406 | 20.430 | −16.064 | 1.00 | 30.71 | C |
| ATOM | 34 | CD2 | LEU | A | 18 | −59.977 | 19.173 | −17.703 | 1.00 | 31.87 | C |
| ATOM | 38 | C | LEU | A | 18 | −64.531 | 19.665 | −16.522 | 1.00 | 30.38 | C |
| ATOM | 39 | O | LEU | A | 18 | −64.837 | 18.667 | −15.883 | 1.00 | 29.86 | O |
| ATOM | 41 | N | SER | A | 19 | −64.587 | 20.900 | −16.023 | 1.00 | 30.45 | N |
| ATOM | 42 | CA | SER | A | 19 | −65.335 | 21.276 | −14.815 | 1.00 | 30.37 | C |
| ATOM | 44 | CB | SER | A | 19 | −64.604 | 22.417 | −14.026 | 1.00 | 30.02 | C |
| ATOM | 47 | OG | SER | A | 19 | −64.881 | 23.741 | −14.489 | 1.00 | 28.00 | O |
| ATOM | 49 | C | SER | A | 19 | −66.784 | 21.654 | −15.218 | 1.00 | 31.03 | C |
| ATOM | 50 | O | SER | A | 19 | −67.666 | 21.711 | −14.367 | 1.00 | 30.95 | O |
| ATOM | 52 | N | SER | A | 20 | −67.023 | 21.880 | −16.519 | 1.00 | 31.85 | N |
| ATOM | 53 | CA | SER | A | 20 | −68.355 | 22.247 | −17.051 | 1.00 | 32.37 | C |
| ATOM | 55 | CB | SER | A | 20 | −68.291 | 22.507 | −18.579 | 1.00 | 32.39 | C |
| ATOM | 58 | OG | SER | A | 20 | −67.387 | 23.542 | −18.931 | 1.00 | 31.77 | O |
| ATOM | 60 | C | SER | A | 20 | −69.357 | 21.124 | −16.744 | 1.00 | 33.04 | C |
| ATOM | 61 | O | SER | A | 20 | −69.076 | 20.254 | −15.922 | 1.00 | 33.08 | O |
| ATOM | 63 | N | ASP | A | 21 | −70.522 | 21.136 | −17.393 | 1.00 | 33.88 | N |
| ATOM | 64 | CA | ASP | A | 21 | −71.512 | 20.069 | −17.206 | 1.00 | 34.48 | C |
| ATOM | 66 | CB | ASP | A | 21 | −72.907 | 20.655 | −17.127 | 1.00 | 34.59 | C |
| ATOM | 69 | CG | ASP | A | 21 | −73.022 | 21.661 | −16.006 | 1.00 | 35.54 | C |
| ATOM | 70 | OD1 | ASP | A | 21 | −72.041 | 21.836 | −15.251 | 1.00 | 35.31 | O |
| ATOM | 71 | OD2 | ASP | A | 21 | −74.082 | 22.289 | −15.870 | 1.00 | 38.72 | O |
| ATOM | 72 | C | ASP | A | 21 | −71.409 | 18.975 | −18.260 | 1.00 | 34.94 | C |
| ATOM | 73 | O | ASP | A | 21 | −72.134 | 18.947 | −19.269 | 1.00 | 34.58 | O |
| ATOM | 75 | N | THR | A | 22 | −70.457 | 18.086 | −17.989 | 1.00 | 35.66 | N |
| ATOM | 76 | CA | THR | A | 22 | −70.340 | 16.799 | −18.657 | 1.00 | 36.27 | C |
| ATOM | 78 | CB | THR | A | 22 | −68.895 | 16.576 | −19.168 | 1.00 | 36.30 | C |
| ATOM | 80 | OG1 | THR | A | 22 | −67.968 | 17.278 | −18.322 | 1.00 | 36.04 | O |
| ATOM | 82 | CG2 | THR | A | 22 | −68.755 | 17.088 | −20.604 | 1.00 | 36.11 | C |
| ATOM | 86 | C | THR | A | 22 | −70.792 | 15.714 | −17.648 | 1.00 | 36.83 | C |
| ATOM | 87 | O | THR | A | 22 | −69.968 | 15.022 | −17.035 | 1.00 | 37.05 | O |
| ATOM | 89 | N | ASP | A | 23 | −72.121 | 15.599 | −17.494 | 1.00 | 37.27 | N |
| ATOM | 90 | CA | ASP | A | 23 | −72.790 | 14.802 | −16.441 | 1.00 | 37.25 | C |
| ATOM | 92 | CB | ASP | A | 23 | −72.962 | 15.659 | −15.167 | 1.00 | 37.17 | C |
| ATOM | 95 | CG | ASP | A | 23 | −71.625 | 16.081 | −14.549 | 1.00 | 37.74 | C |
| ATOM | 96 | OD1 | ASP | A | 23 | −70.714 | 15.241 | −14.436 | 1.00 | 38.88 | O |
| ATOM | 97 | OD2 | ASP | A | 23 | −71.472 | 17.256 | −14.164 | 1.00 | 38.91 | O |
| ATOM | 98 | C | ASP | A | 23 | −74.172 | 14.351 | −16.956 | 1.00 | 37.18 | C |

TABLE 3-7-continued

Coordinates of *P. tremuloides* IspS

| ATOM | 99 | O | ASP | A | 23 | −75.137 | 15.112 | −16.846 | 1.00 | 37.10 | O |
|---|---|---|---|---|---|---|---|---|---|---|---|
| ATOM | 101 | N | GLU | A | 24 | −74.280 | 13.134 | −17.501 | 1.00 | 37.23 | N |
| ATOM | 102 | CA | GLU | A | 24 | −75.406 | 12.815 | −18.410 | 1.00 | 37.58 | C |
| ATOM | 104 | CB | GLU | A | 24 | −74.941 | 13.007 | −19.865 | 1.00 | 37.77 | C |
| ATOM | 107 | CG | GLU | A | 24 | −74.424 | 14.417 | −20.239 | 1.00 | 37.98 | C |
| ATOM | 110 | CD | GLU | A | 24 | −74.121 | 14.556 | −21.746 | 1.00 | 38.35 | C |
| ATOM | 111 | OE1 | GLU | A | 24 | −74.284 | 13.564 | −22.503 | 1.00 | 38.12 | O |
| ATOM | 112 | OE2 | GLU | A | 24 | −73.721 | 15.661 | −22.174 | 1.00 | 38.18 | O |
| ATOM | 113 | C | GLU | A | 24 | −76.139 | 11.440 | −18.323 | 1.00 | 37.79 | C |
| ATOM | 114 | O | GLU | A | 24 | −77.323 | 11.397 | −17.960 | 1.00 | 37.90 | O |
| ATOM | 116 | N | SER | A | 25 | −75.462 | 10.345 | −18.696 | 1.00 | 37.92 | N |
| ATOM | 117 | CA | SER | A | 25 | −76.140 | 9.070 | −19.048 | 1.00 | 38.09 | C |
| ATOM | 119 | CB | SER | A | 25 | −75.167 | 8.076 | −19.723 | 1.00 | 38.11 | C |
| ATOM | 122 | OG | SER | A | 25 | −74.503 | 7.239 | −18.787 | 1.00 | 38.02 | O |
| ATOM | 124 | C | SER | A | 25 | −76.917 | 8.374 | −17.907 | 1.00 | 38.42 | C |
| ATOM | 125 | O | SER | A | 25 | −76.635 | 8.581 | −16.724 | 1.00 | 38.15 | O |
| ATOM | 127 | N | ILE | A | 26 | −77.861 | 7.511 | −18.312 | 1.00 | 39.00 | N |
| ATOM | 128 | CA | ILE | A | 26 | −78.993 | 7.042 | −17.476 | 1.00 | 39.30 | C |
| ATOM | 130 | CB | ILE | A | 26 | −78.594 | 5.965 | −16.429 | 1.00 | 39.34 | C |
| ATOM | 132 | CG1 | ILE | A | 26 | −77.892 | 4.791 | −17.120 | 1.00 | 39.37 | C |
| ATOM | 135 | CD1 | ILE | A | 26 | −77.766 | 3.531 | −16.253 | 1.00 | 39.46 | C |
| ATOM | 139 | CG2 | ILE | A | 26 | −79.836 | 5.423 | −15.714 | 1.00 | 39.29 | C |
| ATOM | 143 | C | ILE | A | 26 | −79.716 | 8.260 | −16.852 | 1.00 | 39.66 | C |
| ATOM | 144 | O | ILE | A | 26 | −79.274 | 8.831 | −15.838 | 1.00 | 39.49 | O |
| ATOM | 146 | N | GLU | A | 27 | −80.837 | 8.623 | −17.486 | 1.00 | 39.99 | N |
| ATOM | 147 | CA | GLU | A | 27 | −81.450 | 9.965 | −17.383 | 1.00 | 40.11 | C |
| ATOM | 149 | CB | GLU | A | 27 | −82.395 | 10.183 | −18.587 | 1.00 | 40.19 | C |
| ATOM | 152 | CG | GLU | A | 27 | −81.632 | 10.311 | −19.904 | 1.00 | 40.60 | C |
| ATOM | 155 | CD | GLU | A | 27 | −82.528 | 10.434 | −21.116 | 1.00 | 41.06 | C |
| ATOM | 156 | OE1 | GLU | A | 27 | −83.328 | 9.502 | −21.367 | 1.00 | 41.10 | O |
| ATOM | 157 | OE2 | GLU | A | 27 | −82.409 | 11.458 | −21.830 | 1.00 | 41.36 | O |
| ATOM | 158 | C | GLU | A | 27 | −82.144 | 10.264 | −16.042 | 1.00 | 40.02 | C |
| ATOM | 159 | O | GLU | A | 27 | −81.977 | 9.518 | −15.071 | 1.00 | 40.01 | O |
| ATOM | 161 | N | VAL | A | 28 | −82.899 | 11.370 | −16.005 | 1.00 | 39.84 | N |
| ATOM | 162 | CA | VAL | A | 28 | −83.463 | 11.960 | −14.779 | 1.00 | 39.65 | C |
| ATOM | 164 | CB | VAL | A | 28 | −83.884 | 10.905 | −13.694 | 1.00 | 39.78 | C |
| ATOM | 166 | CG1 | VAL | A | 28 | −84.472 | 11.596 | −12.456 | 1.00 | 39.87 | C |
| ATOM | 170 | CG2 | VAL | A | 28 | −84.887 | 9.880 | −14.274 | 1.00 | 39.49 | C |
| ATOM | 174 | C | VAL | A | 28 | −82.469 | 12.980 | −14.206 | 1.00 | 39.46 | C |
| ATOM | 175 | O | VAL | A | 28 | −82.798 | 13.717 | −13.270 | 1.00 | 39.38 | O |
| ATOM | 177 | N | HIS | A | 29 | −81.264 | 13.025 | −14.786 | 1.00 | 39.30 | N |
| ATOM | 178 | CA | HIS | A | 29 | −80.236 | 14.006 | −14.412 | 1.00 | 39.23 | C |
| ATOM | 180 | CB | HIS | A | 29 | −78.866 | 13.344 | −14.186 | 1.00 | 39.45 | C |
| ATOM | 183 | CG | HIS | A | 29 | −78.910 | 12.139 | −13.296 | 1.00 | 41.29 | C |
| ATOM | 184 | ND1 | HIS | A | 29 | −78.407 | 12.140 | −12.007 | 1.00 | 42.51 | N |
| ATOM | 186 | CE1 | HIS | A | 29 | −78.585 | 10.942 | −11.472 | 1.00 | 43.37 | C |
| ATOM | 188 | NE2 | HIS | A | 29 | −79.181 | 10.164 | −12.365 | 1.00 | 43.18 | N |
| ATOM | 190 | CD2 | HIS | A | 29 | −79.393 | 10.888 | −13.515 | 1.00 | 42.55 | C |
| ATOM | 192 | C | HIS | A | 29 | −80.090 | 15.110 | −15.464 | 1.00 | 38.60 | C |
| ATOM | 193 | O | HIS | A | 29 | −79.049 | 15.774 | −15.499 | 1.00 | 38.61 | O |
| ATOM | 195 | N | LYS | A | 30 | −81.110 | 15.320 | −16.311 | 1.00 | 37.87 | N |
| ATOM | 196 | CA | LYS | A | 30 | −81.265 | 16.610 | −17.001 | 1.00 | 37.22 | C |
| ATOM | 198 | CB | LYS | A | 30 | −82.283 | 16.542 | −18.140 | 1.00 | 37.09 | C |
| ATOM | 201 | CG | LYS | A | 30 | −81.764 | 15.794 | −19.360 | 1.00 | 37.00 | C |
| ATOM | 204 | CD | LYS | A | 30 | −82.831 | 15.653 | −20.457 | 1.00 | 36.89 | C |
| ATOM | 207 | CE | LYS | A | 30 | −82.413 | 14.637 | −21.531 | 1.00 | 36.48 | C |
| ATOM | 210 | NZ | LYS | A | 30 | −83.422 | 14.458 | −22.611 | 1.00 | 35.46 | N |
| ATOM | 214 | C | LYS | A | 30 | −81.648 | 17.649 | −15.938 | 1.00 | 36.88 | C |
| ATOM | 215 | O | LYS | A | 30 | −82.516 | 18.499 | −16.136 | 1.00 | 36.71 | O |
| ATOM | 217 | N | ASP | A | 31 | −80.982 | 17.506 | −14.788 | 1.00 | 36.58 | N |
| ATOM | 218 | CA | ASP | A | 31 | −80.895 | 18.476 | −13.720 | 1.00 | 36.18 | C |
| ATOM | 220 | CB | ASP | A | 31 | −80.518 | 17.751 | −12.396 | 1.00 | 36.20 | C |
| ATOM | 223 | CG | ASP | A | 31 | −79.863 | 18.669 | −11.342 | 1.00 | 36.65 | C |
| ATOM | 224 | OD1 | ASP | A | 31 | −80.055 | 19.901 | −11.390 | 1.00 | 38.17 | O |
| ATOM | 225 | OD2 | ASP | A | 31 | −79.147 | 18.150 | −10.449 | 1.00 | 35.46 | O |
| ATOM | 226 | C | ASP | A | 31 | −79.811 | 19.426 | −14.226 | 1.00 | 35.74 | C |
| ATOM | 227 | O | ASP | A | 31 | −78.628 | 19.279 | −13.918 | 1.00 | 35.44 | O |
| ATOM | 229 | N | LYS | A | 32 | −80.220 | 20.343 | −15.096 | 1.00 | 35.30 | N |
| ATOM | 230 | CA | LYS | A | 32 | −79.360 | 21.449 | −15.507 | 1.00 | 34.69 | C |
| ATOM | 232 | CB | LYS | A | 32 | −78.698 | 21.188 | −16.849 | 1.00 | 34.63 | C |
| ATOM | 235 | CG | LYS | A | 32 | −77.699 | 20.042 | −16.765 | 1.00 | 34.51 | C |
| ATOM | 238 | CD | LYS | A | 32 | −76.953 | 19.853 | −18.078 | 1.00 | 34.48 | C |
| ATOM | 241 | CE | LYS | A | 32 | −76.859 | 18.387 | −18.503 | 1.00 | 33.77 | C |
| ATOM | 244 | NZ | LYS | A | 32 | −77.002 | 18.244 | −19.985 | 1.00 | 32.92 | N |
| ATOM | 248 | C | LYS | A | 32 | −80.162 | 22.745 | −15.459 | 1.00 | 34.01 | C |
| ATOM | 249 | O | LYS | A | 32 | −80.468 | 23.380 | −16.473 | 1.00 | 33.41 | O |
| ATOM | 251 | N | ALA | A | 33 | −80.540 | 23.051 | −14.219 | 1.00 | 33.21 | N |
| ATOM | 252 | CA | ALA | A | 33 | −80.785 | 24.381 | −13.766 | 1.00 | 32.60 | C |

TABLE 3-7-continued

Coordinates of *P. tremuloides* IspS

| ATOM | 254 | CB | ALA | A | 33 | −81.619 | 24.347 | −12.484 | 1.00 | 32.28 | C |
|---|---|---|---|---|---|---|---|---|---|---|---|
| ATOM | 258 | C | ALA | A | 33 | −79.411 | 25.031 | −13.524 | 1.00 | 32.31 | C |
| ATOM | 259 | O | ALA | A | 33 | −79.335 | 26.081 | −12.901 | 1.00 | 32.80 | O |
| ATOM | 261 | N | LYS | A | 34 | −78.323 | 24.389 | −13.968 | 1.00 | 31.70 | N |
| ATOM | 262 | CA | LYS | A | 34 | −77.035 | 25.071 | −14.186 | 1.00 | 31.12 | C |
| ATOM | 264 | CB | LYS | A | 34 | −75.863 | 24.089 | −14.128 | 1.00 | 31.23 | C |
| ATOM | 267 | CG | LYS | A | 34 | −75.118 | 24.077 | −12.791 | 1.00 | 31.76 | C |
| ATOM | 270 | CD | LYS | A | 34 | −73.584 | 24.412 | −12.921 | 1.00 | 31.49 | C |
| ATOM | 273 | CE | LYS | A | 34 | −72.685 | 23.269 | −12.506 | 1.00 | 30.50 | C |
| ATOM | 276 | NZ | LYS | A | 34 | −72.951 | 22.090 | −13.348 | 1.00 | 29.53 | N |
| ATOM | 280 | C | LYS | A | 34 | −77.024 | 25.884 | −15.518 | 1.00 | 30.50 | C |
| ATOM | 281 | O | LYS | A | 34 | −76.977 | 25.353 | −16.625 | 1.00 | 29.82 | O |
| ATOM | 283 | N | LYS | A | 35 | −76.927 | 27.191 | −15.337 | 1.00 | 29.97 | N |
| ATOM | 284 | CA | LYS | A | 35 | −77.632 | 28.233 | −16.098 | 1.00 | 29.41 | C |
| ATOM | 286 | CB | LYS | A | 35 | −78.852 | 27.704 | −16.867 | 1.00 | 29.53 | C |
| ATOM | 289 | CG | LYS | A | 35 | −80.166 | 27.594 | −16.077 | 1.00 | 30.18 | C |
| ATOM | 292 | CD | LYS | A | 35 | −81.030 | 28.858 | −16.203 | 1.00 | 31.25 | C |
| ATOM | 295 | CE | LYS | A | 35 | −82.375 | 28.721 | −15.486 | 1.00 | 31.85 | C |
| ATOM | 298 | NZ | LYS | A | 35 | −83.298 | 29.865 | −15.783 | 1.00 | 31.73 | N |
| ATOM | 302 | C | LYS | A | 35 | −78.053 | 29.277 | −15.026 | 1.00 | 28.53 | C |
| ATOM | 303 | O | LYS | A | 35 | −78.246 | 30.460 | −15.307 | 1.00 | 28.53 | O |
| ATOM | 305 | N | LEU | A | 36 | −78.225 | 28.791 | −13.796 | 1.00 | 27.29 | N |
| ATOM | 306 | CA | LEU | A | 36 | −77.998 | 29.576 | −12.594 | 1.00 | 26.21 | C |
| ATOM | 308 | CB | LEU | A | 36 | −78.088 | 28.679 | −11.364 | 1.00 | 25.76 | C |
| ATOM | 311 | CG | LEU | A | 36 | −79.468 | 28.350 | −10.832 | 1.00 | 24.08 | C |
| ATOM | 313 | CD1 | LEU | A | 36 | −79.376 | 27.233 | −9.836 | 1.00 | 22.16 | C |
| ATOM | 317 | CD2 | LEU | A | 36 | −80.051 | 29.586 | −10.213 | 1.00 | 23.45 | C |
| ATOM | 321 | C | LEU | A | 36 | −76.587 | 30.137 | −12.665 | 1.00 | 25.93 | C |
| ATOM | 322 | O | LEU | A | 36 | −76.290 | 31.221 | −12.137 | 1.00 | 26.11 | O |
| ATOM | 324 | N | GLU | A | 37 | −75.714 | 29.332 | −13.260 | 1.00 | 25.24 | N |
| ATOM | 325 | CA | GLU | A | 37 | −74.381 | 29.739 | −13.650 | 1.00 | 24.85 | C |
| ATOM | 327 | CB | GLU | A | 37 | −73.678 | 28.566 | −14.313 | 1.00 | 24.74 | C |
| ATOM | 330 | CG | GLU | A | 37 | −72.182 | 28.667 | −14.285 | 1.00 | 23.93 | C |
| ATOM | 333 | CD | GLU | A | 37 | −71.519 | 27.490 | −14.937 | 1.00 | 22.32 | C |
| ATOM | 334 | OE1 | GLU | A | 37 | −72.203 | 26.738 | −15.657 | 1.00 | 20.57 | O |
| ATOM | 335 | OE2 | GLU | A | 37 | −70.303 | 27.322 | −14.728 | 1.00 | 22.27 | O |
| ATOM | 336 | C | GLU | A | 37 | −74.391 | 30.927 | −14.600 | 1.00 | 24.69 | C |
| ATOM | 337 | O | GLU | A | 37 | −73.666 | 31.891 | −14.389 | 1.00 | 24.49 | O |
| ATOM | 339 | N | ALA | A | 38 | −75.203 | 30.850 | −15.650 | 1.00 | 24.68 | N |
| ATOM | 340 | CA | ALA | A | 38 | −75.352 | 31.960 | −16.599 | 1.00 | 24.87 | C |
| ATOM | 342 | CB | ALA | A | 38 | −76.453 | 31.656 | −17.609 | 1.00 | 24.53 | C |
| ATOM | 346 | C | ALA | A | 38 | −75.643 | 33.278 | −15.880 | 1.00 | 25.08 | C |
| ATOM | 347 | O | ALA | A | 38 | −75.009 | 34.295 | −16.135 | 1.00 | 25.21 | O |
| ATOM | 349 | N | GLU | A | 39 | −76.591 | 33.228 | −14.956 | 1.00 | 25.35 | N |
| ATOM | 350 | CA | GLU | A | 39 | −77.050 | 34.400 | −14.219 | 1.00 | 25.51 | C |
| ATOM | 352 | CB | GLU | A | 39 | −78.283 | 34.014 | −13.396 | 1.00 | 25.95 | C |
| ATOM | 355 | CG | GLU | A | 39 | −79.302 | 35.119 | −13.136 | 1.00 | 27.03 | C |
| ATOM | 358 | CD | GLU | A | 39 | −80.715 | 34.557 | −12.906 | 1.00 | 28.70 | C |
| ATOM | 359 | OE1 | GLU | A | 39 | −81.006 | 33.416 | −13.346 | 1.00 | 27.40 | O |
| ATOM | 360 | OE2 | GLU | A | 39 | −81.540 | 35.266 | −12.289 | 1.00 | 31.12 | O |
| ATOM | 361 | C | GLU | A | 39 | −75.970 | 34.966 | −13.306 | 1.00 | 25.11 | C |
| ATOM | 362 | O | GLU | A | 39 | −75.870 | 36.167 | −13.164 | 1.00 | 25.28 | O |
| ATOM | 364 | N | VAL | A | 40 | −75.182 | 34.107 | −12.672 | 1.00 | 24.86 | N |
| ATOM | 365 | CA | VAL | A | 40 | −74.079 | 34.568 | −11.824 | 1.00 | 24.69 | C |
| ATOM | 367 | CB | VAL | A | 40 | −73.511 | 33.420 | −10.952 | 1.00 | 24.56 | C |
| ATOM | 369 | CG1 | VAL | A | 40 | −72.239 | 33.857 | −10.240 | 1.00 | 23.69 | C |
| ATOM | 373 | CG2 | VAL | A | 40 | −74.553 | 32.955 | −9.955 | 1.00 | 24.68 | C |
| ATOM | 377 | C | VAL | A | 40 | −72.971 | 35.148 | −12.698 | 1.00 | 24.76 | C |
| ATOM | 378 | O | VAL | A | 40 | −72.337 | 36.139 | −12.362 | 1.00 | 24.16 | O |
| ATOM | 380 | N | ARG | A | 41 | −72.744 | 34.506 | −13.831 | 1.00 | 25.25 | N |
| ATOM | 381 | CA | ARG | A | 41 | −71.727 | 34.948 | −14.769 | 1.00 | 25.66 | C |
| ATOM | 383 | CB | ARG | A | 41 | −71.576 | 33.927 | −15.896 | 1.00 | 25.88 | C |
| ATOM | 386 | CG | ARG | A | 41 | −70.726 | 34.385 | −17.062 | 1.00 | 27.04 | C |
| ATOM | 389 | CD | ARG | A | 41 | −71.519 | 35.178 | −18.095 | 1.00 | 27.90 | C |
| ATOM | 392 | NE | ARG | A | 41 | −70.653 | 35.635 | −19.180 | 1.00 | 29.20 | N |
| ATOM | 394 | CZ | ARG | A | 41 | −70.946 | 36.615 | −20.034 | 1.00 | 29.94 | C |
| ATOM | 395 | NH1 | ARG | A | 41 | −70.077 | 36.945 | −20.980 | 1.00 | 29.86 | N |
| ATOM | 398 | NH2 | ARG | A | 41 | −72.096 | 37.273 | −19.957 | 1.00 | 30.54 | N |
| ATOM | 401 | C | ARG | A | 41 | −72.104 | 36.301 | −15.335 | 1.00 | 25.60 | C |
| ATOM | 402 | O | ARG | A | 41 | −71.237 | 37.113 | −15.612 | 1.00 | 25.77 | O |
| ATOM | 404 | N | ARG | A | 42 | −73.400 | 36.521 | −15.537 | 1.00 | 25.50 | N |
| ATOM | 405 | CA | ARG | A | 42 | −73.900 | 37.810 | −15.979 | 1.00 | 25.39 | C |
| ATOM | 407 | CB | ARG | A | 42 | −75.389 | 37.723 | −16.313 | 1.00 | 25.09 | C |
| ATOM | 410 | CG | ARG | A | 42 | −76.077 | 39.062 | −16.445 | 1.00 | 23.84 | C |
| ATOM | 413 | CD | ARG | A | 42 | −77.459 | 38.906 | −16.980 | 1.00 | 22.37 | C |
| ATOM | 416 | NE | ARG | A | 42 | −78.448 | 38.554 | −15.965 | 1.00 | 21.69 | N |
| ATOM | 418 | CZ | ARG | A | 42 | −79.705 | 38.206 | −16.248 | 1.00 | 22.99 | C |
| ATOM | 419 | NH1 | ARG | A | 42 | −80.122 | 38.146 | −17.517 | 1.00 | 24.16 | N |

TABLE 3-7-continued

Coordinates of *P. tremuloides* IspS

| ATOM | 422 | NH2 | ARG | A | 42 | −80.557 | 37.900 | −15.275 | 1.00 | 22.94 | N |
|------|-----|-----|-----|---|----|---------|--------|---------|------|-------|---|
| ATOM | 425 | C   | ARG | A | 42 | −73.666 | 38.889 | −14.925 | 1.00 | 26.00 | C |
| ATOM | 426 | O   | ARG | A | 42 | −73.173 | 39.959 | −15.244 | 1.00 | 26.17 | O |
| ATOM | 428 | N   | GLU | A | 43 | −74.014 | 38.621 | −13.673 | 1.00 | 26.66 | N |
| ATOM | 429 | CA  | GLU | A | 43 | −73.930 | 39.662 | −12.650 | 1.00 | 27.47 | C |
| ATOM | 431 | CB  | GLU | A | 43 | −74.749 | 39.304 | −11.401 | 1.00 | 27.97 | C |
| ATOM | 434 | CG  | GLU | A | 43 | −76.274 | 39.266 | −11.661 | 1.00 | 31.05 | C |
| ATOM | 437 | CD  | GLU | A | 43 | −76.869 | 40.636 | −12.063 | 1.00 | 34.68 | C |
| ATOM | 438 | OE1 | GLU | A | 43 | −76.804 | 41.571 | −11.222 | 1.00 | 37.63 | O |
| ATOM | 439 | OE2 | GLU | A | 43 | −77.398 | 40.773 | −13.205 | 1.00 | 34.52 | O |
| ATOM | 440 | C   | GLU | A | 43 | −72.494 | 40.035 | −12.275 | 1.00 | 27.15 | C |
| ATOM | 441 | O   | GLU | A | 43 | −72.292 | 41.118 | −11.716 | 1.00 | 27.49 | O |
| ATOM | 443 | N   | ILE | A | 44 | −71.517 | 39.166 | −12.588 | 1.00 | 26.57 | N |
| ATOM | 444 | CA  | ILE | A | 44 | −70.090 | 39.456 | −12.334 | 1.00 | 25.80 | C |
| ATOM | 446 | CB  | ILE | A | 44 | −69.206 | 38.187 | −12.187 | 1.00 | 25.52 | C |
| ATOM | 448 | CG1 | ILE | A | 44 | −69.624 | 37.320 | −11.010 | 1.00 | 24.69 | C |
| ATOM | 451 | CD1 | ILE | A | 44 | −68.828 | 36.061 | −10.899 | 1.00 | 23.08 | C |
| ATOM | 455 | CG2 | ILE | A | 44 | −67.790 | 38.581 | −11.916 | 1.00 | 25.73 | C |
| ATOM | 459 | C   | ILE | A | 44 | −69.522 | 40.286 | −13.472 | 1.00 | 25.40 | C |
| ATOM | 460 | O   | ILE | A | 44 | −68.745 | 41.211 | −13.236 | 1.00 | 25.26 | O |
| ATOM | 462 | N   | ASN | A | 45 | −69.912 | 39.945 | −14.700 | 1.00 | 25.14 | N |
| ATOM | 463 | CA  | ASN | A | 45 | −69.480 | 40.669 | −15.906 | 1.00 | 25.02 | C |
| ATOM | 465 | CB  | ASN | A | 45 | −69.696 | 39.813 | −17.151 | 1.00 | 24.69 | C |
| ATOM | 468 | CG  | ASN | A | 45 | −68.662 | 38.735 | −17.302 | 1.00 | 24.01 | C |
| ATOM | 469 | OD1 | ASN | A | 45 | −67.470 | 39.013 | −17.395 | 1.00 | 23.81 | O |
| ATOM | 470 | ND2 | ASN | A | 45 | −69.111 | 37.490 | −17.344 | 1.00 | 23.28 | N |
| ATOM | 473 | C   | ASN | A | 45 | −70.177 | 42.014 | −16.114 | 1.00 | 25.52 | C |
| ATOM | 474 | O   | ASN | A | 45 | −69.704 | 42.836 | −16.890 | 1.00 | 25.40 | O |
| ATOM | 476 | N   | ASN | A | 46 | −71.308 | 42.210 | −15.437 | 1.00 | 26.33 | N |
| ATOM | 477 | CA  | ASN | A | 46 | −72.085 | 43.453 | −15.468 | 1.00 | 26.72 | C |
| ATOM | 479 | CB  | ASN | A | 46 | −73.102 | 43.404 | −14.322 | 1.00 | 26.31 | C |
| ATOM | 482 | CG  | ASN | A | 46 | −73.935 | 44.641 | −14.209 | 1.00 | 24.24 | C |
| ATOM | 483 | OD1 | ASN | A | 46 | −73.948 | 45.472 | −15.091 | 1.00 | 22.38 | O |
| ATOM | 484 | ND2 | ASN | A | 46 | −74.645 | 44.766 | −13.106 | 1.00 | 21.64 | N |
| ATOM | 487 | C   | ASN | A | 46 | −71.185 | 44.680 | −15.349 | 1.00 | 28.11 | C |
| ATOM | 488 | O   | ASN | A | 46 | −70.603 | 44.933 | −14.304 | 1.00 | 28.16 | O |
| ATOM | 490 | N   | GLU | A | 47 | −71.084 | 45.441 | −16.433 | 1.00 | 29.93 | N |
| ATOM | 491 | CA  | GLU | A | 47 | −70.128 | 46.558 | −16.544 | 1.00 | 31.30 | C |
| ATOM | 493 | CB  | GLU | A | 47 | −69.933 | 46.969 | −18.013 | 1.00 | 31.28 | C |
| ATOM | 496 | CG  | GLU | A | 47 | −69.737 | 45.795 | −19.020 | 1.00 | 32.37 | C |
| ATOM | 499 | CD  | GLU | A | 47 | −71.060 | 45.127 | −19.545 | 1.00 | 32.69 | C |
| ATOM | 500 | OE1 | GLU | A | 47 | −72.055 | 45.833 | −19.816 | 1.00 | 32.16 | O |
| ATOM | 501 | OE2 | GLU | A | 47 | −71.087 | 43.880 | −19.699 | 1.00 | 32.41 | O |
| ATOM | 502 | C   | GLU | A | 47 | −70.582 | 47.774 | −15.729 | 1.00 | 32.47 | C |
| ATOM | 503 | O   | GLU | A | 47 | −69.760 | 48.525 | −15.230 | 1.00 | 32.86 | O |
| ATOM | 505 | N   | LYS | A | 48 | −71.898 | 47.945 | −15.585 | 1.00 | 33.93 | N |
| ATOM | 506 | CA  | LYS | A | 48 | −72.491 | 49.075 | −14.861 | 1.00 | 34.85 | C |
| ATOM | 508 | CB  | LYS | A | 48 | −73.660 | 49.672 | −15.684 | 1.00 | 35.08 | C |
| ATOM | 511 | CG  | LYS | A | 48 | −73.221 | 50.119 | −17.126 | 1.00 | 36.58 | C |
| ATOM | 514 | CD  | LYS | A | 48 | −74.035 | 51.277 | −17.751 | 1.00 | 37.93 | C |
| ATOM | 517 | CE  | LYS | A | 48 | −75.353 | 50.799 | −18.415 | 1.00 | 39.02 | C |
| ATOM | 520 | NZ  | LYS | A | 48 | −75.159 | 49.990 | −19.669 | 1.00 | 39.11 | N |
| ATOM | 524 | C   | LYS | A | 48 | −72.926 | 48.632 | −13.465 | 1.00 | 35.26 | C |
| ATOM | 525 | O   | LYS | A | 48 | −74.011 | 48.954 | −13.015 | 1.00 | 35.04 | O |
| ATOM | 527 | N   | ALA | A | 49 | −72.051 | 47.890 | −12.790 | 1.00 | 36.29 | N |
| ATOM | 528 | CA  | ALA | A | 49 | −72.321 | 47.348 | −11.456 | 1.00 | 37.18 | C |
| ATOM | 530 | CB  | ALA | A | 49 | −71.828 | 45.923 | −11.353 | 1.00 | 37.20 | C |
| ATOM | 534 | C   | ALA | A | 49 | −71.618 | 48.191 | −10.418 | 1.00 | 37.88 | C |
| ATOM | 535 | O   | ALA | A | 49 | −70.480 | 48.610 | −10.638 | 1.00 | 38.17 | O |
| ATOM | 537 | N   | GLU | A | 50 | −72.278 | 48.404 | −9.280  | 1.00 | 38.53 | N |
| ATOM | 538 | CA  | GLU | A | 50 | −71.730 | 49.242 | −8.213  | 1.00 | 39.08 | C |
| ATOM | 540 | CB  | GLU | A | 50 | −72.790 | 49.545 | −7.146  | 1.00 | 39.43 | C |
| ATOM | 543 | CG  | GLU | A | 50 | −72.708 | 50.953 | −6.600  | 1.00 | 40.86 | C |
| ATOM | 546 | CD  | GLU | A | 50 | −73.089 | 52.010 | −7.639  | 1.00 | 42.77 | C |
| ATOM | 547 | OE1 | GLU | A | 50 | −74.225 | 52.530 | −7.570  | 1.00 | 45.07 | O |
| ATOM | 548 | OE2 | GLU | A | 50 | −72.265 | 52.320 | −8.530  | 1.00 | 43.35 | O |
| ATOM | 549 | C   | GLU | A | 50 | −70.560 | 48.521 | −7.600  | 1.00 | 38.89 | C |
| ATOM | 550 | O   | GLU | A | 50 | −70.699 | 47.378 | −7.201  | 1.00 | 39.05 | O |
| ATOM | 552 | N   | PHE | A | 51 | −69.411 | 49.181 | −7.536  | 1.00 | 38.99 | N |
| ATOM | 553 | CA  | PHE | A | 51 | −68.161 | 48.502 | −7.196  | 1.00 | 39.52 | C |
| ATOM | 555 | CB  | PHE | A | 51 | −67.000 | 49.494 | −7.098  | 1.00 | 40.05 | C |
| ATOM | 558 | CG  | PHE | A | 51 | −66.460 | 49.948 | −8.431  | 1.00 | 42.80 | C |
| ATOM | 559 | CD1 | PHE | A | 51 | −66.135 | 49.014 | −9.435  | 1.00 | 45.21 | C |
| ATOM | 561 | CE1 | PHE | A | 51 | −65.612 | 49.425 | −10.675 | 1.00 | 46.12 | C |
| ATOM | 563 | CZ  | PHE | A | 51 | −65.403 | 50.790 | −10.917 | 1.00 | 47.21 | C |
| ATOM | 565 | CE2 | PHE | A | 51 | −65.726 | 51.741 | −9.913  | 1.00 | 46.72 | C |
| ATOM | 567 | CD2 | PHE | A | 51 | −66.247 | 51.310 | −8.679  | 1.00 | 45.05 | C |
| ATOM | 569 | C   | PHE | A | 51 | −68.223 | 47.687 | −5.905  | 1.00 | 39.05 | C |

TABLE 3-7-continued

Coordinates of *P. tremuloides* IspS

| ATOM | 570 | O   | PHE | A | 51 | −67.897 | 46.506 | −5.900  | 1.00 | 39.28 | O |
|------|-----|-----|-----|---|----|---------|--------|---------|------|-------|---|
| ATOM | 572 | N   | LEU | A | 52 | −68.648 | 48.307 | −4.813  | 1.00 | 38.42 | N |
| ATOM | 573 | CA  | LEU | A | 52 | −68.709 | 47.610 | −3.528  | 1.00 | 37.94 | C |
| ATOM | 575 | CB  | LEU | A | 52 | −69.084 | 48.594 | −2.413  | 1.00 | 38.53 | C |
| ATOM | 578 | CG  | LEU | A | 52 | −68.057 | 49.726 | −2.181  | 1.00 | 40.46 | C |
| ATOM | 580 | CD1 | LEU | A | 52 | −68.691 | 51.101 | −1.787  | 1.00 | 41.88 | C |
| ATOM | 584 | CD2 | LEU | A | 52 | −67.020 | 49.274 | −1.141  | 1.00 | 41.83 | C |
| ATOM | 588 | C   | LEU | A | 52 | −69.667 | 46.406 | −3.532  | 1.00 | 36.72 | C |
| ATOM | 589 | O   | LEU | A | 52 | −69.517 | 45.494 | −2.724  | 1.00 | 36.84 | O |
| ATOM | 591 | N   | THR | A | 53 | −70.649 | 46.398 | −4.431  | 1.00 | 35.37 | N |
| ATOM | 592 | CA  | THR | A | 53 | −71.545 | 45.247 | −4.569  | 1.00 | 34.11 | C |
| ATOM | 594 | CB  | THR | A | 53 | −72.867 | 45.594 | −5.277  | 1.00 | 33.87 | C |
| ATOM | 596 | OG1 | THR | A | 53 | −73.339 | 46.863 | −4.828  | 1.00 | 33.49 | O |
| ATOM | 598 | CG2 | THR | A | 53 | −73.917 | 44.535 | −4.983  | 1.00 | 33.70 | C |
| ATOM | 602 | C   | THR | A | 53 | −70.853 | 44.148 | −5.359  | 1.00 | 33.04 | C |
| ATOM | 603 | O   | THR | A | 53 | −70.893 | 42.977 | −4.973  | 1.00 | 32.90 | O |
| ATOM | 605 | N   | LEU | A | 54 | −70.228 | 44.528 | −6.467  | 1.00 | 31.76 | N |
| ATOM | 606 | CA  | LEU | A | 54 | −69.469 | 43.578 | −7.286  | 1.00 | 31.13 | C |
| ATOM | 608 | CB  | LEU | A | 54 | −68.721 | 44.308 | −8.392  | 1.00 | 30.92 | C |
| ATOM | 611 | CG  | LEU | A | 54 | −68.028 | 43.437 | −9.424  | 1.00 | 30.27 | C |
| ATOM | 613 | CD1 | LEU | A | 54 | −69.034 | 42.769 | −10.310 | 1.00 | 29.56 | C |
| ATOM | 617 | CD2 | LEU | A | 54 | −67.108 | 44.306 | −10.242 | 1.00 | 31.15 | C |
| ATOM | 621 | C   | LEU | A | 54 | −68.466 | 42.808 | −6.443  | 1.00 | 30.60 | C |
| ATOM | 622 | O   | LEU | A | 54 | −68.378 | 41.587 | −6.543  | 1.00 | 30.30 | O |
| ATOM | 624 | N   | LEU | A | 55 | −67.725 | 43.551 | −5.618  | 1.00 | 30.09 | N |
| ATOM | 625 | CA  | LEU | A | 55 | −66.730 | 43.000 | −4.695  | 1.00 | 29.47 | C |
| ATOM | 627 | CB  | LEU | A | 55 | −66.006 | 44.126 | −3.944  | 1.00 | 29.44 | C |
| ATOM | 630 | CG  | LEU | A | 55 | −65.069 | 45.017 | −4.781  | 1.00 | 29.74 | C |
| ATOM | 632 | CD1 | LEU | A | 55 | −64.609 | 46.255 | −4.003  | 1.00 | 29.43 | C |
| ATOM | 636 | CD2 | LEU | A | 55 | −63.859 | 44.234 | −5.286  | 1.00 | 29.64 | C |
| ATOM | 640 | C   | LEU | A | 55 | −67.340 | 42.024 | −3.696  | 1.00 | 28.87 | C |
| ATOM | 641 | O   | LEU | A | 55 | −66.746 | 40.991 | −3.383  | 1.00 | 28.98 | O |
| ATOM | 643 | N   | GLU | A | 56 | −68.525 | 42.330 | −3.198  | 1.00 | 28.01 | N |
| ATOM | 644 | CA  | GLU | A | 56 | −69.160 | 41.419 | −2.256  | 1.00 | 27.64 | C |
| ATOM | 646 | CB  | GLU | A | 56 | −70.172 | 42.173 | −1.395  | 1.00 | 28.19 | C |
| ATOM | 649 | CG  | GLU | A | 56 | −69.497 | 43.167 | −.459   | 1.00 | 29.75 | C |
| ATOM | 652 | CD  | GLU | A | 56 | −70.457 | 43.858 | .478    | 1.00 | 33.04 | C |
| ATOM | 653 | OE1 | GLU | A | 56 | −71.667 | 43.538 | .481    | 1.00 | 34.46 | O |
| ATOM | 654 | OE2 | GLU | A | 56 | −69.988 | 44.737 | 1.226   | 1.00 | 36.78 | O |
| ATOM | 655 | C   | GLU | A | 56 | −69.776 | 40.200 | −2.945  | 1.00 | 26.37 | C |
| ATOM | 656 | O   | GLU | A | 56 | −69.914 | 39.146 | −2.333  | 1.00 | 26.02 | O |
| ATOM | 658 | N   | LEU | A | 57 | −70.134 | 40.347 | −4.218  | 1.00 | 25.30 | N |
| ATOM | 659 | CA  | LEU | A | 57 | −70.569 | 39.212 | −5.036  | 1.00 | 24.17 | C |
| ATOM | 661 | CB  | LEU | A | 57 | −71.125 | 39.680 | −6.382  | 1.00 | 23.71 | C |
| ATOM | 664 | CG  | LEU | A | 57 | −71.417 | 38.568 | −7.390  | 1.00 | 22.27 | C |
| ATOM | 666 | CD1 | LEU | A | 57 | −72.515 | 37.675 | −6.858  | 1.00 | 19.31 | C |
| ATOM | 670 | CD2 | LEU | A | 57 | −71.752 | 39.167 | −8.768  | 1.00 | 20.30 | C |
| ATOM | 674 | C   | LEU | A | 57 | −69.404 | 38.267 | −5.284  | 1.00 | 23.69 | C |
| ATOM | 675 | O   | LEU | A | 57 | −69.547 | 37.051 | −5.136  | 1.00 | 23.83 | O |
| ATOM | 677 | N   | ILE | A | 58 | −68.261 | 38.822 | −5.682  | 1.00 | 22.82 | N |
| ATOM | 678 | CA  | ILE | A | 58 | −67.070 | 38.019 | −5.925  | 1.00 | 22.39 | C |
| ATOM | 680 | CB  | ILE | A | 58 | −65.884 | 38.899 | −6.355  | 1.00 | 22.21 | C |
| ATOM | 682 | CG1 | ILE | A | 58 | −66.088 | 39.386 | −7.792  | 1.00 | 21.83 | C |
| ATOM | 685 | CD1 | ILE | A | 58 | −65.002 | 40.314 | −8.320  | 1.00 | 20.43 | C |
| ATOM | 689 | CG2 | ILE | A | 58 | −64.565 | 38.131 | −6.245  | 1.00 | 22.64 | C |
| ATOM | 693 | C   | ILE | A | 58 | −66.719 | 37.227 | −4.662  | 1.00 | 22.35 | C |
| ATOM | 694 | O   | ILE | A | 58 | −66.520 | 36.002 | −4.706  | 1.00 | 21.95 | O |
| ATOM | 696 | N   | ASP | A | 59 | −66.676 | 37.951 | −3.543  | 1.00 | 22.32 | N |
| ATOM | 697 | CA  | ASP | A | 59 | −66.396 | 37.396 | −2.215  | 1.00 | 22.26 | C |
| ATOM | 699 | CB  | ASP | A | 59 | −66.570 | 38.500 | −1.171  | 1.00 | 22.67 | C |
| ATOM | 702 | CG  | ASP | A | 59 | −66.126 | 38.092 | .213    | 1.00 | 23.91 | C |
| ATOM | 703 | OD1 | ASP | A | 59 | −65.271 | 37.182 | .338    | 1.00 | 23.77 | O |
| ATOM | 704 | OD2 | ASP | A | 59 | −66.641 | 38.718 | 1.178   | 1.00 | 27.12 | O |
| ATOM | 705 | C   | ASP | A | 59 | −67.304 | 36.216 | −1.901  | 1.00 | 21.79 | C |
| ATOM | 706 | O   | ASP | A | 59 | −66.828 | 35.102 | −1.668  | 1.00 | 21.71 | O |
| ATOM | 708 | N   | ASN | A | 60 | −68.610 | 36.466 | −1.926  | 1.00 | 21.51 | N |
| ATOM | 709 | CA  | ASN | A | 60 | −69.619 | 35.418 | −1.759  | 1.00 | 21.28 | C |
| ATOM | 711 | CB  | ASN | A | 60 | −71.012 | 36.006 | −1.958  | 1.00 | 21.25 | C |
| ATOM | 714 | CG  | ASN | A | 60 | −71.476 | 36.827 | −.776   | 1.00 | 21.82 | C |
| ATOM | 715 | OD1 | ASN | A | 60 | −71.067 | 36.598 | .364    | 1.00 | 20.81 | O |
| ATOM | 716 | ND2 | ASN | A | 60 | −72.361 | 37.783 | −1.043  | 1.00 | 23.63 | N |
| ATOM | 719 | C   | ASN | A | 60 | −69.445 | 34.240 | −2.725  | 1.00 | 21.22 | C |
| ATOM | 720 | O   | ASN | A | 60 | −69.444 | 33.053 | −2.303  | 1.00 | 20.95 | O |
| ATOM | 722 | N   | VAL | A | 61 | −69.308 | 34.566 | −4.018  | 1.00 | 20.83 | N |
| ATOM | 723 | CA  | VAL | A | 61 | −69.147 | 33.536 | −5.043  | 1.00 | 20.57 | C |
| ATOM | 725 | CB  | VAL | A | 61 | −68.915 | 34.122 | −6.466  | 1.00 | 20.53 | C |
| ATOM | 727 | CG1 | VAL | A | 61 | −68.382 | 33.042 | −7.430  | 1.00 | 19.44 | C |
| ATOM | 731 | CG2 | VAL | A | 61 | −70.190 | 34.758 | −7.006  | 1.00 | 19.75 | C |

TABLE 3-7-continued

| | | | | | | | | | | | |
|---|---|---|---|---|---|---|---|---|---|---|---|
| ATOM | 735 | C | VAL | A | 61 | −67.981 | 32.646 | −4.644 | 1.00 | 20.62 | C |
| ATOM | 736 | O | VAL | A | 61 | −68.080 | 31.431 | −4.699 | 1.00 | 20.56 | O |
| ATOM | 738 | N | GLN | A | 62 | −66.888 | 33.255 | −4.209 | 1.00 | 20.76 | N |
| ATOM | 739 | CA | GLN | A | 62 | −65.703 | 32.481 | −3.898 | 1.00 | 21.18 | C |
| ATOM | 741 | CB | GLN | A | 62 | −64.461 | 33.379 | −3.824 | 1.00 | 21.39 | C |
| ATOM | 744 | CG | GLN | A | 62 | −64.007 | 33.920 | −5.165 | 1.00 | 21.64 | C |
| ATOM | 747 | CD | GLN | A | 62 | −62.608 | 34.512 | −5.135 | 1.00 | 22.04 | C |
| ATOM | 748 | OE1 | GLN | A | 62 | −61.890 | 34.483 | −6.145 | 1.00 | 23.18 | O |
| ATOM | 749 | NE2 | GLN | A | 62 | −62.217 | 35.062 | −3.989 | 1.00 | 20.39 | N |
| ATOM | 752 | C | GLN | A | 62 | −65.891 | 31.681 | −2.607 | 1.00 | 21.09 | C |
| ATOM | 753 | O | GLN | A | 62 | −65.544 | 30.485 | −2.554 | 1.00 | 21.30 | O |
| ATOM | 755 | N | ARG | A | 63 | −66.448 | 32.325 | −1.583 | 1.00 | 20.63 | N |
| ATOM | 756 | CA | ARG | A | 63 | −66.590 | 31.677 | −.273 | 1.00 | 20.54 | C |
| ATOM | 758 | CB | ARG | A | 63 | −67.025 | 32.686 | .786 | 1.00 | 20.57 | C |
| ATOM | 761 | CG | ARG | A | 63 | −66.031 | 33.823 | .930 | 1.00 | 22.55 | C |
| ATOM | 764 | CD | ARG | A | 63 | −66.214 | 34.632 | 2.179 | 1.00 | 24.93 | C |
| ATOM | 767 | NE | ARG | A | 63 | −66.123 | 33.781 | 3.355 | 1.00 | 27.75 | N |
| ATOM | 769 | CZ | ARG | A | 63 | −66.496 | 34.151 | 4.573 | 1.00 | 30.24 | C |
| ATOM | 770 | NH1 | ARG | A | 63 | −66.971 | 35.385 | 4.782 | 1.00 | 31.79 | N |
| ATOM | 773 | NH2 | ARG | A | 63 | −66.399 | 33.285 | 5.581 | 1.00 | 30.07 | N |
| ATOM | 776 | C | ARG | A | 63 | −67.557 | 30.499 | −.338 | 1.00 | 19.81 | C |
| ATOM | 777 | O | ARG | A | 63 | −67.283 | 29.431 | .209 | 1.00 | 19.67 | O |
| ATOM | 779 | N | LEU | A | 64 | −68.661 | 30.684 | −1.057 | 1.00 | 19.04 | N |
| ATOM | 780 | CA | LEU | A | 64 | −69.636 | 29.617 | −1.246 | 1.00 | 18.44 | C |
| ATOM | 782 | CB | LEU | A | 64 | −70.865 | 30.167 | −1.954 | 1.00 | 18.59 | C |
| ATOM | 785 | CG | LEU | A | 64 | −71.662 | 31.170 | −1.140 | 1.00 | 18.32 | C |
| ATOM | 787 | CD1 | LEU | A | 64 | −72.669 | 31.852 | −2.034 | 1.00 | 18.10 | C |
| ATOM | 791 | CD2 | LEU | A | 64 | −72.334 | 30.444 | .004 | 1.00 | 18.29 | C |
| ATOM | 795 | C | LEU | A | 64 | −69.089 | 28.436 | −2.037 | 1.00 | 17.80 | C |
| ATOM | 796 | O | LEU | A | 64 | −69.802 | 27.453 | −2.252 | 1.00 | 17.79 | O |
| ATOM | 798 | N | GLY | A | 65 | −67.850 | 28.573 | −2.515 | 1.00 | 17.07 | N |
| ATOM | 799 | CA | GLY | A | 65 | −67.084 | 27.480 | −3.081 | 1.00 | 16.27 | C |
| ATOM | 802 | C | GLY | A | 65 | −67.137 | 27.406 | −4.588 | 1.00 | 15.77 | C |
| ATOM | 803 | O | GLY | A | 65 | −66.893 | 26.347 | −5.154 | 1.00 | 15.78 | O |
| ATOM | 805 | N | LEU | A | 66 | −67.439 | 28.521 | −5.246 | 1.00 | 15.24 | N |
| ATOM | 806 | CA | LEU | A | 66 | −67.621 | 28.537 | −6.701 | 1.00 | 14.93 | C |
| ATOM | 808 | CB | LEU | A | 66 | −68.977 | 29.146 | −7.021 | 1.00 | 14.84 | C |
| ATOM | 811 | CG | LEU | A | 66 | −70.204 | 28.334 | −6.619 | 1.00 | 13.97 | C |
| ATOM | 813 | CD1 | LEU | A | 66 | −71.391 | 29.260 | −6.650 | 1.00 | 13.74 | C |
| ATOM | 817 | CD2 | LEU | A | 66 | −70.415 | 27.125 | −7.534 | 1.00 | 11.22 | C |
| ATOM | 821 | C | LEU | A | 66 | −66.533 | 29.314 | −7.454 | 1.00 | 15.09 | C |
| ATOM | 822 | O | LEU | A | 66 | −66.621 | 29.497 | −8.678 | 1.00 | 14.81 | O |
| ATOM | 824 | N | GLY | A | 67 | −65.510 | 29.758 | −6.720 | 1.00 | 15.21 | N |
| ATOM | 825 | CA | GLY | A | 67 | −64.404 | 30.526 | −7.280 | 1.00 | 14.98 | C |
| ATOM | 828 | C | GLY | A | 67 | −63.873 | 29.952 | −8.569 | 1.00 | 14.60 | C |
| ATOM | 829 | O | GLY | A | 67 | −63.891 | 30.619 | −9.579 | 1.00 | 14.63 | O |
| ATOM | 831 | N | TYR | A | 68 | −63.419 | 28.706 | −8.523 | 1.00 | 14.57 | N |
| ATOM | 832 | CA | TYR | A | 68 | −62.831 | 28.029 | −9.688 | 1.00 | 14.72 | C |
| ATOM | 834 | CB | TYR | A | 68 | −62.608 | 26.539 | −9.372 | 1.00 | 14.73 | C |
| ATOM | 837 | CG | TYR | A | 68 | −63.858 | 25.689 | −9.330 | 1.00 | 12.47 | C |
| ATOM | 838 | CD1 | TYR | A | 68 | −64.163 | 24.826 | −10.366 | 1.00 | 10.68 | C |
| ATOM | 840 | CE1 | TYR | A | 68 | −65.310 | 24.043 | −10.340 | 1.00 | 10.55 | C |
| ATOM | 842 | CZ | TYR | A | 68 | −66.163 | 24.119 | −9.258 | 1.00 | 10.41 | C |
| ATOM | 843 | OH | TYR | A | 68 | −67.311 | 23.349 | −9.212 | 1.00 | 6.97 | O |
| ATOM | 845 | CE2 | TYR | A | 68 | −65.864 | 24.979 | −8.210 | 1.00 | 11.44 | C |
| ATOM | 847 | CD2 | TYR | A | 68 | −64.722 | 25.750 | −8.252 | 1.00 | 11.29 | C |
| ATOM | 849 | C | TYR | A | 68 | −63.648 | 28.141 | −10.980 | 1.00 | 15.31 | C |
| ATOM | 850 | O | TYR | A | 68 | −63.106 | 28.230 | −12.083 | 1.00 | 15.01 | O |
| ATOM | 852 | N | ARG | A | 69 | −64.959 | 28.136 | −10.816 | 1.00 | 16.03 | N |
| ATOM | 853 | CA | ARG | A | 69 | −65.884 | 28.083 | −11.922 | 1.00 | 16.67 | C |
| ATOM | 855 | CB | ARG | A | 69 | −67.224 | 27.649 | −11.348 | 1.00 | 16.58 | C |
| ATOM | 858 | CG | ARG | A | 69 | −68.332 | 27.445 | −12.335 | 1.00 | 16.07 | C |
| ATOM | 861 | CD | ARG | A | 69 | −69.378 | 26.578 | −11.701 | 1.00 | 14.26 | C |
| ATOM | 864 | NE | ARG | A | 69 | −68.915 | 25.205 | −11.677 | 1.00 | 12.82 | N |
| ATOM | 866 | CZ | ARG | A | 69 | −69.063 | 24.346 | −12.676 | 1.00 | 12.42 | C |
| ATOM | 867 | NH1 | ARG | A | 69 | −69.676 | 24.694 | −13.792 | 1.00 | 12.27 | N |
| ATOM | 870 | NH2 | ARG | A | 69 | −68.601 | 23.119 | −12.553 | 1.00 | 13.23 | N |
| ATOM | 873 | C | ARG | A | 69 | −66.010 | 29.409 | −12.692 | 1.00 | 17.62 | C |
| ATOM | 874 | O | ARG | A | 69 | −66.281 | 29.401 | −13.892 | 1.00 | 17.10 | O |
| ATOM | 876 | N | PHE | A | 70 | −65.811 | 30.529 | −11.985 | 1.00 | 19.11 | N |
| ATOM | 877 | CA | PHE | A | 70 | −65.936 | 31.891 | −12.530 | 1.00 | 19.96 | C |
| ATOM | 879 | CB | PHE | A | 70 | −67.024 | 32.666 | −11.763 | 1.00 | 19.89 | C |
| ATOM | 882 | CG | PHE | A | 70 | −68.365 | 32.010 | −11.784 | 1.00 | 18.68 | C |
| ATOM | 883 | CD1 | PHE | A | 70 | −69.158 | 32.082 | −12.903 | 1.00 | 18.05 | C |
| ATOM | 885 | CE1 | PHE | A | 70 | −70.376 | 31.452 | −12.938 | 1.00 | 18.03 | C |
| ATOM | 887 | CZ | PHE | A | 70 | −70.825 | 30.754 | −11.851 | 1.00 | 17.26 | C |
| ATOM | 889 | CE2 | PHE | A | 70 | −70.051 | 30.672 | −10.736 | 1.00 | 17.60 | C |
| ATOM | 891 | CD2 | PHE | A | 70 | −68.822 | 31.300 | −10.700 | 1.00 | 17.86 | C |

TABLE 3-7-continued

Coordinates of *P. tremuloides* IspS

| ATOM | 893 | C | PHE | A | 70 | −64.627 | 32.661 | −12.400 | 1.00 | 21.34 | C |
|------|-----|------|-----|---|----|---------|--------|---------|------|-------|---|
| ATOM | 894 | O | PHE | A | 70 | −64.629 | 33.862 | −12.171 | 1.00 | 21.25 | O |
| ATOM | 896 | N | GLU | A | 71 | −63.501 | 31.977 | −12.541 | 1.00 | 23.19 | N |
| ATOM | 897 | CA | GLU | A | 71 | −62.211 | 32.591 | −12.214 | 1.00 | 24.60 | C |
| ATOM | 899 | CB | GLU | A | 71 | −61.127 | 31.524 | −12.073 | 1.00 | 25.03 | C |
| ATOM | 902 | CG | GLU | A | 71 | −59.717 | 32.059 | −11.861 | 1.00 | 27.10 | C |
| ATOM | 905 | CD | GLU | A | 71 | −58.712 | 30.949 | −11.549 | 1.00 | 30.10 | C |
| ATOM | 906 | OE1 | GLU | A | 71 | −59.084 | 30.007 | −10.796 | 1.00 | 32.05 | O |
| ATOM | 907 | OE2 | GLU | A | 71 | −57.558 | 31.027 | −12.051 | 1.00 | 30.50 | O |
| ATOM | 908 | C | GLU | A | 71 | −61.809 | 33.644 | −13.241 | 1.00 | 25.23 | C |
| ATOM | 909 | O | GLU | A | 71 | −61.362 | 34.717 | −12.862 | 1.00 | 25.54 | O |
| ATOM | 911 | N | SER | A | 72 | −61.979 | 33.345 | −14.530 | 1.00 | 25.91 | N |
| ATOM | 912 | CA | SER | A | 72 | −61.641 | 34.294 | −15.588 | 1.00 | 26.37 | C |
| ATOM | 914 | CB | SER | A | 72 | −61.656 | 33.606 | −16.941 | 1.00 | 26.32 | C |
| ATOM | 917 | OG | SER | A | 72 | −62.985 | 33.278 | −17.291 | 1.00 | 27.28 | O |
| ATOM | 919 | C | SER | A | 72 | −62.609 | 35.476 | −15.608 | 1.00 | 26.84 | C |
| ATOM | 920 | O | SER | A | 72 | −62.197 | 36.601 | −15.852 | 1.00 | 27.02 | O |
| ATOM | 922 | N | ASP | A | 73 | −63.893 | 35.214 | −15.361 | 1.00 | 27.45 | N |
| ATOM | 923 | CA | ASP | A | 73 | −64.895 | 36.277 | −15.246 | 1.00 | 27.87 | C |
| ATOM | 925 | CB | ASP | A | 73 | −66.289 | 35.705 | −14.968 | 1.00 | 27.99 | C |
| ATOM | 928 | CG | ASP | A | 73 | −66.842 | 34.913 | −16.140 | 1.00 | 29.49 | C |
| ATOM | 929 | OD1 | ASP | A | 73 | −67.215 | 35.530 | −17.155 | 1.00 | 30.90 | O |
| ATOM | 930 | OD2 | ASP | A | 73 | −66.916 | 33.667 | −16.054 | 1.00 | 31.85 | O |
| ATOM | 931 | C | ASP | A | 73 | −64.518 | 37.221 | −14.121 | 1.00 | 27.86 | C |
| ATOM | 932 | O | ASP | A | 73 | −64.598 | 38.435 | −14.286 | 1.00 | 28.05 | O |
| ATOM | 934 | N | ILE | A | 74 | −64.118 | 36.652 | −12.985 | 1.00 | 27.88 | N |
| ATOM | 935 | CA | ILE | A | 74 | −63.698 | 37.422 | −11.821 | 1.00 | 27.98 | C |
| ATOM | 937 | CB | ILE | A | 74 | −63.348 | 36.521 | −10.637 | 1.00 | 27.71 | C |
| ATOM | 939 | CG1 | ILE | A | 74 | −64.607 | 36.007 | −9.960 | 1.00 | 27.60 | C |
| ATOM | 942 | CD1 | ILE | A | 74 | −64.355 | 34.846 | −9.023 | 1.00 | 27.67 | C |
| ATOM | 946 | CG2 | ILE | A | 74 | −62.551 | 37.272 | −9.621 | 1.00 | 26.82 | C |
| ATOM | 950 | C | ILE | A | 74 | −62.472 | 38.252 | −12.133 | 1.00 | 28.80 | C |
| ATOM | 951 | O | ILE | A | 74 | −62.475 | 39.453 | −11.917 | 1.00 | 29.00 | O |
| ATOM | 953 | N | ARG | A | 75 | −61.415 | 37.616 | −12.628 | 1.00 | 29.80 | N |
| ATOM | 954 | CA | ARG | A | 75 | −60.197 | 38.341 | −12.968 | 1.00 | 30.79 | C |
| ATOM | 956 | CB | ARG | A | 75 | −59.286 | 37.507 | −13.841 | 1.00 | 31.33 | C |
| ATOM | 959 | CG | ARG | A | 75 | −58.506 | 36.441 | −13.115 | 1.00 | 34.25 | C |
| ATOM | 962 | CD | ARG | A | 75 | −57.286 | 36.009 | −13.929 | 1.00 | 37.53 | C |
| ATOM | 965 | NE | ARG | A | 75 | −56.238 | 37.019 | −13.799 | 1.00 | 40.89 | N |
| ATOM | 967 | CZ | ARG | A | 75 | −54.934 | 36.807 | −13.967 | 1.00 | 44.24 | C |
| ATOM | 968 | NH1 | ARG | A | 75 | −54.459 | 35.602 | −14.294 | 1.00 | 45.02 | N |
| ATOM | 971 | NH2 | ARG | A | 75 | −54.089 | 37.821 | −13.796 | 1.00 | 45.88 | N |
| ATOM | 974 | C | ARG | A | 75 | −60.548 | 39.596 | −13.727 | 1.00 | 30.95 | C |
| ATOM | 975 | O | ARG | A | 75 | −60.163 | 40.685 | −13.336 | 1.00 | 31.27 | O |
| ATOM | 977 | N | ARG | A | 76 | −61.293 | 39.435 | −14.815 | 1.00 | 31.31 | N |
| ATOM | 978 | CA | ARG | A | 76 | −61.712 | 40.567 | −15.638 | 1.00 | 31.62 | C |
| ATOM | 980 | CB | ARG | A | 76 | −62.593 | 40.106 | −16.794 | 1.00 | 31.97 | C |
| ATOM | 983 | CG | ARG | A | 76 | −61.833 | 39.392 | −17.895 | 1.00 | 32.91 | C |
| ATOM | 986 | CD | ARG | A | 76 | −62.615 | 39.453 | −19.205 | 1.00 | 34.43 | C |
| ATOM | 989 | NE | ARG | A | 76 | −63.925 | 38.803 | −19.128 | 1.00 | 35.66 | N |
| ATOM | 991 | CZ | ARG | A | 76 | −64.115 | 37.480 | −19.106 | 1.00 | 37.15 | C |
| ATOM | 992 | NH1 | ARG | A | 76 | −63.085 | 36.632 | −19.129 | 1.00 | 37.93 | N |
| ATOM | 995 | NH2 | ARG | A | 76 | −65.347 | 36.992 | −19.048 | 1.00 | 37.64 | N |
| ATOM | 998 | C | ARG | A | 76 | −62.453 | 41.629 | −14.849 | 1.00 | 31.41 | C |
| ATOM | 999 | O | ARG | A | 76 | −62.144 | 42.798 | −14.966 | 1.00 | 31.35 | O |
| ATOM | 1001 | N | ALA | A | 77 | −63.437 | 41.230 | −14.058 | 1.00 | 31.53 | N |
| ATOM | 1002 | CA | ALA | A | 77 | −64.136 | 42.177 | −13.211 | 1.00 | 31.73 | C |
| ATOM | 1004 | CB | ALA | A | 77 | −65.074 | 41.468 | −12.275 | 1.00 | 31.69 | C |
| ATOM | 1008 | C | ALA | A | 77 | −63.107 | 42.950 | −12.423 | 1.00 | 32.23 | C |
| ATOM | 1009 | O | ALA | A | 77 | −63.116 | 44.176 | −12.411 | 1.00 | 32.42 | O |
| ATOM | 1011 | N | LEU | A | 78 | −62.198 | 42.223 | −11.786 | 1.00 | 32.95 | N |
| ATOM | 1012 | CA | LEU | A | 78 | −61.168 | 42.838 | −10.963 | 1.00 | 33.51 | C |
| ATOM | 1014 | CB | LEU | A | 78 | −60.319 | 41.775 | −10.265 | 1.00 | 33.10 | C |
| ATOM | 1017 | CG | LEU | A | 78 | −60.959 | 41.077 | −9.081 | 1.00 | 32.30 | C |
| ATOM | 1019 | CD1 | LEU | A | 78 | −59.960 | 40.104 | −8.472 | 1.00 | 30.80 | C |
| ATOM | 1023 | CD2 | LEU | A | 78 | −61.438 | 42.117 | −8.056 | 1.00 | 31.89 | C |
| ATOM | 1027 | C | LEU | A | 78 | −60.249 | 43.752 | −11.753 | 1.00 | 34.70 | C |
| ATOM | 1028 | O | LEU | A | 78 | −59.790 | 44.753 | −11.214 | 1.00 | 35.18 | O |
| ATOM | 1030 | N | ASP | A | 79 | −59.955 | 43.404 | −13.007 | 1.00 | 35.91 | N |
| ATOM | 1031 | CA | ASP | A | 79 | −59.054 | 44.205 | −13.828 | 1.00 | 36.89 | C |
| ATOM | 1033 | CB | ASP | A | 79 | −58.637 | 43.452 | −15.083 | 1.00 | 37.06 | C |
| ATOM | 1036 | CG | ASP | A | 79 | −57.518 | 44.150 | −15.821 | 1.00 | 38.41 | C |
| ATOM | 1037 | OD1 | ASP | A | 79 | −57.800 | 45.080 | −16.615 | 1.00 | 39.85 | O |
| ATOM | 1038 | OD2 | ASP | A | 79 | −56.347 | 43.775 | −15.592 | 1.00 | 40.78 | O |
| ATOM | 1039 | C | ASP | A | 79 | −59.721 | 45.505 | −14.220 | 1.00 | 37.75 | C |
| ATOM | 1040 | O | ASP | A | 79 | −59.105 | 46.568 | −14.177 | 1.00 | 37.82 | O |
| ATOM | 1042 | N | ARG | A | 80 | −60.984 | 45.401 | −14.615 | 1.00 | 38.99 | N |
| ATOM | 1043 | CA | ARG | A | 80 | −61.814 | 46.558 | −14.923 | 1.00 | 39.88 | C |

TABLE 3-7-continued

Coordinates of *P. tremuloides* IspS

| ATOM | 1045 | CB | ARG | A | 80 | −63.191 | 46.106 | −15.427 | 1.00 | 40.41 | C |
|---|---|---|---|---|---|---|---|---|---|---|---|
| ATOM | 1048 | CG | ARG | A | 80 | −64.025 | 47.183 | −16.122 | 1.00 | 42.77 | C |
| ATOM | 1051 | CD | ARG | A | 80 | −65.347 | 46.624 | −16.718 | 1.00 | 45.79 | C |
| ATOM | 1054 | NE | ARG | A | 80 | −66.107 | 45.799 | −15.765 | 1.00 | 48.55 | N |
| ATOM | 1056 | CZ | ARG | A | 80 | −66.136 | 44.457 | −15.742 | 1.00 | 50.37 | C |
| ATOM | 1057 | NH1 | ARG | A | 80 | −65.450 | 43.724 | −16.636 | 1.00 | 49.78 | N |
| ATOM | 1060 | NH2 | ARG | A | 80 | −66.868 | 43.835 | −14.805 | 1.00 | 50.77 | N |
| ATOM | 1063 | C | ARG | A | 80 | −61.946 | 47.409 | −13.668 | 1.00 | 39.80 | C |
| ATOM | 1064 | O | ARG | A | 80 | −61.840 | 48.630 | −13.742 | 1.00 | 40.37 | O |
| ATOM | 1066 | N | PHE | A | 81 | −62.136 | 46.771 | −12.516 | 1.00 | 39.62 | N |
| ATOM | 1067 | CA | PHE | A | 81 | −62.216 | 47.505 | −11.245 | 1.00 | 39.61 | C |
| ATOM | 1069 | CB | PHE | A | 81 | −62.392 | 46.561 | −10.053 | 1.00 | 39.74 | C |
| ATOM | 1072 | CG | PHE | A | 81 | −62.282 | 47.247 | −8.712 | 1.00 | 38.81 | C |
| ATOM | 1073 | CD1 | PHE | A | 81 | −63.238 | 48.153 | −8.315 | 1.00 | 39.03 | C |
| ATOM | 1075 | CE1 | PHE | A | 81 | −63.153 | 48.787 | −7.100 | 1.00 | 39.69 | C |
| ATOM | 1077 | CZ | PHE | A | 81 | −62.095 | 48.515 | −6.261 | 1.00 | 39.54 | C |
| ATOM | 1079 | CE2 | PHE | A | 81 | −61.134 | 47.608 | −6.647 | 1.00 | 38.66 | C |
| ATOM | 1081 | CD2 | PHE | A | 81 | −61.228 | 46.986 | −7.865 | 1.00 | 38.27 | C |
| ATOM | 1083 | C | PHE | A | 81 | −61.006 | 48.378 | −10.970 | 1.00 | 39.58 | C |
| ATOM | 1084 | O | PHE | A | 81 | −61.165 | 49.535 | −10.581 | 1.00 | 39.76 | O |
| ATOM | 1086 | N | VAL | A | 82 | −59.810 | 47.817 | −11.142 | 1.00 | 39.50 | N |
| ATOM | 1087 | CA | VAL | A | 82 | −58.575 | 48.562 | −10.892 | 1.00 | 39.47 | C |
| ATOM | 1089 | CB | VAL | A | 82 | −57.314 | 47.659 | −10.977 | 1.00 | 39.37 | C |
| ATOM | 1091 | CG1 | VAL | A | 82 | −56.108 | 48.426 | −11.521 | 1.00 | 39.06 | C |
| ATOM | 1095 | CG2 | VAL | A | 82 | −57.009 | 47.079 | −9.614 | 1.00 | 39.23 | C |
| ATOM | 1099 | C | VAL | A | 82 | −58.457 | 49.755 | −11.833 | 1.00 | 39.54 | C |
| ATOM | 1100 | O | VAL | A | 82 | −58.222 | 50.884 | −11.378 | 1.00 | 39.45 | O |
| ATOM | 1102 | N | SER | A | 83 | −58.678 | 49.513 | −13.126 | 1.00 | 39.65 | N |
| ATOM | 1103 | CA | SER | A | 83 | −58.469 | 50.535 | −14.157 | 1.00 | 39.82 | C |
| ATOM | 1105 | CB | SER | A | 83 | −58.196 | 49.880 | −15.526 | 1.00 | 39.84 | C |
| ATOM | 1108 | OG | SER | A | 83 | −59.138 | 48.870 | −15.829 | 1.00 | 40.00 | O |
| ATOM | 1110 | C | SER | A | 83 | −59.617 | 51.561 | −14.219 | 1.00 | 39.62 | C |
| ATOM | 1111 | O | SER | A | 83 | −60.149 | 51.853 | −15.286 | 1.00 | 39.59 | O |
| ATOM | 1113 | N | SER | A | 84 | −59.957 | 52.108 | −13.052 | 1.00 | 39.44 | N |
| ATOM | 1114 | CA | SER | A | 84 | −60.926 | 53.197 | −12.910 | 1.00 | 39.13 | C |
| ATOM | 1116 | CB | SER | A | 84 | −62.238 | 52.834 | −13.618 | 1.00 | 39.03 | C |
| ATOM | 1119 | OG | SER | A | 84 | −62.620 | 51.505 | −13.325 | 1.00 | 37.97 | O |
| ATOM | 1121 | C | SER | A | 84 | −61.243 | 53.580 | −11.446 | 1.00 | 39.17 | C |
| ATOM | 1122 | O | SER | A | 84 | −62.189 | 54.341 | −11.230 | 1.00 | 39.58 | O |
| ATOM | 1124 | N | GLY | A | 85 | −60.482 | 53.077 | −10.457 | 1.00 | 38.74 | N |
| ATOM | 1125 | CA | GLY | A | 85 | −60.795 | 53.282 | −9.024 | 1.00 | 38.26 | C |
| ATOM | 1128 | C | GLY | A | 85 | −61.724 | 52.238 | −8.413 | 1.00 | 37.79 | C |
| ATOM | 1129 | O | GLY | A | 85 | −61.529 | 51.799 | −7.273 | 1.00 | 36.84 | O |
| ATOM | 1131 | N | SER | A | 94 | −63.557 | 54.187 | 1.994 | 1.00 | 28.27 | N |
| ATOM | 1132 | CA | SER | A | 94 | −64.069 | 52.892 | 2.476 | 1.00 | 28.03 | C |
| ATOM | 1134 | CB | SER | A | 94 | −64.856 | 52.225 | 1.359 | 1.00 | 27.84 | C |
| ATOM | 1137 | OG | SER | A | 94 | −65.234 | 50.921 | 1.743 | 1.00 | 28.20 | O |
| ATOM | 1139 | C | SER | A | 94 | −62.992 | 51.910 | 2.934 | 1.00 | 27.83 | C |
| ATOM | 1140 | O | SER | A | 94 | −62.339 | 51.325 | 2.090 | 1.00 | 28.15 | O |
| ATOM | 1142 | N | LEU | A | 95 | −62.815 | 51.705 | 4.245 | 1.00 | 27.70 | N |
| ATOM | 1143 | CA | LEU | A | 95 | −61.813 | 50.728 | 4.751 | 1.00 | 27.59 | C |
| ATOM | 1145 | CB | LEU | A | 95 | −61.692 | 50.747 | 6.282 | 1.00 | 27.49 | C |
| ATOM | 1148 | CG | LEU | A | 95 | −60.871 | 49.596 | 6.909 | 1.00 | 27.47 | C |
| ATOM | 1150 | CD1 | LEU | A | 95 | −59.400 | 49.900 | 6.902 | 1.00 | 27.70 | C |
| ATOM | 1154 | CD2 | LEU | A | 95 | −61.292 | 49.274 | 8.329 | 1.00 | 27.50 | C |
| ATOM | 1158 | C | LEU | A | 95 | −62.173 | 49.314 | 4.318 | 1.00 | 27.71 | C |
| ATOM | 1159 | O | LEU | A | 95 | −61.303 | 48.537 | 3.914 | 1.00 | 27.73 | O |
| ATOM | 1161 | N | HIS | A | 96 | −63.461 | 48.989 | 4.437 | 1.00 | 27.74 | N |
| ATOM | 1162 | CA | HIS | A | 96 | −64.003 | 47.715 | 3.977 | 1.00 | 27.54 | C |
| ATOM | 1164 | CB | HIS | A | 96 | −65.497 | 47.680 | 4.230 | 1.00 | 27.57 | C |
| ATOM | 1167 | CG | HIS | A | 96 | −66.161 | 46.482 | 3.654 | 1.00 | 28.65 | C |
| ATOM | 1168 | ND1 | HIS | A | 96 | −65.790 | 45.201 | 3.988 | 1.00 | 30.59 | N |
| ATOM | 1170 | CE1 | HIS | A | 96 | −66.540 | 44.341 | 3.325 | 1.00 | 31.88 | C |
| ATOM | 1172 | NE2 | HIS | A | 96 | −67.384 | 45.021 | 2.570 | 1.00 | 32.06 | N |
| ATOM | 1174 | CD2 | HIS | A | 96 | −67.166 | 46.364 | 2.758 | 1.00 | 30.47 | C |
| ATOM | 1176 | C | HIS | A | 96 | −63.705 | 47.450 | 2.492 | 1.00 | 27.09 | C |
| ATOM | 1177 | O | HIS | A | 96 | −63.128 | 46.425 | 2.150 | 1.00 | 27.18 | O |
| ATOM | 1179 | N | GLY | A | 97 | −64.079 | 48.386 | 1.625 | 1.00 | 26.55 | N |
| ATOM | 1180 | CA | GLY | A | 97 | −63.760 | 48.300 | .205 | 1.00 | 26.26 | C |
| ATOM | 1183 | C | GLY | A | 97 | −62.277 | 48.112 | −.088 | 1.00 | 26.23 | C |
| ATOM | 1184 | O | GLY | A | 97 | −61.918 | 47.334 | −.974 | 1.00 | 26.39 | O |
| ATOM | 1186 | N | THR | A | 98 | −61.415 | 48.815 | .653 | 1.00 | 25.83 | N |
| ATOM | 1187 | CA | THR | A | 98 | −59.967 | 48.755 | .435 | 1.00 | 25.36 | C |
| ATOM | 1189 | CB | THR | A | 98 | −59.204 | 49.847 | 1.215 | 1.00 | 25.07 | C |
| ATOM | 1191 | OG1 | THR | A | 98 | −59.796 | 51.123 | .980 | 1.00 | 23.62 | O |
| ATOM | 1193 | CG2 | THR | A | 98 | −57.755 | 49.905 | .780 | 1.00 | 24.88 | C |
| ATOM | 1197 | C | THR | A | 98 | −59.416 | 47.389 | .845 | 1.00 | 25.69 | C |
| ATOM | 1198 | O | THR | A | 98 | −58.622 | 46.802 | .111 | 1.00 | 25.66 | O |

TABLE 3-7-continued

Coordinates of *P. tremuloides* IspS

| ATOM | 1200 | N | ALA | A | 99 | −59.847 | 46.890 | 2.008 | 1.00 | 25.95 | N |
|---|---|---|---|---|---|---|---|---|---|---|---|
| ATOM | 1201 | CA | ALA | A | 99 | −59.468 | 45.540 | 2.495 | 1.00 | 25.93 | C |
| ATOM | 1203 | CB | ALA | A | 99 | −59.945 | 45.330 | 3.929 | 1.00 | 25.82 | C |
| ATOM | 1207 | C | ALA | A | 99 | −59.984 | 44.404 | 1.595 | 1.00 | 25.64 | C |
| ATOM | 1208 | O | ALA | A | 99 | −59.204 | 43.599 | 1.102 | 1.00 | 25.38 | O |
| ATOM | 1210 | N | LEU | A | 100 | −61.290 | 44.348 | 1.371 | 1.00 | 25.46 | N |
| ATOM | 1211 | CA | LEU | A | 100 | −61.856 | 43.335 | .474 | 1.00 | 25.55 | C |
| ATOM | 1213 | CB | LEU | A | 100 | −63.361 | 43.540 | .326 | 1.00 | 25.37 | C |
| ATOM | 1216 | CG | LEU | A | 100 | −64.118 | 42.464 | −.443 | 1.00 | 25.41 | C |
| ATOM | 1218 | CD1 | LEU | A | 100 | −64.038 | 41.115 | .281 | 1.00 | 26.01 | C |
| ATOM | 1222 | CD2 | LEU | A | 100 | −65.555 | 42.893 | −.639 | 1.00 | 25.19 | C |
| ATOM | 1226 | C | LEU | A | 100 | −61.196 | 43.353 | −.919 | 1.00 | 25.70 | C |
| ATOM | 1227 | O | LEU | A | 100 | −60.819 | 42.301 | −1.469 | 1.00 | 25.36 | O |
| ATOM | 1229 | N | SER | A | 101 | −61.064 | 44.550 | −1.489 | 1.00 | 25.77 | N |
| ATOM | 1230 | CA | SER | A | 101 | −60.434 | 44.688 | −2.805 | 1.00 | 25.67 | C |
| ATOM | 1232 | CB | SER | A | 101 | −60.629 | 46.098 | −3.375 | 1.00 | 25.83 | C |
| ATOM | 1235 | OG | SER | A | 101 | −59.840 | 47.064 | −2.688 | 1.00 | 26.98 | O |
| ATOM | 1237 | C | SER | A | 101 | −58.947 | 44.336 | −2.756 | 1.00 | 25.01 | C |
| ATOM | 1238 | O | SER | A | 101 | −58.427 | 43.705 | −3.672 | 1.00 | 24.94 | O |
| ATOM | 1240 | N | PHE | A | 102 | −58.270 | 44.737 | −1.687 | 1.00 | 24.30 | N |
| ATOM | 1241 | CA | PHE | A | 102 | −56.852 | 44.436 | −1.560 | 1.00 | 23.99 | C |
| ATOM | 1243 | CB | PHE | A | 102 | −56.295 | 44.963 | −.229 | 1.00 | 23.84 | C |
| ATOM | 1246 | CG | PHE | A | 102 | −54.860 | 44.606 | .027 | 1.00 | 23.24 | C |
| ATOM | 1247 | CD1 | PHE | A | 102 | −53.849 | 45.504 | −.259 | 1.00 | 23.56 | C |
| ATOM | 1249 | CE1 | PHE | A | 102 | −52.507 | 45.182 | −.007 | 1.00 | 24.50 | C |
| ATOM | 1251 | CZ | PHE | A | 102 | −52.175 | 43.941 | .540 | 1.00 | 24.27 | C |
| ATOM | 1253 | CE2 | PHE | A | 102 | −53.180 | 43.042 | .834 | 1.00 | 23.95 | C |
| ATOM | 1255 | CD2 | PHE | A | 102 | −54.520 | 43.376 | .576 | 1.00 | 23.45 | C |
| ATOM | 1257 | C | PHE | A | 102 | −56.673 | 42.928 | −1.679 | 1.00 | 23.65 | C |
| ATOM | 1258 | O | PHE | A | 102 | −55.890 | 42.442 | −2.501 | 1.00 | 23.55 | O |
| ATOM | 1260 | N | ARG | A | 103 | −57.443 | 42.202 | −.880 | 1.00 | 23.20 | N |
| ATOM | 1261 | CA | ARG | A | 103 | −57.298 | 40.765 | −.764 | 1.00 | 22.84 | C |
| ATOM | 1263 | CB | ARG | A | 103 | −58.250 | 40.231 | .291 | 1.00 | 23.01 | C |
| ATOM | 1266 | CG | ARG | A | 103 | −58.054 | 38.774 | .597 | 1.00 | 23.93 | C |
| ATOM | 1269 | CD | ARG | A | 103 | −58.703 | 38.376 | 1.937 | 1.00 | 23.84 | C |
| ATOM | 1272 | NE | ARG | A | 103 | −60.150 | 38.538 | 1.919 | 1.00 | 22.36 | N |
| ATOM | 1274 | CZ | ARG | A | 103 | −60.982 | 37.763 | 1.240 | 1.00 | 20.62 | C |
| ATOM | 1275 | NH1 | ARG | A | 103 | −60.512 | 36.773 | .490 | 1.00 | 20.19 | N |
| ATOM | 1278 | NH2 | ARG | A | 103 | −62.288 | 38.003 | 1.293 | 1.00 | 20.32 | N |
| ATOM | 1281 | C | ARG | A | 103 | −57.602 | 40.117 | −2.082 | 1.00 | 22.34 | C |
| ATOM | 1282 | O | ARG | A | 103 | −56.826 | 39.303 | −2.576 | 1.00 | 22.37 | O |
| ATOM | 1284 | N | LEU | A | 104 | −58.729 | 40.496 | −2.667 | 1.00 | 21.98 | N |
| ATOM | 1285 | CA | LEU | A | 104 | −59.129 | 39.926 | −3.951 | 1.00 | 21.60 | C |
| ATOM | 1287 | CB | LEU | A | 104 | −60.503 | 40.442 | −4.378 | 1.00 | 21.23 | C |
| ATOM | 1290 | CG | LEU | A | 104 | −61.590 | 39.832 | −3.522 | 1.00 | 20.30 | C |
| ATOM | 1292 | CD1 | LEU | A | 104 | −62.949 | 40.401 | −3.856 | 1.00 | 19.53 | C |
| ATOM | 1296 | CD2 | LEU | A | 104 | −61.554 | 38.344 | −3.725 | 1.00 | 19.71 | C |
| ATOM | 1300 | C | LEU | A | 104 | −58.101 | 40.198 | −5.040 | 1.00 | 21.48 | C |
| ATOM | 1301 | O | LEU | A | 104 | −57.743 | 39.294 | −5.780 | 1.00 | 21.62 | O |
| ATOM | 1303 | N | LEU | A | 105 | −57.623 | 41.432 | −5.139 | 1.00 | 21.14 | N |
| ATOM | 1304 | CA | LEU | A | 105 | −56.655 | 41.747 | −6.173 | 1.00 | 21.05 | C |
| ATOM | 1306 | CB | LEU | A | 105 | −56.352 | 43.248 | −6.205 | 1.00 | 20.94 | C |
| ATOM | 1309 | CG | LEU | A | 105 | −57.465 | 44.165 | −6.732 | 1.00 | 20.06 | C |
| ATOM | 1311 | CD1 | LEU | A | 105 | −57.060 | 45.617 | −6.580 | 1.00 | 17.92 | C |
| ATOM | 1315 | CD2 | LEU | A | 105 | −57.804 | 43.857 | −8.174 | 1.00 | 19.18 | C |
| ATOM | 1319 | C | LEU | A | 105 | −55.372 | 40.908 | −5.997 | 1.00 | 21.32 | C |
| ATOM | 1320 | O | LEU | A | 105 | −54.840 | 40.357 | −6.976 | 1.00 | 21.37 | O |
| ATOM | 1322 | N | ARG | A | 106 | −54.893 | 40.777 | −4.763 | 1.00 | 21.25 | N |
| ATOM | 1323 | CA | ARG | A | 106 | −53.678 | 40.003 | −4.528 | 1.00 | 21.33 | C |
| ATOM | 1325 | CB | ARG | A | 106 | −53.151 | 40.211 | −3.117 | 1.00 | 21.53 | C |
| ATOM | 1328 | CG | ARG | A | 106 | −51.772 | 39.588 | −2.917 | 1.00 | 22.60 | C |
| ATOM | 1331 | CD | ARG | A | 106 | −51.098 | 40.091 | −1.666 | 1.00 | 23.60 | C |
| ATOM | 1334 | NE | ARG | A | 106 | −50.374 | 41.330 | −1.897 | 1.00 | 24.60 | N |
| ATOM | 1336 | CZ | ARG | A | 106 | −49.606 | 41.916 | −.989 | 1.00 | 26.54 | C |
| ATOM | 1337 | NH1 | ARG | A | 106 | −49.469 | 41.380 | .225 | 1.00 | 26.98 | N |
| ATOM | 1340 | NH2 | ARG | A | 106 | −48.967 | 43.041 | −1.295 | 1.00 | 27.19 | N |
| ATOM | 1343 | C | ARG | A | 106 | −53.888 | 38.517 | −4.767 | 1.00 | 21.19 | C |
| ATOM | 1344 | O | ARG | A | 106 | −52.998 | 37.821 | −5.278 | 1.00 | 21.18 | O |
| ATOM | 1346 | N | GLN | A | 107 | −55.061 | 38.028 | −4.378 | 1.00 | 21.09 | N |
| ATOM | 1347 | CA | GLN | A | 107 | −55.425 | 36.635 | −4.618 | 1.00 | 20.76 | C |
| ATOM | 1349 | CB | GLN | A | 107 | −56.861 | 36.378 | −4.168 | 1.00 | 20.51 | C |
| ATOM | 1352 | CG | GLN | A | 107 | −57.329 | 34.941 | −4.327 | 1.00 | 19.68 | C |
| ATOM | 1355 | CD | GLN | A | 107 | −58.790 | 34.772 | −4.010 | 1.00 | 18.26 | C |
| ATOM | 1356 | OE1 | GLN | A | 107 | −59.395 | 35.591 | −3.334 | 1.00 | 17.44 | O |
| ATOM | 1357 | NE2 | GLN | A | 107 | −59.366 | 33.698 | −4.497 | 1.00 | 18.48 | N |
| ATOM | 1360 | C | GLN | A | 107 | −55.304 | 36.306 | −6.094 | 1.00 | 20.93 | C |
| ATOM | 1361 | O | GLN | A | 107 | −54.917 | 35.212 | −6.447 | 1.00 | 21.45 | O |
| ATOM | 1363 | N | HIS | A | 108 | −55.642 | 37.260 | −6.951 | 1.00 | 21.09 | N |

TABLE 3-7-continued

Coordinates of *P. tremuloides* IspS

| ATOM | 1364 | CA | HIS | A | 108 | −55.686 | 37.030 | −8.379 | 1.00 | 21.28 | C |
|---|---|---|---|---|---|---|---|---|---|---|---|
| ATOM | 1366 | CB | HIS | A | 108 | −57.024 | 37.541 | −8.913 | 1.00 | 21.02 | C |
| ATOM | 1369 | CG | HIS | A | 108 | −58.182 | 36.706 | −8.478 | 1.00 | 19.70 | C |
| ATOM | 1370 | ND1 | HIS | A | 108 | −58.637 | 35.632 | −9.210 | 1.00 | 19.91 | N |
| ATOM | 1372 | CE1 | HIS | A | 108 | −59.641 | 35.060 | −8.571 | 1.00 | 19.27 | C |
| ATOM | 1374 | NE2 | HIS | A | 108 | −59.851 | 35.720 | −7.449 | 1.00 | 18.10 | N |
| ATOM | 1376 | CD2 | HIS | A | 108 | −58.950 | 36.753 | −7.367 | 1.00 | 18.98 | C |
| ATOM | 1378 | C | HIS | A | 108 | −54.456 | 37.621 | −9.108 | 1.00 | 22.21 | C |
| ATOM | 1379 | O | HIS | A | 108 | −54.505 | 37.980 | −10.304 | 1.00 | 21.80 | O |
| ATOM | 1381 | N | GLY | A | 109 | −53.345 | 37.686 | −8.375 | 1.00 | 23.19 | N |
| ATOM | 1382 | CA | GLY | A | 109 | −52.055 | 38.007 | −8.956 | 1.00 | 24.17 | C |
| ATOM | 1385 | C | GLY | A | 109 | −51.813 | 39.470 | −9.275 | 1.00 | 25.25 | C |
| ATOM | 1386 | O | GLY | A | 109 | −50.767 | 39.802 | −9.845 | 1.00 | 25.26 | O |
| ATOM | 1388 | N | PHE | A | 110 | −52.755 | 40.349 | −8.917 | 1.00 | 26.42 | N |
| ATOM | 1389 | CA | PHE | A | 110 | −52.575 | 41.783 | −9.154 | 1.00 | 27.33 | C |
| ATOM | 1391 | CB | PHE | A | 110 | −53.895 | 42.546 | −9.067 | 1.00 | 27.36 | C |
| ATOM | 1394 | CG | PHE | A | 110 | −54.838 | 42.250 | −10.193 | 1.00 | 27.83 | C |
| ATOM | 1395 | CD1 | PHE | A | 110 | −54.633 | 42.801 | −11.439 | 1.00 | 28.69 | C |
| ATOM | 1397 | CE1 | PHE | A | 110 | −55.490 | 42.529 | −12.488 | 1.00 | 28.91 | C |
| ATOM | 1399 | CZ | PHE | A | 110 | −56.568 | 41.702 | −12.295 | 1.00 | 28.85 | C |
| ATOM | 1401 | CE2 | PHE | A | 110 | −56.787 | 41.146 | −11.060 | 1.00 | 28.67 | C |
| ATOM | 1403 | CD2 | PHE | A | 110 | −55.923 | 41.418 | −10.013 | 1.00 | 28.39 | C |
| ATOM | 1405 | C | PHE | A | 110 | −51.582 | 42.369 | −8.163 | 1.00 | 28.25 | C |
| ATOM | 1406 | O | PHE | A | 110 | −51.449 | 41.890 | −7.024 | 1.00 | 28.71 | O |
| ATOM | 1408 | N | GLU | A | 111 | −50.886 | 43.411 | −8.607 | 1.00 | 29.05 | N |
| ATOM | 1409 | CA | GLU | A | 111 | −49.951 | 44.142 | −7.760 | 1.00 | 29.66 | C |
| ATOM | 1411 | CB | GLU | A | 111 | −48.902 | 44.803 | −8.648 | 1.00 | 30.37 | C |
| ATOM | 1414 | CG | GLU | A | 111 | −47.750 | 45.509 | −7.947 | 1.00 | 33.30 | C |
| ATOM | 1417 | CD | GLU | A | 111 | −46.916 | 46.342 | −8.946 | 1.00 | 38.00 | C |
| ATOM | 1418 | OE1 | GLU | A | 111 | −46.312 | 45.750 | −9.885 | 1.00 | 39.60 | O |
| ATOM | 1419 | OE2 | GLU | A | 111 | −46.886 | 47.594 | −8.802 | 1.00 | 40.87 | O |
| ATOM | 1420 | C | GLU | A | 111 | −50.724 | 45.184 | −6.935 | 1.00 | 28.98 | C |
| ATOM | 1421 | O | GLU | A | 111 | −51.293 | 46.123 | −7.495 | 1.00 | 28.45 | O |
| ATOM | 1423 | N | VAL | A | 112 | −50.787 | 44.961 | −5.618 | 1.00 | 28.47 | N |
| ATOM | 1424 | CA | VAL | A | 112 | −51.284 | 45.950 | −4.655 | 1.00 | 28.09 | C |
| ATOM | 1426 | CB | VAL | A | 112 | −52.564 | 45.501 | −3.908 | 1.00 | 27.76 | C |
| ATOM | 1428 | CG1 | VAL | A | 112 | −53.745 | 45.466 | −4.836 | 1.00 | 27.38 | C |
| ATOM | 1432 | CG2 | VAL | A | 112 | −52.360 | 44.167 | −3.252 | 1.00 | 27.80 | C |
| ATOM | 1436 | C | VAL | A | 112 | −50.193 | 46.199 | −3.631 | 1.00 | 28.15 | C |
| ATOM | 1437 | O | VAL | A | 112 | −49.339 | 45.354 | −3.436 | 1.00 | 27.90 | O |
| ATOM | 1439 | N | SER | A | 113 | −50.241 | 47.354 | −2.974 | 1.00 | 28.54 | N |
| ATOM | 1440 | CA | SER | A | 113 | −49.194 | 47.782 | −2.047 | 1.00 | 28.93 | C |
| ATOM | 1442 | CB | SER | A | 113 | −48.563 | 49.064 | −2.564 | 1.00 | 29.12 | C |
| ATOM | 1445 | OG | SER | A | 113 | −47.692 | 49.644 | −1.619 | 1.00 | 29.57 | O |
| ATOM | 1447 | C | SER | A | 113 | −49.780 | 48.041 | −.685 | 1.00 | 29.13 | C |
| ATOM | 1448 | O | SER | A | 113 | −50.937 | 48.426 | −.581 | 1.00 | 28.90 | O |
| ATOM | 1450 | N | GLN | A | 114 | −48.985 | 47.857 | .367 | 1.00 | 29.84 | N |
| ATOM | 1451 | CA | GLN | A | 114 | −49.524 | 48.019 | 1.736 | 1.00 | 30.40 | C |
| ATOM | 1453 | CB | GLN | A | 114 | −48.568 | 47.507 | 2.830 | 1.00 | 30.34 | C |
| ATOM | 1456 | CG | GLN | A | 114 | −47.199 | 48.159 | 2.844 | 1.00 | 30.61 | C |
| ATOM | 1459 | CD | GLN | A | 114 | −46.456 | 47.928 | 4.147 | 1.00 | 30.77 | C |
| ATOM | 1460 | OE1 | GLN | A | 114 | −46.876 | 47.129 | 4.982 | 1.00 | 31.92 | O |
| ATOM | 1461 | NE2 | GLN | A | 114 | −45.341 | 48.624 | 4.324 | 1.00 | 30.02 | N |
| ATOM | 1464 | C | GLN | A | 114 | −49.939 | 49.440 | 2.068 | 1.00 | 30.62 | C |
| ATOM | 1465 | O | GLN | A | 114 | −50.573 | 49.644 | 3.094 | 1.00 | 30.73 | O |
| ATOM | 1467 | N | GLU | A | 115 | −49.592 | 50.407 | 1.216 | 1.00 | 30.94 | N |
| ATOM | 1468 | CA | GLU | A | 115 | −49.963 | 51.794 | 1.458 | 1.00 | 31.45 | C |
| ATOM | 1470 | CB | GLU | A | 115 | −48.881 | 52.777 | .975 | 1.00 | 31.86 | C |
| ATOM | 1473 | CG | GLU | A | 115 | −48.489 | 52.723 | −.509 | 1.00 | 33.48 | C |
| ATOM | 1476 | CD | GLU | A | 115 | −47.006 | 53.100 | −.759 | 1.00 | 36.13 | C |
| ATOM | 1477 | OE1 | GLU | A | 115 | −46.106 | 52.668 | .022 | 1.00 | 38.72 | O |
| ATOM | 1478 | OE2 | GLU | A | 115 | −46.741 | 53.811 | −1.754 | 1.00 | 35.70 | O |
| ATOM | 1479 | C | GLU | A | 115 | −51.338 | 52.125 | .895 | 1.00 | 31.45 | C |
| ATOM | 1480 | O | GLU | A | 115 | −51.716 | 53.283 | .808 | 1.00 | 31.80 | O |
| ATOM | 1482 | N | ALA | A | 116 | −52.108 | 51.105 | .549 | 1.00 | 31.58 | N |
| ATOM | 1483 | CA | ALA | A | 116 | −53.524 | 51.286 | .284 | 1.00 | 31.67 | C |
| ATOM | 1485 | CB | ALA | A | 116 | −54.071 | 50.092 | −.461 | 1.00 | 31.62 | C |
| ATOM | 1489 | C | ALA | A | 116 | −54.273 | 51.473 | 1.596 | 1.00 | 31.88 | C |
| ATOM | 1490 | O | ALA | A | 116 | −55.428 | 51.874 | 1.604 | 1.00 | 31.82 | O |
| ATOM | 1492 | N | PHE | A | 117 | −53.608 | 51.161 | 2.702 | 1.00 | 32.39 | N |
| ATOM | 1493 | CA | PHE | A | 117 | −54.193 | 51.271 | 4.030 | 1.00 | 32.87 | C |
| ATOM | 1495 | CB | PHE | A | 117 | −53.884 | 50.003 | 4.856 | 1.00 | 32.79 | C |
| ATOM | 1498 | CG | PHE | A | 117 | −54.539 | 48.758 | 4.323 | 1.00 | 31.03 | C |
| ATOM | 1499 | CD1 | PHE | A | 117 | −53.782 | 47.749 | 3.760 | 1.00 | 28.79 | C |
| ATOM | 1501 | CE1 | PHE | A | 117 | −54.379 | 46.620 | 3.265 | 1.00 | 28.36 | C |
| ATOM | 1503 | CZ | PHE | A | 117 | −55.754 | 46.489 | 3.316 | 1.00 | 29.50 | C |
| ATOM | 1505 | CE2 | PHE | A | 117 | −56.527 | 47.493 | 3.872 | 1.00 | 29.91 | C |
| ATOM | 1507 | CD2 | PHE | A | 117 | −55.917 | 48.613 | 4.375 | 1.00 | 30.09 | C |

TABLE 3-7-continued

Coordinates of *P. tremuloides* IspS

| ATOM | 1509 | C | PHE | A | 117 | −53.683 | 52.493 | 4.773 | 1.00 | 33.71 | C |
|---|---|---|---|---|---|---|---|---|---|---|---|
| ATOM | 1510 | O | PHE | A | 117 | −54.012 | 52.678 | 5.937 | 1.00 | 33.61 | O |
| ATOM | 1512 | N | SER | A | 118 | −52.886 | 53.325 | 4.107 | 1.00 | 35.09 | N |
| ATOM | 1513 | CA | SER | A | 118 | −52.186 | 54.429 | 4.779 | 1.00 | 36.12 | C |
| ATOM | 1515 | CB | SER | A | 118 | −51.073 | 54.990 | 3.895 | 1.00 | 36.09 | C |
| ATOM | 1518 | OG | SER | A | 118 | −51.607 | 55.747 | 2.820 | 1.00 | 35.96 | O |
| ATOM | 1520 | C | SER | A | 118 | −53.134 | 55.552 | 5.184 | 1.00 | 37.17 | C |
| ATOM | 1521 | O | SER | A | 118 | −52.873 | 56.255 | 6.166 | 1.00 | 37.22 | O |
| ATOM | 1523 | N | GLY | A | 119 | −54.231 | 55.705 | 4.436 | 1.00 | 38.40 | N |
| ATOM | 1524 | CA | GLY | A | 119 | −55.227 | 56.735 | 4.708 | 1.00 | 39.47 | C |
| ATOM | 1527 | C | GLY | A | 119 | −56.255 | 56.398 | 5.778 | 1.00 | 40.62 | C |
| ATOM | 1528 | O | GLY | A | 119 | −57.259 | 57.086 | 5.877 | 1.00 | 40.74 | O |
| ATOM | 1530 | N | PHE | A | 120 | −56.024 | 55.344 | 6.563 | 1.00 | 42.13 | N |
| ATOM | 1531 | CA | PHE | A | 120 | −56.906 | 54.971 | 7.684 | 1.00 | 43.27 | C |
| ATOM | 1533 | CB | PHE | A | 120 | −57.510 | 53.586 | 7.455 | 1.00 | 43.21 | C |
| ATOM | 1536 | CG | PHE | A | 120 | −58.176 | 53.439 | 6.134 | 1.00 | 42.36 | C |
| ATOM | 1537 | CD1 | PHE | A | 120 | −59.418 | 54.006 | 5.911 | 1.00 | 41.23 | C |
| ATOM | 1539 | CE1 | PHE | A | 120 | −60.035 | 53.880 | 4.691 | 1.00 | 40.87 | C |
| ATOM | 1541 | CZ | PHE | A | 120 | −59.414 | 53.182 | 3.675 | 1.00 | 41.03 | C |
| ATOM | 1543 | CE2 | PHE | A | 120 | −58.167 | 52.618 | 3.883 | 1.00 | 40.92 | C |
| ATOM | 1545 | CD2 | PHE | A | 120 | −57.556 | 52.746 | 5.106 | 1.00 | 41.30 | C |
| ATOM | 1547 | C | PHE | A | 120 | −56.179 | 54.952 | 9.019 | 1.00 | 44.71 | C |
| ATOM | 1548 | O | PHE | A | 120 | −56.732 | 54.489 | 10.025 | 1.00 | 44.80 | O |
| ATOM | 1550 | N | LYS | A | 121 | −54.939 | 55.430 | 9.021 | 1.00 | 46.38 | N |
| ATOM | 1551 | CA | LYS | A | 121 | −54.153 | 55.519 | 10.235 | 1.00 | 47.81 | C |
| ATOM | 1553 | CB | LYS | A | 121 | −52.722 | 55.050 | 9.957 | 1.00 | 47.86 | C |
| ATOM | 1556 | CG | LYS | A | 121 | −52.648 | 53.537 | 9.648 | 1.00 | 48.24 | C |
| ATOM | 1559 | CD | LYS | A | 121 | −51.417 | 53.119 | 8.823 | 1.00 | 49.41 | C |
| ATOM | 1562 | CE | LYS | A | 121 | −50.095 | 53.142 | 9.621 | 1.00 | 49.88 | C |
| ATOM | 1565 | NZ | LYS | A | 121 | −49.944 | 52.005 | 10.584 | 1.00 | 49.89 | N |
| ATOM | 1569 | C | LYS | A | 121 | −54.257 | 56.964 | 10.735 | 1.00 | 49.00 | C |
| ATOM | 1570 | O | LYS | A | 121 | −54.712 | 57.839 | 10.000 | 1.00 | 49.11 | O |
| ATOM | 1572 | N | ASP | A | 122 | −53.899 | 57.206 | 11.995 | 1.00 | 50.51 | N |
| ATOM | 1573 | CA | ASP | A | 122 | −54.078 | 58.537 | 12.596 | 1.00 | 51.46 | C |
| ATOM | 1575 | CB | ASP | A | 122 | −54.604 | 58.443 | 14.050 | 1.00 | 51.29 | C |
| ATOM | 1578 | CG | ASP | A | 122 | −53.570 | 57.919 | 15.036 | 1.00 | 50.73 | C |
| ATOM | 1579 | OD1 | ASP | A | 122 | −52.353 | 58.025 | 14.777 | 1.00 | 49.90 | O |
| ATOM | 1580 | OD2 | ASP | A | 122 | −53.988 | 57.398 | 16.088 | 1.00 | 49.66 | O |
| ATOM | 1581 | C | ASP | A | 122 | −52.792 | 59.358 | 12.502 | 1.00 | 52.60 | C |
| ATOM | 1582 | O | ASP | A | 122 | −51.830 | 58.953 | 11.835 | 1.00 | 52.65 | O |
| ATOM | 1584 | N | GLN | A | 123 | −52.802 | 60.512 | 13.172 | 1.00 | 53.88 | N |
| ATOM | 1585 | CA | GLN | A | 123 | −51.680 | 61.456 | 13.195 | 1.00 | 54.66 | C |
| ATOM | 1587 | CB | GLN | A | 123 | −51.993 | 62.594 | 14.178 | 1.00 | 55.01 | C |
| ATOM | 1590 | CG | GLN | A | 123 | −53.249 | 63.442 | 13.831 | 1.00 | 56.15 | C |
| ATOM | 1593 | CD | GLN | A | 123 | −52.943 | 64.736 | 13.064 | 1.00 | 57.64 | C |
| ATOM | 1594 | OE1 | GLN | A | 123 | −51.779 | 65.102 | 12.859 | 1.00 | 59.10 | O |
| ATOM | 1595 | NE2 | GLN | A | 123 | −54.001 | 65.438 | 12.652 | 1.00 | 57.63 | N |
| ATOM | 1598 | C | GLN | A | 123 | −50.365 | 60.772 | 13.591 | 1.00 | 54.87 | C |
| ATOM | 1599 | O | GLN | A | 123 | −49.309 | 61.078 | 13.034 | 1.00 | 54.67 | O |
| ATOM | 1601 | N | ASN | A | 124 | −50.458 | 59.834 | 14.538 | 1.00 | 55.21 | N |
| ATOM | 1602 | CA | ASN | A | 124 | −49.300 | 59.137 | 15.109 | 1.00 | 55.39 | C |
| ATOM | 1604 | CB | ASN | A | 124 | −49.421 | 59.122 | 16.637 | 1.00 | 55.52 | C |
| ATOM | 1607 | CG | ASN | A | 124 | −49.833 | 60.478 | 17.202 | 1.00 | 55.98 | C |
| ATOM | 1608 | OD1 | ASN | A | 124 | −49.093 | 61.460 | 17.091 | 1.00 | 56.93 | O |
| ATOM | 1609 | ND2 | ASN | A | 124 | −51.026 | 60.540 | 17.797 | 1.00 | 55.99 | N |
| ATOM | 1612 | C | ASN | A | 124 | −49.116 | 57.705 | 14.589 | 1.00 | 55.27 | C |
| ATOM | 1613 | O | ASN | A | 124 | −48.530 | 56.864 | 15.271 | 1.00 | 55.18 | O |
| ATOM | 1615 | N | GLY | A | 125 | −49.626 | 57.430 | 13.391 | 1.00 | 55.18 | N |
| ATOM | 1616 | CA | GLY | A | 125 | −49.311 | 56.190 | 12.672 | 1.00 | 55.08 | C |
| ATOM | 1619 | C | GLY | A | 125 | −49.994 | 54.897 | 13.119 | 1.00 | 54.90 | C |
| ATOM | 1620 | O | GLY | A | 125 | −49.543 | 53.806 | 12.750 | 1.00 | 55.24 | O |
| ATOM | 1622 | N | ASN | A | 126 | −51.072 | 55.008 | 13.900 | 1.00 | 54.23 | N |
| ATOM | 1623 | CA | ASN | A | 126 | −51.871 | 53.853 | 14.329 | 1.00 | 53.39 | C |
| ATOM | 1625 | CB | ASN | A | 126 | −51.927 | 53.782 | 15.852 | 1.00 | 53.27 | C |
| ATOM | 1628 | CG | ASN | A | 126 | −50.596 | 53.425 | 16.466 | 1.00 | 52.81 | C |
| ATOM | 1629 | OD1 | ASN | A | 126 | −49.636 | 53.113 | 15.764 | 1.00 | 52.29 | O |
| ATOM | 1630 | ND2 | ASN | A | 126 | −50.532 | 53.460 | 17.789 | 1.00 | 52.53 | N |
| ATOM | 1633 | C | ASN | A | 126 | −53.274 | 53.978 | 13.771 | 1.00 | 52.82 | C |
| ATOM | 1634 | O | ASN | A | 126 | −53.724 | 55.081 | 13.494 | 1.00 | 52.69 | O |
| ATOM | 1636 | N | PHE | A | 127 | −53.968 | 52.857 | 13.607 | 1.00 | 52.17 | N |
| ATOM | 1637 | CA | PHE | A | 127 | −55.287 | 52.875 | 12.962 | 1.00 | 51.56 | C |
| ATOM | 1639 | CB | PHE | A | 127 | −55.805 | 51.451 | 12.721 | 1.00 | 51.35 | C |
| ATOM | 1642 | CG | PHE | A | 127 | −55.119 | 50.730 | 11.587 | 1.00 | 50.06 | C |
| ATOM | 1643 | CD1 | PHE | A | 127 | −54.068 | 49.856 | 11.831 | 1.00 | 48.90 | C |
| ATOM | 1645 | CE1 | PHE | A | 127 | −53.437 | 49.187 | 10.789 | 1.00 | 47.59 | C |
| ATOM | 1647 | CZ | PHE | A | 127 | −53.857 | 49.383 | 9.495 | 1.00 | 47.40 | C |
| ATOM | 1649 | CE2 | PHE | A | 127 | −54.906 | 50.244 | 9.234 | 1.00 | 47.96 | C |
| ATOM | 1651 | CD2 | PHE | A | 127 | −55.533 | 50.915 | 10.276 | 1.00 | 48.85 | C |

TABLE 3-7-continued

| | | | | | | Coordinates of *P. tremuloides* IspS | | | | |
|---|---|---|---|---|---|---|---|---|---|---|
| ATOM | 1653 | C | PHE | A | 127 | −56.303 | 53.690 | 13.776 | 1.00 | 51.35 C |
| ATOM | 1654 | O | PHE | A | 127 | −56.347 | 53.594 | 15.002 | 1.00 | 51.09 O |
| ATOM | 1656 | N | LEU | A | 128 | −57.100 | 54.500 | 13.083 | 1.00 | 51.15 N |
| ATOM | 1657 | CA | LEU | A | 128 | −58.143 | 55.280 | 13.727 | 1.00 | 51.09 C |
| ATOM | 1659 | CB | LEU | A | 128 | −59.039 | 55.979 | 12.694 | 1.00 | 51.17 C |
| ATOM | 1662 | CG | LEU | A | 128 | −58.463 | 57.046 | 11.746 | 1.00 | 51.31 C |
| ATOM | 1664 | CD1 | LEU | A | 128 | −59.571 | 57.628 | 10.855 | 1.00 | 50.76 C |
| ATOM | 1668 | CD2 | LEU | A | 128 | −57.762 | 58.157 | 12.508 | 1.00 | 50.98 C |
| ATOM | 1672 | C | LEU | A | 128 | −58.996 | 54.353 | 14.581 | 1.00 | 51.06 C |
| ATOM | 1673 | O | LEU | A | 128 | −59.573 | 53.393 | 14.078 | 1.00 | 50.94 O |
| ATOM | 1675 | N | GLU | A | 129 | −59.053 | 54.637 | 15.879 | 1.00 | 51.12 N |
| ATOM | 1676 | CA | GLU | A | 129 | −59.916 | 53.913 | 16.808 | 1.00 | 50.99 C |
| ATOM | 1678 | CB | GLU | A | 129 | −60.019 | 54.665 | 18.132 | 1.00 | 51.14 C |
| ATOM | 1681 | CG | GLU | A | 129 | −58.850 | 54.431 | 19.049 | 1.00 | 52.04 C |
| ATOM | 1684 | CD | GLU | A | 129 | −58.903 | 53.069 | 19.697 | 1.00 | 53.22 C |
| ATOM | 1685 | OE1 | GLU | A | 129 | −58.040 | 52.219 | 19.376 | 1.00 | 54.19 O |
| ATOM | 1686 | OE2 | GLU | A | 129 | −59.823 | 52.848 | 20.516 | 1.00 | 53.51 O |
| ATOM | 1687 | C | GLU | A | 129 | −61.314 | 53.712 | 16.260 | 1.00 | 50.66 C |
| ATOM | 1688 | O | GLU | A | 129 | −61.791 | 52.587 | 16.200 | 1.00 | 50.83 O |
| ATOM | 1690 | N | ASN | A | 130 | −61.960 | 54.799 | 15.839 | 1.00 | 50.28 N |
| ATOM | 1691 | CA | ASN | A | 130 | −63.389 | 54.765 | 15.486 | 1.00 | 50.03 C |
| ATOM | 1693 | CB | ASN | A | 130 | −63.910 | 56.182 | 15.193 | 1.00 | 50.09 C |
| ATOM | 1696 | CG | ASN | A | 130 | −63.286 | 56.805 | 13.960 | 1.00 | 50.37 C |
| ATOM | 1697 | OD1 | ASN | A | 130 | −62.504 | 56.177 | 13.249 | 1.00 | 51.44 O |
| ATOM | 1698 | ND2 | ASN | A | 130 | −63.634 | 58.056 | 13.701 | 1.00 | 50.27 N |
| ATOM | 1701 | C | ASN | A | 130 | −63.804 | 53.782 | 14.369 | 1.00 | 49.56 C |
| ATOM | 1702 | O | ASN | A | 130 | −64.993 | 53.581 | 14.131 | 1.00 | 49.44 O |
| ATOM | 1704 | N | LEU | A | 131 | −62.828 | 53.175 | 13.699 | 1.00 | 49.21 N |
| ATOM | 1705 | CA | LEU | A | 131 | −63.087 | 52.103 | 12.729 | 1.00 | 48.78 C |
| ATOM | 1707 | CB | LEU | A | 131 | −61.846 | 51.832 | 11.875 | 1.00 | 48.64 C |
| ATOM | 1710 | CG | LEU | A | 131 | −61.445 | 52.939 | 10.898 | 1.00 | 48.26 C |
| ATOM | 1712 | CD1 | LEU | A | 131 | −60.029 | 52.709 | 10.375 | 1.00 | 47.76 C |
| ATOM | 1716 | CD2 | LEU | A | 131 | −62.441 | 53.039 | 9.754 | 1.00 | 47.32 C |
| ATOM | 1720 | C | LEU | A | 131 | −63.516 | 50.798 | 13.394 | 1.00 | 48.58 C |
| ATOM | 1721 | O | LEU | A | 131 | −64.093 | 49.939 | 12.731 | 1.00 | 48.64 O |
| ATOM | 1723 | N | LYS | A | 132 | −63.225 | 50.645 | 14.689 | 1.00 | 48.23 N |
| ATOM | 1724 | CA | LYS | A | 132 | −63.650 | 49.474 | 15.465 | 1.00 | 47.80 C |
| ATOM | 1726 | CB | LYS | A | 132 | −63.156 | 49.587 | 16.913 | 1.00 | 47.71 C |
| ATOM | 1729 | CG | LYS | A | 132 | −63.930 | 50.615 | 17.728 | 1.00 | 47.80 C |
| ATOM | 1732 | CD | LYS | A | 132 | −63.430 | 50.779 | 19.153 | 1.00 | 47.75 C |
| ATOM | 1735 | CE | LYS | A | 132 | −64.438 | 51.577 | 19.982 | 1.00 | 47.22 C |
| ATOM | 1738 | NZ | LYS | A | 132 | −63.769 | 52.364 | 21.033 | 1.00 | 46.65 N |
| ATOM | 1742 | C | LYS | A | 132 | −65.182 | 49.308 | 15.446 | 1.00 | 47.56 C |
| ATOM | 1743 | O | LYS | A | 132 | −65.696 | 48.204 | 15.616 | 1.00 | 47.76 O |
| ATOM | 1745 | N | GLU | A | 133 | −65.901 | 50.413 | 15.249 | 1.00 | 47.18 N |
| ATOM | 1746 | CA | GLU | A | 133 | −67.371 | 50.412 | 15.191 | 1.00 | 46.79 C |
| ATOM | 1748 | CB | GLU | A | 133 | −67.898 | 51.850 | 15.337 | 1.00 | 46.95 C |
| ATOM | 1751 | CG | GLU | A | 133 | −67.840 | 52.376 | 16.776 | 1.00 | 47.56 C |
| ATOM | 1754 | CD | GLU | A | 133 | −67.613 | 53.886 | 16.863 | 1.00 | 48.41 C |
| ATOM | 1755 | OE1 | GLU | A | 133 | −68.247 | 54.648 | 16.093 | 1.00 | 47.67 O |
| ATOM | 1756 | OE2 | GLU | A | 133 | −66.798 | 54.304 | 17.721 | 1.00 | 48.92 O |
| ATOM | 1757 | C | GLU | A | 133 | −67.949 | 49.770 | 13.918 | 1.00 | 46.10 C |
| ATOM | 1758 | O | GLU | A | 133 | −69.140 | 49.446 | 13.874 | 1.00 | 46.11 O |
| ATOM | 1760 | N | ASP | A | 134 | −67.103 | 49.601 | 12.896 | 1.00 | 45.11 N |
| ATOM | 1761 | CA | ASP | A | 134 | −67.477 | 48.995 | 11.608 | 1.00 | 44.06 C |
| ATOM | 1763 | CB | ASP | A | 134 | −66.934 | 49.868 | 10.474 | 1.00 | 43.97 C |
| ATOM | 1766 | CG | ASP | A | 134 | −67.380 | 49.411 | 9.104 | 1.00 | 44.08 C |
| ATOM | 1767 | OD1 | ASP | A | 134 | −68.072 | 48.373 | 8.972 | 1.00 | 43.42 O |
| ATOM | 1768 | OD2 | ASP | A | 134 | −67.020 | 50.116 | 8.141 | 1.00 | 44.84 O |
| ATOM | 1769 | C | ASP | A | 134 | −66.910 | 47.570 | 11.526 | 1.00 | 43.12 C |
| ATOM | 1770 | O | ASP | A | 134 | −65.788 | 47.357 | 11.080 | 1.00 | 43.19 O |
| ATOM | 1772 | N | ILE | A | 135 | −67.708 | 46.594 | 11.944 | 1.00 | 41.85 N |
| ATOM | 1773 | CA | ILE | A | 135 | −67.216 | 45.247 | 12.216 | 1.00 | 40.75 C |
| ATOM | 1775 | CB | ILE | A | 135 | −68.183 | 44.507 | 13.170 | 1.00 | 40.80 C |
| ATOM | 1777 | CG1 | ILE | A | 135 | −68.227 | 45.226 | 14.524 | 1.00 | 41.21 C |
| ATOM | 1780 | CD1 | ILE | A | 135 | −69.353 | 46.283 | 14.633 | 1.00 | 42.86 C |
| ATOM | 1784 | CG2 | ILE | A | 135 | −67.776 | 43.063 | 13.373 | 1.00 | 40.88 C |
| ATOM | 1788 | C | ILE | A | 135 | −66.980 | 44.457 | 10.933 | 1.00 | 39.67 C |
| ATOM | 1789 | O | ILE | A | 135 | −66.166 | 43.537 | 10.901 | 1.00 | 39.37 O |
| ATOM | 1791 | N | LYS | A | 136 | −67.690 | 44.828 | 9.877 | 1.00 | 38.62 N |
| ATOM | 1792 | CA | LYS | A | 136 | −67.465 | 44.256 | 8.554 | 1.00 | 37.88 C |
| ATOM | 1794 | CB | LYS | A | 136 | −68.525 | 44.749 | 7.561 | 1.00 | 38.33 C |
| ATOM | 1797 | CG | LYS | A | 136 | −69.955 | 44.342 | 7.879 | 1.00 | 40.17 C |
| ATOM | 1800 | CD | LYS | A | 136 | −70.486 | 43.262 | 6.911 | 1.00 | 42.97 C |
| ATOM | 1803 | CE | LYS | A | 136 | −71.624 | 42.389 | 7.536 | 1.00 | 44.00 C |
| ATOM | 1806 | NZ | LYS | A | 136 | −72.950 | 43.086 | 7.726 | 1.00 | 43.82 N |
| ATOM | 1810 | C | LYS | A | 136 | −66.097 | 44.687 | 8.047 | 1.00 | 36.38 C |
| ATOM | 1811 | O | LYS | A | 136 | −65.399 | 43.914 | 7.388 | 1.00 | 36.24 O |

TABLE 3-7-continued

| | | | | | | | | | | | |
|---|---|---|---|---|---|---|---|---|---|---|---|
| ATOM | 1813 | N | ALA | A | 137 | −65.728 | 45.931 | 8.341 | 1.00 | 34.51 | N |
| ATOM | 1814 | CA | ALA | A | 137 | −64.463 | 46.474 | 7.876 | 1.00 | 33.41 | C |
| ATOM | 1816 | CB | ALA | A | 137 | −64.432 | 47.981 | 8.058 | 1.00 | 33.43 | C |
| ATOM | 1820 | C | ALA | A | 137 | −63.291 | 45.827 | 8.600 | 1.00 | 32.30 | C |
| ATOM | 1821 | O | ALA | A | 137 | −62.288 | 45.481 | 7.995 | 1.00 | 31.89 | O |
| ATOM | 1823 | N | ILE | A | 138 | −63.437 | 45.662 | 9.905 | 1.00 | 31.41 | N |
| ATOM | 1824 | CA | ILE | A | 138 | −62.395 | 45.074 | 10.737 | 1.00 | 30.60 | C |
| ATOM | 1826 | CB | ILE | A | 138 | −62.770 | 45.131 | 12.238 | 1.00 | 30.20 | C |
| ATOM | 1828 | CG1 | ILE | A | 138 | −62.914 | 46.576 | 12.689 | 1.00 | 29.92 | C |
| ATOM | 1831 | CD1 | ILE | A | 138 | −61.681 | 47.414 | 12.417 | 1.00 | 30.50 | C |
| ATOM | 1835 | CG2 | ILE | A | 138 | −61.706 | 44.470 | 13.085 | 1.00 | 29.73 | C |
| ATOM | 1839 | C | ILE | A | 138 | −62.140 | 43.631 | 10.320 | 1.00 | 30.34 | C |
| ATOM | 1840 | O | ILE | A | 138 | −60.972 | 43.203 | 10.212 | 1.00 | 30.65 | O |
| ATOM | 1842 | N | LEU | A | 139 | −63.227 | 42.884 | 10.098 | 1.00 | 29.69 | N |
| ATOM | 1843 | CA | LEU | A | 139 | −63.134 | 41.523 | 9.562 | 1.00 | 29.23 | C |
| ATOM | 1845 | CB | LEU | A | 139 | −64.517 | 40.917 | 9.332 | 1.00 | 28.92 | C |
| ATOM | 1848 | CG | LEU | A | 139 | −65.066 | 40.185 | 10.545 | 1.00 | 29.06 | C |
| ATOM | 1850 | CD1 | LEU | A | 139 | −66.541 | 39.875 | 10.352 | 1.00 | 28.20 | C |
| ATOM | 1854 | CD2 | LEU | A | 139 | −64.250 | 38.922 | 10.813 | 1.00 | 28.59 | C |
| ATOM | 1858 | C | LEU | A | 139 | −62.382 | 41.546 | 8.247 | 1.00 | 29.00 | C |
| ATOM | 1859 | O | LEU | A | 139 | −61.444 | 40.773 | 8.035 | 1.00 | 29.50 | O |
| ATOM | 1861 | N | SER | A | 140 | −62.790 | 42.458 | 7.372 | 1.00 | 28.14 | N |
| ATOM | 1862 | CA | SER | A | 140 | −62.222 | 42.526 | 6.054 | 1.00 | 27.40 | C |
| ATOM | 1864 | CB | SER | A | 140 | −62.912 | 43.619 | 5.260 | 1.00 | 27.35 | C |
| ATOM | 1867 | OG | SER | A | 140 | −63.310 | 43.103 | 4.015 | 1.00 | 28.43 | O |
| ATOM | 1869 | C | SER | A | 140 | −60.720 | 42.777 | 6.123 | 1.00 | 26.77 | C |
| ATOM | 1870 | O | SER | A | 140 | −59.975 | 42.269 | 5.298 | 1.00 | 27.29 | O |
| ATOM | 1872 | N | LEU | A | 141 | −60.285 | 43.563 | 7.105 | 1.00 | 25.89 | N |
| ATOM | 1873 | CA | LEU | A | 141 | −58.872 | 43.897 | 7.283 | 1.00 | 25.20 | C |
| ATOM | 1875 | CB | LEU | A | 141 | −58.717 | 45.164 | 8.155 | 1.00 | 25.00 | C |
| ATOM | 1878 | CG | LEU | A | 141 | −57.298 | 45.670 | 8.489 | 1.00 | 24.35 | C |
| ATOM | 1880 | CD1 | LEU | A | 141 | −56.497 | 45.974 | 7.232 | 1.00 | 22.75 | C |
| ATOM | 1884 | CD2 | LEU | A | 141 | −57.329 | 46.893 | 9.385 | 1.00 | 22.81 | C |
| ATOM | 1888 | C | LEU | A | 141 | −58.140 | 42.721 | 7.920 | 1.00 | 24.92 | C |
| ATOM | 1889 | O | LEU | A | 141 | −57.034 | 42.380 | 7.521 | 1.00 | 24.77 | O |
| ATOM | 1891 | N | TYR | A | 142 | −58.751 | 42.101 | 8.921 | 1.00 | 24.51 | N |
| ATOM | 1892 | CA | TYR | A | 142 | −58.163 | 40.913 | 9.514 | 1.00 | 24.36 | C |
| ATOM | 1894 | CB | TYR | A | 142 | −59.120 | 40.325 | 10.538 | 1.00 | 24.18 | C |
| ATOM | 1897 | CG | TYR | A | 142 | −58.774 | 38.941 | 11.046 | 1.00 | 23.72 | C |
| ATOM | 1898 | CD1 | TYR | A | 142 | −57.878 | 38.763 | 12.091 | 1.00 | 22.97 | C |
| ATOM | 1900 | CE1 | TYR | A | 142 | −57.593 | 37.500 | 12.582 | 1.00 | 24.25 | C |
| ATOM | 1902 | CZ | TYR | A | 142 | −58.229 | 36.386 | 12.030 | 1.00 | 25.75 | C |
| ATOM | 1903 | OH | TYR | A | 142 | −57.967 | 35.100 | 12.500 | 1.00 | 26.97 | O |
| ATOM | 1905 | CE2 | TYR | A | 142 | −59.120 | 36.551 | 10.988 | 1.00 | 25.02 | C |
| ATOM | 1907 | CD2 | TYR | A | 142 | −59.390 | 37.820 | 10.511 | 1.00 | 24.01 | C |
| ATOM | 1909 | C | TYR | A | 142 | −57.877 | 39.896 | 8.423 | 1.00 | 24.39 | C |
| ATOM | 1910 | O | TYR | A | 142 | −56.822 | 39.276 | 8.380 | 1.00 | 24.19 | O |
| ATOM | 1912 | N | GLU | A | 143 | −58.841 | 39.760 | 7.527 | 1.00 | 24.59 | N |
| ATOM | 1913 | CA | GLU | A | 143 | −58.820 | 38.728 | 6.521 | 1.00 | 24.70 | C |
| ATOM | 1915 | CB | GLU | A | 143 | −60.194 | 38.636 | 5.853 | 1.00 | 24.69 | C |
| ATOM | 1918 | CG | GLU | A | 143 | −60.651 | 37.219 | 5.547 | 1.00 | 27.21 | C |
| ATOM | 1921 | CD | GLU | A | 143 | −61.127 | 36.426 | 6.774 | 1.00 | 30.20 | C |
| ATOM | 1922 | OE1 | GLU | A | 143 | −60.261 | 35.776 | 7.393 | 1.00 | 33.40 | O |
| ATOM | 1923 | OE2 | GLU | A | 143 | −62.351 | 36.421 | 7.097 | 1.00 | 30.50 | O |
| ATOM | 1924 | C | GLU | A | 143 | −57.701 | 39.010 | 5.518 | 1.00 | 24.08 | C |
| ATOM | 1925 | O | GLU | A | 143 | −56.984 | 38.090 | 5.126 | 1.00 | 24.53 | O |
| ATOM | 1927 | N | ALA | A | 144 | −57.537 | 40.281 | 5.147 | 1.00 | 23.30 | N |
| ATOM | 1928 | CA | ALA | A | 144 | −56.515 | 40.715 | 4.173 | 1.00 | 22.79 | C |
| ATOM | 1930 | CB | ALA | A | 144 | −56.787 | 42.154 | 3.740 | 1.00 | 22.49 | C |
| ATOM | 1934 | C | ALA | A | 144 | −55.073 | 40.598 | 4.701 | 1.00 | 22.42 | C |
| ATOM | 1935 | O | ALA | A | 144 | −54.128 | 40.380 | 3.935 | 1.00 | 22.36 | O |
| ATOM | 1937 | N | SER | A | 145 | −54.909 | 40.713 | 6.012 | 1.00 | 21.80 | N |
| ATOM | 1938 | CA | SER | A | 145 | −53.593 | 40.822 | 6.600 | 1.00 | 21.36 | C |
| ATOM | 1940 | CB | SER | A | 145 | −53.726 | 41.170 | 8.066 | 1.00 | 21.21 | C |
| ATOM | 1943 | OG | SER | A | 145 | −54.337 | 40.100 | 8.753 | 1.00 | 21.59 | O |
| ATOM | 1945 | C | SER | A | 145 | −52.797 | 39.537 | 6.476 | 1.00 | 21.30 | C |
| ATOM | 1946 | O | SER | A | 145 | −51.571 | 39.533 | 6.701 | 1.00 | 21.50 | O |
| ATOM | 1948 | N | PHE | A | 146 | −53.488 | 38.439 | 6.154 | 1.00 | 21.00 | N |
| ATOM | 1949 | CA | PHE | A | 146 | −52.827 | 37.127 | 6.030 | 1.00 | 20.41 | C |
| ATOM | 1951 | CB | PHE | A | 146 | −53.796 | 35.979 | 6.338 | 1.00 | 20.20 | C |
| ATOM | 1954 | CG | PHE | A | 146 | −54.130 | 35.873 | 7.798 | 1.00 | 19.91 | C |
| ATOM | 1955 | CD1 | PHE | A | 146 | −53.382 | 35.087 | 8.637 | 1.00 | 20.48 | C |
| ATOM | 1957 | CE1 | PHE | A | 146 | −53.679 | 35.012 | 9.992 | 1.00 | 20.59 | C |
| ATOM | 1959 | CZ | PHE | A | 146 | −54.731 | 35.740 | 10.508 | 1.00 | 19.15 | C |
| ATOM | 1961 | CE2 | PHE | A | 146 | −55.464 | 36.536 | 9.691 | 1.00 | 19.10 | C |
| ATOM | 1963 | CD2 | PHE | A | 146 | −55.155 | 36.615 | 8.343 | 1.00 | 20.16 | C |
| ATOM | 1965 | C | PHE | A | 146 | −52.174 | 36.964 | 4.680 | 1.00 | 19.76 | C |
| ATOM | 1966 | O | PHE | A | 146 | −51.305 | 36.116 | 4.523 | 1.00 | 19.46 | O |

TABLE 3-7-continued

| | | | | | | | | | | | |
|---|---|---|---|---|---|---|---|---|---|---|---|
| ATOM | 1968 | N | LEU | A | 147 | −52.550 | 37.819 | 3.729 | 1.00 | 19.34 | N |
| ATOM | 1969 | CA | LEU | A | 147 | −51.933 | 37.804 | 2.402 | 1.00 | 19.13 | C |
| ATOM | 1971 | CB | LEU | A | 147 | −52.905 | 38.367 | 1.347 | 1.00 | 18.67 | C |
| ATOM | 1974 | CG | LEU | A | 147 | −53.964 | 37.334 | .919 | 1.00 | 18.11 | C |
| ATOM | 1976 | CD1 | LEU | A | 147 | −55.090 | 37.248 | 1.961 | 1.00 | 15.10 | C |
| ATOM | 1980 | CD2 | LEU | A | 147 | −54.494 | 37.609 | −.499 | 1.00 | 16.50 | C |
| ATOM | 1984 | C | LEU | A | 147 | −50.582 | 38.525 | 2.369 | 1.00 | 19.10 | C |
| ATOM | 1985 | O | LEU | A | 147 | −49.992 | 38.715 | 1.311 | 1.00 | 19.44 | O |
| ATOM | 1987 | N | ALA | A | 148 | −50.075 | 38.882 | 3.542 | 1.00 | 19.13 | N |
| ATOM | 1988 | CA | ALA | A | 148 | −48.967 | 39.806 | 3.664 | 1.00 | 18.84 | C |
| ATOM | 1990 | CB | ALA | A | 148 | −48.762 | 40.167 | 5.117 | 1.00 | 18.78 | C |
| ATOM | 1994 | C | ALA | A | 148 | −47.723 | 39.184 | 3.113 | 1.00 | 18.85 | C |
| ATOM | 1995 | O | ALA | A | 148 | −47.548 | 37.975 | 3.206 | 1.00 | 18.80 | O |
| ATOM | 1997 | N | LEU | A | 149 | −46.869 | 40.013 | 2.523 | 1.00 | 19.08 | N |
| ATOM | 1998 | CA | LEU | A | 149 | −45.507 | 39.601 | 2.215 | 1.00 | 19.32 | C |
| ATOM | 2000 | CB | LEU | A | 149 | −45.056 | 40.145 | .863 | 1.00 | 19.14 | C |
| ATOM | 2003 | CG | LEU | A | 149 | −45.819 | 39.650 | −.364 | 1.00 | 19.16 | C |
| ATOM | 2005 | CD1 | LEU | A | 149 | −45.036 | 39.929 | −1.645 | 1.00 | 18.43 | C |
| ATOM | 2009 | CD2 | LEU | A | 149 | −46.089 | 38.175 | −.259 | 1.00 | 20.09 | C |
| ATOM | 2013 | C | LEU | A | 149 | −44.527 | 40.029 | 3.304 | 1.00 | 19.60 | C |
| ATOM | 2014 | O | LEU | A | 149 | −44.797 | 40.916 | 4.113 | 1.00 | 19.20 | O |
| ATOM | 2016 | N | GLU | A | 150 | −43.384 | 39.361 | 3.309 | 1.00 | 20.42 | N |
| ATOM | 2017 | CA | GLU | A | 150 | −42.286 | 39.674 | 4.215 | 1.00 | 21.03 | C |
| ATOM | 2019 | CB | GLU | A | 150 | −41.098 | 38.741 | 3.948 | 1.00 | 21.03 | C |
| ATOM | 2022 | CG | GLU | A | 150 | −40.491 | 38.176 | 5.205 | 1.00 | 22.23 | C |
| ATOM | 2025 | CD | GLU | A | 150 | −39.433 | 37.117 | 4.941 | 1.00 | 24.34 | C |
| ATOM | 2026 | OE1 | GLU | A | 150 | −39.189 | 36.786 | 3.753 | 1.00 | 24.53 | O |
| ATOM | 2027 | OE2 | GLU | A | 150 | −38.843 | 36.625 | 5.940 | 1.00 | 25.82 | O |
| ATOM | 2028 | C | GLU | A | 150 | −41.887 | 41.130 | 4.011 | 1.00 | 21.29 | C |
| ATOM | 2029 | O | GLU | A | 150 | −41.619 | 41.544 | 2.885 | 1.00 | 21.13 | O |
| ATOM | 2031 | N | GLY | A | 151 | −41.893 | 41.903 | 5.094 | 1.00 | 21.89 | N |
| ATOM | 2032 | CA | GLY | A | 151 | −41.636 | 43.341 | 5.030 | 1.00 | 22.25 | C |
| ATOM | 2035 | C | GLY | A | 151 | −42.871 | 44.221 | 5.152 | 1.00 | 22.67 | C |
| ATOM | 2036 | O | GLY | A | 151 | −42.757 | 45.397 | 5.462 | 1.00 | 22.84 | O |
| ATOM | 2038 | N | GLU | A | 152 | −44.055 | 43.669 | 4.918 | 1.00 | 23.19 | N |
| ATOM | 2039 | CA | GLU | A | 152 | −45.263 | 44.474 | 4.937 | 1.00 | 23.76 | C |
| ATOM | 2041 | CB | GLU | A | 152 | −46.350 | 43.813 | 4.100 | 1.00 | 23.79 | C |
| ATOM | 2044 | CG | GLU | A | 152 | −46.037 | 43.890 | 2.615 | 1.00 | 23.98 | C |
| ATOM | 2047 | CD | GLU | A | 152 | −47.147 | 43.368 | 1.749 | 1.00 | 23.72 | C |
| ATOM | 2048 | OE1 | GLU | A | 152 | −47.226 | 43.771 | .574 | 1.00 | 22.11 | O |
| ATOM | 2049 | OE2 | GLU | A | 152 | −47.939 | 42.542 | 2.241 | 1.00 | 25.41 | O |
| ATOM | 2050 | C | GLU | A | 152 | −45.722 | 44.719 | 6.365 | 1.00 | 24.47 | C |
| ATOM | 2051 | O | GLU | A | 152 | −46.586 | 44.006 | 6.906 | 1.00 | 24.70 | O |
| ATOM | 2053 | N | ASN | A | 153 | −45.134 | 45.744 | 6.969 | 1.00 | 25.00 | N |
| ATOM | 2054 | CA | ASN | A | 153 | −45.287 | 45.978 | 8.404 | 1.00 | 25.59 | C |
| ATOM | 2056 | CB | ASN | A | 153 | −44.221 | 46.957 | 8.902 | 1.00 | 25.55 | C |
| ATOM | 2059 | CG | ASN | A | 153 | −44.386 | 48.331 | 8.308 | 1.00 | 25.57 | C |
| ATOM | 2060 | OD1 | ASN | A | 153 | −44.114 | 48.557 | 7.128 | 1.00 | 24.52 | O |
| ATOM | 2061 | ND2 | ASN | A | 153 | −44.867 | 49.256 | 9.117 | 1.00 | 27.05 | N |
| ATOM | 2064 | C | ASN | A | 153 | −46.679 | 46.486 | 8.772 | 1.00 | 25.92 | C |
| ATOM | 2065 | O | ASN | A | 153 | −47.172 | 46.238 | 9.872 | 1.00 | 26.02 | O |
| ATOM | 2067 | N | ILE | A | 154 | −47.310 | 47.197 | 7.847 | 1.00 | 26.35 | N |
| ATOM | 2068 | CA | ILE | A | 154 | −48.638 | 47.751 | 8.082 | 1.00 | 26.57 | C |
| ATOM | 2070 | CB | ILE | A | 154 | −49.013 | 48.779 | 7.007 | 1.00 | 26.45 | C |
| ATOM | 2072 | CG1 | ILE | A | 154 | −48.159 | 50.023 | 7.164 | 1.00 | 26.36 | C |
| ATOM | 2075 | CD1 | ILE | A | 154 | −48.060 | 50.790 | 5.883 | 1.00 | 27.92 | C |
| ATOM | 2079 | CG2 | ILE | A | 154 | −50.467 | 49.152 | 7.089 | 1.00 | 26.25 | C |
| ATOM | 2083 | C | ILE | A | 154 | −49.674 | 46.643 | 8.111 | 1.00 | 26.96 | C |
| ATOM | 2084 | O | ILE | A | 154 | −50.650 | 46.741 | 8.851 | 1.00 | 27.12 | O |
| ATOM | 2086 | N | LEU | A | 155 | −49.467 | 45.588 | 7.320 | 1.00 | 27.35 | N |
| ATOM | 2087 | CA | LEU | A | 155 | −50.422 | 44.475 | 7.304 | 1.00 | 27.76 | C |
| ATOM | 2089 | CB | LEU | A | 155 | −50.238 | 43.594 | 6.067 | 1.00 | 27.73 | C |
| ATOM | 2092 | CG | LEU | A | 155 | −51.090 | 43.990 | 4.875 | 1.00 | 27.31 | C |
| ATOM | 2094 | CD1 | LEU | A | 155 | −50.980 | 45.456 | 4.683 | 1.00 | 28.13 | C |
| ATOM | 2098 | CD2 | LEU | A | 155 | −50.633 | 43.262 | 3.623 | 1.00 | 27.79 | C |
| ATOM | 2102 | C | LEU | A | 155 | −50.340 | 43.642 | 8.582 | 1.00 | 28.22 | C |
| ATOM | 2103 | O | LEU | A | 155 | −51.361 | 43.237 | 9.112 | 1.00 | 27.95 | O |
| ATOM | 2105 | N | ASP | A | 156 | −49.128 | 43.395 | 9.068 | 1.00 | 28.95 | N |
| ATOM | 2106 | CA | ASP | A | 156 | −48.944 | 42.723 | 10.348 | 1.00 | 29.71 | C |
| ATOM | 2108 | CB | ASP | A | 156 | −47.450 | 42.461 | 10.639 | 1.00 | 30.23 | C |
| ATOM | 2111 | CG | ASP | A | 156 | −46.938 | 41.125 | 10.027 | 1.00 | 32.82 | C |
| ATOM | 2112 | OD1 | ASP | A | 156 | −47.765 | 40.240 | 9.658 | 1.00 | 36.27 | O |
| ATOM | 2113 | OD2 | ASP | A | 156 | −45.700 | 40.961 | 9.923 | 1.00 | 34.48 | O |
| ATOM | 2114 | C | ASP | A | 156 | −49.570 | 43.539 | 11.469 | 1.00 | 29.66 | C |
| ATOM | 2115 | O | ASP | A | 156 | −50.109 | 42.969 | 12.425 | 1.00 | 29.81 | O |
| ATOM | 2117 | N | GLU | A | 157 | −49.514 | 44.866 | 11.345 | 1.00 | 29.69 | N |
| ATOM | 2118 | CA | GLU | A | 157 | −50.129 | 45.768 | 12.329 | 1.00 | 29.57 | C |
| ATOM | 2120 | CB | GLU | A | 157 | −49.581 | 47.186 | 12.178 | 1.00 | 29.71 | C |

TABLE 3-7-continued

| | | | | | | | | | | | |
|---|---|---|---|---|---|---|---|---|---|---|---|
| \multicolumn{12}{|c|}{Coordinates of *P. tremuloides* IspS} |
| ATOM | 2123 | CG | GLU | A | 157 | −48.164 | 47.326 | 12.712 | 1.00 | 30.53 | C |
| ATOM | 2126 | CD | GLU | A | 157 | −47.455 | 48.544 | 12.169 | 1.00 | 31.96 | C |
| ATOM | 2127 | OE1 | GLU | A | 157 | −48.167 | 49.491 | 11.741 | 1.00 | 33.56 | O |
| ATOM | 2128 | OE2 | GLU | A | 157 | −46.195 | 48.546 | 12.166 | 1.00 | 31.54 | O |
| ATOM | 2129 | C | GLU | A | 157 | −51.649 | 45.771 | 12.230 | 1.00 | 29.16 | C |
| ATOM | 2130 | O | GLU | A | 157 | −52.330 | 45.819 | 13.241 | 1.00 | 29.00 | O |
| ATOM | 2132 | N | ALA | A | 158 | −52.172 | 45.716 | 11.010 | 1.00 | 28.86 | N |
| ATOM | 2133 | CA | ALA | A | 158 | −53.606 | 45.570 | 10.792 | 1.00 | 28.79 | C |
| ATOM | 2135 | CB | ALA | A | 158 | −53.893 | 45.456 | 9.301 | 1.00 | 28.44 | C |
| ATOM | 2139 | C | ALA | A | 158 | −54.171 | 44.352 | 11.536 | 1.00 | 28.93 | C |
| ATOM | 2140 | O | ALA | A | 158 | −55.265 | 44.402 | 12.098 | 1.00 | 28.77 | O |
| ATOM | 2142 | N | LYS | A | 159 | −53.416 | 43.260 | 11.528 | 1.00 | 29.19 | N |
| ATOM | 2143 | CA | LYS | A | 159 | −53.849 | 42.022 | 12.143 | 1.00 | 29.57 | C |
| ATOM | 2145 | CB | LYS | A | 159 | −52.929 | 40.880 | 11.710 | 1.00 | 29.62 | C |
| ATOM | 2148 | CG | LYS | A | 159 | −53.297 | 39.513 | 12.258 | 1.00 | 30.27 | C |
| ATOM | 2151 | CD | LYS | A | 159 | −52.765 | 38.365 | 11.387 | 1.00 | 31.78 | C |
| ATOM | 2154 | CE | LYS | A | 159 | −51.259 | 38.132 | 11.525 | 1.00 | 33.15 | C |
| ATOM | 2157 | NZ | LYS | A | 159 | −50.911 | 36.696 | 11.248 | 1.00 | 33.88 | N |
| ATOM | 2161 | C | LYS | A | 159 | −53.866 | 42.160 | 13.670 | 1.00 | 29.99 | C |
| ATOM | 2162 | O | LYS | A | 159 | −54.767 | 41.642 | 14.332 | 1.00 | 30.29 | O |
| ATOM | 2164 | N | VAL | A | 160 | −52.886 | 42.862 | 14.236 | 1.00 | 30.07 | N |
| ATOM | 2165 | CA | VAL | A | 160 | −52.840 | 43.047 | 15.696 | 1.00 | 30.03 | C |
| ATOM | 2167 | CB | VAL | A | 160 | −51.520 | 43.691 | 16.162 | 1.00 | 29.88 | C |
| ATOM | 2169 | CG1 | VAL | A | 160 | −51.515 | 43.863 | 17.671 | 1.00 | 28.94 | C |
| ATOM | 2173 | CG2 | VAL | A | 160 | −50.341 | 42.848 | 15.707 | 1.00 | 30.23 | C |
| ATOM | 2177 | C | VAL | A | 160 | −53.996 | 43.925 | 16.149 | 1.00 | 30.05 | C |
| ATOM | 2178 | O | VAL | A | 160 | −54.544 | 43.752 | 17.234 | 1.00 | 30.31 | O |
| ATOM | 2180 | N | PHE | A | 161 | −54.355 | 44.862 | 15.290 | 1.00 | 30.08 | N |
| ATOM | 2181 | CA | PHE | A | 161 | −55.407 | 45.808 | 15.558 | 1.00 | 30.09 | C |
| ATOM | 2183 | CB | PHE | A | 161 | −55.255 | 46.993 | 14.598 | 1.00 | 29.92 | C |
| ATOM | 2186 | CG | PHE | A | 161 | −56.370 | 47.974 | 14.654 | 1.00 | 28.52 | C |
| ATOM | 2187 | CD1 | PHE | A | 161 | −56.347 | 49.005 | 15.554 | 1.00 | 27.92 | C |
| ATOM | 2189 | CE1 | PHE | A | 161 | −57.361 | 49.903 | 15.600 | 1.00 | 28.06 | C |
| ATOM | 2191 | CZ | PHE | A | 161 | −58.411 | 49.783 | 14.733 | 1.00 | 28.76 | C |
| ATOM | 2193 | CE2 | PHE | A | 161 | −58.441 | 48.757 | 13.826 | 1.00 | 28.31 | C |
| ATOM | 2195 | CD2 | PHE | A | 161 | −57.429 | 47.869 | 13.789 | 1.00 | 28.16 | C |
| ATOM | 2197 | C | PHE | A | 161 | −56.746 | 45.123 | 15.388 | 1.00 | 30.55 | C |
| ATOM | 2198 | O | PHE | A | 161 | −57.598 | 45.203 | 16.258 | 1.00 | 30.53 | O |
| ATOM | 2200 | N | ALA | A | 162 | −56.930 | 44.438 | 14.271 | 1.00 | 31.34 | N |
| ATOM | 2201 | CA | ALA | A | 162 | −58.193 | 43.770 | 14.023 | 1.00 | 32.26 | C |
| ATOM | 2203 | CB | ALA | A | 162 | −58.217 | 43.139 | 12.643 | 1.00 | 32.31 | C |
| ATOM | 2207 | C | ALA | A | 162 | −58.500 | 42.734 | 15.118 | 1.00 | 33.09 | C |
| ATOM | 2208 | O | ALA | A | 162 | −59.557 | 42.814 | 15.735 | 1.00 | 33.83 | O |
| ATOM | 2210 | N | ILE | A | 163 | −57.587 | 41.799 | 15.393 | 1.00 | 33.59 | N |
| ATOM | 2211 | CA | ILE | A | 163 | −57.826 | 40.799 | 16.438 | 1.00 | 34.02 | C |
| ATOM | 2213 | CB | ILE | A | 163 | −56.597 | 39.907 | 16.745 | 1.00 | 33.98 | C |
| ATOM | 2215 | CG1 | ILE | A | 163 | −56.235 | 39.008 | 15.566 | 1.00 | 34.37 | C |
| ATOM | 2218 | CD1 | ILE | A | 163 | −54.878 | 38.317 | 15.722 | 1.00 | 34.38 | C |
| ATOM | 2222 | CG2 | ILE | A | 163 | −56.883 | 38.995 | 17.919 | 1.00 | 33.38 | C |
| ATOM | 2226 | C | ILE | A | 163 | −58.225 | 41.472 | 17.744 | 1.00 | 34.75 | C |
| ATOM | 2227 | O | ILE | A | 163 | −59.189 | 41.064 | 18.373 | 1.00 | 35.03 | O |
| ATOM | 2229 | N | SER | A | 164 | −57.501 | 42.504 | 18.156 | 1.00 | 35.76 | N |
| ATOM | 2230 | CA | SER | A | 164 | −57.763 | 43.117 | 19.463 | 1.00 | 36.59 | C |
| ATOM | 2232 | CB | SER | A | 164 | −56.828 | 44.293 | 19.735 | 1.00 | 36.59 | C |
| ATOM | 2235 | OG | SER | A | 164 | −57.350 | 45.485 | 19.164 | 1.00 | 36.46 | O |
| ATOM | 2237 | C | SER | A | 164 | −59.196 | 43.611 | 19.556 | 1.00 | 37.42 | C |
| ATOM | 2238 | O | SER | A | 164 | −59.860 | 43.420 | 20.571 | 1.00 | 37.38 | O |
| ATOM | 2240 | N | HIS | A | 165 | −59.661 | 44.251 | 18.486 | 1.00 | 38.51 | N |
| ATOM | 2241 | CA | HIS | A | 165 | −60.990 | 44.851 | 18.467 | 1.00 | 39.40 | C |
| ATOM | 2243 | CB | HIS | A | 165 | −61.008 | 46.097 | 17.574 | 1.00 | 39.76 | C |
| ATOM | 2246 | CG | HIS | A | 165 | −60.467 | 47.323 | 18.251 | 1.00 | 42.06 | C |
| ATOM | 2247 | ND1 | HIS | A | 165 | −59.205 | 47.821 | 18.000 | 1.00 | 44.21 | N |
| ATOM | 2249 | CE1 | HIS | A | 165 | −58.998 | 48.893 | 18.748 | 1.00 | 45.04 | C |
| ATOM | 2251 | NE2 | HIS | A | 165 | −60.080 | 49.106 | 19.478 | 1.00 | 44.99 | N |
| ATOM | 2253 | CD2 | HIS | A | 165 | −61.011 | 48.135 | 19.192 | 1.00 | 43.76 | C |
| ATOM | 2255 | C | HIS | A | 165 | −62.078 | 43.872 | 18.060 | 1.00 | 39.38 | C |
| ATOM | 2256 | O | HIS | A | 165 | −63.248 | 44.244 | 18.067 | 1.00 | 39.43 | O |
| ATOM | 2258 | N | LEU | A | 166 | −61.683 | 42.632 | 17.745 | 1.00 | 39.54 | N |
| ATOM | 2259 | CA | LEU | A | 166 | −62.589 | 41.550 | 17.326 | 1.00 | 39.55 | C |
| ATOM | 2261 | CB | LEU | A | 166 | −62.001 | 40.766 | 16.154 | 1.00 | 39.28 | C |
| ATOM | 2264 | CG | LEU | A | 166 | −62.156 | 41.339 | 14.752 | 1.00 | 38.23 | C |
| ATOM | 2266 | CD1 | LEU | A | 166 | −61.361 | 40.501 | 13.805 | 1.00 | 37.53 | C |
| ATOM | 2270 | CD2 | LEU | A | 166 | −63.594 | 41.367 | 14.332 | 1.00 | 37.21 | C |
| ATOM | 2274 | C | LEU | A | 166 | −62.842 | 40.555 | 18.438 | 1.00 | 40.08 | C |
| ATOM | 2275 | O | LEU | A | 166 | −63.991 | 40.220 | 18.733 | 1.00 | 40.42 | O |
| ATOM | 2277 | N | LYS | A | 167 | −61.766 | 40.074 | 19.052 | 1.00 | 40.58 | N |
| ATOM | 2278 | CA | LYS | A | 167 | −61.875 | 39.090 | 20.133 | 1.00 | 41.09 | C |
| ATOM | 2280 | CB | LYS | A | 167 | −60.491 | 38.632 | 20.595 | 1.00 | 41.13 | C |

TABLE 3-7-continued

Coordinates of *P. tremuloides* IspS

| ATOM | 2283 | CG | LYS | A | 167 | −59.897 | 39.399 | 21.768 | 1.00 | 42.16 | C |
|---|---|---|---|---|---|---|---|---|---|---|---|
| ATOM | 2286 | CD | LYS | A | 167 | −58.421 | 39.035 | 22.013 | 1.00 | 44.45 | C |
| ATOM | 2289 | CE | LYS | A | 167 | −58.070 | 37.561 | 21.654 | 1.00 | 45.56 | C |
| ATOM | 2292 | NZ | LYS | A | 167 | −56.610 | 37.237 | 21.798 | 1.00 | 46.20 | N |
| ATOM | 2296 | C | LYS | A | 167 | −62.678 | 39.584 | 21.337 | 1.00 | 41.23 | C |
| ATOM | 2297 | O | LYS | A | 167 | −62.994 | 38.793 | 22.215 | 1.00 | 41.47 | O |
| ATOM | 2299 | N | GLU | A | 168 | −62.995 | 40.884 | 21.352 | 1.00 | 41.49 | N |
| ATOM | 2300 | CA | GLU | A | 168 | −63.704 | 41.583 | 22.437 | 1.00 | 41.42 | C |
| ATOM | 2302 | CB | GLU | A | 168 | −65.201 | 41.730 | 22.100 | 1.00 | 41.27 | C |
| ATOM | 2305 | CG | GLU | A | 168 | −65.995 | 40.424 | 22.016 | 1.00 | 41.01 | C |
| ATOM | 2308 | CD | GLU | A | 168 | −66.928 | 40.328 | 20.787 | 1.00 | 40.84 | C |
| ATOM | 2309 | OE1 | GLU | A | 168 | −66.701 | 41.040 | 19.770 | 1.00 | 39.82 | O |
| ATOM | 2310 | OE2 | GLU | A | 168 | −67.884 | 39.509 | 20.845 | 1.00 | 39.04 | O |
| ATOM | 2311 | C | GLU | A | 168 | −63.484 | 41.004 | 23.843 | 1.00 | 41.66 | C |
| ATOM | 2312 | O | GLU | A | 168 | −62.435 | 41.231 | 24.469 | 1.00 | 41.46 | O |
| ATOM | 2314 | N | GLU | A | 172 | −71.668 | 38.961 | 21.192 | 1.00 | 55.65 | N |
| ATOM | 2315 | CA | GLU | A | 172 | −73.052 | 39.153 | 20.721 | 1.00 | 56.00 | C |
| ATOM | 2317 | CB | GLU | A | 172 | −73.876 | 37.880 | 20.937 | 1.00 | 56.27 | C |
| ATOM | 2320 | CG | GLU | A | 172 | −73.198 | 36.620 | 20.390 | 1.00 | 57.12 | C |
| ATOM | 2323 | CD | GLU | A | 172 | −74.056 | 35.363 | 20.516 | 1.00 | 58.18 | C |
| ATOM | 2324 | OE1 | GLU | A | 172 | −75.300 | 35.480 | 20.622 | 1.00 | 58.84 | O |
| ATOM | 2325 | OE2 | GLU | A | 172 | −73.480 | 34.249 | 20.498 | 1.00 | 58.98 | O |
| ATOM | 2326 | C | GLU | A | 172 | −73.766 | 40.386 | 21.334 | 1.00 | 55.70 | C |
| ATOM | 2327 | O | GLU | A | 172 | −74.956 | 40.347 | 21.688 | 1.00 | 54.95 | O |
| ATOM | 2329 | N | LYS | A | 173 | −72.987 | 41.458 | 21.486 | 1.00 | 55.58 | N |
| ATOM | 2330 | CA | LYS | A | 173 | −73.496 | 42.831 | 21.466 | 1.00 | 55.43 | C |
| ATOM | 2332 | CB | LYS | A | 173 | −72.649 | 43.741 | 22.357 | 1.00 | 55.51 | C |
| ATOM | 2335 | CG | LYS | A | 173 | −72.527 | 43.223 | 23.793 | 1.00 | 56.07 | C |
| ATOM | 2338 | CD | LYS | A | 173 | −72.803 | 44.291 | 24.868 | 1.00 | 55.87 | C |
| ATOM | 2341 | CE | LYS | A | 173 | −73.111 | 43.642 | 26.221 | 1.00 | 55.20 | C |
| ATOM | 2344 | NZ | LYS | A | 173 | −72.893 | 44.576 | 27.348 | 1.00 | 54.63 | N |
| ATOM | 2348 | C | LYS | A | 173 | −73.449 | 43.297 | 20.009 | 1.00 | 55.01 | C |
| ATOM | 2349 | O | LYS | A | 173 | −74.091 | 44.274 | 19.625 | 1.00 | 54.97 | O |
| ATOM | 2351 | N | ILE | A | 174 | −72.647 | 42.581 | 19.223 | 1.00 | 54.57 | N |
| ATOM | 2352 | CA | ILE | A | 174 | −72.713 | 42.550 | 17.767 | 1.00 | 54.22 | C |
| ATOM | 2354 | CB | ILE | A | 174 | −71.429 | 41.845 | 17.227 | 1.00 | 54.21 | C |
| ATOM | 2356 | CG1 | ILE | A | 174 | −70.196 | 42.724 | 17.474 | 1.00 | 54.73 | C |
| ATOM | 2359 | CD1 | ILE | A | 174 | −68.858 | 41.949 | 17.553 | 1.00 | 55.78 | C |
| ATOM | 2363 | CG2 | ILE | A | 174 | −71.532 | 41.504 | 15.759 | 1.00 | 54.06 | C |
| ATOM | 2367 | C | ILE | A | 174 | −73.957 | 41.744 | 17.384 | 1.00 | 53.88 | C |
| ATOM | 2368 | O | ILE | A | 174 | −74.587 | 41.134 | 18.250 | 1.00 | 53.83 | O |
| ATOM | 2370 | N | GLY | A | 175 | −74.332 | 41.747 | 16.107 | 1.00 | 53.59 | N |
| ATOM | 2371 | CA | GLY | A | 175 | −75.351 | 40.817 | 15.613 | 1.00 | 53.51 | C |
| ATOM | 2374 | C | GLY | A | 175 | −75.130 | 39.395 | 16.126 | 1.00 | 53.43 | C |
| ATOM | 2375 | O | GLY | A | 175 | −74.119 | 39.105 | 16.760 | 1.00 | 53.80 | O |
| ATOM | 2377 | N | LYS | A | 176 | −76.070 | 38.495 | 15.861 | 1.00 | 53.10 | N |
| ATOM | 2378 | CA | LYS | A | 176 | −75.926 | 37.098 | 16.286 | 1.00 | 52.68 | C |
| ATOM | 2380 | CB | LYS | A | 176 | −77.291 | 36.522 | 16.677 | 1.00 | 52.99 | C |
| ATOM | 2383 | CG | LYS | A | 176 | −78.003 | 37.387 | 17.746 | 1.00 | 54.12 | C |
| ATOM | 2386 | CD | LYS | A | 176 | −79.201 | 36.697 | 18.436 | 1.00 | 54.57 | C |
| ATOM | 2389 | CE | LYS | A | 176 | −79.503 | 37.369 | 19.792 | 1.00 | 54.79 | C |
| ATOM | 2392 | NZ | LYS | A | 176 | −80.458 | 36.598 | 20.653 | 1.00 | 55.20 | N |
| ATOM | 2396 | C | LYS | A | 176 | −75.246 | 36.267 | 15.196 | 1.00 | 51.83 | C |
| ATOM | 2397 | O | LYS | A | 176 | −74.393 | 35.433 | 15.486 | 1.00 | 51.69 | O |
| ATOM | 2399 | N | GLU | A | 177 | −75.609 | 36.520 | 13.940 | 1.00 | 50.90 | N |
| ATOM | 2400 | CA | GLU | A | 177 | −74.975 | 35.854 | 12.800 | 1.00 | 50.19 | C |
| ATOM | 2402 | CB | GLU | A | 177 | −75.792 | 36.062 | 11.507 | 1.00 | 50.41 | C |
| ATOM | 2405 | CG | GLU | A | 177 | −75.506 | 37.368 | 10.735 | 1.00 | 51.03 | C |
| ATOM | 2408 | CD | GLU | A | 177 | −76.403 | 37.572 | 9.507 | 1.00 | 52.17 | C |
| ATOM | 2409 | OE1 | GLU | A | 177 | −75.955 | 38.276 | 8.569 | 1.00 | 52.63 | O |
| ATOM | 2410 | OE2 | GLU | A | 177 | −77.546 | 37.048 | 9.479 | 1.00 | 52.03 | O |
| ATOM | 2411 | C | GLU | A | 177 | −73.549 | 36.369 | 12.607 | 1.00 | 49.10 | C |
| ATOM | 2412 | O | GLU | A | 177 | −72.626 | 35.597 | 12.321 | 1.00 | 49.53 | O |
| ATOM | 2414 | N | LEU | A | 178 | −73.388 | 37.681 | 12.770 | 1.00 | 47.39 | N |
| ATOM | 2415 | CA | LEU | A | 178 | −72.110 | 38.371 | 12.575 | 1.00 | 45.63 | C |
| ATOM | 2417 | CB | LEU | A | 178 | −72.352 | 39.877 | 12.615 | 1.00 | 45.59 | C |
| ATOM | 2420 | CG | LEU | A | 178 | −71.280 | 40.809 | 12.085 | 1.00 | 45.45 | C |
| ATOM | 2422 | CD1 | LEU | A | 178 | −70.969 | 40.515 | 10.620 | 1.00 | 45.45 | C |
| ATOM | 2426 | CD2 | LEU | A | 178 | −71.765 | 42.233 | 12.279 | 1.00 | 44.63 | C |
| ATOM | 2430 | C | LEU | A | 178 | −71.095 | 37.979 | 13.634 | 1.00 | 44.06 | C |
| ATOM | 2431 | O | LEU | A | 178 | −69.902 | 38.012 | 13.387 | 1.00 | 43.70 | O |
| ATOM | 2433 | N | ALA | A | 179 | −71.586 | 37.611 | 14.810 | 1.00 | 42.54 | N |
| ATOM | 2434 | CA | ALA | A | 179 | −70.753 | 37.041 | 15.847 | 1.00 | 41.66 | C |
| ATOM | 2436 | CB | ALA | A | 179 | −71.545 | 36.884 | 17.122 | 1.00 | 41.69 | C |
| ATOM | 2440 | C | ALA | A | 179 | −70.193 | 35.695 | 15.416 | 1.00 | 40.75 | C |
| ATOM | 2441 | O | ALA | A | 179 | −69.078 | 35.351 | 15.769 | 1.00 | 40.61 | O |
| ATOM | 2443 | N | GLU | A | 180 | −70.974 | 34.931 | 14.664 | 1.00 | 39.88 | N |
| ATOM | 2444 | CA | GLU | A | 180 | −70.518 | 33.639 | 14.143 | 1.00 | 39.40 | C |

TABLE 3-7-continued

Coordinates of *P. tremuloides* IspS

| ATOM | 2446 | CB | GLU | A | 180 | −71.710 | 32.781 | 13.718 | 1.00 | 39.74 | C |
| --- | --- | --- | --- | --- | --- | --- | --- | --- | --- | --- | --- |
| ATOM | 2449 | CG | GLU | A | 180 | −72.650 | 32.415 | 14.865 | 1.00 | 40.88 | C |
| ATOM | 2452 | CD | GLU | A | 180 | −73.913 | 31.710 | 14.398 | 1.00 | 42.02 | C |
| ATOM | 2453 | OE1 | GLU | A | 180 | −74.380 | 32.022 | 13.271 | 1.00 | 43.05 | O |
| ATOM | 2454 | OE2 | GLU | A | 180 | −74.437 | 30.857 | 15.166 | 1.00 | 41.93 | O |
| ATOM | 2455 | C | GLU | A | 180 | −69.565 | 33.805 | 12.960 | 1.00 | 38.29 | C |
| ATOM | 2456 | O | GLU | A | 180 | −68.739 | 32.940 | 12.699 | 1.00 | 38.23 | O |
| ATOM | 2458 | N | GLN | A | 181 | −69.704 | 34.911 | 12.240 | 1.00 | 36.92 | N |
| ATOM | 2459 | CA | GLN | A | 181 | −68.748 | 35.299 | 11.223 | 1.00 | 35.74 | C |
| ATOM | 2461 | CB | GLN | A | 181 | −69.272 | 36.516 | 10.463 | 1.00 | 35.94 | C |
| ATOM | 2464 | CG | GLN | A | 181 | −68.931 | 36.537 | 8.975 | 1.00 | 36.93 | C |
| ATOM | 2467 | CD | GLN | A | 181 | −69.693 | 35.492 | 8.176 | 1.00 | 37.72 | C |
| ATOM | 2468 | OE1 | GLN | A | 181 | −70.769 | 35.067 | 8.567 | 1.00 | 38.78 | O |
| ATOM | 2469 | NE2 | GLN | A | 181 | −69.139 | 35.083 | 7.050 | 1.00 | 38.11 | N |
| ATOM | 2472 | C | GLN | A | 181 | −67.406 | 35.632 | 11.881 | 1.00 | 34.64 | C |
| ATOM | 2473 | O | GLN | A | 181 | −66.348 | 35.411 | 11.294 | 1.00 | 34.73 | O |
| ATOM | 2475 | N | VAL | A | 182 | −67.448 | 36.158 | 13.102 | 1.00 | 33.29 | N |
| ATOM | 2476 | CA | VAL | A | 182 | −66.224 | 36.488 | 13.842 | 1.00 | 32.28 | C |
| ATOM | 2478 | CB | VAL | A | 182 | −66.433 | 37.653 | 14.855 | 1.00 | 32.10 | C |
| ATOM | 2480 | CG1 | VAL | A | 182 | −66.328 | 38.991 | 14.166 | 1.00 | 31.51 | C |
| ATOM | 2484 | CG2 | VAL | A | 182 | −65.420 | 37.594 | 15.957 | 1.00 | 31.69 | C |
| ATOM | 2488 | C | VAL | A | 182 | −65.613 | 35.298 | 14.575 | 1.00 | 31.49 | C |
| ATOM | 2489 | O | VAL | A | 182 | −64.396 | 35.230 | 14.668 | 1.00 | 31.43 | O |
| ATOM | 2491 | N | SER | A | 183 | −66.422 | 34.378 | 15.106 | 1.00 | 30.56 | N |
| ATOM | 2492 | CA | SER | A | 183 | −65.860 | 33.174 | 15.744 | 1.00 | 30.16 | C |
| ATOM | 2494 | CB | SER | A | 183 | −66.926 | 32.253 | 16.327 | 1.00 | 30.29 | C |
| ATOM | 2497 | OG | SER | A | 183 | −67.796 | 32.934 | 17.214 | 1.00 | 32.35 | O |
| ATOM | 2499 | C | SER | A | 183 | −65.111 | 32.403 | 14.692 | 1.00 | 29.30 | C |
| ATOM | 2500 | O | SER | A | 183 | −63.974 | 31.981 | 14.903 | 1.00 | 29.32 | O |
| ATOM | 2502 | N | HIS | A | 184 | −65.768 | 32.252 | 13.546 | 1.00 | 28.24 | N |
| ATOM | 2503 | CA | HIS | A | 184 | −65.215 | 31.578 | 12.379 | 1.00 | 27.36 | C |
| ATOM | 2505 | CB | HIS | A | 184 | −66.245 | 31.653 | 11.254 | 1.00 | 27.41 | C |
| ATOM | 2508 | CG | HIS | A | 184 | −65.930 | 30.807 | 10.064 | 1.00 | 26.90 | C |
| ATOM | 2509 | ND1 | HIS | A | 184 | −65.484 | 29.511 | 10.166 | 1.00 | 27.76 | N |
| ATOM | 2511 | CE1 | HIS | A | 184 | −65.321 | 29.009 | 8.955 | 1.00 | 27.47 | C |
| ATOM | 2513 | NE2 | HIS | A | 184 | −65.661 | 29.929 | 8.075 | 1.00 | 26.52 | N |
| ATOM | 2515 | CD2 | HIS | A | 184 | −66.059 | 31.058 | 8.742 | 1.00 | 26.61 | C |
| ATOM | 2517 | C | HIS | A | 184 | −63.898 | 32.200 | 11.940 | 1.00 | 26.69 | C |
| ATOM | 2518 | O | HIS | A | 184 | −62.881 | 31.525 | 11.862 | 1.00 | 26.44 | O |
| ATOM | 2520 | N | ALA | A | 185 | −63.909 | 33.498 | 11.675 | 1.00 | 26.11 | N |
| ATOM | 2521 | CA | ALA | A | 185 | −62.711 | 34.176 | 11.205 | 1.00 | 25.63 | C |
| ATOM | 2523 | CB | ALA | A | 185 | −62.970 | 35.627 | 11.109 | 1.00 | 25.74 | C |
| ATOM | 2527 | C | ALA | A | 185 | −61.552 | 33.917 | 12.153 | 1.00 | 25.33 | C |
| ATOM | 2528 | O | ALA | A | 185 | −60.451 | 33.572 | 11.725 | 1.00 | 25.79 | O |
| ATOM | 2530 | N | LEU | A | 186 | −61.814 | 34.066 | 13.450 | 1.00 | 24.77 | N |
| ATOM | 2531 | CA | LEU | A | 186 | −60.776 | 33.940 | 14.470 | 1.00 | 24.05 | C |
| ATOM | 2533 | CB | LEU | A | 186 | −61.256 | 34.498 | 15.814 | 1.00 | 23.63 | C |
| ATOM | 2536 | CG | LEU | A | 186 | −61.516 | 36.012 | 15.903 | 1.00 | 22.51 | C |
| ATOM | 2538 | CD1 | LEU | A | 186 | −62.057 | 36.399 | 17.266 | 1.00 | 20.79 | C |
| ATOM | 2542 | CD2 | LEU | A | 186 | −60.273 | 36.793 | 15.613 | 1.00 | 21.13 | C |
| ATOM | 2546 | C | LEU | A | 186 | −60.316 | 32.497 | 14.613 | 1.00 | 24.02 | C |
| ATOM | 2547 | O | LEU | A | 186 | −59.169 | 32.250 | 14.943 | 1.00 | 24.27 | O |
| ATOM | 2549 | N | GLU | A | 187 | −61.201 | 31.543 | 14.347 | 1.00 | 23.88 | N |
| ATOM | 2550 | CA | GLU | A | 187 | −60.836 | 30.117 | 14.348 | 1.00 | 23.53 | C |
| ATOM | 2552 | CB | GLU | A | 187 | −62.029 | 29.270 | 13.919 | 1.00 | 23.66 | C |
| ATOM | 2555 | CG | GLU | A | 187 | −61.945 | 27.828 | 14.316 | 1.00 | 25.26 | C |
| ATOM | 2558 | CD | GLU | A | 187 | −63.049 | 26.971 | 13.693 | 1.00 | 28.04 | C |
| ATOM | 2559 | OE1 | GLU | A | 187 | −63.672 | 27.393 | 12.681 | 1.00 | 28.67 | O |
| ATOM | 2560 | OE2 | GLU | A | 187 | −63.288 | 25.858 | 14.225 | 1.00 | 29.72 | O |
| ATOM | 2561 | C | GLU | A | 187 | −59.686 | 29.838 | 13.395 | 1.00 | 22.92 | C |
| ATOM | 2562 | O | GLU | A | 187 | −58.765 | 29.091 | 13.729 | 1.00 | 22.53 | O |
| ATOM | 2564 | N | LEU | A | 188 | −59.763 | 30.446 | 12.209 | 1.00 | 22.46 | N |
| ATOM | 2565 | CA | LEU | A | 188 | −58.799 | 30.246 | 11.121 | 1.00 | 22.07 | C |
| ATOM | 2567 | CB | LEU | A | 188 | −58.802 | 28.794 | 10.635 | 1.00 | 22.11 | C |
| ATOM | 2570 | CG | LEU | A | 188 | −57.876 | 28.362 | 9.493 | 1.00 | 22.17 | C |
| ATOM | 2572 | CD1 | LEU | A | 188 | −56.456 | 28.051 | 9.961 | 1.00 | 21.62 | C |
| ATOM | 2576 | CD2 | LEU | A | 188 | −58.464 | 27.134 | 8.822 | 1.00 | 22.40 | C |
| ATOM | 2580 | C | LEU | A | 188 | −59.237 | 31.137 | 9.985 | 1.00 | 21.69 | C |
| ATOM | 2581 | O | LEU | A | 188 | −60.380 | 31.075 | 9.563 | 1.00 | 21.53 | O |
| ATOM | 2583 | N | PRO | A | 189 | −58.333 | 31.973 | 9.474 | 1.00 | 21.46 | N |
| ATOM | 2584 | CA | PRO | A | 189 | −58.745 | 32.935 | 8.472 | 1.00 | 21.18 | C |
| ATOM | 2586 | CB | PRO | A | 189 | −57.592 | 33.936 | 8.486 | 1.00 | 21.03 | C |
| ATOM | 2589 | CG | PRO | A | 189 | −56.423 | 33.118 | 8.757 | 1.00 | 21.21 | C |
| ATOM | 2592 | CD | PRO | A | 189 | −56.873 | 31.992 | 9.668 | 1.00 | 21.61 | C |
| ATOM | 2595 | C | PRO | A | 189 | −58.946 | 32.314 | 7.076 | 1.00 | 20.96 | C |
| ATOM | 2596 | O | PRO | A | 189 | −58.418 | 31.247 | 6.793 | 1.00 | 21.02 | O |
| ATOM | 2597 | N | LEU | A | 190 | −59.714 | 32.994 | 6.226 | 1.00 | 20.89 | N |
| ATOM | 2598 | CA | LEU | A | 190 | −60.018 | 32.533 | 4.867 | 1.00 | 20.74 | C |

TABLE 3-7-continued

Coordinates of *P. tremuloides* IspS

| ATOM | 2600 | CB | LEU | A | 190 | −60.597 | 33.690 | 4.053 | 1.00 | 20.76 | C |
|---|---|---|---|---|---|---|---|---|---|---|---|
| ATOM | 2603 | CG | LEU | A | 190 | −62.090 | 33.924 | 4.259 | 1.00 | 21.35 | C |
| ATOM | 2605 | CD1 | LEU | A | 190 | −62.537 | 35.196 | 3.578 | 1.00 | 20.54 | C |
| ATOM | 2609 | CD2 | LEU | A | 190 | −62.889 | 32.712 | 3.720 | 1.00 | 23.39 | C |
| ATOM | 2613 | C | LEU | A | 190 | −58.814 | 31.971 | 4.112 | 1.00 | 20.35 | C |
| ATOM | 2614 | O | LEU | A | 190 | −58.859 | 30.871 | 3.546 | 1.00 | 20.08 | O |
| ATOM | 2616 | N | HIS | A | 191 | −57.734 | 32.746 | 4.132 | 1.00 | 19.81 | N |
| ATOM | 2617 | CA | HIS | A | 191 | −56.537 | 32.448 | 3.364 | 1.00 | 18.89 | C |
| ATOM | 2619 | CB | HIS | A | 191 | −55.548 | 33.592 | 3.536 | 1.00 | 18.92 | C |
| ATOM | 2622 | CG | HIS | A | 191 | −54.372 | 33.520 | 2.623 | 1.00 | 18.51 | C |
| ATOM | 2623 | ND1 | HIS | A | 191 | −54.482 | 33.647 | 1.258 | 1.00 | 18.08 | N |
| ATOM | 2625 | CE1 | HIS | A | 191 | −53.281 | 33.544 | .718 | 1.00 | 18.96 | C |
| ATOM | 2627 | NE2 | HIS | A | 191 | −52.397 | 33.371 | 1.684 | 1.00 | 17.01 | N |
| ATOM | 2629 | CD2 | HIS | A | 191 | −53.054 | 33.355 | 2.884 | 1.00 | 17.94 | C |
| ATOM | 2631 | C | HIS | A | 191 | −55.889 | 31.142 | 3.759 | 1.00 | 18.32 | C |
| ATOM | 2632 | O | HIS | A | 191 | −55.217 | 30.531 | 2.942 | 1.00 | 17.98 | O |
| ATOM | 2634 | N | ARG | A | 192 | −56.093 | 30.719 | 5.006 | 1.00 | 18.06 | N |
| ATOM | 2635 | CA | ARG | A | 192 | −55.502 | 29.480 | 5.523 | 1.00 | 17.99 | C |
| ATOM | 2637 | CB | ARG | A | 192 | −54.940 | 29.722 | 6.909 | 1.00 | 17.77 | C |
| ATOM | 2640 | CG | ARG | A | 192 | −53.822 | 30.683 | 6.881 | 1.00 | 18.47 | C |
| ATOM | 2643 | CD | ARG | A | 192 | −53.082 | 30.748 | 8.196 | 1.00 | 19.80 | C |
| ATOM | 2646 | NE | ARG | A | 192 | −52.174 | 31.900 | 8.224 | 1.00 | 20.33 | N |
| ATOM | 2648 | CZ | ARG | A | 192 | −51.176 | 32.048 | 9.077 | 1.00 | 20.10 | C |
| ATOM | 2649 | NH1 | ARG | A | 192 | −50.928 | 31.113 | 9.972 | 1.00 | 21.72 | N |
| ATOM | 2652 | NH2 | ARG | A | 192 | −50.407 | 33.119 | 9.019 | 1.00 | 20.79 | N |
| ATOM | 2655 | C | ARG | A | 192 | −56.477 | 28.311 | 5.590 | 1.00 | 18.00 | C |
| ATOM | 2656 | O | ARG | A | 192 | −56.067 | 27.170 | 5.871 | 1.00 | 18.21 | O |
| ATOM | 2658 | N | ARG | A | 193 | −57.758 | 28.588 | 5.335 | 1.00 | 17.59 | N |
| ATOM | 2659 | CA | ARG | A | 193 | −58.779 | 27.563 | 5.382 | 1.00 | 17.16 | C |
| ATOM | 2661 | CB | ARG | A | 193 | −60.141 | 28.164 | 5.741 | 1.00 | 17.45 | C |
| ATOM | 2664 | CG | ARG | A | 193 | −61.109 | 27.132 | 6.322 | 1.00 | 18.70 | C |
| ATOM | 2667 | CD | ARG | A | 193 | −62.479 | 27.682 | 6.686 | 1.00 | 20.20 | C |
| ATOM | 2670 | NE | ARG | A | 193 | −62.423 | 28.682 | 7.751 | 1.00 | 22.59 | N |
| ATOM | 2672 | CZ | ARG | A | 193 | −62.386 | 28.435 | 9.067 | 1.00 | 24.12 | C |
| ATOM | 2673 | NH1 | ARG | A | 193 | −62.395 | 27.198 | 9.575 | 1.00 | 22.66 | N |
| ATOM | 2676 | NH2 | ARG | A | 193 | −62.348 | 29.469 | 9.898 | 1.00 | 26.36 | N |
| ATOM | 2679 | C | ARG | A | 193 | −58.871 | 26.842 | 4.058 | 1.00 | 16.63 | C |
| ATOM | 2680 | O | ARG | A | 193 | −58.861 | 27.461 | 3.005 | 1.00 | 15.93 | O |
| ATOM | 2682 | N | THR | A | 194 | −58.955 | 25.518 | 4.149 | 1.00 | 16.72 | N |
| ATOM | 2683 | CA | THR | A | 194 | −59.332 | 24.638 | 3.051 | 1.00 | 16.88 | C |
| ATOM | 2685 | CB | THR | A | 194 | −59.520 | 23.250 | 3.592 | 1.00 | 16.43 | C |
| ATOM | 2687 | OG1 | THR | A | 194 | −58.252 | 22.605 | 3.583 | 1.00 | 17.74 | O |
| ATOM | 2689 | CG2 | THR | A | 194 | −60.454 | 22.441 | 2.754 | 1.00 | 18.43 | C |
| ATOM | 2693 | C | THR | A | 194 | −60.607 | 25.112 | 2.384 | 1.00 | 17.28 | C |
| ATOM | 2694 | O | THR | A | 194 | −61.441 | 25.734 | 3.022 | 1.00 | 17.44 | O |
| ATOM | 2696 | N | GLN | A | 195 | −60.765 | 24.855 | 1.091 | 1.00 | 18.05 | N |
| ATOM | 2697 | CA | GLN | A | 195 | −61.925 | 25.402 | .397 | 1.00 | 18.76 | C |
| ATOM | 2699 | CB | GLN | A | 195 | −61.768 | 25.381 | −1.114 | 1.00 | 18.87 | C |
| ATOM | 2702 | CG | GLN | A | 195 | −63.145 | 25.523 | −1.761 | 1.00 | 20.75 | C |
| ATOM | 2705 | CD | GLN | A | 195 | −63.095 | 25.922 | −3.179 | 1.00 | 23.41 | C |
| ATOM | 2706 | OE1 | GLN | A | 195 | −62.031 | 26.088 | −3.733 | 1.00 | 27.07 | O |
| ATOM | 2707 | NE2 | GLN | A | 195 | −64.248 | 26.090 | −3.791 | 1.00 | 25.02 | N |
| ATOM | 2710 | C | GLN | A | 195 | −63.243 | 24.704 | .765 | 1.00 | 18.93 | C |
| ATOM | 2711 | O | GLN | A | 195 | −64.169 | 25.333 | 1.291 | 1.00 | 19.42 | O |
| ATOM | 2713 | N | ARG | A | 196 | −63.345 | 23.418 | .443 | 1.00 | 18.90 | N |
| ATOM | 2714 | CA | ARG | A | 196 | −64.577 | 22.685 | .663 | 1.00 | 18.68 | C |
| ATOM | 2716 | CB | ARG | A | 196 | −64.356 | 21.186 | .454 | 1.00 | 18.53 | C |
| ATOM | 2719 | CG | ARG | A | 196 | −64.851 | 20.644 | −.888 | 1.00 | 18.31 | C |
| ATOM | 2722 | CD | ARG | A | 196 | −64.705 | 21.622 | −2.037 | 1.00 | 17.93 | C |
| ATOM | 2725 | NE | ARG | A | 196 | −65.930 | 21.720 | −2.834 | 1.00 | 18.52 | N |
| ATOM | 2727 | CZ | ARG | A | 196 | −66.480 | 22.857 | −3.256 | 1.00 | 18.63 | C |
| ATOM | 2728 | NH1 | ARG | A | 196 | −65.938 | 24.014 | −2.937 | 1.00 | 19.84 | N |
| ATOM | 2731 | NH2 | ARG | A | 196 | −67.582 | 22.844 | −3.999 | 1.00 | 18.53 | N |
| ATOM | 2734 | C | ARG | A | 196 | −65.070 | 22.982 | 2.061 | 1.00 | 19.02 | C |
| ATOM | 2735 | O | ARG | A | 196 | −66.276 | 23.085 | 2.284 | 1.00 | 19.30 | O |
| ATOM | 2737 | N | LEU | A | 197 | −64.127 | 23.152 | 2.990 | 1.00 | 19.09 | N |
| ATOM | 2738 | CA | LEU | A | 197 | −64.444 | 23.432 | 4.379 | 1.00 | 19.19 | C |
| ATOM | 2740 | CB | LEU | A | 197 | −63.203 | 23.346 | 5.262 | 1.00 | 19.14 | C |
| ATOM | 2743 | CG | LEU | A | 197 | −63.135 | 22.097 | 6.130 | 1.00 | 19.99 | C |
| ATOM | 2745 | CD1 | LEU | A | 197 | −64.476 | 21.899 | 6.811 | 1.00 | 21.56 | C |
| ATOM | 2749 | CD2 | LEU | A | 197 | −62.016 | 22.198 | 7.161 | 1.00 | 20.06 | C |
| ATOM | 2753 | C | LEU | A | 197 | −65.071 | 24.781 | 4.553 | 1.00 | 19.52 | C |
| ATOM | 2754 | O | LEU | A | 197 | −66.052 | 24.902 | 5.252 | 1.00 | 19.85 | O |
| ATOM | 2756 | N | GLU | A | 198 | −64.488 | 25.803 | 3.941 | 1.00 | 20.11 | N |
| ATOM | 2757 | CA | GLU | A | 198 | −65.051 | 27.147 | 3.986 | 1.00 | 20.47 | C |
| ATOM | 2759 | CB | GLU | A | 198 | −64.079 | 28.156 | 3.385 | 1.00 | 20.84 | C |
| ATOM | 2762 | CG | GLU | A | 198 | −64.659 | 29.539 | 3.069 | 1.00 | 22.30 | C |
| ATOM | 2765 | CD | GLU | A | 198 | −65.206 | 30.260 | 4.283 | 1.00 | 24.40 | C |

TABLE 3-7-continued

Coordinates of *P. tremuloides* IspS

| ATOM | 2766 | OE1 | GLU | A | 198 | −64.852 | 29.894 | 5.418 | 1.00 | 25.34 | O |
|---|---|---|---|---|---|---|---|---|---|---|---|
| ATOM | 2767 | OE2 | GLU | A | 198 | −65.991 | 31.217 | 4.106 | 1.00 | 26.83 | O |
| ATOM | 2768 | C | GLU | A | 198 | −66.360 | 27.186 | 3.226 | 1.00 | 20.57 | C |
| ATOM | 2769 | O | GLU | A | 198 | −67.212 | 28.009 | 3.529 | 1.00 | 20.65 | O |
| ATOM | 2771 | N | ALA | A | 199 | −66.519 | 26.298 | 2.240 | 1.00 | 20.76 | N |
| ATOM | 2772 | CA | ALA | A | 199 | −67.751 | 26.229 | 1.452 | 1.00 | 20.52 | C |
| ATOM | 2774 | CB | ALA | A | 199 | −67.521 | 25.492 | .166 | 1.00 | 20.44 | C |
| ATOM | 2778 | C | ALA | A | 199 | −68.907 | 25.611 | 2.232 | 1.00 | 20.55 | C |
| ATOM | 2779 | O | ALA | A | 199 | −69.988 | 26.158 | 2.202 | 1.00 | 20.17 | O |
| ATOM | 2781 | N | VAL | A | 200 | −68.701 | 24.493 | 2.933 | 1.00 | 21.10 | N |
| ATOM | 2782 | CA | VAL | A | 200 | −69.791 | 23.935 | 3.774 | 1.00 | 21.51 | C |
| ATOM | 2784 | CB | VAL | A | 200 | −69.509 | 22.576 | 4.485 | 1.00 | 21.18 | C |
| ATOM | 2786 | CG1 | VAL | A | 200 | −69.618 | 21.460 | 3.525 | 1.00 | 21.27 | C |
| ATOM | 2790 | CG2 | VAL | A | 200 | −68.161 | 22.569 | 5.200 | 1.00 | 21.23 | C |
| ATOM | 2794 | C | VAL | A | 200 | −70.170 | 24.905 | 4.860 | 1.00 | 21.99 | C |
| ATOM | 2795 | O | VAL | A | 200 | −71.338 | 25.022 | 5.186 | 1.00 | 22.99 | O |
| ATOM | 2797 | N | TRP | A | 201 | −69.204 | 25.590 | 5.440 | 1.00 | 22.10 | N |
| ATOM | 2798 | CA | TRP | A | 201 | −69.551 | 26.565 | 6.433 | 1.00 | 22.58 | C |
| ATOM | 2800 | CB | TRP | A | 201 | −68.315 | 27.144 | 7.121 | 1.00 | 22.92 | C |
| ATOM | 2803 | CG | TRP | A | 201 | −68.667 | 27.957 | 8.310 | 1.00 | 23.65 | C |
| ATOM | 2804 | CD1 | TRP | A | 201 | −68.758 | 27.520 | 9.588 | 1.00 | 25.08 | C |
| ATOM | 2806 | NE1 | TRP | A | 201 | −69.127 | 28.549 | 10.417 | 1.00 | 26.35 | N |
| ATOM | 2808 | CE2 | TRP | A | 201 | −69.290 | 29.683 | 9.669 | 1.00 | 25.48 | C |
| ATOM | 2809 | CD2 | TRP | A | 201 | −69.010 | 29.344 | 8.332 | 1.00 | 24.77 | C |
| ATOM | 2810 | CE3 | TRP | A | 201 | −69.095 | 30.336 | 7.355 | 1.00 | 24.92 | C |
| ATOM | 2812 | CZ3 | TRP | A | 201 | −69.450 | 31.616 | 7.739 | 1.00 | 24.96 | C |
| ATOM | 2814 | CH2 | TRP | A | 201 | −69.720 | 31.918 | 9.078 | 1.00 | 25.08 | C |
| ATOM | 2816 | CZ2 | TRP | A | 201 | −69.648 | 30.968 | 10.056 | 1.00 | 24.68 | C |
| ATOM | 2818 | C | TRP | A | 201 | −70.351 | 27.662 | 5.758 | 1.00 | 22.71 | C |
| ATOM | 2819 | O | TRP | A | 201 | −71.482 | 27.921 | 6.140 | 1.00 | 22.76 | O |
| ATOM | 2821 | N | SER | A | 202 | −69.776 | 28.272 | 4.727 | 1.00 | 23.04 | N |
| ATOM | 2822 | CA | SER | A | 202 | −70.335 | 29.500 | 4.165 | 1.00 | 23.29 | C |
| ATOM | 2824 | CB | SER | A | 202 | −69.304 | 30.205 | 3.290 | 1.00 | 23.20 | C |
| ATOM | 2827 | OG | SER | A | 202 | −68.306 | 30.807 | 4.111 | 1.00 | 23.07 | O |
| ATOM | 2829 | C | SER | A | 202 | −71.666 | 29.341 | 3.432 | 1.00 | 23.66 | C |
| ATOM | 2830 | O | SER | A | 202 | −72.392 | 30.310 | 3.265 | 1.00 | 23.38 | O |
| ATOM | 2832 | N | ILE | A | 203 | −71.996 | 28.124 | 3.016 | 1.00 | 24.49 | N |
| ATOM | 2833 | CA | ILE | A | 203 | −73.321 | 27.859 | 2.460 | 1.00 | 25.07 | C |
| ATOM | 2835 | CB | ILE | A | 203 | −73.391 | 26.530 | 1.653 | 1.00 | 24.74 | C |
| ATOM | 2837 | CG1 | ILE | A | 203 | −72.494 | 26.587 | .423 | 1.00 | 24.36 | C |
| ATOM | 2840 | CD1 | ILE | A | 203 | −72.344 | 25.255 | −.281 | 1.00 | 23.81 | C |
| ATOM | 2844 | CG2 | ILE | A | 203 | −74.795 | 26.292 | 1.156 | 1.00 | 24.45 | C |
| ATOM | 2848 | C | ILE | A | 203 | −74.338 | 27.858 | 3.607 | 1.00 | 25.91 | C |
| ATOM | 2849 | O | ILE | A | 203 | −75.350 | 28.554 | 3.546 | 1.00 | 26.26 | O |
| ATOM | 2851 | N | GLU | A | 204 | −74.051 | 27.104 | 4.662 | 1.00 | 26.69 | N |
| ATOM | 2852 | CA | GLU | A | 204 | −74.929 | 27.053 | 5.824 | 1.00 | 27.40 | C |
| ATOM | 2854 | CB | GLU | A | 204 | −74.286 | 26.217 | 6.931 | 1.00 | 27.65 | C |
| ATOM | 2857 | CG | GLU | A | 204 | −75.132 | 26.032 | 8.183 | 1.00 | 29.02 | C |
| ATOM | 2860 | CD | GLU | A | 204 | −76.530 | 25.491 | 7.903 | 1.00 | 30.44 | C |
| ATOM | 2861 | OE1 | GLU | A | 204 | −76.746 | 24.858 | 6.844 | 1.00 | 31.22 | O |
| ATOM | 2862 | OE2 | GLU | A | 204 | −77.417 | 25.703 | 8.753 | 1.00 | 31.96 | O |
| ATOM | 2863 | C | GLU | A | 204 | −75.258 | 28.451 | 6.342 | 1.00 | 27.61 | C |
| ATOM | 2864 | O | GLU | A | 204 | −76.409 | 28.778 | 6.526 | 1.00 | 27.78 | O |
| ATOM | 2866 | N | ALA | A | 205 | −74.240 | 29.274 | 6.547 | 1.00 | 28.15 | N |
| ATOM | 2867 | CA | ALA | A | 205 | −74.416 | 30.637 | 7.050 | 1.00 | 28.41 | C |
| ATOM | 2869 | CB | ALA | A | 205 | −73.062 | 31.285 | 7.274 | 1.00 | 28.41 | C |
| ATOM | 2873 | C | ALA | A | 205 | −75.234 | 31.520 | 6.136 | 1.00 | 28.84 | C |
| ATOM | 2874 | O | ALA | A | 205 | −76.050 | 32.302 | 6.610 | 1.00 | 28.54 | O |
| ATOM | 2876 | N | TYR | A | 206 | −74.978 | 31.408 | 4.832 | 1.00 | 29.84 | N |
| ATOM | 2877 | CA | TYR | A | 206 | −75.581 | 32.281 | 3.805 | 1.00 | 30.41 | C |
| ATOM | 2879 | CB | TYR | A | 206 | −74.801 | 32.170 | 2.493 | 1.00 | 30.20 | C |
| ATOM | 2882 | CG | TYR | A | 206 | −75.180 | 33.173 | 1.425 | 1.00 | 29.62 | C |
| ATOM | 2883 | CD1 | TYR | A | 206 | −74.721 | 34.482 | 1.484 | 1.00 | 30.32 | C |
| ATOM | 2885 | CE1 | TYR | A | 206 | −75.047 | 35.412 | .489 | 1.00 | 29.70 | C |
| ATOM | 2887 | CZ | TYR | A | 206 | −75.830 | 35.028 | −.578 | 1.00 | 28.41 | C |
| ATOM | 2888 | OH | TYR | A | 206 | −76.155 | 35.956 | −1.548 | 1.00 | 26.74 | O |
| ATOM | 2890 | CE2 | TYR | A | 206 | −76.291 | 33.724 | −.659 | 1.00 | 28.16 | C |
| ATOM | 2892 | CD2 | TYR | A | 206 | −75.958 | 32.806 | .335 | 1.00 | 28.39 | C |
| ATOM | 2894 | C | TYR | A | 206 | −77.038 | 31.918 | 3.561 | 1.00 | 31.15 | C |
| ATOM | 2895 | O | TYR | A | 206 | −77.858 | 32.781 | 3.268 | 1.00 | 31.30 | O |
| ATOM | 2897 | N | ARG | A | 207 | −77.341 | 30.631 | 3.676 | 1.00 | 32.05 | N |
| ATOM | 2898 | CA | ARG | A | 207 | −78.691 | 30.128 | 3.555 | 1.00 | 32.81 | C |
| ATOM | 2900 | CB | ARG | A | 207 | −78.684 | 28.623 | 3.813 | 1.00 | 32.86 | C |
| ATOM | 2903 | CG | ARG | A | 207 | −80.028 | 27.941 | 3.673 | 1.00 | 34.01 | C |
| ATOM | 2906 | CD | ARG | A | 207 | −80.066 | 26.632 | 4.450 | 1.00 | 35.11 | C |
| ATOM | 2909 | NE | ARG | A | 207 | −79.096 | 25.669 | 3.939 | 1.00 | 35.35 | N |
| ATOM | 2911 | CZ | ARG | A | 207 | −79.353 | 24.737 | 3.022 | 1.00 | 36.00 | C |
| ATOM | 2912 | NH1 | ARG | A | 207 | −80.562 | 24.611 | 2.478 | 1.00 | 35.55 | N |

TABLE 3-7-continued

Coordinates of *P. tremuloides* IspS

| ATOM | 2915 | NH2 | ARG | A | 207 | −78.381 | 23.918 | 2.640 | 1.00 | 37.05 | N |
|---|---|---|---|---|---|---|---|---|---|---|---|
| ATOM | 2918 | C | ARG | A | 207 | −79.609 | 30.826 | 4.550 | 1.00 | 33.57 | C |
| ATOM | 2919 | O | ARG | A | 207 | −80.783 | 31.003 | 4.263 | 1.00 | 33.82 | O |
| ATOM | 2921 | N | LYS | A | 208 | −79.064 | 31.223 | 5.707 | 1.00 | 34.58 | N |
| ATOM | 2922 | CA | LYS | A | 208 | −79.835 | 31.830 | 6.812 | 1.00 | 35.21 | C |
| ATOM | 2924 | CB | LYS | A | 208 | −79.137 | 31.599 | 8.159 | 1.00 | 35.05 | C |
| ATOM | 2927 | CG | LYS | A | 208 | −78.847 | 30.147 | 8.496 | 1.00 | 34.78 | C |
| ATOM | 2930 | CD | LYS | A | 208 | −78.583 | 29.974 | 9.980 | 1.00 | 34.44 | C |
| ATOM | 2933 | CE | LYS | A | 208 | −77.992 | 28.619 | 10.309 | 1.00 | 34.16 | C |
| ATOM | 2936 | NZ | LYS | A | 208 | −76.540 | 28.693 | 10.572 | 1.00 | 33.81 | N |
| ATOM | 2940 | C | LYS | A | 208 | −80.075 | 33.333 | 6.663 | 1.00 | 36.06 | C |
| ATOM | 2941 | O | LYS | A | 208 | −81.032 | 33.857 | 7.226 | 1.00 | 36.19 | O |
| ATOM | 2943 | N | LYS | A | 209 | −79.197 | 34.032 | 5.946 | 1.00 | 36.93 | N |
| ATOM | 2944 | CA | LYS | A | 209 | −79.412 | 35.445 | 5.652 | 1.00 | 37.77 | C |
| ATOM | 2946 | CB | LYS | A | 209 | −78.284 | 35.998 | 4.779 | 1.00 | 38.18 | C |
| ATOM | 2949 | CG | LYS | A | 209 | −76.928 | 36.134 | 5.458 | 1.00 | 39.90 | C |
| ATOM | 2952 | CD | LYS | A | 209 | −75.982 | 37.023 | 4.621 | 1.00 | 42.39 | C |
| ATOM | 2955 | CE | LYS | A | 209 | −74.531 | 37.016 | 5.169 | 1.00 | 44.21 | C |
| ATOM | 2958 | NZ | LYS | A | 209 | −74.350 | 37.688 | 6.509 | 1.00 | 44.75 | N |
| ATOM | 2962 | C | LYS | A | 209 | −80.738 | 35.600 | 4.911 | 1.00 | 37.89 | C |
| ATOM | 2963 | O | LYS | A | 209 | −81.049 | 34.785 | 4.036 | 1.00 | 38.20 | O |
| ATOM | 2965 | N | GLU | A | 210 | −81.518 | 36.632 | 5.243 | 1.00 | 37.87 | N |
| ATOM | 2966 | CA | GLU | A | 210 | −82.847 | 36.797 | 4.630 | 1.00 | 37.72 | C |
| ATOM | 2968 | CB | GLU | A | 210 | −83.821 | 37.578 | 5.549 | 1.00 | 38.19 | C |
| ATOM | 2971 | CG | GLU | A | 210 | −83.850 | 39.130 | 5.404 | 1.00 | 39.68 | C |
| ATOM | 2974 | CD | GLU | A | 210 | −85.270 | 39.736 | 5.534 | 1.00 | 41.27 | C |
| ATOM | 2975 | OE1 | GLU | A | 210 | −86.172 | 39.100 | 6.136 | 1.00 | 41.67 | O |
| ATOM | 2976 | OE2 | GLU | A | 210 | −85.482 | 40.859 | 5.019 | 1.00 | 42.17 | O |
| ATOM | 2977 | C | GLU | A | 210 | −82.760 | 37.394 | 3.219 | 1.00 | 36.68 | C |
| ATOM | 2978 | O | GLU | A | 210 | −83.605 | 37.103 | 2.371 | 1.00 | 36.39 | O |
| ATOM | 2980 | N | ASP | A | 211 | −81.725 | 38.198 | 2.969 | 1.00 | 35.65 | N |
| ATOM | 2981 | CA | ASP | A | 211 | −81.481 | 38.777 | 1.632 | 1.00 | 34.94 | C |
| ATOM | 2983 | CB | ASP | A | 211 | −81.064 | 40.257 | 1.740 | 1.00 | 35.22 | C |
| ATOM | 2986 | CG | ASP | A | 211 | −79.811 | 40.477 | 2.599 | 1.00 | 35.84 | C |
| ATOM | 2987 | OD1 | ASP | A | 211 | −79.379 | 39.557 | 3.341 | 1.00 | 35.60 | O |
| ATOM | 2988 | OD2 | ASP | A | 211 | −79.276 | 41.606 | 2.536 | 1.00 | 36.73 | O |
| ATOM | 2989 | C | ASP | A | 211 | −80.451 | 37.989 | .811 | 1.00 | 33.73 | C |
| ATOM | 2990 | O | ASP | A | 211 | −79.753 | 38.556 | −.021 | 1.00 | 33.40 | O |
| ATOM | 2992 | N | ALA | A | 212 | −80.366 | 36.682 | 1.057 | 1.00 | 32.53 | N |
| ATOM | 2993 | CA | ALA | A | 212 | −79.506 | 35.783 | .293 | 1.00 | 31.40 | C |
| ATOM | 2995 | CB | ALA | A | 212 | −79.569 | 34.382 | .889 | 1.00 | 30.79 | C |
| ATOM | 2999 | C | ALA | A | 212 | −79.940 | 35.762 | −1.176 | 1.00 | 30.60 | C |
| ATOM | 3000 | O | ALA | A | 212 | −81.124 | 35.594 | −1.467 | 1.00 | 30.37 | O |
| ATOM | 3002 | N | ASN | A | 213 | −79.000 | 35.967 | −2.097 | 1.00 | 29.71 | N |
| ATOM | 3003 | CA | ASN | A | 213 | −79.304 | 35.809 | −3.520 | 1.00 | 29.27 | C |
| ATOM | 3005 | CB | ASN | A | 213 | −78.144 | 36.315 | −4.402 | 1.00 | 29.30 | C |
| ATOM | 3008 | CG | ASN | A | 213 | −78.442 | 36.217 | −5.911 | 1.00 | 29.07 | C |
| ATOM | 3009 | OD1 | ASN | A | 213 | −78.437 | 37.215 | −6.624 | 1.00 | 29.38 | O |
| ATOM | 3010 | ND2 | ASN | A | 213 | −78.691 | 35.015 | −6.389 | 1.00 | 28.37 | N |
| ATOM | 3013 | C | ASN | A | 213 | −79.634 | 34.328 | −3.785 | 1.00 | 28.81 | C |
| ATOM | 3014 | O | ASN | A | 213 | −78.784 | 33.455 | −3.658 | 1.00 | 29.04 | O |
| ATOM | 3016 | N | GLN | A | 214 | −80.880 | 34.053 | −4.145 | 1.00 | 28.04 | N |
| ATOM | 3017 | CA | GLN | A | 214 | −81.376 | 32.692 | −4.191 | 1.00 | 27.32 | C |
| ATOM | 3019 | CB | GLN | A | 214 | −82.906 | 32.700 | −4.178 | 1.00 | 27.47 | C |
| ATOM | 3022 | CG | GLN | A | 214 | −83.505 | 33.269 | −2.889 | 1.00 | 27.68 | C |
| ATOM | 3025 | CD | GLN | A | 214 | −83.294 | 32.359 | −1.688 | 1.00 | 27.54 | C |
| ATOM | 3026 | OE1 | GLN | A | 214 | −83.940 | 31.320 | −1.571 | 1.00 | 28.19 | O |
| ATOM | 3027 | NE2 | GLN | A | 214 | −82.392 | 32.748 | −.790 | 1.00 | 26.90 | N |
| ATOM | 3030 | C | GLN | A | 214 | −80.858 | 31.902 | −5.385 | 1.00 | 26.71 | C |
| ATOM | 3031 | O | GLN | A | 214 | −80.863 | 30.668 | −5.355 | 1.00 | 26.91 | O |
| ATOM | 3033 | N | VAL | A | 215 | −80.439 | 32.600 | −6.442 | 1.00 | 25.81 | N |
| ATOM | 3034 | CA | VAL | A | 215 | −79.789 | 31.947 | −7.588 | 1.00 | 24.88 | C |
| ATOM | 3036 | CB | VAL | A | 215 | −79.651 | 32.894 | −8.808 | 1.00 | 24.81 | C |
| ATOM | 3038 | CG1 | VAL | A | 215 | −78.459 | 32.483 | −9.680 | 1.00 | 24.94 | C |
| ATOM | 3042 | CG2 | VAL | A | 215 | −80.935 | 32.907 | −9.620 | 1.00 | 23.74 | C |
| ATOM | 3046 | C | VAL | A | 215 | −78.415 | 31.427 | −7.176 | 1.00 | 24.18 | C |
| ATOM | 3047 | O | VAL | A | 215 | −78.073 | 30.282 | −7.430 | 1.00 | 23.74 | O |
| ATOM | 3049 | N | LEU | A | 216 | −77.650 | 32.283 | −6.510 | 1.00 | 23.78 | N |
| ATOM | 3050 | CA | LEU | A | 216 | −76.299 | 31.961 | −6.036 | 1.00 | 23.33 | C |
| ATOM | 3052 | CB | LEU | A | 216 | −75.680 | 33.195 | −5.373 | 1.00 | 23.10 | C |
| ATOM | 3055 | CG | LEU | A | 216 | −74.194 | 33.192 | −5.059 | 1.00 | 22.91 | C |
| ATOM | 3057 | CD1 | LEU | A | 216 | −73.383 | 32.962 | −6.312 | 1.00 | 22.88 | C |
| ATOM | 3061 | CD2 | LEU | A | 216 | −73.826 | 34.518 | −4.424 | 1.00 | 22.03 | C |
| ATOM | 3065 | C | LEU | A | 216 | −76.333 | 30.797 | −5.050 | 1.00 | 22.92 | C |
| ATOM | 3066 | O | LEU | A | 216 | −75.598 | 29.826 | −5.201 | 1.00 | 23.38 | O |
| ATOM | 3068 | N | LEU | A | 217 | −77.214 | 30.890 | −4.060 | 1.00 | 22.09 | N |
| ATOM | 3069 | CA | LEU | A | 217 | −77.367 | 29.851 | −3.054 | 1.00 | 21.14 | C |
| ATOM | 3071 | CB | LEU | A | 217 | −78.488 | 30.225 | −2.090 | 1.00 | 21.11 | C |

TABLE 3-7-continued

| | | | | | | | | | | |
|---|---|---|---|---|---|---|---|---|---|---|
| colspan="11" | Coordinates of *P. tremuloides* IspS |

| | | | | | | | | | | |
|---|---|---|---|---|---|---|---|---|---|---|
| ATOM | 3074 | CG | LEU | A | 217 | −78.782 | 29.236 | −.961 | 1.00 | 21.08 C |
| ATOM | 3076 | CD1 | LEU | A | 217 | −77.703 | 29.267 | .101 | 1.00 | 19.87 C |
| ATOM | 3080 | CD2 | LEU | A | 217 | −80.146 | 29.535 | −.360 | 1.00 | 21.46 C |
| ATOM | 3084 | C | LEU | A | 217 | −77.682 | 28.517 | −3.685 | 1.00 | 20.38 C |
| ATOM | 3085 | O | LEU | A | 217 | −77.133 | 27.508 | −3.286 | 1.00 | 20.04 O |
| ATOM | 3087 | N | GLU | A | 218 | −78.579 | 28.512 | −4.661 | 1.00 | 19.97 N |
| ATOM | 3088 | CA | GLU | A | 218 | −79.027 | 27.260 | −5.273 | 1.00 | 19.72 C |
| ATOM | 3090 | CB | GLU | A | 218 | −80.220 | 27.499 | −6.212 | 1.00 | 19.87 C |
| ATOM | 3093 | CG | GLU | A | 218 | −81.005 | 26.228 | −6.627 | 1.00 | 21.03 C |
| ATOM | 3096 | CD | GLU | A | 218 | −82.303 | 26.535 | −7.424 | 1.00 | 22.59 C |
| ATOM | 3097 | OE1 | GLU | A | 218 | −82.643 | 27.730 | −7.619 | 1.00 | 23.61 O |
| ATOM | 3098 | OE2 | GLU | A | 218 | −82.983 | 25.578 | −7.863 | 1.00 | 22.31 O |
| ATOM | 3099 | C | GLU | A | 218 | −77.854 | 26.613 | −6.009 | 1.00 | 19.03 C |
| ATOM | 3100 | O | GLU | A | 218 | −77.522 | 25.452 | −5.764 | 1.00 | 18.97 O |
| ATOM | 3102 | N | LEU | A | 219 | −77.203 | 27.381 | −6.878 | 1.00 | 18.06 N |
| ATOM | 3103 | CA | LEU | A | 219 | −76.012 | 26.907 | −7.573 | 1.00 | 17.15 C |
| ATOM | 3105 | CB | LEU | A | 219 | −75.439 | 28.029 | −8.418 | 1.00 | 16.75 C |
| ATOM | 3108 | CG | LEU | A | 219 | −74.196 | 27.717 | −9.231 | 1.00 | 16.01 C |
| ATOM | 3110 | CD1 | LEU | A | 219 | −74.511 | 26.832 | −10.404 | 1.00 | 12.99 C |
| ATOM | 3114 | CD2 | LEU | A | 219 | −73.577 | 29.028 | −9.675 | 1.00 | 16.20 C |
| ATOM | 3118 | C | LEU | A | 219 | −74.973 | 26.409 | −6.570 | 1.00 | 16.75 C |
| ATOM | 3119 | O | LEU | A | 219 | −74.377 | 25.355 | −6.757 | 1.00 | 16.47 O |
| ATOM | 3121 | N | ALA | A | 220 | −74.786 | 27.169 | −5.496 | 1.00 | 16.40 N |
| ATOM | 3122 | CA | ALA | A | 220 | −73.858 | 26.808 | −4.422 | 1.00 | 16.15 C |
| ATOM | 3124 | CB | ALA | A | 220 | −73.906 | 27.830 | −3.302 | 1.00 | 16.13 C |
| ATOM | 3128 | C | ALA | A | 220 | −74.137 | 25.436 | −3.862 | 1.00 | 16.03 C |
| ATOM | 3129 | O | ALA | A | 220 | −73.253 | 24.603 | −3.799 | 1.00 | 16.30 O |
| ATOM | 3131 | N | ILE | A | 221 | −75.371 | 25.201 | −3.447 | 1.00 | 16.24 N |
| ATOM | 3132 | CA | ILE | A | 221 | −75.731 | 23.916 | −2.857 | 1.00 | 16.33 C |
| ATOM | 3134 | CB | ILE | A | 221 | −77.203 | 23.895 | −2.352 | 1.00 | 15.94 C |
| ATOM | 3136 | CG1 | ILE | A | 221 | −77.410 | 24.879 | −1.203 | 1.00 | 15.36 C |
| ATOM | 3139 | CD1 | ILE | A | 221 | −78.842 | 25.234 | −.962 | 1.00 | 14.49 C |
| ATOM | 3143 | CG2 | ILE | A | 221 | −77.571 | 22.537 | −1.836 | 1.00 | 15.18 C |
| ATOM | 3147 | C | ILE | A | 221 | −75.509 | 22.841 | −3.911 | 1.00 | 17.06 C |
| ATOM | 3148 | O | ILE | A | 221 | −74.899 | 21.819 | −3.653 | 1.00 | 16.51 O |
| ATOM | 3150 | N | LEU | A | 222 | −75.981 | 23.138 | −5.117 | 1.00 | 18.53 N |
| ATOM | 3151 | CA | LEU | A | 222 | −76.006 | 22.207 | −6.243 | 1.00 | 19.25 C |
| ATOM | 3153 | CB | LEU | A | 222 | −76.657 | 22.891 | −7.445 | 1.00 | 19.18 C |
| ATOM | 3156 | CG | LEU | A | 222 | −77.037 | 21.972 | −8.597 | 1.00 | 19.65 C |
| ATOM | 3158 | CD1 | LEU | A | 222 | −78.318 | 22.489 | −9.268 | 1.00 | 19.24 C |
| ATOM | 3162 | CD2 | LEU | A | 222 | −75.869 | 21.788 | −9.597 | 1.00 | 18.75 C |
| ATOM | 3166 | C | LEU | A | 222 | −74.618 | 21.751 | −6.630 | 1.00 | 20.07 C |
| ATOM | 3167 | O | LEU | A | 222 | −74.381 | 20.558 | −6.778 | 1.00 | 20.55 O |
| ATOM | 3169 | N | ASP | A | 223 | −73.710 | 22.711 | −6.797 | 1.00 | 20.92 N |
| ATOM | 3170 | CA | ASP | A | 223 | −72.330 | 22.427 | −7.189 | 1.00 | 21.43 C |
| ATOM | 3172 | CB | ASP | A | 223 | −71.621 | 23.723 | −7.585 | 1.00 | 21.63 C |
| ATOM | 3175 | CG | ASP | A | 223 | −70.202 | 23.495 | −8.070 | 1.00 | 22.51 C |
| ATOM | 3176 | OD1 | ASP | A | 223 | −69.296 | 23.282 | −7.225 | 1.00 | 24.67 O |
| ATOM | 3177 | OD2 | ASP | A | 223 | −69.990 | 23.544 | −9.296 | 1.00 | 22.73 O |
| ATOM | 3178 | C | ASP | A | 223 | −71.573 | 21.722 | −6.060 | 1.00 | 21.79 C |
| ATOM | 3179 | O | ASP | A | 223 | −70.843 | 20.764 | −6.313 | 1.00 | 21.73 O |
| ATOM | 3181 | N | TYR | A | 224 | −71.755 | 22.182 | −4.820 | 1.00 | 22.14 N |
| ATOM | 3182 | CA | TYR | A | 224 | −71.120 | 21.529 | −3.686 | 1.00 | 22.22 C |
| ATOM | 3184 | CB | TYR | A | 224 | −71.462 | 22.190 | −2.355 | 1.00 | 22.38 C |
| ATOM | 3187 | CG | TYR | A | 224 | −70.673 | 21.542 | −1.249 | 1.00 | 22.65 C |
| ATOM | 3188 | CD1 | TYR | A | 224 | −69.356 | 21.864 | −1.053 | 1.00 | 22.59 C |
| ATOM | 3190 | CE1 | TYR | A | 224 | −68.622 | 21.258 | −.098 | 1.00 | 23.38 C |
| ATOM | 3192 | CZ | TYR | A | 224 | −69.177 | 20.288 | .670 | 1.00 | 23.22 C |
| ATOM | 3193 | OH | TYR | A | 224 | −68.402 | 19.684 | 1.620 | 1.00 | 23.93 O |
| ATOM | 3195 | CE2 | TYR | A | 224 | −70.483 | 19.931 | .500 | 1.00 | 23.36 C |
| ATOM | 3197 | CD2 | TYR | A | 224 | −71.221 | 20.547 | −.464 | 1.00 | 23.41 C |
| ATOM | 3199 | C | TYR | A | 224 | −71.485 | 20.065 | −3.605 | 1.00 | 22.52 C |
| ATOM | 3200 | O | TYR | A | 224 | −70.641 | 19.233 | −3.311 | 1.00 | 22.93 O |
| ATOM | 3202 | N | ASN | A | 225 | −72.742 | 19.749 | −3.856 | 1.00 | 22.94 N |
| ATOM | 3203 | CA | ASN | A | 225 | −73.187 | 18.374 | −3.801 | 1.00 | 23.44 C |
| ATOM | 3205 | CB | ASN | A | 225 | −74.706 | 18.310 | −3.729 | 1.00 | 23.34 C |
| ATOM | 3208 | CG | ASN | A | 225 | −75.210 | 18.579 | −2.352 | 1.00 | 22.62 C |
| ATOM | 3209 | OD1 | ASN | A | 225 | −74.749 | 17.977 | −1.407 | 1.00 | 23.33 O |
| ATOM | 3210 | ND2 | ASN | A | 225 | −76.146 | 19.494 | −2.223 | 1.00 | 22.52 N |
| ATOM | 3213 | C | ASN | A | 225 | −72.694 | 17.523 | −4.959 | 1.00 | 24.26 C |
| ATOM | 3214 | O | ASN | A | 225 | −72.408 | 16.328 | −4.767 | 1.00 | 24.88 O |
| ATOM | 3216 | N | MET | A | 226 | −72.607 | 18.119 | −6.150 | 1.00 | 24.67 N |
| ATOM | 3217 | CA | MET | A | 226 | −72.167 | 17.395 | −7.349 | 1.00 | 24.95 C |
| ATOM | 3219 | CB | MET | A | 226 | −72.421 | 18.237 | −8.594 | 1.00 | 25.37 C |
| ATOM | 3222 | CG | MET | A | 226 | −71.785 | 17.713 | −9.873 | 1.00 | 27.23 C |
| ATOM | 3225 | SD | MET | A | 226 | −70.837 | 19.010 | −10.708 | 1.00 | 31.73 S |
| ATOM | 3226 | CE | MET | A | 226 | −72.185 | 20.000 | −11.367 | 1.00 | 31.30 C |
| ATOM | 3230 | C | MET | A | 226 | −70.688 | 17.045 | −7.247 | 1.00 | 24.70 C |

TABLE 3-7-continued

Coordinates of *P. tremuloides* IspS

| ATOM | 3231 | O | MET | A | 226 | −70.291 | 15.929 | −7.568 | 1.00 | 24.91 | O |
| ATOM | 3233 | N | ILE | A | 227 | −69.873 | 17.995 | −6.799 | 1.00 | 24.43 | N |
| ATOM | 3234 | CA | ILE | A | 227 | −68.456 | 17.726 | −6.598 | 1.00 | 24.18 | C |
| ATOM | 3236 | CB | ILE | A | 227 | −67.656 | 18.971 | −6.154 | 1.00 | 24.15 | C |
| ATOM | 3238 | CG1 | ILE | A | 227 | −67.628 | 20.021 | −7.253 | 1.00 | 23.64 | C |
| ATOM | 3241 | CD1 | ILE | A | 227 | −66.853 | 21.246 | −6.880 | 1.00 | 23.11 | C |
| ATOM | 3245 | CG2 | ILE | A | 227 | −66.229 | 18.603 | −5.827 | 1.00 | 24.36 | C |
| ATOM | 3249 | C | ILE | A | 227 | −68.329 | 16.645 | −5.546 | 1.00 | 23.98 | C |
| ATOM | 3250 | O | ILE | A | 227 | −67.609 | 15.689 | −5.747 | 1.00 | 24.35 | O |
| ATOM | 3252 | N | GLN | A | 228 | −69.048 | 16.779 | −4.439 | 1.00 | 23.79 | N |
| ATOM | 3253 | CA | GLN | A | 228 | −69.020 | 15.754 | −3.382 | 1.00 | 23.66 | C |
| ATOM | 3255 | CB | GLN | A | 228 | −70.077 | 16.010 | −2.305 | 1.00 | 23.64 | C |
| ATOM | 3258 | CG | GLN | A | 228 | −69.972 | 15.049 | −1.145 | 1.00 | 22.91 | C |
| ATOM | 3261 | CD | GLN | A | 228 | −70.891 | 15.417 | −.033 | 1.00 | 23.26 | C |
| ATOM | 3262 | OE1 | GLN | A | 228 | −72.082 | 15.098 | −.069 | 1.00 | 25.64 | O |
| ATOM | 3263 | NE2 | GLN | A | 228 | −70.357 | 16.083 | .978 | 1.00 | 21.77 | N |
| ATOM | 3266 | C | GLN | A | 228 | −69.243 | 14.349 | −3.893 | 1.00 | 23.54 | C |
| ATOM | 3267 | O | GLN | A | 228 | −68.664 | 13.412 | −3.357 | 1.00 | 23.59 | O |
| ATOM | 3269 | N | SER | A | 229 | −70.105 | 14.194 | −4.893 | 1.00 | 23.27 | N |
| ATOM | 3270 | CA | SER | A | 229 | −70.394 | 12.868 | −5.406 | 1.00 | 23.35 | C |
| ATOM | 3272 | CB | SER | A | 229 | −71.753 | 12.812 | −6.095 | 1.00 | 23.31 | C |
| ATOM | 3275 | OG | SER | A | 229 | −71.836 | 13.823 | −7.060 | 1.00 | 24.31 | O |
| ATOM | 3277 | C | SER | A | 229 | −69.287 | 12.394 | −6.331 | 1.00 | 23.19 | C |
| ATOM | 3278 | O | SER | A | 229 | −69.130 | 11.194 | −6.512 | 1.00 | 23.44 | O |
| ATOM | 3280 | N | VAL | A | 230 | −68.512 | 13.306 | −6.914 | 1.00 | 23.14 | N |
| ATOM | 3281 | CA | VAL | A | 230 | −67.269 | 12.874 | −7.552 | 1.00 | 23.00 | C |
| ATOM | 3283 | CB | VAL | A | 230 | −66.469 | 13.998 | −8.253 | 1.00 | 22.75 | C |
| ATOM | 3285 | CG1 | VAL | A | 230 | −65.091 | 13.470 | −8.667 | 1.00 | 21.87 | C |
| ATOM | 3289 | CG2 | VAL | A | 230 | −67.222 | 14.539 | −9.459 | 1.00 | 21.74 | C |
| ATOM | 3293 | C | VAL | A | 230 | −66.417 | 12.268 | −6.452 | 1.00 | 23.35 | C |
| ATOM | 3294 | O | VAL | A | 230 | −65.917 | 11.173 | −6.589 | 1.00 | 23.68 | O |
| ATOM | 3296 | N | TYR | A | 231 | −66.284 | 12.968 | −5.340 | 1.00 | 23.96 | N |
| ATOM | 3297 | CA | TYR | A | 231 | −65.414 | 12.509 | −4.274 | 1.00 | 24.60 | C |
| ATOM | 3299 | CB | TYR | A | 231 | −65.486 | 13.426 | −3.051 | 1.00 | 24.69 | C |
| ATOM | 3302 | CG | TYR | A | 231 | −64.963 | 14.837 | −3.211 | 1.00 | 24.11 | C |
| ATOM | 3303 | CD1 | TYR | A | 231 | −64.071 | 15.190 | −4.214 | 1.00 | 24.31 | C |
| ATOM | 3305 | CE1 | TYR | A | 231 | −63.592 | 16.491 | −4.322 | 1.00 | 24.63 | C |
| ATOM | 3307 | CZ | TYR | A | 231 | −63.994 | 17.441 | −3.406 | 1.00 | 25.13 | C |
| ATOM | 3308 | OH | TYR | A | 231 | −63.554 | 18.754 | −3.456 | 1.00 | 24.64 | O |
| ATOM | 3310 | CE2 | TYR | A | 231 | −64.863 | 17.086 | −2.402 | 1.00 | 25.76 | C |
| ATOM | 3312 | CD2 | TYR | A | 231 | −65.329 | 15.800 | −2.308 | 1.00 | 24.28 | C |
| ATOM | 3314 | C | TYR | A | 231 | −65.785 | 11.111 | −3.833 | 1.00 | 25.26 | C |
| ATOM | 3315 | O | TYR | A | 231 | −64.917 | 10.315 | −3.488 | 1.00 | 25.44 | O |
| ATOM | 3317 | N | GLN | A | 232 | −67.079 | 10.819 | −3.833 | 1.00 | 26.04 | N |
| ATOM | 3318 | CA | GLN | A | 232 | −67.566 | 9.532 | −3.362 | 1.00 | 26.57 | C |
| ATOM | 3320 | CB | GLN | A | 232 | −69.060 | 9.621 | −3.057 | 1.00 | 26.44 | C |
| ATOM | 3323 | CG | GLN | A | 232 | −69.339 | 10.397 | −1.778 | 1.00 | 26.25 | C |
| ATOM | 3326 | CD | GLN | A | 232 | −70.786 | 10.819 | −1.630 | 1.00 | 26.53 | C |
| ATOM | 3327 | OE1 | GLN | A | 232 | −71.667 | 10.305 | −2.318 | 1.00 | 27.77 | O |
| ATOM | 3328 | NE2 | GLN | A | 232 | −71.040 | 11.759 | −.723 | 1.00 | 25.51 | N |
| ATOM | 3331 | C | GLN | A | 232 | −67.238 | 8.414 | −4.351 | 1.00 | 27.44 | C |
| ATOM | 3332 | O | GLN | A | 232 | −66.852 | 7.319 | −3.935 | 1.00 | 27.33 | O |
| ATOM | 3334 | N | ARG | A | 233 | −67.373 | 8.691 | −5.649 | 1.00 | 28.66 | N |
| ATOM | 3335 | CA | ARG | A | 233 | −66.905 | 7.768 | −6.685 | 1.00 | 29.86 | C |
| ATOM | 3337 | CB | ARG | A | 233 | −67.212 | 8.292 | −8.090 | 1.00 | 30.08 | C |
| ATOM | 3340 | CG | ARG | A | 233 | −66.378 | 7.634 | −9.179 | 1.00 | 32.80 | C |
| ATOM | 3343 | CD | ARG | A | 233 | −66.913 | 7.923 | −10.572 | 1.00 | 36.74 | C |
| ATOM | 3346 | NE | ARG | A | 233 | −66.962 | 9.363 | −10.860 | 1.00 | 40.33 | N |
| ATOM | 3348 | CZ | ARG | A | 233 | −68.069 | 10.119 | −10.891 | 1.00 | 43.12 | C |
| ATOM | 3349 | NH1 | ARG | A | 233 | −69.276 | 9.600 | −10.655 | 1.00 | 44.55 | N |
| ATOM | 3352 | NH2 | ARG | A | 233 | −67.971 | 11.418 | −11.169 | 1.00 | 43.38 | N |
| ATOM | 3355 | C | ARG | A | 233 | −65.401 | 7.518 | −6.514 | 1.00 | 30.34 | C |
| ATOM | 3356 | O | ARG | A | 233 | −64.962 | 6.374 | −6.412 | 1.00 | 30.55 | O |
| ATOM | 3358 | N | ASP | A | 234 | −64.621 | 8.591 | −6.461 | 1.00 | 31.00 | N |
| ATOM | 3359 | CA | ASP | A | 234 | −63.187 | 8.487 | −6.205 | 1.00 | 31.48 | C |
| ATOM | 3361 | CB | ASP | A | 234 | −62.594 | 9.870 | −5.942 | 1.00 | 31.56 | C |
| ATOM | 3364 | CG | ASP | A | 234 | −62.573 | 10.741 | −7.167 | 1.00 | 32.78 | C |
| ATOM | 3365 | OD1 | ASP | A | 234 | −62.911 | 10.249 | −8.276 | 1.00 | 34.25 | O |
| ATOM | 3366 | OD2 | ASP | A | 234 | −62.215 | 11.930 | −7.011 | 1.00 | 34.81 | O |
| ATOM | 3367 | C | ASP | A | 234 | −62.885 | 7.596 | −5.010 | 1.00 | 31.70 | C |
| ATOM | 3368 | O | ASP | A | 234 | −61.985 | 6.780 | −5.053 | 1.00 | 31.56 | O |
| ATOM | 3370 | N | LEU | A | 235 | −63.647 | 7.766 | −3.943 | 1.00 | 32.43 | N |
| ATOM | 3371 | CA | LEU | A | 235 | −63.366 | 7.102 | −2.685 | 1.00 | 33.04 | C |
| ATOM | 3373 | CB | LEU | A | 235 | −64.072 | 7.833 | −1.553 | 1.00 | 32.57 | C |
| ATOM | 3376 | CG | LEU | A | 235 | −63.884 | 7.252 | −.167 | 1.00 | 30.85 | C |
| ATOM | 3378 | CD1 | LEU | A | 235 | −62.428 | 7.261 | .174 | 1.00 | 28.78 | C |
| ATOM | 3382 | CD2 | LEU | A | 235 | −64.703 | 8.050 | .823 | 1.00 | 29.93 | C |
| ATOM | 3386 | C | LEU | A | 235 | −63.789 | 5.637 | −2.686 | 1.00 | 34.69 | C |

TABLE 3-7-continued

Coordinates of *P. tremuloides* IspS

| ATOM | 3387 | O | LEU | A | 235 | −63.123 | 4.812 | −2.065 | 1.00 | 35.29 | O |
|---|---|---|---|---|---|---|---|---|---|---|---|
| ATOM | 3389 | N | ARG | A | 236 | −64.893 | 5.299 | −3.354 | 1.00 | 36.09 | N |
| ATOM | 3390 | CA | ARG | A | 236 | −65.290 | 3.893 | −3.458 | 1.00 | 37.26 | C |
| ATOM | 3392 | CB | ARG | A | 236 | −66.672 | 3.736 | −4.103 | 1.00 | 37.64 | C |
| ATOM | 3395 | CG | ARG | A | 236 | −67.839 | 4.000 | −3.157 | 1.00 | 39.15 | C |
| ATOM | 3398 | CD | ARG | A | 236 | −69.162 | 3.528 | −3.741 | 1.00 | 40.25 | C |
| ATOM | 3401 | NE | ARG | A | 236 | −69.385 | 4.046 | −5.095 | 1.00 | 41.64 | N |
| ATOM | 3403 | CZ | ARG | A | 236 | −69.837 | 5.269 | −5.392 | 1.00 | 42.54 | C |
| ATOM | 3404 | NH1 | ARG | A | 236 | −70.115 | 6.147 | −4.430 | 1.00 | 42.18 | N |
| ATOM | 3407 | NH2 | ARG | A | 236 | −70.012 | 5.621 | −6.668 | 1.00 | 43.04 | N |
| ATOM | 3410 | C | ARG | A | 236 | −64.266 | 3.108 | −4.262 | 1.00 | 37.81 | C |
| ATOM | 3411 | O | ARG | A | 236 | −64.104 | 1.912 | −4.060 | 1.00 | 38.07 | O |
| ATOM | 3413 | N | GLU | A | 237 | −63.584 | 3.801 | −5.168 | 1.00 | 38.69 | N |
| ATOM | 3414 | CA | GLU | A | 237 | −62.639 | 3.189 | −6.102 | 1.00 | 39.45 | C |
| ATOM | 3416 | CB | GLU | A | 237 | −62.452 | 4.108 | −7.338 | 1.00 | 40.25 | C |
| ATOM | 3419 | CG | GLU | A | 237 | −62.268 | 3.387 | −8.710 | 1.00 | 43.02 | C |
| ATOM | 3422 | CD | GLU | A | 237 | −60.835 | 3.458 | −9.287 | 1.00 | 46.64 | C |
| ATOM | 3423 | OE1 | GLU | A | 237 | −60.093 | 4.440 | −8.997 | 1.00 | 48.03 | O |
| ATOM | 3424 | OE2 | GLU | A | 237 | −60.466 | 2.519 | −10.047 | 1.00 | 48.35 | O |
| ATOM | 3425 | C | GLU | A | 237 | −61.310 | 2.905 | −5.408 | 1.00 | 38.70 | C |
| ATOM | 3426 | O | GLU | A | 237 | −60.832 | 1.782 | −5.440 | 1.00 | 38.33 | O |
| ATOM | 3428 | N | THR | A | 238 | −60.726 | 3.908 | −4.764 | 1.00 | 38.40 | N |
| ATOM | 3429 | CA | THR | A | 238 | −59.504 | 3.669 | −4.009 | 1.00 | 38.74 | C |
| ATOM | 3431 | CB | THR | A | 238 | −58.710 | 4.965 | −3.593 | 1.00 | 38.78 | C |
| ATOM | 3433 | OG1 | THR | A | 238 | −59.294 | 5.583 | −2.444 | 1.00 | 38.38 | O |
| ATOM | 3435 | CG2 | THR | A | 238 | −58.612 | 5.963 | −4.743 | 1.00 | 38.94 | C |
| ATOM | 3439 | C | THR | A | 238 | −59.802 | 2.834 | −2.773 | 1.00 | 39.05 | C |
| ATOM | 3440 | O | THR | A | 238 | −58.886 | 2.294 | −2.153 | 1.00 | 39.17 | O |
| ATOM | 3442 | N | SER | A | 239 | −61.076 | 2.717 | −2.408 | 1.00 | 39.34 | N |
| ATOM | 3443 | CA | SER | A | 239 | −61.443 | 1.841 | −1.304 | 1.00 | 39.47 | C |
| ATOM | 3445 | CB | SER | A | 239 | −62.844 | 2.149 | −.792 | 1.00 | 39.34 | C |
| ATOM | 3448 | OG | SER | A | 239 | −63.087 | 1.428 | .396 | 1.00 | 39.94 | O |
| ATOM | 3450 | C | SER | A | 239 | −61.313 | .367 | −1.699 | 1.00 | 39.53 | C |
| ATOM | 3451 | O | SER | A | 239 | −60.834 | −.439 | −.900 | 1.00 | 39.53 | O |
| ATOM | 3453 | N | ARG | A | 240 | −61.728 | .021 | −2.921 | 1.00 | 39.69 | N |
| ATOM | 3454 | CA | ARG | A | 240 | −61.559 | −1.341 | −3.439 | 1.00 | 39.79 | C |
| ATOM | 3456 | CB | ARG | A | 240 | −62.105 | −1.492 | −4.867 | 1.00 | 40.34 | C |
| ATOM | 3459 | CG | ARG | A | 240 | −63.624 | −1.715 | −4.947 | 1.00 | 43.03 | C |
| ATOM | 3462 | CD | ARG | A | 240 | −64.104 | −2.125 | −6.364 | 1.00 | 46.66 | C |
| ATOM | 3465 | NE | ARG | A | 240 | −63.780 | −1.136 | −7.416 | 1.00 | 50.46 | N |
| ATOM | 3467 | CZ | ARG | A | 240 | −64.535 | −.082 | −7.775 | 1.00 | 53.13 | C |
| ATOM | 3468 | NH1 | ARG | A | 240 | −64.112 | .732 | −8.749 | 1.00 | 53.13 | N |
| ATOM | 3471 | NH2 | ARG | A | 240 | −65.707 | .178 | −7.178 | 1.00 | 54.02 | N |
| ATOM | 3474 | C | ARG | A | 240 | −60.089 | −1.704 | −3.414 | 1.00 | 38.94 | C |
| ATOM | 3475 | O | ARG | A | 240 | −59.732 | −2.795 | −2.978 | 1.00 | 39.09 | O |
| ATOM | 3477 | N | TRP | A | 241 | −59.246 | −.775 | −3.862 | 1.00 | 37.92 | N |
| ATOM | 3478 | CA | TRP | A | 241 | −57.787 | −.947 | −3.842 | 1.00 | 36.93 | C |
| ATOM | 3480 | CB | TRP | A | 241 | −57.099 | .318 | −4.388 | 1.00 | 36.57 | C |
| ATOM | 3483 | CG | TRP | A | 241 | −55.624 | .333 | −4.209 | 1.00 | 34.71 | C |
| ATOM | 3484 | CD1 | TRP | A | 241 | −54.702 | −.312 | −4.969 | 1.00 | 33.50 | C |
| ATOM | 3486 | NE1 | TRP | A | 241 | −53.441 | −.068 | −4.482 | 1.00 | 32.62 | N |
| ATOM | 3488 | CE2 | TRP | A | 241 | −53.538 | .747 | −3.392 | 1.00 | 31.16 | C |
| ATOM | 3489 | CD2 | TRP | A | 241 | −54.896 | 1.022 | −3.191 | 1.00 | 32.61 | C |
| ATOM | 3490 | CE3 | TRP | A | 241 | −55.268 | 1.837 | −2.117 | 1.00 | 32.63 | C |
| ATOM | 3492 | CZ3 | TRP | A | 241 | −54.293 | 2.345 | −1.307 | 1.00 | 31.31 | C |
| ATOM | 3494 | CH2 | TRP | A | 241 | −52.956 | 2.053 | −1.537 | 1.00 | 31.81 | C |
| ATOM | 3496 | CZ2 | TRP | A | 241 | −52.560 | 1.252 | −2.577 | 1.00 | 31.18 | C |
| ATOM | 3498 | C | TRP | A | 241 | −57.263 | −1.274 | −2.444 | 1.00 | 36.67 | C |
| ATOM | 3499 | O | TRP | A | 241 | −56.540 | −2.247 | −2.252 | 1.00 | 36.32 | O |
| ATOM | 3501 | N | TRP | A | 242 | −57.647 | −.460 | −1.471 | 1.00 | 36.59 | N |
| ATOM | 3502 | CA | TRP | A | 242 | −57.150 | −.593 | −.100 | 1.00 | 36.80 | C |
| ATOM | 3504 | CB | TRP | A | 242 | −57.694 | .582 | .734 | 1.00 | 36.47 | C |
| ATOM | 3507 | CG | TRP | A | 242 | −57.113 | .754 | 2.107 | 1.00 | 35.59 | C |
| ATOM | 3508 | CD1 | TRP | A | 242 | −57.806 | .831 | 3.270 | 1.00 | 35.14 | C |
| ATOM | 3510 | NE1 | TRP | A | 242 | −56.950 | .999 | 4.328 | 1.00 | 34.47 | N |
| ATOM | 3512 | CE2 | TRP | A | 242 | −55.667 | 1.032 | 3.859 | 1.00 | 34.64 | C |
| ATOM | 3513 | CD2 | TRP | A | 242 | −55.728 | .884 | 2.461 | 1.00 | 35.26 | C |
| ATOM | 3514 | CE3 | TRP | A | 242 | −54.531 | .882 | 1.732 | 1.00 | 35.22 | C |
| ATOM | 3516 | CZ3 | TRP | A | 242 | −53.342 | 1.024 | 2.409 | 1.00 | 34.30 | C |
| ATOM | 3518 | CH2 | TRP | A | 242 | −53.318 | 1.169 | 3.799 | 1.00 | 34.70 | C |
| ATOM | 3520 | CZ2 | TRP | A | 242 | −54.467 | 1.173 | 4.542 | 1.00 | 34.63 | C |
| ATOM | 3522 | C | TRP | A | 242 | −57.482 | −1.975 | .524 | 1.00 | 37.34 | C |
| ATOM | 3523 | O | TRP | A | 242 | −56.628 | −2.623 | 1.126 | 1.00 | 36.53 | O |
| ATOM | 3525 | N | ARG | A | 243 | −58.720 | −2.421 | .348 | 1.00 | 38.54 | N |
| ATOM | 3526 | CA | ARG | A | 243 | −59.149 | −3.734 | .822 | 1.00 | 39.71 | C |
| ATOM | 3528 | CB | ARG | A | 243 | −60.669 | −3.896 | .687 | 1.00 | 40.10 | C |
| ATOM | 3531 | CG | ARG | A | 243 | −61.495 | −3.134 | 1.747 | 1.00 | 42.18 | C |
| ATOM | 3534 | CD | ARG | A | 243 | −62.826 | −2.623 | 1.169 | 1.00 | 45.18 | C |

TABLE 3-7-continued

| | | | | | | | | | | | |
|---|---|---|---|---|---|---|---|---|---|---|---|
| colspan="12" | Coordinates of *P. tremuloides* IspS |
| ATOM | 3537 | NE | ARG | A | 243 | −63.506 | −3.656 | .369 | 1.00 | 48.22 | N |
| ATOM | 3539 | CZ | ARG | A | 243 | −64.374 | −3.431 | −.629 | 1.00 | 49.95 | C |
| ATOM | 3540 | NH1 | ARG | A | 243 | −64.717 | −2.182 | −.991 | 1.00 | 50.13 | N |
| ATOM | 3543 | NH2 | ARG | A | 243 | −64.911 | −4.477 | −1.273 | 1.00 | 49.77 | N |
| ATOM | 3546 | C | ARG | A | 243 | −58.438 | −4.852 | .068 | 1.00 | 40.08 | C |
| ATOM | 3547 | O | ARG | A | 243 | −58.084 | −5.870 | .665 | 1.00 | 40.45 | O |
| ATOM | 3549 | N | ARG | A | 244 | −58.236 | −4.663 | −1.236 | 1.00 | 40.42 | N |
| ATOM | 3550 | CA | ARG | A | 244 | −57.499 | −5.621 | −2.063 | 1.00 | 40.65 | C |
| ATOM | 3552 | CB | ARG | A | 244 | −57.370 | −5.100 | −3.503 | 1.00 | 41.29 | C |
| ATOM | 3555 | CG | ARG | A | 244 | −56.939 | −6.126 | −4.560 | 1.00 | 43.27 | C |
| ATOM | 3558 | CD | ARG | A | 244 | −58.090 | −7.062 | −4.952 | 1.00 | 46.01 | C |
| ATOM | 3561 | NE | ARG | A | 244 | −57.595 | −8.337 | −5.485 | 1.00 | 48.77 | N |
| ATOM | 3563 | CZ | ARG | A | 244 | −57.075 | −9.332 | −4.752 | 1.00 | 51.17 | C |
| ATOM | 3564 | NH1 | ARG | A | 244 | −56.968 | −9.234 | −3.422 | 1.00 | 51.63 | N |
| ATOM | 3567 | NH2 | ARG | A | 244 | −56.656 | −10.448 | −5.353 | 1.00 | 52.11 | N |
| ATOM | 3570 | C | ARG | A | 244 | −56.120 | −5.861 | −1.465 | 1.00 | 40.12 | C |
| ATOM | 3571 | O | ARG | A | 244 | −55.728 | −7.000 | −1.235 | 1.00 | 39.96 | O |
| ATOM | 3573 | N | VAL | A | 245 | −55.399 | −4.778 | −1.201 | 1.00 | 39.78 | N |
| ATOM | 3574 | CA | VAL | A | 245 | −54.099 | −4.858 | −.543 | 1.00 | 39.68 | C |
| ATOM | 3576 | CB | VAL | A | 245 | −53.430 | −3.458 | −.437 | 1.00 | 39.70 | C |
| ATOM | 3578 | CG1 | VAL | A | 245 | −53.133 | −2.914 | −1.824 | 1.00 | 39.54 | C |
| ATOM | 3582 | CG2 | VAL | A | 245 | −52.145 | −3.507 | .395 | 1.00 | 39.41 | C |
| ATOM | 3586 | C | VAL | A | 245 | −54.262 | −5.472 | .841 | 1.00 | 39.73 | C |
| ATOM | 3587 | O | VAL | A | 245 | −53.455 | −6.291 | 1.253 | 1.00 | 39.53 | O |
| ATOM | 3589 | N | GLY | A | 246 | −55.312 | −5.051 | 1.544 | 1.00 | 40.11 | N |
| ATOM | 3590 | CA | GLY | A | 246 | −55.705 | −5.617 | 2.839 | 1.00 | 40.35 | C |
| ATOM | 3593 | C | GLY | A | 246 | −54.621 | −5.648 | 3.894 | 1.00 | 40.58 | C |
| ATOM | 3594 | O | GLY | A | 246 | −54.396 | −6.676 | 4.510 | 1.00 | 40.68 | O |
| ATOM | 3596 | N | LEU | A | 247 | −53.963 | −4.522 | 4.129 | 1.00 | 41.15 | N |
| ATOM | 3597 | CA | LEU | A | 247 | −52.778 | −4.519 | 4.982 | 1.00 | 41.71 | C |
| ATOM | 3599 | CB | LEU | A | 247 | −51.808 | −3.422 | 4.537 | 1.00 | 41.60 | C |
| ATOM | 3602 | CG | LEU | A | 247 | −50.334 | −3.815 | 4.441 | 1.00 | 40.83 | C |
| ATOM | 3604 | CD1 | LEU | A | 247 | −50.158 | −5.014 | 3.539 | 1.00 | 40.54 | C |
| ATOM | 3608 | CD2 | LEU | A | 247 | −49.534 | −2.644 | 3.918 | 1.00 | 39.92 | C |
| ATOM | 3612 | C | LEU | A | 247 | −53.136 | −4.385 | 6.471 | 1.00 | 42.60 | C |
| ATOM | 3613 | O | LEU | A | 247 | −52.588 | −5.111 | 7.313 | 1.00 | 42.06 | O |
| ATOM | 3615 | N | ALA | A | 248 | −54.064 | −3.475 | 6.788 | 1.00 | 43.75 | N |
| ATOM | 3616 | CA | ALA | A | 248 | −54.603 | −3.352 | 8.162 | 1.00 | 44.52 | C |
| ATOM | 3618 | CB | ALA | A | 248 | −55.712 | −2.296 | 8.210 | 1.00 | 44.31 | C |
| ATOM | 3622 | C | ALA | A | 248 | −55.129 | −4.706 | 8.695 | 1.00 | 45.10 | C |
| ATOM | 3623 | O | ALA | A | 248 | −54.969 | −5.041 | 9.875 | 1.00 | 44.96 | O |
| ATOM | 3625 | N | THR | A | 249 | −55.742 | −5.477 | 7.802 | 1.00 | 45.91 | N |
| ATOM | 3626 | CA | THR | A | 249 | −56.328 | −6.768 | 8.154 | 1.00 | 46.50 | C |
| ATOM | 3628 | CB | THR | A | 249 | −57.303 | −7.277 | 7.041 | 1.00 | 46.48 | C |
| ATOM | 3630 | OG1 | THR | A | 249 | −56.583 | −8.039 | 6.063 | 1.00 | 46.20 | O |
| ATOM | 3632 | CG2 | THR | A | 249 | −58.033 | −6.102 | 6.350 | 1.00 | 46.70 | C |
| ATOM | 3636 | C | THR | A | 249 | −55.257 | −7.840 | 8.447 | 1.00 | 47.06 | C |
| ATOM | 3637 | O | THR | A | 249 | −55.531 | −8.813 | 9.159 | 1.00 | 47.22 | O |
| ATOM | 3639 | N | LYS | A | 250 | −54.049 | −7.661 | 7.905 | 1.00 | 47.52 | N |
| ATOM | 3640 | CA | LYS | A | 250 | −52.952 | −8.620 | 8.096 | 1.00 | 47.91 | C |
| ATOM | 3642 | CB | LYS | A | 250 | −52.319 | −8.976 | 6.744 | 1.00 | 48.09 | C |
| ATOM | 3645 | CG | LYS | A | 250 | −52.911 | −10.229 | 6.088 | 1.00 | 48.91 | C |
| ATOM | 3648 | CD | LYS | A | 250 | −52.210 | −11.510 | 6.585 | 1.00 | 49.88 | C |
| ATOM | 3651 | CE | LYS | A | 250 | −53.066 | −12.760 | 6.349 | 1.00 | 50.12 | C |
| ATOM | 3654 | NZ | LYS | A | 250 | −52.385 | −14.011 | 6.791 | 1.00 | 49.99 | N |
| ATOM | 3658 | C | LYS | A | 250 | −51.880 | −8.129 | 9.078 | 1.00 | 48.13 | C |
| ATOM | 3659 | O | LYS | A | 250 | −51.252 | −8.939 | 9.759 | 1.00 | 47.89 | O |
| ATOM | 3661 | N | LEU | A | 251 | −51.667 | −6.812 | 9.134 | 1.00 | 48.63 | N |
| ATOM | 3662 | CA | LEU | A | 251 | −50.758 | −6.187 | 10.114 | 1.00 | 48.83 | C |
| ATOM | 3664 | CB | LEU | A | 251 | −49.981 | −5.020 | 9.485 | 1.00 | 48.74 | C |
| ATOM | 3667 | CG | LEU | A | 251 | −48.569 | −5.296 | 8.960 | 1.00 | 48.51 | C |
| ATOM | 3669 | CD1 | LEU | A | 251 | −48.472 | −6.594 | 8.174 | 1.00 | 47.96 | C |
| ATOM | 3673 | CD2 | LEU | A | 251 | −48.102 | −4.115 | 8.116 | 1.00 | 48.76 | C |
| ATOM | 3677 | C | LEU | A | 251 | −51.559 | −5.703 | 11.324 | 1.00 | 49.17 | C |
| ATOM | 3678 | O | LEU | A | 251 | −52.176 | −4.632 | 11.304 | 1.00 | 49.28 | O |
| ATOM | 3680 | N | HIS | A | 252 | −51.521 | −6.486 | 12.393 | 1.00 | 49.53 | N |
| ATOM | 3681 | CA | HIS | A | 252 | −52.470 | −6.322 | 13.494 | 1.00 | 50.02 | C |
| ATOM | 3683 | CB | HIS | A | 252 | −52.598 | −7.647 | 14.266 | 1.00 | 50.42 | C |
| ATOM | 3686 | CG | HIS | A | 252 | −52.860 | −8.834 | 13.380 | 1.00 | 52.23 | C |
| ATOM | 3687 | ND1 | HIS | A | 252 | −54.032 | −8.989 | 12.667 | 1.00 | 53.75 | N |
| ATOM | 3689 | CE1 | HIS | A | 252 | −53.978 | −10.113 | 11.973 | 1.00 | 54.43 | C |
| ATOM | 3691 | NE2 | HIS | A | 252 | −52.810 | −10.689 | 12.201 | 1.00 | 54.52 | N |
| ATOM | 3693 | CD2 | HIS | A | 252 | −52.090 | −9.910 | 13.077 | 1.00 | 53.70 | C |
| ATOM | 3695 | C | HIS | A | 252 | −52.161 | −5.147 | 14.441 | 1.00 | 49.64 | C |
| ATOM | 3696 | O | HIS | A | 252 | −52.951 | −4.849 | 15.336 | 1.00 | 49.61 | O |
| ATOM | 3698 | N | PHE | A | 253 | −51.027 | −4.483 | 14.229 | 1.00 | 49.37 | N |
| ATOM | 3699 | CA | PHE | A | 253 | −50.652 | −3.273 | 14.973 | 1.00 | 49.15 | C |
| ATOM | 3701 | CB | PHE | A | 253 | −49.144 | −3.273 | 15.260 | 1.00 | 49.07 | C |

TABLE 3-7-continued

Coordinates of *P. tremuloides* IspS

| | | | | | | | | | | |
|---|---|---|---|---|---|---|---|---|---|---|
| ATOM | 3704 | CG | PHE | A | 253 | −48.307 | −3.112 | 14.025 | 1.00 | 48.30 C |
| ATOM | 3705 | CD1 | PHE | A | 253 | −48.028 | −1.851 | 13.518 | 1.00 | 48.10 C |
| ATOM | 3707 | CE1 | PHE | A | 253 | −47.290 | −1.702 | 12.349 | 1.00 | 48.21 C |
| ATOM | 3709 | CZ | PHE | A | 253 | −46.825 | −2.825 | 11.675 | 1.00 | 47.88 C |
| ATOM | 3711 | CE2 | PHE | A | 253 | −47.101 | −4.090 | 12.175 | 1.00 | 47.66 C |
| ATOM | 3713 | CD2 | PHE | A | 253 | −47.842 | −4.226 | 13.338 | 1.00 | 47.74 C |
| ATOM | 3715 | C | PHE | A | 253 | −50.974 | −2.006 | 14.176 | 1.00 | 49.31 C |
| ATOM | 3716 | O | PHE | A | 253 | −50.846 | −.893 | 14.702 | 1.00 | 49.01 O |
| ATOM | 3718 | N | ALA | A | 254 | −51.365 | −2.185 | 12.910 | 1.00 | 49.48 N |
| ATOM | 3719 | CA | ALA | A | 254 | −51.412 | −1.095 | 11.931 | 1.00 | 49.63 C |
| ATOM | 3721 | CB | ALA | A | 254 | −51.344 | −1.663 | 10.524 | 1.00 | 49.64 C |
| ATOM | 3725 | C | ALA | A | 254 | −52.650 | −.224 | 12.061 | 1.00 | 49.77 C |
| ATOM | 3726 | O | ALA | A | 254 | −53.761 | −.735 | 12.219 | 1.00 | 49.86 O |
| ATOM | 3728 | N | ARG | A | 255 | −52.452 | 1.090 | 11.975 | 1.00 | 49.93 N |
| ATOM | 3729 | CA | ARG | A | 255 | −53.562 | 2.042 | 11.908 | 1.00 | 50.27 C |
| ATOM | 3731 | CB | ARG | A | 255 | −53.094 | 3.468 | 12.237 | 1.00 | 50.43 C |
| ATOM | 3734 | CG | ARG | A | 255 | −52.678 | 3.736 | 13.696 | 1.00 | 50.82 C |
| ATOM | 3737 | CD | ARG | A | 255 | −52.242 | 5.211 | 13.887 | 1.00 | 51.32 C |
| ATOM | 3740 | NE | ARG | A | 255 | −51.003 | 5.522 | 13.155 | 1.00 | 51.81 N |
| ATOM | 3742 | CZ | ARG | A | 255 | −50.571 | 6.746 | 12.829 | 1.00 | 51.67 C |
| ATOM | 3743 | NH1 | ARG | A | 255 | −51.264 | 7.839 | 13.146 | 1.00 | 51.63 N |
| ATOM | 3746 | NH2 | ARG | A | 255 | −49.427 | 6.877 | 12.162 | 1.00 | 51.52 N |
| ATOM | 3749 | C | ARG | A | 255 | −54.160 | 2.040 | 10.497 | 1.00 | 50.32 C |
| ATOM | 3750 | O | ARG | A | 255 | −53.416 | 2.081 | 9.504 | 1.00 | 50.35 O |
| ATOM | 3752 | N | ASP | A | 256 | −55.492 | 2.005 | 10.412 | 1.00 | 50.17 N |
| ATOM | 3753 | CA | ASP | A | 256 | −56.190 | 2.090 | 9.128 | 1.00 | 50.18 C |
| ATOM | 3755 | CB | ASP | A | 256 | −57.259 | 1.009 | 9.037 | 1.00 | 50.37 C |
| ATOM | 3758 | CG | ASP | A | 256 | −58.095 | 1.130 | 7.780 | 1.00 | 50.96 C |
| ATOM | 3759 | OD1 | ASP | A | 256 | −59.252 | 1.601 | 7.881 | 1.00 | 52.00 O |
| ATOM | 3760 | OD2 | ASP | A | 256 | −57.581 | .787 | 6.693 | 1.00 | 50.94 O |
| ATOM | 3761 | C | ASP | A | 256 | −56.838 | 3.470 | 8.945 | 1.00 | 49.85 C |
| ATOM | 3762 | O | ASP | A | 256 | −57.812 | 3.804 | 9.624 | 1.00 | 50.13 O |
| ATOM | 3764 | N | ARG | A | 257 | −56.315 | 4.263 | 8.013 | 1.00 | 49.11 N |
| ATOM | 3765 | CA | ARG | A | 257 | −56.712 | 5.665 | 7.913 | 1.00 | 48.59 C |
| ATOM | 3767 | CB | ARG | A | 257 | −55.622 | 6.553 | 8.529 | 1.00 | 48.79 C |
| ATOM | 3770 | CG | ARG | A | 257 | −55.318 | 6.275 | 10.006 | 1.00 | 49.85 C |
| ATOM | 3773 | CD | ARG | A | 257 | −56.538 | 6.480 | 10.908 | 1.00 | 51.01 C |
| ATOM | 3776 | NE | ARG | A | 257 | −56.198 | 7.274 | 12.089 | 1.00 | 51.80 N |
| ATOM | 3778 | CZ | ARG | A | 257 | −55.779 | 6.791 | 13.260 | 1.00 | 52.00 C |
| ATOM | 3779 | NH1 | ARG | A | 257 | −55.643 | 5.486 | 13.468 | 1.00 | 51.64 N |
| ATOM | 3782 | NH2 | ARG | A | 257 | −55.501 | 7.638 | 14.245 | 1.00 | 52.62 N |
| ATOM | 3785 | C | ARG | A | 257 | −56.988 | 6.112 | 6.477 | 1.00 | 47.58 C |
| ATOM | 3786 | O | ARG | A | 257 | −56.476 | 7.144 | 6.031 | 1.00 | 47.40 O |
| ATOM | 3788 | N | LEU | A | 258 | −57.814 | 5.352 | 5.761 | 1.00 | 46.18 N |
| ATOM | 3789 | CA | LEU | A | 258 | −58.094 | 5.672 | 4.358 | 1.00 | 44.78 C |
| ATOM | 3791 | CB | LEU | A | 258 | −58.777 | 4.508 | 3.629 | 1.00 | 44.57 C |
| ATOM | 3794 | CG | LEU | A | 258 | −58.917 | 4.731 | 2.121 | 1.00 | 43.79 C |
| ATOM | 3796 | CD1 | LEU | A | 258 | −57.557 | 4.661 | 1.478 | 1.00 | 43.89 C |
| ATOM | 3800 | CD2 | LEU | A | 258 | −59.850 | 3.733 | 1.492 | 1.00 | 42.88 C |
| ATOM | 3804 | C | LEU | A | 258 | −58.970 | 6.907 | 4.259 | 1.00 | 43.52 C |
| ATOM | 3805 | O | LEU | A | 258 | −58.643 | 7.849 | 3.545 | 1.00 | 43.42 O |
| ATOM | 3807 | N | ILE | A | 259 | −60.080 | 6.895 | 4.983 | 1.00 | 41.98 N |
| ATOM | 3808 | CA | ILE | A | 259 | −61.072 | 7.948 | 4.843 | 1.00 | 40.89 C |
| ATOM | 3810 | CB | ILE | A | 259 | −62.349 | 7.703 | 5.693 | 1.00 | 41.02 C |
| ATOM | 3812 | CG1 | ILE | A | 259 | −62.846 | 6.248 | 5.570 | 1.00 | 41.82 C |
| ATOM | 3815 | CD1 | ILE | A | 259 | −64.029 | 5.872 | 6.508 | 1.00 | 42.29 C |
| ATOM | 3819 | CG2 | ILE | A | 259 | −63.446 | 8.662 | 5.262 | 1.00 | 40.47 C |
| ATOM | 3823 | C | ILE | A | 259 | −60.424 | 9.253 | 5.273 | 1.00 | 39.74 C |
| ATOM | 3824 | O | ILE | A | 259 | −60.607 | 10.291 | 4.635 | 1.00 | 39.25 O |
| ATOM | 3826 | N | GLU | A | 260 | −59.650 | 9.191 | 6.355 | 1.00 | 38.46 N |
| ATOM | 3827 | CA | GLU | A | 260 | −58.951 | 10.366 | 6.846 | 1.00 | 37.44 C |
| ATOM | 3829 | CB | GLU | A | 260 | −58.183 | 10.072 | 8.140 | 1.00 | 37.74 C |
| ATOM | 3832 | CG | GLU | A | 260 | −59.041 | 9.934 | 9.393 | 1.00 | 38.71 C |
| ATOM | 3835 | CD | GLU | A | 260 | −59.469 | 8.501 | 9.693 | 1.00 | 41.00 C |
| ATOM | 3836 | OE1 | GLU | A | 260 | −59.273 | 7.594 | 8.842 | 1.00 | 42.70 O |
| ATOM | 3837 | OE2 | GLU | A | 260 | −60.012 | 8.281 | 10.800 | 1.00 | 42.43 O |
| ATOM | 3838 | C | GLU | A | 260 | −57.995 | 10.841 | 5.764 | 1.00 | 35.94 C |
| ATOM | 3839 | O | GLU | A | 260 | −57.981 | 12.020 | 5.418 | 1.00 | 36.10 O |
| ATOM | 3841 | N | SER | A | 261 | −57.222 | 9.908 | 5.212 | 1.00 | 34.02 N |
| ATOM | 3842 | CA | SER | A | 261 | −56.263 | 10.229 | 4.152 | 1.00 | 32.47 C |
| ATOM | 3844 | CB | SER | A | 261 | −55.407 | 9.015 | 3.774 | 1.00 | 32.51 C |
| ATOM | 3847 | OG | SER | A | 261 | −54.253 | 8.940 | 4.584 | 1.00 | 33.14 O |
| ATOM | 3849 | C | SER | A | 261 | −56.894 | 10.764 | 2.889 | 1.00 | 30.82 C |
| ATOM | 3850 | O | SER | A | 261 | −56.199 | 11.306 | 2.062 | 1.00 | 30.79 O |
| ATOM | 3852 | N | PHE | A | 262 | −58.194 | 10.589 | 2.713 | 1.00 | 29.25 N |
| ATOM | 3853 | CA | PHE | A | 262 | −58.861 | 11.091 | 1.514 | 1.00 | 27.98 C |
| ATOM | 3855 | CB | PHE | A | 262 | −60.011 | 10.185 | 1.119 | 1.00 | 27.57 C |
| ATOM | 3858 | CG | PHE | A | 262 | −60.473 | 10.423 | −.251 | 1.00 | 26.11 C |

TABLE 3-7-continued

| | | | | | | | | | | | |
|---|---|---|---|---|---|---|---|---|---|---|---|
| ATOM | 3859 | CD1 | PHE | A | 262 | −59.763 | 9.914 | −1.318 | 1.00 | 25.14 | C |
| ATOM | 3861 | CE1 | PHE | A | 262 | −60.169 | 10.147 | −2.605 | 1.00 | 24.32 | C |
| ATOM | 3863 | CZ | PHE | A | 262 | −61.284 | 10.917 | −2.840 | 1.00 | 24.36 | C |
| ATOM | 3865 | CE2 | PHE | A | 262 | −61.987 | 11.445 | −1.785 | 1.00 | 25.23 | C |
| ATOM | 3867 | CD2 | PHE | A | 262 | −61.575 | 11.201 | −.492 | 1.00 | 25.61 | C |
| ATOM | 3869 | C | PHE | A | 262 | −59.394 | 12.507 | 1.707 | 1.00 | 27.29 | C |
| ATOM | 3870 | O | PHE | A | 262 | −59.275 | 13.359 | .821 | 1.00 | 27.39 | O |
| ATOM | 3872 | N | TYR | A | 263 | −60.025 | 12.723 | 2.856 | 1.00 | 26.19 | N |
| ATOM | 3873 | CA | TYR | A | 263 | −60.415 | 14.052 | 3.310 | 1.00 | 25.22 | C |
| ATOM | 3875 | CB | TYR | A | 263 | −60.975 | 13.942 | 4.735 | 1.00 | 25.21 | C |
| ATOM | 3878 | CG | TYR | A | 263 | −61.037 | 15.199 | 5.578 | 1.00 | 25.37 | C |
| ATOM | 3879 | CD1 | TYR | A | 263 | −62.020 | 16.152 | 5.385 | 1.00 | 24.95 | C |
| ATOM | 3881 | CE1 | TYR | A | 263 | −62.084 | 17.282 | 6.197 | 1.00 | 26.54 | C |
| ATOM | 3883 | CZ | TYR | A | 263 | −61.158 | 17.455 | 7.229 | 1.00 | 27.44 | C |
| ATOM | 3884 | OH | TYR | A | 263 | −61.186 | 18.567 | 8.059 | 1.00 | 28.97 | O |
| ATOM | 3886 | CE2 | TYR | A | 263 | −60.185 | 16.512 | 7.438 | 1.00 | 27.10 | C |
| ATOM | 3888 | CD2 | TYR | A | 263 | −60.136 | 15.390 | 6.626 | 1.00 | 26.91 | C |
| ATOM | 3890 | C | TYR | A | 263 | −59.190 | 14.946 | 3.238 | 1.00 | 24.29 | C |
| ATOM | 3891 | O | TYR | A | 263 | −59.267 | 16.077 | 2.757 | 1.00 | 24.13 | O |
| ATOM | 3893 | N | TRP | A | 264 | −58.055 | 14.415 | 3.682 | 1.00 | 23.01 | N |
| ATOM | 3894 | CA | TRP | A | 264 | −56.789 | 15.121 | 3.567 | 1.00 | 22.32 | C |
| ATOM | 3896 | CB | TRP | A | 264 | −55.642 | 14.261 | 4.119 | 1.00 | 22.26 | C |
| ATOM | 3899 | CG | TRP | A | 264 | −54.326 | 14.874 | 3.860 | 1.00 | 22.16 | C |
| ATOM | 3900 | CD1 | TRP | A | 264 | −53.614 | 14.821 | 2.699 | 1.00 | 22.68 | C |
| ATOM | 3902 | NE1 | TRP | A | 264 | −52.456 | 15.538 | 2.818 | 1.00 | 23.08 | N |
| ATOM | 3904 | CE2 | TRP | A | 264 | −52.407 | 16.083 | 4.072 | 1.00 | 23.07 | C |
| ATOM | 3905 | CD2 | TRP | A | 264 | −53.579 | 15.686 | 4.753 | 1.00 | 22.18 | C |
| ATOM | 3906 | CE3 | TRP | A | 264 | −53.782 | 16.119 | 6.066 | 1.00 | 22.57 | C |
| ATOM | 3908 | CZ3 | TRP | A | 264 | −52.824 | 16.925 | 6.657 | 1.00 | 23.43 | C |
| ATOM | 3910 | CH2 | TRP | A | 264 | −51.656 | 17.297 | 5.955 | 1.00 | 24.14 | C |
| ATOM | 3912 | CZ2 | TRP | A | 264 | −51.433 | 16.886 | 4.663 | 1.00 | 23.64 | C |
| ATOM | 3914 | C | TRP | A | 264 | −56.485 | 15.523 | 2.112 | 1.00 | 21.50 | C |
| ATOM | 3915 | O | TRP | A | 264 | −56.179 | 16.682 | 1.820 | 1.00 | 21.29 | O |
| ATOM | 3917 | N | ALA | A | 265 | −56.561 | 14.547 | 1.213 | 1.00 | 20.41 | N |
| ATOM | 3918 | CA | ALA | A | 265 | −56.242 | 14.760 | −.187 | 1.00 | 19.63 | C |
| ATOM | 3920 | CB | ALA | A | 265 | −56.298 | 13.437 | −.953 | 1.00 | 19.39 | C |
| ATOM | 3924 | C | ALA | A | 265 | −57.176 | 15.792 | −.798 | 1.00 | 19.07 | C |
| ATOM | 3925 | O | ALA | A | 265 | −56.760 | 16.573 | −1.633 | 1.00 | 18.99 | O |
| ATOM | 3927 | N | VAL | A | 266 | −58.431 | 15.814 | −.359 | 1.00 | 18.78 | N |
| ATOM | 3928 | CA | VAL | A | 266 | −59.396 | 16.828 | −.818 | 1.00 | 18.56 | C |
| ATOM | 3930 | CB | VAL | A | 266 | −60.839 | 16.541 | −.278 | 1.00 | 18.41 | C |
| ATOM | 3932 | CG1 | VAL | A | 266 | −61.405 | 15.298 | −.935 | 1.00 | 18.88 | C |
| ATOM | 3936 | CG2 | VAL | A | 266 | −61.780 | 17.709 | −.505 | 1.00 | 17.21 | C |
| ATOM | 3940 | C | VAL | A | 266 | −58.947 | 18.257 | −.450 | 1.00 | 18.43 | C |
| ATOM | 3941 | O | VAL | A | 266 | −59.250 | 19.200 | −1.171 | 1.00 | 18.83 | O |
| ATOM | 3943 | N | GLY | A | 267 | −58.230 | 18.411 | .663 | 1.00 | 17.96 | N |
| ATOM | 3944 | CA | GLY | A | 267 | −57.714 | 19.712 | 1.067 | 1.00 | 17.45 | C |
| ATOM | 3947 | C | GLY | A | 267 | −56.687 | 20.180 | .070 | 1.00 | 17.20 | C |
| ATOM | 3948 | O | GLY | A | 267 | −56.574 | 21.365 | −.215 | 1.00 | 17.41 | O |
| ATOM | 3950 | N | VAL | A | 268 | −55.959 | 19.219 | −.480 | 1.00 | 16.88 | N |
| ATOM | 3951 | CA | VAL | A | 268 | −54.822 | 19.487 | −1.319 | 1.00 | 16.62 | C |
| ATOM | 3953 | CB | VAL | A | 268 | −53.833 | 18.300 | −1.290 | 1.00 | 16.19 | C |
| ATOM | 3955 | CG1 | VAL | A | 268 | −52.691 | 18.536 | −2.240 | 1.00 | 15.50 | C |
| ATOM | 3959 | CG2 | VAL | A | 268 | −53.310 | 18.121 | .103 | 1.00 | 15.30 | C |
| ATOM | 3963 | C | VAL | A | 268 | −55.262 | 19.788 | −2.736 | 1.00 | 17.15 | C |
| ATOM | 3964 | O | VAL | A | 268 | −54.748 | 20.710 | −3.350 | 1.00 | 17.12 | O |
| ATOM | 3966 | N | ALA | A | 269 | −56.217 | 19.014 | −3.243 | 1.00 | 17.99 | N |
| ATOM | 3967 | CA | ALA | A | 269 | −56.688 | 19.158 | −4.622 | 1.00 | 18.79 | C |
| ATOM | 3969 | CB | ALA | A | 269 | −55.958 | 18.183 | −5.551 | 1.00 | 18.26 | C |
| ATOM | 3973 | C | ALA | A | 269 | −58.196 | 18.938 | −4.672 | 1.00 | 19.70 | C |
| ATOM | 3974 | O | ALA | A | 269 | −58.665 | 17.834 | −4.958 | 1.00 | 19.50 | O |
| ATOM | 3976 | N | PHE | A | 270 | −58.945 | 20.011 | −4.417 | 1.00 | 21.09 | N |
| ATOM | 3977 | CA | PHE | A | 270 | −60.393 | 19.910 | −4.211 | 1.00 | 22.32 | C |
| ATOM | 3979 | CB | PHE | A | 270 | −60.925 | 21.108 | −3.404 | 1.00 | 22.49 | C |
| ATOM | 3982 | CG | PHE | A | 270 | −61.193 | 22.321 | −4.246 | 1.00 | 23.31 | C |
| ATOM | 3983 | CD1 | PHE | A | 270 | −62.423 | 22.483 | −4.883 | 1.00 | 24.16 | C |
| ATOM | 3985 | CE1 | PHE | A | 270 | −62.662 | 23.569 | −5.683 | 1.00 | 23.84 | C |
| ATOM | 3987 | CZ | PHE | A | 270 | −61.675 | 24.497 | −5.871 | 1.00 | 23.93 | C |
| ATOM | 3989 | CE2 | PHE | A | 270 | −60.448 | 24.349 | −5.242 | 1.00 | 23.33 | C |
| ATOM | 3991 | CD2 | PHE | A | 270 | −60.213 | 23.268 | −4.443 | 1.00 | 23.11 | C |
| ATOM | 3993 | C | PHE | A | 270 | −61.173 | 19.820 | −5.515 | 1.00 | 23.21 | C |
| ATOM | 3994 | O | PHE | A | 270 | −62.142 | 19.069 | −5.599 | 1.00 | 23.48 | O |
| ATOM | 3996 | N | GLU | A | 271 | −60.771 | 20.599 | −6.522 | 1.00 | 24.16 | N |
| ATOM | 3997 | CA | GLU | A | 271 | −61.595 | 20.744 | −7.741 | 1.00 | 25.01 | C |
| ATOM | 3999 | CB | GLU | A | 271 | −61.065 | 21.863 | −8.655 | 1.00 | 25.19 | C |
| ATOM | 4002 | CG | GLU | A | 271 | −59.563 | 21.909 | −8.794 | 1.00 | 27.45 | C |
| ATOM | 4005 | CD | GLU | A | 271 | −58.857 | 22.910 | −7.857 | 1.00 | 30.03 | C |
| ATOM | 4006 | OE1 | GLU | A | 271 | −58.905 | 24.145 | −8.147 | 1.00 | 29.41 | O |

TABLE 3-7-continued

| | | | | | | | | | | |
|---|---|---|---|---|---|---|---|---|---|---|
| ATOM | 4007 | OE2 | GLU | A | 271 | −58.227 | 22.431 | −6.865 | 1.00 | 30.71 O |
| ATOM | 4008 | C | GLU | A | 271 | −61.799 | 19.391 | −8.484 | 1.00 | 24.95 C |
| ATOM | 4009 | O | GLU | A | 271 | −60.972 | 18.480 | −8.352 | 1.00 | 25.70 O |
| ATOM | 4011 | N | PRO | A | 272 | −62.918 | 19.242 | −9.224 | 1.00 | 24.59 N |
| ATOM | 4012 | CA | PRO | A | 272 | −63.399 | 17.915 | −9.656 | 1.00 | 24.38 C |
| ATOM | 4014 | CB | PRO | A | 272 | −64.675 | 18.243 | −10.430 | 1.00 | 24.25 C |
| ATOM | 4017 | CG | PRO | A | 272 | −65.105 | 19.536 | −9.869 | 1.00 | 24.53 C |
| ATOM | 4020 | CD | PRO | A | 272 | −63.855 | 20.295 | −9.639 | 1.00 | 24.42 C |
| ATOM | 4023 | C | PRO | A | 272 | −62.475 | 17.111 | −10.549 | 1.00 | 24.29 C |
| ATOM | 4024 | O | PRO | A | 272 | −62.406 | 15.886 | −10.410 | 1.00 | 24.45 O |
| ATOM | 4025 | N | GLN | A | 273 | −61.777 | 17.781 | −11.462 | 1.00 | 24.13 N |
| ATOM | 4026 | CA | GLN | A | 273 | −60.998 | 17.064 | −12.461 | 1.00 | 24.13 C |
| ATOM | 4028 | CB | GLN | A | 273 | −60.523 | 17.983 | −13.567 | 1.00 | 23.84 C |
| ATOM | 4031 | CG | GLN | A | 273 | −59.556 | 19.041 | −13.117 | 1.00 | 24.37 C |
| ATOM | 4034 | CD | GLN | A | 273 | −60.222 | 20.360 | −12.775 | 1.00 | 25.22 C |
| ATOM | 4035 | OE1 | GLN | A | 273 | −61.392 | 20.412 | −12.367 | 1.00 | 25.71 O |
| ATOM | 4036 | NE2 | GLN | A | 273 | −59.468 | 21.441 | −12.932 | 1.00 | 24.95 N |
| ATOM | 4039 | C | GLN | A | 273 | −59.808 | 16.327 | −11.877 | 1.00 | 24.33 C |
| ATOM | 4040 | O | GLN | A | 273 | −59.224 | 15.486 | −12.555 | 1.00 | 24.91 O |
| ATOM | 4042 | N | TYR | A | 274 | −59.462 | 16.607 | −10.626 | 1.00 | 24.27 N |
| ATOM | 4043 | CA | TYR | A | 274 | −58.211 | 16.119 | −10.067 | 1.00 | 24.38 C |
| ATOM | 4045 | CB | TYR | A | 274 | −57.639 | 17.180 | −9.138 | 1.00 | 24.36 C |
| ATOM | 4048 | CG | TYR | A | 274 | −57.066 | 18.398 | −9.819 | 1.00 | 24.35 C |
| ATOM | 4049 | CD1 | TYR | A | 274 | −56.249 | 18.291 | −10.935 | 1.00 | 24.13 C |
| ATOM | 4051 | CE1 | TYR | A | 274 | −55.716 | 19.409 | −11.542 | 1.00 | 23.75 C |
| ATOM | 4053 | CZ | TYR | A | 274 | −55.968 | 20.646 | −11.019 | 1.00 | 24.14 C |
| ATOM | 4054 | OH | TYR | A | 274 | −55.431 | 21.762 | −11.597 | 1.00 | 24.45 O |
| ATOM | 4056 | CE2 | TYR | A | 274 | −56.755 | 20.780 | −9.903 | 1.00 | 24.92 C |
| ATOM | 4058 | CD2 | TYR | A | 274 | −57.297 | 19.658 | −9.308 | 1.00 | 24.74 C |
| ATOM | 4060 | C | TYR | A | 274 | −58.319 | 14.796 | −9.310 | 1.00 | 24.63 C |
| ATOM | 4061 | O | TYR | A | 274 | −57.681 | 14.613 | −8.276 | 1.00 | 24.47 O |
| ATOM | 4063 | N | SER | A | 275 | −59.097 | 13.852 | −9.821 | 1.00 | 25.00 N |
| ATOM | 4064 | CA | SER | A | 275 | −59.254 | 12.575 | −9.116 | 1.00 | 25.11 C |
| ATOM | 4066 | CB | SER | A | 275 | −60.244 | 11.664 | −9.842 | 1.00 | 25.14 C |
| ATOM | 4069 | OG | SER | A | 275 | −61.537 | 12.252 | −9.852 | 1.00 | 25.96 O |
| ATOM | 4071 | C | SER | A | 275 | −57.907 | 11.885 | −8.963 | 1.00 | 24.94 C |
| ATOM | 4072 | O | SER | A | 275 | −57.544 | 11.439 | −7.877 | 1.00 | 24.57 O |
| ATOM | 4074 | N | ASP | A | 276 | −57.149 | 11.822 | −10.052 | 1.00 | 25.01 N |
| ATOM | 4075 | CA | ASP | A | 276 | −55.840 | 11.187 | −9.990 | 1.00 | 24.92 C |
| ATOM | 4077 | CB | ASP | A | 276 | −55.102 | 11.257 | −11.324 | 1.00 | 25.02 C |
| ATOM | 4080 | CG | ASP | A | 276 | −55.827 | 10.495 | −12.407 | 1.00 | 26.27 C |
| ATOM | 4081 | OD1 | ASP | A | 276 | −56.372 | 9.411 | −12.080 | 1.00 | 26.65 O |
| ATOM | 4082 | OD2 | ASP | A | 276 | −55.880 | 10.991 | −13.563 | 1.00 | 28.21 O |
| ATOM | 4083 | C | ASP | A | 276 | −55.026 | 11.798 | −8.881 | 1.00 | 24.30 C |
| ATOM | 4084 | O | ASP | A | 276 | −54.454 | 11.064 | −8.099 | 1.00 | 24.64 O |
| ATOM | 4086 | N | CYS | A | 277 | −55.005 | 13.124 | −8.772 | 1.00 | 23.61 N |
| ATOM | 4087 | CA | CYS | A | 277 | −54.210 | 13.746 | −7.715 | 1.00 | 22.91 C |
| ATOM | 4089 | CB | CYS | A | 277 | −54.262 | 15.268 | −7.748 | 1.00 | 22.83 C |
| ATOM | 4092 | SG | CYS | A | 277 | −53.048 | 15.994 | −6.615 | 1.00 | 22.43 S |
| ATOM | 4094 | C | CYS | A | 277 | −54.653 | 13.251 | −6.357 | 1.00 | 22.39 C |
| ATOM | 4095 | O | CYS | A | 277 | −53.822 | 12.833 | −5.559 | 1.00 | 22.23 O |
| ATOM | 4097 | N | ARG | A | 278 | −55.962 | 13.262 | −6.115 | 1.00 | 22.01 N |
| ATOM | 4098 | CA | ARG | A | 278 | −56.519 | 12.813 | −4.829 | 1.00 | 21.40 C |
| ATOM | 4100 | CB | ARG | A | 278 | −58.021 | 13.053 | −4.753 | 1.00 | 21.07 C |
| ATOM | 4103 | CG | ARG | A | 278 | −58.382 | 14.509 | −4.754 | 1.00 | 20.39 C |
| ATOM | 4106 | CD | ARG | A | 278 | −59.852 | 14.698 | −4.527 | 1.00 | 20.05 C |
| ATOM | 4109 | NE | ARG | A | 278 | −60.683 | 14.331 | −5.675 | 1.00 | 18.86 N |
| ATOM | 4111 | CZ | ARG | A | 278 | −60.993 | 15.144 | −6.679 | 1.00 | 18.58 C |
| ATOM | 4112 | NH1 | ARG | A | 278 | −60.530 | 16.391 | −6.730 | 1.00 | 18.45 N |
| ATOM | 4115 | NH2 | ARG | A | 278 | −61.775 | 14.702 | −7.647 | 1.00 | 19.04 N |
| ATOM | 4118 | C | ARG | A | 278 | −56.224 | 11.358 | −4.530 | 1.00 | 21.12 C |
| ATOM | 4119 | O | ARG | A | 278 | −55.804 | 11.050 | −3.434 | 1.00 | 21.59 O |
| ATOM | 4121 | N | ASN | A | 279 | −56.412 | 10.467 | −5.493 | 1.00 | 20.94 N |
| ATOM | 4122 | CA | ASN | A | 279 | −56.168 | 9.044 | −5.243 | 1.00 | 21.08 C |
| ATOM | 4124 | CB | ASN | A | 279 | −56.672 | 8.182 | −6.401 | 1.00 | 21.54 C |
| ATOM | 4127 | CG | ASN | A | 279 | −58.199 | 8.346 | −6.642 | 1.00 | 23.94 C |
| ATOM | 4128 | OD1 | ASN | A | 279 | −58.920 | 8.941 | −5.823 | 1.00 | 26.47 O |
| ATOM | 4129 | ND2 | ASN | A | 279 | −58.685 | 7.825 | −7.769 | 1.00 | 25.52 N |
| ATOM | 4132 | C | ASN | A | 279 | −54.699 | 8.798 | −4.972 | 1.00 | 20.30 C |
| ATOM | 4133 | O | ASN | A | 279 | −54.337 | 8.200 | −3.977 | 1.00 | 19.95 O |
| ATOM | 4135 | N | SER | A | 280 | −53.851 | 9.297 | −5.856 | 1.00 | 20.02 N |
| ATOM | 4136 | CA | SER | A | 280 | −52.409 | 9.335 | −5.612 | 1.00 | 19.32 C |
| ATOM | 4138 | CB | SER | A | 280 | −51.725 | 10.304 | −6.580 | 1.00 | 19.35 C |
| ATOM | 4141 | OG | SER | A | 280 | −50.624 | 9.705 | −7.212 | 1.00 | 19.77 O |
| ATOM | 4143 | C | SER | A | 280 | −52.122 | 9.745 | −4.166 | 1.00 | 18.55 C |
| ATOM | 4144 | O | SER | A | 280 | −51.514 | 8.976 | −3.436 | 1.00 | 18.98 O |
| ATOM | 4146 | N | VAL | A | 281 | −52.580 | 10.923 | −3.743 | 1.00 | 17.45 N |
| ATOM | 4147 | CA | VAL | A | 281 | −52.235 | 11.444 | −2.416 | 1.00 | 17.01 C |

TABLE 3-7-continued

Coordinates of *P. tremuloides* IspS

| ATOM | 4149 | CB | VAL | A | 281 | −52.650 | 12.934 | −2.235 | 1.00 | 17.20 | C |
|---|---|---|---|---|---|---|---|---|---|---|---|
| ATOM | 4151 | CG1 | VAL | A | 281 | −52.492 | 13.376 | −.787 | 1.00 | 16.76 | C |
| ATOM | 4155 | CG2 | VAL | A | 281 | −51.826 | 13.847 | −3.128 | 1.00 | 17.13 | C |
| ATOM | 4159 | C | VAL | A | 281 | −52.861 | 10.607 | −1.301 | 1.00 | 16.82 | C |
| ATOM | 4160 | O | VAL | A | 281 | −52.217 | 10.314 | −.289 | 1.00 | 16.81 | O |
| ATOM | 4162 | N | ALA | A | 282 | −54.118 | 10.225 | −1.481 | 1.00 | 16.55 | N |
| ATOM | 4163 | CA | ALA | A | 282 | −54.774 | 9.304 | −.559 | 1.00 | 16.31 | C |
| ATOM | 4165 | CB | ALA | A | 282 | −56.174 | 8.951 | −1.060 | 1.00 | 16.08 | C |
| ATOM | 4169 | C | ALA | A | 282 | −53.946 | 8.036 | −.355 | 1.00 | 16.31 | C |
| ATOM | 4170 | O | ALA | A | 282 | −53.671 | 7.653 | .762 | 1.00 | 16.16 | O |
| ATOM | 4172 | N | LYS | A | 283 | −53.539 | 7.395 | −1.443 | 1.00 | 16.92 | N |
| ATOM | 4173 | CA | LYS | A | 283 | −52.773 | 6.139 | −1.368 | 1.00 | 17.39 | C |
| ATOM | 4175 | CB | LYS | A | 283 | −52.454 | 5.596 | −2.773 | 1.00 | 17.31 | C |
| ATOM | 4178 | CG | LYS | A | 283 | −53.680 | 5.066 | −3.519 | 1.00 | 17.85 | C |
| ATOM | 4181 | CD | LYS | A | 283 | −53.389 | 4.527 | −4.941 | 1.00 | 18.98 | C |
| ATOM | 4184 | CE | LYS | A | 283 | −54.709 | 4.275 | −5.718 | 1.00 | 19.79 | C |
| ATOM | 4187 | NZ | LYS | A | 283 | −54.695 | 3.091 | −6.625 | 1.00 | 20.11 | N |
| ATOM | 4191 | C | LYS | A | 283 | −51.483 | 6.338 | −.591 | 1.00 | 17.82 | C |
| ATOM | 4192 | O | LYS | A | 283 | −51.170 | 5.577 | .331 | 1.00 | 17.37 | O |
| ATOM | 4194 | N | MET | A | 284 | −50.744 | 7.381 | −.964 | 1.00 | 18.49 | N |
| ATOM | 4195 | CA | MET | A | 284 | −49.434 | 7.622 | −.373 | 1.00 | 18.82 | C |
| ATOM | 4197 | CB | MET | A | 284 | −48.688 | 8.795 | −1.047 | 1.00 | 18.84 | C |
| ATOM | 4200 | CG | MET | A | 284 | −48.118 | 8.506 | −2.444 | 1.00 | 18.47 | C |
| ATOM | 4203 | SD | MET | A | 284 | −47.540 | 6.819 | −2.718 | 1.00 | 19.50 | S |
| ATOM | 4204 | CE | MET | A | 284 | −49.088 | 5.982 | −3.094 | 1.00 | 19.36 | C |
| ATOM | 4208 | C | MET | A | 284 | −49.575 | 7.848 | 1.115 | 1.00 | 18.95 | C |
| ATOM | 4209 | O | MET | A | 284 | −48.901 | 7.166 | 1.892 | 1.00 | 19.29 | O |
| ATOM | 4211 | N | PHE | A | 285 | −50.465 | 8.762 | 1.507 | 1.00 | 18.94 | N |
| ATOM | 4212 | CA | PHE | A | 285 | −50.671 | 9.082 | 2.930 | 1.00 | 19.26 | C |
| ATOM | 4214 | CB | PHE | A | 285 | −51.714 | 10.185 | 3.073 | 1.00 | 19.72 | C |
| ATOM | 4217 | CG | PHE | A | 285 | −51.575 | 11.016 | 4.328 | 1.00 | 21.97 | C |
| ATOM | 4218 | CD1 | PHE | A | 285 | −50.335 | 11.202 | 4.954 | 1.00 | 24.49 | C |
| ATOM | 4220 | CE1 | PHE | A | 285 | −50.209 | 11.996 | 6.086 | 1.00 | 25.11 | C |
| ATOM | 4222 | CZ | PHE | A | 285 | −51.321 | 12.634 | 6.597 | 1.00 | 26.40 | C |
| ATOM | 4224 | CE2 | PHE | A | 285 | −52.566 | 12.470 | 5.977 | 1.00 | 26.44 | C |
| ATOM | 4226 | CD2 | PHE | A | 285 | −52.678 | 11.670 | 4.846 | 1.00 | 24.55 | C |
| ATOM | 4228 | C | PHE | A | 285 | −51.097 | 7.879 | 3.770 | 1.00 | 18.74 | C |
| ATOM | 4229 | O | PHE | A | 285 | −50.700 | 7.729 | 4.924 | 1.00 | 18.31 | O |
| ATOM | 4231 | N | SER | A | 286 | −51.903 | 7.019 | 3.169 | 1.00 | 18.49 | N |
| ATOM | 4232 | CA | SER | A | 286 | −52.281 | 5.772 | 3.791 | 1.00 | 18.38 | C |
| ATOM | 4234 | CB | SER | A | 286 | −53.302 | 5.065 | 2.926 | 1.00 | 18.45 | C |
| ATOM | 4237 | OG | SER | A | 286 | −54.389 | 5.949 | 2.687 | 1.00 | 19.82 | O |
| ATOM | 4239 | C | SER | A | 286 | −51.070 | 4.888 | 4.048 | 1.00 | 18.08 | C |
| ATOM | 4240 | O | SER | A | 286 | −50.931 | 4.376 | 5.146 | 1.00 | 18.18 | O |
| ATOM | 4242 | N | PHE | A | 287 | −50.195 | 4.714 | 3.054 | 1.00 | 17.72 | N |
| ATOM | 4243 | CA | PHE | A | 287 | −48.911 | 4.024 | 3.279 | 1.00 | 17.23 | C |
| ATOM | 4245 | CB | PHE | A | 287 | −48.133 | 3.801 | 1.977 | 1.00 | 17.09 | C |
| ATOM | 4248 | CG | PHE | A | 287 | −48.513 | 2.555 | 1.258 | 1.00 | 17.26 | C |
| ATOM | 4249 | CD1 | PHE | A | 287 | −48.220 | 1.315 | 1.802 | 1.00 | 18.31 | C |
| ATOM | 4251 | CE1 | PHE | A | 287 | −48.583 | .129 | 1.131 | 1.00 | 18.47 | C |
| ATOM | 4253 | CZ | PHE | A | 287 | −49.237 | .198 | −.091 | 1.00 | 17.88 | C |
| ATOM | 4255 | CE2 | PHE | A | 287 | −49.530 | 1.441 | −.642 | 1.00 | 17.57 | C |
| ATOM | 4257 | CD2 | PHE | A | 287 | −49.168 | 2.608 | .031 | 1.00 | 17.79 | C |
| ATOM | 4259 | C | PHE | A | 287 | −48.022 | 4.787 | 4.277 | 1.00 | 16.92 | C |
| ATOM | 4260 | O | PHE | A | 287 | −47.369 | 4.173 | 5.143 | 1.00 | 17.18 | O |
| ATOM | 4262 | N | VAL | A | 288 | −47.989 | 6.113 | 4.174 | 1.00 | 16.00 | N |
| ATOM | 4263 | CA | VAL | A | 288 | −47.148 | 6.883 | 5.080 | 1.00 | 15.45 | C |
| ATOM | 4265 | CB | VAL | A | 288 | −47.289 | 8.399 | 4.863 | 1.00 | 15.21 | C |
| ATOM | 4267 | CG1 | VAL | A | 288 | −46.433 | 9.162 | 5.852 | 1.00 | 14.24 | C |
| ATOM | 4271 | CG2 | VAL | A | 288 | −46.898 | 8.757 | 3.450 | 1.00 | 14.46 | C |
| ATOM | 4275 | C | VAL | A | 288 | −47.479 | 6.499 | 6.527 | 1.00 | 15.46 | C |
| ATOM | 4276 | O | VAL | A | 288 | −46.590 | 6.160 | 7.299 | 1.00 | 14.79 | O |
| ATOM | 4278 | N | THR | A | 289 | −48.759 | 6.494 | 6.880 | 1.00 | 15.62 | N |
| ATOM | 4279 | CA | THR | A | 289 | −49.110 | 6.272 | 8.274 | 1.00 | 16.09 | C |
| ATOM | 4281 | CB | THR | A | 289 | −50.602 | 6.557 | 8.588 | 1.00 | 15.72 | C |
| ATOM | 4283 | OG1 | THR | A | 289 | −51.422 | 5.827 | 7.708 | 1.00 | 16.52 | O |
| ATOM | 4285 | CG2 | THR | A | 289 | −50.927 | 8.007 | 8.371 | 1.00 | 16.56 | C |
| ATOM | 4289 | C | THR | A | 289 | −48.677 | 4.879 | 8.727 | 1.00 | 16.34 | C |
| ATOM | 4290 | O | THR | A | 289 | −48.234 | 4.707 | 9.881 | 1.00 | 16.68 | O |
| ATOM | 4292 | N | ILE | A | 290 | −48.737 | 3.904 | 7.820 | 1.00 | 16.29 | N |
| ATOM | 4293 | CA | ILE | A | 290 | −48.347 | 2.538 | 8.166 | 1.00 | 16.56 | C |
| ATOM | 4295 | CB | ILE | A | 290 | −48.734 | 1.516 | 7.096 | 1.00 | 16.48 | C |
| ATOM | 4297 | CG1 | ILE | A | 290 | −50.247 | 1.440 | 6.944 | 1.00 | 16.91 | C |
| ATOM | 4300 | CD1 | ILE | A | 290 | −50.677 | .564 | 5.811 | 1.00 | 16.52 | C |
| ATOM | 4304 | CG2 | ILE | A | 290 | −48.262 | .145 | 7.488 | 1.00 | 16.52 | C |
| ATOM | 4308 | C | ILE | A | 290 | −46.842 | 2.456 | 8.402 | 1.00 | 16.94 | C |
| ATOM | 4309 | O | ILE | A | 290 | −46.404 | 1.968 | 9.443 | 1.00 | 17.06 | O |
| ATOM | 4311 | N | ILE | A | 291 | −46.048 | 2.942 | 7.451 | 1.00 | 17.22 | N |

TABLE 3-7-continued

Coordinates of *P. tremuloides* IspS

| ATOM | 4312 | CA | ILE | A | 291 | −44.595 | 2.969 | 7.640 | 1.00 | 17.20 | C |
|---|---|---|---|---|---|---|---|---|---|---|---|
| ATOM | 4314 | CB | ILE | A | 291 | −43.842 | 3.534 | 6.405 | 1.00 | 17.32 | C |
| ATOM | 4316 | CG1 | ILE | A | 291 | −44.172 | 2.744 | 5.125 | 1.00 | 17.61 | C |
| ATOM | 4319 | CD1 | ILE | A | 291 | −44.004 | 1.265 | 5.250 | 1.00 | 18.21 | C |
| ATOM | 4323 | CG2 | ILE | A | 291 | −42.336 | 3.550 | 6.637 | 1.00 | 16.64 | C |
| ATOM | 4327 | C | ILE | A | 291 | −44.262 | 3.794 | 8.886 | 1.00 | 17.36 | C |
| ATOM | 4328 | O | ILE | A | 291 | −43.420 | 3.413 | 9.670 | 1.00 | 17.06 | O |
| ATOM | 4330 | N | ASP | A | 292 | −44.950 | 4.906 | 9.093 | 1.00 | 18.12 | N |
| ATOM | 4331 | CA | ASP | A | 292 | −44.627 | 5.755 | 10.227 | 1.00 | 18.83 | C |
| ATOM | 4333 | CB | ASP | A | 292 | −45.511 | 7.017 | 10.285 | 1.00 | 19.22 | C |
| ATOM | 4336 | CG | ASP | A | 292 | −45.185 | 7.920 | 11.485 | 1.00 | 19.93 | C |
| ATOM | 4337 | OD1 | ASP | A | 292 | −44.062 | 8.460 | 11.544 | 1.00 | 21.80 | O |
| ATOM | 4338 | OD2 | ASP | A | 292 | −46.048 | 8.080 | 12.375 | 1.00 | 20.46 | O |
| ATOM | 4339 | C | ASP | A | 292 | −44.745 | 4.947 | 11.509 | 1.00 | 18.96 | C |
| ATOM | 4340 | O | ASP | A | 292 | −43.902 | 5.094 | 12.394 | 1.00 | 19.05 | O |
| ATOM | 4342 | N | ASP | A | 293 | −45.774 | 4.097 | 11.610 | 1.00 | 19.05 | N |
| ATOM | 4343 | CA | ASP | A | 293 | −45.951 | 3.273 | 12.817 | 1.00 | 18.99 | C |
| ATOM | 4345 | CB | ASP | A | 293 | −47.237 | 2.443 | 12.790 | 1.00 | 18.95 | C |
| ATOM | 4348 | CG | ASP | A | 293 | −48.496 | 3.272 | 12.921 | 1.00 | 19.27 | C |
| ATOM | 4349 | OD1 | ASP | A | 293 | −48.483 | 4.361 | 13.523 | 1.00 | 21.51 | O |
| ATOM | 4350 | OD2 | ASP | A | 293 | −49.536 | 2.812 | 12.421 | 1.00 | 19.61 | O |
| ATOM | 4351 | C | ASP | A | 293 | −44.783 | 2.322 | 12.935 | 1.00 | 19.07 | C |
| ATOM | 4352 | O | ASP | A | 293 | −44.244 | 2.135 | 14.024 | 1.00 | 19.35 | O |
| ATOM | 4354 | N | ILE | A | 294 | −44.390 | 1.730 | 11.805 | 1.00 | 19.10 | N |
| ATOM | 4355 | CA | ILE | A | 294 | −43.320 | .727 | 11.786 | 1.00 | 19.04 | C |
| ATOM | 4357 | CB | ILE | A | 294 | −43.137 | .109 | 10.386 | 1.00 | 18.49 | C |
| ATOM | 4359 | CG1 | ILE | A | 294 | −44.343 | −.754 | 10.038 | 1.00 | 17.60 | C |
| ATOM | 4362 | CD1 | ILE | A | 294 | −44.204 | −1.504 | 8.752 | 1.00 | 16.77 | C |
| ATOM | 4366 | CG2 | ILE | A | 294 | −41.895 | −.745 | 10.348 | 1.00 | 18.77 | C |
| ATOM | 4370 | C | ILE | A | 294 | −41.974 | 1.273 | 12.298 | 1.00 | 19.55 | C |
| ATOM | 4371 | O | ILE | A | 294 | −41.234 | .550 | 12.974 | 1.00 | 19.75 | O |
| ATOM | 4373 | N | TYR | A | 295 | −41.649 | 2.525 | 11.983 | 1.00 | 19.75 | N |
| ATOM | 4374 | CA | TYR | A | 295 | −40.411 | 3.103 | 12.476 | 1.00 | 19.91 | C |
| ATOM | 4376 | CB | TYR | A | 295 | −39.856 | 4.178 | 11.542 | 1.00 | 19.66 | C |
| ATOM | 4379 | CG | TYR | A | 295 | −39.206 | 3.695 | 10.245 | 1.00 | 18.19 | C |
| ATOM | 4380 | CD1 | TYR | A | 295 | −37.821 | 3.727 | 10.075 | 1.00 | 16.19 | C |
| ATOM | 4382 | CE1 | TYR | A | 295 | −37.222 | 3.331 | 8.882 | 1.00 | 14.68 | C |
| ATOM | 4384 | CZ | TYR | A | 295 | −38.004 | 2.906 | 7.828 | 1.00 | 15.04 | C |
| ATOM | 4385 | OH | TYR | A | 295 | −37.428 | 2.485 | 6.631 | 1.00 | 12.25 | O |
| ATOM | 4387 | CE2 | TYR | A | 295 | −39.383 | 2.871 | 7.975 | 1.00 | 16.48 | C |
| ATOM | 4389 | CD2 | TYR | A | 295 | −39.975 | 3.271 | 9.172 | 1.00 | 17.01 | C |
| ATOM | 4391 | C | TYR | A | 295 | −40.647 | 3.677 | 13.858 | 1.00 | 20.73 | C |
| ATOM | 4392 | O | TYR | A | 295 | −39.749 | 3.635 | 14.717 | 1.00 | 21.64 | O |
| ATOM | 4394 | N | ASP | A | 296 | −41.843 | 4.200 | 14.103 | 1.00 | 21.38 | N |
| ATOM | 4395 | CA | ASP | A | 296 | −42.100 | 4.865 | 15.391 | 1.00 | 22.20 | C |
| ATOM | 4397 | CB | ASP | A | 296 | −43.421 | 5.644 | 15.391 | 1.00 | 22.69 | C |
| ATOM | 4400 | CG | ASP | A | 296 | −43.567 | 6.548 | 16.607 | 1.00 | 23.85 | C |
| ATOM | 4401 | OD1 | ASP | A | 296 | −42.568 | 7.179 | 17.014 | 1.00 | 25.49 | O |
| ATOM | 4402 | OD2 | ASP | A | 296 | −44.689 | 6.648 | 17.145 | 1.00 | 26.12 | O |
| ATOM | 4403 | C | ASP | A | 296 | −42.106 | 3.890 | 16.549 | 1.00 | 22.10 | C |
| ATOM | 4404 | O | ASP | A | 296 | −41.376 | 4.082 | 17.506 | 1.00 | 22.14 | O |
| ATOM | 4406 | N | VAL | A | 297 | −42.900 | 2.828 | 16.435 | 1.00 | 22.25 | N |
| ATOM | 4407 | CA | VAL | A | 297 | −43.163 | 1.937 | 17.570 | 1.00 | 22.22 | C |
| ATOM | 4409 | CB | VAL | A | 297 | −44.635 | 2.116 | 18.057 | 1.00 | 22.07 | C |
| ATOM | 4411 | CG1 | VAL | A | 297 | −44.958 | 3.587 | 18.215 | 1.00 | 21.63 | C |
| ATOM | 4415 | CG2 | VAL | A | 297 | −45.618 | 1.459 | 17.099 | 1.00 | 20.76 | C |
| ATOM | 4419 | C | VAL | A | 297 | −42.861 | .422 | 17.373 | 1.00 | 22.49 | C |
| ATOM | 4420 | O | VAL | A | 297 | −42.517 | −.255 | 18.343 | 1.00 | 22.40 | O |
| ATOM | 4422 | N | TYR | A | 298 | −42.990 | −.117 | 16.157 | 1.00 | 22.69 | N |
| ATOM | 4423 | CA | TYR | A | 298 | −43.065 | −1.579 | 15.993 | 1.00 | 22.90 | C |
| ATOM | 4425 | CB | TYR | A | 298 | −44.089 | −1.974 | 14.934 | 1.00 | 22.77 | C |
| ATOM | 4428 | CG | TYR | A | 298 | −44.341 | −3.469 | 14.932 | 1.00 | 23.74 | C |
| ATOM | 4429 | CD1 | TYR | A | 298 | −45.249 | −4.043 | 15.819 | 1.00 | 25.72 | C |
| ATOM | 4431 | CE1 | TYR | A | 298 | −45.484 | −5.435 | 15.833 | 1.00 | 26.12 | C |
| ATOM | 4433 | CZ | TYR | A | 298 | −44.798 | −6.247 | 14.954 | 1.00 | 25.59 | C |
| ATOM | 4434 | OH | TYR | A | 298 | −45.027 | −7.593 | 14.970 | 1.00 | 25.33 | O |
| ATOM | 4436 | CE2 | TYR | A | 298 | −43.890 | −5.702 | 14.062 | 1.00 | 24.79 | C |
| ATOM | 4438 | CD2 | TYR | A | 298 | −43.661 | −4.317 | 14.061 | 1.00 | 24.20 | C |
| ATOM | 4440 | C | TYR | A | 298 | −41.750 | −2.258 | 15.649 | 1.00 | 23.02 | C |
| ATOM | 4441 | O | TYR | A | 298 | −41.387 | −3.257 | 16.256 | 1.00 | 22.80 | O |
| ATOM | 4443 | N | GLY | A | 299 | −41.069 | −1.747 | 14.634 | 1.00 | 23.47 | N |
| ATOM | 4444 | CA | GLY | A | 299 | −39.839 | −2.361 | 14.149 | 1.00 | 23.36 | C |
| ATOM | 4447 | C | GLY | A | 299 | −38.631 | −1.978 | 14.984 | 1.00 | 23.27 | C |
| ATOM | 4448 | O | GLY | A | 299 | −38.532 | −.858 | 15.501 | 1.00 | 23.35 | O |
| ATOM | 4450 | N | THR | A | 300 | −37.702 | −2.918 | 15.098 | 1.00 | 23.11 | N |
| ATOM | 4451 | CA | THR | A | 300 | −36.459 | −2.682 | 15.797 | 1.00 | 22.90 | C |
| ATOM | 4453 | CB | THR | A | 300 | −35.869 | −3.957 | 16.386 | 1.00 | 22.83 | C |
| ATOM | 4455 | OG1 | THR | A | 300 | −35.328 | −4.756 | 15.328 | 1.00 | 22.61 | O |

TABLE 3-7-continued

| | | | | | | | | | | |
|---|---|---|---|---|---|---|---|---|---|---|
| ATOM | 4457 | CG2 | THR | A | 300 | −36.928 | −4.732 | 17.162 | 1.00 | 22.18 C |
| ATOM | 4461 | C | THR | A | 300 | −35.482 | −2.120 | 14.796 | 1.00 | 23.00 C |
| ATOM | 4462 | O | THR | A | 300 | −35.606 | −2.364 | 13.602 | 1.00 | 23.13 O |
| ATOM | 4464 | N | LEU | A | 301 | −34.496 | −1.394 | 15.309 | 1.00 | 23.07 N |
| ATOM | 4465 | CA | LEU | A | 301 | −33.596 | −.572 | 14.498 | 1.00 | 22.84 C |
| ATOM | 4467 | CB | LEU | A | 301 | −32.515 | .007 | 15.403 | 1.00 | 22.80 C |
| ATOM | 4470 | CG | LEU | A | 301 | −31.965 | 1.412 | 15.182 | 1.00 | 22.39 C |
| ATOM | 4472 | CD1 | LEU | A | 301 | −32.983 | 2.365 | 14.587 | 1.00 | 22.44 C |
| ATOM | 4476 | CD2 | LEU | A | 301 | −31.482 | 1.919 | 16.536 | 1.00 | 22.19 C |
| ATOM | 4480 | C | LEU | A | 301 | −32.964 | −1.358 | 13.361 | 1.00 | 22.95 C |
| ATOM | 4481 | O | LEU | A | 301 | −32.910 | −.888 | 12.232 | 1.00 | 22.50 O |
| ATOM | 4483 | N | ASP | A | 302 | −32.511 | −2.569 | 13.673 | 1.00 | 23.35 N |
| ATOM | 4484 | CA | ASP | A | 302 | −31.929 | −3.469 | 12.670 | 1.00 | 23.65 C |
| ATOM | 4486 | CB | ASP | A | 302 | −31.332 | −4.747 | 13.328 | 1.00 | 24.12 C |
| ATOM | 4489 | CG | ASP | A | 302 | −29.984 | −4.498 | 14.057 | 1.00 | 25.23 C |
| ATOM | 4490 | OD1 | ASP | A | 302 | −29.003 | −4.051 | 13.409 | 1.00 | 26.43 O |
| ATOM | 4491 | OD2 | ASP | A | 302 | −29.896 | −4.780 | 15.277 | 1.00 | 26.92 O |
| ATOM | 4492 | C | ASP | A | 302 | −32.945 | −3.859 | 11.581 | 1.00 | 23.11 C |
| ATOM | 4493 | O | ASP | A | 302 | −32.544 | −4.086 | 10.445 | 1.00 | 23.05 O |
| ATOM | 4495 | N | GLU | A | 303 | −34.235 | −3.965 | 11.927 | 1.00 | 22.63 N |
| ATOM | 4496 | CA | GLU | A | 303 | −35.295 | −4.248 | 10.931 | 1.00 | 22.40 C |
| ATOM | 4498 | CB | GLU | A | 303 | −36.625 | −4.675 | 11.589 | 1.00 | 22.20 C |
| ATOM | 4501 | CG | GLU | A | 303 | −36.537 | −5.956 | 12.426 | 1.00 | 22.66 C |
| ATOM | 4504 | CD | GLU | A | 303 | −37.832 | −6.341 | 13.159 | 1.00 | 22.69 C |
| ATOM | 4505 | OE1 | GLU | A | 303 | −38.614 | −5.449 | 13.568 | 1.00 | 22.23 O |
| ATOM | 4506 | OE2 | GLU | A | 303 | −38.051 | −7.558 | 13.338 | 1.00 | 21.64 O |
| ATOM | 4507 | C | GLU | A | 303 | −35.533 | −3.017 | 10.067 | 1.00 | 22.35 C |
| ATOM | 4508 | O | GLU | A | 303 | −35.658 | −3.105 | 8.841 | 1.00 | 22.27 O |
| ATOM | 4510 | N | LEU | A | 304 | −35.597 | −1.866 | 10.724 | 1.00 | 22.34 N |
| ATOM | 4511 | CA | LEU | A | 304 | −35.776 | −.607 | 10.040 | 1.00 | 22.26 C |
| ATOM | 4513 | CB | LEU | A | 304 | −35.861 | .537 | 11.052 | 1.00 | 22.49 C |
| ATOM | 4516 | CG | LEU | A | 304 | −37.089 | .517 | 11.973 | 1.00 | 23.05 C |
| ATOM | 4518 | CD1 | LEU | A | 304 | −37.109 | 1.708 | 12.932 | 1.00 | 23.46 C |
| ATOM | 4522 | CD2 | LEU | A | 304 | −38.353 | .511 | 11.142 | 1.00 | 23.96 C |
| ATOM | 4526 | C | LEU | A | 304 | −34.634 | −.383 | 9.063 | 1.00 | 22.09 C |
| ATOM | 4527 | O | LEU | A | 304 | −34.873 | .094 | 7.969 | 1.00 | 22.32 O |
| ATOM | 4529 | N | GLU | A | 305 | −33.408 | −.740 | 9.450 | 1.00 | 21.91 N |
| ATOM | 4530 | CA | GLU | A | 305 | −32.259 | −.685 | 8.541 | 1.00 | 21.93 C |
| ATOM | 4532 | CB | GLU | A | 305 | −30.988 | −1.194 | 9.219 | 1.00 | 22.35 C |
| ATOM | 4535 | CG | GLU | A | 305 | −30.363 | −.258 | 10.249 | 1.00 | 24.12 C |
| ATOM | 4538 | CD | GLU | A | 305 | −29.751 | 1.002 | 9.649 | 1.00 | 26.11 C |
| ATOM | 4539 | OE1 | GLU | A | 305 | −29.275 | 1.846 | 10.454 | 1.00 | 25.68 O |
| ATOM | 4540 | OE2 | GLU | A | 305 | −29.756 | 1.146 | 8.391 | 1.00 | 27.67 O |
| ATOM | 4541 | C | GLU | A | 305 | −32.475 | −1.524 | 7.295 | 1.00 | 21.54 C |
| ATOM | 4542 | O | GLU | A | 305 | −32.010 | −1.162 | 6.220 | 1.00 | 21.75 O |
| ATOM | 4544 | N | LEU | A | 306 | −33.155 | −2.660 | 7.448 | 1.00 | 21.21 N |
| ATOM | 4545 | CA | LEU | A | 306 | −33.459 | −3.557 | 6.316 | 1.00 | 20.66 C |
| ATOM | 4547 | CB | LEU | A | 306 | −33.880 | −4.956 | 6.795 | 1.00 | 20.26 C |
| ATOM | 4550 | CG | LEU | A | 306 | −32.725 | −5.854 | 7.220 | 1.00 | 19.57 C |
| ATOM | 4552 | CD1 | LEU | A | 306 | −33.261 | −7.150 | 7.777 | 1.00 | 20.18 C |
| ATOM | 4556 | CD2 | LEU | A | 306 | −31.791 | −6.120 | 6.061 | 1.00 | 18.29 C |
| ATOM | 4560 | C | LEU | A | 306 | −34.535 | −2.967 | 5.416 | 1.00 | 20.23 C |
| ATOM | 4561 | O | LEU | A | 306 | −34.412 | −2.966 | 4.197 | 1.00 | 19.97 O |
| ATOM | 4563 | N | PHE | A | 307 | −35.588 | −2.457 | 6.023 | 1.00 | 19.99 N |
| ATOM | 4564 | CA | PHE | A | 307 | −36.635 | −1.861 | 5.237 | 1.00 | 20.00 C |
| ATOM | 4566 | CB | PHE | A | 307 | −37.771 | −1.388 | 6.118 | 1.00 | 20.08 C |
| ATOM | 4569 | CG | PHE | A | 307 | −39.011 | −1.115 | 5.370 | 1.00 | 19.05 C |
| ATOM | 4570 | CD1 | PHE | A | 307 | −39.895 | −2.118 | 5.119 | 1.00 | 18.77 C |
| ATOM | 4572 | CE1 | PHE | A | 307 | −41.037 | −1.873 | 4.421 | 1.00 | 20.07 C |
| ATOM | 4574 | CZ | PHE | A | 307 | −41.296 | −.621 | 3.959 | 1.00 | 19.63 C |
| ATOM | 4576 | CE2 | PHE | A | 307 | −40.411 | .391 | 4.199 | 1.00 | 19.27 C |
| ATOM | 4578 | CD2 | PHE | A | 307 | −39.278 | .142 | 4.900 | 1.00 | 19.17 C |
| ATOM | 4580 | C | PHE | A | 307 | −36.087 | −.695 | 4.447 | 1.00 | 20.25 C |
| ATOM | 4581 | O | PHE | A | 307 | −36.356 | −.589 | 3.242 | 1.00 | 20.08 O |
| ATOM | 4583 | N | THR | A | 308 | −35.325 | .167 | 5.137 | 1.00 | 20.51 N |
| ATOM | 4584 | CA | THR | A | 308 | −34.737 | 1.379 | 4.538 | 1.00 | 20.60 C |
| ATOM | 4586 | CB | THR | A | 308 | −33.860 | 2.177 | 5.541 | 1.00 | 20.41 C |
| ATOM | 4588 | OG1 | THR | A | 308 | −34.672 | 2.661 | 6.611 | 1.00 | 20.05 O |
| ATOM | 4590 | CG2 | THR | A | 308 | −33.198 | 3.376 | 4.864 | 1.00 | 20.38 C |
| ATOM | 4594 | C | THR | A | 308 | −33.895 | 1.009 | 3.331 | 1.00 | 20.82 C |
| ATOM | 4595 | O | THR | A | 308 | −34.057 | 1.571 | 2.243 | 1.00 | 20.45 O |
| ATOM | 4597 | N | ASP | A | 309 | −33.020 | .031 | 3.522 | 1.00 | 21.32 N |
| ATOM | 4598 | CA | ASP | A | 309 | −32.138 | −.399 | 2.449 | 1.00 | 21.88 C |
| ATOM | 4600 | CB | ASP | A | 309 | −31.042 | −1.324 | 2.971 | 1.00 | 22.44 C |
| ATOM | 4603 | CG | ASP | A | 309 | −30.164 | −1.847 | 1.857 | 1.00 | 25.69 C |
| ATOM | 4604 | OD1 | ASP | A | 309 | −29.599 | −1.010 | 1.089 | 1.00 | 28.02 O |
| ATOM | 4605 | OD2 | ASP | A | 309 | −30.076 | −3.100 | 1.730 | 1.00 | 30.59 O |
| ATOM | 4606 | C | ASP | A | 309 | −32.928 | −1.085 | 1.357 | 1.00 | 21.17 C |

TABLE 3-7-continued

Coordinates of *P. tremuloides* IspS

| ATOM | 4607 | O | ASP | A | 309 | −32.601 | −.948 | .188 | 1.00 | 20.95 | O |
|---|---|---|---|---|---|---|---|---|---|---|---|
| ATOM | 4609 | N | ALA | A | 310 | −33.965 | −1.818 | 1.757 | 1.00 | 20.99 | N |
| ATOM | 4610 | CA | ALA | A | 310 | −34.885 | −2.474 | .828 | 1.00 | 20.91 | C |
| ATOM | 4612 | CB | ALA | A | 310 | −35.931 | −3.244 | 1.591 | 1.00 | 20.77 | C |
| ATOM | 4616 | C | ALA | A | 310 | −35.567 | −1.501 | −.123 | 1.00 | 21.08 | C |
| ATOM | 4617 | O | ALA | A | 310 | −35.745 | −1.816 | −1.305 | 1.00 | 20.76 | O |
| ATOM | 4619 | N | VAL | A | 311 | −35.958 | −.334 | .402 | 1.00 | 21.51 | N |
| ATOM | 4620 | CA | VAL | A | 311 | −36.594 | .719 | −.396 | 1.00 | 21.50 | C |
| ATOM | 4622 | CB | VAL | A | 311 | −37.424 | 1.715 | .477 | 1.00 | 21.73 | C |
| ATOM | 4624 | CG1 | VAL | A | 311 | −38.724 | 1.076 | .941 | 1.00 | 21.01 | C |
| ATOM | 4628 | CG2 | VAL | A | 311 | −37.765 | 2.993 | −.292 | 1.00 | 21.88 | C |
| ATOM | 4632 | C | VAL | A | 311 | −35.553 | 1.445 | −1.230 | 1.00 | 21.67 | C |
| ATOM | 4633 | O | VAL | A | 311 | −35.811 | 1.728 | −2.389 | 1.00 | 21.71 | O |
| ATOM | 4635 | N | GLU | A | 312 | −34.381 | 1.724 | −.663 | 1.00 | 22.25 | N |
| ATOM | 4636 | CA | GLU | A | 312 | −33.248 | 2.284 | −1.443 | 1.00 | 23.00 | C |
| ATOM | 4638 | CB | GLU | A | 312 | −31.951 | 2.331 | −.608 | 1.00 | 23.36 | C |
| ATOM | 4641 | CG | GLU | A | 312 | −31.897 | 3.383 | .511 | 1.00 | 24.72 | C |
| ATOM | 4644 | CD | GLU | A | 312 | −30.526 | 3.469 | 1.189 | 1.00 | 27.09 | C |
| ATOM | 4645 | OE1 | GLU | A | 312 | −30.083 | 4.608 | 1.458 | 1.00 | 30.07 | O |
| ATOM | 4646 | OE2 | GLU | A | 312 | −29.885 | 2.418 | 1.454 | 1.00 | 27.86 | O |
| ATOM | 4647 | C | GLU | A | 312 | −32.954 | 1.498 | −2.731 | 1.00 | 23.13 | C |
| ATOM | 4648 | O | GLU | A | 312 | −32.851 | 2.064 | −3.803 | 1.00 | 22.88 | O |
| ATOM | 4650 | N | ARG | A | 313 | −32.819 | .188 | −2.615 | 1.00 | 23.74 | N |
| ATOM | 4651 | CA | ARG | A | 313 | −32.400 | −.628 | −3.743 | 1.00 | 24.46 | C |
| ATOM | 4653 | CB | ARG | A | 313 | −31.758 | −1.916 | −3.232 | 1.00 | 25.01 | C |
| ATOM | 4656 | CG | ARG | A | 313 | −30.421 | −1.667 | −2.481 | 1.00 | 27.74 | C |
| ATOM | 4659 | CD | ARG | A | 313 | −29.715 | −2.963 | −2.072 | 1.00 | 31.41 | C |
| ATOM | 4662 | NE | ARG | A | 313 | −30.675 | −3.921 | −1.499 | 1.00 | 34.94 | N |
| ATOM | 4664 | CZ | ARG | A | 313 | −31.203 | −4.974 | −2.138 | 1.00 | 37.87 | C |
| ATOM | 4665 | NH1 | ARG | A | 313 | −30.861 | −5.282 | −3.402 | 1.00 | 38.35 | N |
| ATOM | 4668 | NH2 | ARG | A | 313 | −32.079 | −5.746 | −1.495 | 1.00 | 38.82 | N |
| ATOM | 4671 | C | ARG | A | 313 | −33.523 | −.914 | −4.739 | 1.00 | 24.27 | C |
| ATOM | 4672 | O | ARG | A | 313 | −33.257 | −1.178 | −5.898 | 1.00 | 24.17 | O |
| ATOM | 4674 | N | TRP | A | 314 | −34.770 | −.873 | −4.282 | 1.00 | 24.59 | N |
| ATOM | 4675 | CA | TRP | A | 314 | −35.939 | −1.042 | −5.142 | 1.00 | 24.66 | C |
| ATOM | 4677 | CB | TRP | A | 314 | −36.175 | .234 | −5.961 | 1.00 | 24.39 | C |
| ATOM | 4680 | CG | TRP | A | 314 | −37.575 | .382 | −6.386 | 1.00 | 22.61 | C |
| ATOM | 4681 | CD1 | TRP | A | 314 | −38.073 | .204 | −7.635 | 1.00 | 21.66 | C |
| ATOM | 4683 | NE1 | TRP | A | 314 | −39.429 | .403 | −7.634 | 1.00 | 21.42 | N |
| ATOM | 4685 | CE2 | TRP | A | 314 | −39.829 | .707 | −6.360 | 1.00 | 20.99 | C |
| ATOM | 4686 | CD2 | TRP | A | 314 | −38.683 | .701 | −5.550 | 1.00 | 21.41 | C |
| ATOM | 4687 | CE3 | TRP | A | 314 | −38.817 | .991 | −4.191 | 1.00 | 21.48 | C |
| ATOM | 4689 | CZ3 | TRP | A | 314 | −40.080 | 1.277 | −3.693 | 1.00 | 21.38 | C |
| ATOM | 4691 | CH2 | TRP | A | 314 | −41.204 | 1.269 | −4.523 | 1.00 | 20.84 | C |
| ATOM | 4693 | CZ2 | TRP | A | 314 | −41.099 | .985 | −5.857 | 1.00 | 20.87 | C |
| ATOM | 4695 | C | TRP | A | 314 | −35.831 | −2.286 | −6.038 | 1.00 | 25.65 | C |
| ATOM | 4696 | O | TRP | A | 314 | −36.069 | −2.238 | −7.259 | 1.00 | 25.69 | O |
| ATOM | 4698 | N | ASP | A | 315 | −35.480 | −3.400 | −5.404 | 1.00 | 26.79 | N |
| ATOM | 4699 | CA | ASP | A | 315 | −35.253 | −4.667 | −6.087 | 1.00 | 28.01 | C |
| ATOM | 4701 | CB | ASP | A | 315 | −33.801 | −5.097 | −5.890 | 1.00 | 28.07 | C |
| ATOM | 4704 | CG | ASP | A | 315 | −33.553 | −6.536 | −6.296 | 1.00 | 29.92 | C |
| ATOM | 4705 | OD1 | ASP | A | 315 | −34.262 | −7.026 | −7.197 | 1.00 | 32.58 | O |
| ATOM | 4706 | OD2 | ASP | A | 315 | −32.648 | −7.194 | −5.722 | 1.00 | 32.73 | O |
| ATOM | 4707 | C | ASP | A | 315 | −36.202 | −5.710 | −5.518 | 1.00 | 28.91 | C |
| ATOM | 4708 | O | ASP | A | 315 | −36.019 | −6.163 | −4.399 | 1.00 | 29.17 | O |
| ATOM | 4710 | N | VAL | A | 316 | −37.218 | −6.091 | −6.283 | 1.00 | 30.25 | N |
| ATOM | 4711 | CA | VAL | A | 316 | −38.233 | −7.012 | −5.778 | 1.00 | 31.47 | C |
| ATOM | 4713 | CB | VAL | A | 316 | −39.396 | −7.156 | −6.755 | 1.00 | 31.56 | C |
| ATOM | 4715 | CG1 | VAL | A | 316 | −40.668 | −7.590 | −6.027 | 1.00 | 30.99 | C |
| ATOM | 4719 | CG2 | VAL | A | 316 | −39.033 | −8.141 | −7.862 | 1.00 | 31.84 | C |
| ATOM | 4723 | C | VAL | A | 316 | −37.663 | −8.405 | −5.540 | 1.00 | 32.86 | C |
| ATOM | 4724 | O | VAL | A | 316 | −38.170 | −9.153 | −4.708 | 1.00 | 32.99 | O |
| ATOM | 4726 | N | ASN | A | 317 | −36.607 | −8.750 | −6.278 | 1.00 | 34.55 | N |
| ATOM | 4727 | CA | ASN | A | 317 | −35.940 | −10.060 | −6.160 | 1.00 | 35.53 | C |
| ATOM | 4729 | CB | ASN | A | 317 | −35.013 | −10.298 | −7.367 | 1.00 | 35.68 | C |
| ATOM | 4732 | CG | ASN | A | 317 | −35.752 | −10.264 | −8.713 | 1.00 | 35.92 | C |
| ATOM | 4733 | OD1 | ASN | A | 317 | −36.634 | −11.092 | −8.971 | 1.00 | 36.95 | O |
| ATOM | 4734 | ND2 | ASN | A | 317 | −35.368 | −9.323 | −9.585 | 1.00 | 34.17 | N |
| ATOM | 4737 | C | ASN | A | 317 | −35.126 | −10.225 | −4.871 | 1.00 | 36.40 | C |
| ATOM | 4738 | O | ASN | A | 317 | −34.385 | −11.195 | −4.747 | 1.00 | 36.47 | O |
| ATOM | 4740 | N | ALA | A | 318 | −35.239 | −9.265 | −3.944 | 1.00 | 37.52 | N |
| ATOM | 4741 | CA | ALA | A | 318 | −34.614 | −9.335 | −2.613 | 1.00 | 38.45 | C |
| ATOM | 4743 | CB | ALA | A | 318 | −33.371 | −8.465 | −2.557 | 1.00 | 38.43 | C |
| ATOM | 4747 | C | ALA | A | 318 | −35.631 | −8.902 | −1.554 | 1.00 | 39.28 | C |
| ATOM | 4748 | O | ALA | A | 318 | −35.361 | −8.094 | −.662 | 1.00 | 39.55 | O |
| ATOM | 4750 | N | ILE | A | 319 | −36.823 | −9.456 | −1.698 | 1.00 | 40.17 | N |
| ATOM | 4751 | CA | ILE | A | 319 | −37.905 | −9.310 | −.740 | 1.00 | 40.49 | C |
| ATOM | 4753 | CB | ILE | A | 319 | −39.275 | −9.588 | −1.469 | 1.00 | 40.64 | C |

TABLE 3-7-continued

Coordinates of *P. tremuloides* IspS

| ATOM | 4755 | CG1 | ILE | A | 319 | −40.473 | −9.078 | −.683 | 1.00 | 40.88 | C |
|------|------|-----|-----|---|-----|---------|--------|-------|------|-------|---|
| ATOM | 4758 | CD1 | ILE | A | 319 | −41.799 | −9.535 | −1.280 | 1.00 | 40.86 | C |
| ATOM | 4762 | CG2 | ILE | A | 319 | −39.460 | −11.082 | −1.801 | 1.00 | 40.50 | C |
| ATOM | 4766 | C | ILE | A | 319 | −37.656 | −10.319 | .393 | 1.00 | 40.69 | C |
| ATOM | 4767 | O | ILE | A | 319 | −38.136 | −10.138 | 1.504 | 1.00 | 40.88 | O |
| ATOM | 4769 | N | ASN | A | 320 | −36.886 | −11.374 | .104 | 1.00 | 40.79 | N |
| ATOM | 4770 | CA | ASN | A | 320 | −36.689 | −12.483 | 1.049 | 1.00 | 40.64 | C |
| ATOM | 4772 | CB | ASN | A | 320 | −36.240 | −13.761 | .314 | 1.00 | 40.73 | C |
| ATOM | 4775 | CG | ASN | A | 320 | −37.370 | −14.422 | −.468 | 1.00 | 40.98 | C |
| ATOM | 4776 | OD1 | ASN | A | 320 | −38.556 | −14.309 | −.119 | 1.00 | 40.77 | O |
| ATOM | 4777 | ND2 | ASN | A | 320 | −37.001 | −15.131 | −1.529 | 1.00 | 41.31 | N |
| ATOM | 4780 | C | ASN | A | 320 | −35.711 | −12.175 | 2.169 | 1.00 | 40.16 | C |
| ATOM | 4781 | O | ASN | A | 320 | −35.546 | −12.978 | 3.077 | 1.00 | 40.15 | O |
| ATOM | 4783 | N | ASP | A | 321 | −35.067 | −11.017 | 2.101 | 1.00 | 39.66 | N |
| ATOM | 4784 | CA | ASP | A | 321 | −34.111 | −10.615 | 3.126 | 1.00 | 39.51 | C |
| ATOM | 4786 | CB | ASP | A | 321 | −33.114 | −9.571 | 2.575 | 1.00 | 40.17 | C |
| ATOM | 4789 | CG | ASP | A | 321 | −32.595 | −9.904 | 1.152 | 1.00 | 42.12 | C |
| ATOM | 4790 | OD1 | ASP | A | 321 | −32.425 | −11.115 | .820 | 1.00 | 44.15 | O |
| ATOM | 4791 | OD2 | ASP | A | 321 | −32.354 | −8.934 | .375 | 1.00 | 43.28 | O |
| ATOM | 4792 | C | ASP | A | 321 | −34.851 | −10.030 | 4.337 | 1.00 | 38.27 | C |
| ATOM | 4793 | O | ASP | A | 321 | −34.304 | −9.987 | 5.443 | 1.00 | 38.15 | O |
| ATOM | 4795 | N | LEU | A | 322 | −36.089 | −9.583 | 4.108 | 1.00 | 36.72 | N |
| ATOM | 4796 | CA | LEU | A | 322 | −36.887 | −8.875 | 5.104 | 1.00 | 35.38 | C |
| ATOM | 4798 | CB | LEU | A | 322 | −37.894 | −7.942 | 4.422 | 1.00 | 35.15 | C |
| ATOM | 4801 | CG | LEU | A | 322 | −37.370 | −6.840 | 3.503 | 1.00 | 34.83 | C |
| ATOM | 4803 | CD1 | LEU | A | 322 | −38.479 | −6.286 | 2.626 | 1.00 | 34.45 | C |
| ATOM | 4807 | CD2 | LEU | A | 322 | −36.742 | −5.740 | 4.316 | 1.00 | 34.89 | C |
| ATOM | 4811 | C | LEU | A | 322 | −37.683 | −9.834 | 5.963 | 1.00 | 34.57 | C |
| ATOM | 4812 | O | LEU | A | 322 | −37.975 | −10.933 | 5.527 | 1.00 | 34.27 | O |
| ATOM | 4814 | N | PRO | A | 323 | −38.039 | −9.402 | 7.189 | 1.00 | 33.93 | N |
| ATOM | 4815 | CA | PRO | A | 323 | −39.070 | −9.917 | 8.067 | 1.00 | 33.49 | C |
| ATOM | 4817 | CB | PRO | A | 323 | −39.151 | −8.840 | 9.141 | 1.00 | 33.31 | C |
| ATOM | 4820 | CG | PRO | A | 323 | −37.791 | −8.419 | 9.311 | 1.00 | 33.67 | C |
| ATOM | 4823 | CD | PRO | A | 323 | −37.154 | −8.496 | 7.941 | 1.00 | 34.20 | C |
| ATOM | 4826 | C | PRO | A | 323 | −40.429 | −10.036 | 7.425 | 1.00 | 33.33 | C |
| ATOM | 4827 | O | PRO | A | 323 | −40.776 | −9.232 | 6.579 | 1.00 | 33.35 | O |
| ATOM | 4828 | N | ASP | A | 324 | −41.209 | −11.005 | 7.891 | 1.00 | 33.37 | N |
| ATOM | 4829 | CA | ASP | A | 324 | −42.511 | −11.329 | 7.313 | 1.00 | 33.36 | C |
| ATOM | 4831 | CB | ASP | A | 324 | −43.137 | −12.542 | 8.037 | 1.00 | 33.59 | C |
| ATOM | 4834 | CG | ASP | A | 324 | −42.496 | −13.881 | 7.619 | 1.00 | 34.18 | C |
| ATOM | 4835 | OD1 | ASP | A | 324 | −41.885 | −13.915 | 6.518 | 1.00 | 36.44 | O |
| ATOM | 4836 | OD2 | ASP | A | 324 | −42.607 | −14.887 | 8.371 | 1.00 | 32.19 | O |
| ATOM | 4837 | C | ASP | A | 324 | −43.484 | −10.149 | 7.289 | 1.00 | 32.90 | C |
| ATOM | 4838 | O | ASP | A | 324 | −44.108 | −9.885 | 6.255 | 1.00 | 33.36 | O |
| ATOM | 4840 | N | TYR | A | 325 | −43.606 | −9.423 | 8.392 | 1.00 | 32.10 | N |
| ATOM | 4841 | CA | TYR | A | 325 | −44.515 | −8.279 | 8.400 | 1.00 | 31.65 | C |
| ATOM | 4843 | CB | TYR | A | 325 | −44.718 | −7.726 | 9.815 | 1.00 | 31.68 | C |
| ATOM | 4846 | CG | TYR | A | 325 | −43.618 | −6.846 | 10.352 | 1.00 | 31.35 | C |
| ATOM | 4847 | CD1 | TYR | A | 325 | −42.507 | −7.389 | 10.992 | 1.00 | 31.31 | C |
| ATOM | 4849 | CE1 | TYR | A | 325 | −41.497 | −6.574 | 11.504 | 1.00 | 31.46 | C |
| ATOM | 4851 | CZ | TYR | A | 325 | −41.613 | −5.192 | 11.392 | 1.00 | 32.41 | C |
| ATOM | 4852 | OH | TYR | A | 325 | −40.637 | −4.336 | 11.893 | 1.00 | 32.78 | O |
| ATOM | 4854 | CE2 | TYR | A | 325 | −42.723 | −4.644 | 10.769 | 1.00 | 32.17 | C |
| ATOM | 4856 | CD2 | TYR | A | 325 | −43.713 | −5.470 | 10.261 | 1.00 | 31.47 | C |
| ATOM | 4858 | C | TYR | A | 325 | −44.094 | −7.179 | 7.424 | 1.00 | 31.17 | C |
| ATOM | 4859 | O | TYR | A | 325 | −44.947 | −6.458 | 6.920 | 1.00 | 31.09 | O |
| ATOM | 4861 | N | MET | A | 326 | −42.796 | −7.068 | 7.145 | 1.00 | 30.73 | N |
| ATOM | 4862 | CA | MET | A | 326 | −42.277 | −6.036 | 6.225 | 1.00 | 30.49 | C |
| ATOM | 4864 | CB | MET | A | 326 | −40.832 | −5.702 | 6.565 | 1.00 | 30.16 | C |
| ATOM | 4867 | CG | MET | A | 326 | −40.725 | −4.918 | 7.830 | 1.00 | 29.57 | C |
| ATOM | 4870 | SD | MET | A | 326 | −39.057 | −4.376 | 8.166 | 1.00 | 28.39 | S |
| ATOM | 4871 | CE | MET | A | 326 | −39.407 | −2.787 | 8.933 | 1.00 | 26.18 | C |
| ATOM | 4875 | C | MET | A | 326 | −42.371 | −6.418 | 4.748 | 1.00 | 30.59 | C |
| ATOM | 4876 | O | MET | A | 326 | −42.786 | −5.603 | 3.920 | 1.00 | 30.48 | O |
| ATOM | 4878 | N | LYS | A | 327 | −41.936 | −7.643 | 4.438 | 1.00 | 30.68 | N |
| ATOM | 4879 | CA | LYS | A | 327 | −42.170 | −8.299 | 3.143 | 1.00 | 30.56 | C |
| ATOM | 4881 | CB | LYS | A | 327 | −42.267 | −9.830 | 3.326 | 1.00 | 30.84 | C |
| ATOM | 4884 | CG | LYS | A | 327 | −41.052 | −10.607 | 2.844 | 1.00 | 32.35 | C |
| ATOM | 4887 | CD | LYS | A | 327 | −40.990 | −12.019 | 3.412 | 1.00 | 34.43 | C |
| ATOM | 4890 | CE | LYS | A | 327 | −40.221 | −12.941 | 2.462 | 1.00 | 35.77 | C |
| ATOM | 4893 | NZ | LYS | A | 327 | −39.691 | −14.162 | 3.150 | 1.00 | 37.20 | N |
| ATOM | 4897 | C | LYS | A | 327 | −43.453 | −7.811 | 2.515 | 1.00 | 29.89 | C |
| ATOM | 4898 | O | LYS | A | 327 | −43.447 | −7.220 | 1.436 | 1.00 | 29.85 | O |
| ATOM | 4900 | N | LEU | A | 328 | −44.544 | −8.046 | 3.230 | 1.00 | 29.10 | N |
| ATOM | 4901 | CA | LEU | A | 328 | −45.871 | −7.781 | 2.730 | 1.00 | 28.77 | C |
| ATOM | 4903 | CB | LEU | A | 328 | −46.899 | −8.336 | 3.709 | 1.00 | 28.81 | C |
| ATOM | 4906 | CG | LEU | A | 328 | −48.349 | −8.364 | 3.257 | 1.00 | 28.82 | C |
| ATOM | 4908 | CD1 | LEU | A | 328 | −48.519 | −9.260 | 2.046 | 1.00 | 29.09 | C |

TABLE 3-7-continued

| | | | | | | | | | | |
|---|---|---|---|---|---|---|---|---|---|---|
| ATOM | 4912 | CD2 | LEU | A | 328 | −49.202 | −8.845 | 4.411 | 1.00 | 29.16 C |
| ATOM | 4916 | C | LEU | A | 328 | −46.057 | −6.291 | 2.564 | 1.00 | 28.61 C |
| ATOM | 4917 | O | LEU | A | 328 | −46.582 | −5.828 | 1.554 | 1.00 | 29.00 O |
| ATOM | 4919 | N | CYS | A | 329 | −45.612 | −5.532 | 3.557 | 1.00 | 28.24 N |
| ATOM | 4920 | CA | CYS | A | 329 | −45.737 | −4.086 | 3.504 | 1.00 | 27.95 C |
| ATOM | 4922 | CB | CYS | A | 329 | −45.311 | −3.459 | 4.834 | 1.00 | 28.21 C |
| ATOM | 4925 | SG | CYS | A | 329 | −45.280 | −1.630 | 4.817 | 1.00 | 32.39 S |
| ATOM | 4927 | C | CYS | A | 329 | −44.921 | −3.541 | 2.327 | 1.00 | 26.34 C |
| ATOM | 4928 | O | CYS | A | 329 | −45.459 | −2.853 | 1.475 | 1.00 | 26.23 O |
| ATOM | 4930 | N | PHE | A | 330 | −43.642 | −3.882 | 2.269 | 1.00 | 24.82 N |
| ATOM | 4931 | CA | PHE | A | 330 | −42.790 | −3.514 | 1.130 | 1.00 | 23.82 C |
| ATOM | 4933 | CB | PHE | A | 330 | −41.397 | −4.137 | 1.283 | 1.00 | 23.64 C |
| ATOM | 4936 | CG | PHE | A | 330 | −40.492 | −3.873 | .117 | 1.00 | 22.63 C |
| ATOM | 4937 | CD1 | PHE | A | 330 | −39.845 | −2.658 | −.008 | 1.00 | 21.68 C |
| ATOM | 4939 | CE1 | PHE | A | 330 | −39.020 | −2.393 | −1.082 | 1.00 | 21.07 C |
| ATOM | 4941 | CZ | PHE | A | 330 | −38.829 | −3.343 | −2.046 | 1.00 | 22.00 C |
| ATOM | 4943 | CE2 | PHE | A | 330 | −39.474 | −4.568 | −1.944 | 1.00 | 22.60 C |
| ATOM | 4945 | CD2 | PHE | A | 330 | −40.309 | −4.824 | −.865 | 1.00 | 22.36 C |
| ATOM | 4947 | C | PHE | A | 330 | −43.348 | −3.863 | −.281 | 1.00 | 22.99 C |
| ATOM | 4948 | O | PHE | A | 330 | −43.350 | −3.012 | −1.182 | 1.00 | 22.98 O |
| ATOM | 4950 | N | LEU | A | 331 | −43.789 | −5.101 | −.492 | 1.00 | 21.65 N |
| ATOM | 4951 | CA | LEU | A | 331 | −44.306 | −5.484 | −1.816 | 1.00 | 20.74 C |
| ATOM | 4953 | CB | LEU | A | 331 | −44.573 | −6.990 | −1.912 | 1.00 | 20.57 C |
| ATOM | 4956 | CG | LEU | A | 331 | −44.959 | −7.575 | −3.277 | 1.00 | 19.82 C |
| ATOM | 4958 | CD1 | LEU | A | 331 | −43.936 | −7.246 | −4.329 | 1.00 | 19.00 C |
| ATOM | 4962 | CD2 | LEU | A | 331 | −45.128 | −9.092 | −3.165 | 1.00 | 19.11 C |
| ATOM | 4966 | C | LEU | A | 331 | −45.568 | −4.710 | −2.159 | 1.00 | 19.98 C |
| ATOM | 4967 | O | LEU | A | 331 | −45.753 | −4.324 | −3.300 | 1.00 | 20.15 O |
| ATOM | 4969 | N | ALA | A | 332 | −46.431 | −4.495 | −1.172 | 1.00 | 19.09 N |
| ATOM | 4970 | CA | ALA | A | 332 | −47.619 | −3.675 | −1.353 | 1.00 | 18.46 C |
| ATOM | 4972 | CB | ALA | A | 332 | −48.406 | −3.587 | −.045 | 1.00 | 18.20 C |
| ATOM | 4976 | C | ALA | A | 332 | −47.248 | −2.279 | −1.856 | 1.00 | 17.91 C |
| ATOM | 4977 | O | ALA | A | 332 | −47.890 | −1.745 | −2.744 | 1.00 | 17.98 O |
| ATOM | 4979 | N | LEU | A | 333 | −46.197 | −1.706 | −1.295 | 1.00 | 17.62 N |
| ATOM | 4980 | CA | LEU | A | 333 | −45.753 | −.353 | −1.637 | 1.00 | 17.60 C |
| ATOM | 4982 | CB | LEU | A | 333 | −44.725 | .132 | −.598 | 1.00 | 17.59 C |
| ATOM | 4985 | CG | LEU | A | 333 | −44.122 | 1.533 | −.761 | 1.00 | 17.16 C |
| ATOM | 4987 | CD1 | LEU | A | 333 | −45.166 | 2.629 | −.554 | 1.00 | 16.99 C |
| ATOM | 4991 | CD2 | LEU | A | 333 | −42.979 | 1.704 | .200 | 1.00 | 15.89 C |
| ATOM | 4995 | C | LEU | A | 333 | −45.100 | −.320 | −3.005 | 1.00 | 17.70 C |
| ATOM | 4996 | O | LEU | A | 333 | −45.321 | .603 | −3.795 | 1.00 | 17.86 O |
| ATOM | 4998 | N | TYR | A | 334 | −44.248 | −1.319 | −3.234 | 1.00 | 17.63 N |
| ATOM | 4999 | CA | TYR | A | 334 | −43.542 | −1.531 | −4.489 | 1.00 | 17.44 C |
| ATOM | 5001 | CB | TYR | A | 334 | −42.893 | −2.908 | −4.444 | 1.00 | 17.50 C |
| ATOM | 5004 | CG | TYR | A | 334 | −41.897 | −3.169 | −5.523 | 1.00 | 18.03 C |
| ATOM | 5005 | CD1 | TYR | A | 334 | −40.698 | −2.473 | −5.569 | 1.00 | 18.83 C |
| ATOM | 5007 | CE1 | TYR | A | 334 | −39.764 | −2.725 | −6.542 | 1.00 | 18.13 C |
| ATOM | 5009 | CZ | TYR | A | 334 | −40.016 | −3.678 | −7.478 | 1.00 | 18.78 C |
| ATOM | 5010 | OH | TYR | A | 334 | −39.096 | −3.929 | −8.439 | 1.00 | 21.71 O |
| ATOM | 5012 | CE2 | TYR | A | 334 | −41.180 | −4.391 | −7.462 | 1.00 | 19.74 C |
| ATOM | 5014 | CD2 | TYR | A | 334 | −42.118 | −4.139 | −6.472 | 1.00 | 19.59 C |
| ATOM | 5016 | C | TYR | A | 334 | −44.500 | −1.497 | −5.649 | 1.00 | 17.43 C |
| ATOM | 5017 | O | TYR | A | 334 | −44.264 | −.803 | −6.636 | 1.00 | 17.64 O |
| ATOM | 5019 | N | ASN | A | 335 | −45.589 | −2.253 | −5.504 | 1.00 | 17.30 N |
| ATOM | 5020 | CA | ASN | A | 335 | −46.574 | −2.448 | −6.553 | 1.00 | 17.23 C |
| ATOM | 5022 | CB | ASN | A | 335 | −47.544 | −3.551 | −6.166 | 1.00 | 17.32 C |
| ATOM | 5025 | CG | ASN | A | 335 | −46.952 | −4.920 | −6.332 | 1.00 | 18.16 C |
| ATOM | 5026 | OD1 | ASN | A | 335 | −45.913 | −5.090 | −6.989 | 1.00 | 18.99 O |
| ATOM | 5027 | ND2 | ASN | A | 335 | −47.616 | −5.921 | −5.749 | 1.00 | 18.49 N |
| ATOM | 5030 | C | ASN | A | 335 | −47.365 | −1.218 | −6.812 | 1.00 | 17.12 C |
| ATOM | 5031 | O | ASN | A | 335 | −47.613 | −.852 | −7.965 | 1.00 | 17.36 O |
| ATOM | 5033 | N | THR | A | 336 | −47.789 | −.602 | −5.722 | 1.00 | 17.20 N |
| ATOM | 5034 | CA | THR | A | 336 | −48.601 | .593 | −5.779 | 1.00 | 17.36 C |
| ATOM | 5036 | CB | THR | A | 336 | −48.888 | 1.104 | −4.381 | 1.00 | 17.20 C |
| ATOM | 5038 | OG1 | THR | A | 336 | −49.611 | .103 | −3.657 | 1.00 | 16.26 O |
| ATOM | 5040 | CG2 | THR | A | 336 | −49.688 | 2.384 | −4.452 | 1.00 | 17.18 C |
| ATOM | 5044 | C | THR | A | 336 | −47.893 | 1.691 | −6.550 | 1.00 | 17.84 C |
| ATOM | 5045 | O | THR | A | 336 | −48.511 | 2.388 | −7.360 | 1.00 | 18.07 O |
| ATOM | 5047 | N | ILE | A | 337 | −46.595 | 1.831 | −6.298 | 1.00 | 18.14 N |
| ATOM | 5048 | CA | ILE | A | 337 | −45.817 | 2.904 | −6.895 | 1.00 | 18.50 C |
| ATOM | 5050 | CB | ILE | A | 337 | −44.584 | 3.209 | −6.066 | 1.00 | 18.31 C |
| ATOM | 5052 | CG1 | ILE | A | 337 | −45.014 | 3.997 | −4.837 | 1.00 | 18.58 C |
| ATOM | 5055 | CD1 | ILE | A | 337 | −44.043 | 3.866 | −3.735 | 1.00 | 20.66 C |
| ATOM | 5059 | CG2 | ILE | A | 337 | −43.570 | 3.988 | −6.867 | 1.00 | 16.98 C |
| ATOM | 5063 | C | ILE | A | 337 | −45.447 | 2.548 | −8.314 | 1.00 | 19.29 C |
| ATOM | 5064 | O | ILE | A | 337 | −45.556 | 3.387 | −9.214 | 1.00 | 19.17 O |
| ATOM | 5066 | N | ASN | A | 338 | −45.033 | 1.299 | −8.513 | 1.00 | 20.16 N |
| ATOM | 5067 | CA | ASN | A | 338 | −44.861 | .767 | −9.864 | 1.00 | 20.93 C |

TABLE 3-7-continued

| | | | | | | | | | | |
|---|---|---|---|---|---|---|---|---|---|---|
| ATOM | 5069 | CB | ASN | A | 338 | −44.409 | −.695 | −9.830 | 1.00 | 21.07 C |
| ATOM | 5072 | CG | ASN | A | 338 | −42.953 | −.845 | −9.439 | 1.00 | 21.61 C |
| ATOM | 5073 | OD1 | ASN | A | 338 | −42.232 | .143 | −9.308 | 1.00 | 22.40 O |
| ATOM | 5074 | ND2 | ASN | A | 338 | −42.509 | −2.086 | −9.260 | 1.00 | 21.92 N |
| ATOM | 5077 | C | ASN | A | 338 | −46.123 | .914 | −10.719 | 1.00 | 21.44 C |
| ATOM | 5078 | O | ASN | A | 338 | −46.022 | 1.202 | −11.904 | 1.00 | 21.25 O |
| ATOM | 5080 | N | GLU | A | 339 | −47.303 | .747 | −10.128 | 1.00 | 22.21 N |
| ATOM | 5081 | CA | GLU | A | 339 | −48.532 | 1.000 | −10.880 | 1.00 | 23.31 C |
| ATOM | 5083 | CB | GLU | A | 339 | −49.768 | .464 | −10.164 | 1.00 | 24.13 C |
| ATOM | 5086 | CG | GLU | A | 339 | −50.146 | −.936 | −10.660 | 1.00 | 28.69 C |
| ATOM | 5089 | CD | GLU | A | 339 | −50.939 | −1.740 | −9.638 | 1.00 | 35.06 C |
| ATOM | 5090 | OE1 | GLU | A | 339 | −51.899 | −1.136 | −9.067 | 1.00 | 39.51 O |
| ATOM | 5091 | OE2 | GLU | A | 339 | −50.596 | −2.952 | −9.414 | 1.00 | 36.64 O |
| ATOM | 5092 | C | GLU | A | 339 | −48.725 | 2.463 | −11.269 | 1.00 | 22.71 C |
| ATOM | 5093 | O | GLU | A | 339 | −49.215 | 2.743 | −12.372 | 1.00 | 22.48 O |
| ATOM | 5095 | N | ILE | A | 340 | −48.339 | 3.390 | −10.390 | 1.00 | 22.19 N |
| ATOM | 5096 | CA | ILE | A | 340 | −48.406 | 4.813 | −10.734 | 1.00 | 21.64 C |
| ATOM | 5098 | CB | ILE | A | 340 | −48.135 | 5.739 | −9.538 | 1.00 | 21.33 C |
| ATOM | 5100 | CG1 | ILE | A | 340 | −49.229 | 5.596 | −8.482 | 1.00 | 21.29 C |
| ATOM | 5103 | CD1 | ILE | A | 340 | −48.925 | 6.306 | −7.150 | 1.00 | 20.00 C |
| ATOM | 5107 | CG2 | ILE | A | 340 | −48.091 | 7.177 | −9.982 | 1.00 | 20.28 C |
| ATOM | 5111 | C | ILE | A | 340 | −47.414 | 5.128 | −11.861 | 1.00 | 21.78 C |
| ATOM | 5112 | O | ILE | A | 340 | −47.786 | 5.826 | −12.818 | 1.00 | 22.13 O |
| ATOM | 5114 | N | ALA | A | 341 | −46.179 | 4.609 | −11.771 | 1.00 | 21.34 N |
| ATOM | 5115 | CA | ALA | A | 341 | −45.147 | 4.892 | −12.787 | 1.00 | 21.03 C |
| ATOM | 5117 | CB | ALA | A | 341 | −43.837 | 4.268 | −12.406 | 1.00 | 20.55 C |
| ATOM | 5121 | C | ALA | A | 341 | −45.592 | 4.426 | −14.183 | 1.00 | 21.32 C |
| ATOM | 5122 | O | ALA | A | 341 | −45.228 | 5.036 | −15.217 | 1.00 | 21.11 O |
| ATOM | 5124 | N | TYR | A | 342 | −46.393 | 3.355 | −14.196 | 1.00 | 21.45 N |
| ATOM | 5125 | CA | TYR | A | 342 | −47.008 | 2.861 | −15.414 | 1.00 | 21.41 C |
| ATOM | 5127 | CB | TYR | A | 342 | −47.627 | 1.468 | −15.208 | 1.00 | 21.31 C |
| ATOM | 5130 | CG | TYR | A | 342 | −48.336 | .957 | −16.450 | 1.00 | 19.60 C |
| ATOM | 5131 | CD1 | TYR | A | 342 | −47.613 | .463 | −17.521 | 1.00 | 16.69 C |
| ATOM | 5133 | CE1 | TYR | A | 342 | −48.231 | .032 | −18.643 | 1.00 | 15.50 C |
| ATOM | 5135 | CZ | TYR | A | 342 | −49.595 | .085 | −18.728 | 1.00 | 15.88 C |
| ATOM | 5136 | OH | TYR | A | 342 | −50.196 | −.352 | −19.877 | 1.00 | 16.46 O |
| ATOM | 5138 | CE2 | TYR | A | 342 | −50.352 | .558 | −17.681 | 1.00 | 16.50 C |
| ATOM | 5140 | CD2 | TYR | A | 342 | −49.725 | .997 | −16.556 | 1.00 | 18.17 C |
| ATOM | 5142 | C | TYR | A | 342 | −48.064 | 3.830 | −15.899 | 1.00 | 22.08 C |
| ATOM | 5143 | O | TYR | A | 342 | −48.094 | 4.169 | −17.048 | 1.00 | 22.07 O |
| ATOM | 5145 | N | ASP | A | 343 | −48.942 | 4.283 | −15.032 | 1.00 | 23.41 N |
| ATOM | 5146 | CA | ASP | A | 343 | −49.970 | 5.211 | −15.481 | 1.00 | 24.66 C |
| ATOM | 5148 | CB | ASP | A | 343 | −50.851 | 5.674 | −14.318 | 1.00 | 25.10 C |
| ATOM | 5151 | CG | ASP | A | 343 | −51.720 | 4.552 | −13.732 | 1.00 | 26.06 C |
| ATOM | 5152 | OD1 | ASP | A | 343 | −52.107 | 3.613 | −14.477 | 1.00 | 26.39 O |
| ATOM | 5153 | OD2 | ASP | A | 343 | −52.032 | 4.642 | −12.516 | 1.00 | 27.29 O |
| ATOM | 5154 | C | ASP | A | 343 | −49.316 | 6.420 | −16.142 | 1.00 | 25.22 C |
| ATOM | 5155 | O | ASP | A | 343 | −49.755 | 6.874 | −17.192 | 1.00 | 25.47 O |
| ATOM | 5157 | N | ASN | A | 344 | −48.260 | 6.936 | −15.528 | 1.00 | 25.87 N |
| ATOM | 5158 | CA | ASN | A | 344 | −47.508 | 8.042 | −16.127 | 1.00 | 26.41 C |
| ATOM | 5160 | CB | ASN | A | 344 | −46.498 | 8.605 | −15.134 | 1.00 | 26.56 C |
| ATOM | 5163 | CG | ASN | A | 344 | −47.152 | 9.407 | −14.073 | 1.00 | 26.95 C |
| ATOM | 5164 | OD1 | ASN | A | 344 | −47.495 | 10.568 | −14.296 | 1.00 | 29.13 O |
| ATOM | 5165 | ND2 | ASN | A | 344 | −47.367 | 8.799 | −12.916 | 1.00 | 26.36 N |
| ATOM | 5168 | C | ASN | A | 344 | −46.785 | 7.674 | −17.416 | 1.00 | 26.53 C |
| ATOM | 5169 | O | ASN | A | 344 | −46.658 | 8.508 | −18.304 | 1.00 | 26.74 O |
| ATOM | 5171 | N | LEU | A | 345 | −46.280 | 6.448 | −17.510 | 1.00 | 26.56 N |
| ATOM | 5172 | CA | LEU | A | 345 | −45.634 | 6.019 | −18.739 | 1.00 | 26.37 C |
| ATOM | 5174 | CB | LEU | A | 345 | −44.890 | 4.693 | −18.550 | 1.00 | 26.32 C |
| ATOM | 5177 | CG | LEU | A | 345 | −43.995 | 4.339 | −19.750 | 1.00 | 25.96 C |
| ATOM | 5179 | CD1 | LEU | A | 345 | −42.706 | 5.133 | −19.665 | 1.00 | 25.07 C |
| ATOM | 5183 | CD2 | LEU | A | 345 | −43.724 | 2.835 | −19.874 | 1.00 | 24.75 C |
| ATOM | 5187 | C | LEU | A | 345 | −46.679 | 5.908 | −19.856 | 1.00 | 26.38 C |
| ATOM | 5188 | O | LEU | A | 345 | −46.435 | 6.335 | −20.966 | 1.00 | 26.52 O |
| ATOM | 5190 | N | LYS | A | 346 | −47.839 | 5.340 | −19.563 | 1.00 | 26.59 N |
| ATOM | 5191 | CA | LYS | A | 346 | −48.880 | 5.176 | −20.572 | 1.00 | 26.89 C |
| ATOM | 5193 | CB | LYS | A | 346 | −50.065 | 4.367 | −20.011 | 1.00 | 26.80 C |
| ATOM | 5196 | CG | LYS | A | 346 | −51.073 | 3.931 | −21.062 | 1.00 | 26.26 C |
| ATOM | 5199 | CD | LYS | A | 346 | −52.210 | 3.080 | −20.517 | 1.00 | 26.15 C |
| ATOM | 5202 | CE | LYS | A | 346 | −53.227 | 3.849 | −19.689 | 1.00 | 26.40 C |
| ATOM | 5205 | NZ | LYS | A | 346 | −53.136 | 3.506 | −18.223 | 1.00 | 27.67 N |
| ATOM | 5209 | C | LYS | A | 346 | −49.372 | 6.537 | −21.071 | 1.00 | 27.52 C |
| ATOM | 5210 | O | LYS | A | 346 | −49.562 | 6.742 | −22.272 | 1.00 | 27.57 O |
| ATOM | 5212 | N | ASP | A | 347 | −49.567 | 7.472 | −20.148 | 1.00 | 28.10 N |
| ATOM | 5213 | CA | ASP | A | 347 | −50.309 | 8.689 | −20.465 | 1.00 | 28.58 C |
| ATOM | 5215 | CB | ASP | A | 347 | −51.305 | 9.017 | −19.329 | 1.00 | 28.85 C |
| ATOM | 5218 | CG | ASP | A | 347 | −52.426 | 7.950 | −19.197 | 1.00 | 30.01 C |
| ATOM | 5219 | OD1 | ASP | A | 347 | −52.827 | 7.349 | −20.223 | 1.00 | 30.51 O |

TABLE 3-7-continued

Coordinates of *P. tremuloides* IspS

| | | | | | | | | | | |
|---|---|---|---|---|---|---|---|---|---|---|
| ATOM | 5220 | OD2 | ASP | A | 347 | −52.910 | 7.704 | −18.069 | 1.00 | 32.61 O |
| ATOM | 5221 | C | ASP | A | 347 | −49.407 | 9.871 | −20.804 | 1.00 | 28.22 C |
| ATOM | 5222 | O | ASP | A | 347 | −49.778 | 10.710 | −21.611 | 1.00 | 28.39 O |
| ATOM | 5224 | N | LYS | A | 348 | −48.228 | 9.930 | −20.206 | 1.00 | 28.03 N |
| ATOM | 5225 | CA | LYS | A | 348 | −47.301 | 11.021 | −20.467 | 1.00 | 28.01 C |
| ATOM | 5227 | CB | LYS | A | 348 | −46.785 | 11.648 | −19.164 | 1.00 | 28.39 C |
| ATOM | 5230 | CG | LYS | A | 348 | −47.834 | 12.305 | −18.257 | 1.00 | 30.18 C |
| ATOM | 5233 | CD | LYS | A | 348 | −47.143 | 12.898 | −17.003 | 1.00 | 32.40 C |
| ATOM | 5236 | CE | LYS | A | 348 | −48.124 | 13.121 | −15.874 | 1.00 | 33.59 C |
| ATOM | 5239 | NZ | LYS | A | 348 | −49.319 | 13.878 | −16.341 | 1.00 | 35.48 N |
| ATOM | 5243 | C | LYS | A | 348 | −46.107 | 10.551 | −21.260 | 1.00 | 27.25 C |
| ATOM | 5244 | O | LYS | A | 348 | −45.241 | 11.345 | −21.566 | 1.00 | 27.60 O |
| ATOM | 5246 | N | GLY | A | 349 | −46.036 | 9.271 | −21.583 | 1.00 | 26.47 N |
| ATOM | 5247 | CA | GLY | A | 349 | −44.863 | 8.742 | −22.261 | 1.00 | 26.01 C |
| ATOM | 5250 | C | GLY | A | 349 | −43.559 | 9.109 | −21.587 | 1.00 | 25.67 C |
| ATOM | 5251 | O | GLY | A | 349 | −42.613 | 9.472 | −22.250 | 1.00 | 25.85 O |
| ATOM | 5253 | N | GLU | A | 350 | −43.498 | 9.032 | −20.269 | 1.00 | 25.55 N |
| ATOM | 5254 | CA | GLU | A | 350 | −42.272 | 9.374 | −19.555 | 1.00 | 25.76 C |
| ATOM | 5256 | CB | GLU | A | 350 | −42.332 | 10.814 | −19.021 | 1.00 | 26.34 C |
| ATOM | 5259 | CG | GLU | A | 350 | −42.179 | 11.928 | −20.106 | 1.00 | 29.04 C |
| ATOM | 5262 | CD | GLU | A | 350 | −40.745 | 12.101 | −20.598 | 1.00 | 32.08 C |
| ATOM | 5263 | OE1 | GLU | A | 350 | −39.853 | 12.170 | −19.716 | 1.00 | 35.46 O |
| ATOM | 5264 | OE2 | GLU | A | 350 | −40.516 | 12.174 | −21.839 | 1.00 | 31.64 O |
| ATOM | 5265 | C | GLU | A | 350 | −42.084 | 8.414 | −18.400 | 1.00 | 24.87 C |
| ATOM | 5266 | O | GLU | A | 350 | −43.067 | 8.046 | −17.760 | 1.00 | 25.16 O |
| ATOM | 5268 | N | ASN | A | 351 | −40.833 | 8.009 | −18.145 | 1.00 | 23.71 N |
| ATOM | 5269 | CA | ASN | A | 351 | −40.494 | 7.189 | −16.980 | 1.00 | 22.88 C |
| ATOM | 5271 | CB | ASN | A | 351 | −39.351 | 6.229 | −17.287 | 1.00 | 22.88 C |
| ATOM | 5274 | CG | ASN | A | 351 | −39.141 | 5.215 | −16.184 | 1.00 | 22.98 C |
| ATOM | 5275 | OD1 | ASN | A | 351 | −39.006 | 5.584 | −15.035 | 1.00 | 22.68 O |
| ATOM | 5276 | ND2 | ASN | A | 351 | −39.139 | 3.924 | −16.529 | 1.00 | 24.38 N |
| ATOM | 5279 | C | ASN | A | 351 | −40.126 | 8.058 | −15.786 | 1.00 | 22.40 C |
| ATOM | 5280 | O | ASN | A | 351 | −39.097 | 8.741 | −15.785 | 1.00 | 22.66 O |
| ATOM | 5282 | N | ILE | A | 352 | −40.965 | 8.021 | −14.760 | 1.00 | 21.55 N |
| ATOM | 5283 | CA | ILE | A | 352 | −40.770 | 8.860 | −13.591 | 1.00 | 20.75 C |
| ATOM | 5285 | CB | ILE | A | 352 | −42.002 | 9.788 | −13.360 | 1.00 | 20.95 C |
| ATOM | 5287 | CG1 | ILE | A | 352 | −43.263 | 8.970 | −13.022 | 1.00 | 20.82 C |
| ATOM | 5290 | CD1 | ILE | A | 352 | −44.237 | 9.698 | −12.122 | 1.00 | 20.21 C |
| ATOM | 5294 | CG2 | ILE | A | 352 | −42.266 | 10.669 | −14.582 | 1.00 | 19.85 C |
| ATOM | 5298 | C | ILE | A | 352 | −40.516 | 8.016 | −12.339 | 1.00 | 20.37 C |
| ATOM | 5299 | O | ILE | A | 352 | −40.574 | 8.513 | −11.224 | 1.00 | 20.55 O |
| ATOM | 5301 | N | LEU | A | 353 | −40.236 | 6.733 | −12.519 | 1.00 | 19.98 N |
| ATOM | 5302 | CA | LEU | A | 353 | −40.061 | 5.828 | −11.387 | 1.00 | 19.42 C |
| ATOM | 5304 | CB | LEU | A | 353 | −39.894 | 4.392 | −11.870 | 1.00 | 19.27 C |
| ATOM | 5307 | CG | LEU | A | 353 | −39.989 | 3.318 | −10.799 | 1.00 | 19.01 C |
| ATOM | 5309 | CD1 | LEU | A | 353 | −41.164 | 3.574 | −9.867 | 1.00 | 18.35 C |
| ATOM | 5313 | CD2 | LEU | A | 353 | −40.085 | 1.938 | −11.468 | 1.00 | 18.74 C |
| ATOM | 5317 | C | LEU | A | 353 | −38.890 | 6.240 | −10.523 | 1.00 | 19.11 C |
| ATOM | 5318 | O | LEU | A | 353 | −39.022 | 6.319 | −9.314 | 1.00 | 18.96 O |
| ATOM | 5320 | N | PRO | A | 354 | −37.746 | 6.549 | −11.142 | 1.00 | 19.06 N |
| ATOM | 5321 | CA | PRO | A | 354 | −36.631 | 7.069 | −10.367 | 1.00 | 19.29 C |
| ATOM | 5323 | CB | PRO | A | 354 | −35.749 | 7.717 | −11.438 | 1.00 | 19.25 C |
| ATOM | 5326 | CG | PRO | A | 354 | −35.997 | 6.942 | −12.638 | 1.00 | 19.08 C |
| ATOM | 5329 | CD | PRO | A | 354 | −37.409 | 6.472 | −12.572 | 1.00 | 19.00 C |
| ATOM | 5332 | C | PRO | A | 354 | −37.024 | 8.122 | −9.328 | 1.00 | 19.33 C |
| ATOM | 5333 | O | PRO | A | 354 | −36.534 | 8.057 | −8.193 | 1.00 | 19.73 O |
| ATOM | 5334 | N | TYR | A | 355 | −37.891 | 9.063 | −9.721 | 1.00 | 18.83 N |
| ATOM | 5335 | CA | TYR | A | 355 | −38.206 | 10.221 | −8.898 | 1.00 | 18.79 C |
| ATOM | 5337 | CB | TYR | A | 355 | −38.836 | 11.359 | −9.707 | 1.00 | 19.10 C |
| ATOM | 5340 | CG | TYR | A | 355 | −38.142 | 11.708 | −11.009 | 1.00 | 20.15 C |
| ATOM | 5341 | CD1 | TYR | A | 355 | −36.940 | 12.403 | −11.027 | 1.00 | 20.78 C |
| ATOM | 5343 | CE1 | TYR | A | 355 | −36.321 | 12.719 | −12.232 | 1.00 | 22.19 C |
| ATOM | 5345 | CZ | TYR | A | 355 | −36.918 | 12.347 | −13.438 | 1.00 | 22.19 C |
| ATOM | 5346 | OH | TYR | A | 355 | −36.341 | 12.660 | −14.657 | 1.00 | 23.29 O |
| ATOM | 5348 | CE2 | TYR | A | 355 | −38.113 | 11.677 | −13.430 | 1.00 | 21.62 C |
| ATOM | 5350 | CD2 | TYR | A | 355 | −38.720 | 11.371 | −12.227 | 1.00 | 21.05 C |
| ATOM | 5352 | C | TYR | A | 355 | −39.155 | 9.864 | −7.777 | 1.00 | 18.43 C |
| ATOM | 5353 | O | TYR | A | 355 | −39.081 | 10.460 | −6.709 | 1.00 | 18.61 O |
| ATOM | 5355 | N | LEU | A | 356 | −40.058 | 8.917 | −8.023 | 1.00 | 17.92 N |
| ATOM | 5356 | CA | LEU | A | 356 | −40.993 | 8.467 | −6.994 | 1.00 | 17.38 C |
| ATOM | 5358 | CB | LEU | A | 356 | −42.136 | 7.658 | −7.597 | 1.00 | 17.17 C |
| ATOM | 5361 | CG | LEU | A | 356 | −42.956 | 8.366 | −8.682 | 1.00 | 17.56 C |
| ATOM | 5363 | CD1 | LEU | A | 356 | −43.933 | 7.419 | −9.371 | 1.00 | 17.47 C |
| ATOM | 5367 | CD2 | LEU | A | 356 | −43.698 | 9.548 | −8.112 | 1.00 | 18.08 C |
| ATOM | 5371 | C | LEU | A | 356 | −40.241 | 7.623 | −5.978 | 1.00 | 17.10 C |
| ATOM | 5372 | O | LEU | A | 356 | −40.332 | 7.859 | −4.783 | 1.00 | 17.62 O |
| ATOM | 5374 | N | THR | A | 357 | −39.464 | 6.656 | −6.442 | 1.00 | 16.64 N |
| ATOM | 5375 | CA | THR | A | 357 | −38.775 | 5.769 | −5.513 | 1.00 | 16.18 C |

TABLE 3-7-continued

| | | | | | | | | | | |
|---|---|---|---|---|---|---|---|---|---|---|
| ATOM | 5377 | CB | THR | A | 357 | −38.104 | 4.554 | −6.213 | 1.00 | 16.04 | C |
| ATOM | 5379 | OG1 | THR | A | 357 | −37.092 | 4.996 | −7.123 | 1.00 | 15.93 | O |
| ATOM | 5381 | CG2 | THR | A | 357 | −39.142 | 3.732 | −6.962 | 1.00 | 14.99 | C |
| ATOM | 5385 | C | THR | A | 357 | −37.764 | 6.544 | −4.686 | 1.00 | 16.16 | C |
| ATOM | 5386 | O | THR | A | 357 | −37.599 | 6.278 | −3.506 | 1.00 | 16.07 | O |
| ATOM | 5388 | N | LYS | A | 358 | −37.107 | 7.524 | −5.291 | 1.00 | 16.20 | N |
| ATOM | 5389 | CA | LYS | A | 358 | −36.186 | 8.365 | −4.543 | 1.00 | 16.46 | C |
| ATOM | 5391 | CB | LYS | A | 358 | −35.518 | 9.386 | −5.453 | 1.00 | 16.80 | C |
| ATOM | 5394 | CG | LYS | A | 358 | −34.612 | 10.388 | −4.741 | 1.00 | 18.30 | C |
| ATOM | 5397 | CD | LYS | A | 358 | −33.352 | 9.738 | −4.168 | 1.00 | 20.21 | C |
| ATOM | 5400 | CE | LYS | A | 358 | −32.335 | 10.811 | −3.768 | 1.00 | 21.96 | C |
| ATOM | 5403 | NZ | LYS | A | 358 | −31.163 | 10.275 | −3.019 | 1.00 | 22.95 | N |
| ATOM | 5407 | C | LYS | A | 358 | −36.936 | 9.083 | −3.440 | 1.00 | 16.26 | C |
| ATOM | 5408 | O | LYS | A | 358 | −36.448 | 9.161 | −2.320 | 1.00 | 16.15 | O |
| ATOM | 5410 | N | ALA | A | 359 | −38.126 | 9.593 | −3.763 | 1.00 | 16.11 | N |
| ATOM | 5411 | CA | ALA | A | 359 | −38.937 | 10.332 | −2.798 | 1.00 | 16.10 | C |
| ATOM | 5413 | CB | ALA | A | 359 | −40.221 | 10.768 | −3.406 | 1.00 | 15.71 | C |
| ATOM | 5417 | C | ALA | A | 359 | −39.215 | 9.476 | −1.588 | 1.00 | 16.52 | C |
| ATOM | 5418 | O | ALA | A | 359 | −39.247 | 9.970 | −.442 | 1.00 | 16.82 | O |
| ATOM | 5420 | N | TRP | A | 360 | −39.398 | 8.187 | −1.843 | 1.00 | 16.79 | N |
| ATOM | 5421 | CA | TRP | A | 360 | −39.704 | 7.247 | −.780 | 1.00 | 17.25 | C |
| ATOM | 5423 | CB | TRP | A | 360 | −40.390 | 6.006 | −1.352 | 1.00 | 17.41 | C |
| ATOM | 5426 | CG | TRP | A | 360 | −41.852 | 6.129 | −1.318 | 1.00 | 17.06 | C |
| ATOM | 5427 | CD1 | TRP | A | 360 | −42.664 | 6.451 | −2.346 | 1.00 | 17.94 | C |
| ATOM | 5429 | NE1 | TRP | A | 360 | −43.967 | 6.489 | −1.926 | 1.00 | 18.03 | N |
| ATOM | 5431 | CE2 | TRP | A | 360 | −44.002 | 6.193 | −.592 | 1.00 | 17.72 | C |
| ATOM | 5432 | CD2 | TRP | A | 360 | −42.684 | 5.965 | −.179 | 1.00 | 16.60 | C |
| ATOM | 5433 | CE3 | TRP | A | 360 | −42.441 | 5.654 | 1.155 | 1.00 | 16.65 | C |
| ATOM | 5435 | CZ3 | TRP | A | 360 | −43.508 | 5.573 | 2.022 | 1.00 | 16.91 | C |
| ATOM | 5437 | CH2 | TRP | A | 360 | −44.811 | 5.807 | 1.586 | 1.00 | 17.82 | C |
| ATOM | 5439 | CZ2 | TRP | A | 360 | −45.080 | 6.114 | .282 | 1.00 | 18.49 | C |
| ATOM | 5441 | C | TRP | A | 360 | −38.490 | 6.865 | .073 | 1.00 | 17.52 | C |
| ATOM | 5442 | O | TRP | A | 360 | −38.603 | 6.767 | 1.297 | 1.00 | 17.38 | O |
| ATOM | 5444 | N | ALA | A | 361 | −37.344 | 6.651 | −.568 | 1.00 | 17.82 | N |
| ATOM | 5445 | CA | ALA | A | 361 | −36.122 | 6.336 | .157 | 1.00 | 18.11 | C |
| ATOM | 5447 | CB | ALA | A | 361 | −34.982 | 6.050 | −.805 | 1.00 | 17.92 | C |
| ATOM | 5451 | C | ALA | A | 361 | −35.781 | 7.507 | 1.063 | 1.00 | 18.52 | C |
| ATOM | 5452 | O | ALA | A | 361 | −35.434 | 7.327 | 2.229 | 1.00 | 18.48 | O |
| ATOM | 5454 | N | ASP | A | 362 | −35.911 | 8.711 | .521 | 1.00 | 19.16 | N |
| ATOM | 5455 | CA | ASP | A | 362 | −35.627 | 9.925 | 1.276 | 1.00 | 19.90 | C |
| ATOM | 5457 | CB | ASP | A | 362 | −35.797 | 11.167 | .387 | 1.00 | 20.39 | C |
| ATOM | 5460 | CG | ASP | A | 362 | −34.596 | 11.424 | −.530 | 1.00 | 21.84 | C |
| ATOM | 5461 | OD1 | ASP | A | 362 | −33.630 | 10.625 | −.561 | 1.00 | 22.88 | O |
| ATOM | 5462 | OD2 | ASP | A | 362 | −34.630 | 12.453 | −1.231 | 1.00 | 24.83 | O |
| ATOM | 5463 | C | ASP | A | 362 | −36.532 | 10.039 | 2.510 | 1.00 | 19.91 | C |
| ATOM | 5464 | O | ASP | A | 362 | −36.074 | 10.427 | 3.591 | 1.00 | 19.76 | O |
| ATOM | 5466 | N | LEU | A | 363 | −37.813 | 9.707 | 2.346 | 1.00 | 19.95 | N |
| ATOM | 5467 | CA | LEU | A | 363 | −38.747 | 9.688 | 3.478 | 1.00 | 19.85 | C |
| ATOM | 5469 | CB | LEU | A | 363 | −40.175 | 9.415 | 3.006 | 1.00 | 19.70 | C |
| ATOM | 5472 | CG | LEU | A | 363 | −41.219 | 9.293 | 4.123 | 1.00 | 18.58 | C |
| ATOM | 5474 | CD1 | LEU | A | 363 | −41.189 | 10.551 | 4.965 | 1.00 | 18.37 | C |
| ATOM | 5478 | CD2 | LEU | A | 363 | −42.597 | 9.073 | 3.551 | 1.00 | 16.43 | C |
| ATOM | 5482 | C | LEU | A | 363 | −38.368 | 8.613 | 4.488 | 1.00 | 20.24 | C |
| ATOM | 5483 | O | LEU | A | 363 | −38.314 | 8.875 | 5.691 | 1.00 | 20.52 | O |
| ATOM | 5485 | N | CYS | A | 364 | −38.129 | 7.397 | 3.997 | 1.00 | 20.29 | N |
| ATOM | 5486 | CA | CYS | A | 364 | −37.741 | 6.308 | 4.874 | 1.00 | 20.39 | C |
| ATOM | 5488 | CB | CYS | A | 364 | −37.595 | 4.985 | 4.111 | 1.00 | 20.37 | C |
| ATOM | 5491 | SG | CYS | A | 364 | −39.208 | 4.201 | 3.666 | 1.00 | 20.69 | S |
| ATOM | 5493 | C | CYS | A | 364 | −36.467 | 6.683 | 5.646 | 1.00 | 20.59 | C |
| ATOM | 5494 | O | CYS | A | 364 | −36.386 | 6.445 | 6.863 | 1.00 | 20.82 | O |
| ATOM | 5496 | N | ASN | A | 365 | −35.495 | 7.314 | 4.980 | 1.00 | 20.35 | N |
| ATOM | 5497 | CA | ASN | A | 365 | −34.282 | 7.716 | 5.697 | 1.00 | 20.14 | C |
| ATOM | 5499 | CB | ASN | A | 365 | −33.188 | 8.203 | 4.754 | 1.00 | 20.18 | C |
| ATOM | 5502 | CG | ASN | A | 365 | −32.359 | 7.064 | 4.184 | 1.00 | 20.55 | C |
| ATOM | 5503 | OD1 | ASN | A | 365 | −31.706 | 6.316 | 4.925 | 1.00 | 20.40 | O |
| ATOM | 5504 | ND2 | ASN | A | 365 | −32.365 | 6.938 | 2.854 | 1.00 | 21.25 | N |
| ATOM | 5507 | C | ASN | A | 365 | −34.590 | 8.746 | 6.779 | 1.00 | 19.92 | C |
| ATOM | 5508 | O | ASN | A | 365 | −33.997 | 8.685 | 7.857 | 1.00 | 19.94 | O |
| ATOM | 5510 | N | ALA | A | 366 | −35.531 | 9.658 | 6.507 | 1.00 | 19.58 | N |
| ATOM | 5511 | CA | ALA | A | 366 | −36.036 | 10.578 | 7.537 | 1.00 | 19.39 | C |
| ATOM | 5513 | CB | ALA | A | 366 | −37.083 | 11.507 | 6.971 | 1.00 | 18.79 | C |
| ATOM | 5517 | C | ALA | A | 366 | −36.597 | 9.784 | 8.730 | 1.00 | 19.75 | C |
| ATOM | 5518 | O | ALA | A | 366 | −36.215 | 10.049 | 9.891 | 1.00 | 19.53 | O |
| ATOM | 5520 | N | PHE | A | 367 | −37.460 | 8.797 | 8.447 | 1.00 | 19.69 | N |
| ATOM | 5521 | CA | PHE | A | 367 | −37.985 | 7.925 | 9.502 | 1.00 | 20.11 | C |
| ATOM | 5523 | CB | PHE | A | 367 | −38.952 | 6.857 | 8.967 | 1.00 | 20.47 | C |
| ATOM | 5526 | CG | PHE | A | 367 | −40.293 | 7.370 | 8.494 | 1.00 | 21.35 | C |
| ATOM | 5527 | CD1 | PHE | A | 367 | −40.985 | 8.347 | 9.180 | 1.00 | 21.54 | C |

TABLE 3-7-continued

Coordinates of *P. tremuloides* IspS

| ATOM | 5529 | CE1 | PHE | A | 367 | −42.224 | 8.775 | 8.732 | 1.00 | 21.47 | C |
|------|------|-----|-----|---|-----|---------|-------|-------|------|-------|---|
| ATOM | 5531 | CZ  | PHE | A | 367 | −42.798 | 8.213 | 7.612 | 1.00 | 21.87 | C |
| ATOM | 5533 | CE2 | PHE | A | 367 | −42.135 | 7.230 | 6.924 | 1.00 | 22.60 | C |
| ATOM | 5535 | CD2 | PHE | A | 367 | −40.894 | 6.798 | 7.373 | 1.00 | 22.90 | C |
| ATOM | 5537 | C   | PHE | A | 367 | −36.871 | 7.179 | 10.252 | 1.00 | 20.12 | C |
| ATOM | 5538 | O   | PHE | A | 367 | −36.940 | 7.009 | 11.476 | 1.00 | 19.88 | O |
| ATOM | 5540 | N   | LEU | A | 368 | −35.868 | 6.696 | 9.516 | 1.00 | 20.30 | N |
| ATOM | 5541 | CA  | LEU | A | 368 | −34.775 | 5.931 | 10.133 | 1.00 | 20.19 | C |
| ATOM | 5543 | CB  | LEU | A | 368 | −33.783 | 5.413 | 9.085 | 1.00 | 20.08 | C |
| ATOM | 5546 | CG  | LEU | A | 368 | −32.743 | 4.363 | 9.514 | 1.00 | 19.30 | C |
| ATOM | 5548 | CD1 | LEU | A | 368 | −33.384 | 3.227 | 10.260 | 1.00 | 18.66 | C |
| ATOM | 5552 | CD2 | LEU | A | 368 | −31.968 | 3.807 | 8.319 | 1.00 | 18.16 | C |
| ATOM | 5556 | C   | LEU | A | 368 | −34.063 | 6.812 | 11.128 | 1.00 | 20.41 | C |
| ATOM | 5557 | O   | LEU | A | 368 | −33.842 | 6.407 | 12.257 | 1.00 | 20.01 | O |
| ATOM | 5559 | N   | GLN | A | 369 | −33.751 | 8.036 | 10.711 | 1.00 | 20.89 | N |
| ATOM | 5560 | CA  | GLN | A | 369 | −33.037 | 8.970 | 11.564 | 1.00 | 21.49 | C |
| ATOM | 5562 | CB  | GLN | A | 369 | −32.782 | 10.280 | 10.832 | 1.00 | 21.58 | C |
| ATOM | 5565 | CG  | GLN | A | 369 | −32.071 | 11.359 | 11.677 | 1.00 | 21.20 | C |
| ATOM | 5568 | CD  | GLN | A | 369 | −30.639 | 11.006 | 11.976 | 1.00 | 20.04 | C |
| ATOM | 5569 | OE1 | GLN | A | 369 | −30.282 | 10.650 | 13.108 | 1.00 | 19.10 | O |
| ATOM | 5570 | NE2 | GLN | A | 369 | −29.803 | 11.095 | 10.956 | 1.00 | 18.75 | N |
| ATOM | 5573 | C   | GLN | A | 369 | −33.763 | 9.265 | 12.870 | 1.00 | 22.21 | C |
| ATOM | 5574 | O   | GLN | A | 369 | −33.122 | 9.343 | 13.909 | 1.00 | 22.41 | O |
| ATOM | 5576 | N   | GLU | A | 370 | −35.080 | 9.455 | 12.822 | 1.00 | 23.05 | N |
| ATOM | 5577 | CA  | GLU | A | 370 | −35.856 | 9.718 | 14.046 | 1.00 | 23.71 | C |
| ATOM | 5579 | CB  | GLU | A | 370 | −37.329 | 10.041 | 13.726 | 1.00 | 24.04 | C |
| ATOM | 5582 | CG  | GLU | A | 370 | −37.484 | 11.293 | 12.862 | 1.00 | 26.84 | C |
| ATOM | 5585 | CD  | GLU | A | 370 | −38.897 | 11.910 | 12.834 | 1.00 | 30.36 | C |
| ATOM | 5586 | OE1 | GLU | A | 370 | −39.886 | 11.161 | 12.586 | 1.00 | 31.90 | O |
| ATOM | 5587 | OE2 | GLU | A | 370 | −38.992 | 13.164 | 13.014 | 1.00 | 31.62 | O |
| ATOM | 5588 | C   | GLU | A | 370 | −35.755 | 8.523 | 14.994 | 1.00 | 23.60 | C |
| ATOM | 5589 | O   | GLU | A | 370 | −35.534 | 8.689 | 16.199 | 1.00 | 23.33 | O |
| ATOM | 5591 | N   | ALA | A | 371 | −35.904 | 7.322 | 14.435 | 1.00 | 23.72 | N |
| ATOM | 5592 | CA  | ALA | A | 371 | −35.771 | 6.091 | 15.201 | 1.00 | 23.91 | C |
| ATOM | 5594 | CB  | ALA | A | 371 | −35.991 | 4.868 | 14.312 | 1.00 | 23.76 | C |
| ATOM | 5598 | C   | ALA | A | 371 | −34.392 | 6.051 | 15.840 | 1.00 | 24.20 | C |
| ATOM | 5599 | O   | ALA | A | 371 | −34.277 | 5.804 | 17.035 | 1.00 | 24.54 | O |
| ATOM | 5601 | N   | LYS | A | 372 | −33.355 | 6.333 | 15.049 | 1.00 | 24.38 | N |
| ATOM | 5602 | CA  | LYS | A | 372 | −31.979 | 6.273 | 15.530 | 1.00 | 24.39 | C |
| ATOM | 5604 | CB  | LYS | A | 372 | −30.970 | 6.466 | 14.393 | 1.00 | 24.43 | C |
| ATOM | 5607 | CG  | LYS | A | 372 | −30.623 | 5.164 | 13.645 | 1.00 | 25.20 | C |
| ATOM | 5610 | CD  | LYS | A | 372 | −29.188 | 5.149 | 13.069 | 1.00 | 26.09 | C |
| ATOM | 5613 | CE  | LYS | A | 372 | −29.114 | 5.437 | 11.557 | 1.00 | 27.01 | C |
| ATOM | 5616 | NZ  | LYS | A | 372 | −29.002 | 4.200 | 10.709 | 1.00 | 26.82 | N |
| ATOM | 5620 | C   | LYS | A | 372 | −31.717 | 7.268 | 16.645 | 1.00 | 24.59 | C |
| ATOM | 5621 | O   | LYS | A | 372 | −31.096 | 6.908 | 17.627 | 1.00 | 25.13 | O |
| ATOM | 5623 | N   | TRP | A | 373 | −32.181 | 8.507 | 16.520 | 1.00 | 24.78 | N |
| ATOM | 5624 | CA  | TRP | A | 373 | −32.006 | 9.473 | 17.610 | 1.00 | 24.90 | C |
| ATOM | 5626 | CB  | TRP | A | 373 | −32.565 | 10.863 | 17.266 | 1.00 | 24.75 | C |
| ATOM | 5629 | CG  | TRP | A | 373 | −31.701 | 11.677 | 16.338 | 1.00 | 23.59 | C |
| ATOM | 5630 | CD1 | TRP | A | 373 | −30.344 | 11.663 | 16.259 | 1.00 | 22.38 | C |
| ATOM | 5632 | NE1 | TRP | A | 373 | −29.915 | 12.539 | 15.298 | 1.00 | 21.59 | N |
| ATOM | 5634 | CE2 | TRP | A | 373 | −30.999 | 13.162 | 14.744 | 1.00 | 21.69 | C |
| ATOM | 5635 | CD2 | TRP | A | 373 | −32.147 | 12.644 | 15.376 | 1.00 | 22.41 | C |
| ATOM | 5636 | CE3 | TRP | A | 373 | −33.409 | 13.110 | 14.976 | 1.00 | 21.98 | C |
| ATOM | 5638 | CZ3 | TRP | A | 373 | −33.480 | 14.072 | 13.979 | 1.00 | 22.08 | C |
| ATOM | 5640 | CH2 | TRP | A | 373 | −32.313 | 14.567 | 13.366 | 1.00 | 22.31 | C |
| ATOM | 5642 | CZ2 | TRP | A | 373 | −31.067 | 14.124 | 13.736 | 1.00 | 21.87 | C |
| ATOM | 5644 | C   | TRP | A | 373 | −32.678 | 8.970 | 18.881 | 1.00 | 25.53 | C |
| ATOM | 5645 | O   | TRP | A | 373 | −32.101 | 9.072 | 19.972 | 1.00 | 25.99 | O |
| ATOM | 5647 | N   | LEU | A | 374 | −33.881 | 8.420 | 18.739 | 1.00 | 25.84 | N |
| ATOM | 5648 | CA  | LEU | A | 374 | −34.667 | 7.980 | 19.893 | 1.00 | 26.29 | C |
| ATOM | 5650 | CB  | LEU | A | 374 | −36.070 | 7.562 | 19.443 | 1.00 | 26.32 | C |
| ATOM | 5653 | CG  | LEU | A | 374 | −37.227 | 7.646 | 20.444 | 1.00 | 26.39 | C |
| ATOM | 5655 | CD1 | LEU | A | 374 | −38.456 | 8.286 | 19.761 | 1.00 | 26.95 | C |
| ATOM | 5659 | CD2 | LEU | A | 374 | −37.583 | 6.281 | 21.050 | 1.00 | 26.24 | C |
| ATOM | 5663 | C   | LEU | A | 374 | −33.982 | 6.824 | 20.623 | 1.00 | 26.77 | C |
| ATOM | 5664 | O   | LEU | A | 374 | −33.995 | 6.758 | 21.860 | 1.00 | 26.95 | O |
| ATOM | 5666 | N   | TYR | A | 375 | −33.383 | 5.919 | 19.854 | 1.00 | 27.23 | N |
| ATOM | 5667 | CA  | TYR | A | 375 | −32.706 | 4.761 | 20.425 | 1.00 | 27.74 | C |
| ATOM | 5669 | CB  | TYR | A | 375 | −32.195 | 3.814 | 19.328 | 1.00 | 27.78 | C |
| ATOM | 5672 | CG  | TYR | A | 375 | −31.526 | 2.556 | 19.848 | 1.00 | 28.74 | C |
| ATOM | 5673 | CD1 | TYR | A | 375 | −32.264 | 1.394 | 20.090 | 1.00 | 29.61 | C |
| ATOM | 5675 | CE1 | TYR | A | 375 | −31.652 | .232 | 20.573 | 1.00 | 29.89 | C |
| ATOM | 5677 | CZ  | TYR | A | 375 | −30.287 | .226 | 20.817 | 1.00 | 30.15 | C |
| ATOM | 5678 | OH  | TYR | A | 375 | −29.676 | −.917 | 21.286 | 1.00 | 30.57 | O |
| ATOM | 5680 | CE2 | TYR | A | 375 | −29.530 | 1.367 | 20.579 | 1.00 | 30.05 | C |
| ATOM | 5682 | CD2 | TYR | A | 375 | −30.152 | 2.522 | 20.096 | 1.00 | 29.74 | C |

TABLE 3-7-continued

Coordinates of *P. tremuloides* IspS

| ATOM | 5684 | C | TYR | A | 375 | −31.553 | 5.248 | 21.275 | 1.00 | 27.97 | C |
|------|------|------|-----|---|-----|---------|--------|--------|------|-------|---|
| ATOM | 5685 | O | TYR | A | 375 | −31.404 | 4.837 | 22.422 | 1.00 | 28.00 | O |
| ATOM | 5687 | N | ASN | A | 376 | −30.763 | 6.158 | 20.719 | 1.00 | 28.32 | N |
| ATOM | 5688 | CA | ASN | A | 376 | −29.531 | 6.590 | 21.368 | 1.00 | 28.71 | C |
| ATOM | 5690 | CB | ASN | A | 376 | −28.569 | 7.161 | 20.329 | 1.00 | 28.60 | C |
| ATOM | 5693 | CG | ASN | A | 376 | −28.215 | 6.159 | 19.255 | 1.00 | 28.32 | C |
| ATOM | 5694 | OD1 | ASN | A | 376 | −27.961 | 4.977 | 19.527 | 1.00 | 25.72 | O |
| ATOM | 5695 | ND2 | ASN | A | 376 | −28.195 | 6.631 | 18.015 | 1.00 | 29.29 | N |
| ATOM | 5698 | C | ASN | A | 376 | −29.728 | 7.617 | 22.484 | 1.00 | 29.05 | C |
| ATOM | 5699 | O | ASN | A | 376 | −28.752 | 8.021 | 23.136 | 1.00 | 29.03 | O |
| ATOM | 5701 | N | LYS | A | 377 | −30.977 | 8.021 | 22.716 | 1.00 | 29.16 | N |
| ATOM | 5702 | CA | LYS | A | 377 | −31.254 | 9.178 | 23.549 | 1.00 | 29.27 | C |
| ATOM | 5704 | CB | LYS | A | 377 | −31.051 | 8.879 | 25.050 | 1.00 | 29.52 | C |
| ATOM | 5707 | CG | LYS | A | 377 | −32.202 | 8.112 | 25.723 | 1.00 | 30.36 | C |
| ATOM | 5710 | CD | LYS | A | 377 | −32.202 | 6.638 | 25.340 | 1.00 | 31.54 | C |
| ATOM | 5713 | CE | LYS | A | 377 | −33.322 | 5.862 | 26.031 | 1.00 | 32.30 | C |
| ATOM | 5716 | NZ | LYS | A | 377 | −33.559 | 4.509 | 25.411 | 1.00 | 32.13 | N |
| ATOM | 5720 | C | LYS | A | 377 | −30.337 | 10.299 | 23.080 | 1.00 | 28.92 | C |
| ATOM | 5721 | O | LYS | A | 377 | −29.590 | 10.867 | 23.875 | 1.00 | 28.94 | O |
| ATOM | 5723 | N | SER | A | 378 | −30.377 | 10.575 | 21.776 | 1.00 | 28.52 | N |
| ATOM | 5724 | CA | SER | A | 378 | −29.652 | 11.700 | 21.201 | 1.00 | 28.30 | C |
| ATOM | 5726 | CB | SER | A | 378 | −29.623 | 11.620 | 19.678 | 1.00 | 28.33 | C |
| ATOM | 5729 | OG | SER | A | 378 | −28.919 | 10.482 | 19.237 | 1.00 | 29.36 | O |
| ATOM | 5731 | C | SER | A | 378 | −30.355 | 12.977 | 21.594 | 1.00 | 27.97 | C |
| ATOM | 5732 | O | SER | A | 378 | −31.483 | 12.947 | 22.108 | 1.00 | 27.91 | O |
| ATOM | 5734 | N | THR | A | 379 | −29.684 | 14.098 | 21.344 | 1.00 | 27.60 | N |
| ATOM | 5735 | CA | THR | A | 379 | −30.257 | 15.422 | 21.581 | 1.00 | 27.24 | C |
| ATOM | 5737 | CB | THR | A | 379 | −29.929 | 15.950 | 23.002 | 1.00 | 27.23 | C |
| ATOM | 5739 | OG1 | THR | A | 379 | −28.512 | 16.102 | 23.158 | 1.00 | 26.85 | O |
| ATOM | 5741 | CG2 | THR | A | 379 | −30.467 | 15.007 | 24.067 | 1.00 | 27.48 | C |
| ATOM | 5745 | C | THR | A | 379 | −29.738 | 16.414 | 20.548 | 1.00 | 26.83 | C |
| ATOM | 5746 | O | THR | A | 379 | −28.834 | 17.190 | 20.844 | 1.00 | 26.69 | O |
| ATOM | 5748 | N | PRO | A | 380 | −30.305 | 16.390 | 19.331 | 1.00 | 26.56 | N |
| ATOM | 5749 | CA | PRO | A | 380 | −29.884 | 17.315 | 18.278 | 1.00 | 26.52 | C |
| ATOM | 5751 | CB | PRO | A | 380 | −30.380 | 16.648 | 16.992 | 1.00 | 26.46 | C |
| ATOM | 5754 | CG | PRO | A | 380 | −31.281 | 15.533 | 17.408 | 1.00 | 26.41 | C |
| ATOM | 5757 | CD | PRO | A | 380 | −31.395 | 15.508 | 18.887 | 1.00 | 26.53 | C |
| ATOM | 5760 | C | PRO | A | 380 | −30.469 | 18.728 | 18.386 | 1.00 | 26.55 | C |
| ATOM | 5761 | O | PRO | A | 380 | −31.472 | 18.966 | 19.063 | 1.00 | 26.69 | O |
| ATOM | 5762 | N | THR | A | 381 | −29.840 | 19.661 | 17.692 | 1.00 | 26.51 | N |
| ATOM | 5763 | CA | THR | A | 381 | −30.299 | 21.034 | 17.699 | 1.00 | 26.51 | C |
| ATOM | 5765 | CB | THR | A | 381 | −29.261 | 21.955 | 17.033 | 1.00 | 26.99 | C |
| ATOM | 5767 | OG1 | THR | A | 381 | −28.919 | 21.431 | 15.732 | 1.00 | 27.65 | O |
| ATOM | 5769 | CG2 | THR | A | 381 | −28.003 | 22.082 | 17.930 | 1.00 | 26.41 | C |
| ATOM | 5773 | C | THR | A | 381 | −31.635 | 21.167 | 16.970 | 1.00 | 26.06 | C |
| ATOM | 5774 | O | THR | A | 381 | −31.972 | 20.347 | 16.112 | 1.00 | 26.03 | O |
| ATOM | 5776 | N | PHE | A | 382 | −32.386 | 22.218 | 17.294 | 1.00 | 25.52 | N |
| ATOM | 5777 | CA | PHE | A | 382 | −33.681 | 22.436 | 16.654 | 1.00 | 24.83 | C |
| ATOM | 5779 | CB | PHE | A | 382 | −34.284 | 23.793 | 17.011 | 1.00 | 24.53 | C |
| ATOM | 5782 | CG | PHE | A | 382 | −35.495 | 24.113 | 16.211 | 1.00 | 23.77 | C |
| ATOM | 5783 | CD1 | PHE | A | 382 | −36.745 | 23.715 | 16.637 | 1.00 | 24.50 | C |
| ATOM | 5785 | CE1 | PHE | A | 382 | −37.873 | 23.977 | 15.878 | 1.00 | 24.49 | C |
| ATOM | 5787 | CZ | PHE | A | 382 | −37.744 | 24.630 | 14.673 | 1.00 | 24.41 | C |
| ATOM | 5789 | CE2 | PHE | A | 382 | −36.490 | 25.014 | 14.235 | 1.00 | 23.88 | C |
| ATOM | 5791 | CD2 | PHE | A | 382 | −35.381 | 24.752 | 14.999 | 1.00 | 23.29 | C |
| ATOM | 5793 | C | PHE | A | 382 | −33.542 | 22.342 | 15.150 | 1.00 | 24.49 | C |
| ATOM | 5794 | O | PHE | A | 382 | −34.361 | 21.731 | 14.485 | 1.00 | 24.32 | O |
| ATOM | 5796 | N | ASP | A | 383 | −32.498 | 22.969 | 14.627 | 1.00 | 24.42 | N |
| ATOM | 5797 | CA | ASP | A | 383 | −32.257 | 23.005 | 13.190 | 1.00 | 24.19 | C |
| ATOM | 5799 | CB | ASP | A | 383 | −31.101 | 23.966 | 12.867 | 1.00 | 24.21 | C |
| ATOM | 5802 | CG | ASP | A | 383 | −31.473 | 25.423 | 13.050 | 1.00 | 23.72 | C |
| ATOM | 5803 | OD1 | ASP | A | 383 | −32.634 | 25.794 | 12.837 | 1.00 | 25.60 | O |
| ATOM | 5804 | OD2 | ASP | A | 383 | −30.594 | 26.220 | 13.383 | 1.00 | 24.03 | O |
| ATOM | 5805 | C | ASP | A | 383 | −31.982 | 21.612 | 12.599 | 1.00 | 24.06 | C |
| ATOM | 5806 | O | ASP | A | 383 | −32.393 | 21.342 | 11.473 | 1.00 | 24.00 | O |
| ATOM | 5808 | N | ASP | A | 384 | −31.298 | 20.739 | 13.336 | 1.00 | 23.78 | N |
| ATOM | 5809 | CA | ASP | A | 384 | −31.078 | 19.379 | 12.848 | 1.00 | 24.11 | C |
| ATOM | 5811 | CB | ASP | A | 384 | −29.981 | 18.651 | 13.632 | 1.00 | 24.54 | C |
| ATOM | 5814 | CG | ASP | A | 384 | −28.573 | 19.009 | 13.159 | 1.00 | 26.32 | C |
| ATOM | 5815 | OD1 | ASP | A | 384 | −28.441 | 19.852 | 12.232 | 1.00 | 28.55 | O |
| ATOM | 5816 | OD2 | ASP | A | 384 | −27.599 | 18.451 | 13.728 | 1.00 | 27.18 | O |
| ATOM | 5817 | C | ASP | A | 384 | −32.351 | 18.550 | 12.905 | 1.00 | 23.83 | C |
| ATOM | 5818 | O | ASP | A | 384 | −32.670 | 17.825 | 11.955 | 1.00 | 24.24 | O |
| ATOM | 5820 | N | TYR | A | 385 | −33.070 | 18.637 | 14.017 | 1.00 | 23.31 | N |
| ATOM | 5821 | CA | TYR | A | 385 | −34.294 | 17.861 | 14.179 | 1.00 | 22.89 | C |
| ATOM | 5823 | CB | TYR | A | 385 | −34.833 | 17.979 | 15.608 | 1.00 | 22.86 | C |
| ATOM | 5826 | CG | TYR | A | 385 | −36.144 | 17.245 | 15.807 | 1.00 | 22.65 | C |
| ATOM | 5827 | CD1 | TYR | A | 385 | −36.163 | 15.868 | 16.030 | 1.00 | 22.36 | C |

TABLE 3-7-continued

| | | | | | Coordinates of *P. tremuloides* IspS | | | | | |
|---|---|---|---|---|---|---|---|---|---|---|
| ATOM | 5829 | CE1 | TYR | A | 385 | −37.351 | 15.189 | 16.206 | 1.00 | 22.77 C |
| ATOM | 5831 | CZ | TYR | A | 385 | −38.545 | 15.887 | 16.146 | 1.00 | 23.54 C |
| ATOM | 5832 | OH | TYR | A | 385 | −39.733 | 15.212 | 16.309 | 1.00 | 24.38 O |
| ATOM | 5834 | CE2 | TYR | A | 385 | −38.554 | 17.258 | 15.913 | 1.00 | 22.76 C |
| ATOM | 5836 | CD2 | TYR | A | 385 | −37.360 | 17.923 | 15.744 | 1.00 | 22.12 C |
| ATOM | 5838 | C | TYR | A | 385 | −35.375 | 18.299 | 13.190 | 1.00 | 22.55 C |
| ATOM | 5839 | O | TYR | A | 385 | −36.050 | 17.467 | 12.584 | 1.00 | 22.85 O |
| ATOM | 5841 | N | PHE | A | 386 | −35.537 | 19.609 | 13.042 | 1.00 | 22.08 N |
| ATOM | 5842 | CA | PHE | A | 386 | −36.626 | 20.155 | 12.248 | 1.00 | 21.62 C |
| ATOM | 5844 | CB | PHE | A | 386 | −36.857 | 21.628 | 12.568 | 1.00 | 21.73 C |
| ATOM | 5847 | CG | PHE | A | 386 | −38.033 | 22.209 | 11.851 | 1.00 | 21.54 C |
| ATOM | 5848 | CD1 | PHE | A | 386 | −39.311 | 21.933 | 12.273 | 1.00 | 21.29 C |
| ATOM | 5850 | CE1 | PHE | A | 386 | −40.380 | 22.444 | 11.623 | 1.00 | 22.11 C |
| ATOM | 5852 | CZ | PHE | A | 386 | −40.193 | 23.240 | 10.517 | 1.00 | 23.28 C |
| ATOM | 5854 | CE2 | PHE | A | 386 | −38.920 | 23.502 | 10.069 | 1.00 | 23.10 C |
| ATOM | 5856 | CD2 | PHE | A | 386 | −37.853 | 22.989 | 10.737 | 1.00 | 22.15 C |
| ATOM | 5858 | C | PHE | A | 386 | −36.369 | 19.987 | 10.769 | 1.00 | 21.09 C |
| ATOM | 5859 | O | PHE | A | 386 | −37.278 | 19.700 | 10.006 | 1.00 | 20.91 O |
| ATOM | 5861 | N | GLY | A | 387 | −35.127 | 20.177 | 10.362 | 1.00 | 20.68 N |
| ATOM | 5862 | CA | GLY | A | 387 | −34.747 | 19.917 | 8.985 | 1.00 | 20.43 C |
| ATOM | 5865 | C | GLY | A | 387 | −35.151 | 18.521 | 8.544 | 1.00 | 19.95 C |
| ATOM | 5866 | O | GLY | A | 387 | −35.553 | 18.327 | 7.398 | 1.00 | 20.24 O |
| ATOM | 5868 | N | ASN | A | 388 | −35.032 | 17.554 | 9.451 | 1.00 | 19.12 N |
| ATOM | 5869 | CA | ASN | A | 388 | −35.451 | 16.182 | 9.202 | 1.00 | 18.73 C |
| ATOM | 5871 | CB | ASN | A | 388 | −34.744 | 15.272 | 10.205 | 1.00 | 18.90 C |
| ATOM | 5874 | CG | ASN | A | 388 | −34.863 | 13.795 | 9.871 | 1.00 | 18.35 C |
| ATOM | 5875 | OD1 | ASN | A | 388 | −34.163 | 13.284 | 8.993 | 1.00 | 17.24 O |
| ATOM | 5876 | ND2 | ASN | A | 388 | −35.714 | 13.092 | 10.614 | 1.00 | 17.01 N |
| ATOM | 5879 | C | ASN | A | 388 | −36.968 | 16.033 | 9.350 | 1.00 | 18.65 C |
| ATOM | 5880 | O | ASN | A | 388 | −37.624 | 15.370 | 8.551 | 1.00 | 18.82 O |
| ATOM | 5882 | N | ALA | A | 389 | −37.527 | 16.670 | 10.371 | 1.00 | 18.38 N |
| ATOM | 5883 | CA | ALA | A | 389 | −38.926 | 16.477 | 10.728 | 1.00 | 18.02 C |
| ATOM | 5885 | CB | ALA | A | 389 | −39.203 | 17.107 | 12.084 | 1.00 | 17.83 C |
| ATOM | 5889 | C | ALA | A | 389 | −39.949 | 16.966 | 9.700 | 1.00 | 17.90 C |
| ATOM | 5890 | O | ALA | A | 389 | −41.095 | 16.544 | 9.760 | 1.00 | 17.74 O |
| ATOM | 5892 | N | TRP | A | 390 | −39.585 | 17.860 | 8.783 | 1.00 | 18.11 N |
| ATOM | 5893 | CA | TRP | A | 390 | −40.543 | 18.254 | 7.731 | 1.00 | 18.46 C |
| ATOM | 5895 | CB | TRP | A | 390 | −40.459 | 19.737 | 7.329 | 1.00 | 18.59 C |
| ATOM | 5898 | CG | TRP | A | 390 | −39.143 | 20.224 | 6.821 | 1.00 | 19.26 C |
| ATOM | 5899 | CD1 | TRP | A | 390 | −38.224 | 20.947 | 7.519 | 1.00 | 20.64 C |
| ATOM | 5901 | NE1 | TRP | A | 390 | −37.138 | 21.224 | 6.729 | 1.00 | 20.62 N |
| ATOM | 5903 | CE2 | TRP | A | 390 | −37.352 | 20.694 | 5.485 | 1.00 | 19.57 C |
| ATOM | 5904 | CD2 | TRP | A | 390 | −38.607 | 20.066 | 5.504 | 1.00 | 19.15 C |
| ATOM | 5905 | CE3 | TRP | A | 390 | −39.060 | 19.448 | 4.344 | 1.00 | 20.13 C |
| ATOM | 5907 | CZ3 | TRP | A | 390 | −38.254 | 19.477 | 3.224 | 1.00 | 20.27 C |
| ATOM | 5909 | CH2 | TRP | A | 390 | −37.017 | 20.110 | 3.239 | 1.00 | 19.38 C |
| ATOM | 5911 | CZ2 | TRP | A | 390 | −36.549 | 20.724 | 4.356 | 1.00 | 19.49 C |
| ATOM | 5913 | C | TRP | A | 390 | −40.407 | 17.343 | 6.527 | 1.00 | 18.73 C |
| ATOM | 5914 | O | TRP | A | 390 | −41.369 | 17.143 | 5.788 | 1.00 | 18.32 O |
| ATOM | 5916 | N | LYS | A | 391 | −39.200 | 16.806 | 6.336 | 1.00 | 19.30 N |
| ATOM | 5917 | CA | LYS | A | 391 | −38.969 | 15.692 | 5.404 | 1.00 | 19.70 C |
| ATOM | 5919 | CB | LYS | A | 391 | −37.459 | 15.392 | 5.244 | 1.00 | 19.92 C |
| ATOM | 5922 | CG | LYS | A | 391 | −36.812 | 15.953 | 3.935 | 1.00 | 22.08 C |
| ATOM | 5925 | CD | LYS | A | 391 | −35.257 | 16.217 | 4.040 | 1.00 | 23.92 C |
| ATOM | 5928 | CE | LYS | A | 391 | −34.918 | 17.698 | 4.426 | 1.00 | 24.43 C |
| ATOM | 5931 | NZ | LYS | A | 391 | −33.699 | 17.901 | 5.307 | 1.00 | 23.23 N |
| ATOM | 5935 | C | LYS | A | 391 | −39.731 | 14.441 | 5.861 | 1.00 | 19.46 C |
| ATOM | 5936 | O | LYS | A | 391 | −40.284 | 13.709 | 5.032 | 1.00 | 20.07 O |
| ATOM | 5938 | N | SER | A | 392 | −39.793 | 14.202 | 7.170 | 1.00 | 18.95 N |
| ATOM | 5939 | CA | SER | A | 392 | −40.455 | 12.998 | 7.666 | 1.00 | 18.63 C |
| ATOM | 5941 | CB | SER | A | 392 | −39.850 | 12.508 | 9.000 | 1.00 | 18.75 C |
| ATOM | 5944 | OG | SER | A | 392 | −40.314 | 13.230 | 10.126 | 1.00 | 18.94 O |
| ATOM | 5946 | C | SER | A | 392 | −41.964 | 13.152 | 7.771 | 1.00 | 18.20 C |
| ATOM | 5947 | O | SER | A | 392 | −42.654 | 12.182 | 8.031 | 1.00 | 18.12 O |
| ATOM | 5949 | N | SER | A | 393 | −42.477 | 14.360 | 7.567 | 1.00 | 18.07 N |
| ATOM | 5950 | CA | SER | A | 393 | −43.929 | 14.591 | 7.556 | 1.00 | 18.02 C |
| ATOM | 5952 | CB | SER | A | 393 | −44.229 | 16.078 | 7.504 | 1.00 | 18.08 C |
| ATOM | 5955 | OG | SER | A | 393 | −43.995 | 16.558 | 6.192 | 1.00 | 18.01 O |
| ATOM | 5957 | C | SER | A | 393 | −44.594 | 13.971 | 6.340 | 1.00 | 17.87 C |
| ATOM | 5958 | O | SER | A | 393 | −45.778 | 13.661 | 6.372 | 1.00 | 18.03 O |
| ATOM | 5960 | N | SER | A | 394 | −43.823 | 13.841 | 5.264 | 1.00 | 17.69 N |
| ATOM | 5961 | CA | SER | A | 394 | −44.284 | 13.306 | 3.989 | 1.00 | 17.59 C |
| ATOM | 5963 | CB | SER | A | 394 | −45.329 | 12.180 | 4.149 | 1.00 | 17.61 C |
| ATOM | 5966 | OG | SER | A | 394 | −46.648 | 12.681 | 4.294 | 1.00 | 17.18 O |
| ATOM | 5968 | C | SER | A | 394 | −44.828 | 14.415 | 3.115 | 1.00 | 17.42 C |
| ATOM | 5969 | O | SER | A | 394 | −45.345 | 14.146 | 2.024 | 1.00 | 17.31 O |
| ATOM | 5971 | N | GLY | A | 395 | −44.711 | 15.654 | 3.592 | 1.00 | 17.23 N |
| ATOM | 5972 | CA | GLY | A | 395 | −45.088 | 16.827 | 2.807 | 1.00 | 17.26 C |

TABLE 3-7-continued

| | | | | | | | | | | |
|---|---|---|---|---|---|---|---|---|---|---|
| ATOM | 5975 | C | GLY | A | 395 | −44.478 | 16.749 | 1.415 | 1.00 | 17.29 C |
| ATOM | 5976 | O | GLY | A | 395 | −45.203 | 16.653 | .413 | 1.00 | 18.06 O |
| ATOM | 5978 | N | PRO | A | 396 | −43.145 | 16.754 | 1.331 | 1.00 | 16.72 N |
| ATOM | 5979 | CA | PRO | A | 396 | −42.582 | 16.610 | .006 | 1.00 | 16.40 C |
| ATOM | 5981 | CB | PRO | A | 396 | −41.080 | 16.549 | .259 | 1.00 | 16.62 C |
| ATOM | 5984 | CG | PRO | A | 396 | −40.903 | 16.749 | 1.775 | 1.00 | 17.11 C |
| ATOM | 5987 | CD | PRO | A | 396 | −42.157 | 17.252 | 2.296 | 1.00 | 16.87 C |
| ATOM | 5990 | C | PRO | A | 396 | −43.053 | 15.374 | −.748 | 1.00 | 15.89 C |
| ATOM | 5991 | O | PRO | A | 396 | −43.501 | 15.498 | −1.894 | 1.00 | 15.90 O |
| ATOM | 5992 | N | LEU | A | 397 | −42.973 | 14.197 | −.135 | 1.00 | 15.27 N |
| ATOM | 5993 | CA | LEU | A | 397 | −43.287 | 12.976 | −.886 | 1.00 | 14.57 C |
| ATOM | 5995 | CB | LEU | A | 397 | −43.332 | 11.733 | −.008 | 1.00 | 14.36 C |
| ATOM | 5998 | CG | LEU | A | 397 | −43.541 | 10.431 | −.781 | 1.00 | 14.02 C |
| ATOM | 6000 | CD1 | LEU | A | 397 | −42.690 | 9.348 | −.206 | 1.00 | 15.04 C |
| ATOM | 6004 | CD2 | LEU | A | 397 | −44.985 | 9.976 | −.805 | 1.00 | 13.75 C |
| ATOM | 6008 | C | LEU | A | 397 | −44.618 | 13.182 | −1.542 | 1.00 | 14.39 C |
| ATOM | 6009 | O | LEU | A | 397 | −44.736 | 12.999 | −2.745 | 1.00 | 14.57 O |
| ATOM | 6011 | N | GLN | A | 398 | −45.604 | 13.607 | −.751 | 1.00 | 14.08 N |
| ATOM | 6012 | CA | GLN | A | 398 | −46.962 | 13.828 | −1.245 | 1.00 | 13.91 C |
| ATOM | 6014 | CB | GLN | A | 398 | −47.860 | 14.363 | −.136 | 1.00 | 13.99 C |
| ATOM | 6017 | CG | GLN | A | 398 | −48.274 | 13.321 | .909 | 1.00 | 14.01 C |
| ATOM | 6020 | CD | GLN | A | 398 | −49.189 | 13.902 | 1.983 | 1.00 | 13.41 C |
| ATOM | 6021 | OE1 | GLN | A | 398 | −49.941 | 14.847 | 1.740 | 1.00 | 14.65 O |
| ATOM | 6022 | NE2 | GLN | A | 398 | −49.122 | 13.344 | 3.168 | 1.00 | 12.17 N |
| ATOM | 6025 | C | GLN | A | 398 | −47.015 | 14.800 | −2.403 | 1.00 | 13.84 C |
| ATOM | 6026 | O | GLN | A | 398 | −47.677 | 14.547 | −3.396 | 1.00 | 13.46 O |
| ATOM | 6028 | N | LEU | A | 399 | −46.319 | 15.922 | −2.272 | 1.00 | 14.11 N |
| ATOM | 6029 | CA | LEU | A | 399 | −46.359 | 16.942 | −3.315 | 1.00 | 14.37 C |
| ATOM | 6031 | CB | LEU | A | 399 | −45.900 | 18.282 | −2.756 | 1.00 | 14.26 C |
| ATOM | 6034 | CG | LEU | A | 399 | −46.882 | 18.830 | −1.704 | 1.00 | 14.44 C |
| ATOM | 6036 | CD1 | LEU | A | 399 | −46.250 | 19.960 | −.919 | 1.00 | 16.43 C |
| ATOM | 6040 | CD2 | LEU | A | 399 | −48.191 | 19.304 | −2.317 | 1.00 | 12.20 C |
| ATOM | 6044 | C | LEU | A | 399 | −45.582 | 16.525 | −4.578 | 1.00 | 14.68 C |
| ATOM | 6045 | O | LEU | A | 399 | −46.043 | 16.784 | −5.687 | 1.00 | 14.70 O |
| ATOM | 6047 | N | ILE | A | 400 | −44.443 | 15.844 | −4.419 | 1.00 | 14.92 N |
| ATOM | 6048 | CA | ILE | A | 400 | −43.748 | 15.221 | −5.564 | 1.00 | 15.08 C |
| ATOM | 6050 | CB | ILE | A | 400 | −42.549 | 14.355 | −5.129 | 1.00 | 15.35 C |
| ATOM | 6052 | CG1 | ILE | A | 400 | −41.406 | 15.254 | −4.611 | 1.00 | 16.83 C |
| ATOM | 6055 | CD1 | ILE | A | 400 | −40.234 | 14.490 | −3.958 | 1.00 | 17.18 C |
| ATOM | 6059 | CG2 | ILE | A | 400 | −42.060 | 13.486 | −6.292 | 1.00 | 14.03 C |
| ATOM | 6063 | C | ILE | A | 400 | −44.682 | 14.329 | −6.358 | 1.00 | 15.08 C |
| ATOM | 6064 | O | ILE | A | 400 | −44.672 | 14.362 | −7.574 | 1.00 | 15.18 O |
| ATOM | 6066 | N | PHE | A | 401 | −45.474 | 13.524 | −5.650 | 1.00 | 15.16 N |
| ATOM | 6067 | CA | PHE | A | 401 | −46.501 | 12.674 | −6.258 | 1.00 | 14.90 C |
| ATOM | 6069 | CB | PHE | A | 401 | −47.052 | 11.663 | −5.240 | 1.00 | 14.51 C |
| ATOM | 6072 | CG | PHE | A | 401 | −46.294 | 10.378 | −5.201 | 1.00 | 12.92 C |
| ATOM | 6073 | CD1 | PHE | A | 401 | −46.727 | 9.282 | −5.931 | 1.00 | 11.98 C |
| ATOM | 6075 | CE1 | PHE | A | 401 | −46.032 | 8.093 | −5.917 | 1.00 | 11.20 C |
| ATOM | 6077 | CZ | PHE | A | 401 | −44.881 | 7.985 | −5.165 | 1.00 | 12.03 C |
| ATOM | 6079 | CE2 | PHE | A | 401 | −44.431 | 9.078 | −4.428 | 1.00 | 11.98 C |
| ATOM | 6081 | CD2 | PHE | A | 401 | −45.143 | 10.263 | −4.453 | 1.00 | 12.09 C |
| ATOM | 6083 | C | PHE | A | 401 | −47.641 | 13.509 | −6.806 | 1.00 | 15.39 C |
| ATOM | 6084 | O | PHE | A | 401 | −48.183 | 13.215 | −7.858 | 1.00 | 15.51 O |
| ATOM | 6086 | N | ALA | A | 402 | −48.022 | 14.545 | −6.080 | 1.00 | 16.15 N |
| ATOM | 6087 | CA | ALA | A | 402 | −49.110 | 15.393 | −6.525 | 1.00 | 16.90 C |
| ATOM | 6089 | CB | ALA | A | 402 | −49.391 | 16.473 | −5.505 | 1.00 | 16.99 C |
| ATOM | 6093 | C | ALA | A | 402 | −48.722 | 16.003 | −7.856 | 1.00 | 17.50 C |
| ATOM | 6094 | O | ALA | A | 402 | −49.549 | 16.100 | −8.770 | 1.00 | 17.48 O |
| ATOM | 6096 | N | TYR | A | 403 | −47.444 | 16.367 | −7.963 | 1.00 | 18.28 N |
| ATOM | 6097 | CA | TYR | A | 403 | −46.916 | 17.046 | −9.142 | 1.00 | 18.94 C |
| ATOM | 6099 | CB | TYR | A | 403 | −45.412 | 17.252 | −9.043 | 1.00 | 19.03 C |
| ATOM | 6102 | CG | TYR | A | 403 | −44.823 | 17.801 | −10.314 | 1.00 | 19.79 C |
| ATOM | 6103 | CD1 | TYR | A | 403 | −44.973 | 19.138 | −10.652 | 1.00 | 20.80 C |
| ATOM | 6105 | CE1 | TYR | A | 403 | −44.436 | 19.643 | −11.827 | 1.00 | 20.73 C |
| ATOM | 6107 | CZ | TYR | A | 403 | −43.759 | 18.804 | −12.674 | 1.00 | 21.16 C |
| ATOM | 6108 | OH | TYR | A | 403 | −43.231 | 19.283 | −13.836 | 1.00 | 22.98 O |
| ATOM | 6110 | CE2 | TYR | A | 403 | −43.608 | 17.476 | −12.370 | 1.00 | 21.23 C |
| ATOM | 6112 | CD2 | TYR | A | 403 | −44.137 | 16.980 | −11.195 | 1.00 | 20.93 C |
| ATOM | 6114 | C | TYR | A | 403 | −47.198 | 16.293 | −10.413 | 1.00 | 19.39 C |
| ATOM | 6115 | O | TYR | A | 403 | −47.567 | 16.904 | −11.422 | 1.00 | 19.57 O |
| ATOM | 6117 | N | PHE | A | 404 | −47.023 | 14.976 | −10.376 | 1.00 | 19.74 N |
| ATOM | 6118 | CA | PHE | A | 404 | −47.239 | 14.177 | −11.573 | 1.00 | 20.35 C |
| ATOM | 6120 | CB | PHE | A | 404 | −46.533 | 12.841 | −11.466 | 1.00 | 19.96 C |
| ATOM | 6123 | CG | PHE | A | 404 | −45.048 | 12.971 | −11.387 | 1.00 | 18.81 C |
| ATOM | 6124 | CD1 | PHE | A | 404 | −44.292 | 13.115 | −12.528 | 1.00 | 17.42 C |
| ATOM | 6126 | CE1 | PHE | A | 404 | −42.935 | 13.239 | −12.457 | 1.00 | 17.24 C |
| ATOM | 6128 | CZ | PHE | A | 404 | −42.312 | 13.237 | −11.237 | 1.00 | 17.40 C |
| ATOM | 6130 | CE2 | PHE | A | 404 | −43.056 | 13.106 | −10.093 | 1.00 | 17.72 C |

TABLE 3-7-continued

Coordinates of *P. tremuloides* IspS

| ATOM | 6132 | CD2 | PHE | A | 404 | −44.413 | 12.975 | −10.170 | 1.00 | 17.93 | C |
|---|---|---|---|---|---|---|---|---|---|---|---|
| ATOM | 6134 | C | PHE | A | 404 | −48.713 | 13.994 | −11.894 | 1.00 | 21.59 | C |
| ATOM | 6135 | O | PHE | A | 404 | −49.072 | 13.717 | −13.046 | 1.00 | 21.71 | O |
| ATOM | 6137 | N | ALA | A | 405 | −49.572 | 14.169 | −10.896 | 1.00 | 22.87 | N |
| ATOM | 6138 | CA | ALA | A | 405 | −50.990 | 13.939 | −11.099 | 1.00 | 24.06 | C |
| ATOM | 6140 | CB | ALA | A | 405 | −51.604 | 13.408 | −9.833 | 1.00 | 24.15 | C |
| ATOM | 6144 | C | ALA | A | 405 | −51.724 | 15.192 | −11.556 | 1.00 | 25.21 | C |
| ATOM | 6145 | O | ALA | A | 405 | −52.876 | 15.114 | −11.939 | 1.00 | 25.51 | O |
| ATOM | 6147 | N | VAL | A | 406 | −51.056 | 16.336 | −11.530 | 1.00 | 26.52 | N |
| ATOM | 6148 | CA | VAL | A | 406 | −51.713 | 17.617 | −11.759 | 1.00 | 27.68 | C |
| ATOM | 6150 | CB | VAL | A | 406 | −51.694 | 18.406 | −10.434 | 1.00 | 27.60 | C |
| ATOM | 6152 | CG1 | VAL | A | 406 | −51.654 | 19.913 | −10.663 | 1.00 | 28.07 | C |
| ATOM | 6156 | CG2 | VAL | A | 406 | −52.883 | 18.009 | −9.596 | 1.00 | 27.41 | C |
| ATOM | 6160 | C | VAL | A | 406 | −51.097 | 18.429 | −12.925 | 1.00 | 29.10 | C |
| ATOM | 6161 | O | VAL | A | 406 | −51.810 | 19.104 | −13.678 | 1.00 | 28.53 | O |
| ATOM | 6163 | N | VAL | A | 407 | −49.772 | 18.356 | −13.059 | 1.00 | 30.90 | N |
| ATOM | 6164 | CA | VAL | A | 407 | −49.052 | 19.003 | −14.151 | 1.00 | 32.15 | C |
| ATOM | 6166 | CB | VAL | A | 407 | −47.574 | 19.228 | −13.777 | 1.00 | 32.25 | C |
| ATOM | 6168 | CG1 | VAL | A | 407 | −46.770 | 19.780 | −14.964 | 1.00 | 32.22 | C |
| ATOM | 6172 | CG2 | VAL | A | 407 | −47.490 | 20.154 | −12.583 | 1.00 | 32.25 | C |
| ATOM | 6176 | C | VAL | A | 407 | −49.134 | 18.160 | −15.421 | 1.00 | 33.36 | C |
| ATOM | 6177 | O | VAL | A | 407 | −48.688 | 17.009 | −15.454 | 1.00 | 33.40 | O |
| ATOM | 6179 | N | GLN | A | 408 | −49.693 | 18.767 | −16.463 | 1.00 | 34.93 | N |
| ATOM | 6180 | CA | GLN | A | 408 | −49.930 | 18.102 | −17.749 | 1.00 | 36.16 | C |
| ATOM | 6182 | CB | GLN | A | 408 | −50.779 | 19.016 | −18.638 | 1.00 | 36.63 | C |
| ATOM | 6185 | CG | GLN | A | 408 | −51.625 | 18.270 | −19.672 | 1.00 | 38.95 | C |
| ATOM | 6188 | CD | GLN | A | 408 | −52.991 | 18.930 | −19.887 | 1.00 | 41.80 | C |
| ATOM | 6189 | OE1 | GLN | A | 408 | −53.739 | 19.150 | −18.921 | 1.00 | 43.40 | O |
| ATOM | 6190 | NE2 | GLN | A | 408 | −53.323 | 19.244 | −21.151 | 1.00 | 41.68 | N |
| ATOM | 6193 | C | GLN | A | 408 | −48.630 | 17.725 | −18.470 | 1.00 | 36.22 | C |
| ATOM | 6194 | O | GLN | A | 408 | −48.456 | 16.588 | −18.920 | 1.00 | 35.86 | O |
| ATOM | 6196 | N | ASN | A | 409 | −47.726 | 18.694 | −18.578 | 1.00 | 36.64 | N |
| ATOM | 6197 | CA | ASN | A | 409 | −46.400 | 18.441 | −19.136 | 1.00 | 36.85 | C |
| ATOM | 6199 | CB | ASN | A | 409 | −46.134 | 19.306 | −20.373 | 1.00 | 36.73 | C |
| ATOM | 6202 | CG | ASN | A | 409 | −46.808 | 18.752 | −21.604 | 1.00 | 36.19 | C |
| ATOM | 6203 | OD1 | ASN | A | 409 | −46.178 | 18.072 | −22.420 | 1.00 | 35.00 | O |
| ATOM | 6204 | ND2 | ASN | A | 409 | −48.110 | 18.994 | −21.720 | 1.00 | 34.99 | N |
| ATOM | 6207 | C | ASN | A | 409 | −45.312 | 18.613 | −18.095 | 1.00 | 36.96 | C |
| ATOM | 6208 | O | ASN | A | 409 | −45.032 | 19.720 | −17.618 | 1.00 | 36.81 | O |
| ATOM | 6210 | N | ILE | A | 410 | −44.713 | 17.488 | −17.734 | 1.00 | 37.10 | N |
| ATOM | 6211 | CA | ILE | A | 410 | −43.625 | 17.508 | −16.792 | 1.00 | 37.27 | C |
| ATOM | 6213 | CB | ILE | A | 410 | −43.265 | 16.092 | −16.295 | 1.00 | 37.38 | C |
| ATOM | 6215 | CG1 | ILE | A | 410 | −42.745 | 15.209 | −17.426 | 1.00 | 37.84 | C |
| ATOM | 6218 | CD1 | ILE | A | 410 | −42.416 | 13.824 | −16.985 | 1.00 | 38.96 | C |
| ATOM | 6222 | CG2 | ILE | A | 410 | −44.491 | 15.437 | −15.676 | 1.00 | 37.67 | C |
| ATOM | 6226 | C | ILE | A | 410 | −42.467 | 18.179 | −17.492 | 1.00 | 37.12 | C |
| ATOM | 6227 | O | ILE | A | 410 | −42.150 | 17.839 | −18.617 | 1.00 | 36.87 | O |
| ATOM | 6229 | N | LYS | A | 411 | −41.896 | 19.187 | −16.851 | 1.00 | 37.38 | N |
| ATOM | 6230 | CA | LYS | A | 411 | −40.680 | 19.813 | −17.332 | 1.00 | 37.73 | C |
| ATOM | 6232 | CB | LYS | A | 411 | −40.756 | 21.332 | −17.171 | 1.00 | 38.15 | C |
| ATOM | 6235 | CG | LYS | A | 411 | −41.979 | 21.962 | −17.837 | 1.00 | 39.89 | C |
| ATOM | 6238 | CD | LYS | A | 411 | −41.797 | 23.463 | −18.080 | 1.00 | 42.48 | C |
| ATOM | 6241 | CE | LYS | A | 411 | −43.029 | 24.069 | −18.795 | 1.00 | 44.22 | C |
| ATOM | 6244 | NZ | LYS | A | 411 | −42.977 | 25.576 | −18.904 | 1.00 | 45.31 | N |
| ATOM | 6248 | C | LYS | A | 411 | −39.562 | 19.244 | −16.489 | 1.00 | 37.38 | C |
| ATOM | 6249 | O | LYS | A | 411 | −39.721 | 19.112 | −15.281 | 1.00 | 37.28 | O |
| ATOM | 6251 | N | LYS | A | 412 | −38.445 | 18.886 | −17.122 | 1.00 | 37.24 | N |
| ATOM | 6252 | CA | LYS | A | 412 | −37.333 | 18.243 | −16.413 | 1.00 | 36.95 | C |
| ATOM | 6254 | CB | LYS | A | 412 | −36.286 | 17.701 | −17.384 | 1.00 | 37.14 | C |
| ATOM | 6257 | CG | LYS | A | 412 | −35.233 | 16.818 | −16.720 | 1.00 | 37.89 | C |
| ATOM | 6260 | CD | LYS | A | 412 | −34.334 | 16.125 | −17.757 | 1.00 | 39.54 | C |
| ATOM | 6263 | CE | LYS | A | 412 | −33.263 | 17.068 | −18.348 | 1.00 | 40.08 | C |
| ATOM | 6266 | NZ | LYS | A | 412 | −32.161 | 17.399 | −17.376 | 1.00 | 40.16 | N |
| ATOM | 6270 | C | LYS | A | 412 | −36.664 | 19.177 | −15.419 | 1.00 | 36.42 | C |
| ATOM | 6271 | O | LYS | A | 412 | −36.246 | 18.728 | −14.357 | 1.00 | 36.56 | O |
| ATOM | 6273 | N | GLU | A | 413 | −36.570 | 20.466 | −15.744 | 1.00 | 35.77 | N |
| ATOM | 6274 | CA | GLU | A | 413 | −35.948 | 21.423 | −14.820 | 1.00 | 35.38 | C |
| ATOM | 6276 | CB | GLU | A | 413 | −35.688 | 22.792 | −15.489 | 1.00 | 35.73 | C |
| ATOM | 6279 | CG | GLU | A | 413 | −36.510 | 24.013 | −14.973 | 1.00 | 37.10 | C |
| ATOM | 6282 | CD | GLU | A | 413 | −35.621 | 25.235 | −14.633 | 1.00 | 38.51 | C |
| ATOM | 6283 | OE1 | GLU | A | 413 | −34.778 | 25.125 | −13.714 | 1.00 | 39.24 | O |
| ATOM | 6284 | OE2 | GLU | A | 413 | −35.768 | 26.306 | −15.266 | 1.00 | 39.04 | O |
| ATOM | 6285 | C | GLU | A | 413 | −36.760 | 21.551 | −13.522 | 1.00 | 34.43 | C |
| ATOM | 6286 | O | GLU | A | 413 | −36.196 | 21.801 | −12.460 | 1.00 | 34.34 | O |
| ATOM | 6288 | N | GLU | A | 414 | −38.074 | 21.360 | −13.616 | 1.00 | 33.45 | N |
| ATOM | 6289 | CA | GLU | A | 414 | −38.956 | 21.407 | −12.452 | 1.00 | 32.80 | C |
| ATOM | 6291 | CB | GLU | A | 414 | −40.435 | 21.425 | −12.864 | 1.00 | 32.83 | C |
| ATOM | 6294 | CG | GLU | A | 414 | −40.923 | 22.736 | −13.478 | 1.00 | 33.15 | C |

TABLE 3-7-continued

| | | | | | Coordinates of *P. tremuloides* IspS | | | | | |
|---|---|---|---|---|---|---|---|---|---|---|
| ATOM | 6297 | CD | GLU | A | 414 | −42.360 | 22.668 | −14.003 | 1.00 | 33.82 | C |
| ATOM | 6298 | OE1 | GLU | A | 414 | −42.876 | 21.560 | −14.231 | 1.00 | 35.31 | O |
| ATOM | 6299 | OE2 | GLU | A | 414 | −42.985 | 23.727 | −14.204 | 1.00 | 33.98 | O |
| ATOM | 6300 | C | GLU | A | 414 | −38.715 | 20.222 | −11.536 | 1.00 | 32.18 | C |
| ATOM | 6301 | O | GLU | A | 414 | −38.407 | 20.409 | −10.372 | 1.00 | 32.25 | O |
| ATOM | 6303 | N | ILE | A | 415 | −38.863 | 19.002 | −12.044 | 1.00 | 31.63 | N |
| ATOM | 6304 | CA | ILE | A | 415 | −38.725 | 17.819 | −11.181 | 1.00 | 31.28 | C |
| ATOM | 6306 | CB | ILE | A | 415 | −39.131 | 16.472 | −11.852 | 1.00 | 31.14 | C |
| ATOM | 6308 | CG1 | ILE | A | 415 | −38.349 | 16.204 | −13.133 | 1.00 | 31.13 | C |
| ATOM | 6311 | CD1 | ILE | A | 415 | −38.786 | 14.926 | −13.836 | 1.00 | 30.72 | C |
| ATOM | 6315 | CG2 | ILE | A | 415 | −40.611 | 16.454 | −12.160 | 1.00 | 31.12 | C |
| ATOM | 6319 | C | ILE | A | 415 | −37.316 | 17.705 | −10.636 | 1.00 | 31.08 | C |
| ATOM | 6320 | O | ILE | A | 415 | −37.105 | 17.188 | −9.539 | 1.00 | 31.22 | O |
| ATOM | 6322 | N | GLU | A | 416 | −36.345 | 18.208 | −11.381 | 1.00 | 30.67 | N |
| ATOM | 6323 | CA | GLU | A | 416 | −34.998 | 18.270 | −10.850 | 1.00 | 30.55 | C |
| ATOM | 6325 | CB | GLU | A | 416 | −34.011 | 18.654 | −11.955 | 1.00 | 30.91 | C |
| ATOM | 6328 | CG | GLU | A | 416 | −32.654 | 17.967 | −11.845 | 1.00 | 32.55 | C |
| ATOM | 6331 | CD | GLU | A | 416 | −31.802 | 18.130 | −13.109 | 1.00 | 34.91 | C |
| ATOM | 6332 | OE1 | GLU | A | 416 | −32.337 | 18.563 | −14.161 | 1.00 | 35.53 | O |
| ATOM | 6333 | OE2 | GLU | A | 416 | −30.590 | 17.816 | −13.052 | 1.00 | 36.45 | O |
| ATOM | 6334 | C | GLU | A | 416 | −34.962 | 19.249 | −9.650 | 1.00 | 29.74 | C |
| ATOM | 6335 | O | GLU | A | 416 | −34.143 | 19.097 | −8.738 | 1.00 | 29.73 | O |
| ATOM | 6337 | N | ASN | A | 417 | −35.864 | 20.234 | −9.652 | 1.00 | 28.69 | N |
| ATOM | 6338 | CA | ASN | A | 417 | −36.060 | 21.134 | −8.503 | 1.00 | 27.92 | C |
| ATOM | 6340 | CB | ASN | A | 417 | −36.632 | 22.477 | −8.963 | 1.00 | 27.75 | C |
| ATOM | 6343 | CG | ASN | A | 417 | −35.572 | 23.532 | −9.095 | 1.00 | 26.84 | C |
| ATOM | 6344 | OD1 | ASN | A | 417 | −35.160 | 24.132 | −8.105 | 1.00 | 24.88 | O |
| ATOM | 6345 | ND2 | ASN | A | 417 | −35.117 | 23.765 | −10.318 | 1.00 | 26.28 | N |
| ATOM | 6348 | C | ASN | A | 417 | −36.917 | 20.580 | −7.356 | 1.00 | 27.41 | C |
| ATOM | 6349 | O | ASN | A | 417 | −36.650 | 20.838 | −6.187 | 1.00 | 27.15 | O |
| ATOM | 6351 | N | LEU | A | 418 | −37.955 | 19.834 | −7.675 | 1.00 | 27.09 | N |
| ATOM | 6352 | CA | LEU | A | 418 | −38.694 | 19.156 | −6.628 | 1.00 | 27.02 | C |
| ATOM | 6354 | CB | LEU | A | 418 | −39.921 | 18.423 | −7.200 | 1.00 | 26.95 | C |
| ATOM | 6357 | CG | LEU | A | 418 | −41.030 | 19.284 | −7.826 | 1.00 | 25.97 | C |
| ATOM | 6359 | CD1 | LEU | A | 418 | −42.127 | 18.429 | −8.447 | 1.00 | 24.88 | C |
| ATOM | 6363 | CD2 | LEU | A | 418 | −41.623 | 20.226 | −6.803 | 1.00 | 24.50 | C |
| ATOM | 6367 | C | LEU | A | 418 | −37.763 | 18.196 | −5.860 | 1.00 | 27.26 | C |
| ATOM | 6368 | O | LEU | A | 418 | −37.834 | 18.123 | −4.644 | 1.00 | 27.07 | O |
| ATOM | 6370 | N | GLN | A | 419 | −36.873 | 17.494 | −6.561 | 1.00 | 27.67 | N |
| ATOM | 6371 | CA | GLN | A | 419 | −35.924 | 16.575 | −5.909 | 1.00 | 28.28 | C |
| ATOM | 6373 | CB | GLN | A | 419 | −35.155 | 15.758 | −6.945 | 1.00 | 28.36 | C |
| ATOM | 6376 | CG | GLN | A | 419 | −35.747 | 14.375 | −7.146 | 1.00 | 29.43 | C |
| ATOM | 6379 | CD | GLN | A | 419 | −35.052 | 13.573 | −8.215 | 1.00 | 29.76 | C |
| ATOM | 6380 | OE1 | GLN | A | 419 | −34.355 | 14.112 | −9.066 | 1.00 | 29.93 | O |
| ATOM | 6381 | NE2 | GLN | A | 419 | −35.252 | 12.270 | −8.184 | 1.00 | 31.33 | N |
| ATOM | 6384 | C | GLN | A | 419 | −34.922 | 17.219 | −4.947 | 1.00 | 28.73 | C |
| ATOM | 6385 | O | GLN | A | 419 | −34.540 | 16.608 | −3.952 | 1.00 | 28.90 | O |
| ATOM | 6387 | N | LYS | A | 420 | −34.490 | 18.440 | −5.240 | 1.00 | 29.27 | N |
| ATOM | 6388 | CA | LYS | A | 420 | −33.608 | 19.166 | −4.335 | 1.00 | 29.81 | C |
| ATOM | 6390 | CB | LYS | A | 420 | −32.758 | 20.163 | −5.129 | 1.00 | 30.24 | C |
| ATOM | 6393 | CG | LYS | A | 420 | −31.592 | 19.513 | −5.867 | 1.00 | 31.75 | C |
| ATOM | 6396 | CD | LYS | A | 420 | −31.259 | 20.217 | −7.183 | 1.00 | 34.14 | C |
| ATOM | 6399 | CE | LYS | A | 420 | −30.140 | 19.463 | −7.953 | 1.00 | 36.21 | C |
| ATOM | 6402 | NZ | LYS | A | 420 | −30.073 | 19.759 | −9.439 | 1.00 | 36.76 | N |
| ATOM | 6406 | C | LYS | A | 420 | −34.375 | 19.872 | −3.204 | 1.00 | 29.98 | C |
| ATOM | 6407 | O | LYS | A | 420 | −33.759 | 20.547 | −2.384 | 1.00 | 30.44 | O |
| ATOM | 6409 | N | TYR | A | 421 | −35.706 | 19.694 | −3.162 | 1.00 | 30.07 | N |
| ATOM | 6410 | CA | TYR | A | 421 | −36.646 | 20.309 | −2.171 | 1.00 | 29.73 | C |
| ATOM | 6412 | CB | TYR | A | 421 | −36.298 | 19.949 | −.712 | 1.00 | 29.59 | C |
| ATOM | 6415 | CG | TYR | A | 421 | −36.386 | 18.468 | −.470 | 1.00 | 30.57 | C |
| ATOM | 6416 | CD1 | TYR | A | 421 | −37.582 | 17.785 | −.643 | 1.00 | 30.87 | C |
| ATOM | 6418 | CE1 | TYR | A | 421 | −37.665 | 16.414 | −.448 | 1.00 | 31.28 | C |
| ATOM | 6420 | CZ | TYR | A | 421 | −36.549 | 15.705 | −.068 | 1.00 | 31.90 | C |
| ATOM | 6421 | OH | TYR | A | 421 | −36.620 | 14.347 | .124 | 1.00 | 32.43 | O |
| ATOM | 6423 | CE2 | TYR | A | 421 | −35.355 | 16.354 | .119 | 1.00 | 32.68 | C |
| ATOM | 6425 | CD2 | TYR | A | 421 | −35.274 | 17.736 | −.095 | 1.00 | 32.42 | C |
| ATOM | 6427 | C | TYR | A | 421 | −36.850 | 21.816 | −2.347 | 1.00 | 29.24 | C |
| ATOM | 6428 | O | TYR | A | 421 | −36.709 | 22.590 | −1.401 | 1.00 | 29.26 | O |
| ATOM | 6430 | N | HIS | A | 422 | −37.219 | 22.214 | −3.563 | 1.00 | 28.65 | N |
| ATOM | 6431 | CA | HIS | A | 422 | −37.540 | 23.604 | −3.859 | 1.00 | 28.26 | C |
| ATOM | 6433 | CB | HIS | A | 422 | −38.150 | 23.715 | −5.256 | 1.00 | 28.33 | C |
| ATOM | 6436 | CG | HIS | A | 422 | −38.299 | 25.124 | −5.748 | 1.00 | 28.44 | C |
| ATOM | 6437 | ND1 | HIS | A | 422 | −37.225 | 25.904 | −6.106 | 1.00 | 28.97 | N |
| ATOM | 6439 | CE1 | HIS | A | 422 | −37.660 | 27.082 | −6.520 | 1.00 | 29.40 | C |
| ATOM | 6441 | NE2 | HIS | A | 422 | −38.977 | 27.090 | −6.443 | 1.00 | 28.14 | N |
| ATOM | 6443 | CD2 | HIS | A | 422 | −39.399 | 25.879 | −5.965 | 1.00 | 27.76 | C |
| ATOM | 6445 | C | HIS | A | 422 | −38.511 | 24.147 | −2.816 | 1.00 | 27.74 | C |
| ATOM | 6446 | O | HIS | A | 422 | −39.357 | 23.408 | −2.310 | 1.00 | 27.53 | O |

TABLE 3-7-continued

| | | | | | | | | | | | |
|---|---|---|---|---|---|---|---|---|---|---|---|
| ATOM | 6448 | N | ASP | A | 423 | −38.384 | 25.437 | −2.505 | 1.00 | 27.12 | N |
| ATOM | 6449 | CA | ASP | A | 423 | −39.186 | 26.072 | −1.454 | 1.00 | 26.63 | C |
| ATOM | 6451 | CB | ASP | A | 423 | −38.877 | 27.575 | −1.349 | 1.00 | 27.05 | C |
| ATOM | 6454 | CG | ASP | A | 423 | −37.456 | 27.875 | −.851 | 1.00 | 28.35 | C |
| ATOM | 6455 | OD1 | ASP | A | 423 | −36.951 | 27.121 | .018 | 1.00 | 30.99 | O |
| ATOM | 6456 | OD2 | ASP | A | 423 | −36.860 | 28.884 | −1.322 | 1.00 | 27.89 | O |
| ATOM | 6457 | C | ASP | A | 423 | −40.689 | 25.883 | −1.698 | 1.00 | 25.71 | C |
| ATOM | 6458 | O | ASP | A | 423 | −41.487 | 25.831 | −.749 | 1.00 | 26.26 | O |
| ATOM | 6460 | N | ILE | A | 424 | −41.075 | 25.781 | −2.966 | 1.00 | 24.01 | N |
| ATOM | 6461 | CA | ILE | A | 424 | −42.479 | 25.596 | −3.327 | 1.00 | 22.72 | C |
| ATOM | 6463 | CB | ILE | A | 424 | −42.639 | 25.391 | −4.843 | 1.00 | 22.40 | C |
| ATOM | 6465 | CG1 | ILE | A | 424 | −44.029 | 25.668 | −5.318 | 1.00 | 21.78 | C |
| ATOM | 6468 | CD1 | ILE | A | 424 | −44.086 | 25.499 | −6.793 | 1.00 | 22.22 | C |
| ATOM | 6472 | CG2 | ILE | A | 424 | −42.340 | 23.985 | −5.255 | 1.00 | 22.87 | C |
| ATOM | 6476 | C | ILE | A | 424 | −43.103 | 24.442 | −2.562 | 1.00 | 21.91 | C |
| ATOM | 6477 | O | ILE | A | 424 | −44.238 | 24.574 | −2.115 | 1.00 | 21.73 | O |
| ATOM | 6479 | N | ILE | A | 425 | −42.365 | 23.334 | −2.399 | 1.00 | 21.23 | N |
| ATOM | 6480 | CA | ILE | A | 425 | −42.853 | 22.173 | −1.634 | 1.00 | 20.73 | C |
| ATOM | 6482 | CB | ILE | A | 425 | −42.622 | 20.820 | −2.330 | 1.00 | 20.10 | C |
| ATOM | 6484 | CG1 | ILE | A | 425 | −41.158 | 20.409 | −2.290 | 1.00 | 18.72 | C |
| ATOM | 6487 | CD1 | ILE | A | 425 | −40.923 | 19.075 | −2.948 | 1.00 | 18.27 | C |
| ATOM | 6491 | CG2 | ILE | A | 425 | −43.146 | 20.840 | −3.741 | 1.00 | 19.57 | C |
| ATOM | 6495 | C | ILE | A | 425 | −42.252 | 22.060 | −.242 | 1.00 | 21.21 | C |
| ATOM | 6496 | O | ILE | A | 425 | −42.810 | 21.370 | .613 | 1.00 | 21.30 | O |
| ATOM | 6498 | N | SER | A | 426 | −41.129 | 22.721 | −.002 | 1.00 | 21.56 | N |
| ATOM | 6499 | CA | SER | A | 426 | −40.492 | 22.620 | 1.299 | 1.00 | 22.23 | C |
| ATOM | 6501 | CB | SER | A | 426 | −39.043 | 23.082 | 1.234 | 1.00 | 22.36 | C |
| ATOM | 6504 | OG | SER | A | 426 | −38.977 | 24.501 | 1.342 | 1.00 | 24.09 | O |
| ATOM | 6506 | C | SER | A | 426 | −41.242 | 23.460 | 2.334 | 1.00 | 22.39 | C |
| ATOM | 6507 | O | SER | A | 426 | −41.390 | 23.051 | 3.491 | 1.00 | 22.95 | O |
| ATOM | 6509 | N | ARG | A | 427 | −41.701 | 24.643 | 1.937 | 1.00 | 22.08 | N |
| ATOM | 6510 | CA | ARG | A | 427 | −42.332 | 25.541 | 2.905 | 1.00 | 21.87 | C |
| ATOM | 6512 | CB | ARG | A | 427 | −42.466 | 26.955 | 2.345 | 1.00 | 21.99 | C |
| ATOM | 6515 | CG | ARG | A | 427 | −41.170 | 27.696 | 2.493 | 1.00 | 23.36 | C |
| ATOM | 6518 | CD | ARG | A | 427 | −40.954 | 28.727 | 1.433 | 1.00 | 26.07 | C |
| ATOM | 6521 | NE | ARG | A | 427 | −39.680 | 29.407 | 1.667 | 1.00 | 28.18 | N |
| ATOM | 6523 | CZ | ARG | A | 427 | −39.127 | 30.298 | .844 | 1.00 | 29.21 | C |
| ATOM | 6524 | NH1 | ARG | A | 427 | −39.723 | 30.633 | −.298 | 1.00 | 28.60 | N |
| ATOM | 6527 | NH2 | ARG | A | 427 | −37.962 | 30.854 | 1.173 | 1.00 | 30.48 | N |
| ATOM | 6530 | C | ARG | A | 427 | −43.651 | 25.003 | 3.434 | 1.00 | 21.21 | C |
| ATOM | 6531 | O | ARG | A | 427 | −43.817 | 24.891 | 4.645 | 1.00 | 21.11 | O |
| ATOM | 6533 | N | PRO | A | 428 | −44.573 | 24.622 | 2.541 | 1.00 | 20.52 | N |
| ATOM | 6534 | CA | PRO | A | 428 | −45.789 | 23.999 | 3.040 | 1.00 | 20.27 | C |
| ATOM | 6536 | CB | PRO | A | 428 | −46.410 | 23.369 | 1.791 | 1.00 | 20.44 | C |
| ATOM | 6539 | CG | PRO | A | 428 | −45.864 | 24.119 | .666 | 1.00 | 20.63 | C |
| ATOM | 6542 | CD | PRO | A | 428 | −44.521 | 24.644 | 1.074 | 1.00 | 20.54 | C |
| ATOM | 6545 | C | PRO | A | 428 | −45.450 | 22.917 | 4.050 | 1.00 | 19.75 | C |
| ATOM | 6546 | O | PRO | A | 428 | −46.089 | 22.834 | 5.095 | 1.00 | 19.77 | O |
| ATOM | 6547 | N | SER | A | 429 | −44.424 | 22.123 | 3.747 | 1.00 | 18.97 | N |
| ATOM | 6548 | CA | SER | A | 429 | −44.008 | 21.045 | 4.636 | 1.00 | 18.45 | C |
| ATOM | 6550 | CB | SER | A | 429 | −42.954 | 20.180 | 3.972 | 1.00 | 18.35 | C |
| ATOM | 6553 | OG | SER | A | 429 | −43.452 | 19.716 | 2.733 | 1.00 | 19.12 | O |
| ATOM | 6555 | C | SER | A | 429 | −43.519 | 21.525 | 5.985 | 1.00 | 17.97 | C |
| ATOM | 6556 | O | SER | A | 429 | −43.733 | 20.846 | 6.968 | 1.00 | 17.88 | O |
| ATOM | 6558 | N | HIS | A | 430 | −42.879 | 22.689 | 6.053 | 1.00 | 17.73 | N |
| ATOM | 6559 | CA | HIS | A | 430 | −42.593 | 23.289 | 7.359 | 1.00 | 17.71 | C |
| ATOM | 6561 | CB | HIS | A | 430 | −41.937 | 24.668 | 7.241 | 1.00 | 17.97 | C |
| ATOM | 6564 | CG | HIS | A | 430 | −40.558 | 24.663 | 6.651 | 1.00 | 18.87 | C |
| ATOM | 6565 | ND1 | HIS | A | 430 | −39.940 | 23.524 | 6.186 | 1.00 | 19.85 | N |
| ATOM | 6567 | CE1 | HIS | A | 430 | −38.746 | 23.836 | 5.709 | 1.00 | 19.43 | C |
| ATOM | 6569 | NE2 | HIS | A | 430 | −38.573 | 25.137 | 5.838 | 1.00 | 19.06 | N |
| ATOM | 6571 | CD2 | HIS | A | 430 | −39.693 | 25.681 | 6.418 | 1.00 | 19.32 | C |
| ATOM | 6573 | C | HIS | A | 430 | −43.914 | 23.444 | 8.131 | 1.00 | 17.31 | C |
| ATOM | 6574 | O | HIS | A | 430 | −44.023 | 23.013 | 9.287 | 1.00 | 17.06 | O |
| ATOM | 6576 | N | ILE | A | 431 | −44.913 | 24.050 | 7.475 | 1.00 | 16.74 | N |
| ATOM | 6577 | CA | ILE | A | 431 | −46.218 | 24.304 | 8.091 | 1.00 | 16.15 | C |
| ATOM | 6579 | CB | ILE | A | 431 | −47.174 | 25.057 | 7.174 | 1.00 | 16.18 | C |
| ATOM | 6581 | CG1 | ILE | A | 431 | −46.613 | 26.428 | 6.801 | 1.00 | 17.05 | C |
| ATOM | 6584 | CD1 | ILE | A | 431 | −46.441 | 27.352 | 7.994 | 1.00 | 18.34 | C |
| ATOM | 6588 | CG2 | ILE | A | 431 | −48.496 | 25.263 | 7.860 | 1.00 | 15.28 | C |
| ATOM | 6592 | C | ILE | A | 431 | −46.899 | 23.021 | 8.476 | 1.00 | 15.75 | C |
| ATOM | 6593 | O | ILE | A | 431 | −47.624 | 22.980 | 9.445 | 1.00 | 15.95 | O |
| ATOM | 6595 | N | PHE | A | 432 | −46.663 | 21.969 | 7.714 | 1.00 | 15.59 | N |
| ATOM | 6596 | CA | PHE | A | 432 | −47.192 | 20.652 | 8.041 | 1.00 | 15.52 | C |
| ATOM | 6598 | CB | PHE | A | 432 | −46.837 | 19.683 | 6.913 | 1.00 | 15.23 | C |
| ATOM | 6601 | CG | PHE | A | 432 | −47.451 | 18.318 | 7.031 | 1.00 | 15.98 | C |
| ATOM | 6602 | CD1 | PHE | A | 432 | −48.324 | 17.972 | 8.052 | 1.00 | 16.55 | C |
| ATOM | 6604 | CE1 | PHE | A | 432 | −48.867 | 16.700 | 8.102 | 1.00 | 16.04 | C |

TABLE 3-7-continued

| | | | | | | | | | | | |
|---|---|---|---|---|---|---|---|---|---|---|---|
| ATOM | 6606 | CZ | PHE | A | 432 | −48.559 | 15.774 | 7.130 | 1.00 | 15.29 | C |
| ATOM | 6608 | CE2 | PHE | A | 432 | −47.718 | 16.107 | 6.114 | 1.00 | 15.37 | C |
| ATOM | 6610 | CD2 | PHE | A | 432 | −47.172 | 17.364 | 6.061 | 1.00 | 16.74 | C |
| ATOM | 6612 | C | PHE | A | 432 | −46.640 | 20.191 | 9.392 | 1.00 | 15.54 | C |
| ATOM | 6613 | O | PHE | A | 432 | −47.383 | 20.006 | 10.343 | 1.00 | 15.37 | O |
| ATOM | 6615 | N | ARG | A | 433 | −45.328 | 20.041 | 9.483 | 1.00 | 15.98 | N |
| ATOM | 6616 | CA | ARG | A | 433 | −44.695 | 19.542 | 10.709 | 1.00 | 16.20 | C |
| ATOM | 6618 | CB | ARG | A | 433 | −43.176 | 19.476 | 10.526 | 1.00 | 15.85 | C |
| ATOM | 6621 | CG | ARG | A | 433 | −42.411 | 19.183 | 11.804 | 1.00 | 16.11 | C |
| ATOM | 6624 | CD | ARG | A | 433 | −42.848 | 17.890 | 12.489 | 1.00 | 15.70 | C |
| ATOM | 6627 | NE | ARG | A | 433 | −42.811 | 16.747 | 11.588 | 1.00 | 15.64 | N |
| ATOM | 6629 | CZ | ARG | A | 433 | −43.377 | 15.571 | 11.838 | 1.00 | 16.27 | C |
| ATOM | 6630 | NH1 | ARG | A | 433 | −44.029 | 15.359 | 12.965 | 1.00 | 16.82 | N |
| ATOM | 6633 | NH2 | ARG | A | 433 | −43.302 | 14.598 | 10.948 | 1.00 | 16.96 | N |
| ATOM | 6636 | C | ARG | A | 433 | −45.029 | 20.411 | 11.935 | 1.00 | 16.46 | C |
| ATOM | 6637 | O | ARG | A | 433 | −45.296 | 19.890 | 13.031 | 1.00 | 16.31 | O |
| ATOM | 6639 | N | LEU | A | 434 | −45.006 | 21.731 | 11.724 | 1.00 | 16.47 | N |
| ATOM | 6640 | CA | LEU | A | 434 | −45.123 | 22.701 | 12.800 | 1.00 | 15.98 | C |
| ATOM | 6642 | CB | LEU | A | 434 | −44.771 | 24.114 | 12.303 | 1.00 | 15.83 | C |
| ATOM | 6645 | CG | LEU | A | 434 | −43.287 | 24.486 | 12.218 | 1.00 | 14.95 | C |
| ATOM | 6647 | CD1 | LEU | A | 434 | −43.130 | 25.918 | 11.826 | 1.00 | 15.09 | C |
| ATOM | 6651 | CD2 | LEU | A | 434 | −42.600 | 24.281 | 13.536 | 1.00 | 14.37 | C |
| ATOM | 6655 | C | LEU | A | 434 | −46.517 | 22.660 | 13.387 | 1.00 | 16.19 | C |
| ATOM | 6656 | O | LEU | A | 434 | −46.669 | 22.564 | 14.604 | 1.00 | 15.92 | O |
| ATOM | 6658 | N | CYS | A | 435 | −47.529 | 22.715 | 12.520 | 1.00 | 16.78 | N |
| ATOM | 6659 | CA | CYS | A | 435 | −48.936 | 22.591 | 12.940 | 1.00 | 17.48 | C |
| ATOM | 6661 | CB | CYS | A | 435 | −49.870 | 22.617 | 11.726 | 1.00 | 17.54 | C |
| ATOM | 6664 | SG | CYS | A | 435 | −50.110 | 24.233 | 10.985 | 1.00 | 18.80 | S |
| ATOM | 6666 | C | CYS | A | 435 | −49.192 | 21.296 | 13.708 | 1.00 | 17.84 | C |
| ATOM | 6667 | O | CYS | A | 435 | −50.043 | 21.250 | 14.597 | 1.00 | 17.92 | O |
| ATOM | 6669 | N | ASN | A | 436 | −48.446 | 20.257 | 13.333 | 1.00 | 18.24 | N |
| ATOM | 6670 | CA | ASN | A | 436 | −48.603 | 18.913 | 13.846 | 1.00 | 18.50 | C |
| ATOM | 6672 | CB | ASN | A | 436 | −47.936 | 17.949 | 12.867 | 1.00 | 18.63 | C |
| ATOM | 6675 | CG | ASN | A | 436 | −48.156 | 16.487 | 13.213 | 1.00 | 18.58 | C |
| ATOM | 6676 | OD1 | ASN | A | 436 | −48.810 | 16.129 | 14.185 | 1.00 | 18.80 | O |
| ATOM | 6677 | ND2 | ASN | A | 436 | −47.588 | 15.633 | 12.398 | 1.00 | 19.29 | N |
| ATOM | 6680 | C | ASN | A | 436 | −47.975 | 18.755 | 15.210 | 1.00 | 18.83 | C |
| ATOM | 6681 | O | ASN | A | 436 | −48.551 | 18.153 | 16.115 | 1.00 | 19.00 | O |
| ATOM | 6683 | N | ASP | A | 437 | −46.763 | 19.255 | 15.351 | 1.00 | 19.29 | N |
| ATOM | 6684 | CA | ASP | A | 437 | −46.097 | 19.179 | 16.634 | 1.00 | 19.62 | C |
| ATOM | 6686 | CB | ASP | A | 437 | −44.615 | 19.522 | 16.510 | 1.00 | 19.45 | C |
| ATOM | 6689 | CG | ASP | A | 437 | −43.849 | 18.480 | 15.734 | 1.00 | 19.36 | C |
| ATOM | 6690 | OD1 | ASP | A | 437 | −44.491 | 17.586 | 15.158 | 1.00 | 19.89 | O |
| ATOM | 6691 | OD2 | ASP | A | 437 | −42.608 | 18.543 | 15.699 | 1.00 | 19.86 | O |
| ATOM | 6692 | C | ASP | A | 437 | −46.799 | 20.106 | 17.597 | 1.00 | 20.01 | C |
| ATOM | 6693 | O | ASP | A | 437 | −46.916 | 19.790 | 18.779 | 1.00 | 20.30 | O |
| ATOM | 6695 | N | LEU | A | 438 | −47.288 | 21.233 | 17.092 | 1.00 | 20.40 | N |
| ATOM | 6696 | CA | LEU | A | 438 | −47.996 | 22.174 | 17.940 | 1.00 | 21.03 | C |
| ATOM | 6698 | CB | LEU | A | 438 | −48.510 | 23.363 | 17.126 | 1.00 | 21.01 | C |
| ATOM | 6701 | CG | LEU | A | 438 | −47.575 | 24.565 | 17.078 | 1.00 | 20.32 | C |
| ATOM | 6703 | CD1 | LEU | A | 438 | −47.938 | 25.524 | 15.952 | 1.00 | 19.14 | C |
| ATOM | 6707 | CD2 | LEU | A | 438 | −47.611 | 25.263 | 18.415 | 1.00 | 19.73 | C |
| ATOM | 6711 | C | LEU | A | 438 | −49.153 | 21.496 | 18.679 | 1.00 | 21.81 | C |
| ATOM | 6712 | O | LEU | A | 438 | −49.277 | 21.633 | 19.902 | 1.00 | 21.55 | O |
| ATOM | 6714 | N | ALA | A | 439 | −49.973 | 20.754 | 17.932 | 1.00 | 22.76 | N |
| ATOM | 6715 | CA | ALA | A | 439 | −51.138 | 20.055 | 18.486 | 1.00 | 23.58 | C |
| ATOM | 6717 | CB | ALA | A | 439 | −51.905 | 19.360 | 17.386 | 1.00 | 23.57 | C |
| ATOM | 6721 | C | ALA | A | 439 | −50.746 | 19.042 | 19.542 | 1.00 | 24.47 | C |
| ATOM | 6722 | O | ALA | A | 439 | −51.386 | 18.951 | 20.575 | 1.00 | 24.63 | O |
| ATOM | 6724 | N | SER | A | 440 | −49.685 | 18.291 | 19.276 | 1.00 | 25.78 | N |
| ATOM | 6725 | CA | SER | A | 440 | −49.242 | 17.227 | 20.168 | 1.00 | 26.84 | C |
| ATOM | 6727 | CB | SER | A | 440 | −48.566 | 16.130 | 19.353 | 1.00 | 26.92 | C |
| ATOM | 6730 | OG | SER | A | 440 | −47.321 | 16.582 | 18.859 | 1.00 | 27.46 | O |
| ATOM | 6732 | C | SER | A | 440 | −48.270 | 17.691 | 21.244 | 1.00 | 27.68 | C |
| ATOM | 6733 | O | SER | A | 440 | −47.934 | 16.923 | 22.132 | 1.00 | 28.00 | O |
| ATOM | 6735 | N | ALA | A | 441 | −47.822 | 18.935 | 21.174 | 1.00 | 28.83 | N |
| ATOM | 6736 | CA | ALA | A | 441 | −46.760 | 19.419 | 22.056 | 1.00 | 29.73 | C |
| ATOM | 6738 | CB | ALA | A | 441 | −46.529 | 20.910 | 21.841 | 1.00 | 29.84 | C |
| ATOM | 6742 | C | ALA | A | 441 | −46.982 | 19.132 | 23.539 | 1.00 | 30.57 | C |
| ATOM | 6743 | O | ALA | A | 441 | −46.306 | 18.274 | 24.093 | 1.00 | 30.50 | O |
| ATOM | 6745 | N | SER | A | 442 | −47.929 | 19.827 | 24.172 | 1.00 | 31.90 | N |
| ATOM | 6746 | CA | SER | A | 442 | −47.999 | 19.862 | 25.654 | 1.00 | 32.95 | C |
| ATOM | 6748 | CB | SER | A | 442 | −49.043 | 20.870 | 26.169 | 1.00 | 32.91 | C |
| ATOM | 6751 | OG | SER | A | 442 | −50.331 | 20.614 | 25.650 | 1.00 | 33.50 | O |
| ATOM | 6753 | C | SER | A | 442 | −48.219 | 18.497 | 26.289 | 1.00 | 33.69 | C |
| ATOM | 6754 | O | SER | A | 442 | −47.754 | 18.246 | 27.397 | 1.00 | 33.59 | O |
| ATOM | 6756 | N | ALA | A | 443 | −48.922 | 17.623 | 25.578 | 1.00 | 34.93 | N |
| ATOM | 6757 | CA | ALA | A | 443 | −49.050 | 16.231 | 25.980 | 1.00 | 35.81 | C |

TABLE 3-7-continued

| | | | | | | Coordinates of *P. tremuloides* IspS | | | | |
|---|---|---|---|---|---|---|---|---|---|---|
| ATOM | 6759 | CB | ALA | A | 443 | −49.981 | 15.488 | 25.030 | 1.00 | 35.72 C |
| ATOM | 6763 | C | ALA | A | 443 | −47.663 | 15.580 | 25.996 | 1.00 | 36.71 C |
| ATOM | 6764 | O | ALA | A | 443 | −47.198 | 15.115 | 27.047 | 1.00 | 36.94 O |
| ATOM | 6766 | N | GLU | A | 444 | −46.999 | 15.567 | 24.838 | 1.00 | 37.47 N |
| ATOM | 6767 | CA | GLU | A | 444 | −45.688 | 14.930 | 24.718 | 1.00 | 37.93 C |
| ATOM | 6769 | CB | GLU | A | 444 | −45.164 | 14.996 | 23.277 | 1.00 | 37.99 C |
| ATOM | 6772 | CG | GLU | A | 444 | −45.952 | 14.100 | 22.326 | 1.00 | 39.24 C |
| ATOM | 6775 | CD | GLU | A | 444 | −45.419 | 14.080 | 20.886 | 1.00 | 41.03 C |
| ATOM | 6776 | OE1 | GLU | A | 444 | −44.612 | 14.958 | 20.510 | 1.00 | 42.16 O |
| ATOM | 6777 | OE2 | GLU | A | 444 | −45.827 | 13.178 | 20.119 | 1.00 | 42.36 O |
| ATOM | 6778 | C | GLU | A | 444 | −44.694 | 15.534 | 25.708 | 1.00 | 38.09 C |
| ATOM | 6779 | O | GLU | A | 444 | −43.924 | 14.803 | 26.324 | 1.00 | 38.17 O |
| ATOM | 6781 | N | ILE | A | 445 | −44.739 | 16.851 | 25.889 | 1.00 | 38.41 N |
| ATOM | 6782 | CA | ILE | A | 445 | −43.829 | 17.530 | 26.814 | 1.00 | 38.75 C |
| ATOM | 6784 | CB | ILE | A | 445 | −43.802 | 19.065 | 26.587 | 1.00 | 38.69 C |
| ATOM | 6786 | CG1 | ILE | A | 445 | −43.314 | 19.396 | 25.170 | 1.00 | 38.18 C |
| ATOM | 6789 | CD1 | ILE | A | 445 | −43.702 | 20.775 | 24.712 | 1.00 | 37.58 C |
| ATOM | 6793 | CG2 | ILE | A | 445 | −42.909 | 19.753 | 27.617 | 1.00 | 38.26 C |
| ATOM | 6797 | C | ILE | A | 445 | −44.243 | 17.194 | 28.246 | 1.00 | 39.35 C |
| ATOM | 6798 | O | ILE | A | 445 | −45.039 | 17.901 | 28.870 | 1.00 | 39.44 O |
| ATOM | 6800 | N | ALA | A | 446 | −43.696 | 16.092 | 28.750 | 1.00 | 40.02 N |
| ATOM | 6801 | CA | ALA | A | 446 | −44.082 | 15.540 | 30.045 | 1.00 | 40.51 C |
| ATOM | 6803 | CB | ALA | A | 446 | −43.815 | 16.552 | 31.170 | 1.00 | 40.55 C |
| ATOM | 6807 | C | ALA | A | 446 | −45.559 | 15.130 | 30.029 | 1.00 | 40.86 C |
| ATOM | 6808 | O | ALA | A | 446 | −46.407 | 16.021 | 30.121 | 1.00 | 40.77 O |
| ATOM | 6810 | N | ARG | A | 447 | −45.925 | 13.842 | 29.899 | 1.00 | 41.31 N |
| ATOM | 6811 | CA | ARG | A | 447 | −45.072 | 12.633 | 29.691 | 1.00 | 41.58 C |
| ATOM | 6813 | CB | ARG | A | 447 | −45.272 | 12.092 | 28.258 | 1.00 | 41.84 C |
| ATOM | 6816 | CG | ARG | A | 447 | −46.667 | 11.495 | 27.991 | 1.00 | 42.69 C |
| ATOM | 6819 | CD | ARG | A | 447 | −46.778 | 10.901 | 26.582 | 1.00 | 43.92 C |
| ATOM | 6822 | NE | ARG | A | 447 | −47.764 | 11.589 | 25.744 | 1.00 | 45.34 N |
| ATOM | 6824 | CZ | ARG | A | 447 | −47.887 | 11.435 | 24.420 | 1.00 | 46.56 C |
| ATOM | 6825 | NH1 | ARG | A | 447 | −47.077 | 10.623 | 23.742 | 1.00 | 46.71 N |
| ATOM | 6828 | NH2 | ARG | A | 447 | −48.828 | 12.107 | 23.757 | 1.00 | 46.97 N |
| ATOM | 6831 | C | ARG | A | 447 | −43.581 | 12.728 | 30.054 | 1.00 | 41.38 C |
| ATOM | 6832 | O | ARG | A | 447 | −43.231 | 12.747 | 31.238 | 1.00 | 41.92 O |
| ATOM | 6834 | N | GLY | A | 448 | −42.710 | 12.736 | 29.051 | 1.00 | 40.88 N |
| ATOM | 6835 | CA | GLY | A | 448 | −41.312 | 13.128 | 29.234 | 1.00 | 40.44 C |
| ATOM | 6838 | C | GLY | A | 448 | −40.579 | 13.316 | 27.915 | 1.00 | 40.08 C |
| ATOM | 6839 | O | GLY | A | 448 | −39.364 | 13.488 | 27.901 | 1.00 | 40.05 O |
| ATOM | 6841 | N | GLU | A | 449 | −41.323 | 13.332 | 26.809 | 1.00 | 39.56 N |
| ATOM | 6842 | CA | GLU | A | 449 | −40.750 | 13.132 | 25.486 | 1.00 | 39.19 C |
| ATOM | 6844 | CB | GLU | A | 449 | −41.827 | 12.668 | 24.502 | 1.00 | 39.52 C |
| ATOM | 6847 | CG | GLU | A | 449 | −42.403 | 11.290 | 24.810 | 1.00 | 40.61 C |
| ATOM | 6850 | CD | GLU | A | 449 | −43.348 | 10.782 | 23.715 | 1.00 | 42.21 C |
| ATOM | 6851 | OE1 | GLU | A | 449 | −43.068 | 11.019 | 22.503 | 1.00 | 41.83 O |
| ATOM | 6852 | OE2 | GLU | A | 449 | −44.368 | 10.141 | 24.082 | 1.00 | 42.41 O |
| ATOM | 6853 | C | GLU | A | 449 | −40.037 | 14.365 | 24.921 | 1.00 | 38.34 C |
| ATOM | 6854 | O | GLU | A | 449 | −40.511 | 15.497 | 25.031 | 1.00 | 38.01 O |
| ATOM | 6856 | N | THR | A | 450 | −38.904 | 14.106 | 24.279 | 1.00 | 37.37 N |
| ATOM | 6857 | CA | THR | A | 450 | −38.047 | 15.138 | 23.726 | 1.00 | 36.37 C |
| ATOM | 6859 | CB | THR | A | 450 | −36.607 | 14.985 | 24.285 | 1.00 | 36.39 C |
| ATOM | 6861 | OG1 | THR | A | 450 | −35.846 | 16.153 | 23.982 | 1.00 | 36.63 O |
| ATOM | 6863 | CG2 | THR | A | 450 | −35.888 | 13.749 | 23.706 | 1.00 | 36.52 C |
| ATOM | 6867 | C | THR | A | 450 | −38.013 | 15.100 | 22.190 | 1.00 | 35.36 C |
| ATOM | 6868 | O | THR | A | 450 | −37.175 | 15.764 | 21.583 | 1.00 | 35.43 O |
| ATOM | 6870 | N | ALA | A | 451 | −38.917 | 14.338 | 21.563 | 1.00 | 33.98 N |
| ATOM | 6871 | CA | ALA | A | 451 | −38.920 | 14.182 | 20.096 | 1.00 | 32.81 C |
| ATOM | 6873 | CB | ALA | A | 451 | −39.030 | 12.708 | 19.708 | 1.00 | 32.99 C |
| ATOM | 6877 | C | ALA | A | 451 | −40.043 | 14.987 | 19.459 | 1.00 | 31.46 C |
| ATOM | 6878 | O | ALA | A | 451 | −41.050 | 14.432 | 18.996 | 1.00 | 31.06 O |
| ATOM | 6880 | N | ASN | A | 452 | −39.848 | 16.302 | 19.432 | 1.00 | 29.88 N |
| ATOM | 6881 | CA | ASN | A | 452 | −40.881 | 17.225 | 18.973 | 1.00 | 28.81 C |
| ATOM | 6883 | CB | ASN | A | 452 | −41.957 | 17.329 | 20.051 | 1.00 | 28.57 C |
| ATOM | 6886 | CG | ASN | A | 452 | −42.969 | 18.380 | 19.757 | 1.00 | 28.30 C |
| ATOM | 6887 | OD1 | ASN | A | 452 | −42.622 | 19.517 | 19.468 | 1.00 | 29.35 O |
| ATOM | 6888 | ND2 | ASN | A | 452 | −44.236 | 18.018 | 19.836 | 1.00 | 28.36 N |
| ATOM | 6891 | C | ASN | A | 452 | −40.285 | 18.590 | 18.641 | 1.00 | 27.76 C |
| ATOM | 6892 | O | ASN | A | 452 | −39.365 | 19.018 | 19.296 | 1.00 | 28.04 O |
| ATOM | 6894 | N | SER | A | 453 | −40.807 | 19.269 | 17.630 | 1.00 | 26.77 N |
| ATOM | 6895 | CA | SER | A | 453 | −40.226 | 20.533 | 17.182 | 1.00 | 26.38 C |
| ATOM | 6897 | CB | SER | A | 453 | −40.912 | 21.015 | 15.903 | 1.00 | 26.40 C |
| ATOM | 6900 | OG | SER | A | 453 | −40.796 | 20.044 | 14.876 | 1.00 | 25.79 O |
| ATOM | 6902 | C | SER | A | 453 | −40.253 | 21.643 | 18.233 | 1.00 | 26.12 C |
| ATOM | 6903 | O | SER | A | 453 | −39.280 | 22.361 | 18.385 | 1.00 | 25.97 O |
| ATOM | 6905 | N | VAL | A | 454 | −41.368 | 21.784 | 18.942 | 1.00 | 26.15 N |
| ATOM | 6906 | CA | VAL | A | 454 | −41.518 | 22.780 | 20.022 | 1.00 | 26.21 C |
| ATOM | 6908 | CB | VAL | A | 454 | −42.975 | 22.818 | 20.532 | 1.00 | 26.04 C |

TABLE 3-7-continued

| | | | | | Coordinates of *P. tremuloides* IspS | | | | | |
|---|---|---|---|---|---|---|---|---|---|---|
| ATOM | 6910 | CG1 | VAL | A | 454 | −43.122 | 23.787 | 21.694 | 1.00 | 25.24 | C |
| ATOM | 6914 | CG2 | VAL | A | 454 | −43.913 | 23.190 | 19.401 | 1.00 | 26.32 | C |
| ATOM | 6918 | C | VAL | A | 454 | −40.617 | 22.451 | 21.211 | 1.00 | 26.63 | C |
| ATOM | 6919 | O | VAL | A | 454 | −40.173 | 23.328 | 21.959 | 1.00 | 26.53 | O |
| ATOM | 6921 | N | SER | A | 455 | −40.374 | 21.160 | 21.380 | 1.00 | 27.21 | N |
| ATOM | 6922 | CA | SER | A | 455 | −39.541 | 20.651 | 22.437 | 1.00 | 27.60 | C |
| ATOM | 6924 | CB | SER | A | 455 | −39.677 | 19.141 | 22.490 | 1.00 | 27.31 | C |
| ATOM | 6927 | OG | SER | A | 455 | −38.922 | 18.625 | 23.545 | 1.00 | 28.13 | O |
| ATOM | 6929 | C | SER | A | 455 | −38.096 | 21.045 | 22.181 | 1.00 | 28.29 | C |
| ATOM | 6930 | O | SER | A | 455 | −37.445 | 21.628 | 23.043 | 1.00 | 28.63 | O |
| ATOM | 6932 | N | CYS | A | 456 | −37.599 | 20.748 | 20.988 | 1.00 | 29.04 | N |
| ATOM | 6933 | CA | CYS | A | 456 | −36.219 | 21.082 | 20.640 | 1.00 | 29.65 | C |
| ATOM | 6935 | CB | CYS | A | 456 | −35.868 | 20.535 | 19.256 | 1.00 | 29.52 | C |
| ATOM | 6938 | SG | CYS | A | 456 | −35.959 | 18.734 | 19.163 | 1.00 | 29.71 | S |
| ATOM | 6940 | C | CYS | A | 456 | −35.955 | 22.589 | 20.710 | 1.00 | 30.26 | C |
| ATOM | 6941 | O | CYS | A | 456 | −34.887 | 23.007 | 21.162 | 1.00 | 30.49 | O |
| ATOM | 6943 | N | TYR | A | 457 | −36.924 | 23.399 | 20.283 | 1.00 | 30.88 | N |
| ATOM | 6944 | CA | TYR | A | 457 | −36.767 | 24.850 | 20.308 | 1.00 | 31.45 | C |
| ATOM | 6946 | CB | TYR | A | 457 | −37.967 | 25.557 | 19.648 | 1.00 | 31.55 | C |
| ATOM | 6949 | CG | TYR | A | 457 | −37.691 | 26.991 | 19.178 | 1.00 | 32.09 | C |
| ATOM | 6950 | CD1 | TYR | A | 457 | −37.378 | 27.269 | 17.843 | 1.00 | 31.69 | C |
| ATOM | 6952 | CE1 | TYR | A | 457 | −37.128 | 28.569 | 17.418 | 1.00 | 31.73 | C |
| ATOM | 6954 | CZ | TYR | A | 457 | −37.186 | 29.613 | 18.328 | 1.00 | 32.84 | C |
| ATOM | 6955 | OH | TYR | A | 457 | −36.945 | 30.917 | 17.927 | 1.00 | 33.81 | O |
| ATOM | 6957 | CE2 | TYR | A | 457 | −37.492 | 29.364 | 19.658 | 1.00 | 32.72 | C |
| ATOM | 6959 | CD2 | TYR | A | 457 | −37.746 | 28.064 | 20.074 | 1.00 | 32.44 | C |
| ATOM | 6961 | C | TYR | A | 457 | −36.571 | 25.295 | 21.758 | 1.00 | 31.99 | C |
| ATOM | 6962 | O | TYR | A | 457 | −35.648 | 26.053 | 22.052 | 1.00 | 31.98 | O |
| ATOM | 6964 | N | MET | A | 458 | −37.419 | 24.799 | 22.661 | 1.00 | 32.76 | N |
| ATOM | 6965 | CA | MET | A | 458 | −37.211 | 24.987 | 24.105 | 1.00 | 33.37 | C |
| ATOM | 6967 | CB | MET | A | 458 | −38.151 | 24.097 | 24.921 | 1.00 | 33.43 | C |
| ATOM | 6970 | CG | MET | A | 458 | −39.570 | 24.593 | 25.059 | 1.00 | 33.70 | C |
| ATOM | 6973 | SD | MET | A | 458 | −40.641 | 23.312 | 25.737 | 1.00 | 34.59 | S |
| ATOM | 6974 | CE | MET | A | 458 | −39.709 | 22.763 | 27.179 | 1.00 | 34.71 | C |
| ATOM | 6978 | C | MET | A | 458 | −35.784 | 24.641 | 24.517 | 1.00 | 33.78 | C |
| ATOM | 6979 | O | MET | A | 458 | −35.101 | 25.437 | 25.151 | 1.00 | 33.73 | O |
| ATOM | 6981 | N | ARG | A | 459 | −35.347 | 23.445 | 24.145 | 1.00 | 34.46 | N |
| ATOM | 6982 | CA | ARG | A | 459 | −34.051 | 22.926 | 24.581 | 1.00 | 35.15 | C |
| ATOM | 6984 | CB | ARG | A | 459 | −33.876 | 21.447 | 24.171 | 1.00 | 35.68 | C |
| ATOM | 6987 | CG | ARG | A | 459 | −32.494 | 20.864 | 24.500 | 1.00 | 37.23 | C |
| ATOM | 6990 | CD | ARG | A | 459 | −32.491 | 19.345 | 24.752 | 1.00 | 39.80 | C |
| ATOM | 6993 | NE | ARG | A | 459 | −33.140 | 18.538 | 23.711 | 1.00 | 42.88 | N |
| ATOM | 6995 | CZ | ARG | A | 459 | −32.704 | 18.407 | 22.453 | 1.00 | 45.43 | C |
| ATOM | 6996 | NH1 | ARG | A | 459 | −31.615 | 19.062 | 22.035 | 1.00 | 47.50 | N |
| ATOM | 6999 | NH2 | ARG | A | 459 | −33.366 | 17.629 | 21.595 | 1.00 | 44.77 | N |
| ATOM | 7002 | C | ARG | A | 459 | −32.878 | 23.749 | 24.072 | 1.00 | 34.92 | C |
| ATOM | 7003 | O | ARG | A | 459 | −32.007 | 24.109 | 24.849 | 1.00 | 35.06 | O |
| ATOM | 7005 | N | THR | A | 460 | −32.854 | 24.047 | 22.778 | 1.00 | 34.96 | N |
| ATOM | 7006 | CA | THR | A | 460 | −31.674 | 24.678 | 22.163 | 1.00 | 34.91 | C |
| ATOM | 7008 | CB | THR | A | 460 | −31.494 | 24.263 | 20.680 | 1.00 | 34.88 | C |
| ATOM | 7010 | OG1 | THR | A | 460 | −32.330 | 25.067 | 19.841 | 1.00 | 34.39 | O |
| ATOM | 7012 | CG2 | THR | A | 460 | −31.825 | 22.776 | 20.488 | 1.00 | 35.44 | C |
| ATOM | 7016 | C | THR | A | 460 | −31.672 | 26.210 | 22.258 | 1.00 | 34.78 | C |
| ATOM | 7017 | O | THR | A | 460 | −30.673 | 26.837 | 21.911 | 1.00 | 34.92 | O |
| ATOM | 7019 | N | LYS | A | 461 | −32.781 | 26.806 | 22.701 | 1.00 | 34.41 | N |
| ATOM | 7020 | CA | LYS | A | 461 | −32.811 | 28.231 | 23.039 | 1.00 | 34.25 | C |
| ATOM | 7022 | CB | LYS | A | 461 | −33.921 | 28.947 | 22.265 | 1.00 | 34.56 | C |
| ATOM | 7025 | CG | LYS | A | 461 | −33.717 | 28.986 | 20.750 | 1.00 | 35.84 | C |
| ATOM | 7028 | CD | LYS | A | 461 | −32.519 | 29.859 | 20.347 | 1.00 | 37.64 | C |
| ATOM | 7031 | CE | LYS | A | 461 | −32.232 | 29.804 | 18.838 | 1.00 | 38.44 | C |
| ATOM | 7034 | NZ | LYS | A | 461 | −33.141 | 30.671 | 18.027 | 1.00 | 38.31 | N |
| ATOM | 7038 | C | LYS | A | 461 | −32.974 | 28.476 | 24.544 | 1.00 | 33.73 | C |
| ATOM | 7039 | O | LYS | A | 461 | −32.994 | 29.626 | 24.983 | 1.00 | 33.23 | O |
| ATOM | 7041 | N | GLY | A | 462 | −33.078 | 27.395 | 25.321 | 1.00 | 33.48 | N |
| ATOM | 7042 | CA | GLY | A | 462 | −33.173 | 27.464 | 26.784 | 1.00 | 33.23 | C |
| ATOM | 7045 | C | GLY | A | 462 | −34.332 | 28.320 | 27.239 | 1.00 | 32.95 | C |
| ATOM | 7046 | O | GLY | A | 462 | −34.144 | 29.258 | 28.004 | 1.00 | 33.17 | O |
| ATOM | 7048 | N | ILE | A | 463 | −35.528 | 28.000 | 26.757 | 1.00 | 32.52 | N |
| ATOM | 7049 | CA | ILE | A | 463 | −36.694 | 28.843 | 26.971 | 1.00 | 32.32 | C |
| ATOM | 7051 | CB | ILE | A | 463 | −37.006 | 29.724 | 25.734 | 1.00 | 32.47 | C |
| ATOM | 7053 | CG1 | ILE | A | 463 | −37.152 | 28.866 | 24.463 | 1.00 | 32.41 | C |
| ATOM | 7056 | CD1 | ILE | A | 463 | −37.359 | 29.675 | 23.191 | 1.00 | 32.02 | C |
| ATOM | 7060 | CG2 | ILE | A | 463 | −35.937 | 30.810 | 25.571 | 1.00 | 32.44 | C |
| ATOM | 7064 | C | ILE | A | 463 | −37.902 | 28.006 | 27.309 | 1.00 | 32.15 | C |
| ATOM | 7065 | O | ILE | A | 463 | −37.886 | 26.799 | 27.145 | 1.00 | 32.01 | O |
| ATOM | 7067 | N | SER | A | 464 | −38.950 | 28.670 | 27.780 | 1.00 | 32.27 | N |
| ATOM | 7068 | CA | SER | A | 464 | −40.163 | 28.006 | 28.239 | 1.00 | 32.52 | C |
| ATOM | 7070 | CB | SER | A | 464 | −40.964 | 28.974 | 29.110 | 1.00 | 32.65 | C |

TABLE 3-7-continued

| | | | | Coordinates of *P. tremuloides* IspS | | | | | | |
|---|---|---|---|---|---|---|---|---|---|---|
| ATOM | 7073 | OG | SER | A | 464 | −41.112 | 30.224 | 28.457 | 1.00 | 32.69 O |
| ATOM | 7075 | C | SER | A | 464 | −41.036 | 27.522 | 27.079 | 1.00 | 32.53 C |
| ATOM | 7076 | O | SER | A | 464 | −40.968 | 28.069 | 25.986 | 1.00 | 32.62 O |
| ATOM | 7078 | N | GLU | A | 465 | −41.857 | 26.500 | 27.332 | 1.00 | 32.47 N |
| ATOM | 7079 | CA | GLU | A | 465 | −42.836 | 26.010 | 26.353 | 1.00 | 32.33 C |
| ATOM | 7081 | CB | GLU | A | 465 | −43.689 | 24.868 | 26.935 | 1.00 | 32.34 C |
| ATOM | 7084 | CG | GLU | A | 465 | −44.756 | 24.312 | 25.974 | 1.00 | 32.37 C |
| ATOM | 7087 | CD | GLU | A | 465 | −45.675 | 23.279 | 26.611 | 1.00 | 32.47 C |
| ATOM | 7088 | OE1 | GLU | A | 465 | −45.297 | 22.659 | 27.630 | 1.00 | 31.63 O |
| ATOM | 7089 | OE2 | GLU | A | 465 | −46.785 | 23.086 | 26.074 | 1.00 | 32.77 O |
| ATOM | 7090 | C | GLU | A | 465 | −43.758 | 27.124 | 25.864 | 1.00 | 32.33 C |
| ATOM | 7091 | O | GLU | A | 465 | −44.078 | 27.183 | 24.676 | 1.00 | 32.60 O |
| ATOM | 7093 | N | GLU | A | 466 | −44.196 | 28.001 | 26.767 | 1.00 | 32.08 N |
| ATOM | 7094 | CA | GLU | A | 466 | −45.085 | 29.097 | 26.380 | 1.00 | 31.79 C |
| ATOM | 7096 | CB | GLU | A | 466 | −45.606 | 29.832 | 27.624 | 1.00 | 31.91 C |
| ATOM | 7099 | CG | GLU | A | 466 | −46.503 | 31.041 | 27.304 | 1.00 | 32.82 C |
| ATOM | 7102 | CD | GLU | A | 466 | −47.426 | 31.472 | 28.452 | 1.00 | 33.67 C |
| ATOM | 7103 | OE1 | GLU | A | 466 | −47.519 | 30.756 | 29.478 | 1.00 | 35.09 O |
| ATOM | 7104 | OE2 | GLU | A | 466 | −48.077 | 32.533 | 28.312 | 1.00 | 33.12 O |
| ATOM | 7105 | C | GLU | A | 466 | −44.392 | 30.052 | 25.386 | 1.00 | 31.13 C |
| ATOM | 7106 | O | GLU | A | 466 | −45.032 | 30.603 | 24.492 | 1.00 | 30.87 O |
| ATOM | 7108 | N | LEU | A | 467 | −43.077 | 30.194 | 25.531 | 1.00 | 30.57 N |
| ATOM | 7109 | CA | LEU | A | 467 | −42.265 | 31.102 | 24.708 | 1.00 | 30.18 C |
| ATOM | 7111 | CB | LEU | A | 467 | −41.055 | 31.604 | 25.524 | 1.00 | 30.38 C |
| ATOM | 7114 | CG | LEU | A | 467 | −40.674 | 33.087 | 25.463 | 1.00 | 30.39 C |
| ATOM | 7116 | CD1 | LEU | A | 467 | −41.608 | 33.900 | 26.362 | 1.00 | 30.23 C |
| ATOM | 7120 | CD2 | LEU | A | 467 | −39.214 | 33.308 | 25.872 | 1.00 | 30.31 C |
| ATOM | 7124 | C | LEU | A | 467 | −41.773 | 30.401 | 23.439 | 1.00 | 29.47 C |
| ATOM | 7125 | O | LEU | A | 467 | −41.660 | 31.010 | 22.382 | 1.00 | 29.17 O |
| ATOM | 7127 | N | ALA | A | 468 | −41.445 | 29.121 | 23.562 | 1.00 | 28.93 N |
| ATOM | 7128 | CA | ALA | A | 468 | −41.095 | 28.310 | 22.404 | 1.00 | 28.45 C |
| ATOM | 7130 | CB | ALA | A | 468 | −40.613 | 26.935 | 22.830 | 1.00 | 28.10 C |
| ATOM | 7134 | C | ALA | A | 468 | −42.306 | 28.193 | 21.494 | 1.00 | 28.08 C |
| ATOM | 7135 | O | ALA | A | 468 | −42.179 | 28.321 | 20.285 | 1.00 | 28.24 O |
| ATOM | 7137 | N | THR | A | 469 | −43.479 | 27.964 | 22.080 | 1.00 | 27.58 N |
| ATOM | 7138 | CA | THR | A | 469 | −44.719 | 27.870 | 21.322 | 1.00 | 27.26 C |
| ATOM | 7140 | CB | THR | A | 469 | −45.928 | 27.710 | 22.261 | 1.00 | 27.28 C |
| ATOM | 7142 | OG1 | THR | A | 469 | −46.063 | 26.330 | 22.627 | 1.00 | 27.55 O |
| ATOM | 7144 | CG2 | THR | A | 469 | −47.222 | 28.185 | 21.597 | 1.00 | 27.34 C |
| ATOM | 7148 | C | THR | A | 469 | −44.916 | 29.099 | 20.449 | 1.00 | 27.10 C |
| ATOM | 7149 | O | THR | A | 469 | −45.176 | 28.989 | 19.250 | 1.00 | 27.11 O |
| ATOM | 7151 | N | GLU | A | 470 | −44.774 | 30.267 | 21.061 | 1.00 | 26.88 N |
| ATOM | 7152 | CA | GLU | A | 470 | −44.944 | 31.542 | 20.376 | 1.00 | 26.84 C |
| ATOM | 7154 | CB | GLU | A | 470 | −44.832 | 32.663 | 21.400 | 1.00 | 27.07 C |
| ATOM | 7157 | CG | GLU | A | 470 | −45.357 | 34.003 | 20.958 | 1.00 | 28.47 C |
| ATOM | 7160 | CD | GLU | A | 470 | −45.140 | 35.087 | 22.008 | 1.00 | 30.51 C |
| ATOM | 7161 | OE1 | GLU | A | 470 | −45.029 | 34.775 | 23.221 | 1.00 | 31.53 O |
| ATOM | 7162 | OE2 | GLU | A | 470 | −45.083 | 36.269 | 21.608 | 1.00 | 32.59 O |
| ATOM | 7163 | C | GLU | A | 470 | −43.926 | 31.750 | 19.239 | 1.00 | 26.48 C |
| ATOM | 7164 | O | GLU | A | 470 | −44.261 | 32.296 | 18.184 | 1.00 | 26.29 O |
| ATOM | 7166 | N | SER | A | 471 | −42.686 | 31.316 | 19.452 | 1.00 | 26.12 N |
| ATOM | 7167 | CA | SER | A | 471 | −41.660 | 31.386 | 18.408 | 1.00 | 25.85 C |
| ATOM | 7169 | CB | SER | A | 471 | −40.296 | 30.933 | 18.941 | 1.00 | 25.96 C |
| ATOM | 7172 | OG | SER | A | 471 | −39.656 | 31.939 | 19.711 | 1.00 | 26.53 O |
| ATOM | 7174 | C | SER | A | 471 | −42.036 | 30.529 | 17.208 | 1.00 | 25.35 C |
| ATOM | 7175 | O | SER | A | 471 | −41.761 | 30.899 | 16.067 | 1.00 | 25.43 O |
| ATOM | 7177 | N | VAL | A | 472 | −42.653 | 29.381 | 17.482 | 1.00 | 24.95 N |
| ATOM | 7178 | CA | VAL | A | 472 | −43.097 | 28.451 | 16.438 | 1.00 | 24.65 C |
| ATOM | 7180 | CB | VAL | A | 472 | −43.485 | 27.055 | 17.024 | 1.00 | 24.57 C |
| ATOM | 7182 | CG1 | VAL | A | 472 | −44.257 | 26.222 | 16.016 | 1.00 | 23.23 C |
| ATOM | 7186 | CG2 | VAL | A | 472 | −42.232 | 26.309 | 17.494 | 1.00 | 23.83 C |
| ATOM | 7190 | C | VAL | A | 472 | −44.252 | 29.039 | 15.631 | 1.00 | 24.71 C |
| ATOM | 7191 | O | VAL | A | 472 | −44.369 | 28.776 | 14.440 | 1.00 | 24.63 O |
| ATOM | 7193 | N | MET | A | 473 | −45.073 | 29.866 | 16.269 | 1.00 | 24.79 N |
| ATOM | 7194 | CA | MET | A | 473 | −46.143 | 30.591 | 15.565 | 1.00 | 24.94 C |
| ATOM | 7196 | CB | MET | A | 473 | −47.059 | 31.266 | 16.576 | 1.00 | 25.11 C |
| ATOM | 7199 | CG | MET | A | 473 | −47.683 | 30.335 | 17.560 | 1.00 | 25.11 C |
| ATOM | 7202 | SD | MET | A | 473 | −48.967 | 29.391 | 16.780 | 1.00 | 25.35 S |
| ATOM | 7203 | CE | MET | A | 473 | −50.064 | 29.163 | 18.189 | 1.00 | 26.11 C |
| ATOM | 7207 | C | MET | A | 473 | −45.613 | 31.672 | 14.605 | 1.00 | 24.86 C |
| ATOM | 7208 | O | MET | A | 473 | −46.132 | 31.849 | 13.513 | 1.00 | 24.57 O |
| ATOM | 7210 | N | ASN | A | 474 | −44.589 | 32.405 | 15.032 | 1.00 | 24.89 N |
| ATOM | 7211 | CA | ASN | A | 474 | −43.951 | 33.383 | 14.166 | 1.00 | 25.00 C |
| ATOM | 7213 | CB | ASN | A | 474 | −43.009 | 34.278 | 14.966 | 1.00 | 25.12 C |
| ATOM | 7216 | CG | ASN | A | 474 | −43.700 | 34.966 | 16.127 | 1.00 | 25.77 C |
| ATOM | 7217 | OD1 | ASN | A | 474 | −43.058 | 35.312 | 17.114 | 1.00 | 26.96 O |
| ATOM | 7218 | ND2 | ASN | A | 474 | −45.015 | 35.163 | 16.021 | 1.00 | 26.31 N |
| ATOM | 7221 | C | ASN | A | 474 | −43.195 | 32.707 | 13.024 | 1.00 | 24.84 C |

TABLE 3-7-continued

Coordinates of *P. tremuloides* IspS

| ATOM | 7222 | O | ASN | A | 474 | −42.979 | 33.313 | 11.973 | 1.00 | 25.07 | O |
|---|---|---|---|---|---|---|---|---|---|---|---|
| ATOM | 7224 | N | LEU | A | 475 | −42.792 | 31.455 | 13.227 | 1.00 | 24.46 | N |
| ATOM | 7225 | CA | LEU | A | 475 | −42.218 | 30.671 | 12.142 | 1.00 | 24.06 | C |
| ATOM | 7227 | CB | LEU | A | 475 | −41.596 | 29.367 | 12.653 | 1.00 | 24.27 | C |
| ATOM | 7230 | CG | LEU | A | 475 | −40.307 | 29.072 | 11.886 | 1.00 | 25.08 | C |
| ATOM | 7232 | CD1 | LEU | A | 475 | −39.207 | 30.000 | 12.419 | 1.00 | 25.89 | C |
| ATOM | 7236 | CD2 | LEU | A | 475 | −39.887 | 27.622 | 11.985 | 1.00 | 25.33 | C |
| ATOM | 7240 | C | LEU | A | 475 | −43.278 | 30.365 | 11.085 | 1.00 | 23.26 | C |
| ATOM | 7241 | O | LEU | A | 475 | −43.018 | 30.479 | 9.884 | 1.00 | 22.90 | O |
| ATOM | 7243 | N | ILE | A | 476 | −44.471 | 29.978 | 11.534 | 1.00 | 22.53 | N |
| ATOM | 7244 | CA | ILE | A | 476 | −45.544 | 29.632 | 10.606 | 1.00 | 21.93 | C |
| ATOM | 7246 | CB | ILE | A | 476 | −46.773 | 29.017 | 11.308 | 1.00 | 21.58 | C |
| ATOM | 7248 | CG1 | ILE | A | 476 | −46.499 | 27.550 | 11.664 | 1.00 | 21.32 | C |
| ATOM | 7251 | CD1 | ILE | A | 476 | −47.552 | 26.902 | 12.598 | 1.00 | 20.33 | C |
| ATOM | 7255 | CG2 | ILE | A | 476 | −47.994 | 29.104 | 10.428 | 1.00 | 20.46 | C |
| ATOM | 7259 | C | ILE | A | 476 | −45.926 | 30.887 | 9.853 | 1.00 | 22.07 | C |
| ATOM | 7260 | O | ILE | A | 476 | −46.007 | 30.869 | 8.626 | 1.00 | 22.47 | O |
| ATOM | 7262 | N | ASP | A | 477 | −46.122 | 31.982 | 10.584 | 1.00 | 21.81 | N |
| ATOM | 7263 | CA | ASP | A | 477 | −46.483 | 33.245 | 9.970 | 1.00 | 21.56 | C |
| ATOM | 7265 | CB | ASP | A | 477 | −46.643 | 34.337 | 11.032 | 1.00 | 21.89 | C |
| ATOM | 7268 | CG | ASP | A | 477 | −47.962 | 34.217 | 11.817 | 1.00 | 23.39 | C |
| ATOM | 7269 | OD1 | ASP | A | 477 | −48.854 | 33.441 | 11.375 | 1.00 | 24.41 | O |
| ATOM | 7270 | OD2 | ASP | A | 477 | −48.103 | 34.902 | 12.875 | 1.00 | 23.80 | O |
| ATOM | 7271 | C | ASP | A | 477 | −45.425 | 33.626 | 8.947 | 1.00 | 21.06 | C |
| ATOM | 7272 | O | ASP | A | 477 | −45.759 | 33.913 | 7.795 | 1.00 | 20.78 | O |
| ATOM | 7274 | N | GLU | A | 478 | −44.156 | 33.591 | 9.361 | 1.00 | 20.63 | N |
| ATOM | 7275 | CA | GLU | A | 478 | −43.027 | 33.919 | 8.467 | 1.00 | 20.45 | C |
| ATOM | 7277 | CB | GLU | A | 478 | −41.680 | 33.793 | 9.200 | 1.00 | 20.66 | C |
| ATOM | 7280 | CG | GLU | A | 478 | −40.422 | 34.044 | 8.339 | 1.00 | 22.27 | C |
| ATOM | 7283 | CD | GLU | A | 478 | −39.107 | 33.579 | 9.018 | 1.00 | 24.72 | C |
| ATOM | 7284 | OE1 | GLU | A | 478 | −38.553 | 34.367 | 9.817 | 1.00 | 26.19 | O |
| ATOM | 7285 | OE2 | GLU | A | 478 | −38.619 | 32.442 | 8.745 | 1.00 | 25.66 | O |
| ATOM | 7286 | C | GLU | A | 478 | −43.041 | 33.042 | 7.217 | 1.00 | 19.54 | C |
| ATOM | 7287 | O | GLU | A | 478 | −42.879 | 33.544 | 6.102 | 1.00 | 19.02 | O |
| ATOM | 7289 | N | THR | A | 479 | −43.250 | 31.743 | 7.413 | 1.00 | 18.76 | N |
| ATOM | 7290 | CA | THR | A | 479 | −43.358 | 30.808 | 6.294 | 1.00 | 18.45 | C |
| ATOM | 7292 | CB | THR | A | 479 | −43.503 | 29.339 | 6.774 | 1.00 | 18.26 | C |
| ATOM | 7294 | OG1 | THR | A | 479 | −42.334 | 28.955 | 7.494 | 1.00 | 17.30 | O |
| ATOM | 7296 | CG2 | THR | A | 479 | −43.669 | 28.394 | 5.592 | 1.00 | 17.93 | C |
| ATOM | 7300 | C | THR | A | 479 | −44.504 | 31.173 | 5.314 | 1.00 | 18.39 | C |
| ATOM | 7301 | O | THR | A | 479 | −44.280 | 31.200 | 4.103 | 1.00 | 18.58 | O |
| ATOM | 7303 | N | TRP | A | 480 | −45.709 | 31.457 | 5.818 | 1.00 | 17.85 | N |
| ATOM | 7304 | CA | TRP | A | 480 | −46.801 | 31.909 | 4.942 | 1.00 | 17.44 | C |
| ATOM | 7306 | CB | TRP | A | 480 | −48.086 | 32.225 | 5.728 | 1.00 | 17.67 | C |
| ATOM | 7309 | CG | TRP | A | 480 | −48.969 | 31.042 | 5.888 | 1.00 | 17.09 | C |
| ATOM | 7310 | CD1 | TRP | A | 480 | −48.996 | 30.195 | 6.936 | 1.00 | 16.76 | C |
| ATOM | 7312 | NE1 | TRP | A | 480 | −49.914 | 29.216 | 6.724 | 1.00 | 17.08 | N |
| ATOM | 7314 | CE2 | TRP | A | 480 | −50.501 | 29.410 | 5.507 | 1.00 | 17.86 | C |
| ATOM | 7315 | CD2 | TRP | A | 480 | −49.930 | 30.559 | 4.954 | 1.00 | 17.15 | C |
| ATOM | 7316 | CE3 | TRP | A | 480 | −50.356 | 30.980 | 3.696 | 1.00 | 18.31 | C |
| ATOM | 7318 | CZ3 | TRP | A | 480 | −51.337 | 30.244 | 3.039 | 1.00 | 19.10 | C |
| ATOM | 7320 | CH2 | TRP | A | 480 | −51.897 | 29.107 | 3.622 | 1.00 | 18.83 | C |
| ATOM | 7322 | CZ2 | TRP | A | 480 | −51.493 | 28.673 | 4.855 | 1.00 | 18.86 | C |
| ATOM | 7324 | C | TRP | A | 480 | −46.426 | 33.124 | 4.097 | 1.00 | 17.10 | C |
| ATOM | 7325 | O | TRP | A | 480 | −46.824 | 33.215 | 2.943 | 1.00 | 17.22 | O |
| ATOM | 7327 | N | LYS | A | 481 | −45.675 | 34.062 | 4.659 | 1.00 | 16.60 | N |
| ATOM | 7328 | CA | LYS | A | 481 | −45.275 | 35.215 | 3.886 | 1.00 | 16.23 | C |
| ATOM | 7330 | CB | LYS | A | 481 | −44.566 | 36.243 | 4.747 | 1.00 | 16.42 | C |
| ATOM | 7333 | CG | LYS | A | 481 | −45.417 | 36.954 | 5.769 | 1.00 | 16.42 | C |
| ATOM | 7336 | CD | LYS | A | 481 | −44.555 | 37.979 | 6.505 | 1.00 | 16.40 | C |
| ATOM | 7339 | CE | LYS | A | 481 | −45.199 | 38.504 | 7.782 | 1.00 | 16.66 | C |
| ATOM | 7342 | NZ | LYS | A | 481 | −44.184 | 38.717 | 8.846 | 1.00 | 16.72 | N |
| ATOM | 7346 | C | LYS | A | 481 | −44.357 | 34.782 | 2.767 | 1.00 | 15.94 | C |
| ATOM | 7347 | O | LYS | A | 481 | −44.451 | 35.291 | 1.674 | 1.00 | 16.09 | O |
| ATOM | 7349 | N | LYS | A | 482 | −43.461 | 33.849 | 3.034 | 1.00 | 15.98 | N |
| ATOM | 7350 | CA | LYS | A | 482 | −42.559 | 33.369 | 1.996 | 1.00 | 16.30 | C |
| ATOM | 7352 | CB | LYS | A | 482 | −41.409 | 32.563 | 2.594 | 1.00 | 16.51 | C |
| ATOM | 7355 | CG | LYS | A | 482 | −40.354 | 33.445 | 3.286 | 1.00 | 17.46 | C |
| ATOM | 7358 | CD | LYS | A | 482 | −39.486 | 32.647 | 4.241 | 1.00 | 18.48 | C |
| ATOM | 7361 | CE | LYS | A | 482 | −38.625 | 33.548 | 5.096 | 1.00 | 18.94 | C |
| ATOM | 7364 | NZ | LYS | A | 482 | −37.865 | 32.773 | 6.129 | 1.00 | 20.40 | N |
| ATOM | 7368 | C | LYS | A | 482 | −43.296 | 32.561 | .938 | 1.00 | 16.40 | C |
| ATOM | 7369 | O | LYS | A | 482 | −42.941 | 32.614 | −.229 | 1.00 | 16.85 | O |
| ATOM | 7371 | N | MET | A | 483 | −44.328 | 31.824 | 1.332 | 1.00 | 16.57 | N |
| ATOM | 7372 | CA | MET | A | 483 | −45.149 | 31.100 | .366 | 1.00 | 16.67 | C |
| ATOM | 7374 | CB | MET | A | 483 | −46.128 | 30.156 | 1.057 | 1.00 | 16.55 | C |
| ATOM | 7377 | CG | MET | A | 483 | −45.496 | 28.923 | 1.675 | 1.00 | 16.50 | C |
| ATOM | 7380 | SD | MET | A | 483 | −46.715 | 27.684 | 2.194 | 1.00 | 17.39 | S |

TABLE 3-7-continued

Coordinates of *P. tremuloides* IspS

| ATOM | 7381 | CE | MET | A | 483 | −47.937 | 28.704 | 3.025 | 1.00 | 17.27 | C |
|---|---|---|---|---|---|---|---|---|---|---|---|
| ATOM | 7385 | C | MET | A | 483 | −45.928 | 32.069 | −.495 | 1.00 | 17.06 | C |
| ATOM | 7386 | O | MET | A | 483 | −46.027 | 31.867 | −1.688 | 1.00 | 17.17 | O |
| ATOM | 7388 | N | ASN | A | 484 | −46.483 | 33.110 | .118 | 1.00 | 17.72 | N |
| ATOM | 7389 | CA | ASN | A | 484 | −47.305 | 34.093 | −.587 | 1.00 | 18.35 | C |
| ATOM | 7391 | CB | ASN | A | 484 | −47.861 | 35.129 | .397 | 1.00 | 18.26 | C |
| ATOM | 7394 | CG | ASN | A | 484 | −48.994 | 34.601 | 1.248 | 1.00 | 17.35 | C |
| ATOM | 7395 | OD1 | ASN | A | 484 | −49.597 | 33.577 | .934 | 1.00 | 17.54 | O |
| ATOM | 7396 | ND2 | ASN | A | 484 | −49.304 | 35.317 | 2.331 | 1.00 | 14.10 | N |
| ATOM | 7399 | C | ASN | A | 484 | −46.541 | 34.839 | −1.677 | 1.00 | 19.51 | C |
| ATOM | 7400 | O | ASN | A | 484 | −47.123 | 35.250 | −2.685 | 1.00 | 19.49 | O |
| ATOM | 7402 | N | LYS | A | 485 | −45.243 | 35.035 | −1.463 | 1.00 | 20.86 | N |
| ATOM | 7403 | CA | LYS | A | 485 | −44.394 | 35.681 | −2.456 | 1.00 | 22.12 | C |
| ATOM | 7405 | CB | LYS | A | 485 | −43.070 | 36.092 | −1.823 | 1.00 | 22.08 | C |
| ATOM | 7408 | CG | LYS | A | 485 | −42.229 | 37.060 | −2.641 | 1.00 | 23.09 | C |
| ATOM | 7411 | CD | LYS | A | 485 | −40.783 | 37.072 | −2.109 | 1.00 | 25.38 | C |
| ATOM | 7414 | CE | LYS | A | 485 | −40.098 | 38.460 | −2.135 | 1.00 | 26.12 | C |
| ATOM | 7417 | NZ | LYS | A | 485 | −38.943 | 38.555 | −3.086 | 1.00 | 26.61 | N |
| ATOM | 7421 | C | LYS | A | 485 | −44.164 | 34.743 | −3.656 | 1.00 | 23.36 | C |
| ATOM | 7422 | O | LYS | A | 485 | −44.120 | 35.191 | −4.802 | 1.00 | 23.00 | O |
| ATOM | 7424 | N | GLU | A | 486 | −44.027 | 33.442 | −3.400 | 1.00 | 24.99 | N |
| ATOM | 7425 | CA | GLU | A | 486 | −43.902 | 32.479 | −4.491 | 1.00 | 26.35 | C |
| ATOM | 7427 | CB | GLU | A | 486 | −43.627 | 31.061 | −3.978 | 1.00 | 26.55 | C |
| ATOM | 7430 | CG | GLU | A | 486 | −42.985 | 30.130 | −5.033 | 1.00 | 28.29 | C |
| ATOM | 7433 | CD | GLU | A | 486 | −41.466 | 30.324 | −5.191 | 1.00 | 31.11 | C |
| ATOM | 7434 | OE1 | GLU | A | 486 | −40.981 | 30.466 | −6.341 | 1.00 | 32.07 | O |
| ATOM | 7435 | OE2 | GLU | A | 486 | −40.744 | 30.335 | −4.159 | 1.00 | 33.04 | O |
| ATOM | 7436 | C | GLU | A | 486 | −45.157 | 32.501 | −5.362 | 1.00 | 27.13 | C |
| ATOM | 7437 | O | GLU | A | 486 | −45.064 | 32.618 | −6.583 | 1.00 | 27.57 | O |
| ATOM | 7439 | N | LYS | A | 487 | −46.325 | 32.422 | −4.739 | 1.00 | 28.12 | N |
| ATOM | 7440 | CA | LYS | A | 487 | −47.582 | 32.378 | −5.485 | 1.00 | 29.12 | C |
| ATOM | 7442 | CB | LYS | A | 487 | −48.788 | 32.260 | −4.542 | 1.00 | 29.21 | C |
| ATOM | 7445 | CG | LYS | A | 487 | −50.167 | 32.296 | −5.235 | 1.00 | 28.57 | C |
| ATOM | 7448 | CD | LYS | A | 487 | −50.403 | 31.040 | −6.036 | 1.00 | 27.91 | C |
| ATOM | 7451 | CE | LYS | A | 487 | −51.615 | 31.141 | −6.936 | 1.00 | 28.38 | C |
| ATOM | 7454 | NZ | LYS | A | 487 | −52.874 | 31.460 | −6.211 | 1.00 | 28.03 | N |
| ATOM | 7458 | C | LYS | A | 487 | −47.756 | 33.603 | −6.352 | 1.00 | 30.18 | C |
| ATOM | 7459 | O | LYS | A | 487 | −48.308 | 33.514 | −7.446 | 1.00 | 30.21 | O |
| ATOM | 7461 | N | LEU | A | 488 | −47.295 | 34.743 | −5.844 | 1.00 | 31.64 | N |
| ATOM | 7462 | CA | LEU | A | 488 | −47.422 | 36.026 | −6.532 | 1.00 | 32.65 | C |
| ATOM | 7464 | CB | LEU | A | 488 | −47.426 | 37.144 | −5.494 | 1.00 | 32.43 | C |
| ATOM | 7467 | CG | LEU | A | 488 | −48.091 | 38.446 | −5.907 | 1.00 | 32.50 | C |
| ATOM | 7469 | CD1 | LEU | A | 488 | −49.593 | 38.288 | −5.943 | 1.00 | 32.66 | C |
| ATOM | 7473 | CD2 | LEU | A | 488 | −47.707 | 39.554 | −4.943 | 1.00 | 33.38 | C |
| ATOM | 7477 | C | LEU | A | 488 | −46.286 | 36.242 | −7.542 | 1.00 | 33.99 | C |
| ATOM | 7478 | O | LEU | A | 488 | −46.536 | 36.539 | −8.705 | 1.00 | 33.72 | O |
| ATOM | 7480 | N | GLY | A | 489 | −45.046 | 36.045 | −7.091 | 1.00 | 35.85 | N |
| ATOM | 7481 | CA | GLY | A | 489 | −43.845 | 36.361 | −7.874 | 1.00 | 37.37 | C |
| ATOM | 7484 | C | GLY | A | 489 | −43.278 | 35.221 | −8.709 | 1.00 | 38.76 | C |
| ATOM | 7485 | O | GLY | A | 489 | −42.414 | 34.467 | −8.250 | 1.00 | 39.06 | O |
| ATOM | 7487 | N | GLY | A | 490 | −43.760 | 35.119 | −9.947 | 1.00 | 40.26 | N |
| ATOM | 7488 | CA | GLY | A | 490 | −43.285 | 34.130 | −10.927 | 1.00 | 41.03 | C |
| ATOM | 7491 | C | GLY | A | 490 | −42.193 | 33.194 | −10.436 | 1.00 | 41.61 | C |
| ATOM | 7492 | O | GLY | A | 490 | −41.010 | 33.547 | −10.423 | 1.00 | 41.62 | O |
| ATOM | 7494 | N | SER | A | 491 | −42.590 | 31.996 | −10.023 | 1.00 | 42.17 | N |
| ATOM | 7495 | CA | SER | A | 491 | −41.619 | 30.962 | −9.662 | 1.00 | 42.54 | C |
| ATOM | 7497 | CB | SER | A | 491 | −42.279 | 29.909 | −8.741 | 1.00 | 42.63 | C |
| ATOM | 7500 | OG | SER | A | 491 | −43.451 | 29.345 | −9.294 | 1.00 | 42.44 | O |
| ATOM | 7502 | C | SER | A | 491 | −41.032 | 30.349 | −10.952 | 1.00 | 42.50 | C |
| ATOM | 7503 | O | SER | A | 491 | −41.117 | 30.961 | −12.030 | 1.00 | 42.57 | O |
| ATOM | 7505 | N | LEU | A | 492 | −40.405 | 29.177 | −10.843 | 1.00 | 42.18 | N |
| ATOM | 7506 | CA | LEU | A | 492 | −40.185 | 28.333 | −12.021 | 1.00 | 41.96 | C |
| ATOM | 7508 | CB | LEU | A | 492 | −39.110 | 27.270 | −11.782 | 1.00 | 42.39 | C |
| ATOM | 7511 | CG | LEU | A | 492 | −37.695 | 27.671 | −11.353 | 1.00 | 44.21 | C |
| ATOM | 7513 | CD1 | LEU | A | 492 | −36.783 | 26.438 | −11.498 | 1.00 | 45.26 | C |
| ATOM | 7517 | CD2 | LEU | A | 492 | −37.120 | 28.896 | −12.129 | 1.00 | 45.51 | C |
| ATOM | 7521 | C | LEU | A | 492 | −41.479 | 27.610 | −12.356 | 1.00 | 40.88 | C |
| ATOM | 7522 | O | LEU | A | 492 | −41.713 | 27.244 | −13.504 | 1.00 | 40.78 | O |
| ATOM | 7524 | N | PHE | A | 493 | −42.308 | 27.409 | −11.339 | 1.00 | 39.61 | N |
| ATOM | 7525 | CA | PHE | A | 493 | −43.500 | 26.595 | −11.460 | 1.00 | 38.85 | C |
| ATOM | 7527 | CB | PHE | A | 493 | −43.783 | 25.911 | −10.124 | 1.00 | 38.62 | C |
| ATOM | 7530 | CG | PHE | A | 493 | −42.725 | 24.937 | −9.713 | 1.00 | 37.16 | C |
| ATOM | 7531 | CD1 | PHE | A | 493 | −42.901 | 23.587 | −9.916 | 1.00 | 35.26 | C |
| ATOM | 7533 | CE1 | PHE | A | 493 | −41.934 | 22.698 | −9.546 | 1.00 | 34.86 | C |
| ATOM | 7535 | CZ | PHE | A | 493 | −40.769 | 23.143 | −8.966 | 1.00 | 35.09 | C |
| ATOM | 7537 | CE2 | PHE | A | 493 | −40.574 | 24.482 | −8.759 | 1.00 | 35.45 | C |
| ATOM | 7539 | CD2 | PHE | A | 493 | −41.549 | 25.374 | −9.130 | 1.00 | 36.36 | C |
| ATOM | 7541 | C | PHE | A | 493 | −44.714 | 27.412 | −11.890 | 1.00 | 38.62 | C |

TABLE 3-7-continued

| | | | | | | | | | | | |
|---|---|---|---|---|---|---|---|---|---|---|---|
| ATOM | 7542 | O | PHE | A | 493 | −44.756 | 28.621 | −11.702 | 1.00 | 38.86 | O |
| ATOM | 7544 | N | ALA | A | 494 | −45.698 | 26.731 | −12.469 | 1.00 | 38.32 | N |
| ATOM | 7545 | CA | ALA | A | 494 | −46.977 | 27.337 | −12.843 | 1.00 | 38.09 | C |
| ATOM | 7547 | CB | ALA | A | 494 | −47.658 | 26.486 | −13.906 | 1.00 | 38.17 | C |
| ATOM | 7551 | C | ALA | A | 494 | −47.891 | 27.479 | −11.623 | 1.00 | 37.76 | C |
| ATOM | 7552 | O | ALA | A | 494 | −48.039 | 26.541 | −10.845 | 1.00 | 38.15 | O |
| ATOM | 7554 | N | LYS | A | 495 | −48.541 | 28.629 | −11.484 | 1.00 | 37.15 | N |
| ATOM | 7555 | CA | LYS | A | 495 | −49.321 | 28.947 | −10.270 | 1.00 | 36.53 | C |
| ATOM | 7557 | CB | LYS | A | 495 | −50.116 | 30.258 | −10.477 | 1.00 | 36.90 | C |
| ATOM | 7560 | CG | LYS | A | 495 | −49.235 | 31.524 | −10.582 | 1.00 | 37.72 | C |
| ATOM | 7563 | CD | LYS | A | 495 | −50.061 | 32.826 | −10.585 | 1.00 | 38.87 | C |
| ATOM | 7566 | CE | LYS | A | 495 | −49.140 | 34.065 | −10.665 | 1.00 | 39.78 | C |
| ATOM | 7569 | NZ | LYS | A | 495 | −49.786 | 35.369 | −10.282 | 1.00 | 39.78 | N |
| ATOM | 7573 | C | LYS | A | 495 | −50.238 | 27.809 | −9.724 | 1.00 | 35.25 | C |
| ATOM | 7574 | O | LYS | A | 495 | −50.261 | 27.563 | −8.523 | 1.00 | 34.91 | O |
| ATOM | 7576 | N | PRO | A | 496 | −50.978 | 27.107 | −10.599 | 1.00 | 33.76 | N |
| ATOM | 7577 | CA | PRO | A | 496 | −51.846 | 26.015 | −10.162 | 1.00 | 32.74 | C |
| ATOM | 7579 | CB | PRO | A | 496 | −52.222 | 25.340 | −11.474 | 1.00 | 32.99 | C |
| ATOM | 7582 | CG | PRO | A | 496 | −52.337 | 26.470 | −12.385 | 1.00 | 33.75 | C |
| ATOM | 7585 | CD | PRO | A | 496 | −51.196 | 27.400 | −12.022 | 1.00 | 33.83 | C |
| ATOM | 7588 | C | PRO | A | 496 | −51.194 | 24.998 | −9.267 | 1.00 | 31.24 | C |
| ATOM | 7589 | O | PRO | A | 496 | −51.822 | 24.522 | −8.331 | 1.00 | 31.54 | O |
| ATOM | 7590 | N | PHE | A | 497 | −49.954 | 24.642 | −9.566 | 1.00 | 29.40 | N |
| ATOM | 7591 | CA | PHE | A | 497 | −49.229 | 23.726 | −8.708 | 1.00 | 27.76 | C |
| ATOM | 7593 | CB | PHE | A | 497 | −48.162 | 22.948 | −9.474 | 1.00 | 27.62 | C |
| ATOM | 7596 | CG | PHE | A | 497 | −47.351 | 22.040 | −8.597 | 1.00 | 26.33 | C |
| ATOM | 7597 | CD1 | PHE | A | 497 | −47.944 | 20.969 | −7.974 | 1.00 | 24.96 | C |
| ATOM | 7599 | CE1 | PHE | A | 497 | −47.218 | 20.151 | −7.156 | 1.00 | 25.04 | C |
| ATOM | 7601 | CZ | PHE | A | 497 | −45.875 | 20.396 | −6.940 | 1.00 | 24.79 | C |
| ATOM | 7603 | CE2 | PHE | A | 497 | −45.274 | 21.457 | −7.549 | 1.00 | 24.73 | C |
| ATOM | 7605 | CD2 | PHE | A | 497 | −46.010 | 22.282 | −8.366 | 1.00 | 25.48 | C |
| ATOM | 7607 | C | PHE | A | 497 | −48.592 | 24.407 | −7.494 | 1.00 | 26.59 | C |
| ATOM | 7608 | O | PHE | A | 497 | −48.361 | 23.738 | −6.500 | 1.00 | 26.77 | O |
| ATOM | 7610 | N | VAL | A | 498 | −48.291 | 25.704 | −7.535 | 1.00 | 24.83 | N |
| ATOM | 7611 | CA | VAL | A | 498 | −47.869 | 26.338 | −6.289 | 1.00 | 23.86 | C |
| ATOM | 7613 | CB | VAL | A | 498 | −47.181 | 27.722 | −6.455 | 1.00 | 23.47 | C |
| ATOM | 7615 | CG1 | VAL | A | 498 | −48.163 | 28.755 | −6.759 | 1.00 | 24.57 | C |
| ATOM | 7619 | CG2 | VAL | A | 498 | −46.151 | 27.690 | −7.551 | 1.00 | 23.54 | C |
| ATOM | 7623 | C | VAL | A | 498 | −49.094 | 26.396 | −5.355 | 1.00 | 22.97 | C |
| ATOM | 7624 | O | VAL | A | 498 | −48.978 | 26.130 | −4.161 | 1.00 | 23.39 | O |
| ATOM | 7626 | N | GLU | A | 499 | −50.268 | 26.687 | −5.903 | 1.00 | 21.68 | N |
| ATOM | 7627 | CA | GLU | A | 499 | −51.473 | 26.719 | −5.106 | 1.00 | 20.84 | C |
| ATOM | 7629 | CB | GLU | A | 499 | −52.677 | 27.136 | −5.930 | 1.00 | 20.99 | C |
| ATOM | 7632 | CG | GLU | A | 499 | −53.957 | 27.352 | −5.099 | 1.00 | 21.25 | C |
| ATOM | 7635 | CD | GLU | A | 499 | −53.930 | 28.630 | −4.265 | 1.00 | 21.77 | C |
| ATOM | 7636 | OE1 | GLU | A | 499 | −52.982 | 29.448 | −4.383 | 1.00 | 20.74 | O |
| ATOM | 7637 | OE2 | GLU | A | 499 | −54.876 | 28.812 | −3.476 | 1.00 | 22.76 | O |
| ATOM | 7638 | C | GLU | A | 499 | −51.766 | 25.371 | −4.497 | 1.00 | 20.35 | C |
| ATOM | 7639 | O | GLU | A | 499 | −52.137 | 25.308 | −3.318 | 1.00 | 20.78 | O |
| ATOM | 7641 | N | THR | A | 500 | −51.629 | 24.286 | −5.264 | 1.00 | 19.40 | N |
| ATOM | 7642 | CA | THR | A | 500 | −51.894 | 22.970 | −4.667 | 1.00 | 18.94 | C |
| ATOM | 7644 | CB | THR | A | 500 | −51.993 | 21.782 | −5.683 | 1.00 | 18.96 | C |
| ATOM | 7646 | OG1 | THR | A | 500 | −50.708 | 21.475 | −6.202 | 1.00 | 19.44 | O |
| ATOM | 7648 | CG2 | THR | A | 500 | −52.991 | 22.071 | −6.835 | 1.00 | 18.75 | C |
| ATOM | 7652 | C | THR | A | 500 | −50.895 | 22.674 | −3.526 | 1.00 | 18.20 | C |
| ATOM | 7653 | O | THR | A | 500 | −51.280 | 22.100 | −2.519 | 1.00 | 17.68 | O |
| ATOM | 7655 | N | ALA | A | 501 | −49.646 | 23.119 | −3.666 | 1.00 | 17.49 | N |
| ATOM | 7656 | CA | ALA | A | 501 | −48.663 | 23.021 | −2.593 | 1.00 | 17.18 | C |
| ATOM | 7658 | CB | ALA | A | 501 | −47.348 | 23.563 | −3.051 | 1.00 | 16.98 | C |
| ATOM | 7662 | C | ALA | A | 501 | −49.120 | 23.770 | −1.338 | 1.00 | 17.38 | C |
| ATOM | 7663 | O | ALA | A | 501 | −49.098 | 23.219 | −.230 | 1.00 | 17.45 | O |
| ATOM | 7665 | N | ILE | A | 502 | −49.517 | 25.031 | −1.508 | 1.00 | 17.29 | N |
| ATOM | 7666 | CA | ILE | A | 502 | −49.971 | 25.857 | −.386 | 1.00 | 17.07 | C |
| ATOM | 7668 | CB | ILE | A | 502 | −50.353 | 27.304 | −.846 | 1.00 | 17.09 | C |
| ATOM | 7670 | CG1 | ILE | A | 502 | −49.092 | 28.069 | −1.286 | 1.00 | 17.17 | C |
| ATOM | 7673 | CD1 | ILE | A | 502 | −49.345 | 29.345 | −2.116 | 1.00 | 16.25 | C |
| ATOM | 7677 | CG2 | ILE | A | 502 | −51.110 | 28.076 | .265 | 1.00 | 16.14 | C |
| ATOM | 7681 | C | ILE | A | 502 | −51.155 | 25.168 | .285 | 1.00 | 17.24 | C |
| ATOM | 7682 | O | ILE | A | 502 | −51.265 | 25.163 | 1.516 | 1.00 | 17.03 | O |
| ATOM | 7684 | N | ASN | A | 503 | −52.022 | 24.559 | −.522 | 1.00 | 17.32 | N |
| ATOM | 7685 | CA | ASN | A | 503 | −53.167 | 23.823 | .022 | 1.00 | 17.75 | C |
| ATOM | 7687 | CB | ASN | A | 503 | −53.986 | 23.221 | −1.121 | 1.00 | 17.70 | C |
| ATOM | 7690 | CG | ASN | A | 503 | −54.760 | 24.261 | −1.888 | 1.00 | 18.41 | C |
| ATOM | 7691 | OD1 | ASN | A | 503 | −55.058 | 25.334 | −1.382 | 1.00 | 18.94 | O |
| ATOM | 7692 | ND2 | ASN | A | 503 | −55.107 | 23.939 | −3.119 | 1.00 | 20.42 | N |
| ATOM | 7695 | C | ASN | A | 503 | −52.803 | 22.727 | 1.075 | 1.00 | 17.74 | C |
| ATOM | 7696 | O | ASN | A | 503 | −53.619 | 22.387 | 1.949 | 1.00 | 17.96 | O |
| ATOM | 7698 | N | LEU | A | 504 | −51.589 | 22.185 | .993 | 1.00 | 17.23 | N |

TABLE 3-7-continued

| | | | | | | | | | | | |
|---|---|---|---|---|---|---|---|---|---|---|---|
| Coordinates of P. tremuloides IspS | | | | | | | | | | | |
| ATOM | 7699 | CA | LEU | A | 504 | −51.105 | 21.249 | 1.994 | 1.00 | 17.10 | C |
| ATOM | 7701 | CB | LEU | A | 504 | −49.745 | 20.686 | 1.583 | 1.00 | 17.28 | C |
| ATOM | 7704 | CG | LEU | A | 504 | −49.213 | 19.528 | 2.426 | 1.00 | 17.29 | C |
| ATOM | 7706 | CD1 | LEU | A | 504 | −49.570 | 18.196 | 1.762 | 1.00 | 17.22 | C |
| ATOM | 7710 | CD2 | LEU | A | 504 | −47.708 | 19.686 | 2.616 | 1.00 | 16.83 | C |
| ATOM | 7714 | C | LEU | A | 504 | −50.971 | 21.939 | 3.347 | 1.00 | 16.97 | C |
| ATOM | 7715 | O | LEU | A | 504 | −51.237 | 21.330 | 4.379 | 1.00 | 16.84 | O |
| ATOM | 7717 | N | ALA | A | 505 | −50.535 | 23.201 | 3.330 | 1.00 | 16.90 | N |
| ATOM | 7718 | CA | ALA | A | 505 | −50.433 | 24.015 | 4.540 | 1.00 | 16.68 | C |
| ATOM | 7720 | CB | ALA | A | 505 | −49.739 | 25.309 | 4.243 | 1.00 | 16.54 | C |
| ATOM | 7724 | C | ALA | A | 505 | −51.826 | 24.281 | 5.074 | 1.00 | 16.77 | C |
| ATOM | 7725 | O | ALA | A | 505 | −52.087 | 24.123 | 6.266 | 1.00 | 16.80 | O |
| ATOM | 7727 | N | ARG | A | 506 | −52.726 | 24.664 | 4.172 | 1.00 | 16.82 | N |
| ATOM | 7728 | CA | ARG | A | 506 | −54.128 | 24.875 | 4.521 | 1.00 | 16.84 | C |
| ATOM | 7730 | CB | ARG | A | 506 | −54.944 | 25.274 | 3.286 | 1.00 | 16.86 | C |
| ATOM | 7733 | CG | ARG | A | 506 | −54.649 | 26.661 | 2.795 | 1.00 | 16.27 | C |
| ATOM | 7736 | CD | ARG | A | 506 | −55.586 | 27.090 | 1.726 | 1.00 | 15.26 | C |
| ATOM | 7739 | NE | ARG | A | 506 | −55.240 | 28.436 | 1.273 | 1.00 | 15.31 | N |
| ATOM | 7741 | CZ | ARG | A | 506 | −54.744 | 28.758 | .082 | 1.00 | 14.28 | C |
| ATOM | 7742 | NH1 | ARG | A | 506 | −54.519 | 27.856 | −.856 | 1.00 | 14.12 | N |
| ATOM | 7745 | NH2 | ARG | A | 506 | −54.471 | 30.018 | −.176 | 1.00 | 15.94 | N |
| ATOM | 7748 | C | ARG | A | 506 | −54.732 | 23.631 | 5.122 | 1.00 | 16.96 | C |
| ATOM | 7749 | O | ARG | A | 506 | −55.480 | 23.707 | 6.089 | 1.00 | 16.71 | O |
| ATOM | 7751 | N | GLN | A | 507 | −54.415 | 22.481 | 4.542 | 1.00 | 17.37 | N |
| ATOM | 7752 | CA | GLN | A | 507 | −54.962 | 21.233 | 5.048 | 1.00 | 17.87 | C |
| ATOM | 7754 | CB | GLN | A | 507 | −54.712 | 20.075 | 4.087 | 1.00 | 17.80 | C |
| ATOM | 7757 | CG | GLN | A | 507 | −55.293 | 18.740 | 4.571 | 1.00 | 17.24 | C |
| ATOM | 7760 | CD | GLN | A | 507 | −56.777 | 18.805 | 4.860 | 1.00 | 16.23 | C |
| ATOM | 7761 | OE1 | GLN | A | 507 | −57.506 | 19.585 | 4.250 | 1.00 | 16.66 | O |
| ATOM | 7762 | NE2 | GLN | A | 507 | −57.233 | 17.980 | 5.790 | 1.00 | 14.96 | N |
| ATOM | 7765 | C | GLN | A | 507 | −54.401 | 20.890 | 6.423 | 1.00 | 18.28 | C |
| ATOM | 7766 | O | GLN | A | 507 | −55.148 | 20.419 | 7.287 | 1.00 | 18.53 | O |
| ATOM | 7768 | N | SER | A | 508 | −53.096 | 21.113 | 6.609 | 1.00 | 18.50 | N |
| ATOM | 7769 | CA | SER | A | 508 | −52.435 | 20.924 | 7.908 | 1.00 | 18.54 | C |
| ATOM | 7771 | CB | SER | A | 508 | −50.979 | 21.385 | 7.856 | 1.00 | 18.40 | C |
| ATOM | 7774 | OG | SER | A | 508 | −50.259 | 20.694 | 6.857 | 1.00 | 18.51 | O |
| ATOM | 7776 | C | SER | A | 508 | −53.147 | 21.752 | 8.942 | 1.00 | 18.78 | C |
| ATOM | 7777 | O | SER | A | 508 | −53.535 | 21.278 | 10.006 | 1.00 | 18.33 | O |
| ATOM | 7779 | N | HIS | A | 509 | −53.324 | 23.014 | 8.599 | 1.00 | 19.37 | N |
| ATOM | 7780 | CA | HIS | A | 509 | −54.014 | 23.922 | 9.466 | 1.00 | 19.92 | C |
| ATOM | 7782 | CB | HIS | A | 509 | −54.126 | 25.295 | 8.818 | 1.00 | 20.07 | C |
| ATOM | 7785 | CG | HIS | A | 509 | −53.000 | 26.188 | 9.174 | 1.00 | 19.82 | C |
| ATOM | 7786 | ND1 | HIS | A | 509 | −52.079 | 26.631 | 8.255 | 1.00 | 19.73 | N |
| ATOM | 7788 | CE1 | HIS | A | 509 | −51.187 | 27.383 | 8.866 | 1.00 | 20.25 | C |
| ATOM | 7790 | NE2 | HIS | A | 509 | −51.485 | 27.426 | 10.149 | 1.00 | 21.66 | N |
| ATOM | 7792 | CD2 | HIS | A | 509 | −52.615 | 26.682 | 10.368 | 1.00 | 20.98 | C |
| ATOM | 7794 | C | HIS | A | 509 | −55.389 | 23.448 | 9.839 | 1.00 | 20.41 | C |
| ATOM | 7795 | O | HIS | A | 509 | −55.821 | 23.694 | 10.934 | 1.00 | 20.22 | O |
| ATOM | 7797 | N | CYS | A | 510 | −56.093 | 22.808 | 8.918 | 1.00 | 21.33 | N |
| ATOM | 7798 | CA | CYS | A | 510 | −57.470 | 22.396 | 9.189 | 1.00 | 22.03 | C |
| ATOM | 7800 | CB | CYS | A | 510 | −58.278 | 22.383 | 7.894 | 1.00 | 21.90 | C |
| ATOM | 7803 | SG | CYS | A | 510 | −58.522 | 24.055 | 7.270 | 1.00 | 21.93 | S |
| ATOM | 7805 | C | CYS | A | 510 | −57.527 | 21.054 | 9.908 | 1.00 | 22.60 | C |
| ATOM | 7806 | O | CYS | A | 510 | −58.423 | 20.822 | 10.706 | 1.00 | 22.23 | O |
| ATOM | 7808 | N | THR | A | 511 | −56.553 | 20.194 | 9.627 | 1.00 | 23.67 | N |
| ATOM | 7809 | CA | THR | A | 511 | −56.421 | 18.920 | 10.305 | 1.00 | 24.81 | C |
| ATOM | 7811 | CB | THR | A | 511 | −55.437 | 18.000 | 9.565 | 1.00 | 24.70 | C |
| ATOM | 7813 | OG1 | THR | A | 511 | −56.071 | 17.485 | 8.394 | 1.00 | 24.45 | O |
| ATOM | 7815 | CG2 | THR | A | 511 | −55.003 | 16.844 | 10.448 | 1.00 | 24.23 | C |
| ATOM | 7819 | C | THR | A | 511 | −55.965 | 19.086 | 11.756 | 1.00 | 26.22 | C |
| ATOM | 7820 | O | THR | A | 511 | −56.685 | 18.717 | 12.679 | 1.00 | 26.12 | O |
| ATOM | 7822 | N | TYR | A | 512 | −54.775 | 19.643 | 11.959 | 1.00 | 28.08 | N |
| ATOM | 7823 | CA | TYR | A | 512 | −54.177 | 19.657 | 13.298 | 1.00 | 29.63 | C |
| ATOM | 7825 | CB | TYR | A | 512 | −52.663 | 19.783 | 13.238 | 1.00 | 29.67 | C |
| ATOM | 7828 | CG | TYR | A | 512 | −52.117 | 18.579 | 12.560 | 1.00 | 29.56 | C |
| ATOM | 7829 | CD1 | TYR | A | 512 | −51.965 | 17.395 | 13.246 | 1.00 | 29.66 | C |
| ATOM | 7831 | CE1 | TYR | A | 512 | −51.507 | 16.273 | 12.614 | 1.00 | 30.94 | C |
| ATOM | 7833 | CZ | TYR | A | 512 | −51.217 | 16.326 | 11.263 | 1.00 | 32.04 | C |
| ATOM | 7834 | OH | TYR | A | 512 | −50.757 | 15.209 | 10.608 | 1.00 | 33.78 | O |
| ATOM | 7836 | CE2 | TYR | A | 512 | −51.390 | 17.492 | 10.557 | 1.00 | 31.29 | C |
| ATOM | 7838 | CD2 | TYR | A | 512 | −51.847 | 18.600 | 11.205 | 1.00 | 30.53 | C |
| ATOM | 7840 | C | TYR | A | 512 | −54.812 | 20.676 | 14.206 | 1.00 | 31.11 | C |
| ATOM | 7841 | O | TYR | A | 512 | −55.494 | 20.277 | 15.139 | 1.00 | 31.34 | O |
| ATOM | 7843 | N | HIS | A | 513 | −54.583 | 21.969 | 13.966 | 1.00 | 32.89 | N |
| ATOM | 7844 | CA | HIS | A | 513 | −55.505 | 23.023 | 14.442 | 1.00 | 34.48 | C |
| ATOM | 7846 | CB | HIS | A | 513 | −56.372 | 23.461 | 13.225 | 1.00 | 35.13 | C |
| ATOM | 7849 | CG | HIS | A | 513 | −57.704 | 24.108 | 13.529 | 1.00 | 37.10 | C |
| ATOM | 7850 | ND1 | HIS | A | 513 | −58.265 | 25.040 | 12.678 | 1.00 | 38.69 | N |

TABLE 3-7-continued

| | | | | | Coordinates of *P. tremuloides* IspS | | | | | |
|---|---|---|---|---|---|---|---|---|---|---|
| ATOM | 7852 | CE1 | HIS | A | 513 | −59.442 | 25.416 | 13.151 | 1.00 | 39.23 | C |
| ATOM | 7854 | NE2 | HIS | A | 513 | −59.678 | 24.751 | 14.268 | 1.00 | 38.18 | N |
| ATOM | 7856 | CD2 | HIS | A | 513 | −58.615 | 23.915 | 14.519 | 1.00 | 38.17 | C |
| ATOM | 7858 | C | HIS | A | 513 | −56.337 | 22.503 | 15.610 | 1.00 | 35.00 | C |
| ATOM | 7859 | O | HIS | A | 513 | −56.302 | 23.074 | 16.712 | 1.00 | 35.48 | O |
| ATOM | 7861 | N | ASN | A | 514 | −57.079 | 21.419 | 15.351 | 1.00 | 35.23 | N |
| ATOM | 7862 | CA | ASN | A | 514 | −57.934 | 20.768 | 16.347 | 1.00 | 35.46 | C |
| ATOM | 7864 | CB | ASN | A | 514 | −58.342 | 19.343 | 15.903 | 1.00 | 35.39 | C |
| ATOM | 7867 | CG | ASN | A | 514 | −59.383 | 19.345 | 14.786 | 1.00 | 34.01 | C |
| ATOM | 7868 | OD1 | ASN | A | 514 | −59.336 | 20.185 | 13.896 | 1.00 | 33.36 | O |
| ATOM | 7869 | ND2 | ASN | A | 514 | −60.315 | 18.406 | 14.833 | 1.00 | 31.13 | N |
| ATOM | 7872 | C | ASN | A | 514 | −57.464 | 20.751 | 17.818 | 1.00 | 36.15 | C |
| ATOM | 7873 | O | ASN | A | 514 | −56.397 | 20.211 | 18.153 | 1.00 | 36.13 | O |
| ATOM | 7875 | N | GLY | A | 515 | −58.277 | 21.430 | 18.640 | 1.00 | 36.95 | N |
| ATOM | 7876 | CA | GLY | A | 515 | −58.427 | 21.235 | 20.079 | 1.00 | 37.43 | C |
| ATOM | 7879 | C | GLY | A | 515 | −59.724 | 20.470 | 20.381 | 1.00 | 38.18 | C |
| ATOM | 7880 | O | GLY | A | 515 | −59.636 | 19.418 | 21.021 | 1.00 | 38.57 | O |
| ATOM | 7882 | N | ASP | A | 516 | −60.930 | 20.921 | 19.969 | 1.00 | 38.73 | N |
| ATOM | 7883 | CA | ASP | A | 516 | −61.249 | 22.194 | 19.293 | 1.00 | 39.26 | C |
| ATOM | 7885 | CB | ASP | A | 516 | −61.607 | 21.904 | 17.845 | 1.00 | 39.51 | C |
| ATOM | 7888 | CG | ASP | A | 516 | −60.523 | 22.291 | 16.894 | 1.00 | 42.32 | C |
| ATOM | 7889 | OD1 | ASP | A | 516 | −59.613 | 23.084 | 17.286 | 1.00 | 45.56 | O |
| ATOM | 7890 | OD2 | ASP | A | 516 | −60.578 | 21.797 | 15.740 | 1.00 | 45.52 | O |
| ATOM | 7891 | C | ASP | A | 516 | −62.466 | 22.913 | 19.884 | 1.00 | 39.38 | C |
| ATOM | 7892 | O | ASP | A | 516 | −63.032 | 22.454 | 20.880 | 1.00 | 39.74 | O |
| ATOM | 7894 | N | ALA | A | 517 | −62.850 | 24.038 | 19.259 | 1.00 | 39.40 | N |
| ATOM | 7895 | CA | ALA | A | 517 | −64.140 | 24.752 | 19.481 | 1.00 | 39.50 | C |
| ATOM | 7897 | CB | ALA | A | 517 | −65.117 | 24.403 | 18.333 | 1.00 | 39.27 | C |
| ATOM | 7901 | C | ALA | A | 517 | −64.837 | 24.566 | 20.863 | 1.00 | 39.90 | C |
| ATOM | 7902 | O | ALA | A | 517 | −64.173 | 24.428 | 21.899 | 1.00 | 39.89 | O |
| ATOM | 7904 | N | HIS | A | 518 | −66.175 | 24.617 | 20.876 | 1.00 | 40.33 | N |
| ATOM | 7905 | CA | HIS | A | 518 | −66.973 | 24.112 | 22.016 | 1.00 | 40.73 | C |
| ATOM | 7907 | CB | HIS | A | 518 | −68.091 | 25.092 | 22.396 | 1.00 | 41.22 | C |
| ATOM | 7910 | CG | HIS | A | 518 | −67.578 | 26.419 | 22.866 | 1.00 | 43.58 | C |
| ATOM | 7911 | ND1 | HIS | A | 518 | −67.426 | 26.725 | 24.207 | 1.00 | 45.88 | N |
| ATOM | 7913 | CE1 | HIS | A | 518 | −66.938 | 27.950 | 24.320 | 1.00 | 46.42 | C |
| ATOM | 7915 | NE2 | HIS | A | 518 | −66.760 | 28.446 | 23.102 | 1.00 | 46.25 | N |
| ATOM | 7917 | CD2 | HIS | A | 518 | −67.145 | 27.506 | 22.174 | 1.00 | 45.24 | C |
| ATOM | 7919 | C | HIS | A | 518 | −67.526 | 22.725 | 21.655 | 1.00 | 40.17 | C |
| ATOM | 7920 | O | HIS | A | 518 | −68.738 | 22.501 | 21.571 | 1.00 | 40.02 | O |
| ATOM | 7922 | N | THR | A | 519 | −66.581 | 21.812 | 21.448 | 1.00 | 39.64 | N |
| ATOM | 7923 | CA | THR | A | 519 | −66.808 | 20.466 | 20.918 | 1.00 | 39.16 | C |
| ATOM | 7925 | CB | THR | A | 519 | −67.414 | 20.469 | 19.453 | 1.00 | 39.16 | C |
| ATOM | 7927 | OG1 | THR | A | 519 | −66.847 | 21.529 | 18.665 | 1.00 | 39.04 | O |
| ATOM | 7929 | CG2 | THR | A | 519 | −68.942 | 20.633 | 19.480 | 1.00 | 38.82 | C |
| ATOM | 7933 | C | THR | A | 519 | −65.428 | 19.771 | 20.978 | 1.00 | 38.85 | C |
| ATOM | 7934 | O | THR | A | 519 | −64.391 | 20.433 | 20.878 | 1.00 | 38.66 | O |
| ATOM | 7936 | N | SER | A | 520 | −65.407 | 18.455 | 21.170 | 1.00 | 38.37 | N |
| ATOM | 7937 | CA | SER | A | 520 | −64.160 | 17.745 | 21.500 | 1.00 | 38.08 | C |
| ATOM | 7939 | CB | SER | A | 520 | −64.514 | 16.320 | 21.931 | 1.00 | 38.06 | C |
| ATOM | 7942 | OG | SER | A | 520 | −64.560 | 15.475 | 20.805 | 1.00 | 38.66 | O |
| ATOM | 7944 | C | SER | A | 520 | −63.136 | 17.771 | 20.327 | 1.00 | 37.86 | C |
| ATOM | 7945 | O | SER | A | 520 | −63.420 | 18.369 | 19.289 | 1.00 | 37.50 | O |
| ATOM | 7947 | N | PRO | A | 521 | −61.948 | 17.122 | 20.482 | 1.00 | 37.98 | N |
| ATOM | 7948 | CA | PRO | A | 521 | −60.944 | 17.170 | 19.379 | 1.00 | 37.92 | C |
| ATOM | 7950 | CB | PRO | A | 521 | −59.674 | 16.527 | 19.987 | 1.00 | 37.87 | C |
| ATOM | 7953 | CG | PRO | A | 521 | −60.091 | 15.919 | 21.330 | 1.00 | 38.28 | C |
| ATOM | 7956 | CD | PRO | A | 521 | −61.577 | 16.137 | 21.526 | 1.00 | 38.13 | C |
| ATOM | 7959 | C | PRO | A | 521 | −61.432 | 16.446 | 18.110 | 1.00 | 37.96 | C |
| ATOM | 7960 | O | PRO | A | 521 | −61.769 | 17.118 | 17.140 | 1.00 | 38.09 | O |
| ATOM | 7961 | N | ASP | A | 522 | −61.483 | 15.108 | 18.107 | 1.00 | 38.07 | N |
| ATOM | 7962 | CA | ASP | A | 522 | −62.351 | 14.393 | 17.161 | 1.00 | 38.14 | C |
| ATOM | 7964 | CB | ASP | A | 522 | −62.132 | 12.877 | 17.204 | 1.00 | 38.31 | C |
| ATOM | 7967 | CG | ASP | A | 522 | −60.769 | 12.456 | 16.640 | 1.00 | 39.45 | C |
| ATOM | 7968 | OD1 | ASP | A | 522 | −60.160 | 13.200 | 15.827 | 1.00 | 39.72 | O |
| ATOM | 7969 | OD2 | ASP | A | 522 | −60.302 | 11.361 | 17.025 | 1.00 | 41.59 | O |
| ATOM | 7970 | C | ASP | A | 522 | −63.760 | 14.780 | 17.591 | 1.00 | 37.92 | C |
| ATOM | 7971 | O | ASP | A | 522 | −63.908 | 15.608 | 18.474 | 1.00 | 38.01 | O |
| ATOM | 7973 | N | GLU | A | 523 | −64.799 | 14.239 | 16.974 | 1.00 | 37.79 | N |
| ATOM | 7974 | CA | GLU | A | 523 | −66.150 | 14.818 | 17.121 | 1.00 | 37.83 | C |
| ATOM | 7976 | CB | GLU | A | 523 | −66.618 | 14.919 | 18.591 | 1.00 | 37.85 | C |
| ATOM | 7979 | CG | GLU | A | 523 | −66.346 | 13.678 | 19.483 | 1.00 | 39.40 | C |
| ATOM | 7982 | CD | GLU | A | 523 | −66.916 | 13.802 | 20.931 | 1.00 | 41.49 | C |
| ATOM | 7983 | OE1 | GLU | A | 523 | −67.714 | 14.737 | 21.207 | 1.00 | 42.81 | O |
| ATOM | 7984 | OE2 | GLU | A | 523 | −66.566 | 12.957 | 21.800 | 1.00 | 42.04 | O |
| ATOM | 7985 | C | GLU | A | 523 | −66.242 | 16.203 | 16.430 | 1.00 | 37.51 | C |
| ATOM | 7986 | O | GLU | A | 523 | −67.338 | 16.751 | 16.283 | 1.00 | 37.70 | O |
| ATOM | 7988 | N | LEU | A | 524 | −65.097 | 16.775 | 16.043 | 1.00 | 37.03 | N |

TABLE 3-7-continued

| | | | | | | | | | | | |
|---|---|---|---|---|---|---|---|---|---|---|---|
| ATOM | 7989 | CA | LEU | A | 524 | −65.044 | 17.863 | 15.067 | 1.00 | 36.58 | C |
| ATOM | 7991 | CB | LEU | A | 524 | −64.174 | 19.022 | 15.559 | 1.00 | 36.56 | C |
| ATOM | 7994 | CG | LEU | A | 524 | −63.963 | 20.225 | 14.624 | 1.00 | 36.35 | C |
| ATOM | 7996 | CD1 | LEU | A | 524 | −63.400 | 21.376 | 15.418 | 1.00 | 35.74 | C |
| ATOM | 8000 | CD2 | LEU | A | 524 | −65.242 | 20.681 | 13.910 | 1.00 | 36.53 | C |
| ATOM | 8004 | C | LEU | A | 524 | −64.478 | 17.287 | 13.782 | 1.00 | 36.20 | C |
| ATOM | 8005 | O | LEU | A | 524 | −65.106 | 17.363 | 12.733 | 1.00 | 36.14 | O |
| ATOM | 8007 | N | THR | A | 525 | −63.298 | 16.686 | 13.869 | 1.00 | 35.83 | N |
| ATOM | 8008 | CA | THR | A | 525 | −62.756 | 15.935 | 12.748 | 1.00 | 35.66 | C |
| ATOM | 8010 | CB | THR | A | 525 | −61.585 | 15.015 | 13.173 | 1.00 | 35.48 | C |
| ATOM | 8012 | OG1 | THR | A | 525 | −60.776 | 15.678 | 14.152 | 1.00 | 35.55 | O |
| ATOM | 8014 | CG2 | THR | A | 525 | −60.720 | 14.641 | 11.978 | 1.00 | 34.73 | C |
| ATOM | 8018 | C | THR | A | 525 | −63.875 | 15.098 | 12.123 | 1.00 | 35.89 | C |
| ATOM | 8019 | O | THR | A | 525 | −64.040 | 15.095 | 10.909 | 1.00 | 35.98 | O |
| ATOM | 8021 | N | ARG | A | 526 | −64.667 | 14.420 | 12.954 | 1.00 | 36.06 | N |
| ATOM | 8022 | CA | ARG | A | 526 | −65.739 | 13.574 | 12.448 | 1.00 | 36.18 | C |
| ATOM | 8024 | CB | ARG | A | 526 | −66.340 | 12.718 | 13.555 | 1.00 | 36.56 | C |
| ATOM | 8027 | CG | ARG | A | 526 | −67.416 | 11.754 | 13.054 | 1.00 | 38.35 | C |
| ATOM | 8030 | CD | ARG | A | 526 | −67.781 | 10.702 | 14.092 | 1.00 | 41.00 | C |
| ATOM | 8033 | NE | ARG | A | 526 | −67.740 | 11.207 | 15.470 | 1.00 | 43.08 | N |
| ATOM | 8035 | CZ | ARG | A | 526 | −68.637 | 12.033 | 16.024 | 1.00 | 44.51 | C |
| ATOM | 8036 | NH1 | ARG | A | 526 | −69.681 | 12.500 | 15.336 | 1.00 | 44.46 | N |
| ATOM | 8039 | NH2 | ARG | A | 526 | −68.476 | 12.406 | 17.288 | 1.00 | 45.02 | N |
| ATOM | 8042 | C | ARG | A | 526 | −66.834 | 14.384 | 11.774 | 1.00 | 35.68 | C |
| ATOM | 8043 | O | ARG | A | 526 | −67.253 | 14.035 | 10.675 | 1.00 | 35.84 | O |
| ATOM | 8045 | N | LYS | A | 527 | −67.309 | 15.447 | 12.424 | 1.00 | 35.06 | N |
| ATOM | 8046 | CA | LYS | A | 527 | −68.285 | 16.343 | 11.780 | 1.00 | 34.61 | C |
| ATOM | 8048 | CB | LYS | A | 527 | −68.680 | 17.528 | 12.683 | 1.00 | 34.74 | C |
| ATOM | 8051 | CG | LYS | A | 527 | −69.818 | 17.225 | 13.651 | 1.00 | 35.40 | C |
| ATOM | 8054 | CD | LYS | A | 527 | −70.301 | 18.452 | 14.441 | 1.00 | 35.99 | C |
| ATOM | 8057 | CE | LYS | A | 527 | −71.280 | 18.021 | 15.556 | 1.00 | 36.42 | C |
| ATOM | 8060 | NZ | LYS | A | 527 | −71.652 | 19.095 | 16.530 | 1.00 | 36.31 | N |
| ATOM | 8064 | C | LYS | A | 527 | −67.723 | 16.860 | 10.457 | 1.00 | 33.77 | C |
| ATOM | 8065 | O | LYS | A | 527 | −68.377 | 16.763 | 9.423 | 1.00 | 33.75 | O |
| ATOM | 8067 | N | ARG | A | 528 | −66.501 | 17.388 | 10.499 | 1.00 | 32.71 | N |
| ATOM | 8068 | CA | ARG | A | 528 | −65.840 | 17.929 | 9.310 | 1.00 | 31.79 | C |
| ATOM | 8070 | CB | ARG | A | 528 | −64.425 | 18.464 | 9.644 | 1.00 | 31.74 | C |
| ATOM | 8073 | CG | ARG | A | 528 | −64.419 | 19.844 | 10.330 | 1.00 | 30.90 | C |
| ATOM | 8076 | CD | ARG | A | 528 | −63.021 | 20.439 | 10.527 | 1.00 | 29.75 | C |
| ATOM | 8079 | NE | ARG | A | 528 | −63.098 | 21.745 | 11.190 | 1.00 | 29.55 | N |
| ATOM | 8081 | CZ | ARG | A | 528 | −62.056 | 22.513 | 11.528 | 1.00 | 29.96 | C |
| ATOM | 8082 | NH1 | ARG | A | 528 | −60.801 | 22.145 | 11.284 | 1.00 | 29.74 | N |
| ATOM | 8085 | NH2 | ARG | A | 528 | −62.269 | 23.677 | 12.130 | 1.00 | 30.71 | N |
| ATOM | 8088 | C | ARG | A | 528 | −65.796 | 16.904 | 8.172 | 1.00 | 30.99 | C |
| ATOM | 8089 | O | ARG | A | 528 | −66.226 | 17.206 | 7.068 | 1.00 | 30.97 | O |
| ATOM | 8091 | N | VAL | A | 529 | −65.313 | 15.694 | 8.450 | 1.00 | 30.12 | N |
| ATOM | 8092 | CA | VAL | A | 529 | −65.239 | 14.631 | 7.438 | 1.00 | 29.43 | C |
| ATOM | 8094 | CB | VAL | A | 529 | −64.557 | 13.354 | 7.972 | 1.00 | 29.39 | C |
| ATOM | 8096 | CG1 | VAL | A | 529 | −64.785 | 12.187 | 7.023 | 1.00 | 28.89 | C |
| ATOM | 8100 | CG2 | VAL | A | 529 | −63.062 | 13.589 | 8.186 | 1.00 | 29.44 | C |
| ATOM | 8104 | C | VAL | A | 529 | −66.609 | 14.243 | 6.887 | 1.00 | 28.95 | C |
| ATOM | 8105 | O | VAL | A | 529 | −66.755 | 14.016 | 5.690 | 1.00 | 29.09 | O |
| ATOM | 8107 | N | LEU | A | 530 | −67.615 | 14.153 | 7.744 | 1.00 | 28.18 | N |
| ATOM | 8108 | CA | LEU | A | 530 | −68.956 | 13.874 | 7.246 | 1.00 | 27.72 | C |
| ATOM | 8110 | CB | LEU | A | 530 | −69.971 | 13.715 | 8.395 | 1.00 | 27.75 | C |
| ATOM | 8113 | CG | LEU | A | 530 | −70.334 | 12.274 | 8.775 | 1.00 | 27.36 | C |
| ATOM | 8115 | CD1 | LEU | A | 530 | −69.096 | 11.415 | 9.050 | 1.00 | 26.86 | C |
| ATOM | 8119 | CD2 | LEU | A | 530 | −71.273 | 12.279 | 9.968 | 1.00 | 27.14 | C |
| ATOM | 8123 | C | LEU | A | 530 | −69.401 | 14.963 | 6.256 | 1.00 | 27.16 | C |
| ATOM | 8124 | O | LEU | A | 530 | −69.861 | 14.652 | 5.161 | 1.00 | 27.42 | O |
| ATOM | 8126 | N | SER | A | 531 | −69.230 | 16.229 | 6.635 | 1.00 | 26.21 | N |
| ATOM | 8127 | CA | SER | A | 531 | −69.730 | 17.359 | 5.853 | 1.00 | 25.12 | C |
| ATOM | 8129 | CB | SER | A | 531 | −69.519 | 18.657 | 6.618 | 1.00 | 25.01 | C |
| ATOM | 8132 | OG | SER | A | 531 | −68.167 | 18.791 | 6.985 | 1.00 | 23.94 | O |
| ATOM | 8134 | C | SER | A | 531 | −69.055 | 17.476 | 4.507 | 1.00 | 24.48 | C |
| ATOM | 8135 | O | SER | A | 531 | −69.687 | 17.886 | 3.538 | 1.00 | 24.14 | O |
| ATOM | 8137 | N | VAL | A | 532 | −67.774 | 17.115 | 4.461 | 1.00 | 23.89 | N |
| ATOM | 8138 | CA | VAL | A | 532 | −66.962 | 17.226 | 3.246 | 1.00 | 23.53 | C |
| ATOM | 8140 | CB | VAL | A | 532 | −65.470 | 17.437 | 3.575 | 1.00 | 23.09 | C |
| ATOM | 8142 | CG1 | VAL | A | 532 | −64.633 | 17.355 | 2.348 | 1.00 | 22.32 | C |
| ATOM | 8146 | CG2 | VAL | A | 532 | −65.268 | 18.773 | 4.198 | 1.00 | 23.07 | C |
| ATOM | 8150 | C | VAL | A | 532 | −67.100 | 16.028 | 2.316 | 1.00 | 23.67 | C |
| ATOM | 8151 | O | VAL | A | 532 | −67.137 | 16.209 | 1.099 | 1.00 | 23.58 | O |
| ATOM | 8153 | N | ILE | A | 533 | −67.187 | 14.824 | 2.886 | 1.00 | 23.85 | N |
| ATOM | 8154 | CA | ILE | A | 533 | −67.172 | 13.578 | 2.107 | 1.00 | 24.08 | C |
| ATOM | 8156 | CB | ILE | A | 533 | −66.172 | 12.555 | 2.691 | 1.00 | 24.10 | C |
| ATOM | 8158 | CG1 | ILE | A | 533 | −64.745 | 13.079 | 2.631 | 1.00 | 23.47 | C |
| ATOM | 8161 | CD1 | ILE | A | 533 | −64.178 | 13.083 | 1.255 | 1.00 | 23.42 | C |

TABLE 3-7-continued

| | | | | Coordinates of *P. tremuloides* IspS | | | | | | |
|---|---|---|---|---|---|---|---|---|---|---|
| ATOM | 8165 | CG2 | ILE | A | 533 | −66.254 | 11.231 | 1.932 | 1.00 | 24.56 C |
| ATOM | 8169 | C | ILE | A | 533 | −68.522 | 12.859 | 1.990 | 1.00 | 24.27 C |
| ATOM | 8170 | O | ILE | A | 533 | −68.991 | 12.620 | .887 | 1.00 | 24.34 O |
| ATOM | 8172 | N | THR | A | 534 | −69.133 | 12.487 | 3.111 | 1.00 | 24.57 N |
| ATOM | 8173 | CA | THR | A | 534 | −70.279 | 11.564 | 3.072 | 1.00 | 24.92 C |
| ATOM | 8175 | CB | THR | A | 534 | −70.200 | 10.522 | 4.207 | 1.00 | 24.93 C |
| ATOM | 8177 | OG1 | THR | A | 534 | −70.491 | 11.149 | 5.458 | 1.00 | 25.28 O |
| ATOM | 8179 | CG2 | THR | A | 534 | −68.804 | 9.885 | 4.257 | 1.00 | 24.75 C |
| ATOM | 8183 | C | THR | A | 534 | −71.673 | 12.209 | 3.083 | 1.00 | 25.00 C |
| ATOM | 8184 | O | THR | A | 534 | −72.601 | 11.646 | 2.522 | 1.00 | 24.94 O |
| ATOM | 8186 | N | GLU | A | 535 | −71.821 | 13.374 | 3.708 | 1.00 | 25.26 N |
| ATOM | 8187 | CA | GLU | A | 535 | −73.132 | 14.024 | 3.833 | 1.00 | 25.34 C |
| ATOM | 8189 | CB | GLU | A | 535 | −73.333 | 14.523 | 5.255 | 1.00 | 25.44 C |
| ATOM | 8192 | CG | GLU | A | 535 | −73.753 | 13.424 | 6.196 | 1.00 | 25.80 C |
| ATOM | 8195 | CD | GLU | A | 535 | −74.307 | 13.963 | 7.468 | 1.00 | 25.72 C |
| ATOM | 8196 | OE1 | GLU | A | 535 | −75.375 | 13.487 | 7.881 | 1.00 | 24.50 O |
| ATOM | 8197 | OE2 | GLU | A | 535 | −73.678 | 14.877 | 8.039 | 1.00 | 27.03 O |
| ATOM | 8198 | C | GLU | A | 535 | −73.363 | 15.179 | 2.859 | 1.00 | 25.26 C |
| ATOM | 8199 | O | GLU | A | 535 | −72.686 | 16.206 | 2.939 | 1.00 | 25.02 O |
| ATOM | 8201 | N | PRO | A | 536 | −74.351 | 15.030 | 1.959 | 1.00 | 25.25 N |
| ATOM | 8202 | CA | PRO | A | 536 | −74.655 | 16.111 | 1.050 | 1.00 | 25.18 C |
| ATOM | 8204 | CB | PRO | A | 536 | −75.661 | 15.484 | .076 | 1.00 | 25.15 C |
| ATOM | 8207 | CG | PRO | A | 536 | −75.825 | 14.077 | .476 | 1.00 | 24.98 C |
| ATOM | 8210 | CD | PRO | A | 536 | −75.363 | 13.965 | 1.868 | 1.00 | 25.26 C |
| ATOM | 8213 | C | PRO | A | 536 | −75.289 | 17.265 | 1.801 | 1.00 | 25.30 C |
| ATOM | 8214 | O | PRO | A | 536 | −75.826 | 17.070 | 2.883 | 1.00 | 25.57 O |
| ATOM | 8215 | N | ILE | A | 537 | −75.213 | 18.458 | 1.230 | 1.00 | 25.36 N |
| ATOM | 8216 | CA | ILE | A | 537 | −75.807 | 19.638 | 1.827 | 1.00 | 25.34 C |
| ATOM | 8218 | CB | ILE | A | 537 | −75.201 | 20.918 | 1.221 | 1.00 | 25.14 C |
| ATOM | 8220 | CG1 | ILE | A | 537 | −73.787 | 21.131 | 1.744 | 1.00 | 24.32 C |
| ATOM | 8223 | CD1 | ILE | A | 537 | −73.228 | 22.472 | 1.406 | 1.00 | 23.22 C |
| ATOM | 8227 | CG2 | ILE | A | 537 | −76.030 | 22.131 | 1.569 | 1.00 | 25.54 C |
| ATOM | 8231 | C | ILE | A | 537 | −77.313 | 19.603 | 1.611 | 1.00 | 25.67 C |
| ATOM | 8232 | O | ILE | A | 537 | −77.786 | 19.132 | .579 | 1.00 | 25.47 O |
| ATOM | 8234 | N | LEU | A | 538 | −78.071 | 20.088 | 2.586 | 1.00 | 26.22 N |
| ATOM | 8235 | CA | LEU | A | 538 | −79.514 | 20.051 | 2.467 | 1.00 | 26.65 C |
| ATOM | 8237 | CB | LEU | A | 538 | −80.213 | 20.525 | 3.749 | 1.00 | 26.78 C |
| ATOM | 8240 | CG | LEU | A | 538 | −80.162 | 19.609 | 4.989 | 1.00 | 26.64 C |
| ATOM | 8242 | CD1 | LEU | A | 538 | −81.218 | 20.033 | 6.007 | 1.00 | 26.16 C |
| ATOM | 8246 | CD2 | LEU | A | 538 | −80.346 | 18.138 | 4.633 | 1.00 | 26.12 C |
| ATOM | 8250 | C | LEU | A | 538 | −79.925 | 20.881 | 1.262 | 1.00 | 27.08 C |
| ATOM | 8253 | N | PRO | A | 539 | −80.786 | 20.306 | .414 | 1.00 | 28.03 N |
| ATOM | 8254 | CA | PRO | A | 539 | −81.117 | 20.855 | −.888 | 1.00 | 28.44 C |
| ATOM | 8256 | CB | PRO | A | 539 | −82.093 | 19.828 | −1.449 | 1.00 | 28.40 C |
| ATOM | 8259 | CG | PRO | A | 539 | −82.793 | 19.328 | −.253 | 1.00 | 28.30 C |
| ATOM | 8262 | CD | PRO | A | 539 | −81.720 | 19.228 | .787 | 1.00 | 28.11 C |
| ATOM | 8265 | C | PRO | A | 539 | −81.813 | 22.194 | −.804 | 1.00 | 28.89 C |
| ATOM | 8266 | O | PRO | A | 539 | −82.396 | 22.535 | .226 | 1.00 | 28.97 O |
| ATOM | 8267 | N | PHE | A | 540 | −81.774 | 22.932 | −1.906 | 1.00 | 29.32 N |
| ATOM | 8268 | CA | PHE | A | 540 | −82.380 | 24.245 | −1.962 | 1.00 | 29.50 C |
| ATOM | 8270 | CB | PHE | A | 540 | −82.146 | 24.874 | −3.326 | 1.00 | 29.56 C |
| ATOM | 8273 | CG | PHE | A | 540 | −82.757 | 26.227 | −3.463 | 1.00 | 29.75 C |
| ATOM | 8274 | CD1 | PHE | A | 540 | −83.874 | 26.429 | −4.255 | 1.00 | 29.47 C |
| ATOM | 8276 | CE1 | PHE | A | 540 | −84.441 | 27.681 | −4.364 | 1.00 | 29.46 C |
| ATOM | 8278 | CZ | PHE | A | 540 | −83.901 | 28.743 | −3.674 | 1.00 | 29.81 C |
| ATOM | 8280 | CE2 | PHE | A | 540 | −82.791 | 28.553 | −2.877 | 1.00 | 30.21 C |
| ATOM | 8282 | CD2 | PHE | A | 540 | −82.229 | 27.300 | −2.770 | 1.00 | 30.17 C |
| ATOM | 8284 | C | PHE | A | 540 | −83.865 | 24.129 | −1.722 | 1.00 | 29.66 C |
| ATOM | 8285 | O | PHE | A | 540 | −84.568 | 23.551 | −2.545 | 1.00 | 29.66 O |
| ATOM | 8287 | N | GLU | A | 541 | −84.337 | 24.673 | −.601 | 1.00 | 29.90 N |
| ATOM | 8288 | CA | GLU | A | 541 | −85.761 | 24.605 | −.233 | 1.00 | 30.06 C |
| ATOM | 8290 | CB | GLU | A | 541 | −85.951 | 23.724 | 1.017 | 1.00 | 30.15 C |
| ATOM | 8293 | CG | GLU | A | 541 | −87.411 | 23.361 | 1.367 | 1.00 | 30.64 C |
| ATOM | 8296 | CD | GLU | A | 541 | −88.091 | 24.351 | 2.322 | 1.00 | 31.35 C |
| ATOM | 8297 | OE1 | GLU | A | 541 | −87.468 | 25.370 | 2.680 | 1.00 | 32.67 O |
| ATOM | 8298 | OE2 | GLU | A | 541 | −89.254 | 24.114 | 2.719 | 1.00 | 30.48 O |
| ATOM | 8299 | C | GLU | A | 541 | −86.315 | 26.011 | −.010 | 1.00 | 29.89 C |
| ATOM | 8300 | O | GLU | A | 541 | −86.835 | 26.636 | −.936 | 1.00 | 29.71 O |
| ATOM | 8302 | N | LEU | B | 17 | −69.666 | −25.325 | 2.227 | 1.00 | 33.20 N |
| ATOM | 8303 | CA | LEU | B | 17 | −69.356 | −25.417 | .755 | 1.00 | 33.49 C |
| ATOM | 8305 | CB | LEU | B | 17 | −70.240 | −26.475 | .048 | 1.00 | 33.44 C |
| ATOM | 8308 | CG | LEU | B | 17 | −70.077 | −27.986 | .328 | 1.00 | 33.60 C |
| ATOM | 8310 | CD1 | LEU | B | 17 | −71.285 | −28.778 | −.217 | 1.00 | 32.76 C |
| ATOM | 8314 | CD2 | LEU | B | 17 | −68.763 | −28.553 | −.230 | 1.00 | 33.21 C |
| ATOM | 8318 | C | LEU | B | 17 | −69.513 | −24.044 | .055 | 1.00 | 33.54 C |
| ATOM | 8319 | O | LEU | B | 17 | −70.550 | −23.380 | .195 | 1.00 | 33.77 O |
| ATOM | 8323 | N | LEU | B | 18 | −68.481 | −23.637 | −.696 | 1.00 | 33.44 N |
| ATOM | 8324 | CA | LEU | B | 18 | −68.476 | −22.362 | −1.454 | 1.00 | 33.07 C |

TABLE 3-7-continued

Coordinates of *P. tremuloides* IspS

| ATOM | 8326 | CB | LEU | B | 18 | −67.029 | −21.960 | −1.840 | 1.00 | 33.21 | C |
|---|---|---|---|---|---|---|---|---|---|---|---|
| ATOM | 8329 | CG | LEU | B | 18 | −66.065 | −21.488 | −.721 | 1.00 | 34.06 | C |
| ATOM | 8331 | CD1 | LEU | B | 18 | −64.607 | −21.351 | −1.235 | 1.00 | 34.51 | C |
| ATOM | 8335 | CD2 | LEU | B | 18 | −66.516 | −20.164 | −.061 | 1.00 | 33.43 | C |
| ATOM | 8339 | C | LEU | B | 18 | −69.379 | −22.400 | −2.714 | 1.00 | 32.37 | C |
| ATOM | 8340 | O | LEU | B | 18 | −69.710 | −21.355 | −3.274 | 1.00 | 32.29 | O |
| ATOM | 8342 | N | SER | B | 19 | −69.765 | −23.597 | −3.153 | 1.00 | 31.62 | N |
| ATOM | 8343 | CA | SER | B | 19 | −70.711 | −23.749 | −4.253 | 1.00 | 31.16 | C |
| ATOM | 8345 | CB | SER | B | 19 | −70.443 | −25.067 | −5.033 | 1.00 | 31.09 | C |
| ATOM | 8348 | OG | SER | B | 19 | −70.977 | −26.243 | −4.421 | 1.00 | 29.36 | O |
| ATOM | 8350 | C | SER | B | 19 | −72.168 | −23.663 | −3.759 | 1.00 | 31.45 | C |
| ATOM | 8351 | O | SER | B | 19 | −73.076 | −23.432 | −4.551 | 1.00 | 31.13 | O |
| ATOM | 8353 | N | SER | B | 20 | −72.386 | −23.824 | −2.451 | 1.00 | 31.91 | N |
| ATOM | 8354 | CA | SER | B | 20 | −73.749 | −23.900 | −1.879 | 1.00 | 32.34 | C |
| ATOM | 8356 | CB | SER | B | 20 | −73.706 | −24.122 | −.357 | 1.00 | 32.35 | C |
| ATOM | 8359 | OG | SER | B | 20 | −73.393 | −25.473 | −.055 | 1.00 | 32.34 | O |
| ATOM | 8361 | C | SER | B | 20 | −74.601 | −22.670 | −2.204 | 1.00 | 32.69 | C |
| ATOM | 8362 | O | SER | B | 20 | −74.072 | −21.600 | −2.487 | 1.00 | 32.89 | O |
| ATOM | 8364 | N | ASP | B | 21 | −75.921 | −22.831 | −2.119 | 1.00 | 33.13 | N |
| ATOM | 8365 | CA | ASP | B | 21 | −76.874 | −21.901 | −2.745 | 1.00 | 33.40 | C |
| ATOM | 8367 | CB | ASP | B | 21 | −78.179 | −22.628 | −3.045 | 1.00 | 33.64 | C |
| ATOM | 8370 | CG | ASP | B | 21 | −77.943 | −23.883 | −3.828 | 1.00 | 35.35 | C |
| ATOM | 8371 | OD1 | ASP | B | 21 | −77.031 | −23.866 | −4.684 | 1.00 | 38.26 | O |
| ATOM | 8372 | OD2 | ASP | B | 21 | −78.631 | −24.890 | −3.590 | 1.00 | 37.55 | O |
| ATOM | 8373 | C | ASP | B | 21 | −77.141 | −20.649 | −1.940 | 1.00 | 33.23 | C |
| ATOM | 8374 | O | ASP | B | 21 | −78.039 | −20.616 | −1.106 | 1.00 | 32.91 | O |
| ATOM | 8376 | N | THR | B | 22 | −76.348 | −19.621 | −2.229 | 1.00 | 33.46 | N |
| ATOM | 8377 | CA | THR | B | 22 | −76.443 | −18.307 | −1.593 | 1.00 | 33.79 | C |
| ATOM | 8379 | CB | THR | B | 22 | −76.460 | −18.378 | −.016 | 1.00 | 33.74 | C |
| ATOM | 8381 | OG1 | THR | B | 22 | −75.426 | −19.250 | .460 | 1.00 | 32.97 | O |
| ATOM | 8383 | CG2 | THR | B | 22 | −77.805 | −18.838 | .535 | 1.00 | 33.55 | C |
| ATOM | 8387 | C | THR | B | 22 | −75.217 | −17.479 | −2.018 | 1.00 | 34.24 | C |
| ATOM | 8388 | O | THR | B | 22 | −74.102 | −17.988 | −1.892 | 1.00 | 33.95 | O |
| ATOM | 8390 | N | ASP | B | 23 | −75.361 | −16.248 | −2.543 | 1.00 | 34.99 | N |
| ATOM | 8391 | CA | ASP | B | 23 | −76.603 | −15.620 | −3.103 | 1.00 | 35.61 | C |
| ATOM | 8393 | CB | ASP | B | 23 | −77.242 | −16.538 | −4.170 | 1.00 | 35.51 | C |
| ATOM | 8396 | CG | ASP | B | 23 | −76.196 | −17.236 | −5.034 | 1.00 | 36.08 | C |
| ATOM | 8397 | OD1 | ASP | B | 23 | −75.084 | −16.685 | −5.194 | 1.00 | 35.58 | O |
| ATOM | 8398 | OD2 | ASP | B | 23 | −76.473 | −18.344 | −5.541 | 1.00 | 37.65 | O |
| ATOM | 8399 | C | ASP | B | 23 | −77.662 | −15.083 | −2.097 | 1.00 | 36.10 | C |
| ATOM | 8400 | O | ASP | B | 23 | −78.644 | −15.770 | −1.799 | 1.00 | 36.13 | O |
| ATOM | 8402 | N | GLU | B | 24 | −77.487 | −13.845 | −1.616 | 1.00 | 36.74 | N |
| ATOM | 8403 | CA | GLU | B | 24 | −78.358 | −13.316 | −.543 | 1.00 | 37.59 | C |
| ATOM | 8405 | CB | GLU | B | 24 | −77.765 | −13.666 | .838 | 1.00 | 37.88 | C |
| ATOM | 8408 | CG | GLU | B | 24 | −77.624 | −15.173 | 1.120 | 1.00 | 38.51 | C |
| ATOM | 8411 | CD | GLU | B | 24 | −77.314 | −15.510 | 2.588 | 1.00 | 39.48 | C |
| ATOM | 8412 | OE1 | GLU | B | 24 | −77.171 | −14.581 | 3.434 | 1.00 | 39.60 | O |
| ATOM | 8413 | OE2 | GLU | B | 24 | −77.221 | −16.725 | 2.884 | 1.00 | 39.51 | O |
| ATOM | 8414 | C | GLU | B | 24 | −78.730 | −11.809 | −.559 | 1.00 | 38.11 | C |
| ATOM | 8415 | O | GLU | B | 24 | −79.840 | −11.453 | −.972 | 1.00 | 38.20 | O |
| ATOM | 8417 | N | SER | B | 25 | −77.825 | −10.941 | −.089 | 1.00 | 38.70 | N |
| ATOM | 8418 | CA | SER | B | 25 | −78.192 | −9.560 | .312 | 1.00 | 39.21 | C |
| ATOM | 8420 | CB | SER | B | 25 | −76.995 | −8.783 | .916 | 1.00 | 39.29 | C |
| ATOM | 8423 | OG | SER | B | 25 | −76.267 | −8.037 | −.056 | 1.00 | 39.40 | O |
| ATOM | 8425 | C | SER | B | 25 | −78.853 | −8.738 | −.802 | 1.00 | 39.69 | C |
| ATOM | 8426 | O | SER | B | 25 | −78.707 | −9.050 | −1.995 | 1.00 | 39.75 | O |
| ATOM | 8428 | N | ILE | B | 26 | −79.544 | −7.670 | −.378 | 1.00 | 40.21 | N |
| ATOM | 8429 | CA | ILE | B | 26 | −80.554 | −6.962 | −1.189 | 1.00 | 40.55 | C |
| ATOM | 8431 | CB | ILE | B | 26 | −79.925 | −6.082 | −2.319 | 1.00 | 40.66 | C |
| ATOM | 8433 | CG1 | ILE | B | 26 | −79.083 | −4.951 | −1.700 | 1.00 | 40.73 | C |
| ATOM | 8436 | CD1 | ILE | B | 26 | −78.596 | −3.877 | −2.698 | 1.00 | 40.68 | C |
| ATOM | 8440 | CG2 | ILE | B | 26 | −81.018 | −5.475 | −3.203 | 1.00 | 40.88 | C |
| ATOM | 8444 | C | ILE | B | 26 | −81.575 | −7.999 | −1.714 | 1.00 | 40.72 | C |
| ATOM | 8445 | O | ILE | B | 26 | −81.311 | −8.710 | −2.690 | 1.00 | 40.80 | O |
| ATOM | 8447 | N | GLU | B | 27 | −82.729 | −8.070 | −1.037 | 1.00 | 40.86 | N |
| ATOM | 8448 | CA | GLU | B | 27 | −83.694 | −9.190 | −1.160 | 1.00 | 40.88 | C |
| ATOM | 8450 | CB | GLU | B | 27 | −84.782 | −9.060 | −.061 | 1.00 | 40.95 | C |
| ATOM | 8453 | CG | GLU | B | 27 | −84.235 | −9.257 | 1.379 | 1.00 | 41.28 | C |
| ATOM | 8456 | CD | GLU | B | 27 | −85.123 | −8.657 | 2.484 | 1.00 | 41.74 | C |
| ATOM | 8457 | OE1 | GLU | B | 27 | −85.593 | −7.504 | 2.344 | 1.00 | 41.14 | O |
| ATOM | 8458 | OE2 | GLU | B | 27 | −85.332 | −9.337 | 3.514 | 1.00 | 42.36 | O |
| ATOM | 8459 | C | GLU | B | 27 | −84.290 | −9.355 | −2.587 | 1.00 | 40.75 | C |
| ATOM | 8460 | O | GLU | B | 27 | −83.664 | −8.936 | −3.569 | 1.00 | 40.88 | O |
| ATOM | 8462 | N | VAL | B | 28 | −85.461 | −9.994 | −2.712 | 1.00 | 40.40 | N |
| ATOM | 8463 | CA | VAL | B | 28 | −86.033 | −10.361 | −4.027 | 1.00 | 39.97 | C |
| ATOM | 8465 | CB | VAL | B | 28 | −86.034 | −9.157 | −5.053 | 1.00 | 40.03 | C |
| ATOM | 8467 | CG1 | VAL | B | 28 | −86.494 | −9.600 | −6.444 | 1.00 | 39.63 | C |
| ATOM | 8471 | CG2 | VAL | B | 28 | −86.900 | −7.994 | −4.525 | 1.00 | 39.86 | C |

TABLE 3-7-continued

Coordinates of *P. tremuloides* IspS

| ATOM | 8475 | C | VAL | B | 28 | −85.335 | −11.600 | −4.625 | 1.00 | 39.63 | C |
|---|---|---|---|---|---|---|---|---|---|---|---|
| ATOM | 8476 | O | VAL | B | 28 | −85.858 | −12.204 | −5.567 | 1.00 | 39.63 | O |
| ATOM | 8478 | N | HIS | B | 29 | −84.175 | −11.980 | −4.069 | 1.00 | 39.21 | N |
| ATOM | 8479 | CA | HIS | B | 29 | −83.431 | −13.177 | −4.504 | 1.00 | 38.81 | C |
| ATOM | 8481 | CB | HIS | B | 29 | −81.914 | −12.913 | −4.665 | 1.00 | 38.97 | C |
| ATOM | 8484 | CG | HIS | B | 29 | −81.571 | −11.721 | −5.512 | 1.00 | 39.99 | C |
| ATOM | 8485 | ND1 | HIS | B | 29 | −81.181 | −11.825 | −6.834 | 1.00 | 40.79 | N |
| ATOM | 8487 | CE1 | HIS | B | 29 | −80.931 | −10.615 | −7.312 | 1.00 | 40.76 | C |
| ATOM | 8489 | NE2 | HIS | B | 29 | −81.134 | −9.734 | −6.346 | 1.00 | 40.27 | N |
| ATOM | 8491 | CD2 | HIS | B | 29 | −81.525 | −10.400 | −5.209 | 1.00 | 40.17 | C |
| ATOM | 8493 | C | HIS | B | 29 | −83.611 | −14.340 | −3.523 | 1.00 | 38.05 | C |
| ATOM | 8494 | O | HIS | B | 29 | −82.782 | −15.259 | −3.526 | 1.00 | 38.02 | O |
| ATOM | 8496 | N | LYS | B | 30 | −84.667 | −14.321 | −2.694 | 1.00 | 37.06 | N |
| ATOM | 8497 | CA | LYS | B | 30 | −85.107 | −15.559 | −2.022 | 1.00 | 36.33 | C |
| ATOM | 8499 | CB | LYS | B | 30 | −86.056 | −15.286 | −.836 | 1.00 | 36.27 | C |
| ATOM | 8502 | CG | LYS | B | 30 | −85.352 | −14.818 | .461 | 1.00 | 36.09 | C |
| ATOM | 8505 | CD | LYS | B | 30 | −86.355 | −14.599 | 1.612 | 1.00 | 36.03 | C |
| ATOM | 8508 | CE | LYS | B | 30 | −85.811 | −13.659 | 2.701 | 1.00 | 36.24 | C |
| ATOM | 8511 | NZ | LYS | B | 30 | −86.802 | −13.356 | 3.789 | 1.00 | 35.65 | N |
| ATOM | 8515 | C | LYS | B | 30 | −85.710 | −16.510 | −3.094 | 1.00 | 35.69 | C |
| ATOM | 8516 | O | LYS | B | 30 | −86.706 | −17.205 | −2.879 | 1.00 | 35.35 | O |
| ATOM | 8518 | N | ASP | B | 31 | −85.075 | −16.484 | −4.268 | 1.00 | 35.13 | N |
| ATOM | 8519 | CA | ASP | B | 31 | −85.145 | −17.519 | −5.282 | 1.00 | 34.64 | C |
| ATOM | 8521 | CB | ASP | B | 31 | −84.592 | −16.962 | −6.623 | 1.00 | 34.60 | C |
| ATOM | 8524 | CG | ASP | B | 31 | −84.419 | −18.032 | −7.725 | 1.00 | 34.24 | C |
| ATOM | 8525 | OD1 | ASP | B | 31 | −84.914 | −19.165 | −7.570 | 1.00 | 34.58 | O |
| ATOM | 8526 | OD2 | ASP | B | 31 | −83.776 | −17.732 | −8.761 | 1.00 | 31.56 | O |
| ATOM | 8527 | C | ASP | B | 31 | −84.304 | −18.675 | −4.721 | 1.00 | 34.31 | C |
| ATOM | 8528 | O | ASP | B | 31 | −83.122 | −18.838 | −5.038 | 1.00 | 34.03 | O |
| ATOM | 8530 | N | LYS | B | 32 | −84.917 | −19.429 | −3.813 | 1.00 | 33.94 | N |
| ATOM | 8531 | CA | LYS | B | 32 | −84.380 | −20.710 | −3.369 | 1.00 | 33.36 | C |
| ATOM | 8533 | CB | LYS | B | 32 | −83.772 | −20.607 | −1.973 | 1.00 | 33.45 | C |
| ATOM | 8536 | CG | LYS | B | 32 | −82.540 | −19.693 | −1.951 | 1.00 | 33.56 | C |
| ATOM | 8539 | CD | LYS | B | 32 | −82.025 | −19.455 | −.532 | 1.00 | 34.17 | C |
| ATOM | 8542 | CE | LYS | B | 32 | −81.671 | −17.987 | −.283 | 1.00 | 34.16 | C |
| ATOM | 8545 | NZ | LYS | B | 32 | −80.746 | −17.437 | −1.311 | 1.00 | 34.07 | N |
| ATOM | 8549 | C | LYS | B | 32 | −85.490 | −21.764 | −3.499 | 1.00 | 32.57 | C |
| ATOM | 8550 | O | LYS | B | 32 | −85.908 | −22.412 | −2.538 | 1.00 | 32.10 | O |
| ATOM | 8552 | N | ALA | B | 33 | −85.976 | −21.859 | −4.738 | 1.00 | 31.66 | N |
| ATOM | 8553 | CA | ALA | B | 33 | −86.576 | −23.055 | −5.259 | 1.00 | 30.94 | C |
| ATOM | 8555 | CB | ALA | B | 33 | −87.247 | −22.773 | −6.597 | 1.00 | 30.47 | C |
| ATOM | 8559 | C | ALA | B | 33 | −85.442 | −24.081 | −5.403 | 1.00 | 30.55 | C |
| ATOM | 8560 | O | ALA | B | 33 | −85.684 | −25.230 | −5.751 | 1.00 | 31.12 | O |
| ATOM | 8562 | N | LYS | B | 34 | −84.200 | −23.660 | −5.161 | 1.00 | 29.73 | N |
| ATOM | 8563 | CA | LYS | B | 34 | −83.107 | −24.585 | −4.839 | 1.00 | 29.09 | C |
| ATOM | 8565 | CB | LYS | B | 34 | −81.776 | −23.817 | −4.865 | 1.00 | 29.30 | C |
| ATOM | 8568 | CG | LYS | B | 34 | −80.678 | −24.474 | −5.726 | 1.00 | 29.76 | C |
| ATOM | 8571 | CD | LYS | B | 34 | −79.633 | −23.458 | −6.283 | 1.00 | 28.74 | C |
| ATOM | 8574 | CE | LYS | B | 34 | −78.417 | −24.186 | −6.890 | 1.00 | 27.56 | C |
| ATOM | 8577 | NZ | LYS | B | 34 | −78.745 | −25.174 | −7.935 | 1.00 | 26.16 | N |
| ATOM | 8581 | C | LYS | B | 34 | −83.376 | −25.320 | −3.472 | 1.00 | 28.37 | C |
| ATOM | 8582 | O | LYS | B | 34 | −83.254 | −24.755 | −2.374 | 1.00 | 27.82 | O |
| ATOM | 8584 | N | LYS | B | 35 | −83.635 | −26.620 | −3.604 | 1.00 | 27.53 | N |
| ATOM | 8585 | CA | LYS | B | 35 | −84.629 | −27.429 | −2.851 | 1.00 | 26.77 | C |
| ATOM | 8587 | CB | LYS | B | 35 | −85.729 | −26.602 | −2.170 | 1.00 | 26.81 | C |
| ATOM | 8590 | CG | LYS | B | 35 | −87.089 | −26.520 | −2.907 | 1.00 | 27.05 | C |
| ATOM | 8593 | CD | LYS | B | 35 | −88.096 | −27.604 | −2.452 | 1.00 | 27.41 | C |
| ATOM | 8596 | CE | LYS | B | 35 | −89.394 | −27.636 | −3.300 | 1.00 | 27.21 | C |
| ATOM | 8599 | NZ | LYS | B | 35 | −90.501 | −26.792 | −2.762 | 1.00 | 26.28 | N |
| ATOM | 8603 | C | LYS | B | 35 | −85.257 | −28.357 | −3.920 | 1.00 | 26.03 | C |
| ATOM | 8604 | O | LYS | B | 35 | −85.853 | −29.386 | −3.626 | 1.00 | 26.00 | O |
| ATOM | 8606 | N | LEU | B | 36 | −85.171 | −27.909 | −5.168 | 1.00 | 24.98 | N |
| ATOM | 8607 | CA | LEU | B | 36 | −85.095 | −28.783 | −6.319 | 1.00 | 24.02 | C |
| ATOM | 8609 | CB | LEU | B | 36 | −85.004 | −27.930 | −7.594 | 1.00 | 23.83 | C |
| ATOM | 8612 | CG | LEU | B | 36 | −86.208 | −27.103 | −8.062 | 1.00 | 22.23 | C |
| ATOM | 8614 | CD1 | LEU | B | 36 | −85.762 | −25.873 | −8.802 | 1.00 | 19.93 | C |
| ATOM | 8618 | CD2 | LEU | B | 36 | −87.092 | −27.930 | −8.951 | 1.00 | 22.11 | C |
| ATOM | 8622 | C | LEU | B | 36 | −83.834 | −29.659 | −6.185 | 1.00 | 23.58 | C |
| ATOM | 8623 | O | LEU | B | 36 | −83.840 | −30.842 | −6.508 | 1.00 | 23.38 | O |
| ATOM | 8625 | N | GLU | B | 37 | −82.742 | −29.046 | −5.739 | 1.00 | 23.18 | N |
| ATOM | 8626 | CA | GLU | B | 37 | −81.510 | −29.753 | −5.396 | 1.00 | 22.88 | C |
| ATOM | 8628 | CB | GLU | B | 37 | −80.466 | −28.766 | −4.855 | 1.00 | 22.76 | C |
| ATOM | 8631 | CG | GLU | B | 37 | −79.038 | −29.297 | −4.874 | 1.00 | 22.24 | C |
| ATOM | 8634 | CD | GLU | B | 37 | −78.085 | −28.505 | −4.009 | 1.00 | 21.06 | C |
| ATOM | 8635 | OE1 | GLU | B | 37 | −78.368 | −27.331 | −3.737 | 1.00 | 19.65 | O |
| ATOM | 8636 | OE2 | GLU | B | 37 | −77.037 | −29.059 | −3.615 | 1.00 | 20.62 | O |
| ATOM | 8637 | C | GLU | B | 37 | −81.748 | −30.856 | −4.364 | 1.00 | 22.95 | C |
| ATOM | 8638 | O | GLU | B | 37 | −81.164 | −31.933 | −4.458 | 1.00 | 22.99 | O |

TABLE 3-7-continued

| | | | | | | Coordinates of *P. tremuloides* IspS | | | | |
|---|---|---|---|---|---|---|---|---|---|---|
| ATOM | 8640 | N | ALA | B | 38 | −82.591 | −30.575 | −3.372 | 1.00 | 23.02 N |
| ATOM | 8641 | CA | ALA | B | 38 | −82.973 | −31.565 | −2.364 | 1.00 | 22.93 C |
| ATOM | 8643 | CB | ALA | B | 38 | −83.966 | −30.959 | −1.374 | 1.00 | 22.73 C |
| ATOM | 8647 | C | ALA | B | 38 | −83.580 | −32.778 | −3.044 | 1.00 | 23.05 C |
| ATOM | 8648 | O | ALA | B | 38 | −83.170 | −33.909 | −2.813 | 1.00 | 22.52 O |
| ATOM | 8650 | N | GLU | B | 39 | −84.546 | −32.506 | −3.912 | 1.00 | 23.66 N |
| ATOM | 8651 | CA | GLU | B | 39 | −85.273 | −33.534 | −4.642 | 1.00 | 24.08 C |
| ATOM | 8653 | CB | GLU | B | 39 | −86.403 | −32.891 | −5.453 | 1.00 | 24.28 C |
| ATOM | 8656 | CG | GLU | B | 39 | −87.405 | −33.869 | −6.075 | 1.00 | 25.14 C |
| ATOM | 8659 | CD | GLU | B | 39 | −88.773 | −33.227 | −6.341 | 1.00 | 26.43 C |
| ATOM | 8660 | OE1 | GLU | B | 39 | −89.232 | −32.381 | −5.519 | 1.00 | 25.90 O |
| ATOM | 8661 | OE2 | GLU | B | 39 | −89.387 | −33.584 | −7.375 | 1.00 | 26.99 O |
| ATOM | 8662 | C | GLU | B | 39 | −84.362 | −34.359 | −5.545 | 1.00 | 24.18 C |
| ATOM | 8663 | O | GLU | B | 39 | −84.483 | −35.579 | −5.575 | 1.00 | 24.32 O |
| ATOM | 8665 | N | VAL | B | 40 | −83.450 | −33.710 | −6.269 | 1.00 | 24.43 N |
| ATOM | 8666 | CA | VAL | B | 40 | −82.533 | −34.437 | −7.153 | 1.00 | 24.59 C |
| ATOM | 8668 | CB | VAL | B | 40 | −81.734 | −33.496 | −8.087 | 1.00 | 24.65 C |
| ATOM | 8670 | CG1 | VAL | B | 40 | −80.611 | −34.258 | −8.792 | 1.00 | 24.14 C |
| ATOM | 8674 | CG2 | VAL | B | 40 | −82.662 | −32.852 | −9.106 | 1.00 | 23.89 C |
| ATOM | 8678 | C | VAL | B | 40 | −81.592 | −35.304 | −6.328 | 1.00 | 24.99 C |
| ATOM | 8679 | O | VAL | B | 40 | −81.265 | −36.407 | −6.717 | 1.00 | 24.77 O |
| ATOM | 8681 | N | ARG | B | 41 | −81.184 | −34.811 | −5.171 | 1.00 | 25.79 N |
| ATOM | 8682 | CA | ARG | B | 41 | −80.387 | −35.613 | −4.248 | 1.00 | 26.75 C |
| ATOM | 8684 | CB | ARG | B | 41 | −80.032 | −34.823 | −2.998 | 1.00 | 27.38 C |
| ATOM | 8687 | CG | ARG | B | 41 | −78.568 | −34.777 | −2.757 | 1.00 | 30.18 C |
| ATOM | 8690 | CD | ARG | B | 41 | −78.281 | −34.610 | −1.273 | 1.00 | 34.43 C |
| ATOM | 8693 | NE | ARG | B | 41 | −76.896 | −34.198 | −1.016 | 1.00 | 37.07 N |
| ATOM | 8695 | CZ | ARG | B | 41 | −76.350 | −33.045 | −1.416 | 1.00 | 38.54 C |
| ATOM | 8696 | NH1 | ARG | B | 41 | −75.083 | −32.797 | −1.112 | 1.00 | 40.04 N |
| ATOM | 8699 | NH2 | ARG | B | 41 | −77.037 | −32.145 | −2.128 | 1.00 | 38.45 N |
| ATOM | 8702 | C | ARG | B | 41 | −81.081 | −36.860 | −3.762 | 1.00 | 26.60 C |
| ATOM | 8703 | O | ARG | B | 41 | −80.446 | −37.894 | −3.627 | 1.00 | 26.89 O |
| ATOM | 8705 | N | ARG | B | 42 | −82.363 | −36.733 | −3.423 | 1.00 | 26.41 N |
| ATOM | 8706 | CA | ARG | B | 42 | −83.159 | −37.870 | −3.002 | 1.00 | 26.09 C |
| ATOM | 8708 | CB | ARG | B | 42 | −84.588 | −37.452 | −2.674 | 1.00 | 25.99 C |
| ATOM | 8711 | CG | ARG | B | 42 | −85.426 | −38.562 | −2.049 | 1.00 | 25.45 C |
| ATOM | 8714 | CD | ARG | B | 42 | −86.783 | −38.078 | −1.645 | 1.00 | 24.26 C |
| ATOM | 8717 | NE | ARG | B | 42 | −87.549 | −37.602 | −2.794 | 1.00 | 23.73 N |
| ATOM | 8719 | CZ | ARG | B | 42 | −88.547 | −36.722 | −2.717 | 1.00 | 24.51 C |
| ATOM | 8720 | NH1 | ARG | B | 42 | −88.912 | −36.195 | −1.545 | 1.00 | 24.99 N |
| ATOM | 8723 | NH2 | ARG | B | 42 | −89.185 | −36.354 | −3.816 | 1.00 | 24.46 N |
| ATOM | 8726 | C | ARG | B | 42 | −83.167 | −38.894 | −4.118 | 1.00 | 26.28 C |
| ATOM | 8727 | O | ARG | B | 42 | −82.864 | −40.054 | −3.888 | 1.00 | 26.39 O |
| ATOM | 8729 | N | GLU | B | 43 | −83.476 | −38.460 | −5.334 | 1.00 | 26.52 N |
| ATOM | 8730 | CA | GLU | B | 43 | −83.476 | −39.370 | −6.479 | 1.00 | 27.00 C |
| ATOM | 8732 | CB | GLU | B | 43 | −83.982 | −38.676 | −7.753 | 1.00 | 27.50 C |
| ATOM | 8735 | CG | GLU | B | 43 | −85.469 | −38.275 | −7.699 | 1.00 | 29.78 C |
| ATOM | 8738 | CD | GLU | B | 43 | −86.342 | −39.301 | −6.974 | 1.00 | 32.52 C |
| ATOM | 8739 | OE1 | GLU | B | 43 | −86.388 | −40.455 | −7.445 | 1.00 | 35.06 O |
| ATOM | 8740 | OE2 | GLU | B | 43 | −86.966 | −38.963 | −5.936 | 1.00 | 33.80 O |
| ATOM | 8741 | C | GLU | B | 43 | −82.147 | −40.059 | −6.769 | 1.00 | 26.37 C |
| ATOM | 8742 | O | GLU | B | 43 | −82.162 | −41.126 | −7.355 | 1.00 | 26.63 O |
| ATOM | 8744 | N | ILE | B | 44 | −81.018 | −39.472 | −6.373 | 1.00 | 25.85 N |
| ATOM | 8745 | CA | ILE | B | 44 | −79.717 | −40.126 | −6.555 | 1.00 | 25.55 C |
| ATOM | 8747 | CB | ILE | B | 44 | −78.547 | −39.121 | −6.692 | 1.00 | 25.26 C |
| ATOM | 8749 | CG1 | ILE | B | 44 | −78.706 | −38.273 | −7.953 | 1.00 | 24.47 C |
| ATOM | 8752 | CD1 | ILE | B | 44 | −77.690 | −37.163 | −8.114 | 1.00 | 23.21 C |
| ATOM | 8756 | CG2 | ILE | B | 44 | −77.207 | −39.863 | −6.778 | 1.00 | 25.35 C |
| ATOM | 8760 | C | ILE | B | 44 | −79.404 | −41.109 | −5.428 | 1.00 | 25.84 C |
| ATOM | 8761 | O | ILE | B | 44 | −78.925 | −42.208 | −5.698 | 1.00 | 25.97 O |
| ATOM | 8763 | N | ASN | B | 45 | −79.663 | −40.708 | −4.177 | 1.00 | 26.25 N |
| ATOM | 8764 | CA | ASN | B | 45 | −79.403 | −41.542 | −2.983 | 1.00 | 26.34 C |
| ATOM | 8766 | CB | ASN | B | 45 | −79.284 | −40.681 | −1.719 | 1.00 | 26.01 C |
| ATOM | 8769 | CG | ASN | B | 45 | −78.072 | −39.789 | −1.723 | 1.00 | 24.65 C |
| ATOM | 8770 | OD1 | ASN | B | 45 | −76.957 | −40.226 | −1.434 | 1.00 | 22.47 O |
| ATOM | 8771 | ND2 | ASN | B | 45 | −78.288 | −38.516 | −2.009 | 1.00 | 23.36 N |
| ATOM | 8774 | C | ASN | B | 45 | −80.488 | −42.586 | −2.731 | 1.00 | 27.18 C |
| ATOM | 8775 | O | ASN | B | 45 | −80.374 | −43.390 | −1.806 | 1.00 | 27.30 O |
| ATOM | 8777 | N | ASN | B | 46 | −81.553 | −42.541 | −3.527 | 1.00 | 28.17 N |
| ATOM | 8778 | CA | ASN | B | 46 | −82.619 | −43.536 | −3.489 | 1.00 | 29.02 C |
| ATOM | 8780 | CB | ASN | B | 46 | −83.558 | −43.289 | −4.665 | 1.00 | 29.05 C |
| ATOM | 8783 | CG | ASN | B | 46 | −84.615 | −44.345 | −4.806 | 1.00 | 28.82 C |
| ATOM | 8784 | OD1 | ASN | B | 46 | −84.861 | −45.132 | −3.895 | 1.00 | 28.14 O |
| ATOM | 8785 | ND2 | ASN | B | 46 | −85.255 | −44.369 | −5.968 | 1.00 | 29.67 N |
| ATOM | 8788 | C | ASN | B | 46 | −82.076 | −44.958 | −3.549 | 1.00 | 30.14 C |
| ATOM | 8789 | O | ASN | B | 46 | −81.566 | −45.408 | −4.581 | 1.00 | 30.30 O |
| ATOM | 8791 | N | GLU | B | 47 | −82.218 | −45.674 | −2.446 | 1.00 | 31.36 N |
| ATOM | 8792 | CA | GLU | B | 47 | −81.575 | −46.968 | −2.295 | 1.00 | 32.61 C |

TABLE 3-7-continued

| | | | | | | | | | | |
|---|---|---|---|---|---|---|---|---|---|---|
| ATOM | 8794 | CB | GLU | B | 47 | −81.617 | −47.430 | −.823 | 1.00 | 33.09 C |
| ATOM | 8797 | CG | GLU | B | 47 | −80.974 | −46.466 | .218 | 1.00 | 34.19 C |
| ATOM | 8800 | CD | GLU | B | 47 | −81.919 | −45.337 | .721 | 1.00 | 34.57 C |
| ATOM | 8801 | OE1 | GLU | B | 47 | −82.911 | −45.012 | .029 | 1.00 | 34.53 O |
| ATOM | 8802 | OE2 | GLU | B | 47 | −81.652 | −44.762 | 1.805 | 1.00 | 34.30 O |
| ATOM | 8803 | C | GLU | B | 47 | −82.205 | −48.046 | −3.172 | 1.00 | 33.18 C |
| ATOM | 8804 | O | GLU | B | 47 | −81.604 | −49.088 | −3.370 | 1.00 | 33.44 O |
| ATOM | 8806 | N | LYS | B | 48 | −83.408 | −47.808 | −3.692 | 1.00 | 34.11 N |
| ATOM | 8807 | CA | LYS | B | 48 | −84.164 | −48.853 | −4.396 | 1.00 | 34.85 C |
| ATOM | 8809 | CB | LYS | B | 48 | −85.379 | −49.254 | −3.542 | 1.00 | 35.09 C |
| ATOM | 8812 | CG | LYS | B | 48 | −85.003 | −49.723 | −2.127 | 1.00 | 36.00 C |
| ATOM | 8815 | CD | LYS | B | 48 | −86.174 | −50.338 | −1.350 | 1.00 | 37.13 C |
| ATOM | 8818 | CE | LYS | B | 48 | −87.312 | −49.340 | −1.094 | 1.00 | 37.90 C |
| ATOM | 8821 | NZ | LYS | B | 48 | −86.908 | −48.161 | −.272 | 1.00 | 38.31 N |
| ATOM | 8825 | C | LYS | B | 48 | −84.586 | −48.487 | −5.835 | 1.00 | 35.13 C |
| ATOM | 8826 | O | LYS | B | 48 | −85.544 | −49.030 | −6.361 | 1.00 | 34.60 O |
| ATOM | 8828 | N | ALA | B | 49 | −83.858 | −47.576 | −6.474 | 1.00 | 36.09 N |
| ATOM | 8829 | CA | ALA | B | 49 | −84.093 | −47.261 | −7.886 | 1.00 | 36.87 C |
| ATOM | 8831 | CB | ALA | B | 49 | −83.550 | −45.880 | −8.238 | 1.00 | 36.73 C |
| ATOM | 8835 | C | ALA | B | 49 | −83.406 | −48.325 | −8.714 | 1.00 | 37.56 C |
| ATOM | 8836 | O | ALA | B | 49 | −82.315 | −48.761 | −8.363 | 1.00 | 37.62 O |
| ATOM | 8838 | N | GLU | B | 50 | −84.028 | −48.754 | −9.807 | 1.00 | 38.54 N |
| ATOM | 8839 | CA | GLU | B | 50 | −83.399 | −49.772 | −10.652 | 1.00 | 39.40 C |
| ATOM | 8841 | CB | GLU | B | 50 | −84.380 | −50.384 | −11.673 | 1.00 | 39.71 C |
| ATOM | 8844 | CG | GLU | B | 50 | −83.959 | −51.808 | −12.179 | 1.00 | 41.33 C |
| ATOM | 8847 | CD | GLU | B | 50 | −83.733 | −52.860 | −11.039 | 1.00 | 42.88 C |
| ATOM | 8848 | OE1 | GLU | B | 50 | −84.683 | −53.628 | −10.718 | 1.00 | 42.94 O |
| ATOM | 8849 | OE2 | GLU | B | 50 | −82.603 | −52.921 | −10.472 | 1.00 | 42.96 O |
| ATOM | 8850 | C | GLU | B | 50 | −82.171 | −49.163 | −11.330 | 1.00 | 39.43 C |
| ATOM | 8851 | O | GLU | B | 50 | −82.211 | −48.017 | −11.791 | 1.00 | 39.66 O |
| ATOM | 8853 | N | PHE | B | 51 | −81.084 | −49.929 | −11.376 | 1.00 | 39.32 N |
| ATOM | 8854 | CA | PHE | B | 51 | −79.763 | −49.360 | −11.636 | 1.00 | 39.32 C |
| ATOM | 8856 | CB | PHE | B | 51 | −78.675 | −50.429 | −11.476 | 1.00 | 39.62 C |
| ATOM | 8859 | CG | PHE | B | 51 | −78.470 | −50.889 | −10.032 | 1.00 | 41.82 C |
| ATOM | 8860 | CD1 | PHE | B | 51 | −78.093 | −49.978 | −9.032 | 1.00 | 42.93 C |
| ATOM | 8862 | CE1 | PHE | B | 51 | −77.892 | −50.391 | −7.705 | 1.00 | 43.30 C |
| ATOM | 8864 | CZ | PHE | B | 51 | −78.059 | −51.729 | −7.359 | 1.00 | 44.33 C |
| ATOM | 8866 | CE2 | PHE | B | 51 | −78.430 | −52.659 | −8.341 | 1.00 | 44.75 C |
| ATOM | 8868 | CD2 | PHE | B | 51 | −78.633 | −52.234 | −9.677 | 1.00 | 44.06 C |
| ATOM | 8870 | C | PHE | B | 51 | −79.646 | −48.625 | −12.976 | 1.00 | 38.57 C |
| ATOM | 8871 | O | PHE | B | 51 | −79.045 | −47.564 | −13.046 | 1.00 | 38.50 O |
| ATOM | 8873 | N | LEU | B | 52 | −80.262 | −49.155 | −14.024 | 1.00 | 37.99 N |
| ATOM | 8874 | CA | LEU | B | 52 | −80.176 | −48.539 | −15.351 | 1.00 | 37.42 C |
| ATOM | 8876 | CB | LEU | B | 52 | −80.774 | −49.476 | −16.399 | 1.00 | 37.66 C |
| ATOM | 8879 | CG | LEU | B | 52 | −80.502 | −49.168 | −17.876 | 1.00 | 38.39 C |
| ATOM | 8881 | CD1 | LEU | B | 52 | −80.171 | −50.452 | −18.652 | 1.00 | 38.46 C |
| ATOM | 8885 | CD2 | LEU | B | 52 | −81.703 | −48.432 | −18.500 | 1.00 | 39.23 C |
| ATOM | 8889 | C | LEU | B | 52 | −80.824 | −47.143 | −15.431 | 1.00 | 36.69 C |
| ATOM | 8890 | O | LEU | B | 52 | −80.383 | −46.312 | −16.224 | 1.00 | 36.59 O |
| ATOM | 8892 | N | THR | B | 53 | −81.859 | −46.879 | −14.625 | 1.00 | 35.87 N |
| ATOM | 8893 | CA | THR | B | 53 | −82.409 | −45.510 | −14.513 | 1.00 | 34.91 C |
| ATOM | 8895 | CB | THR | B | 53 | −83.784 | −45.421 | −13.805 | 1.00 | 34.72 C |
| ATOM | 8897 | OG1 | THR | B | 53 | −84.724 | −46.269 | −14.455 | 1.00 | 34.04 O |
| ATOM | 8899 | CG2 | THR | B | 53 | −84.316 | −43.981 | −13.855 | 1.00 | 34.81 C |
| ATOM | 8903 | C | THR | B | 53 | −81.454 | −44.642 | −13.722 | 1.00 | 34.05 C |
| ATOM | 8904 | O | THR | B | 53 | −81.170 | −43.513 | −14.121 | 1.00 | 34.16 O |
| ATOM | 8906 | N | LEU | B | 54 | −80.987 | −45.167 | −12.593 | 1.00 | 32.84 N |
| ATOM | 8907 | CA | LEU | B | 54 | −80.027 | −44.461 | −11.772 | 1.00 | 32.16 C |
| ATOM | 8909 | CB | LEU | B | 54 | −79.506 | −45.354 | −10.662 | 1.00 | 32.27 C |
| ATOM | 8912 | CG | LEU | B | 54 | −78.521 | −44.702 | −9.698 | 1.00 | 32.56 C |
| ATOM | 8914 | CD1 | LEU | B | 54 | −79.275 | −43.760 | −8.769 | 1.00 | 32.38 C |
| ATOM | 8918 | CD2 | LEU | B | 54 | −77.755 | −45.789 | −8.917 | 1.00 | 33.29 C |
| ATOM | 8922 | C | LEU | B | 54 | −78.870 | −44.006 | −12.634 | 1.00 | 31.50 C |
| ATOM | 8923 | O | LEU | B | 54 | −78.509 | −42.840 | −12.607 | 1.00 | 31.98 O |
| ATOM | 8925 | N | LEU | B | 55 | −78.297 | −44.914 | −13.418 | 1.00 | 30.43 N |
| ATOM | 8926 | CA | LEU | B | 55 | −77.220 | −44.540 | −14.333 | 1.00 | 29.36 C |
| ATOM | 8928 | CB | LEU | B | 55 | −76.765 | −45.733 | −15.173 | 1.00 | 29.23 C |
| ATOM | 8931 | CG | LEU | B | 55 | −76.157 | −46.902 | −14.391 | 1.00 | 28.60 C |
| ATOM | 8933 | CD1 | LEU | B | 55 | −75.697 | −48.004 | −15.348 | 1.00 | 27.60 C |
| ATOM | 8937 | CD2 | LEU | B | 55 | −75.020 | −46.440 | −13.469 | 1.00 | 27.20 C |
| ATOM | 8941 | C | LEU | B | 55 | −77.678 | −43.406 | −15.230 | 1.00 | 28.60 C |
| ATOM | 8942 | O | LEU | B | 55 | −77.063 | −42.365 | −15.267 | 1.00 | 28.17 O |
| ATOM | 8944 | N | GLU | B | 56 | −78.786 | −43.594 | −15.919 | 1.00 | 28.23 N |
| ATOM | 8945 | CA | GLU | B | 56 | −79.326 | −42.530 | −16.759 | 1.00 | 28.64 C |
| ATOM | 8947 | CB | GLU | B | 56 | −80.567 | −43.031 | −17.524 | 1.00 | 29.27 C |
| ATOM | 8950 | CG | GLU | B | 56 | −80.229 | −43.783 | −18.829 | 1.00 | 31.73 C |
| ATOM | 8953 | CD | GLU | B | 56 | −81.265 | −44.860 | −19.206 | 1.00 | 35.52 C |
| ATOM | 8954 | OE1 | GLU | B | 56 | −82.474 | −44.693 | −18.889 | 1.00 | 36.97 O |

TABLE 3-7-continued

| | | | | | | | | | | | |
|---|---|---|---|---|---|---|---|---|---|---|---|
| ATOM | 8955 | OE2 | GLU | B | 56 | −80.856 | −45.877 | −19.825 | 1.00 | 37.55 | O |
| ATOM | 8956 | C | GLU | B | 56 | −79.632 | −41.203 | −15.995 | 1.00 | 27.77 | C |
| ATOM | 8957 | O | GLU | B | 56 | −79.561 | −40.103 | −16.582 | 1.00 | 27.84 | O |
| ATOM | 8959 | N | LEU | B | 57 | −79.976 | −41.303 | −14.710 | 1.00 | 26.29 | N |
| ATOM | 8960 | CA | LEU | B | 57 | −80.158 | −40.120 | −13.895 | 1.00 | 25.06 | C |
| ATOM | 8962 | CB | LEU | B | 57 | −80.724 | −40.462 | −12.514 | 1.00 | 24.83 | C |
| ATOM | 8965 | CG | LEU | B | 57 | −80.952 | −39.298 | −11.544 | 1.00 | 23.72 | C |
| ATOM | 8967 | CD1 | LEU | B | 57 | −81.909 | −38.278 | −12.117 | 1.00 | 21.43 | C |
| ATOM | 8971 | CD2 | LEU | B | 57 | −81.477 | −39.830 | −10.227 | 1.00 | 22.41 | C |
| ATOM | 8975 | C | LEU | B | 57 | −78.801 | −39.459 | −13.780 | 1.00 | 24.40 | C |
| ATOM | 8976 | O | LEU | B | 57 | −78.591 | −38.373 | −14.306 | 1.00 | 24.70 | O |
| ATOM | 8978 | N | ILE | B | 58 | −77.855 | −40.133 | −13.144 | 1.00 | 23.56 | N |
| ATOM | 8979 | CA | ILE | B | 58 | −76.509 | −39.574 | −12.991 | 1.00 | 22.91 | C |
| ATOM | 8981 | CB | ILE | B | 58 | −75.454 | −40.635 | −12.599 | 1.00 | 22.49 | C |
| ATOM | 8983 | CG1 | ILE | B | 58 | −75.753 | −41.251 | −11.235 | 1.00 | 22.09 | C |
| ATOM | 8986 | CD1 | ILE | B | 58 | −74.936 | −42.464 | −10.926 | 1.00 | 20.88 | C |
| ATOM | 8990 | CG2 | ILE | B | 58 | −74.103 | −39.992 | −12.534 | 1.00 | 22.63 | C |
| ATOM | 8994 | C | ILE | B | 58 | −76.062 | −38.927 | −14.302 | 1.00 | 22.64 | C |
| ATOM | 8995 | O | ILE | B | 58 | −75.603 | −37.796 | −14.315 | 1.00 | 22.38 | O |
| ATOM | 8997 | N | ASP | B | 59 | −76.228 | −39.646 | −15.404 | 1.00 | 22.56 | N |
| ATOM | 8998 | CA | ASP | B | 59 | −75.715 | −39.196 | −16.684 | 1.00 | 22.76 | C |
| ATOM | 9000 | CB | ASP | B | 59 | −75.926 | −40.269 | −17.757 | 1.00 | 22.93 | C |
| ATOM | 9003 | CG | ASP | B | 59 | −75.274 | −39.904 | −19.088 | 1.00 | 24.58 | C |
| ATOM | 9004 | OD1 | ASP | B | 59 | −74.157 | −39.322 | −19.081 | 1.00 | 25.70 | O |
| ATOM | 9005 | OD2 | ASP | B | 59 | −75.897 | −40.186 | −20.142 | 1.00 | 27.51 | O |
| ATOM | 9006 | C | ASP | B | 59 | −76.343 | −37.863 | −17.104 | 1.00 | 22.40 | C |
| ATOM | 9007 | O | ASP | B | 59 | −75.634 | −36.939 | −17.520 | 1.00 | 22.40 | O |
| ATOM | 9009 | N | ASN | B | 60 | −77.662 | −37.767 | −16.991 | 1.00 | 21.91 | N |
| ATOM | 9010 | CA | ASN | B | 60 | −78.349 | −36.500 | −17.217 | 1.00 | 21.70 | C |
| ATOM | 9012 | CB | ASN | B | 60 | −79.867 | −36.674 | −17.088 | 1.00 | 22.12 | C |
| ATOM | 9015 | CG | ASN | B | 60 | −80.477 | −37.390 | −18.268 | 1.00 | 22.76 | C |
| ATOM | 9016 | OD1 | ASN | B | 60 | −80.027 | −37.233 | −19.393 | 1.00 | 24.28 | O |
| ATOM | 9017 | ND2 | ASN | B | 60 | −81.515 | −38.172 | −18.017 | 1.00 | 24.36 | N |
| ATOM | 9020 | C | ASN | B | 60 | −77.898 | −35.427 | −16.234 | 1.00 | 21.17 | C |
| ATOM | 9021 | O | ASN | B | 60 | −77.700 | −34.273 | −16.614 | 1.00 | 20.85 | O |
| ATOM | 9023 | N | VAL | B | 61 | −77.745 | −35.805 | −14.968 | 1.00 | 20.60 | N |
| ATOM | 9024 | CA | VAL | B | 61 | −77.382 | −34.841 | −13.942 | 1.00 | 20.48 | C |
| ATOM | 9026 | CB | VAL | B | 61 | −77.277 | −35.490 | −12.551 | 1.00 | 20.26 | C |
| ATOM | 9028 | CG1 | VAL | B | 61 | −76.585 | −34.562 | −11.565 | 1.00 | 19.92 | C |
| ATOM | 9032 | CG2 | VAL | B | 61 | −78.668 | −35.857 | −12.049 | 1.00 | 20.66 | C |
| ATOM | 9036 | C | VAL | B | 61 | −76.068 | −34.208 | −14.335 | 1.00 | 20.66 | C |
| ATOM | 9037 | O | VAL | B | 61 | −75.871 | −32.998 | −14.182 | 1.00 | 20.74 | O |
| ATOM | 9039 | N | GLN | B | 62 | −75.187 | −35.048 | −14.875 | 1.00 | 20.92 | N |
| ATOM | 9040 | CA | GLN | B | 62 | −73.854 | −34.636 | −15.285 | 1.00 | 20.69 | C |
| ATOM | 9042 | CB | GLN | B | 62 | −72.917 | −35.847 | −15.404 | 1.00 | 20.77 | C |
| ATOM | 9045 | CG | GLN | B | 62 | −72.456 | −36.369 | −14.035 | 1.00 | 20.91 | C |
| ATOM | 9048 | CD | GLN | B | 62 | −71.328 | −37.383 | −14.112 | 1.00 | 20.75 | C |
| ATOM | 9049 | OE1 | GLN | B | 62 | −70.512 | −37.498 | −13.192 | 1.00 | 20.93 | O |
| ATOM | 9050 | NE2 | GLN | B | 62 | −71.291 | −38.135 | −15.195 | 1.00 | 20.39 | N |
| ATOM | 9053 | C | GLN | B | 62 | −73.900 | −33.834 | −16.567 | 1.00 | 20.32 | C |
| ATOM | 9054 | O | GLN | B | 62 | −73.410 | −32.712 | −16.569 | 1.00 | 20.79 | O |
| ATOM | 9056 | N | ARG | B | 63 | −74.512 | −34.373 | −17.625 | 1.00 | 19.87 | N |
| ATOM | 9057 | CA | ARG | B | 63 | −74.520 | −33.696 | −18.940 | 1.00 | 19.81 | C |
| ATOM | 9059 | CB | ARG | B | 63 | −75.240 | −34.536 | −20.013 | 1.00 | 19.75 | C |
| ATOM | 9062 | CG | ARG | B | 63 | −74.492 | −35.846 | −20.345 | 1.00 | 21.69 | C |
| ATOM | 9065 | CD | ARG | B | 63 | −75.158 | −36.786 | −21.368 | 1.00 | 24.89 | C |
| ATOM | 9068 | NE | ARG | B | 63 | −74.674 | −36.558 | −22.741 | 1.00 | 29.32 | N |
| ATOM | 9070 | CZ | ARG | B | 63 | −75.323 | −35.878 | −23.702 | 1.00 | 33.71 | C |
| ATOM | 9071 | NH1 | ARG | B | 63 | −76.537 | −35.345 | −23.510 | 1.00 | 36.67 | N |
| ATOM | 9074 | NH2 | ARG | B | 63 | −74.761 | −35.736 | −24.894 | 1.00 | 34.58 | N |
| ATOM | 9077 | C | ARG | B | 63 | −75.099 | −32.276 | −18.822 | 1.00 | 19.39 | C |
| ATOM | 9078 | O | ARG | B | 63 | −74.553 | −31.310 | −19.395 | 1.00 | 19.63 | O |
| ATOM | 9080 | N | LEU | B | 64 | −76.155 | −32.148 | −18.017 | 1.00 | 18.62 | N |
| ATOM | 9081 | CA | LEU | B | 64 | −76.811 | −30.856 | −17.753 | 1.00 | 17.96 | C |
| ATOM | 9083 | CB | LEU | B | 64 | −78.136 | −31.077 | −17.008 | 1.00 | 17.97 | C |
| ATOM | 9086 | CG | LEU | B | 64 | −79.264 | −31.737 | −17.809 | 1.00 | 17.08 | C |
| ATOM | 9088 | CD1 | LEU | B | 64 | −80.276 | −32.354 | −16.879 | 1.00 | 15.15 | C |
| ATOM | 9092 | CD2 | LEU | B | 64 | −79.904 | −30.734 | −18.737 | 1.00 | 15.30 | C |
| ATOM | 9096 | C | LEU | B | 64 | −75.975 | −29.847 | −16.966 | 1.00 | 17.39 | C |
| ATOM | 9097 | O | LEU | B | 64 | −76.370 | −28.685 | −16.825 | 1.00 | 17.38 | O |
| ATOM | 9099 | N | GLY | B | 65 | −74.848 | −30.286 | −16.432 | 1.00 | 16.73 | N |
| ATOM | 9100 | CA | GLY | B | 65 | −73.917 | −29.374 | −15.818 | 1.00 | 16.65 | C |
| ATOM | 9103 | C | GLY | B | 65 | −74.077 | −29.249 | −14.319 | 1.00 | 16.68 | C |
| ATOM | 9104 | O | GLY | B | 65 | −73.565 | −28.302 | −13.718 | 1.00 | 16.79 | O |
| ATOM | 9106 | N | LEU | B | 66 | −74.758 | −30.209 | −13.702 | 1.00 | 16.60 | N |
| ATOM | 9107 | CA | LEU | B | 66 | −74.978 | −30.177 | −12.264 | 1.00 | 16.58 | C |
| ATOM | 9109 | CB | LEU | B | 66 | −76.465 | −30.389 | −11.957 | 1.00 | 16.35 | C |
| ATOM | 9112 | CG | LEU | B | 66 | −77.363 | −29.187 | −12.234 | 1.00 | 15.57 | C |

TABLE 3-7-continued

| | | | | | | | | | | |
|---|---|---|---|---|---|---|---|---|---|---|
| ATOM | 9114 | CD1 | LEU | B | 66 | −78.828 | −29.602 | −12.163 | 1.00 | 15.26 C |
| ATOM | 9118 | CD2 | LEU | B | 66 | −77.063 | −28.051 | −11.270 | 1.00 | 13.66 C |
| ATOM | 9122 | C | LEU | B | 66 | −74.129 | −31.203 | −11.513 | 1.00 | 16.94 C |
| ATOM | 9123 | O | LEU | B | 66 | −74.152 | −31.251 | −10.279 | 1.00 | 17.50 O |
| ATOM | 9125 | N | GLY | B | 67 | −73.373 | −32.017 | −12.236 | 1.00 | 17.03 N |
| ATOM | 9126 | CA | GLY | B | 67 | −72.541 | −33.036 | −11.602 | 1.00 | 17.13 C |
| ATOM | 9129 | C | GLY | B | 67 | −71.642 | −32.557 | −10.461 | 1.00 | 17.08 C |
| ATOM | 9130 | O | GLY | B | 67 | −71.378 | −33.317 | −9.522 | 1.00 | 17.33 O |
| ATOM | 9132 | N | TYR | B | 68 | −71.159 | −31.316 | −10.541 | 1.00 | 16.83 N |
| ATOM | 9133 | CA | TYR | B | 68 | −70.217 | −30.804 | −9.552 | 1.00 | 16.64 C |
| ATOM | 9135 | CB | TYR | B | 68 | −69.654 | −29.437 | −9.951 | 1.00 | 16.25 C |
| ATOM | 9138 | CG | TYR | B | 68 | −70.609 | −28.273 | −9.802 | 1.00 | 13.51 C |
| ATOM | 9139 | CD1 | TYR | B | 68 | −70.521 | −27.411 | −8.738 | 1.00 | 10.49 C |
| ATOM | 9141 | CE1 | TYR | B | 68 | −71.407 | −26.342 | −8.608 | 1.00 | 10.25 C |
| ATOM | 9143 | CZ | TYR | B | 68 | −72.382 | −26.135 | −9.555 | 1.00 | 9.74 C |
| ATOM | 9144 | OH | TYR | B | 68 | −73.253 | −25.086 | −9.450 | 1.00 | 7.62 O |
| ATOM | 9146 | CE2 | TYR | B | 68 | −72.484 | −26.978 | −10.625 | 1.00 | 11.14 C |
| ATOM | 9148 | CD2 | TYR | B | 68 | −71.603 | −28.037 | −10.748 | 1.00 | 12.56 C |
| ATOM | 9150 | C | TYR | B | 68 | −70.828 | −30.700 | −8.172 | 1.00 | 17.79 C |
| ATOM | 9151 | O | TYR | B | 68 | −70.107 | −30.811 | −7.182 | 1.00 | 18.00 O |
| ATOM | 9153 | N | ARG | B | 69 | −72.146 | −30.485 | −8.090 | 1.00 | 18.85 N |
| ATOM | 9154 | CA | ARG | B | 69 | −72.784 | −30.269 | −6.789 | 1.00 | 19.46 C |
| ATOM | 9156 | CB | ARG | B | 69 | −73.708 | −29.047 | −6.819 | 1.00 | 19.23 C |
| ATOM | 9159 | CG | ARG | B | 69 | −75.030 | −29.219 | −7.509 | 1.00 | 18.83 C |
| ATOM | 9162 | CD | ARG | B | 69 | −76.053 | −28.192 | −6.985 | 1.00 | 17.73 C |
| ATOM | 9165 | NE | ARG | B | 69 | −75.642 | −26.830 | −7.297 | 1.00 | 16.01 N |
| ATOM | 9167 | CZ | ARG | B | 69 | −75.330 | −25.889 | −6.417 | 1.00 | 14.68 C |
| ATOM | 9168 | NH1 | ARG | B | 69 | −75.400 | −26.093 | −5.112 | 1.00 | 14.99 N |
| ATOM | 9171 | NH2 | ARG | B | 69 | −74.959 | −24.707 | −6.861 | 1.00 | 15.04 N |
| ATOM | 9174 | C | ARG | B | 69 | −73.490 | −31.489 | −6.234 | 1.00 | 20.50 C |
| ATOM | 9175 | O | ARG | B | 69 | −74.084 | −31.418 | −5.163 | 1.00 | 20.67 O |
| ATOM | 9177 | N | PHE | B | 70 | −73.416 | −32.607 | −6.959 | 1.00 | 22.04 N |
| ATOM | 9178 | CA | PHE | B | 70 | −73.853 | −33.917 | −6.450 | 1.00 | 23.03 C |
| ATOM | 9180 | CB | PHE | B | 70 | −75.081 | −34.428 | −7.211 | 1.00 | 22.94 C |
| ATOM | 9183 | CG | PHE | B | 70 | −76.236 | −33.503 | −7.157 | 1.00 | 21.78 C |
| ATOM | 9184 | CD1 | PHE | B | 70 | −77.024 | −33.441 | −6.028 | 1.00 | 20.54 C |
| ATOM | 9186 | CE1 | PHE | B | 70 | −78.076 | −32.571 | −5.959 | 1.00 | 20.32 C |
| ATOM | 9188 | CZ | PHE | B | 70 | −78.353 | −31.752 | −7.025 | 1.00 | 20.73 C |
| ATOM | 9190 | CE2 | PHE | B | 70 | −77.564 | −31.796 | −8.160 | 1.00 | 21.24 C |
| ATOM | 9192 | CD2 | PHE | B | 70 | −76.511 | −32.665 | −8.220 | 1.00 | 21.22 C |
| ATOM | 9194 | C | PHE | B | 70 | −72.765 | −34.962 | −6.570 | 1.00 | 24.33 C |
| ATOM | 9195 | O | PHE | B | 70 | −73.069 | −36.142 | −6.614 | 1.00 | 24.56 O |
| ATOM | 9197 | N | GLU | B | 71 | −71.500 | −34.547 | −6.624 | 1.00 | 26.01 N |
| ATOM | 9198 | CA | GLU | B | 71 | −70.413 | −35.506 | −6.804 | 1.00 | 27.04 C |
| ATOM | 9200 | CB | GLU | B | 71 | −69.042 | −34.824 | −6.885 | 1.00 | 27.48 C |
| ATOM | 9203 | CG | GLU | B | 71 | −67.851 | −35.816 | −6.794 | 1.00 | 28.94 C |
| ATOM | 9206 | CD | GLU | B | 71 | −66.491 | −35.192 | −7.081 | 1.00 | 30.38 C |
| ATOM | 9207 | OE1 | GLU | B | 71 | −66.398 | −34.192 | −7.835 | 1.00 | 30.52 O |
| ATOM | 9208 | OE2 | GLU | B | 71 | −65.501 | −35.730 | −6.544 | 1.00 | 32.16 O |
| ATOM | 9209 | C | GLU | B | 71 | −70.436 | −36.531 | −5.680 | 1.00 | 27.46 C |
| ATOM | 9210 | O | GLU | B | 71 | −70.449 | −37.723 | −5.937 | 1.00 | 27.67 O |
| ATOM | 9212 | N | SER | B | 72 | −70.464 | −36.087 | −4.435 | 1.00 | 28.04 N |
| ATOM | 9213 | CA | SER | B | 72 | −70.381 | −37.044 | −3.348 | 1.00 | 28.86 C |
| ATOM | 9215 | CB | SER | B | 72 | −70.388 | −36.340 | −1.983 | 1.00 | 29.09 C |
| ATOM | 9218 | OG | SER | B | 72 | −71.649 | −35.751 | −1.687 | 1.00 | 30.21 O |
| ATOM | 9220 | C | SER | B | 72 | −71.519 | −38.058 | −3.481 | 1.00 | 29.30 C |
| ATOM | 9221 | O | SER | B | 72 | −71.304 | −39.265 | −3.384 | 1.00 | 29.24 O |
| ATOM | 9223 | N | ASP | B | 73 | −72.719 | −37.560 | −3.756 | 1.00 | 30.03 N |
| ATOM | 9224 | CA | ASP | B | 73 | −73.897 | −38.417 | −3.874 | 1.00 | 30.63 C |
| ATOM | 9226 | CB | ASP | B | 73 | −75.184 | −37.598 | −4.116 | 1.00 | 30.74 C |
| ATOM | 9229 | CG | ASP | B | 73 | −75.419 | −36.509 | −3.052 | 1.00 | 31.84 C |
| ATOM | 9230 | OD1 | ASP | B | 73 | −75.562 | −36.830 | −1.841 | 1.00 | 31.70 O |
| ATOM | 9231 | OD2 | ASP | B | 73 | −75.473 | −35.317 | −3.443 | 1.00 | 33.81 O |
| ATOM | 9232 | C | ASP | B | 73 | −73.722 | −39.443 | −4.994 | 1.00 | 30.81 C |
| ATOM | 9233 | O | ASP | B | 73 | −74.130 | −40.590 | −4.835 | 1.00 | 31.39 O |
| ATOM | 9235 | N | ILE | B | 74 | −73.122 | −39.031 | −6.112 | 1.00 | 30.96 N |
| ATOM | 9236 | CA | ILE | B | 74 | −72.917 | −39.912 | −7.282 | 1.00 | 31.04 C |
| ATOM | 9238 | CB | ILE | B | 74 | −72.461 | −39.114 | −8.524 | 1.00 | 30.88 C |
| ATOM | 9240 | CG1 | ILE | B | 74 | −73.585 | −38.213 | −9.018 | 1.00 | 30.99 C |
| ATOM | 9243 | CD1 | ILE | B | 74 | −73.105 | −37.120 | −9.923 | 1.00 | 31.54 C |
| ATOM | 9247 | CG2 | ILE | B | 74 | −72.052 | −40.035 | −9.642 | 1.00 | 29.85 C |
| ATOM | 9251 | C | ILE | B | 74 | −71.885 | −41.005 | −6.999 | 1.00 | 31.45 C |
| ATOM | 9252 | O | ILE | B | 74 | −72.098 | −42.165 | −7.347 | 1.00 | 31.31 O |
| ATOM | 9254 | N | ARG | B | 75 | −70.768 | −40.628 | −6.380 | 1.00 | 31.93 N |
| ATOM | 9255 | CA | ARG | B | 75 | −69.778 | −41.601 | −5.947 | 1.00 | 32.38 C |
| ATOM | 9257 | CB | ARG | B | 75 | −68.629 | −40.959 | −5.137 | 1.00 | 32.87 C |
| ATOM | 9260 | CG | ARG | B | 75 | −67.310 | −40.751 | −5.915 | 1.00 | 35.01 C |
| ATOM | 9263 | CD | ARG | B | 75 | −66.089 | −40.489 | −5.003 | 1.00 | 37.62 C |

TABLE 3-7-continued

| | | | | | | | | | | | |
|---|---|---|---|---|---|---|---|---|---|---|---|
| ATOM | 9266 | NE | ARG | B | 75 | −65.260 | −41.687 | −4.783 | 1.00 | 41.03 | N |
| ATOM | 9268 | CZ | ARG | B | 75 | −64.461 | −42.253 | −5.700 | 1.00 | 44.29 | C |
| ATOM | 9269 | NH1 | ARG | B | 75 | −64.385 | −41.751 | −6.931 | 1.00 | 46.22 | N |
| ATOM | 9272 | NH2 | ARG | B | 75 | −63.741 | −43.341 | −5.404 | 1.00 | 44.30 | N |
| ATOM | 9275 | C | ARG | B | 75 | −70.478 | −42.673 | −5.126 | 1.00 | 32.18 | C |
| ATOM | 9276 | O | ARG | B | 75 | −70.307 | −43.849 | −5.398 | 1.00 | 32.19 | O |
| ATOM | 9278 | N | ARG | B | 76 | −71.280 | −42.275 | −4.143 | 1.00 | 32.21 | N |
| ATOM | 9279 | CA | ARG | B | 76 | −71.975 | −43.256 | −3.307 | 1.00 | 32.61 | C |
| ATOM | 9281 | CB | ARG | B | 76 | −72.737 | −42.582 | −2.162 | 1.00 | 32.75 | C |
| ATOM | 9284 | CG | ARG | B | 76 | −71.880 | −42.320 | −.929 | 1.00 | 33.44 | C |
| ATOM | 9287 | CD | ARG | B | 76 | −72.720 | −42.046 | .334 | 1.00 | 34.16 | C |
| ATOM | 9290 | NE | ARG | B | 76 | −73.797 | −41.074 | .124 | 1.00 | 34.53 | N |
| ATOM | 9292 | CZ | ARG | B | 76 | −73.627 | −39.765 | −.063 | 1.00 | 34.38 | C |
| ATOM | 9293 | NH1 | ARG | B | 76 | −72.414 | −39.219 | −.092 | 1.00 | 34.34 | N |
| ATOM | 9296 | NH2 | ARG | B | 76 | −74.689 | −38.993 | −.241 | 1.00 | 34.71 | N |
| ATOM | 9299 | C | ARG | B | 76 | −72.918 | −44.159 | −4.112 | 1.00 | 32.81 | C |
| ATOM | 9300 | O | ARG | B | 76 | −72.863 | −45.379 | −3.995 | 1.00 | 32.86 | O |
| ATOM | 9302 | N | ALA | B | 77 | −73.780 | −43.559 | −4.923 | 1.00 | 33.10 | N |
| ATOM | 9303 | CA | ALA | B | 77 | −74.655 | −44.307 | −5.813 | 1.00 | 33.27 | C |
| ATOM | 9305 | CB | ALA | B | 77 | −75.321 | −43.366 | −6.770 | 1.00 | 33.26 | C |
| ATOM | 9309 | C | ALA | B | 77 | −73.884 | −45.370 | −6.578 | 1.00 | 33.80 | C |
| ATOM | 9310 | O | ALA | B | 77 | −74.235 | −46.542 | −6.559 | 1.00 | 33.75 | O |
| ATOM | 9312 | N | LEU | B | 78 | −72.816 | −44.952 | −7.242 | 1.00 | 34.77 | N |
| ATOM | 9313 | CA | LEU | B | 78 | −71.987 | −45.868 | −8.019 | 1.00 | 35.41 | C |
| ATOM | 9315 | CB | LEU | B | 78 | −70.845 | −45.109 | −8.702 | 1.00 | 35.01 | C |
| ATOM | 9318 | CG | LEU | B | 78 | −71.220 | −44.092 | −9.782 | 1.00 | 34.37 | C |
| ATOM | 9320 | CD1 | LEU | B | 78 | −69.945 | −43.502 | −10.381 | 1.00 | 33.93 | C |
| ATOM | 9324 | CD2 | LEU | B | 78 | −72.109 | −44.692 | −10.873 | 1.00 | 32.94 | C |
| ATOM | 9328 | C | LEU | B | 78 | −71.409 | −46.974 | −7.142 | 1.00 | 36.50 | C |
| ATOM | 9329 | O | LEU | B | 78 | −71.336 | −48.124 | −7.552 | 1.00 | 36.87 | O |
| ATOM | 9331 | N | ASP | B | 79 | −71.005 | −46.619 | −5.931 | 1.00 | 37.74 | N |
| ATOM | 9332 | CA | ASP | B | 79 | −70.308 | −47.545 | −5.056 | 1.00 | 38.74 | C |
| ATOM | 9334 | CB | ASP | B | 79 | −69.787 | −46.810 | −3.819 | 1.00 | 38.99 | C |
| ATOM | 9337 | CG | ASP | B | 79 | −68.499 | −47.386 | −3.313 | 1.00 | 40.08 | C |
| ATOM | 9338 | OD1 | ASP | B | 79 | −68.494 | −48.591 | −2.976 | 1.00 | 42.32 | O |
| ATOM | 9339 | OD2 | ASP | B | 79 | −67.494 | −46.638 | −3.261 | 1.00 | 41.24 | O |
| ATOM | 9340 | C | ASP | B | 79 | −71.207 | −48.705 | −4.645 | 1.00 | 39.42 | C |
| ATOM | 9341 | O | ASP | B | 79 | −70.736 | −49.835 | −4.505 | 1.00 | 39.58 | O |
| ATOM | 9343 | N | ARG | B | 80 | −72.495 | −48.424 | −4.450 | 1.00 | 40.26 | N |
| ATOM | 9344 | CA | ARG | B | 80 | −73.471 | −49.470 | −4.143 | 1.00 | 40.92 | C |
| ATOM | 9346 | CB | ARG | B | 80 | −74.823 | −48.881 | −3.716 | 1.00 | 41.46 | C |
| ATOM | 9349 | CG | ARG | B | 80 | −74.871 | −48.247 | −2.308 | 1.00 | 42.87 | C |
| ATOM | 9352 | CD | ARG | B | 80 | −76.316 | −47.826 | −1.936 | 1.00 | 44.62 | C |
| ATOM | 9355 | NE | ARG | B | 80 | −76.946 | −46.968 | −2.949 | 1.00 | 45.87 | N |
| ATOM | 9357 | CZ | ARG | B | 80 | −76.741 | −45.651 | −3.089 | 1.00 | 46.82 | C |
| ATOM | 9358 | NH1 | ARG | B | 80 | −75.905 | −44.989 | −2.282 | 1.00 | 46.27 | N |
| ATOM | 9361 | NH2 | ARG | B | 80 | −77.378 | −44.988 | −4.059 | 1.00 | 47.22 | N |
| ATOM | 9364 | C | ARG | B | 80 | −73.667 | −50.341 | −5.371 | 1.00 | 40.77 | C |
| ATOM | 9365 | O | ARG | B | 80 | −73.642 | −51.563 | −5.275 | 1.00 | 41.06 | O |
| ATOM | 9367 | N | PHE | B | 81 | −73.863 | −49.705 | −6.520 | 1.00 | 40.56 | N |
| ATOM | 9368 | CA | PHE | B | 81 | −73.986 | −50.418 | −7.787 | 1.00 | 40.59 | C |
| ATOM | 9370 | CB | PHE | B | 81 | −73.984 | −49.426 | −8.956 | 1.00 | 40.73 | C |
| ATOM | 9373 | CG | PHE | B | 81 | −73.898 | −50.063 | −10.323 | 1.00 | 40.84 | C |
| ATOM | 9374 | CD1 | PHE | B | 81 | −75.000 | −50.668 | −10.893 | 1.00 | 41.39 | C |
| ATOM | 9376 | CE1 | PHE | B | 81 | −74.925 | −51.236 | −12.167 | 1.00 | 41.67 | C |
| ATOM | 9378 | CZ | PHE | B | 81 | −73.741 | −51.191 | −12.877 | 1.00 | 41.33 | C |
| ATOM | 9380 | CE2 | PHE | B | 81 | −72.638 | −50.580 | −12.326 | 1.00 | 41.19 | C |
| ATOM | 9382 | CD2 | PHE | B | 81 | −72.720 | −50.012 | −11.057 | 1.00 | 41.39 | C |
| ATOM | 9384 | C | PHE | B | 81 | −72.871 | −51.441 | −7.953 | 1.00 | 40.47 | C |
| ATOM | 9385 | O | PHE | B | 81 | −73.134 | −52.583 | −8.311 | 1.00 | 40.85 | O |
| ATOM | 9387 | N | VAL | B | 82 | −71.633 | −51.051 | −7.683 | 1.00 | 40.26 | N |
| ATOM | 9388 | CA | VAL | B | 82 | −70.522 | −51.986 | −7.821 | 1.00 | 40.24 | C |
| ATOM | 9390 | CB | VAL | B | 82 | −69.173 | −51.386 | −7.379 | 1.00 | 40.28 | C |
| ATOM | 9392 | CG1 | VAL | B | 82 | −68.164 | −52.493 | −7.063 | 1.00 | 39.98 | C |
| ATOM | 9396 | CG2 | VAL | B | 82 | −68.644 | −50.462 | −8.451 | 1.00 | 40.09 | C |
| ATOM | 9400 | C | VAL | B | 82 | −70.788 | −53.230 | −7.005 | 1.00 | 40.16 | C |
| ATOM | 9401 | O | VAL | B | 82 | −70.880 | −54.313 | −7.559 | 1.00 | 40.13 | O |
| ATOM | 9403 | N | SER | B | 83 | −70.953 | −53.056 | −5.698 | 1.00 | 40.26 | N |
| ATOM | 9404 | CA | SER | B | 83 | −71.070 | −54.174 | −4.749 | 1.00 | 40.43 | C |
| ATOM | 9406 | CB | SER | B | 83 | −70.797 | −53.666 | −3.331 | 1.00 | 40.54 | C |
| ATOM | 9409 | OG | SER | B | 83 | −71.256 | −52.330 | −3.191 | 1.00 | 40.89 | O |
| ATOM | 9411 | C | SER | B | 83 | −72.415 | −54.912 | −4.831 | 1.00 | 40.34 | C |
| ATOM | 9412 | O | SER | B | 83 | −73.137 | −55.046 | −3.845 | 1.00 | 39.99 | O |
| ATOM | 9414 | N | SER | B | 84 | −72.698 | −55.400 | −6.038 | 1.00 | 40.57 | N |
| ATOM | 9415 | CA | SER | B | 84 | −73.902 | −56.154 | −6.411 | 1.00 | 40.63 | C |
| ATOM | 9417 | CB | SER | B | 84 | −75.154 | −55.679 | −5.651 | 1.00 | 40.56 | C |
| ATOM | 9420 | OG | SER | B | 84 | −75.292 | −54.268 | −5.663 | 1.00 | 39.82 | O |
| ATOM | 9422 | C | SER | B | 84 | −74.104 | −56.026 | −7.940 | 1.00 | 40.85 | C |

TABLE 3-7-continued

Coordinates of *P. tremuloides* IspS

| ATOM | 9423 | O | SER | B | 84 | −75.104 | −55.462 | −8.395 | 1.00 | 41.24 | O |
|---|---|---|---|---|---|---|---|---|---|---|---|
| ATOM | 9425 | N | GLY | B | 85 | −73.136 | −56.524 | −8.720 | 1.00 | 40.75 | N |
| ATOM | 9426 | CA | GLY | B | 85 | −73.201 | −56.506 | −10.191 | 1.00 | 40.64 | C |
| ATOM | 9429 | C | GLY | B | 85 | −73.225 | −55.120 | −10.815 | 1.00 | 40.64 | C |
| ATOM | 9430 | O | GLY | B | 85 | −74.133 | −54.794 | −11.590 | 1.00 | 40.32 | O |
| ATOM | 9432 | N | THR | B | 93 | −74.847 | −57.360 | −18.759 | 1.00 | 36.30 | N |
| ATOM | 9433 | CA | THR | B | 93 | −75.593 | −58.129 | −19.774 | 1.00 | 35.99 | C |
| ATOM | 9435 | CB | THR | B | 93 | −76.251 | −59.379 | −19.152 | 1.00 | 35.87 | C |
| ATOM | 9437 | OG1 | THR | B | 93 | −76.347 | −60.389 | −20.158 | 1.00 | 35.64 | O |
| ATOM | 9439 | CG2 | THR | B | 93 | −77.646 | −59.062 | −18.548 | 1.00 | 34.95 | C |
| ATOM | 9443 | C | THR | B | 93 | −76.625 | −57.274 | −20.583 | 1.00 | 35.90 | C |
| ATOM | 9444 | O | THR | B | 93 | −77.764 | −57.688 | −20.843 | 1.00 | 35.74 | O |
| ATOM | 9446 | N | SER | B | 94 | −76.175 | −56.076 | −20.963 | 1.00 | 35.58 | N |
| ATOM | 9447 | CA | SER | B | 94 | −76.874 | −55.150 | −21.866 | 1.00 | 34.97 | C |
| ATOM | 9449 | CB | SER | B | 94 | −78.074 | −54.472 | −21.190 | 1.00 | 35.06 | C |
| ATOM | 9452 | OG | SER | B | 94 | −77.702 | −53.260 | −20.541 | 1.00 | 34.37 | O |
| ATOM | 9454 | C | SER | B | 94 | −75.831 | −54.097 | −22.232 | 1.00 | 34.39 | C |
| ATOM | 9455 | O | SER | B | 94 | −75.212 | −53.518 | −21.341 | 1.00 | 34.11 | O |
| ATOM | 9457 | N | LEU | B | 95 | −75.619 | −53.864 | −23.522 | 1.00 | 33.77 | N |
| ATOM | 9458 | CA | LEU | B | 95 | −74.490 | −53.045 | −23.952 | 1.00 | 33.33 | C |
| ATOM | 9460 | CB | LEU | B | 95 | −74.373 | −53.010 | −25.475 | 1.00 | 33.30 | C |
| ATOM | 9463 | CG | LEU | B | 95 | −73.154 | −52.246 | −26.006 | 1.00 | 33.27 | C |
| ATOM | 9465 | CD1 | LEU | B | 95 | −71.909 | −52.455 | −25.137 | 1.00 | 32.89 | C |
| ATOM | 9469 | CD2 | LEU | B | 95 | −72.864 | −52.649 | −27.438 | 1.00 | 33.19 | C |
| ATOM | 9473 | C | LEU | B | 95 | −74.551 | −51.623 | −23.413 | 1.00 | 33.00 | C |
| ATOM | 9474 | O | LEU | B | 95 | −73.588 | −51.151 | −22.809 | 1.00 | 32.83 | O |
| ATOM | 9476 | N | HIS | B | 96 | −75.678 | −50.949 | −23.633 | 1.00 | 32.64 | N |
| ATOM | 9477 | CA | HIS | B | 96 | −75.853 | −49.576 | −23.171 | 1.00 | 32.39 | C |
| ATOM | 9479 | CB | HIS | B | 96 | −77.246 | −49.069 | −23.527 | 1.00 | 32.64 | C |
| ATOM | 9482 | CG | HIS | B | 96 | −77.528 | −47.689 | −23.025 | 1.00 | 34.16 | C |
| ATOM | 9483 | ND1 | HIS | B | 96 | −76.565 | −46.703 | −22.981 | 1.00 | 36.21 | N |
| ATOM | 9485 | CE1 | HIS | B | 96 | −77.096 | −45.594 | −22.496 | 1.00 | 36.92 | C |
| ATOM | 9487 | NE2 | HIS | B | 96 | −78.371 | −45.827 | −22.227 | 1.00 | 37.06 | N |
| ATOM | 9489 | CD2 | HIS | B | 96 | −78.664 | −47.130 | −22.548 | 1.00 | 35.43 | C |
| ATOM | 9491 | C | HIS | B | 96 | −75.612 | −49.445 | −21.665 | 1.00 | 31.78 | C |
| ATOM | 9492 | O | HIS | B | 96 | −74.936 | −48.523 | −21.215 | 1.00 | 31.95 | O |
| ATOM | 9494 | N | GLY | B | 97 | −76.156 | −50.372 | −20.887 | 1.00 | 31.10 | N |
| ATOM | 9495 | CA | GLY | B | 97 | −75.907 | −50.396 | −19.446 | 1.00 | 30.52 | C |
| ATOM | 9498 | C | GLY | B | 97 | −74.434 | −50.532 | −19.085 | 1.00 | 29.95 | C |
| ATOM | 9499 | O | GLY | B | 97 | −73.936 | −49.797 | −18.241 | 1.00 | 30.21 | O |
| ATOM | 9501 | N | THR | B | 98 | −73.740 | −51.470 | −19.726 | 1.00 | 29.15 | N |
| ATOM | 9502 | CA | THR | B | 98 | −72.314 | −51.690 | −19.490 | 1.00 | 28.55 | C |
| ATOM | 9504 | CB | THR | B | 98 | −71.803 | −52.955 | −20.248 | 1.00 | 28.48 | C |
| ATOM | 9506 | OG1 | THR | B | 98 | −72.678 | −54.066 | −19.997 | 1.00 | 28.41 | O |
| ATOM | 9508 | CG2 | THR | B | 98 | −70.405 | −53.331 | −19.816 | 1.00 | 27.74 | C |
| ATOM | 9512 | C | THR | B | 98 | −71.492 | −50.452 | −19.894 | 1.00 | 28.31 | C |
| ATOM | 9513 | O | THR | B | 98 | −70.658 | −49.979 | −19.127 | 1.00 | 28.13 | O |
| ATOM | 9515 | N | ALA | B | 99 | −71.750 | −49.910 | −21.080 | 1.00 | 28.04 | N |
| ATOM | 9516 | CA | ALA | B | 99 | −70.984 | −48.758 | −21.578 | 1.00 | 27.88 | C |
| ATOM | 9518 | CB | ALA | B | 99 | −71.387 | −48.406 | −23.014 | 1.00 | 27.78 | C |
| ATOM | 9522 | C | ALA | B | 99 | −71.127 | −47.538 | −20.684 | 1.00 | 27.62 | C |
| ATOM | 9523 | O | ALA | B | 99 | −70.135 | −46.885 | −20.361 | 1.00 | 27.84 | O |
| ATOM | 9525 | N | LEU | B | 100 | −72.357 | −47.233 | −20.290 | 1.00 | 27.20 | N |
| ATOM | 9526 | CA | LEU | B | 100 | −72.613 | −46.088 | −19.422 | 1.00 | 27.08 | C |
| ATOM | 9528 | CB | LEU | B | 100 | −74.122 | −45.900 | −19.230 | 1.00 | 26.95 | C |
| ATOM | 9531 | CG | LEU | B | 100 | −74.560 | −44.715 | −18.367 | 1.00 | 26.27 | C |
| ATOM | 9533 | CD1 | LEU | B | 100 | −73.753 | −43.478 | −18.734 | 1.00 | 26.19 | C |
| ATOM | 9537 | CD2 | LEU | B | 100 | −76.052 | −44.445 | −18.504 | 1.00 | 25.20 | C |
| ATOM | 9541 | C | LEU | B | 100 | −71.928 | −46.221 | −18.046 | 1.00 | 27.23 | C |
| ATOM | 9542 | O | LEU | B | 100 | −71.368 | −45.243 | −17.523 | 1.00 | 27.16 | O |
| ATOM | 9544 | N | SER | B | 101 | −71.980 | −47.429 | −17.472 | 1.00 | 27.00 | N |
| ATOM | 9545 | CA | SER | B | 101 | −71.475 | −47.682 | −16.117 | 1.00 | 26.63 | C |
| ATOM | 9547 | CB | SER | B | 101 | −72.039 | −48.992 | −15.568 | 1.00 | 26.49 | C |
| ATOM | 9550 | OG | SER | B | 101 | −71.758 | −50.063 | −16.442 | 1.00 | 26.38 | O |
| ATOM | 9552 | C | SER | B | 101 | −69.956 | −47.740 | −16.090 | 1.00 | 26.47 | C |
| ATOM | 9553 | O | SER | B | 101 | −69.326 | −47.324 | −15.121 | 1.00 | 26.35 | O |
| ATOM | 9555 | N | PHE | B | 102 | −69.381 | −48.288 | −17.154 | 1.00 | 26.29 | N |
| ATOM | 9556 | CA | PHE | B | 102 | −67.934 | −48.332 | −17.322 | 1.00 | 25.91 | C |
| ATOM | 9558 | CB | PHE | B | 102 | −67.588 | −49.005 | −18.652 | 1.00 | 25.96 | C |
| ATOM | 9561 | CG | PHE | B | 102 | −66.133 | −49.020 | −18.958 | 1.00 | 25.81 | C |
| ATOM | 9562 | CD1 | PHE | B | 102 | −65.360 | −50.115 | −18.633 | 1.00 | 25.96 | C |
| ATOM | 9564 | CE1 | PHE | B | 102 | −63.999 | −50.122 | −18.909 | 1.00 | 26.94 | C |
| ATOM | 9566 | CZ | PHE | B | 102 | −63.403 | −49.026 | −19.519 | 1.00 | 26.27 | C |
| ATOM | 9568 | CE2 | PHE | B | 102 | −64.174 | −47.930 | −19.848 | 1.00 | 26.19 | C |
| ATOM | 9570 | CD2 | PHE | B | 102 | −65.531 | −47.933 | −19.573 | 1.00 | 26.04 | C |
| ATOM | 9572 | C | PHE | B | 102 | −67.416 | −46.911 | −17.315 | 1.00 | 25.56 | C |
| ATOM | 9573 | O | PHE | B | 102 | −66.486 | −46.564 | −16.568 | 1.00 | 25.37 | O |
| ATOM | 9575 | N | ARG | B | 103 | −68.050 | −46.095 | −18.152 | 1.00 | 25.20 | N |

TABLE 3-7-continued

| | | | | | | | | | | | |
|---|---|---|---|---|---|---|---|---|---|---|---|
| ATOM | 9576 | CA | ARG | B | 103 | −67.663 | −44.696 | −18.322 | 1.00 | 25.09 | C |
| ATOM | 9578 | CB | ARG | B | 103 | −68.510 | −44.026 | −19.400 | 1.00 | 25.12 | C |
| ATOM | 9581 | CG | ARG | B | 103 | −68.194 | −42.561 | −19.572 | 1.00 | 25.41 | C |
| ATOM | 9584 | CD | ARG | B | 103 | −68.744 | −42.035 | −20.889 | 1.00 | 26.68 | C |
| ATOM | 9587 | NE | ARG | B | 103 | −70.197 | −41.843 | −20.877 | 1.00 | 27.49 | N |
| ATOM | 9589 | CZ | ARG | B | 103 | −70.826 | −40.851 | −20.246 | 1.00 | 26.56 | C |
| ATOM | 9590 | NH1 | ARG | B | 103 | −70.139 | −39.963 | −19.531 | 1.00 | 27.11 | N |
| ATOM | 9593 | NH2 | ARG | B | 103 | −72.148 | −40.759 | −20.310 | 1.00 | 25.20 | N |
| ATOM | 9596 | C | ARG | B | 103 | −67.785 | −43.898 | −17.033 | 1.00 | 24.61 | C |
| ATOM | 9597 | O | ARG | B | 103 | −66.865 | −43.168 | −16.659 | 1.00 | 24.67 | O |
| ATOM | 9599 | N | LEU | B | 104 | −68.927 | −44.013 | −16.371 | 1.00 | 23.79 | N |
| ATOM | 9600 | CA | LEU | B | 104 | −69.125 | −43.263 | −15.148 | 1.00 | 23.23 | C |
| ATOM | 9602 | CB | LEU | B | 104 | −70.591 | −43.342 | −14.693 | 1.00 | 23.01 | C |
| ATOM | 9605 | CG | LEU | B | 104 | −71.607 | −42.620 | −15.584 | 1.00 | 21.36 | C |
| ATOM | 9607 | CD1 | LEU | B | 104 | −73.002 | −42.860 | −15.067 | 1.00 | 19.31 | C |
| ATOM | 9611 | CD2 | LEU | B | 104 | −71.310 | −41.157 | −15.633 | 1.00 | 19.57 | C |
| ATOM | 9615 | C | LEU | B | 104 | −68.156 | −43.781 | −14.071 | 1.00 | 23.15 | C |
| ATOM | 9616 | O | LEU | B | 104 | −67.445 | −43.007 | −13.423 | 1.00 | 23.40 | O |
| ATOM | 9618 | N | LEU | B | 105 | −68.106 | −45.091 | −13.894 | 1.00 | 22.79 | N |
| ATOM | 9619 | CA | LEU | B | 105 | −67.203 | −45.659 | −12.916 | 1.00 | 22.40 | C |
| ATOM | 9621 | CB | LEU | B | 105 | −67.303 | −47.178 | −12.912 | 1.00 | 22.42 | C |
| ATOM | 9624 | CG | LEU | B | 105 | −68.505 | −47.709 | −12.163 | 1.00 | 21.82 | C |
| ATOM | 9626 | CD1 | LEU | B | 105 | −68.810 | −49.120 | −12.591 | 1.00 | 21.95 | C |
| ATOM | 9630 | CD2 | LEU | B | 105 | −68.201 | −47.648 | −10.692 | 1.00 | 22.14 | C |
| ATOM | 9634 | C | LEU | B | 105 | −65.767 | −45.239 | −13.196 | 1.00 | 22.33 | C |
| ATOM | 9635 | O | LEU | B | 105 | −65.049 | −44.823 | −12.275 | 1.00 | 22.13 | O |
| ATOM | 9637 | N | ARG | B | 106 | −65.331 | −45.342 | −14.451 | 1.00 | 22.08 | N |
| ATOM | 9638 | CA | ARG | B | 106 | −63.953 | −44.973 | −14.730 | 1.00 | 22.20 | C |
| ATOM | 9640 | CB | ARG | B | 106 | −63.521 | −45.266 | −16.151 | 1.00 | 22.33 | C |
| ATOM | 9643 | CG | ARG | B | 106 | −62.075 | −44.827 | −16.329 | 1.00 | 23.60 | C |
| ATOM | 9646 | CD | ARG | B | 106 | −61.383 | −45.445 | −17.513 | 1.00 | 24.71 | C |
| ATOM | 9649 | NE | ARG | B | 106 | −61.078 | −46.852 | −17.319 | 1.00 | 24.66 | N |
| ATOM | 9651 | CZ | ARG | B | 106 | −60.418 | −47.582 | −18.206 | 1.00 | 25.75 | C |
| ATOM | 9652 | NH1 | ARG | B | 106 | −59.995 | −47.028 | −19.337 | 1.00 | 26.41 | N |
| ATOM | 9655 | NH2 | ARG | B | 106 | −60.182 | −48.866 | −17.971 | 1.00 | 26.54 | N |
| ATOM | 9658 | C | ARG | B | 106 | −63.732 | −43.504 | −14.438 | 1.00 | 21.75 | C |
| ATOM | 9659 | O | ARG | B | 106 | −62.801 | −43.145 | −13.725 | 1.00 | 21.50 | O |
| ATOM | 9661 | N | GLN | B | 107 | −64.609 | −42.680 | −15.003 | 1.00 | 21.69 | N |
| ATOM | 9662 | CA | GLN | B | 107 | −64.630 | −41.239 | −14.794 | 1.00 | 21.64 | C |
| ATOM | 9664 | CB | GLN | B | 107 | −65.964 | −40.664 | −15.261 | 1.00 | 21.71 | C |
| ATOM | 9667 | CG | GLN | B | 107 | −66.169 | −39.178 | −14.929 | 1.00 | 21.97 | C |
| ATOM | 9670 | CD | GLN | B | 107 | −67.588 | −38.723 | −15.172 | 1.00 | 21.54 | C |
| ATOM | 9671 | OE1 | GLN | B | 107 | −68.355 | −39.365 | −15.906 | 1.00 | 20.08 | O |
| ATOM | 9672 | NE2 | GLN | B | 107 | −67.948 | −37.600 | −14.556 | 1.00 | 21.45 | N |
| ATOM | 9675 | C | GLN | B | 107 | −64.454 | −40.850 | −13.352 | 1.00 | 21.70 | C |
| ATOM | 9676 | O | GLN | B | 107 | −63.776 | −39.865 | −13.078 | 1.00 | 22.14 | O |
| ATOM | 9678 | N | HIS | B | 108 | −65.091 | −41.599 | −12.450 | 1.00 | 21.53 | N |
| ATOM | 9679 | CA | HIS | B | 108 | −65.049 | −41.326 | −11.019 | 1.00 | 21.63 | C |
| ATOM | 9681 | CB | HIS | B | 108 | −66.447 | −41.535 | −10.429 | 1.00 | 21.47 | C |
| ATOM | 9684 | CG | HIS | B | 108 | −67.416 | −40.445 | −10.752 | 1.00 | 20.91 | C |
| ATOM | 9685 | ND1 | HIS | B | 108 | −67.541 | −39.315 | −9.976 | 1.00 | 20.66 | N |
| ATOM | 9687 | CE1 | HIS | B | 108 | −68.476 | −38.535 | −10.490 | 1.00 | 20.90 | C |
| ATOM | 9689 | NE2 | HIS | B | 108 | −68.966 | −39.118 | −11.567 | 1.00 | 19.67 | N |
| ATOM | 9691 | CD2 | HIS | B | 108 | −68.326 | −40.320 | −11.747 | 1.00 | 20.76 | C |
| ATOM | 9693 | C | HIS | B | 108 | −64.024 | −42.209 | −10.269 | 1.00 | 22.22 | C |
| ATOM | 9694 | O | HIS | B | 108 | −64.220 | −42.553 | −9.104 | 1.00 | 22.17 | O |
| ATOM | 9696 | N | GLY | B | 109 | −62.950 | −42.613 | −10.933 | 1.00 | 22.91 | N |
| ATOM | 9697 | CA | GLY | B | 109 | −61.846 | −43.288 | −10.245 | 1.00 | 23.85 | C |
| ATOM | 9700 | C | GLY | B | 109 | −61.986 | −44.748 | −9.800 | 1.00 | 24.50 | C |
| ATOM | 9701 | O | GLY | B | 109 | −61.053 | −45.306 | −9.189 | 1.00 | 24.12 | O |
| ATOM | 9703 | N | PHE | B | 110 | −63.128 | −45.371 | −10.094 | 1.00 | 25.16 | N |
| ATOM | 9704 | CA | PHE | B | 110 | −63.309 | −46.791 | −9.800 | 1.00 | 25.67 | C |
| ATOM | 9706 | CB | PHE | B | 110 | −64.782 | −47.187 | −9.891 | 1.00 | 25.80 | C |
| ATOM | 9709 | CG | PHE | B | 110 | −65.625 | −46.656 | −8.772 | 1.00 | 26.12 | C |
| ATOM | 9710 | CD1 | PHE | B | 110 | −65.564 | −47.230 | −7.510 | 1.00 | 27.13 | C |
| ATOM | 9712 | CE1 | PHE | B | 110 | −66.353 | −46.751 | −6.468 | 1.00 | 27.42 | C |
| ATOM | 9714 | CZ | PHE | B | 110 | −67.215 | −45.691 | −6.692 | 1.00 | 26.93 | C |
| ATOM | 9716 | CE2 | PHE | B | 110 | −67.284 | −45.119 | −7.954 | 1.00 | 26.49 | C |
| ATOM | 9718 | CD2 | PHE | B | 110 | −66.494 | −45.601 | −8.981 | 1.00 | 25.96 | C |
| ATOM | 9720 | C | PHE | B | 110 | −62.505 | −47.615 | −10.793 | 1.00 | 25.92 | C |
| ATOM | 9721 | O | PHE | B | 110 | −62.232 | −47.157 | −11.898 | 1.00 | 26.41 | O |
| ATOM | 9723 | N | GLU | B | 111 | −62.134 | −48.832 | −10.406 | 1.00 | 26.06 | N |
| ATOM | 9724 | CA | GLU | B | 111 | −61.403 | −49.724 | −11.304 | 1.00 | 26.17 | C |
| ATOM | 9726 | CB | GLU | B | 111 | −60.444 | −50.609 | −10.511 | 1.00 | 26.50 | C |
| ATOM | 9729 | CG | GLU | B | 111 | −59.372 | −51.272 | −11.374 | 1.00 | 28.11 | C |
| ATOM | 9732 | CD | GLU | B | 111 | −58.607 | −52.377 | −10.646 | 1.00 | 30.70 | C |
| ATOM | 9733 | OE1 | GLU | B | 111 | −58.660 | −52.436 | −9.390 | 1.00 | 31.99 | O |
| ATOM | 9734 | OE2 | GLU | B | 111 | −57.948 | −53.190 | −11.338 | 1.00 | 32.09 | O |

TABLE 3-7-continued

Coordinates of *P. tremuloides* IspS

| ATOM | 9735 | C | GLU | B | 111 | −62.355 | −50.598 | −12.130 | 1.00 | 25.60 | C |
|---|---|---|---|---|---|---|---|---|---|---|---|
| ATOM | 9736 | O | GLU | B | 111 | −63.116 | −51.388 | −11.585 | 1.00 | 25.48 | O |
| ATOM | 9738 | N | VAL | B | 112 | −62.314 | −50.439 | −13.447 | 1.00 | 25.24 | N |
| ATOM | 9739 | CA | VAL | B | 112 | −63.026 | −51.331 | −14.357 | 1.00 | 24.90 | C |
| ATOM | 9741 | CB | VAL | B | 112 | −64.308 | −50.712 | −14.908 | 1.00 | 24.92 | C |
| ATOM | 9743 | CG1 | VAL | B | 112 | −65.268 | −50.437 | −13.771 | 1.00 | 25.26 | C |
| ATOM | 9747 | CG2 | VAL | B | 112 | −63.999 | −49.450 | −15.706 | 1.00 | 24.77 | C |
| ATOM | 9751 | C | VAL | B | 112 | −62.144 | −51.701 | −15.522 | 1.00 | 24.66 | C |
| ATOM | 9752 | O | VAL | B | 112 | −61.217 | −50.964 | −15.862 | 1.00 | 23.80 | O |
| ATOM | 9754 | N | SER | B | 113 | −62.467 | −52.842 | −16.132 | 1.00 | 24.88 | N |
| ATOM | 9755 | CA | SER | B | 113 | −61.604 | −53.494 | −17.109 | 1.00 | 25.21 | C |
| ATOM | 9757 | CB | SER | B | 113 | −61.286 | −54.913 | −16.654 | 1.00 | 24.94 | C |
| ATOM | 9760 | OG | SER | B | 113 | −60.357 | −55.523 | −17.528 | 1.00 | 24.31 | O |
| ATOM | 9762 | C | SER | B | 113 | −62.233 | −53.532 | −18.492 | 1.00 | 25.88 | C |
| ATOM | 9763 | O | SER | B | 113 | −63.446 | −53.651 | −18.630 | 1.00 | 25.86 | O |
| ATOM | 9765 | N | GLN | B | 114 | −61.406 | −53.438 | −19.526 | 1.00 | 26.92 | N |
| ATOM | 9766 | CA | GLN | B | 114 | −61.928 | −53.491 | −20.880 | 1.00 | 27.83 | C |
| ATOM | 9768 | CB | GLN | B | 114 | −60.846 | −53.194 | −21.917 | 1.00 | 27.75 | C |
| ATOM | 9771 | CG | GLN | B | 114 | −59.559 | −53.952 | −21.726 | 1.00 | 28.05 | C |
| ATOM | 9774 | CD | GLN | B | 114 | −58.739 | −54.077 | −23.007 | 1.00 | 28.39 | C |
| ATOM | 9775 | OE1 | GLN | B | 114 | −59.086 | −53.515 | −24.051 | 1.00 | 29.05 | O |
| ATOM | 9776 | NE2 | GLN | B | 114 | −57.637 | −54.808 | −22.925 | 1.00 | 27.62 | N |
| ATOM | 9779 | C | GLN | B | 114 | −62.615 | −54.827 | −21.158 | 1.00 | 28.78 | C |
| ATOM | 9780 | O | GLN | B | 114 | −63.484 | −54.905 | −22.022 | 1.00 | 29.10 | O |
| ATOM | 9782 | N | GLU | B | 115 | −62.248 | −55.861 | −20.401 | 1.00 | 29.99 | N |
| ATOM | 9783 | CA | GLU | B | 115 | −62.888 | −57.181 | −20.505 | 1.00 | 30.89 | C |
| ATOM | 9785 | CB | GLU | B | 115 | −62.252 | −58.202 | −19.549 | 1.00 | 31.10 | C |
| ATOM | 9788 | CG | GLU | B | 115 | −60.740 | −58.394 | −19.697 | 1.00 | 32.35 | C |
| ATOM | 9791 | CD | GLU | B | 115 | −60.320 | −58.796 | −21.106 | 1.00 | 34.20 | C |
| ATOM | 9792 | OE1 | GLU | B | 115 | −60.965 | −59.699 | −21.688 | 1.00 | 34.94 | O |
| ATOM | 9793 | OE2 | GLU | B | 115 | −59.348 | −58.201 | −21.634 | 1.00 | 35.60 | O |
| ATOM | 9794 | C | GLU | B | 115 | −64.380 | −57.120 | −20.224 | 1.00 | 31.26 | C |
| ATOM | 9795 | O | GLU | B | 115 | −65.125 | −57.971 | −20.691 | 1.00 | 31.54 | O |
| ATOM | 9797 | N | ALA | B | 116 | −64.825 | −56.127 | −19.465 | 1.00 | 31.91 | N |
| ATOM | 9798 | CA | ALA | B | 116 | −66.255 | −55.937 | −19.259 | 1.00 | 32.69 | C |
| ATOM | 9800 | CB | ALA | B | 116 | −66.521 | −54.648 | −18.513 | 1.00 | 32.62 | C |
| ATOM | 9804 | C | ALA | B | 116 | −66.999 | −55.950 | −20.597 | 1.00 | 33.33 | C |
| ATOM | 9805 | O | ALA | B | 116 | −68.156 | −56.364 | −20.668 | 1.00 | 33.26 | O |
| ATOM | 9807 | N | PHE | B | 117 | −66.316 | −55.521 | −21.655 | 1.00 | 34.16 | N |
| ATOM | 9808 | CA | PHE | B | 117 | −66.889 | −55.498 | −22.996 | 1.00 | 34.98 | C |
| ATOM | 9810 | CB | PHE | B | 117 | −66.310 | −54.314 | −23.766 | 1.00 | 35.02 | C |
| ATOM | 9813 | CG | PHE | B | 117 | −66.868 | −52.997 | −23.345 | 1.00 | 35.06 | C |
| ATOM | 9814 | CD1 | PHE | B | 117 | −66.061 | −52.046 | −22.729 | 1.00 | 35.33 | C |
| ATOM | 9816 | CE1 | PHE | B | 117 | −66.576 | −50.825 | −22.342 | 1.00 | 35.16 | C |
| ATOM | 9818 | CZ | PHE | B | 117 | −67.907 | −50.544 | −22.570 | 1.00 | 35.37 | C |
| ATOM | 9820 | CE2 | PHE | B | 117 | −68.723 | −51.488 | −23.187 | 1.00 | 35.28 | C |
| ATOM | 9822 | CD2 | PHE | B | 117 | −68.201 | −52.701 | −23.571 | 1.00 | 34.68 | C |
| ATOM | 9824 | C | PHE | B | 117 | −66.676 | −56.766 | −23.830 | 1.00 | 35.86 | C |
| ATOM | 9825 | O | PHE | B | 117 | −66.934 | −56.755 | −25.037 | 1.00 | 35.91 | O |
| ATOM | 9827 | N | SER | B | 118 | −66.215 | −57.853 | −23.212 | 1.00 | 36.98 | N |
| ATOM | 9828 | CA | SER | B | 118 | −65.924 | −59.086 | −23.960 | 1.00 | 37.76 | C |
| ATOM | 9830 | CB | SER | B | 118 | −64.836 | −59.907 | −23.262 | 1.00 | 37.73 | C |
| ATOM | 9833 | OG | SER | B | 118 | −65.272 | −60.346 | −21.987 | 1.00 | 37.77 | O |
| ATOM | 9835 | C | SER | B | 118 | −67.178 | −59.939 | −24.215 | 1.00 | 38.48 | C |
| ATOM | 9836 | O | SER | B | 118 | −67.207 | −60.724 | −25.157 | 1.00 | 38.42 | O |
| ATOM | 9838 | N | GLY | B | 119 | −68.221 | −59.765 | −23.407 | 1.00 | 39.51 | N |
| ATOM | 9839 | CA | GLY | B | 119 | −69.481 | −60.473 | −23.629 | 1.00 | 40.51 | C |
| ATOM | 9842 | C | GLY | B | 119 | −70.287 | −60.034 | −24.848 | 1.00 | 41.51 | C |
| ATOM | 9843 | O | GLY | B | 119 | −71.444 | −60.433 | −25.002 | 1.00 | 41.53 | O |
| ATOM | 9845 | N | PHE | B | 120 | −69.688 | −59.210 | −25.709 | 1.00 | 42.79 | N |
| ATOM | 9846 | CA | PHE | B | 120 | −70.382 | −58.621 | −26.864 | 1.00 | 43.81 | C |
| ATOM | 9848 | CB | PHE | B | 120 | −70.643 | −57.121 | −26.601 | 1.00 | 43.76 | C |
| ATOM | 9851 | CG | PHE | B | 120 | −71.367 | −56.853 | −25.293 | 1.00 | 43.65 | C |
| ATOM | 9852 | CD1 | PHE | B | 120 | −72.762 | −56.874 | −25.230 | 1.00 | 43.48 | C |
| ATOM | 9854 | CE1 | PHE | B | 120 | −73.437 | −56.650 | −24.023 | 1.00 | 43.03 | C |
| ATOM | 9856 | CZ | PHE | B | 120 | −72.717 | −56.413 | −22.865 | 1.00 | 43.09 | C |
| ATOM | 9858 | CE2 | PHE | B | 120 | −71.323 | −56.397 | −22.909 | 1.00 | 43.38 | C |
| ATOM | 9860 | CD2 | PHE | B | 120 | −70.655 | −56.619 | −24.120 | 1.00 | 43.41 | C |
| ATOM | 9862 | C | PHE | B | 120 | −69.607 | −58.832 | −28.175 | 1.00 | 44.81 | C |
| ATOM | 9863 | O | PHE | B | 120 | −69.930 | −58.238 | −29.205 | 1.00 | 44.65 | O |
| ATOM | 9865 | N | LYS | B | 121 | −68.602 | −59.705 | −28.126 | 1.00 | 46.19 | N |
| ATOM | 9866 | CA | LYS | B | 121 | −67.757 | −60.004 | −29.272 | 1.00 | 47.31 | C |
| ATOM | 9868 | CB | LYS | B | 121 | −66.275 | −59.928 | −28.870 | 1.00 | 47.47 | C |
| ATOM | 9871 | CG | LYS | B | 121 | −65.743 | −58.495 | −28.637 | 1.00 | 48.13 | C |
| ATOM | 9874 | CD | LYS | B | 121 | −64.532 | −58.439 | −27.675 | 1.00 | 48.89 | C |
| ATOM | 9877 | CE | LYS | B | 121 | −63.261 | −59.094 | −28.241 | 1.00 | 49.20 | C |
| ATOM | 9880 | NZ | LYS | B | 121 | −62.541 | −58.232 | −29.218 | 1.00 | 49.04 | N |
| ATOM | 9884 | C | LYS | B | 121 | −68.096 | −61.400 | −29.810 | 1.00 | 48.15 | C |

TABLE 3-7-continued

Coordinates of *P. tremuloides* IspS

| ATOM | 9885 | O | LYS | B | 121 | −68.199 | −62.361 | −29.043 | 1.00 | 48.36 | O |
|---|---|---|---|---|---|---|---|---|---|---|---|
| ATOM | 9887 | N | ASP | B | 122 | −68.270 | −61.510 | −31.126 | 1.00 | 49.04 | N |
| ATOM | 9888 | CA | ASP | B | 122 | −68.611 | −62.788 | −31.754 | 1.00 | 49.60 | C |
| ATOM | 9890 | CB | ASP | B | 122 | −69.070 | −62.596 | −33.217 | 1.00 | 49.52 | C |
| ATOM | 9893 | CG | ASP | B | 122 | −67.989 | −62.015 | −34.126 | 1.00 | 49.18 | C |
| ATOM | 9894 | OD1 | ASP | B | 122 | −66.792 | −62.306 | −33.938 | 1.00 | 48.96 | O |
| ATOM | 9895 | OD2 | ASP | B | 122 | −68.351 | −61.268 | −35.057 | 1.00 | 48.82 | O |
| ATOM | 9896 | C | ASP | B | 122 | −67.455 | −63.785 | −31.651 | 1.00 | 50.31 | C |
| ATOM | 9897 | O | ASP | B | 122 | −66.369 | −63.441 | −31.171 | 1.00 | 50.33 | O |
| ATOM | 9899 | N | GLN | B | 123 | −67.705 | −65.014 | −32.098 | 1.00 | 51.05 | N |
| ATOM | 9900 | CA | GLN | B | 123 | −66.716 | −66.095 | −32.057 | 1.00 | 51.61 | C |
| ATOM | 9902 | CB | GLN | B | 123 | −67.263 | −67.330 | −32.785 | 1.00 | 51.82 | C |
| ATOM | 9905 | CG | GLN | B | 123 | −68.483 | −67.986 | −32.117 | 1.00 | 52.32 | C |
| ATOM | 9908 | CD | GLN | B | 123 | −68.117 | −69.137 | −31.184 | 1.00 | 52.64 | C |
| ATOM | 9909 | OE1 | GLN | B | 123 | −67.146 | −69.062 | −30.432 | 1.00 | 53.02 | O |
| ATOM | 9910 | NE2 | GLN | B | 123 | −68.904 | −70.207 | −31.230 | 1.00 | 52.04 | N |
| ATOM | 9913 | C | GLN | B | 123 | −65.358 | −65.694 | −32.659 | 1.00 | 51.78 | C |
| ATOM | 9914 | O | GLN | B | 123 | −64.309 | −66.000 | −32.090 | 1.00 | 51.67 | O |
| ATOM | 9916 | N | ASN | B | 124 | −65.388 | −65.004 | −33.799 | 1.00 | 52.05 | N |
| ATOM | 9917 | CA | ASN | B | 124 | −64.166 | −64.547 | −34.473 | 1.00 | 52.25 | C |
| ATOM | 9919 | CB | ASN | B | 124 | −64.486 | −64.042 | −35.884 | 1.00 | 52.25 | C |
| ATOM | 9922 | CG | ASN | B | 124 | −64.911 | −65.158 | −36.819 | 1.00 | 51.88 | C |
| ATOM | 9923 | OD1 | ASN | B | 124 | −65.918 | −65.825 | −36.592 | 1.00 | 51.43 | O |
| ATOM | 9924 | ND2 | ASN | B | 124 | −64.144 | −65.364 | −37.880 | 1.00 | 51.23 | N |
| ATOM | 9927 | C | ASN | B | 124 | −63.382 | −63.466 | −33.716 | 1.00 | 52.43 | C |
| ATOM | 9928 | O | ASN | B | 124 | −62.189 | −63.287 | −33.959 | 1.00 | 52.33 | O |
| ATOM | 9930 | N | GLY | B | 125 | −64.051 | −62.747 | −32.815 | 1.00 | 52.66 | N |
| ATOM | 9931 | CA | GLY | B | 125 | −63.396 | −61.745 | −31.968 | 1.00 | 52.68 | C |
| ATOM | 9934 | C | GLY | B | 125 | −63.916 | −60.329 | −32.135 | 1.00 | 52.63 | C |
| ATOM | 9935 | O | GLY | B | 125 | −63.539 | −59.447 | −31.367 | 1.00 | 52.57 | O |
| ATOM | 9937 | N | ASN | B | 126 | −64.782 | −60.117 | −33.129 | 1.00 | 52.54 | N |
| ATOM | 9938 | CA | ASN | B | 126 | −65.343 | −58.793 | −33.443 | 1.00 | 52.41 | C |
| ATOM | 9940 | CB | ASN | B | 126 | −65.575 | −58.671 | −34.949 | 1.00 | 52.40 | C |
| ATOM | 9943 | CG | ASN | B | 126 | −64.322 | −58.951 | −35.751 | 1.00 | 52.64 | C |
| ATOM | 9944 | OD1 | ASN | B | 126 | −63.426 | −59.665 | −35.297 | 1.00 | 52.77 | O |
| ATOM | 9945 | ND2 | ASN | B | 126 | −64.249 | −58.390 | −36.952 | 1.00 | 53.00 | N |
| ATOM | 9948 | C | ASN | B | 126 | −66.656 | −58.524 | −32.712 | 1.00 | 52.10 | C |
| ATOM | 9949 | O | ASN | B | 126 | −67.253 | −59.432 | −32.153 | 1.00 | 52.27 | O |
| ATOM | 9951 | N | PHE | B | 127 | −67.111 | −57.279 | −32.724 | 1.00 | 51.61 | N |
| ATOM | 9952 | CA | PHE | B | 127 | −68.362 | −56.936 | −32.055 | 1.00 | 51.23 | C |
| ATOM | 9954 | CB | PHE | B | 127 | −68.506 | −55.416 | −31.905 | 1.00 | 51.21 | C |
| ATOM | 9957 | CG | PHE | B | 127 | −67.702 | −54.848 | −30.770 | 1.00 | 50.58 | C |
| ATOM | 9958 | CD1 | PHE | B | 127 | −66.513 | −54.192 | −31.003 | 1.00 | 50.15 | C |
| ATOM | 9960 | CE1 | PHE | B | 127 | −65.777 | −53.686 | −29.948 | 1.00 | 50.15 | C |
| ATOM | 9962 | CZ | PHE | B | 127 | −66.225 | −53.839 | −28.647 | 1.00 | 49.71 | C |
| ATOM | 9964 | CE2 | PHE | B | 127 | −67.399 | −54.496 | −28.405 | 1.00 | 49.50 | C |
| ATOM | 9966 | CD2 | PHE | B | 127 | −68.132 | −54.999 | −29.459 | 1.00 | 49.99 | C |
| ATOM | 9968 | C | PHE | B | 127 | −69.537 | −57.505 | −32.821 | 1.00 | 50.99 | C |
| ATOM | 9969 | O | PHE | B | 127 | −69.468 | −57.641 | −34.040 | 1.00 | 50.92 | O |
| ATOM | 9971 | N | LEU | B | 128 | −70.609 | −57.840 | −32.106 | 1.00 | 50.83 | N |
| ATOM | 9972 | CA | LEU | B | 128 | −71.799 | −58.422 | −32.731 | 1.00 | 50.76 | C |
| ATOM | 9974 | CB | LEU | B | 128 | −72.780 | −58.953 | −31.669 | 1.00 | 50.80 | C |
| ATOM | 9977 | CG | LEU | B | 128 | −72.341 | −60.098 | −30.734 | 1.00 | 50.91 | C |
| ATOM | 9979 | CD1 | LEU | B | 128 | −73.483 | −60.532 | −29.813 | 1.00 | 50.61 | C |
| ATOM | 9983 | CD2 | LEU | B | 128 | −71.818 | −61.303 | −31.497 | 1.00 | 50.79 | C |
| ATOM | 9987 | C | LEU | B | 128 | −72.500 | −57.407 | −33.646 | 1.00 | 50.55 | C |
| ATOM | 9988 | O | LEU | B | 128 | −73.105 | −56.455 | −33.171 | 1.00 | 50.34 | O |
| ATOM | 9990 | N | GLU | B | 129 | −72.402 | −57.628 | −34.957 | 1.00 | 50.50 | N |
| ATOM | 9991 | CA | GLU | B | 129 | −73.038 | −56.783 | −35.982 | 1.00 | 50.48 | C |
| ATOM | 9993 | CB | GLU | B | 129 | −73.150 | −57.551 | −37.310 | 1.00 | 50.68 | C |
| ATOM | 9996 | CG | GLU | B | 129 | −72.262 | −57.024 | −38.434 | 1.00 | 51.36 | C |
| ATOM | 9999 | CD | GLU | B | 129 | −72.799 | −55.745 | −39.060 | 1.00 | 51.88 | C |
| ATOM | 10000 | OE1 | GLU | B | 129 | −72.110 | −54.707 | −38.961 | 1.00 | 52.72 | O |
| ATOM | 10001 | OE2 | GLU | B | 129 | −73.906 | −55.773 | −39.643 | 1.00 | 51.58 | O |
| ATOM | 10002 | C | GLU | B | 129 | −74.428 | −56.264 | −35.629 | 1.00 | 50.25 | C |
| ATOM | 10003 | O | GLU | B | 129 | −74.737 | −55.110 | −35.899 | 1.00 | 50.18 | O |
| ATOM | 10005 | N | ASN | B | 130 | −75.263 | −57.125 | −35.047 | 1.00 | 50.06 | N |
| ATOM | 10006 | CA | ASN | B | 130 | −76.678 | −56.806 | −34.785 | 1.00 | 49.71 | C |
| ATOM | 10008 | CB | ASN | B | 130 | −77.477 | −58.100 | −34.550 | 1.00 | 49.69 | C |
| ATOM | 10011 | CG | ASN | B | 130 | −77.053 | −58.837 | −33.291 | 1.00 | 49.39 | C |
| ATOM | 10012 | OD1 | ASN | B | 130 | −76.357 | −59.848 | −33.361 | 1.00 | 48.74 | O |
| ATOM | 10013 | ND2 | ASN | B | 130 | −77.468 | −58.329 | −32.134 | 1.00 | 48.99 | N |
| ATOM | 10016 | C | ASN | B | 130 | −76.934 | −55.800 | −33.646 | 1.00 | 49.37 | C |
| ATOM | 10017 | O | ASN | B | 130 | −78.083 | −55.456 | −33.366 | 1.00 | 49.29 | O |
| ATOM | 10019 | N | LEU | B | 131 | −75.868 | −55.336 | −32.996 | 1.00 | 48.98 | N |
| ATOM | 10020 | CA | LEU | B | 131 | −75.957 | −54.279 | −31.988 | 1.00 | 48.56 | C |
| ATOM | 10022 | CB | LEU | B | 131 | −74.797 | −54.392 | −30.991 | 1.00 | 48.44 | C |
| ATOM | 10025 | CG | LEU | B | 131 | −74.759 | −55.671 | −30.148 | 1.00 | 48.19 | C |

TABLE 3-7-continued

| | | | | | Coordinates of *P. tremuloides* IspS | | | | | |
|---|---|---|---|---|---|---|---|---|---|---|
| ATOM | 10027 | CD1 | LEU | B | 131 | −73.382 | −55.852 | −29.523 | 1.00 | 47.23 C |
| ATOM | 10031 | CD2 | LEU | B | 131 | −75.861 | −55.670 | −29.083 | 1.00 | 47.77 C |
| ATOM | 10035 | C | LEU | B | 131 | −75.968 | −52.875 | −32.604 | 1.00 | 48.29 C |
| ATOM | 10036 | O | LEU | B | 131 | −76.022 | −51.895 | −31.874 | 1.00 | 48.44 O |
| ATOM | 10038 | N | LYS | B | 132 | −75.927 | −52.771 | −33.934 | 1.00 | 47.95 N |
| ATOM | 10039 | CA | LYS | B | 132 | −76.020 | −51.471 | −34.621 | 1.00 | 47.64 C |
| ATOM | 10041 | CB | LYS | B | 132 | −75.548 | −51.590 | −36.080 | 1.00 | 47.63 C |
| ATOM | 10044 | CG | LYS | B | 132 | −76.595 | −52.235 | −36.998 | 1.00 | 48.19 C |
| ATOM | 10047 | CD | LYS | B | 132 | −76.111 | −52.483 | −38.429 | 1.00 | 48.16 C |
| ATOM | 10050 | CE | LYS | B | 132 | −77.239 | −53.040 | −39.290 | 1.00 | 47.23 C |
| ATOM | 10053 | NZ | LYS | B | 132 | −76.725 | −53.936 | −40.331 | 1.00 | 47.01 N |
| ATOM | 10057 | C | LYS | B | 132 | −77.449 | −50.907 | −34.597 | 1.00 | 47.13 C |
| ATOM | 10058 | O | LYS | B | 132 | −77.683 | −49.772 | −35.005 | 1.00 | 46.87 O |
| ATOM | 10060 | N | GLU | B | 133 | −78.403 | −51.716 | −34.149 | 1.00 | 46.77 N |
| ATOM | 10061 | CA | GLU | B | 133 | −79.806 | −51.315 | −34.107 | 1.00 | 46.49 C |
| ATOM | 10063 | CB | GLU | B | 133 | −80.691 | −52.458 | −34.622 | 1.00 | 46.56 C |
| ATOM | 10066 | CG | GLU | B | 133 | −80.732 | −52.515 | −36.155 | 1.00 | 47.01 C |
| ATOM | 10069 | CD | GLU | B | 133 | −80.737 | −53.926 | −36.715 | 1.00 | 47.40 C |
| ATOM | 10070 | OE1 | GLU | B | 133 | −81.500 | −54.775 | −36.206 | 1.00 | 47.97 O |
| ATOM | 10071 | OE2 | GLU | B | 133 | −79.983 | −54.177 | −37.679 | 1.00 | 47.22 O |
| ATOM | 10072 | C | GLU | B | 133 | −80.260 | −50.830 | −32.723 | 1.00 | 45.92 C |
| ATOM | 10073 | O | GLU | B | 133 | −81.369 | −50.308 | −32.600 | 1.00 | 46.14 O |
| ATOM | 10075 | N | ASP | B | 134 | −79.424 | −51.002 | −31.691 | 1.00 | 44.98 N |
| ATOM | 10076 | CA | ASP | B | 134 | −79.611 | −50.277 | −30.428 | 1.00 | 44.14 C |
| ATOM | 10078 | CB | ASP | B | 134 | −79.375 | −51.162 | −29.197 | 1.00 | 43.95 C |
| ATOM | 10081 | CG | ASP | B | 134 | −79.646 | −50.419 | −27.883 | 1.00 | 43.57 C |
| ATOM | 10082 | OD1 | ASP | B | 134 | −80.014 | −49.230 | −27.919 | 1.00 | 42.21 O |
| ATOM | 10083 | OD2 | ASP | B | 134 | −79.488 | −51.011 | −26.802 | 1.00 | 43.69 O |
| ATOM | 10084 | C | ASP | B | 134 | −78.662 | −49.073 | −30.426 | 1.00 | 43.47 C |
| ATOM | 10085 | O | ASP | B | 134 | −77.478 | −49.196 | −30.104 | 1.00 | 43.55 O |
| ATOM | 10087 | N | ILE | B | 135 | −79.198 | −47.908 | −30.776 | 1.00 | 42.47 N |
| ATOM | 10088 | CA | ILE | B | 135 | −78.375 | −46.739 | −31.033 | 1.00 | 41.65 C |
| ATOM | 10090 | CB | ILE | B | 135 | −79.080 | −45.783 | −32.012 | 1.00 | 41.45 C |
| ATOM | 10092 | CG1 | ILE | B | 135 | −78.877 | −46.313 | −33.434 | 1.00 | 41.74 C |
| ATOM | 10095 | CD1 | ILE | B | 135 | −79.174 | −45.331 | −34.540 | 1.00 | 42.77 C |
| ATOM | 10099 | CG2 | ILE | B | 135 | −78.533 | −44.391 | −31.905 | 1.00 | 41.68 C |
| ATOM | 10103 | C | ILE | B | 135 | −77.901 | −46.059 | −29.746 | 1.00 | 41.14 C |
| ATOM | 10104 | O | ILE | B | 135 | −76.752 | −45.624 | −29.676 | 1.00 | 41.11 O |
| ATOM | 10106 | N | LYS | B | 136 | −78.742 | −45.998 | −28.714 | 1.00 | 40.53 N |
| ATOM | 10107 | CA | LYS | B | 136 | −78.281 | −45.480 | −27.409 | 1.00 | 40.10 C |
| ATOM | 10109 | CB | LYS | B | 136 | −79.431 | −45.361 | −26.375 | 1.00 | 40.40 C |
| ATOM | 10112 | CG | LYS | B | 136 | −79.910 | −46.697 | −25.786 | 1.00 | 42.49 C |
| ATOM | 10115 | CD | LYS | B | 136 | −81.002 | −46.574 | −24.698 | 1.00 | 44.79 C |
| ATOM | 10118 | CE | LYS | B | 136 | −81.599 | −47.994 | −24.363 | 1.00 | 46.03 C |
| ATOM | 10121 | NZ | LYS | B | 136 | −82.231 | −48.149 | −22.994 | 1.00 | 46.23 N |
| ATOM | 10125 | C | LYS | B | 136 | −77.104 | −46.327 | −26.863 | 1.00 | 38.85 C |
| ATOM | 10126 | O | LYS | B | 136 | −76.246 | −45.806 | −26.143 | 1.00 | 38.91 O |
| ATOM | 10128 | N | ALA | B | 137 | −77.062 | −47.617 | −27.219 | 1.00 | 37.27 N |
| ATOM | 10129 | CA | ALA | B | 137 | −75.935 | −48.486 | −26.864 | 1.00 | 35.88 C |
| ATOM | 10131 | CB | ALA | B | 137 | −76.255 | −49.952 | −27.116 | 1.00 | 35.69 C |
| ATOM | 10135 | C | ALA | B | 137 | −74.708 | −48.085 | −27.645 | 1.00 | 34.63 C |
| ATOM | 10136 | O | ALA | B | 137 | −73.647 | −47.894 | −27.055 | 1.00 | 34.70 O |
| ATOM | 10138 | N | ILE | B | 138 | −74.845 | −47.946 | −28.965 | 1.00 | 33.12 N |
| ATOM | 10139 | CA | ILE | B | 138 | −73.693 | −47.597 | −29.805 | 1.00 | 31.97 C |
| ATOM | 10141 | CB | ILE | B | 138 | −74.020 | −47.572 | −31.296 | 1.00 | 31.50 C |
| ATOM | 10143 | CG1 | ILE | B | 138 | −74.433 | −48.955 | −31.774 | 1.00 | 31.28 C |
| ATOM | 10146 | CD1 | ILE | B | 138 | −73.460 | −50.052 | −31.417 | 1.00 | 30.86 C |
| ATOM | 10150 | CG2 | ILE | B | 138 | −72.819 | −47.138 | −32.073 | 1.00 | 30.61 C |
| ATOM | 10154 | C | ILE | B | 138 | −73.124 | −46.245 | −29.413 | 1.00 | 31.57 C |
| ATOM | 10155 | O | ILE | B | 138 | −71.909 | −46.090 | −29.305 | 1.00 | 31.77 O |
| ATOM | 10157 | N | LEU | B | 139 | −73.997 | −45.268 | −29.192 | 1.00 | 30.92 N |
| ATOM | 10158 | CA | LEU | B | 139 | −73.555 | −43.962 | −28.713 | 1.00 | 30.29 C |
| ATOM | 10160 | CB | LEU | B | 139 | −74.732 | −43.000 | −28.530 | 1.00 | 30.13 C |
| ATOM | 10163 | CG | LEU | B | 139 | −74.778 | −41.890 | −29.574 | 1.00 | 29.96 C |
| ATOM | 10165 | CD1 | LEU | B | 139 | −73.496 | −41.060 | −29.508 | 1.00 | 28.26 C |
| ATOM | 10169 | CD2 | LEU | B | 139 | −76.022 | −41.019 | −29.397 | 1.00 | 29.48 C |
| ATOM | 10173 | C | LEU | B | 139 | −72.835 | −44.136 | −27.397 | 1.00 | 29.95 C |
| ATOM | 10174 | O | LEU | B | 139 | −71.709 | −43.687 | −27.232 | 1.00 | 30.45 O |
| ATOM | 10176 | N | SER | B | 140 | −73.492 | −44.807 | −26.463 | 1.00 | 29.33 N |
| ATOM | 10177 | CA | SER | B | 140 | −72.916 | −45.061 | −25.150 | 1.00 | 28.84 C |
| ATOM | 10179 | CB | SER | B | 140 | −73.900 | −45.878 | −24.298 | 1.00 | 28.93 C |
| ATOM | 10182 | OG | SER | B | 140 | −73.527 | −45.870 | −22.930 | 1.00 | 30.33 O |
| ATOM | 10184 | C | SER | B | 140 | −71.555 | −45.770 | −25.243 | 1.00 | 27.78 C |
| ATOM | 10185 | O | SER | B | 140 | −70.637 | −45.454 | −24.489 | 1.00 | 27.46 O |
| ATOM | 10187 | N | LEU | B | 141 | −71.432 | −46.719 | −26.167 | 1.00 | 26.82 N |
| ATOM | 10188 | CA | LEU | B | 141 | −70.178 | −47.433 | −26.348 | 1.00 | 26.34 C |
| ATOM | 10190 | CB | LEU | B | 141 | −70.366 | −48.658 | −27.256 | 1.00 | 26.16 C |
| ATOM | 10193 | CG | LEU | B | 141 | −69.098 | −49.472 | −27.584 | 1.00 | 26.09 C |

TABLE 3-7-continued

| | | | | | | | | | | | |
|---|---|---|---|---|---|---|---|---|---|---|---|
| ATOM | 10195 | CD1 | LEU | B | 141 | −68.355 | −49.960 | −26.330 | 1.00 | 24.64 | C |
| ATOM | 10199 | CD2 | LEU | B | 141 | −69.455 | −50.643 | −28.481 | 1.00 | 25.94 | C |
| ATOM | 10203 | C | LEU | B | 141 | −69.124 | −46.476 | −26.914 | 1.00 | 25.89 | C |
| ATOM | 10204 | O | LEU | B | 141 | −68.025 | −46.346 | −26.366 | 1.00 | 25.77 | O |
| ATOM | 10206 | N | TYR | B | 142 | −69.471 | −45.809 | −28.008 | 1.00 | 25.41 | N |
| ATOM | 10207 | CA | TYR | B | 142 | −68.609 | −44.804 | −28.610 | 1.00 | 25.03 | C |
| ATOM | 10209 | CB | TYR | B | 142 | −69.399 | −43.982 | −29.617 | 1.00 | 24.80 | C |
| ATOM | 10212 | CG | TYR | B | 142 | −68.736 | −42.695 | −30.043 | 1.00 | 24.47 | C |
| ATOM | 10213 | CD1 | TYR | B | 142 | −67.761 | −42.686 | −31.029 | 1.00 | 24.18 | C |
| ATOM | 10215 | CE1 | TYR | B | 142 | −67.166 | −41.516 | −31.438 | 1.00 | 24.70 | C |
| ATOM | 10217 | CZ | TYR | B | 142 | −67.548 | −40.315 | −30.871 | 1.00 | 25.80 | C |
| ATOM | 10218 | OH | TYR | B | 142 | −66.940 | −39.129 | −31.279 | 1.00 | 27.63 | O |
| ATOM | 10220 | CE2 | TYR | B | 142 | −68.522 | −40.299 | −29.890 | 1.00 | 25.57 | C |
| ATOM | 10222 | CD2 | TYR | B | 142 | −69.110 | −41.485 | −29.485 | 1.00 | 24.73 | C |
| ATOM | 10224 | C | TYR | B | 142 | −68.095 | −43.883 | −27.537 | 1.00 | 25.17 | C |
| ATOM | 10225 | O | TYR | B | 142 | −66.886 | −43.732 | −27.360 | 1.00 | 25.40 | O |
| ATOM | 10227 | N | GLU | B | 143 | −69.038 | −43.293 | −26.807 | 1.00 | 25.12 | N |
| ATOM | 10228 | CA | GLU | B | 143 | −68.744 | −42.256 | −25.828 | 1.00 | 25.10 | C |
| ATOM | 10230 | CB | GLU | B | 143 | −70.046 | −41.726 | −25.226 | 1.00 | 25.33 | C |
| ATOM | 10233 | CG | GLU | B | 143 | −70.006 | −40.244 | −24.849 | 1.00 | 27.57 | C |
| ATOM | 10236 | CD | GLU | B | 143 | −70.321 | −39.313 | −26.023 | 1.00 | 30.43 | C |
| ATOM | 10237 | OE1 | GLU | B | 143 | −69.343 | −38.764 | −26.583 | 1.00 | 32.89 | O |
| ATOM | 10238 | OE2 | GLU | B | 143 | −71.526 | −39.130 | −26.377 | 1.00 | 30.86 | O |
| ATOM | 10239 | C | GLU | B | 143 | −67.794 | −42.746 | −24.729 | 1.00 | 24.43 | C |
| ATOM | 10240 | O | GLU | B | 143 | −67.026 | −41.959 | −24.179 | 1.00 | 24.06 | O |
| ATOM | 10242 | N | ALA | B | 144 | −67.840 | −44.050 | −24.449 | 1.00 | 24.01 | N |
| ATOM | 10243 | CA | ALA | B | 144 | −67.033 | −44.681 | −23.399 | 1.00 | 23.74 | C |
| ATOM | 10245 | CB | ALA | B | 144 | −67.726 | −45.943 | −22.883 | 1.00 | 23.48 | C |
| ATOM | 10249 | C | ALA | B | 144 | −65.631 | −45.025 | −23.864 | 1.00 | 23.57 | C |
| ATOM | 10250 | O | ALA | B | 144 | −64.720 | −45.171 | −23.060 | 1.00 | 23.69 | O |
| ATOM | 10252 | N | SER | B | 145 | −65.455 | −45.168 | −25.165 | 1.00 | 23.45 | N |
| ATOM | 10253 | CA | SER | B | 145 | −64.168 | −45.568 | −25.701 | 1.00 | 23.44 | C |
| ATOM | 10255 | CB | SER | B | 145 | −64.300 | −45.856 | −27.214 | 1.00 | 23.63 | C |
| ATOM | 10258 | OG | SER | B | 145 | −64.822 | −44.748 | −27.952 | 1.00 | 24.24 | O |
| ATOM | 10260 | C | SER | B | 145 | −63.065 | −44.520 | −25.416 | 1.00 | 23.24 | C |
| ATOM | 10261 | O | SER | B | 145 | −61.877 | −44.848 | −25.288 | 1.00 | 23.25 | O |
| ATOM | 10263 | N | PHE | B | 146 | −63.454 | −43.257 | −25.285 | 1.00 | 22.92 | N |
| ATOM | 10264 | CA | PHE | B | 146 | −62.464 | −42.189 | −25.170 | 1.00 | 22.35 | C |
| ATOM | 10266 | CB | PHE | B | 146 | −63.090 | −40.837 | −25.478 | 1.00 | 22.09 | C |
| ATOM | 10269 | CG | PHE | B | 146 | −63.505 | −40.717 | −26.911 | 1.00 | 22.40 | C |
| ATOM | 10270 | CD1 | PHE | B | 146 | −62.619 | −40.229 | −27.868 | 1.00 | 21.98 | C |
| ATOM | 10272 | CE1 | PHE | B | 146 | −62.985 | −40.156 | −29.201 | 1.00 | 21.80 | C |
| ATOM | 10274 | CZ | PHE | B | 146 | −64.241 | −40.579 | −29.594 | 1.00 | 21.91 | C |
| ATOM | 10276 | CE2 | PHE | B | 146 | −65.123 | −41.098 | −28.649 | 1.00 | 22.29 | C |
| ATOM | 10278 | CD2 | PHE | B | 146 | −64.751 | −41.170 | −27.323 | 1.00 | 22.34 | C |
| ATOM | 10280 | C | PHE | B | 146 | −61.762 | −42.208 | −23.837 | 1.00 | 21.91 | C |
| ATOM | 10281 | O | PHE | B | 146 | −60.669 | −41.683 | −23.733 | 1.00 | 22.30 | O |
| ATOM | 10283 | N | LEU | B | 147 | −62.361 | −42.864 | −22.841 | 1.00 | 21.27 | N |
| ATOM | 10284 | CA | LEU | B | 147 | −61.727 | −43.050 | −21.535 | 1.00 | 20.49 | C |
| ATOM | 10286 | CB | LEU | B | 147 | −62.791 | −43.333 | −20.478 | 1.00 | 20.14 | C |
| ATOM | 10289 | CG | LEU | B | 147 | −63.609 | −42.109 | −20.102 | 1.00 | 18.87 | C |
| ATOM | 10291 | CD1 | LEU | B | 147 | −64.813 | −42.020 | −20.959 | 1.00 | 15.94 | C |
| ATOM | 10295 | CD2 | LEU | B | 147 | −63.988 | −42.189 | −18.642 | 1.00 | 18.62 | C |
| ATOM | 10299 | C | LEU | B | 147 | −60.678 | −44.163 | −21.498 | 1.00 | 20.41 | C |
| ATOM | 10300 | O | LEU | B | 147 | −60.243 | −44.552 | −20.415 | 1.00 | 20.44 | O |
| ATOM | 10302 | N | ALA | B | 148 | −60.268 | −44.664 | −22.662 | 1.00 | 20.28 | N |
| ATOM | 10303 | CA | ALA | B | 148 | −59.330 | −45.784 | −22.745 | 1.00 | 20.33 | C |
| ATOM | 10305 | CB | ALA | B | 148 | −59.188 | −46.231 | −24.194 | 1.00 | 20.15 | C |
| ATOM | 10309 | C | ALA | B | 148 | −57.952 | −45.462 | −22.170 | 1.00 | 20.54 | C |
| ATOM | 10310 | O | ALA | B | 148 | −57.435 | −44.366 | −22.341 | 1.00 | 20.23 | O |
| ATOM | 10312 | N | LEU | B | 149 | −57.366 | −46.435 | −21.486 | 1.00 | 21.19 | N |
| ATOM | 10313 | CA | LEU | B | 149 | −55.969 | −46.354 | −21.067 | 1.00 | 22.02 | C |
| ATOM | 10315 | CB | LEU | B | 149 | −55.768 | −47.073 | −19.725 | 1.00 | 21.90 | C |
| ATOM | 10318 | CG | LEU | B | 149 | −56.541 | −46.496 | −18.523 | 1.00 | 21.50 | C |
| ATOM | 10320 | CD1 | LEU | B | 149 | −55.979 | −47.006 | −17.223 | 1.00 | 20.96 | C |
| ATOM | 10324 | CD2 | LEU | B | 149 | −56.520 | −44.974 | −18.505 | 1.00 | 20.95 | C |
| ATOM | 10328 | C | LEU | B | 149 | −55.054 | −46.930 | −22.159 | 1.00 | 22.84 | C |
| ATOM | 10329 | O | LEU | B | 149 | −55.507 | −47.678 | −23.017 | 1.00 | 22.91 | O |
| ATOM | 10331 | N | GLU | B | 150 | −53.781 | −46.550 | −22.163 | 1.00 | 23.93 | N |
| ATOM | 10332 | CA | GLU | B | 150 | −52.858 | −47.071 | −23.174 | 1.00 | 25.03 | C |
| ATOM | 10334 | CB | GLU | B | 150 | −51.472 | −46.431 | −23.012 | 1.00 | 25.41 | C |
| ATOM | 10337 | CG | GLU | B | 150 | −50.530 | −46.608 | −24.213 | 1.00 | 27.44 | C |
| ATOM | 10340 | CD | GLU | B | 150 | −49.132 | −45.987 | −23.992 | 1.00 | 30.04 | C |
| ATOM | 10341 | OE1 | GLU | B | 150 | −48.925 | −45.330 | −22.943 | 1.00 | 31.41 | O |
| ATOM | 10342 | OE2 | GLU | B | 150 | −48.242 | −46.161 | −24.867 | 1.00 | 30.34 | O |
| ATOM | 10343 | C | GLU | B | 150 | −52.787 | −48.600 | −23.024 | 1.00 | 25.36 | C |
| ATOM | 10344 | O | GLU | B | 150 | −52.613 | −49.098 | −21.911 | 1.00 | 25.58 | O |
| ATOM | 10346 | N | GLY | B | 151 | −52.968 | −49.337 | −24.122 | 1.00 | 25.79 | N |

TABLE 3-7-continued

Coordinates of *P. tremuloides* IspS

| ATOM | 10347 | CA | GLY | B | 151 | −52.959 | −50.816 | −24.086 | 1.00 | 26.11 | C |
|---|---|---|---|---|---|---|---|---|---|---|---|
| ATOM | 10350 | C | GLY | B | 151 | −54.323 | −51.522 | −24.047 | 1.00 | 26.44 | C |
| ATOM | 10351 | O | GLY | B | 151 | −54.393 | −52.747 | −24.135 | 1.00 | 26.91 | O |
| ATOM | 10353 | N | GLU | B | 152 | −55.407 | −50.768 | −23.899 | 1.00 | 26.58 | N |
| ATOM | 10354 | CA | GLU | B | 152 | −56.757 | −51.319 | −23.971 | 1.00 | 26.57 | C |
| ATOM | 10356 | CB | GLU | B | 152 | −57.697 | −50.531 | −23.065 | 1.00 | 26.74 | C |
| ATOM | 10359 | CG | GLU | B | 152 | −57.291 | −50.595 | −21.596 | 1.00 | 27.63 | C |
| ATOM | 10362 | CD | GLU | B | 152 | −58.271 | −49.893 | −20.668 | 1.00 | 28.86 | C |
| ATOM | 10363 | OE1 | GLU | B | 152 | −58.239 | −50.192 | −19.449 | 1.00 | 28.80 | O |
| ATOM | 10364 | OE2 | GLU | B | 152 | −59.066 | −49.044 | −21.154 | 1.00 | 29.26 | O |
| ATOM | 10365 | C | GLU | B | 152 | −57.254 | −51.303 | −25.415 | 1.00 | 26.53 | C |
| ATOM | 10366 | O | GLU | B | 152 | −57.937 | −50.381 | −25.869 | 1.00 | 26.00 | O |
| ATOM | 10368 | N | ASN | B | 153 | −56.888 | −52.354 | −26.127 | 1.00 | 26.77 | N |
| ATOM | 10369 | CA | ASN | B | 153 | −57.189 | −52.498 | −27.545 | 1.00 | 27.05 | C |
| ATOM | 10371 | CB | ASN | B | 153 | −56.345 | −53.640 | −28.104 | 1.00 | 27.12 | C |
| ATOM | 10374 | CG | ASN | B | 153 | −56.770 | −54.992 | −27.549 | 1.00 | 27.81 | C |
| ATOM | 10375 | OD1 | ASN | B | 153 | −56.540 | −55.307 | −26.379 | 1.00 | 27.65 | O |
| ATOM | 10376 | ND2 | ASN | B | 153 | −57.426 | −55.782 | −28.382 | 1.00 | 29.43 | N |
| ATOM | 10379 | C | ASN | B | 153 | −58.659 | −52.788 | −27.873 | 1.00 | 27.09 | C |
| ATOM | 10380 | O | ASN | B | 153 | −59.053 | −52.658 | −29.029 | 1.00 | 27.11 | O |
| ATOM | 10382 | N | ILE | B | 154 | −59.448 | −53.223 | −26.884 | 1.00 | 27.17 | N |
| ATOM | 10383 | CA | ILE | B | 154 | −60.865 | −53.544 | −27.100 | 1.00 | 27.11 | C |
| ATOM | 10385 | CB | ILE | B | 154 | −61.454 | −54.369 | −25.956 | 1.00 | 26.99 | C |
| ATOM | 10387 | CG1 | ILE | B | 154 | −60.811 | −55.750 | −25.907 | 1.00 | 27.16 | C |
| ATOM | 10390 | CD1 | ILE | B | 154 | −61.309 | −56.622 | −24.746 | 1.00 | 27.41 | C |
| ATOM | 10394 | CG2 | ILE | B | 154 | −62.953 | −54.519 | −26.124 | 1.00 | 26.65 | C |
| ATOM | 10398 | C | ILE | B | 154 | −61.704 | −52.284 | −27.229 | 1.00 | 27.43 | C |
| ATOM | 10399 | O | ILE | B | 154 | −62.718 | −52.279 | −27.939 | 1.00 | 27.39 | O |
| ATOM | 10401 | N | LEU | B | 155 | −61.296 | −51.226 | −26.522 | 1.00 | 27.76 | N |
| ATOM | 10402 | CA | LEU | B | 155 | −61.964 | −49.918 | −26.609 | 1.00 | 27.75 | C |
| ATOM | 10404 | CB | LEU | B | 155 | −61.578 | −49.024 | −25.430 | 1.00 | 27.31 | C |
| ATOM | 10407 | CG | LEU | B | 155 | −61.968 | −49.544 | −24.052 | 1.00 | 26.64 | C |
| ATOM | 10409 | CD1 | LEU | B | 155 | −61.444 | −48.631 | −22.981 | 1.00 | 25.82 | C |
| ATOM | 10413 | CD2 | LEU | B | 155 | −63.465 | −49.674 | −23.944 | 1.00 | 26.45 | C |
| ATOM | 10417 | C | LEU | B | 155 | −61.620 | −49.226 | −27.924 | 1.00 | 28.32 | C |
| ATOM | 10418 | O | LEU | B | 155 | −62.499 | −48.672 | −28.583 | 1.00 | 28.72 | O |
| ATOM | 10420 | N | ASP | B | 156 | −60.348 | −49.264 | −28.309 | 1.00 | 28.84 | N |
| ATOM | 10421 | CA | ASP | B | 156 | −59.934 | −48.737 | −29.601 | 1.00 | 29.43 | C |
| ATOM | 10423 | CB | ASP | B | 156 | −58.423 | −48.928 | −29.823 | 1.00 | 29.92 | C |
| ATOM | 10426 | CG | ASP | B | 156 | −57.566 | −47.912 | −29.045 | 1.00 | 31.35 | C |
| ATOM | 10427 | OD1 | ASP | B | 156 | −57.803 | −46.680 | −29.162 | 1.00 | 33.23 | O |
| ATOM | 10428 | OD2 | ASP | B | 156 | −56.640 | −48.351 | −28.324 | 1.00 | 33.08 | O |
| ATOM | 10429 | C | ASP | B | 156 | −60.719 | −49.411 | −30.717 | 1.00 | 29.36 | C |
| ATOM | 10430 | O | ASP | B | 156 | −61.075 | −48.768 | −31.697 | 1.00 | 29.33 | O |
| ATOM | 10432 | N | GLU | B | 157 | −60.981 | −50.705 | −30.558 | 1.00 | 29.63 | N |
| ATOM | 10433 | CA | GLU | B | 157 | −61.845 | −51.457 | −31.479 | 1.00 | 29.98 | C |
| ATOM | 10435 | CB | GLU | B | 157 | −61.729 | −52.971 | −31.234 | 1.00 | 30.30 | C |
| ATOM | 10438 | CG | GLU | B | 157 | −60.664 | −53.647 | −32.087 | 1.00 | 31.79 | C |
| ATOM | 10441 | CD | GLU | B | 157 | −60.075 | −54.901 | −31.439 | 1.00 | 33.87 | C |
| ATOM | 10442 | OE1 | GLU | B | 157 | −60.793 | −55.560 | −30.640 | 1.00 | 35.07 | O |
| ATOM | 10443 | OE2 | GLU | B | 157 | −58.894 | −55.223 | −31.743 | 1.00 | 33.70 | O |
| ATOM | 10444 | C | GLU | B | 157 | −63.304 | −51.030 | −31.349 | 1.00 | 29.53 | C |
| ATOM | 10445 | O | GLU | B | 157 | −63.999 | −50.878 | −32.351 | 1.00 | 29.53 | O |
| ATOM | 10447 | N | ALA | B | 158 | −63.758 | −50.853 | −30.112 | 1.00 | 29.11 | N |
| ATOM | 10448 | CA | ALA | B | 158 | −65.104 | −50.370 | −29.840 | 1.00 | 28.87 | C |
| ATOM | 10450 | CB | ALA | B | 158 | −65.307 | −50.195 | −28.351 | 1.00 | 28.82 | C |
| ATOM | 10454 | C | ALA | B | 158 | −65.383 | −49.065 | −30.567 | 1.00 | 28.73 | C |
| ATOM | 10455 | O | ALA | B | 158 | −66.485 | −48.857 | −31.065 | 1.00 | 28.80 | O |
| ATOM | 10457 | N | LYS | B | 159 | −64.385 | −48.197 | −30.642 | 1.00 | 28.65 | N |
| ATOM | 10458 | CA | LYS | B | 159 | −64.553 | −46.910 | −31.296 | 1.00 | 28.98 | C |
| ATOM | 10460 | CB | LYS | B | 159 | −63.439 | −45.950 | −30.857 | 1.00 | 29.16 | C |
| ATOM | 10463 | CG | LYS | B | 159 | −63.558 | −44.536 | −31.426 | 1.00 | 29.82 | C |
| ATOM | 10466 | CD | LYS | B | 159 | −62.812 | −43.493 | −30.592 | 1.00 | 30.96 | C |
| ATOM | 10469 | CE | LYS | B | 159 | −61.295 | −43.610 | −30.691 | 1.00 | 31.57 | C |
| ATOM | 10472 | NZ | LYS | B | 159 | −60.630 | −42.426 | −30.079 | 1.00 | 31.49 | N |
| ATOM | 10476 | C | LYS | B | 159 | −64.594 | −47.041 | −32.826 | 1.00 | 29.08 | C |
| ATOM | 10477 | O | LYS | B | 159 | −65.385 | −46.372 | −33.486 | 1.00 | 28.73 | O |
| ATOM | 10479 | N | VAL | B | 160 | −63.736 | −47.891 | −33.386 | 1.00 | 29.53 | N |
| ATOM | 10480 | CA | VAL | B | 160 | −63.686 | −48.087 | −34.836 | 1.00 | 29.89 | C |
| ATOM | 10482 | CB | VAL | B | 160 | −62.466 | −48.971 | −35.282 | 1.00 | 29.93 | C |
| ATOM | 10484 | CG1 | VAL | B | 160 | −62.576 | −49.375 | −36.756 | 1.00 | 29.58 | C |
| ATOM | 10488 | CG2 | VAL | B | 160 | −61.152 | −48.244 | −35.040 | 1.00 | 29.41 | C |
| ATOM | 10492 | C | VAL | B | 160 | −65.001 | −48.723 | −35.263 | 1.00 | 30.32 | C |
| ATOM | 10493 | O | VAL | B | 160 | −65.507 | −48.459 | −36.362 | 1.00 | 30.41 | O |
| ATOM | 10495 | N | PHE | B | 161 | −65.558 | −49.540 | −34.371 | 1.00 | 30.83 | N |
| ATOM | 10496 | CA | PHE | B | 161 | −66.854 | −50.178 | −34.599 | 1.00 | 31.34 | C |
| ATOM | 10498 | CB | PHE | B | 161 | −67.090 | −51.321 | −33.599 | 1.00 | 31.34 | C |
| ATOM | 10501 | CG | PHE | B | 161 | −68.492 | −51.834 | −33.603 | 1.00 | 31.09 | C |

TABLE 3-7-continued

| | | | | | | | | | | |
|---|---|---|---|---|---|---|---|---|---|---|
| ATOM | 10502 | CD1 | PHE | B | 161 | −68.940 | −52.636 | −34.633 | 1.00 | 31.61 C |
| ATOM | 10504 | CE1 | PHE | B | 161 | −70.249 | −53.098 | −34.649 | 1.00 | 31.48 C |
| ATOM | 10506 | CZ | PHE | B | 161 | −71.114 | −52.748 | −33.628 | 1.00 | 30.76 C |
| ATOM | 10508 | CE2 | PHE | B | 161 | −70.677 | −51.944 | −32.606 | 1.00 | 30.19 C |
| ATOM | 10510 | CD2 | PHE | B | 161 | −69.378 | −51.486 | −32.597 | 1.00 | 30.70 C |
| ATOM | 10512 | C | PHE | B | 161 | −67.992 | −49.173 | −34.504 | 1.00 | 31.65 C |
| ATOM | 10513 | O | PHE | B | 161 | −68.785 | −49.038 | −35.432 | 1.00 | 31.62 O |
| ATOM | 10515 | N | ALA | B | 162 | −68.068 | −48.483 | −33.373 | 1.00 | 32.26 N |
| ATOM | 10516 | CA | ALA | B | 162 | −69.135 | −47.519 | −33.129 | 1.00 | 32.84 C |
| ATOM | 10518 | CB | ALA | B | 162 | −68.948 | −46.854 | −31.778 | 1.00 | 32.66 C |
| ATOM | 10522 | C | ALA | B | 162 | −69.224 | −46.474 | −34.245 | 1.00 | 33.40 C |
| ATOM | 10523 | O | ALA | B | 162 | −70.229 | −46.408 | −34.937 | 1.00 | 33.45 O |
| ATOM | 10525 | N | ILE | B | 163 | −68.164 | −45.697 | −34.444 | 1.00 | 34.38 N |
| ATOM | 10526 | CA | ILE | B | 163 | −68.166 | −44.610 | −35.439 | 1.00 | 35.23 C |
| ATOM | 10528 | CB | ILE | B | 163 | −66.734 | −44.062 | −35.733 | 1.00 | 35.18 C |
| ATOM | 10530 | CG1 | ILE | B | 163 | −66.092 | −43.457 | −34.488 | 1.00 | 35.21 C |
| ATOM | 10533 | CD1 | ILE | B | 163 | −64.620 | −43.171 | −34.663 | 1.00 | 35.96 C |
| ATOM | 10537 | CG2 | ILE | B | 163 | −66.778 | −42.977 | −36.799 | 1.00 | 34.72 C |
| ATOM | 10541 | C | ILE | B | 163 | −68.778 | −45.052 | −36.766 | 1.00 | 36.18 C |
| ATOM | 10542 | O | ILE | B | 163 | −69.588 | −44.335 | −37.360 | 1.00 | 35.87 O |
| ATOM | 10544 | N | SER | B | 164 | −68.379 | −46.240 | −37.217 | 1.00 | 37.67 N |
| ATOM | 10545 | CA | SER | B | 164 | −68.761 | −46.752 | −38.539 | 1.00 | 38.74 C |
| ATOM | 10547 | CB | SER | B | 164 | −68.104 | −48.117 | −38.815 | 1.00 | 38.80 C |
| ATOM | 10550 | OG | SER | B | 164 | −68.733 | −49.158 | −38.077 | 1.00 | 39.07 O |
| ATOM | 10552 | C | SER | B | 164 | −70.277 | −46.861 | −38.699 | 1.00 | 39.51 C |
| ATOM | 10553 | O | SER | B | 164 | −70.820 | −46.494 | −39.737 | 1.00 | 39.96 O |
| ATOM | 10555 | N | HIS | B | 165 | −70.962 | −47.363 | −37.680 | 1.00 | 40.28 N |
| ATOM | 10556 | CA | HIS | B | 165 | −72.410 | −47.485 | −37.767 | 1.00 | 41.07 C |
| ATOM | 10558 | CB | HIS | B | 165 | −72.911 | −48.686 | −36.957 | 1.00 | 41.38 C |
| ATOM | 10561 | CG | HIS | B | 165 | −72.571 | −50.005 | −37.587 | 1.00 | 42.65 C |
| ATOM | 10562 | ND1 | HIS | B | 165 | −71.647 | −50.875 | −37.046 | 1.00 | 43.54 N |
| ATOM | 10564 | CE1 | HIS | B | 165 | −71.535 | −51.938 | −37.825 | 1.00 | 43.54 C |
| ATOM | 10566 | NE2 | HIS | B | 165 | −72.346 | −51.785 | −38.858 | 1.00 | 43.25 N |
| ATOM | 10568 | CD2 | HIS | B | 165 | −73.001 | −50.582 | −38.737 | 1.00 | 43.31 C |
| ATOM | 10570 | C | HIS | B | 165 | −73.125 | −46.193 | −37.380 | 1.00 | 41.21 C |
| ATOM | 10571 | O | HIS | B | 165 | −74.257 | −45.980 | −37.805 | 1.00 | 41.53 O |
| ATOM | 10573 | N | LEU | B | 166 | −72.459 | −45.326 | −36.614 | 1.00 | 41.32 N |
| ATOM | 10574 | CA | LEU | B | 166 | −73.042 | −44.039 | −36.201 | 1.00 | 41.31 C |
| ATOM | 10576 | CB | LEU | B | 166 | −72.317 | −43.460 | −34.973 | 1.00 | 41.14 C |
| ATOM | 10579 | CG | LEU | B | 166 | −72.732 | −43.975 | −33.589 | 1.00 | 40.03 C |
| ATOM | 10581 | CD1 | LEU | B | 166 | −71.673 | −43.634 | −32.579 | 1.00 | 38.86 C |
| ATOM | 10585 | CD2 | LEU | B | 166 | −74.077 | −43.421 | −33.151 | 1.00 | 38.52 C |
| ATOM | 10589 | C | LEU | B | 166 | −73.045 | −42.992 | −37.313 | 1.00 | 41.80 C |
| ATOM | 10590 | O | LEU | B | 166 | −74.006 | −42.230 | −37.442 | 1.00 | 41.73 O |
| ATOM | 10592 | N | LYS | B | 167 | −71.982 | −42.947 | −38.116 | 1.00 | 42.47 N |
| ATOM | 10593 | CA | LYS | B | 167 | −71.847 | −41.891 | −39.137 | 1.00 | 43.00 C |
| ATOM | 10595 | CB | LYS | B | 167 | −70.416 | −41.822 | −39.702 | 1.00 | 43.12 C |
| ATOM | 10598 | CG | LYS | B | 167 | −69.937 | −43.068 | −40.450 | 1.00 | 44.12 C |
| ATOM | 10601 | CD | LYS | B | 167 | −69.138 | −42.725 | −41.736 | 1.00 | 45.36 C |
| ATOM | 10604 | CE | LYS | B | 167 | −67.898 | −41.842 | −41.483 | 1.00 | 45.65 C |
| ATOM | 10607 | NZ | LYS | B | 167 | −67.267 | −41.400 | −42.762 | 1.00 | 44.94 N |
| ATOM | 10611 | C | LYS | B | 167 | −72.873 | −41.950 | −40.283 | 1.00 | 42.99 C |
| ATOM | 10612 | O | LYS | B | 167 | −72.826 | −41.124 | −41.182 | 1.00 | 42.95 O |
| ATOM | 10614 | N | GLU | B | 168 | −73.791 | −42.912 | −40.244 | 1.00 | 43.23 N |
| ATOM | 10615 | CA | GLU | B | 168 | −74.928 | −42.940 | −41.167 | 1.00 | 43.44 C |
| ATOM | 10617 | CB | GLU | B | 168 | −74.652 | −43.969 | −42.272 | 1.00 | 43.58 C |
| ATOM | 10620 | CG | GLU | B | 168 | −73.918 | −43.363 | −43.501 | 1.00 | 44.36 C |
| ATOM | 10623 | CD | GLU | B | 168 | −72.618 | −44.082 | −43.895 | 1.00 | 44.53 C |
| ATOM | 10624 | OE1 | GLU | B | 168 | −71.853 | −44.494 | −42.992 | 1.00 | 44.71 O |
| ATOM | 10625 | OE2 | GLU | B | 168 | −72.351 | −44.197 | −45.115 | 1.00 | 43.31 O |
| ATOM | 10626 | C | GLU | B | 168 | −76.263 | −43.214 | −40.442 | 1.00 | 43.24 C |
| ATOM | 10627 | O | GLU | B | 168 | −76.932 | −42.291 | −39.942 | 1.00 | 42.54 O |
| ATOM | 10629 | N | GLY | B | 175 | −83.548 | −42.037 | −36.239 | 1.00 | 49.43 N |
| ATOM | 10630 | CA | GLY | B | 175 | −84.473 | −41.266 | −35.416 | 1.00 | 49.54 C |
| ATOM | 10633 | C | GLY | B | 175 | −84.709 | −39.884 | −36.001 | 1.00 | 49.76 C |
| ATOM | 10634 | O | GLY | B | 175 | −84.828 | −39.741 | −37.220 | 1.00 | 49.70 O |
| ATOM | 10636 | N | LYS | B | 176 | −84.766 | −38.870 | −35.131 | 1.00 | 49.95 N |
| ATOM | 10637 | CA | LYS | B | 176 | −85.014 | −37.468 | −35.534 | 1.00 | 50.05 C |
| ATOM | 10639 | CB | LYS | B | 176 | −86.522 | −37.225 | −35.730 | 1.00 | 50.27 C |
| ATOM | 10642 | CG | LYS | B | 176 | −87.301 | −36.813 | −34.460 | 1.00 | 51.33 C |
| ATOM | 10645 | CD | LYS | B | 176 | −88.553 | −37.658 | −34.202 | 1.00 | 52.21 C |
| ATOM | 10648 | CE | LYS | B | 176 | −88.841 | −37.754 | −32.695 | 1.00 | 52.36 C |
| ATOM | 10651 | NZ | LYS | B | 176 | −90.029 | −38.607 | −32.422 | 1.00 | 52.15 N |
| ATOM | 10655 | C | LYS | B | 176 | −84.427 | −36.432 | −34.554 | 1.00 | 49.75 C |
| ATOM | 10656 | O | LYS | B | 176 | −83.990 | −35.370 | −34.972 | 1.00 | 49.88 O |
| ATOM | 10658 | N | GLU | B | 177 | −84.473 | −36.729 | −33.254 | 1.00 | 49.46 N |
| ATOM | 10659 | CA | GLU | B | 177 | −83.769 | −35.959 | −32.221 | 1.00 | 48.92 C |
| ATOM | 10661 | CB | GLU | B | 177 | −84.628 | −35.813 | −30.946 | 1.00 | 49.03 C |

TABLE 3-7-continued

Coordinates of *P. tremuloides* IspS

| ATOM | 10664 | CG | GLU | B | 177 | −84.196 | −36.691 | −29.732 | 1.00 | 49.60 | C |
|---|---|---|---|---|---|---|---|---|---|---|---|
| ATOM | 10667 | CD | GLU | B | 177 | −85.278 | −36.871 | −28.662 | 1.00 | 50.10 | C |
| ATOM | 10668 | OE1 | GLU | B | 177 | −84.998 | −37.576 | −27.670 | 1.00 | 49.78 | O |
| ATOM | 10669 | OE2 | GLU | B | 177 | −86.401 | −36.336 | −28.808 | 1.00 | 50.78 | O |
| ATOM | 10670 | C | GLU | B | 177 | −82.469 | −36.703 | −31.924 | 1.00 | 48.19 | C |
| ATOM | 10671 | O | GLU | B | 177 | −81.421 | −36.085 | −31.721 | 1.00 | 48.68 | O |
| ATOM | 10673 | N | LEU | B | 178 | −82.557 | −38.037 | −31.900 | 1.00 | 46.98 | N |
| ATOM | 10674 | CA | LEU | B | 178 | −81.398 | −38.924 | −31.817 | 1.00 | 45.91 | C |
| ATOM | 10676 | CB | LEU | B | 178 | −81.838 | −40.387 | −31.945 | 1.00 | 45.70 | C |
| ATOM | 10679 | CG | LEU | B | 178 | −81.111 | −41.408 | −31.074 | 1.00 | 45.24 | C |
| ATOM | 10681 | CD1 | LEU | B | 178 | −81.498 | −41.225 | −29.609 | 1.00 | 44.88 | C |
| ATOM | 10685 | CD2 | LEU | B | 178 | −81.413 | −42.826 | −31.539 | 1.00 | 44.19 | C |
| ATOM | 10689 | C | LEU | B | 178 | −80.423 | −38.571 | −32.934 | 1.00 | 45.27 | C |
| ATOM | 10690 | O | LEU | B | 178 | −79.211 | −38.624 | −32.759 | 1.00 | 44.99 | O |
| ATOM | 10692 | N | ALA | B | 179 | −80.970 | −38.203 | −34.088 | 1.00 | 44.75 | N |
| ATOM | 10693 | CA | ALA | B | 179 | −80.174 | −37.661 | −35.181 | 1.00 | 44.24 | C |
| ATOM | 10695 | CB | ALA | B | 179 | −81.088 | −37.069 | −36.231 | 1.00 | 44.30 | C |
| ATOM | 10699 | C | ALA | B | 179 | −79.192 | −36.602 | −34.683 | 1.00 | 43.65 | C |
| ATOM | 10700 | O | ALA | B | 179 | −78.028 | −36.604 | −35.061 | 1.00 | 43.56 | O |
| ATOM | 10702 | N | GLU | B | 180 | −79.675 | −35.707 | −33.827 | 1.00 | 43.01 | N |
| ATOM | 10703 | CA | GLU | B | 180 | −78.863 | −34.610 | −33.311 | 1.00 | 42.49 | C |
| ATOM | 10705 | CB | GLU | B | 180 | −79.749 | −33.477 | −32.789 | 1.00 | 42.85 | C |
| ATOM | 10708 | CG | GLU | B | 180 | −80.574 | −32.800 | −33.881 | 1.00 | 44.23 | C |
| ATOM | 10711 | CD | GLU | B | 180 | −80.991 | −31.382 | −33.519 | 1.00 | 45.80 | C |
| ATOM | 10712 | OE1 | GLU | B | 180 | −80.098 | −30.580 | −33.156 | 1.00 | 46.69 | O |
| ATOM | 10713 | OE2 | GLU | B | 180 | −82.203 | −31.065 | −33.610 | 1.00 | 46.71 | O |
| ATOM | 10714 | C | GLU | B | 180 | −77.944 | −35.075 | −32.210 | 1.00 | 41.39 | C |
| ATOM | 10715 | O | GLU | B | 180 | −76.843 | −34.562 | −32.071 | 1.00 | 41.27 | O |
| ATOM | 10717 | N | GLN | B | 181 | −78.404 | −36.035 | −31.419 | 1.00 | 40.20 | N |
| ATOM | 10718 | CA | GLN | B | 181 | −77.570 | −36.632 | −30.394 | 1.00 | 39.45 | C |
| ATOM | 10720 | CB | GLN | B | 181 | −78.280 | −37.809 | −29.736 | 1.00 | 39.88 | C |
| ATOM | 10723 | CG | GLN | B | 181 | −78.005 | −37.959 | −28.249 | 1.00 | 41.64 | C |
| ATOM | 10726 | CD | GLN | B | 181 | −78.873 | −37.036 | −27.404 | 1.00 | 44.00 | C |
| ATOM | 10727 | OE1 | GLN | B | 181 | −80.109 | −36.992 | −27.581 | 1.00 | 45.65 | O |
| ATOM | 10728 | NE2 | GLN | B | 181 | −78.235 | −36.291 | −26.474 | 1.00 | 43.41 | N |
| ATOM | 10731 | C | GLN | B | 181 | −76.270 | −37.120 | −31.003 | 1.00 | 38.28 | C |
| ATOM | 10732 | O | GLN | B | 181 | −75.203 | −36.767 | −30.523 | 1.00 | 38.27 | O |
| ATOM | 10734 | N | VAL | B | 182 | −76.358 | −37.911 | −32.072 | 1.00 | 37.05 | N |
| ATOM | 10735 | CA | VAL | B | 182 | −75.160 | −38.515 | −32.675 | 1.00 | 36.20 | C |
| ATOM | 10737 | CB | VAL | B | 182 | −75.486 | −39.661 | −33.681 | 1.00 | 36.11 | C |
| ATOM | 10739 | CG1 | VAL | B | 182 | −76.493 | −40.641 | −33.080 | 1.00 | 36.13 | C |
| ATOM | 10743 | CG2 | VAL | B | 182 | −75.977 | −39.106 | −35.004 | 1.00 | 36.06 | C |
| ATOM | 10747 | C | VAL | B | 182 | −74.238 | −37.495 | −33.364 | 1.00 | 35.44 | C |
| ATOM | 10748 | O | VAL | B | 182 | −73.012 | −37.682 | −33.375 | 1.00 | 35.19 | O |
| ATOM | 10750 | N | SER | B | 183 | −74.811 | −36.432 | −33.936 | 1.00 | 34.41 | N |
| ATOM | 10751 | CA | SER | B | 183 | −73.998 | −35.416 | −34.630 | 1.00 | 33.74 | C |
| ATOM | 10753 | CB | SER | B | 183 | −74.858 | −34.438 | −35.422 | 1.00 | 33.58 | C |
| ATOM | 10756 | OG | SER | B | 183 | −76.003 | −35.085 | −35.925 | 1.00 | 34.52 | O |
| ATOM | 10758 | C | SER | B | 183 | −73.184 | −34.644 | −33.625 | 1.00 | 32.88 | C |
| ATOM | 10759 | O | SER | B | 183 | −72.055 | −34.251 | −33.906 | 1.00 | 33.25 | O |
| ATOM | 10761 | N | HIS | B | 184 | −73.788 | −34.427 | −32.461 | 1.00 | 31.83 | N |
| ATOM | 10762 | CA | HIS | B | 184 | −73.150 | −33.787 | −31.326 | 1.00 | 30.98 | C |
| ATOM | 10764 | CB | HIS | B | 184 | −74.188 | −33.627 | −30.212 | 1.00 | 31.14 | C |
| ATOM | 10767 | CG | HIS | B | 184 | −73.710 | −32.849 | −29.030 | 1.00 | 31.91 | C |
| ATOM | 10768 | ND1 | HIS | B | 184 | −73.326 | −31.527 | −29.114 | 1.00 | 33.18 | N |
| ATOM | 10770 | CE1 | HIS | B | 184 | −72.960 | −31.107 | −27.914 | 1.00 | 33.10 | C |
| ATOM | 10772 | NE2 | HIS | B | 184 | −73.106 | −32.102 | −27.056 | 1.00 | 31.85 | N |
| ATOM | 10774 | CD2 | HIS | B | 184 | −73.583 | −33.200 | −27.727 | 1.00 | 31.86 | C |
| ATOM | 10776 | C | HIS | B | 184 | −71.968 | −34.632 | −30.865 | 1.00 | 30.13 | C |
| ATOM | 10777 | O | HIS | B | 184 | −70.863 | −34.122 | −30.709 | 1.00 | 29.95 | O |
| ATOM | 10779 | N | ALA | B | 185 | −72.194 | −35.931 | −30.683 | 1.00 | 29.27 | N |
| ATOM | 10780 | CA | ALA | B | 185 | −71.123 | −36.856 | −30.281 | 1.00 | 28.64 | C |
| ATOM | 10782 | CB | ALA | B | 185 | −71.689 | −38.233 | −29.986 | 1.00 | 28.44 | C |
| ATOM | 10786 | C | ALA | B | 185 | −70.017 | −36.965 | −31.330 | 1.00 | 28.08 | C |
| ATOM | 10787 | O | ALA | B | 185 | −68.839 | −37.043 | −30.992 | 1.00 | 28.26 | O |
| ATOM | 10789 | N | LEU | B | 186 | −70.394 | −36.984 | −32.602 | 1.00 | 27.40 | N |
| ATOM | 10790 | CA | LEU | B | 186 | −69.412 | −37.101 | −33.674 | 1.00 | 26.84 | C |
| ATOM | 10792 | CB | LEU | B | 186 | −70.088 | −37.481 | −35.000 | 1.00 | 26.75 | C |
| ATOM | 10795 | CG | LEU | B | 186 | −70.085 | −38.983 | −35.320 | 1.00 | 26.70 | C |
| ATOM | 10797 | CD1 | LEU | B | 186 | −70.214 | −39.868 | −34.075 | 1.00 | 27.07 | C |
| ATOM | 10801 | CD2 | LEU | B | 186 | −71.179 | −39.306 | −36.303 | 1.00 | 26.29 | C |
| ATOM | 10805 | C | LEU | B | 186 | −68.594 | −35.822 | −33.815 | 1.00 | 26.45 | C |
| ATOM | 10806 | O | LEU | B | 186 | −67.449 | −35.875 | −34.237 | 1.00 | 26.48 | O |
| ATOM | 10808 | N | GLU | B | 187 | −69.186 | −34.685 | −33.454 | 1.00 | 25.93 | N |
| ATOM | 10809 | CA | GLU | B | 187 | −68.479 | −33.406 | −33.403 | 1.00 | 25.57 | C |
| ATOM | 10811 | CB | GLU | B | 187 | −69.447 | −32.310 | −32.962 | 1.00 | 25.61 | C |
| ATOM | 10814 | CG | GLU | B | 187 | −69.035 | −30.899 | −33.325 | 1.00 | 26.29 | C |
| ATOM | 10817 | CD | GLU | B | 187 | −69.930 | −29.857 | −32.671 | 1.00 | 27.10 | C |

TABLE 3-7-continued

Coordinates of *P. tremuloides* IspS

| ATOM | 10818 | OE1 | GLU | B | 187 | −70.312 | −30.057 | −31.487 | 1.00 | 26.51 | O |
|------|-------|-----|-----|---|-----|---------|---------|---------|------|-------|---|
| ATOM | 10819 | OE2 | GLU | B | 187 | −70.251 | −28.846 | −33.344 | 1.00 | 27.54 | O |
| ATOM | 10820 | C | GLU | B | 187 | −67.307 | −33.490 | −32.418 | 1.00 | 25.13 | C |
| ATOM | 10821 | O | GLU | B | 187 | −66.155 | −33.165 | −32.749 | 1.00 | 24.85 | O |
| ATOM | 10823 | N | LEU | B | 188 | −67.625 | −33.938 | −31.204 | 1.00 | 24.58 | N |
| ATOM | 10824 | CA | LEU | B | 188 | −66.644 | −34.137 | −30.148 | 1.00 | 24.06 | C |
| ATOM | 10826 | CB | LEU | B | 188 | −66.343 | −32.817 | −29.451 | 1.00 | 24.12 | C |
| ATOM | 10829 | CG | LEU | B | 188 | −65.042 | −32.714 | −28.670 | 1.00 | 23.61 | C |
| ATOM | 10831 | CD1 | LEU | B | 188 | −63.895 | −32.872 | −29.629 | 1.00 | 23.12 | C |
| ATOM | 10835 | CD2 | LEU | B | 188 | −64.976 | −31.368 | −27.964 | 1.00 | 23.18 | C |
| ATOM | 10839 | C | LEU | B | 188 | −67.248 | −35.087 | −29.140 | 1.00 | 23.70 | C |
| ATOM | 10840 | O | LEU | B | 188 | −68.392 | −34.901 | −28.743 | 1.00 | 23.68 | O |
| ATOM | 10842 | N | PRO | B | 189 | −66.493 | −36.106 | −28.713 | 1.00 | 23.34 | N |
| ATOM | 10843 | CA | PRO | B | 189 | −67.031 | −36.983 | −27.692 | 1.00 | 23.08 | C |
| ATOM | 10845 | CB | PRO | B | 189 | −66.018 | −38.115 | −27.638 | 1.00 | 22.96 | C |
| ATOM | 10848 | CG | PRO | B | 189 | −64.743 | −37.452 | −27.940 | 1.00 | 23.22 | C |
| ATOM | 10851 | CD | PRO | B | 189 | −65.059 | −36.350 | −28.929 | 1.00 | 23.54 | C |
| ATOM | 10854 | C | PRO | B | 189 | −67.053 | −36.229 | −26.387 | 1.00 | 22.86 | C |
| ATOM | 10855 | O | PRO | B | 189 | −66.284 | −35.285 | −26.215 | 1.00 | 23.03 | O |
| ATOM | 10856 | N | LEU | B | 190 | −67.912 | −36.628 | −25.465 | 1.00 | 22.56 | N |
| ATOM | 10857 | CA | LEU | B | 190 | −68.152 | −35.773 | −24.323 | 1.00 | 22.41 | C |
| ATOM | 10859 | CB | LEU | B | 190 | −69.567 | −35.970 | −23.766 | 1.00 | 23.04 | C |
| ATOM | 10862 | CG | LEU | B | 190 | −69.853 | −37.136 | −22.848 | 1.00 | 23.41 | C |
| ATOM | 10864 | CD1 | LEU | B | 190 | −69.303 | −36.733 | −21.481 | 1.00 | 25.02 | C |
| ATOM | 10868 | CD2 | LEU | B | 190 | −71.342 | −37.411 | −22.820 | 1.00 | 21.69 | C |
| ATOM | 10872 | C | LEU | B | 190 | −67.065 | −35.899 | −23.266 | 1.00 | 21.56 | C |
| ATOM | 10873 | O | LEU | B | 190 | −66.860 | −34.976 | −22.477 | 1.00 | 21.67 | O |
| ATOM | 10875 | N | HIS | B | 191 | −66.320 | −36.998 | −23.283 | 1.00 | 20.39 | N |
| ATOM | 10876 | CA | HIS | B | 191 | −65.089 | −37.037 | −22.490 | 1.00 | 19.40 | C |
| ATOM | 10878 | CB | HIS | B | 191 | −64.399 | −38.393 | −22.597 | 1.00 | 19.19 | C |
| ATOM | 10881 | CG | HIS | B | 191 | −63.222 | −38.530 | −21.689 | 1.00 | 19.32 | C |
| ATOM | 10882 | ND1 | HIS | B | 191 | −63.347 | −38.562 | −20.317 | 1.00 | 20.95 | N |
| ATOM | 10884 | CE1 | HIS | B | 191 | −62.145 | −38.659 | −19.771 | 1.00 | 21.15 | C |
| ATOM | 10886 | NE2 | HIS | B | 191 | −61.245 | −38.689 | −20.741 | 1.00 | 19.36 | N |
| ATOM | 10888 | CD2 | HIS | B | 191 | −61.893 | −38.604 | −21.948 | 1.00 | 19.49 | C |
| ATOM | 10890 | C | HIS | B | 191 | −64.094 | −35.913 | −22.841 | 1.00 | 18.62 | C |
| ATOM | 10891 | O | HIS | B | 191 | −63.150 | −35.677 | −22.085 | 1.00 | 18.59 | O |
| ATOM | 10893 | N | ARG | B | 192 | −64.307 | −35.216 | −23.957 | 1.00 | 17.72 | N |
| ATOM | 10894 | CA | ARG | B | 192 | −63.394 | −34.150 | −24.394 | 1.00 | 17.57 | C |
| ATOM | 10896 | CB | ARG | B | 192 | −62.838 | −34.504 | −25.773 | 1.00 | 17.81 | C |
| ATOM | 10899 | CG | ARG | B | 192 | −61.971 | −35.736 | −25.781 | 1.00 | 18.59 | C |
| ATOM | 10902 | CD | ARG | B | 192 | −61.484 | −36.067 | −27.181 | 1.00 | 20.10 | C |
| ATOM | 10905 | NE | ARG | B | 192 | −60.462 | −37.116 | −27.165 | 1.00 | 21.62 | N |
| ATOM | 10907 | CZ | ARG | B | 192 | −59.919 | −37.648 | −28.254 | 1.00 | 22.77 | C |
| ATOM | 10908 | NH1 | ARG | B | 192 | −60.304 | −37.248 | −29.454 | 1.00 | 24.20 | N |
| ATOM | 10911 | NH2 | ARG | B | 192 | −58.987 | −38.581 | −28.149 | 1.00 | 23.37 | N |
| ATOM | 10914 | C | ARG | B | 192 | −63.983 | −32.726 | −24.440 | 1.00 | 17.01 | C |
| ATOM | 10915 | O | ARG | B | 192 | −63.242 | −31.739 | −24.526 | 1.00 | 15.78 | O |
| ATOM | 10917 | N | ARG | B | 193 | −65.309 | −32.634 | −24.392 | 1.00 | 17.01 | N |
| ATOM | 10918 | CA | ARG | B | 193 | −66.015 | −31.350 | −24.453 | 1.00 | 16.99 | C |
| ATOM | 10920 | CB | ARG | B | 193 | −67.476 | −31.582 | −24.892 | 1.00 | 17.29 | C |
| ATOM | 10923 | CG | ARG | B | 193 | −68.192 | −30.318 | −25.377 | 1.00 | 18.42 | C |
| ATOM | 10926 | CD | ARG | B | 193 | −69.664 | −30.559 | −25.646 | 1.00 | 19.63 | C |
| ATOM | 10929 | NE | ARG | B | 193 | −69.912 | −31.592 | −26.648 | 1.00 | 21.16 | N |
| ATOM | 10931 | CZ | ARG | B | 193 | −69.868 | −31.398 | −27.971 | 1.00 | 23.56 | C |
| ATOM | 10932 | NH1 | ARG | B | 193 | −69.575 | −30.210 | −28.496 | 1.00 | 23.37 | N |
| ATOM | 10935 | NH2 | ARG | B | 193 | −70.112 | −32.413 | −28.789 | 1.00 | 25.37 | N |
| ATOM | 10938 | C | ARG | B | 193 | −65.974 | −30.658 | −23.087 | 1.00 | 16.46 | C |
| ATOM | 10939 | O | ARG | B | 193 | −66.040 | −31.323 | −22.034 | 1.00 | 16.47 | O |
| ATOM | 10941 | N | THR | B | 194 | −65.864 | −29.335 | −23.078 | 1.00 | 15.84 | N |
| ATOM | 10942 | CA | THR | B | 194 | −65.886 | −28.629 | −21.799 | 1.00 | 15.67 | C |
| ATOM | 10944 | CB | THR | B | 194 | −65.354 | −27.199 | −21.884 | 1.00 | 15.48 | C |
| ATOM | 10946 | OG1 | THR | B | 194 | −66.077 | −26.478 | −22.882 | 1.00 | 15.55 | O |
| ATOM | 10948 | CG2 | THR | B | 194 | −63.877 | −27.189 | −22.211 | 1.00 | 14.65 | C |
| ATOM | 10952 | C | THR | B | 194 | −67.310 | −28.613 | −21.270 | 1.00 | 15.79 | C |
| ATOM | 10953 | O | THR | B | 194 | −68.264 | −28.652 | −22.030 | 1.00 | 15.73 | O |
| ATOM | 10955 | N | GLN | B | 195 | −67.444 | −28.557 | −19.957 | 1.00 | 16.20 | N |
| ATOM | 10956 | CA | GLN | B | 195 | −68.737 | −28.711 | −19.328 | 1.00 | 16.84 | C |
| ATOM | 10958 | CB | GLN | B | 195 | −68.601 | −28.781 | −17.816 | 1.00 | 17.07 | C |
| ATOM | 10961 | CG | GLN | B | 195 | −69.921 | −28.440 | −17.153 | 1.00 | 18.86 | C |
| ATOM | 10964 | CD | GLN | B | 195 | −69.999 | −28.875 | −15.746 | 1.00 | 20.95 | C |
| ATOM | 10965 | OE1 | GLN | B | 195 | −69.099 | −29.511 | −15.245 | 1.00 | 24.63 | O |
| ATOM | 10966 | NE2 | GLN | B | 195 | −71.071 | −28.529 | −15.082 | 1.00 | 22.36 | N |
| ATOM | 10969 | C | GLN | B | 195 | −69.757 | −27.623 | −19.669 | 1.00 | 16.93 | C |
| ATOM | 10970 | O | GLN | B | 195 | −70.858 | −27.931 | −20.136 | 1.00 | 16.98 | O |
| ATOM | 10972 | N | ARG | B | 196 | −69.430 | −26.366 | −19.386 | 1.00 | 16.92 | N |
| ATOM | 10973 | CA | ARG | B | 196 | −70.358 | −25.301 | −19.685 | 1.00 | 17.06 | C |
| ATOM | 10975 | CB | ARG | B | 196 | −69.719 | −23.932 | −19.459 | 1.00 | 17.00 | C |

TABLE 3-7-continued

Coordinates of *P. tremuloides* IspS

| ATOM | 10978 | CG | ARG | B | 196 | −70.095 | −23.289 | −18.120 | 1.00 | 17.09 | C |
|---|---|---|---|---|---|---|---|---|---|---|---|
| ATOM | 10981 | CD | ARG | B | 196 | −70.283 | −24.320 | −16.995 | 1.00 | 17.56 | C |
| ATOM | 10984 | NE | ARG | B | 196 | −71.452 | −24.043 | −16.146 | 1.00 | 17.64 | N |
| ATOM | 10986 | CZ | ARG | B | 196 | −72.289 | −24.965 | −15.664 | 1.00 | 17.93 | C |
| ATOM | 10987 | NH1 | ARG | B | 196 | −72.136 | −26.244 | −15.966 | 1.00 | 17.72 | N |
| ATOM | 10990 | NH2 | ARG | B | 196 | −73.305 | −24.611 | −14.878 | 1.00 | 18.27 | N |
| ATOM | 10993 | C | ARG | B | 196 | −70.881 | −25.481 | −21.098 | 1.00 | 17.42 | C |
| ATOM | 10994 | O | ARG | B | 196 | −72.079 | −25.519 | −21.317 | 1.00 | 17.66 | O |
| ATOM | 10996 | N | LEU | B | 197 | −69.984 | −25.676 | −22.044 | 1.00 | 18.04 | N |
| ATOM | 10997 | CA | LEU | B | 197 | −70.379 | −25.925 | −23.425 | 1.00 | 18.51 | C |
| ATOM | 10999 | CB | LEU | B | 197 | −69.133 | −26.085 | −24.289 | 1.00 | 18.52 | C |
| ATOM | 11002 | CG | LEU | B | 197 | −68.998 | −25.185 | −25.508 | 1.00 | 18.06 | C |
| ATOM | 11004 | CD1 | LEU | B | 197 | −68.209 | −23.932 | −25.205 | 1.00 | 15.52 | C |
| ATOM | 11008 | CD2 | LEU | B | 197 | −68.293 | −26.002 | −26.574 | 1.00 | 20.21 | C |
| ATOM | 11012 | C | LEU | B | 197 | −71.290 | −27.163 | −23.580 | 1.00 | 19.14 | C |
| ATOM | 11013 | O | LEU | B | 197 | −72.226 | −27.150 | −24.372 | 1.00 | 19.52 | O |
| ATOM | 11015 | N | GLU | B | 198 | −71.030 | −28.235 | −22.842 | 1.00 | 19.72 | N |
| ATOM | 11016 | CA | GLU | B | 198 | −71.918 | −29.396 | −22.909 | 1.00 | 20.43 | C |
| ATOM | 11018 | CB | GLU | B | 198 | −71.272 | −30.631 | −22.270 | 1.00 | 20.65 | C |
| ATOM | 11021 | CG | GLU | B | 198 | −72.176 | −31.880 | −22.172 | 1.00 | 22.51 | C |
| ATOM | 11024 | CD | GLU | B | 198 | −72.635 | −32.460 | −23.522 | 1.00 | 25.57 | C |
| ATOM | 11025 | OE1 | GLU | B | 198 | −72.315 | −31.896 | −24.581 | 1.00 | 28.90 | O |
| ATOM | 11026 | OE2 | GLU | B | 198 | −73.326 | −33.506 | −23.540 | 1.00 | 28.09 | O |
| ATOM | 11027 | C | GLU | B | 198 | −73.271 | −29.101 | −22.259 | 1.00 | 20.72 | C |
| ATOM | 11028 | O | GLU | B | 198 | −74.281 | −29.693 | −22.644 | 1.00 | 20.82 | O |
| ATOM | 11030 | N | ALA | B | 199 | −73.282 | −28.199 | −21.270 | 1.00 | 20.86 | N |
| ATOM | 11031 | CA | ALA | B | 199 | −74.508 | −27.814 | −20.565 | 1.00 | 20.66 | C |
| ATOM | 11033 | CB | ALA | B | 199 | −74.176 | −27.013 | −19.326 | 1.00 | 20.36 | C |
| ATOM | 11037 | C | ALA | B | 199 | −75.472 | −27.033 | −21.461 | 1.00 | 20.84 | C |
| ATOM | 11038 | O | ALA | B | 199 | −76.644 | −27.404 | −21.590 | 1.00 | 20.84 | O |
| ATOM | 11040 | N | VAL | B | 200 | −75.002 | −25.961 | −22.092 | 1.00 | 21.12 | N |
| ATOM | 11041 | CA | VAL | B | 200 | −75.903 | −25.177 | −22.942 | 1.00 | 21.60 | C |
| ATOM | 11043 | CB | VAL | B | 200 | −75.215 | −24.042 | −23.701 | 1.00 | 21.30 | C |
| ATOM | 11045 | CG1 | VAL | B | 200 | −74.660 | −23.055 | −22.738 | 1.00 | 21.26 | C |
| ATOM | 11049 | CG2 | VAL | B | 200 | −74.135 | −24.575 | −24.626 | 1.00 | 21.28 | C |
| ATOM | 11053 | C | VAL | B | 200 | −76.603 | −26.077 | −23.944 | 1.00 | 22.32 | C |
| ATOM | 11054 | O | VAL | B | 200 | −77.791 | −25.908 | −24.218 | 1.00 | 22.32 | O |
| ATOM | 11056 | N | TRP | B | 201 | −75.872 | −27.047 | −24.472 | 1.00 | 23.16 | N |
| ATOM | 11057 | CA | TRP | B | 201 | −76.441 | −27.946 | −25.454 | 1.00 | 24.02 | C |
| ATOM | 11059 | CB | TRP | B | 201 | −75.348 | −28.718 | −26.195 | 1.00 | 24.36 | C |
| ATOM | 11062 | CG | TRP | B | 201 | −75.898 | −29.510 | −27.331 | 1.00 | 24.84 | C |
| ATOM | 11063 | CD1 | TRP | B | 201 | −76.060 | −29.092 | −28.613 | 1.00 | 25.41 | C |
| ATOM | 11065 | NE1 | TRP | B | 201 | −76.599 | −30.094 | −29.374 | 1.00 | 25.61 | N |
| ATOM | 11067 | CE2 | TRP | B | 201 | −76.807 | −31.184 | −28.579 | 1.00 | 25.34 | C |
| ATOM | 11068 | CD2 | TRP | B | 201 | −76.374 | −30.847 | −27.279 | 1.00 | 25.56 | C |
| ATOM | 11069 | CE3 | TRP | B | 201 | −76.466 | −31.800 | −26.264 | 1.00 | 27.13 | C |
| ATOM | 11071 | CZ3 | TRP | B | 201 | −76.989 | −33.046 | −26.574 | 1.00 | 28.66 | C |
| ATOM | 11073 | CH2 | TRP | B | 201 | −77.419 | −33.347 | −27.885 | 1.00 | 28.01 | C |
| ATOM | 11075 | CZ2 | TRP | B | 201 | −77.332 | −32.425 | −28.894 | 1.00 | 26.09 | C |
| ATOM | 11077 | C | TRP | B | 201 | −77.411 | −28.938 | −24.833 | 1.00 | 24.22 | C |
| ATOM | 11078 | O | TRP | B | 201 | −78.473 | −29.172 | −25.383 | 1.00 | 24.83 | O |
| ATOM | 11080 | N | SER | B | 202 | −77.034 | −29.541 | −23.715 | 1.00 | 24.39 | N |
| ATOM | 11081 | CA | SER | B | 202 | −77.818 | −30.626 | −23.144 | 1.00 | 24.50 | C |
| ATOM | 11083 | CB | SER | B | 202 | −76.968 | −31.455 | −22.184 | 1.00 | 24.42 | C |
| ATOM | 11086 | OG | SER | B | 202 | −75.848 | −32.021 | −22.848 | 1.00 | 23.80 | O |
| ATOM | 11088 | C | SER | B | 202 | −79.067 | −30.099 | −22.441 | 1.00 | 24.98 | C |
| ATOM | 11089 | O | SER | B | 202 | −80.057 | −30.816 | −22.324 | 1.00 | 24.73 | O |
| ATOM | 11091 | N | ILE | B | 203 | −79.032 | −28.849 | −21.982 | 1.00 | 25.60 | N |
| ATOM | 11092 | CA | ILE | B | 203 | −80.219 | −28.255 | −21.372 | 1.00 | 25.98 | C |
| ATOM | 11094 | CB | ILE | B | 203 | −79.908 | −26.967 | −20.591 | 1.00 | 25.85 | C |
| ATOM | 11096 | CG1 | ILE | B | 203 | −79.086 | −27.326 | −19.348 | 1.00 | 25.76 | C |
| ATOM | 11099 | CD1 | ILE | B | 203 | −78.779 | −26.159 | −18.431 | 1.00 | 26.28 | C |
| ATOM | 11103 | CG2 | ILE | B | 203 | −81.212 | −26.253 | −20.206 | 1.00 | 24.51 | C |
| ATOM | 11107 | C | ILE | B | 203 | −81.280 | −28.016 | −22.443 | 1.00 | 26.67 | C |
| ATOM | 11108 | O | ILE | B | 203 | −82.428 | −28.398 | −22.260 | 1.00 | 26.96 | O |
| ATOM | 11110 | N | GLU | B | 204 | −80.879 | −27.412 | −23.563 | 1.00 | 27.30 | N |
| ATOM | 11111 | CA | GLU | B | 204 | −81.758 | −27.205 | −24.720 | 1.00 | 27.49 | C |
| ATOM | 11113 | CB | GLU | B | 204 | −81.036 | −26.384 | −25.804 | 1.00 | 27.67 | C |
| ATOM | 11116 | CG | GLU | B | 204 | −81.849 | −26.077 | −27.073 | 1.00 | 28.50 | C |
| ATOM | 11119 | CD | GLU | B | 204 | −82.987 | −25.072 | −26.855 | 1.00 | 29.81 | C |
| ATOM | 11120 | OE1 | GLU | B | 204 | −83.158 | −24.600 | −25.711 | 1.00 | 31.40 | O |
| ATOM | 11121 | OE2 | GLU | B | 204 | −83.710 | −24.750 | −27.832 | 1.00 | 29.57 | O |
| ATOM | 11122 | C | GLU | B | 204 | −82.201 | −28.542 | −25.287 | 1.00 | 27.52 | C |
| ATOM | 11123 | O | GLU | B | 204 | −83.321 | −28.667 | −25.738 | 1.00 | 27.67 | O |
| ATOM | 11125 | N | ALA | B | 205 | −81.326 | −29.539 | −25.266 | 1.00 | 27.74 | N |
| ATOM | 11126 | CA | ALA | B | 205 | −81.684 | −30.872 | −25.728 | 1.00 | 28.09 | C |
| ATOM | 11128 | CB | ALA | B | 205 | −80.472 | −31.789 | −25.726 | 1.00 | 27.75 | C |
| ATOM | 11132 | C | ALA | B | 205 | −82.771 | −31.448 | −24.839 | 1.00 | 28.81 | C |

TABLE 3-7-continued

Coordinates of *P. tremuloides* IspS

| ATOM | 11133 | O | ALA | B | 205 | −83.811 | −31.877 | −25.325 | 1.00 | 28.90 | O |
|---|---|---|---|---|---|---|---|---|---|---|---|
| ATOM | 11135 | N | TYR | B | 206 | −82.517 | −31.433 | −23.531 | 1.00 | 29.72 | N |
| ATOM | 11136 | CA | TYR | B | 206 | −83.408 | −32.020 | −22.527 | 1.00 | 30.30 | C |
| ATOM | 11138 | CB | TYR | B | 206 | −82.760 | −31.915 | −21.149 | 1.00 | 30.24 | C |
| ATOM | 11141 | CG | TYR | B | 206 | −83.276 | −32.889 | −20.127 | 1.00 | 29.79 | C |
| ATOM | 11142 | CD1 | TYR | B | 206 | −83.055 | −34.245 | −20.286 | 1.00 | 30.71 | C |
| ATOM | 11144 | CE1 | TYR | B | 206 | −83.498 | −35.161 | −19.360 | 1.00 | 30.78 | C |
| ATOM | 11146 | CZ | TYR | B | 206 | −84.159 | −34.731 | −18.238 | 1.00 | 30.03 | C |
| ATOM | 11147 | OH | TYR | B | 206 | −84.582 | −35.684 | −17.343 | 1.00 | 30.51 | O |
| ATOM | 11149 | CE2 | TYR | B | 206 | −84.394 | −33.379 | −18.042 | 1.00 | 29.42 | C |
| ATOM | 11151 | CD2 | TYR | B | 206 | −83.945 | −32.463 | −18.989 | 1.00 | 29.05 | C |
| ATOM | 11153 | C | TYR | B | 206 | −84.744 | −31.308 | −22.467 | 1.00 | 31.19 | C |
| ATOM | 11154 | O | TYR | B | 206 | −85.790 | −31.930 | −22.311 | 1.00 | 31.44 | O |
| ATOM | 11156 | N | ARG | B | 207 | −84.683 | −29.988 | −22.558 | 1.00 | 32.21 | N |
| ATOM | 11157 | CA | ARG | B | 207 | −85.853 | −29.128 | −22.521 | 1.00 | 33.04 | C |
| ATOM | 11159 | CB | ARG | B | 207 | −85.394 | −27.700 | −22.843 | 1.00 | 32.86 | C |
| ATOM | 11162 | CG | ARG | B | 207 | −86.441 | −26.637 | −22.846 | 1.00 | 32.82 | C |
| ATOM | 11165 | CD | ARG | B | 207 | −85.905 | −25.360 | −23.462 | 1.00 | 32.76 | C |
| ATOM | 11168 | NE | ARG | B | 207 | −85.148 | −24.561 | −22.504 | 1.00 | 32.80 | N |
| ATOM | 11170 | CZ | ARG | B | 207 | −85.676 | −23.709 | −21.628 | 1.00 | 33.40 | C |
| ATOM | 11171 | NH1 | ARG | B | 207 | −86.989 | −23.526 | −21.555 | 1.00 | 34.29 | N |
| ATOM | 11174 | NH2 | ARG | B | 207 | −84.884 | −23.030 | −20.808 | 1.00 | 33.89 | N |
| ATOM | 11177 | C | ARG | B | 207 | −86.971 | −29.606 | −23.478 | 1.00 | 34.14 | C |
| ATOM | 11178 | O | ARG | B | 207 | −88.144 | −29.521 | −23.128 | 1.00 | 34.34 | O |
| ATOM | 11180 | N | LYS | B | 208 | −86.607 | −30.137 | −24.652 | 1.00 | 35.32 | N |
| ATOM | 11181 | CA | LYS | B | 208 | −87.581 | −30.535 | −25.688 | 1.00 | 36.16 | C |
| ATOM | 11183 | CB | LYS | B | 208 | −86.960 | −30.468 | −27.090 | 1.00 | 36.01 | C |
| ATOM | 11186 | CG | LYS | B | 208 | −86.126 | −29.234 | −27.368 | 1.00 | 35.85 | C |
| ATOM | 11189 | CD | LYS | B | 208 | −85.934 | −29.023 | −28.861 | 1.00 | 35.98 | C |
| ATOM | 11192 | CE | LYS | B | 208 | −84.774 | −28.086 | −29.186 | 1.00 | 35.63 | C |
| ATOM | 11195 | NZ | LYS | B | 208 | −83.566 | −28.843 | −29.596 | 1.00 | 35.17 | N |
| ATOM | 11199 | C | LYS | B | 208 | −88.166 | −31.937 | −25.490 | 1.00 | 37.25 | C |
| ATOM | 11200 | O | LYS | B | 208 | −89.212 | −32.250 | −26.054 | 1.00 | 37.50 | O |
| ATOM | 11202 | N | LYS | B | 209 | −87.484 | −32.788 | −24.730 | 1.00 | 38.58 | N |
| ATOM | 11203 | CA | LYS | B | 209 | −88.026 | −34.106 | −24.383 | 1.00 | 39.89 | C |
| ATOM | 11205 | CB | LYS | B | 209 | −87.013 | −34.923 | −23.578 | 1.00 | 40.23 | C |
| ATOM | 11208 | CG | LYS | B | 209 | −85.914 | −35.604 | −24.373 | 1.00 | 41.47 | C |
| ATOM | 11211 | CD | LYS | B | 209 | −84.858 | −36.178 | −23.417 | 1.00 | 43.71 | C |
| ATOM | 11214 | CE | LYS | B | 209 | −84.448 | −37.612 | −23.764 | 1.00 | 45.15 | C |
| ATOM | 11217 | NZ | LYS | B | 209 | −85.390 | −38.621 | −23.163 | 1.00 | 45.73 | N |
| ATOM | 11221 | C | LYS | B | 209 | −89.288 | −33.950 | −23.530 | 1.00 | 40.51 | C |
| ATOM | 11222 | O | LYS | B | 209 | −89.230 | −33.367 | −22.441 | 1.00 | 40.84 | O |
| ATOM | 11224 | N | GLU | B | 210 | −90.418 | −34.477 | −24.000 | 1.00 | 40.92 | N |
| ATOM | 11225 | CA | GLU | B | 210 | −91.652 | −34.386 | −23.223 | 1.00 | 41.27 | C |
| ATOM | 11227 | CB | GLU | B | 210 | −92.855 | −34.935 | −23.998 | 1.00 | 41.77 | C |
| ATOM | 11230 | CG | GLU | B | 210 | −92.822 | −36.446 | −24.265 | 1.00 | 43.47 | C |
| ATOM | 11233 | CD | GLU | B | 210 | −94.049 | −36.922 | −25.032 | 1.00 | 45.23 | C |
| ATOM | 11234 | OE1 | GLU | B | 210 | −95.188 | −36.590 | −24.612 | 1.00 | 45.02 | O |
| ATOM | 11235 | OE2 | GLU | B | 210 | −93.863 | −37.629 | −26.053 | 1.00 | 46.74 | O |
| ATOM | 11236 | C | GLU | B | 210 | −91.494 | −35.121 | −21.895 | 1.00 | 40.71 | C |
| ATOM | 11237 | O | GLU | B | 210 | −91.996 | −34.667 | −20.864 | 1.00 | 40.99 | O |
| ATOM | 11239 | N | ASP | B | 211 | −90.773 | −36.240 | −21.924 | 1.00 | 39.76 | N |
| ATOM | 11240 | CA | ASP | B | 211 | −90.533 | −37.050 | −20.721 | 1.00 | 38.96 | C |
| ATOM | 11242 | CB | ASP | B | 211 | −90.151 | −38.476 | −21.123 | 1.00 | 39.10 | C |
| ATOM | 11245 | CG | ASP | B | 211 | −89.101 | −38.499 | −22.212 | 1.00 | 40.26 | C |
| ATOM | 11246 | OD1 | ASP | B | 211 | −89.327 | −37.827 | −23.254 | 1.00 | 41.25 | O |
| ATOM | 11247 | OD2 | ASP | B | 211 | −88.055 | −39.160 | −22.020 | 1.00 | 41.66 | O |
| ATOM | 11248 | C | ASP | B | 211 | −89.440 | −36.468 | −19.826 | 1.00 | 37.75 | C |
| ATOM | 11249 | O | ASP | B | 211 | −89.009 | −37.131 | −18.892 | 1.00 | 37.62 | O |
| ATOM | 11251 | N | ALA | B | 212 | −88.989 | −35.245 | −20.115 | 1.00 | 36.47 | N |
| ATOM | 11252 | CA | ALA | B | 212 | −87.941 | −34.587 | −19.335 | 1.00 | 35.36 | C |
| ATOM | 11254 | CB | ALA | B | 212 | −87.516 | −33.294 | −20.011 | 1.00 | 35.23 | C |
| ATOM | 11258 | C | ALA | B | 212 | −88.423 | −34.307 | −17.920 | 1.00 | 34.40 | C |
| ATOM | 11259 | O | ALA | B | 212 | −89.559 | −33.870 | −17.728 | 1.00 | 34.42 | O |
| ATOM | 11261 | N | ASN | B | 213 | −87.565 | −34.574 | −16.937 | 1.00 | 33.24 | N |
| ATOM | 11262 | CA | ASN | B | 213 | −87.890 | −34.333 | −15.533 | 1.00 | 32.67 | C |
| ATOM | 11264 | CB | ASN | B | 213 | −86.840 | −34.986 | −14.623 | 1.00 | 32.58 | C |
| ATOM | 11267 | CG | ASN | B | 213 | −87.204 | −34.912 | −13.152 | 1.00 | 32.67 | C |
| ATOM | 11268 | OD1 | ASN | B | 213 | −87.891 | −33.994 | −12.722 | 1.00 | 32.62 | O |
| ATOM | 11269 | ND2 | ASN | B | 213 | −86.734 | −35.882 | −12.371 | 1.00 | 33.18 | N |
| ATOM | 11272 | C | ASN | B | 213 | −87.990 | −32.825 | −15.266 | 1.00 | 32.19 | C |
| ATOM | 11273 | O | ASN | B | 213 | −87.010 | −32.092 | −15.376 | 1.00 | 32.38 | O |
| ATOM | 11275 | N | GLN | B | 214 | −89.182 | −32.356 | −14.923 | 1.00 | 31.48 | N |
| ATOM | 11276 | CA | GLN | B | 214 | −89.389 | −30.924 | −14.756 | 1.00 | 30.85 | C |
| ATOM | 11278 | CB | GLN | B | 214 | −90.889 | −30.581 | −14.693 | 1.00 | 30.82 | C |
| ATOM | 11281 | CG | GLN | B | 214 | −91.684 | −30.869 | −16.002 | 1.00 | 30.80 | C |
| ATOM | 11284 | CD | GLN | B | 214 | −90.990 | −30.378 | −17.291 | 1.00 | 29.69 | C |
| ATOM | 11285 | OE1 | GLN | B | 214 | −90.893 | −29.174 | −17.543 | 1.00 | 29.07 | O |

TABLE 3-7-continued

| | | | | | Coordinates of *P. tremuloides* IspS | | | | | |
|---|---|---|---|---|---|---|---|---|---|---|
| ATOM | 11286 | NE2 | GLN | B | 214 | −90.526 | −31.321 | −18.113 | 1.00 | 27.71 | N |
| ATOM | 11289 | C | GLN | B | 214 | −88.638 | −30.369 | −13.543 | 1.00 | 30.37 | C |
| ATOM | 11290 | O | GLN | B | 214 | −88.263 | −29.200 | −13.533 | 1.00 | 30.80 | O |
| ATOM | 11292 | N | VAL | B | 215 | −88.393 | −31.200 | −12.532 | 1.00 | 29.54 | N |
| ATOM | 11293 | CA | VAL | B | 215 | −87.566 | −30.779 | −11.395 | 1.00 | 28.56 | C |
| ATOM | 11295 | CB | VAL | B | 215 | −87.564 | −31.818 | −10.260 | 1.00 | 28.64 | C |
| ATOM | 11297 | CG1 | VAL | B | 215 | −86.758 | −31.299 | −9.075 | 1.00 | 27.94 | C |
| ATOM | 11301 | CG2 | VAL | B | 215 | −88.999 | −32.167 | −9.856 | 1.00 | 28.26 | C |
| ATOM | 11305 | C | VAL | B | 215 | −86.124 | −30.545 | −11.845 | 1.00 | 27.63 | C |
| ATOM | 11306 | O | VAL | B | 215 | −85.566 | −29.472 | −11.615 | 1.00 | 27.58 | O |
| ATOM | 11308 | N | LEU | B | 216 | −85.546 | −31.548 | −12.504 | 1.00 | 26.37 | N |
| ATOM | 11309 | CA | LEU | B | 216 | −84.143 | −31.509 | −12.930 | 1.00 | 25.47 | C |
| ATOM | 11311 | CB | LEU | B | 216 | −83.714 | −32.866 | −13.490 | 1.00 | 25.46 | C |
| ATOM | 11314 | CG | LEU | B | 216 | −82.274 | −32.995 | −13.979 | 1.00 | 24.97 | C |
| ATOM | 11316 | CD1 | LEU | B | 216 | −81.289 | −32.640 | −12.883 | 1.00 | 24.62 | C |
| ATOM | 11320 | CD2 | LEU | B | 216 | −82.042 | −34.407 | −14.472 | 1.00 | 24.55 | C |
| ATOM | 11324 | C | LEU | B | 216 | −83.861 | −30.447 | −13.972 | 1.00 | 24.68 | C |
| ATOM | 11325 | O | LEU | B | 216 | −82.819 | −29.820 | −13.929 | 1.00 | 24.91 | O |
| ATOM | 11327 | N | LEU | B | 217 | −84.776 | −30.269 | −14.916 | 1.00 | 23.79 | N |
| ATOM | 11328 | CA | LEU | B | 217 | −84.625 | −29.260 | −15.960 | 1.00 | 23.13 | C |
| ATOM | 11330 | CB | LEU | B | 217 | −85.765 | −29.384 | −16.972 | 1.00 | 23.36 | C |
| ATOM | 11333 | CG | LEU | B | 217 | −85.808 | −28.374 | −18.123 | 1.00 | 23.18 | C |
| ATOM | 11335 | CD1 | LEU | B | 217 | −84.462 | −28.268 | −18.796 | 1.00 | 22.69 | C |
| ATOM | 11339 | CD2 | LEU | B | 217 | −86.861 | −28.786 | −19.126 | 1.00 | 23.38 | C |
| ATOM | 11343 | C | LEU | B | 217 | −84.631 | −27.853 | −15.383 | 1.00 | 22.51 | C |
| ATOM | 11344 | O | LEU | B | 217 | −83.903 | −26.973 | −15.855 | 1.00 | 22.08 | O |
| ATOM | 11346 | N | GLU | B | 218 | −85.481 | −27.647 | −14.375 | 1.00 | 21.84 | N |
| ATOM | 11347 | CA | GLU | B | 218 | −85.619 | −26.339 | −13.725 | 1.00 | 21.26 | C |
| ATOM | 11349 | CB | GLU | B | 218 | −86.813 | −26.341 | −12.768 | 1.00 | 21.27 | C |
| ATOM | 11352 | CG | GLU | B | 218 | −87.206 | −24.956 | −12.246 | 1.00 | 21.35 | C |
| ATOM | 11355 | CD | GLU | B | 218 | −88.501 | −24.964 | −11.441 | 1.00 | 20.89 | C |
| ATOM | 11356 | OE1 | GLU | B | 218 | −89.097 | −26.052 | −11.263 | 1.00 | 20.47 | O |
| ATOM | 11357 | OE2 | GLU | B | 218 | −88.915 | −23.874 | −10.986 | 1.00 | 20.15 | O |
| ATOM | 11358 | C | GLU | B | 218 | −84.348 | −26.001 | −12.969 | 1.00 | 20.58 | C |
| ATOM | 11359 | O | GLU | B | 218 | −83.877 | −24.865 | −12.982 | 1.00 | 20.31 | O |
| ATOM | 11361 | N | LEU | B | 219 | −83.802 | −27.015 | −12.312 | 1.00 | 19.87 | N |
| ATOM | 11362 | CA | LEU | B | 219 | −82.559 | −26.885 | −11.592 | 1.00 | 19.12 | C |
| ATOM | 11364 | CB | LEU | B | 219 | −82.310 | −28.132 | −10.746 | 1.00 | 18.58 | C |
| ATOM | 11367 | CG | LEU | B | 219 | −81.159 | −28.054 | −9.762 | 1.00 | 17.07 | C |
| ATOM | 11369 | CD1 | LEU | B | 219 | −81.321 | −26.847 | −8.872 | 1.00 | 16.10 | C |
| ATOM | 11373 | CD2 | LEU | B | 219 | −81.107 | −29.311 | −8.954 | 1.00 | 15.22 | C |
| ATOM | 11377 | C | LEU | B | 219 | −81.443 | −26.675 | −12.599 | 1.00 | 19.16 | C |
| ATOM | 11378 | O | LEU | B | 219 | −80.684 | −25.721 | −12.478 | 1.00 | 19.42 | O |
| ATOM | 11380 | N | ALA | B | 220 | −81.368 | −27.546 | −13.606 | 1.00 | 19.04 | N |
| ATOM | 11381 | CA | ALA | B | 220 | −80.356 | −27.431 | −14.669 | 1.00 | 19.04 | C |
| ATOM | 11383 | CB | ALA | B | 220 | −80.648 | −28.398 | −15.817 | 1.00 | 18.64 | C |
| ATOM | 11387 | C | ALA | B | 220 | −80.257 | −26.004 | −15.196 | 1.00 | 19.06 | C |
| ATOM | 11388 | O | ALA | B | 220 | −79.159 | −25.472 | −15.321 | 1.00 | 19.08 | O |
| ATOM | 11390 | N | ILE | B | 221 | −81.410 | −25.393 | −15.475 | 1.00 | 19.19 | N |
| ATOM | 11391 | CA | ILE | B | 221 | −81.473 | −24.016 | −15.963 | 1.00 | 19.22 | C |
| ATOM | 11393 | CB | ILE | B | 221 | −82.898 | −23.638 | −16.423 | 1.00 | 19.03 | C |
| ATOM | 11395 | CG1 | ILE | B | 221 | −83.229 | −24.323 | −17.755 | 1.00 | 18.52 | C |
| ATOM | 11398 | CD1 | ILE | B | 221 | −84.687 | −24.645 | −17.928 | 1.00 | 17.52 | C |
| ATOM | 11402 | CG2 | ILE | B | 221 | −83.024 | −22.121 | −16.564 | 1.00 | 18.03 | C |
| ATOM | 11406 | C | ILE | B | 221 | −81.030 | −23.013 | −14.906 | 1.00 | 19.62 | C |
| ATOM | 11407 | O | ILE | B | 221 | −80.137 | −22.190 | −15.136 | 1.00 | 19.53 | O |
| ATOM | 11409 | N | LEU | B | 222 | −81.666 | −23.096 | −13.745 | 1.00 | 20.27 | N |
| ATOM | 11410 | CA | LEU | B | 222 | −81.412 | −22.161 | −12.654 | 1.00 | 20.63 | C |
| ATOM | 11412 | CB | LEU | B | 222 | −82.203 | −22.561 | −11.412 | 1.00 | 20.50 | C |
| ATOM | 11415 | CG | LEU | B | 222 | −82.195 | −21.523 | −10.296 | 1.00 | 20.76 | C |
| ATOM | 11417 | CD1 | LEU | B | 222 | −83.439 | −21.675 | −9.431 | 1.00 | 21.02 | C |
| ATOM | 11421 | CD2 | LEU | B | 222 | −80.924 | −21.625 | −9.453 | 1.00 | 20.21 | C |
| ATOM | 11425 | C | LEU | B | 222 | −79.925 | −22.089 | −12.341 | 1.00 | 20.98 | C |
| ATOM | 11426 | O | LEU | B | 222 | −79.337 | −21.011 | −12.381 | 1.00 | 21.40 | O |
| ATOM | 11428 | N | ASP | B | 223 | −79.319 | −23.240 | −12.064 | 1.00 | 21.24 | N |
| ATOM | 11429 | CA | ASP | B | 223 | −77.907 | −23.298 | −11.709 | 1.00 | 21.48 | C |
| ATOM | 11431 | CB | ASP | B | 223 | −77.509 | −24.724 | −11.314 | 1.00 | 21.66 | C |
| ATOM | 11434 | CG | ASP | B | 223 | −76.168 | −24.792 | −10.589 | 1.00 | 22.70 | C |
| ATOM | 11435 | OD1 | ASP | B | 223 | −75.095 | −24.775 | −11.244 | 1.00 | 24.25 | O |
| ATOM | 11436 | OD2 | ASP | B | 223 | −76.190 | −24.893 | −9.349 | 1.00 | 24.85 | O |
| ATOM | 11437 | C | ASP | B | 223 | −77.017 | −22.768 | −12.835 | 1.00 | 21.64 | C |
| ATOM | 11438 | O | ASP | B | 223 | −76.035 | −22.104 | −12.548 | 1.00 | 21.66 | O |
| ATOM | 11440 | N | TYR | B | 224 | −77.361 | −23.023 | −14.100 | 1.00 | 22.07 | N |
| ATOM | 11441 | CA | TYR | B | 224 | −76.517 | −22.561 | −15.218 | 1.00 | 22.47 | C |
| ATOM | 11443 | CB | TYR | B | 224 | −76.980 | −23.111 | −16.589 | 1.00 | 22.35 | C |
| ATOM | 11446 | CG | TYR | B | 224 | −76.032 | −22.733 | −17.724 | 1.00 | 22.25 | C |
| ATOM | 11447 | CD1 | TYR | B | 224 | −75.002 | −23.576 | −18.116 | 1.00 | 21.46 | C |
| ATOM | 11449 | CE1 | TYR | B | 224 | −74.126 | −23.216 | −19.135 | 1.00 | 21.43 | C |

TABLE 3-7-continued

| | | | | | | | | | | |
|---|---|---|---|---|---|---|---|---|---|---|
| ATOM | 11451 | CZ | TYR | B | 224 | −74.260 | −21.991 | −19.761 | 1.00 | 21.62 C |
| ATOM | 11452 | OH | TYR | B | 224 | −73.387 | −21.618 | −20.760 | 1.00 | 20.46 O |
| ATOM | 11454 | CE2 | TYR | B | 224 | −75.270 | −21.132 | −19.387 | 1.00 | 22.04 C |
| ATOM | 11456 | CD2 | TYR | B | 224 | −76.144 | −21.500 | −18.373 | 1.00 | 22.73 C |
| ATOM | 11458 | C | TYR | B | 224 | −76.414 | −21.023 | −15.262 | 1.00 | 23.06 C |
| ATOM | 11459 | O | TYR | B | 224 | −75.323 | −20.467 | −15.507 | 1.00 | 22.89 O |
| ATOM | 11461 | N | ASN | B | 225 | −77.543 | −20.350 | −15.027 | 1.00 | 23.66 N |
| ATOM | 11462 | CA | ASN | B | 225 | −77.593 | −18.884 | −15.072 | 1.00 | 24.16 C |
| ATOM | 11464 | CB | ASN | B | 225 | −79.040 | −18.367 | −15.107 | 1.00 | 24.12 C |
| ATOM | 11467 | CG | ASN | B | 225 | −79.778 | −18.761 | −16.365 | 1.00 | 23.89 C |
| ATOM | 11468 | OD1 | ASN | B | 225 | −79.182 | −18.877 | −17.437 | 1.00 | 24.33 O |
| ATOM | 11469 | ND2 | ASN | B | 225 | −81.088 | −18.965 | −16.244 | 1.00 | 22.05 N |
| ATOM | 11472 | C | ASN | B | 225 | −76.880 | −18.265 | −13.881 | 1.00 | 24.73 C |
| ATOM | 11473 | O | ASN | B | 225 | −76.195 | −17.247 | −14.027 | 1.00 | 25.09 O |
| ATOM | 11475 | N | MET | B | 226 | −77.067 | −18.864 | −12.703 | 1.00 | 25.15 N |
| ATOM | 11476 | CA | MET | B | 226 | −76.423 | −18.390 | −11.479 | 1.00 | 25.53 C |
| ATOM | 11478 | CB | MET | B | 226 | −76.806 | −19.278 | −10.282 | 1.00 | 26.11 C |
| ATOM | 11481 | CG | MET | B | 226 | −75.905 | −19.169 | −9.023 | 1.00 | 27.59 C |
| ATOM | 11484 | SD | MET | B | 226 | −75.676 | −20.788 | −8.214 | 1.00 | 30.67 S |
| ATOM | 11485 | CE | MET | B | 226 | −77.308 | −21.005 | −7.476 | 1.00 | 29.78 C |
| ATOM | 11489 | C | MET | B | 226 | −74.920 | −18.380 | −11.692 | 1.00 | 25.16 C |
| ATOM | 11490 | O | MET | B | 226 | −74.258 | −17.387 | −11.391 | 1.00 | 25.10 O |
| ATOM | 11492 | N | ILE | B | 227 | −74.388 | −19.473 | −12.239 | 1.00 | 24.88 N |
| ATOM | 11493 | CA | ILE | B | 227 | −72.944 | −19.564 | −12.501 | 1.00 | 24.70 C |
| ATOM | 11495 | CB | ILE | B | 227 | −72.476 | −20.994 | −12.882 | 1.00 | 24.45 C |
| ATOM | 11497 | CG1 | ILE | B | 227 | −72.656 | −21.947 | −11.695 | 1.00 | 23.80 C |
| ATOM | 11500 | CD1 | ILE | B | 227 | −72.094 | −23.332 | −11.885 | 1.00 | 21.97 C |
| ATOM | 11504 | CG2 | ILE | B | 227 | −71.030 | −20.969 | −13.266 | 1.00 | 24.90 C |
| ATOM | 11508 | C | ILE | B | 227 | −72.529 | −18.550 | −13.566 | 1.00 | 24.45 C |
| ATOM | 11509 | O | ILE | B | 227 | −71.578 | −17.810 | −13.373 | 1.00 | 24.42 O |
| ATOM | 11511 | N | GLN | B | 228 | −73.264 | −18.484 | −14.668 | 1.00 | 24.31 N |
| ATOM | 11512 | CA | GLN | B | 228 | −73.038 | −17.414 | −15.639 | 1.00 | 24.19 C |
| ATOM | 11514 | CB | GLN | B | 228 | −74.143 | −17.363 | −16.688 | 1.00 | 24.02 C |
| ATOM | 11517 | CG | GLN | B | 228 | −73.788 | −16.488 | −17.864 | 1.00 | 23.42 C |
| ATOM | 11520 | CD | GLN | B | 228 | −74.807 | −16.567 | −18.983 | 1.00 | 23.70 C |
| ATOM | 11521 | OE1 | GLN | B | 228 | −75.790 | −15.813 | −19.015 | 1.00 | 24.07 O |
| ATOM | 11522 | NE2 | GLN | B | 228 | −74.564 | −17.465 | −19.927 | 1.00 | 23.49 N |
| ATOM | 11525 | C | GLN | B | 228 | −72.913 | −16.037 | −14.987 | 1.00 | 24.37 C |
| ATOM | 11526 | O | GLN | B | 228 | −72.145 | −15.210 | −15.470 | 1.00 | 24.45 O |
| ATOM | 11528 | N | SER | B | 229 | −73.653 | −15.776 | −13.909 | 1.00 | 24.45 N |
| ATOM | 11529 | CA | SER | B | 229 | −73.578 | −14.459 | −13.264 | 1.00 | 24.76 C |
| ATOM | 11531 | CB | SER | B | 229 | −74.815 | −14.163 | −12.397 | 1.00 | 24.84 C |
| ATOM | 11534 | OG | SER | B | 229 | −74.711 | −14.718 | −11.096 | 1.00 | 25.81 O |
| ATOM | 11536 | C | SER | B | 229 | −72.270 | −14.279 | −12.469 | 1.00 | 24.64 C |
| ATOM | 11537 | O | SER | B | 229 | −71.726 | −13.172 | −12.408 | 1.00 | 24.95 O |
| ATOM | 11539 | N | VAL | B | 230 | −71.751 | −15.350 | −11.878 | 1.00 | 24.20 N |
| ATOM | 11540 | CA | VAL | B | 230 | −70.415 | −15.277 | −11.299 | 1.00 | 23.99 C |
| ATOM | 11542 | CB | VAL | B | 230 | −70.006 | −16.581 | −10.574 | 1.00 | 23.92 C |
| ATOM | 11544 | CG1 | VAL | B | 230 | −68.546 | −16.510 | −10.105 | 1.00 | 23.71 C |
| ATOM | 11548 | CG2 | VAL | B | 230 | −70.923 | −16.853 | −9.409 | 1.00 | 23.52 C |
| ATOM | 11552 | C | VAL | B | 230 | −69.386 | −14.966 | −12.400 | 1.00 | 24.12 C |
| ATOM | 11553 | O | VAL | B | 230 | −68.397 | −14.291 | −12.136 | 1.00 | 24.01 O |
| ATOM | 11555 | N | TYR | B | 231 | −69.612 | −15.461 | −13.621 | 1.00 | 24.30 N |
| ATOM | 11556 | CA | TYR | B | 231 | −68.672 | −15.235 | −14.728 | 1.00 | 24.53 C |
| ATOM | 11558 | CB | TYR | B | 231 | −68.997 | −16.104 | −15.946 | 1.00 | 24.08 C |
| ATOM | 11561 | CG | TYR | B | 231 | −68.892 | −17.605 | −15.754 | 1.00 | 23.29 C |
| ATOM | 11562 | CD1 | TYR | B | 231 | −68.173 | −18.168 | −14.706 | 1.00 | 23.08 C |
| ATOM | 11564 | CE1 | TYR | B | 231 | −68.073 | −19.547 | −14.565 | 1.00 | 22.01 C |
| ATOM | 11566 | CZ | TYR | B | 231 | −68.685 | −20.369 | −15.479 | 1.00 | 21.16 C |
| ATOM | 11567 | OH | TYR | B | 231 | −68.607 | −21.746 | −15.353 | 1.00 | 20.18 O |
| ATOM | 11569 | CE2 | TYR | B | 231 | −69.387 | −19.825 | −16.523 | 1.00 | 21.64 C |
| ATOM | 11571 | CD2 | TYR | B | 231 | −69.476 | −18.464 | −16.662 | 1.00 | 22.15 C |
| ATOM | 11573 | C | TYR | B | 231 | −68.658 | −13.772 | −15.166 | 1.00 | 25.37 C |
| ATOM | 11574 | O | TYR | B | 231 | −67.602 | −13.221 | −15.528 | 1.00 | 25.25 O |
| ATOM | 11576 | N | GLN | B | 232 | −69.832 | −13.148 | −15.129 | 1.00 | 26.11 N |
| ATOM | 11577 | CA | GLN | B | 232 | −69.978 | −11.797 | −15.622 | 1.00 | 26.68 C |
| ATOM | 11579 | CB | GLN | B | 232 | −71.430 | −11.541 | −15.995 | 1.00 | 26.45 C |
| ATOM | 11582 | CG | GLN | B | 232 | −71.883 | −12.385 | −17.176 | 1.00 | 25.67 C |
| ATOM | 11585 | CD | GLN | B | 232 | −73.388 | −12.394 | −17.381 | 1.00 | 24.91 C |
| ATOM | 11586 | OE1 | GLN | B | 232 | −74.140 | −11.761 | −16.637 | 1.00 | 24.81 O |
| ATOM | 11587 | NE2 | GLN | B | 232 | −73.834 | −13.113 | −18.407 | 1.00 | 23.39 N |
| ATOM | 11590 | C | GLN | B | 232 | −69.445 | −10.802 | −14.593 | 1.00 | 27.90 C |
| ATOM | 11591 | O | GLN | B | 232 | −68.909 | −9.752 | −14.958 | 1.00 | 27.96 O |
| ATOM | 11593 | N | ARG | B | 233 | −69.572 | −11.145 | −13.312 | 1.00 | 29.35 N |
| ATOM | 11594 | CA | ARG | B | 233 | −68.908 | −10.396 | −12.241 | 1.00 | 30.59 C |
| ATOM | 11596 | CB | ARG | B | 233 | −69.490 | −10.775 | −10.867 | 1.00 | 30.99 C |
| ATOM | 11599 | CG | ARG | B | 233 | −68.824 | −10.114 | −9.661 | 1.00 | 32.72 C |
| ATOM | 11602 | CD | ARG | B | 233 | −69.695 | −10.210 | −8.391 | 1.00 | 35.70 C |

TABLE 3-7-continued

| | | | | | | | | | | |
|---|---|---|---|---|---|---|---|---|---|---|
| ATOM | 11605 | NE | ARG | B | 233 | −70.162 | −11.578 | −8.086 | 1.00 | 38.29 N |
| ATOM | 11607 | CZ | ARG | B | 233 | −71.403 | −12.053 | −8.276 | 1.00 | 39.65 C |
| ATOM | 11608 | NH1 | ARG | B | 233 | −72.367 | −11.287 | −8.787 | 1.00 | 40.23 N |
| ATOM | 11611 | NH2 | ARG | B | 233 | −71.687 | −13.320 | −7.949 | 1.00 | 39.61 N |
| ATOM | 11614 | C | ARG | B | 233 | −67.390 | −10.632 | −12.303 | 1.00 | 31.10 C |
| ATOM | 11615 | O | ARG | B | 233 | −66.615 | −9.693 | −12.181 | 1.00 | 31.19 O |
| ATOM | 11617 | N | ASP | B | 234 | −66.954 | −11.868 | −12.517 | 1.00 | 31.91 N |
| ATOM | 11618 | CA | ASP | B | 234 | −65.530 | −12.102 | −12.750 | 1.00 | 32.63 C |
| ATOM | 11620 | CB | ASP | B | 234 | −65.220 | −13.566 | −13.090 | 1.00 | 32.53 C |
| ATOM | 11623 | CG | ASP | B | 234 | −65.336 | −14.493 | −11.894 | 1.00 | 32.90 C |
| ATOM | 11624 | OD1 | ASP | B | 234 | −65.477 | −14.028 | −10.746 | 1.00 | 33.06 O |
| ATOM | 11625 | OD2 | ASP | B | 234 | −65.293 | −15.713 | −12.107 | 1.00 | 34.22 O |
| ATOM | 11626 | C | ASP | B | 234 | −65.058 | −11.206 | −13.886 | 1.00 | 33.10 C |
| ATOM | 11627 | O | ASP | B | 234 | −64.097 | −10.458 | −13.723 | 1.00 | 33.55 O |
| ATOM | 11629 | N | LEU | B | 235 | −65.753 | −11.256 | −15.017 | 1.00 | 33.49 N |
| ATOM | 11630 | CA | LEU | B | 235 | −65.311 | −10.550 | −16.216 | 1.00 | 34.06 C |
| ATOM | 11632 | CB | LEU | B | 235 | −66.139 | −10.996 | −17.422 | 1.00 | 33.80 C |
| ATOM | 11635 | CG | LEU | B | 235 | −65.769 | −10.403 | −18.775 | 1.00 | 32.13 C |
| ATOM | 11637 | CD1 | LEU | B | 235 | −64.303 | −10.679 | −19.050 | 1.00 | 30.94 C |
| ATOM | 11641 | CD2 | LEU | B | 235 | −66.670 | −10.959 | −19.870 | 1.00 | 29.93 C |
| ATOM | 11645 | C | LEU | B | 235 | −65.345 | −9.023 | −16.103 | 1.00 | 35.40 C |
| ATOM | 11646 | O | LEU | B | 235 | −64.500 | −8.352 | −16.682 | 1.00 | 35.61 O |
| ATOM | 11648 | N | ARG | B | 236 | −66.327 | −8.473 | −15.386 | 1.00 | 36.92 N |
| ATOM | 11649 | CA | ARG | B | 236 | −66.380 | −7.019 | −15.137 | 1.00 | 38.06 C |
| ATOM | 11651 | CB | ARG | B | 236 | −67.650 | −6.607 | −14.367 | 1.00 | 38.43 C |
| ATOM | 11654 | CG | ARG | B | 236 | −68.882 | −6.321 | −15.230 | 1.00 | 39.58 C |
| ATOM | 11657 | CD | ARG | B | 236 | −69.958 | −5.520 | −14.459 | 1.00 | 40.93 C |
| ATOM | 11660 | NE | ARG | B | 236 | −70.383 | −6.149 | −13.199 | 1.00 | 41.74 N |
| ATOM | 11662 | CZ | ARG | B | 236 | −71.208 | −7.195 | −13.095 | 1.00 | 42.20 C |
| ATOM | 11663 | NH1 | ARG | B | 236 | −71.719 | −7.784 | −14.175 | 1.00 | 41.61 N |
| ATOM | 11666 | NH2 | ARG | B | 236 | −71.517 | −7.672 | −11.892 | 1.00 | 42.99 N |
| ATOM | 11669 | C | ARG | B | 236 | −65.170 | −6.550 | −14.343 | 1.00 | 38.57 C |
| ATOM | 11670 | O | ARG | B | 236 | −64.593 | −5.524 | −14.665 | 1.00 | 38.61 O |
| ATOM | 11672 | N | GLU | B | 237 | −64.822 | −7.292 | −13.291 | 1.00 | 39.42 N |
| ATOM | 11673 | CA | GLU | B | 237 | −63.625 | −7.017 | −12.480 | 1.00 | 40.18 C |
| ATOM | 11675 | CB | GLU | B | 237 | −63.471 | −8.033 | −11.317 | 1.00 | 40.67 C |
| ATOM | 11678 | CG | GLU | B | 237 | −64.336 | −7.750 | −10.057 | 1.00 | 42.61 C |
| ATOM | 11681 | CD | GLU | B | 237 | −64.258 | −8.858 | −8.961 | 1.00 | 45.07 C |
| ATOM | 11682 | OE1 | GLU | B | 237 | −64.051 | −10.066 | −9.282 | 1.00 | 46.74 O |
| ATOM | 11683 | OE2 | GLU | B | 237 | −64.436 | −8.511 | −7.764 | 1.00 | 45.87 O |
| ATOM | 11684 | C | GLU | B | 237 | −62.352 | −7.024 | −13.344 | 1.00 | 39.93 C |
| ATOM | 11685 | O | GLU | B | 237 | −61.593 | −6.050 | −13.332 | 1.00 | 39.96 O |
| ATOM | 11687 | N | THR | B | 238 | −62.123 | −8.104 | −14.095 | 1.00 | 39.56 N |
| ATOM | 11688 | CA | THR | B | 238 | −60.900 | −8.200 | −14.895 | 1.00 | 39.42 C |
| ATOM | 11690 | CB | THR | B | 238 | −60.492 | −9.666 | −15.268 | 1.00 | 39.39 C |
| ATOM | 11692 | OG1 | THR | B | 238 | −61.222 | −10.123 | −16.413 | 1.00 | 39.37 O |
| ATOM | 11694 | CG2 | THR | B | 238 | −60.683 | −10.612 | −14.095 | 1.00 | 38.73 C |
| ATOM | 11698 | C | THR | B | 238 | −60.961 | −7.326 | −16.156 | 1.00 | 39.48 C |
| ATOM | 11699 | O | THR | B | 238 | −59.930 | −7.062 | −16.761 | 1.00 | 39.48 O |
| ATOM | 11701 | N | SER | B | 239 | −62.149 | −6.871 | −16.549 | 1.00 | 39.62 N |
| ATOM | 11702 | CA | SER | B | 239 | −62.264 | −5.882 | −17.631 | 1.00 | 39.63 C |
| ATOM | 11704 | CB | SER | B | 239 | −63.689 | −5.810 | −18.172 | 1.00 | 39.56 C |
| ATOM | 11707 | OG | SER | B | 239 | −63.945 | −6.917 | −19.010 | 1.00 | 38.96 O |
| ATOM | 11709 | C | SER | B | 239 | −61.796 | −4.496 | −17.181 | 1.00 | 39.99 C |
| ATOM | 11710 | O | SER | B | 239 | −61.108 | −3.807 | −17.933 | 1.00 | 40.10 O |
| ATOM | 11712 | N | ARG | B | 240 | −62.168 | −4.088 | −15.965 | 1.00 | 40.35 N |
| ATOM | 11713 | CA | ARG | B | 240 | −61.624 | −2.864 | −15.363 | 1.00 | 40.68 C |
| ATOM | 11715 | CB | ARG | B | 240 | −62.025 | −2.712 | −13.881 | 1.00 | 41.26 C |
| ATOM | 11718 | CG | ARG | B | 240 | −63.231 | −1.782 | −13.621 | 1.00 | 43.86 C |
| ATOM | 11721 | CD | ARG | B | 240 | −63.334 | −1.375 | −12.130 | 1.00 | 47.07 C |
| ATOM | 11724 | NE | ARG | B | 240 | −63.365 | −2.537 | −11.222 | 1.00 | 50.14 N |
| ATOM | 11726 | CZ | ARG | B | 240 | −64.462 | −3.077 | −10.671 | 1.00 | 52.32 C |
| ATOM | 11727 | NH1 | ARG | B | 240 | −64.342 | −4.141 | −9.875 | 1.00 | 53.16 N |
| ATOM | 11730 | NH2 | ARG | B | 240 | −65.677 | −2.577 | −10.899 | 1.00 | 53.18 N |
| ATOM | 11733 | C | ARG | B | 240 | −60.113 | −2.914 | −15.464 | 1.00 | 39.91 C |
| ATOM | 11734 | O | ARG | B | 240 | −59.490 | −2.000 | −15.988 | 1.00 | 39.86 O |
| ATOM | 11736 | N | TRP | B | 241 | −59.541 | −4.002 | −14.962 | 1.00 | 39.14 N |
| ATOM | 11737 | CA | TRP | B | 241 | −58.105 | −4.217 | −15.004 | 1.00 | 38.37 C |
| ATOM | 11739 | CB | TRP | B | 241 | −57.773 | −5.635 | −14.521 | 1.00 | 38.17 C |
| ATOM | 11742 | CG | TRP | B | 241 | −56.373 | −6.005 | −14.773 | 1.00 | 36.58 C |
| ATOM | 11743 | CD1 | TRP | B | 241 | −55.290 | −5.668 | −14.022 | 1.00 | 36.32 C |
| ATOM | 11745 | NE1 | TRP | B | 241 | −54.152 | −6.176 | −14.587 | 1.00 | 35.63 N |
| ATOM | 11747 | CE2 | TRP | B | 241 | −54.494 | −6.846 | −15.731 | 1.00 | 34.31 C |
| ATOM | 11748 | CD2 | TRP | B | 241 | −55.883 | −6.757 | −15.874 | 1.00 | 33.99 C |
| ATOM | 11749 | CE3 | TRP | B | 241 | −56.484 | −7.357 | −16.977 | 1.00 | 33.28 C |
| ATOM | 11751 | CZ3 | TRP | B | 241 | −55.691 | −8.034 | −17.883 | 1.00 | 32.79 C |
| ATOM | 11753 | CH2 | TRP | B | 241 | −54.313 | −8.101 | −17.720 | 1.00 | 33.06 C |
| ATOM | 11755 | CZ2 | TRP | B | 241 | −53.697 | −7.515 | −16.648 | 1.00 | 34.16 C |

TABLE 3-7-continued

| | | | | | Coordinates of P. tremuloides IspS | | | | | |
|---|---|---|---|---|---|---|---|---|---|---|
| ATOM | 11757 | C | TRP | B | 241 | −57.561 | −3.999 | −16.409 | 1.00 | 38.25 | C |
| ATOM | 11758 | O | TRP | B | 241 | −56.607 | −3.252 | −16.603 | 1.00 | 38.13 | O |
| ATOM | 11760 | N | TRP | B | 242 | −58.186 | −4.644 | −17.386 | 1.00 | 38.21 | N |
| ATOM | 11761 | CA | TRP | B | 242 | −57.695 | −4.628 | −18.765 | 1.00 | 38.27 | C |
| ATOM | 11763 | CB | TRP | B | 242 | −58.479 | −5.640 | −19.609 | 1.00 | 38.31 | C |
| ATOM | 11766 | CG | TRP | B | 242 | −57.948 | −5.872 | −20.990 | 1.00 | 38.61 | C |
| ATOM | 11767 | CD1 | TRP | B | 242 | −58.642 | −5.754 | −22.156 | 1.00 | 39.11 | C |
| ATOM | 11769 | NE1 | TRP | B | 242 | −57.828 | −6.046 | −23.224 | 1.00 | 39.31 | N |
| ATOM | 11771 | CE2 | TRP | B | 242 | −56.582 | −6.363 | −22.759 | 1.00 | 38.95 | C |
| ATOM | 11772 | CD2 | TRP | B | 242 | −56.617 | −6.263 | −21.356 | 1.00 | 38.66 | C |
| ATOM | 11773 | CE3 | TRP | B | 242 | −55.454 | −6.528 | −20.637 | 1.00 | 38.98 | C |
| ATOM | 11775 | CZ3 | TRP | B | 242 | −54.314 | −6.886 | −21.326 | 1.00 | 39.20 | C |
| ATOM | 11777 | CH2 | TRP | B | 242 | −54.313 | −6.985 | −22.716 | 1.00 | 39.12 | C |
| ATOM | 11779 | CZ2 | TRP | B | 242 | −55.434 | −6.724 | −23.451 | 1.00 | 39.22 | C |
| ATOM | 11781 | C | TRP | B | 242 | −57.739 | −3.241 | −19.400 | 1.00 | 38.27 | C |
| ATOM | 11782 | O | TRP | B | 242 | −56.814 | −2.873 | −20.108 | 1.00 | 37.81 | O |
| ATOM | 11784 | N | ARG | B | 243 | −58.809 | −2.489 | −19.140 | 1.00 | 38.79 | N |
| ATOM | 11785 | CA | ARG | B | 243 | −58.936 | −1.097 | −19.607 | 1.00 | 39.37 | C |
| ATOM | 11787 | CB | ARG | B | 243 | −60.351 | −.552 | −19.346 | 1.00 | 39.66 | C |
| ATOM | 11790 | CG | ARG | B | 243 | −61.324 | −.792 | −20.520 | 1.00 | 41.96 | C |
| ATOM | 11793 | CD | ARG | B | 243 | −62.687 | −1.338 | −20.085 | 1.00 | 44.82 | C |
| ATOM | 11796 | NE | ARG | B | 243 | −63.461 | −.380 | −19.296 | 1.00 | 47.15 | N |
| ATOM | 11798 | CZ | ARG | B | 243 | −64.389 | −.704 | −18.386 | 1.00 | 49.26 | C |
| ATOM | 11799 | NH1 | ARG | B | 243 | −64.685 | −1.976 | −18.109 | 1.00 | 49.18 | N |
| ATOM | 11802 | NH2 | ARG | B | 243 | −65.028 | .262 | −17.729 | 1.00 | 50.40 | N |
| ATOM | 11805 | C | ARG | B | 243 | −57.890 | −.183 | −18.980 | 1.00 | 39.28 | C |
| ATOM | 11806 | O | ARG | B | 243 | −57.246 | .577 | −19.681 | 1.00 | 39.40 | O |
| ATOM | 11808 | N | ARG | B | 244 | −57.724 | −.282 | −17.665 | 1.00 | 39.52 | N |
| ATOM | 11809 | CA | ARG | B | 244 | −56.734 | .489 | −16.888 | 1.00 | 39.61 | C |
| ATOM | 11811 | CB | ARG | B | 244 | −56.774 | .041 | −15.409 | 1.00 | 40.25 | C |
| ATOM | 11814 | CG | ARG | B | 244 | −56.115 | .971 | −14.383 | 1.00 | 42.01 | C |
| ATOM | 11817 | CD | ARG | B | 244 | −57.029 | 2.154 | −14.017 | 1.00 | 44.39 | C |
| ATOM | 11820 | NE | ARG | B | 244 | −56.391 | 3.115 | −13.103 | 1.00 | 46.36 | N |
| ATOM | 11822 | CZ | ARG | B | 244 | −55.434 | 3.984 | −13.441 | 1.00 | 48.06 | C |
| ATOM | 11823 | NH1 | ARG | B | 244 | −54.951 | 4.043 | −14.686 | 1.00 | 48.90 | N |
| ATOM | 11826 | NH2 | ARG | B | 244 | −54.947 | 4.805 | −12.519 | 1.00 | 48.82 | N |
| ATOM | 11829 | C | ARG | B | 244 | −55.323 | .322 | −17.437 | 1.00 | 38.83 | C |
| ATOM | 11830 | O | ARG | B | 244 | −54.594 | 1.300 | −17.567 | 1.00 | 38.39 | O |
| ATOM | 11832 | N | VAL | B | 245 | −54.953 | −.922 | −17.738 | 1.00 | 38.52 | N |
| ATOM | 11833 | CA | VAL | B | 245 | −53.694 | −1.241 | −18.437 | 1.00 | 38.43 | C |
| ATOM | 11835 | CB | VAL | B | 245 | −53.491 | −2.760 | −18.614 | 1.00 | 38.31 | C |
| ATOM | 11837 | CG1 | VAL | B | 245 | −53.247 | −3.426 | −17.283 | 1.00 | 37.77 | C |
| ATOM | 11841 | CG2 | VAL | B | 245 | −52.344 | −3.036 | −19.561 | 1.00 | 37.66 | C |
| ATOM | 11845 | C | VAL | B | 245 | −53.650 | −.638 | −19.832 | 1.00 | 38.68 | C |
| ATOM | 11846 | O | VAL | B | 245 | −52.615 | −.153 | −20.247 | 1.00 | 38.57 | O |
| ATOM | 11848 | N | GLY | B | 246 | −54.765 | −.724 | −20.559 | 1.00 | 39.26 | N |
| ATOM | 11849 | CA | GLY | B | 246 | −54.974 | −.012 | −21.834 | 1.00 | 39.62 | C |
| ATOM | 11852 | C | GLY | B | 246 | −53.962 | −.262 | −22.942 | 1.00 | 40.08 | C |
| ATOM | 11853 | O | GLY | B | 246 | −53.617 | .650 | −23.700 | 1.00 | 39.89 | O |
| ATOM | 11855 | N | LEU | B | 247 | −53.502 | −1.500 | −23.062 | 1.00 | 40.75 | N |
| ATOM | 11856 | CA | LEU | B | 247 | −52.347 | −1.778 | −23.905 | 1.00 | 41.34 | C |
| ATOM | 11858 | CB | LEU | B | 247 | −51.655 | −3.065 | −23.459 | 1.00 | 41.15 | C |
| ATOM | 11861 | CG | LEU | B | 247 | −50.132 | −3.026 | −23.298 | 1.00 | 40.49 | C |
| ATOM | 11863 | CD1 | LEU | B | 247 | −49.622 | −1.769 | −22.605 | 1.00 | 39.50 | C |
| ATOM | 11867 | CD2 | LEU | B | 247 | −49.695 | −4.242 | −22.526 | 1.00 | 39.98 | C |
| ATOM | 11871 | C | LEU | B | 247 | −52.744 | −1.836 | −25.370 | 1.00 | 42.50 | C |
| ATOM | 11872 | O | LEU | B | 247 | −52.005 | −1.358 | −26.225 | 1.00 | 42.33 | O |
| ATOM | 11874 | N | ALA | B | 248 | −53.925 | −2.390 | −25.654 | 1.00 | 44.14 | N |
| ATOM | 11875 | CA | ALA | B | 248 | −54.439 | −2.494 | −27.041 | 1.00 | 45.16 | C |
| ATOM | 11877 | CB | ALA | B | 248 | −55.705 | −3.347 | −27.087 | 1.00 | 45.15 | C |
| ATOM | 11881 | C | ALA | B | 248 | −54.692 | −1.140 | −27.739 | 1.00 | 45.98 | C |
| ATOM | 11882 | O | ALA | B | 248 | −54.604 | −1.053 | −28.971 | 1.00 | 46.37 | O |
| ATOM | 11884 | N | THR | B | 249 | −55.004 | −.095 | −26.975 | 1.00 | 46.64 | N |
| ATOM | 11885 | CA | THR | B | 249 | −55.142 | 1.234 | −27.570 | 1.00 | 47.25 | C |
| ATOM | 11887 | CB | THR | B | 249 | −55.905 | 2.253 | −26.655 | 1.00 | 47.44 | C |
| ATOM | 11889 | OG1 | THR | B | 249 | −55.001 | 2.845 | −25.706 | 1.00 | 47.52 | O |
| ATOM | 11891 | CG2 | THR | B | 249 | −57.104 | 1.592 | −25.928 | 1.00 | 47.44 | C |
| ATOM | 11895 | C | THR | B | 249 | −53.756 | 1.793 | −27.931 | 1.00 | 47.59 | C |
| ATOM | 11896 | O | THR | B | 249 | −53.553 | 2.279 | −29.049 | 1.00 | 48.07 | O |
| ATOM | 11898 | N | LYS | B | 250 | −52.808 | 1.710 | −26.995 | 1.00 | 47.67 | N |
| ATOM | 11899 | CA | LYS | B | 250 | −51.469 | 2.299 | −27.185 | 1.00 | 47.68 | C |
| ATOM | 11901 | CB | LYS | B | 250 | −50.793 | 2.553 | −25.833 | 1.00 | 47.68 | C |
| ATOM | 11904 | CG | LYS | B | 250 | −51.428 | 3.673 | −24.999 | 1.00 | 47.77 | C |
| ATOM | 11907 | CD | LYS | B | 250 | −51.142 | 5.086 | −25.552 | 1.00 | 47.59 | C |
| ATOM | 11910 | CE | LYS | B | 250 | −49.676 | 5.496 | −25.441 | 1.00 | 46.75 | C |
| ATOM | 11913 | NZ | LYS | B | 250 | −49.479 | 6.878 | −25.948 | 1.00 | 46.49 | N |
| ATOM | 11917 | C | LYS | B | 250 | −50.541 | 1.465 | −28.082 | 1.00 | 47.72 | C |
| ATOM | 11918 | O | LYS | B | 250 | −49.591 | 1.988 | −28.663 | 1.00 | 47.54 | O |

TABLE 3-7-continued

Coordinates of *P. tremuloides* IspS

| ATOM | 11920 | N | LEU | B | 251 | −50.804 | .169 | −28.184 | 1.00 | 47.82 | N |
|---|---|---|---|---|---|---|---|---|---|---|---|
| ATOM | 11921 | CA | LEU | B | 251 | −50.072 | −.675 | −29.118 | 1.00 | 47.96 | C |
| ATOM | 11923 | CB | LEU | B | 251 | −49.584 | −1.970 | −28.447 | 1.00 | 48.04 | C |
| ATOM | 11926 | CG | LEU | B | 251 | −48.109 | −2.064 | −28.033 | 1.00 | 47.39 | C |
| ATOM | 11928 | CD1 | LEU | B | 251 | −47.659 | −.881 | −27.186 | 1.00 | 46.47 | C |
| ATOM | 11932 | CD2 | LEU | B | 251 | −47.894 | −3.376 | −27.304 | 1.00 | 46.78 | C |
| ATOM | 11936 | C | LEU | B | 251 | −50.985 | −.964 | −30.306 | 1.00 | 48.19 | C |
| ATOM | 11937 | O | LEU | B | 251 | −51.975 | −1.693 | −30.194 | 1.00 | 48.38 | O |
| ATOM | 11939 | N | HIS | B | 252 | −50.627 | −.396 | −31.449 | 1.00 | 48.42 | N |
| ATOM | 11940 | CA | HIS | B | 252 | −51.521 | −.329 | −32.601 | 1.00 | 48.62 | C |
| ATOM | 11942 | CB | HIS | B | 252 | −51.110 | .850 | −33.492 | 1.00 | 48.99 | C |
| ATOM | 11945 | CG | HIS | B | 252 | −51.000 | 2.145 | −32.742 | 1.00 | 50.56 | C |
| ATOM | 11946 | ND1 | HIS | B | 252 | −52.095 | 2.935 | −32.453 | 1.00 | 52.11 | N |
| ATOM | 11948 | CE1 | HIS | B | 252 | −51.704 | 3.993 | −31.766 | 1.00 | 52.68 | C |
| ATOM | 11950 | NE2 | HIS | B | 252 | −50.397 | 3.912 | −31.585 | 1.00 | 52.86 | N |
| ATOM | 11952 | CD2 | HIS | B | 252 | −49.932 | 2.764 | −32.181 | 1.00 | 51.68 | C |
| ATOM | 11954 | C | HIS | B | 252 | −51.582 | −1.636 | −33.383 | 1.00 | 48.14 | C |
| ATOM | 11955 | O | HIS | B | 252 | −52.615 | −1.975 | −33.935 | 1.00 | 48.02 | O |
| ATOM | 11957 | N | PHE | B | 253 | −50.481 | −2.372 | −33.405 | 1.00 | 48.10 | N |
| ATOM | 11958 | CA | PHE | B | 253 | −50.422 | −3.702 | −34.044 | 1.00 | 48.18 | C |
| ATOM | 11960 | CB | PHE | B | 253 | −48.965 | −4.070 | −34.375 | 1.00 | 48.16 | C |
| ATOM | 11963 | CG | PHE | B | 253 | −48.119 | −4.311 | −33.163 | 1.00 | 47.85 | C |
| ATOM | 11964 | CD1 | PHE | B | 253 | −47.900 | −5.596 | −32.702 | 1.00 | 48.56 | C |
| ATOM | 11966 | CE1 | PHE | B | 253 | −47.140 | −5.812 | −31.576 | 1.00 | 48.98 | C |
| ATOM | 11968 | CZ | PHE | B | 253 | −46.602 | −4.729 | −30.895 | 1.00 | 48.50 | C |
| ATOM | 11970 | CE2 | PHE | B | 253 | −46.817 | −3.454 | −31.349 | 1.00 | 47.40 | C |
| ATOM | 11972 | CD2 | PHE | B | 253 | −47.569 | −3.249 | −32.465 | 1.00 | 47.22 | C |
| ATOM | 11974 | C | PHE | B | 253 | −51.038 | −4.819 | −33.185 | 1.00 | 48.30 | C |
| ATOM | 11975 | O | PHE | B | 253 | −51.344 | −5.903 | −33.691 | 1.00 | 47.63 | O |
| ATOM | 11977 | N | ALA | B | 254 | −51.204 | −4.541 | −31.888 | 1.00 | 48.86 | N |
| ATOM | 11978 | CA | ALA | B | 254 | −51.653 | −5.531 | −30.903 | 1.00 | 49.13 | C |
| ATOM | 11980 | CB | ALA | B | 254 | −51.290 | −5.071 | −29.494 | 1.00 | 49.02 | C |
| ATOM | 11984 | C | ALA | B | 254 | −53.153 | −5.806 | −30.982 | 1.00 | 49.46 | C |
| ATOM | 11985 | O | ALA | B | 254 | −53.967 | −4.870 | −31.011 | 1.00 | 49.50 | O |
| ATOM | 11987 | N | ARG | B | 255 | −53.501 | −7.097 | −31.006 | 1.00 | 49.75 | N |
| ATOM | 11988 | CA | ARG | B | 255 | −54.896 | −7.549 | −30.918 | 1.00 | 49.89 | C |
| ATOM | 11990 | CB | ARG | B | 255 | −55.028 | −9.051 | −31.245 | 1.00 | 49.94 | C |
| ATOM | 11993 | CG | ARG | B | 255 | −54.839 | −9.439 | −32.724 | 1.00 | 49.93 | C |
| ATOM | 11996 | CD | ARG | B | 255 | −54.709 | −10.967 | −32.904 | 1.00 | 49.79 | C |
| ATOM | 11999 | NE | ARG | B | 255 | −53.527 | −11.505 | −32.219 | 1.00 | 50.11 | N |
| ATOM | 12001 | CZ | ARG | B | 255 | −53.276 | −12.801 | −32.010 | 1.00 | 50.54 | C |
| ATOM | 12002 | NH1 | ARG | B | 255 | −54.117 | −13.736 | −32.439 | 1.00 | 51.36 | N |
| ATOM | 12005 | NH2 | ARG | B | 255 | −52.175 | −13.172 | −31.360 | 1.00 | 50.21 | N |
| ATOM | 12008 | C | ARG | B | 255 | −55.425 | −7.308 | −29.511 | 1.00 | 49.83 | C |
| ATOM | 12009 | O | ARG | B | 255 | −54.666 | −6.975 | −28.599 | 1.00 | 49.95 | O |
| ATOM | 12011 | N | ASP | B | 256 | −56.736 | −7.463 | −29.350 | 1.00 | 49.72 | N |
| ATOM | 12012 | CA | ASP | B | 256 | −57.360 | −7.483 | −28.034 | 1.00 | 49.55 | C |
| ATOM | 12014 | CB | ASP | B | 256 | −58.183 | −6.222 | −27.812 | 1.00 | 49.52 | C |
| ATOM | 12017 | CG | ASP | B | 256 | −59.134 | −6.362 | −26.654 | 1.00 | 50.30 | C |
| ATOM | 12018 | OD1 | ASP | B | 256 | −60.310 | −5.944 | −26.780 | 1.00 | 50.45 | O |
| ATOM | 12019 | OD2 | ASP | B | 256 | −58.702 | −6.926 | −25.622 | 1.00 | 51.68 | O |
| ATOM | 12020 | C | ASP | B | 256 | −58.254 | −8.721 | −27.931 | 1.00 | 49.15 | C |
| ATOM | 12021 | O | ASP | B | 256 | −59.159 | −8.901 | −28.737 | 1.00 | 49.28 | O |
| ATOM | 12023 | N | ARG | B | 257 | −57.998 | −9.565 | −26.937 | 1.00 | 48.61 | N |
| ATOM | 12024 | CA | ARG | B | 257 | −58.743 | −10.809 | −26.765 | 1.00 | 48.20 | C |
| ATOM | 12026 | CB | ARG | B | 257 | −57.949 | −11.984 | −27.373 | 1.00 | 48.41 | C |
| ATOM | 12029 | CG | ARG | B | 257 | −57.505 | −11.799 | −28.821 | 1.00 | 49.37 | C |
| ATOM | 12032 | CD | ARG | B | 257 | −58.693 | −11.636 | −29.784 | 1.00 | 50.80 | C |
| ATOM | 12035 | NE | ARG | B | 257 | −58.908 | −12.814 | −30.627 | 1.00 | 52.11 | N |
| ATOM | 12037 | CZ | ARG | B | 257 | −58.678 | −12.876 | −31.944 | 1.00 | 52.99 | C |
| ATOM | 12038 | NH1 | ARG | B | 257 | −58.214 | −11.820 | −32.623 | 1.00 | 52.37 | N |
| ATOM | 12041 | NH2 | ARG | B | 257 | −58.918 | −14.016 | −32.596 | 1.00 | 52.97 | N |
| ATOM | 12044 | C | ARG | B | 257 | −59.032 | −11.089 | −25.280 | 1.00 | 47.32 | C |
| ATOM | 12045 | O | ARG | B | 257 | −58.579 | −12.101 | −24.735 | 1.00 | 47.46 | O |
| ATOM | 12047 | N | LEU | B | 258 | −59.770 | −10.201 | −24.616 | 1.00 | 45.94 | N |
| ATOM | 12048 | CA | LEU | B | 258 | −60.108 | −10.430 | −23.205 | 1.00 | 44.67 | C |
| ATOM | 12050 | CB | LEU | B | 258 | −60.332 | −9.130 | −22.438 | 1.00 | 44.61 | C |
| ATOM | 12053 | CG | LEU | B | 258 | −60.422 | −9.323 | −20.920 | 1.00 | 43.83 | C |
| ATOM | 12055 | CD1 | LEU | B | 258 | −59.045 | −9.552 | −20.339 | 1.00 | 43.48 | C |
| ATOM | 12059 | CD2 | LEU | B | 258 | −61.073 | −8.139 | −20.262 | 1.00 | 43.85 | C |
| ATOM | 12063 | C | LEU | B | 258 | −61.347 | −11.286 | −23.090 | 1.00 | 43.49 | C |
| ATOM | 12064 | O | LEU | B | 258 | −61.375 | −12.220 | −22.295 | 1.00 | 43.84 | O |
| ATOM | 12066 | N | ILE | B | 259 | −62.364 | −10.968 | −23.883 | 1.00 | 41.92 | N |
| ATOM | 12067 | CA | ILE | B | 259 | −63.617 | −11.711 | −23.841 | 1.00 | 40.80 | C |
| ATOM | 12069 | CB | ILE | B | 259 | −64.718 | −11.132 | −24.783 | 1.00 | 41.05 | C |
| ATOM | 12071 | CG1 | ILE | B | 259 | −64.852 | −9.598 | −24.653 | 1.00 | 41.61 | C |
| ATOM | 12074 | CD1 | ILE | B | 259 | −65.200 | −8.874 | −25.985 | 1.00 | 42.16 | C |
| ATOM | 12078 | CG2 | ILE | B | 259 | −66.065 | −11.816 | −24.496 | 1.00 | 40.46 | C |

TABLE 3-7-continued

Coordinates of *P. tremuloides* IspS

| ATOM | 12082 | C | ILE | B | 259 | −63.319 | −13.151 | −24.250 | 1.00 | 39.50 | C |
|---|---|---|---|---|---|---|---|---|---|---|---|
| ATOM | 12083 | O | ILE | B | 259 | −63.782 | −14.082 | −23.598 | 1.00 | 39.30 | O |
| ATOM | 12085 | N | GLU | B | 260 | −62.524 | −13.318 | −25.316 | 1.00 | 37.99 | N |
| ATOM | 12086 | CA | GLU | B | 260 | −62.120 | −14.652 | −25.812 | 1.00 | 36.60 | C |
| ATOM | 12088 | CB | GLU | B | 260 | −61.329 | −14.574 | −27.142 | 1.00 | 36.75 | C |
| ATOM | 12091 | CG | GLU | B | 260 | −62.167 | −14.319 | −28.425 | 1.00 | 37.79 | C |
| ATOM | 12094 | CD | GLU | B | 260 | −62.134 | −12.851 | −28.905 | 1.00 | 39.47 | C |
| ATOM | 12095 | OE1 | GLU | B | 260 | −62.207 | −11.923 | −28.055 | 1.00 | 39.97 | O |
| ATOM | 12096 | OE2 | GLU | B | 260 | −62.033 | −12.628 | −30.139 | 1.00 | 40.31 | O |
| ATOM | 12097 | C | GLU | B | 260 | −61.282 | −15.381 | −24.770 | 1.00 | 34.83 | C |
| ATOM | 12098 | O | GLU | B | 260 | −61.465 | −16.568 | −24.544 | 1.00 | 34.69 | O |
| ATOM | 12100 | N | SER | B | 261 | −60.365 | −14.669 | −24.131 | 1.00 | 32.89 | N |
| ATOM | 12101 | CA | SER | B | 261 | −59.508 | −15.292 | −23.139 | 1.00 | 31.48 | C |
| ATOM | 12103 | CB | SER | B | 261 | −58.341 | −14.376 | −22.768 | 1.00 | 31.55 | C |
| ATOM | 12106 | OG | SER | B | 261 | −57.298 | −14.493 | −23.728 | 1.00 | 31.75 | O |
| ATOM | 12108 | C | SER | B | 261 | −60.294 | −15.716 | −21.900 | 1.00 | 30.04 | C |
| ATOM | 12109 | O | SER | B | 261 | −59.921 | −16.674 | −21.208 | 1.00 | 29.70 | O |
| ATOM | 12111 | N | PHE | B | 262 | −61.389 | −15.021 | −21.618 | 1.00 | 28.25 | N |
| ATOM | 12112 | CA | PHE | B | 262 | −62.203 | −15.404 | −20.480 | 1.00 | 26.75 | C |
| ATOM | 12114 | CB | PHE | B | 262 | −63.111 | −14.278 | −20.009 | 1.00 | 26.36 | C |
| ATOM | 12117 | CG | PHE | B | 262 | −63.532 | −14.453 | −18.603 | 1.00 | 24.33 | C |
| ATOM | 12118 | CD1 | PHE | B | 262 | −62.697 | −14.092 | −17.584 | 1.00 | 22.66 | C |
| ATOM | 12120 | CE1 | PHE | B | 262 | −63.047 | −14.283 | −16.301 | 1.00 | 22.65 | C |
| ATOM | 12122 | CZ | PHE | B | 262 | −64.245 | −14.873 | −16.007 | 1.00 | 23.93 | C |
| ATOM | 12124 | CE2 | PHE | B | 262 | −65.076 | −15.267 | −17.010 | 1.00 | 24.08 | C |
| ATOM | 12126 | CD2 | PHE | B | 262 | −64.711 | −15.067 | −18.304 | 1.00 | 23.96 | C |
| ATOM | 12128 | C | PHE | B | 262 | −63.017 | −16.660 | −20.751 | 1.00 | 26.02 | C |
| ATOM | 12129 | O | PHE | B | 262 | −63.074 | −17.546 | −19.909 | 1.00 | 26.32 | O |
| ATOM | 12131 | N | TYR | B | 263 | −63.652 | −16.732 | −21.915 | 1.00 | 24.98 | N |
| ATOM | 12132 | CA | TYR | B | 263 | −64.299 | −17.969 | −22.396 | 1.00 | 24.14 | C |
| ATOM | 12134 | CB | TYR | B | 263 | −64.701 | −17.756 | −23.853 | 1.00 | 24.00 | C |
| ATOM | 12137 | CG | TYR | B | 263 | −65.080 | −18.961 | −24.667 | 1.00 | 24.32 | C |
| ATOM | 12138 | CD1 | TYR | B | 263 | −66.302 | −19.604 | −24.489 | 1.00 | 25.03 | C |
| ATOM | 12140 | CE1 | TYR | B | 263 | −66.666 | −20.694 | −25.285 | 1.00 | 25.81 | C |
| ATOM | 12142 | CZ | TYR | B | 263 | −65.798 | −21.132 | −26.287 | 1.00 | 27.06 | C |
| ATOM | 12143 | OH | TYR | B | 263 | −66.106 | −22.191 | −27.123 | 1.00 | 27.14 | O |
| ATOM | 12145 | CE2 | TYR | B | 263 | −64.590 | −20.489 | −26.479 | 1.00 | 26.80 | C |
| ATOM | 12147 | CD2 | TYR | B | 263 | −64.250 | −19.404 | −25.680 | 1.00 | 25.65 | C |
| ATOM | 12149 | C | TYR | B | 263 | −63.351 | −19.162 | −22.256 | 1.00 | 23.35 | C |
| ATOM | 12150 | O | TYR | B | 263 | −63.712 | −20.219 | −21.740 | 1.00 | 22.80 | O |
| ATOM | 12152 | N | TRP | B | 264 | −62.119 | −18.955 | −22.702 | 1.00 | 22.64 | N |
| ATOM | 12153 | CA | TRP | B | 264 | −61.047 | −19.918 | −22.523 | 1.00 | 21.95 | C |
| ATOM | 12155 | CB | TRP | B | 264 | −59.737 | −19.334 | −23.061 | 1.00 | 21.84 | C |
| ATOM | 12158 | CG | TRP | B | 264 | −58.603 | −20.278 | −22.964 | 1.00 | 22.90 | C |
| ATOM | 12159 | CD1 | TRP | B | 264 | −57.700 | −20.387 | −21.943 | 1.00 | 23.98 | C |
| ATOM | 12161 | NE1 | TRP | B | 264 | −56.800 | −21.386 | −22.214 | 1.00 | 23.95 | N |
| ATOM | 12163 | CE2 | TRP | B | 264 | −57.124 | −21.949 | −23.417 | 1.00 | 23.51 | C |
| ATOM | 12164 | CD2 | TRP | B | 264 | −58.252 | −21.273 | −23.915 | 1.00 | 23.40 | C |
| ATOM | 12165 | CE3 | TRP | B | 264 | −58.776 | −21.652 | −25.147 | 1.00 | 23.68 | C |
| ATOM | 12167 | CZ3 | TRP | B | 264 | −58.178 | −22.669 | −25.826 | 1.00 | 24.44 | C |
| ATOM | 12169 | CH2 | TRP | B | 264 | −57.060 | −23.324 | −25.310 | 1.00 | 24.97 | C |
| ATOM | 12171 | CZ2 | TRP | B | 264 | −56.521 | −22.978 | −24.103 | 1.00 | 24.44 | C |
| ATOM | 12173 | C | TRP | B | 264 | −60.897 | −20.326 | −21.050 | 1.00 | 21.11 | C |
| ATOM | 12174 | O | TRP | B | 264 | −60.768 | −21.511 | −20.748 | 1.00 | 20.98 | O |
| ATOM | 12176 | N | ALA | B | 265 | −60.916 | −19.344 | −20.147 | 1.00 | 20.17 | N |
| ATOM | 12177 | CA | ALA | B | 265 | −60.774 | −19.602 | −18.712 | 1.00 | 19.36 | C |
| ATOM | 12179 | CB | ALA | B | 265 | −60.621 | −18.305 | −17.944 | 1.00 | 19.30 | C |
| ATOM | 12183 | C | ALA | B | 265 | −61.947 | −20.397 | −18.171 | 1.00 | 18.63 | C |
| ATOM | 12184 | O | ALA | B | 265 | −61.763 | −21.349 | −17.434 | 1.00 | 18.64 | O |
| ATOM | 12186 | N | VAL | B | 266 | −63.159 | −20.034 | −18.557 | 1.00 | 18.11 | N |
| ATOM | 12187 | CA | VAL | B | 266 | −64.335 | −20.758 | −18.075 | 1.00 | 17.60 | C |
| ATOM | 12189 | CB | VAL | B | 266 | −65.652 | −20.221 | −18.675 | 1.00 | 17.38 | C |
| ATOM | 12191 | CG1 | VAL | B | 266 | −65.902 | −18.803 | −18.199 | 1.00 | 17.09 | C |
| ATOM | 12195 | CG2 | VAL | B | 266 | −66.817 | −21.120 | −18.312 | 1.00 | 15.40 | C |
| ATOM | 12199 | C | VAL | B | 266 | −64.221 | −22.246 | −18.376 | 1.00 | 17.67 | C |
| ATOM | 12200 | O | VAL | B | 266 | −64.766 | −23.058 | −17.647 | 1.00 | 18.27 | O |
| ATOM | 12202 | N | GLY | B | 267 | −63.516 | −22.607 | −19.444 | 1.00 | 17.43 | N |
| ATOM | 12203 | CA | GLY | B | 267 | −63.316 | −24.013 | −19.789 | 1.00 | 16.98 | C |
| ATOM | 12206 | C | GLY | B | 267 | −62.253 | −24.683 | −18.947 | 1.00 | 16.55 | C |
| ATOM | 12207 | O | GLY | B | 267 | −62.360 | −25.859 | −18.609 | 1.00 | 16.37 | O |
| ATOM | 12209 | N | VAL | B | 268 | −61.215 | −23.939 | −18.608 | 1.00 | 16.30 | N |
| ATOM | 12210 | CA | VAL | B | 268 | −60.160 | −24.500 | −17.794 | 1.00 | 16.23 | C |
| ATOM | 12212 | CB | VAL | B | 268 | −58.893 | −23.651 | −17.840 | 1.00 | 15.68 | C |
| ATOM | 12214 | CG1 | VAL | B | 268 | −57.857 | −24.194 | −16.894 | 1.00 | 15.01 | C |
| ATOM | 12218 | CG2 | VAL | B | 268 | −58.361 | −23.674 | −19.235 | 1.00 | 15.01 | C |
| ATOM | 12222 | C | VAL | B | 268 | −60.654 | −24.718 | −16.374 | 1.00 | 16.86 | C |
| ATOM | 12223 | O | VAL | B | 268 | −60.421 | −25.784 | −15.813 | 1.00 | 16.93 | O |
| ATOM | 12225 | N | ALA | B | 269 | −61.362 | −23.733 | −15.817 | 1.00 | 17.64 | N |

TABLE 3-7-continued

Coordinates of *P. tremuloides* IspS

| ATOM | 12226 | CA | ALA | B | 269 | −61.911 | −23.838 | −14.461 | 1.00 | 18.46 | C |
|------|-------|-----|-----|---|-----|---------|---------|---------|------|-------|---|
| ATOM | 12228 | CB | ALA | B | 269 | −60.958 | −23.215 | −13.472 | 1.00 | 18.15 | C |
| ATOM | 12232 | C | ALA | B | 269 | −63.312 | −23.213 | −14.340 | 1.00 | 19.34 | C |
| ATOM | 12233 | O | ALA | B | 269 | −63.448 | −22.030 | −14.047 | 1.00 | 19.78 | O |
| ATOM | 12235 | N | PHE | B | 270 | −64.347 | −24.028 | −14.529 | 1.00 | 20.34 | N |
| ATOM | 12236 | CA | PHE | B | 270 | −65.724 | −23.535 | −14.631 | 1.00 | 21.21 | C |
| ATOM | 12238 | CB | PHE | B | 270 | −66.564 | −24.483 | −15.482 | 1.00 | 21.34 | C |
| ATOM | 12241 | CG | PHE | B | 270 | −67.083 | −25.667 | −14.718 | 1.00 | 22.46 | C |
| ATOM | 12242 | CD1 | PHE | B | 270 | −68.294 | −25.596 | −14.039 | 1.00 | 23.19 | C |
| ATOM | 12244 | CE1 | PHE | B | 270 | −68.756 | −26.672 | −13.315 | 1.00 | 23.27 | C |
| ATOM | 12246 | CZ | PHE | B | 270 | −68.003 | −27.836 | −13.258 | 1.00 | 23.35 | C |
| ATOM | 12248 | CE2 | PHE | B | 270 | −66.794 | −27.918 | −13.932 | 1.00 | 22.73 | C |
| ATOM | 12250 | CD2 | PHE | B | 270 | −66.340 | −26.843 | −14.646 | 1.00 | 22.88 | C |
| ATOM | 12252 | C | PHE | B | 270 | −66.464 | −23.366 | −13.316 | 1.00 | 21.98 | C |
| ATOM | 12253 | O | PHE | B | 270 | −67.408 | −22.583 | −13.268 | 1.00 | 21.93 | O |
| ATOM | 12255 | N | GLU | B | 271 | −66.102 | −24.126 | −12.275 | 1.00 | 23.01 | N |
| ATOM | 12256 | CA | GLU | B | 271 | −66.929 | −24.142 | −11.037 | 1.00 | 23.99 | C |
| ATOM | 12258 | CB | GLU | B | 271 | −66.679 | −25.353 | −10.113 | 1.00 | 24.25 | C |
| ATOM | 12261 | CG | GLU | B | 271 | −65.286 | −25.877 | −10.092 | 1.00 | 26.22 | C |
| ATOM | 12264 | CD | GLU | B | 271 | −65.013 | −26.914 | −11.183 | 1.00 | 29.01 | C |
| ATOM | 12265 | OE1 | GLU | B | 271 | −65.563 | −28.032 | −11.090 | 1.00 | 31.36 | O |
| ATOM | 12266 | OE2 | GLU | B | 271 | −64.232 | −26.622 | −12.121 | 1.00 | 30.98 | O |
| ATOM | 12267 | C | GLU | B | 271 | −66.795 | −22.831 | −10.281 | 1.00 | 23.90 | C |
| ATOM | 12268 | O | GLU | B | 271 | −65.702 | −22.296 | −10.181 | 1.00 | 24.29 | O |
| ATOM | 12270 | N | PRO | B | 272 | −67.913 | −22.316 | −9.745 | 1.00 | 24.09 | N |
| ATOM | 12271 | CA | PRO | B | 272 | −68.005 | −20.885 | −9.428 | 1.00 | 24.11 | C |
| ATOM | 12273 | CB | PRO | B | 272 | −69.380 | −20.751 | −8.751 | 1.00 | 24.03 | C |
| ATOM | 12276 | CG | PRO | B | 272 | −70.083 | −22.069 | −8.997 | 1.00 | 24.12 | C |
| ATOM | 12279 | CD | PRO | B | 272 | −69.013 | −23.083 | −9.132 | 1.00 | 23.99 | C |
| ATOM | 12282 | C | PRO | B | 272 | −66.900 | −20.386 | −8.501 | 1.00 | 24.28 | C |
| ATOM | 12283 | O | PRO | B | 272 | −66.421 | −19.261 | −8.676 | 1.00 | 24.40 | O |
| ATOM | 12284 | N | GLN | B | 273 | −66.480 | −21.222 | −7.547 | 1.00 | 24.20 | N |
| ATOM | 12285 | CA | GLN | B | 273 | −65.500 | −20.809 | −6.551 | 1.00 | 24.20 | C |
| ATOM | 12287 | CB | GLN | B | 273 | −65.437 | −21.840 | −5.426 | 1.00 | 24.42 | C |
| ATOM | 12290 | CG | GLN | B | 273 | −64.750 | −23.176 | −5.775 | 1.00 | 25.17 | C |
| ATOM | 12293 | CD | GLN | B | 273 | −65.717 | −24.334 | −6.007 | 1.00 | 26.13 | C |
| ATOM | 12294 | OE1 | GLN | B | 273 | −66.857 | −24.141 | −6.453 | 1.00 | 27.46 | O |
| ATOM | 12295 | NE2 | GLN | B | 273 | −65.251 | −25.554 | −5.721 | 1.00 | 25.05 | N |
| ATOM | 12298 | C | GLN | B | 273 | −64.086 | −20.546 | −7.088 | 1.00 | 24.27 | C |
| ATOM | 12299 | O | GLN | B | 273 | −63.221 | −20.151 | −6.329 | 1.00 | 24.32 | O |
| ATOM | 12301 | N | TYR | B | 274 | −63.842 | −20.759 | −8.380 | 1.00 | 24.59 | N |
| ATOM | 12302 | CA | TYR | B | 274 | −62.509 | −20.551 | −8.962 | 1.00 | 24.85 | C |
| ATOM | 12304 | CB | TYR | B | 274 | −62.129 | −21.724 | −9.880 | 1.00 | 24.62 | C |
| ATOM | 12307 | CG | TYR | B | 274 | −62.009 | −23.054 | −9.184 | 1.00 | 24.35 | C |
| ATOM | 12308 | CD1 | TYR | B | 274 | −61.395 | −23.169 | −7.946 | 1.00 | 24.62 | C |
| ATOM | 12310 | CE1 | TYR | B | 274 | −61.280 | −24.391 | −7.314 | 1.00 | 25.10 | C |
| ATOM | 12312 | CZ | TYR | B | 274 | −61.771 | −25.525 | −7.920 | 1.00 | 24.92 | C |
| ATOM | 12313 | OH | TYR | B | 274 | −61.661 | −26.748 | −7.299 | 1.00 | 24.73 | O |
| ATOM | 12315 | CE2 | TYR | B | 274 | −62.366 | −25.437 | −9.150 | 1.00 | 24.76 | C |
| ATOM | 12317 | CD2 | TYR | B | 274 | −62.477 | −24.203 | −9.779 | 1.00 | 24.70 | C |
| ATOM | 12319 | C | TYR | B | 274 | −62.409 | −19.235 | −9.745 | 1.00 | 25.27 | C |
| ATOM | 12320 | O | TYR | B | 274 | −61.956 | −19.210 | −10.895 | 1.00 | 25.42 | O |
| ATOM | 12322 | N | SER | B | 275 | −62.808 | −18.134 | −9.121 | 1.00 | 25.40 | N |
| ATOM | 12323 | CA | SER | B | 275 | −62.755 | −16.849 | −9.802 | 1.00 | 25.43 | C |
| ATOM | 12325 | CB | SER | B | 275 | −63.615 | −15.814 | −9.071 | 1.00 | 25.53 | C |
| ATOM | 12328 | OG | SER | B | 275 | −65.006 | −16.068 | −9.291 | 1.00 | 25.52 | O |
| ATOM | 12330 | C | SER | B | 275 | −61.300 | −16.403 | −9.948 | 1.00 | 25.36 | C |
| ATOM | 12331 | O | SER | B | 275 | −60.885 | −15.903 | −10.996 | 1.00 | 25.17 | O |
| ATOM | 12333 | N | ASP | B | 276 | −60.517 | −16.617 | −8.901 | 1.00 | 25.41 | N |
| ATOM | 12334 | CA | ASP | B | 276 | −59.095 | −16.353 | −8.979 | 1.00 | 25.42 | C |
| ATOM | 12336 | CB | ASP | B | 276 | −58.390 | −16.794 | −7.712 | 1.00 | 25.44 | C |
| ATOM | 12339 | CG | ASP | B | 276 | −58.728 | −15.925 | −6.558 | 1.00 | 26.32 | C |
| ATOM | 12340 | OD1 | ASP | B | 276 | −59.302 | −14.857 | −6.818 | 1.00 | 27.50 | O |
| ATOM | 12341 | OD2 | ASP | B | 276 | −58.442 | −16.299 | −5.398 | 1.00 | 30.16 | O |
| ATOM | 12342 | C | ASP | B | 276 | −58.495 | −17.069 | −10.157 | 1.00 | 25.20 | C |
| ATOM | 12343 | O | ASP | B | 276 | −57.745 | −16.461 | −10.929 | 1.00 | 25.66 | O |
| ATOM | 12345 | N | CYS | B | 277 | −58.814 | −18.353 | −10.305 | 1.00 | 24.60 | N |
| ATOM | 12346 | CA | CYS | B | 277 | −58.228 | −19.110 | −11.391 | 1.00 | 24.30 | C |
| ATOM | 12348 | CB | CYS | B | 277 | −58.684 | −20.561 | −11.392 | 1.00 | 24.28 | C |
| ATOM | 12351 | SG | CYS | B | 277 | −57.737 | −21.574 | −12.569 | 1.00 | 23.82 | S |
| ATOM | 12353 | C | CYS | B | 277 | −58.593 | −18.448 | −12.698 | 1.00 | 24.09 | C |
| ATOM | 12354 | O | CYS | B | 277 | −57.727 | −18.013 | −13.450 | 1.00 | 23.87 | O |
| ATOM | 12356 | N | ARG | B | 278 | −59.893 | −18.329 | −12.933 | 1.00 | 23.98 | N |
| ATOM | 12357 | CA | ARG | B | 278 | −60.400 | −17.746 | −14.171 | 1.00 | 23.98 | C |
| ATOM | 12359 | CB | ARG | B | 278 | −61.917 | −17.556 | −14.123 | 1.00 | 23.93 | C |
| ATOM | 12362 | CG | ARG | B | 278 | −62.662 | −18.871 | −14.283 | 1.00 | 24.07 | C |
| ATOM | 12365 | CD | ARG | B | 278 | −64.132 | −18.670 | −14.607 | 1.00 | 24.48 | C |
| ATOM | 12368 | NE | ARG | B | 278 | −64.874 | −18.141 | −13.472 | 1.00 | 23.75 | N |

TABLE 3-7-continued

Coordinates of *P. tremuloides* IspS

| ATOM | 12370 | CZ | ARG | B | 278 | −65.254 | −18.856 | −12.419 | 1.00 | 23.72 | C |
|---|---|---|---|---|---|---|---|---|---|---|---|
| ATOM | 12371 | NH1 | ARG | B | 278 | −64.973 | −20.149 | −12.326 | 1.00 | 22.86 | N |
| ATOM | 12374 | NH2 | ARG | B | 278 | −65.927 | −18.262 | −11.443 | 1.00 | 25.08 | N |
| ATOM | 12377 | C | ARG | B | 278 | −59.701 | −16.453 | −14.491 | 1.00 | 23.56 | C |
| ATOM | 12378 | O | ARG | B | 278 | −59.296 | −16.265 | −15.628 | 1.00 | 23.87 | O |
| ATOM | 12380 | N | ASN | B | 279 | −59.512 | −15.593 | −13.495 | 1.00 | 23.24 | N |
| ATOM | 12381 | CA | ASN | B | 279 | −58.854 | −14.301 | −13.734 | 1.00 | 23.48 | C |
| ATOM | 12383 | CB | ASN | B | 279 | −59.055 | −13.340 | −12.574 | 1.00 | 24.05 | C |
| ATOM | 12386 | CG | ASN | B | 279 | −60.510 | −13.017 | −12.346 | 1.00 | 26.58 | C |
| ATOM | 12387 | OD1 | ASN | B | 279 | −61.378 | −13.310 | −13.189 | 1.00 | 28.96 | O |
| ATOM | 12388 | ND2 | ASN | B | 279 | −60.799 | −12.416 | −11.194 | 1.00 | 30.30 | N |
| ATOM | 12391 | C | ASN | B | 279 | −57.376 | −14.404 | −14.027 | 1.00 | 22.58 | C |
| ATOM | 12392 | O | ASN | B | 279 | −56.903 | −13.749 | −14.941 | 1.00 | 22.73 | O |
| ATOM | 12394 | N | SER | B | 280 | −56.648 | −15.205 | −13.251 | 1.00 | 21.62 | N |
| ATOM | 12395 | CA | SER | B | 280 | −55.243 | −15.483 | −13.550 | 1.00 | 20.73 | C |
| ATOM | 12397 | CB | SER | B | 280 | −54.696 | −16.597 | −12.659 | 1.00 | 20.85 | C |
| ATOM | 12400 | OG | SER | B | 280 | −53.805 | −16.099 | −11.683 | 1.00 | 21.55 | O |
| ATOM | 12402 | C | SER | B | 280 | −55.091 | −15.896 | −15.004 | 1.00 | 20.04 | C |
| ATOM | 12403 | O | SER | B | 280 | −54.293 | −15.312 | −15.738 | 1.00 | 19.87 | O |
| ATOM | 12405 | N | VAL | B | 281 | −55.875 | −16.893 | −15.413 | 1.00 | 19.24 | N |
| ATOM | 12406 | CA | VAL | B | 281 | −55.720 | −17.491 | −16.720 | 1.00 | 18.77 | C |
| ATOM | 12408 | CB | VAL | B | 281 | −56.482 | −18.834 | −16.815 | 1.00 | 18.74 | C |
| ATOM | 12410 | CG1 | VAL | B | 281 | −56.467 | −19.404 | −18.251 | 1.00 | 18.34 | C |
| ATOM | 12414 | CG2 | VAL | B | 281 | −55.863 | −19.844 | −15.848 | 1.00 | 18.13 | C |
| ATOM | 12418 | C | VAL | B | 281 | −56.142 | −16.486 | −17.787 | 1.00 | 18.89 | C |
| ATOM | 12419 | O | VAL | B | 281 | −55.483 | −16.364 | −18.832 | 1.00 | 18.75 | O |
| ATOM | 12421 | N | ALA | B | 282 | −57.210 | −15.739 | −17.505 | 1.00 | 18.85 | N |
| ATOM | 12422 | CA | ALA | B | 282 | −57.709 | −14.723 | −18.439 | 1.00 | 18.80 | C |
| ATOM | 12424 | CB | ALA | B | 282 | −59.051 | −14.191 | −17.991 | 1.00 | 18.32 | C |
| ATOM | 12428 | C | ALA | B | 282 | −56.718 | −13.576 | −18.615 | 1.00 | 18.94 | C |
| ATOM | 12429 | O | ALA | B | 282 | −56.582 | −13.021 | −19.700 | 1.00 | 19.16 | O |
| ATOM | 12431 | N | LYS | B | 283 | −56.022 | −13.211 | −17.553 | 1.00 | 19.24 | N |
| ATOM | 12432 | CA | LYS | B | 283 | −55.037 | −12.145 | −17.658 | 1.00 | 19.62 | C |
| ATOM | 12434 | CB | LYS | B | 283 | −54.649 | −11.615 | −16.276 | 1.00 | 19.68 | C |
| ATOM | 12437 | CG | LYS | B | 283 | −55.779 | −10.923 | −15.518 | 1.00 | 19.95 | C |
| ATOM | 12440 | CD | LYS | B | 283 | −55.265 | −10.398 | −14.196 | 1.00 | 21.72 | C |
| ATOM | 12443 | CE | LYS | B | 283 | −56.364 | −10.236 | −13.164 | 1.00 | 23.83 | C |
| ATOM | 12446 | NZ | LYS | B | 283 | −56.129 | −9.003 | −12.351 | 1.00 | 24.72 | N |
| ATOM | 12450 | C | LYS | B | 283 | −53.802 | −12.643 | −18.396 | 1.00 | 19.77 | C |
| ATOM | 12451 | O | LYS | B | 283 | −53.237 | −11.929 | −19.208 | 1.00 | 20.05 | O |
| ATOM | 12453 | N | MET | B | 284 | −53.387 | −13.871 | −18.117 | 1.00 | 19.88 | N |
| ATOM | 12454 | CA | MET | B | 284 | −52.136 | −14.367 | −18.652 | 1.00 | 19.90 | C |
| ATOM | 12456 | CB | MET | B | 284 | −51.719 | −15.676 | −17.960 | 1.00 | 20.08 | C |
| ATOM | 12459 | CG | MET | B | 284 | −51.125 | −15.505 | −16.560 | 1.00 | 20.62 | C |
| ATOM | 12462 | SD | MET | B | 284 | −49.782 | −14.295 | −16.485 | 1.00 | 23.69 | S |
| ATOM | 12463 | CE | MET | B | 284 | −50.600 | −12.872 | −15.754 | 1.00 | 23.82 | C |
| ATOM | 12467 | C | MET | B | 284 | −52.257 | −14.572 | −20.145 | 1.00 | 19.82 | C |
| ATOM | 12468 | O | MET | B | 284 | −51.326 | −14.269 | −20.889 | 1.00 | 20.21 | O |
| ATOM | 12470 | N | PHE | B | 285 | −53.401 | −15.088 | −20.579 | 1.00 | 19.72 | N |
| ATOM | 12471 | CA | PHE | B | 285 | −53.620 | −15.428 | −21.986 | 1.00 | 19.66 | C |
| ATOM | 12473 | CB | PHE | B | 285 | −54.863 | −16.324 | −22.114 | 1.00 | 20.09 | C |
| ATOM | 12476 | CG | PHE | B | 285 | −54.986 | −17.077 | −23.427 | 1.00 | 21.18 | C |
| ATOM | 12477 | CD1 | PHE | B | 285 | −53.877 | −17.362 | −24.232 | 1.00 | 22.86 | C |
| ATOM | 12479 | CE1 | PHE | B | 285 | −54.013 | −18.070 | −25.424 | 1.00 | 22.58 | C |
| ATOM | 12481 | CZ | PHE | B | 285 | −55.254 | −18.518 | −25.806 | 1.00 | 23.49 | C |
| ATOM | 12483 | CE2 | PHE | B | 285 | −56.365 | −18.254 | −25.002 | 1.00 | 23.36 | C |
| ATOM | 12485 | CD2 | PHE | B | 285 | −56.222 | −17.551 | −23.823 | 1.00 | 21.76 | C |
| ATOM | 12487 | C | PHE | B | 285 | −53.781 | −14.148 | −22.781 | 1.00 | 19.18 | C |
| ATOM | 12488 | O | PHE | B | 285 | −53.333 | −14.046 | −23.914 | 1.00 | 18.98 | O |
| ATOM | 12490 | N | SER | B | 286 | −54.410 | −13.161 | −22.164 | 1.00 | 18.92 | N |
| ATOM | 12491 | CA | SER | B | 286 | −54.488 | −11.843 | −22.753 | 1.00 | 19.15 | C |
| ATOM | 12493 | CB | SER | B | 286 | −55.292 | −10.894 | −21.863 | 1.00 | 19.38 | C |
| ATOM | 12496 | OG | SER | B | 286 | −56.684 | −11.180 | −21.957 | 1.00 | 20.24 | O |
| ATOM | 12498 | C | SER | B | 286 | −53.106 | −11.267 | −23.032 | 1.00 | 18.91 | C |
| ATOM | 12499 | O | SER | B | 286 | −52.894 | −10.668 | −24.087 | 1.00 | 19.48 | O |
| ATOM | 12501 | N | PHE | B | 287 | −52.172 | −11.446 | −22.102 | 1.00 | 18.48 | N |
| ATOM | 12502 | CA | PHE | B | 287 | −50.768 | −11.065 | −22.339 | 1.00 | 18.30 | C |
| ATOM | 12504 | CB | PHE | B | 287 | −49.958 | −11.035 | −21.044 | 1.00 | 18.27 | C |
| ATOM | 12507 | CG | PHE | B | 287 | −50.040 | −9.740 | −20.324 | 1.00 | 18.59 | C |
| ATOM | 12508 | CD1 | PHE | B | 287 | −49.375 | −8.624 | −20.813 | 1.00 | 20.02 | C |
| ATOM | 12510 | CE1 | PHE | B | 287 | −49.456 | −7.410 | −20.152 | 1.00 | 20.57 | C |
| ATOM | 12512 | CZ | PHE | B | 287 | −50.208 | −7.308 | −18.985 | 1.00 | 20.02 | C |
| ATOM | 12514 | CE2 | PHE | B | 287 | −50.869 | −8.417 | −18.503 | 1.00 | 19.78 | C |
| ATOM | 12516 | CD2 | PHE | B | 287 | −50.781 | −9.623 | −19.164 | 1.00 | 19.05 | C |
| ATOM | 12518 | C | PHE | B | 287 | −50.067 | −11.978 | −23.339 | 1.00 | 18.01 | C |
| ATOM | 12519 | O | PHE | B | 287 | −49.374 | −11.498 | −24.229 | 1.00 | 18.00 | O |
| ATOM | 12521 | N | VAL | B | 288 | −50.236 | −13.286 | −23.194 | 1.00 | 17.69 | N |
| ATOM | 12522 | CA | VAL | B | 288 | −49.720 | −14.206 | −24.197 | 1.00 | 17.66 | C |

TABLE 3-7-continued

| | | | | | | | | | | | |
|---|---|---|---|---|---|---|---|---|---|---|---|
| \multicolumn{12}{c}{Coordinates of *P. tremuloides* IspS} |
| ATOM | 12524 | CB | VAL | B | 288 | −50.168 | −15.649 | −23.930 | 1.00 | 17.37 | C |
| ATOM | 12526 | CG1 | VAL | B | 288 | −49.937 | −16.529 | −25.134 | 1.00 | 16.24 | C |
| ATOM | 12530 | CG2 | VAL | B | 288 | −49.414 | −16.185 | −22.758 | 1.00 | 17.21 | C |
| ATOM | 12534 | C | VAL | B | 288 | −50.081 | −13.761 | −25.633 | 1.00 | 18.08 | C |
| ATOM | 12535 | O | VAL | B | 288 | −49.207 | −13.710 | −26.492 | 1.00 | 18.08 | O |
| ATOM | 12537 | N | THR | B | 289 | −51.327 | −13.396 | −25.895 | 1.00 | 18.42 | N |
| ATOM | 12538 | CA | THR | B | 289 | −51.683 | −13.001 | −27.256 | 1.00 | 19.33 | C |
| ATOM | 12540 | CB | THR | B | 289 | −53.171 | −12.736 | −27.401 | 1.00 | 19.35 | C |
| ATOM | 12542 | OG1 | THR | B | 289 | −53.573 | −11.895 | −26.321 | 1.00 | 21.59 | O |
| ATOM | 12544 | CG2 | THR | B | 289 | −53.973 | −14.046 | −27.350 | 1.00 | 19.09 | C |
| ATOM | 12548 | C | THR | B | 289 | −50.901 | −11.766 | −27.723 | 1.00 | 19.71 | C |
| ATOM | 12549 | O | THR | B | 289 | −50.469 | −11.707 | −28.891 | 1.00 | 19.88 | O |
| ATOM | 12551 | N | ILE | B | 290 | −50.689 | −10.796 | −26.829 | 1.00 | 19.94 | N |
| ATOM | 12552 | CA | ILE | B | 290 | −49.943 | −9.585 | −27.225 | 1.00 | 20.39 | C |
| ATOM | 12554 | CB | ILE | B | 290 | −50.069 | −8.410 | −26.221 | 1.00 | 20.50 | C |
| ATOM | 12556 | CG1 | ILE | B | 290 | −51.510 | −8.137 | −25.823 | 1.00 | 21.25 | C |
| ATOM | 12559 | CD1 | ILE | B | 290 | −51.650 | −6.854 | −25.002 | 1.00 | 21.58 | C |
| ATOM | 12563 | CG2 | ILE | B | 290 | −49.546 | −7.134 | −26.853 | 1.00 | 20.39 | C |
| ATOM | 12567 | C | ILE | B | 290 | −48.434 | −9.840 | −27.438 | 1.00 | 20.45 | C |
| ATOM | 12568 | O | ILE | B | 290 | −47.853 | −9.317 | −28.393 | 1.00 | 20.76 | O |
| ATOM | 12570 | N | ILE | B | 291 | −47.808 | −10.616 | −26.546 | 1.00 | 20.21 | N |
| ATOM | 12571 | CA | ILE | B | 291 | −46.375 | −10.869 | −26.618 | 1.00 | 19.87 | C |
| ATOM | 12573 | CB | ILE | B | 291 | −45.840 | −11.603 | −25.407 | 1.00 | 19.79 | C |
| ATOM | 12575 | CG1 | ILE | B | 291 | −46.205 | −10.879 | −24.102 | 1.00 | 19.71 | C |
| ATOM | 12578 | CD1 | ILE | B | 291 | −45.326 | −9.734 | −23.748 | 1.00 | 19.77 | C |
| ATOM | 12582 | CG2 | ILE | B | 291 | −44.336 | −11.747 | −25.516 | 1.00 | 18.91 | C |
| ATOM | 12586 | C | ILE | B | 291 | −46.134 | −11.735 | −27.825 | 1.00 | 20.44 | C |
| ATOM | 12587 | O | ILE | B | 291 | −45.233 | −11.481 | −28.600 | 1.00 | 20.35 | O |
| ATOM | 12589 | N | ASP | B | 292 | −46.965 | −12.751 | −28.005 | 1.00 | 21.33 | N |
| ATOM | 12590 | CA | ASP | B | 292 | −46.915 | −13.563 | −29.228 | 1.00 | 22.13 | C |
| ATOM | 12592 | CB | ASP | B | 292 | −48.120 | −14.508 | −29.316 | 1.00 | 22.40 | C |
| ATOM | 12595 | CG | ASP | B | 292 | −47.847 | −15.741 | −30.160 | 1.00 | 23.47 | C |
| ATOM | 12596 | OD1 | ASP | B | 292 | −46.852 | −15.765 | −30.923 | 1.00 | 24.83 | O |
| ATOM | 12597 | OD2 | ASP | B | 292 | −48.637 | −16.707 | −30.038 | 1.00 | 25.22 | O |
| ATOM | 12598 | C | ASP | B | 292 | −46.856 | −12.716 | −30.507 | 1.00 | 22.28 | C |
| ATOM | 12599 | O | ASP | B | 292 | −46.088 | −13.033 | −31.399 | 1.00 | 22.73 | O |
| ATOM | 12601 | N | ASP | B | 293 | −47.656 | −11.658 | −30.611 | 1.00 | 22.22 | N |
| ATOM | 12602 | CA | ASP | B | 293 | −47.630 | −10.828 | −31.822 | 1.00 | 22.43 | C |
| ATOM | 12604 | CB | ASP | B | 293 | −48.840 | −9.894 | −31.885 | 1.00 | 23.03 | C |
| ATOM | 12607 | CG | ASP | B | 293 | −50.157 | −10.644 | −31.959 | 1.00 | 24.69 | C |
| ATOM | 12608 | OD1 | ASP | B | 293 | −50.113 | −11.900 | −32.025 | 1.00 | 28.66 | O |
| ATOM | 12609 | OD2 | ASP | B | 293 | −51.231 | −9.986 | −31.930 | 1.00 | 23.57 | O |
| ATOM | 12610 | C | ASP | B | 293 | −46.354 | −9.997 | −31.921 | 1.00 | 21.94 | C |
| ATOM | 12611 | O | ASP | B | 293 | −45.898 | −9.674 | −33.019 | 1.00 | 22.31 | O |
| ATOM | 12613 | N | ILE | B | 294 | −45.783 | −9.643 | −30.780 | 1.00 | 21.05 | N |
| ATOM | 12614 | CA | ILE | B | 294 | −44.513 | −8.941 | −30.770 | 1.00 | 20.53 | C |
| ATOM | 12616 | CB | ILE | B | 294 | −44.166 | −8.448 | −29.344 | 1.00 | 20.42 | C |
| ATOM | 12618 | CG1 | ILE | B | 294 | −45.150 | −7.349 | −28.945 | 1.00 | 19.66 | C |
| ATOM | 12621 | CD1 | ILE | B | 294 | −45.057 | −6.956 | −27.536 | 1.00 | 18.81 | C |
| ATOM | 12625 | CG2 | ILE | B | 294 | −42.726 | −7.924 | −29.253 | 1.00 | 19.99 | C |
| ATOM | 12629 | C | ILE | B | 294 | −43.416 | −9.845 | −31.343 | 1.00 | 20.44 | C |
| ATOM | 12630 | O | ILE | B | 294 | −42.650 | −9.431 | −32.205 | 1.00 | 20.17 | O |
| ATOM | 12632 | N | TYR | B | 295 | −43.355 | −11.088 | −30.886 | 1.00 | 20.65 | N |
| ATOM | 12633 | CA | TYR | B | 295 | −42.313 | −12.008 | −31.353 | 1.00 | 20.76 | C |
| ATOM | 12635 | CB | TYR | B | 295 | −42.145 | −13.198 | −30.412 | 1.00 | 20.29 | C |
| ATOM | 12638 | CG | TYR | B | 295 | −41.393 | −12.926 | −29.129 | 1.00 | 17.92 | C |
| ATOM | 12639 | CD1 | TYR | B | 295 | −40.117 | −13.409 | −28.936 | 1.00 | 17.62 | C |
| ATOM | 12641 | CE1 | TYR | B | 295 | −39.427 | −13.195 | −27.747 | 1.00 | 17.12 | C |
| ATOM | 12643 | CZ | TYR | B | 295 | −40.022 | −12.493 | −26.730 | 1.00 | 16.61 | C |
| ATOM | 12644 | OH | TYR | B | 295 | −39.357 | −12.281 | −25.528 | 1.00 | 14.46 | O |
| ATOM | 12646 | CE2 | TYR | B | 295 | −41.296 | −12.008 | −26.911 | 1.00 | 16.82 | C |
| ATOM | 12648 | CD2 | TYR | B | 295 | −41.972 | −12.235 | −28.102 | 1.00 | 16.39 | C |
| ATOM | 12650 | C | TYR | B | 295 | −42.619 | −12.519 | −32.749 | 1.00 | 21.65 | C |
| ATOM | 12651 | O | TYR | B | 295 | −41.698 | −12.751 | −33.540 | 1.00 | 22.13 | O |
| ATOM | 12653 | N | ASP | B | 296 | −43.905 | −12.677 | −33.049 | 1.00 | 22.47 | N |
| ATOM | 12654 | CA | ASP | B | 296 | −44.327 | −13.316 | −34.285 | 1.00 | 23.52 | C |
| ATOM | 12656 | CB | ASP | B | 296 | −45.761 | −13.851 | −34.185 | 1.00 | 23.99 | C |
| ATOM | 12659 | CG | ASP | B | 296 | −46.134 | −14.744 | −35.369 | 1.00 | 26.22 | C |
| ATOM | 12660 | OD1 | ASP | B | 296 | −45.508 | −15.832 | −35.538 | 1.00 | 27.70 | O |
| ATOM | 12661 | OD2 | ASP | B | 296 | −47.052 | −14.348 | −36.128 | 1.00 | 28.78 | O |
| ATOM | 12662 | C | ASP | B | 296 | −44.228 | −12.392 | −35.478 | 1.00 | 23.68 | C |
| ATOM | 12663 | O | ASP | B | 296 | −43.673 | −12.784 | −36.502 | 1.00 | 24.01 | O |
| ATOM | 12665 | N | VAL | B | 297 | −44.765 | −11.178 | −35.364 | 1.00 | 23.90 | N |
| ATOM | 12666 | CA | VAL | B | 297 | −44.801 | −10.273 | −36.524 | 1.00 | 23.99 | C |
| ATOM | 12668 | CB | VAL | B | 297 | −46.251 | −10.003 | −36.973 | 1.00 | 23.87 | C |
| ATOM | 12670 | CG1 | VAL | B | 297 | −46.949 | −11.310 | −37.197 | 1.00 | 23.75 | C |
| ATOM | 12674 | CG2 | VAL | B | 297 | −47.002 | −9.136 | −35.966 | 1.00 | 23.05 | C |
| ATOM | 12678 | C | VAL | B | 297 | −44.060 | −8.940 | −36.383 | 1.00 | 24.27 | C |

TABLE 3-7-continued

| | | | | | | | | | | | |
|---|---|---|---|---|---|---|---|---|---|---|---|
| ATOM | 12679 | O | VAL | B | 297 | −43.485 | −8.465 | −37.342 | 1.00 | 23.84 | O |
| ATOM | 12681 | N | TYR | B | 298 | −44.058 | −8.347 | −35.199 | 1.00 | 24.87 | N |
| ATOM | 12682 | CA | TYR | B | 298 | −43.760 | −6.926 | −35.078 | 1.00 | 25.67 | C |
| ATOM | 12684 | CB | TYR | B | 298 | −44.656 | −6.294 | −34.010 | 1.00 | 26.06 | C |
| ATOM | 12687 | CG | TYR | B | 298 | −44.520 | −4.789 | −33.932 | 1.00 | 27.95 | C |
| ATOM | 12688 | CD1 | TYR | B | 298 | −45.097 | −3.968 | −34.901 | 1.00 | 29.74 | C |
| ATOM | 12690 | CE1 | TYR | B | 298 | −44.982 | −2.574 | −34.843 | 1.00 | 29.93 | C |
| ATOM | 12692 | CZ | TYR | B | 298 | −44.282 | −1.991 | −33.806 | 1.00 | 29.96 | C |
| ATOM | 12693 | OH | TYR | B | 298 | −44.165 | −.631 | −33.746 | 1.00 | 30.01 | O |
| ATOM | 12695 | CE2 | TYR | B | 298 | −43.697 | −2.777 | −32.829 | 1.00 | 30.39 | C |
| ATOM | 12697 | CD2 | TYR | B | 298 | −43.811 | −4.181 | −32.899 | 1.00 | 29.96 | C |
| ATOM | 12699 | C | TYR | B | 298 | −42.318 | −6.592 | −34.755 | 1.00 | 25.76 | C |
| ATOM | 12700 | O | TYR | B | 298 | −41.696 | −5.830 | −35.470 | 1.00 | 26.54 | O |
| ATOM | 12702 | N | GLY | B | 299 | −41.798 | −7.111 | −33.653 | 1.00 | 25.89 | N |
| ATOM | 12703 | CA | GLY | B | 299 | −40.473 | −6.706 | −33.167 | 1.00 | 25.78 | C |
| ATOM | 12706 | C | GLY | B | 299 | −39.346 | −7.341 | −33.951 | 1.00 | 25.52 | C |
| ATOM | 12707 | O | GLY | B | 299 | −39.513 | −8.410 | −34.525 | 1.00 | 26.04 | O |
| ATOM | 12709 | N | THR | B | 300 | −38.196 | −6.685 | −33.990 | 1.00 | 25.32 | N |
| ATOM | 12710 | CA | THR | B | 300 | −37.063 | −7.237 | −34.716 | 1.00 | 25.16 | C |
| ATOM | 12712 | CB | THR | B | 300 | −36.088 | −6.164 | −35.295 | 1.00 | 25.08 | C |
| ATOM | 12714 | OG1 | THR | B | 300 | −35.191 | −5.710 | −34.281 | 1.00 | 25.07 | O |
| ATOM | 12716 | CG2 | THR | B | 300 | −36.833 | −4.978 | −35.875 | 1.00 | 25.08 | C |
| ATOM | 12720 | C | THR | B | 300 | −36.324 | −8.139 | −33.771 | 1.00 | 25.13 | C |
| ATOM | 12721 | O | THR | B | 300 | −36.335 | −7.950 | −32.570 | 1.00 | 25.28 | O |
| ATOM | 12723 | N | LEU | B | 301 | −35.662 | −9.129 | −34.332 | 1.00 | 25.50 | N |
| ATOM | 12724 | CA | LEU | B | 301 | −34.918 | −10.093 | −33.538 | 1.00 | 25.42 | C |
| ATOM | 12726 | CB | LEU | B | 301 | −34.148 | −11.020 | −34.479 | 1.00 | 25.17 | C |
| ATOM | 12729 | CG | LEU | B | 301 | −33.624 | −12.338 | −33.941 | 1.00 | 24.95 | C |
| ATOM | 12731 | CD1 | LEU | B | 301 | −34.715 | −13.233 | −33.437 | 1.00 | 24.42 | C |
| ATOM | 12735 | CD2 | LEU | B | 301 | −32.900 | −12.998 | −35.080 | 1.00 | 26.50 | C |
| ATOM | 12739 | C | LEU | B | 301 | −33.995 | −9.425 | −32.485 | 1.00 | 25.54 | C |
| ATOM | 12740 | O | LEU | B | 301 | −33.843 | −9.959 | −31.394 | 1.00 | 25.35 | O |
| ATOM | 12742 | N | ASP | B | 302 | −33.417 | −8.257 | −32.782 | 1.00 | 25.68 | N |
| ATOM | 12743 | CA | ASP | B | 302 | −32.598 | −7.550 | −31.774 | 1.00 | 26.02 | C |
| ATOM | 12745 | CB | ASP | B | 302 | −31.800 | −6.377 | −32.378 | 1.00 | 26.37 | C |
| ATOM | 12748 | CG | ASP | B | 302 | −30.563 | −6.833 | −33.167 | 1.00 | 28.27 | C |
| ATOM | 12749 | OD1 | ASP | B | 302 | −29.508 | −6.156 | −33.048 | 1.00 | 29.05 | O |
| ATOM | 12750 | OD2 | ASP | B | 302 | −30.652 | −7.852 | −33.910 | 1.00 | 31.04 | O |
| ATOM | 12751 | C | ASP | B | 302 | −33.472 | −7.037 | −30.630 | 1.00 | 25.69 | C |
| ATOM | 12752 | O | ASP | B | 302 | −33.110 | −7.142 | −29.447 | 1.00 | 25.90 | O |
| ATOM | 12754 | N | GLU | B | 303 | −34.622 | −6.473 | −30.993 | 1.00 | 25.04 | N |
| ATOM | 12755 | CA | GLU | B | 303 | −35.600 | −6.029 | −30.011 | 1.00 | 24.33 | C |
| ATOM | 12757 | CB | GLU | B | 303 | −36.783 | −5.346 | −30.697 | 1.00 | 24.20 | C |
| ATOM | 12760 | CG | GLU | B | 303 | −36.399 | −4.109 | −31.466 | 1.00 | 24.23 | C |
| ATOM | 12763 | CD | GLU | B | 303 | −37.589 | −3.382 | −32.063 | 1.00 | 24.23 | C |
| ATOM | 12764 | OE1 | GLU | B | 303 | −38.496 | −4.065 | −32.604 | 1.00 | 22.66 | O |
| ATOM | 12765 | OE2 | GLU | B | 303 | −37.592 | −2.121 | −31.995 | 1.00 | 23.93 | O |
| ATOM | 12766 | C | GLU | B | 303 | −36.103 | −7.212 | −29.193 | 1.00 | 23.87 | C |
| ATOM | 12767 | O | GLU | B | 303 | −36.396 | −7.058 | −28.011 | 1.00 | 23.59 | O |
| ATOM | 12769 | N | LEU | B | 304 | −36.204 | −8.383 | −29.825 | 1.00 | 23.39 | N |
| ATOM | 12770 | CA | LEU | B | 304 | −36.766 | −9.570 | −29.166 | 1.00 | 23.23 | C |
| ATOM | 12772 | CB | LEU | B | 304 | −37.180 | −10.624 | −30.208 | 1.00 | 22.83 | C |
| ATOM | 12775 | CG | LEU | B | 304 | −38.381 | −10.217 | −31.074 | 1.00 | 22.06 | C |
| ATOM | 12777 | CD1 | LEU | B | 304 | −38.822 | −11.321 | −32.037 | 1.00 | 20.11 | C |
| ATOM | 12781 | CD2 | LEU | B | 304 | −39.551 | −9.800 | −30.163 | 1.00 | 21.94 | C |
| ATOM | 12785 | C | LEU | B | 304 | −35.810 | −10.147 | −28.106 | 1.00 | 23.37 | C |
| ATOM | 12786 | O | LEU | B | 304 | −36.248 | −10.785 | −27.141 | 1.00 | 23.22 | O |
| ATOM | 12788 | N | GLU | B | 305 | −34.514 | −9.892 | −28.283 | 1.00 | 23.30 | N |
| ATOM | 12789 | CA | GLU | B | 305 | −33.512 | −10.308 | −27.324 | 1.00 | 23.18 | C |
| ATOM | 12791 | CB | GLU | B | 305 | −32.114 | −10.176 | −27.899 | 1.00 | 23.58 | C |
| ATOM | 12794 | CG | GLU | B | 305 | −31.832 | −11.142 | −29.047 | 1.00 | 25.27 | C |
| ATOM | 12797 | CD | GLU | B | 305 | −31.306 | −12.488 | −28.585 | 1.00 | 27.91 | C |
| ATOM | 12798 | OE1 | GLU | B | 305 | −30.946 | −13.303 | −29.470 | 1.00 | 29.87 | O |
| ATOM | 12799 | OE2 | GLU | B | 305 | −31.244 | −12.728 | −27.351 | 1.00 | 29.28 | O |
| ATOM | 12800 | C | GLU | B | 305 | −33.633 | −9.440 | −26.104 | 1.00 | 22.52 | C |
| ATOM | 12801 | O | GLU | B | 305 | −33.793 | −9.956 | −25.005 | 1.00 | 23.39 | O |
| ATOM | 12803 | N | LEU | B | 306 | −33.576 | −8.124 | −26.274 | 1.00 | 21.51 | N |
| ATOM | 12804 | CA | LEU | B | 306 | −33.715 | −7.224 | −25.114 | 1.00 | 20.70 | C |
| ATOM | 12806 | CB | LEU | B | 306 | −33.899 | −5.764 | −25.544 | 1.00 | 20.59 | C |
| ATOM | 12809 | CG | LEU | B | 306 | −32.769 | −5.065 | −26.293 | 1.00 | 20.12 | C |
| ATOM | 12811 | CD1 | LEU | B | 306 | −32.992 | −3.576 | −26.203 | 1.00 | 19.89 | C |
| ATOM | 12815 | CD2 | LEU | B | 306 | −31.402 | −5.437 | −25.739 | 1.00 | 19.81 | C |
| ATOM | 12819 | C | LEU | B | 306 | −34.896 | −7.645 | −24.237 | 1.00 | 19.91 | C |
| ATOM | 12820 | O | LEU | B | 306 | −34.771 | −7.778 | −23.031 | 1.00 | 19.53 | O |
| ATOM | 12822 | N | PHE | B | 307 | −36.030 | −7.883 | −24.872 | 1.00 | 19.48 | N |
| ATOM | 12823 | CA | PHE | B | 307 | −37.231 | −8.267 | −24.170 | 1.00 | 19.36 | C |
| ATOM | 12825 | CB | PHE | B | 307 | −38.400 | −8.406 | −25.138 | 1.00 | 19.54 | C |
| ATOM | 12828 | CG | PHE | B | 307 | −39.729 | −8.296 | −24.482 | 1.00 | 19.66 | C |

TABLE 3-7-continued

| | | | | | | | | | | |
|---|---|---|---|---|---|---|---|---|---|---|
| ATOM | 12829 | CD1 | PHE | B | 307 | −40.365 | −7.079 | −24.400 | 1.00 | 21.03 C |
| ATOM | 12831 | CE1 | PHE | B | 307 | −41.590 | −6.968 | −23.787 | 1.00 | 21.62 C |
| ATOM | 12833 | CZ | PHE | B | 307 | −42.182 | −8.072 | −23.248 | 1.00 | 20.25 C |
| ATOM | 12835 | CE2 | PHE | B | 307 | −41.553 | −9.292 | −23.329 | 1.00 | 20.07 C |
| ATOM | 12837 | CD2 | PHE | B | 307 | −40.338 | −9.400 | −23.939 | 1.00 | 19.62 C |
| ATOM | 12839 | C | PHE | B | 307 | −37.039 | −9.577 | −23.443 | 1.00 | 19.22 C |
| ATOM | 12840 | O | PHE | B | 307 | −37.354 | −9.684 | −22.260 | 1.00 | 19.50 O |
| ATOM | 12842 | N | THR | B | 308 | −36.532 | −10.583 | −24.143 | 1.00 | 18.96 N |
| ATOM | 12843 | CA | THR | B | 308 | −36.321 | −11.874 | −23.511 | 1.00 | 18.84 C |
| ATOM | 12845 | CB | THR | B | 308 | −35.774 | −12.879 | −24.490 | 1.00 | 18.62 C |
| ATOM | 12847 | OG1 | THR | B | 308 | −36.687 | −12.988 | −25.579 | 1.00 | 18.88 O |
| ATOM | 12849 | CG2 | THR | B | 308 | −35.626 | −14.228 | −23.833 | 1.00 | 18.74 C |
| ATOM | 12853 | C | THR | B | 308 | −35.384 | −11.737 | −22.317 | 1.00 | 19.04 C |
| ATOM | 12854 | O | THR | B | 308 | −35.686 | −12.244 | −21.233 | 1.00 | 18.69 O |
| ATOM | 12856 | N | ASP | B | 309 | −34.264 | −11.031 | −22.511 | 1.00 | 19.36 N |
| ATOM | 12857 | CA | ASP | B | 309 | −33.335 | −10.751 | −21.421 | 1.00 | 19.65 C |
| ATOM | 12859 | CB | ASP | B | 309 | −32.121 | −9.983 | −21.942 | 1.00 | 19.92 C |
| ATOM | 12862 | CG | ASP | B | 309 | −31.171 | −9.536 | −20.814 | 1.00 | 23.51 C |
| ATOM | 12863 | OD1 | ASP | B | 309 | −30.520 | −10.412 | −20.175 | 1.00 | 27.27 O |
| ATOM | 12864 | OD2 | ASP | B | 309 | −31.076 | −8.299 | −20.561 | 1.00 | 27.40 O |
| ATOM | 12865 | C | ASP | B | 309 | −34.048 | −9.977 | −20.295 | 1.00 | 19.08 C |
| ATOM | 12866 | O | ASP | B | 309 | −33.912 | −10.308 | −19.124 | 1.00 | 18.55 O |
| ATOM | 12868 | N | ALA | B | 310 | −34.836 | −8.975 | −20.665 | 1.00 | 18.93 N |
| ATOM | 12869 | CA | ALA | B | 310 | −35.546 | −8.151 | −19.688 | 1.00 | 19.12 C |
| ATOM | 12871 | CB | ALA | B | 310 | −36.346 | −7.062 | −20.380 | 1.00 | 18.79 C |
| ATOM | 12875 | C | ALA | B | 310 | −36.462 | −8.965 | −18.784 | 1.00 | 19.36 C |
| ATOM | 12876 | O | ALA | B | 310 | −36.560 | −8.696 | −17.577 | 1.00 | 19.58 O |
| ATOM | 12878 | N | VAL | B | 311 | −37.143 | −9.942 | −19.370 | 1.00 | 19.61 N |
| ATOM | 12879 | CA | VAL | B | 311 | −37.996 | −10.845 | −18.611 | 1.00 | 19.68 C |
| ATOM | 12881 | CB | VAL | B | 311 | −38.867 | −11.682 | −19.555 | 1.00 | 19.46 C |
| ATOM | 12883 | CG1 | VAL | B | 311 | −39.948 | −10.825 | −20.123 | 1.00 | 18.49 C |
| ATOM | 12887 | CG2 | VAL | B | 311 | −39.469 | −12.863 | −18.843 | 1.00 | 19.31 C |
| ATOM | 12891 | C | VAL | B | 311 | −37.161 | −11.726 | −17.673 | 1.00 | 20.46 C |
| ATOM | 12892 | O | VAL | B | 311 | −37.479 | −11.843 | −16.494 | 1.00 | 20.25 O |
| ATOM | 12894 | N | GLU | B | 312 | −36.085 | −12.317 | −18.189 | 1.00 | 21.67 N |
| ATOM | 12895 | CA | GLU | B | 312 | −35.198 | −13.168 | −17.384 | 1.00 | 22.65 C |
| ATOM | 12897 | CB | GLU | B | 312 | −34.056 | −13.708 | −18.239 | 1.00 | 23.03 C |
| ATOM | 12900 | CG | GLU | B | 312 | −34.454 | −14.764 | −19.261 | 1.00 | 24.88 C |
| ATOM | 12903 | CD | GLU | B | 312 | −33.335 | −15.077 | −20.267 | 1.00 | 27.34 C |
| ATOM | 12904 | OE1 | GLU | B | 312 | −33.485 | −16.057 | −21.028 | 1.00 | 29.07 O |
| ATOM | 12905 | OE2 | GLU | B | 312 | −32.316 | −14.342 | −20.313 | 1.00 | 28.63 O |
| ATOM | 12906 | C | GLU | B | 312 | −34.598 | −12.443 | −16.167 | 1.00 | 23.09 C |
| ATOM | 12907 | O | GLU | B | 312 | −34.506 | −13.007 | −15.082 | 1.00 | 23.04 O |
| ATOM | 12909 | N | ARG | B | 313 | −34.186 | −11.199 | −16.335 | 1.00 | 23.67 N |
| ATOM | 12910 | CA | ARG | B | 313 | −33.590 | −10.486 | −15.222 | 1.00 | 24.60 C |
| ATOM | 12912 | CB | ARG | B | 313 | −32.609 | −9.436 | −15.735 | 1.00 | 25.26 C |
| ATOM | 12915 | CG | ARG | B | 313 | −31.333 | −10.030 | −16.398 | 1.00 | 27.83 C |
| ATOM | 12918 | CD | ARG | B | 313 | −30.289 | −8.943 | −16.754 | 1.00 | 31.87 C |
| ATOM | 12921 | NE | ARG | B | 313 | −30.922 | −7.793 | −17.430 | 1.00 | 35.71 N |
| ATOM | 12923 | CZ | ARG | B | 313 | −31.341 | −6.661 | −16.837 | 1.00 | 38.42 C |
| ATOM | 12924 | NH1 | ARG | B | 313 | −31.189 | −6.452 | −15.522 | 1.00 | 39.15 N |
| ATOM | 12927 | NH2 | ARG | B | 313 | −31.919 | −5.711 | −17.576 | 1.00 | 39.25 N |
| ATOM | 12930 | C | ARG | B | 313 | −34.638 | −9.879 | −14.280 | 1.00 | 24.67 C |
| ATOM | 12931 | O | ARG | B | 313 | −34.359 | −9.645 | −13.117 | 1.00 | 24.09 O |
| ATOM | 12933 | N | TRP | B | 314 | −35.843 | −9.635 | −14.781 | 1.00 | 25.60 N |
| ATOM | 12934 | CA | TRP | B | 314 | −36.971 | −9.180 | −13.951 | 1.00 | 26.20 C |
| ATOM | 12936 | CB | TRP | B | 314 | −37.488 | −10.339 | −13.097 | 1.00 | 25.90 C |
| ATOM | 12939 | CG | TRP | B | 314 | −38.912 | −10.184 | −12.662 | 1.00 | 23.93 C |
| ATOM | 12940 | CD1 | TRP | B | 314 | −39.355 | −9.854 | −11.424 | 1.00 | 22.76 C |
| ATOM | 12942 | NE1 | TRP | B | 314 | −40.727 | −9.804 | −11.412 | 1.00 | 21.93 N |
| ATOM | 12944 | CE2 | TRP | B | 314 | −41.189 | −10.107 | −12.659 | 1.00 | 20.38 C |
| ATOM | 12945 | CD2 | TRP | B | 314 | −40.074 | −10.352 | −13.473 | 1.00 | 21.17 C |
| ATOM | 12946 | CE3 | TRP | B | 314 | −40.277 | −10.684 | −14.811 | 1.00 | 20.19 C |
| ATOM | 12948 | CZ3 | TRP | B | 314 | −41.549 | −10.766 | −15.280 | 1.00 | 19.79 C |
| ATOM | 12950 | CH2 | TRP | B | 314 | −42.640 | −10.512 | −14.445 | 1.00 | 21.00 C |
| ATOM | 12952 | CZ2 | TRP | B | 314 | −42.474 | −10.179 | −13.130 | 1.00 | 20.60 C |
| ATOM | 12954 | C | TRP | B | 314 | −36.620 | −7.966 | −13.076 | 1.00 | 27.57 C |
| ATOM | 12955 | O | TRP | B | 314 | −36.890 | −7.935 | −11.870 | 1.00 | 27.56 O |
| ATOM | 12957 | N | ASP | B | 315 | −36.039 | −6.959 | −13.718 | 1.00 | 29.12 N |
| ATOM | 12958 | CA | ASP | B | 315 | −35.452 | −5.822 | −13.027 | 1.00 | 30.46 C |
| ATOM | 12960 | CB | ASP | B | 315 | −33.935 | −5.796 | −13.315 | 1.00 | 30.84 C |
| ATOM | 12963 | CG | ASP | B | 315 | −33.227 | −4.551 | −12.772 | 1.00 | 32.75 C |
| ATOM | 12964 | OD1 | ASP | B | 315 | −33.747 | −3.904 | −11.830 | 1.00 | 35.67 O |
| ATOM | 12965 | OD2 | ASP | B | 315 | −32.128 | −4.222 | −13.295 | 1.00 | 34.91 O |
| ATOM | 12966 | C | ASP | B | 315 | −36.157 | −4.592 | −13.557 | 1.00 | 31.10 C |
| ATOM | 12967 | O | ASP | B | 315 | −35.888 | −4.157 | −14.674 | 1.00 | 31.35 O |
| ATOM | 12969 | N | VAL | B | 316 | −37.088 | −4.044 | −12.781 | 1.00 | 32.06 N |
| ATOM | 12970 | CA | VAL | B | 316 | −37.864 | −2.896 | −13.262 | 1.00 | 32.65 C |

TABLE 3-7-continued

Coordinates of *P. tremuloides* IspS

| ATOM | 12972 | CB | VAL | B | 316 | −39.016 | −2.510 | −12.334 | 1.00 | 32.45 | C |
|---|---|---|---|---|---|---|---|---|---|---|---|
| ATOM | 12974 | CG1 | VAL | B | 316 | −39.911 | −1.499 | −13.012 | 1.00 | 32.15 | C |
| ATOM | 12978 | CG2 | VAL | B | 316 | −38.490 | −1.960 | −11.040 | 1.00 | 32.91 | C |
| ATOM | 12982 | C | VAL | B | 316 | −36.964 | −1.692 | −13.442 | 1.00 | 33.43 | C |
| ATOM | 12983 | O | VAL | B | 316 | −37.228 | −.854 | −14.294 | 1.00 | 33.74 | O |
| ATOM | 12985 | N | ASN | B | 317 | −35.881 | −1.628 | −12.663 | 1.00 | 34.29 | N |
| ATOM | 12986 | CA | ASN | B | 317 | −34.937 | −.510 | −12.730 | 1.00 | 34.63 | C |
| ATOM | 12988 | CB | ASN | B | 317 | −33.995 | −.526 | −11.505 | 1.00 | 34.50 | C |
| ATOM | 12991 | CG | ASN | B | 317 | −34.692 | −.084 | −10.201 | 1.00 | 34.08 | C |
| ATOM | 12992 | OD1 | ASN | B | 317 | −35.198 | 1.042 | −10.104 | 1.00 | 33.72 | O |
| ATOM | 12993 | ND2 | ASN | B | 317 | −34.690 | −.961 | −9.193 | 1.00 | 31.22 | N |
| ATOM | 12996 | C | ASN | B | 317 | −34.124 | −.481 | −14.029 | 1.00 | 35.21 | C |
| ATOM | 12997 | O | ASN | B | 317 | −33.196 | .296 | −14.127 | 1.00 | 35.52 | O |
| ATOM | 12999 | N | ALA | B | 318 | −34.470 | −1.318 | −15.013 | 1.00 | 35.89 | N |
| ATOM | 13000 | CA | ALA | B | 318 | −33.757 | −1.382 | −16.299 | 1.00 | 36.48 | C |
| ATOM | 13002 | CB | ALA | B | 318 | −32.727 | −2.508 | −16.253 | 1.00 | 36.49 | C |
| ATOM | 13006 | C | ALA | B | 318 | −34.695 | −1.525 | −17.534 | 1.00 | 37.02 | C |
| ATOM | 13007 | O | ALA | B | 318 | −34.297 | −1.984 | −18.616 | 1.00 | 36.52 | O |
| ATOM | 13009 | N | ILE | B | 319 | −35.952 | −1.137 | −17.339 | 1.00 | 37.76 | N |
| ATOM | 13010 | CA | ILE | B | 319 | −36.848 | −.733 | −18.424 | 1.00 | 38.08 | C |
| ATOM | 13012 | CB | ILE | B | 319 | −37.926 | .247 | −17.893 | 1.00 | 38.11 | C |
| ATOM | 13014 | CG1 | ILE | B | 319 | −39.110 | −.495 | −17.293 | 1.00 | 38.08 | C |
| ATOM | 13017 | CD1 | ILE | B | 319 | −40.068 | .451 | −16.596 | 1.00 | 38.27 | C |
| ATOM | 13021 | CG2 | ILE | B | 319 | −38.408 | 1.189 | −18.996 | 1.00 | 37.84 | C |
| ATOM | 13025 | C | ILE | B | 319 | −36.134 | .053 | −19.516 | 1.00 | 38.29 | C |
| ATOM | 13026 | O | ILE | B | 319 | −36.192 | −.324 | −20.677 | 1.00 | 38.68 | O |
| ATOM | 13028 | N | ASN | B | 320 | −35.460 | 1.141 | −19.125 | 1.00 | 38.36 | N |
| ATOM | 13029 | CA | ASN | B | 320 | −34.977 | 2.168 | −20.074 | 1.00 | 38.17 | C |
| ATOM | 13031 | CB | ASN | B | 320 | −34.278 | 3.331 | −19.331 | 1.00 | 38.16 | C |
| ATOM | 13034 | CG | ASN | B | 320 | −35.258 | 4.207 | −18.514 | 1.00 | 37.87 | C |
| ATOM | 13035 | OD1 | ASN | B | 320 | −36.366 | 4.542 | −18.955 | 1.00 | 36.50 | O |
| ATOM | 13036 | ND2 | ASN | B | 320 | −34.827 | 4.589 | −17.322 | 1.00 | 38.12 | N |
| ATOM | 13039 | C | ASN | B | 320 | −34.082 | 1.643 | −21.206 | 1.00 | 37.78 | C |
| ATOM | 13040 | O | ASN | B | 320 | −33.856 | 2.332 | −22.181 | 1.00 | 37.76 | O |
| ATOM | 13042 | N | ASP | B | 321 | −33.600 | .416 | −21.083 | 1.00 | 37.46 | N |
| ATOM | 13043 | CA | ASP | B | 321 | −32.852 | −.224 | −22.162 | 1.00 | 37.25 | C |
| ATOM | 13045 | CB | ASP | B | 321 | −32.091 | −1.467 | −21.629 | 1.00 | 37.83 | C |
| ATOM | 13048 | CG | ASP | B | 321 | −31.351 | −1.207 | −20.285 | 1.00 | 39.33 | C |
| ATOM | 13049 | OD1 | ASP | B | 321 | −31.247 | −.021 | −19.871 | 1.00 | 40.72 | O |
| ATOM | 13050 | OD2 | ASP | B | 321 | −30.887 | −2.199 | −19.648 | 1.00 | 39.62 | O |
| ATOM | 13051 | C | ASP | B | 321 | −33.764 | −.636 | −23.339 | 1.00 | 35.99 | C |
| ATOM | 13052 | O | ASP | B | 321 | −33.273 | −.904 | −24.436 | 1.00 | 35.87 | O |
| ATOM | 13054 | N | LEU | B | 322 | −35.076 | −.674 | −23.111 | 1.00 | 34.66 | N |
| ATOM | 13055 | CA | LEU | B | 322 | −36.024 | −1.263 | −24.061 | 1.00 | 33.77 | C |
| ATOM | 13057 | CB | LEU | B | 322 | −37.180 | −1.961 | −23.327 | 1.00 | 33.65 | C |
| ATOM | 13060 | CG | LEU | B | 322 | −36.994 | −3.260 | −22.544 | 1.00 | 32.41 | C |
| ATOM | 13062 | CD1 | LEU | B | 322 | −38.223 | −3.482 | −21.693 | 1.00 | 31.54 | C |
| ATOM | 13066 | CD2 | LEU | B | 322 | −36.769 | −4.432 | −23.460 | 1.00 | 30.73 | C |
| ATOM | 13070 | C | LEU | B | 322 | −36.670 | −.243 | −24.982 | 1.00 | 33.32 | C |
| ATOM | 13071 | O | LEU | B | 322 | −36.910 | .893 | −24.570 | 1.00 | 33.37 | O |
| ATOM | 13073 | N | PRO | B | 323 | −37.005 | −.667 | −26.218 | 1.00 | 32.72 | N |
| ATOM | 13074 | CA | PRO | B | 323 | −37.856 | .068 | −27.126 | 1.00 | 32.42 | C |
| ATOM | 13076 | CB | PRO | B | 323 | −38.239 | −.985 | −28.158 | 1.00 | 32.28 | C |
| ATOM | 13079 | CG | PRO | B | 323 | −37.098 | −1.849 | −28.231 | 1.00 | 32.46 | C |
| ATOM | 13082 | CD | PRO | B | 323 | −36.498 | −1.891 | −26.857 | 1.00 | 32.79 | C |
| ATOM | 13085 | C | PRO | B | 323 | −39.115 | .576 | −26.453 | 1.00 | 32.50 | C |
| ATOM | 13086 | O | PRO | B | 323 | −39.655 | −.083 | −25.550 | 1.00 | 32.46 | O |
| ATOM | 13087 | N | ASP | B | 324 | −39.590 | 1.725 | −26.923 | 1.00 | 32.44 | N |
| ATOM | 13088 | CA | ASP | B | 324 | −40.729 | 2.387 | −26.318 | 1.00 | 32.44 | C |
| ATOM | 13090 | CB | ASP | B | 324 | −41.059 | 3.678 | −27.071 | 1.00 | 32.91 | C |
| ATOM | 13093 | CG | ASP | B | 324 | −40.241 | 4.873 | −26.576 | 1.00 | 34.17 | C |
| ATOM | 13094 | OD1 | ASP | B | 324 | −39.507 | 4.728 | −25.562 | 1.00 | 35.83 | O |
| ATOM | 13095 | OD2 | ASP | B | 324 | −40.351 | 5.960 | −27.196 | 1.00 | 35.42 | O |
| ATOM | 13096 | C | ASP | B | 324 | −41.967 | 1.504 | −26.186 | 1.00 | 31.78 | C |
| ATOM | 13097 | O | ASP | B | 324 | −42.546 | 1.440 | −25.102 | 1.00 | 31.77 | O |
| ATOM | 13099 | N | TYR | B | 325 | −42.368 | .821 | −27.258 | 1.00 | 30.99 | N |
| ATOM | 13100 | CA | TYR | B | 325 | −43.519 | −.086 | −27.167 | 1.00 | 30.49 | C |
| ATOM | 13102 | CB | TYR | B | 325 | −43.941 | −.640 | −28.536 | 1.00 | 30.28 | C |
| ATOM | 13105 | CG | TYR | B | 325 | −43.027 | −1.688 | −29.134 | 1.00 | 30.25 | C |
| ATOM | 13106 | CD1 | TYR | B | 325 | −41.917 | −1.332 | −29.893 | 1.00 | 29.81 | C |
| ATOM | 13108 | CE1 | TYR | B | 325 | −41.089 | −2.300 | −30.449 | 1.00 | 29.74 | C |
| ATOM | 13110 | CZ | TYR | B | 325 | −41.371 | −3.643 | −30.258 | 1.00 | 30.22 | C |
| ATOM | 13111 | OH | TYR | B | 325 | −40.565 | −4.625 | −30.805 | 1.00 | 31.28 | O |
| ATOM | 13113 | CE2 | TYR | B | 325 | −42.466 | −4.015 | −29.519 | 1.00 | 30.23 | C |
| ATOM | 13115 | CD2 | TYR | B | 325 | −43.288 | −3.038 | −28.963 | 1.00 | 30.49 | C |
| ATOM | 13117 | C | TYR | B | 325 | −43.284 | −1.221 | −26.168 | 1.00 | 30.14 | C |
| ATOM | 13118 | O | TYR | B | 325 | −44.219 | −1.638 | −25.483 | 1.00 | 30.19 | O |
| ATOM | 13120 | N | MET | B | 326 | −42.048 | −1.700 | −26.060 | 1.00 | 29.74 | N |

TABLE 3-7-continued

Coordinates of *P. tremuloides* IspS

| ATOM | 13121 | CA | MET | B | 326 | −41.755 | −2.820 | −25.155 | 1.00 | 29.82 | C |
|---|---|---|---|---|---|---|---|---|---|---|---|
| ATOM | 13123 | CB | MET | B | 326 | −40.461 | −3.541 | −25.549 | 1.00 | 29.69 | C |
| ATOM | 13126 | CG | MET | B | 326 | −40.650 | −4.510 | −26.686 | 1.00 | 28.83 | C |
| ATOM | 13129 | SD | MET | B | 326 | −39.123 | −5.272 | −27.204 | 1.00 | 26.99 | S |
| ATOM | 13130 | CE | MET | B | 326 | −39.761 | −6.499 | −28.328 | 1.00 | 29.13 | C |
| ATOM | 13134 | C | MET | B | 326 | −41.696 | −2.402 | −23.683 | 1.00 | 29.92 | C |
| ATOM | 13135 | O | MET | B | 326 | −42.032 | −3.204 | −22.801 | 1.00 | 29.75 | O |
| ATOM | 13137 | N | LYS | B | 327 | −41.251 | −1.166 | −23.429 | 1.00 | 29.68 | N |
| ATOM | 13138 | CA | LYS | B | 327 | −41.318 | −.578 | −22.088 | 1.00 | 29.46 | C |
| ATOM | 13140 | CB | LYS | B | 327 | −41.016 | .921 | −22.114 | 1.00 | 29.93 | C |
| ATOM | 13143 | CG | LYS | B | 327 | −39.572 | 1.305 | −21.951 | 1.00 | 31.63 | C |
| ATOM | 13146 | CD | LYS | B | 327 | −39.410 | 2.803 | −22.249 | 1.00 | 34.93 | C |
| ATOM | 13149 | CE | LYS | B | 327 | −37.986 | 3.291 | −22.021 | 1.00 | 36.86 | C |
| ATOM | 13152 | NZ | LYS | B | 327 | −37.642 | 4.436 | −22.917 | 1.00 | 37.83 | N |
| ATOM | 13156 | C | LYS | B | 327 | −42.708 | −.752 | −21.531 | 1.00 | 28.46 | C |
| ATOM | 13157 | O | LYS | B | 327 | −42.879 | −1.314 | −20.461 | 1.00 | 28.54 | O |
| ATOM | 13159 | N | LEU | B | 328 | −43.696 | −.258 | −22.268 | 1.00 | 27.39 | N |
| ATOM | 13160 | CA | LEU | B | 328 | −45.056 | −.216 | −21.785 | 1.00 | 26.79 | C |
| ATOM | 13162 | CB | LEU | B | 328 | −45.946 | .519 | −22.773 | 1.00 | 26.68 | C |
| ATOM | 13165 | CG | LEU | B | 328 | −47.265 | 1.034 | −22.212 | 1.00 | 26.00 | C |
| ATOM | 13167 | CD1 | LEU | B | 328 | −47.010 | 1.964 | −21.036 | 1.00 | 24.88 | C |
| ATOM | 13171 | CD2 | LEU | B | 328 | −48.051 | 1.740 | −23.308 | 1.00 | 24.55 | C |
| ATOM | 13175 | C | LEU | B | 328 | −45.560 | −1.628 | −21.587 | 1.00 | 26.70 | C |
| ATOM | 13176 | O | LEU | B | 328 | −46.110 | −1.983 | −20.543 | 1.00 | 27.03 | O |
| ATOM | 13178 | N | CYS | B | 329 | −45.341 | −2.453 | −22.591 | 1.00 | 26.39 | N |
| ATOM | 13179 | CA | CYS | B | 329 | −45.750 | −3.843 | −22.524 | 1.00 | 26.12 | C |
| ATOM | 13181 | CB | CYS | B | 329 | −45.382 | −4.526 | −23.838 | 1.00 | 26.47 | C |
| ATOM | 13184 | SG | CYS | B | 329 | −45.857 | −6.236 | −23.880 | 1.00 | 30.60 | S |
| ATOM | 13186 | C | CYS | B | 329 | −45.124 | −4.568 | −21.319 | 1.00 | 24.45 | C |
| ATOM | 13187 | O | CYS | B | 329 | −45.829 | −5.105 | −20.486 | 1.00 | 23.93 | O |
| ATOM | 13189 | N | PHE | B | 330 | −43.801 | −4.553 | −21.228 | 1.00 | 23.30 | N |
| ATOM | 13190 | CA | PHE | B | 330 | −43.087 | −5.220 | −20.141 | 1.00 | 22.47 | C |
| ATOM | 13192 | CB | PHE | B | 330 | −41.575 | −5.019 | −20.267 | 1.00 | 22.42 | C |
| ATOM | 13195 | CG | PHE | B | 330 | −40.800 | −5.518 | −19.076 | 1.00 | 22.37 | C |
| ATOM | 13196 | CD1 | PHE | B | 330 | −40.502 | −6.864 | −18.940 | 1.00 | 22.47 | C |
| ATOM | 13198 | CE1 | PHE | B | 330 | −39.799 | −7.339 | −17.836 | 1.00 | 21.64 | C |
| ATOM | 13200 | CZ | PHE | B | 330 | −39.379 | −6.472 | −16.866 | 1.00 | 21.50 | C |
| ATOM | 13202 | CE2 | PHE | B | 330 | −39.659 | −5.122 | −16.983 | 1.00 | 21.92 | C |
| ATOM | 13204 | CD2 | PHE | B | 330 | −40.374 | −4.648 | −18.084 | 1.00 | 22.29 | C |
| ATOM | 13206 | C | PHE | B | 330 | −43.524 | −4.739 | −18.765 | 1.00 | 21.87 | C |
| ATOM | 13207 | O | PHE | B | 330 | −43.779 | −5.552 | −17.875 | 1.00 | 21.98 | O |
| ATOM | 13209 | N | LEU | B | 331 | −43.594 | −3.427 | −18.573 | 1.00 | 20.88 | N |
| ATOM | 13210 | CA | LEU | B | 331 | −43.997 | −2.894 | −17.276 | 1.00 | 20.25 | C |
| ATOM | 13212 | CB | LEU | B | 331 | −43.927 | −1.354 | −17.257 | 1.00 | 20.06 | C |
| ATOM | 13215 | CG | LEU | B | 331 | −44.124 | −.628 | −15.912 | 1.00 | 19.21 | C |
| ATOM | 13217 | CD1 | LEU | B | 331 | −43.542 | −1.408 | −14.737 | 1.00 | 18.78 | C |
| ATOM | 13221 | CD2 | LEU | B | 331 | −43.555 | .770 | −15.957 | 1.00 | 15.75 | C |
| ATOM | 13225 | C | LEU | B | 331 | −45.398 | −3.408 | −16.902 | 1.00 | 19.99 | C |
| ATOM | 13226 | O | LEU | B | 331 | −45.606 | −3.860 | −15.771 | 1.00 | 19.67 | O |
| ATOM | 13228 | N | ALA | B | 332 | −46.336 | −3.373 | −17.860 | 1.00 | 19.56 | N |
| ATOM | 13229 | CA | ALA | B | 332 | −47.695 | −3.882 | −17.629 | 1.00 | 19.24 | C |
| ATOM | 13231 | CB | ALA | B | 332 | −48.528 | −3.802 | −18.891 | 1.00 | 18.58 | C |
| ATOM | 13235 | C | ALA | B | 332 | −47.637 | −5.321 | −17.108 | 1.00 | 19.23 | C |
| ATOM | 13236 | O | ALA | B | 332 | −48.235 | −5.650 | −16.079 | 1.00 | 19.18 | O |
| ATOM | 13238 | N | LEU | B | 333 | −46.891 | −6.162 | −17.816 | 1.00 | 19.16 | N |
| ATOM | 13239 | CA | LEU | B | 333 | −46.727 | −7.554 | −17.438 | 1.00 | 19.08 | C |
| ATOM | 13241 | CB | LEU | B | 333 | −45.830 | −8.260 | −18.462 | 1.00 | 18.97 | C |
| ATOM | 13244 | CG | LEU | B | 333 | −45.511 | −9.758 | −18.307 | 1.00 | 19.18 | C |
| ATOM | 13246 | CD1 | LEU | B | 333 | −46.779 | −10.611 | −18.121 | 1.00 | 18.09 | C |
| ATOM | 13250 | CD2 | LEU | B | 333 | −44.676 | −10.262 | −19.499 | 1.00 | 17.17 | C |
| ATOM | 13254 | C | LEU | B | 333 | −46.111 | −7.616 | −16.042 | 1.00 | 19.16 | C |
| ATOM | 13255 | O | LEU | B | 333 | −46.629 | −8.279 | −15.137 | 1.00 | 18.97 | O |
| ATOM | 13257 | N | TYR | B | 334 | −45.013 | −6.887 | −15.884 | 1.00 | 19.23 | N |
| ATOM | 13258 | CA | TYR | B | 334 | −44.212 | −6.906 | −14.664 | 1.00 | 19.33 | C |
| ATOM | 13260 | CB | TYR | B | 334 | −43.092 | −5.873 | −14.785 | 1.00 | 19.43 | C |
| ATOM | 13263 | CG | TYR | B | 334 | −42.190 | −5.748 | −13.596 | 1.00 | 19.44 | C |
| ATOM | 13264 | CD1 | TYR | B | 334 | −41.006 | −6.464 | −13.524 | 1.00 | 20.60 | C |
| ATOM | 13266 | CE1 | TYR | B | 334 | −40.148 | −6.347 | −12.442 | 1.00 | 20.77 | C |
| ATOM | 13268 | CZ | TYR | B | 334 | −40.474 | −5.503 | −11.417 | 1.00 | 21.51 | C |
| ATOM | 13269 | OH | TYR | B | 334 | −39.628 | −5.387 | −10.353 | 1.00 | 21.42 | O |
| ATOM | 13271 | CE2 | TYR | B | 334 | −41.646 | −4.768 | −11.466 | 1.00 | 22.15 | C |
| ATOM | 13273 | CD2 | TYR | B | 334 | −42.495 | −4.892 | −12.565 | 1.00 | 20.55 | C |
| ATOM | 13275 | C | TYR | B | 334 | −45.065 | −6.614 | −13.443 | 1.00 | 19.37 | C |
| ATOM | 13276 | O | TYR | B | 334 | −44.980 | −7.337 | −12.441 | 1.00 | 19.94 | O |
| ATOM | 13278 | N | ASN | B | 335 | −45.888 | −5.565 | −13.527 | 1.00 | 18.83 | N |
| ATOM | 13279 | CA | ASN | B | 335 | −46.784 | −5.236 | −12.443 | 1.00 | 18.37 | C |
| ATOM | 13281 | CB | ASN | B | 335 | −47.452 | −3.896 | −12.675 | 1.00 | 18.52 | C |
| ATOM | 13284 | CG | ASN | B | 335 | −46.493 | −2.742 | −12.518 | 1.00 | 19.27 | C |

TABLE 3-7-continued

Coordinates of *P. tremuloides* IspS

| ATOM | 13285 | OD1 | ASN | B | 335 | −45.421 | −2.906 | −11.953 | 1.00 | 21.25 | O |
|---|---|---|---|---|---|---|---|---|---|---|---|
| ATOM | 13286 | ND2 | ASN | B | 335 | −46.872 | −1.566 | −13.022 | 1.00 | 19.24 | N |
| ATOM | 13289 | C | ASN | B | 335 | −47.812 | −6.333 | −12.291 | 1.00 | 18.22 | C |
| ATOM | 13290 | O | ASN | B | 335 | −47.966 | −6.891 | −11.207 | 1.00 | 18.53 | O |
| ATOM | 13292 | N | THR | B | 336 | −48.481 | −6.697 | −13.379 | 1.00 | 17.95 | N |
| ATOM | 13293 | CA | THR | B | 336 | −49.525 | −7.728 | −13.301 | 1.00 | 17.61 | C |
| ATOM | 13295 | CB | THR | B | 336 | −49.980 | −8.204 | −14.676 | 1.00 | 17.36 | C |
| ATOM | 13297 | OG1 | THR | B | 336 | −50.249 | −7.065 | −15.500 | 1.00 | 17.02 | O |
| ATOM | 13299 | CG2 | THR | B | 336 | −51.228 | −9.044 | −14.551 | 1.00 | 16.07 | C |
| ATOM | 13303 | C | THR | B | 336 | −49.065 | −8.941 | −12.501 | 1.00 | 17.75 | C |
| ATOM | 13304 | O | THR | B | 336 | −49.788 | −9.429 | −11.621 | 1.00 | 18.09 | O |
| ATOM | 13306 | N | ILE | B | 337 | −47.859 | −9.411 | −12.785 | 1.00 | 17.69 | N |
| ATOM | 13307 | CA | ILE | B | 337 | −47.384 | −10.630 | −12.165 | 1.00 | 17.74 | C |
| ATOM | 13309 | CB | ILE | B | 337 | −46.228 | −11.245 | −12.949 | 1.00 | 17.40 | C |
| ATOM | 13311 | CG1 | ILE | B | 337 | −46.795 | −11.865 | −14.227 | 1.00 | 18.44 | C |
| ATOM | 13314 | CD1 | ILE | B | 337 | −45.767 | −12.192 | −15.300 | 1.00 | 19.26 | C |
| ATOM | 13318 | CG2 | ILE | B | 337 | −45.568 | −12.320 | −12.152 | 1.00 | 16.25 | C |
| ATOM | 13322 | C | ILE | B | 337 | −47.053 | −10.395 | −10.699 | 1.00 | 18.32 | C |
| ATOM | 13323 | O | ILE | B | 337 | −47.497 | −11.175 | −9.838 | 1.00 | 18.06 | O |
| ATOM | 13325 | N | ASN | B | 338 | −46.321 | −9.311 | −10.404 | 1.00 | 18.89 | N |
| ATOM | 13326 | CA | ASN | B | 338 | −45.985 | −8.978 | −9.007 | 1.00 | 19.49 | C |
| ATOM | 13328 | CB | ASN | B | 338 | −45.189 | −7.690 | −8.917 | 1.00 | 19.43 | C |
| ATOM | 13331 | CG | ASN | B | 338 | −43.789 | −7.836 | −9.444 | 1.00 | 20.83 | C |
| ATOM | 13332 | OD1 | ASN | B | 338 | −43.292 | −8.954 | −9.634 | 1.00 | 21.52 | O |
| ATOM | 13333 | ND2 | ASN | B | 338 | −43.124 | −6.697 | −9.676 | 1.00 | 22.32 | N |
| ATOM | 13336 | C | ASN | B | 338 | −47.229 | −8.835 | −8.146 | 1.00 | 20.05 | C |
| ATOM | 13337 | O | ASN | B | 338 | −47.182 | −9.055 | −6.953 | 1.00 | 19.81 | O |
| ATOM | 13339 | N | GLU | B | 339 | −48.337 | −8.459 | −8.770 | 1.00 | 20.81 | N |
| ATOM | 13340 | CA | GLU | B | 339 | −49.589 | −8.347 | −8.086 | 1.00 | 21.81 | C |
| ATOM | 13342 | CB | GLU | B | 339 | −50.563 | −7.544 | −8.933 | 1.00 | 22.69 | C |
| ATOM | 13345 | CG | GLU | B | 339 | −51.240 | −6.422 | −8.148 | 1.00 | 27.28 | C |
| ATOM | 13348 | CD | GLU | B | 339 | −52.571 | −5.959 | −8.768 | 1.00 | 32.79 | C |
| ATOM | 13349 | OE1 | GLU | B | 339 | −52.761 | −4.713 | −8.897 | 1.00 | 36.20 | O |
| ATOM | 13350 | OE2 | GLU | B | 339 | −53.416 | −6.837 | −9.114 | 1.00 | 34.35 | O |
| ATOM | 13351 | C | GLU | B | 339 | −50.170 | −9.732 | −7.762 | 1.00 | 21.59 | C |
| ATOM | 13352 | O | GLU | B | 339 | −50.690 | −9.946 | −6.666 | 1.00 | 21.38 | O |
| ATOM | 13354 | N | ILE | B | 340 | −50.094 | −10.676 | −8.700 | 1.00 | 21.48 | N |
| ATOM | 13355 | CA | ILE | B | 340 | −50.486 | −12.049 | −8.384 | 1.00 | 21.27 | C |
| ATOM | 13357 | CB | ILE | B | 340 | −50.437 | −12.990 | −9.603 | 1.00 | 21.17 | C |
| ATOM | 13359 | CG1 | ILE | B | 340 | −51.478 | −12.589 | −10.643 | 1.00 | 20.99 | C |
| ATOM | 13362 | CD1 | ILE | B | 340 | −51.245 | −13.202 | −12.017 | 1.00 | 19.72 | C |
| ATOM | 13366 | CG2 | ILE | B | 340 | −50.702 | −14.444 | −9.177 | 1.00 | 21.09 | C |
| ATOM | 13370 | C | ILE | B | 340 | −49.557 | −12.585 | −7.278 | 1.00 | 21.40 | C |
| ATOM | 13371 | O | ILE | B | 340 | −50.023 | −13.238 | −6.334 | 1.00 | 21.74 | O |
| ATOM | 13373 | N | ALA | B | 341 | −48.256 | −12.301 | −7.380 | 1.00 | 20.90 | N |
| ATOM | 13374 | CA | ALA | B | 341 | −47.312 | −12.721 | −6.349 | 1.00 | 20.62 | C |
| ATOM | 13376 | CB | ALA | B | 341 | −45.922 | −12.260 | −6.694 | 1.00 | 20.53 | C |
| ATOM | 13380 | C | ALA | B | 341 | −47.720 | −12.195 | −4.969 | 1.00 | 20.59 | C |
| ATOM | 13381 | O | ALA | B | 341 | −47.606 | −12.901 | −3.950 | 1.00 | 20.57 | O |
| ATOM | 13383 | N | TYR | B | 342 | −48.208 | −10.958 | −4.949 | 1.00 | 20.62 | N |
| ATOM | 13384 | CA | TYR | B | 342 | −48.600 | −10.303 | −3.707 | 1.00 | 20.59 | C |
| ATOM | 13386 | CB | TYR | B | 342 | −48.790 | −8.792 | −3.907 | 1.00 | 20.05 | C |
| ATOM | 13389 | CG | TYR | B | 342 | −49.309 | −8.143 | −2.674 | 1.00 | 18.29 | C |
| ATOM | 13390 | CD1 | TYR | B | 342 | −48.443 | −7.683 | −1.698 | 1.00 | 17.62 | C |
| ATOM | 13392 | CE1 | TYR | B | 342 | −48.914 | −7.111 | −.518 | 1.00 | 17.91 | C |
| ATOM | 13394 | CZ | TYR | B | 342 | −50.285 | −7.005 | −.298 | 1.00 | 18.18 | C |
| ATOM | 13395 | OH | TYR | B | 342 | −50.763 | −6.433 | .877 | 1.00 | 16.00 | O |
| ATOM | 13397 | CE2 | TYR | B | 342 | −51.169 | −7.467 | −1.275 | 1.00 | 18.10 | C |
| ATOM | 13399 | CD2 | TYR | B | 342 | −50.670 | −8.037 | −2.450 | 1.00 | 17.67 | C |
| ATOM | 13401 | C | TYR | B | 342 | −49.863 | −10.928 | −3.118 | 1.00 | 21.48 | C |
| ATOM | 13402 | O | TYR | B | 342 | −49.960 | −11.089 | −1.913 | 1.00 | 20.91 | O |
| ATOM | 13404 | N | ASP | B | 343 | −50.832 | −11.273 | −3.959 | 1.00 | 22.93 | N |
| ATOM | 13405 | CA | ASP | B | 343 | −52.048 | −11.925 | −3.470 | 1.00 | 24.30 | C |
| ATOM | 13407 | CB | ASP | B | 343 | −53.010 | −12.282 | −4.608 | 1.00 | 24.59 | C |
| ATOM | 13410 | CG | ASP | B | 343 | −53.577 | −11.060 | −5.334 | 1.00 | 26.66 | C |
| ATOM | 13411 | OD1 | ASP | B | 343 | −53.619 | −9.936 | −4.756 | 1.00 | 28.24 | O |
| ATOM | 13412 | OD2 | ASP | B | 343 | −54.004 | −11.247 | −6.506 | 1.00 | 29.56 | O |
| ATOM | 13413 | C | ASP | B | 343 | −51.660 | −13.208 | −2.761 | 1.00 | 24.97 | C |
| ATOM | 13414 | O | ASP | B | 343 | −52.128 | −13.495 | −1.658 | 1.00 | 24.95 | O |
| ATOM | 13416 | N | ASN | B | 344 | −50.792 | −13.973 | −3.413 | 1.00 | 25.90 | N |
| ATOM | 13417 | CA | ASN | B | 344 | −50.322 | −15.252 | −2.884 | 1.00 | 26.59 | C |
| ATOM | 13419 | CB | ASN | B | 344 | −49.623 | −16.043 | −3.978 | 1.00 | 26.74 | C |
| ATOM | 13422 | CG | ASN | B | 344 | −50.594 | −16.639 | −4.933 | 1.00 | 28.21 | C |
| ATOM | 13423 | OD1 | ASN | B | 344 | −51.080 | −17.737 | −4.688 | 1.00 | 32.10 | O |
| ATOM | 13424 | ND2 | ASN | B | 344 | −50.923 | −15.916 | −6.016 | 1.00 | 28.40 | N |
| ATOM | 13427 | C | ASN | B | 344 | −49.421 | −15.146 | −1.655 | 1.00 | 26.78 | C |
| ATOM | 13428 | O | ASN | B | 344 | −49.424 | −16.053 | −.821 | 1.00 | 27.06 | O |
| ATOM | 13430 | N | LEU | B | 345 | −48.647 | −14.067 | −1.533 | 1.00 | 26.74 | N |

TABLE 3-7-continued

Coordinates of *P. tremuloides* IspS

| ATOM | 13431 | CA | LEU | B | 345 | −47.970 | −13.793 | −.261 | 1.00 | 26.59 | C |
|---|---|---|---|---|---|---|---|---|---|---|---|
| ATOM | 13433 | CB | LEU | B | 345 | −47.005 | −12.618 | −.396 | 1.00 | 26.25 | C |
| ATOM | 13436 | CG | LEU | B | 345 | −46.046 | −12.376 | .764 | 1.00 | 24.65 | C |
| ATOM | 13438 | CD1 | LEU | B | 345 | −45.258 | −13.621 | 1.115 | 1.00 | 22.50 | C |
| ATOM | 13442 | CD2 | LEU | B | 345 | −45.119 | −11.251 | .387 | 1.00 | 23.54 | C |
| ATOM | 13446 | C | LEU | B | 345 | −49.004 | −13.503 | .840 | 1.00 | 27.00 | C |
| ATOM | 13447 | O | LEU | B | 345 | −48.903 | −14.014 | 1.947 | 1.00 | 26.93 | O |
| ATOM | 13449 | N | LYS | B | 346 | −50.008 | −12.697 | .518 | 1.00 | 27.54 | N |
| ATOM | 13450 | CA | LYS | B | 346 | −51.012 | −12.300 | 1.491 | 1.00 | 27.96 | C |
| ATOM | 13452 | CB | LYS | B | 346 | −51.998 | −11.288 | .889 | 1.00 | 28.13 | C |
| ATOM | 13455 | CG | LYS | B | 346 | −52.822 | −10.527 | 1.926 | 1.00 | 28.70 | C |
| ATOM | 13458 | CD | LYS | B | 346 | −53.781 | −9.526 | 1.281 | 1.00 | 29.73 | C |
| ATOM | 13461 | CE | LYS | B | 346 | −55.205 | −10.063 | 1.133 | 1.00 | 31.17 | C |
| ATOM | 13464 | NZ | LYS | B | 346 | −55.839 | −9.661 | −.171 | 1.00 | 32.83 | N |
| ATOM | 13468 | C | LYS | B | 346 | −51.788 | −13.498 | 1.984 | 1.00 | 28.31 | C |
| ATOM | 13469 | O | LYS | B | 346 | −52.074 | −13.600 | 3.177 | 1.00 | 28.52 | O |
| ATOM | 13471 | N | ASP | B | 347 | −52.149 | −14.396 | 1.075 | 1.00 | 28.56 | N |
| ATOM | 13472 | CA | ASP | B | 347 | −53.102 | −15.441 | 1.427 | 1.00 | 29.11 | C |
| ATOM | 13474 | CB | ASP | B | 347 | −54.068 | −15.736 | .268 | 1.00 | 29.50 | C |
| ATOM | 13477 | CG | ASP | B | 347 | −54.902 | −14.500 | −.150 | 1.00 | 31.04 | C |
| ATOM | 13478 | OD1 | ASP | B | 347 | −54.961 | −13.500 | .616 | 1.00 | 31.35 | O |
| ATOM | 13479 | OD2 | ASP | B | 347 | −55.496 | −14.534 | −1.261 | 1.00 | 33.39 | O |
| ATOM | 13480 | C | ASP | B | 347 | −52.403 | −16.699 | 1.891 | 1.00 | 28.79 | C |
| ATOM | 13481 | O | ASP | B | 347 | −52.824 | −17.321 | 2.854 | 1.00 | 29.02 | O |
| ATOM | 13483 | N | LYS | B | 348 | −51.326 | −17.068 | 1.222 | 1.00 | 28.74 | N |
| ATOM | 13484 | CA | LYS | B | 348 | −50.612 | −18.293 | 1.564 | 1.00 | 28.84 | C |
| ATOM | 13486 | CB | LYS | B | 348 | −50.290 | −19.101 | .299 | 1.00 | 29.24 | C |
| ATOM | 13489 | CG | LYS | B | 348 | −51.513 | −19.470 | −.576 | 1.00 | 30.97 | C |
| ATOM | 13492 | CD | LYS | B | 348 | −51.051 | −20.300 | −1.803 | 1.00 | 33.66 | C |
| ATOM | 13495 | CE | LYS | B | 348 | −52.033 | −20.244 | −2.989 | 1.00 | 34.52 | C |
| ATOM | 13498 | NZ | LYS | B | 348 | −53.445 | −20.542 | −2.607 | 1.00 | 35.61 | N |
| ATOM | 13502 | C | LYS | B | 348 | −49.330 | −18.029 | 2.358 | 1.00 | 27.97 | C |
| ATOM | 13503 | O | LYS | B | 348 | −48.763 | −18.948 | 2.925 | 1.00 | 27.88 | O |
| ATOM | 13505 | N | GLY | B | 349 | −48.874 | −16.785 | 2.403 | 1.00 | 27.21 | N |
| ATOM | 13506 | CA | GLY | B | 349 | −47.625 | −16.473 | 3.075 | 1.00 | 26.87 | C |
| ATOM | 13509 | C | GLY | B | 349 | −46.437 | −17.227 | 2.514 | 1.00 | 26.71 | C |
| ATOM | 13510 | O | GLY | B | 349 | −45.576 | −17.669 | 3.271 | 1.00 | 26.65 | O |
| ATOM | 13512 | N | GLU | B | 350 | −46.409 | −17.390 | 1.191 | 1.00 | 26.61 | N |
| ATOM | 13513 | CA | GLU | B | 350 | −45.263 | −17.953 | .470 | 1.00 | 26.43 | C |
| ATOM | 13515 | CB | GLU | B | 350 | −45.624 | −19.310 | −.128 | 1.00 | 26.85 | C |
| ATOM | 13518 | CG | GLU | B | 350 | −45.685 | −20.453 | .888 | 1.00 | 29.63 | C |
| ATOM | 13521 | CD | GLU | B | 350 | −44.304 | −21.036 | 1.227 | 1.00 | 34.21 | C |
| ATOM | 13522 | OE1 | GLU | B | 350 | −43.417 | −21.045 | .328 | 1.00 | 36.93 | O |
| ATOM | 13523 | OE2 | GLU | B | 350 | −44.106 | −21.498 | 2.384 | 1.00 | 35.89 | O |
| ATOM | 13524 | C | GLU | B | 350 | −44.900 | −16.981 | −.637 | 1.00 | 25.49 | C |
| ATOM | 13525 | O | GLU | B | 350 | −45.774 | −16.312 | −1.181 | 1.00 | 25.35 | O |
| ATOM | 13527 | N | ASN | B | 351 | −43.616 | −16.866 | −.955 | 1.00 | 24.74 | N |
| ATOM | 13528 | CA | ASN | B | 351 | −43.206 | −16.046 | −2.090 | 1.00 | 24.47 | C |
| ATOM | 13530 | CB | ASN | B | 351 | −41.851 | −15.369 | −1.867 | 1.00 | 24.94 | C |
| ATOM | 13533 | CG | ASN | B | 351 | −41.428 | −14.489 | −3.062 | 1.00 | 26.98 | C |
| ATOM | 13534 | OD1 | ASN | B | 351 | −41.976 | −14.605 | −4.170 | 1.00 | 28.96 | O |
| ATOM | 13535 | ND2 | ASN | B | 351 | −40.457 | −13.601 | −2.834 | 1.00 | 29.55 | N |
| ATOM | 13538 | C | ASN | B | 351 | −43.095 | −16.918 | −3.303 | 1.00 | 23.33 | C |
| ATOM | 13539 | O | ASN | B | 351 | −42.120 | −17.641 | −3.429 | 1.00 | 23.47 | O |
| ATOM | 13541 | N | ILE | B | 352 | −44.060 | −16.823 | −4.208 | 1.00 | 22.09 | N |
| ATOM | 13542 | CA | ILE | B | 352 | −44.048 | −17.644 | −5.410 | 1.00 | 21.22 | C |
| ATOM | 13544 | CB | ILE | B | 352 | −45.452 | −18.213 | −5.675 | 1.00 | 21.23 | C |
| ATOM | 13546 | CG1 | ILE | B | 352 | −46.464 | −17.080 | −5.913 | 1.00 | 21.11 | C |
| ATOM | 13549 | CD1 | ILE | B | 352 | −47.346 | −17.305 | −7.126 | 1.00 | 20.33 | C |
| ATOM | 13553 | CG2 | ILE | B | 352 | −45.875 | −19.116 | −4.519 | 1.00 | 19.79 | C |
| ATOM | 13557 | C | ILE | B | 352 | −43.508 | −16.947 | −6.689 | 1.00 | 20.88 | C |
| ATOM | 13558 | O | ILE | B | 352 | −43.486 | −17.553 | −7.758 | 1.00 | 20.76 | O |
| ATOM | 13560 | N | LEU | B | 353 | −43.030 | −15.705 | −6.574 | 1.00 | 20.44 | N |
| ATOM | 13561 | CA | LEU | B | 353 | −42.603 | −14.907 | −7.750 | 1.00 | 19.84 | C |
| ATOM | 13563 | CB | LEU | B | 353 | −42.055 | −13.527 | −7.325 | 1.00 | 19.67 | C |
| ATOM | 13566 | CG | LEU | B | 353 | −42.003 | −12.339 | −8.311 | 1.00 | 18.47 | C |
| ATOM | 13568 | CD1 | LEU | B | 353 | −43.306 | −12.083 | −9.008 | 1.00 | 17.03 | C |
| ATOM | 13572 | CD2 | LEU | B | 353 | −41.604 | −11.064 | −7.597 | 1.00 | 17.08 | C |
| ATOM | 13576 | C | LEU | B | 353 | −41.587 | −15.628 | −8.633 | 1.00 | 19.81 | C |
| ATOM | 13577 | O | LEU | B | 353 | −41.720 | −15.596 | −9.851 | 1.00 | 19.55 | O |
| ATOM | 13579 | N | PRO | B | 354 | −40.578 | −16.299 | −8.024 | 1.00 | 20.01 | N |
| ATOM | 13580 | CA | PRO | B | 354 | −39.571 | −17.010 | −8.822 | 1.00 | 19.73 | C |
| ATOM | 13582 | CB | PRO | B | 354 | −38.781 | −17.796 | −7.779 | 1.00 | 19.55 | C |
| ATOM | 13585 | CG | PRO | B | 354 | −38.928 | −17.037 | −6.542 | 1.00 | 19.61 | C |
| ATOM | 13588 | CD | PRO | B | 354 | −40.289 | −16.413 | −6.578 | 1.00 | 19.90 | C |
| ATOM | 13591 | C | PRO | B | 354 | −40.187 | −17.971 | −9.804 | 1.00 | 19.87 | C |
| ATOM | 13592 | O | PRO | B | 354 | −39.693 | −18.103 | −10.918 | 1.00 | 20.08 | O |
| ATOM | 13593 | N | TYR | B | 355 | −41.264 | −18.636 | −9.387 | 1.00 | 20.14 | N |

TABLE 3-7-continued

| | | | | | | | | | | |
|---|---|---|---|---|---|---|---|---|---|---|
| ATOM | 13594 | CA | TYR | B | 355 | −41.909 | −19.665 | −10.216 | 1.00 | 20.24 | C |
| ATOM | 13596 | CB | TYR | B | 355 | −42.878 | −20.520 | −9.394 | 1.00 | 20.40 | C |
| ATOM | 13599 | CG | TYR | B | 355 | −42.189 | −21.153 | −8.214 | 1.00 | 21.82 | C |
| ATOM | 13600 | CD1 | TYR | B | 355 | −41.119 | −21.999 | −8.412 | 1.00 | 22.86 | C |
| ATOM | 13602 | CE1 | TYR | B | 355 | −40.457 | −22.564 | −7.353 | 1.00 | 25.07 | C |
| ATOM | 13604 | CZ | TYR | B | 355 | −40.850 | −22.285 | −6.053 | 1.00 | 25.58 | C |
| ATOM | 13605 | OH | TYR | B | 355 | −40.153 | −22.887 | −5.020 | 1.00 | 27.33 | O |
| ATOM | 13607 | CE2 | TYR | B | 355 | −41.918 | −21.433 | −5.815 | 1.00 | 23.93 | C |
| ATOM | 13609 | CD2 | TYR | B | 355 | −42.577 | −20.867 | −6.900 | 1.00 | 23.10 | C |
| ATOM | 13611 | C | TYR | B | 355 | −42.625 | −19.001 | −11.361 | 1.00 | 19.67 | C |
| ATOM | 13612 | O | TYR | B | 355 | −42.455 | −19.405 | −12.510 | 1.00 | 19.75 | O |
| ATOM | 13614 | N | LEU | B | 356 | −43.385 | −17.954 | −11.030 | 1.00 | 18.97 | N |
| ATOM | 13615 | CA | LEU | B | 356 | −44.180 | −17.205 | −12.004 | 1.00 | 18.26 | C |
| ATOM | 13617 | CB | LEU | B | 356 | −45.039 | −16.157 | −11.293 | 1.00 | 18.03 | C |
| ATOM | 13620 | CG | LEU | B | 356 | −46.056 | −16.727 | −10.312 | 1.00 | 18.13 | C |
| ATOM | 13622 | CD1 | LEU | B | 356 | −46.691 | −15.613 | −9.500 | 1.00 | 19.37 | C |
| ATOM | 13626 | CD2 | LEU | B | 356 | −47.106 | −17.521 | −11.046 | 1.00 | 17.93 | C |
| ATOM | 13630 | C | LEU | B | 356 | −43.298 | −16.536 | −13.056 | 1.00 | 17.76 | C |
| ATOM | 13631 | O | LEU | B | 356 | −43.598 | −16.567 | −14.259 | 1.00 | 16.93 | O |
| ATOM | 13633 | N | THR | B | 357 | −42.201 | −15.949 | −12.600 | 1.00 | 17.56 | N |
| ATOM | 13634 | CA | THR | B | 357 | −41.335 | −15.215 | −13.501 | 1.00 | 17.63 | C |
| ATOM | 13636 | CB | THR | B | 357 | −40.438 | −14.236 | −12.759 | 1.00 | 17.69 | C |
| ATOM | 13638 | OG1 | THR | B | 357 | −39.530 | −14.974 | −11.934 | 1.00 | 18.39 | O |
| ATOM | 13640 | CG2 | THR | B | 357 | −41.288 | −13.242 | −11.927 | 1.00 | 16.47 | C |
| ATOM | 13644 | C | THR | B | 357 | −40.477 | −16.145 | −14.356 | 1.00 | 17.55 | C |
| ATOM | 13645 | O | THR | B | 357 | −40.154 | −15.793 | −15.498 | 1.00 | 17.17 | O |
| ATOM | 13647 | N | LYS | B | 358 | −40.127 | −17.321 | −13.824 | 1.00 | 17.37 | N |
| ATOM | 13648 | CA | LYS | B | 358 | −39.462 | −18.337 | −14.649 | 1.00 | 17.55 | C |
| ATOM | 13650 | CB | LYS | B | 358 | −39.030 | −19.542 | −13.827 | 1.00 | 17.87 | C |
| ATOM | 13653 | CG | LYS | B | 358 | −38.450 | −20.718 | −14.640 | 1.00 | 18.75 | C |
| ATOM | 13656 | CD | LYS | B | 358 | −37.013 | −20.497 | −15.112 | 1.00 | 20.18 | C |
| ATOM | 13659 | CE | LYS | B | 358 | −36.361 | −21.843 | −15.457 | 1.00 | 21.49 | C |
| ATOM | 13662 | NZ | LYS | B | 358 | −35.189 | −21.702 | −16.361 | 1.00 | 22.89 | N |
| ATOM | 13666 | C | LYS | B | 358 | −40.403 | −18.777 | −15.754 | 1.00 | 17.43 | C |
| ATOM | 13667 | O | LYS | B | 358 | −40.031 | −18.775 | −16.926 | 1.00 | 17.52 | O |
| ATOM | 13669 | N | ALA | B | 359 | −41.633 | −19.120 | −15.384 | 1.00 | 17.42 | N |
| ATOM | 13670 | CA | ALA | B | 359 | −42.654 | −19.471 | −16.359 | 1.00 | 17.52 | C |
| ATOM | 13672 | CB | ALA | B | 359 | −44.011 | −19.434 | −15.738 | 1.00 | 17.16 | C |
| ATOM | 13676 | C | ALA | B | 359 | −42.585 | −18.521 | −17.531 | 1.00 | 18.18 | C |
| ATOM | 13677 | O | ALA | B | 359 | −42.513 | −18.956 | −18.675 | 1.00 | 18.50 | O |
| ATOM | 13679 | N | TRP | B | 360 | −42.556 | −17.223 | −17.245 | 1.00 | 19.14 | N |
| ATOM | 13680 | CA | TRP | B | 360 | −42.526 | −16.206 | −18.301 | 1.00 | 19.77 | C |
| ATOM | 13682 | CB | TRP | B | 360 | −42.922 | −14.837 | −17.746 | 1.00 | 20.15 | C |
| ATOM | 13685 | CG | TRP | B | 360 | −44.377 | −14.653 | −17.813 | 1.00 | 20.50 | C |
| ATOM | 13686 | CD1 | TRP | B | 360 | −45.259 | −14.729 | −16.788 | 1.00 | 22.15 | C |
| ATOM | 13688 | NE1 | TRP | B | 360 | −46.536 | −14.533 | −17.248 | 1.00 | 22.84 | N |
| ATOM | 13690 | CE2 | TRP | B | 360 | −46.487 | −14.348 | −18.603 | 1.00 | 21.68 | C |
| ATOM | 13691 | CD2 | TRP | B | 360 | −45.134 | −14.418 | −18.987 | 1.00 | 20.85 | C |
| ATOM | 13692 | CE3 | TRP | B | 360 | −44.802 | −14.253 | −20.334 | 1.00 | 21.21 | C |
| ATOM | 13694 | CZ3 | TRP | B | 360 | −45.821 | −14.025 | −21.245 | 1.00 | 20.75 | C |
| ATOM | 13696 | CH2 | TRP | B | 360 | −47.166 | −13.961 | −20.827 | 1.00 | 21.21 | C |
| ATOM | 13698 | CZ2 | TRP | B | 360 | −47.515 | −14.123 | −19.516 | 1.00 | 20.97 | C |
| ATOM | 13700 | C | TRP | B | 360 | −41.215 | −16.110 | −19.081 | 1.00 | 19.96 | C |
| ATOM | 13701 | O | TRP | B | 360 | −41.242 | −15.791 | −20.271 | 1.00 | 19.94 | O |
| ATOM | 13703 | N | ALA | B | 361 | −40.089 | −16.368 | −18.420 | 1.00 | 20.14 | N |
| ATOM | 13704 | CA | ALA | B | 361 | −38.790 | −16.437 | −19.102 | 1.00 | 20.41 | C |
| ATOM | 13706 | CB | ALA | B | 361 | −37.676 | −16.581 | −18.102 | 1.00 | 20.67 | C |
| ATOM | 13710 | C | ALA | B | 361 | −38.763 | −17.618 | −20.041 | 1.00 | 20.55 | C |
| ATOM | 13711 | O | ALA | B | 361 | −38.330 | −17.510 | −21.187 | 1.00 | 20.76 | O |
| ATOM | 13713 | N | ASP | B | 362 | −39.230 | −18.749 | −19.534 | 1.00 | 20.57 | N |
| ATOM | 13714 | CA | ASP | B | 362 | −39.360 | −19.965 | −20.326 | 1.00 | 20.97 | C |
| ATOM | 13716 | CB | ASP | B | 362 | −39.984 | −21.082 | −19.470 | 1.00 | 21.39 | C |
| ATOM | 13719 | CG | ASP | B | 362 | −38.938 | −21.902 | −18.693 | 1.00 | 22.80 | C |
| ATOM | 13720 | OD1 | ASP | B | 362 | −38.836 | −23.109 | −18.970 | 1.00 | 28.57 | O |
| ATOM | 13721 | OD2 | ASP | B | 362 | −38.210 | −21.384 | −17.825 | 1.00 | 22.78 | O |
| ATOM | 13722 | C | ASP | B | 362 | −40.179 | −19.748 | −21.618 | 1.00 | 20.66 | C |
| ATOM | 13723 | O | ASP | B | 362 | −39.740 | −20.141 | −22.701 | 1.00 | 20.69 | O |
| ATOM | 13725 | N | LEU | B | 363 | −41.346 | −19.110 | −21.501 | 1.00 | 20.22 | N |
| ATOM | 13726 | CA | LEU | B | 363 | −42.245 | −18.885 | −22.648 | 1.00 | 19.82 | C |
| ATOM | 13728 | CB | LEU | B | 363 | −43.592 | −18.327 | −22.164 | 1.00 | 19.11 | C |
| ATOM | 13731 | CG | LEU | B | 363 | −44.644 | −17.945 | −23.209 | 1.00 | 17.02 | C |
| ATOM | 13733 | CD1 | LEU | B | 363 | −44.829 | −19.033 | −24.214 | 1.00 | 16.20 | C |
| ATOM | 13737 | CD2 | LEU | B | 363 | −45.979 | −17.618 | −22.586 | 1.00 | 14.21 | C |
| ATOM | 13741 | C | LEU | B | 363 | −41.633 | −17.950 | −23.706 | 1.00 | 20.76 | C |
| ATOM | 13742 | O | LEU | B | 363 | −41.656 | −18.235 | −24.910 | 1.00 | 21.00 | O |
| ATOM | 13744 | N | CYS | B | 364 | −41.088 | −16.826 | −23.253 | 1.00 | 21.42 | N |
| ATOM | 13745 | CA | CYS | B | 364 | −40.427 | −15.884 | −24.147 | 1.00 | 21.67 | C |
| ATOM | 13747 | CB | CYS | B | 364 | −39.969 | −14.639 | −23.376 | 1.00 | 21.86 | C |

TABLE 3-7-continued

Coordinates of *P. tremuloides* IspS

| ATOM | 13750 | SG | CYS | B | 364 | −41.327 | −13.638 | −22.722 | 1.00 | 23.36 | S |
|---|---|---|---|---|---|---|---|---|---|---|---|
| ATOM | 13752 | C | CYS | B | 364 | −39.229 | −16.547 | −24.835 | 1.00 | 21.52 | C |
| ATOM | 13753 | O | CYS | B | 364 | −39.010 | −16.323 | −26.037 | 1.00 | 21.67 | O |
| ATOM | 13755 | N | ASN | B | 365 | −38.454 | −17.352 | −24.095 | 1.00 | 20.83 | N |
| ATOM | 13756 | CA | ASN | B | 365 | −37.306 | −18.025 | −24.713 | 1.00 | 20.65 | C |
| ATOM | 13758 | CB | ASN | B | 365 | −36.425 | −18.756 | −23.691 | 1.00 | 20.74 | C |
| ATOM | 13761 | CG | ASN | B | 365 | −35.330 | −17.865 | −23.100 | 1.00 | 20.53 | C |
| ATOM | 13762 | OD1 | ASN | B | 365 | −34.553 | −17.229 | −23.830 | 1.00 | 18.26 | O |
| ATOM | 13763 | ND2 | ASN | B | 365 | −35.252 | −17.841 | −21.763 | 1.00 | 20.69 | N |
| ATOM | 13766 | C | ASN | B | 365 | −37.756 | −18.987 | −25.811 | 1.00 | 20.43 | C |
| ATOM | 13767 | O | ASN | B | 365 | −36.998 | −19.253 | −26.759 | 1.00 | 20.11 | O |
| ATOM | 13769 | N | ALA | B | 366 | −38.987 | −19.492 | −25.667 | 1.00 | 20.01 | N |
| ATOM | 13770 | CA | ALA | B | 366 | −39.618 | −20.340 | −26.665 | 1.00 | 19.70 | C |
| ATOM | 13772 | CB | ALA | B | 366 | −40.766 | −21.113 | −26.045 | 1.00 | 19.53 | C |
| ATOM | 13776 | C | ALA | B | 366 | −40.099 | −19.494 | −27.838 | 1.00 | 19.74 | C |
| ATOM | 13777 | O | ALA | B | 366 | −39.846 | −19.824 | −28.989 | 1.00 | 19.61 | O |
| ATOM | 13779 | N | PHE | B | 367 | −40.791 | −18.399 | −27.553 | 1.00 | 19.99 | N |
| ATOM | 13780 | CA | PHE | B | 367 | −41.138 | −17.446 | −28.606 | 1.00 | 20.36 | C |
| ATOM | 13782 | CB | PHE | B | 367 | −41.805 | −16.194 | −28.026 | 1.00 | 20.62 | C |
| ATOM | 13785 | CG | PHE | B | 367 | −43.200 | −16.403 | −27.537 | 1.00 | 21.75 | C |
| ATOM | 13786 | CD1 | PHE | B | 367 | −44.136 | −17.071 | −28.315 | 1.00 | 23.00 | C |
| ATOM | 13788 | CE1 | PHE | B | 367 | −45.435 | −17.242 | −27.874 | 1.00 | 23.60 | C |
| ATOM | 13790 | CZ | PHE | B | 367 | −45.819 | −16.731 | −26.648 | 1.00 | 23.64 | C |
| ATOM | 13792 | CE2 | PHE | B | 367 | −44.901 | −16.049 | −25.871 | 1.00 | 23.56 | C |
| ATOM | 13794 | CD2 | PHE | B | 367 | −43.599 | −15.883 | −26.316 | 1.00 | 22.91 | C |
| ATOM | 13796 | C | PHE | B | 367 | −39.906 | −16.986 | −29.393 | 1.00 | 20.19 | C |
| ATOM | 13797 | O | PHE | B | 367 | −39.934 | −16.903 | −30.615 | 1.00 | 19.98 | O |
| ATOM | 13799 | N | LEU | B | 368 | −38.839 | −16.659 | −28.675 | 1.00 | 20.24 | N |
| ATOM | 13800 | CA | LEU | B | 368 | −37.629 | −16.161 | −29.298 | 1.00 | 20.31 | C |
| ATOM | 13802 | CB | LEU | B | 368 | −36.569 | −15.900 | −28.232 | 1.00 | 20.27 | C |
| ATOM | 13805 | CG | LEU | B | 368 | −35.235 | −15.313 | −28.694 | 1.00 | 20.12 | C |
| ATOM | 13807 | CD1 | LEU | B | 368 | −35.417 | −14.069 | −29.592 | 1.00 | 20.05 | C |
| ATOM | 13811 | CD2 | LEU | B | 368 | −34.409 | −14.987 | −27.465 | 1.00 | 18.60 | C |
| ATOM | 13815 | C | LEU | B | 368 | −37.122 | −17.179 | −30.295 | 1.00 | 20.53 | C |
| ATOM | 13816 | O | LEU | B | 368 | −36.844 | −16.844 | −31.446 | 1.00 | 20.49 | O |
| ATOM | 13818 | N | GLN | B | 369 | −37.032 | −18.426 | −29.832 | 1.00 | 20.80 | N |
| ATOM | 13819 | CA | GLN | B | 369 | −36.565 | −19.557 | −30.638 | 1.00 | 20.90 | C |
| ATOM | 13821 | CB | GLN | B | 369 | −36.614 | −20.857 | −29.815 | 1.00 | 20.98 | C |
| ATOM | 13824 | CG | GLN | B | 369 | −36.343 | −22.159 | −30.576 | 1.00 | 20.75 | C |
| ATOM | 13827 | CD | GLN | B | 369 | −34.946 | −22.238 | −31.126 | 1.00 | 20.29 | C |
| ATOM | 13828 | OE1 | GLN | B | 369 | −34.718 | −21.984 | −32.305 | 1.00 | 20.17 | O |
| ATOM | 13829 | NE2 | GLN | B | 369 | −33.996 | −22.581 | −30.272 | 1.00 | 20.33 | N |
| ATOM | 13832 | C | GLN | B | 369 | −37.365 | −19.718 | −31.910 | 1.00 | 21.04 | C |
| ATOM | 13833 | O | GLN | B | 369 | −36.803 | −20.097 | −32.929 | 1.00 | 20.82 | O |
| ATOM | 13835 | N | GLU | B | 370 | −38.668 | −19.453 | −31.863 | 1.00 | 21.80 | N |
| ATOM | 13836 | CA | GLU | B | 370 | −39.480 | −19.512 | −33.087 | 1.00 | 22.73 | C |
| ATOM | 13838 | CB | GLU | B | 370 | −40.996 | −19.518 | −32.801 | 1.00 | 23.18 | C |
| ATOM | 13841 | CG | GLU | B | 370 | −41.449 | −20.608 | −31.809 | 1.00 | 25.92 | C |
| ATOM | 13844 | CD | GLU | B | 370 | −42.927 | −21.064 | −31.957 | 1.00 | 29.74 | C |
| ATOM | 13845 | OE1 | GLU | B | 370 | −43.840 | −20.191 | −32.101 | 1.00 | 30.13 | O |
| ATOM | 13846 | OE2 | GLU | B | 370 | −43.156 | −22.316 | −31.892 | 1.00 | 31.94 | O |
| ATOM | 13847 | C | GLU | B | 370 | −39.079 | −18.358 | −34.016 | 1.00 | 22.62 | C |
| ATOM | 13848 | O | GLU | B | 370 | −38.933 | −18.565 | −35.221 | 1.00 | 22.53 | O |
| ATOM | 13850 | N | ALA | B | 371 | −38.864 | −17.166 | −33.456 | 1.00 | 22.65 | N |
| ATOM | 13851 | CA | ALA | B | 371 | −38.427 | −16.023 | −34.254 | 1.00 | 22.95 | C |
| ATOM | 13853 | CB | ALA | B | 371 | −38.375 | −14.753 | −33.424 | 1.00 | 22.97 | C |
| ATOM | 13857 | C | ALA | B | 371 | −37.070 | −16.296 | −34.891 | 1.00 | 23.13 | C |
| ATOM | 13858 | O | ALA | B | 371 | −36.900 | −16.063 | −36.091 | 1.00 | 23.38 | O |
| ATOM | 13860 | N | LYS | B | 372 | −36.113 | −16.804 | −34.107 | 1.00 | 23.15 | N |
| ATOM | 13861 | CA | LYS | B | 372 | −34.776 | −17.102 | −34.640 | 1.00 | 23.10 | C |
| ATOM | 13863 | CB | LYS | B | 372 | −33.808 | −17.633 | −33.575 | 1.00 | 22.85 | C |
| ATOM | 13866 | CG | LYS | B | 372 | −33.414 | −16.616 | −32.514 | 1.00 | 24.28 | C |
| ATOM | 13869 | CD | LYS | B | 372 | −31.973 | −16.806 | −31.969 | 1.00 | 26.34 | C |
| ATOM | 13872 | CE | LYS | B | 372 | −31.919 | −17.407 | −30.544 | 1.00 | 27.84 | C |
| ATOM | 13875 | NZ | LYS | B | 372 | −31.673 | −16.405 | −29.458 | 1.00 | 27.93 | N |
| ATOM | 13879 | C | LYS | B | 372 | −34.887 | −18.093 | −35.790 | 1.00 | 23.16 | C |
| ATOM | 13880 | O | LYS | B | 372 | −34.231 | −17.920 | −36.804 | 1.00 | 23.73 | O |
| ATOM | 13882 | N | TRP | B | 373 | −35.720 | −19.122 | −35.658 | 1.00 | 23.11 | N |
| ATOM | 13883 | CA | TRP | B | 373 | −35.844 | −20.094 | −36.742 | 1.00 | 22.99 | C |
| ATOM | 13885 | CB | TRP | B | 373 | −36.746 | −21.274 | −36.370 | 1.00 | 22.71 | C |
| ATOM | 13888 | CG | TRP | B | 373 | −36.081 | −22.343 | −35.562 | 1.00 | 20.71 | C |
| ATOM | 13889 | CD1 | TRP | B | 373 | −34.770 | −22.740 | −35.623 | 1.00 | 19.89 | C |
| ATOM | 13891 | NE1 | TRP | B | 373 | −34.540 | −23.757 | −34.734 | 1.00 | 19.05 | N |
| ATOM | 13893 | CE2 | TRP | B | 373 | −35.715 | −24.050 | −34.090 | 1.00 | 18.91 | C |
| ATOM | 13894 | CD2 | TRP | B | 373 | −36.707 | −23.184 | −34.599 | 1.00 | 18.41 | C |
| ATOM | 13895 | CE3 | TRP | B | 373 | −38.007 | −23.288 | −34.105 | 1.00 | 15.66 | C |
| ATOM | 13897 | CZ3 | TRP | B | 373 | −38.271 | −24.216 | −33.130 | 1.00 | 15.41 | C |
| ATOM | 13899 | CH2 | TRP | B | 373 | −37.276 | −25.069 | −32.647 | 1.00 | 16.33 | C |

TABLE 3-7-continued

Coordinates of *P. tremuloides* IspS

| ATOM | 13901 | CZ2 | TRP | B | 373 | −35.994 | −25.005 | −33.112 | 1.00 | 17.53 | C |
|------|-------|-----|-----|---|-----|---------|---------|---------|------|-------|---|
| ATOM | 13903 | C | TRP | B | 373 | −36.374 | −19.416 | −37.991 | 1.00 | 23.59 | C |
| ATOM | 13904 | O | TRP | B | 373 | −35.878 | −19.653 | −39.096 | 1.00 | 23.60 | O |
| ATOM | 13906 | N | LEU | B | 374 | −37.374 | −18.559 | −37.801 | 1.00 | 24.32 | N |
| ATOM | 13907 | CA | LEU | B | 374 | −38.008 | −17.859 | −38.915 | 1.00 | 24.66 | C |
| ATOM | 13909 | CB | LEU | B | 374 | −39.181 | −17.019 | −38.428 | 1.00 | 24.85 | C |
| ATOM | 13912 | CG | LEU | B | 374 | −40.112 | −16.449 | −39.496 | 1.00 | 25.45 | C |
| ATOM | 13914 | CD1 | LEU | B | 374 | −41.002 | −17.535 | −40.070 | 1.00 | 24.83 | C |
| ATOM | 13918 | CD2 | LEU | B | 374 | −40.959 | −15.293 | −38.885 | 1.00 | 26.92 | C |
| ATOM | 13922 | C | LEU | B | 374 | −37.009 | −16.975 | −39.618 | 1.00 | 24.64 | C |
| ATOM | 13923 | O | LEU | B | 374 | −36.934 | −16.992 | −40.830 | 1.00 | 24.33 | O |
| ATOM | 13925 | N | TYR | B | 375 | −36.232 | −16.220 | −38.850 | 1.00 | 25.09 | N |
| ATOM | 13926 | CA | TYR | B | 375 | −35.283 | −15.274 | −39.433 | 1.00 | 25.71 | C |
| ATOM | 13928 | CB | TYR | B | 375 | −34.534 | −14.479 | −38.349 | 1.00 | 25.91 | C |
| ATOM | 13931 | CG | TYR | B | 375 | −33.536 | −13.468 | −38.892 | 1.00 | 27.11 | C |
| ATOM | 13932 | CD1 | TYR | B | 375 | −33.950 | −12.200 | −39.305 | 1.00 | 27.98 | C |
| ATOM | 13934 | CE1 | TYR | B | 375 | −33.039 | −11.271 | −39.811 | 1.00 | 28.61 | C |
| ATOM | 13936 | CZ | TYR | B | 375 | −31.693 | −11.605 | −39.904 | 1.00 | 29.13 | C |
| ATOM | 13937 | OH | TYR | B | 375 | −30.790 | −10.685 | −40.397 | 1.00 | 29.83 | O |
| ATOM | 13939 | CE2 | TYR | B | 375 | −31.256 | −12.863 | −39.501 | 1.00 | 28.79 | C |
| ATOM | 13941 | CD2 | TYR | B | 375 | −32.177 | −13.783 | −38.995 | 1.00 | 28.03 | C |
| ATOM | 13943 | C | TYR | B | 375 | −34.305 | −16.036 | −40.301 | 1.00 | 25.64 | C |
| ATOM | 13944 | O | TYR | B | 375 | −34.201 | −15.788 | −41.503 | 1.00 | 25.74 | O |
| ATOM | 13946 | N | ASN | B | 376 | −33.635 | −17.000 | −39.685 | 1.00 | 25.73 | N |
| ATOM | 13947 | CA | ASN | B | 376 | −32.599 | −17.777 | −40.346 | 1.00 | 25.78 | C |
| ATOM | 13949 | CB | ASN | B | 376 | −31.739 | −18.497 | −39.303 | 1.00 | 25.73 | C |
| ATOM | 13952 | CG | ASN | B | 376 | −31.155 | −17.565 | −38.273 | 1.00 | 25.13 | C |
| ATOM | 13953 | OD1 | ASN | B | 376 | −30.491 | −16.590 | −38.601 | 1.00 | 25.53 | O |
| ATOM | 13954 | ND2 | ASN | B | 376 | −31.389 | −17.874 | −37.013 | 1.00 | 24.64 | N |
| ATOM | 13957 | C | ASN | B | 376 | −33.126 | −18.824 | −41.332 | 1.00 | 26.04 | C |
| ATOM | 13958 | O | ASN | B | 376 | −32.343 | −19.644 | −41.807 | 1.00 | 26.36 | O |
| ATOM | 13960 | N | LYS | B | 377 | −34.428 | −18.824 | −41.632 | 1.00 | 26.16 | N |
| ATOM | 13961 | CA | LYS | B | 377 | −35.012 | −19.811 | −42.552 | 1.00 | 26.27 | C |
| ATOM | 13963 | CB | LYS | B | 377 | −34.575 | −19.538 | −44.010 | 1.00 | 26.51 | C |
| ATOM | 13966 | CG | LYS | B | 377 | −35.470 | −18.561 | −44.802 | 1.00 | 28.01 | C |
| ATOM | 13969 | CD | LYS | B | 377 | −34.629 | −17.592 | −45.667 | 1.00 | 29.99 | C |
| ATOM | 13972 | CE | LYS | B | 377 | −35.493 | −16.605 | −46.465 | 1.00 | 31.02 | C |
| ATOM | 13975 | NZ | LYS | B | 377 | −36.420 | −15.819 | −45.589 | 1.00 | 32.17 | N |
| ATOM | 13979 | C | LYS | B | 377 | −34.647 | −21.243 | −42.150 | 1.00 | 25.93 | C |
| ATOM | 13980 | O | LYS | B | 377 | −34.380 | −22.084 | −43.003 | 1.00 | 25.82 | O |
| ATOM | 13982 | N | SER | B | 378 | −34.637 | −21.522 | −40.852 | 1.00 | 25.65 | N |
| ATOM | 13983 | CA | SER | B | 378 | −34.324 | −22.860 | −40.385 | 1.00 | 25.54 | C |
| ATOM | 13985 | CB | SER | B | 378 | −34.132 | −22.877 | −38.882 | 1.00 | 25.41 | C |
| ATOM | 13988 | OG | SER | B | 378 | −32.905 | −22.269 | −38.570 | 1.00 | 25.67 | O |
| ATOM | 13990 | C | SER | B | 378 | −35.412 | −23.838 | −40.790 | 1.00 | 25.62 | C |
| ATOM | 13991 | O | SER | B | 378 | −36.495 | −23.435 | −41.199 | 1.00 | 25.70 | O |
| ATOM | 13993 | N | THR | B | 379 | −35.108 | −25.129 | −40.690 | 1.00 | 25.66 | N |
| ATOM | 13994 | CA | THR | B | 379 | −36.038 | −26.175 | −41.097 | 1.00 | 25.55 | C |
| ATOM | 13996 | CB | THR | B | 379 | −35.788 | −26.635 | −42.546 | 1.00 | 25.59 | C |
| ATOM | 13998 | OG1 | THR | B | 379 | −34.391 | −26.899 | −42.736 | 1.00 | 25.46 | O |
| ATOM | 14000 | CG2 | THR | B | 379 | −36.255 | −25.574 | −43.528 | 1.00 | 25.88 | C |
| ATOM | 14004 | C | THR | B | 379 | −35.886 | −27.348 | −40.160 | 1.00 | 25.45 | C |
| ATOM | 14005 | O | THR | B | 379 | −35.372 | −28.393 | −40.548 | 1.00 | 25.70 | O |
| ATOM | 14007 | N | PRO | B | 380 | −36.335 | −27.179 | −38.915 | 1.00 | 25.37 | N |
| ATOM | 14008 | CA | PRO | B | 380 | −36.144 | −28.182 | −37.876 | 1.00 | 25.22 | C |
| ATOM | 14010 | CB | PRO | B | 380 | −36.500 | −27.437 | −36.583 | 1.00 | 25.19 | C |
| ATOM | 14013 | CG | PRO | B | 380 | −36.643 | −26.021 | −36.955 | 1.00 | 25.83 | C |
| ATOM | 14016 | CD | PRO | B | 380 | −37.025 | −25.998 | −38.390 | 1.00 | 25.71 | C |
| ATOM | 14019 | C | PRO | B | 380 | −37.052 | −29.379 | −38.009 | 1.00 | 24.82 | C |
| ATOM | 14020 | O | PRO | B | 380 | −38.143 | −29.280 | −38.575 | 1.00 | 24.84 | O |
| ATOM | 14021 | N | THR | B | 381 | −36.607 | −30.493 | −37.436 | 1.00 | 24.42 | N |
| ATOM | 14022 | CA | THR | B | 381 | −37.386 | −31.712 | −37.429 | 1.00 | 23.99 | C |
| ATOM | 14024 | CB | THR | B | 381 | −36.614 | −32.873 | −36.789 | 1.00 | 23.99 | C |
| ATOM | 14026 | OG1 | THR | B | 381 | −36.339 | −32.575 | −35.418 | 1.00 | 24.02 | O |
| ATOM | 14028 | CG2 | THR | B | 381 | −35.302 | −33.117 | −37.524 | 1.00 | 23.76 | C |
| ATOM | 14032 | C | THR | B | 381 | −38.649 | −31.461 | −36.636 | 1.00 | 23.78 | C |
| ATOM | 14033 | O | THR | B | 381 | −38.700 | −30.548 | −35.813 | 1.00 | 23.89 | O |
| ATOM | 14035 | N | PHE | B | 382 | −39.672 | −32.267 | −36.889 | 1.00 | 23.53 | N |
| ATOM | 14036 | CA | PHE | B | 382 | −40.905 | −32.204 | −36.105 | 1.00 | 22.97 | C |
| ATOM | 14038 | CB | PHE | B | 382 | −41.870 | −33.305 | −36.527 | 1.00 | 22.89 | C |
| ATOM | 14041 | CG | PHE | B | 382 | −43.079 | −33.394 | −35.655 | 1.00 | 22.26 | C |
| ATOM | 14042 | CD1 | PHE | B | 382 | −44.189 | −32.601 | −35.910 | 1.00 | 21.65 | C |
| ATOM | 14044 | CE1 | PHE | B | 382 | −45.300 | −32.672 | −35.099 | 1.00 | 20.87 | C |
| ATOM | 14046 | CZ | PHE | B | 382 | −45.310 | −33.534 | −34.016 | 1.00 | 20.36 | C |
| ATOM | 14048 | CE2 | PHE | B | 382 | −44.204 | −34.317 | −33.744 | 1.00 | 20.52 | C |
| ATOM | 14050 | CD2 | PHE | B | 382 | −43.098 | −34.243 | −34.556 | 1.00 | 21.17 | C |
| ATOM | 14052 | C | PHE | B | 382 | −40.677 | −32.329 | −34.605 | 1.00 | 22.69 | C |
| ATOM | 14053 | O | PHE | B | 382 | −41.341 | −31.657 | −33.834 | 1.00 | 22.44 | O |

TABLE 3-7-continued

Coordinates of *P. tremuloides* IspS

| ATOM | 14055 | N | ASP | B | 383 | −39.764 | −33.205 | −34.191 | 1.00 | 22.52 | N |
|---|---|---|---|---|---|---|---|---|---|---|---|
| ATOM | 14056 | CA | ASP | B | 383 | −39.491 | −33.375 | −32.765 | 1.00 | 22.50 | C |
| ATOM | 14058 | CB | ASP | B | 383 | −38.531 | −34.525 | −32.527 | 1.00 | 22.43 | C |
| ATOM | 14061 | CG | ASP | B | 383 | −39.174 | −35.863 | −32.711 | 1.00 | 22.71 | C |
| ATOM | 14062 | OD1 | ASP | B | 383 | −40.359 | −35.945 | −33.074 | 1.00 | 22.89 | O |
| ATOM | 14063 | OD2 | ASP | B | 383 | −38.470 | −36.856 | −32.492 | 1.00 | 25.17 | O |
| ATOM | 14064 | C | ASP | B | 383 | −38.954 | −32.116 | −32.091 | 1.00 | 22.43 | C |
| ATOM | 14065 | O | ASP | B | 383 | −39.438 | −31.758 | −31.014 | 1.00 | 22.40 | O |
| ATOM | 14067 | N | ASP | B | 384 | −37.966 | −31.464 | −32.713 | 1.00 | 22.37 | N |
| ATOM | 14068 | CA | ASP | B | 384 | −37.422 | −30.191 | −32.213 | 1.00 | 22.61 | C |
| ATOM | 14070 | CB | ASP | B | 384 | −36.317 | −29.648 | −33.124 | 1.00 | 22.82 | C |
| ATOM | 14073 | CG | ASP | B | 384 | −34.963 | −30.208 | −32.807 | 1.00 | 23.40 | C |
| ATOM | 14074 | OD1 | ASP | B | 384 | −34.847 | −30.973 | −31.832 | 1.00 | 25.33 | O |
| ATOM | 14075 | OD2 | ASP | B | 384 | −34.009 | −29.891 | −33.545 | 1.00 | 24.26 | O |
| ATOM | 14076 | C | ASP | B | 384 | −38.482 | −29.113 | −32.130 | 1.00 | 22.56 | C |
| ATOM | 14077 | O | ASP | B | 384 | −38.598 | −28.429 | −31.108 | 1.00 | 22.48 | O |
| ATOM | 14079 | N | TYR | B | 385 | −39.227 | −28.963 | −33.227 | 1.00 | 22.36 | N |
| ATOM | 14080 | CA | TYR | B | 385 | −40.170 | −27.870 | −33.402 | 1.00 | 22.18 | C |
| ATOM | 14082 | CB | TYR | B | 385 | −40.738 | −27.867 | −34.812 | 1.00 | 22.05 | C |
| ATOM | 14085 | CG | TYR | B | 385 | −41.818 | −26.834 | −35.019 | 1.00 | 22.60 | C |
| ATOM | 14086 | CD1 | TYR | B | 385 | −41.493 | −25.553 | −35.437 | 1.00 | 23.64 | C |
| ATOM | 14088 | CE1 | TYR | B | 385 | −42.462 | −24.580 | −35.630 | 1.00 | 25.00 | C |
| ATOM | 14090 | CZ | TYR | B | 385 | −43.788 | −24.882 | −35.410 | 1.00 | 26.86 | C |
| ATOM | 14091 | OH | TYR | B | 385 | −44.734 | −23.883 | −35.622 | 1.00 | 28.48 | O |
| ATOM | 14093 | CE2 | TYR | B | 385 | −44.149 | −26.171 | −34.980 | 1.00 | 25.95 | C |
| ATOM | 14095 | CD2 | TYR | B | 385 | −43.158 | −27.133 | −34.790 | 1.00 | 23.94 | C |
| ATOM | 14097 | C | TYR | B | 385 | −41.319 | −27.986 | −32.446 | 1.00 | 22.13 | C |
| ATOM | 14098 | O | TYR | B | 385 | −41.703 | −27.017 | −31.808 | 1.00 | 22.95 | O |
| ATOM | 14100 | N | PHE | B | 386 | −41.899 | −29.169 | −32.380 | 1.00 | 21.80 | N |
| ATOM | 14101 | CA | PHE | B | 386 | −43.048 | −29.394 | −31.525 | 1.00 | 21.62 | C |
| ATOM | 14103 | CB | PHE | B | 386 | −43.624 | −30.795 | −31.768 | 1.00 | 21.73 | C |
| ATOM | 14106 | CG | PHE | B | 386 | −44.834 | −31.104 | −30.952 | 1.00 | 21.27 | C |
| ATOM | 14107 | CD1 | PHE | B | 386 | −46.034 | −30.447 | −31.196 | 1.00 | 22.55 | C |
| ATOM | 14109 | CE1 | PHE | B | 386 | −47.164 | −30.732 | −30.448 | 1.00 | 23.14 | C |
| ATOM | 14111 | CZ | PHE | B | 386 | −47.095 | −31.699 | −29.446 | 1.00 | 23.20 | C |
| ATOM | 14113 | CE2 | PHE | B | 386 | −45.896 | −32.358 | −29.208 | 1.00 | 21.57 | C |
| ATOM | 14115 | CD2 | PHE | B | 386 | −44.781 | −32.057 | −29.959 | 1.00 | 20.29 | C |
| ATOM | 14117 | C | PHE | B | 386 | −42.630 | −29.226 | −30.073 | 1.00 | 21.34 | C |
| ATOM | 14118 | O | PHE | B | 386 | −43.353 | −28.639 | −29.284 | 1.00 | 21.44 | O |
| ATOM | 14120 | N | GLY | B | 387 | −41.447 | −29.725 | −29.736 | 1.00 | 20.84 | N |
| ATOM | 14121 | CA | GLY | B | 387 | −40.935 | −29.618 | −28.387 | 1.00 | 20.57 | C |
| ATOM | 14124 | C | GLY | B | 387 | −40.854 | −28.186 | −27.916 | 1.00 | 20.26 | C |
| ATOM | 14125 | O | GLY | B | 387 | −40.930 | −27.908 | −26.724 | 1.00 | 20.86 | O |
| ATOM | 14127 | N | ASN | B | 388 | −40.691 | −27.268 | −28.852 | 1.00 | 19.81 | N |
| ATOM | 14128 | CA | ASN | B | 388 | −40.758 | −25.853 | −28.536 | 1.00 | 19.51 | C |
| ATOM | 14130 | CB | ASN | B | 388 | −39.877 | −25.086 | −29.508 | 1.00 | 19.42 | C |
| ATOM | 14133 | CG | ASN | B | 388 | −39.593 | −23.700 | −29.045 | 1.00 | 19.26 | C |
| ATOM | 14134 | OD1 | ASN | B | 388 | −38.916 | −23.513 | −28.038 | 1.00 | 18.93 | O |
| ATOM | 14135 | ND2 | ASN | B | 388 | −40.105 | −22.709 | −29.774 | 1.00 | 17.99 | N |
| ATOM | 14138 | C | ASN | B | 388 | −42.200 | −25.320 | −28.604 | 1.00 | 19.41 | C |
| ATOM | 14139 | O | ASN | B | 388 | −42.591 | −24.447 | −27.833 | 1.00 | 19.58 | O |
| ATOM | 14141 | N | ALA | B | 389 | −42.989 | −25.848 | −29.532 | 1.00 | 19.11 | N |
| ATOM | 14142 | CA | ALA | B | 389 | −44.313 | −25.307 | −29.808 | 1.00 | 18.87 | C |
| ATOM | 14144 | CB | ALA | B | 389 | −44.897 | −25.949 | −31.060 | 1.00 | 18.87 | C |
| ATOM | 14148 | C | ALA | B | 389 | −45.264 | −25.460 | −28.634 | 1.00 | 18.51 | C |
| ATOM | 14149 | O | ALA | B | 389 | −45.916 | −24.511 | −28.262 | 1.00 | 18.33 | O |
| ATOM | 14151 | N | TRP | B | 390 | −45.344 | −26.652 | −28.054 | 1.00 | 18.73 | N |
| ATOM | 14152 | CA | TRP | B | 390 | −46.258 | −26.887 | −26.935 | 1.00 | 18.74 | C |
| ATOM | 14154 | CB | TRP | B | 390 | −46.389 | −28.377 | −26.569 | 1.00 | 18.75 | C |
| ATOM | 14157 | CG | TRP | B | 390 | −45.166 | −29.122 | −26.019 | 1.00 | 18.46 | C |
| ATOM | 14158 | CD1 | TRP | B | 390 | −44.390 | −30.001 | −26.705 | 1.00 | 18.75 | C |
| ATOM | 14160 | NE1 | TRP | B | 390 | −43.417 | −30.519 | −25.897 | 1.00 | 17.56 | N |
| ATOM | 14162 | CE2 | TRP | B | 390 | −43.559 | −30.005 | −24.642 | 1.00 | 16.67 | C |
| ATOM | 14163 | CD2 | TRP | B | 390 | −44.661 | −29.124 | −24.674 | 1.00 | 17.50 | C |
| ATOM | 14164 | CE3 | TRP | B | 390 | −45.008 | −28.448 | −23.505 | 1.00 | 18.38 | C |
| ATOM | 14166 | CZ3 | TRP | B | 390 | −44.251 | −28.685 | −22.347 | 1.00 | 18.34 | C |
| ATOM | 14168 | CH2 | TRP | B | 390 | −43.164 | −29.573 | −22.361 | 1.00 | 16.75 | C |
| ATOM | 14170 | CZ2 | TRP | B | 390 | −42.805 | −30.234 | −23.495 | 1.00 | 15.75 | C |
| ATOM | 14172 | C | TRP | B | 390 | −45.861 | −26.066 | −25.727 | 1.00 | 18.91 | C |
| ATOM | 14173 | O | TRP | B | 390 | −46.707 | −25.691 | −24.919 | 1.00 | 19.02 | O |
| ATOM | 14175 | N | LYS | B | 391 | −44.570 | −25.787 | −25.612 | 1.00 | 18.95 | N |
| ATOM | 14176 | CA | LYS | B | 391 | −44.085 | −24.810 | −24.643 | 1.00 | 18.85 | C |
| ATOM | 14178 | CB | LYS | B | 391 | −42.544 | −24.888 | −24.508 | 1.00 | 19.52 | C |
| ATOM | 14181 | CG | LYS | B | 391 | −42.023 | −25.373 | −23.143 | 1.00 | 21.17 | C |
| ATOM | 14184 | CD | LYS | B | 391 | −40.516 | −25.689 | −23.191 | 1.00 | 22.87 | C |
| ATOM | 14187 | CE | LYS | B | 391 | −40.251 | −27.159 | −23.508 | 1.00 | 23.91 | C |
| ATOM | 14190 | NZ | LYS | B | 391 | −38.938 | −27.354 | −24.191 | 1.00 | 25.44 | N |
| ATOM | 14194 | C | LYS | B | 391 | −44.537 | −23.400 | −25.032 | 1.00 | 17.57 | C |

TABLE 3-7-continued

| | | | | | Coordinates of *P. tremuloides* IspS | | | | | |
|---|---|---|---|---|---|---|---|---|---|---|
| ATOM | 14195 | O | LYS | B | 391 | −44.937 | −22.629 | −24.180 | 1.00 | 17.66 O |
| ATOM | 14197 | N | SER | B | 392 | −44.490 | −23.068 | −26.314 | 1.00 | 16.65 N |
| ATOM | 14198 | CA | SER | B | 392 | −44.879 | −21.718 | −26.764 | 1.00 | 16.27 C |
| ATOM | 14200 | CB | SER | B | 392 | −44.241 | −21.375 | −28.119 | 1.00 | 16.22 C |
| ATOM | 14203 | OG | SER | B | 392 | −44.937 | −21.969 | −29.207 | 1.00 | 15.94 O |
| ATOM | 14205 | C | SER | B | 392 | −46.384 | −21.504 | −26.866 | 1.00 | 15.87 C |
| ATOM | 14206 | O | SER | B | 392 | −46.825 | −20.395 | −27.093 | 1.00 | 15.56 O |
| ATOM | 14208 | N | SER | B | 393 | −47.167 | −22.568 | −26.724 | 1.00 | 15.92 N |
| ATOM | 14209 | CA | SER | B | 393 | −48.629 | −22.474 | −26.718 | 1.00 | 15.80 C |
| ATOM | 14211 | CB | SER | B | 393 | −49.240 | −23.867 | −26.630 | 1.00 | 15.78 C |
| ATOM | 14214 | OG | SER | B | 393 | −49.025 | −24.426 | −25.348 | 1.00 | 15.00 O |
| ATOM | 14216 | C | SER | B | 393 | −49.097 | −21.646 | −25.533 | 1.00 | 15.94 C |
| ATOM | 14217 | O | SER | B | 393 | −50.115 | −20.948 | −25.599 | 1.00 | 15.60 O |
| ATOM | 14219 | N | SER | B | 394 | −48.296 | −21.740 | −24.471 | 1.00 | 16.14 N |
| ATOM | 14220 | CA | SER | B | 394 | −48.487 | −21.091 | −23.177 | 1.00 | 16.31 C |
| ATOM | 14222 | CB | SER | B | 394 | −49.062 | −19.662 | −23.271 | 1.00 | 16.18 C |
| ATOM | 14225 | OG | SER | B | 394 | −50.472 | −19.649 | −23.358 | 1.00 | 16.57 O |
| ATOM | 14227 | C | SER | B | 394 | −49.316 | −22.006 | −22.297 | 1.00 | 16.34 C |
| ATOM | 14228 | O | SER | B | 394 | −49.822 | −21.595 | −21.261 | 1.00 | 16.47 O |
| ATOM | 14230 | N | GLY | B | 395 | −49.403 | −23.268 | −22.702 | 1.00 | 16.55 N |
| ATOM | 14231 | CA | GLY | B | 395 | −50.103 | −24.282 | −21.927 | 1.00 | 16.79 C |
| ATOM | 14234 | C | GLY | B | 395 | −49.543 | −24.391 | −20.534 | 1.00 | 16.80 C |
| ATOM | 14235 | O | GLY | B | 395 | −50.222 | −24.083 | −19.556 | 1.00 | 16.74 O |
| ATOM | 14237 | N | PRO | B | 396 | −48.291 | −24.824 | −20.430 | 1.00 | 17.07 N |
| ATOM | 14238 | CA | PRO | B | 396 | −47.698 | −24.930 | −19.103 | 1.00 | 17.18 C |
| ATOM | 14240 | CB | PRO | B | 396 | −46.273 | −25.399 | −19.386 | 1.00 | 17.09 C |
| ATOM | 14243 | CG | PRO | B | 396 | −46.087 | −25.237 | −20.874 | 1.00 | 17.77 C |
| ATOM | 14246 | CD | PRO | B | 396 | −47.424 | −25.390 | −21.470 | 1.00 | 17.20 C |
| ATOM | 14249 | C | PRO | B | 396 | −47.707 | −23.615 | −18.313 | 1.00 | 17.17 C |
| ATOM | 14250 | O | PRO | B | 396 | −47.921 | −23.644 | −17.089 | 1.00 | 17.10 O |
| ATOM | 14251 | N | LEU | B | 397 | −47.499 | −22.475 | −18.983 | 1.00 | 17.04 N |
| ATOM | 14252 | CA | LEU | B | 397 | −47.513 | −21.183 | −18.261 | 1.00 | 16.77 C |
| ATOM | 14254 | CB | LEU | B | 397 | −47.116 | −19.969 | −19.135 | 1.00 | 16.84 C |
| ATOM | 14257 | CG | LEU | B | 397 | −47.145 | −18.576 | −18.458 | 1.00 | 16.91 C |
| ATOM | 14259 | CD1 | LEU | B | 397 | −46.577 | −18.641 | −17.096 | 1.00 | 18.36 C |
| ATOM | 14263 | CD2 | LEU | B | 397 | −46.373 | −17.515 | −19.196 | 1.00 | 16.88 C |
| ATOM | 14267 | C | LEU | B | 397 | −48.894 | −20.988 | −17.682 | 1.00 | 16.24 C |
| ATOM | 14268 | O | LEU | B | 397 | −49.051 | −20.710 | −16.494 | 1.00 | 16.09 O |
| ATOM | 14270 | N | GLN | B | 398 | −49.902 | −21.173 | −18.515 | 1.00 | 15.72 N |
| ATOM | 14271 | CA | GLN | B | 398 | −51.262 | −21.093 | −18.024 | 1.00 | 15.49 C |
| ATOM | 14273 | CB | GLN | B | 398 | −52.267 | −21.387 | −19.120 | 1.00 | 15.51 C |
| ATOM | 14276 | CG | GLN | B | 398 | −52.371 | −20.275 | −20.118 | 1.00 | 16.12 C |
| ATOM | 14279 | CD | GLN | B | 398 | −53.436 | −20.545 | −21.114 | 1.00 | 17.86 C |
| ATOM | 14280 | OE1 | GLN | B | 398 | −54.509 | −21.028 | −20.757 | 1.00 | 20.99 O |
| ATOM | 14281 | NE2 | GLN | B | 398 | −53.170 | −20.239 | −22.374 | 1.00 | 18.31 N |
| ATOM | 14284 | C | GLN | B | 398 | −51.471 | −22.040 | −16.873 | 1.00 | 15.03 C |
| ATOM | 14285 | O | GLN | B | 398 | −51.974 | −21.638 | −15.843 | 1.00 | 15.21 O |
| ATOM | 14287 | N | LEU | B | 399 | −51.065 | −23.291 | −17.022 | 1.00 | 14.72 N |
| ATOM | 14288 | CA | LEU | B | 399 | −51.361 | −24.254 | −15.978 | 1.00 | 14.65 C |
| ATOM | 14290 | CB | LEU | B | 399 | −51.201 | −25.688 | −16.475 | 1.00 | 14.44 C |
| ATOM | 14293 | CG | LEU | B | 399 | −52.250 | −26.191 | −17.478 | 1.00 | 14.28 C |
| ATOM | 14295 | CD1 | LEU | B | 399 | −51.907 | −27.633 | −17.846 | 1.00 | 15.50 C |
| ATOM | 14299 | CD2 | LEU | B | 399 | −53.713 | −26.077 | −16.986 | 1.00 | 10.96 C |
| ATOM | 14303 | C | LEU | B | 399 | −50.554 | −23.995 | −14.704 | 1.00 | 14.88 C |
| ATOM | 14304 | O | LEU | B | 399 | −51.100 | −24.161 | −13.618 | 1.00 | 15.21 O |
| ATOM | 14306 | N | ILE | B | 400 | −49.291 | −23.562 | −14.810 | 1.00 | 14.91 N |
| ATOM | 14307 | CA | ILE | B | 400 | −48.532 | −23.174 | −13.607 | 1.00 | 14.89 C |
| ATOM | 14309 | CB | ILE | B | 400 | −47.158 | −22.574 | −13.907 | 1.00 | 15.19 C |
| ATOM | 14311 | CG1 | ILE | B | 400 | −46.189 | −23.674 | −14.353 | 1.00 | 16.76 C |
| ATOM | 14314 | CD1 | ILE | B | 400 | −44.777 | −23.162 | −14.716 | 1.00 | 18.19 C |
| ATOM | 14318 | CG2 | ILE | B | 400 | −46.603 | −21.906 | −12.665 | 1.00 | 13.65 C |
| ATOM | 14322 | C | ILE | B | 400 | −49.288 | −22.137 | −12.819 | 1.00 | 14.77 C |
| ATOM | 14323 | O | ILE | B | 400 | −49.485 | −22.302 | −11.632 | 1.00 | 15.36 O |
| ATOM | 14325 | N | PHE | B | 401 | −49.717 | −21.071 | −13.486 | 1.00 | 14.59 N |
| ATOM | 14326 | CA | PHE | B | 401 | −50.491 | −20.001 | −12.844 | 1.00 | 14.22 C |
| ATOM | 14328 | CB | PHE | B | 401 | −50.825 | −18.900 | −13.845 | 1.00 | 14.12 C |
| ATOM | 14331 | CG | PHE | B | 401 | −49.803 | −17.790 | −13.872 | 1.00 | 13.83 C |
| ATOM | 14332 | CD1 | PHE | B | 401 | −50.012 | −16.623 | −13.173 | 1.00 | 12.77 C |
| ATOM | 14334 | CE1 | PHE | B | 401 | −49.074 | −15.629 | −13.189 | 1.00 | 13.09 C |
| ATOM | 14336 | CZ | PHE | B | 401 | −47.906 | −15.781 | −13.902 | 1.00 | 12.96 C |
| ATOM | 14338 | CE2 | PHE | B | 401 | −47.684 | −16.928 | −14.592 | 1.00 | 12.86 C |
| ATOM | 14340 | CD2 | PHE | B | 401 | −48.622 | −17.932 | −14.574 | 1.00 | 13.30 C |
| ATOM | 14342 | C | PHE | B | 401 | −51.765 | −20.478 | −12.212 | 1.00 | 14.26 C |
| ATOM | 14343 | O | PHE | B | 401 | −52.184 | −19.944 | −11.207 | 1.00 | 13.90 O |
| ATOM | 14345 | N | ALA | B | 402 | −52.377 | −21.480 | −12.828 | 1.00 | 15.09 N |
| ATOM | 14346 | CA | ALA | B | 402 | −53.641 | −22.054 | −12.364 | 1.00 | 15.76 C |
| ATOM | 14348 | CB | ALA | B | 402 | −54.264 | −22.899 | −13.454 | 1.00 | 15.57 C |
| ATOM | 14352 | C | ALA | B | 402 | −53.417 | −22.896 | −11.129 | 1.00 | 16.63 C |

TABLE 3-7-continued

Coordinates of *P. tremuloides* IspS

| ATOM | 14353 | O | ALA | B | 402 | −54.284 | −22.970 | −10.259 | 1.00 | 17.00 | O |
|------|-------|---|-----|---|-----|---------|---------|---------|------|-------|---|
| ATOM | 14355 | N | TYR | B | 403 | −52.253 | −23.544 | −11.060 | 1.00 | 17.50 | N |
| ATOM | 14356 | CA | TYR | B | 403 | −51.885 | −24.317 | −9.894 | 1.00 | 17.86 | C |
| ATOM | 14358 | CB | TYR | B | 403 | −50.486 | −24.911 | −10.038 | 1.00 | 17.73 | C |
| ATOM | 14361 | CG | TYR | B | 403 | −50.006 | −25.576 | −8.764 | 1.00 | 18.24 | C |
| ATOM | 14362 | CD1 | TYR | B | 403 | −50.401 | −26.867 | −8.436 | 1.00 | 18.12 | C |
| ATOM | 14364 | CE1 | TYR | B | 403 | −49.971 | −27.476 | −7.273 | 1.00 | 18.07 | C |
| ATOM | 14366 | CZ | TYR | B | 403 | −49.145 | −26.790 | −6.409 | 1.00 | 18.62 | C |
| ATOM | 14367 | OH | TYR | B | 403 | −48.727 | −27.383 | −5.244 | 1.00 | 17.70 | O |
| ATOM | 14369 | CE2 | TYR | B | 403 | −48.748 | −25.499 | −6.703 | 1.00 | 18.93 | C |
| ATOM | 14371 | CD2 | TYR | B | 403 | −49.177 | −24.901 | −7.876 | 1.00 | 18.88 | C |
| ATOM | 14373 | C | TYR | B | 403 | −51.966 | −23.461 | −8.630 | 1.00 | 18.48 | C |
| ATOM | 14374 | O | TYR | B | 403 | −52.494 | −23.908 | −7.616 | 1.00 | 18.66 | O |
| ATOM | 14376 | N | PHE | B | 404 | −51.468 | −22.232 | −8.682 | 1.00 | 18.91 | N |
| ATOM | 14377 | CA | PHE | B | 404 | −51.400 | −21.430 | −7.468 | 1.00 | 19.53 | C |
| ATOM | 14379 | CB | PHE | B | 404 | −50.395 | −20.325 | −7.644 | 1.00 | 19.35 | C |
| ATOM | 14382 | CG | PHE | B | 404 | −49.014 | −20.808 | −7.799 | 1.00 | 18.79 | C |
| ATOM | 14383 | CD1 | PHE | B | 404 | −48.311 | −21.246 | −6.701 | 1.00 | 17.67 | C |
| ATOM | 14385 | CE1 | PHE | B | 404 | −47.001 | −21.683 | −6.832 | 1.00 | 18.44 | C |
| ATOM | 14387 | CZ | PHE | B | 404 | −46.384 | −21.688 | −8.078 | 1.00 | 18.44 | C |
| ATOM | 14389 | CE2 | PHE | B | 404 | −47.083 | −21.245 | −9.190 | 1.00 | 18.79 | C |
| ATOM | 14391 | CD2 | PHE | B | 404 | −48.396 | −20.805 | −9.047 | 1.00 | 18.90 | C |
| ATOM | 14393 | C | PHE | B | 404 | −52.733 | −20.817 | −7.072 | 1.00 | 20.49 | C |
| ATOM | 14394 | O | PHE | B | 404 | −52.925 | −20.389 | −5.924 | 1.00 | 19.95 | O |
| ATOM | 14396 | N | ALA | B | 405 | −53.636 | −20.756 | −8.043 | 1.00 | 21.92 | N |
| ATOM | 14397 | CA | ALA | B | 405 | −54.918 | −20.106 | −7.872 | 1.00 | 23.09 | C |
| ATOM | 14399 | CB | ALA | B | 405 | −55.333 | −19.426 | −9.167 | 1.00 | 23.15 | C |
| ATOM | 14403 | C | ALA | B | 405 | −55.959 | −21.113 | −7.446 | 1.00 | 24.23 | C |
| ATOM | 14404 | O | ALA | B | 405 | −57.003 | −20.726 | −6.925 | 1.00 | 24.33 | O |
| ATOM | 14406 | N | VAL | B | 406 | −55.657 | −22.399 | −7.662 | 1.00 | 25.80 | N |
| ATOM | 14407 | CA | VAL | B | 406 | −56.569 | −23.511 | −7.355 | 1.00 | 26.88 | C |
| ATOM | 14409 | CB | VAL | B | 406 | −56.640 | −24.514 | −8.512 | 1.00 | 26.64 | C |
| ATOM | 14411 | CG1 | VAL | B | 406 | −57.132 | −25.854 | −8.012 | 1.00 | 27.24 | C |
| ATOM | 14415 | CG2 | VAL | B | 406 | −57.547 | −23.986 | −9.593 | 1.00 | 26.45 | C |
| ATOM | 14419 | C | VAL | B | 406 | −56.161 | −24.266 | −6.094 | 1.00 | 27.91 | C |
| ATOM | 14420 | O | VAL | B | 406 | −56.932 | −24.345 | −5.155 | 1.00 | 28.28 | O |
| ATOM | 14422 | N | VAL | B | 407 | −54.954 | −24.825 | −6.087 | 1.00 | 29.25 | N |
| ATOM | 14423 | CA | VAL | B | 407 | −54.443 | −25.573 | −4.941 | 1.00 | 30.16 | C |
| ATOM | 14425 | CB | VAL | B | 407 | −53.128 | −26.276 | −5.279 | 1.00 | 30.04 | C |
| ATOM | 14427 | CG1 | VAL | B | 407 | −52.482 | −26.831 | −4.032 | 1.00 | 30.42 | C |
| ATOM | 14431 | CG2 | VAL | B | 407 | −53.378 | −27.376 | −6.280 | 1.00 | 30.14 | C |
| ATOM | 14435 | C | VAL | B | 407 | −54.208 | −24.646 | −3.755 | 1.00 | 31.34 | C |
| ATOM | 14436 | O | VAL | B | 407 | −53.535 | −23.618 | −3.876 | 1.00 | 31.46 | O |
| ATOM | 14438 | N | GLN | B | 408 | −54.753 | −25.032 | −2.604 | 1.00 | 32.63 | N |
| ATOM | 14439 | CA | GLN | B | 408 | −54.727 | −24.191 | −1.417 | 1.00 | 33.51 | C |
| ATOM | 14441 | CB | GLN | B | 408 | −55.891 | −24.572 | −.514 | 1.00 | 33.84 | C |
| ATOM | 14444 | CG | GLN | B | 408 | −56.161 | −23.548 | .577 | 1.00 | 35.49 | C |
| ATOM | 14447 | CD | GLN | B | 408 | −57.623 | −23.161 | .656 | 1.00 | 37.61 | C |
| ATOM | 14448 | OE1 | GLN | B | 408 | −58.519 | −24.006 | .501 | 1.00 | 38.23 | O |
| ATOM | 14449 | NE2 | GLN | B | 408 | −57.876 | −21.874 | .893 | 1.00 | 38.64 | N |
| ATOM | 14452 | C | GLN | B | 408 | −53.399 | −24.274 | −.647 | 1.00 | 33.72 | C |
| ATOM | 14453 | O | GLN | B | 408 | −52.852 | −23.253 | −.204 | 1.00 | 33.52 | O |
| ATOM | 14455 | N | ASN | B | 409 | −52.889 | −25.491 | −.490 | 1.00 | 33.95 | N |
| ATOM | 14456 | CA | ASN | B | 409 | −51.642 | −25.707 | .226 | 1.00 | 34.16 | C |
| ATOM | 14458 | CB | ASN | B | 409 | −51.865 | −26.665 | 1.391 | 1.00 | 34.25 | C |
| ATOM | 14461 | CG | ASN | B | 409 | −52.756 | −26.069 | 2.459 | 1.00 | 34.39 | C |
| ATOM | 14462 | OD1 | ASN | B | 409 | −52.269 | −25.577 | 3.480 | 1.00 | 34.40 | O |
| ATOM | 14463 | ND2 | ASN | B | 409 | −54.070 | −26.089 | 2.222 | 1.00 | 34.12 | N |
| ATOM | 14466 | C | ASN | B | 409 | −50.582 | −26.244 | −.709 | 1.00 | 34.12 | C |
| ATOM | 14467 | O | ASN | B | 409 | −50.578 | −27.422 | −1.046 | 1.00 | 34.41 | O |
| ATOM | 14469 | N | ILE | B | 410 | −49.681 | −25.369 | −1.127 | 1.00 | 34.07 | N |
| ATOM | 14470 | CA | ILE | B | 410 | −48.699 | −25.718 | −2.138 | 1.00 | 34.08 | C |
| ATOM | 14472 | CB | ILE | B | 410 | −48.138 | −24.455 | −2.840 | 1.00 | 34.15 | C |
| ATOM | 14474 | CG1 | ILE | B | 410 | −47.274 | −23.610 | −1.891 | 1.00 | 34.26 | C |
| ATOM | 14477 | CD1 | ILE | B | 410 | −47.216 | −22.139 | −2.249 | 1.00 | 34.10 | C |
| ATOM | 14481 | CG2 | ILE | B | 410 | −49.290 | −23.634 | −3.404 | 1.00 | 34.49 | C |
| ATOM | 14485 | C | ILE | B | 410 | −47.586 | −26.553 | −1.533 | 1.00 | 33.93 | C |
| ATOM | 14486 | O | ILE | B | 410 | −47.181 | −26.317 | −.405 | 1.00 | 33.80 | O |
| ATOM | 14488 | N | LYS | B | 411 | −47.123 | −27.546 | −2.285 | 1.00 | 34.12 | N |
| ATOM | 14489 | CA | LYS | B | 411 | −46.012 | −28.395 | −1.874 | 1.00 | 34.45 | C |
| ATOM | 14491 | CB | LYS | B | 411 | −46.414 | −29.873 | −1.907 | 1.00 | 34.67 | C |
| ATOM | 14494 | CG | LYS | B | 411 | −47.850 | −30.130 | −1.460 | 1.00 | 35.79 | C |
| ATOM | 14497 | CD | LYS | B | 411 | −48.102 | −31.586 | −1.052 | 1.00 | 37.60 | C |
| ATOM | 14500 | CE | LYS | B | 411 | −49.450 | −31.728 | −.309 | 1.00 | 38.80 | C |
| ATOM | 14503 | NZ | LYS | B | 411 | −49.568 | −32.992 | .488 | 1.00 | 39.20 | N |
| ATOM | 14507 | C | LYS | B | 411 | −44.843 | −28.132 | −2.810 | 1.00 | 34.33 | C |
| ATOM | 14508 | O | LYS | B | 411 | −45.038 | −27.956 | −4.006 | 1.00 | 34.14 | O |
| ATOM | 14510 | N | LYS | B | 412 | −43.631 | −28.102 | −2.265 | 1.00 | 34.50 | N |

TABLE 3-7-continued

| | | | | | | | | | | | |
|---|---|---|---|---|---|---|---|---|---|---|---|
| ATOM | 14511 | CA | LYS | B | 412 | −42.460 | −27.688 | −3.042 | 1.00 | 34.69 | C |
| ATOM | 14513 | CB | LYS | B | 412 | −41.242 | −27.398 | −2.154 | 1.00 | 35.13 | C |
| ATOM | 14516 | CG | LYS | B | 412 | −41.205 | −25.960 | −1.613 | 1.00 | 36.90 | C |
| ATOM | 14519 | CD | LYS | B | 412 | −40.079 | −25.749 | −.588 | 1.00 | 38.57 | C |
| ATOM | 14522 | CE | LYS | B | 412 | −40.546 | −24.852 | .555 | 1.00 | 39.55 | C |
| ATOM | 14525 | NZ | LYS | B | 412 | −39.491 | −24.644 | 1.587 | 1.00 | 40.83 | N |
| ATOM | 14529 | C | LYS | B | 412 | −42.075 | −28.687 | −4.103 | 1.00 | 34.13 | C |
| ATOM | 14530 | O | LYS | B | 412 | −41.468 | −28.308 | −5.093 | 1.00 | 34.21 | O |
| ATOM | 14532 | N | GLU | B | 413 | −42.408 | −29.958 | −3.910 | 1.00 | 33.54 | N |
| ATOM | 14533 | CA | GLU | B | 413 | −42.095 | −30.949 | −4.933 | 1.00 | 33.19 | C |
| ATOM | 14535 | CB | GLU | B | 413 | −41.886 | −32.335 | −4.330 | 1.00 | 33.44 | C |
| ATOM | 14538 | CG | GLU | B | 413 | −43.127 | −33.037 | −3.807 | 1.00 | 34.37 | C |
| ATOM | 14541 | CD | GLU | B | 413 | −42.834 | −34.490 | −3.499 | 1.00 | 35.56 | C |
| ATOM | 14542 | OE1 | GLU | B | 413 | −42.662 | −35.264 | −4.471 | 1.00 | 35.30 | O |
| ATOM | 14543 | OE2 | GLU | B | 413 | −42.751 | −34.847 | −2.297 | 1.00 | 36.69 | O |
| ATOM | 14544 | C | GLU | B | 413 | −43.157 | −30.965 | −6.029 | 1.00 | 32.47 | C |
| ATOM | 14545 | O | GLU | B | 413 | −42.846 | −31.232 | −7.193 | 1.00 | 32.28 | O |
| ATOM | 14547 | N | GLU | B | 414 | −44.403 | −30.676 | −5.652 | 1.00 | 31.58 | N |
| ATOM | 14548 | CA | GLU | B | 414 | −45.482 | −30.512 | −6.614 | 1.00 | 30.99 | C |
| ATOM | 14550 | CB | GLU | B | 414 | −46.781 | −30.101 | −5.927 | 1.00 | 30.98 | C |
| ATOM | 14553 | CG | GLU | B | 414 | −47.732 | −31.245 | −5.642 | 1.00 | 31.82 | C |
| ATOM | 14556 | CD | GLU | B | 414 | −49.100 | −30.774 | −5.138 | 1.00 | 34.29 | C |
| ATOM | 14557 | OE1 | GLU | B | 414 | −49.258 | −29.581 | −4.777 | 1.00 | 35.53 | O |
| ATOM | 14558 | OE2 | GLU | B | 414 | −50.036 | −31.603 | −5.101 | 1.00 | 36.44 | O |
| ATOM | 14559 | C | GLU | B | 414 | −45.104 | −29.455 | −7.628 | 1.00 | 30.59 | C |
| ATOM | 14560 | O | GLU | B | 414 | −45.169 | −29.687 | −8.828 | 1.00 | 30.37 | O |
| ATOM | 14562 | N | ILE | B | 415 | −44.684 | −28.295 | −7.140 | 1.00 | 30.49 | N |
| ATOM | 14563 | CA | ILE | B | 415 | −44.367 | −27.177 | −8.028 | 1.00 | 30.40 | C |
| ATOM | 14565 | CB | ILE | B | 415 | −44.412 | −25.797 | −7.320 | 1.00 | 30.40 | C |
| ATOM | 14567 | CG1 | ILE | B | 415 | −43.235 | −25.589 | −6.388 | 1.00 | 30.36 | C |
| ATOM | 14570 | CD1 | ILE | B | 415 | −43.373 | −24.313 | −5.611 | 1.00 | 31.01 | C |
| ATOM | 14574 | CG2 | ILE | B | 415 | −45.686 | −25.644 | −6.523 | 1.00 | 30.85 | C |
| ATOM | 14578 | C | ILE | B | 415 | −43.037 | −27.347 | −8.730 | 1.00 | 30.12 | C |
| ATOM | 14579 | O | ILE | B | 415 | −42.870 | −26.865 | −9.840 | 1.00 | 30.42 | O |
| ATOM | 14581 | N | GLU | B | 416 | −42.095 | −28.030 | −8.099 | 1.00 | 29.75 | N |
| ATOM | 14582 | CA | GLU | B | 416 | −40.799 | −28.249 | −8.719 | 1.00 | 29.70 | C |
| ATOM | 14584 | CB | GLU | B | 416 | −39.825 | −28.777 | −7.690 | 1.00 | 30.02 | C |
| ATOM | 14587 | CG | GLU | B | 416 | −38.386 | −28.426 | −7.948 | 1.00 | 31.20 | C |
| ATOM | 14590 | CD | GLU | B | 416 | −37.523 | −28.839 | −6.776 | 1.00 | 32.91 | C |
| ATOM | 14591 | OE1 | GLU | B | 416 | −38.008 | −28.723 | −5.632 | 1.00 | 32.37 | O |
| ATOM | 14592 | OE2 | GLU | B | 416 | −36.377 | −29.294 | −6.994 | 1.00 | 35.31 | O |
| ATOM | 14593 | C | GLU | B | 416 | −40.917 | −29.222 | −9.890 | 1.00 | 29.24 | C |
| ATOM | 14594 | O | GLU | B | 416 | −40.121 | −29.177 | −10.835 | 1.00 | 28.86 | O |
| ATOM | 14596 | N | ASN | B | 417 | −41.915 | −30.097 | −9.819 | 1.00 | 28.81 | N |
| ATOM | 14597 | CA | ASN | B | 417 | −42.252 | −30.960 | −10.941 | 1.00 | 28.66 | C |
| ATOM | 14599 | CB | ASN | B | 417 | −43.165 | −32.105 | −10.503 | 1.00 | 28.72 | C |
| ATOM | 14602 | CG | ASN | B | 417 | −42.379 | −33.285 | −9.973 | 1.00 | 29.78 | C |
| ATOM | 14603 | OD1 | ASN | B | 417 | −41.887 | −34.108 | −10.744 | 1.00 | 30.39 | O |
| ATOM | 14604 | ND2 | ASN | B | 417 | −42.223 | −33.358 | −8.653 | 1.00 | 31.45 | N |
| ATOM | 14607 | C | ASN | B | 417 | −42.888 | −30.183 | −12.067 | 1.00 | 28.32 | C |
| ATOM | 14608 | O | ASN | B | 417 | −42.611 | −30.456 | −13.232 | 1.00 | 27.95 | O |
| ATOM | 14610 | N | LEU | B | 418 | −43.740 | −29.217 | −11.713 | 1.00 | 28.23 | N |
| ATOM | 14611 | CA | LEU | B | 418 | −44.349 | −28.313 | −12.697 | 1.00 | 27.92 | C |
| ATOM | 14613 | CB | LEU | B | 418 | −45.298 | −27.320 | −12.023 | 1.00 | 27.48 | C |
| ATOM | 14616 | CG | LEU | B | 418 | −46.636 | −27.896 | −11.553 | 1.00 | 27.02 | C |
| ATOM | 14618 | CD1 | LEU | B | 418 | −47.393 | −26.882 | −10.691 | 1.00 | 26.70 | C |
| ATOM | 14622 | CD2 | LEU | B | 418 | −47.499 | −28.355 | −12.720 | 1.00 | 25.90 | C |
| ATOM | 14626 | C | LEU | B | 418 | −43.275 | −27.567 | −13.491 | 1.00 | 28.20 | C |
| ATOM | 14627 | O | LEU | B | 418 | −43.310 | −27.541 | −14.733 | 1.00 | 27.90 | O |
| ATOM | 14629 | N | GLN | B | 419 | −42.308 | −26.995 | −12.770 | 1.00 | 28.43 | N |
| ATOM | 14630 | CA | GLN | B | 419 | −41.170 | −26.315 | −13.395 | 1.00 | 28.72 | C |
| ATOM | 14632 | CB | GLN | B | 419 | −40.223 | −25.746 | −12.347 | 1.00 | 28.81 | C |
| ATOM | 14635 | CG | GLN | B | 419 | −40.592 | −24.332 | −11.946 | 1.00 | 30.14 | C |
| ATOM | 14638 | CD | GLN | B | 419 | −39.535 | −23.671 | −11.092 | 1.00 | 32.05 | C |
| ATOM | 14639 | OE1 | GLN | B | 419 | −39.246 | −22.477 | −11.257 | 1.00 | 33.88 | O |
| ATOM | 14640 | NE2 | GLN | B | 419 | −38.948 | −24.437 | −10.170 | 1.00 | 31.84 | N |
| ATOM | 14643 | C | GLN | B | 419 | −40.390 | −27.179 | −14.370 | 1.00 | 28.83 | C |
| ATOM | 14644 | O | GLN | B | 419 | −39.922 | −26.668 | −15.386 | 1.00 | 28.72 | O |
| ATOM | 14646 | N | LYS | B | 420 | −40.265 | −28.475 | −14.067 | 1.00 | 29.21 | N |
| ATOM | 14647 | CA | LYS | B | 420 | −39.613 | −29.451 | −14.968 | 1.00 | 29.26 | C |
| ATOM | 14649 | CB | LYS | B | 420 | −38.924 | −30.555 | −14.143 | 1.00 | 29.42 | C |
| ATOM | 14652 | CG | LYS | B | 420 | −37.800 | −30.052 | −13.207 | 1.00 | 30.58 | C |
| ATOM | 14655 | CD | LYS | B | 420 | −37.373 | −31.113 | −12.151 | 1.00 | 32.35 | C |
| ATOM | 14658 | CE | LYS | B | 420 | −36.572 | −30.506 | −10.955 | 1.00 | 33.05 | C |
| ATOM | 14661 | NZ | LYS | B | 420 | −36.520 | −31.368 | −9.702 | 1.00 | 32.62 | N |
| ATOM | 14665 | C | LYS | B | 420 | −40.579 | −30.057 | −16.021 | 1.00 | 28.96 | C |
| ATOM | 14666 | O | LYS | B | 420 | −40.216 | −30.965 | −16.753 | 1.00 | 28.66 | O |
| ATOM | 14668 | N | TYR | B | 421 | −41.804 | −29.543 | −16.088 | 1.00 | 29.01 | N |

TABLE 3-7-continued

| | | | | | | Coordinates of *P. tremuloides* IspS | | | | |
|---|---|---|---|---|---|---|---|---|---|---|
| ATOM | 14669 | CA | TYR | B | 421 | −42.777 | −29.893 | −17.134 | 1.00 | 29.16 C |
| ATOM | 14671 | CB | TYR | B | 421 | −42.209 | −29.602 | −18.534 | 1.00 | 29.48 C |
| ATOM | 14674 | CG | TYR | B | 421 | −41.968 | −28.127 | −18.773 | 1.00 | 31.04 C |
| ATOM | 14675 | CD1 | TYR | B | 421 | −43.018 | −27.219 | −18.716 | 1.00 | 32.54 C |
| ATOM | 14677 | CE1 | TYR | B | 421 | −42.815 | −25.878 | −18.914 | 1.00 | 33.35 C |
| ATOM | 14679 | CZ | TYR | B | 421 | −41.556 | −25.413 | −19.193 | 1.00 | 34.56 C |
| ATOM | 14680 | OH | TYR | B | 421 | −41.377 | −24.066 | −19.384 | 1.00 | 37.99 O |
| ATOM | 14682 | CE2 | TYR | B | 421 | −40.490 | −26.278 | −19.267 | 1.00 | 33.56 C |
| ATOM | 14684 | CD2 | TYR | B | 421 | −40.702 | −27.638 | −19.051 | 1.00 | 32.75 C |
| ATOM | 14686 | C | TYR | B | 421 | −43.345 | −31.311 | −17.042 | 1.00 | 28.60 C |
| ATOM | 14687 | O | TYR | B | 421 | −43.395 | −32.046 | −18.025 | 1.00 | 28.49 O |
| ATOM | 14689 | N | HIS | B | 422 | −43.808 | −31.662 | −15.846 | 1.00 | 28.18 N |
| ATOM | 14690 | CA | HIS | B | 422 | −44.507 | −32.919 | −15.594 | 1.00 | 27.66 C |
| ATOM | 14692 | CB | HIS | B | 422 | −45.082 | −32.914 | −14.180 | 1.00 | 27.73 C |
| ATOM | 14695 | CG | HIS | B | 422 | −45.500 | −34.264 | −13.685 | 1.00 | 28.14 C |
| ATOM | 14696 | ND1 | HIS | B | 422 | −44.597 | −35.195 | −13.217 | 1.00 | 29.15 N |
| ATOM | 14698 | CE1 | HIS | B | 422 | −45.247 | −36.277 | −12.829 | 1.00 | 29.50 C |
| ATOM | 14700 | NE2 | HIS | B | 422 | −46.539 | −36.078 | −13.022 | 1.00 | 28.69 N |
| ATOM | 14702 | CD2 | HIS | B | 422 | −46.724 | −34.827 | −13.552 | 1.00 | 27.24 C |
| ATOM | 14704 | C | HIS | B | 422 | −45.650 | −33.164 | −16.575 | 1.00 | 27.29 C |
| ATOM | 14705 | O | HIS | B | 422 | −46.463 | −32.269 | −16.853 | 1.00 | 26.86 O |
| ATOM | 14707 | N | ASP | B | 423 | −45.712 | −34.402 | −17.060 | 1.00 | 26.96 N |
| ATOM | 14708 | CA | ASP | B | 423 | −46.772 | −34.883 | −17.952 | 1.00 | 26.78 C |
| ATOM | 14710 | CB | ASP | B | 423 | −46.792 | −36.413 | −17.939 | 1.00 | 27.01 C |
| ATOM | 14713 | CG | ASP | B | 423 | −45.594 | −37.018 | −18.646 | 1.00 | 28.21 C |
| ATOM | 14714 | OD1 | ASP | B | 423 | −45.100 | −36.378 | −19.602 | 1.00 | 31.33 O |
| ATOM | 14715 | OD2 | ASP | B | 423 | −45.153 | −38.130 | −18.262 | 1.00 | 28.39 O |
| ATOM | 14716 | C | ASP | B | 423 | −48.187 | −34.383 | −17.651 | 1.00 | 26.21 C |
| ATOM | 14717 | O | ASP | B | 423 | −49.015 | −34.336 | −18.556 | 1.00 | 26.75 O |
| ATOM | 14719 | N | ILE | B | 424 | −48.463 | −34.042 | −16.391 | 1.00 | 25.11 N |
| ATOM | 14720 | CA | ILE | B | 424 | −49.773 | −33.553 | −15.956 | 1.00 | 23.82 C |
| ATOM | 14722 | CB | ILE | B | 424 | −49.798 | −33.310 | −14.439 | 1.00 | 23.67 C |
| ATOM | 14724 | CG1 | ILE | B | 424 | −51.196 | −32.990 | −13.938 | 1.00 | 22.97 C |
| ATOM | 14727 | CD1 | ILE | B | 424 | −51.220 | −32.693 | −12.465 | 1.00 | 22.06 C |
| ATOM | 14731 | CG2 | ILE | B | 424 | −48.859 | −32.171 | −14.065 | 1.00 | 24.35 C |
| ATOM | 14735 | C | ILE | B | 424 | −50.102 | −32.265 | −16.669 | 1.00 | 23.08 C |
| ATOM | 14736 | O | ILE | B | 424 | −51.265 | −32.025 | −17.023 | 1.00 | 22.99 O |
| ATOM | 14738 | N | ILE | B | 425 | −49.082 | −31.436 | −16.886 | 1.00 | 22.22 N |
| ATOM | 14739 | CA | ILE | B | 425 | −49.282 | −30.199 | −17.633 | 1.00 | 21.61 C |
| ATOM | 14741 | CB | ILE | B | 425 | −48.796 | −28.959 | −16.848 | 1.00 | 21.18 C |
| ATOM | 14743 | CG1 | ILE | B | 425 | −47.279 | −28.853 | −16.804 | 1.00 | 19.47 C |
| ATOM | 14746 | CD1 | ILE | B | 425 | −46.850 | −27.581 | −16.140 | 1.00 | 18.00 C |
| ATOM | 14750 | CG2 | ILE | B | 425 | −49.357 | −28.977 | −15.428 | 1.00 | 20.75 C |
| ATOM | 14754 | C | ILE | B | 425 | −48.665 | −30.255 | −19.033 | 1.00 | 21.73 C |
| ATOM | 14755 | O | ILE | B | 425 | −49.100 | −29.523 | −19.912 | 1.00 | 21.75 O |
| ATOM | 14757 | N | SER | B | 426 | −47.686 | −31.134 | −19.258 | 1.00 | 21.74 N |
| ATOM | 14758 | CA | SER | B | 426 | −47.016 | −31.174 | −20.560 | 1.00 | 21.53 C |
| ATOM | 14760 | CB | SER | B | 426 | −45.639 | −31.876 | −20.516 | 1.00 | 21.66 C |
| ATOM | 14763 | OG | SER | B | 426 | −45.724 | −33.281 | −20.405 | 1.00 | 22.19 O |
| ATOM | 14765 | C | SER | B | 426 | −47.922 | −31.798 | −21.582 | 1.00 | 21.19 C |
| ATOM | 14766 | O | SER | B | 426 | −47.950 | −31.358 | −22.721 | 1.00 | 21.37 O |
| ATOM | 14768 | N | ARG | B | 427 | −48.692 | −32.800 | −21.177 | 1.00 | 20.91 N |
| ATOM | 14769 | CA | ARG | B | 427 | −49.532 | −33.504 | −22.143 | 1.00 | 20.78 C |
| ATOM | 14771 | CB | ARG | B | 427 | −50.038 | −34.840 | −21.616 | 1.00 | 20.94 C |
| ATOM | 14774 | CG | ARG | B | 427 | −49.006 | −35.887 | −21.874 | 1.00 | 22.76 C |
| ATOM | 14777 | CD | ARG | B | 427 | −49.158 | −37.101 | −21.025 | 1.00 | 26.75 C |
| ATOM | 14780 | NE | ARG | B | 427 | −47.960 | −37.927 | −21.185 | 1.00 | 29.36 N |
| ATOM | 14782 | CZ | ARG | B | 427 | −47.574 | −38.887 | −20.352 | 1.00 | 30.25 C |
| ATOM | 14783 | NH1 | ARG | B | 427 | −48.293 | −39.179 | −19.266 | 1.00 | 30.27 N |
| ATOM | 14786 | NH2 | ARG | B | 427 | −46.447 | −39.547 | −20.611 | 1.00 | 31.25 N |
| ATOM | 14789 | C | ARG | B | 427 | −50.646 | −32.650 | −22.668 | 1.00 | 20.07 C |
| ATOM | 14790 | O | ARG | B | 427 | −50.724 | −32.466 | −23.866 | 1.00 | 20.13 O |
| ATOM | 14792 | N | PRO | B | 428 | −51.482 | −32.091 | −21.786 | 1.00 | 19.38 N |
| ATOM | 14793 | CA | PRO | B | 428 | −52.533 | −31.202 | −22.264 | 1.00 | 19.05 C |
| ATOM | 14795 | CB | PRO | B | 428 | −53.046 | −30.547 | −20.990 | 1.00 | 19.13 C |
| ATOM | 14798 | CG | PRO | B | 428 | −52.696 | −31.476 | −19.918 | 1.00 | 19.55 C |
| ATOM | 14801 | CD | PRO | B | 428 | −51.443 | −32.161 | −20.319 | 1.00 | 19.20 C |
| ATOM | 14804 | C | PRO | B | 428 | −52.016 | −30.135 | −23.227 | 1.00 | 18.84 C |
| ATOM | 14805 | O | PRO | B | 428 | −52.688 | −29.802 | −24.205 | 1.00 | 18.73 O |
| ATOM | 14806 | N | SER | B | 429 | −50.828 | −29.608 | −22.964 | 1.00 | 18.57 N |
| ATOM | 14807 | CA | SER | B | 429 | −50.208 | −28.679 | −23.899 | 1.00 | 18.64 C |
| ATOM | 14809 | CB | SER | B | 429 | −48.960 | −28.086 | −23.291 | 1.00 | 18.46 C |
| ATOM | 14812 | OG | SER | B | 429 | −49.141 | −27.980 | −21.911 | 1.00 | 19.08 O |
| ATOM | 14814 | C | SER | B | 429 | −49.877 | −29.315 | −25.260 | 1.00 | 18.52 C |
| ATOM | 14815 | O | SER | B | 429 | −49.886 | −28.633 | −26.276 | 1.00 | 19.02 O |
| ATOM | 14817 | N | HIS | B | 430 | −49.579 | −30.606 | −25.297 | 1.00 | 18.29 N |
| ATOM | 14818 | CA | HIS | B | 430 | −49.457 | −31.273 | −26.583 | 1.00 | 18.25 C |
| ATOM | 14820 | CB | HIS | B | 430 | −49.085 | −32.765 | −26.467 | 1.00 | 18.40 C |

TABLE 3-7-continued

Coordinates of *P. tremuloides* IspS

| ATOM | 14823 | CG | HIS | B | 430 | −47.753 | −33.024 | −25.806 | 1.00 | 19.41 | C |
|---|---|---|---|---|---|---|---|---|---|---|---|
| ATOM | 14824 | ND1 | HIS | B | 430 | −46.776 | −32.055 | −25.657 | 1.00 | 19.55 | N |
| ATOM | 14826 | CE1 | HIS | B | 430 | −45.729 | −32.576 | −25.043 | 1.00 | 17.77 | C |
| ATOM | 14828 | NE2 | HIS | B | 430 | −45.981 | −33.849 | −24.800 | 1.00 | 18.52 | N |
| ATOM | 14830 | CD2 | HIS | B | 430 | −47.232 | −34.160 | −25.277 | 1.00 | 19.19 | C |
| ATOM | 14832 | C | HIS | B | 430 | −50.789 | −31.105 | −27.306 | 1.00 | 17.93 | C |
| ATOM | 14833 | O | HIS | B | 430 | −50.816 | −30.599 | −28.417 | 1.00 | 18.54 | O |
| ATOM | 14835 | N | ILE | B | 431 | −51.897 | −31.479 | −26.665 | 1.00 | 17.34 | N |
| ATOM | 14836 | CA | ILE | B | 431 | −53.217 | −31.372 | −27.301 | 1.00 | 16.58 | C |
| ATOM | 14838 | CB | ILE | B | 431 | −54.400 | −31.738 | −26.375 | 1.00 | 16.53 | C |
| ATOM | 14840 | CG1 | ILE | B | 431 | −54.225 | −33.123 | −25.728 | 1.00 | 16.06 | C |
| ATOM | 14843 | CD1 | ILE | B | 431 | −54.069 | −34.212 | −26.698 | 1.00 | 16.05 | C |
| ATOM | 14847 | CG2 | ILE | B | 431 | −55.701 | −31.666 | −27.149 | 1.00 | 15.49 | C |
| ATOM | 14851 | C | ILE | B | 431 | −53.431 | −29.949 | −27.748 | 1.00 | 16.35 | C |
| ATOM | 14852 | O | ILE | B | 431 | −53.856 | −29.712 | −28.860 | 1.00 | 16.74 | O |
| ATOM | 14854 | N | PHE | B | 432 | −53.110 | −29.003 | −26.881 | 1.00 | 16.15 | N |
| ATOM | 14855 | CA | PHE | B | 432 | −53.353 | −27.577 | −27.145 | 1.00 | 16.19 | C |
| ATOM | 14857 | CB | PHE | B | 432 | −52.811 | −26.776 | −25.956 | 1.00 | 16.36 | C |
| ATOM | 14860 | CG | PHE | B | 432 | −53.007 | −25.295 | −26.043 | 1.00 | 16.54 | C |
| ATOM | 14861 | CD1 | PHE | B | 432 | −53.869 | −24.708 | −26.946 | 1.00 | 16.55 | C |
| ATOM | 14863 | CE1 | PHE | B | 432 | −54.007 | −23.334 | −26.974 | 1.00 | 17.89 | C |
| ATOM | 14865 | CZ | PHE | B | 432 | −53.305 | −22.538 | −26.080 | 1.00 | 17.96 | C |
| ATOM | 14867 | CE2 | PHE | B | 432 | −52.461 | −23.114 | −25.169 | 1.00 | 17.30 | C |
| ATOM | 14869 | CD2 | PHE | B | 432 | −52.323 | −24.482 | −25.151 | 1.00 | 17.54 | C |
| ATOM | 14871 | C | PHE | B | 432 | −52.726 | −27.104 | −28.452 | 1.00 | 15.93 | C |
| ATOM | 14872 | O | PHE | B | 432 | −53.398 | −26.525 | −29.303 | 1.00 | 15.63 | O |
| ATOM | 14874 | N | ARG | B | 433 | −51.438 | −27.387 | −28.594 | 1.00 | 15.79 | N |
| ATOM | 14875 | CA | ARG | B | 433 | −50.674 | −27.044 | −29.778 | 1.00 | 15.74 | C |
| ATOM | 14877 | CB | ARG | B | 433 | −49.196 | −27.279 | −29.470 | 1.00 | 15.68 | C |
| ATOM | 14880 | CG | ARG | B | 433 | −48.259 | −27.218 | −30.665 | 1.00 | 16.39 | C |
| ATOM | 14883 | CD | ARG | B | 433 | −48.348 | −25.919 | −31.388 | 1.00 | 16.27 | C |
| ATOM | 14886 | NE | ARG | B | 433 | −47.969 | −24.850 | −30.492 | 1.00 | 17.34 | N |
| ATOM | 14888 | CZ | ARG | B | 433 | −48.210 | −23.565 | −30.703 | 1.00 | 17.89 | C |
| ATOM | 14889 | NH1 | ARG | B | 433 | −48.834 | −23.142 | −31.803 | 1.00 | 16.79 | N |
| ATOM | 14892 | NH2 | ARG | B | 433 | −47.805 | −22.701 | −29.792 | 1.00 | 18.53 | N |
| ATOM | 14895 | C | ARG | B | 433 | −51.114 | −27.852 | −31.011 | 1.00 | 15.85 | C |
| ATOM | 14896 | O | ARG | B | 433 | −51.197 | −27.328 | −32.120 | 1.00 | 15.40 | O |
| ATOM | 14898 | N | LEU | B | 434 | −51.381 | −29.134 | −30.813 | 1.00 | 16.18 | N |
| ATOM | 14899 | CA | LEU | B | 434 | −51.794 | −29.986 | −31.902 | 1.00 | 16.58 | C |
| ATOM | 14901 | CB | LEU | B | 434 | −51.802 | −31.453 | −31.468 | 1.00 | 16.79 | C |
| ATOM | 14904 | CG | LEU | B | 434 | −50.408 | −32.055 | −31.232 | 1.00 | 17.49 | C |
| ATOM | 14906 | CD1 | LEU | B | 434 | −50.486 | −33.548 | −30.864 | 1.00 | 16.63 | C |
| ATOM | 14910 | CD2 | LEU | B | 434 | −49.511 | −31.836 | −32.467 | 1.00 | 18.00 | C |
| ATOM | 14914 | C | LEU | B | 434 | −53.158 | −29.559 | −32.423 | 1.00 | 17.07 | C |
| ATOM | 14915 | O | LEU | B | 434 | −53.333 | −29.442 | −33.633 | 1.00 | 17.44 | O |
| ATOM | 14917 | N | CYS | B | 435 | −54.118 | −29.308 | −31.532 | 1.00 | 17.23 | N |
| ATOM | 14918 | CA | CYS | B | 435 | −55.419 | −28.778 | −31.947 | 1.00 | 17.44 | C |
| ATOM | 14920 | CB | CYS | B | 435 | −56.301 | −28.529 | −30.746 | 1.00 | 17.38 | C |
| ATOM | 14923 | SG | CYS | B | 435 | −56.825 | −29.993 | −29.971 | 1.00 | 17.90 | S |
| ATOM | 14925 | C | CYS | B | 435 | −55.295 | −27.460 | −32.696 | 1.00 | 17.78 | C |
| ATOM | 14926 | O | CYS | B | 435 | −55.978 | −27.232 | −33.701 | 1.00 | 17.44 | O |
| ATOM | 14928 | N | ASN | B | 436 | −54.442 | −26.585 | −32.178 | 1.00 | 18.31 | N |
| ATOM | 14929 | CA | ASN | B | 436 | −54.248 | −25.267 | −32.769 | 1.00 | 19.14 | C |
| ATOM | 14931 | CB | ASN | B | 436 | −53.392 | −24.394 | −31.844 | 1.00 | 19.31 | C |
| ATOM | 14934 | CG | ASN | B | 436 | −52.984 | −23.068 | −32.478 | 1.00 | 20.07 | C |
| ATOM | 14935 | OD1 | ASN | B | 436 | −53.456 | −22.686 | −33.555 | 1.00 | 22.72 | O |
| ATOM | 14936 | ND2 | ASN | B | 436 | −52.099 | −22.356 | −31.800 | 1.00 | 20.90 | N |
| ATOM | 14939 | C | ASN | B | 436 | −53.615 | −25.345 | −34.157 | 1.00 | 19.51 | C |
| ATOM | 14940 | O | ASN | B | 436 | −54.173 | −24.840 | −35.131 | 1.00 | 19.79 | O |
| ATOM | 14942 | N | ASP | B | 437 | −52.446 | −25.965 | −34.245 | 1.00 | 19.85 | N |
| ATOM | 14943 | CA | ASP | B | 437 | −51.754 | −26.058 | −35.517 | 1.00 | 20.01 | C |
| ATOM | 14945 | CB | ASP | B | 437 | −50.340 | −26.638 | −35.331 | 1.00 | 20.00 | C |
| ATOM | 14948 | CG | ASP | B | 437 | −49.397 | −25.675 | −34.557 | 1.00 | 21.23 | C |
| ATOM | 14949 | OD1 | ASP | B | 437 | −49.902 | −24.749 | −33.877 | 1.00 | 22.90 | O |
| ATOM | 14950 | OD2 | ASP | B | 437 | −48.149 | −25.821 | −34.632 | 1.00 | 22.18 | O |
| ATOM | 14951 | C | ASP | B | 437 | −52.629 | −26.838 | −36.512 | 1.00 | 20.00 | C |
| ATOM | 14952 | O | ASP | B | 437 | −52.678 | −26.491 | −37.695 | 1.00 | 20.02 | O |
| ATOM | 14954 | N | LEU | B | 438 | −53.372 | −27.836 | −36.021 | 1.00 | 20.02 | N |
| ATOM | 14955 | CA | LEU | B | 438 | −54.352 | −28.558 | −36.858 | 1.00 | 20.18 | C |
| ATOM | 14957 | CB | LEU | B | 438 | −55.144 | −29.593 | −36.049 | 1.00 | 19.88 | C |
| ATOM | 14960 | CG | LEU | B | 438 | −54.699 | −31.050 | −36.142 | 1.00 | 18.97 | C |
| ATOM | 14962 | CD1 | LEU | B | 438 | −55.537 | −31.869 | −35.200 | 1.00 | 18.86 | C |
| ATOM | 14966 | CD2 | LEU | B | 438 | −54.818 | −31.585 | −37.550 | 1.00 | 16.23 | C |
| ATOM | 14970 | C | LEU | B | 438 | −55.358 | −27.644 | −37.564 | 1.00 | 20.60 | C |
| ATOM | 14971 | O | LEU | B | 438 | −55.717 | −27.889 | −38.712 | 1.00 | 20.30 | O |
| ATOM | 14973 | N | ALA | B | 439 | −55.825 | −26.620 | −36.853 | 1.00 | 21.39 | N |
| ATOM | 14974 | CA | ALA | B | 439 | −56.802 | −25.654 | −37.377 | 1.00 | 21.96 | C |
| ATOM | 14976 | CB | ALA | B | 439 | −57.306 | −24.741 | −36.242 | 1.00 | 21.77 | C |

TABLE 3-7-continued

Coordinates of *P. tremuloides* IspS

| ATOM | 14980 | C | ALA | B | 439 | −56.214 | −24.805 | −38.494 | 1.00 | 22.47 | C |
| ATOM | 14981 | O | ALA | B | 439 | −56.850 | −24.559 | −39.517 | 1.00 | 22.13 | O |
| ATOM | 14983 | N | SER | B | 440 | −54.983 | −24.370 | −38.282 | 1.00 | 23.40 | N |
| ATOM | 14984 | CA | SER | B | 440 | −54.337 | −23.428 | −39.169 | 1.00 | 24.40 | C |
| ATOM | 14986 | CB | SER | B | 440 | −53.423 | −22.529 | −38.342 | 1.00 | 24.44 | C |
| ATOM | 14989 | OG | SER | B | 440 | −52.994 | −23.206 | −37.166 | 1.00 | 25.19 | O |
| ATOM | 14991 | C | SER | B | 440 | −53.544 | −24.103 | −40.289 | 1.00 | 25.15 | C |
| ATOM | 14992 | O | SER | B | 440 | −53.093 | −23.424 | −41.210 | 1.00 | 25.24 | O |
| ATOM | 14994 | N | ALA | B | 441 | −53.392 | −25.428 | −40.222 | 1.00 | 25.99 | N |
| ATOM | 14995 | CA | ALA | B | 441 | −52.488 | −26.160 | −41.119 | 1.00 | 26.53 | C |
| ATOM | 14997 | CB | ALA | B | 441 | −52.532 | −27.655 | −40.830 | 1.00 | 26.26 | C |
| ATOM | 15001 | C | ALA | B | 441 | −52.726 | −25.903 | −42.608 | 1.00 | 27.31 | C |
| ATOM | 15002 | O | ALA | B | 441 | −51.811 | −25.489 | −43.310 | 1.00 | 27.26 | O |
| ATOM | 15004 | N | SER | B | 442 | −53.940 | −26.134 | −43.098 | 1.00 | 28.45 | N |
| ATOM | 15005 | CA | SER | B | 442 | −54.138 | −26.138 | −44.545 | 1.00 | 29.47 | C |
| ATOM | 15007 | CB | SER | B | 442 | −55.477 | −26.769 | −44.936 | 1.00 | 29.40 | C |
| ATOM | 15010 | OG | SER | B | 442 | −56.454 | −25.784 | −45.181 | 1.00 | 30.36 | O |
| ATOM | 15012 | C | SER | B | 442 | −53.966 | −24.731 | −45.125 | 1.00 | 30.22 | C |
| ATOM | 15013 | O | SER | B | 442 | −53.304 | −24.562 | −46.139 | 1.00 | 30.26 | O |
| ATOM | 15015 | N | ALA | B | 443 | −54.537 | −23.729 | −44.467 | 1.00 | 31.38 | N |
| ATOM | 15016 | CA | ALA | B | 443 | −54.308 | −22.333 | −44.835 | 1.00 | 32.22 | C |
| ATOM | 15018 | CB | ALA | B | 443 | −55.057 | −21.410 | −43.893 | 1.00 | 32.28 | C |
| ATOM | 15022 | C | ALA | B | 443 | −52.820 | −21.992 | −44.818 | 1.00 | 33.12 | C |
| ATOM | 15023 | O | ALA | B | 443 | −52.302 | −21.419 | −45.766 | 1.00 | 33.24 | O |
| ATOM | 15025 | N | GLU | B | 444 | −52.136 | −22.351 | −43.736 | 1.00 | 34.43 | N |
| ATOM | 15026 | CA | GLU | B | 444 | −50.711 | −22.033 | −43.582 | 1.00 | 35.35 | C |
| ATOM | 15028 | CB | GLU | B | 444 | −50.237 | −22.271 | −42.134 | 1.00 | 35.46 | C |
| ATOM | 15031 | CG | GLU | B | 444 | −50.757 | −21.227 | −41.126 | 1.00 | 36.42 | C |
| ATOM | 15034 | CD | GLU | B | 444 | −50.178 | −21.376 | −39.708 | 1.00 | 37.82 | C |
| ATOM | 15035 | OE1 | GLU | B | 444 | −49.965 | −22.506 | −39.224 | 1.00 | 37.92 | O |
| ATOM | 15036 | OE2 | GLU | B | 444 | −49.955 | −20.344 | −39.049 | 1.00 | 40.09 | O |
| ATOM | 15037 | C | GLU | B | 444 | −49.840 | −22.794 | −44.594 | 1.00 | 35.87 | C |
| ATOM | 15038 | O | GLU | B | 444 | −48.870 | −22.239 | −45.107 | 1.00 | 35.85 | O |
| ATOM | 15040 | N | ILE | B | 445 | −50.193 | −24.048 | −44.883 | 1.00 | 36.63 | N |
| ATOM | 15041 | CA | ILE | B | 445 | −49.517 | −24.837 | −45.928 | 1.00 | 37.21 | C |
| ATOM | 15043 | CB | ILE | B | 445 | −49.854 | −26.366 | −45.832 | 1.00 | 37.15 | C |
| ATOM | 15045 | CG1 | ILE | B | 445 | −49.181 | −26.991 | −44.609 | 1.00 | 36.85 | C |
| ATOM | 15048 | CD1 | ILE | B | 445 | −49.867 | −28.244 | −44.102 | 1.00 | 36.62 | C |
| ATOM | 15052 | CG2 | ILE | B | 445 | −49.416 | −27.120 | −47.093 | 1.00 | 36.66 | C |
| ATOM | 15056 | C | ILE | B | 445 | −49.933 | −24.289 | −47.290 | 1.00 | 37.88 | C |
| ATOM | 15057 | O | ILE | B | 445 | −50.926 | −24.733 | −47.874 | 1.00 | 38.20 | O |
| ATOM | 15059 | N | ALA | B | 446 | −49.175 | −23.314 | −47.785 | 1.00 | 38.56 | N |
| ATOM | 15060 | CA | ALA | B | 446 | −49.544 | −22.575 | −48.992 | 1.00 | 39.03 | C |
| ATOM | 15062 | CB | ALA | B | 446 | −49.833 | −23.522 | −50.169 | 1.00 | 39.19 | C |
| ATOM | 15066 | C | ALA | B | 446 | −50.768 | −21.740 | −48.685 | 1.00 | 39.42 | C |
| ATOM | 15067 | O | ALA | B | 446 | −51.866 | −22.288 | −48.742 | 1.00 | 39.26 | O |
| ATOM | 15069 | N | ARG | B | 447 | −50.650 | −20.443 | −48.361 | 1.00 | 40.06 | N |
| ATOM | 15070 | CA | ARG | B | 447 | −49.426 | −19.589 | −48.361 | 1.00 | 40.54 | C |
| ATOM | 15072 | CB | ARG | B | 447 | −49.276 | −18.901 | −46.986 | 1.00 | 40.70 | C |
| ATOM | 15075 | CG | ARG | B | 447 | −50.121 | −17.634 | −46.836 | 1.00 | 41.82 | C |
| ATOM | 15078 | CD | ARG | B | 447 | −50.292 | −17.234 | −45.377 | 1.00 | 42.99 | C |
| ATOM | 15081 | NE | ARG | B | 447 | −51.628 | −17.546 | −44.864 | 1.00 | 44.22 | N |
| ATOM | 15083 | CZ | ARG | B | 447 | −51.924 | −17.766 | −43.580 | 1.00 | 46.00 | C |
| ATOM | 15084 | NH1 | ARG | B | 447 | −50.977 | −17.730 | −42.633 | 1.00 | 46.34 | N |
| ATOM | 15087 | NH2 | ARG | B | 447 | −53.184 | −18.039 | −43.236 | 1.00 | 46.39 | N |
| ATOM | 15090 | C | ARG | B | 447 | −48.095 | −20.208 | −48.837 | 1.00 | 40.35 | C |
| ATOM | 15091 | O | ARG | B | 447 | −47.897 | −20.403 | −50.038 | 1.00 | 40.95 | O |
| ATOM | 15093 | N | GLY | B | 448 | −47.170 | −20.442 | −47.918 | 1.00 | 39.87 | N |
| ATOM | 15094 | CA | GLY | B | 448 | −46.020 | −21.306 | −48.162 | 1.00 | 39.52 | C |
| ATOM | 15097 | C | GLY | B | 448 | −45.258 | −21.517 | −46.865 | 1.00 | 39.26 | C |
| ATOM | 15098 | O | GLY | B | 448 | −44.071 | −21.842 | −46.885 | 1.00 | 39.15 | O |
| ATOM | 15100 | N | GLU | B | 449 | −45.966 | −21.344 | −45.742 | 1.00 | 38.85 | N |
| ATOM | 15101 | CA | GLU | B | 449 | −45.365 | −21.215 | −44.426 | 1.00 | 38.45 | C |
| ATOM | 15103 | CB | GLU | B | 449 | −46.288 | −20.472 | −43.444 | 1.00 | 38.76 | C |
| ATOM | 15106 | CG | GLU | B | 449 | −46.346 | −18.943 | −43.636 | 1.00 | 40.34 | C |
| ATOM | 15109 | CD | GLU | B | 449 | −47.486 | −18.257 | −42.839 | 1.00 | 42.09 | C |
| ATOM | 15110 | OE1 | GLU | B | 449 | −47.897 | −18.787 | −41.780 | 1.00 | 43.23 | O |
| ATOM | 15111 | OE2 | GLU | B | 449 | −47.972 | −17.184 | −43.274 | 1.00 | 42.13 | O |
| ATOM | 15112 | C | GLU | B | 449 | −45.073 | −22.600 | −43.906 | 1.00 | 37.54 | C |
| ATOM | 15113 | O | GLU | B | 449 | −45.810 | −23.553 | −44.167 | 1.00 | 37.34 | O |
| ATOM | 15115 | N | THR | B | 450 | −43.986 | −22.688 | −43.159 | 1.00 | 36.47 | N |
| ATOM | 15116 | CA | THR | B | 450 | −43.459 | −23.950 | −42.702 | 1.00 | 35.65 | C |
| ATOM | 15118 | CB | THR | B | 450 | −42.017 | −24.105 | −43.245 | 1.00 | 35.81 | C |
| ATOM | 15120 | OG1 | THR | B | 450 | −41.593 | −25.465 | −43.109 | 1.00 | 37.67 | O |
| ATOM | 15122 | CG2 | THR | B | 450 | −41.029 | −23.152 | −42.538 | 1.00 | 36.21 | C |
| ATOM | 15126 | C | THR | B | 450 | −43.528 | −24.084 | −41.166 | 1.00 | 34.22 | C |
| ATOM | 15127 | O | THR | B | 450 | −43.165 | −25.127 | −40.619 | 1.00 | 34.00 | O |
| ATOM | 15129 | N | ALA | B | 451 | −44.024 | −23.034 | −40.495 | 1.00 | 32.69 | N |

TABLE 3-7-continued

| | | | | | | | | | | | |
|---|---|---|---|---|---|---|---|---|---|---|---|
| ATOM | 15130 | CA | ALA | B | 451 | −44.144 | −22.974 | −39.026 | 1.00 | 31.28 | C |
| ATOM | 15132 | CB | ALA | B | 451 | −43.952 | −21.546 | −38.545 | 1.00 | 31.06 | C |
| ATOM | 15136 | C | ALA | B | 451 | −45.495 | −23.500 | −38.547 | 1.00 | 29.97 | C |
| ATOM | 15137 | O | ALA | B | 451 | −46.337 | −22.735 | −38.082 | 1.00 | 30.08 | O |
| ATOM | 15139 | N | ASN | B | 452 | −45.690 | −24.809 | −38.656 | 1.00 | 28.19 | N |
| ATOM | 15140 | CA | ASN | B | 452 | −46.935 | −25.444 | −38.272 | 1.00 | 26.73 | C |
| ATOM | 15142 | CB | ASN | B | 452 | −47.929 | −25.339 | −39.422 | 1.00 | 26.45 | C |
| ATOM | 15145 | CG | ASN | B | 452 | −49.311 | −25.832 | −39.057 | 1.00 | 25.38 | C |
| ATOM | 15146 | OD1 | ASN | B | 452 | −49.608 | −27.004 | −39.195 | 1.00 | 24.57 | O |
| ATOM | 15147 | ND2 | ASN | B | 452 | −50.171 | −24.928 | −38.618 | 1.00 | 24.44 | N |
| ATOM | 15150 | C | ASN | B | 452 | −46.631 | −26.889 | −37.952 | 1.00 | 26.05 | C |
| ATOM | 15151 | O | ASN | B | 452 | −45.930 | −27.544 | −38.695 | 1.00 | 26.21 | O |
| ATOM | 15153 | N | SER | B | 453 | −47.131 | −27.388 | −36.834 | 1.00 | 25.30 | N |
| ATOM | 15154 | CA | SER | B | 453 | −46.843 | −28.760 | −36.432 | 1.00 | 24.72 | C |
| ATOM | 15156 | CB | SER | B | 453 | −47.638 | −29.139 | −35.174 | 1.00 | 24.81 | C |
| ATOM | 15159 | OG | SER | B | 453 | −47.143 | −28.455 | −34.031 | 1.00 | 24.36 | O |
| ATOM | 15161 | C | SER | B | 453 | −47.111 | −29.770 | −37.543 | 1.00 | 24.12 | C |
| ATOM | 15162 | O | SER | B | 453 | −46.325 | −30.679 | −37.743 | 1.00 | 24.33 | O |
| ATOM | 15164 | N | VAL | B | 454 | −48.202 | −29.606 | −38.272 | 1.00 | 23.57 | N |
| ATOM | 15165 | CA | VAL | B | 454 | −48.546 | −30.541 | −39.328 | 1.00 | 23.27 | C |
| ATOM | 15167 | CB | VAL | B | 454 | −50.001 | −30.361 | −39.795 | 1.00 | 23.06 | C |
| ATOM | 15169 | CG1 | VAL | B | 454 | −50.363 | −31.385 | −40.829 | 1.00 | 22.41 | C |
| ATOM | 15173 | CG2 | VAL | B | 454 | −50.946 | −30.489 | −38.622 | 1.00 | 22.80 | C |
| ATOM | 15177 | C | VAL | B | 454 | −47.581 | −30.473 | −40.521 | 1.00 | 23.83 | C |
| ATOM | 15178 | O | VAL | B | 454 | −47.370 | −31.493 | −41.175 | 1.00 | 24.48 | O |
| ATOM | 15180 | N | SER | B | 455 | −46.981 | −29.309 | −40.803 | 1.00 | 23.99 | N |
| ATOM | 15181 | CA | SER | B | 455 | −45.978 | −29.198 | −41.881 | 1.00 | 24.22 | C |
| ATOM | 15183 | CB | SER | B | 455 | −45.577 | −27.767 | −42.111 | 1.00 | 24.02 | C |
| ATOM | 15186 | OG | SER | B | 455 | −46.655 | −27.098 | −42.689 | 1.00 | 25.57 | O |
| ATOM | 15188 | C | SER | B | 455 | −44.708 | −29.949 | −41.582 | 1.00 | 24.65 | C |
| ATOM | 15189 | O | SER | B | 455 | −44.211 | −30.700 | −42.417 | 1.00 | 25.23 | O |
| ATOM | 15191 | N | CYS | B | 456 | −44.151 | −29.700 | −40.405 | 1.00 | 24.82 | N |
| ATOM | 15192 | CA | CYS | B | 456 | −43.024 | −30.462 | −39.935 | 1.00 | 24.81 | C |
| ATOM | 15194 | CB | CYS | B | 456 | −42.765 | −30.170 | −38.470 | 1.00 | 24.92 | C |
| ATOM | 15197 | SG | CYS | B | 456 | −42.139 | −28.541 | −38.190 | 1.00 | 25.18 | S |
| ATOM | 15199 | C | CYS | B | 456 | −43.304 | −31.938 | −40.124 | 1.00 | 24.84 | C |
| ATOM | 15200 | O | CYS | B | 456 | −42.507 | −32.634 | −40.728 | 1.00 | 25.34 | O |
| ATOM | 15202 | N | TYR | B | 457 | −44.442 | −32.421 | −39.644 | 1.00 | 24.75 | N |
| ATOM | 15203 | CA | TYR | B | 457 | −44.735 | −33.838 | −39.778 | 1.00 | 24.85 | C |
| ATOM | 15205 | CB | TYR | B | 457 | −46.069 | −34.197 | −39.142 | 1.00 | 24.64 | C |
| ATOM | 15208 | CG | TYR | B | 457 | −46.057 | −35.537 | −38.451 | 1.00 | 24.00 | C |
| ATOM | 15209 | CD1 | TYR | B | 457 | −45.846 | −35.635 | −37.083 | 1.00 | 24.19 | C |
| ATOM | 15211 | CE1 | TYR | B | 457 | −45.848 | −36.873 | −36.436 | 1.00 | 23.72 | C |
| ATOM | 15213 | CZ | TYR | B | 457 | −46.059 | −38.025 | −37.170 | 1.00 | 23.27 | C |
| ATOM | 15214 | OH | TYR | B | 457 | −46.063 | −39.244 | −36.554 | 1.00 | 22.94 | O |
| ATOM | 15216 | CE2 | TYR | B | 457 | −46.268 | −37.961 | −38.528 | 1.00 | 23.68 | C |
| ATOM | 15218 | CD2 | TYR | B | 457 | −46.265 | −36.711 | −39.163 | 1.00 | 24.16 | C |
| ATOM | 15220 | C | TYR | B | 457 | −44.676 | −34.267 | −41.251 | 1.00 | 25.30 | C |
| ATOM | 15221 | O | TYR | B | 457 | −43.965 | −35.208 | −41.584 | 1.00 | 24.94 | O |
| ATOM | 15223 | N | MET | B | 458 | −45.388 | −33.569 | −42.134 | 1.00 | 26.02 | N |
| ATOM | 15224 | CA | MET | B | 458 | −45.207 | −33.775 | −43.585 | 1.00 | 26.76 | C |
| ATOM | 15226 | CB | MET | B | 458 | −45.913 | −32.685 | −44.407 | 1.00 | 26.84 | C |
| ATOM | 15229 | CG | MET | B | 458 | −47.419 | −32.720 | −44.429 | 1.00 | 27.32 | C |
| ATOM | 15232 | SD | MET | B | 458 | −48.092 | −31.238 | −45.229 | 1.00 | 27.76 | S |
| ATOM | 15233 | CE | MET | B | 458 | −47.283 | −31.311 | −46.830 | 1.00 | 26.95 | C |
| ATOM | 15237 | C | MET | B | 458 | −43.723 | −33.759 | −43.996 | 1.00 | 27.06 | C |
| ATOM | 15238 | O | MET | B | 458 | −43.192 | −34.746 | −44.485 | 1.00 | 26.94 | O |
| ATOM | 15240 | N | ARG | B | 459 | −43.069 | −32.624 | −43.800 | 1.00 | 27.58 | N |
| ATOM | 15241 | CA | ARG | B | 459 | −41.720 | −32.419 | −44.289 | 1.00 | 28.38 | C |
| ATOM | 15243 | CB | ARG | B | 459 | −41.313 | −30.965 | −44.041 | 1.00 | 28.96 | C |
| ATOM | 15246 | CG | ARG | B | 459 | −39.862 | −30.642 | −44.328 | 1.00 | 31.93 | C |
| ATOM | 15249 | CD | ARG | B | 459 | −39.656 | −29.139 | −44.480 | 1.00 | 36.88 | C |
| ATOM | 15252 | NE | ARG | B | 459 | −40.318 | −28.349 | −43.427 | 1.00 | 41.70 | N |
| ATOM | 15254 | CZ | ARG | B | 459 | −39.890 | −28.241 | −42.161 | 1.00 | 45.68 | C |
| ATOM | 15255 | NH1 | ARG | B | 459 | −38.795 | −28.899 | −41.751 | 1.00 | 48.08 | N |
| ATOM | 15258 | NH2 | ARG | B | 459 | −40.566 | −27.489 | −41.284 | 1.00 | 45.92 | N |
| ATOM | 15261 | C | ARG | B | 459 | −40.717 | −33.401 | −43.672 | 1.00 | 28.03 | C |
| ATOM | 15262 | O | ARG | B | 459 | −39.829 | −33.881 | −44.356 | 1.00 | 28.13 | O |
| ATOM | 15264 | N | THR | B | 460 | −40.882 | −33.711 | −42.393 | 1.00 | 27.88 | N |
| ATOM | 15265 | CA | THR | B | 460 | −40.002 | −34.635 | −41.664 | 1.00 | 27.75 | C |
| ATOM | 15267 | CB | THR | B | 460 | −40.240 | −34.502 | −40.134 | 1.00 | 27.79 | C |
| ATOM | 15269 | OG1 | THR | B | 460 | −39.805 | −33.209 | −39.689 | 1.00 | 27.98 | O |
| ATOM | 15271 | CG2 | THR | B | 460 | −39.519 | −35.589 | −39.356 | 1.00 | 27.46 | C |
| ATOM | 15275 | C | THR | B | 460 | −40.171 | −36.114 | −42.045 | 1.00 | 27.72 | C |
| ATOM | 15276 | O | THR | B | 460 | −39.211 | −36.857 | −42.069 | 1.00 | 27.60 | O |
| ATOM | 15278 | N | LYS | B | 461 | −41.398 | −36.538 | −42.313 | 1.00 | 28.05 | N |
| ATOM | 15279 | CA | LYS | B | 461 | −41.701 | −37.929 | −42.649 | 1.00 | 28.25 | C |
| ATOM | 15281 | CB | LYS | B | 461 | −42.972 | −38.381 | −41.914 | 1.00 | 28.32 | C |

TABLE 3-7-continued

| | | | | | | | | | | |
|---|---|---|---|---|---|---|---|---|---|---|
| ATOM | 15284 | CG | LYS | B | 461 | −42.767 | −38.763 | −40.453 | 1.00 | 28.57 C |
| ATOM | 15287 | CD | LYS | B | 461 | −42.569 | −40.271 | −40.299 | 1.00 | 29.79 C |
| ATOM | 15290 | CE | LYS | B | 461 | −41.913 | −40.651 | −38.970 | 1.00 | 30.32 C |
| ATOM | 15293 | NZ | LYS | B | 461 | −42.651 | −40.184 | −37.749 | 1.00 | 30.60 N |
| ATOM | 15297 | C | LYS | B | 461 | −41.876 | −38.139 | −44.155 | 1.00 | 28.50 C |
| ATOM | 15298 | O | LYS | B | 461 | −42.071 | −39.269 | −44.598 | 1.00 | 28.58 O |
| ATOM | 15300 | N | GLY | B | 462 | −41.818 | −37.057 | −44.933 | 1.00 | 28.79 N |
| ATOM | 15301 | CA | GLY | B | 462 | −41.978 | −37.114 | −46.385 | 1.00 | 29.04 C |
| ATOM | 15304 | C | GLY | B | 462 | −43.333 | −37.610 | −46.853 | 1.00 | 29.39 C |
| ATOM | 15305 | O | GLY | B | 462 | −43.410 | −38.452 | −47.738 | 1.00 | 29.53 O |
| ATOM | 15307 | N | ILE | B | 463 | −44.406 | −37.081 | −46.270 | 1.00 | 29.91 N |
| ATOM | 15308 | CA | ILE | B | 463 | −45.764 | −37.552 | −46.572 | 1.00 | 30.27 C |
| ATOM | 15310 | CB | ILE | B | 463 | −46.333 | −38.444 | −45.433 | 1.00 | 30.13 C |
| ATOM | 15312 | CG1 | ILE | B | 463 | −46.308 | −37.706 | −44.092 | 1.00 | 30.22 C |
| ATOM | 15315 | CD1 | ILE | B | 463 | −46.983 | −38.462 | −42.965 | 1.00 | 30.14 C |
| ATOM | 15319 | CG2 | ILE | B | 463 | −45.558 | −39.740 | −45.340 | 1.00 | 29.85 C |
| ATOM | 15323 | C | ILE | B | 463 | −46.775 | −36.429 | −46.881 | 1.00 | 30.75 C |
| ATOM | 15324 | O | ILE | B | 463 | −46.595 | −35.270 | −46.495 | 1.00 | 30.52 O |
| ATOM | 15326 | N | SER | B | 464 | −47.842 | −36.822 | −47.581 | 1.00 | 31.33 N |
| ATOM | 15327 | CA | SER | B | 464 | −48.951 | −35.944 | −47.952 | 1.00 | 31.68 C |
| ATOM | 15329 | CB | SER | B | 464 | −49.948 | −36.709 | −48.830 | 1.00 | 32.02 C |
| ATOM | 15332 | OG | SER | B | 464 | −50.547 | −37.793 | −48.123 | 1.00 | 32.84 O |
| ATOM | 15334 | C | SER | B | 464 | −49.705 | −35.396 | −46.747 | 1.00 | 31.62 C |
| ATOM | 15335 | O | SER | B | 464 | −49.897 | −36.097 | −45.747 | 1.00 | 31.69 O |
| ATOM | 15337 | N | GLU | B | 465 | −50.165 | −34.153 | −46.874 | 1.00 | 31.42 N |
| ATOM | 15338 | CA | GLU | B | 465 | −50.881 | −33.466 | −45.803 | 1.00 | 31.20 C |
| ATOM | 15340 | CB | GLU | B | 465 | −51.465 | −32.141 | −46.324 | 1.00 | 31.33 C |
| ATOM | 15343 | CG | GLU | B | 465 | −52.441 | −31.455 | −45.359 | 1.00 | 31.42 C |
| ATOM | 15346 | CD | GLU | B | 465 | −52.768 | −30.006 | −45.712 | 1.00 | 31.30 C |
| ATOM | 15347 | OE1 | GLU | B | 465 | −52.325 | −29.490 | −46.765 | 1.00 | 30.56 O |
| ATOM | 15348 | OE2 | GLU | B | 465 | −53.487 | −29.380 | −44.906 | 1.00 | 31.84 O |
| ATOM | 15349 | C | GLU | B | 465 | −51.985 | −34.325 | −45.202 | 1.00 | 30.97 C |
| ATOM | 15350 | O | GLU | B | 465 | −52.175 | −34.327 | −43.992 | 1.00 | 30.72 O |
| ATOM | 15352 | N | GLU | B | 466 | −52.709 | −35.052 | −46.055 | 1.00 | 30.98 N |
| ATOM | 15353 | CA | GLU | B | 466 | −53.865 | −35.833 | −45.618 | 1.00 | 30.65 C |
| ATOM | 15355 | CB | GLU | B | 466 | −54.553 | −36.541 | −46.788 | 1.00 | 30.62 C |
| ATOM | 15358 | CG | GLU | B | 466 | −55.733 | −37.401 | −46.336 | 1.00 | 31.50 C |
| ATOM | 15361 | CD | GLU | B | 466 | −56.353 | −38.240 | −47.446 | 1.00 | 33.14 C |
| ATOM | 15362 | OE1 | GLU | B | 466 | −56.512 | −37.736 | −48.581 | 1.00 | 34.40 O |
| ATOM | 15363 | OE2 | GLU | B | 466 | −56.699 | −39.413 | −47.173 | 1.00 | 33.21 O |
| ATOM | 15364 | C | GLU | B | 466 | −53.477 | −36.851 | −44.564 | 1.00 | 30.17 C |
| ATOM | 15365 | O | GLU | B | 466 | −54.215 | −37.049 | −43.606 | 1.00 | 30.46 O |
| ATOM | 15367 | N | LEU | B | 467 | −52.333 | −37.506 | −44.726 | 1.00 | 29.59 N |
| ATOM | 15368 | CA | LEU | B | 467 | −51.953 | −38.540 | −43.769 | 1.00 | 29.19 C |
| ATOM | 15370 | CB | LEU | B | 467 | −51.640 | −39.869 | −44.476 | 1.00 | 29.27 C |
| ATOM | 15373 | CG | LEU | B | 467 | −50.356 | −40.081 | −45.268 | 1.00 | 29.84 C |
| ATOM | 15375 | CD1 | LEU | B | 467 | −49.341 | −40.761 | −44.357 | 1.00 | 31.06 C |
| ATOM | 15379 | CD2 | LEU | B | 467 | −50.589 | −40.920 | −46.523 | 1.00 | 29.47 C |
| ATOM | 15383 | C | LEU | B | 467 | −50.865 | −38.092 | −42.794 | 1.00 | 28.54 C |
| ATOM | 15384 | O | LEU | B | 467 | −50.490 | −38.834 | −41.894 | 1.00 | 28.28 O |
| ATOM | 15386 | N | ALA | B | 468 | −50.388 | −36.862 | −42.962 | 1.00 | 28.04 N |
| ATOM | 15387 | CA | ALA | B | 468 | −49.682 | −36.158 | −41.893 | 1.00 | 27.54 C |
| ATOM | 15389 | CB | ALA | B | 468 | −48.922 | −34.970 | −42.435 | 1.00 | 27.34 C |
| ATOM | 15393 | C | ALA | B | 468 | −50.711 | −35.698 | −40.865 | 1.00 | 27.17 C |
| ATOM | 15394 | O | ALA | B | 468 | −50.482 | −35.801 | −39.662 | 1.00 | 27.40 O |
| ATOM | 15396 | N | THR | B | 469 | −51.841 | −35.182 | −41.349 | 1.00 | 26.57 N |
| ATOM | 15397 | CA | THR | B | 469 | −52.957 | −34.795 | −40.490 | 1.00 | 25.87 C |
| ATOM | 15399 | CB | THR | B | 469 | −54.130 | −34.297 | −41.328 | 1.00 | 25.53 C |
| ATOM | 15401 | OG1 | THR | B | 469 | −53.737 | −33.111 | −42.025 | 1.00 | 24.99 O |
| ATOM | 15403 | CG2 | THR | B | 469 | −55.316 | −33.993 | −40.453 | 1.00 | 24.62 C |
| ATOM | 15407 | C | THR | B | 469 | −53.412 | −35.988 | −39.669 | 1.00 | 25.95 C |
| ATOM | 15408 | O | THR | B | 469 | −53.551 | −35.925 | −38.450 | 1.00 | 25.80 O |
| ATOM | 15410 | N | GLU | B | 470 | −53.618 | −37.091 | −40.367 | 1.00 | 26.06 N |
| ATOM | 15411 | CA | GLU | B | 470 | −54.043 | −38.344 | −39.756 | 1.00 | 26.10 C |
| ATOM | 15413 | CB | GLU | B | 470 | −54.057 | −39.436 | −40.848 | 1.00 | 26.60 C |
| ATOM | 15416 | CG | GLU | B | 470 | −55.038 | −40.587 | −40.646 | 1.00 | 28.01 C |
| ATOM | 15419 | CD | GLU | B | 470 | −54.553 | −41.897 | −41.286 | 1.00 | 29.05 C |
| ATOM | 15420 | OE1 | GLU | B | 470 | −54.298 | −41.930 | −42.515 | 1.00 | 27.96 O |
| ATOM | 15421 | OE2 | GLU | B | 470 | −54.435 | −42.892 | −40.536 | 1.00 | 30.42 O |
| ATOM | 15422 | C | GLU | B | 470 | −53.148 | −38.746 | −38.557 | 1.00 | 25.28 C |
| ATOM | 15423 | O | GLU | B | 470 | −53.629 | −39.266 | −37.556 | 1.00 | 25.08 O |
| ATOM | 15425 | N | SER | B | 471 | −51.850 | −38.497 | −38.654 | 1.00 | 24.70 N |
| ATOM | 15426 | CA | SER | B | 471 | −50.930 | −38.906 | −37.599 | 1.00 | 24.26 C |
| ATOM | 15428 | CB | SER | B | 471 | −49.494 | −38.842 | −38.085 | 1.00 | 24.11 C |
| ATOM | 15431 | OG | SER | B | 471 | −49.315 | −39.693 | −39.186 | 1.00 | 23.98 O |
| ATOM | 15433 | C | SER | B | 471 | −51.085 | −38.029 | −36.377 | 1.00 | 23.92 C |
| ATOM | 15434 | O | SER | B | 471 | −51.240 | −38.530 | −35.270 | 1.00 | 24.09 O |
| ATOM | 15436 | N | VAL | B | 472 | −51.032 | −36.719 | −36.582 | 1.00 | 23.48 N |

TABLE 3-7-continued

Coordinates of *P. tremuloides* IspS

| ATOM | 15437 | CA | VAL | B | 472 | −51.279 | −35.774 | −35.510 | 1.00 | 23.15 | C |
|---|---|---|---|---|---|---|---|---|---|---|---|
| ATOM | 15439 | CB | VAL | B | 472 | −51.377 | −34.332 | −36.045 | 1.00 | 23.03 | C |
| ATOM | 15441 | CG1 | VAL | B | 472 | −51.739 | −33.347 | −34.929 | 1.00 | 21.74 | C |
| ATOM | 15445 | CG2 | VAL | B | 472 | −50.067 | −33.945 | −36.728 | 1.00 | 22.27 | C |
| ATOM | 15449 | C | VAL | B | 472 | −52.572 | −36.192 | −34.830 | 1.00 | 23.49 | C |
| ATOM | 15450 | O | VAL | B | 472 | −52.663 | −36.276 | −33.614 | 1.00 | 23.29 | O |
| ATOM | 15452 | N | MET | B | 473 | −53.573 | −36.508 | −35.626 | 1.00 | 24.34 | N |
| ATOM | 15453 | CA | MET | B | 473 | −54.850 | −36.901 | −35.070 | 1.00 | 24.93 | C |
| ATOM | 15455 | CB | MET | B | 473 | −55.816 | −37.266 | −36.190 | 1.00 | 25.09 | C |
| ATOM | 15458 | CG | MET | B | 473 | −57.191 | −36.788 | −35.912 | 1.00 | 26.94 | C |
| ATOM | 15461 | SD | MET | B | 473 | −57.328 | −35.035 | −36.251 | 1.00 | 29.69 | S |
| ATOM | 15462 | CE | MET | B | 473 | −58.316 | −35.080 | −37.775 | 1.00 | 29.12 | C |
| ATOM | 15466 | C | MET | B | 473 | −54.668 | −38.072 | −34.100 | 1.00 | 25.00 | C |
| ATOM | 15467 | O | MET | B | 473 | −55.135 | −38.018 | −32.963 | 1.00 | 24.78 | O |
| ATOM | 15469 | N | ASN | B | 474 | −53.965 | −39.110 | −34.556 | 1.00 | 25.30 | N |
| ATOM | 15470 | CA | ASN | B | 474 | −53.681 | −40.293 | −33.738 | 1.00 | 25.55 | C |
| ATOM | 15472 | CB | ASN | B | 474 | −53.143 | −41.439 | −34.601 | 1.00 | 25.82 | C |
| ATOM | 15475 | CG | ASN | B | 474 | −54.243 | −42.137 | −35.402 | 1.00 | 27.62 | C |
| ATOM | 15476 | OD1 | ASN | B | 474 | −54.238 | −42.102 | −36.638 | 1.00 | 29.33 | O |
| ATOM | 15477 | ND2 | ASN | B | 474 | −55.196 | −42.780 | −34.697 | 1.00 | 28.58 | N |
| ATOM | 15480 | C | ASN | B | 474 | −52.711 | −40.034 | −32.592 | 1.00 | 25.20 | C |
| ATOM | 15481 | O | ASN | B | 474 | −52.711 | −40.773 | −31.621 | 1.00 | 25.71 | O |
| ATOM | 15483 | N | LEU | B | 475 | −51.883 | −38.999 | −32.704 | 1.00 | 24.65 | N |
| ATOM | 15484 | CA | LEU | B | 475 | −50.987 | −38.595 | −31.614 | 1.00 | 24.04 | C |
| ATOM | 15486 | CB | LEU | B | 475 | −49.939 | −37.626 | −32.142 | 1.00 | 23.88 | C |
| ATOM | 15489 | CG | LEU | B | 475 | −48.837 | −37.285 | −31.164 | 1.00 | 23.70 | C |
| ATOM | 15491 | CD1 | LEU | B | 475 | −47.936 | −38.471 | −31.004 | 1.00 | 23.97 | C |
| ATOM | 15495 | CD2 | LEU | B | 475 | −48.088 | −36.104 | −31.679 | 1.00 | 23.99 | C |
| ATOM | 15499 | C | LEU | B | 475 | −51.747 | −37.940 | −30.453 | 1.00 | 23.65 | C |
| ATOM | 15500 | O | LEU | B | 475 | −51.323 | −38.014 | −29.299 | 1.00 | 23.74 | O |
| ATOM | 15502 | N | ILE | B | 476 | −52.858 | −37.282 | −30.766 | 1.00 | 23.15 | N |
| ATOM | 15503 | CA | ILE | B | 476 | −53.728 | −36.711 | −29.742 | 1.00 | 22.50 | C |
| ATOM | 15505 | CB | ILE | B | 476 | −54.779 | −35.755 | −30.359 | 1.00 | 22.27 | C |
| ATOM | 15507 | CG1 | ILE | B | 476 | −54.099 | −34.508 | −30.910 | 1.00 | 20.55 | C |
| ATOM | 15510 | CD1 | ILE | B | 476 | −55.000 | −33.671 | −31.693 | 1.00 | 19.19 | C |
| ATOM | 15514 | CG2 | ILE | B | 476 | −55.817 | −35.363 | −29.336 | 1.00 | 22.15 | C |
| ATOM | 15518 | C | ILE | B | 476 | −54.398 | −37.849 | −28.985 | 1.00 | 22.40 | C |
| ATOM | 15519 | O | ILE | B | 476 | −54.316 | −37.900 | −27.767 | 1.00 | 22.32 | O |
| ATOM | 15521 | N | ASP | B | 477 | −55.023 | −38.777 | −29.708 | 1.00 | 22.37 | N |
| ATOM | 15522 | CA | ASP | B | 477 | −55.616 | −39.975 | −29.090 | 1.00 | 22.55 | C |
| ATOM | 15524 | CB | ASP | B | 477 | −55.996 | −41.007 | −30.151 | 1.00 | 22.67 | C |
| ATOM | 15527 | CG | ASP | B | 477 | −57.262 | −40.636 | −30.892 | 1.00 | 24.93 | C |
| ATOM | 15528 | OD1 | ASP | B | 477 | −57.690 | −39.458 | −30.818 | 1.00 | 28.87 | O |
| ATOM | 15529 | OD2 | ASP | B | 477 | −57.847 | −41.523 | −31.549 | 1.00 | 27.92 | O |
| ATOM | 15530 | C | ASP | B | 477 | −54.675 | −40.622 | −28.083 | 1.00 | 22.10 | C |
| ATOM | 15531 | O | ASP | B | 477 | −55.048 | −40.877 | −26.938 | 1.00 | 21.83 | O |
| ATOM | 15533 | N | GLU | B | 478 | −53.444 | −40.867 | −28.510 | 1.00 | 21.73 | N |
| ATOM | 15534 | CA | GLU | B | 478 | −52.472 | −41.506 | −27.645 | 1.00 | 21.69 | C |
| ATOM | 15536 | CB | GLU | B | 478 | −51.233 | −41.920 | −28.437 | 1.00 | 21.97 | C |
| ATOM | 15539 | CG | GLU | B | 478 | −50.786 | −43.360 | −28.150 | 1.00 | 24.18 | C |
| ATOM | 15542 | CD | GLU | B | 478 | −51.793 | −44.429 | −28.618 | 1.00 | 27.03 | C |
| ATOM | 15543 | OE1 | GLU | B | 478 | −51.599 | −45.627 | −28.285 | 1.00 | 29.15 | O |
| ATOM | 15544 | OE2 | GLU | B | 478 | −52.770 | −44.080 | −29.323 | 1.00 | 28.37 | O |
| ATOM | 15545 | C | GLU | B | 478 | −52.107 | −40.608 | −26.449 | 1.00 | 20.97 | C |
| ATOM | 15546 | O | GLU | B | 478 | −51.928 | −41.110 | −25.316 | 1.00 | 21.15 | O |
| ATOM | 15548 | N | THR | B | 479 | −52.031 | −39.291 | −26.687 | 1.00 | 19.82 | N |
| ATOM | 15549 | CA | THR | B | 479 | −51.787 | −38.319 | −25.604 | 1.00 | 18.59 | C |
| ATOM | 15551 | CB | THR | B | 479 | −51.587 | −36.897 | −26.129 | 1.00 | 17.95 | C |
| ATOM | 15553 | OG1 | THR | B | 479 | −50.291 | −36.779 | −26.712 | 1.00 | 17.43 | O |
| ATOM | 15555 | CG2 | THR | B | 479 | −51.654 | −35.938 | −25.009 | 1.00 | 17.90 | C |
| ATOM | 15559 | C | THR | B | 479 | −52.927 | −38.342 | −24.580 | 1.00 | 18.16 | C |
| ATOM | 15560 | O | THR | B | 479 | −52.695 | −38.339 | −23.383 | 1.00 | 18.06 | O |
| ATOM | 15562 | N | TRP | B | 480 | −54.160 | −38.390 | −25.057 | 1.00 | 17.77 | N |
| ATOM | 15563 | CA | TRP | B | 480 | −55.301 | −38.493 | −24.169 | 1.00 | 17.54 | C |
| ATOM | 15565 | CB | TRP | B | 480 | −56.605 | −38.464 | −24.970 | 1.00 | 17.49 | C |
| ATOM | 15568 | CG | TRP | B | 480 | −57.239 | −37.099 | −25.028 | 1.00 | 17.53 | C |
| ATOM | 15569 | CD1 | TRP | B | 480 | −57.150 | −36.186 | −26.041 | 1.00 | 17.04 | C |
| ATOM | 15571 | NE1 | TRP | B | 480 | −57.857 | −35.067 | −25.721 | 1.00 | 16.57 | N |
| ATOM | 15573 | CE2 | TRP | B | 480 | −58.423 | −35.236 | −24.484 | 1.00 | 16.41 | C |
| ATOM | 15574 | CD2 | TRP | B | 480 | −58.055 | −36.498 | −24.020 | 1.00 | 16.68 | C |
| ATOM | 15575 | CE3 | TRP | B | 480 | −58.507 | −36.914 | −22.765 | 1.00 | 16.92 | C |
| ATOM | 15577 | CZ3 | TRP | B | 480 | −59.300 | −36.076 | −22.039 | 1.00 | 16.97 | C |
| ATOM | 15579 | CH2 | TRP | B | 480 | −59.654 | −34.823 | −22.524 | 1.00 | 16.91 | C |
| ATOM | 15581 | CZ2 | TRP | B | 480 | −59.223 | −34.383 | −23.742 | 1.00 | 16.89 | C |
| ATOM | 15583 | C | TRP | B | 480 | −55.232 | −39.760 | −23.334 | 1.00 | 17.75 | C |
| ATOM | 15584 | O | TRP | B | 480 | −55.582 | −39.747 | −22.164 | 1.00 | 17.74 | O |
| ATOM | 15586 | N | LYS | B | 481 | −54.784 | −40.861 | −23.933 | 1.00 | 18.09 | N |
| ATOM | 15587 | CA | LYS | B | 481 | −54.721 | −42.124 | −23.210 | 1.00 | 18.10 | C |

TABLE 3-7-continued

Coordinates of *P. tremuloides* IspS

| ATOM | 15589 | CB | LYS | B | 481 | −54.277 | −43.282 | −24.115 | 1.00 | 18.01 | C |
|---|---|---|---|---|---|---|---|---|---|---|---|
| ATOM | 15592 | CG | LYS | B | 481 | −55.311 | −43.803 | −25.114 | 1.00 | 16.89 | C |
| ATOM | 15595 | CD | LYS | B | 481 | −54.613 | −44.663 | −26.199 | 1.00 | 15.83 | C |
| ATOM | 15598 | CE | LYS | B | 481 | −55.587 | −45.500 | −27.025 | 1.00 | 14.74 | C |
| ATOM | 15601 | NZ | LYS | B | 481 | −55.119 | −45.725 | −28.413 | 1.00 | 12.34 | N |
| ATOM | 15605 | C | LYS | B | 481 | −53.750 | −41.970 | −22.054 | 1.00 | 18.46 | C |
| ATOM | 15606 | O | LYS | B | 481 | −53.976 | −42.494 | −20.969 | 1.00 | 18.44 | O |
| ATOM | 15608 | N | LYS | B | 482 | −52.662 | −41.252 | −22.279 | 1.00 | 18.80 | N |
| ATOM | 15609 | CA | LYS | B | 482 | −51.727 | −41.019 | −21.192 | 1.00 | 19.58 | C |
| ATOM | 15611 | CB | LYS | B | 482 | −50.425 | −40.424 | −21.727 | 1.00 | 20.03 | C |
| ATOM | 15614 | CG | LYS | B | 482 | −49.499 | −41.500 | −22.277 | 1.00 | 22.03 | C |
| ATOM | 15617 | CD | LYS | B | 482 | −48.706 | −41.063 | −23.506 | 1.00 | 24.87 | C |
| ATOM | 15620 | CE | LYS | B | 482 | −47.908 | −42.268 | −24.066 | 1.00 | 26.65 | C |
| ATOM | 15623 | NZ | LYS | B | 482 | −47.287 | −41.996 | −25.408 | 1.00 | 28.80 | N |
| ATOM | 15627 | C | LYS | B | 482 | −52.363 | −40.156 | −20.096 | 1.00 | 19.56 | C |
| ATOM | 15628 | O | LYS | B | 482 | −52.367 | −40.537 | −18.926 | 1.00 | 19.19 | O |
| ATOM | 15630 | N | MET | B | 483 | −52.922 | −39.013 | −20.483 | 1.00 | 20.00 | N |
| ATOM | 15631 | CA | MET | B | 483 | −53.677 | −38.165 | −19.552 | 1.00 | 20.37 | C |
| ATOM | 15633 | CB | MET | B | 483 | −54.426 | −37.057 | −20.295 | 1.00 | 20.25 | C |
| ATOM | 15636 | CG | MET | B | 483 | −53.529 | −35.951 | −20.807 | 1.00 | 20.52 | C |
| ATOM | 15639 | SD | MET | B | 483 | −54.461 | −34.483 | −21.225 | 1.00 | 20.47 | S |
| ATOM | 15640 | CE | MET | B | 483 | −55.361 | −35.084 | −22.649 | 1.00 | 22.07 | C |
| ATOM | 15644 | C | MET | B | 483 | −54.668 | −38.981 | −18.741 | 1.00 | 20.72 | C |
| ATOM | 15645 | O | MET | B | 483 | −54.809 | −38.779 | −17.543 | 1.00 | 20.37 | O |
| ATOM | 15647 | N | ASN | B | 484 | −55.345 | −39.910 | −19.403 | 1.00 | 21.57 | N |
| ATOM | 15648 | CA | ASN | B | 484 | −56.339 | −40.731 | −18.744 | 1.00 | 22.46 | C |
| ATOM | 15650 | CB | ASN | B | 484 | −57.042 | −41.631 | −19.765 | 1.00 | 22.23 | C |
| ATOM | 15653 | CG | ASN | B | 484 | −58.118 | −40.900 | −20.576 | 1.00 | 21.61 | C |
| ATOM | 15654 | OD1 | ASN | B | 484 | −58.412 | −39.722 | −20.362 | 1.00 | 20.25 | O |
| ATOM | 15655 | ND2 | ASN | B | 484 | −58.720 | −41.622 | −21.510 | 1.00 | 20.80 | N |
| ATOM | 15658 | C | ASN | B | 484 | −55.723 | −41.555 | −17.598 | 1.00 | 23.83 | C |
| ATOM | 15659 | O | ASN | B | 484 | −56.262 | −41.591 | −16.484 | 1.00 | 23.76 | O |
| ATOM | 15661 | N | LYS | B | 485 | −54.585 | −42.190 | −17.868 | 1.00 | 25.69 | N |
| ATOM | 15662 | CA | LYS | B | 485 | −53.854 | −42.937 | −16.843 | 1.00 | 27.11 | C |
| ATOM | 15664 | CB | LYS | B | 485 | −52.679 | −43.712 | −17.447 | 1.00 | 27.13 | C |
| ATOM | 15667 | CG | LYS | B | 485 | −52.073 | −44.755 | −16.489 | 1.00 | 28.85 | C |
| ATOM | 15670 | CD | LYS | B | 485 | −51.643 | −46.082 | −17.187 | 1.00 | 31.17 | C |
| ATOM | 15673 | CE | LYS | B | 485 | −50.150 | −46.132 | −17.555 | 1.00 | 32.11 | C |
| ATOM | 15676 | NZ | LYS | B | 485 | −49.291 | −46.282 | −16.344 | 1.00 | 33.08 | N |
| ATOM | 15680 | C | LYS | B | 485 | −53.370 | −42.035 | −15.701 | 1.00 | 28.37 | C |
| ATOM | 15681 | O | LYS | B | 485 | −53.288 | −42.481 | −14.563 | 1.00 | 28.59 | O |
| ATOM | 15683 | N | GLU | B | 486 | −53.083 | −40.766 | −15.980 | 1.00 | 29.89 | N |
| ATOM | 15684 | CA | GLU | B | 486 | −52.683 | −39.849 | −14.910 | 1.00 | 31.09 | C |
| ATOM | 15686 | CB | GLU | B | 486 | −52.174 | −38.511 | −15.470 | 1.00 | 31.55 | C |
| ATOM | 15689 | CG | GLU | B | 486 | −51.059 | −37.851 | −14.643 | 1.00 | 32.69 | C |
| ATOM | 15692 | CD | GLU | B | 486 | −49.785 | −38.689 | −14.605 | 1.00 | 34.51 | C |
| ATOM | 15693 | OE1 | GLU | B | 486 | −49.104 | −38.682 | −13.557 | 1.00 | 36.35 | O |
| ATOM | 15694 | OE2 | GLU | B | 486 | −49.476 | −39.368 | −15.611 | 1.00 | 34.55 | O |
| ATOM | 15695 | C | GLU | B | 486 | −53.836 | −39.615 | −13.939 | 1.00 | 31.70 | C |
| ATOM | 15696 | O | GLU | B | 486 | −53.684 | −39.868 | −12.750 | 1.00 | 31.90 | O |
| ATOM | 15698 | N | LYS | B | 487 | −54.983 | −39.164 | −14.453 | 1.00 | 32.71 | N |
| ATOM | 15699 | CA | LYS | B | 487 | −56.177 | −38.856 | −13.629 | 1.00 | 33.57 | C |
| ATOM | 15701 | CB | LYS | B | 487 | −57.343 | −38.402 | −14.519 | 1.00 | 33.54 | C |
| ATOM | 15704 | CG | LYS | B | 487 | −58.703 | −38.196 | −13.823 | 1.00 | 33.45 | C |
| ATOM | 15707 | CD | LYS | B | 487 | −58.686 | −37.024 | −12.866 | 1.00 | 33.71 | C |
| ATOM | 15710 | CE | LYS | B | 487 | −59.906 | −36.996 | −11.931 | 1.00 | 34.48 | C |
| ATOM | 15713 | NZ | LYS | B | 487 | −61.123 | −36.378 | −12.526 | 1.00 | 35.03 | N |
| ATOM | 15717 | C | LYS | B | 487 | −56.626 | −40.046 | −12.802 | 1.00 | 34.60 | C |
| ATOM | 15718 | O | LYS | B | 487 | −57.126 | −39.892 | −11.681 | 1.00 | 34.55 | O |
| ATOM | 15720 | N | LEU | B | 488 | −56.453 | −41.233 | −13.371 | 1.00 | 35.94 | N |
| ATOM | 15721 | CA | LEU | B | 488 | −56.878 | −42.451 | −12.723 | 1.00 | 37.00 | C |
| ATOM | 15723 | CB | LEU | B | 488 | −57.280 | −43.489 | −13.778 | 1.00 | 36.90 | C |
| ATOM | 15726 | CG | LEU | B | 488 | −58.081 | −44.714 | −13.312 | 1.00 | 37.52 | C |
| ATOM | 15728 | CD1 | LEU | B | 488 | −58.758 | −44.536 | −11.946 | 1.00 | 38.76 | C |
| ATOM | 15732 | CD2 | LEU | B | 488 | −59.121 | −45.084 | −14.346 | 1.00 | 38.42 | C |
| ATOM | 15736 | C | LEU | B | 488 | −55.786 | −42.980 | −11.803 | 1.00 | 38.02 | C |
| ATOM | 15737 | O | LEU | B | 488 | −56.063 | −43.315 | −10.653 | 1.00 | 38.19 | O |
| ATOM | 15739 | N | GLY | B | 489 | −54.550 | −43.016 | −12.298 | 1.00 | 39.44 | N |
| ATOM | 15740 | CA | GLY | B | 489 | −53.441 | −43.710 | −11.621 | 1.00 | 40.62 | C |
| ATOM | 15743 | C | GLY | B | 489 | −52.563 | −42.837 | −10.740 | 1.00 | 41.76 | C |
| ATOM | 15744 | O | GLY | B | 489 | −51.357 | −42.703 | −10.988 | 1.00 | 41.83 | O |
| ATOM | 15746 | N | GLY | B | 490 | −53.183 | −42.230 | −9.726 | 1.00 | 43.10 | N |
| ATOM | 15747 | CA | GLY | B | 490 | −52.481 | −41.538 | −8.636 | 1.00 | 43.82 | C |
| ATOM | 15750 | C | GLY | B | 490 | −51.131 | −40.924 | −8.967 | 1.00 | 44.31 | C |
| ATOM | 15751 | O | GLY | B | 490 | −50.084 | −41.560 | −8.831 | 1.00 | 44.25 | O |
| ATOM | 15753 | N | SER | B | 491 | −51.161 | −39.672 | −9.396 | 1.00 | 44.87 | N |
| ATOM | 15754 | CA | SER | B | 491 | −49.939 | −38.892 | −9.575 | 1.00 | 45.22 | C |
| ATOM | 15756 | CB | SER | B | 491 | −50.224 | −37.723 | −10.537 | 1.00 | 45.34 | C |

TABLE 3-7-continued

Coordinates of *P. tremuloides* IspS

| ATOM | 15759 | OG  | SER | B | 491 | −51.411 | −37.032 | −10.166 | 1.00 | 45.38 | O |
|------|-------|-----|-----|---|-----|---------|---------|---------|------|-------|---|
| ATOM | 15761 | C   | SER | B | 491 | −49.419 | −38.389 | −8.203  | 1.00 | 45.14 | C |
| ATOM | 15762 | O   | SER | B | 491 | −49.896 | −38.824 | −7.140  | 1.00 | 45.11 | O |
| ATOM | 15764 | N   | LEU | B | 492 | −48.429 | −37.491 | −8.227  | 1.00 | 44.77 | N |
| ATOM | 15765 | CA  | LEU | B | 492 | −48.046 | −36.752 | −7.018  | 1.00 | 44.31 | C |
| ATOM | 15767 | CB  | LEU | B | 492 | −46.726 | −35.971 | −7.188  | 1.00 | 44.55 | C |
| ATOM | 15770 | CG  | LEU | B | 492 | −45.530 | −36.546 | −7.972  | 1.00 | 45.73 | C |
| ATOM | 15772 | CD1 | LEU | B | 492 | −44.373 | −35.556 | −7.859  | 1.00 | 46.25 | C |
| ATOM | 15776 | CD2 | LEU | B | 492 | −45.084 | −37.972 | −7.530  | 1.00 | 46.14 | C |
| ATOM | 15780 | C   | LEU | B | 492 | −49.151 | −35.760 | −6.703  | 1.00 | 43.30 | C |
| ATOM | 15781 | O   | LEU | B | 492 | −49.315 | −35.370 | −5.555  | 1.00 | 43.49 | O |
| ATOM | 15783 | N   | PHE | B | 493 | −49.903 | −35.367 | −7.735  | 1.00 | 42.05 | N |
| ATOM | 15784 | CA  | PHE | B | 493 | −50.822 | −34.239 | −7.668  | 1.00 | 41.03 | C |
| ATOM | 15786 | CB  | PHE | B | 493 | −50.913 | −33.549 | −9.028  | 1.00 | 40.81 | C |
| ATOM | 15789 | CG  | PHE | B | 493 | −49.696 | −32.771 | −9.408  | 1.00 | 38.96 | C |
| ATOM | 15790 | CD1 | PHE | B | 493 | −49.651 | −31.408 | −9.233  | 1.00 | 37.06 | C |
| ATOM | 15792 | CE1 | PHE | B | 493 | −48.543 | −30.697 | −9.603  | 1.00 | 36.41 | C |
| ATOM | 15794 | CZ  | PHE | B | 493 | −47.471 | −31.341 | −10.158 | 1.00 | 35.87 | C |
| ATOM | 15796 | CE2 | PHE | B | 493 | −47.507 | −32.690 | −10.343 | 1.00 | 36.39 | C |
| ATOM | 15798 | CD2 | PHE | B | 493 | −48.612 | −33.400 | −9.977  | 1.00 | 37.36 | C |
| ATOM | 15800 | C   | PHE | B | 493 | −52.240 | −34.603 | −7.268  | 1.00 | 40.76 | C |
| ATOM | 15801 | O   | PHE | B | 493 | −52.686 | −35.733 | −7.419  | 1.00 | 40.35 | O |
| ATOM | 15803 | N   | ALA | B | 494 | −52.943 | −33.584 | −6.790  | 1.00 | 40.72 | N |
| ATOM | 15804 | CA  | ALA | B | 494 | −54.355 | −33.658 | −6.471  | 1.00 | 40.68 | C |
| ATOM | 15806 | CB  | ALA | B | 494 | −54.786 | −32.362 | −5.770  | 1.00 | 40.70 | C |
| ATOM | 15810 | C   | ALA | B | 494 | −55.175 | −33.851 | −7.744  | 1.00 | 40.59 | C |
| ATOM | 15811 | O   | ALA | B | 494 | −55.013 | −33.099 | −8.716  | 1.00 | 40.95 | O |
| ATOM | 15813 | N   | LYS | B | 495 | −56.071 | −34.835 | −7.733  | 1.00 | 40.12 | N |
| ATOM | 15814 | CA  | LYS | B | 495 | −57.000 | −35.047 | −8.854  | 1.00 | 39.67 | C |
| ATOM | 15816 | CB  | LYS | B | 495 | −58.008 | −36.166 | −8.520  | 1.00 | 39.98 | C |
| ATOM | 15819 | CG  | LYS | B | 495 | −57.388 | −37.590 | −8.496  | 1.00 | 40.57 | C |
| ATOM | 15822 | CD  | LYS | B | 495 | −58.468 | −38.688 | −8.419  | 1.00 | 41.18 | C |
| ATOM | 15825 | CE  | LYS | B | 495 | −57.878 | −40.065 | −8.132  | 1.00 | 41.28 | C |
| ATOM | 15828 | NZ  | LYS | B | 495 | −58.736 | −41.159 | −8.671  | 1.00 | 41.39 | N |
| ATOM | 15832 | C   | LYS | B | 495 | −57.717 | −33.752 | −9.333  | 1.00 | 38.82 | C |
| ATOM | 15833 | O   | LYS | B | 495 | −57.847 | −33.535 | −10.537 | 1.00 | 38.70 | O |
| ATOM | 15835 | N   | PRO | B | 496 | −58.169 | −32.890 | −8.397  | 1.00 | 37.71 | N |
| ATOM | 15836 | CA  | PRO | B | 496 | −58.701 | −31.551 | −8.687  | 1.00 | 36.80 | C |
| ATOM | 15838 | CB  | PRO | B | 496 | −58.820 | −30.937 | −7.304  | 1.00 | 36.94 | C |
| ATOM | 15841 | CG  | PRO | B | 496 | −59.255 | −32.073 | −6.483  | 1.00 | 37.90 | C |
| ATOM | 15844 | CD  | PRO | B | 496 | −58.534 | −33.294 | −7.030  | 1.00 | 37.86 | C |
| ATOM | 15847 | C   | PRO | B | 496 | −57.845 | −30.625 | −9.536  | 1.00 | 35.57 | C |
| ATOM | 15848 | O   | PRO | B | 496 | −58.389 | −29.693 | −10.139 | 1.00 | 35.93 | O |
| ATOM | 15849 | N   | PHE | B | 497 | −56.527 | −30.836 | −9.546  | 1.00 | 33.52 | N |
| ATOM | 15850 | CA  | PHE | B | 497 | −55.654 | −30.083 | −10.439 | 1.00 | 31.34 | C |
| ATOM | 15852 | CB  | PHE | B | 497 | −54.355 | −29.710 | −9.750  | 1.00 | 30.86 | C |
| ATOM | 15855 | CG  | PHE | B | 497 | −53.394 | −28.989 | −10.634 | 1.00 | 29.04 | C |
| ATOM | 15856 | CD1 | PHE | B | 497 | −53.639 | −27.700 | −11.022 | 1.00 | 27.89 | C |
| ATOM | 15858 | CE1 | PHE | B | 497 | −52.752 | −27.028 | −11.834 | 1.00 | 27.39 | C |
| ATOM | 15860 | CZ  | PHE | B | 497 | −51.599 | −27.653 | −12.259 | 1.00 | 27.40 | C |
| ATOM | 15862 | CE2 | PHE | B | 497 | −51.341 | −28.941 | −11.877 | 1.00 | 27.44 | C |
| ATOM | 15864 | CD2 | PHE | B | 497 | −52.236 | −29.604 | −11.074 | 1.00 | 28.18 | C |
| ATOM | 15866 | C   | PHE | B | 497 | −55.390 | −30.870 | −11.714 | 1.00 | 30.24 | C |
| ATOM | 15867 | O   | PHE | B | 497 | −55.301 | −30.266 | −12.786 | 1.00 | 30.39 | O |
| ATOM | 15869 | N   | VAL | B | 498 | −55.295 | −32.200 | −11.630 | 1.00 | 28.50 | N |
| ATOM | 15870 | CA  | VAL | B | 498 | −55.076 | −32.983 | −12.854 | 1.00 | 27.54 | C |
| ATOM | 15872 | CB  | VAL | B | 498 | −54.778 | −34.472 | −12.611 | 1.00 | 27.34 | C |
| ATOM | 15874 | CG1 | VAL | B | 498 | −56.027 | −35.194 | −12.262 | 1.00 | 28.14 | C |
| ATOM | 15878 | CG2 | VAL | B | 498 | −53.731 | −34.649 | −11.530 | 1.00 | 27.04 | C |
| ATOM | 15882 | C   | VAL | B | 498 | −56.277 | −32.857 | −13.784 | 1.00 | 26.60 | C |
| ATOM | 15883 | O   | VAL | B | 498 | −56.129 | −32.864 | −14.995 | 1.00 | 26.33 | O |
| ATOM | 15885 | N   | GLU | B | 499 | −57.468 | −32.731 | −13.214 | 1.00 | 25.87 | N |
| ATOM | 15886 | CA  | GLU | B | 499 | −58.662 | −32.484 | −14.022 | 1.00 | 25.20 | C |
| ATOM | 15888 | CB  | GLU | B | 499 | −59.975 | −32.639 | −13.206 | 1.00 | 25.26 | C |
| ATOM | 15891 | CG  | GLU | B | 499 | −61.287 | −32.694 | −14.028 | 1.00 | 25.16 | C |
| ATOM | 15894 | CD  | GLU | B | 499 | −61.422 | −33.922 | −14.973 | 1.00 | 26.79 | C |
| ATOM | 15895 | OE1 | GLU | B | 499 | −60.607 | −34.880 | −14.928 | 1.00 | 26.39 | O |
| ATOM | 15896 | OE2 | GLU | B | 499 | −62.379 | −33.926 | −15.785 | 1.00 | 27.83 | O |
| ATOM | 15897 | C   | GLU | B | 499 | −58.542 | −31.097 | −14.641 | 1.00 | 24.27 | C |
| ATOM | 15898 | O   | GLU | B | 499 | −58.819 | −30.948 | −15.832 | 1.00 | 24.32 | O |
| ATOM | 15900 | N   | THR | B | 500 | −58.098 | −30.093 | −13.882 | 1.00 | 22.90 | N |
| ATOM | 15901 | CA  | THR | B | 500 | −58.027 | −28.764 | −14.487 | 1.00 | 22.29 | C |
| ATOM | 15903 | CB  | THR | B | 500 | −57.908 | −27.592 | −13.488 | 1.00 | 22.43 | C |
| ATOM | 15905 | OG1 | THR | B | 500 | −56.536 | −27.259 | −13.274 | 1.00 | 22.65 | O |
| ATOM | 15907 | CG2 | THR | B | 500 | −58.614 | −27.899 | −12.183 | 1.00 | 22.84 | C |
| ATOM | 15911 | C   | THR | B | 500 | −56.940 | −28.671 | −15.565 | 1.00 | 21.20 | C |
| ATOM | 15912 | O   | THR | B | 500 | −57.120 | −27.939 | −16.536 | 1.00 | 21.06 | O |
| ATOM | 15914 | N   | ALA | B | 501 | −55.845 | −29.414 | −15.422 | 1.00 | 19.88 | N |

TABLE 3-7-continued

Coordinates of *P. tremuloides* IspS

| ATOM | 15915 | CA | ALA | B | 501 | −54.906 | −29.574 | −16.537 | 1.00 | 19.24 | C |
| ATOM | 15917 | CB | ALA | B | 501 | −53.704 | −30.393 | −16.115 | 1.00 | 19.22 | C |
| ATOM | 15921 | C | ALA | B | 501 | −55.581 | −30.226 | −17.757 | 1.00 | 18.68 | C |
| ATOM | 15922 | O | ALA | B | 501 | −55.427 | −29.768 | −18.881 | 1.00 | 18.32 | O |
| ATOM | 15924 | N | ILE | B | 502 | −56.324 | −31.300 | −17.523 | 1.00 | 18.11 | N |
| ATOM | 15925 | CA | ILE | B | 502 | −57.023 | −31.988 | −18.591 | 1.00 | 17.68 | C |
| ATOM | 15927 | CB | ILE | B | 502 | −57.750 | −33.251 | −18.059 | 1.00 | 17.63 | C |
| ATOM | 15929 | CG1 | ILE | B | 502 | −56.713 | −34.350 | −17.769 | 1.00 | 18.16 | C |
| ATOM | 15932 | CD1 | ILE | B | 502 | −57.253 | −35.645 | −17.115 | 1.00 | 17.02 | C |
| ATOM | 15936 | CG2 | ILE | B | 502 | −58.756 | −33.762 | −19.063 | 1.00 | 16.93 | C |
| ATOM | 15940 | C | ILE | B | 502 | −57.990 | −31.030 | −19.289 | 1.00 | 17.50 | C |
| ATOM | 15941 | O | ILE | B | 502 | −58.153 | −31.071 | −20.512 | 1.00 | 17.62 | O |
| ATOM | 15943 | N | ASN | B | 503 | −58.604 | −30.139 | −18.524 | 1.00 | 17.23 | N |
| ATOM | 15944 | CA | ASN | B | 503 | −59.545 | −29.184 | −19.102 | 1.00 | 17.07 | C |
| ATOM | 15946 | CB | ASN | B | 503 | −60.184 | −28.327 | −18.016 | 1.00 | 17.21 | C |
| ATOM | 15949 | CG | ASN | B | 503 | −61.155 | −29.094 | −17.176 | 1.00 | 17.29 | C |
| ATOM | 15950 | OD1 | ASN | B | 503 | −61.721 | −30.097 | −17.609 | 1.00 | 16.66 | O |
| ATOM | 15951 | ND2 | ASN | B | 503 | −61.365 | −28.621 | −15.958 | 1.00 | 19.16 | N |
| ATOM | 15954 | C | ASN | B | 503 | −58.920 | −28.270 | −20.149 | 1.00 | 16.59 | C |
| ATOM | 15955 | O | ASN | B | 503 | −59.611 | −27.811 | −21.071 | 1.00 | 16.67 | O |
| ATOM | 15957 | N | LEU | B | 504 | −57.629 | −27.992 | −20.014 | 1.00 | 15.79 | N |
| ATOM | 15958 | CA | LEU | B | 504 | −56.948 | −27.204 | −21.031 | 1.00 | 15.44 | C |
| ATOM | 15960 | CB | LEU | B | 504 | −55.530 | −26.865 | −20.609 | 1.00 | 15.07 | C |
| ATOM | 15963 | CG | LEU | B | 504 | −54.933 | −25.837 | −21.552 | 1.00 | 14.21 | C |
| ATOM | 15965 | CD1 | LEU | B | 504 | −54.246 | −24.726 | −20.800 | 1.00 | 14.21 | C |
| ATOM | 15969 | CD2 | LEU | B | 504 | −54.000 | −26.538 | −22.462 | 1.00 | 14.27 | C |
| ATOM | 15973 | C | LEU | B | 504 | −56.954 | −27.933 | −22.375 | 1.00 | 15.59 | C |
| ATOM | 15974 | O | LEU | B | 504 | −57.177 | −27.323 | −23.414 | 1.00 | 15.30 | O |
| ATOM | 15976 | N | ALA | B | 505 | −56.732 | −29.242 | −22.341 | 1.00 | 15.89 | N |
| ATOM | 15977 | CA | ALA | B | 505 | −56.914 | −30.073 | −23.514 | 1.00 | 16.23 | C |
| ATOM | 15979 | CB | ALA | B | 505 | −56.608 | −31.483 | −23.188 | 1.00 | 16.05 | C |
| ATOM | 15983 | C | ALA | B | 505 | −58.352 | −29.955 | −24.010 | 1.00 | 16.69 | C |
| ATOM | 15984 | O | ALA | B | 505 | −58.598 | −29.738 | −25.204 | 1.00 | 16.88 | O |
| ATOM | 15986 | N | ARG | B | 506 | −59.300 | −30.071 | −23.090 | 1.00 | 16.88 | N |
| ATOM | 15987 | CA | ARG | B | 506 | −60.709 | −29.972 | −23.457 | 1.00 | 17.20 | C |
| ATOM | 15989 | CB | ARG | B | 506 | −61.630 | −30.170 | −22.248 | 1.00 | 17.34 | C |
| ATOM | 15992 | CG | ARG | B | 506 | −61.549 | −31.537 | −21.614 | 1.00 | 17.46 | C |
| ATOM | 15995 | CD | ARG | B | 506 | −62.837 | −31.917 | −20.962 | 1.00 | 17.48 | C |
| ATOM | 15998 | NE | ARG | B | 506 | −62.783 | −33.280 | −20.435 | 1.00 | 18.37 | N |
| ATOM | 16000 | CZ | ARG | B | 506 | −62.404 | −33.613 | −19.201 | 1.00 | 19.03 | C |
| ATOM | 16001 | NH1 | ARG | B | 506 | −62.008 | −32.690 | −18.324 | 1.00 | 18.83 | N |
| ATOM | 16004 | NH2 | ARG | B | 506 | −62.415 | −34.892 | −18.841 | 1.00 | 19.72 | N |
| ATOM | 16007 | C | ARG | B | 506 | −61.038 | −28.646 | −24.114 | 1.00 | 17.32 | C |
| ATOM | 16008 | O | ARG | B | 506 | −61.754 | −28.622 | −25.111 | 1.00 | 17.41 | O |
| ATOM | 16010 | N | GLN | B | 507 | −60.540 | −27.543 | −23.564 | 1.00 | 17.59 | N |
| ATOM | 16011 | CA | GLN | B | 507 | −60.864 | −26.233 | −24.139 | 1.00 | 18.05 | C |
| ATOM | 16013 | CB | GLN | B | 507 | −60.382 | −25.090 | −23.258 | 1.00 | 18.16 | C |
| ATOM | 16016 | CG | GLN | B | 507 | −60.798 | −23.709 | −23.764 | 1.00 | 17.57 | C |
| ATOM | 16019 | CD | GLN | B | 507 | −62.291 | −23.508 | −23.723 | 1.00 | 17.42 | C |
| ATOM | 16020 | OE1 | GLN | B | 507 | −62.953 | −23.959 | −22.800 | 1.00 | 17.55 | O |
| ATOM | 16021 | NE2 | GLN | B | 507 | −62.832 | −22.823 | −24.722 | 1.00 | 17.56 | N |
| ATOM | 16024 | C | GLN | B | 507 | −60.258 | −26.060 | −25.521 | 1.00 | 18.49 | C |
| ATOM | 16025 | O | GLN | B | 507 | −60.855 | −25.413 | −26.380 | 1.00 | 18.73 | O |
| ATOM | 16027 | N | SER | B | 508 | −59.066 | −26.619 | −25.724 | 1.00 | 18.85 | N |
| ATOM | 16028 | CA | SER | B | 508 | −58.427 | −26.621 | −27.037 | 1.00 | 19.07 | C |
| ATOM | 16030 | CB | SER | B | 508 | −57.108 | −27.364 | −26.969 | 1.00 | 19.04 | C |
| ATOM | 16033 | OG | SER | B | 508 | −56.304 | −26.772 | −25.979 | 1.00 | 20.10 | O |
| ATOM | 16035 | C | SER | B | 508 | −59.305 | −27.296 | −28.065 | 1.00 | 19.12 | C |
| ATOM | 16036 | O | SER | B | 508 | −59.438 | −26.827 | −29.187 | 1.00 | 19.00 | O |
| ATOM | 16038 | N | HIS | B | 509 | −59.905 | −28.409 | −27.674 | 1.00 | 19.26 | N |
| ATOM | 16039 | CA | HIS | B | 509 | −60.814 | −29.095 | −28.559 | 1.00 | 19.33 | C |
| ATOM | 16041 | CB | HIS | B | 509 | −61.275 | −30.412 | −27.959 | 1.00 | 19.30 | C |
| ATOM | 16044 | CG | HIS | B | 509 | −60.263 | −31.501 | −28.067 | 1.00 | 18.71 | C |
| ATOM | 16045 | ND1 | HIS | B | 509 | −59.941 | −32.089 | −29.267 | 1.00 | 18.57 | N |
| ATOM | 16047 | CE1 | HIS | B | 509 | −59.020 | −33.012 | −29.064 | 1.00 | 19.07 | C |
| ATOM | 16049 | NE2 | HIS | B | 509 | −58.738 | −33.044 | −27.774 | 1.00 | 18.52 | N |
| ATOM | 16051 | CD2 | HIS | B | 509 | −59.499 | −32.105 | −27.129 | 1.00 | 18.43 | C |
| ATOM | 16053 | C | HIS | B | 509 | −62.017 | −28.251 | −28.878 | 1.00 | 19.60 | C |
| ATOM | 16054 | O | HIS | B | 509 | −62.491 | −28.286 | −29.969 | 1.00 | 19.68 | O |
| ATOM | 16056 | N | CYS | B | 510 | −62.540 | −27.502 | −27.932 | 1.00 | 20.12 | N |
| ATOM | 16057 | CA | CYS | B | 510 | −63.748 | −26.738 | −28.216 | 1.00 | 20.63 | C |
| ATOM | 16059 | CB | CYS | B | 510 | −64.493 | −26.492 | −26.915 | 1.00 | 20.70 | C |
| ATOM | 16062 | SG | CYS | B | 510 | −64.856 | −28.020 | −26.065 | 1.00 | 22.93 | S |
| ATOM | 16064 | C | CYS | B | 510 | −63.465 | −25.422 | −28.950 | 1.00 | 20.55 | C |
| ATOM | 16065 | O | CYS | B | 510 | −64.338 | −24.881 | −29.622 | 1.00 | 20.16 | O |
| ATOM | 16067 | N | THR | B | 511 | −62.236 | −24.933 | −28.827 | 1.00 | 20.89 | N |
| ATOM | 16068 | CA | THR | B | 511 | −61.833 | −23.654 | −29.378 | 1.00 | 21.32 | C |
| ATOM | 16070 | CB | THR | B | 511 | −60.682 | −23.107 | −28.550 | 1.00 | 20.76 | C |

TABLE 3-7-continued

| | | | | | | | | | | | |
|---|---|---|---|---|---|---|---|---|---|---|---|
| colspan="12" | Coordinates of *P. tremuloides* IspS |

| ATOM | 16072 | OG1 | THR | B | 511 | −61.208 | −22.619 | −27.324 | 1.00 | 19.50 | O |
| ATOM | 16074 | CG2 | THR | B | 511 | −59.961 | −21.994 | −29.253 | 1.00 | 19.79 | C |
| ATOM | 16078 | C | THR | B | 511 | −61.417 | −23.735 | −30.851 | 1.00 | 23.11 | C |
| ATOM | 16079 | O | THR | B | 511 | −61.910 | −22.992 | −31.694 | 1.00 | 22.75 | O |
| ATOM | 16081 | N | TYR | B | 512 | −60.501 | −24.646 | −31.152 | 1.00 | 25.46 | N |
| ATOM | 16082 | CA | TYR | B | 512 | −59.867 | −24.704 | −32.462 | 1.00 | 27.09 | C |
| ATOM | 16084 | CB | TYR | B | 512 | −58.397 | −25.107 | −32.327 | 1.00 | 27.16 | C |
| ATOM | 16087 | CG | TYR | B | 512 | −57.598 | −24.056 | −31.582 | 1.00 | 27.26 | C |
| ATOM | 16088 | CD1 | TYR | B | 512 | −57.300 | −22.834 | −32.182 | 1.00 | 28.18 | C |
| ATOM | 16090 | CE1 | TYR | B | 512 | −56.583 | −21.844 | −31.511 | 1.00 | 27.98 | C |
| ATOM | 16092 | CZ | TYR | B | 512 | −56.164 | −22.068 | −30.226 | 1.00 | 27.72 | C |
| ATOM | 16093 | OH | TYR | B | 512 | −55.462 | −21.072 | −29.584 | 1.00 | 27.09 | O |
| ATOM | 16095 | CE2 | TYR | B | 512 | −56.453 | −23.281 | −29.602 | 1.00 | 27.52 | C |
| ATOM | 16097 | CD2 | TYR | B | 512 | −57.171 | −24.262 | −30.278 | 1.00 | 26.68 | C |
| ATOM | 16099 | C | TYR | B | 512 | −60.633 | −25.623 | −33.382 | 1.00 | 28.79 | C |
| ATOM | 16100 | O | TYR | B | 512 | −61.050 | −25.179 | −34.444 | 1.00 | 28.98 | O |
| ATOM | 16102 | N | HIS | B | 513 | −60.789 | −26.893 | −32.991 | 1.00 | 31.06 | N |
| ATOM | 16103 | CA | HIS | B | 513 | −61.865 | −27.800 | −33.492 | 1.00 | 33.07 | C |
| ATOM | 16105 | CB | HIS | B | 513 | −62.740 | −28.208 | −32.265 | 1.00 | 33.66 | C |
| ATOM | 16108 | CG | HIS | B | 513 | −64.181 | −28.602 | −32.535 | 1.00 | 34.73 | C |
| ATOM | 16109 | ND1 | HIS | B | 513 | −65.035 | −27.903 | −33.367 | 1.00 | 35.70 | N |
| ATOM | 16111 | CE1 | HIS | B | 513 | −66.234 | −28.464 | −33.343 | 1.00 | 35.40 | C |
| ATOM | 16113 | NE2 | HIS | B | 513 | −66.206 | −29.469 | −32.491 | 1.00 | 35.10 | N |
| ATOM | 16115 | CD2 | HIS | B | 513 | −64.943 | −29.565 | −31.956 | 1.00 | 35.07 | C |
| ATOM | 16117 | C | HIS | B | 513 | −62.692 | −27.179 | −34.623 | 1.00 | 34.03 | C |
| ATOM | 16118 | O | HIS | B | 513 | −63.003 | −27.848 | −35.627 | 1.00 | 34.55 | O |
| ATOM | 16120 | N | ASN | B | 514 | −63.047 | −25.906 | −34.444 | 1.00 | 34.65 | N |
| ATOM | 16121 | CA | ASN | B | 514 | −63.713 | −25.123 | −35.483 | 1.00 | 35.15 | C |
| ATOM | 16123 | CB | ASN | B | 514 | −63.845 | −23.643 | −35.070 | 1.00 | 35.01 | C |
| ATOM | 16126 | CG | ASN | B | 514 | −64.704 | −23.456 | −33.820 | 1.00 | 33.48 | C |
| ATOM | 16127 | OD1 | ASN | B | 514 | −64.787 | −24.343 | −32.968 | 1.00 | 30.92 | O |
| ATOM | 16128 | ND2 | ASN | B | 514 | −65.327 | −22.295 | −33.703 | 1.00 | 32.16 | N |
| ATOM | 16131 | C | ASN | B | 514 | −63.192 | −25.274 | −36.942 | 1.00 | 36.08 | C |
| ATOM | 16132 | O | ASN | B | 514 | −62.010 | −25.051 | −37.254 | 1.00 | 35.69 | O |
| ATOM | 16134 | N | GLY | B | 515 | −64.119 | −25.765 | −37.772 | 1.00 | 37.15 | N |
| ATOM | 16135 | CA | GLY | B | 515 | −64.224 | −25.493 | −39.177 | 1.00 | 37.94 | C |
| ATOM | 16138 | C | GLY | B | 515 | −65.269 | −24.384 | −39.284 | 1.00 | 39.01 | C |
| ATOM | 16139 | O | GLY | B | 515 | −64.904 | −23.286 | −39.702 | 1.00 | 39.58 | O |
| ATOM | 16141 | N | ASP | B | 516 | −66.550 | −24.585 | −38.909 | 1.00 | 39.95 | N |
| ATOM | 16142 | CA | ASP | B | 516 | −67.167 | −25.810 | −38.349 | 1.00 | 40.65 | C |
| ATOM | 16144 | CB | ASP | B | 516 | −67.296 | −25.652 | −36.836 | 1.00 | 41.09 | C |
| ATOM | 16147 | CG | ASP | B | 516 | −66.318 | −26.511 | −36.063 | 1.00 | 43.63 | C |
| ATOM | 16148 | OD1 | ASP | B | 516 | −65.697 | −27.434 | −36.662 | 1.00 | 45.83 | O |
| ATOM | 16149 | OD2 | ASP | B | 516 | −66.152 | −26.246 | −34.843 | 1.00 | 47.12 | O |
| ATOM | 16150 | C | ASP | B | 516 | −68.603 | −26.067 | −38.853 | 1.00 | 40.78 | C |
| ATOM | 16151 | O | ASP | B | 516 | −69.134 | −25.301 | −39.660 | 1.00 | 41.28 | O |
| ATOM | 16153 | N | ALA | B | 517 | −69.222 | −27.141 | −38.349 | 1.00 | 40.66 | N |
| ATOM | 16154 | CA | ALA | B | 517 | −70.675 | −27.396 | −38.468 | 1.00 | 40.60 | C |
| ATOM | 16156 | CB | ALA | B | 517 | −71.422 | −26.622 | −37.359 | 1.00 | 40.27 | C |
| ATOM | 16160 | C | ALA | B | 517 | −71.295 | −27.106 | −39.862 | 1.00 | 40.79 | C |
| ATOM | 16161 | O | ALA | B | 517 | −70.654 | −27.296 | −40.899 | 1.00 | 40.67 | O |
| ATOM | 16163 | N | HIS | B | 518 | −72.562 | −26.696 | −39.874 | 1.00 | 41.13 | N |
| ATOM | 16164 | CA | HIS | B | 518 | −73.162 | −26.033 | −41.039 | 1.00 | 41.60 | C |
| ATOM | 16166 | CB | HIS | B | 518 | −74.446 | −26.756 | −41.480 | 1.00 | 42.24 | C |
| ATOM | 16169 | CG | HIS | B | 518 | −74.207 | −28.179 | −41.910 | 1.00 | 45.54 | C |
| ATOM | 16170 | ND1 | HIS | B | 518 | −73.441 | −28.509 | −43.012 | 1.00 | 48.51 | N |
| ATOM | 16172 | CE1 | HIS | B | 518 | −73.392 | −29.825 | −43.140 | 1.00 | 48.79 | C |
| ATOM | 16174 | NE2 | HIS | B | 518 | −74.092 | −30.364 | −42.156 | 1.00 | 49.12 | N |
| ATOM | 16176 | CD2 | HIS | B | 518 | −74.608 | −29.357 | −41.369 | 1.00 | 48.28 | C |
| ATOM | 16178 | C | HIS | B | 518 | −73.377 | −24.545 | −40.686 | 1.00 | 40.84 | C |
| ATOM | 16179 | O | HIS | B | 518 | −74.487 | −23.997 | −40.769 | 1.00 | 40.60 | O |
| ATOM | 16181 | N | THR | B | 519 | −72.261 | −23.932 | −40.275 | 1.00 | 40.10 | N |
| ATOM | 16182 | CA | THR | B | 519 | −72.143 | −22.521 | −39.878 | 1.00 | 39.39 | C |
| ATOM | 16184 | CB | THR | B | 519 | −72.561 | −22.263 | −38.393 | 1.00 | 39.40 | C |
| ATOM | 16186 | OG1 | THR | B | 519 | −71.823 | −23.131 | −37.517 | 1.00 | 39.55 | O |
| ATOM | 16188 | CG2 | THR | B | 519 | −74.074 | −22.460 | −38.178 | 1.00 | 38.98 | C |
| ATOM | 16192 | C | THR | B | 519 | −70.654 | −22.164 | −40.059 | 1.00 | 38.81 | C |
| ATOM | 16193 | O | THR | B | 519 | −69.800 | −23.050 | −40.067 | 1.00 | 38.48 | O |
| ATOM | 16195 | N | SER | B | 520 | −70.338 | −20.881 | −40.199 | 1.00 | 38.19 | N |
| ATOM | 16196 | CA | SER | B | 520 | −68.959 | −20.453 | −40.521 | 1.00 | 37.77 | C |
| ATOM | 16198 | CB | SER | B | 520 | −68.983 | −18.976 | −40.960 | 1.00 | 37.76 | C |
| ATOM | 16201 | OG | SER | B | 520 | −68.760 | −18.106 | −39.870 | 1.00 | 38.49 | O |
| ATOM | 16203 | C | SER | B | 520 | −67.974 | −20.724 | −39.340 | 1.00 | 37.24 | C |
| ATOM | 16204 | O | SER | B | 520 | −68.394 | −21.267 | −38.320 | 1.00 | 36.89 | O |
| ATOM | 16206 | N | PRO | B | 521 | −66.671 | −20.350 | −39.472 | 1.00 | 36.96 | N |
| ATOM | 16207 | CA | PRO | B | 521 | −65.692 | −20.638 | −38.396 | 1.00 | 36.80 | C |
| ATOM | 16209 | CB | PRO | B | 521 | −64.320 | −20.354 | −39.041 | 1.00 | 36.68 | C |
| ATOM | 16212 | CG | PRO | B | 521 | −64.599 | −19.593 | −40.309 | 1.00 | 37.19 | C |

TABLE 3-7-continued

| | | | | | Coordinates of *P. tremuloides* IspS | | | | | |
|---|---|---|---|---|---|---|---|---|---|---|
| ATOM | 16215 | CD | PRO | B | 521 | −66.091 | −19.469 | −40.507 | 1.00 | 37.10 | C |
| ATOM | 16218 | C | PRO | B | 521 | −65.915 | −19.763 | −37.168 | 1.00 | 36.68 | C |
| ATOM | 16219 | O | PRO | B | 521 | −66.233 | −20.289 | −36.105 | 1.00 | 36.90 | O |
| ATOM | 16220 | N | ASP | B | 522 | −65.744 | −18.445 | −37.298 | 1.00 | 36.61 | N |
| ATOM | 16221 | CA | ASP | B | 522 | −66.373 | −17.528 | −36.347 | 1.00 | 36.58 | C |
| ATOM | 16223 | CB | ASP | B | 522 | −65.938 | −16.070 | −36.543 | 1.00 | 36.82 | C |
| ATOM | 16226 | CG | ASP | B | 522 | −64.456 | −15.846 | −36.243 | 1.00 | 37.94 | C |
| ATOM | 16227 | OD1 | ASP | B | 522 | −63.848 | −16.627 | −35.473 | 1.00 | 39.62 | O |
| ATOM | 16228 | OD2 | ASP | B | 522 | −63.891 | −14.876 | −36.790 | 1.00 | 39.40 | O |
| ATOM | 16229 | C | ASP | B | 522 | −67.836 | −17.718 | −36.681 | 1.00 | 36.12 | C |
| ATOM | 16230 | O | ASP | B | 522 | −68.150 | −18.306 | −37.702 | 1.00 | 35.98 | O |
| ATOM | 16232 | N | GLU | B | 523 | −68.732 | −17.249 | −35.830 | 1.00 | 35.69 | N |
| ATOM | 16233 | CA | GLU | B | 523 | −70.152 | −17.605 | −35.927 | 1.00 | 35.46 | C |
| ATOM | 16235 | CB | GLU | B | 523 | −70.703 | −17.560 | −37.379 | 1.00 | 35.51 | C |
| ATOM | 16238 | CG | GLU | B | 523 | −70.535 | −16.175 | −38.061 | 1.00 | 36.11 | C |
| ATOM | 16241 | CD | GLU | B | 523 | −70.854 | −16.136 | −39.572 | 1.00 | 36.72 | C |
| ATOM | 16242 | OE1 | GLU | B | 523 | −71.848 | −16.767 | −40.013 | 1.00 | 37.20 | O |
| ATOM | 16243 | OE2 | GLU | B | 523 | −70.101 | −15.452 | −40.314 | 1.00 | 35.53 | O |
| ATOM | 16244 | C | GLU | B | 523 | −70.440 | −18.943 | −35.216 | 1.00 | 34.97 | C |
| ATOM | 16245 | O | GLU | B | 523 | −71.557 | −19.148 | −34.765 | 1.00 | 35.02 | O |
| ATOM | 16247 | N | LEU | B | 524 | −69.462 | −19.846 | −35.099 | 1.00 | 34.59 | N |
| ATOM | 16248 | CA | LEU | B | 524 | −69.503 | −20.832 | −34.004 | 1.00 | 34.45 | C |
| ATOM | 16250 | CB | LEU | B | 524 | −68.735 | −22.136 | −34.286 | 1.00 | 34.21 | C |
| ATOM | 16253 | CG | LEU | B | 524 | −69.530 | −23.434 | −34.508 | 1.00 | 33.92 | C |
| ATOM | 16255 | CD1 | LEU | B | 524 | −68.657 | −24.627 | −34.227 | 1.00 | 32.21 | C |
| ATOM | 16259 | CD2 | LEU | B | 524 | −70.794 | −23.520 | −33.641 | 1.00 | 34.06 | C |
| ATOM | 16263 | C | LEU | B | 524 | −68.901 | −20.162 | −32.791 | 1.00 | 34.38 | C |
| ATOM | 16264 | O | LEU | B | 524 | −69.535 | −20.067 | −31.741 | 1.00 | 34.49 | O |
| ATOM | 16266 | N | THR | B | 525 | −67.670 | −19.688 | −32.958 | 1.00 | 34.30 | N |
| ATOM | 16267 | CA | THR | B | 525 | −66.913 | −19.073 | −31.874 | 1.00 | 34.23 | C |
| ATOM | 16269 | CB | THR | B | 525 | −65.570 | −18.524 | −32.380 | 1.00 | 34.04 | C |
| ATOM | 16271 | OG1 | THR | B | 525 | −64.894 | −19.549 | −33.112 | 1.00 | 33.83 | O |
| ATOM | 16273 | CG2 | THR | B | 525 | −64.689 | −18.087 | −31.227 | 1.00 | 33.37 | C |
| ATOM | 16277 | C | THR | B | 525 | −67.702 | −17.960 | −31.184 | 1.00 | 34.46 | C |
| ATOM | 16278 | O | THR | B | 525 | −67.684 | −17.858 | −29.955 | 1.00 | 34.57 | O |
| ATOM | 16280 | N | ARG | B | 526 | −68.401 | −17.144 | −31.969 | 1.00 | 34.54 | N |
| ATOM | 16281 | CA | ARG | B | 526 | −69.200 | −16.056 | −31.418 | 1.00 | 34.60 | C |
| ATOM | 16283 | CB | ARG | B | 526 | −69.571 | −15.059 | −32.513 | 1.00 | 35.04 | C |
| ATOM | 16286 | CG | ARG | B | 526 | −70.256 | −13.800 | −32.013 | 1.00 | 37.13 | C |
| ATOM | 16289 | CD | ARG | B | 526 | −70.143 | −12.656 | −33.026 | 1.00 | 39.87 | C |
| ATOM | 16292 | NE | ARG | B | 526 | −70.353 | −13.075 | −34.420 | 1.00 | 42.28 | N |
| ATOM | 16294 | CZ | ARG | B | 526 | −71.543 | −13.292 | −35.000 | 1.00 | 44.26 | C |
| ATOM | 16295 | NH1 | ARG | B | 526 | −72.685 | −13.159 | −34.320 | 1.00 | 44.66 | N |
| ATOM | 16298 | NH2 | ARG | B | 526 | −71.593 | −13.658 | −36.279 | 1.00 | 44.49 | N |
| ATOM | 16301 | C | ARG | B | 526 | −70.448 | −16.593 | −30.735 | 1.00 | 33.91 | C |
| ATOM | 16302 | O | ARG | B | 526 | −70.848 | −16.074 | −29.704 | 1.00 | 33.74 | O |
| ATOM | 16304 | N | LYS | B | 527 | −71.048 | −17.637 | −31.306 | 1.00 | 33.39 | N |
| ATOM | 16305 | CA | LYS | B | 527 | −72.240 | −18.252 | −30.722 | 1.00 | 33.15 | C |
| ATOM | 16307 | CB | LYS | B | 527 | −72.837 | −19.332 | −31.639 | 1.00 | 33.42 | C |
| ATOM | 16310 | CG | LYS | B | 527 | −73.898 | −18.804 | −32.609 | 1.00 | 34.55 | C |
| ATOM | 16313 | CD | LYS | B | 527 | −74.643 | −19.919 | −33.358 | 1.00 | 35.43 | C |
| ATOM | 16316 | CE | LYS | B | 527 | −75.230 | −19.383 | −34.667 | 1.00 | 36.11 | C |
| ATOM | 16319 | NZ | LYS | B | 527 | −76.076 | −20.372 | −35.384 | 1.00 | 37.04 | N |
| ATOM | 16323 | C | LYS | B | 527 | −71.925 | −18.865 | −29.378 | 1.00 | 32.36 | C |
| ATOM | 16324 | O | LYS | B | 527 | −72.589 | −18.584 | −28.387 | 1.00 | 32.56 | O |
| ATOM | 16326 | N | ARG | B | 528 | −70.909 | −19.713 | −29.358 | 1.00 | 31.53 | N |
| ATOM | 16327 | CA | ARG | B | 528 | −70.502 | −20.401 | −28.138 | 1.00 | 30.77 | C |
| ATOM | 16329 | CB | ARG | B | 528 | −69.283 | −21.286 | −28.414 | 1.00 | 30.55 | C |
| ATOM | 16332 | CG | ARG | B | 528 | −69.624 | −22.519 | −29.252 | 1.00 | 29.48 | C |
| ATOM | 16335 | CD | ARG | B | 528 | −68.418 | −23.417 | −29.493 | 1.00 | 28.05 | C |
| ATOM | 16338 | NE | ARG | B | 528 | −68.811 | −24.774 | −29.880 | 1.00 | 26.55 | N |
| ATOM | 16340 | CZ | ARG | B | 528 | −67.968 | −25.719 | −30.288 | 1.00 | 25.87 | C |
| ATOM | 16341 | NH1 | ARG | B | 528 | −66.668 | −25.472 | −30.385 | 1.00 | 26.33 | N |
| ATOM | 16344 | NH2 | ARG | B | 528 | −68.424 | −26.920 | −30.615 | 1.00 | 25.49 | N |
| ATOM | 16347 | C | ARG | B | 528 | −70.225 | −19.415 | −27.004 | 1.00 | 30.42 | C |
| ATOM | 16348 | O | ARG | B | 528 | −70.721 | −19.582 | −25.885 | 1.00 | 30.30 | O |
| ATOM | 16350 | N | VAL | B | 529 | −69.455 | −18.376 | −27.307 | 1.00 | 29.96 | N |
| ATOM | 16351 | CA | VAL | B | 529 | −69.194 | −17.312 | −26.342 | 1.00 | 29.47 | C |
| ATOM | 16353 | CB | VAL | B | 529 | −68.261 | −16.227 | −26.932 | 1.00 | 29.40 | C |
| ATOM | 16355 | CG1 | VAL | B | 529 | −68.269 | −14.968 | −26.081 | 1.00 | 29.18 | C |
| ATOM | 16359 | CG2 | VAL | B | 529 | −66.845 | −16.782 | −27.062 | 1.00 | 28.90 | C |
| ATOM | 16363 | C | VAL | B | 529 | −70.516 | −16.723 | −25.841 | 1.00 | 28.98 | C |
| ATOM | 16364 | O | VAL | B | 529 | −70.759 | −16.682 | −24.641 | 1.00 | 28.97 | O |
| ATOM | 16366 | N | LEU | B | 530 | −71.384 | −16.308 | −26.752 | 1.00 | 28.54 | N |
| ATOM | 16367 | CA | LEU | B | 530 | −72.709 | −15.824 | −26.353 | 1.00 | 28.23 | C |
| ATOM | 16369 | CB | LEU | B | 530 | −73.631 | −15.604 | −27.559 | 1.00 | 28.09 | C |
| ATOM | 16372 | CG | LEU | B | 530 | −73.767 | −14.150 | −28.007 | 1.00 | 28.15 | C |
| ATOM | 16374 | CD1 | LEU | B | 530 | −72.412 | −13.570 | −28.406 | 1.00 | 27.99 | C |

TABLE 3-7-continued

| | | | | | | | | | | | |
|---|---|---|---|---|---|---|---|---|---|---|---|
| ATOM | 16378 | CD2 | LEU | B | 530 | −74.784 | −14.034 | −29.150 | 1.00 | 28.85 | C |
| ATOM | 16382 | C | LEU | B | 530 | −73.389 | −16.767 | −25.367 | 1.00 | 27.88 | C |
| ATOM | 16383 | O | LEU | B | 530 | −73.932 | −16.319 | −24.363 | 1.00 | 28.11 | O |
| ATOM | 16385 | N | SER | B | 531 | −73.352 | −18.066 | −25.652 | 1.00 | 27.28 | N |
| ATOM | 16386 | CA | SER | B | 531 | −74.081 | −19.049 | −24.849 | 1.00 | 26.68 | C |
| ATOM | 16388 | CB | SER | B | 531 | −74.209 | −20.363 | −25.612 | 1.00 | 26.68 | C |
| ATOM | 16391 | OG | SER | B | 531 | −72.970 | −21.033 | −25.681 | 1.00 | 26.67 | O |
| ATOM | 16393 | C | SER | B | 531 | −73.410 | −19.312 | −23.514 | 1.00 | 26.20 | C |
| ATOM | 16394 | O | SER | B | 531 | −74.076 | −19.550 | −22.511 | 1.00 | 25.86 | O |
| ATOM | 16396 | N | VAL | B | 532 | −72.085 | −19.281 | −23.512 | 1.00 | 25.86 | N |
| ATOM | 16397 | CA | VAL | B | 532 | −71.320 | −19.562 | −22.306 | 1.00 | 25.51 | C |
| ATOM | 16399 | CB | VAL | B | 532 | −69.891 | −20.055 | −22.651 | 1.00 | 25.34 | C |
| ATOM | 16401 | CG1 | VAL | B | 532 | −68.955 | −19.932 | −21.460 | 1.00 | 24.01 | C |
| ATOM | 16405 | CG2 | VAL | B | 532 | −69.950 | −21.484 | −23.158 | 1.00 | 24.95 | C |
| ATOM | 16409 | C | VAL | B | 532 | −71.271 | −18.357 | −21.373 | 1.00 | 25.52 | C |
| ATOM | 16410 | O | VAL | B | 532 | −71.377 | −18.523 | −20.164 | 1.00 | 25.82 | O |
| ATOM | 16412 | N | ILE | B | 533 | −71.137 | −17.158 | −21.935 | 1.00 | 25.39 | N |
| ATOM | 16413 | CA | ILE | B | 533 | −70.875 | −15.954 | −21.151 | 1.00 | 25.48 | C |
| ATOM | 16415 | CB | ILE | B | 533 | −69.666 | −15.185 | −21.732 | 1.00 | 25.30 | C |
| ATOM | 16417 | CG1 | ILE | B | 533 | −68.375 | −15.928 | −21.451 | 1.00 | 24.91 | C |
| ATOM | 16420 | CD1 | ILE | B | 533 | −68.118 | −16.120 | −19.989 | 1.00 | 25.00 | C |
| ATOM | 16424 | CG2 | ILE | B | 533 | −69.553 | −13.797 | −21.130 | 1.00 | 25.81 | C |
| ATOM | 16428 | C | ILE | B | 533 | −72.065 | −14.983 | −21.030 | 1.00 | 25.77 | C |
| ATOM | 16429 | O | ILE | B | 533 | −72.537 | −14.707 | −19.928 | 1.00 | 25.77 | O |
| ATOM | 16431 | N | THR | B | 534 | −72.541 | −14.442 | −22.142 | 1.00 | 25.98 | N |
| ATOM | 16432 | CA | THR | B | 534 | −73.446 | −13.295 | −22.064 | 1.00 | 26.31 | C |
| ATOM | 16434 | CB | THR | B | 534 | −73.094 | −12.253 | −23.143 | 1.00 | 26.21 | C |
| ATOM | 16436 | OG1 | THR | B | 534 | −72.914 | −12.909 | −24.397 | 1.00 | 26.72 | O |
| ATOM | 16438 | CG2 | THR | B | 534 | −71.795 | −11.535 | −22.781 | 1.00 | 25.97 | C |
| ATOM | 16442 | C | THR | B | 534 | −74.961 | −13.621 | −22.064 | 1.00 | 26.50 | C |
| ATOM | 16443 | O | THR | B | 534 | −75.713 | −12.974 | −21.344 | 1.00 | 26.67 | O |
| ATOM | 16445 | N | GLU | B | 535 | −75.410 | −14.616 | −22.829 | 1.00 | 26.55 | N |
| ATOM | 16446 | CA | GLU | B | 535 | −76.851 | −14.892 | −22.961 | 1.00 | 26.50 | C |
| ATOM | 16448 | CB | GLU | B | 535 | −77.197 | −15.197 | −24.426 | 1.00 | 26.68 | C |
| ATOM | 16451 | CG | GLU | B | 535 | −77.226 | −13.936 | −25.296 | 1.00 | 27.68 | C |
| ATOM | 16454 | CD | GLU | B | 535 | −78.193 | −14.014 | −26.475 | 1.00 | 28.75 | C |
| ATOM | 16455 | OE1 | GLU | B | 535 | −79.370 | −13.588 | −26.330 | 1.00 | 27.72 | O |
| ATOM | 16456 | OE2 | GLU | B | 535 | −77.762 | −14.492 | −27.549 | 1.00 | 30.06 | O |
| ATOM | 16457 | C | GLU | B | 535 | −77.355 | −16.019 | −22.056 | 1.00 | 26.19 | C |
| ATOM | 16458 | O | GLU | B | 535 | −77.021 | −17.171 | −22.279 | 1.00 | 26.15 | O |
| ATOM | 16460 | N | PRO | B | 536 | −78.186 | −15.697 | −21.047 | 1.00 | 26.05 | N |
| ATOM | 16461 | CA | PRO | B | 536 | −78.692 | −16.763 | −20.196 | 1.00 | 26.05 | C |
| ATOM | 16463 | CB | PRO | B | 536 | −79.495 | −16.018 | −19.118 | 1.00 | 25.87 | C |
| ATOM | 16466 | CG | PRO | B | 536 | −79.140 | −14.621 | −19.239 | 1.00 | 25.88 | C |
| ATOM | 16469 | CD | PRO | B | 536 | −78.760 | −14.402 | −20.660 | 1.00 | 26.21 | C |
| ATOM | 16472 | C | PRO | B | 536 | −79.608 | −17.717 | −20.943 | 1.00 | 26.14 | C |
| ATOM | 16473 | O | PRO | B | 536 | −80.173 | −17.359 | −21.973 | 1.00 | 25.99 | O |
| ATOM | 16474 | N | ILE | B | 537 | −79.746 | −18.924 | −20.411 | 1.00 | 26.38 | N |
| ATOM | 16475 | CA | ILE | B | 537 | −80.662 | −19.905 | −20.960 | 1.00 | 26.58 | C |
| ATOM | 16477 | CB | ILE | B | 537 | −80.443 | −21.292 | −20.333 | 1.00 | 26.47 | C |
| ATOM | 16479 | CG1 | ILE | B | 537 | −79.023 | −21.789 | −20.600 | 1.00 | 26.38 | C |
| ATOM | 16482 | CD1 | ILE | B | 537 | −78.709 | −23.102 | −19.907 | 1.00 | 26.40 | C |
| ATOM | 16486 | CG2 | ILE | B | 537 | −81.430 | −22.300 | −20.890 | 1.00 | 26.71 | C |
| ATOM | 16490 | C | ILE | B | 537 | −82.072 | −19.420 | −20.657 | 1.00 | 26.93 | C |
| ATOM | 16491 | O | ILE | B | 537 | −82.347 | −18.965 | −19.545 | 1.00 | 26.81 | O |
| ATOM | 16493 | N | LEU | B | 538 | −82.963 | −19.491 | −21.641 | 1.00 | 27.36 | N |
| ATOM | 16494 | CA | LEU | B | 538 | −84.309 | −18.984 | −21.439 | 1.00 | 27.68 | C |
| ATOM | 16496 | CB | LEU | B | 538 | −85.181 | −19.094 | −22.698 | 1.00 | 27.75 | C |
| ATOM | 16499 | CG | LEU | B | 538 | −84.782 | −18.291 | −23.949 | 1.00 | 27.47 | C |
| ATOM | 16501 | CD1 | LEU | B | 538 | −85.992 | −18.109 | −24.844 | 1.00 | 27.11 | C |
| ATOM | 16505 | CD2 | LEU | B | 538 | −84.164 | −16.933 | −23.621 | 1.00 | 26.99 | C |
| ATOM | 16509 | C | LEU | B | 538 | −84.919 | −19.752 | −20.288 | 1.00 | 28.01 | C |
| ATOM | 16512 | N | PRO | B | 539 | −85.645 | −19.046 | −19.421 | 1.00 | 28.69 | N |
| ATOM | 16513 | CA | PRO | B | 539 | −86.028 | −19.631 | −18.152 | 1.00 | 29.05 | C |
| ATOM | 16515 | CB | PRO | B | 539 | −86.640 | −18.452 | −17.397 | 1.00 | 29.08 | C |
| ATOM | 16518 | CG | PRO | B | 539 | −87.144 | −17.548 | −18.447 | 1.00 | 28.86 | C |
| ATOM | 16521 | CD | PRO | B | 539 | −86.298 | −17.748 | −19.660 | 1.00 | 28.62 | C |
| ATOM | 16524 | C | PRO | B | 539 | −87.035 | −20.767 | −18.259 | 1.00 | 29.51 | C |
| ATOM | 16525 | O | PRO | B | 539 | −87.665 | −20.970 | −19.297 | 1.00 | 29.23 | O |
| ATOM | 16526 | N | PHE | B | 540 | −87.164 | −21.500 | −17.159 | 1.00 | 30.25 | N |
| ATOM | 16527 | CA | PHE | B | 540 | −88.089 | −22.613 | −17.070 | 1.00 | 30.56 | C |
| ATOM | 16529 | CB | PHE | B | 540 | −87.971 | −23.297 | −15.708 | 1.00 | 30.73 | C |
| ATOM | 16532 | CG | PHE | B | 540 | −88.848 | −24.499 | −15.567 | 1.00 | 30.49 | C |
| ATOM | 16533 | CD1 | PHE | B | 540 | −89.910 | −24.505 | −14.683 | 1.00 | 30.32 | C |
| ATOM | 16535 | CE1 | PHE | B | 540 | −90.718 | −25.614 | −14.568 | 1.00 | 30.59 | C |
| ATOM | 16537 | CZ | PHE | B | 540 | −90.475 | −26.722 | −15.346 | 1.00 | 30.55 | C |
| ATOM | 16539 | CE2 | PHE | B | 540 | −89.420 | −26.720 | −16.234 | 1.00 | 30.68 | C |
| ATOM | 16541 | CD2 | PHE | B | 540 | −88.619 | −25.617 | −16.342 | 1.00 | 30.43 | C |

TABLE 3-7-continued

Coordinates of *P. tremuloides* IspS

| | | | | | | | | | | | |
|---|---|---|---|---|---|---|---|---|---|---|---|
| ATOM | 16543 | C | PHE | B | 540 | −89.507 | −22.120 | −17.257 | 1.00 | 30.76 | C |
| ATOM | 16544 | O | PHE | B | 540 | −89.967 | −21.257 | −16.508 | 1.00 | 30.59 | O |
| ATOM | 16546 | N | GLU | B | 541 | −90.184 | −22.677 | −18.259 | 1.00 | 31.13 | N |
| ATOM | 16547 | CA | GLU | B | 541 | −91.553 | −22.289 | −18.608 | 1.00 | 31.45 | C |
| ATOM | 16549 | CB | GLU | B | 541 | −91.525 | −21.186 | −19.680 | 1.00 | 31.60 | C |
| ATOM | 16552 | CG | GLU | B | 541 | −92.860 | −20.454 | −19.911 | 1.00 | 32.56 | C |
| ATOM | 16555 | CD | GLU | B | 541 | −93.773 | −21.133 | −20.935 | 1.00 | 33.64 | C |
| ATOM | 16556 | OE1 | GLU | B | 541 | −93.261 | −21.922 | −21.771 | 1.00 | 35.06 | O |
| ATOM | 16557 | OE2 | GLU | B | 541 | −95.002 | −20.868 | −20.901 | 1.00 | 32.44 | O |
| ATOM | 16558 | C | GLU | B | 541 | −92.326 | −23.510 | −19.105 | 1.00 | 31.31 | C |
| ATOM | 16559 | O | GLU | B | 541 | −92.860 | −24.286 | −18.310 | 1.00 | 31.30 | O |
| ATOM | 16562 | MG | MG | C | 1 | −42.844 | 11.427 | 13.309 | 1.00 | 46.29 | MG |
| ATOM | 16561 | MG | MG | C | 2 | −46.615 | −18.454 | −33.231 | 1.00 | 48.45 | MG |
| ATOM | 16563 | O | HOH | E | 1 | −50.507 | −5.408 | −4.491 | 1.00 | 17.42 | O |
| ATOM | 16566 | O | HOH | E | 2 | −64.748 | −36.007 | −11.725 | 1.00 | 2.00 | O |
| ATOM | 16569 | O | HOH | E | 3 | −40.643 | −2.220 | −34.996 | 1.00 | 2.00 | O |
| ATOM | 16572 | O | HOH | E | 4 | −36.090 | −9.757 | −37.074 | 1.00 | 17.20 | O |
| ATOM | 16575 | O | HOH | E | 5 | −46.117 | −37.662 | −22.916 | 1.00 | 17.03 | O |
| ATOM | 16578 | O | HOH | E | 6 | −49.541 | 35.476 | 6.921 | 1.00 | 14.03 | O |
| ATOM | 16581 | O | HOH | E | 7 | −32.288 | 27.572 | 16.443 | 1.00 | 13.16 | O |
| ATOM | 16584 | O | HOH | E | 8 | −50.706 | 10.207 | −15.061 | 1.00 | 18.73 | O |
| ATOM | 16587 | O | HOH | E | 9 | −77.188 | 36.767 | −9.218 | 1.00 | 8.05 | O |
| ATOM | 16590 | O | HOH | E | 10 | −90.260 | −31.248 | −21.071 | 1.00 | 2.00 | O |
| ATOM | 16593 | O | HOH | E | 11 | −70.920 | −33.414 | −3.884 | 1.00 | 9.35 | O |
| ATOM | 16596 | O | HOH | E | 12 | −37.761 | −21.294 | −9.249 | 1.00 | 25.78 | O |
| ATOM | 16599 | O | HOH | E | 13 | −76.050 | 23.855 | −18.293 | 1.00 | 2.00 | O |
| ATOM | 16602 | O | HOH | E | 14 | −76.876 | −19.575 | −22.856 | 1.00 | 19.25 | O |
| ATOM | 16605 | O | HOH | E | 15 | −40.936 | 11.629 | −24.832 | 1.00 | 22.29 | O |
| ATOM | 16608 | O | HOH | E | 16 | −85.551 | 34.832 | 3.260 | 1.00 | 25.14 | O |
| ATOM | 16611 | O | HOH | E | 17 | −56.825 | 31.771 | −7.464 | 1.00 | 17.27 | O |
| ATOM | 16614 | O | HOH | E | 18 | −76.222 | 39.261 | −.613 | 1.00 | 25.47 | O |

Example 4

Three-Dimensional Structure of *P. alba* IspS

I. Expression of 6xHis-Tagged IspS

N-terminally 6xHis-tagged IspS was expressed and purified from strain MD09-167. Construction of MD09-167 is described in Example 2. The growth procedure is suitable for histidine tagged enzymes expressed in BL21(λDE3)pLysS cells. A 10 ml of overnight culture was prepared for each 1 L of planned growth. The appropriate antibiotics (50 mg/ml kanamycin, 50 mg/ml chloramphenicol, and/or 50 mg/ml Carbenecillin) was added to 10 ml of LB medium in a 25 ml flask and was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1L day culture was inoculated with 10 ml of overnight culture and grown at 30-37° C. with shaking at ~220 rpm until the $OD_{600}$ reached ~0.4-0.6. Day cultures were then induced with 400 μM IPTG and allowed to continue growing at 30° C. with shaking at 220 rpm for ~5-6 hours. Cells were then harvested by centrifugation at 10,000xg for 10 min, 4° C. Following Harvest, cells were used directly or stored at −80° C. until ready to process II. Purification of 6xHis-Tagged IspS For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 40-50 ml of lysis buffer was used per 1L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 μl). The lysate was then clarified by centrifuging the lysate at 30,000xg for 30 min, 4° C. in a Sorvall Discovery 90SE ultracentrifuge. The supernatant was removed and retained. A sample of the "clarified lysate" was saved for activity assay and gel analysis (~100 μl).

The clarified lysate was run over HisTrap HP columns (GE healthcare) using a gradient from 0-100% Ni buffer B. Following loading of the lysate on the column, the column was washed with Ni wash buffer (50 mM $NaH_2PO_4$, 300 mm NaCl, 20 mM imidazole, ph 8.0). The his-tagged IspS was then eluted from the column using a gradient from 0-100% Ni elution buffer (50 mM $NaH_2PO_4$, 300 mM NaCl, 500 mM imidazole, ph 8.0) and fractions containing the his-tagged IspS were collected. The column was then washed with Ni stripping buffer (20 mM $NaH_2PO_4$, 0.5 m NaCl, 50 mM EDTA, ph 7.4). Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a Hi Prep 26/10 Desalting column (GE healthcare) packed with Sephadex G25 resin. The G-25 buffer consisted of 50 mM HEPES, 50 mM NaCl, and 1 mM DTT, pH 7.4. The desired sample was then chromatographed on Hi Trap Q HP column (GE) (Q seph buffer A was 50 mM Tris, 0.05 M NaCl, 1 mM DTT, pH 7.6. Q seph buffer B was 50 mM Tris, 1.0 M NaCl, 1 mM DTT, pH 7.6) and concentrated if necessary. Sample buffer was then exchanged by passing sample over a Hi Prep 26/10 Desalting column (GE healthcare) packed with Sephadex G25 resin. A final polishing step of Gel filtration is used as necessary. Pass the sample over a Hi Load 26/60 Superdex 200 prep grade (GE) in gel filtration buffer: (50 mM HEPES, 150 mM NaCl, 1 mM DTT, pH 7.4). Fractions were then analyzed and concentrated. The samples were then stored at −80° C.

TEV Cleavage (IspS from Strains MD09-165 and MD09-167)

For digestion, enzymes were purified through a Ni charged sepharose (GE Healthcare) and desalted into 50 mM HEPES, 50 mM NaCl pH 7.4 buffer containing 1 mM DTT. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (which is also tagged), and impurities. The Ni column pass though and washes were analyzed using SDS-PAGE gel (NUPAGE, Invitrogen) and DMAPP activity assays. Samples containing pure enzyme were pooled and desalted into 50 mM NaCl pH 7.4 buffer containing 1 mM DTT and stored at −80° C.

III. Crystal Structure Determination

The enzyme expressed from MD09-167 was purified and a concentrated protein solution was then prepared for surveying possible crystallization conditions. The protein was purified independently and surveyed as described below. All in-house crystallization screens were set up using the hanging drop vapor diffusion method. At a minimum, the protein was surveyed using the following commercial screens: the Crystal Screen from Hampton Research (Aliso Viejo, Calif.) and the JCSG+ Suite from Qiagen (Valencia, Calif.).

A truncated *P. alba* IspS construct featuring two additional residues before the twin-arginine motif was generated (MD09-167). This construct contains a C-terminal histidine-tag, and crystallization experiments were set up with the tag either cleaved or not cleaved, at varying protein concentrations, and with or without sodium pyrophosphate. Initial crystallization screens were setup using the Crystal Screen from Hampton Research and the JCSG+ Suite from Qiagen. Crystals of protein derived from MD09-167 were observed in numerous conditions; optimization included 528 variations of pH, precipitating agents, concentrations, and inhibitors. From the optimization experiments, twenty different MD09-167 crystals were screened in-house for diffraction. In an effort to improve the resolution, various crystal freezing conditions were tested, with the effect of improving the diffraction limits from 10 Å to 6.5 Å. Upon further optimization of both crystallization and freezing conditions, a crystal composed of non-cleaved histidine-tagged protein was obtained that diffracted to 2.7 Å in house. The large, rod-shaped crystals belong to the tetragonal space group $P4_32_12$, and have unit cell dimensions a=156.8, b=156.8, c=142.5. The crystals were grown by mixing 2 μL of protein (9 mg/ml protein) with 2 μL of precipitant solution (0.2 M NaMalonate, pH 7.0 and 18% (wt/vol) polyethylene glycol 3350) and equilibrated against 500 μL of precipitant. Prior to flash-freezing the crystal in liquid nitrogen, the crystals were cryoprotected by swishing through 0.2 M NaMalonate, pH 7.0, 18% (wt/vol) polyethylene glycol 3350, and 25% (wt/vol) ethylene glycol.

An identical crystal was prepared and sent to Stanford Synchrotron Radiation Laboratory, and data were collected at Beamline 11-1. Data were integrated using Mosflm (Leslie, A. (1998) J. of Appl. Crystallography 30, 1036-1040) and scaled using SCALA (Collaborative Computational Project, N. (1994) Acta Crystallographica Section D 50, 760-763). The data were phased with MOLREP (Vagin, A., and Teplyakov, A. (1997) J. of Appl. Crystallography 30, 1022-1025), using the IspS from *P. tremuloides* (Example 3) as the starting model. The crystal contains one dimer in the asymmetric unit with a solvent content of 64%. Data collection and refinement statistics are given in Table 4-1.

Refinement with Refmac5 (Collaborative Computational Project, N. (1994) Acta Crystallographica Section D 50, 760-763) was used with iterative manual rebuilding steps using the visualization program Coot (Emsley, P., and Cowtan, K. (2004) Acta Crystallographica Section D 60, 2126-2132). During refinement, the geometry of the protein was checked using Molprobity (Davis, I. W., et al. (2007) Nucl. Acids Res., 35:W375-W383). The coordinates are provided in Table 4-2.

TABLE 4-1

Data Collection and Refinement Statistics

| Data Collection | |
| --- | --- |
| Space Group | $P4_32_12$ |
| Cell dimensions | |
| A, b, c (Å) | 156.8, 156.8, 142.5 |
| α, β, γ, (°) | 90.0, 90.0, 90.0 |
| Resolution (Å) | 45.5-2.30 |
| $R_{merge}$ | 8.2 (60.6)[a] |
| <I/σI> | 10.0 (2.2) |
| Completeness (%) | 99.1 (96.2) |
| Redundancy | 4.7 (4.3) |
| Refinement | |
| Resolution (Å) | 38.0-2.30 |
| No. measured reflections | 366320 |
| No. Unique reflections | 74242 |
| $R_{work}$ | 20.7 |
| $R_{free}$ | 24.2 |
| rmsd bonds, (Å) | 0.012 |
| rmsd angles, (°) | 1.206 |
| No. of Atoms | |
| Protein | 8689 |
| Water | 205 |

[a]Values in parenthesis refer to highest resolution shell.

TABLE 4-2

Coordinates of *P. alba* IspS

```
HEADER    --- XX-XXX-9-  xxxx
COMPND    ---
REMARK  3
REMARK  3   REFINEMENT.
REMARK  3    PROGRAM:    REFMAC 5.5.0088
REMARK  3    AUTHORS:  MURSHUDOV, VAGIN, DODSON
REMARK  3
REMARK  3    REFINEMENT TARGET: MAXIMUM LIKELIHOOD
REMARK  3
REMARK  3   DATA USED IN REFINEMENT.
REMARK  3    RESOLUTION RANGE HIGH (ANGSTROMS):  2.30
REMARK  3    RESOLUTION RANGE LOW  (ANGSTROMS):   43.66
REMARK  3    DATA CUTOFF  (SIGMA(F)): NONE
REMARK  3    COMPLETENESS FOR RANGE    (%): 98.90
```

TABLE 4-2-continued

Coordinates of *P. alba* IspS

| | |
|---|---|
| REMARK 3 | NUMBER OF REFLECTIONS: 74242 |
| REMARK 3 | |
| REMARK 3 | FIT TO DATA USED IN REFINEMENT. |
| REMARK 3 | CROSS-VALIDATION METHOD: THROUGHOUT |
| REMARK 3 | FREE R VALUE TEST SET SELECTION: RANDOM  p |
| REMARK 3 | R VALUE  (WORKING + TEST SET): 0.20949 |
| REMARK 3 | R VALUE  (WORKING SET): 0.20777 |
| REMARK 3 | FREE R VALUE: 0.24192 |
| REMARK 3 | FREE R VALUE TEST SET SIZE (%): 5.1 |
| REMARK 3 | FREE R VALUE TEST SET COUNT: 3968 |
| REMARK 3 | |
| REMARK 3 | FIT IN THE HIGHEST RESOLUTION BIN. |
| REMARK 3 | TOTAL NUMBER OF BINS USED: 20 |
| REMARK 3 | BIN RESOLUTION RANGE HIGH: 2.300 |
| REMARK 3 | BIN RESOLUTION RANGE LOW: 2.360 |
| REMARK 3 | REFLECTION IN BIN  (WORKING SET): 5205 |
| REMARK 3 | BIN COMPLETENESS (WORKING + TEST) (%): 95.11 |
| REMARK 3 | BIN R VALUE  (WORKING SET): 0.350 |
| REMARK 3 | BIN FREE R VALUE SET COUNT: 257 |
| REMARK 3 | BIN FREE R VALUE: 0.364 |
| REMARK 3 | |
| REMARK 3 | NUMBER OF NON-HYDROGEN ATOMS USED IN REFINEMENT. |
| REMARK 3 | ALL ATOMS: 8894 |
| REMARK 3 | |
| REMARK 3 | B VALUES. |
| REMARK 3 | FROM WILSON PLOT  (A**2): NULL |
| REMARK 3 | MEAN B VALUE  (OVERALL, A**2): 28.532 |
| REMARK 3 | OVERALL ANISOTROPIC B VALUE. |
| REMARK 3 |   B11 (A**2): 0.19 |
| REMARK 3 |   B22 (A**2): 0.19 |
| REMARK 3 |   B33 (A**2): −0.39 |
| REMARK 3 |   B12 (A**2): −0.00 |
| REMARK 3 |   B13 (A**2): −0.00 |
| REMARK 3 |   B23 (A**2): 0.00 |
| REMARK 3 | |
| REMARK 3 | ESTIMATED OVERALL COORDINATE ERROR. |
| REMARK 3 | ESU BASED ON R VALUE  (A): 0.234 |
| REMARK 3 | ESU BASED ON FREE R VALUE  (A): 0.197 |
| REMARK 3 | ESU BASED ON MAXIMUM LIKELIHOOD    (A): 0.132 |
| REMARK 3 | ESU FOR B VALUES BASED ON MAXIMUM LIKELIHOOD (A**2): 12.016 |
| REMARK 3 | |
| REMARK 3 | CORRELATION COEFFICIENTS. |
| REMARK 3 | CORRELATION COEFFICIENT FO-FC: 0.949 |
| REMARK 3 | CORRELATION COEFFICIENT FO-FC FREE: 0.932 |
| REMARK 3 | |
| REMARK 3 | RMS DEVIATIONS FROM IDEAL VALUES   COUNT  RMS  WEIGHT |
| REMARK 3 | BOND LENGTHS REFINED ATOMS    (A): 8874; 0.012; 0.022 |
| REMARK 3 | BOND LENGTHS OTHERS    (A): 6064; 0.001; 0.020 |
| REMARK 3 | BOND ANGLES REFINED ATOMS (DEGREES): 12007; 1.206; 1.952 |
| REMARK 3 | BOND ANGLES OTHERS  (DEGREES): 14720; 0.851; 3.000 |
| REMARK 3 | TORSION ANGLES, PERIOD 1  (DEGREES): 1070; 5.228; 5.000 |
| REMARK 3 | TORSION ANGLES, PERIOD 2 (DEGREES): 460; 35.290; 24.304 |
| REMARK 3 | TORSION ANGLES, PERIOD 3 (DEGREES): 1582; 14.921; 15.000 |
| REMARK 3 | TORSION ANGLES, PERIOD 4 (DEGREES): 61; 16.584; 15.000 |
| REMARK 3 | CHIRAL-CENTER RESTRAINTS  (A**3): 1314; 0.072; 0.200 |
| REMARK 3 | GENERAL PLANES REFINED ATOMS    (A): 9879; 0.005; 0.020 |
| REMARK 3 | GENERAL PLANES OTHERS  (A): 1878; 0.001; 0.020 |
| REMARK 3 | |
| REMARK 3 | ISOTROPIC THERMAL FACTOR RESTRAINTS.  COUNT  RMS  WEIGHT |
| REMARK 3 | MAIN-CHAIN BOND REFINED ATOMS  (A**2): 5310; 1.592; 3.000 |
| REMARK 3 | MAIN-CHAIN BOND OTHER ATOMS    (A**2): 2148; 0.457; 3.000 |
| REMARK 3 | MAIN-CHAIN ANGLE REFINED ATOMS  (A**2): 8546; 3.009; 5.000 |
| REMARK 3 | SIDE-CHAIN BOND REFINED ATOMS  (A**2): 3564; 4.694; 8.000 |
| REMARK 3 | SIDE-CHAIN ANGLE REFINED ATOMS  (A**2): 3455; 7.036; 11.000 |
| REMARK 3 | |
| REMARK 3 | NCS RESTRAINTS STATISTICS |
| REMARK 3 | NUMBER OF DIFFERENT NCS GROUPS: 1 |
| REMARK 3 | |
| REMARK 3 | NCS GROUP NUMBER:   1 |
| REMARK 3 |  CHAIN NAMES:  A B |
| REMARK 3 |  NUMBER OF COMPONENTS NCS GROUP: 1 |
| REMARK 3 |  COMPONENT C  SSSEQI   TO   C   SSSEQI CODE |
| REMARK 3 |   1 A   1 A 560   4 |
| REMARK 3 |   1  B 1   B 560   4 |
| REMARK 3 |    GROUP   CHAIN  COUNT  RMS   WEIGHT |
| REMARK 3 | MEDIUM POSITIONAL  1  1  (A): 7275; 0.30; 0.50 |

TABLE 4-2-continued

Coordinates of *P. alba* IspS

| | | | | | | | | | | | |
|---|---|---|---|---|---|---|---|---|---|---|---|
| REMARK | 3 | MEDIUM THERMAL   1  1  (A**2):  7275; 0.78; 2.00 | | | | | | | | | |
| REMARK | 3 | | | | | | | | | | |
| REMARK | 3 | TWIN DETAILS | | | | | | | | | |
| REMARK | 3 | NUMBER OF TWIN DOMAINS: NULL | | | | | | | | | |
| REMARK | 3 | | | | | | | | | | |
| REMARK | 3 | | | | | | | | | | |
| REMARK | 3 | TLS DETAILS | | | | | | | | | |
| REMARK | 3 | NUMBER OF TLS GROUPS:  2 | | | | | | | | | |
| REMARK | 3 | ATOM RECORD CONTAINS RESIDUAL B FACTORS ONLY | | | | | | | | | |
| REMARK | 3 | | | | | | | | | | |
| REMARK | 3 | TLS GROUP:  1 | | | | | | | | | |
| REMARK | 3 |  NUMBER OF COMPONENTS GROUP:  1 | | | | | | | | | |
| REMARK | 3 |  COMPONENTS    C SSSEQI TO C SSSEQI | | | | | | | | | |
| REMARK | 3 |  RESIDUE RANGE: A   -10 A 9999 | | | | | | | | | |
| REMARK | 3 |  ORIGIN FOR THE GROUP (A):   55.1340 -22.7990  1.5640 | | | | | | | | | |
| REMARK | 3 |  T TENSOR | | | | | | | | | |
| REMARK | 3 |   T11:  0.1012 T22:  0.0842 | | | | | | | | | |
| REMARK | 3 |   T33:  0.0487 T12:  -0.0797 | | | | | | | | | |
| REMARK | 3 |   T13:  -0.0129 T23:  -0.0050 | | | | | | | | | |
| REMARK | 3 |  L TENSOR | | | | | | | | | |
| REMARK | 3 |   L11:  0.4547 L22:  1.7223 | | | | | | | | | |
| REMARK | 3 |   L33:  0.4716 L12:  -0.3910 | | | | | | | | | |
| REMARK | 3 |   L13:  0.0096 L23:  0.1512 | | | | | | | | | |
| REMARK | 3 |  S TENSOR | | | | | | | | | |
| REMARK | 3 |   S11:  0.0834 S12:  -0.1118 S13:  0.0428 | | | | | | | | | |
| REMARK | 3 |   S21:  -0.0018 S22:  -0.0458 S23:  -0.0748 | | | | | | | | | |
| REMARK | 3 |   S31:  -0.0352 S32:  0.0105 S33:  -0.0376 | | | | | | | | | |
| REMARK | 3 | | | | | | | | | | |
| REMARK | 3 | TLS GROUP:  2 | | | | | | | | | |
| REMARK | 3 |  NUMBER OF COMPONENTS GROUP: 1 | | | | | | | | | |
| REMARK | 3 |  COMPONENTS    C SSSEQI  TO C SSSEQI | | | | | | | | | |
| REMARK | 3 |  RESIDUE RANGE: B  -10 B  9999 | | | | | | | | | |
| REMARK | 3 |  ORIGIN FOR THE GROUP (A): 61.5680 28.1500 -20.5740 | | | | | | | | | |
| REMARK | 3 |  T TENSOR | | | | | | | | | |
| REMARK | 3 |   T11:  0.1284 T22:  0.1262 | | | | | | | | | |
| REMARK | 3 |   T33:  0.1080 T12:  0.0397 | | | | | | | | | |
| REMARK | 3 |   T13:  -0.0366 T23:  0.0120 | | | | | | | | | |
| REMARK | 3 |  L TENSOR | | | | | | | | | |
| REMARK | 3 |   L11:  1.1443 L22:  0.6715 | | | | | | | | | |
| REMARK | 3 |   L33:  0.8680 L12:  0.4490 | | | | | | | | | |
| REMARK | 3 |   L13:  0.6089 L23:  0.2346 | | | | | | | | | |
| REMARK | 3 |  S TENSOR | | | | | | | | | |
| REMARK | 3 |   S11:  0.0652 S12:  0.1638 S13:  0.0430 | | | | | | | | | |
| REMARK | 3 |   S21:  0.0628 S22:  -0.0956 S23:  -0.0492 | | | | | | | | | |
| REMARK | 3 |   S31:  -0.0269 S32:  0.2044 S33:  0.0305 | | | | | | | | | |
| REMARK | 3 | | | | | | | | | | |
| REMARK | 3 | | | | | | | | | | |
| REMARK | 3 |  BULK SOLVENT MODELLING. | | | | | | | | | |
| REMARK | 3 |  METHOD USED: MASK | | | | | | | | | |
| REMARK | 3 |  PARAMETERS FOR MASK CALCULATION | | | | | | | | | |
| REMARK | 3 |  VDW PROBE RADIUS:  1.40 | | | | | | | | | |
| REMARK | 3 |  ION PROBE RADIUS:  0.80 | | | | | | | | | |
| REMARK | 3 |  SHRINKAGE RADIUS:  0.80 | | | | | | | | | |
| REMARK | 3 | | | | | | | | | | |
| REMARK | 3 |  OTHER REFINEMENT REMARKS: | | | | | | | | | |
| REMARK | 3 |  HYDROGENS HAVE BEEN ADDED IN THE RIDING POSITIONS | | | | | | | | | |
| REMARK | 3 |  U VALUES:  RESIDUAL ONLY | | | | | | | | | |
| REMARK | 3 | | | | | | | | | | |
| REMARK | 3 |  OTHER REFINEMENT REMARKS:   1. RESIDUES A39, A539, A541 ARE | | | | | | | | | |
| REMARK | 3 |  RAMACHANDRAN OUTLIERS AND ARE LOCATED IN POOR DENSITY. | | | | | | | | | |
| LINKR | | ASN A 512  THR A 517   gap | | | | | | | | | |
| LINKR | | SER B 18  ILE B 24   gap | | | | | | | | | |
| LINKR | | ASN B 512  THR B 517   gap | | | | | | | | | |
| CRYST1 | | 156.800 156.800 142.480 90.00 90.00 90.00 P 43 21 2 | | | | | | | | | |
| SCALE1 | | 0.006378 0.000000 0.000000  0.00000 | | | | | | | | | |
| SCALE2 | | -0.000000 0.006378 0.000000  0.00000 | | | | | | | | | |
| SCALE3 | | 0.000000 -0.000000 0.007019  0.00000 | | | | | | | | | |
| ATOM | 1 | N | ALA | A | 23 | 59.766 | -33.590 | -29.936 | 1.00 | 64.60 | A N |
| ATOM | 2 | CA | ALA | A | 23 | 60.006 | -32.892 | -28.637 | 1.00 | 65.14 | A C |
| ATOM | 4 | CB | ALA | A | 23 | 60.361 | -33.912 | -27.536 | 1.00 | 65.26 | A C |
| ATOM | 8 | C | ALA | A | 23 | 61.108 | -31.833 | -28.796 | 1.00 | 64.48 | A C |
| ATOM | 9 | O | ALA | A | 23 | 62.101 | -32.081 | -29.489 | 1.00 | 64.58 | A O |
| ATOM | 13 | N | ASN | A | 24 | 60.937 | -30.692 | -28.111 | 1.00 | 63.60 | A N |
| ATOM | 14 | CA | ASN | A | 24 | 61.661 | -29.425 | -28.393 | 1.00 | 63.75 | A C |
| ATOM | 16 | CB | ASN | A | 24 | 60.620 | -28.275 | -28.535 | 1.00 | 65.26 | A C |

TABLE 4-2-continued

Coordinates of *P. alba* IspS

| ATOM | 19 | CG | ASN | A | 24 | 61.091 | −27.095 | −29.448 | 1.00 | 66.51 | A | C |
| ATOM | 20 | OD1 | ASN | A | 24 | 62.282 | −26.926 | −29.744 | 1.00 | 66.15 | A | O |
| ATOM | 21 | ND2 | ASN | A | 24 | 60.132 | −26.265 | −29.865 | 1.00 | 65.85 | A | N |
| ATOM | 24 | C | ASN | A | 24 | 62.780 | −29.018 | −27.379 | 1.00 | 61.71 | A | C |
| ATOM | 25 | O | ASN | A | 24 | 62.970 | −29.635 | −26.325 | 1.00 | 60.31 | A | O |
| ATOM | 27 | N | TYR | A | 25 | 63.472 | −27.935 | −27.748 | 1.00 | 59.76 | A | N |
| ATOM | 28 | CA | TYR | A | 25 | 64.743 | −27.478 | −27.188 | 1.00 | 57.41 | A | C |
| ATOM | 30 | CB | TYR | A | 25 | 65.795 | −27.490 | −28.311 | 1.00 | 56.05 | A | C |
| ATOM | 33 | CG | TYR | A | 25 | 65.932 | −28.808 | −29.027 | 1.00 | 47.11 | A | C |
| ATOM | 34 | CD1 | TYR | A | 25 | 66.574 | −29.878 | −28.415 | 1.00 | 37.57 | A | C |
| ATOM | 36 | CE1 | TYR | A | 25 | 66.711 | −31.092 | −29.059 | 1.00 | 36.77 | A | C |
| ATOM | 38 | CZ | TYR | A | 25 | 66.203 | −31.268 | −30.344 | 1.00 | 28.44 | A | C |
| ATOM | 39 | OH | TYR | A | 25 | 66.356 | −32.509 | −30.967 | 1.00 | 27.40 | A | O |
| ATOM | 41 | CE2 | TYR | A | 25 | 65.558 | −30.217 | −30.979 | 1.00 | 25.06 | A | C |
| ATOM | 43 | CD2 | TYR | A | 25 | 65.426 | −28.988 | −30.317 | 1.00 | 37.00 | A | C |
| ATOM | 45 | C | TYR | A | 25 | 64.687 | −26.036 | −26.661 | 1.00 | 57.89 | A | C |
| ATOM | 46 | O | TYR | A | 25 | 65.729 | −25.384 | −26.543 | 1.00 | 56.82 | A | O |
| ATOM | 48 | N | GLU | A | 26 | 63.490 | −25.529 | −26.363 | 1.00 | 59.48 | A | N |
| ATOM | 49 | CA | GLU | A | 26 | 63.341 | −24.135 | −25.907 | 1.00 | 60.53 | A | C |
| ATOM | 51 | CB | GLU | A | 26 | 61.868 | −23.677 | −25.947 | 1.00 | 61.98 | A | C |
| ATOM | 54 | CG | GLU | A | 26 | 61.348 | −23.344 | −27.364 | 1.00 | 67.81 | A | C |
| ATOM | 57 | CD | GLU | A | 26 | 61.904 | −22.027 | −27.939 | 1.00 | 76.35 | A | C |
| ATOM | 58 | OE1 | GLU | A | 26 | 61.559 | −20.940 | −27.414 | 1.00 | 79.99 | A | O |
| ATOM | 59 | OE2 | GLU | A | 26 | 62.671 | −22.083 | −28.931 | 1.00 | 78.41 | A | O |
| ATOM | 60 | C | GLU | A | 26 | 63.936 | −23.968 | −24.504 | 1.00 | 57.46 | A | C |
| ATOM | 61 | O | GLU | A | 26 | 63.895 | −24.895 | −23.710 | 1.00 | 55.07 | A | O |
| ATOM | 63 | N | PRO | A | 27 | 64.507 | −22.787 | −24.210 | 1.00 | 56.78 | A | N |
| ATOM | 64 | CA | PRO | A | 27 | 65.154 | −22.598 | −22.915 | 1.00 | 56.84 | A | C |
| ATOM | 66 | CB | PRO | A | 27 | 65.814 | −21.217 | −23.045 | 1.00 | 57.69 | A | C |
| ATOM | 69 | CG | PRO | A | 27 | 65.016 | −20.504 | −24.075 | 1.00 | 58.63 | A | C |
| ATOM | 72 | CD | PRO | A | 27 | 64.502 | −21.552 | −25.017 | 1.00 | 57.02 | A | C |
| ATOM | 75 | C | PRO | A | 27 | 64.169 | −22.625 | −21.736 | 1.00 | 55.20 | A | C |
| ATOM | 76 | O | PRO | A | 27 | 62.977 | −22.370 | −21.913 | 1.00 | 54.56 | A | O |
| ATOM | 77 | N | ASN | A | 28 | 64.673 | −22.977 | −20.560 | 1.00 | 53.26 | A | N |
| ATOM | 78 | CA | ASN | A | 28 | 63.936 | −22.792 | −19.328 | 1.00 | 53.80 | A | C |
| ATOM | 80 | CB | ASN | A | 28 | 64.226 | −23.922 | −18.345 | 1.00 | 55.37 | A | C |
| ATOM | 83 | CG | ASN | A | 28 | 63.955 | −25.285 | −18.938 | 1.00 | 57.15 | A | C |
| ATOM | 84 | OD1 | ASN | A | 28 | 62.803 | −25.708 | −19.041 | 1.00 | 59.44 | A | O |
| ATOM | 85 | ND2 | ASN | A | 28 | 65.019 | −25.984 | −19.329 | 1.00 | 56.57 | A | N |
| ATOM | 88 | C | ASN | A | 28 | 64.302 | −21.453 | −18.702 | 1.00 | 52.53 | A | C |
| ATOM | 89 | O | ASN | A | 28 | 65.445 | −20.999 | −18.790 | 1.00 | 51.17 | A | O |
| ATOM | 91 | N | SER | A | 29 | 63.318 | −20.836 | −18.057 | 1.00 | 52.53 | A | N |
| ATOM | 92 | CA | SER | A | 29 | 63.497 | −19.563 | −17.340 | 1.00 | 52.63 | A | C |
| ATOM | 94 | CB | SER | A | 29 | 62.153 | −19.136 | −16.735 | 1.00 | 53.29 | A | C |
| ATOM | 97 | OG | SER | A | 29 | 61.572 | −20.222 | −16.014 | 1.00 | 52.43 | A | O |
| ATOM | 99 | C | SER | A | 29 | 64.545 | −19.616 | −16.215 | 1.00 | 51.47 | A | C |
| ATOM | 100 | O | SER | A | 29 | 64.999 | −18.576 | −15.746 | 1.00 | 51.59 | A | O |
| ATOM | 102 | N | TRP | A | 30 | 64.891 | −20.826 | −15.774 | 1.00 | 50.43 | A | N |
| ATOM | 103 | CA | TRP | A | 30 | 65.901 | −21.041 | −14.731 | 1.00 | 50.20 | A | C |
| ATOM | 105 | CB | TRP | A | 30 | 65.343 | −21.978 | −13.637 | 1.00 | 50.36 | A | C |
| ATOM | 108 | CG | TRP | A | 30 | 64.573 | −23.177 | −14.155 | 1.00 | 51.86 | A | C |
| ATOM | 109 | CD1 | TRP | A | 30 | 63.214 | −23.313 | −14.211 | 1.00 | 56.08 | A | C |
| ATOM | 111 | NE1 | TRP | A | 30 | 62.880 | −24.533 | −14.750 | 1.00 | 60.74 | A | N |
| ATOM | 113 | CE2 | TRP | A | 30 | 64.029 | −25.215 | −15.051 | 1.00 | 54.80 | A | C |
| ATOM | 114 | CD2 | TRP | A | 30 | 65.119 | −24.392 | −14.688 | 1.00 | 51.20 | A | C |
| ATOM | 115 | CE3 | TRP | A | 30 | 66.419 | −24.862 | −14.894 | 1.00 | 57.41 | A | C |
| ATOM | 117 | CZ3 | TRP | A | 30 | 66.591 | −26.131 | −15.460 | 1.00 | 60.80 | A | C |
| ATOM | 119 | CH2 | TRP | A | 30 | 65.483 | −26.925 | −15.807 | 1.00 | 61.30 | A | C |
| ATOM | 121 | CZ2 | TRP | A | 30 | 64.199 | −26.484 | −15.611 | 1.00 | 60.79 | A | C |
| ATOM | 123 | C | TRP | A | 30 | 67.266 | −21.562 | −15.250 | 1.00 | 49.62 | A | C |
| ATOM | 124 | O | TRP | A | 30 | 68.187 | −21.761 | −14.454 | 1.00 | 48.73 | A | O |
| ATOM | 126 | N | ASP | A | 31 | 67.411 | −21.778 | −16.561 | 1.00 | 49.12 | A | N |
| ATOM | 127 | CA | ASP | A | 31 | 68.692 | −22.273 | −17.113 | 1.00 | 48.38 | A | C |
| ATOM | 129 | CB | ASP | A | 31 | 68.649 | −22.407 | −18.638 | 1.00 | 48.56 | A | C |
| ATOM | 132 | CG | ASP | A | 31 | 67.723 | −23.505 | −19.108 | 1.00 | 47.65 | A | C |
| ATOM | 133 | OD1 | ASP | A | 31 | 67.602 | −24.547 | −18.429 | 1.00 | 50.40 | A | O |
| ATOM | 134 | OD2 | ASP | A | 31 | 67.117 | −23.313 | −20.175 | 1.00 | 49.25 | A | O |
| ATOM | 135 | C | ASP | A | 31 | 69.801 | −21.307 | −16.760 | 1.00 | 47.85 | A | C |
| ATOM | 136 | O | ASP | A | 31 | 69.563 | −20.102 | −16.691 | 1.00 | 47.37 | A | O |
| ATOM | 138 | N | TYR | A | 32 | 71.010 | −21.821 | −16.546 | 1.00 | 46.83 | A | N |
| ATOM | 139 | CA | TYR | A | 32 | 72.126 | −20.945 | −16.201 | 1.00 | 47.06 | A | C |
| ATOM | 141 | CB | TYR | A | 32 | 73.335 | −21.742 | −15.707 | 1.00 | 44.99 | A | C |
| ATOM | 144 | CG | TYR | A | 32 | 73.105 | −22.461 | −14.388 | 1.00 | 41.43 | A | C |
| ATOM | 145 | CD1 | TYR | A | 32 | 72.786 | −21.755 | −13.213 | 1.00 | 36.43 | A | C |
| ATOM | 147 | CE1 | TYR | A | 32 | 72.587 | −22.428 | −12.008 | 1.00 | 26.59 | A | C |
| ATOM | 149 | CZ | TYR | A | 32 | 72.708 | −23.786 | −11.980 | 1.00 | 28.34 | A | C |
| ATOM | 150 | OH | TYR | A | 32 | 72.521 | −24.456 | −10.829 | 1.00 | 27.28 | A | O |
| ATOM | 152 | CE2 | TYR | A | 32 | 73.043 | −24.506 | −13.113 | 1.00 | 33.62 | A | C |

TABLE 4-2-continued

Coordinates of *P. alba* IspS

| ATOM | 154 | CD2 | TYR | A | 32 | 73.241 | −23.843 | −14.302 | 1.00 | 36.99 | A | C |
|------|-----|-----|-----|---|----|--------|---------|---------|------|-------|---|---|
| ATOM | 156 | C | TYR | A | 32 | 72.520 | −19.999 | −17.343 | 1.00 | 49.23 | A | C |
| ATOM | 157 | O | TYR | A | 32 | 73.087 | −18.945 | −17.081 | 1.00 | 46.64 | A | O |
| ATOM | 159 | N | ASP | A | 33 | 72.229 | −20.380 | −18.591 | 1.00 | 53.18 | A | N |
| ATOM | 160 | CA | ASP | A | 33 | 72.441 | −19.503 | −19.758 | 1.00 | 56.33 | A | C |
| ATOM | 162 | CB | ASP | A | 33 | 72.191 | −20.264 | −21.080 | 1.00 | 56.22 | A | C |
| ATOM | 165 | CG | ASP | A | 33 | 73.311 | −21.266 | −21.435 | 1.00 | 55.52 | A | C |
| ATOM | 166 | OD1 | ASP | A | 33 | 74.495 | −21.027 | −21.103 | 1.00 | 50.09 | A | O |
| ATOM | 167 | OD2 | ASP | A | 33 | 73.004 | −22.293 | −22.087 | 1.00 | 54.49 | A | O |
| ATOM | 168 | C | ASP | A | 33 | 71.539 | −18.250 | −19.701 | 1.00 | 60.14 | A | C |
| ATOM | 169 | O | ASP | A | 33 | 71.973 | −17.150 | −20.064 | 1.00 | 59.09 | A | O |
| ATOM | 171 | N | TYR | A | 34 | 70.298 | −18.429 | −19.241 | 1.00 | 64.30 | A | N |
| ATOM | 172 | CA | TYR | A | 34 | 69.300 | −17.346 | −19.158 | 1.00 | 68.93 | A | C |
| ATOM | 174 | CB | TYR | A | 34 | 67.880 | −17.942 | −19.169 | 1.00 | 69.88 | A | C |
| ATOM | 177 | CG | TYR | A | 34 | 66.754 | −16.929 | −19.206 | 1.00 | 79.07 | A | C |
| ATOM | 178 | CD1 | TYR | A | 34 | 66.346 | −16.345 | −20.411 | 1.00 | 87.57 | A | C |
| ATOM | 180 | CE1 | TYR | A | 34 | 65.300 | −15.405 | −20.444 | 1.00 | 90.15 | A | C |
| ATOM | 182 | CZ | TYR | A | 34 | 64.653 | −15.057 | −19.261 | 1.00 | 92.74 | A | C |
| ATOM | 183 | OH | TYR | A | 34 | 63.620 | −14.141 | −19.270 | 1.00 | 95.62 | A | O |
| ATOM | 185 | CE2 | TYR | A | 34 | 65.041 | −15.631 | −18.056 | 1.00 | 89.91 | A | C |
| ATOM | 187 | CD2 | TYR | A | 34 | 66.084 | −16.561 | −18.034 | 1.00 | 85.72 | A | C |
| ATOM | 189 | C | TYR | A | 34 | 69.529 | −16.449 | −17.926 | 1.00 | 70.23 | A | C |
| ATOM | 190 | O | TYR | A | 34 | 69.797 | −15.260 | −18.063 | 1.00 | 70.32 | A | O |
| ATOM | 192 | N | LEU | A | 35 | 69.427 | −17.020 | −16.727 | 1.00 | 73.06 | A | N |
| ATOM | 193 | CA | LEU | A | 35 | 69.867 | −16.341 | −15.501 | 1.00 | 75.25 | A | C |
| ATOM | 195 | CB | LEU | A | 35 | 69.506 | −17.156 | −14.250 | 1.00 | 74.64 | A | C |
| ATOM | 198 | CG | LEU | A | 35 | 68.069 | −17.615 | −13.995 | 1.00 | 71.74 | A | C |
| ATOM | 200 | CD1 | LEU | A | 35 | 68.046 | −18.584 | −12.822 | 1.00 | 67.99 | A | C |
| ATOM | 204 | CD2 | LEU | A | 35 | 67.150 | −16.432 | −13.741 | 1.00 | 67.75 | A | C |
| ATOM | 208 | C | LEU | A | 35 | 71.379 | −16.252 | −15.592 | 1.00 | 78.42 | A | C |
| ATOM | 209 | O | LEU | A | 35 | 71.962 | −16.873 | −16.472 | 1.00 | 80.06 | A | O |
| ATOM | 211 | N | LEU | A | 36 | 72.028 | −15.505 | −14.705 | 1.00 | 81.43 | A | N |
| ATOM | 212 | CA | LEU | A | 36 | 73.494 | −15.583 | −14.598 | 1.00 | 84.46 | A | C |
| ATOM | 214 | CB | LEU | A | 36 | 73.881 | −16.978 | −14.068 | 1.00 | 84.18 | A | C |
| ATOM | 217 | CG | LEU | A | 36 | 75.259 | −17.216 | −13.442 | 1.00 | 84.76 | A | C |
| ATOM | 219 | CD1 | LEU | A | 36 | 75.421 | −16.414 | −12.157 | 1.00 | 87.18 | A | C |
| ATOM | 223 | CD2 | LEU | A | 36 | 75.470 | −18.700 | −13.189 | 1.00 | 83.02 | A | C |
| ATOM | 227 | C | LEU | A | 36 | 74.237 | −15.311 | −15.928 | 1.00 | 86.75 | A | C |
| ATOM | 228 | O | LEU | A | 36 | 75.330 | −15.834 | −16.156 | 1.00 | 86.15 | A | O |
| ATOM | 230 | N | SER | A | 37 | 73.644 | −14.503 | −16.805 | 1.00 | 90.20 | A | N |
| ATOM | 231 | CA | SER | A | 37 | 74.279 | −14.168 | −18.080 | 1.00 | 92.56 | A | C |
| ATOM | 233 | CB | SER | A | 37 | 73.237 | −14.010 | −19.189 | 1.00 | 92.69 | A | C |
| ATOM | 236 | OG | SER | A | 37 | 73.808 | −14.292 | −20.454 | 1.00 | 92.23 | A | O |
| ATOM | 238 | C | SER | A | 37 | 75.107 | −12.893 | −17.907 | 1.00 | 94.60 | A | C |
| ATOM | 239 | O | SER | A | 37 | 74.881 | −12.121 | −16.964 | 1.00 | 94.48 | A | O |
| ATOM | 241 | N | SER | A | 38 | 76.056 | −12.684 | −18.822 | 1.00 | 96.76 | A | N |
| ATOM | 242 | CA | SER | A | 38 | 77.120 | −11.683 | −18.643 | 1.00 | 98.37 | A | C |
| ATOM | 244 | CB | SER | A | 38 | 78.236 | −11.866 | −19.687 | 1.00 | 98.25 | A | C |
| ATOM | 247 | OG | SER | A | 38 | 77.731 | −11.924 | −21.008 | 1.00 | 97.84 | A | O |
| ATOM | 249 | C | SER | A | 38 | 76.642 | −10.232 | −18.666 | 1.00 | 99.95 | A | C |
| ATOM | 250 | O | SER | A | 38 | 76.185 | −9.731 | −19.698 | 1.00 | 100.18 | A | O |
| ATOM | 252 | N | ASP | A | 39 | 76.771 | −9.569 | −17.517 | 1.00 | 101.78 | A | N |
| ATOM | 253 | CA | ASP | A | 39 | 76.622 | −8.115 | −17.417 | 1.00 | 103.16 | A | C |
| ATOM | 255 | CB | ASP | A | 39 | 76.312 | −7.727 | −15.956 | 1.00 | 103.31 | A | C |
| ATOM | 258 | CG | ASP | A | 39 | 75.475 | −6.452 | −15.835 | 1.00 | 103.40 | A | C |
| ATOM | 259 | OD1 | ASP | A | 39 | 75.487 | −5.615 | −16.765 | 1.00 | 100.38 | A | O |
| ATOM | 260 | OD2 | ASP | A | 39 | 74.804 | −6.290 | −14.792 | 1.00 | 103.82 | A | O |
| ATOM | 261 | C | ASP | A | 39 | 77.945 | −7.505 | −17.942 | 1.00 | 104.15 | A | C |
| ATOM | 262 | O | ASP | A | 39 | 78.518 | −8.032 | −18.904 | 1.00 | 104.67 | A | O |
| ATOM | 264 | N | THR | A | 40 | 78.436 | −6.414 | −17.343 | 1.00 | 104.86 | A | N |
| ATOM | 265 | CA | THR | A | 40 | 79.818 | −5.955 | −17.599 | 1.00 | 105.03 | A | C |
| ATOM | 267 | CB | THR | A | 40 | 79.942 | −4.397 | −17.544 | 1.00 | 105.17 | A | C |
| ATOM | 269 | OG1 | THR | A | 40 | 78.774 | −3.789 | −18.111 | 1.00 | 104.08 | A | O |
| ATOM | 271 | CG2 | THR | A | 40 | 81.187 | −3.917 | −18.306 | 1.00 | 103.97 | A | C |
| ATOM | 275 | C | THR | A | 40 | 80.802 | −6.605 | −16.594 | 1.00 | 105.16 | A | C |
| ATOM | 276 | O | THR | A | 40 | 81.804 | −5.992 | −16.206 | 1.00 | 105.14 | A | O |
| ATOM | 278 | N | ASP | A | 41 | 80.509 | −7.851 | −16.198 | 1.00 | 104.87 | A | N |
| ATOM | 279 | CA | ASP | A | 41 | 81.285 | −8.600 | −15.198 | 1.00 | 104.03 | A | C |
| ATOM | 281 | CB | ASP | A | 41 | 80.400 | −8.951 | −13.991 | 1.00 | 103.68 | A | C |
| ATOM | 284 | CG | ASP | A | 41 | 80.063 | −7.737 | −13.126 | 1.00 | 103.58 | A | C |
| ATOM | 285 | OD1 | ASP | A | 41 | 80.402 | −6.594 | −13.506 | 1.00 | 101.01 | A | O |
| ATOM | 286 | OD2 | ASP | A | 41 | 79.455 | −7.929 | −12.053 | 1.00 | 103.04 | A | O |
| ATOM | 287 | C | ASP | A | 41 | 81.884 | −9.883 | −15.807 | 1.00 | 103.35 | A | C |
| ATOM | 288 | O | ASP | A | 41 | 81.159 | −10.738 | −16.329 | 1.00 | 102.89 | A | O |
| ATOM | 290 | N | GLU | A | 42 | 83.210 | −10.005 | −15.715 | 1.00 | 102.70 | A | N |
| ATOM | 291 | CA | GLU | A | 42 | 83.965 | −11.067 | −16.392 | 1.00 | 102.05 | A | C |
| ATOM | 293 | CB | GLU | A | 42 | 85.477 | −10.775 | −16.342 | 1.00 | 101.98 | A | C |
| ATOM | 296 | CG | GLU | A | 42 | 85.924 | −9.517 | −17.102 | 1.00 | 101.14 | A | C |

TABLE 4-2-continued

Coordinates of *P. alba* IspS

| ATOM | 299 | CD | GLU | A | 42 | 87.445 | −9.357 | −17.170 | 1.00 | 99.92 | A | C |
|---|---|---|---|---|---|---|---|---|---|---|---|---|
| ATOM | 300 | OE1 | GLU | A | 42 | 88.174 | −10.198 | −16.603 | 1.00 | 99.06 | A | O |
| ATOM | 301 | OE2 | GLU | A | 42 | 87.916 | −8.384 | −17.797 | 1.00 | 96.85 | A | O |
| ATOM | 302 | C | GLU | A | 42 | 83.700 | −12.466 | −15.820 | 1.00 | 101.77 | A | C |
| ATOM | 303 | O | GLU | A | 42 | 83.463 | −13.410 | −16.582 | 1.00 | 102.06 | A | O |
| ATOM | 305 | N | SER | A | 43 | 83.748 | −12.599 | −14.491 | 1.00 | 100.69 | A | N |
| ATOM | 306 | CA | SER | A | 43 | 83.632 | −13.915 | −13.829 | 1.00 | 99.39 | A | C |
| ATOM | 308 | CB | SER | A | 43 | 84.695 | −14.072 | −12.721 | 1.00 | 99.42 | A | C |
| ATOM | 311 | OG | SER | A | 43 | 84.503 | −13.160 | −11.657 | 1.00 | 98.04 | A | O |
| ATOM | 313 | C | SER | A | 43 | 82.213 | −14.252 | −13.308 | 1.00 | 97.81 | A | C |
| ATOM | 314 | O | SER | A | 43 | 82.054 | −15.108 | −12.424 | 1.00 | 96.95 | A | O |
| ATOM | 316 | N | ILE | A | 44 | 81.195 | −13.579 | −13.859 | 1.00 | 95.85 | A | N |
| ATOM | 317 | CA | ILE | A | 44 | 79.816 | −14.092 | −13.827 | 1.00 | 94.49 | A | C |
| ATOM | 319 | CB | ILE | A | 44 | 78.734 | −12.989 | −14.132 | 1.00 | 94.92 | A | C |
| ATOM | 321 | CG1 | ILE | A | 44 | 78.344 | −12.217 | −12.858 | 1.00 | 95.86 | A | C |
| ATOM | 324 | CD1 | ILE | A | 44 | 77.084 | −11.338 | −13.006 | 1.00 | 93.80 | A | C |
| ATOM | 328 | CG2 | ILE | A | 44 | 77.467 | −13.603 | −14.731 | 1.00 | 94.41 | A | C |
| ATOM | 332 | C | ILE | A | 44 | 79.704 | −15.251 | −14.832 | 1.00 | 92.51 | A | C |
| ATOM | 333 | O | ILE | A | 44 | 78.815 | −16.099 | −14.698 | 1.00 | 91.97 | A | O |
| ATOM | 335 | N | GLU | A | 45 | 80.615 | −15.284 | −15.817 | 1.00 | 90.17 | A | N |
| ATOM | 336 | CA | GLU | A | 45 | 80.662 | −16.342 | −16.845 | 1.00 | 88.08 | A | C |
| ATOM | 338 | CB | GLU | A | 45 | 81.071 | −15.768 | −18.205 | 1.00 | 88.74 | A | C |
| ATOM | 341 | CG | GLU | A | 45 | 79.979 | −14.922 | −18.864 | 1.00 | 91.64 | A | C |
| ATOM | 344 | CD | GLU | A | 45 | 79.561 | −15.416 | −20.250 | 1.00 | 94.30 | A | C |
| ATOM | 345 | OE1 | GLU | A | 45 | 80.265 | −16.268 | −20.839 | 1.00 | 95.27 | A | O |
| ATOM | 346 | OE2 | GLU | A | 45 | 78.513 | −14.946 | −20.746 | 1.00 | 92.80 | A | O |
| ATOM | 347 | C | GLU | A | 45 | 81.570 | −17.536 | −16.521 | 1.00 | 85.08 | A | C |
| ATOM | 348 | O | GLU | A | 45 | 81.331 | −18.638 | −17.021 | 1.00 | 84.95 | A | O |
| ATOM | 350 | N | VAL | A | 46 | 82.620 | −17.323 | −15.727 | 1.00 | 81.35 | A | N |
| ATOM | 351 | CA | VAL | A | 46 | 83.420 | −18.442 | −15.202 | 1.00 | 78.09 | A | C |
| ATOM | 353 | CB | VAL | A | 46 | 84.741 | −17.959 | −14.548 | 1.00 | 78.08 | A | C |
| ATOM | 355 | CG1 | VAL | A | 46 | 85.516 | −19.136 | −13.944 | 1.00 | 78.15 | A | C |
| ATOM | 359 | CG2 | VAL | A | 46 | 85.603 | −17.213 | −15.570 | 1.00 | 79.62 | A | C |
| ATOM | 363 | C | VAL | A | 46 | 82.583 | −19.247 | −14.187 | 1.00 | 74.06 | A | C |
| ATOM | 364 | O | VAL | A | 46 | 82.718 | −20.472 | −14.090 | 1.00 | 73.88 | A | O |
| ATOM | 366 | N | TYR | A | 47 | 81.728 | −18.528 | −13.451 | 1.00 | 68.93 | A | N |
| ATOM | 367 | CA | TYR | A | 47 | 80.741 | −19.086 | −12.512 | 1.00 | 65.54 | A | C |
| ATOM | 369 | CB | TYR | A | 47 | 80.142 | −17.905 | −11.718 | 1.00 | 65.84 | A | C |
| ATOM | 372 | CG | TYR | A | 47 | 79.247 | −18.192 | −10.516 | 1.00 | 68.89 | A | C |
| ATOM | 373 | CD1 | TYR | A | 47 | 79.776 | −18.352 | −9.229 | 1.00 | 72.76 | A | C |
| ATOM | 375 | CE1 | TYR | A | 47 | 78.930 | −18.585 | −8.113 | 1.00 | 72.95 | A | C |
| ATOM | 377 | CZ | TYR | A | 47 | 77.542 | −18.631 | −8.291 | 1.00 | 72.91 | A | C |
| ATOM | 378 | OH | TYR | A | 47 | 76.679 | −18.853 | −7.222 | 1.00 | 53.89 | A | O |
| ATOM | 380 | CE2 | TYR | A | 47 | 77.008 | −18.448 | −9.560 | 1.00 | 71.64 | A | C |
| ATOM | 382 | CD2 | TYR | A | 47 | 77.859 | −18.216 | −10.655 | 1.00 | 72.02 | A | C |
| ATOM | 384 | C | TYR | A | 47 | 79.658 | −19.899 | −13.280 | 1.00 | 61.30 | A | C |
| ATOM | 385 | O | TYR | A | 47 | 79.353 | −21.044 | −12.929 | 1.00 | 59.34 | A | O |
| ATOM | 387 | N | LYS | A | 48 | 79.109 | −19.287 | −14.333 | 1.00 | 56.43 | A | N |
| ATOM | 388 | CA | LYS | A | 48 | 78.171 | −19.918 | −15.284 | 1.00 | 52.55 | A | C |
| ATOM | 390 | CB | LYS | A | 48 | 77.920 | −18.945 | −16.451 | 1.00 | 53.28 | A | C |
| ATOM | 393 | CG | LYS | A | 48 | 76.989 | −19.391 | −17.592 | 1.00 | 55.50 | A | C |
| ATOM | 396 | CD | LYS | A | 48 | 77.428 | −18.712 | −18.913 | 1.00 | 61.02 | A | C |
| ATOM | 399 | CE | LYS | A | 48 | 76.323 | −18.612 | −19.970 | 1.00 | 65.42 | A | C |
| ATOM | 402 | NZ | LYS | A | 48 | 75.608 | −17.279 | −19.985 | 1.00 | 66.42 | A | N |
| ATOM | 406 | C | LYS | A | 48 | 78.673 | −21.255 | −15.828 | 1.00 | 47.94 | A | C |
| ATOM | 407 | O | LYS | A | 48 | 78.023 | −22.273 | −15.643 | 1.00 | 47.33 | A | O |
| ATOM | 409 | N | ASP | A | 49 | 79.822 | −21.250 | −16.496 | 1.00 | 44.41 | A | N |
| ATOM | 410 | CA | ASP | A | 49 | 80.382 | −22.471 | −17.087 | 1.00 | 43.52 | A | C |
| ATOM | 412 | CB | ASP | A | 49 | 81.659 | −22.188 | −17.915 | 1.00 | 44.86 | A | C |
| ATOM | 415 | CG | ASP | A | 49 | 81.387 | −21.342 | −19.179 | 1.00 | 48.93 | A | C |
| ATOM | 416 | OD1 | ASP | A | 49 | 80.230 | −21.330 | −19.679 | 1.00 | 53.55 | A | O |
| ATOM | 417 | OD2 | ASP | A | 49 | 82.339 | −20.689 | −19.670 | 1.00 | 47.52 | A | O |
| ATOM | 418 | C | ASP | A | 49 | 80.680 | −23.512 | −16.011 | 1.00 | 41.34 | A | C |
| ATOM | 419 | O | ASP | A | 49 | 80.564 | −24.715 | −16.263 | 1.00 | 39.75 | A | O |
| ATOM | 421 | N | LYS | A | 50 | 81.052 | −23.055 | −14.813 | 1.00 | 39.19 | A | N |
| ATOM | 422 | CA | LYS | A | 50 | 81.252 | −23.967 | −13.693 | 1.00 | 37.19 | A | C |
| ATOM | 424 | CB | LYS | A | 50 | 81.870 | −23.260 | −12.480 | 1.00 | 39.17 | A | C |
| ATOM | 427 | CG | LYS | A | 50 | 82.291 | −24.204 | −11.330 | 1.00 | 44.35 | A | C |
| ATOM | 430 | CD | LYS | A | 50 | 82.896 | −23.401 | −10.166 | 1.00 | 55.34 | A | C |
| ATOM | 433 | CE | LYS | A | 50 | 84.411 | −23.260 | −10.273 | 1.00 | 59.44 | A | C |
| ATOM | 436 | NZ | LYS | A | 50 | 84.866 | −21.942 | −9.757 | 1.00 | 57.35 | A | N |
| ATOM | 440 | C | LYS | A | 50 | 79.920 | −24.617 | −13.344 | 1.00 | 33.13 | A | C |
| ATOM | 441 | O | LYS | A | 50 | 79.846 | −25.845 | −13.254 | 1.00 | 31.70 | A | O |
| ATOM | 443 | N | ALA | A | 51 | 78.862 | −23.813 | −13.195 | 1.00 | 28.95 | A | N |
| ATOM | 444 | CA | ALA | A | 51 | 77.540 | −24.361 | −12.872 | 1.00 | 27.76 | A | C |
| ATOM | 446 | CB | ALA | A | 51 | 76.523 | −23.233 | −12.640 | 1.00 | 27.51 | A | C |
| ATOM | 450 | C | ALA | A | 51 | 77.030 | −25.359 | −13.942 | 1.00 | 26.48 | A | C |
| ATOM | 451 | O | ALA | A | 51 | 76.596 | −26.462 | −13.615 | 1.00 | 28.45 | A | O |

TABLE 4-2-continued

Coordinates of *P. alba* IspS

| ATOM | 453 | N | LYS | A | 52 | 77.104 | −24.980 | −15.212 | 1.00 | 25.84 | A | N |
| ATOM | 454 | CA | LYS | A | 52 | 76.704 | −25.867 | −16.319 | 1.00 | 25.55 | A | C |
| ATOM | 456 | CB | LYS | A | 52 | 77.062 | −25.228 | −17.679 | 1.00 | 25.87 | A | C |
| ATOM | 459 | CG | LYS | A | 52 | 76.061 | −24.158 | −18.106 | 1.00 | 30.35 | A | C |
| ATOM | 462 | CD | LYS | A | 52 | 76.635 | −23.079 | −19.007 | 1.00 | 29.72 | A | C |
| ATOM | 465 | CE | LYS | A | 52 | 76.636 | −23.486 | −20.493 | 1.00 | 39.59 | A | C |
| ATOM | 468 | NZ | LYS | A | 52 | 77.217 | −22.424 | −21.416 | 1.00 | 37.70 | A | N |
| ATOM | 472 | C | LYS | A | 52 | 77.345 | −27.247 | −16.217 | 1.00 | 25.06 | A | C |
| ATOM | 473 | O | LYS | A | 52 | 76.678 | −28.266 | −16.388 | 1.00 | 24.13 | A | O |
| ATOM | 475 | N | LYS | A | 53 | 78.647 | −27.270 | −15.941 | 1.00 | 25.32 | A | N |
| ATOM | 476 | CA | LYS | A | 53 | 79.407 | −28.529 | −15.862 | 1.00 | 26.67 | A | C |
| ATOM | 478 | CB | LYS | A | 53 | 80.915 | −28.230 | −15.729 | 1.00 | 28.91 | A | C |
| ATOM | 481 | CG | LYS | A | 53 | 81.781 | −29.479 | −15.584 | 1.00 | 38.89 | A | C |
| ATOM | 484 | CD | LYS | A | 53 | 83.274 | −29.214 | −15.866 | 1.00 | 51.52 | A | C |
| ATOM | 487 | CE | LYS | A | 53 | 84.101 | −30.510 | −15.696 | 1.00 | 55.41 | A | C |
| ATOM | 490 | NZ | LYS | A | 53 | 85.467 | −30.399 | −16.280 | 1.00 | 56.50 | A | N |
| ATOM | 494 | C | LYS | A | 53 | 78.940 | −29.439 | −14.705 | 1.00 | 23.90 | A | C |
| ATOM | 495 | O | LYS | A | 53 | 78.751 | −30.648 | −14.893 | 1.00 | 21.50 | A | O |
| ATOM | 497 | N | LEU | A | 54 | 78.770 | −28.847 | −13.523 | 1.00 | 20.73 | A | N |
| ATOM | 498 | CA | LEU | A | 54 | 78.317 | −29.568 | −12.343 | 1.00 | 21.72 | A | C |
| ATOM | 500 | CB | LEU | A | 54 | 78.280 | −28.637 | −11.120 | 1.00 | 21.06 | A | C |
| ATOM | 503 | CG | LEU | A | 54 | 79.601 | −27.919 | −10.778 | 1.00 | 26.70 | A | C |
| ATOM | 505 | CD1 | LEU | A | 54 | 79.389 | −26.832 | −9.753 | 1.00 | 21.18 | A | C |
| ATOM | 509 | CD2 | LEU | A | 54 | 80.674 | −28.909 | −10.299 | 1.00 | 27.08 | A | C |
| ATOM | 513 | C | LEU | A | 54 | 76.927 | −30.132 | −12.611 | 1.00 | 21.21 | A | C |
| ATOM | 514 | O | LEU | A | 54 | 76.642 | −31.304 | −12.353 | 1.00 | 21.09 | A | O |
| ATOM | 516 | N | GLU | A | 55 | 76.073 | −29.270 | −13.144 | 1.00 | 21.62 | A | N |
| ATOM | 517 | CA | GLU | A | 55 | 74.692 | −29.602 | −13.409 | 1.00 | 20.09 | A | C |
| ATOM | 519 | CB | GLU | A | 55 | 73.961 | −28.375 | −13.955 | 1.00 | 20.04 | A | C |
| ATOM | 522 | CG | GLU | A | 55 | 72.497 | −28.639 | −14.395 | 1.00 | 25.33 | A | C |
| ATOM | 525 | CD | GLU | A | 55 | 71.880 | −27.437 | −15.100 | 1.00 | 25.76 | A | C |
| ATOM | 526 | OE1 | GLU | A | 55 | 72.558 | −26.836 | −15.953 | 1.00 | 27.45 | A | O |
| ATOM | 527 | OE2 | GLU | A | 55 | 70.731 | −27.095 | −14.790 | 1.00 | 28.92 | A | O |
| ATOM | 528 | C | GLU | A | 55 | 74.614 | −30.736 | −14.410 | 1.00 | 19.08 | A | C |
| ATOM | 529 | O | GLU | A | 55 | 73.764 | −31.614 | −14.286 | 1.00 | 17.95 | A | O |
| ATOM | 531 | N | ALA | A | 56 | 75.505 | −30.721 | −15.396 | 1.00 | 18.58 | A | N |
| ATOM | 532 | CA | ALA | A | 56 | 75.516 | −31.770 | −16.419 | 1.00 | 18.68 | A | C |
| ATOM | 534 | CB | ALA | A | 56 | 76.589 | −31.476 | −17.477 | 1.00 | 17.67 | A | C |
| ATOM | 538 | C | ALA | A | 56 | 75.782 | −33.105 | −15.784 | 1.00 | 18.70 | A | C |
| ATOM | 539 | O | ALA | A | 56 | 75.164 | −34.107 | −16.140 | 1.00 | 21.50 | A | O |
| ATOM | 541 | N | GLU | A | 57 | 76.717 | −33.118 | −14.840 | 1.00 | 19.66 | A | N |
| ATOM | 542 | CA | GLU | A | 57 | 77.138 | −34.352 | −14.191 | 1.00 | 19.60 | A | C |
| ATOM | 544 | CB | GLU | A | 57 | 78.451 | −34.147 | −13.404 | 1.00 | 21.64 | A | C |
| ATOM | 547 | CG | GLU | A | 57 | 78.990 | −35.425 | −12.709 | 1.00 | 27.13 | A | C |
| ATOM | 550 | CD | GLU | A | 57 | 80.415 | −35.275 | −12.139 | 1.00 | 28.89 | A | C |
| ATOM | 551 | OE1 | GLU | A | 57 | 81.165 | −34.363 | −12.546 | 1.00 | 30.32 | A | O |
| ATOM | 552 | OE2 | GLU | A | 57 | 80.781 | −36.104 | −11.276 | 1.00 | 36.69 | A | O |
| ATOM | 553 | C | GLU | A | 57 | 76.009 | −34.867 | −13.316 | 1.00 | 18.61 | A | C |
| ATOM | 554 | O | GLU | A | 57 | 75.731 | −36.037 | −13.348 | 1.00 | 19.99 | A | O |
| ATOM | 556 | N | VAL | A | 58 | 75.313 | −33.996 | −12.580 | 1.00 | 19.50 | A | N |
| ATOM | 557 | CA | VAL | A | 58 | 74.171 | −34.452 | −11.772 | 1.00 | 18.20 | A | C |
| ATOM | 559 | CB | VAL | A | 58 | 73.603 | −33.329 | −10.893 | 1.00 | 21.45 | A | C |
| ATOM | 561 | CG1 | VAL | A | 58 | 72.374 | −33.841 | −10.141 | 1.00 | 16.09 | A | C |
| ATOM | 565 | CG2 | VAL | A | 58 | 74.659 | −32.800 | −9.918 | 1.00 | 17.59 | A | C |
| ATOM | 569 | C | VAL | A | 58 | 73.062 | −35.007 | −12.676 | 1.00 | 18.18 | A | C |
| ATOM | 570 | O | VAL | A | 58 | 72.461 | −36.063 | −12.402 | 1.00 | 17.53 | A | O |
| ATOM | 572 | N | ARG | A | 59 | 72.841 | −34.337 | −13.802 | 1.00 | 20.36 | A | N |
| ATOM | 573 | CA | ARG | A | 59 | 71.896 | −34.833 | −14.819 | 1.00 | 19.83 | A | C |
| ATOM | 575 | CB | ARG | A | 59 | 71.891 | −33.923 | −16.049 | 1.00 | 20.72 | A | C |
| ATOM | 578 | CG | ARG | A | 59 | 70.959 | −34.357 | −17.180 | 1.00 | 21.44 | A | C |
| ATOM | 581 | CD | ARG | A | 59 | 71.656 | −35.311 | −18.172 | 1.00 | 26.88 | A | C |
| ATOM | 584 | NE | ARG | A | 59 | 70.756 | −35.765 | −19.235 | 1.00 | 26.75 | A | N |
| ATOM | 586 | CZ | ARG | A | 59 | 70.980 | −36.808 | −20.035 | 1.00 | 27.29 | A | C |
| ATOM | 587 | NH1 | ARG | A | 59 | 70.079 | −37.128 | −20.948 | 1.00 | 26.52 | A | N |
| ATOM | 590 | NH2 | ARG | A | 59 | 72.106 | −37.527 | −19.954 | 1.00 | 26.33 | A | N |
| ATOM | 593 | C | ARG | A | 59 | 72.271 | −36.239 | −15.210 | 1.00 | 20.53 | A | C |
| ATOM | 594 | O | ARG | A | 59 | 71.435 | −37.137 | −15.233 | 1.00 | 21.41 | A | O |
| ATOM | 596 | N | ARG | A | 60 | 73.546 | −36.445 | −15.495 | 1.00 | 21.14 | A | N |
| ATOM | 597 | CA | ARG | A | 60 | 73.988 | −37.755 | −15.936 | 1.00 | 19.56 | A | C |
| ATOM | 599 | CB | ARG | A | 60 | 75.477 | −37.765 | −16.209 | 1.00 | 19.04 | A | C |
| ATOM | 602 | CG | ARG | A | 60 | 75.986 | −39.109 | −16.690 | 1.00 | 21.95 | A | C |
| ATOM | 605 | CD | ARG | A | 60 | 77.465 | −39.067 | −16.905 | 1.00 | 21.61 | A | C |
| ATOM | 608 | NE | ARG | A | 60 | 78.162 | −38.960 | −15.637 | 1.00 | 25.86 | A | N |
| ATOM | 610 | CZ | ARG | A | 60 | 79.450 | −38.659 | −15.502 | 1.00 | 27.72 | A | C |
| ATOM | 611 | NH1 | ARG | A | 60 | 79.957 | −38.595 | −14.288 | 1.00 | 27.66 | A | N |
| ATOM | 614 | NH2 | ARG | A | 60 | 80.239 | −38.429 | −16.561 | 1.00 | 24.85 | A | N |
| ATOM | 617 | C | ARG | A | 60 | 73.680 | −38.834 | −14.910 | 1.00 | 20.09 | A | C |
| ATOM | 618 | O | ARG | A | 60 | 73.184 | −39.907 | −15.260 | 1.00 | 19.04 | A | O |

TABLE 4-2-continued

Coordinates of *P. alba* IspS

| ATOM | 620 | N | GLU | A | 61 | 73.987 | −38.556 | −13.652 | 1.00 | 21.36 | A | N |
|---|---|---|---|---|---|---|---|---|---|---|---|---|
| ATOM | 621 | CA | GLU | A | 61 | 73.834 | −39.565 | −12.586 | 1.00 | 21.08 | A | C |
| ATOM | 623 | CB | GLU | A | 61 | 74.503 | −39.095 | −11.291 | 1.00 | 20.78 | A | C |
| ATOM | 626 | CG | GLU | A | 61 | 76.019 | −38.914 | −11.424 | 1.00 | 29.32 | A | C |
| ATOM | 629 | CD | GLU | A | 61 | 76.700 | −40.205 | −11.825 | 1.00 | 33.44 | A | C |
| ATOM | 630 | OE1 | GLU | A | 61 | 76.614 | −41.174 | −11.038 | 1.00 | 32.69 | A | O |
| ATOM | 631 | OE2 | GLU | A | 61 | 77.297 | −40.251 | −12.930 | 1.00 | 36.93 | A | O |
| ATOM | 632 | C | GLU | A | 61 | 72.376 | −39.954 | −12.308 | 1.00 | 19.59 | A | C |
| ATOM | 633 | O | GLU | A | 61 | 72.124 | −41.076 | −11.938 | 1.00 | 21.54 | A | O |
| ATOM | 635 | N | ILE | A | 62 | 71.443 | −39.024 | −12.485 | 1.00 | 20.46 | A | N |
| ATOM | 636 | CA | ILE | A | 62 | 70.019 | −39.298 | −12.290 | 1.00 | 20.63 | A | C |
| ATOM | 638 | CB | ILE | A | 62 | 69.195 | −38.010 | −12.148 | 1.00 | 20.75 | A | C |
| ATOM | 640 | CG1 | ILE | A | 62 | 69.651 | −37.184 | −10.937 | 1.00 | 20.34 | A | C |
| ATOM | 643 | CD1 | ILE | A | 62 | 69.052 | −35.781 | −10.885 | 1.00 | 17.82 | A | C |
| ATOM | 647 | CG2 | ILE | A | 62 | 67.708 | −38.363 | −12.000 | 1.00 | 21.70 | A | C |
| ATOM | 651 | C | ILE | A | 62 | 69.462 | −40.108 | −13.462 | 1.00 | 22.58 | A | C |
| ATOM | 652 | O | ILE | A | 62 | 68.548 | −40.895 | −13.298 | 1.00 | 23.12 | A | O |
| ATOM | 654 | N | ASN | A | 63 | 70.008 | −39.899 | −14.656 | 1.00 | 24.14 | A | N |
| ATOM | 655 | CA | ASN | A | 63 | 69.567 | −40.628 | −15.840 | 1.00 | 22.08 | A | C |
| ATOM | 657 | CB | ASN | A | 63 | 69.839 | −39.776 | −17.071 | 1.00 | 20.09 | A | C |
| ATOM | 660 | CG | ASN | A | 63 | 68.812 | −38.693 | −17.256 | 1.00 | 24.05 | A | C |
| ATOM | 661 | OD1 | ASN | A | 63 | 67.809 | −38.925 | −17.893 | 1.00 | 28.24 | A | O |
| ATOM | 662 | ND2 | ASN | A | 63 | 69.063 | −37.493 | −16.717 | 1.00 | 22.91 | A | N |
| ATOM | 665 | C | ASN | A | 63 | 70.232 | −41.999 | −15.980 | 1.00 | 23.43 | A | C |
| ATOM | 666 | O | ASN | A | 63 | 69.809 | −42.829 | −16.783 | 1.00 | 25.36 | A | O |
| ATOM | 668 | N | ASN | A | 64 | 71.277 | −42.226 | −15.194 | 1.00 | 25.57 | A | N |
| ATOM | 669 | CA | ASN | A | 64 | 72.064 | −43.451 | −15.242 | 1.00 | 27.94 | A | C |
| ATOM | 671 | CB | ASN | A | 64 | 73.151 | −43.357 | −14.165 | 1.00 | 27.54 | A | C |
| ATOM | 674 | CG | ASN | A | 64 | 74.104 | −44.557 | −14.138 | 1.00 | 30.25 | A | C |
| ATOM | 675 | OD1 | ASN | A | 64 | 74.164 | −45.350 | −15.074 | 1.00 | 24.98 | A | O |
| ATOM | 676 | ND2 | ASN | A | 64 | 74.876 | −44.666 | −13.054 | 1.00 | 20.45 | A | N |
| ATOM | 679 | C | ASN | A | 64 | 71.185 | −44.656 | −14.992 | 1.00 | 30.41 | A | C |
| ATOM | 680 | O | ASN | A | 64 | 70.691 | −44.821 | −13.892 | 1.00 | 32.21 | A | O |
| ATOM | 682 | N | GLU | A | 65 | 71.004 | −45.516 | −15.989 | 1.00 | 33.50 | A | N |
| ATOM | 683 | CA | GLU | A | 65 | 70.150 | −46.701 | −15.800 | 1.00 | 35.73 | A | C |
| ATOM | 685 | CB | GLU | A | 65 | 69.578 | −47.175 | −17.129 | 1.00 | 36.73 | A | C |
| ATOM | 688 | CG | GLU | A | 65 | 68.675 | −46.102 | −17.762 | 1.00 | 41.17 | A | C |
| ATOM | 691 | CD | GLU | A | 65 | 67.803 | −46.596 | −18.908 | 1.00 | 48.22 | A | C |
| ATOM | 692 | OE1 | GLU | A | 65 | 67.712 | −47.831 | −19.150 | 1.00 | 47.55 | A | O |
| ATOM | 693 | OE2 | GLU | A | 65 | 67.194 | −45.716 | −19.562 | 1.00 | 48.75 | A | O |
| ATOM | 694 | C | GLU | A | 65 | 70.871 | −47.836 | −15.094 | 1.00 | 36.68 | A | C |
| ATOM | 695 | O | GLU | A | 65 | 70.240 | −48.776 | −14.634 | 1.00 | 37.20 | A | O |
| ATOM | 697 | N | LYS | A | 66 | 72.189 | −47.730 | −14.984 | 1.00 | 36.43 | A | N |
| ATOM | 698 | CA | LYS | A | 66 | 72.999 | −48.790 | −14.404 | 1.00 | 37.11 | A | C |
| ATOM | 700 | CB | LYS | A | 66 | 74.383 | −48.828 | −15.084 | 1.00 | 38.18 | A | C |
| ATOM | 703 | CG | LYS | A | 66 | 74.340 | −48.999 | −16.621 | 1.00 | 41.19 | A | C |
| ATOM | 706 | CD | LYS | A | 66 | 75.757 | −48.982 | −17.252 | 1.00 | 47.45 | A | C |
| ATOM | 709 | CE | LYS | A | 66 | 75.731 | −49.109 | −18.801 | 1.00 | 47.41 | A | C |
| ATOM | 712 | NZ | LYS | A | 66 | 74.829 | −50.210 | −19.287 | 1.00 | 47.24 | A | N |
| ATOM | 716 | C | LYS | A | 66 | 73.166 | −48.635 | −12.890 | 1.00 | 35.98 | A | C |
| ATOM | 717 | O | LYS | A | 66 | 73.803 | −49.470 | −12.252 | 1.00 | 36.59 | A | O |
| ATOM | 719 | N | ALA | A | 67 | 72.594 | −47.585 | −12.309 | 1.00 | 35.32 | A | N |
| ATOM | 720 | CA | ALA | A | 67 | 72.761 | −47.334 | −10.869 | 1.00 | 35.29 | A | C |
| ATOM | 722 | CB | ALA | A | 67 | 72.338 | −45.929 | −10.522 | 1.00 | 34.33 | A | C |
| ATOM | 726 | C | ALA | A | 67 | 71.970 | −48.331 | −10.027 | 1.00 | 35.67 | A | C |
| ATOM | 727 | O | ALA | A | 67 | 70.907 | −48.823 | −10.436 | 1.00 | 34.29 | A | O |
| ATOM | 729 | N | GLU | A | 68 | 72.502 | −48.627 | −8.850 | 1.00 | 36.18 | A | N |
| ATOM | 730 | CA | GLU | A | 68 | 71.759 | −49.403 | −7.869 | 1.00 | 38.84 | A | C |
| ATOM | 732 | CB | GLU | A | 68 | 72.619 | −49.725 | −6.645 | 1.00 | 40.31 | A | C |
| ATOM | 735 | CG | GLU | A | 68 | 72.545 | −51.178 | −6.224 | 1.00 | 51.58 | A | C |
| ATOM | 738 | CD | GLU | A | 68 | 73.198 | −52.108 | −7.240 | 1.00 | 62.21 | A | C |
| ATOM | 739 | OE1 | GLU | A | 68 | 74.352 | −51.827 | −7.646 | 1.00 | 67.12 | A | O |
| ATOM | 740 | OE2 | GLU | A | 68 | 72.558 | −53.114 | −7.632 | 1.00 | 64.39 | A | O |
| ATOM | 741 | C | GLU | A | 68 | 70.558 | −48.554 | −7.476 | 1.00 | 38.64 | A | C |
| ATOM | 742 | O | GLU | A | 68 | 70.672 | −47.332 | −7.342 | 1.00 | 37.36 | A | O |
| ATOM | 744 | N | PHE | A | 69 | 69.407 | −49.194 | −7.315 | 1.00 | 39.25 | A | N |
| ATOM | 745 | CA | PHE | A | 69 | 68.163 | −48.453 | −7.180 | 1.00 | 41.61 | A | C |
| ATOM | 747 | CB | PHE | A | 69 | 66.925 | −49.361 | −7.351 | 1.00 | 43.96 | A | C |
| ATOM | 750 | CG | PHE | A | 69 | 66.460 | −49.487 | −8.795 | 1.00 | 54.44 | A | C |
| ATOM | 751 | CD1 | PHE | A | 69 | 66.310 | −48.336 | −9.610 | 1.00 | 61.05 | A | C |
| ATOM | 753 | CE1 | PHE | A | 69 | 65.882 | −48.429 | −10.943 | 1.00 | 61.96 | A | C |
| ATOM | 755 | CZ | PHE | A | 69 | 65.586 | −49.684 | −11.483 | 1.00 | 65.52 | A | C |
| ATOM | 757 | CE2 | PHE | A | 69 | 65.728 | −50.846 | −10.681 | 1.00 | 65.07 | A | C |
| ATOM | 759 | CD2 | PHE | A | 69 | 66.161 | −50.739 | −9.344 | 1.00 | 62.25 | A | C |
| ATOM | 761 | C | PHE | A | 69 | 68.094 | −47.639 | −5.889 | 1.00 | 39.35 | A | C |
| ATOM | 762 | O | PHE | A | 69 | 67.620 | −46.506 | −5.906 | 1.00 | 34.88 | A | O |
| ATOM | 764 | N | LEU | A | 70 | 68.605 | −48.185 | −4.793 | 1.00 | 38.05 | A | N |
| ATOM | 765 | CA | LEU | A | 70 | 68.642 | −47.417 | −3.547 | 1.00 | 37.39 | A | C |

TABLE 4-2-continued

Coordinates of *P. alba* IspS

| ATOM | 767 | CB | LEU | A | 70 | 68.989 | −48.320 | −2.367 | 1.00 | 38.91 | A | C |
|------|-----|-----|-----|---|----|--------|---------|--------|------|-------|---|---|
| ATOM | 770 | CG | LEU | A | 70 | 68.749 | −47.727 | −0.970 | 1.00 | 45.09 | A | C |
| ATOM | 772 | CD1 | LEU | A | 70 | 67.365 | −47.093 | −0.854 | 1.00 | 42.32 | A | C |
| ATOM | 776 | CD2 | LEU | A | 70 | 68.950 | −48.819 | 0.092 | 1.00 | 48.11 | A | C |
| ATOM | 780 | C | LEU | A | 70 | 69.585 | −46.208 | −3.616 | 1.00 | 35.24 | A | C |
| ATOM | 781 | O | LEU | A | 70 | 69.273 | −45.134 | −3.076 | 1.00 | 33.59 | A | O |
| ATOM | 783 | N | THR | A | 71 | 70.715 | −46.351 | −4.308 | 1.00 | 32.18 | A | N |
| ATOM | 784 | CA | THR | A | 71 | 71.664 | −45.232 | −4.462 | 1.00 | 30.26 | A | C |
| ATOM | 786 | CB | THR | A | 71 | 72.975 | −45.686 | −5.151 | 1.00 | 31.18 | A | C |
| ATOM | 788 | OG1 | THR | A | 71 | 73.583 | −46.737 | −4.380 | 1.00 | 35.88 | A | O |
| ATOM | 790 | CG2 | THR | A | 71 | 73.957 | −44.539 | −5.269 | 1.00 | 32.21 | A | C |
| ATOM | 794 | C | THR | A | 71 | 71.023 | −44.120 | −5.277 | 1.00 | 27.98 | A | C |
| ATOM | 795 | O | THR | A | 71 | 71.215 | −42.940 | −5.011 | 1.00 | 29.70 | A | O |
| ATOM | 797 | N | LEU | A | 72 | 70.235 | −44.508 | −6.258 | 1.00 | 25.13 | A | N |
| ATOM | 798 | CA | LEU | A | 72 | 69.560 | −43.566 | −7.120 | 1.00 | 25.64 | A | C |
| ATOM | 800 | CB | LEU | A | 72 | 68.879 | −44.315 | −8.262 | 1.00 | 24.76 | A | C |
| ATOM | 803 | CG | LEU | A | 72 | 68.348 | −43.417 | −9.367 | 1.00 | 33.13 | A | C |
| ATOM | 805 | CD1 | LEU | A | 72 | 69.500 | −42.625 | −9.999 | 1.00 | 34.90 | A | C |
| ATOM | 809 | CD2 | LEU | A | 72 | 67.635 | −44.244 | −10.419 | 1.00 | 33.87 | A | C |
| ATOM | 813 | C | LEU | A | 72 | 68.515 | −42.792 | −6.344 | 1.00 | 25.13 | A | C |
| ATOM | 814 | O | LEU | A | 72 | 68.442 | −41.559 | −6.423 | 1.00 | 24.06 | A | O |
| ATOM | 816 | N | LEU | A | 73 | 67.705 | −43.530 | −5.593 | 1.00 | 24.72 | A | N |
| ATOM | 817 | CA | LEU | A | 73 | 66.685 | −42.926 | −4.767 | 1.00 | 24.94 | A | C |
| ATOM | 819 | CB | LEU | A | 73 | 65.863 | −43.986 | −4.053 | 1.00 | 25.13 | A | C |
| ATOM | 822 | CG | LEU | A | 73 | 65.002 | −44.831 | −4.983 | 1.00 | 24.35 | A | C |
| ATOM | 824 | CD1 | LEU | A | 73 | 64.535 | −46.087 | −4.255 | 1.00 | 25.41 | A | C |
| ATOM | 828 | CD2 | LEU | A | 73 | 63.853 | −44.027 | −5.559 | 1.00 | 20.54 | A | C |
| ATOM | 832 | C | LEU | A | 73 | 67.279 | −41.941 | −3.776 | 1.00 | 24.82 | A | C |
| ATOM | 833 | O | LEU | A | 73 | 66.697 | −40.868 | −3.534 | 1.00 | 24.80 | A | O |
| ATOM | 835 | N | GLU | A | 74 | 68.432 | −42.287 | −3.213 | 1.00 | 23.25 | A | N |
| ATOM | 836 | CA | GLU | A | 74 | 69.094 | −41.412 | −2.258 | 1.00 | 23.34 | A | C |
| ATOM | 838 | CB | GLU | A | 74 | 70.095 | −42.214 | −1.406 | 1.00 | 24.35 | A | C |
| ATOM | 841 | CG | GLU | A | 74 | 69.391 | −43.188 | −0.427 | 1.00 | 32.72 | A | C |
| ATOM | 844 | CD | GLU | A | 74 | 70.321 | −43.919 | 0.537 | 1.00 | 43.15 | A | C |
| ATOM | 845 | OE1 | GLU | A | 74 | 71.558 | −43.826 | 0.407 | 1.00 | 44.90 | A | O |
| ATOM | 846 | OE2 | GLU | A | 74 | 69.799 | −44.603 | 1.438 | 1.00 | 48.93 | A | O |
| ATOM | 847 | C | GLU | A | 74 | 69.729 | −40.186 | −2.941 | 1.00 | 22.43 | A | C |
| ATOM | 848 | O | GLU | A | 74 | 69.785 | −39.096 | −2.362 | 1.00 | 24.16 | A | O |
| ATOM | 850 | N | LEU | A | 75 | 70.183 | −40.335 | −4.177 | 1.00 | 22.16 | A | N |
| ATOM | 851 | CA | LEU | A | 75 | 70.613 | −39.180 | −4.959 | 1.00 | 20.37 | A | C |
| ATOM | 853 | CB | LEU | A | 75 | 71.150 | −39.622 | −6.304 | 1.00 | 22.89 | A | C |
| ATOM | 856 | CG | LEU | A | 75 | 71.569 | −38.495 | −7.268 | 1.00 | 22.68 | A | C |
| ATOM | 858 | CD1 | LEU | A | 75 | 72.741 | −37.711 | −6.687 | 1.00 | 15.06 | A | C |
| ATOM | 862 | CD2 | LEU | A | 75 | 71.934 | −39.153 | −8.602 | 1.00 | 25.81 | A | C |
| ATOM | 866 | C | LEU | A | 75 | 69.465 | −38.220 | −5.224 | 1.00 | 20.23 | A | C |
| ATOM | 867 | O | LEU | A | 75 | 69.629 | −37.017 | −5.137 | 1.00 | 23.40 | A | O |
| ATOM | 869 | N | ILE | A | 76 | 68.307 | −38.754 | −5.582 | 1.00 | 21.55 | A | N |
| ATOM | 870 | CA | ILE | A | 76 | 67.174 | −37.912 | −5.923 | 1.00 | 23.06 | A | C |
| ATOM | 872 | CB | ILE | A | 76 | 65.974 | −38.746 | −6.401 | 1.00 | 22.62 | A | C |
| ATOM | 874 | CG1 | ILE | A | 76 | 66.259 | −39.323 | −7.790 | 1.00 | 24.94 | A | C |
| ATOM | 877 | CD1 | ILE | A | 76 | 65.388 | −40.527 | −8.171 | 1.00 | 19.96 | A | C |
| ATOM | 881 | CG2 | ILE | A | 76 | 64.717 | −37.881 | −6.400 | 1.00 | 19.22 | A | C |
| ATOM | 885 | C | ILE | A | 76 | 66.755 | −37.093 | −4.711 | 1.00 | 24.28 | A | C |
| ATOM | 886 | O | ILE | A | 76 | 66.472 | −35.896 | −4.821 | 1.00 | 26.54 | A | O |
| ATOM | 888 | N | ASP | A | 77 | 66.717 | −37.761 | −3.563 | 1.00 | 23.78 | A | N |
| ATOM | 889 | CA | ASP | A | 77 | 66.327 | −37.154 | −2.298 | 1.00 | 24.77 | A | C |
| ATOM | 891 | CB | ASP | A | 77 | 66.306 | −38.227 | −1.200 | 1.00 | 23.52 | A | C |
| ATOM | 894 | CG | ASP | A | 77 | 65.627 | −37.769 | 0.071 | 1.00 | 30.63 | A | C |
| ATOM | 895 | OD1 | ASP | A | 77 | 64.773 | −36.826 | 0.038 | 1.00 | 30.60 | A | O |
| ATOM | 896 | OD2 | ASP | A | 77 | 65.941 | −38.387 | 1.119 | 1.00 | 33.55 | A | O |
| ATOM | 897 | C | ASP | A | 77 | 67.308 | −36.068 | −1.909 | 1.00 | 25.16 | A | C |
| ATOM | 898 | O | ASP | A | 77 | 66.907 | −34.999 | −1.440 | 1.00 | 24.30 | A | O |
| ATOM | 900 | N | ASN | A | 78 | 68.602 | −36.348 | −2.093 | 1.00 | 25.18 | A | N |
| ATOM | 901 | CA | ASN | A | 78 | 69.643 | −35.372 | −1.765 | 1.00 | 23.87 | A | C |
| ATOM | 903 | CB | ASN | A | 78 | 71.032 | −36.003 | −1.918 | 1.00 | 27.24 | A | C |
| ATOM | 906 | CG | ASN | A | 78 | 71.448 | −36.844 | −0.701 | 1.00 | 29.01 | A | C |
| ATOM | 907 | OD1 | ASN | A | 78 | 71.108 | −36.503 | 0.421 | 1.00 | 29.64 | A | O |
| ATOM | 908 | ND2 | ASN | A | 78 | 72.208 | −37.933 | −0.928 | 1.00 | 22.29 | A | N |
| ATOM | 911 | C | ASN | A | 78 | 69.482 | −34.154 | −2.679 | 1.00 | 23.28 | A | C |
| ATOM | 912 | O | ASN | A | 78 | 69.488 | −32.988 | −2.235 | 1.00 | 22.07 | A | O |
| ATOM | 914 | N | VAL | A | 79 | 69.293 | −34.431 | −3.962 | 1.00 | 21.38 | A | N |
| ATOM | 915 | CA | VAL | A | 79 | 69.097 | −33.364 | −4.947 | 1.00 | 22.16 | A | C |
| ATOM | 917 | CB | VAL | A | 79 | 68.883 | −33.961 | −6.357 | 1.00 | 23.08 | A | C |
| ATOM | 919 | CG1 | VAL | A | 79 | 68.336 | −32.907 | −7.305 | 1.00 | 19.92 | A | C |
| ATOM | 923 | CG2 | VAL | A | 79 | 70.195 | −34.593 | −6.876 | 1.00 | 18.18 | A | C |
| ATOM | 927 | C | VAL | A | 79 | 67.892 | −32.487 | −4.573 | 1.00 | 21.06 | A | C |
| ATOM | 928 | O | VAL | A | 79 | 67.950 | −31.257 | −4.642 | 1.00 | 22.39 | A | O |
| ATOM | 930 | N | GLN | A | 80 | 66.805 | −33.109 | −4.155 | 1.00 | 20.41 | A | N |

TABLE 4-2-continued

Coordinates of *P. alba* IspS

| ATOM | 931 | CA | GLN | A | 80 | 65.613 | −32.315 | −3.760 | 1.00 | 21.13 | A | C |
|---|---|---|---|---|---|---|---|---|---|---|---|---|
| ATOM | 933 | CB | GLN | A | 80 | 64.376 | −33.203 | −3.656 | 1.00 | 19.81 | A | C |
| ATOM | 936 | CG | GLN | A | 80 | 64.025 | −33.857 | −5.004 | 1.00 | 16.22 | A | C |
| ATOM | 939 | CD | GLN | A | 80 | 62.628 | −34.460 | −5.034 | 1.00 | 23.03 | A | C |
| ATOM | 940 | OE1 | GLN | A | 80 | 61.984 | −34.492 | −6.087 | 1.00 | 19.49 | A | O |
| ATOM | 941 | NE2 | GLN | A | 80 | 62.146 | −34.930 | −3.873 | 1.00 | 19.16 | A | N |
| ATOM | 944 | C | GLN | A | 80 | 65.829 | −31.542 | −2.465 | 1.00 | 22.00 | A | C |
| ATOM | 945 | O | GLN | A | 80 | 65.497 | −30.360 | −2.366 | 1.00 | 25.58 | A | O |
| ATOM | 947 | N | ARG | A | 81 | 66.399 | −32.200 | −1.475 | 1.00 | 20.76 | A | N |
| ATOM | 948 | CA | ARG | A | 81 | 66.557 | −31.579 | −0.171 | 1.00 | 22.60 | A | C |
| ATOM | 950 | CB | ARG | A | 81 | 67.004 | −32.619 | 0.840 | 1.00 | 22.73 | A | C |
| ATOM | 953 | CG | ARG | A | 81 | 65.896 | −33.644 | 1.107 | 1.00 | 27.58 | A | C |
| ATOM | 956 | CD | ARG | A | 81 | 66.200 | −34.449 | 2.360 | 1.00 | 26.39 | A | C |
| ATOM | 959 | NE | ARG | A | 81 | 66.352 | −33.563 | 3.508 | 1.00 | 33.93 | A | N |
| ATOM | 961 | CZ | ARG | A | 81 | 66.523 | −33.991 | 4.754 | 1.00 | 44.75 | A | C |
| ATOM | 962 | NH1 | ARG | A | 81 | 66.529 | −35.296 | 5.011 | 1.00 | 46.21 | A | N |
| ATOM | 965 | NH2 | ARG | A | 81 | 66.665 | −33.114 | 5.747 | 1.00 | 38.64 | A | N |
| ATOM | 968 | C | ARG | A | 81 | 67.534 | −30.418 | −0.225 | 1.00 | 21.64 | A | C |
| ATOM | 969 | O | ARG | A | 81 | 67.329 | −29.389 | 0.424 | 1.00 | 22.17 | A | O |
| ATOM | 971 | N | LEU | A | 82 | 68.575 | −30.578 | −1.032 | 1.00 | 18.90 | A | N |
| ATOM | 972 | CA | LEU | A | 82 | 69.556 | −29.522 | −1.230 | 1.00 | 16.62 | A | C |
| ATOM | 974 | CB | LEU | A | 82 | 70.796 | −30.076 | −1.937 | 1.00 | 15.07 | A | C |
| ATOM | 977 | CG | LEU | A | 82 | 71.610 | −31.097 | −1.137 | 1.00 | 19.59 | A | C |
| ATOM | 979 | CD1 | LEU | A | 82 | 72.585 | −31.806 | −2.061 | 1.00 | 19.94 | A | C |
| ATOM | 983 | CD2 | LEU | A | 82 | 72.325 | −30.424 | 0.043 | 1.00 | 16.09 | A | C |
| ATOM | 987 | C | LEU | A | 82 | 68.998 | −28.356 | −2.013 | 1.00 | 17.05 | A | C |
| ATOM | 988 | O | LEU | A | 82 | 69.691 | −27.374 | −2.197 | 1.00 | 18.11 | A | O |
| ATOM | 990 | N | GLY | A | 83 | 67.759 | −28.470 | −2.490 | 1.00 | 19.79 | A | N |
| ATOM | 991 | CA | GLY | A | 83 | 67.064 | −27.359 | −3.130 | 1.00 | 20.72 | A | C |
| ATOM | 994 | C | GLY | A | 83 | 67.100 | −27.353 | −4.651 | 1.00 | 21.28 | A | C |
| ATOM | 995 | O | GLY | A | 83 | 66.622 | −26.412 | −5.277 | 1.00 | 21.81 | A | O |
| ATOM | 997 | N | LEU | A | 84 | 67.620 | −28.418 | −5.254 | 1.00 | 22.14 | A | N |
| ATOM | 998 | CA | LEU | A | 84 | 67.836 | −28.450 | −6.704 | 1.00 | 22.65 | A | C |
| ATOM | 1000 | CB | LEU | A | 84 | 69.193 | −29.092 | −6.998 | 1.00 | 20.71 | A | C |
| ATOM | 1003 | CG | LEU | A | 84 | 70.398 | −28.272 | −6.564 | 1.00 | 21.65 | A | C |
| ATOM | 1005 | CD1 | LEU | A | 84 | 71.625 | −29.158 | −6.493 | 1.00 | 18.26 | A | C |
| ATOM | 1009 | CD2 | LEU | A | 84 | 70.634 | −27.090 | −7.483 | 1.00 | 14.55 | A | C |
| ATOM | 1013 | C | LEU | A | 84 | 66.744 | −29.200 | −7.505 | 1.00 | 24.69 | A | C |
| ATOM | 1014 | O | LEU | A | 84 | 66.853 | −29.305 | −8.734 | 1.00 | 24.25 | A | O |
| ATOM | 1016 | N | GLY | A | 85 | 65.718 | −29.718 | −6.826 | 1.00 | 23.20 | A | N |
| ATOM | 1017 | CA | GLY | A | 85 | 64.646 | −30.512 | −7.476 | 1.00 | 24.92 | A | C |
| ATOM | 1020 | C | GLY | A | 85 | 63.962 | −29.846 | −8.659 | 1.00 | 24.61 | A | C |
| ATOM | 1021 | O | GLY | A | 85 | 63.792 | −30.465 | −9.714 | 1.00 | 26.70 | A | O |
| ATOM | 1023 | N | TYR | A | 86 | 63.625 | −28.570 | −8.511 | 1.00 | 26.13 | A | N |
| ATOM | 1024 | CA | TYR | A | 86 | 63.032 | −27.765 | −9.616 | 1.00 | 27.13 | A | C |
| ATOM | 1026 | CB | TYR | A | 86 | 62.880 | −26.295 | −9.195 | 1.00 | 25.38 | A | C |
| ATOM | 1029 | CG | TYR | A | 86 | 64.180 | −25.458 | −9.276 | 1.00 | 21.72 | A | C |
| ATOM | 1030 | CD1 | TYR | A | 86 | 64.428 | −24.637 | −10.362 | 1.00 | 19.43 | A | C |
| ATOM | 1032 | CE1 | TYR | A | 86 | 65.582 | −23.874 | −10.435 | 1.00 | 24.50 | A | C |
| ATOM | 1034 | CZ | TYR | A | 86 | 66.513 | −23.916 | −9.398 | 1.00 | 20.21 | A | C |
| ATOM | 1035 | OH | TYR | A | 86 | 67.655 | −23.164 | −9.489 | 1.00 | 16.34 | A | O |
| ATOM | 1037 | CE2 | TYR | A | 86 | 66.287 | −24.695 | −8.297 | 1.00 | 15.09 | A | C |
| ATOM | 1039 | CD2 | TYR | A | 86 | 65.123 | −25.470 | −8.235 | 1.00 | 20.89 | A | C |
| ATOM | 1041 | C | TYR | A | 86 | 63.861 | −27.803 | −10.904 | 1.00 | 28.47 | A | C |
| ATOM | 1042 | O | TYR | A | 86 | 63.369 | −27.573 | −12.003 | 1.00 | 33.02 | A | O |
| ATOM | 1044 | N | ARG | A | 87 | 65.140 | −28.075 | −10.752 | 1.00 | 28.58 | A | N |
| ATOM | 1045 | CA | ARG | A | 87 | 66.067 | −28.023 | −11.854 | 1.00 | 28.18 | A | C |
| ATOM | 1047 | CB | ARG | A | 87 | 67.395 | −27.694 | −11.215 | 1.00 | 29.83 | A | C |
| ATOM | 1050 | CG | ARG | A | 87 | 68.405 | −27.210 | −12.098 | 1.00 | 31.31 | A | C |
| ATOM | 1053 | CD | ARG | A | 87 | 69.334 | −26.189 | −11.405 | 1.00 | 29.77 | A | C |
| ATOM | 1056 | NE | ARG | A | 87 | 69.857 | −25.501 | −12.548 | 1.00 | 28.60 | A | N |
| ATOM | 1058 | CZ | ARG | A | 87 | 69.522 | −24.301 | −12.934 | 1.00 | 21.90 | A | C |
| ATOM | 1059 | NH1 | ARG | A | 87 | 70.033 | −23.874 | −14.064 | 1.00 | 36.21 | A | N |
| ATOM | 1062 | NH2 | ARG | A | 87 | 68.772 | −23.510 | −12.182 | 1.00 | 22.93 | A | N |
| ATOM | 1065 | C | ARG | A | 87 | 66.115 | −29.349 | −12.639 | 1.00 | 27.31 | A | C |
| ATOM | 1066 | O | ARG | A | 87 | 66.425 | −29.375 | −13.824 | 1.00 | 27.32 | A | O |
| ATOM | 1068 | N | PHE | A | 88 | 65.773 | −30.448 | −11.982 | 1.00 | 26.33 | A | N |
| ATOM | 1069 | CA | PHE | A | 88 | 65.973 | −31.773 | −12.557 | 1.00 | 26.77 | A | C |
| ATOM | 1071 | CB | PHE | A | 88 | 66.993 | −32.547 | −11.717 | 1.00 | 24.89 | A | C |
| ATOM | 1074 | CG | PHE | A | 88 | 68.349 | −31.933 | −11.722 | 1.00 | 24.57 | A | C |
| ATOM | 1075 | CD1 | PHE | A | 88 | 69.151 | −32.027 | −12.851 | 1.00 | 22.34 | A | C |
| ATOM | 1077 | CE1 | PHE | A | 88 | 70.407 | −31.449 | −12.879 | 1.00 | 24.25 | A | C |
| ATOM | 1079 | CZ | PHE | A | 88 | 70.870 | −30.733 | −11.773 | 1.00 | 24.17 | A | C |
| ATOM | 1081 | CE2 | PHE | A | 88 | 70.069 | −30.614 | −10.653 | 1.00 | 22.88 | A | C |
| ATOM | 1083 | CD2 | PHE | A | 88 | 68.808 | −31.217 | −10.629 | 1.00 | 21.57 | A | C |
| ATOM | 1085 | C | PHE | A | 88 | 64.687 | −32.558 | −12.629 | 1.00 | 27.69 | A | C |
| ATOM | 1086 | O | PHE | A | 88 | 64.708 | −33.773 | −12.532 | 1.00 | 28.94 | A | O |
| ATOM | 1088 | N | GLU | A | 89 | 63.571 | −31.870 | −12.834 | 1.00 | 29.75 | A | N |

TABLE 4-2-continued

Coordinates of *P. alba* IspS

| ATOM | 1089 | CA | GLU | A | 89 | 62.274 | −32.508 | −12.692 | 1.00 | 32.99 | A | C |
|------|------|-----|-----|---|----|--------|---------|---------|------|-------|---|---|
| ATOM | 1091 | CB | GLU | A | 89 | 61.102 | −31.513 | −12.765 | 1.00 | 33.37 | A | C |
| ATOM | 1094 | CG | GLU | A | 89 | 59.763 | −32.231 | −12.470 | 1.00 | 46.55 | A | C |
| ATOM | 1097 | CD | GLU | A | 89 | 58.580 | −31.316 | −12.217 | 1.00 | 57.05 | A | C |
| ATOM | 1098 | OE1 | GLU | A | 89 | 58.729 | −30.328 | −11.448 | 1.00 | 60.68 | A | O |
| ATOM | 1099 | OE2 | GLU | A | 89 | 57.496 | −31.622 | −12.775 | 1.00 | 57.95 | A | O |
| ATOM | 1100 | C | GLU | A | 89 | 62.042 | −33.637 | −13.678 | 1.00 | 32.53 | A | C |
| ATOM | 1101 | O | GLU | A | 89 | 61.662 | −34.736 | −13.269 | 1.00 | 32.44 | A | O |
| ATOM | 1103 | N | SER | A | 90 | 62.244 | −33.379 | −14.965 | 1.00 | 31.61 | A | N |
| ATOM | 1104 | CA | SER | A | 90 | 62.011 | −34.420 | −15.965 | 1.00 | 32.03 | A | C |
| ATOM | 1106 | CB | SER | A | 90 | 62.136 | −33.884 | −17.397 | 1.00 | 32.86 | A | C |
| ATOM | 1109 | OG | SER | A | 90 | 63.207 | −32.968 | −17.531 | 1.00 | 41.77 | A | O |
| ATOM | 1111 | C | SER | A | 90 | 62.947 | −35.591 | −15.756 | 1.00 | 29.81 | A | C |
| ATOM | 1112 | O | SER | A | 90 | 62.586 | −36.718 | −16.032 | 1.00 | 31.36 | A | O |
| ATOM | 1114 | N | ASP | A | 91 | 64.154 | −35.326 | −15.256 | 1.00 | 28.19 | A | N |
| ATOM | 1115 | CA | ASP | A | 91 | 65.126 | −36.396 | −15.014 | 1.00 | 24.23 | A | C |
| ATOM | 1117 | CB | ASP | A | 91 | 66.521 | −35.807 | −14.750 | 1.00 | 23.78 | A | C |
| ATOM | 1120 | CG | ASP | A | 91 | 66.966 | −34.819 | −15.851 | 1.00 | 27.08 | A | C |
| ATOM | 1121 | OD1 | ASP | A | 91 | 67.311 | −35.261 | −16.954 | 1.00 | 33.39 | A | O |
| ATOM | 1122 | OD2 | ASP | A | 91 | 66.968 | −33.601 | −15.619 | 1.00 | 36.51 | A | O |
| ATOM | 1123 | C | ASP | A | 91 | 64.657 | −37.237 | −13.820 | 1.00 | 25.06 | A | C |
| ATOM | 1124 | O | ASP | A | 91 | 64.691 | −38.467 | −13.864 | 1.00 | 22.54 | A | O |
| ATOM | 1126 | N | ILE | A | 92 | 64.213 | −36.573 | −12.749 | 1.00 | 22.98 | A | N |
| ATOM | 1127 | CA | ILE | A | 92 | 63.739 | −37.290 | −11.568 | 1.00 | 23.78 | A | C |
| ATOM | 1129 | CB | ILE | A | 92 | 63.401 | −36.337 | −10.446 | 1.00 | 22.94 | A | C |
| ATOM | 1131 | CG1 | ILE | A | 92 | 64.687 | −35.861 | −9.804 | 1.00 | 19.21 | A | C |
| ATOM | 1134 | CD1 | ILE | A | 92 | 64.563 | −34.555 | −9.062 | 1.00 | 17.83 | A | C |
| ATOM | 1138 | CG2 | ILE | A | 92 | 62.526 | −37.040 | −9.414 | 1.00 | 23.71 | A | C |
| ATOM | 1142 | C | ILE | A | 92 | 62.509 | −38.135 | −11.919 | 1.00 | 24.89 | A | C |
| ATOM | 1143 | O | ILE | A | 92 | 62.486 | −39.327 | −11.669 | 1.00 | 23.25 | A | O |
| ATOM | 1145 | N | ARG | A | 93 | 61.513 | −37.524 | −12.542 | 1.00 | 26.25 | A | N |
| ATOM | 1146 | CA | ARG | A | 93 | 60.331 | −38.275 | −12.964 | 1.00 | 28.67 | A | C |
| ATOM | 1148 | CB | ARG | A | 93 | 59.345 | −37.394 | −13.747 | 1.00 | 30.12 | A | C |
| ATOM | 1151 | CG | ARG | A | 93 | 58.786 | −36.167 | −13.040 | 1.00 | 34.31 | A | C |
| ATOM | 1154 | CD | ARG | A | 93 | 57.781 | −35.434 | −14.024 | 1.00 | 38.26 | A | C |
| ATOM | 1157 | NE | ARG | A | 93 | 56.850 | −36.429 | −14.548 | 1.00 | 40.69 | A | N |
| ATOM | 1159 | CZ | ARG | A | 93 | 55.847 | −36.955 | −13.847 | 1.00 | 45.91 | A | C |
| ATOM | 1160 | NH1 | ARG | A | 93 | 55.602 | −36.551 | −12.602 | 1.00 | 47.58 | A | N |
| ATOM | 1163 | NH2 | ARG | A | 93 | 55.059 | −37.874 | −14.392 | 1.00 | 49.96 | A | N |
| ATOM | 1166 | C | ARG | A | 93 | 60.712 | −39.443 | −13.877 | 1.00 | 28.48 | A | C |
| ATOM | 1167 | O | ARG | A | 93 | 60.134 | −40.512 | −13.783 | 1.00 | 28.33 | A | O |
| ATOM | 1169 | N | GLY | A | 94 | 61.655 | −39.219 | −14.790 | 1.00 | 27.77 | A | N |
| ATOM | 1170 | CA | GLY | A | 94 | 62.097 | −40.281 | −15.692 | 1.00 | 26.95 | A | C |
| ATOM | 1173 | C | GLY | A | 94 | 62.607 | −41.477 | −14.914 | 1.00 | 28.30 | A | C |
| ATOM | 1174 | O | GLY | A | 94 | 62.298 | −42.631 | −15.231 | 1.00 | 30.24 | A | O |
| ATOM | 1176 | N | ALA | A | 95 | 63.390 | −41.203 | −13.882 | 1.00 | 25.47 | A | N |
| ATOM | 1177 | CA | ALA | A | 95 | 64.045 | −42.254 | −13.123 | 1.00 | 25.65 | A | C |
| ATOM | 1179 | CB | ALA | A | 95 | 65.183 | −41.658 | −12.263 | 1.00 | 23.46 | A | C |
| ATOM | 1183 | C | ALA | A | 95 | 63.044 | −42.991 | −12.250 | 1.00 | 25.68 | A | C |
| ATOM | 1184 | O | ALA | A | 95 | 63.149 | −44.208 | −12.070 | 1.00 | 27.08 | A | O |
| ATOM | 1186 | N | LEU | A | 96 | 62.073 | −42.266 | −11.711 | 1.00 | 24.42 | A | N |
| ATOM | 1187 | CA | LEU | A | 96 | 61.032 | −42.899 | −10.893 | 1.00 | 25.56 | A | C |
| ATOM | 1189 | CB | LEU | A | 96 | 60.201 | −41.851 | −10.150 | 1.00 | 24.25 | A | C |
| ATOM | 1192 | CG | LEU | A | 96 | 60.979 | −41.085 | −9.090 | 1.00 | 26.81 | A | C |
| ATOM | 1194 | CD1 | LEU | A | 96 | 60.175 | −39.926 | −8.563 | 1.00 | 21.85 | A | C |
| ATOM | 1198 | CD2 | LEU | A | 96 | 61.365 | −42.017 | −7.974 | 1.00 | 23.10 | A | C |
| ATOM | 1202 | C | LEU | A | 96 | 60.121 | −43.764 | −11.755 | 1.00 | 27.28 | A | C |
| ATOM | 1203 | O | LEU | A | 96 | 59.707 | −44.848 | −11.352 | 1.00 | 24.29 | A | O |
| ATOM | 1205 | N | ASP | A | 97 | 59.805 | −43.278 | −12.952 | 1.00 | 31.37 | A | N |
| ATOM | 1206 | CA | ASP | A | 97 | 59.040 | −44.080 | −13.895 | 1.00 | 34.30 | A | C |
| ATOM | 1208 | CB | ASP | A | 97 | 58.875 | −43.351 | −15.205 | 1.00 | 34.30 | A | C |
| ATOM | 1211 | CG | ASP | A | 97 | 57.901 | −44.050 | −16.125 | 1.00 | 47.50 | A | C |
| ATOM | 1212 | OD1 | ASP | A | 97 | 58.360 | −44.783 | −17.041 | 1.00 | 55.79 | A | O |
| ATOM | 1213 | OD2 | ASP | A | 97 | 56.676 | −43.884 | −15.908 | 1.00 | 54.69 | A | O |
| ATOM | 1214 | C | ASP | A | 97 | 59.735 | −45.428 | −14.131 | 1.00 | 35.14 | A | C |
| ATOM | 1215 | O | ASP | A | 97 | 59.110 | −46.485 | −14.136 | 1.00 | 34.56 | A | O |
| ATOM | 1217 | N | ARG | A | 98 | 61.043 | −45.376 | −14.299 | 1.00 | 36.78 | A | N |
| ATOM | 1218 | CA | ARG | A | 98 | 61.813 | −46.568 | −14.600 | 1.00 | 38.34 | A | C |
| ATOM | 1220 | CB | ARG | A | 98 | 63.232 | −46.187 | −15.013 | 1.00 | 38.88 | A | C |
| ATOM | 1223 | CG | ARG | A | 98 | 63.620 | −46.641 | −16.400 | 1.00 | 43.64 | A | C |
| ATOM | 1226 | CD | ARG | A | 98 | 64.485 | −45.611 | −17.145 | 1.00 | 43.57 | A | C |
| ATOM | 1229 | NE | ARG | A | 98 | 65.396 | −44.847 | −16.278 | 1.00 | 39.48 | A | N |
| ATOM | 1231 | CZ | ARG | A | 98 | 65.577 | −43.522 | −16.340 | 1.00 | 34.93 | A | C |
| ATOM | 1232 | NH1 | ARG | A | 98 | 64.927 | −42.778 | −17.238 | 1.00 | 36.94 | A | N |
| ATOM | 1235 | NH2 | ARG | A | 98 | 66.431 | −42.932 | −15.512 | 1.00 | 36.51 | A | N |
| ATOM | 1238 | C | ARG | A | 98 | 61.842 | −47.475 | −13.379 | 1.00 | 37.58 | A | C |
| ATOM | 1239 | O | ARG | A | 98 | 61.787 | −48.692 | −13.519 | 1.00 | 38.96 | A | O |
| ATOM | 1241 | N | PHE | A | 99 | 61.928 | −46.879 | −12.192 | 1.00 | 35.87 | A | N |

TABLE 4-2-continued

Coordinates of *P. alba* IspS

| ATOM | 1242 | CA | PHE | A | 99 | 61.924 | −47.629 | −10.948 | 1.00 | 36.10 | A | C |
|------|------|-----|-----|---|-----|--------|---------|---------|------|-------|---|---|
| ATOM | 1244 | CB | PHE | A | 99 | 62.170 | −46.693 | −9.756 | 1.00 | 37.12 | A | C |
| ATOM | 1247 | CG | PHE | A | 99 | 62.224 | −47.401 | −8.427 | 1.00 | 34.31 | A | C |
| ATOM | 1248 | CD1 | PHE | A | 99 | 63.223 | −48.307 | −8.162 | 1.00 | 37.07 | A | C |
| ATOM | 1250 | CE1 | PHE | A | 99 | 63.275 | −48.973 | −6.943 | 1.00 | 37.15 | A | C |
| ATOM | 1252 | CZ | PHE | A | 99 | 62.322 | −48.714 | −5.970 | 1.00 | 35.62 | A | C |
| ATOM | 1254 | CE2 | PHE | A | 99 | 61.329 | −47.799 | −6.221 | 1.00 | 30.23 | A | C |
| ATOM | 1256 | CD2 | PHE | A | 99 | 61.271 | −47.153 | −7.444 | 1.00 | 34.40 | A | C |
| ATOM | 1258 | C | PHE | A | 99 | 60.614 | −48.406 | −10.759 | 1.00 | 36.72 | A | C |
| ATOM | 1259 | O | PHE | A | 99 | 60.617 | −49.513 | −10.213 | 1.00 | 37.39 | A | O |
| ATOM | 1261 | N | VAL | A | 100 | 59.502 | −47.838 | −11.202 | 1.00 | 35.36 | A | N |
| ATOM | 1262 | CA | VAL | A | 100 | 58.258 | −48.570 | −11.191 | 1.00 | 38.56 | A | C |
| ATOM | 1264 | CB | VAL | A | 100 | 57.054 | −47.635 | −11.263 | 1.00 | 40.72 | A | C |
| ATOM | 1266 | CG1 | VAL | A | 100 | 55.755 | −48.457 | −11.465 | 1.00 | 37.62 | A | C |
| ATOM | 1270 | CG2 | VAL | A | 100 | 56.985 | −46.787 | −9.999 | 1.00 | 33.69 | A | C |
| ATOM | 1274 | C | VAL | A | 100 | 58.202 | −49.563 | −12.367 | 1.00 | 41.18 | A | C |
| ATOM | 1275 | O | VAL | A | 100 | 57.974 | −50.760 | −12.164 | 1.00 | 40.05 | A | O |
| ATOM | 1277 | N | SER | A | 101 | 58.437 | −49.072 | −13.585 | 1.00 | 42.95 | A | N |
| ATOM | 1278 | CA | SER | A | 101 | 58.207 | −49.880 | −14.799 | 1.00 | 45.08 | A | C |
| ATOM | 1280 | CB | SER | A | 101 | 58.507 | −49.087 | −16.079 | 1.00 | 46.29 | A | C |
| ATOM | 1283 | OG | SER | A | 101 | 59.856 | −49.282 | −16.492 | 1.00 | 50.51 | A | O |
| ATOM | 1285 | C | SER | A | 101 | 59.010 | −51.169 | −14.802 | 1.00 | 44.71 | A | C |
| ATOM | 1286 | O | SER | A | 101 | 58.550 | −52.167 | −15.313 | 1.00 | 46.34 | A | O |
| ATOM | 1288 | N | SER | A | 102 | 60.200 | −51.136 | −14.218 | 1.00 | 44.39 | A | N |
| ATOM | 1289 | CA | SER | A | 102 | 61.053 | −52.306 | −14.113 | 1.00 | 45.16 | A | C |
| ATOM | 1291 | CB | SER | A | 102 | 62.506 | −51.847 | −13.944 | 1.00 | 46.36 | A | C |
| ATOM | 1294 | OG | SER | A | 102 | 62.747 | −51.406 | −12.615 | 1.00 | 47.55 | A | O |
| ATOM | 1296 | C | SER | A | 102 | 60.712 | −53.225 | −12.925 | 1.00 | 45.37 | A | C |
| ATOM | 1297 | O | SER | A | 102 | 61.418 | −54.185 | −12.672 | 1.00 | 44.04 | A | O |
| ATOM | 1299 | N | GLY | A | 103 | 59.669 | −52.904 | −12.167 | 1.00 | 46.21 | A | N |
| ATOM | 1300 | CA | GLY | A | 103 | 59.343 | −53.663 | −10.955 | 1.00 | 46.61 | A | C |
| ATOM | 1303 | C | GLY | A | 103 | 60.241 | −53.437 | −9.745 | 1.00 | 45.81 | A | C |
| ATOM | 1304 | O | GLY | A | 103 | 60.133 | −54.155 | −8.747 | 1.00 | 46.61 | A | O |
| ATOM | 1306 | N | GLY | A | 104 | 61.123 | −52.444 | −9.817 | 1.00 | 45.47 | A | N |
| ATOM | 1307 | CA | GLY | A | 104 | 62.011 | −52.136 | −8.702 | 1.00 | 44.33 | A | C |
| ATOM | 1310 | C | GLY | A | 104 | 61.271 | −51.766 | −7.434 | 1.00 | 42.90 | A | C |
| ATOM | 1311 | O | GLY | A | 104 | 61.640 | −52.210 | −6.339 | 1.00 | 43.32 | A | O |
| ATOM | 1313 | N | PHE | A | 105 | 60.228 | −50.955 | −7.574 | 1.00 | 41.44 | A | N |
| ATOM | 1314 | CA | PHE | A | 105 | 59.401 | −50.578 | −6.426 | 1.00 | 42.25 | A | C |
| ATOM | 1316 | CB | PHE | A | 105 | 58.309 | −49.569 | −6.800 | 1.00 | 40.65 | A | C |
| ATOM | 1319 | CG | PHE | A | 105 | 57.434 | −49.159 | −5.634 | 1.00 | 39.69 | A | C |
| ATOM | 1320 | CD1 | PHE | A | 105 | 57.991 | −48.615 | −4.485 | 1.00 | 35.48 | A | C |
| ATOM | 1322 | CE1 | PHE | A | 105 | 57.189 | −48.232 | −3.411 | 1.00 | 38.34 | A | C |
| ATOM | 1324 | CZ | PHE | A | 105 | 55.816 | −48.397 | −3.486 | 1.00 | 41.55 | A | C |
| ATOM | 1326 | CE2 | PHE | A | 105 | 55.253 | −48.938 | −4.612 | 1.00 | 38.70 | A | C |
| ATOM | 1328 | CD2 | PHE | A | 105 | 56.058 | −49.308 | −5.687 | 1.00 | 42.66 | A | C |
| ATOM | 1330 | C | PHE | A | 105 | 58.765 | −51.800 | −5.799 | 1.00 | 43.53 | A | C |
| ATOM | 1331 | O | PHE | A | 105 | 58.700 | −51.904 | −4.584 | 1.00 | 42.87 | A | O |
| ATOM | 1333 | N | ASP | A | 106 | 58.297 | −52.729 | −6.623 | 1.00 | 46.74 | A | N |
| ATOM | 1334 | CA | ASP | A | 106 | 57.714 | −53.948 | −6.093 | 1.00 | 49.25 | A | C |
| ATOM | 1336 | CB | ASP | A | 106 | 57.058 | −54.776 | −7.199 | 1.00 | 52.47 | A | C |
| ATOM | 1339 | CG | ASP | A | 106 | 55.671 | −55.256 | −6.807 | 1.00 | 60.96 | A | C |
| ATOM | 1340 | OD1 | ASP | A | 106 | 54.826 | −54.386 | −6.468 | 1.00 | 69.59 | A | O |
| ATOM | 1341 | OD2 | ASP | A | 106 | 55.436 | −56.486 | −6.828 | 1.00 | 66.22 | A | O |
| ATOM | 1342 | C | ASP | A | 106 | 58.775 | −54.756 | −5.354 | 1.00 | 48.33 | A | C |
| ATOM | 1343 | O | ASP | A | 106 | 58.521 | −55.290 | −4.271 | 1.00 | 48.27 | A | O |
| ATOM | 1345 | N | ALA | A | 107 | 59.971 | −54.821 | −5.927 | 1.00 | 46.84 | A | N |
| ATOM | 1346 | CA | ALA | A | 107 | 61.096 | −55.440 | −5.246 | 1.00 | 45.49 | A | C |
| ATOM | 1348 | CB | ALA | A | 107 | 62.380 | −55.283 | −6.070 | 1.00 | 46.29 | A | C |
| ATOM | 1352 | C | ALA | A | 107 | 61.285 | −54.846 | −3.853 | 1.00 | 44.32 | A | C |
| ATOM | 1353 | O | ALA | A | 107 | 61.248 | −55.581 | −2.861 | 1.00 | 45.24 | A | O |
| ATOM | 1355 | N | VAL | A | 108 | 61.468 | −53.527 | −3.752 | 1.00 | 42.93 | A | N |
| ATOM | 1356 | CA | VAL | A | 108 | 61.877 | −52.954 | −2.458 | 1.00 | 40.66 | A | C |
| ATOM | 1358 | CB | VAL | A | 108 | 62.288 | −51.469 | −2.511 | 1.00 | 41.66 | A | C |
| ATOM | 1360 | CG1 | VAL | A | 108 | 63.411 | −51.263 | −3.531 | 1.00 | 48.84 | A | C |
| ATOM | 1364 | CG2 | VAL | A | 108 | 61.078 | −50.566 | −2.778 | 1.00 | 34.77 | A | C |
| ATOM | 1368 | C | VAL | A | 108 | 60.835 | −53.130 | −1.373 | 1.00 | 39.03 | A | C |
| ATOM | 1369 | O | VAL | A | 108 | 61.198 | −53.207 | −0.210 | 1.00 | 38.61 | A | O |
| ATOM | 1371 | N | THR | A | 109 | 59.558 | −53.220 | −1.739 | 1.00 | 39.24 | A | N |
| ATOM | 1372 | CA | THR | A | 109 | 58.504 | −53.460 | −0.747 | 1.00 | 40.61 | A | C |
| ATOM | 1374 | CB | THR | A | 109 | 57.078 | −53.384 | −1.330 | 1.00 | 40.51 | A | C |
| ATOM | 1376 | OG1 | THR | A | 109 | 56.840 | −54.523 | −2.162 | 1.00 | 40.09 | A | O |
| ATOM | 1378 | CG2 | THR | A | 109 | 56.853 | −52.075 | −2.115 | 1.00 | 38.58 | A | C |
| ATOM | 1382 | C | THR | A | 109 | 58.656 | −54.815 | −0.042 | 1.00 | 42.53 | A | C |
| ATOM | 1383 | O | THR | A | 109 | 58.130 | −54.999 | 1.061 | 1.00 | 42.34 | A | O |
| ATOM | 1385 | N | LYS | A | 110 | 59.365 | −55.751 | −0.673 | 1.00 | 44.78 | A | N |
| ATOM | 1386 | CA | LYS | A | 110 | 59.616 | −57.080 | −0.082 | 1.00 | 47.15 | A | C |
| ATOM | 1388 | CB | LYS | A | 110 | 59.788 | −58.164 | −1.164 | 1.00 | 48.00 | A | C |

TABLE 4-2-continued

Coordinates of *P. alba* IspS

| ATOM | 1391 | CG | LYS | A | 110 | 58.761 | −58.189 | −2.295 | 1.00 | 52.11 | A | C |
|------|------|-----|-----|---|-----|--------|---------|--------|------|-------|---|---|
| ATOM | 1394 | CD | LYS | A | 110 | 57.351 | −58.484 | −1.819 | 1.00 | 60.28 | A | C |
| ATOM | 1397 | CE | LYS | A | 110 | 56.382 | −58.578 | −3.010 | 1.00 | 65.15 | A | C |
| ATOM | 1400 | NZ | LYS | A | 110 | 55.021 | −58.046 | −2.683 | 1.00 | 64.69 | A | N |
| ATOM | 1404 | C | LYS | A | 110 | 60.873 | −57.096 | 0.778 | 1.00 | 46.28 | A | C |
| ATOM | 1405 | O | LYS | A | 110 | 61.028 | −57.984 | 1.603 | 1.00 | 47.54 | A | O |
| ATOM | 1407 | N | THR | A | 111 | 61.770 | −56.131 | 0.570 | 1.00 | 46.36 | A | N |
| ATOM | 1408 | CA | THR | A | 111 | 63.123 | −56.191 | 1.133 | 1.00 | 45.50 | A | C |
| ATOM | 1410 | CB | THR | A | 111 | 64.197 | −56.315 | 0.003 | 1.00 | 47.36 | A | C |
| ATOM | 1412 | OG1 | THR | A | 111 | 64.312 | −55.076 | −0.711 | 1.00 | 50.35 | A | O |
| ATOM | 1414 | CG2 | THR | A | 111 | 63.837 | −57.451 | −1.000 | 1.00 | 47.26 | A | C |
| ATOM | 1418 | C | THR | A | 111 | 63.530 | −55.041 | 2.061 | 1.00 | 44.00 | A | C |
| ATOM | 1419 | O | THR | A | 111 | 64.272 | −55.284 | 3.019 | 1.00 | 44.86 | A | O |
| ATOM | 1421 | N | SER | A | 112 | 63.078 | −53.806 | 1.798 | 1.00 | 40.92 | A | N |
| ATOM | 1422 | CA | SER | A | 112 | 63.645 | −52.611 | 2.480 | 1.00 | 37.38 | A | C |
| ATOM | 1424 | CB | SER | A | 112 | 64.723 | −51.988 | 1.578 | 1.00 | 38.61 | A | C |
| ATOM | 1427 | OG | SER | A | 112 | 65.350 | −50.861 | 2.173 | 1.00 | 42.50 | A | O |
| ATOM | 1429 | C | SER | A | 112 | 62.600 | −51.542 | 2.889 | 1.00 | 33.43 | A | C |
| ATOM | 1430 | O | SER | A | 112 | 61.986 | −50.896 | 2.037 | 1.00 | 31.07 | A | O |
| ATOM | 1432 | N | LEU | A | 113 | 62.399 | −51.372 | 4.194 | 1.00 | 29.38 | A | N |
| ATOM | 1433 | CA | LEU | A | 113 | 61.529 | −50.323 | 4.709 | 1.00 | 29.45 | A | C |
| ATOM | 1435 | CB | LEU | A | 113 | 61.443 | −50.353 | 6.241 | 1.00 | 29.86 | A | C |
| ATOM | 1438 | CG | LEU | A | 113 | 60.553 | −49.263 | 6.868 | 1.00 | 31.38 | A | C |
| ATOM | 1440 | CD1 | LEU | A | 113 | 59.109 | −49.437 | 6.427 | 1.00 | 29.65 | A | C |
| ATOM | 1444 | CD2 | LEU | A | 113 | 60.631 | −49.299 | 8.378 | 1.00 | 33.60 | A | C |
| ATOM | 1448 | C | LEU | A | 113 | 62.017 | −48.954 | 4.268 | 1.00 | 28.16 | A | C |
| ATOM | 1449 | O | LEU | A | 113 | 61.237 | −48.138 | 3.810 | 1.00 | 29.40 | A | O |
| ATOM | 1451 | N | HIS | A | 114 | 63.308 | −48.706 | 4.417 | 1.00 | 27.25 | A | N |
| ATOM | 1452 | CA | HIS | A | 114 | 63.902 | −47.461 | 3.960 | 1.00 | 28.38 | A | C |
| ATOM | 1454 | CB | HIS | A | 114 | 65.418 | −47.448 | 4.175 | 1.00 | 29.85 | A | C |
| ATOM | 1457 | CG | HIS | A | 114 | 66.073 | −46.214 | 3.663 | 1.00 | 29.52 | A | C |
| ATOM | 1458 | ND1 | HIS | A | 114 | 65.529 | −44.961 | 3.846 | 1.00 | 36.46 | A | N |
| ATOM | 1460 | CE1 | HIS | A | 114 | 66.310 | −44.057 | 3.281 | 1.00 | 35.11 | A | C |
| ATOM | 1462 | NE2 | HIS | A | 114 | 67.322 | −44.682 | 2.711 | 1.00 | 36.38 | A | N |
| ATOM | 1464 | CD2 | HIS | A | 114 | 67.197 | −46.033 | 2.937 | 1.00 | 36.40 | A | C |
| ATOM | 1466 | C | HIS | A | 114 | 63.595 | −47.220 | 2.493 | 1.00 | 27.08 | A | C |
| ATOM | 1467 | O | HIS | A | 114 | 63.089 | −46.166 | 2.127 | 1.00 | 25.36 | A | O |
| ATOM | 1469 | N | GLY | A | 115 | 63.884 | −48.214 | 1.665 | 1.00 | 27.32 | A | N |
| ATOM | 1470 | CA | GLY | A | 115 | 63.647 | −48.120 | 0.234 | 1.00 | 25.75 | A | C |
| ATOM | 1473 | C | GLY | A | 115 | 62.184 | −47.904 | −0.102 | 1.00 | 26.39 | A | C |
| ATOM | 1474 | O | GLY | A | 115 | 61.858 | −47.150 | −1.041 | 1.00 | 26.71 | A | O |
| ATOM | 1476 | N | THR | A | 116 | 61.306 | −48.567 | 0.657 | 1.00 | 24.29 | A | N |
| ATOM | 1477 | CA | THR | A | 116 | 59.865 | −48.470 | 0.431 | 1.00 | 24.57 | A | C |
| ATOM | 1479 | CB | THR | A | 116 | 59.111 | −49.555 | 1.168 | 1.00 | 25.44 | A | C |
| ATOM | 1481 | OG1 | THR | A | 116 | 59.620 | −50.825 | 0.738 | 1.00 | 27.83 | A | O |
| ATOM | 1483 | CG2 | THR | A | 116 | 57.589 | −49.476 | 0.868 | 1.00 | 20.09 | A | C |
| ATOM | 1487 | C | THR | A | 116 | 59.307 | −47.113 | 0.832 | 1.00 | 25.48 | A | C |
| ATOM | 1488 | O | THR | A | 116 | 58.594 | −46.491 | 0.046 | 1.00 | 25.53 | A | O |
| ATOM | 1490 | N | ALA | A | 117 | 59.659 | −46.647 | 2.028 | 1.00 | 23.44 | A | N |
| ATOM | 1491 | CA | ALA | A | 117 | 59.194 | −45.356 | 2.505 | 1.00 | 24.19 | A | C |
| ATOM | 1493 | CB | ALA | A | 117 | 59.478 | −45.193 | 4.016 | 1.00 | 23.46 | A | C |
| ATOM | 1497 | C | ALA | A | 117 | 59.791 | −44.201 | 1.699 | 1.00 | 24.21 | A | C |
| ATOM | 1498 | O | ALA | A | 117 | 59.112 | −43.225 | 1.436 | 1.00 | 23.16 | A | O |
| ATOM | 1500 | N | LEU | A | 118 | 61.048 | −44.301 | 1.286 | 1.00 | 24.65 | A | N |
| ATOM | 1501 | CA | LEU | A | 118 | 61.631 | −43.222 | 0.443 | 1.00 | 25.43 | A | C |
| ATOM | 1503 | CB | LEU | A | 118 | 63.157 | −43.356 | 0.339 | 1.00 | 24.64 | A | C |
| ATOM | 1506 | CG | LEU | A | 118 | 63.924 | −42.343 | −0.519 | 1.00 | 29.58 | A | C |
| ATOM | 1508 | CD1 | LEU | A | 118 | 63.697 | −40.923 | −0.069 | 1.00 | 22.30 | A | C |
| ATOM | 1512 | CD2 | LEU | A | 118 | 65.403 | −42.690 | −0.477 | 1.00 | 24.34 | A | C |
| ATOM | 1516 | C | LEU | A | 118 | 60.986 | −43.203 | −0.936 | 1.00 | 24.40 | A | C |
| ATOM | 1517 | O | LEU | A | 118 | 60.497 | −42.172 | −1.409 | 1.00 | 24.21 | A | O |
| ATOM | 1519 | N | SER | A | 119 | 60.943 | −44.362 | −1.580 | 1.00 | 25.13 | A | N |
| ATOM | 1520 | CA | SER | A | 119 | 60.368 | −44.416 | −2.916 | 1.00 | 23.95 | A | C |
| ATOM | 1522 | CB | SER | A | 119 | 60.589 | −45.779 | −3.563 | 1.00 | 25.32 | A | C |
| ATOM | 1525 | OG | SER | A | 119 | 59.934 | −46.812 | −2.867 | 1.00 | 26.72 | A | O |
| ATOM | 1527 | C | SER | A | 119 | 58.892 | −44.054 | −2.902 | 1.00 | 23.29 | A | C |
| ATOM | 1528 | O | SER | A | 119 | 58.429 | −43.326 | −3.770 | 1.00 | 23.89 | A | O |
| ATOM | 1530 | N | PHE | A | 120 | 58.162 | −44.537 | −1.903 | 1.00 | 22.65 | A | N |
| ATOM | 1531 | CA | PHE | A | 120 | 56.760 | −44.152 | −1.715 | 1.00 | 22.34 | A | C |
| ATOM | 1533 | CB | PHE | A | 120 | 56.202 | −44.766 | −0.422 | 1.00 | 22.44 | A | C |
| ATOM | 1536 | CG | PHE | A | 120 | 54.758 | −44.427 | −0.154 | 1.00 | 23.67 | A | C |
| ATOM | 1537 | CD1 | PHE | A | 120 | 53.752 | −45.312 | −0.480 | 1.00 | 26.16 | A | C |
| ATOM | 1539 | CE1 | PHE | A | 120 | 52.413 | −45.001 | −0.220 | 1.00 | 26.81 | A | C |
| ATOM | 1541 | CZ | PHE | A | 120 | 52.092 | −43.791 | 0.378 | 1.00 | 23.94 | A | C |
| ATOM | 1543 | CE2 | PHE | A | 120 | 53.089 | −42.932 | 0.722 | 1.00 | 23.73 | A | C |
| ATOM | 1545 | CD2 | PHE | A | 120 | 54.414 | −43.240 | 0.454 | 1.00 | 25.92 | A | C |
| ATOM | 1547 | C | PHE | A | 120 | 56.606 | −42.630 | −1.669 | 1.00 | 20.61 | A | C |
| ATOM | 1548 | O | PHE | A | 120 | 55.759 | −42.066 | −2.345 | 1.00 | 19.01 | A | O |

TABLE 4-2-continued

Coordinates of P. alba IspS

| ATOM | 1550 | N | ARG | A | 121 | 57.410 | −41.966 | −0.850 | 1.00 | 19.18 | A | N |
|---|---|---|---|---|---|---|---|---|---|---|---|---|
| ATOM | 1551 | CA | ARG | A | 121 | 57.326 | −40.506 | −0.775 | 1.00 | 20.59 | A | C |
| ATOM | 1553 | CB | ARG | A | 121 | 58.263 | −39.962 | 0.293 | 1.00 | 20.27 | A | C |
| ATOM | 1556 | CG | ARG | A | 121 | 58.293 | −38.443 | 0.373 | 1.00 | 20.89 | A | C |
| ATOM | 1559 | CD | ARG | A | 121 | 58.902 | −37.979 | 1.690 | 1.00 | 25.20 | A | C |
| ATOM | 1562 | NE | ARG | A | 121 | 60.315 | −38.344 | 1.819 | 1.00 | 23.57 | A | N |
| ATOM | 1564 | CZ | ARG | A | 121 | 61.313 | −37.708 | 1.209 | 1.00 | 23.54 | A | C |
| ATOM | 1565 | NH1 | ARG | A | 121 | 61.068 | −36.674 | 0.414 | 1.00 | 25.58 | A | N |
| ATOM | 1568 | NH2 | ARG | A | 121 | 62.566 | −38.101 | 1.399 | 1.00 | 26.88 | A | N |
| ATOM | 1571 | C | ARG | A | 121 | 57.648 | −39.851 | −2.127 | 1.00 | 19.48 | A | C |
| ATOM | 1572 | O | ARG | A | 121 | 56.909 | −38.997 | −2.609 | 1.00 | 19.29 | A | O |
| ATOM | 1574 | N | LEU | A | 122 | 58.759 | −40.238 | −2.730 | 1.00 | 18.56 | A | N |
| ATOM | 1575 | CA | LEU | A | 122 | 59.159 | −39.613 | −4.017 | 1.00 | 20.57 | A | C |
| ATOM | 1577 | CB | LEU | A | 122 | 60.537 | −40.098 | −4.452 | 1.00 | 18.26 | A | C |
| ATOM | 1580 | CG | LEU | A | 122 | 61.666 | −39.788 | −3.466 | 1.00 | 21.60 | A | C |
| ATOM | 1582 | CD1 | LEU | A | 122 | 62.946 | −40.470 | −3.896 | 1.00 | 21.70 | A | C |
| ATOM | 1586 | CD2 | LEU | A | 122 | 61.855 | −38.314 | −3.393 | 1.00 | 16.48 | A | C |
| ATOM | 1590 | C | LEU | A | 122 | 58.121 | −39.881 | −5.129 | 1.00 | 20.63 | A | C |
| ATOM | 1591 | O | LEU | A | 122 | 57.780 | −39.002 | −5.914 | 1.00 | 21.52 | A | O |
| ATOM | 1593 | N | LEU | A | 123 | 57.594 | −41.088 | −5.167 | 1.00 | 20.62 | A | N |
| ATOM | 1594 | CA | LEU | A | 123 | 56.623 | −41.439 | −6.195 | 1.00 | 20.75 | A | C |
| ATOM | 1596 | CB | LEU | A | 123 | 56.330 | −42.919 | −6.128 | 1.00 | 20.28 | A | C |
| ATOM | 1599 | CG | LEU | A | 123 | 57.412 | −43.829 | −6.735 | 1.00 | 22.58 | A | C |
| ATOM | 1601 | CD1 | LEU | A | 123 | 57.134 | −45.289 | −6.354 | 1.00 | 20.41 | A | C |
| ATOM | 1605 | CD2 | LEU | A | 123 | 57.468 | −43.716 | −8.242 | 1.00 | 19.56 | A | C |
| ATOM | 1609 | C | LEU | A | 123 | 55.345 | −40.604 | −6.046 | 1.00 | 21.54 | A | C |
| ATOM | 1610 | O | LEU | A | 123 | 54.858 | −39.995 | −7.011 | 1.00 | 20.27 | A | O |
| ATOM | 1612 | N | ARG | A | 124 | 54.820 | −40.534 | −4.829 | 1.00 | 22.21 | A | N |
| ATOM | 1613 | CA | ARG | A | 124 | 53.585 | −39.797 | −4.615 | 1.00 | 20.97 | A | C |
| ATOM | 1615 | CB | ARG | A | 124 | 52.987 | −40.096 | −3.246 | 1.00 | 19.35 | A | C |
| ATOM | 1618 | CG | ARG | A | 124 | 51.792 | −39.228 | −2.932 | 1.00 | 23.37 | A | C |
| ATOM | 1621 | CD | ARG | A | 124 | 51.015 | −39.762 | −1.753 | 1.00 | 23.81 | A | C |
| ATOM | 1624 | NE | ARG | A | 124 | 50.298 | −41.008 | −2.048 | 1.00 | 20.90 | A | N |
| ATOM | 1626 | CZ | ARG | A | 124 | 49.550 | −41.652 | −1.158 | 1.00 | 23.68 | A | C |
| ATOM | 1627 | NH1 | ARG | A | 124 | 49.450 | −41.192 | 0.085 | 1.00 | 19.23 | A | N |
| ATOM | 1630 | NH2 | ARG | A | 124 | 48.900 | −42.746 | −1.502 | 1.00 | 20.41 | A | N |
| ATOM | 1633 | C | ARG | A | 124 | 53.831 | −38.321 | −4.814 | 1.00 | 18.12 | A | C |
| ATOM | 1634 | O | ARG | A | 124 | 53.021 | −37.627 | −5.402 | 1.00 | 21.48 | A | O |
| ATOM | 1636 | N | GLN | A | 125 | 54.959 | −37.831 | −4.343 | 1.00 | 20.20 | A | N |
| ATOM | 1637 | CA | GLN | A | 125 | 55.321 | −36.430 | −4.584 | 1.00 | 21.03 | A | C |
| ATOM | 1639 | CB | GLN | A | 125 | 56.744 | −36.147 | −4.080 | 1.00 | 21.65 | A | C |
| ATOM | 1642 | CG | GLN | A | 125 | 57.280 | −34.765 | −4.498 | 1.00 | 20.36 | A | C |
| ATOM | 1645 | CD | GLN | A | 125 | 58.726 | −34.527 | −4.121 | 1.00 | 26.60 | A | C |
| ATOM | 1646 | OE1 | GLN | A | 125 | 59.381 | −35.390 | −3.526 | 1.00 | 21.64 | A | O |
| ATOM | 1647 | NE2 | GLN | A | 125 | 59.247 | −33.352 | −4.492 | 1.00 | 18.29 | A | N |
| ATOM | 1650 | C | GLN | A | 125 | 55.266 | −36.089 | −6.080 | 1.00 | 21.86 | A | C |
| ATOM | 1651 | O | GLN | A | 125 | 54.826 | −34.999 | −6.477 | 1.00 | 23.50 | A | O |
| ATOM | 1653 | N | HIS | A | 126 | 55.739 | −37.011 | −6.912 | 1.00 | 22.17 | A | N |
| ATOM | 1654 | CA | HIS | A | 126 | 55.787 | −36.760 | −8.350 | 1.00 | 23.23 | A | C |
| ATOM | 1656 | CB | HIS | A | 126 | 57.100 | −37.293 | −8.904 | 1.00 | 23.41 | A | C |
| ATOM | 1659 | CG | HIS | A | 126 | 58.250 | −36.415 | −8.563 | 1.00 | 20.04 | A | C |
| ATOM | 1660 | ND1 | HIS | A | 126 | 58.516 | −35.260 | −9.256 | 1.00 | 26.32 | A | N |
| ATOM | 1662 | CE1 | HIS | A | 126 | 59.541 | −34.646 | −8.700 | 1.00 | 22.03 | A | C |
| ATOM | 1664 | NE2 | HIS | A | 126 | 59.942 | −35.359 | −7.667 | 1.00 | 19.54 | A | N |
| ATOM | 1666 | CD2 | HIS | A | 126 | 59.139 | −36.463 | −7.548 | 1.00 | 18.20 | A | C |
| ATOM | 1668 | C | HIS | A | 126 | 54.568 | −37.274 | −9.096 | 1.00 | 25.26 | A | C |
| ATOM | 1669 | O | HIS | A | 126 | 54.602 | −37.438 | −10.311 | 1.00 | 26.07 | A | O |
| ATOM | 1671 | N | GLY | A | 127 | 53.479 | −37.528 | −8.371 | 1.00 | 25.78 | A | N |
| ATOM | 1672 | CA | GLY | A | 127 | 52.198 | −37.783 | −9.033 | 1.00 | 24.01 | A | C |
| ATOM | 1675 | C | GLY | A | 127 | 51.898 | −39.232 | −9.348 | 1.00 | 23.73 | A | C |
| ATOM | 1676 | O | GLY | A | 127 | 50.879 | −39.513 | −9.937 | 1.00 | 28.90 | A | O |
| ATOM | 1678 | N | PHE | A | 128 | 52.763 | −40.163 | −8.977 | 1.00 | 23.33 | A | N |
| ATOM | 1679 | CA | PHE | A | 128 | 52.490 | −41.563 | −9.251 | 1.00 | 25.32 | A | C |
| ATOM | 1681 | CB | PHE | A | 128 | 53.775 | −42.381 | −9.271 | 1.00 | 23.93 | A | C |
| ATOM | 1684 | CG | PHE | A | 128 | 54.725 | −42.003 | −10.366 | 1.00 | 26.62 | A | C |
| ATOM | 1685 | CD1 | PHE | A | 128 | 54.739 | −42.698 | −11.555 | 1.00 | 27.05 | A | C |
| ATOM | 1687 | CE1 | PHE | A | 128 | 55.633 | −42.369 | −12.551 | 1.00 | 30.59 | A | C |
| ATOM | 1689 | CZ | PHE | A | 128 | 56.513 | −41.321 | −12.368 | 1.00 | 33.45 | A | C |
| ATOM | 1691 | CE2 | PHE | A | 128 | 56.500 | −40.627 | −11.187 | 1.00 | 30.11 | A | C |
| ATOM | 1693 | CD2 | PHE | A | 128 | 55.629 | −40.979 | −10.194 | 1.00 | 25.68 | A | C |
| ATOM | 1695 | C | PHE | A | 128 | 51.535 | −42.136 | −8.193 | 1.00 | 28.35 | A | C |
| ATOM | 1696 | O | PHE | A | 128 | 51.473 | −41.657 | −7.062 | 1.00 | 28.35 | A | O |
| ATOM | 1698 | N | GLU | A | 129 | 50.828 | −43.178 | −8.584 | 1.00 | 30.58 | A | N |
| ATOM | 1699 | CA | GLU | A | 129 | 49.896 | −43.880 | −7.739 | 1.00 | 33.23 | A | C |
| ATOM | 1701 | CB | GLU | A | 129 | 48.816 | −44.578 | −8.589 | 1.00 | 34.45 | A | C |
| ATOM | 1704 | CG | GLU | A | 129 | 47.751 | −43.588 | −9.137 | 1.00 | 47.35 | A | C |
| ATOM | 1707 | CD | GLU | A | 129 | 46.460 | −44.250 | −9.690 | 1.00 | 59.81 | A | C |
| ATOM | 1708 | OE1 | GLU | A | 129 | 45.701 | −43.545 | −10.403 | 1.00 | 60.68 | A | O |

TABLE 4-2-continued

Coordinates of *P. alba* IspS

| ATOM | 1709 | OE2 | GLU | A | 129 | 46.191 | −45.448 | −9.409 | 1.00 | 66.05 | A | O |
|---|---|---|---|---|---|---|---|---|---|---|---|---|
| ATOM | 1710 | C | GLU | A | 129 | 50.630 | −44.910 | −6.913 | 1.00 | 30.73 | A | C |
| ATOM | 1711 | O | GLU | A | 129 | 51.213 | −45.846 | −7.455 | 1.00 | 30.68 | A | O |
| ATOM | 1713 | N | VAL | A | 130 | 50.610 | −44.735 | −5.601 | 1.00 | 27.24 | A | N |
| ATOM | 1714 | CA | VAL | A | 130 | 51.116 | −45.775 | −4.718 | 1.00 | 26.66 | A | C |
| ATOM | 1716 | CB | VAL | A | 130 | 52.486 | −45.414 | −4.131 | 1.00 | 26.82 | A | C |
| ATOM | 1718 | CG1 | VAL | A | 130 | 53.534 | −45.415 | −5.233 | 1.00 | 26.47 | A | C |
| ATOM | 1722 | CG2 | VAL | A | 130 | 52.439 | −44.045 | −3.428 | 1.00 | 22.87 | A | C |
| ATOM | 1726 | C | VAL | A | 130 | 50.101 | −45.976 | −3.618 | 1.00 | 25.49 | A | C |
| ATOM | 1727 | O | VAL | A | 130 | 49.328 | −45.069 | −3.314 | 1.00 | 23.94 | A | O |
| ATOM | 1729 | N | SER | A | 131 | 50.094 | −47.168 | −3.035 | 1.00 | 25.58 | A | N |
| ATOM | 1730 | CA | SER | A | 131 | 49.112 | −47.518 | −2.021 | 1.00 | 25.94 | A | C |
| ATOM | 1732 | CB | SER | A | 131 | 48.356 | −48.780 | −2.443 | 1.00 | 29.50 | A | C |
| ATOM | 1735 | OG | SER | A | 131 | 47.847 | −49.475 | −1.304 | 1.00 | 28.83 | A | O |
| ATOM | 1737 | C | SER | A | 131 | 49.764 | −47.783 | −0.707 | 1.00 | 23.83 | A | C |
| ATOM | 1738 | O | SER | A | 131 | 50.909 | −48.214 | −0.668 | 1.00 | 24.97 | A | O |
| ATOM | 1740 | N | GLN | A | 132 | 49.015 | −47.581 | 0.375 | 1.00 | 24.32 | A | N |
| ATOM | 1741 | CA | GLN | A | 132 | 49.526 | −47.858 | 1.733 | 1.00 | 25.61 | A | C |
| ATOM | 1743 | CB | GLN | A | 132 | 48.516 | −47.393 | 2.800 | 1.00 | 24.08 | A | C |
| ATOM | 1746 | CG | GLN | A | 132 | 47.161 | −48.125 | 2.806 | 1.00 | 27.85 | A | C |
| ATOM | 1749 | CD | GLN | A | 132 | 46.283 | −47.760 | 4.011 | 1.00 | 25.79 | A | C |
| ATOM | 1750 | OE1 | GLN | A | 132 | 46.644 | −46.918 | 4.824 | 1.00 | 26.01 | A | O |
| ATOM | 1751 | NE2 | GLN | A | 132 | 45.129 | −48.398 | 4.118 | 1.00 | 27.24 | A | N |
| ATOM | 1754 | C | GLN | A | 132 | 49.904 | −49.353 | 1.924 | 1.00 | 26.55 | A | C |
| ATOM | 1755 | O | GLN | A | 132 | 50.751 | −49.702 | 2.742 | 1.00 | 23.45 | A | O |
| ATOM | 1757 | N | GLU | A | 133 | 49.299 | −50.236 | 1.147 | 1.00 | 26.74 | A | N |
| ATOM | 1758 | CA | GLU | A | 133 | 49.661 | −51.643 | 1.243 | 1.00 | 30.43 | A | C |
| ATOM | 1760 | CB | GLU | A | 133 | 48.627 | −52.582 | 0.584 | 1.00 | 31.92 | A | C |
| ATOM | 1763 | CG | GLU | A | 133 | 48.242 | −52.326 | −0.834 | 1.00 | 41.00 | A | C |
| ATOM | 1766 | CD | GLU | A | 133 | 46.890 | −52.992 | −1.251 | 1.00 | 47.38 | A | C |
| ATOM | 1767 | OE1 | GLU | A | 133 | 45.793 | −52.388 | −1.115 | 1.00 | 48.99 | A | O |
| ATOM | 1768 | OE2 | GLU | A | 133 | 46.944 | −54.114 | −1.767 | 1.00 | 48.11 | A | O |
| ATOM | 1769 | C | GLU | A | 133 | 51.104 | −51.920 | 0.816 | 1.00 | 30.03 | A | C |
| ATOM | 1770 | O | GLU | A | 133 | 51.634 | −52.980 | 1.099 | 1.00 | 30.56 | A | O |
| ATOM | 1772 | N | ALA | A | 134 | 51.779 | −50.944 | 0.220 | 1.00 | 30.33 | A | N |
| ATOM | 1773 | CA | ALA | A | 134 | 53.229 | −51.050 | 0.026 | 1.00 | 29.74 | A | C |
| ATOM | 1775 | CB | ALA | A | 134 | 53.759 | −49.793 | −0.603 | 1.00 | 28.04 | A | C |
| ATOM | 1779 | C | ALA | A | 134 | 53.976 | −51.319 | 1.333 | 1.00 | 30.69 | A | C |
| ATOM | 1780 | O | ALA | A | 134 | 55.073 | −51.845 | 1.323 | 1.00 | 31.48 | A | O |
| ATOM | 1782 | N | PHE | A | 135 | 53.377 | 50.946 | 2.454 | 1.00 | 31.85 | A | N |
| ATOM | 1783 | CA | PHE | A | 135 | 53.987 | −51.134 | 3.762 | 1.00 | 31.97 | A | C |
| ATOM | 1785 | CB | PHE | A | 135 | 53.673 | −49.906 | 4.633 | 1.00 | 29.56 | A | C |
| ATOM | 1788 | CG | PHE | A | 135 | 54.296 | −48.619 | 4.122 | 1.00 | 28.98 | A | C |
| ATOM | 1789 | CD1 | PHE | A | 135 | 53.549 | −47.697 | 3.402 | 1.00 | 24.38 | A | C |
| ATOM | 1791 | CE1 | PHE | A | 135 | 54.120 | −46.519 | 2.916 | 1.00 | 21.90 | A | C |
| ATOM | 1793 | CZ | PHE | A | 135 | 55.450 | −46.254 | 3.153 | 1.00 | 24.74 | A | C |
| ATOM | 1795 | CE2 | PHE | A | 135 | 56.215 | −47.169 | 3.850 | 1.00 | 26.09 | A | C |
| ATOM | 1797 | CD2 | PHE | A | 135 | 55.635 | −48.350 | 4.336 | 1.00 | 28.54 | A | C |
| ATOM | 1799 | C | PHE | A | 135 | 53.522 | −52.442 | 4.470 | 1.00 | 34.24 | A | C |
| ATOM | 1800 | O | PHE | A | 135 | 53.953 | −52.727 | 5.590 | 1.00 | 33.24 | A | O |
| ATOM | 1802 | N | SER | A | 136 | 52.667 | −53.235 | 3.825 | 1.00 | 35.02 | A | N |
| ATOM | 1803 | CA | SER | A | 136 | 52.050 | −54.394 | 4.506 | 1.00 | 37.80 | A | C |
| ATOM | 1805 | CB | SER | A | 136 | 50.943 | −55.039 | 3.654 | 1.00 | 37.47 | A | C |
| ATOM | 1808 | OG | SER | A | 136 | 51.480 | −55.711 | 2.531 | 1.00 | 37.80 | A | O |
| ATOM | 1810 | C | SER | A | 136 | 53.065 | −55.448 | 4.966 | 1.00 | 38.21 | A | C |
| ATOM | 1811 | O | SER | A | 136 | 52.917 | −56.015 | 6.045 | 1.00 | 40.62 | A | O |
| ATOM | 1813 | N | GLY | A | 137 | 54.120 | −55.662 | 4.188 | 1.00 | 38.95 | A | N |
| ATOM | 1814 | CA | GLY | A | 137 | 55.167 | −56.606 | 4.562 | 1.00 | 38.95 | A | C |
| ATOM | 1817 | C | GLY | A | 137 | 56.057 | −56.211 | 5.738 | 1.00 | 39.26 | A | C |
| ATOM | 1818 | O | GLY | A | 137 | 57.001 | −56.924 | 6.045 | 1.00 | 39.28 | A | O |
| ATOM | 1820 | N | PHE | A | 138 | 55.770 | −55.096 | 6.405 | 1.00 | 39.21 | A | N |
| ATOM | 1821 | CA | PHE | A | 138 | 56.593 | −54.643 | 7.532 | 1.00 | 40.53 | A | C |
| ATOM | 1823 | CB | PHE | A | 138 | 57.131 | −53.223 | 7.260 | 1.00 | 38.00 | A | C |
| ATOM | 1826 | CG | PHE | A | 138 | 57.991 | −53.154 | 6.039 | 1.00 | 34.18 | A | C |
| ATOM | 1827 | CD1 | PHE | A | 138 | 59.251 | −53.731 | 6.040 | 1.00 | 34.73 | A | C |
| ATOM | 1829 | CE1 | PHE | A | 138 | 60.049 | −53.705 | 4.893 | 1.00 | 34.21 | A | C |
| ATOM | 1831 | CZ | PHE | A | 138 | 59.572 | −53.132 | 3.736 | 1.00 | 30.84 | A | C |
| ATOM | 1833 | CE2 | PHE | A | 138 | 58.307 | −52.565 | 3.720 | 1.00 | 32.61 | A | C |
| ATOM | 1835 | CD2 | PHE | A | 138 | 57.522 | −52.590 | 4.867 | 1.00 | 33.77 | A | C |
| ATOM | 1837 | C | PHE | A | 138 | 55.837 | −54.727 | 8.856 | 1.00 | 43.36 | A | C |
| ATOM | 1838 | O | PHE | A | 138 | 56.261 | −54.163 | 9.862 | 1.00 | 43.05 | A | O |
| ATOM | 1840 | N | LYS | A | 139 | 54.727 | −55.455 | 8.852 | 1.00 | 47.23 | A | N |
| ATOM | 1841 | CA | LYS | A | 139 | 53.884 | −55.562 | 10.029 | 1.00 | 51.13 | A | C |
| ATOM | 1843 | CB | LYS | A | 139 | 52.457 | −55.086 | 9.696 | 1.00 | 51.78 | A | C |
| ATOM | 1846 | CG | LYS | A | 139 | 52.392 | −53.546 | 9.534 | 1.00 | 54.28 | A | C |
| ATOM | 1849 | CD | LYS | A | 139 | 51.184 | −53.029 | 8.748 | 1.00 | 61.08 | A | C |
| ATOM | 1852 | CE | LYS | A | 139 | 49.951 | −52.824 | 9.631 | 1.00 | 64.23 | A | C |
| ATOM | 1855 | NZ | LYS | A | 139 | 50.121 | −51.700 | 10.603 | 1.00 | 59.56 | A | N |

TABLE 4-2-continued

Coordinates of P. alba IspS

| ATOM | 1859 | C | LYS | A | 139 | 53.964 | −56.984 | 10.582 | 1.00 | 53.19 | A | C |
|---|---|---|---|---|---|---|---|---|---|---|---|---|
| ATOM | 1860 | O | LYS | A | 139 | 54.306 | −57.915 | 9.856 | 1.00 | 54.52 | A | O |
| ATOM | 1862 | N | ASP | A | 140 | 53.715 | −57.124 | 11.886 | 1.00 | 55.49 | A | N |
| ATOM | 1863 | CA | ASP | A | 140 | 53.821 | −58.410 | 12.591 | 1.00 | 56.32 | A | C |
| ATOM | 1865 | CB | ASP | A | 140 | 54.282 | −58.194 | 14.050 | 1.00 | 56.20 | A | C |
| ATOM | 1868 | CG | ASP | A | 140 | 53.262 | −57.437 | 14.902 | 1.00 | 53.48 | A | C |
| ATOM | 1869 | OD1 | ASP | A | 140 | 52.109 | −57.244 | 14.468 | 1.00 | 47.36 | A | O |
| ATOM | 1870 | OD2 | ASP | A | 140 | 53.627 | −57.019 | 16.016 | 1.00 | 50.19 | A | O |
| ATOM | 1871 | C | ASP | A | 140 | 52.503 | −59.184 | 12.535 | 1.00 | 58.61 | A | C |
| ATOM | 1872 | O | ASP | A | 140 | 51.591 | −58.814 | 11.787 | 1.00 | 57.83 | A | O |
| ATOM | 1874 | N | GLN | A | 141 | 52.409 | −60.260 | 13.321 | 1.00 | 61.75 | A | N |
| ATOM | 1875 | CA | GLN | A | 141 | 51.191 | −61.083 | 13.382 | 1.00 | 63.46 | A | C |
| ATOM | 1877 | CB | GLN | A | 141 | 51.350 | −62.206 | 14.419 | 1.00 | 64.54 | A | C |
| ATOM | 1880 | CG | GLN | A | 141 | 52.401 | −63.260 | 14.080 | 1.00 | 67.62 | A | C |
| ATOM | 1883 | CD | GLN | A | 141 | 52.236 | −64.534 | 14.912 | 1.00 | 71.72 | A | C |
| ATOM | 1884 | OE1 | GLN | A | 141 | 51.201 | −65.200 | 14.845 | 1.00 | 71.94 | A | O |
| ATOM | 1885 | NE2 | GLN | A | 141 | 53.256 | −64.873 | 15.698 | 1.00 | 69.09 | A | N |
| ATOM | 1888 | C | GLN | A | 141 | 49.927 | −60.264 | 13.708 | 1.00 | 63.18 | A | C |
| ATOM | 1889 | O | GLN | A | 141 | 48.854 | −60.539 | 13.161 | 1.00 | 63.42 | A | O |
| ATOM | 1891 | N | ASN | A | 142 | 50.071 | −59.265 | 14.585 | 1.00 | 62.04 | A | N |
| ATOM | 1892 | CA | ASN | A | 142 | 48.948 | −58.447 | 15.067 | 1.00 | 61.76 | A | C |
| ATOM | 1894 | CB | ASN | A | 142 | 49.211 | −58.041 | 16.521 | 1.00 | 62.74 | A | C |
| ATOM | 1897 | CG | ASN | A | 142 | 49.124 | −59.216 | 17.476 | 1.00 | 64.28 | A | C |
| ATOM | 1898 | OD1 | ASN | A | 142 | 48.147 | −59.967 | 17.461 | 1.00 | 65.28 | A | O |
| ATOM | 1899 | ND2 | ASN | A | 142 | 50.143 | −59.379 | 18.314 | 1.00 | 61.18 | A | N |
| ATOM | 1902 | C | ASN | A | 142 | 48.609 | −57.182 | 14.259 | 1.00 | 60.73 | A | C |
| ATOM | 1903 | O | ASN | A | 142 | 47.790 | −56.374 | 14.696 | 1.00 | 60.76 | A | O |
| ATOM | 1905 | N | GLY | A | 143 | 49.223 | −57.006 | 13.094 | 1.00 | 58.94 | A | N |
| ATOM | 1906 | CA | GLY | A | 143 | 48.969 | −55.823 | 12.273 | 1.00 | 58.11 | A | C |
| ATOM | 1909 | C | GLY | A | 143 | 49.577 | −54.533 | 12.818 | 1.00 | 56.81 | A | C |
| ATOM | 1910 | O | GLY | A | 143 | 49.040 | −53.451 | 12.596 | 1.00 | 56.75 | A | O |
| ATOM | 1912 | N | ASN | A | 144 | 50.684 | −54.658 | 13.551 | 1.00 | 54.34 | A | N |
| ATOM | 1913 | CA | ASN | A | 144 | 51.452 | −53.517 | 14.036 | 1.00 | 51.31 | A | C |
| ATOM | 1915 | CB | ASN | A | 144 | 51.523 | −53.532 | 15.561 | 1.00 | 50.99 | A | C |
| ATOM | 1918 | CG | ASN | A | 144 | 50.156 | −53.394 | 16.203 | 1.00 | 54.98 | A | C |
| ATOM | 1919 | OD1 | ASN | A | 144 | 49.390 | −52.496 | 15.861 | 1.00 | 57.50 | A | O |
| ATOM | 1920 | ND2 | ASN | A | 144 | 49.836 | −54.291 | 17.129 | 1.00 | 54.41 | A | N |
| ATOM | 1923 | C | ASN | A | 144 | 52.842 | −53.594 | 13.421 | 1.00 | 47.91 | A | C |
| ATOM | 1924 | O | ASN | A | 144 | 53.314 | −54.678 | 13.096 | 1.00 | 45.74 | A | O |
| ATOM | 1926 | N | PHE | A | 145 | 53.487 | −52.450 | 13.225 | 1.00 | 45.60 | A | N |
| ATOM | 1927 | CA | PHE | A | 145 | 54.827 | −52.432 | 12.636 | 1.00 | 42.79 | A | C |
| ATOM | 1929 | CB | PHE | A | 145 | 55.315 | −50.995 | 12.429 | 1.00 | 41.21 | A | C |
| ATOM | 1932 | CG | PHE | A | 145 | 54.767 | −50.342 | 11.190 | 1.00 | 34.59 | A | C |
| ATOM | 1933 | CD1 | PHE | A | 145 | 53.612 | −49.583 | 11.241 | 1.00 | 28.50 | A | C |
| ATOM | 1935 | CE1 | PHE | A | 145 | 53.097 | −48.999 | 10.107 | 1.00 | 33.37 | A | C |
| ATOM | 1937 | CZ | PHE | A | 145 | 53.749 | −49.159 | 8.890 | 1.00 | 34.40 | A | C |
| ATOM | 1939 | CE2 | PHE | A | 145 | 54.909 | −49.912 | 8.827 | 1.00 | 36.36 | A | C |
| ATOM | 1941 | CD2 | PHE | A | 145 | 55.403 | −50.508 | 9.971 | 1.00 | 33.35 | A | C |
| ATOM | 1943 | C | PHE | A | 145 | 55.811 | −53.220 | 13.509 | 1.00 | 43.43 | A | C |
| ATOM | 1944 | O | PHE | A | 145 | 55.739 | −53.168 | 14.740 | 1.00 | 39.77 | A | O |
| ATOM | 1946 | N | LEU | A | 146 | 56.719 | −53.949 | 12.862 | 1.00 | 45.03 | A | N |
| ATOM | 1947 | CA | LEU | A | 146 | 57.658 | −54.811 | 13.574 | 1.00 | 47.52 | A | C |
| ATOM | 1949 | CB | LEU | A | 146 | 58.571 | −55.562 | 12.600 | 1.00 | 48.77 | A | C |
| ATOM | 1952 | CG | LEU | A | 146 | 57.939 | −56.744 | 11.854 | 1.00 | 51.30 | A | C |
| ATOM | 1954 | CD1 | LEU | A | 146 | 58.802 | −57.157 | 10.656 | 1.00 | 53.93 | A | C |
| ATOM | 1958 | CD2 | LEU | A | 146 | 57.724 | −57.920 | 12.803 | 1.00 | 50.78 | A | C |
| ATOM | 1962 | C | LEU | A | 146 | 58.503 | −53.994 | 14.521 | 1.00 | 47.29 | A | C |
| ATOM | 1963 | O | LEU | A | 146 | 59.085 | −53.004 | 14.122 | 1.00 | 46.58 | A | O |
| ATOM | 1965 | N | GLU | A | 147 | 58.546 | −54.418 | 15.778 | 1.00 | 48.15 | A | N |
| ATOM | 1966 | CA | GLU | A | 147 | 59.333 | −53.766 | 16.818 | 1.00 | 49.25 | A | C |
| ATOM | 1968 | CB | GLU | A | 147 | 59.243 | −54.591 | 18.121 | 1.00 | 51.28 | A | C |
| ATOM | 1971 | CG | GLU | A | 147 | 59.923 | −53.979 | 19.359 | 1.00 | 56.00 | A | C |
| ATOM | 1974 | CD | GLU | A | 147 | 59.228 | −52.725 | 19.877 | 1.00 | 63.07 | A | C |
| ATOM | 1975 | OE1 | GLU | A | 147 | 58.125 | −52.395 | 19.387 | 1.00 | 66.00 | A | O |
| ATOM | 1976 | OE2 | GLU | A | 147 | 59.788 | −52.068 | 20.785 | 1.00 | 66.72 | A | O |
| ATOM | 1977 | C | GLU | A | 147 | 60.791 | −53.608 | 16.404 | 1.00 | 47.26 | A | C |
| ATOM | 1978 | O | GLU | A | 147 | 61.365 | −52.554 | 16.584 | 1.00 | 46.13 | A | O |
| ATOM | 1980 | N | ASN | A | 148 | 61.383 | −54.649 | 15.830 | 1.00 | 47.30 | A | N |
| ATOM | 1981 | CA | ASN | A | 148 | 62.824 | −54.639 | 15.564 | 1.00 | 48.47 | A | C |
| ATOM | 1983 | CB | ASN | A | 148 | 63.333 | −56.046 | 15.259 | 1.00 | 49.35 | A | C |
| ATOM | 1986 | CG | ASN | A | 148 | 62.710 | −56.636 | 14.014 | 1.00 | 55.86 | A | C |
| ATOM | 1987 | OD1 | ASN | A | 148 | 62.358 | −55.913 | 13.075 | 1.00 | 62.15 | A | O |
| ATOM | 1988 | ND2 | ASN | A | 148 | 62.566 | −57.959 | 13.994 | 1.00 | 57.68 | A | N |
| ATOM | 1991 | C | ASN | A | 148 | 63.268 | −53.665 | 14.470 | 1.00 | 48.40 | A | C |
| ATOM | 1992 | O | ASN | A | 148 | 64.470 | −53.493 | 14.255 | 1.00 | 48.76 | A | O |
| ATOM | 1994 | N | LEU | A | 149 | 62.308 | −53.037 | 13.781 | 1.00 | 47.17 | A | N |
| ATOM | 1995 | CA | LEU | A | 149 | 62.612 | −52.012 | 12.775 | 1.00 | 45.22 | A | C |
| ATOM | 1997 | CB | LEU | A | 149 | 61.391 | −51.719 | 11.883 | 1.00 | 44.21 | A | C |

TABLE 4-2-continued

Coordinates of *P. alba* IspS

| ATOM | 2000 | CG | LEU | A | 149 | 60.901 | −52.874 | 10.985 | 1.00 | 45.00 | A | C |
|---|---|---|---|---|---|---|---|---|---|---|---|---|
| ATOM | 2002 | CD1 | LEU | A | 149 | 59.457 | −52.641 | 10.487 | 1.00 | 35.64 | A | C |
| ATOM | 2006 | CD2 | LEU | A | 149 | 61.859 | −53.134 | 9.818 | 1.00 | 40.71 | A | C |
| ATOM | 2010 | C | LEU | A | 149 | 63.119 | −50.719 | 13.427 | 1.00 | 44.14 | A | C |
| ATOM | 2011 | O | LEU | A | 149 | 63.767 | −49.915 | 12.767 | 1.00 | 43.38 | A | O |
| ATOM | 2013 | N | LYS | A | 150 | 62.848 | −50.535 | 14.723 | 1.00 | 43.89 | A | N |
| ATOM | 2014 | CA | LYS | A | 150 | 63.299 | −49.345 | 15.459 | 1.00 | 43.64 | A | C |
| ATOM | 2016 | CB | LYS | A | 150 | 62.834 | −49.395 | 16.921 | 1.00 | 44.18 | A | C |
| ATOM | 2019 | CG | LYS | A | 150 | 63.567 | −50.438 | 17.776 | 1.00 | 45.80 | A | C |
| ATOM | 2022 | CD | LYS | A | 150 | 62.990 | −50.566 | 19.179 | 1.00 | 46.45 | A | C |
| ATOM | 2025 | CE | LYS | A | 150 | 63.602 | −51.772 | 19.932 | 1.00 | 46.45 | A | C |
| ATOM | 2028 | NZ | LYS | A | 150 | 63.600 | −51.578 | 21.410 | 1.00 | 44.46 | A | N |
| ATOM | 2032 | C | LYS | A | 150 | 64.816 | −49.166 | 15.418 | 1.00 | 43.28 | A | C |
| ATOM | 2033 | O | LYS | A | 150 | 65.307 | −48.058 | 15.547 | 1.00 | 43.46 | A | O |
| ATOM | 2035 | N | GLU | A | 151 | 65.548 | −50.262 | 15.231 | 1.00 | 43.96 | A | N |
| ATOM | 2036 | CA | GLU | A | 151 | 67.016 | −50.229 | 15.193 | 1.00 | 44.86 | A | C |
| ATOM | 2038 | CB | GLU | A | 151 | 67.590 | −51.660 | 15.231 | 1.00 | 46.17 | A | C |
| ATOM | 2041 | CG | GLU | A | 151 | 67.109 | −52.575 | 16.391 | 1.00 | 48.12 | A | C |
| ATOM | 2044 | CD | GLU | A | 151 | 67.468 | −52.062 | 17.783 | 1.00 | 57.25 | A | C |
| ATOM | 2045 | OE1 | GLU | A | 151 | 68.205 | −51.057 | 17.895 | 1.00 | 58.32 | A | O |
| ATOM | 2046 | OE2 | GLU | A | 151 | 67.010 | −52.679 | 18.776 | 1.00 | 64.54 | A | O |
| ATOM | 2047 | C | GLU | A | 151 | 67.568 | −49.510 | 13.960 | 1.00 | 44.01 | A | C |
| ATOM | 2048 | O | GLU | A | 151 | 68.687 | −49.009 | 13.987 | 1.00 | 45.27 | A | O |
| ATOM | 2050 | N | ASP | A | 152 | 66.778 | −49.481 | 12.887 | 1.00 | 43.54 | A | N |
| ATOM | 2051 | CA | ASP | A | 152 | 67.182 | −48.939 | 11.586 | 1.00 | 42.81 | A | C |
| ATOM | 2053 | CB | ASP | A | 152 | 66.628 | −49.846 | 10.469 | 1.00 | 42.48 | A | C |
| ATOM | 2056 | CG | ASP | A | 152 | 67.076 | −49.431 | 9.065 | 1.00 | 44.12 | A | C |
| ATOM | 2057 | OD1 | ASP | A | 152 | 67.707 | −48.356 | 8.890 | 1.00 | 44.74 | A | O |
| ATOM | 2058 | OD2 | ASP | A | 152 | 66.785 | −50.208 | 8.122 | 1.00 | 43.55 | A | O |
| ATOM | 2059 | C | ASP | A | 152 | 66.619 | −47.524 | 11.481 | 1.00 | 41.46 | A | C |
| ATOM | 2060 | O | ASP | A | 152 | 65.557 | −47.307 | 10.902 | 1.00 | 41.35 | A | O |
| ATOM | 2062 | N | ILE | A | 153 | 67.345 | −46.569 | 12.045 | 1.00 | 39.78 | A | N |
| ATOM | 2063 | CA | ILE | A | 153 | 66.816 | −45.228 | 12.270 | 1.00 | 39.72 | A | C |
| ATOM | 2065 | CB | ILE | A | 153 | 67.695 | −44.468 | 13.244 | 1.00 | 40.91 | A | C |
| ATOM | 2067 | CG1 | ILE | A | 153 | 67.578 | −45.131 | 14.627 | 1.00 | 43.16 | A | C |
| ATOM | 2070 | CD1 | ILE | A | 153 | 68.849 | −45.081 | 15.411 | 1.00 | 50.21 | A | C |
| ATOM | 2074 | CG2 | ILE | A | 153 | 67.288 | −42.997 | 13.309 | 1.00 | 36.49 | A | C |
| ATOM | 2078 | C | ILE | A | 153 | 66.625 | −44.422 | 10.992 | 1.00 | 39.38 | A | C |
| ATOM | 2079 | O | ILE | A | 153 | 65.718 | −43.606 | 10.902 | 1.00 | 38.41 | A | O |
| ATOM | 2081 | N | LYS | A | 154 | 67.483 | −44.667 | 10.011 | 1.00 | 38.77 | A | N |
| ATOM | 2082 | CA | LYS | A | 154 | 67.316 | −44.131 | 8.675 | 1.00 | 38.08 | A | C |
| ATOM | 2084 | CB | LYS | A | 154 | 68.439 | −44.657 | 7.771 | 1.00 | 39.94 | A | C |
| ATOM | 2087 | CG | LYS | A | 154 | 69.030 | −43.679 | 6.791 | 1.00 | 46.34 | A | C |
| ATOM | 2090 | CD | LYS | A | 154 | 69.998 | −44.418 | 5.833 | 1.00 | 57.75 | A | C |
| ATOM | 2093 | CE | LYS | A | 154 | 71.163 | −43.526 | 5.362 | 1.00 | 63.86 | A | C |
| ATOM | 2096 | NZ | LYS | A | 154 | 72.090 | −43.113 | 6.477 | 1.00 | 66.28 | A | N |
| ATOM | 2100 | C | LYS | A | 154 | 65.966 | −44.582 | 8.123 | 1.00 | 34.45 | A | C |
| ATOM | 2101 | O | LYS | A | 154 | 65.265 | −43.806 | 7.491 | 1.00 | 34.91 | A | O |
| ATOM | 2103 | N | ALA | A | 155 | 65.602 | −45.841 | 8.360 | 1.00 | 31.65 | A | N |
| ATOM | 2104 | CA | ALA | A | 155 | 64.367 | −46.382 | 7.796 | 1.00 | 29.70 | A | C |
| ATOM | 2106 | CB | ALA | A | 155 | 64.349 | −47.881 | 7.905 | 1.00 | 28.03 | A | C |
| ATOM | 2110 | C | ALA | A | 155 | 63.147 | −45.772 | 8.484 | 1.00 | 29.53 | A | C |
| ATOM | 2111 | O | ALA | A | 155 | 62.118 | −45.546 | 7.862 | 1.00 | 28.76 | A | O |
| ATOM | 2113 | N | ILE | A | 156 | 63.291 | −45.483 | 9.769 | 1.00 | 28.30 | A | N |
| ATOM | 2114 | CA | ILE | A | 156 | 62.218 | −44.941 | 10.574 | 1.00 | 29.28 | A | C |
| ATOM | 2116 | CB | ILE | A | 156 | 62.573 | −45.035 | 12.062 | 1.00 | 30.53 | A | C |
| ATOM | 2118 | CG1 | ILE | A | 156 | 62.606 | −46.500 | 12.498 | 1.00 | 32.30 | A | C |
| ATOM | 2121 | CD1 | ILE | A | 156 | 61.294 | −47.182 | 12.411 | 1.00 | 34.89 | A | C |
| ATOM | 2125 | CG2 | ILE | A | 156 | 61.599 | −44.209 | 12.894 | 1.00 | 35.42 | A | C |
| ATOM | 2129 | C | ILE | A | 156 | 61.957 | −43.486 | 10.232 | 1.00 | 26.18 | A | C |
| ATOM | 2130 | O | ILE | A | 156 | 60.816 | −43.061 | 10.146 | 1.00 | 25.91 | A | O |
| ATOM | 2132 | N | LEU | A | 157 | 63.026 | −42.738 | 10.049 | 1.00 | 25.45 | A | N |
| ATOM | 2133 | CA | LEU | A | 157 | 62.941 | −41.363 | 9.595 | 1.00 | 27.66 | A | C |
| ATOM | 2135 | CB | LEU | A | 157 | 64.320 | −40.773 | 9.381 | 1.00 | 28.15 | A | C |
| ATOM | 2138 | CG | LEU | A | 157 | 64.937 | −39.982 | 10.520 | 1.00 | 34.36 | A | C |
| ATOM | 2140 | CD1 | LEU | A | 157 | 66.210 | −39.356 | 9.983 | 1.00 | 31.72 | A | C |
| ATOM | 2144 | CD2 | LEU | A | 157 | 63.996 | −38.917 | 11.050 | 1.00 | 32.16 | A | C |
| ATOM | 2148 | C | LEU | A | 157 | 62.215 | −41.330 | 8.271 | 1.00 | 27.68 | A | C |
| ATOM | 2149 | O | LEU | A | 157 | 61.279 | −40.551 | 8.073 | 1.00 | 26.10 | A | O |
| ATOM | 2151 | N | SER | A | 158 | 62.658 | −42.199 | 7.371 | 1.00 | 26.74 | A | N |
| ATOM | 2152 | CA | SER | A | 158 | 62.074 | −42.255 | 6.064 | 1.00 | 27.94 | A | C |
| ATOM | 2154 | CB | SER | A | 158 | 62.861 | −43.219 | 5.198 | 1.00 | 27.98 | A | C |
| ATOM | 2157 | OG | SER | A | 158 | 62.518 | −43.042 | 3.845 | 1.00 | 44.57 | A | O |
| ATOM | 2159 | C | SER | A | 158 | 60.573 | −42.600 | 6.186 | 1.00 | 25.94 | A | C |
| ATOM | 2160 | O | SER | A | 158 | 59.730 | −41.938 | 5.574 | 1.00 | 23.44 | A | O |
| ATOM | 2162 | N | LEU | A | 159 | 60.227 | −43.568 | 7.034 | 1.00 | 24.38 | A | N |
| ATOM | 2163 | CA | LEU | A | 159 | 58.807 | −43.865 | 7.292 | 1.00 | 23.67 | A | C |
| ATOM | 2165 | CB | LEU | A | 159 | 58.667 | −45.082 | 8.206 | 1.00 | 23.04 | A | C |

TABLE 4-2-continued

Coordinates of *P. alba* IspS

| ATOM | 2168 | CG | LEU | A | 159 | 57.261 | −45.601 | 8.496 | 1.00 | 23.72 | A | C |
|---|---|---|---|---|---|---|---|---|---|---|---|---|
| ATOM | 2170 | CD1 | LEU | A | 159 | 56.577 | −46.056 | 7.202 | 1.00 | 19.76 | A | C |
| ATOM | 2174 | CD2 | LEU | A | 159 | 57.295 | −46.735 | 9.527 | 1.00 | 24.23 | A | C |
| ATOM | 2178 | C | LEU | A | 159 | 58.065 | −42.651 | 7.881 | 1.00 | 22.73 | A | C |
| ATOM | 2179 | O | LEU | A | 159 | 56.955 | −42.353 | 7.468 | 1.00 | 25.33 | A | O |
| ATOM | 2181 | N | TYR | A | 160 | 58.676 | −41.950 | 8.834 | 1.00 | 21.28 | A | N |
| ATOM | 2182 | CA | TYR | A | 160 | 58.069 | −40.740 | 9.406 | 1.00 | 19.99 | A | C |
| ATOM | 2184 | CB | TYR | A | 160 | 58.966 | −40.158 | 10.499 | 1.00 | 16.21 | A | C |
| ATOM | 2187 | CG | TYR | A | 160 | 58.612 | −38.765 | 11.028 | 1.00 | 15.97 | A | C |
| ATOM | 2188 | CD1 | TYR | A | 160 | 57.726 | −38.581 | 12.074 | 1.00 | 20.63 | A | C |
| ATOM | 2190 | CE1 | TYR | A | 160 | 57.431 | −37.309 | 12.550 | 1.00 | 23.21 | A | C |
| ATOM | 2192 | CZ | TYR | A | 160 | 58.069 | −36.229 | 12.008 | 1.00 | 24.75 | A | C |
| ATOM | 2193 | OH | TYR | A | 160 | 57.813 | −34.949 | 12.441 | 1.00 | 37.71 | A | O |
| ATOM | 2195 | CE2 | TYR | A | 160 | 58.962 | −36.401 | 10.988 | 1.00 | 27.54 | A | C |
| ATOM | 2197 | CD2 | TYR | A | 160 | 59.228 | −37.648 | 10.513 | 1.00 | 27.04 | A | C |
| ATOM | 2199 | C | TYR | A | 160 | 57.758 | −39.715 | 8.301 | 1.00 | 20.86 | A | C |
| ATOM | 2200 | O | TYR | A | 160 | 56.670 | −39.148 | 8.261 | 1.00 | 19.44 | A | O |
| ATOM | 2202 | N | GLU | A | 161 | 58.691 | −39.529 | 7.376 | 1.00 | 22.74 | A | N |
| ATOM | 2203 | CA | GLU | A | 161 | 58.562 | −38.479 | 6.366 | 1.00 | 22.29 | A | C |
| ATOM | 2205 | CB | GLU | A | 161 | 59.869 | −38.239 | 5.586 | 1.00 | 22.32 | A | C |
| ATOM | 2208 | CG | GLU | A | 161 | 61.065 | −37.781 | 6.403 | 1.00 | 25.25 | A | C |
| ATOM | 2211 | CD | GLU | A | 161 | 60.985 | −36.329 | 6.883 | 1.00 | 29.78 | A | C |
| ATOM | 2212 | OE1 | GLU | A | 161 | 59.985 | −35.612 | 6.600 | 1.00 | 30.17 | A | O |
| ATOM | 2213 | OE2 | GLU | A | 161 | 61.934 | −35.925 | 7.588 | 1.00 | 23.68 | A | O |
| ATOM | 2214 | C | GLU | A | 161 | 57.477 | −38.855 | 5.384 | 1.00 | 23.03 | A | C |
| ATOM | 2215 | O | GLU | A | 161 | 56.726 | −37.983 | 4.954 | 1.00 | 23.28 | A | O |
| ATOM | 2217 | N | ALA | A | 162 | 57.404 | −40.139 | 5.031 | 1.00 | 19.57 | A | N |
| ATOM | 2218 | CA | ALA | A | 162 | 56.377 | −40.621 | 4.113 | 1.00 | 20.19 | A | C |
| ATOM | 2220 | CB | ALA | A | 162 | 56.619 | −42.067 | 3.743 | 1.00 | 17.81 | A | C |
| ATOM | 2224 | C | ALA | A | 162 | 54.968 | −40.459 | 4.674 | 1.00 | 20.85 | A | C |
| ATOM | 2225 | O | ALA | A | 162 | 54.042 | −40.179 | 3.921 | 1.00 | 20.56 | A | O |
| ATOM | 2227 | N | SER | A | 163 | 54.795 | −40.651 | 5.983 | 1.00 | 21.00 | A | N |
| ATOM | 2228 | CA | SER | A | 163 | 53.453 | −40.617 | 6.584 | 1.00 | 20.15 | A | C |
| ATOM | 2230 | CB | SER | A | 163 | 53.512 | −40.917 | 8.077 | 1.00 | 20.26 | A | C |
| ATOM | 2233 | OG | SER | A | 163 | 54.223 | −39.914 | 8.772 | 1.00 | 22.70 | A | O |
| ATOM | 2235 | C | SER | A | 163 | 52.758 | −39.276 | 6.398 | 1.00 | 20.14 | A | C |
| ATOM | 2236 | O | SER | A | 163 | 51.553 | −39.212 | 6.412 | 1.00 | 21.29 | A | O |
| ATOM | 2238 | N | PHE | A | 164 | 53.505 | −38.194 | 6.207 | 1.00 | 21.91 | A | N |
| ATOM | 2239 | CA | PHE | A | 164 | 52.852 | −36.893 | 6.012 | 1.00 | 21.51 | A | C |
| ATOM | 2241 | CB | PHE | A | 164 | 53.783 | −35.742 | 6.353 | 1.00 | 21.26 | A | C |
| ATOM | 2244 | CG | PHE | A | 164 | 54.107 | −35.680 | 7.823 | 1.00 | 20.56 | A | C |
| ATOM | 2245 | CD1 | PHE | A | 164 | 53.300 | −34.984 | 8.692 | 1.00 | 19.82 | A | C |
| ATOM | 2247 | CE1 | PHE | A | 164 | 53.593 | −34.950 | 10.044 | 1.00 | 20.99 | A | C |
| ATOM | 2249 | CZ | PHE | A | 164 | 54.694 | −35.621 | 10.537 | 1.00 | 19.87 | A | C |
| ATOM | 2251 | CE2 | PHE | A | 164 | 55.491 | −36.343 | 9.683 | 1.00 | 22.05 | A | C |
| ATOM | 2253 | CD2 | PHE | A | 164 | 55.178 | −36.390 | 8.335 | 1.00 | 19.04 | A | C |
| ATOM | 2255 | C | PHE | A | 164 | 52.235 | −36.724 | 4.651 | 1.00 | 20.83 | A | C |
| ATOM | 2256 | O | PHE | A | 164 | 51.564 | −35.732 | 4.420 | 1.00 | 20.53 | A | O |
| ATOM | 2258 | N | LEU | A | 165 | 52.434 | −37.694 | 3.759 | 1.00 | 21.43 | A | N |
| ATOM | 2259 | CA | LEU | A | 165 | 51.817 | −37.634 | 2.443 | 1.00 | 21.34 | A | C |
| ATOM | 2261 | CB | LEU | A | 165 | 52.808 | −38.064 | 1.356 | 1.00 | 21.77 | A | C |
| ATOM | 2264 | CG | LEU | A | 165 | 53.927 | −37.066 | 0.985 | 1.00 | 24.00 | A | C |
| ATOM | 2266 | CD1 | LEU | A | 165 | 55.125 | −37.119 | 1.950 | 1.00 | 24.11 | A | C |
| ATOM | 2270 | CD2 | LEU | A | 165 | 54.414 | −37.300 | −0.424 | 1.00 | 21.22 | A | C |
| ATOM | 2274 | C | LEU | A | 165 | 50.496 | −38.420 | 2.372 | 1.00 | 21.79 | A | C |
| ATOM | 2275 | O | LEU | A | 165 | 49.967 | −38.657 | 1.306 | 1.00 | 24.21 | A | O |
| ATOM | 2277 | N | ALA | A | 166 | 49.957 | −38.775 | 3.523 | 1.00 | 21.05 | A | N |
| ATOM | 2278 | CA | ALA | A | 166 | 48.760 | −39.562 | 3.627 | 1.00 | 21.13 | A | C |
| ATOM | 2280 | CB | ALA | A | 166 | 48.449 | −39.848 | 5.112 | 1.00 | 16.14 | A | C |
| ATOM | 2284 | C | ALA | A | 166 | 47.564 | −38.887 | 2.998 | 1.00 | 22.34 | A | C |
| ATOM | 2285 | O | ALA | A | 166 | 47.448 | −37.664 | 3.031 | 1.00 | 23.04 | A | O |
| ATOM | 2287 | N | LEU | A | 167 | 46.670 | −39.710 | 2.446 | 1.00 | 22.65 | A | N |
| ATOM | 2288 | CA | LEU | A | 167 | 45.315 | −39.299 | 2.123 | 1.00 | 22.73 | A | C |
| ATOM | 2290 | CB | LEU | A | 167 | 44.903 | −39.929 | 0.805 | 1.00 | 22.79 | A | C |
| ATOM | 2293 | CG | LEU | A | 167 | 45.870 | −39.733 | −0.367 | 1.00 | 29.42 | A | C |
| ATOM | 2295 | CD1 | LEU | A | 167 | 45.269 | −40.327 | −1.669 | 1.00 | 17.64 | A | C |
| ATOM | 2299 | CD2 | LEU | A | 167 | 46.250 | −38.249 | −0.540 | 1.00 | 18.14 | A | C |
| ATOM | 2303 | C | LEU | A | 167 | 44.351 | −39.758 | 3.235 | 1.00 | 23.82 | A | C |
| ATOM | 2304 | O | LEU | A | 167 | 44.694 | −40.592 | 4.059 | 1.00 | 22.47 | A | O |
| ATOM | 2306 | N | GLU | A | 168 | 43.139 | −39.228 | 3.239 | 1.00 | 24.07 | A | N |
| ATOM | 2307 | CA | GLU | A | 168 | 42.132 | −39.692 | 4.157 | 1.00 | 25.29 | A | C |
| ATOM | 2309 | CB | GLU | A | 168 | 40.818 | −38.931 | 3.943 | 1.00 | 27.27 | A | C |
| ATOM | 2312 | CG | GLU | A | 168 | 40.738 | −37.525 | 4.576 | 1.00 | 30.92 | A | C |
| ATOM | 2315 | CD | GLU | A | 168 | 39.356 | −36.894 | 4.371 | 1.00 | 38.89 | A | C |
| ATOM | 2316 | OE1 | GLU | A | 168 | 38.996 | −36.617 | 3.199 | 1.00 | 36.18 | A | O |
| ATOM | 2317 | OE2 | GLU | A | 168 | 38.626 | −36.700 | 5.379 | 1.00 | 42.80 | A | O |
| ATOM | 2318 | C | GLU | A | 168 | 41.902 | −41.186 | 3.935 | 1.00 | 25.25 | A | C |
| ATOM | 2319 | O | GLU | A | 168 | 41.855 | −41.652 | 2.798 | 1.00 | 22.24 | A | O |

TABLE 4-2-continued

Coordinates of *P. alba* IspS

| ATOM | 2321 | N | GLY | A | 169 | 41.748 | −41.928 | 5.034 | 1.00 | 24.73 | A | N |
| ATOM | 2322 | CA | GLY | A | 169 | 41.540 | −43.370 | 4.977 | 1.00 | 21.86 | A | C |
| ATOM | 2325 | C | GLY | A | 169 | 42.785 | −44.213 | 5.048 | 1.00 | 21.58 | A | C |
| ATOM | 2326 | O | GLY | A | 169 | 42.692 | −45.426 | 5.190 | 1.00 | 24.46 | A | O |
| ATOM | 2328 | N | GLU | A | 170 | 43.956 | −43.598 | 4.967 | 1.00 | 20.95 | A | N |
| ATOM | 2329 | CA | GLU | A | 170 | 45.179 | −44.378 | 4.872 | 1.00 | 21.33 | A | C |
| ATOM | 2331 | CB | GLU | A | 170 | 46.219 | −43.717 | 3.960 | 1.00 | 16.76 | A | C |
| ATOM | 2334 | CG | GLU | A | 170 | 45.778 | −43.588 | 2.518 | 1.00 | 22.22 | A | C |
| ATOM | 2337 | CD | GLU | A | 170 | 46.915 | −43.209 | 1.542 | 1.00 | 28.05 | A | C |
| ATOM | 2338 | OE1 | GLU | A | 170 | 47.070 | −43.885 | 0.497 | 1.00 | 32.07 | A | O |
| ATOM | 2339 | OE2 | GLU | A | 170 | 47.654 | −42.242 | 1.822 | 1.00 | 24.57 | A | O |
| ATOM | 2340 | C | GLU | A | 170 | 45.699 | −44.577 | 6.271 | 1.00 | 21.42 | A | C |
| ATOM | 2341 | O | GLU | A | 170 | 46.699 | −43.979 | 6.686 | 1.00 | 21.14 | A | O |
| ATOM | 2343 | N | ASN | A | 171 | 45.000 | −45.435 | 6.992 | 1.00 | 21.46 | A | N |
| ATOM | 2344 | CA | ASN | A | 171 | 45.247 | −45.636 | 8.406 | 1.00 | 23.53 | A | C |
| ATOM | 2346 | CB | ASN | A | 171 | 44.197 | −46.587 | 8.999 | 1.00 | 24.69 | A | C |
| ATOM | 2349 | CG | ASN | A | 171 | 44.256 | −47.982 | 8.375 | 1.00 | 28.66 | A | C |
| ATOM | 2350 | OD1 | ASN | A | 171 | 43.992 | −48.155 | 7.177 | 1.00 | 21.35 | A | O |
| ATOM | 2351 | ND2 | ASN | A | 171 | 44.645 | −48.972 | 9.178 | 1.00 | 19.68 | A | N |
| ATOM | 2354 | C | ASN | A | 171 | 46.648 | −46.164 | 8.692 | 1.00 | 24.20 | A | C |
| ATOM | 2355 | O | ASN | A | 171 | 47.193 | −45.894 | 9.753 | 1.00 | 24.52 | A | O |
| ATOM | 2357 | N | ILE | A | 172 | 47.217 | −46.909 | 7.745 | 1.00 | 25.20 | A | N |
| ATOM | 2358 | CA | ILE | A | 172 | 48.549 | −47.478 | 7.893 | 1.00 | 27.16 | A | C |
| ATOM | 2360 | CB | ILE | A | 172 | 48.898 | −48.455 | 6.738 | 1.00 | 27.07 | A | C |
| ATOM | 2362 | CG1 | ILE | A | 172 | 47.981 | −49.677 | 6.764 | 1.00 | 30.96 | A | C |
| ATOM | 2365 | CD1 | ILE | A | 172 | 48.252 | −50.653 | 5.616 | 1.00 | 34.90 | A | C |
| ATOM | 2369 | CG2 | ILE | A | 172 | 50.354 | −48.935 | 6.825 | 1.00 | 23.91 | A | C |
| ATOM | 2373 | C | ILE | A | 172 | 49.595 | −46.348 | 8.004 | 1.00 | 28.36 | A | C |
| ATOM | 2374 | O | ILE | A | 172 | 50.534 | −46.443 | 8.787 | 1.00 | 29.81 | A | O |
| ATOM | 2376 | N | LEU | A | 173 | 49.393 | −45.268 | 7.264 | 1.00 | 27.42 | A | N |
| ATOM | 2377 | CA | LEU | A | 173 | 50.326 | −44.141 | 7.300 | 1.00 | 27.76 | A | C |
| ATOM | 2379 | CB | LEU | A | 173 | 50.138 | −43.217 | 6.096 | 1.00 | 27.01 | A | C |
| ATOM | 2382 | CG | LEU | A | 173 | 50.933 | −43.554 | 4.842 | 1.00 | 27.25 | A | C |
| ATOM | 2384 | CD1 | LEU | A | 173 | 50.747 | −44.951 | 4.446 | 1.00 | 27.88 | A | C |
| ATOM | 2388 | CD2 | LEU | A | 173 | 50.482 | −42.633 | 3.687 | 1.00 | 29.35 | A | C |
| ATOM | 2392 | C | LEU | A | 173 | 50.197 | −43.362 | 8.605 | 1.00 | 26.43 | A | C |
| ATOM | 2393 | O | LEU | A | 173 | 51.201 | −42.925 | 9.141 | 1.00 | 25.15 | A | O |
| ATOM | 2395 | N | ASP | A | 174 | 48.981 | −43.205 | 9.121 | 1.00 | 24.34 | A | N |
| ATOM | 2396 | CA | ASP | A | 174 | 48.792 | −42.610 | 10.443 | 1.00 | 26.66 | A | C |
| ATOM | 2398 | CB | ASP | A | 174 | 47.310 | −42.444 | 10.771 | 1.00 | 27.51 | A | C |
| ATOM | 2401 | CG | ASP | A | 174 | 46.649 | −41.327 | 9.959 | 1.00 | 34.04 | A | C |
| ATOM | 2402 | OD1 | ASP | A | 174 | 47.363 | −40.551 | 9.305 | 1.00 | 40.90 | A | O |
| ATOM | 2403 | OD2 | ASP | A | 174 | 45.406 | −41.228 | 9.980 | 1.00 | 42.95 | A | O |
| ATOM | 2404 | C | ASP | A | 174 | 49.438 | −43.451 | 11.539 | 1.00 | 27.18 | A | C |
| ATOM | 2405 | O | ASP | A | 174 | 50.099 | −42.926 | 12.432 | 1.00 | 28.53 | A | O |
| ATOM | 2407 | N | GLU | A | 175 | 49.228 | −44.756 | 11.480 | 1.00 | 28.79 | A | N |
| ATOM | 2408 | CA | GLU | A | 175 | 49.843 | −45.659 | 12.431 | 1.00 | 29.42 | A | C |
| ATOM | 2410 | CB | GLU | A | 175 | 49.321 | −47.083 | 12.237 | 1.00 | 29.10 | A | C |
| ATOM | 2413 | CG | GLU | A | 175 | 47.835 | −47.244 | 12.560 | 1.00 | 36.91 | A | C |
| ATOM | 2416 | CD | GLU | A | 175 | 47.189 | −48.421 | 11.819 | 1.00 | 41.63 | A | C |
| ATOM | 2417 | OE1 | GLU | A | 175 | 47.928 | −49.311 | 11.327 | 1.00 | 42.73 | A | O |
| ATOM | 2418 | OE2 | GLU | A | 175 | 45.946 | −48.436 | 11.719 | 1.00 | 39.01 | A | O |
| ATOM | 2419 | C | GLU | A | 175 | 51.356 | −45.616 | 12.230 | 1.00 | 27.89 | A | C |
| ATOM | 2420 | O | GLU | A | 175 | 52.100 | −45.726 | 13.180 | 1.00 | 27.43 | A | O |
| ATOM | 2422 | N | ALA | A | 176 | 51.797 | −45.473 | 10.982 | 1.00 | 27.66 | A | N |
| ATOM | 2423 | CA | ALA | A | 176 | 53.225 | −45.370 | 10.668 | 1.00 | 28.24 | A | C |
| ATOM | 2425 | CB | ALA | A | 176 | 53.428 | −45.280 | 9.153 | 1.00 | 26.14 | A | C |
| ATOM | 2429 | C | ALA | A | 176 | 53.872 | −44.173 | 11.387 | 1.00 | 27.46 | A | C |
| ATOM | 2430 | O | ALA | A | 176 | 54.970 | −44.276 | 11.929 | 1.00 | 27.53 | A | O |
| ATOM | 2432 | N | LYS | A | 177 | 53.155 | −43.055 | 11.418 | 1.00 | 26.90 | A | N |
| ATOM | 2433 | CA | LYS | A | 177 | 53.626 | −41.840 | 12.060 | 1.00 | 27.36 | A | C |
| ATOM | 2435 | CB | LYS | A | 177 | 52.670 | −40.666 | 11.775 | 1.00 | 26.52 | A | C |
| ATOM | 2438 | CG | LYS | A | 177 | 53.138 | −39.310 | 12.294 | 1.00 | 26.21 | A | C |
| ATOM | 2441 | CD | LYS | A | 177 | 52.073 | −38.200 | 12.199 | 1.00 | 27.44 | A | C |
| ATOM | 2444 | CE | LYS | A | 177 | 51.689 | −37.893 | 10.754 | 1.00 | 28.20 | A | C |
| ATOM | 2447 | NZ | LYS | A | 177 | 50.565 | −36.898 | 10.663 | 1.00 | 27.57 | A | N |
| ATOM | 2451 | C | LYS | A | 177 | 53.783 | −42.067 | 13.558 | 1.00 | 28.77 | A | C |
| ATOM | 2452 | O | LYS | A | 177 | 54.830 | −41.743 | 14.117 | 1.00 | 28.26 | A | O |
| ATOM | 2454 | N | VAL | A | 178 | 52.749 | −42.617 | 14.196 | 1.00 | 29.28 | A | N |
| ATOM | 2455 | CA | VAL | A | 178 | 52.737 | −42.855 | 15.654 | 1.00 | 27.74 | A | C |
| ATOM | 2457 | CB | VAL | A | 178 | 51.409 | −43.524 | 16.103 | 1.00 | 28.79 | A | C |
| ATOM | 2459 | CG1 | VAL | A | 178 | 51.481 | −44.089 | 17.585 | 1.00 | 22.40 | A | C |
| ATOM | 2463 | CG2 | VAL | A | 178 | 50.228 | −42.565 | 15.919 | 1.00 | 23.47 | A | C |
| ATOM | 2467 | C | VAL | A | 178 | 53.907 | −43.758 | 16.025 | 1.00 | 29.18 | A | C |
| ATOM | 2468 | O | VAL | A | 178 | 54.651 | −43.485 | 16.955 | 1.00 | 30.11 | A | O |
| ATOM | 2470 | N | PHE | A | 179 | 54.058 | −44.838 | 15.273 | 1.00 | 28.49 | A | N |
| ATOM | 2471 | CA | PHE | A | 179 | 55.168 | −45.759 | 15.448 | 1.00 | 28.24 | A | C |
| ATOM | 2473 | CB | PHE | A | 179 | 54.990 | −46.915 | 14.466 | 1.00 | 28.43 | A | C |

TABLE 4-2-continued

Coordinates of *P. alba* IspS

| | | | | | | | | | | | |
|---|---|---|---|---|---|---|---|---|---|---|---|
| ATOM | 2476 | CG | PHE | A | 179 | 56.115 | −47.880 | 14.457 | 1.00 | 29.30 | A | C |
| ATOM | 2477 | CD1 | PHE | A | 179 | 56.233 | −48.824 | 15.453 | 1.00 | 30.81 | A | C |
| ATOM | 2479 | CE1 | PHE | A | 179 | 57.278 | −49.725 | 15.441 | 1.00 | 28.19 | A | C |
| ATOM | 2481 | CZ | PHE | A | 179 | 58.208 | −49.687 | 14.431 | 1.00 | 30.08 | A | C |
| ATOM | 2483 | CE2 | PHE | A | 179 | 58.089 | −48.755 | 13.424 | 1.00 | 30.12 | A | C |
| ATOM | 2485 | CD2 | PHE | A | 179 | 57.051 | −47.860 | 13.444 | 1.00 | 29.06 | A | C |
| ATOM | 2487 | C | PHE | A | 179 | 56.555 | −45.097 | 15.276 | 1.00 | 28.33 | A | C |
| ATOM | 2488 | O | PHE | A | 179 | 57.435 | −45.283 | 16.104 | 1.00 | 25.10 | A | O |
| ATOM | 2490 | N | ALA | A | 180 | 56.757 | −44.332 | 14.204 | 1.00 | 28.10 | A | N |
| ATOM | 2491 | CA | ALA | A | 180 | 58.054 | −43.728 | 13.971 | 1.00 | 26.76 | A | C |
| ATOM | 2493 | CB | ALA | A | 180 | 58.150 | −43.168 | 12.577 | 1.00 | 24.69 | A | C |
| ATOM | 2497 | C | ALA | A | 180 | 58.382 | −42.652 | 15.034 | 1.00 | 29.09 | A | C |
| ATOM | 2498 | O | ALA | A | 180 | 59.485 | −42.646 | 15.586 | 1.00 | 27.52 | A | O |
| ATOM | 2500 | N | ILE | A | 181 | 57.420 | −41.775 | 15.319 | 1.00 | 28.79 | A | N |
| ATOM | 2501 | CA | ILE | A | 181 | 57.591 | −40.717 | 16.285 | 1.00 | 30.81 | A | C |
| ATOM | 2503 | CB | ILE | A | 181 | 56.310 | −39.865 | 16.483 | 1.00 | 31.36 | A | C |
| ATOM | 2505 | CG1 | ILE | A | 181 | 56.105 | −38.909 | 15.302 | 1.00 | 38.18 | A | C |
| ATOM | 2508 | CD1 | ILE | A | 181 | 54.765 | −38.081 | 15.352 | 1.00 | 37.32 | A | C |
| ATOM | 2512 | CG2 | ILE | A | 181 | 56.415 | −39.000 | 17.738 | 1.00 | 34.50 | A | C |
| ATOM | 2516 | C | ILE | A | 181 | 58.002 | −41.293 | 17.629 | 1.00 | 33.92 | A | C |
| ATOM | 2517 | O | ILE | A | 181 | 58.908 | −40.757 | 18.270 | 1.00 | 32.34 | A | O |
| ATOM | 2519 | N | SER | A | 182 | 57.359 | −42.383 | 18.045 | 1.00 | 34.21 | A | N |
| ATOM | 2520 | CA | SER | A | 182 | 57.608 | −42.923 | 19.361 | 1.00 | 37.21 | A | C |
| ATOM | 2522 | CB | SER | A | 182 | 56.573 | −43.991 | 19.721 | 1.00 | 37.94 | A | C |
| ATOM | 2525 | OG | SER | A | 182 | 56.744 | −45.180 | 18.958 | 1.00 | 41.64 | A | O |
| ATOM | 2527 | C | SER | A | 182 | 59.030 | −43.474 | 19.473 | 1.00 | 38.60 | A | C |
| ATOM | 2528 | O | SER | A | 182 | 59.618 | −43.437 | 20.553 | 1.00 | 40.23 | A | O |
| ATOM | 2530 | N | HIS | A | 183 | 59.570 | −43.982 | 18.366 | 1.00 | 38.90 | A | N |
| ATOM | 2531 | CA | HIS | A | 183 | 60.933 | −44.519 | 18.342 | 1.00 | 40.39 | A | C |
| ATOM | 2533 | CB | HIS | A | 183 | 61.054 | −45.715 | 17.401 | 1.00 | 39.71 | A | C |
| ATOM | 2536 | CG | HIS | A | 183 | 60.270 | −46.913 | 17.839 | 1.00 | 46.09 | A | C |
| ATOM | 2537 | ND1 | HIS | A | 183 | 60.409 | −47.479 | 19.089 | 1.00 | 52.45 | A | N |
| ATOM | 2539 | CE1 | HIS | A | 183 | 59.597 | −48.516 | 19.192 | 1.00 | 55.12 | A | C |
| ATOM | 2541 | NE2 | HIS | A | 183 | 58.945 | −48.648 | 18.051 | 1.00 | 54.77 | A | N |
| ATOM | 2543 | CD2 | HIS | A | 183 | 59.349 | −47.660 | 17.188 | 1.00 | 47.51 | A | C |
| ATOM | 2545 | C | HIS | A | 183 | 61.972 | −43.469 | 17.945 | 1.00 | 41.16 | A | C |
| ATOM | 2546 | O | HIS | A | 183 | 63.162 | −43.724 | 18.087 | 1.00 | 44.04 | A | O |
| ATOM | 2548 | N | LEU | A | 184 | 61.536 | −42.314 | 17.439 | 1.00 | 38.00 | A | N |
| ATOM | 2549 | CA | LEU | A | 184 | 62.448 | −41.207 | 17.193 | 1.00 | 37.65 | A | C |
| ATOM | 2551 | CB | LEU | A | 184 | 62.018 | −40.400 | 15.968 | 1.00 | 34.76 | A | C |
| ATOM | 2554 | CG | LEU | A | 184 | 62.130 | −41.133 | 14.624 | 1.00 | 35.32 | A | C |
| ATOM | 2556 | CD1 | LEU | A | 184 | 61.311 | −40.390 | 13.576 | 1.00 | 22.44 | A | C |
| ATOM | 2560 | CD2 | LEU | A | 184 | 63.579 | −41.297 | 14.167 | 1.00 | 24.78 | A | C |
| ATOM | 2564 | C | LEU | A | 184 | 62.591 | −40.267 | 18.400 | 1.00 | 37.45 | A | C |
| ATOM | 2565 | O | LEU | A | 184 | 63.620 | −39.647 | 18.551 | 1.00 | 33.63 | A | O |
| ATOM | 2567 | N | LYS | A | 185 | 61.558 | −40.165 | 19.231 | 1.00 | 40.96 | A | N |
| ATOM | 2568 | CA | LYS | A | 185 | 61.490 | −39.158 | 20.286 | 1.00 | 46.25 | A | C |
| ATOM | 2570 | CB | LYS | A | 185 | 60.062 | −39.043 | 20.825 | 1.00 | 47.18 | A | C |
| ATOM | 2573 | CG | LYS | A | 185 | 59.568 | −37.619 | 20.940 | 1.00 | 54.79 | A | C |
| ATOM | 2576 | CD | LYS | A | 185 | 58.037 | −37.534 | 21.071 | 1.00 | 62.29 | A | C |
| ATOM | 2579 | CE | LYS | A | 185 | 57.489 | −36.307 | 20.328 | 1.00 | 65.20 | A | C |
| ATOM | 2582 | NZ | LYS | A | 185 | 56.019 | −36.110 | 20.508 | 1.00 | 64.22 | A | N |
| ATOM | 2586 | C | LYS | A | 185 | 62.412 | −39.502 | 21.447 | 1.00 | 50.17 | A | C |
| ATOM | 2587 | O | LYS | A | 185 | 62.835 | −38.626 | 22.190 | 1.00 | 50.48 | A | O |
| ATOM | 2589 | N | GLU | A | 186 | 62.695 | −40.786 | 21.608 | 1.00 | 54.79 | A | N |
| ATOM | 2590 | CA | GLU | A | 186 | 63.492 | −41.268 | 22.714 | 1.00 | 59.57 | A | C |
| ATOM | 2592 | CB | GLU | A | 186 | 62.748 | −42.417 | 23.422 | 1.00 | 61.31 | A | C |
| ATOM | 2595 | CG | GLU | A | 186 | 61.324 | −42.053 | 23.918 | 1.00 | 65.37 | A | C |
| ATOM | 2598 | CD | GLU | A | 186 | 61.289 | −40.817 | 24.837 | 1.00 | 71.20 | A | C |
| ATOM | 2599 | OE1 | GLU | A | 186 | 62.279 | −40.570 | 25.570 | 1.00 | 72.40 | A | O |
| ATOM | 2600 | OE2 | GLU | A | 186 | 60.266 | −40.090 | 24.826 | 1.00 | 69.58 | A | O |
| ATOM | 2601 | C | GLU | A | 186 | 64.859 | −41.715 | 22.199 | 1.00 | 61.26 | A | C |
| ATOM | 2602 | O | GLU | A | 186 | 65.344 | −42.800 | 22.545 | 1.00 | 61.31 | A | O |
| ATOM | 2604 | N | LEU | A | 187 | 65.474 | −40.871 | 21.368 | 1.00 | 61.95 | A | N |
| ATOM | 2605 | CA | LEU | A | 187 | 66.803 | −41.144 | 20.832 | 1.00 | 62.48 | A | C |
| ATOM | 2607 | CB | LEU | A | 187 | 66.795 | −41.069 | 19.309 | 1.00 | 61.46 | A | C |
| ATOM | 2610 | CG | LEU | A | 187 | 66.046 | −42.207 | 18.622 | 1.00 | 60.67 | A | C |
| ATOM | 2612 | CD1 | LEU | A | 187 | 66.159 | −42.112 | 17.107 | 1.00 | 54.64 | A | C |
| ATOM | 2616 | CD2 | LEU | A | 187 | 66.571 | −43.549 | 19.105 | 1.00 | 60.19 | A | C |
| ATOM | 2620 | C | LEU | A | 187 | 67.848 | −40.185 | 21.403 | 1.00 | 64.11 | A | C |
| ATOM | 2621 | O | LEU | A | 187 | 67.646 | −38.964 | 21.436 | 1.00 | 63.36 | A | O |
| ATOM | 2623 | N | SER | A | 188 | 68.968 | −40.764 | 21.842 | 1.00 | 66.14 | A | N |
| ATOM | 2624 | CA | SER | A | 188 | 70.064 | −40.014 | 22.460 | 1.00 | 66.96 | A | C |
| ATOM | 2626 | CB | SER | A | 188 | 70.591 | −40.762 | 23.685 | 1.00 | 67.57 | A | C |
| ATOM | 2629 | OG | SER | A | 188 | 69.575 | −40.923 | 24.660 | 1.00 | 70.39 | A | O |
| ATOM | 2631 | C | SER | A | 188 | 71.203 | −39.809 | 21.472 | 1.00 | 66.59 | A | C |
| ATOM | 2632 | O | SER | A | 188 | 71.607 | −40.744 | 20.766 | 1.00 | 64.52 | A | O |
| ATOM | 2634 | N | GLU | A | 189 | 71.720 | −38.583 | 21.438 | 1.00 | 67.77 | A | N |

TABLE 4-2-continued

Coordinates of *P. alba* IspS

| ATOM | 2635 | CA | GLU | A | 189 | 72.847 | −38.231 | 20.578 | 1.00 | 69.56 | A | C |
|---|---|---|---|---|---|---|---|---|---|---|---|---|
| ATOM | 2637 | CB | GLU | A | 189 | 73.248 | −36.765 | 20.791 | 1.00 | 70.17 | A | C |
| ATOM | 2640 | CG | GLU | A | 189 | 74.339 | −36.266 | 19.841 | 1.00 | 73.91 | A | C |
| ATOM | 2643 | CD | GLU | A | 189 | 74.480 | −34.742 | 19.820 | 1.00 | 79.04 | A | C |
| ATOM | 2644 | OE1 | GLU | A | 189 | 73.752 | −34.043 | 20.565 | 1.00 | 78.69 | A | O |
| ATOM | 2645 | OE2 | GLU | A | 189 | 75.329 | −34.244 | 19.044 | 1.00 | 81.94 | A | O |
| ATOM | 2646 | C | GLU | A | 189 | 74.039 | −39.156 | 20.818 | 1.00 | 70.07 | A | C |
| ATOM | 2647 | O | GLU | A | 189 | 74.733 | −39.517 | 19.875 | 1.00 | 68.55 | A | O |
| ATOM | 2649 | N | GLU | A | 190 | 74.260 | −39.536 | 22.078 | 1.00 | 71.69 | A | N |
| ATOM | 2650 | CA | GLU | A | 190 | 75.327 | −40.477 | 22.448 | 1.00 | 72.75 | A | C |
| ATOM | 2652 | CB | GLU | A | 190 | 75.285 | −40.796 | 23.952 | 1.00 | 73.95 | A | C |
| ATOM | 2655 | CG | GLU | A | 190 | 76.108 | −39.856 | 24.832 | 1.00 | 77.12 | A | C |
| ATOM | 2658 | CD | GLU | A | 190 | 75.626 | −38.415 | 24.801 | 1.00 | 81.42 | A | C |
| ATOM | 2659 | OE1 | GLU | A | 190 | 74.514 | −38.146 | 24.284 | 1.00 | 82.03 | A | O |
| ATOM | 2660 | OE2 | GLU | A | 190 | 76.372 | −37.546 | 25.303 | 1.00 | 83.94 | A | O |
| ATOM | 2661 | C | GLU | A | 190 | 75.242 | −41.777 | 21.654 | 1.00 | 72.09 | A | C |
| ATOM | 2662 | O | GLU | A | 190 | 76.225 | −42.207 | 21.051 | 1.00 | 72.00 | A | O |
| ATOM | 2664 | N | LYS | A | 191 | 74.058 | −42.384 | 21.648 | 1.00 | 71.50 | A | N |
| ATOM | 2665 | CA | LYS | A | 191 | 73.837 | −43.669 | 20.977 | 1.00 | 71.87 | A | C |
| ATOM | 2667 | CB | LYS | A | 191 | 72.406 | −44.167 | 21.222 | 1.00 | 72.85 | A | C |
| ATOM | 2670 | CG | LYS | A | 191 | 71.999 | −44.262 | 22.685 | 1.00 | 77.73 | A | C |
| ATOM | 2673 | CD | LYS | A | 191 | 72.705 | −45.417 | 23.395 | 1.00 | 84.01 | A | C |
| ATOM | 2676 | CE | LYS | A | 191 | 72.961 | −45.117 | 24.873 | 1.00 | 85.51 | A | C |
| ATOM | 2679 | NZ | LYS | A | 191 | 74.197 | −45.799 | 25.352 | 1.00 | 86.45 | A | N |
| ATOM | 2683 | C | LYS | A | 191 | 74.081 | −43.581 | 19.467 | 1.00 | 70.30 | A | C |
| ATOM | 2684 | O | LYS | A | 191 | 74.929 | −44.293 | 18.923 | 1.00 | 70.06 | A | O |
| ATOM | 2686 | N | ILE | A | 192 | 73.337 | −42.700 | 18.803 | 1.00 | 68.27 | A | N |
| ATOM | 2687 | CA | ILE | A | 192 | 73.412 | −42.559 | 17.344 | 1.00 | 67.41 | A | C |
| ATOM | 2689 | CB | ILE | A | 192 | 72.021 | −42.259 | 16.721 | 1.00 | 66.84 | A | C |
| ATOM | 2691 | CG1 | ILE | A | 192 | 71.413 | −40.959 | 17.266 | 1.00 | 66.08 | A | C |
| ATOM | 2694 | CD1 | ILE | A | 192 | 70.180 | −40.498 | 16.516 | 1.00 | 61.79 | A | C |
| ATOM | 2698 | CG2 | ILE | A | 192 | 71.079 | −43.397 | 17.011 | 1.00 | 66.67 | A | C |
| ATOM | 2702 | C | ILE | A | 192 | 74.418 | −41.476 | 16.984 | 1.00 | 66.49 | A | C |
| ATOM | 2703 | O | ILE | A | 192 | 75.005 | −40.860 | 17.864 | 1.00 | 65.60 | A | O |
| ATOM | 2705 | N | GLY | A | 193 | 74.623 | −41.241 | 15.694 | 1.00 | 66.38 | A | N |
| ATOM | 2706 | CA | GLY | A | 193 | 75.553 | −40.195 | 15.259 | 1.00 | 66.52 | A | C |
| ATOM | 2709 | C | GLY | A | 193 | 75.264 | −38.810 | 15.831 | 1.00 | 65.05 | A | C |
| ATOM | 2710 | O | GLY | A | 193 | 74.192 | −38.557 | 16.396 | 1.00 | 64.86 | A | O |
| ATOM | 2712 | N | LYS | A | 194 | 76.235 | −37.910 | 15.701 | 1.00 | 62.68 | A | N |
| ATOM | 2713 | CA | LYS | A | 194 | 75.958 | −36.492 | 15.879 | 1.00 | 61.11 | A | C |
| ATOM | 2715 | CB | LYS | A | 194 | 77.243 | −35.657 | 15.953 | 1.00 | 62.09 | A | C |
| ATOM | 2718 | CG | LYS | A | 194 | 78.355 | −36.254 | 16.839 | 1.00 | 69.49 | A | C |
| ATOM | 2721 | CD | LYS | A | 194 | 79.386 | −35.198 | 17.291 | 1.00 | 73.25 | A | C |
| ATOM | 2724 | CE | LYS | A | 194 | 80.488 | −35.828 | 18.136 | 1.00 | 73.20 | A | C |
| ATOM | 2727 | NZ | LYS | A | 194 | 81.352 | −34.809 | 18.783 | 1.00 | 72.29 | A | N |
| ATOM | 2731 | C | LYS | A | 194 | 75.096 | −36.058 | 14.680 | 1.00 | 58.07 | A | C |
| ATOM | 2732 | O | LYS | A | 194 | 74.119 | −35.337 | 14.842 | 1.00 | 56.95 | A | O |
| ATOM | 2734 | N | GLU | A | 195 | 75.447 | −36.528 | 13.484 | 1.00 | 54.22 | A | N |
| ATOM | 2735 | CA | GLU | A | 195 | 74.722 | −36.140 | 12.287 | 1.00 | 53.49 | A | C |
| ATOM | 2737 | CB | GLU | A | 195 | 75.507 | −36.489 | 11.005 | 1.00 | 53.97 | A | C |
| ATOM | 2740 | CG | GLU | A | 195 | 75.487 | −37.950 | 10.549 | 1.00 | 60.23 | A | C |
| ATOM | 2743 | CD | GLU | A | 195 | 76.394 | −38.208 | 9.329 | 1.00 | 66.28 | A | C |
| ATOM | 2744 | OE1 | GLU | A | 195 | 76.046 | −39.079 | 8.500 | 1.00 | 68.96 | A | O |
| ATOM | 2745 | OE2 | GLU | A | 195 | 77.450 | −37.544 | 9.194 | 1.00 | 62.48 | A | O |
| ATOM | 2746 | C | GLU | A | 195 | 73.296 | −36.714 | 12.261 | 1.00 | 50.83 | A | C |
| ATOM | 2747 | O | GLU | A | 195 | 72.363 | −36.050 | 11.773 | 1.00 | 48.97 | A | O |
| ATOM | 2749 | N | LEU | A | 196 | 73.125 | −37.925 | 12.792 | 1.00 | 46.53 | A | N |
| ATOM | 2750 | CA | LEU | A | 196 | 71.808 | −38.556 | 12.821 | 1.00 | 43.53 | A | C |
| ATOM | 2752 | CB | LEU | A | 196 | 71.892 | −40.048 | 13.130 | 1.00 | 43.43 | A | C |
| ATOM | 2755 | CG | LEU | A | 196 | 71.893 | −40.894 | 11.870 | 1.00 | 43.50 | A | C |
| ATOM | 2757 | CD1 | LEU | A | 196 | 72.472 | −42.286 | 12.143 | 1.00 | 46.58 | A | C |
| ATOM | 2761 | CD2 | LEU | A | 196 | 70.472 | −40.959 | 11.279 | 1.00 | 43.97 | A | C |
| ATOM | 2765 | C | LEU | A | 196 | 70.881 | −37.857 | 13.799 | 1.00 | 40.68 | A | C |
| ATOM | 2766 | O | LEU | A | 196 | 69.731 | −37.587 | 13.461 | 1.00 | 40.50 | A | O |
| ATOM | 2768 | N | ALA | A | 197 | 71.383 | −37.531 | 14.983 | 1.00 | 36.99 | A | N |
| ATOM | 2769 | CA | ALA | A | 197 | 70.584 | −36.804 | 15.961 | 1.00 | 35.57 | A | C |
| ATOM | 2771 | CB | ALA | A | 197 | 71.364 | −36.595 | 17.246 | 1.00 | 33.51 | A | C |
| ATOM | 2775 | C | ALA | A | 197 | 70.119 | −35.460 | 15.406 | 1.00 | 35.11 | A | C |
| ATOM | 2776 | O | ALA | A | 197 | 68.995 | −35.042 | 15.677 | 1.00 | 35.72 | A | O |
| ATOM | 2778 | N | GLU | A | 198 | 70.986 | −34.778 | 14.653 | 1.00 | 33.60 | A | N |
| ATOM | 2779 | CA | GLU | A | 198 | 70.605 | −33.513 | 14.002 | 1.00 | 35.29 | A | C |
| ATOM | 2781 | CB | GLU | A | 198 | 71.836 | −32.795 | 13.432 | 1.00 | 36.22 | A | C |
| ATOM | 2784 | CG | GLU | A | 198 | 72.762 | −32.235 | 14.540 | 1.00 | 50.06 | A | C |
| ATOM | 2787 | CD | GLU | A | 198 | 74.148 | −31.764 | 14.057 | 1.00 | 60.04 | A | C |
| ATOM | 2788 | OE1 | GLU | A | 198 | 74.806 | −32.492 | 13.272 | 1.00 | 66.90 | A | O |
| ATOM | 2789 | OE2 | GLU | A | 198 | 74.585 | −30.667 | 14.491 | 1.00 | 63.26 | A | O |
| ATOM | 2790 | C | GLU | A | 198 | 69.534 | −33.754 | 12.916 | 1.00 | 31.70 | A | C |
| ATOM | 2791 | O | GLU | A | 198 | 68.608 | −32.969 | 12.768 | 1.00 | 33.74 | A | O |

TABLE 4-2-continued

Coordinates of *P. alba* IspS

| | | | | | | | | | | | | |
|---|---|---|---|---|---|---|---|---|---|---|---|---|
| ATOM | 2793 | N | GLN | A | 199 | 69.647 | −34.857 | 12.201 | 1.00 | 28.08 | A | N |
| ATOM | 2794 | CA | GLN | A | 199 | 68.694 | −35.215 | 11.158 | 1.00 | 29.52 | A | C |
| ATOM | 2796 | CB | GLN | A | 199 | 69.315 | −36.342 | 10.323 | 1.00 | 30.33 | A | C |
| ATOM | 2799 | CG | GLN | A | 199 | 68.764 | −36.594 | 8.954 | 1.00 | 42.18 | A | C |
| ATOM | 2802 | CD | GLN | A | 199 | 69.077 | −35.489 | 7.927 | 1.00 | 53.91 | A | C |
| ATOM | 2803 | OE1 | GLN | A | 199 | 68.161 | −34.927 | 7.316 | 1.00 | 54.02 | A | O |
| ATOM | 2804 | NE2 | GLN | A | 199 | 70.359 | −35.211 | 7.705 | 1.00 | 47.12 | A | N |
| ATOM | 2807 | C | GLN | A | 199 | 67.326 | −35.566 | 11.828 | 1.00 | 27.82 | A | C |
| ATOM | 2808 | O | GLN | A | 199 | 66.277 | −35.071 | 11.419 | 1.00 | 24.92 | A | O |
| ATOM | 2810 | N | VAL | A | 200 | 67.361 | −36.329 | 12.922 | 1.00 | 27.96 | A | N |
| ATOM | 2811 | CA | VAL | A | 200 | 66.162 | −36.642 | 13.712 | 1.00 | 26.88 | A | C |
| ATOM | 2813 | CB | VAL | A | 200 | 66.485 | −37.637 | 14.821 | 1.00 | 28.23 | A | C |
| ATOM | 2815 | CG1 | VAL | A | 200 | 66.795 | −39.011 | 14.204 | 1.00 | 29.92 | A | C |
| ATOM | 2819 | CG2 | VAL | A | 200 | 65.342 | −37.736 | 15.839 | 1.00 | 23.69 | A | C |
| ATOM | 2823 | C | VAL | A | 200 | 65.496 | −35.422 | 14.336 | 1.00 | 27.44 | A | C |
| ATOM | 2824 | O | VAL | A | 200 | 64.277 | −35.274 | 14.235 | 1.00 | 26.51 | A | O |
| ATOM | 2826 | N | ASN | A | 201 | 66.288 | −34.536 | 14.946 | 1.00 | 27.44 | A | N |
| ATOM | 2827 | CA | ASN | A | 201 | 65.754 | −33.319 | 15.554 | 1.00 | 29.08 | A | C |
| ATOM | 2829 | CB | ASN | A | 201 | 66.835 | −32.603 | 16.398 | 1.00 | 30.46 | A | C |
| ATOM | 2832 | CG | ASN | A | 201 | 67.362 | −33.468 | 17.575 | 1.00 | 34.58 | A | C |
| ATOM | 2833 | OD1 | ASN | A | 201 | 66.665 | −34.330 | 18.124 | 1.00 | 43.42 | A | O |
| ATOM | 2834 | ND2 | ASN | A | 201 | 68.604 | −33.231 | 17.947 | 1.00 | 39.12 | A | N |
| ATOM | 2837 | C | ASN | A | 201 | 65.140 | −32.337 | 14.530 | 1.00 | 28.73 | A | C |
| ATOM | 2838 | O | ASN | A | 201 | 64.107 | −31.710 | 14.783 | 1.00 | 27.87 | A | O |
| ATOM | 2840 | N | HIS | A | 202 | 65.784 | −32.192 | 13.382 | 1.00 | 27.02 | A | N |
| ATOM | 2841 | CA | HIS | A | 202 | 65.237 | −31.386 | 12.299 | 1.00 | 26.81 | A | C |
| ATOM | 2843 | CB | HIS | A | 202 | 66.303 | −31.281 | 11.211 | 1.00 | 27.94 | A | C |
| ATOM | 2846 | CG | HIS | A | 202 | 65.862 | −30.625 | 9.942 | 1.00 | 26.52 | A | C |
| ATOM | 2847 | ND1 | HIS | A | 202 | 65.804 | −29.258 | 9.788 | 1.00 | 29.59 | A | N |
| ATOM | 2849 | CE1 | HIS | A | 202 | 65.435 | −28.970 | 8.554 | 1.00 | 28.13 | A | C |
| ATOM | 2851 | NE2 | HIS | A | 202 | 65.288 | −30.102 | 7.890 | 1.00 | 26.07 | A | N |
| ATOM | 2853 | CD2 | HIS | A | 202 | 65.564 | −31.150 | 8.733 | 1.00 | 26.24 | A | C |
| ATOM | 2855 | C | HIS | A | 202 | 63.901 | −32.018 | 11.785 | 1.00 | 25.69 | A | C |
| ATOM | 2856 | O | HIS | A | 202 | 62.890 | −31.339 | 11.667 | 1.00 | 21.65 | A | O |
| ATOM | 2858 | N | ALA | A | 203 | 63.867 | −33.315 | 11.553 | 1.00 | 25.23 | A | N |
| ATOM | 2859 | CA | ALA | A | 203 | 62.598 | −33.931 | 11.112 | 1.00 | 25.49 | A | C |
| ATOM | 2861 | CB | ALA | A | 203 | 62.812 | −35.337 | 10.748 | 1.00 | 24.59 | A | C |
| ATOM | 2865 | C | ALA | A | 203 | 61.489 | −33.824 | 12.173 | 1.00 | 27.25 | A | C |
| ATOM | 2866 | O | ALA | A | 203 | 60.321 | −33.627 | 11.837 | 1.00 | 29.18 | A | O |
| ATOM | 2868 | N | LEU | A | 204 | 61.839 | −33.928 | 13.451 | 1.00 | 26.81 | A | N |
| ATOM | 2869 | CA | LEU | A | 204 | 60.807 | −33.831 | 14.517 | 1.00 | 26.42 | A | C |
| ATOM | 2871 | CB | LEU | A | 204 | 61.317 | −34.405 | 15.850 | 1.00 | 24.88 | A | C |
| ATOM | 2874 | CG | LEU | A | 204 | 61.517 | −35.936 | 15.832 | 1.00 | 26.48 | A | C |
| ATOM | 2876 | CD1 | LEU | A | 204 | 62.119 | −36.465 | 17.114 | 1.00 | 26.30 | A | C |
| ATOM | 2880 | CD2 | LEU | A | 204 | 60.203 | −36.639 | 15.557 | 1.00 | 23.97 | A | C |
| ATOM | 2884 | C | LEU | A | 204 | 60.305 | −32.392 | 14.672 | 1.00 | 27.71 | A | C |
| ATOM | 2885 | O | LEU | A | 204 | 59.148 | −32.160 | 15.001 | 1.00 | 27.30 | A | O |
| ATOM | 2887 | N | GLU | A | 205 | 61.183 | −31.430 | 14.415 | 1.00 | 27.31 | A | N |
| ATOM | 2888 | CA | GLU | A | 205 | 60.805 | −30.037 | 14.394 | 1.00 | 27.78 | A | C |
| ATOM | 2890 | CB | GLU | A | 205 | 62.015 | −29.143 | 14.068 | 1.00 | 27.71 | A | C |
| ATOM | 2893 | CG | GLU | A | 205 | 61.697 | −27.658 | 14.056 | 1.00 | 29.29 | A | C |
| ATOM | 2896 | CD | GLU | A | 205 | 62.860 | −26.816 | 13.541 | 1.00 | 37.90 | A | C |
| ATOM | 2897 | OE1 | GLU | A | 205 | 63.289 | −27.047 | 12.395 | 1.00 | 32.00 | A | O |
| ATOM | 2898 | OE2 | GLU | A | 205 | 63.349 | −25.930 | 14.288 | 1.00 | 44.77 | A | O |
| ATOM | 2899 | C | GLU | A | 205 | 59.729 | −29.859 | 13.348 | 1.00 | 27.03 | A | C |
| ATOM | 2900 | O | GLU | A | 205 | 58.699 | −29.270 | 13.627 | 1.00 | 27.56 | A | O |
| ATOM | 2902 | N | LEU | A | 206 | 59.982 | −30.359 | 12.144 | 1.00 | 25.59 | A | N |
| ATOM | 2903 | CA | LEU | A | 206 | 59.004 | −30.289 | 11.062 | 1.00 | 25.22 | A | C |
| ATOM | 2905 | CB | LEU | A | 206 | 58.886 | −28.840 | 10.561 | 1.00 | 24.64 | A | C |
| ATOM | 2908 | CG | LEU | A | 206 | 57.694 | −28.433 | 9.711 | 1.00 | 24.27 | A | C |
| ATOM | 2910 | CD1 | LEU | A | 206 | 56.411 | −28.371 | 10.529 | 1.00 | 17.46 | A | C |
| ATOM | 2914 | CD2 | LEU | A | 206 | 57.955 | −27.063 | 9.063 | 1.00 | 21.01 | A | C |
| ATOM | 2918 | C | LEU | A | 206 | 59.416 | −31.196 | 9.917 | 1.00 | 24.56 | A | C |
| ATOM | 2919 | O | LEU | A | 206 | 60.540 | −31.118 | 9.444 | 1.00 | 25.68 | A | O |
| ATOM | 2921 | N | PRO | A | 207 | 58.492 | −32.045 | 9.437 | 1.00 | 24.29 | A | N |
| ATOM | 2922 | CA | PRO | A | 207 | 58.784 | −32.963 | 8.354 | 1.00 | 23.07 | A | C |
| ATOM | 2924 | CB | PRO | A | 207 | 57.522 | −33.795 | 8.289 | 1.00 | 25.30 | A | C |
| ATOM | 2927 | CG | PRO | A | 207 | 56.469 | −32.830 | 8.679 | 1.00 | 25.11 | A | C |
| ATOM | 2930 | CD | PRO | A | 207 | 57.058 | −32.039 | 9.765 | 1.00 | 23.79 | A | C |
| ATOM | 2933 | C | PRO | A | 207 | 59.003 | −32.256 | 7.014 | 1.00 | 21.55 | A | C |
| ATOM | 2934 | O | PRO | A | 207 | 58.522 | −31.166 | 6.819 | 1.00 | 22.11 | A | O |
| ATOM | 2935 | N | LEU | A | 208 | 59.694 | −32.924 | 6.102 | 1.00 | 22.41 | A | N |
| ATOM | 2936 | CA | LEU | A | 208 | 60.022 | −32.401 | 4.805 | 1.00 | 22.23 | A | C |
| ATOM | 2938 | CB | LEU | A | 208 | 60.690 | −33.496 | 3.997 | 1.00 | 26.10 | A | C |
| ATOM | 2941 | CG | LEU | A | 208 | 62.061 | −33.942 | 4.475 | 1.00 | 32.53 | A | C |
| ATOM | 2943 | CD1 | LEU | A | 208 | 62.395 | −35.348 | 3.945 | 1.00 | 35.78 | A | C |
| ATOM | 2947 | CD2 | LEU | A | 208 | 63.091 | −32.897 | 4.009 | 1.00 | 35.33 | A | C |
| ATOM | 2951 | C | LEU | A | 208 | 58.814 | −31.930 | 4.019 | 1.00 | 23.30 | A | C |

TABLE 4-2-continued

Coordinates of *P. alba* IspS

| ATOM | 2952 | O | LEU | A | 208 | 58.865 | −30.914 | 3.333 | 1.00 | 27.80 | A | O |
|---|---|---|---|---|---|---|---|---|---|---|---|---|
| ATOM | 2954 | N | HIS | A | 209 | 57.733 | −32.688 | 4.081 | 1.00 | 21.48 | A | N |
| ATOM | 2955 | CA | HIS | A | 209 | 56.531 | −32.356 | 3.333 | 1.00 | 20.94 | A | C |
| ATOM | 2957 | CB | HIS | A | 209 | 55.497 | −33.453 | 3.521 | 1.00 | 20.23 | A | C |
| ATOM | 2960 | CG | HIS | A | 209 | 54.347 | −33.380 | 2.571 | 1.00 | 21.97 | A | C |
| ATOM | 2961 | ND1 | HIS | A | 209 | 54.509 | −33.408 | 1.200 | 1.00 | 19.00 | A | N |
| ATOM | 2963 | CE1 | HIS | A | 209 | 53.316 | −33.366 | 0.621 | 1.00 | 17.86 | A | C |
| ATOM | 2965 | NE2 | HIS | A | 209 | 52.392 | −33.319 | 1.568 | 1.00 | 20.62 | A | N |
| ATOM | 2967 | CD2 | HIS | A | 209 | 53.011 | −33.333 | 2.797 | 1.00 | 17.40 | A | C |
| ATOM | 2969 | C | HIS | A | 209 | 55.890 | −31.039 | 3.769 | 1.00 | 20.60 | A | C |
| ATOM | 2970 | O | HIS | A | 209 | 55.095 | −30.479 | 3.030 | 1.00 | 22.10 | A | O |
| ATOM | 2972 | N | ARG | A | 210 | 56.182 | −30.578 | 4.970 | 1.00 | 19.06 | A | N |
| ATOM | 2973 | CA | ARG | A | 210 | 55.590 | −29.330 | 5.442 | 1.00 | 21.68 | A | C |
| ATOM | 2975 | CB | ARG | A | 210 | 54.984 | −29.513 | 6.825 | 1.00 | 21.62 | A | C |
| ATOM | 2978 | CG | ARG | A | 210 | 53.868 | −30.527 | 6.845 | 1.00 | 21.69 | A | C |
| ATOM | 2981 | CD | ARG | A | 210 | 53.157 | −30.548 | 8.198 | 1.00 | 21.87 | A | C |
| ATOM | 2984 | NE | ARG | A | 210 | 52.032 | −31.469 | 8.145 | 1.00 | 28.50 | A | N |
| ATOM | 2986 | CZ | ARG | A | 210 | 51.306 | −31.867 | 9.185 | 1.00 | 27.73 | A | C |
| ATOM | 2987 | NH1 | ARG | A | 210 | 51.565 | −31.422 | 10.396 | 1.00 | 25.20 | A | N |
| ATOM | 2990 | NH2 | ARG | A | 210 | 50.306 | −32.732 | 9.001 | 1.00 | 22.65 | A | N |
| ATOM | 2993 | C | ARG | A | 210 | 56.554 | −28.162 | 5.510 | 1.00 | 23.56 | A | C |
| ATOM | 2994 | O | ARG | A | 210 | 56.098 | −27.052 | 5.712 | 1.00 | 25.20 | A | O |
| ATOM | 2996 | N | ARG | A | 211 | 57.861 | −28.390 | 5.317 | 1.00 | 22.15 | A | N |
| ATOM | 2997 | CA | ARG | A | 211 | 58.824 | −27.328 | 5.454 | 1.00 | 22.08 | A | C |
| ATOM | 2999 | CB | ARG | A | 211 | 60.164 | −27.898 | 5.911 | 1.00 | 21.53 | A | C |
| ATOM | 3002 | CG | ARG | A | 211 | 61.184 | −26.803 | 6.252 | 1.00 | 25.30 | A | C |
| ATOM | 3005 | CD | ARG | A | 211 | 62.498 | −27.377 | 6.683 | 1.00 | 23.90 | A | C |
| ATOM | 3008 | NE | ARG | A | 211 | 62.394 | −28.298 | 7.815 | 1.00 | 20.68 | A | N |
| ATOM | 3010 | CZ | ARG | A | 211 | 62.577 | −27.968 | 9.097 | 1.00 | 29.21 | A | C |
| ATOM | 3011 | NH1 | ARG | A | 211 | 62.842 | −26.723 | 9.458 | 1.00 | 31.64 | A | N |
| ATOM | 3014 | NH2 | ARG | A | 211 | 62.482 | −28.895 | 10.040 | 1.00 | 33.26 | A | N |
| ATOM | 3017 | C | ARG | A | 211 | 58.995 | −26.636 | 4.124 | 1.00 | 22.87 | A | C |
| ATOM | 3018 | O | ARG | A | 211 | 58.943 | −27.308 | 3.080 | 1.00 | 23.69 | A | O |
| ATOM | 3020 | N | THR | A | 212 | 59.225 | −25.313 | 4.131 | 1.00 | 21.93 | A | N |
| ATOM | 3021 | CA | THR | A | 212 | 59.457 | −24.587 | 2.846 | 1.00 | 22.40 | A | C |
| ATOM | 3023 | CB | THR | A | 212 | 59.553 | −23.073 | 3.006 | 1.00 | 21.65 | A | C |
| ATOM | 3025 | OG1 | THR | A | 212 | 60.391 | −22.782 | 4.111 | 1.00 | 28.79 | A | O |
| ATOM | 3027 | CG2 | THR | A | 212 | 58.204 | −22.457 | 3.215 | 1.00 | 21.41 | A | C |
| ATOM | 3031 | C | THR | A | 212 | 60.748 | −25.035 | 2.161 | 1.00 | 24.44 | A | C |
| ATOM | 3032 | O | THR | A | 212 | 61.667 | −25.593 | 2.790 | 1.00 | 22.73 | A | O |
| ATOM | 3034 | N | GLN | A | 213 | 60.831 | −24.769 | 0.862 | 1.00 | 24.88 | A | N |
| ATOM | 3035 | CA | GLN | A | 213 | 61.890 | −25.361 | 0.042 | 1.00 | 23.30 | A | C |
| ATOM | 3037 | CB | GLN | A | 213 | 61.510 | −25.230 | −1.431 | 1.00 | 22.38 | A | C |
| ATOM | 3040 | CG | GLN | A | 213 | 62.232 | −26.167 | −2.392 | 1.00 | 26.87 | A | C |
| ATOM | 3043 | CD | GLN | A | 213 | 63.551 | −25.606 | −2.913 | 1.00 | 30.03 | A | C |
| ATOM | 3044 | OE1 | GLN | A | 213 | 64.199 | −24.764 | −2.277 | 1.00 | 31.33 | A | O |
| ATOM | 3045 | NE2 | GLN | A | 213 | 63.969 | −26.095 | −4.062 | 1.00 | 27.33 | A | N |
| ATOM | 3048 | C | GLN | A | 213 | 63.238 | −24.674 | 0.385 | 1.00 | 23.77 | A | C |
| ATOM | 3049 | O | GLN | A | 213 | 64.269 | −25.339 | 0.641 | 1.00 | 23.11 | A | O |
| ATOM | 3051 | N | ARG | A | 214 | 63.242 | −23.348 | 0.444 | 1.00 | 22.75 | A | N |
| ATOM | 3052 | CA | ARG | A | 214 | 64.496 | −22.646 | 0.771 | 1.00 | 22.94 | A | C |
| ATOM | 3054 | CB | ARG | A | 214 | 64.351 | −21.150 | 0.591 | 1.00 | 21.67 | A | C |
| ATOM | 3057 | CG | ARG | A | 214 | 64.105 | −20.728 | −0.863 | 1.00 | 25.36 | A | C |
| ATOM | 3060 | CD | ARG | A | 214 | 65.370 | −20.851 | −1.745 | 1.00 | 25.37 | A | C |
| ATOM | 3063 | NE | ARG | A | 214 | 65.517 | −22.198 | −2.265 | 1.00 | 19.85 | A | N |
| ATOM | 3065 | CZ | ARG | A | 214 | 66.500 | −22.609 | −3.067 | 1.00 | 22.24 | A | C |
| ATOM | 3066 | NH1 | ARG | A | 214 | 67.440 | −21.780 | −3.482 | 1.00 | 23.25 | A | N |
| ATOM | 3069 | NH2 | ARG | A | 214 | 66.530 | −23.870 | −3.478 | 1.00 | 21.78 | A | N |
| ATOM | 3072 | C | ARG | A | 214 | 65.045 | −22.987 | 2.163 | 1.00 | 22.57 | A | C |
| ATOM | 3073 | O | ARG | A | 214 | 66.276 | −23.153 | 2.325 | 1.00 | 22.67 | A | O |
| ATOM | 3075 | N | LEU | A | 215 | 64.168 | −23.142 | 3.156 | 1.00 | 21.88 | A | N |
| ATOM | 3076 | CA | LEU | A | 215 | 64.640 | −23.425 | 4.534 | 1.00 | 22.10 | A | C |
| ATOM | 3078 | CB | LEU | A | 215 | 63.530 | −23.342 | 5.574 | 1.00 | 23.69 | A | C |
| ATOM | 3081 | CG | LEU | A | 215 | 63.166 | −22.064 | 6.320 | 1.00 | 34.74 | A | C |
| ATOM | 3083 | CD1 | LEU | A | 215 | 64.377 | −21.478 | 7.038 | 1.00 | 30.99 | A | C |
| ATOM | 3087 | CD2 | LEU | A | 215 | 62.022 | −22.394 | 7.334 | 1.00 | 34.69 | A | C |
| ATOM | 3091 | C | LEU | A | 215 | 65.225 | −24.807 | 4.601 | 1.00 | 21.97 | A | C |
| ATOM | 3092 | O | LEU | A | 215 | 66.251 | −25.033 | 5.243 | 1.00 | 23.04 | A | O |
| ATOM | 3094 | N | GLU | A | 216 | 64.563 | −25.759 | 3.964 | 1.00 | 22.38 | A | N |
| ATOM | 3095 | CA | GLU | A | 216 | 65.143 | −27.091 | 3.849 | 1.00 | 23.79 | A | C |
| ATOM | 3097 | CB | GLU | A | 216 | 64.203 | −28.054 | 3.092 | 1.00 | 24.11 | A | C |
| ATOM | 3100 | CG | GLU | A | 216 | 64.735 | −29.469 | 3.009 | 1.00 | 23.98 | A | C |
| ATOM | 3103 | CD | GLU | A | 216 | 65.092 | −30.054 | 4.372 | 1.00 | 30.09 | A | C |
| ATOM | 3104 | OE1 | GLU | A | 216 | 64.489 | −29.635 | 5.368 | 1.00 | 38.31 | A | O |
| ATOM | 3105 | OE2 | GLU | A | 216 | 65.963 | −30.950 | 4.462 | 1.00 | 31.71 | A | O |
| ATOM | 3106 | C | GLU | A | 216 | 66.495 | −27.043 | 3.151 | 1.00 | 22.00 | A | C |
| ATOM | 3107 | O | GLU | A | 216 | 67.417 | −27.725 | 3.566 | 1.00 | 25.42 | A | O |
| ATOM | 3109 | N | ALA | A | 217 | 66.609 | −26.265 | 2.075 | 1.00 | 21.69 | A | N |

TABLE 4-2-continued

Coordinates of *P. alba* IspS

| ATOM | 3110 | CA | ALA | A | 217 | 67.860 | −26.207 | 1.307 | 1.00 | 21.04 | A | C |
|---|---|---|---|---|---|---|---|---|---|---|---|---|
| ATOM | 3112 | CB | ALA | A | 217 | 67.713 | −25.322 | 0.057 | 1.00 | 16.62 | A | C |
| ATOM | 3116 | C | ALA | A | 217 | 68.997 | −25.695 | 2.170 | 1.00 | 22.50 | A | C |
| ATOM | 3117 | O | ALA | A | 217 | 70.086 | −26.294 | 2.207 | 1.00 | 24.32 | A | O |
| ATOM | 3119 | N | VAL | A | 218 | 68.754 | −24.598 | 2.880 | 1.00 | 22.51 | A | N |
| ATOM | 3120 | CA | VAL | A | 218 | 69.841 | −23.970 | 3.638 | 1.00 | 23.74 | A | C |
| ATOM | 3122 | CB | VAL | A | 218 | 69.501 | −22.546 | 4.127 | 1.00 | 24.58 | A | C |
| ATOM | 3124 | CG1 | VAL | A | 218 | 68.630 | −22.593 | 5.350 | 1.00 | 23.58 | A | C |
| ATOM | 3128 | CG2 | VAL | A | 218 | 70.816 | −21.738 | 4.397 | 1.00 | 28.37 | A | C |
| ATOM | 3132 | C | VAL | A | 218 | 70.244 | −24.871 | 4.785 | 1.00 | 23.83 | A | C |
| ATOM | 3133 | O | VAL | A | 218 | 71.408 | −24.959 | 5.120 | 1.00 | 28.06 | A | O |
| ATOM | 3135 | N | TRP | A | 219 | 69.292 | −25.582 | 5.366 | 1.00 | 25.17 | A | N |
| ATOM | 3136 | CA | TRP | A | 219 | 69.614 | −26.553 | 6.384 | 1.00 | 24.87 | A | C |
| ATOM | 3138 | CB | TRP | A | 219 | 68.353 | −27.038 | 7.105 | 1.00 | 25.79 | A | C |
| ATOM | 3141 | CG | TRP | A | 219 | 68.684 | −27.877 | 8.273 | 1.00 | 25.24 | A | C |
| ATOM | 3142 | CD1 | TRP | A | 219 | 68.904 | −27.444 | 9.559 | 1.00 | 26.80 | A | C |
| ATOM | 3144 | NE1 | TRP | A | 219 | 69.218 | −28.508 | 10.361 | 1.00 | 24.26 | A | N |
| ATOM | 3146 | CE2 | TRP | A | 219 | 69.240 | −29.648 | 9.604 | 1.00 | 28.74 | A | C |
| ATOM | 3147 | CD2 | TRP | A | 219 | 68.921 | −29.281 | 8.274 | 1.00 | 20.92 | A | C |
| ATOM | 3148 | CE3 | TRP | A | 219 | 68.869 | −30.273 | 7.291 | 1.00 | 28.67 | A | C |
| ATOM | 3150 | CZ3 | TRP | A | 219 | 69.133 | −31.587 | 7.659 | 1.00 | 31.01 | A | C |
| ATOM | 3152 | CH2 | TRP | A | 219 | 69.464 | −31.920 | 8.991 | 1.00 | 31.59 | A | C |
| ATOM | 3154 | CZ2 | TRP | A | 219 | 69.524 | −30.968 | 9.974 | 1.00 | 31.18 | A | C |
| ATOM | 3156 | C | TRP | A | 219 | 70.368 | −27.756 | 5.817 | 1.00 | 23.79 | A | C |
| ATOM | 3157 | O | TRP | A | 219 | 71.341 | −28.186 | 6.403 | 1.00 | 26.06 | A | O |
| ATOM | 3159 | N | SER | A | 220 | 69.912 | −28.314 | 4.700 | 1.00 | 23.59 | A | N |
| ATOM | 3160 | CA | SER | A | 220 | 70.515 | −29.556 | 4.168 | 1.00 | 23.50 | A | C |
| ATOM | 3162 | CB | SER | A | 220 | 69.604 | −30.197 | 3.104 | 1.00 | 23.55 | A | C |
| ATOM | 3165 | OG | SER | A | 220 | 68.632 | −31.034 | 3.711 | 1.00 | 29.70 | A | O |
| ATOM | 3167 | C | SER | A | 220 | 71.909 | −29.365 | 3.572 | 1.00 | 23.39 | A | C |
| ATOM | 3168 | O | SER | A | 220 | 72.739 | −30.270 | 3.630 | 1.00 | 25.12 | A | O |
| ATOM | 3170 | N | ILE | A | 221 | 72.141 | −28.206 | 2.976 | 1.00 | 23.77 | A | N |
| ATOM | 3171 | CA | ILE | A | 221 | 73.448 | −27.844 | 2.429 | 1.00 | 27.11 | A | C |
| ATOM | 3173 | CB | ILE | A | 221 | 73.397 | −26.472 | 1.704 | 1.00 | 26.36 | A | C |
| ATOM | 3175 | CG1 | ILE | A | 221 | 72.680 | −26.608 | 0.360 | 1.00 | 22.83 | A | C |
| ATOM | 3178 | CD1 | ILE | A | 221 | 72.358 | −25.299 | −0.336 | 1.00 | 15.93 | A | C |
| ATOM | 3182 | CG2 | ILE | A | 221 | 74.804 | −25.940 | 1.473 | 1.00 | 28.45 | A | C |
| ATOM | 3186 | C | ILE | A | 221 | 74.509 | −27.769 | 3.525 | 1.00 | 28.33 | A | C |
| ATOM | 3187 | O | ILE | A | 221 | 75.621 | −28.265 | 3.366 | 1.00 | 28.37 | A | O |
| ATOM | 3189 | N | GLU | A | 222 | 74.165 | −27.148 | 4.640 | 1.00 | 29.36 | A | N |
| ATOM | 3190 | CA | GLU | A | 222 | 75.089 | −27.078 | 5.770 | 1.00 | 29.36 | A | C |
| ATOM | 3192 | CB | GLU | A | 222 | 74.540 | −26.124 | 6.842 | 1.00 | 29.54 | A | C |
| ATOM | 3195 | CG | GLU | A | 222 | 75.301 | −26.042 | 8.170 | 1.00 | 37.23 | A | C |
| ATOM | 3198 | CD | GLU | A | 222 | 76.756 | −25.564 | 8.041 | 1.00 | 40.53 | A | C |
| ATOM | 3199 | OE1 | GLU | A | 222 | 77.153 | −25.010 | 6.984 | 1.00 | 44.11 | A | O |
| ATOM | 3200 | OE2 | GLU | A | 222 | 77.499 | −25.737 | 9.030 | 1.00 | 46.46 | A | O |
| ATOM | 3201 | C | GLU | A | 222 | 75.311 | −28.503 | 6.286 | 1.00 | 29.13 | A | C |
| ATOM | 3202 | O | GLU | A | 222 | 76.438 | −28.891 | 6.532 | 1.00 | 28.56 | A | O |
| ATOM | 3204 | N | ALA | A | 223 | 74.246 | −29.305 | 6.379 | 1.00 | 28.23 | A | N |
| ATOM | 3205 | CA | ALA | A | 223 | 74.377 | −30.670 | 6.882 | 1.00 | 27.59 | A | C |
| ATOM | 3207 | CB | ALA | A | 223 | 73.003 | −31.344 | 7.026 | 1.00 | 29.69 | A | C |
| ATOM | 3211 | C | ALA | A | 223 | 75.255 | −31.497 | 5.959 | 1.00 | 28.61 | A | C |
| ATOM | 3212 | O | ALA | A | 223 | 76.131 | −32.225 | 6.420 | 1.00 | 28.90 | A | O |
| ATOM | 3214 | N | TYR | A | 224 | 74.995 | −31.386 | 4.657 | 1.00 | 27.73 | A | N |
| ATOM | 3215 | CA | TYR | A | 224 | 75.677 | −32.186 | 3.652 | 1.00 | 28.06 | A | C |
| ATOM | 3217 | CB | TYR | A | 224 | 75.020 | −31.964 | 2.284 | 1.00 | 26.68 | A | C |
| ATOM | 3220 | CG | TYR | A | 224 | 75.272 | −33.036 | 1.247 | 1.00 | 23.01 | A | C |
| ATOM | 3221 | CD1 | TYR | A | 224 | 74.715 | −34.296 | 1.372 | 1.00 | 24.54 | A | C |
| ATOM | 3223 | CE1 | TYR | A | 224 | 74.929 | −35.278 | 0.410 | 1.00 | 28.25 | A | C |
| ATOM | 3225 | CZ | TYR | A | 224 | 75.687 | −34.995 | −0.710 | 1.00 | 26.14 | A | C |
| ATOM | 3226 | OH | TYR | A | 224 | 75.902 | −35.965 | −1.669 | 1.00 | 30.14 | A | O |
| ATOM | 3228 | CE2 | TYR | A | 224 | 76.244 | −33.755 | −0.859 | 1.00 | 24.49 | A | C |
| ATOM | 3230 | CD2 | TYR | A | 224 | 76.030 | −32.772 | 0.112 | 1.00 | 25.46 | A | C |
| ATOM | 3232 | C | TYR | A | 224 | 77.166 | −31.809 | 3.607 | 1.00 | 28.75 | A | C |
| ATOM | 3233 | O | TYR | A | 224 | 78.029 | −32.671 | 3.448 | 1.00 | 27.95 | A | O |
| ATOM | 3235 | N | ARG | A | 225 | 77.452 | −30.525 | 3.769 | 1.00 | 29.70 | A | N |
| ATOM | 3236 | CA | ARG | A | 225 | 78.833 | −30.042 | 3.733 | 1.00 | 34.37 | A | C |
| ATOM | 3238 | CB | ARG | A | 225 | 78.874 | −28.525 | 3.945 | 1.00 | 34.39 | A | C |
| ATOM | 3241 | CG | ARG | A | 225 | 80.182 | −27.914 | 3.518 | 1.00 | 42.08 | A | C |
| ATOM | 3244 | CD | ARG | A | 225 | 80.440 | −26.599 | 4.201 | 1.00 | 44.17 | A | C |
| ATOM | 3247 | NE | ARG | A | 225 | 79.492 | −25.587 | 3.768 | 1.00 | 33.41 | A | N |
| ATOM | 3249 | CZ | ARG | A | 225 | 79.757 | −24.598 | 2.921 | 1.00 | 31.84 | A | C |
| ATOM | 3250 | NH1 | ARG | A | 225 | 80.969 | −24.440 | 2.360 | 1.00 | 26.16 | A | N |
| ATOM | 3253 | NH2 | ARG | A | 225 | 78.789 | −23.732 | 2.647 | 1.00 | 28.39 | A | N |
| ATOM | 3256 | C | ARG | A | 225 | 79.731 | −30.720 | 4.782 | 1.00 | 34.95 | A | C |
| ATOM | 3257 | O | ARG | A | 225 | 80.924 | −30.847 | 4.571 | 1.00 | 33.72 | A | O |
| ATOM | 3259 | N | LYS | A | 226 | 79.148 | −31.153 | 5.897 | 1.00 | 38.87 | A | N |
| ATOM | 3260 | CA | LYS | A | 226 | 79.895 | −31.805 | 6.980 | 1.00 | 41.98 | A | C |

TABLE 4-2-continued

Coordinates of *P. alba* IspS

| ATOM | 3262 | CB | LYS | A | 226 | 79.195 | −31.585 | 8.323 | 1.00 | 41.81 | A | C |
|------|------|-----|-----|---|-----|--------|---------|--------|------|-------|---|---|
| ATOM | 3265 | CG | LYS | A | 226 | 79.118 | −30.139 | 8.760 | 1.00 | 43.92 | A | C |
| ATOM | 3268 | CD | LYS | A | 226 | 78.200 | −30.008 | 9.967 | 1.00 | 48.86 | A | C |
| ATOM | 3271 | CE | LYS | A | 226 | 77.814 | −28.571 | 10.214 | 1.00 | 50.51 | A | C |
| ATOM | 3274 | NZ | LYS | A | 226 | 76.638 | −28.436 | 11.125 | 1.00 | 50.92 | A | N |
| ATOM | 3278 | C  | LYS | A | 226 | 80.099 | −33.305 | 6.780 | 1.00 | 43.06 | A | C |
| ATOM | 3279 | O  | LYS | A | 226 | 80.952 | −33.885 | 7.435 | 1.00 | 43.06 | A | O |
| ATOM | 3281 | N  | LYS | A | 227 | 79.322 | −33.938 | 5.905 | 1.00 | 44.99 | A | N |
| ATOM | 3282 | CA | LYS | A | 227 | 79.499 | −35.372 | 5.641 | 1.00 | 46.76 | A | C |
| ATOM | 3284 | CB | LYS | A | 227 | 78.334 | −35.933 | 4.840 | 1.00 | 46.98 | A | C |
| ATOM | 3287 | CG | LYS | A | 227 | 76.994 | −35.858 | 5.523 | 1.00 | 51.16 | A | C |
| ATOM | 3290 | CD | LYS | A | 227 | 76.018 | −36.864 | 4.900 | 1.00 | 58.14 | A | C |
| ATOM | 3293 | CE | LYS | A | 227 | 74.634 | −36.793 | 5.566 | 1.00 | 65.96 | A | C |
| ATOM | 3296 | NZ | LYS | A | 227 | 74.529 | −37.575 | 6.846 | 1.00 | 67.08 | A | N |
| ATOM | 3300 | C  | LYS | A | 227 | 80.786 | −35.607 | 4.854 | 1.00 | 48.34 | A | C |
| ATOM | 3301 | O  | LYS | A | 227 | 80.992 | −34.995 | 3.799 | 1.00 | 48.62 | A | O |
| ATOM | 3303 | N  | GLU | A | 228 | 81.638 | −36.503 | 5.359 | 1.00 | 49.33 | A | N |
| ATOM | 3304 | CA | GLU | A | 228 | 82.956 | −36.761 | 4.757 | 1.00 | 49.51 | A | C |
| ATOM | 3306 | CB | GLU | A | 228 | 83.814 | −37.641 | 5.689 | 1.00 | 50.88 | A | C |
| ATOM | 3309 | CG | GLU | A | 228 | 85.196 | −38.038 | 5.113 | 1.00 | 58.59 | A | C |
| ATOM | 3312 | CD | GLU | A | 228 | 86.120 | −38.742 | 6.127 | 1.00 | 63.27 | A | C |
| ATOM | 3313 | OE1 | GLU | A | 228 | 86.715 | −38.048 | 6.986 | 1.00 | 63.25 | A | O |
| ATOM | 3314 | OE2 | GLU | A | 228 | 86.269 | −39.985 | 6.040 | 1.00 | 60.49 | A | O |
| ATOM | 3315 | C  | GLU | A | 228 | 82.839 | −37.401 | 3.370 | 1.00 | 47.39 | A | C |
| ATOM | 3316 | O  | GLU | A | 228 | 83.681 | −37.153 | 2.503 | 1.00 | 48.29 | A | O |
| ATOM | 3318 | N  | ASP | A | 229 | 81.792 | −38.204 | 3.173 | 1.00 | 43.95 | A | N |
| ATOM | 3319 | CA | ASP | A | 229 | 81.528 | −38.887 | 1.903 | 1.00 | 42.40 | A | C |
| ATOM | 3321 | CB | ASP | A | 229 | 81.004 | −40.301 | 2.198 | 1.00 | 44.51 | A | C |
| ATOM | 3324 | CG | ASP | A | 229 | 79.635 | −40.288 | 2.889 | 1.00 | 48.08 | A | C |
| ATOM | 3325 | OD1 | ASP | A | 229 | 79.412 | −39.414 | 3.764 | 1.00 | 52.32 | A | O |
| ATOM | 3326 | OD2 | ASP | A | 229 | 78.791 | −41.154 | 2.563 | 1.00 | 55.55 | A | O |
| ATOM | 3327 | C  | ASP | A | 229 | 80.505 | −38.161 | 1.001 | 1.00 | 39.47 | A | C |
| ATOM | 3328 | O  | ASP | A | 229 | 79.905 | −38.774 | 0.111 | 1.00 | 38.26 | A | O |
| ATOM | 3330 | N  | ALA | A | 230 | 80.287 | −36.871 | 1.232 | 1.00 | 35.85 | A | N |
| ATOM | 3331 | CA | ALA | A | 230 | 79.406 | −36.089 | 0.360 | 1.00 | 34.54 | A | C |
| ATOM | 3333 | CB | ALA | A | 230 | 79.252 | −34.654 | 0.911 | 1.00 | 34.43 | A | C |
| ATOM | 3337 | C  | ALA | A | 230 | 79.943 | −36.039 | −1.075 | 1.00 | 31.71 | A | C |
| ATOM | 3338 | O  | ALA | A | 230 | 81.139 | −35.893 | −1.293 | 1.00 | 31.71 | A | O |
| ATOM | 3340 | N  | ASN | A | 231 | 79.052 | −36.149 | −2.048 | 1.00 | 30.30 | A | N |
| ATOM | 3341 | CA | ASN | A | 231 | 79.405 | −35.899 | −3.445 | 1.00 | 29.41 | A | C |
| ATOM | 3343 | CB | ASN | A | 231 | 78.209 | −36.246 | −4.341 | 1.00 | 28.84 | A | C |
| ATOM | 3346 | CG | ASN | A | 231 | 78.477 | −36.010 | −5.831 | 1.00 | 33.88 | A | C |
| ATOM | 3347 | OD1 | ASN | A | 231 | 79.040 | −34.979 | −6.245 | 1.00 | 29.21 | A | O |
| ATOM | 3348 | ND2 | ASN | A | 231 | 78.034 | −36.955 | −6.647 | 1.00 | 39.93 | A | N |
| ATOM | 3351 | C  | ASN | A | 231 | 79.790 | −34.424 | −3.610 | 1.00 | 28.30 | A | C |
| ATOM | 3352 | O  | ASN | A | 231 | 78.954 | −33.553 | −3.407 | 1.00 | 29.80 | A | O |
| ATOM | 3354 | N  | GLN | A | 232 | 81.032 | −34.144 | −3.987 | 1.00 | 26.07 | A | N |
| ATOM | 3355 | CA | GLN | A | 232 | 81.501 | −32.758 | −4.080 | 1.00 | 26.86 | A | C |
| ATOM | 3357 | CB | GLN | A | 232 | 83.033 | −32.713 | −4.132 | 1.00 | 28.05 | A | C |
| ATOM | 3360 | CG | GLN | A | 232 | 83.748 | −33.343 | −2.907 | 1.00 | 32.80 | A | C |
| ATOM | 3363 | CD | GLN | A | 232 | 83.312 | −32.742 | −1.576 | 1.00 | 33.27 | A | C |
| ATOM | 3364 | OE1 | GLN | A | 232 | 83.561 | −31.573 | −1.287 | 1.00 | 32.93 | A | O |
| ATOM | 3365 | NE2 | GLN | A | 232 | 82.657 | −33.550 | −0.762 | 1.00 | 34.64 | A | N |
| ATOM | 3368 | C  | GLN | A | 232 | 80.914 | −31.962 | −5.265 | 1.00 | 26.08 | A | C |
| ATOM | 3369 | O  | GLN | A | 232 | 80.757 | −30.731 | −5.179 | 1.00 | 26.37 | A | O |
| ATOM | 3371 | N  | VAL | A | 233 | 80.598 | −32.647 | −6.363 | 1.00 | 23.92 | A | N |
| ATOM | 3372 | CA | VAL | A | 233 | 79.939 | −32.005 | −7.513 | 1.00 | 23.21 | A | C |
| ATOM | 3374 | CB | VAL | A | 233 | 79.852 | −32.957 | −8.737 | 1.00 | 24.28 | A | C |
| ATOM | 3376 | CG1 | VAL | A | 233 | 78.831 | −32.450 | −9.732 | 1.00 | 19.74 | A | C |
| ATOM | 3380 | CG2 | VAL | A | 233 | 81.256 | −33.115 | −9.399 | 1.00 | 23.81 | A | C |
| ATOM | 3384 | C  | VAL | A | 233 | 78.535 | −31.501 | −7.127 | 1.00 | 23.21 | A | C |
| ATOM | 3385 | O  | VAL | A | 233 | 78.180 | −30.351 | −7.391 | 1.00 | 21.93 | A | O |
| ATOM | 3387 | N  | LEU | A | 234 | 77.774 | −32.344 | −6.435 | 1.00 | 22.20 | A | N |
| ATOM | 3388 | CA | LEU | A | 234 | 76.438 | −31.982 | −5.981 | 1.00 | 22.67 | A | C |
| ATOM | 3390 | CB | LEU | A | 234 | 75.746 | −33.221 | −5.425 | 1.00 | 24.22 | A | C |
| ATOM | 3393 | CG | LEU | A | 234 | 74.276 | −33.151 | −4.995 | 1.00 | 25.50 | A | C |
| ATOM | 3395 | CD1 | LEU | A | 234 | 73.370 | −32.553 | −6.102 | 1.00 | 18.15 | A | C |
| ATOM | 3399 | CD2 | LEU | A | 234 | 73.833 | −34.547 | −4.622 | 1.00 | 18.42 | A | C |
| ATOM | 3403 | C  | LEU | A | 234 | 76.469 | −30.846 | −4.941 | 1.00 | 23.82 | A | C |
| ATOM | 3404 | O  | LEU | A | 234 | 75.701 | −29.896 | −5.041 | 1.00 | 24.91 | A | O |
| ATOM | 3406 | N  | LEU | A | 235 | 77.374 | −30.930 | −3.966 | 1.00 | 23.57 | A | N |
| ATOM | 3407 | CA | LEU | A | 235 | 77.510 | −29.892 | −2.946 | 1.00 | 22.98 | A | C |
| ATOM | 3409 | CB | LEU | A | 235 | 78.597 | −30.259 | −1.944 | 1.00 | 24.41 | A | C |
| ATOM | 3412 | CG | LEU | A | 235 | 78.878 | −29.265 | −0.815 | 1.00 | 26.92 | A | C |
| ATOM | 3414 | CD1 | LEU | A | 235 | 77.604 | −29.078 | 0.019 | 1.00 | 15.89 | A | C |
| ATOM | 3418 | CD2 | LEU | A | 235 | 80.061 | −29.754 | 0.038 | 1.00 | 18.04 | A | C |
| ATOM | 3422 | C  | LEU | A | 235 | 77.842 | −28.566 | −3.580 | 1.00 | 20.58 | A | C |
| ATOM | 3423 | O  | LEU | A | 235 | 77.236 | −27.545 | −3.277 | 1.00 | 19.83 | A | O |

TABLE 4-2-continued

Coordinates of *P. alba* IspS

| ATOM | 3425 | N | GLU | A | 236 | 78.801 | −28.572 | −4.482 | 1.00 | 22.61 | A | N |
|---|---|---|---|---|---|---|---|---|---|---|---|---|
| ATOM | 3426 | CA | GLU | A | 236 | 79.170 | −27.327 | −5.122 | 1.00 | 22.75 | A | C |
| ATOM | 3428 | CB | GLU | A | 236 | 80.383 | −27.502 | −6.026 | 1.00 | 22.70 | A | C |
| ATOM | 3431 | CG | GLU | A | 236 | 80.871 | −26.189 | −6.606 | 1.00 | 23.04 | A | C |
| ATOM | 3434 | CD | GLU | A | 236 | 82.258 | −26.245 | −7.215 | 1.00 | 27.07 | A | C |
| ATOM | 3435 | OE1 | GLU | A | 236 | 82.771 | −27.340 | −7.541 | 1.00 | 33.98 | A | O |
| ATOM | 3436 | OE2 | GLU | A | 236 | 82.838 | −25.154 | −7.363 | 1.00 | 30.70 | A | O |
| ATOM | 3437 | C | GLU | A | 236 | 77.973 | −26.757 | −5.875 | 1.00 | 21.06 | A | C |
| ATOM | 3438 | O | GLU | A | 236 | 77.621 | −25.602 | −5.693 | 1.00 | 23.31 | A | O |
| ATOM | 3440 | N | LEU | A | 237 | 77.318 | −27.567 | −6.691 | 1.00 | 22.06 | A | N |
| ATOM | 3441 | CA | LEU | A | 237 | 76.183 | −27.054 | −7.480 | 1.00 | 19.57 | A | C |
| ATOM | 3443 | CB | LEU | A | 237 | 75.566 | −28.155 | −8.336 | 1.00 | 15.98 | A | C |
| ATOM | 3446 | CG | LEU | A | 237 | 74.366 | −27.737 | −9.187 | 1.00 | 15.57 | A | C |
| ATOM | 3448 | CD1 | LEU | A | 237 | 74.786 | −26.710 | −10.243 | 1.00 | 14.06 | A | C |
| ATOM | 3452 | CD2 | LEU | A | 237 | 73.740 | −28.975 | −9.837 | 1.00 | 15.04 | A | C |
| ATOM | 3456 | C | LEU | A | 237 | 75.133 | −26.460 | −6.562 | 1.00 | 19.31 | A | C |
| ATOM | 3457 | O | LEU | A | 237 | 74.608 | −25.393 | −6.820 | 1.00 | 20.86 | A | O |
| ATOM | 3459 | N | ALA | A | 238 | 74.846 | −27.161 | −5.474 | 1.00 | 19.04 | A | N |
| ATOM | 3460 | CA | ALA | A | 238 | 73.834 | −26.739 | −4.531 | 1.00 | 18.52 | A | C |
| ATOM | 3462 | CB | ALA | A | 238 | 73.675 | −27.811 | −3.413 | 1.00 | 18.25 | A | C |
| ATOM | 3466 | C | ALA | A | 238 | 74.193 | −25.392 | −3.927 | 1.00 | 19.60 | A | C |
| ATOM | 3467 | O | ALA | A | 238 | 73.350 | −24.489 | −3.794 | 1.00 | 21.50 | A | O |
| ATOM | 3469 | N | ILE | A | 239 | 75.448 | −25.233 | −3.539 | 1.00 | 19.28 | A | N |
| ATOM | 3470 | CA | ILE | A | 239 | 75.849 | −23.943 | −2.994 | 1.00 | 19.80 | A | C |
| ATOM | 3472 | CB | ILE | A | 239 | 77.274 | −23.988 | −2.476 | 1.00 | 20.00 | A | C |
| ATOM | 3474 | CG1 | ILE | A | 239 | 77.319 | −24.875 | −1.218 | 1.00 | 17.31 | A | C |
| ATOM | 3477 | CD1 | ILE | A | 239 | 78.704 | −25.050 | −0.668 | 1.00 | 21.36 | A | C |
| ATOM | 3481 | CG2 | ILE | A | 239 | 77.786 | −22.592 | −2.202 | 1.00 | 17.51 | A | C |
| ATOM | 3485 | C | ILE | A | 239 | 75.665 | −22.871 | −4.062 | 1.00 | 20.41 | A | C |
| ATOM | 3486 | O | ILE | A | 239 | 75.042 | −21.848 | −3.806 | 1.00 | 19.36 | A | O |
| ATOM | 3488 | N | LEU | A | 240 | 76.198 | −23.118 | −5.258 | 1.00 | 21.30 | A | N |
| ATOM | 3489 | CA | LEU | A | 240 | 76.149 | −22.135 | −6.356 | 1.00 | 21.36 | A | C |
| ATOM | 3491 | CB | LEU | A | 240 | 76.776 | −22.696 | −7.645 | 1.00 | 22.81 | A | C |
| ATOM | 3494 | CG | LEU | A | 240 | 78.227 | −22.426 | −7.967 | 1.00 | 30.14 | A | C |
| ATOM | 3496 | CD1 | LEU | A | 240 | 78.568 | −23.128 | −9.255 | 1.00 | 32.64 | A | C |
| ATOM | 3500 | CD2 | LEU | A | 240 | 79.131 | −22.906 | −6.840 | 1.00 | 37.35 | A | C |
| ATOM | 3504 | C | LEU | A | 240 | 74.719 | −21.794 | −6.687 | 1.00 | 20.26 | A | C |
| ATOM | 3505 | O | LEU | A | 240 | 74.394 | −20.648 | −6.875 | 1.00 | 21.20 | A | O |
| ATOM | 3507 | N | ASP | A | 241 | 73.864 | −22.806 | −6.784 | 1.00 | 19.89 | A | N |
| ATOM | 3508 | CA | ASP | A | 241 | 72.482 | −22.569 | −7.156 | 1.00 | 20.98 | A | C |
| ATOM | 3510 | CB | ASP | A | 241 | 71.727 | −23.866 | −7.456 | 1.00 | 20.86 | A | C |
| ATOM | 3513 | CG | ASP | A | 241 | 70.487 | −23.614 | −8.317 | 1.00 | 26.59 | A | C |
| ATOM | 3514 | OD1 | ASP | A | 241 | 69.370 | −23.431 | −7.778 | 1.00 | 23.99 | A | O |
| ATOM | 3515 | OD2 | ASP | A | 241 | 70.638 | −23.525 | −9.538 | 1.00 | 24.62 | A | O |
| ATOM | 3516 | C | ASP | A | 241 | 71.741 | −21.775 | −6.091 | 1.00 | 21.28 | A | C |
| ATOM | 3517 | O | ASP | A | 241 | 70.980 | −20.872 | −6.411 | 1.00 | 22.40 | A | O |
| ATOM | 3519 | N | TYR | A | 242 | 71.967 | −22.089 | −4.828 | 1.00 | 20.15 | A | N |
| ATOM | 3520 | CA | TYR | A | 242 | 71.259 | −21.393 | −3.771 | 1.00 | 20.85 | A | C |
| ATOM | 3522 | CB | TYR | A | 242 | 71.568 | −22.050 | −2.438 | 1.00 | 22.45 | A | C |
| ATOM | 3525 | CG | TYR | A | 242 | 70.857 | −21.437 | −1.265 | 1.00 | 23.33 | A | C |
| ATOM | 3526 | CD1 | TYR | A | 242 | 69.691 | −21.998 | −0.761 | 1.00 | 18.55 | A | C |
| ATOM | 3528 | CE1 | TYR | A | 242 | 69.041 | −21.418 | 0.330 | 1.00 | 24.47 | A | C |
| ATOM | 3530 | CZ | TYR | A | 242 | 69.569 | −20.276 | 0.908 | 1.00 | 18.54 | A | C |
| ATOM | 3531 | OH | TYR | A | 242 | 68.956 | −19.675 | 1.972 | 1.00 | 25.94 | A | O |
| ATOM | 3533 | CE2 | TYR | A | 242 | 70.713 | −19.709 | 0.406 | 1.00 | 21.27 | A | C |
| ATOM | 3535 | CD2 | TYR | A | 242 | 71.346 | −20.283 | −0.666 | 1.00 | 19.29 | A | C |
| ATOM | 3537 | C | TYR | A | 242 | 71.620 | −19.907 | −3.718 | 1.00 | 22.79 | A | C |
| ATOM | 3538 | O | TYR | A | 242 | 70.727 | −19.047 | −3.526 | 1.00 | 22.49 | A | O |
| ATOM | 3540 | N | ASN | A | 243 | 72.912 | −19.603 | −3.864 | 1.00 | 20.76 | A | N |
| ATOM | 3541 | CA | ASN | A | 243 | 73.375 | −18.205 | −3.845 | 1.00 | 22.06 | A | C |
| ATOM | 3543 | CB | ASN | A | 243 | 74.906 | −18.124 | −3.672 | 1.00 | 20.78 | A | C |
| ATOM | 3546 | CG | ASN | A | 243 | 75.349 | −18.533 | −2.275 | 1.00 | 25.87 | A | C |
| ATOM | 3547 | OD1 | ASN | A | 243 | 74.529 | −18.590 | −1.347 | 1.00 | 27.54 | A | O |
| ATOM | 3548 | ND2 | ASN | A | 243 | 76.639 | −18.815 | −2.110 | 1.00 | 19.91 | A | N |
| ATOM | 3551 | C | ASN | A | 243 | 72.933 | −17.409 | −5.066 | 1.00 | 21.72 | A | C |
| ATOM | 3552 | O | ASN | A | 243 | 72.662 | −16.203 | −4.983 | 1.00 | 22.95 | A | O |
| ATOM | 3554 | N | MET | A | 244 | 72.846 | −18.070 | −6.205 | 1.00 | 21.84 | A | N |
| ATOM | 3555 | CA | MET | A | 244 | 72.301 | −17.412 | −7.384 | 1.00 | 23.63 | A | C |
| ATOM | 3557 | CB | MET | A | 244 | 72.478 | −18.316 | −8.582 | 1.00 | 23.14 | A | C |
| ATOM | 3560 | CG | MET | A | 244 | 71.729 | −17.885 | −9.801 | 1.00 | 25.17 | A | C |
| ATOM | 3563 | SD | MET | A | 244 | 71.520 | −19.311 | −10.849 | 1.00 | 37.78 | A | S |
| ATOM | 3564 | CE | MET | A | 244 | 70.066 | −20.130 | −10.156 | 1.00 | 36.34 | A | C |
| ATOM | 3568 | C | MET | A | 244 | 70.810 | −17.060 | −7.194 | 1.00 | 24.55 | A | C |
| ATOM | 3569 | O | MET | A | 244 | 70.367 | −15.958 | −7.524 | 1.00 | 27.20 | A | O |
| ATOM | 3571 | N | ILE | A | 245 | 70.029 | −17.988 | −6.665 | 1.00 | 23.34 | A | N |
| ATOM | 3572 | CA | ILE | A | 245 | 68.612 | −17.708 | −6.487 | 1.00 | 23.03 | A | C |
| ATOM | 3574 | CB | ILE | A | 245 | 67.828 | −18.961 | −6.067 | 1.00 | 23.79 | A | C |
| ATOM | 3576 | CG1 | ILE | A | 245 | 67.753 | −19.935 | −7.251 | 1.00 | 24.90 | A | C |

TABLE 4-2-continued

Coordinates of *P. alba* IspS

| ATOM | 3579 | CD1 | ILE | A | 245 | 67.053 | −21.262 | −6.934 | 1.00 | 20.17 | A | C |
|---|---|---|---|---|---|---|---|---|---|---|---|---|
| ATOM | 3583 | CG2 | ILE | A | 245 | 66.428 | −18.579 | −5.537 | 1.00 | 18.88 | A | C |
| ATOM | 3587 | C | ILE | A | 245 | 68.452 | −16.565 | −5.475 | 1.00 | 22.27 | A | C |
| ATOM | 3588 | O | ILE | A | 245 | 67.673 | −15.646 | −5.689 | 1.00 | 23.18 | A | O |
| ATOM | 3590 | N | GLN | A | 246 | 69.222 | −16.618 | −4.400 | 1.00 | 21.78 | A | N |
| ATOM | 3591 | CA | GLN | A | 246 | 69.201 | −15.585 | −3.385 | 1.00 | 22.32 | A | C |
| ATOM | 3593 | CB | GLN | A | 246 | 70.192 | −15.913 | −2.267 | 1.00 | 22.29 | A | C |
| ATOM | 3596 | CG | GLN | A | 246 | 70.105 | −14.977 | −1.079 | 1.00 | 22.47 | A | C |
| ATOM | 3599 | CD | GLN | A | 246 | 71.193 | −15.238 | −0.086 | 1.00 | 23.64 | A | C |
| ATOM | 3600 | OE1 | GLN | A | 246 | 72.333 | −14.876 | −0.330 | 1.00 | 30.86 | A | O |
| ATOM | 3601 | NE2 | GLN | A | 246 | 70.855 | −15.897 | 1.046 | 1.00 | 27.00 | A | N |
| ATOM | 3604 | C | GLN | A | 246 | 69.519 | −14.220 | −3.969 | 1.00 | 25.79 | A | C |
| ATOM | 3605 | O | GLN | A | 246 | 68.906 | −13.227 | −3.574 | 1.00 | 28.66 | A | O |
| ATOM | 3607 | N | SER | A | 247 | 70.448 | −14.156 | −4.918 | 1.00 | 24.24 | A | N |
| ATOM | 3608 | CA | SER | A | 247 | 70.741 | −12.881 | −5.566 | 1.00 | 25.76 | A | C |
| ATOM | 3610 | CB | SER | A | 247 | 71.984 | −12.957 | −6.460 | 1.00 | 25.65 | A | C |
| ATOM | 3613 | OG | SER | A | 247 | 71.670 | −13.655 | −7.661 | 1.00 | 32.02 | A | O |
| ATOM | 3615 | C | SER | A | 247 | 69.557 | −12.390 | −6.377 | 1.00 | 24.68 | A | C |
| ATOM | 3616 | O | SER | A | 247 | 69.434 | −11.184 | −6.615 | 1.00 | 26.69 | A | O |
| ATOM | 3618 | N | VAL | A | 248 | 68.700 | −13.295 | −6.833 | 1.00 | 23.54 | A | N |
| ATOM | 3619 | CA | VAL | A | 248 | 67.456 | −12.855 | −7.466 | 1.00 | 23.71 | A | C |
| ATOM | 3621 | CB | VAL | A | 248 | 66.766 | −13.966 | −8.265 | 1.00 | 26.06 | A | C |
| ATOM | 3623 | CG1 | VAL | A | 248 | 65.435 | −13.455 | −8.867 | 1.00 | 19.39 | A | C |
| ATOM | 3627 | CG2 | VAL | A | 248 | 67.716 | −14.472 | −9.386 | 1.00 | 23.18 | A | C |
| ATOM | 3631 | C | VAL | A | 248 | 66.521 | −12.281 | −6.398 | 1.00 | 25.20 | A | C |
| ATOM | 3632 | O | VAL | A | 248 | 65.871 | −11.268 | −6.617 | 1.00 | 28.02 | A | O |
| ATOM | 3634 | N | TYR | A | 249 | 66.482 | −12.898 | −5.231 | 1.00 | 23.81 | A | N |
| ATOM | 3635 | CA | TYR | A | 249 | 65.652 | −12.372 | −4.165 | 1.00 | 27.09 | A | C |
| ATOM | 3637 | CB | TYR | A | 249 | 65.642 | −13.297 | −2.919 | 1.00 | 27.78 | A | C |
| ATOM | 3640 | CG | TYR | A | 249 | 65.127 | −14.716 | −3.122 | 1.00 | 22.87 | A | C |
| ATOM | 3641 | CD1 | TYR | A | 249 | 64.358 | −15.066 | −4.225 | 1.00 | 20.29 | A | C |
| ATOM | 3643 | CE1 | TYR | A | 249 | 63.892 | −16.351 | −4.383 | 1.00 | 20.19 | A | C |
| ATOM | 3645 | CZ | TYR | A | 249 | 64.185 | −17.292 | −3.431 | 1.00 | 24.01 | A | C |
| ATOM | 3646 | OH | TYR | A | 249 | 63.731 | −18.576 | −3.586 | 1.00 | 21.28 | A | O |
| ATOM | 3648 | CE2 | TYR | A | 249 | 64.938 | −16.969 | −2.329 | 1.00 | 17.32 | A | C |
| ATOM | 3650 | CD2 | TYR | A | 249 | 65.402 | −15.698 | −2.185 | 1.00 | 22.81 | A | C |
| ATOM | 3652 | C | TYR | A | 249 | 66.152 | −10.995 | −3.752 | 1.00 | 28.26 | A | C |
| ATOM | 3653 | O | TYR | A | 249 | 65.361 | −10.086 | −3.502 | 1.00 | 28.96 | A | O |
| ATOM | 3655 | N | GLN | A | 250 | 67.470 | −10.835 | −3.655 | 1.00 | 30.13 | A | N |
| ATOM | 3656 | CA | GLN | A | 250 | 68.017 | −9.558 | −3.209 | 1.00 | 29.19 | A | C |
| ATOM | 3658 | CB | GLN | A | 250 | 69.523 | −9.646 | −2.980 | 1.00 | 29.25 | A | C |
| ATOM | 3661 | CG | GLN | A | 250 | 69.842 | −10.420 | −1.714 | 1.00 | 27.79 | A | C |
| ATOM | 3664 | CD | GLN | A | 250 | 71.234 | −11.016 | −1.662 | 1.00 | 32.54 | A | C |
| ATOM | 3665 | OE1 | GLN | A | 250 | 72.048 | −10.868 | −2.584 | 1.00 | 30.29 | A | O |
| ATOM | 3666 | NE2 | GLN | A | 250 | 71.510 | −11.717 | −0.573 | 1.00 | 28.97 | A | N |
| ATOM | 3669 | C | GLN | A | 250 | 67.616 | −8.450 | −4.174 | 1.00 | 29.47 | A | C |
| ATOM | 3670 | O | GLN | A | 250 | 67.253 | −7.356 | −3.727 | 1.00 | 30.74 | A | O |
| ATOM | 3672 | N | ARG | A | 251 | 67.600 | −8.748 | −5.471 | 1.00 | 29.60 | A | N |
| ATOM | 3673 | CA | ARG | A | 251 | 67.112 | −7.789 | −6.465 | 1.00 | 30.89 | A | C |
| ATOM | 3675 | CB | ARG | A | 251 | 67.463 | −8.185 | −7.905 | 1.00 | 32.50 | A | C |
| ATOM | 3678 | CG | ARG | A | 251 | 67.113 | −7.073 | −8.936 | 1.00 | 40.34 | A | C |
| ATOM | 3681 | CD | ARG | A | 251 | 67.748 | −7.272 | −10.319 | 1.00 | 50.67 | A | C |
| ATOM | 3684 | NE | ARG | A | 251 | 67.564 | −8.647 | −10.781 | 1.00 | 60.70 | A | N |
| ATOM | 3686 | CZ | ARG | A | 251 | 68.526 | −9.565 | −10.909 | 1.00 | 68.22 | A | C |
| ATOM | 3687 | NH1 | ARG | A | 251 | 69.808 | −9.281 | −10.650 | 1.00 | 66.48 | A | N |
| ATOM | 3690 | NH2 | ARG | A | 251 | 68.200 | −10.793 | −11.318 | 1.00 | 67.68 | A | N |
| ATOM | 3693 | C | ARG | A | 251 | 65.621 | −7.568 | −6.373 | 1.00 | 30.00 | A | C |
| ATOM | 3694 | O | ARG | A | 251 | 65.156 | −6.438 | −6.483 | 1.00 | 31.03 | A | O |
| ATOM | 3696 | N | ASP | A | 252 | 64.855 | −8.637 | −6.197 | 1.00 | 29.66 | A | N |
| ATOM | 3697 | CA | ASP | A | 252 | 63.422 | −8.487 | −6.004 | 1.00 | 27.76 | A | C |
| ATOM | 3699 | CB | ASP | A | 252 | 62.766 | −9.838 | −5.688 | 1.00 | 28.05 | A | C |
| ATOM | 3702 | CG | ASP | A | 252 | 62.734 | −10.802 | −6.881 | 1.00 | 31.72 | A | C |
| ATOM | 3703 | OD1 | ASP | A | 252 | 62.980 | −10.396 | −8.039 | 1.00 | 32.65 | A | O |
| ATOM | 3704 | OD2 | ASP | A | 252 | 62.453 | −11.998 | −6.635 | 1.00 | 31.73 | A | O |
| ATOM | 3705 | C | ASP | A | 252 | 63.149 | −7.507 | −4.849 | 1.00 | 27.28 | A | C |
| ATOM | 3706 | O | ASP | A | 252 | 62.343 | −6.590 | −4.965 | 1.00 | 28.15 | A | O |
| ATOM | 3708 | N | LEU | A | 253 | 63.831 | −7.709 | −3.738 | 1.00 | 28.14 | A | N |
| ATOM | 3709 | CA | LEU | A | 253 | 63.621 | −6.912 | −2.539 | 1.00 | 29.87 | A | C |
| ATOM | 3711 | CB | LEU | A | 253 | 64.347 | −7.566 | −1.372 | 1.00 | 29.41 | A | C |
| ATOM | 3714 | CG | LEU | A | 253 | 64.118 | −6.971 | −0.001 | 1.00 | 34.75 | A | C |
| ATOM | 3716 | CD1 | LEU | A | 253 | 62.630 | −6.934 | 0.321 | 1.00 | 26.24 | A | C |
| ATOM | 3720 | CD2 | LEU | A | 253 | 64.893 | −7.766 | 1.038 | 1.00 | 36.83 | A | C |
| ATOM | 3724 | C | LEU | A | 253 | 64.071 | −5.451 | −2.681 | 1.00 | 31.45 | A | C |
| ATOM | 3725 | O | LEU | A | 253 | 63.406 | −4.547 | −2.168 | 1.00 | 32.50 | A | O |
| ATOM | 3727 | N | ARG | A | 254 | 65.180 | −5.203 | −3.364 | 1.00 | 33.17 | A | N |
| ATOM | 3728 | CA | ARG | A | 254 | 65.632 | −3.810 | −3.557 | 1.00 | 34.97 | A | C |
| ATOM | 3730 | CB | ARG | A | 254 | 66.973 | −3.726 | −4.297 | 1.00 | 35.48 | A | C |
| ATOM | 3733 | CG | ARG | A | 254 | 68.190 | −3.919 | −3.399 | 1.00 | 40.57 | A | C |

TABLE 4-2-continued

Coordinates of *P. alba* IspS

| ATOM | 3736 | CD | ARG | A | 254 | 69.493 | −3.551 | −4.113 | 1.00 | 42.70 | A | C |
|---|---|---|---|---|---|---|---|---|---|---|---|---|
| ATOM | 3739 | NE | ARG | A | 254 | 69.666 | −4.290 | −5.366 | 1.00 | 42.33 | A | N |
| ATOM | 3741 | CZ | ARG | A | 254 | 70.190 | −5.516 | −5.483 | 1.00 | 43.80 | A | C |
| ATOM | 3742 | NH1 | ARG | A | 254 | 70.619 | −6.197 | −4.422 | 1.00 | 40.69 | A | N |
| ATOM | 3745 | NH2 | ARG | A | 254 | 70.293 | −6.067 | −6.689 | 1.00 | 45.83 | A | N |
| ATOM | 3748 | C | ARG | A | 254 | 64.563 | −3.054 | −4.316 | 1.00 | 34.14 | A | C |
| ATOM | 3749 | O | ARG | A | 254 | 64.154 | −1.977 | −3.915 | 1.00 | 35.76 | A | O |
| ATOM | 3751 | N | GLU | A | 255 | 64.096 | −3.667 | −5.390 | 1.00 | 34.42 | A | N |
| ATOM | 3752 | CA | GLU | A | 255 | 63.024 | −3.139 | −6.221 | 1.00 | 36.63 | A | C |
| ATOM | 3754 | CB | GLU | A | 255 | 62.724 | −4.179 | −7.296 | 1.00 | 38.74 | A | C |
| ATOM | 3757 | CG | GLU | A | 255 | 61.825 | −3.773 | −8.455 | 1.00 | 50.85 | A | C |
| ATOM | 3760 | CD | GLU | A | 255 | 61.681 | −4.909 | −9.497 | 1.00 | 60.07 | A | C |
| ATOM | 3761 | OE1 | GLU | A | 255 | 62.720 | −5.463 | −9.957 | 1.00 | 60.17 | A | O |
| ATOM | 3762 | OE2 | GLU | A | 255 | 60.523 | −5.246 | −9.844 | 1.00 | 63.55 | A | O |
| ATOM | 3763 | C | GLU | A | 255 | 61.756 | −2.831 | −5.420 | 1.00 | 36.27 | A | C |
| ATOM | 3764 | O | GLU | A | 255 | 61.129 | −1.794 | −5.593 | 1.00 | 39.35 | A | O |
| ATOM | 3766 | N | THR | A | 256 | 61.383 | −3.739 | −4.539 | 1.00 | 33.73 | A | N |
| ATOM | 3767 | CA | THR | A | 256 | 60.151 | −3.622 | −3.790 | 1.00 | 31.80 | A | C |
| ATOM | 3769 | CB | THR | A | 256 | 59.703 | −5.018 | −3.323 | 1.00 | 30.64 | A | C |
| ATOM | 3771 | OG1 | THR | A | 256 | 59.309 | −5.757 | −4.469 | 1.00 | 33.76 | A | O |
| ATOM | 3773 | CG2 | THR | A | 256 | 58.537 | −4.966 | −2.325 | 1.00 | 32.44 | A | C |
| ATOM | 3777 | C | THR | A | 256 | 60.360 | −2.667 | −2.618 | 1.00 | 30.31 | A | C |
| ATOM | 3778 | O | THR | A | 256 | 59.460 | −1.916 | −2.260 | 1.00 | 29.39 | A | O |
| ATOM | 3780 | N | SER | A | 257 | 61.544 | −2.705 | −2.022 | 1.00 | 30.11 | A | N |
| ATOM | 3781 | CA | SER | A | 257 | 61.920 | −1.693 | −1.036 | 1.00 | 33.18 | A | C |
| ATOM | 3783 | CB | SER | A | 257 | 63.327 | −1.943 | −0.475 | 1.00 | 32.22 | A | C |
| ATOM | 3786 | OG | SER | A | 257 | 63.336 | −3.128 | 0.297 | 1.00 | 33.34 | A | O |
| ATOM | 3788 | C | SER | A | 257 | 61.834 | −0.281 | −1.621 | 1.00 | 33.22 | A | C |
| ATOM | 3789 | O | SER | A | 257 | 61.449 | 0.638 | −0.907 | 1.00 | 33.37 | A | O |
| ATOM | 3791 | N | ARG | A | 258 | 62.173 | −0.111 | −2.901 | 1.00 | 32.43 | A | N |
| ATOM | 3792 | CA | ARG | A | 258 | 62.019 | 1.204 | −3.565 | 1.00 | 35.63 | A | C |
| ATOM | 3794 | CB | ARG | A | 258 | 62.525 | 1.207 | −5.024 | 1.00 | 38.19 | A | C |
| ATOM | 3797 | CG | ARG | A | 258 | 63.974 | 1.629 | −5.235 | 1.00 | 43.51 | A | C |
| ATOM | 3800 | CD | ARG | A | 258 | 64.204 | 2.128 | −6.670 | 1.00 | 49.21 | A | C |
| ATOM | 3803 | NE | ARG | A | 258 | 63.874 | 1.127 | −7.692 | 1.00 | 50.92 | A | N |
| ATOM | 3805 | CZ | ARG | A | 258 | 64.697 | 0.173 | −8.133 | 1.00 | 57.27 | A | C |
| ATOM | 3806 | NH1 | ARG | A | 258 | 64.275 | −0.679 | −9.060 | 1.00 | 57.78 | A | N |
| ATOM | 3809 | NH2 | ARG | A | 258 | 65.935 | 0.050 | −7.653 | 1.00 | 60.74 | A | N |
| ATOM | 3812 | C | ARG | A | 258 | 60.571 | 1.623 | −3.602 | 1.00 | 33.91 | A | C |
| ATOM | 3813 | O | ARG | A | 258 | 60.254 | 2.753 | −3.318 | 1.00 | 33.23 | A | O |
| ATOM | 3815 | N | TRP | A | 259 | 59.697 | 0.714 | −4.015 | 1.00 | 33.11 | A | N |
| ATOM | 3816 | CA | TRP | A | 259 | 58.266 | 1.003 | −4.026 | 1.00 | 32.00 | A | C |
| ATOM | 3818 | CB | TRP | A | 259 | 57.487 | −0.183 | −4.587 | 1.00 | 31.64 | A | C |
| ATOM | 3821 | CG | TRP | A | 259 | 56.053 | −0.155 | −4.267 | 1.00 | 27.92 | A | C |
| ATOM | 3822 | CD1 | TRP | A | 259 | 55.084 | 0.569 | −4.900 | 1.00 | 32.00 | A | C |
| ATOM | 3824 | NE1 | TRP | A | 259 | 53.861 | 0.357 | −4.299 | 1.00 | 30.37 | A | N |
| ATOM | 3826 | CE2 | TRP | A | 259 | 54.033 | −0.523 | −3.264 | 1.00 | 26.02 | A | C |
| ATOM | 3827 | CD2 | TRP | A | 259 | 55.400 | −0.861 | −3.211 | 1.00 | 28.92 | A | C |
| ATOM | 3828 | CE3 | TRP | A | 259 | 55.839 | −1.732 | −2.212 | 1.00 | 24.22 | A | C |
| ATOM | 3830 | CZ3 | TRP | A | 259 | 54.932 | −2.229 | −1.337 | 1.00 | 28.49 | A | C |
| ATOM | 3832 | CH2 | TRP | A | 259 | 53.584 | −1.882 | −1.425 | 1.00 | 32.67 | A | C |
| ATOM | 3834 | CZ2 | TRP | A | 259 | 53.125 | −1.025 | −2.382 | 1.00 | 22.99 | A | C |
| ATOM | 3836 | C | TRP | A | 259 | 57.753 | 1.358 | −2.623 | 1.00 | 31.98 | A | C |
| ATOM | 3837 | O | TRP | A | 259 | 56.957 | 2.274 | −2.465 | 1.00 | 34.30 | A | O |
| ATOM | 3839 | N | TRP | A | 260 | 58.224 | 0.639 | −1.611 | 1.00 | 30.69 | A | N |
| ATOM | 3840 | CA | TRP | A | 260 | 57.676 | 0.755 | −0.270 | 1.00 | 29.45 | A | C |
| ATOM | 3842 | CB | TRP | A | 260 | 58.190 | −0.399 | 0.578 | 1.00 | 29.19 | A | C |
| ATOM | 3845 | CG | TRP | A | 260 | 57.621 | −0.512 | 1.985 | 1.00 | 32.70 | A | C |
| ATOM | 3846 | CD1 | TRP | A | 260 | 58.333 | −0.569 | 3.137 | 1.00 | 31.86 | A | C |
| ATOM | 3848 | NE1 | TRP | A | 260 | 57.489 | −0.698 | 4.209 | 1.00 | 33.52 | A | N |
| ATOM | 3850 | CE2 | TRP | A | 260 | 56.202 | −0.741 | 3.762 | 1.00 | 27.99 | A | C |
| ATOM | 3851 | CD2 | TRP | A | 260 | 56.240 | −0.627 | 2.364 | 1.00 | 25.33 | A | C |
| ATOM | 3852 | CE3 | TRP | A | 260 | 55.038 | −0.632 | 1.658 | 1.00 | 28.45 | A | C |
| ATOM | 3854 | CZ3 | TRP | A | 260 | 53.863 | −0.755 | 2.356 | 1.00 | 24.24 | A | C |
| ATOM | 3856 | CH2 | TRP | A | 260 | 53.859 | −0.875 | 3.741 | 1.00 | 29.24 | A | C |
| ATOM | 3858 | CZ2 | TRP | A | 260 | 55.017 | −0.858 | 4.466 | 1.00 | 31.81 | A | C |
| ATOM | 3860 | C | TRP | A | 260 | 58.052 | 2.102 | 0.332 | 1.00 | 29.67 | A | C |
| ATOM | 3861 | O | TRP | A | 260 | 57.218 | 2.763 | 0.934 | 1.00 | 26.76 | A | O |
| ATOM | 3863 | N | ARG | A | 261 | 59.288 | 2.528 | 0.111 | 1.00 | 32.87 | A | N |
| ATOM | 3864 | CA | AARG | A | 261 | 59.778 | 3.810 | 0.630 | 0.50 | 35.92 | A | C |
| ATOM | 3865 | CA | BARG | A | 261 | 59.768 | 3.809 | 0.649 | 0.50 | 35.98 | A | C |
| ATOM | 3868 | CB | AARG | A | 261 | 61.299 | 3.917 | 0.447 | 0.50 | 36.14 | A | C |
| ATOM | 3869 | CB | BARG | A | 261 | 61.293 | 3.938 | 0.514 | 0.50 | 36.20 | A | C |
| ATOM | 3874 | CG | AARG | A | 261 | 62.081 | 3.255 | 1.576 | 0.50 | 40.00 | A | C |
| ATOM | 3875 | CG | BARG | A | 261 | 61.962 | 4.656 | 1.691 | 0.50 | 40.66 | A | C |
| ATOM | 3880 | CD | AARG | A | 261 | 63.347 | 2.553 | 1.086 | 0.50 | 45.53 | A | C |
| ATOM | 3881 | CD | BARG | A | 261 | 61.787 | 3.877 | 3.002 | 0.50 | 44.00 | A | C |
| ATOM | 3886 | NE | AARG | A | 261 | 63.970 | 3.229 | −0.049 | 0.50 | 45.59 | A | N |

TABLE 4-2-continued

Coordinates of *P. alba* IspS

| ATOM | 3887 | NE | BARG | A | 261 | 62.789 | 4.234 | 4.005 | 0.50 | 45.46 | A | N |
|---|---|---|---|---|---|---|---|---|---|---|---|---|
| ATOM | 3890 | CZ | AARG | A | 261 | 64.845 | 2.643 | −0.856 | 0.50 | 42.15 | A | C |
| ATOM | 3891 | CZ | BARG | A | 261 | 62.660 | 5.236 | 4.869 | 0.50 | 50.02 | A | C |
| ATOM | 3892 | NH1 | AARG | A | 261 | 65.188 | 1.382 | −0.637 | 0.50 | 33.28 | A | N |
| ATOM | 3893 | NH1 | BARG | A | 261 | 61.567 | 5.987 | 4.861 | 0.50 | 49.40 | A | N |
| ATOM | 3898 | NH2 | AARG | A | 261 | 65.370 | 3.311 | −1.874 | 0.50 | 42.47 | A | N |
| ATOM | 3899 | NH2 | BARG | A | 261 | 63.625 | 5.484 | 5.745 | 0.50 | 49.02 | A | N |
| ATOM | 3904 | C | ARG | A | 261 | 59.061 | 4.997 | −0.024 | 1.00 | 37.61 | A | C |
| ATOM | 3905 | O | ARG | A | 261 | 58.729 | 5.981 | 0.642 | 1.00 | 38.28 | A | O |
| ATOM | 3907 | N | ARG | A | 262 | 58.808 | 4.897 | −1.327 | 1.00 | 38.01 | A | N |
| ATOM | 3908 | CA | ARG | A | 262 | 58.026 | 5.922 | −2.019 | 1.00 | 39.29 | A | C |
| ATOM | 3910 | CB | ARG | A | 262 | 57.878 | 5.607 | −3.516 | 1.00 | 42.22 | A | C |
| ATOM | 3913 | CG | ARG | A | 262 | 59.136 | 5.898 | −4.350 | 1.00 | 52.27 | A | C |
| ATOM | 3916 | CD | ARG | A | 262 | 58.787 | 6.242 | −5.811 | 1.00 | 62.63 | A | C |
| ATOM | 3919 | NE | ARG | A | 262 | 57.884 | 5.261 | −6.428 | 1.00 | 67.61 | A | N |
| ATOM | 3921 | CZ | ARG | A | 262 | 58.273 | 4.146 | −7.054 | 1.00 | 71.86 | A | C |
| ATOM | 3922 | NH1 | ARG | A | 262 | 59.567 | 3.837 | −7.171 | 1.00 | 69.63 | A | N |
| ATOM | 3925 | NH2 | ARG | A | 262 | 57.354 | 3.328 | −7.566 | 1.00 | 71.10 | A | N |
| ATOM | 3928 | C | ARG | A | 262 | 56.646 | 6.038 | −1.398 | 1.00 | 35.13 | A | C |
| ATOM | 3929 | O | ARG | A | 262 | 56.192 | 7.127 | −1.072 | 1.00 | 39.41 | A | O |
| ATOM | 3931 | N | VAL | A | 263 | 55.978 | 4.913 | −1.229 | 1.00 | 31.29 | A | N |
| ATOM | 3932 | CA | VAL | A | 263 | 54.684 | 4.899 | −0.577 | 1.00 | 28.48 | A | C |
| ATOM | 3934 | CB | VAL | A | 263 | 54.116 | 3.501 | −0.518 | 1.00 | 26.56 | A | C |
| ATOM | 3936 | CG1 | VAL | A | 263 | 53.801 | 3.029 | −1.925 | 1.00 | 30.17 | A | C |
| ATOM | 3940 | CG2 | VAL | A | 263 | 52.879 | 3.480 | 0.354 | 1.00 | 27.85 | A | C |
| ATOM | 3944 | C | VAL | A | 263 | 54.745 | 5.479 | 0.844 | 1.00 | 28.20 | A | C |
| ATOM | 3945 | O | VAL | A | 263 | 53.801 | 6.150 | 1.259 | 1.00 | 26.93 | A | O |
| ATOM | 3947 | N | GLY | A | 264 | 55.847 | 5.199 | 1.559 | 1.00 | 28.31 | A | N |
| ATOM | 3948 | CA | GLY | A | 264 | 56.160 | 5.750 | 2.871 | 1.00 | 27.54 | A | C |
| ATOM | 3951 | C | GLY | A | 264 | 55.063 | 5.691 | 3.909 | 1.00 | 29.80 | A | C |
| ATOM | 3952 | O | GLY | A | 264 | 54.978 | 6.560 | 4.760 | 1.00 | 32.57 | A | O |
| ATOM | 3954 | N | LEU | A | 265 | 54.219 | 4.673 | 3.842 | 1.00 | 32.96 | A | N |
| ATOM | 3955 | CA | LEU | A | 265 | 53.026 | 4.593 | 4.679 | 1.00 | 36.19 | A | C |
| ATOM | 3957 | CB | LEU | A | 265 | 52.050 | 3.553 | 4.111 | 1.00 | 34.50 | A | C |
| ATOM | 3960 | CG | LEU | A | 265 | 50.568 | 3.516 | 4.505 | 1.00 | 36.39 | A | C |
| ATOM | 3962 | CD1 | LEU | A | 265 | 49.833 | 4.834 | 4.299 | 1.00 | 27.01 | A | C |
| ATOM | 3966 | CD2 | LEU | A | 265 | 49.858 | 2.406 | 3.721 | 1.00 | 31.32 | A | C |
| ATOM | 3970 | C | LEU | A | 265 | 53.376 | 4.316 | 6.151 | 1.00 | 40.47 | A | C |
| ATOM | 3971 | O | LEU | A | 265 | 52.828 | 4.964 | 7.046 | 1.00 | 41.90 | A | O |
| ATOM | 3973 | N | ALA | A | 266 | 54.306 | 3.402 | 6.413 | 1.00 | 45.05 | A | N |
| ATOM | 3974 | CA | ALA | A | 266 | 54.692 | 3.097 | 7.803 | 1.00 | 48.60 | A | C |
| ATOM | 3976 | CB | ALA | A | 266 | 55.536 | 1.834 | 7.871 | 1.00 | 49.61 | A | C |
| ATOM | 3980 | C | ALA | A | 266 | 55.414 | 4.263 | 8.486 | 1.00 | 50.25 | A | C |
| ATOM | 3981 | O | ALA | A | 266 | 55.437 | 4.354 | 9.709 | 1.00 | 53.50 | A | O |
| ATOM | 3983 | N | THR | A | 267 | 55.989 | 5.161 | 7.693 | 1.00 | 51.71 | A | N |
| ATOM | 3984 | CA | THR | A | 267 | 56.599 | 6.383 | 8.220 | 1.00 | 50.87 | A | C |
| ATOM | 3986 | CB | THR | A | 267 | 57.494 | 7.042 | 7.158 | 1.00 | 50.67 | A | C |
| ATOM | 3988 | OG1 | THR | A | 267 | 58.268 | 6.030 | 6.501 | 1.00 | 54.33 | A | O |
| ATOM | 3990 | CG2 | THR | A | 267 | 58.420 | 8.057 | 7.783 | 1.00 | 53.96 | A | C |
| ATOM | 3994 | C | THR | A | 267 | 55.537 | 7.383 | 8.678 | 1.00 | 49.72 | A | C |
| ATOM | 3995 | O | THR | A | 267 | 55.657 | 7.966 | 9.753 | 1.00 | 51.35 | A | O |
| ATOM | 3997 | N | LYS | A | 268 | 54.494 | 7.567 | 7.870 | 1.00 | 47.73 | A | N |
| ATOM | 3998 | CA | LYS | A | 268 | 53.515 | 8.655 | 8.074 | 1.00 | 45.94 | A | C |
| ATOM | 4000 | CB | LYS | A | 268 | 52.935 | 9.113 | 6.720 | 1.00 | 46.30 | A | C |
| ATOM | 4003 | CG | LYS | A | 268 | 53.986 | 9.658 | 5.725 | 1.00 | 47.05 | A | C |
| ATOM | 4006 | CD | LYS | A | 268 | 54.376 | 11.104 | 6.011 | 1.00 | 49.29 | A | C |
| ATOM | 4009 | CE | LYS | A | 268 | 55.573 | 11.543 | 5.161 | 1.00 | 52.85 | A | C |
| ATOM | 4012 | NZ | LYS | A | 268 | 55.780 | 13.020 | 5.207 | 1.00 | 54.81 | A | N |
| ATOM | 4016 | C | LYS | A | 268 | 52.378 | 8.275 | 9.024 | 1.00 | 44.32 | A | C |
| ATOM | 4017 | O | LYS | A | 268 | 51.749 | 9.148 | 9.610 | 1.00 | 44.98 | A | O |
| ATOM | 4019 | N | LEU | A | 269 | 52.095 | 6.980 | 9.138 | 1.00 | 43.49 | A | N |
| ATOM | 4020 | CA | LEU | A | 269 | 51.151 | 6.457 | 10.122 | 1.00 | 43.04 | A | C |
| ATOM | 4022 | CB | LEU | A | 269 | 50.429 | 5.222 | 9.561 | 1.00 | 42.92 | A | C |
| ATOM | 4025 | CG | LEU | A | 269 | 49.100 | 5.381 | 8.814 | 1.00 | 42.16 | A | C |
| ATOM | 4027 | CD1 | LEU | A | 269 | 49.147 | 6.491 | 7.813 | 1.00 | 38.88 | A | C |
| ATOM | 4031 | CD2 | LEU | A | 269 | 48.721 | 4.062 | 8.144 | 1.00 | 40.39 | A | C |
| ATOM | 4035 | C | LEU | A | 269 | 51.943 | 6.068 | 11.380 | 1.00 | 43.46 | A | C |
| ATOM | 4036 | O | LEU | A | 269 | 52.741 | 5.132 | 11.344 | 1.00 | 45.75 | A | O |
| ATOM | 4038 | N | HIS | A | 270 | 51.718 | 6.762 | 12.489 | 1.00 | 42.57 | A | N |
| ATOM | 4039 | CA | HIS | A | 270 | 52.559 | 6.585 | 13.689 | 1.00 | 42.20 | A | C |
| ATOM | 4041 | CB | HIS | A | 270 | 52.334 | 7.730 | 14.706 | 1.00 | 43.68 | A | C |
| ATOM | 4044 | CG | HIS | A | 270 | 52.315 | 9.101 | 14.088 | 1.00 | 55.54 | A | C |
| ATOM | 4045 | ND1 | HIS | A | 270 | 53.195 | 9.489 | 13.097 | 1.00 | 59.69 | A | N |
| ATOM | 4047 | CE1 | HIS | A | 270 | 52.936 | 10.737 | 12.746 | 1.00 | 62.20 | A | C |
| ATOM | 4049 | NE2 | HIS | A | 270 | 51.925 | 11.177 | 13.475 | 1.00 | 61.94 | A | N |
| ATOM | 4051 | CD2 | HIS | A | 270 | 51.515 | 10.173 | 14.321 | 1.00 | 61.38 | A | C |
| ATOM | 4053 | C | HIS | A | 270 | 52.340 | 5.224 | 14.372 | 1.00 | 37.82 | A | C |
| ATOM | 4054 | O | HIS | A | 270 | 53.221 | 4.720 | 15.063 | 1.00 | 35.89 | A | O |

TABLE 4-2-continued

Coordinates of *P. alba* IspS

| ATOM | 4056 | N | PHE | A | 271 | 51.160 | 4.649 | 14.178 | 1.00 | 34.74 | A | N |
|---|---|---|---|---|---|---|---|---|---|---|---|---|
| ATOM | 4057 | CA | PHE | A | 271 | 50.818 | 3.349 | 14.756 | 1.00 | 35.98 | A | C |
| ATOM | 4059 | CB | PHE | A | 271 | 49.297 | 3.246 | 14.975 | 1.00 | 36.24 | A | C |
| ATOM | 4062 | CG | PHE | A | 271 | 48.513 | 3.176 | 13.700 | 1.00 | 32.72 | A | C |
| ATOM | 4063 | CD1 | PHE | A | 271 | 48.245 | 1.962 | 13.107 | 1.00 | 36.61 | A | C |
| ATOM | 4065 | CE1 | PHE | A | 271 | 47.542 | 1.895 | 11.905 | 1.00 | 41.78 | A | C |
| ATOM | 4067 | CZ | PHE | A | 271 | 47.106 | 3.050 | 11.293 | 1.00 | 39.23 | A | C |
| ATOM | 4069 | CE2 | PHE | A | 271 | 47.370 | 4.267 | 11.868 | 1.00 | 40.49 | A | C |
| ATOM | 4071 | CD2 | PHE | A | 271 | 48.081 | 4.330 | 13.072 | 1.00 | 36.58 | A | C |
| ATOM | 4073 | C | PHE | A | 271 | 51.277 | 2.144 | 13.928 | 1.00 | 36.24 | A | C |
| ATOM | 4074 | O | PHE | A | 271 | 51.232 | 1.028 | 14.425 | 1.00 | 36.55 | A | O |
| ATOM | 4076 | N | ALA | A | 272 | 51.705 | 2.352 | 12.681 | 1.00 | 36.36 | A | N |
| ATOM | 4077 | CA | ALA | A | 272 | 51.905 | 1.217 | 11.753 | 1.00 | 38.44 | A | C |
| ATOM | 4079 | CB | ALA | A | 272 | 51.767 | 1.683 | 10.299 | 1.00 | 37.11 | A | C |
| ATOM | 4083 | C | ALA | A | 272 | 53.235 | 0.493 | 11.939 | 1.00 | 37.87 | A | C |
| ATOM | 4084 | O | ALA | A | 272 | 54.260 | 1.128 | 12.126 | 1.00 | 38.46 | A | O |
| ATOM | 4086 | N | ARG | A | 273 | 53.199 | −0.838 | 11.895 | 1.00 | 39.95 | A | N |
| ATOM | 4087 | CA | ARG | A | 273 | 54.415 | −1.651 | 11.843 | 1.00 | 42.71 | A | C |
| ATOM | 4089 | CB | ARG | A | 273 | 54.161 | −3.077 | 12.354 | 1.00 | 44.71 | A | C |
| ATOM | 4092 | CG | ARG | A | 273 | 53.612 | −3.232 | 13.785 | 1.00 | 52.26 | A | C |
| ATOM | 4095 | CD | ARG | A | 273 | 53.137 | −4.699 | 14.060 | 1.00 | 58.75 | A | C |
| ATOM | 4098 | NE | ARG | A | 273 | 51.872 | −5.018 | 13.384 | 1.00 | 59.61 | A | N |
| ATOM | 4100 | CZ | ARG | A | 273 | 51.440 | −6.241 | 13.062 | 1.00 | 65.74 | A | C |
| ATOM | 4101 | NH1 | ARG | A | 273 | 52.168 | −7.320 | 13.327 | 1.00 | 72.19 | A | N |
| ATOM | 4104 | NH2 | ARG | A | 273 | 50.268 | −6.390 | 12.441 | 1.00 | 62.91 | A | N |
| ATOM | 4107 | C | ARG | A | 273 | 54.886 | −1.731 | 10.387 | 1.00 | 41.28 | A | C |
| ATOM | 4108 | O | ARG | A | 273 | 54.067 | −1.896 | 9.486 | 1.00 | 42.18 | A | O |
| ATOM | 4110 | N | ASP | A | 274 | 56.195 | −1.605 | 10.171 | 1.00 | 40.00 | A | N |
| ATOM | 4111 | CA | ASP | A | 274 | 56.819 | −1.798 | 8.854 | 1.00 | 38.76 | A | C |
| ATOM | 4113 | CB | ASP | A | 274 | 57.983 | −0.808 | 8.684 | 1.00 | 38.55 | A | C |
| ATOM | 4116 | CG | ASP | A | 274 | 58.733 | −0.993 | 7.370 | 1.00 | 42.03 | A | C |
| ATOM | 4117 | OD1 | ASP | A | 274 | 58.666 | −2.086 | 6.781 | 1.00 | 39.25 | A | O |
| ATOM | 4118 | OD2 | ASP | A | 274 | 59.404 | −0.044 | 6.918 | 1.00 | 46.81 | A | O |
| ATOM | 4119 | C | ASP | A | 274 | 57.306 | −3.260 | 8.725 | 1.00 | 37.31 | A | C |
| ATOM | 4120 | O | ASP | A | 274 | 58.281 | −3.644 | 9.349 | 1.00 | 36.99 | A | O |
| ATOM | 4122 | N | ARG | A | 275 | 56.612 | −4.069 | 7.925 | 1.00 | 37.37 | A | N |
| ATOM | 4123 | CA | ARG | A | 275 | 56.889 | −5.498 | 7.826 | 1.00 | 37.69 | A | C |
| ATOM | 4125 | CB | ARG | A | 275 | 55.702 | −6.299 | 8.391 | 1.00 | 39.25 | A | C |
| ATOM | 4128 | CG | ARG | A | 275 | 55.490 | −6.180 | 9.913 | 1.00 | 47.84 | A | C |
| ATOM | 4131 | CD | ARG | A | 275 | 56.044 | −7.381 | 10.697 | 1.00 | 59.27 | A | C |
| ATOM | 4134 | NE | ARG | A | 275 | 55.924 | −7.187 | 12.150 | 1.00 | 68.25 | A | N |
| ATOM | 4136 | CZ | ARG | A | 275 | 56.679 | −6.355 | 12.886 | 1.00 | 74.47 | A | C |
| ATOM | 4137 | NH1 | ARG | A | 275 | 57.641 | −5.618 | 12.324 | 1.00 | 74.61 | A | N |
| ATOM | 4140 | NH2 | ARG | A | 275 | 56.473 | −6.252 | 14.204 | 1.00 | 72.98 | A | N |
| ATOM | 4143 | C | ARG | A | 275 | 57.168 | −5.943 | 6.388 | 1.00 | 36.06 | A | C |
| ATOM | 4144 | O | ARG | A | 275 | 56.729 | −7.017 | 5.973 | 1.00 | 35.65 | A | O |
| ATOM | 4146 | N | LEU | A | 276 | 57.898 | −5.137 | 5.623 | 1.00 | 35.38 | A | N |
| ATOM | 4147 | CA | LEU | A | 276 | 58.209 | −5.505 | 4.231 | 1.00 | 34.05 | A | C |
| ATOM | 4149 | CB | LEU | A | 276 | 58.824 | −4.340 | 3.438 | 1.00 | 35.05 | A | C |
| ATOM | 4152 | CG | LEU | A | 276 | 59.320 | −4.741 | 2.049 | 1.00 | 34.24 | A | C |
| ATOM | 4154 | CD1 | LEU | A | 276 | 58.157 | −5.203 | 1.208 | 1.00 | 37.51 | A | C |
| ATOM | 4158 | CD2 | LEU | A | 276 | 60.030 | −3.629 | 1.374 | 1.00 | 37.66 | A | C |
| ATOM | 4162 | C | LEU | A | 276 | 59.147 | −6.698 | 4.170 | 1.00 | 31.37 | A | C |
| ATOM | 4163 | O | LEU | A | 276 | 58.890 | −7.636 | 3.443 | 1.00 | 30.37 | A | O |
| ATOM | 4165 | N | ILE | A | 277 | 60.221 | −6.664 | 4.950 | 1.00 | 30.01 | A | N |
| ATOM | 4166 | CA | ILE | A | 277 | 61.242 | −7.701 | 4.870 | 1.00 | 29.44 | A | C |
| ATOM | 4168 | CB | ILE | A | 277 | 62.459 | −7.360 | 5.755 | 1.00 | 30.70 | A | C |
| ATOM | 4170 | CG1 | ILE | A | 277 | 63.124 | −6.061 | 5.253 | 1.00 | 35.07 | A | C |
| ATOM | 4173 | CD1 | ILE | A | 277 | 64.038 | −5.345 | 6.291 | 1.00 | 36.73 | A | C |
| ATOM | 4177 | CG2 | ILE | A | 277 | 63.463 | −8.487 | 5.705 | 1.00 | 27.89 | A | C |
| ATOM | 4181 | C | ILE | A | 277 | 60.654 | −9.045 | 5.267 | 1.00 | 28.92 | A | C |
| ATOM | 4182 | O | ILE | A | 277 | 60.847 | −10.054 | 4.583 | 1.00 | 28.83 | A | O |
| ATOM | 4184 | N | GLU | A | 278 | 59.905 | −9.048 | 6.359 | 1.00 | 27.84 | A | N |
| ATOM | 4185 | CA | GLU | A | 278 | 59.220 | −10.244 | 6.818 | 1.00 | 29.71 | A | C |
| ATOM | 4187 | CB | GLU | A | 278 | 58.538 | −9.966 | 8.161 | 1.00 | 30.64 | A | C |
| ATOM | 4190 | CG | GLU | A | 278 | 59.515 | −9.600 | 9.291 | 1.00 | 41.88 | A | C |
| ATOM | 4193 | CD | GLU | A | 278 | 59.736 | −8.097 | 9.493 | 1.00 | 50.18 | A | C |
| ATOM | 4194 | OE1 | GLU | A | 278 | 59.920 | −7.333 | 8.508 | 1.00 | 48.05 | A | O |
| ATOM | 4195 | OE2 | GLU | A | 278 | 59.742 | −7.686 | 10.673 | 1.00 | 59.82 | A | O |
| ATOM | 4196 | C | GLU | A | 278 | 58.197 | −10.733 | 5.761 | 1.00 | 28.62 | A | C |
| ATOM | 4197 | O | GLU | A | 278 | 58.066 | −11.929 | 5.519 | 1.00 | 28.77 | A | O |
| ATOM | 4199 | N | SER | A | 279 | 57.509 | −9.791 | 5.114 | 1.00 | 25.67 | A | N |
| ATOM | 4200 | CA | SER | A | 279 | 56.510 | −10.111 | 4.115 | 1.00 | 25.01 | A | C |
| ATOM | 4202 | CB | SER | A | 279 | 55.694 | −8.869 | 3.762 | 1.00 | 26.35 | A | C |
| ATOM | 4205 | OG | SER | A | 279 | 54.839 | −8.541 | 4.839 | 1.00 | 32.90 | A | O |
| ATOM | 4207 | C | SER | A | 279 | 57.152 | −10.682 | 2.875 | 1.00 | 24.05 | A | C |
| ATOM | 4208 | O | SER | A | 279 | 56.560 | −11.514 | 2.223 | 1.00 | 23.50 | A | O |
| ATOM | 4210 | N | PHE | A | 280 | 58.365 | −10.237 | 2.551 | 1.00 | 21.71 | A | N |

TABLE 4-2-continued

Coordinates of *P. alba* IspS

| ATOM | 4211 | CA | PHE | A | 280 | 59.091 | −10.801 | 1.419 | 1.00 | 23.37 | A | C |
|---|---|---|---|---|---|---|---|---|---|---|---|---|
| ATOM | 4213 | CB | PHE | A | 280 | 60.266 | −9.902 | 1.017 | 1.00 | 25.01 | A | C |
| ATOM | 4216 | CG | PHE | A | 280 | 60.841 | −10.261 | −0.298 | 1.00 | 22.72 | A | C |
| ATOM | 4217 | CD1 | PHE | A | 280 | 60.259 | −9.812 | −1.466 | 1.00 | 26.45 | A | C |
| ATOM | 4219 | CE1 | PHE | A | 280 | 60.747 | −10.180 | −2.677 | 1.00 | 25.95 | A | C |
| ATOM | 4221 | CZ | PHE | A | 280 | 61.836 | −11.022 | −2.737 | 1.00 | 25.35 | A | C |
| ATOM | 4223 | CE2 | PHE | A | 280 | 62.415 | −11.486 | −1.584 | 1.00 | 24.77 | A | C |
| ATOM | 4225 | CD2 | PHE | A | 280 | 61.917 | −11.108 | −0.370 | 1.00 | 26.82 | A | C |
| ATOM | 4227 | C | PHE | A | 280 | 59.599 | −12.226 | 1.709 | 1.00 | 23.03 | A | C |
| ATOM | 4228 | O | PHE | A | 280 | 59.491 | −13.103 | 0.863 | 1.00 | 25.85 | A | O |
| ATOM | 4230 | N | TYR | A | 281 | 60.156 | −12.429 | 2.896 | 1.00 | 23.11 | A | N |
| ATOM | 4231 | CA | TYR | A | 281 | 60.546 | −13.751 | 3.392 | 1.00 | 24.07 | A | C |
| ATOM | 4233 | CB | TYR | A | 281 | 61.140 | −13.640 | 4.806 | 1.00 | 24.19 | A | C |
| ATOM | 4236 | CG | TYR | A | 281 | 61.313 | −14.958 | 5.545 | 1.00 | 26.46 | A | C |
| ATOM | 4237 | CD1 | TYR | A | 281 | 62.469 | −15.728 | 5.401 | 1.00 | 28.95 | A | C |
| ATOM | 4239 | CE1 | TYR | A | 281 | 62.607 | −16.960 | 6.070 | 1.00 | 32.82 | A | C |
| ATOM | 4241 | CZ | TYR | A | 281 | 61.584 | −17.403 | 6.899 | 1.00 | 23.73 | A | C |
| ATOM | 4242 | OH | TYR | A | 281 | 61.699 | −18.572 | 7.602 | 1.00 | 37.06 | A | O |
| ATOM | 4244 | CE2 | TYR | A | 281 | 60.463 | −16.627 | 7.091 | 1.00 | 27.38 | A | C |
| ATOM | 4246 | CD2 | TYR | A | 281 | 60.336 | −15.409 | 6.424 | 1.00 | 28.38 | A | C |
| ATOM | 4248 | C | TYR | A | 281 | 59.327 | −14.681 | 3.339 | 1.00 | 23.90 | A | C |
| ATOM | 4249 | O | TYR | A | 281 | 59.407 | −15.778 | 2.841 | 1.00 | 22.03 | A | O |
| ATOM | 4251 | N | TRP | A | 282 | 58.178 | −14.190 | 3.769 | 1.00 | 24.19 | A | N |
| ATOM | 4252 | CA | TRP | A | 282 | 56.946 | −14.940 | 3.645 | 1.00 | 23.89 | A | C |
| ATOM | 4254 | CB | TRP | A | 282 | 55.772 | −14.098 | 4.127 | 1.00 | 24.11 | A | C |
| ATOM | 4257 | CG | TRP | A | 282 | 54.466 | −14.809 | 4.037 | 1.00 | 24.19 | A | C |
| ATOM | 4258 | CD1 | TRP | A | 282 | 53.597 | −14.786 | 2.998 | 1.00 | 22.17 | A | C |
| ATOM | 4260 | NE1 | TRP | A | 282 | 52.491 | −15.562 | 3.279 | 1.00 | 24.03 | A | N |
| ATOM | 4262 | CE2 | TRP | A | 282 | 52.657 | −16.120 | 4.518 | 1.00 | 27.44 | A | C |
| ATOM | 4263 | CD2 | TRP | A | 282 | 53.888 | −15.656 | 5.029 | 1.00 | 23.48 | A | C |
| ATOM | 4264 | CE3 | TRP | A | 282 | 54.291 | −16.075 | 6.296 | 1.00 | 29.21 | A | C |
| ATOM | 4266 | CZ3 | TRP | A | 282 | 53.470 | −16.930 | 7.001 | 1.00 | 30.47 | A | C |
| ATOM | 4268 | CH2 | TRP | A | 282 | 52.255 | −17.363 | 6.468 | 1.00 | 29.72 | A | C |
| ATOM | 4270 | CZ2 | TRP | A | 282 | 51.830 | −16.962 | 5.233 | 1.00 | 25.51 | A | C |
| ATOM | 4272 | C | TRP | A | 282 | 56.717 | −15.400 | 2.195 | 1.00 | 24.21 | A | C |
| ATOM | 4273 | O | TRP | A | 282 | 56.504 | −16.587 | 1.947 | 1.00 | 22.03 | A | O |
| ATOM | 4275 | N | ALA | A | 283 | 56.806 | −14.455 | 1.259 | 1.00 | 22.23 | A | N |
| ATOM | 4276 | CA | ALA | A | 283 | 56.573 | −14.706 | −0.165 | 1.00 | 20.96 | A | C |
| ATOM | 4278 | CB | ALA | A | 283 | 56.663 | −13.402 | −0.961 | 1.00 | 18.60 | A | C |
| ATOM | 4282 | C | ALA | A | 283 | 57.522 | −15.728 | −0.781 | 1.00 | 21.39 | A | C |
| ATOM | 4283 | O | ALA | A | 283 | 57.118 | −16.474 | −1.679 | 1.00 | 20.52 | A | O |
| ATOM | 4285 | N | VAL | A | 284 | 58.769 | −15.754 | −0.318 | 1.00 | 22.30 | A | N |
| ATOM | 4286 | CA | VAL | A | 284 | 59.758 | −16.758 | −0.764 | 1.00 | 23.58 | A | C |
| ATOM | 4288 | CB | VAL | A | 284 | 61.144 | −16.478 | −0.111 | 1.00 | 24.57 | A | C |
| ATOM | 4290 | CG1 | VAL | A | 284 | 61.727 | −15.180 | −0.672 | 1.00 | 19.22 | A | C |
| ATOM | 4294 | CG2 | VAL | A | 284 | 62.095 | −17.641 | −0.320 | 1.00 | 19.35 | A | C |
| ATOM | 4298 | C | VAL | A | 284 | 59.302 | −18.202 | −0.456 | 1.00 | 24.32 | A | C |
| ATOM | 4299 | O | VAL | A | 284 | 59.566 | −19.151 | −1.208 | 1.00 | 23.82 | A | O |
| ATOM | 4301 | N | GLY | A | 285 | 58.599 | −18.369 | 0.649 | 1.00 | 24.47 | A | N |
| ATOM | 4302 | CA | GLY | A | 285 | 57.973 | −19.648 | 0.958 | 1.00 | 21.25 | A | C |
| ATOM | 4305 | C | GLY | A | 285 | 56.907 | −20.048 | −0.031 | 1.00 | 20.54 | A | C |
| ATOM | 4306 | O | GLY | A | 285 | 56.745 | −21.226 | −0.300 | 1.00 | 22.10 | A | O |
| ATOM | 4308 | N | VAL | A | 286 | 56.162 | −19.078 | −0.547 | 1.00 | 22.33 | A | N |
| ATOM | 4309 | CA | VAL | A | 286 | 55.029 | −19.347 | −1.441 | 1.00 | 20.31 | A | C |
| ATOM | 4311 | CB | VAL | A | 286 | 54.045 | −18.169 | −1.463 | 1.00 | 23.35 | A | C |
| ATOM | 4313 | CG1 | VAL | A | 286 | 52.961 | −18.408 | −2.468 | 1.00 | 22.65 | A | C |
| ATOM | 4317 | CG2 | VAL | A | 286 | 53.388 | −17.973 | −0.051 | 1.00 | 22.60 | A | C |
| ATOM | 4321 | C | VAL | A | 286 | 55.529 | −19.659 | −2.834 | 1.00 | 22.01 | A | C |
| ATOM | 4322 | O | VAL | A | 286 | 55.056 | −20.605 | −3.472 | 1.00 | 22.74 | A | O |
| ATOM | 4324 | N | ALA | A | 287 | 56.540 | −18.915 | −3.279 | 1.00 | 21.32 | A | N |
| ATOM | 4325 | CA | ALA | A | 287 | 57.034 | −19.003 | −4.629 | 1.00 | 20.30 | A | C |
| ATOM | 4327 | CB | ALA | A | 287 | 56.297 | −17.991 | −5.503 | 1.00 | 21.67 | A | C |
| ATOM | 4331 | C | ALA | A | 287 | 58.540 | −18.779 | −4.678 | 1.00 | 23.56 | A | C |
| ATOM | 4332 | O | ALA | A | 287 | 59.038 | −17.632 | −4.868 | 1.00 | 25.80 | A | O |
| ATOM | 4334 | N | PHE | A | 288 | 59.286 | −19.860 | −4.502 | 1.00 | 21.24 | A | N |
| ATOM | 4335 | CA | PHE | A | 288 | 60.720 | −19.748 | −4.348 | 1.00 | 22.02 | A | C |
| ATOM | 4337 | CB | PHE | A | 288 | 61.254 | −20.872 | −3.493 | 1.00 | 22.68 | A | C |
| ATOM | 4340 | CG | PHE | A | 288 | 61.372 | −22.180 | −4.225 | 1.00 | 26.97 | A | C |
| ATOM | 4341 | CD1 | PHE | A | 288 | 62.541 | −22.512 | −4.885 | 1.00 | 31.37 | A | C |
| ATOM | 4343 | CE1 | PHE | A | 288 | 62.649 | −23.713 | −5.570 | 1.00 | 35.11 | A | C |
| ATOM | 4345 | CZ | PHE | A | 288 | 61.587 | −24.584 | −5.596 | 1.00 | 29.46 | A | C |
| ATOM | 4347 | CE2 | PHE | A | 288 | 60.415 | −24.273 | −4.937 | 1.00 | 33.40 | A | C |
| ATOM | 4349 | CD2 | PHE | A | 288 | 60.310 | −23.067 | −4.255 | 1.00 | 33.76 | A | C |
| ATOM | 4351 | C | PHE | A | 288 | 61.451 | −19.743 | −5.697 | 1.00 | 26.03 | A | C |
| ATOM | 4352 | O | PHE | A | 288 | 62.568 | −19.226 | −5.784 | 1.00 | 25.19 | A | O |
| ATOM | 4354 | N | GLU | A | 289 | 60.836 | −20.322 | −6.734 | 1.00 | 27.65 | A | N |
| ATOM | 4355 | CA | GLU | A | 289 | 61.515 | −20.489 | −8.023 | 1.00 | 30.57 | A | C |
| ATOM | 4357 | CB | GLU | A | 289 | 60.643 | −21.265 | −9.023 | 1.00 | 32.76 | A | C |

TABLE 4-2-continued

Coordinates of *P. alba* IspS

| ATOM | 4360 | CG | GLU | A | 289 | 60.270 | −22.716 | −8.620 | 1.00 | 35.64 | A | C |
|---|---|---|---|---|---|---|---|---|---|---|---|---|
| ATOM | 4363 | CD | GLU | A | 289 | 58.926 | −22.861 | −7.872 | 1.00 | 42.73 | A | C |
| ATOM | 4364 | OE1 | GLU | A | 289 | 58.488 | −21.920 | −7.160 | 1.00 | 37.11 | A | O |
| ATOM | 4365 | OE2 | GLU | A | 289 | 58.306 | −23.949 | −8.008 | 1.00 | 42.82 | A | O |
| ATOM | 4366 | C | GLU | A | 289 | 61.916 | −19.123 | −8.599 | 1.00 | 30.30 | A | C |
| ATOM | 4367 | O | GLU | A | 289 | 61.153 | −18.141 | −8.491 | 1.00 | 29.03 | A | O |
| ATOM | 4369 | N | PRO | A | 290 | 63.115 | −19.049 | −9.204 | 1.00 | 28.09 | A | N |
| ATOM | 4370 | CA | PRO | A | 290 | 63.664 | −17.754 | −9.554 | 1.00 | 29.01 | A | C |
| ATOM | 4372 | CB | PRO | A | 290 | 65.013 | −18.089 | −10.205 | 1.00 | 29.11 | A | C |
| ATOM | 4375 | CG | PRO | A | 290 | 64.972 | −19.515 | −10.485 | 1.00 | 29.92 | A | C |
| ATOM | 4378 | CD | PRO | A | 290 | 64.059 | −20.129 | −9.491 | 1.00 | 29.29 | A | C |
| ATOM | 4381 | C | PRO | A | 290 | 62.789 | −16.958 | −10.500 | 1.00 | 28.51 | A | C |
| ATOM | 4382 | O | PRO | A | 290 | 62.732 | −15.737 | −10.385 | 1.00 | 28.65 | A | O |
| ATOM | 4383 | N | GLN | A | 291 | 62.099 | −17.650 | −11.397 | 1.00 | 27.75 | A | N |
| ATOM | 4384 | CA | GLN | A | 291 | 61.250 | −16.998 | −12.382 | 1.00 | 28.53 | A | C |
| ATOM | 4386 | CB | GLN | A | 291 | 60.845 | −17.961 | −13.519 | 1.00 | 27.02 | A | C |
| ATOM | 4389 | CG | GLN | A | 291 | 59.893 | −19.074 | −13.155 | 1.00 | 31.90 | A | C |
| ATOM | 4392 | CD | GLN | A | 291 | 60.583 | −20.284 | −12.532 | 1.00 | 38.40 | A | C |
| ATOM | 4393 | OE1 | GLN | A | 291 | 61.709 | −20.183 | −12.037 | 1.00 | 39.73 | A | O |
| ATOM | 4394 | NE2 | GLN | A | 291 | 59.911 | −21.449 | −12.576 | 1.00 | 32.16 | A | N |
| ATOM | 4397 | C | GLN | A | 291 | 59.993 | −16.369 | −11.795 | 1.00 | 29.44 | A | C |
| ATOM | 4398 | O | GLN | A | 291 | 59.343 | −15.592 | −12.496 | 1.00 | 31.07 | A | O |
| ATOM | 4400 | N | TYR | A | 292 | 59.633 | −16.690 | −10.547 | 1.00 | 28.42 | A | N |
| ATOM | 4401 | CA | TYR | A | 292 | 58.398 | −16.147 | −9.951 | 1.00 | 27.91 | A | C |
| ATOM | 4403 | CB | TYR | A | 292 | 57.733 | −17.182 | −9.046 | 1.00 | 30.21 | A | C |
| ATOM | 4406 | CG | TYR | A | 292 | 57.131 | −18.402 | −9.740 | 1.00 | 31.70 | A | C |
| ATOM | 4407 | CD1 | TYR | A | 292 | 56.502 | −18.299 | −10.975 | 1.00 | 31.99 | A | C |
| ATOM | 4409 | CE1 | TYR | A | 292 | 55.951 | −19.407 | −11.591 | 1.00 | 39.31 | A | C |
| ATOM | 4411 | CZ | TYR | A | 292 | 55.999 | −20.641 | −10.970 | 1.00 | 38.20 | A | C |
| ATOM | 4412 | OH | TYR | A | 292 | 55.441 | −21.716 | −11.596 | 1.00 | 45.03 | A | O |
| ATOM | 4414 | CE2 | TYR | A | 292 | 56.601 | −20.781 | −9.735 | 1.00 | 42.05 | A | C |
| ATOM | 4416 | CD2 | TYR | A | 292 | 57.166 | −19.663 | −9.126 | 1.00 | 39.69 | A | C |
| ATOM | 4418 | C | TYR | A | 292 | 58.594 | −14.816 | −9.182 | 1.00 | 28.53 | A | C |
| ATOM | 4419 | O | TYR | A | 292 | 57.989 | −14.590 | −8.118 | 1.00 | 25.90 | A | O |
| ATOM | 4421 | N | SER | A | 293 | 59.398 | −13.916 | −9.747 | 1.00 | 28.30 | A | N |
| ATOM | 4422 | CA | SER | A | 293 | 59.641 | −12.601 | −9.135 | 1.00 | 28.09 | A | C |
| ATOM | 4424 | CB | SER | A | 293 | 60.602 | −11.763 | −10.009 | 1.00 | 29.47 | A | C |
| ATOM | 4427 | OG | SER | A | 293 | 61.965 | −11.924 | −9.592 | 1.00 | 29.79 | A | O |
| ATOM | 4429 | C | SER | A | 293 | 58.352 | −11.808 | −8.874 | 1.00 | 28.45 | A | C |
| ATOM | 4430 | O | SER | A | 293 | 58.189 | −11.199 | −7.805 | 1.00 | 28.09 | A | O |
| ATOM | 4432 | N | ASP | A | 294 | 57.449 | −11.808 | −9.855 | 1.00 | 26.88 | A | N |
| ATOM | 4433 | CA | ASP | A | 294 | 56.223 | −11.048 | −9.784 | 1.00 | 25.77 | A | C |
| ATOM | 4435 | CB | ASP | A | 294 | 55.461 | −11.124 | −11.117 | 1.00 | 28.17 | A | C |
| ATOM | 4438 | CG | ASP | A | 294 | 56.157 | −10.395 | −12.248 | 1.00 | 34.74 | A | C |
| ATOM | 4439 | OD1 | ASP | A | 294 | 56.956 | −9.462 | −12.000 | 1.00 | 36.83 | A | O |
| ATOM | 4440 | OD2 | ASP | A | 294 | 55.888 | −10.765 | −13.412 | 1.00 | 45.26 | A | O |
| ATOM | 4441 | C | ASP | A | 294 | 55.313 | −11.591 | −8.684 | 1.00 | 28.84 | A | C |
| ATOM | 4442 | O | ASP | A | 294 | 54.585 | −10.823 | −8.009 | 1.00 | 29.14 | A | O |
| ATOM | 4444 | N | CYS | A | 295 | 55.322 | −12.912 | −8.517 | 1.00 | 26.55 | A | N |
| ATOM | 4445 | CA | CYS | A | 295 | 54.540 | −13.511 | −7.464 | 1.00 | 27.07 | A | C |
| ATOM | 4447 | CB | CYS | A | 295 | 54.524 | −15.043 | −7.567 | 1.00 | 28.06 | A | C |
| ATOM | 4450 | SG | CYS | A | 295 | 53.328 | −15.810 | −6.436 | 1.00 | 26.81 | A | S |
| ATOM | 4452 | C | CYS | A | 295 | 55.044 | −13.060 | −6.100 | 1.00 | 25.39 | A | C |
| ATOM | 4453 | O | CYS | A | 295 | 54.254 | −12.597 | −5.284 | 1.00 | 26.37 | A | O |
| ATOM | 4455 | N | ARG | A | 296 | 56.345 | −13.169 | −5.861 | 1.00 | 24.67 | A | N |
| ATOM | 4456 | CA | ARG | A | 296 | 56.923 | −12.732 | −4.592 | 1.00 | 24.65 | A | C |
| ATOM | 4458 | CB | ARG | A | 296 | 58.437 | −12.963 | −4.543 | 1.00 | 25.23 | A | C |
| ATOM | 4461 | CG | ARG | A | 296 | 58.835 | −14.418 | −4.502 | 1.00 | 22.91 | A | C |
| ATOM | 4464 | CD | ARG | A | 296 | 60.318 | −14.618 | −4.304 | 1.00 | 19.82 | A | C |
| ATOM | 4467 | NE | ARG | A | 296 | 61.076 | −14.305 | −5.507 | 1.00 | 19.18 | A | N |
| ATOM | 4469 | CZ | ARG | A | 296 | 61.223 | −15.096 | −6.561 | 1.00 | 22.17 | A | C |
| ATOM | 4470 | NH1 | ARG | A | 296 | 60.647 | −16.274 | −6.620 | 1.00 | 26.97 | A | N |
| ATOM | 4473 | NH2 | ARG | A | 296 | 61.933 | −14.676 | −7.592 | 1.00 | 26.83 | A | N |
| ATOM | 4476 | C | ARG | A | 296 | 56.651 | −11.249 | −4.321 | 1.00 | 24.07 | A | C |
| ATOM | 4477 | O | ARG | A | 296 | 56.264 | −10.893 | −3.221 | 1.00 | 24.88 | A | O |
| ATOM | 4479 | N | ASN | A | 297 | 56.849 | −10.408 | −5.325 | 1.00 | 23.19 | A | N |
| ATOM | 4480 | CA | ASN | A | 297 | 56.624 | −8.982 | −5.192 | 1.00 | 24.62 | A | C |
| ATOM | 4482 | CB | ASN | A | 297 | 57.063 | −8.215 | −6.463 | 1.00 | 25.20 | A | C |
| ATOM | 4485 | CG | ASN | A | 297 | 58.598 | −8.235 | −6.676 | 1.00 | 30.05 | A | C |
| ATOM | 4486 | OD1 | ASN | A | 297 | 59.359 | −8.502 | −5.753 | 1.00 | 36.93 | A | O |
| ATOM | 4487 | ND2 | ASN | A | 297 | 59.039 | −7.959 | −7.903 | 1.00 | 25.92 | A | N |
| ATOM | 4490 | C | ASN | A | 297 | 55.152 | −8.696 | −4.866 | 1.00 | 24.78 | A | C |
| ATOM | 4491 | O | ASN | A | 297 | 54.871 | −7.960 | −3.926 | 1.00 | 22.91 | A | O |
| ATOM | 4493 | N | SER | A | 298 | 54.236 | −9.305 | −5.613 | 1.00 | 23.57 | A | N |
| ATOM | 4494 | CA | SER | A | 298 | 52.813 | −9.173 | −5.338 | 1.00 | 25.11 | A | C |
| ATOM | 4496 | CB | SER | A | 298 | 51.968 | −10.060 | −6.272 | 1.00 | 24.10 | A | C |
| ATOM | 4499 | OG | SER | A | 298 | 51.678 | −9.429 | −7.493 | 1.00 | 32.64 | A | O |
| ATOM | 4501 | C | SER | A | 298 | 52.475 | −9.579 | −3.916 | 1.00 | 22.38 | A | C |

TABLE 4-2-continued

Coordinates of *P. alba* IspS

| ATOM | 4502 | O | SER | A | 298 | 51.809 | −8.846 | −3.192 | 1.00 | 24.02 | A | O |
|---|---|---|---|---|---|---|---|---|---|---|---|---|
| ATOM | 4504 | N | VAL | A | 299 | 52.857 | −10.791 | −3.552 | 1.00 | 21.05 | A | N |
| ATOM | 4505 | CA | VAL | A | 299 | 52.520 | −11.321 | −2.237 | 1.00 | 20.22 | A | C |
| ATOM | 4507 | CB | VAL | A | 299 | 52.949 | −12.794 | −2.091 | 1.00 | 20.34 | A | C |
| ATOM | 4509 | CG1 | VAL | A | 299 | 52.838 | −13.258 | −0.650 | 1.00 | 22.69 | A | C |
| ATOM | 4513 | CG2 | VAL | A | 299 | 52.089 | −13.647 | −2.954 | 1.00 | 18.14 | A | C |
| ATOM | 4517 | C | VAL | A | 299 | 53.124 | −10.468 | −1.133 | 1.00 | 19.72 | A | C |
| ATOM | 4518 | O | VAL | A | 299 | 52.466 | −10.220 | −0.122 | 1.00 | 21.66 | A | O |
| ATOM | 4520 | N | ALA | A | 300 | 54.342 | −9.970 | −1.342 | 1.00 | 19.58 | A | N |
| ATOM | 4521 | CA | ALA | A | 300 | 55.011 | −9.150 | −0.320 | 1.00 | 21.43 | A | C |
| ATOM | 4523 | CB | ALA | A | 300 | 56.486 | −8.987 | −0.667 | 1.00 | 19.80 | A | C |
| ATOM | 4527 | C | ALA | A | 300 | 54.339 | −7.779 | −0.181 | 1.00 | 21.64 | A | C |
| ATOM | 4528 | O | ALA | A | 300 | 54.232 | −7.202 | 0.922 | 1.00 | 21.71 | A | O |
| ATOM | 4530 | N | LYS | A | 301 | 53.872 | −7.255 | −1.303 | 1.00 | 22.14 | A | N |
| ATOM | 4531 | CA | LYS | A | 301 | 53.204 | −5.964 | −1.281 | 1.00 | 21.36 | A | C |
| ATOM | 4533 | CB | LYS | A | 301 | 52.984 | −5.439 | −2.690 | 1.00 | 20.86 | A | C |
| ATOM | 4536 | CG | LYS | A | 301 | 54.236 | −4.921 | −3.366 | 1.00 | 19.27 | A | C |
| ATOM | 4539 | CD | LYS | A | 301 | 53.965 | −4.388 | −4.792 | 1.00 | 19.50 | A | C |
| ATOM | 4542 | CE | LYS | A | 301 | 55.276 | −3.879 | −5.400 | 1.00 | 29.29 | A | C |
| ATOM | 4545 | NZ | LYS | A | 301 | 55.116 | −3.235 | −6.741 | 1.00 | 34.09 | A | N |
| ATOM | 4549 | C | LYS | A | 301 | 51.879 | −6.131 | −0.548 | 1.00 | 21.48 | A | C |
| ATOM | 4550 | O | LYS | A | 301 | 51.540 | −5.352 | 0.338 | 1.00 | 22.68 | A | O |
| ATOM | 4552 | N | MET | A | 302 | 51.160 | −7.192 | −0.878 | 1.00 | 20.39 | A | N |
| ATOM | 4553 | CA | MET | A | 302 | 49.849 | −7.409 | −0.282 | 1.00 | 20.92 | A | C |
| ATOM | 4555 | CB | MET | A | 302 | 49.133 | −8.583 | −0.969 | 1.00 | 20.09 | A | C |
| ATOM | 4558 | CG | MET | A | 302 | 48.712 | −8.266 | −2.405 | 1.00 | 19.65 | A | C |
| ATOM | 4561 | SD | MET | A | 302 | 47.843 | −6.709 | −2.587 | 1.00 | 28.88 | A | S |
| ATOM | 4562 | CE | MET | A | 302 | 49.185 | −5.629 | −3.034 | 1.00 | 23.45 | A | C |
| ATOM | 4566 | C | MET | A | 302 | 49.937 | −7.677 | 1.199 | 1.00 | 22.54 | A | C |
| ATOM | 4567 | O | MET | A | 302 | 49.185 | −7.097 | 1.998 | 1.00 | 24.84 | A | O |
| ATOM | 4569 | N | PHE | A | 303 | 50.861 | −8.551 | 1.579 | 1.00 | 22.29 | A | N |
| ATOM | 4570 | CA | PHE | A | 303 | 51.019 | −8.862 | 2.982 | 1.00 | 22.99 | A | C |
| ATOM | 4572 | CB | PHE | A | 303 | 51.984 | −10.050 | 3.159 | 1.00 | 25.28 | A | C |
| ATOM | 4575 | CG | PHE | A | 303 | 51.716 | −10.891 | 4.387 | 1.00 | 30.30 | A | C |
| ATOM | 4576 | CD1 | PHE | A | 303 | 50.589 | −10.683 | 5.192 | 1.00 | 34.42 | A | C |
| ATOM | 4578 | CE1 | PHE | A | 303 | 50.371 | −11.460 | 6.324 | 1.00 | 42.97 | A | C |
| ATOM | 4580 | CZ | PHE | A | 303 | 51.274 | −12.459 | 6.657 | 1.00 | 41.14 | A | C |
| ATOM | 4582 | CE2 | PHE | A | 303 | 52.381 | −12.678 | 5.871 | 1.00 | 34.43 | A | C |
| ATOM | 4584 | CD2 | PHE | A | 303 | 52.599 | −11.899 | 4.741 | 1.00 | 36.11 | A | C |
| ATOM | 4586 | C | PHE | A | 303 | 51.455 | −7.625 | 3.816 | 1.00 | 21.77 | A | C |
| ATOM | 4587 | O | PHE | A | 303 | 51.033 | −7.464 | 4.938 | 1.00 | 23.38 | A | O |
| ATOM | 4589 | N | SER | A | 304 | 52.270 | −6.755 | 3.244 | 1.00 | 20.77 | A | N |
| ATOM | 4590 | CA | SER | A | 304 | 52.648 | −5.517 | 3.876 | 1.00 | 21.72 | A | C |
| ATOM | 4592 | CB | SER | A | 304 | 53.638 | −4.750 | 2.997 | 1.00 | 24.31 | A | C |
| ATOM | 4595 | OG | SER | A | 304 | 54.847 | −5.480 | 2.795 | 1.00 | 28.25 | A | O |
| ATOM | 4597 | C | SER | A | 304 | 51.440 | −4.622 | 4.150 | 1.00 | 23.63 | A | C |
| ATOM | 4598 | O | SER | A | 304 | 51.387 | −4.005 | 5.212 | 1.00 | 24.50 | A | O |
| ATOM | 4600 | N | PHE | A | 305 | 50.497 | −4.541 | 3.205 | 1.00 | 23.27 | A | N |
| ATOM | 4601 | CA | PHE | A | 305 | 49.230 | −3.804 | 3.424 | 1.00 | 21.89 | A | C |
| ATOM | 4603 | CB | PHE | A | 305 | 48.466 | −3.560 | 2.113 | 1.00 | 22.71 | A | C |
| ATOM | 4606 | CG | PHE | A | 305 | 48.938 | −2.345 | 1.368 | 1.00 | 20.52 | A | C |
| ATOM | 4607 | CD1 | PHE | A | 305 | 48.659 | −1.073 | 1.850 | 1.00 | 24.16 | A | C |
| ATOM | 4609 | CE1 | PHE | A | 305 | 49.097 | 0.050 | 1.181 | 1.00 | 23.31 | A | C |
| ATOM | 4611 | CZ | PHE | A | 305 | 49.826 | −0.078 | 0.013 | 1.00 | 23.43 | A | C |
| ATOM | 4613 | CE2 | PHE | A | 305 | 50.120 | −1.337 | −0.478 | 1.00 | 29.03 | A | C |
| ATOM | 4615 | CD2 | PHE | A | 305 | 49.682 | −2.469 | 0.219 | 1.00 | 22.45 | A | C |
| ATOM | 4617 | C | PHE | A | 305 | 48.313 | −4.499 | 4.393 | 1.00 | 20.95 | A | C |
| ATOM | 4618 | O | PHE | A | 305 | 47.674 | −3.849 | 5.226 | 1.00 | 20.99 | A | O |
| ATOM | 4620 | N | VAL | A | 306 | 48.255 | −5.821 | 4.309 | 1.00 | 20.76 | A | N |
| ATOM | 4621 | CA | VAL | A | 306 | 47.434 | −6.575 | 5.229 | 1.00 | 19.75 | A | C |
| ATOM | 4623 | CB | VAL | A | 306 | 47.506 | −8.080 | 4.963 | 1.00 | 22.66 | A | C |
| ATOM | 4625 | CG1 | VAL | A | 306 | 46.885 | −8.886 | 6.091 | 1.00 | 16.37 | A | C |
| ATOM | 4629 | CG2 | VAL | A | 306 | 46.790 | −8.388 | 3.645 | 1.00 | 21.60 | A | C |
| ATOM | 4633 | C | VAL | A | 306 | 47.823 | −6.224 | 6.636 | 1.00 | 22.33 | A | C |
| ATOM | 4634 | O | VAL | A | 306 | 46.962 | −5.861 | 7.435 | 1.00 | 24.20 | A | O |
| ATOM | 4636 | N | THR | A | 307 | 49.108 | −6.225 | 6.945 | 1.00 | 24.63 | A | N |
| ATOM | 4637 | CA | THR | A | 307 | 49.502 | −6.040 | 8.344 | 1.00 | 26.20 | A | C |
| ATOM | 4639 | CB | THR | A | 307 | 51.009 | −6.313 | 8.570 | 1.00 | 26.67 | A | C |
| ATOM | 4641 | OG1 | THR | A | 307 | 51.771 | −5.398 | 7.828 | 1.00 | 36.85 | A | O |
| ATOM | 4643 | CG2 | THR | A | 307 | 51.386 | −7.698 | 8.106 | 1.00 | 31.58 | A | C |
| ATOM | 4647 | C | THR | A | 307 | 49.092 | −4.669 | 8.895 | 1.00 | 25.04 | A | C |
| ATOM | 4648 | O | THR | A | 307 | 48.668 | −4.547 | 10.049 | 1.00 | 26.45 | A | O |
| ATOM | 4650 | N | ILE | A | 308 | 49.172 | −3.647 | 8.060 | 1.00 | 23.77 | A | N |
| ATOM | 4651 | CA | ILE | A | 308 | 48.761 | −2.299 | 8.445 | 1.00 | 23.18 | A | C |
| ATOM | 4653 | CB | ILE | A | 308 | 49.219 | −1.270 | 7.409 | 1.00 | 24.44 | A | C |
| ATOM | 4655 | CG1 | ILE | A | 308 | 50.742 | −1.206 | 7.371 | 1.00 | 29.53 | A | C |
| ATOM | 4658 | CD1 | ILE | A | 308 | 51.267 | −0.355 | 6.265 | 1.00 | 30.91 | A | C |
| ATOM | 4662 | CG2 | ILE | A | 308 | 48.639 | 0.078 | 7.714 | 1.00 | 23.42 | A | C |

TABLE 4-2-continued

Coordinates of *P. alba* IspS

| ATOM | 4666 | C | ILE | A | 308 | 47.252 | −2.223 | 8.554 | 1.00 | 20.59 | A | C |
|------|------|-----|-----|---|-----|--------|--------|--------|------|-------|---|---|
| ATOM | 4667 | O | ILE | A | 308 | 46.723 | −1.650 | 9.506 | 1.00 | 20.09 | A | O |
| ATOM | 4669 | N | ILE | A | 309 | 46.551 | −2.802 | 7.585 | 1.00 | 20.24 | A | N |
| ATOM | 4670 | CA | ILE | A | 309 | 45.093 | −2.712 | 7.594 | 1.00 | 22.80 | A | C |
| ATOM | 4672 | CB | ILE | A | 309 | 44.466 | −3.173 | 6.284 | 1.00 | 24.10 | A | C |
| ATOM | 4674 | CG1 | ILE | A | 309 | 44.927 | −2.279 | 5.128 | 1.00 | 25.79 | A | C |
| ATOM | 4677 | CD1 | ILE | A | 309 | 44.234 | −1.018 | 5.079 | 1.00 | 37.61 | A | C |
| ATOM | 4681 | CG2 | ILE | A | 309 | 42.941 | −3.162 | 6.360 | 1.00 | 17.79 | A | C |
| ATOM | 4685 | C | ILE | A | 309 | 44.584 | −3.521 | 8.777 | 1.00 | 23.44 | A | C |
| ATOM | 4686 | O | ILE | A | 309 | 43.626 | −3.118 | 9.447 | 1.00 | 23.95 | A | O |
| ATOM | 4688 | N | ASP | A | 310 | 45.278 | −4.617 | 9.076 | 1.00 | 24.85 | A | N |
| ATOM | 4689 | CA | ASP | A | 310 | 44.942 | −5.453 | 10.226 | 1.00 | 25.67 | A | C |
| ATOM | 4691 | CB | ASP | A | 310 | 45.823 | −6.716 | 10.278 | 1.00 | 29.93 | A | C |
| ATOM | 4694 | CG | ASP | A | 310 | 45.316 | −7.775 | 11.294 | 1.00 | 34.30 | A | C |
| ATOM | 4695 | OD1 | ASP | A | 310 | 44.106 | −7.830 | 11.573 | 1.00 | 46.69 | A | O |
| ATOM | 4696 | OD2 | ASP | A | 310 | 46.139 | −8.566 | 11.790 | 1.00 | 50.27 | A | O |
| ATOM | 4697 | C | ASP | A | 310 | 45.084 | −4.658 | 11.501 | 1.00 | 23.92 | A | C |
| ATOM | 4698 | O | ASP | A | 310 | 44.202 | −4.696 | 12.344 | 1.00 | 23.74 | A | O |
| ATOM | 4700 | N | ASP | A | 311 | 46.167 | −3.903 | 11.648 | 1.00 | 23.61 | A | N |
| ATOM | 4701 | CA | ASP | A | 311 | 46.302 | −3.063 | 12.840 | 1.00 | 24.15 | A | C |
| ATOM | 4703 | CB | ASP | A | 311 | 47.653 | −2.346 | 12.864 | 1.00 | 25.79 | A | C |
| ATOM | 4706 | CG | ASP | A | 311 | 48.811 | −3.283 | 13.157 | 1.00 | 33.35 | A | C |
| ATOM | 4707 | OD1 | ASP | A | 311 | 48.578 | −4.327 | 13.802 | 1.00 | 37.00 | A | O |
| ATOM | 4708 | OD2 | ASP | A | 311 | 49.951 | −2.976 | 12.720 | 1.00 | 42.12 | A | O |
| ATOM | 4709 | C | ASP | A | 311 | 45.185 | −2.013 | 12.963 | 1.00 | 22.01 | A | C |
| ATOM | 4710 | O | ASP | A | 311 | 44.750 | −1.689 | 14.066 | 1.00 | 20.06 | A | O |
| ATOM | 4712 | N | ILE | A | 312 | 44.738 | −1.486 | 11.827 | 1.00 | 20.61 | A | N |
| ATOM | 4713 | CA | ILE | A | 312 | 43.693 | −0.467 | 11.814 | 1.00 | 20.98 | A | C |
| ATOM | 4715 | CB | ILE | A | 312 | 43.462 | 0.111 | 10.392 | 1.00 | 20.72 | A | C |
| ATOM | 4717 | CG1 | ILE | A | 312 | 44.605 | 1.043 | 10.000 | 1.00 | 19.24 | A | C |
| ATOM | 4720 | CD1 | ILE | A | 312 | 44.576 | 1.481 | 8.508 | 1.00 | 18.67 | A | C |
| ATOM | 4724 | CG2 | ILE | A | 312 | 42.163 | 0.844 | 10.337 | 1.00 | 17.52 | A | C |
| ATOM | 4728 | C | ILE | A | 312 | 42.403 | −1.049 | 12.373 | 1.00 | 21.29 | A | C |
| ATOM | 4729 | O | ILE | A | 312 | 41.781 | −0.462 | 13.259 | 1.00 | 22.89 | A | O |
| ATOM | 4731 | N | TYR | A | 313 | 42.036 | −2.232 | 11.905 | 1.00 | 21.99 | A | N |
| ATOM | 4732 | CA | TYR | A | 313 | 40.816 | −2.852 | 12.362 | 1.00 | 22.07 | A | C |
| ATOM | 4734 | CB | TYR | A | 313 | 40.395 | −3.962 | 11.408 | 1.00 | 21.44 | A | C |
| ATOM | 4737 | CG | TYR | A | 313 | 39.668 | −3.483 | 10.187 | 1.00 | 17.68 | A | C |
| ATOM | 4738 | CD1 | TYR | A | 313 | 38.273 | −3.567 | 10.095 | 1.00 | 17.60 | A | C |
| ATOM | 4740 | CE1 | TYR | A | 313 | 37.601 | −3.157 | 8.927 | 1.00 | 18.93 | A | C |
| ATOM | 4742 | CZ | TYR | A | 313 | 38.333 | −2.642 | 7.866 | 1.00 | 20.93 | A | C |
| ATOM | 4743 | OH | TYR | A | 313 | 37.713 | −2.225 | 6.703 | 1.00 | 21.19 | A | O |
| ATOM | 4745 | CE2 | TYR | A | 313 | 39.705 | −2.556 | 7.953 | 1.00 | 21.64 | A | C |
| ATOM | 4747 | CD2 | TYR | A | 313 | 40.361 | −2.958 | 9.111 | 1.00 | 20.65 | A | C |
| ATOM | 4749 | C | TYR | A | 313 | 40.929 | −3.399 | 13.761 | 1.00 | 24.20 | A | C |
| ATOM | 4750 | O | TYR | A | 313 | 39.957 | −3.362 | 14.526 | 1.00 | 25.90 | A | O |
| ATOM | 4752 | N | ASP | A | 314 | 42.119 | −3.872 | 14.108 | 1.00 | 26.32 | A | N |
| ATOM | 4753 | CA | ASP | A | 314 | 42.339 | −4.552 | 15.395 | 1.00 | 27.33 | A | C |
| ATOM | 4755 | CB | ASP | A | 314 | 43.622 | −5.398 | 15.321 | 1.00 | 29.31 | A | C |
| ATOM | 4758 | CG | ASP | A | 314 | 43.891 | −6.217 | 16.598 | 1.00 | 33.13 | A | C |
| ATOM | 4759 | OD1 | ASP | A | 314 | 42.985 | −6.889 | 17.107 | 1.00 | 38.25 | A | O |
| ATOM | 4760 | OD2 | ASP | A | 314 | 45.038 | −6.219 | 17.065 | 1.00 | 42.87 | A | O |
| ATOM | 4761 | C | ASP | A | 314 | 42.415 | −3.565 | 16.560 | 1.00 | 25.83 | A | C |
| ATOM | 4762 | O | ASP | A | 314 | 41.786 | −3.798 | 17.589 | 1.00 | 24.11 | A | O |
| ATOM | 4764 | N | VAL | A | 315 | 43.168 | −2.469 | 16.419 | 1.00 | 25.13 | A | N |
| ATOM | 4765 | CA | VAL | A | 315 | 43.388 | −1.571 | 17.581 | 1.00 | 23.81 | A | C |
| ATOM | 4767 | CB | VAL | A | 315 | 44.803 | −1.707 | 18.175 | 1.00 | 24.08 | A | C |
| ATOM | 4769 | CG1 | VAL | A | 315 | 44.920 | −3.047 | 18.917 | 1.00 | 27.01 | A | C |
| ATOM | 4773 | CG2 | VAL | A | 315 | 45.876 | −1.542 | 17.111 | 1.00 | 18.89 | A | C |
| ATOM | 4777 | C | VAL | A | 315 | 43.121 | −0.091 | 17.390 | 1.00 | 24.28 | A | C |
| ATOM | 4778 | O | VAL | A | 315 | 42.626 | 0.550 | 18.316 | 1.00 | 25.60 | A | O |
| ATOM | 4780 | N | TYR | A | 316 | 43.452 | 0.454 | 16.218 | 1.00 | 23.17 | A | N |
| ATOM | 4781 | CA | TYR | A | 316 | 43.463 | 1.888 | 16.012 | 1.00 | 22.03 | A | C |
| ATOM | 4783 | CB | TYR | A | 316 | 44.468 | 2.250 | 14.921 | 1.00 | 24.42 | A | C |
| ATOM | 4786 | CG | TYR | A | 316 | 44.780 | 3.741 | 14.847 | 1.00 | 24.19 | A | C |
| ATOM | 4787 | CD1 | TYR | A | 316 | 45.669 | 4.330 | 15.734 | 1.00 | 22.67 | A | C |
| ATOM | 4789 | CE1 | TYR | A | 316 | 45.956 | 5.710 | 15.664 | 1.00 | 26.80 | A | C |
| ATOM | 4791 | CZ | TYR | A | 316 | 45.343 | 6.487 | 14.689 | 1.00 | 23.98 | A | C |
| ATOM | 4792 | OH | TYR | A | 316 | 45.616 | 7.825 | 14.594 | 1.00 | 23.58 | A | O |
| ATOM | 4794 | CE2 | TYR | A | 316 | 44.462 | 5.915 | 13.802 | 1.00 | 27.54 | A | C |
| ATOM | 4796 | CD2 | TYR | A | 316 | 44.188 | 4.553 | 13.880 | 1.00 | 23.46 | A | C |
| ATOM | 4798 | C | TYR | A | 316 | 42.109 | 2.489 | 15.659 | 1.00 | 21.60 | A | C |
| ATOM | 4799 | O | TYR | A | 316 | 41.709 | 3.471 | 16.256 | 1.00 | 21.67 | A | O |
| ATOM | 4801 | N | GLY | A | 317 | 41.407 | 1.917 | 14.684 | 1.00 | 22.29 | A | N |
| ATOM | 4802 | CA | GLY | A | 317 | 40.150 | 2.510 | 14.186 | 1.00 | 21.66 | A | C |
| ATOM | 4805 | C | GLY | A | 317 | 38.877 | 2.302 | 15.016 | 1.00 | 22.48 | A | C |
| ATOM | 4806 | O | GLY | A | 317 | 38.613 | 1.212 | 15.566 | 1.00 | 20.21 | A | O |
| ATOM | 4808 | N | THR | A | 318 | 38.050 | 3.335 | 15.090 | 1.00 | 21.00 | A | N |

TABLE 4-2-continued

Coordinates of *P. alba* IspS

| ATOM | 4809 | CA | THR | A | 318 | 36.756 | 3.163 | 15.737 | 1.00 | 22.14 | A | C |
|---|---|---|---|---|---|---|---|---|---|---|---|---|
| ATOM | 4811 | CB | THR | A | 318 | 36.126 | 4.472 | 16.125 | 1.00 | 20.46 | A | C |
| ATOM | 4813 | OG1 | THR | A | 318 | 35.835 | 5.197 | 14.935 | 1.00 | 20.90 | A | O |
| ATOM | 4815 | CG2 | THR | A | 318 | 37.073 | 5.280 | 17.008 | 1.00 | 21.19 | A | C |
| ATOM | 4819 | C | THR | A | 318 | 35.844 | 2.436 | 14.759 | 1.00 | 21.63 | A | C |
| ATOM | 4820 | O | THR | A | 318 | 36.110 | 2.395 | 13.550 | 1.00 | 21.76 | A | O |
| ATOM | 4822 | N | LEU | A | 319 | 34.777 | 1.864 | 15.297 | 1.00 | 20.18 | A | N |
| ATOM | 4823 | CA | LEU | A | 319 | 33.830 | 1.067 | 14.514 | 1.00 | 22.24 | A | C |
| ATOM | 4825 | CB | LEU | A | 319 | 32.701 | 0.551 | 15.416 | 1.00 | 22.04 | A | C |
| ATOM | 4828 | CG | LEU | A | 319 | 32.239 | −0.897 | 15.249 | 1.00 | 31.30 | A | C |
| ATOM | 4830 | CD1 | LEU | A | 319 | 33.410 | −1.842 | 15.024 | 1.00 | 25.53 | A | C |
| ATOM | 4834 | CD2 | LEU | A | 319 | 31.421 | −1.339 | 16.464 | 1.00 | 34.06 | A | C |
| ATOM | 4838 | C | LEU | A | 319 | 33.258 | 1.867 | 13.347 | 1.00 | 23.17 | A | C |
| ATOM | 4839 | O | LEU | A | 319 | 33.195 | 1.361 | 12.226 | 1.00 | 23.56 | A | O |
| ATOM | 4841 | N | ASP | A | 320 | 32.877 | 3.118 | 13.610 | 1.00 | 23.84 | A | N |
| ATOM | 4842 | CA | ASP | A | 320 | 32.388 | 4.035 | 12.580 | 1.00 | 26.41 | A | C |
| ATOM | 4844 | CB | ASP | A | 320 | 31.999 | 5.411 | 13.174 | 1.00 | 28.62 | A | C |
| ATOM | 4847 | CG | ASP | A | 320 | 30.753 | 5.370 | 14.089 | 1.00 | 34.92 | A | C |
| ATOM | 4848 | OD1 | ASP | A | 320 | 29.889 | 4.480 | 13.934 | 1.00 | 40.85 | A | O |
| ATOM | 4849 | OD2 | ASP | A | 320 | 30.633 | 6.273 | 14.960 | 1.00 | 45.71 | A | O |
| ATOM | 4850 | C | ASP | A | 320 | 33.454 | 4.260 | 11.490 | 1.00 | 25.67 | A | C |
| ATOM | 4851 | O | ASP | A | 320 | 33.133 | 4.313 | 10.319 | 1.00 | 26.46 | A | O |
| ATOM | 4853 | N | GLU | A | 321 | 34.713 | 4.420 | 11.879 | 1.00 | 24.15 | A | N |
| ATOM | 4854 | CA | GLU | A | 321 | 35.787 | 4.613 | 10.895 | 1.00 | 22.51 | A | C |
| ATOM | 4856 | CB | GLU | A | 321 | 37.102 | 4.984 | 11.579 | 1.00 | 21.98 | A | C |
| ATOM | 4859 | CG | GLU | A | 321 | 37.114 | 6.354 | 12.250 | 1.00 | 22.24 | A | C |
| ATOM | 4862 | CD | GLU | A | 321 | 38.425 | 6.622 | 13.009 | 1.00 | 26.20 | A | C |
| ATOM | 4863 | OE1 | GLU | A | 321 | 39.060 | 5.664 | 13.490 | 1.00 | 22.42 | A | O |
| ATOM | 4864 | OE2 | GLU | A | 321 | 38.823 | 7.795 | 13.126 | 1.00 | 26.34 | A | O |
| ATOM | 4865 | C | GLU | A | 321 | 35.997 | 3.346 | 10.075 | 1.00 | 22.83 | A | C |
| ATOM | 4866 | O | GLU | A | 321 | 36.239 | 3.410 | 8.869 | 1.00 | 20.72 | A | O |
| ATOM | 4868 | N | LEU | A | 322 | 35.902 | 2.191 | 10.735 | 1.00 | 21.58 | A | N |
| ATOM | 4869 | CA | LEU | A | 322 | 36.126 | 0.944 | 10.053 | 1.00 | 21.00 | A | C |
| ATOM | 4871 | CB | LEU | A | 322 | 36.303 | −0.196 | 11.051 | 1.00 | 20.31 | A | C |
| ATOM | 4874 | CG | LEU | A | 322 | 37.454 | −0.038 | 12.044 | 1.00 | 21.17 | A | C |
| ATOM | 4876 | CD1 | LEU | A | 322 | 37.523 | −1.242 | 12.977 | 1.00 | 21.39 | A | C |
| ATOM | 4880 | CD2 | LEU | A | 322 | 38.778 | 0.167 | 11.355 | 1.00 | 21.53 | A | C |
| ATOM | 4884 | C | LEU | A | 322 | 34.998 | 0.636 | 9.065 | 1.00 | 22.33 | A | C |
| ATOM | 4885 | O | LEU | A | 322 | 35.233 | −0.029 | 8.055 | 1.00 | 23.58 | A | O |
| ATOM | 4887 | N | GLU | A | 323 | 33.784 | 1.099 | 9.351 | 1.00 | 23.50 | A | N |
| ATOM | 4888 | CA | GLU | A | 323 | 32.687 | 0.991 | 8.396 | 1.00 | 23.70 | A | C |
| ATOM | 4890 | CB | GLU | A | 323 | 31.342 | 1.418 | 9.002 | 1.00 | 25.90 | A | C |
| ATOM | 4893 | CG | GLU | A | 323 | 30.728 | 0.464 | 10.031 | 1.00 | 31.83 | A | C |
| ATOM | 4896 | CD | GLU | A | 323 | 29.981 | −0.734 | 9.421 | 1.00 | 38.05 | A | C |
| ATOM | 4897 | OE1 | GLU | A | 323 | 29.503 | −1.575 | 10.218 | 1.00 | 40.48 | A | O |
| ATOM | 4898 | OE2 | GLU | A | 323 | 29.875 | −0.839 | 8.170 | 1.00 | 39.62 | A | O |
| ATOM | 4899 | C | GLU | A | 323 | 32.991 | 1.873 | 7.193 | 1.00 | 23.25 | A | C |
| ATOM | 4900 | O | GLU | A | 323 | 32.756 | 1.466 | 6.043 | 1.00 | 20.74 | A | O |
| ATOM | 4902 | N | LEU | A | 324 | 33.507 | 3.082 | 7.434 | 1.00 | 22.29 | A | N |
| ATOM | 4903 | CA | LEU | A | 324 | 33.832 | 3.961 | 6.302 | 1.00 | 23.80 | A | C |
| ATOM | 4905 | CB | LEU | A | 324 | 34.286 | 5.340 | 6.768 | 1.00 | 25.06 | A | C |
| ATOM | 4908 | CG | LEU | A | 324 | 33.225 | 6.246 | 7.386 | 1.00 | 30.71 | A | C |
| ATOM | 4910 | CD1 | LEU | A | 324 | 33.874 | 7.501 | 8.031 | 1.00 | 27.53 | A | C |
| ATOM | 4914 | CD2 | LEU | A | 324 | 32.178 | 6.642 | 6.330 | 1.00 | 32.67 | A | C |
| ATOM | 4918 | C | LEU | A | 324 | 34.888 | 3.306 | 5.399 | 1.00 | 22.01 | A | C |
| ATOM | 4919 | O | LEU | A | 324 | 34.739 | 3.259 | 4.180 | 1.00 | 23.37 | A | O |
| ATOM | 4921 | N | PHE | A | 325 | 35.916 | 2.736 | 6.003 | 1.00 | 21.76 | A | N |
| ATOM | 4922 | CA | PHE | A | 325 | 36.998 | 2.111 | 5.239 | 1.00 | 21.09 | A | C |
| ATOM | 4924 | CB | PHE | A | 325 | 38.125 | 1.683 | 6.176 | 1.00 | 20.33 | A | C |
| ATOM | 4927 | CG | PHE | A | 325 | 39.389 | 1.362 | 5.465 | 1.00 | 18.41 | A | C |
| ATOM | 4928 | CD1 | PHE | A | 325 | 40.259 | 2.364 | 5.107 | 1.00 | 19.45 | A | C |
| ATOM | 4930 | CE1 | PHE | A | 325 | 41.431 | 2.078 | 4.437 | 1.00 | 17.94 | A | C |
| ATOM | 4932 | CZ | PHE | A | 325 | 41.746 | 0.809 | 4.112 | 1.00 | 18.28 | A | C |
| ATOM | 4934 | CE2 | PHE | A | 325 | 40.879 | −0.223 | 4.450 | 1.00 | 27.60 | A | C |
| ATOM | 4936 | CD2 | PHE | A | 325 | 39.702 | 0.070 | 5.143 | 1.00 | 19.26 | A | C |
| ATOM | 4938 | C | PHE | A | 325 | 36.516 | 0.919 | 4.430 | 1.00 | 19.97 | A | C |
| ATOM | 4939 | O | PHE | A | 325 | 36.797 | 0.802 | 3.238 | 1.00 | 19.86 | A | O |
| ATOM | 4941 | N | THR | A | 326 | 35.785 | 0.036 | 5.094 | 1.00 | 21.26 | A | N |
| ATOM | 4942 | CA | THR | A | 326 | 35.189 | −1.144 | 4.453 | 1.00 | 20.87 | A | C |
| ATOM | 4944 | CB | THR | A | 326 | 34.294 | −1.897 | 5.435 | 1.00 | 21.86 | A | C |
| ATOM | 4946 | OG1 | THR | A | 326 | 35.065 | −2.222 | 6.594 | 1.00 | 24.18 | A | O |
| ATOM | 4948 | CG2 | THR | A | 326 | 33.754 | −3.180 | 4.828 | 1.00 | 15.64 | A | C |
| ATOM | 4952 | C | THR | A | 326 | 34.364 | −0.770 | 3.234 | 1.00 | 21.47 | A | C |
| ATOM | 4953 | O | THR | A | 326 | 34.581 | −1.306 | 2.146 | 1.00 | 20.27 | A | O |
| ATOM | 4955 | N | ASP | A | 327 | 33.454 | 0.183 | 3.422 | 1.00 | 23.46 | A | N |
| ATOM | 4956 | CA | ASP | A | 327 | 32.624 | 0.717 | 2.342 | 1.00 | 24.01 | A | C |
| ATOM | 4958 | CB | ASP | A | 327 | 31.644 | 1.747 | 2.914 | 1.00 | 24.35 | A | C |
| ATOM | 4961 | CG | ASP | A | 327 | 30.821 | 2.461 | 1.837 | 1.00 | 33.07 | A | C |

TABLE 4-2-continued

Coordinates of *P. alba* IspS

| ATOM | 4962 | OD1 | ASP | A | 327 | 29.907 | 1.827 | 1.249 | 1.00 | 35.22 | A | O |
|---|---|---|---|---|---|---|---|---|---|---|---|---|
| ATOM | 4963 | OD2 | ASP | A | 327 | 31.080 | 3.674 | 1.594 | 1.00 | 39.61 | A | O |
| ATOM | 4964 | C | ASP | A | 327 | 33.486 | 1.322 | 1.210 | 1.00 | 24.37 | A | C |
| ATOM | 4965 | O | ASP | A | 327 | 33.203 | 1.124 | 0.026 | 1.00 | 24.49 | A | O |
| ATOM | 4967 | N | ALA | A | 328 | 34.547 | 2.038 | 1.568 | 1.00 | 23.77 | A | N |
| ATOM | 4968 | CA | ALA | A | 328 | 35.410 | 2.652 | 0.559 | 1.00 | 21.98 | A | C |
| ATOM | 4970 | CB | ALA | A | 328 | 36.444 | 3.553 | 1.211 | 1.00 | 20.52 | A | C |
| ATOM | 4974 | C | ALA | A | 328 | 36.101 | 1.571 | −0.290 | 1.00 | 20.95 | A | C |
| ATOM | 4975 | O | ALA | A | 328 | 36.252 | 1.727 | −1.498 | 1.00 | 19.89 | A | O |
| ATOM | 4977 | N | VAL | A | 329 | 36.504 | 0.475 | 0.341 | 1.00 | 19.74 | A | N |
| ATOM | 4978 | CA | VAL | A | 329 | 37.136 | −0.623 | −0.385 | 1.00 | 18.98 | A | C |
| ATOM | 4980 | CB | VAL | A | 329 | 37.802 | −1.638 | 0.563 | 1.00 | 18.57 | A | C |
| ATOM | 4982 | CG1 | VAL | A | 329 | 38.961 | −0.957 | 1.330 | 1.00 | 15.41 | A | C |
| ATOM | 4986 | CG2 | VAL | A | 329 | 38.301 | −2.860 | −0.184 | 1.00 | 19.70 | A | C |
| ATOM | 4990 | C | VAL | A | 329 | 36.100 | −1.269 | −1.289 | 1.00 | 21.12 | A | C |
| ATOM | 4991 | O | VAL | A | 329 | 36.383 | −1.524 | −2.448 | 1.00 | 23.23 | A | O |
| ATOM | 4993 | N | GLU | A | 330 | 34.882 | −1.455 | −0.799 | 1.00 | 22.69 | A | N |
| ATOM | 4994 | CA | GLU | A | 330 | 33.828 | −2.078 | −1.610 | 1.00 | 24.26 | A | C |
| ATOM | 4996 | CB | GLU | A | 330 | 32.564 | −2.299 | −0.789 | 1.00 | 24.45 | A | C |
| ATOM | 4999 | CG | GLU | A | 330 | 32.659 | −3.424 | 0.254 | 1.00 | 32.15 | A | C |
| ATOM | 5002 | CD | GLU | A | 330 | 31.415 | −3.522 | 1.181 | 1.00 | 37.11 | A | C |
| ATOM | 5003 | OE1 | GLU | A | 330 | 31.335 | −4.497 | 1.946 | 1.00 | 41.56 | A | O |
| ATOM | 5004 | OE2 | GLU | A | 330 | 30.536 | −2.629 | 1.162 | 1.00 | 37.97 | A | O |
| ATOM | 5005 | C | GLU | A | 330 | 33.484 | −1.252 | −2.842 | 1.00 | 24.43 | A | C |
| ATOM | 5006 | O | GLU | A | 330 | 33.372 | −1.785 | −3.931 | 1.00 | 23.22 | A | O |
| ATOM | 5008 | N | ARG | A | 331 | 33.305 | 0.048 | −2.659 | 1.00 | 24.59 | A | N |
| ATOM | 5009 | CA | AARG | A | 331 | 32.926 | 0.933 | −3.762 | 0.50 | 25.42 | A | C |
| ATOM | 5010 | CA | BARG | A | 331 | 32.924 | 0.934 | −3.762 | 0.50 | 25.53 | A | C |
| ATOM | 5013 | CB | AARG | A | 331 | 32.331 | 2.240 | −3.217 | 0.50 | 25.39 | A | C |
| ATOM | 5014 | CB | BARG | A | 331 | 32.311 | 2.238 | −3.215 | 0.50 | 25.60 | A | C |
| ATOM | 5019 | CG | AARG | A | 331 | 30.912 | 2.068 | −2.616 | 0.50 | 29.35 | A | C |
| ATOM | 5020 | CG | BARG | A | 331 | 31.013 | 1.984 | −2.402 | 0.50 | 30.09 | A | C |
| ATOM | 5025 | CD | AARG | A | 331 | 30.467 | 3.348 | −1.936 | 0.50 | 31.41 | A | C |
| ATOM | 5026 | CD | BARG | A | 331 | 30.354 | 3.255 | −1.877 | 0.50 | 32.13 | A | C |
| ATOM | 5031 | NE | AARG | A | 331 | 31.254 | 4.455 | −2.460 | 0.50 | 36.48 | A | N |
| ATOM | 5032 | NE | BARG | A | 331 | 29.105 | 3.539 | −2.578 | 0.50 | 39.36 | A | N |
| ATOM | 5035 | CZ | AARG | A | 331 | 32.146 | 5.140 | −1.754 | 0.50 | 36.08 | A | C |
| ATOM | 5036 | CZ | BARG | A | 331 | 27.909 | 3.144 | −2.156 | 0.50 | 40.76 | A | C |
| ATOM | 5037 | NH1 | AARG | A | 331 | 32.820 | 6.106 | −2.332 | 0.50 | 37.83 | A | N |
| ATOM | 5038 | NH1 | BARG | A | 331 | 27.798 | 2.459 | −1.027 | 0.50 | 40.70 | A | N |
| ATOM | 5043 | NH2 | AARG | A | 331 | 32.348 | 4.880 | −0.471 | 0.50 | 33.30 | A | N |
| ATOM | 5044 | NH2 | BARG | A | 331 | 26.824 | 3.439 | −2.854 | 0.50 | 39.88 | A | N |
| ATOM | 5049 | C | ARG | A | 331 | 34.092 | 1.210 | −4.719 | 1.00 | 24.63 | A | C |
| ATOM | 5050 | O | ARG | A | 331 | 33.886 | 1.403 | −5.905 | 1.00 | 25.83 | A | O |
| ATOM | 5052 | N | TRP | A | 332 | 35.315 | 1.224 | −4.198 | 1.00 | 23.38 | A | N |
| ATOM | 5053 | CA | TRP | A | 332 | 36.540 | 1.354 | −5.008 | 1.00 | 22.12 | A | C |
| ATOM | 5055 | CB | TRP | A | 332 | 36.827 | 0.035 | −5.797 | 1.00 | 22.05 | A | C |
| ATOM | 5058 | CG | TRP | A | 332 | 38.233 | −0.101 | −6.263 | 1.00 | 19.00 | A | C |
| ATOM | 5059 | CD1 | TRP | A | 332 | 38.704 | 0.112 | −7.524 | 1.00 | 20.39 | A | C |
| ATOM | 5061 | NE1 | TRP | A | 332 | 40.077 | −0.096 | −7.562 | 1.00 | 21.23 | A | N |
| ATOM | 5063 | CE2 | TRP | A | 332 | 40.509 | −0.451 | −6.312 | 1.00 | 14.45 | A | C |
| ATOM | 5064 | CD2 | TRP | A | 332 | 39.381 | −0.461 | −5.462 | 1.00 | 22.97 | A | C |
| ATOM | 5065 | CE3 | TRP | A | 332 | 39.558 | −0.801 | −4.120 | 1.00 | 19.44 | A | C |
| ATOM | 5067 | CZ3 | TRP | A | 332 | 40.841 | −1.098 | −3.666 | 1.00 | 21.88 | A | C |
| ATOM | 5069 | CH2 | TRP | A | 332 | 41.936 | −1.073 | −4.536 | 1.00 | 23.07 | A | C |
| ATOM | 5071 | CZ2 | TRP | A | 332 | 41.787 | −0.751 | −5.859 | 1.00 | 27.36 | A | C |
| ATOM | 5073 | C | TRP | A | 332 | 36.468 | 2.569 | −5.923 | 1.00 | 21.31 | A | C |
| ATOM | 5074 | O | TRP | A | 332 | 36.673 | 2.481 | −7.133 | 1.00 | 21.30 | A | O |
| ATOM | 5076 | N | ASP | A | 333 | 36.203 | 3.715 | −5.311 | 1.00 | 23.84 | A | N |
| ATOM | 5077 | CA | ASP | A | 333 | 35.996 | 4.962 | −6.028 | 1.00 | 25.51 | A | C |
| ATOM | 5079 | CB | ASP | A | 333 | 34.525 | 5.365 | −5.884 | 1.00 | 28.49 | A | C |
| ATOM | 5082 | CG | ASP | A | 333 | 34.207 | 6.764 | −6.429 | 1.00 | 31.34 | A | C |
| ATOM | 5083 | OD1 | ASP | A | 333 | 35.061 | 7.438 | −7.055 | 1.00 | 37.88 | A | O |
| ATOM | 5084 | OD2 | ASP | A | 333 | 33.054 | 7.180 | −6.224 | 1.00 | 35.04 | A | O |
| ATOM | 5085 | C | ASP | A | 333 | 36.901 | 6.000 | −5.408 | 1.00 | 25.74 | A | C |
| ATOM | 5086 | O | ASP | A | 333 | 36.638 | 6.473 | −4.315 | 1.00 | 27.33 | A | O |
| ATOM | 5088 | N | VAL | A | 334 | 37.950 | 6.377 | −6.131 | 1.00 | 25.22 | A | N |
| ATOM | 5089 | CA | VAL | A | 334 | 38.913 | 7.315 | −5.629 | 1.00 | 24.40 | A | C |
| ATOM | 5091 | CB | VAL | A | 334 | 40.154 | 7.336 | −6.508 | 1.00 | 23.40 | A | C |
| ATOM | 5093 | CG1 | VAL | A | 334 | 41.277 | 8.090 | −5.851 | 1.00 | 22.78 | A | C |
| ATOM | 5097 | CG2 | VAL | A | 334 | 39.839 | 7.911 | −7.873 | 1.00 | 22.06 | A | C |
| ATOM | 5101 | C | VAL | A | 334 | 38.336 | 8.721 | −5.512 | 1.00 | 28.91 | A | C |
| ATOM | 5102 | O | VAL | A | 334 | 38.857 | 9.535 | −4.750 | 1.00 | 29.34 | A | O |
| ATOM | 5104 | N | ASN | A | 335 | 37.261 | 9.015 | −6.246 | 1.00 | 30.93 | A | N |
| ATOM | 5105 | CA | ASN | A | 335 | 36.668 | 10.356 | −6.204 | 1.00 | 32.90 | A | C |
| ATOM | 5107 | CB | ASN | A | 335 | 35.767 | 10.617 | −7.430 | 1.00 | 33.01 | A | C |
| ATOM | 5110 | CG | ASN | A | 335 | 36.539 | 10.559 | −8.768 | 1.00 | 35.09 | A | C |
| ATOM | 5111 | OD1 | ASN | A | 335 | 37.513 | 11.293 | −8.972 | 1.00 | 31.46 | A | O |

TABLE 4-2-continued

Coordinates of *P. alba* IspS

| ATOM | 5112 | ND2 | ASN | A | 335 | 36.080 | 9.693 | −9.690 | 1.00 | 29.46 | A | N |
|---|---|---|---|---|---|---|---|---|---|---|---|---|
| ATOM | 5115 | C | ASN | A | 335 | 35.889 | 10.616 | −4.916 | 1.00 | 35.23 | A | C |
| ATOM | 5116 | O | ASN | A | 335 | 35.438 | 11.744 | −4.718 | 1.00 | 37.55 | A | O |
| ATOM | 5118 | N | ALA | A | 336 | 35.737 | 9.588 | −4.062 | 1.00 | 36.18 | A | N |
| ATOM | 5119 | CA | ALA | A | 336 | 35.107 | 9.702 | −2.717 | 1.00 | 38.28 | A | C |
| ATOM | 5121 | CB | ALA | A | 336 | 33.972 | 8.678 | −2.600 | 1.00 | 37.37 | A | C |
| ATOM | 5125 | C | ALA | A | 336 | 36.067 | 9.540 | −1.501 | 1.00 | 38.39 | A | C |
| ATOM | 5126 | O | ALA | A | 336 | 35.632 | 9.516 | −0.357 | 1.00 | 40.53 | A | O |
| ATOM | 5128 | N | ILE | A | 337 | 37.357 | 9.392 | −1.766 | 1.00 | 39.34 | A | N |
| ATOM | 5129 | CA | ILE | A | 337 | 38.442 | 9.438 | −0.767 | 1.00 | 39.49 | A | C |
| ATOM | 5131 | CB | ILE | A | 337 | 39.770 | 9.736 | −1.552 | 1.00 | 41.71 | A | C |
| ATOM | 5133 | CG1 | ILE | A | 337 | 41.026 | 9.661 | −0.714 | 1.00 | 45.87 | A | C |
| ATOM | 5136 | CD1 | ILE | A | 337 | 42.218 | 10.171 | −1.518 | 1.00 | 45.13 | A | C |
| ATOM | 5140 | CG2 | ILE | A | 337 | 39.745 | 11.124 | −2.199 | 1.00 | 40.01 | A | C |
| ATOM | 5144 | C | ILE | A | 337 | 38.231 | 10.470 | 0.388 | 1.00 | 41.00 | A | C |
| ATOM | 5145 | O | ILE | A | 337 | 38.497 | 10.165 | 1.550 | 1.00 | 41.18 | A | O |
| ATOM | 5147 | N | ASN | A | 338 | 37.726 | 11.667 | 0.070 | 1.00 | 39.57 | A | N |
| ATOM | 5148 | CA | ASN | A | 338 | 37.503 | 12.723 | 1.064 | 1.00 | 39.05 | A | C |
| ATOM | 5150 | CB | ASN | A | 338 | 37.154 | 14.057 | 0.369 | 1.00 | 38.88 | A | C |
| ATOM | 5153 | CG | ASN | A | 338 | 38.379 | 14.735 | −0.240 | 1.00 | 38.68 | A | C |
| ATOM | 5154 | OD1 | ASN | A | 338 | 39.518 | 14.355 | 0.056 | 1.00 | 37.66 | A | O |
| ATOM | 5155 | ND2 | ASN | A | 338 | 38.154 | 15.740 | −1.091 | 1.00 | 32.26 | A | N |
| ATOM | 5158 | C | ASN | A | 338 | 36.484 | 12.420 | 2.180 | 1.00 | 38.52 | A | C |
| ATOM | 5159 | O | ASN | A | 338 | 36.443 | 13.142 | 3.179 | 1.00 | 36.24 | A | O |
| ATOM | 5161 | N | ASP | A | 339 | 35.695 | 11.360 | 2.017 | 1.00 | 37.68 | A | N |
| ATOM | 5162 | CA | ASP | A | 339 | 34.804 | 10.866 | 3.080 | 1.00 | 38.81 | A | C |
| ATOM | 5164 | CB | ASP | A | 339 | 33.943 | 9.699 | 2.546 | 1.00 | 41.47 | A | C |
| ATOM | 5167 | CG | ASP | A | 339 | 32.967 | 10.110 | 1.435 | 1.00 | 45.43 | A | C |
| ATOM | 5168 | OD1 | ASP | A | 339 | 32.684 | 11.323 | 1.284 | 1.00 | 49.71 | A | O |
| ATOM | 5169 | OD2 | ASP | A | 339 | 32.466 | 9.191 | 0.738 | 1.00 | 42.53 | A | O |
| ATOM | 5170 | C | ASP | A | 339 | 35.566 | 10.336 | 4.319 | 1.00 | 36.47 | A | C |
| ATOM | 5171 | O | ASP | A | 339 | 35.045 | 10.344 | 5.440 | 1.00 | 37.33 | A | O |
| ATOM | 5173 | N | LEU | A | 340 | 36.777 | 9.835 | 4.088 | 1.00 | 31.99 | A | N |
| ATOM | 5174 | CA | LEU | A | 340 | 37.551 | 9.126 | 5.099 | 1.00 | 28.85 | A | C |
| ATOM | 5176 | CB | LEU | A | 340 | 38.562 | 8.206 | 4.419 | 1.00 | 26.83 | A | C |
| ATOM | 5179 | CG | LEU | A | 340 | 38.040 | 7.105 | 3.512 | 1.00 | 26.05 | A | C |
| ATOM | 5181 | CD1 | LEU | A | 340 | 39.177 | 6.481 | 2.697 | 1.00 | 19.73 | A | C |
| ATOM | 5185 | CD2 | LEU | A | 340 | 37.335 | 6.075 | 4.347 | 1.00 | 28.12 | A | C |
| ATOM | 5189 | C | LEU | A | 340 | 38.342 | 10.102 | 5.973 | 1.00 | 27.33 | A | C |
| ATOM | 5190 | O | LEU | A | 340 | 38.664 | 11.198 | 5.525 | 1.00 | 28.68 | A | O |
| ATOM | 5192 | N | PRO | A | 341 | 38.698 | 9.681 | 7.199 | 1.00 | 24.34 | A | N |
| ATOM | 5193 | CA | PRO | A | 341 | 39.596 | 10.458 | 8.061 | 1.00 | 24.84 | A | C |
| ATOM | 5195 | CB | PRO | A | 341 | 39.422 | 9.801 | 9.439 | 1.00 | 26.28 | A | C |
| ATOM | 5198 | CG | PRO | A | 341 | 38.974 | 8.411 | 9.152 | 1.00 | 25.66 | A | C |
| ATOM | 5201 | CD | PRO | A | 341 | 38.256 | 8.427 | 7.838 | 1.00 | 23.02 | A | C |
| ATOM | 5204 | C | PRO | A | 341 | 41.037 | 10.361 | 7.585 | 1.00 | 23.92 | A | C |
| ATOM | 5205 | O | PRO | A | 341 | 41.409 | 9.379 | 6.966 | 1.00 | 23.65 | A | O |
| ATOM | 5206 | N | ASP | A | 342 | 41.835 | 11.381 | 7.878 | 1.00 | 24.01 | A | N |
| ATOM | 5207 | CA | ASP | A | 342 | 43.159 | 11.568 | 7.257 | 1.00 | 24.20 | A | C |
| ATOM | 5209 | CB | ASP | A | 342 | 43.956 | 12.647 | 8.021 | 1.00 | 24.30 | A | C |
| ATOM | 5212 | CG | ASP | A | 342 | 43.410 | 14.066 | 7.807 | 1.00 | 32.75 | A | C |
| ATOM | 5213 | OD1 | ASP | A | 342 | 42.564 | 14.253 | 6.896 | 1.00 | 33.36 | A | O |
| ATOM | 5214 | OD2 | ASP | A | 342 | 43.842 | 14.998 | 8.548 | 1.00 | 38.90 | A | O |
| ATOM | 5215 | C | ASP | A | 342 | 44.009 | 10.276 | 7.125 | 1.00 | 23.76 | A | C |
| ATOM | 5216 | O | ASP | A | 342 | 44.523 | 9.958 | 6.030 | 1.00 | 23.73 | A | O |
| ATOM | 5218 | N | TYR | A | 343 | 44.148 | 9.524 | 8.216 | 1.00 | 21.13 | A | N |
| ATOM | 5219 | CA | TYR | A | 343 | 45.020 | 8.355 | 8.192 | 1.00 | 20.93 | A | C |
| ATOM | 5221 | CB | TYR | A | 343 | 45.222 | 7.786 | 9.584 | 1.00 | 20.26 | A | C |
| ATOM | 5224 | CG | TYR | A | 343 | 44.066 | 7.002 | 10.157 | 1.00 | 23.08 | A | C |
| ATOM | 5225 | CD1 | TYR | A | 343 | 43.048 | 7.626 | 10.855 | 1.00 | 18.13 | A | C |
| ATOM | 5227 | CE1 | TYR | A | 343 | 42.009 | 6.903 | 11.384 | 1.00 | 27.05 | A | C |
| ATOM | 5229 | CZ | TYR | A | 343 | 41.994 | 5.521 | 11.239 | 1.00 | 24.51 | A | C |
| ATOM | 5230 | OH | TYR | A | 343 | 40.978 | 4.744 | 11.763 | 1.00 | 27.02 | A | O |
| ATOM | 5232 | CE2 | TYR | A | 343 | 43.012 | 4.892 | 10.571 | 1.00 | 23.11 | A | C |
| ATOM | 5234 | CD2 | TYR | A | 343 | 44.034 | 5.625 | 10.048 | 1.00 | 21.57 | A | C |
| ATOM | 5236 | C | TYR | A | 343 | 44.515 | 7.299 | 7.210 | 1.00 | 21.42 | A | C |
| ATOM | 5237 | O | TYR | A | 343 | 45.303 | 6.590 | 6.572 | 1.00 | 20.42 | A | O |
| ATOM | 5239 | N | MET | A | 344 | 43.204 | 7.235 | 7.053 | 1.00 | 20.78 | A | N |
| ATOM | 5240 | CA | MET | A | 344 | 42.599 | 6.275 | 6.146 | 1.00 | 22.17 | A | C |
| ATOM | 5242 | CB | MET | A | 344 | 41.151 | 5.989 | 6.556 | 1.00 | 21.39 | A | C |
| ATOM | 5245 | CG | MET | A | 344 | 41.055 | 5.081 | 7.781 | 1.00 | 19.99 | A | C |
| ATOM | 5248 | SD | MET | A | 344 | 39.358 | 4.723 | 8.256 | 1.00 | 25.10 | A | S |
| ATOM | 5249 | CE | MET | A | 344 | 39.531 | 3.255 | 9.301 | 1.00 | 20.13 | A | C |
| ATOM | 5253 | C | MET | A | 344 | 42.676 | 6.742 | 4.696 | 1.00 | 22.77 | A | C |
| ATOM | 5254 | O | MET | A | 344 | 42.854 | 5.928 | 3.799 | 1.00 | 23.66 | A | O |
| ATOM | 5256 | N | LYS | A | 345 | 42.553 | 8.045 | 4.454 | 1.00 | 24.61 | A | N |
| ATOM | 5257 | CA | LYS | A | 345 | 42.676 | 8.561 | 3.080 | 1.00 | 23.37 | A | C |
| ATOM | 5259 | CB | LYS | A | 345 | 42.640 | 10.084 | 3.016 | 1.00 | 26.29 | A | C |

TABLE 4-2-continued

Coordinates of *P. alba* IspS

| ATOM | 5262 | CG | LYS | A | 345 | 41.362 | 10.721 | 3.574 | 1.00 | 35.34 | A | C |
|---|---|---|---|---|---|---|---|---|---|---|---|---|
| ATOM | 5265 | CD | LYS | A | 345 | 41.422 | 12.243 | 3.653 | 1.00 | 37.03 | A | C |
| ATOM | 5268 | CE | LYS | A | 345 | 41.242 | 12.907 | 2.298 | 1.00 | 40.90 | A | C |
| ATOM | 5271 | NZ | LYS | A | 345 | 40.766 | 14.317 | 2.466 | 1.00 | 40.33 | A | N |
| ATOM | 5275 | C | LYS | A | 345 | 43.996 | 8.084 | 2.536 | 1.00 | 20.93 | A | C |
| ATOM | 5276 | O | LYS | A | 345 | 44.055 | 7.542 | 1.448 | 1.00 | 20.13 | A | O |
| ATOM | 5278 | N | LEU | A | 346 | 45.051 | 8.262 | 3.317 | 1.00 | 19.43 | A | N |
| ATOM | 5279 | CA | LEU | A | 346 | 46.392 | 7.947 | 2.861 | 1.00 | 19.97 | A | C |
| ATOM | 5281 | CB | LEU | A | 346 | 47.424 | 8.456 | 3.868 | 1.00 | 20.42 | A | C |
| ATOM | 5284 | CG | LEU | A | 346 | 48.885 | 8.424 | 3.430 | 1.00 | 24.60 | A | C |
| ATOM | 5286 | CD1 | LEU | A | 346 | 49.118 | 9.356 | 2.220 | 1.00 | 17.76 | A | C |
| ATOM | 5290 | CD2 | LEU | A | 346 | 49.789 | 8.796 | 4.594 | 1.00 | 27.43 | A | C |
| ATOM | 5294 | C | LEU | A | 346 | 46.534 | 6.470 | 2.661 | 1.00 | 21.21 | A | C |
| ATOM | 5295 | O | LEU | A | 346 | 47.029 | 6.024 | 1.655 | 1.00 | 21.29 | A | O |
| ATOM | 5297 | N | CYS | A | 347 | 46.051 | 5.698 | 3.624 | 1.00 | 23.15 | A | N |
| ATOM | 5298 | CA | CYS | A | 347 | 46.178 | 4.259 | 3.575 | 1.00 | 23.21 | A | C |
| ATOM | 5300 | CB | CYS | A | 347 | 45.760 | 3.653 | 4.943 | 1.00 | 25.14 | A | C |
| ATOM | 5303 | SG | CYS | A | 347 | 45.888 | 1.868 | 4.961 | 1.00 | 38.60 | A | S |
| ATOM | 5305 | C | CYS | A | 347 | 45.353 | 3.712 | 2.408 | 1.00 | 20.58 | A | C |
| ATOM | 5306 | O | CYS | A | 347 | 45.825 | 2.883 | 1.599 | 1.00 | 19.70 | A | O |
| ATOM | 5308 | N | PHE | A | 348 | 44.134 | 4.214 | 2.287 | 1.00 | 19.65 | A | N |
| ATOM | 5309 | CA | PHE | A | 348 | 43.299 | 3.863 | 1.155 | 1.00 | 19.61 | A | C |
| ATOM | 5311 | CB | PHE | A | 348 | 41.965 | 4.567 | 1.206 | 1.00 | 19.08 | A | C |
| ATOM | 5314 | CG | PHE | A | 348 | 41.070 | 4.192 | 0.080 | 1.00 | 18.31 | A | C |
| ATOM | 5315 | CD1 | PHE | A | 348 | 40.420 | 2.990 | 0.083 | 1.00 | 22.66 | A | C |
| ATOM | 5317 | CE1 | PHE | A | 348 | 39.594 | 2.623 | −0.973 | 1.00 | 23.56 | A | C |
| ATOM | 5319 | CZ | PHE | A | 348 | 39.444 | 3.455 | −2.043 | 1.00 | 21.10 | A | C |
| ATOM | 5321 | CE2 | PHE | A | 348 | 40.096 | 4.662 | −2.069 | 1.00 | 20.44 | A | C |
| ATOM | 5323 | CD2 | PHE | A | 348 | 40.907 | 5.031 | −1.011 | 1.00 | 24.44 | A | C |
| ATOM | 5325 | C | PHE | A | 348 | 43.951 | 4.141 | −0.197 | 1.00 | 19.37 | A | C |
| ATOM | 5326 | O | PHE | A | 348 | 44.056 | 3.244 | −1.037 | 1.00 | 17.63 | A | O |
| ATOM | 5328 | N | LEU | A | 349 | 44.408 | 5.367 | −0.413 | 1.00 | 16.49 | A | N |
| ATOM | 5329 | CA | LEU | A | 349 | 44.896 | 5.727 | −1.740 | 1.00 | 17.38 | A | C |
| ATOM | 5331 | CB | LEU | A | 349 | 45.157 | 7.229 | −1.849 | 1.00 | 18.66 | A | C |
| ATOM | 5334 | CG | LEU | A | 349 | 45.633 | 7.793 | −3.200 | 1.00 | 18.16 | A | C |
| ATOM | 5336 | CD1 | LEU | A | 349 | 44.756 | 7.364 | −4.359 | 1.00 | 16.21 | A | C |
| ATOM | 5340 | CD2 | LEU | A | 349 | 45.700 | 9.321 | −3.091 | 1.00 | 13.49 | A | C |
| ATOM | 5344 | C | LEU | A | 349 | 46.147 | 4.936 | −2.076 | 1.00 | 18.98 | A | C |
| ATOM | 5345 | O | LEU | A | 349 | 46.338 | 4.550 | −3.229 | 1.00 | 18.83 | A | O |
| ATOM | 5347 | N | ALA | A | 350 | 46.988 | 4.663 | −1.078 | 1.00 | 19.12 | A | N |
| ATOM | 5348 | CA | ALA | A | 350 | 48.147 | 3.791 | −1.316 | 1.00 | 20.75 | A | C |
| ATOM | 5350 | CB | ALA | A | 350 | 49.056 | 3.651 | −0.061 | 1.00 | 19.54 | A | C |
| ATOM | 5354 | C | ALA | A | 350 | 47.716 | 2.426 | −1.805 | 1.00 | 18.92 | A | C |
| ATOM | 5355 | O | ALA | A | 350 | 48.254 | 1.953 | −2.787 | 1.00 | 24.29 | A | O |
| ATOM | 5357 | N | LEU | A | 351 | 46.776 | 1.795 | −1.118 | 1.00 | 19.04 | A | N |
| ATOM | 5358 | CA | LEU | A | 351 | 46.259 | 0.458 | −1.506 | 1.00 | 19.56 | A | C |
| ATOM | 5360 | CB | LEU | A | 351 | 45.172 | −0.018 | −0.503 | 1.00 | 20.96 | A | C |
| ATOM | 5363 | CG | LEU | A | 351 | 44.558 | −1.412 | −0.691 | 1.00 | 24.54 | A | C |
| ATOM | 5365 | CD1 | LEU | A | 351 | 45.630 | −2.485 | −0.530 | 1.00 | 21.96 | A | C |
| ATOM | 5369 | CD2 | LEU | A | 351 | 43.419 | −1.645 | 0.287 | 1.00 | 20.98 | A | C |
| ATOM | 5373 | C | LEU | A | 351 | 45.637 | 0.519 | −2.884 | 1.00 | 19.78 | A | C |
| ATOM | 5374 | O | LEU | A | 351 | 45.941 | −0.293 | −3.762 | 1.00 | 20.30 | A | O |
| ATOM | 5376 | N | TYR | A | 352 | 44.744 | 1.496 | −3.056 | 1.00 | 19.85 | A | N |
| ATOM | 5377 | CA | TYR | A | 352 | 44.057 | 1.755 | −4.316 | 1.00 | 17.66 | A | C |
| ATOM | 5379 | CB | TYR | A | 352 | 43.296 | 3.075 | −4.210 | 1.00 | 20.69 | A | C |
| ATOM | 5382 | CG | TYR | A | 352 | 42.369 | 3.409 | −5.357 | 1.00 | 16.64 | A | C |
| ATOM | 5383 | CD1 | TYR | A | 352 | 41.126 | 2.831 | −5.453 | 1.00 | 21.99 | A | C |
| ATOM | 5385 | CE1 | TYR | A | 352 | 40.246 | 3.146 | −6.517 | 1.00 | 23.38 | A | C |
| ATOM | 5387 | CZ | TYR | A | 352 | 40.618 | 4.062 | −7.458 | 1.00 | 18.80 | A | C |
| ATOM | 5388 | OH | TYR | A | 352 | 39.759 | 4.352 | −8.509 | 1.00 | 23.84 | A | O |
| ATOM | 5390 | CE2 | TYR | A | 352 | 41.867 | 4.678 | −7.364 | 1.00 | 18.76 | A | C |
| ATOM | 5392 | CD2 | TYR | A | 352 | 42.727 | 4.353 | −6.316 | 1.00 | 18.81 | A | C |
| ATOM | 5394 | C | TYR | A | 352 | 45.036 | 1.781 | −5.468 | 1.00 | 17.34 | A | C |
| ATOM | 5395 | O | TYR | A | 352 | 44.892 | 1.025 | −6.435 | 1.00 | 17.23 | A | O |
| ATOM | 5397 | N | ASN | A | 353 | 46.046 | 2.633 | −5.374 | 1.00 | 17.53 | A | N |
| ATOM | 5398 | CA | ASN | A | 353 | 47.037 | 2.724 | −6.448 | 1.00 | 18.17 | A | C |
| ATOM | 5400 | CB | ASN | A | 353 | 48.000 | 3.874 | −6.213 | 1.00 | 18.33 | A | C |
| ATOM | 5403 | CG | ASN | A | 353 | 47.348 | 5.216 | −6.429 | 1.00 | 21.12 | A | C |
| ATOM | 5404 | OD1 | ASN | A | 353 | 46.297 | 5.299 | −7.068 | 1.00 | 16.85 | A | O |
| ATOM | 5405 | ND2 | ASN | A | 353 | 47.972 | 6.277 | −5.919 | 1.00 | 12.84 | A | N |
| ATOM | 5408 | C | ASN | A | 353 | 47.819 | 1.441 | −6.640 | 1.00 | 20.04 | A | C |
| ATOM | 5409 | O | ASN | A | 353 | 48.074 | 1.037 | −7.770 | 1.00 | 19.38 | A | O |
| ATOM | 5411 | N | THR | A | 354 | 48.201 | 0.790 | −5.542 | 1.00 | 19.93 | A | N |
| ATOM | 5412 | CA | THR | A | 354 | 48.989 | −0.408 | −5.668 | 1.00 | 19.28 | A | C |
| ATOM | 5414 | CB | THR | A | 354 | 49.441 | −0.944 | −4.307 | 1.00 | 21.85 | A | C |
| ATOM | 5416 | OG1 | THR | A | 354 | 50.234 | 0.055 | −3.636 | 1.00 | 18.52 | A | O |
| ATOM | 5418 | CG2 | THR | A | 354 | 50.267 | −2.217 | −4.509 | 1.00 | 20.83 | A | C |
| ATOM | 5422 | C | THR | A | 354 | 48.210 | −1.475 | −6.410 | 1.00 | 19.60 | A | C |

TABLE 4-2-continued

Coordinates of *P. alba* IspS

| ATOM | 5423 | O | THR | A | 354 | 48.749 | −2.127 | −7.287 | 1.00 | 21.37 | A | O |
|---|---|---|---|---|---|---|---|---|---|---|---|---|
| ATOM | 5425 | N | ILE | A | 355 | 46.939 | −1.651 | −6.065 | 1.00 | 19.20 | A | N |
| ATOM | 5426 | CA | ILE | A | 355 | 46.126 | −2.677 | −6.694 | 1.00 | 18.48 | A | C |
| ATOM | 5428 | CB | ILE | A | 355 | 44.795 | −2.901 | −5.921 | 1.00 | 18.37 | A | C |
| ATOM | 5430 | CG1 | ILE | A | 355 | 45.061 | −3.350 | −4.483 | 1.00 | 20.38 | A | C |
| ATOM | 5433 | CD1 | ILE | A | 355 | 46.192 | −4.335 | −4.324 | 1.00 | 29.16 | A | C |
| ATOM | 5437 | CG2 | ILE | A | 355 | 43.883 | −3.902 | −6.618 | 1.00 | 18.31 | A | C |
| ATOM | 5441 | C | ILE | A | 355 | 45.879 | −2.313 | −8.176 | 1.00 | 19.56 | A | C |
| ATOM | 5442 | O | ILE | A | 355 | 45.989 | −3.176 | −9.061 | 1.00 | 18.02 | A | O |
| ATOM | 5444 | N | ASN | A | 356 | 45.581 | −1.042 | −8.450 | 1.00 | 18.36 | A | N |
| ATOM | 5445 | CA | ASN | A | 356 | 45.340 | −0.616 | −9.819 | 1.00 | 18.34 | A | C |
| ATOM | 5447 | CB | ASN | A | 356 | 44.863 | 0.832 | −9.900 | 1.00 | 17.65 | A | C |
| ATOM | 5450 | CG | ASN | A | 356 | 43.476 | 1.028 | −9.334 | 1.00 | 16.23 | A | C |
| ATOM | 5451 | OD1 | ASN | A | 356 | 42.725 | 0.075 | −9.138 | 1.00 | 19.91 | A | O |
| ATOM | 5452 | ND2 | ASN | A | 356 | 43.116 | 2.290 | −9.083 | 1.00 | 20.98 | A | N |
| ATOM | 5455 | C | ASN | A | 356 | 46.564 | −0.825 | −10.703 | 1.00 | 19.43 | A | C |
| ATOM | 5456 | O | ASN | A | 356 | 46.422 | −1.142 | −11.887 | 1.00 | 20.70 | A | O |
| ATOM | 5458 | N | GLU | A | 357 | 47.753 | −0.671 | −10.132 | 1.00 | 20.68 | A | N |
| ATOM | 5459 | CA | AGLU | A | 357 | 48.994 | −0.866 | −10.888 | 0.50 | 21.52 | A | C |
| ATOM | 5460 | CA | BGLU | A | 357 | 49.010 | −0.884 | −10.874 | 0.50 | 20.35 | A | C |
| ATOM | 5463 | CB | AGLU | A | 357 | 50.194 | −0.231 | −10.148 | 0.50 | 22.00 | A | C |
| ATOM | 5464 | CB | BGLU | A | 357 | 50.217 | −0.366 | −10.079 | 0.50 | 20.11 | A | C |
| ATOM | 5469 | CG | AGLU | A | 357 | 50.380 | 1.275 | −10.466 | 0.50 | 28.65 | A | C |
| ATOM | 5470 | CG | BGLU | A | 357 | 51.579 | −0.813 | −10.618 | 0.50 | 19.78 | A | C |
| ATOM | 5475 | CD | AGLU | A | 357 | 50.846 | 2.136 | −9.291 | 0.50 | 33.37 | A | C |
| ATOM | 5476 | CD | BGLU | A | 357 | 52.743 | −0.147 | −9.918 | 0.50 | 23.84 | A | C |
| ATOM | 5477 | OE1 | AGLU | A | 357 | 51.301 | 1.583 | −8.270 | 0.50 | 33.65 | A | O |
| ATOM | 5478 | OE1 | BGLU | A | 357 | 52.594 | 0.268 | −8.744 | 0.50 | 29.12 | A | O |
| ATOM | 5479 | OE2 | AGLU | A | 357 | 50.754 | 3.387 | −9.402 | 0.50 | 37.95 | A | O |
| ATOM | 5480 | OE2 | BGLU | A | 357 | 53.816 | −0.051 | −10.544 | 0.50 | 25.37 | A | O |
| ATOM | 5481 | C | GLU | A | 357 | 49.201 | −2.360 | −11.206 | 1.00 | 19.73 | A | C |
| ATOM | 5482 | O | GLU | A | 357 | 49.669 | −2.716 | −12.285 | 1.00 | 18.33 | A | O |
| ATOM | 5484 | N | ILE | A | 358 | 48.822 | −3.231 | −10.280 | 1.00 | 20.56 | A | N |
| ATOM | 5485 | CA | ILE | A | 358 | 48.876 | −4.659 | −10.536 | 1.00 | 20.75 | A | C |
| ATOM | 5487 | CB | ILE | A | 358 | 48.706 | −5.508 | −9.260 | 1.00 | 22.24 | A | C |
| ATOM | 5489 | CG1 | ILE | A | 358 | 49.953 | −5.357 | −8.385 | 1.00 | 23.28 | A | C |
| ATOM | 5492 | CD1 | ILE | A | 358 | 49.763 | −5.808 | −6.885 | 1.00 | 20.16 | A | C |
| ATOM | 5496 | CG2 | ILE | A | 358 | 48.505 | −7.015 | −9.623 | 1.00 | 19.35 | A | C |
| ATOM | 5500 | C | ILE | A | 358 | 47.841 | −5.018 | −11.601 | 1.00 | 21.23 | A | C |
| ATOM | 5501 | O | ILE | A | 358 | 48.119 | −5.810 | −12.489 | 1.00 | 22.96 | A | O |
| ATOM | 5503 | N | ALA | A | 359 | 46.665 | −4.418 | −11.544 | 1.00 | 21.80 | A | N |
| ATOM | 5504 | CA | ALA | A | 359 | 45.693 | −4.608 | −12.625 | 1.00 | 20.99 | A | C |
| ATOM | 5506 | CB | ALA | A | 359 | 44.394 | −3.864 | −12.316 | 1.00 | 19.18 | A | C |
| ATOM | 5510 | C | ALA | A | 359 | 46.272 | −4.131 | −13.952 | 1.00 | 20.71 | A | C |
| ATOM | 5511 | O | ALA | A | 359 | 46.094 | −4.789 | −14.991 | 1.00 | 19.81 | A | O |
| ATOM | 5513 | N | TYR | A | 360 | 46.943 | −2.972 | −13.948 | 1.00 | 20.31 | A | N |
| ATOM | 5514 | CA | TYR | A | 360 | 47.532 | −2.470 | −15.209 | 1.00 | 18.47 | A | C |
| ATOM | 5516 | CB | TYR | A | 360 | 48.199 | −1.099 | −15.038 | 1.00 | 18.10 | A | C |
| ATOM | 5519 | CG | TYR | A | 360 | 48.851 | −0.625 | −16.318 | 1.00 | 15.44 | A | C |
| ATOM | 5520 | CD1 | TYR | A | 360 | 48.097 | −0.026 | −17.321 | 1.00 | 12.29 | A | C |
| ATOM | 5522 | CE1 | TYR | A | 360 | 48.666 | 0.360 | −18.518 | 1.00 | 9.88 | A | C |
| ATOM | 5524 | CZ | TYR | A | 360 | 50.010 | 0.118 | −18.751 | 1.00 | 13.42 | A | C |
| ATOM | 5525 | OH | TYR | A | 360 | 50.565 | 0.520 | −19.932 | 1.00 | 16.96 | A | O |
| ATOM | 5527 | CE2 | TYR | A | 360 | 50.790 | −0.485 | −17.786 | 1.00 | 8.89 | A | C |
| ATOM | 5529 | CD2 | TYR | A | 360 | 50.203 | −0.861 | −16.568 | 1.00 | 13.09 | A | C |
| ATOM | 5531 | C | TYR | A | 360 | 48.519 | −3.512 | −15.761 | 1.00 | 19.61 | A | C |
| ATOM | 5532 | O | TYR | A | 360 | 48.396 | −3.939 | −16.901 | 1.00 | 21.66 | A | O |
| ATOM | 5534 | N | ASP | A | 361 | 49.453 | −3.976 | −14.931 | 1.00 | 20.81 | A | N |
| ATOM | 5535 | CA | ASP | A | 361 | 50.465 | −4.969 | −15.377 | 1.00 | 22.44 | A | C |
| ATOM | 5537 | CB | ASP | A | 361 | 51.307 | −5.501 | −14.218 | 1.00 | 23.16 | A | C |
| ATOM | 5540 | CG | ASP | A | 361 | 52.175 | −4.431 | −13.551 | 1.00 | 29.65 | A | C |
| ATOM | 5541 | OD1 | ASP | A | 361 | 52.375 | −3.309 | −14.095 | 1.00 | 30.92 | A | O |
| ATOM | 5542 | OD2 | ASP | A | 361 | 52.684 | −4.754 | −12.462 | 1.00 | 39.54 | A | O |
| ATOM | 5543 | C | ASP | A | 361 | 49.828 | −6.163 | −16.063 | 1.00 | 21.86 | A | C |
| ATOM | 5544 | O | ASP | A | 361 | 50.296 | −6.612 | −17.095 | 1.00 | 20.13 | A | O |
| ATOM | 5546 | N | ASN | A | 362 | 48.751 | −6.668 | −15.482 | 1.00 | 22.54 | A | N |
| ATOM | 5547 | CA | ASN | A | 362 | 48.066 | −7.813 | −16.036 | 1.00 | 23.29 | A | C |
| ATOM | 5549 | CB | ASN | A | 362 | 47.121 | −8.407 | −15.005 | 1.00 | 26.74 | A | C |
| ATOM | 5552 | CG | ASN | A | 362 | 47.831 | −9.340 | −14.072 | 1.00 | 27.43 | A | C |
| ATOM | 5553 | OD1 | ASN | A | 362 | 47.917 | −10.526 | −14.337 | 1.00 | 26.92 | A | O |
| ATOM | 5554 | ND2 | ASN | A | 362 | 48.403 | −8.797 | −13.004 | 1.00 | 30.27 | A | N |
| ATOM | 5557 | C | ASN | A | 362 | 47.324 | −7.491 | −17.322 | 1.00 | 24.48 | A | C |
| ATOM | 5558 | O | ASN | A | 362 | 47.420 | −8.243 | −18.278 | 1.00 | 23.43 | A | O |
| ATOM | 5560 | N | LEU | A | 363 | 46.628 | −6.354 | −17.362 | 1.00 | 23.94 | A | N |
| ATOM | 5561 | CA | LEU | A | 363 | 45.966 | −5.918 | −18.581 | 1.00 | 22.60 | A | C |
| ATOM | 5563 | CB | LEU | A | 363 | 45.287 | −4.570 | −18.389 | 1.00 | 20.18 | A | C |
| ATOM | 5566 | CG | LEU | A | 363 | 44.590 | −3.967 | −19.601 | 1.00 | 23.96 | A | C |
| ATOM | 5568 | CD1 | LEU | A | 363 | 43.503 | −4.907 | −20.108 | 1.00 | 14.88 | A | C |

TABLE 4-2-continued

Coordinates of *P. alba* IspS

| ATOM | 5572 | CD2 | LEU | A | 363 | 44.030 | −2.552 | −19.279 | 1.00 | 17.49 | A | C |
|---|---|---|---|---|---|---|---|---|---|---|---|---|
| ATOM | 5576 | C | LEU | A | 363 | 46.985 | −5.838 | −19.707 | 1.00 | 23.16 | A | C |
| ATOM | 5577 | O | LEU | A | 363 | 46.734 | −6.307 | −20.800 | 1.00 | 24.96 | A | O |
| ATOM | 5579 | N | LYS | A | 364 | 48.143 | −5.263 | −19.432 | 1.00 | 24.48 | A | N |
| ATOM | 5580 | CA | LYS | A | 364 | 49.149 | −5.054 | −20.469 | 1.00 | 23.95 | A | C |
| ATOM | 5582 | CB | LYS | A | 364 | 50.288 | −4.165 | −19.964 | 1.00 | 23.52 | A | C |
| ATOM | 5585 | CG | LYS | A | 364 | 51.326 | −3.846 | −21.033 | 1.00 | 28.36 | A | C |
| ATOM | 5588 | CD | LYS | A | 364 | 52.416 | −2.904 | −20.568 | 1.00 | 33.18 | A | C |
| ATOM | 5591 | CE | LYS | A | 364 | 53.575 | −3.616 | −19.903 | 1.00 | 29.42 | A | C |
| ATOM | 5594 | NZ | LYS | A | 364 | 53.277 | −3.791 | −18.504 | 1.00 | 34.02 | A | N |
| ATOM | 5598 | C | LYS | A | 364 | 49.752 | −6.361 | −20.967 | 1.00 | 25.61 | A | C |
| ATOM | 5599 | O | LYS | A | 364 | 50.000 | −6.488 | −22.163 | 1.00 | 24.47 | A | O |
| ATOM | 5601 | N | ASP | A | 365 | 50.020 | −7.304 | −20.053 | 1.00 | 26.63 | A | N |
| ATOM | 5602 | CA | ASP | A | 365 | 50.760 | −8.530 | −20.395 | 1.00 | 29.60 | A | C |
| ATOM | 5604 | CB | ASP | A | 365 | 51.663 | −8.970 | −19.235 | 1.00 | 28.67 | A | C |
| ATOM | 5607 | CG | ASP | A | 365 | 52.733 | −7.936 | −18.896 | 1.00 | 38.74 | A | C |
| ATOM | 5608 | OD1 | ASP | A | 365 | 52.986 | −7.008 | −19.711 | 1.00 | 45.92 | A | O |
| ATOM | 5609 | OD2 | ASP | A | 365 | 53.314 | −8.040 | −17.799 | 1.00 | 47.56 | A | O |
| ATOM | 5610 | C | ASP | A | 365 | 49.867 | −9.705 | −20.793 | 1.00 | 30.41 | A | C |
| ATOM | 5611 | O | ASP | A | 365 | 50.295 | −10.549 | −21.574 | 1.00 | 30.84 | A | O |
| ATOM | 5613 | N | LYS | A | 366 | 48.655 | −9.775 | −20.238 | 1.00 | 29.91 | A | N |
| ATOM | 5614 | CA | LYS | A | 366 | 47.732 | −10.890 | −20.515 | 1.00 | 31.66 | A | C |
| ATOM | 5616 | CB | LYS | A | 366 | 47.282 | −11.573 | −19.222 | 1.00 | 31.27 | A | C |
| ATOM | 5619 | CG | LYS | A | 366 | 48.393 | −12.030 | −18.325 | 1.00 | 37.24 | A | C |
| ATOM | 5622 | CD | LYS | A | 366 | 47.831 | −12.620 | −17.023 | 1.00 | 51.74 | A | C |
| ATOM | 5625 | CE | LYS | A | 366 | 48.938 | −13.013 | −16.050 | 1.00 | 58.01 | A | C |
| ATOM | 5628 | NZ | LYS | A | 366 | 49.938 | −13.909 | −16.721 | 1.00 | 65.78 | A | N |
| ATOM | 5632 | C | LYS | A | 366 | 46.493 | −10.433 | −21.260 | 1.00 | 31.36 | A | C |
| ATOM | 5633 | O | LYS | A | 366 | 45.638 | −11.244 | −21.579 | 1.00 | 34.55 | A | O |
| ATOM | 5635 | N | GLY | A | 367 | 46.372 | −9.139 | −21.516 | 1.00 | 29.56 | A | N |
| ATOM | 5636 | CA | GLY | A | 367 | 45.215 | −8.637 | −22.233 | 1.00 | 28.57 | A | C |
| ATOM | 5639 | C | GLY | A | 367 | 43.893 | −8.799 | −21.503 | 1.00 | 28.83 | A | C |
| ATOM | 5640 | O | GLY | A | 367 | 42.846 | −8.755 | −22.145 | 1.00 | 29.71 | A | O |
| ATOM | 5642 | N | GLU | A | 368 | 43.921 | −8.940 | −20.174 | 1.00 | 27.22 | A | N |
| ATOM | 5643 | CA | GLU | A | 368 | 42.685 | −9.147 | −19.396 | 1.00 | 27.74 | A | C |
| ATOM | 5645 | CB | GLU | A | 368 | 42.648 | −10.563 | −18.784 | 1.00 | 28.93 | A | C |
| ATOM | 5648 | CG | GLU | A | 368 | 42.646 | −11.732 | −19.784 | 1.00 | 38.81 | A | C |
| ATOM | 5651 | CD | GLU | A | 368 | 41.343 | −11.888 | −20.567 | 1.00 | 47.54 | A | C |
| ATOM | 5652 | OE1 | GLU | A | 368 | 40.389 | −11.104 | −20.360 | 1.00 | 49.64 | A | O |
| ATOM | 5653 | OE2 | GLU | A | 368 | 41.284 | −12.808 | −21.410 | 1.00 | 54.32 | A | O |
| ATOM | 5654 | C | GLU | A | 368 | 42.543 | −8.135 | −18.268 | 1.00 | 24.49 | A | C |
| ATOM | 5655 | O | GLU | A | 368 | 43.499 | −7.861 | −17.565 | 1.00 | 25.04 | A | O |
| ATOM | 5657 | N | ASN | A | 369 | 41.345 | −7.610 | −18.068 | 1.00 | 23.64 | A | N |
| ATOM | 5658 | CA | ASN | A | 369 | 41.070 | −6.743 | −16.922 | 1.00 | 23.23 | A | C |
| ATOM | 5660 | CB | ASN | A | 369 | 39.965 | −5.744 | −17.246 | 1.00 | 23.47 | A | C |
| ATOM | 5663 | CG | ASN | A | 369 | 39.625 | −4.846 | −16.059 | 1.00 | 26.64 | A | C |
| ATOM | 5664 | OD1 | ASN | A | 369 | 40.103 | −5.046 | −14.935 | 1.00 | 27.47 | A | O |
| ATOM | 5665 | ND2 | ASN | A | 369 | 38.801 | −3.848 | −16.310 | 1.00 | 21.10 | A | N |
| ATOM | 5668 | C | ASN | A | 369 | 40.646 | −7.564 | −15.716 | 1.00 | 22.50 | A | C |
| ATOM | 5669 | O | ASN | A | 369 | 39.515 | −8.037 | −15.662 | 1.00 | 23.28 | A | O |
| ATOM | 5671 | N | ILE | A | 370 | 41.548 | −7.697 | −14.749 | 1.00 | 20.03 | A | N |
| ATOM | 5672 | CA | ILE | A | 370 | 41.339 | −8.531 | −13.587 | 1.00 | 20.96 | A | C |
| ATOM | 5674 | CB | ILE | A | 370 | 42.596 | −9.422 | −13.301 | 1.00 | 22.00 | A | C |
| ATOM | 5676 | CG1 | ILE | A | 370 | 43.822 | −8.555 | −12.918 | 1.00 | 22.25 | A | C |
| ATOM | 5679 | CD1 | ILE | A | 370 | 44.991 | −9.307 | −12.305 | 1.00 | 24.22 | A | C |
| ATOM | 5683 | CG2 | ILE | A | 370 | 42.925 | −10.275 | −14.521 | 1.00 | 22.49 | A | C |
| ATOM | 5687 | C | ILE | A | 370 | 41.038 | −7.700 | −12.345 | 1.00 | 22.36 | A | C |
| ATOM | 5688 | O | ILE | A | 370 | 40.934 | −8.245 | −11.246 | 1.00 | 23.94 | A | O |
| ATOM | 5690 | N | LEU | A | 371 | 40.927 | −6.388 | −12.500 | 1.00 | 21.80 | A | N |
| ATOM | 5691 | CA | LEU | A | 371 | 40.640 | −5.508 | −11.350 | 1.00 | 22.30 | A | C |
| ATOM | 5693 | CB | LEU | A | 371 | 40.420 | −4.071 | −11.808 | 1.00 | 20.64 | A | C |
| ATOM | 5696 | CG | LEU | A | 371 | 40.364 | −3.036 | −10.684 | 1.00 | 22.73 | A | C |
| ATOM | 5698 | CD1 | LEU | A | 371 | 41.588 | −3.133 | −9.844 | 1.00 | 17.10 | A | C |
| ATOM | 5702 | CD2 | LEU | A | 371 | 40.230 | −1.641 | −11.247 | 1.00 | 17.41 | A | C |
| ATOM | 5706 | C | LEU | A | 371 | 39.477 | −5.941 | −10.442 | 1.00 | 22.81 | A | C |
| ATOM | 5707 | O | LEU | A | 371 | 39.636 | −5.947 | −9.221 | 1.00 | 25.48 | A | O |
| ATOM | 5709 | N | PRO | A | 372 | 38.323 | −6.322 | −11.018 | 1.00 | 24.23 | A | N |
| ATOM | 5710 | CA | PRO | A | 372 | 37.194 | −6.750 | −10.172 | 1.00 | 24.59 | A | C |
| ATOM | 5712 | CB | PRO | A | 372 | 36.136 | −7.207 | −11.186 | 1.00 | 25.42 | A | C |
| ATOM | 5715 | CG | PRO | A | 372 | 36.502 | −6.557 | −12.470 | 1.00 | 27.16 | A | C |
| ATOM | 5718 | CD | PRO | A | 372 | 37.991 | −6.388 | −12.457 | 1.00 | 26.65 | A | C |
| ATOM | 5721 | C | PRO | A | 372 | 37.520 | −7.921 | −9.235 | 1.00 | 24.27 | A | C |
| ATOM | 5722 | O | PRO | A | 372 | 36.936 | −8.036 | −8.165 | 1.00 | 24.63 | A | O |
| ATOM | 5723 | N | TYR | A | 373 | 38.444 | −8.778 | −9.629 | 1.00 | 22.56 | A | N |
| ATOM | 5724 | CA | TYR | A | 373 | 38.785 | −9.923 | −8.804 | 1.00 | 23.41 | A | C |
| ATOM | 5726 | CB | TYR | A | 373 | 39.355 | −11.030 | −9.678 | 1.00 | 25.44 | A | C |
| ATOM | 5729 | CG | TYR | A | 373 | 38.520 | −11.288 | −10.950 | 1.00 | 28.81 | A | C |
| ATOM | 5730 | CD1 | TYR | A | 373 | 37.220 | −11.783 | −10.877 | 1.00 | 39.04 | A | C |

TABLE 4-2-continued

Coordinates of *P. alba* IspS

| ATOM | 5732 | CE1 | TYR | A | 373 | 36.452 | -12.013 | -12.040 | 1.00 | 38.13 | A | C |
|---|---|---|---|---|---|---|---|---|---|---|---|---|
| ATOM | 5734 | CZ | TYR | A | 373 | 36.999 | -11.743 | -13.272 | 1.00 | 39.16 | A | C |
| ATOM | 5735 | OH | TYR | A | 373 | 36.279 | -11.950 | -14.425 | 1.00 | 47.13 | A | O |
| ATOM | 5737 | CE2 | TYR | A | 373 | 38.284 | -11.243 | -13.361 | 1.00 | 40.64 | A | C |
| ATOM | 5739 | CD2 | TYR | A | 373 | 39.037 | -11.025 | -12.208 | 1.00 | 30.70 | A | C |
| ATOM | 5741 | C | TYR | A | 373 | 39.750 | -9.516 | -7.676 | 1.00 | 24.07 | A | C |
| ATOM | 5742 | O | TYR | A | 373 | 39.657 | -10.021 | -6.574 | 1.00 | 24.75 | A | O |
| ATOM | 5744 | N | LEU | A | 374 | 40.640 | -8.562 | -7.935 | 1.00 | 21.92 | A | N |
| ATOM | 5745 | CA | LEU | A | 374 | 41.543 | -8.065 | -6.904 | 1.00 | 20.05 | A | C |
| ATOM | 5747 | CB | LEU | A | 374 | 42.697 | -7.268 | -7.533 | 1.00 | 18.59 | A | C |
| ATOM | 5750 | CG | LEU | A | 374 | 43.440 | -7.920 | -8.708 | 1.00 | 21.18 | A | C |
| ATOM | 5752 | CD1 | LEU | A | 374 | 44.568 | -7.012 | -9.281 | 1.00 | 15.63 | A | C |
| ATOM | 5756 | CD2 | LEU | A | 374 | 44.002 | -9.288 | -8.329 | 1.00 | 21.62 | A | C |
| ATOM | 5760 | C | LEU | A | 374 | 40.748 | -7.194 | -5.916 | 1.00 | 19.90 | A | C |
| ATOM | 5761 | O | LEU | A | 374 | 40.908 | -7.312 | -4.711 | 1.00 | 21.65 | A | O |
| ATOM | 5763 | N | THR | A | 375 | 39.875 | -6.324 | -6.403 | 1.00 | 19.48 | A | N |
| ATOM | 5764 | CA | THR | A | 375 | 39.118 | -5.465 | -5.482 | 1.00 | 20.29 | A | C |
| ATOM | 5766 | CB | THR | A | 375 | 38.419 | -4.297 | -6.219 | 1.00 | 21.53 | A | C |
| ATOM | 5768 | OG1 | THR | A | 375 | 37.533 | -4.818 | -7.222 | 1.00 | 23.71 | A | O |
| ATOM | 5770 | CG2 | THR | A | 375 | 39.458 | -3.379 | -6.875 | 1.00 | 17.49 | A | C |
| ATOM | 5774 | C | THR | A | 375 | 38.093 | -6.269 | -4.665 | 1.00 | 20.82 | A | C |
| ATOM | 5775 | O | THR | A | 375 | 37.854 | -5.989 | -3.499 | 1.00 | 23.34 | A | O |
| ATOM | 5777 | N | LYS | A | 376 | 37.510 | -7.299 | -5.243 | 1.00 | 21.46 | A | N |
| ATOM | 5778 | CA | LYS | A | 376 | 36.592 | -8.149 | -4.476 | 1.00 | 22.11 | A | C |
| ATOM | 5780 | CB | LYS | A | 376 | 35.915 | -9.162 | -5.411 | 1.00 | 24.77 | A | C |
| ATOM | 5783 | CG | LYS | A | 376 | 35.075 | -10.225 | -4.732 | 1.00 | 30.99 | A | C |
| ATOM | 5786 | CD | LYS | A | 376 | 33.828 | -9.640 | -4.119 | 1.00 | 37.68 | A | C |
| ATOM | 5789 | CE | LYS | A | 376 | 32.933 | -10.753 | -3.552 | 1.00 | 43.15 | A | C |
| ATOM | 5792 | NZ | LYS | A | 376 | 32.101 | -10.264 | -2.422 | 1.00 | 47.30 | A | N |
| ATOM | 5796 | C | LYS | A | 376 | 37.324 | -8.858 | -3.345 | 1.00 | 20.58 | A | C |
| ATOM | 5797 | O | LYS | A | 376 | 36.805 | -8.964 | -2.259 | 1.00 | 22.25 | A | O |
| ATOM | 5799 | N | ALA | A | 377 | 38.522 | -9.369 | -3.612 | 1.00 | 20.81 | A | N |
| ATOM | 5800 | CA | ALA | A | 377 | 39.307 | -10.072 | -2.597 | 1.00 | 19.65 | A | C |
| ATOM | 5802 | CB | ALA | A | 377 | 40.581 | -10.615 | -3.187 | 1.00 | 20.54 | A | C |
| ATOM | 5806 | C | ALA | A | 377 | 39.635 | -9.157 | -1.438 | 1.00 | 22.21 | A | C |
| ATOM | 5807 | O | ALA | A | 377 | 39.599 | -9.577 | -0.265 | 1.00 | 24.06 | A | O |
| ATOM | 5809 | N | TRP | A | 378 | 39.918 | -7.892 | -1.748 | 1.00 | 20.95 | A | N |
| ATOM | 5810 | CA | TRP | A | 378 | 40.154 | -6.899 | -0.686 | 1.00 | 19.91 | A | C |
| ATOM | 5812 | CB | TRP | A | 378 | 40.823 | -5.645 | -1.240 | 1.00 | 19.12 | A | C |
| ATOM | 5815 | CG | TRP | A | 378 | 42.266 | -5.807 | -1.234 | 1.00 | 18.82 | A | C |
| ATOM | 5816 | CD1 | TRP | A | 378 | 43.045 | -6.192 | -2.261 | 1.00 | 17.16 | A | C |
| ATOM | 5818 | NE1 | TRP | A | 378 | 44.343 | -6.281 | -1.858 | 1.00 | 20.04 | A | N |
| ATOM | 5820 | CE2 | TRP | A | 378 | 44.416 | -5.964 | -0.528 | 1.00 | 15.91 | A | C |
| ATOM | 5821 | CD2 | TRP | A | 378 | 43.115 | -5.692 | -0.098 | 1.00 | 19.67 | A | C |
| ATOM | 5822 | CE3 | TRP | A | 378 | 42.903 | -5.345 | 1.237 | 1.00 | 17.94 | A | C |
| ATOM | 5824 | CZ3 | TRP | A | 378 | 43.989 | -5.290 | 2.080 | 1.00 | 22.51 | A | C |
| ATOM | 5826 | CH2 | TRP | A | 378 | 45.271 | -5.571 | 1.624 | 1.00 | 15.95 | A | C |
| ATOM | 5828 | CZ2 | TRP | A | 378 | 45.510 | -5.902 | 0.324 | 1.00 | 15.79 | A | C |
| ATOM | 5830 | C | TRP | A | 378 | 38.908 | -6.516 | 0.109 | 1.00 | 19.57 | A | C |
| ATOM | 5831 | O | TRP | A | 378 | 38.994 | -6.297 | 1.313 | 1.00 | 19.10 | A | O |
| ATOM | 5833 | N | ALA | A | 379 | 37.779 | -6.386 | -0.577 | 1.00 | 17.51 | A | N |
| ATOM | 5834 | CA | ALA | A | 379 | 36.511 | -6.130 | 0.083 | 1.00 | 18.56 | A | C |
| ATOM | 5836 | CB | ALA | A | 379 | 35.377 | -5.971 | -0.957 | 1.00 | 19.21 | A | C |
| ATOM | 5840 | C | ALA | A | 379 | 36.179 | -7.267 | 1.040 | 1.00 | 20.27 | A | C |
| ATOM | 5841 | O | ALA | A | 379 | 35.706 | -7.046 | 2.155 | 1.00 | 22.16 | A | O |
| ATOM | 5843 | N | ASP | A | 380 | 36.405 | -8.495 | 0.601 | 1.00 | 20.50 | A | N |
| ATOM | 5844 | CA | ASP | A | 380 | 36.081 | -9.638 | 1.448 | 1.00 | 21.17 | A | C |
| ATOM | 5846 | CB | ASP | A | 380 | 36.238 | -10.964 | 0.695 | 1.00 | 21.00 | A | C |
| ATOM | 5849 | CG | ASP | A | 380 | 35.187 | -11.187 | -0.412 | 1.00 | 21.43 | A | C |
| ATOM | 5850 | OD1 | ASP | A | 380 | 34.167 | -10.468 | -0.515 | 1.00 | 25.52 | A | O |
| ATOM | 5851 | OD2 | ASP | A | 380 | 35.379 | -12.153 | -1.177 | 1.00 | 29.89 | A | O |
| ATOM | 5852 | C | ASP | A | 380 | 37.009 | -9.625 | 2.662 | 1.00 | 21.11 | A | C |
| ATOM | 5853 | O | ASP | A | 380 | 36.589 | -9.925 | 3.778 | 1.00 | 25.31 | A | O |
| ATOM | 5855 | N | LEU | A | 381 | 38.273 | -9.283 | 2.456 | 1.00 | 21.14 | A | N |
| ATOM | 5856 | CA | LEU | A | 381 | 39.216 | -9.230 | 3.581 | 1.00 | 20.85 | A | C |
| ATOM | 5858 | CB | LEU | A | 381 | 40.641 | -8.952 | 3.113 | 1.00 | 19.68 | A | C |
| ATOM | 5861 | CG | LEU | A | 381 | 41.690 | -8.904 | 4.212 | 1.00 | 22.69 | A | C |
| ATOM | 5863 | CD1 | LEU | A | 381 | 41.645 | -10.153 | 5.076 | 1.00 | 17.32 | A | C |
| ATOM | 5867 | CD2 | LEU | A | 381 | 43.038 | -8.730 | 3.552 | 1.00 | 20.69 | A | C |
| ATOM | 5871 | C | LEU | A | 381 | 38.781 | -8.183 | 4.584 | 1.00 | 18.62 | A | C |
| ATOM | 5872 | O | LEU | A | 381 | 38.690 | -8.459 | 5.778 | 1.00 | 20.47 | A | O |
| ATOM | 5874 | N | CYS | A | 382 | 38.457 | -6.990 | 4.102 | 1.00 | 21.03 | A | N |
| ATOM | 5875 | CA | CYS | A | 382 | 38.090 | -5.891 | 5.023 | 1.00 | 20.56 | A | C |
| ATOM | 5877 | CB | CYS | A | 382 | 38.032 | -4.551 | 4.283 | 1.00 | 21.31 | A | C |
| ATOM | 5880 | SG | CYS | A | 382 | 39.664 | -3.962 | 3.712 | 1.00 | 24.85 | A | S |
| ATOM | 5882 | C | CYS | A | 382 | 36.799 | -6.217 | 5.764 | 1.00 | 19.73 | A | C |
| ATOM | 5883 | O | CYS | A | 382 | 36.676 | -5.968 | 6.959 | 1.00 | 23.50 | A | O |
| ATOM | 5885 | N | ASN | A | 383 | 35.850 | -6.829 | 5.080 | 1.00 | 21.14 | A | N |

TABLE 4-2-continued

Coordinates of *P. alba* IspS

| ATOM | 5886 | CA | ASN | A | 383 | 34.646 | −7.367 | 5.742 | 1.00 | 21.35 | A | C |
|---|---|---|---|---|---|---|---|---|---|---|---|---|
| ATOM | 5888 | CB | ASN | A | 383 | 33.630 | −7.901 | 4.721 | 1.00 | 21.45 | A | C |
| ATOM | 5891 | CG | ASN | A | 383 | 32.701 | −6.810 | 4.213 | 1.00 | 26.00 | A | C |
| ATOM | 5892 | OD1 | ASN | A | 383 | 31.849 | −6.300 | 4.960 | 1.00 | 32.37 | A | O |
| ATOM | 5893 | ND2 | ASN | A | 383 | 32.875 | −6.426 | 2.948 | 1.00 | 24.66 | A | N |
| ATOM | 5896 | C | ASN | A | 383 | 34.936 | −8.458 | 6.753 | 1.00 | 21.61 | A | C |
| ATOM | 5897 | O | ASN | A | 383 | 34.282 | −8.523 | 7.780 | 1.00 | 22.90 | A | O |
| ATOM | 5899 | N | ALA | A | 384 | 35.900 | −9.328 | 6.486 | 1.00 | 21.49 | A | N |
| ATOM | 5900 | CA | ALA | A | 384 | 36.234 | −10.330 | 7.505 | 1.00 | 19.41 | A | C |
| ATOM | 5902 | CB | ALA | A | 384 | 37.163 | −11.414 | 6.934 | 1.00 | 15.55 | A | C |
| ATOM | 5906 | C | ALA | A | 384 | 36.851 | −9.602 | 8.744 | 1.00 | 18.65 | A | C |
| ATOM | 5907 | O | ALA | A | 384 | 36.449 | −9.851 | 9.886 | 1.00 | 18.75 | A | O |
| ATOM | 5909 | N | PHE | A | 385 | 37.785 | −8.682 | 8.517 | 1.00 | 18.91 | A | N |
| ATOM | 5910 | CA | PHE | A | 385 | 38.319 | −7.831 | 9.626 | 1.00 | 20.64 | A | C |
| ATOM | 5912 | CB | PHE | A | 385 | 39.311 | −6.773 | 9.127 | 1.00 | 21.86 | A | C |
| ATOM | 5915 | CG | PHE | A | 385 | 40.647 | −7.296 | 8.653 | 1.00 | 18.71 | A | C |
| ATOM | 5916 | CD1 | PHE | A | 385 | 41.305 | −8.317 | 9.312 | 1.00 | 27.92 | A | C |
| ATOM | 5918 | CE1 | PHE | A | 385 | 42.566 | −8.754 | 8.889 | 1.00 | 23.74 | A | C |
| ATOM | 5920 | CZ | PHE | A | 385 | 43.190 | −8.126 | 7.810 | 1.00 | 25.70 | A | C |
| ATOM | 5922 | CE2 | PHE | A | 385 | 42.544 | −7.058 | 7.171 | 1.00 | 24.54 | A | C |
| ATOM | 5924 | CD2 | PHE | A | 385 | 41.296 | −6.652 | 7.608 | 1.00 | 22.39 | A | C |
| ATOM | 5926 | C | PHE | A | 385 | 37.199 | −7.059 | 10.362 | 1.00 | 21.40 | A | C |
| ATOM | 5927 | O | PHE | A | 385 | 37.158 | −7.013 | 11.590 | 1.00 | 24.82 | A | O |
| ATOM | 5929 | N | LEU | A | 386 | 36.293 | −6.439 | 9.621 | 1.00 | 21.38 | A | N |
| ATOM | 5930 | CA | LEU | A | 386 | 35.174 | −5.721 | 10.254 | 1.00 | 20.88 | A | C |
| ATOM | 5932 | CB | LEU | A | 386 | 34.226 | −5.138 | 9.186 | 1.00 | 20.67 | A | C |
| ATOM | 5935 | CG | LEU | A | 386 | 33.068 | −4.256 | 9.667 | 1.00 | 24.05 | A | C |
| ATOM | 5937 | CD1 | LEU | A | 386 | 33.624 | −2.975 | 10.307 | 1.00 | 17.84 | A | C |
| ATOM | 5941 | CD2 | LEU | A | 386 | 32.096 | −3.922 | 8.539 | 1.00 | 14.02 | A | C |
| ATOM | 5945 | C | LEU | A | 386 | 34.390 | −6.629 | 11.200 | 1.00 | 20.84 | A | C |
| ATOM | 5946 | O | LEU | A | 386 | 34.093 | −6.263 | 12.350 | 1.00 | 22.03 | A | O |
| ATOM | 5948 | N | GLN | A | 387 | 34.050 | −7.816 | 10.725 | 1.00 | 21.21 | A | N |
| ATOM | 5949 | CA | GLN | A | 387 | 33.315 | −8.754 | 11.561 | 1.00 | 22.62 | A | C |
| ATOM | 5951 | CB | GLN | A | 387 | 33.016 | −10.052 | 10.816 | 1.00 | 23.54 | A | C |
| ATOM | 5954 | CG | GLN | A | 387 | 32.222 | −11.067 | 11.634 | 1.00 | 23.83 | A | C |
| ATOM | 5957 | CD | GLN | A | 387 | 30.830 | −10.587 | 11.951 | 1.00 | 23.98 | A | C |
| ATOM | 5958 | OE1 | GLN | A | 387 | 30.560 | −10.108 | 13.050 | 1.00 | 26.91 | A | O |
| ATOM | 5959 | NE2 | GLN | A | 387 | 29.933 | −10.715 | 10.987 | 1.00 | 30.18 | A | N |
| ATOM | 5962 | C | GLN | A | 387 | 34.082 | −9.045 | 12.847 | 1.00 | 23.68 | A | C |
| ATOM | 5963 | O | GLN | A | 387 | 33.491 | −9.080 | 13.933 | 1.00 | 21.96 | A | O |
| ATOM | 5965 | N | GLU | A | 388 | 35.393 | −9.237 | 12.738 | 1.00 | 24.58 | A | N |
| ATOM | 5966 | CA | GLU | A | 388 | 36.209 | −9.469 | 13.935 | 1.00 | 24.13 | A | C |
| ATOM | 5968 | CB | GLU | A | 388 | 37.684 | −9.705 | 13.601 | 1.00 | 23.71 | A | C |
| ATOM | 5971 | CG | GLU | A | 388 | 37.932 | −11.099 | 13.059 | 1.00 | 31.30 | A | C |
| ATOM | 5974 | CD | GLU | A | 388 | 39.385 | −11.373 | 12.675 | 1.00 | 36.02 | A | C |
| ATOM | 5975 | OE1 | GLU | A | 388 | 40.209 | −10.407 | 12.511 | 1.00 | 32.55 | A | O |
| ATOM | 5976 | OE2 | GLU | A | 388 | 39.674 | −12.582 | 12.531 | 1.00 | 30.48 | A | O |
| ATOM | 5977 | C | GLU | A | 388 | 36.108 | −8.308 | 14.885 | 1.00 | 21.29 | A | C |
| ATOM | 5978 | O | GLU | A | 388 | 35.996 | −8.503 | 16.091 | 1.00 | 19.35 | A | O |
| ATOM | 5980 | N | ALA | A | 389 | 36.164 | −7.098 | 14.343 | 1.00 | 20.43 | A | N |
| ATOM | 5981 | CA | ALA | A | 389 | 36.155 | −5.918 | 15.196 | 1.00 | 19.95 | A | C |
| ATOM | 5983 | CB | ALA | A | 389 | 36.443 | −4.670 | 14.404 | 1.00 | 17.61 | A | C |
| ATOM | 5987 | C | ALA | A | 389 | 34.797 | −5.816 | 15.883 | 1.00 | 20.79 | A | C |
| ATOM | 5988 | O | ALA | A | 389 | 34.724 | −5.453 | 17.045 | 1.00 | 22.39 | A | O |
| ATOM | 5990 | N | LYS | A | 390 | 33.729 | −6.150 | 15.162 | 1.00 | 21.47 | A | N |
| ATOM | 5991 | CA | LYS | A | 390 | 32.387 | −6.056 | 15.711 | 1.00 | 22.95 | A | C |
| ATOM | 5993 | CB | LYS | A | 390 | 31.347 | −6.272 | 14.611 | 1.00 | 22.84 | A | C |
| ATOM | 5996 | CG | LYS | A | 390 | 31.150 | −5.048 | 13.739 | 1.00 | 25.85 | A | C |
| ATOM | 5999 | CD | LYS | A | 390 | 30.033 | −5.259 | 12.719 | 1.00 | 33.32 | A | C |
| ATOM | 6002 | CE | LYS | A | 390 | 29.796 | −4.002 | 11.896 | 1.00 | 31.02 | A | C |
| ATOM | 6005 | NZ | LYS | A | 390 | 28.888 | −4.249 | 10.737 | 1.00 | 29.50 | A | N |
| ATOM | 6009 | C | LYS | A | 390 | 32.187 | −7.065 | 16.837 | 1.00 | 24.05 | A | C |
| ATOM | 6010 | O | LYS | A | 390 | 31.632 | −6.753 | 17.885 | 1.00 | 24.65 | A | O |
| ATOM | 6012 | N | TRP | A | 391 | 32.641 | −8.283 | 16.616 | 1.00 | 24.13 | A | N |
| ATOM | 6013 | CA | TRP | A | 391 | 32.563 | −9.303 | 17.650 | 1.00 | 24.58 | A | C |
| ATOM | 6015 | CB | TRP | A | 391 | 33.143 | −10.619 | 17.154 | 1.00 | 23.28 | A | C |
| ATOM | 6018 | CG | TRP | A | 391 | 32.225 | −11.389 | 16.264 | 1.00 | 23.35 | A | C |
| ATOM | 6019 | CD1 | TRP | A | 391 | 30.864 | −11.354 | 16.250 | 1.00 | 21.14 | A | C |
| ATOM | 6021 | NE1 | TRP | A | 391 | 30.373 | −12.235 | 15.311 | 1.00 | 24.01 | A | N |
| ATOM | 6023 | CE2 | TRP | A | 391 | 31.428 | −12.876 | 14.721 | 1.00 | 24.82 | A | C |
| ATOM | 6024 | CD2 | TRP | A | 391 | 32.610 | −12.365 | 15.298 | 1.00 | 19.00 | A | C |
| ATOM | 6025 | CE3 | TRP | A | 391 | 33.838 | −12.866 | 14.868 | 1.00 | 23.69 | A | C |
| ATOM | 6027 | CZ3 | TRP | A | 391 | 33.850 | −13.832 | 13.882 | 1.00 | 17.43 | A | C |
| ATOM | 6029 | CH2 | TRP | A | 391 | 32.657 | −14.317 | 13.325 | 1.00 | 20.76 | A | C |
| ATOM | 6031 | CZ2 | TRP | A | 391 | 31.444 | −13.852 | 13.722 | 1.00 | 22.46 | A | C |
| ATOM | 6033 | C | TRP | A | 391 | 33.288 | −8.885 | 18.920 | 1.00 | 25.69 | A | C |
| ATOM | 6034 | O | TRP | A | 391 | 32.775 | −9.100 | 20.029 | 1.00 | 25.53 | A | O |
| ATOM | 6036 | N | LEU | A | 392 | 34.463 | −8.286 | 18.764 | 1.00 | 25.73 | A | N |

TABLE 4-2-continued

Coordinates of *P. alba* IspS

| ATOM | 6037 | CA | LEU | A | 392 | 35.227 | −7.805 | 19.918 | 1.00 | 28.86 | A | C |
|---|---|---|---|---|---|---|---|---|---|---|---|---|
| ATOM | 6039 | CB | LEU | A | 392 | 36.604 | −7.319 | 19.470 | 1.00 | 30.60 | A | C |
| ATOM | 6042 | CG | LEU | A | 392 | 37.653 | −7.119 | 20.559 | 1.00 | 36.67 | A | C |
| ATOM | 6044 | CD1 | LEU | A | 392 | 39.053 | −7.245 | 19.946 | 1.00 | 40.63 | A | C |
| ATOM | 6048 | CD2 | LEU | A | 392 | 37.478 | −5.762 | 21.262 | 1.00 | 44.84 | A | C |
| ATOM | 6052 | C | LEU | A | 392 | 34.491 | −6.698 | 20.687 | 1.00 | 28.06 | A | C |
| ATOM | 6053 | O | LEU | A | 392 | 34.347 | −6.775 | 21.910 | 1.00 | 28.35 | A | O |
| ATOM | 6055 | N | TYR | A | 393 | 34.014 | −5.684 | 19.972 | 1.00 | 26.84 | A | N |
| ATOM | 6056 | CA | TYR | A | 393 | 33.328 | −4.551 | 20.604 | 1.00 | 27.94 | A | C |
| ATOM | 6058 | CB | TYR | A | 393 | 32.933 | −3.512 | 19.543 | 1.00 | 29.05 | A | C |
| ATOM | 6061 | CG | TYR | A | 393 | 32.189 | −2.306 | 20.078 | 1.00 | 33.13 | A | C |
| ATOM | 6062 | CD1 | TYR | A | 393 | 32.877 | −1.226 | 20.635 | 1.00 | 38.76 | A | C |
| ATOM | 6064 | CE1 | TYR | A | 393 | 32.198 | −0.112 | 21.146 | 1.00 | 40.86 | A | C |
| ATOM | 6066 | CZ | TYR | A | 393 | 30.817 | −0.066 | 21.085 | 1.00 | 42.91 | A | C |
| ATOM | 6067 | OH | TYR | A | 393 | 30.143 | 1.030 | 21.583 | 1.00 | 50.26 | A | O |
| ATOM | 6069 | CE2 | TYR | A | 393 | 30.107 | −1.123 | 20.526 | 1.00 | 40.58 | A | C |
| ATOM | 6071 | CD2 | TYR | A | 393 | 30.801 | −2.236 | 20.021 | 1.00 | 39.09 | A | C |
| ATOM | 6073 | C | TYR | A | 393 | 32.079 | −4.996 | 21.374 | 1.00 | 27.58 | A | C |
| ATOM | 6074 | O | TYR | A | 393 | 31.853 | −4.573 | 22.506 | 1.00 | 26.98 | A | O |
| ATOM | 6076 | N | ASN | A | 394 | 31.282 | −5.851 | 20.738 | 1.00 | 27.69 | A | N |
| ATOM | 6077 | CA | ASN | A | 394 | 30.010 | −6.312 | 21.272 | 1.00 | 27.80 | A | C |
| ATOM | 6079 | CB | ASN | A | 394 | 29.091 | −6.716 | 20.120 | 1.00 | 26.84 | A | C |
| ATOM | 6082 | CG | ASN | A | 394 | 28.616 | −5.521 | 19.324 | 1.00 | 28.06 | A | C |
| ATOM | 6083 | OD1 | ASN | A | 394 | 28.225 | −4.498 | 19.890 | 1.00 | 31.10 | A | O |
| ATOM | 6084 | ND2 | ASN | A | 394 | 28.644 | −5.636 | 18.010 | 1.00 | 32.05 | A | N |
| ATOM | 6087 | C | ASN | A | 394 | 30.156 | −7.458 | 22.261 | 1.00 | 29.31 | A | C |
| ATOM | 6088 | O | ASN | A | 394 | 29.158 | −7.944 | 22.801 | 1.00 | 29.60 | A | O |
| ATOM | 6090 | N | LYS | A | 395 | 31.402 | −7.865 | 22.511 | 1.00 | 30.96 | A | N |
| ATOM | 6091 | CA | LYS | A | 395 | 31.706 | −9.034 | 23.329 | 1.00 | 32.88 | A | C |
| ATOM | 6093 | CB | LYS | A | 395 | 31.443 | −8.749 | 24.815 | 1.00 | 34.38 | A | C |
| ATOM | 6096 | CG | LYS | A | 395 | 32.374 | −7.690 | 25.445 | 1.00 | 42.56 | A | C |
| ATOM | 6099 | CD | LYS | A | 395 | 31.603 | −6.475 | 25.978 | 1.00 | 50.78 | A | C |
| ATOM | 6102 | CE | LYS | A | 395 | 32.434 | −5.652 | 26.968 | 1.00 | 54.57 | A | C |
| ATOM | 6105 | NZ | LYS | A | 395 | 31.610 | −4.582 | 27.621 | 1.00 | 55.82 | A | N |
| ATOM | 6109 | C | LYS | A | 395 | 30.923 | −10.279 | 22.863 | 1.00 | 32.85 | A | C |
| ATOM | 6110 | O | LYS | A | 395 | 30.490 | −11.090 | 23.686 | 1.00 | 34.23 | A | O |
| ATOM | 6112 | N | SER | A | 396 | 30.765 | −10.431 | 21.546 | 1.00 | 31.79 | A | N |
| ATOM | 6113 | CA | SER | A | 396 | 30.034 | −11.571 | 20.970 | 1.00 | 30.45 | A | C |
| ATOM | 6115 | CB | SER | A | 396 | 29.868 | −11.402 | 19.464 | 1.00 | 29.95 | A | C |
| ATOM | 6118 | OG | SER | A | 396 | 29.007 | −10.318 | 19.148 | 1.00 | 31.64 | A | O |
| ATOM | 6120 | C | SER | A | 396 | 30.730 | −12.899 | 21.259 | 1.00 | 29.40 | A | C |
| ATOM | 6121 | O | SER | A | 396 | 31.933 | −12.948 | 21.512 | 1.00 | 31.77 | A | O |
| ATOM | 6123 | N | THR | A | 397 | 29.948 | −13.971 | 21.222 | 1.00 | 28.99 | A | N |
| ATOM | 6124 | CA | THR | A | 397 | 30.423 | −15.315 | 21.529 | 1.00 | 27.69 | A | C |
| ATOM | 6126 | CB | THR | A | 397 | 29.822 | −15.821 | 22.880 | 1.00 | 28.85 | A | C |
| ATOM | 6128 | OG1 | THR | A | 397 | 28.392 | −15.908 | 22.774 | 1.00 | 29.53 | A | O |
| ATOM | 6130 | CG2 | THR | A | 397 | 30.183 | −14.877 | 24.028 | 1.00 | 27.66 | A | C |
| ATOM | 6134 | C | THR | A | 397 | 30.017 | −16.273 | 20.407 | 1.00 | 26.90 | A | C |
| ATOM | 6135 | O | THR | A | 397 | 29.316 | −17.266 | 20.658 | 1.00 | 29.05 | A | O |
| ATOM | 6137 | N | PRO | A | 398 | 30.466 | −16.003 | 19.168 | 1.00 | 23.74 | A | N |
| ATOM | 6138 | CA | PRO | A | 398 | 30.051 | −16.849 | 18.046 | 1.00 | 23.94 | A | C |
| ATOM | 6140 | CB | PRO | A | 398 | 30.741 | −16.196 | 16.855 | 1.00 | 23.33 | A | C |
| ATOM | 6143 | CG | PRO | A | 398 | 32.020 | −15.684 | 17.456 | 1.00 | 24.23 | A | C |
| ATOM | 6146 | CD | PRO | A | 398 | 31.632 | −15.176 | 18.816 | 1.00 | 23.86 | A | C |
| ATOM | 6149 | C | PRO | A | 398 | 30.558 | −18.274 | 18.192 | 1.00 | 22.60 | A | C |
| ATOM | 6150 | O | PRO | A | 398 | 31.522 | −18.516 | 18.905 | 1.00 | 23.64 | A | O |
| ATOM | 6151 | N | THR | A | 399 | 29.918 | −19.210 | 17.511 | 1.00 | 22.40 | A | N |
| ATOM | 6152 | CA | THR | A | 399 | 30.354 | −20.602 | 17.542 | 1.00 | 21.81 | A | C |
| ATOM | 6154 | CB | THR | A | 399 | 29.367 | −21.499 | 16.770 | 1.00 | 23.98 | A | C |
| ATOM | 6156 | OG1 | THR | A | 399 | 29.377 | −21.129 | 15.376 | 1.00 | 24.75 | A | O |
| ATOM | 6158 | CG2 | THR | A | 399 | 27.909 | −21.381 | 17.366 | 1.00 | 14.91 | A | C |
| ATOM | 6162 | C | THR | A | 399 | 31.716 | −20.718 | 16.882 | 1.00 | 22.61 | A | C |
| ATOM | 6163 | O | THR | A | 399 | 32.127 | −19.807 | 16.181 | 1.00 | 26.36 | A | O |
| ATOM | 6165 | N | PHE | A | 400 | 32.411 | −21.839 | 17.094 | 1.00 | 23.40 | A | N |
| ATOM | 6166 | CA | PHE | A | 400 | 33.704 | −22.095 | 16.443 | 1.00 | 22.11 | A | C |
| ATOM | 6168 | CB | PHE | A | 400 | 34.252 | −23.474 | 16.814 | 1.00 | 22.13 | A | C |
| ATOM | 6171 | CG | PHE | A | 400 | 35.471 | −23.874 | 16.008 | 1.00 | 24.27 | A | C |
| ATOM | 6172 | CD1 | PHE | A | 400 | 36.709 | −23.344 | 16.297 | 1.00 | 25.15 | A | C |
| ATOM | 6174 | CE1 | PHE | A | 400 | 37.825 | −23.700 | 15.562 | 1.00 | 27.59 | A | C |
| ATOM | 6176 | CZ | PHE | A | 400 | 37.706 | −24.594 | 14.508 | 1.00 | 24.77 | A | C |
| ATOM | 6178 | CE2 | PHE | A | 400 | 36.485 | −25.112 | 14.212 | 1.00 | 26.28 | A | C |
| ATOM | 6180 | CD2 | PHE | A | 400 | 35.370 | −24.765 | 14.961 | 1.00 | 27.15 | A | C |
| ATOM | 6182 | C | PHE | A | 400 | 33.607 | −22.031 | 14.942 | 1.00 | 22.50 | A | C |
| ATOM | 6183 | O | PHE | A | 400 | 34.444 | −21.431 | 14.291 | 1.00 | 24.88 | A | O |
| ATOM | 6185 | N | ASP | A | 401 | 32.592 | −22.671 | 14.386 | 1.00 | 23.39 | A | N |
| ATOM | 6186 | CA | ASP | A | 401 | 32.403 | −22.692 | 12.937 | 1.00 | 24.28 | A | C |
| ATOM | 6188 | CB | ASP | A | 401 | 31.188 | −23.522 | 12.564 | 1.00 | 23.91 | A | C |
| ATOM | 6191 | CG | ASP | A | 401 | 31.358 | −24.979 | 12.941 | 1.00 | 28.76 | A | C |

TABLE 4-2-continued

Coordinates of *P. alba* IspS

| ATOM | 6192 | OD1 | ASP | A | 401 | 32.437 | −25.532 | 12.673 | 1.00 | 27.85 | A | O |
|---|---|---|---|---|---|---|---|---|---|---|---|---|
| ATOM | 6193 | OD2 | ASP | A | 401 | 30.423 | −25.559 | 13.533 | 1.00 | 36.29 | A | O |
| ATOM | 6194 | C | ASP | A | 401 | 32.284 | −21.294 | 12.338 | 1.00 | 25.29 | A | C |
| ATOM | 6195 | O | ASP | A | 401 | 32.891 | −21.033 | 11.298 | 1.00 | 24.72 | A | O |
| ATOM | 6197 | N | ASP | A | 402 | 31.512 | −20.417 | 12.991 | 1.00 | 25.45 | A | N |
| ATOM | 6198 | CA | ASP | A | 402 | 31.359 | −19.016 | 12.557 | 1.00 | 25.75 | A | C |
| ATOM | 6200 | CB | ASP | A | 402 | 30.248 | −18.298 | 13.337 | 1.00 | 24.45 | A | C |
| ATOM | 6203 | CG | ASP | A | 402 | 28.864 | −18.808 | 13.005 | 1.00 | 31.45 | A | C |
| ATOM | 6204 | OD1 | ASP | A | 402 | 28.671 | −19.403 | 11.913 | 1.00 | 37.61 | A | O |
| ATOM | 6205 | OD2 | ASP | A | 402 | 27.959 | −18.589 | 13.847 | 1.00 | 37.38 | A | O |
| ATOM | 6206 | C | ASP | A | 402 | 32.664 | −18.196 | 12.708 | 1.00 | 25.83 | A | C |
| ATOM | 6207 | O | ASP | A | 402 | 33.042 | −17.481 | 11.782 | 1.00 | 26.75 | A | O |
| ATOM | 6209 | N | TYR | A | 403 | 33.329 | −18.301 | 13.861 | 1.00 | 23.13 | A | N |
| ATOM | 6210 | CA | TYR | A | 403 | 34.579 | −17.565 | 14.082 | 1.00 | 24.59 | A | C |
| ATOM | 6212 | CB | TYR | A | 403 | 35.098 | −17.728 | 15.511 | 1.00 | 24.61 | A | C |
| ATOM | 6215 | CG | TYR | A | 403 | 36.334 | −16.894 | 15.730 | 1.00 | 28.40 | A | C |
| ATOM | 6216 | CD1 | TYR | A | 403 | 36.236 | −15.532 | 15.998 | 1.00 | 32.59 | A | C |
| ATOM | 6218 | CE1 | TYR | A | 403 | 37.367 | −14.758 | 16.178 | 1.00 | 34.56 | A | C |
| ATOM | 6220 | CZ | TYR | A | 403 | 38.607 | −15.340 | 16.074 | 1.00 | 33.11 | A | C |
| ATOM | 6221 | OH | TYR | A | 403 | 39.730 | −14.586 | 16.261 | 1.00 | 39.07 | A | O |
| ATOM | 6223 | CE2 | TYR | A | 403 | 38.730 | −16.683 | 15.799 | 1.00 | 36.49 | A | C |
| ATOM | 6225 | CD2 | TYR | A | 403 | 37.598 | −17.450 | 15.621 | 1.00 | 29.76 | A | C |
| ATOM | 6227 | C | TYR | A | 403 | 35.694 | −17.999 | 13.161 | 1.00 | 24.10 | A | C |
| ATOM | 6228 | O | TYR | A | 403 | 36.406 | −17.162 | 12.585 | 1.00 | 24.93 | A | O |
| ATOM | 6230 | N | PHE | A | 404 | 35.873 | −19.315 | 13.073 | 1.00 | 23.56 | A | N |
| ATOM | 6231 | CA | PHE | A | 404 | 36.904 | −19.899 | 12.235 | 1.00 | 22.27 | A | C |
| ATOM | 6233 | CB | PHE | A | 404 | 37.024 | −21.394 | 12.494 | 1.00 | 21.27 | A | C |
| ATOM | 6236 | CG | PHE | A | 404 | 38.023 | −22.073 | 11.628 | 1.00 | 21.41 | A | C |
| ATOM | 6237 | CD1 | PHE | A | 404 | 39.364 | −21.747 | 11.713 | 1.00 | 23.52 | A | C |
| ATOM | 6239 | CE1 | PHE | A | 404 | 40.280 | −22.365 | 10.908 | 1.00 | 20.75 | A | C |
| ATOM | 6241 | CZ | PHE | A | 404 | 39.877 | −23.310 | 10.012 | 1.00 | 19.51 | A | C |
| ATOM | 6243 | CE2 | PHE | A | 404 | 38.550 | −23.641 | 9.903 | 1.00 | 24.73 | A | C |
| ATOM | 6245 | CD2 | PHE | A | 404 | 37.627 | −23.022 | 10.701 | 1.00 | 25.71 | A | C |
| ATOM | 6247 | C | PHE | A | 404 | 36.611 | −19.655 | 10.769 | 1.00 | 23.34 | A | C |
| ATOM | 6248 | O | PHE | A | 404 | 37.539 | −19.400 | 9.990 | 1.00 | 24.39 | A | O |
| ATOM | 6250 | N | GLY | A | 405 | 35.338 | −19.738 | 10.387 | 1.00 | 23.21 | A | N |
| ATOM | 6251 | CA | GLY | A | 405 | 34.937 | −19.437 | 9.004 | 1.00 | 24.54 | A | C |
| ATOM | 6254 | C | GLY | A | 405 | 35.401 | −18.050 | 8.580 | 1.00 | 24.99 | A | C |
| ATOM | 6255 | O | GLY | A | 405 | 35.994 | −17.879 | 7.533 | 1.00 | 28.71 | A | O |
| ATOM | 6257 | N | ASN | A | 406 | 35.145 | −17.062 | 9.423 | 1.00 | 24.64 | A | N |
| ATOM | 6258 | CA | ASN | A | 406 | 35.613 | −15.697 | 9.202 | 1.00 | 23.03 | A | C |
| ATOM | 6260 | CB | ASN | A | 406 | 34.943 | −14.761 | 10.193 | 1.00 | 22.91 | A | C |
| ATOM | 6263 | CG | ASN | A | 406 | 35.200 | −13.294 | 9.881 | 1.00 | 22.65 | A | C |
| ATOM | 6264 | OD1 | ASN | A | 406 | 34.666 | −12.755 | 8.927 | 1.00 | 21.35 | A | O |
| ATOM | 6265 | ND2 | ASN | A | 406 | 35.999 | −12.646 | 10.709 | 1.00 | 10.69 | A | N |
| ATOM | 6268 | C | ASN | A | 406 | 37.137 | −15.589 | 9.322 | 1.00 | 22.38 | A | C |
| ATOM | 6269 | O | ASN | A | 406 | 37.770 | −14.927 | 8.512 | 1.00 | 22.73 | A | O |
| ATOM | 6271 | N | ALA | A | 407 | 37.717 | −16.273 | 10.311 | 1.00 | 21.38 | A | N |
| ATOM | 6272 | CA | ALA | A | 407 | 39.138 | −16.136 | 10.630 | 1.00 | 19.47 | A | C |
| ATOM | 6274 | CB | ALA | A | 407 | 39.437 | −16.829 | 11.920 | 1.00 | 18.28 | A | C |
| ATOM | 6278 | C | ALA | A | 407 | 40.118 | −16.626 | 9.546 | 1.00 | 21.80 | A | C |
| ATOM | 6279 | O | ALA | A | 407 | 41.210 | −16.042 | 9.394 | 1.00 | 20.64 | A | O |
| ATOM | 6281 | N | TRP | A | 408 | 39.767 | −17.691 | 8.817 | 1.00 | 20.25 | A | N |
| ATOM | 6282 | CA | TRP | A | 408 | 40.648 | −18.153 | 7.738 | 1.00 | 21.62 | A | C |
| ATOM | 6284 | CB | TRP | A | 408 | 40.410 | −19.619 | 7.303 | 1.00 | 20.05 | A | C |
| ATOM | 6287 | CG | TRP | A | 408 | 39.101 | −20.016 | 6.707 | 1.00 | 20.37 | A | C |
| ATOM | 6288 | CD1 | TRP | A | 408 | 38.120 | −20.717 | 7.331 | 1.00 | 22.39 | A | C |
| ATOM | 6290 | NE1 | TRP | A | 408 | 37.081 | −20.959 | 6.468 | 1.00 | 22.00 | A | N |
| ATOM | 6292 | CE2 | TRP | A | 408 | 37.389 | −20.445 | 5.242 | 1.00 | 25.44 | A | C |
| ATOM | 6293 | CD2 | TRP | A | 408 | 38.661 | −19.852 | 5.342 | 1.00 | 24.30 | A | C |
| ATOM | 6294 | CE3 | TRP | A | 408 | 39.204 | −19.239 | 4.215 | 1.00 | 21.11 | A | C |
| ATOM | 6296 | CZ3 | TRP | A | 408 | 38.484 | −19.231 | 3.054 | 1.00 | 23.35 | A | C |
| ATOM | 6298 | CH2 | TRP | A | 408 | 37.218 | −19.843 | 2.972 | 1.00 | 25.47 | A | C |
| ATOM | 6300 | CZ2 | TRP | A | 408 | 36.656 | −20.454 | 4.058 | 1.00 | 28.32 | A | C |
| ATOM | 6302 | C | TRP | A | 408 | 40.645 | −17.193 | 6.560 | 1.00 | 21.64 | A | C |
| ATOM | 6303 | O | TRP | A | 408 | 41.626 | −17.105 | 5.835 | 1.00 | 25.03 | A | O |
| ATOM | 6305 | N | LYS | A | 409 | 39.555 | −16.457 | 6.393 | 1.00 | 21.99 | A | N |
| ATOM | 6306 | CA | LYS | A | 409 | 39.512 | −15.343 | 5.452 | 1.00 | 20.54 | A | C |
| ATOM | 6308 | CB | LYS | A | 409 | 38.064 | −14.918 | 5.204 | 1.00 | 21.65 | A | C |
| ATOM | 6311 | CG | LYS | A | 409 | 37.258 | −15.966 | 4.401 | 1.00 | 26.50 | A | C |
| ATOM | 6314 | CD | LYS | A | 409 | 35.889 | −15.427 | 3.920 | 1.00 | 37.40 | A | C |
| ATOM | 6317 | CE | LYS | A | 409 | 34.998 | −16.525 | 3.284 | 1.00 | 37.80 | A | C |
| ATOM | 6320 | NZ | LYS | A | 409 | 34.458 | −17.478 | 4.334 | 1.00 | 45.51 | A | N |
| ATOM | 6324 | C | LYS | A | 409 | 40.336 | −14.142 | 5.947 | 1.00 | 20.29 | A | C |
| ATOM | 6325 | O | LYS | A | 409 | 41.041 | −13.522 | 5.166 | 1.00 | 19.77 | A | O |
| ATOM | 6327 | N | SER | A | 410 | 40.238 | −13.822 | 7.240 | 1.00 | 20.14 | A | N |
| ATOM | 6328 | CA | SER | A | 410 | 40.942 | −12.689 | 7.809 | 1.00 | 20.34 | A | C |
| ATOM | 6330 | CB | SER | A | 410 | 40.355 | −12.306 | 9.171 | 1.00 | 21.88 | A | C |

TABLE 4-2-continued

Coordinates of *P. alba* IspS

| ATOM | 6333 | OG | SER | A | 410 | 40.776 | −13.162 | 10.222 | 1.00 | 22.69 | A | O |
|---|---|---|---|---|---|---|---|---|---|---|---|---|
| ATOM | 6335 | C | SER | A | 410 | 42.444 | −12.915 | 7.940 | 1.00 | 21.36 | A | C |
| ATOM | 6336 | O | SER | A | 410 | 43.181 | −11.974 | 8.121 | 1.00 | 25.27 | A | O |
| ATOM | 6338 | N | SER | A | 411 | 42.894 | −14.159 | 7.853 | 1.00 | 21.66 | A | N |
| ATOM | 6339 | CA | SER | A | 411 | 44.323 | −14.472 | 7.749 | 1.00 | 19.61 | A | C |
| ATOM | 6341 | CB | SER | A | 411 | 44.498 | −15.982 | 7.515 | 1.00 | 20.08 | A | C |
| ATOM | 6344 | OG | SER | A | 411 | 44.053 | −16.360 | 6.210 | 1.00 | 16.88 | A | O |
| ATOM | 6346 | C | SER | A | 411 | 44.978 | −13.744 | 6.578 | 1.00 | 19.91 | A | C |
| ATOM | 6347 | O | SER | A | 411 | 46.162 | −13.450 | 6.635 | 1.00 | 21.95 | A | O |
| ATOM | 6349 | N | SER | A | 412 | 44.191 | −13.545 | 5.514 | 1.00 | 21.23 | A | N |
| ATOM | 6350 | CA | SER | A | 412 | 44.583 | −13.016 | 4.210 | 1.00 | 22.76 | A | C |
| ATOM | 6352 | CB | SER | A | 412 | 45.556 | −11.838 | 4.292 | 1.00 | 23.35 | A | C |
| ATOM | 6355 | OG | SER | A | 412 | 46.887 | −12.243 | 4.513 | 1.00 | 23.24 | A | O |
| ATOM | 6357 | C | SER | A | 412 | 45.145 | −14.076 | 3.279 | 1.00 | 24.50 | A | C |
| ATOM | 6358 | O | SER | A | 412 | 45.498 | −13.765 | 2.140 | 1.00 | 25.91 | A | O |
| ATOM | 6360 | N | GLY | A | 413 | 45.193 | −15.324 | 3.726 | 1.00 | 21.84 | A | N |
| ATOM | 6361 | CA | GLY | A | 413 | 45.631 | −16.399 | 2.840 | 1.00 | 21.18 | A | C |
| ATOM | 6364 | C | GLY | A | 413 | 44.883 | −16.434 | 1.512 | 1.00 | 21.67 | A | C |
| ATOM | 6365 | O | GLY | A | 413 | 45.486 | −16.563 | 0.421 | 1.00 | 23.81 | A | O |
| ATOM | 6367 | N | PRO | A | 414 | 43.563 | −16.338 | 1.573 | 1.00 | 19.53 | A | N |
| ATOM | 6368 | CA | PRO | A | 414 | 42.874 | −16.401 | 0.317 | 1.00 | 20.30 | A | C |
| ATOM | 6370 | CB | PRO | A | 414 | 41.403 | −16.323 | 0.743 | 1.00 | 21.26 | A | C |
| ATOM | 6373 | CG | PRO | A | 414 | 41.405 | −16.957 | 2.086 | 1.00 | 19.47 | A | C |
| ATOM | 6376 | CD | PRO | A | 414 | 42.621 | −16.372 | 2.708 | 1.00 | 18.13 | A | C |
| ATOM | 6379 | C | PRO | A | 414 | 43.244 | −15.251 | −0.621 | 1.00 | 20.27 | A | C |
| ATOM | 6380 | O | PRO | A | 414 | 43.472 | −15.460 | −1.813 | 1.00 | 21.85 | A | O |
| ATOM | 6381 | N | LEU | A | 415 | 43.319 | −14.047 | −0.088 | 1.00 | 22.69 | A | N |
| ATOM | 6382 | CA | LEU | A | 415 | 43.651 | −12.894 | −0.914 | 1.00 | 21.21 | A | C |
| ATOM | 6384 | CB | LEU | A | 415 | 43.542 | −11.617 | −0.091 | 1.00 | 23.62 | A | C |
| ATOM | 6387 | CG | LEU | A | 415 | 44.014 | −10.325 | −0.761 | 1.00 | 25.57 | A | C |
| ATOM | 6389 | CD1 | LEU | A | 415 | 43.140 | −9.131 | −0.331 | 1.00 | 24.96 | A | C |
| ATOM | 6393 | CD2 | LEU | A | 415 | 45.473 | −10.080 | −0.413 | 1.00 | 23.56 | A | C |
| ATOM | 6397 | C | LEU | A | 415 | 45.037 | −13.046 | −1.495 | 1.00 | 20.90 | A | C |
| ATOM | 6398 | O | LEU | A | 415 | 45.251 | −12.774 | −2.673 | 1.00 | 20.89 | A | O |
| ATOM | 6400 | N | GLN | A | 416 | 45.991 | −13.480 | −0.682 | 1.00 | 20.64 | A | N |
| ATOM | 6401 | CA | GLN | A | 416 | 47.343 | −13.694 | −1.193 | 1.00 | 21.69 | A | C |
| ATOM | 6403 | CB | GLN | A | 416 | 48.251 | −14.217 | −0.111 | 1.00 | 22.06 | A | C |
| ATOM | 6406 | CG | GLN | A | 416 | 48.534 | −13.218 | 0.973 | 1.00 | 22.59 | A | C |
| ATOM | 6409 | CD | GLN | A | 416 | 49.502 | −13.765 | 1.993 | 1.00 | 26.11 | A | C |
| ATOM | 6410 | OE1 | GLN | A | 416 | 50.390 | −14.547 | 1.671 | 1.00 | 29.66 | A | O |
| ATOM | 6411 | NE2 | GLN | A | 416 | 49.336 | −13.354 | 3.230 | 1.00 | 25.39 | A | N |
| ATOM | 6414 | C | GLN | A | 416 | 47.377 | −14.662 | −2.355 | 1.00 | 22.17 | A | C |
| ATOM | 6415 | O | GLN | A | 416 | 48.115 | −14.479 | −3.326 | 1.00 | 23.08 | A | O |
| ATOM | 6417 | N | LEU | A | 417 | 46.557 | −15.693 | −2.258 | 1.00 | 22.31 | A | N |
| ATOM | 6418 | CA | LEU | A | 417 | 46.551 | −16.738 | −3.261 | 1.00 | 21.08 | A | C |
| ATOM | 6420 | CB | LEU | A | 417 | 45.990 | −18.030 | −2.654 | 1.00 | 21.91 | A | C |
| ATOM | 6423 | CG | LEU | A | 417 | 46.945 | −18.669 | −1.639 | 1.00 | 19.81 | A | C |
| ATOM | 6425 | CD1 | LEU | A | 417 | 46.344 | −19.945 | −1.113 | 1.00 | 14.21 | A | C |
| ATOM | 6429 | CD2 | LEU | A | 417 | 48.346 | −18.927 | −2.256 | 1.00 | 18.26 | A | C |
| ATOM | 6433 | C | LEU | A | 417 | 45.790 | −16.309 | −4.513 | 1.00 | 20.42 | A | C |
| ATOM | 6434 | O | LEU | A | 417 | 46.103 | −16.788 | −5.593 | 1.00 | 22.88 | A | O |
| ATOM | 6436 | N | VAL | A | 418 | 44.810 | −15.411 | −4.392 | 1.00 | 19.02 | A | N |
| ATOM | 6437 | CA | VAL | A | 418 | 44.225 | −14.779 | −5.577 | 1.00 | 18.67 | A | C |
| ATOM | 6439 | CB | VAL | A | 418 | 42.998 | −13.900 | −5.236 | 1.00 | 20.97 | A | C |
| ATOM | 6441 | CG1 | VAL | A | 418 | 41.818 | −14.753 | −4.788 | 1.00 | 18.15 | A | C |
| ATOM | 6445 | CG2 | VAL | A | 418 | 42.578 | −13.054 | −6.466 | 1.00 | 20.23 | A | C |
| ATOM | 6449 | C | VAL | A | 418 | 45.294 | −13.951 | −6.316 | 1.00 | 21.16 | A | C |
| ATOM | 6450 | O | VAL | A | 418 | 45.461 | −14.083 | −7.528 | 1.00 | 22.26 | A | O |
| ATOM | 6452 | N | PHE | A | 419 | 46.042 | −13.109 | −5.596 | 1.00 | 21.17 | A | N |
| ATOM | 6453 | CA | PHE | A | 419 | 47.119 | −12.364 | −6.258 | 1.00 | 21.54 | A | C |
| ATOM | 6455 | CB | PHE | A | 419 | 47.765 | −11.331 | −5.319 | 1.00 | 23.17 | A | C |
| ATOM | 6458 | CG | PHE | A | 419 | 46.958 | −10.072 | −5.184 | 1.00 | 21.42 | A | C |
| ATOM | 6459 | CD1 | PHE | A | 419 | 47.326 | −8.931 | −5.865 | 1.00 | 22.64 | A | C |
| ATOM | 6461 | CE1 | PHE | A | 419 | 46.556 | −7.776 | −5.772 | 1.00 | 25.28 | A | C |
| ATOM | 6463 | CZ | PHE | A | 419 | 45.400 | −7.762 | −5.000 | 1.00 | 19.63 | A | C |
| ATOM | 6465 | CE2 | PHE | A | 419 | 45.006 | −8.907 | −4.339 | 1.00 | 19.52 | A | C |
| ATOM | 6467 | CD2 | PHE | A | 419 | 45.780 | −10.056 | −4.431 | 1.00 | 16.56 | A | C |
| ATOM | 6469 | C | PHE | A | 419 | 48.170 | −13.309 | −6.836 | 1.00 | 23.38 | A | C |
| ATOM | 6470 | O | PHE | A | 419 | 48.675 | −13.070 | −7.931 | 1.00 | 25.01 | A | O |
| ATOM | 6472 | N | ALA | A | 420 | 48.485 | −14.385 | −6.112 | 1.00 | 23.32 | A | N |
| ATOM | 6473 | CA | ALA | A | 420 | 49.475 | −15.361 | −6.567 | 1.00 | 23.26 | A | C |
| ATOM | 6475 | CB | ALA | A | 420 | 49.690 | −16.442 | −5.494 | 1.00 | 23.21 | A | C |
| ATOM | 6479 | C | ALA | A | 420 | 49.055 | −15.988 | −7.887 | 1.00 | 23.77 | A | C |
| ATOM | 6480 | O | ALA | A | 420 | 49.844 | −16.087 | −8.828 | 1.00 | 25.95 | A | O |
| ATOM | 6482 | N | TYR | A | 421 | 47.794 | −16.363 | −7.978 | 1.00 | 23.54 | A | N |
| ATOM | 6483 | CA | TYR | A | 421 | 47.263 | −16.960 | −9.198 | 1.00 | 23.07 | A | C |
| ATOM | 6485 | CB | TYR | A | 421 | 45.749 | −17.152 | −9.089 | 1.00 | 21.91 | A | C |
| ATOM | 6488 | CG | TYR | A | 421 | 45.100 | −17.619 | −10.361 | 1.00 | 27.04 | A | C |

TABLE 4-2-continued

Coordinates of *P. alba* IspS

| ATOM | 6489 | CD1 | TYR | A | 421 | 44.986 | −18.967 | −10.667 | 1.00 | 27.50 | A | C |
|---|---|---|---|---|---|---|---|---|---|---|---|---|
| ATOM | 6491 | CE1 | TYR | A | 421 | 44.387 | −19.382 | −11.857 | 1.00 | 24.79 | A | C |
| ATOM | 6493 | CZ | TYR | A | 421 | 43.913 | −18.448 | −12.741 | 1.00 | 29.31 | A | C |
| ATOM | 6494 | OH | TYR | A | 421 | 43.313 | −18.816 | −13.933 | 1.00 | 31.42 | A | O |
| ATOM | 6496 | CE2 | TYR | A | 421 | 44.033 | −17.116 | −12.450 | 1.00 | 27.45 | A | C |
| ATOM | 6498 | CD2 | TYR | A | 421 | 44.619 | −16.714 | −11.274 | 1.00 | 28.49 | A | C |
| ATOM | 6500 | C | TYR | A | 421 | 47.595 | −16.104 | −10.417 | 1.00 | 24.43 | A | C |
| ATOM | 6501 | O | TYR | A | 421 | 48.121 | −16.591 | −11.394 | 1.00 | 24.22 | A | O |
| ATOM | 6503 | N | PHE | A | 422 | 47.276 | −14.823 | −10.369 | 1.00 | 26.68 | A | N |
| ATOM | 6504 | CA | PHE | A | 422 | 47.503 | −13.956 | −11.530 | 1.00 | 25.20 | A | C |
| ATOM | 6506 | CB | PHE | A | 422 | 46.767 | −12.615 | −11.366 | 1.00 | 24.18 | A | C |
| ATOM | 6509 | CG | PHE | A | 422 | 45.256 | −12.751 | −11.365 | 1.00 | 22.43 | A | C |
| ATOM | 6510 | CD1 | PHE | A | 422 | 44.575 | −13.050 | −12.530 | 1.00 | 24.26 | A | C |
| ATOM | 6512 | CE1 | PHE | A | 422 | 43.211 | −13.195 | −12.532 | 1.00 | 19.71 | A | C |
| ATOM | 6514 | CZ | PHE | A | 422 | 42.501 | −13.018 | −11.375 | 1.00 | 23.62 | A | C |
| ATOM | 6516 | CE2 | PHE | A | 422 | 43.173 | −12.692 | −10.206 | 1.00 | 23.66 | A | C |
| ATOM | 6518 | CD2 | PHE | A | 422 | 44.528 | −12.584 | −10.209 | 1.00 | 23.28 | A | C |
| ATOM | 6520 | C | PHE | A | 422 | 48.995 | −13.758 | −11.820 | 1.00 | 25.13 | A | C |
| ATOM | 6521 | O | PHE | A | 422 | 49.373 | −13.524 | −12.938 | 1.00 | 26.88 | A | O |
| ATOM | 6523 | N | ALA | A | 423 | 49.848 | −13.890 | −10.816 | 1.00 | 26.63 | A | N |
| ATOM | 6524 | CA | ALA | A | 423 | 51.276 | −13.786 | −11.044 | 1.00 | 25.44 | A | C |
| ATOM | 6526 | CB | ALA | A | 423 | 51.948 | −13.230 | −9.802 | 1.00 | 23.79 | A | C |
| ATOM | 6530 | C | ALA | A | 423 | 51.971 | −15.094 | −11.494 | 1.00 | 26.97 | A | C |
| ATOM | 6531 | O | ALA | A | 423 | 53.081 | −15.036 | −12.004 | 1.00 | 27.50 | A | O |
| ATOM | 6533 | N | VAL | A | 424 | 51.374 | −16.264 | −11.299 | 1.00 | 28.07 | A | N |
| ATOM | 6534 | CA | VAL | A | 424 | 52.066 | −17.507 | −11.685 | 1.00 | 29.42 | A | C |
| ATOM | 6536 | CB | VAL | A | 424 | 52.283 | −18.495 | −10.493 | 1.00 | 29.38 | A | C |
| ATOM | 6538 | CG1 | VAL | A | 424 | 52.977 | −17.799 | −9.333 | 1.00 | 25.33 | A | C |
| ATOM | 6542 | CG2 | VAL | A | 424 | 50.996 | −19.113 | −10.041 | 1.00 | 22.76 | A | C |
| ATOM | 6546 | C | VAL | A | 424 | 51.408 | −18.251 | −12.844 | 1.00 | 33.66 | A | C |
| ATOM | 6547 | O | VAL | A | 424 | 52.053 | −19.079 | −13.490 | 1.00 | 35.50 | A | O |
| ATOM | 6549 | N | VAL | A | 425 | 50.146 | −17.965 | −13.127 | 1.00 | 35.54 | A | N |
| ATOM | 6550 | CA | VAL | A | 425 | 49.462 | −18.645 | −14.216 | 1.00 | 39.97 | A | C |
| ATOM | 6552 | CB | VAL | A | 425 | 47.958 | −18.802 | −13.917 | 1.00 | 41.70 | A | C |
| ATOM | 6554 | CG1 | VAL | A | 425 | 47.191 | −19.173 | −15.166 | 1.00 | 40.48 | A | C |
| ATOM | 6558 | CG2 | VAL | A | 425 | 47.747 | −19.848 | −12.808 | 1.00 | 38.62 | A | C |
| ATOM | 6562 | C | VAL | A | 425 | 49.640 | −17.919 | −15.547 | 1.00 | 43.30 | A | C |
| ATOM | 6563 | O | VAL | A | 425 | 49.391 | −16.728 | −15.649 | 1.00 | 45.08 | A | O |
| ATOM | 6565 | N | GLN | A | 426 | 50.020 | −18.681 | −16.567 | 1.00 | 47.38 | A | N |
| ATOM | 6566 | CA | GLN | A | 426 | 50.299 | −18.169 | −17.911 | 1.00 | 50.63 | A | C |
| ATOM | 6568 | CB | GLN | A | 426 | 50.890 | −19.311 | −18.767 | 1.00 | 52.86 | A | C |
| ATOM | 6571 | CG | GLN | A | 426 | 51.846 | −18.861 | −19.889 | 1.00 | 62.22 | A | C |
| ATOM | 6574 | CD | GLN | A | 426 | 52.389 | −20.034 | −20.719 | 1.00 | 68.68 | A | C |
| ATOM | 6575 | OE1 | GLN | A | 426 | 52.756 | −21.079 | −20.174 | 1.00 | 74.04 | A | O |
| ATOM | 6576 | NE2 | GLN | A | 426 | 52.439 | −19.857 | −22.039 | 1.00 | 69.99 | A | N |
| ATOM | 6579 | C | GLN | A | 426 | 49.041 | −17.602 | −18.573 | 1.00 | 48.57 | A | C |
| ATOM | 6580 | O | GLN | A | 426 | 49.002 | −16.441 | −18.976 | 1.00 | 49.10 | A | O |
| ATOM | 6582 | N | ASN | A | 427 | 48.014 | −18.437 | −18.675 | 1.00 | 46.60 | A | N |
| ATOM | 6583 | CA | ASN | A | 427 | 46.748 | −18.043 | −19.265 | 1.00 | 44.60 | A | C |
| ATOM | 6585 | CB | ASN | A | 427 | 46.429 | −18.906 | −20.487 | 1.00 | 44.23 | A | C |
| ATOM | 6588 | CG | ASN | A | 427 | 47.362 | −18.637 | −21.657 | 1.00 | 46.94 | A | C |
| ATOM | 6589 | OD1 | ASN | A | 427 | 47.181 | −17.674 | −22.416 | 1.00 | 45.67 | A | O |
| ATOM | 6590 | ND2 | ASN | A | 427 | 48.363 | −19.501 | −21.818 | 1.00 | 41.48 | A | N |
| ATOM | 6593 | C | ASN | A | 427 | 45.649 | −18.200 | −18.231 | 1.00 | 42.84 | A | C |
| ATOM | 6594 | O | ASN | A | 427 | 45.421 | −19.292 | −17.709 | 1.00 | 42.87 | A | O |
| ATOM | 6596 | N | ILE | A | 428 | 44.957 | −17.105 | −17.973 | 1.00 | 40.25 | A | N |
| ATOM | 6597 | CA | ILE | A | 428 | 43.853 | −17.067 | −17.038 | 1.00 | 40.59 | A | C |
| ATOM | 6599 | CB | ILE | A | 428 | 43.459 | −15.599 | −16.777 | 1.00 | 41.62 | A | C |
| ATOM | 6601 | CG1 | ILE | A | 428 | 44.629 | −14.848 | −16.128 | 1.00 | 40.01 | A | C |
| ATOM | 6604 | CD1 | ILE | A | 428 | 44.658 | −13.322 | −16.465 | 1.00 | 35.27 | A | C |
| ATOM | 6608 | CG2 | ILE | A | 428 | 42.222 | −15.507 | −15.910 | 1.00 | 44.80 | A | C |
| ATOM | 6612 | C | ILE | A | 428 | 42.693 | −17.839 | −17.658 | 1.00 | 41.08 | A | C |
| ATOM | 6613 | O | ILE | A | 428 | 42.553 | −17.846 | −18.880 | 1.00 | 42.37 | A | O |
| ATOM | 6615 | N | LYS | A | 429 | 41.896 | −18.518 | −16.832 | 1.00 | 40.25 | A | N |
| ATOM | 6616 | CA | LYS | A | 429 | 40.658 | −19.174 | −17.289 | 1.00 | 39.88 | A | C |
| ATOM | 6618 | CB | LYS | A | 429 | 40.765 | −20.701 | −17.218 | 1.00 | 40.54 | A | C |
| ATOM | 6621 | CG | LYS | A | 429 | 41.990 | −21.287 | −17.914 | 1.00 | 44.77 | A | C |
| ATOM | 6624 | CD | LYS | A | 429 | 42.057 | −22.807 | −17.758 | 1.00 | 51.10 | A | C |
| ATOM | 6627 | CE | LYS | A | 429 | 43.171 | −23.422 | −18.624 | 1.00 | 55.81 | A | C |
| ATOM | 6630 | NZ | LYS | A | 429 | 43.150 | −24.926 | −18.619 | 1.00 | 55.50 | A | N |
| ATOM | 6634 | C | LYS | A | 429 | 39.503 | −18.725 | −16.422 | 1.00 | 38.57 | A | C |
| ATOM | 6635 | O | LYS | A | 429 | 39.622 | −18.686 | −15.203 | 1.00 | 37.64 | A | O |
| ATOM | 6637 | N | LYS | A | 430 | 38.387 | −18.402 | −17.057 | 1.00 | 39.36 | A | N |
| ATOM | 6638 | CA | LYS | A | 430 | 37.202 | −17.914 | −16.377 | 1.00 | 41.11 | A | C |
| ATOM | 6640 | CB | LYS | A | 430 | 36.047 | −17.755 | −17.374 | 1.00 | 42.76 | A | C |
| ATOM | 6643 | CG | LYS | A | 430 | 34.811 | −17.033 | −16.805 | 1.00 | 52.15 | A | C |
| ATOM | 6646 | CD | LYS | A | 430 | 33.595 | −17.025 | −17.779 | 1.00 | 62.30 | A | C |
| ATOM | 6649 | CE | LYS | A | 430 | 33.214 | −18.434 | −18.289 | 1.00 | 67.69 | A | C |

TABLE 4-2-continued

Coordinates of *P. alba* IspS

| ATOM | 6652 | NZ | LYS | A | 430 | 33.285 | −19.518 | −17.240 | 1.00 | 70.45 | A | N |
|------|------|------|-----|---|-----|--------|---------|---------|------|-------|---|---|
| ATOM | 6656 | C | LYS | A | 430 | 36.760 | −18.829 | −15.242 | 1.00 | 39.57 | A | C |
| ATOM | 6657 | O | LYS | A | 430 | 36.417 | −18.359 | −14.164 | 1.00 | 40.96 | A | O |
| ATOM | 6659 | N | GLU | A | 431 | 36.750 | −20.128 | −15.481 | 1.00 | 38.13 | A | N |
| ATOM | 6660 | CA | GLU | A | 431 | 36.268 | −21.066 | −14.481 | 1.00 | 38.67 | A | C |
| ATOM | 6662 | CB | GLU | A | 431 | 36.170 | −22.473 | −15.077 | 1.00 | 40.19 | A | C |
| ATOM | 6665 | CG | GLU | A | 431 | 35.497 | −23.511 | −14.161 | 1.00 | 48.81 | A | C |
| ATOM | 6668 | CD | GLU | A | 431 | 35.757 | −24.965 | −14.584 | 1.00 | 61.18 | A | C |
| ATOM | 6669 | OE1 | GLU | A | 431 | 36.689 | −25.202 | −15.394 | 1.00 | 63.32 | A | O |
| ATOM | 6670 | OE2 | GLU | A | 431 | 35.035 | −25.871 | −14.094 | 1.00 | 62.58 | A | O |
| ATOM | 6671 | C | GLU | A | 431 | 37.190 | −21.073 | −13.259 | 1.00 | 36.48 | A | C |
| ATOM | 6672 | O | GLU | A | 431 | 36.734 | −21.199 | −12.129 | 1.00 | 36.23 | A | O |
| ATOM | 6674 | N | GLU | A | 432 | 38.488 | −20.954 | −13.497 | 1.00 | 33.62 | A | N |
| ATOM | 6675 | CA | GLU | A | 432 | 39.445 | −20.894 | −12.420 | 1.00 | 32.85 | A | C |
| ATOM | 6677 | CB | GLU | A | 432 | 40.866 | −20.914 | −12.983 | 1.00 | 33.14 | A | C |
| ATOM | 6680 | CG | GLU | A | 432 | 41.222 | −22.249 | −13.661 | 1.00 | 32.44 | A | C |
| ATOM | 6683 | CD | GLU | A | 432 | 42.707 | −22.372 | −14.031 | 1.00 | 39.53 | A | C |
| ATOM | 6684 | OE1 | GLU | A | 432 | 43.375 | −21.332 | −14.238 | 1.00 | 36.98 | A | O |
| ATOM | 6685 | OE2 | GLU | A | 432 | 43.201 | −23.522 | −14.119 | 1.00 | 43.09 | A | O |
| ATOM | 6686 | C | GLU | A | 432 | 39.184 | −19.665 | −11.532 | 1.00 | 32.20 | A | C |
| ATOM | 6687 | O | GLU | A | 432 | 39.045 | −19.781 | −10.320 | 1.00 | 30.88 | A | O |
| ATOM | 6689 | N | ILE | A | 433 | 39.068 | −18.493 | −12.134 | 1.00 | 32.33 | A | N |
| ATOM | 6690 | CA | ILE | A | 433 | 38.908 | −17.281 | −11.335 | 1.00 | 34.37 | A | C |
| ATOM | 6692 | CB | ILE | A | 433 | 39.317 | −15.983 | −12.109 | 1.00 | 33.78 | A | C |
| ATOM | 6694 | CG1 | ILE | A | 433 | 38.480 | −15.704 | −13.327 | 1.00 | 38.66 | A | C |
| ATOM | 6697 | CD1 | ILE | A | 433 | 39.103 | −14.565 | −14.169 | 1.00 | 38.73 | A | C |
| ATOM | 6701 | CG2 | ILE | A | 433 | 40.739 | −16.106 | −12.614 | 1.00 | 35.34 | A | C |
| ATOM | 6705 | C | ILE | A | 433 | 37.524 | −17.235 | −10.645 | 1.00 | 33.31 | A | C |
| ATOM | 6706 | O | ILE | A | 433 | 37.414 | −16.838 | −9.485 | 1.00 | 33.97 | A | O |
| ATOM | 6708 | N | GLU | A | 434 | 36.501 | −17.744 | −11.305 | 1.00 | 30.95 | A | N |
| ATOM | 6709 | CA | GLU | A | 434 | 35.221 | −17.944 | −10.643 | 1.00 | 32.93 | A | C |
| ATOM | 6711 | CB | GLU | A | 434 | 34.242 | −18.683 | −11.551 | 1.00 | 33.75 | A | C |
| ATOM | 6714 | CG | GLU | A | 434 | 32.961 | −17.939 | −11.781 | 1.00 | 46.39 | A | C |
| ATOM | 6717 | CD | GLU | A | 434 | 33.044 | −17.044 | −12.995 | 1.00 | 58.82 | A | C |
| ATOM | 6718 | OE1 | GLU | A | 434 | 32.768 | −17.555 | −14.111 | 1.00 | 63.42 | A | O |
| ATOM | 6719 | OE2 | GLU | A | 434 | 33.383 | −15.842 | −12.828 | 1.00 | 62.69 | A | O |
| ATOM | 6720 | C | GLU | A | 434 | 35.349 | −18.777 | −9.367 | 1.00 | 31.62 | A | C |
| ATOM | 6721 | O | GLU | A | 434 | 34.681 | −18.501 | −8.378 | 1.00 | 30.48 | A | O |
| ATOM | 6723 | N | ASN | A | 435 | 36.149 | −19.844 | −9.428 | 1.00 | 29.51 | A | N |
| ATOM | 6724 | CA | ASN | A | 435 | 36.342 | −20.710 | −8.285 | 1.00 | 27.90 | A | C |
| ATOM | 6726 | CB | ASN | A | 435 | 36.878 | −22.070 | −8.714 | 1.00 | 28.27 | A | C |
| ATOM | 6729 | CG | ASN | A | 435 | 35.756 | −23.015 | −9.168 | 1.00 | 33.33 | A | C |
| ATOM | 6730 | OD1 | ASN | A | 435 | 35.103 | −23.671 | −8.354 | 1.00 | 37.87 | A | O |
| ATOM | 6731 | ND2 | ASN | A | 435 | 35.524 | −23.063 | −10.466 | 1.00 | 29.41 | A | N |
| ATOM | 6734 | C | ASN | A | 435 | 37.212 | −20.060 | −7.199 | 1.00 | 25.58 | A | C |
| ATOM | 6735 | O | ASN | A | 435 | 36.985 | −20.285 | −6.037 | 1.00 | 23.42 | A | O |
| ATOM | 6737 | N | LEU | A | 436 | 38.163 | −19.221 | −7.582 | 1.00 | 25.17 | A | N |
| ATOM | 6738 | CA | LEU | A | 436 | 38.861 | −18.411 | −6.597 | 1.00 | 27.41 | A | C |
| ATOM | 6740 | CB | LEU | A | 436 | 39.909 | −17.535 | −7.240 | 1.00 | 26.64 | A | C |
| ATOM | 6743 | CG | LEU | A | 436 | 41.090 | −18.252 | −7.868 | 1.00 | 26.99 | A | C |
| ATOM | 6745 | CD1 | LEU | A | 436 | 42.017 | −17.177 | −8.425 | 1.00 | 26.84 | A | C |
| ATOM | 6749 | CD2 | LEU | A | 436 | 41.819 | −19.140 | −6.861 | 1.00 | 23.22 | A | C |
| ATOM | 6753 | C | LEU | A | 436 | 37.892 | −17.536 | −5.800 | 1.00 | 28.45 | A | C |
| ATOM | 6754 | O | LEU | A | 436 | 37.991 | −17.504 | −4.587 | 1.00 | 29.36 | A | O |
| ATOM | 6756 | N | GLN | A | 437 | 36.936 | −16.891 | −6.465 | 1.00 | 30.08 | A | N |
| ATOM | 6757 | CA | GLN | A | 437 | 35.973 | −16.014 | −5.778 | 1.00 | 32.71 | A | C |
| ATOM | 6759 | CB | GLN | A | 437 | 35.120 | −15.210 | −6.760 | 1.00 | 34.60 | A | C |
| ATOM | 6762 | CG | GLN | A | 437 | 35.934 | −14.322 | −7.670 | 1.00 | 40.35 | A | C |
| ATOM | 6765 | CD | GLN | A | 437 | 35.165 | −13.112 | −8.186 | 1.00 | 41.37 | A | C |
| ATOM | 6766 | OE1 | GLN | A | 437 | 34.156 | −13.238 | −8.889 | 1.00 | 39.37 | A | O |
| ATOM | 6767 | NE2 | GLN | A | 437 | 35.667 | −11.931 | −7.865 | 1.00 | 36.34 | A | N |
| ATOM | 6770 | C | GLN | A | 437 | 35.034 | −16.781 | −4.887 | 1.00 | 32.09 | A | C |
| ATOM | 6771 | O | GLN | A | 437 | 34.485 | −16.215 | −3.930 | 1.00 | 31.31 | A | O |
| ATOM | 6773 | N | LYS | A | 438 | 34.824 | −18.058 | −5.192 | 1.00 | 31.99 | A | N |
| ATOM | 6774 | CA | LYS | A | 438 | 34.012 | −18.893 | −4.314 | 1.00 | 33.99 | A | C |
| ATOM | 6776 | CB | LYS | A | 438 | 33.202 | −19.913 | −5.124 | 1.00 | 35.73 | A | C |
| ATOM | 6779 | CG | LYS | A | 438 | 32.247 | −19.275 | −6.153 | 1.00 | 45.89 | A | C |
| ATOM | 6782 | CD | LYS | A | 438 | 31.513 | −20.316 | −7.024 | 1.00 | 55.14 | A | C |
| ATOM | 6785 | CE | LYS | A | 438 | 30.386 | −19.644 | −7.869 | 1.00 | 63.38 | A | C |
| ATOM | 6788 | NZ | LYS | A | 438 | 29.546 | −20.589 | −8.694 | 1.00 | 60.75 | A | N |
| ATOM | 6792 | C | LYS | A | 438 | 34.865 | −19.586 | −3.236 | 1.00 | 31.23 | A | C |
| ATOM | 6793 | O | LYS | A | 438 | 34.392 | −20.495 | −2.582 | 1.00 | 32.53 | A | O |
| ATOM | 6795 | N | TYR | A | 439 | 36.106 | −19.154 | −3.025 | 1.00 | 29.33 | A | N |
| ATOM | 6796 | CA | TYR | A | 439 | 36.987 | −19.827 | −2.037 | 1.00 | 30.37 | A | C |
| ATOM | 6798 | CB | TYR | A | 439 | 36.580 | −19.469 | −0.619 | 1.00 | 30.63 | A | C |
| ATOM | 6801 | CG | TYR | A | 439 | 36.618 | −18.009 | −0.425 | 1.00 | 34.45 | A | C |
| ATOM | 6802 | CD1 | TYR | A | 439 | 37.797 | −17.379 | −0.140 | 1.00 | 34.10 | A | C |
| ATOM | 6804 | CE1 | TYR | A | 439 | 37.843 | −16.017 | 0.018 | 1.00 | 46.73 | A | C |

TABLE 4-2-continued

Coordinates of *P. alba* IspS

| ATOM | 6806 | CZ | TYR | A | 439 | 36.696 | −15.271 | −0.125 | 1.00 | 42.16 | A | C |
|---|---|---|---|---|---|---|---|---|---|---|---|---|
| ATOM | 6807 | OH | TYR | A | 439 | 36.764 | −13.915 | 0.022 | 1.00 | 47.04 | A | O |
| ATOM | 6809 | CE2 | TYR | A | 439 | 35.511 | −15.873 | −0.425 | 1.00 | 40.10 | A | C |
| ATOM | 6811 | CD2 | TYR | A | 439 | 35.471 | −17.237 | −0.574 | 1.00 | 40.92 | A | C |
| ATOM | 6813 | C | TYR | A | 439 | 37.069 | −21.348 | −2.189 | 1.00 | 28.38 | A | C |
| ATOM | 6814 | O | TYR | A | 439 | 36.845 | −22.103 | −1.260 | 1.00 | 29.86 | A | O |
| ATOM | 6816 | N | HIS | A | 440 | 37.398 | −21.772 | −3.393 | 1.00 | 28.22 | A | N |
| ATOM | 6817 | CA | HIS | A | 440 | 37.588 | −23.162 | −3.706 | 1.00 | 27.43 | A | C |
| ATOM | 6819 | CB | HIS | A | 440 | 38.015 | −23.245 | −5.154 | 1.00 | 27.12 | A | C |
| ATOM | 6822 | CG | HIS | A | 440 | 38.138 | −24.635 | −5.681 | 1.00 | 32.93 | A | C |
| ATOM | 6823 | ND1 | HIS | A | 440 | 39.347 | −25.286 | −5.776 | 1.00 | 33.95 | A | N |
| ATOM | 6825 | CE1 | HIS | A | 440 | 39.159 | −26.476 | −6.317 | 1.00 | 37.85 | A | C |
| ATOM | 6827 | NE2 | HIS | A | 440 | 37.873 | −26.615 | −6.576 | 1.00 | 39.10 | A | N |
| ATOM | 6829 | CD2 | HIS | A | 440 | 37.213 | −25.475 | −6.197 | 1.00 | 32.98 | A | C |
| ATOM | 6831 | C | HIS | A | 440 | 38.672 | −23.786 | −2.837 | 1.00 | 28.12 | A | C |
| ATOM | 6832 | O | HIS | A | 440 | 39.654 | −23.120 | −2.456 | 1.00 | 28.00 | A | O |
| ATOM | 6834 | N | ASP | A | 441 | 38.503 | −25.080 | −2.588 | 1.00 | 26.13 | A | N |
| ATOM | 6835 | CA | ASP | A | 441 | 39.400 | −25.896 | −1.767 | 1.00 | 26.61 | A | C |
| ATOM | 6837 | CB | ASP | A | 441 | 39.147 | −27.387 | −2.031 | 1.00 | 27.37 | A | C |
| ATOM | 6840 | CG | ASP | A | 441 | 37.763 | −27.853 | −1.564 | 1.00 | 29.75 | A | C |
| ATOM | 6841 | OD1 | ASP | A | 441 | 37.167 | −27.195 | −0.690 | 1.00 | 33.53 | A | O |
| ATOM | 6842 | OD2 | ASP | A | 441 | 37.280 | −28.881 | −2.096 | 1.00 | 42.48 | A | O |
| ATOM | 6843 | C | ASP | A | 441 | 40.881 | −25.637 | −1.966 | 1.00 | 25.58 | A | C |
| ATOM | 6844 | O | ASP | A | 441 | 41.660 | −25.729 | −1.031 | 1.00 | 24.77 | A | O |
| ATOM | 6846 | N | THR | A | 442 | 41.277 | −25.366 | −3.193 | 1.00 | 24.56 | A | N |
| ATOM | 6847 | CA | THR | A | 442 | 42.673 | −25.189 | −3.491 | 1.00 | 25.67 | A | C |
| ATOM | 6849 | CB | THR | A | 442 | 42.868 | −24.892 | −4.992 | 1.00 | 27.90 | A | C |
| ATOM | 6851 | OG1 | THR | A | 442 | 42.233 | −25.923 | −5.760 | 1.00 | 35.85 | A | O |
| ATOM | 6853 | CG2 | THR | A | 442 | 44.321 | −24.853 | −5.349 | 1.00 | 30.00 | A | C |
| ATOM | 6857 | C | THR | A | 442 | 43.224 | −24.046 | −2.635 | 1.00 | 24.91 | A | C |
| ATOM | 6858 | O | THR | A | 442 | 44.337 | −24.143 | −2.151 | 1.00 | 25.25 | A | O |
| ATOM | 6860 | N | ILE | A | 443 | 42.444 | −22.980 | −2.426 | 1.00 | 22.84 | A | N |
| ATOM | 6861 | CA | ILE | A | 443 | 42.947 | −21.824 | −1.701 | 1.00 | 22.34 | A | C |
| ATOM | 6863 | CB | ILE | A | 443 | 42.756 | −20.489 | −2.471 | 1.00 | 22.85 | A | C |
| ATOM | 6865 | CG1 | ILE | A | 443 | 41.323 | −20.006 | −2.467 | 1.00 | 21.22 | A | C |
| ATOM | 6868 | CD1 | ILE | A | 443 | 41.213 | −18.584 | −3.057 | 1.00 | 21.90 | A | C |
| ATOM | 6872 | CG2 | ILE | A | 443 | 43.241 | −20.606 | −3.900 | 1.00 | 18.47 | A | C |
| ATOM | 6876 | C | ILE | A | 443 | 42.392 | −21.728 | −0.294 | 1.00 | 23.52 | A | C |
| ATOM | 6877 | O | ILE | A | 443 | 43.045 | −21.179 | 0.600 | 1.00 | 24.12 | A | O |
| ATOM | 6879 | N | SER | A | 444 | 41.229 | −22.322 | −0.060 | 1.00 | 24.10 | A | N |
| ATOM | 6880 | CA | SER | A | 444 | 40.649 | −22.275 | 1.259 | 1.00 | 23.55 | A | C |
| ATOM | 6882 | CB | SER | A | 444 | 39.190 | −22.705 | 1.213 | 1.00 | 25.69 | A | C |
| ATOM | 6885 | OG | SER | A | 444 | 39.087 | −24.090 | 0.993 | 1.00 | 26.17 | A | O |
| ATOM | 6887 | C | SER | A | 444 | 41.453 | −23.163 | 2.210 | 1.00 | 24.88 | A | C |
| ATOM | 6888 | O | SER | A | 444 | 41.745 | −22.766 | 3.322 | 1.00 | 26.85 | A | O |
| ATOM | 6890 | N | ARG | A | 445 | 41.866 | −24.344 | 1.776 | 1.00 | 22.69 | A | N |
| ATOM | 6891 | CA | ARG | A | 445 | 42.481 | −25.273 | 2.732 | 1.00 | 23.70 | A | C |
| ATOM | 6893 | CB | ARG | A | 445 | 42.542 | −26.686 | 2.164 | 1.00 | 24.49 | A | C |
| ATOM | 6896 | CG | ARG | A | 445 | 41.178 | −27.309 | 2.168 | 1.00 | 24.68 | A | C |
| ATOM | 6899 | CD | ARG | A | 445 | 41.233 | −28.614 | 1.536 | 1.00 | 35.00 | A | C |
| ATOM | 6902 | NE | ARG | A | 445 | 39.915 | −29.227 | 1.462 | 1.00 | 41.73 | A | N |
| ATOM | 6904 | CZ | ARG | A | 445 | 39.533 | −30.015 | 0.465 | 1.00 | 40.99 | A | C |
| ATOM | 6905 | NH1 | ARG | A | 445 | 40.365 | −30.263 | −0.544 | 1.00 | 41.35 | A | N |
| ATOM | 6908 | NH2 | ARG | A | 445 | 38.333 | −30.562 | 0.478 | 1.00 | 38.98 | A | N |
| ATOM | 6911 | C | ARG | A | 445 | 43.820 | −24.835 | 3.305 | 1.00 | 23.32 | A | C |
| ATOM | 6912 | O | ARG | A | 445 | 44.022 | −24.930 | 4.514 | 1.00 | 23.11 | A | O |
| ATOM | 6914 | N | PRO | A | 446 | 44.722 | −24.325 | 2.458 | 1.00 | 23.47 | A | N |
| ATOM | 6915 | CA | PRO | A | 446 | 45.955 | −23.766 | 2.988 | 1.00 | 21.78 | A | C |
| ATOM | 6917 | CB | PRO | A | 446 | 46.703 | −23.284 | 1.751 | 1.00 | 21.26 | A | C |
| ATOM | 6920 | CG | PRO | A | 446 | 46.082 | −23.962 | 0.618 | 1.00 | 26.11 | A | C |
| ATOM | 6923 | CD | PRO | A | 446 | 44.688 | −24.299 | 0.985 | 1.00 | 25.66 | A | C |
| ATOM | 6926 | C | PRO | A | 446 | 45.677 | −22.599 | 3.903 | 1.00 | 20.98 | A | C |
| ATOM | 6927 | O | PRO | A | 446 | 46.397 | −22.418 | 4.875 | 1.00 | 22.87 | A | O |
| ATOM | 6928 | N | SER | A | 447 | 44.620 | −21.845 | 3.619 | 1.00 | 21.42 | A | N |
| ATOM | 6929 | CA | SER | A | 447 | 44.230 | −20.731 | 4.469 | 1.00 | 20.70 | A | C |
| ATOM | 6931 | CB | SER | A | 447 | 43.183 | −19.827 | 3.806 | 1.00 | 21.82 | A | C |
| ATOM | 6934 | OG | SER | A | 447 | 43.690 | −19.313 | 2.556 | 1.00 | 20.36 | A | O |
| ATOM | 6936 | C | SER | A | 447 | 43.777 | −21.209 | 5.822 | 1.00 | 22.31 | A | C |
| ATOM | 6937 | O | SER | A | 447 | 44.075 | −20.554 | 6.820 | 1.00 | 23.84 | A | O |
| ATOM | 6939 | N | HIS | A | 448 | 43.104 | −22.358 | 5.876 | 1.00 | 21.04 | A | N |
| ATOM | 6940 | CA | HIS | A | 448 | 42.712 | −22.952 | 7.144 | 1.00 | 20.19 | A | C |
| ATOM | 6942 | CB | HIS | A | 448 | 42.004 | −24.317 | 6.968 | 1.00 | 21.41 | A | C |
| ATOM | 6945 | CG | HIS | A | 448 | 40.675 | −24.253 | 6.277 | 1.00 | 21.38 | A | C |
| ATOM | 6946 | ND1 | HIS | A | 448 | 39.944 | −25.382 | 5.969 | 1.00 | 29.82 | A | N |
| ATOM | 6948 | CE1 | HIS | A | 448 | 38.812 | −25.025 | 5.382 | 1.00 | 29.77 | A | C |
| ATOM | 6950 | NE2 | HIS | A | 448 | 38.790 | −23.705 | 5.289 | 1.00 | 24.12 | A | N |
| ATOM | 6952 | CD2 | HIS | A | 448 | 39.939 | −23.202 | 5.844 | 1.00 | 24.45 | A | C |
| ATOM | 6954 | C | HIS | A | 448 | 43.959 | −23.180 | 7.969 | 1.00 | 20.74 | A | C |

TABLE 4-2-continued

Coordinates of *P. alba* IspS

| ATOM | 6955 | O | HIS | A | 448 | 44.002 | −22.864 | 9.156 | 1.00 | 21.08 | A | O |
|---|---|---|---|---|---|---|---|---|---|---|---|---|
| ATOM | 6957 | N | ILE | A | 449 | 44.979 | −23.756 | 7.340 | 1.00 | 23.35 | A | N |
| ATOM | 6958 | CA | ILE | A | 449 | 46.212 | −24.095 | 8.052 | 1.00 | 23.10 | A | C |
| ATOM | 6960 | CB | ILE | A | 449 | 47.188 | −24.850 | 7.162 | 1.00 | 24.84 | A | C |
| ATOM | 6962 | CG1 | ILE | A | 449 | 46.563 | −26.145 | 6.663 | 1.00 | 26.29 | A | C |
| ATOM | 6965 | CD1 | ILE | A | 449 | 46.302 | −27.059 | 7.721 | 1.00 | 29.80 | A | C |
| ATOM | 6969 | CG2 | ILE | A | 449 | 48.490 | −25.168 | 7.926 | 1.00 | 20.98 | A | C |
| ATOM | 6973 | C | ILE | A | 449 | 46.928 | −22.848 | 8.571 | 1.00 | 22.77 | A | C |
| ATOM | 6974 | O | ILE | A | 449 | 47.479 | −22.863 | 9.658 | 1.00 | 23.35 | A | O |
| ATOM | 6976 | N | PHE | A | 450 | 46.918 | −21.796 | 7.764 | 1.00 | 22.40 | A | N |
| ATOM | 6977 | CA | PHE | A | 450 | 47.527 | −20.514 | 8.097 | 1.00 | 23.32 | A | C |
| ATOM | 6979 | CB | PHE | A | 450 | 47.411 | −19.599 | 6.857 | 1.00 | 25.81 | A | C |
| ATOM | 6982 | CG | PHE | A | 450 | 47.936 | −18.168 | 7.029 | 1.00 | 26.15 | A | C |
| ATOM | 6983 | CD1 | PHE | A | 450 | 48.744 | −17.792 | 8.083 | 1.00 | 29.10 | A | C |
| ATOM | 6985 | CE1 | PHE | A | 450 | 49.178 | −16.483 | 8.205 | 1.00 | 27.29 | A | C |
| ATOM | 6987 | CZ | PHE | A | 450 | 48.850 | −15.548 | 7.238 | 1.00 | 27.02 | A | C |
| ATOM | 6989 | CE2 | PHE | A | 450 | 48.056 | −15.914 | 6.167 | 1.00 | 30.51 | A | C |
| ATOM | 6991 | CD2 | PHE | A | 450 | 47.625 | −17.214 | 6.062 | 1.00 | 23.58 | A | C |
| ATOM | 6993 | C | PHE | A | 450 | 46.854 | −19.966 | 9.342 | 1.00 | 22.59 | A | C |
| ATOM | 6994 | O | PHE | A | 450 | 47.505 | −19.733 | 10.370 | 1.00 | 23.10 | A | O |
| ATOM | 6996 | N | ARG | A | 451 | 45.538 | −19.856 | 9.327 | 1.00 | 22.00 | A | N |
| ATOM | 6997 | CA | ARG | A | 451 | 44.884 | −19.370 | 10.531 | 1.00 | 22.22 | A | C |
| ATOM | 6999 | CB | ARG | A | 451 | 43.396 | −19.215 | 10.307 | 1.00 | 20.08 | A | C |
| ATOM | 7002 | CG | ARG | A | 451 | 42.583 | −18.918 | 11.559 | 1.00 | 20.62 | A | C |
| ATOM | 7005 | CD | ARG | A | 451 | 43.123 | −17.713 | 12.310 | 1.00 | 20.48 | A | C |
| ATOM | 7008 | NE | ARG | A | 451 | 43.009 | −16.489 | 11.536 | 1.00 | 22.29 | A | N |
| ATOM | 7010 | CZ | ARG | A | 451 | 43.506 | −15.318 | 11.908 | 1.00 | 22.48 | A | C |
| ATOM | 7011 | NH1 | ARG | A | 451 | 44.207 | −15.207 | 13.027 | 1.00 | 20.34 | A | N |
| ATOM | 7014 | NH2 | ARG | A | 451 | 43.317 | −14.259 | 11.149 | 1.00 | 22.06 | A | N |
| ATOM | 7017 | C | ARG | A | 451 | 45.183 | −20.281 | 11.740 | 1.00 | 22.94 | A | C |
| ATOM | 7018 | O | ARG | A | 451 | 45.522 | −19.806 | 12.825 | 1.00 | 22.52 | A | O |
| ATOM | 7020 | N | LEU | A | 452 | 45.044 | −21.587 | 11.561 | 1.00 | 23.09 | A | N |
| ATOM | 7021 | CA | LEU | A | 452 | 45.208 | −22.500 | 12.700 | 1.00 | 22.53 | A | C |
| ATOM | 7023 | CB | LEU | A | 452 | 44.799 | −23.931 | 12.332 | 1.00 | 19.50 | A | C |
| ATOM | 7026 | CG | LEU | A | 452 | 43.313 | −24.152 | 12.034 | 1.00 | 22.38 | A | C |
| ATOM | 7028 | CD1 | LEU | A | 452 | 43.089 | −25.564 | 11.548 | 1.00 | 17.99 | A | C |
| ATOM | 7032 | CD2 | LEU | A | 452 | 42.403 | −23.854 | 13.257 | 1.00 | 20.44 | A | C |
| ATOM | 7036 | C | LEU | A | 452 | 46.632 | −22.453 | 13.278 | 1.00 | 22.42 | A | C |
| ATOM | 7037 | O | LEU | A | 452 | 46.793 | −22.522 | 14.485 | 1.00 | 24.48 | A | O |
| ATOM | 7039 | N | CYS | A | 453 | 47.656 | −22.340 | 12.433 | 1.00 | 22.44 | A | N |
| ATOM | 7040 | CA | CYS | A | 453 | 49.031 | −22.312 | 12.933 | 1.00 | 24.59 | A | C |
| ATOM | 7042 | CB | CYS | A | 453 | 50.051 | −22.425 | 11.804 | 1.00 | 26.01 | A | C |
| ATOM | 7045 | SG | CYS | A | 453 | 50.255 | −24.066 | 11.075 | 1.00 | 27.17 | A | S |
| ATOM | 7047 | C | CYS | A | 453 | 49.283 | −21.015 | 13.709 | 1.00 | 28.20 | A | C |
| ATOM | 7048 | O | CYS | A | 453 | 49.935 | −21.023 | 14.753 | 1.00 | 31.95 | A | O |
| ATOM | 7050 | N | ASN | A | 454 | 48.768 | −19.901 | 13.184 | 1.00 | 28.25 | A | N |
| ATOM | 7051 | CA | ASN | A | 454 | 48.874 | −18.600 | 13.832 | 1.00 | 25.74 | A | C |
| ATOM | 7053 | CB | ASN | A | 454 | 48.292 | −17.509 | 12.914 | 1.00 | 25.90 | A | C |
| ATOM | 7056 | CG | ASN | A | 454 | 48.465 | −16.083 | 13.470 | 1.00 | 26.47 | A | C |
| ATOM | 7057 | OD1 | ASN | A | 454 | 48.991 | −15.875 | 14.552 | 1.00 | 40.48 | A | O |
| ATOM | 7058 | ND2 | ASN | A | 454 | 48.002 | −15.108 | 12.715 | 1.00 | 31.43 | A | N |
| ATOM | 7061 | C | ASN | A | 454 | 48.183 | −18.595 | 15.180 | 1.00 | 26.43 | A | C |
| ATOM | 7062 | O | ASN | A | 454 | 48.774 | −18.191 | 16.180 | 1.00 | 28.40 | A | O |
| ATOM | 7064 | N | ASP | A | 455 | 46.927 | −19.024 | 15.205 | 1.00 | 26.39 | A | N |
| ATOM | 7065 | CA | ASP | A | 455 | 46.154 | −19.022 | 16.434 | 1.00 | 25.96 | A | C |
| ATOM | 7067 | CB | ASP | A | 455 | 44.695 | −19.399 | 16.185 | 1.00 | 26.38 | A | C |
| ATOM | 7070 | CG | ASP | A | 455 | 43.848 | −18.229 | 15.635 | 1.00 | 30.58 | A | C |
| ATOM | 7071 | OD1 | ASP | A | 455 | 44.407 | −17.210 | 15.161 | 1.00 | 23.66 | A | O |
| ATOM | 7072 | OD2 | ASP | A | 455 | 42.597 | −18.359 | 15.672 | 1.00 | 27.94 | A | O |
| ATOM | 7073 | C | ASP | A | 455 | 46.775 | −19.977 | 17.451 | 1.00 | 28.81 | A | C |
| ATOM | 7074 | O | ASP | A | 455 | 46.716 | −19.705 | 18.659 | 1.00 | 29.70 | A | O |
| ATOM | 7076 | N | LEU | A | 456 | 47.368 | −21.081 | 16.982 | 1.00 | 28.29 | A | N |
| ATOM | 7077 | CA | LEU | A | 456 | 48.072 | −21.997 | 17.886 | 1.00 | 29.09 | A | C |
| ATOM | 7079 | CB | LEU | A | 456 | 48.609 | −23.237 | 17.180 | 1.00 | 28.53 | A | C |
| ATOM | 7082 | CG | LEU | A | 456 | 47.613 | −24.345 | 16.893 | 1.00 | 30.92 | A | C |
| ATOM | 7084 | CD1 | LEU | A | 456 | 48.213 | −25.380 | 15.920 | 1.00 | 27.62 | A | C |
| ATOM | 7088 | CD2 | LEU | A | 456 | 47.182 | −24.972 | 18.197 | 1.00 | 26.10 | A | C |
| ATOM | 7092 | C | LEU | A | 456 | 49.240 | −21.292 | 18.552 | 1.00 | 30.48 | A | C |
| ATOM | 7093 | O | LEU | A | 456 | 49.465 | −21.492 | 19.733 | 1.00 | 30.20 | A | O |
| ATOM | 7095 | N | ALA | A | 457 | 49.965 | −20.458 | 17.807 | 1.00 | 30.94 | A | N |
| ATOM | 7096 | CA | ALA | A | 457 | 51.170 | −19.838 | 18.350 | 1.00 | 30.89 | A | C |
| ATOM | 7098 | CB | ALA | A | 457 | 51.906 | −19.078 | 17.293 | 1.00 | 28.28 | A | C |
| ATOM | 7102 | C | ALA | A | 457 | 50.847 | −18.917 | 19.515 | 1.00 | 32.02 | A | C |
| ATOM | 7103 | O | ALA | A | 457 | 51.601 | −18.841 | 20.466 | 1.00 | 34.01 | A | O |
| ATOM | 7105 | N | SER | A | 458 | 49.728 | −18.222 | 19.441 | 1.00 | 34.20 | A | N |
| ATOM | 7106 | CA | SER | A | 458 | 49.383 | −17.264 | 20.468 | 1.00 | 35.38 | A | C |
| ATOM | 7108 | CB | SER | A | 458 | 48.963 | −15.943 | 19.823 | 1.00 | 36.92 | A | C |
| ATOM | 7111 | OG | SER | A | 458 | 47.792 | −16.106 | 19.042 | 1.00 | 42.95 | A | O |

TABLE 4-2-continued

Coordinates of *P. alba* IspS

| ATOM | 7113 | C | SER | A | 458 | 48.282 | −17.746 | 21.385 | 1.00 | 34.92 | A | C |
|---|---|---|---|---|---|---|---|---|---|---|---|---|
| ATOM | 7114 | O | SER | A | 458 | 47.901 | −17.026 | 22.295 | 1.00 | 37.00 | A | O |
| ATOM | 7116 | N | ALA | A | 459 | 47.772 | −18.955 | 21.178 | 1.00 | 34.97 | A | N |
| ATOM | 7117 | CA | ALA | A | 459 | 46.608 | −19.381 | 21.934 | 1.00 | 34.82 | A | C |
| ATOM | 7119 | CB | ALA | A | 459 | 46.246 | −20.833 | 21.642 | 1.00 | 33.75 | A | C |
| ATOM | 7123 | C | ALA | A | 459 | 46.827 | −19.195 | 23.424 | 1.00 | 36.34 | A | C |
| ATOM | 7124 | O | ALA | A | 459 | 46.042 | −18.506 | 24.078 | 1.00 | 34.86 | A | O |
| ATOM | 7126 | N | SER | A | 460 | 47.892 | −19.805 | 23.948 | 1.00 | 39.24 | A | N |
| ATOM | 7127 | CA | SER | A | 460 | 48.081 | −19.909 | 25.403 | 1.00 | 42.73 | A | C |
| ATOM | 7129 | CB | SER | A | 460 | 49.266 | −20.832 | 25.765 | 1.00 | 43.60 | A | C |
| ATOM | 7132 | OG | SER | A | 460 | 50.520 | −20.221 | 25.514 | 1.00 | 50.63 | A | O |
| ATOM | 7134 | C | SER | A | 460 | 48.188 | −18.543 | 26.093 | 1.00 | 42.82 | A | C |
| ATOM | 7135 | O | SER | A | 460 | 47.591 | −18.342 | 27.150 | 1.00 | 45.33 | A | O |
| ATOM | 7137 | N | ALA | A | 461 | 48.894 | −17.598 | 25.482 | 1.00 | 43.05 | A | N |
| ATOM | 7138 | CA | ALA | A | 461 | 49.000 | −16.245 | 26.037 | 1.00 | 43.65 | A | C |
| ATOM | 7140 | CB | ALA | A | 461 | 50.032 | −15.414 | 25.263 | 1.00 | 42.89 | A | C |
| ATOM | 7144 | C | ALA | A | 461 | 47.647 | −15.539 | 26.035 | 1.00 | 44.95 | A | C |
| ATOM | 7145 | O | ALA | A | 461 | 47.237 | −14.969 | 27.045 | 1.00 | 46.39 | A | O |
| ATOM | 7147 | N | GLU | A | 462 | 46.947 | −15.588 | 24.905 | 1.00 | 45.01 | A | N |
| ATOM | 7148 | CA | GLU | A | 462 | 45.666 | −14.906 | 24.787 | 1.00 | 43.89 | A | C |
| ATOM | 7150 | CB | GLU | A | 462 | 45.159 | −14.966 | 23.346 | 1.00 | 44.36 | A | C |
| ATOM | 7153 | CG | GLU | A | 462 | 46.045 | −14.140 | 22.394 | 1.00 | 46.73 | A | C |
| ATOM | 7156 | CD | GLU | A | 462 | 45.617 | −14.211 | 20.936 | 1.00 | 48.39 | A | C |
| ATOM | 7157 | OE1 | GLU | A | 462 | 44.548 | −14.792 | 20.655 | 1.00 | 52.33 | A | O |
| ATOM | 7158 | OE2 | GLU | A | 462 | 46.361 | −13.686 | 20.071 | 1.00 | 51.40 | A | O |
| ATOM | 7159 | C | GLU | A | 462 | 44.653 | −15.472 | 25.763 | 1.00 | 42.95 | A | C |
| ATOM | 7160 | O | GLU | A | 462 | 43.856 | −14.731 | 26.336 | 1.00 | 43.58 | A | O |
| ATOM | 7162 | N | ILE | A | 463 | 44.710 | −16.776 | 25.985 | 1.00 | 42.70 | A | N |
| ATOM | 7163 | CA | ILE | A | 463 | 43.782 | −17.436 | 26.897 | 1.00 | 44.06 | A | C |
| ATOM | 7165 | CB | ILE | A | 463 | 43.862 | −18.971 | 26.773 | 1.00 | 43.11 | A | C |
| ATOM | 7167 | CG1 | ILE | A | 463 | 43.216 | −19.427 | 25.461 | 1.00 | 43.65 | A | C |
| ATOM | 7170 | CD1 | ILE | A | 463 | 43.585 | −20.854 | 25.026 | 1.00 | 35.99 | A | C |
| ATOM | 7174 | CG2 | ILE | A | 463 | 43.180 | −19.641 | 27.948 | 1.00 | 43.57 | A | C |
| ATOM | 7178 | C | ILE | A | 463 | 44.055 | −17.028 | 28.344 | 1.00 | 46.68 | A | C |
| ATOM | 7179 | O | ILE | A | 463 | 43.119 | −16.877 | 29.134 | 1.00 | 47.89 | A | O |
| ATOM | 7181 | N | ALA | A | 464 | 45.334 | −16.854 | 28.678 | 1.00 | 47.67 | A | N |
| ATOM | 7182 | CA | ALA | A | 464 | 45.744 | −16.469 | 30.028 | 1.00 | 48.52 | A | C |
| ATOM | 7184 | CB | ALA | A | 464 | 47.240 | −16.690 | 30.214 | 1.00 | 47.57 | A | C |
| ATOM | 7188 | C | ALA | A | 464 | 45.365 | −15.013 | 30.335 | 1.00 | 49.52 | A | C |
| ATOM | 7189 | O | ALA | A | 464 | 45.060 | −14.690 | 31.477 | 1.00 | 49.39 | A | O |
| ATOM | 7191 | N | ARG | A | 465 | 45.362 | −14.153 | 29.311 | 1.00 | 50.44 | A | N |
| ATOM | 7192 | CA | ARG | A | 465 | 44.869 | −12.768 | 29.442 | 1.00 | 51.06 | A | C |
| ATOM | 7194 | CB | ARG | A | 465 | 45.373 | −11.889 | 28.285 | 1.00 | 51.52 | A | C |
| ATOM | 7197 | CG | ARG | A | 465 | 46.878 | −11.770 | 28.142 | 1.00 | 55.59 | A | C |
| ATOM | 7200 | CD | ARG | A | 465 | 47.250 | −10.670 | 27.135 | 1.00 | 58.49 | A | C |
| ATOM | 7203 | NE | ARG | A | 465 | 48.351 | −11.095 | 26.268 | 1.00 | 64.38 | A | N |
| ATOM | 7205 | CZ | ARG | A | 465 | 48.272 | −11.296 | 24.947 | 1.00 | 68.81 | A | C |
| ATOM | 7206 | NH1 | ARG | A | 465 | 47.138 | −11.087 | 24.269 | 1.00 | 68.12 | A | N |
| ATOM | 7209 | NH2 | ARG | A | 465 | 49.356 | −11.696 | 24.282 | 1.00 | 69.02 | A | N |
| ATOM | 7212 | C | ARG | A | 465 | 43.330 | −12.663 | 29.474 | 1.00 | 50.68 | A | C |
| ATOM | 7213 | O | ARG | A | 465 | 42.785 | −11.559 | 29.542 | 1.00 | 50.12 | A | O |
| ATOM | 7215 | N | GLY | A | 466 | 42.635 | −13.795 | 29.397 | 1.00 | 51.02 | A | N |
| ATOM | 7216 | CA | GLY | A | 466 | 41.175 | −13.811 | 29.340 | 1.00 | 50.69 | A | C |
| ATOM | 7219 | C | GLY | A | 466 | 40.582 | −13.347 | 28.015 | 1.00 | 49.88 | A | C |
| ATOM | 7220 | O | GLY | A | 466 | 39.478 | −12.817 | 27.989 | 1.00 | 50.15 | A | O |
| ATOM | 7222 | N | GLU | A | 467 | 41.304 | −13.545 | 26.914 | 1.00 | 49.42 | A | N |
| ATOM | 7223 | CA | GLU | A | 467 | 40.783 | −13.204 | 25.591 | 1.00 | 48.91 | A | C |
| ATOM | 7225 | CB | GLU | A | 467 | 41.897 | −12.706 | 24.677 | 1.00 | 49.79 | A | C |
| ATOM | 7228 | CG | GLU | A | 467 | 42.400 | −11.308 | 25.017 | 1.00 | 54.31 | A | C |
| ATOM | 7231 | CD | GLU | A | 467 | 43.488 | −10.836 | 24.059 | 1.00 | 62.07 | A | C |
| ATOM | 7232 | OE1 | GLU | A | 467 | 43.370 | −11.106 | 22.831 | 1.00 | 58.12 | A | O |
| ATOM | 7233 | OE2 | GLU | A | 467 | 44.457 | −10.198 | 24.543 | 1.00 | 65.78 | A | O |
| ATOM | 7234 | C | GLU | A | 467 | 40.046 | −14.372 | 24.923 | 1.00 | 46.84 | A | C |
| ATOM | 7235 | O | GLU | A | 467 | 40.258 | −15.543 | 25.245 | 1.00 | 46.20 | A | O |
| ATOM | 7237 | N | THR | A | 468 | 39.182 | −14.009 | 23.983 | 1.00 | 44.02 | A | N |
| ATOM | 7238 | CA | THR | A | 468 | 38.326 | −14.934 | 23.255 | 1.00 | 41.85 | A | C |
| ATOM | 7240 | CB | THR | A | 468 | 36.893 | −14.390 | 23.234 | 1.00 | 41.87 | A | C |
| ATOM | 7242 | OG1 | THR | A | 468 | 36.268 | −14.693 | 24.475 | 1.00 | 44.70 | A | O |
| ATOM | 7244 | CG2 | THR | A | 468 | 36.079 | −14.983 | 22.064 | 1.00 | 43.08 | A | C |
| ATOM | 7248 | C | THR | A | 468 | 38.732 | −15.112 | 21.793 | 1.00 | 39.84 | A | C |
| ATOM | 7249 | O | THR | A | 468 | 38.459 | −16.149 | 21.206 | 1.00 | 40.48 | A | O |
| ATOM | 7251 | N | ALA | A | 469 | 39.366 | −14.098 | 21.210 | 1.00 | 36.45 | A | N |
| ATOM | 7252 | CA | ALA | A | 469 | 39.501 | −14.004 | 19.772 | 1.00 | 35.32 | A | C |
| ATOM | 7254 | CB | ALA | A | 469 | 39.721 | −12.524 | 19.353 | 1.00 | 34.04 | A | C |
| ATOM | 7258 | C | ALA | A | 469 | 40.636 | −14.890 | 19.278 | 1.00 | 32.68 | A | C |
| ATOM | 7259 | O | ALA | A | 469 | 41.677 | −14.392 | 18.837 | 1.00 | 33.79 | A | O |
| ATOM | 7261 | N | ASN | A | 470 | 40.399 | −16.201 | 19.338 | 1.00 | 29.47 | A | N |
| ATOM | 7262 | CA | ASN | A | 470 | 41.373 | −17.233 | 18.951 | 1.00 | 27.64 | A | C |

TABLE 4-2-continued

Coordinates of *P. alba* IspS

| ATOM | 7264 | CB | ASN | A | 470 | 42.374 | −17.461 | 20.088 | 1.00 | 27.10 | A | C |
|------|------|-----|-----|---|-----|--------|---------|--------|------|-------|---|---|
| ATOM | 7267 | CG | ASN | A | 470 | 43.550 | −18.304 | 19.660 | 1.00 | 28.28 | A | C |
| ATOM | 7268 | OD1 | ASN | A | 470 | 43.450 | −19.524 | 19.605 | 1.00 | 34.80 | A | O |
| ATOM | 7269 | ND2 | ASN | A | 470 | 44.676 | −17.657 | 19.346 | 1.00 | 30.77 | A | N |
| ATOM | 7272 | C | ASN | A | 470 | 40.651 | −18.546 | 18.607 | 1.00 | 27.38 | A | C |
| ATOM | 7273 | O | ASN | A | 470 | 39.675 | −18.909 | 19.274 | 1.00 | 28.84 | A | O |
| ATOM | 7275 | N | SER | A | 471 | 41.115 | −19.259 | 17.580 | 1.00 | 25.73 | A | N |
| ATOM | 7276 | CA | SER | A | 471 | 40.413 | −20.476 | 17.127 | 1.00 | 25.56 | A | C |
| ATOM | 7278 | CB | SER | A | 471 | 41.033 | −21.026 | 15.831 | 1.00 | 24.86 | A | C |
| ATOM | 7281 | OG | SER | A | 471 | 40.941 | −20.066 | 14.773 | 1.00 | 24.10 | A | O |
| ATOM | 7283 | C | SER | A | 471 | 40.387 | −21.555 | 18.208 | 1.00 | 25.57 | A | C |
| ATOM | 7284 | O | SER | A | 471 | 39.370 | −22.234 | 18.392 | 1.00 | 28.49 | A | O |
| ATOM | 7286 | N | VAL | A | 472 | 41.487 | −21.689 | 18.940 | 1.00 | 24.63 | A | N |
| ATOM | 7287 | CA | VAL | A | 472 | 41.573 | −22.638 | 20.058 | 1.00 | 24.83 | A | C |
| ATOM | 7289 | CB | VAL | A | 472 | 42.976 | −22.647 | 20.681 | 1.00 | 24.78 | A | C |
| ATOM | 7291 | CG1 | VAL | A | 472 | 43.062 | −23.699 | 21.804 | 1.00 | 24.97 | A | C |
| ATOM | 7295 | CG2 | VAL | A | 472 | 44.025 | −22.919 | 19.612 | 1.00 | 24.81 | A | C |
| ATOM | 7299 | C | VAL | A | 472 | 40.585 | −22.302 | 21.161 | 1.00 | 25.99 | A | C |
| ATOM | 7300 | O | VAL | A | 472 | 39.878 | −23.166 | 21.682 | 1.00 | 27.14 | A | O |
| ATOM | 7302 | N | SER | A | 473 | 40.548 | −21.027 | 21.517 | 1.00 | 28.17 | A | N |
| ATOM | 7303 | CA | SER | A | 473 | 39.639 | −20.538 | 22.539 | 1.00 | 27.38 | A | C |
| ATOM | 7305 | CB | SER | A | 473 | 39.877 | −19.048 | 22.775 | 1.00 | 28.17 | A | C |
| ATOM | 7308 | OG | SER | A | 473 | 38.904 | −18.546 | 23.666 | 1.00 | 36.50 | A | O |
| ATOM | 7310 | C | SER | A | 473 | 38.199 | −20.785 | 22.134 | 1.00 | 26.74 | A | C |
| ATOM | 7311 | O | SER | A | 473 | 37.391 | −21.244 | 22.942 | 1.00 | 26.77 | A | O |
| ATOM | 7313 | N | CYS | A | 474 | 37.872 | −20.526 | 20.874 | 1.00 | 26.84 | A | N |
| ATOM | 7314 | CA | CYS | A | 474 | 36.513 | −20.796 | 20.410 | 1.00 | 27.97 | A | C |
| ATOM | 7316 | CB | CYS | A | 474 | 36.248 | −20.181 | 19.037 | 1.00 | 28.57 | A | C |
| ATOM | 7319 | SG | CYS | A | 474 | 36.094 | −18.392 | 19.116 | 1.00 | 37.03 | A | S |
| ATOM | 7321 | C | CYS | A | 474 | 36.219 | −22.290 | 20.396 | 1.00 | 27.00 | A | C |
| ATOM | 7322 | O | CYS | A | 474 | 35.094 | −22.698 | 20.680 | 1.00 | 27.66 | A | O |
| ATOM | 7324 | N | TYR | A | 475 | 37.221 | −23.106 | 20.076 | 1.00 | 26.04 | A | N |
| ATOM | 7325 | CA | TYR | A | 475 | 37.015 | −24.547 | 20.082 | 1.00 | 25.17 | A | C |
| ATOM | 7327 | CB | TYR | A | 475 | 38.209 | −25.290 | 19.486 | 1.00 | 24.75 | A | C |
| ATOM | 7330 | CG | TYR | A | 475 | 37.853 | −26.656 | 18.929 | 1.00 | 28.24 | A | C |
| ATOM | 7331 | CD1 | TYR | A | 475 | 37.516 | −26.821 | 17.587 | 1.00 | 32.56 | A | C |
| ATOM | 7333 | CE1 | TYR | A | 475 | 37.192 | −28.071 | 17.081 | 1.00 | 36.43 | A | C |
| ATOM | 7335 | CZ | TYR | A | 475 | 37.199 | −29.178 | 17.923 | 1.00 | 34.35 | A | C |
| ATOM | 7336 | OH | TYR | A | 475 | 36.886 | −30.419 | 17.441 | 1.00 | 43.05 | A | O |
| ATOM | 7338 | CE2 | TYR | A | 475 | 37.533 | −29.045 | 19.246 | 1.00 | 34.85 | A | C |
| ATOM | 7340 | CD2 | TYR | A | 475 | 37.858 | −27.783 | 19.747 | 1.00 | 34.43 | A | C |
| ATOM | 7342 | C | TYR | A | 475 | 36.749 | −25.003 | 21.518 | 1.00 | 26.37 | A | C |
| ATOM | 7343 | O | TYR | A | 475 | 35.869 | −25.833 | 21.752 | 1.00 | 27.21 | A | O |
| ATOM | 7345 | N | MET | A | 476 | 37.481 | −24.438 | 22.479 | 1.00 | 26.99 | A | N |
| ATOM | 7346 | CA | MET | A | 476 | 37.252 | −24.759 | 23.901 | 1.00 | 26.98 | A | C |
| ATOM | 7348 | CB | MET | A | 476 | 38.202 | −23.971 | 24.789 | 1.00 | 26.60 | A | C |
| ATOM | 7351 | CG | MET | A | 476 | 39.652 | −24.384 | 24.656 | 1.00 | 30.73 | A | C |
| ATOM | 7354 | SD | MET | A | 476 | 40.740 | −23.174 | 25.392 | 1.00 | 36.77 | A | S |
| ATOM | 7355 | CE | MET | A | 476 | 39.937 | −22.903 | 26.995 | 1.00 | 30.88 | A | C |
| ATOM | 7359 | C | MET | A | 476 | 35.826 | −24.444 | 24.319 | 1.00 | 26.91 | A | C |
| ATOM | 7360 | O | MET | A | 476 | 35.137 | −25.270 | 24.911 | 1.00 | 28.08 | A | O |
| ATOM | 7362 | N | ARG | A | 477 | 35.386 | −23.237 | 24.009 | 1.00 | 28.18 | A | N |
| ATOM | 7363 | CA | ARG | A | 477 | 34.058 | −22.797 | 24.398 | 1.00 | 29.26 | A | C |
| ATOM | 7365 | CB | ARG | A | 477 | 33.880 | −21.314 | 24.079 | 1.00 | 28.98 | A | C |
| ATOM | 7368 | CG | ARG | A | 477 | 32.520 | −20.733 | 24.449 | 1.00 | 32.12 | A | C |
| ATOM | 7371 | CD | ARG | A | 477 | 32.537 | −19.223 | 24.275 | 1.00 | 40.29 | A | C |
| ATOM | 7374 | NE | ARG | A | 477 | 32.786 | −18.815 | 22.888 | 1.00 | 44.21 | A | N |
| ATOM | 7376 | CZ | ARG | A | 477 | 33.290 | −17.637 | 22.514 | 1.00 | 46.88 | A | C |
| ATOM | 7377 | NH1 | ARG | A | 477 | 33.619 | −16.721 | 23.420 | 1.00 | 48.90 | A | N |
| ATOM | 7380 | NH2 | ARG | A | 477 | 33.469 | −17.371 | 21.222 | 1.00 | 45.48 | A | N |
| ATOM | 7383 | C | ARG | A | 477 | 32.971 | −23.620 | 23.702 | 1.00 | 29.87 | A | C |
| ATOM | 7384 | O | ARG | A | 477 | 32.006 | −24.035 | 24.352 | 1.00 | 31.04 | A | O |
| ATOM | 7386 | N | THR | A | 478 | 33.110 | −23.852 | 22.397 | 1.00 | 28.61 | A | N |
| ATOM | 7387 | CA | THR | A | 478 | 32.044 | −24.539 | 21.657 | 1.00 | 28.83 | A | C |
| ATOM | 7389 | CB | THR | A | 478 | 32.216 | −24.430 | 20.131 | 1.00 | 28.55 | A | C |
| ATOM | 7391 | OG1 | THR | A | 478 | 32.238 | −23.056 | 19.746 | 1.00 | 26.42 | A | O |
| ATOM | 7393 | CG2 | THR | A | 478 | 31.034 | −25.107 | 19.407 | 1.00 | 30.41 | A | C |
| ATOM | 7397 | C | THR | A | 478 | 31.911 | −26.014 | 22.075 | 1.00 | 28.98 | A | C |
| ATOM | 7398 | O | THR | A | 478 | 30.822 | −26.467 | 22.400 | 1.00 | 28.85 | A | O |
| ATOM | 7400 | N | LYS | A | 479 | 33.013 | −26.758 | 22.074 | 1.00 | 29.87 | A | N |
| ATOM | 7401 | CA | LYS | A | 479 | 32.969 | −28.157 | 22.516 | 1.00 | 30.10 | A | C |
| ATOM | 7403 | CB | LYS | A | 479 | 34.143 | −28.960 | 21.938 | 1.00 | 30.29 | A | C |
| ATOM | 7406 | CG | LYS | A | 479 | 34.249 | −28.964 | 20.406 | 1.00 | 33.64 | A | C |
| ATOM | 7409 | CD | LYS | A | 479 | 33.118 | −29.688 | 19.695 | 1.00 | 42.31 | A | C |
| ATOM | 7412 | CE | LYS | A | 479 | 33.306 | −29.581 | 18.174 | 1.00 | 47.79 | A | C |
| ATOM | 7415 | NZ | LYS | A | 479 | 32.463 | −30.535 | 17.381 | 1.00 | 47.97 | A | N |
| ATOM | 7419 | C | LYS | A | 479 | 32.936 | −28.290 | 24.057 | 1.00 | 30.88 | A | C |
| ATOM | 7420 | O | LYS | A | 479 | 32.660 | −29.360 | 24.576 | 1.00 | 30.47 | A | O |

TABLE 4-2-continued

Coordinates of *P. alba* IspS

| ATOM | 7422 | N | GLY | A | 480 | 33.223 | −27.207 | 24.781 | 1.00 | 31.72 | A | N |
|------|------|-----|-----|---|-----|--------|---------|--------|------|-------|---|---|
| ATOM | 7423 | CA | GLY | A | 480 | 33.206 | −27.231 | 26.248 | 1.00 | 31.97 | A | C |
| ATOM | 7426 | C | GLY | A | 480 | 34.311 | −28.088 | 26.843 | 1.00 | 31.96 | A | C |
| ATOM | 7427 | O | GLY | A | 480 | 34.044 | −28.932 | 27.722 | 1.00 | 31.49 | A | O |
| ATOM | 7429 | N | ILE | A | 481 | 35.544 | −27.847 | 26.382 | 1.00 | 29.64 | A | N |
| ATOM | 7430 | CA | ILE | A | 481 | 36.702 | −28.660 | 26.747 | 1.00 | 29.31 | A | C |
| ATOM | 7432 | CB | ILE | A | 481 | 37.044 | −29.668 | 25.621 | 1.00 | 29.72 | A | C |
| ATOM | 7434 | CG1 | ILE | A | 481 | 37.398 | −28.940 | 24.302 | 1.00 | 30.04 | A | C |
| ATOM | 7437 | CD1 | ILE | A | 481 | 37.581 | −29.865 | 23.094 | 1.00 | 25.37 | A | C |
| ATOM | 7441 | CG2 | ILE | A | 481 | 35.865 | −30.602 | 25.391 | 1.00 | 29.26 | A | C |
| ATOM | 7445 | C | ILE | A | 481 | 37.926 | −27.807 | 27.052 | 1.00 | 31.21 | A | C |
| ATOM | 7446 | O | ILE | A | 481 | 37.964 | −26.613 | 26.746 | 1.00 | 32.82 | A | O |
| ATOM | 7448 | N | SER | A | 482 | 38.939 | −28.439 | 27.634 | 1.00 | 32.10 | A | N |
| ATOM | 7449 | CA | SER | A | 482 | 40.162 | −27.756 | 28.052 | 1.00 | 31.77 | A | C |
| ATOM | 7451 | CB | SER | A | 482 | 41.010 | −28.718 | 28.874 | 1.00 | 32.78 | A | C |
| ATOM | 7454 | OG | SER | A | 482 | 41.130 | −29.963 | 28.191 | 1.00 | 34.52 | A | O |
| ATOM | 7456 | C | SER | A | 482 | 41.000 | −27.281 | 26.883 | 1.00 | 32.56 | A | C |
| ATOM | 7457 | O | SER | A | 482 | 40.839 | −27.765 | 25.763 | 1.00 | 35.17 | A | O |
| ATOM | 7459 | N | GLU | A | 483 | 41.931 | −26.369 | 27.161 | 1.00 | 32.02 | A | N |
| ATOM | 7460 | CA | GLU | A | 483 | 42.928 | −25.941 | 26.186 | 1.00 | 33.48 | A | C |
| ATOM | 7462 | CB | GLU | A | 483 | 43.916 | −24.948 | 26.815 | 1.00 | 33.20 | A | C |
| ATOM | 7465 | CG | GLU | A | 483 | 45.047 | −24.524 | 25.877 | 1.00 | 33.67 | A | C |
| ATOM | 7468 | CD | GLU | A | 483 | 45.858 | −23.351 | 26.389 | 1.00 | 40.22 | A | C |
| ATOM | 7469 | OE1 | GLU | A | 483 | 45.594 | −22.861 | 27.519 | 1.00 | 43.03 | A | O |
| ATOM | 7470 | OE2 | GLU | A | 483 | 46.774 | −22.916 | 25.657 | 1.00 | 38.81 | A | O |
| ATOM | 7471 | C | GLU | A | 483 | 43.714 | −27.102 | 25.558 | 1.00 | 35.98 | A | C |
| ATOM | 7472 | O | GLU | A | 483 | 43.954 | −27.120 | 24.335 | 1.00 | 37.13 | A | O |
| ATOM | 7474 | N | GLU | A | 484 | 44.134 | −28.045 | 26.393 | 1.00 | 36.43 | A | N |
| ATOM | 7475 | CA | GLU | A | 484 | 44.980 | −29.149 | 25.948 | 1.00 | 37.19 | A | C |
| ATOM | 7477 | CB | GLU | A | 484 | 45.523 | −29.932 | 27.153 | 1.00 | 39.57 | A | C |
| ATOM | 7480 | CG | GLU | A | 484 | 46.686 | −30.866 | 26.813 | 1.00 | 49.47 | A | C |
| ATOM | 7483 | CD | GLU | A | 484 | 47.292 | −31.543 | 28.041 | 1.00 | 62.43 | A | C |
| ATOM | 7484 | OE1 | GLU | A | 484 | 47.606 | −30.824 | 29.026 | 1.00 | 66.87 | A | O |
| ATOM | 7485 | OE2 | GLU | A | 484 | 47.459 | −32.791 | 28.014 | 1.00 | 63.06 | A | O |
| ATOM | 7486 | C | GLU | A | 484 | 44.226 | −30.084 | 25.005 | 1.00 | 35.28 | A | C |
| ATOM | 7487 | O | GLU | A | 484 | 44.768 | −30.493 | 23.976 | 1.00 | 33.82 | A | O |
| ATOM | 7489 | N | LEU | A | 485 | 42.989 | −30.433 | 25.351 | 1.00 | 33.95 | A | N |
| ATOM | 7490 | CA | LEU | A | 485 | 42.175 | −31.227 | 24.425 | 1.00 | 33.76 | A | C |
| ATOM | 7492 | CB | LEU | A | 485 | 40.886 | −31.745 | 25.069 | 1.00 | 34.55 | A | C |
| ATOM | 7495 | CG | LEU | A | 485 | 40.968 | −33.207 | 25.551 | 1.00 | 39.74 | A | C |
| ATOM | 7497 | CD1 | LEU | A | 485 | 42.126 | −33.394 | 26.541 | 1.00 | 40.89 | A | C |
| ATOM | 7501 | CD2 | LEU | A | 485 | 39.647 | −33.669 | 26.180 | 1.00 | 42.87 | A | C |
| ATOM | 7505 | C | LEU | A | 485 | 41.870 | −30.436 | 23.155 | 1.00 | 32.05 | A | C |
| ATOM | 7506 | O | LEU | A | 485 | 41.963 | −30.972 | 22.062 | 1.00 | 30.76 | A | O |
| ATOM | 7508 | N | ALA | A | 486 | 41.522 | −29.164 | 23.308 | 1.00 | 30.65 | A | N |
| ATOM | 7509 | CA | ALA | A | 486 | 41.225 | −28.305 | 22.164 | 1.00 | 29.72 | A | C |
| ATOM | 7511 | CB | ALA | A | 486 | 40.771 | −26.933 | 22.648 | 1.00 | 28.94 | A | C |
| ATOM | 7515 | C | ALA | A | 486 | 42.435 | −28.176 | 21.228 | 1.00 | 30.16 | A | C |
| ATOM | 7516 | O | ALA | A | 486 | 42.310 | −28.256 | 19.998 | 1.00 | 32.78 | A | O |
| ATOM | 7518 | N | THR | A | 487 | 43.607 | −27.990 | 21.816 | 1.00 | 29.51 | A | N |
| ATOM | 7519 | CA | THR | A | 487 | 44.836 | −27.889 | 21.068 | 1.00 | 29.35 | A | C |
| ATOM | 7521 | CB | THR | A | 487 | 46.016 | −27.585 | 22.018 | 1.00 | 31.65 | A | C |
| ATOM | 7523 | OG1 | THR | A | 487 | 45.866 | −26.262 | 22.551 | 1.00 | 34.58 | A | O |
| ATOM | 7525 | CG2 | THR | A | 487 | 47.356 | −27.676 | 21.303 | 1.00 | 29.45 | A | C |
| ATOM | 7529 | C | THR | A | 487 | 45.083 | −29.179 | 20.293 | 1.00 | 30.58 | A | C |
| ATOM | 7530 | O | THR | A | 487 | 45.510 | −29.148 | 19.136 | 1.00 | 30.56 | A | O |
| ATOM | 7532 | N | GLU | A | 488 | 44.778 | −30.311 | 20.912 | 1.00 | 30.73 | A | N |
| ATOM | 7533 | CA | GLU | A | 488 | 44.909 | −31.596 | 20.251 | 1.00 | 31.69 | A | C |
| ATOM | 7535 | CB | GLU | A | 488 | 44.559 | −32.726 | 21.226 | 1.00 | 34.61 | A | C |
| ATOM | 7538 | CG | GLU | A | 488 | 44.929 | −34.158 | 20.782 | 1.00 | 42.91 | A | C |
| ATOM | 7541 | CD | GLU | A | 488 | 44.468 | −35.230 | 21.805 | 1.00 | 51.83 | A | C |
| ATOM | 7542 | OE1 | GLU | A | 488 | 45.312 | −36.038 | 22.257 | 1.00 | 53.97 | A | O |
| ATOM | 7543 | OE2 | GLU | A | 488 | 43.263 | −35.252 | 22.169 | 1.00 | 57.42 | A | O |
| ATOM | 7544 | C | GLU | A | 488 | 43.990 | −31.653 | 19.039 | 1.00 | 30.86 | A | C |
| ATOM | 7545 | O | GLU | A | 488 | 44.406 | −32.077 | 17.959 | 1.00 | 30.25 | A | O |
| ATOM | 7547 | N | SER | A | 489 | 42.742 | −31.226 | 19.216 | 1.00 | 28.77 | A | N |
| ATOM | 7548 | CA | SER | A | 489 | 41.759 | −31.338 | 18.153 | 1.00 | 29.03 | A | C |
| ATOM | 7550 | CB | SER | A | 489 | 40.361 | −31.004 | 18.646 | 1.00 | 28.33 | A | C |
| ATOM | 7553 | OG | SER | A | 489 | 40.002 | −31.853 | 19.725 | 1.00 | 37.93 | A | O |
| ATOM | 7555 | C | SER | A | 489 | 42.124 | −30.416 | 17.000 | 1.00 | 28.35 | A | C |
| ATOM | 7556 | O | SER | A | 489 | 41.905 | −30.761 | 15.842 | 1.00 | 29.09 | A | O |
| ATOM | 7558 | N | VAL | A | 490 | 42.683 | −29.257 | 17.327 | 1.00 | 27.58 | A | N |
| ATOM | 7559 | CA | VAL | A | 490 | 43.156 | −28.332 | 16.308 | 1.00 | 27.37 | A | C |
| ATOM | 7561 | CB | VAL | A | 490 | 43.492 | −26.971 | 16.899 | 1.00 | 27.54 | A | C |
| ATOM | 7563 | CG1 | VAL | A | 490 | 44.224 | −26.084 | 15.887 | 1.00 | 23.38 | A | C |
| ATOM | 7567 | CG2 | VAL | A | 490 | 42.186 | −26.322 | 17.351 | 1.00 | 26.23 | A | C |
| ATOM | 7571 | C | VAL | A | 490 | 44.308 | −28.940 | 15.538 | 1.00 | 27.62 | A | C |
| ATOM | 7572 | O | VAL | A | 490 | 44.316 | −28.869 | 14.319 | 1.00 | 28.81 | A | O |

TABLE 4-2-continued

Coordinates of *P. alba* IspS

| ATOM | 7574 | N | MET | A | 491 | 45.242 | −29.589 | 16.225 | 1.00 | 29.11 | A | N |
| ATOM | 7575 | CA | MET | A | 491 | 46.328 | −30.317 | 15.530 | 1.00 | 28.74 | A | C |
| ATOM | 7577 | CB | MET | A | 491 | 47.254 | −31.019 | 16.529 | 1.00 | 32.05 | A | C |
| ATOM | 7580 | CG | MET | A | 491 | 48.053 | −30.105 | 17.437 | 1.00 | 34.71 | A | C |
| ATOM | 7583 | SD | MET | A | 491 | 49.345 | −29.289 | 16.533 | 1.00 | 54.88 | A | S |
| ATOM | 7584 | CE | MET | A | 491 | 50.240 | −28.583 | 17.932 | 1.00 | 61.26 | A | C |
| ATOM | 7588 | C | MET | A | 491 | 45.764 | −31.376 | 14.592 | 1.00 | 27.27 | A | C |
| ATOM | 7589 | O | MET | A | 491 | 46.251 | −31.544 | 13.480 | 1.00 | 29.18 | A | O |
| ATOM | 7591 | N | ASN | A | 492 | 44.742 | −32.102 | 15.042 | 1.00 | 24.90 | A | N |
| ATOM | 7592 | CA | ASN | A | 492 | 44.112 | −33.108 | 14.194 | 1.00 | 24.42 | A | C |
| ATOM | 7594 | CB | ASN | A | 492 | 43.117 | −33.973 | 14.976 | 1.00 | 27.09 | A | C |
| ATOM | 7597 | CG | ASN | A | 492 | 43.790 | −34.834 | 16.076 | 1.00 | 32.10 | A | C |
| ATOM | 7598 | OD1 | ASN | A | 492 | 45.011 | −35.022 | 16.111 | 1.00 | 36.38 | A | O |
| ATOM | 7599 | ND2 | ASN | A | 492 | 42.971 | −35.342 | 16.983 | 1.00 | 29.67 | A | N |
| ATOM | 7602 | C | ASN | A | 492 | 43.416 | −32.509 | 12.971 | 1.00 | 21.31 | A | C |
| ATOM | 7603 | O | ASN | A | 492 | 43.365 | −33.141 | 11.924 | 1.00 | 19.60 | A | O |
| ATOM | 7605 | N | LEU | A | 493 | 42.864 | −31.312 | 13.119 | 1.00 | 19.85 | A | N |
| ATOM | 7606 | CA | LEU | A | 493 | 42.208 | −30.609 | 12.026 | 1.00 | 21.49 | A | C |
| ATOM | 7608 | CB | LEU | A | 493 | 41.438 | −29.402 | 12.570 | 1.00 | 22.55 | A | C |
| ATOM | 7611 | CG | LEU | A | 493 | 40.562 | −28.537 | 11.637 | 1.00 | 30.39 | A | C |
| ATOM | 7613 | CD1 | LEU | A | 493 | 39.640 | −29.355 | 10.718 | 1.00 | 30.23 | A | C |
| ATOM | 7617 | CD2 | LEU | A | 493 | 39.693 | −27.559 | 12.479 | 1.00 | 23.06 | A | C |
| ATOM | 7621 | C | LEU | A | 493 | 43.253 | −30.196 | 10.988 | 1.00 | 20.61 | A | C |
| ATOM | 7622 | O | LEU | A | 493 | 43.024 | −30.298 | 9.781 | 1.00 | 21.55 | A | O |
| ATOM | 7624 | N | ILE | A | 494 | 44.427 | −29.800 | 11.463 | 1.00 | 19.95 | A | N |
| ATOM | 7625 | CA | ILE | A | 494 | 45.529 | −29.519 | 10.574 | 1.00 | 21.52 | A | C |
| ATOM | 7627 | CB | ILE | A | 494 | 46.739 | −28.978 | 11.329 | 1.00 | 20.44 | A | C |
| ATOM | 7629 | CG1 | ILE | A | 494 | 46.492 | −27.511 | 11.724 | 1.00 | 22.83 | A | C |
| ATOM | 7632 | CD1 | ILE | A | 494 | 47.454 | −27.023 | 12.815 | 1.00 | 19.27 | A | C |
| ATOM | 7636 | CG2 | ILE | A | 494 | 47.989 | −29.041 | 10.489 | 1.00 | 18.64 | A | C |
| ATOM | 7640 | C | ILE | A | 494 | 45.898 | −30.764 | 9.762 | 1.00 | 22.01 | A | C |
| ATOM | 7641 | O | ILE | A | 494 | 46.021 | −30.688 | 8.539 | 1.00 | 25.12 | A | O |
| ATOM | 7643 | N | ASP | A | 495 | 46.087 | −31.885 | 10.437 | 1.00 | 20.80 | A | N |
| ATOM | 7644 | CA | ASP | A | 495 | 46.397 | −33.138 | 9.773 | 1.00 | 21.60 | A | C |
| ATOM | 7646 | CB | ASP | A | 495 | 46.473 | −34.281 | 10.791 | 1.00 | 22.75 | A | C |
| ATOM | 7649 | CG | ASP | A | 495 | 47.682 | −34.161 | 11.731 | 1.00 | 24.78 | A | C |
| ATOM | 7650 | OD1 | ASP | A | 495 | 48.662 | −33.458 | 11.379 | 1.00 | 31.93 | A | O |
| ATOM | 7651 | OD2 | ASP | A | 495 | 47.641 | −34.762 | 12.831 | 1.00 | 35.25 | A | O |
| ATOM | 7652 | C | ASP | A | 495 | 45.346 | −33.462 | 8.740 | 1.00 | 22.09 | A | C |
| ATOM | 7653 | O | ASP | A | 495 | 45.666 | −33.770 | 7.596 | 1.00 | 22.13 | A | O |
| ATOM | 7655 | N | GLU | A | 496 | 44.087 | −33.342 | 9.134 | 1.00 | 23.17 | A | N |
| ATOM | 7656 | CA | GLU | A | 496 | 42.972 | −33.693 | 8.258 | 1.00 | 25.14 | A | C |
| ATOM | 7658 | CB | GLU | A | 496 | 41.643 | −33.501 | 8.984 | 1.00 | 26.79 | A | C |
| ATOM | 7661 | CG | GLU | A | 496 | 40.397 | −33.761 | 8.177 | 1.00 | 35.71 | A | C |
| ATOM | 7664 | CD | GLU | A | 496 | 39.117 | −33.280 | 8.886 | 1.00 | 44.71 | A | C |
| ATOM | 7665 | OE1 | GLU | A | 496 | 38.810 | −33.788 | 9.987 | 1.00 | 47.95 | A | O |
| ATOM | 7666 | OE2 | GLU | A | 496 | 38.416 | −32.402 | 8.328 | 1.00 | 50.58 | A | O |
| ATOM | 7667 | C | GLU | A | 496 | 43.032 | −32.834 | 7.024 | 1.00 | 24.17 | A | C |
| ATOM | 7668 | O | GLU | A | 496 | 42.890 | −33.344 | 5.909 | 1.00 | 23.57 | A | O |
| ATOM | 7670 | N | THR | A | 497 | 43.271 | −31.535 | 7.232 | 1.00 | 23.07 | A | N |
| ATOM | 7671 | CA | THR | A | 497 | 43.327 | −30.575 | 6.143 | 1.00 | 21.41 | A | C |
| ATOM | 7673 | CB | THR | A | 497 | 43.465 | −29.157 | 6.674 | 1.00 | 22.58 | A | C |
| ATOM | 7675 | OG1 | THR | A | 497 | 42.381 | −28.887 | 7.575 | 1.00 | 25.05 | A | O |
| ATOM | 7677 | CG2 | THR | A | 497 | 43.436 | −28.162 | 5.551 | 1.00 | 17.59 | A | C |
| ATOM | 7681 | C | THR | A | 497 | 44.481 | −30.901 | 5.175 | 1.00 | 22.39 | A | C |
| ATOM | 7682 | O | THR | A | 497 | 44.304 | −30.840 | 3.961 | 1.00 | 20.87 | A | O |
| ATOM | 7684 | N | TRP | A | 498 | 45.641 | −31.275 | 5.718 | 1.00 | 20.20 | A | N |
| ATOM | 7685 | CA | TRP | A | 498 | 46.743 | −31.748 | 4.888 | 1.00 | 21.37 | A | C |
| ATOM | 7687 | CB | TRP | A | 498 | 47.973 | −32.065 | 5.760 | 1.00 | 18.97 | A | C |
| ATOM | 7690 | CG | TRP | A | 498 | 48.874 | −30.887 | 5.894 | 1.00 | 21.52 | A | C |
| ATOM | 7691 | CD1 | TRP | A | 498 | 48.969 | −30.038 | 6.953 | 1.00 | 13.13 | A | C |
| ATOM | 7693 | NE1 | TRP | A | 498 | 49.885 | −29.084 | 6.704 | 1.00 | 21.91 | A | N |
| ATOM | 7695 | CE2 | TRP | A | 498 | 50.399 | −29.277 | 5.454 | 1.00 | 19.92 | A | C |
| ATOM | 7696 | CD2 | TRP | A | 498 | 49.780 | −30.409 | 4.920 | 1.00 | 17.93 | A | C |
| ATOM | 7697 | CE3 | TRP | A | 498 | 50.135 | −30.832 | 3.646 | 1.00 | 23.82 | A | C |
| ATOM | 7699 | CZ3 | TRP | A | 498 | 51.097 | −30.125 | 2.961 | 1.00 | 24.54 | A | C |
| ATOM | 7701 | CH2 | TRP | A | 498 | 51.705 | −29.007 | 3.526 | 1.00 | 25.21 | A | C |
| ATOM | 7703 | CZ2 | TRP | A | 498 | 51.375 | −28.572 | 4.775 | 1.00 | 24.04 | A | C |
| ATOM | 7705 | C | TRP | A | 498 | 46.387 | −32.963 | 4.013 | 1.00 | 19.42 | A | C |
| ATOM | 7706 | O | TRP | A | 498 | 46.715 | −33.008 | 2.836 | 1.00 | 20.26 | A | O |
| ATOM | 7708 | N | LYS | A | 499 | 45.727 | −33.944 | 4.588 | 1.00 | 19.66 | A | N |
| ATOM | 7709 | CA | LYS | A | 499 | 45.320 | −35.113 | 3.824 | 1.00 | 21.18 | A | C |
| ATOM | 7711 | CB | LYS | A | 499 | 44.554 | −36.105 | 4.701 | 1.00 | 20.73 | A | C |
| ATOM | 7714 | CG | LYS | A | 499 | 45.406 | −36.825 | 5.766 | 1.00 | 20.29 | A | C |
| ATOM | 7717 | CD | LYS | A | 499 | 44.547 | −37.888 | 6.525 | 1.00 | 21.48 | A | C |
| ATOM | 7720 | CE | LYS | A | 499 | 45.126 | −38.323 | 7.841 | 1.00 | 21.99 | A | C |
| ATOM | 7723 | NZ | LYS | A | 499 | 44.166 | −39.231 | 8.565 | 1.00 | 24.95 | A | N |
| ATOM | 7727 | C | LYS | A | 499 | 44.451 | −34.701 | 2.655 | 1.00 | 20.41 | A | C |

TABLE 4-2-continued

Coordinates of *P. alba* IspS

| ATOM | 7728 | O | LYS | A | 499 | 44.532 | −35.278 | 1.598 | 1.00 | 23.27 | A | O |
|---|---|---|---|---|---|---|---|---|---|---|---|---|
| ATOM | 7730 | N | LYS | A | 500 | 43.628 | −33.688 | 2.842 | 1.00 | 20.82 | A | N |
| ATOM | 7731 | CA | LYS | A | 500 | 42.761 | −33.233 | 1.779 | 1.00 | 23.10 | A | C |
| ATOM | 7733 | CB | LYS | A | 500 | 41.613 | −32.392 | 2.351 | 1.00 | 24.87 | A | C |
| ATOM | 7736 | CG | LYS | A | 500 | 40.575 | −33.199 | 3.110 | 1.00 | 24.42 | A | C |
| ATOM | 7739 | CD | LYS | A | 500 | 39.505 | −32.282 | 3.741 | 1.00 | 34.06 | A | C |
| ATOM | 7742 | CE | LYS | A | 500 | 38.487 | −33.073 | 4.598 | 1.00 | 33.59 | A | C |
| ATOM | 7745 | NZ | LYS | A | 500 | 37.318 | −32.261 | 5.058 | 1.00 | 39.36 | A | N |
| ATOM | 7749 | C | LYS | A | 500 | 43.529 | −32.461 | 0.703 | 1.00 | 22.13 | A | C |
| ATOM | 7750 | O | LYS | A | 500 | 43.233 | −32.586 | −0.469 | 1.00 | 23.08 | A | O |
| ATOM | 7752 | N | MET | A | 501 | 44.516 | −31.665 | 1.088 | 1.00 | 22.16 | A | N |
| ATOM | 7753 | CA | MET | A | 501 | 45.324 | −30.960 | 0.101 | 1.00 | 19.81 | A | C |
| ATOM | 7755 | CB | MET | A | 501 | 46.228 | −29.944 | 0.770 | 1.00 | 19.32 | A | C |
| ATOM | 7758 | CG | MET | A | 501 | 45.516 | −28.822 | 1.490 | 1.00 | 21.43 | A | C |
| ATOM | 7761 | SD | MET | A | 501 | 46.681 | −27.490 | 1.974 | 1.00 | 27.05 | A | S |
| ATOM | 7762 | CE | MET | A | 501 | 47.856 | −28.310 | 3.053 | 1.00 | 23.38 | A | C |
| ATOM | 7766 | C | MET | A | 501 | 46.176 | −31.946 | −0.698 | 1.00 | 18.61 | A | C |
| ATOM | 7767 | O | MET | A | 501 | 46.410 | −31.758 | −1.888 | 1.00 | 18.54 | A | O |
| ATOM | 7769 | N | ASN | A | 502 | 46.658 | −32.991 | −0.037 | 1.00 | 19.21 | A | N |
| ATOM | 7770 | CA | ASN | A | 502 | 47.440 | −34.013 | −0.717 | 1.00 | 18.62 | A | C |
| ATOM | 7772 | CB | ASN | A | 502 | 47.922 | −35.069 | 0.277 | 1.00 | 18.18 | A | C |
| ATOM | 7775 | CG | ASN | A | 502 | 48.980 | −34.544 | 1.216 | 1.00 | 20.41 | A | C |
| ATOM | 7776 | OD1 | ASN | A | 502 | 49.635 | −33.522 | 0.933 | 1.00 | 20.85 | A | O |
| ATOM | 7777 | ND2 | ASN | A | 502 | 49.167 | −35.244 | 2.353 | 1.00 | 14.88 | A | N |
| ATOM | 7780 | C | ASN | A | 502 | 46.629 | −34.674 | −1.815 | 1.00 | 20.92 | A | C |
| ATOM | 7781 | O | ASN | A | 502 | 47.140 | −34.963 | −2.889 | 1.00 | 21.10 | A | O |
| ATOM | 7783 | N | LYS | A | 503 | 45.361 | −34.902 | −1.548 | 1.00 | 21.59 | A | N |
| ATOM | 7784 | CA | LYS | A | 503 | 44.492 | −35.487 | −2.543 | 1.00 | 26.84 | A | C |
| ATOM | 7786 | CB | LYS | A | 503 | 43.158 | −35.894 | −1.907 | 1.00 | 25.07 | A | C |
| ATOM | 7789 | CG | LYS | A | 503 | 42.272 | −36.688 | −2.832 | 1.00 | 31.50 | A | C |
| ATOM | 7792 | CD | LYS | A | 503 | 41.048 | −37.279 | −2.122 | 1.00 | 37.63 | A | C |
| ATOM | 7795 | CE | LYS | A | 503 | 40.180 | −38.027 | −3.135 | 1.00 | 42.50 | A | C |
| ATOM | 7798 | NZ | LYS | A | 503 | 38.799 | −38.319 | −2.637 | 1.00 | 39.80 | A | N |
| ATOM | 7802 | C | LYS | A | 503 | 44.265 | −34.554 | −3.751 | 1.00 | 26.24 | A | C |
| ATOM | 7803 | O | LYS | A | 503 | 44.388 | −34.969 | −4.896 | 1.00 | 24.15 | A | O |
| ATOM | 7805 | N | GLU | A | 504 | 43.937 | −33.301 | −3.477 | 1.00 | 28.57 | A | N |
| ATOM | 7806 | CA | GLU | A | 504 | 43.681 | −32.298 | −4.520 | 1.00 | 28.52 | A | C |
| ATOM | 7808 | CB | GLU | A | 504 | 43.343 | −30.946 | −3.865 | 1.00 | 30.61 | A | C |
| ATOM | 7811 | CG | GLU | A | 504 | 42.958 | −29.790 | −4.821 | 1.00 | 38.94 | A | C |
| ATOM | 7814 | CD | GLU | A | 504 | 41.566 | −29.921 | −5.427 | 1.00 | 46.58 | A | C |
| ATOM | 7815 | OE1 | GLU | A | 504 | 41.310 | −29.262 | −6.453 | 1.00 | 52.18 | A | O |
| ATOM | 7816 | OE2 | GLU | A | 504 | 40.723 | −30.683 | −4.896 | 1.00 | 53.41 | A | O |
| ATOM | 7817 | C | GLU | A | 504 | 44.920 | −32.185 | −5.412 | 1.00 | 27.76 | A | C |
| ATOM | 7818 | O | GLU | A | 504 | 44.814 | −32.059 | −6.628 | 1.00 | 26.82 | A | O |
| ATOM | 7820 | N | LYS | A | 505 | 46.101 | −32.268 | −4.805 | 1.00 | 25.80 | A | N |
| ATOM | 7821 | CA | LYS | A | 505 | 47.338 | −32.166 | −5.559 | 1.00 | 26.51 | A | C |
| ATOM | 7823 | CB | LYS | A | 505 | 48.533 | −32.046 | −4.617 | 1.00 | 23.37 | A | C |
| ATOM | 7826 | CG | LYS | A | 505 | 49.916 | −32.048 | −5.295 | 1.00 | 23.18 | A | C |
| ATOM | 7829 | CD | LYS | A | 505 | 50.165 | −30.869 | −6.209 | 1.00 | 27.18 | A | C |
| ATOM | 7832 | CE | LYS | A | 505 | 51.471 | −31.033 | −7.011 | 1.00 | 21.66 | A | C |
| ATOM | 7835 | NZ | LYS | A | 505 | 52.684 | −30.936 | −6.205 | 1.00 | 31.62 | A | N |
| ATOM | 7839 | C | LYS | A | 505 | 47.531 | −33.360 | −6.491 | 1.00 | 28.51 | A | C |
| ATOM | 7840 | O | LYS | A | 505 | 48.058 | −33.230 | −7.598 | 1.00 | 28.28 | A | O |
| ATOM | 7842 | N | LEU | A | 506 | 47.137 | −34.520 | −6.011 | 1.00 | 31.86 | A | N |
| ATOM | 7843 | CA | LEU | A | 506 | 47.448 | −35.765 | −6.663 | 1.00 | 36.04 | A | C |
| ATOM | 7845 | CB | LEU | A | 506 | 47.288 | −36.918 | −5.682 | 1.00 | 37.63 | A | C |
| ATOM | 7848 | CG | LEU | A | 506 | 48.038 | −38.207 | −5.980 | 1.00 | 42.29 | A | C |
| ATOM | 7850 | CD1 | LEU | A | 506 | 49.507 | −37.926 | −6.154 | 1.00 | 35.85 | A | C |
| ATOM | 7854 | CD2 | LEU | A | 506 | 47.800 | −39.204 | −4.820 | 1.00 | 46.05 | A | C |
| ATOM | 7858 | C | LEU | A | 506 | 46.558 | −35.972 | −7.872 | 1.00 | 37.67 | A | C |
| ATOM | 7859 | O | LEU | A | 506 | 47.003 | −36.495 | −8.875 | 1.00 | 38.71 | A | O |
| ATOM | 7861 | N | GLY | A | 507 | 45.309 | −35.552 | −7.797 | 1.00 | 39.52 | A | N |
| ATOM | 7862 | CA | GLY | A | 507 | 44.443 | −35.753 | −8.922 | 1.00 | 43.92 | A | C |
| ATOM | 7865 | C | GLY | A | 507 | 43.260 | −34.842 | −8.940 | 1.00 | 46.84 | A | C |
| ATOM | 7866 | O | GLY | A | 507 | 42.912 | −34.221 | −7.932 | 1.00 | 49.96 | A | O |
| ATOM | 7868 | N | GLY | A | 508 | 42.676 | −34.743 | −10.122 | 1.00 | 49.06 | A | N |
| ATOM | 7869 | CA | GLY | A | 508 | 41.363 | −34.150 | −10.302 | 1.00 | 50.99 | A | C |
| ATOM | 7872 | C | GLY | A | 508 | 41.194 | −32.736 | −9.777 | 1.00 | 50.71 | A | C |
| ATOM | 7873 | O | GLY | A | 508 | 40.122 | −32.409 | −9.241 | 1.00 | 52.36 | A | O |
| ATOM | 7875 | N | SER | A | 509 | 42.203 | −31.880 | −9.918 | 1.00 | 47.13 | A | N |
| ATOM | 7876 | CA | SER | A | 509 | 41.952 | −30.484 | −9.528 | 1.00 | 47.06 | A | C |
| ATOM | 7878 | CB | SER | A | 509 | 43.191 | −29.736 | −8.981 | 1.00 | 45.68 | A | C |
| ATOM | 7881 | OG | SER | A | 509 | 42.806 | −28.477 | −8.381 | 1.00 | 42.36 | A | O |
| ATOM | 7883 | C | SER | A | 509 | 41.382 | −29.749 | −10.715 | 1.00 | 44.82 | A | C |
| ATOM | 7884 | O | SER | A | 509 | 41.689 | −30.070 | −11.852 | 1.00 | 42.86 | A | O |
| ATOM | 7886 | N | LEU | A | 510 | 40.554 | −28.756 | −10.416 | 1.00 | 45.06 | A | N |
| ATOM | 7887 | CA | LEU | A | 510 | 40.113 | −27.777 | −11.399 | 1.00 | 45.40 | A | C |
| ATOM | 7889 | CB | LEU | A | 510 | 38.958 | −26.930 | −10.832 | 1.00 | 47.41 | A | C |

TABLE 4-2-continued

Coordinates of *P. alba* IspS

| ATOM | 7892 | CG | LEU | A | 510 | 37.786 | −27.690 | −10.165 | 1.00 | 55.26 | A | C |
|---|---|---|---|---|---|---|---|---|---|---|---|---|
| ATOM | 7894 | CD1 | LEU | A | 510 | 36.624 | −26.741 | −9.788 | 1.00 | 57.58 | A | C |
| ATOM | 7898 | CD2 | LEU | A | 510 | 37.270 | −28.882 | −11.042 | 1.00 | 61.12 | A | C |
| ATOM | 7902 | C | LEU | A | 510 | 41.286 | −26.872 | −11.801 | 1.00 | 42.51 | A | C |
| ATOM | 7903 | O | LEU | A | 510 | 41.294 | −26.326 | −12.901 | 1.00 | 44.42 | A | O |
| ATOM | 7905 | N | PHE | A | 511 | 42.267 | −26.730 | −10.908 | 1.00 | 37.23 | A | N |
| ATOM | 7906 | CA | PHE | A | 511 | 43.472 | −25.953 | −11.166 | 1.00 | 34.84 | A | C |
| ATOM | 7908 | CB | PHE | A | 511 | 43.886 | −25.210 | −9.902 | 1.00 | 34.34 | A | C |
| ATOM | 7911 | CG | PHE | A | 511 | 42.953 | −24.144 | −9.522 | 1.00 | 28.92 | A | C |
| ATOM | 7912 | CD1 | PHE | A | 511 | 43.120 | −22.857 | −10.008 | 1.00 | 29.05 | A | C |
| ATOM | 7914 | CE1 | PHE | A | 511 | 42.239 | −21.868 | −9.667 | 1.00 | 31.91 | A | C |
| ATOM | 7916 | CZ | PHE | A | 511 | 41.166 | −22.149 | −8.835 | 1.00 | 34.31 | A | C |
| ATOM | 7918 | CE2 | PHE | A | 511 | 40.987 | −23.436 | −8.353 | 1.00 | 31.94 | A | C |
| ATOM | 7920 | CD2 | PHE | A | 511 | 41.879 | −24.420 | −8.705 | 1.00 | 28.15 | A | C |
| ATOM | 7922 | C | PHE | A | 511 | 44.646 | −26.806 | −11.627 | 1.00 | 33.67 | A | C |
| ATOM | 7923 | O | PHE | A | 511 | 44.729 | −27.979 | −11.330 | 1.00 | 32.95 | A | O |
| ATOM | 7925 | N | ALA | A | 512 | 45.581 | −26.186 | −12.334 | 1.00 | 35.25 | A | N |
| ATOM | 7926 | CA | ALA | A | 512 | 46.800 | −26.873 | −12.750 | 1.00 | 35.70 | A | C |
| ATOM | 7928 | CB | ALA | A | 512 | 47.539 | −26.051 | −13.813 | 1.00 | 34.66 | A | C |
| ATOM | 7932 | C | ALA | A | 512 | 47.707 | −27.148 | −11.529 | 1.00 | 36.10 | A | C |
| ATOM | 7933 | O | ALA | A | 512 | 47.699 | −26.406 | −10.547 | 1.00 | 36.63 | A | O |
| ATOM | 7935 | N | LYS | A | 513 | 48.475 | −28.225 | −11.603 | 1.00 | 36.02 | A | N |
| ATOM | 7936 | CA | LYS | A | 513 | 49.284 | −28.673 | −10.484 | 1.00 | 37.34 | A | C |
| ATOM | 7938 | CB | LYS | A | 513 | 50.063 | −29.942 | −10.849 | 1.00 | 37.46 | A | C |
| ATOM | 7941 | CG | LYS | A | 513 | 49.162 | −31.182 | −10.883 | 1.00 | 43.80 | A | C |
| ATOM | 7944 | CD | LYS | A | 513 | 49.963 | −32.482 | −10.925 | 1.00 | 50.12 | A | C |
| ATOM | 7947 | CE | LYS | A | 513 | 49.023 | −33.696 | −10.922 | 1.00 | 56.16 | A | C |
| ATOM | 7950 | NZ | LYS | A | 513 | 49.717 | −34.969 | −10.585 | 1.00 | 55.05 | A | N |
| ATOM | 7954 | C | LYS | A | 513 | 50.214 | −27.622 | −9.884 | 1.00 | 35.55 | A | C |
| ATOM | 7955 | O | LYS | A | 513 | 50.337 | −27.571 | −8.679 | 1.00 | 34.97 | A | O |
| ATOM | 7957 | N | PRO | A | 514 | 50.850 | −26.775 | −10.715 | 1.00 | 33.86 | A | N |
| ATOM | 7958 | CA | PRO | A | 514 | 51.776 | −25.809 | −10.137 | 1.00 | 30.23 | A | C |
| ATOM | 7960 | CB | PRO | A | 514 | 52.402 | −25.116 | −11.359 | 1.00 | 30.51 | A | C |
| ATOM | 7963 | CG | PRO | A | 514 | 52.125 | −26.036 | −12.529 | 1.00 | 34.84 | A | C |
| ATOM | 7966 | CD | PRO | A | 514 | 50.855 | −26.753 | −12.197 | 1.00 | 35.73 | A | C |
| ATOM | 7969 | C | PRO | A | 514 | 51.082 | −24.796 | −9.233 | 1.00 | 27.77 | A | C |
| ATOM | 7970 | O | PRO | A | 514 | 51.627 | −24.406 | −8.205 | 1.00 | 30.05 | A | O |
| ATOM | 7971 | N | PHE | A | 515 | 49.886 | −24.373 | −9.587 | 1.00 | 25.77 | A | N |
| ATOM | 7972 | CA | PHE | A | 515 | 49.195 | −23.428 | −8.732 | 1.00 | 24.83 | A | C |
| ATOM | 7974 | CB | PHE | A | 515 | 48.074 | −22.699 | −9.462 | 1.00 | 23.92 | A | C |
| ATOM | 7977 | CG | PHE | A | 515 | 47.262 | −21.818 | −8.557 | 1.00 | 26.15 | A | C |
| ATOM | 7978 | CD1 | PHE | A | 515 | 47.779 | −20.626 | −8.087 | 1.00 | 25.26 | A | C |
| ATOM | 7980 | CE1 | PHE | A | 515 | 47.041 | −19.832 | −7.203 | 1.00 | 25.88 | A | C |
| ATOM | 7982 | CZ | PHE | A | 515 | 45.780 | −20.227 | −6.804 | 1.00 | 22.17 | A | C |
| ATOM | 7984 | CE2 | PHE | A | 515 | 45.266 | −21.432 | −7.253 | 1.00 | 23.27 | A | C |
| ATOM | 7986 | CD2 | PHE | A | 515 | 46.011 | −22.225 | −8.108 | 1.00 | 26.63 | A | C |
| ATOM | 7988 | C | PHE | A | 515 | 48.675 | −24.143 | −7.460 | 1.00 | 24.34 | A | C |
| ATOM | 7989 | O | PHE | A | 515 | 48.794 | −23.599 | −6.371 | 1.00 | 23.33 | A | O |
| ATOM | 7991 | N | VAL | A | 516 | 48.156 | −25.369 | −7.588 | 1.00 | 22.98 | A | N |
| ATOM | 7992 | CA | VAL | A | 516 | 47.815 | −26.159 | −6.401 | 1.00 | 22.66 | A | C |
| ATOM | 7994 | CB | VAL | A | 516 | 47.387 | −27.605 | −6.706 | 1.00 | 24.87 | A | C |
| ATOM | 7996 | CG1 | VAL | A | 516 | 46.149 | −27.671 | −7.666 | 1.00 | 22.01 | A | C |
| ATOM | 8000 | CG2 | VAL | A | 516 | 47.109 | −28.387 | −5.377 | 1.00 | 17.25 | A | C |
| ATOM | 8004 | C | VAL | A | 516 | 49.022 | −26.187 | −5.432 | 1.00 | 22.26 | A | C |
| ATOM | 8005 | O | VAL | A | 516 | 48.861 | −25.964 | −4.228 | 1.00 | 21.22 | A | O |
| ATOM | 8007 | N | GLU | A | 517 | 50.213 | −26.411 | −5.976 | 1.00 | 21.70 | A | N |
| ATOM | 8008 | CA | GLU | A | 517 | 51.456 | −26.510 | −5.188 | 1.00 | 22.29 | A | C |
| ATOM | 8010 | CB | GLU | A | 517 | 52.584 | −27.047 | −6.072 | 1.00 | 22.50 | A | C |
| ATOM | 8013 | CG | GLU | A | 517 | 53.939 | −27.283 | −5.376 | 1.00 | 19.35 | A | C |
| ATOM | 8016 | CD | GLU | A | 517 | 53.941 | −28.451 | −4.347 | 1.00 | 27.61 | A | C |
| ATOM | 8017 | OE1 | GLU | A | 517 | 52.962 | −29.218 | −4.228 | 1.00 | 23.47 | A | O |
| ATOM | 8018 | OE2 | GLU | A | 517 | 54.940 | −28.605 | −3.631 | 1.00 | 30.16 | A | O |
| ATOM | 8019 | C | GLU | A | 517 | 51.847 | −25.157 | −4.576 | 1.00 | 22.35 | A | C |
| ATOM | 8020 | O | GLU | A | 517 | 52.253 | −25.096 | −3.404 | 1.00 | 26.83 | A | O |
| ATOM | 8022 | N | THR | A | 518 | 51.709 | −24.082 | −5.354 | 1.00 | 21.58 | A | N |
| ATOM | 8023 | CA | THR | A | 518 | 51.902 | −22.731 | −4.836 | 1.00 | 24.40 | A | C |
| ATOM | 8025 | CB | THR | A | 518 | 51.689 | −21.634 | −5.925 | 1.00 | 26.67 | A | C |
| ATOM | 8027 | OG1 | THR | A | 518 | 52.642 | −21.808 | −6.973 | 1.00 | 23.81 | A | O |
| ATOM | 8029 | CG2 | THR | A | 518 | 51.876 | −20.228 | −5.351 | 1.00 | 24.26 | A | C |
| ATOM | 8033 | C | THR | A | 518 | 50.969 | −22.518 | −3.644 | 1.00 | 25.98 | A | C |
| ATOM | 8034 | O | THR | A | 518 | 51.400 | −22.003 | −2.596 | 1.00 | 25.54 | A | O |
| ATOM | 8036 | N | ALA | A | 519 | 49.717 | −22.968 | −3.774 | 1.00 | 23.55 | A | N |
| ATOM | 8037 | CA | ALA | A | 519 | 48.772 | −22.859 | −2.676 | 1.00 | 23.19 | A | C |
| ATOM | 8039 | CB | ALA | A | 519 | 47.375 | −23.219 | −3.096 | 1.00 | 20.70 | A | C |
| ATOM | 8043 | C | ALA | A | 519 | 49.182 | −23.644 | −1.436 | 1.00 | 23.29 | A | C |
| ATOM | 8044 | O | ALA | A | 519 | 49.096 | −23.125 | −0.286 | 1.00 | 24.26 | A | O |
| ATOM | 8046 | N | ILE | A | 520 | 49.673 | −24.853 | −1.639 | 1.00 | 21.17 | A | N |
| ATOM | 8047 | CA | ILE | A | 520 | 50.097 | −25.677 | −0.500 | 1.00 | 19.87 | A | C |

TABLE 4-2-continued

Coordinates of P. alba IspS

| ATOM | 8049 | CB | ILE | A | 520 | 50.425 | −27.126 | −0.957 | 1.00 | 20.77 | A | C |
|---|---|---|---|---|---|---|---|---|---|---|---|---|
| ATOM | 8051 | CG1 | ILE | A | 520 | 49.146 | −27.857 | −1.421 | 1.00 | 20.74 | A | C |
| ATOM | 8054 | CD1 | ILE | A | 520 | 49.421 | −29.223 | −2.184 | 1.00 | 19.45 | A | C |
| ATOM | 8058 | CG2 | ILE | A | 520 | 51.083 | −27.909 | 0.152 | 1.00 | 16.11 | A | C |
| ATOM | 8062 | C | ILE | A | 520 | 51.288 | −25.003 | 0.202 | 1.00 | 20.17 | A | C |
| ATOM | 8063 | O | ILE | A | 520 | 51.384 | −25.018 | 1.437 | 1.00 | 19.37 | A | O |
| ATOM | 8065 | N | ASN | A | 521 | 52.166 | −24.366 | −0.574 | 1.00 | 21.54 | A | N |
| ATOM | 8066 | CA | ASN | A | 521 | 53.299 | −23.620 | 0.014 | 1.00 | 20.54 | A | C |
| ATOM | 8068 | CB | ASN | A | 521 | 54.188 | −22.992 | −1.066 | 1.00 | 21.56 | A | C |
| ATOM | 8071 | CG | ASN | A | 521 | 54.966 | −24.024 | −1.867 | 1.00 | 24.44 | A | C |
| ATOM | 8072 | OD1 | ASN | A | 521 | 55.198 | −25.124 | −1.399 | 1.00 | 19.38 | A | O |
| ATOM | 8073 | ND2 | ASN | A | 521 | 55.365 | −23.666 | −3.084 | 1.00 | 18.91 | A | N |
| ATOM | 8076 | C | ASN | A | 521 | 52.892 | −22.559 | 1.017 | 1.00 | 19.40 | A | C |
| ATOM | 8077 | O | ASN | A | 521 | 53.621 | −22.274 | 1.946 | 1.00 | 20.79 | A | O |
| ATOM | 8079 | N | LEU | A | 522 | 51.724 | −21.961 | 0.870 | 1.00 | 22.97 | A | N |
| ATOM | 8080 | CA | LEU | A | 522 | 51.287 | −21.020 | 1.894 | 1.00 | 22.18 | A | C |
| ATOM | 8082 | CB | LEU | A | 522 | 49.999 | −20.375 | 1.480 | 1.00 | 21.54 | A | C |
| ATOM | 8085 | CG | LEU | A | 522 | 49.371 | −19.451 | 2.528 | 1.00 | 28.84 | A | C |
| ATOM | 8087 | CD1 | LEU | A | 522 | 49.451 | −18.040 | 2.067 | 1.00 | 28.12 | A | C |
| ATOM | 8091 | CD2 | LEU | A | 522 | 47.923 | −19.860 | 2.764 | 1.00 | 22.93 | A | C |
| ATOM | 8095 | C | LEU | A | 522 | 51.128 | −21.739 | 3.258 | 1.00 | 23.98 | A | C |
| ATOM | 8096 | O | LEU | A | 522 | 51.440 | −21.191 | 4.335 | 1.00 | 27.60 | A | O |
| ATOM | 8098 | N | ALA | A | 523 | 50.655 | −22.966 | 3.219 | 1.00 | 20.93 | A | N |
| ATOM | 8099 | CA | ALA | A | 523 | 50.483 | −23.745 | 4.435 | 1.00 | 20.65 | A | C |
| ATOM | 8101 | CB | ALA | A | 523 | 49.688 | −25.053 | 4.123 | 1.00 | 18.52 | A | C |
| ATOM | 8105 | C | ALA | A | 523 | 51.858 | −24.069 | 5.025 | 1.00 | 19.62 | A | C |
| ATOM | 8106 | O | ALA | A | 523 | 52.066 | −23.988 | 6.225 | 1.00 | 19.29 | A | O |
| ATOM | 8108 | N | ARG | A | 524 | 52.790 | −24.453 | 4.158 | 1.00 | 21.30 | A | N |
| ATOM | 8109 | CA | ARG | A | 524 | 54.160 | −24.730 | 4.566 | 1.00 | 19.62 | A | C |
| ATOM | 8111 | CB | ARG | A | 524 | 54.994 | −25.155 | 3.355 | 1.00 | 19.24 | A | C |
| ATOM | 8114 | CG | ARG | A | 524 | 54.604 | −26.493 | 2.752 | 1.00 | 20.08 | A | C |
| ATOM | 8117 | CD | ARG | A | 524 | 55.572 | −26.973 | 1.663 | 1.00 | 16.22 | A | C |
| ATOM | 8120 | NE | ARG | A | 524 | 55.254 | −28.341 | 1.267 | 1.00 | 17.63 | A | N |
| ATOM | 8122 | CZ | ARG | A | 524 | 54.851 | −28.736 | 0.065 | 1.00 | 22.37 | A | C |
| ATOM | 8123 | NH1 | ARG | A | 524 | 54.705 | −27.877 | −0.917 | 1.00 | 22.88 | A | N |
| ATOM | 8126 | NH2 | ARG | A | 524 | 54.577 | −30.020 | −0.153 | 1.00 | 22.48 | A | N |
| ATOM | 8129 | C | ARG | A | 524 | 54.783 | −23.497 | 5.211 | 1.00 | 18.86 | A | C |
| ATOM | 8130 | O | ARG | A | 524 | 55.416 | −23.587 | 6.243 | 1.00 | 20.03 | A | O |
| ATOM | 8132 | N | GLN | A | 525 | 54.627 | −22.344 | 4.577 | 1.00 | 21.45 | A | N |
| ATOM | 8133 | CA | GLN | A | 525 | 55.227 | −21.127 | 5.095 | 1.00 | 23.44 | A | C |
| ATOM | 8135 | CB | GLN | A | 525 | 55.050 | −19.940 | 4.126 | 1.00 | 24.10 | A | C |
| ATOM | 8138 | CG | GLN | A | 525 | 55.702 | −18.631 | 4.655 | 1.00 | 27.82 | A | C |
| ATOM | 8141 | CD | GLN | A | 525 | 57.200 | −18.783 | 4.854 | 1.00 | 31.75 | A | C |
| ATOM | 8142 | OE1 | GLN | A | 525 | 57.858 | −19.483 | 4.107 | 1.00 | 35.59 | A | O |
| ATOM | 8143 | NE2 | GLN | A | 525 | 57.741 | −18.116 | 5.854 | 1.00 | 35.48 | A | N |
| ATOM | 8146 | C | GLN | A | 525 | 54.618 | −20.823 | 6.442 | 1.00 | 21.93 | A | C |
| ATOM | 8147 | O | GLN | A | 525 | 55.301 | −20.367 | 7.349 | 1.00 | 24.82 | A | O |
| ATOM | 8149 | N | SER | A | 526 | 53.335 | −21.125 | 6.588 | 1.00 | 23.48 | A | N |
| ATOM | 8150 | CA | SER | A | 526 | 52.645 | −20.951 | 7.865 | 1.00 | 21.99 | A | C |
| ATOM | 8152 | CB | SER | A | 526 | 51.157 | −21.240 | 7.721 | 1.00 | 21.77 | A | C |
| ATOM | 8155 | OG | SER | A | 526 | 50.545 | −20.385 | 6.756 | 1.00 | 27.32 | A | O |
| ATOM | 8157 | C | SER | A | 526 | 53.245 | −21.829 | 8.945 | 1.00 | 24.68 | A | C |
| ATOM | 8158 | O | SER | A | 526 | 53.518 | −21.362 | 10.061 | 1.00 | 24.00 | A | O |
| ATOM | 8160 | N | HIS | A | 527 | 53.480 | −23.096 | 8.630 | 1.00 | 24.99 | A | N |
| ATOM | 8161 | CA | HIS | A | 527 | 54.171 | −23.962 | 9.610 | 1.00 | 28.16 | A | C |
| ATOM | 8163 | CB | HIS | A | 527 | 54.357 | −25.381 | 9.073 | 1.00 | 29.27 | A | C |
| ATOM | 8166 | CG | HIS | A | 527 | 53.101 | −26.172 | 9.090 | 1.00 | 25.87 | A | C |
| ATOM | 8167 | ND1 | HIS | A | 527 | 52.548 | −26.642 | 10.258 | 1.00 | 26.45 | A | N |
| ATOM | 8169 | CE1 | HIS | A | 527 | 51.424 | −27.278 | 9.982 | 1.00 | 25.98 | A | C |
| ATOM | 8171 | NE2 | HIS | A | 527 | 51.211 | −27.201 | 8.681 | 1.00 | 24.15 | A | N |
| ATOM | 8173 | CD2 | HIS | A | 527 | 52.241 | −26.501 | 8.102 | 1.00 | 26.74 | A | C |
| ATOM | 8175 | C | HIS | A | 527 | 55.523 | −23.428 | 10.010 | 1.00 | 28.59 | A | C |
| ATOM | 8176 | O | HIS | A | 527 | 55.911 | −23.545 | 11.155 | 1.00 | 29.28 | A | O |
| ATOM | 8178 | N | CYS | A | 528 | 56.233 | −22.863 | 9.042 | 1.00 | 29.41 | A | N |
| ATOM | 8179 | CA | CYS | A | 528 | 57.620 | −22.452 | 9.236 | 1.00 | 32.72 | A | C |
| ATOM | 8181 | CB | CYS | A | 528 | 58.325 | −22.320 | 7.884 | 1.00 | 30.69 | A | C |
| ATOM | 8184 | SG | CYS | A | 528 | 58.709 | −23.947 | 7.199 | 1.00 | 30.00 | A | S |
| ATOM | 8186 | C | CYS | A | 528 | 57.731 | −21.150 | 10.027 | 1.00 | 35.27 | A | C |
| ATOM | 8187 | O | CYS | A | 528 | 58.642 | −20.983 | 10.799 | 1.00 | 35.65 | A | O |
| ATOM | 8189 | N | THR | A | 529 | 56.784 | −20.249 | 9.814 | 1.00 | 39.06 | A | N |
| ATOM | 8190 | CA | THR | A | 529 | 56.751 | −18.951 | 10.470 | 1.00 | 40.10 | A | C |
| ATOM | 8192 | CB | THR | A | 529 | 55.848 | −18.006 | 9.689 | 1.00 | 40.17 | A | C |
| ATOM | 8194 | OG1 | THR | A | 529 | 56.529 | −17.624 | 8.491 | 1.00 | 38.25 | A | O |
| ATOM | 8196 | CG2 | THR | A | 529 | 55.488 | −16.770 | 10.521 | 1.00 | 39.82 | A | C |
| ATOM | 8200 | C | THR | A | 529 | 56.265 | −19.016 | 11.911 | 1.00 | 42.32 | A | C |
| ATOM | 8201 | O | THR | A | 529 | 56.803 | −18.308 | 12.775 | 1.00 | 43.34 | A | O |
| ATOM | 8203 | N | TYR | A | 530 | 55.263 | −19.854 | 12.173 | 1.00 | 44.35 | A | N |
| ATOM | 8204 | CA | TYR | A | 530 | 54.693 | −19.966 | 13.505 | 1.00 | 46.00 | A | C |

TABLE 4-2-continued

Coordinates of *P. alba* IspS

| ATOM | 8206 | CB | TYR | A | 530 | 53.166 | −20.032 | 13.439 | 1.00 | 44.27 | A | C |
|------|------|-----|-----|---|-----|--------|---------|--------|------|-------|---|---|
| ATOM | 8209 | CG | TYR | A | 530 | 52.609 | −18.762 | 12.860 | 1.00 | 37.30 | A | C |
| ATOM | 8210 | CD1 | TYR | A | 530 | 52.537 | −17.608 | 13.623 | 1.00 | 41.32 | A | C |
| ATOM | 8212 | CE1 | TYR | A | 530 | 52.068 | −16.421 | 13.084 | 1.00 | 36.85 | A | C |
| ATOM | 8214 | CZ | TYR | A | 530 | 51.680 | −16.379 | 11.772 | 1.00 | 34.37 | A | C |
| ATOM | 8215 | OH | TYR | A | 530 | 51.224 | −15.203 | 11.239 | 1.00 | 42.34 | A | O |
| ATOM | 8217 | CE2 | TYR | A | 530 | 51.754 | −17.510 | 10.987 | 1.00 | 37.02 | A | C |
| ATOM | 8219 | CD2 | TYR | A | 530 | 52.225 | −18.687 | 11.535 | 1.00 | 33.51 | A | C |
| ATOM | 8221 | C | TYR | A | 530 | 55.343 | −21.106 | 14.288 | 1.00 | 51.39 | A | C |
| ATOM | 8222 | O | TYR | A | 530 | 54.775 | −22.175 | 14.481 | 1.00 | 52.31 | A | O |
| ATOM | 8224 | N | HIS | A | 531 | 56.561 | −20.811 | 14.740 | 1.00 | 58.00 | A | N |
| ATOM | 8225 | CA | HIS | A | 531 | 57.399 | −21.680 | 15.572 | 1.00 | 61.94 | A | C |
| ATOM | 8227 | CB | HIS | A | 531 | 58.753 | −21.900 | 14.875 | 1.00 | 62.85 | A | C |
| ATOM | 8230 | CG | HIS | A | 531 | 59.575 | −20.646 | 14.738 | 1.00 | 65.82 | A | C |
| ATOM | 8231 | ND1 | HIS | A | 531 | 59.608 | −19.895 | 13.579 | 1.00 | 70.80 | A | N |
| ATOM | 8233 | CE1 | HIS | A | 531 | 60.404 | −18.852 | 13.752 | 1.00 | 66.74 | A | C |
| ATOM | 8235 | NE2 | HIS | A | 531 | 60.883 | −18.894 | 14.982 | 1.00 | 63.48 | A | N |
| ATOM | 8237 | CD2 | HIS | A | 531 | 60.381 | −20.004 | 15.620 | 1.00 | 65.00 | A | C |
| ATOM | 8239 | C | HIS | A | 531 | 57.655 | −20.986 | 16.920 | 1.00 | 64.85 | A | C |
| ATOM | 8240 | O | HIS | A | 531 | 57.504 | −19.758 | 17.030 | 1.00 | 64.46 | A | O |
| ATOM | 8242 | N | ASN | A | 532 | 58.067 | −21.766 | 17.926 | 1.00 | 67.27 | A | N |
| ATOM | 8243 | CA | ASN | A | 532 | 58.496 | −21.224 | 19.224 | 1.00 | 68.94 | A | C |
| ATOM | 8245 | CB | ASN | A | 532 | 57.603 | −21.755 | 20.366 | 1.00 | 70.24 | A | C |
| ATOM | 8248 | CG | ASN | A | 532 | 56.240 | −21.039 | 20.445 | 1.00 | 75.92 | A | C |
| ATOM | 8249 | OD1 | ASN | A | 532 | 55.500 | −20.950 | 19.452 | 1.00 | 78.73 | A | O |
| ATOM | 8250 | ND2 | ASN | A | 532 | 55.906 | −20.536 | 21.638 | 1.00 | 74.91 | A | N |
| ATOM | 8253 | C | ASN | A | 532 | 59.981 | −21.534 | 19.481 | 1.00 | 68.89 | A | C |
| ATOM | 8254 | O | ASN | A | 532 | 60.352 | −22.156 | 20.484 | 1.00 | 68.53 | A | O |
| ATOM | 8256 | N | THR | A | 537 | 67.332 | −21.795 | 21.607 | 1.00 | 92.68 | A | N |
| ATOM | 8257 | CA | THR | A | 537 | 66.924 | −20.612 | 20.853 | 1.00 | 93.30 | A | C |
| ATOM | 8259 | CB | THR | A | 537 | 66.958 | −20.873 | 19.320 | 1.00 | 93.55 | A | C |
| ATOM | 8261 | OG1 | THR | A | 537 | 68.054 | −21.736 | 18.994 | 1.00 | 94.33 | A | O |
| ATOM | 8263 | CG2 | THR | A | 537 | 67.102 | −19.564 | 18.539 | 1.00 | 93.26 | A | C |
| ATOM | 8267 | C | THR | A | 537 | 65.513 | −20.160 | 21.260 | 1.00 | 93.42 | A | C |
| ATOM | 8268 | O | THR | A | 537 | 64.724 | −20.952 | 21.790 | 1.00 | 93.83 | A | O |
| ATOM | 8270 | N | SER | A | 538 | 65.215 | −18.883 | 21.009 | 1.00 | 92.90 | A | N |
| ATOM | 8271 | CA | SER | A | 538 | 63.908 | −18.278 | 21.299 | 1.00 | 92.33 | A | C |
| ATOM | 8273 | CB | SER | A | 538 | 64.113 | −17.011 | 22.137 | 1.00 | 92.35 | A | C |
| ATOM | 8276 | OG | SER | A | 538 | 64.875 | −16.046 | 21.429 | 1.00 | 90.48 | A | O |
| ATOM | 8278 | C | SER | A | 538 | 63.159 | −17.940 | 19.991 | 1.00 | 91.91 | A | C |
| ATOM | 8279 | O | SER | A | 538 | 63.751 | −18.023 | 18.918 | 1.00 | 90.87 | A | O |
| ATOM | 8281 | N | PRO | A | 539 | 61.852 | −17.583 | 20.077 | 1.00 | 92.14 | A | N |
| ATOM | 8282 | CA | PRO | A | 539 | 61.015 | −17.108 | 18.952 | 1.00 | 91.90 | A | C |
| ATOM | 8284 | CB | PRO | A | 539 | 59.778 | −16.550 | 19.670 | 1.00 | 92.24 | A | C |
| ATOM | 8287 | CG | PRO | A | 539 | 59.602 | −17.482 | 20.811 | 1.00 | 93.29 | A | C |
| ATOM | 8290 | CD | PRO | A | 539 | 61.005 | −17.907 | 21.244 | 1.00 | 92.54 | A | C |
| ATOM | 8293 | C | PRO | A | 539 | 61.663 | −16.079 | 17.996 | 1.00 | 90.64 | A | C |
| ATOM | 8294 | O | PRO | A | 539 | 62.570 | −16.453 | 17.254 | 1.00 | 90.97 | A | O |
| ATOM | 8295 | N | ASP | A | 540 | 61.200 | −14.823 | 17.973 | 1.00 | 88.91 | A | N |
| ATOM | 8296 | CA | ASP | A | 540 | 61.764 | −13.832 | 17.045 | 1.00 | 87.34 | A | C |
| ATOM | 8298 | CB | ASP | A | 540 | 60.995 | −12.501 | 17.090 | 1.00 | 88.16 | A | C |
| ATOM | 8301 | CG | ASP | A | 540 | 61.064 | −11.734 | 15.767 | 1.00 | 91.26 | A | C |
| ATOM | 8302 | OD1 | ASP | A | 540 | 62.082 | −11.847 | 15.046 | 1.00 | 92.68 | A | O |
| ATOM | 8303 | OD2 | ASP | A | 540 | 60.095 | −11.012 | 15.445 | 1.00 | 92.20 | A | O |
| ATOM | 8304 | C | ASP | A | 540 | 63.249 | −13.623 | 17.357 | 1.00 | 83.97 | A | C |
| ATOM | 8305 | O | ASP | A | 540 | 63.608 | −12.904 | 18.291 | 1.00 | 84.17 | A | O |
| ATOM | 8307 | N | GLU | A | 541 | 64.085 | −14.261 | 16.542 | 1.00 | 80.01 | A | N |
| ATOM | 8308 | CA | GLU | A | 541 | 65.522 | −14.464 | 16.780 | 1.00 | 77.67 | A | C |
| ATOM | 8310 | CB | GLU | A | 541 | 65.870 | −14.669 | 18.260 | 1.00 | 78.10 | A | C |
| ATOM | 8313 | CG | GLU | A | 541 | 67.352 | −14.486 | 18.565 | 1.00 | 81.78 | A | C |
| ATOM | 8316 | CD | GLU | A | 541 | 67.610 | −13.838 | 19.922 | 1.00 | 88.80 | A | C |
| ATOM | 8317 | OE1 | GLU | A | 541 | 67.125 | −12.702 | 20.144 | 1.00 | 90.81 | A | O |
| ATOM | 8318 | OE2 | GLU | A | 541 | 68.306 | −14.453 | 20.761 | 1.00 | 88.82 | A | O |
| ATOM | 8319 | C | GLU | A | 541 | 65.937 | −15.699 | 15.973 | 1.00 | 73.57 | A | C |
| ATOM | 8320 | O | GLU | A | 541 | 66.977 | −15.711 | 15.311 | 1.00 | 73.68 | A | O |
| ATOM | 8322 | N | LEU | A | 542 | 65.116 | −16.743 | 16.054 | 1.00 | 68.45 | A | N |
| ATOM | 8323 | CA | LEU | A | 542 | 65.113 | −17.805 | 15.051 | 1.00 | 64.32 | A | C |
| ATOM | 8325 | CB | LEU | A | 542 | 64.264 | −18.994 | 15.512 | 1.00 | 64.16 | A | C |
| ATOM | 8328 | CG | LEU | A | 542 | 64.082 | −20.157 | 14.527 | 1.00 | 66.34 | A | C |
| ATOM | 8330 | CD1 | LEU | A | 542 | 63.430 | −21.367 | 15.221 | 1.00 | 64.49 | A | C |
| ATOM | 8334 | CD2 | LEU | A | 542 | 65.418 | −20.547 | 13.870 | 1.00 | 67.67 | A | C |
| ATOM | 8338 | C | LEU | A | 542 | 64.583 | −17.236 | 13.731 | 1.00 | 59.26 | A | C |
| ATOM | 8339 | O | LEU | A | 542 | 65.135 | −17.512 | 12.679 | 1.00 | 56.08 | A | O |
| ATOM | 8341 | N | THR | A | 543 | 63.525 | −16.431 | 13.807 | 1.00 | 55.75 | A | N |
| ATOM | 8342 | CA | THR | A | 543 | 63.001 | −15.694 | 12.652 | 1.00 | 53.99 | A | C |
| ATOM | 8344 | CB | THR | A | 543 | 61.827 | −14.798 | 13.080 | 1.00 | 52.82 | A | C |
| ATOM | 8346 | OG1 | THR | A | 543 | 60.796 | −15.613 | 13.647 | 1.00 | 55.45 | A | O |
| ATOM | 8348 | CG2 | THR | A | 543 | 61.266 | −13.999 | 11.910 | 1.00 | 47.21 | A | C |

TABLE 4-2-continued

Coordinates of *P. alba* IspS

| ATOM | 8352 | C | THR | A | 543 | 64.055 | −14.811 | 11.984 | 1.00 | 53.90 | A | C |
|---|---|---|---|---|---|---|---|---|---|---|---|---|
| ATOM | 8353 | O | THR | A | 543 | 64.132 | −14.738 | 10.754 | 1.00 | 53.78 | A | O |
| ATOM | 8355 | N | ARG | A | 544 | 64.861 | −14.141 | 12.807 | 1.00 | 53.78 | A | N |
| ATOM | 8356 | CA | ARG | A | 544 | 65.880 | −13.214 | 12.320 | 1.00 | 53.00 | A | C |
| ATOM | 8358 | CB | ARG | A | 544 | 66.482 | −12.402 | 13.487 | 1.00 | 54.30 | A | C |
| ATOM | 8361 | CG | ARG | A | 544 | 67.763 | −11.600 | 13.148 | 1.00 | 58.88 | A | C |
| ATOM | 8364 | CD | ARG | A | 544 | 68.416 | −10.977 | 14.395 | 1.00 | 68.64 | A | C |
| ATOM | 8367 | NE | ARG | A | 544 | 68.769 | −11.968 | 15.421 | 1.00 | 75.29 | A | N |
| ATOM | 8369 | CZ | ARG | A | 544 | 69.815 | −12.799 | 15.370 | 1.00 | 78.84 | A | C |
| ATOM | 8370 | NH1 | ARG | A | 544 | 70.654 | −12.793 | 14.334 | 1.00 | 78.60 | A | N |
| ATOM | 8373 | NH2 | ARG | A | 544 | 70.023 | −13.656 | 16.367 | 1.00 | 78.30 | A | N |
| ATOM | 8376 | C | ARG | A | 544 | 66.977 | −13.965 | 11.591 | 1.00 | 50.00 | A | C |
| ATOM | 8377 | O | ARG | A | 544 | 67.503 | −13.474 | 10.602 | 1.00 | 49.41 | A | O |
| ATOM | 8379 | N | LYS | A | 545 | 67.342 | −15.131 | 12.113 | 1.00 | 47.99 | A | N |
| ATOM | 8380 | CA | LYS | A | 545 | 68.378 | −15.955 | 11.497 | 1.00 | 48.74 | A | C |
| ATOM | 8382 | CB | LYS | A | 545 | 68.824 | −17.088 | 12.442 | 1.00 | 50.27 | A | C |
| ATOM | 8385 | CG | LYS | A | 545 | 69.814 | −16.611 | 13.534 | 1.00 | 59.32 | A | C |
| ATOM | 8388 | CD | LYS | A | 545 | 70.549 | −17.761 | 14.252 | 1.00 | 64.78 | A | C |
| ATOM | 8391 | CE | LYS | A | 545 | 71.708 | −17.208 | 15.089 | 1.00 | 70.21 | A | C |
| ATOM | 8394 | NZ | LYS | A | 545 | 72.591 | −18.251 | 15.680 | 1.00 | 71.30 | A | N |
| ATOM | 8398 | C | LYS | A | 545 | 67.892 | −16.520 | 10.167 | 1.00 | 44.99 | A | C |
| ATOM | 8399 | O | LYS | A | 545 | 68.642 | −16.585 | 9.194 | 1.00 | 42.74 | A | O |
| ATOM | 8401 | N | ARG | A | 546 | 66.624 | −16.911 | 10.141 | 1.00 | 43.75 | A | N |
| ATOM | 8402 | CA | ARG | A | 546 | 66.006 | −17.452 | 8.934 | 1.00 | 42.43 | A | C |
| ATOM | 8404 | CB | ARG | A | 546 | 64.624 | −18.006 | 9.244 | 1.00 | 41.43 | A | C |
| ATOM | 8407 | CG | ARG | A | 546 | 64.725 | −19.301 | 10.007 | 1.00 | 34.91 | A | C |
| ATOM | 8410 | CD | ARG | A | 546 | 63.396 | −19.926 | 10.297 | 1.00 | 35.83 | A | C |
| ATOM | 8413 | NE | ARG | A | 546 | 63.616 | −21.251 | 10.863 | 1.00 | 35.94 | A | N |
| ATOM | 8415 | CZ | ARG | A | 546 | 62.659 | −22.099 | 11.220 | 1.00 | 36.20 | A | C |
| ATOM | 8416 | NH1 | ARG | A | 546 | 61.380 | −21.769 | 11.093 | 1.00 | 37.38 | A | N |
| ATOM | 8419 | NH2 | ARG | A | 546 | 62.992 | −23.276 | 11.743 | 1.00 | 39.23 | A | N |
| ATOM | 8422 | C | ARG | A | 546 | 65.963 | −16.413 | 7.826 | 1.00 | 42.22 | A | C |
| ATOM | 8423 | O | ARG | A | 546 | 66.372 | −16.706 | 6.704 | 1.00 | 42.78 | A | O |
| ATOM | 8425 | N | VAL | A | 547 | 65.537 | −15.192 | 8.153 | 1.00 | 40.65 | A | N |
| ATOM | 8426 | CA | VAL | A | 547 | 65.599 | −14.085 | 7.193 | 1.00 | 40.43 | A | C |
| ATOM | 8428 | CB | VAL | A | 547 | 65.055 | −12.771 | 7.810 | 1.00 | 41.44 | A | C |
| ATOM | 8430 | CG1 | VAL | A | 547 | 65.454 | −11.568 | 6.974 | 1.00 | 43.77 | A | C |
| ATOM | 8434 | CG2 | VAL | A | 547 | 63.543 | −12.847 | 7.984 | 1.00 | 37.89 | A | C |
| ATOM | 8438 | C | VAL | A | 547 | 67.028 | −13.846 | 6.715 | 1.00 | 40.76 | A | C |
| ATOM | 8439 | O | VAL | A | 547 | 67.269 | −13.551 | 5.547 | 1.00 | 41.64 | A | O |
| ATOM | 8441 | N | LEU | A | 548 | 67.978 | −13.952 | 7.632 | 1.00 | 39.02 | A | N |
| ATOM | 8442 | CA | LEU | A | 548 | 69.369 | −13.763 | 7.283 | 1.00 | 37.94 | A | C |
| ATOM | 8444 | CB | LEU | A | 548 | 70.239 | −13.775 | 8.544 | 1.00 | 38.42 | A | C |
| ATOM | 8447 | CG | LEU | A | 548 | 71.184 | −12.599 | 8.823 | 1.00 | 45.83 | A | C |
| ATOM | 8449 | CD1 | LEU | A | 548 | 70.487 | −11.217 | 8.801 | 1.00 | 41.58 | A | C |
| ATOM | 8453 | CD2 | LEU | A | 548 | 71.866 | −12.861 | 10.179 | 1.00 | 43.53 | A | C |
| ATOM | 8457 | C | LEU | A | 548 | 69.805 | −14.866 | 6.305 | 1.00 | 36.31 | A | C |
| ATOM | 8458 | O | LEU | A | 548 | 70.419 | −14.589 | 5.281 | 1.00 | 37.41 | A | O |
| ATOM | 8460 | N | SER | A | 549 | 69.471 | −16.115 | 6.607 | 1.00 | 33.80 | A | N |
| ATOM | 8461 | CA | SER | A | 549 | 69.995 | −17.230 | 5.830 | 1.00 | 32.40 | A | C |
| ATOM | 8463 | CB | SER | A | 549 | 69.914 | −18.526 | 6.640 | 1.00 | 32.69 | A | C |
| ATOM | 8466 | OG | SER | A | 549 | 68.573 | −18.865 | 6.912 | 1.00 | 33.82 | A | O |
| ATOM | 8468 | C | SER | A | 549 | 69.258 | −17.374 | 4.497 | 1.00 | 29.96 | A | C |
| ATOM | 8469 | O | SER | A | 549 | 69.816 | −17.884 | 3.525 | 1.00 | 28.51 | A | O |
| ATOM | 8471 | N | VAL | A | 550 | 68.017 | −16.896 | 4.444 | 1.00 | 28.34 | A | N |
| ATOM | 8472 | CA | VAL | A | 550 | 67.218 | −16.982 | 3.232 | 1.00 | 26.12 | A | C |
| ATOM | 8474 | CB | VAL | A | 550 | 65.754 | −17.231 | 3.551 | 1.00 | 27.43 | A | C |
| ATOM | 8476 | CG1 | VAL | A | 550 | 64.912 | −17.149 | 2.274 | 1.00 | 22.74 | A | C |
| ATOM | 8480 | CG2 | VAL | A | 550 | 65.603 | −18.589 | 4.190 | 1.00 | 20.03 | A | C |
| ATOM | 8484 | C | VAL | A | 550 | 67.352 | −15.777 | 2.320 | 1.00 | 27.26 | A | C |
| ATOM | 8485 | O | VAL | A | 550 | 67.466 | −15.933 | 1.101 | 1.00 | 26.44 | A | O |
| ATOM | 8487 | N | ILE | A | 551 | 67.367 | −14.575 | 2.877 | 1.00 | 28.59 | A | N |
| ATOM | 8488 | CA | ILE | A | 551 | 67.457 | −13.380 | 2.037 | 1.00 | 30.46 | A | C |
| ATOM | 8490 | CB | ILE | A | 551 | 66.537 | −12.274 | 2.537 | 1.00 | 31.18 | A | C |
| ATOM | 8492 | CG1 | ILE | A | 551 | 65.093 | −12.747 | 2.553 | 1.00 | 29.53 | A | C |
| ATOM | 8495 | CD1 | ILE | A | 551 | 64.570 | −13.145 | 1.191 | 1.00 | 40.54 | A | C |
| ATOM | 8499 | CG2 | ILE | A | 551 | 66.697 | −11.023 | 1.653 | 1.00 | 29.98 | A | C |
| ATOM | 8503 | C | ILE | A | 551 | 68.841 | −12.746 | 1.941 | 1.00 | 31.12 | A | C |
| ATOM | 8504 | O | ILE | A | 551 | 69.329 | −12.460 | 0.843 | 1.00 | 30.57 | A | O |
| ATOM | 8506 | N | THR | A | 552 | 69.453 | −12.486 | 3.090 | 1.00 | 33.43 | A | N |
| ATOM | 8507 | CA | THR | A | 552 | 70.551 | −11.541 | 3.150 | 1.00 | 35.23 | A | C |
| ATOM | 8509 | CB | THR | A | 552 | 70.422 | −10.661 | 4.419 | 1.00 | 38.85 | A | C |
| ATOM | 8511 | OG1 | THR | A | 552 | 70.734 | −11.431 | 5.583 | 1.00 | 49.74 | A | O |
| ATOM | 8513 | CG2 | THR | A | 552 | 69.002 | −10.115 | 4.567 | 1.00 | 34.09 | A | C |
| ATOM | 8517 | C | THR | A | 552 | 71.979 | −12.148 | 3.020 | 1.00 | 35.34 | A | C |
| ATOM | 8518 | O | THR | A | 552 | 72.805 | −11.623 | 2.259 | 1.00 | 34.57 | A | O |
| ATOM | 8520 | N | GLU | A | 553 | 72.273 | −13.222 | 3.752 | 1.00 | 35.04 | A | N |
| ATOM | 8521 | CA | GLU | A | 553 | 73.628 | −13.801 | 3.777 | 1.00 | 36.99 | A | C |

TABLE 4-2-continued

Coordinates of P. alba IspS

| ATOM | 8523 | CB | GLU | A | 553 | 74.020 | −14.209 | 5.200 | 1.00 | 38.28 | A | C |
|---|---|---|---|---|---|---|---|---|---|---|---|---|
| ATOM | 8526 | CG | GLU | A | 553 | 74.412 | −13.034 | 6.080 | 1.00 | 46.45 | A | C |
| ATOM | 8529 | CD | GLU | A | 553 | 75.002 | −13.456 | 7.418 | 1.00 | 57.04 | A | C |
| ATOM | 8530 | OE1 | GLU | A | 553 | 75.499 | −12.564 | 8.142 | 1.00 | 60.01 | A | O |
| ATOM | 8531 | OE2 | GLU | A | 553 | 74.972 | −14.667 | 7.750 | 1.00 | 60.27 | A | O |
| ATOM | 8532 | C | GLU | A | 553 | 73.756 | −15.027 | 2.879 | 1.00 | 35.15 | A | C |
| ATOM | 8533 | O | GLU | A | 553 | 73.085 | −16.016 | 3.094 | 1.00 | 33.64 | A | O |
| ATOM | 8535 | N | PRO | A | 554 | 74.649 | −14.979 | 1.890 | 1.00 | 35.47 | A | N |
| ATOM | 8536 | CA | PRO | A | 554 | 74.878 | −16.177 | 1.087 | 1.00 | 33.93 | A | C |
| ATOM | 8538 | CB | PRO | A | 554 | 75.924 | −15.722 | 0.056 | 1.00 | 35.05 | A | C |
| ATOM | 8541 | CG | PRO | A | 554 | 75.825 | −14.234 | 0.044 | 1.00 | 35.89 | A | C |
| ATOM | 8544 | CD | PRO | A | 554 | 75.486 | −13.854 | 1.441 | 1.00 | 36.23 | A | C |
| ATOM | 8547 | C | PRO | A | 554 | 75.426 | −17.330 | 1.903 | 1.00 | 31.36 | A | C |
| ATOM | 8548 | O | PRO | A | 554 | 75.880 | −17.153 | 3.018 | 1.00 | 31.42 | A | O |
| ATOM | 8549 | N | ILE | A | 555 | 75.349 | −18.518 | 1.342 | 1.00 | 30.82 | A | N |
| ATOM | 8550 | CA | ILE | A | 555 | 75.946 | −19.684 | 1.957 | 1.00 | 31.22 | A | C |
| ATOM | 8552 | CB | ILE | A | 555 | 75.349 | −20.985 | 1.366 | 1.00 | 30.17 | A | C |
| ATOM | 8554 | CG1 | ILE | A | 555 | 73.862 | −21.095 | 1.715 | 1.00 | 30.75 | A | C |
| ATOM | 8557 | CD1 | ILE | A | 555 | 73.166 | −22.359 | 1.159 | 1.00 | 26.65 | A | C |
| ATOM | 8561 | CG2 | ILE | A | 555 | 76.096 | −22.190 | 1.874 | 1.00 | 29.43 | A | C |
| ATOM | 8565 | C | ILE | A | 555 | 77.455 | −19.589 | 1.694 | 1.00 | 30.28 | A | C |
| ATOM | 8566 | O | ILE | A | 555 | 77.853 | −19.201 | 0.607 | 1.00 | 27.19 | A | O |
| ATOM | 8568 | N | LEU | A | 556 | 78.273 | −19.924 | 2.693 | 1.00 | 31.81 | A | N |
| ATOM | 8569 | CA | LEU | A | 556 | 79.736 | −19.843 | 2.571 | 1.00 | 33.19 | A | C |
| ATOM | 8571 | CB | LEU | A | 556 | 80.432 | −20.311 | 3.857 | 1.00 | 33.04 | A | C |
| ATOM | 8574 | CG | LEU | A | 556 | 80.327 | −19.370 | 5.071 | 1.00 | 40.15 | A | C |
| ATOM | 8576 | CD1 | LEU | A | 556 | 80.560 | −20.126 | 6.367 | 1.00 | 44.82 | A | C |
| ATOM | 8580 | CD2 | LEU | A | 556 | 81.297 | −18.182 | 4.960 | 1.00 | 40.79 | A | C |
| ATOM | 8584 | C | LEU | A | 556 | 80.195 | −20.687 | 1.391 | 1.00 | 33.20 | A | C |
| ATOM | 8585 | O | LEU | A | 556 | 79.754 | −21.814 | 1.234 | 1.00 | 34.64 | A | O |
| ATOM | 8587 | N | PRO | A | 557 | 81.093 | −20.150 | 0.560 | 1.00 | 34.80 | A | N |
| ATOM | 8588 | CA | PRO | A | 557 | 81.389 | −20.817 | −0.707 | 1.00 | 34.59 | A | C |
| ATOM | 8590 | CB | PRO | A | 557 | 82.379 | −19.878 | −1.402 | 1.00 | 35.42 | A | C |
| ATOM | 8593 | CG | PRO | A | 557 | 82.956 | −19.016 | −0.316 | 1.00 | 37.04 | A | C |
| ATOM | 8596 | CD | PRO | A | 557 | 82.005 | −19.023 | 0.846 | 1.00 | 35.67 | A | C |
| ATOM | 8599 | C | PRO | A | 557 | 82.003 | −22.187 | −0.532 | 1.00 | 34.31 | A | C |
| ATOM | 8600 | O | PRO | A | 557 | 82.598 | −22.485 | 0.497 | 1.00 | 34.81 | A | O |
| ATOM | 8601 | N | PHE | A | 558 | 81.824 | −23.015 | −1.548 | 1.00 | 34.16 | A | N |
| ATOM | 8602 | CA | PHE | A | 558 | 82.422 | −24.328 | −1.595 | 1.00 | 34.90 | A | C |
| ATOM | 8604 | CB | PHE | A | 558 | 82.071 | −24.950 | −2.929 | 1.00 | 32.02 | A | C |
| ATOM | 8607 | CG | PHE | A | 558 | 82.786 | −26.220 | −3.210 | 1.00 | 33.45 | A | C |
| ATOM | 8608 | CD1 | PHE | A | 558 | 83.795 | −26.268 | −4.157 | 1.00 | 35.45 | A | C |
| ATOM | 8610 | CE1 | PHE | A | 558 | 84.443 | −27.463 | −4.429 | 1.00 | 39.71 | A | C |
| ATOM | 8612 | CZ | PHE | A | 558 | 84.082 | −28.618 | −3.750 | 1.00 | 40.59 | A | C |
| ATOM | 8614 | CE2 | PHE | A | 558 | 83.074 | −28.575 | −2.805 | 1.00 | 37.21 | A | C |
| ATOM | 8616 | CD2 | PHE | A | 558 | 82.440 | −27.382 | −2.536 | 1.00 | 34.24 | A | C |
| ATOM | 8618 | C | PHE | A | 558 | 83.950 | −24.247 | −1.466 | 1.00 | 37.69 | A | C |
| ATOM | 8619 | O | PHE | A | 558 | 84.563 | −23.354 | −2.050 | 1.00 | 35.80 | A | O |
| ATOM | 8621 | N | GLU | A | 559 | 84.547 | −25.183 | −0.726 | 1.00 | 42.77 | A | N |
| ATOM | 8622 | CA | GLU | A | 559 | 86.019 | −25.260 | −0.597 | 1.00 | 49.59 | A | C |
| ATOM | 8624 | CB | GLU | A | 559 | 86.454 | −25.349 | 0.882 | 1.00 | 50.56 | A | C |
| ATOM | 8627 | CG | GLU | A | 559 | 86.515 | −23.989 | 1.607 | 1.00 | 54.49 | A | C |
| ATOM | 8630 | CD | GLU | A | 559 | 87.615 | −23.913 | 2.683 | 1.00 | 62.33 | A | C |
| ATOM | 8631 | OE1 | GLU | A | 559 | 88.034 | −24.964 | 3.225 | 1.00 | 60.02 | A | O |
| ATOM | 8632 | OE2 | GLU | A | 559 | 88.065 | −22.786 | 2.989 | 1.00 | 62.02 | A | O |
| ATOM | 8633 | C | GLU | A | 559 | 86.678 | −26.368 | −1.464 | 1.00 | 52.68 | A | C |
| ATOM | 8634 | O | GLU | A | 559 | 86.943 | −26.123 | −2.636 | 1.00 | 54.35 | A | O |
| ATOM | 8636 | N | ARG | A | 560 | 86.938 | −27.551 | −0.895 | 1.00 | 55.62 | A | N |
| ATOM | 8637 | CA | ARG | A | 560 | 87.722 | −28.662 | −1.529 | 1.00 | 58.23 | A | C |
| ATOM | 8639 | CB | ARG | A | 560 | 88.710 | −28.199 | −2.636 | 1.00 | 59.46 | A | C |
| ATOM | 8642 | CG | ARG | A | 560 | 88.211 | −28.475 | −4.084 | 1.00 | 65.26 | A | C |
| ATOM | 8645 | CD | ARG | A | 560 | 88.672 | −27.426 | −5.136 | 1.00 | 70.99 | A | C |
| ATOM | 8648 | NE | ARG | A | 560 | 87.572 | −27.065 | −6.051 | 1.00 | 76.26 | A | N |
| ATOM | 8650 | CZ | ARG | A | 560 | 87.471 | −25.927 | −6.754 | 1.00 | 78.60 | A | C |
| ATOM | 8651 | NH1 | ARG | A | 560 | 88.419 | −24.990 | −6.703 | 1.00 | 78.10 | A | N |
| ATOM | 8654 | NH2 | ARG | A | 560 | 86.402 | −25.724 | −7.529 | 1.00 | 77.34 | A | N |
| ATOM | 8657 | C | ARG | A | 560 | 88.497 | −29.449 | −0.470 | 1.00 | 57.56 | A | C |
| ATOM | 8658 | O | ARG | A | 560 | 89.485 | −28.950 | 0.077 | 1.00 | 57.69 | A | O |
| ATOM | 8660 | N | ALA | B | 23 | 68.865 | 37.021 | 10.784 | 1.00 | 63.55 | B | N |
| ATOM | 8661 | CA | ALA | B | 23 | 69.934 | 36.293 | 10.034 | 1.00 | 63.42 | B | C |
| ATOM | 8663 | CB | ALA | B | 23 | 71.193 | 36.204 | 10.865 | 1.00 | 63.20 | B | C |
| ATOM | 8667 | C | ALA | B | 23 | 69.468 | 34.898 | 9.638 | 1.00 | 63.10 | B | C |
| ATOM | 8668 | O | ALA | B | 23 | 68.478 | 34.404 | 10.177 | 1.00 | 63.23 | B | O |
| ATOM | 8672 | N | ASN | B | 24 | 70.182 | 34.274 | 8.698 | 1.00 | 62.83 | B | N |
| ATOM | 8673 | CA | ASN | B | 24 | 69.852 | 32.919 | 8.208 | 1.00 | 62.89 | B | C |
| ATOM | 8675 | CB | ASN | B | 24 | 68.986 | 33.004 | 6.939 | 1.00 | 64.13 | B | C |
| ATOM | 8678 | CG | ASN | B | 24 | 68.555 | 31.630 | 6.414 | 1.00 | 66.01 | B | C |
| ATOM | 8679 | OD1 | ASN | B | 24 | 67.998 | 30.809 | 7.149 | 1.00 | 66.06 | B | O |

TABLE 4-2-continued

Coordinates of P. alba IspS

| ATOM | 8680 | ND2 | ASN | B | 24 | 68.801 | 31.389 | 5.132 | 1.00 | 66.01 | B | N |
|------|------|-----|-----|---|----|--------|--------|-------|------|-------|---|---|
| ATOM | 8683 | C | ASN | B | 24 | 71.083 | 32.041 | 7.929 | 1.00 | 60.68 | B | C |
| ATOM | 8684 | O | ASN | B | 24 | 71.878 | 32.334 | 7.029 | 1.00 | 60.33 | B | O |
| ATOM | 8686 | N | TYR | B | 25 | 71.215 | 30.959 | 8.699 | 1.00 | 58.42 | B | N |
| ATOM | 8687 | CA | TYR | B | 25 | 72.299 | 29.991 | 8.529 | 1.00 | 56.45 | B | C |
| ATOM | 8689 | CB | TYR | B | 25 | 73.034 | 29.771 | 9.854 | 1.00 | 54.20 | B | C |
| ATOM | 8692 | CG | TYR | B | 25 | 73.585 | 31.045 | 10.447 | 1.00 | 45.61 | B | C |
| ATOM | 8693 | CD1 | TYR | B | 25 | 74.573 | 31.785 | 9.789 | 1.00 | 37.42 | B | C |
| ATOM | 8695 | CE1 | TYR | B | 25 | 75.070 | 32.965 | 10.343 | 1.00 | 34.67 | B | C |
| ATOM | 8697 | CZ | TYR | B | 25 | 74.575 | 33.398 | 11.567 | 1.00 | 26.79 | B | C |
| ATOM | 8698 | OH | TYR | B | 25 | 75.031 | 34.555 | 12.166 | 1.00 | 22.69 | B | O |
| ATOM | 8700 | CE2 | TYR | B | 25 | 73.602 | 32.674 | 12.215 | 1.00 | 26.03 | B | C |
| ATOM | 8702 | CD2 | TYR | B | 25 | 73.112 | 31.521 | 11.660 | 1.00 | 34.02 | B | C |
| ATOM | 8704 | C | TYR | B | 25 | 71.835 | 28.640 | 7.990 | 1.00 | 57.64 | B | C |
| ATOM | 8705 | O | TYR | B | 25 | 72.641 | 27.717 | 7.901 | 1.00 | 57.97 | B | O |
| ATOM | 8707 | N | GLU | B | 26 | 70.560 | 28.511 | 7.620 | 1.00 | 59.08 | B | N |
| ATOM | 8708 | CA | GLU | B | 26 | 70.045 | 27.223 | 7.118 | 1.00 | 60.48 | B | C |
| ATOM | 8710 | CB | GLU | B | 26 | 68.510 | 27.159 | 7.198 | 1.00 | 61.50 | B | C |
| ATOM | 8713 | CG | GLU | B | 26 | 67.992 | 27.065 | 8.651 | 1.00 | 68.14 | B | C |
| ATOM | 8716 | CD | GLU | B | 26 | 66.579 | 26.483 | 8.775 | 1.00 | 76.80 | B | C |
| ATOM | 8717 | OE1 | GLU | B | 26 | 66.038 | 25.934 | 7.784 | 1.00 | 81.59 | B | O |
| ATOM | 8718 | OE2 | GLU | B | 26 | 66.008 | 26.568 | 9.885 | 1.00 | 80.08 | B | O |
| ATOM | 8719 | C | GLU | B | 26 | 70.551 | 26.918 | 5.694 | 1.00 | 58.35 | B | C |
| ATOM | 8720 | O | GLU | B | 26 | 70.748 | 27.837 | 4.898 | 1.00 | 55.74 | B | O |
| ATOM | 8722 | N | PRO | B | 27 | 70.785 | 25.623 | 5.389 | 1.00 | 58.14 | B | N |
| ATOM | 8723 | CA | PRO | B | 27 | 71.383 | 25.254 | 4.106 | 1.00 | 57.29 | B | C |
| ATOM | 8725 | CB | PRO | B | 27 | 71.677 | 23.759 | 4.265 | 1.00 | 58.74 | B | C |
| ATOM | 8728 | CG | PRO | B | 27 | 70.648 | 23.277 | 5.248 | 1.00 | 58.92 | B | C |
| ATOM | 8731 | CD | PRO | B | 27 | 70.460 | 24.434 | 6.207 | 1.00 | 58.03 | B | C |
| ATOM | 8734 | C | PRO | B | 27 | 70.427 | 25.464 | 2.951 | 1.00 | 56.06 | B | C |
| ATOM | 8735 | O | PRO | B | 27 | 69.206 | 25.463 | 3.137 | 1.00 | 56.00 | B | O |
| ATOM | 8736 | N | ASN | B | 28 | 70.993 | 25.657 | 1.768 | 1.00 | 54.96 | B | N |
| ATOM | 8737 | CA | ASN | B | 28 | 70.214 | 25.706 | 0.536 | 1.00 | 54.67 | B | C |
| ATOM | 8739 | CB | ASN | B | 28 | 70.821 | 26.721 | −0.448 | 1.00 | 55.69 | B | C |
| ATOM | 8742 | CG | ASN | B | 28 | 71.032 | 28.083 | 0.184 | 1.00 | 56.97 | B | C |
| ATOM | 8743 | OD1 | ASN | B | 28 | 70.102 | 28.660 | 0.744 | 1.00 | 59.86 | B | O |
| ATOM | 8744 | ND2 | ASN | B | 28 | 72.262 | 28.593 | 0.118 | 1.00 | 57.20 | B | N |
| ATOM | 8747 | C | ASN | B | 28 | 70.152 | 24.318 | −0.095 | 1.00 | 52.96 | B | C |
| ATOM | 8748 | O | ASN | B | 28 | 71.036 | 23.469 | 0.110 | 1.00 | 50.45 | B | O |
| ATOM | 8750 | N | SER | B | 29 | 69.092 | 24.090 | −0.858 | 1.00 | 52.74 | B | N |
| ATOM | 8751 | CA | SER | B | 29 | 68.943 | 22.848 | −1.620 | 1.00 | 53.12 | B | C |
| ATOM | 8753 | CB | SER | B | 29 | 67.530 | 22.783 | −2.229 | 1.00 | 53.87 | B | C |
| ATOM | 8756 | OG | SER | B | 29 | 67.129 | 24.045 | −2.769 | 1.00 | 50.23 | B | O |
| ATOM | 8758 | C | SER | B | 29 | 70.021 | 22.689 | −2.717 | 1.00 | 52.24 | B | C |
| ATOM | 8759 | O | SER | B | 29 | 70.258 | 21.579 | −3.202 | 1.00 | 53.74 | B | O |
| ATOM | 8761 | N | TRP | B | 30 | 70.662 | 23.796 | −3.095 | 1.00 | 50.38 | B | N |
| ATOM | 8762 | CA | TRP | B | 30 | 71.696 | 23.793 | −4.132 | 1.00 | 49.96 | B | C |
| ATOM | 8764 | CB | TRP | B | 30 | 71.494 | 24.969 | −5.109 | 1.00 | 49.93 | B | C |
| ATOM | 8767 | CG | TRP | B | 30 | 71.028 | 26.273 | −4.513 | 1.00 | 51.10 | B | C |
| ATOM | 8768 | CD1 | TRP | B | 30 | 69.736 | 26.720 | −4.435 | 1.00 | 57.17 | B | C |
| ATOM | 8770 | NE1 | TRP | B | 30 | 69.700 | 27.965 | −3.840 | 1.00 | 60.59 | B | N |
| ATOM | 8772 | CE2 | TRP | B | 30 | 70.981 | 28.348 | −3.534 | 1.00 | 55.40 | B | C |
| ATOM | 8773 | CD2 | TRP | B | 30 | 71.846 | 27.311 | −3.947 | 1.00 | 52.14 | B | C |
| ATOM | 8774 | CE3 | TRP | B | 30 | 73.224 | 27.459 | −3.736 | 1.00 | 57.76 | B | C |
| ATOM | 8776 | CZ3 | TRP | B | 30 | 73.692 | 28.628 | −3.134 | 1.00 | 59.65 | B | C |
| ATOM | 8778 | CH2 | TRP | B | 30 | 72.807 | 29.640 | −2.735 | 1.00 | 60.19 | B | C |
| ATOM | 8780 | CZ2 | TRP | B | 30 | 71.450 | 29.517 | −2.921 | 1.00 | 60.67 | B | C |
| ATOM | 8782 | C | TRP | B | 30 | 73.158 | 23.763 | −3.617 | 1.00 | 48.98 | B | C |
| ATOM | 8783 | O | TRP | B | 30 | 74.074 | 23.547 | −4.408 | 1.00 | 47.49 | B | O |
| ATOM | 8785 | N | ASP | B | 31 | 73.376 | 23.974 | −2.317 | 1.00 | 47.96 | B | N |
| ATOM | 8786 | CA | ASP | B | 31 | 74.734 | 23.951 | −1.732 | 1.00 | 47.91 | B | C |
| ATOM | 8788 | CB | ASP | B | 31 | 74.661 | 24.026 | −0.202 | 1.00 | 47.75 | B | C |
| ATOM | 8791 | CG | ASP | B | 31 | 74.301 | 25.413 | 0.310 | 1.00 | 50.81 | B | C |
| ATOM | 8792 | OD1 | ASP | B | 31 | 74.399 | 26.417 | −0.447 | 1.00 | 52.74 | B | O |
| ATOM | 8793 | OD2 | ASP | B | 31 | 73.939 | 25.489 | 1.505 | 1.00 | 54.84 | B | O |
| ATOM | 8794 | C | ASP | B | 31 | 75.545 | 22.705 | −2.113 | 1.00 | 47.82 | B | C |
| ATOM | 8795 | O | ASP | B | 31 | 74.989 | 21.614 | −2.241 | 1.00 | 46.75 | B | O |
| ATOM | 8797 | N | TYR | B | 32 | 76.861 | 22.863 | −2.267 | 1.00 | 47.95 | B | N |
| ATOM | 8798 | CA | TYR | B | 32 | 77.729 | 21.724 | −2.620 | 1.00 | 48.39 | B | C |
| ATOM | 8800 | CB | TYR | B | 32 | 79.107 | 22.187 | −3.111 | 1.00 | 46.33 | B | C |
| ATOM | 8803 | CG | TYR | B | 32 | 79.061 | 22.966 | −4.404 | 1.00 | 42.06 | B | C |
| ATOM | 8804 | CD1 | TYR | B | 32 | 78.597 | 22.375 | −5.600 | 1.00 | 32.87 | B | C |
| ATOM | 8806 | CE1 | TYR | B | 32 | 78.565 | 23.094 | −6.785 | 1.00 | 24.91 | B | C |
| ATOM | 8808 | CZ | TYR | B | 32 | 78.983 | 24.416 | −6.780 | 1.00 | 29.67 | B | C |
| ATOM | 8809 | OH | TYR | B | 32 | 78.959 | 25.162 | −7.917 | 1.00 | 28.02 | B | O |
| ATOM | 8811 | CE2 | TYR | B | 32 | 79.435 | 25.021 | −5.609 | 1.00 | 33.06 | B | C |
| ATOM | 8813 | CD2 | TYR | B | 32 | 79.481 | 24.295 | −4.442 | 1.00 | 38.13 | B | C |
| ATOM | 8815 | C | TYR | B | 32 | 77.912 | 20.694 | −1.496 | 1.00 | 50.79 | B | C |

TABLE 4-2-continued

Coordinates of *P. alba* IspS

| ATOM | 8816 | O | TYR | B | 32 | 78.332 | 19.566 | −1.774 | 1.00 | 49.23 | B | O |
|---|---|---|---|---|---|---|---|---|---|---|---|---|
| ATOM | 8818 | N | ASP | B | 33 | 77.621 | 21.082 | −0.247 | 1.00 | 54.28 | B | N |
| ATOM | 8819 | CA | ASP | B | 33 | 77.619 | 20.140 | 0.897 | 1.00 | 56.96 | B | C |
| ATOM | 8821 | CB | ASP | B | 33 | 77.480 | 20.882 | 2.244 | 1.00 | 56.67 | B | C |
| ATOM | 8824 | CG | ASP | B | 33 | 78.786 | 21.540 | 2.715 | 1.00 | 54.94 | B | C |
| ATOM | 8825 | OD1 | ASP | B | 33 | 79.876 | 21.054 | 2.353 | 1.00 | 51.15 | B | O |
| ATOM | 8826 | OD2 | ASP | B | 33 | 78.720 | 22.540 | 3.471 | 1.00 | 53.38 | B | O |
| ATOM | 8827 | C | ASP | B | 33 | 76.479 | 19.130 | 0.751 | 1.00 | 60.30 | B | C |
| ATOM | 8828 | O | ASP | B | 33 | 76.675 | 17.922 | 0.940 | 1.00 | 59.85 | B | O |
| ATOM | 8830 | N | TYR | B | 34 | 75.299 | 19.650 | 0.402 | 1.00 | 64.90 | B | N |
| ATOM | 8831 | CA | TYR | B | 34 | 74.073 | 18.860 | 0.224 | 1.00 | 69.43 | B | C |
| ATOM | 8833 | CB | TYR | B | 34 | 72.841 | 19.789 | 0.239 | 1.00 | 70.86 | B | C |
| ATOM | 8836 | CG | TYR | B | 34 | 71.502 | 19.080 | 0.363 | 1.00 | 79.22 | B | C |
| ATOM | 8837 | CD1 | TYR | B | 34 | 70.964 | 18.781 | 1.617 | 1.00 | 87.20 | B | C |
| ATOM | 8839 | CE1 | TYR | B | 34 | 69.737 | 18.137 | 1.740 | 1.00 | 89.29 | B | C |
| ATOM | 8841 | CZ | TYR | B | 34 | 69.029 | 17.792 | 0.600 | 1.00 | 92.08 | B | C |
| ATOM | 8842 | OH | TYR | B | 34 | 67.812 | 17.157 | 0.722 | 1.00 | 95.47 | B | O |
| ATOM | 8844 | CE2 | TYR | B | 34 | 69.537 | 18.085 | −0.659 | 1.00 | 89.29 | B | C |
| ATOM | 8846 | CD2 | TYR | B | 34 | 70.767 | 18.728 | −0.770 | 1.00 | 85.21 | B | C |
| ATOM | 8848 | C | TYR | B | 34 | 74.118 | 18.028 | −1.070 | 1.00 | 70.87 | B | C |
| ATOM | 8849 | O | TYR | B | 34 | 73.976 | 16.808 | −1.022 | 1.00 | 71.02 | B | O |
| ATOM | 8851 | N | LEU | B | 35 | 74.306 | 18.686 | −2.217 | 1.00 | 73.23 | B | N |
| ATOM | 8852 | CA | LEU | B | 35 | 74.646 | 17.990 | −3.465 | 1.00 | 75.05 | B | C |
| ATOM | 8854 | CB | LEU | B | 35 | 74.518 | 18.928 | −4.672 | 1.00 | 73.87 | B | C |
| ATOM | 8857 | CG | LEU | B | 35 | 73.181 | 19.646 | −4.918 | 1.00 | 72.69 | B | C |
| ATOM | 8859 | CD1 | LEU | B | 35 | 73.321 | 20.646 | −6.063 | 1.00 | 69.30 | B | C |
| ATOM | 8863 | CD2 | LEU | B | 35 | 72.033 | 18.678 | −5.204 | 1.00 | 66.46 | B | C |
| ATOM | 8867 | C | LEU | B | 35 | 76.092 | 17.517 | −3.304 | 1.00 | 78.50 | B | C |
| ATOM | 8868 | O | LEU | B | 35 | 76.785 | 17.996 | −2.414 | 1.00 | 79.84 | B | O |
| ATOM | 8870 | N | LEU | B | 36 | 76.554 | 16.580 | −4.126 | 1.00 | 81.41 | B | N |
| ATOM | 8871 | CA | LEU | B | 36 | 77.964 | 16.142 | −4.067 | 1.00 | 84.34 | B | C |
| ATOM | 8873 | CB | LEU | B | 36 | 78.905 | 17.267 | −4.546 | 1.00 | 84.18 | B | C |
| ATOM | 8876 | CG | LEU | B | 36 | 79.015 | 17.545 | −6.043 | 1.00 | 85.03 | B | C |
| ATOM | 8878 | CD1 | LEU | B | 36 | 79.771 | 18.850 | −6.269 | 1.00 | 85.63 | B | C |
| ATOM | 8882 | CD2 | LEU | B | 36 | 79.688 | 16.379 | −6.768 | 1.00 | 84.74 | B | C |
| ATOM | 8886 | C | LEU | B | 36 | 78.429 | 15.663 | −2.676 | 1.00 | 86.98 | B | C |
| ATOM | 8887 | O | LEU | B | 36 | 79.490 | 16.072 | −2.193 | 1.00 | 87.19 | B | O |
| ATOM | 8889 | N | SER | B | 37 | 77.637 | 14.812 | −2.029 | 1.00 | 90.52 | B | N |
| ATOM | 8890 | CA | SER | B | 37 | 78.077 | 14.126 | −0.804 | 1.00 | 92.80 | B | C |
| ATOM | 8892 | CB | SER | B | 37 | 77.125 | 14.406 | 0.375 | 1.00 | 93.04 | B | C |
| ATOM | 8895 | OG | SER | B | 37 | 76.054 | 13.477 | 0.440 | 1.00 | 93.00 | B | O |
| ATOM | 8897 | C | SER | B | 37 | 78.202 | 12.623 | −1.103 | 1.00 | 94.93 | B | C |
| ATOM | 8898 | O | SER | B | 37 | 77.529 | 12.105 | −2.009 | 1.00 | 95.38 | B | O |
| ATOM | 8900 | N | SER | B | 38 | 79.068 | 11.936 | −0.353 | 1.00 | 96.53 | B | N |
| ATOM | 8901 | CA | SER | B | 38 | 79.407 | 10.533 | −0.635 | 1.00 | 97.64 | B | C |
| ATOM | 8903 | CB | SER | B | 38 | 80.710 | 10.135 | 0.070 | 1.00 | 97.75 | B | C |
| ATOM | 8906 | OG | SER | B | 38 | 80.469 | 9.681 | 1.391 | 1.00 | 98.14 | B | O |
| ATOM | 8908 | C | SER | B | 38 | 78.277 | 9.586 | −0.222 | 1.00 | 98.41 | B | C |
| ATOM | 8909 | O | SER | B | 38 | 78.104 | 8.514 | −0.802 | 1.00 | 98.59 | B | O |
| ATOM | 8911 | N | ILE | B | 44 | 83.839 | 12.635 | −5.393 | 1.00 | 94.49 | B | N |
| ATOM | 8912 | CA | ILE | B | 44 | 82.761 | 13.547 | −5.022 | 1.00 | 93.90 | B | C |
| ATOM | 8914 | CB | ILE | B | 44 | 81.411 | 12.780 | −4.783 | 1.00 | 94.49 | B | C |
| ATOM | 8916 | CG1 | ILE | B | 44 | 81.066 | 11.873 | −5.977 | 1.00 | 95.23 | B | C |
| ATOM | 8919 | CD1 | ILE | B | 44 | 79.671 | 11.239 | −5.902 | 1.00 | 93.84 | B | C |
| ATOM | 8923 | CG2 | ILE | B | 44 | 80.260 | 13.748 | −4.553 | 1.00 | 94.85 | B | C |
| ATOM | 8927 | C | ILE | B | 44 | 83.150 | 14.379 | −3.786 | 1.00 | 92.23 | B | C |
| ATOM | 8928 | O | ILE | B | 44 | 82.375 | 15.230 | −3.340 | 1.00 | 92.29 | B | O |
| ATOM | 8930 | N | GLU | B | 45 | 84.357 | 14.149 | −3.257 | 1.00 | 89.93 | B | N |
| ATOM | 8931 | CA | GLU | B | 45 | 84.858 | 14.871 | −2.079 | 1.00 | 88.17 | B | C |
| ATOM | 8933 | CB | GLU | B | 45 | 85.549 | 13.906 | −1.114 | 1.00 | 88.70 | B | C |
| ATOM | 8936 | CG | GLU | B | 45 | 84.632 | 12.834 | −0.533 | 1.00 | 91.80 | B | C |
| ATOM | 8939 | CD | GLU | B | 45 | 85.373 | 11.838 | 0.361 | 1.00 | 95.23 | B | C |
| ATOM | 8940 | OE1 | GLU | B | 45 | 86.408 | 12.215 | 0.962 | 1.00 | 95.84 | B | O |
| ATOM | 8941 | OE2 | GLU | B | 45 | 84.916 | 10.676 | 0.465 | 1.00 | 93.58 | B | O |
| ATOM | 8942 | C | GLU | B | 45 | 85.821 | 16.011 | −2.435 | 1.00 | 85.13 | B | C |
| ATOM | 8943 | O | GLU | B | 45 | 85.588 | 17.159 | −2.053 | 1.00 | 84.84 | B | O |
| ATOM | 8945 | N | VAL | B | 46 | 86.909 | 15.693 | −3.139 | 1.00 | 81.48 | B | N |
| ATOM | 8946 | CA | VAL | B | 46 | 87.890 | 16.710 | −3.562 | 1.00 | 78.17 | B | C |
| ATOM | 8948 | CB | VAL | B | 46 | 89.203 | 16.066 | −4.107 | 1.00 | 78.25 | B | C |
| ATOM | 8950 | CG1 | VAL | B | 46 | 90.111 | 17.117 | −4.756 | 1.00 | 77.80 | B | C |
| ATOM | 8954 | CG2 | VAL | B | 46 | 89.942 | 15.339 | −2.989 | 1.00 | 78.65 | B | C |
| ATOM | 8958 | C | VAL | B | 46 | 87.271 | 17.647 | −4.609 | 1.00 | 74.01 | B | C |
| ATOM | 8959 | O | VAL | B | 46 | 87.633 | 18.815 | −4.691 | 1.00 | 74.42 | B | O |
| ATOM | 8961 | N | TYR | B | 47 | 86.343 | 17.111 | −5.397 | 1.00 | 68.89 | B | N |
| ATOM | 8962 | CA | TYR | B | 47 | 85.530 | 17.877 | −6.341 | 1.00 | 65.57 | B | C |
| ATOM | 8964 | CB | TYR | B | 47 | 84.662 | 16.884 | −7.117 | 1.00 | 65.80 | B | C |
| ATOM | 8967 | CG | TYR | B | 47 | 83.812 | 17.399 | −8.261 | 1.00 | 68.62 | B | C |
| ATOM | 8968 | CD1 | TYR | B | 47 | 84.261 | 17.333 | −9.579 | 1.00 | 72.47 | B | C |

TABLE 4-2-continued

Coordinates of *P. alba* IspS

| ATOM | 8970 | CE1 | TYR | B | 47 | 83.452 | 17.766 | −10.647 | 1.00 | 72.49 | B | C |
|---|---|---|---|---|---|---|---|---|---|---|---|---|
| ATOM | 8972 | CZ | TYR | B | 47 | 82.165 | 18.246 | −10.397 | 1.00 | 73.07 | B | C |
| ATOM | 8973 | OH | TYR | B | 47 | 81.346 | 18.679 | −11.437 | 1.00 | 56.23 | B | O |
| ATOM | 8975 | CE2 | TYR | B | 47 | 81.697 | 18.296 | −9.090 | 1.00 | 72.24 | B | C |
| ATOM | 8977 | CD2 | TYR | B | 47 | 82.516 | 17.861 | −8.036 | 1.00 | 72.42 | B | C |
| ATOM | 8979 | C | TYR | B | 47 | 84.670 | 18.905 | −5.585 | 1.00 | 61.56 | B | C |
| ATOM | 8980 | O | TYR | B | 47 | 84.605 | 20.068 | −5.981 | 1.00 | 60.03 | B | O |
| ATOM | 8982 | N | LYS | B | 48 | 84.041 | 18.471 | −4.488 | 1.00 | 57.03 | B | N |
| ATOM | 8983 | CA | LYS | B | 48 | 83.250 | 19.350 | −3.606 | 1.00 | 53.54 | B | C |
| ATOM | 8985 | CB | LYS | B | 48 | 82.637 | 18.549 | −2.448 | 1.00 | 53.56 | B | C |
| ATOM | 8988 | CG | LYS | B | 48 | 81.822 | 19.383 | −1.449 | 1.00 | 55.92 | B | C |
| ATOM | 8991 | CD | LYS | B | 48 | 81.250 | 18.518 | −0.323 | 1.00 | 61.31 | B | C |
| ATOM | 8994 | CE | LYS | B | 48 | 82.258 | 18.292 | 0.806 | 1.00 | 65.33 | B | C |
| ATOM | 8997 | NZ | LYS | B | 48 | 81.669 | 17.565 | 1.968 | 1.00 | 65.45 | B | N |
| ATOM | 9001 | C | LYS | B | 48 | 84.064 | 20.505 | −3.023 | 1.00 | 49.39 | B | C |
| ATOM | 9002 | O | LYS | B | 48 | 83.614 | 21.643 | −3.014 | 1.00 | 48.79 | B | O |
| ATOM | 9004 | N | ASP | B | 49 | 85.252 | 20.197 | −2.526 | 1.00 | 45.46 | B | N |
| ATOM | 9005 | CA | ASP | B | 49 | 86.102 | 21.189 | −1.878 | 1.00 | 44.14 | B | C |
| ATOM | 9007 | CB | ASP | B | 49 | 87.217 | 20.505 | −1.049 | 1.00 | 45.26 | B | C |
| ATOM | 9010 | CG | ASP | B | 49 | 86.675 | 19.718 | 0.166 | 1.00 | 48.58 | B | C |
| ATOM | 9011 | OD1 | ASP | B | 49 | 85.493 | 19.908 | 0.553 | 1.00 | 51.70 | B | O |
| ATOM | 9012 | OD2 | ASP | B | 49 | 87.447 | 18.916 | 0.745 | 1.00 | 47.26 | B | O |
| ATOM | 9013 | C | ASP | B | 49 | 86.707 | 22.135 | −2.910 | 1.00 | 40.94 | B | C |
| ATOM | 9014 | O | ASP | B | 49 | 87.065 | 23.274 | −2.581 | 1.00 | 38.32 | B | O |
| ATOM | 9016 | N | LYS | B | 50 | 86.830 | 21.655 | −4.151 | 1.00 | 38.29 | B | N |
| ATOM | 9017 | CA | LYS | B | 50 | 87.259 | 22.502 | −5.260 | 1.00 | 36.73 | B | C |
| ATOM | 9019 | CB | LYS | B | 50 | 87.580 | 21.669 | −6.500 | 1.00 | 38.18 | B | C |
| ATOM | 9022 | CG | LYS | B | 50 | 88.431 | 22.387 | −7.554 | 1.00 | 44.48 | B | C |
| ATOM | 9025 | CD | LYS | B | 50 | 89.936 | 22.153 | −7.346 | 1.00 | 56.72 | B | C |
| ATOM | 9028 | CE | LYS | B | 50 | 90.744 | 22.329 | −8.644 | 1.00 | 59.64 | B | C |
| ATOM | 9031 | NZ | LYS | B | 50 | 90.457 | 21.259 | −9.654 | 1.00 | 56.87 | B | N |
| ATOM | 9035 | C | LYS | B | 50 | 86.141 | 23.497 | −5.555 | 1.00 | 33.08 | B | C |
| ATOM | 9036 | O | LYS | B | 50 | 86.391 | 24.692 | −5.665 | 1.00 | 32.79 | B | O |
| ATOM | 9038 | N | ALA | B | 51 | 84.905 | 23.011 | −5.635 | 1.00 | 28.99 | B | N |
| ATOM | 9039 | CA | ALA | B | 51 | 83.779 | 23.878 | −5.971 | 1.00 | 28.45 | B | C |
| ATOM | 9041 | CB | ALA | B | 51 | 82.493 | 23.070 | −6.203 | 1.00 | 26.35 | B | C |
| ATOM | 9045 | C | ALA | B | 51 | 83.570 | 24.969 | −4.908 | 1.00 | 25.62 | B | C |
| ATOM | 9046 | O | ALA | B | 51 | 83.382 | 26.125 | −5.250 | 1.00 | 27.03 | B | O |
| ATOM | 9048 | N | LYS | B | 52 | 83.640 | 24.605 | −3.639 | 1.00 | 23.23 | B | N |
| ATOM | 9049 | CA | LYS | B | 52 | 83.402 | 25.549 | −2.558 | 1.00 | 25.12 | B | C |
| ATOM | 9051 | CB | LYS | B | 52 | 83.462 | 24.826 | −1.222 | 1.00 | 26.00 | B | C |
| ATOM | 9054 | CG | LYS | B | 52 | 82.247 | 23.917 | −0.950 | 1.00 | 32.90 | B | C |
| ATOM | 9057 | CD | LYS | B | 52 | 82.548 | 22.836 | 0.119 | 1.00 | 33.42 | B | C |
| ATOM | 9060 | CE | LYS | B | 52 | 82.519 | 23.382 | 1.545 | 1.00 | 38.08 | B | C |
| ATOM | 9063 | NZ | LYS | B | 52 | 83.221 | 22.478 | 2.543 | 1.00 | 41.70 | B | N |
| ATOM | 9067 | C | LYS | B | 52 | 84.382 | 26.734 | −2.559 | 1.00 | 25.93 | B | C |
| ATOM | 9068 | O | LYS | B | 52 | 83.977 | 27.889 | −2.356 | 1.00 | 25.95 | B | O |
| ATOM | 9070 | N | LYS | B | 53 | 85.659 | 26.441 | −2.800 | 1.00 | 24.65 | B | N |
| ATOM | 9071 | CA | LYS | B | 53 | 86.713 | 27.468 | −2.865 | 1.00 | 26.16 | B | C |
| ATOM | 9073 | CB | LYS | B | 53 | 88.072 | 26.795 | −3.053 | 1.00 | 28.69 | B | C |
| ATOM | 9076 | CG | LYS | B | 53 | 89.272 | 27.687 | −2.785 | 1.00 | 38.87 | B | C |
| ATOM | 9079 | CD | LYS | B | 53 | 90.559 | 26.848 | −2.633 | 1.00 | 49.83 | B | C |
| ATOM | 9082 | CE | LYS | B | 53 | 91.819 | 27.730 | −2.464 | 1.00 | 57.01 | B | C |
| ATOM | 9085 | NZ | LYS | B | 53 | 91.931 | 28.843 | −3.484 | 1.00 | 55.43 | B | N |
| ATOM | 9089 | C | LYS | B | 53 | 86.476 | 28.458 | −4.011 | 1.00 | 23.98 | B | C |
| ATOM | 9090 | O | LYS | B | 53 | 86.553 | 29.666 | −3.818 | 1.00 | 22.54 | B | O |
| ATOM | 9092 | N | LEU | B | 54 | 86.180 | 27.918 | −5.188 | 1.00 | 22.61 | B | N |
| ATOM | 9093 | CA | LEU | B | 54 | 85.881 | 28.705 | −6.377 | 1.00 | 23.43 | B | C |
| ATOM | 9095 | CB | LEU | B | 54 | 85.746 | 27.787 | −7.601 | 1.00 | 25.24 | B | C |
| ATOM | 9098 | CG | LEU | B | 54 | 86.885 | 26.810 | −7.946 | 1.00 | 24.59 | B | C |
| ATOM | 9100 | CD1 | LEU | B | 54 | 86.382 | 25.820 | −8.997 | 1.00 | 16.54 | B | C |
| ATOM | 9104 | CD2 | LEU | B | 54 | 88.140 | 27.524 | −8.433 | 1.00 | 26.50 | B | C |
| ATOM | 9108 | C | LEU | B | 54 | 84.602 | 29.524 | −6.185 | 1.00 | 22.18 | B | C |
| ATOM | 9109 | O | LEU | B | 54 | 84.580 | 30.696 | −6.496 | 1.00 | 20.99 | B | O |
| ATOM | 9111 | N | GLU | B | 55 | 83.544 | 28.909 | −5.656 | 1.00 | 21.18 | B | N |
| ATOM | 9112 | CA | GLU | B | 55 | 82.297 | 29.631 | −5.346 | 1.00 | 19.85 | B | C |
| ATOM | 9114 | CB | GLU | B | 55 | 81.221 | 28.667 | −4.811 | 1.00 | 19.93 | B | C |
| ATOM | 9117 | CG | GLU | B | 55 | 79.945 | 29.338 | −4.252 | 1.00 | 21.78 | B | C |
| ATOM | 9120 | CD | GLU | B | 55 | 78.928 | 28.318 | −3.683 | 1.00 | 25.47 | B | C |
| ATOM | 9121 | OE1 | GLU | B | 55 | 79.358 | 27.408 | −2.970 | 1.00 | 25.89 | B | O |
| ATOM | 9122 | OE2 | GLU | B | 55 | 77.712 | 28.432 | −3.943 | 1.00 | 30.12 | B | O |
| ATOM | 9123 | C | GLU | B | 55 | 82.507 | 30.751 | −4.333 | 1.00 | 16.88 | B | C |
| ATOM | 9124 | O | GLU | B | 55 | 81.902 | 31.810 | −4.444 | 1.00 | 18.42 | B | O |
| ATOM | 9126 | N | ALA | B | 56 | 83.331 | 30.498 | −3.332 | 1.00 | 17.01 | B | N |
| ATOM | 9127 | CA | ALA | B | 56 | 83.662 | 31.512 | −2.318 | 1.00 | 17.77 | B | C |
| ATOM | 9129 | CB | ALA | B | 56 | 84.639 | 30.933 | −1.285 | 1.00 | 14.61 | B | C |
| ATOM | 9133 | C | ALA | B | 56 | 84.260 | 32.750 | −2.974 | 1.00 | 16.65 | B | C |
| ATOM | 9134 | O | ALA | B | 56 | 83.866 | 33.892 | −2.698 | 1.00 | 17.77 | B | O |

TABLE 4-2-continued

Coordinates of P. alba IspS

| ATOM | 9136 | N | GLU | B | 57 | 85.192 | 32.504 | −3.881 | 1.00 | 17.66 | B | N |
|------|------|------|------|---|----|--------|--------|--------|------|-------|---|---|
| ATOM | 9137 | CA | GLU | B | 57 | 85.891 | 33.568 | −4.576 | 1.00 | 19.52 | B | C |
| ATOM | 9139 | CB | GLU | B | 57 | 87.061 | 32.978 | −5.370 | 1.00 | 20.51 | B | C |
| ATOM | 9142 | CG | GLU | B | 57 | 87.856 | 34.013 | −6.123 | 1.00 | 28.03 | B | C |
| ATOM | 9145 | CD | GLU | B | 57 | 89.220 | 33.529 | −6.584 | 1.00 | 29.71 | B | C |
| ATOM | 9146 | OE1 | GLU | B | 57 | 89.788 | 32.582 | −5.980 | 1.00 | 32.81 | B | O |
| ATOM | 9147 | OE2 | GLU | B | 57 | 89.714 | 34.123 | −7.558 | 1.00 | 32.47 | B | O |
| ATOM | 9148 | C | GLU | B | 57 | 84.926 | 34.373 | −5.464 | 1.00 | 18.10 | B | C |
| ATOM | 9149 | O | GLU | B | 57 | 84.956 | 35.612 | −5.451 | 1.00 | 17.86 | B | O |
| ATOM | 9151 | N | VAL | B | 58 | 84.052 | 33.683 | −6.201 | 1.00 | 15.98 | B | N |
| ATOM | 9152 | CA | VAL | B | 58 | 83.038 | 34.371 | −6.998 | 1.00 | 15.98 | B | C |
| ATOM | 9154 | CB | VAL | B | 58 | 82.222 | 33.394 | −7.875 | 1.00 | 18.04 | B | C |
| ATOM | 9156 | CG1 | VAL | B | 58 | 81.131 | 34.128 | −8.663 | 1.00 | 15.64 | B | C |
| ATOM | 9160 | CG2 | VAL | B | 58 | 83.138 | 32.696 | −8.844 | 1.00 | 18.23 | B | C |
| ATOM | 9164 | C | VAL | B | 58 | 82.135 | 35.203 | −6.089 | 1.00 | 14.38 | B | C |
| ATOM | 9165 | O | VAL | B | 58 | 81.813 | 36.330 | −6.395 | 1.00 | 12.91 | B | O |
| ATOM | 9167 | N | ARG | B | 59 | 81.773 | 34.666 | −4.935 | 1.00 | 18.23 | B | N |
| ATOM | 9168 | CA | ARG | B | 59 | 80.953 | 35.412 | −3.976 | 1.00 | 19.65 | B | C |
| ATOM | 9170 | CB | ARG | B | 59 | 80.619 | 34.534 | −2.741 | 1.00 | 22.03 | B | C |
| ATOM | 9173 | CG | ARG | B | 59 | 79.877 | 35.245 | −1.579 | 1.00 | 22.47 | B | C |
| ATOM | 9176 | CD | ARG | B | 59 | 80.840 | 36.086 | −0.641 | 1.00 | 25.58 | B | C |
| ATOM | 9179 | NE | ARG | B | 59 | 80.117 | 36.788 | 0.431 | 1.00 | 24.31 | B | N |
| ATOM | 9181 | CZ | ARG | B | 59 | 80.644 | 37.698 | 1.250 | 1.00 | 27.67 | B | C |
| ATOM | 9182 | NH1 | ARG | B | 59 | 79.881 | 38.260 | 2.182 | 1.00 | 25.80 | B | N |
| ATOM | 9185 | NH2 | ARG | B | 59 | 81.926 | 38.056 | 1.146 | 1.00 | 25.89 | B | N |
| ATOM | 9188 | C | ARG | B | 59 | 81.673 | 36.705 | −3.578 | 1.00 | 19.80 | B | C |
| ATOM | 9189 | O | ARG | B | 59 | 81.077 | 37.780 | −3.578 | 1.00 | 21.68 | B | O |
| ATOM | 9191 | N | ARG | B | 60 | 82.953 | 36.603 | −3.241 | 1.00 | 20.03 | B | N |
| ATOM | 9192 | CA | ARG | B | 60 | 83.717 | 37.782 | −2.820 | 1.00 | 18.94 | B | C |
| ATOM | 9194 | CB | ARG | B | 60 | 85.145 | 37.411 | −2.468 | 1.00 | 19.04 | B | C |
| ATOM | 9197 | CG | ARG | B | 60 | 86.020 | 38.589 | −2.002 | 1.00 | 22.87 | B | C |
| ATOM | 9200 | CD | ARG | B | 60 | 87.442 | 38.164 | −1.777 | 1.00 | 19.95 | B | C |
| ATOM | 9203 | NE | ARG | B | 60 | 88.075 | 37.838 | −3.049 | 1.00 | 25.88 | B | N |
| ATOM | 9205 | CZ | ARG | B | 60 | 89.176 | 37.106 | −3.209 | 1.00 | 26.18 | B | C |
| ATOM | 9206 | NH1 | ARG | B | 60 | 89.836 | 36.578 | −2.176 | 1.00 | 24.93 | B | N |
| ATOM | 9209 | NH2 | ARG | B | 60 | 89.620 | 36.904 | −4.435 | 1.00 | 23.40 | B | N |
| ATOM | 9212 | C | ARG | B | 60 | 83.718 | 38.843 | −3.915 | 1.00 | 18.30 | B | C |
| ATOM | 9213 | O | ARG | B | 60 | 83.427 | 40.007 | −3.650 | 1.00 | 16.21 | B | O |
| ATOM | 9215 | N | GLU | B | 61 | 84.015 | 38.434 | −5.140 | 1.00 | 18.15 | B | N |
| ATOM | 9216 | CA | GLU | B | 61 | 84.066 | 39.367 | −6.264 | 1.00 | 18.45 | B | C |
| ATOM | 9218 | CB | GLU | B | 61 | 84.564 | 38.663 | −7.523 | 1.00 | 18.70 | B | C |
| ATOM | 9221 | CG | GLU | B | 61 | 86.037 | 38.270 | −7.425 | 1.00 | 25.62 | B | C |
| ATOM | 9224 | CD | GLU | B | 61 | 86.901 | 39.429 | −6.970 | 1.00 | 31.59 | B | C |
| ATOM | 9225 | OE1 | GLU | B | 61 | 86.893 | 40.488 | −7.648 | 1.00 | 33.81 | B | O |
| ATOM | 9226 | OE2 | GLU | B | 61 | 87.559 | 39.290 | −5.918 | 1.00 | 30.53 | B | O |
| ATOM | 9227 | C | GLU | B | 61 | 82.734 | 40.062 | −6.528 | 1.00 | 17.97 | B | C |
| ATOM | 9228 | O | GLU | B | 61 | 82.711 | 41.245 | −6.761 | 1.00 | 19.38 | B | O |
| ATOM | 9230 | N | ILE | B | 62 | 81.617 | 39.356 | −6.435 | 1.00 | 17.52 | B | N |
| ATOM | 9231 | CA | ILE | B | 62 | 80.341 | 40.023 | −6.594 | 1.00 | 18.58 | B | C |
| ATOM | 9233 | CB | ILE | B | 62 | 79.169 | 39.006 | −6.731 | 1.00 | 19.89 | B | C |
| ATOM | 9235 | CG1 | ILE | B | 62 | 79.343 | 38.137 | −7.974 | 1.00 | 21.73 | B | C |
| ATOM | 9238 | CD1 | ILE | B | 62 | 78.456 | 36.881 | −8.000 | 1.00 | 15.32 | B | C |
| ATOM | 9242 | CG2 | ILE | B | 62 | 77.810 | 39.738 | −6.823 | 1.00 | 21.38 | B | C |
| ATOM | 9246 | C | ILE | B | 62 | 80.071 | 41.005 | −5.433 | 1.00 | 19.09 | B | C |
| ATOM | 9247 | O | ILE | B | 62 | 79.379 | 41.984 | −5.615 | 1.00 | 20.23 | B | O |
| ATOM | 9249 | N | ASN | B | 63 | 80.606 | 40.732 | −4.244 | 1.00 | 20.89 | B | N |
| ATOM | 9250 | CA | ASN | B | 63 | 80.300 | 41.510 | −3.024 | 1.00 | 21.02 | B | C |
| ATOM | 9252 | CB | ASN | B | 63 | 80.355 | 40.597 | −1.783 | 1.00 | 20.11 | B | C |
| ATOM | 9255 | CG | ASN | B | 63 | 79.061 | 39.859 | −1.543 | 1.00 | 25.79 | B | C |
| ATOM | 9256 | OD1 | ASN | B | 63 | 78.128 | 40.417 | −0.976 | 1.00 | 29.46 | B | O |
| ATOM | 9257 | ND2 | ASN | B | 63 | 78.999 | 38.591 | −1.957 | 1.00 | 22.36 | B | N |
| ATOM | 9260 | C | ASN | B | 63 | 81.262 | 42.671 | −2.838 | 1.00 | 23.00 | B | C |
| ATOM | 9261 | O | ASN | B | 63 | 81.077 | 43.514 | −1.968 | 1.00 | 22.33 | B | O |
| ATOM | 9263 | N | ASN | B | 64 | 82.292 | 42.697 | −3.674 | 1.00 | 25.47 | B | N |
| ATOM | 9264 | CA | ASN | B | 64 | 83.322 | 43.708 | −3.630 | 1.00 | 27.17 | B | C |
| ATOM | 9266 | CB | ASN | B | 64 | 84.400 | 43.341 | −4.646 | 1.00 | 28.05 | B | C |
| ATOM | 9269 | CG | ASN | B | 64 | 85.562 | 44.319 | −4.642 | 1.00 | 28.60 | B | C |
| ATOM | 9270 | OD1 | ASN | B | 64 | 85.793 | 45.052 | −3.663 | 1.00 | 21.94 | B | O |
| ATOM | 9271 | ND2 | ASN | B | 64 | 86.299 | 44.331 | −5.732 | 1.00 | 18.57 | B | N |
| ATOM | 9274 | C | ASN | B | 64 | 82.840 | 45.121 | −3.922 | 1.00 | 29.58 | B | C |
| ATOM | 9275 | O | ASN | B | 64 | 82.518 | 45.441 | −5.073 | 1.00 | 30.80 | B | O |
| ATOM | 9277 | N | GLU | B | 65 | 82.848 | 45.977 | −2.901 | 1.00 | 31.46 | B | N |
| ATOM | 9278 | CA | GLU | B | 65 | 82.308 | 47.333 | −3.039 | 1.00 | 34.52 | B | C |
| ATOM | 9280 | CB | GLU | B | 65 | 81.787 | 47.849 | −1.680 | 1.00 | 36.07 | B | C |
| ATOM | 9283 | CG | GLU | B | 65 | 80.519 | 47.079 | −1.202 | 1.00 | 40.76 | B | C |
| ATOM | 9286 | CD | GLU | B | 65 | 79.853 | 47.631 | 0.070 | 1.00 | 46.69 | B | C |
| ATOM | 9287 | OE1 | GLU | B | 65 | 79.267 | 46.807 | 0.819 | 1.00 | 45.52 | B | O |
| ATOM | 9288 | OE2 | GLU | B | 65 | 79.891 | 48.862 | 0.314 | 1.00 | 44.38 | B | O |

TABLE 4-2-continued

Coordinates of *P. alba* IspS

| ATOM | 9289 | C | GLU | B | 65 | 83.299 | 48.314 | −3.700 | 1.00 | 34.91 | B | C |
|---|---|---|---|---|---|---|---|---|---|---|---|---|
| ATOM | 9290 | O | GLU | B | 65 | 82.903 | 49.396 | −4.110 | 1.00 | 35.59 | B | O |
| ATOM | 9292 | N | LYS | B | 66 | 84.561 | 47.909 | −3.843 | 1.00 | 34.28 | B | N |
| ATOM | 9293 | CA | LYS | B | 66 | 85.599 | 48.730 | −4.488 | 1.00 | 35.18 | B | C |
| ATOM | 9295 | CB | LYS | B | 66 | 86.982 | 48.469 | −3.863 | 1.00 | 35.99 | B | C |
| ATOM | 9298 | CG | LYS | B | 66 | 87.045 | 48.467 | −2.339 | 1.00 | 38.17 | B | C |
| ATOM | 9301 | CD | LYS | B | 66 | 88.463 | 48.112 | −1.873 | 1.00 | 44.44 | B | C |
| ATOM | 9304 | CE | LYS | B | 66 | 88.568 | 47.948 | −0.356 | 1.00 | 45.69 | B | C |
| ATOM | 9307 | NZ | LYS | B | 66 | 87.722 | 48.925 | 0.382 | 1.00 | 46.38 | B | N |
| ATOM | 9311 | C | LYS | B | 66 | 85.706 | 48.474 | −5.997 | 1.00 | 33.33 | B | C |
| ATOM | 9312 | O | LYS | B | 66 | 86.472 | 49.135 | −6.685 | 1.00 | 31.57 | B | O |
| ATOM | 9314 | N | ALA | B | 67 | 84.959 | 47.506 | −6.507 | 1.00 | 33.36 | B | N |
| ATOM | 9315 | CA | ALA | B | 67 | 85.026 | 47.165 | −7.925 | 1.00 | 34.20 | B | C |
| ATOM | 9317 | CB | ALA | B | 67 | 84.218 | 45.897 | −8.204 | 1.00 | 33.29 | B | C |
| ATOM | 9321 | C | ALA | B | 67 | 84.525 | 48.322 | −8.800 | 1.00 | 33.66 | B | C |
| ATOM | 9322 | O | ALA | B | 67 | 83.650 | 49.084 | −8.405 | 1.00 | 30.94 | B | O |
| ATOM | 9324 | N | GLU | B | 68 | 85.105 | 48.461 | −9.983 | 1.00 | 35.83 | B | N |
| ATOM | 9325 | CA | GLU | B | 68 | 84.593 | 49.428 | −10.952 | 1.00 | 38.70 | B | C |
| ATOM | 9327 | CB | GLU | B | 68 | 85.515 | 49.528 | −12.176 | 1.00 | 40.06 | B | C |
| ATOM | 9330 | CG | GLU | B | 68 | 85.648 | 50.931 | −12.771 | 1.00 | 49.30 | B | C |
| ATOM | 9333 | CD | GLU | B | 68 | 86.723 | 51.762 | −12.087 | 1.00 | 60.51 | B | C |
| ATOM | 9334 | OE1 | GLU | B | 68 | 86.676 | 51.895 | −10.839 | 1.00 | 64.15 | B | O |
| ATOM | 9335 | OE2 | GLU | B | 68 | 87.615 | 52.287 | −12.800 | 1.00 | 64.74 | B | O |
| ATOM | 9336 | C | GLU | B | 68 | 83.188 | 48.938 | −11.336 | 1.00 | 38.52 | B | C |
| ATOM | 9337 | O | GLU | B | 68 | 82.979 | 47.736 | −11.557 | 1.00 | 35.34 | B | O |
| ATOM | 9339 | N | PHE | B | 69 | 82.231 | 49.862 | −11.388 | 1.00 | 39.72 | B | N |
| ATOM | 9340 | CA | PHE | B | 69 | 80.824 | 49.499 | −11.583 | 1.00 | 40.88 | B | C |
| ATOM | 9342 | CB | PHE | B | 69 | 79.890 | 50.704 | −11.385 | 1.00 | 43.17 | B | C |
| ATOM | 9345 | CG | PHE | B | 69 | 79.457 | 50.916 | −9.936 | 1.00 | 53.21 | B | C |
| ATOM | 9346 | CD1 | PHE | B | 69 | 78.868 | 49.875 | −9.202 | 1.00 | 61.30 | B | C |
| ATOM | 9348 | CE1 | PHE | B | 69 | 78.463 | 50.062 | −7.870 | 1.00 | 62.25 | B | C |
| ATOM | 9350 | CZ | PHE | B | 69 | 78.638 | 51.301 | −7.260 | 1.00 | 64.99 | B | C |
| ATOM | 9352 | CE2 | PHE | B | 69 | 79.218 | 52.351 | −7.978 | 1.00 | 65.67 | B | C |
| ATOM | 9354 | CD2 | PHE | B | 69 | 79.621 | 52.156 | −9.312 | 1.00 | 63.60 | B | C |
| ATOM | 9356 | C | PHE | B | 69 | 80.540 | 48.786 | −12.914 | 1.00 | 38.20 | B | C |
| ATOM | 9357 | O | PHE | B | 69 | 79.713 | 47.862 | −12.946 | 1.00 | 35.79 | B | O |
| ATOM | 9359 | N | LEU | B | 70 | 81.237 | 49.159 | −13.983 | 1.00 | 34.86 | B | N |
| ATOM | 9360 | CA | LEU | B | 70 | 81.085 | 48.435 | −15.256 | 1.00 | 35.39 | B | C |
| ATOM | 9362 | CB | LEU | B | 70 | 81.786 | 49.157 | −16.411 | 1.00 | 35.66 | B | C |
| ATOM | 9365 | CG | LEU | B | 70 | 81.573 | 48.513 | −17.786 | 1.00 | 42.16 | B | C |
| ATOM | 9367 | CD1 | LEU | B | 70 | 80.104 | 48.554 | −18.171 | 1.00 | 42.12 | B | C |
| ATOM | 9371 | CD2 | LEU | B | 70 | 82.425 | 49.189 | −18.855 | 1.00 | 49.16 | B | C |
| ATOM | 9375 | C | LEU | B | 70 | 81.603 | 46.999 | −15.160 | 1.00 | 32.47 | B | C |
| ATOM | 9376 | O | LEU | B | 70 | 80.945 | 46.071 | −15.596 | 1.00 | 31.99 | B | O |
| ATOM | 9378 | N | THR | B | 71 | 82.790 | 46.834 | −14.592 | 1.00 | 31.77 | B | N |
| ATOM | 9379 | CA | THR | B | 71 | 83.396 | 45.516 | −14.366 | 1.00 | 30.39 | B | C |
| ATOM | 9381 | CB | THR | B | 71 | 84.794 | 45.678 | −13.756 | 1.00 | 31.06 | B | C |
| ATOM | 9383 | OG1 | THR | B | 71 | 85.585 | 46.494 | −14.633 | 1.00 | 34.93 | B | O |
| ATOM | 9385 | CG2 | THR | B | 71 | 85.476 | 44.322 | −13.563 | 1.00 | 31.45 | B | C |
| ATOM | 9389 | C | THR | B | 71 | 82.533 | 44.619 | −13.460 | 1.00 | 27.80 | B | C |
| ATOM | 9390 | O | THR | B | 71 | 82.450 | 43.412 | −13.675 | 1.00 | 27.97 | B | O |
| ATOM | 9392 | N | LEU | B | 72 | 81.878 | 45.215 | −12.467 | 1.00 | 25.13 | B | N |
| ATOM | 9393 | CA | LEU | B | 72 | 80.955 | 44.476 | −11.614 | 1.00 | 24.98 | B | C |
| ATOM | 9395 | CB | LEU | B | 72 | 80.511 | 45.327 | −10.443 | 1.00 | 24.24 | B | C |
| ATOM | 9398 | CG | LEU | B | 72 | 79.716 | 44.642 | −9.339 | 1.00 | 33.31 | B | C |
| ATOM | 9400 | CD1 | LEU | B | 72 | 80.492 | 43.465 | −8.715 | 1.00 | 32.42 | B | C |
| ATOM | 9404 | CD2 | LEU | B | 72 | 79.346 | 45.677 | −8.266 | 1.00 | 35.81 | B | C |
| ATOM | 9408 | C | LEU | B | 72 | 79.736 | 44.026 | −12.410 | 1.00 | 24.17 | B | C |
| ATOM | 9409 | O | LEU | B | 72 | 79.330 | 42.888 | −12.318 | 1.00 | 21.92 | B | O |
| ATOM | 9411 | N | LEU | B | 73 | 79.158 | 44.928 | −13.196 | 1.00 | 24.75 | B | N |
| ATOM | 9412 | CA | LEU | B | 73 | 78.018 | 44.568 | −14.012 | 1.00 | 25.30 | B | C |
| ATOM | 9414 | CB | LEU | B | 73 | 77.467 | 45.786 | −14.758 | 1.00 | 25.87 | B | C |
| ATOM | 9417 | CG | LEU | B | 73 | 76.666 | 46.820 | −13.948 | 1.00 | 26.49 | B | C |
| ATOM | 9419 | CD1 | LEU | B | 73 | 76.237 | 47.980 | −14.845 | 1.00 | 24.24 | B | C |
| ATOM | 9423 | CD2 | LEU | B | 73 | 75.462 | 46.210 | −13.265 | 1.00 | 20.11 | B | C |
| ATOM | 9427 | C | LEU | B | 73 | 78.383 | 43.437 | −14.996 | 1.00 | 24.80 | B | C |
| ATOM | 9428 | O | LEU | B | 73 | 77.630 | 42.492 | −15.150 | 1.00 | 24.71 | B | O |
| ATOM | 9430 | N | GLU | B | 74 | 79.530 | 43.526 | −15.650 | 1.00 | 23.04 | B | N |
| ATOM | 9431 | CA | GLU | B | 74 | 79.934 | 42.456 | −16.561 | 1.00 | 24.32 | B | C |
| ATOM | 9433 | CB | GLU | B | 74 | 81.164 | 42.873 | −17.383 | 1.00 | 24.31 | B | C |
| ATOM | 9436 | CG | GLU | B | 74 | 80.842 | 43.894 | −18.492 | 1.00 | 35.06 | B | C |
| ATOM | 9439 | CD | GLU | B | 74 | 82.069 | 44.669 | −19.044 | 1.00 | 42.57 | B | C |
| ATOM | 9440 | OE1 | GLU | B | 74 | 83.235 | 44.254 | −18.819 | 1.00 | 41.46 | B | O |
| ATOM | 9441 | OE2 | GLU | B | 74 | 81.844 | 45.714 | −19.713 | 1.00 | 49.19 | B | O |
| ATOM | 9442 | C | GLU | B | 74 | 80.187 | 41.124 | −15.811 | 1.00 | 23.65 | B | C |
| ATOM | 9443 | O | GLU | B | 74 | 79.951 | 40.034 | −16.343 | 1.00 | 24.23 | B | O |
| ATOM | 9445 | N | LEU | B | 75 | 80.667 | 41.208 | −14.579 | 1.00 | 22.21 | B | N |
| ATOM | 9446 | CA | LEU | B | 75 | 80.888 | 40.012 | −13.794 | 1.00 | 20.79 | B | C |

TABLE 4-2-continued

Coordinates of P. alba IspS

| ATOM | 9448 | CB | LEU | B | 75 | 81.548 | 40.334 | −12.445 | 1.00 | 19.72 | B | C |
|---|---|---|---|---|---|---|---|---|---|---|---|---|
| ATOM | 9451 | CG | LEU | B | 75 | 81.715 | 39.168 | −11.461 | 1.00 | 19.52 | B | C |
| ATOM | 9453 | CD1 | LEU | B | 75 | 82.486 | 38.032 | −12.119 | 1.00 | 16.13 | B | C |
| ATOM | 9457 | CD2 | LEU | B | 75 | 82.437 | 39.647 | −10.211 | 1.00 | 21.45 | B | C |
| ATOM | 9461 | C | LEU | B | 75 | 79.553 | 39.335 | −13.576 | 1.00 | 19.44 | B | C |
| ATOM | 9462 | O | LEU | B | 75 | 79.445 | 38.130 | −13.753 | 1.00 | 21.48 | B | O |
| ATOM | 9464 | N | ILE | B | 76 | 78.543 | 40.115 | −13.197 | 1.00 | 19.42 | B | N |
| ATOM | 9465 | CA | ILE | B | 76 | 77.230 | 39.579 | −12.907 | 1.00 | 21.46 | B | C |
| ATOM | 9467 | CB | ILE | B | 76 | 76.256 | 40.654 | −12.379 | 1.00 | 23.58 | B | C |
| ATOM | 9469 | CG1 | ILE | B | 76 | 76.708 | 41.135 | −10.996 | 1.00 | 24.75 | B | C |
| ATOM | 9472 | CD1 | ILE | B | 76 | 75.987 | 42.362 | −10.509 | 1.00 | 22.54 | B | C |
| ATOM | 9476 | CG2 | ILE | B | 76 | 74.826 | 40.102 | −12.297 | 1.00 | 15.99 | B | C |
| ATOM | 9480 | C | ILE | B | 76 | 76.632 | 38.972 | −14.151 | 1.00 | 23.08 | B | C |
| ATOM | 9481 | O | ILE | B | 76 | 75.984 | 37.933 | −14.081 | 1.00 | 24.81 | B | O |
| ATOM | 9483 | N | ASP | B | 77 | 76.854 | 39.610 | −15.293 | 1.00 | 23.68 | B | N |
| ATOM | 9484 | CA | ASP | B | 77 | 76.279 | 39.122 | −16.545 | 1.00 | 23.98 | B | C |
| ATOM | 9486 | CB | ASP | B | 77 | 76.545 | 40.109 | −17.669 | 1.00 | 24.72 | B | C |
| ATOM | 9489 | CG | ASP | B | 77 | 75.708 | 39.838 | −18.906 | 1.00 | 28.60 | B | C |
| ATOM | 9490 | OD1 | ASP | B | 77 | 74.657 | 39.176 | −18.811 | 1.00 | 27.91 | B | O |
| ATOM | 9491 | OD2 | ASP | B | 77 | 76.095 | 40.332 | −19.984 | 1.00 | 33.20 | B | O |
| ATOM | 9492 | C | ASP | B | 77 | 76.900 | 37.791 | −16.896 | 1.00 | 22.93 | B | C |
| ATOM | 9493 | O | ASP | B | 77 | 76.206 | 36.855 | −17.301 | 1.00 | 21.74 | B | O |
| ATOM | 9495 | N | ASN | B | 78 | 78.211 | 37.703 | −16.733 | 1.00 | 21.06 | B | N |
| ATOM | 9496 | CA | ASN | B | 78 | 78.925 | 36.463 | −17.029 | 1.00 | 22.27 | B | C |
| ATOM | 9498 | CB | ASN | B | 78 | 80.438 | 36.637 | −16.866 | 1.00 | 25.30 | B | C |
| ATOM | 9501 | CG | ASN | B | 78 | 81.081 | 37.404 | −18.019 | 1.00 | 26.72 | B | C |
| ATOM | 9502 | OD1 | ASN | B | 78 | 80.708 | 37.233 | −19.156 | 1.00 | 23.36 | B | O |
| ATOM | 9503 | ND2 | ASN | B | 78 | 82.081 | 38.219 | −17.714 | 1.00 | 21.70 | B | N |
| ATOM | 9506 | C | ASN | B | 78 | 78.458 | 35.353 | −16.109 | 1.00 | 21.56 | B | C |
| ATOM | 9507 | O | ASN | B | 78 | 78.201 | 34.240 | −16.549 | 1.00 | 20.19 | B | O |
| ATOM | 9509 | N | VAL | B | 79 | 78.340 | 35.664 | −14.825 | 1.00 | 20.29 | B | N |
| ATOM | 9510 | CA | VAL | B | 79 | 77.917 | 34.672 | −13.843 | 1.00 | 21.77 | B | C |
| ATOM | 9512 | CB | VAL | B | 79 | 77.857 | 35.306 | −12.419 | 1.00 | 23.62 | B | C |
| ATOM | 9514 | CG1 | VAL | B | 79 | 77.001 | 34.467 | −11.466 | 1.00 | 19.36 | B | C |
| ATOM | 9518 | CG2 | VAL | B | 79 | 79.265 | 35.515 | −11.862 | 1.00 | 19.30 | B | C |
| ATOM | 9522 | C | VAL | B | 79 | 76.552 | 34.064 | −14.217 | 1.00 | 22.02 | B | C |
| ATOM | 9523 | O | VAL | B | 79 | 76.349 | 32.862 | −14.107 | 1.00 | 22.00 | B | O |
| ATOM | 9525 | N | GLN | B | 80 | 75.630 | 34.910 | −14.672 | 1.00 | 21.01 | B | N |
| ATOM | 9526 | CA | GLN | B | 80 | 74.265 | 34.482 | −15.024 | 1.00 | 19.29 | B | C |
| ATOM | 9528 | CB | GLN | B | 80 | 73.343 | 35.686 | −15.126 | 1.00 | 15.00 | B | C |
| ATOM | 9531 | CG | GLN | B | 80 | 73.128 | 36.374 | −13.771 | 1.00 | 17.76 | B | C |
| ATOM | 9534 | CD | GLN | B | 80 | 71.957 | 37.344 | −13.766 | 1.00 | 21.46 | B | C |
| ATOM | 9535 | OE1 | GLN | B | 80 | 71.283 | 37.519 | −12.744 | 1.00 | 24.61 | B | O |
| ATOM | 9536 | NE2 | GLN | B | 80 | 71.702 | 37.966 | −14.903 | 1.00 | 18.12 | B | N |
| ATOM | 9539 | C | GLN | B | 80 | 74.244 | 33.713 | −16.339 | 1.00 | 21.60 | B | C |
| ATOM | 9540 | O | GLN | B | 80 | 73.655 | 32.624 | −16.426 | 1.00 | 23.34 | B | O |
| ATOM | 9542 | N | ARG | B | 81 | 74.930 | 34.258 | −17.340 | 1.00 | 19.85 | B | N |
| ATOM | 9543 | CA | ARG | B | 81 | 75.018 | 33.618 | −18.651 | 1.00 | 21.31 | B | C |
| ATOM | 9545 | CB | ARG | B | 81 | 75.744 | 34.528 | −19.651 | 1.00 | 22.39 | B | C |
| ATOM | 9548 | CG | ARG | B | 81 | 74.902 | 35.779 | −19.950 | 1.00 | 24.93 | B | C |
| ATOM | 9551 | CD | ARG | B | 81 | 75.364 | 36.514 | −21.183 | 1.00 | 27.95 | B | C |
| ATOM | 9554 | NE | ARG | B | 81 | 75.370 | 35.628 | −22.346 | 1.00 | 33.40 | B | N |
| ATOM | 9556 | CZ | ARG | B | 81 | 75.597 | 36.035 | −23.594 | 1.00 | 44.92 | B | C |
| ATOM | 9557 | NH1 | ARG | B | 81 | 75.801 | 37.326 | −23.849 | 1.00 | 43.90 | B | N |
| ATOM | 9560 | NH2 | ARG | B | 81 | 75.593 | 35.149 | −24.597 | 1.00 | 41.12 | B | N |
| ATOM | 9563 | C | ARG | B | 81 | 75.669 | 32.256 | −18.590 | 1.00 | 20.24 | B | C |
| ATOM | 9564 | O | ARG | B | 81 | 75.228 | 31.322 | −19.268 | 1.00 | 23.90 | B | O |
| ATOM | 9566 | N | LEU | B | 82 | 76.683 | 32.119 | −17.747 | 1.00 | 18.56 | B | N |
| ATOM | 9567 | CA | LEU | B | 82 | 77.374 | 30.837 | −17.558 | 1.00 | 17.31 | B | C |
| ATOM | 9569 | CB | LEU | B | 82 | 78.723 | 31.056 | −16.857 | 1.00 | 17.11 | B | C |
| ATOM | 9572 | CG | LEU | B | 82 | 79.810 | 31.804 | −17.660 | 1.00 | 23.24 | B | C |
| ATOM | 9574 | CD1 | LEU | B | 82 | 80.870 | 32.349 | −16.695 | 1.00 | 14.65 | B | C |
| ATOM | 9578 | CD2 | LEU | B | 82 | 80.450 | 30.919 | −18.756 | 1.00 | 16.24 | B | C |
| ATOM | 9582 | C | LEU | B | 82 | 76.546 | 29.833 | −16.757 | 1.00 | 16.56 | B | C |
| ATOM | 9583 | O | LEU | B | 82 | 76.966 | 28.708 | −16.571 | 1.00 | 17.24 | B | O |
| ATOM | 9585 | N | GLY | B | 83 | 75.391 | 30.245 | −16.253 | 1.00 | 19.51 | B | N |
| ATOM | 9586 | CA | GLY | B | 83 | 74.459 | 29.326 | −15.600 | 1.00 | 20.32 | B | C |
| ATOM | 9589 | C | GLY | B | 83 | 74.479 | 29.334 | −14.085 | 1.00 | 21.68 | B | C |
| ATOM | 9590 | O | GLY | B | 83 | 73.823 | 28.495 | −13.459 | 1.00 | 24.50 | B | O |
| ATOM | 9592 | N | LEU | B | 84 | 75.188 | 30.288 | −13.480 | 1.00 | 21.90 | B | N |
| ATOM | 9593 | CA | LEU | B | 84 | 75.440 | 30.252 | −12.043 | 1.00 | 23.56 | B | C |
| ATOM | 9595 | CB | LEU | B | 84 | 76.918 | 30.462 | −11.762 | 1.00 | 21.53 | B | C |
| ATOM | 9598 | CG | LEU | B | 84 | 77.914 | 29.392 | −12.227 | 1.00 | 22.51 | B | C |
| ATOM | 9600 | CD1 | LEU | B | 84 | 79.332 | 30.012 | −12.350 | 1.00 | 17.35 | B | C |
| ATOM | 9604 | CD2 | LEU | B | 84 | 77.936 | 28.211 | −11.274 | 1.00 | 14.52 | B | C |
| ATOM | 9608 | C | LEU | B | 84 | 74.614 | 31.286 | −11.267 | 1.00 | 24.75 | B | C |
| ATOM | 9609 | O | LEU | B | 84 | 74.793 | 31.464 | −10.050 | 1.00 | 23.23 | B | O |
| ATOM | 9611 | N | GLY | B | 85 | 73.704 | 31.946 | −11.957 | 1.00 | 20.07 | B | N |

TABLE 4-2-continued

Coordinates of *P. alba* IspS

| ATOM | 9612 | CA | GLY | B | 85 | 72.905 | 32.986 | −11.331 | 1.00 | 23.42 | B | C |
|------|------|-----|-----|---|----|--------|--------|---------|------|-------|---|---|
| ATOM | 9615 | C | GLY | B | 85 | 72.103 | 32.548 | −10.128 | 1.00 | 23.55 | B | C |
| ATOM | 9616 | O | GLY | B | 85 | 72.051 | 33.276 | −9.129 | 1.00 | 24.14 | B | O |
| ATOM | 9618 | N | TYR | B | 86 | 71.493 | 31.358 | −10.216 | 1.00 | 25.41 | B | N |
| ATOM | 9619 | CA | TYR | B | 86 | 70.653 | 30.780 | −9.138 | 1.00 | 24.89 | B | C |
| ATOM | 9621 | CB | TYR | B | 86 | 70.088 | 29.405 | −9.555 | 1.00 | 23.46 | B | C |
| ATOM | 9624 | CG | TYR | B | 86 | 71.098 | 28.272 | −9.477 | 1.00 | 20.27 | B | C |
| ATOM | 9625 | CD1 | TYR | B | 86 | 71.113 | 27.378 | −8.409 | 1.00 | 18.85 | B | C |
| ATOM | 9627 | CE1 | TYR | B | 86 | 72.051 | 26.334 | −8.361 | 1.00 | 21.28 | B | C |
| ATOM | 9629 | CZ | TYR | B | 86 | 72.972 | 26.173 | −9.391 | 1.00 | 21.08 | B | C |
| ATOM | 9630 | OH | TYR | B | 86 | 73.936 | 25.171 | −9.372 | 1.00 | 14.76 | B | O |
| ATOM | 9632 | CE2 | TYR | B | 86 | 72.949 | 27.035 | −10.447 | 1.00 | 15.78 | B | C |
| ATOM | 9634 | CD2 | TYR | B | 86 | 72.029 | 28.084 | −10.477 | 1.00 | 18.71 | B | C |
| ATOM | 9636 | C | TYR | B | 86 | 71.418 | 30.580 | −7.843 | 1.00 | 27.93 | B | C |
| ATOM | 9637 | O | TYR | B | 86 | 70.847 | 30.313 | −6.788 | 1.00 | 29.61 | B | O |
| ATOM | 9639 | N | ARG | B | 87 | 72.730 | 30.655 | −7.953 | 1.00 | 27.91 | B | N |
| ATOM | 9640 | CA | ARG | B | 87 | 73.620 | 30.275 | −6.899 | 1.00 | 27.88 | B | C |
| ATOM | 9642 | CB | ARG | B | 87 | 74.812 | 29.611 | −7.587 | 1.00 | 30.15 | B | C |
| ATOM | 9645 | CG | ARG | B | 87 | 75.709 | 28.864 | −6.734 | 1.00 | 30.85 | B | C |
| ATOM | 9648 | CD | ARG | B | 87 | 76.316 | 27.640 | −7.442 | 1.00 | 29.13 | B | C |
| ATOM | 9651 | NE | ARG | B | 87 | 76.612 | 26.804 | −6.332 | 1.00 | 26.20 | B | N |
| ATOM | 9653 | CZ | ARG | B | 87 | 75.932 | 25.744 | −5.944 | 1.00 | 24.61 | B | C |
| ATOM | 9654 | NH1 | ARG | B | 87 | 76.289 | 25.177 | −4.803 | 1.00 | 36.76 | B | N |
| ATOM | 9657 | NH2 | ARG | B | 87 | 74.970 | 25.210 | −6.680 | 1.00 | 26.43 | B | N |
| ATOM | 9660 | C | ARG | B | 87 | 74.038 | 31.512 | −6.147 | 1.00 | 27.03 | B | C |
| ATOM | 9661 | O | ARG | B | 87 | 74.506 | 31.421 | −5.028 | 1.00 | 25.59 | B | O |
| ATOM | 9663 | N | PHE | B | 88 | 73.855 | 32.679 | −6.776 | 1.00 | 28.24 | B | N |
| ATOM | 9664 | CA | PHE | B | 88 | 74.438 | 33.940 | −6.297 | 1.00 | 28.26 | B | C |
| ATOM | 9666 | CB | PHE | B | 88 | 75.605 | 34.341 | −7.210 | 1.00 | 25.39 | B | C |
| ATOM | 9669 | CG | PHE | B | 88 | 76.807 | 33.456 | −7.079 | 1.00 | 25.44 | B | C |
| ATOM | 9670 | CD1 | PHE | B | 88 | 77.569 | 33.468 | −5.924 | 1.00 | 18.49 | B | C |
| ATOM | 9672 | CE1 | PHE | B | 88 | 78.678 | 32.671 | −5.811 | 1.00 | 25.00 | B | C |
| ATOM | 9674 | CZ | PHE | B | 88 | 79.048 | 31.820 | −6.862 | 1.00 | 22.42 | B | C |
| ATOM | 9676 | CE2 | PHE | B | 88 | 78.292 | 31.788 | −8.000 | 1.00 | 19.97 | B | C |
| ATOM | 9678 | CD2 | PHE | B | 88 | 77.180 | 32.609 | −8.112 | 1.00 | 21.12 | B | C |
| ATOM | 9680 | C | PHE | B | 88 | 73.404 | 35.074 | −6.240 | 1.00 | 29.32 | B | C |
| ATOM | 9681 | O | PHE | B | 88 | 73.756 | 36.270 | −6.250 | 1.00 | 29.34 | B | O |
| ATOM | 9683 | N | GLU | B | 89 | 72.140 | 34.695 | −6.141 | 1.00 | 29.21 | B | N |
| ATOM | 9684 | CA | GLU | B | 89 | 71.049 | 35.650 | −6.224 | 1.00 | 32.70 | B | C |
| ATOM | 9686 | CB | GLU | B | 89 | 69.701 | 34.937 | −6.103 | 1.00 | 33.74 | B | C |
| ATOM | 9689 | CG | GLU | B | 89 | 68.512 | 35.887 | −6.195 | 1.00 | 45.69 | B | C |
| ATOM | 9692 | CD | GLU | B | 89 | 67.208 | 35.206 | −6.586 | 1.00 | 55.76 | B | C |
| ATOM | 9693 | OE1 | GLU | B | 89 | 67.250 | 34.124 | −7.225 | 1.00 | 57.29 | B | O |
| ATOM | 9694 | OE2 | GLU | B | 89 | 66.142 | 35.787 | −6.272 | 1.00 | 58.91 | B | O |
| ATOM | 9695 | C | GLU | B | 89 | 71.156 | 36.755 | −5.186 | 1.00 | 31.50 | B | C |
| ATOM | 9696 | O | GLU | B | 89 | 71.011 | 37.913 | −5.516 | 1.00 | 33.00 | B | O |
| ATOM | 9698 | N | SER | B | 90 | 71.421 | 36.425 | −3.935 | 1.00 | 31.61 | B | N |
| ATOM | 9699 | CA | SER | B | 90 | 71.404 | 37.470 | −2.907 | 1.00 | 31.80 | B | C |
| ATOM | 9701 | CB | SER | B | 90 | 71.315 | 36.860 | −1.490 | 1.00 | 32.58 | B | C |
| ATOM | 9704 | OG | SER | B | 90 | 72.570 | 36.431 | −0.986 | 1.00 | 41.51 | B | O |
| ATOM | 9706 | C | SER | B | 90 | 72.600 | 38.420 | −3.061 | 1.00 | 29.63 | B | C |
| ATOM | 9707 | O | SER | B | 90 | 72.524 | 39.599 | −2.730 | 1.00 | 30.79 | B | O |
| ATOM | 9709 | N | ASP | B | 91 | 73.707 | 37.902 | −3.576 | 1.00 | 26.77 | B | N |
| ATOM | 9710 | CA | ASP | B | 91 | 74.889 | 38.721 | −3.783 | 1.00 | 24.01 | B | C |
| ATOM | 9712 | CB | ASP | B | 91 | 76.103 | 37.821 | −4.010 | 1.00 | 25.50 | B | C |
| ATOM | 9715 | CG | ASP | B | 91 | 76.251 | 36.765 | −2.909 | 1.00 | 26.74 | B | C |
| ATOM | 9716 | OD1 | ASP | B | 91 | 76.655 | 37.118 | −1.779 | 1.00 | 29.64 | B | O |
| ATOM | 9717 | OD2 | ASP | B | 91 | 75.922 | 35.587 | −3.167 | 1.00 | 39.56 | B | O |
| ATOM | 9718 | C | ASP | B | 91 | 74.638 | 39.638 | −4.962 | 1.00 | 22.71 | B | C |
| ATOM | 9719 | O | ASP | B | 91 | 74.987 | 40.816 | −4.931 | 1.00 | 19.92 | B | O |
| ATOM | 9721 | N | ILE | B | 92 | 73.984 | 39.105 | −5.989 | 1.00 | 22.65 | B | N |
| ATOM | 9722 | CA | ILE | B | 92 | 73.661 | 39.888 | −7.185 | 1.00 | 22.89 | B | C |
| ATOM | 9724 | CB | ILE | B | 92 | 73.071 | 39.000 | −8.272 | 1.00 | 22.20 | B | C |
| ATOM | 9726 | CG1 | ILE | B | 92 | 74.203 | 38.179 | −8.899 | 1.00 | 22.79 | B | C |
| ATOM | 9729 | CD1 | ILE | B | 92 | 73.755 | 36.921 | −9.639 | 1.00 | 17.50 | B | C |
| ATOM | 9733 | CG2 | ILE | B | 92 | 72.332 | 39.853 | −9.316 | 1.00 | 20.85 | B | C |
| ATOM | 9737 | C | ILE | B | 92 | 72.710 | 41.049 | −6.869 | 1.00 | 24.13 | B | C |
| ATOM | 9738 | O | ILE | B | 92 | 72.974 | 42.200 | −7.246 | 1.00 | 22.72 | B | O |
| ATOM | 9740 | N | ARG | B | 93 | 71.624 | 40.744 | −6.167 | 1.00 | 24.93 | B | N |
| ATOM | 9741 | CA | ARG | B | 93 | 70.659 | 41.766 | −5.731 | 1.00 | 27.69 | B | C |
| ATOM | 9743 | CB | ARG | B | 93 | 69.522 | 41.150 | −4.895 | 1.00 | 29.92 | B | C |
| ATOM | 9746 | CG | ARG | B | 93 | 68.573 | 40.217 | −5.631 | 1.00 | 32.70 | B | C |
| ATOM | 9749 | CD | ARG | B | 93 | 67.427 | 39.746 | −4.685 | 1.00 | 39.32 | B | C |
| ATOM | 9752 | NE | ARG | B | 93 | 66.650 | 40.894 | −4.231 | 1.00 | 40.88 | B | N |
| ATOM | 9754 | CZ | ARG | B | 93 | 65.793 | 41.575 | −4.993 | 1.00 | 47.67 | B | C |
| ATOM | 9755 | NH1 | ARG | B | 93 | 65.565 | 41.216 | −6.262 | 1.00 | 47.75 | B | N |
| ATOM | 9758 | NH2 | ARG | B | 93 | 65.147 | 42.622 | −4.484 | 1.00 | 51.17 | B | N |
| ATOM | 9761 | C | ARG | B | 93 | 71.322 | 42.797 | −4.865 | 1.00 | 26.85 | B | C |

TABLE 4-2-continued

Coordinates of *P. alba* IspS

| | | | | | | | | | | | |
|---|---|---|---|---|---|---|---|---|---|---|---|
| ATOM | 9762 | O | ARG | B | 93 | 71.039 | 43.980 | −4.983 | 1.00 | 28.19 | B | O |
| ATOM | 9764 | N | GLY | B | 94 | 72.186 | 42.340 | −3.966 | 1.00 | 26.87 | B | N |
| ATOM | 9765 | CA | GLY | B | 94 | 72.934 | 43.248 | −3.122 | 1.00 | 27.08 | B | C |
| ATOM | 9768 | C | GLY | B | 94 | 73.776 | 44.208 | −3.939 | 1.00 | 27.51 | B | C |
| ATOM | 9769 | O | GLY | B | 94 | 73.809 | 45.401 | −3.656 | 1.00 | 31.87 | B | O |
| ATOM | 9771 | N | ALA | B | 95 | 74.464 | 43.704 | −4.957 | 1.00 | 25.26 | B | N |
| ATOM | 9772 | CA | ALA | B | 95 | 75.283 | 44.564 | −5.793 | 1.00 | 23.60 | B | C |
| ATOM | 9774 | CB | ALA | B | 95 | 76.133 | 43.743 | −6.728 | 1.00 | 21.73 | B | C |
| ATOM | 9778 | C | ALA | B | 95 | 74.397 | 45.521 | −6.578 | 1.00 | 23.80 | B | C |
| ATOM | 9779 | O | ALA | B | 95 | 74.670 | 46.712 | −6.666 | 1.00 | 23.61 | B | O |
| ATOM | 9781 | N | LEU | B | 96 | 73.322 | 45.005 | −7.152 | 1.00 | 25.22 | B | N |
| ATOM | 9782 | CA | LEU | B | 96 | 72.452 | 45.858 | −7.955 | 1.00 | 26.19 | B | C |
| ATOM | 9784 | CB | LEU | B | 96 | 71.359 | 45.040 | −8.659 | 1.00 | 25.27 | B | C |
| ATOM | 9787 | CG | LEU | B | 96 | 71.931 | 44.096 | −9.719 | 1.00 | 26.21 | B | C |
| ATOM | 9789 | CD1 | LEU | B | 96 | 70.839 | 43.152 | −10.263 | 1.00 | 20.34 | B | C |
| ATOM | 9793 | CD2 | LEU | B | 96 | 72.591 | 44.898 | −10.840 | 1.00 | 19.97 | B | C |
| ATOM | 9797 | C | LEU | B | 96 | 71.855 | 46.943 | −7.070 | 1.00 | 27.60 | B | C |
| ATOM | 9798 | O | LEU | B | 96 | 71.741 | 48.080 | −7.486 | 1.00 | 25.32 | B | O |
| ATOM | 9800 | N | ASP | B | 97 | 71.510 | 46.589 | −5.834 | 1.00 | 30.71 | B | N |
| ATOM | 9801 | CA | ASP | B | 97 | 70.894 | 47.534 | −4.922 | 1.00 | 34.41 | B | C |
| ATOM | 9803 | CB | ASP | B | 97 | 70.407 | 46.810 | −3.668 | 1.00 | 36.18 | B | C |
| ATOM | 9806 | CG | ASP | B | 97 | 69.603 | 47.704 | −2.770 | 1.00 | 46.19 | B | C |
| ATOM | 9807 | OD1 | ASP | B | 97 | 70.026 | 47.902 | −1.611 | 1.00 | 56.68 | B | O |
| ATOM | 9808 | OD2 | ASP | B | 97 | 68.567 | 48.239 | −3.235 | 1.00 | 53.71 | B | O |
| ATOM | 9809 | C | ASP | B | 97 | 71.855 | 48.672 | −4.568 | 1.00 | 35.18 | B | C |
| ATOM | 9810 | O | ASP | B | 97 | 71.452 | 49.829 | −4.438 | 1.00 | 35.44 | B | O |
| ATOM | 9812 | N | ARG | B | 98 | 73.128 | 48.328 | −4.428 | 1.00 | 37.40 | B | N |
| ATOM | 9813 | CA | ARG | B | 98 | 74.183 | 49.305 | −4.148 | 1.00 | 38.06 | B | C |
| ATOM | 9815 | CB | ARG | B | 98 | 75.536 | 48.601 | −3.947 | 1.00 | 39.12 | B | C |
| ATOM | 9818 | CG | ARG | B | 98 | 76.260 | 48.876 | −2.626 | 1.00 | 41.93 | B | C |
| ATOM | 9821 | CD | ARG | B | 98 | 76.328 | 47.616 | −1.786 | 1.00 | 44.63 | B | C |
| ATOM | 9824 | NE | ARG | B | 98 | 77.027 | 46.541 | −2.495 | 1.00 | 40.39 | B | N |
| ATOM | 9826 | CZ | ARG | B | 98 | 76.878 | 45.243 | −2.248 | 1.00 | 33.84 | B | C |
| ATOM | 9827 | NH1 | ARG | B | 98 | 76.044 | 44.819 | −1.303 | 1.00 | 38.65 | B | N |
| ATOM | 9830 | NH2 | ARG | B | 98 | 77.564 | 44.360 | −2.963 | 1.00 | 35.04 | B | N |
| ATOM | 9833 | C | ARG | B | 98 | 74.298 | 50.240 | −5.337 | 1.00 | 37.03 | B | C |
| ATOM | 9834 | O | ARG | B | 98 | 74.388 | 51.452 | −5.189 | 1.00 | 35.80 | B | O |
| ATOM | 9836 | N | PHE | B | 99 | 74.289 | 49.641 | −6.522 | 1.00 | 36.87 | B | N |
| ATOM | 9837 | CA | PHE | B | 99 | 74.457 | 50.365 | −7.767 | 1.00 | 36.19 | B | C |
| ATOM | 9839 | CB | PHE | B | 99 | 74.402 | 49.380 | −8.927 | 1.00 | 36.62 | B | C |
| ATOM | 9842 | CG | PHE | B | 99 | 74.636 | 49.997 | −10.260 | 1.00 | 33.49 | B | C |
| ATOM | 9843 | CD1 | PHE | B | 99 | 75.826 | 50.641 | −10.534 | 1.00 | 38.87 | B | C |
| ATOM | 9845 | CE1 | PHE | B | 99 | 76.054 | 51.211 | −11.773 | 1.00 | 37.59 | B | C |
| ATOM | 9847 | CZ | PHE | B | 99 | 75.087 | 51.116 | −12.749 | 1.00 | 36.98 | B | C |
| ATOM | 9849 | CE2 | PHE | B | 99 | 73.901 | 50.457 | −12.486 | 1.00 | 29.58 | B | C |
| ATOM | 9851 | CD2 | PHE | B | 99 | 73.677 | 49.916 | −11.252 | 1.00 | 33.52 | B | C |
| ATOM | 9853 | C | PHE | B | 99 | 73.396 | 51.431 | −7.953 | 1.00 | 36.68 | B | C |
| ATOM | 9854 | O | PHE | B | 99 | 73.686 | 52.516 | −8.465 | 1.00 | 37.64 | B | O |
| ATOM | 9856 | N | VAL | B | 100 | 72.170 | 51.134 | −7.540 | 1.00 | 36.30 | B | N |
| ATOM | 9857 | CA | VAL | B | 100 | 71.102 | 52.123 | −7.615 | 1.00 | 38.42 | B | C |
| ATOM | 9859 | CB | VAL | B | 100 | 69.704 | 51.479 | −7.546 | 1.00 | 39.36 | B | C |
| ATOM | 9861 | CG1 | VAL | B | 100 | 68.625 | 52.555 | −7.520 | 1.00 | 38.06 | B | C |
| ATOM | 9865 | CG2 | VAL | B | 100 | 69.486 | 50.541 | −8.738 | 1.00 | 35.08 | B | C |
| ATOM | 9869 | C | VAL | B | 100 | 71.258 | 53.138 | −6.489 | 1.00 | 40.92 | B | C |
| ATOM | 9870 | O | VAL | B | 100 | 71.400 | 54.336 | −6.745 | 1.00 | 41.13 | B | O |
| ATOM | 9872 | N | SER | B | 101 | 71.261 | 52.643 | −5.251 | 1.00 | 42.85 | B | N |
| ATOM | 9873 | CA | SER | B | 101 | 71.290 | 53.499 | −4.056 | 1.00 | 44.85 | B | C |
| ATOM | 9875 | CB | SER | B | 101 | 71.364 | 52.641 | −2.783 | 1.00 | 45.99 | B | C |
| ATOM | 9878 | OG | SER | B | 101 | 72.670 | 52.116 | −2.592 | 1.00 | 48.88 | B | O |
| ATOM | 9880 | C | SER | B | 101 | 72.435 | 54.514 | −4.026 | 1.00 | 44.67 | B | C |
| ATOM | 9881 | O | SER | B | 101 | 72.314 | 55.554 | −3.390 | 1.00 | 45.09 | B | O |
| ATOM | 9883 | N | SER | B | 102 | 73.546 | 54.195 | −4.685 | 1.00 | 44.99 | B | N |
| ATOM | 9884 | CA | SER | B | 102 | 74.709 | 55.078 | −4.710 | 1.00 | 45.30 | B | C |
| ATOM | 9886 | CB | SER | B | 102 | 76.001 | 54.249 | −4.754 | 1.00 | 45.54 | B | C |
| ATOM | 9889 | OG | SER | B | 102 | 76.305 | 53.829 | −6.074 | 1.00 | 46.99 | B | O |
| ATOM | 9891 | C | SER | B | 102 | 74.680 | 56.051 | −5.892 | 1.00 | 44.38 | B | C |
| ATOM | 9892 | O | SER | B | 102 | 75.651 | 56.748 | −6.133 | 1.00 | 44.36 | B | O |
| ATOM | 9894 | N | GLY | B | 103 | 73.579 | 56.086 | −6.632 | 1.00 | 45.09 | B | N |
| ATOM | 9895 | CA | GLY | B | 103 | 73.474 | 56.931 | −7.820 | 1.00 | 46.00 | B | C |
| ATOM | 9898 | C | GLY | B | 103 | 74.299 | 56.453 | −9.007 | 1.00 | 45.92 | B | C |
| ATOM | 9899 | O | GLY | B | 103 | 74.416 | 57.159 | −10.016 | 1.00 | 45.89 | B | O |
| ATOM | 9901 | N | GLY | B | 104 | 74.861 | 55.251 | −8.900 | 1.00 | 45.67 | B | N |
| ATOM | 9902 | CA | GLY | B | 104 | 75.678 | 54.681 | −9.965 | 1.00 | 45.47 | B | C |
| ATOM | 9905 | C | GLY | B | 104 | 74.878 | 54.459 | −11.234 | 1.00 | 45.06 | B | C |
| ATOM | 9906 | O | GLY | B | 104 | 75.402 | 54.617 | −12.343 | 1.00 | 46.05 | B | O |
| ATOM | 9908 | N | PHE | B | 105 | 73.603 | 54.114 | −11.074 | 1.00 | 43.92 | B | N |
| ATOM | 9909 | CA | PHE | B | 105 | 72.735 | 53.885 | −12.220 | 1.00 | 44.36 | B | C |
| ATOM | 9911 | CB | PHE | B | 105 | 71.423 | 53.191 | −11.814 | 1.00 | 42.94 | B | C |

TABLE 4-2-continued

Coordinates of *P. alba* IspS

| ATOM | 9914 | CG | PHE | B | 105 | 70.454 | 53.021 | −12.957 | 1.00 | 42.37 | B | C |
|---|---|---|---|---|---|---|---|---|---|---|---|---|
| ATOM | 9915 | CD1 | PHE | B | 105 | 70.829 | 52.332 | −14.103 | 1.00 | 36.91 | B | C |
| ATOM | 9917 | CE1 | PHE | B | 105 | 69.952 | 52.182 | −15.166 | 1.00 | 37.47 | B | C |
| ATOM | 9919 | CZ | PHE | B | 105 | 68.680 | 52.719 | −15.094 | 1.00 | 41.23 | B | C |
| ATOM | 9921 | CE2 | PHE | B | 105 | 68.291 | 53.412 | −13.959 | 1.00 | 42.58 | B | C |
| ATOM | 9923 | CD2 | PHE | B | 105 | 69.178 | 53.564 | −12.897 | 1.00 | 44.83 | B | C |
| ATOM | 9925 | C | PHE | B | 105 | 72.459 | 55.200 | −12.938 | 1.00 | 45.55 | B | C |
| ATOM | 9926 | O | PHE | B | 105 | 72.515 | 55.272 | −14.165 | 1.00 | 46.03 | B | O |
| ATOM | 9928 | N | ASP | B | 106 | 72.181 | 56.251 | −12.184 | 1.00 | 48.32 | B | N |
| ATOM | 9929 | CA | ASP | B | 106 | 71.949 | 57.544 | −12.816 | 1.00 | 50.02 | B | C |
| ATOM | 9931 | CB | ASP | B | 106 | 71.521 | 58.609 | −11.799 | 1.00 | 51.66 | B | C |
| ATOM | 9934 | CG | ASP | B | 106 | 70.532 | 59.608 | −12.389 | 1.00 | 59.23 | B | C |
| ATOM | 9935 | OD1 | ASP | B | 106 | 70.967 | 60.722 | −12.764 | 1.00 | 68.92 | B | O |
| ATOM | 9936 | OD2 | ASP | B | 106 | 69.329 | 59.265 | −12.503 | 1.00 | 64.95 | B | O |
| ATOM | 9937 | C | ASP | B | 106 | 73.202 | 57.974 | −13.594 | 1.00 | 48.61 | B | C |
| ATOM | 9938 | O | ASP | B | 106 | 73.086 | 58.477 | −14.710 | 1.00 | 49.31 | B | O |
| ATOM | 9940 | N | ALA | B | 107 | 74.384 | 57.740 | −13.017 | 1.00 | 46.79 | B | N |
| ATOM | 9941 | CA | ALA | B | 107 | 75.666 | 58.062 | −13.663 | 1.00 | 45.20 | B | C |
| ATOM | 9943 | CB | ALA | B | 107 | 76.843 | 57.556 | −12.813 | 1.00 | 45.79 | B | C |
| ATOM | 9947 | C | ALA | B | 107 | 75.773 | 57.487 | −15.070 | 1.00 | 44.20 | B | C |
| ATOM | 9948 | O | ALA | B | 107 | 76.122 | 58.209 | −16.012 | 1.00 | 43.29 | B | O |
| ATOM | 9950 | N | VAL | B | 108 | 75.468 | 56.193 | −15.214 | 1.00 | 42.78 | B | N |
| ATOM | 9951 | CA | VAL | B | 108 | 75.678 | 55.509 | −16.490 | 1.00 | 41.56 | B | C |
| ATOM | 9953 | CB | VAL | B | 108 | 75.580 | 53.961 | −16.398 | 1.00 | 42.67 | B | C |
| ATOM | 9955 | CG1 | VAL | B | 108 | 76.575 | 53.424 | −15.362 | 1.00 | 47.74 | B | C |
| ATOM | 9959 | CG2 | VAL | B | 108 | 74.146 | 53.506 | −16.103 | 1.00 | 37.79 | B | C |
| ATOM | 9963 | C | VAL | B | 108 | 74.736 | 56.019 | −17.565 | 1.00 | 40.56 | B | C |
| ATOM | 9964 | O | VAL | B | 108 | 75.140 | 56.108 | −18.716 | 1.00 | 41.01 | B | O |
| ATOM | 9966 | N | THR | B | 109 | 73.502 | 56.372 | −17.201 | 1.00 | 40.25 | B | N |
| ATOM | 9967 | CA | THR | B | 109 | 72.547 | 56.895 | −18.191 | 1.00 | 41.97 | B | C |
| ATOM | 9969 | CB | THR | B | 109 | 71.113 | 57.091 | −17.604 | 1.00 | 41.78 | B | C |
| ATOM | 9971 | OG1 | THR | B | 109 | 71.096 | 58.187 | −16.682 | 1.00 | 41.41 | B | O |
| ATOM | 9973 | CG2 | THR | B | 109 | 70.628 | 55.818 | −16.897 | 1.00 | 40.99 | B | C |
| ATOM | 9977 | C | THR | B | 109 | 73.024 | 58.197 | −18.874 | 1.00 | 43.11 | B | C |
| ATOM | 9978 | O | THR | B | 109 | 72.439 | 58.614 | −19.887 | 1.00 | 42.41 | B | O |
| ATOM | 9980 | N | LYS | B | 110 | 74.077 | 58.819 | −18.328 | 1.00 | 44.55 | B | N |
| ATOM | 9981 | CA | LYS | B | 110 | 74.712 | 60.008 | −18.934 | 1.00 | 46.75 | B | C |
| ATOM | 9983 | CB | LYS | B | 110 | 75.089 | 61.044 | −17.862 | 1.00 | 47.58 | B | C |
| ATOM | 9986 | CG | LYS | B | 110 | 74.109 | 61.209 | −16.687 | 1.00 | 52.76 | B | C |
| ATOM | 9989 | CD | LYS | B | 110 | 72.754 | 61.764 | −17.101 | 1.00 | 59.40 | B | C |
| ATOM | 9992 | CE | LYS | B | 110 | 71.958 | 62.222 | −15.878 | 1.00 | 63.05 | B | C |
| ATOM | 9995 | NZ | LYS | B | 110 | 70.552 | 62.553 | −16.225 | 1.00 | 62.78 | B | N |
| ATOM | 9999 | C | LYS | B | 110 | 75.976 | 59.657 | −19.743 | 1.00 | 46.76 | B | C |
| ATOM | 10000 | O | LYS | B | 110 | 76.282 | 60.317 | −20.748 | 1.00 | 47.35 | B | O |
| ATOM | 10002 | N | THR | B | 111 | 76.697 | 58.619 | −19.304 | 1.00 | 46.07 | B | N |
| ATOM | 10003 | CA | THR | B | 111 | 77.998 | 58.251 | −19.878 | 1.00 | 44.96 | B | C |
| ATOM | 10005 | CB | THR | B | 111 | 79.002 | 57.862 | −18.753 | 1.00 | 46.02 | B | C |
| ATOM | 10007 | OG1 | THR | B | 111 | 78.445 | 56.851 | −17.896 | 1.00 | 46.80 | B | O |
| ATOM | 10009 | CG2 | THR | B | 111 | 79.355 | 59.091 | −17.907 | 1.00 | 48.57 | B | C |
| ATOM | 10013 | C | THR | B | 111 | 77.980 | 57.145 | −20.961 | 1.00 | 43.55 | B | C |
| ATOM | 10014 | O | THR | B | 111 | 78.579 | 57.326 | −22.031 | 1.00 | 43.45 | B | O |
| ATOM | 10016 | N | SER | B | 112 | 77.288 | 56.026 | −20.695 | 1.00 | 40.85 | B | N |
| ATOM | 10017 | CA | SER | B | 112 | 77.475 | 54.771 | −21.460 | 1.00 | 38.21 | B | C |
| ATOM | 10019 | CB | SER | B | 112 | 78.367 | 53.817 | −20.654 | 1.00 | 38.70 | B | C |
| ATOM | 10022 | OG | SER | B | 112 | 78.963 | 52.840 | −21.489 | 1.00 | 42.04 | B | O |
| ATOM | 10024 | C | SER | B | 112 | 76.191 | 54.013 | −21.850 | 1.00 | 35.38 | B | C |
| ATOM | 10025 | O | SER | B | 112 | 75.380 | 53.635 | −20.990 | 1.00 | 33.95 | B | O |
| ATOM | 10027 | N | LEU | B | 113 | 76.039 | 53.751 | −23.146 | 1.00 | 32.47 | B | N |
| ATOM | 10028 | CA | LEU | B | 113 | 74.920 | 52.960 | −23.647 | 1.00 | 30.72 | B | C |
| ATOM | 10030 | CB | LEU | B | 113 | 74.878 | 52.958 | −25.174 | 1.00 | 30.16 | B | C |
| ATOM | 10033 | CG | LEU | B | 113 | 73.792 | 52.095 | −25.831 | 1.00 | 29.63 | B | C |
| ATOM | 10035 | CD1 | LEU | B | 113 | 72.399 | 52.493 | −25.368 | 1.00 | 27.97 | B | C |
| ATOM | 10039 | CD2 | LEU | B | 113 | 73.891 | 52.182 | −27.341 | 1.00 | 34.38 | B | C |
| ATOM | 10043 | C | LEU | B | 113 | 75.025 | 51.529 | −23.144 | 1.00 | 30.25 | B | C |
| ATOM | 10044 | O | LEU | B | 113 | 74.071 | 51.011 | −22.567 | 1.00 | 29.96 | B | O |
| ATOM | 10046 | N | HIS | B | 114 | 76.182 | 50.901 | −23.371 | 1.00 | 29.63 | B | N |
| ATOM | 10047 | CA | HIS | B | 114 | 76.423 | 49.536 | −22.917 | 1.00 | 29.61 | B | C |
| ATOM | 10049 | CB | HIS | B | 114 | 77.874 | 49.098 | −23.189 | 1.00 | 28.64 | B | C |
| ATOM | 10052 | CG | HIS | B | 114 | 78.237 | 47.786 | −22.557 | 1.00 | 30.75 | B | C |
| ATOM | 10053 | ND1 | HIS | B | 114 | 77.483 | 46.642 | −22.722 | 1.00 | 32.60 | B | N |
| ATOM | 10055 | CE1 | HIS | B | 114 | 78.039 | 45.648 | −22.048 | 1.00 | 36.57 | B | C |
| ATOM | 10057 | NE2 | HIS | B | 114 | 79.126 | 46.105 | −21.449 | 1.00 | 37.27 | B | N |
| ATOM | 10059 | CD2 | HIS | B | 114 | 79.271 | 47.439 | −21.750 | 1.00 | 36.73 | B | C |
| ATOM | 10061 | C | HIS | B | 114 | 76.095 | 49.445 | −21.426 | 1.00 | 28.21 | B | C |
| ATOM | 10062 | O | HIS | B | 114 | 75.330 | 48.587 | −21.002 | 1.00 | 24.16 | B | O |
| ATOM | 10064 | N | GLY | B | 115 | 76.666 | 50.363 | −20.651 | 1.00 | 26.67 | B | N |
| ATOM | 10065 | CA | GLY | B | 115 | 76.454 | 50.389 | −19.215 | 1.00 | 25.56 | B | C |
| ATOM | 10068 | C | GLY | B | 115 | 74.993 | 50.506 | −18.845 | 1.00 | 25.02 | B | C |

TABLE 4-2-continued

| | | | | | | | | | | | | |
|---|---|---|---|---|---|---|---|---|---|---|---|---|
| ATOM | 10069 | O | GLY | B | 115 | 74.544 | 49.881 | −17.891 | 1.00 | 25.22 | B | O |
| ATOM | 10071 | N | THR | B | 116 | 74.255 | 51.327 | −19.585 | 1.00 | 24.92 | B | N |
| ATOM | 10072 | CA | THR | B | 116 | 72.854 | 51.580 | −19.282 | 1.00 | 23.97 | B | C |
| ATOM | 10074 | CB | THR | B | 116 | 72.386 | 52.889 | −19.917 | 1.00 | 24.60 | B | C |
| ATOM | 10076 | OG1 | THR | B | 116 | 73.118 | 53.974 | −19.331 | 1.00 | 30.58 | B | O |
| ATOM | 10078 | CG2 | THR | B | 116 | 70.907 | 53.144 | −19.699 | 1.00 | 21.02 | B | C |
| ATOM | 10082 | C | THR | B | 116 | 72.002 | 50.387 | −19.711 | 1.00 | 26.00 | B | C |
| ATOM | 10083 | O | THR | B | 116 | 71.102 | 49.976 | −18.967 | 1.00 | 27.03 | B | O |
| ATOM | 10085 | N | ALA | B | 117 | 72.304 | 49.799 | −20.868 | 1.00 | 25.43 | B | N |
| ATOM | 10086 | CA | ALA | B | 117 | 71.505 | 48.662 | −21.378 | 1.00 | 25.89 | B | C |
| ATOM | 10088 | CB | ALA | B | 117 | 71.933 | 48.268 | −22.811 | 1.00 | 24.62 | B | C |
| ATOM | 10092 | C | ALA | B | 117 | 71.643 | 47.470 | −20.448 | 1.00 | 24.68 | B | C |
| ATOM | 10093 | O | ALA | B | 117 | 70.652 | 46.837 | −20.047 | 1.00 | 24.91 | B | O |
| ATOM | 10095 | N | LEU | B | 118 | 72.883 | 47.160 | −20.117 | 1.00 | 23.09 | B | N |
| ATOM | 10096 | CA | LEU | B | 118 | 73.178 | 46.044 | −19.230 | 1.00 | 23.36 | B | C |
| ATOM | 10098 | CB | LEU | B | 118 | 74.686 | 45.887 | −19.068 | 1.00 | 23.58 | B | C |
| ATOM | 10101 | CG | LEU | B | 118 | 75.181 | 44.714 | −18.231 | 1.00 | 26.99 | B | C |
| ATOM | 10103 | CD1 | LEU | B | 118 | 74.478 | 43.412 | −18.671 | 1.00 | 21.92 | B | C |
| ATOM | 10107 | CD2 | LEU | B | 118 | 76.708 | 44.613 | −18.322 | 1.00 | 19.81 | B | C |
| ATOM | 10111 | C | LEU | B | 118 | 72.521 | 46.257 | −17.880 | 1.00 | 22.07 | B | C |
| ATOM | 10112 | O | LEU | B | 118 | 71.777 | 45.405 | −17.412 | 1.00 | 21.86 | B | O |
| ATOM | 10114 | N | SER | B | 119 | 72.753 | 47.417 | −17.273 | 1.00 | 23.56 | B | N |
| ATOM | 10115 | CA | SER | B | 119 | 72.214 | 47.677 | −15.938 | 1.00 | 23.71 | B | C |
| ATOM | 10117 | CB | SER | B | 119 | 72.787 | 48.959 | −15.318 | 1.00 | 25.08 | B | C |
| ATOM | 10120 | OG | SER | B | 119 | 72.384 | 50.147 | −15.974 | 1.00 | 25.85 | B | O |
| ATOM | 10122 | C | SER | B | 119 | 70.697 | 47.691 | −15.957 | 1.00 | 22.91 | B | C |
| ATOM | 10123 | O | SER | B | 119 | 70.050 | 47.212 | −15.017 | 1.00 | 23.88 | B | O |
| ATOM | 10125 | N | PHE | B | 120 | 70.124 | 48.197 | −17.036 | 1.00 | 21.99 | B | N |
| ATOM | 10126 | CA | PHE | B | 120 | 68.674 | 48.240 | −17.144 | 1.00 | 22.07 | B | C |
| ATOM | 10128 | CB | PHE | B | 120 | 68.269 | 48.927 | −18.441 | 1.00 | 22.76 | B | C |
| ATOM | 10131 | CG | PHE | B | 120 | 66.792 | 48.936 | −18.703 | 1.00 | 23.93 | B | C |
| ATOM | 10132 | CD1 | PHE | B | 120 | 66.012 | 50.026 | −18.329 | 1.00 | 24.72 | B | C |
| ATOM | 10134 | CE1 | PHE | B | 120 | 64.651 | 50.041 | −18.588 | 1.00 | 21.87 | B | C |
| ATOM | 10136 | CZ | PHE | B | 120 | 64.064 | 48.965 | −19.235 | 1.00 | 25.59 | B | C |
| ATOM | 10138 | CE2 | PHE | B | 120 | 64.831 | 47.875 | −19.615 | 1.00 | 21.43 | B | C |
| ATOM | 10140 | CD2 | PHE | B | 120 | 66.187 | 47.870 | −19.355 | 1.00 | 26.77 | B | C |
| ATOM | 10142 | C | PHE | B | 120 | 68.138 | 46.820 | −17.108 | 1.00 | 22.44 | B | C |
| ATOM | 10143 | O | PHE | B | 120 | 67.232 | 46.510 | −16.330 | 1.00 | 23.78 | B | O |
| ATOM | 10145 | N | ARG | B | 121 | 68.708 | 45.967 | −17.954 | 1.00 | 20.63 | B | N |
| ATOM | 10146 | CA | ARG | B | 121 | 68.315 | 44.563 | −18.023 | 1.00 | 22.16 | B | C |
| ATOM | 10148 | CB | ARG | B | 121 | 69.116 | 43.838 | −19.109 | 1.00 | 20.34 | B | C |
| ATOM | 10151 | CG | ARG | B | 121 | 68.782 | 42.387 | −19.214 | 1.00 | 22.78 | B | C |
| ATOM | 10154 | CD | ARG | B | 121 | 69.278 | 41.785 | −20.511 | 1.00 | 23.57 | B | C |
| ATOM | 10157 | NE | ARG | B | 121 | 70.735 | 41.705 | −20.574 | 1.00 | 22.85 | B | N |
| ATOM | 10159 | CZ | ARG | B | 121 | 71.486 | 40.804 | −19.954 | 1.00 | 21.72 | B | C |
| ATOM | 10160 | NH1 | ARG | B | 121 | 70.943 | 39.879 | −19.173 | 1.00 | 27.91 | B | N |
| ATOM | 10163 | NH2 | ARG | B | 121 | 72.797 | 40.835 | −20.117 | 1.00 | 22.89 | B | N |
| ATOM | 10166 | C | ARG | B | 121 | 68.467 | 43.826 | −16.691 | 1.00 | 20.89 | B | C |
| ATOM | 10167 | O | ARG | B | 121 | 67.536 | 43.185 | −16.244 | 1.00 | 22.14 | B | O |
| ATOM | 10169 | N | LEU | B | 122 | 69.634 | 43.918 | −16.075 | 1.00 | 19.65 | B | N |
| ATOM | 10170 | CA | LEU | B | 122 | 69.877 | 43.198 | −14.829 | 1.00 | 21.62 | B | C |
| ATOM | 10172 | CB | LEU | B | 122 | 71.342 | 43.312 | −14.409 | 1.00 | 19.60 | B | C |
| ATOM | 10175 | CG | LEU | B | 122 | 72.377 | 42.726 | −15.362 | 1.00 | 20.38 | B | C |
| ATOM | 10177 | CD1 | LEU | B | 122 | 73.745 | 43.081 | −14.843 | 1.00 | 20.38 | B | C |
| ATOM | 10181 | CD2 | LEU | B | 122 | 72.217 | 41.193 | −15.508 | 1.00 | 15.76 | B | C |
| ATOM | 10185 | C | LEU | B | 122 | 68.947 | 43.705 | −13.710 | 1.00 | 22.20 | B | C |
| ATOM | 10186 | O | LEU | B | 122 | 68.419 | 42.921 | −12.921 | 1.00 | 22.69 | B | O |
| ATOM | 10188 | N | LEU | B | 123 | 68.712 | 45.009 | −13.681 | 1.00 | 23.60 | B | N |
| ATOM | 10189 | CA | LEU | B | 123 | 67.893 | 45.608 | −12.624 | 1.00 | 24.18 | B | C |
| ATOM | 10191 | CB | LEU | B | 123 | 67.931 | 47.130 | −12.701 | 1.00 | 21.92 | B | C |
| ATOM | 10194 | CG | LEU | B | 123 | 69.156 | 47.757 | −12.041 | 1.00 | 22.98 | B | C |
| ATOM | 10196 | CD1 | LEU | B | 123 | 69.363 | 49.223 | −12.487 | 1.00 | 19.39 | B | C |
| ATOM | 10200 | CD2 | LEU | B | 123 | 68.981 | 47.662 | −10.548 | 1.00 | 20.14 | B | C |
| ATOM | 10204 | C | LEU | B | 123 | 66.466 | 45.120 | −12.738 | 1.00 | 23.74 | B | C |
| ATOM | 10205 | O | LEU | B | 123 | 65.855 | 44.696 | −11.753 | 1.00 | 21.87 | B | O |
| ATOM | 10207 | N | ARG | B | 124 | 65.947 | 45.176 | −13.951 | 1.00 | 23.61 | B | N |
| ATOM | 10208 | CA | ARG | B | 124 | 64.580 | 44.747 | −14.194 | 1.00 | 22.51 | B | C |
| ATOM | 10210 | CB | ARG | B | 124 | 64.101 | 45.189 | −15.566 | 1.00 | 21.92 | B | C |
| ATOM | 10213 | CG | ARG | B | 124 | 62.624 | 44.861 | −15.768 | 1.00 | 23.90 | B | C |
| ATOM | 10216 | CD | ARG | B | 124 | 62.050 | 45.560 | −16.965 | 1.00 | 23.86 | B | C |
| ATOM | 10219 | NE | ARG | B | 124 | 61.591 | 46.926 | −16.676 | 1.00 | 24.72 | B | N |
| ATOM | 10221 | CZ | ARG | B | 124 | 61.083 | 47.743 | −17.601 | 1.00 | 24.21 | B | C |
| ATOM | 10222 | NH1 | ARG | B | 124 | 60.998 | 47.363 | −18.872 | 1.00 | 21.36 | B | N |
| ATOM | 10225 | NH2 | ARG | B | 124 | 60.671 | 48.955 | −17.265 | 1.00 | 25.66 | B | N |
| ATOM | 10228 | C | ARG | B | 124 | 64.420 | 43.247 | −14.052 | 1.00 | 22.28 | B | C |
| ATOM | 10229 | O | ARG | B | 124 | 63.435 | 42.768 | −13.479 | 1.00 | 23.53 | B | O |
| ATOM | 10231 | N | GLN | B | 125 | 65.389 | 42.490 | −14.549 | 1.00 | 23.20 | B | N |
| ATOM | 10232 | CA | GLN | B | 125 | 65.371 | 41.051 | −14.344 | 1.00 | 20.98 | B | C |

TABLE 4-2-continued

Coordinates of *P. alba* IspS

| ATOM | 10234 | CB  | GLN | B | 125 | 66.693 | 40.426 | −14.832 | 1.00 | 22.19 | B | C |
|------|-------|-----|-----|---|-----|--------|--------|---------|------|-------|---|---|
| ATOM | 10237 | CG  | GLN | B | 125 | 66.800 | 38.889 | −14.619 | 1.00 | 17.52 | B | C |
| ATOM | 10240 | CD  | GLN | B | 125 | 68.218 | 38.364 | −14.797 | 1.00 | 23.28 | B | C |
| ATOM | 10241 | OE1 | GLN | B | 125 | 69.105 | 39.069 | −15.273 | 1.00 | 19.79 | B | O |
| ATOM | 10242 | NE2 | GLN | B | 125 | 68.435 | 37.121 | −14.405 | 1.00 | 17.64 | B | N |
| ATOM | 10245 | C   | GLN | B | 125 | 65.164 | 40.777 | −12.847 | 1.00 | 23.00 | B | C |
| ATOM | 10246 | O   | GLN | B | 125 | 64.420 | 39.865 | −12.453 | 1.00 | 24.90 | B | O |
| ATOM | 10248 | N   | HIS | B | 126 | 65.828 | 41.561 | −12.005 | 1.00 | 20.88 | B | N |
| ATOM | 10249 | CA  | HIS | B | 126 | 65.780 | 41.310 | −10.576 | 1.00 | 22.19 | B | C |
| ATOM | 10251 | CB  | HIS | B | 126 | 67.179 | 41.491 | −9.966  | 1.00 | 22.02 | B | C |
| ATOM | 10254 | CG  | HIS | B | 126 | 68.109 | 40.381 | −10.310 | 1.00 | 21.58 | B | C |
| ATOM | 10255 | ND1 | HIS | B | 126 | 68.196 | 39.230 | −9.557  | 1.00 | 24.31 | B | N |
| ATOM | 10257 | CE1 | HIS | B | 126 | 69.090 | 38.425 | −10.103 | 1.00 | 23.72 | B | C |
| ATOM | 10259 | NE2 | HIS | B | 126 | 69.560 | 38.997 | −11.199 | 1.00 | 20.64 | B | N |
| ATOM | 10261 | CD2 | HIS | B | 126 | 68.960 | 40.218 | −11.353 | 1.00 | 17.59 | B | C |
| ATOM | 10263 | C   | HIS | B | 126 | 64.742 | 42.137 | −9.829  | 1.00 | 23.10 | B | C |
| ATOM | 10264 | O   | HIS | B | 126 | 64.850 | 42.311 | −8.624  | 1.00 | 23.65 | B | O |
| ATOM | 10266 | N   | GLY | B | 127 | 63.739 | 42.655 | −10.529 | 1.00 | 25.00 | B | N |
| ATOM | 10267 | CA  | GLY | B | 127 | 62.577 | 43.232 | −9.849  | 1.00 | 24.96 | B | C |
| ATOM | 10270 | C   | GLY | B | 127 | 62.665 | 44.712 | −9.523  | 1.00 | 27.27 | B | C |
| ATOM | 10271 | O   | GLY | B | 127 | 61.701 | 45.275 | −9.007  | 1.00 | 31.01 | B | O |
| ATOM | 10273 | N   | PHE | B | 128 | 63.798 | 45.353 | −9.818  | 1.00 | 27.09 | B | N |
| ATOM | 10274 | CA  | PHE | B | 128 | 63.946 | 46.787 | −9.589  | 1.00 | 27.86 | B | C |
| ATOM | 10276 | CB  | PHE | B | 128 | 65.418 | 47.218 | −9.615  | 1.00 | 28.07 | B | C |
| ATOM | 10279 | CG  | PHE | B | 128 | 66.208 | 46.655 | −8.482  | 1.00 | 28.18 | B | C |
| ATOM | 10280 | CD1 | PHE | B | 128 | 66.303 | 47.336 | −7.294  | 1.00 | 28.13 | B | C |
| ATOM | 10282 | CE1 | PHE | B | 128 | 67.003 | 46.811 | −6.249  | 1.00 | 33.20 | B | C |
| ATOM | 10284 | CZ  | PHE | B | 128 | 67.592 | 45.571 | −6.362  | 1.00 | 34.73 | B | C |
| ATOM | 10286 | CE2 | PHE | B | 128 | 67.479 | 44.871 | −7.535  | 1.00 | 30.35 | B | C |
| ATOM | 10288 | CD2 | PHE | B | 128 | 66.785 | 45.409 | −8.580  | 1.00 | 26.88 | B | C |
| ATOM | 10290 | C   | PHE | B | 128 | 63.150 | 47.567 | −10.605 | 1.00 | 30.22 | B | C |
| ATOM | 10291 | O   | PHE | B | 128 | 62.932 | 47.122 | −11.725 | 1.00 | 30.38 | B | O |
| ATOM | 10293 | N   | GLU | B | 129 | 62.703 | 48.739 | −10.185 | 1.00 | 31.72 | B | N |
| ATOM | 10294 | CA  | GLU | B | 129 | 61.883 | 49.589 | −10.999 | 1.00 | 32.85 | B | C |
| ATOM | 10296 | CB  | GLU | B | 129 | 60.995 | 50.460 | −10.091 | 1.00 | 35.17 | B | C |
| ATOM | 10299 | CG  | GLU | B | 129 | 59.781 | 51.091 | −10.797 | 1.00 | 46.55 | B | C |
| ATOM | 10302 | CD  | GLU | B | 129 | 59.293 | 52.392 | −10.153 | 1.00 | 59.19 | B | C |
| ATOM | 10303 | OE1 | GLU | B | 129 | 59.590 | 52.647 | −8.963  | 1.00 | 62.18 | B | O |
| ATOM | 10304 | OE2 | GLU | B | 129 | 58.598 | 53.169 | −10.850 | 1.00 | 66.91 | B | O |
| ATOM | 10305 | C   | GLU | B | 129 | 62.833 | 50.455 | −11.828 | 1.00 | 30.85 | B | C |
| ATOM | 10306 | O   | GLU | B | 129 | 63.634 | 51.200 | −11.283 | 1.00 | 34.34 | B | O |
| ATOM | 10308 | N   | VAL | B | 130 | 62.773 | 50.339 | −13.140 | 1.00 | 28.74 | B | N |
| ATOM | 10309 | CA  | VAL | B | 130 | 63.538 | 51.222 | −14.013 | 1.00 | 27.95 | B | C |
| ATOM | 10311 | CB  | VAL | B | 130 | 64.783 | 50.533 | −14.591 | 1.00 | 28.89 | B | C |
| ATOM | 10313 | CG1 | VAL | B | 130 | 65.800 | 50.323 | −13.491 | 1.00 | 29.52 | B | C |
| ATOM | 10317 | CG2 | VAL | B | 130 | 64.422 | 49.201 | −15.242 | 1.00 | 25.33 | B | C |
| ATOM | 10321 | C   | VAL | B | 130 | 62.647 | 51.707 | −15.142 | 1.00 | 27.27 | B | C |
| ATOM | 10322 | O   | VAL | B | 130 | 61.695 | 51.033 | −15.506 | 1.00 | 26.56 | B | O |
| ATOM | 10324 | N   | SER | B | 131 | 62.969 | 52.872 | −15.692 | 1.00 | 27.05 | B | N |
| ATOM | 10325 | CA  | SER | B | 131 | 62.140 | 53.510 | −16.713 | 1.00 | 27.56 | B | C |
| ATOM | 10327 | CB  | SER | B | 131 | 61.864 | 54.978 | −16.339 | 1.00 | 29.10 | B | C |
| ATOM | 10330 | OG  | SER | B | 131 | 61.318 | 55.713 | −17.434 | 1.00 | 34.05 | B | O |
| ATOM | 10332 | C   | SER | B | 131 | 62.871 | 53.470 | −18.031 | 1.00 | 26.59 | B | C |
| ATOM | 10333 | O   | SER | B | 131 | 64.091 | 53.530 | −18.056 | 1.00 | 27.34 | B | O |
| ATOM | 10335 | N   | GLN | B | 132 | 62.125 | 53.379 | −19.127 | 1.00 | 26.19 | B | N |
| ATOM | 10336 | CA  | GLN | B | 132 | 62.718 | 53.487 | −20.450 | 1.00 | 26.48 | B | C |
| ATOM | 10338 | CB  | GLN | B | 132 | 61.660 | 53.267 | −21.528 | 1.00 | 26.03 | B | C |
| ATOM | 10341 | CG  | GLN | B | 132 | 60.477 | 54.223 | −21.463 | 1.00 | 26.99 | B | C |
| ATOM | 10344 | CD  | GLN | B | 132 | 59.623 | 54.191 | −22.711 | 1.00 | 29.29 | B | C |
| ATOM | 10345 | OE1 | GLN | B | 132 | 59.822 | 53.355 | −23.602 | 1.00 | 27.92 | B | O |
| ATOM | 10346 | NE2 | GLN | B | 132 | 58.662 | 55.110 | −22.787 | 1.00 | 28.13 | B | N |
| ATOM | 10349 | C   | GLN | B | 132 | 63.404 | 54.840 | −20.664 | 1.00 | 28.30 | B | C |
| ATOM | 10350 | O   | GLN | B | 132 | 64.219 | 54.978 | −21.568 | 1.00 | 29.48 | B | O |
| ATOM | 10352 | N   | GLU | B | 133 | 63.073 | 55.840 | −19.846 | 1.00 | 30.19 | B | N |
| ATOM | 10353 | CA  | GLU | B | 133 | 63.686 | 57.179 | −19.974 | 1.00 | 32.53 | B | C |
| ATOM | 10355 | CB  | GLU | B | 133 | 62.976 | 58.238 | −19.113 | 1.00 | 33.08 | B | C |
| ATOM | 10358 | CG  | GLU | B | 133 | 61.500 | 58.466 | −19.448 | 1.00 | 38.45 | B | C |
| ATOM | 10361 | CD  | GLU | B | 133 | 61.264 | 59.001 | −20.854 | 1.00 | 45.49 | B | C |
| ATOM | 10362 | OE1 | GLU | B | 133 | 62.178 | 59.632 | −21.439 | 1.00 | 49.73 | B | O |
| ATOM | 10363 | OE2 | GLU | B | 133 | 60.144 | 58.798 | −21.376 | 1.00 | 46.47 | B | O |
| ATOM | 10364 | C   | GLU | B | 133 | 65.155 | 57.140 | −19.609 | 1.00 | 31.46 | B | C |
| ATOM | 10365 | O   | GLU | B | 133 | 65.884 | 58.069 | −19.912 | 1.00 | 32.50 | B | O |
| ATOM | 10367 | N   | ALA | B | 134 | 65.584 | 56.061 | −18.964 | 1.00 | 30.90 | B | N |
| ATOM | 10368 | CA  | ALA | B | 134 | 67.002 | 55.760 | −18.824 | 1.00 | 30.86 | B | C |
| ATOM | 10370 | CB  | ALA | B | 134 | 67.185 | 54.385 | −18.224 | 1.00 | 28.22 | B | C |
| ATOM | 10374 | C   | ALA | B | 134 | 67.723 | 55.849 | −20.170 | 1.00 | 31.89 | B | C |
| ATOM | 10375 | O   | ALA | B | 134 | 68.913 | 56.107 | −20.222 | 1.00 | 34.24 | B | O |
| ATOM | 10377 | N   | PHE | B | 135 | 66.997 | 55.657 | −21.261 | 1.00 | 33.61 | B | N |

TABLE 4-2-continued

Coordinates of *P. alba* IspS

| ATOM | 10378 | CA  | PHE | B | 135 | 67.597 | 55.727 | −22.588 | 1.00 | 34.02 | B | C |
| ---- | ----- | --- | --- | - | --- | ------ | ------ | ------- | ---- | ----- | - | - |
| ATOM | 10380 | CB  | PHE | B | 135 | 67.014 | 54.608 | −23.456 | 1.00 | 32.07 | B | C |
| ATOM | 10383 | CG  | PHE | B | 135 | 67.399 | 53.261 | −22.980 | 1.00 | 28.15 | B | C |
| ATOM | 10384 | CD1 | PHE | B | 135 | 66.564 | 52.535 | −22.159 | 1.00 | 26.04 | B | C |
| ATOM | 10386 | CE1 | PHE | B | 135 | 66.955 | 51.280 | −21.677 | 1.00 | 24.62 | B | C |
| ATOM | 10388 | CZ  | PHE | B | 135 | 68.188 | 50.768 | −22.013 | 1.00 | 27.19 | B | C |
| ATOM | 10390 | CE2 | PHE | B | 135 | 69.039 | 51.497 | −22.821 | 1.00 | 28.77 | B | C |
| ATOM | 10392 | CD2 | PHE | B | 135 | 68.648 | 52.740 | −23.294 | 1.00 | 30.81 | B | C |
| ATOM | 10394 | C   | PHE | B | 135 | 67.454 | 57.082 | −23.281 | 1.00 | 36.30 | B | C |
| ATOM | 10395 | O   | PHE | B | 135 | 67.929 | 57.245 | −24.414 | 1.00 | 37.39 | B | O |
| ATOM | 10397 | N   | SER | B | 136 | 66.840 | 58.058 | −22.611 | 1.00 | 37.55 | B | N |
| ATOM | 10398 | CA  | SER | B | 136 | 66.566 | 59.356 | −23.244 | 1.00 | 38.94 | B | C |
| ATOM | 10400 | CB  | SER | B | 136 | 65.767 | 60.282 | −22.305 | 1.00 | 39.41 | B | C |
| ATOM | 10403 | OG  | SER | B | 136 | 66.461 | 60.527 | −21.086 | 1.00 | 40.01 | B | O |
| ATOM | 10405 | C   | SER | B | 136 | 67.848 | 60.047 | −23.724 | 1.00 | 39.27 | B | C |
| ATOM | 10406 | O   | SER | B | 136 | 67.839 | 60.721 | −24.753 | 1.00 | 41.19 | B | O |
| ATOM | 10408 | N   | GLY | B | 137 | 68.949 | 59.847 | −23.010 | 1.00 | 38.96 | B | N |
| ATOM | 10409 | CA  | GLY | B | 137 | 70.199 | 60.526 | −23.333 | 1.00 | 39.72 | B | C |
| ATOM | 10412 | C   | GLY | B | 137 | 70.897 | 60.111 | −24.622 | 1.00 | 39.94 | B | C |
| ATOM | 10413 | O   | GLY | B | 137 | 71.863 | 60.761 | −25.027 | 1.00 | 40.11 | B | O |
| ATOM | 10415 | N   | PHE | B | 138 | 70.432 | 59.038 | −25.265 | 1.00 | 40.41 | B | N |
| ATOM | 10416 | CA  | PHE | B | 138 | 71.074 | 58.516 | −26.490 | 1.00 | 41.42 | B | C |
| ATOM | 10418 | CB  | PHE | B | 138 | 71.367 | 57.019 | −26.332 | 1.00 | 40.22 | B | C |
| ATOM | 10421 | CG  | PHE | B | 138 | 72.080 | 56.695 | −25.064 | 1.00 | 37.60 | B | C |
| ATOM | 10422 | CD1 | PHE | B | 138 | 73.441 | 56.898 | −24.959 | 1.00 | 35.26 | B | C |
| ATOM | 10424 | CE1 | PHE | B | 138 | 74.103 | 56.628 | −23.776 | 1.00 | 35.62 | B | C |
| ATOM | 10426 | CZ  | PHE | B | 138 | 73.400 | 56.170 | −22.682 | 1.00 | 34.61 | B | C |
| ATOM | 10428 | CE2 | PHE | B | 138 | 72.035 | 55.974 | −22.773 | 1.00 | 32.75 | B | C |
| ATOM | 10430 | CD2 | PHE | B | 138 | 71.383 | 56.235 | −23.955 | 1.00 | 35.81 | B | C |
| ATOM | 10432 | C   | PHE | B | 138 | 70.254 | 58.760 | −27.758 | 1.00 | 43.98 | B | C |
| ATOM | 10433 | O   | PHE | B | 138 | 70.642 | 58.317 | −28.843 | 1.00 | 43.19 | B | O |
| ATOM | 10435 | N   | LYS | B | 139 | 69.128 | 59.460 | −27.609 | 1.00 | 47.54 | B | N |
| ATOM | 10436 | CA  | LYS | B | 139 | 68.279 | 59.824 | −28.734 | 1.00 | 51.04 | B | C |
| ATOM | 10438 | CB  | LYS | B | 139 | 66.799 | 59.812 | −28.322 | 1.00 | 51.46 | B | C |
| ATOM | 10441 | CG  | LYS | B | 139 | 66.192 | 58.391 | −28.258 | 1.00 | 55.89 | B | C |
| ATOM | 10444 | CD  | LYS | B | 139 | 64.883 | 58.314 | −27.450 | 1.00 | 59.90 | B | C |
| ATOM | 10447 | CE  | LYS | B | 139 | 63.667 | 58.845 | −28.219 | 1.00 | 63.07 | B | C |
| ATOM | 10450 | NZ  | LYS | B | 139 | 63.073 | 57.860 | −29.172 | 1.00 | 58.78 | B | N |
| ATOM | 10454 | C   | LYS | B | 139 | 68.699 | 61.198 | −29.255 | 1.00 | 53.29 | B | C |
| ATOM | 10455 | O   | LYS | B | 139 | 68.986 | 62.106 | −28.470 | 1.00 | 54.74 | B | O |
| ATOM | 10457 | N   | ASP | B | 140 | 68.743 | 61.339 | −30.579 | 1.00 | 55.19 | B | N |
| ATOM | 10458 | CA  | ASP | B | 140 | 69.183 | 62.580 | −31.216 | 1.00 | 56.63 | B | C |
| ATOM | 10460 | CB  | ASP | B | 140 | 69.663 | 62.312 | −32.662 | 1.00 | 55.93 | B | C |
| ATOM | 10463 | CG  | ASP | B | 140 | 68.528 | 61.932 | −33.627 | 1.00 | 54.78 | B | C |
| ATOM | 10464 | OD1 | ASP | B | 140 | 67.331 | 62.035 | −33.273 | 1.00 | 48.15 | B | O |
| ATOM | 10465 | OD2 | ASP | B | 140 | 68.847 | 61.518 | −34.763 | 1.00 | 51.45 | B | O |
| ATOM | 10466 | C   | ASP | B | 140 | 68.090 | 63.656 | −31.172 | 1.00 | 59.23 | B | C |
| ATOM | 10467 | O   | ASP | B | 140 | 67.021 | 63.456 | −30.576 | 1.00 | 59.10 | B | O |
| ATOM | 10469 | N   | GLN | B | 141 | 68.385 | 64.794 | −31.803 | 1.00 | 62.19 | B | N |
| ATOM | 10470 | CA  | GLN | B | 141 | 67.447 | 65.918 | −31.951 | 1.00 | 63.69 | B | C |
| ATOM | 10472 | CB  | GLN | B | 141 | 67.947 | 66.889 | −33.034 | 1.00 | 64.14 | B | C |
| ATOM | 10475 | CG  | GLN | B | 141 | 69.332 | 67.484 | −32.792 | 1.00 | 67.32 | B | C |
| ATOM | 10478 | CD  | GLN | B | 141 | 69.331 | 68.608 | −31.775 | 1.00 | 70.44 | B | C |
| ATOM | 10479 | OE1 | GLN | B | 141 | 68.722 | 68.506 | −30.710 | 1.00 | 70.76 | B | O |
| ATOM | 10480 | NE2 | GLN | B | 141 | 70.032 | 69.686 | −32.097 | 1.00 | 68.92 | B | N |
| ATOM | 10483 | C   | GLN | B | 141 | 66.032 | 65.451 | −32.314 | 1.00 | 63.72 | B | C |
| ATOM | 10484 | O   | GLN | B | 141 | 65.086 | 65.649 | −31.544 | 1.00 | 63.99 | B | O |
| ATOM | 10486 | N   | ASN | B | 142 | 65.912 | 64.804 | −33.473 | 1.00 | 63.20 | B | N |
| ATOM | 10487 | CA  | ASN | B | 142 | 64.622 | 64.348 | −33.997 | 1.00 | 62.48 | B | C |
| ATOM | 10489 | CB  | ASN | B | 142 | 64.795 | 63.752 | −35.399 | 1.00 | 62.80 | B | C |
| ATOM | 10492 | CG  | ASN | B | 142 | 65.133 | 64.801 | −36.442 | 1.00 | 64.18 | B | C |
| ATOM | 10493 | OD1 | ASN | B | 142 | 64.277 | 65.195 | −37.234 | 1.00 | 64.38 | B | O |
| ATOM | 10494 | ND2 | ASN | B | 142 | 66.381 | 65.261 | −36.446 | 1.00 | 61.04 | B | N |
| ATOM | 10497 | C   | ASN | B | 142 | 63.913 | 63.330 | −33.100 | 1.00 | 61.50 | B | C |
| ATOM | 10498 | O   | ASN | B | 142 | 62.686 | 63.236 | −33.128 | 1.00 | 61.52 | B | O |
| ATOM | 10500 | N   | GLY | B | 143 | 64.685 | 62.579 | −32.311 | 1.00 | 59.99 | B | N |
| ATOM | 10501 | CA  | GLY | B | 143 | 64.141 | 61.554 | −31.415 | 1.00 | 58.60 | B | C |
| ATOM | 10504 | C   | GLY | B | 143 | 64.432 | 60.122 | −31.846 | 1.00 | 57.01 | B | C |
| ATOM | 10505 | O   | GLY | B | 143 | 63.800 | 59.186 | −31.353 | 1.00 | 57.12 | B | O |
| ATOM | 10507 | N   | ASN | B | 144 | 65.374 | 59.963 | −32.778 | 1.00 | 54.93 | B | N |
| ATOM | 10508 | CA  | ASN | B | 144 | 65.892 | 58.658 | −33.197 | 1.00 | 52.65 | B | C |
| ATOM | 10510 | CB  | ASN | B | 144 | 66.171 | 58.636 | −34.709 | 1.00 | 52.20 | B | C |
| ATOM | 10513 | CG  | ASN | B | 144 | 64.960 | 59.056 | −35.545 | 1.00 | 55.56 | B | C |
| ATOM | 10514 | OD1 | ASN | B | 144 | 64.720 | 60.251 | −35.772 | 1.00 | 57.00 | B | O |
| ATOM | 10515 | ND2 | ASN | B | 144 | 64.208 | 58.073 | −36.026 | 1.00 | 53.61 | B | N |
| ATOM | 10518 | C   | ASN | B | 144 | 67.189 | 58.393 | −32.442 | 1.00 | 49.76 | B | C |
| ATOM | 10519 | O   | ASN | B | 144 | 67.842 | 59.331 | −32.005 | 1.00 | 48.69 | B | O |
| ATOM | 10521 | N   | PHE | B | 145 | 67.569 | 57.126 | −32.281 | 1.00 | 47.64 | B | N |

TABLE 4-2-continued

| | | | | Coordinates of *P. alba* IspS | | | | | | | |
|---|---|---|---|---|---|---|---|---|---|---|---|
| ATOM | 10522 | CA | PHE | B | 145 | 68.855 | 56.807 | −31.638 | 1.00 | 44.61 | B | C |
| ATOM | 10524 | CB | PHE | B | 145 | 69.028 | 55.293 | −31.433 | 1.00 | 43.24 | B | C |
| ATOM | 10527 | CG | PHE | B | 145 | 68.385 | 54.778 | −30.171 | 1.00 | 37.63 | B | C |
| ATOM | 10528 | CD1 | PHE | B | 145 | 67.113 | 54.240 | −30.192 | 1.00 | 30.84 | B | C |
| ATOM | 10530 | CE1 | PHE | B | 145 | 66.516 | 53.777 | −29.038 | 1.00 | 32.98 | B | C |
| ATOM | 10532 | CZ | PHE | B | 145 | 67.188 | 53.849 | −27.839 | 1.00 | 35.80 | B | C |
| ATOM | 10534 | CE2 | PHE | B | 145 | 68.462 | 54.383 | −27.796 | 1.00 | 36.24 | B | C |
| ATOM | 10536 | CD2 | PHE | B | 145 | 69.052 | 54.851 | −28.958 | 1.00 | 35.52 | B | C |
| ATOM | 10538 | C | PHE | B | 145 | 70.014 | 57.381 | −32.452 | 1.00 | 44.54 | B | C |
| ATOM | 10539 | O | PHE | B | 145 | 69.957 | 57.418 | −33.679 | 1.00 | 43.23 | B | O |
| ATOM | 10541 | N | LEU | B | 146 | 71.051 | 57.846 | −31.761 | 1.00 | 45.81 | B | N |
| ATOM | 10542 | CA | LEU | B | 146 | 72.210 | 58.429 | −32.429 | 1.00 | 47.80 | B | C |
| ATOM | 10544 | CB | LEU | B | 146 | 73.211 | 58.969 | −31.402 | 1.00 | 48.75 | B | C |
| ATOM | 10547 | CG | LEU | B | 146 | 72.777 | 60.256 | −30.682 | 1.00 | 50.65 | B | C |
| ATOM | 10549 | CD1 | LEU | B | 146 | 73.588 | 60.481 | −29.409 | 1.00 | 52.76 | B | C |
| ATOM | 10553 | CD2 | LEU | B | 146 | 72.894 | 61.455 | −31.605 | 1.00 | 50.35 | B | C |
| ATOM | 10557 | C | LEU | B | 146 | 72.860 | 57.390 | −33.344 | 1.00 | 48.09 | B | C |
| ATOM | 10558 | O | LEU | B | 146 | 73.014 | 56.241 | −32.960 | 1.00 | 47.53 | B | O |
| ATOM | 10560 | N | GLU | B | 147 | 73.217 | 57.803 | −34.559 | 1.00 | 49.06 | B | N |
| ATOM | 10561 | CA | GLU | B | 147 | 73.758 | 56.896 | −35.582 | 1.00 | 49.97 | B | C |
| ATOM | 10563 | CB | GLU | B | 147 | 73.868 | 57.627 | −36.934 | 1.00 | 51.58 | B | C |
| ATOM | 10566 | CG | GLU | B | 147 | 74.260 | 56.747 | −38.147 | 1.00 | 56.44 | B | C |
| ATOM | 10569 | CD | GLU | B | 147 | 73.083 | 55.980 | −38.761 | 1.00 | 62.69 | B | C |
| ATOM | 10570 | OE1 | GLU | B | 147 | 71.979 | 56.554 | −38.876 | 1.00 | 64.99 | B | O |
| ATOM | 10571 | OE2 | GLU | B | 147 | 73.267 | 54.806 | −39.153 | 1.00 | 66.36 | B | O |
| ATOM | 10572 | C | GLU | B | 147 | 75.132 | 56.348 | −35.201 | 1.00 | 49.04 | B | C |
| ATOM | 10573 | O | GLU | B | 147 | 75.434 | 55.185 | −35.479 | 1.00 | 47.66 | B | O |
| ATOM | 10575 | N | ASN | B | 148 | 75.961 | 57.187 | −34.579 | 1.00 | 48.87 | B | N |
| ATOM | 10576 | CA | ASN | B | 148 | 77.347 | 56.814 | −34.262 | 1.00 | 49.90 | B | C |
| ATOM | 10578 | CB | ASN | B | 148 | 78.202 | 58.067 | −33.992 | 1.00 | 51.02 | B | C |
| ATOM | 10581 | CG | ASN | B | 148 | 78.031 | 58.610 | −32.576 | 1.00 | 56.07 | B | C |
| ATOM | 10582 | OD1 | ASN | B | 148 | 78.936 | 58.492 | −31.742 | 1.00 | 61.26 | B | O |
| ATOM | 10583 | ND2 | ASN | B | 148 | 76.868 | 59.198 | −32.297 | 1.00 | 58.99 | B | N |
| ATOM | 10586 | C | ASN | B | 148 | 77.497 | 55.801 | −33.110 | 1.00 | 48.73 | B | C |
| ATOM | 10587 | O | ASN | B | 148 | 78.611 | 55.402 | −32.776 | 1.00 | 49.75 | B | O |
| ATOM | 10589 | N | LEU | B | 149 | 76.382 | 55.390 | −32.507 | 1.00 | 47.68 | B | N |
| ATOM | 10590 | CA | LEU | B | 149 | 76.389 | 54.305 | −31.515 | 1.00 | 46.24 | B | C |
| ATOM | 10592 | CB | LEU | B | 149 | 75.105 | 54.326 | −30.675 | 1.00 | 44.68 | B | C |
| ATOM | 10595 | CG | LEU | B | 149 | 74.933 | 55.554 | −29.764 | 1.00 | 43.56 | B | C |
| ATOM | 10597 | CD1 | LEU | B | 149 | 73.479 | 55.709 | −29.326 | 1.00 | 39.02 | B | C |
| ATOM | 10601 | CD2 | LEU | B | 149 | 75.853 | 55.508 | −28.553 | 1.00 | 40.99 | B | C |
| ATOM | 10605 | C | LEU | B | 149 | 76.588 | 52.934 | −32.184 | 1.00 | 45.14 | B | C |
| ATOM | 10606 | O | LEU | B | 149 | 77.087 | 52.003 | −31.546 | 1.00 | 44.56 | B | O |
| ATOM | 10608 | N | LYS | B | 150 | 76.239 | 52.828 | −33.470 | 1.00 | 43.79 | B | N |
| ATOM | 10609 | CA | LYS | B | 150 | 76.438 | 51.593 | −34.246 | 1.00 | 43.54 | B | C |
| ATOM | 10611 | CB | LYS | B | 150 | 75.933 | 51.764 | −35.682 | 1.00 | 43.61 | B | C |
| ATOM | 10614 | CG | LYS | B | 150 | 76.894 | 52.553 | −36.587 | 1.00 | 46.08 | B | C |
| ATOM | 10617 | CD | LYS | B | 150 | 76.268 | 52.898 | −37.924 | 1.00 | 46.55 | B | C |
| ATOM | 10620 | CE | LYS | B | 150 | 77.268 | 53.562 | −38.861 | 1.00 | 44.81 | B | C |
| ATOM | 10623 | NZ | LYS | B | 150 | 76.697 | 53.648 | −40.228 | 1.00 | 43.17 | B | N |
| ATOM | 10627 | C | LYS | B | 150 | 77.893 | 51.098 | −34.291 | 1.00 | 43.90 | B | C |
| ATOM | 10628 | O | LYS | B | 150 | 78.127 | 49.952 | −34.663 | 1.00 | 43.76 | B | O |
| ATOM | 10630 | N | GLU | B | 151 | 78.854 | 51.963 | −33.953 | 1.00 | 44.36 | B | N |
| ATOM | 10631 | CA | AGLU | B | 151 | 80.275 | 51.600 | −33.889 | 0.50 | 45.03 | B | C |
| ATOM | 10632 | CA | BGLU | B | 151 | 80.259 | 51.556 | −33.922 | 0.50 | 44.55 | B | C |
| ATOM | 10635 | CB | AGLU | B | 151 | 81.158 | 52.860 | −33.903 | 0.50 | 45.31 | B | C |
| ATOM | 10636 | CB | BGLU | B | 151 | 81.192 | 52.765 | −34.101 | 0.50 | 44.49 | B | C |
| ATOM | 10641 | CG | AGLU | B | 151 | 81.067 | 53.700 | −35.176 | 0.50 | 46.10 | B | C |
| ATOM | 10642 | CG | BGLU | B | 151 | 80.988 | 53.561 | −35.408 | 0.50 | 42.68 | B | C |
| ATOM | 10647 | CD | AGLU | B | 151 | 81.927 | 54.953 | −35.116 | 0.50 | 46.35 | B | C |
| ATOM | 10648 | CD | BGLU | B | 151 | 81.246 | 52.747 | −36.675 | 0.50 | 39.43 | B | C |
| ATOM | 10649 | OE1 | AGLU | B | 151 | 82.923 | 54.965 | −34.361 | 0.50 | 46.87 | B | O |
| ATOM | 10650 | OE1 | BGLU | B | 151 | 82.082 | 51.820 | −36.641 | 0.50 | 33.96 | B | O |
| ATOM | 10651 | OE2 | AGLU | B | 151 | 81.610 | 55.927 | −35.830 | 0.50 | 47.69 | B | O |
| ATOM | 10652 | OE2 | BGLU | B | 151 | 80.611 | 53.048 | −37.711 | 0.50 | 33.24 | B | O |
| ATOM | 10653 | C | GLU | B | 151 | 80.593 | 50.796 | −32.629 | 1.00 | 44.92 | B | C |
| ATOM | 10654 | O | GLU | B | 151 | 81.544 | 50.008 | −32.603 | 1.00 | 45.51 | B | O |
| ATOM | 10656 | N | ASP | B | 152 | 79.806 | 51.022 | −31.573 | 1.00 | 43.91 | B | N |
| ATOM | 10657 | CA | ASP | B | 152 | 79.998 | 50.341 | −30.286 | 1.00 | 43.25 | B | C |
| ATOM | 10659 | CB | ASP | B | 152 | 79.682 | 51.305 | −29.129 | 1.00 | 42.94 | B | C |
| ATOM | 10662 | CG | ASP | B | 152 | 80.049 | 50.733 | −27.762 | 1.00 | 45.23 | B | C |
| ATOM | 10663 | OD1 | ASP | B | 152 | 80.532 | 49.581 | −27.686 | 1.00 | 44.55 | B | O |
| ATOM | 10664 | OD2 | ASP | B | 152 | 79.861 | 51.449 | −26.754 | 1.00 | 46.70 | B | O |
| ATOM | 10665 | C | ASP | B | 152 | 79.118 | 49.076 | −30.217 | 1.00 | 42.56 | B | C |
| ATOM | 10666 | O | ASP | B | 152 | 78.040 | 49.079 | −29.619 | 1.00 | 42.14 | B | O |
| ATOM | 10668 | N | ILE | B | 153 | 79.596 | 47.994 | −30.826 | 1.00 | 41.74 | B | N |
| ATOM | 10669 | CA | ILE | B | 153 | 78.793 | 46.777 | −31.016 | 1.00 | 40.19 | B | C |
| ATOM | 10671 | CB | ILE | B | 153 | 79.541 | 45.753 | −31.887 | 1.00 | 41.10 | B | C |

TABLE 4-2-continued

Coordinates of *P. alba* IspS

| ATOM | 10673 | CG1 | ILE | B | 153 | 79.823 | 46.346 | −33.276 | 1.00 | 43.65 | B | C |
|---|---|---|---|---|---|---|---|---|---|---|---|---|
| ATOM | 10676 | CD1 | ILE | B | 153 | 81.312 | 46.361 | −33.649 | 1.00 | 51.03 | B | C |
| ATOM | 10680 | CG2 | ILE | B | 153 | 78.717 | 44.468 | −32.025 | 1.00 | 37.99 | B | C |
| ATOM | 10684 | C | ILE | B | 153 | 78.407 | 46.112 | −29.702 | 1.00 | 39.38 | B | C |
| ATOM | 10685 | O | ILE | B | 153 | 77.333 | 45.532 | −29.578 | 1.00 | 39.13 | B | O |
| ATOM | 10687 | N | LYS | B | 154 | 79.306 | 46.185 | −28.732 | 1.00 | 38.79 | B | N |
| ATOM | 10688 | CA | LYS | B | 154 | 79.039 | 45.739 | −27.379 | 1.00 | 38.18 | B | C |
| ATOM | 10690 | CB | LYS | B | 154 | 80.232 | 46.100 | −26.488 | 1.00 | 40.20 | B | C |
| ATOM | 10693 | CG | LYS | B | 154 | 80.401 | 45.276 | −25.243 | 1.00 | 45.47 | B | C |
| ATOM | 10696 | CD | LYS | B | 154 | 81.444 | 45.920 | −24.337 | 1.00 | 55.39 | B | C |
| ATOM | 10699 | CE | LYS | B | 154 | 82.112 | 44.908 | −23.420 | 1.00 | 61.69 | B | C |
| ATOM | 10702 | NZ | LYS | B | 154 | 83.180 | 44.159 | −24.141 | 1.00 | 65.48 | B | N |
| ATOM | 10706 | C | LYS | B | 154 | 77.772 | 46.418 | −26.863 | 1.00 | 35.45 | B | C |
| ATOM | 10707 | O | LYS | B | 154 | 76.867 | 45.753 | −26.351 | 1.00 | 34.35 | B | O |
| ATOM | 10709 | N | ALA | B | 155 | 77.702 | 47.740 | −27.023 | 1.00 | 32.93 | B | N |
| ATOM | 10710 | CA | ALA | B | 155 | 76.556 | 48.512 | −26.536 | 1.00 | 30.98 | B | C |
| ATOM | 10712 | CB | ALA | B | 155 | 76.862 | 50.001 | −26.539 | 1.00 | 28.88 | B | C |
| ATOM | 10716 | C | ALA | B | 155 | 75.300 | 48.222 | −27.344 | 1.00 | 30.46 | B | C |
| ATOM | 10717 | O | ALA | B | 155 | 74.190 | 48.256 | −26.799 | 1.00 | 31.94 | B | O |
| ATOM | 10719 | N | ILE | B | 156 | 75.457 | 47.925 | −28.632 | 1.00 | 29.25 | B | N |
| ATOM | 10720 | CA | ILE | B | 156 | 74.293 | 47.587 | −29.471 | 1.00 | 29.09 | B | C |
| ATOM | 10722 | CB | ILE | B | 156 | 74.595 | 47.690 | −30.966 | 1.00 | 28.51 | B | C |
| ATOM | 10724 | CG1 | ILE | B | 156 | 75.094 | 49.091 | −31.310 | 1.00 | 31.99 | B | C |
| ATOM | 10727 | CD1 | ILE | B | 156 | 74.186 | 50.194 | −30.831 | 1.00 | 34.35 | B | C |
| ATOM | 10731 | CG2 | ILE | B | 156 | 73.331 | 47.424 | −31.791 | 1.00 | 32.40 | B | C |
| ATOM | 10735 | C | ILE | B | 156 | 73.710 | 46.207 | −29.149 | 1.00 | 27.53 | B | C |
| ATOM | 10736 | O | ILE | B | 156 | 72.504 | 46.040 | −29.207 | 1.00 | 26.96 | B | O |
| ATOM | 10738 | N | LEU | B | 157 | 74.557 | 45.234 | −28.806 | 1.00 | 26.87 | B | N |
| ATOM | 10739 | CA | LEU | B | 157 | 74.082 | 43.932 | −28.339 | 1.00 | 28.36 | B | C |
| ATOM | 10741 | CB | LEU | B | 157 | 75.228 | 42.972 | −28.089 | 1.00 | 29.14 | B | C |
| ATOM | 10744 | CG | LEU | B | 157 | 75.829 | 42.284 | −29.298 | 1.00 | 33.60 | B | C |
| ATOM | 10746 | CD1 | LEU | B | 157 | 77.039 | 41.499 | −28.814 | 1.00 | 34.46 | B | C |
| ATOM | 10750 | CD2 | LEU | B | 157 | 74.802 | 41.359 | −29.938 | 1.00 | 34.45 | B | C |
| ATOM | 10754 | C | LEU | B | 157 | 73.345 | 44.078 | −27.029 | 1.00 | 27.60 | B | C |
| ATOM | 10755 | O | LEU | B | 157 | 72.273 | 43.506 | −26.850 | 1.00 | 26.85 | B | O |
| ATOM | 10757 | N | SER | B | 158 | 73.944 | 44.835 | −26.114 | 1.00 | 27.41 | B | N |
| ATOM | 10758 | CA | SER | B | 158 | 73.348 | 45.048 | −24.804 | 1.00 | 28.54 | B | C |
| ATOM | 10760 | CB | SER | B | 158 | 74.277 | 45.838 | −23.896 | 1.00 | 27.73 | B | C |
| ATOM | 10763 | OG | SER | B | 158 | 75.455 | 45.098 | −23.664 | 1.00 | 38.76 | B | O |
| ATOM | 10765 | C | SER | B | 158 | 72.015 | 45.762 | −24.937 | 1.00 | 26.50 | B | C |
| ATOM | 10766 | O | SER | B | 158 | 71.080 | 45.412 | −24.253 | 1.00 | 24.81 | B | O |
| ATOM | 10768 | N | LEU | B | 159 | 71.927 | 46.739 | −25.835 | 1.00 | 25.52 | B | N |
| ATOM | 10769 | CA | LEU | B | 159 | 70.659 | 47.441 | −26.078 | 1.00 | 24.28 | B | C |
| ATOM | 10771 | CB | LEU | B | 159 | 70.858 | 48.603 | −27.043 | 1.00 | 24.65 | B | C |
| ATOM | 10774 | CG | LEU | B | 159 | 69.626 | 49.433 | −27.397 | 1.00 | 24.51 | B | C |
| ATOM | 10776 | CD1 | LEU | B | 159 | 68.956 | 49.970 | −26.131 | 1.00 | 18.59 | B | C |
| ATOM | 10780 | CD2 | LEU | B | 159 | 70.046 | 50.557 | −28.350 | 1.00 | 23.65 | B | C |
| ATOM | 10784 | C | LEU | B | 159 | 69.624 | 46.484 | −26.647 | 1.00 | 23.61 | B | C |
| ATOM | 10785 | O | LEU | B | 159 | 68.469 | 46.488 | −26.226 | 1.00 | 25.84 | B | O |
| ATOM | 10787 | N | TYR | B | 160 | 70.046 | 45.665 | −27.602 | 1.00 | 21.32 | B | N |
| ATOM | 10788 | CA | TYR | B | 160 | 69.176 | 44.661 | −28.182 | 1.00 | 19.66 | B | C |
| ATOM | 10790 | CB | TYR | B | 160 | 69.963 | 43.869 | −29.209 | 1.00 | 18.24 | B | C |
| ATOM | 10793 | CG | TYR | B | 160 | 69.268 | 42.660 | −29.777 | 1.00 | 17.21 | B | C |
| ATOM | 10794 | CD1 | TYR | B | 160 | 68.354 | 42.773 | −30.807 | 1.00 | 23.20 | B | C |
| ATOM | 10796 | CE1 | TYR | B | 160 | 67.735 | 41.642 | −31.345 | 1.00 | 27.22 | B | C |
| ATOM | 10798 | CZ | TYR | B | 160 | 68.049 | 40.398 | −30.847 | 1.00 | 27.43 | B | C |
| ATOM | 10799 | OH | TYR | B | 160 | 67.454 | 39.267 | −31.356 | 1.00 | 42.06 | B | O |
| ATOM | 10801 | CE2 | TYR | B | 160 | 68.952 | 40.273 | −29.823 | 1.00 | 29.75 | B | C |
| ATOM | 10803 | CD2 | TYR | B | 160 | 69.558 | 41.398 | −29.300 | 1.00 | 27.84 | B | C |
| ATOM | 10805 | C | TYR | B | 160 | 68.611 | 43.735 | −27.102 | 1.00 | 21.10 | B | C |
| ATOM | 10806 | O | TYR | B | 160 | 67.392 | 43.479 | −27.061 | 1.00 | 20.13 | B | O |
| ATOM | 10808 | N | GLU | B | 161 | 69.491 | 43.246 | −26.223 | 1.00 | 22.83 | B | N |
| ATOM | 10809 | CA | GLU | B | 161 | 69.086 | 42.289 | −25.195 | 1.00 | 22.44 | B | C |
| ATOM | 10811 | CB | GLU | B | 161 | 70.292 | 41.754 | −24.422 | 1.00 | 22.12 | B | C |
| ATOM | 10814 | CG | GLU | B | 161 | 71.263 | 40.919 | −25.261 | 1.00 | 25.71 | B | C |
| ATOM | 10817 | CD | GLU | B | 161 | 70.733 | 39.523 | −25.628 | 1.00 | 27.66 | B | C |
| ATOM | 10818 | OE1 | GLU | B | 161 | 69.565 | 39.178 | −25.328 | 1.00 | 34.19 | B | O |
| ATOM | 10819 | OE2 | GLU | B | 161 | 71.505 | 38.754 | −26.223 | 1.00 | 23.37 | B | O |
| ATOM | 10820 | C | GLU | B | 161 | 68.120 | 42.947 | −24.227 | 1.00 | 22.70 | B | C |
| ATOM | 10821 | O | GLU | B | 161 | 67.144 | 42.332 | −23.790 | 1.00 | 23.48 | B | O |
| ATOM | 10823 | N | ALA | B | 162 | 68.396 | 44.199 | −23.899 | 1.00 | 20.82 | B | N |
| ATOM | 10824 | CA | ALA | B | 162 | 67.568 | 44.936 | −22.974 | 1.00 | 21.15 | B | C |
| ATOM | 10826 | CB | ALA | B | 162 | 68.202 | 46.260 | −22.655 | 1.00 | 18.59 | B | C |
| ATOM | 10830 | C | ALA | B | 162 | 66.170 | 45.145 | −23.528 | 1.00 | 22.41 | B | C |
| ATOM | 10831 | O | ALA | B | 162 | 65.197 | 45.161 | −22.765 | 1.00 | 24.55 | B | O |
| ATOM | 10833 | N | SER | B | 163 | 66.063 | 45.300 | −24.845 | 1.00 | 21.15 | B | N |
| ATOM | 10834 | CA | SER | B | 163 | 64.781 | 45.630 | −25.451 | 1.00 | 22.45 | B | C |
| ATOM | 10836 | CB | SER | B | 163 | 64.925 | 45.885 | −26.971 | 1.00 | 22.21 | B | C |

TABLE 4-2-continued

| | | | | | | | | | | | | |
|---|---|---|---|---|---|---|---|---|---|---|---|---|
| \multicolumn{13}{c}{Coordinates of *P. alba* IspS} |
| ATOM | 10839 | OG | SER | B | 163 | 65.265 | 44.708 | −27.695 | 1.00 | 22.00 | B | O |
| ATOM | 10841 | C | SER | B | 163 | 63.725 | 44.554 | −25.191 | 1.00 | 22.67 | B | C |
| ATOM | 10842 | O | SER | B | 163 | 62.529 | 44.867 | −25.088 | 1.00 | 22.75 | B | O |
| ATOM | 10844 | N | PHE | B | 164 | 64.149 | 43.297 | −25.057 | 1.00 | 22.13 | B | N |
| ATOM | 10845 | CA | PHE | B | 164 | 63.175 | 42.225 | −24.898 | 1.00 | 22.96 | B | C |
| ATOM | 10847 | CB | PHE | B | 164 | 63.789 | 40.856 | −25.224 | 1.00 | 22.93 | B | C |
| ATOM | 10850 | CG | PHE | B | 164 | 64.027 | 40.683 | −26.692 | 1.00 | 22.93 | B | C |
| ATOM | 10851 | CD1 | PHE | B | 164 | 63.027 | 40.169 | −27.515 | 1.00 | 24.94 | B | C |
| ATOM | 10853 | CE1 | PHE | B | 164 | 63.205 | 40.072 | −28.886 | 1.00 | 20.58 | B | C |
| ATOM | 10855 | CZ | PHE | B | 164 | 64.377 | 40.516 | −29.455 | 1.00 | 20.41 | B | C |
| ATOM | 10857 | CE2 | PHE | B | 164 | 65.387 | 41.073 | −28.633 | 1.00 | 24.66 | B | C |
| ATOM | 10859 | CD2 | PHE | B | 164 | 65.186 | 41.171 | −27.271 | 1.00 | 19.04 | B | C |
| ATOM | 10861 | C | PHE | B | 164 | 62.492 | 42.257 | −23.547 | 1.00 | 22.65 | B | C |
| ATOM | 10862 | O | PHE | B | 164 | 61.512 | 41.539 | −23.338 | 1.00 | 23.15 | B | O |
| ATOM | 10864 | N | LEU | B | 165 | 62.952 | 43.122 | −22.642 | 1.00 | 22.52 | B | N |
| ATOM | 10865 | CA | LEU | B | 165 | 62.341 | 43.187 | −21.315 | 1.00 | 21.55 | B | C |
| ATOM | 10867 | CB | LEU | B | 165 | 63.392 | 43.432 | −20.237 | 1.00 | 23.26 | B | C |
| ATOM | 10870 | CG | LEU | B | 165 | 64.195 | 42.197 | −19.851 | 1.00 | 23.00 | B | C |
| ATOM | 10872 | CD1 | LEU | B | 165 | 65.339 | 41.953 | −20.829 | 1.00 | 20.20 | B | C |
| ATOM | 10876 | CD2 | LEU | B | 165 | 64.728 | 42.347 | −18.432 | 1.00 | 23.73 | B | C |
| ATOM | 10880 | C | LEU | B | 165 | 61.258 | 44.228 | −21.256 | 1.00 | 22.76 | B | C |
| ATOM | 10881 | O | LEU | B | 165 | 60.804 | 44.591 | −20.174 | 1.00 | 23.40 | B | O |
| ATOM | 10883 | N | ALA | B | 166 | 60.822 | 44.692 | −22.426 | 1.00 | 22.61 | B | N |
| ATOM | 10884 | CA | ALA | B | 166 | 59.900 | 45.804 | −22.517 | 1.00 | 23.27 | B | C |
| ATOM | 10886 | CB | ALA | B | 166 | 59.693 | 46.181 | −23.973 | 1.00 | 21.35 | B | C |
| ATOM | 10890 | C | ALA | B | 166 | 58.565 | 45.464 | −21.899 | 1.00 | 22.57 | B | C |
| ATOM | 10891 | O | ALA | B | 166 | 58.155 | 44.325 | −21.932 | 1.00 | 24.73 | B | O |
| ATOM | 10893 | N | LEU | B | 167 | 57.906 | 46.463 | −21.338 | 1.00 | 23.68 | B | N |
| ATOM | 10894 | CA | LEU | B | 167 | 56.489 | 46.397 | −21.010 | 1.00 | 25.21 | B | C |
| ATOM | 10896 | CB | LEU | B | 167 | 56.234 | 47.072 | −19.671 | 1.00 | 25.95 | B | C |
| ATOM | 10899 | CG | LEU | B | 167 | 57.098 | 46.586 | −18.506 | 1.00 | 29.63 | B | C |
| ATOM | 10901 | CD1 | LEU | B | 167 | 56.644 | 47.255 | −17.228 | 1.00 | 27.25 | B | C |
| ATOM | 10905 | CD2 | LEU | B | 167 | 57.012 | 45.081 | −18.375 | 1.00 | 25.26 | B | C |
| ATOM | 10909 | C | LEU | B | 167 | 55.663 | 47.096 | −22.097 | 1.00 | 26.22 | B | C |
| ATOM | 10910 | O | LEU | B | 167 | 56.203 | 47.772 | −22.981 | 1.00 | 28.50 | B | O |
| ATOM | 10912 | N | GLU | B | 168 | 54.352 | 46.917 | −22.039 | 1.00 | 26.78 | B | N |
| ATOM | 10913 | CA | GLU | B | 168 | 53.440 | 47.650 | −22.919 | 1.00 | 27.31 | B | C |
| ATOM | 10915 | CB | GLU | B | 168 | 52.004 | 47.290 | −22.578 | 1.00 | 28.21 | B | C |
| ATOM | 10918 | CG | GLU | B | 168 | 51.505 | 46.007 | −23.166 | 1.00 | 35.50 | B | C |
| ATOM | 10921 | CD | GLU | B | 168 | 49.971 | 45.971 | −23.198 | 1.00 | 43.15 | B | C |
| ATOM | 10922 | OE1 | GLU | B | 168 | 49.400 | 45.294 | −22.314 | 1.00 | 41.77 | B | O |
| ATOM | 10923 | OE2 | GLU | B | 168 | 49.352 | 46.633 | −24.084 | 1.00 | 44.65 | B | O |
| ATOM | 10924 | C | GLU | B | 168 | 53.584 | 49.172 | −22.760 | 1.00 | 25.57 | B | C |
| ATOM | 10925 | O | GLU | B | 168 | 53.595 | 49.675 | −21.638 | 1.00 | 25.79 | B | O |
| ATOM | 10927 | N | GLY | B | 169 | 53.657 | 49.887 | −23.880 | 1.00 | 25.49 | B | N |
| ATOM | 10928 | CA | GLY | B | 169 | 53.772 | 51.356 | −23.887 | 1.00 | 24.53 | B | C |
| ATOM | 10931 | C | GLY | B | 169 | 55.226 | 51.835 | −23.860 | 1.00 | 25.77 | B | C |
| ATOM | 10932 | O | GLY | B | 169 | 55.504 | 53.029 | −24.003 | 1.00 | 25.33 | B | O |
| ATOM | 10934 | N | GLU | B | 170 | 56.170 | 50.916 | −23.681 | 1.00 | 24.26 | B | N |
| ATOM | 10935 | CA | GLU | B | 170 | 57.563 | 51.316 | −23.691 | 1.00 | 24.47 | B | C |
| ATOM | 10937 | CB | GLU | B | 170 | 58.409 | 50.390 | −22.809 | 1.00 | 23.98 | B | C |
| ATOM | 10940 | CG | GLU | B | 170 | 58.085 | 50.601 | −21.322 | 1.00 | 27.09 | B | C |
| ATOM | 10943 | CD | GLU | B | 170 | 58.979 | 49.840 | −20.370 | 1.00 | 32.50 | B | C |
| ATOM | 10944 | OE1 | GLU | B | 170 | 59.047 | 50.248 | −19.187 | 1.00 | 33.97 | B | O |
| ATOM | 10945 | OE2 | GLU | B | 170 | 59.600 | 48.835 | −20.791 | 1.00 | 33.76 | B | O |
| ATOM | 10946 | C | GLU | B | 170 | 58.057 | 51.391 | −25.122 | 1.00 | 25.33 | B | C |
| ATOM | 10947 | O | GLU | B | 170 | 58.854 | 50.580 | −25.562 | 1.00 | 25.77 | B | O |
| ATOM | 10949 | N | ASN | B | 171 | 57.583 | 52.405 | −25.838 | 1.00 | 25.86 | B | N |
| ATOM | 10950 | CA | ASN | B | 171 | 57.942 | 52.584 | −27.238 | 1.00 | 26.42 | B | C |
| ATOM | 10952 | CB | ASN | B | 171 | 57.206 | 53.793 | −27.826 | 1.00 | 26.53 | B | C |
| ATOM | 10955 | CG | ASN | B | 171 | 57.401 | 55.060 | −26.997 | 1.00 | 32.07 | B | C |
| ATOM | 10956 | OD1 | ASN | B | 171 | 56.890 | 55.173 | −25.877 | 1.00 | 29.89 | B | O |
| ATOM | 10957 | ND2 | ASN | B | 171 | 58.153 | 56.012 | −27.539 | 1.00 | 28.86 | B | N |
| ATOM | 10960 | C | ASN | B | 171 | 59.449 | 52.727 | −27.472 | 1.00 | 27.85 | B | C |
| ATOM | 10961 | O | ASN | B | 171 | 59.962 | 52.316 | −28.511 | 1.00 | 29.62 | B | O |
| ATOM | 10963 | N | ILE | B | 172 | 60.163 | 53.299 | −26.512 | 1.00 | 28.75 | B | N |
| ATOM | 10964 | CA | ILE | B | 172 | 61.596 | 53.523 | −26.679 | 1.00 | 29.05 | B | C |
| ATOM | 10966 | CB | ILE | B | 172 | 62.175 | 54.382 | −25.549 | 1.00 | 29.12 | B | C |
| ATOM | 10968 | CG1 | ILE | B | 172 | 61.608 | 55.804 | −25.644 | 1.00 | 31.03 | B | C |
| ATOM | 10971 | CD1 | ILE | B | 172 | 61.983 | 56.695 | −24.488 | 1.00 | 32.54 | B | C |
| ATOM | 10975 | CG2 | ILE | B | 172 | 63.686 | 54.472 | −25.651 | 1.00 | 28.63 | B | C |
| ATOM | 10979 | C | ILE | B | 172 | 62.337 | 52.200 | −26.804 | 1.00 | 30.66 | B | C |
| ATOM | 10980 | O | ILE | B | 172 | 63.244 | 52.075 | −27.629 | 1.00 | 32.83 | B | O |
| ATOM | 10982 | N | LEU | B | 173 | 61.922 | 51.200 | −26.029 | 1.00 | 30.45 | B | N |
| ATOM | 10983 | CA | LEU | B | 173 | 62.542 | 49.875 | −26.103 | 1.00 | 28.89 | B | C |
| ATOM | 10985 | CB | LEU | B | 173 | 62.098 | 49.006 | −24.923 | 1.00 | 28.96 | B | C |
| ATOM | 10988 | CG | LEU | B | 173 | 62.869 | 49.210 | −23.615 | 1.00 | 28.06 | B | C |
| ATOM | 10990 | CD1 | LEU | B | 173 | 63.107 | 50.664 | −23.324 | 1.00 | 28.03 | B | C |

TABLE 4-2-continued

Coordinates of *P. alba* IspS

| ATOM | 10994 | CD2 | LEU | B | 173 | 62.101 | 48.562 | −22.474 | 1.00 | 28.74 | B | C |
|---|---|---|---|---|---|---|---|---|---|---|---|---|
| ATOM | 10998 | C | LEU | B | 173 | 62.221 | 49.191 | −27.433 | 1.00 | 28.15 | B | C |
| ATOM | 10999 | O | LEU | B | 173 | 63.094 | 48.582 | −28.049 | 1.00 | 29.10 | B | O |
| ATOM | 11001 | N | ASP | B | 174 | 60.976 | 49.298 | −27.878 | 1.00 | 27.45 | B | N |
| ATOM | 11002 | CA | ASP | B | 174 | 60.586 | 48.825 | −29.222 | 1.00 | 28.78 | B | C |
| ATOM | 11004 | CB | ASP | B | 174 | 59.117 | 49.152 | −29.509 | 1.00 | 29.66 | B | C |
| ATOM | 11007 | CG | ASP | B | 174 | 58.140 | 48.181 | −28.843 | 1.00 | 36.16 | B | C |
| ATOM | 11008 | OD1 | ASP | B | 174 | 58.535 | 47.387 | −27.960 | 1.00 | 45.20 | B | O |
| ATOM | 11009 | OD2 | ASP | B | 174 | 56.954 | 48.219 | −29.219 | 1.00 | 44.48 | B | O |
| ATOM | 11010 | C | ASP | B | 174 | 61.439 | 49.465 | −30.314 | 1.00 | 28.84 | B | C |
| ATOM | 11011 | O | ASP | B | 174 | 61.879 | 48.805 | −31.254 | 1.00 | 30.79 | B | O |
| ATOM | 11013 | N | GLU | B | 175 | 61.660 | 50.760 | −30.193 | 1.00 | 29.80 | B | N |
| ATOM | 11014 | CA | GLU | B | 175 | 62.492 | 51.469 | −31.151 | 1.00 | 30.39 | B | C |
| ATOM | 11016 | CB | GLU | B | 175 | 62.349 | 52.977 | −30.949 | 1.00 | 30.54 | B | C |
| ATOM | 11019 | CG | GLU | B | 175 | 60.948 | 53.528 | −31.292 | 1.00 | 35.87 | B | C |
| ATOM | 11022 | CD | GLU | B | 175 | 60.612 | 54.872 | −30.601 | 1.00 | 42.68 | B | C |
| ATOM | 11023 | OE1 | GLU | B | 175 | 61.530 | 55.551 | −30.070 | 1.00 | 40.27 | B | O |
| ATOM | 11024 | OE2 | GLU | B | 175 | 59.413 | 55.246 | −30.602 | 1.00 | 43.14 | B | O |
| ATOM | 11025 | C | GLU | B | 175 | 63.944 | 51.005 | −30.982 | 1.00 | 30.18 | B | C |
| ATOM | 11026 | O | GLU | B | 175 | 64.660 | 50.798 | −31.969 | 1.00 | 30.45 | B | O |
| ATOM | 11028 | N | ALA | B | 176 | 64.359 | 50.807 | −29.732 | 1.00 | 28.90 | B | N |
| ATOM | 11029 | CA | ALA | B | 176 | 65.695 | 50.272 | −29.433 | 1.00 | 27.90 | B | C |
| ATOM | 11031 | CB | ALA | B | 176 | 65.829 | 49.984 | −27.974 | 1.00 | 26.60 | B | C |
| ATOM | 11035 | C | ALA | B | 176 | 65.973 | 49.011 | −30.228 | 1.00 | 27.63 | B | C |
| ATOM | 11036 | O | ALA | B | 176 | 67.037 | 48.867 | −30.823 | 1.00 | 27.16 | B | O |
| ATOM | 11038 | N | LYS | B | 177 | 64.992 | 48.118 | −30.253 | 1.00 | 27.87 | B | N |
| ATOM | 11039 | CA | LYS | B | 177 | 65.143 | 46.821 | −30.902 | 1.00 | 27.75 | B | C |
| ATOM | 11041 | CB | LYS | B | 177 | 63.983 | 45.879 | −30.524 | 1.00 | 25.44 | B | C |
| ATOM | 11044 | CG | LYS | B | 177 | 63.931 | 44.587 | −31.332 | 1.00 | 27.36 | B | C |
| ATOM | 11047 | CD | LYS | B | 177 | 63.211 | 43.426 | −30.638 | 1.00 | 31.71 | B | C |
| ATOM | 11050 | CE | LYS | B | 177 | 61.774 | 43.731 | −30.205 | 1.00 | 32.14 | B | C |
| ATOM | 11053 | NZ | LYS | B | 177 | 61.287 | 42.780 | −29.169 | 1.00 | 25.79 | B | N |
| ATOM | 11057 | C | LYS | B | 177 | 65.251 | 46.964 | −32.419 | 1.00 | 29.31 | B | C |
| ATOM | 11058 | O | LYS | B | 177 | 66.057 | 46.272 | −33.042 | 1.00 | 30.76 | B | O |
| ATOM | 11060 | N | VAL | B | 178 | 64.420 | 47.828 | −33.006 | 1.00 | 30.40 | B | N |
| ATOM | 11061 | CA | VAL | B | 178 | 64.425 | 48.056 | −34.460 | 1.00 | 29.52 | B | C |
| ATOM | 11063 | CB | VAL | B | 178 | 63.367 | 49.122 | −34.909 | 1.00 | 29.52 | B | C |
| ATOM | 11065 | CG1 | VAL | B | 178 | 63.644 | 49.609 | −36.351 | 1.00 | 27.87 | B | C |
| ATOM | 11069 | CG2 | VAL | B | 178 | 61.941 | 48.598 | −34.790 | 1.00 | 27.79 | B | C |
| ATOM | 11073 | C | VAL | B | 178 | 65.797 | 48.585 | −34.819 | 1.00 | 30.34 | B | C |
| ATOM | 11074 | O | VAL | B | 178 | 66.452 | 48.101 | −35.752 | 1.00 | 31.89 | B | O |
| ATOM | 11076 | N | PHE | B | 179 | 66.229 | 49.575 | −34.047 | 1.00 | 30.22 | B | N |
| ATOM | 11077 | CA | PHE | B | 179 | 67.516 | 50.223 | −34.258 | 1.00 | 29.99 | B | C |
| ATOM | 11079 | CB | PHE | B | 179 | 67.688 | 51.372 | −33.260 | 1.00 | 29.89 | B | C |
| ATOM | 11082 | CG | PHE | B | 179 | 69.056 | 51.967 | −33.262 | 1.00 | 29.85 | B | C |
| ATOM | 11083 | CD1 | PHE | B | 179 | 69.476 | 52.745 | −34.322 | 1.00 | 30.02 | B | C |
| ATOM | 11085 | CE1 | PHE | B | 179 | 70.743 | 53.287 | −34.335 | 1.00 | 30.08 | B | C |
| ATOM | 11087 | CZ | PHE | B | 179 | 71.607 | 53.063 | −33.276 | 1.00 | 31.16 | B | C |
| ATOM | 11089 | CE2 | PHE | B | 179 | 71.207 | 52.288 | −32.215 | 1.00 | 32.64 | B | C |
| ATOM | 11091 | CD2 | PHE | B | 179 | 69.929 | 51.735 | −32.213 | 1.00 | 31.27 | B | C |
| ATOM | 11093 | C | PHE | B | 179 | 68.694 | 49.251 | −34.147 | 1.00 | 30.91 | B | C |
| ATOM | 11094 | O | PHE | B | 179 | 69.531 | 49.183 | −35.054 | 1.00 | 33.53 | B | O |
| ATOM | 11096 | N | ALA | B | 180 | 68.763 | 48.502 | −33.049 | 1.00 | 29.27 | B | N |
| ATOM | 11097 | CA | ALA | B | 180 | 69.898 | 47.602 | −32.831 | 1.00 | 28.27 | B | C |
| ATOM | 11099 | CB | ALA | B | 180 | 69.951 | 47.121 | −31.393 | 1.00 | 26.03 | B | C |
| ATOM | 11103 | C | ALA | B | 180 | 69.886 | 46.429 | −33.794 | 1.00 | 28.76 | B | C |
| ATOM | 11104 | O | ALA | B | 180 | 70.928 | 46.013 | −34.264 | 1.00 | 30.14 | B | O |
| ATOM | 11106 | N | ILE | B | 181 | 68.713 | 45.903 | −34.105 | 1.00 | 30.72 | B | N |
| ATOM | 11107 | CA | ILE | B | 181 | 68.621 | 44.841 | −35.108 | 1.00 | 32.83 | B | C |
| ATOM | 11109 | CB | ILE | B | 181 | 67.160 | 44.382 | −35.331 | 1.00 | 32.27 | B | C |
| ATOM | 11111 | CG1 | ILE | B | 181 | 66.724 | 43.407 | −34.235 | 1.00 | 37.17 | B | C |
| ATOM | 11114 | CD1 | ILE | B | 181 | 65.238 | 42.897 | −34.385 | 1.00 | 36.59 | B | C |
| ATOM | 11118 | CG2 | ILE | B | 181 | 66.995 | 43.703 | −36.694 | 1.00 | 34.78 | B | C |
| ATOM | 11122 | C | ILE | B | 181 | 69.217 | 45.289 | −36.452 | 1.00 | 34.90 | B | C |
| ATOM | 11123 | O | ILE | B | 181 | 69.973 | 44.539 | −37.078 | 1.00 | 35.81 | B | O |
| ATOM | 11125 | N | SER | B | 182 | 68.885 | 46.501 | −36.893 | 1.00 | 36.36 | B | N |
| ATOM | 11126 | CA | SER | B | 182 | 69.314 | 46.952 | −38.229 | 1.00 | 38.78 | B | C |
| ATOM | 11128 | CB | SER | B | 182 | 68.701 | 48.315 | −38.607 | 1.00 | 38.10 | B | C |
| ATOM | 11131 | OG | SER | B | 182 | 69.333 | 49.382 | −37.919 | 1.00 | 41.06 | B | O |
| ATOM | 11133 | C | SER | B | 182 | 70.840 | 46.992 | −38.350 | 1.00 | 39.40 | B | C |
| ATOM | 11134 | O | SER | B | 182 | 71.385 | 46.696 | −39.407 | 1.00 | 40.69 | B | O |
| ATOM | 11136 | N | HIS | B | 183 | 71.532 | 47.334 | −37.269 | 1.00 | 40.96 | B | N |
| ATOM | 11137 | CA | HIS | B | 183 | 72.998 | 47.410 | −37.315 | 1.00 | 41.22 | B | C |
| ATOM | 11139 | CB | HIS | B | 183 | 73.503 | 48.563 | −36.448 | 1.00 | 40.88 | B | C |
| ATOM | 11142 | CG | HIS | B | 183 | 73.160 | 49.899 | −37.014 | 1.00 | 46.75 | B | C |
| ATOM | 11143 | ND1 | HIS | B | 183 | 72.264 | 50.757 | −36.415 | 1.00 | 50.90 | B | N |
| ATOM | 11145 | CE1 | HIS | B | 183 | 72.134 | 51.840 | −37.161 | 1.00 | 54.30 | B | C |
| ATOM | 11147 | NE2 | HIS | B | 183 | 72.896 | 51.704 | −38.231 | 1.00 | 53.96 | B | N |

TABLE 4-2-continued

Coordinates of *P. alba* IspS

| ATOM | 11149 | CD2 | HIS | B | 183 | 73.543 | 50.495 | −38.167 | 1.00 | 48.27 | B | C |
|---|---|---|---|---|---|---|---|---|---|---|---|---|
| ATOM | 11151 | C | HIS | B | 183 | 73.703 | 46.112 | −36.955 | 1.00 | 40.72 | B | C |
| ATOM | 11152 | O | HIS | B | 183 | 74.900 | 46.003 | −37.173 | 1.00 | 42.77 | B | O |
| ATOM | 11154 | N | LEU | B | 184 | 72.973 | 45.128 | −36.432 | 1.00 | 39.36 | B | N |
| ATOM | 11155 | CA | LEU | B | 184 | 73.590 | 43.855 | −36.043 | 1.00 | 38.20 | B | C |
| ATOM | 11157 | CB | LEU | B | 184 | 72.887 | 43.260 | −34.811 | 1.00 | 36.21 | B | C |
| ATOM | 11160 | CG | LEU | B | 184 | 73.193 | 43.912 | −33.457 | 1.00 | 33.67 | B | C |
| ATOM | 11162 | CD1 | LEU | B | 184 | 72.210 | 43.448 | −32.429 | 1.00 | 23.99 | B | C |
| ATOM | 11166 | CD2 | LEU | B | 184 | 74.618 | 43.608 | −33.002 | 1.00 | 27.65 | B | C |
| ATOM | 11170 | C | LEU | B | 184 | 73.628 | 42.823 | −37.179 | 1.00 | 40.01 | B | C |
| ATOM | 11171 | O | LEU | B | 184 | 74.596 | 42.065 | −37.301 | 1.00 | 37.78 | B | O |
| ATOM | 11173 | N | LYS | B | 185 | 72.590 | 42.763 | −38.006 | 1.00 | 43.51 | B | N |
| ATOM | 11174 | CA | LYS | B | 185 | 72.541 | 41.685 | −39.001 | 1.00 | 48.61 | B | C |
| ATOM | 11176 | CB | LYS | B | 185 | 71.099 | 41.321 | −39.391 | 1.00 | 49.10 | B | C |
| ATOM | 11179 | CG | LYS | B | 185 | 70.449 | 42.148 | −40.488 | 1.00 | 55.39 | B | C |
| ATOM | 11182 | CD | LYS | B | 185 | 68.962 | 41.760 | −40.670 | 1.00 | 62.71 | B | C |
| ATOM | 11185 | CE | LYS | B | 185 | 68.785 | 40.320 | −41.201 | 1.00 | 66.06 | B | C |
| ATOM | 11188 | NZ | LYS | B | 185 | 67.354 | 39.952 | −41.448 | 1.00 | 65.27 | B | N |
| ATOM | 11192 | C | LYS | B | 185 | 73.431 | 41.961 | −40.218 | 1.00 | 50.99 | B | C |
| ATOM | 11193 | O | LYS | B | 185 | 73.784 | 41.040 | −40.944 | 1.00 | 51.11 | B | O |
| ATOM | 11195 | N | GLU | B | 186 | 73.828 | 43.213 | −40.403 | 1.00 | 54.84 | B | N |
| ATOM | 11196 | CA | GLU | B | 186 | 74.706 | 43.569 | −41.513 | 1.00 | 59.61 | B | C |
| ATOM | 11198 | CB | GLU | B | 186 | 74.519 | 45.052 | −41.895 | 1.00 | 60.90 | B | C |
| ATOM | 11201 | CG | GLU | B | 186 | 73.110 | 45.425 | −42.369 | 1.00 | 64.87 | B | C |
| ATOM | 11204 | CD | GLU | B | 186 | 72.750 | 44.835 | −43.733 | 1.00 | 70.39 | B | C |
| ATOM | 11205 | OE1 | GLU | B | 186 | 73.310 | 45.292 | −44.758 | 1.00 | 71.34 | B | O |
| ATOM | 11206 | OE2 | GLU | B | 186 | 71.889 | 43.925 | −43.777 | 1.00 | 69.40 | B | O |
| ATOM | 11207 | C | GLU | B | 186 | 76.197 | 43.293 | −41.233 | 1.00 | 60.98 | B | C |
| ATOM | 11208 | O | GLU | B | 186 | 77.017 | 43.423 | −42.139 | 1.00 | 61.95 | B | O |
| ATOM | 11210 | N | LEU | B | 187 | 76.549 | 42.907 | −40.004 | 1.00 | 62.28 | B | N |
| ATOM | 11211 | CA | LEU | B | 187 | 77.964 | 42.855 | −39.581 | 1.00 | 62.62 | B | C |
| ATOM | 11213 | CB | LEU | B | 187 | 78.078 | 42.851 | −38.054 | 1.00 | 61.51 | B | C |
| ATOM | 11216 | CG | LEU | B | 187 | 77.507 | 44.076 | −37.343 | 1.00 | 60.53 | B | C |
| ATOM | 11218 | CD1 | LEU | B | 187 | 77.696 | 43.951 | −35.843 | 1.00 | 56.66 | B | C |
| ATOM | 11222 | CD2 | LEU | B | 187 | 78.131 | 45.375 | −37.861 | 1.00 | 60.27 | B | C |
| ATOM | 11226 | C | LEU | B | 187 | 78.736 | 41.662 | −40.143 | 1.00 | 64.20 | B | C |
| ATOM | 11227 | O | LEU | B | 187 | 78.216 | 40.546 | −40.198 | 1.00 | 64.08 | B | O |
| ATOM | 11229 | N | SER | B | 188 | 79.987 | 41.914 | −40.533 | 1.00 | 65.99 | B | N |
| ATOM | 11230 | CA | SER | B | 188 | 80.843 | 40.903 | −41.168 | 1.00 | 67.23 | B | C |
| ATOM | 11232 | CB | SER | B | 188 | 81.579 | 41.514 | −42.370 | 1.00 | 67.61 | B | C |
| ATOM | 11235 | OG | SER | B | 188 | 82.193 | 40.517 | −43.168 | 1.00 | 68.97 | B | O |
| ATOM | 11237 | C | SER | B | 188 | 81.862 | 40.357 | −40.172 | 1.00 | 67.24 | B | C |
| ATOM | 11238 | O | SER | B | 188 | 82.548 | 41.136 | −39.507 | 1.00 | 66.19 | B | O |
| ATOM | 11240 | N | GLU | B | 189 | 81.970 | 39.026 | −40.093 | 1.00 | 68.52 | B | N |
| ATOM | 11241 | CA | GLU | B | 189 | 82.944 | 38.357 | −39.206 | 1.00 | 70.09 | B | C |
| ATOM | 11243 | CB | GLU | B | 189 | 82.912 | 36.818 | −39.372 | 1.00 | 70.61 | B | C |
| ATOM | 11246 | CG | GLU | B | 189 | 84.084 | 36.079 | −38.655 | 1.00 | 74.42 | B | C |
| ATOM | 11249 | CD | GLU | B | 189 | 83.884 | 34.571 | −38.451 | 1.00 | 78.48 | B | C |
| ATOM | 11250 | OE1 | GLU | B | 189 | 82.846 | 34.014 | −38.868 | 1.00 | 78.02 | B | O |
| ATOM | 11251 | OE2 | GLU | B | 189 | 84.790 | 33.939 | −37.857 | 1.00 | 81.03 | B | O |
| ATOM | 11252 | C | GLU | B | 189 | 84.366 | 38.869 | −39.429 | 1.00 | 70.71 | B | C |
| ATOM | 11253 | O | GLU | B | 189 | 85.214 | 38.768 | −38.538 | 1.00 | 69.61 | B | O |
| ATOM | 11255 | N | GLU | B | 190 | 84.619 | 39.412 | −40.617 | 1.00 | 71.86 | B | N |
| ATOM | 11256 | CA | GLU | B | 190 | 85.936 | 39.921 | −40.967 | 1.00 | 73.09 | B | C |
| ATOM | 11258 | CB | GLU | B | 190 | 86.081 | 39.953 | −42.492 | 1.00 | 74.22 | B | C |
| ATOM | 11261 | CG | GLU | B | 190 | 85.947 | 38.559 | −43.117 | 1.00 | 77.50 | B | C |
| ATOM | 11264 | CD | GLU | B | 190 | 85.806 | 38.582 | −44.623 | 1.00 | 80.99 | B | C |
| ATOM | 11265 | OE1 | GLU | B | 190 | 86.833 | 38.752 | −45.309 | 1.00 | 81.25 | B | O |
| ATOM | 11266 | OE2 | GLU | B | 190 | 84.674 | 38.400 | −45.121 | 1.00 | 84.29 | B | O |
| ATOM | 11267 | C | GLU | B | 190 | 86.227 | 41.289 | −40.324 | 1.00 | 72.73 | B | C |
| ATOM | 11268 | O | GLU | B | 190 | 87.328 | 41.505 | −39.808 | 1.00 | 72.35 | B | O |
| ATOM | 11270 | N | LYS | B | 191 | 85.246 | 42.195 | −40.334 | 1.00 | 72.21 | B | N |
| ATOM | 11271 | CA | LYS | B | 191 | 85.414 | 43.512 | −39.697 | 1.00 | 72.24 | B | C |
| ATOM | 11273 | CB | LYS | B | 191 | 84.208 | 44.417 | −39.967 | 1.00 | 73.12 | B | C |
| ATOM | 11276 | CG | LYS | B | 191 | 84.121 | 44.922 | −41.378 | 1.00 | 78.07 | B | C |
| ATOM | 11279 | CD | LYS | B | 191 | 82.949 | 45.868 | −41.546 | 1.00 | 83.68 | B | C |
| ATOM | 11282 | CE | LYS | B | 191 | 82.589 | 46.014 | −43.012 | 1.00 | 85.64 | B | C |
| ATOM | 11285 | NZ | LYS | B | 191 | 81.322 | 46.764 | −43.228 | 1.00 | 85.74 | B | N |
| ATOM | 11289 | C | LYS | B | 191 | 85.587 | 43.362 | −38.192 | 1.00 | 70.52 | B | C |
| ATOM | 11290 | O | LYS | B | 191 | 86.656 | 43.635 | −37.640 | 1.00 | 69.35 | B | O |
| ATOM | 11292 | N | ILE | B | 192 | 84.515 | 42.917 | −37.546 | 1.00 | 68.76 | B | N |
| ATOM | 11293 | CA | ILE | B | 192 | 84.498 | 42.712 | −36.102 | 1.00 | 67.68 | B | C |
| ATOM | 11295 | CB | ILE | B | 192 | 83.059 | 42.833 | −35.544 | 1.00 | 67.45 | B | C |
| ATOM | 11297 | CG1 | ILE | B | 192 | 82.129 | 41.758 | −36.137 | 1.00 | 66.91 | B | C |
| ATOM | 11300 | CD1 | ILE | B | 192 | 80.731 | 41.750 | −35.544 | 1.00 | 62.95 | B | C |
| ATOM | 11304 | CG2 | ILE | B | 192 | 82.495 | 44.217 | −35.848 | 1.00 | 67.23 | B | C |
| ATOM | 11308 | C | ILE | B | 192 | 85.101 | 41.346 | −35.781 | 1.00 | 66.59 | B | C |
| ATOM | 11309 | O | ILE | B | 192 | 85.310 | 40.533 | −36.678 | 1.00 | 65.89 | B | O |

TABLE 4-2-continued

| | | | | | | | | | | | |
|---|---|---|---|---|---|---|---|---|---|---|---|
| \multicolumn{12}{c}{Coordinates of *P. alba* IspS} |
| ATOM | 11311 | N | GLY | B | 193 | 85.381 | 41.092 | −34.508 | 1.00 | 65.99 | B | N |
| ATOM | 11312 | CA | GLY | B | 193 | 85.987 | 39.820 | −34.095 | 1.00 | 66.09 | B | C |
| ATOM | 11315 | C | GLY | B | 193 | 85.240 | 38.558 | −34.522 | 1.00 | 65.01 | B | C |
| ATOM | 11316 | O | GLY | B | 193 | 84.047 | 38.599 | −34.838 | 1.00 | 65.07 | B | O |
| ATOM | 11318 | N | LYS | B | 194 | 85.950 | 37.431 | −34.522 | 1.00 | 63.20 | B | N |
| ATOM | 11319 | CA | LYS | B | 194 | 85.349 | 36.125 | −34.810 | 1.00 | 61.59 | B | C |
| ATOM | 11321 | CB | LYS | B | 194 | 86.420 | 35.045 | −35.024 | 1.00 | 62.81 | B | C |
| ATOM | 11324 | CG | LYS | B | 194 | 87.707 | 35.553 | −35.719 | 1.00 | 69.11 | B | C |
| ATOM | 11327 | CD | LYS | B | 194 | 88.577 | 34.426 | −36.265 | 1.00 | 73.14 | B | C |
| ATOM | 11330 | CE | LYS | B | 194 | 89.964 | 34.937 | −36.630 | 1.00 | 73.97 | B | C |
| ATOM | 11333 | NZ | LYS | B | 194 | 90.701 | 33.974 | −37.486 | 1.00 | 72.97 | B | N |
| ATOM | 11337 | C | LYS | B | 194 | 84.449 | 35.739 | −33.642 | 1.00 | 58.97 | B | C |
| ATOM | 11338 | O | LYS | B | 194 | 83.352 | 35.227 | −33.848 | 1.00 | 58.12 | B | O |
| ATOM | 11340 | N | GLU | B | 195 | 84.916 | 36.004 | −32.419 | 1.00 | 56.35 | B | N |
| ATOM | 11341 | CA | GLU | B | 195 | 84.129 | 35.732 | −31.211 | 1.00 | 54.87 | B | C |
| ATOM | 11343 | CB | GLU | B | 195 | 84.997 | 35.779 | −29.942 | 1.00 | 55.37 | B | C |
| ATOM | 11346 | CG | GLU | B | 195 | 85.305 | 37.173 | −29.405 | 1.00 | 59.74 | B | C |
| ATOM | 11349 | CD | GLU | B | 195 | 86.263 | 37.147 | −28.214 | 1.00 | 65.81 | B | C |
| ATOM | 11350 | OE1 | GLU | B | 195 | 85.953 | 37.804 | −27.195 | 1.00 | 68.11 | B | O |
| ATOM | 11351 | OE2 | GLU | B | 195 | 87.321 | 36.478 | −28.292 | 1.00 | 62.87 | B | O |
| ATOM | 11352 | C | GLU | B | 195 | 82.938 | 36.687 | −31.088 | 1.00 | 52.05 | B | C |
| ATOM | 11353 | O | GLU | B | 195 | 81.881 | 36.302 | −30.569 | 1.00 | 51.42 | B | O |
| ATOM | 11355 | N | LEU | B | 196 | 83.104 | 37.917 | −31.575 | 1.00 | 48.06 | B | N |
| ATOM | 11356 | CA | LEU | B | 196 | 82.024 | 38.902 | −31.518 | 1.00 | 44.72 | B | C |
| ATOM | 11358 | CB | LEU | B | 196 | 82.556 | 40.327 | −31.685 | 1.00 | 44.61 | B | C |
| ATOM | 11361 | CG | LEU | B | 196 | 81.759 | 41.396 | −30.928 | 1.00 | 44.98 | B | C |
| ATOM | 11363 | CD1 | LEU | B | 196 | 81.934 | 41.257 | −29.418 | 1.00 | 47.04 | B | C |
| ATOM | 11367 | CD2 | LEU | B | 196 | 82.168 | 42.798 | −31.387 | 1.00 | 45.98 | B | C |
| ATOM | 11371 | C | LEU | B | 196 | 80.918 | 38.607 | −32.538 | 1.00 | 41.82 | B | C |
| ATOM | 11372 | O | LEU | B | 196 | 79.750 | 38.849 | −32.256 | 1.00 | 40.86 | B | O |
| ATOM | 11374 | N | ALA | B | 197 | 81.273 | 38.069 | −33.705 | 1.00 | 39.07 | B | N |
| ATOM | 11375 | CA | ALA | B | 197 | 80.260 | 37.639 | −34.679 | 1.00 | 37.43 | B | C |
| ATOM | 11377 | CB | ALA | B | 197 | 80.898 | 37.300 | −36.021 | 1.00 | 36.56 | B | C |
| ATOM | 11381 | C | ALA | B | 197 | 79.487 | 36.437 | −34.146 | 1.00 | 36.90 | B | C |
| ATOM | 11382 | O | ALA | B | 197 | 78.300 | 36.286 | −34.411 | 1.00 | 39.21 | B | O |
| ATOM | 11384 | N | GLU | B | 198 | 80.166 | 35.574 | −33.404 | 1.00 | 36.09 | B | N |
| ATOM | 11385 | CA | GLU | B | 198 | 79.496 | 34.465 | −32.744 | 1.00 | 36.69 | B | C |
| ATOM | 11387 | CB | GLU | B | 198 | 80.519 | 33.469 | −32.174 | 1.00 | 38.24 | B | C |
| ATOM | 11390 | CG | GLU | B | 198 | 81.044 | 32.504 | −33.263 | 1.00 | 49.87 | B | C |
| ATOM | 11393 | CD | GLU | B | 198 | 82.379 | 31.814 | −32.933 | 1.00 | 59.13 | B | C |
| ATOM | 11394 | OE1 | GLU | B | 198 | 82.981 | 32.093 | −31.870 | 1.00 | 66.73 | B | O |
| ATOM | 11395 | OE2 | GLU | B | 198 | 82.824 | 30.983 | −33.760 | 1.00 | 62.01 | B | O |
| ATOM | 11396 | C | GLU | B | 198 | 78.522 | 34.985 | −31.677 | 1.00 | 32.99 | B | C |
| ATOM | 11397 | O | GLU | B | 198 | 77.413 | 34.491 | −31.592 | 1.00 | 34.75 | B | O |
| ATOM | 11399 | N | GLN | B | 199 | 78.913 | 36.001 | −30.908 | 1.00 | 29.51 | B | N |
| ATOM | 11400 | CA | GLN | B | 199 | 77.997 | 36.612 | −29.945 | 1.00 | 29.35 | B | C |
| ATOM | 11402 | CB | GLN | B | 199 | 78.656 | 37.722 | −29.115 | 1.00 | 30.73 | B | C |
| ATOM | 11405 | CG | GLN | B | 199 | 79.775 | 37.269 | −28.142 | 1.00 | 39.02 | B | C |
| ATOM | 11408 | CD | GLN | B | 199 | 79.280 | 36.756 | −26.781 | 1.00 | 51.63 | B | C |
| ATOM | 11409 | OE1 | GLN | B | 199 | 78.074 | 36.694 | −26.513 | 1.00 | 54.70 | B | O |
| ATOM | 11410 | NE2 | GLN | B | 199 | 80.229 | 36.385 | −25.912 | 1.00 | 48.54 | B | N |
| ATOM | 11413 | C | GLN | B | 199 | 76.783 | 37.171 | −30.668 | 1.00 | 28.02 | B | C |
| ATOM | 11414 | O | GLN | B | 199 | 75.660 | 36.876 | −30.286 | 1.00 | 26.21 | B | O |
| ATOM | 11416 | N | VAL | B | 200 | 77.008 | 37.933 | −31.739 | 1.00 | 27.32 | B | N |
| ATOM | 11417 | CA | VAL | B | 200 | 75.911 | 38.572 | −32.485 | 1.00 | 27.54 | B | C |
| ATOM | 11419 | CB | VAL | B | 200 | 76.453 | 39.523 | −33.589 | 1.00 | 28.36 | B | C |
| ATOM | 11421 | CG1 | VAL | B | 200 | 77.351 | 40.596 | −32.963 | 1.00 | 29.95 | B | C |
| ATOM | 11425 | CG2 | VAL | B | 200 | 75.324 | 40.190 | −34.359 | 1.00 | 26.02 | B | C |
| ATOM | 11429 | C | VAL | B | 200 | 74.949 | 37.540 | −33.088 | 1.00 | 27.67 | B | C |
| ATOM | 11430 | O | VAL | B | 200 | 73.738 | 37.684 | −32.976 | 1.00 | 26.60 | B | O |
| ATOM | 11432 | N | ASN | B | 201 | 75.484 | 36.489 | −33.705 | 1.00 | 28.51 | B | N |
| ATOM | 11433 | CA | ASN | B | 201 | 74.636 | 35.429 | −34.266 | 1.00 | 29.14 | B | C |
| ATOM | 11435 | CB | ASN | B | 201 | 75.477 | 34.473 | −35.110 | 1.00 | 29.87 | B | C |
| ATOM | 11438 | CG | ASN | B | 201 | 76.085 | 35.156 | −36.340 | 1.00 | 35.29 | B | C |
| ATOM | 11439 | OD1 | ASN | B | 201 | 75.519 | 36.111 | −36.876 | 1.00 | 40.73 | B | O |
| ATOM | 11440 | ND2 | ASN | B | 201 | 77.240 | 34.666 | −36.786 | 1.00 | 36.68 | B | N |
| ATOM | 11443 | C | ASN | B | 201 | 73.866 | 34.654 | −33.186 | 1.00 | 28.87 | B | C |
| ATOM | 11444 | O | ASN | B | 201 | 72.728 | 34.266 | −33.380 | 1.00 | 30.14 | B | O |
| ATOM | 11446 | N | HIS | B | 202 | 74.488 | 34.432 | −32.039 | 1.00 | 28.36 | B | N |
| ATOM | 11447 | CA | HIS | B | 202 | 73.802 | 33.791 | −30.935 | 1.00 | 27.61 | B | C |
| ATOM | 11449 | CB | HIS | B | 202 | 74.777 | 33.640 | −29.779 | 1.00 | 28.85 | B | C |
| ATOM | 11452 | CG | HIS | B | 202 | 74.225 | 32.906 | −28.604 | 1.00 | 27.09 | B | C |
| ATOM | 11453 | ND1 | HIS | B | 202 | 73.851 | 31.583 | −28.665 | 1.00 | 23.27 | B | N |
| ATOM | 11455 | CE1 | HIS | B | 202 | 73.430 | 31.198 | −27.473 | 1.00 | 31.18 | B | C |
| ATOM | 11457 | NE2 | HIS | B | 202 | 73.510 | 32.228 | −26.646 | 1.00 | 29.63 | B | N |
| ATOM | 11459 | CD2 | HIS | B | 202 | 74.018 | 33.304 | −27.326 | 1.00 | 26.11 | B | C |
| ATOM | 11461 | C | HIS | B | 202 | 72.606 | 34.649 | −30.537 | 1.00 | 26.71 | B | C |
| ATOM | 11462 | O | HIS | B | 202 | 71.478 | 34.167 | −30.448 | 1.00 | 26.81 | B | O |

TABLE 4-2-continued

Coordinates of *P. alba* IspS

| ATOM | 11464 | N | ALA | B | 203 | 72.850 | 35.941 | −30.355 | 1.00 | 27.12 | B | N |
|------|-------|------|-----|---|-----|--------|--------|---------|------|-------|---|---|
| ATOM | 11465 | CA | ALA | B | 203 | 71.799 | 36.880 | −29.978 | 1.00 | 26.93 | B | C |
| ATOM | 11467 | CB | ALA | B | 203 | 72.402 | 38.252 | −29.671 | 1.00 | 25.40 | B | C |
| ATOM | 11471 | C | ALA | B | 203 | 70.689 | 37.000 | −31.026 | 1.00 | 28.19 | B | C |
| ATOM | 11472 | O | ALA | B | 203 | 69.521 | 37.124 | −30.667 | 1.00 | 32.01 | B | O |
| ATOM | 11474 | N | LEU | B | 204 | 71.041 | 36.991 | −32.309 | 1.00 | 27.53 | B | N |
| ATOM | 11475 | CA | LEU | B | 204 | 70.039 | 37.155 | −33.359 | 1.00 | 27.75 | B | C |
| ATOM | 11477 | CB | LEU | B | 204 | 70.657 | 37.643 | −34.688 | 1.00 | 28.47 | B | C |
| ATOM | 11480 | CG | LEU | B | 204 | 71.244 | 39.070 | −34.727 | 1.00 | 28.70 | B | C |
| ATOM | 11482 | CD1 | LEU | B | 204 | 71.765 | 39.386 | −36.107 | 1.00 | 29.73 | B | C |
| ATOM | 11486 | CD2 | LEU | B | 204 | 70.227 | 40.118 | −34.324 | 1.00 | 26.53 | B | C |
| ATOM | 11490 | C | LEU | B | 204 | 69.259 | 35.862 | −33.570 | 1.00 | 28.30 | B | C |
| ATOM | 11491 | O | LEU | B | 204 | 68.130 | 35.899 | −34.012 | 1.00 | 29.24 | B | O |
| ATOM | 11493 | N | GLU | B | 205 | 69.849 | 34.721 | −33.240 | 1.00 | 28.21 | B | N |
| ATOM | 11494 | CA | GLU | B | 205 | 69.089 | 33.481 | −33.215 | 1.00 | 27.87 | B | C |
| ATOM | 11496 | CB | GLU | B | 205 | 70.020 | 32.319 | −32.906 | 1.00 | 27.30 | B | C |
| ATOM | 11499 | CG | GLU | B | 205 | 69.340 | 30.975 | −32.757 | 1.00 | 31.98 | B | C |
| ATOM | 11502 | CD | GLU | B | 205 | 70.312 | 29.900 | −32.313 | 1.00 | 38.53 | B | C |
| ATOM | 11503 | OE1 | GLU | B | 205 | 70.900 | 30.036 | −31.211 | 1.00 | 37.57 | B | O |
| ATOM | 11504 | OE2 | GLU | B | 205 | 70.500 | 28.926 | −33.072 | 1.00 | 44.27 | B | O |
| ATOM | 11505 | C | GLU | B | 205 | 67.953 | 33.579 | −32.177 | 1.00 | 28.31 | B | C |
| ATOM | 11506 | O | GLU | B | 205 | 66.799 | 33.221 | −32.455 | 1.00 | 28.82 | B | O |
| ATOM | 11508 | N | LEU | B | 206 | 68.288 | 34.069 | −30.985 | 1.00 | 27.57 | B | N |
| ATOM | 11509 | CA | LEU | B | 206 | 67.320 | 34.184 | −29.894 | 1.00 | 26.20 | B | C |
| ATOM | 11511 | CB | LEU | B | 206 | 66.913 | 32.791 | −29.389 | 1.00 | 24.32 | B | C |
| ATOM | 11514 | CG | LEU | B | 206 | 65.658 | 32.728 | −28.529 | 1.00 | 26.26 | B | C |
| ATOM | 11516 | CD1 | LEU | B | 206 | 64.389 | 33.063 | −29.342 | 1.00 | 20.27 | B | C |
| ATOM | 11520 | CD2 | LEU | B | 206 | 65.519 | 31.347 | −27.850 | 1.00 | 22.33 | B | C |
| ATOM | 11524 | C | LEU | B | 206 | 67.953 | 34.958 | −28.753 | 1.00 | 24.67 | B | C |
| ATOM | 11525 | O | LEU | B | 206 | 69.042 | 34.609 | −28.322 | 1.00 | 25.77 | B | O |
| ATOM | 11527 | N | PRO | B | 207 | 67.274 | 35.992 | −28.247 | 1.00 | 22.87 | B | N |
| ATOM | 11528 | CA | PRO | B | 207 | 67.814 | 36.834 | −27.206 | 1.00 | 22.69 | B | C |
| ATOM | 11530 | CB | PRO | B | 207 | 66.802 | 37.980 | −27.138 | 1.00 | 24.47 | B | C |
| ATOM | 11533 | CG | PRO | B | 207 | 65.548 | 37.352 | −27.566 | 1.00 | 22.66 | B | C |
| ATOM | 11536 | CD | PRO | B | 207 | 65.953 | 36.470 | −28.679 | 1.00 | 24.94 | B | C |
| ATOM | 11539 | C | PRO | B | 207 | 67.835 | 36.135 | −25.879 | 1.00 | 22.68 | B | C |
| ATOM | 11540 | O | PRO | B | 207 | 67.086 | 35.181 | −25.683 | 1.00 | 21.77 | B | O |
| ATOM | 11541 | N | LEU | B | 208 | 68.661 | 36.645 | −24.967 | 1.00 | 23.36 | B | N |
| ATOM | 11542 | CA | LEU | B | 208 | 68.863 | 36.031 | −23.652 | 1.00 | 22.82 | B | C |
| ATOM | 11544 | CB | LEU | B | 208 | 69.783 | 36.906 | −22.799 | 1.00 | 26.09 | B | C |
| ATOM | 11547 | CG | LEU | B | 208 | 71.296 | 36.760 | −22.912 | 1.00 | 29.62 | B | C |
| ATOM | 11549 | CD1 | LEU | B | 208 | 71.965 | 37.877 | −22.134 | 1.00 | 35.38 | B | C |
| ATOM | 11553 | CD2 | LEU | B | 208 | 71.688 | 35.403 | −22.345 | 1.00 | 31.33 | B | C |
| ATOM | 11557 | C | LEU | B | 208 | 67.554 | 35.893 | −22.915 | 1.00 | 22.27 | B | C |
| ATOM | 11558 | O | LEU | B | 208 | 67.304 | 34.901 | −22.272 | 1.00 | 23.52 | B | O |
| ATOM | 11560 | N | HIS | B | 209 | 66.710 | 36.912 | −23.010 | 1.00 | 19.79 | B | N |
| ATOM | 11561 | CA | HIS | B | 209 | 65.496 | 36.918 | −22.232 | 1.00 | 19.81 | B | C |
| ATOM | 11563 | CB | HIS | B | 209 | 64.819 | 38.278 | −22.387 | 1.00 | 18.57 | B | C |
| ATOM | 11566 | CG | HIS | B | 209 | 63.665 | 38.491 | −21.464 | 1.00 | 20.89 | B | C |
| ATOM | 11567 | ND1 | HIS | B | 209 | 63.798 | 38.455 | −20.095 | 1.00 | 18.30 | B | N |
| ATOM | 11569 | CE1 | HIS | B | 209 | 62.624 | 38.687 | −19.537 | 1.00 | 19.90 | B | C |
| ATOM | 11571 | NE2 | HIS | B | 209 | 61.732 | 38.865 | −20.497 | 1.00 | 24.74 | B | N |
| ATOM | 11573 | CD2 | HIS | B | 209 | 62.357 | 38.745 | −21.713 | 1.00 | 19.23 | B | C |
| ATOM | 11575 | C | HIS | B | 209 | 64.550 | 35.775 | −22.659 | 1.00 | 18.96 | B | C |
| ATOM | 11576 | O | HIS | B | 209 | 63.638 | 35.417 | −21.928 | 1.00 | 20.40 | B | O |
| ATOM | 11578 | N | ARG | B | 210 | 64.771 | 35.214 | −23.838 | 1.00 | 17.53 | B | N |
| ATOM | 11579 | CA | ARG | B | 210 | 63.921 | 34.159 | −24.339 | 1.00 | 21.00 | B | C |
| ATOM | 11581 | CB | ARG | B | 210 | 63.417 | 34.519 | −25.736 | 1.00 | 21.58 | B | C |
| ATOM | 11584 | CG | ARG | B | 210 | 62.558 | 35.776 | −25.720 | 1.00 | 25.30 | B | C |
| ATOM | 11587 | CD | ARG | B | 210 | 61.972 | 36.079 | −27.098 | 1.00 | 26.92 | B | C |
| ATOM | 11590 | NE | ARG | B | 210 | 61.038 | 37.199 | −27.044 | 1.00 | 26.04 | B | N |
| ATOM | 11592 | CZ | ARG | B | 210 | 60.373 | 37.677 | −28.089 | 1.00 | 25.39 | B | C |
| ATOM | 11593 | NH1 | ARG | B | 210 | 60.529 | 37.128 | −29.286 | 1.00 | 28.28 | B | N |
| ATOM | 11596 | NH2 | ARG | B | 210 | 59.530 | 38.704 | −27.933 | 1.00 | 26.88 | B | N |
| ATOM | 11599 | C | ARG | B | 210 | 64.564 | 32.786 | −24.362 | 1.00 | 21.01 | B | C |
| ATOM | 11600 | O | ARG | B | 210 | 63.852 | 31.814 | −24.500 | 1.00 | 22.57 | B | O |
| ATOM | 11602 | N | ARG | B | 211 | 65.881 | 32.694 | −24.190 | 1.00 | 21.79 | B | N |
| ATOM | 11603 | CA | ARG | B | 211 | 66.560 | 31.387 | −24.219 | 1.00 | 21.96 | B | C |
| ATOM | 11605 | CB | ARG | B | 211 | 68.017 | 31.568 | −24.607 | 1.00 | 20.36 | B | C |
| ATOM | 11608 | CG | ARG | B | 211 | 68.659 | 30.320 | −25.118 | 1.00 | 25.64 | B | C |
| ATOM | 11611 | CD | ARG | B | 211 | 70.125 | 30.557 | −25.409 | 1.00 | 25.18 | B | C |
| ATOM | 11614 | NE | ARG | B | 211 | 70.339 | 31.518 | −26.488 | 1.00 | 22.19 | B | N |
| ATOM | 11616 | CZ | ARG | B | 211 | 70.325 | 31.219 | −27.789 | 1.00 | 31.36 | B | C |
| ATOM | 11617 | NH1 | ARG | B | 211 | 70.100 | 29.974 | −28.203 | 1.00 | 32.36 | B | N |
| ATOM | 11620 | NH2 | ARG | B | 211 | 70.545 | 32.174 | −28.692 | 1.00 | 31.10 | B | N |
| ATOM | 11623 | C | ARG | B | 211 | 66.482 | 30.715 | −22.858 | 1.00 | 21.08 | B | C |
| ATOM | 11624 | O | ARG | B | 211 | 66.562 | 31.380 | −21.829 | 1.00 | 23.84 | B | O |
| ATOM | 11626 | N | THR | B | 212 | 66.332 | 29.401 | −22.841 | 1.00 | 21.62 | B | N |

TABLE 4-2-continued

Coordinates of *P. alba* IspS

| ATOM | 11627 | CA | THR | B | 212 | 66.258 | 28.663 | −21.584 | 1.00 | 22.86 | B | C |
|------|-------|-----|-----|---|-----|--------|--------|---------|------|-------|---|---|
| ATOM | 11629 | CB | THR | B | 212 | 65.883 | 27.196 | −21.796 | 1.00 | 24.07 | B | C |
| ATOM | 11631 | OG1 | THR | B | 212 | 66.761 | 26.625 | −22.770 | 1.00 | 31.00 | B | O |
| ATOM | 11633 | CG2 | THR | B | 212 | 64.443 | 27.050 | −22.274 | 1.00 | 19.45 | B | C |
| ATOM | 11637 | C | THR | B | 212 | 67.628 | 28.725 | −20.923 | 1.00 | 23.79 | B | C |
| ATOM | 11638 | O | THR | B | 212 | 68.643 | 28.997 | −21.580 | 1.00 | 23.93 | B | O |
| ATOM | 11640 | N | GLN | B | 213 | 67.656 | 28.454 | −19.630 | 1.00 | 23.05 | B | N |
| ATOM | 11641 | CA | GLN | B | 213 | 68.850 | 28.713 | −18.832 | 1.00 | 21.92 | B | C |
| ATOM | 11643 | CB | GLN | B | 213 | 68.513 | 28.620 | −17.345 | 1.00 | 21.12 | B | C |
| ATOM | 11646 | CG | GLN | B | 213 | 69.466 | 29.407 | −16.398 | 1.00 | 26.64 | B | C |
| ATOM | 11649 | CD | GLN | B | 213 | 70.578 | 28.551 | −15.863 | 1.00 | 26.56 | B | C |
| ATOM | 11650 | OE1 | GLN | B | 213 | 70.991 | 27.565 | −16.490 | 1.00 | 26.61 | B | O |
| ATOM | 11651 | NE2 | GLN | B | 213 | 71.079 | 28.915 | −14.701 | 1.00 | 20.90 | B | N |
| ATOM | 11654 | C | GLN | B | 213 | 69.985 | 27.753 | −19.202 | 1.00 | 20.81 | B | C |
| ATOM | 11655 | O | GLN | B | 213 | 71.121 | 28.187 | −19.439 | 1.00 | 20.28 | B | O |
| ATOM | 11657 | N | ARG | B | 214 | 69.690 | 26.457 | −19.252 | 1.00 | 20.19 | B | N |
| ATOM | 11658 | CA | ARG | B | 214 | 70.746 | 25.484 | −19.544 | 1.00 | 21.47 | B | C |
| ATOM | 11660 | CB | ARG | B | 214 | 70.290 | 24.041 | −19.386 | 1.00 | 21.13 | B | C |
| ATOM | 11663 | CG | ARG | B | 214 | 69.953 | 23.656 | −17.970 | 1.00 | 21.84 | B | C |
| ATOM | 11666 | CD | ARG | B | 214 | 71.190 | 23.470 | −17.110 | 1.00 | 24.31 | B | C |
| ATOM | 11669 | NE | ARG | B | 214 | 71.582 | 24.706 | −16.457 | 1.00 | 25.78 | B | N |
| ATOM | 11671 | CZ | ARG | B | 214 | 72.655 | 24.854 | −15.693 | 1.00 | 23.08 | B | C |
| ATOM | 11672 | NH1 | ARG | B | 214 | 73.481 | 23.834 | −15.486 | 1.00 | 23.99 | B | N |
| ATOM | 11675 | NH2 | ARG | B | 214 | 72.915 | 26.046 | −15.155 | 1.00 | 19.12 | B | N |
| ATOM | 11678 | C | ARG | B | 214 | 71.327 | 25.675 | −20.919 | 1.00 | 20.24 | B | C |
| ATOM | 11679 | O | ARG | B | 214 | 72.531 | 25.534 | −21.070 | 1.00 | 20.21 | B | O |
| ATOM | 11681 | N | LEU | B | 215 | 70.506 | 26.014 | −21.910 | 1.00 | 19.38 | B | N |
| ATOM | 11682 | CA | LEU | B | 215 | 71.021 | 26.177 | −23.278 | 1.00 | 21.93 | B | C |
| ATOM | 11684 | CB | LEU | B | 215 | 69.896 | 26.332 | −24.294 | 1.00 | 23.52 | B | C |
| ATOM | 11687 | CG | LEU | B | 215 | 69.313 | 25.060 | −24.892 | 1.00 | 32.95 | B | C |
| ATOM | 11689 | CD1 | LEU | B | 215 | 70.415 | 24.335 | −25.695 | 1.00 | 29.05 | B | C |
| ATOM | 11693 | CD2 | LEU | B | 215 | 68.102 | 25.417 | −25.789 | 1.00 | 29.82 | B | C |
| ATOM | 11697 | C | LEU | B | 215 | 71.983 | 27.354 | −23.406 | 1.00 | 22.32 | B | C |
| ATOM | 11698 | O | LEU | B | 215 | 73.016 | 27.231 | −24.041 | 1.00 | 22.96 | B | O |
| ATOM | 11700 | N | GLU | B | 216 | 71.631 | 28.488 | −22.806 | 1.00 | 23.34 | B | N |
| ATOM | 11701 | CA | GLU | B | 216 | 72.543 | 29.621 | −22.693 | 1.00 | 23.77 | B | C |
| ATOM | 11703 | CB | GLU | B | 216 | 71.860 | 30.793 | −21.958 | 1.00 | 24.84 | B | C |
| ATOM | 11706 | CG | GLU | B | 216 | 72.711 | 32.044 | −21.844 | 1.00 | 26.26 | B | C |
| ATOM | 11709 | CD | GLU | B | 216 | 73.313 | 32.494 | −23.185 | 1.00 | 29.08 | B | C |
| ATOM | 11710 | OE1 | GLU | B | 216 | 72.657 | 32.349 | −24.232 | 1.00 | 30.45 | B | O |
| ATOM | 11711 | OE2 | GLU | B | 216 | 74.452 | 33.006 | −23.181 | 1.00 | 29.22 | B | O |
| ATOM | 11712 | C | GLU | B | 216 | 73.815 | 29.224 | −21.940 | 1.00 | 23.03 | B | C |
| ATOM | 11713 | O | GLU | B | 216 | 74.910 | 29.595 | −22.331 | 1.00 | 25.15 | B | O |
| ATOM | 11715 | N | ALA | B | 217 | 73.692 | 28.461 | −20.865 | 1.00 | 21.75 | B | N |
| ATOM | 11716 | CA | ALA | B | 217 | 74.889 | 28.141 | −20.110 | 1.00 | 21.54 | B | C |
| ATOM | 11718 | CB | ALA | B | 217 | 74.557 | 27.429 | −18.817 | 1.00 | 18.56 | B | C |
| ATOM | 11722 | C | ALA | B | 217 | 75.880 | 27.336 | −20.949 | 1.00 | 22.53 | B | C |
| ATOM | 11723 | O | ALA | B | 217 | 77.092 | 27.634 | −20.954 | 1.00 | 24.18 | B | O |
| ATOM | 11725 | N | VAL | B | 218 | 75.380 | 26.356 | −21.693 | 1.00 | 24.24 | B | N |
| ATOM | 11726 | CA | VAL | B | 218 | 76.264 | 25.447 | −22.423 | 1.00 | 24.89 | B | C |
| ATOM | 11728 | CB | VAL | B | 218 | 75.544 | 24.155 | −22.910 | 1.00 | 26.35 | B | C |
| ATOM | 11730 | CG1 | VAL | B | 218 | 74.605 | 24.436 | −24.089 | 1.00 | 24.54 | B | C |
| ATOM | 11734 | CG2 | VAL | B | 218 | 76.595 | 23.062 | −23.278 | 1.00 | 27.94 | B | C |
| ATOM | 11738 | C | VAL | B | 218 | 76.947 | 26.169 | −23.569 | 1.00 | 24.67 | B | C |
| ATOM | 11739 | O | VAL | B | 218 | 78.083 | 25.880 | −23.877 | 1.00 | 26.68 | B | O |
| ATOM | 11741 | N | TRP | B | 219 | 76.260 | 27.128 | −24.179 | 1.00 | 25.65 | B | N |
| ATOM | 11742 | CA | TRP | B | 219 | 76.875 | 27.976 | −25.199 | 1.00 | 24.72 | B | C |
| ATOM | 11744 | CB | TRP | B | 219 | 75.789 | 28.722 | −25.996 | 1.00 | 26.46 | B | C |
| ATOM | 11747 | CG | TRP | B | 219 | 76.344 | 29.516 | −27.131 | 1.00 | 27.34 | B | C |
| ATOM | 11748 | CD1 | TRP | B | 219 | 76.444 | 29.122 | −28.431 | 1.00 | 29.10 | B | C |
| ATOM | 11750 | NE1 | TRP | B | 219 | 77.032 | 30.117 | −29.184 | 1.00 | 26.04 | B | N |
| ATOM | 11752 | CE2 | TRP | B | 219 | 77.329 | 31.171 | −28.366 | 1.00 | 26.96 | B | C |
| ATOM | 11753 | CD2 | TRP | B | 219 | 76.916 | 30.826 | −27.063 | 1.00 | 22.98 | B | C |
| ATOM | 11754 | CE3 | TRP | B | 219 | 77.110 | 31.745 | −26.030 | 1.00 | 29.02 | B | C |
| ATOM | 11756 | CZ3 | TRP | B | 219 | 77.708 | 32.965 | −26.327 | 1.00 | 30.21 | B | C |
| ATOM | 11758 | CH2 | TRP | B | 219 | 78.117 | 33.273 | −27.620 | 1.00 | 28.87 | B | C |
| ATOM | 11760 | CZ2 | TRP | B | 219 | 77.937 | 32.390 | −28.657 | 1.00 | 32.64 | B | C |
| ATOM | 11762 | C | TRP | B | 219 | 77.855 | 28.978 | −24.584 | 1.00 | 23.76 | B | C |
| ATOM | 11763 | O | TRP | B | 219 | 78.924 | 29.224 | −25.124 | 1.00 | 27.15 | B | O |
| ATOM | 11765 | N | SER | B | 220 | 77.495 | 29.574 | −23.456 | 1.00 | 23.73 | B | N |
| ATOM | 11766 | CA | SER | B | 220 | 78.330 | 30.616 | −22.874 | 1.00 | 23.51 | B | C |
| ATOM | 11768 | CB | SER | B | 220 | 77.573 | 31.395 | −21.803 | 1.00 | 22.98 | B | C |
| ATOM | 11771 | OG | SER | B | 220 | 76.786 | 32.384 | −22.416 | 1.00 | 25.03 | B | C |
| ATOM | 11773 | C | SER | B | 220 | 79.606 | 30.054 | −22.286 | 1.00 | 24.58 | B | C |
| ATOM | 11774 | O | SER | B | 220 | 80.623 | 30.723 | −22.291 | 1.00 | 26.26 | B | O |
| ATOM | 11776 | N | ILE | B | 221 | 79.542 | 28.837 | −21.755 | 1.00 | 24.53 | B | N |
| ATOM | 11777 | CA | ILE | B | 221 | 80.726 | 28.191 | −21.221 | 1.00 | 25.43 | B | C |
| ATOM | 11779 | CB | ILE | B | 221 | 80.380 | 26.930 | −20.433 | 1.00 | 24.62 | B | C |

TABLE 4-2-continued

Coordinates of *P. alba* IspS

| ATOM | 11781 | CG1 | ILE | B | 221 | 79.697 | 27.327 | −19.128 | 1.00 | 21.02 | B | C |
|---|---|---|---|---|---|---|---|---|---|---|---|---|
| ATOM | 11784 | CD1 | ILE | B | 221 | 78.873 | 26.217 | −18.505 | 1.00 | 18.22 | B | C |
| ATOM | 11788 | CG2 | ILE | B | 221 | 81.634 | 26.132 | −20.129 | 1.00 | 24.19 | B | C |
| ATOM | 11792 | C | ILE | B | 221 | 81.711 | 27.866 | −22.347 | 1.00 | 28.11 | B | C |
| ATOM | 11793 | O | ILE | B | 221 | 82.907 | 28.122 | −22.224 | 1.00 | 25.44 | B | O |
| ATOM | 11795 | N | GLU | B | 222 | 81.208 | 27.331 | −23.452 | 1.00 | 29.17 | B | N |
| ATOM | 11796 | CA | GLU | B | 222 | 82.064 | 27.117 | −24.612 | 1.00 | 30.37 | B | C |
| ATOM | 11798 | CB | GLU | B | 222 | 81.305 | 26.393 | −25.728 | 1.00 | 31.94 | B | C |
| ATOM | 11801 | CG | GLU | B | 222 | 82.195 | 25.909 | −26.897 | 1.00 | 37.68 | B | C |
| ATOM | 11804 | CD | GLU | B | 222 | 83.413 | 25.100 | −26.431 | 1.00 | 40.63 | B | C |
| ATOM | 11805 | OE1 | GLU | B | 222 | 83.347 | 24.445 | −25.362 | 1.00 | 46.08 | B | O |
| ATOM | 11806 | OE2 | GLU | B | 222 | 84.437 | 25.133 | −27.136 | 1.00 | 49.29 | B | O |
| ATOM | 11807 | C | GLU | B | 222 | 82.681 | 28.425 | −25.139 | 1.00 | 29.60 | B | C |
| ATOM | 11808 | O | GLU | B | 222 | 83.845 | 28.445 | −25.474 | 1.00 | 31.39 | B | O |
| ATOM | 11810 | N | ALA | B | 223 | 81.917 | 29.511 | −25.198 | 1.00 | 29.46 | B | N |
| ATOM | 11811 | CA | ALA | B | 223 | 82.460 | 30.794 | −25.669 | 1.00 | 27.98 | B | C |
| ATOM | 11813 | CB | ALA | B | 223 | 81.354 | 31.779 | −25.924 | 1.00 | 27.66 | B | C |
| ATOM | 11817 | C | ALA | B | 223 | 83.446 | 31.378 | −24.672 | 1.00 | 29.38 | B | C |
| ATOM | 11818 | O | ALA | B | 223 | 84.539 | 31.784 | −25.049 | 1.00 | 30.35 | B | O |
| ATOM | 11820 | N | TYR | B | 224 | 83.073 | 31.405 | −23.393 | 1.00 | 29.56 | B | N |
| ATOM | 11821 | CA | TYR | B | 224 | 83.948 | 31.970 | −22.364 | 1.00 | 28.89 | B | C |
| ATOM | 11823 | CB | TYR | B | 224 | 83.281 | 31.910 | −20.991 | 1.00 | 27.75 | B | C |
| ATOM | 11826 | CG | TYR | B | 224 | 83.845 | 32.869 | −19.962 | 1.00 | 21.93 | B | C |
| ATOM | 11827 | CD1 | TYR | B | 224 | 83.706 | 34.246 | −20.111 | 1.00 | 25.72 | B | C |
| ATOM | 11829 | CE1 | TYR | B | 224 | 84.200 | 35.134 | −19.150 | 1.00 | 28.65 | B | C |
| ATOM | 11831 | CZ | TYR | B | 224 | 84.823 | 34.646 | −18.019 | 1.00 | 26.53 | B | C |
| ATOM | 11832 | OH | TYR | B | 224 | 85.322 | 35.516 | −17.065 | 1.00 | 31.14 | B | O |
| ATOM | 11834 | CE2 | TYR | B | 224 | 84.959 | 33.293 | −17.849 | 1.00 | 24.43 | B | C |
| ATOM | 11836 | CD2 | TYR | B | 224 | 84.464 | 32.409 | −18.827 | 1.00 | 24.32 | B | C |
| ATOM | 11838 | C | TYR | B | 224 | 85.280 | 31.227 | −22.319 | 1.00 | 30.12 | B | C |
| ATOM | 11839 | O | TYR | B | 224 | 86.333 | 31.827 | −22.135 | 1.00 | 30.99 | B | O |
| ATOM | 11841 | N | ARG | B | 225 | 85.220 | 29.915 | −22.486 | 1.00 | 31.92 | B | N |
| ATOM | 11842 | CA | ARG | B | 225 | 86.409 | 29.069 | −22.478 | 1.00 | 34.85 | B | C |
| ATOM | 11844 | CB | ARG | B | 225 | 85.991 | 27.615 | −22.733 | 1.00 | 34.71 | B | C |
| ATOM | 11847 | CG | ARG | B | 225 | 87.030 | 26.604 | −22.328 | 1.00 | 41.35 | B | C |
| ATOM | 11850 | CD | ARG | B | 225 | 86.910 | 25.349 | −23.161 | 1.00 | 44.42 | B | C |
| ATOM | 11853 | NE | ARG | B | 225 | 85.793 | 24.534 | −22.728 | 1.00 | 29.27 | B | N |
| ATOM | 11855 | CZ | ARG | B | 225 | 85.866 | 23.584 | −21.803 | 1.00 | 26.94 | B | C |
| ATOM | 11856 | NH1 | ARG | B | 225 | 87.007 | 23.300 | −21.189 | 1.00 | 22.41 | B | N |
| ATOM | 11859 | NH2 | ARG | B | 225 | 84.776 | 22.892 | −21.496 | 1.00 | 24.98 | B | N |
| ATOM | 11862 | C | ARG | B | 225 | 87.452 | 29.515 | −23.529 | 1.00 | 36.03 | B | C |
| ATOM | 11863 | O | ARG | B | 225 | 88.644 | 29.365 | −23.320 | 1.00 | 34.54 | B | O |
| ATOM | 11865 | N | LYS | B | 226 | 86.986 | 30.054 | −24.655 | 1.00 | 39.58 | B | N |
| ATOM | 11866 | CA | LYS | B | 226 | 87.860 | 30.507 | −25.732 | 1.00 | 41.75 | B | C |
| ATOM | 11868 | CB | LYS | B | 226 | 87.114 | 30.457 | −27.069 | 1.00 | 41.97 | B | C |
| ATOM | 11871 | CG | LYS | B | 226 | 86.581 | 29.085 | −27.431 | 1.00 | 44.77 | B | C |
| ATOM | 11874 | CD | LYS | B | 226 | 86.073 | 29.053 | −28.870 | 1.00 | 49.54 | B | C |
| ATOM | 11877 | CE | LYS | B | 226 | 85.298 | 27.780 | −29.192 | 1.00 | 50.36 | B | C |
| ATOM | 11880 | NZ | LYS | B | 226 | 83.891 | 28.078 | −29.559 | 1.00 | 51.17 | B | N |
| ATOM | 11884 | C | LYS | B | 226 | 88.421 | 31.919 | −25.534 | 1.00 | 43.33 | B | C |
| ATOM | 11885 | O | LYS | B | 226 | 89.259 | 32.355 | −26.324 | 1.00 | 43.89 | B | O |
| ATOM | 11887 | N | LYS | B | 227 | 87.962 | 32.642 | −24.514 | 1.00 | 45.03 | B | N |
| ATOM | 11888 | CA | LYS | B | 227 | 88.498 | 33.981 | −24.226 | 1.00 | 47.42 | B | C |
| ATOM | 11890 | CB | LYS | B | 227 | 87.508 | 34.828 | −23.413 | 1.00 | 47.85 | B | C |
| ATOM | 11893 | CG | LYS | B | 227 | 86.288 | 35.318 | −24.172 | 1.00 | 50.13 | B | C |
| ATOM | 11896 | CD | LYS | B | 227 | 85.580 | 36.442 | −23.402 | 1.00 | 56.73 | B | C |
| ATOM | 11899 | CE | LYS | B | 227 | 84.102 | 36.545 | −23.774 | 1.00 | 64.18 | B | C |
| ATOM | 11902 | NZ | LYS | B | 227 | 83.858 | 36.666 | −25.249 | 1.00 | 66.49 | B | N |
| ATOM | 11906 | C | LYS | B | 227 | 89.814 | 33.870 | −23.453 | 1.00 | 48.79 | B | C |
| ATOM | 11907 | O | LYS | B | 227 | 89.862 | 33.243 | −22.382 | 1.00 | 49.31 | B | O |
| ATOM | 11909 | N | GLU | B | 228 | 90.873 | 34.484 | −23.987 | 1.00 | 48.99 | B | N |
| ATOM | 11910 | CA | GLU | B | 228 | 92.184 | 34.472 | −23.327 | 1.00 | 49.23 | B | C |
| ATOM | 11912 | CB | GLU | B | 228 | 93.265 | 35.098 | −24.220 | 1.00 | 50.17 | B | C |
| ATOM | 11915 | CG | GLU | B | 228 | 94.651 | 35.139 | −23.556 | 1.00 | 56.84 | B | C |
| ATOM | 11918 | CD | GLU | B | 228 | 95.805 | 35.113 | −24.551 | 1.00 | 62.65 | B | C |
| ATOM | 11919 | OE1 | GLU | B | 228 | 95.772 | 35.883 | −25.536 | 1.00 | 63.14 | B | O |
| ATOM | 11920 | OE2 | GLU | B | 228 | 96.753 | 34.324 | −24.336 | 1.00 | 62.24 | B | O |
| ATOM | 11921 | C | GLU | B | 228 | 92.150 | 35.184 | −21.972 | 1.00 | 46.82 | B | C |
| ATOM | 11922 | O | GLU | B | 228 | 92.875 | 34.808 | −21.048 | 1.00 | 47.31 | B | O |
| ATOM | 11924 | N | ASP | B | 229 | 91.304 | 36.202 | −21.859 | 1.00 | 43.57 | B | N |
| ATOM | 11925 | CA | ASP | B | 229 | 91.168 | 36.959 | −20.621 | 1.00 | 42.02 | B | C |
| ATOM | 11927 | CB | ASP | B | 229 | 90.946 | 38.439 | −20.943 | 1.00 | 43.47 | B | C |
| ATOM | 11930 | CG | ASP | B | 229 | 89.751 | 38.661 | −21.854 | 1.00 | 47.72 | B | C |
| ATOM | 11931 | OD1 | ASP | B | 229 | 89.491 | 37.784 | −22.704 | 1.00 | 51.55 | B | O |
| ATOM | 11932 | OD2 | ASP | B | 229 | 89.079 | 39.704 | −21.726 | 1.00 | 55.81 | B | O |
| ATOM | 11933 | C | ASP | B | 229 | 90.035 | 36.448 | −19.714 | 1.00 | 38.44 | B | C |
| ATOM | 11934 | O | ASP | B | 229 | 89.667 | 37.131 | −18.769 | 1.00 | 37.66 | B | O |
| ATOM | 11936 | N | ALA | B | 230 | 89.489 | 35.261 | −19.983 | 1.00 | 35.09 | B | N |

TABLE 4-2-continued

Coordinates of *P. alba* IspS

| ATOM | 11937 | CA | ALA | B | 230 | 88.432 | 34.696 | −19.131 | 1.00 | 33.38 | B | C |
|---|---|---|---|---|---|---|---|---|---|---|---|---|
| ATOM | 11939 | CB | ALA | B | 230 | 87.915 | 33.392 | −19.704 | 1.00 | 33.10 | B | C |
| ATOM | 11943 | C | ALA | B | 230 | 88.934 | 34.465 | −17.711 | 1.00 | 32.12 | B | C |
| ATOM | 11944 | O | ALA | B | 230 | 90.070 | 34.048 | −17.495 | 1.00 | 30.75 | B | O |
| ATOM | 11946 | N | ASN | B | 231 | 88.080 | 34.738 | −16.736 | 1.00 | 30.68 | B | N |
| ATOM | 11947 | CA | ASN | B | 231 | 88.422 | 34.453 | −15.359 | 1.00 | 29.53 | B | C |
| ATOM | 11949 | CB | ASN | B | 231 | 87.456 | 35.129 | −14.388 | 1.00 | 29.88 | B | C |
| ATOM | 11952 | CG | ASN | B | 231 | 87.820 | 34.867 | −12.947 | 1.00 | 33.58 | B | C |
| ATOM | 11953 | OD1 | ASN | B | 231 | 87.935 | 33.714 | −12.520 | 1.00 | 31.88 | B | O |
| ATOM | 11954 | ND2 | ASN | B | 231 | 88.032 | 35.936 | −12.189 | 1.00 | 42.97 | B | N |
| ATOM | 11957 | C | ASN | B | 231 | 88.388 | 32.960 | −15.152 | 1.00 | 27.93 | B | C |
| ATOM | 11958 | O | ASN | B | 231 | 87.334 | 32.338 | −15.276 | 1.00 | 26.52 | B | O |
| ATOM | 11960 | N | GLN | B | 232 | 89.539 | 32.398 | −14.806 | 1.00 | 27.85 | B | N |
| ATOM | 11961 | CA | GLN | B | 232 | 89.696 | 30.945 | −14.719 | 1.00 | 28.06 | B | C |
| ATOM | 11963 | CB | GLN | B | 232 | 91.178 | 30.574 | −14.669 | 1.00 | 27.87 | B | C |
| ATOM | 11966 | CG | GLN | B | 232 | 91.958 | 30.978 | −15.931 | 1.00 | 33.14 | B | C |
| ATOM | 11969 | CD | GLN | B | 232 | 91.460 | 30.284 | −17.202 | 1.00 | 35.07 | B | C |
| ATOM | 11970 | OE1 | GLN | B | 232 | 91.496 | 29.059 | −17.301 | 1.00 | 37.93 | B | O |
| ATOM | 11971 | NE2 | GLN | B | 232 | 91.003 | 31.069 | −18.177 | 1.00 | 32.06 | B | N |
| ATOM | 11974 | C | GLN | B | 232 | 88.940 | 30.326 | −13.538 | 1.00 | 27.32 | B | C |
| ATOM | 11975 | O | GLN | B | 232 | 88.472 | 29.175 | −13.625 | 1.00 | 28.40 | B | O |
| ATOM | 11977 | N | VAL | B | 233 | 88.814 | 31.081 | −12.449 | 1.00 | 23.84 | B | N |
| ATOM | 11978 | CA | VAL | B | 233 | 88.047 | 30.625 | −11.305 | 1.00 | 23.03 | B | C |
| ATOM | 11980 | CB | VAL | B | 233 | 88.182 | 31.592 | −10.105 | 1.00 | 23.26 | B | C |
| ATOM | 11982 | CG1 | VAL | B | 233 | 87.102 | 31.342 | −9.096 | 1.00 | 19.84 | B | C |
| ATOM | 11986 | CG2 | VAL | B | 233 | 89.581 | 31.440 | −9.438 | 1.00 | 25.03 | B | C |
| ATOM | 11990 | C | VAL | B | 233 | 86.583 | 30.457 | −11.713 | 1.00 | 23.81 | B | C |
| ATOM | 11991 | O | VAL | B | 233 | 85.990 | 29.405 | −11.492 | 1.00 | 23.11 | B | O |
| ATOM | 11993 | N | LEU | B | 234 | 86.014 | 31.491 | −12.330 | 1.00 | 22.26 | B | N |
| ATOM | 11994 | CA | LEU | B | 234 | 84.630 | 31.454 | −12.733 | 1.00 | 22.19 | B | C |
| ATOM | 11996 | CB | LEU | B | 234 | 84.219 | 32.814 | −13.267 | 1.00 | 22.77 | B | C |
| ATOM | 11999 | CG | LEU | B | 234 | 82.774 | 33.046 | −13.690 | 1.00 | 21.02 | B | C |
| ATOM | 12001 | CD1 | LEU | B | 234 | 81.821 | 32.913 | −12.510 | 1.00 | 13.82 | B | C |
| ATOM | 12005 | CD2 | LEU | B | 234 | 82.673 | 34.433 | −14.302 | 1.00 | 18.88 | B | C |
| ATOM | 12009 | C | LEU | B | 234 | 84.402 | 30.345 | −13.776 | 1.00 | 22.30 | B | C |
| ATOM | 12010 | O | LEU | B | 234 | 83.411 | 29.637 | −13.717 | 1.00 | 20.57 | B | O |
| ATOM | 12012 | N | LEU | B | 235 | 85.344 | 30.188 | −14.702 | 1.00 | 22.73 | B | N |
| ATOM | 12013 | CA | LEU | B | 235 | 85.219 | 29.215 | −15.783 | 1.00 | 22.64 | B | C |
| ATOM | 12015 | CB | LEU | B | 235 | 86.431 | 29.277 | −16.707 | 1.00 | 23.38 | B | C |
| ATOM | 12018 | CG | LEU | B | 235 | 86.482 | 28.297 | −17.885 | 1.00 | 26.34 | B | C |
| ATOM | 12020 | CD1 | LEU | B | 235 | 85.223 | 28.417 | −18.756 | 1.00 | 16.79 | B | C |
| ATOM | 12024 | CD2 | LEU | B | 235 | 87.756 | 28.530 | −18.717 | 1.00 | 19.46 | B | C |
| ATOM | 12028 | C | LEU | B | 235 | 85.121 | 27.835 | −15.206 | 1.00 | 21.21 | B | C |
| ATOM | 12029 | O | LEU | B | 235 | 84.249 | 27.054 | −15.565 | 1.00 | 20.49 | B | O |
| ATOM | 12031 | N | GLU | B | 236 | 86.038 | 27.550 | −14.301 | 1.00 | 22.20 | B | N |
| ATOM | 12032 | CA | GLU | B | 236 | 86.112 | 26.249 | −13.692 | 1.00 | 22.88 | B | C |
| ATOM | 12034 | CB | GLU | B | 236 | 87.348 | 26.114 | −12.787 | 1.00 | 22.27 | B | C |
| ATOM | 12037 | CG | GLU | B | 236 | 87.471 | 24.721 | −12.224 | 1.00 | 25.07 | B | C |
| ATOM | 12040 | CD | GLU | B | 236 | 88.782 | 24.458 | −11.508 | 1.00 | 30.11 | B | C |
| ATOM | 12041 | OE1 | GLU | B | 236 | 89.489 | 25.432 | −11.145 | 1.00 | 32.54 | B | O |
| ATOM | 12042 | OE2 | GLU | B | 236 | 89.081 | 23.254 | −11.316 | 1.00 | 28.82 | B | O |
| ATOM | 12043 | C | GLU | B | 236 | 84.852 | 25.988 | −12.902 | 1.00 | 21.39 | B | C |
| ATOM | 12044 | O | GLU | B | 236 | 84.299 | 24.885 | −12.977 | 1.00 | 23.11 | B | O |
| ATOM | 12046 | N | LEU | B | 237 | 84.395 | 26.989 | −12.154 | 1.00 | 19.15 | B | N |
| ATOM | 12047 | CA | LEU | B | 237 | 83.205 | 26.805 | −11.340 | 1.00 | 17.76 | B | C |
| ATOM | 12049 | CB | LEU | B | 237 | 82.892 | 28.060 | −10.548 | 1.00 | 15.89 | B | C |
| ATOM | 12052 | CG | LEU | B | 237 | 81.682 | 27.946 | −9.637 | 1.00 | 14.28 | B | C |
| ATOM | 12054 | CD1 | LEU | B | 237 | 81.846 | 26.791 | −8.650 | 1.00 | 8.37 | B | C |
| ATOM | 12058 | CD2 | LEU | B | 237 | 81.476 | 29.262 | −8.914 | 1.00 | 13.97 | B | C |
| ATOM | 12062 | C | LEU | B | 237 | 82.035 | 26.434 | −12.255 | 1.00 | 18.88 | B | C |
| ATOM | 12063 | O | LEU | B | 237 | 81.303 | 25.467 | −11.980 | 1.00 | 21.48 | B | O |
| ATOM | 12065 | N | ALA | B | 238 | 81.911 | 27.163 | −13.362 | 1.00 | 16.52 | B | N |
| ATOM | 12066 | CA | ALA | B | 238 | 80.791 | 27.010 | −14.287 | 1.00 | 18.32 | B | C |
| ATOM | 12068 | CB | ALA | B | 238 | 80.871 | 28.022 | −15.404 | 1.00 | 16.15 | B | C |
| ATOM | 12072 | C | ALA | B | 238 | 80.759 | 25.621 | −14.881 | 1.00 | 20.18 | B | C |
| ATOM | 12073 | O | ALA | B | 238 | 79.683 | 25.009 | −14.973 | 1.00 | 22.18 | B | O |
| ATOM | 12075 | N | ILE | B | 239 | 81.932 | 25.132 | −15.293 | 1.00 | 19.80 | B | N |
| ATOM | 12076 | CA | ILE | B | 239 | 82.039 | 23.792 | −15.821 | 1.00 | 19.87 | B | C |
| ATOM | 12078 | CB | ILE | B | 239 | 83.461 | 23.458 | −16.279 | 1.00 | 20.01 | B | C |
| ATOM | 12080 | CG1 | ILE | B | 239 | 83.800 | 24.223 | −17.567 | 1.00 | 21.51 | B | C |
| ATOM | 12083 | CD1 | ILE | B | 239 | 85.250 | 23.962 | −18.074 | 1.00 | 19.39 | B | C |
| ATOM | 12087 | CG2 | ILE | B | 239 | 83.601 | 21.955 | −16.508 | 1.00 | 13.60 | B | C |
| ATOM | 12091 | C | ILE | B | 239 | 81.589 | 22.800 | −14.757 | 1.00 | 21.11 | B | C |
| ATOM | 12092 | O | ILE | B | 239 | 80.781 | 21.917 | −15.030 | 1.00 | 22.06 | B | O |
| ATOM | 12094 | N | LEU | B | 240 | 82.090 | 22.968 | −13.543 | 1.00 | 21.72 | B | N |
| ATOM | 12095 | CA | LEU | B | 240 | 81.820 | 22.022 | −12.474 | 1.00 | 23.21 | B | C |
| ATOM | 12097 | CB | LEU | B | 240 | 82.645 | 22.326 | −11.208 | 1.00 | 23.26 | B | C |
| ATOM | 12100 | CG | LEU | B | 240 | 83.815 | 21.443 | −10.789 | 1.00 | 32.42 | B | C |

TABLE 4-2-continued

Coordinates of *P. alba* IspS

| ATOM | 12102 | CD1 | LEU | B | 240 | 84.539 | 20.728 | −11.964 | 1.00 | 33.31 | B | C |
|---|---|---|---|---|---|---|---|---|---|---|---|---|
| ATOM | 12106 | CD2 | LEU | B | 240 | 84.799 | 22.287 | −9.940 | 1.00 | 30.31 | B | C |
| ATOM | 12110 | C | LEU | B | 240 | 80.353 | 22.027 | −12.106 | 1.00 | 21.05 | B | C |
| ATOM | 12111 | O | LEU | B | 240 | 79.753 | 20.969 | −11.972 | 1.00 | 23.99 | B | O |
| ATOM | 12113 | N | ASP | B | 241 | 79.800 | 23.205 | −11.876 | 1.00 | 20.47 | B | N |
| ATOM | 12114 | CA | ASP | B | 241 | 78.395 | 23.319 | −11.512 | 1.00 | 20.64 | B | C |
| ATOM | 12116 | CB | ASP | B | 241 | 78.004 | 24.779 | −11.273 | 1.00 | 21.72 | B | C |
| ATOM | 12119 | CG | ASP | B | 241 | 76.721 | 24.920 | −10.461 | 1.00 | 25.74 | B | C |
| ATOM | 12120 | OD1 | ASP | B | 241 | 75.606 | 24.991 | −11.048 | 1.00 | 24.61 | B | O |
| ATOM | 12121 | OD2 | ASP | B | 241 | 76.829 | 24.948 | −9.231 | 1.00 | 20.16 | B | O |
| ATOM | 12122 | C | ASP | B | 241 | 77.513 | 22.698 | −12.610 | 1.00 | 20.65 | B | C |
| ATOM | 12123 | O | ASP | B | 241 | 76.609 | 21.925 | −12.306 | 1.00 | 20.46 | B | O |
| ATOM | 12125 | N | TYR | B | 242 | 77.816 | 22.985 | −13.876 | 1.00 | 20.03 | B | N |
| ATOM | 12126 | CA | TYR | B | 242 | 76.993 | 22.490 | −14.981 | 1.00 | 21.97 | B | C |
| ATOM | 12128 | CB | TYR | B | 242 | 77.486 | 23.024 | −16.327 | 1.00 | 21.09 | B | C |
| ATOM | 12131 | CG | TYR | B | 242 | 76.593 | 22.662 | −17.515 | 1.00 | 21.48 | B | C |
| ATOM | 12132 | CD1 | TYR | B | 242 | 75.662 | 23.564 | −18.022 | 1.00 | 20.87 | B | C |
| ATOM | 12134 | CE1 | TYR | B | 242 | 74.844 | 23.217 | −19.112 | 1.00 | 23.37 | B | C |
| ATOM | 12136 | CZ | TYR | B | 242 | 74.986 | 21.976 | −19.706 | 1.00 | 19.51 | B | C |
| ATOM | 12137 | OH | TYR | B | 242 | 74.216 | 21.612 | −20.777 | 1.00 | 27.52 | B | O |
| ATOM | 12139 | CE2 | TYR | B | 242 | 75.914 | 21.084 | −19.226 | 1.00 | 19.92 | B | C |
| ATOM | 12141 | CD2 | TYR | B | 242 | 76.702 | 21.429 | −18.138 | 1.00 | 21.77 | B | C |
| ATOM | 12143 | C | TYR | B | 242 | 76.922 | 20.967 | −15.033 | 1.00 | 22.49 | B | C |
| ATOM | 12144 | O | TYR | B | 242 | 75.836 | 20.393 | −15.206 | 1.00 | 22.20 | B | O |
| ATOM | 12146 | N | ASN | B | 243 | 78.082 | 20.324 | −14.937 | 1.00 | 22.43 | B | N |
| ATOM | 12147 | CA | ASN | B | 243 | 78.157 | 18.857 | −14.990 | 1.00 | 22.60 | B | C |
| ATOM | 12149 | CB | ASN | B | 243 | 79.601 | 18.375 | −15.194 | 1.00 | 20.63 | B | C |
| ATOM | 12152 | CG | ASN | B | 243 | 80.153 | 18.766 | −16.560 | 1.00 | 25.15 | B | C |
| ATOM | 12153 | OD1 | ASN | B | 243 | 79.389 | 18.975 | −17.507 | 1.00 | 28.79 | B | O |
| ATOM | 12154 | ND2 | ASN | B | 243 | 81.478 | 18.871 | −16.670 | 1.00 | 18.72 | B | N |
| ATOM | 12157 | C | ASN | B | 243 | 77.546 | 18.240 | −13.741 | 1.00 | 20.99 | B | C |
| ATOM | 12158 | O | ASN | B | 243 | 76.966 | 17.154 | −13.795 | 1.00 | 22.45 | B | O |
| ATOM | 12160 | N | MET | B | 244 | 77.646 | 18.942 | −12.626 | 1.00 | 19.24 | B | N |
| ATOM | 12161 | CA | MET | B | 244 | 76.979 | 18.480 | −11.426 | 1.00 | 22.91 | B | C |
| ATOM | 12163 | CB | MET | B | 244 | 77.363 | 19.339 | −10.230 | 1.00 | 22.09 | B | C |
| ATOM | 12166 | CG | MET | B | 244 | 76.629 | 18.976 | −8.959 | 1.00 | 26.36 | B | C |
| ATOM | 12169 | SD | MET | B | 244 | 76.675 | 20.330 | −7.774 | 1.00 | 40.41 | B | S |
| ATOM | 12170 | CE | MET | B | 244 | 75.425 | 21.413 | −8.512 | 1.00 | 38.87 | B | C |
| ATOM | 12174 | C | MET | B | 244 | 75.449 | 18.467 | −11.621 | 1.00 | 23.24 | B | C |
| ATOM | 12175 | O | MET | B | 244 | 74.793 | 17.460 | −11.333 | 1.00 | 24.26 | B | O |
| ATOM | 12177 | N | ILE | B | 245 | 74.898 | 19.569 | −12.120 | 1.00 | 22.08 | B | N |
| ATOM | 12178 | CA | ILE | B | 245 | 73.457 | 19.669 | −12.309 | 1.00 | 21.64 | B | C |
| ATOM | 12180 | CB | ILE | B | 245 | 73.036 | 21.093 | −12.702 | 1.00 | 22.89 | B | C |
| ATOM | 12182 | CG1 | ILE | B | 245 | 73.240 | 22.044 | −11.518 | 1.00 | 22.42 | B | C |
| ATOM | 12185 | CD1 | ILE | B | 245 | 72.776 | 23.512 | −11.793 | 1.00 | 23.27 | B | C |
| ATOM | 12189 | CG2 | ILE | B | 245 | 71.558 | 21.129 | −13.161 | 1.00 | 20.97 | B | C |
| ATOM | 12193 | C | ILE | B | 245 | 73.037 | 18.640 | −13.356 | 1.00 | 21.34 | B | C |
| ATOM | 12194 | O | ILE | B | 245 | 72.069 | 17.912 | −13.180 | 1.00 | 21.20 | B | O |
| ATOM | 12196 | N | GLN | B | 246 | 73.803 | 18.526 | −14.423 | 1.00 | 21.82 | B | N |
| ATOM | 12197 | CA | GLN | B | 246 | 73.522 | 17.493 | −15.396 | 1.00 | 22.03 | B | C |
| ATOM | 12199 | CB | GLN | B | 246 | 74.574 | 17.464 | −16.484 | 1.00 | 22.15 | B | C |
| ATOM | 12202 | CG | GLN | B | 246 | 74.215 | 16.563 | −17.638 | 1.00 | 21.61 | B | C |
| ATOM | 12205 | CD | GLN | B | 246 | 75.271 | 16.560 | −18.695 | 1.00 | 21.70 | B | C |
| ATOM | 12206 | OE1 | GLN | B | 246 | 76.364 | 16.058 | −18.472 | 1.00 | 32.02 | B | O |
| ATOM | 12207 | NE2 | GLN | B | 246 | 74.962 | 17.133 | −19.861 | 1.00 | 24.97 | B | N |
| ATOM | 12210 | C | GLN | B | 246 | 73.417 | 16.121 | −14.743 | 1.00 | 24.58 | B | C |
| ATOM | 12211 | O | GLN | B | 246 | 72.529 | 15.355 | −15.097 | 1.00 | 24.66 | B | O |
| ATOM | 12213 | N | SER | B | 247 | 74.285 | 15.797 | −13.784 | 1.00 | 23.32 | B | N |
| ATOM | 12214 | CA | SER | B | 247 | 74.229 | 14.455 | −13.209 | 1.00 | 25.50 | B | C |
| ATOM | 12216 | CB | SER | B | 247 | 75.468 | 14.111 | −12.354 | 1.00 | 24.49 | B | C |
| ATOM | 12219 | OG | SER | B | 247 | 75.372 | 14.688 | −11.056 | 1.00 | 30.70 | B | O |
| ATOM | 12221 | C | SER | B | 247 | 72.932 | 14.269 | −12.417 | 1.00 | 25.70 | B | C |
| ATOM | 12222 | O | SER | B | 247 | 72.401 | 13.167 | −12.346 | 1.00 | 26.49 | B | O |
| ATOM | 12224 | N | VAL | B | 248 | 72.412 | 15.338 | −11.833 | 1.00 | 25.46 | B | N |
| ATOM | 12225 | CA | VAL | B | 248 | 71.079 | 15.268 | −11.244 | 1.00 | 25.37 | B | C |
| ATOM | 12227 | CB | VAL | B | 248 | 70.708 | 16.577 | −10.534 | 1.00 | 25.38 | B | C |
| ATOM | 12229 | CG1 | VAL | B | 248 | 69.289 | 16.493 | −9.982 | 1.00 | 21.73 | B | C |
| ATOM | 12233 | CG2 | VAL | B | 248 | 71.737 | 16.887 | −9.411 | 1.00 | 21.11 | B | C |
| ATOM | 12237 | C | VAL | B | 248 | 70.019 | 14.910 | −12.324 | 1.00 | 27.50 | B | C |
| ATOM | 12238 | O | VAL | B | 248 | 69.186 | 14.022 | −12.114 | 1.00 | 30.45 | B | O |
| ATOM | 12240 | N | TYR | B | 249 | 70.069 | 15.575 | −13.475 | 1.00 | 25.85 | B | N |
| ATOM | 12241 | CA | TYR | B | 249 | 69.129 | 15.288 | −14.571 | 1.00 | 26.78 | B | C |
| ATOM | 12243 | CB | TYR | B | 249 | 69.407 | 16.170 | −15.807 | 1.00 | 25.46 | B | C |
| ATOM | 12246 | CG | TYR | B | 249 | 69.297 | 17.684 | −15.619 | 1.00 | 24.49 | B | C |
| ATOM | 12247 | CD1 | TYR | B | 249 | 68.579 | 18.237 | −14.570 | 1.00 | 19.54 | B | C |
| ATOM | 12249 | CE1 | TYR | B | 249 | 68.456 | 19.592 | −14.429 | 1.00 | 21.35 | B | C |
| ATOM | 12251 | CZ | TYR | B | 249 | 69.059 | 20.421 | −15.335 | 1.00 | 23.71 | B | C |
| ATOM | 12252 | OH | TYR | B | 249 | 68.955 | 21.768 | −15.170 | 1.00 | 24.97 | B | O |

TABLE 4-2-continued

Coordinates of *P. alba* IspS

| ATOM | 12254 | CE2 | TYR | B | 249 | 69.757 | 19.909 | −16.406 | 1.00 | 21.28 | B | C |
|---|---|---|---|---|---|---|---|---|---|---|---|---|
| ATOM | 12256 | CD2 | TYR | B | 249 | 69.880 | 18.553 | −16.539 | 1.00 | 22.56 | B | C |
| ATOM | 12258 | C | TYR | B | 249 | 69.190 | 13.819 | −15.025 | 1.00 | 28.33 | B | C |
| ATOM | 12259 | O | TYR | B | 249 | 68.153 | 13.182 | −15.264 | 1.00 | 27.41 | B | O |
| ATOM | 12261 | N | GLN | B | 250 | 70.411 | 13.317 | −15.184 | 1.00 | 27.94 | B | N |
| ATOM | 12262 | CA | GLN | B | 250 | 70.647 | 11.928 | −15.547 | 1.00 | 28.73 | B | C |
| ATOM | 12264 | CB | GLN | B | 250 | 72.140 | 11.676 | −15.770 | 1.00 | 28.24 | B | C |
| ATOM | 12267 | CG | GLN | B | 250 | 72.701 | 12.430 | −16.993 | 1.00 | 26.66 | B | C |
| ATOM | 12270 | CD | GLN | B | 250 | 74.230 | 12.432 | −17.049 | 1.00 | 30.68 | B | C |
| ATOM | 12271 | OE1 | GLN | B | 250 | 74.890 | 12.107 | −16.073 | 1.00 | 28.92 | B | O |
| ATOM | 12272 | NE2 | GLN | B | 250 | 74.792 | 12.819 | −18.196 | 1.00 | 27.40 | B | N |
| ATOM | 12275 | C | GLN | B | 250 | 70.044 | 10.973 | −14.505 | 1.00 | 29.66 | B | C |
| ATOM | 12276 | O | GLN | B | 250 | 69.393 | 10.007 | −14.868 | 1.00 | 30.79 | B | O |
| ATOM | 12278 | N | ARG | B | 251 | 70.179 | 11.263 | −13.219 | 1.00 | 30.47 | B | N |
| ATOM | 12279 | CA | ARG | B | 251 | 69.458 | 10.465 | −12.218 | 1.00 | 31.78 | B | C |
| ATOM | 12281 | CB | ARG | B | 251 | 69.915 | 10.799 | −10.792 | 1.00 | 32.21 | B | C |
| ATOM | 12284 | CG | ARG | B | 251 | 69.243 | 9.926 | −9.703 | 1.00 | 39.99 | B | C |
| ATOM | 12287 | CD | ARG | B | 251 | 69.850 | 10.113 | −8.314 | 1.00 | 51.23 | B | C |
| ATOM | 12290 | NE | ARG | B | 251 | 70.143 | 11.526 | −8.019 | 1.00 | 62.83 | B | N |
| ATOM | 12292 | CZ | ARG | B | 251 | 71.360 | 12.091 | −7.992 | 1.00 | 67.84 | B | C |
| ATOM | 12293 | NH1 | ARG | B | 251 | 72.469 | 11.384 | −8.228 | 1.00 | 66.43 | B | N |
| ATOM | 12296 | NH2 | ARG | B | 251 | 71.470 | 13.391 | −7.716 | 1.00 | 67.17 | B | N |
| ATOM | 12299 | C | ARG | B | 251 | 67.914 | 10.585 | −12.351 | 1.00 | 31.19 | B | C |
| ATOM | 12300 | O | ARG | B | 251 | 67.212 | 9.576 | −12.358 | 1.00 | 31.09 | B | O |
| ATOM | 12302 | N | ASP | B | 252 | 67.397 | 11.806 | −12.450 | 1.00 | 29.49 | B | N |
| ATOM | 12303 | CA | ASP | B | 252 | 65.973 | 12.026 | −12.633 | 1.00 | 27.24 | B | C |
| ATOM | 12305 | CB | ASP | B | 252 | 65.686 | 13.502 | −12.947 | 1.00 | 28.05 | B | C |
| ATOM | 12308 | CG | ASP | B | 252 | 66.003 | 14.474 | −11.791 | 1.00 | 30.79 | B | C |
| ATOM | 12309 | OD1 | ASP | B | 252 | 66.059 | 14.063 | −10.612 | 1.00 | 31.73 | B | O |
| ATOM | 12310 | OD2 | ASP | B | 252 | 66.155 | 15.691 | −12.096 | 1.00 | 28.66 | B | O |
| ATOM | 12311 | C | ASP | B | 252 | 65.474 | 11.193 | −13.831 | 1.00 | 28.33 | B | C |
| ATOM | 12312 | O | ASP | B | 252 | 64.457 | 10.512 | −13.754 | 1.00 | 28.67 | B | O |
| ATOM | 12314 | N | LEU | B | 253 | 66.203 | 11.267 | −14.940 | 1.00 | 28.59 | B | N |
| ATOM | 12315 | CA | LEU | B | 253 | 65.850 | 10.580 | −16.179 | 1.00 | 29.23 | B | C |
| ATOM | 12317 | CB | LEU | B | 253 | 66.735 | 11.070 | −17.332 | 1.00 | 26.17 | B | C |
| ATOM | 12320 | CG | LEU | B | 253 | 66.435 | 10.484 | −18.704 | 1.00 | 32.56 | B | C |
| ATOM | 12322 | CD1 | LEU | B | 253 | 64.988 | 10.790 | −19.120 | 1.00 | 22.29 | B | C |
| ATOM | 12326 | CD2 | LEU | B | 253 | 67.448 | 10.988 | −19.739 | 1.00 | 36.23 | B | C |
| ATOM | 12330 | C | LEU | B | 253 | 65.945 | 9.055 | −16.093 | 1.00 | 30.46 | B | C |
| ATOM | 12331 | O | LEU | B | 253 | 65.246 | 8.361 | −16.831 | 1.00 | 29.74 | B | O |
| ATOM | 12333 | N | ARG | B | 254 | 66.819 | 8.537 | −15.231 | 1.00 | 32.61 | B | N |
| ATOM | 12334 | CA | ARG | B | 254 | 66.942 | 7.083 | −15.057 | 1.00 | 35.04 | B | C |
| ATOM | 12336 | CB | ARG | B | 254 | 68.241 | 6.682 | −14.330 | 1.00 | 36.65 | B | C |
| ATOM | 12339 | CG | ARG | B | 254 | 69.522 | 6.685 | −15.202 | 1.00 | 39.59 | B | C |
| ATOM | 12342 | CD | ARG | B | 254 | 70.676 | 5.892 | −14.532 | 1.00 | 45.23 | B | C |
| ATOM | 12345 | NE | ARG | B | 254 | 71.001 | 6.378 | −13.184 | 1.00 | 43.70 | B | N |
| ATOM | 12347 | CZ | ARG | B | 254 | 71.747 | 7.452 | −12.921 | 1.00 | 44.00 | B | C |
| ATOM | 12348 | NH1 | ARG | B | 254 | 72.276 | 8.181 | −13.910 | 1.00 | 39.76 | B | N |
| ATOM | 12351 | NH2 | ARG | B | 254 | 71.961 | 7.807 | −11.659 | 1.00 | 43.71 | B | N |
| ATOM | 12354 | C | ARG | B | 254 | 65.720 | 6.574 | −14.306 | 1.00 | 34.86 | B | C |
| ATOM | 12355 | O | ARG | B | 254 | 65.111 | 5.593 | −14.712 | 1.00 | 35.53 | B | O |
| ATOM | 12357 | N | GLU | B | 255 | 65.346 | 7.291 | −13.251 | 1.00 | 34.73 | B | N |
| ATOM | 12358 | CA | GLU | B | 255 | 64.149 | 7.011 | −12.450 | 1.00 | 37.10 | B | C |
| ATOM | 12360 | CB | GLU | B | 255 | 64.060 | 8.073 | −11.345 | 1.00 | 39.63 | B | C |
| ATOM | 12363 | CG | GLU | B | 255 | 63.692 | 7.589 | −9.941 | 1.00 | 52.09 | B | C |
| ATOM | 12366 | CD | GLU | B | 255 | 64.217 | 8.541 | −8.844 | 1.00 | 59.96 | B | C |
| ATOM | 12367 | OE1 | GLU | B | 255 | 65.456 | 8.703 | −8.728 | 1.00 | 62.20 | B | O |
| ATOM | 12368 | OE2 | GLU | B | 255 | 63.393 | 9.120 | −8.103 | 1.00 | 63.44 | B | O |
| ATOM | 12369 | C | GLU | B | 255 | 62.851 | 7.043 | −13.298 | 1.00 | 37.49 | B | C |
| ATOM | 12370 | O | GLU | B | 255 | 61.983 | 6.172 | −13.179 | 1.00 | 38.24 | B | O |
| ATOM | 12372 | N | THR | B | 256 | 62.726 | 8.066 | −14.139 | 1.00 | 33.48 | B | N |
| ATOM | 12373 | CA | THR | B | 256 | 61.550 | 8.236 | −14.970 | 1.00 | 32.03 | B | C |
| ATOM | 12375 | CB | THR | B | 256 | 61.489 | 9.676 | −15.484 | 1.00 | 28.82 | B | C |
| ATOM | 12377 | OG1 | THR | B | 256 | 61.258 | 10.518 | −14.365 | 1.00 | 31.10 | B | O |
| ATOM | 12379 | CG2 | THR | B | 256 | 60.378 | 9.886 | −16.462 | 1.00 | 32.38 | B | C |
| ATOM | 12383 | C | THR | B | 256 | 61.529 | 7.209 | −16.104 | 1.00 | 31.37 | B | C |
| ATOM | 12384 | O | THR | B | 256 | 60.465 | 6.736 | −16.483 | 1.00 | 30.12 | B | O |
| ATOM | 12386 | N | SER | B | 257 | 62.704 | 6.859 | −16.632 | 1.00 | 32.20 | B | N |
| ATOM | 12387 | CA | SER | B | 257 | 62.816 | 5.812 | −17.662 | 1.00 | 32.63 | B | C |
| ATOM | 12389 | CB | SER | B | 257 | 64.257 | 5.674 | −18.156 | 1.00 | 32.05 | B | C |
| ATOM | 12392 | OG | SER | B | 257 | 64.640 | 6.805 | −18.913 | 1.00 | 35.00 | B | O |
| ATOM | 12394 | C | SER | B | 257 | 62.329 | 4.460 | −17.135 | 1.00 | 32.30 | B | C |
| ATOM | 12395 | O | SER | B | 257 | 61.626 | 3.731 | −17.836 | 1.00 | 32.52 | B | O |
| ATOM | 12397 | N | ARG | B | 258 | 62.687 | 4.150 | −15.893 | 1.00 | 31.83 | B | N |
| ATOM | 12398 | CA | ARG | B | 258 | 62.215 | 2.934 | −15.244 | 1.00 | 35.46 | B | C |
| ATOM | 12400 | CB | ARG | B | 258 | 62.737 | 2.777 | −13.798 | 1.00 | 37.72 | B | C |
| ATOM | 12403 | CG | ARG | B | 258 | 64.138 | 2.136 | −13.696 | 1.00 | 46.00 | B | C |
| ATOM | 12406 | CD | ARG | B | 258 | 64.423 | 1.530 | −12.295 | 1.00 | 51.03 | B | C |

TABLE 4-2-continued

Coordinates of *P. alba* IspS

| ATOM | 12409 | NE | ARG | B | 258 | 64.165 | 2.474 | −11.198 | 1.00 | 52.82 | B | N |
|---|---|---|---|---|---|---|---|---|---|---|---|---|
| ATOM | 12411 | CZ | ARG | B | 258 | 65.033 | 3.368 | −10.717 | 1.00 | 56.37 | B | C |
| ATOM | 12412 | NH1 | ARG | B | 258 | 64.663 | 4.155 | −9.715 | 1.00 | 57.59 | B | N |
| ATOM | 12415 | NH2 | ARG | B | 258 | 66.261 | 3.492 | −11.219 | 1.00 | 58.73 | B | N |
| ATOM | 12418 | C | ARG | B | 258 | 60.715 | 2.938 | −15.235 | 1.00 | 33.44 | B | C |
| ATOM | 12419 | O | ARG | B | 258 | 60.098 | 1.963 | −15.640 | 1.00 | 34.72 | B | O |
| ATOM | 12421 | N | TRP | B | 259 | 60.132 | 4.032 | −14.773 | 1.00 | 31.58 | B | N |
| ATOM | 12422 | CA | TRP | B | 259 | 58.695 | 4.182 | −14.811 | 1.00 | 31.82 | B | C |
| ATOM | 12424 | CB | TRP | B | 259 | 58.281 | 5.561 | −14.324 | 1.00 | 32.08 | B | C |
| ATOM | 12427 | CG | TRP | B | 259 | 56.866 | 5.918 | −14.621 | 1.00 | 27.02 | B | C |
| ATOM | 12428 | CD1 | TRP | B | 259 | 55.764 | 5.504 | −13.935 | 1.00 | 30.20 | B | C |
| ATOM | 12430 | NE1 | TRP | B | 259 | 54.632 | 6.051 | −14.491 | 1.00 | 34.18 | B | N |
| ATOM | 12432 | CE2 | TRP | B | 259 | 54.991 | 6.832 | −15.558 | 1.00 | 25.57 | B | C |
| ATOM | 12433 | CD2 | TRP | B | 259 | 56.394 | 6.780 | −15.666 | 1.00 | 26.24 | B | C |
| ATOM | 12434 | CE3 | TRP | B | 259 | 57.015 | 7.473 | −16.706 | 1.00 | 21.19 | B | C |
| ATOM | 12436 | CZ3 | TRP | B | 259 | 56.238 | 8.204 | −17.569 | 1.00 | 25.68 | B | C |
| ATOM | 12438 | CH2 | TRP | B | 259 | 54.848 | 8.253 | −17.423 | 1.00 | 31.07 | B | C |
| ATOM | 12440 | CZ2 | TRP | B | 259 | 54.209 | 7.562 | −16.425 | 1.00 | 26.47 | B | C |
| ATOM | 12442 | C | TRP | B | 259 | 58.158 | 3.980 | −16.222 | 1.00 | 31.90 | B | C |
| ATOM | 12443 | O | TRP | B | 259 | 57.209 | 3.231 | −16.416 | 1.00 | 34.40 | B | O |
| ATOM | 12445 | N | TRP | B | 260 | 58.755 | 4.650 | −17.201 | 1.00 | 29.58 | B | N |
| ATOM | 12446 | CA | TRP | B | 260 | 58.219 | 4.623 | −18.564 | 1.00 | 29.21 | B | C |
| ATOM | 12448 | CB | TRP | B | 260 | 59.020 | 5.542 | −19.471 | 1.00 | 28.39 | B | C |
| ATOM | 12451 | CG | TRP | B | 260 | 58.463 | 5.760 | −20.832 | 1.00 | 31.21 | B | C |
| ATOM | 12452 | CD1 | TRP | B | 260 | 59.128 | 5.613 | −22.011 | 1.00 | 32.56 | B | C |
| ATOM | 12454 | NE1 | TRP | B | 260 | 58.305 | 5.952 | −23.056 | 1.00 | 35.69 | B | N |
| ATOM | 12456 | CE2 | TRP | B | 260 | 57.088 | 6.341 | −22.564 | 1.00 | 28.01 | B | C |
| ATOM | 12457 | CD2 | TRP | B | 260 | 57.140 | 6.220 | −21.171 | 1.00 | 26.28 | B | C |
| ATOM | 12458 | CE3 | TRP | B | 260 | 56.006 | 6.556 | −20.426 | 1.00 | 29.49 | B | C |
| ATOM | 12460 | CZ3 | TRP | B | 260 | 54.871 | 6.979 | −21.092 | 1.00 | 27.25 | B | C |
| ATOM | 12462 | CH2 | TRP | B | 260 | 54.851 | 7.081 | −22.477 | 1.00 | 26.73 | B | C |
| ATOM | 12464 | CZ2 | TRP | B | 260 | 55.947 | 6.764 | −23.232 | 1.00 | 32.88 | B | C |
| ATOM | 12466 | C | TRP | B | 260 | 58.244 | 3.226 | −19.150 | 1.00 | 27.50 | B | C |
| ATOM | 12467 | O | TRP | B | 260 | 57.308 | 2.844 | −19.832 | 1.00 | 23.27 | B | O |
| ATOM | 12469 | N | ARG | B | 261 | 59.324 | 2.503 | −18.865 | 1.00 | 29.60 | B | N |
| ATOM | 12470 | CA | ARG | B | 261 | 59.551 | 1.144 | −19.348 | 1.00 | 34.53 | B | C |
| ATOM | 12472 | CB | ARG | B | 261 | 60.971 | 0.697 | −18.977 | 1.00 | 35.16 | B | C |
| ATOM | 12475 | CG | ARG | B | 261 | 61.605 | −0.290 | −19.932 | 1.00 | 46.23 | B | C |
| ATOM | 12478 | CD | ARG | B | 261 | 63.068 | −0.626 | −19.554 | 1.00 | 55.36 | B | C |
| ATOM | 12481 | NE | ARG | B | 261 | 63.895 | 0.584 | −19.412 | 1.00 | 60.95 | B | N |
| ATOM | 12483 | CZ | ARG | B | 261 | 64.475 | 1.013 | −18.281 | 1.00 | 63.65 | B | C |
| ATOM | 12484 | NH1 | ARG | B | 261 | 65.189 | 2.134 | −18.300 | 1.00 | 57.86 | B | N |
| ATOM | 12487 | NH2 | ARG | B | 261 | 64.369 | 0.342 | −17.130 | 1.00 | 65.79 | B | N |
| ATOM | 12490 | C | ARG | B | 261 | 58.509 | 0.198 | −18.741 | 1.00 | 37.14 | B | C |
| ATOM | 12491 | O | ARG | B | 261 | 57.920 | −0.634 | −19.435 | 1.00 | 39.01 | B | O |
| ATOM | 12493 | N | ARG | B | 262 | 58.284 | 0.360 | −17.442 | 1.00 | 38.02 | B | N |
| ATOM | 12494 | CA | ARG | B | 262 | 57.177 | −0.268 | −16.716 | 1.00 | 39.33 | B | C |
| ATOM | 12496 | CB | ARG | B | 262 | 57.015 | 0.410 | −15.345 | 1.00 | 43.52 | B | C |
| ATOM | 12499 | CG | ARG | B | 262 | 56.465 | −0.472 | −14.256 | 1.00 | 52.63 | B | C |
| ATOM | 12502 | CD | ARG | B | 262 | 57.576 | −1.181 | −13.525 | 1.00 | 62.09 | B | C |
| ATOM | 12505 | NE | ARG | B | 262 | 57.050 | −2.325 | −12.786 | 1.00 | 69.73 | B | N |
| ATOM | 12507 | CZ | ARG | B | 262 | 56.722 | −3.494 | −13.333 | 1.00 | 71.95 | B | C |
| ATOM | 12508 | NH1 | ARG | B | 262 | 56.865 | −3.698 | −14.642 | 1.00 | 69.88 | B | N |
| ATOM | 12511 | NH2 | ARG | B | 262 | 56.243 | −4.462 | −12.561 | 1.00 | 73.11 | B | N |
| ATOM | 12514 | C | ARG | B | 262 | 55.852 | −0.134 | −17.434 | 1.00 | 34.28 | B | C |
| ATOM | 12515 | O | ARG | B | 262 | 55.161 | −1.109 | −17.686 | 1.00 | 36.30 | B | O |
| ATOM | 12517 | N | VAL | B | 263 | 55.504 | 1.100 | −17.747 | 1.00 | 30.95 | B | N |
| ATOM | 12518 | CA | VAL | B | 263 | 54.232 | 1.419 | −18.372 | 1.00 | 28.88 | B | C |
| ATOM | 12520 | CB | VAL | B | 263 | 53.991 | 2.937 | −18.339 | 1.00 | 29.02 | B | C |
| ATOM | 12522 | CG1 | VAL | B | 263 | 53.972 | 3.419 | −16.887 | 1.00 | 31.64 | B | C |
| ATOM | 12526 | CG2 | VAL | B | 263 | 52.725 | 3.282 | −19.018 | 1.00 | 23.71 | B | C |
| ATOM | 12530 | C | VAL | B | 263 | 54.178 | 0.879 | −19.806 | 1.00 | 28.33 | B | C |
| ATOM | 12531 | O | VAL | B | 263 | 53.120 | 0.527 | −20.282 | 1.00 | 28.41 | B | O |
| ATOM | 12533 | N | GLY | B | 264 | 55.328 | 0.793 | −20.473 | 1.00 | 28.72 | B | N |
| ATOM | 12534 | CA | GLY | B | 264 | 55.455 | 0.142 | −21.782 | 1.00 | 28.49 | B | C |
| ATOM | 12537 | C | GLY | B | 264 | 54.407 | 0.496 | −22.813 | 1.00 | 29.83 | B | C |
| ATOM | 12538 | O | GLY | B | 264 | 54.075 | −0.304 | −23.665 | 1.00 | 33.27 | B | O |
| ATOM | 12540 | N | LEU | B | 265 | 53.866 | 1.692 | −22.740 | 1.00 | 32.92 | B | N |
| ATOM | 12541 | CA | LEU | B | 265 | 52.709 | 2.035 | −23.561 | 1.00 | 36.59 | B | C |
| ATOM | 12543 | CB | LEU | B | 265 | 52.038 | 3.282 | −22.981 | 1.00 | 34.56 | B | C |
| ATOM | 12546 | CG | LEU | B | 265 | 50.645 | 3.685 | −23.411 | 1.00 | 34.01 | B | C |
| ATOM | 12548 | CD1 | LEU | B | 265 | 49.599 | 2.606 | −23.171 | 1.00 | 25.90 | B | C |
| ATOM | 12552 | CD2 | LEU | B | 265 | 50.267 | 4.994 | −22.672 | 1.00 | 34.22 | B | C |
| ATOM | 12556 | C | LEU | B | 265 | 53.113 | 2.229 | −25.033 | 1.00 | 41.17 | B | C |
| ATOM | 12557 | O | LEU | B | 265 | 52.405 | 1.785 | −25.947 | 1.00 | 40.79 | B | O |
| ATOM | 12559 | N | ALA | B | 266 | 54.263 | 2.867 | −25.250 | 1.00 | 45.34 | B | N |
| ATOM | 12560 | CA | ALA | B | 266 | 54.839 | 3.029 | −26.591 | 1.00 | 49.21 | B | C |
| ATOM | 12562 | CB | ALA | B | 266 | 56.169 | 3.765 | −26.497 | 1.00 | 51.02 | B | C |

TABLE 4-2-continued

Coordinates of *P. alba* IspS

| ATOM | 12566 | C | ALA | B | 266 | 55.042 | 1.697 | −27.325 | 1.00 | 51.05 | B | C |
|---|---|---|---|---|---|---|---|---|---|---|---|---|
| ATOM | 12567 | O | ALA | B | 266 | 54.816 | 1.605 | −28.525 | 1.00 | 54.29 | B | O |
| ATOM | 12569 | N | THR | B | 267 | 55.487 | 0.674 | −26.602 | 1.00 | 51.62 | B | N |
| ATOM | 12570 | CA | THR | B | 267 | 55.674 | −0.659 | −27.166 | 1.00 | 50.64 | B | C |
| ATOM | 12572 | CB | THR | B | 267 | 56.249 | −1.603 | −26.109 | 1.00 | 50.95 | B | C |
| ATOM | 12574 | OG1 | THR | B | 267 | 57.237 | −0.904 | −25.348 | 1.00 | 53.05 | B | O |
| ATOM | 12576 | CG2 | THR | B | 267 | 56.856 | −2.837 | −26.747 | 1.00 | 53.61 | B | C |
| ATOM | 12580 | C | THR | B | 267 | 54.363 | −1.270 | −27.629 | 1.00 | 49.87 | B | C |
| ATOM | 12581 | O | THR | B | 267 | 54.276 | −1.822 | −28.729 | 1.00 | 52.54 | B | O |
| ATOM | 12583 | N | LYS | B | 268 | 53.345 | −1.168 | −26.781 | 1.00 | 47.07 | B | N |
| ATOM | 12584 | CA | LYS | B | 268 | 52.106 | −1.927 | −26.953 | 1.00 | 45.30 | B | C |
| ATOM | 12586 | CB | LYS | B | 268 | 51.514 | −2.270 | −25.578 | 1.00 | 45.48 | B | C |
| ATOM | 12589 | CG | LYS | B | 268 | 52.430 | −3.115 | −24.675 | 1.00 | 45.38 | B | C |
| ATOM | 12592 | CD | LYS | B | 268 | 52.465 | −4.594 | −25.090 | 1.00 | 49.05 | B | C |
| ATOM | 12595 | CE | LYS | B | 268 | 53.528 | −5.398 | −24.328 | 1.00 | 51.83 | B | C |
| ATOM | 12598 | NZ | LYS | B | 268 | 53.838 | −6.705 | −24.985 | 1.00 | 54.82 | B | N |
| ATOM | 12602 | C | LYS | B | 268 | 51.078 | −1.207 | −27.819 | 1.00 | 43.95 | B | C |
| ATOM | 12603 | O | LYS | B | 268 | 50.152 | −1.829 | −28.343 | 1.00 | 44.75 | B | O |
| ATOM | 12605 | N | LEU | B | 269 | 51.229 | 0.105 | −27.947 | 1.00 | 43.27 | B | N |
| ATOM | 12606 | CA | LEU | B | 269 | 50.456 | 0.896 | −28.900 | 1.00 | 42.83 | B | C |
| ATOM | 12608 | CB | LEU | B | 269 | 50.081 | 2.274 | −28.316 | 1.00 | 42.53 | B | C |
| ATOM | 12611 | CG | LEU | B | 269 | 48.694 | 2.512 | −27.709 | 1.00 | 42.48 | B | C |
| ATOM | 12613 | CD1 | LEU | B | 269 | 48.340 | 1.537 | −26.633 | 1.00 | 40.39 | B | C |
| ATOM | 12617 | CD2 | LEU | B | 269 | 48.603 | 3.935 | −27.181 | 1.00 | 43.69 | B | C |
| ATOM | 12621 | C | LEU | B | 269 | 51.341 | 1.081 | −30.134 | 1.00 | 43.67 | B | C |
| ATOM | 12622 | O | LEU | B | 269 | 52.298 | 1.875 | −30.115 | 1.00 | 44.75 | B | O |
| ATOM | 12624 | N | HIS | B | 270 | 51.014 | 0.353 | −31.200 | 1.00 | 42.52 | B | N |
| ATOM | 12625 | CA | HIS | B | 270 | 51.820 | 0.323 | −32.430 | 1.00 | 42.36 | B | C |
| ATOM | 12627 | CB | HIS | B | 270 | 51.297 | −0.765 | −33.406 | 1.00 | 44.29 | B | C |
| ATOM | 12630 | CG | HIS | B | 270 | 50.914 | −2.062 | −32.743 | 1.00 | 55.81 | B | C |
| ATOM | 12631 | ND1 | HIS | B | 270 | 51.604 | −2.596 | −31.670 | 1.00 | 59.93 | B | N |
| ATOM | 12633 | CE1 | HIS | B | 270 | 51.038 | −3.734 | −31.307 | 1.00 | 61.45 | B | C |
| ATOM | 12635 | NE2 | HIS | B | 270 | 50.011 | −3.964 | −32.106 | 1.00 | 62.50 | B | N |
| ATOM | 12637 | CD2 | HIS | B | 270 | 49.910 | −2.935 | −33.012 | 1.00 | 61.72 | B | C |
| ATOM | 12639 | C | HIS | B | 270 | 51.862 | 1.683 | −33.164 | 1.00 | 38.47 | B | C |
| ATOM | 12640 | O | HIS | B | 270 | 52.821 | 1.980 | −33.872 | 1.00 | 36.44 | B | O |
| ATOM | 12642 | N | PHE | B | 271 | 50.813 | 2.487 | −33.019 | 1.00 | 34.67 | B | N |
| ATOM | 12643 | CA | PHE | B | 271 | 50.782 | 3.831 | −33.616 | 1.00 | 35.53 | B | C |
| ATOM | 12645 | CB | PHE | B | 271 | 49.327 | 4.306 | −33.814 | 1.00 | 35.09 | B | C |
| ATOM | 12648 | CG | PHE | B | 271 | 48.598 | 4.542 | −32.527 | 1.00 | 32.41 | B | C |
| ATOM | 12649 | CD1 | PHE | B | 271 | 48.680 | 5.764 | −31.891 | 1.00 | 36.89 | B | C |
| ATOM | 12651 | CE1 | PHE | B | 271 | 48.031 | 5.986 | −30.662 | 1.00 | 42.82 | B | C |
| ATOM | 12653 | CZ | PHE | B | 271 | 47.311 | 4.955 | −30.061 | 1.00 | 41.42 | B | C |
| ATOM | 12655 | CE2 | PHE | B | 271 | 47.234 | 3.714 | −30.695 | 1.00 | 43.35 | B | C |
| ATOM | 12657 | CD2 | PHE | B | 271 | 47.881 | 3.516 | −31.920 | 1.00 | 37.61 | B | C |
| ATOM | 12659 | C | PHE | B | 271 | 51.570 | 4.893 | −32.797 | 1.00 | 37.13 | B | C |
| ATOM | 12660 | O | PHE | B | 271 | 51.846 | 5.976 | −33.321 | 1.00 | 37.34 | B | O |
| ATOM | 12662 | N | ALA | B | 272 | 51.940 | 4.589 | −31.543 | 1.00 | 37.26 | B | N |
| ATOM | 12663 | CA | ALA | B | 272 | 52.442 | 5.634 | −30.600 | 1.00 | 38.89 | B | C |
| ATOM | 12665 | CB | ALA | B | 272 | 52.094 | 5.270 | −29.140 | 1.00 | 36.66 | B | C |
| ATOM | 12669 | C | ALA | B | 272 | 53.938 | 5.971 | −30.703 | 1.00 | 39.07 | B | C |
| ATOM | 12670 | O | ALA | B | 272 | 54.797 | 5.092 | −30.725 | 1.00 | 39.92 | B | O |
| ATOM | 12672 | N | ARG | B | 273 | 54.230 | 7.265 | −30.746 | 1.00 | 41.88 | B | N |
| ATOM | 12673 | CA | ARG | B | 273 | 55.598 | 7.754 | −30.590 | 1.00 | 43.68 | B | C |
| ATOM | 12675 | CB | ARG | B | 273 | 55.688 | 9.247 | −30.928 | 1.00 | 45.24 | B | C |
| ATOM | 12678 | CG | ARG | B | 273 | 55.566 | 9.610 | −32.409 | 1.00 | 54.15 | B | C |
| ATOM | 12681 | CD | ARG | B | 273 | 55.488 | 11.141 | −32.589 | 1.00 | 58.80 | B | C |
| ATOM | 12684 | NE | ARG | B | 273 | 54.171 | 11.685 | −32.226 | 1.00 | 59.04 | B | N |
| ATOM | 12686 | CZ | ARG | B | 273 | 53.934 | 12.957 | −31.892 | 1.00 | 67.66 | B | C |
| ATOM | 12687 | NH1 | ARG | B | 273 | 54.925 | 13.849 | −31.851 | 1.00 | 73.10 | B | N |
| ATOM | 12690 | NH2 | ARG | B | 273 | 52.699 | 13.348 | −31.579 | 1.00 | 66.54 | B | N |
| ATOM | 12693 | C | ARG | B | 273 | 56.033 | 7.570 | −29.146 | 1.00 | 42.37 | B | C |
| ATOM | 12694 | O | ARG | B | 273 | 55.259 | 7.841 | −28.231 | 1.00 | 44.16 | B | O |
| ATOM | 12696 | N | ASP | B | 274 | 57.259 | 7.102 | −28.953 | 1.00 | 41.17 | B | N |
| ATOM | 12697 | CA | ASP | B | 274 | 57.943 | 7.200 | −27.663 | 1.00 | 39.65 | B | C |
| ATOM | 12699 | CB | ASP | B | 274 | 58.887 | 6.003 | −27.479 | 1.00 | 37.65 | B | C |
| ATOM | 12702 | CG | ASP | B | 274 | 59.781 | 6.132 | −26.246 | 1.00 | 41.72 | B | C |
| ATOM | 12703 | OD1 | ASP | B | 274 | 59.773 | 7.202 | −25.594 | 1.00 | 40.60 | B | O |
| ATOM | 12704 | OD2 | ASP | B | 274 | 60.514 | 5.165 | −25.926 | 1.00 | 46.31 | B | O |
| ATOM | 12705 | C | ASP | B | 274 | 58.730 | 8.542 | −27.618 | 1.00 | 39.30 | B | C |
| ATOM | 12706 | O | ASP | B | 274 | 59.720 | 8.711 | −28.349 | 1.00 | 38.18 | B | O |
| ATOM | 12708 | N | ARG | B | 275 | 58.307 | 9.459 | −26.744 | 1.00 | 38.02 | B | N |
| ATOM | 12709 | CA | ARG | B | 275 | 58.890 | 10.796 | −26.645 | 1.00 | 38.08 | B | C |
| ATOM | 12711 | CB | ARG | B | 275 | 57.833 | 11.834 | −27.058 | 1.00 | 39.92 | B | C |
| ATOM | 12714 | CG | ARG | B | 275 | 57.840 | 12.200 | −28.556 | 1.00 | 47.80 | B | C |
| ATOM | 12717 | CD | ARG | B | 275 | 58.691 | 13.450 | −28.835 | 1.00 | 61.16 | B | C |
| ATOM | 12720 | NE | ARG | B | 275 | 58.526 | 13.945 | −30.206 | 1.00 | 68.47 | B | N |
| ATOM | 12722 | CZ | ARG | B | 275 | 59.096 | 13.401 | −31.281 | 1.00 | 74.79 | B | C |

TABLE 4-2-continued

Coordinates of *P. alba* IspS

| ATOM | 12723 | NH1 | ARG | B | 275 | 59.875 | 12.326 | −31.169 | 1.00 | 76.37 | B | N |
|---|---|---|---|---|---|---|---|---|---|---|---|---|
| ATOM | 12726 | NH2 | ARG | B | 275 | 58.876 | 13.926 | −32.484 | 1.00 | 75.18 | B | N |
| ATOM | 12729 | C | ARG | B | 275 | 59.425 | 11.147 | −25.254 | 1.00 | 37.19 | B | C |
| ATOM | 12730 | O | ARG | B | 275 | 59.433 | 12.316 | −24.879 | 1.00 | 36.87 | B | O |
| ATOM | 12732 | N | LEU | B | 276 | 59.886 | 10.160 | −24.485 | 1.00 | 37.00 | B | N |
| ATOM | 12733 | CA | LEU | B | 276 | 60.295 | 10.426 | −23.098 | 1.00 | 34.98 | B | C |
| ATOM | 12735 | CB | LEU | B | 276 | 60.573 | 9.134 | −22.292 | 1.00 | 36.67 | B | C |
| ATOM | 12738 | CG | LEU | B | 276 | 60.890 | 9.375 | −20.797 | 1.00 | 35.76 | B | C |
| ATOM | 12740 | CD1 | LEU | B | 276 | 59.754 | 10.147 | −20.115 | 1.00 | 33.92 | B | C |
| ATOM | 12744 | CD2 | LEU | B | 276 | 61.169 | 8.113 | −20.053 | 1.00 | 36.13 | B | C |
| ATOM | 12748 | C | LEU | B | 276 | 61.503 | 11.363 | −23.013 | 1.00 | 32.92 | B | C |
| ATOM | 12749 | O | LEU | B | 276 | 61.435 | 12.361 | −22.318 | 1.00 | 31.67 | B | O |
| ATOM | 12751 | N | ILE | B | 277 | 62.582 | 11.055 | −23.725 | 1.00 | 30.95 | B | N |
| ATOM | 12752 | CA | ILE | B | 277 | 63.822 | 11.841 | −23.617 | 1.00 | 29.96 | B | C |
| ATOM | 12754 | CB | ILE | B | 277 | 64.948 | 11.249 | −24.510 | 1.00 | 31.64 | B | C |
| ATOM | 12756 | CG1 | ILE | B | 277 | 65.404 | 9.882 | −23.979 | 1.00 | 34.19 | B | C |
| ATOM | 12759 | CD1 | ILE | B | 277 | 66.155 | 9.043 | −25.015 | 1.00 | 37.10 | B | C |
| ATOM | 12763 | CG2 | ILE | B | 277 | 66.155 | 12.185 | −24.569 | 1.00 | 30.97 | B | C |
| ATOM | 12767 | C | ILE | B | 277 | 63.591 | 13.296 | −24.024 | 1.00 | 29.71 | B | C |
| ATOM | 12768 | O | ILE | B | 277 | 64.075 | 14.213 | −23.367 | 1.00 | 29.06 | B | O |
| ATOM | 12770 | N | GLU | B | 278 | 62.851 | 13.492 | −25.113 | 1.00 | 28.47 | B | N |
| ATOM | 12771 | CA | GLU | B | 278 | 62.515 | 14.814 | −25.599 | 1.00 | 30.52 | B | C |
| ATOM | 12773 | CB | GLU | B | 278 | 61.773 | 14.746 | −26.949 | 1.00 | 32.74 | B | C |
| ATOM | 12776 | CG | GLU | B | 278 | 62.616 | 14.225 | −28.148 | 1.00 | 44.05 | B | C |
| ATOM | 12779 | CD | GLU | B | 278 | 62.477 | 12.706 | −28.437 | 1.00 | 50.83 | B | C |
| ATOM | 12780 | OE1 | GLU | B | 278 | 62.589 | 11.868 | −27.508 | 1.00 | 47.29 | B | O |
| ATOM | 12781 | OE2 | GLU | B | 278 | 62.263 | 12.357 | −29.624 | 1.00 | 59.50 | B | O |
| ATOM | 12782 | C | GLU | B | 278 | 61.650 | 15.529 | −24.554 | 1.00 | 29.96 | B | C |
| ATOM | 12783 | O | GLU | B | 278 | 61.811 | 16.720 | −24.328 | 1.00 | 29.51 | B | O |
| ATOM | 12785 | N | SER | B | 279 | 60.753 | 14.787 | −23.900 | 1.00 | 27.64 | B | N |
| ATOM | 12786 | CA | SER | B | 279 | 59.880 | 15.369 | −22.906 | 1.00 | 24.85 | B | C |
| ATOM | 12788 | CB | SER | B | 279 | 58.779 | 14.387 | −22.528 | 1.00 | 25.36 | B | C |
| ATOM | 12791 | OG | SER | B | 279 | 57.866 | 14.222 | −23.614 | 1.00 | 31.09 | B | O |
| ATOM | 12793 | C | SER | B | 279 | 60.692 | 15.817 | −21.689 | 1.00 | 24.19 | B | C |
| ATOM | 12794 | O | SER | B | 279 | 60.402 | 16.841 | −21.072 | 1.00 | 20.81 | B | O |
| ATOM | 12796 | N | PHE | B | 280 | 61.726 | 15.060 | −21.358 | 1.00 | 22.21 | B | N |
| ATOM | 12797 | CA | PHE | B | 280 | 62.538 | 15.405 | −20.233 | 1.00 | 22.68 | B | C |
| ATOM | 12799 | CB | PHE | B | 280 | 63.394 | 14.219 | −19.801 | 1.00 | 23.70 | B | C |
| ATOM | 12802 | CG | PHE | B | 280 | 63.993 | 14.420 | −18.458 | 1.00 | 22.17 | B | C |
| ATOM | 12803 | CD1 | PHE | B | 280 | 63.282 | 14.110 | −17.326 | 1.00 | 26.73 | B | C |
| ATOM | 12805 | CE1 | PHE | B | 280 | 63.815 | 14.336 | −16.082 | 1.00 | 28.79 | B | C |
| ATOM | 12807 | CZ | PHE | B | 280 | 65.071 | 14.912 | −15.977 | 1.00 | 26.30 | B | C |
| ATOM | 12809 | CE2 | PHE | B | 280 | 65.767 | 15.240 | −17.094 | 1.00 | 23.82 | B | C |
| ATOM | 12811 | CD2 | PHE | B | 280 | 65.224 | 15.010 | −18.332 | 1.00 | 25.89 | B | C |
| ATOM | 12813 | C | PHE | B | 280 | 63.421 | 16.639 | −20.521 | 1.00 | 23.35 | B | C |
| ATOM | 12814 | O | PHE | B | 280 | 63.538 | 17.546 | −19.684 | 1.00 | 22.15 | B | O |
| ATOM | 12816 | N | TYR | B | 281 | 64.035 | 16.663 | −21.702 | 1.00 | 22.05 | B | N |
| ATOM | 12817 | CA | TYR | B | 281 | 64.744 | 17.845 | −22.179 | 1.00 | 22.89 | B | C |
| ATOM | 12819 | CB | TYR | B | 281 | 65.243 | 17.599 | −23.613 | 1.00 | 24.85 | B | C |
| ATOM | 12822 | CG | TYR | B | 281 | 65.725 | 18.824 | −24.340 | 1.00 | 27.86 | B | C |
| ATOM | 12823 | CD1 | TYR | B | 281 | 67.038 | 19.263 | −24.199 | 1.00 | 29.60 | B | C |
| ATOM | 12825 | CE1 | TYR | B | 281 | 67.481 | 20.396 | −24.830 | 1.00 | 30.12 | B | C |
| ATOM | 12827 | CZ | TYR | B | 281 | 66.619 | 21.106 | −25.645 | 1.00 | 27.86 | B | C |
| ATOM | 12828 | OH | TYR | B | 281 | 67.094 | 22.218 | −26.293 | 1.00 | 40.12 | B | O |
| ATOM | 12830 | CE2 | TYR | B | 281 | 65.321 | 20.681 | −25.831 | 1.00 | 27.61 | B | C |
| ATOM | 12832 | CD2 | TYR | B | 281 | 64.880 | 19.541 | −25.164 | 1.00 | 26.08 | B | C |
| ATOM | 12834 | C | TYR | B | 281 | 63.774 | 19.033 | −22.107 | 1.00 | 23.97 | B | C |
| ATOM | 12835 | O | TYR | B | 281 | 64.114 | 20.107 | −21.638 | 1.00 | 23.50 | B | O |
| ATOM | 12837 | N | TRP | B | 282 | 62.535 | 18.821 | −22.522 | 1.00 | 23.00 | B | N |
| ATOM | 12838 | CA | TRP | B | 282 | 61.567 | 19.906 | −22.475 | 1.00 | 23.33 | B | C |
| ATOM | 12840 | CB | TRP | B | 282 | 60.235 | 19.447 | −23.059 | 1.00 | 22.37 | B | C |
| ATOM | 12843 | CG | TRP | B | 282 | 59.154 | 20.412 | −22.895 | 1.00 | 22.74 | B | C |
| ATOM | 12844 | CD1 | TRP | B | 282 | 58.337 | 20.555 | −21.821 | 1.00 | 22.39 | B | C |
| ATOM | 12846 | NE1 | TRP | B | 282 | 57.435 | 21.564 | −22.047 | 1.00 | 23.45 | B | N |
| ATOM | 12848 | CE2 | TRP | B | 282 | 57.667 | 22.082 | −23.291 | 1.00 | 23.69 | B | C |
| ATOM | 12849 | CD2 | TRP | B | 282 | 58.742 | 21.375 | −23.850 | 1.00 | 22.10 | B | C |
| ATOM | 12850 | CE3 | TRP | B | 282 | 59.184 | 21.712 | −25.131 | 1.00 | 26.55 | B | C |
| ATOM | 12852 | CZ3 | TRP | B | 282 | 58.546 | 22.733 | −25.798 | 1.00 | 28.88 | B | C |
| ATOM | 12854 | CH2 | TRP | B | 282 | 57.483 | 23.424 | −25.210 | 1.00 | 30.17 | B | C |
| ATOM | 12856 | CZ2 | TRP | B | 282 | 57.028 | 23.111 | −23.960 | 1.00 | 27.03 | B | C |
| ATOM | 12858 | C | TRP | B | 282 | 61.418 | 20.387 | −21.028 | 1.00 | 22.80 | B | C |
| ATOM | 12859 | O | TRP | B | 282 | 61.406 | 21.593 | −20.769 | 1.00 | 20.61 | B | O |
| ATOM | 12861 | N | ALA | B | 283 | 61.308 | 19.431 | −20.103 | 1.00 | 21.05 | B | N |
| ATOM | 12862 | CA | ALA | B | 283 | 61.084 | 19.723 | −18.692 | 1.00 | 20.62 | B | C |
| ATOM | 12864 | CB | ALA | B | 283 | 60.816 | 18.452 | −17.899 | 1.00 | 18.78 | B | C |
| ATOM | 12868 | C | ALA | B | 283 | 62.249 | 20.468 | −18.081 | 1.00 | 19.81 | B | C |
| ATOM | 12869 | O | ALA | B | 283 | 62.048 | 21.246 | −17.179 | 1.00 | 19.59 | B | O |
| ATOM | 12871 | N | VAL | B | 284 | 63.459 | 20.228 | −18.570 | 1.00 | 21.14 | B | N |

TABLE 4-2-continued

Coordinates of *P. alba* IspS

| ATOM | 12872 | CA | VAL | B | 284 | 64.621 | 20.924 | −18.054 | 1.00 | 22.45 | B | C |
|---|---|---|---|---|---|---|---|---|---|---|---|---|
| ATOM | 12874 | CB | VAL | B | 284 | 65.935 | 20.350 | −18.615 | 1.00 | 25.86 | B | C |
| ATOM | 12876 | CG1 | VAL | B | 284 | 66.234 | 18.966 | −17.953 | 1.00 | 18.72 | B | C |
| ATOM | 12880 | CG2 | VAL | B | 284 | 67.075 | 21.325 | −18.378 | 1.00 | 20.18 | B | C |
| ATOM | 12884 | C | VAL | B | 284 | 64.537 | 22.416 | −18.333 | 1.00 | 23.71 | B | C |
| ATOM | 12885 | O | VAL | B | 284 | 64.993 | 23.221 | −17.526 | 1.00 | 22.26 | B | O |
| ATOM | 12887 | N | GLY | B | 285 | 63.948 | 22.793 | −19.464 | 1.00 | 21.46 | B | N |
| ATOM | 12888 | CA | GLY | B | 285 | 63.763 | 24.215 | −19.762 | 1.00 | 20.96 | B | C |
| ATOM | 12891 | C | GLY | B | 285 | 62.773 | 24.857 | −18.808 | 1.00 | 21.82 | B | C |
| ATOM | 12892 | O | GLY | B | 285 | 62.909 | 26.011 | −18.460 | 1.00 | 21.74 | B | O |
| ATOM | 12894 | N | VAL | B | 286 | 61.794 | 24.090 | −18.345 | 1.00 | 22.60 | B | N |
| ATOM | 12895 | CA | VAL | B | 286 | 60.781 | 24.620 | −17.450 | 1.00 | 20.48 | B | C |
| ATOM | 12897 | CB | VAL | B | 286 | 59.539 | 23.732 | −17.498 | 1.00 | 23.12 | B | C |
| ATOM | 12899 | CG1 | VAL | B | 286 | 58.485 | 24.177 | −16.490 | 1.00 | 20.49 | B | C |
| ATOM | 12903 | CG2 | VAL | B | 286 | 58.976 | 23.732 | −18.955 | 1.00 | 17.84 | B | C |
| ATOM | 12907 | C | VAL | B | 286 | 61.309 | 24.792 | −16.046 | 1.00 | 20.31 | B | C |
| ATOM | 12908 | O | VAL | B | 286 | 61.106 | 25.842 | −15.436 | 1.00 | 22.39 | B | O |
| ATOM | 12910 | N | ALA | B | 287 | 61.979 | 23.772 | −15.527 | 1.00 | 19.27 | B | N |
| ATOM | 12911 | CA | ALA | B | 287 | 62.563 | 23.827 | −14.186 | 1.00 | 20.62 | B | C |
| ATOM | 12913 | CB | ALA | B | 287 | 61.690 | 23.117 | −13.227 | 1.00 | 22.01 | B | C |
| ATOM | 12917 | C | ALA | B | 287 | 63.988 | 23.242 | −14.163 | 1.00 | 21.88 | B | C |
| ATOM | 12918 | O | ALA | B | 287 | 64.196 | 22.022 | −14.069 | 1.00 | 24.85 | B | O |
| ATOM | 12920 | N | PHE | B | 288 | 64.972 | 24.115 | −14.247 | 1.00 | 20.90 | B | N |
| ATOM | 12921 | CA | PHE | B | 288 | 66.345 | 23.674 | −14.426 | 1.00 | 21.67 | B | C |
| ATOM | 12923 | CB | PHE | B | 288 | 67.122 | 24.674 | −15.275 | 1.00 | 22.83 | B | C |
| ATOM | 12926 | CG | PHE | B | 288 | 67.541 | 25.900 | −14.520 | 1.00 | 23.91 | B | C |
| ATOM | 12927 | CD1 | PHE | B | 288 | 68.710 | 25.905 | −13.784 | 1.00 | 33.80 | B | C |
| ATOM | 12929 | CE1 | PHE | B | 288 | 69.088 | 27.037 | −13.074 | 1.00 | 37.48 | B | C |
| ATOM | 12931 | CZ | PHE | B | 288 | 68.287 | 28.167 | −13.095 | 1.00 | 31.38 | B | C |
| ATOM | 12933 | CE2 | PHE | B | 288 | 67.137 | 28.167 | −13.821 | 1.00 | 36.32 | B | C |
| ATOM | 12935 | CD2 | PHE | B | 288 | 66.761 | 27.029 | −14.529 | 1.00 | 34.62 | B | C |
| ATOM | 12937 | C | PHE | B | 288 | 67.047 | 23.497 | −13.099 | 1.00 | 24.48 | B | C |
| ATOM | 12938 | O | PHE | B | 288 | 68.005 | 22.741 | −13.031 | 1.00 | 23.65 | B | O |
| ATOM | 12940 | N | GLU | B | 289 | 66.587 | 24.190 | −12.057 | 1.00 | 26.02 | B | N |
| ATOM | 12941 | CA | GLU | B | 289 | 67.310 | 24.197 | −10.792 | 1.00 | 29.62 | B | C |
| ATOM | 12943 | CB | GLU | B | 289 | 66.689 | 25.166 | −9.776 | 1.00 | 31.32 | B | C |
| ATOM | 12946 | CG | GLU | B | 289 | 66.721 | 26.644 | −10.177 | 1.00 | 36.70 | B | C |
| ATOM | 12949 | CD | GLU | B | 289 | 65.440 | 27.118 | −10.890 | 1.00 | 45.07 | B | C |
| ATOM | 12950 | OE1 | GLU | B | 289 | 65.081 | 28.295 | −10.677 | 1.00 | 47.42 | B | O |
| ATOM | 12951 | OE2 | GLU | B | 289 | 64.793 | 26.352 | −11.659 | 1.00 | 39.96 | B | O |
| ATOM | 12952 | C | GLU | B | 289 | 67.350 | 22.795 | −10.180 | 1.00 | 29.55 | B | C |
| ATOM | 12953 | O | GLU | B | 289 | 66.350 | 22.084 | −10.180 | 1.00 | 30.10 | B | O |
| ATOM | 12955 | N | PRO | B | 290 | 68.495 | 22.419 | −9.606 | 1.00 | 29.22 | B | N |
| ATOM | 12956 | CA | PRO | B | 290 | 68.716 | 21.062 | −9.120 | 1.00 | 28.35 | B | C |
| ATOM | 12958 | CB | PRO | B | 290 | 69.998 | 21.185 | −8.304 | 1.00 | 29.34 | B | C |
| ATOM | 12961 | CG | PRO | B | 290 | 70.632 | 22.443 | −8.746 | 1.00 | 31.20 | B | C |
| ATOM | 12964 | CD | PRO | B | 290 | 69.568 | 23.338 | −9.199 | 1.00 | 29.41 | B | C |
| ATOM | 12967 | C | PRO | B | 290 | 67.597 | 20.503 | −8.245 | 1.00 | 27.13 | B | C |
| ATOM | 12968 | O | PRO | B | 290 | 67.211 | 19.356 | −8.429 | 1.00 | 26.99 | B | O |
| ATOM | 12969 | N | GLN | B | 291 | 67.073 | 21.317 | −7.333 | 1.00 | 26.56 | B | N |
| ATOM | 12970 | CA | GLN | B | 291 | 66.043 | 20.889 | −6.395 | 1.00 | 28.08 | B | C |
| ATOM | 12972 | CB | GLN | B | 291 | 65.903 | 21.923 | −5.273 | 1.00 | 28.20 | B | C |
| ATOM | 12975 | CG | GLN | B | 291 | 65.226 | 23.240 | −5.649 | 1.00 | 29.54 | B | C |
| ATOM | 12978 | CD | GLN | B | 291 | 66.216 | 24.301 | −6.116 | 1.00 | 39.09 | B | C |
| ATOM | 12979 | OE1 | GLN | B | 291 | 67.318 | 23.982 | −6.604 | 1.00 | 38.40 | B | O |
| ATOM | 12980 | NE2 | GLN | B | 291 | 65.835 | 25.579 | −5.957 | 1.00 | 34.88 | B | N |
| ATOM | 12983 | C | GLN | B | 291 | 64.631 | 20.595 | −6.967 | 1.00 | 28.38 | B | C |
| ATOM | 12984 | O | GLN | B | 291 | 63.778 | 20.058 | −6.256 | 1.00 | 28.46 | B | O |
| ATOM | 12986 | N | TYR | B | 292 | 64.375 | 20.955 | −8.219 | 1.00 | 28.39 | B | N |
| ATOM | 12987 | CA | TYR | B | 292 | 63.043 | 20.732 | −8.817 | 1.00 | 29.49 | B | C |
| ATOM | 12989 | CB | TYR | B | 292 | 62.665 | 21.897 | −9.751 | 1.00 | 29.50 | B | C |
| ATOM | 12992 | CG | TYR | B | 292 | 62.448 | 23.230 | −9.077 | 1.00 | 31.00 | B | C |
| ATOM | 12993 | CD1 | TYR | B | 292 | 61.801 | 23.327 | −7.844 | 1.00 | 32.31 | B | C |
| ATOM | 12995 | CE1 | TYR | B | 292 | 61.595 | 24.565 | −7.235 | 1.00 | 36.98 | B | C |
| ATOM | 12997 | CZ | TYR | B | 292 | 62.016 | 25.723 | −7.869 | 1.00 | 39.38 | B | C |
| ATOM | 12998 | OH | TYR | B | 292 | 61.804 | 26.951 | −7.281 | 1.00 | 45.92 | B | O |
| ATOM | 13000 | CE2 | TYR | B | 292 | 62.634 | 25.655 | −9.106 | 1.00 | 42.09 | B | C |
| ATOM | 13002 | CD2 | TYR | B | 292 | 62.849 | 24.413 | −9.701 | 1.00 | 39.44 | B | C |
| ATOM | 13004 | C | TYR | B | 292 | 62.942 | 19.410 | −9.590 | 1.00 | 28.42 | B | C |
| ATOM | 13005 | O | TYR | B | 292 | 62.355 | 19.362 | −10.659 | 1.00 | 27.22 | B | O |
| ATOM | 13007 | N | SER | B | 293 | 63.523 | 18.344 | −9.050 | 1.00 | 28.09 | B | N |
| ATOM | 13008 | CA | SER | B | 293 | 63.430 | 17.036 | −9.669 | 1.00 | 28.01 | B | C |
| ATOM | 13010 | CB | SER | B | 293 | 64.181 | 15.987 | −8.824 | 1.00 | 29.51 | B | C |
| ATOM | 13013 | OG | SER | B | 293 | 65.590 | 16.068 | −9.070 | 1.00 | 30.76 | B | O |
| ATOM | 13015 | C | SER | B | 293 | 61.973 | 16.635 | −9.898 | 1.00 | 26.55 | B | C |
| ATOM | 13016 | O | SER | B | 293 | 61.634 | 16.155 | −10.968 | 1.00 | 28.86 | B | O |
| ATOM | 13018 | N | ASP | B | 294 | 61.120 | 16.853 | −8.907 | 1.00 | 25.23 | B | N |
| ATOM | 13019 | CA | ASP | B | 294 | 59.721 | 16.469 | −9.000 | 1.00 | 28.08 | B | C |

TABLE 4-2-continued

Coordinates of *P. alba* IspS

| ATOM | 13021 | CB | ASP | B | 294 | 58.962 | 16.785 | −7.696 | 1.00 | 28.58 | B | C |
|---|---|---|---|---|---|---|---|---|---|---|---|---|
| ATOM | 13024 | CG | ASP | B | 294 | 59.432 | 15.942 | −6.522 | 1.00 | 37.32 | B | C |
| ATOM | 13025 | OD1 | ASP | B | 294 | 60.154 | 14.943 | −6.741 | 1.00 | 36.71 | B | O |
| ATOM | 13026 | OD2 | ASP | B | 294 | 59.094 | 16.301 | −5.363 | 1.00 | 45.41 | B | O |
| ATOM | 13027 | C | ASP | B | 294 | 59.019 | 17.171 | −10.163 | 1.00 | 28.26 | B | C |
| ATOM | 13028 | O | ASP | B | 294 | 58.249 | 16.544 | −10.891 | 1.00 | 27.19 | B | O |
| ATOM | 13030 | N | CYS | B | 295 | 59.261 | 18.477 | −10.298 | 1.00 | 26.75 | B | N |
| ATOM | 13031 | CA | CYS | B | 295 | 58.687 | 19.249 | −11.376 | 1.00 | 24.72 | B | C |
| ATOM | 13033 | CB | CYS | B | 295 | 59.091 | 20.714 | −11.313 | 1.00 | 24.78 | B | C |
| ATOM | 13036 | SG | CYS | B | 295 | 58.157 | 21.730 | −12.489 | 1.00 | 24.85 | B | S |
| ATOM | 13038 | C | CYS | B | 295 | 59.090 | 18.651 | −12.702 | 1.00 | 25.01 | B | C |
| ATOM | 13039 | O | CYS | B | 295 | 58.222 | 18.397 | −13.539 | 1.00 | 23.90 | B | O |
| ATOM | 13041 | N | ARG | B | 296 | 60.386 | 18.396 | −12.893 | 1.00 | 24.46 | B | N |
| ATOM | 13042 | CA | ARG | B | 296 | 60.851 | 17.831 | −14.172 | 1.00 | 24.09 | B | C |
| ATOM | 13044 | CB | ARG | B | 296 | 62.369 | 17.647 | −14.205 | 1.00 | 24.77 | B | C |
| ATOM | 13047 | CG | ARG | B | 296 | 63.153 | 18.936 | −14.354 | 1.00 | 23.30 | B | C |
| ATOM | 13050 | CD | ARG | B | 296 | 64.643 | 18.682 | −14.514 | 1.00 | 19.69 | B | C |
| ATOM | 13053 | NE | ARG | B | 296 | 65.243 | 18.178 | −13.289 | 1.00 | 19.76 | B | N |
| ATOM | 13055 | CZ | ARG | B | 296 | 65.634 | 18.927 | −12.254 | 1.00 | 24.50 | B | C |
| ATOM | 13056 | NH1 | ARG | B | 296 | 65.496 | 20.255 | −12.255 | 1.00 | 25.75 | B | N |
| ATOM | 13059 | NH2 | ARG | B | 296 | 66.166 | 18.328 | −11.191 | 1.00 | 27.06 | B | N |
| ATOM | 13062 | C | ARG | B | 296 | 60.185 | 16.495 | −14.463 | 1.00 | 23.06 | B | C |
| ATOM | 13063 | O | ARG | B | 296 | 59.718 | 16.245 | −15.597 | 1.00 | 22.98 | B | O |
| ATOM | 13065 | N | ASN | B | 297 | 60.138 | 15.641 | −13.447 | 1.00 | 22.07 | B | N |
| ATOM | 13066 | CA | ASN | B | 297 | 59.565 | 14.316 | −13.609 | 1.00 | 24.36 | B | C |
| ATOM | 13068 | CB | ASN | B | 297 | 59.763 | 13.460 | −12.364 | 1.00 | 24.91 | B | C |
| ATOM | 13071 | CG | ASN | B | 297 | 61.206 | 13.110 | −12.150 | 1.00 | 31.79 | B | C |
| ATOM | 13072 | OD1 | ASN | B | 297 | 61.998 | 13.156 | −13.095 | 1.00 | 38.41 | B | O |
| ATOM | 13073 | ND2 | ASN | B | 297 | 61.570 | 12.757 | −10.911 | 1.00 | 29.95 | B | N |
| ATOM | 13076 | C | ASN | B | 297 | 58.095 | 14.399 | −13.952 | 1.00 | 24.42 | B | C |
| ATOM | 13077 | O | ASN | B | 297 | 57.622 | 13.726 | −14.876 | 1.00 | 23.19 | B | O |
| ATOM | 13079 | N | SER | B | 298 | 57.393 | 15.242 | −13.215 | 1.00 | 23.97 | B | N |
| ATOM | 13080 | CA | SER | B | 298 | 55.976 | 15.474 | −13.444 | 1.00 | 24.63 | B | C |
| ATOM | 13082 | CB | SER | B | 298 | 55.466 | 16.475 | −12.403 | 1.00 | 25.85 | B | C |
| ATOM | 13085 | OG | SER | B | 298 | 54.275 | 16.038 | −11.808 | 1.00 | 36.11 | B | O |
| ATOM | 13087 | C | SER | B | 298 | 55.694 | 16.009 | −14.851 | 1.00 | 23.06 | B | C |
| ATOM | 13088 | O | SER | B | 298 | 54.827 | 15.490 | −15.572 | 1.00 | 21.42 | B | O |
| ATOM | 13090 | N | VAL | B | 299 | 56.412 | 17.066 | −15.240 | 1.00 | 20.75 | B | N |
| ATOM | 13091 | CA | VAL | B | 299 | 56.238 | 17.639 | −16.554 | 1.00 | 18.08 | B | C |
| ATOM | 13093 | CB | VAL | B | 299 | 57.037 | 18.933 | −16.690 | 1.00 | 19.98 | B | C |
| ATOM | 13095 | CG1 | VAL | B | 299 | 57.029 | 19.453 | −18.146 | 1.00 | 20.35 | B | C |
| ATOM | 13099 | CG2 | VAL | B | 299 | 56.457 | 19.960 | −15.770 | 1.00 | 21.88 | B | C |
| ATOM | 13103 | C | VAL | B | 299 | 56.636 | 16.633 | −17.648 | 1.00 | 19.45 | B | C |
| ATOM | 13104 | O | VAL | B | 299 | 55.996 | 16.570 | −18.700 | 1.00 | 17.92 | B | O |
| ATOM | 13106 | N | ALA | B | 300 | 57.665 | 15.826 | −17.393 | 1.00 | 18.10 | B | N |
| ATOM | 13107 | CA | ALA | B | 300 | 58.147 | 14.869 | −18.404 | 1.00 | 19.47 | B | C |
| ATOM | 13109 | CB | ALA | B | 300 | 59.535 | 14.263 | −18.011 | 1.00 | 15.98 | B | C |
| ATOM | 13113 | C | ALA | B | 300 | 57.121 | 13.762 | −18.590 | 1.00 | 20.75 | B | C |
| ATOM | 13114 | O | ALA | B | 300 | 56.813 | 13.354 | −19.714 | 1.00 | 21.28 | B | O |
| ATOM | 13116 | N | LYS | B | 301 | 56.573 | 13.283 | −17.482 | 1.00 | 21.38 | B | N |
| ATOM | 13117 | CA | LYS | B | 301 | 55.560 | 12.239 | −17.553 | 1.00 | 20.81 | B | C |
| ATOM | 13119 | CB | LYS | B | 301 | 55.187 | 11.785 | −16.160 | 1.00 | 20.47 | B | C |
| ATOM | 13122 | CG | LYS | B | 301 | 56.259 | 10.978 | −15.481 | 1.00 | 20.34 | B | C |
| ATOM | 13125 | CD | LYS | B | 301 | 55.758 | 10.422 | −14.150 | 1.00 | 20.67 | B | C |
| ATOM | 13128 | CE | LYS | B | 301 | 56.846 | 9.711 | −13.349 | 1.00 | 28.61 | B | C |
| ATOM | 13131 | NZ | LYS | B | 301 | 56.310 | 9.346 | −11.992 | 1.00 | 31.10 | B | N |
| ATOM | 13135 | C | LYS | B | 301 | 54.313 | 12.719 | −18.283 | 1.00 | 19.17 | B | C |
| ATOM | 13136 | O | LYS | B | 301 | 53.752 | 11.998 | −19.088 | 1.00 | 19.72 | B | O |
| ATOM | 13138 | N | MET | B | 302 | 53.880 | 13.940 | −17.995 | 1.00 | 18.82 | B | N |
| ATOM | 13139 | CA | MET | B | 302 | 52.656 | 14.473 | −18.598 | 1.00 | 19.48 | B | C |
| ATOM | 13141 | CB | MET | B | 302 | 52.169 | 15.752 | −17.900 | 1.00 | 18.45 | B | C |
| ATOM | 13144 | CG | MET | B | 302 | 51.728 | 15.582 | −16.463 | 1.00 | 16.26 | B | C |
| ATOM | 13147 | SD | MET | B | 302 | 50.418 | 14.399 | −16.251 | 1.00 | 27.62 | B | S |
| ATOM | 13148 | CE | MET | B | 302 | 51.337 | 12.933 | −15.824 | 1.00 | 23.65 | B | C |
| ATOM | 13152 | C | MET | B | 302 | 52.860 | 14.765 | −20.067 | 1.00 | 21.47 | B | C |
| ATOM | 13153 | O | MET | B | 302 | 52.007 | 14.431 | −20.896 | 1.00 | 23.42 | B | O |
| ATOM | 13155 | N | PHE | B | 303 | 53.966 | 15.404 | −20.412 | 1.00 | 21.99 | B | N |
| ATOM | 13156 | CA | PHE | B | 303 | 54.225 | 15.621 | −21.834 | 1.00 | 22.67 | B | C |
| ATOM | 13158 | CB | PHE | B | 303 | 55.475 | 16.466 | −22.069 | 1.00 | 23.73 | B | C |
| ATOM | 13161 | CG | PHE | B | 303 | 55.398 | 17.344 | −23.304 | 1.00 | 31.04 | B | C |
| ATOM | 13162 | CD1 | PHE | B | 303 | 54.200 | 17.518 | −24.009 | 1.00 | 29.05 | B | C |
| ATOM | 13164 | CE1 | PHE | B | 303 | 54.144 | 18.322 | −25.144 | 1.00 | 42.79 | B | C |
| ATOM | 13166 | CZ | PHE | B | 303 | 55.280 | 18.986 | −25.577 | 1.00 | 41.71 | B | C |
| ATOM | 13168 | CE2 | PHE | B | 303 | 56.469 | 18.843 | −24.877 | 1.00 | 37.08 | B | C |
| ATOM | 13170 | CD2 | PHE | B | 303 | 56.525 | 18.023 | −23.742 | 1.00 | 37.60 | B | C |
| ATOM | 13172 | C | PHE | B | 303 | 54.312 | 14.315 | −22.621 | 1.00 | 21.08 | B | C |
| ATOM | 13173 | O | PHE | B | 303 | 53.799 | 14.238 | −23.733 | 1.00 | 21.61 | B | O |
| ATOM | 13175 | N | SER | B | 304 | 54.907 | 13.277 | −22.036 | 1.00 | 21.32 | B | N |

TABLE 4-2-continued

Coordinates of *P. alba* IspS

| ATOM | 13176 | CA | SER | B | 304 | 54.949 | 11.965 | −22.692 | 1.00 | 20.73 | B | C |
|---|---|---|---|---|---|---|---|---|---|---|---|---|
| ATOM | 13178 | CB | SER | B | 304 | 55.700 | 10.941 | −21.850 | 1.00 | 22.39 | B | C |
| ATOM | 13181 | OG | SER | B | 304 | 57.032 | 11.374 | −21.573 | 1.00 | 24.34 | B | O |
| ATOM | 13183 | C | SER | B | 304 | 53.551 | 11.444 | −22.967 | 1.00 | 21.58 | B | C |
| ATOM | 13184 | O | SER | B | 304 | 53.296 | 10.929 | −24.034 | 1.00 | 23.78 | B | O |
| ATOM | 13186 | N | PHE | B | 305 | 52.639 | 11.591 | −22.011 | 1.00 | 21.21 | B | N |
| ATOM | 13187 | CA | PHE | B | 305 | 51.256 | 11.195 | −22.225 | 1.00 | 19.19 | B | C |
| ATOM | 13189 | CB | PHE | B | 305 | 50.487 | 11.141 | −20.903 | 1.00 | 21.39 | B | C |
| ATOM | 13192 | CG | PHE | B | 305 | 50.574 | 9.814 | −20.230 | 1.00 | 22.98 | B | C |
| ATOM | 13193 | CD1 | PHE | B | 305 | 49.894 | 8.742 | −20.738 | 1.00 | 22.59 | B | C |
| ATOM | 13195 | CE1 | PHE | B | 305 | 49.983 | 7.507 | −20.135 | 1.00 | 23.64 | B | C |
| ATOM | 13197 | CZ | PHE | B | 305 | 50.747 | 7.338 | −19.024 | 1.00 | 24.33 | B | C |
| ATOM | 13199 | CE2 | PHE | B | 305 | 51.435 | 8.406 | −18.505 | 1.00 | 27.51 | B | C |
| ATOM | 13201 | CD2 | PHE | B | 305 | 51.349 | 9.634 | −19.112 | 1.00 | 22.45 | B | C |
| ATOM | 13203 | C | PHE | B | 305 | 50.542 | 12.110 | −23.197 | 1.00 | 20.45 | B | C |
| ATOM | 13204 | O | PHE | B | 305 | 49.770 | 11.631 | −24.020 | 1.00 | 19.27 | B | O |
| ATOM | 13206 | N | VAL | B | 306 | 50.791 | 13.421 | −23.126 | 1.00 | 20.75 | B | N |
| ATOM | 13207 | CA | VAL | B | 306 | 50.184 | 14.351 | −24.081 | 1.00 | 19.25 | B | C |
| ATOM | 13209 | CB | VAL | B | 306 | 50.655 | 15.809 | −23.878 | 1.00 | 22.43 | B | C |
| ATOM | 13211 | CG1 | VAL | B | 306 | 50.202 | 16.687 | −25.012 | 1.00 | 14.46 | B | C |
| ATOM | 13215 | CG2 | VAL | B | 306 | 50.145 | 16.385 | −22.528 | 1.00 | 16.22 | B | C |
| ATOM | 13219 | C | VAL | B | 306 | 50.464 | 13.914 | −25.511 | 1.00 | 22.34 | B | C |
| ATOM | 13220 | O | VAL | B | 306 | 49.566 | 13.856 | −26.316 | 1.00 | 23.30 | B | O |
| ATOM | 13222 | N | THR | B | 307 | 51.696 | 13.555 | −25.830 | 1.00 | 25.01 | B | N |
| ATOM | 13223 | CA | THR | B | 307 | 52.025 | 13.284 | −27.227 | 1.00 | 26.57 | B | C |
| ATOM | 13225 | CB | THR | B | 307 | 53.520 | 13.087 | −27.435 | 1.00 | 26.12 | B | C |
| ATOM | 13227 | OG1 | THR | B | 307 | 53.909 | 11.896 | −26.774 | 1.00 | 40.17 | B | O |
| ATOM | 13229 | CG2 | THR | B | 307 | 54.339 | 14.252 | −26.872 | 1.00 | 33.09 | B | C |
| ATOM | 13233 | C | THR | B | 307 | 51.284 | 12.043 | −27.757 | 1.00 | 26.12 | B | C |
| ATOM | 13234 | O | THR | B | 307 | 50.866 | 12.016 | −28.903 | 1.00 | 25.66 | B | O |
| ATOM | 13236 | N | ILE | B | 308 | 51.139 | 11.031 | −26.908 | 1.00 | 24.81 | B | N |
| ATOM | 13237 | CA | ILE | B | 308 | 50.352 | 9.833 | −27.215 | 1.00 | 23.60 | B | C |
| ATOM | 13239 | CB | ILE | B | 308 | 50.545 | 8.768 | −26.118 | 1.00 | 25.72 | B | C |
| ATOM | 13241 | CG1 | ILE | B | 308 | 51.994 | 8.263 | −26.119 | 1.00 | 27.99 | B | C |
| ATOM | 13244 | CD1 | ILE | B | 308 | 52.272 | 7.297 | −24.983 | 1.00 | 28.28 | B | C |
| ATOM | 13248 | CG2 | ILE | B | 308 | 49.588 | 7.595 | −26.318 | 1.00 | 24.09 | B | C |
| ATOM | 13252 | C | ILE | B | 308 | 48.865 | 10.144 | −27.337 | 1.00 | 22.14 | B | C |
| ATOM | 13253 | O | ILE | B | 308 | 48.245 | 9.781 | −28.321 | 1.00 | 22.79 | B | O |
| ATOM | 13255 | N | ILE | B | 309 | 48.292 | 10.823 | −26.344 | 1.00 | 20.84 | B | N |
| ATOM | 13256 | CA | ILE | B | 309 | 46.882 | 11.147 | −26.371 | 1.00 | 21.20 | B | C |
| ATOM | 13258 | CB | ILE | B | 309 | 46.435 | 11.822 | −25.093 | 1.00 | 22.62 | B | C |
| ATOM | 13260 | CG1 | ILE | B | 309 | 46.643 | 10.910 | −23.874 | 1.00 | 26.22 | B | C |
| ATOM | 13263 | CD1 | ILE | B | 309 | 45.698 | 9.823 | −23.812 | 1.00 | 38.91 | B | C |
| ATOM | 13267 | CG2 | ILE | B | 309 | 44.993 | 12.206 | −25.188 | 1.00 | 18.44 | B | C |
| ATOM | 13271 | C | ILE | B | 309 | 46.612 | 12.069 | −27.563 | 1.00 | 22.75 | B | C |
| ATOM | 13272 | O | ILE | B | 309 | 45.645 | 11.896 | −28.307 | 1.00 | 23.59 | B | O |
| ATOM | 13274 | N | ASP | B | 310 | 47.506 | 13.010 | −27.796 | 1.00 | 22.88 | B | N |
| ATOM | 13275 | CA | ASP | B | 310 | 47.402 | 13.867 | −28.991 | 1.00 | 24.17 | B | C |
| ATOM | 13277 | CB | ASP | B | 310 | 48.606 | 14.828 | −29.062 | 1.00 | 25.25 | B | C |
| ATOM | 13280 | CG | ASP | B | 310 | 48.464 | 15.924 | −30.125 | 1.00 | 31.57 | B | C |
| ATOM | 13281 | OD1 | ASP | B | 310 | 47.362 | 16.203 | −30.614 | 1.00 | 41.50 | B | O |
| ATOM | 13282 | OD2 | ASP | B | 310 | 49.503 | 16.528 | −30.461 | 1.00 | 46.26 | B | O |
| ATOM | 13283 | C | ASP | B | 310 | 47.268 | 13.005 | −30.264 | 1.00 | 23.28 | B | C |
| ATOM | 13284 | O | ASP | B | 310 | 46.344 | 13.216 | −31.032 | 1.00 | 22.28 | B | O |
| ATOM | 13286 | N | ASP | B | 311 | 48.139 | 12.012 | −30.464 | 1.00 | 23.05 | B | N |
| ATOM | 13287 | CA | ASP | B | 311 | 48.040 | 11.175 | −31.666 | 1.00 | 25.68 | B | C |
| ATOM | 13289 | CB | ASP | B | 311 | 49.146 | 10.136 | −31.720 | 1.00 | 27.71 | B | C |
| ATOM | 13292 | CG | ASP | B | 311 | 50.509 | 10.741 | −31.947 | 1.00 | 35.42 | B | C |
| ATOM | 13293 | OD1 | ASP | B | 311 | 50.567 | 11.862 | −32.501 | 1.00 | 39.96 | B | O |
| ATOM | 13294 | OD2 | ASP | B | 311 | 51.516 | 10.092 | −31.558 | 1.00 | 44.33 | B | O |
| ATOM | 13295 | C | ASP | B | 311 | 46.703 | 10.442 | −31.770 | 1.00 | 24.73 | B | C |
| ATOM | 13296 | O | ASP | B | 311 | 46.168 | 10.275 | −32.866 | 1.00 | 25.59 | B | O |
| ATOM | 13298 | N | ILE | B | 312 | 46.169 | 9.998 | −30.640 | 1.00 | 21.14 | B | N |
| ATOM | 13299 | CA | ILE | B | 312 | 44.901 | 9.300 | −30.658 | 1.00 | 20.46 | B | C |
| ATOM | 13301 | CB | ILE | B | 312 | 44.558 | 8.792 | −29.225 | 1.00 | 21.25 | B | C |
| ATOM | 13303 | CG1 | ILE | B | 312 | 45.428 | 7.566 | −28.870 | 1.00 | 22.56 | B | C |
| ATOM | 13306 | CD1 | ILE | B | 312 | 45.327 | 7.127 | −27.386 | 1.00 | 15.81 | B | C |
| ATOM | 13310 | CG2 | ILE | B | 312 | 43.089 | 8.428 | −29.087 | 1.00 | 17.97 | B | C |
| ATOM | 13314 | C | ILE | B | 312 | 43.803 | 10.213 | −31.251 | 1.00 | 22.04 | B | C |
| ATOM | 13315 | O | ILE | B | 312 | 43.047 | 9.805 | −32.119 | 1.00 | 21.87 | B | O |
| ATOM | 13317 | N | TYR | B | 313 | 43.700 | 11.445 | −30.756 | 1.00 | 24.10 | B | N |
| ATOM | 13318 | CA | TYR | B | 313 | 42.717 | 12.413 | −31.269 | 1.00 | 22.33 | B | C |
| ATOM | 13320 | CB | TYR | B | 313 | 42.602 | 13.613 | −30.321 | 1.00 | 22.53 | B | C |
| ATOM | 13323 | CG | TYR | B | 313 | 41.860 | 13.350 | −29.049 | 1.00 | 18.01 | B | C |
| ATOM | 13324 | CD1 | TYR | B | 313 | 40.533 | 13.713 | −28.908 | 1.00 | 15.63 | B | C |
| ATOM | 13326 | CE1 | TYR | B | 313 | 39.838 | 13.478 | −27.730 | 1.00 | 18.26 | B | C |
| ATOM | 13328 | CZ | TYR | B | 313 | 40.489 | 12.864 | −26.664 | 1.00 | 22.61 | B | C |
| ATOM | 13329 | OH | TYR | B | 313 | 39.833 | 12.629 | −25.474 | 1.00 | 18.89 | B | O |

TABLE 4-2-continued

Coordinates of *P. alba* IspS

| ATOM | 13331 | CE2 | TYR | B | 313 | 41.811 | 12.496 | −26.785 | 1.00 | 23.65 | B | C |
| ATOM | 13333 | CD2 | TYR | B | 313 | 42.486 | 12.734 | −27.977 | 1.00 | 22.64 | B | C |
| ATOM | 13335 | C | TYR | B | 313 | 43.080 | 12.921 | −32.665 | 1.00 | 22.74 | B | C |
| ATOM | 13336 | O | TYR | B | 313 | 42.214 | 13.176 | −33.481 | 1.00 | 22.56 | B | O |
| ATOM | 13338 | N | ASP | B | 314 | 44.365 | 13.066 | −32.950 | 1.00 | 25.71 | B | N |
| ATOM | 13339 | CA | ASP | B | 314 | 44.768 | 13.652 | −34.221 | 1.00 | 26.66 | B | C |
| ATOM | 13341 | CB | ASP | B | 314 | 46.227 | 14.059 | −34.185 | 1.00 | 28.17 | B | C |
| ATOM | 13344 | CG | ASP | B | 314 | 46.668 | 14.758 | −35.459 | 1.00 | 34.44 | B | C |
| ATOM | 13345 | OD1 | ASP | B | 314 | 45.874 | 15.565 | −35.987 | 1.00 | 35.69 | B | O |
| ATOM | 13346 | OD2 | ASP | B | 314 | 47.809 | 14.501 | −35.924 | 1.00 | 42.75 | B | O |
| ATOM | 13347 | C | ASP | B | 314 | 44.529 | 12.699 | −35.409 | 1.00 | 26.37 | B | C |
| ATOM | 13348 | O | ASP | B | 314 | 43.935 | 13.112 | −36.405 | 1.00 | 24.33 | B | O |
| ATOM | 13350 | N | VAL | B | 315 | 44.949 | 11.441 | −35.282 | 1.00 | 24.78 | B | N |
| ATOM | 13351 | CA | VAL | B | 315 | 44.922 | 10.484 | −36.415 | 1.00 | 25.23 | B | C |
| ATOM | 13353 | CB | VAL | B | 315 | 46.340 | 10.251 | −36.987 | 1.00 | 23.87 | B | C |
| ATOM | 13355 | CG1 | VAL | B | 315 | 46.851 | 11.532 | −37.688 | 1.00 | 27.00 | B | C |
| ATOM | 13359 | CG2 | VAL | B | 315 | 47.289 | 9.792 | −35.902 | 1.00 | 22.09 | B | C |
| ATOM | 13363 | C | VAL | B | 315 | 44.305 | 9.096 | −36.185 | 1.00 | 25.17 | B | C |
| ATOM | 13364 | O | VAL | B | 315 | 43.729 | 8.544 | −37.109 | 1.00 | 27.94 | B | O |
| ATOM | 13366 | N | TYR | B | 316 | 44.426 | 8.520 | −34.993 | 1.00 | 24.11 | B | N |
| ATOM | 13367 | CA | TYR | B | 316 | 44.020 | 7.122 | −34.779 | 1.00 | 23.73 | B | C |
| ATOM | 13369 | CB | TYR | B | 316 | 44.867 | 6.522 | −33.672 | 1.00 | 25.65 | B | C |
| ATOM | 13372 | CG | TYR | B | 316 | 44.824 | 5.019 | −33.620 | 1.00 | 27.69 | B | C |
| ATOM | 13373 | CD1 | TYR | B | 316 | 45.597 | 4.235 | −34.499 | 1.00 | 25.15 | B | C |
| ATOM | 13375 | CE1 | TYR | B | 316 | 45.550 | 2.814 | −34.447 | 1.00 | 25.74 | B | C |
| ATOM | 13377 | CZ | TYR | B | 316 | 44.740 | 2.208 | −33.503 | 1.00 | 24.05 | B | C |
| ATOM | 13378 | OH | TYR | B | 316 | 44.669 | 0.862 | −33.392 | 1.00 | 25.86 | B | O |
| ATOM | 13380 | CE2 | TYR | B | 316 | 43.966 | 2.972 | −32.630 | 1.00 | 31.18 | B | C |
| ATOM | 13382 | CD2 | TYR | B | 316 | 44.012 | 4.368 | −32.692 | 1.00 | 27.68 | B | C |
| ATOM | 13384 | C | TYR | B | 316 | 42.540 | 6.883 | −34.427 | 1.00 | 23.79 | B | C |
| ATOM | 13385 | O | TYR | B | 316 | 41.897 | 5.976 | −34.977 | 1.00 | 23.24 | B | O |
| ATOM | 13387 | N | GLY | B | 317 | 41.999 | 7.665 | −33.502 | 1.00 | 21.86 | B | N |
| ATOM | 13388 | CA | GLY | B | 317 | 40.677 | 7.383 | −32.966 | 1.00 | 20.83 | B | C |
| ATOM | 13391 | C | GLY | B | 317 | 39.577 | 7.917 | −33.858 | 1.00 | 23.66 | B | C |
| ATOM | 13392 | O | GLY | B | 317 | 39.701 | 9.008 | −34.444 | 1.00 | 21.52 | B | O |
| ATOM | 13394 | N | THR | B | 318 | 38.490 | 7.152 | −33.975 | 1.00 | 22.28 | B | N |
| ATOM | 13395 | CA | THR | B | 318 | 37.315 | 7.674 | −34.607 | 1.00 | 22.27 | B | C |
| ATOM | 13397 | CB | THR | B | 318 | 36.314 | 6.564 | −34.989 | 1.00 | 23.50 | B | C |
| ATOM | 13399 | OG1 | THR | B | 318 | 35.746 | 6.006 | −33.803 | 1.00 | 25.49 | B | O |
| ATOM | 13401 | CG2 | THR | B | 318 | 37.006 | 5.456 | −35.807 | 1.00 | 21.97 | B | C |
| ATOM | 13405 | C | THR | B | 318 | 36.625 | 8.610 | −33.638 | 1.00 | 23.75 | B | C |
| ATOM | 13406 | O | THR | B | 318 | 36.823 | 8.542 | −32.412 | 1.00 | 23.62 | B | O |
| ATOM | 13408 | N | LEU | B | 319 | 35.757 | 9.446 | −34.189 | 1.00 | 22.45 | B | N |
| ATOM | 13409 | CA | LEU | B | 319 | 35.009 | 10.398 | −33.393 | 1.00 | 24.74 | B | C |
| ATOM | 13411 | CB | LEU | B | 319 | 34.040 | 11.176 | −34.274 | 1.00 | 24.05 | B | C |
| ATOM | 13414 | CG | LEU | B | 319 | 33.903 | 12.670 | −34.012 | 1.00 | 34.66 | B | C |
| ATOM | 13416 | CD1 | LEU | B | 319 | 35.268 | 13.345 | −33.825 | 1.00 | 22.94 | B | C |
| ATOM | 13420 | CD2 | LEU | B | 319 | 33.063 | 13.338 | −35.150 | 1.00 | 33.27 | B | C |
| ATOM | 13424 | C | LEU | B | 319 | 34.273 | 9.736 | −32.238 | 1.00 | 24.81 | B | C |
| ATOM | 13425 | O | LEU | B | 319 | 34.300 | 10.224 | −31.127 | 1.00 | 27.70 | B | O |
| ATOM | 13427 | N | ASP | B | 320 | 33.637 | 8.605 | −32.498 | 1.00 | 26.74 | B | N |
| ATOM | 13428 | CA | ASP | B | 320 | 32.910 | 7.881 | −31.469 | 1.00 | 26.27 | B | C |
| ATOM | 13430 | CB | ASP | B | 320 | 32.192 | 6.650 | −32.064 | 1.00 | 29.58 | B | C |
| ATOM | 13433 | CG | ASP | B | 320 | 30.855 | 6.977 | −32.760 | 1.00 | 35.82 | B | C |
| ATOM | 13434 | OD1 | ASP | B | 320 | 30.397 | 8.145 | −32.767 | 1.00 | 38.73 | B | O |
| ATOM | 13435 | OD2 | ASP | B | 320 | 30.261 | 6.018 | −33.315 | 1.00 | 45.55 | B | O |
| ATOM | 13436 | C | ASP | B | 320 | 33.857 | 7.413 | −30.361 | 1.00 | 23.93 | B | C |
| ATOM | 13437 | O | ASP | B | 320 | 33.509 | 7.435 | −29.199 | 1.00 | 23.76 | B | O |
| ATOM | 13439 | N | GLU | B | 321 | 35.044 | 6.951 | −30.724 | 1.00 | 23.54 | B | N |
| ATOM | 13440 | CA | GLU | B | 321 | 35.977 | 6.478 | −29.721 | 1.00 | 22.08 | B | C |
| ATOM | 13442 | CB | GLU | B | 321 | 37.129 | 5.748 | −30.378 | 1.00 | 21.78 | B | C |
| ATOM | 13445 | CG | GLU | B | 321 | 36.748 | 4.435 | −31.077 | 1.00 | 21.27 | B | C |
| ATOM | 13448 | CD | GLU | B | 321 | 37.959 | 3.809 | −31.762 | 1.00 | 25.99 | B | C |
| ATOM | 13449 | OE1 | GLU | B | 321 | 38.908 | 4.571 | −32.114 | 1.00 | 24.28 | B | O |
| ATOM | 13450 | OE2 | GLU | B | 321 | 37.983 | 2.569 | −31.922 | 1.00 | 26.77 | B | O |
| ATOM | 13451 | C | GLU | B | 321 | 36.506 | 7.668 | −28.909 | 1.00 | 22.57 | B | C |
| ATOM | 13452 | O | GLU | B | 321 | 36.761 | 7.548 | −27.714 | 1.00 | 21.71 | B | O |
| ATOM | 13454 | N | LEU | B | 322 | 36.665 | 8.813 | −29.569 | 1.00 | 21.65 | B | N |
| ATOM | 13455 | CA | LEU | B | 322 | 37.187 | 9.993 | −28.909 | 1.00 | 22.06 | B | C |
| ATOM | 13457 | CB | LEU | B | 322 | 37.611 | 11.059 | −29.909 | 1.00 | 20.94 | B | C |
| ATOM | 13460 | CG | LEU | B | 322 | 38.692 | 10.615 | −30.885 | 1.00 | 20.78 | B | C |
| ATOM | 13462 | CD1 | LEU | B | 322 | 38.999 | 11.683 | −31.924 | 1.00 | 17.20 | B | C |
| ATOM | 13466 | CD2 | LEU | B | 322 | 39.949 | 10.199 | −30.146 | 1.00 | 17.86 | B | C |
| ATOM | 13470 | C | LEU | B | 322 | 36.169 | 10.546 | −27.927 | 1.00 | 23.46 | B | C |
| ATOM | 13471 | O | LEU | B | 322 | 36.555 | 11.005 | −26.852 | 1.00 | 24.73 | B | O |
| ATOM | 13473 | N | GLU | B | 323 | 34.880 | 10.460 | −28.243 | 1.00 | 21.53 | B | N |
| ATOM | 13474 | CA | GLU | B | 323 | 33.875 | 10.850 | −27.261 | 1.00 | 23.97 | B | C |
| ATOM | 13476 | CB | GLU | B | 323 | 32.469 | 10.840 | −27.851 | 1.00 | 26.47 | B | C |

TABLE 4-2-continued

Coordinates of *P. alba* IspS

| ATOM | 13479 | CG | GLU | B | 323 | 32.292 | 11.810 | −29.011 | 1.00 | 31.79 | B | C |
|---|---|---|---|---|---|---|---|---|---|---|---|---|
| ATOM | 13482 | CD | GLU | B | 323 | 31.723 | 13.145 | −28.600 | 1.00 | 39.43 | B | C |
| ATOM | 13483 | OE1 | GLU | B | 323 | 31.263 | 13.876 | −29.515 | 1.00 | 44.91 | B | O |
| ATOM | 13484 | OE2 | GLU | B | 323 | 31.713 | 13.459 | −27.383 | 1.00 | 40.00 | B | O |
| ATOM | 13485 | C | GLU | B | 323 | 33.930 | 9.940 | −26.030 | 1.00 | 24.87 | B | C |
| ATOM | 13486 | O | GLU | B | 323 | 33.810 | 10.409 | −24.899 | 1.00 | 23.87 | B | O |
| ATOM | 13488 | N | LEU | B | 324 | 34.129 | 8.643 | −26.238 | 1.00 | 24.68 | B | N |
| ATOM | 13489 | CA | LEU | B | 324 | 34.224 | 7.719 | −25.099 | 1.00 | 24.65 | B | C |
| ATOM | 13491 | CB | LEU | B | 324 | 34.330 | 6.249 | −25.566 | 1.00 | 25.50 | B | C |
| ATOM | 13494 | CG | LEU | B | 324 | 33.033 | 5.612 | −26.107 | 1.00 | 31.61 | B | C |
| ATOM | 13496 | CD1 | LEU | B | 324 | 33.328 | 4.286 | −26.843 | 1.00 | 26.20 | B | C |
| ATOM | 13500 | CD2 | LEU | B | 324 | 32.020 | 5.401 | −24.966 | 1.00 | 29.59 | B | C |
| ATOM | 13504 | C | LEU | B | 324 | 35.403 | 8.054 | −24.199 | 1.00 | 22.74 | B | C |
| ATOM | 13505 | O | LEU | B | 324 | 35.294 | 7.976 | −22.983 | 1.00 | 22.76 | B | O |
| ATOM | 13507 | N | PHE | B | 325 | 36.539 | 8.406 | −24.794 | 1.00 | 21.75 | B | N |
| ATOM | 13508 | CA | PHE | B | 325 | 37.765 | 8.651 | −24.017 | 1.00 | 19.99 | B | C |
| ATOM | 13510 | CB | PHE | B | 325 | 38.977 | 8.726 | −24.943 | 1.00 | 18.14 | B | C |
| ATOM | 13513 | CG | PHE | B | 325 | 40.293 | 8.727 | −24.222 | 1.00 | 20.43 | B | C |
| ATOM | 13514 | CD1 | PHE | B | 325 | 40.921 | 7.542 | −23.911 | 1.00 | 20.73 | B | C |
| ATOM | 13516 | CE1 | PHE | B | 325 | 42.133 | 7.529 | −23.250 | 1.00 | 18.54 | B | C |
| ATOM | 13518 | CZ | PHE | B | 325 | 42.741 | 8.712 | −22.890 | 1.00 | 18.75 | B | C |
| ATOM | 13520 | CE2 | PHE | B | 325 | 42.129 | 9.912 | −23.189 | 1.00 | 29.13 | B | C |
| ATOM | 13522 | CD2 | PHE | B | 325 | 40.901 | 9.918 | −23.855 | 1.00 | 20.29 | B | C |
| ATOM | 13524 | C | PHE | B | 325 | 37.660 | 9.930 | −23.215 | 1.00 | 19.39 | B | C |
| ATOM | 13525 | O | PHE | B | 325 | 38.067 | 9.999 | −22.050 | 1.00 | 21.89 | B | O |
| ATOM | 13527 | N | THR | B | 326 | 37.153 | 10.956 | −23.872 | 1.00 | 20.85 | B | N |
| ATOM | 13528 | CA | THR | B | 326 | 36.929 | 12.251 | −23.274 | 1.00 | 21.29 | B | C |
| ATOM | 13530 | CB | THR | B | 326 | 36.274 | 13.175 | −24.300 | 1.00 | 22.64 | B | C |
| ATOM | 13532 | OG1 | THR | B | 326 | 37.159 | 13.340 | −25.420 | 1.00 | 21.93 | B | O |
| ATOM | 13534 | CG2 | THR | B | 326 | 35.978 | 14.532 | −23.685 | 1.00 | 15.42 | B | C |
| ATOM | 13538 | C | THR | B | 326 | 36.034 | 12.107 | −22.056 | 1.00 | 21.59 | B | C |
| ATOM | 13539 | O | THR | B | 326 | 36.334 | 12.624 | −21.006 | 1.00 | 22.13 | B | O |
| ATOM | 13541 | N | ASP | B | 327 | 34.952 | 11.363 | −22.213 | 1.00 | 25.12 | B | N |
| ATOM | 13542 | CA | ASP | B | 327 | 33.991 | 11.091 | −21.144 | 1.00 | 24.52 | B | C |
| ATOM | 13544 | CB | ASP | B | 327 | 32.805 | 10.309 | −21.729 | 1.00 | 26.23 | B | C |
| ATOM | 13547 | CG | ASP | B | 327 | 31.880 | 9.726 | −20.654 | 1.00 | 35.17 | B | C |
| ATOM | 13548 | OD1 | ASP | B | 327 | 31.041 | 10.485 | −20.095 | 1.00 | 38.22 | B | O |
| ATOM | 13549 | OD2 | ASP | B | 327 | 31.994 | 8.499 | −20.370 | 1.00 | 41.20 | B | O |
| ATOM | 13550 | C | ASP | B | 327 | 34.635 | 10.320 | −20.002 | 1.00 | 24.61 | B | C |
| ATOM | 13551 | O | ASP | B | 327 | 34.422 | 10.642 | −18.824 | 1.00 | 25.19 | B | O |
| ATOM | 13553 | N | ALA | B | 328 | 35.440 | 9.313 | −20.339 | 1.00 | 22.67 | B | N |
| ATOM | 13554 | CA | ALA | B | 328 | 36.152 | 8.535 | −19.326 | 1.00 | 21.90 | B | C |
| ATOM | 13556 | CB | ALA | B | 328 | 36.923 | 7.388 | −19.966 | 1.00 | 21.68 | B | C |
| ATOM | 13560 | C | ALA | B | 328 | 37.102 | 9.399 | −18.487 | 1.00 | 21.10 | B | C |
| ATOM | 13561 | O | ALA | B | 328 | 37.245 | 9.183 | −17.287 | 1.00 | 20.62 | B | O |
| ATOM | 13563 | N | VAL | B | 329 | 37.762 | 10.356 | −19.118 | 1.00 | 18.66 | B | N |
| ATOM | 13564 | CA | VAL | B | 329 | 38.652 | 11.232 | −18.405 | 1.00 | 18.17 | B | C |
| ATOM | 13566 | CB | VAL | B | 329 | 39.547 | 12.030 | −19.362 | 1.00 | 18.54 | B | C |
| ATOM | 13568 | CG1 | VAL | B | 329 | 40.599 | 11.070 | −20.002 | 1.00 | 20.31 | B | C |
| ATOM | 13572 | CG2 | VAL | B | 329 | 40.267 | 13.148 | −18.630 | 1.00 | 16.84 | B | C |
| ATOM | 13576 | C | VAL | B | 329 | 37.841 | 12.144 | −17.498 | 1.00 | 22.27 | B | C |
| ATOM | 13577 | O | VAL | B | 329 | 38.210 | 12.343 | −16.342 | 1.00 | 24.05 | B | O |
| ATOM | 13579 | N | GLU | B | 330 | 36.725 | 12.664 | −17.999 | 1.00 | 22.49 | B | N |
| ATOM | 13580 | CA | GLU | B | 330 | 35.830 | 13.499 | −17.185 | 1.00 | 24.53 | B | C |
| ATOM | 13582 | CB | GLU | B | 330 | 34.638 | 14.006 | −18.032 | 1.00 | 23.64 | B | C |
| ATOM | 13585 | CG | GLU | B | 330 | 35.054 | 15.060 | −19.039 | 1.00 | 29.46 | B | C |
| ATOM | 13588 | CD | GLU | B | 330 | 33.972 | 15.467 | −20.043 | 1.00 | 36.72 | B | C |
| ATOM | 13589 | OE1 | GLU | B | 330 | 34.141 | 16.536 | −20.688 | 1.00 | 38.15 | B | O |
| ATOM | 13590 | OE2 | GLU | B | 330 | 32.969 | 14.739 | −20.205 | 1.00 | 39.50 | B | O |
| ATOM | 13591 | C | GLU | B | 330 | 35.321 | 12.765 | −15.952 | 1.00 | 25.12 | B | C |
| ATOM | 13592 | O | GLU | B | 330 | 35.371 | 13.295 | −14.850 | 1.00 | 24.76 | B | O |
| ATOM | 13594 | N | ARG | B | 331 | 34.843 | 11.537 | −16.129 | 1.00 | 26.13 | B | N |
| ATOM | 13595 | CA | AARG | B | 331 | 34.264 | 10.779 | −15.016 | 0.50 | 25.43 | B | C |
| ATOM | 13596 | CA | BARG | B | 331 | 34.261 | 10.787 | −15.019 | 0.50 | 25.52 | B | C |
| ATOM | 13599 | CB | AARG | B | 331 | 33.385 | 9.643 | −15.539 | 0.50 | 25.68 | B | C |
| ATOM | 13600 | CB | BARG | B | 331 | 33.350 | 9.683 | −15.563 | 0.50 | 25.87 | B | C |
| ATOM | 13605 | CG | AARG | B | 331 | 32.054 | 10.133 | −16.144 | 0.50 | 29.23 | B | C |
| ATOM | 13606 | CG | BARG | B | 331 | 32.115 | 10.255 | −16.312 | 0.50 | 29.59 | B | C |
| ATOM | 13611 | CD | AARG | B | 331 | 31.197 | 8.990 | −16.686 | 0.50 | 32.54 | B | C |
| ATOM | 13612 | CD | BARG | B | 331 | 31.212 | 9.190 | −16.943 | 0.50 | 32.56 | B | C |
| ATOM | 13617 | NE | AARG | B | 331 | 32.007 | 8.014 | −17.403 | 0.50 | 39.07 | B | N |
| ATOM | 13618 | NE | BARG | B | 331 | 30.097 | 9.778 | −17.691 | 0.50 | 37.34 | B | N |
| ATOM | 13621 | CZ | AARG | B | 331 | 32.223 | 6.766 | −17.000 | 0.50 | 36.77 | B | C |
| ATOM | 13622 | CZ | BARG | B | 331 | 28.967 | 10.208 | −17.135 | 0.50 | 40.94 | B | C |
| ATOM | 13623 | NH1 | AARG | B | 331 | 31.656 | 6.300 | −15.886 | 0.50 | 38.70 | B | N |
| ATOM | 13624 | NH1 | BARG | B | 331 | 28.782 | 10.113 | −15.825 | 0.50 | 38.56 | B | N |
| ATOM | 13629 | NH2 | AARG | B | 331 | 32.998 | 5.985 | −17.733 | 0.50 | 33.12 | B | N |
| ATOM | 13630 | NH2 | BARG | B | 331 | 28.016 | 10.734 | −17.891 | 0.50 | 39.98 | B | N |

TABLE 4-2-continued

| Coordinates of *P. alba* IspS | | | | | | | | | | | |
|---|---|---|---|---|---|---|---|---|---|---|---|
| ATOM | 13635 | C | ARG | B | 331 | 35.327 | 10.245 | −14.044 | 1.00 | 25.39 | B C |
| ATOM | 13636 | O | ARG | B | 331 | 35.081 | 10.116 | −12.841 | 1.00 | 23.54 | B O |
| ATOM | 13638 | N | TRP | B | 332 | 36.509 | 9.935 | −14.559 | 1.00 | 24.49 | B N |
| ATOM | 13639 | CA | TRP | B | 332 | 37.622 | 9.451 | −13.737 | 1.00 | 22.84 | B C |
| ATOM | 13641 | CB | TRP | B | 332 | 38.153 | 10.576 | −12.838 | 1.00 | 19.58 | B C |
| ATOM | 13644 | CG | TRP | B | 332 | 39.557 | 10.379 | −12.453 | 1.00 | 19.36 | B C |
| ATOM | 13645 | CD1 | TRP | B | 332 | 40.027 | 9.997 | −11.234 | 1.00 | 18.47 | B C |
| ATOM | 13647 | NE1 | TRP | B | 332 | 41.393 | 9.903 | −11.264 | 1.00 | 21.06 | B N |
| ATOM | 13649 | CE2 | TRP | B | 332 | 41.831 | 10.202 | −12.524 | 1.00 | 17.15 | B C |
| ATOM | 13650 | CD2 | TRP | B | 332 | 40.701 | 10.503 | −13.302 | 1.00 | 20.00 | B C |
| ATOM | 13651 | CE3 | TRP | B | 332 | 40.875 | 10.827 | −14.648 | 1.00 | 16.76 | B C |
| ATOM | 13653 | CZ3 | TRP | B | 332 | 42.149 | 10.869 | −15.154 | 1.00 | 18.63 | B C |
| ATOM | 13655 | CH2 | TRP | B | 332 | 43.257 | 10.567 | −14.354 | 1.00 | 21.96 | B C |
| ATOM | 13657 | CZ2 | TRP | B | 332 | 43.115 | 10.241 | −13.033 | 1.00 | 23.99 | B C |
| ATOM | 13659 | C | TRP | B | 332 | 37.252 | 8.223 | −12.919 | 1.00 | 21.89 | B C |
| ATOM | 13660 | O | TRP | B | 332 | 37.517 | 8.160 | −11.715 | 1.00 | 21.86 | B O |
| ATOM | 13662 | N | ASP | B | 333 | 36.660 | 7.240 | −13.591 | 1.00 | 22.25 | B N |
| ATOM | 13663 | CA | ASP | B | 333 | 36.126 | 6.051 | −12.932 | 1.00 | 24.19 | B C |
| ATOM | 13665 | CB | ASP | B | 333 | 34.598 | 5.972 | −13.154 | 1.00 | 24.72 | B C |
| ATOM | 13668 | CG | ASP | B | 333 | 33.947 | 4.754 | −12.473 | 1.00 | 28.67 | B C |
| ATOM | 13669 | OD1 | ASP | B | 333 | 34.580 | 4.096 | −11.612 | 1.00 | 32.90 | B O |
| ATOM | 13670 | OD2 | ASP | B | 333 | 32.773 | 4.466 | −12.795 | 1.00 | 34.32 | B O |
| ATOM | 13671 | C | ASP | B | 333 | 36.796 | 4.790 | −13.490 | 1.00 | 24.39 | B C |
| ATOM | 13672 | O | ASP | B | 333 | 36.486 | 4.352 | −14.599 | 1.00 | 23.16 | B O |
| ATOM | 13674 | N | VAL | B | 334 | 37.673 | 4.183 | −12.699 | 1.00 | 24.63 | B N |
| ATOM | 13675 | CA | VAL | B | 334 | 38.392 | 3.011 | −13.157 | 1.00 | 25.01 | B C |
| ATOM | 13677 | CB | VAL | B | 334 | 39.571 | 2.670 | −12.260 | 1.00 | 24.07 | B C |
| ATOM | 13679 | CG1 | VAL | B | 334 | 40.484 | 1.692 | −12.972 | 1.00 | 22.74 | B C |
| ATOM | 13683 | CG2 | VAL | B | 334 | 39.094 | 2.132 | −10.916 | 1.00 | 22.48 | B C |
| ATOM | 13687 | C | VAL | B | 334 | 37.471 | 1.805 | −13.298 | 1.00 | 28.84 | B C |
| ATOM | 13688 | O | VAL | B | 334 | 37.724 | 0.960 | −14.132 | 1.00 | 30.66 | B O |
| ATOM | 13690 | N | ASN | B | 335 | 36.384 | 1.751 | −12.530 | 1.00 | 30.57 | B N |
| ATOM | 13691 | CA | ASN | B | 335 | 35.396 | 0.670 | −12.667 | 1.00 | 32.76 | B C |
| ATOM | 13693 | CB | ASN | B | 335 | 34.426 | 0.659 | −11.474 | 1.00 | 32.97 | B C |
| ATOM | 13696 | CG | ASN | B | 335 | 35.150 | 0.526 | −10.136 | 1.00 | 36.11 | B C |
| ATOM | 13697 | OD1 | ASN | B | 335 | 35.846 | −0.464 | −9.891 | 1.00 | 32.01 | B O |
| ATOM | 13698 | ND2 | ASN | B | 335 | 35.002 | 1.537 | −9.272 | 1.00 | 31.45 | B N |
| ATOM | 13701 | C | ASN | B | 335 | 34.595 | 0.714 | −13.973 | 1.00 | 33.61 | B C |
| ATOM | 13702 | O | ASN | B | 335 | 33.783 | −0.158 | −14.187 | 1.00 | 32.20 | B O |
| ATOM | 13704 | N | ALA | B | 336 | 34.819 | 1.725 | −14.821 | 1.00 | 35.40 | B N |
| ATOM | 13705 | CA | ALA | B | 336 | 34.165 | 1.832 | −16.139 | 1.00 | 37.44 | B C |
| ATOM | 13707 | CB | ALA | B | 336 | 33.391 | 3.153 | −16.239 | 1.00 | 36.12 | B C |
| ATOM | 13711 | C | ALA | B | 336 | 35.147 | 1.708 | −17.306 | 1.00 | 37.97 | B C |
| ATOM | 13712 | O | ALA | B | 336 | 34.797 | 1.970 | −18.451 | 1.00 | 40.52 | B O |
| ATOM | 13714 | N | ILE | B | 337 | 36.371 | 1.291 | −17.006 | 1.00 | 39.74 | B N |
| ATOM | 13715 | CA | ILE | B | 337 | 37.417 | 1.027 | −18.010 | 1.00 | 39.19 | B C |
| ATOM | 13717 | CB | ILE | B | 337 | 38.706 | 0.448 | −17.308 | 1.00 | 40.69 | B C |
| ATOM | 13719 | CG1 | ILE | B | 337 | 39.903 | 0.392 | −18.237 | 1.00 | 45.92 | B C |
| ATOM | 13722 | CD1 | ILE | B | 337 | 41.134 | −0.183 | −17.566 | 1.00 | 45.35 | B C |
| ATOM | 13726 | CG2 | ILE | B | 337 | 38.488 | −0.946 | −16.773 | 1.00 | 38.80 | B C |
| ATOM | 13730 | C | ILE | B | 337 | 36.959 | 0.093 | −19.138 | 1.00 | 39.32 | B C |
| ATOM | 13731 | O | ILE | B | 337 | 37.385 | 0.260 | −20.278 | 1.00 | 39.83 | B O |
| ATOM | 13733 | N | ASN | B | 338 | 36.080 | −0.866 | −18.837 | 1.00 | 37.82 | B N |
| ATOM | 13734 | CA | ASN | B | 338 | 35.609 | −1.831 | −19.854 | 1.00 | 38.11 | B C |
| ATOM | 13736 | CB | ASN | B | 338 | 34.944 | −3.076 | −19.201 | 1.00 | 37.75 | B C |
| ATOM | 13739 | CG | ASN | B | 338 | 35.970 | −4.092 | −18.627 | 1.00 | 38.84 | B C |
| ATOM | 13740 | OD1 | ASN | B | 338 | 37.163 | −4.064 | −18.937 | 1.00 | 33.79 | B O |
| ATOM | 13741 | ND2 | ASN | B | 338 | 35.479 | −5.010 | −17.801 | 1.00 | 36.06 | B N |
| ATOM | 13744 | C | ASN | B | 338 | 34.705 | −1.253 | −20.973 | 1.00 | 36.95 | B C |
| ATOM | 13745 | O | ASN | B | 338 | 34.464 | −1.915 | −21.965 | 1.00 | 36.60 | B O |
| ATOM | 13747 | N | ASP | B | 339 | 34.243 | −0.019 | −20.839 | 1.00 | 37.98 | B N |
| ATOM | 13748 | CA | ASP | B | 339 | 33.479 | 0.647 | −21.920 | 1.00 | 38.56 | B C |
| ATOM | 13750 | CB | ASP | B | 339 | 32.804 | 1.938 | −21.394 | 1.00 | 40.02 | B C |
| ATOM | 13753 | CG | ASP | B | 339 | 31.899 | 1.706 | −20.161 | 1.00 | 44.52 | B C |
| ATOM | 13754 | OD1 | ASP | B | 339 | 31.430 | 0.568 | −19.940 | 1.00 | 49.31 | B O |
| ATOM | 13755 | OD2 | ASP | B | 339 | 31.641 | 2.690 | −19.430 | 1.00 | 45.68 | B O |
| ATOM | 13756 | C | ASP | B | 339 | 34.381 | 1.036 | −23.110 | 1.00 | 34.68 | B C |
| ATOM | 13757 | O | ASP | B | 339 | 33.918 | 1.279 | −24.221 | 1.00 | 34.99 | B O |
| ATOM | 13759 | N | LEU | B | 340 | 35.674 | 1.116 | −22.855 | 1.00 | 31.43 | B N |
| ATOM | 13760 | CA | LEU | B | 340 | 36.619 | 1.597 | −23.846 | 1.00 | 29.09 | B C |
| ATOM | 13762 | CB | LEU | B | 340 | 37.803 | 2.257 | −23.138 | 1.00 | 27.62 | B C |
| ATOM | 13765 | CG | LEU | B | 340 | 37.483 | 3.472 | −22.279 | 1.00 | 26.44 | B C |
| ATOM | 13767 | CD1 | LEU | B | 340 | 38.682 | 3.873 | −21.426 | 1.00 | 20.10 | B C |
| ATOM | 13771 | CD2 | LEU | B | 340 | 37.050 | 4.595 | −23.174 | 1.00 | 24.57 | B C |
| ATOM | 13775 | C | LEU | B | 340 | 37.145 | 0.464 | −24.725 | 1.00 | 25.95 | B C |
| ATOM | 13776 | O | LEU | B | 340 | 37.281 | −0.666 | −24.260 | 1.00 | 26.50 | B O |
| ATOM | 13778 | N | PRO | B | 341 | 37.472 | 0.773 | −25.984 | 1.00 | 24.08 | B N |
| ATOM | 13779 | CA | PRO | B | 341 | 38.167 | −0.187 | −26.836 | 1.00 | 24.62 | B C |

TABLE 4-2-continued

Coordinates of *P. alba* IspS

| ATOM | 13781 | CB | PRO | B | 341 | 38.191 | 0.493 | −28.218 | 1.00 | 24.85 | B | C |
|---|---|---|---|---|---|---|---|---|---|---|---|---|
| ATOM | 13784 | CG | PRO | B | 341 | 38.063 | 1.910 | −27.954 | 1.00 | 26.60 | B | C |
| ATOM | 13787 | CD | PRO | B | 341 | 37.281 | 2.065 | −26.661 | 1.00 | 25.30 | B | C |
| ATOM | 13790 | C | PRO | B | 341 | 39.564 | −0.443 | −26.320 | 1.00 | 23.26 | B | C |
| ATOM | 13791 | O | PRO | B | 341 | 40.103 | 0.360 | −25.544 | 1.00 | 21.32 | B | O |
| ATOM | 13792 | N | ASP | B | 342 | 40.134 | −1.571 | −26.725 | 1.00 | 23.87 | B | N |
| ATOM | 13793 | CA | ASP | B | 342 | 41.289 | −2.122 | −26.026 | 1.00 | 23.29 | B | C |
| ATOM | 13795 | CB | ASP | B | 342 | 41.767 | −3.425 | −26.696 | 1.00 | 25.56 | B | C |
| ATOM | 13798 | CG | ASP | B | 342 | 40.790 | −4.605 | −26.491 | 1.00 | 31.22 | B | C |
| ATOM | 13799 | OD1 | ASP | B | 342 | 39.943 | −4.549 | −25.566 | 1.00 | 32.95 | B | O |
| ATOM | 13800 | OD2 | ASP | B | 342 | 40.889 | −5.599 | −27.254 | 1.00 | 37.04 | B | O |
| ATOM | 13801 | C | ASP | B | 342 | 42.436 | −1.120 | −25.929 | 1.00 | 22.80 | B | C |
| ATOM | 13802 | O | ASP | B | 342 | 43.042 | −0.938 | −24.845 | 1.00 | 21.42 | B | O |
| ATOM | 13804 | N | TYR | B | 343 | 42.747 | −0.457 | −27.039 | 1.00 | 20.42 | B | N |
| ATOM | 13805 | CA | TYR | B | 343 | 43.912 | 0.428 | −27.038 | 1.00 | 20.57 | B | C |
| ATOM | 13807 | CB | TYR | B | 343 | 44.273 | 0.888 | −28.460 | 1.00 | 20.66 | B | C |
| ATOM | 13810 | CG | TYR | B | 343 | 43.398 | 1.977 | −29.041 | 1.00 | 23.23 | B | C |
| ATOM | 13811 | CD1 | TYR | B | 343 | 42.233 | 1.680 | −29.747 | 1.00 | 20.78 | B | C |
| ATOM | 13813 | CE1 | TYR | B | 343 | 41.441 | 2.700 | −30.274 | 1.00 | 26.89 | B | C |
| ATOM | 13815 | CZ | TYR | B | 343 | 41.836 | 4.026 | −30.103 | 1.00 | 23.64 | B | C |
| ATOM | 13816 | OH | TYR | B | 343 | 41.124 | 5.055 | −30.630 | 1.00 | 26.31 | B | O |
| ATOM | 13818 | CE2 | TYR | B | 343 | 42.993 | 4.332 | −29.437 | 1.00 | 22.44 | B | C |
| ATOM | 13820 | CD2 | TYR | B | 343 | 43.765 | 3.316 | −28.910 | 1.00 | 23.71 | B | C |
| ATOM | 13822 | C | TYR | B | 343 | 43.689 | 1.603 | −26.069 | 1.00 | 20.00 | B | C |
| ATOM | 13823 | O | TYR | B | 343 | 44.602 | 2.031 | −25.396 | 1.00 | 18.99 | B | O |
| ATOM | 13825 | N | MET | B | 344 | 42.459 | 2.080 | −25.966 | 1.00 | 20.82 | B | N |
| ATOM | 13826 | CA | MET | B | 344 | 42.145 | 3.158 | −25.030 | 1.00 | 20.77 | B | C |
| ATOM | 13828 | CB | MET | B | 344 | 40.819 | 3.806 | −25.392 | 1.00 | 20.51 | B | C |
| ATOM | 13831 | CG | MET | B | 344 | 40.953 | 4.773 | −26.564 | 1.00 | 21.38 | B | C |
| ATOM | 13834 | SD | MET | B | 344 | 39.418 | 5.528 | −27.088 | 1.00 | 22.33 | B | S |
| ATOM | 13835 | CE | MET | B | 344 | 40.022 | 6.860 | −28.132 | 1.00 | 16.19 | B | C |
| ATOM | 13839 | C | MET | B | 344 | 42.134 | 2.677 | −23.591 | 1.00 | 22.13 | B | C |
| ATOM | 13840 | O | MET | B | 344 | 42.497 | 3.420 | −22.682 | 1.00 | 20.90 | B | O |
| ATOM | 13842 | N | LYS | B | 345 | 41.731 | 1.427 | −23.402 | 1.00 | 23.38 | B | N |
| ATOM | 13843 | CA | LYS | B | 345 | 41.726 | 0.791 | −22.077 | 1.00 | 24.79 | B | C |
| ATOM | 13845 | CB | LYS | B | 345 | 41.476 | −0.712 | −22.211 | 1.00 | 27.00 | B | C |
| ATOM | 13848 | CG | LYS | B | 345 | 40.331 | −1.290 | −21.421 | 1.00 | 35.72 | B | C |
| ATOM | 13851 | CD | LYS | B | 345 | 39.732 | −2.426 | −22.257 | 1.00 | 37.84 | B | C |
| ATOM | 13854 | CE | LYS | B | 345 | 38.753 | −3.251 | −21.507 | 1.00 | 39.59 | B | C |
| ATOM | 13857 | NZ | LYS | B | 345 | 37.824 | −3.918 | −22.467 | 1.00 | 43.84 | B | N |
| ATOM | 13861 | C | LYS | B | 345 | 43.082 | 0.957 | −21.458 | 1.00 | 21.39 | B | C |
| ATOM | 13862 | O | LYS | B | 345 | 43.214 | 1.460 | −20.349 | 1.00 | 21.62 | B | O |
| ATOM | 13864 | N | LEU | B | 346 | 44.086 | 0.500 | −22.192 | 1.00 | 19.29 | B | N |
| ATOM | 13865 | CA | LEU | B | 346 | 45.449 | 0.496 | −21.723 | 1.00 | 20.97 | B | C |
| ATOM | 13867 | CB | LEU | B | 346 | 46.322 | −0.210 | −22.743 | 1.00 | 21.36 | B | C |
| ATOM | 13870 | CG | LEU | B | 346 | 47.675 | −0.639 | −22.223 | 1.00 | 23.78 | B | C |
| ATOM | 13872 | CD1 | LEU | B | 346 | 47.477 | −1.675 | −21.112 | 1.00 | 20.34 | B | C |
| ATOM | 13876 | CD2 | LEU | B | 346 | 48.444 | −1.253 | −23.370 | 1.00 | 27.71 | B | C |
| ATOM | 13880 | C | LEU | B | 346 | 45.958 | 1.908 | −21.486 | 1.00 | 21.00 | B | C |
| ATOM | 13881 | O | LEU | B | 346 | 46.523 | 2.225 | −20.433 | 1.00 | 21.92 | B | O |
| ATOM | 13883 | N | CYS | B | 347 | 45.753 | 2.763 | −22.469 | 1.00 | 19.96 | B | N |
| ATOM | 13884 | CA | CYS | B | 347 | 46.241 | 4.139 | −22.383 | 1.00 | 21.49 | B | C |
| ATOM | 13886 | CB | CYS | B | 347 | 45.945 | 4.847 | −23.725 | 1.00 | 23.29 | B | C |
| ATOM | 13889 | SG | CYS | B | 347 | 46.580 | 6.488 | −23.807 | 1.00 | 37.91 | B | S |
| ATOM | 13891 | C | CYS | B | 347 | 45.571 | 4.880 | −21.211 | 1.00 | 19.02 | B | C |
| ATOM | 13892 | O | CYS | B | 347 | 46.215 | 5.622 | −20.460 | 1.00 | 16.76 | B | O |
| ATOM | 13894 | N | PHE | B | 348 | 44.271 | 4.649 | −21.038 | 1.00 | 18.76 | B | N |
| ATOM | 13895 | CA | PHE | B | 348 | 43.529 | 5.306 | −19.983 | 1.00 | 18.67 | B | C |
| ATOM | 13897 | CB | PHE | B | 348 | 42.035 | 5.009 | −20.055 | 1.00 | 17.98 | B | C |
| ATOM | 13900 | CG | PHE | B | 348 | 41.269 | 5.635 | −18.939 | 1.00 | 17.07 | B | C |
| ATOM | 13901 | CD1 | PHE | B | 348 | 41.030 | 6.990 | −18.933 | 1.00 | 21.41 | B | C |
| ATOM | 13903 | CE1 | PHE | B | 348 | 40.352 | 7.592 | −17.885 | 1.00 | 23.96 | B | C |
| ATOM | 13905 | CZ | PHE | B | 348 | 39.939 | 6.844 | −16.815 | 1.00 | 21.12 | B | C |
| ATOM | 13907 | CE2 | PHE | B | 348 | 40.191 | 5.484 | −16.803 | 1.00 | 22.43 | B | C |
| ATOM | 13909 | CD2 | PHE | B | 348 | 40.867 | 4.894 | −17.855 | 1.00 | 21.94 | B | C |
| ATOM | 13911 | C | PHE | B | 348 | 44.032 | 4.868 | −18.616 | 1.00 | 18.84 | B | C |
| ATOM | 13912 | O | PHE | B | 348 | 44.286 | 5.700 | −17.738 | 1.00 | 17.72 | B | O |
| ATOM | 13914 | N | LEU | B | 349 | 44.174 | 3.562 | −18.429 | 1.00 | 17.46 | B | N |
| ATOM | 13915 | CA | LEU | B | 349 | 44.520 | 3.063 | −17.118 | 1.00 | 18.56 | B | C |
| ATOM | 13917 | CB | LEU | B | 349 | 44.388 | 1.545 | −17.053 | 1.00 | 19.12 | B | C |
| ATOM | 13920 | CG | LEU | B | 349 | 44.690 | 0.832 | −15.727 | 1.00 | 19.64 | B | C |
| ATOM | 13922 | CD1 | LEU | B | 349 | 44.000 | 1.519 | −14.535 | 1.00 | 13.56 | B | C |
| ATOM | 13926 | CD2 | LEU | B | 349 | 44.259 | −0.634 | −15.855 | 1.00 | 11.45 | B | C |
| ATOM | 13930 | C | LEU | B | 349 | 45.926 | 3.532 | −16.771 | 1.00 | 19.38 | B | C |
| ATOM | 13931 | O | LEU | B | 349 | 46.196 | 3.873 | −15.620 | 1.00 | 16.91 | B | O |
| ATOM | 13933 | N | ALA | B | 350 | 46.810 | 3.590 | −17.774 | 1.00 | 21.32 | B | N |
| ATOM | 13934 | CA | ALA | B | 350 | 48.189 | 4.094 | −17.560 | 1.00 | 20.38 | B | C |
| ATOM | 13936 | CB | ALA | B | 350 | 49.004 | 3.959 | −18.854 | 1.00 | 20.36 | B | C |

TABLE 4-2-continued

Coordinates of *P. alba* IspS

| ATOM | 13940 | C | ALA | B | 350 | 48.232 | 5.538 | −17.068 | 1.00 | 17.92 | B | C |
|------|-------|------|------|---|-----|--------|--------|---------|------|-------|---|---|
| ATOM | 13941 | O | ALA | B | 350 | 48.948 | 5.872 | −16.148 | 1.00 | 15.97 | B | O |
| ATOM | 13943 | N | LEU | B | 351 | 47.493 | 6.400 | −17.747 | 1.00 | 19.62 | B | N |
| ATOM | 13944 | CA | LEU | B | 351 | 47.334 | 7.796 | −17.357 | 1.00 | 18.33 | B | C |
| ATOM | 13946 | CB | LEU | B | 351 | 46.440 | 8.505 | −18.390 | 1.00 | 21.12 | B | C |
| ATOM | 13949 | CG | LEU | B | 351 | 46.123 | 9.988 | −18.131 | 1.00 | 23.41 | B | C |
| ATOM | 13951 | CD1 | LEU | B | 351 | 47.364 | 10.823 | −18.236 | 1.00 | 19.59 | B | C |
| ATOM | 13955 | CD2 | LEU | B | 351 | 45.052 | 10.462 | −19.098 | 1.00 | 22.85 | B | C |
| ATOM | 13959 | C | LEU | B | 351 | 46.694 | 7.924 | −15.972 | 1.00 | 18.87 | B | C |
| ATOM | 13960 | O | LEU | B | 351 | 47.165 | 8.709 | −15.117 | 1.00 | 19.16 | B | O |
| ATOM | 13962 | N | TYR | B | 352 | 45.604 | 7.176 | −15.780 | 1.00 | 16.72 | B | N |
| ATOM | 13963 | CA | TYR | B | 352 | 44.870 | 7.128 | −14.520 | 1.00 | 16.75 | B | C |
| ATOM | 13965 | CB | TYR | B | 352 | 43.799 | 6.040 | −14.614 | 1.00 | 18.50 | B | C |
| ATOM | 13968 | CG | TYR | B | 352 | 42.765 | 5.984 | −13.519 | 1.00 | 17.16 | B | C |
| ATOM | 13969 | CD1 | TYR | B | 352 | 41.688 | 6.868 | −13.514 | 1.00 | 22.74 | B | C |
| ATOM | 13971 | CE1 | TYR | B | 352 | 40.702 | 6.807 | −12.524 | 1.00 | 21.64 | B | C |
| ATOM | 13973 | CZ | TYR | B | 352 | 40.788 | 5.858 | −11.535 | 1.00 | 21.98 | B | C |
| ATOM | 13974 | OH | TYR | B | 352 | 39.800 | 5.795 | −10.560 | 1.00 | 25.58 | B | O |
| ATOM | 13976 | CE2 | TYR | B | 352 | 41.861 | 4.956 | −11.528 | 1.00 | 19.79 | B | C |
| ATOM | 13978 | CD2 | TYR | B | 352 | 42.828 | 5.022 | −12.524 | 1.00 | 17.06 | B | C |
| ATOM | 13980 | C | TYR | B | 352 | 45.801 | 6.835 | −13.363 | 1.00 | 16.79 | B | C |
| ATOM | 13981 | O | TYR | B | 352 | 45.874 | 7.601 | −12.384 | 1.00 | 17.65 | B | O |
| ATOM | 13983 | N | ASN | B | 353 | 46.534 | 5.734 | −13.460 | 1.00 | 16.33 | B | N |
| ATOM | 13984 | CA | ASN | B | 353 | 47.437 | 5.356 | −12.361 | 1.00 | 18.36 | B | C |
| ATOM | 13986 | CB | ASN | B | 353 | 48.058 | 3.995 | −12.629 | 1.00 | 15.27 | B | C |
| ATOM | 13989 | CG | ASN | B | 353 | 47.068 | 2.864 | −12.502 | 1.00 | 19.46 | B | C |
| ATOM | 13990 | OD1 | ASN | B | 353 | 45.965 | 3.037 | −11.982 | 1.00 | 17.65 | B | O |
| ATOM | 13991 | ND2 | ASN | B | 353 | 47.463 | 1.677 | −12.969 | 1.00 | 15.56 | B | N |
| ATOM | 13994 | C | ASN | B | 353 | 48.538 | 6.420 | −12.127 | 1.00 | 18.63 | B | C |
| ATOM | 13995 | O | ASN | B | 353 | 48.930 | 6.688 | −10.994 | 1.00 | 13.58 | B | O |
| ATOM | 13997 | N | THR | B | 354 | 49.012 | 7.047 | −13.210 | 1.00 | 19.49 | B | N |
| ATOM | 13998 | CA | THR | B | 354 | 50.102 | 7.999 | −13.110 | 1.00 | 17.67 | B | C |
| ATOM | 14000 | CB | THR | B | 354 | 50.610 | 8.406 | −14.501 | 1.00 | 20.08 | B | C |
| ATOM | 14002 | OG1 | THR | B | 354 | 51.004 | 7.243 | −15.238 | 1.00 | 18.36 | B | O |
| ATOM | 14004 | CG2 | THR | B | 354 | 51.789 | 9.381 | −14.389 | 1.00 | 17.15 | B | C |
| ATOM | 14008 | C | THR | B | 354 | 49.634 | 9.239 | −12.347 | 1.00 | 18.15 | B | C |
| ATOM | 14009 | O | THR | B | 354 | 50.316 | 9.713 | −11.462 | 1.00 | 18.88 | B | O |
| ATOM | 14011 | N | ILE | B | 355 | 48.454 | 9.728 | −12.694 | 1.00 | 16.69 | B | N |
| ATOM | 14012 | CA | ILE | B | 355 | 47.908 | 10.920 | −12.095 | 1.00 | 17.85 | B | C |
| ATOM | 14014 | CB | ILE | B | 355 | 46.657 | 11.416 | −12.875 | 1.00 | 18.34 | B | C |
| ATOM | 14016 | CG1 | ILE | B | 355 | 46.999 | 11.833 | −14.317 | 1.00 | 21.17 | B | C |
| ATOM | 14019 | CD1 | ILE | B | 355 | 48.356 | 12.354 | −14.519 | 1.00 | 25.46 | B | C |
| ATOM | 14023 | CG2 | ILE | B | 355 | 45.993 | 12.558 | −12.164 | 1.00 | 19.09 | B | C |
| ATOM | 14027 | C | ILE | B | 355 | 47.550 | 10.632 | −10.630 | 1.00 | 17.55 | B | C |
| ATOM | 14028 | O | ILE | B | 355 | 47.954 | 11.376 | −9.729 | 1.00 | 14.98 | B | O |
| ATOM | 14030 | N | ASN | B | 356 | 46.806 | 9.557 | −10.387 | 1.00 | 17.07 | B | N |
| ATOM | 14031 | CA | ASN | B | 356 | 46.532 | 9.152 | −9.008 | 1.00 | 18.16 | B | C |
| ATOM | 14033 | CB | ASN | B | 356 | 45.687 | 7.874 | −8.941 | 1.00 | 17.23 | B | C |
| ATOM | 14036 | CG | ASN | B | 356 | 44.314 | 8.080 | −9.531 | 1.00 | 17.52 | B | C |
| ATOM | 14037 | OD1 | ASN | B | 356 | 43.925 | 9.217 | −9.798 | 1.00 | 25.68 | B | O |
| ATOM | 14038 | ND2 | ASN | B | 356 | 43.592 | 7.004 | −9.782 | 1.00 | 19.09 | B | N |
| ATOM | 14041 | C | ASN | B | 356 | 47.783 | 9.003 | −8.161 | 1.00 | 19.24 | B | C |
| ATOM | 14042 | O | ASN | B | 356 | 47.765 | 9.283 | −6.975 | 1.00 | 22.07 | B | O |
| ATOM | 14044 | N | GLU | B | 357 | 48.885 | 8.596 | −8.752 | 1.00 | 21.23 | B | N |
| ATOM | 14045 | CA | GLU | B | 357 | 50.112 | 8.425 | −7.967 | 1.00 | 19.96 | B | C |
| ATOM | 14047 | CB | GLU | B | 357 | 51.064 | 7.495 | −8.708 | 1.00 | 18.90 | B | C |
| ATOM | 14050 | CG | GLU | B | 357 | 52.445 | 7.346 | −8.117 | 1.00 | 34.11 | B | C |
| ATOM | 14053 | CD | GLU | B | 357 | 53.308 | 6.403 | −8.934 | 1.00 | 49.89 | B | C |
| ATOM | 14054 | OE1 | GLU | B | 357 | 54.545 | 6.565 | −8.899 | 1.00 | 54.67 | B | O |
| ATOM | 14055 | OE2 | GLU | B | 357 | 52.742 | 5.520 | −9.630 | 1.00 | 62.79 | B | O |
| ATOM | 14056 | C | GLU | B | 357 | 50.738 | 9.782 | −7.660 | 1.00 | 18.63 | B | C |
| ATOM | 14057 | O | GLU | B | 357 | 51.308 | 9.983 | −6.589 | 1.00 | 17.61 | B | O |
| ATOM | 14059 | N | ILE | B | 358 | 50.625 | 10.741 | −8.571 | 1.00 | 20.13 | B | N |
| ATOM | 14060 | CA | ILE | B | 358 | 51.074 | 12.094 | −8.246 | 1.00 | 19.81 | B | C |
| ATOM | 14062 | CB | ILE | B | 358 | 51.160 | 12.978 | −9.495 | 1.00 | 23.03 | B | C |
| ATOM | 14064 | CG1 | ILE | B | 358 | 52.286 | 12.481 | −10.418 | 1.00 | 23.28 | B | C |
| ATOM | 14067 | CD1 | ILE | B | 358 | 52.104 | 12.900 | −11.898 | 1.00 | 17.88 | B | C |
| ATOM | 14071 | CG2 | ILE | B | 358 | 51.438 | 14.454 | −9.111 | 1.00 | 18.37 | B | C |
| ATOM | 14075 | C | ILE | B | 358 | 50.150 | 12.692 | −7.164 | 1.00 | 19.64 | B | C |
| ATOM | 14076 | O | ILE | B | 358 | 50.621 | 13.279 | −6.196 | 1.00 | 18.49 | B | O |
| ATOM | 14078 | N | ALA | B | 359 | 48.835 | 12.505 | −7.298 | 1.00 | 21.04 | B | N |
| ATOM | 14079 | CA | ALA | B | 359 | 47.910 | 12.942 | −6.247 | 1.00 | 19.40 | B | C |
| ATOM | 14081 | CB | ALA | B | 359 | 46.510 | 12.504 | −6.556 | 1.00 | 16.36 | B | C |
| ATOM | 14085 | C | ALA | B | 359 | 48.371 | 12.364 | −4.920 | 1.00 | 21.14 | B | C |
| ATOM | 14086 | O | ALA | B | 359 | 48.372 | 13.050 | −3.874 | 1.00 | 22.13 | B | O |
| ATOM | 14088 | N | TYR | B | 360 | 48.815 | 11.109 | −4.955 | 1.00 | 19.16 | B | N |
| ATOM | 14089 | CA | TYR | B | 360 | 49.215 | 10.452 | −3.712 | 1.00 | 18.42 | B | C |
| ATOM | 14091 | CB | TYR | B | 360 | 49.446 | 8.947 | −3.887 | 1.00 | 15.75 | B | C |

TABLE 4-2-continued

Coordinates of *P. alba* IspS

| ATOM | 14094 | CG | TYR | B | 360 | 49.888 | 8.307 | −2.601 | 1.00 | 12.33 | B | C |
|---|---|---|---|---|---|---|---|---|---|---|---|---|
| ATOM | 14095 | CD1 | TYR | B | 360 | 48.972 | 7.920 | −1.649 | 1.00 | 13.40 | B | C |
| ATOM | 14097 | CE1 | TYR | B | 360 | 49.371 | 7.368 | −0.458 | 1.00 | 9.59 | B | C |
| ATOM | 14099 | CZ | TYR | B | 360 | 50.716 | 7.214 | −0.194 | 1.00 | 15.43 | B | C |
| ATOM | 14100 | OH | TYR | B | 360 | 51.132 | 6.646 | 1.000 | 1.00 | 13.06 | B | O |
| ATOM | 14102 | CE2 | TYR | B | 360 | 51.646 | 7.606 | −1.132 | 1.00 | 12.26 | B | C |
| ATOM | 14104 | CD2 | TYR | B | 360 | 51.233 | 8.143 | −2.315 | 1.00 | 12.87 | B | C |
| ATOM | 14106 | C | TYR | B | 360 | 50.424 | 11.100 | −3.064 | 1.00 | 16.88 | B | C |
| ATOM | 14107 | O | TYR | B | 360 | 50.434 | 11.292 | −1.857 | 1.00 | 16.26 | B | O |
| ATOM | 14109 | N | ASP | B | 361 | 51.445 | 11.406 | −3.855 | 1.00 | 19.15 | B | N |
| ATOM | 14110 | CA | ASP | B | 361 | 52.668 | 12.027 | −3.354 | 1.00 | 20.70 | B | C |
| ATOM | 14112 | CB | ASP | B | 361 | 53.668 | 12.338 | −4.492 | 1.00 | 22.88 | B | C |
| ATOM | 14115 | CG | ASP | B | 361 | 54.242 | 11.079 | −5.177 | 1.00 | 30.52 | B | C |
| ATOM | 14116 | OD1 | ASP | B | 361 | 54.385 | 10.017 | −4.519 | 1.00 | 34.42 | B | O |
| ATOM | 14117 | OD2 | ASP | B | 361 | 54.556 | 11.171 | −6.382 | 1.00 | 37.22 | B | O |
| ATOM | 14118 | C | ASP | B | 361 | 52.319 | 13.350 | −2.676 | 1.00 | 22.70 | B | C |
| ATOM | 14119 | O | ASP | B | 361 | 52.856 | 13.697 | −1.635 | 1.00 | 21.32 | B | O |
| ATOM | 14121 | N | ASN | B | 362 | 51.427 | 14.097 | −3.308 | 1.00 | 22.85 | B | N |
| ATOM | 14122 | CA | ASN | B | 362 | 50.995 | 15.345 | −2.761 | 1.00 | 23.65 | B | C |
| ATOM | 14124 | CB | ASN | B | 362 | 50.210 | 16.111 | −3.804 | 1.00 | 25.00 | B | C |
| ATOM | 14127 | CG | ASN | B | 362 | 51.100 | 16.886 | −4.672 | 1.00 | 30.68 | B | C |
| ATOM | 14128 | OD1 | ASN | B | 362 | 51.508 | 17.995 | −4.301 | 1.00 | 29.31 | B | O |
| ATOM | 14129 | ND2 | ASN | B | 362 | 51.492 | 16.295 | −5.823 | 1.00 | 34.07 | B | N |
| ATOM | 14132 | C | ASN | B | 362 | 50.178 | 15.225 | −1.495 | 1.00 | 22.70 | B | C |
| ATOM | 14133 | O | ASN | B | 362 | 50.337 | 16.038 | −0.590 | 1.00 | 22.27 | B | O |
| ATOM | 14135 | N | LEU | B | 363 | 49.292 | 14.249 | −1.438 | 1.00 | 20.22 | B | N |
| ATOM | 14136 | CA | LEU | B | 363 | 48.564 | 14.000 | −0.210 | 1.00 | 20.99 | B | C |
| ATOM | 14138 | CB | LEU | B | 363 | 47.544 | 12.874 | −0.388 | 1.00 | 19.03 | B | C |
| ATOM | 14141 | CG | LEU | B | 363 | 46.668 | 12.477 | 0.809 | 1.00 | 22.46 | B | C |
| ATOM | 14143 | CD1 | LEU | B | 363 | 45.834 | 13.657 | 1.352 | 1.00 | 16.50 | B | C |
| ATOM | 14147 | CD2 | LEU | B | 363 | 45.757 | 11.304 | 0.456 | 1.00 | 15.67 | B | C |
| ATOM | 14151 | C | LEU | B | 363 | 49.582 | 13.669 | 0.868 | 1.00 | 21.81 | B | C |
| ATOM | 14152 | O | LEU | B | 363 | 49.546 | 14.234 | 1.950 | 1.00 | 22.89 | B | O |
| ATOM | 14154 | N | LYS | B | 364 | 50.531 | 12.798 | 0.558 | 1.00 | 24.05 | B | N |
| ATOM | 14155 | CA | LYS | B | 364 | 51.494 | 12.362 | 1.566 | 1.00 | 24.81 | B | C |
| ATOM | 14157 | CB | LYS | B | 364 | 52.416 | 11.272 | 1.015 | 1.00 | 24.82 | B | C |
| ATOM | 14160 | CG | LYS | B | 364 | 53.281 | 10.584 | 2.058 | 1.00 | 27.90 | B | C |
| ATOM | 14163 | CD | LYS | B | 364 | 54.170 | 9.479 | 1.430 | 1.00 | 31.07 | B | C |
| ATOM | 14166 | CE | LYS | B | 364 | 55.496 | 9.983 | 0.869 | 1.00 | 27.35 | B | C |
| ATOM | 14169 | NZ | LYS | B | 364 | 55.461 | 10.244 | −0.578 | 1.00 | 39.19 | B | N |
| ATOM | 14173 | C | LYS | B | 364 | 52.340 | 13.526 | 2.066 | 1.00 | 26.11 | B | C |
| ATOM | 14174 | O | LYS | B | 364 | 52.554 | 13.650 | 3.281 | 1.00 | 23.11 | B | O |
| ATOM | 14176 | N | ASP | B | 365 | 52.838 | 14.349 | 1.133 | 1.00 | 25.89 | B | N |
| ATOM | 14177 | CA | ASP | B | 365 | 53.864 | 15.347 | 1.466 | 1.00 | 29.64 | B | C |
| ATOM | 14179 | CB | ASP | B | 365 | 54.815 | 15.590 | 0.286 | 1.00 | 31.01 | B | C |
| ATOM | 14182 | CG | ASP | B | 365 | 55.574 | 14.334 | −0.135 | 1.00 | 40.18 | B | C |
| ATOM | 14183 | OD1 | ASP | B | 365 | 55.800 | 13.438 | 0.719 | 1.00 | 43.63 | B | O |
| ATOM | 14184 | OD2 | ASP | B | 365 | 55.939 | 14.257 | −1.336 | 1.00 | 47.50 | B | O |
| ATOM | 14185 | C | ASP | B | 365 | 53.276 | 16.680 | 1.907 | 1.00 | 29.07 | B | C |
| ATOM | 14186 | O | ASP | B | 365 | 53.883 | 17.378 | 2.696 | 1.00 | 31.54 | B | O |
| ATOM | 14188 | N | LYS | B | 366 | 52.104 | 17.028 | 1.395 | 1.00 | 28.84 | B | N |
| ATOM | 14189 | CA | LYS | B | 366 | 51.490 | 18.322 | 1.681 | 1.00 | 31.06 | B | C |
| ATOM | 14191 | CB | LYS | B | 366 | 51.269 | 19.114 | 0.382 | 1.00 | 31.40 | B | C |
| ATOM | 14194 | CG | LYS | B | 366 | 52.545 | 19.404 | −0.401 | 1.00 | 37.02 | B | C |
| ATOM | 14197 | CD | LYS | B | 366 | 52.242 | 20.235 | −1.658 | 1.00 | 53.13 | B | C |
| ATOM | 14200 | CE | LYS | B | 366 | 53.336 | 20.108 | −2.732 | 1.00 | 58.38 | B | C |
| ATOM | 14203 | NZ | LYS | B | 366 | 54.714 | 20.334 | −2.185 | 1.00 | 64.76 | B | N |
| ATOM | 14207 | C | LYS | B | 366 | 50.172 | 18.210 | 2.446 | 1.00 | 31.50 | B | C |
| ATOM | 14208 | O | LYS | B | 366 | 49.653 | 19.220 | 2.915 | 1.00 | 33.61 | B | O |
| ATOM | 14210 | N | GLY | B | 367 | 49.631 | 17.002 | 2.579 | 1.00 | 28.68 | B | N |
| ATOM | 14211 | CA | GLY | B | 367 | 48.409 | 16.804 | 3.338 | 1.00 | 27.28 | B | C |
| ATOM | 14214 | C | GLY | B | 367 | 47.191 | 17.406 | 2.685 | 1.00 | 27.99 | B | C |
| ATOM | 14215 | O | GLY | B | 367 | 46.250 | 17.788 | 3.386 | 1.00 | 28.42 | B | O |
| ATOM | 14217 | N | GLU | B | 368 | 47.203 | 17.468 | 1.347 | 1.00 | 27.86 | B | N |
| ATOM | 14218 | CA | GLU | B | 368 | 46.081 | 17.979 | 0.547 | 1.00 | 27.52 | B | C |
| ATOM | 14220 | CB | GLU | B | 368 | 46.450 | 19.330 | −0.095 | 1.00 | 30.43 | B | C |
| ATOM | 14223 | CG | GLU | B | 368 | 46.948 | 20.426 | 0.862 | 1.00 | 39.15 | B | C |
| ATOM | 14226 | CD | GLU | B | 368 | 45.836 | 21.137 | 1.619 | 1.00 | 47.36 | B | C |
| ATOM | 14227 | OE1 | GLU | B | 368 | 44.658 | 20.703 | 1.548 | 1.00 | 49.41 | B | O |
| ATOM | 14228 | OE2 | GLU | B | 368 | 46.162 | 22.142 | 2.291 | 1.00 | 53.64 | B | O |
| ATOM | 14229 | C | GLU | B | 368 | 45.713 | 17.032 | −0.591 | 1.00 | 24.33 | B | C |
| ATOM | 14230 | O | GLU | B | 368 | 46.584 | 16.536 | −1.308 | 1.00 | 22.31 | B | O |
| ATOM | 14232 | N | ASN | B | 369 | 44.421 | 16.800 | −0.764 | 1.00 | 23.20 | B | N |
| ATOM | 14233 | CA | ASN | B | 369 | 43.909 | 16.123 | −1.947 | 1.00 | 23.98 | B | C |
| ATOM | 14235 | CB | ASN | B | 369 | 42.532 | 15.541 | −1.671 | 1.00 | 23.61 | B | C |
| ATOM | 14238 | CG | ASN | B | 369 | 42.019 | 14.665 | −2.820 | 1.00 | 28.43 | B | C |
| ATOM | 14239 | OD1 | ASN | B | 369 | 42.646 | 14.562 | −3.880 | 1.00 | 27.91 | B | O |
| ATOM | 14240 | ND2 | ASN | B | 369 | 40.871 | 14.015 | −2.597 | 1.00 | 22.66 | B | N |

TABLE 4-2-continued

Coordinates of *P. alba* IspS

| ATOM | 14243 | C | ASN | B | 369 | 43.806 | 17.093 | −3.129 | 1.00 | 23.36 | B | C |
|---|---|---|---|---|---|---|---|---|---|---|---|---|
| ATOM | 14244 | O | ASN | B | 369 | 42.863 | 17.874 | −3.200 | 1.00 | 24.65 | B | O |
| ATOM | 14246 | N | ILE | B | 370 | 44.751 | 17.015 | −4.059 | 1.00 | 21.14 | B | N |
| ATOM | 14247 | CA | ILE | B | 370 | 44.723 | 17.849 | −5.249 | 1.00 | 21.55 | B | C |
| ATOM | 14249 | CB | ILE | B | 370 | 46.137 | 18.417 | −5.572 | 1.00 | 22.76 | B | C |
| ATOM | 14251 | CG1 | ILE | B | 370 | 47.140 | 17.296 | −5.847 | 1.00 | 22.92 | B | C |
| ATOM | 14254 | CD1 | ILE | B | 370 | 48.345 | 17.766 | −6.586 | 1.00 | 25.13 | B | C |
| ATOM | 14258 | CG2 | ILE | B | 370 | 46.639 | 19.311 | −4.433 | 1.00 | 21.02 | B | C |
| ATOM | 14262 | C | ILE | B | 370 | 44.180 | 17.118 | −6.492 | 1.00 | 22.16 | B | C |
| ATOM | 14263 | O | ILE | B | 370 | 44.222 | 17.661 | −7.593 | 1.00 | 21.34 | B | O |
| ATOM | 14265 | N | LEU | B | 371 | 43.669 | 15.898 | −6.330 | 1.00 | 20.03 | B | N |
| ATOM | 14266 | CA | LEU | B | 371 | 43.260 | 15.105 | −7.485 | 1.00 | 20.80 | B | C |
| ATOM | 14268 | CB | LEU | B | 371 | 42.735 | 13.735 | −7.052 | 1.00 | 19.94 | B | C |
| ATOM | 14271 | CG | LEU | B | 371 | 42.452 | 12.746 | −8.191 | 1.00 | 22.27 | B | C |
| ATOM | 14273 | CD1 | LEU | B | 371 | 43.736 | 12.396 | −8.973 | 1.00 | 16.64 | B | C |
| ATOM | 14277 | CD2 | LEU | B | 371 | 41.792 | 11.477 | −7.642 | 1.00 | 18.00 | B | C |
| ATOM | 14281 | C | LEU | B | 371 | 42.219 | 15.800 | −8.387 | 1.00 | 22.85 | B | C |
| ATOM | 14282 | O | LEU | B | 371 | 42.340 | 15.738 | −9.623 | 1.00 | 24.00 | B | O |
| ATOM | 14284 | N | PRO | B | 372 | 41.201 | 16.468 | −7.787 | 1.00 | 23.30 | B | N |
| ATOM | 14285 | CA | PRO | B | 372 | 40.201 | 17.090 | −8.648 | 1.00 | 23.58 | B | C |
| ATOM | 14287 | CB | PRO | B | 372 | 39.225 | 17.761 | −7.670 | 1.00 | 24.01 | B | C |
| ATOM | 14290 | CG | PRO | B | 372 | 39.457 | 17.118 | −6.376 | 1.00 | 28.41 | B | C |
| ATOM | 14293 | CD | PRO | B | 372 | 40.897 | 16.685 | −6.359 | 1.00 | 25.80 | B | C |
| ATOM | 14296 | C | PRO | B | 372 | 40.804 | 18.105 | −9.604 | 1.00 | 22.18 | B | C |
| ATOM | 14297 | O | PRO | B | 372 | 40.310 | 18.227 | −10.701 | 1.00 | 23.54 | B | O |
| ATOM | 14298 | N | TYR | B | 373 | 41.867 | 18.790 | −9.195 | 1.00 | 21.49 | B | N |
| ATOM | 14299 | CA | TYR | B | 373 | 42.552 | 19.781 | −10.047 | 1.00 | 24.02 | B | C |
| ATOM | 14301 | CB | TYR | B | 373 | 43.456 | 20.714 | −9.213 | 1.00 | 25.06 | B | C |
| ATOM | 14304 | CG | TYR | B | 373 | 42.747 | 21.255 | −7.971 | 1.00 | 28.99 | B | C |
| ATOM | 14305 | CD1 | TYR | B | 373 | 41.617 | 22.058 | −8.083 | 1.00 | 37.98 | B | C |
| ATOM | 14307 | CE1 | TYR | B | 373 | 40.932 | 22.510 | −6.958 | 1.00 | 38.97 | B | C |
| ATOM | 14309 | CZ | TYR | B | 373 | 41.378 | 22.165 | −5.709 | 1.00 | 40.12 | B | C |
| ATOM | 14310 | OH | TYR | B | 373 | 40.713 | 22.610 | −4.589 | 1.00 | 48.27 | B | O |
| ATOM | 14312 | CE2 | TYR | B | 373 | 42.488 | 21.359 | −5.568 | 1.00 | 40.83 | B | C |
| ATOM | 14314 | CD2 | TYR | B | 373 | 43.160 | 20.898 | −6.702 | 1.00 | 33.96 | B | C |
| ATOM | 14316 | C | TYR | B | 373 | 43.366 | 19.107 | −11.147 | 1.00 | 25.44 | B | C |
| ATOM | 14317 | O | TYR | B | 373 | 43.388 | 19.591 | −12.283 | 1.00 | 26.29 | B | O |
| ATOM | 14319 | N | LEU | B | 374 | 44.013 | 17.980 | −10.834 | 1.00 | 24.17 | B | N |
| ATOM | 14320 | CA | LEU | B | 374 | 44.808 | 17.285 | −11.844 | 1.00 | 20.73 | B | C |
| ATOM | 14322 | CB | LEU | B | 374 | 45.721 | 16.236 | −11.224 | 1.00 | 20.86 | B | C |
| ATOM | 14325 | CG | LEU | B | 374 | 46.684 | 16.702 | −10.130 | 1.00 | 20.24 | B | C |
| ATOM | 14327 | CD1 | LEU | B | 374 | 47.543 | 15.508 | −9.612 | 1.00 | 16.80 | B | C |
| ATOM | 14331 | CD2 | LEU | B | 374 | 47.562 | 17.841 | −10.572 | 1.00 | 17.67 | B | C |
| ATOM | 14335 | C | LEU | B | 374 | 43.891 | 16.659 | −12.869 | 1.00 | 18.95 | B | C |
| ATOM | 14336 | O | LEU | B | 374 | 44.166 | 16.700 | −14.059 | 1.00 | 20.39 | B | O |
| ATOM | 14338 | N | THR | B | 375 | 42.772 | 16.107 | −12.439 | 1.00 | 20.66 | B | N |
| ATOM | 14339 | CA | THR | B | 375 | 41.896 | 15.466 | −13.399 | 1.00 | 19.66 | B | C |
| ATOM | 14341 | CB | THR | B | 375 | 40.958 | 14.480 | −12.726 | 1.00 | 21.51 | B | C |
| ATOM | 14343 | OG1 | THR | B | 375 | 40.128 | 15.161 | −11.787 | 1.00 | 22.47 | B | O |
| ATOM | 14345 | CG2 | THR | B | 375 | 41.788 | 13.374 | −12.020 | 1.00 | 15.76 | B | C |
| ATOM | 14349 | C | THR | B | 375 | 41.130 | 16.486 | −14.248 | 1.00 | 22.51 | B | C |
| ATOM | 14350 | O | THR | B | 375 | 40.859 | 16.249 | −15.429 | 1.00 | 23.67 | B | O |
| ATOM | 14352 | N | LYS | B | 376 | 40.798 | 17.631 | −13.670 | 1.00 | 23.19 | B | N |
| ATOM | 14353 | CA | LYS | B | 376 | 40.133 | 18.683 | −14.434 | 1.00 | 24.29 | B | C |
| ATOM | 14355 | CB | LYS | B | 376 | 39.727 | 19.837 | −13.517 | 1.00 | 25.69 | B | C |
| ATOM | 14358 | CG | LYS | B | 376 | 38.961 | 20.963 | −14.212 | 1.00 | 32.29 | B | C |
| ATOM | 14361 | CD | LYS | B | 376 | 37.580 | 20.536 | −14.716 | 1.00 | 36.20 | B | C |
| ATOM | 14364 | CE | LYS | B | 376 | 36.881 | 21.706 | −15.449 | 1.00 | 39.50 | B | C |
| ATOM | 14367 | NZ | LYS | B | 376 | 35.532 | 21.322 | −15.952 | 1.00 | 46.03 | B | N |
| ATOM | 14371 | C | LYS | B | 376 | 41.050 | 19.181 | −15.535 | 1.00 | 21.89 | B | C |
| ATOM | 14372 | O | LYS | B | 376 | 40.614 | 19.403 | −16.653 | 1.00 | 24.65 | B | O |
| ATOM | 14374 | N | ALA | B | 377 | 42.325 | 19.356 | −15.222 | 1.00 | 20.03 | B | N |
| ATOM | 14375 | CA | ALA | B | 377 | 43.294 | 19.765 | −16.228 | 1.00 | 18.15 | B | C |
| ATOM | 14377 | CB | ALA | B | 377 | 44.692 | 19.870 | −15.637 | 1.00 | 18.15 | B | C |
| ATOM | 14381 | C | ALA | B | 377 | 43.283 | 18.775 | −17.366 | 1.00 | 18.11 | B | C |
| ATOM | 14382 | O | ALA | B | 377 | 43.257 | 19.189 | −18.533 | 1.00 | 18.41 | B | O |
| ATOM | 14384 | N | TRP | B | 378 | 43.258 | 17.473 | −17.059 | 1.00 | 17.59 | B | N |
| ATOM | 14385 | CA | TRP | B | 378 | 43.221 | 16.492 | −18.146 | 1.00 | 19.76 | B | C |
| ATOM | 14387 | CB | TRP | B | 378 | 43.567 | 15.063 | −17.701 | 1.00 | 20.21 | B | C |
| ATOM | 14390 | CG | TRP | B | 378 | 45.032 | 14.853 | −17.733 | 1.00 | 19.57 | B | C |
| ATOM | 14391 | CD1 | TRP | B | 378 | 45.905 | 14.995 | −16.696 | 1.00 | 16.98 | B | C |
| ATOM | 14393 | NE1 | TRP | B | 378 | 47.183 | 14.779 | −17.128 | 1.00 | 19.55 | B | N |
| ATOM | 14395 | CE2 | TRP | B | 378 | 47.152 | 14.483 | −18.466 | 1.00 | 17.20 | B | C |
| ATOM | 14396 | CD2 | TRP | B | 378 | 45.816 | 14.528 | −18.878 | 1.00 | 17.73 | B | C |
| ATOM | 14397 | CE3 | TRP | B | 378 | 45.512 | 14.282 | −20.216 | 1.00 | 19.66 | B | C |
| ATOM | 14399 | CZ3 | TRP | B | 378 | 46.530 | 13.995 | −21.082 | 1.00 | 21.97 | B | C |
| ATOM | 14401 | CH2 | TRP | B | 378 | 47.851 | 13.935 | −20.644 | 1.00 | 21.81 | B | C |
| ATOM | 14403 | CZ2 | TRP | B | 378 | 48.188 | 14.197 | −19.340 | 1.00 | 20.44 | B | C |

TABLE 4-2-continued

Coordinates of P. alba IspS

| ATOM | 14405 | C | TRP | B | 378 | 41.919 | 16.552 | −18.924 | 1.00 | 19.35 | B | C |
| ATOM | 14406 | O | TRP | B | 378 | 41.929 | 16.331 | −20.136 | 1.00 | 20.96 | B | O |
| ATOM | 14408 | N | ALA | B | 379 | 40.821 | 16.846 | −18.242 | 1.00 | 17.74 | B | N |
| ATOM | 14409 | CA | ALA | B | 379 | 39.499 | 16.867 | −18.893 | 1.00 | 20.62 | B | C |
| ATOM | 14411 | CB | ALA | B | 379 | 38.337 | 17.003 | −17.854 | 1.00 | 20.87 | B | C |
| ATOM | 14415 | C | ALA | B | 379 | 39.443 | 18.014 | −19.877 | 1.00 | 20.85 | B | C |
| ATOM | 14416 | O | ALA | B | 379 | 38.957 | 17.853 | −20.998 | 1.00 | 22.78 | B | O |
| ATOM | 14418 | N | ASP | B | 380 | 39.966 | 19.164 | −19.467 | 1.00 | 19.02 | B | N |
| ATOM | 14419 | CA | ASP | B | 380 | 40.048 | 20.318 | −20.354 | 1.00 | 20.32 | B | C |
| ATOM | 14421 | CB | ASP | B | 380 | 40.580 | 21.538 | −19.611 | 1.00 | 22.48 | B | C |
| ATOM | 14424 | CG | ASP | B | 380 | 39.628 | 22.029 | −18.535 | 1.00 | 22.07 | B | C |
| ATOM | 14425 | OD1 | ASP | B | 380 | 38.441 | 21.626 | −18.530 | 1.00 | 25.90 | B | O |
| ATOM | 14426 | OD2 | ASP | B | 380 | 40.081 | 22.808 | −17.697 | 1.00 | 25.80 | B | O |
| ATOM | 14427 | C | ASP | B | 380 | 40.920 | 20.075 | −21.561 | 1.00 | 20.78 | B | C |
| ATOM | 14428 | O | ASP | B | 380 | 40.604 | 20.529 | −22.650 | 1.00 | 24.69 | B | O |
| ATOM | 14430 | N | LEU | B | 381 | 42.016 | 19.361 | −21.385 | 1.00 | 20.48 | B | N |
| ATOM | 14431 | CA | LEU | B | 381 | 42.894 | 19.074 | −22.504 | 1.00 | 19.96 | B | C |
| ATOM | 14433 | CB | LEU | B | 381 | 44.226 | 18.505 | −22.047 | 1.00 | 18.35 | B | C |
| ATOM | 14436 | CG | LEU | B | 381 | 45.196 | 18.161 | −23.167 | 1.00 | 22.53 | B | C |
| ATOM | 14438 | CD1 | LEU | B | 381 | 45.503 | 19.376 | −24.030 | 1.00 | 16.10 | B | C |
| ATOM | 14442 | CD2 | LEU | B | 381 | 46.453 | 17.579 | −22.589 | 1.00 | 16.33 | B | C |
| ATOM | 14446 | C | LEU | B | 381 | 42.197 | 18.127 | −23.456 | 1.00 | 19.12 | B | C |
| ATOM | 14447 | O | LEU | B | 381 | 42.162 | 18.365 | −24.641 | 1.00 | 19.21 | B | O |
| ATOM | 14449 | N | CYS | B | 382 | 41.610 | 17.060 | −22.943 | 1.00 | 20.99 | B | N |
| ATOM | 14450 | CA | CYS | B | 382 | 40.929 | 16.115 | −23.842 | 1.00 | 19.91 | B | C |
| ATOM | 14452 | CB | CYS | B | 382 | 40.480 | 14.866 | −23.077 | 1.00 | 19.91 | B | C |
| ATOM | 14455 | SG | CYS | B | 382 | 41.915 | 13.875 | −22.517 | 1.00 | 24.88 | B | S |
| ATOM | 14457 | C | CYS | B | 382 | 39.775 | 16.780 | −24.594 | 1.00 | 19.49 | B | C |
| ATOM | 14458 | O | CYS | B | 382 | 39.598 | 16.514 | −25.774 | 1.00 | 22.41 | B | O |
| ATOM | 14460 | N | ASN | B | 383 | 39.013 | 17.660 | −23.938 | 1.00 | 19.54 | B | N |
| ATOM | 14461 | CA | ASN | B | 383 | 37.953 | 18.433 | −24.628 | 1.00 | 19.38 | B | C |
| ATOM | 14463 | CB | ASN | B | 383 | 37.078 | 19.250 | −23.644 | 1.00 | 17.80 | B | C |
| ATOM | 14466 | CG | ASN | B | 383 | 35.976 | 18.410 | −23.013 | 1.00 | 21.83 | B | C |
| ATOM | 14467 | OD1 | ASN | B | 383 | 35.030 | 18.011 | −23.692 | 1.00 | 28.68 | B | O |
| ATOM | 14468 | ND2 | ASN | B | 383 | 36.105 | 18.115 | −21.715 | 1.00 | 19.68 | B | N |
| ATOM | 14471 | C | ASN | B | 383 | 38.514 | 19.360 | −25.704 | 1.00 | 20.03 | B | C |
| ATOM | 14472 | O | ASN | B | 383 | 37.876 | 19.576 | −26.722 | 1.00 | 21.15 | B | O |
| ATOM | 14474 | N | ALA | B | 384 | 39.708 | 19.905 | −25.491 | 1.00 | 19.68 | B | N |
| ATOM | 14475 | CA | ALA | B | 384 | 40.312 | 20.759 | −26.500 | 1.00 | 18.25 | B | C |
| ATOM | 14477 | CB | ALA | B | 384 | 41.412 | 21.600 | −25.902 | 1.00 | 16.95 | B | C |
| ATOM | 14481 | C | ALA | B | 384 | 40.799 | 19.897 | −27.676 | 1.00 | 19.74 | B | C |
| ATOM | 14482 | O | ALA | B | 384 | 40.642 | 20.274 | −28.845 | 1.00 | 20.58 | B | O |
| ATOM | 14484 | N | PHE | B | 385 | 41.308 | 18.706 | −27.396 | 1.00 | 19.10 | B | N |
| ATOM | 14485 | CA | PHE | B | 385 | 41.644 | 17.783 | −28.492 | 1.00 | 19.23 | B | C |
| ATOM | 14487 | CB | PHE | B | 385 | 42.336 | 16.521 | −27.964 | 1.00 | 19.77 | B | C |
| ATOM | 14490 | CG | PHE | B | 385 | 43.757 | 16.714 | −27.473 | 1.00 | 20.37 | B | C |
| ATOM | 14491 | CD1 | PHE | B | 385 | 44.639 | 17.573 | −28.099 | 1.00 | 29.85 | B | C |
| ATOM | 14493 | CE1 | PHE | B | 385 | 45.940 | 17.681 | −27.665 | 1.00 | 22.48 | B | C |
| ATOM | 14495 | CZ | PHE | B | 385 | 46.382 | 16.924 | −26.617 | 1.00 | 24.37 | B | C |
| ATOM | 14497 | CE2 | PHE | B | 385 | 45.540 | 16.037 | −26.022 | 1.00 | 19.74 | B | C |
| ATOM | 14499 | CD2 | PHE | B | 385 | 44.238 | 15.934 | −26.441 | 1.00 | 22.30 | B | C |
| ATOM | 14501 | C | PHE | B | 385 | 40.375 | 17.371 | −29.231 | 1.00 | 19.10 | B | C |
| ATOM | 14502 | O | PHE | B | 385 | 40.352 | 17.236 | −30.447 | 1.00 | 20.62 | B | O |
| ATOM | 14504 | N | LEU | B | 386 | 39.293 | 17.190 | −28.487 | 1.00 | 20.82 | B | N |
| ATOM | 14505 | CA | LEU | B | 386 | 38.062 | 16.710 | −29.088 | 1.00 | 19.64 | B | C |
| ATOM | 14507 | CB | LEU | B | 386 | 37.033 | 16.356 | −28.010 | 1.00 | 17.81 | B | C |
| ATOM | 14510 | CG | LEU | B | 386 | 35.711 | 15.780 | −28.547 | 1.00 | 24.89 | B | C |
| ATOM | 14512 | CD1 | LEU | B | 386 | 35.866 | 14.382 | −29.197 | 1.00 | 17.85 | B | C |
| ATOM | 14516 | CD2 | LEU | B | 386 | 34.649 | 15.792 | −27.450 | 1.00 | 13.88 | B | C |
| ATOM | 14520 | C | LEU | B | 386 | 37.531 | 17.758 | −30.044 | 1.00 | 19.89 | B | C |
| ATOM | 14521 | O | LEU | B | 386 | 37.114 | 17.439 | −31.142 | 1.00 | 22.28 | B | O |
| ATOM | 14523 | N | GLN | B | 387 | 37.561 | 19.018 | −29.629 | 1.00 | 22.06 | B | N |
| ATOM | 14524 | CA | GLN | B | 387 | 37.101 | 20.123 | −30.479 | 1.00 | 21.92 | B | C |
| ATOM | 14526 | CB | GLN | B | 387 | 37.163 | 21.490 | −29.736 | 1.00 | 23.65 | B | C |
| ATOM | 14529 | CG | GLN | B | 387 | 36.756 | 22.718 | −30.578 | 1.00 | 24.14 | B | C |
| ATOM | 14532 | CD | GLN | B | 387 | 35.325 | 22.625 | −31.073 | 1.00 | 16.59 | B | C |
| ATOM | 14533 | OE1 | GLN | B | 387 | 35.071 | 22.082 | −32.132 | 1.00 | 26.49 | B | O |
| ATOM | 14534 | NE2 | GLN | B | 387 | 34.397 | 23.060 | −30.270 | 1.00 | 21.29 | B | N |
| ATOM | 14537 | C | GLN | B | 387 | 37.902 | 20.163 | −31.769 | 1.00 | 20.75 | B | C |
| ATOM | 14538 | O | GLN | B | 387 | 37.326 | 20.380 | −32.815 | 1.00 | 21.62 | B | O |
| ATOM | 14540 | N | GLU | B | 388 | 39.211 | 19.914 | −31.714 | 1.00 | 21.58 | B | N |
| ATOM | 14541 | CA | GLU | B | 388 | 40.045 | 19.919 | −32.920 | 1.00 | 22.44 | B | C |
| ATOM | 14543 | CB | GLU | B | 388 | 41.538 | 19.854 | −32.588 | 1.00 | 25.28 | B | C |
| ATOM | 14546 | CG | GLU | B | 388 | 42.068 | 21.146 | −31.939 | 1.00 | 32.65 | B | C |
| ATOM | 14549 | CD | GLU | B | 388 | 43.555 | 21.107 | −31.568 | 1.00 | 35.29 | B | C |
| ATOM | 14550 | OE1 | GLU | B | 388 | 44.121 | 20.004 | −31.343 | 1.00 | 36.54 | B | O |
| ATOM | 14551 | OE2 | GLU | B | 388 | 44.158 | 22.197 | −31.498 | 1.00 | 33.60 | B | O |
| ATOM | 14552 | C | GLU | B | 388 | 39.688 | 18.754 | −33.825 | 1.00 | 21.97 | B | C |

TABLE 4-2-continued

Coordinates of *P. alba* IspS

| ATOM | 14553 | O | GLU | B | 388 | 39.651 | 18.903 | −35.039 | 1.00 | 21.50 | B | O |
|---|---|---|---|---|---|---|---|---|---|---|---|---|
| ATOM | 14555 | N | ALA | B | 389 | 39.381 | 17.607 | −33.236 | 1.00 | 21.26 | B | N |
| ATOM | 14556 | CA | ALA | B | 389 | 39.026 | 16.445 | −34.048 | 1.00 | 21.14 | B | C |
| ATOM | 14558 | CB | ALA | B | 389 | 38.959 | 15.156 | −33.221 | 1.00 | 20.09 | B | C |
| ATOM | 14562 | C | ALA | B | 389 | 37.707 | 16.691 | −34.731 | 1.00 | 19.85 | B | C |
| ATOM | 14563 | O | ALA | B | 389 | 37.538 | 16.311 | −35.875 | 1.00 | 20.01 | B | O |
| ATOM | 14565 | N | LYS | B | 390 | 36.771 | 17.324 | −34.040 | 1.00 | 19.84 | B | N |
| ATOM | 14566 | CA | LYS | B | 390 | 35.453 | 17.575 | −34.629 | 1.00 | 22.05 | B | C |
| ATOM | 14568 | CB | LYS | B | 390 | 34.455 | 18.051 | −33.572 | 1.00 | 24.20 | B | C |
| ATOM | 14571 | CG | LYS | B | 390 | 33.969 | 17.003 | −32.647 | 1.00 | 22.59 | B | C |
| ATOM | 14574 | CD | LYS | B | 390 | 32.947 | 17.600 | −31.704 | 1.00 | 34.38 | B | C |
| ATOM | 14577 | CE | LYS | B | 390 | 32.409 | 16.563 | −30.729 | 1.00 | 32.22 | B | C |
| ATOM | 14580 | NZ | LYS | B | 390 | 31.908 | 17.280 | −29.517 | 1.00 | 30.01 | B | N |
| ATOM | 14584 | C | LYS | B | 390 | 35.491 | 18.607 | −35.745 | 1.00 | 21.67 | B | C |
| ATOM | 14585 | O | LYS | B | 390 | 34.748 | 18.501 | −36.709 | 1.00 | 21.81 | B | O |
| ATOM | 14587 | N | TRP | B | 391 | 36.349 | 19.609 | −35.593 | 1.00 | 22.17 | B | N |
| ATOM | 14588 | CA | TRP | B | 391 | 36.538 | 20.662 | −36.605 | 1.00 | 22.08 | B | C |
| ATOM | 14590 | CB | TRP | B | 391 | 37.462 | 21.803 | −36.091 | 1.00 | 20.61 | B | C |
| ATOM | 14593 | CG | TRP | B | 391 | 36.758 | 22.833 | −35.264 | 1.00 | 21.47 | B | C |
| ATOM | 14594 | CD1 | TRP | B | 391 | 35.444 | 23.170 | −35.325 | 1.00 | 21.71 | B | C |
| ATOM | 14596 | NE1 | TRP | B | 391 | 35.169 | 24.177 | −34.438 | 1.00 | 25.90 | B | N |
| ATOM | 14598 | CE2 | TRP | B | 391 | 36.322 | 24.519 | −33.791 | 1.00 | 19.12 | B | C |
| ATOM | 14599 | CD2 | TRP | B | 391 | 37.345 | 23.702 | −34.295 | 1.00 | 20.50 | B | C |
| ATOM | 14600 | CE3 | TRP | B | 391 | 38.639 | 23.845 | −33.778 | 1.00 | 23.66 | B | C |
| ATOM | 14602 | CZ3 | TRP | B | 391 | 38.860 | 24.792 | −32.811 | 1.00 | 18.30 | B | C |
| ATOM | 14604 | CH2 | TRP | B | 391 | 37.825 | 25.605 | −32.338 | 1.00 | 18.94 | B | C |
| ATOM | 14606 | CZ2 | TRP | B | 391 | 36.546 | 25.480 | −32.804 | 1.00 | 20.38 | B | C |
| ATOM | 14608 | C | TRP | B | 391 | 37.132 | 20.090 | −37.860 | 1.00 | 22.57 | B | C |
| ATOM | 14609 | O | TRP | B | 391 | 36.765 | 20.495 | −38.976 | 1.00 | 18.85 | B | O |
| ATOM | 14611 | N | LEU | B | 392 | 38.089 | 19.189 | −37.676 | 1.00 | 23.55 | B | N |
| ATOM | 14612 | CA | LEU | B | 392 | 38.703 | 18.505 | −38.812 | 1.00 | 27.40 | B | C |
| ATOM | 14614 | CB | LEU | B | 392 | 39.929 | 17.704 | −38.359 | 1.00 | 28.77 | B | C |
| ATOM | 14617 | CG | LEU | B | 392 | 40.742 | 17.113 | −39.517 | 1.00 | 37.78 | B | C |
| ATOM | 14619 | CD1 | LEU | B | 392 | 41.420 | 18.237 | −40.349 | 1.00 | 40.60 | B | C |
| ATOM | 14623 | CD2 | LEU | B | 392 | 41.775 | 16.124 | −38.979 | 1.00 | 38.73 | B | C |
| ATOM | 14627 | C | LEU | B | 392 | 37.674 | 17.591 | −39.509 | 1.00 | 25.45 | B | C |
| ATOM | 14628 | O | LEU | B | 392 | 37.457 | 17.687 | −40.714 | 1.00 | 24.87 | B | O |
| ATOM | 14630 | N | TYR | B | 393 | 36.998 | 16.748 | −38.744 | 1.00 | 24.92 | B | N |
| ATOM | 14631 | CA | TYR | B | 393 | 35.977 | 15.878 | −39.329 | 1.00 | 27.07 | B | C |
| ATOM | 14633 | CB | TYR | B | 393 | 35.261 | 15.065 | −38.248 | 1.00 | 27.20 | B | C |
| ATOM | 14636 | CG | TYR | B | 393 | 34.250 | 14.084 | −38.801 | 1.00 | 32.35 | B | C |
| ATOM | 14637 | CD1 | TYR | B | 393 | 34.635 | 12.817 | −39.240 | 1.00 | 36.10 | B | C |
| ATOM | 14639 | CE1 | TYR | B | 393 | 33.685 | 11.915 | −39.762 | 1.00 | 41.26 | B | C |
| ATOM | 14641 | CZ | TYR | B | 393 | 32.347 | 12.292 | −39.829 | 1.00 | 42.05 | B | C |
| ATOM | 14642 | OH | TYR | B | 393 | 31.387 | 11.441 | −40.331 | 1.00 | 49.85 | B | O |
| ATOM | 14644 | CE2 | TYR | B | 393 | 31.959 | 13.542 | −39.397 | 1.00 | 40.87 | B | C |
| ATOM | 14646 | CD2 | TYR | B | 393 | 32.906 | 14.426 | −38.890 | 1.00 | 37.12 | B | C |
| ATOM | 14648 | C | TYR | B | 393 | 34.940 | 16.684 | −40.109 | 1.00 | 26.51 | B | C |
| ATOM | 14649 | O | TYR | B | 393 | 34.686 | 16.403 | −41.270 | 1.00 | 26.33 | B | O |
| ATOM | 14651 | N | ASN | B | 394 | 34.341 | 17.685 | −39.460 | 1.00 | 26.40 | B | N |
| ATOM | 14652 | CA | ASN | B | 394 | 33.277 | 18.486 | −40.081 | 1.00 | 27.32 | B | C |
| ATOM | 14654 | CB | ASN | B | 394 | 32.442 | 19.175 | −38.993 | 1.00 | 28.58 | B | C |
| ATOM | 14657 | CG | ASN | B | 394 | 31.679 | 18.176 | −38.123 | 1.00 | 28.94 | B | C |
| ATOM | 14658 | OD1 | ASN | B | 394 | 31.111 | 17.223 | −38.628 | 1.00 | 34.61 | B | O |
| ATOM | 14659 | ND2 | ASN | B | 394 | 31.632 | 18.420 | −36.833 | 1.00 | 30.26 | B | N |
| ATOM | 14662 | C | ASN | B | 394 | 33.781 | 19.513 | −41.110 | 1.00 | 27.48 | B | C |
| ATOM | 14663 | O | ASN | B | 394 | 32.997 | 20.225 | −41.670 | 1.00 | 27.41 | B | O |
| ATOM | 14665 | N | LYS | B | 395 | 35.089 | 19.562 | −41.372 | 1.00 | 29.77 | B | N |
| ATOM | 14666 | CA | LYS | B | 395 | 35.702 | 20.601 | −42.222 | 1.00 | 31.41 | B | C |
| ATOM | 14668 | CB | LYS | B | 395 | 35.413 | 20.316 | −43.699 | 1.00 | 33.28 | B | C |
| ATOM | 14671 | CG | LYS | B | 395 | 36.114 | 19.035 | −44.217 | 1.00 | 41.09 | B | C |
| ATOM | 14674 | CD | LYS | B | 395 | 35.295 | 18.354 | −45.321 | 1.00 | 50.28 | B | C |
| ATOM | 14677 | CE | LYS | B | 395 | 36.139 | 17.389 | −46.164 | 1.00 | 54.00 | B | C |
| ATOM | 14680 | NZ | LYS | B | 395 | 36.929 | 16.446 | −45.322 | 1.00 | 54.63 | B | N |
| ATOM | 14684 | C | LYS | B | 395 | 35.303 | 22.041 | −41.811 | 1.00 | 31.59 | B | C |
| ATOM | 14685 | O | LYS | B | 395 | 35.164 | 22.939 | −42.649 | 1.00 | 32.31 | B | O |
| ATOM | 14687 | N | SER | B | 396 | 35.137 | 22.249 | −40.504 | 1.00 | 30.78 | B | N |
| ATOM | 14688 | CA | SER | B | 396 | 34.832 | 23.558 | −39.971 | 1.00 | 29.21 | B | C |
| ATOM | 14690 | CB | SER | B | 396 | 34.656 | 23.475 | −38.479 | 1.00 | 29.18 | B | C |
| ATOM | 14693 | OG | SER | B | 396 | 33.613 | 22.573 | −38.184 | 1.00 | 28.88 | B | O |
| ATOM | 14695 | C | SER | B | 396 | 35.962 | 24.492 | −40.327 | 1.00 | 28.15 | B | C |
| ATOM | 14696 | O | SER | B | 396 | 37.054 | 24.038 | −40.604 | 1.00 | 30.53 | B | O |
| ATOM | 14698 | N | THR | B | 397 | 35.666 | 25.788 | −40.360 | 1.00 | 26.95 | B | N |
| ATOM | 14699 | CA | THR | B | 397 | 36.617 | 26.847 | −40.705 | 1.00 | 25.06 | B | C |
| ATOM | 14701 | CB | THR | B | 397 | 36.309 | 27.435 | −42.117 | 1.00 | 27.07 | B | C |
| ATOM | 14703 | OG1 | THR | B | 397 | 34.924 | 27.817 | −42.180 | 1.00 | 25.75 | B | O |
| ATOM | 14705 | CG2 | THR | B | 397 | 36.576 | 26.369 | −43.218 | 1.00 | 27.27 | B | C |
| ATOM | 14709 | C | THR | B | 397 | 36.509 | 27.959 | −39.641 | 1.00 | 24.96 | B | C |

TABLE 4-2-continued

Coordinates of *P. alba* IspS

| ATOM | 14710 | O | THR | B | 397 | 36.177 | 29.100 | −39.937 | 1.00 | 24.56 | B | O |
|---|---|---|---|---|---|---|---|---|---|---|---|---|
| ATOM | 14712 | N | PRO | B | 398 | 36.791 | 27.622 | −38.388 | 1.00 | 21.45 | B | N |
| ATOM | 14713 | CA | PRO | B | 398 | 36.633 | 28.604 | −37.323 | 1.00 | 22.11 | B | C |
| ATOM | 14715 | CB | PRO | B | 398 | 37.058 | 27.831 | −36.068 | 1.00 | 22.56 | B | C |
| ATOM | 14718 | CG | PRO | B | 398 | 37.975 | 26.737 | −36.622 | 1.00 | 23.07 | B | C |
| ATOM | 14721 | CD | PRO | B | 398 | 37.438 | 26.379 | −37.933 | 1.00 | 20.76 | B | C |
| ATOM | 14724 | C | PRO | B | 398 | 37.525 | 29.813 | −37.478 | 1.00 | 19.82 | B | C |
| ATOM | 14725 | O | PRO | B | 398 | 38.602 | 29.720 | −38.032 | 1.00 | 22.01 | B | O |
| ATOM | 14726 | N | THR | B | 399 | 37.093 | 30.930 | −36.920 | 1.00 | 17.51 | B | N |
| ATOM | 14727 | CA | THR | B | 399 | 37.889 | 32.130 | −36.915 | 1.00 | 15.86 | B | C |
| ATOM | 14729 | CB | THR | B | 399 | 37.165 | 33.304 | −36.225 | 1.00 | 17.11 | B | C |
| ATOM | 14731 | OG1 | THR | B | 399 | 37.060 | 32.998 | −34.850 | 1.00 | 14.13 | B | O |
| ATOM | 14733 | CG2 | THR | B | 399 | 35.717 | 33.586 | −36.827 | 1.00 | 8.38 | B | C |
| ATOM | 14737 | C | THR | B | 399 | 39.152 | 31.912 | −36.130 | 1.00 | 16.82 | B | C |
| ATOM | 14738 | O | THR | B | 399 | 39.258 | 30.995 | −35.292 | 1.00 | 16.62 | B | O |
| ATOM | 14740 | N | PHE | B | 400 | 40.099 | 32.806 | −36.356 | 1.00 | 17.90 | B | N |
| ATOM | 14741 | CA | PHE | B | 400 | 41.335 | 32.771 | −35.628 | 1.00 | 20.04 | B | C |
| ATOM | 14743 | CB | PHE | B | 400 | 42.240 | 33.952 | −35.999 | 1.00 | 19.33 | B | C |
| ATOM | 14746 | CG | PHE | B | 400 | 43.454 | 34.023 | −35.144 | 1.00 | 22.23 | B | C |
| ATOM | 14747 | CD1 | PHE | B | 400 | 44.521 | 33.161 | −35.374 | 1.00 | 25.77 | B | C |
| ATOM | 14749 | CE1 | PHE | B | 400 | 45.663 | 33.194 | −34.559 | 1.00 | 23.21 | B | C |
| ATOM | 14751 | CZ | PHE | B | 400 | 45.721 | 34.093 | −33.485 | 1.00 | 22.27 | B | C |
| ATOM | 14753 | CE2 | PHE | B | 400 | 44.655 | 34.955 | −33.244 | 1.00 | 24.82 | B | C |
| ATOM | 14755 | CD2 | PHE | B | 400 | 43.524 | 34.914 | −34.075 | 1.00 | 25.67 | B | C |
| ATOM | 14757 | C | PHE | B | 400 | 41.113 | 32.770 | −34.120 | 1.00 | 20.59 | B | C |
| ATOM | 14758 | O | PHE | B | 400 | 41.692 | 31.965 | −33.427 | 1.00 | 19.12 | B | O |
| ATOM | 14760 | N | ASP | B | 401 | 40.339 | 33.726 | −33.612 | 1.00 | 19.68 | B | N |
| ATOM | 14761 | CA | ASP | B | 401 | 40.065 | 33.780 | −32.186 | 1.00 | 20.55 | B | C |
| ATOM | 14763 | CB | ASP | B | 401 | 39.100 | 34.942 | −31.855 | 1.00 | 19.50 | B | C |
| ATOM | 14766 | CG | ASP | B | 401 | 39.771 | 36.314 | −31.977 | 1.00 | 26.06 | B | C |
| ATOM | 14767 | OD1 | ASP | B | 401 | 41.024 | 36.425 | −31.871 | 1.00 | 27.25 | B | O |
| ATOM | 14768 | OD2 | ASP | B | 401 | 39.040 | 37.283 | −32.190 | 1.00 | 31.85 | B | O |
| ATOM | 14769 | C | ASP | B | 401 | 39.518 | 32.467 | −31.609 | 1.00 | 19.11 | B | C |
| ATOM | 14770 | O | ASP | B | 401 | 39.910 | 32.084 | −30.525 | 1.00 | 15.67 | B | O |
| ATOM | 14772 | N | ASP | B | 402 | 38.582 | 31.816 | −32.294 | 1.00 | 18.01 | B | N |
| ATOM | 14773 | CA | ASP | B | 402 | 38.058 | 30.539 | −31.800 | 1.00 | 20.72 | B | C |
| ATOM | 14775 | CB | ASP | B | 402 | 36.784 | 30.151 | −32.556 | 1.00 | 21.12 | B | C |
| ATOM | 14778 | CG | ASP | B | 402 | 35.608 | 31.018 | −32.192 | 1.00 | 24.45 | B | C |
| ATOM | 14779 | OD1 | ASP | B | 402 | 35.626 | 31.614 | −31.100 | 1.00 | 34.43 | B | O |
| ATOM | 14780 | OD2 | ASP | B | 402 | 34.655 | 31.099 | −32.986 | 1.00 | 33.91 | B | O |
| ATOM | 14781 | C | ASP | B | 402 | 39.102 | 29.413 | −31.902 | 1.00 | 20.64 | B | C |
| ATOM | 14782 | O | ASP | B | 402 | 39.301 | 28.658 | −30.946 | 1.00 | 20.80 | B | O |
| ATOM | 14784 | N | TYR | B | 403 | 39.796 | 29.322 | −33.037 | 1.00 | 17.89 | B | N |
| ATOM | 14785 | CA | TYR | B | 403 | 40.782 | 28.278 | −33.195 | 1.00 | 20.95 | B | C |
| ATOM | 14787 | CB | TYR | B | 403 | 41.398 | 28.285 | −34.593 | 1.00 | 24.16 | B | C |
| ATOM | 14790 | CG | TYR | B | 403 | 42.415 | 27.191 | −34.774 | 1.00 | 25.07 | B | C |
| ATOM | 14791 | CD1 | TYR | B | 403 | 41.994 | 25.920 | −35.085 | 1.00 | 33.87 | B | C |
| ATOM | 14793 | CE1 | TYR | B | 403 | 42.869 | 24.897 | −35.245 | 1.00 | 36.88 | B | C |
| ATOM | 14795 | CZ | TYR | B | 403 | 44.210 | 25.112 | −35.091 | 1.00 | 36.98 | B | C |
| ATOM | 14796 | OH | TYR | B | 403 | 45.014 | 24.010 | −35.296 | 1.00 | 43.37 | B | O |
| ATOM | 14798 | CE2 | TYR | B | 403 | 44.688 | 26.381 | −34.763 | 1.00 | 35.63 | B | C |
| ATOM | 14800 | CD2 | TYR | B | 403 | 43.772 | 27.416 | −34.602 | 1.00 | 28.89 | B | C |
| ATOM | 14802 | C | TYR | B | 403 | 41.897 | 28.421 | −32.195 | 1.00 | 20.62 | B | C |
| ATOM | 14803 | O | TYR | B | 403 | 42.306 | 27.462 | −31.567 | 1.00 | 21.48 | B | O |
| ATOM | 14805 | N | PHE | B | 404 | 42.401 | 29.633 | −32.053 | 1.00 | 21.49 | B | N |
| ATOM | 14806 | CA | PHE | B | 404 | 43.555 | 29.869 | −31.181 | 1.00 | 21.36 | B | C |
| ATOM | 14808 | CB | PHE | B | 404 | 44.194 | 31.232 | −31.479 | 1.00 | 20.72 | B | C |
| ATOM | 14811 | CG | PHE | B | 404 | 45.349 | 31.561 | −30.618 | 1.00 | 18.53 | B | C |
| ATOM | 14812 | CD1 | PHE | B | 404 | 46.497 | 30.774 | −30.637 | 1.00 | 24.02 | B | C |
| ATOM | 14814 | CE1 | PHE | B | 404 | 47.570 | 31.076 | −29.822 | 1.00 | 19.40 | B | C |
| ATOM | 14816 | CZ | PHE | B | 404 | 47.510 | 32.189 | −28.985 | 1.00 | 21.28 | B | C |
| ATOM | 14818 | CE2 | PHE | B | 404 | 46.382 | 32.969 | −28.957 | 1.00 | 24.12 | B | C |
| ATOM | 14820 | CD2 | PHE | B | 404 | 45.306 | 32.658 | −29.776 | 1.00 | 23.06 | B | C |
| ATOM | 14822 | C | PHE | B | 404 | 43.125 | 29.726 | −29.740 | 1.00 | 21.63 | B | C |
| ATOM | 14823 | O | PHE | B | 404 | 43.825 | 29.110 | −28.945 | 1.00 | 17.99 | B | O |
| ATOM | 14825 | N | GLY | B | 405 | 41.946 | 30.249 | −29.399 | 1.00 | 22.47 | B | N |
| ATOM | 14826 | CA | GLY | B | 405 | 41.436 | 30.071 | −28.039 | 1.00 | 22.00 | B | C |
| ATOM | 14829 | C | GLY | B | 405 | 41.509 | 28.604 | −27.605 | 1.00 | 23.01 | B | C |
| ATOM | 14830 | O | GLY | B | 405 | 41.945 | 28.286 | −26.503 | 1.00 | 25.26 | B | O |
| ATOM | 14832 | N | ASN | B | 406 | 41.049 | 27.711 | −28.474 | 1.00 | 21.92 | B | N |
| ATOM | 14833 | CA | ASN | B | 406 | 41.158 | 26.281 | −28.253 | 1.00 | 21.40 | B | C |
| ATOM | 14835 | CB | ASN | B | 406 | 40.293 | 25.515 | −29.253 | 1.00 | 21.75 | B | C |
| ATOM | 14838 | CG | ASN | B | 406 | 40.155 | 24.061 | −28.891 | 1.00 | 24.28 | B | C |
| ATOM | 14839 | OD1 | ASN | B | 406 | 39.504 | 23.735 | −27.911 | 1.00 | 22.62 | B | O |
| ATOM | 14840 | ND2 | ASN | B | 406 | 40.776 | 23.176 | −29.681 | 1.00 | 16.03 | B | N |
| ATOM | 14843 | C | ASN | B | 406 | 42.606 | 25.765 | −28.361 | 1.00 | 20.04 | B | C |
| ATOM | 14844 | O | ASN | B | 406 | 43.029 | 24.937 | −27.563 | 1.00 | 20.34 | B | O |
| ATOM | 14846 | N | ALA | B | 407 | 43.348 | 26.236 | −29.353 | 1.00 | 18.11 | B | N |

TABLE 4-2-continued

Coordinates of *P. alba* IspS

| ATOM | 14847 | CA | ALA | B | 407 | 44.675 | 25.668 | −29.610 | 1.00 | 19.56 | B | C |
|---|---|---|---|---|---|---|---|---|---|---|---|---|
| ATOM | 14849 | CB | ALA | B | 407 | 45.224 | 26.153 | −30.939 | 1.00 | 16.25 | B | C |
| ATOM | 14853 | C | ALA | B | 407 | 45.701 | 25.884 | −28.493 | 1.00 | 20.02 | B | C |
| ATOM | 14854 | O | ALA | B | 407 | 46.604 | 25.031 | −28.294 | 1.00 | 20.33 | B | O |
| ATOM | 14856 | N | TRP | B | 408 | 45.611 | 27.007 | −27.782 | 1.00 | 18.45 | B | N |
| ATOM | 14857 | CA | TRP | B | 408 | 46.564 | 27.232 | −26.710 | 1.00 | 20.53 | B | C |
| ATOM | 14859 | CB | TRP | B | 408 | 46.737 | 28.706 | −26.290 | 1.00 | 19.32 | B | C |
| ATOM | 14862 | CG | TRP | B | 408 | 45.544 | 29.473 | −25.694 | 1.00 | 19.23 | B | C |
| ATOM | 14863 | CD1 | TRP | B | 408 | 44.789 | 30.419 | −26.330 | 1.00 | 22.29 | B | C |
| ATOM | 14865 | NE1 | TRP | B | 408 | 43.833 | 30.934 | −25.473 | 1.00 | 20.57 | B | N |
| ATOM | 14867 | CE2 | TRP | B | 408 | 43.966 | 30.336 | −24.257 | 1.00 | 21.54 | B | C |
| ATOM | 14868 | CD2 | TRP | B | 408 | 45.052 | 29.418 | −24.351 | 1.00 | 22.09 | B | C |
| ATOM | 14869 | CE3 | TRP | B | 408 | 45.409 | 28.682 | −23.214 | 1.00 | 22.59 | B | C |
| ATOM | 14871 | CZ3 | TRP | B | 408 | 44.687 | 28.893 | −22.028 | 1.00 | 23.88 | B | C |
| ATOM | 14873 | CH2 | TRP | B | 408 | 43.606 | 29.809 | −21.980 | 1.00 | 21.62 | B | C |
| ATOM | 14875 | CZ2 | TRP | B | 408 | 43.244 | 30.540 | −23.076 | 1.00 | 24.64 | B | C |
| ATOM | 14877 | C | TRP | B | 408 | 46.269 | 26.329 | −25.543 | 1.00 | 20.19 | B | C |
| ATOM | 14878 | O | TRP | B | 408 | 47.159 | 26.031 | −24.773 | 1.00 | 24.69 | B | O |
| ATOM | 14880 | N | LYS | B | 409 | 45.040 | 25.858 | −25.431 | 1.00 | 19.87 | B | N |
| ATOM | 14881 | CA | LYS | B | 409 | 44.720 | 24.842 | −24.443 | 1.00 | 20.66 | B | C |
| ATOM | 14883 | CB | LYS | B | 409 | 43.222 | 24.797 | −24.163 | 1.00 | 18.56 | B | C |
| ATOM | 14886 | CG | LYS | B | 409 | 42.667 | 26.085 | −23.503 | 1.00 | 25.88 | B | C |
| ATOM | 14889 | CD | LYS | B | 409 | 41.159 | 26.021 | −23.179 | 1.00 | 33.24 | B | C |
| ATOM | 14892 | CE | LYS | B | 409 | 40.581 | 27.370 | −22.701 | 1.00 | 37.85 | B | C |
| ATOM | 14895 | NZ | LYS | B | 409 | 40.211 | 28.350 | −23.840 | 1.00 | 45.13 | B | N |
| ATOM | 14899 | C | LYS | B | 409 | 45.248 | 23.476 | −24.902 | 1.00 | 20.55 | B | C |
| ATOM | 14900 | O | LYS | B | 409 | 45.859 | 22.746 | −24.116 | 1.00 | 18.30 | B | O |
| ATOM | 14902 | N | SER | B | 410 | 45.068 | 23.178 | −26.186 | 1.00 | 20.61 | B | N |
| ATOM | 14903 | CA | SER | B | 410 | 45.448 | 21.878 | −26.756 | 1.00 | 20.11 | B | C |
| ATOM | 14905 | CB | SER | B | 410 | 44.882 | 21.701 | −28.183 | 1.00 | 21.28 | B | C |
| ATOM | 14908 | OG | SER | B | 410 | 45.676 | 22.371 | −29.177 | 1.00 | 18.53 | B | O |
| ATOM | 14910 | C | SER | B | 410 | 46.943 | 21.693 | −26.827 | 1.00 | 21.39 | B | C |
| ATOM | 14911 | O | SER | B | 410 | 47.400 | 20.598 | −27.087 | 1.00 | 21.38 | B | O |
| ATOM | 14913 | N | SER | B | 411 | 47.703 | 22.775 | −26.667 | 1.00 | 22.35 | B | N |
| ATOM | 14914 | CA | SER | B | 411 | 49.155 | 22.694 | −26.608 | 1.00 | 20.21 | B | C |
| ATOM | 14916 | CB | SER | B | 411 | 49.790 | 24.084 | −26.486 | 1.00 | 21.74 | B | C |
| ATOM | 14919 | OG | SER | B | 411 | 49.520 | 24.719 | −25.216 | 1.00 | 20.26 | B | O |
| ATOM | 14921 | C | SER | B | 411 | 49.584 | 21.872 | −25.411 | 1.00 | 19.55 | B | C |
| ATOM | 14922 | O | SER | B | 411 | 50.645 | 21.322 | −25.433 | 1.00 | 19.31 | B | O |
| ATOM | 14924 | N | SER | B | 412 | 48.738 | 21.814 | −24.380 | 1.00 | 21.60 | B | N |
| ATOM | 14925 | CA | SER | B | 412 | 49.017 | 21.190 | −23.068 | 1.00 | 22.15 | B | C |
| ATOM | 14927 | CB | SER | B | 412 | 49.701 | 19.819 | −23.183 | 1.00 | 22.20 | B | C |
| ATOM | 14930 | OG | SER | B | 412 | 51.094 | 19.930 | −23.403 | 1.00 | 20.47 | B | O |
| ATOM | 14932 | C | SER | B | 412 | 49.810 | 22.101 | −22.119 | 1.00 | 21.31 | B | C |
| ATOM | 14933 | O | SER | B | 412 | 50.103 | 21.730 | −20.970 | 1.00 | 21.57 | B | O |
| ATOM | 14935 | N | GLY | B | 413 | 50.107 | 23.308 | −22.574 | 1.00 | 18.89 | B | N |
| ATOM | 14936 | CA | GLY | B | 413 | 50.807 | 24.295 | −21.751 | 1.00 | 19.18 | B | C |
| ATOM | 14939 | C | GLY | B | 413 | 50.152 | 24.531 | −20.408 | 1.00 | 19.27 | B | C |
| ATOM | 14940 | O | GLY | B | 413 | 50.809 | 24.440 | −19.363 | 1.00 | 20.22 | B | O |
| ATOM | 14942 | N | PRO | B | 414 | 48.851 | 24.815 | −20.412 | 1.00 | 17.74 | B | N |
| ATOM | 14943 | CA | PRO | B | 414 | 48.178 | 25.038 | −19.143 | 1.00 | 20.20 | B | C |
| ATOM | 14945 | CB | PRO | B | 414 | 46.720 | 25.297 | −19.567 | 1.00 | 20.76 | B | C |
| ATOM | 14948 | CG | PRO | B | 414 | 46.881 | 25.963 | −20.871 | 1.00 | 16.96 | B | C |
| ATOM | 14951 | CD | PRO | B | 414 | 47.965 | 25.139 | −21.537 | 1.00 | 18.57 | B | C |
| ATOM | 14954 | C | PRO | B | 414 | 48.247 | 23.840 | −18.218 | 1.00 | 20.58 | B | C |
| ATOM | 14955 | O | PRO | B | 414 | 48.536 | 23.995 | −17.047 | 1.00 | 20.97 | B | O |
| ATOM | 14956 | N | LEU | B | 415 | 48.005 | 22.654 | −18.768 | 1.00 | 22.11 | B | N |
| ATOM | 14957 | CA | LEU | B | 415 | 48.040 | 21.432 | −17.994 | 1.00 | 21.93 | B | C |
| ATOM | 14959 | CB | LEU | B | 415 | 47.677 | 20.224 | −18.870 | 1.00 | 22.71 | B | C |
| ATOM | 14962 | CG | LEU | B | 415 | 47.827 | 18.842 | −18.222 | 1.00 | 24.25 | B | C |
| ATOM | 14964 | CD1 | LEU | B | 415 | 46.773 | 17.860 | −18.751 | 1.00 | 21.18 | B | C |
| ATOM | 14968 | CD2 | LEU | B | 415 | 49.234 | 18.290 | −18.421 | 1.00 | 23.53 | B | C |
| ATOM | 14972 | C | LEU | B | 415 | 49.420 | 21.225 | −17.393 | 1.00 | 22.23 | B | C |
| ATOM | 14973 | O | LEU | B | 415 | 49.540 | 20.955 | −16.209 | 1.00 | 21.62 | B | O |
| ATOM | 14975 | N | GLN | B | 416 | 50.459 | 21.330 | −18.214 | 1.00 | 21.75 | B | N |
| ATOM | 14976 | CA | GLN | B | 416 | 51.824 | 21.221 | −17.701 | 1.00 | 20.58 | B | C |
| ATOM | 14978 | CB | GLN | B | 416 | 52.834 | 21.502 | −18.790 | 1.00 | 19.97 | B | C |
| ATOM | 14981 | CG | GLN | B | 416 | 52.840 | 20.447 | −19.842 | 1.00 | 19.48 | B | C |
| ATOM | 14984 | CD | GLN | B | 416 | 53.920 | 20.659 | −20.837 | 1.00 | 26.66 | B | C |
| ATOM | 14985 | OE1 | GLN | B | 416 | 55.002 | 21.132 | −20.494 | 1.00 | 29.08 | B | O |
| ATOM | 14986 | NE2 | GLN | B | 416 | 53.658 | 20.284 | −22.089 | 1.00 | 24.07 | B | N |
| ATOM | 14989 | C | GLN | B | 416 | 52.062 | 22.162 | −16.544 | 1.00 | 21.03 | B | C |
| ATOM | 14990 | O | GLN | B | 416 | 52.701 | 21.799 | −15.558 | 1.00 | 23.28 | B | O |
| ATOM | 14992 | N | LEU | B | 417 | 51.545 | 23.374 | −16.636 | 1.00 | 19.90 | B | N |
| ATOM | 14993 | CA | LEU | B | 417 | 51.878 | 24.340 | −15.611 | 1.00 | 20.19 | B | C |
| ATOM | 14995 | CB | LEU | B | 417 | 51.770 | 25.766 | −16.117 | 1.00 | 20.53 | B | C |
| ATOM | 14998 | CG | LEU | B | 417 | 52.799 | 26.171 | −17.174 | 1.00 | 17.82 | B | C |
| ATOM | 15000 | CD1 | LEU | B | 417 | 52.466 | 27.556 | −17.758 | 1.00 | 18.27 | B | C |

TABLE 4-2-continued

Coordinates of *P. alba* IspS

| ATOM | 15004 | CD2 | LEU | B | 417 | 54.219 | 26.142 | −16.607 | 1.00 | 18.14 | B | C |
|---|---|---|---|---|---|---|---|---|---|---|---|---|
| ATOM | 15008 | C   | LEU | B | 417 | 51.034 | 24.114 | −14.371 | 1.00 | 20.73 | B | C |
| ATOM | 15009 | O   | LEU | B | 417 | 51.472 | 24.460 | −13.291 | 1.00 | 21.82 | B | O |
| ATOM | 15011 | N   | VAL | B | 418 | 49.841 | 23.516 | −14.500 | 1.00 | 21.29 | B | N |
| ATOM | 15012 | CA  | VAL | B | 418 | 49.081 | 23.104 | −13.310 | 1.00 | 20.26 | B | C |
| ATOM | 15014 | CB  | VAL | B | 418 | 47.702 | 22.530 | −13.655 | 1.00 | 21.33 | B | C |
| ATOM | 15016 | CG1 | VAL | B | 418 | 46.715 | 23.671 | −14.083 | 1.00 | 17.04 | B | C |
| ATOM | 15020 | CG2 | VAL | B | 418 | 47.139 | 21.793 | −12.468 | 1.00 | 19.19 | B | C |
| ATOM | 15024 | C   | VAL | B | 418 | 49.929 | 22.077 | −12.549 | 1.00 | 21.33 | B | C |
| ATOM | 15025 | O   | VAL | B | 418 | 50.114 | 22.181 | −11.350 | 1.00 | 21.65 | B | O |
| ATOM | 15027 | N   | PHE | B | 419 | 50.498 | 21.125 | −13.269 | 1.00 | 18.97 | B | N |
| ATOM | 15028 | CA  | PHE | B | 419 | 51.345 | 20.140 | −12.648 | 1.00 | 19.89 | B | C |
| ATOM | 15030 | CB  | PHE | B | 419 | 51.657 | 19.015 | −13.610 | 1.00 | 19.38 | B | C |
| ATOM | 15033 | CG  | PHE | B | 419 | 50.563 | 17.967 | −13.689 | 1.00 | 19.90 | B | C |
| ATOM | 15034 | CD1 | PHE | B | 419 | 50.670 | 16.777 | −12.971 | 1.00 | 18.98 | B | C |
| ATOM | 15036 | CE1 | PHE | B | 419 | 49.668 | 15.827 | −13.011 | 1.00 | 19.09 | B | C |
| ATOM | 15038 | CZ  | PHE | B | 419 | 48.533 | 16.046 | −13.802 | 1.00 | 20.18 | B | C |
| ATOM | 15040 | CE2 | PHE | B | 419 | 48.424 | 17.216 | −14.534 | 1.00 | 18.86 | B | C |
| ATOM | 15042 | CD2 | PHE | B | 419 | 49.436 | 18.178 | −14.460 | 1.00 | 17.01 | B | C |
| ATOM | 15044 | C   | PHE | B | 419 | 52.620 | 20.762 | −12.087 | 1.00 | 20.16 | B | C |
| ATOM | 15045 | O   | PHE | B | 419 | 53.021 | 20.417 | −10.991 | 1.00 | 20.38 | B | O |
| ATOM | 15047 | N   | ALA | B | 420 | 53.239 | 21.684 | −12.812 | 1.00 | 20.42 | B | N |
| ATOM | 15048 | CA  | ALA | B | 420 | 54.427 | 22.338 | −12.289 | 1.00 | 23.24 | B | C |
| ATOM | 15050 | CB  | ALA | B | 420 | 55.062 | 23.322 | −13.324 | 1.00 | 21.28 | B | C |
| ATOM | 15054 | C   | ALA | B | 420 | 54.061 | 23.045 | −10.988 | 1.00 | 24.47 | B | C |
| ATOM | 15055 | O   | ALA | B | 420 | 54.800 | 22.943 | −10.007 | 1.00 | 25.28 | B | O |
| ATOM | 15057 | N   | TYR | B | 421 | 52.889 | 23.683 | −10.947 | 1.00 | 24.54 | B | N |
| ATOM | 15058 | CA  | TYR | B | 421 | 52.478 | 24.429 | −9.753  | 1.00 | 23.69 | B | C |
| ATOM | 15060 | CB  | TYR | B | 421 | 51.039 | 24.958 | −9.879  | 1.00 | 23.32 | B | C |
| ATOM | 15063 | CG  | TYR | B | 421 | 50.497 | 25.608 | −8.616  | 1.00 | 24.00 | B | C |
| ATOM | 15064 | CD1 | TYR | B | 421 | 50.904 | 26.885 | −8.220  | 1.00 | 27.39 | B | C |
| ATOM | 15066 | CE1 | TYR | B | 421 | 50.418 | 27.466 | −7.053  | 1.00 | 26.70 | B | C |
| ATOM | 15068 | CZ  | TYR | B | 421 | 49.527 | 26.759 | −6.268  | 1.00 | 27.74 | B | C |
| ATOM | 15069 | OH  | TYR | B | 421 | 49.003 | 27.300 | −5.109  | 1.00 | 29.86 | B | O |
| ATOM | 15071 | CE2 | TYR | B | 421 | 49.129 | 25.503 | −6.642  | 1.00 | 26.17 | B | C |
| ATOM | 15073 | CD2 | TYR | B | 421 | 49.616 | 24.931 | −7.797  | 1.00 | 28.12 | B | C |
| ATOM | 15075 | C   | TYR | B | 421 | 52.618 | 23.546 | −8.524  | 1.00 | 25.70 | B | C |
| ATOM | 15076 | O   | TYR | B | 421 | 53.296 | 23.894 | −7.553  | 1.00 | 25.07 | B | O |
| ATOM | 15078 | N   | PHE | B | 422 | 52.001 | 22.374 | −8.560  | 1.00 | 26.45 | B | N |
| ATOM | 15079 | CA  | PHE | B | 422 | 51.998 | 21.538 | −7.363  | 1.00 | 23.99 | B | C |
| ATOM | 15081 | CB  | PHE | B | 422 | 50.959 | 20.448 | −7.476  | 1.00 | 23.45 | B | C |
| ATOM | 15084 | CG  | PHE | B | 422 | 49.564 | 20.962 | −7.545  | 1.00 | 21.76 | B | C |
| ATOM | 15085 | CD1 | PHE | B | 422 | 48.963 | 21.499 | −6.425  | 1.00 | 22.67 | B | C |
| ATOM | 15087 | CE1 | PHE | B | 422 | 47.677 | 21.970 | −6.487  | 1.00 | 22.09 | B | C |
| ATOM | 15089 | CZ  | PHE | B | 422 | 46.996 | 21.931 | −7.682  | 1.00 | 23.94 | B | C |
| ATOM | 15091 | CE2 | PHE | B | 422 | 47.594 | 21.400 | −8.798  | 1.00 | 24.20 | B | C |
| ATOM | 15093 | CD2 | PHE | B | 422 | 48.852 | 20.905 | −8.722  | 1.00 | 21.31 | B | C |
| ATOM | 15095 | C   | PHE | B | 422 | 53.386 | 20.973 | −7.060  | 1.00 | 25.00 | B | C |
| ATOM | 15096 | O   | PHE | B | 422 | 53.687 | 20.659 | −5.916  | 1.00 | 27.56 | B | O |
| ATOM | 15098 | N   | ALA | B | 423 | 54.245 | 20.878 | −8.067  | 1.00 | 24.59 | B | N |
| ATOM | 15099 | CA  | ALA | B | 423 | 55.591 | 20.352 | −7.857  | 1.00 | 24.37 | B | C |
| ATOM | 15101 | CB  | ALA | B | 423 | 56.065 | 19.705 | −9.117  | 1.00 | 21.00 | B | C |
| ATOM | 15105 | C   | ALA | B | 423 | 56.647 | 21.370 | −7.363  | 1.00 | 26.64 | B | C |
| ATOM | 15106 | O   | ALA | B | 423 | 57.710 | 20.965 | −6.870  | 1.00 | 30.03 | B | O |
| ATOM | 15108 | N   | VAL | B | 424 | 56.397 | 22.664 | −7.547  | 1.00 | 27.57 | B | N |
| ATOM | 15109 | CA  | VAL | B | 424 | 57.351 | 23.700 | −7.160  | 1.00 | 29.54 | B | C |
| ATOM | 15111 | CB  | VAL | B | 424 | 57.704 | 24.619 | −8.341  | 1.00 | 29.56 | B | C |
| ATOM | 15113 | CG1 | VAL | B | 424 | 58.149 | 23.780 | −9.552  | 1.00 | 26.25 | B | C |
| ATOM | 15117 | CG2 | VAL | B | 424 | 56.527 | 25.557 | −8.684  | 1.00 | 22.59 | B | C |
| ATOM | 15121 | C   | VAL | B | 424 | 56.887 | 24.597 | −6.011  | 1.00 | 32.82 | B | C |
| ATOM | 15122 | O   | VAL | B | 424 | 57.704 | 25.262 | −5.422  | 1.00 | 34.23 | B | O |
| ATOM | 15124 | N   | VAL | B | 425 | 55.593 | 24.633 | −5.713  | 1.00 | 34.79 | B | N |
| ATOM | 15125 | CA  | VAL | B | 425 | 55.076 | 25.505 | −4.675  | 1.00 | 38.89 | B | C |
| ATOM | 15127 | CB  | VAL | B | 425 | 53.717 | 26.073 | −5.071  | 1.00 | 39.09 | B | C |
| ATOM | 15129 | CG1 | VAL | B | 425 | 53.005 | 26.649 | −3.867  | 1.00 | 38.93 | B | C |
| ATOM | 15133 | CG2 | VAL | B | 425 | 53.911 | 27.138 | −6.142  | 1.00 | 37.94 | B | C |
| ATOM | 15137 | C   | VAL | B | 425 | 54.946 | 24.779 | −3.343  | 1.00 | 43.65 | B | C |
| ATOM | 15138 | O   | VAL | B | 425 | 54.204 | 23.803 | −3.242  | 1.00 | 45.04 | B | O |
| ATOM | 15140 | N   | GLN | B | 426 | 55.647 | 25.279 | −2.322  | 1.00 | 47.45 | B | N |
| ATOM | 15141 | CA  | GLN | B | 426 | 55.676 | 24.630 | −1.008  | 1.00 | 50.46 | B | C |
| ATOM | 15143 | CB  | GLN | B | 426 | 56.627 | 25.368 | −0.053  | 1.00 | 53.33 | B | C |
| ATOM | 15146 | CG  | GLN | B | 426 | 58.129 | 25.084 | −0.275  | 1.00 | 61.88 | B | C |
| ATOM | 15149 | CD  | GLN | B | 426 | 59.034 | 25.792 | 0.746   | 1.00 | 68.89 | B | C |
| ATOM | 15150 | OE1 | GLN | B | 426 | 59.973 | 26.503 | 0.376   | 1.00 | 73.47 | B | O |
| ATOM | 15151 | NE2 | GLN | B | 426 | 58.742 | 25.602 | 2.034   | 1.00 | 69.40 | B | N |
| ATOM | 15154 | C   | GLN | B | 426 | 54.285 | 24.519 | −0.377  | 1.00 | 48.54 | B | C |
| ATOM | 15155 | O   | GLN | B | 426 | 53.887 | 23.437 | 0.037   | 1.00 | 49.02 | B | O |
| ATOM | 15157 | N   | ASN | B | 427 | 53.554 | 25.633 | −0.316  | 1.00 | 46.21 | B | N |

TABLE 4-2-continued

Coordinates of *P. alba* IspS

| ATOM | 15158 | CA | ASN | B | 427 | 52.232 | 25.673 | 0.318 | 1.00 | 44.18 | B | C |
|------|-------|-----|-----|---|-----|--------|--------|--------|------|-------|---|---|
| ATOM | 15160 | CB | ASN | B | 427 | 52.271 | 26.578 | 1.552 | 1.00 | 45.10 | B | C |
| ATOM | 15163 | CG | ASN | B | 427 | 53.065 | 25.963 | 2.691 | 1.00 | 46.27 | B | C |
| ATOM | 15164 | OD1 | ASN | B | 427 | 52.520 | 25.213 | 3.510 | 1.00 | 43.08 | B | O |
| ATOM | 15165 | ND2 | ASN | B | 427 | 54.366 | 26.235 | 2.717 | 1.00 | 38.93 | B | N |
| ATOM | 15168 | C | ASN | B | 427 | 51.156 | 26.170 | −0.631 | 1.00 | 42.56 | B | C |
| ATOM | 15169 | O | ASN | B | 427 | 51.127 | 27.352 | −0.981 | 1.00 | 42.40 | B | O |
| ATOM | 15171 | N | ILE | B | 428 | 50.256 | 25.276 | −1.024 | 1.00 | 40.21 | B | N |
| ATOM | 15172 | CA | ILE | B | 428 | 49.250 | 25.617 | −2.008 | 1.00 | 40.37 | B | C |
| ATOM | 15174 | CB | ILE | B | 428 | 48.597 | 24.364 | −2.634 | 1.00 | 41.28 | B | C |
| ATOM | 15176 | CG1 | ILE | B | 428 | 47.742 | 23.600 | −1.630 | 1.00 | 40.63 | B | C |
| ATOM | 15179 | CD1 | ILE | B | 428 | 46.969 | 22.501 | −2.264 | 1.00 | 38.48 | B | C |
| ATOM | 15183 | CG2 | ILE | B | 428 | 49.675 | 23.424 | −3.196 | 1.00 | 43.55 | B | C |
| ATOM | 15187 | C | ILE | B | 428 | 48.200 | 26.516 | −1.391 | 1.00 | 40.76 | B | C |
| ATOM | 15188 | O | ILE | B | 428 | 47.902 | 26.395 | −0.201 | 1.00 | 41.46 | B | O |
| ATOM | 15190 | N | LYS | B | 429 | 47.657 | 27.422 | −2.198 | 1.00 | 39.80 | B | N |
| ATOM | 15191 | CA | LYS | B | 429 | 46.602 | 28.323 | −1.759 | 1.00 | 39.22 | B | C |
| ATOM | 15193 | CB | LYS | B | 429 | 47.071 | 29.776 | −1.808 | 1.00 | 39.67 | B | C |
| ATOM | 15196 | CG | LYS | B | 429 | 48.269 | 30.048 | −0.920 | 1.00 | 45.60 | B | C |
| ATOM | 15199 | CD | LYS | B | 429 | 48.879 | 31.429 | −1.157 | 1.00 | 50.03 | B | C |
| ATOM | 15202 | CE | LYS | B | 429 | 50.249 | 31.534 | −0.469 | 1.00 | 53.38 | B | C |
| ATOM | 15205 | NZ | LYS | B | 429 | 50.713 | 32.937 | −0.367 | 1.00 | 55.16 | B | N |
| ATOM | 15209 | C | LYS | B | 429 | 45.389 | 28.158 | −2.637 | 1.00 | 38.88 | B | C |
| ATOM | 15210 | O | LYS | B | 429 | 45.492 | 27.998 | −3.854 | 1.00 | 37.10 | B | O |
| ATOM | 15212 | N | LYS | B | 430 | 44.229 | 28.230 | −2.007 | 1.00 | 40.34 | B | N |
| ATOM | 15213 | CA | LYS | B | 430 | 42.985 | 27.967 | −2.682 | 1.00 | 41.57 | B | C |
| ATOM | 15215 | CB | LYS | B | 430 | 41.820 | 28.099 | −1.691 | 1.00 | 44.11 | B | C |
| ATOM | 15218 | CG | LYS | B | 430 | 40.448 | 27.690 | −2.234 | 1.00 | 52.05 | B | C |
| ATOM | 15221 | CD | LYS | B | 430 | 39.363 | 27.760 | −1.142 | 1.00 | 63.27 | B | C |
| ATOM | 15224 | CE | LYS | B | 430 | 38.943 | 29.200 | −0.822 | 1.00 | 67.72 | B | C |
| ATOM | 15227 | NZ | LYS | B | 430 | 38.124 | 29.784 | −1.928 | 1.00 | 71.21 | B | N |
| ATOM | 15231 | C | LYS | B | 430 | 42.802 | 28.927 | −3.843 | 1.00 | 39.97 | B | C |
| ATOM | 15232 | O | LYS | B | 430 | 42.358 | 28.523 | −4.913 | 1.00 | 39.98 | B | O |
| ATOM | 15234 | N | GLU | B | 431 | 43.130 | 30.198 | −3.639 | 1.00 | 39.37 | B | N |
| ATOM | 15235 | CA | GLU | B | 431 | 42.843 | 31.191 | −4.666 | 1.00 | 39.18 | B | C |
| ATOM | 15237 | CB | GLU | B | 431 | 42.743 | 32.612 | −4.088 | 1.00 | 40.15 | B | C |
| ATOM | 15240 | CG | GLU | B | 431 | 44.049 | 33.364 | −3.837 | 1.00 | 50.24 | B | C |
| ATOM | 15243 | CD | GLU | B | 431 | 43.829 | 34.872 | −3.580 | 1.00 | 60.38 | B | C |
| ATOM | 15244 | OE1 | GLU | B | 431 | 43.114 | 35.532 | −4.376 | 1.00 | 62.25 | B | O |
| ATOM | 15245 | OE2 | GLU | B | 431 | 44.376 | 35.396 | −2.582 | 1.00 | 62.66 | B | O |
| ATOM | 15246 | C | GLU | B | 431 | 43.813 | 31.070 | −5.848 | 1.00 | 35.93 | B | C |
| ATOM | 15247 | O | GLU | B | 431 | 43.442 | 31.367 | −6.982 | 1.00 | 34.81 | B | O |
| ATOM | 15249 | N | GLU | B | 432 | 45.034 | 30.618 | −5.585 | 1.00 | 33.41 | B | N |
| ATOM | 15250 | CA | GLU | B | 432 | 45.965 | 30.298 | −6.660 | 1.00 | 33.72 | B | C |
| ATOM | 15252 | CB | GLU | B | 432 | 47.353 | 29.955 | −6.109 | 1.00 | 33.21 | B | C |
| ATOM | 15255 | CG | GLU | B | 432 | 48.085 | 31.141 | −5.456 | 1.00 | 32.22 | B | C |
| ATOM | 15258 | CD | GLU | B | 432 | 49.493 | 30.803 | −4.956 | 1.00 | 37.75 | B | C |
| ATOM | 15259 | OE1 | GLU | B | 432 | 49.791 | 29.622 | −4.631 | 1.00 | 34.91 | B | O |
| ATOM | 15260 | OE2 | GLU | B | 432 | 50.317 | 31.745 | −4.883 | 1.00 | 45.57 | B | O |
| ATOM | 15261 | C | GLU | B | 432 | 45.406 | 29.146 | −7.507 | 1.00 | 33.26 | B | C |
| ATOM | 15262 | O | GLU | B | 432 | 45.304 | 29.260 | −8.728 | 1.00 | 34.10 | B | O |
| ATOM | 15264 | N | ILE | B | 433 | 44.992 | 28.056 | −6.873 | 1.00 | 33.07 | B | N |
| ATOM | 15265 | CA | ILE | B | 433 | 44.509 | 26.923 | −7.661 | 1.00 | 34.77 | B | C |
| ATOM | 15267 | CB | ILE | B | 433 | 44.529 | 25.571 | −6.921 | 1.00 | 33.31 | B | C |
| ATOM | 15269 | CG1 | ILE | B | 433 | 43.828 | 25.602 | −5.594 | 1.00 | 39.69 | B | C |
| ATOM | 15272 | CD1 | ILE | B | 433 | 44.565 | 24.744 | −4.570 | 1.00 | 40.72 | B | C |
| ATOM | 15276 | CG2 | ILE | B | 433 | 45.949 | 25.194 | −6.576 | 1.00 | 37.35 | B | C |
| ATOM | 15280 | C | ILE | B | 433 | 43.190 | 27.234 | −8.334 | 1.00 | 33.17 | B | C |
| ATOM | 15281 | O | ILE | B | 433 | 42.938 | 26.745 | −9.419 | 1.00 | 34.85 | B | O |
| ATOM | 15283 | N | GLU | B | 434 | 42.384 | 28.100 | −7.750 | 1.00 | 31.81 | B | N |
| ATOM | 15284 | CA | GLU | B | 434 | 41.167 | 28.532 | −8.428 | 1.00 | 33.28 | B | C |
| ATOM | 15286 | CB | GLU | B | 434 | 40.259 | 29.351 | −7.499 | 1.00 | 36.58 | B | C |
| ATOM | 15289 | CG | GLU | B | 434 | 39.295 | 28.482 | −6.669 | 1.00 | 45.80 | B | C |
| ATOM | 15292 | CD | GLU | B | 434 | 38.349 | 29.297 | −5.797 | 1.00 | 58.22 | B | C |
| ATOM | 15293 | OE1 | GLU | B | 434 | 38.744 | 30.392 | −5.318 | 1.00 | 61.60 | B | O |
| ATOM | 15294 | OE2 | GLU | B | 434 | 37.204 | 28.834 | −5.597 | 1.00 | 62.57 | B | O |
| ATOM | 15295 | C | GLU | B | 434 | 41.470 | 29.333 | −9.681 | 1.00 | 31.01 | B | C |
| ATOM | 15296 | O | GLU | B | 434 | 40.724 | 29.260 | −10.669 | 1.00 | 32.01 | B | O |
| ATOM | 15298 | N | ASN | B | 435 | 42.546 | 30.108 | −9.641 | 1.00 | 27.38 | B | N |
| ATOM | 15299 | CA | ASN | B | 435 | 42.931 | 30.894 | −10.794 | 1.00 | 28.08 | B | C |
| ATOM | 15301 | CB | ASN | B | 435 | 43.789 | 32.084 | −10.362 | 1.00 | 28.78 | B | C |
| ATOM | 15304 | CG | ASN | B | 435 | 42.934 | 33.315 | −10.028 | 1.00 | 32.39 | B | C |
| ATOM | 15305 | OD1 | ASN | B | 435 | 42.351 | 33.953 | −10.913 | 1.00 | 39.25 | B | O |
| ATOM | 15306 | ND2 | ASN | B | 435 | 42.835 | 33.621 | −8.761 | 1.00 | 27.21 | B | N |
| ATOM | 15309 | C | ASN | B | 435 | 43.603 | 30.038 | −11.878 | 1.00 | 27.27 | B | C |
| ATOM | 15310 | O | ASN | B | 435 | 43.453 | 30.315 | −13.060 | 1.00 | 28.23 | B | O |
| ATOM | 15312 | N | LEU | B | 436 | 44.310 | 28.984 | −11.483 | 1.00 | 27.03 | B | N |
| ATOM | 15313 | CA | LEU | B | 436 | 44.817 | 28.023 | −12.463 | 1.00 | 28.24 | B | C |

TABLE 4-2-continued

Coordinates of *P. alba* IspS

| ATOM | 15315 | CB | LEU | B | 436 | 45.623 | 26.891 | −11.820 | 1.00 | 27.45 | B | C |
|---|---|---|---|---|---|---|---|---|---|---|---|---|
| ATOM | 15318 | CG | LEU | B | 436 | 46.900 | 27.257 | −11.062 | 1.00 | 26.99 | B | C |
| ATOM | 15320 | CD1 | LEU | B | 436 | 47.517 | 26.029 | −10.392 | 1.00 | 25.59 | B | C |
| ATOM | 15324 | CD2 | LEU | B | 436 | 47.879 | 27.938 | −11.979 | 1.00 | 26.36 | B | C |
| ATOM | 15328 | C | LEU | B | 436 | 43.639 | 27.442 | −13.231 | 1.00 | 29.56 | B | C |
| ATOM | 15329 | O | LEU | B | 436 | 43.671 | 27.408 | −14.445 | 1.00 | 30.09 | B | O |
| ATOM | 15331 | N | GLN | B | 437 | 42.577 | 27.034 | −12.535 | 1.00 | 32.04 | B | N |
| ATOM | 15332 | CA | GLN | B | 437 | 41.444 | 26.395 | −13.212 | 1.00 | 33.09 | B | C |
| ATOM | 15334 | CB | GLN | B | 437 | 40.418 | 25.838 | −12.226 | 1.00 | 34.27 | B | C |
| ATOM | 15337 | CG | GLN | B | 437 | 40.927 | 24.764 | −11.314 | 1.00 | 38.74 | B | C |
| ATOM | 15340 | CD | GLN | B | 437 | 39.827 | 23.808 | −10.859 | 1.00 | 42.01 | B | C |
| ATOM | 15341 | OE1 | GLN | B | 437 | 39.776 | 22.664 | −11.304 | 1.00 | 38.35 | B | O |
| ATOM | 15342 | NE2 | GLN | B | 437 | 38.949 | 24.275 | −9.971 | 1.00 | 34.39 | B | N |
| ATOM | 15345 | C | GLN | B | 437 | 40.736 | 27.365 | −14.137 | 1.00 | 32.68 | B | C |
| ATOM | 15346 | O | GLN | B | 437 | 40.030 | 26.933 | −15.041 | 1.00 | 33.51 | B | O |
| ATOM | 15348 | N | LYS | B | 438 | 40.886 | 28.663 | −13.893 | 1.00 | 31.93 | B | N |
| ATOM | 15349 | CA | LYS | B | 438 | 40.284 | 29.683 | −14.765 | 1.00 | 34.40 | B | C |
| ATOM | 15351 | CB | LYS | B | 438 | 39.717 | 30.835 | −13.933 | 1.00 | 36.15 | B | C |
| ATOM | 15354 | CG | LYS | B | 438 | 38.461 | 30.443 | −13.155 | 1.00 | 46.92 | B | C |
| ATOM | 15357 | CD | LYS | B | 438 | 38.218 | 31.319 | −11.915 | 1.00 | 56.20 | B | C |
| ATOM | 15360 | CE | LYS | B | 438 | 36.928 | 30.868 | −11.170 | 1.00 | 62.26 | B | C |
| ATOM | 15363 | NZ | LYS | B | 438 | 36.666 | 31.585 | −9.878 | 1.00 | 59.98 | B | N |
| ATOM | 15367 | C | LYS | B | 438 | 41.268 | 30.207 | −15.810 | 1.00 | 31.95 | B | C |
| ATOM | 15368 | O | LYS | B | 438 | 40.973 | 31.152 | −16.523 | 1.00 | 34.95 | B | O |
| ATOM | 15370 | N | TYR | B | 439 | 42.429 | 29.584 | −15.901 | 1.00 | 30.59 | B | N |
| ATOM | 15371 | CA | TYR | B | 439 | 43.454 | 29.951 | −16.874 | 1.00 | 31.05 | B | C |
| ATOM | 15373 | CB | TYR | B | 439 | 42.995 | 29.728 | −18.308 | 1.00 | 31.76 | B | C |
| ATOM | 15376 | CG | TYR | B | 439 | 42.559 | 28.327 | −18.592 | 1.00 | 35.31 | B | C |
| ATOM | 15377 | CD1 | TYR | B | 439 | 43.486 | 27.367 | −18.911 | 1.00 | 31.89 | B | C |
| ATOM | 15379 | CE1 | TYR | B | 439 | 43.110 | 26.094 | −19.190 | 1.00 | 44.43 | B | C |
| ATOM | 15381 | CZ | TYR | B | 439 | 41.785 | 25.748 | −19.147 | 1.00 | 43.22 | B | C |
| ATOM | 15382 | OH | TYR | B | 439 | 41.462 | 24.467 | −19.437 | 1.00 | 43.75 | B | O |
| ATOM | 15384 | CE2 | TYR | B | 439 | 40.808 | 26.685 | −18.827 | 1.00 | 40.92 | B | C |
| ATOM | 15386 | CD2 | TYR | B | 439 | 41.202 | 27.970 | −18.554 | 1.00 | 39.09 | B | C |
| ATOM | 15388 | C | TYR | B | 439 | 43.888 | 31.383 | −16.714 | 1.00 | 29.52 | B | C |
| ATOM | 15389 | O | TYR | B | 439 | 43.889 | 32.157 | −17.664 | 1.00 | 29.95 | B | O |
| ATOM | 15391 | N | HIS | B | 440 | 44.266 | 31.718 | −15.493 | 1.00 | 29.00 | B | N |
| ATOM | 15392 | CA | HIS | B | 440 | 44.898 | 32.986 | −15.198 | 1.00 | 27.83 | B | C |
| ATOM | 15394 | CB | HIS | B | 440 | 45.457 | 32.918 | −13.782 | 1.00 | 27.70 | B | C |
| ATOM | 15397 | CG | HIS | B | 440 | 45.905 | 34.238 | −13.250 | 1.00 | 34.45 | B | C |
| ATOM | 15398 | ND1 | HIS | B | 440 | 47.203 | 34.688 | −13.373 | 1.00 | 33.50 | B | N |
| ATOM | 15400 | CE1 | HIS | B | 440 | 47.301 | 35.881 | −12.815 | 1.00 | 35.67 | B | C |
| ATOM | 15402 | NE2 | HIS | B | 440 | 46.117 | 36.217 | −12.336 | 1.00 | 38.29 | B | N |
| ATOM | 15404 | CD2 | HIS | B | 440 | 45.226 | 35.208 | −12.599 | 1.00 | 32.67 | B | C |
| ATOM | 15406 | C | HIS | B | 440 | 46.052 | 33.277 | −16.167 | 1.00 | 27.83 | B | C |
| ATOM | 15407 | O | HIS | B | 440 | 46.792 | 32.364 | −16.577 | 1.00 | 23.95 | B | O |
| ATOM | 15409 | N | ASP | B | 441 | 46.206 | 34.557 | −16.499 | 1.00 | 27.43 | B | N |
| ATOM | 15410 | CA | ASP | B | 441 | 47.296 | 35.072 | −17.343 | 1.00 | 25.55 | B | C |
| ATOM | 15412 | CB | ASP | B | 441 | 47.448 | 36.575 | −17.122 | 1.00 | 26.88 | B | C |
| ATOM | 15415 | CG | ASP | B | 441 | 46.214 | 37.382 | −17.555 | 1.00 | 32.29 | B | C |
| ATOM | 15416 | OD1 | ASP | B | 441 | 45.520 | 36.981 | −18.519 | 1.00 | 32.54 | B | O |
| ATOM | 15417 | OD2 | ASP | B | 441 | 45.947 | 38.424 | −16.910 | 1.00 | 38.34 | B | O |
| ATOM | 15418 | C | ASP | B | 441 | 48.665 | 34.427 | −17.077 | 1.00 | 25.73 | B | C |
| ATOM | 15419 | O | ASP | B | 441 | 49.455 | 34.247 | −18.009 | 1.00 | 26.54 | B | O |
| ATOM | 15421 | N | THR | B | 442 | 48.956 | 34.084 | −15.822 | 1.00 | 24.23 | B | N |
| ATOM | 15422 | CA | THR | B | 442 | 50.254 | 33.441 | −15.475 | 1.00 | 25.82 | B | C |
| ATOM | 15424 | CB | THR | B | 442 | 50.317 | 33.025 | −13.995 | 1.00 | 26.22 | B | C |
| ATOM | 15426 | OG1 | THR | B | 442 | 50.066 | 34.173 | −13.192 | 1.00 | 32.69 | B | O |
| ATOM | 15428 | CG2 | THR | B | 442 | 51.692 | 32.497 | −13.624 | 1.00 | 28.30 | B | C |
| ATOM | 15432 | C | THR | B | 442 | 50.562 | 32.211 | −16.317 | 1.00 | 22.08 | B | C |
| ATOM | 15433 | O | THR | B | 442 | 51.699 | 31.994 | −16.697 | 1.00 | 21.58 | B | O |
| ATOM | 15435 | N | ILE | B | 443 | 49.538 | 31.421 | −16.605 | 1.00 | 22.63 | B | N |
| ATOM | 15436 | CA | ILE | B | 443 | 49.703 | 30.173 | −17.329 | 1.00 | 21.27 | B | C |
| ATOM | 15438 | CB | ILE | B | 443 | 49.127 | 28.948 | −16.523 | 1.00 | 21.12 | B | C |
| ATOM | 15440 | CG1 | ILE | B | 443 | 47.612 | 28.928 | −16.433 | 1.00 | 22.72 | B | C |
| ATOM | 15443 | CD1 | ILE | B | 443 | 47.033 | 27.558 | −15.846 | 1.00 | 18.38 | B | C |
| ATOM | 15447 | CG2 | ILE | B | 443 | 49.685 | 28.915 | −15.113 | 1.00 | 22.19 | B | C |
| ATOM | 15451 | C | ILE | B | 443 | 49.151 | 30.266 | −18.751 | 1.00 | 21.71 | B | C |
| ATOM | 15452 | O | ILE | B | 443 | 49.603 | 29.544 | −19.632 | 1.00 | 22.40 | B | O |
| ATOM | 15454 | N | SER | B | 444 | 48.220 | 31.189 | −19.008 | 1.00 | 23.19 | B | N |
| ATOM | 15455 | CA | SER | B | 444 | 47.657 | 31.292 | −20.344 | 1.00 | 21.64 | B | C |
| ATOM | 15457 | CB | SER | B | 444 | 46.339 | 32.028 | −20.345 | 1.00 | 21.22 | B | C |
| ATOM | 15460 | OG | SER | B | 444 | 46.478 | 33.360 | −19.936 | 1.00 | 26.99 | B | O |
| ATOM | 15462 | C | SER | B | 444 | 48.652 | 31.930 | −21.295 | 1.00 | 22.27 | B | C |
| ATOM | 15463 | O | SER | B | 444 | 48.885 | 31.427 | −22.399 | 1.00 | 25.52 | B | O |
| ATOM | 15465 | N | ARG | B | 445 | 49.293 | 33.001 | −20.867 | 1.00 | 21.71 | B | N |
| ATOM | 15466 | CA | ARG | B | 445 | 50.158 | 33.724 | −21.788 | 1.00 | 21.57 | B | C |
| ATOM | 15468 | CB | ARG | B | 445 | 50.571 | 35.066 | −21.210 | 1.00 | 22.03 | B | C |

TABLE 4-2-continued

| | | | | Coordinates of *P. alba* IspS | | | | | | | |
|---|---|---|---|---|---|---|---|---|---|---|---|
| ATOM | 15471 | CG | ARG | B | 445 | 49.356 | 35.981 | −21.031 | 1.00 | 23.51 | B | C |
| ATOM | 15474 | CD | ARG | B | 445 | 49.746 | 37.392 | −20.947 | 1.00 | 35.75 | B | C |
| ATOM | 15477 | NE | ARG | B | 445 | 48.625 | 38.263 | −20.586 | 1.00 | 46.32 | B | N |
| ATOM | 15479 | CZ | ARG | B | 445 | 48.524 | 38.956 | −19.448 | 1.00 | 42.95 | B | C |
| ATOM | 15480 | NH1 | ARG | B | 445 | 49.463 | 38.885 | −18.497 | 1.00 | 41.13 | B | N |
| ATOM | 15483 | NH2 | ARG | B | 445 | 47.463 | 39.730 | −19.261 | 1.00 | 41.39 | B | N |
| ATOM | 15486 | C | ARG | B | 445 | 51.341 | 32.921 | −22.275 | 1.00 | 22.15 | B | C |
| ATOM | 15487 | O | ARG | B | 445 | 51.581 | 32.896 | −23.460 | 1.00 | 21.06 | B | O |
| ATOM | 15489 | N | PRO | B | 446 | 52.064 | 32.233 | −21.371 | 1.00 | 20.64 | B | N |
| ATOM | 15490 | CA | PRO | B | 446 | 53.093 | 31.345 | −21.884 | 1.00 | 20.55 | B | C |
| ATOM | 15492 | CB | PRO | B | 446 | 53.766 | 30.765 | −20.628 | 1.00 | 21.36 | B | C |
| ATOM | 15495 | CG | PRO | B | 446 | 53.127 | 31.394 | −19.456 | 1.00 | 26.98 | B | C |
| ATOM | 15498 | CD | PRO | B | 446 | 52.065 | 32.353 | −19.908 | 1.00 | 22.16 | B | C |
| ATOM | 15501 | C | PRO | B | 446 | 52.529 | 30.224 | −22.761 | 1.00 | 19.46 | B | C |
| ATOM | 15502 | O | PRO | B | 446 | 53.196 | 29.757 | −23.671 | 1.00 | 19.46 | B | O |
| ATOM | 15503 | N | SER | B | 447 | 51.316 | 29.781 | −22.494 | 1.00 | 21.05 | B | N |
| ATOM | 15504 | CA | SER | B | 447 | 50.692 | 28.808 | −23.397 | 1.00 | 21.90 | B | C |
| ATOM | 15506 | CB | SER | B | 447 | 49.439 | 28.196 | −22.759 | 1.00 | 22.29 | B | C |
| ATOM | 15509 | OG | SER | B | 447 | 49.766 | 27.644 | −21.480 | 1.00 | 23.50 | B | O |
| ATOM | 15511 | C | SER | B | 447 | 50.398 | 29.439 | −24.765 | 1.00 | 20.46 | B | C |
| ATOM | 15512 | O | SER | B | 447 | 50.526 | 28.757 | −25.772 | 1.00 | 18.99 | B | O |
| ATOM | 15514 | N | HIS | B | 448 | 50.065 | 30.736 | −24.809 | 1.00 | 18.56 | B | N |
| ATOM | 15515 | CA | HIS | B | 448 | 49.869 | 31.424 | −26.102 | 1.00 | 19.59 | B | C |
| ATOM | 15517 | CB | HIS | B | 448 | 49.575 | 32.940 | −25.943 | 1.00 | 20.25 | B | C |
| ATOM | 15520 | CG | HIS | B | 448 | 48.262 | 33.260 | −25.299 | 1.00 | 17.92 | B | C |
| ATOM | 15521 | ND1 | HIS | B | 448 | 47.442 | 32.305 | −24.739 | 1.00 | 28.87 | B | N |
| ATOM | 15523 | CE1 | HIS | B | 448 | 46.352 | 32.881 | −24.262 | 1.00 | 28.11 | B | C |
| ATOM | 15525 | NE2 | HIS | B | 448 | 46.445 | 34.180 | −24.475 | 1.00 | 27.76 | B | N |
| ATOM | 15527 | CD2 | HIS | B | 448 | 47.635 | 34.443 | −25.110 | 1.00 | 27.89 | B | C |
| ATOM | 15529 | C | HIS | B | 448 | 51.144 | 31.279 | −26.940 | 1.00 | 20.44 | B | C |
| ATOM | 15530 | O | HIS | B | 448 | 51.091 | 30.897 | −28.104 | 1.00 | 22.27 | B | O |
| ATOM | 15532 | N | ILE | B | 449 | 52.280 | 31.587 | −26.330 | 1.00 | 21.15 | B | N |
| ATOM | 15533 | CA | ILE | B | 449 | 53.582 | 31.551 | −26.989 | 1.00 | 22.39 | B | C |
| ATOM | 15535 | CB | ILE | B | 449 | 54.724 | 32.020 | −26.038 | 1.00 | 24.30 | B | C |
| ATOM | 15537 | CG1 | ILE | B | 449 | 54.491 | 33.446 | −25.519 | 1.00 | 23.85 | B | C |
| ATOM | 15540 | CD1 | ILE | B | 449 | 54.478 | 34.442 | −26.532 | 1.00 | 25.54 | B | C |
| ATOM | 15544 | CG2 | ILE | B | 449 | 56.112 | 31.942 | −26.722 | 1.00 | 18.30 | B | C |
| ATOM | 15548 | C | ILE | B | 449 | 53.927 | 30.142 | −27.449 | 1.00 | 22.56 | B | C |
| ATOM | 15549 | O | ILE | B | 449 | 54.427 | 29.944 | −28.551 | 1.00 | 24.34 | B | O |
| ATOM | 15551 | N | PHE | B | 450 | 53.688 | 29.163 | −26.586 | 1.00 | 23.02 | B | N |
| ATOM | 15552 | CA | PHE | B | 450 | 53.918 | 27.756 | −26.916 | 1.00 | 21.54 | B | C |
| ATOM | 15554 | CB | PHE | B | 450 | 53.473 | 26.918 | −25.716 | 1.00 | 23.75 | B | C |
| ATOM | 15557 | CG | PHE | B | 450 | 53.594 | 25.410 | −25.887 | 1.00 | 24.61 | B | C |
| ATOM | 15558 | CD1 | PHE | B | 450 | 54.374 | 24.827 | −26.878 | 1.00 | 26.66 | B | C |
| ATOM | 15560 | CE1 | PHE | B | 450 | 54.457 | 23.457 | −26.978 | 1.00 | 27.03 | B | C |
| ATOM | 15562 | CZ | PHE | B | 450 | 53.801 | 22.643 | −26.064 | 1.00 | 24.83 | B | C |
| ATOM | 15564 | CE2 | PHE | B | 450 | 53.052 | 23.206 | −25.056 | 1.00 | 28.16 | B | C |
| ATOM | 15566 | CD2 | PHE | B | 450 | 52.960 | 24.581 | −24.968 | 1.00 | 24.61 | B | C |
| ATOM | 15568 | C | PHE | B | 450 | 53.191 | 27.358 | −28.205 | 1.00 | 20.99 | B | C |
| ATOM | 15569 | O | PHE | B | 450 | 53.819 | 26.924 | −29.186 | 1.00 | 21.24 | B | O |
| ATOM | 15571 | N | ARG | B | 451 | 51.884 | 27.569 | −28.229 | 1.00 | 19.94 | B | N |
| ATOM | 15572 | CA | ARG | B | 451 | 51.098 | 27.288 | −29.420 | 1.00 | 20.74 | B | C |
| ATOM | 15574 | CB | ARG | B | 451 | 49.621 | 27.595 | −29.169 | 1.00 | 22.47 | B | C |
| ATOM | 15577 | CG | ARG | B | 451 | 48.730 | 27.505 | −30.419 | 1.00 | 25.35 | B | C |
| ATOM | 15580 | CD | ARG | B | 451 | 48.936 | 26.192 | −31.191 | 1.00 | 23.31 | B | C |
| ATOM | 15583 | NE | ARG | B | 451 | 48.475 | 25.041 | −30.448 | 1.00 | 19.56 | B | N |
| ATOM | 15585 | CZ | ARG | B | 451 | 48.731 | 23.772 | −30.790 | 1.00 | 23.42 | B | C |
| ATOM | 15586 | NH1 | ARG | B | 451 | 49.495 | 23.478 | −31.840 | 1.00 | 19.04 | B | N |
| ATOM | 15589 | NH2 | ARG | B | 451 | 48.232 | 22.788 | −30.062 | 1.00 | 18.74 | B | N |
| ATOM | 15592 | C | ARG | B | 451 | 51.588 | 28.065 | −30.632 | 1.00 | 19.72 | B | C |
| ATOM | 15593 | O | ARG | B | 451 | 51.806 | 27.489 | −31.685 | 1.00 | 19.96 | B | O |
| ATOM | 15595 | N | LEU | B | 452 | 51.786 | 29.369 | −30.495 | 1.00 | 21.57 | B | N |
| ATOM | 15596 | CA | LEU | B | 452 | 52.199 | 30.177 | −31.659 | 1.00 | 20.99 | B | C |
| ATOM | 15598 | CB | LEU | B | 452 | 52.191 | 31.663 | −31.330 | 1.00 | 18.72 | B | C |
| ATOM | 15601 | CG | LEU | B | 452 | 50.805 | 32.248 | −31.082 | 1.00 | 18.91 | B | C |
| ATOM | 15603 | CD1 | LEU | B | 452 | 50.863 | 33.633 | −30.405 | 1.00 | 15.37 | B | C |
| ATOM | 15607 | CD2 | LEU | B | 452 | 50.033 | 32.299 | −32.401 | 1.00 | 22.45 | B | C |
| ATOM | 15611 | C | LEU | B | 452 | 53.557 | 29.757 | −32.201 | 1.00 | 21.75 | B | C |
| ATOM | 15612 | O | LEU | B | 452 | 53.753 | 29.726 | −33.427 | 1.00 | 24.82 | B | O |
| ATOM | 15614 | N | CYS | B | 453 | 54.513 | 29.472 | −31.315 | 1.00 | 22.18 | B | N |
| ATOM | 15615 | CA | CYS | B | 453 | 55.844 | 29.031 | −31.758 | 1.00 | 22.41 | B | C |
| ATOM | 15617 | CB | CYS | B | 453 | 56.801 | 28.918 | −30.589 | 1.00 | 25.19 | B | C |
| ATOM | 15620 | SG | CYS | B | 453 | 57.373 | 30.478 | −29.922 | 1.00 | 28.92 | B | S |
| ATOM | 15622 | C | CYS | B | 453 | 55.744 | 27.682 | −32.476 | 1.00 | 23.45 | B | C |
| ATOM | 15623 | O | CYS | B | 453 | 56.283 | 27.514 | −33.545 | 1.00 | 25.24 | B | O |
| ATOM | 15625 | N | ASN | B | 454 | 55.004 | 26.743 | −31.901 | 1.00 | 23.96 | B | N |
| ATOM | 15626 | CA | ASN | B | 454 | 54.755 | 25.463 | −32.555 | 1.00 | 25.23 | B | C |
| ATOM | 15628 | CB | ASN | B | 454 | 53.889 | 24.583 | −31.643 | 1.00 | 25.52 | B | C |

TABLE 4-2-continued

Coordinates of P. alba IspS

| ATOM | 15631 | CG | ASN | B | 454 | 53.627 | 23.178 | −32.218 | 1.00 | 30.70 | B | C |
|---|---|---|---|---|---|---|---|---|---|---|---|---|
| ATOM | 15632 | OD1 | ASN | B | 454 | 54.124 | 22.811 | −33.295 | 1.00 | 41.50 | B | O |
| ATOM | 15633 | ND2 | ASN | B | 454 | 52.848 | 22.382 | −31.480 | 1.00 | 30.45 | B | N |
| ATOM | 15636 | C | ASN | B | 454 | 54.103 | 25.614 | −33.935 | 1.00 | 26.69 | B | C |
| ATOM | 15637 | O | ASN | B | 454 | 54.551 | 25.039 | −34.924 | 1.00 | 25.94 | B | O |
| ATOM | 15639 | N | ASP | B | 455 | 53.039 | 26.393 | −34.006 | 1.00 | 25.79 | B | N |
| ATOM | 15640 | CA | ASP | B | 455 | 52.334 | 26.528 | −35.265 | 1.00 | 24.91 | B | C |
| ATOM | 15642 | CB | ASP | B | 455 | 50.983 | 27.213 | −35.077 | 1.00 | 24.32 | B | C |
| ATOM | 15645 | CG | ASP | B | 455 | 49.932 | 26.296 | −34.475 | 1.00 | 27.79 | B | C |
| ATOM | 15646 | OD1 | ASP | B | 455 | 50.267 | 25.171 | −34.053 | 1.00 | 23.64 | B | O |
| ATOM | 15647 | OD2 | ASP | B | 455 | 48.753 | 26.715 | −34.422 | 1.00 | 29.77 | B | O |
| ATOM | 15648 | C | ASP | B | 455 | 53.169 | 27.290 | −36.278 | 1.00 | 25.89 | B | C |
| ATOM | 15649 | O | ASP | B | 455 | 53.081 | 27.002 | −37.471 | 1.00 | 26.97 | B | O |
| ATOM | 15651 | N | LEU | B | 456 | 53.950 | 28.267 | −35.829 | 1.00 | 25.05 | B | N |
| ATOM | 15652 | CA | LEU | B | 456 | 54.864 | 28.975 | −36.734 | 1.00 | 27.30 | B | C |
| ATOM | 15654 | CB | LEU | B | 456 | 55.706 | 30.009 | −35.981 | 1.00 | 28.50 | B | C |
| ATOM | 15657 | CG | LEU | B | 456 | 55.165 | 31.412 | −35.754 | 1.00 | 31.82 | B | C |
| ATOM | 15659 | CD1 | LEU | B | 456 | 56.033 | 32.147 | −34.720 | 1.00 | 27.46 | B | C |
| ATOM | 15663 | CD2 | LEU | B | 456 | 55.143 | 32.136 | −37.066 | 1.00 | 27.67 | B | C |
| ATOM | 15667 | C | LEU | B | 456 | 55.831 | 27.999 | −37.417 | 1.00 | 29.38 | B | C |
| ATOM | 15668 | O | LEU | B | 456 | 56.116 | 28.138 | −38.610 | 1.00 | 27.77 | B | O |
| ATOM | 15670 | N | ALA | B | 457 | 56.332 | 27.022 | −36.653 | 1.00 | 29.83 | B | N |
| ATOM | 15671 | CA | ALA | B | 457 | 57.349 | 26.087 | −37.157 | 1.00 | 31.91 | B | C |
| ATOM | 15673 | CB | ALA | B | 457 | 58.006 | 25.277 | −35.983 | 1.00 | 28.83 | B | C |
| ATOM | 15677 | C | ALA | B | 457 | 56.801 | 25.140 | −38.232 | 1.00 | 32.51 | B | C |
| ATOM | 15678 | O | ALA | B | 457 | 57.519 | 24.802 | −39.166 | 1.00 | 34.24 | B | O |
| ATOM | 15680 | N | SER | B | 458 | 55.541 | 24.723 | −38.123 | 1.00 | 33.79 | B | N |
| ATOM | 15681 | CA | SER | B | 458 | 54.957 | 23.822 | −39.135 | 1.00 | 34.87 | B | C |
| ATOM | 15683 | CB | SER | B | 458 | 54.113 | 22.751 | −38.446 | 1.00 | 34.97 | B | C |
| ATOM | 15686 | OG | SER | B | 458 | 53.080 | 23.347 | −37.693 | 1.00 | 39.44 | B | O |
| ATOM | 15688 | C | SER | B | 458 | 54.094 | 24.531 | −40.189 | 1.00 | 33.97 | B | C |
| ATOM | 15689 | O | SER | B | 458 | 53.555 | 23.888 | −41.097 | 1.00 | 34.54 | B | O |
| ATOM | 15691 | N | ALA | B | 459 | 53.951 | 25.845 | −40.077 | 1.00 | 34.50 | B | N |
| ATOM | 15692 | CA | ALA | B | 459 | 52.971 | 26.580 | −40.907 | 1.00 | 33.99 | B | C |
| ATOM | 15694 | CB | ALA | B | 459 | 53.033 | 28.075 | −40.597 | 1.00 | 31.89 | B | C |
| ATOM | 15698 | C | ALA | B | 459 | 53.174 | 26.357 | −42.408 | 1.00 | 35.22 | B | C |
| ATOM | 15699 | O | ALA | B | 459 | 52.247 | 25.966 | −43.129 | 1.00 | 33.66 | B | O |
| ATOM | 15701 | N | SER | B | 460 | 54.386 | 26.616 | −42.878 | 1.00 | 37.80 | B | N |
| ATOM | 15702 | CA | SER | B | 460 | 54.671 | 26.532 | −44.308 | 1.00 | 42.19 | B | C |
| ATOM | 15704 | CB | SER | B | 460 | 56.131 | 26.863 | −44.593 | 1.00 | 41.81 | B | C |
| ATOM | 15707 | OG | SER | B | 460 | 56.959 | 25.873 | −44.007 | 1.00 | 52.01 | B | O |
| ATOM | 15709 | C | SER | B | 460 | 54.306 | 25.164 | −44.903 | 1.00 | 42.35 | B | C |
| ATOM | 15710 | O | SER | B | 460 | 53.632 | 25.107 | −45.925 | 1.00 | 43.43 | B | O |
| ATOM | 15712 | N | ALA | B | 461 | 54.718 | 24.073 | −44.264 | 1.00 | 42.83 | B | N |
| ATOM | 15713 | CA | ALA | B | 461 | 54.384 | 22.738 | −44.780 | 1.00 | 42.85 | B | C |
| ATOM | 15715 | CB | ALA | B | 461 | 55.110 | 21.645 | −44.000 | 1.00 | 42.43 | B | C |
| ATOM | 15719 | C | ALA | B | 461 | 52.881 | 22.504 | −44.737 | 1.00 | 43.66 | B | C |
| ATOM | 15720 | O | ALA | B | 461 | 52.300 | 22.003 | −45.696 | 1.00 | 44.63 | B | O |
| ATOM | 15722 | N | GLU | B | 462 | 52.253 | 22.884 | −43.627 | 1.00 | 43.99 | B | N |
| ATOM | 15723 | CA | GLU | B | 462 | 50.839 | 22.611 | −43.422 | 1.00 | 43.23 | B | C |
| ATOM | 15725 | CB | GLU | B | 462 | 50.439 | 22.868 | −41.960 | 1.00 | 43.40 | B | C |
| ATOM | 15728 | CG | GLU | B | 462 | 51.049 | 21.826 | −40.996 | 1.00 | 44.25 | B | C |
| ATOM | 15731 | CD | GLU | B | 462 | 50.581 | 21.932 | −39.541 | 1.00 | 47.19 | B | C |
| ATOM | 15732 | OE1 | GLU | B | 462 | 49.667 | 22.724 | −39.235 | 1.00 | 52.18 | B | O |
| ATOM | 15733 | OE2 | GLU | B | 462 | 51.140 | 21.208 | −38.685 | 1.00 | 50.84 | B | O |
| ATOM | 15734 | C | GLU | B | 462 | 49.979 | 23.397 | −44.405 | 1.00 | 43.66 | B | C |
| ATOM | 15735 | O | GLU | B | 462 | 48.979 | 22.885 | −44.919 | 1.00 | 43.54 | B | O |
| ATOM | 15737 | N | ILE | B | 463 | 50.388 | 24.624 | −44.701 | 1.00 | 43.85 | B | N |
| ATOM | 15738 | CA | ILE | B | 463 | 49.678 | 25.443 | −45.670 | 1.00 | 43.45 | B | C |
| ATOM | 15740 | CB | ILE | B | 463 | 50.147 | 26.910 | −45.599 | 1.00 | 42.49 | B | C |
| ATOM | 15742 | CG1 | ILE | B | 463 | 49.640 | 27.547 | −44.298 | 1.00 | 43.11 | B | C |
| ATOM | 15745 | CD1 | ILE | B | 463 | 50.272 | 28.903 | −43.970 | 1.00 | 34.75 | B | C |
| ATOM | 15749 | CG2 | ILE | B | 463 | 49.658 | 27.714 | −46.809 | 1.00 | 40.80 | B | C |
| ATOM | 15753 | C | ILE | B | 463 | 49.836 | 24.863 | −47.086 | 1.00 | 46.39 | B | C |
| ATOM | 15754 | O | ILE | B | 463 | 48.888 | 24.891 | −47.885 | 1.00 | 48.52 | B | O |
| ATOM | 15756 | N | ALA | B | 464 | 51.016 | 24.324 | −47.387 | 1.00 | 47.05 | B | N |
| ATOM | 15757 | CA | ALA | B | 464 | 51.302 | 23.784 | −48.719 | 1.00 | 48.40 | B | C |
| ATOM | 15759 | CB | ALA | B | 464 | 52.809 | 23.523 | −48.896 | 1.00 | 46.81 | B | C |
| ATOM | 15763 | C | ALA | B | 464 | 50.489 | 22.516 | −48.985 | 1.00 | 49.19 | B | C |
| ATOM | 15764 | O | ALA | B | 464 | 50.121 | 22.260 | −50.125 | 1.00 | 49.95 | B | O |
| ATOM | 15766 | N | ARG | B | 465 | 50.195 | 21.739 | −47.941 | 1.00 | 49.76 | B | N |
| ATOM | 15767 | CA | ARG | B | 465 | 49.306 | 20.569 | −48.075 | 1.00 | 51.15 | B | C |
| ATOM | 15769 | CB | ARG | B | 465 | 49.490 | 19.572 | −46.925 | 1.00 | 51.61 | B | C |
| ATOM | 15772 | CG | ARG | B | 465 | 50.880 | 18.967 | −46.767 | 1.00 | 55.53 | B | C |
| ATOM | 15775 | CD | ARG | B | 465 | 50.935 | 18.153 | −45.476 | 1.00 | 58.91 | B | C |
| ATOM | 15778 | NE | ARG | B | 465 | 52.181 | 18.367 | −44.734 | 1.00 | 65.49 | B | N |
| ATOM | 15780 | CZ | ARG | B | 465 | 52.308 | 18.305 | −43.404 | 1.00 | 67.24 | B | C |
| ATOM | 15781 | NH1 | ARG | B | 465 | 51.261 | 18.048 | −42.620 | 1.00 | 67.28 | B | N |

TABLE 4-2-continued

Coordinates of *P. alba* IspS

| ATOM | 15784 | NH2 | ARG | B | 465 | 53.500 | 18.517 | −42.849 | 1.00 | 67.61 | B | N |
|---|---|---|---|---|---|---|---|---|---|---|---|---|
| ATOM | 15787 | C | ARG | B | 465 | 47.831 | 20.956 | −48.095 | 1.00 | 51.06 | B | C |
| ATOM | 15788 | O | ARG | B | 465 | 46.971 | 20.082 | −48.199 | 1.00 | 50.83 | B | O |
| ATOM | 15790 | N | GLY | B | 466 | 47.533 | 22.247 | −47.958 | 1.00 | 50.91 | B | N |
| ATOM | 15791 | CA | GLY | B | 466 | 46.152 | 22.716 | −47.896 | 1.00 | 50.39 | B | C |
| ATOM | 15794 | C | GLY | B | 466 | 45.486 | 22.489 | −46.547 | 1.00 | 49.96 | B | C |
| ATOM | 15795 | O | GLY | B | 466 | 44.259 | 22.509 | −46.466 | 1.00 | 48.27 | B | O |
| ATOM | 15797 | N | GLU | B | 467 | 46.279 | 22.272 | −45.492 | 1.00 | 48.91 | B | N |
| ATOM | 15798 | CA | GLU | B | 467 | 45.730 | 22.134 | −44.139 | 1.00 | 48.83 | B | C |
| ATOM | 15800 | CB | GLU | B | 467 | 46.683 | 21.365 | −43.215 | 1.00 | 50.22 | B | C |
| ATOM | 15803 | CG | GLU | B | 467 | 46.967 | 19.930 | −43.661 | 1.00 | 54.30 | B | C |
| ATOM | 15806 | CD | GLU | B | 467 | 47.790 | 19.116 | −42.653 | 1.00 | 62.14 | B | C |
| ATOM | 15807 | OE1 | GLU | B | 467 | 47.867 | 19.491 | −41.458 | 1.00 | 59.06 | B | O |
| ATOM | 15808 | OE2 | GLU | B | 467 | 48.354 | 18.078 | −43.069 | 1.00 | 67.03 | B | O |
| ATOM | 15809 | C | GLU | B | 467 | 45.424 | 23.515 | −43.548 | 1.00 | 47.13 | B | C |
| ATOM | 15810 | O | GLU | B | 467 | 46.114 | 24.497 | −43.847 | 1.00 | 47.48 | B | O |
| ATOM | 15812 | N | THR | B | 468 | 44.375 | 23.586 | −42.732 | 1.00 | 42.97 | B | N |
| ATOM | 15813 | CA | THR | B | 468 | 43.954 | 24.835 | −42.125 | 1.00 | 40.67 | B | C |
| ATOM | 15815 | CB | THR | B | 468 | 42.508 | 25.173 | −42.518 | 1.00 | 42.48 | B | C |
| ATOM | 15817 | OG1 | THR | B | 468 | 41.661 | 24.045 | −42.263 | 1.00 | 42.18 | B | O |
| ATOM | 15819 | CG2 | THR | B | 468 | 42.418 | 25.574 | −43.978 | 1.00 | 40.21 | B | C |
| ATOM | 15823 | C | THR | B | 468 | 44.074 | 24.847 | −40.585 | 1.00 | 38.82 | B | C |
| ATOM | 15824 | O | THR | B | 468 | 43.912 | 25.902 | −39.956 | 1.00 | 36.40 | B | O |
| ATOM | 15826 | N | ALA | B | 469 | 44.376 | 23.688 | −39.996 | 1.00 | 36.08 | B | N |
| ATOM | 15827 | CA | ALA | B | 469 | 44.455 | 23.532 | −38.542 | 1.00 | 35.79 | B | C |
| ATOM | 15829 | CB | ALA | B | 469 | 44.222 | 22.068 | −38.167 | 1.00 | 35.44 | B | C |
| ATOM | 15833 | C | ALA | B | 469 | 45.812 | 24.041 | −38.008 | 1.00 | 33.99 | B | C |
| ATOM | 15834 | O | ALA | B | 469 | 46.668 | 23.262 | −37.602 | 1.00 | 35.58 | B | O |
| ATOM | 15836 | N | ASN | B | 470 | 45.972 | 25.363 | −38.014 | 1.00 | 30.53 | B | N |
| ATOM | 15837 | CA | ASN | B | 470 | 47.231 | 26.025 | −37.741 | 1.00 | 25.50 | B | C |
| ATOM | 15839 | CB | ASN | B | 470 | 48.175 | 25.826 | −38.924 | 1.00 | 24.65 | B | C |
| ATOM | 15842 | CG | ASN | B | 470 | 49.538 | 26.437 | −38.688 | 1.00 | 24.87 | B | C |
| ATOM | 15843 | OD1 | ASN | B | 470 | 49.730 | 27.634 | −38.868 | 1.00 | 29.42 | B | O |
| ATOM | 15844 | ND2 | ASN | B | 470 | 50.501 | 25.609 | −38.281 | 1.00 | 29.64 | B | N |
| ATOM | 15847 | C | ASN | B | 470 | 46.974 | 27.515 | −37.559 | 1.00 | 24.47 | B | C |
| ATOM | 15848 | O | ASN | B | 470 | 46.291 | 28.128 | −38.365 | 1.00 | 25.58 | B | O |
| ATOM | 15850 | N | SER | B | 471 | 47.564 | 28.104 | −36.536 | 1.00 | 23.87 | B | N |
| ATOM | 15851 | CA | SER | B | 471 | 47.303 | 29.492 | −36.181 | 1.00 | 22.68 | B | C |
| ATOM | 15853 | CB | SER | B | 471 | 48.100 | 29.848 | −34.917 | 1.00 | 23.21 | B | C |
| ATOM | 15856 | OG | SER | B | 471 | 47.655 | 29.026 | −33.835 | 1.00 | 25.29 | B | O |
| ATOM | 15858 | C | SER | B | 471 | 47.606 | 30.484 | −37.296 | 1.00 | 22.53 | B | C |
| ATOM | 15859 | O | SER | B | 471 | 46.853 | 31.454 | −37.500 | 1.00 | 18.89 | B | O |
| ATOM | 15861 | N | VAL | B | 472 | 48.692 | 30.241 | −38.031 | 1.00 | 22.65 | B | N |
| ATOM | 15862 | CA | VAL | B | 472 | 49.105 | 31.147 | −39.088 | 1.00 | 21.42 | B | C |
| ATOM | 15864 | CB | VAL | B | 472 | 50.518 | 30.828 | −39.641 | 1.00 | 21.25 | B | C |
| ATOM | 15866 | CG1 | VAL | B | 472 | 50.905 | 31.826 | −40.704 | 1.00 | 17.98 | B | C |
| ATOM | 15870 | CG2 | VAL | B | 472 | 51.546 | 30.823 | −38.538 | 1.00 | 20.99 | B | C |
| ATOM | 15874 | C | VAL | B | 472 | 48.090 | 31.055 | −40.204 | 1.00 | 21.80 | B | C |
| ATOM | 15875 | O | VAL | B | 472 | 47.694 | 32.062 | −40.783 | 1.00 | 22.50 | B | O |
| ATOM | 15877 | N | SER | B | 473 | 47.659 | 29.841 | −40.498 | 1.00 | 24.12 | B | N |
| ATOM | 15878 | CA | SER | B | 473 | 46.680 | 29.630 | −41.544 | 1.00 | 25.40 | B | C |
| ATOM | 15880 | CB | SER | B | 473 | 46.400 | 28.146 | −41.745 | 1.00 | 26.05 | B | C |
| ATOM | 15883 | OG | SER | B | 473 | 45.232 | 27.940 | −42.515 | 1.00 | 32.34 | B | O |
| ATOM | 15885 | C | SER | B | 473 | 45.400 | 30.375 | −41.202 | 1.00 | 24.34 | B | C |
| ATOM | 15886 | O | SER | B | 473 | 44.847 | 31.051 | −42.064 | 1.00 | 23.63 | B | O |
| ATOM | 15888 | N | CYS | B | 474 | 44.921 | 30.280 | −39.960 | 1.00 | 23.27 | B | N |
| ATOM | 15889 | CA | CYS | B | 474 | 43.642 | 30.961 | −39.612 | 1.00 | 24.54 | B | C |
| ATOM | 15891 | CB | CYS | B | 474 | 43.162 | 30.643 | −38.196 | 1.00 | 26.93 | B | C |
| ATOM | 15894 | SG | CYS | B | 474 | 42.488 | 29.053 | −38.026 | 1.00 | 32.90 | B | S |
| ATOM | 15896 | C | CYS | B | 474 | 43.784 | 32.442 | −39.678 | 1.00 | 22.35 | B | C |
| ATOM | 15897 | O | CYS | B | 474 | 42.866 | 33.138 | −40.073 | 1.00 | 25.09 | B | O |
| ATOM | 15899 | N | TYR | B | 475 | 44.934 | 32.933 | −39.257 | 1.00 | 21.83 | B | N |
| ATOM | 15900 | CA | TYR | B | 475 | 45.190 | 34.340 | −39.332 | 1.00 | 22.48 | B | C |
| ATOM | 15902 | CB | TYR | B | 475 | 46.530 | 34.700 | −38.700 | 1.00 | 21.91 | B | C |
| ATOM | 15905 | CG | TYR | B | 475 | 46.519 | 36.065 | −38.080 | 1.00 | 23.95 | B | C |
| ATOM | 15906 | CD1 | TYR | B | 475 | 46.386 | 36.237 | −36.704 | 1.00 | 34.09 | B | C |
| ATOM | 15908 | CE1 | TYR | B | 475 | 46.373 | 37.512 | −36.136 | 1.00 | 35.55 | B | C |
| ATOM | 15910 | CZ | TYR | B | 475 | 46.497 | 38.611 | −36.954 | 1.00 | 34.14 | B | C |
| ATOM | 15911 | OH | TYR | B | 475 | 46.491 | 39.895 | −36.448 | 1.00 | 48.07 | B | O |
| ATOM | 15913 | CE2 | TYR | B | 475 | 46.635 | 38.456 | −38.307 | 1.00 | 35.92 | B | C |
| ATOM | 15915 | CD2 | TYR | B | 475 | 46.644 | 37.188 | −38.863 | 1.00 | 31.67 | B | C |
| ATOM | 15917 | C | TYR | B | 475 | 45.105 | 34.802 | −40.780 | 1.00 | 22.81 | B | C |
| ATOM | 15918 | O | TYR | B | 475 | 44.474 | 35.831 | −41.063 | 1.00 | 21.86 | B | O |
| ATOM | 15920 | N | MET | B | 476 | 45.690 | 34.038 | −41.702 | 1.00 | 23.95 | B | N |
| ATOM | 15921 | CA | MET | B | 476 | 45.575 | 34.362 | −43.138 | 1.00 | 23.98 | B | C |
| ATOM | 15923 | CB | MET | B | 476 | 46.227 | 33.304 | −44.022 | 1.00 | 23.03 | B | C |
| ATOM | 15926 | CG | MET | B | 476 | 47.734 | 33.236 | −43.917 | 1.00 | 31.57 | B | C |
| ATOM | 15929 | SD | MET | B | 476 | 48.370 | 31.791 | −44.783 | 1.00 | 35.82 | B | S |

TABLE 4-2-continued

Coordinates of *P. alba* IspS

| ATOM | 15930 | CE | MET | B | 476 | 47.693 | 31.997 | −46.420 | 1.00 | 24.22 | B | C |
|---|---|---|---|---|---|---|---|---|---|---|---|---|
| ATOM | 15934 | C | MET | B | 476 | 44.141 | 34.491 | −43.607 | 1.00 | 23.68 | B | C |
| ATOM | 15935 | O | MET | B | 476 | 43.773 | 35.478 | −44.264 | 1.00 | 22.64 | B | O |
| ATOM | 15937 | N | ARG | B | 477 | 43.345 | 33.465 | −43.322 | 1.00 | 25.52 | B | N |
| ATOM | 15938 | CA | ARG | B | 477 | 41.970 | 33.395 | −43.827 | 1.00 | 25.98 | B | C |
| ATOM | 15940 | CB | ARG | B | 477 | 41.428 | 31.967 | −43.725 | 1.00 | 26.64 | B | C |
| ATOM | 15943 | CG | ARG | B | 477 | 42.138 | 31.022 | −44.683 | 1.00 | 33.11 | B | C |
| ATOM | 15946 | CD | ARG | B | 477 | 41.835 | 29.543 | −44.464 | 1.00 | 39.31 | B | C |
| ATOM | 15949 | NE | ARG | B | 477 | 42.179 | 29.067 | −43.121 | 1.00 | 44.33 | B | N |
| ATOM | 15951 | CZ | ARG | B | 477 | 41.305 | 28.880 | −42.129 | 1.00 | 46.94 | B | C |
| ATOM | 15952 | NH1 | ARG | B | 477 | 40.009 | 29.127 | −42.300 | 1.00 | 48.55 | B | N |
| ATOM | 15955 | NH2 | ARG | B | 477 | 41.736 | 28.447 | −40.947 | 1.00 | 49.68 | B | N |
| ATOM | 15958 | C | ARG | B | 477 | 41.058 | 34.367 | −43.100 | 1.00 | 25.86 | B | C |
| ATOM | 15959 | O | ARG | B | 477 | 40.157 | 34.945 | −43.720 | 1.00 | 28.90 | B | O |
| ATOM | 15961 | N | THR | B | 478 | 41.277 | 34.546 | −41.797 | 1.00 | 24.19 | B | N |
| ATOM | 15962 | CA | THR | B | 478 | 40.461 | 35.474 | −41.024 | 1.00 | 25.34 | B | C |
| ATOM | 15964 | CB | THR | B | 478 | 40.684 | 35.343 | −39.479 | 1.00 | 25.12 | B | C |
| ATOM | 15966 | OG1 | THR | B | 478 | 40.006 | 34.185 | −38.996 | 1.00 | 20.79 | B | O |
| ATOM | 15968 | CG2 | THR | B | 478 | 40.152 | 36.574 | −38.707 | 1.00 | 21.35 | B | C |
| ATOM | 15972 | C | THR | B | 478 | 40.692 | 36.916 | −41.477 | 1.00 | 25.19 | B | C |
| ATOM | 15973 | O | THR | B | 478 | 39.741 | 37.646 | −41.606 | 1.00 | 24.19 | B | O |
| ATOM | 15975 | N | LYS | B | 479 | 41.944 | 37.316 | −41.698 | 1.00 | 25.64 | B | N |
| ATOM | 15976 | CA | LYS | B | 479 | 42.261 | 38.694 | −42.081 | 1.00 | 27.05 | B | C |
| ATOM | 15978 | CB | LYS | B | 479 | 43.538 | 39.169 | −41.392 | 1.00 | 28.04 | B | C |
| ATOM | 15981 | CG | LYS | B | 479 | 43.434 | 39.286 | −39.858 | 1.00 | 32.43 | B | C |
| ATOM | 15984 | CD | LYS | B | 479 | 42.899 | 40.662 | −39.421 | 1.00 | 41.92 | B | C |
| ATOM | 15987 | CE | LYS | B | 479 | 42.652 | 40.733 | −37.915 | 1.00 | 48.99 | B | C |
| ATOM | 15990 | NZ | LYS | B | 479 | 42.370 | 42.129 | −37.475 | 1.00 | 48.92 | B | N |
| ATOM | 15994 | C | LYS | B | 479 | 42.368 | 38.915 | −43.593 | 1.00 | 28.30 | B | C |
| ATOM | 15995 | O | LYS | B | 479 | 42.444 | 40.064 | −44.042 | 1.00 | 30.46 | B | O |
| ATOM | 15997 | N | GLY | B | 480 | 42.335 | 37.844 | −44.384 | 1.00 | 27.75 | B | N |
| ATOM | 15998 | CA | GLY | B | 480 | 42.483 | 37.962 | −45.838 | 1.00 | 27.63 | B | C |
| ATOM | 16001 | C | GLY | B | 480 | 43.873 | 38.401 | −46.270 | 1.00 | 27.82 | B | C |
| ATOM | 16002 | O | GLY | B | 480 | 44.014 | 39.224 | −47.167 | 1.00 | 28.13 | B | O |
| ATOM | 16004 | N | ILE | B | 481 | 44.910 | 37.846 | −45.638 | 1.00 | 27.16 | B | N |
| ATOM | 16005 | CA | ILE | B | 481 | 46.294 | 38.221 | −45.964 | 1.00 | 27.84 | B | C |
| ATOM | 16007 | CB | ILE | B | 481 | 46.978 | 39.002 | −44.812 | 1.00 | 27.50 | B | C |
| ATOM | 16009 | CG1 | ILE | B | 481 | 47.018 | 38.173 | −43.515 | 1.00 | 26.34 | B | C |
| ATOM | 16012 | CD1 | ILE | B | 481 | 47.775 | 38.847 | −42.350 | 1.00 | 23.73 | B | C |
| ATOM | 16016 | CG2 | ILE | B | 481 | 46.260 | 40.328 | −44.607 | 1.00 | 27.59 | B | C |
| ATOM | 16020 | C | ILE | B | 481 | 47.138 | 37.024 | −46.393 | 1.00 | 28.16 | B | C |
| ATOM | 16021 | O | ILE | B | 481 | 46.725 | 35.888 | −46.255 | 1.00 | 30.84 | B | O |
| ATOM | 16023 | N | SER | B | 482 | 48.305 | 37.308 | −46.954 | 1.00 | 30.02 | B | N |
| ATOM | 16024 | CA | SER | B | 482 | 49.283 | 36.301 | −47.364 | 1.00 | 30.53 | B | C |
| ATOM | 16026 | CB | SER | B | 482 | 50.364 | 36.989 | −48.173 | 1.00 | 30.13 | B | C |
| ATOM | 16029 | OG | SER | B | 482 | 50.971 | 37.996 | −47.377 | 1.00 | 28.80 | B | O |
| ATOM | 16031 | C | SER | B | 482 | 49.968 | 35.638 | −46.164 | 1.00 | 31.57 | B | C |
| ATOM | 16032 | O | SER | B | 482 | 50.006 | 36.209 | −45.074 | 1.00 | 31.84 | B | O |
| ATOM | 16034 | N | GLU | B | 483 | 50.548 | 34.461 | −46.390 | 1.00 | 30.45 | B | N |
| ATOM | 16035 | CA | GLU | B | 483 | 51.308 | 33.774 | −45.371 | 1.00 | 31.95 | B | C |
| ATOM | 16037 | CB | GLU | B | 483 | 51.969 | 32.521 | −45.952 | 1.00 | 32.69 | B | C |
| ATOM | 16040 | CG | GLU | B | 483 | 52.874 | 31.797 | −44.939 | 1.00 | 35.01 | B | C |
| ATOM | 16043 | CD | GLU | B | 483 | 53.216 | 30.353 | −45.314 | 1.00 | 41.67 | B | C |
| ATOM | 16044 | OE1 | GLU | B | 483 | 52.776 | 29.875 | −46.389 | 1.00 | 39.44 | B | O |
| ATOM | 16045 | OE2 | GLU | B | 483 | 53.939 | 29.701 | −44.511 | 1.00 | 39.15 | B | O |
| ATOM | 16046 | C | GLU | B | 483 | 52.353 | 34.672 | −44.706 | 1.00 | 32.33 | B | C |
| ATOM | 16047 | O | GLU | B | 483 | 52.486 | 34.704 | −43.482 | 1.00 | 33.44 | B | O |
| ATOM | 16049 | N | GLU | B | 484 | 53.073 | 35.412 | −45.522 | 1.00 | 33.10 | B | N |
| ATOM | 16050 | CA | GLU | B | 484 | 54.133 | 36.271 | −45.054 | 1.00 | 35.44 | B | C |
| ATOM | 16052 | CB | GLU | B | 484 | 54.806 | 36.958 | −46.254 | 1.00 | 37.40 | B | C |
| ATOM | 16055 | CG | GLU | B | 484 | 56.049 | 37.754 | −45.888 | 1.00 | 47.37 | B | C |
| ATOM | 16058 | CD | GLU | B | 484 | 56.678 | 38.484 | −47.076 | 1.00 | 61.47 | B | C |
| ATOM | 16059 | OE1 | GLU | B | 484 | 56.049 | 38.576 | −48.162 | 1.00 | 64.59 | B | O |
| ATOM | 16060 | OE2 | GLU | B | 484 | 57.815 | 38.975 | −46.906 | 1.00 | 63.79 | B | O |
| ATOM | 16061 | C | GLU | B | 484 | 53.636 | 37.330 | −44.064 | 1.00 | 33.41 | B | C |
| ATOM | 16062 | O | GLU | B | 484 | 54.285 | 37.580 | −43.049 | 1.00 | 30.95 | B | O |
| ATOM | 16064 | N | LEU | B | 485 | 52.516 | 37.974 | −44.375 | 1.00 | 31.70 | B | N |
| ATOM | 16065 | CA | LEU | B | 485 | 51.982 | 39.005 | −43.489 | 1.00 | 31.52 | B | C |
| ATOM | 16067 | CB | LEU | B | 485 | 50.969 | 39.899 | −44.218 | 1.00 | 33.56 | B | C |
| ATOM | 16070 | CG | LEU | B | 485 | 51.561 | 40.942 | −45.174 | 1.00 | 37.32 | B | C |
| ATOM | 16072 | CD1 | LEU | B | 485 | 50.509 | 41.463 | −46.157 | 1.00 | 36.05 | B | C |
| ATOM | 16076 | CD2 | LEU | B | 485 | 52.180 | 42.087 | −44.377 | 1.00 | 42.57 | B | C |
| ATOM | 16080 | C | LEU | B | 485 | 51.360 | 38.383 | −42.229 | 1.00 | 28.30 | B | C |
| ATOM | 16081 | O | LEU | B | 485 | 51.426 | 38.957 | −41.157 | 1.00 | 25.25 | B | O |
| ATOM | 16083 | N | ALA | B | 486 | 50.782 | 37.201 | −42.367 | 1.00 | 26.73 | B | N |
| ATOM | 16084 | CA | ALA | B | 486 | 50.173 | 36.528 | −41.243 | 1.00 | 26.36 | B | C |
| ATOM | 16086 | CB | ALA | B | 486 | 49.358 | 35.304 | −41.718 | 1.00 | 23.95 | B | C |
| ATOM | 16090 | C | ALA | B | 486 | 51.281 | 36.134 | −40.269 | 1.00 | 24.95 | B | C |

TABLE 4-2-continued

Coordinates of *P. alba* IspS

| ATOM | 16091 | O | ALA | B | 486 | 51.141 | 36.267 | −39.048 | 1.00 | 22.96 | B | O |
|------|-------|-----|-----|---|-----|--------|--------|---------|------|-------|---|---|
| ATOM | 16093 | N | THR | B | 487 | 52.397 | 35.706 | −40.835 | 1.00 | 25.77 | B | N |
| ATOM | 16094 | CA | THR | B | 487 | 53.581 | 35.312 | −40.069 | 1.00 | 27.48 | B | C |
| ATOM | 16096 | CB | THR | B | 487 | 54.654 | 34.714 | −41.004 | 1.00 | 29.14 | B | C |
| ATOM | 16098 | OG1 | THR | B | 487 | 54.120 | 33.537 | −41.647 | 1.00 | 29.56 | B | O |
| ATOM | 16100 | CG2 | THR | B | 487 | 55.884 | 34.343 | −40.234 | 1.00 | 24.58 | B | C |
| ATOM | 16104 | C | THR | B | 487 | 54.142 | 36.492 | −39.306 | 1.00 | 26.57 | B | C |
| ATOM | 16105 | O | THR | B | 487 | 54.450 | 36.400 | −38.119 | 1.00 | 22.40 | B | O |
| ATOM | 16107 | N | GLU | B | 488 | 54.225 | 37.624 | −39.977 | 1.00 | 28.65 | B | N |
| ATOM | 16108 | CA | GLU | B | 488 | 54.627 | 38.869 | −39.311 | 1.00 | 31.12 | B | C |
| ATOM | 16110 | CB | GLU | B | 488 | 54.701 | 40.012 | −40.336 | 1.00 | 33.28 | B | C |
| ATOM | 16113 | CG | GLU | B | 488 | 55.304 | 41.334 | −39.844 | 1.00 | 43.15 | B | C |
| ATOM | 16116 | CD | GLU | B | 488 | 55.275 | 42.458 | −40.908 | 1.00 | 50.77 | B | C |
| ATOM | 16117 | OE1 | GLU | B | 488 | 54.732 | 42.270 | −42.023 | 1.00 | 51.52 | B | O |
| ATOM | 16118 | OE2 | GLU | B | 488 | 55.802 | 43.548 | −40.611 | 1.00 | 57.46 | B | O |
| ATOM | 16119 | C | GLU | B | 488 | 53.669 | 39.187 | −38.131 | 1.00 | 28.39 | B | C |
| ATOM | 16120 | O | GLU | B | 488 | 54.129 | 39.472 | −37.027 | 1.00 | 25.62 | B | O |
| ATOM | 16122 | N | SER | B | 489 | 52.354 | 39.090 | −38.351 | 1.00 | 25.99 | B | N |
| ATOM | 16123 | CA | SER | B | 489 | 51.379 | 39.404 | −37.281 | 1.00 | 27.20 | B | C |
| ATOM | 16125 | CB | SER | B | 489 | 49.923 | 39.418 | −37.770 | 1.00 | 24.76 | B | C |
| ATOM | 16128 | OG | SER | B | 489 | 49.709 | 40.444 | −38.695 | 1.00 | 30.59 | B | O |
| ATOM | 16130 | C | SER | B | 489 | 51.473 | 38.435 | −36.118 | 1.00 | 25.26 | B | C |
| ATOM | 16131 | O | SER | B | 489 | 51.327 | 38.835 | −34.979 | 1.00 | 25.76 | B | O |
| ATOM | 16133 | N | VAL | B | 490 | 51.703 | 37.165 | −36.401 | 1.00 | 24.32 | B | N |
| ATOM | 16134 | CA | VAL | B | 490 | 51.890 | 36.201 | −35.318 | 1.00 | 24.64 | B | C |
| ATOM | 16136 | CB | VAL | B | 490 | 51.905 | 34.758 | −35.847 | 1.00 | 24.98 | B | C |
| ATOM | 16138 | CG1 | VAL | B | 490 | 52.313 | 33.755 | −34.747 | 1.00 | 24.04 | B | C |
| ATOM | 16142 | CG2 | VAL | B | 490 | 50.555 | 34.409 | −36.395 | 1.00 | 20.83 | B | C |
| ATOM | 16146 | C | VAL | B | 490 | 53.133 | 36.517 | −34.465 | 1.00 | 25.21 | B | C |
| ATOM | 16147 | O | VAL | B | 490 | 53.084 | 36.405 | −33.252 | 1.00 | 26.85 | B | O |
| ATOM | 16149 | N | MET | B | 491 | 54.221 | 36.962 | −35.085 | 1.00 | 27.17 | B | N |
| ATOM | 16150 | CA | MET | B | 491 | 55.441 | 37.314 | −34.345 | 1.00 | 27.17 | B | C |
| ATOM | 16152 | CB | MET | B | 491 | 56.619 | 37.595 | −35.286 | 1.00 | 29.59 | B | C |
| ATOM | 16155 | CG | MET | B | 491 | 56.984 | 36.475 | −36.254 | 1.00 | 32.48 | B | C |
| ATOM | 16158 | SD | MET | B | 491 | 58.082 | 35.259 | −35.532 | 1.00 | 54.54 | B | S |
| ATOM | 16159 | CE | MET | B | 491 | 58.676 | 34.476 | −37.042 | 1.00 | 58.30 | B | C |
| ATOM | 16163 | C | MET | B | 491 | 55.183 | 38.545 | −33.498 | 1.00 | 26.01 | B | C |
| ATOM | 16164 | O | MET | B | 491 | 55.677 | 38.646 | −32.387 | 1.00 | 27.29 | B | O |
| ATOM | 16166 | N | ASN | B | 492 | 54.414 | 39.494 | −34.024 | 1.00 | 25.33 | B | N |
| ATOM | 16167 | CA | ASN | B | 492 | 54.027 | 40.675 | −33.241 | 1.00 | 25.11 | B | C |
| ATOM | 16169 | CB | ASN | B | 492 | 53.294 | 41.713 | −34.100 | 1.00 | 26.44 | B | C |
| ATOM | 16172 | CG | ASN | B | 492 | 54.206 | 42.393 | −35.135 | 1.00 | 31.18 | B | C |
| ATOM | 16173 | OD1 | ASN | B | 492 | 55.413 | 42.496 | −34.944 | 1.00 | 41.61 | B | O |
| ATOM | 16174 | ND2 | ASN | B | 492 | 53.610 | 42.884 | −36.226 | 1.00 | 31.04 | B | N |
| ATOM | 16177 | C | ASN | B | 492 | 53.163 | 40.308 | −32.025 | 1.00 | 21.95 | B | C |
| ATOM | 16178 | O | ASN | B | 492 | 53.310 | 40.913 | −30.977 | 1.00 | 23.50 | B | O |
| ATOM | 16180 | N | LEU | B | 493 | 52.272 | 39.332 | −32.176 | 1.00 | 16.94 | B | N |
| ATOM | 16181 | CA | LEU | B | 493 | 51.452 | 38.837 | −31.078 | 1.00 | 19.50 | B | C |
| ATOM | 16183 | CB | LEU | B | 493 | 50.401 | 37.871 | −31.626 | 1.00 | 20.12 | B | C |
| ATOM | 16186 | CG | LEU | B | 493 | 49.330 | 37.252 | −30.730 | 1.00 | 29.36 | B | C |
| ATOM | 16188 | CD1 | LEU | B | 493 | 48.557 | 38.309 | −29.904 | 1.00 | 28.24 | B | C |
| ATOM | 16192 | CD2 | LEU | B | 493 | 48.355 | 36.399 | −31.599 | 1.00 | 21.19 | B | C |
| ATOM | 16196 | C | LEU | B | 493 | 52.359 | 38.162 | −30.021 | 1.00 | 19.84 | B | C |
| ATOM | 16197 | O | LEU | B | 493 | 52.219 | 38.393 | −28.819 | 1.00 | 19.40 | B | O |
| ATOM | 16199 | N | ILE | B | 494 | 53.326 | 37.380 | −30.477 | 1.00 | 20.01 | B | N |
| ATOM | 16200 | CA | ILE | B | 494 | 54.330 | 36.845 | −29.569 | 1.00 | 20.75 | B | C |
| ATOM | 16202 | CB | ILE | B | 494 | 55.346 | 35.966 | −30.315 | 1.00 | 20.42 | B | C |
| ATOM | 16204 | CG1 | ILE | B | 494 | 54.646 | 34.675 | −30.739 | 1.00 | 16.69 | B | C |
| ATOM | 16207 | CD1 | ILE | B | 494 | 55.474 | 33.814 | −31.610 | 1.00 | 19.06 | B | C |
| ATOM | 16211 | CG2 | ILE | B | 494 | 56.521 | 35.613 | −29.418 | 1.00 | 20.38 | B | C |
| ATOM | 16215 | C | ILE | B | 494 | 55.009 | 37.965 | −28.770 | 1.00 | 20.30 | B | C |
| ATOM | 16216 | O | ILE | B | 494 | 55.087 | 37.890 | −27.548 | 1.00 | 20.50 | B | O |
| ATOM | 16218 | N | ASP | B | 495 | 55.429 | 39.026 | −29.442 | 1.00 | 20.29 | B | N |
| ATOM | 16219 | CA | ASP | B | 495 | 56.042 | 40.169 | −28.763 | 1.00 | 20.00 | B | C |
| ATOM | 16221 | CB | ASP | B | 495 | 56.476 | 41.235 | −29.773 | 1.00 | 19.65 | B | C |
| ATOM | 16224 | CG | ASP | B | 495 | 57.672 | 40.795 | −30.609 | 1.00 | 22.70 | B | C |
| ATOM | 16225 | OD1 | ASP | B | 495 | 58.358 | 39.819 | −30.243 | 1.00 | 32.40 | B | O |
| ATOM | 16226 | OD2 | ASP | B | 495 | 57.943 | 41.429 | −31.644 | 1.00 | 33.90 | B | O |
| ATOM | 16227 | C | ASP | B | 495 | 55.140 | 40.800 | −27.717 | 1.00 | 22.04 | B | C |
| ATOM | 16228 | O | ASP | B | 495 | 55.567 | 41.053 | −26.588 | 1.00 | 23.10 | B | O |
| ATOM | 16230 | N | GLU | B | 496 | 53.897 | 41.061 | −28.088 | 1.00 | 23.21 | B | N |
| ATOM | 16231 | CA | GLU | B | 496 | 52.959 | 41.715 | −27.191 | 1.00 | 25.03 | B | C |
| ATOM | 16233 | CB | GLU | B | 496 | 51.643 | 42.007 | −27.902 | 1.00 | 24.60 | B | C |
| ATOM | 16236 | CG | GLU | B | 496 | 51.772 | 43.101 | −28.938 | 1.00 | 34.66 | B | C |
| ATOM | 16239 | CD | GLU | B | 496 | 52.250 | 44.433 | −28.354 | 1.00 | 43.94 | B | C |
| ATOM | 16240 | OE1 | GLU | B | 496 | 53.248 | 44.980 | −28.880 | 1.00 | 45.89 | B | O |
| ATOM | 16241 | OE2 | GLU | B | 496 | 51.633 | 44.926 | −27.377 | 1.00 | 48.24 | B | O |
| ATOM | 16242 | C | GLU | B | 496 | 52.693 | 40.840 | −26.003 | 1.00 | 23.68 | B | C |

TABLE 4-2-continued

Coordinates of P. alba IspS

| ATOM | 16243 | O | GLU | B | 496 | 52.579 | 41.339 | −24.882 | 1.00 | 23.34 | B | O |
|---|---|---|---|---|---|---|---|---|---|---|---|---|
| ATOM | 16245 | N | THR | B | 497 | 52.606 | 39.534 | −26.257 | 1.00 | 21.60 | B | N |
| ATOM | 16246 | CA | THR | B | 497 | 52.340 | 38.571 | −25.214 | 1.00 | 21.88 | B | C |
| ATOM | 16248 | CB | THR | B | 497 | 52.112 | 37.168 | −25.799 | 1.00 | 22.84 | B | C |
| ATOM | 16250 | OG1 | THR | B | 497 | 51.067 | 37.231 | −26.790 | 1.00 | 24.32 | B | O |
| ATOM | 16252 | CG2 | THR | B | 497 | 51.719 | 36.222 | −24.710 | 1.00 | 18.88 | B | C |
| ATOM | 16256 | C | THR | B | 497 | 53.510 | 38.565 | −24.217 | 1.00 | 21.49 | B | C |
| ATOM | 16257 | O | THR | B | 497 | 53.295 | 38.521 | −23.022 | 1.00 | 20.84 | B | O |
| ATOM | 16259 | N | TRP | B | 498 | 54.737 | 38.654 | −24.715 | 1.00 | 19.80 | B | N |
| ATOM | 16260 | CA | TRP | B | 498 | 55.892 | 38.786 | −23.847 | 1.00 | 21.21 | B | C |
| ATOM | 16262 | CB | TRP | B | 498 | 57.194 | 38.771 | −24.641 | 1.00 | 20.21 | B | C |
| ATOM | 16265 | CG | TRP | B | 498 | 57.821 | 37.406 | −24.729 | 1.00 | 22.28 | B | C |
| ATOM | 16266 | CD1 | TRP | B | 498 | 57.768 | 36.547 | −25.786 | 1.00 | 18.79 | B | C |
| ATOM | 16268 | NE1 | TRP | B | 498 | 58.454 | 35.404 | −25.497 | 1.00 | 23.07 | B | N |
| ATOM | 16270 | CE2 | TRP | B | 498 | 58.985 | 35.508 | −24.241 | 1.00 | 18.89 | B | C |
| ATOM | 16271 | CD2 | TRP | B | 498 | 58.603 | 36.756 | −23.726 | 1.00 | 23.52 | B | C |
| ATOM | 16272 | CE3 | TRP | B | 498 | 59.019 | 37.107 | −22.439 | 1.00 | 25.36 | B | C |
| ATOM | 16274 | CZ3 | TRP | B | 498 | 59.775 | 36.204 | −21.715 | 1.00 | 24.20 | B | C |
| ATOM | 16276 | CH2 | TRP | B | 498 | 60.147 | 34.974 | −22.259 | 1.00 | 20.69 | B | C |
| ATOM | 16278 | CZ2 | TRP | B | 498 | 59.759 | 34.607 | −23.516 | 1.00 | 25.94 | B | C |
| ATOM | 16280 | C | TRP | B | 498 | 55.844 | 40.048 | −22.992 | 1.00 | 21.86 | B | C |
| ATOM | 16281 | O | TRP | B | 498 | 56.199 | 40.028 | −21.809 | 1.00 | 22.63 | B | O |
| ATOM | 16283 | N | LYS | B | 499 | 55.404 | 41.147 | −23.576 | 1.00 | 22.03 | B | N |
| ATOM | 16284 | CA | LYS | B | 499 | 55.328 | 42.379 | −22.823 | 1.00 | 22.69 | B | C |
| ATOM | 16286 | CB | LYS | B | 499 | 54.851 | 43.541 | −23.692 | 1.00 | 23.12 | B | C |
| ATOM | 16289 | CG | LYS | B | 499 | 55.860 | 43.971 | −24.779 | 1.00 | 19.45 | B | C |
| ATOM | 16292 | CD | LYS | B | 499 | 55.348 | 45.181 | −25.597 | 1.00 | 20.45 | B | C |
| ATOM | 16295 | CE | LYS | B | 499 | 56.178 | 45.364 | −26.882 | 1.00 | 24.37 | B | C |
| ATOM | 16298 | NZ | LYS | B | 499 | 55.795 | 46.603 | −27.636 | 1.00 | 25.22 | B | N |
| ATOM | 16302 | C | LYS | B | 499 | 54.438 | 42.197 | −21.603 | 1.00 | 23.79 | B | C |
| ATOM | 16303 | O | LYS | B | 499 | 54.781 | 42.641 | −20.506 | 1.00 | 26.86 | B | O |
| ATOM | 16305 | N | LYS | B | 500 | 53.332 | 41.492 | −21.776 | 1.00 | 24.19 | B | N |
| ATOM | 16306 | CA | LYS | B | 500 | 52.421 | 41.226 | −20.670 | 1.00 | 24.67 | B | C |
| ATOM | 16308 | CB | LYS | B | 500 | 51.083 | 40.762 | −21.234 | 1.00 | 27.83 | B | C |
| ATOM | 16311 | CG | LYS | B | 500 | 50.405 | 41.905 | −21.987 | 1.00 | 27.12 | B | C |
| ATOM | 16314 | CD | LYS | B | 500 | 49.172 | 41.461 | −22.733 | 1.00 | 34.50 | B | C |
| ATOM | 16317 | CE | LYS | B | 500 | 48.524 | 42.638 | −23.450 | 1.00 | 34.28 | B | C |
| ATOM | 16320 | NZ | LYS | B | 500 | 47.799 | 42.149 | −24.632 | 1.00 | 42.60 | B | N |
| ATOM | 16324 | C | LYS | B | 500 | 52.951 | 40.237 | −19.628 | 1.00 | 23.00 | B | C |
| ATOM | 16325 | O | LYS | B | 500 | 52.735 | 40.416 | −18.443 | 1.00 | 24.58 | B | O |
| ATOM | 16327 | N | MET | B | 501 | 53.669 | 39.208 | −20.055 | 1.00 | 22.99 | B | N |
| ATOM | 16328 | CA | MET | B | 501 | 54.321 | 38.326 | −19.099 | 1.00 | 20.54 | B | C |
| ATOM | 16330 | CB | MET | B | 501 | 55.005 | 37.163 | −19.801 | 1.00 | 20.14 | B | C |
| ATOM | 16333 | CG | MET | B | 501 | 54.036 | 36.223 | −20.472 | 1.00 | 24.64 | B | C |
| ATOM | 16336 | SD | MET | B | 501 | 54.785 | 34.668 | −21.007 | 1.00 | 29.22 | B | S |
| ATOM | 16337 | CE | MET | B | 501 | 56.131 | 35.198 | −22.016 | 1.00 | 26.22 | B | C |
| ATOM | 16341 | C | MET | B | 501 | 55.330 | 39.112 | −18.278 | 1.00 | 19.87 | B | C |
| ATOM | 16342 | O | MET | B | 501 | 55.398 | 38.941 | −17.069 | 1.00 | 23.88 | B | O |
| ATOM | 16344 | N | ASN | B | 502 | 56.096 | 39.979 | −18.928 | 1.00 | 18.65 | B | N |
| ATOM | 16345 | CA | ASN | B | 502 | 57.129 | 40.749 | −18.260 | 1.00 | 19.97 | B | C |
| ATOM | 16347 | CB | ASN | B | 502 | 57.837 | 41.683 | −19.265 | 1.00 | 18.67 | B | C |
| ATOM | 16350 | CG | ASN | B | 502 | 58.811 | 40.958 | −20.196 | 1.00 | 22.60 | B | C |
| ATOM | 16351 | OD1 | ASN | B | 502 | 59.178 | 39.788 | −19.987 | 1.00 | 22.42 | B | O |
| ATOM | 16352 | ND2 | ASN | B | 502 | 59.273 | 41.685 | −21.224 | 1.00 | 16.81 | B | N |
| ATOM | 16355 | C | ASN | B | 502 | 56.523 | 41.576 | −17.119 | 1.00 | 22.98 | B | C |
| ATOM | 16356 | O | ASN | B | 502 | 57.114 | 41.713 | −16.027 | 1.00 | 24.16 | B | O |
| ATOM | 16358 | N | LYS | B | 503 | 55.342 | 42.136 | −17.376 | 1.00 | 24.97 | B | N |
| ATOM | 16359 | CA | LYS | B | 503 | 54.643 | 42.934 | −16.369 | 1.00 | 28.54 | B | C |
| ATOM | 16361 | CB | LYS | B | 503 | 53.493 | 43.719 | −17.003 | 1.00 | 27.67 | B | C |
| ATOM | 16364 | CG | LYS | B | 503 | 52.638 | 44.472 | −16.012 | 1.00 | 33.09 | B | C |
| ATOM | 16367 | CD | LYS | B | 503 | 51.658 | 45.394 | −16.757 | 1.00 | 41.49 | B | C |
| ATOM | 16370 | CE | LYS | B | 503 | 50.925 | 46.355 | −15.801 | 1.00 | 47.16 | B | C |
| ATOM | 16373 | NZ | LYS | B | 503 | 49.615 | 46.854 | −16.376 | 1.00 | 45.45 | B | N |
| ATOM | 16377 | C | LYS | B | 503 | 54.141 | 42.058 | −15.221 | 1.00 | 28.95 | B | C |
| ATOM | 16378 | O | LYS | B | 503 | 54.307 | 42.396 | −14.056 | 1.00 | 30.69 | B | O |
| ATOM | 16380 | N | GLU | B | 504 | 53.522 | 40.938 | −15.546 | 1.00 | 30.28 | B | N |
| ATOM | 16381 | CA | GLU | B | 504 | 53.101 | 39.983 | −14.508 | 1.00 | 31.89 | B | C |
| ATOM | 16383 | CB | GLU | B | 504 | 52.551 | 38.690 | −15.149 | 1.00 | 33.44 | B | C |
| ATOM | 16386 | CG | GLU | B | 504 | 51.701 | 37.808 | −14.225 | 1.00 | 38.98 | B | C |
| ATOM | 16389 | CD | GLU | B | 504 | 50.382 | 38.465 | −13.829 | 1.00 | 47.41 | B | C |
| ATOM | 16390 | OE1 | GLU | B | 504 | 49.897 | 38.183 | −12.715 | 1.00 | 52.15 | B | O |
| ATOM | 16391 | OE2 | GLU | B | 504 | 49.841 | 39.277 | −14.618 | 1.00 | 50.82 | B | O |
| ATOM | 16392 | C | GLU | B | 504 | 54.267 | 39.675 | −13.555 | 1.00 | 29.72 | B | C |
| ATOM | 16393 | O | GLU | B | 504 | 54.119 | 39.732 | −12.335 | 1.00 | 31.31 | B | O |
| ATOM | 16395 | N | LYS | B | 505 | 55.433 | 39.388 | −14.114 | 1.00 | 28.05 | B | N |
| ATOM | 16396 | CA | LYS | B | 505 | 56.601 | 38.981 | −13.323 | 1.00 | 27.17 | B | C |
| ATOM | 16398 | CB | LYS | B | 505 | 57.735 | 38.562 | −14.266 | 1.00 | 25.64 | B | C |
| ATOM | 16401 | CG | LYS | B | 505 | 59.066 | 38.259 | −13.594 | 1.00 | 26.00 | B | C |

TABLE 4-2-continued

Coordinates of *P. alba* IspS

| ATOM | 16404 | CD | LYS | B | 505 | 58.995 | 37.017 | −12.710 | 1.00 | 25.01 | B | C |
|---|---|---|---|---|---|---|---|---|---|---|---|---|
| ATOM | 16407 | CE | LYS | B | 505 | 60.305 | 36.802 | −11.941 | 1.00 | 22.47 | B | C |
| ATOM | 16410 | NZ | LYS | B | 505 | 61.449 | 36.651 | −12.865 | 1.00 | 30.06 | B | N |
| ATOM | 16414 | C | LYS | B | 505 | 57.080 | 40.122 | −12.423 | 1.00 | 29.79 | B | C |
| ATOM | 16415 | O | LYS | B | 505 | 57.422 | 39.943 | −11.258 | 1.00 | 30.03 | B | O |
| ATOM | 16417 | N | LEU | B | 506 | 57.092 | 41.306 | −12.993 | 1.00 | 33.92 | B | N |
| ATOM | 16418 | CA | LEU | B | 506 | 57.667 | 42.466 | −12.352 | 1.00 | 37.31 | B | C |
| ATOM | 16420 | CB | LEU | B | 506 | 57.784 | 43.589 | −13.383 | 1.00 | 37.37 | B | C |
| ATOM | 16423 | CG | LEU | B | 506 | 58.791 | 44.692 | −13.143 | 1.00 | 42.52 | B | C |
| ATOM | 16425 | CD1 | LEU | B | 506 | 60.133 | 44.138 | −12.685 | 1.00 | 39.23 | B | C |
| ATOM | 16429 | CD2 | LEU | B | 506 | 58.933 | 45.485 | −14.443 | 1.00 | 47.19 | B | C |
| ATOM | 16433 | C | LEU | B | 506 | 56.838 | 42.932 | −11.174 | 1.00 | 39.52 | B | C |
| ATOM | 16434 | O | LEU | B | 506 | 57.386 | 43.311 | −10.144 | 1.00 | 40.98 | B | O |
| ATOM | 16436 | N | GLY | B | 507 | 55.521 | 42.894 | −11.319 | 1.00 | 42.30 | B | N |
| ATOM | 16437 | CA | GLY | B | 507 | 54.656 | 43.514 | −10.336 | 1.00 | 45.83 | B | C |
| ATOM | 16440 | C | GLY | B | 507 | 53.330 | 42.824 | −10.120 | 1.00 | 49.02 | B | C |
| ATOM | 16441 | O | GLY | B | 507 | 52.686 | 42.354 | −11.062 | 1.00 | 51.49 | B | O |
| ATOM | 16443 | N | GLY | B | 508 | 52.953 | 42.755 | −8.846 | 1.00 | 51.72 | B | N |
| ATOM | 16444 | CA | GLY | B | 508 | 51.591 | 42.445 | −8.415 | 1.00 | 52.78 | B | C |
| ATOM | 16447 | C | GLY | B | 508 | 50.900 | 41.218 | −8.984 | 1.00 | 51.93 | B | C |
| ATOM | 16448 | O | GLY | B | 508 | 49.723 | 41.287 | −9.375 | 1.00 | 54.01 | B | O |
| ATOM | 16450 | N | SER | B | 509 | 51.595 | 40.092 | −9.038 | 1.00 | 49.18 | B | N |
| ATOM | 16451 | CA | ASER | B | 509 | 50.977 | 38.831 | −9.421 | 0.50 | 48.36 | B | C |
| ATOM | 16452 | CA | BSER | B | 509 | 50.890 | 38.872 | −9.440 | 0.50 | 48.06 | B | C |
| ATOM | 16455 | CB | ASER | B | 509 | 52.060 | 37.834 | −9.871 | 0.50 | 48.19 | B | C |
| ATOM | 16456 | CB | BSER | B | 509 | 51.793 | 37.829 | −10.102 | 0.50 | 47.86 | B | C |
| ATOM | 16461 | OG | ASER | B | 509 | 53.237 | 37.924 | −9.070 | 0.50 | 46.36 | B | O |
| ATOM | 16462 | OG | BSER | B | 509 | 50.997 | 36.778 | −10.655 | 0.50 | 43.78 | B | O |
| ATOM | 16465 | C | SER | B | 509 | 50.184 | 38.268 | −8.237 | 1.00 | 47.03 | B | C |
| ATOM | 16466 | O | SER | B | 509 | 50.561 | 38.492 | −7.083 | 1.00 | 45.61 | B | O |
| ATOM | 16468 | N | LEU | B | 510 | 49.118 | 37.529 | −8.528 | 1.00 | 46.26 | B | N |
| ATOM | 16469 | CA | LEU | B | 510 | 48.442 | 36.736 | −7.513 | 1.00 | 45.94 | B | C |
| ATOM | 16471 | CB | LEU | B | 510 | 47.146 | 36.129 | −8.067 | 1.00 | 47.18 | B | C |
| ATOM | 16474 | CG | LEU | B | 510 | 46.198 | 37.118 | −8.781 | 1.00 | 53.98 | B | C |
| ATOM | 16476 | CD1 | LEU | B | 510 | 44.910 | 36.427 | −9.230 | 1.00 | 58.51 | B | C |
| ATOM | 16480 | CD2 | LEU | B | 510 | 45.873 | 38.358 | −7.911 | 1.00 | 59.66 | B | C |
| ATOM | 16484 | C | LEU | B | 510 | 49.432 | 35.643 | −7.040 | 1.00 | 43.67 | B | C |
| ATOM | 16485 | O | LEU | B | 510 | 49.486 | 35.316 | −5.843 | 1.00 | 45.41 | B | O |
| ATOM | 16487 | N | PHE | B | 511 | 50.262 | 35.156 | −7.969 | 1.00 | 37.67 | B | N |
| ATOM | 16488 | CA | PHE | B | 511 | 51.233 | 34.089 | −7.707 | 1.00 | 35.65 | B | C |
| ATOM | 16490 | CB | PHE | B | 511 | 51.418 | 33.218 | −8.967 | 1.00 | 34.37 | B | C |
| ATOM | 16493 | CG | PHE | B | 511 | 50.169 | 32.496 | −9.394 | 1.00 | 29.50 | B | C |
| ATOM | 16494 | CD1 | PHE | B | 511 | 49.935 | 31.208 | −8.981 | 1.00 | 27.92 | B | C |
| ATOM | 16496 | CE1 | PHE | B | 511 | 48.772 | 30.537 | −9.360 | 1.00 | 32.35 | B | C |
| ATOM | 16498 | CZ | PHE | B | 511 | 47.838 | 31.173 | −10.146 | 1.00 | 33.79 | B | C |
| ATOM | 16500 | CE2 | PHE | B | 511 | 48.062 | 32.483 | −10.557 | 1.00 | 31.04 | B | C |
| ATOM | 16502 | CD2 | PHE | B | 511 | 49.213 | 33.128 | −10.180 | 1.00 | 27.15 | B | C |
| ATOM | 16504 | C | PHE | B | 511 | 52.596 | 34.603 | −7.235 | 1.00 | 35.79 | B | C |
| ATOM | 16505 | O | PHE | B | 511 | 52.977 | 35.747 | −7.481 | 1.00 | 36.71 | B | O |
| ATOM | 16507 | N | ALA | B | 512 | 53.343 | 33.747 | −6.555 | 1.00 | 36.55 | B | N |
| ATOM | 16508 | CA | ALA | B | 512 | 54.681 | 34.127 | −6.137 | 1.00 | 37.34 | B | C |
| ATOM | 16510 | CB | ALA | B | 512 | 55.203 | 33.149 | −5.078 | 1.00 | 36.86 | B | C |
| ATOM | 16514 | C | ALA | B | 512 | 55.593 | 34.159 | −7.380 | 1.00 | 37.03 | B | C |
| ATOM | 16515 | O | ALA | B | 512 | 55.400 | 33.384 | −8.315 | 1.00 | 35.37 | B | O |
| ATOM | 16517 | N | LYS | B | 513 | 56.575 | 35.061 | −7.381 | 1.00 | 37.04 | B | N |
| ATOM | 16518 | CA | LYS | B | 513 | 57.500 | 35.233 | −8.519 | 1.00 | 36.97 | B | C |
| ATOM | 16520 | CB | LYS | B | 513 | 58.511 | 36.341 | −8.230 | 1.00 | 36.08 | B | C |
| ATOM | 16523 | CG | LYS | B | 513 | 57.877 | 37.716 | −8.124 | 1.00 | 43.23 | B | C |
| ATOM | 16526 | CD | LYS | B | 513 | 58.928 | 38.808 | −7.942 | 1.00 | 51.27 | B | C |
| ATOM | 16529 | CE | LYS | B | 513 | 58.301 | 40.198 | −7.948 | 1.00 | 56.81 | B | C |
| ATOM | 16532 | NZ | LYS | B | 513 | 59.264 | 41.260 | −8.368 | 1.00 | 56.22 | B | N |
| ATOM | 16536 | C | LYS | B | 513 | 58.236 | 33.964 | −9.006 | 1.00 | 34.73 | B | C |
| ATOM | 16537 | O | LYS | B | 513 | 58.529 | 33.847 | −10.184 | 1.00 | 35.14 | B | O |
| ATOM | 16539 | N | PRO | B | 514 | 58.539 | 33.019 | −8.111 | 1.00 | 33.75 | B | N |
| ATOM | 16540 | CA | PRO | B | 514 | 59.171 | 31.801 | −8.618 | 1.00 | 31.10 | B | C |
| ATOM | 16542 | CB | PRO | B | 514 | 59.475 | 30.993 | −7.350 | 1.00 | 31.76 | B | C |
| ATOM | 16545 | CG | PRO | B | 514 | 59.565 | 32.013 | −6.258 | 1.00 | 33.72 | B | C |
| ATOM | 16548 | CD | PRO | B | 514 | 58.575 | 33.088 | −6.636 | 1.00 | 34.82 | B | C |
| ATOM | 16551 | C | PRO | B | 514 | 58.274 | 30.994 | −9.531 | 1.00 | 29.47 | B | C |
| ATOM | 16552 | O | PRO | B | 514 | 58.761 | 30.432 | −10.505 | 1.00 | 31.73 | B | O |
| ATOM | 16553 | N | PHE | B | 515 | 56.980 | 30.921 | −9.229 | 1.00 | 27.01 | B | N |
| ATOM | 16554 | CA | PHE | B | 515 | 56.080 | 30.186 | −10.095 | 1.00 | 24.99 | B | C |
| ATOM | 16556 | CB | PHE | B | 515 | 54.791 | 29.771 | −9.412 | 1.00 | 22.89 | B | C |
| ATOM | 16559 | CG | PHE | B | 515 | 53.802 | 29.171 | −10.366 | 1.00 | 25.51 | B | C |
| ATOM | 16560 | CD1 | PHE | B | 515 | 54.021 | 27.920 | −10.902 | 1.00 | 26.17 | B | C |
| ATOM | 16562 | CE1 | PHE | B | 515 | 53.126 | 27.366 | −11.810 | 1.00 | 26.76 | B | C |
| ATOM | 16564 | CZ | PHE | B | 515 | 52.039 | 28.081 | −12.196 | 1.00 | 22.84 | B | C |
| ATOM | 16566 | CE2 | PHE | B | 515 | 51.816 | 29.356 | −11.661 | 1.00 | 20.66 | B | C |

TABLE 4-2-continued

Coordinates of *P. alba* IspS

| ATOM | 16568 | CD2 | PHE | B | 515 | 52.695 | 29.884 | −10.779 | 1.00 | 22.38 | B | C |
|---|---|---|---|---|---|---|---|---|---|---|---|---|
| ATOM | 16570 | C | PHE | B | 515 | 55.789 | 31.000 | −11.364 | 1.00 | 24.60 | B | C |
| ATOM | 16571 | O | PHE | B | 515 | 55.775 | 30.452 | −12.455 | 1.00 | 25.39 | B | O |
| ATOM | 16573 | N | VAL | B | 516 | 55.598 | 32.301 | −11.241 | 1.00 | 23.02 | B | N |
| ATOM | 16574 | CA | VAL | B | 516 | 55.459 | 33.127 | −12.435 | 1.00 | 22.33 | B | C |
| ATOM | 16576 | CB | VAL | B | 516 | 55.339 | 34.620 | −12.126 | 1.00 | 23.22 | B | C |
| ATOM | 16578 | CG1 | VAL | B | 516 | 54.200 | 34.904 | −11.108 | 1.00 | 23.93 | B | C |
| ATOM | 16582 | CG2 | VAL | B | 516 | 55.087 | 35.401 | −13.412 | 1.00 | 19.34 | B | C |
| ATOM | 16586 | C | VAL | B | 516 | 56.633 | 32.914 | −13.403 | 1.00 | 22.95 | B | C |
| ATOM | 16587 | O | VAL | B | 516 | 56.435 | 32.854 | −14.629 | 1.00 | 23.90 | B | O |
| ATOM | 16589 | N | GLU | B | 517 | 57.834 | 32.776 | −12.854 | 1.00 | 21.79 | B | N |
| ATOM | 16590 | CA | GLU | B | 517 | 59.049 | 32.572 | −13.651 | 1.00 | 22.46 | B | C |
| ATOM | 16592 | CB | GLU | B | 517 | 60.298 | 32.804 | −12.771 | 1.00 | 24.28 | B | C |
| ATOM | 16595 | CG | GLU | B | 517 | 61.663 | 32.717 | −13.489 | 1.00 | 22.17 | B | C |
| ATOM | 16598 | CD | GLU | B | 517 | 61.902 | 33.823 | −14.511 | 1.00 | 26.69 | B | C |
| ATOM | 16599 | OE1 | GLU | B | 517 | 61.121 | 34.806 | −14.594 | 1.00 | 26.06 | B | O |
| ATOM | 16600 | OE2 | GLU | B | 517 | 62.892 | 33.702 | −15.252 | 1.00 | 29.10 | B | O |
| ATOM | 16601 | C | GLU | B | 517 | 59.098 | 31.172 | −14.273 | 1.00 | 21.73 | B | C |
| ATOM | 16602 | O | GLU | B | 517 | 59.505 | 31.018 | −15.415 | 1.00 | 24.57 | B | O |
| ATOM | 16604 | N | THR | B | 518 | 58.717 | 30.151 | −13.512 | 1.00 | 23.11 | B | N |
| ATOM | 16605 | CA | THR | B | 518 | 58.574 | 28.798 | −14.050 | 1.00 | 22.81 | B | C |
| ATOM | 16607 | CB | THR | B | 518 | 58.094 | 27.811 | −12.963 | 1.00 | 24.80 | B | C |
| ATOM | 16609 | OG1 | THR | B | 518 | 59.091 | 27.713 | −11.936 | 1.00 | 21.57 | B | O |
| ATOM | 16611 | CG2 | THR | B | 518 | 57.851 | 26.398 | −13.562 | 1.00 | 21.21 | B | C |
| ATOM | 16615 | C | THR | B | 518 | 57.599 | 28.819 | −15.245 | 1.00 | 23.51 | B | C |
| ATOM | 16616 | O | THR | B | 518 | 57.850 | 28.237 | −16.297 | 1.00 | 22.08 | B | O |
| ATOM | 16618 | N | ALA | B | 519 | 56.515 | 29.554 | −15.105 | 1.00 | 21.37 | B | N |
| ATOM | 16619 | CA | ALA | B | 519 | 55.553 | 29.635 | −16.188 | 1.00 | 21.72 | B | C |
| ATOM | 16621 | CB | ALA | B | 519 | 54.308 | 30.395 | −15.737 | 1.00 | 20.07 | B | C |
| ATOM | 16625 | C | ALA | B | 519 | 56.190 | 30.272 | −17.429 | 1.00 | 20.28 | B | C |
| ATOM | 16626 | O | ALA | B | 519 | 56.043 | 29.775 | −18.555 | 1.00 | 19.22 | B | O |
| ATOM | 16628 | N | ILE | B | 520 | 56.935 | 31.350 | −17.227 | 1.00 | 19.49 | B | N |
| ATOM | 16629 | CA | ILE | B | 520 | 57.552 | 32.014 | −18.366 | 1.00 | 18.67 | B | C |
| ATOM | 16631 | CB | ILE | B | 520 | 58.218 | 33.311 | −17.947 | 1.00 | 19.91 | B | C |
| ATOM | 16633 | CG1 | ILE | B | 520 | 57.161 | 34.343 | −17.572 | 1.00 | 21.75 | B | C |
| ATOM | 16636 | CD1 | ILE | B | 520 | 57.701 | 35.559 | −16.769 | 1.00 | 20.13 | B | C |
| ATOM | 16640 | CG2 | ILE | B | 520 | 59.083 | 33.848 | −19.091 | 1.00 | 18.40 | B | C |
| ATOM | 16644 | C | ILE | B | 520 | 58.573 | 31.106 | −19.044 | 1.00 | 18.88 | B | C |
| ATOM | 16645 | O | ILE | B | 520 | 58.740 | 31.162 | −20.255 | 1.00 | 20.10 | B | O |
| ATOM | 16647 | N | ASN | B | 521 | 59.256 | 30.264 | −18.268 | 1.00 | 18.94 | B | N |
| ATOM | 16648 | CA | ASN | B | 521 | 60.166 | 29.282 | −18.848 | 1.00 | 21.21 | B | C |
| ATOM | 16650 | CB | ASN | B | 521 | 60.849 | 28.442 | −17.757 | 1.00 | 23.50 | B | C |
| ATOM | 16653 | CG | ASN | B | 521 | 61.829 | 29.269 | −16.895 | 1.00 | 26.39 | B | C |
| ATOM | 16654 | OD1 | ASN | B | 521 | 62.321 | 30.339 | −17.308 | 1.00 | 20.77 | B | O |
| ATOM | 16655 | ND2 | ASN | B | 521 | 62.126 | 28.755 | −15.700 | 1.00 | 21.46 | B | N |
| ATOM | 16658 | C | ASN | B | 521 | 59.486 | 28.367 | −19.862 | 1.00 | 19.68 | B | C |
| ATOM | 16659 | O | ASN | B | 521 | 60.113 | 27.923 | −20.824 | 1.00 | 22.84 | B | O |
| ATOM | 16661 | N | LEU | B | 522 | 58.208 | 28.091 | −19.692 | 1.00 | 20.02 | B | N |
| ATOM | 16662 | CA | LEU | B | 522 | 57.544 | 27.288 | −20.700 | 1.00 | 22.98 | B | C |
| ATOM | 16664 | CB | LEU | B | 522 | 56.093 | 27.008 | −20.356 | 1.00 | 23.26 | B | C |
| ATOM | 16667 | CG | LEU | B | 522 | 55.375 | 26.269 | −21.493 | 1.00 | 25.82 | B | C |
| ATOM | 16669 | CD1 | LEU | B | 522 | 55.246 | 24.827 | −21.145 | 1.00 | 31.80 | B | C |
| ATOM | 16673 | CD2 | LEU | B | 522 | 54.016 | 26.847 | −21.730 | 1.00 | 25.39 | B | C |
| ATOM | 16677 | C | LEU | B | 522 | 57.625 | 28.024 | −22.040 | 1.00 | 22.13 | B | C |
| ATOM | 16678 | O | LEU | B | 522 | 57.880 | 27.402 | −23.081 | 1.00 | 25.60 | B | O |
| ATOM | 16680 | N | ALA | B | 523 | 57.441 | 29.336 | −22.015 | 1.00 | 17.13 | B | N |
| ATOM | 16681 | CA | ALA | B | 523 | 57.550 | 30.111 | −23.240 | 1.00 | 19.20 | B | C |
| ATOM | 16683 | CB | ALA | B | 523 | 57.176 | 31.574 | −23.011 | 1.00 | 18.47 | B | C |
| ATOM | 16687 | C | ALA | B | 523 | 58.936 | 30.029 | −23.786 | 1.00 | 18.17 | B | C |
| ATOM | 16688 | O | ALA | B | 523 | 59.102 | 29.951 | −24.972 | 1.00 | 18.29 | B | O |
| ATOM | 16690 | N | ARG | B | 524 | 59.937 | 30.084 | −22.904 | 1.00 | 20.77 | B | N |
| ATOM | 16691 | CA | ARG | B | 524 | 61.325 | 30.052 | −23.343 | 1.00 | 20.63 | B | C |
| ATOM | 16693 | CB | ARG | B | 524 | 62.285 | 30.303 | −22.162 | 1.00 | 22.45 | B | C |
| ATOM | 16696 | CG | ARG | B | 524 | 62.178 | 31.723 | −21.612 | 1.00 | 20.20 | B | C |
| ATOM | 16699 | CD | ARG | B | 524 | 63.201 | 32.015 | −20.574 | 1.00 | 17.77 | B | C |
| ATOM | 16702 | NE | ARG | B | 524 | 63.198 | 33.425 | −20.165 | 1.00 | 17.96 | B | N |
| ATOM | 16704 | CZ | ARG | B | 524 | 62.938 | 33.867 | −18.944 | 1.00 | 20.16 | B | C |
| ATOM | 16705 | NH1 | ARG | B | 524 | 62.638 | 33.025 | −17.961 | 1.00 | 24.53 | B | N |
| ATOM | 16708 | NH2 | ARG | B | 524 | 63.015 | 35.165 | −18.692 | 1.00 | 19.14 | B | N |
| ATOM | 16711 | C | ARG | B | 524 | 61.643 | 28.717 | −23.998 | 1.00 | 19.90 | B | C |
| ATOM | 16712 | O | ARG | B | 524 | 62.287 | 28.679 | −25.017 | 1.00 | 19.59 | B | O |
| ATOM | 16714 | N | GLN | B | 525 | 61.179 | 27.632 | −23.398 | 1.00 | 21.47 | B | N |
| ATOM | 16715 | CA | GLN | B | 525 | 61.387 | 26.314 | −23.961 | 1.00 | 22.83 | B | C |
| ATOM | 16717 | CB | GLN | B | 525 | 60.887 | 25.221 | −23.002 | 1.00 | 21.14 | B | C |
| ATOM | 16720 | CG | GLN | B | 525 | 61.193 | 23.820 | −23.486 | 1.00 | 26.80 | B | C |
| ATOM | 16723 | CD | GLN | B | 525 | 62.683 | 23.560 | −23.672 | 1.00 | 31.34 | B | C |
| ATOM | 16724 | OE1 | GLN | B | 525 | 63.453 | 23.736 | −22.757 | 1.00 | 30.44 | B | O |
| ATOM | 16725 | NE2 | GLN | B | 525 | 63.075 | 23.120 | −24.851 | 1.00 | 33.52 | B | N |

TABLE 4-2-continued

Coordinates of *P. alba* IspS

| | | | | | | | | | | | |
|---|---|---|---|---|---|---|---|---|---|---|---|
| ATOM | 16728 | C | GLN | B | 525 | 60.721 | 26.191 | −25.332 | 1.00 | 23.13 | B | C |
| ATOM | 16729 | O | GLN | B | 525 | 61.251 | 25.517 | −26.226 | 1.00 | 24.85 | B | O |
| ATOM | 16731 | N | SER | B | 526 | 59.586 | 26.856 | −25.507 | 1.00 | 21.76 | B | N |
| ATOM | 16732 | CA | SER | B | 526 | 58.916 | 26.851 | −26.788 | 1.00 | 20.34 | B | C |
| ATOM | 16734 | CB | SER | B | 526 | 57.571 | 27.570 | −26.692 | 1.00 | 21.50 | B | C |
| ATOM | 16737 | OG | SER | B | 526 | 56.684 | 26.836 | −25.851 | 1.00 | 24.20 | B | O |
| ATOM | 16739 | C | SER | B | 526 | 59.779 | 27.479 | −27.833 | 1.00 | 21.36 | B | C |
| ATOM | 16740 | O | SER | B | 526 | 59.917 | 26.945 | −28.944 | 1.00 | 20.48 | B | O |
| ATOM | 16742 | N | HIS | B | 527 | 60.376 | 28.622 | −27.513 | 1.00 | 24.54 | B | N |
| ATOM | 16743 | CA | HIS | B | 527 | 61.245 | 29.288 | −28.500 | 1.00 | 26.44 | B | C |
| ATOM | 16745 | CB | HIS | B | 527 | 61.754 | 30.633 | −27.984 | 1.00 | 28.07 | B | C |
| ATOM | 16748 | CG | HIS | B | 527 | 60.721 | 31.719 | −27.999 | 1.00 | 25.63 | B | C |
| ATOM | 16749 | ND1 | HIS | B | 527 | 60.369 | 32.390 | −29.144 | 1.00 | 25.98 | B | N |
| ATOM | 16751 | CE1 | HIS | B | 527 | 59.433 | 33.278 | −28.867 | 1.00 | 25.15 | B | C |
| ATOM | 16753 | NE2 | HIS | B | 527 | 59.162 | 33.209 | −27.579 | 1.00 | 25.73 | B | N |
| ATOM | 16755 | CD2 | HIS | B | 527 | 59.961 | 32.245 | −27.009 | 1.00 | 29.05 | B | C |
| ATOM | 16757 | C | HIS | B | 527 | 62.431 | 28.401 | −28.858 | 1.00 | 28.50 | B | C |
| ATOM | 16758 | O | HIS | B | 527 | 62.881 | 28.401 | −29.992 | 1.00 | 29.68 | B | O |
| ATOM | 16760 | N | CYS | B | 528 | 62.930 | 27.631 | −27.893 | 1.00 | 28.29 | B | N |
| ATOM | 16761 | CA | CYS | B | 528 | 64.161 | 26.887 | −28.104 | 1.00 | 32.46 | B | C |
| ATOM | 16763 | CB | CYS | B | 528 | 64.855 | 26.629 | −26.769 | 1.00 | 32.27 | B | C |
| ATOM | 16766 | SG | CYS | B | 528 | 65.481 | 28.140 | −26.015 | 1.00 | 29.31 | B | S |
| ATOM | 16768 | C | CYS | B | 528 | 63.912 | 25.578 | −28.852 | 1.00 | 34.73 | B | C |
| ATOM | 16769 | O | CYS | B | 528 | 64.732 | 25.149 | −29.651 | 1.00 | 34.26 | B | O |
| ATOM | 16771 | N | THR | B | 529 | 62.760 | 24.979 | −28.597 | 1.00 | 37.83 | B | N |
| ATOM | 16772 | CA | THR | B | 529 | 62.332 | 23.742 | −29.230 | 1.00 | 39.52 | B | C |
| ATOM | 16774 | CB | THR | B | 529 | 61.225 | 23.101 | −28.376 | 1.00 | 39.20 | B | C |
| ATOM | 16776 | OG1 | THR | B | 529 | 61.806 | 22.677 | −27.142 | 1.00 | 39.54 | B | O |
| ATOM | 16778 | CG2 | THR | B | 529 | 60.595 | 21.913 | −29.067 | 1.00 | 38.45 | B | C |
| ATOM | 16782 | C | THR | B | 529 | 61.853 | 23.955 | −30.672 | 1.00 | 41.75 | B | C |
| ATOM | 16783 | O | THR | B | 529 | 62.213 | 23.186 | −31.559 | 1.00 | 41.23 | B | O |
| ATOM | 16785 | N | TYR | B | 530 | 61.062 | 25.001 | −30.908 | 1.00 | 44.34 | B | N |
| ATOM | 16786 | CA | TYR | B | 530 | 60.511 | 25.268 | −32.252 | 1.00 | 46.43 | B | C |
| ATOM | 16788 | CB | TYR | B | 530 | 59.041 | 25.705 | −32.158 | 1.00 | 44.01 | B | C |
| ATOM | 16791 | CG | TYR | B | 530 | 58.222 | 24.607 | −31.519 | 1.00 | 40.79 | B | C |
| ATOM | 16792 | CD1 | TYR | B | 530 | 57.972 | 23.409 | −32.208 | 1.00 | 40.31 | B | C |
| ATOM | 16794 | CE1 | TYR | B | 530 | 57.243 | 22.359 | −31.620 | 1.00 | 35.61 | B | C |
| ATOM | 16796 | CZ | TYR | B | 530 | 56.793 | 22.481 | −30.317 | 1.00 | 34.00 | B | C |
| ATOM | 16797 | OH | TYR | B | 530 | 56.080 | 21.443 | −29.749 | 1.00 | 38.96 | B | O |
| ATOM | 16799 | CE2 | TYR | B | 530 | 57.043 | 23.661 | −29.596 | 1.00 | 36.22 | B | C |
| ATOM | 16801 | CD2 | TYR | B | 530 | 57.760 | 24.716 | −30.202 | 1.00 | 32.71 | B | C |
| ATOM | 16803 | C | TYR | B | 530 | 61.389 | 26.233 | −33.046 | 1.00 | 51.24 | B | C |
| ATOM | 16804 | O | TYR | B | 530 | 61.027 | 27.367 | −33.322 | 1.00 | 52.48 | B | O |
| ATOM | 16806 | N | HIS | B | 531 | 62.574 | 25.735 | −33.384 | 1.00 | 57.86 | B | N |
| ATOM | 16807 | CA | HIS | B | 531 | 63.502 | 26.374 | −34.322 | 1.00 | 61.42 | B | C |
| ATOM | 16809 | CB | HIS | B | 531 | 64.946 | 26.178 | −33.832 | 1.00 | 61.98 | B | C |
| ATOM | 16812 | CG | HIS | B | 531 | 65.332 | 24.737 | −33.645 | 1.00 | 64.97 | B | C |
| ATOM | 16813 | ND1 | HIS | B | 531 | 65.394 | 24.135 | −32.404 | 1.00 | 69.47 | B | N |
| ATOM | 16815 | CE1 | HIS | B | 531 | 65.742 | 22.868 | −32.545 | 1.00 | 66.30 | B | C |
| ATOM | 16817 | NE2 | HIS | B | 531 | 65.906 | 22.625 | −33.833 | 1.00 | 67.05 | B | N |
| ATOM | 16819 | CD2 | HIS | B | 531 | 65.650 | 23.774 | −34.544 | 1.00 | 64.50 | B | C |
| ATOM | 16821 | C | HIS | B | 531 | 63.342 | 25.741 | −35.718 | 1.00 | 63.69 | B | C |
| ATOM | 16822 | O | HIS | B | 531 | 62.596 | 24.762 | −35.878 | 1.00 | 61.87 | B | O |
| ATOM | 16824 | N | ASN | B | 532 | 64.041 | 26.314 | −36.709 | 1.00 | 66.30 | B | N |
| ATOM | 16825 | CA | ASN | B | 532 | 64.175 | 25.735 | −38.056 | 1.00 | 68.40 | B | C |
| ATOM | 16827 | CB | ASN | B | 532 | 63.285 | 26.481 | −39.070 | 1.00 | 69.94 | B | C |
| ATOM | 16830 | CG | ASN | B | 532 | 61.830 | 25.955 | −39.112 | 1.00 | 74.76 | B | C |
| ATOM | 16831 | OD1 | ASN | B | 532 | 61.471 | 25.002 | −38.420 | 1.00 | 78.95 | B | O |
| ATOM | 16832 | ND2 | ASN | B | 532 | 60.999 | 26.584 | −39.941 | 1.00 | 74.30 | B | N |
| ATOM | 16835 | C | ASN | B | 532 | 65.637 | 25.768 | −38.523 | 1.00 | 67.88 | B | C |
| ATOM | 16836 | O | ASN | B | 532 | 66.527 | 25.213 | −37.869 | 1.00 | 66.63 | B | O |
| ATOM | 16838 | N | THR | B | 537 | 73.132 | 23.732 | −39.964 | 1.00 | 92.67 | B | N |
| ATOM | 16839 | CA | THR | B | 537 | 72.461 | 22.617 | −39.298 | 1.00 | 92.98 | B | C |
| ATOM | 16841 | CB | THR | B | 537 | 72.529 | 22.759 | −37.760 | 1.00 | 93.23 | B | C |
| ATOM | 16843 | OG1 | THR | B | 537 | 73.841 | 23.182 | −37.370 | 1.00 | 94.15 | B | O |
| ATOM | 16845 | CG2 | THR | B | 537 | 72.203 | 21.436 | −37.073 | 1.00 | 93.23 | B | C |
| ATOM | 16849 | C | THR | B | 537 | 70.993 | 22.511 | −39.725 | 1.00 | 92.54 | B | C |
| ATOM | 16850 | O | THR | B | 537 | 70.356 | 23.517 | −40.039 | 1.00 | 92.39 | B | O |
| ATOM | 16852 | N | SER | B | 538 | 70.470 | 21.286 | −39.728 | 1.00 | 92.35 | B | N |
| ATOM | 16853 | CA | SER | B | 538 | 69.082 | 21.011 | −40.126 | 1.00 | 92.17 | B | C |
| ATOM | 16855 | CB | SER | B | 538 | 68.996 | 19.620 | −40.773 | 1.00 | 92.20 | B | C |
| ATOM | 16858 | OG | SER | B | 538 | 69.869 | 18.702 | −40.139 | 1.00 | 90.38 | B | O |
| ATOM | 16860 | C | SER | B | 538 | 68.120 | 21.123 | −38.928 | 1.00 | 91.96 | B | C |
| ATOM | 16861 | O | SER | B | 538 | 68.571 | 21.300 | −37.795 | 1.00 | 91.29 | B | O |
| ATOM | 16863 | N | PRO | B | 539 | 66.793 | 21.049 | −39.177 | 1.00 | 92.14 | B | N |
| ATOM | 16864 | CA | PRO | B | 539 | 65.805 | 21.088 | −38.083 | 1.00 | 91.67 | B | C |
| ATOM | 16866 | CB | PRO | B | 539 | 64.457 | 20.853 | −38.796 | 1.00 | 92.19 | B | C |
| ATOM | 16869 | CG | PRO | B | 539 | 64.760 | 20.744 | −40.270 | 1.00 | 93.38 | B | C |

TABLE 4-2-continued

Coordinates of *P. alba* IspS

| ATOM | 16872 | CD | PRO | B | 539 | 66.147 | 21.257 | −40.486 | 1.00 | 92.84 | B | C |
|---|---|---|---|---|---|---|---|---|---|---|---|---|
| ATOM | 16875 | C | PRO | B | 539 | 66.045 | 20.051 | −36.975 | 1.00 | 90.54 | B | C |
| ATOM | 16876 | O | PRO | B | 539 | 66.309 | 20.431 | −35.832 | 1.00 | 90.62 | B | O |
| ATOM | 16877 | N | ASP | B | 540 | 65.954 | 18.763 | −37.298 | 1.00 | 88.88 | B | N |
| ATOM | 16878 | CA | ASP | B | 540 | 66.455 | 17.730 | −36.392 | 1.00 | 87.42 | B | C |
| ATOM | 16880 | CB | ASP | B | 540 | 66.043 | 16.330 | −36.860 | 1.00 | 88.42 | B | C |
| ATOM | 16883 | CG | ASP | B | 540 | 64.596 | 15.999 | −36.524 | 1.00 | 91.80 | B | C |
| ATOM | 16884 | OD1 | ASP | B | 540 | 64.173 | 16.250 | −35.369 | 1.00 | 91.87 | B | O |
| ATOM | 16885 | OD2 | ASP | B | 540 | 63.893 | 15.468 | −37.417 | 1.00 | 93.61 | B | O |
| ATOM | 16886 | C | ASP | B | 540 | 67.972 | 17.858 | −36.375 | 1.00 | 84.38 | B | C |
| ATOM | 16887 | O | ASP | B | 540 | 68.541 | 18.552 | −37.212 | 1.00 | 84.49 | B | O |
| ATOM | 16889 | N | GLU | B | 541 | 68.626 | 17.214 | −35.416 | 1.00 | 80.82 | B | N |
| ATOM | 16890 | CA | GLU | B | 541 | 70.100 | 17.233 | −35.315 | 1.00 | 78.19 | B | C |
| ATOM | 16892 | CB | GLU | B | 541 | 70.777 | 16.841 | −36.642 | 1.00 | 79.32 | B | C |
| ATOM | 16895 | CG | GLU | B | 541 | 70.278 | 15.495 | −37.189 | 1.00 | 82.73 | B | C |
| ATOM | 16898 | CD | GLU | B | 541 | 71.283 | 14.798 | −38.084 | 1.00 | 87.94 | B | C |
| ATOM | 16899 | OE1 | GLU | B | 541 | 72.444 | 14.620 | −37.648 | 1.00 | 90.11 | B | O |
| ATOM | 16900 | OE2 | GLU | B | 541 | 70.904 | 14.416 | −39.216 | 1.00 | 88.49 | B | O |
| ATOM | 16901 | C | GLU | B | 541 | 70.682 | 18.540 | −34.751 | 1.00 | 73.56 | B | C |
| ATOM | 16902 | O | GLU | B | 541 | 71.815 | 18.556 | −34.273 | 1.00 | 73.40 | B | O |
| ATOM | 16904 | N | LEU | B | 542 | 69.927 | 19.632 | −34.816 | 1.00 | 68.80 | B | N |
| ATOM | 16905 | CA | LEU | B | 542 | 70.113 | 20.705 | −33.848 | 1.00 | 64.68 | B | C |
| ATOM | 16907 | CB | LEU | B | 542 | 69.553 | 22.044 | −34.340 | 1.00 | 64.53 | B | C |
| ATOM | 16910 | CG | LEU | B | 542 | 69.909 | 23.238 | −33.441 | 1.00 | 64.65 | B | C |
| ATOM | 16912 | CD1 | LEU | B | 542 | 69.389 | 24.543 | −34.021 | 1.00 | 63.68 | B | C |
| ATOM | 16916 | CD2 | LEU | B | 542 | 71.420 | 23.328 | −33.196 | 1.00 | 66.71 | B | C |
| ATOM | 16920 | C | LEU | B | 542 | 69.415 | 20.250 | −32.563 | 1.00 | 60.16 | B | C |
| ATOM | 16921 | O | LEU | B | 542 | 69.954 | 20.410 | −31.474 | 1.00 | 56.80 | B | O |
| ATOM | 16923 | N | THR | B | 543 | 68.239 | 19.641 | −32.702 | 1.00 | 56.33 | B | N |
| ATOM | 16924 | CA | THR | B | 543 | 67.526 | 19.101 | −31.546 | 1.00 | 54.58 | B | C |
| ATOM | 16926 | CB | THR | B | 543 | 66.124 | 18.577 | −31.927 | 1.00 | 52.91 | B | C |
| ATOM | 16928 | OG1 | THR | B | 543 | 65.436 | 19.560 | −32.707 | 1.00 | 55.01 | B | O |
| ATOM | 16930 | CG2 | THR | B | 543 | 65.311 | 18.285 | −30.686 | 1.00 | 50.48 | B | C |
| ATOM | 16934 | C | THR | B | 543 | 68.322 | 17.979 | −30.862 | 1.00 | 54.20 | B | C |
| ATOM | 16935 | O | THR | B | 543 | 68.443 | 17.967 | −29.631 | 1.00 | 53.54 | B | O |
| ATOM | 16937 | N | ARG | B | 544 | 68.859 | 17.042 | −31.650 | 1.00 | 53.07 | B | N |
| ATOM | 16938 | CA | ARG | B | 544 | 69.633 | 15.927 | −31.084 | 1.00 | 52.95 | B | C |
| ATOM | 16940 | CB | ARG | B | 544 | 69.966 | 14.867 | −32.153 | 1.00 | 53.76 | B | C |
| ATOM | 16943 | CG | ARG | B | 544 | 71.147 | 13.934 | −31.807 | 1.00 | 59.59 | B | C |
| ATOM | 16946 | CD | ARG | B | 544 | 71.594 | 13.065 | −32.998 | 1.00 | 69.45 | B | C |
| ATOM | 16949 | NE | ARG | B | 544 | 72.185 | 13.844 | −34.099 | 1.00 | 74.98 | B | N |
| ATOM | 16951 | CZ | ARG | B | 544 | 73.462 | 14.230 | −34.184 | 1.00 | 78.91 | B | C |
| ATOM | 16952 | NH1 | ARG | B | 544 | 74.342 | 13.930 | −33.226 | 1.00 | 79.02 | B | N |
| ATOM | 16955 | NH2 | ARG | B | 544 | 73.866 | 14.932 | −35.244 | 1.00 | 79.30 | B | N |
| ATOM | 16958 | C | ARG | B | 544 | 70.914 | 16.423 | −30.396 | 1.00 | 50.09 | B | C |
| ATOM | 16959 | O | ARG | B | 544 | 71.349 | 15.822 | −29.418 | 1.00 | 49.18 | B | O |
| ATOM | 16961 | N | LYS | B | 545 | 71.512 | 17.495 | −30.920 | 1.00 | 47.95 | B | N |
| ATOM | 16962 | CA | LYS | B | 545 | 72.733 | 18.060 | −30.332 | 1.00 | 49.20 | B | C |
| ATOM | 16964 | CB | LYS | B | 545 | 73.452 | 19.034 | −31.290 | 1.00 | 50.06 | B | C |
| ATOM | 16967 | CG | LYS | B | 545 | 74.568 | 18.354 | −32.088 | 1.00 | 58.27 | B | C |
| ATOM | 16970 | CD | LYS | B | 545 | 75.488 | 19.319 | −32.834 | 1.00 | 65.12 | B | C |
| ATOM | 16973 | CE | LYS | B | 545 | 76.657 | 18.535 | −33.467 | 1.00 | 70.31 | B | C |
| ATOM | 16976 | NZ | LYS | B | 545 | 77.822 | 19.378 | −33.889 | 1.00 | 72.09 | B | N |
| ATOM | 16980 | C | LYS | B | 545 | 72.446 | 18.743 | −29.008 | 1.00 | 46.91 | B | C |
| ATOM | 16981 | O | LYS | B | 545 | 73.292 | 18.769 | −28.115 | 1.00 | 48.01 | B | O |
| ATOM | 16983 | N | ARG | B | 546 | 71.248 | 19.288 | −28.873 | 1.00 | 44.64 | B | N |
| ATOM | 16984 | CA | ARG | B | 546 | 70.871 | 19.937 | −27.632 | 1.00 | 43.28 | B | C |
| ATOM | 16986 | CB | ARG | B | 546 | 69.730 | 20.917 | −27.871 | 1.00 | 43.53 | B | C |
| ATOM | 16989 | CG | ARG | B | 546 | 70.222 | 22.144 | −28.634 | 1.00 | 38.72 | B | C |
| ATOM | 16992 | CD | ARG | B | 546 | 69.107 | 23.107 | −28.977 | 1.00 | 38.25 | B | C |
| ATOM | 16995 | NE | ARG | B | 546 | 69.662 | 24.350 | −29.501 | 1.00 | 33.40 | B | N |
| ATOM | 16997 | CZ | ARG | B | 546 | 68.947 | 25.364 | −29.967 | 1.00 | 37.10 | B | C |
| ATOM | 16998 | NH1 | ARG | B | 546 | 67.619 | 25.316 | −29.984 | 1.00 | 37.22 | B | N |
| ATOM | 17001 | NH2 | ARG | B | 546 | 69.578 | 26.440 | −30.425 | 1.00 | 44.86 | B | N |
| ATOM | 17004 | C | ARG | B | 546 | 70.554 | 18.916 | −26.552 | 1.00 | 42.26 | B | C |
| ATOM | 17005 | O | ARG | B | 546 | 70.990 | 19.067 | −25.419 | 1.00 | 42.38 | B | O |
| ATOM | 17007 | N | VAL | B | 547 | 69.847 | 17.851 | −26.909 | 1.00 | 41.23 | B | N |
| ATOM | 17008 | CA | VAL | B | 547 | 69.610 | 16.766 | −25.965 | 1.00 | 40.03 | B | C |
| ATOM | 17010 | CB | VAL | B | 547 | 68.784 | 15.617 | −26.584 | 1.00 | 41.02 | B | C |
| ATOM | 17012 | CG1 | VAL | B | 547 | 68.755 | 14.403 | −25.652 | 1.00 | 42.61 | B | C |
| ATOM | 17016 | CG2 | VAL | B | 547 | 67.388 | 16.087 | −26.894 | 1.00 | 35.48 | B | C |
| ATOM | 17020 | C | VAL | B | 547 | 70.949 | 16.242 | −25.511 | 1.00 | 40.46 | B | C |
| ATOM | 17021 | O | VAL | B | 547 | 71.157 | 16.006 | −24.324 | 1.00 | 42.73 | B | O |
| ATOM | 17023 | N | LEU | B | 548 | 71.869 | 16.070 | −26.454 | 1.00 | 39.76 | B | N |
| ATOM | 17024 | CA | LEU | B | 548 | 73.210 | 15.609 | −26.116 | 1.00 | 39.29 | B | C |
| ATOM | 17026 | CB | LEU | B | 548 | 74.089 | 15.436 | −27.368 | 1.00 | 39.65 | B | C |
| ATOM | 17029 | CG | LEU | B | 548 | 74.394 | 13.996 | −27.805 | 1.00 | 45.33 | B | C |
| ATOM | 17031 | CD1 | LEU | B | 548 | 73.140 | 13.267 | −28.315 | 1.00 | 42.95 | B | C |

TABLE 4-2-continued

Coordinates of P. alba IspS

| ATOM | 17035 | CD2 | LEU | B | 548 | 75.493 | 13.998 | −28.880 | 1.00 | 46.14 | B | C |
| --- | --- | --- | --- | --- | --- | --- | --- | --- | --- | --- | --- | --- |
| ATOM | 17039 | C | LEU | B | 548 | 73.895 | 16.545 | −25.107 | 1.00 | 37.32 | B | C |
| ATOM | 17040 | O | LEU | B | 548 | 74.409 | 16.086 | −24.085 | 1.00 | 39.63 | B | O |
| ATOM | 17042 | N | SER | B | 549 | 73.895 | 17.844 | −25.389 | 1.00 | 33.98 | B | N |
| ATOM | 17043 | CA | SER | B | 549 | 74.656 | 18.804 | −24.587 | 1.00 | 32.24 | B | C |
| ATOM | 17045 | CB | SER | B | 549 | 74.859 | 20.074 | −25.377 | 1.00 | 32.05 | B | C |
| ATOM | 17048 | OG | SER | B | 549 | 73.605 | 20.666 | −25.577 | 1.00 | 34.09 | B | O |
| ATOM | 17050 | C | SER | B | 549 | 73.979 | 19.171 | −23.280 | 1.00 | 30.34 | B | C |
| ATOM | 17051 | O | SER | B | 549 | 74.643 | 19.569 | −22.328 | 1.00 | 32.04 | B | O |
| ATOM | 17053 | N | VAL | B | 550 | 72.658 | 19.064 | −23.232 | 1.00 | 28.62 | B | N |
| ATOM | 17054 | CA | VAL | B | 550 | 71.932 | 19.383 | −22.014 | 1.00 | 26.79 | B | C |
| ATOM | 17056 | CB | VAL | B | 550 | 70.551 | 19.991 | −22.299 | 1.00 | 26.82 | B | C |
| ATOM | 17058 | CG1 | VAL | B | 550 | 69.800 | 20.186 | −21.022 | 1.00 | 22.61 | B | C |
| ATOM | 17062 | CG2 | VAL | B | 550 | 70.688 | 21.353 | −23.017 | 1.00 | 18.25 | B | C |
| ATOM | 17066 | C | VAL | B | 550 | 71.828 | 18.162 | −21.097 | 1.00 | 29.02 | B | C |
| ATOM | 17067 | O | VAL | B | 550 | 72.112 | 18.264 | −19.906 | 1.00 | 28.22 | B | O |
| ATOM | 17069 | N | ILE | B | 551 | 71.481 | 16.999 | −21.652 | 1.00 | 30.73 | B | N |
| ATOM | 17070 | CA | ILE | B | 551 | 71.234 | 15.812 | −20.832 | 1.00 | 31.06 | B | C |
| ATOM | 17072 | CB | ILE | B | 551 | 70.034 | 14.999 | −21.334 | 1.00 | 31.51 | B | C |
| ATOM | 17074 | CG1 | ILE | B | 551 | 68.763 | 15.849 | −21.376 | 1.00 | 30.36 | B | C |
| ATOM | 17077 | CD1 | ILE | B | 551 | 68.327 | 16.382 | −20.035 | 1.00 | 37.56 | B | C |
| ATOM | 17081 | CG2 | ILE | B | 551 | 69.854 | 13.747 | −20.460 | 1.00 | 29.79 | B | C |
| ATOM | 17085 | C | ILE | B | 551 | 72.395 | 14.829 | −20.762 | 1.00 | 32.00 | B | C |
| ATOM | 17086 | O | ILE | B | 551 | 72.795 | 14.419 | −19.678 | 1.00 | 31.17 | B | O |
| ATOM | 17088 | N | THR | B | 552 | 72.903 | 14.418 | −21.917 | 1.00 | 34.78 | B | N |
| ATOM | 17089 | CA | THR | B | 552 | 73.696 | 13.200 | −21.985 | 1.00 | 35.86 | B | C |
| ATOM | 17091 | CB | THR | B | 552 | 73.372 | 12.395 | −23.266 | 1.00 | 38.74 | B | C |
| ATOM | 17093 | OG1 | THR | B | 552 | 73.836 | 13.097 | −24.419 | 1.00 | 47.68 | B | O |
| ATOM | 17095 | CG2 | THR | B | 552 | 71.879 | 12.179 | −23.414 | 1.00 | 30.46 | B | C |
| ATOM | 17099 | C | THR | B | 552 | 75.204 | 13.447 | −21.829 | 1.00 | 36.32 | B | C |
| ATOM | 17100 | O | THR | B | 552 | 75.870 | 12.723 | −21.082 | 1.00 | 37.04 | B | O |
| ATOM | 17102 | N | GLU | B | 553 | 75.753 | 14.469 | −22.483 | 1.00 | 36.21 | B | N |
| ATOM | 17103 | CA | GLU | B | 553 | 77.217 | 14.663 | −22.459 | 1.00 | 37.69 | B | C |
| ATOM | 17105 | CB | GLU | B | 553 | 77.744 | 14.854 | −23.887 | 1.00 | 40.39 | B | C |
| ATOM | 17108 | CG | GLU | B | 553 | 77.790 | 13.550 | −24.700 | 1.00 | 47.06 | B | C |
| ATOM | 17111 | CD | GLU | B | 553 | 78.488 | 13.705 | −26.052 | 1.00 | 57.90 | B | C |
| ATOM | 17112 | OE1 | GLU | B | 553 | 79.380 | 12.877 | −26.353 | 1.00 | 60.24 | B | O |
| ATOM | 17113 | OE2 | GLU | B | 553 | 78.145 | 14.649 | −26.810 | 1.00 | 60.91 | B | O |
| ATOM | 17114 | C | GLU | B | 553 | 77.701 | 15.811 | −21.563 | 1.00 | 35.39 | B | C |
| ATOM | 17115 | O | GLU | B | 553 | 77.311 | 16.947 | −21.751 | 1.00 | 34.26 | B | O |
| ATOM | 17117 | N | PRO | B | 554 | 78.574 | 15.515 | −20.589 | 1.00 | 36.02 | B | N |
| ATOM | 17118 | CA | PRO | B | 554 | 79.201 | 16.596 | −19.827 | 1.00 | 34.71 | B | C |
| ATOM | 17120 | CB | PRO | B | 554 | 80.207 | 15.875 | −18.918 | 1.00 | 34.87 | B | C |
| ATOM | 17123 | CG | PRO | B | 554 | 79.840 | 14.450 | −18.926 | 1.00 | 37.61 | B | C |
| ATOM | 17126 | CD | PRO | B | 554 | 79.055 | 14.183 | −20.176 | 1.00 | 37.77 | B | C |
| ATOM | 17129 | C | PRO | B | 554 | 79.954 | 17.593 | −20.699 | 1.00 | 33.50 | B | C |
| ATOM | 17130 | O | PRO | B | 554 | 80.283 | 17.322 | −21.858 | 1.00 | 34.84 | B | O |
| ATOM | 17131 | N | ILE | B | 555 | 80.209 | 18.757 | −20.132 | 1.00 | 32.88 | B | N |
| ATOM | 17132 | CA | ILE | B | 555 | 81.096 | 19.725 | −20.750 | 1.00 | 33.21 | B | C |
| ATOM | 17134 | CB | ILE | B | 555 | 80.876 | 21.140 | −20.138 | 1.00 | 32.95 | B | C |
| ATOM | 17136 | CG1 | ILE | B | 555 | 79.500 | 21.664 | −20.567 | 1.00 | 32.79 | B | C |
| ATOM | 17139 | CD1 | ILE | B | 555 | 79.137 | 23.039 | −20.029 | 1.00 | 29.41 | B | C |
| ATOM | 17143 | CG2 | ILE | B | 555 | 81.957 | 22.100 | −20.587 | 1.00 | 30.93 | B | C |
| ATOM | 17147 | C | ILE | B | 555 | 82.511 | 19.220 | −20.501 | 1.00 | 32.07 | B | C |
| ATOM | 17148 | O | ILE | B | 555 | 82.789 | 18.686 | −19.434 | 1.00 | 30.59 | B | O |
| ATOM | 17150 | N | LEU | B | 556 | 83.391 | 19.367 | −21.484 | 1.00 | 32.81 | B | N |
| ATOM | 17151 | CA | LEU | B | 556 | 84.761 | 18.848 | −21.362 | 1.00 | 34.73 | B | C |
| ATOM | 17153 | CB | LEU | B | 556 | 85.564 | 19.045 | −22.669 | 1.00 | 34.99 | B | C |
| ATOM | 17156 | CG | LEU | B | 556 | 85.005 | 18.383 | −23.948 | 1.00 | 39.49 | B | C |
| ATOM | 17158 | CD1 | LEU | B | 556 | 85.738 | 18.858 | −25.230 | 1.00 | 42.15 | B | C |
| ATOM | 17162 | CD2 | LEU | B | 556 | 85.067 | 16.866 | −23.827 | 1.00 | 40.24 | B | C |
| ATOM | 17166 | C | LEU | B | 556 | 85.454 | 19.540 | −20.179 | 1.00 | 34.19 | B | C |
| ATOM | 17167 | O | LEU | B | 556 | 85.268 | 20.731 | −19.971 | 1.00 | 35.29 | B | O |
| ATOM | 17169 | N | PRO | B | 557 | 86.252 | 18.795 | −19.401 | 1.00 | 34.37 | B | N |
| ATOM | 17170 | CA | PRO | B | 557 | 86.764 | 19.369 | −18.152 | 1.00 | 34.58 | B | C |
| ATOM | 17172 | CB | PRO | B | 557 | 87.532 | 18.209 | −17.506 | 1.00 | 34.08 | B | C |
| ATOM | 17175 | CG | PRO | B | 557 | 87.851 | 17.281 | −18.607 | 1.00 | 35.29 | B | C |
| ATOM | 17178 | CD | PRO | B | 557 | 86.815 | 17.462 | −19.685 | 1.00 | 34.74 | B | C |
| ATOM | 17181 | C | PRO | B | 557 | 87.672 | 20.587 | −18.327 | 1.00 | 34.93 | B | C |
| ATOM | 17182 | O | PRO | B | 557 | 88.198 | 20.847 | −19.407 | 1.00 | 35.00 | B | O |
| ATOM | 17183 | N | PHE | B | 558 | 87.827 | 21.332 | −17.245 | 1.00 | 35.20 | B | N |
| ATOM | 17184 | CA | PHE | B | 558 | 88.627 | 22.539 | −17.251 | 1.00 | 35.65 | B | C |
| ATOM | 17186 | CB | PHE | B | 558 | 88.342 | 23.308 | −15.962 | 1.00 | 32.90 | B | C |
| ATOM | 17189 | CG | PHE | B | 558 | 89.329 | 24.400 | −15.656 | 1.00 | 35.99 | B | C |
| ATOM | 17190 | CD1 | PHE | B | 558 | 90.270 | 24.248 | −14.636 | 1.00 | 38.91 | B | C |
| ATOM | 17192 | CE1 | PHE | B | 558 | 91.172 | 25.264 | −14.339 | 1.00 | 40.56 | B | C |
| ATOM | 17194 | CZ | PHE | B | 558 | 91.140 | 26.448 | −15.062 | 1.00 | 39.35 | B | C |
| ATOM | 17196 | CE2 | PHE | B | 558 | 90.208 | 26.608 | −16.074 | 1.00 | 38.08 | B | C |

TABLE 4-2-continued

Coordinates of P. alba IspS

| ATOM | 17198 | CD2 | PHE | B | 558 | 89.311 | 25.589 | −16.367 | 1.00 | 36.76 | B | C |
|---|---|---|---|---|---|---|---|---|---|---|---|---|
| ATOM | 17200 | C | PHE | B | 558 | 90.119 | 22.174 | −17.388 | 1.00 | 38.66 | B | C |
| ATOM | 17201 | O | PHE | B | 558 | 90.588 | 21.221 | −16.768 | 1.00 | 35.43 | B | O |
| ATOM | 17203 | N | GLU | B | 559 | 90.841 | 22.934 | −18.210 | 1.00 | 43.59 | B | N |
| ATOM | 17204 | CA | GLU | B | 559 | 92.278 | 22.725 | −18.437 | 1.00 | 49.37 | B | C |
| ATOM | 17206 | CB | GLU | B | 559 | 92.527 | 22.302 | −19.886 | 1.00 | 50.25 | B | C |
| ATOM | 17209 | CG | GLU | B | 559 | 92.467 | 20.803 | −20.151 | 1.00 | 55.23 | B | C |
| ATOM | 17212 | CD | GLU | B | 559 | 92.918 | 20.460 | −21.569 | 1.00 | 62.27 | B | C |
| ATOM | 17213 | OE1 | GLU | B | 559 | 92.093 | 20.605 | −22.507 | 1.00 | 58.80 | B | O |
| ATOM | 17214 | OE2 | GLU | B | 559 | 94.100 | 20.059 | −21.736 | 1.00 | 59.57 | B | O |
| ATOM | 17215 | C | GLU | B | 559 | 93.083 | 24.001 | −18.161 | 1.00 | 52.39 | B | C |
| ATOM | 17216 | O | GLU | B | 559 | 92.772 | 25.061 | −18.707 | 1.00 | 52.68 | B | O |
| ATOM | 17218 | N | ARG | B | 560 | 94.128 | 23.886 | −17.343 | 1.00 | 55.22 | B | N |
| ATOM | 17219 | CA | ARG | B | 560 | 95.025 | 25.016 | −17.043 | 1.00 | 57.60 | B | C |
| ATOM | 17221 | CB | ARG | B | 560 | 95.966 | 24.658 | −15.890 | 1.00 | 58.83 | B | C |
| ATOM | 17224 | CG | ARG | B | 560 | 95.247 | 24.332 | −14.589 | 1.00 | 63.59 | B | C |
| ATOM | 17227 | CD | ARG | B | 560 | 95.488 | 25.362 | −13.492 | 1.00 | 69.13 | B | C |
| ATOM | 17230 | NE | ARG | B | 560 | 94.390 | 25.393 | −12.522 | 1.00 | 75.07 | B | N |
| ATOM | 17232 | CZ | ARG | B | 560 | 94.070 | 24.398 | −11.686 | 1.00 | 78.47 | B | C |
| ATOM | 17233 | NH1 | ARG | B | 560 | 94.752 | 23.252 | −11.675 | 1.00 | 78.68 | B | N |
| ATOM | 17236 | NH2 | ARG | B | 560 | 93.047 | 24.545 | −10.847 | 1.00 | 78.46 | B | N |
| ATOM | 17239 | C | ARG | B | 560 | 95.856 | 25.404 | −18.261 | 1.00 | 57.16 | B | C |
| ATOM | 17240 | O | ARG | B | 560 | 95.920 | 26.575 | −18.624 | 1.00 | 57.13 | B | O |
| ATOM | 17242 | O | HOH | W | 1 | 67.396 | 39.491 | −23.826 | 1.00 | 20.98 | W | O |
| ATOM | 17245 | O | HOH | W | 2 | 46.505 | 15.035 | −3.469 | 1.00 | 20.88 | W | O |
| ATOM | 17248 | O | HOH | W | 3 | 36.160 | 7.031 | −16.321 | 1.00 | 25.10 | W | O |
| ATOM | 17251 | O | HOH | W | 4 | 34.395 | 30.503 | −35.530 | 1.00 | 17.73 | W | O |
| ATOM | 17254 | O | HOH | W | 5 | 37.638 | 17.344 | −11.502 | 1.00 | 32.45 | W | O |
| ATOM | 17257 | O | HOH | W | 6 | 65.819 | −37.512 | 3.562 | 1.00 | 29.91 | W | O |
| ATOM | 17260 | O | HOH | W | 7 | 56.866 | −34.130 | −11.051 | 1.00 | 31.56 | W | O |
| ATOM | 17263 | O | HOH | W | 8 | 43.972 | −6.315 | −15.500 | 1.00 | 23.40 | W | O |
| ATOM | 17266 | O | HOH | W | 9 | 60.228 | −40.852 | 2.964 | 1.00 | 21.46 | W | O |
| ATOM | 17269 | O | HOH | W | 10 | 43.012 | 23.511 | −17.712 | 1.00 | 41.96 | W | O |
| ATOM | 17272 | O | HOH | W | 11 | 38.135 | 14.576 | −14.888 | 1.00 | 28.05 | W | O |
| ATOM | 17275 | O | HOH | W | 12 | 57.728 | −35.432 | 5.083 | 1.00 | 24.61 | W | O |
| ATOM | 17278 | O | HOH | W | 13 | 57.235 | −51.809 | −9.446 | 1.00 | 34.71 | W | O |
| ATOM | 17281 | O | HOH | W | 14 | 66.193 | 38.695 | −7.571 | 1.00 | 26.05 | W | O |
| ATOM | 17284 | O | HOH | W | 15 | 36.482 | −23.763 | 3.380 | 1.00 | 35.70 | W | O |
| ATOM | 17287 | O | HOH | W | 16 | 63.221 | −40.097 | 3.528 | 1.00 | 27.60 | W | O |
| ATOM | 17290 | O | HOH | W | 17 | 73.515 | 25.429 | 6.453 | 1.00 | 49.84 | W | O |
| ATOM | 17293 | O | HOH | W | 18 | 53.192 | 45.369 | −20.010 | 1.00 | 31.15 | W | O |
| ATOM | 17296 | O | HOH | W | 19 | 77.678 | 42.352 | 1.054 | 1.00 | 32.86 | W | O |
| ATOM | 17299 | O | HOH | W | 20 | 48.264 | −34.170 | 15.244 | 1.00 | 46.42 | W | O |
| ATOM | 17302 | O | HOH | W | 21 | 39.547 | 35.857 | −35.345 | 1.00 | 19.86 | W | O |
| ATOM | 17305 | O | HOH | W | 22 | 35.404 | −1.739 | −16.317 | 1.00 | 27.73 | W | O |
| ATOM | 17308 | O | HOH | W | 23 | 62.314 | 8.273 | −25.549 | 1.00 | 44.96 | W | O |
| ATOM | 17311 | O | HOH | W | 24 | 42.306 | 22.146 | −12.509 | 1.00 | 21.07 | W | O |
| ATOM | 17314 | O | HOH | W | 25 | 41.363 | 11.085 | −35.066 | 1.00 | 18.32 | W | O |
| ATOM | 17317 | O | HOH | W | 26 | 46.155 | −26.355 | −2.836 | 1.00 | 27.33 | W | O |
| ATOM | 17320 | O | HOH | W | 27 | 73.732 | 29.702 | −30.702 | 1.00 | 33.09 | W | O |
| ATOM | 17323 | O | HOH | W | 28 | 55.875 | −54.406 | 1.824 | 1.00 | 32.16 | W | O |
| ATOM | 17326 | O | HOH | W | 29 | 55.002 | 28.302 | −1.446 | 1.00 | 42.39 | W | O |
| ATOM | 17329 | O | HOH | W | 30 | 45.510 | −23.435 | −12.887 | 1.00 | 39.50 | W | O |
| ATOM | 17332 | O | HOH | W | 31 | 53.296 | 48.691 | −18.974 | 1.00 | 46.53 | W | O |
| ATOM | 17335 | O | HOH | W | 32 | 65.749 | −34.978 | 8.760 | 1.00 | 23.25 | W | O |
| ATOM | 17338 | O | HOH | W | 33 | 41.864 | −40.579 | 7.567 | 1.00 | 27.81 | W | O |
| ATOM | 17341 | O | HOH | W | 34 | 62.501 | 38.943 | −10.518 | 1.00 | 24.84 | W | O |
| ATOM | 17344 | O | HOH | W | 35 | 62.874 | −31.234 | 17.475 | 1.00 | 40.25 | W | O |
| ATOM | 17347 | O | HOH | W | 36 | 72.629 | −36.786 | 2.592 | 1.00 | 26.17 | W | O |
| ATOM | 17350 | O | HOH | W | 37 | 33.607 | 7.834 | −9.701 | 1.00 | 45.87 | W | O |
| ATOM | 17353 | O | HOH | W | 38 | 77.284 | −36.310 | −9.186 | 1.00 | 41.42 | W | O |
| ATOM | 17356 | O | HOH | W | 39 | 77.331 | 43.278 | −25.049 | 1.00 | 30.11 | W | O |
| ATOM | 17359 | O | HOH | W | 40 | 39.966 | −6.135 | −21.236 | 1.00 | 39.64 | W | O |
| ATOM | 17362 | O | HOH | W | 41 | 53.845 | −3.289 | 6.774 | 1.00 | 27.25 | W | O |
| ATOM | 17365 | O | HOH | W | 42 | 39.457 | 24.448 | −15.702 | 1.00 | 31.86 | W | O |
| ATOM | 17368 | O | HOH | W | 43 | 50.941 | −47.129 | 15.355 | 1.00 | 37.33 | W | O |
| ATOM | 17371 | O | HOH | W | 44 | 31.147 | 15.698 | −26.421 | 1.00 | 31.90 | W | O |
| ATOM | 17374 | O | HOH | W | 45 | 75.880 | 39.481 | −22.456 | 1.00 | 24.94 | W | O |
| ATOM | 17377 | O | HOH | W | 46 | 54.871 | 30.920 | −42.208 | 1.00 | 31.91 | W | O |
| ATOM | 17380 | O | HOH | W | 47 | 65.261 | −50.315 | 5.447 | 1.00 | 32.59 | W | O |
| ATOM | 17383 | O | HOH | W | 48 | 71.408 | −9.056 | −6.457 | 1.00 | 27.35 | W | O |
| ATOM | 17386 | O | HOH | W | 49 | 68.507 | −42.622 | −19.180 | 1.00 | 39.04 | W | O |
| ATOM | 17389 | O | HOH | W | 50 | 40.635 | −32.994 | −1.450 | 1.00 | 29.96 | W | O |
| ATOM | 17392 | O | HOH | W | 51 | 43.834 | 39.340 | −19.280 | 1.00 | 44.69 | W | O |
| ATOM | 17395 | O | HOH | W | 52 | 49.324 | −10.510 | −8.611 | 1.00 | 22.83 | W | O |
| ATOM | 17398 | O | HOH | W | 53 | 73.154 | −41.586 | −3.585 | 1.00 | 28.18 | W | O |
| ATOM | 17401 | O | HOH | W | 54 | 74.167 | −32.081 | 10.431 | 1.00 | 38.80 | W | O |
| ATOM | 17404 | O | HOH | W | 55 | 32.208 | −24.041 | 27.564 | 1.00 | 36.12 | W | O |

TABLE 4-2-continued

Coordinates of *P. alba* IspS

| ATOM | 17407 | O | HOH | W | 56 | 81.358 | 51.348 | −21.846 | 1.00 | 36.22 | W | O |
|------|-------|---|-----|---|----|--------|--------|---------|------|-------|---|---|
| ATOM | 17410 | O | HOH | W | 57 | 28.049 | −9.147 | 14.182 | 1.00 | 28.08 | W | O |
| ATOM | 17413 | O | HOH | W | 58 | 53.295 | −33.548 | −8.420 | 1.00 | 32.02 | W | O |
| ATOM | 17416 | O | HOH | W | 59 | 33.141 | −27.930 | 14.065 | 1.00 | 49.40 | W | O |
| ATOM | 17419 | O | HOH | W | 60 | 73.963 | 42.850 | −22.320 | 1.00 | 27.05 | W | O |
| ATOM | 17422 | O | HOH | W | 61 | 57.737 | 18.482 | −4.811 | 1.00 | 40.88 | W | O |
| ATOM | 17425 | O | HOH | W | 62 | 41.825 | 42.820 | −42.173 | 1.00 | 33.38 | W | O |
| ATOM | 17428 | O | HOH | W | 63 | 32.765 | 16.578 | −23.918 | 1.00 | 31.22 | W | O |
| ATOM | 17431 | O | HOH | W | 64 | 37.857 | 13.924 | −10.555 | 1.00 | 34.26 | W | O |
| ATOM | 17434 | O | HOH | W | 65 | 89.849 | 19.986 | −14.523 | 1.00 | 30.80 | W | O |
| ATOM | 17437 | O | HOH | W | 66 | 28.309 | −3.232 | 7.889 | 1.00 | 33.97 | W | O |
| ATOM | 17440 | O | HOH | W | 67 | 81.027 | 23.484 | 4.883 | 1.00 | 29.67 | W | O |
| ATOM | 17443 | O | HOH | W | 68 | 92.000 | 34.104 | −14.235 | 1.00 | 25.36 | W | O |
| ATOM | 17446 | O | HOH | W | 69 | 33.611 | −22.981 | 9.544 | 1.00 | 26.38 | W | O |
| ATOM | 17449 | O | HOH | W | 70 | 69.544 | 29.746 | 3.258 | 1.00 | 45.00 | W | O |
| ATOM | 17452 | O | HOH | W | 71 | 33.580 | 19.200 | −28.527 | 1.00 | 28.54 | W | O |
| ATOM | 17455 | O | HOH | W | 72 | 60.973 | −6.895 | 13.133 | 1.00 | 51.02 | W | O |
| ATOM | 17458 | O | HOH | W | 73 | 63.662 | −53.195 | 6.160 | 1.00 | 31.10 | W | O |
| ATOM | 17461 | O | HOH | W | 74 | 40.501 | 13.400 | 9.740 | 1.00 | 29.39 | W | O |
| ATOM | 17464 | O | HOH | W | 75 | 31.268 | −0.700 | −16.248 | 1.00 | 38.68 | W | O |
| ATOM | 17467 | O | HOH | W | 76 | 64.405 | 12.253 | −9.311 | 1.00 | 32.15 | W | O |
| ATOM | 17470 | O | HOH | W | 77 | 51.823 | −41.573 | −13.076 | 1.00 | 38.60 | W | O |
| ATOM | 17473 | O | HOH | W | 78 | 52.094 | −48.948 | −6.963 | 1.00 | 36.07 | W | O |
| ATOM | 17476 | O | HOH | W | 79 | 65.280 | −37.041 | 19.710 | 1.00 | 36.79 | W | O |
| ATOM | 17479 | O | HOH | W | 80 | 73.752 | −42.738 | −1.116 | 1.00 | 42.80 | W | O |
| ATOM | 17482 | O | HOH | W | 81 | 33.127 | 5.296 | 2.323 | 1.00 | 34.50 | W | O |
| ATOM | 17485 | O | HOH | W | 82 | 52.917 | 19.244 | −39.930 | 1.00 | 38.53 | W | O |
| ATOM | 17488 | O | HOH | W | 83 | 31.947 | −16.214 | −2.242 | 1.00 | 42.38 | W | O |
| ATOM | 17491 | O | HOH | W | 84 | 44.466 | 34.961 | −48.175 | 1.00 | 39.18 | W | O |
| ATOM | 17494 | O | HOH | W | 85 | 73.801 | 10.513 | −12.397 | 1.00 | 34.17 | W | O |
| ATOM | 17497 | O | HOH | W | 86 | 56.162 | −30.900 | 13.891 | 1.00 | 36.49 | W | O |
| ATOM | 17500 | O | HOH | W | 87 | 58.302 | 40.830 | −34.099 | 1.00 | 38.00 | W | O |
| ATOM | 17503 | O | HOH | W | 88 | 67.361 | 57.337 | −12.595 | 1.00 | 35.90 | W | O |
| ATOM | 17506 | O | HOH | W | 89 | 36.407 | 16.844 | −14.535 | 1.00 | 34.76 | W | O |
| ATOM | 17509 | O | HOH | W | 90 | 36.526 | −2.835 | −11.577 | 1.00 | 29.09 | W | O |
| ATOM | 17512 | O | HOH | W | 91 | 63.568 | 38.471 | −8.120 | 1.00 | 33.00 | W | O |
| ATOM | 17515 | O | HOH | W | 92 | 31.876 | −24.706 | −14.685 | 1.00 | 47.13 | W | O |
| ATOM | 17518 | O | HOH | W | 93 | 57.122 | 46.180 | −41.231 | 1.00 | 38.56 | W | O |
| ATOM | 17521 | O | HOH | W | 94 | 40.989 | 25.119 | −38.866 | 1.00 | 34.26 | W | O |
| ATOM | 17524 | O | HOH | W | 95 | 70.573 | 35.539 | −11.174 | 1.00 | 34.26 | W | O |
| ATOM | 17527 | O | HOH | W | 96 | 67.166 | −18.296 | −0.056 | 1.00 | 21.97 | W | O |
| ATOM | 17530 | O | HOH | W | 97 | 68.329 | −19.165 | −2.481 | 1.00 | 27.46 | W | O |
| ATOM | 17533 | O | HOH | W | 98 | 46.453 | −46.459 | −0.096 | 1.00 | 23.67 | W | O |
| ATOM | 17536 | O | HOH | W | 99 | 64.859 | −27.821 | −0.476 | 1.00 | 23.74 | W | O |
| ATOM | 17539 | O | HOH | W | 100 | 49.889 | −41.983 | −4.752 | 1.00 | 19.81 | W | O |
| ATOM | 17542 | O | HOH | W | 101 | 63.104 | −35.094 | −0.981 | 1.00 | 21.48 | W | O |
| ATOM | 17545 | O | HOH | W | 102 | 46.208 | 22.160 | −21.251 | 1.00 | 17.27 | W | O |
| ATOM | 17548 | O | HOH | W | 103 | 44.240 | 21.517 | −19.373 | 1.00 | 18.97 | W | O |
| ATOM | 17551 | O | HOH | W | 104 | 60.940 | −21.568 | −0.115 | 1.00 | 20.52 | W | O |
| ATOM | 17554 | O | HOH | W | 105 | 58.540 | −23.194 | −0.426 | 1.00 | 28.03 | W | O |
| ATOM | 17557 | O | HOH | W | 106 | 52.842 | −31.073 | −2.319 | 1.00 | 18.19 | W | O |
| ATOM | 17560 | O | HOH | W | 107 | 50.708 | −32.784 | −1.585 | 1.00 | 21.26 | W | O |
| ATOM | 17563 | O | HOH | W | 108 | 42.573 | 24.337 | −31.730 | 1.00 | 23.68 | W | O |
| ATOM | 17566 | O | HOH | W | 109 | 41.632 | −13.280 | 2.319 | 1.00 | 19.40 | W | O |
| ATOM | 17569 | O | HOH | W | 110 | 40.075 | −12.128 | 0.609 | 1.00 | 22.13 | W | O |
| ATOM | 17572 | O | HOH | W | 111 | 61.623 | 26.993 | −12.882 | 1.00 | 31.00 | W | O |
| ATOM | 17575 | O | HOH | W | 112 | 53.819 | 33.804 | −16.115 | 1.00 | 25.71 | W | O |
| ATOM | 17578 | O | HOH | W | 113 | 45.232 | 4.296 | −9.419 | 1.00 | 19.63 | W | O |
| ATOM | 17581 | O | HOH | W | 114 | 67.086 | 25.456 | −18.731 | 1.00 | 20.32 | W | O |
| ATOM | 17584 | O | HOH | W | 115 | 69.127 | −23.507 | −5.191 | 1.00 | 19.05 | W | O |
| ATOM | 17587 | O | HOH | W | 116 | 40.100 | −27.766 | 7.117 | 1.00 | 26.86 | W | O |
| ATOM | 17590 | O | HOH | W | 117 | 41.450 | 14.502 | −35.661 | 1.00 | 21.87 | W | O |
| ATOM | 17593 | O | HOH | W | 118 | 39.215 | 14.175 | −36.764 | 1.00 | 21.90 | W | O |
| ATOM | 17596 | O | HOH | W | 119 | 61.445 | 47.858 | −13.974 | 1.00 | 30.41 | W | O |
| ATOM | 17599 | O | HOH | W | 120 | 42.487 | −37.324 | 1.207 | 1.00 | 19.42 | W | O |
| ATOM | 17602 | O | HOH | W | 121 | 41.098 | −41.117 | 0.324 | 1.00 | 20.14 | W | O |
| ATOM | 17605 | O | HOH | W | 122 | 58.612 | −35.406 | −0.839 | 1.00 | 24.21 | W | O |
| ATOM | 17608 | O | HOH | W | 123 | 50.164 | 1.626 | −14.069 | 1.00 | 17.73 | W | O |
| ATOM | 17611 | O | HOH | W | 124 | 50.992 | −34.804 | 12.341 | 1.00 | 30.50 | W | O |
| ATOM | 17614 | O | HOH | W | 125 | 70.666 | 34.211 | −26.020 | 1.00 | 27.41 | W | O |
| ATOM | 17617 | O | HOH | W | 126 | 57.737 | −13.710 | −12.328 | 1.00 | 35.35 | W | O |
| ATOM | 17620 | O | HOH | W | 127 | 75.308 | 25.160 | −13.718 | 1.00 | 16.25 | W | O |
| ATOM | 17623 | O | HOH | W | 128 | 60.917 | −29.336 | 2.205 | 1.00 | 27.11 | W | O |
| ATOM | 17626 | O | HOH | W | 129 | 37.974 | −12.318 | −6.397 | 1.00 | 29.33 | W | O |
| ATOM | 17629 | O | HOH | W | 130 | 63.665 | −29.882 | −4.118 | 1.00 | 31.17 | W | O |
| ATOM | 17632 | O | HOH | W | 131 | 61.715 | −32.330 | −8.029 | 1.00 | 41.88 | W | O |
| ATOM | 17635 | O | HOH | W | 132 | 72.648 | 30.403 | −18.375 | 1.00 | 23.01 | W | O |
| ATOM | 17638 | O | HOH | W | 133 | 53.042 | 17.634 | −10.102 | 1.00 | 23.18 | W | O |

TABLE 4-2-continued

Coordinates of P. alba IspS

| ATOM | 17641 | O | HOH | W | 134 | 60.025 | 38.653 | −17.369 | 1.00 | 20.09 | W | O |
|---|---|---|---|---|---|---|---|---|---|---|---|---|
| ATOM | 17644 | O | HOH | W | 135 | 61.712 | 36.617 | −16.767 | 1.00 | 26.79 | W | O |
| ATOM | 17647 | O | HOH | W | 136 | 61.300 | 41.278 | −13.860 | 1.00 | 21.09 | W | O |
| ATOM | 17650 | O | HOH | W | 137 | 62.073 | −31.149 | 7.450 | 1.00 | 33.22 | W | O |
| ATOM | 17653 | O | HOH | W | 138 | 55.630 | −21.810 | −5.863 | 1.00 | 43.72 | W | O |
| ATOM | 17656 | O | HOH | W | 139 | 42.191 | 33.282 | −26.587 | 1.00 | 21.30 | W | O |
| ATOM | 17659 | O | HOH | W | 140 | 46.789 | 38.171 | −22.658 | 1.00 | 44.17 | W | O |
| ATOM | 17662 | O | HOH | W | 141 | 32.524 | 32.302 | −32.556 | 1.00 | 27.94 | W | O |
| ATOM | 17665 | O | HOH | W | 142 | 83.918 | 41.902 | −15.045 | 1.00 | 20.74 | W | O |
| ATOM | 17668 | O | HOH | W | 143 | 57.939 | −30.258 | 0.884 | 1.00 | 32.72 | W | O |
| ATOM | 17671 | O | HOH | W | 144 | 48.703 | −35.022 | 7.181 | 1.00 | 37.63 | W | O |
| ATOM | 17674 | O | HOH | W | 145 | 66.347 | 31.640 | −19.130 | 1.00 | 30.26 | W | O |
| ATOM | 17677 | O | HOH | W | 146 | 64.998 | 30.057 | −17.211 | 1.00 | 22.53 | W | O |
| ATOM | 17680 | O | HOH | W | 147 | 65.134 | 27.653 | −18.405 | 1.00 | 22.78 | W | O |
| ATOM | 17683 | O | HOH | W | 148 | 66.094 | 38.403 | −18.347 | 1.00 | 23.57 | W | O |
| ATOM | 17686 | O | HOH | W | 149 | 35.459 | 0.990 | 18.585 | 1.00 | 22.46 | W | O |
| ATOM | 17689 | O | HOH | W | 150 | 71.717 | −45.326 | −18.716 | 1.00 | 33.34 | W | O |
| ATOM | 17692 | O | HOH | W | 151 | 50.671 | 5.704 | −4.812 | 1.00 | 26.81 | W | O |
| ATOM | 17695 | O | HOH | W | 152 | 61.207 | −27.443 | −25.202 | 1.00 | 50.62 | W | O |
| ATOM | 17698 | O | HOH | W | 153 | 74.197 | −28.017 | −17.761 | 1.00 | 32.53 | W | O |
| ATOM | 17701 | O | HOH | W | 154 | 39.585 | −1.129 | 16.289 | 1.00 | 21.92 | W | O |
| ATOM | 17704 | O | HOH | W | 155 | 62.622 | −29.524 | −0.090 | 1.00 | 32.78 | W | O |
| ATOM | 17707 | O | HOH | W | 156 | 70.598 | −25.384 | −3.982 | 1.00 | 23.20 | W | O |
| ATOM | 17710 | O | HOH | W | 157 | 56.563 | −33.832 | −0.616 | 1.00 | 27.25 | W | O |
| ATOM | 17713 | O | HOH | W | 158 | 51.474 | −35.440 | −5.147 | 1.00 | 26.23 | W | O |
| ATOM | 17716 | O | HOH | W | 159 | 49.890 | −35.190 | −2.859 | 1.00 | 23.25 | W | O |
| ATOM | 17719 | O | HOH | W | 160 | 53.387 | −33.463 | −5.052 | 1.00 | 31.52 | W | O |
| ATOM | 17722 | O | HOH | W | 161 | 64.357 | −36.964 | 7.375 | 1.00 | 28.26 | W | O |
| ATOM | 17725 | O | HOH | W | 162 | 64.771 | −39.173 | 5.737 | 1.00 | 31.93 | W | O |
| ATOM | 17728 | O | HOH | W | 163 | 40.629 | −47.274 | 5.327 | 1.00 | 20.11 | W | O |
| ATOM | 17731 | O | HOH | W | 164 | 49.479 | −36.987 | 8.266 | 1.00 | 38.74 | W | O |
| ATOM | 17734 | O | HOH | W | 165 | 50.017 | −31.400 | 12.975 | 1.00 | 31.54 | W | O |
| ATOM | 17737 | O | HOH | W | 166 | 72.235 | −28.166 | 9.021 | 1.00 | 33.15 | W | O |
| ATOM | 17740 | O | HOH | W | 167 | 75.744 | −38.559 | −1.129 | 1.00 | 34.88 | W | O |
| ATOM | 17743 | O | HOH | W | 168 | 60.678 | −3.886 | 6.560 | 1.00 | 43.68 | W | O |
| ATOM | 17746 | O | HOH | W | 169 | 54.251 | −10.331 | 7.262 | 1.00 | 44.60 | W | O |
| ATOM | 17749 | O | HOH | W | 170 | 55.713 | −14.623 | −10.880 | 1.00 | 27.94 | W | O |
| ATOM | 17752 | O | HOH | W | 171 | 34.828 | 7.528 | 15.394 | 1.00 | 23.35 | W | O |
| ATOM | 17755 | O | HOH | W | 172 | 30.137 | −4.012 | 5.182 | 1.00 | 32.68 | W | O |
| ATOM | 17758 | O | HOH | W | 173 | 38.389 | −13.593 | −1.858 | 1.00 | 55.11 | W | O |
| ATOM | 17761 | O | HOH | W | 174 | 36.850 | −1.221 | 17.151 | 1.00 | 23.53 | W | O |
| ATOM | 17764 | O | HOH | W | 175 | 38.073 | −28.751 | 3.642 | 1.00 | 47.59 | W | O |
| ATOM | 17767 | O | HOH | W | 176 | 36.616 | −30.178 | 2.331 | 1.00 | 40.67 | W | O |
| ATOM | 17770 | O | HOH | W | 177 | 42.744 | −37.262 | 9.632 | 1.00 | 29.50 | W | O |
| ATOM | 17773 | O | HOH | W | 178 | 42.616 | −35.921 | 11.849 | 1.00 | 42.95 | W | O |
| ATOM | 17776 | O | HOH | W | 179 | 57.767 | −25.689 | −1.640 | 1.00 | 31.54 | W | O |
| ATOM | 17779 | O | HOH | W | 180 | 78.821 | 47.464 | −4.619 | 1.00 | 41.91 | W | O |
| ATOM | 17782 | O | HOH | W | 181 | 72.583 | 36.467 | −26.619 | 1.00 | 34.41 | W | O |
| ATOM | 17785 | O | HOH | W | 182 | 58.768 | 41.958 | −26.296 | 1.00 | 36.05 | W | O |
| ATOM | 17788 | O | HOH | W | 183 | 58.524 | 37.308 | −31.915 | 1.00 | 27.65 | W | O |
| ATOM | 17791 | O | HOH | W | 184 | 59.204 | 34.222 | −32.284 | 1.00 | 31.17 | W | O |
| ATOM | 17794 | O | HOH | W | 185 | 67.396 | 24.341 | −21.206 | 1.00 | 28.49 | W | O |
| ATOM | 17797 | O | HOH | W | 186 | 73.538 | 21.133 | −16.293 | 1.00 | 20.45 | W | O |
| ATOM | 17800 | O | HOH | W | 187 | 85.397 | 37.797 | −17.665 | 1.00 | 32.53 | W | O |
| ATOM | 17803 | O | HOH | W | 188 | 63.942 | 25.997 | −4.112 | 1.00 | 54.26 | W | O |
| ATOM | 17806 | O | HOH | W | 189 | 53.679 | 16.888 | −7.621 | 1.00 | 33.46 | W | O |
| ATOM | 17809 | O | HOH | W | 190 | 34.187 | 3.648 | −33.715 | 1.00 | 31.20 | W | O |
| ATOM | 17812 | O | HOH | W | 191 | 38.654 | −3.056 | −28.664 | 1.00 | 31.71 | W | O |
| ATOM | 17815 | O | HOH | W | 192 | 36.665 | 19.812 | −19.436 | 1.00 | 30.48 | W | O |
| ATOM | 17818 | O | HOH | W | 193 | 38.939 | 22.647 | −22.845 | 1.00 | 25.48 | W | O |
| ATOM | 17821 | O | HOH | W | 194 | 33.628 | 27.331 | −38.304 | 1.00 | 38.64 | W | O |
| ATOM | 17824 | O | HOH | W | 195 | 41.094 | 33.581 | −28.770 | 1.00 | 21.68 | W | O |
| ATOM | 17827 | O | HOH | W | 196 | 37.378 | 31.618 | −27.424 | 1.00 | 46.50 | W | O |
| ATOM | 17830 | O | HOH | W | 197 | 37.702 | 28.581 | −29.110 | 1.00 | 25.65 | W | O |
| ATOM | 17833 | O | HOH | W | 198 | 60.016 | 20.154 | −7.770 | 1.00 | 31.81 | W | O |
| ATOM | 17836 | O | HOH | W | 199 | 44.586 | 28.481 | 1.221 | 1.00 | 33.43 | W | O |
| ATOM | 17839 | O | HOH | W | 200 | 38.150 | 20.885 | −9.839 | 1.00 | 37.13 | W | O |
| ATOM | 17842 | O | HOH | W | 201 | 44.203 | 35.043 | −19.031 | 1.00 | 37.68 | W | O |
| ATOM | 17845 | O | HOH | W | 202 | 43.620 | 33.989 | −22.475 | 1.00 | 31.80 | W | O |
| ATOM | 17848 | O | HOH | W | 203 | 56.689 | 23.953 | −42.205 | 1.00 | 38.64 | W | O |
| ATOM | 17851 | O | HOH | W | 204 | 59.706 | 41.117 | −16.030 | 1.00 | 22.92 | W | O |
| ATOM | 17854 | O | HOH | W | 205 | 55.135 | 39.948 | −8.848 | 1.00 | 53.09 | W | O |
| END | | | | | | | | | | | | |

Example 5

Engineering *Populus alba* Isoprene Synthase for Improved Activity

This example described methods to identify *P. alba* isoprene synthase (IspS) variants with increased activity, sites for protein engineering studies were chosen based on the crystal structure of the enzyme. Twenty-five site evaluation libraries (SELs) were analyzed for specific activity, and subsequently ranked according to their performance relative to controls.

I. SEL Plasmid Backbone

Figure 39:
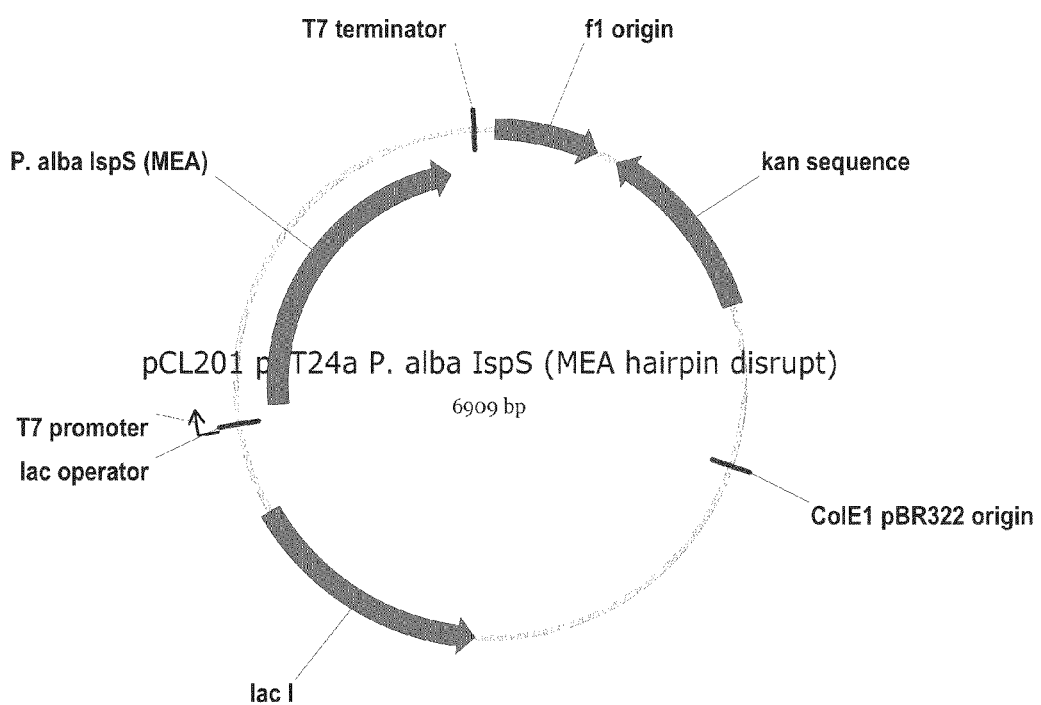
FIG. 39 provides a map of plasmid pCL201 (pET24a *P. alba* IspS (MEA hairpin disrupt)).

The plasmid backbone used to generate the 25 SELs was constructed by QuikChange (Stratagene) PCR on the template pDu39 (see U.S. patent application Ser. No. 12/429, 143). The PCR reaction mixtures were as follows: 1 µl pDu39, 5 µl 10×PfuUltra HF buffer, 1 µl dNTPs, 1 µl (50 µM) MEA Hairpin Disrupt (pET) F (Table 4-1), 1 µl (50 µM) MEA Hairpin Disrupt (pET) R (Table 5-1), 2 µl DMSO, 39 µl diH$_2$O, 1 µl PfuUltra HF Polymerase (Stratagene). The PCR Cycling Parameters for QuikChange were as follows: 1. 95° C. 1 min, 2. 95° C. 50 sec, 3. 60° C. 50 sec, 4, 68° C. 7 min, 5. Repeat steps 2-4 for 18 cycles, 6. 68° C. 7 min. The PCR product was treated with 1 µl DpnI (Roche) for 3 hours, and then 1 µl of the entire reaction was transformed into chemically competent *E. coli* Top10 cells (Invitrogen), recovered, and plated according to the manufacturer's recommendations. The next day, positive colonies were chosen for growth, plasmid purification (Qiagen) and sequencing (Quintara Biosciences). Plasmids which harbored the correct base changes introduced using the Quikchange Site-Directed Mutagenesis Kit (Stratagene) were selected for sequencing of the entire open reading frame to confirm the integrity of the coding sequence. One of these plasmids, pCL201 (see FIGS. 39-41), was selected as the backbone for construction of the 25 SELs (Verdezyne).

II. 25 Site Evaluation Libraries

Figure 42:
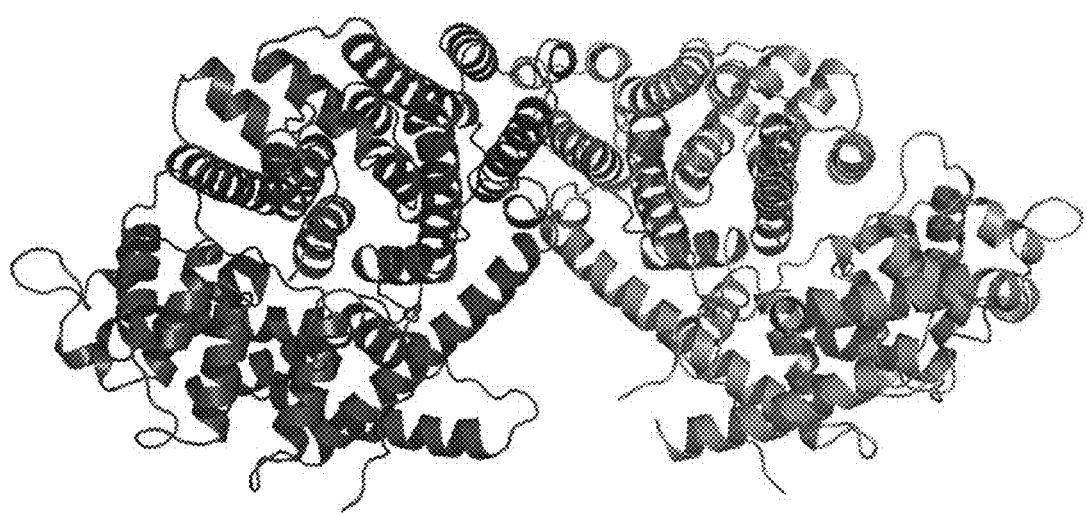
FIG. 42 provides the three-dimensional structure of *P. alba* IspS shown as a dimer. Chain A is in dark gray and chain B is in light gray.
Figure 43:
FIG. 43 provides a monomer view of the structure of *P. alba* IspS.
Figure 44:
FIG. 44 provides a view of the structure of 25 sites chosen for SEL in stick diagram on the ribbon diagram backbone of the *P. alba* IspS monomer.
Figure 46:
FIG. 46 provides the location of surface hydrophobic residue sites 469 and 494 of *P. alba* IspS.
Figure 47:
FIG. 47 provides the location of flexible loop residue sites 443, 453 and 515 of *P. alba* IspS.
Figure 48:
FIG. 48 provides the location of negatively charged residue site 323 of *P. alba* IspS dimer.
Figure 49:
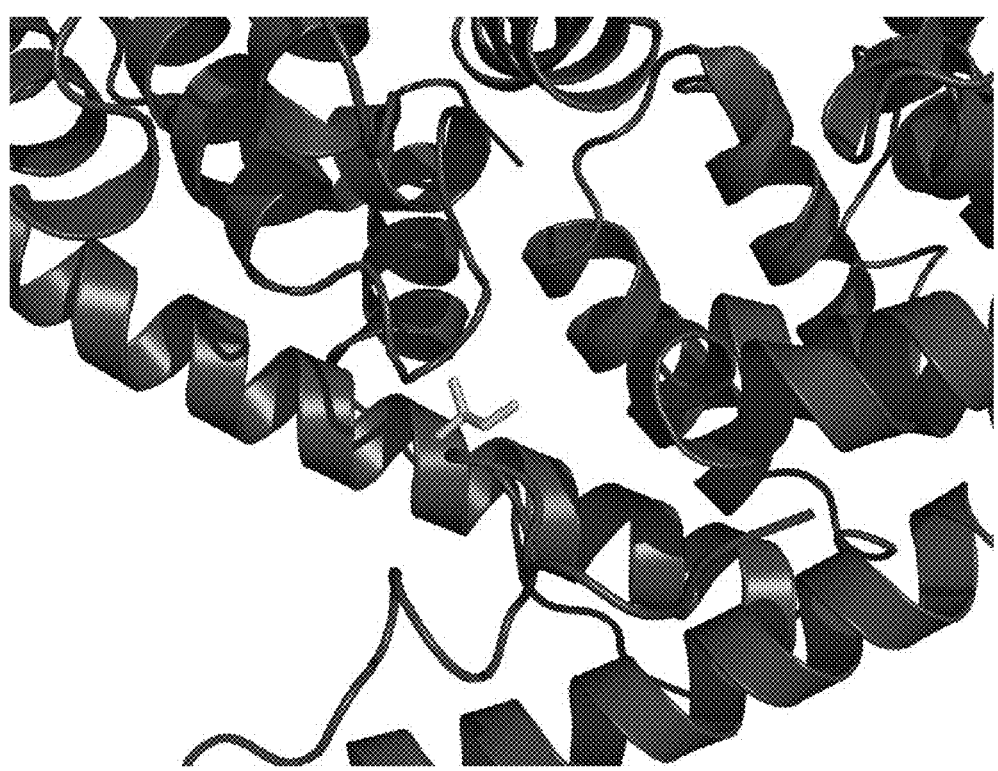
FIG. 49 provides the location of hinge residue site 229 of the *P. alba* IspS.
Figure 50:
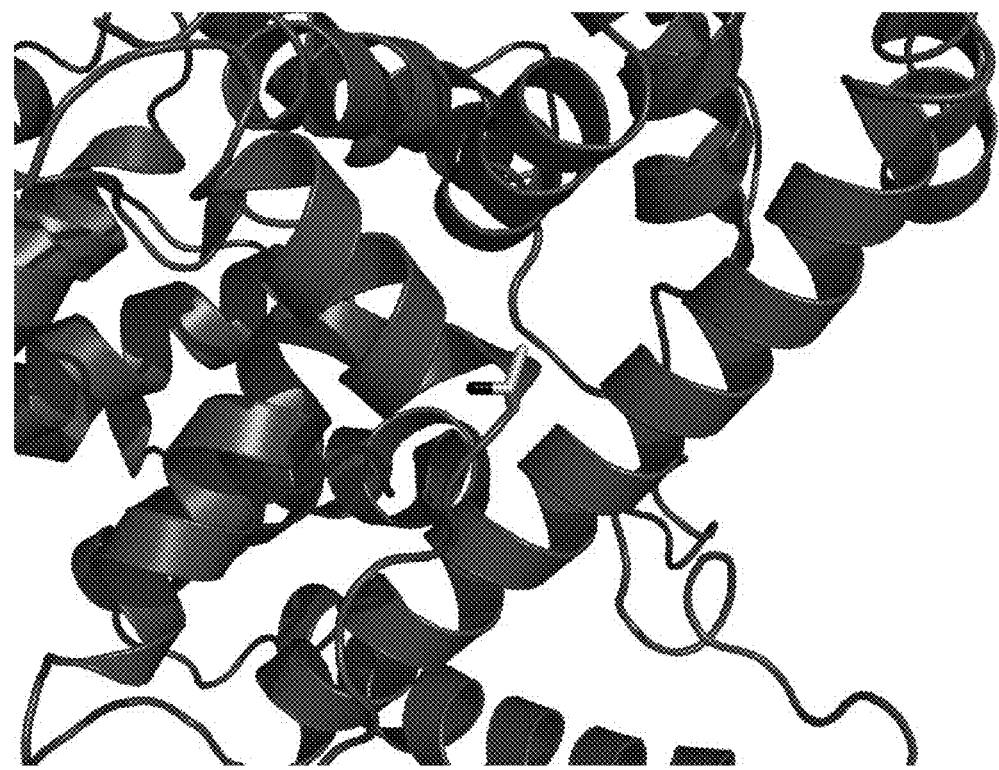
FIG. 50 provides the location of site 536 of *P. alba* IspS.

Sites for the 25 SELs were chosen based upon the crystal structure of *P. alba* IspS (Example 4). Table 5-2 lists all sites and a description of their putative role within the enzyme. Alterations in surface hydrophobic residues may affect protein folding, solubility or activity. Sites in the "hinge region" are located in a helix that spans the N-terminus and the C-terminus, and may dictate how those two halves of the enzyme interact with each other. Sites in the "negatively charged area" are in a region of the protein with a high density of acidic residues, which may somehow regulate activity. Sites within the "flexible loops" are proximal to the active site, and may affect substrate binding, as would sites that are directly within the active site (see Table 5-2). FIG. 42 shows the structure of an IspS dimer, and FIG. 43 shows a monomer. FIG. 44 shows all 25 sites chosen for SELs in stick diagram on the ribbon diagram backbone of the IspS monomer. SELs were generated in the pCL201 plasmid backbone. Plasmids harboring IspS variants were transformed into BL21 DE3 pLysS (Invitrogen) and delivered as glycerol stocks for subsequent growth and screening. FIG. 45 shows the layout of a typical 96-well plate containing 4 complete libraries to be screened for isoprene production and protein concentration. In some cases, where a specific substitution could not be isolated, the wild type codon was substituted instead.

TABLE 5-2

Sites for SEL

| Description | Sites for SEL |
| --- | --- |
| Surface hydrophobic residues | I28, V30, L130, G153, V299, L303, L469, L494 |
| Hinge region | R198, I229, L260 |
| Negatively charged area | D311, D323 |
| Flexible loops | A443, A453, N454, H515, A519, E525 |
| Active site | F388, N438, E451 |
| Miscellaneous | D345, R528, T536 |

III. DMAPP Assay

A) Growth and Induction

1. Prepared Patch Plates from Glycerol Stock Plates. Using a V&S 96 pin Replication Tool, cultures were patched onto a LB Agar 35 CMP/50 Kan large patch plates from overnight glycerol stock plates. Plates were incubated at 30° C. overnight for 20 to 24 hr. Cultures can be stored at 4° C. for up to a week.

TABLE 5-1

Primer sequences

| | |
| --- | --- |
| MEA Hairpin Disrupt (pET) F | ggagatatacatatggaagcacgtcgctctgcgaactacgaacctaa (SEQ ID NO: 46) |
| MMEA Hairpin Disrupt (pET) R | ttaggttcgtagttcgcagagcgacgtgcttccatatgtatatctcc (SEQ ID NO: 47) |
| T7 Forward | taatacgactcactataggg (SEQ ID NO: 48) |
| T7 Reverse | gctagttattgctcagcgg (SEQ ID NO: 49) |
| 1000 | gcactgtctttccgtctgctgc (SEQ ID NO: 50) |
| QB1493 | cttcggcaacgcatggaaat (SEQ ID NO: 51) |
| A-rev | ctcgtacaggctcaggatag (SEQ ID NO: 52) |
| A-rev2 | ttacgtcccaacgctcaact (SEQ ID NO: 53) |

2. Prepared Overnight Growth Plates. 500 mL of LB 35 CMP/50 Kan media were prepared. 300 µL/well of LB 35 CMP/50 Kan media were dispensed into deep 96 well plates (VWR). Using a V&S Replication Tool, the patch inoculum was transferred into deep 96 well plate by touching the tool pins to respective patch and using a circular motion to coat the pins with inoculum. The media was inoculated by dipping the tool then shaking the pin within the well. The overnight growth plates were sealed using a Breathe-Easier Sealing Membrane (Diversified Biotech). The plates were incubated in a Vertiga Shaking Incubator at 30° C. with shaking at 800 rpm overnight for 16 to 18 hr.

3. Prepared Day Growth Plate. Deep 96 well plates were prepared by dispensing 588 µL/well of LB 35 CMP/50 Kan media. Overnight growth plates were removed from the incubator. Overnight cultures were diluted 50-fold and 12 µL of overnight culture were transferred to day growth plates containing 588 µL/well of LB media containing antiobiotics. Overnight growth plates were sealed with new Breathe-Easier Sealing Membranes. Cultures were incubated at 30° C. and 800 rpm for 2.5 hr. Frozen 12 mM IPTG (Sigma) vials were removed from –20° C. and placed in a hood to thaw.

4. $OD_{600}$ Plate Read of Overnight, Induction, and Harvest. 150 µL 1×PBS were dispensed into 96 well Costar Read Plates (#9017). 50 µL of culture samples were transferred to Read Plates. The $OD_{600}$ reading was recorded using a Spectramax Plate Reader (Molecular Devices).

5. Induction. Electronic multi-channel pipettors were prepared to dispense 4×20 µL/well of IPTG (if 4× replicates). The multi-dispense option in the electronic pipettor was adjusted if more replicates was necessary. Thawed 12 mM IPTG was poured into 50 mL or 100 mL sterile reservoirs. 20 µL/well of IPTG into each 600 µL/well culture. Overnight growth plates were resealed. Cultures were incubated at 30° C. and 800 rpm for 4 hr. $OD_{600}$ readings of plates were recorded according instructions above.

6. Harvest. 400 µL of induced culture were transferred to 800 µL Grenier storage plates. Plates were centrifuged at 3300 rpm for 20 min at 2° to 8° C. in a low speed benchtop centrifuge. Supernatants were discarded, pellets should stay in the conical bottom well. Residual supernatants were slapped out onto a paper towel on the benchtop. Plates were sealed with an aluminum foil membrane (Beckman-Coulter). Plates were covered with a plastic plate lid if available. Storage plates were labeled accordingly and stored frozen at –80° C.

B) DMAPP Assay

Plates containing induced cell pellets were removed from the –80° C. freezer and allowed to thaw on the benchtop for 30 minutes prior to lysis. 200 µl of lysis buffer (50 mM Tris pH 8, 25 mM $MgCl_2$, 74 µg/ml DNase I, 250 U/ml lysozyme, 0.1% Tween 20, 0.5 mM PMSF) was added to each pellet, and plates were incubated on an Eppendorf Thermomixer at 25° C. for 30 minutes at 1200 rpm. After lysis, plates were centrifuged at 3450 rpm for 15 minutes at 4° C. Supernatants were then removed and diluted 10-fold prior to DMAPP assay. 80 µl of the diluted supernatant was added to 20 µl of the DMAPP working stock (20 mM DMAPP in 0.1 M Phosphate Buffer pH 8.2, DMAPP triammonium salt, Cayman chemicals) in a Zinsser glass block. Blocks were then sealed with aluminum sealing membranes, and incubated in Thermomixers at 25° C. for 30 minutes at 450 rpm. Reactions were stopped by incubating blocks on Thermomixers at 70° C. for 12 minutes at 450 rpm. GC-MS was then used for headspace measurements to calculate the amount of isoprene produced by each lysates.

Headspace Assay. A sample of 200 µl of the desired culture is inoculated into 2 ml CTC headspace vials (Agilent vial Catalog No. 5188 2753, and cap Catalog No. 5188 2759). The cap was screwed on tightly and the vials were incubated at 37° C. with shaking at 250 rpm. After 30 minutes the vials were removed from the incubator and cooled briefly with ambient tap water. The vials were placed into the CombiPal Headspace auto sampler for analysis by GC-MS. The analysis was performed using an Agilent 6890 GC/MS system interfaced with a CTC Analytics CombiPAL autosampler operating in headspace mode. An Agilent HP-5MS GC/MS column (30 m×0.25 mm; 0.25 µm film thickness) was used for separation of analytes. The sampler was set up to inject 500 µL of headspace gas. The GC/MS method utilized helium as the carrier gas at a flow of 1 ml/min. The injection port was held at 250° C. with a split ratio of 50:1. The oven temperature was held at 37° C. for the 2 min duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 µg/L to 200 µg/L. The limit of detection was estimated to be 50-100 ng/L using this method.

IV. Rapid ELISA Protocol Using 96-Well PVDF Filter Plates:

Frozen liquid alkaline phosphatase substrate was removed from the freezer and allowed to come to room temperature. PVDF plates (Millipore, Whatman) are pre-wetted by adding 50 µl 50% MeOH per well. Calibration curve samples are prepared in blue PCR plates (Bio-Rad plates are good for low volumes). Normally, 10 µl of 100 ug/ml standard was added to 90 µl TBSD for 1:10 dilution, followed by 1:2 serial dilutions in TBSD. TBSD was 50 mM Tris pH 8, 150 mM NaCl, 0.1% Na deoxycholate (from a 10% w/v solution in 50% EtOH stock), 0.05% Na azide). Samples were prepared in one or more dilutions in blue PCR plate (or suitable low volume plate). 100 µl $H_2O$ was added to PVDF plate and removed by vacuum and washed with $H_2O$ (2×100 µl). A microtiter plate vacuum manifold, set for 10-15 in. Hg vacuum, was used. 50 µl TBSD was added to PVDF plate. Calibrators and samples were added to the PVDF plate, usually in duplicate, allowed to sit 5 min. or longer, and then removed by vacuum. 50 µl blocking buffer (TBST+1% BSA; TBST was 50 mM Tris pH 8, 150 mM NaCl, 0.1% Tween 80, 0.05% Na azide) was added to the PVDF plate and let sit 15 min. or longer. 1° antibody was prepared in blocking buffer (about 1:2000 dilution, depending on target). 2° antibody in blocking buffer (normally goat anti-rabbit alkaline phospahatase conjugate, 1:2000 dilution). PVDF plate was vacuumed and 50 µl 1° antibody was added. The plate was allowed to sit for 5 min. or longer and then vacuumed. The plate was washed 4 times with 200 µl TBST. The 2° antibody was added at a 1:2000 dilution and allowed to sit for 5 min. or longer and then the 2° antibody was removed by vacuum. The plate was washed 4 times with 200 µl TBST. 120 µl of Alkaline phosphatase substrate solution, p-nitrophenyl phosphate liquid substrate (Sigma #N7653), was added to the plate. Color development was monitored and stop reaction when appropriate, normally 10-30 min. The color reaction was stopped by transferring 80 µl to a clear microtiter plate, or by adding 50 µl 3N NaOH followed by transferring 130 µl to clear microtiter plate. The absorbance of each reaction was read in plate reader at 405 nm. Data was exported as a .txt file and imported into an Excel spreadsheet. The average of calibrator replicates was calculated and standard curves were plotted as $A_{405}$ (x-axis) and µg/ml (y-axis). Best curve fit were determined using linear, power, or exponential algorithms. For best results, only the calibrator range that corresponded to the sample range was used. Because Excel may have difficulty with the entire calibrator range, multiple smaller ranges may be used. Best curve fit equations were used to calculate concentrations of samples. Optimum antibody concentrations were determined empirically. Usual concentrations ran between 1:1000 and 1:8000, but results may vary with target immunogenicity, animal response, and assay concentration range.

V. Results

Site evaluation libraries were screened for specific activity. The performance of variant molecules was determined by activity on a substrate dimethylallyldiphosphate (DMAPP) per unit weight of the molecule (see above). Variant molecules were ranked relative to the parental molecule. The performance index was calculated as activity per unit weight relative to the parental molecule. The parental molecule had a performance index of one, by definition. Activity of the parental molecule was calculated as the average of 22-24 assays of the parental molecule. A performance index greater than one indicates an improved molecule.

The positions of some high performing variants mapped onto the crystal structure of *P. alba* IspS are shown in FIGS. 46 through 50. These include but are not limited to sites 469 and 494 (surface hydrophobic, see Table 5-2 and FIG. 46), 443, 453, and 515 (flexible loops, see Table 5-2 and FIG. 47), 323 (negatively charged area, see Table 5-2 and FIG. 48), 229 (hinge region, see Table 5-2 and FIG. 49), and 536 (miscellaneous, see Table 5-2 and FIG. 50). The specific amino acid changes at these sites include but are not limited to I229V, I229L, D323M, A443S, A453I, A453L, A453N, L469A, L494C, L494G, L494I, L494P, L494V, H515M, T536F, T536Y, T536V, T536I, T536M, T536H, T536C, and T536L. Table 5-3 shows a list of variants at sites based on performance index.

Sites 198, 438, and 451 have a low tolerance for substitution as evidenced by all variants displaying reduced specific activity. Similarly, site 528 shows a low tolerance for substitution, with only a conservative variant lysine residue producing activity similar to the parental arginine.

TABLE 5-3

Performance indices of variants

| site | variant | performance index |
|---|---|---|
| I28 | W | 1.53 |
| I28 | T | 1.25 |
| I28 | R | 1.05 |
| I28 | Y | 1.02 |
| I28 | G | 0.93 |
| I28 | F | 0.84 |
| I28 | S | 0.75 |
| I28 | N | 0.73 |
| I28 | V | 0.72 |
| I28 | M | 0.72 |
| I28 | P | 0.71 |
| I28 | A | 0.71 |
| I28 | L | 0.68 |
| I28 | E | 0.59 |
| I28 | D | 0.57 |
| I28 | C | 0.53 |
| L130 | W | 1.54 |
| L130 | K | 1.54 |
| L130 | S | 1.48 |
| L130 | Y | 1.37 |
| L130 | R | 1.30 |
| L130 | V | 1.22 |
| L130 | I | 1.20 |
| L130 | E | 1.06 |
| L130 | D | 1.04 |
| L130 | Q | 0.96 |
| L130 | G | 0.95 |
| L130 | A | 0.93 |
| L130 | M | 0.87 |
| L130 | C | 0.81 |
| L130 | P | 0.43 |
| I229 | V | 4.41 |
| I229 | L | 3.77 |
| I229 | C | 1.35 |
| I229 | T | 1.33 |
| I229 | P | 1.22 |
| I229 | N | 1.04 |
| I229 | S | 0.92 |
| I229 | W | 0.85 |
| I229 | Q | 0.69 |
| I229 | F | 0.60 |
| I229 | M | 0.56 |
| I229 | E | 0.54 |
| I229 | A | 0.48 |
| I229 | H | 0.47 |
| I229 | G | 0.45 |
| I229 | Y | 0.42 |
| I229 | K | 0.24 |
| I229 | D | 0.17 |
| I229 | R | 0.07 |
| R198 | D | 0.68 |
| R198 | G | 0.39 |
| R198 | V | 0.36 |
| R198 | T | 0.19 |
| R198 | S | 0.15 |
| R198 | H | 0.15 |
| R198 | A | 0.11 |
| R198 | C | 0.11 |
| R198 | I | 0.10 |
| R198 | M | 0.09 |
| R198 | N | 0.03 |
| R198 | F | 0.02 |
| R198 | Y | 0.02 |
| R198 | H | 0.01 |
| R198 | L | 0.01 |
| D311 | M | 3.10 |
| D311 | F | 1.46 |
| D311 | L | 1.23 |
| D311 | G | 1.22 |
| D311 | I | 1.21 |
| D311 | A | 1.12 |
| D311 | T | 1.10 |
| D311 | R | 1.08 |
| D311 | V | 1.06 |
| D311 | E | 1.02 |
| D311 | K | 0.95 |
| D311 | S | 0.89 |
| D311 | W | 0.82 |
| D311 | Q | 0.67 |
| D345 | Y | 0.84 |
| D345 | I | 0.73 |
| D345 | K | 0.69 |
| D345 | L | 0.65 |
| D345 | E | 0.61 |
| D345 | N | 0.58 |
| D345 | T | 0.56 |
| D345 | Q | 0.56 |
| D345 | G | 0.55 |
| D345 | V | 0.51 |
| D345 | A | 0.50 |
| D345 | W | 0.46 |
| D345 | C | 0.43 |
| D345 | M | 0.43 |
| D345 | S | 0.41 |
| D345 | R | 0.40 |
| D345 | P | 0.35 |
| A443 | S | 1.79 |
| A443 | G | 1.28 |
| A443 | R | 1.19 |
| A443 | Q | 1.01 |
| A443 | H | 0.28 |
| A443 | L | 0.27 |
| A443 | N | 0.24 |
| A443 | F | 0.24 |
| A443 | I | 0.18 |
| A443 | V | 0.18 |
| A443 | T | 0.12 |
| A443 | P | 0.10 |
| F388 | L | 1.06 |
| F388 | Y | 0.88 |

TABLE 5-3-continued

Performance indices of variants

| site | variant | performance index |
|---|---|---|
| F388 | H | 0.73 |
| F388 | P | 0.26 |
| F388 | K | 0.25 |
| F388 | S | 0.25 |
| F388 | T | 0.25 |
| F388 | Q | 0.18 |
| F388 | V | 0.15 |
| F388 | G | 0.10 |
| F388 | R | 0.09 |
| F388 | C | 0.09 |
| F388 | D | 0.09 |
| F388 | A | 0.08 |
| N454 | S | 0.49 |
| N454 | G | 0.33 |
| N454 | H | 0.28 |
| N454 | T | 0.24 |
| N454 | D | 0.20 |
| N454 | A | 0.15 |
| N454 | E | 0.14 |
| N454 | Q | 0.11 |
| N454 | L | 0.05 |
| N454 | W | 0.05 |
| N454 | F | 0.03 |
| N454 | I | 0.03 |
| N454 | Y | 0.02 |
| N454 | V | 0.02 |
| N454 | R | 0.02 |
| N454 | C | 0.02 |
| N454 | P | 0.02 |
| N454 | M | 0.02 |
| L469 | A | 1.45 |
| L469 | Q | 1.06 |
| L469 | S | 0.97 |
| L469 | L | 0.96 |
| L469 | R | 0.78 |
| L469 | I | 0.75 |
| L469 | V | 0.74 |
| L469 | C | 0.71 |
| L469 | H | 0.66 |
| L469 | T | 0.63 |
| L469 | F | 0.60 |
| L469 | N | 0.57 |
| L469 | Y | 0.47 |
| L469 | W | 0.42 |
| L469 | P | 0.35 |
| L469 | G | 0.01 |
| A519 | H | 1.41 |
| A519 | S | 1.27 |
| A519 | G | 1.21 |
| A519 | W | 1.17 |
| A519 | T | 1.12 |
| A519 | K | 0.93 |
| A519 | F | 0.78 |
| A519 | R | 0.61 |
| A519 | C | 0.60 |
| A519 | Q | 0.58 |
| A519 | E | 0.44 |
| A519 | Y | 0.42 |
| A519 | V | 0.40 |
| A519 | L | 0.39 |
| A519 | D | 0.23 |
| A519 | P | 0.04 |
| H515 | M | 2.00 |
| H515 | Q | 1.05 |
| H515 | N | 0.97 |
| H515 | R | 0.97 |
| H515 | G | 0.93 |
| H515 | H | 0.81 |
| H515 | Y | 0.75 |
| H515 | I | 0.72 |
| H515 | A | 0.71 |
| H515 | E | 0.64 |
| H515 | F | 0.59 |
| H515 | D | 0.59 |
| H515 | L | 0.58 |
| H515 | V | 0.56 |
| H515 | C | 0.50 |
| H515 | T | 0.50 |
| H515 | W | 0.43 |
| H515 | S | 0.38 |
| H515 | P | 0.03 |
| V30 | K | 1.06 |
| V30 | I | 0.90 |
| V30 | E | 0.86 |
| V30 | W | 0.85 |
| V30 | Y | 0.81 |
| V30 | G | 0.80 |
| V30 | F | 0.76 |
| V30 | Q | 0.72 |
| V30 | C | 0.72 |
| V30 | P | 0.67 |
| V30 | R | 0.65 |
| V30 | L | 0.65 |
| V30 | D | 0.64 |
| V30 | T | 0.61 |
| V30 | A | 0.60 |
| V30 | S | 0.60 |
| V30 | M | 0.57 |
| V30 | N | 0.53 |
| G153 | K | 1.19 |
| G153 | H | 1.18 |
| G153 | L | 1.16 |
| G153 | W | 1.08 |
| G153 | Y | 0.99 |
| G153 | N | 0.91 |
| G153 | R | 0.90 |
| G153 | S | 0.80 |
| G153 | Q | 0.79 |
| G153 | A | 0.75 |
| G153 | T | 0.74 |
| G153 | P | 0.72 |
| G153 | D | 0.72 |
| G153 | C | 0.69 |
| G153 | M | 0.68 |
| G153 | V | 0.64 |
| L260 | N | 1.12 |
| L260 | M | 1.10 |
| L260 | I | 1.04 |
| L260 | H | 0.93 |
| L260 | V | 0.67 |
| L260 | W | 0.40 |
| L260 | Q | 0.37 |
| L260 | A | 0.34 |
| L260 | P | 0.32 |
| L260 | Y | 0.30 |
| L260 | G | 0.22 |
| L260 | K | 0.15 |
| L260 | S | 0.11 |
| L260 | E | 0.07 |
| L260 | T | 0.05 |
| L260 | R | 0.05 |
| L260 | D | 0.03 |
| V299 | L | 0.978 |
| V299 | A | 0.346 |
| V299 | T | 0.318 |
| V299 | S | 0.130 |
| V299 | M | 0.115 |
| V299 | N | 0.101 |
| V299 | K | 0.068 |
| V299 | R | 0.061 |
| V299 | W | 0.056 |
| V299 | G | 0.050 |
| V299 | H | 0.042 |
| V299 | E | 0.040 |
| V299 | Y | 0.032 |
| V299 | D | 0.025 |
| V299 | P | 0.00 |
| D323 | M | 1.92 |
| D323 | W | 1.76 |
| D323 | Y | 1.38 |

TABLE 5-3-continued

Performance indices of variants

| site | variant | performance index |
|---|---|---|
| D323 | F | 1.33 |
| D323 | I | 1.27 |
| D323 | S | 1.22 |
| D323 | V | 1.10 |
| D323 | N | 1.07 |
| D323 | A | 1.03 |
| D323 | G | 1.03 |
| D323 | Q | 1.03 |
| D323 | K | 1.00 |
| D323 | T | 0.97 |
| D323 | L | 0.93 |
| D323 | C | 0.92 |
| D323 | R | 0.90 |
| D323 | E | 0.75 |
| L303 | I | 1.11 |
| L303 | M | 1.07 |
| L303 | V | 0.93 |
| L303 | C | 0.85 |
| L303 | S | 0.78 |
| L303 | E | 0.77 |
| L303 | W | 0.74 |
| L303 | T | 0.71 |
| L303 | P | 0.71 |
| L303 | H | 0.59 |
| L303 | Q | 0.58 |
| L303 | G | 0.55 |
| L303 | D | 0.54 |
| L303 | A | 0.52 |
| L303 | R | 0.49 |
| E451 | G | 0.16 |
| E451 | K | 0.15 |
| E451 | S | 0.14 |
| E451 | I | 0.13 |
| E451 | H | 0.13 |
| E451 | Q | 0.13 |
| E451 | V | 0.12 |
| E451 | L | 0.12 |
| E451 | F | 0.12 |
| E451 | Y | 0.12 |
| E451 | W | 0.12 |
| E451 | T | 0.12 |
| E451 | D | 0.12 |
| E451 | R | 0.11 |
| E451 | N | 0.10 |
| E451 | C | 0.09 |
| E451 | A | 0.09 |
| E451 | P | 0.08 |
| N438 | W | 1.02 |
| N438 | K | 0.34 |
| N438 | P | 0.31 |
| N438 | I | 0.29 |
| N438 | R | 0.28 |
| N438 | V | 0.20 |
| N438 | Q | 0.20 |
| N438 | L | 0.19 |
| N438 | M | 0.18 |
| N438 | S | 0.17 |
| N438 | H | 0.16 |
| N438 | Y | 0.15 |
| N438 | F | 0.14 |
| N438 | T | 0.13 |
| N438 | C | 0.12 |
| N438 | E | 0.12 |
| N438 | G | 0.11 |
| N438 | A | 0.11 |
| N438 | D | 0.11 |
| L494 | P | 2.64 |
| L494 | C | 1.89 |
| L494 | I | 1.71 |
| L494 | V | 1.57 |
| L494 | S | 1.38 |
| L494 | G | 1.30 |
| L494 | D | 1.04 |
| L494 | E | 0.87 |
| L494 | H | 0.70 |
| L494 | K | 0.68 |
| L494 | Y | 0.66 |
| L494 | Q | 0.63 |
| L494 | N | 0.58 |
| L494 | R | 0.41 |
| L494 | A | 0.39 |
| L494 | W | 0.37 |
| L494 | T | 0.08 |
| A453 | N | 2.99 |
| A453 | I | 1.77 |
| A453 | V | 1.08 |
| A453 | T | 0.53 |
| A453 | Y | 0.43 |
| A453 | E | 0.39 |
| A453 | H | 0.37 |
| A453 | F | 0.35 |
| A453 | C | 0.35 |
| A453 | S | 0.34 |
| A453 | W | 0.22 |
| A453 | R | 0.21 |
| A453 | D | 0.10 |
| A453 | K | 0.05 |
| A453 | P | 0.03 |
| A453 | G | 0.02 |
| E525 | S | 1.62 |
| E525 | T | 1.25 |
| E525 | R | 1.24 |
| E525 | K | 1.22 |
| E525 | V | 1.17 |
| E525 | H | 1.09 |
| E525 | L | 1.07 |
| E525 | F | 1.05 |
| E525 | W | 1.05 |
| E525 | Q | 1.05 |
| E525 | G | 1.00 |
| E525 | M | 0.95 |
| E525 | C | 0.92 |
| E525 | A | 0.91 |
| E525 | P | 0.74 |
| E525 | N | 0.71 |
| E525 | D | 0.68 |
| R528 | K | 1.00 |
| R528 | F | 0.58 |
| R528 | H | 0.49 |
| R528 | M | 0.46 |
| R528 | V | 0.45 |
| R528 | L | 0.25 |
| R528 | Y | 0.23 |
| R528 | T | 0.21 |
| R528 | C | 0.21 |
| R528 | E | 0.20 |
| R528 | S | 0.17 |
| R528 | A | 0.16 |
| R528 | N | 0.15 |
| R528 | G | 0.11 |
| R528 | W | 0.07 |
| R528 | D | 0.05 |
| R528 | P | 0.02 |
| T536 | F | 3.60 |
| T536 | Y | 2.62 |
| T536 | V | 2.56 |
| T536 | I | 2.44 |
| T536 | M | 1.62 |
| T536 | H | 1.50 |
| T536 | C | 1.48 |
| T536 | L | 1.43 |
| T536 | K | 1.37 |
| T536 | A | 1.31 |
| T536 | S | 1.29 |
| T536 | G | 1.04 |
| T536 | R | 0.96 |
| T536 | N | 0.55 |
| T536 | E | 0.22 |

TABLE 5-3-continued

Performance indices of variants

| site | variant | performance index |
|---|---|---|
| T536 | D | 0.18 |
| T536 | P | 0.05 |

The entire library of T536, variants from all SELs which displayed the highest performance indices, and some control variants which displayed low performance indices were re-assayed for activity as described above. Table 5-4 shows the results from these assays. Results are presented as performance vs. wild-type (unmodified) molecule. Wild-type performance was determined as the average of 51 separate grown cultures. Results were variable between assays but results were in very good agreement with the primary screen results, indicating the assay is reliable. Beneficial sites for variation include but are not limited to flexible loop sites A453, H515, and A443; hydrophobic surface sites L494 and L469 and miscellaneous site T536. The highest performing variants, i.e. those that displayed a performance index greater than 1.5, were A453N, T536C, L494P, T536I, T536F, T536Y, and L494C.

TABLE 5-4

Performance indices of following retest.

| site | variant | performance index |
|---|---|---|
| A453 | N | 2.31 |
| T536 | C | 1.88 |
| L494 | P | 1.82 |
| T536 | I | 1.73 |
| T536 | F | 1.73 |
| T536 | Y | 1.73 |
| L494 | C | 1.56 |
| T536 | A | 1.48 |
| L494 | V | 1.48 |
| T536 | K | 1.46 |
| T536 | L | 1.46 |
| L494 | G | 1.39 |
| T536 | R | 1.36 |
| H515 | M | 1.34 |
| A453 | I | 1.31 |
| T536 | V | 1.27 |
| A443 | S | 1.16 |
| L494 | I | 1.10 |
| T536 | M | 1.09 |
| L469 | A | 1.09 |
| D323 | M | 0.95 |
| T536 | H | 0.94 |
| T536 | G | 0.90 |
| I229 | V | 0.89 |
| I229 | L | 0.89 |
| T536 | S | 0.72 |
| T536 | N | 0.49 |
| T536 | D | 0.17 |
| T536 | E | 0.16 |
| E451 | S | 0.14 |
| R528 | D | 0.11 |
| N438 | E | 0.10 |
| E451 | I | 0.08 |
| T536 | P | 0.08 |
| R528 | P | 0.05 |

Example 6

P. alba Isoprene Synthase Combinatorial Analysis, Expression, Crystallization, Activity, and Tm The P. alba isoprene synthase (IspS) SEL and enrichment studies identified several independent mutations displaying higher in vitro activity than the wild type (WT) enzyme. The experiments described below were aimed to determine if these mutations were mutually beneficial in combination with one another, and to determine if there were additional beneficial biochemical properties of any of the more active variants.
Methods Three P. alba Isoprene Synthase (IspS) variants which demonstrated high performance index values relative to wild type in the SEL activity assay were chosen for further study. A fourth variant, previously isolated by a selection for randomly mutagenized IspS enzymes that tolerated protracted, high MVA pathway flux, was also included in the combinatorial analysis. These four variants harbored the mutations A453N, G491S (previously referred to as G507S), L494P, and T536C. In all possible combinations, these four mutations generated 16 possible variants of IspS. For ease of reference, the 16 variants to be assayed were annotated as containing the possible combinations of mutations N (A453N), S (G491S), P (L494P), or C (T536C), or WT (no mutations) in a given IspS molecule.

The 16 variants were based upon the vector backbone MD09-163 (encoding the WT enzyme, see FIG. 60), which harbors a TEV protease site and 6×His tag at the C-terminal end of IspS. Variants were generated using the QuikChange Multi Site-Directed Mutagenesis Kit (Stratagene) according to the manufacturer's recommended protocol (see below for PCR reaction and cycling parameters). Since the mutations encoding G491S and L494P are within six nucleotides of each other, it was necessary to use an oligonucleotide harboring both mutations in addition to the single oligonucleotides for those mutations in the QuikChange Multi reaction in order to generate all 16 possible combinations of mutations. The QuikChange Multi reaction was transformed into chemically competent E. coli TOP10 cells (Invitrogen) according to the manufacturer's recommended protocol and plated onto LB Kan50 selective media plates. Colonies resistant to kanamycin were directly screened by PCR and verified by sequencing using the primers QB1493 and T7 Reverse (Quintara Biosciences). In some cases, if a certain variant was not isolated from the QuickChange Multi reaction, a modified version of QuikChange Mutagenesis (Stratagene) was employed to generate a given variant (see below for PCR reaction and cycling parameters). These two techniques yielded all 16 possible combinatorial variants of N, S, P, or C, which were subjected to complete sequencing using the primers T7 Forward, EL-1000, QB1493, A-rev, A-rev2, and T7 Reverse (see Table 6-1). TOP10 cells were grown in selective medium, and plasmids were purified (Qiagen) and then transformed into chemically competent BL21 DE3 pLysS (Invitrogen) according to the manufacturer's recommended protocol, prior to expression of the IspS variants. All variants of IspS were purified and analyzed for specific activity relative to WT (see FIG. 62).

In a separate set of constructs, the T536F mutation (shown to be a thermostable variant of IspS) was also introduced into both the MD09-163 and pDW101 backbones. This mutation was introduced by the QuikChange mutagenesis methodology described above (see below for PCR reaction and cycling parameters), and similarly transformed into BL21 DE3 pLysS (Invitrogen) for expression. These variants were assayed for their effect on IspS expression and melting point relative to WT.
QuikChange Multi Site-Directed Mutagenesis
9 µl H₂O
2.5 µl 10× QuikChange Multi reaction buffer
0.5 µl QuikSolution
1 µl DNA template (100 ng MD09-163)
2 µl each primer (200 ng each of N, S, P, C, SP)
1 µl dNTP mix
1 µl QuikChange Multi enzyme blend
QuikChange Multi Site-Directed Mutagenesis—Cycling Parameters
1) 95° C.—4 min
2) 95° C.—1 min
3) 53° C.—1 min
4) 65° C.—14 min
5) goto Step 2—30×
6) 4° C.—for holding
QuikChange Mutagenesis (Modified)
35 µl H₂O
5 µl 10×Pfu Ultra II rxn Buffer
6 µl 2.5 mM dNTPs (Roche)
1 µl 20 µM Primer 1 (e.g. G507S QC 2 For or alba T536F For)
1 µl 20 µM Primer 2 (e.g. G507S QC 2 Rev or alba T536F Rev)
1 µl Pfu Ultra II HS Polymerase (Stratagene)
1 µl DNA template (e.g. 100 ng MD09-163 or pDW101)
QuikChange Mutagenesis—Cycling Parameters
1) 95° C.—4 min
2) 95° C.—20 sec
3) 52° C.—20 sec
4) 68° C.—7 min
5) goto Step 2—5×
6) 95° C.—20 sec
7) 55° C.—20 sec
8) 68° C.—7 min
9) goto Step 2—20×
10) 68° C.—10 min
11) 4° C.—for holding

TABLE 6-1

| Primers | |
|---|---|
| alba A453N For (N) | gcgcgtggtgaaaccaacaatagcgtttcttgttac (SEQ ID NO: 54) |
| QC G5075 For (S) | agatgaacaaggaaaaactgagtggtagcctgttcgcgaaa (SEQ ID NO: 55) |
| alba L494P For (P) | gaaaaactgggtggtagcccgttcgcgaaaccgttcg (SEQ ID NO: 56) |
| alba T536C For (C) | gttctgtctgtaatctgcgaaccgattctgccgtttg (SEQ ID NO: 57) |
| alba G491S L494P For (SP) | gaacaaggaaaaactgagtggtagcccgttcgcgaaaccgttcg (SEQ ID NO: 58) |
| G507S QC 2 For | gaaaaactgagtggtagcctgttcgcgaaac (SEQ ID NO: 59) |
| G507S QC 2 Rev | aggctaccactcagttttccttgttcatct (SEQ ID NO: 60) |
| alba T536F For | gttctgtctgtaatctttgaaccgattctgccgtttg (SEQ ID NO: 61) |
| alba T536F Rev | cggttcaaagattacagacagaacgcgtt (SEQ ID NO: 62) |
| T7 Forward | taatacgactcactataggg (SEQ ID NO: 48) |
| T7 Reverse | gctagttattgctcagcgg (SEQ ID NO: 49) |
| EL-1000 | gcactgtctttccgtctgctgc (SEQ ID NO: 50) |
| A-rev | ctcgtacaggctcaggatag (SEQ ID NO: 52) |
| A-rev-2 | ttacgtcccaacgctcaact (SEQ ID NO: 53) |
| QB1493 | cttcggcaacgcatggaaat (SEQ ID NO: 51) |

TABLE 6-2

| Plasmids: | |
|---|---|
| MD09-163 | pET24a-*P. alba* TRC (MEA WT) C-Term (+) TEV, His tag |
| pDW87 | pET24a-*P. alba* TRC (MEA T536F) C-Term (+) TEV, His tag |
| pDW95 | pET24a-*P. alba* TRC (MEA L494P T536F) C-Term (+) TEV, His tag |
| pDW99 | pET24a-*P. alba* TRC (MEA A453N) C-Term (+) TEV, His tag |
| pDW100 | pET24a-*P. alba* TRC (MEA G491S) C-Term (+) TEV, His tag |

TABLE 6-2-continued

| Plasmids: | |
|---|---|
| pDW101 | pET24a-*P. alba* TRC (MEA L494P) C-Term (+) TEV, His tag |
| pDW102 | pET24a-*P. alba* TRC (MEA T536C) C-Term (+) TEV, His tag |
| pDW103 | pET24a-*P. alba* TRC (MEA A453N G491S) C-Term (+) TEV, His tag |
| pDW104 | pET24a-*P. alba* TRC (MEA A453N L494P) C-Term (+) TEV, His tag |
| pDW105 | pET24a-*P. alba* TRC (MEA A453N T536C) C-Term (+) TEV, His tag |
| pDW106 | pET24a-*P. alba* TRC (MEA A453N G491S L494P) C-Term (+) TEV, His tag |
| pDW107 | pET24a-*P. alba* TRC (MEA A453N G491S T536C) C-Term (+) TEV, His tag |
| pDW108 | pET24a-*P. alba* TRC (MEA A453N L494P T536C) C-Term (+) TEV, His tag |
| pDW109 | pET24a-*P. alba* TRC (MEA A453N G491S L494P T536C) C-Term (+) TEV, His tag |
| pDW110 | pET24a-*P. alba* TRC (MEA G491S L494P) C-Term (+) TEV, His tag |
| pDW111 | pET24a-*P. alba* TRC (MEA G491S T536C) C-Term (+) TEV, His tag |
| pDW112 | pET24a-*P. alba* TRC (MEA G491S L494P T536C) C-Term (+) TEV, His tag |
| pDW113 | pET24a-*P. alba* TRC (MEA L494P T536C) C-Term (+) TEV, His tag |

TABLE 6-3

| Strains: | |
|---|---|
| MD09-167 | BL21(DE3) pLysS, MD09-163 (WT) |
| DW363 | BL21(DE3) pLysS, pDW87 |
| DW381 | BL21(DE3) pLysS, pDW95 |
| DW397 | BL21(DE3) pLysS, pDW99 (N) |
| DW398 | BL21(DE3) pLysS, pDW100 (S) |
| DW399 | BL21(DE3) pLysS, pDW101 (P) |
| DW400 | BL21(DE3) pLysS, pDW102 (C) |
| DW401 | BL21(DE3) pLysS, pDW103 (NS) |
| DW402 | BL21(DE3) pLysS, pDW104 (NP) |
| DW403 | BL21(DE3) pLysS, pDW105 (NC) |
| DW404 | BL21(DE3) pLysS, pDW106 (NSP) |
| DW405 | BL21(DE3) pLysS, pDW107 (NSC) |
| DW406 | BL21(DE3) pLysS, pDW108 (NPC) |
| DW407 | BL21(DE3) pLysS, pDW109 (NSPC) |
| DW408 | BL21(DE3) pLysS, pDW110 (SP) |
| DW409 | BL21(DE3) pLysS, pDW111 (SC) |
| DW410 | BL21(DE3) pLysS, pDW112 (SPC) |
| DW411 | BL21(DE3) pLysS, pDW1113 (PC) |

1) Amino Acid Sequence of *P. alba* MEA (+) TEV - MD09-163 (WT)

(SEQ ID NO: 63)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLGGSLFAKPFVETAINLARQSHCTYHNGDAHTSPDELTRKRVLSVITEPILPFERENLYFQG

LEHHHHHH

DNA sequence of MD09-163

(SEQ ID NO: 64)

tggcgaatgggacgcgccctgtagcggcgcattaagcgcggcgggtgtggtggttacgcgcagcgtgaccgctacacttgccagcgccctag cgcccgctccttcgctttcttcccttcctttctcgccacgttcgccggctttccccgtcaagctctaaatcgggggctccctttagggttc cgatttagtgctttacggcacctcgaccccaaaaaacttgattagggtgatggttcacgtagtgggccatcgccctgatagacggttttcg ccctttgacgttggagtccacgttcttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaaccccatttgtttattttttctaaatacattcaaatatgtatccgctcatgaa ttaattcttagaaaaactcatcgagcatcaaatgaaactgcaatttattcatatcaggattatcaataccatatttttgaaaaagccgtttc tgtaatgaaggagaaaactcaccgaggcagttccataggatggcaagatcctggtatcggtctgcgattccgactcgtccaacatcaataca -continued

```
acctattaatttcccctcgtcaaaaataaggttatcaagtgagaaatcaccatgagtgacgactgaatccggtgagaatggcaaaagtttat
gcatttctttccagacttgttcaacaggccagccattacgctcgtcatcaaaatcactcgcatcaaccaaaccgttattcattcgtgattgc
gcctgagcgagacgaaatacgcgatcgctgttaaaaggacaattacaaacaggaatcgaatgcaaccggcgcaggaacactgccagcgcatc
aacaatattttcacctgaatcaggatattcttctaatacctggaatgctgttttcccggggatcgcagtggtgagtaaccatgcatcatcag
gagtacggataaaatgcttgatggtcggaagaggcataaattccgtcagccagtttagtctgaccatctcatctgtaacatcattggcaacg
ctaccttttgccatgtttcagaaacaactctggcgcatcgggcttcccatacaatcgatagattgtcgcacctgattgcccgacattatcgcg
agcccatttataccatataaatcagcatccatgttggaatttaatcgcggcctagagcaagacgtttcccgttgaatatggctcataacac
cccttgtattactgtttatgtaagcagacagtttattgttcatgaccaaaatccttaacgtgagttttcgttccactgagcgtcagaccc
cgtagaaaagatcaaaggatcttcttgagatcctttttttctgcgcgtaatctgctgcttgcaaacaaaaaaaccaccgctaccagcggtgg
tttgtttgccggatcaagagctaccaactctttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagtggcga
taagtcgtgtcttaccgggttggactcaagacgatagttaccggataaggcgcagcggtcgggctgaacgggggggttcgtgcacacagccca
gcttggagcgaacgacctacaccgaactgagatacctacagcgtgagctatgagaaagcgccacgcttcccgaagggagaaaggcggacagg
tatccggtaagcggcagggtcggaacaggagagcgcacgagggagcttccaggggggaaacgcctggtatctttatagtcctgtcgggtttcg
ccacctctgacttgagcgtcgatttttgtgatgctcgtcagggggggcggagcctatggaaaaacgccagcaacgcggccttttttacggttcc
tggccttttgctggccttttgctcacatgttcttcctgcgttatcccctgattctgtggataaccgtattaccgcctttgagtgagctgat
accgctcgccgcagccgaacgaccgagcgcagcgagtcagtgagcgaggaagcggaagagcgcctgatgcggtattttctccttacgcatct
gtgcggtatttcacaccgcatatatggtgcactctcagtacaatctgctctgatgccgcatagttaagccagtatacactccgctatcgcta
cgtgactgggtcatggctgcgccccgacacccgccaacacccgctgacgcgccctgacgggcttgtctgctcccggcatccgcttacagaca
agctgtgaccgtctccgggagctgcatgtgtcagaggttttcaccgtcatcaccgaaacgcgcgaggcagctgcggtaaagctcatcagcgt
ggtcgtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaagggggatttctgttcatgggggtaatgataccgatgaa
acgagagaggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcacccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcgggagagg
cggtttgcgtattgggcgccagggtggtttttcttttcaccagtgagacgggcaacagctgattgcccttcaccgcctggccctgagagagt
tgcagcaagcggtccacgctggtttgccccagcaggcgaaaatcctgtttgatggtggttaacggcgggataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
```

-continued

```
actgtttgcccgccagttgttgtgccacgcggttgggaatgtaattcagctccgccatcgccgcttccacttttttcccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatgcaaggagat
ggcgcccaacagtcccccggccacggggcctgccaccatacccacgccgaaacaagcgctcatgagcccgaagtggcgagcccgatcttccc
catcggtgatgtcggcgatataggcgccagcaaccgcacctgtggcgccggtgatgccggccacgatgcgtccggcgtagaggatcgagatc
tcgatcccgcgaaattaatacgactcactatagggggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctgggttaccgtttcgagtctgatatccgtggtgcgctggatcgttcgtttcctccggcggct
tcgatgcggtaaccaagactccctgcacggtacggcactgtctttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggtctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttcttcgtaaccattatcgacgatatctacgatgtatacggcaccctg
gacgaactggagctgtttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgacctttgacgactacttcggcaacgcatggaaatcctct
tctggccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccgcaaatagcgttt
cttgttacatgcgcactaaaggtatctccgaagaactggctaccgaaagcgtgatgaatctgatcgatgaaacctggaaaaagatgaacaag
gaaaaactgggtggtagcctgttcgcgaaaccgttcgtggaaaccgcgatcaacctggcacgtcaatctcactgcacttatcataacggcga
cgcgcatacctctccggatgagctgacccgcaaacgcgttctgtctgtaatcactgaaccgattctgccgtttgaacgcgaaaacctgtatt
ttcagggcctcgagcaccaccaccaccaccactgagatccggctgctaacaaagcccgaaaggaagctgagttggctgctgccaccgctgag
caataactagcataacccccttggggcctctaaacgggtcttgaggggttttttgctgaaaggaggaactatatccggat
```

2) Amino Acid Sequence of *P. alba* MEA A453N (+) TEV - pDW99 (N)

(SEQ ID NO: 65)

MEARRSANYEPNSWDYDYLLSSDTDESIEVYKDKAKKLEAEVRREINNEKAEFLTLLELID
NVQRLGLGYRFESDIRGALDRFVSSGGFDAVTKTSLHGTALSFRLLRQHGFEVSQEAFSGF
KDQNGNFLENLKEDIKAILSLYEASFLALEGENILDEAKVFAISHLKELSEEKIGKELAEQVN
HALELPLHRRTQRLEAVWSIEAYRKKEDANQVLLELAILDYNMIQSVYQRDLRETSRWWR
RVGLATKLHFARDRLIESFYWAVGVAFEPQYSDCRNSVAKMFSFVTIIDDIYDVYGTLDEL
ELFTDAVERWDVNAINDLPDYMKLCFLALYNTINEIAYDNLKDKGENILPYLTKAWADLC
NAFLQEAKWLYNKSTPTFDDYFGNAWKSSSGPLQLVFAYFAVVQNIKKEEIENLQKYHDTI
SRPSHIFRLCNDLASASAEIARGETNNSVSCYMRTKGISEELATESVMNLIDETWKKMNKE
KLGGSLFAKPFVETAINLARQSHCTYHNGDAHTSPDELTRKRVLSVITEPILPFERENLYFQG
LEHHHHHH

DNA sequence of pDW99

(SEQ ID NO: 66)

```
tggcgaatgggacgcgccctgtagcggcgcattaagcgcggcgggtgtggtggttacgcgcagcgtgaccgctacacttgccagcgccctag
cgcccgctcctttcgctttcttcccttcctttctcgccacgttcgccggctttccccgtcaagctctaaatcgggggctcccttagggttc
```

```
cgatttagtgctttacggcacctcgaccccaaaaaacttgattagggtgatggttcacgtagtgggccatcgccctgatagacggttttcg ccctttgacgttggagtccacgttctttaatagtggactcttgttccaaactggaacaacactcaacccatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaaccccatttgtttattttctaaatacattcaaatatgtatccgctcatgaa ttaattcttagaaaaactcatcgagcatcaaatgaaactgcaatttattcatatcaggattatcaataccatattttgaaaaagccgtttc tgtaatgaaggagaaaactcaccgaggcagttccataggatggcaagatcctggtatcggtctgcgattccgactcgtccaacatcaataca acctattaatttccccctcgtcaaaaataaggttatcaagtgagaaatcaccatgagtgacgactgaatccggtgagaatggcaaaagtttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg ctacctttgccatgtttcagaaacaactctggcgcatcgggcttcccatacaatcgatagattgtcgcacctgattgcccgacattatcgcg agcccatttatacccatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc cgtagaaaagatcaaaggatcttcttgagatcctttttttctgcgcgtaatctgctgcttgcaaacaaaaaaaccaccgctaccagcggtgg tttgtttgccggatcaagagctaccaactcttttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga taagtcgtgtcttaccgggttggactcaagacgatagttaccggataaggcgcagcggtcgggctgaacggggggttcgtgcacacagccca gcttggagcgaacgacctacaccgaactgagatacctacagcgtgagctatgagaaagcgccacgcttcccgaagggagaaaggcggacagg tatccggtaagcggcagggtcggaacaggagagcgcacgagggagcttccaggggaaacgcctggtatctttatagtcctgtcgggtttcg ccacctctgacttgagcgtcgatttttgtgatgctcgtcaggggggcggagcctatggaaaaacgccagcaacgcggcctttttacggttcc tggccttttgctggccttttgctcacatgttcttcctgcgttatcccctgattctgtggataaccgtattaccgcctttgagtgagctgat accgctcgccgcagccgaacgaccgagcgcagcgagtcagtgagcgaggaagcggaagagcgcctgatgcggtattttctccttacgcatct gtgcggtatttcacaccgcatatatggtgcactctcagtacaatctgctctgatgccgcatagttaagccagtatacactccgctatcgcta cgtgactgggtcatggctgcgccccgacacccgccaacacccgctgacgcgccctgacgggcttgtctgctcccggcatccgcttacagaca agctgtgaccgtctccgggagctgcatgtgtcagaggttttcaccgtcatcaccgaaacgcgcgaggcagctgcggtaaagctcatcagcgt ggtcgtgaagcgattcacagatgtctgcctgttcatccgcgtccagctcgttgagtttctccagaagcgttaatgtctggcttctgataaag cgggccatgttaagggcggttttttcctgtttggtcactgatgcctccgtgtaagggggatttctgttcatgggggtaatgataccgatgaa acgagagaggatgctcacgatacgggttactgatgatgaacatgcccggttactggaacgttgtgagggtaaacaactggcggtatggatgc ggcgggaccagagaaaaatcactcagggtcaatgccagcgcttcgttaatacagatgtaggtgttccacagggtagccagcagcatcctgcg atgcagatccggaacataatggtgcagggcgctgacttccgcgtttccagactttacgaaacacggaaaccgaagaccattcatgttgttgc tcaggtcgcagacgttttgcagcagcagtcgcttcacgttcgctcgcgtatcggtgattcattctgctaaccagtaaggcaacccc gccagc ctagccgggtcctcaacgacaggagcacgatcatgcgcacccgtgggccgccatgccggcgataatggcctgcttctcgccgaaacgtttg gtggcgggaccagtgacgaaggcttgagcgagggcgtgcaagattccgaataccgcaagcgacaggccgatcatcgtcgcgctccagcgaaa gcggtcctcgccgaaaatgacccagagcgctgccggcacctgtcctacgagttgcatgataaagaagacagtcataagtgcggcgacgatag tcatgccccgcgcccaccggaaggagctgactgggttgaaggctctcaagggcatcggtcgagatcccggtgcctaatgagtgagctaactt acattaattgcgttgcgctcactgcccgctttccagtcgggaaacctgtcgtgccagctgcattaatgaatcggccaacgcgcgggagagg cggtttgcgtattgggcgccagggtggtttttcttttcaccagtgagacgggcaacagctgattgcccttcaccgcctggccctgagagagt tgcagcaagcggtccacgctggtttgccccagcaggcgaaaatcctgtttgatggtggttaacggcgggatataacatgagctgtcttcggt atcgtcgtatcccactaccgagatatccgcaccaacgcgcagcccggactcggtaatggcgcgcattgcgcccagcgccatctgatcgttgg
```

-continued

```
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggttgggaatgtaattcagctccgccatcgccgcttccactttttcccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccaaggaatggtgcatgcaaggagat
ggcgcccaacagtcccccggccacgggcctgccaccatacccacgccgaaacaagcgctcatgagcccgaagtggcgagcccgatcttccc
catcggtgatgtcggcgatataggcgccagcaaccgcacctgtggcgccggtgatgccggcacgatgcgtccggcgtagaggatcgagatc
tcgatcccgcgaaattaatacgactcactatagggggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaattctgaccctgctgga
actgattgacaacgtccagcgcctgggcctgggttaccgtttcgagtctgatatccgtggtgcgctggatcgcttcgtttcctccggcggct
tcgatgcggtaaccaagacttccctgcacggtacggcactgtcttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttctttcgtaaccattatcgacgatatctacgatgtatacggcaccctg
gacgaactggagctgtttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgacctttgacgactacttcggcaacgcatggaaatcctct
tctggcccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccAACaatagcgttt
cttgttacatgcgcactaaaggtatctccgaagaactggctaccgaaagcgtgatgaatctgatcgatgaaacctggaaaaagatgaacaag
gaaaaactgggtggtagcctgttcgcgaaaccgttcgtggaaaccgcgatcaacctggcacgtcaatctcactgcacttatcataacggcga
cgcgcataccctctccggatgagctgacccgcaaacgcgttctgtctgtaatcactgaaccgattctgccgttttgaacgcgaaaacctgtatt
ttcagggcctcgagcaccaccaccaccaccactgagatccggctgctaacaaagcccgaaaggaagctgagttggctgctgccaccgctgag
caataactagcataaccccttgggccctctaaacgggtcttgaggggttttttgctgaaaggaggaactatatccggat
```

3) Amino Acid Sequence of *P. alba* MEA G491S (+) TEV - pDW100 (S)

(SEQ ID NO: 67)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

-continued

SRPSHIFRLCNDLASASAEIARGETANSVSCYMRTKGISEELATESVMNLIDETWKKMNKE

KLSGSLFAKPFVETAINLARQSHCTYHNGDAHTSPDELTRKRVLSVITEPILPFERENLYFQG

LEHHHHHH

DNA sequence of pDW100

(SEQ ID NO: 68)

```
tggcgaatgggacgcgccctgtagcggcgcattaagcgcggcgggtgtggtggttacgcgcagcgtgaccgctacacttgccagcgccctag
cgcccgctcctttcgctttcttcccttcctttctcgccacgttcgccggctttccccgtcaagctctaaatcggggggctcccttagggttc
cgatttagtgctttacggcacctcgaccccaaaaaacttgattagggtgatggttcacgtagtgggccatcgccctgatagacggttttcg
ccctttgacgttggagtccacgttctttaatagtggactcttgttccaaactggaacaacactcaaccctatctcggtctattcttttgatt
tataagggattttgccgatttcggcctattggttaaaaaatgagctgatttaacaaaaatttaacgcgaattttaacaaaatattaacgttt
acaatttcaggtggcacttttcggggaaatgtgcgcggaaccccctatttgtttatttttctaaatacattcaaatatgtatccgctcatgaa
ttaattcttagaaaaactcatcgagcatcaaatgaaactgcaatttattcatatcaggattatcaataccatattttgaaaaagccgtttc
tgtaatgaaggagaaaactcaccgaggcagttccataggatggcaagatcctggtatcggtctgcgattccgactcgtccaacatcaataca
acctattaatttcccctcgtcaaaaataaggttatcaagtgagaaatcaccatgagtgacgactgaatccggtgagaatggcaaaagtttat
gcatttctttccagacttgttcaacaggccagccattacgctcgtcatcaaaatcactcgcatcaaccaaaccgttattcattcgtgattgc
gcctgagcgagacgaaatacgcgatcgctgttaaaaggacaattacaaacaggaatcgaatgcaaccggcgcaggaacactgccagcgcatc
aacaatattttcacctgaatcaggatattcttctaatacctggaatgctgttttcccggggatcgcagtggtgagtaaccatgcatcatcag
gagtacggataaaatgcttgatggtcggaagaggcataaattccgtcagccagtttagtctgaccatctcatctgtaacatcattggcaacg
ctacctttgccatgtttcagaaacaactctggcgcatcgggcttcccatacaatcgatagattgtcgcacctgattgcccgacattatcgcg
agcccatttatacccatataaatcagcatccatgttggaatttaatcgcggcctagagcaagacgtttcccgttgaatatggctcataacac
cccttgtattactgtttatgtaagcagacagttttattgttcatgaccaaaatcccttaacgtgagttttcgttccactgagcgtcagaccc
cgtagaaaagatcaaaggatcttcttgagatcctttttttctgcgcgtaatctgctgcttgcaaacaaaaaaaccaccgctaccagcggtgg
tttgtttgccggatcaagagctaccaactctttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagtggcga
taagtcgtgtcttaccgggttggactcaagacgatagttaccggataaggcgcagcggtcgggctgaacggggggttcgtgcacacagccca
gcttggagcgaacgacctacaccgaactgagataccctacagcgtgagctatgagaaagcgccacgcttcccgaagggagaaaggcggacagg
tatccggtaagcggcagggtcggaacaggagagcgcacgagggagcttccaggggaaacgcctggtatctttatagtcctgtcgggtttcg
ccacctctgacttgagcgtcgatttttgtgatgctcgtcaggggggcggagcctatggaaaaacgccagcaacgcggcctttttacggttcc
tggccttttgctggccttttgctcacatgttctttcctgcgttatcccctgattctgtggataaccgtattaccgcctttgagtgagctgat
accgctcgccgcagccgaacgaccgagcgcagcgagtcagtgagcgaggaagcggaagagcgcctgatgcggtattttctccttacgcatct
gtgcggtatttcacaccgcatatatggtgcactctcagtacaatctgctctgatgccgcatagttaagccagtatacactccgctatcgcta
cgtgactgggtcatggctgcgccccgacacccgccaacaccgctgacgcgccctgacgggcttgtctgctcccggcatccgcttacagaca
agctgtgaccgtctccgggagctgcatgtgtcagaggttttcaccgtcatcaccgaaacgcgcgaggcagctgcggtaaagctcatcagcgt
ggtcgtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaagggggatttctgttcatgggggtaatgataccgatgaa
acgagagaggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcacccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
```

-continued

```
gcggtcctcgccgaaaatgacccagagcgctgccggcacctgtcctacgagttgcatgataaagaagacagtcataagtgcggcgacgatag tcatgccccgcgcccaccggaaggagctgactgggttgaaggctctcaagggcatcggtcgagatcccggtgcctaatgagtgagctaactt acattaattgcgttgcgctcactgcccgctttccagtcgggaaacctgtcgtgccagctgcattaatgaatcggccaacgcgcggggagagg cggtttgcgtattgggcgccagggtggttttttcttttcaccagtgagacgggcaacagctgattgccctcaccgcctggccctgagagagt tgcagcaagcggtccacgctggtttgcccagcaggcgaaaatcctgtttgatggtggttaacggcgggatataacatgagctgtcttcggt atcgtcgtatcccactaccgagatatccgcaccaacgcgcagcccggactcggtaatggcgcgcattgcgcccagcgccatctgatcgttgg caaccagcatcgcagtgggaacgatgccctcattcagcatttgcatggtttgttgaaaaccggacatggcactccagtcgccttcccgttcc gctatcggctgaatttgattgcgagtgagatatttatgccagccagccagacgcagacgcgccgagacagaacttaatgggcccgctaacag cgcgatttgctggtgacccaatgcgaccagatgctccacgcccagtcgcgtaccgtcttcatgggagaaaataatactgttgatgggtgtct ggtcagagacatcaagaaataacgccggaacattagtgcaggcagcttccacagcaatggcatcctggtcatccagcggatagttaatgatc agcccactgacgcgttgcgcgagaagattgtgcaccgccgctttacaggcttcgacgccgcttcgttctaccatcgacaccaccacgctggc acccagttgatcggcgcgagatttaatcgccgcgacaatttgcgacggcgcgtgcagggccagactggaggtggcaacgccaatcagcaacg actgtttgcccgccagttgttgtgccacgcggttgggaatgtaattcagctccgccatcgccgcttccacttttttcccgcgttttcgcagaa acgtggctggcctggttcaccacgcgggaaacggtctgataagagacaccggcatactctgcgacatcgtataacgttactggtttcacatt caccaccctgaattgactctcttccgggcgctatcatgccataccgcgaaaggttttgcgccattcgatggtgtccgggatctcgacgctct cccttatgcgactcctgcattaggaagcagcccagtagtaggttgaggccgttgagcaccgccgccgcaaggaatggtgcatgcaaggagat ggcgcccaacagtcccccggccacggggcctgccaccatacccacgccgaaacaagcgctcatgagcccgaagtggcgagcccgatcttccc catcggtgatgtcggcgatataggcgccagcaaccgcacctgtggcgccggtgatgccggccacgatgcgtccggcgtagaggatcgagatc tcgatcccgcgaaattaatacgactcactataggggaattgtgagcggataacaattcccctctagaaataattttgtttaactttaagaag gagatatacatatggaagctcgtcgttctgcgaactacgaacctaacagctgggactatgattacctgctgtcctccgacacggacgagtcc atcgaagtatacaaagacaaagcgaaaaagctggaagccgaagttcgtcgcgagattaataacgaaaaagcagaatttctgaccctgctgga actgattgacaacgtccagcgcctgggcctgggttaccgtttcgagtctgatatccgtggtgcgctggatcgcttcgtttcctccggcggct tcgatgcggtaaccaagacttccctgcacggtacggcactgtctttccgtctgctgcgtcaacacggttttgaggtttctcaggaagcgttc agcggcttcaaagaccaaaacggcaacttcctggagaacctgaaggaagatatcaaagctatcctgagcctgtacgaggccagcttcctggc tctggaaggcgaaaacatcctggacgaggcgaaggttttcgcaatctctcatctgaaagaactgtctgaagaaaagatcggtaaagagctgg cagaacaggtgaaccatgcactggaactgccactgcatcgccgtactcagcgtctggaagcagtatggtctatcgaggcctaccgtaaaaag gaggacgcgaatcaggttctgctggagctggcaattctggattacaacatgatccagtctgtataccagcgtgatctgcgtgaaacgtcccg ttggtggcgtcgtgtgggtctggcgaccaaactgcactttgctcgtgaccgcctgattgagagcttctactgggccgtgggtgtagcattcg aaccgcaatactccgactgccgtaactccgtcgcaaaaatgttttctttcgtaaccattatcgacgatatctacgatgtatacggcaccctg gacgaactggagctgtttactgatgcagttgagcgttgggacgtaaacgccatcaacgacctgccggattacatgaaactgtgctttctggc tctgtataacactattaacgaaatcgcctacgacaacctgaaagataaaggtgagaacatcctgccgtatctgaccaaagcctgggctgacc tgtgcaacgctttcctgcaagaagccaagtggctgtacaacaaatctactccgacctttgacgactacttcggcaacgcatggaaatcctct tctggcccgctgcaactggtgttcgcttacttcgctgtcgtgcagaacattaaaaaggaagagatcgaaaacctgcaaaaataccatgacac catctctcgtccttcccatatcttccgtctgtgcaatgacctggctagcgcgtctgcggaaattgcgcgtggtgaaaccgcaaatagcgttt cttgttacatgcgcactaaaggtatctccgaagaactggctaccgaaagcgtgatgaatctgatcgatgaaacctggaaaaagatgaacaag gaaaaactgAGTggtagcctgttcgcgaaaccgttcgtggaaaccgcgatcaacctggcacgtcaatctcactgcacttatcataacggcga cgcgcatacctctccggatgagctgacccgcaaacgcgttctgtctgtaatcactgaaccgattctgccgtttgaacgcgaaaacctgtatt ttcagggcctcgagcaccaccaccaccaccactgagatccggctgctaacaaagcccgaaaggaagctgagttggctgctgccaccgctgag caataactagcataaccccttggggcctctaaacgggtcttgaggggttttttgctgaaaggaggaactatatccggat
```

4) Amino Acid Sequence of P. alba MEA L494P (+) TEV - pDW101 (P)  (SEQ ID NO: 69)

MEARRSANYEPNSWDYDYLLSSDTDESIEVYKDKAKKLEAEVRREINNEKAEFLTLLELID
NVQRLGLGYRFESDIRGALDRFVSSGGFDAVTKTSLHGTALSFRLLRQHGFEVSQEAFSGF
KDQNGNFLENLKEDIKAILSLYEASFLALEGENILDEAKVFAISHLKELSEEKIGKELAEQVN
HALELPLHRRTQRLEAVWSIEAYRKKEDANQVLLELAILDYNMIQSVYQRDLRETSRWWR
RVGLATKLHFARDRLIESFYWAVGVAFEPQYSDCRNSVAKMFSFVTIIDDIYDVYGTLDEL
ELFTDAVERWDVNAINDLPDYMKLCFLALYNTINEIAYDNLKDKGENILPYLTKAWADLC
NAFLQEAKWLYNKSTPTFDDYFGNAWKSSSGPLQLVPAYFAVVQNIKKEEIENLQKYHDTI
SRPSHIFRLCNDLASASAEIARGETANSVSCYMRTKGISEELATESVMNLIDETWKKMNKE
KLGGSPFAKPFVETAINLARQSHCTYHNGDAHTSPDELTRKRVLSVITEPILPFERENLYFQG
LEHHHHHH

DNA sequence of pDW101  (SEQ ID NO: 70)

tggcgaatgggacgcgccctgtagcggcgcattaagcgcggcgggtgtggtggttacgcgcagcgtgaccgctacacttgccagcgccctag
cgcccgctcctttcgctttcttcccttcctttctcgccacgttcgccggctttccccgtcaagctctaaatcggggggctcccttagggttc
cgatttagtgctttacggcacctcgaccccaaaaaacttgattagggtgatggttcacgtagtgggccatcgccctgatagacggttttcg
ccctttgacgttggagtccacgttctttaatagtggactcttgttccaaactggaacaacactcaacccatctcggtctattcttttgatt
tataagggattttgccgatttcggcctattggttaaaaaatgagctgatttaacaaaaatttaacgcgaattttaacaaaatattaacgttt
acaatttcaggtggcacttttcggggaaatgtgcgcggaaccccctatttgtttatttttctaaatacattcaaatatgtatccgctcatgaa
ttaattcttagaaaaactcatcgagcatcaaatgaaactgcaatttattcatatcaggattatcaataccatattttttgaaaaagccgtttc
tgtaatgaaggagaaaactcaccgaggcagttccataggatggcaagatcctggtatcggtctgcgattccgactcgtccaacatcaataca
acctattaatttcccctcgtcaaaaataaggttatcaagtgagaaatcaccatgagtgacgactgaatccggtgagaatggcaaaagtttat
gcatttctttccagacttgttcaacaggccagccattacgctcgtcatcaaaatcactcgcatcaaccaaaccgttattcattcgtgattgc
gcctgagcgagacgaaatacgcgatcgctgttaaaaggacaattacaaacaggaatcgaatgcaaccggcgcaggaacactgccagcgcatc
aacaatattttcacctgaatcaggatattcttctaatacctggaatgctgtttccggggatcgcagtggtgagtaaccatgcatcatcag
gagtacggataaaatgcttgatggtcggaagaggcataaattccgtcagccagtttagtctgaccatctcatctgtaacatcattggcaacg
ctacctttgccatgtttcagaaacaactctggcgcatcgggcttcccatacaatcgatagattgtcgcacctgattgcccgacattatcgcg
agcccatttatacccatataaatcagcatccatgttggaatttaatcgcggcctagagcaagacgtttcccgttgaatatggctcataacac
cccttgtattactgtttatgtaagcagacagttttattgttcatgaccaaaatcccttaacgtgagttttcgttccactgagcgtcagaccc
cgtagaaaagatcaaaggatcttcttgagatcctttttttctgcgcgtaatctgctgcttgcaaacaaaaaaaccaccgctaccagcggtgg
tttgtttgccggatcaagagctaccaactctttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagtggcga
taagtcgtgtcttaccgggttggactcaagacgatagttaccggataaggcgcagcggtcgggctgaacggggggttcgtgcacacagccca
gcttggagcgaacgacctacaccgaactgagatacctacagcgtgagctatgagaaagcgccacgcttcccgaagggagaaaggcggacagg
tatccggtaagcggcagggtcggaacaggagagcgcacgagggagcttccaggggaaacgcctggtatctttatagtcctgtcgggtttcg
ccacctctgacttgagcgtcgatttttgtgatgctcgtcaggggggcggagcctatggaaaaacgccagcaacgcggcctttttacggttcc
tggccttttgctggccttttgctcacatgttctttcctgcgttatcccctgattctgtggataaccgtattaccgcctttgagtgagctgat
accgctcgccgcagccgaacgaccgagcgcagcgagtcagtgagcgaggaagcggaagagcgcctgatgcggtattttctccttacgcatct
gtgcggtatttcacaccgcatatatggtgcactctcagtacaatctgctctgatgccgcatagttaagccagtatacactccgctatcgcta
cgtgactgggtcatggctgcgccccgacacccgccaacacccgctgacgcgccctgacgggcttgtctgctcccggcatccgcttacagaca
agctgtgaccgtctccgggagctgcatgtgtcagaggttttcaccgtcatcaccgaaacgcgcgaggcagctgcggtaaagctcatcagcgt -continued ggtcgtgaagcgattcacagatgtctgcctgttcatccgcgtccagctcgttgagtttctccagaagcgttaatgtctggcttctgataaag cgggccatgttaagggcggttttttcctgtttggtcactgatgcctccgtgtaaggggggattctgttcatgggggtaatgataccgatgaa acgagagaggatgctcacgatacgggttactgatgatgaacatgcccggttactggaacgttgtgagggtaaacaactggcggtatggatgc ggcgggaccagagaaaaatcactcagggtcaatgccagcgcttcgttaatacagatgtaggtgttccacagggtagccagcagcatcctgcg atgcagatccggaacataatggtgcagggcgctgacttccgcgtttccagactttacgaaacacggaaaccgaagaccattcatgttgttgc tcaggtcgcagacgttttgcagcagcagtcgcttcacgttcgctcgcgtatcggtgattcattctgctaaccagtaaggcaaccccgccagc ctagccgggtcctcaacgacaggagcacgatcatgcgcaccgtggggccgccatgccggcgataatggcctgcttctcgccgaaacgtttg gtggcgggaccagtgacgaaggcttgagcgagggcgtgcaagattccgaataccgcaagcgacaggccgatcatcgtcgcgctccagcgaaa gcggtcctcgccgaaaatgacccagagcgctgccggcacctgtcctacgagttgcatgataaagaagacagtcataagtgcggcgacgatag tcatgccccgcgcccaccggaaggagctgactgggttgaaggctctcaagggcatcggtcgagatcccggtgcctaatgagtgagctaactt acattaattgcgttgcgctcactgcccgctttccagtcgggaaacctgtcgtgccagctgcattaatgaatcggccaacgcgcgggagagg cggtttgcgtattgggcgccagggtggtttttcttttcaccagtgagacgggcaacagctgattgcccttcaccgcctggccctgagagagt tgcagcaagcggtccacgctggtttgcccagcaggcgaaaatcctgtttgatggtggttaacggcgggataacatgagctgtcttcggt atcgtcgtatcccactaccgagatatccgcaccaacgcgcagcccggactcggtaatggcgcgcattgcgcccagcgccatctgatcgttgg caaccagcatcgcagtgggaacgatgccctcattcagcatttgcatggtttgttgaaaaccggacatggcactccagtcgccttcccgttcc gctatcggctgaatttgattgcgagtgagatatttatgccagccagccagacgcagacgcgccgagacagaacttaatgggcccgctaacag cgcgatttgctggtgacccaatgcgaccagatgctccacgcccagtcgcgtaccgtcttcatgggagaaaataatactgttgatgggtgtct ggtcagagacatcaagaaataacgccggaacattagtgcaggcagcttccacagcaatggcatcctggtcatccagcggatagttaatgatc agcccactgacgcgttgcgcgagaagattgtgcaccgccgctttacaggcttcgacgccgcttcgttctaccatcgacaccaccacgctggc acccagttgatcggcgcgagatttaatcgccgcgacaatttgcgacggcgcgtgcagggccagactggaggtggcaacgccaatcagcaacg actgtttgcccgccagttgttgtgccacgcggtgggaatgtaattcagctccgccatcgccgcttccacttttttccgcgttttcgcagaa acgtggctggcctggttcaccacgcgggaaacggtctgataagagacaccggcatactctgcgacatcgtataacgttactggtttcacatt caccaccctgaattgactctcttccgggcgctatcatgccataccgcgaaaggttttgcgccattcgatggtgtccgggatctcgacgctct cccttatgcgactcctgcattaggaagcagcccagtagtaggttgaggccgttgagcaccgccgccgcaaggaatggtgcatgcaaggagat ggcgcccaacagtcccccggccacggggcctgccaccatacccacgccgaaacaagcgctcatgagcccgaagtggcgagcccgatcttccc catcggtgatgtcggcgatataggcgccagcaaccgcacctgtggcgccggtgatgccggccacgatgcgtccggcgtagaggatcgagatc tcgatcccgcgaaattaatacgactcactatagggggaattgtgagcggataacaattcccctctagaaataattttgtttaactttaagaag gagatatacatatggaagctcgtcgttctgcgaactacgaacctaacagctgggactatgattacctgctgtcctccgacacggacgagtcc atcgaagtatacaaagacaaagcgaaaaagctggaagccgaagttcgtcgcgagattaataacgaaaaagcagaatttctgaccctgctgga actgattgacaacgtccagcgcctgggcctgggttaccgtttcgagtctgatatccgtggtgcgctggatcgcttcgtttcctccggcggct tcgatgcggtaaccaagacttccctgcacggtacggcactgtctttccgtctgctgcgtcaacacggttttgaggtttctcaggaagcgttc agcggcttcaaagaccaaaacggcaacttcctggagaacctgaaggaagatatcaaagctatcctgagcctgtacgaggccagcttcctggc tctggaaggcgaaaacatcctggacgaggcgaaggttttcgcaatctctcatctgaaagaactgtctgaagaaaagatcggtaaagagctgg cagaacaggtgaaccatgcactggaactgccactgcatcgccgtactcagcgctctggaagcagtatggtctatcgaggcctaccgtaaaaag gaggacgcgaatcaggttctgctggagctggcaattctggattacaacatgatccagtctgtataccagcgtgatctgcgtgaaacgtcccg ttggtggcgtcgtgtgggtctggcgaccaaactgcactttgctcgtgaccgcctgattgagagcttctactgggccgtgggtgtagcattcg aaccgcaatactccgactgccgtaactccgtcgcaaaaatgttttctttcgtaaccattatcgacgatatctacgatgtatacggcaccctg gacgaactggagctgtttactgatgcagttgagcgttgggacgtaaacgccatcaacgacctgccggattacatgaaactgtgctttctggc tctgtataacactattaacgaaatcgcctacgacaacctgaaagataaaggtgagaacatcctgccgtatctgaccaaagcctgggctgacc tgtgcaacgctttcctgcaagaagccaagtggctgtacaacaaatctactccgacctttgacgactacttcggcaacgcatggaaatcctct tctggcccgctgcaactggtgttcgcttacttcgctgtcgtgcagaacattaaaaaggaagagatcgaaaacctgcaaaaataccatgacac -continued catctctcgtccttcccatatcttccgtctgtgcaatgacctggctagcgcgtctgcggaaattgcgcgtggtgaaaccgcaaatagcgttt cttgttacatgcgcactaaaggtatctccgaagaactggctaccgaaagcgtgatgaatctgatcgatgaaacctggaaaaagatgaacaag gaaaaactgggtggtagcCCGttcgcgaaaccgttcgtggaaaccgcgatcaacctggcacgtcaatctcactgcacttatcataacggcga cgcgcatacctctccggatgagctgacccgcaaacgcgttctgtctgtaatcactgaaccgattctgccgtttgaacgcgaaaacctgtatt ttcagggcctcgagcaccaccaccaccaccactgagatccggctgctaacaaagcccgaaaggaagctgagttggctgctgccaccgctgag caataactagcataaccccttgggcctctaaacgggtcttgaggggttttttgctgaaaggaggaactatatccggat 5) Amino Acid Sequence of P. alba MEA T536C (+) TEV - pDW102 (C)

(SEQ ID NO: 71)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLGGSLFAKPFVETAINLARQSHCTYHNGDAHTSPDELTRKRVLSVICEPILPFERENLYFQG

LEHHHHHH

DNA sequence of pDW102

(SEQ ID NO: 72)

tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcggggggctcccttaggggttc cgatttagtgctttacggcacctcgaccccaaaaaacttgattagggtgatggttcacgtagtgggccatcgccctgatagacggttttcg ccctttgacgttggagtccacgttctttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaacccctatttgtttatttttctaaatacattcaaatatgtatccgctcatgaa ttaattcttagaaaaactcatcgagcatcaaatgaaactgcaatttattcatatcaggattatcaataccatattttgaaaaagccgtttc tgtaatgaaggagaaaactcaccgaggcagttccataggatggcaagatcctggtatcggtctgcgattccgactcgtccaacatcaataca acctattaatttcccctcgtcaaaaataaggttatcaagtgagaaatcaccatgagtgacgactgaatccggtgagaatggcaaaagttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg ctacctttgccatgtttcagaaacaactctggcgcatcgggcttcccatacaatcgatagattgtcgcacctgattgcccgacattatcgcg agcccatttatacccatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc cgtagaaaagatcaaaggatcttcttgagatcctttttttctgcgcgtaatctgctgcttgcaaacaaaaaaaccaccgctaccagcggtgg tttgtttgccggatcaagagctaccaactctttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga taagtcgtgtcttaccgggttggactcaagacgatagttaccggataaggcgcagcggtcgggctgaacggggggttcgtgcacacagccca gcttggagcgaacgacctacaccgaactgagatacctacagcgtgagctatgagaaagcgccacgcttcccgaagggagaaaggcggacagg tatccggtaagcggcagggtcggaacaggagagcgcacgagggagcttccagggggaaacgcctggtatctttatagtcctgtcgggtttcg -continued ccacctctgacttgagcgtcgattttgtgatgctcgtcaggggggcggagcctatggaaaaacgccagcaacgcggccttttttacggttcc tggccttttgctggccttttgctcacatgttcttcctgcgttatccctgattctgtggataaccgtattaccgcctttgagtgagctgat accgctcgccgcagccgaacgaccgagcgcagcgagtcagtgagcgaggaagcggaagagcgcctgatgcggtattttctccttacgcatct gtgcggtatttcacaccgcatatatggtgcactctcagtacaatctgctctgatgccgcatagttaagccagtatacactccgctatcgcta cgtgactgggtcatggctgcgccccgacacccgccaacacccgctgacgcgccctgacgggcttgtctgctcccggcatccgcttacagaca agctgtgaccgtctccgggagctgcatgtgtcagaggttttcaccgtcatcaccgaaacgcgcgaggcagctgcggtaaagctcatcagcgt ggtcgtgaagcgattcacagatgtctgcctgttcatccgcgtccagctcgttgagtttctccagaagcgttaatgtctggcttctgataaag cgggccatgttaagggcggtttttttcctgttggtcactgatgcctccgtgtaagggggatttctgttcatgggggtaatgataccgatgaa acgagagaggatgctcacgatacgggttactgatgatgaacatgcccggttactggaacgttgtgagggtaaacaactggcggtatggatgc ggcgggaccagagaaaaatcactcagggtcaatgccagcgcttcgttaatacagatgtaggtgttccacagggtagccagcagcatcctgcg atgcagatccggaacataatggtgcagggcgctgacttccgcgtttccagactttacgaaacacggaaaccgaagaccattcatgttgttgc tcaggtcgcagacgttttgcagcagcagtcgcttcacgttcgctcgcgtatcggtgattcattctgctaaccagtaaggcaaccccgccagc ctagccgggtcctcaacgacaggagcacgatcatgcgcacccgtggggccgccatgccggcgataatggcctgcttctcgccgaaacgtttg gtggcgggaccagtgacgaaggcttgagcgagggcgtgcaagattccgaataccgcaagcgacaggccgatcatcgtcgcgctccagcgaaa gcggtcctcgccgaaaatgacccagagcgctgccggcacctgtcctacgagttgcatgataaagaagacagtcataagtgcggcgacgatag tcatgcccgcgcccaccggaaggagctgactgggttgaaggctctcaagggcatcggtcgagatcccggtgcctaatgagtgagctaactt acattaattgcgttgcgctcactgcccgctttccagtcgggaaacctgtcgtgccagctgcattaatgaatcggccaacgcgcgggagagg cggtttgcgtattgggcgccagggtggttttcttttcaccagtgagacgggcaacagctgattgcccttcaccgcctggccctgagagagt tgcagcaagcggtccacgctggtttgccccagcaggcgaaaatcctgtttgatggtggttaacggcgggataacatgagctgtcttcggt atcgtcgtatcccactaccgagatatccgcaccaacgcgcagcccggactcggtaatggcgcgcattgcgcccagcgccatctgatcgttgg caaccagcatcgcagtgggaacgatgccctcattcagcatttgcatggtttgttgaaaaccggacatggcactccagtcgccttcccgttcc gctatcggctgaatttgattgcgagtgagatatttatgccagccagccagacgcagacgcgccgagacagaacttaatgggcccgctaacag cgcgatttgctggtgacccaatgcgaccagatgctccacgcccagtcgcgtaccgtcttcatgggagaaaataatactgttgatgggtgtct ggtcagagacatcaagaaataacgccggaacattagtgcaggcagcttccacagcaatggcatcctggtcatccagcggatagttaatgatc agcccactgacgcgttgcgcgagaagattgtgcaccgccgctttacaggcttcgacgccgcttcgttctaccatcgacaccaccacgctggc acccagttgatcggcgcgagatttaatcgccgcgacaatttgcgacggcgcgtgcagggccagactggaggtggcaacgccaatcagcaacg actgtttgcccgccagttgttgtgccacgcggtttgggaatgtaattcagctccgccatcgccgcttccacttttttccgcgcgttttcgcagaa acgtggctggcctggttcaccacgcgggaaacggtctgataagagacaccggcatactctgcgacatcgtataacgttactggtttcacatt caccaccctgaattgactctcttccgggcgctatcatgccataccgcgaaaggttttgcgccattcgatggtgtccgggatctcgacgctct cccttatgcgactcctgcattaggaagcagcccagtagtaggttgaggccgttgagcaccgccgccgcaaggaatggtgcatgcaaggagat ggcgcccaacagtcccccggccacggggcctgccaccataccacgccgaaacaagcgctcatgagcccgaagtggcgagcccgatcttccc catcggtgatgtcggcgatataggcgccagcaaccgcacctgtggcgccggtgatgccggccacgatgcgtccggcgtagaggatcgagatc tcgatcccgcgaaattaatacgactcactataggggaattgtgagcggataacaattcccctctagaaataattttgttaactttaagaag gagatatacatatggaagctcgtcgttctgcgaactacgaacctaacagctgggactatgattacctgctgtcctccgacacggacgagtcc atcgaagtatacaaagacaaagcgaaaaagctggaagccgaagttcgtcgcgagattaataacgaaaaagcagaatttctgaccctgctgga actgattgacaacgtccagcgcctgggcctgggttaccgtttcgagtctgatatccgtggtgcgctggatcgcttcgtttcctcggcggct tcgatgcggtaaccaagacttcctgcacggtacggcactgtctttccgtctgctgcgtcaacacggttttgagggtttctcaggaagcgttc agcggcttcaaagaccaaaacggcaacttcctggagaacctgaaggaagatatcaaagctatcctgagcctgtacgaggccagcttcctggc tctggaaggcgaaaacatcctggacgaggcgaaggttttcgcaatctctcatctgaaagaactgtctgaagaaaagatcggtaaagagctgg cagaacaggtgaaccatgcactggaactgccactgcatcgccgtactcagcgtctggaagcagtatggtctatcgaggcctaccgtaaaaag gaggacgcgaatcaggttctgctggagctggcaattctggattacaacatgatccagtctgtataccagcgtgatctgcgtgaaacgtcccg -continued ttggtggcgtcgtgtgggtctggcgaccaaactgcactttgctcgtgaccgcctgattgagagcttctactgggccgtgggtgtagcattcg aaccgcaatactccgactgccgtaactccgtcgcaaaaatgttttctttcgtaaccattatcgacgatatctacgatgtatacggcaccctg gacgaactggagctgtttactgatgcagttgagcgttgggacgtaaacgccatcaacgacctgccggattacatgaaactgtgctttctggc tctgtataacactattaacgaaatcgcctacgacaacctgaaagataaaggtgagaacatcctgccgtatctgaccaaagcctgggctgacc tgtgcaacgctttcctgcaagaagccaagtggctgtacaacaaatctactccgacctttgacgactacttcggcaacgcatggaaatcctct tctggcccgctgcaactggtgttcgcttacttcgctgtcgtgcagaacattaaaaaggaagagatcgaaaacctgcaaaataccatgacac catctctcgtccttcccatatcttccgtctgtgcaatgacctggctagcgcgtctgcggaaattgcgcgtggtgaaaccgcaaatagcgttt cttgttacatgcgcactaaaggtatctccgaagaactggctaccgaaagcgtgatgaatctgatcgatgaaacctggaaaaagatgaacaag gaaaaactgggtggtagcctgttcgcgaaaccgttcgtggaaaccgcgatcaacctggcacgtcaatctcactgcacttatcataacggcga cgcgcataccttctccggatgagctgacccgcaaacgcgttctgtctgtaatcTGCgaaccgattctgccgtttgaacgcgaaaacctgtatt tcagggcctcgagcaccaccaccaccaccactgagatccggctgctaacaaagcccgaaggaagctgagttggctgctgccaccgctgag caataactagcataaccccttggggcctctaaacgggtcttgaggggttttttgctgaaaggaggaactatatccggat 6) Amino Acid Sequence of *P. alba* MEA A453N G491S (+) TEV - pDW103 (NS)

(SEQ ID NO: 73)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETNNSVSCYMRTKGISEELATESVMNLIDETWKKMNKE

KLSGSLFAKPFVETAINLARQSHCTYHNGDAHTSPDELTRKRVLSVITEPILPFERENLYFQG

LEHHHHHH

DNA sequence of pDW103

(SEQ ID NO: 74)

tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcggggggctcccttttagggttc cgatttagtgctttacggcacctcgaccccaaaaaacttgattagggtgatggttcacgtagtgggccatcgccctgatagacggttttcg ccctttgacgttggagtccacgttctttaatagtggactcttgttccaaactggaacaacactcaaccctatctcggtctattcttttgatt tataaggggattttgccgatttcggcctattggttaaaaaatgagctgatttaacaaaaatttaacgcgaattttaacaaaatattaacgttt acaatttcaggtggcacttttcggggaaatgtgcgcggaaccccctatttgtttatttttctaaatacattcaaatatgtatccgctcatgaa ttaattcttagaaaaactcatcgagcatcaaatgaaactgcaatttattcatatcaggattatcaataccatattttgaaaaagccgtttc tgtaatgaaggagaaaactcaccgaggcagttccataggatggcaagatcctggtatcggtctgcgattccgactcgtccaacatcaataca acctattaatttcccctcgtcaaaaataaggttatcaagtgagaaatcaccatgagtgacgactgaatccggtgagaatggcaaaagtttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg ctacctttgccatgtttcagaaacaactctggcgcatcgggcttcccatacaatcgatagattgtcgcacctgattgcccgacattatcgcg agcccatttatacccatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc -continued cgtagaaaagatcaaaggatcttcttgagatccttttttttctgcgcgtaatctgctgcttgcaaacaaaaaaaccaccgctaccagcggtgg tttgtttgccggatcaagagctaccaactcttttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga taagtcgtgtcttaccgggttggactcaagacgatagttaccggataaggcgcagcggtcgggctgaacgggggggttcgtgcacacagccca gcttggagcgaacgacctacaccgaactgagatacctacagcgtgagctatgagaaagcgccacgcttcccgaagggagaaaggcggacagg tatccggtaagcggcagggtcggaacaggagagcgcacgagggagcttccaggggggaaacgcctggtatctttatagtcctgtcgggtttcg ccacctctgacttgagcgtcgattttttgtgatgctcgtcagggggggcggagcctatggaaaaacgccagcaacgcggccttttttacggttcc tggccttttgctggccttttgctcacatgttcttttcctgcgttatccctgattctgtggataaccgtattaccgcctttgagtgagctgat accgctcgccgcagccaacgaccgagcgcagcgagtcagtgagcgaggaagcggaagagcgcctgatgcggtattttctccttacgcatct gtgcggtatttcacaccgcatatatggtgcactctcagtacaatctgctctgatgccgcatagttaagccagtatacactccgctatcgcta cgtgactgggtcatggctgcgccccgacacccgccaacacccgctgacgcgccctgacgggcttgtctgctcccggcatccgcttacagaca agctgtgaccgtctccgggagctgcatgtgtcagaggttttcaccgtcatcaccgaaacgcgcgaggcagctgcggtaaagctcatcagcgt ggtcgtgaagcgattcacagatgtctgcctgttcatccgcgtccagctcgttgagtttctccagaagcgttaatgtctggcttctgataaag cgggccatgttaagggcggttttttcctgtttggtcactgatgcctccgtgtaaggggggatttctgttcatgggggtaatgataccgatgaa acgagagaggatgctcacgatacgggttactgatgatgaacatgcccggttactggaacgttgtgagggtaaacaactggcggtatggatgc ggcgggaccagagaaaaatcactcagggtcaatgccagcgcttcgttaatacagatgtaggtgttccacagggtagccagcagcatcctgcg atgcagatccggaacataatggtgcagggcgctgacttccgcgtttccagactttacgaaacacggaaaccgaagaccattcatgttgttgc tcaggtcgcagacgttttgcagcagcagtcgcttcacgttcgctcgcgtatcggtgattcattctgctaaccagtaaggcaacccccgccagc ctagccgggtcctcaacgacaggagcacgatcatgcgcaccgtggggccgccatgccggcgataatggcctgcttctcgccgaaacgtttg gtggcgggaccagtgacgaaggcttgagcgagggcgtgcaagattccgaataccgcaagcgacaggccgatcatcgtcgcgctccagcgaaa gcggtcctcgccgaaaatgacccagagcgctgccggcacctgtcctacgagttgcatgataaagaagacagtcataagtgcggcgacgatag tcatgccccgcgcccaccggaaggagctgactgggttgaaggctctcaagggcatcggtcgagatcccggtgcctaatgagtgagctaactt acattaattgcgttgcgctcactgcccgctttccagtcgggaaacctgtcgtgccagctgcattaatgaatcggccaacgcgcgggagagg cggtttgcgtattgggcgccagggtggtttttcttttcaccagtgagacgggcaacagctgattgcccttcaccgcctggccctgagagagt tgcagcaagcggtccacgctggtttgcccagcaggcgaaaatcctgtttgatggtggttaacggcgggatataacatgagctgtcttcggt atcgtcgtatcccactaccgagatatccgcaccaacgcgcagcccggactcggtaatggcgcgcattgcgcccagcgccatctgatcgttgg caaccagcatcgcagtgggaacgatgccctcattcagcatttgcatggtttgttgaaaaaccggacatggcactccagtcgccttcccgttcc gctatcggctgaatttgattgcgagtgagatatttatgccagccagccagacgcagacgcgccgagacagaacttaatgggcccgctaacag cgcgatttgctggtgacccaatgcgaccagatgctccacgcccagtcgcgtaccgtcttcatgggagaaaataatactgttgatgggtgtct ggtcagagacatcaagaaataacgccggaacattagtgcaggcagcttccacagcaatggcatcctggtcatccagcggatagttaatgatc agcccactgacgcgttgcgcgagaagattgtgcaccgccgctttacaggcttcgacgccgcttcgttctaccatcgacaccaccacgctggc acccagttgatcggcgcgagatttaatcgccgcgacaatttgcgacggcgcgtgcagggccagactggaggtggcaacgccaatcagcaacg actgtttgcccgccagttgttgtgccacgcggttgggaatgtaattcagctccgccatcgccgcttccacttttttcccgcgttttcgcagaa acgtggctggcctggttcaccacgcgggaaacggtctgataagagacaccggcatactctgcgacatcgtataacgttactggtttcacatt caccaccctgaattgactctcttccgggcgctatcatgccataccgcgaaaggttttgcgccattcgatggtgtccgggatctcgacgctct cccttatgcgactcctgcattaggaagcagcccagtagtaggttgaggccgttgagcaccgccgccaaggaatggtgcatgcaaggagat ggcgcccaacagtcccccggccacggggcctgccaccatacccacgccgaaacaagcgctcatgagcccgaagtggcgagcccgatcttccc catcggtgatgtcggcgatataggcgccagcaaccgcacctgtggcgccggtgatgccggccacgatgcgtccggcgtagaggatcgagatc tcgatcccgcgaaattaatacgactcactatagggggaattgtgagcggataacaattcccctctagaaataattttgtttaactttaagaag gagatatacatatggaagctcgtcgttctgcgaactacgaacctaacagctgggactatgattacctgctgtcctccgacacggacgagtcc atcgaagtatacaaagacaaagcgaaaaagctggaagccgaagttcgtcgcgagattaataacgaaaaagcagaatttctgaccctgctgga -continued

```
actgattgacaacgtccagcgcctgggcctgggttaccgtttcgagtctgatatccgtggtgcgctggatcgcttcgtttcctccggcggct
tcgatgcggtaaccaagacttccctgcacggtacggcactgtcttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaaacatcctggacgaggcgaaggtttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggtctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttctttcgtaaccattatcgacgatatctacgatgtatacggcaccctg
gacgaactggagctgtttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgaccttttgacgactacttcggcaacgcatggaaatcctct
tctggcccgctgcaactggtgttcgcttacttcgctgtcgtgcagaacattaaaaaggaagagatcgaaaacctgcaaaataccatgacac
catctctcgtccttcccatatcttccgtctgtgcaatgacctggctagcgcgtctgcggaaattgcgcgtggtgaaaccaacaatagcgttt
cttgttacatgcgcactaaaggtatctccgaagaactggctaccgaaagcgtgatgaatctgatcgatgaaacctggaaaaagatgaacaag
gaaaaaactgAGTggtagcctgttcgcgaaaccgttcgtggaaaccgcgatcaacctggcacgtcaatctcactgcacttatcataacggcga
cgcgcatacctctccggatgagctgacccgcaaacgcgttctgtctgtaatcactgaaccgattctgccgtttgaacgcgaaaacctgtatt
ttcagggcctcgagcaccaccaccaccaccactgagatccggctgctaacaaagcccgaaggaagctgagttggctgctgccaccgctgag
caataactagcataaccccttggggcctctaaacgggtcttgaggggttttttgctgaaaggaggaactatatccggat
```

7) Amino Acid Sequence of P. alba MEA A453N L494P (+) TEV - pDW104 (NP)

(SEQ ID NO: 75)

MEARRSANYEPNSWDYDYLLSSDTDESIEVYKDKAKKLEAEVRREINNEKAEFLTLLELID
NVQRLGLGYRFESDIRGALDRFVSSGGFDAVTKTSLHGTALSFRLLRQHGFEVSQEAFSGF
KDQNGNFLENLKEDIKAILSLYEASFLALEGENILDEAKVFAISHLKELSEEKIGKELAEQVN
HALELPLHRRTQRLEAVWSIEAYRKKEDANQVLLELAILDYNMIQSVYQRDLRETSRWWR
RVGLATKLHFARDRLIESFYWAVGVAFEPQYSDCRNSVAKMFSFVTIIDDIYDVYGTLDEL
ELFTDAVERWDVNAINDLPDYMKLCFLALYNTINEIAYDNLKDKGENILPYLTKAWADLC
NAFLQEAKWLYNKSTPTFDDYFGNAWKSSSGPLQLVFAYFAVVQNIKKEEIENLQKYHDTI
SRPSHIFRLCNDLASASAEIARGETNNSVSCYMRTKGISEELATESVMNLIDETWKKMNKE
KLGGSPFAKPFVETAINLARQSHCTYHNGDAHTSPDELTRKRVLSVITEPILPFERENLYFQG
LEHHHHHH

DNA sequence of pDW104

(SEQ ID NO: 76)

```
tggcgaatgggacgcgccctgtagcggcgcattaagcgcggcgggtgtggtggttacgcgcagcgtgaccgctacacttgccagcgccctag
cgcccgctcctttcgctttcttcccttcctttctcgccacgttcgccggctttccccgtcaagctctaaatcggggggctccctttagggttc
cgatttagtgctttacggcacctcgaccccaaaaaacttgattagggtgatggttcacgtagtgggccatcgccctgatagacggttttttcg
ccctttgacgttggagtccacgttctttaatagtggactcttgttccaaactggaacaacactcaaccctatctcggtctattcttttgatt
tataagggattttgccgatttcggcctattggttaaaaaatgagctgatttaacaaaaatttaacgcgaattttaacaaaatattaacgttt
acaatttcaggtggcacttttcggggaaatgtgcgcggaacccctatttgtttatttttctaaatacattcaaatatgtatccgctcatgaa
ttaattcttagaaaaactcatcgagcatcaaatgaaactgcaatttattcatatcaggattatcaataccatattttgaaaaagccgtttc
tgtaatgaaggagaaaactcaccgaggcagttccataggatggcaagatcctggtatcggtctgcgattccgactcgtccaacatcaataca
acctattaatttccctcgtcaaaaataaggttatcaagtgagaaatcaccatgagtgacgactgaatccggtgagaatggcaaaagtttat
gcatttctttccagacttgttcaacaggccagccattacgctcgtcatcaaaatcactcgcatcaaccaaaccgttattcattcgtgattgc
```

-continued

```
gcctgagcgagacgaaatacgcgatcgctgttaaaaggacaattacaaacaggaatcgaatgcaaccggcgcaggaacactgccagcgcatc
aacaatattttcacctgaatcaggatattcttctaatacctggaatgctgttttcccggggatcgcagtggtgagtaaccatgcatcatcag
gagtacggataaaatgcttgatggtcggaagaggcataaattccgtcagccagtttagtctgaccatctcatctgtaacatcattggcaacg
ctacctttgccatgttttcagaaacaactctggcgcatcgggcttcccatacaatcgatagattgtcgcacctgattgcccgacattatcgcg
agcccatttataccatataaatcagcatccatgttggaatttaatcgcggcctagagcaagacgtttcccgttgaatatggctcataacac
cccttgtattactgtttatgtaagcagacagttttattgttcatgaccaaaatcccttaacgtgagttttcgttccactgagcgtcagaccc
cgtagaaaagatcaaggatcttcttgagatcctttttttctgcgcgtaatctgctgcttgcaaacaaaaaaaccaccgctaccagcggtgg
tttgtttgccggatcaagagctaccaactcttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagtggcga
taagtcgtgtcttaccgggttggactcaagacgatagttaccggataaggcgcagcggtcgggctgaacgggggttcgtgcacacagccca
gcttggagcgaacgacctacaccgaactgagatacctacagcgtgagctatgagaaagcgccacgcttcccgaagggagaaaggcggacagg
tatccggtaagcggcagggtcggaacaggagagcgcacgagggagcttccaggggaaacgcctggtatctttatagtcctgtcgggtttcg
ccacctctgacttgagcgtcgatttttgtgatgctcgtcaggggggcggagcctatggaaaaacgccagcaacgcggcctttttacggttcc
tggccttttgctggccttttgctcacatgttctttcctgcgttatcccctgattctgtggataaccgtattaccgcctttgagtgagctgat
accgctcgccgcagccgaacgaccgagcgcagcgagtcagtgagcgaggaagcggaagagcgcctgatgcggtattttctccttacgcatct
gtgcggtatttcacaccgcatatatggtgcactctcagtacaatctgctctgatgccgcatagttaagccagtatacactccgctatcgcta
cgtgactgggtcatggctgcgccccgacacccgccaacaccgctgacgcgccctgacgggcttgtctgctcccggcatccgcttacagaca
agctgtgaccgtctccgggagctgcatgtgtcagaggttttcaccgtcatcaccgaaacgcgcgaggcagctgcggtaaagctcatcagcgt
ggtcgtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaagggggatttctgttcatgggggtaatgataccgatgaa
acgagagaggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcacccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcgggagagg
cggtttgcgtattgggcgccagggtggtttttcttttcaccagtgagacgggcaacagctgattgcccttcaccgcctggccctgagagagt
tgcagcaagcggtccacgctggtttgccccagcaggcgaaaatcctgtttgatggtggttaacggcgggatataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagcagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggttgggaatgtaattcagctccgccatcgccgcttccacttttcccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
```

-continued

```
cccttatgcgactcctgcattaggaagcagcccagtagtaggttgaggccgttgagcaccgccgccgcaaggaatggtgcatgcaaggagat
ggcgcccaacagtcccccggccacggggcctgccaccataccacgccgaaacaagcgctcatgagcccgaagtggcgagcccgatcttccc
catcggtgatgtcggcgatataggcgccagcaaccgcacctgtggcgccggtgatgccggccacgatgcgtccggcgtagaggatcgagatc
tcgatcccgcgaaattaatacgactcactatagggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctgggttaccgtttcgagtctgatatccgtggtgcgctggatcgcttcgtttcctccggcggct
tcgatgcggtaaccaagacttccctgcacggtacggcactgtctttccgtctgctgcgtcaacacggttttgaggtttctcaggaagcgttc
agcggcttcaaagaccaaacggcaacttcctggagaacctgaaggaagatatcaaagctatcctgagcctgtacgaggccagcttcctggc
tctgaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttctttcgtaaccattatcgacgatatctacgatgtatacggcaccctg
gacgaactggagctgttttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgacctttgacgactacttcggcaacgcatggaaatcctct
tctggcccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccaacaatagcgttt
cttgttacatgcgcactaaaggtatctccgaagaactggctaccgaaagcgtgatgaatctgatcgatgaaacctggaaaaagatgaacaag
gaaaaactgggtggtagcccgttcgcgaaaccgttcgtggaaaccgcgatcaacctggcacgtcaatctcactgcacttatcataacggcga
cgcgcataccctctccggatgagctgacccgcaaacgcgttctgtctgtaatcactgaaccgattctgccgtttgaacgcgaaaacctgtatt
ttcagggcctcgagcaccaccaccaccaccactgagatccggctgctaacaaagcccgaaaggaagctgagttggctgctgccaccgctgag
caataactagcataaccccttggggcctctaaacgggtcttgaggggttttttgctgaaaggaggaactatatccggat
```

8) Amino Acid Sequence of *P. alba* MEA A453N T536C (+) TEV - pDW105 (NC)

(SEQ ID NO: 77)

MEARRSANYEPNSWDYDYLLSSDTDESIEVYKDKAKKLEAEVRREINNEKAEFLTLLELID
NVQRLGLGYRFESDIRGALDRFVSSGGFDAVTKTSLHGTALSFRLLRQHGFEVSQEAFSGF
KDQNGNFLENLKEDIKAILSLYEASFLALEGENILDEAKVFAISHLKELSEEKIGKELAEQVN
HALELPLHRRTQRLEAVWSIEAYRKKEDANQVLLELAILDYNMIQSVYQRDLRETSRWWR
RVGLATKLHFARDRLIESFYWAVGVAFEPQYSDCRNSVAKMFSFVTIIDDIYDVYGTLDEL
ELFTDAVERWDVNAINDLPDYMKLCFLALYNTINEIAYDNLKDKGENILPYLTKAWADLC
NAFLQEAKWLYNKSTPTFDDYFGNAWKSSSGPLQLVFAYFAVVQNIKKEEIENLQKYHDTI
SRPSHIFRLCNDLASASAEIARGETNNSVSCYMRTKGISEELATESVMNLIDETWKKMNKE
KLGGSLFAKPFVETAINLARQSHCTYHNGDAHTSPDELTRKRVLSVICEPILPFERENLYFQG
LEHHHHHH

DNA sequence of pDW105

(SEQ ID NO: 78)

```
tggcgaatgggacgcgccctgtagcggcgcattaagcgcggcgggtgtggtggttacgcgcagcgtgaccgctacacttgccagcgccctag
cgcccgctcctttcgctttcttcccttcctttctcgccacgttcgccggctttccccgtcaagctctaaatcgggggctcccttagggttc
cgatttagtgctttacggcacctcgaccccaaaaaacttgattagggtgatggttcacgtagtgggccatcgccctgatagacggttttcg
cccctttgacgttggagtccacgttctttaatagtggactcttgttccaaactggaacaacactcaaccctatctcggtctattcttttgatt
```

-continued

```
tataagggattttgccgatttcggcctattggttaaaaaatgagctgatttaacaaaaatttaacgcgaattttaacaaaatattaacgttt
acaatttcaggtggcacttttcggggaaatgtgcgcggaaccccctatttgtttattttttctaaatacattcaaatatgtatccgctcatgaa
ttaattcttagaaaaactcatcgagcatcaaatgaaactgcaatttattcatatcaggattatcaataccatattttttgaaaaagccgtttc
tgtaatgaaggagaaaactcaccgaggcagttccataggatggcaagatcctggtatcggtctgcgattccgactcgtccaacatcaataca
acctattaatttcccctcgtcaaaaataaggttatcaagtgagaaatcaccatgagtgacgactgaatccggtgagaatggcaaaagtttat
gcatttcttccagacttgttcaacaggccagccattacgctcgtcatcaaaatcactcgcatcaaccaaaccgttattcattcgtgattgc
gcctgagcgagacgaaatacgcgatcgctgttaaaaggacaattacaaacaggaatcgaatgcaaccggcgcaggaacactgccagcgcatc
aacaatattttcacctgaatcaggatattcttctaatacctggaatgctgtttcccggggatcgcagtggtgagtaaccatgcatcatcag
gagtacggataaaatgcttgatggtcggaagaggcataaattccgtcagccagtttagtctgaccatctcatctgtaacatcattggcaacg
ctacctttgccatgtttcagaaacaactctggcgcatcgggcttcccatacaatcgatagattgtcgcacctgattgcccgacattatcgcg
agcccatttatacccatataaatcagcatccatgttggaatttaatcgcggcctagagcaagacgtttcccgttgaatatggctcataacac
cccttgtattactgtttatgtaagcagacagttttattgttcatgaccaaaatcccttaacgtgagttttcgttccactgagcgtcagaccc
cgtagaaaagatcaaaggatcttcttgagatcctttttttctgcgcgtaatctgctgcttgcaaacaaaaaaaccaccgctaccagcggtgg
tttgtttgccggatcaagagctaccaactctttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagtggcga
taagtcgtgtcttaccgggttggactcaagacgatagttaccggataaggcgcagcggtcgggctgaacggggggttcgtgcacacagccca
gcttggagcgaacgacctacaccgaactgagatacctacagcgtgagctatgagaaagcgccacgcttcccgaagggagaaaggcggacagg
tatccggtaagcggcagggtcggaacaggagagcgcacgagggagcttccaggggaaacgcctggtatctttatagtcctgtcgggtttcg
ccacctctgacttgagcgtcgatttttgtgatgctcgtcaggggggcggagcctatggaaaaacgccagcaacgcggcctttttacggttcc
tggccttttgctggccttttgctcacatgttctttcctgcgttatcccctgattctgtggataaccgtattaccgcctttgagtgagctgat
accgctcgccgcagccgaacgaccgagcgcagcgagtcagtgagcgaggaagcggaagagcgcctgatgcggtattttctccttacgcatct
gtgcggtatttcacaccgcatatatggtgcactctcagtacaatctgctctgatgccgcatagttaagccagtatacactccgctatcgcta
cgtgactgggtcatggctgcgccccgacacccgccaacacccgctgacgcgccctgacgggcttgtctgctcccggcatccgcttacagaca
agctgtgaccgtctccgggagctgcatgtgtcagaggttttcaccgtcatcaccgaaacgcgcgaggcagctgcggtaaagctcatcagcgt
ggtcgtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaagggggatttctgttcatgggggtaatgataccgatgaa
acgagagaggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcacccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctgagagagt
tgcagcaagcggtccacgctggtttgccccagcaggcgaaaatcctgtttgatggtggttaacggcgggatataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
```

-continued

```
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggtttgggaatgtaattcagctccgccatcgccgcttccactttttcccgcgcttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatgcaaggagat
ggcgcccaacagtccccggcacggggcctgccaccataccacgccgaaacaagcgctcatgagcccgaagtggcgagcccgatcttccc
catcggtgatgtcggcgatataggcgccagcaaccgcacctgtggcgccggtgatgccggccacgatgcgtccggcgtagaggatcgagatc
tcgatcccgcgaaattaatacgactcactatagggggaattgtgagcggataacaattcccctctagaaataatttttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctgggttaccgtttcgagtctgatatccgtggtgcgctggatcgcttcgtttcctccggcggct
tcgatgcggtaaccaagacttccctgcacggtacggcactgtctttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttctttcgtaaccattatcgacgatatctacgatgtatacggcaccctg
gacgaactggagctgtttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgacctttgacgactacttcggcaacgcatggaaatcctct
tctggccccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccaacaatagcgttt
cttgttacatgcgcactaaaggtatctccgaagaactggctaccgaaagcgtgatgaatctgatcgatgaaacctggaaaaagatgaacaag
gaaaaactgggtggtagcctgttcgcgaaaccgttcgtggaaaccgcgatcaacctggcacgtcaatctcactgcacttatcataacggcga
cgcgcataccctctccggatgagctgacccgcaaacgcgttctgtctgtaatctgcgaaccgattctgccgtttgaacgcgaaaacctgtatt
ttcagggcctcgagcaccaccaccaccaccactgagatccggctgctaacaaagcccgaaaggaagctgagttggctgctgccaccgctgag
caataactagcataaccccttggggcctctaaacgggtcttgaggggttttttgctgaaaggaggaactatatccggat
```

9) Amino Acid Sequence of *P. alba* MEA A453N G491S L494P (+) TEV - pDW106 (NSP)

(SEQ ID NO: 79)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETNNSVSCYMRTKGISEELATESVMNLIDETWKKMNKE

-continued

KLSGSPFAKPFVETAINLARQSHCTYHNGDAHTSPDELTRKRVLSVITEPILPFERENLYFQG

LEHHHHHH

DNA sequence of pDW106

(SEQ ID NO: 80)

tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcggggggctcccctttagggttc cgatttagtgctttacggcacctcgaccccaaaaaacttgattagggtgatggttcacgtagtgggccatcgccctgatagacggttttttcg ccctttgacgttggagtccacgttctttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaacccctatttgtttatttttctaaatacattcaaatatgtatccgctcatgaa ttaattcttagaaaaactcatcgagcatcaaatgaaactgcaatttattcatatcaggattatcaataccatattttgaaaaagccgtttc tgtaatgaaggagaaaactcaccgaggcagttccataggatggcaagatcctggtatcggtctgcgattccgactcgtccaacatcaataca acctattaatttcccctcgtcaaaaataaggttatcaagtgagaaatcaccatgagtgacgactgaatccggtgagaatggcaaaagtttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg ctacctttgccatgtttcagaaacaactctggcgcatcgggcttcccatacaatcgatagattgtcgcacctgattgcccgacattatcgcg agcccatttatacccatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc cgtagaaaagatcaaaggatcttcttgagatccttttttttctgcgcgtaatctgctgcttgcaaacaaaaaaaccaccgctaccagcggtgg tttgtttgccggatcaagagctaccaactctttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga taagtcgtgtcttaccgggttggactcaagacgatagttaccggataaggcgcagcggtcgggctgaacggggggttcgtgcacacagccca gcttggagcgaacgacctacaccgaactgagataccTacagcgtgagctatgagaaagcgccacgcttcccgaagggagaaaggcggacagg tatccggtaagcggcagggtcggaacaggagagcgcacgagggagcttccaggggggaaacgcctggtatctttatagtcctgtcgggtttcg ccacctctgacttgagcgtcgatttttgtgatgctcgtcaggggggcggagcctatggaaaaacgccagcaacgcggcctttttacggttcc tggccttttgctggccttttgctcacatgttctttcctgcgttatcccctgattctgtggataaccgtattaccgcctttgagtgagctgat accgctcgccgcagccgaacgaccgagcgcagcgagtcagtgagcgaggaagcggaagagcgcctgatgcggtattttctccttacgcatct gtgcggtatttcacaccgcatatatggtgcactctcagtacaatctgctctgatgccgcatagttaagccagtatacactccgctatcgcta cgtgactgggtcatggctgcgccccgacacccgccaacaccgctgacgcgccctgacgggcttgtctgctcccggcatccgcttacagaca agctgtgaccgtctccgggagctgcatgtgtcagaggttttcaccgtcatcaccgaaacgcgcgaggcagctgcggtaaagctcatcagcgt ggtcgtgaagcgattcacagatgtctgcctgttcatccgcgtccagctcgttgagtttctccagaagcgttaatgtctggcttctgataaag cgggccatgttaagggcggttttttcctgtttggtcactgatgcctccgtgtaagggggatttctgttcatgggggtaatgataccgatgaa acgagagaggatgctcacgatacgggttactgatgatgaacatgcccggttactggaacgttgtgagggtaaacaactggcggtatggatgc ggcgggaccagagaaaaatcactcagggtcaatgccagcgcttcgttaatacagatgtaggtgttccacagggtagccagcagcatcctgcg atgcagatccggaacataatggtgcagggcgctgacttccgcgtttccagactttacgaaacacggaaaccgaagaccattcatgttgttgc tcaggtcgcagacgttttgcagcagcagtcgcttcacgttcgctcgcgtatcggtgattcattctgctaaccagtaaggcaaccccgccagc ctagccgggtcctcaacgacaggagcacgatcatgcgcacccgtggggccgccatgccggcgataatggcctgcttctcgccgaaacgtttg gtggcgggaccagtgacgaaggcttgagcgagggcgtgcaagattccgaataccgcaagcgacaggccgatcatcgtcgcgctccagcgaaa gcggtcctcgccgaaaatgacccagagcgctgccggcacctgtcctacgagttgcatgataaagaagacagtcataagtgcggcgacgatag -continued

```
tcatgccccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcggggagagg
cggtttgcgtattgggcgccagggtggttttttcttttcaccagtgagacgggcaacagctgattgcccttcaccgcctggccctgagagagt
tgcagcaagcggtccacgctggtttgccccagcaggcgaaaatcctgtttgatggtggttaacggcgggatataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggttggaatgtaattcagctccgccatcgccgcttccacttttttcccgcgttttcgcagaa
acgtggctggcctggttcaccacgcggaaacggtctgataagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatgcaaggagat
ggcgcccaacagtcccccggccacggggcctgccaccataccccgccgaaacaagcgctcatgagcccgaagtggcgagcccgatcttccc
catcggtgatgtcggcgatataggcgccagcaaccgcacctgtggcgccggtgatgccgccacgatgcgtccggcgtagaggatcgagatc
tcgatcccgcgaaattaatacgactcactatagggaattgtgagcggataacaattcccctctagaaataattttgttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctgggttaccgtttcgagtctgatatccgtggtgcgctggatcgcttcgtttcctccggcggct
tcgatgcggtaaccaagacttccctgcacggtacggcactgtcttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttctttcgtaaccattatcgacgatatctacgatgtatacggcaccctg
gacgaactggagctgtttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgacctttgacgactacttcggcaacgcatggaaatcctct
tctggcccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccaacaatagcgttt
cttgttacatgcgcactaaaggtatctccgaagaactggctaccgaaagcgtgatgaatctgatcgatgaaacctggaaaaagatgaacaag
gaaaaactgagtggtagcccgttcgcgaaaccgttcgtggaaaccgcgatcaacctggcacgtcaatctcactgcacttatcataacggcga
cgcgcatacctctccggatgagctgacccgcaaacgcgttctgtctgtaatcactgaaccgattctgccgtttgaacgcgaaaacctgtatt
ttcagggcctcgagcaccaccaccaccaccactgagatccggctgctaacaaagcccgaaaggaagctgagttggctgctgccaccgctgag
caataactagcataaccccttggggcctctaaacgggtcttgaggggttttttgctgaaaggaggaactatatccggat
```

10) Amino Acid Sequence of *P. alba* MEA A453N G491S T536C (+) TEV - pDW107 (NSC)

(SEQ ID NO: 81)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

-continued

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETNNSVSCYMRTKGISEELATESVMNLIDETWKKMNKE

KLSGSLFAKPFVETAINLARQSHCTYHNGDAHTSPDELTRKRVLSVICEPILPFERENLYFQG

LEHHHHHH

DNA sequence of pDW107

(SEQ ID NO: 82)

tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcgggggctccctttagggttc cgatttagtgctttacggcacctcgaccccaaaaaacttgattagggtgatggttcacgtagtgggccatcgccctgatagacggttttcg cccctttgacgttggagtccacgttctttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaacccctatttgtttatttttctaaatacattcaaatatgtatccgctcatgaa ttaattcttagaaaaactcatcgagcatcaaatgaaactgcaatttattcatatcaggattatcaataccatatttttgaaaaagccgtttc tgtaatgaaggagaaaactcaccgaggcagttccataggatggcaagatcctggtatcggtctgcgattccgactcgtccaacatcaataca acctattaatttcccctcgtcaaaaataaggttatcaagtgagaaatcaccatgagtgacgactgaatccggtgagaatggcaaaagtttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg ctaccttttgccatgtttcagaaacaactctggcgcatcgggcttcccatacaatcgatagattgtcgcacctgattgcccgacattatcgcg agcccatttataccccatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc cgtagaaaagatcaaaggatcttcttgagatcctttttttctgcgcgtaatctgctgcttgcaaacaaaaaaaccaccgctaccagcggtgg tttgtttgccggatcaagagctaccaactctttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga taagtcgtgtcttaccgggttggactcaagacgatagttaccggataaggcgcagcggtcgggctgaacggggggttcgtgcacacagccca gcttggagcgaacgacctacaccgaactgagatacctacagcgtgagctatgagaaagcgccacgcttcccgaagggagaaaggcggacagg tatccggtaagcggcagggtcggaacaggagagcgcacgagggagcttccaggggaaacgcctggtatctttatagtcctgtcgggtttcg ccacctctgacttgagcgtcgatttttgtgatgctcgtcaggggggcggagcctatggaaaaacgccagcaacgcggcctttttacggttcc tggccttttgctggccttttgctcacatgttctttcctgcgttatccctgattctgtggataaccgtattaccgcctttgagtgagctgat accgctcgccgcagccgaacgaccgagcgcagcgagtcagtgagcgaggaagcggaagagcgcctgatgcggtattttctccttacgcatct gtgcggtatttcacaccgcatatatggtgcactctcagtacaatctgctctgatgccgcatagttaagccagtatacactccgctatcgcta cgtgactgggtcatggctgcgccccgacacccgccaacaccgctgacgcgccctgacgggcttgtctgctcccggcatccgcttacagaca agctgtgaccgtctccgggagctgcatgtgtcagaggttttcaccgtcatcaccgaaacgcgcgaggcagctgcggtaaagctcatcagcgt ggtcgtgaagcgattcacagatgtctgcctgttcatccgcgtccagctcgttgagtttctccagaagcgttaatgtctggcttctgataaag cgggccatgttaagggcggttttttcctgtttggtcactgatgcctccgtgtaagggggatttctgttcatgggggtaatgataccgatgaa acgagagaggatgctcacgatacgggttactgatgatgaacatgcccggttactggaacgttgtgagggtaaacaactggcggtatggatgc -continued

```
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcaccegtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctgagagagt
tgcagcaagcggtccacgctggtttgcccagcaggcgaaaatcctgtttgatggtggttaacggcgggataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggttgggaatgtaattcagctccgccatcgccgcttccacttttttcccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccaaggaatggtgcatgcaaggagat
ggcgcccaacagtcccccggccacggggcctgccaccatacccacgccgaaacaagcgctcatgagcccgaagtggcgagcccgatcttccc
catcggtgatgtcggcgatataggcgccagcaaccgcacctgtggcgccggtgatgccggccacgatgcgtccggcgtagaggatcgagatc
tcgatcccgcgaaattaatacgactcactataggggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctggggttaccgtttcgagtctgatatccgtggtgcgctggatcgcttcgtttcctccggcggct
tcgatgcggtaaccaagacttccctgcacggtacggcactgtcttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctgaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttctttcgtaaccattatcgacgatatctacgatgtatacggcaccctg
gacgaactggagctgtttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgacctttgacgactacttcggcaacgcatggaaatcctct
tctggcccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccaacaatagcgttt
cttgttacatgcgcactaaaggtatctccgaagaactggctaccgaaagcgtgatgaatctgatcgatgaaacctggaaaaagatgaacaag
gaaaaactgagtggtagcctgttcgcgaaaccgttcgtggaaaccgcgatcaacctggcacgtcaatctcactgcactttatcataacggcga
```

-continued cgcgcatacctctccggatgagctgacccgcaaacgcgttctgtctgtaatctgcgaaccgattctgccgtttgaacgcgaaaacctgtatt ttcagggcctcgagcaccaccaccaccaccactgagatccggctgctaacaaagcccgaaaggaagctgagttggctgctgccaccgctgag caataactagcataaccccttggggcctctaaacgggtcttgaggggttttttgctgaaaggaggaactatatccggat 11) Amino Acid Sequence of *P. alba* MEA A453N L494P T536C (+) TEV - pDW108 (NPC)

(SEQ ID NO: 83)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETNNSVSCYMRTKGISEELATESVMNLIDETWKKMNKE

KLGGSPFAKPFVETAINLARQSHCTYHNGDAHTSPDELTRKRVLSVICEPILPFERENLYFQG

LEHHHHHH

DNA sequence of pDW108

(SEQ ID NO: 84)

tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcggggggctccctttagggttc cgatttagtgctttacggcacctcgaccccaaaaaacttgattagggtgatggttcacgtagtgggccatcgccctgatagacggttttttcg cccttttgacgttggagtccacgttctttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaacccctatttgtttatttttctaaatacattcaaatatgtatccgctcatgaa ttaattcttagaaaaactcatcgagcatcaaatgaaactgcaatttattcatatcaggattatcaataccatatttttgaaaaagccgtttc tgtaatgaaggagaaaactcaccgaggcagttccataggatggcaagatcctggtatcggtctgcgattccgactcgtccaacatcaataca acctattaatttccctcgtcaaaaataaggttatcaagtgagaaatcaccatgagtgacgactgaatccggtgagaatggcaaaagtttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg ctacctttgccatgtttcagaaacaactctggcgcatcgggcttcccatacaatcgatagattgtcgcacctgattgcccgacattatcgcg agcccatttatacccatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc cgtagaaaagatcaaaggatcttcttgagatcctttttttctgcgcgtaatctgctgcttgcaaacaaaaaaaccaccgctaccagcggtgg tttgtttgccggatcaagagctaccaactctttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga taagtcgtgtcttaccgggttggactcaagacgatagttaccggataaggcgcagcggtcgggctgaacggggggttcgtgcacacagccca gcttggagcgaacgacctacaccgaactgagatacctacagcgtgagctatgagaaagcgccacgcttcccgaagggagaaaggcggacagg tatccggtaagcggcagggtcggaacaggagagcgcacgagggagcttccagggggaaacgcctggtatctttatagtcctgtcgggtttcg ccacctctgacttgagcgtcgatttttgtgatgctcgtcaggggggcggagcctatggaaaaacgccagcaacgcggcctttttacggttcc tggccttttgctggccttttgctcacatgttctttcctgcgttatccctgattctgtggataaccgtattaccgcctttgagtgagctgat accgctcgccgcagccgaacgaccgagcgcagcgagtcagtgagcgaggaagcggaagagcgcctgatgcggtattttctccttacgcatct -continued gtgcggtatttcacaccgcatatatggtgcactctcagtacaatctgctctgatgccgcatagttaagccagtatacactccgctatcgcta cgtgactgggtcatggctgcgccccgacaccgcaacaccgctgacgcgcctgacgggcttgtctgctccggcatccgcttacagaca agctgtgaccgtctccgggagctgcatgtgtcagaggttttcaccgtcatcaccgaaacgcgcgaggcagctgcggtaaagctcatcagcgt ggtcgtgaagcgattcacagatgtctgcctgttcatccgcgtccagctcgttgagtttctccagaagcgttaatgtctggcttctgataaag cgggccatgttaagggcggtttttcctgtttggtcactgatgcctccgtgtaaggggatttctgttcatgggggtaatgataccgatgaa acgagagaggatgctcacgatacgggttactgatgatgaacatgcccggttactggaacgttgtgagggtaaacaactggcggtatggatgc ggcgggaccagagaaaaatcactcagggtcaatgccagcgcttcgttaatacagatgtaggtgttccacagggtagccagcagcatcctgcg atgcagatccggaacataatggtgcagggcgctgacttccgcgtttccagactttacgaaacacggaaaccgaagaccattcatgttgttgc tcaggtcgcagacgttttgcagcagcagtcgcttcacgttcgctcgcgtatcggtgattcattctgctaaccagtaaggcaaccccgccagc ctagccgggtcctcaacgacaggagcacgatcatgcgcaccgtggggccgccatgccggcgataatggcctgcttctcgccgaaacgtttg gtggcgggaccagtgacgaaggcttgagcgagggcgtgcaagattccgaataccgcaagcgacaggccgatcatcgtcgcgctccagcgaaa gcggtcctcgccgaaaatgacccagagcgctgccggcacctgtcctacgagttgcatgataaagaagacagtcataagtgcggcgacgatag tcatgccccgcgcccaccggaaggagctgactgggttgaaggctctcaagggcatcggtcgatcccggtgcctaatgagtgagctaactt acattaattgcgttgcgctcactgcccgctttccagtcgggaaacctgtcgtgccagctgcattaatgaatcggccaacgcgcgggagagg cggtttgcgtattgggcgccagggtggttttcttttcaccagtgagacgggcaacagctgattgcccttcaccgcctggccctgagagagt tgcagcaagcggtccacgctggtttgccccagcaggcgaaaatcctgtttgatggtggttaacggcgggatataacatgagctgtcttcggt atcgtcgtatcccactaccgagatatccgcaccaacgcgcagcccggactcggtaatggcgcgcattgcgcccagcgccatctgatcgttgg caaccagcatcgcagtgggaacgatgccctcattcagcatttgcatggtttgttgaaaaccggacatggcactccagtcgccttcccgttcc gctatcggctgaatttgattgcgagtgagatatttatgccagccagccagacgcagacgcgccgagacagaacttaatgggcccgctaacag cgcgatttgctggtgacccaatgcgaccagatgctccacgcccagtcgcgtaccgtcttcatgggagaaaataatactgttgatgggtgtct ggtcagagacatcaagaaataacgccggaacattagtgcaggcagcttccacagcaatggcatcctggtcatccagcggatagttaatgatc agcccactgacgcgttgcgcgagaagattgtgcaccgccgctttacaggcttcgacgccgcttcgttctaccatcgacaccaccacgctggc acccagttgatcggcgcgagatttaatcgccgcgacaatttgcgacggcgcgtgcagggccagactggaggtggcaacgccaatcagcaacg actgtttgcccgccagttgttgtgccacgcggttgggaatgtaattcagctccgccatcgccgcttccactttttcccgcgttttcgcagaa acgtggctggcctggttcaccacgcgggaaacggtctgataagagacaccggcatactctgcgacatcgtataacgttactggtttcacatt caccaccctgaattgactctcttccgggcgctatcatgccataccgcgaaaggttttgcgccattcgatggtgtccgggatctcgacgctct cccttatgcgactcctgcattaggaagcagcccagtagtaggttgaggccgttgagcaccgccgccgcaaggaatggtgcatgcaaggagat ggcgcccaacagtccccggccacggggcctgccaccatacccacgccgaaacaagcgctcatgagcccgaagtggcgagcccgatcttccc catcggtgatgtcggcgatataggcgccagcaaccgcacctgtggcgccggtgatgccggccacgatgcgtccggcgtagaggatcgagatc tcgatcccgcgaaattaatacgactcactataggggaattgtgagcggataacaattcccctctagaaataattttgtttaactttaagaag gagatatacatatggaagctcgtcgttctgcgaactacgaacctaacagctgggactatgattacctgctgtcctccgacacggacgagtcc atcgaagtatacaaagacaaagcgaaaaagctggaagccgaagttcgtcgcgagattaataacgaaaaagcagaatttctgaccctgctgga actgattgacaacgtccagcgcctgggcctgggttaccgtttcgagtctgatatccgtggtgcgctggatcgcttcgtttcctccggcggct tcgatgcggtaaccaagacttccctgcacggtacggcactgtcttccgtctgctgcgtcaacacggttttgaggtttctcaggaagcgttc agcggcttcaaagaccaaaacggcaacttcctggagaacctgaaggaagatatcaaagctatcctgagcctgtacgaggccagcttcctggc tctggaaggcgaaaacatcctggacgaggcgaaggtttcgcaatctctcatctgaaagaactgtctgaagaaaagatcggtaaagagctgg cagaacaggtgaaccatgcactggaactgccactgcatcgccgtactcagcgtctggaagcagtatggtctatcgaggcctaccgtaaaaag gaggacgcgaatcaggttctgctggagctggcaattctggattacaacatgatccagtctgtataccagcgtgatctgcgtgaaacgtcccg ttggtggcgtcgtgtgggtctggcgaccaaactgcactttgctcgtgaccgcctgattgagagcttctactgggccgtgggtgtagcattcg aaccgcaatactccgactgccgtaactccgtcgcaaaaatgttttctttcgtaaccattatcgacgatatctacgatgtatacggcacctg gacgaactggagctgtttactgatgcagttgagcgttgggacgtaaacgccatcaacgacctgccggattacatgaaactgtgctttctggc -continued

```
tctgtataacactattaacgaaatcgcctacgacaacctgaaagataaaggtgagaacatcctgccgtatctgaccaaagcctgggctgacc tgtgcaacgctttcctgcaagaagccaagtggctgtacaacaaatctactccgacctttgacgactacttcggcaacgcatggaaatcctct tctggcccgctgcaactggtgttcgcttacttcgctgtcgtgcagaacattaaaaaggaagagatcgaaacctgcaaaaataccatgacac catctctcgtccttcccatatcttccgtctgtgcaatgacctggctagcgcgtctgcggaaattgcgcgtggtgaaaccaacaatagcgttt cttgttacatgcgcactaaaggtatctccgaagaactggctaccgaaagcgtgatgaatctgatcgatgaaacctggaaaagatgaacaag gaaaaactgggtggtagcccgttcgcgaaaccgttcgtgaaaccgcgatcaacctggcacgtcaatctcactgcacttatcataacggcga cgcgcatacctctccggatgagctgacccgcaaacgcgttctgtctgtaatctgcgaaccgattctgccgtttgaacgcgaaaacctgtatt ttcagggcctcgagcaccaccaccaccaccactgagatccggctgctaacaaagcccgaaggaagctgagttggctgctgccaccgctgag caataactagcataaccccttggggcctctaaacgggtcttgaggggttttttgctgaaaggaggaactatatccggat
```

12) Amino Acid Sequence of *P. alba* MEA A453N G491S L494P T536C (+) TEV - pDW109 (NSPC)

(SEQ ID NO: 85)

```
MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETNNSVSCYMRTKGISEELATESVMNLIDETWKKMNKE

KLSGSPFAKPFVETAINLARQSHCTYHNGDAHTSPDELTRKRVLSVICEPILPFERENLYFQG

LEHHHHHH
```

DNA sequence of pDW109

(SEQ ID NO: 86)

```
tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcggggggctccctttagggttc cgatttagtgctttacggcacctcgaccccaaaaaacttgattagggtgatggttcacgtagtgggccatcgccctgatagacggttttttcg ccctttgacgttggagtccacgttctttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaaccctatttgttatttttctaaatacattcaaatatgtatccgctcatgaa ttaattcttagaaaaactcatcgagcatcaaatgaaactgcaatttattcatatcaggattatcaataccatatttttgaaaaagccgtttc tgtaatgaaggagaaaactcaccgaggcagttccataggatggcaagatcctggtatcggtctgcgattccgactcgtccaacatcaataca acctattaatttccctcgtcaaaaataaggttatcaagtgagaaatcaccatgagtgacgactgaatccggtgagaatggcaaaagtttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgtttcccgggatcgcagtggtgagtaaccatgcatcatcag gagtacggataaaatgcttgatggtcggaagaggcataaattccgtcagccagtttagtctgaccatctcatctgtaacatcattggcaacg ctacctttgccatgtttcagaaacaactctggcgcatcgggcttcccatacaatcgatagattgtcgcacctgattgcccgacattatcgcg agcccatttatacccatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc cgtagaaaagatcaaaggatcttcttgagatccttttttctgcgcgtaatctgctgcttgcaaacaaaaaaaccaccgctaccagcggtgg tttgtttgccggatcaagagctaccaactctttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga
```

-continued taagtcgtgtcttaccgggttggactcaagacgatagttaccggataaggcgcagcggtcgggctgaacggggggttcgtgcacacagccca
gcttggagcgaacgacctacaccgaactgagatacctacagcgtgagctatgagaaagcgccacgcttcccgaagggagaaaggcggacagg
tatccggtaagcggcagggtcggaacaggagagcgcacgagggagcttccaggggggaaacgcctggtatctttatagtcctgtcgggtttcg
ccacctctgacttgagcgtcgattttgtgatgctcgtcaggggggcggagcctatggaaaaacgccagcaacgcggcctttttacggttcc
tggccttttgctggccttttgctcacatgttctttcctgcgttatcccctgattctgtggataaccgtattaccgcctttgagtgagctgat
accgctcgccgcagccgaacgaccgagcgcagcgagtcagtgagcgaggaagcggaagagcgcctgatgcggtattttctccttacgcatct
gtgcggtatttcacaccgcatatatggtgcactctcagtacaatctgctctgatgccgcatagttaagccagtatacactccgctatcgcta
cgtgactgggtcatggctgcgccccgacacccgccaacacccgctgacgcgcctgacgggcttgtctgctcccggcatccgcttacagaca
agctgtgaccgtctccgggagctgcatgtgtcagaggttttcaccgtcatcaccgaaacgcgcgaggcagctgcggtaaagctcatcagcgt
ggtcgtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaaggggggatttctgttcatgggggtaatgataccgatgaa
acgagagaggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcacccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctgagagagt
tgcagcaagcggtccacgctggtttgccccagcaggcgaaaatcctgtttgatggtggttaacggcgggatataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggttgggaatgtaattcagctccgccatcgccgcttccacttttttcccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatgcaaggagat
ggcgcccaacagtccccggccacggggcctgccaccatacccacgccgaaacaagcgctcatgagcccgaagtggcgagcccgatcttccc
catcggtgatgtcggcgatataggcgccagcaaccgcacctgtggcgccggtgatgccggccacgatgcgtccgcgtagaggatcgagatc
tcgatcccgcgaaattaatacgactcactatagggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctgggttaccgtttcgagtctgatatccgtggtgcgctggatcgcttcgtttcctccggcggct
tcgatgcggtaaccaagacttccctgcacggtacggcactgtcttccgtctgctgcgtcaacacggttttgagggtttctcaggaagcgttc -continued agcggcttcaaagaccaaaacggcaacttcctggagaacctgaaggaagatatcaaagctatcctgagcctgtacgaggccagcttcctggc tctggaaggcgaaaacatcctggacgaggcgaaggttttcgcaatctctcatctgaaagaactgtctgaagaaaagatcggtaaagagctgg cagaacaggtgaaccatgcactggaactgccactgcatcgccgtactcagcgtctggaagcagtatggtctatcgaggcctaccgtaaaaag gaggacgcgaatcaggttctgctggagctggcaattctggattacaacatgatccagtctgtataccagcgtgatctgcgtgaaacgtcccg ttggtggcgtcgtgtgggtctggcgaccaaactgcactttgctcgtgaccgcctgattgagagcttctactgggccgtgggtgtagcattcg aaccgcaatactccgactgccgtaactccgtcgcaaaaatgttttctttcgtaaccattatcgacgatatctacgatgtatacggcaccctg gacgaactggagctgtttactgatgcagttgagcgttgggacgtaaacgccatcaacgacctgccggattacatgaaactgtgctttctggc tctgtataacactattaacgaaatcgcctacgacaacctgaaagataaaggtgagaacatcctgccgtatctgaccaaagcctgggctgacc tgtgcaacgctttcctgcaagaagccaagtggctgtacaacaaatctactccgacctttgacgactacttcggcaacgcatggaaatcctct tctggcccgctgcaactggtgttcgcttacttcgctgtcgtgcagaacattaaaaaggaagagatcgaaaacctgcaaaatacatgacac catctctcgtccttcccatatcttccgtctgtgcaatgacctggctagcgcgtctgcggaaattgcgcgtggtgaaaccaacaatagcgttt cttgttacatgcgcactaaaggtatctccgaagaactggctaccgaaagcgtgatgaatctgatcgatgaaacctggaaaaagatgaacaag gaaaaactgagtggtagcccgttcgcgaaaccgttcgtggaaaccgcgatcaacctggcacgtcaatctcactgcacttatcataacggcga cgcgcataccctctccggatgagctgacccgcaaacgcgttctgtctgtaatctgcgaaccgattctgccgtttgaacgcgaaaacctgtatt ttcagggcctcgagcaccaccaccaccaccactgagatccggctgctaacaaagcccgaaaggaagctgagttggctgctgccaccgctgag caataactagcataacccccttggggcctctaaacgggtcttgaggggttttttgctgaaaggaggaactatatccggat 13) Amino Acid Sequence of P. alba MEA G491S L494P (+) TEV - pDW110 (SP)

(SEQ ID NO: 87)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLSGSPFAKPFVETAINLARQSHCTYHNGDAHTSPDELTRKRVLSVITEPILPFERENLYFQG

LEHHHHHH

DNA sequence of pDW110

(SEQ ID NO: 88)

tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcggggctcccttagggttc cgatttagtgctttacggcacctcgaccccaaaaaacttgattagggtgatggttcacgtagtgggccatcgccctgatagacggttttcg ccctttgacgttggagtccacgttctttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaacccctatttgtttatttttctaaatacattcaaatatgtatccgctcatgaa ttaattcttagaaaaactcatcgagcatcaaatgaaactgcaatttattcatatcaggattatcaataccatattttgaaaaagccgtttc tgtaatgaaggagaaaactcaccgaggcagttccataggatggcaagatcctggtatcggtctgcgattccgactcgtccaacatcaataca acctattaatttccctcgtcaaaataaggttatcaagtgagaaatcaccatgagtgacgactgaatccggtgagaatggcaaaagtttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg -continued ctacctttgccatgtttcagaaacaactctggcgcatcgggcttcccatacaatcgatagattgtcgcacctgattgcccgacattatcgcg
agcccatttatacccatataaatcagcatccatgttggaatttaatcgcggcctagagcaagacgtttcccgttgaatatggctcataacac
cccttgtattactgtttatgtaagcagacagttttattgttcatgaccaaaatcccttaacgtgagttttcgttccactgagcgtcagaccc
cgtagaaaagatcaaaggatcttcttgagatccttttttttctgcgcgtaatctgctgcttgcaaacaaaaaaaccaccgctaccagcggtgg
tttgtttgccggatcaagagctaccaactcttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagtggcga
taagtcgtgtcttaccgggttggactcaagacgatagttaccggataaggcgcagcggtcgggctgaacggggggttcgtgcacacagccca
gcttggagcgaacgacctacaccgaactgagatacctacagcgtgagctatgagaaagcgccacgcttcccgaagggagaaaggcggacagg
tatccggtaagcggcagggtcggaacaggagagcgcacgagggagcttccaggggaaacgcctggtatctttatagtcctgtcgggtttcg
ccacctctgacttgagcgtcgattttgtgatgctcgtcaggggcggagcctatggaaaaacgccagcaacgcggccttttacggttcc
tggccttttgctggccttttgctcacatgttctttcctgcgttatcccctgattctgtggataaccgtattaccgcctttgagtgagctgat
accgctcgccgcagccgaacgaccgagcgcagcgagtcagtgagcgaggaagcggaagagcgcctgatgcggtattttctccttacgcatct
gtgcggtatttcacaccgcatatatggtgcactctcagtacaatctgctctgatgccgcatagttaagccagtatacactccgctatcgcta
cgtgactgggtcatggctgcgccccgacaccgccaacaccgctgacgcgccctgacgggcttgtctgctcccggcatccgcttacagaca
agctgtgaccgtctccgggagctgcatgtgtcagaggttttcaccgtcatcaccgaaacgcgcgaggcagctgcggtaaagctcatcagcgt
ggtcgtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaagggggatttctgttcatgggggtaatgataccgatgaa
acgagagaggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcaccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcggggagagg
cggtttgcgtattgggcgccagggtggttttcttttcaccagtgagacgggcaacagctgattgcccttcaccgcctggccctgagagagt
tgcagcaagcggtccacgctggtttgccccagcaggcgaaaatcctgtttgatggtggttaacggcgggataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggttgggaatgtaattcagctccgccatcgccgcttccacttttcccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatgcaaggagat
ggcgcccaacagtccccggccacggggcctgccaccataccaccgcgaaacaagcgctcatgagcccgaagtggcgagcccgatcttccc -continued

```
catcggtgatgtcggcgatataggcgccagcaaccgcacctgtggcgccggtgatgccggccacgatgcgtccggcgtagaggatcgagatc
tcgatcccgcgaaattaatacgactcactatagggggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaattctgaccctgctgga
actgattgacaacgtccagcgcctgggcctgggttaccgtttcgagtctgatatccgtggtgcgctggatcgcttcgtttcctccggcgct
tcgatgcggtaaccaagacttccctgcacggtacggcactgtctttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggcgtgggtgtagcattcg
aaccgcaatactccgactgccgtaactccgtcgcaaaaatgttttctttcgtaaccattatcgacgatatctacgatgtatacggcaccctg
gacgaactggagctgtttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgcttcctgcaagaagccaagtggctgtacaacaaatctactccgacctttgacgactacttcggcaacgcatggaaatcctct
tctggcccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccgcaaatagcgttt
cttgttacatgcgcactaaaggtatctccgaagaactggctaccgaaagcgtgatgaatctgatcgatgaaacctggaaaaagatgaacaag
gaaaaactgagtggtagcccgttcgcgaaaccgttcgtggaaaccgcgatcaacctggcacgtcaatctcactgcacttatcataacggcga
cgcgcatacctctccggatgagctgacccgcaaacgcgttctgtctgtaatcactgaaccgattctgccgtttgaacgcgaaaacctgtatt
ttcagggcctcgagcaccaccaccaccaccactgagatccggctgctaacaaagcccgaaaggaagctgagttggctgctgccaccgctgag
caataactagcataacccctttggggcctctaaacgggtcttgaggggttttttgctgaaaggaggaactatatccggat
```

14) Amino Acid Sequence of *P. alba* MEA G491S T536C (+) TEV - pDW111 (SC)
(SEQ ID NO: 89)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLSGSLFAKPFVETAINLARQSHCTYHNGDAHTSPDELTRKRVLSVICEPILPFERENLYFQG

LEHHHHHH

DNA sequence of pDW111
(SEQ ID NO: 90)

```
tggcgaatgggacgcgccctgtagcggcgcattaagcgcggcgggtgtggtggttacgcgcagcgtgaccgctacacttgccagcgccctag
cgcccgctcctttcgctttcttcccttcctttctcgccacgttcgccggctttccccgtcaagctctaaatcggggggctcccttagggttc
cgatttagtgctttacggcacctcgaccccaaaaaacttgattagggtgatggttcacgtagtgggccatcgccctgatagacggttttcg
cccttgacgttggagtccacgttctttaatagtggactcttgttccaaactggaacaacactcaaccctatctcggtctattcttttgatt
tataagggattttgccgatttcggcctattggttaaaaaatgagctgatttaacaaaaatttaacgcgaattttaacaaaatattaacgttt
acaatttcaggtggcacttttcggggaaatgtgcgcggaaccccctatttgtttatttttctaaatacattcaaatatgtatccgctcatgaa
ttaattcttagaaaaactcatcgagcatcaaatgaaactgcaatttattcatatcaggattatcaataccatattttttgaaaaagccgtttc
```

```
tgtaatgaaggagaaaactcaccgaggcagttccataggatggcaagatcctggtatcggtctgcgattccgactcgtccaacatcaataca
acctattaatttccctcgtcaaaaataaggttatcaagtgagaaatcaccatgagtgacgactgaatccggtgagaatggcaaaagtttat
gcatttctttccagacttgttcaacaggccagccattacgctcgtcatcaaaatcactcgcatcaaccaaaccgttattcattcgtgattgc
gcctgagcgagacgaaatacgcgatcgctgttaaaaggacaattacaaacaggaatcgaatgcaaccggcgcaggaacactgccagcgcatc
aacaatattttcacctgaatcaggatattcttctaatacctggaatgctgttttcccggggatcgcagtggtgagtaaccatgcatcatcag
gagtacggataaaatgcttgatggtcggaagaggcataaattccgtcagccagtttagtctgaccatctcatctgtaacatcattggcaacg
ctacctttgccatgtttcagaaacaactctggcgcatcgggcttcccatacaatcgatagattgtcgcacctgattgcccgacattatcgcg
agcccatttatacccatataaatcagcatccatgttggaatttaatcgcggcctagagcaagacgtttcccgttgaatatggctcataacac
cccttgtattactgtttatgtaagcagacagttttattgttcatgaccaaaatcccttaacgtgagttttcgttccactgagcgtcagaccc
cgtagaaaagatcaaaggatcttcttgagatccttttttttctgcgcgtaatctgctgcttgcaaacaaaaaaaccaccgctaccagcggtgg
tttgtttgccggatcaagagctaccaactcttttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagtggcga
taagtcgtgtcttaccgggttggactcaagacgatagttaccggataaggcgcagcggtcgggctgaacggggggttcgtgcacacagccca
gcttggagcgaacgacctacaccgaactgagatacctacagcgtgagctatgagaaagcgccacgcttcccgaagggagaaaggcggacagg
tatccggtaagcggcagggtcggaacaggagagcgcacgagggagcttccaggggaaacgcctggtatctttatagtcctgtcgggtttcg
ccacctctgacttgagcgtcgatttttgtgatgctcgtcaggggggcggagcctatggaaaaacgccagcaacgcggcctttttacggttcc
tggccttttgctggccttttgctcacatgttctttcctgcgttatcccctgattctgtggataaccgtattaccgcctttgagtgagctgat
accgctcgccgcagccgaacgaccgagcgcagcgagtcagtgagcgaggaagcggaagagcgcctgatgcggtattttctccttacgcatct
gtgcggtatttcacaccgcatatatggtgcactctcagtacaatctgctctgatgccgcatagttaagccagtatacactccgctatcgcta
cgtgactgggtcatggctgcgccccgacacccgccaacacccgctgacgcgccctgacgggcttgtctgctcccggcatccgcttacagaca
agctgtgaccgtctccgggagctgcatgtgtcagaggttttcaccgtcatcaccgaaacgcgcgaggcagctgcggtaaagctcatcagcgt
ggtcgtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaagggggatttctgttcatgggggtaatgataccgatgaa
acgagagaggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcacccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgcccaccgaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctgagagagt
tgcagcaagcggtccacgctggtttgccccagcaggcgaaaatcctgtttgatggtggttaacggcgggatataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagtaatgatc
agcccactgacgcgttgcgcgagaagattgtgcaccgccgctttacaggcttcgacgccgcttcgttctaccatcgacaccaccacgctggc
```

-continued

```
acccagttgatcggcgcgagatttaatcgccgcgacaatttgcgacggcgcgtgcagggccagactggaggtggcaacgccaatcagcaacg
actgtttgcccgccagttgttgtgccacgcggtttgggaatgtaattcagctccgccatcgccgcttccacttttttcccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatgcaaggagat
ggcgcccaacagtcccccggccacggggcctgccaccatacccacgccgaaacaagcgctcatgagcccgaagtggcgagcccgatcttccc
catcggtgatgtcggcgatataggcgccagcaaccgcacctgtggcgccggtgatgccggccacgatgcgtccggcgtagaggatcgagatc
tcgatcccgcgaaattaatacgactcactatagggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctgggttaccgtttcgagtctgatatccgtggtgcgctggatcgcttcgtttcctccggcggct
tcgatgcggtaaccaagacttcctgcacggtacggcactgtcttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttctttcgtaaccattatcgacgatatctacgatgtatacggcaccctg
gacgaactggagctgttttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgacctttgacgactacttcggcaacgcatggaaatcctct
tctggcccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccgcaaatagcgttt
cttgttacatgcgcactaaaggtatctccgaagaactggctaccgaaagcgtgatgaatctgatcgatgaaacctggaaaaagatgaacaag
gaaaaactgagtggtagcctgttcgcgaaaccgttcgtggaaaccgcgatcaacctggcacgtcaatctcactgcacttatcataacggcga
cgcgcataccctccggatgagctgacccgcaaacgcgttctgtctgtaatctgcgaaccgattctgccgtttgaacgcgaaaacctgtatt
ttcagggcctcgagcaccaccaccaccaccactgagatccggctgctaacaaagcccgaaaggaagctgagttggctgctgccaccgctgag
caataactagcataaccccttggggcctctaaacgggtcttgaggggttttttgctgaaaggaggaactatatccggat
```

15) Amino Acid Sequence of P. alba MEA G491S L494P T536C (+) TEV - pDW112 (SPC)

(SEQ ID NO: 91)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLSGSPFAKPFVETAINLARQSHCTYHNGDAHTSPDELTRKRVLSVICEPILPFERENLYFQG

LEHHHHHH

DNA sequence of pDW112

(SEQ ID NO: 92)

tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcggggggctccctttagggttc cgatttagtgctttacggcacctcgaccccaaaaaacttgattagggtgatggttcacgtagtgggccatcgccctgatagacggttttttcg ccctttgacgttggagtccacgttctttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaacccctatttgtttatttttctaaatacattcaaatatgtatccgctcatgaa ttaattcttagaaaaactcatcgagcatcaaatgaaactgcaatttattcatatcaggattatcaataccatattttgaaaaagccgtttc tgtaatgaaggagaaaactcaccgaggcagttccataggatggcaagatcctggtatcggtctgcgattccgactcgtccaacatcaataca acctattaatttcccctcgtcaaaaataaggttatcaagtgagaaatcaccatgagtgacgactgaatccggtgagaatggcaaaagtttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg ctacctttgccatgtttcagaaacaactctggcgcatcgggcttcccatacaatcgatagattgtcgcacctgattgcccgacattatcgcg agcccatttatacccatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc cgtagaaaagatcaaaggatcttcttgagatcctttttttctgcgcgtaatctgctgcttgcaaacaaaaaaaccaccgctaccagcggtgg tttgtttgccggatcaagagctaccaactctttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga taagtcgtgtcttaccgggttggactcaagacgatagttaccggataaggcgcagcggtcgggctgaacggggggttcgtgcacacagccca gcttggagcgaacgacctacaccgaactgagatacctacagcgtgagctatgagaaagcgccacgcttcccgaagggagaaaggcggacagg tatccggtaagcggcagggtcggaacaggagagcgcacgagggagcttccaggggaaacgcctggtatctttatagtcctgtcgggtttcg ccacctctgacttgagcgtcgatttttgtgatgctcgtcaggggggcggagcctatggaaaaacgccagcaacgcggcctttttacggttcc tggccttttgctggccttttgctcacatgttctttcctgcgttatcccctgattctgtggataaccgtattaccgcctttgagtgagctgat accgctcgccgcagccgaacgaccgagcgcagcgagtcagtgagcgaggaagcggaagagcgcctgatgcggtattttctccttacgcatct gtgcggtatttcacaccgcatatatggtgcactctcagtacaatctgctctgatgccgcatagttaagccagtatacactccgctatcgcta cgtgactgggtcatggctgcgccccgacacccgccaacacccgctgacgcgccctgacgggcttgtctgctcccggcatccgcttacagaca agctgtgaccgtctccgggagctgcatgtgtcagaggttttcaccgtcatcaccgaaacgcgcgaggcagctgcggtaaagctcatcagcgt ggtcgtgaagcgattcacagatgtctgcctgttcatccgcgtccagctcgttgagtttctccagaagcgttaatgtctggcttctgataaag cgggccatgttaagggcggttttttcctgtttggtcactgatgcctccgtgtaaggggggattctgttcatgggggtaatgataccgatgaa acgagagaggatgctcacgatacgggttactgatgatgaacatgcccggttactggaacgttgtgagggtaaacaactggcggtatggatgc ggcgggaccagagaaaaatcactcagggtcaatgccagcgcttcgttaatacagatgtaggtgttccacagggtagccagcagcatcctgcg atgcagatccggaacataatggtgcagggcgctgacttccgcgtttccagactttacgaaacacggaaaccgaagaccattcatgttgttgc tcaggtcgcagacgttttgcagcagcagtcgcttcacgttcgctcgcgtatcggtgattcattctgctaaccagtaaggcaaccccgccagc ctagccgggtcctcaacgacaggagcacgatcatgcgcacccgtggggccgccatgccggcgataatggcctgcttctcgccgaaacgtttg gtggcgggaccagtgacgaaggcttgagcgagggcgtgcaagattccgaataccgcaagcgacaggccgatcatcgtcgcgctccagcgaaa gcggtcctcgccgaaaatgacccagagcgctgccggcacctgtcctacgagttgcatgataaagaagacagtcataagtgcggcgacgatag tcatgccccgcgcccaccggaaggagctgactgggttgaaggctctcaagggcatcggtcgagatcccggtgcctaatgagtgagctaactt acattaattgcgttgcgctcactgcccgctttccagtcgggaaacctgtcgtgccagctgcattaatgaatcggccaacgcgcggggagagg -continued

```
cggtttgcgtattgggcgccagggtggtttttcttttcaccagtgagacgggcaacagctgattgcccttcaccgcctggccctgagagagt
tgcagcaagcggtccacgctggtttgccccagcaggcgaaaatcctgtttgatggtggttaacggcgggatataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggcagactggaggtggcaacgccaatcagcaacg
actgtttgcccgccagttgttgtgccacgcggttgggaatgtaattcagctccgccatcgccgcttccacttttccccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccaaggaatggtgcatgcaaggagat
ggcgcccaacagtccccggccacggggcctgccaccatacccacgccgaaacaagcgctcatgagcccgaagtggcgagcccgatcttccc
catcggtgatgtcggcgatataggcgccagcaaccgcacctgtggcgccggtgatgccggccacgatgcgtccggcgtagaggatcgagatc
tcgatcccgcgaaattaatacgactcactataggggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctgggttaccgtttcgagtctgatatccgtggtgcgctggatcgcttcgtttcctccggcggct
tcgatgcggtaaccaagacttccctgcacggtacggcactgtcttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttctttcgtaaccattatcgacgatatctacgatgtatacggcaccctg
gacgaactggagctgttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgacctttgacgactacttcggcaacgcatggaaatcctct
tctggcccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccgcaaatagcgttt
cttgttacatgcgcactaaaggtatctccgaagaactggctaccgaaagcgtgatgaatctgatcgatgaaacctggaaaaagatgaacaag
gaaaaactgagtggtagcccgttcgcgaaaccgttcgtggaaaccgcgatcaacctggcacgtcaatctcactgcacttatcataacggcga
cgcgcataccctccggatgagctgacccgcaaacgcgttctgtctgtaatctgcgaaccgattctgccgtttgaacgcgaaaacctgtatt
ttcagggcctcgagcaccaccaccaccaccactgagatccggctgctaacaaagcccgaaaggaagctgagttggctgctgccaccgctgag
caataactagcataaccccttggggcctctaaacgggtcttgaggggttttttgctgaaaggaggaactatatccggat
```

16) Amino Acid Sequence of *P. alba* MEA L494P T536C (+) TEV - pDW113 (PC)

(SEQ ID NO: 93)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLGGSPFAKPFVETAINLARQSHCTYHNGDAHTSPDELTRKRVLSVICEPILPFERENLYFQG

LEHHHHHH

DNA sequence of pDW113

(SEQ ID NO: 94)

tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcggggggctcccttagggttc cgatttagtgctttacggcacctcgaccccaaaaaacttgattagggtgatggttcacgtagtgggccatcgccctgatagacggttttcg ccctttgacgttggagtccacgttctttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaacccctatttgtttatttttctaaatacattcaaatatgtatccgctcatgaa ttaattcttagaaaaactcatcgagcatcaaatgaaactgcaatttattcatatcaggattatcaataccatattttttgaaaaagccgttc tgtaatgaaggagaaaactcaccgaggcagttccataggatggcaagatcctggtatcggtctgcgattccgactcgtccaacatcaataca acctattaatttcccctcgtcaaaaataaggttatcaagtgagaaatcaccatgagtgacgactgaatccggtgagaatggcaaaagtttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg ctacctttgccatgtttcagaaacaactctggcgcatcgggcttcccatacaatcgatagattgtcgcacctgattgcccgacattatcgcg agcccatttatacccatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc cgtagaaaagatcaaaggatcttcttgagatcctttttttctgcgcgtaatctgctgcttgcaaacaaaaaaaccaccgctaccagcggtgg tttgtttgccggatcaagagctaccaactctttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga taagtcgtgtcttaccgggttggactcaagacgatagttaccggataaggcgcagcggtcgggctgaacggggggttcgtgcacacagccca gcttggagcgaacgacctacaccgaactgagatacctacagcgtgagctatgagaaagcgccacgcttcccgaagggagaaaggcggacagg tatccggtaagcggcagggtcggaacaggagagcgcacgagggagcttccagggggaaacgcctggtatctttatagtcctgtcgggtttcg ccacctctgacttgagcgtcgatttttgtgatgctcgtcaggggggcggagcctatggaaaaacgccagcaacgcggcctttttacggttcc tggccttttgctggccttttgctcacatgttctttcctgcgttatcccctgattctgtggataaccgtattaccgcctttgagtgagctgat accgctcgccgcagccgaacgaccgagcgcagcgagtcagtgagcgaggaagcggaagagcgcctgatgcggtattttctccttacgcatct gtgcggtatttcacaccgcatatatggtgcactctcagtacaatctgctctgatgccgcatagttaagccagtatacactccgctatcgcta cgtgactgggtcatggctgcgccccgacacccgccaacacccgctgacgcgccctgacgggcttgtctgctcccggcatccgcttacagaca agctgtgaccgtctccgggagctgcatgtgtcagaggttttcaccgtcatcaccgaaacgcgcgaggcagctgcggtaaagctcatcagcgt ggtcgtgaagcgattcacagatgtctgcctgttcatccgcgtccagctcgttgagtttctccagaagcgttaatgtctggcttctgataaag cgggccatgttaagggcggttttttcctgtttggtcactgatgcctccgtgtaagggggatttctgttcatgggggtaatgataccgatgaa acgagagaggatgctcacgatacgggttactgatgatgaacatgcccggttactggaacgttgtgagggtaaacaactggcggtatggatgc ggcgggaccagagaaaaatcactcagggtcaatgccagcgcttcgttaatacagatgtaggtgttccacagggtagccagcagcatcctgcg atgcagatccggaacataatggtgcagggcgctgacttccgcgtttccagactttacgaaacacggaaaccgaagaccattcatgttgttgc

```
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcaccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcggggagagg
cggtttgcgtattgggcgccagggtggttttcttttcaccagtgagacgggcaacagctgattgcccttcaccgcctggccctgagagagt
tgcagcaagcggtccacgctggtttgcccagcaggcgaaaatcctgtttgatggtggttaacggcgggataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagctttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgaccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggttgggaatgtaattcagctccgccatcgccgcttccacttttttcccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccaaggaatggtgcatgcaaggagat
ggcgcccaacagtcccccggccacggggcctgccaccatacccacgccgaaacaagcgctcatgagcccgaagtggcgagcccgatcttccc
catcggtgatgtcggcgatataggcgccagcaaccgcacctgtggcgccggtgatgccgccacgatgcgtccggcgtagaggatcgagatc
tcgatcccgcgaaattaatacgactcactataggggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctggttaccgtttcgagtctgatatccgtggtgcgctggatcgcttcgtttcctccggcggct
tcgatgcggtaaccaagacttccctgcacggtacggcactgtctttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaacatcctggacgaggcgaaggttttcgcaatctctcatctgaaagaactgtctgaagaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggccgtgggtgtagcattcg
aaccgcaatactccgactgccgtaactccgtcgcaaaaatgttttctttcgtaaccattatcgacgatatctacgatgtatacggcaccctg
gacgaactggagctgtttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgaccttgacgactacttcggcaacgcatggaaatcctct
tctggcccgctgcaactggtgttcgcttacttcgctgtcgtgcagaacattaaaaaggaagagatcgaaaacctgcaaaaataccatgacac
catctctcgtccttcccatatcttccgtctgtgcaatgacctggctagcgcgtctgcggaaattgcgcgtggtgaaaccgcaaatagcgttt
cttgttacatgcgcactaaaggtatctccgaagaactggctaccgaaagcgtgatgaatctgatcgatgaaacctggaaaagatgaacaag
gaaaaactgggtggtagcccgttcgcgaaaccgttcgtggaaaccgcgatcaacctggcacgtcaatctcactgcacttatcataacggcga
cgcgcatacctctccggatgagctgacccgcaaacgcgttctgtctgtaatctgcgaaccgattctgccgttgaacgcgaaaacctgtatt
ttcagggcctcgagcaccaccaccaccaccactgagatccggctgctaacaaagcccgaaaggaagctgagttggctgctgccaccgctgag
```

-continued caataactagcataaccccttggggcctctaaacgggtcttgaggggttttttgctgaaaggaggaactatatccggat Amino Acid Sequence of P. alba MEA T536F (+) TEV - pDW87 (SEQ ID NO: 95)

MEARRSANYEPNSWDYDYLLSSDTDESIEVYKDKAKKLEAEVRREINNEKAEFLTLLELID
NVQRLGLGYRFESDIRGALDRFVSSGGFDAVTKTSLHGTALSFRLLRQHGFEVSQEAFSGF
KDQNGNFLENLKEDIKAILSLYEASFLALEGENILDEAKVFAISHLKELSEEKIGKELAEQVN
HALELPLHRRTQRLEAVWSIEAYRKKEDANQVLLELAILDYNMIQSVYQRDLRETSRWWR
RVGLATKLHFARDRLIESFYWAVGVAFEPQYSDCRNSVAKMFSFVTIIDDIYDVYGTLDEL
ELFTDAVERWDVNAINDLPDYMKLCFLALYNTINEIAYDNLKDKGENILPYLTKAWADLC
NAFLQEAKWLYNKSTPTFDDYFGNAWKSSSGPLQLVFAYFAVVQNIKKEEIENLQKYHDTI
SRPSHIFRLCNDLASASAEIARGETANSVSCYMRTKGISEELATESVMNLIDETWKKMNKE
KLGGSLFAKPFVETAINLARQSHCTYHNGDAHTSPDELTRKRVLSVIFEPILPFERENLYFQG
LEHHHHHH

DNA sequence of pDW87 (SEQ ID NO: 96)

tggcgaatgggacgcgccctgtagcggcgcattaagcgcggcgggtgtggtggttacgcgcagcgtgaccgctacacttgccagcgccctag
cgcccgctcctttcgctttcttcccttcctttctcgccacgttcgccggctttccccgtcaagctctaaatcggggggctcccttagggttc
cgatttagtgctttacggcacctcgaccccaaaaaacttgattagggtgatggttcacgtagtgggccatcgccctgatagacggttttcg
ccctttgacgttggagtccacgttctttaatagtggactcttgttccaaactggaacaacactcaaccctatctcggtctattcttttgatt
tataagggattttgccgatttcggcctattggttaaaaatgagctgatttaacaaaaatttaacgcgaattttaacaaaatattaacgttt
acaatttcaggtggcacttttcggggaaatgtgcgcggaacccctatttgtttatttttctaaatacattcaaatatgtatccgctcatgaa
ttaattcttagaaaaactcatcgagcatcaaatgaaactgcaatttattcatatcaggattatcaataccatatttttgaaaaagccgtttc
tgtaatgaaggagaaaactcaccgaggcagttccataggatggcaagatcctggtatcggtctgcgattccgactcgtccaacatcaataca
acctattaatttcccctcgtcaaaaataaggttatcaagtgagaaatcaccatgagtgacgactgaatccggtgagaatggcaaaagtttat
gcatttctttccagacttgttcaacaggccagccattacgctcgtcatcaaaatcactcgcatcaaccaaaccgttattcattcgtgattgc
gcctgagcgagacgaaatacgcgatcgctgttaaaaggacaattacaaacaggaatcgaatgcaaccggcgcaggaacactgccagcgcatc
aacaatattttcacctgaatcaggatattcttctaatacctggaatgctgtttttcccggggatcgcagtggtgagtaaccatgcatcatcag
gagtacggataaaatgcttgatggtcggaagaggcataaattccgtcagccagtttagtctgaccatctcatctgtaacatcattggcaacg
ctacctttgccatgtttcagaaacaactctggcgcatcgggcttcccatacaatcgatagattgtcgcacctgattgcccgacattatcgcg
agcccatttatacccatataaatcagcatccatgttggaatttaatcgcggcctagagcaagacgtttcccgttgaatatggctcataacac
cccttgtattactgtttatgtaagcagacagttttattgttcatgaccaaaatcccttaacgtgagttttcgttccactgagcgtcagaccc
cgtagaaaagatcaaaggatcttcttgagatccttttttttctgcgcgtaatctgctgcttgcaaacaaaaaaaccaccgctaccagcggtgg
tttgtttgccggatcaagagctaccaactctttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagtggcga
taagtcgtgtcttaccgggttggactcaagacgatagttaccggataaggcgcagcggtcgggctgaacggggggttcgtgcacacagccca
gcttggagcgaacgacctacaccgaactgagatacctacagcgtgagctatgagaaagcgccacgcttcccgaagggagaaaggcggacagg
tatccggtaagcggcagggtcggaacaggagagcgcacgagggagcttccaggggaaacgcctggtatctttatagtcctgtcgggtttcg
ccacctctgacttgagcgtcgatttttgtgatgctcgtcaggggggcggagcctatggaaaaacgccagcaacgcggcctttttacggttcc
tggccttttgctggccttttgctcacatgttcttcctgcgttatcccctgattctgtggataaccgtattaccgcctttgagtgagctgat
accgctcgccgcagccgaacgaccgagcgcagcgagtcagtgagcgaggaagcggaagagcgcctgatgcggtattttctccttacgcatct
gtgcggtatttcacaccgcatatatggtgcactctcagtacaatctgctctgatgccgcatagttaagccagtatacactccgctatcgcta
cgtgactgggtcatggctgcgccccgacacccgccaacacccgctgacgcgccctgacgggcttgtctgctcccggcatccgcttacagaca -continued

```
agctgtgaccgtctccgggagctgcatgtgtcagaggttttcaccgtcatcaccgaaacgcgcgaggcagctgcggtaaagctcatcagcgt
ggtcgtgaagcgattcacagatgtctgcctgttcatccgcgtccagctcgttgagtttctccagaagcgttaatgtctggcttctgataaag
cgggccatgttaagggcggttttttcctgtttggtcactgatgcctccgtgtaagggggatttctgttcatgggggtaatgataccgatgaa
acgagagaggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcagcatcctgcg
atgcagatccggaacataatggtgcagggcgctgacttccgcgtttccagactttacgaaacacggaaaccgaagaccattcatgttgttgc
tcaggtcgcagacgttttgcagcagcagtcgcttcacgttcgctcgcgtatcggtgattcattctgctaaccagtaaggcaaccccgccagc
ctagccgggtcctcaacgacaggagcacgatcatgcgcaccgtggggccgccatgccggcgataatggcctgcttctcgccgaaacgtttg
gtggcgggaccagtgacgaaggcttgagcgagggcgtgcaagattccgaataccgcaagcgacaggccgatcatcgtcgcgctccagcgaaa
gcggtcctcgccgaaaatgacccagagcgctgccggcacctgtcctacgagttgcatgataaagaagacagtcataagtgcggcgacgatag
tcatgccccgcgcccaccggaaggagctgactgggttgaaggctctcaagggcatcggtcgagatcccggtgcctaatgagtgagctaactt
acattaattgcgttgcgctcactgcccgctttccagtcgggaaacctgtcgtgccagctgcattaatgaatcggccaacgcgcgggagagg
cggtttgcgtattgggcgccagggtggttttcttttcaccagtgagacgggcaacagctgattgcccttcaccgcctggccctgagagagt
tgcagcaagcggtccacgctggtttgccccagcaggcgaaaatcctgtttgatggtggttaacggcgggataacatgagctgtcttcggt
atcgtcgtatcccactaccgagatatccgcaccaacgcgcagcccggactcggtaatggcgcgcattgcgcccagcgccatctgatcgttgg
caaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggcccgctaacag
cgcgatttgctggtgacccaatgcgaccagatgctccacgcccagtcgcgtaccgtcttcatgggagaaaataatactgttgatgggtgtct
ggtcagagacatcaagaaataacgccggaacattagtgcaggcagcttccacagcaatggcatcctggtcatccagcggatagttaatgatc
agcccactgacgcgttgcgcgagaagattgtgcaccgccgctttacaggcttcgacgccgcttcgttctaccatcgacaccaccacgctggc
acccagttgatcggcgcgagatttaatcgccgcgacaatttgcgacggcgcgtgcagggccagactggaggtggcaacgccaatcagcaacg
actgtttgcccgccagttgttgtgccacgcggttgggaatgtaattcagctccgccatcgccgcttccacttttttcccgcgttttcgcagaa
acgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatgcaaggagat
ggcgcccaacagtcccccggccacggggcctgccaccatacccacgccgaaacaagcgctcatgagcccgaagtggcgagcccgatcttccc
catcggtgatgtcggcgatataggcgccagcaaccgcacctgtggcgccggtgatgccggccacgatgcgtccggcgtagaggatcgagatc
tcgatcccgcgaaattaatacgactcactatagggaattgtgagcggataacaattcccctctagaaataattttgtttaactttaagaag
gagatatacatatggaagctcgtcgttctgcgaactacgaacctaacagctgggactatgattacctgctgtcctccgacacggacgagtcc
atcgaagtatacaaagacaaagcgaaaaagctggaagccgaagttcgtcgcgagattaataacgaaaaagcagaatttctgaccctgctgga
actgattgacaacgtccagcgcctgggcctgggttaccgtttcgagtctgatatccgtggtgcgctggatcgcttcgtttcctccggcggct
tcgatgcggtaaccaagacttccctgcacggtacggcactgtcttttccgtctgctgcgtcaacacggttttgaggtttctcaggaagcgttc
agcggcttcaaagaccaaaacggcaacttcctggagaacctgaaggaagatatcaaagctatcctgagcctgtacgaggccagcttcctggc
tctggaaggcgaaaacatcctggacgaggcgaaggttttcgcaatctctcatctgaaagaactgtctgaagaaaagatcggtaaagagctgg
cagaacaggtgaaccatgcactggaactgccactgcatcgccgtactcagcgtctggaagcagtatggtctatcgaggcctaccgtaaaaag
gaggacgcgaatcaggttctgctggagctggcaattctggattacaacatgatccagtctgtataccagcgtgatctgcgtgaaacgtcccg
ttggtggcgtcgtgtgggtctggcgaccaaactgcactttgctcgtgaccgcctgattgagagcttctactgggcgtgggtgtagcattcg
aaccgcaatactccgactgccgtaactccgtcgcaaaaatgttttctttcgtaaccattatcgacgatatctacgatgtatacggcaccctg
gacgaactggagctgtttactgatgcagttgagcgttgggacgtaaacgccatcaacgacctgccggattacatgaaactgtgctttctggc
tctgtataacactattaacgaaatcgcctacgacaacctgaaagataaaggtgagaacatcctgccgtatctgaccaaagcctgggctgacc
tgtgcaacgctttcctgcaagaagccaagtggctgtacaacaaatctactccgacctttgacgactacttcggcaacgcatggaaatcctct
```

-continued tctggcccgctgcaactggtgttcgcttacttcgctgtcgtgcagaacattaaaaggaagagatcgaaaacctgcaaaaataccatgacac catctctcgtccttcccatatcttccgtctgtgcaatgacctggctagcgcgtctgcggaaattgcgcgtggtgaaaccgcaaatagcgttt cttgttacatgcgcactaaaggtatctccgaagaactggctaccgaaagcgtgatgaatctgatcgatgaaacctggaaaaagatgaacaag gaaaaactgggtggtagcctgttcgcgaaaccgttcgtggaaaccgcgatcaacctggcacgtcaatctcactgcacttatcataacggcga cgcgcatacctctccggatgagctgacccgcaaacgcgttctgtctgtaatctttgaaccgattctgccgtttgaacgcgaaaacctgtatt ttcagggcctcgagcaccaccaccaccaccactgagatccggctgctaacaaagcccgaaaggaagctgagttggctgctgccaccgctgag caataactagcataaccccttggggcctctaaacgggtcttgaggggttttttgctgaaaggaggaactatatccggat Amino Acid Sequence of *P. alba* MEA L494P T536F (+) TEV - pDW95 (SEQ ID NO: 97)

MEARRSANYEPNSWDYDYLLSSDTDESIEVYKDKAKKLEAEVRREINNEKAEFLTLLELID

NVQRLGLGYRFESDIRGALDRFVSSGGFDAVTKTSLHGTALSFRLLRQHGFEVSQEAFSGF

KDQNGNFLENLKEDIKAILSLYEASFLALEGENILDEAKVFAISHLKELSEEKIGKELAEQVN

HALELPLHRRTQRLEAVWSIEAYRKKEDANQVLLELAILDYNMIQSVYQRDLRETSRWWR

RVGLATKLHFARDRLIESFYWAVGVAFEPQYSDCRNSVAKMFSFVTIIDDIYDVYGTLDEL

ELFTDAVERWDVNAINDLPDYMKLCFLALYNTINEIAYDNLKDKGENILPYLTKAWADLC

NAFLQEAKWLYNKSTPTFDDYFGNAWKSSSGPLQLVFAYFAVVQNIKKEEIENLQKYHDTI

SRPSHIFRLCNDLASASAEIARGETANSVSCYMRTKGISEELATESVMNLIDETWKKMNKE

KLGGSPFAKPFVETAINLARQSHCTYHNGDAHTSPDELTRKRVLSVIFEPILPFERENLYFQG

LEHHHHHH

DNA sequence of pDW95 (SEQ ID NO: 98)

tggcgaatgggacgcgccctgtagcggcgcattaagcgcggcgggtgtggtggttacgcgcagcgtgaccgctacacttgccagcgccctag cgcccgctcctttcgctttcttcccttcctttctcgccacgttcgccggctttccccgtcaagctctaaatcggggctcccttagggttc cgatttagtgctttacggcacctcgaccccaaaaaacttgattagggtgatggttcacgtagtgggccatcgccctgatagacggttttcg ccctttgacgttggagtccacgttctttaatagtggactcttgttccaaactggaacaacactcaaccctatctcggtctattcttttgatt tataagggattttgccgatttcggcctattggttaaaaaatgagctgatttaacaaaaatttaacgcgaattttaacaaaatattaacgttt acaatttcaggtggcacttttcggggaaatgtgcgcggaaccccctatttgtttatttttctaaatacattcaaatatgtatccgctcatgaa ttaattcttagaaaaactcatcgagcatcaaatgaaactgcaatttattcatatcaggattatcaataccatatttttgaaaaagccgtttc tgtaatgaaggagaaaactcaccgaggcagttccataggatggcaagatcctggtatcggtctgcgattccgactcgtccaacatcaataca acctattaatttcccctcgtcaaaaataaggttatcaagtgagaaatcaccatgagtgacgactgaatccggtgagaatggcaaaagtttat gcatttctttccagacttgttcaacaggccagccattacgctcgtcatcaaaatcactcgcatcaaccaaaccgttattcattcgtgattgc gcctgagcgagacgaaatacgcgatcgctgttaaaaggacaattacaaacaggaatcgaatgcaaccggcgcaggaacactgccagcgcatc aacaatattttcacctgaatcaggatattcttctaatacctggaatgctgttttcccggggatcgcagtggtgagtaaccatgcatcatcag gagtacggataaaatgcttgatggtcggaagaggcataaattccgtcagccagtttagtctgaccatctcatctgtaacatcattggcaacg ctacctttgccatgtttcagaaacaactctggcgcatcgggcttcccatacaatcgatagattgtcgcacctgattgcccgacattatcgcg agcccatttatacccatataaatcagcatccatgttggaatttaatcgcggcctagagcaagacgtttcccgttgaatatggctcataacac cccttgtattactgtttatgtaagcagacagttttattgttcatgaccaaaatcccttaacgtgagttttcgttccactgagcgtcagaccc cgtagaaagatcaaaggatcttcttgagatcctttttttctgcgcgtaatctgctgcttgcaaacaaaaaaaccaccgctaccagcggtgg tttgtttgccggatcaagagctaccaactctttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggcga taagtcgtgtcttaccgggttggactcaagacgatagttaccggataaggcgcagcggtcgggctgaacggggggttcgtgcacacagccca gcttggagcgaacgacctacaccgaactgagatacctacagcgtgagctatgagaaagcgccacgcttcccgaagggagaaaggcggacagg -continued tatccggtaagcggcagggtcggaacaggagagcgcacgagggagcttccaggggaaacgcctggtatctttatagtcctgtcgggtttcg ccacctctgacttgagcgtcgattttttgtgatgctcgtcaggggggcggagcctatggaaaaacgccagcaacgcggcctttttacggttcc tggccttttgctggccttttgctcacatgttctttcctgcgttatcccctgattctgtggataaccgtattaccgcctttgagtgagctgat accgctcgccgcagccgaacgaccgagcgcagcgagtcagtgagcgaggaagcggaagagcgcctgatgcggtattttctccttacgcatct gtgcggtatttcacaccgcatatatggtgcactctcagtacaatctgctctgatgccgcatagttaagccagtatacactccgctatcgcta cgtgactgggtcatggctgcgccccgacacccgccaacacccgctgacgcgccctgacgggcttgtctgctcccggcatccgcttacagaca agctgtgaccgtctccgggagctgcatgtgtcagaggttttcaccgtcatcaccgaaacgcgcgaggcagctgcggtaaagctcatcagcgt ggtcgtgaagcgattcacagatgtctgcctgttcatccgcgtccagctcgttgagtttctccagaagcgttaatgtctggcttctgataaag cgggccatgttaagggcggttttttcctgtttggtcactgatgcctccgtgtaagggggattttctgttcatgggggtaatgataccgatgaa acgagagaggatgctcacgatacgggttactgatgatgaacatgcccggttactggaacgttgtgagggtaaacaactggcggtatggatgc ggcgggaccagagaaaaatcactcagggtcaatgccagcgcttcgttaatacagatgtaggtgttccacagggtagccagcagcatcctgcg atgcagatccggaacataatggtgcagggcgctgacttccgcgtttccagactttacgaaacacggaaaccgaagaccattcatgttgttgc tcaggtcgcagacgttttgcagcagcagtcgcttcacgttcgctcgcgtatcggtgattcattctgctaaccagtaaggcaaccccgccagc ctagccgggtcctcaacgacaggagcacgatcatgcgcacccgtggggccgccatgccggcgataatggcctgcttctcgccgaaacgtttg gtggcgggaccagtgacgaaggcttgagcgagggcgtgcaagattccgaataccgcaagcgacaggccgatcatcgtcgcgctccagcgaaa gcggtcctcgccgaaaatgacccagagcgctgccggcacctgtcctacgagttgcatgataaagaagacagtcataagtgcggcgacgatag tcatgccccgcgcccaccggaaggagctgactgggttgaaggctctcaagggcatcggtcgagatcccggtgcctaatgagtgagctaactt acattaattgcgttgcgctcactgcccgctttccagtcgggaaacctgtcgtgccagctgcattaatgaatcggccaacgcgcggggagagg cggtttgcgtattgggcgccagggtggtttttcttttcaccagtgagacgggcaacagctgattgcccttcaccgcctggccctgagagagt tgcagcaagcggtccacgctggtttgccccagcaggcgaaaatcctgtttgatggtggttaacggcgggatataacatgagctgtcttcggt atcgtcgtatcccactaccgagatatccgcaccaacgcgcagcccggactcggtaatggcgcgcattgcgcccagcgccatctgatcgttgg caaccagcatcgcagtgggaacgatgccctcattcagcatttgcatggtttgttgaaaaccggacatggcactccagtcgccttcccgttcc gctatcggctgaatttgattgcgagtgagatatttatgccagccagccagacgcagacgcgccgagacagaacttaatgggcccgctaacag cgcgatttgctggtgacccaatgcgaccagatgctccacgcccagtcgcgtaccgtcttcatgggagaaaataatactgttgatgggtgtct ggtcagagacatcaagaaataacgccggaacattagtgcaggcagcttccacagcaatggcatcctggtcatccagcggatagttaatgatc agcccactgacgcgttgcgcgagaagattgtgcaccgccgctttacaggcttcgacgccgcttcgttctaccatcgacaccaccacgctggc acccagttgatcggcgcgagatttaatcgccgcgacaatttgcgacggcgcgtgcagggccagactggaggtggcaacgccaatcagcaacg actgtttgcccgccagttgttgtgccacgcggttgggaatgtaattcagctccgccatcgccgcttccactttttcccgcgttttcgcagaa acgtggctggcctggttcaccacgcgggaaacggtctgataagagacaccggcatactctgcgacatcgtataacgttactggtttcacatt caccaccctgaattgactctcttccgggcgctatcatgccataccgcgaaaggttttgcgccattcgatggtgtccgggatctcgacgctct cccttatgcgactcctgcattaggaagcagcccagtagtaggttgaggccgttgagcaccgccgccgcaaggaatggtgcatgcaaggagat ggcgcccaacagtccccggccacggggcctgccaccatacccacgccgaaacaagcgctcatgagcccgaagtggcgagcccgatcttccc catcggtgatgtcggcgatataggcgccagcaaccgcacctgtggcgccggtgatgccggccacgatgcgtccggcgtagaggatcgagatc tcgatcccgcgaaattaatacgactcactatagggggaattgtgagcggataacaattcccctctagaaataattttgtttaactttaagaag gagatatacatatggaagctcgtcgttctgcgaactacgaacctaacagctgggactatgattacctgctgtcctccgacacggacgagtcc atcgaagtatacaaagacaaagcgaaaaagctggaagccgaagttcgtcgcgagattaataacgaaaaagcagaatttctgaccctgctgga actgattgacaacgtccagcgcctgggcctgggttaccgtttcgagtctgatatccgtggtgcgctggatcgcttcgtttcctccggcggct tcgatgcggtaaccaagacttccctgcacggtacggcactgtctttccgtctgctgcgtcaacacggttttgaggtttctcaggaagcgttc agcggcttcaaagaccaaaacggcaacttcctggagaacctgaaggaagatatcaaagctatcctgagcctgtacgaggccagcttcctggc tctgaaggcgaaaacatcctggacgaggcgaaggttttcgcaatctctcatctgaaagaactgtctgaagaaaagatcggtaaagagctgg cagaacaggtgaaccatgcactggaactgccactgcatcgccgtactcagcgtctggaagcagtatggtctatcgaggcctaccgtaaaaag -continued

```
gaggacgcgaatcaggttctgctggagctggcaattctggattacaacatgatccagtctgtataccagcgtgatctgcgtgaaacgtcccg ttggtggcgtcgtgtgggtctggcgaccaaactgcactttgctcgtgaccgcctgattgagagcttctactgggccgtgggtgtagcattcg aaccgcaatactccgactgccgtaactccgtcgcaaaaatgttttctttcgtaaccattatcgacgatatctacgatgtatacggcaccctg gacgaactggagctgtttactgatgcagttgagcgttgggacgtaaacgccatcaacgacctgccggattacatgaaactgtgctttctggc tctgtataacactattaacgaaatcgcctacgacaacctgaaagataaaggtgagaacatcctgccgtatctgaccaaagcctgggctgacc tgtgcaacgcttcctgcaagaagccaagtggctgtacaacaaatctactccgacctttgacgactacttcggcaacgcatggaaatcctct tctggcccgctgcaactggtgttcgcttacttcgctgtcgtgcagaacattaaaaaggaagagatcgaaaacctgcaaaaataccatgacac catctctcgtccttcccatatcttccgtctgtgcaatgacctggctagcgcgtctgcggaaattgcgcgtggtgaaaccgcaaatagcgttt cttgttacatgcgcactaaaggtatctccgaagaactggctaccgaaagcgtgatgaatctgatcgatgaaacctggaaaaagatgaacaag gaaaaactgggtggtagcccgttcgcgaaaccgttcgtggaaaccgcgatcaacctggcacgtcaatctcactgcacttatcataacggcga cgcgcatacctctccggatgagctgacccgcaaacgcgttctgtctgtaatctttgaaccgattctgccgtttgaacgcgaaaacctgtatt ttcagggcctcgagcaccaccaccaccaccactgagatccggctgctaacaaagcccgaaaggaagctgagttggctgctgccaccgctgag caataactagcataaccccttggggcctctaaacgggtcttgaggggttttttgctgaaaggaggaactatatccggat
```

Example 7

Biochemical Analysis of P. alba IspS Variants

As denoted in Example 8, P (L494P), SP (G491S, L494P) and SPC (G491S, L494P, T536C) isoprene synthase amino acid variants were determined to contain increased specific activity compared to WT isoprene synthase with the P variant containing the greatest specific activity (2.0 times greater than WT). The KMs of the P, SP, and SPC isoprene synthase amino acid variants were less than the KM of the WT isoprene synthase. In addition, the kcat of the β isoprene synthase amino acid variant was greater than the WT isoprene synthase. These results indicate that the P, SP and SPC amino acid variants of isoprene synthase may improve the efficiency (isoprene production rate/[Isoprene synthase]) of production of isoprene in vivo leading to an improved process for isoprene production.

Methods
Materials:
  Lysis Buffer: Ni wash+0.5 mM PMST, 0.01% Tween-20, 1 mg/ml lysozyme, 0.2 mg/ml
  DNase
  Ni wash buffer: 50 mM NaH2PO4, 300 mM NaCl, 20 mM Imidazole, pH 8.0
  Ni elution buffer: 50 mM NaH2PO4, 300 mM NaCl, 500 mM Imidazole, pH 8.0
  PD-10 buffer: 50 mM Tris, 0.05 M NaCl, pH 8.0

Expression:
  1. Overnight culture grown in 3 mL of LB broth at 30 C with $Kan_{50}$, $Chlor_{25}$
  2. Transfer 50 uL of overnight culture into 100 mL of fresh LB with antibiotic
  3. Grow at 37 C, 250 RPM for 3.5 hours
  4. Induce with 400 uM IPTG at OD600~0.4
  5. Reduce temp to 30 C and shake for 4 hours.
  6. Transfer cells into 50 mL tubes and spin 25 min at 3800 RPM
  7. Decant supernatant and repeat centrifugation step with remaining media
  8. Decant supernatant
  9. Store pellets at −80 C Purification:
  1. Initial Purification—Resuspend the pellet in 3 ml of fresh lysis buffer. Break cells by passing them through the French Press using the small cylinder. Centrifuge samples for 1 hour at 30,000×G and collect the supernatant. Retain pellet in order to test for presence of insoluble protein. Pre equilibrate 0.5 mL Ni Sepharose 6 Fast Flow resin (Amersham) in a 20 ml disposable column with 10 mL of Ni wash buffer. Add protein to column and shake for 60 min at 4 C to bind protein. Elute protein with 2.5 mL Ni elution buffer.
  2. Buffer Exchange—Equilibrate a PD-10 column (GE Healthcare) with 25 mL of PD-10 buffer. Load protein on to column and elute with 3.5 mL of PD-10 buffer.
  3. Analyze samples using SDS-PAGE to determine relative purity of pellet (p), supernatant (s), and after both columns (ni).
  4. Aliquot protein and store at −80 C.

Specific Activity Measurement—
10 uL of purified enzyme was incubated with 4 mM DMAPP, 50 mM MgCl2 in a buffer containing 50 mM Tris and 50 mM NaCl (pH=8) to a final volume of 100 uL for 15 min. at 30 C in gas tight 2 mL vials. Reactions were terminated with the addition of 100 uL of 250 uM EDTA, pH=8. Samples were analyzed by GC-MS to determine the concentration of isoprene in the headspace of the vials. All specific activity measurements were performed in triplicate.

$k_{cat}$ and $K_M$ Determination—
10 uL of purified enzyme was incubated with DMAPP at concentrations ranging from 1.25 to 20 mM DMAPP in a buffer containing 50 mM Tris, 50 mM MgCl2 and 50 mM NaCl (pH=8) to a final volume of 100 uL for 15 min. at 30 C in gas tight 2 mL vials. Reactions were terminated with the addition of 100 uL of 250 mM EDTA, pH=8. Samples were analyzed by GC-MS to determine the concentration of isoprene in the headspace of the vials. Data were analyzed using Kaleidagraph and fit to following equation for uncompetitive substrate inhibition: rate/E=kcat*S/(KM+S*(1+S/Ki)). All kinetic assays were performed in triplicate.

Protein Concentration Determination—
Protein concentration was determined by measuring the absorbance of each protein solution at 280 nm on a Helwlett Pachard 8453 UV-Vis spectrophotometer and converting the absorbance to protein concentration using the extinction coefficient as determined on the Expasy website (Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607). The protein concentrations of isoprene synthase variants assayed for $K_M$ and $k_{cat}$ determination were verified by comparative gel electrophoresis of a dilution series of each protein (FIG. 61).

Results/Discussion:

The specific activity of each protein was determined (FIG. 62 and Table 7-4). The specific acitivity of the β isoprene synthase amino acid variant was 2-fold greater than the specific activity of the WT isoprene synthase. The specific activities of the SP and SPC variants were greater than the WT isoprene synthase but less than the β isoprene synthase variant. All other isoprene synthases tested in this study displayed equal or decreased activity compared to the WT isoprene synthase.

The rate of conversion of DMAPP to isoprene was analyzed over a range of DMAPP concentrations in order to determine the kcat and KM parameters for WT, P, SP and SPC isoprene synthase amino acid variants (FIG. 63, Table 7-5). The enzymes all exhibited rate profiles consistent with uncompetitive substrate inhibition by DMAPP. The KMs of the P, SP, and SPC isoprene synthase variants were less than the KM of the WT isoprene synthase. In addition, the kcat of the β isoprene synthase variant was greater than the kcat of the WT isoprene synthase (Table 7-5)

The L494 residue was chosen for SEL studies because it is a hydrophobic residue within a surface-exposed loop of P. alba IspS. However, we observed that proline is conserved at this site in an alignment of other terpene synthase enzymes. Other Populus species isoprene synthases, along with IspS from P. Montana (Kudzu), and various other terpene synthase enzymes such as M. spicata limonene synthase, S. officinalis bornyl diphosphate synthase, N. tabacum epi-aristolochene synthase were aligned relative to P. alba IspS using the ClustalW algorithm in AlignX of the Vector NTI software (Invitrogen). FIG. 59 shows that at position 494, many other terpene synthase enzymes have a proline residue, suggesting that proline at that position not only is conserved, but that deviation from the consensus could lead to enzymes that are less efficient. Since position 494 is not near the active site of the enzyme, proline may provide stabilization to that specific loop of IspS and hence secondarily enhance the overall kinetic parameters of IspS.

TABLE 7-4

Specific activity of isoprene synthase amino acid variants.
Reactions contained 4 mM DMAPP, 50 mM NaCl, 50 mM Tris pH = 8.
Reactions were performed at 30° C.

| Variant | S.A. (nmol/mg/min) | Variant S.A./ WT S.A. |
|---|---|---|
| P | 950 ± 40 | 2.0 |
| C | 430 ± 10 | 0.9 |
| N | 170 ± 30 | 0.4 |
| PC | 490 ± 20 | 1.0 |
| SP | 770 ± 40 | 1.6 |
| NS | 480 ± 40 | 1.0 |
| NC | 420 ± 30 | 0.9 |
| SPC | 630 ± 40 | 1.3 |
| WT | 480 ± 20 | 1.0 |
| S | 480 ± 20 | 1.0 |
| SC | 440 ± 20 | 0.9 |
| NP | 490 ± 20 | 1.0 |
| NPC | 440 ± 20 | 0.9 |
| NSP | 465 ± 2 | 1.0 |

TABLE 7-4-continued

Specific activity of isoprene synthase amino acid variants.
Reactions contained 4 mM DMAPP, 50 mM NaCl, 50 mM Tris pH = 8.
Reactions were performed at 30° C.

| Variant | S.A. (nmol/mg/min) | Variant S.A./ WT S.A. |
|---|---|---|
| NSC | 390 ± 20 | 0.8 |
| NSPC | 502 ± 6 | 1.1 |

TABLE 7-5 kcat, KM and Ki for WT, P, SP, and SPC amino acid variants of isoprene synthase. Kcat, KM and Ki were calculated for each trial and then averaged. The reported error is one standard deviation of the three trials that were performed.

| Variant | $k_{cat}$ | $K_M$ | $K_{iDMAPP}$ |
|---|---|---|---|
| WT | 1.5 ± 0.6 | 7 ± 4 | 16 ± 9 |
| P | 2.1 ± 0.1 | 3.6 ± 0.5 | 13 ± 1 |
| SP | 1.2 ± 0.1 | 4.4 ± 0.3 | 18 ± 1 |
| SPC | 1.5 ± 0.4 | 3.5 ± 0.8 | 25 ± 21 |

Example 8

Expression and Purification of IspS-L494P

Expression of 6×His-Tagged IspS-L494P

N-terminally 6×His-tagged IspS was expressed and purified from strain DW399. The growth procedure is suitable for histidine tagged enzymes expressed in BL21(λDE3)pLysS cells. 10 ml of overnight culture was prepared for each 1 L of planned growth. The appropriate antibiotics (50 ug/ml kanamycin, 50 ug/ml chloramphenicol) were added to 10 ml of LB medium in a 25 ml flask which was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1L day culture was inoculated with 10 ml of overnight culture and grown at 30-37° C. with shaking at ~220 rpm until the $OD_{600}$ reached ~0.4-0.6. Day cultures were then induced with 400 µM IPTG and allowed to continue growing at 30° C. with shaking at 220 rpm for ~5-6 hours. Cells were then harvested by centrifugation at 10,000×g for 10 min, 4° C. Following harvest, cells were used directly or stored at −80° C. until ready to process.

Purification of 6×His-Tagged IspS

For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 40-50 ml of lysis buffer was used per 1L of cell pellet. Cells were then incubated on ice for approximately 30 min. The cell suspension was then lysed fully by passing 2-3 times through a french pressure cell (large french press cell at 1200 psi/High setting) until lysate appeared clear. A sample of the lysate was saved for activity assay and gel analysis (~100 µl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 µl).

The clarified lysate was run over HisTrap HP columns (GE healthcare) using a gradient from 0-100% Ni buffer B. Following loading of the lysate on the column, the column was washed with Ni wash buffer (50 mM NaH$_2$PO$_4$, 300 mm NaCl, 20 mM imidazole, ph 8.0). The his-tagged IspS was then eluted from the column using a gradient from 0-100% Ni elution buffer (50 mM NaH$_2$PO$_4$, 300 mM NaCl, 500 mM imidazole, ph 8.0) and fractions containing the his-tagged IspS were collected. The column was then washed with Ni stripping buffer (20 mM NaH2PO4, 0.5 m NaCl, 50 mM EDTA, ph 7.4). Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a Hi Prep 26/10 Desalting column (GE heathcare) packed with Sephadex G25 resin. The G-25 buffer consisted of 50 mM HEPES, 50 mM NaCl, and 1 mM DTT, pH 7.4. Fractions were then analyzed and concentrated. The samples were then stored at −80° C.

TEV Cleavage (IspS-L494P from Strains DW399)

Strain DW399 is described in Example 6. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (which is also tagged), and impurities. The Ni column pass though and washes were analyzed using SDS-PAGE gel (NUPAGE, Invitrogen; FIG. 51) and DMAPP activity assays. Samples containing pure enzyme were pooled and desalted into 50 mM NaCl pH 7.4 buffer containing 1 mM DTT and stored at −80° C.

Crystal Structure Determination

The enzyme expressed from strain DW399 was purified as described and a concentrated protein solution was then prepared for surveying possible crystallization conditions. The enzyme was purified independently and surveyed as described below. All in-house crystallization screens were set up using the hanging drop vapor diffusion method. At a minimum, the protein was surveyed using the following commercial screens: the Crystal Screen from Hampton Research (Aliso Viejo, Calif.) and the JCSG+ Suite from Qiagen (Valencia, Calif.).

Initial crystallization screens were setup using the Crystal Screen from Hampton Research and the JCSG+ Suite from Qiagen. Crystals of the protein derived from DW399 were observed in numerous conditions; optimization included 200 variations of pH, precipitating agents, concentrations, and inhibitors. From the optimization experiments, ten different crystals derived from strain DW399 were screened in-house for diffraction. A crystal composed of IspS-L494P protein was obtained that diffracted to 3.2 Å in house. The large, rod-shaped crystals belong to the tetragonal space group P4$_3$2$_1$2, and have unit cell dimensions a=155.8, b=155.8, c=143.7. The crystals were grown by mixing 2 μL of protein (10 mg/ml protein) with 2 μL of precipitant solution [0.02 M MgCl$_2$, 0.1 M HEPES pH 7.5, 22% (wt/vol) Polyacrylic acid 5100 Na salt] and equilibrated against 500 μL of precipitant.

Prior to flash-freezing the crystal in liquid nitrogen, the crystals were cryoprotected by swishing through 0.02 M MgCl$_2$, 0.1 M HEPES pH 7.5, 22% (wt/vol) Polyacrylic acid 5100 Na salt, and 25% (wt/vol) ethylene glycol.

Data were integrated using Mosflm (Leslie, A. (1998) J. of Appl. Crystallography 30, 1036-1040) and scaled using SCALA (Collaborative Computational Project, N. (1994) Acta Crystallographica Section D 50, 760-763). The data were phased with MOLREP (Vagin, A., and Teplyakov, A. (1997) J. of Appl. Crystallography 30, 1022-1025), using the previously determined structure of IspS from *P. alba* as the starting model. The crystal contains one dimer in the asymmetric unit with a solvent content of 63%. Data collection and refinement statistics are given in Table 8-1.

Refinement with Refmac5 (Collaborative Computational Project, N. (1994) Acta Crystallographica Section D 50, 760-763) was used with iterative manual rebuilding steps using the visualization program Coot (Emsley, P., and Cowtan, K. (2004) Acta Crystallographica Section D 60, 2126-2132). During refinement, the geometry of the protein was checked using Molprobity (Davis, I. W., et al. (2007) Nucl. Acids Res., 35:W375-W383).

The structure consists of two helical domains, a C-terminal domain containing the active site and N-terminal domain with unknown function. The electron density clearly supports the presence of a proline at position 494 in the enzyme derived from strain DW399 (FIG. 52). Structural alignment of the wild type IspS and IspS-L494P show that the overall fold is unchanged, however the conformation of the loop containing residues 490-497 does vary between the wild type and variant proteins (FIG. 53). Coordinates are provided in Table 8-2.

TABLE 8-1

Data Collection and Refinement Statistics for IspS-L494P

| Data Collection | |
|---|---|
| Space Group | P4$_3$2$_1$2 |
| Cell dimensions | |
| A, b, c (Å) | 155.8, 155.8, 143.6 |
| α, β, γ, (°) | 90.0, 90.0, 90.0 |
| Resolution (Å) | 25.7-3.20 |
| R$_{merge}$ | 16.6 (40.5)$^a$ |
| <I/σI> | 5.7 (2.1) |
| Completeness (%) | 98.8 (95.1) |
| Redundancy | 3.4 (2.4) |
| Refinement | |
| Resolution (Å) | 25.7-3.20 |
| No. measured reflections | 99059 |
| No. Unique reflections | 27845 |
| R$_{work}$ | 23.5 |
| R$_{free}$ | 28.6 |
| rmsd bonds, (Å) | 0.005 |
| rmsd angles, (°) | 0.756 |
| No. of Atoms | |
| Protein | 8654 |
| Water | 4 |

$^a$Values in parenthesis refer to highest resolution shell.

TABLE 8-2

Coordinates for L494P Structure

| ATOM | 1 | N | ALA | A | 7 | 58.967 | −33.368 | −28.452 | 1.00 | 32.46 | A | N |
|---|---|---|---|---|---|---|---|---|---|---|---|---|
| ATOM | 2 | CA | ALA | A | 7 | 60.455 | −33.320 | −28.515 | 1.00 | 32.33 | A | C |
| ATOM | 4 | CB | ALA | A | 7 | 60.968 | −34.329 | −29.538 | 1.00 | 32.27 | A | C |
| ATOM | 8 | C | ALA | A | 7 | 60.928 | −31.913 | −28.869 | 1.00 | 32.20 | A | C |
| ATOM | 9 | O | ALA | A | 7 | 61.175 | −31.618 | −30.038 | 1.00 | 31.89 | A | O |

TABLE 8-2-continued

Coordinates for L494P Structure

| ATOM | 13 | N | ASN | A | 8 | 61.056 | −31.054 | −27.855 | 1.00 | 32.28 | A | N |
|---|---|---|---|---|---|---|---|---|---|---|---|---|
| ATOM | 14 | CA | ASN | A | 8 | 61.414 | −29.646 | −28.067 | 1.00 | 32.54 | A | C |
| ATOM | 16 | CB | ASN | A | 8 | 60.171 | −28.754 | −27.938 | 1.00 | 32.84 | A | C |
| ATOM | 19 | CG | ASN | A | 8 | 60.193 | −27.562 | −28.897 | 1.00 | 33.76 | A | C |
| ATOM | 20 | OD1 | ASN | A | 8 | 61.242 | −26.964 | −29.150 | 1.00 | 34.16 | A | O |
| ATOM | 21 | ND2 | ASN | A | 8 | 59.027 | −27.215 | −29.432 | 1.00 | 34.29 | A | N |
| ATOM | 24 | C | ASN | A | 8 | 62.519 | −29.158 | −27.125 | 1.00 | 32.38 | A | C |
| ATOM | 25 | O | ASN | A | 8 | 62.774 | −29.764 | −26.081 | 1.00 | 31.88 | A | O |
| ATOM | 27 | N | TYR | A | 9 | 63.148 | −28.045 | −27.510 | 1.00 | 32.53 | A | N |
| ATOM | 28 | CA | TYR | A | 9 | 64.378 | −27.551 | −26.881 | 1.00 | 32.48 | A | C |
| ATOM | 30 | CB | TYR | A | 9 | 65.529 | −27.650 | −27.886 | 1.00 | 32.17 | A | C |
| ATOM | 33 | CG | TYR | A | 9 | 65.491 | −28.904 | −28.713 | 1.00 | 31.92 | A | C |
| ATOM | 34 | CD1 | TYR | A | 9 | 65.999 | −30.097 | −28.214 | 1.00 | 32.88 | A | C |
| ATOM | 36 | CE1 | TYR | A | 9 | 65.963 | −31.258 | −28.964 | 1.00 | 32.64 | A | C |
| ATOM | 38 | CZ | TYR | A | 9 | 65.409 | −31.241 | −30.230 | 1.00 | 32.19 | A | C |
| ATOM | 39 | OH | TYR | A | 9 | 65.370 | −32.394 | −30.978 | 1.00 | 31.19 | A | O |
| ATOM | 41 | CE2 | TYR | A | 9 | 64.892 | −30.067 | −30.748 | 1.00 | 31.99 | A | C |
| ATOM | 43 | CD2 | TYR | A | 9 | 64.933 | −28.906 | −29.987 | 1.00 | 31.30 | A | C |
| ATOM | 45 | C | TYR | A | 9 | 64.297 | −26.100 | −26.401 | 1.00 | 32.65 | A | C |
| ATOM | 46 | O | TYR | A | 9 | 65.333 | −25.490 | −26.119 | 1.00 | 32.90 | A | O |
| ATOM | 48 | N | GLU | A | 10 | 63.089 | −25.547 | −26.304 | 1.00 | 32.35 | A | N |
| ATOM | 49 | CA | GLU | A | 10 | 62.923 | −24.126 | −25.971 | 1.00 | 32.21 | A | C |
| ATOM | 51 | CB | GLU | A | 10 | 61.450 | −23.711 | −26.089 | 1.00 | 32.51 | A | C |
| ATOM | 54 | CG | GLU | A | 10 | 60.880 | −23.803 | −27.509 | 1.00 | 34.11 | A | C |
| ATOM | 57 | CD | GLU | A | 10 | 61.671 | −23.001 | −28.542 | 1.00 | 35.77 | A | C |
| ATOM | 58 | OE1 | GLU | A | 10 | 62.114 | −21.874 | −28.223 | 1.00 | 35.78 | A | O |
| ATOM | 59 | OE2 | GLU | A | 10 | 61.841 | −23.503 | −29.677 | 1.00 | 35.44 | A | O |
| ATOM | 60 | C | GLU | A | 10 | 63.473 | −23.814 | −24.572 | 1.00 | 31.42 | A | C |
| ATOM | 61 | O | GLU | A | 10 | 63.467 | −24.684 | −23.700 | 1.00 | 31.43 | A | O |
| ATOM | 63 | N | PRO | A | 11 | 63.953 | −22.572 | −24.359 | 1.00 | 30.52 | A | N |
| ATOM | 64 | CA | PRO | A | 11 | 64.709 | −22.252 | −23.148 | 1.00 | 30.13 | A | C |
| ATOM | 66 | CB | PRO | A | 11 | 65.263 | −20.857 | −23.449 | 1.00 | 30.16 | A | C |
| ATOM | 69 | CG | PRO | A | 11 | 64.250 | −20.247 | −24.336 | 1.00 | 30.10 | A | C |
| ATOM | 72 | CD | PRO | A | 11 | 63.722 | −21.372 | −25.186 | 1.00 | 30.45 | A | C |
| ATOM | 75 | C | PRO | A | 11 | 63.856 | −22.208 | −21.886 | 1.00 | 29.77 | A | C |
| ATOM | 76 | O | PRO | A | 11 | 62.763 | −21.645 | −21.902 | 1.00 | 30.21 | A | O |
| ATOM | 77 | N | ASN | A | 12 | 64.357 | −22.802 | −20.807 | 1.00 | 29.24 | A | N |
| ATOM | 78 | CA | ASN | A | 12 | 63.717 | −22.692 | −19.501 | 1.00 | 28.99 | A | C |
| ATOM | 80 | CB | ASN | A | 12 | 64.148 | −23.841 | −18.588 | 1.00 | 28.99 | A | C |
| ATOM | 83 | CG | ASN | A | 12 | 63.744 | −25.201 | −19.128 | 1.00 | 28.62 | A | C |
| ATOM | 84 | OD1 | ASN | A | 12 | 62.558 | −25.498 | −19.268 | 1.00 | 29.36 | A | O |
| ATOM | 85 | ND2 | ASN | A | 12 | 64.731 | −26.038 | −19.423 | 1.00 | 27.55 | A | N |
| ATOM | 88 | C | ASN | A | 12 | 64.083 | −21.348 | −18.872 | 1.00 | 28.99 | A | C |
| ATOM | 89 | O | ASN | A | 12 | 65.197 | −20.853 | −19.062 | 1.00 | 29.27 | A | O |
| ATOM | 91 | N | SER | A | 13 | 63.146 | −20.760 | −18.131 | 1.00 | 28.65 | A | N |
| ATOM | 92 | CA | SER | A | 13 | 63.365 | −19.461 | −17.482 | 1.00 | 28.22 | A | C |
| ATOM | 94 | CB | SER | A | 13 | 62.052 | −18.933 | −16.893 | 1.00 | 28.27 | A | C |
| ATOM | 97 | OG | SER | A | 13 | 61.433 | −19.905 | −16.067 | 1.00 | 27.86 | A | O |
| ATOM | 99 | C | SER | A | 13 | 64.437 | −19.531 | −16.388 | 1.00 | 27.86 | A | C |
| ATOM | 100 | O | SER | A | 13 | 65.127 | −18.545 | −16.117 | 1.00 | 27.35 | A | O |
| ATOM | 102 | N | TRP | A | 14 | 64.573 | −20.704 | −15.775 | 1.00 | 27.59 | A | N |
| ATOM | 103 | CA | TRP | A | 14 | 65.538 | −20.919 | −14.697 | 1.00 | 27.37 | A | C |
| ATOM | 105 | CB | TRP | A | 14 | 64.967 | −21.893 | −13.649 | 1.00 | 27.41 | A | C |
| ATOM | 108 | CG | TRP | A | 14 | 64.246 | −23.092 | −14.212 | 1.00 | 28.21 | A | C |
| ATOM | 109 | CD1 | TRP | A | 14 | 62.894 | −23.246 | −14.346 | 1.00 | 29.22 | A | C |
| ATOM | 111 | NE1 | TRP | A | 14 | 62.607 | −24.471 | −14.897 | 1.00 | 29.08 | A | N |
| ATOM | 113 | CE2 | TRP | A | 14 | 63.781 | −25.138 | −15.127 | 1.00 | 29.46 | A | C |
| ATOM | 114 | CD2 | TRP | A | 14 | 64.836 | −24.299 | −14.706 | 1.00 | 28.64 | A | C |
| ATOM | 115 | CE3 | TRP | A | 14 | 66.153 | −24.754 | −14.836 | 1.00 | 29.12 | A | C |
| ATOM | 117 | CZ3 | TRP | A | 14 | 66.373 | −26.014 | −15.377 | 1.00 | 30.29 | A | C |
| ATOM | 119 | CH2 | TRP | A | 14 | 65.303 | −26.825 | −15.788 | 1.00 | 30.52 | A | C |
| ATOM | 121 | CZ2 | TRP | A | 14 | 64.004 | −26.406 | −15.670 | 1.00 | 30.11 | A | C |
| ATOM | 123 | C | TRP | A | 14 | 66.912 | −21.401 | −15.189 | 1.00 | 27.25 | A | C |
| ATOM | 124 | O | TRP | A | 14 | 67.776 | −21.723 | −14.378 | 1.00 | 27.30 | A | O |
| ATOM | 126 | N | ASP | A | 15 | 67.127 | −21.435 | −16.503 | 1.00 | 27.11 | A | N |
| ATOM | 127 | CA | ASP | A | 15 | 68.419 | −21.859 | −17.055 | 1.00 | 27.19 | A | C |
| ATOM | 129 | CB | ASP | A | 15 | 68.371 | −21.911 | −18.587 | 1.00 | 27.21 | A | C |
| ATOM | 132 | CG | ASP | A | 15 | 67.685 | −23.157 | −19.117 | 1.00 | 27.43 | A | C |
| ATOM | 133 | OD1 | ASP | A | 15 | 67.686 | −24.200 | −18.426 | 1.00 | 26.27 | A | O |
| ATOM | 134 | OD2 | ASP | A | 15 | 67.154 | −23.094 | −20.246 | 1.00 | 29.06 | A | O |
| ATOM | 135 | C | ASP | A | 15 | 69.562 | −20.941 | −16.625 | 1.00 | 27.45 | A | C |
| ATOM | 136 | O | ASP | A | 15 | 69.347 | −19.773 | −16.302 | 1.00 | 27.69 | A | O |
| ATOM | 138 | N | TYR | A | 16 | 70.778 | −21.479 | −16.633 | 1.00 | 27.65 | A | N |
| ATOM | 139 | CA | TYR | A | 16 | 71.968 | −20.698 | −16.299 | 1.00 | 27.87 | A | C |
| ATOM | 141 | CB | TYR | A | 16 | 73.122 | −21.618 | −15.890 | 1.00 | 27.97 | A | C |
| ATOM | 144 | CG | TYR | A | 16 | 72.878 | −22.322 | −14.569 | 1.00 | 28.42 | A | C |
| ATOM | 145 | CD1 | TYR | A | 16 | 72.806 | −21.601 | −13.378 | 1.00 | 28.17 | A | C |
| ATOM | 147 | CE1 | TYR | A | 16 | 72.576 | −22.236 | −12.164 | 1.00 | 26.82 | A | C |

TABLE 8-2-continued

Coordinates for L494P Structure

| ATOM | 149 | CZ | TYR | A | 16 | 72.417 | −23.606 | −12.130 | 1.00 | 26.17 | A | C |
|---|---|---|---|---|---|---|---|---|---|---|---|---|
| ATOM | 150 | OH | TYR | A | 16 | 72.191 | −24.230 | −10.929 | 1.00 | 25.22 | A | O |
| ATOM | 152 | CE2 | TYR | A | 16 | 72.485 | −24.348 | −13.296 | 1.00 | 26.88 | A | C |
| ATOM | 154 | CD2 | TYR | A | 16 | 72.715 | −23.704 | −14.509 | 1.00 | 27.97 | A | C |
| ATOM | 156 | C | TYR | A | 16 | 72.389 | −19.774 | −17.445 | 1.00 | 28.24 | A | C |
| ATOM | 157 | O | TYR | A | 16 | 73.125 | −18.814 | −17.225 | 1.00 | 28.23 | A | O |
| ATOM | 159 | N | ASP | A | 17 | 71.929 | −20.071 | −18.660 | 1.00 | 28.81 | A | N |
| ATOM | 160 | CA | ASP | A | 17 | 72.109 | −19.171 | −19.806 | 1.00 | 29.05 | A | C |
| ATOM | 162 | CB | ASP | A | 17 | 71.891 | −19.919 | −21.129 | 1.00 | 28.88 | A | C |
| ATOM | 165 | CG | ASP | A | 17 | 72.965 | −20.962 | −21.406 | 1.00 | 28.36 | A | C |
| ATOM | 166 | OD1 | ASP | A | 17 | 74.154 | −20.593 | −21.514 | 1.00 | 27.28 | A | O |
| ATOM | 167 | OD2 | ASP | A | 17 | 72.614 | −22.154 | −21.539 | 1.00 | 27.24 | A | O |
| ATOM | 168 | C | ASP | A | 17 | 71.140 | −17.987 | −19.726 | 1.00 | 29.57 | A | C |
| ATOM | 169 | O | ASP | A | 17 | 71.501 | −16.858 | −20.062 | 1.00 | 29.32 | A | O |
| ATOM | 171 | N | TYR | A | 18 | 69.916 | −18.260 | −19.274 | 1.00 | 30.37 | A | N |
| ATOM | 172 | CA | TYR | A | 18 | 68.828 | −17.278 | −19.250 | 1.00 | 31.29 | A | C |
| ATOM | 174 | CB | TYR | A | 18 | 67.495 | −18.008 | −19.056 | 1.00 | 31.77 | A | C |
| ATOM | 177 | CG | TYR | A | 18 | 66.249 | −17.171 | −19.266 | 1.00 | 35.14 | A | C |
| ATOM | 178 | CD1 | TYR | A | 18 | 65.523 | −17.255 | −20.456 | 1.00 | 37.79 | A | C |
| ATOM | 180 | CE1 | TYR | A | 18 | 64.370 | −16.503 | −20.650 | 1.00 | 38.22 | A | C |
| ATOM | 182 | CZ | TYR | A | 18 | 63.926 | −15.661 | −19.645 | 1.00 | 38.92 | A | C |
| ATOM | 183 | OH | TYR | A | 18 | 62.785 | −14.918 | −19.837 | 1.00 | 40.58 | A | O |
| ATOM | 185 | CE2 | TYR | A | 18 | 64.623 | −15.565 | −18.451 | 1.00 | 38.20 | A | C |
| ATOM | 187 | CD2 | TYR | A | 18 | 65.775 | −16.321 | −18.265 | 1.00 | 36.98 | A | C |
| ATOM | 189 | C | TYR | A | 18 | 69.043 | −16.237 | −18.149 | 1.00 | 31.48 | A | C |
| ATOM | 190 | O | TYR | A | 18 | 69.094 | −15.039 | −18.426 | 1.00 | 31.70 | A | O |
| ATOM | 192 | N | LEU | A | 19 | 69.156 | −16.699 | −16.905 | 1.00 | 31.72 | A | N |
| ATOM | 193 | CA | LEU | A | 19 | 69.585 | −15.852 | −15.792 | 1.00 | 31.90 | A | C |
| ATOM | 195 | CB | LEU | A | 19 | 69.089 | −16.416 | −14.455 | 1.00 | 31.77 | A | C |
| ATOM | 198 | CG | LEU | A | 19 | 67.574 | −16.531 | −14.261 | 1.00 | 32.74 | A | C |
| ATOM | 200 | CD1 | LEU | A | 19 | 67.248 | −17.518 | −13.141 | 1.00 | 32.00 | A | C |
| ATOM | 204 | CD2 | LEU | A | 19 | 66.943 | −15.164 | −13.989 | 1.00 | 31.72 | A | C |
| ATOM | 208 | C | LEU | A | 19 | 71.106 | −15.825 | −15.806 | 1.00 | 32.37 | A | C |
| ATOM | 209 | O | LEU | A | 19 | 71.727 | −16.380 | −16.712 | 1.00 | 32.67 | A | O |
| ATOM | 211 | N | LEU | A | 20 | 71.709 | −15.174 | −14.815 | 1.00 | 32.83 | A | N |
| ATOM | 212 | CA | LEU | A | 20 | 73.148 | −15.281 | −14.594 | 1.00 | 33.25 | A | C |
| ATOM | 214 | CB | LEU | A | 20 | 73.466 | −16.668 | −14.021 | 1.00 | 33.14 | A | C |
| ATOM | 217 | CG | LEU | A | 20 | 74.826 | −16.886 | −13.356 | 1.00 | 33.70 | A | C |
| ATOM | 219 | CD1 | LEU | A | 20 | 74.988 | −15.984 | −12.139 | 1.00 | 34.63 | A | C |
| ATOM | 223 | CD2 | LEU | A | 20 | 74.985 | −18.351 | −12.969 | 1.00 | 33.93 | A | C |
| ATOM | 227 | C | LEU | A | 20 | 73.947 | −15.025 | −15.880 | 1.00 | 33.88 | A | C |
| ATOM | 228 | O | LEU | A | 20 | 74.771 | −15.848 | −16.292 | 1.00 | 33.76 | A | O |
| ATOM | 230 | N | SER | A | 21 | 73.677 | −13.888 | −16.519 | 1.00 | 34.62 | A | N |
| ATOM | 231 | CA | SER | A | 21 | 74.409 | −13.467 | −17.718 | 1.00 | 35.00 | A | C |
| ATOM | 233 | CB | SER | A | 21 | 73.478 | −13.378 | −18.933 | 1.00 | 35.02 | A | C |
| ATOM | 236 | OG | SER | A | 21 | 73.457 | −14.605 | −19.644 | 1.00 | 34.89 | A | O |
| ATOM | 238 | C | SER | A | 21 | 75.117 | −12.136 | −17.488 | 1.00 | 35.34 | A | C |
| ATOM | 239 | O | SER | A | 21 | 74.711 | −11.334 | −16.639 | 1.00 | 34.98 | A | O |
| ATOM | 241 | N | SER | A | 22 | 76.173 | −11.913 | −18.266 | 1.00 | 35.95 | A | N |
| ATOM | 242 | CA | SER | A | 22 | 77.087 | −10.795 | −18.048 | 1.00 | 36.40 | A | C |
| ATOM | 244 | CB | SER | A | 22 | 78.430 | −11.076 | −18.732 | 1.00 | 36.31 | A | C |
| ATOM | 247 | OG | SER | A | 22 | 78.248 | −11.367 | −20.107 | 1.00 | 35.88 | A | O |
| ATOM | 249 | C | SER | A | 22 | 76.530 | −9.461 | −18.543 | 1.00 | 36.86 | A | C |
| ATOM | 250 | O | SER | A | 22 | 76.493 | −9.205 | −19.751 | 1.00 | 36.97 | A | O |
| ATOM | 252 | N | ASP | A | 23 | 76.099 | −8.619 | −17.603 | 1.00 | 37.22 | A | N |
| ATOM | 253 | CA | ASP | A | 23 | 75.752 | −7.232 | −17.906 | 1.00 | 37.43 | A | C |
| ATOM | 255 | CB | ASP | A | 23 | 75.077 | −6.567 | −16.694 | 1.00 | 37.44 | A | C |
| ATOM | 258 | CG | ASP | A | 23 | 74.428 | −5.228 | −17.030 | 1.00 | 37.60 | A | C |
| ATOM | 259 | OD1 | ASP | A | 23 | 74.332 | −4.869 | −18.223 | 1.00 | 37.88 | A | O |
| ATOM | 260 | OD2 | ASP | A | 23 | 74.003 | −4.531 | −16.084 | 1.00 | 37.64 | A | O |
| ATOM | 261 | C | ASP | A | 23 | 77.049 | −6.517 | −18.299 | 1.00 | 37.55 | A | C |
| ATOM | 262 | O | ASP | A | 23 | 77.168 | −5.993 | −19.410 | 1.00 | 37.66 | A | O |
| ATOM | 264 | N | THR | A | 24 | 78.015 | −6.509 | −17.380 | 1.00 | 37.50 | A | N |
| ATOM | 265 | CA | THR | A | 24 | 79.413 | −6.192 | −17.700 | 1.00 | 37.32 | A | C |
| ATOM | 267 | CB | THR | A | 24 | 79.691 | −4.665 | −17.661 | 1.00 | 37.41 | A | C |
| ATOM | 269 | OG1 | THR | A | 24 | 78.608 | −3.952 | −18.274 | 1.00 | 37.33 | A | O |
| ATOM | 271 | CG2 | THR | A | 24 | 80.991 | −4.330 | −18.392 | 1.00 | 36.82 | A | C |
| ATOM | 275 | C | THR | A | 24 | 80.360 | −6.925 | −16.730 | 1.00 | 37.05 | A | C |
| ATOM | 276 | O | THR | A | 24 | 81.444 | −6.430 | −16.407 | 1.00 | 37.13 | A | O |
| ATOM | 278 | N | ASP | A | 25 | 79.944 | −8.116 | −16.290 | 1.00 | 36.41 | A | N |
| ATOM | 279 | CA | ASP | A | 25 | 80.665 | −8.890 | −15.278 | 1.00 | 35.69 | A | C |
| ATOM | 281 | CB | ASP | A | 25 | 79.714 | −9.307 | −14.149 | 1.00 | 35.42 | A | C |
| ATOM | 284 | CG | ASP | A | 25 | 79.022 | −8.123 | −13.489 | 1.00 | 34.28 | A | C |
| ATOM | 285 | OD1 | ASP | A | 25 | 79.536 | −6.988 | −13.575 | 1.00 | 31.33 | A | O |
| ATOM | 286 | OD2 | ASP | A | 25 | 77.956 | −8.335 | −12.875 | 1.00 | 33.31 | A | O |
| ATOM | 287 | C | ASP | A | 25 | 81.298 | −10.136 | −15.899 | 1.00 | 35.33 | A | C |
| ATOM | 288 | O | ASP | A | 25 | 80.594 | −11.077 | −16.273 | 1.00 | 35.35 | A | O |
| ATOM | 290 | N | GLU | A | 26 | 82.625 | −10.134 | −16.002 | 1.00 | 34.79 | A | N |

TABLE 8-2-continued

Coordinates for L494P Structure

| ATOM | 291 | CA | GLU | A | 26 | 83.372 | −11.273 | −16.546 | 1.00 | 34.55 A | C |
|---|---|---|---|---|---|---|---|---|---|---|---|
| ATOM | 293 | CB | GLU | A | 26 | 84.858 | −10.920 | −16.690 | 1.00 | 34.43 A | C |
| ATOM | 296 | CG | GLU | A | 26 | 85.159 | −9.814 | −17.695 | 1.00 | 33.53 A | C |
| ATOM | 299 | CD | GLU | A | 26 | 86.645 | −9.516 | −17.821 | 1.00 | 31.34 A | C |
| ATOM | 300 | OE1 | GLU | A | 26 | 87.432 | −9.968 | −16.962 | 1.00 | 30.11 A | O |
| ATOM | 301 | OE2 | GLU | A | 26 | 87.026 | −8.822 | −18.785 | 1.00 | 29.48 A | O |
| ATOM | 302 | C | GLU | A | 26 | 83.251 | −12.515 | −15.662 | 1.00 | 34.62 A | C |
| ATOM | 303 | O | GLU | A | 26 | 83.213 | −13.644 | −16.159 | 1.00 | 34.51 A | O |
| ATOM | 305 | N | SER | A | 27 | 83.197 | −12.292 | −14.351 | 1.00 | 34.63 A | N |
| ATOM | 306 | CA | SER | A | 27 | 83.188 | −13.374 | −13.365 | 1.00 | 34.68 A | C |
| ATOM | 308 | CB | SER | A | 27 | 83.367 | −12.794 | −11.957 | 1.00 | 34.79 A | C |
| ATOM | 311 | OG | SER | A | 27 | 82.483 | −11.706 | −11.735 | 1.00 | 34.93 A | O |
| ATOM | 313 | C | SER | A | 27 | 81.930 | −14.252 | −13.416 | 1.00 | 34.53 A | C |
| ATOM | 314 | O | SER | A | 27 | 81.963 | −15.407 | −12.979 | 1.00 | 34.27 A | O |
| ATOM | 316 | N | ILE | A | 28 | 80.831 | −13.709 | −13.942 | 1.00 | 34.31 A | N |
| ATOM | 317 | CA | ILE | A | 28 | 79.602 | −14.484 | −14.119 | 1.00 | 34.09 A | C |
| ATOM | 319 | CB | ILE | A | 28 | 78.412 | −13.598 | −14.561 | 1.00 | 34.14 A | C |
| ATOM | 321 | CG1 | ILE | A | 28 | 78.065 | −12.575 | −13.476 | 1.00 | 34.77 A | C |
| ATOM | 324 | CD1 | ILE | A | 28 | 76.877 | −11.689 | −13.824 | 1.00 | 35.54 A | C |
| ATOM | 328 | CG2 | ILE | A | 28 | 77.190 | −14.457 | −14.860 | 1.00 | 33.66 A | C |
| ATOM | 332 | C | ILE | A | 28 | 79.798 | −15.599 | −15.148 | 1.00 | 33.79 A | C |
| ATOM | 333 | O | ILE | A | 28 | 79.289 | −16.700 | −14.968 | 1.00 | 33.59 A | O |
| ATOM | 335 | N | GLU | A | 29 | 80.552 | −15.315 | −16.210 | 1.00 | 33.59 A | N |
| ATOM | 336 | CA | GLU | A | 29 | 80.739 | −16.270 | −17.313 | 1.00 | 33.41 A | C |
| ATOM | 338 | CB | GLU | A | 29 | 81.273 | −15.556 | −18.564 | 1.00 | 33.57 A | C |
| ATOM | 341 | CG | GLU | A | 29 | 80.268 | −14.599 | −19.206 | 1.00 | 34.79 A | C |
| ATOM | 344 | CD | GLU | A | 29 | 78.994 | −15.293 | −19.675 | 1.00 | 35.14 A | C |
| ATOM | 345 | OE1 | GLU | A | 29 | 79.092 | −16.335 | −20.357 | 1.00 | 35.06 A | O |
| ATOM | 346 | OE2 | GLU | A | 29 | 77.892 | −14.792 | −19.362 | 1.00 | 35.70 A | O |
| ATOM | 347 | C | GLU | A | 29 | 81.627 | −17.476 | −16.984 | 1.00 | 32.74 A | C |
| ATOM | 348 | O | GLU | A | 29 | 81.700 | −18.415 | −17.776 | 1.00 | 32.85 A | O |
| ATOM | 350 | N | VAL | A | 30 | 82.309 | −17.449 | −15.840 | 1.00 | 31.82 A | N |
| ATOM | 351 | CA | VAL | A | 30 | 82.990 | −18.640 | −15.320 | 1.00 | 30.90 A | C |
| ATOM | 353 | CB | VAL | A | 30 | 84.379 | −18.305 | −14.736 | 1.00 | 30.95 A | C |
| ATOM | 355 | CG1 | VAL | A | 30 | 85.158 | −19.583 | −14.445 | 1.00 | 30.39 A | C |
| ATOM | 359 | CG2 | VAL | A | 30 | 85.160 | −17.412 | −15.693 | 1.00 | 30.85 A | C |
| ATOM | 363 | C | VAL | A | 30 | 82.117 | −19.310 | −14.253 | 1.00 | 29.93 A | C |
| ATOM | 364 | O | VAL | A | 30 | 82.088 | −20.533 | −14.149 | 1.00 | 29.30 A | O |
| ATOM | 366 | N | TYR | A | 31 | 81.419 | −18.492 | −13.468 | 1.00 | 29.33 A | N |
| ATOM | 367 | CA | TYR | A | 31 | 80.412 | −18.952 | −12.504 | 1.00 | 28.99 A | C |
| ATOM | 369 | CB | TYR | A | 31 | 79.844 | −17.729 | −11.762 | 1.00 | 29.11 A | C |
| ATOM | 372 | CG | TYR | A | 31 | 78.990 | −18.015 | −10.541 | 1.00 | 29.97 A | C |
| ATOM | 373 | CD1 | TYR | A | 31 | 79.552 | −18.524 | −9.371 | 1.00 | 30.42 A | C |
| ATOM | 375 | CE1 | TYR | A | 31 | 78.767 | −18.768 | −8.241 | 1.00 | 31.07 A | C |
| ATOM | 377 | CZ | TYR | A | 31 | 77.406 | −18.490 | −8.274 | 1.00 | 31.23 A | C |
| ATOM | 378 | OH | TYR | A | 31 | 76.621 | −18.728 | −7.165 | 1.00 | 30.48 A | O |
| ATOM | 380 | CE2 | TYR | A | 31 | 76.829 | −17.972 | −9.420 | 1.00 | 30.59 A | C |
| ATOM | 382 | CD2 | TYR | A | 31 | 77.623 | −17.731 | −10.542 | 1.00 | 31.01 A | C |
| ATOM | 384 | C | TYR | A | 31 | 79.294 | −19.726 | −13.225 | 1.00 | 28.35 A | C |
| ATOM | 385 | O | TYR | A | 31 | 78.896 | −20.815 | −12.802 | 1.00 | 28.24 A | O |
| ATOM | 387 | N | LYS | A | 32 | 78.811 | −19.143 | −14.321 | 1.00 | 27.54 A | N |
| ATOM | 388 | CA | LYS | A | 32 | 77.792 | −19.738 | −15.196 | 1.00 | 26.68 A | C |
| ATOM | 390 | CB | LYS | A | 32 | 77.434 | −18.724 | −16.292 | 1.00 | 27.16 A | C |
| ATOM | 393 | CG | LYS | A | 32 | 76.586 | −19.211 | −17.469 | 1.00 | 27.92 A | C |
| ATOM | 396 | CD | LYS | A | 32 | 76.980 | −18.446 | −18.748 | 1.00 | 29.61 A | C |
| ATOM | 399 | CE | LYS | A | 32 | 75.811 | −18.227 | −19.693 | 1.00 | 30.33 A | C |
| ATOM | 402 | NZ | LYS | A | 32 | 74.948 | −17.083 | −19.266 | 1.00 | 30.04 A | N |
| ATOM | 406 | C | LYS | A | 32 | 78.285 | −21.036 | −15.826 | 1.00 | 25.58 A | C |
| ATOM | 407 | O | LYS | A | 32 | 77.620 | −22.067 | −15.728 | 1.00 | 25.63 A | O |
| ATOM | 409 | N | ASP | A | 33 | 79.448 | −20.974 | −16.475 | 1.00 | 24.33 A | N |
| ATOM | 410 | CA | ASP | A | 33 | 80.056 | −22.154 | −17.106 | 1.00 | 23.26 A | C |
| ATOM | 412 | CB | ASP | A | 33 | 81.367 | −21.783 | −17.822 | 1.00 | 23.36 A | C |
| ATOM | 415 | CG | ASP | A | 33 | 81.142 | −21.100 | −19.173 | 1.00 | 23.27 A | C |
| ATOM | 416 | OD1 | ASP | A | 33 | 79.992 | −21.051 | −19.659 | 1.00 | 23.99 A | O |
| ATOM | 417 | OD2 | ASP | A | 33 | 82.133 | −20.612 | −19.757 | 1.00 | 21.23 A | O |
| ATOM | 418 | C | ASP | A | 33 | 80.313 | −23.278 | −16.099 | 1.00 | 22.17 A | C |
| ATOM | 419 | O | ASP | A | 33 | 80.256 | −24.455 | −16.454 | 1.00 | 21.98 A | O |
| ATOM | 421 | N | LYS | A | 34 | 80.592 | −22.910 | −14.849 | 1.00 | 21.18 A | N |
| ATOM | 422 | CA | LYS | A | 34 | 80.789 | −23.885 | −13.774 | 1.00 | 20.15 A | C |
| ATOM | 424 | CB | LYS | A | 34 | 81.420 | −23.221 | −12.541 | 1.00 | 19.97 A | C |
| ATOM | 427 | CG | LYS | A | 34 | 82.264 | −24.155 | −11.679 | 1.00 | 19.67 A | C |
| ATOM | 430 | CD | LYS | A | 34 | 83.466 | −23.426 | −11.061 | 1.00 | 20.43 A | C |
| ATOM | 433 | CE | LYS | A | 34 | 84.646 | −24.371 | −10.818 | 1.00 | 20.70 A | C |
| ATOM | 436 | NZ | LYS | A | 34 | 85.942 | −23.644 | −10.709 | 1.00 | 17.82 A | N |
| ATOM | 440 | C | LYS | A | 34 | 79.457 | −24.534 | −13.409 | 1.00 | 19.43 A | C |
| ATOM | 441 | O | LYS | A | 34 | 79.368 | −25.759 | −13.320 | 1.00 | 20.13 A | O |
| ATOM | 443 | N | ALA | A | 35 | 78.427 | −23.712 | −13.209 | 1.00 | 17.92 A | N |
| ATOM | 444 | CA | ALA | A | 35 | 77.080 | −24.211 | −12.927 | 1.00 | 16.84 A | C |

TABLE 8-2-continued

Coordinates for L494P Structure

| ATOM | 446 | CB | ALA | A | 35 | 76.086 | −23.063 | −12.871 | 1.00 | 16.71 | A | C |
|------|-----|------|------|---|----|--------|---------|---------|------|-------|---|---|
| ATOM | 450 | C | ALA | A | 35 | 76.656 | −25.222 | −13.984 | 1.00 | 16.12 | A | C |
| ATOM | 451 | O | ALA | A | 35 | 76.317 | −26.360 | −13.663 | 1.00 | 15.55 | A | O |
| ATOM | 453 | N | LYS | A | 36 | 76.703 | −24.798 | −15.245 | 1.00 | 15.82 | A | N |
| ATOM | 454 | CA | LYS | A | 36 | 76.337 | −25.647 | −16.385 | 1.00 | 15.48 | A | C |
| ATOM | 456 | CB | LYS | A | 36 | 76.637 | −24.921 | −17.708 | 1.00 | 15.46 | A | C |
| ATOM | 459 | CG | LYS | A | 36 | 75.690 | −23.752 | −18.007 | 1.00 | 14.99 | A | C |
| ATOM | 462 | CD | LYS | A | 36 | 76.314 | −22.686 | −18.917 | 1.00 | 13.95 | A | C |
| ATOM | 465 | CE | LYS | A | 36 | 76.428 | −23.143 | −20.367 | 1.00 | 13.77 | A | C |
| ATOM | 468 | NZ | LYS | A | 36 | 76.844 | −22.031 | −21.277 | 1.00 | 12.18 | A | N |
| ATOM | 472 | C | LYS | A | 36 | 77.038 | −27.011 | −16.359 | 1.00 | 15.21 | A | C |
| ATOM | 473 | O | LYS | A | 36 | 76.413 | −28.030 | −16.650 | 1.00 | 15.02 | A | O |
| ATOM | 475 | N | LYS | A | 37 | 78.324 | −27.024 | −16.004 | 1.00 | 15.15 | A | N |
| ATOM | 476 | CA | LYS | A | 37 | 79.104 | −28.267 | −15.941 | 1.00 | 15.11 | A | C |
| ATOM | 478 | CB | LYS | A | 37 | 80.602 | −27.970 | −15.781 | 1.00 | 15.02 | A | C |
| ATOM | 481 | CG | LYS | A | 37 | 81.457 | −29.221 | −15.544 | 1.00 | 16.38 | A | C |
| ATOM | 484 | CD | LYS | A | 37 | 82.922 | −29.033 | −15.934 | 1.00 | 16.66 | A | C |
| ATOM | 487 | CE | LYS | A | 37 | 83.714 | −30.321 | −15.703 | 1.00 | 15.63 | A | C |
| ATOM | 490 | NZ | LYS | A | 37 | 85.058 | −30.304 | −16.342 | 1.00 | 14.75 | A | N |
| ATOM | 494 | C | LYS | A | 37 | 78.626 | −29.187 | −14.813 | 1.00 | 15.19 | A | C |
| ATOM | 495 | O | LYS | A | 37 | 78.467 | −30.397 | −15.011 | 1.00 | 15.35 | A | O |
| ATOM | 497 | N | LEU | A | 38 | 78.405 | −28.612 | −13.633 | 1.00 | 14.82 | A | N |
| ATOM | 498 | CA | LEU | A | 38 | 77.904 | −29.372 | −12.488 | 1.00 | 14.29 | A | C |
| ATOM | 500 | CB | LEU | A | 38 | 77.978 | −28.533 | −11.208 | 1.00 | 14.07 | A | C |
| ATOM | 503 | CG | LEU | A | 38 | 79.356 | −28.035 | −10.767 | 1.00 | 13.08 | A | C |
| ATOM | 505 | CD1 | LEU | A | 38 | 79.227 | −27.212 | −9.494 | 1.00 | 10.42 | A | C |
| ATOM | 509 | CD2 | LEU | A | 38 | 80.325 | −29.193 | −10.568 | 1.00 | 12.91 | A | C |
| ATOM | 513 | C | LEU | A | 38 | 76.463 | −29.837 | −12.717 | 1.00 | 14.27 | A | C |
| ATOM | 514 | O | LEU | A | 38 | 76.094 | −30.948 | −12.336 | 1.00 | 14.74 | A | O |
| ATOM | 516 | N | GLU | A | 39 | 75.656 | −28.979 | −13.339 | 1.00 | 13.96 | A | N |
| ATOM | 517 | CA | GLU | A | 39 | 74.263 | −29.296 | −13.651 | 1.00 | 13.65 | A | C |
| ATOM | 519 | CB | GLU | A | 39 | 73.599 | −28.108 | −14.354 | 1.00 | 13.97 | A | C |
| ATOM | 522 | CG | GLU | A | 39 | 72.085 | −28.233 | −14.528 | 1.00 | 14.95 | A | C |
| ATOM | 525 | CD | GLU | A | 39 | 71.485 | −27.097 | −15.345 | 1.00 | 16.13 | A | C |
| ATOM | 526 | OE1 | GLU | A | 39 | 72.200 | −26.522 | −16.200 | 1.00 | 15.33 | A | O |
| ATOM | 527 | OE2 | GLU | A | 39 | 70.291 | −26.787 | −15.136 | 1.00 | 15.50 | A | O |
| ATOM | 528 | C | GLU | A | 39 | 74.160 | −30.536 | −14.534 | 1.00 | 13.24 | A | C |
| ATOM | 529 | O | GLU | A | 39 | 73.290 | −31.379 | −14.327 | 1.00 | 13.19 | A | O |
| ATOM | 531 | N | ALA | A | 40 | 75.050 | −30.635 | −15.517 | 1.00 | 13.18 | A | N |
| ATOM | 532 | CA | ALA | A | 40 | 75.078 | −31.773 | −16.434 | 1.00 | 13.27 | A | C |
| ATOM | 534 | CB | ALA | A | 40 | 76.121 | −31.545 | −17.518 | 1.00 | 13.09 | A | C |
| ATOM | 538 | C | ALA | A | 40 | 75.372 | −33.075 | −15.694 | 1.00 | 13.60 | A | C |
| ATOM | 539 | O | ALA | A | 40 | 74.631 | −34.052 | −15.815 | 1.00 | 13.20 | A | O |
| ATOM | 541 | N | GLU | A | 41 | 76.459 | −33.071 | −14.926 | 1.00 | 14.01 | A | N |
| ATOM | 542 | CA | GLU | A | 41 | 76.892 | −34.243 | −14.162 | 1.00 | 13.91 | A | C |
| ATOM | 544 | CB | GLU | A | 41 | 78.136 | −33.902 | −13.331 | 1.00 | 14.03 | A | C |
| ATOM | 547 | CG | GLU | A | 41 | 78.963 | −35.108 | −12.883 | 1.00 | 14.30 | A | C |
| ATOM | 550 | CD | GLU | A | 41 | 80.385 | −34.740 | −12.450 | 1.00 | 14.59 | A | C |
| ATOM | 551 | OE1 | GLU | A | 41 | 80.750 | −33.545 | −12.486 | 1.00 | 13.71 | A | O |
| ATOM | 552 | OE2 | GLU | A | 41 | 81.147 | −35.655 | −12.077 | 1.00 | 16.03 | A | O |
| ATOM | 553 | C | GLU | A | 41 | 75.766 | −34.772 | −13.268 | 1.00 | 13.65 | A | C |
| ATOM | 554 | O | GLU | A | 41 | 75.536 | −35.976 | −13.210 | 1.00 | 13.97 | A | O |
| ATOM | 556 | N | VAL | A | 42 | 75.058 | −33.872 | −12.592 | 1.00 | 13.32 | A | N |
| ATOM | 557 | CA | VAL | A | 42 | 73.908 | −34.261 | −11.772 | 1.00 | 13.82 | A | C |
| ATOM | 559 | CB | VAL | A | 42 | 73.337 | −33.065 | −10.980 | 1.00 | 13.98 | A | C |
| ATOM | 561 | CG1 | VAL | A | 42 | 72.097 | −33.481 | −10.190 | 1.00 | 11.81 | A | C |
| ATOM | 565 | CG2 | VAL | A | 42 | 74.399 | −32.489 | −10.054 | 1.00 | 14.38 | A | C |
| ATOM | 569 | C | VAL | A | 42 | 72.795 | −34.852 | −12.638 | 1.00 | 14.41 | A | C |
| ATOM | 570 | O | VAL | A | 42 | 72.145 | −35.826 | −12.252 | 1.00 | 14.02 | A | O |
| ATOM | 572 | N | ARG | A | 43 | 72.581 | −34.250 | −13.806 | 1.00 | 15.17 | A | N |
| ATOM | 573 | CA | ARG | A | 43 | 71.602 | −34.748 | −14.771 | 1.00 | 15.29 | A | C |
| ATOM | 575 | CB | ARG | A | 43 | 71.509 | −33.805 | −15.980 | 1.00 | 15.11 | A | C |
| ATOM | 578 | CG | ARG | A | 43 | 70.642 | −34.310 | −17.123 | 1.00 | 15.92 | A | C |
| ATOM | 581 | CD | ARG | A | 43 | 71.411 | −35.191 | −18.114 | 1.00 | 15.67 | A | C |
| ATOM | 584 | NE | ARG | A | 43 | 70.592 | −35.551 | −19.270 | 1.00 | 16.12 | A | N |
| ATOM | 586 | CZ | ARG | A | 43 | 70.913 | −36.472 | −20.177 | 1.00 | 16.78 | A | C |
| ATOM | 587 | NH1 | ARG | A | 43 | 70.082 | −36.721 | −21.183 | 1.00 | 17.28 | A | N |
| ATOM | 590 | NH2 | ARG | A | 43 | 72.053 | −37.151 | −20.093 | 1.00 | 17.42 | A | N |
| ATOM | 593 | C | ARG | A | 43 | 71.965 | −36.162 | −15.216 | 1.00 | 15.15 | A | C |
| ATOM | 594 | O | ARG | A | 43 | 71.100 | −37.037 | −15.276 | 1.00 | 15.51 | A | O |
| ATOM | 596 | N | ARG | A | 44 | 73.241 | −36.374 | −15.531 | 1.00 | 14.58 | A | N |
| ATOM | 597 | CA | ARG | A | 44 | 73.725 | −37.680 | −15.973 | 1.00 | 14.27 | A | C |
| ATOM | 599 | CB | ARG | A | 44 | 75.239 | −37.638 | −16.204 | 1.00 | 14.13 | A | C |
| ATOM | 602 | CG | ARG | A | 44 | 75.837 | −38.956 | −16.685 | 1.00 | 13.74 | A | C |
| ATOM | 605 | CD | ARG | A | 44 | 77.311 | −38.822 | −17.038 | 1.00 | 12.58 | A | C |
| ATOM | 608 | NE | ARG | A | 44 | 78.167 | −38.729 | −15.858 | 1.00 | 10.73 | A | N |
| ATOM | 610 | CZ | ARG | A | 44 | 79.495 | −38.644 | −15.897 | 1.00 | 10.52 | A | C |
| ATOM | 611 | NH1 | ARG | A | 44 | 80.187 | −38.566 | −14.766 | 1.00 | 10.42 | A | N |

TABLE 8-2-continued

Coordinates for L494P Structure

| ATOM | 614 | NH2 | ARG | A | 44 | 80.139 | −38.638 | −17.061 | 1.00 | 11.08 | A | N |
|---|---|---|---|---|---|---|---|---|---|---|---|---|
| ATOM | 617 | C | ARG | A | 44 | 73.391 | −38.772 | −14.963 | 1.00 | 14.55 | A | C |
| ATOM | 618 | O | ARG | A | 44 | 72.868 | −39.825 | −15.327 | 1.00 | 14.69 | A | O |
| ATOM | 620 | N | GLU | A | 45 | 73.690 | −38.506 | −13.694 | 1.00 | 14.88 | A | N |
| ATOM | 621 | CA | GLU | A | 45 | 73.533 | −39.502 | −12.633 | 1.00 | 15.12 | A | C |
| ATOM | 623 | CB | GLU | A | 45 | 74.228 | −39.032 | −11.351 | 1.00 | 15.38 | A | C |
| ATOM | 626 | CG | GLU | A | 45 | 75.737 | −38.939 | −11.473 | 1.00 | 15.34 | A | C |
| ATOM | 629 | CD | GLU | A | 45 | 76.367 | −40.280 | −11.758 | 1.00 | 15.55 | A | C |
| ATOM | 630 | OE1 | GLU | A | 45 | 76.236 | −41.183 | −10.906 | 1.00 | 16.23 | A | O |
| ATOM | 631 | OE2 | GLU | A | 45 | 76.982 | −40.433 | −12.835 | 1.00 | 15.50 | A | O |
| ATOM | 632 | C | GLU | A | 45 | 72.074 | −39.843 | −12.337 | 1.00 | 15.09 | A | C |
| ATOM | 633 | O | GLU | A | 45 | 71.771 | −40.973 | −11.951 | 1.00 | 15.45 | A | O |
| ATOM | 635 | N | ILE | A | 46 | 71.180 | −38.870 | −12.506 | 1.00 | 14.76 | A | N |
| ATOM | 636 | CA | ILE | A | 46 | 69.744 | −39.112 | −12.348 | 1.00 | 14.30 | A | C |
| ATOM | 638 | CB | ILE | A | 46 | 68.926 | −37.795 | −12.366 | 1.00 | 14.11 | A | C |
| ATOM | 640 | CG1 | ILE | A | 46 | 69.239 | −36.947 | −11.130 | 1.00 | 13.91 | A | C |
| ATOM | 643 | CD1 | ILE | A | 46 | 68.714 | −35.524 | −11.210 | 1.00 | 11.51 | A | C |
| ATOM | 647 | CG2 | ILE | A | 46 | 67.439 | −38.092 | −12.399 | 1.00 | 13.21 | A | C |
| ATOM | 651 | C | ILE | A | 46 | 69.232 | −40.051 | −13.446 | 1.00 | 14.04 | A | C |
| ATOM | 652 | O | ILE | A | 46 | 68.418 | −40.939 | −13.175 | 1.00 | 13.88 | A | O |
| ATOM | 654 | N | ASN | A | 47 | 69.725 | −39.856 | −14.671 | 1.00 | 13.76 | A | N |
| ATOM | 655 | CA | ASN | A | 47 | 69.287 | −40.643 | −15.834 | 1.00 | 13.67 | A | C |
| ATOM | 657 | CB | ASN | A | 47 | 69.461 | −39.835 | −17.124 | 1.00 | 13.22 | A | C |
| ATOM | 660 | CG | ASN | A | 47 | 68.546 | −38.636 | −17.190 | 1.00 | 12.47 | A | C |
| ATOM | 661 | OD1 | ASN | A | 47 | 67.387 | −38.694 | −16.774 | 1.00 | 12.16 | A | O |
| ATOM | 662 | ND2 | ASN | A | 47 | 69.058 | −37.539 | −17.722 | 1.00 | 13.14 | A | N |
| ATOM | 665 | C | ASN | A | 47 | 69.994 | −41.987 | −15.994 | 1.00 | 13.91 | A | C |
| ATOM | 666 | O | ASN | A | 47 | 69.587 | −42.808 | −16.817 | 1.00 | 13.86 | A | O |
| ATOM | 668 | N | ASN | A | 48 | 71.048 | −42.205 | −15.213 | 1.00 | 14.42 | A | N |
| ATOM | 669 | CA | ASN | A | 48 | 71.827 | −43.441 | −15.274 | 1.00 | 14.74 | A | C |
| ATOM | 671 | CB | ASN | A | 48 | 72.850 | −43.469 | −14.132 | 1.00 | 14.72 | A | C |
| ATOM | 674 | CG | ASN | A | 48 | 73.753 | −44.679 | −14.183 | 1.00 | 13.04 | A | C |
| ATOM | 675 | OD1 | ASN | A | 48 | 74.135 | −45.138 | −15.256 | 1.00 | 11.75 | A | O |
| ATOM | 676 | ND2 | ASN | A | 48 | 74.106 | −45.199 | −13.017 | 1.00 | 13.70 | A | N |
| ATOM | 679 | C | ASN | A | 48 | 70.947 | −44.693 | −15.222 | 1.00 | 15.25 | A | C |
| ATOM | 680 | O | ASN | A | 48 | 70.371 | −45.016 | −14.186 | 1.00 | 14.91 | A | O |
| ATOM | 682 | N | GLU | A | 49 | 70.855 | −45.385 | −16.355 | 1.00 | 16.44 | A | N |
| ATOM | 683 | CA | GLU | A | 49 | 70.070 | −46.615 | −16.472 | 1.00 | 17.44 | A | C |
| ATOM | 685 | CB | GLU | A | 49 | 70.073 | −47.113 | −17.924 | 1.00 | 17.86 | A | C |
| ATOM | 688 | CG | GLU | A | 49 | 69.434 | −46.153 | −18.947 | 1.00 | 20.47 | A | C |
| ATOM | 691 | CD | GLU | A | 49 | 67.909 | −46.256 | −19.022 | 1.00 | 23.90 | A | C |
| ATOM | 692 | OE1 | GLU | A | 49 | 67.362 | −47.364 | −18.830 | 1.00 | 26.25 | A | O |
| ATOM | 693 | OE2 | GLU | A | 49 | 67.256 | −45.223 | −19.293 | 1.00 | 24.41 | A | O |
| ATOM | 694 | C | GLU | A | 49 | 70.608 | −47.715 | −15.555 | 1.00 | 17.76 | A | C |
| ATOM | 695 | O | GLU | A | 49 | 69.839 | −48.490 | −14.995 | 1.00 | 17.28 | A | O |
| ATOM | 697 | N | LYS | A | 50 | 71.929 | −47.765 | −15.402 | 1.00 | 18.95 | A | N |
| ATOM | 698 | CA | LYS | A | 50 | 72.596 | −48.784 | −14.591 | 1.00 | 19.93 | A | C |
| ATOM | 700 | CB | LYS | A | 50 | 73.871 | −49.267 | −15.298 | 1.00 | 20.28 | A | C |
| ATOM | 703 | CG | LYS | A | 50 | 73.695 | −49.676 | −16.758 | 1.00 | 21.77 | A | C |
| ATOM | 706 | CD | LYS | A | 50 | 74.932 | −50.420 | −17.276 | 1.00 | 23.08 | A | C |
| ATOM | 709 | CE | LYS | A | 50 | 75.158 | −50.200 | −18.772 | 1.00 | 23.59 | A | C |
| ATOM | 712 | NZ | LYS | A | 50 | 73.974 | −50.577 | −19.593 | 1.00 | 23.30 | A | N |
| ATOM | 716 | C | LYS | A | 50 | 72.955 | −48.250 | −13.200 | 1.00 | 20.51 | A | C |
| ATOM | 717 | O | LYS | A | 50 | 74.120 | −48.286 | −12.796 | 1.00 | 20.59 | A | O |
| ATOM | 719 | N | ALA | A | 51 | 71.958 | −47.758 | −12.470 | 1.00 | 21.42 | A | N |
| ATOM | 720 | CA | ALA | A | 51 | 72.171 | −47.241 | −11.116 | 1.00 | 22.31 | A | C |
| ATOM | 722 | CB | ALA | A | 51 | 71.607 | −45.839 | −10.994 | 1.00 | 22.41 | A | C |
| ATOM | 726 | C | ALA | A | 51 | 71.525 | −48.163 | −10.085 | 1.00 | 23.21 | A | C |
| ATOM | 727 | O | ALA | A | 51 | 70.500 | −48.791 | −10.361 | 1.00 | 23.63 | A | O |
| ATOM | 729 | N | GLU | A | 52 | 72.124 | −48.239 | −8.898 | 1.00 | 23.78 | A | N |
| ATOM | 730 | CA | GLU | A | 52 | 71.577 | −49.056 | −7.816 | 1.00 | 24.30 | A | C |
| ATOM | 732 | CB | GLU | A | 52 | 72.590 | −49.208 | −6.675 | 1.00 | 24.41 | A | C |
| ATOM | 735 | CG | GLU | A | 52 | 72.493 | −50.535 | −5.927 | 1.00 | 26.16 | A | C |
| ATOM | 738 | CD | GLU | A | 52 | 72.854 | −51.746 | −6.787 | 1.00 | 27.22 | A | C |
| ATOM | 739 | OE1 | GLU | A | 52 | 73.411 | −51.571 | −7.894 | 1.00 | 27.13 | A | O |
| ATOM | 740 | OE2 | GLU | A | 52 | 72.580 | −52.881 | −6.345 | 1.00 | 28.02 | A | O |
| ATOM | 741 | C | GLU | A | 52 | 70.296 | −48.394 | −7.320 | 1.00 | 24.56 | A | C |
| ATOM | 742 | O | GLU | A | 52 | 70.241 | −47.171 | −7.194 | 1.00 | 25.07 | A | O |
| ATOM | 744 | N | PHE | A | 53 | 69.272 | −49.199 | −7.049 | 1.00 | 24.66 | A | N |
| ATOM | 745 | CA | PHE | A | 53 | 67.932 | −48.672 | −6.762 | 1.00 | 24.68 | A | C |
| ATOM | 747 | CB | PHE | A | 53 | 66.919 | −49.811 | −6.571 | 1.00 | 25.20 | A | C |
| ATOM | 750 | CG | PHE | A | 53 | 66.487 | −50.467 | −7.862 | 1.00 | 28.10 | A | C |
| ATOM | 751 | CD1 | PHE | A | 53 | 65.998 | −49.700 | −8.920 | 1.00 | 30.01 | A | C |
| ATOM | 753 | CE1 | PHE | A | 53 | 65.592 | −50.296 | −10.112 | 1.00 | 30.91 | A | C |
| ATOM | 755 | CZ | PHE | A | 53 | 65.666 | −51.679 | −10.254 | 1.00 | 32.14 | A | C |
| ATOM | 757 | CE2 | PHE | A | 53 | 66.144 | −52.458 | −9.202 | 1.00 | 31.02 | A | C |
| ATOM | 759 | CD2 | PHE | A | 53 | 66.549 | −51.851 | −8.013 | 1.00 | 29.73 | A | C |
| ATOM | 761 | C | PHE | A | 53 | 67.879 | −47.717 | −5.566 | 1.00 | 23.76 | A | C |

TABLE 8-2-continued

Coordinates for L494P Structure

| ATOM | 762 | O | PHE | A | 53 | 67.250 | −46.663 | −5.650 | 1.00 | 23.93 | A | O |
|---|---|---|---|---|---|---|---|---|---|---|---|---|
| ATOM | 764 | N | LEU | A | 54 | 68.535 | −48.075 | −4.465 | 1.00 | 22.52 | A | N |
| ATOM | 765 | CA | LEU | A | 54 | 68.557 | −47.206 | −3.286 | 1.00 | 21.36 | A | C |
| ATOM | 767 | CB | LEU | A | 54 | 69.083 | −47.951 | −2.055 | 1.00 | 21.51 | A | C |
| ATOM | 770 | CG | LEU | A | 54 | 68.781 | −47.281 | −0.708 | 1.00 | 21.41 | A | C |
| ATOM | 772 | CD1 | LEU | A | 54 | 67.301 | −47.429 | −0.372 | 1.00 | 20.97 | A | C |
| ATOM | 776 | CD2 | LEU | A | 54 | 69.653 | −47.855 | 0.412 | 1.00 | 19.73 | A | C |
| ATOM | 780 | C | LEU | A | 54 | 69.401 | −45.959 | −3.541 | 1.00 | 20.27 | A | C |
| ATOM | 781 | O | LEU | A | 54 | 69.000 | −44.856 | −3.175 | 1.00 | 20.35 | A | O |
| ATOM | 783 | N | THR | A | 55 | 70.561 | −46.142 | −4.170 | 1.00 | 19.14 | A | N |
| ATOM | 784 | CA | THR | A | 55 | 71.463 | −45.031 | −4.495 | 1.00 | 18.11 | A | C |
| ATOM | 786 | CB | THR | A | 55 | 72.739 | −45.521 | −5.210 | 1.00 | 18.12 | A | C |
| ATOM | 788 | OG1 | THR | A | 55 | 73.383 | −46.521 | −4.412 | 1.00 | 17.71 | A | O |
| ATOM | 790 | CG2 | THR | A | 55 | 73.707 | −44.363 | −5.451 | 1.00 | 17.05 | A | C |
| ATOM | 794 | C | THR | A | 55 | 70.787 | −43.994 | −5.380 | 1.00 | 17.32 | A | C |
| ATOM | 795 | O | THR | A | 55 | 71.003 | −42.798 | −5.210 | 1.00 | 17.16 | A | O |
| ATOM | 797 | N | LEU | A | 56 | 69.975 | −44.457 | −6.327 | 1.00 | 16.99 | A | N |
| ATOM | 798 | CA | LEU | A | 56 | 69.204 | −43.555 | −7.179 | 1.00 | 17.23 | A | C |
| ATOM | 800 | CB | LEU | A | 56 | 68.488 | −44.324 | −8.295 | 1.00 | 17.55 | A | C |
| ATOM | 803 | CG | LEU | A | 56 | 67.539 | −43.518 | −9.196 | 1.00 | 18.41 | A | C |
| ATOM | 805 | CD1 | LEU | A | 56 | 68.246 | −42.308 | −9.796 | 1.00 | 18.81 | A | C |
| ATOM | 809 | CD2 | LEU | A | 56 | 66.954 | −44.398 | −10.296 | 1.00 | 19.59 | A | C |
| ATOM | 813 | C | LEU | A | 56 | 68.190 | −42.785 | −6.343 | 1.00 | 16.79 | A | C |
| ATOM | 814 | O | LEU | A | 56 | 68.100 | −41.559 | −6.443 | 1.00 | 16.92 | A | O |
| ATOM | 816 | N | LEU | A | 57 | 67.436 | −43.511 | −5.520 | 1.00 | 16.16 | A | N |
| ATOM | 817 | CA | LEU | A | 57 | 66.437 | −42.899 | −4.643 | 1.00 | 15.66 | A | C |
| ATOM | 819 | CB | LEU | A | 57 | 65.700 | −43.972 | −3.833 | 1.00 | 15.19 | A | C |
| ATOM | 822 | CG | LEU | A | 57 | 64.765 | −44.889 | −4.625 | 1.00 | 14.21 | A | C |
| ATOM | 824 | CD1 | LEU | A | 57 | 64.334 | −46.067 | −3.767 | 1.00 | 13.60 | A | C |
| ATOM | 828 | CD2 | LEU | A | 57 | 63.552 | −44.133 | −5.151 | 1.00 | 11.60 | A | C |
| ATOM | 832 | C | LEU | A | 57 | 67.055 | −41.859 | −3.701 | 1.00 | 15.52 | A | C |
| ATOM | 833 | O | LEU | A | 57 | 66.458 | −40.809 | −3.453 | 1.00 | 15.41 | A | O |
| ATOM | 835 | N | GLU | A | 58 | 68.254 | −42.147 | −3.197 | 1.00 | 15.21 | A | N |
| ATOM | 836 | CA | GLU | A | 58 | 68.940 | −41.238 | −2.274 | 1.00 | 14.75 | A | C |
| ATOM | 838 | CB | GLU | A | 58 | 69.981 | −41.988 | −1.430 | 1.00 | 14.86 | A | C |
| ATOM | 841 | CG | GLU | A | 58 | 69.363 | −42.871 | −0.341 | 1.00 | 15.06 | A | C |
| ATOM | 844 | CD | GLU | A | 58 | 70.385 | −43.442 | 0.633 | 1.00 | 16.98 | A | C |
| ATOM | 845 | OE1 | GLU | A | 58 | 71.547 | −42.981 | 0.644 | 1.00 | 19.17 | A | O |
| ATOM | 846 | OE2 | GLU | A | 58 | 70.020 | −44.360 | 1.398 | 1.00 | 18.53 | A | O |
| ATOM | 847 | C | GLU | A | 58 | 69.575 | −40.035 | −2.975 | 1.00 | 14.11 | A | C |
| ATOM | 848 | O | GLU | A | 58 | 69.657 | −38.959 | −2.382 | 1.00 | 14.43 | A | O |
| ATOM | 850 | N | LEU | A | 59 | 70.020 | −40.202 | −4.221 | 1.00 | 13.22 | A | N |
| ATOM | 851 | CA | LEU | A | 59 | 70.528 | −39.065 | −4.999 | 1.00 | 12.44 | A | C |
| ATOM | 853 | CB | LEU | A | 59 | 71.180 | −39.518 | −6.311 | 1.00 | 12.19 | A | C |
| ATOM | 856 | CG | LEU | A | 59 | 71.677 | −38.393 | −7.235 | 1.00 | 10.80 | A | C |
| ATOM | 858 | CD1 | LEU | A | 59 | 72.780 | −37.589 | −6.572 | 1.00 | 9.85 | A | C |
| ATOM | 862 | CD2 | LEU | A | 59 | 72.154 | −38.949 | −8.566 | 1.00 | 9.48 | A | C |
| ATOM | 866 | C | LEU | A | 59 | 69.390 | −38.100 | −5.298 | 1.00 | 12.08 | A | C |
| ATOM | 867 | O | LEU | A | 59 | 69.549 | −36.889 | −5.164 | 1.00 | 11.53 | A | O |
| ATOM | 869 | N | ILE | A | 60 | 68.249 | −38.649 | −5.706 | 1.00 | 12.13 | A | N |
| ATOM | 870 | CA | ILE | A | 60 | 67.048 | −37.856 | −5.955 | 1.00 | 12.54 | A | C |
| ATOM | 872 | CB | ILE | A | 60 | 65.863 | −38.745 | −6.386 | 1.00 | 12.58 | A | C |
| ATOM | 874 | CG1 | ILE | A | 60 | 66.077 | −39.276 | −7.806 | 1.00 | 12.32 | A | C |
| ATOM | 877 | CD1 | ILE | A | 60 | 65.083 | −40.350 | −8.213 | 1.00 | 9.20 | A | C |
| ATOM | 881 | CG2 | ILE | A | 60 | 64.557 | −37.964 | −6.324 | 1.00 | 13.18 | A | C |
| ATOM | 885 | C | ILE | A | 60 | 66.649 | −37.073 | −4.707 | 1.00 | 13.10 | A | C |
| ATOM | 886 | O | ILE | A | 60 | 66.474 | −35.853 | −4.761 | 1.00 | 13.34 | A | O |
| ATOM | 888 | N | ASP | A | 61 | 66.512 | −37.782 | −3.587 | 1.00 | 13.39 | A | N |
| ATOM | 889 | CA | ASP | A | 61 | 66.154 | −37.162 | −2.310 | 1.00 | 13.31 | A | C |
| ATOM | 891 | CB | ASP | A | 61 | 66.150 | −38.205 | −1.185 | 1.00 | 13.34 | A | C |
| ATOM | 894 | CG | ASP | A | 61 | 65.640 | −37.650 | 0.139 | 1.00 | 13.56 | A | C |
| ATOM | 895 | OD1 | ASP | A | 61 | 64.927 | −36.625 | 0.136 | 1.00 | 12.03 | A | O |
| ATOM | 896 | OD2 | ASP | A | 61 | 65.946 | −38.252 | 1.191 | 1.00 | 15.02 | A | O |
| ATOM | 897 | C | ASP | A | 61 | 67.121 | −36.027 | −1.979 | 1.00 | 13.29 | A | C |
| ATOM | 898 | O | ASP | A | 61 | 66.694 | −34.889 | −1.777 | 1.00 | 13.14 | A | O |
| ATOM | 900 | N | ASN | A | 62 | 68.416 | −36.345 | −1.943 | 1.00 | 13.31 | A | N |
| ATOM | 901 | CA | ASN | A | 62 | 69.463 | −35.346 | −1.704 | 1.00 | 13.68 | A | C |
| ATOM | 903 | CB | ASN | A | 62 | 70.865 | −35.972 | −1.816 | 1.00 | 13.84 | A | C |
| ATOM | 906 | CG | ASN | A | 62 | 71.306 | −36.690 | −0.542 | 1.00 | 13.75 | A | C |
| ATOM | 907 | OD1 | ASN | A | 62 | 70.678 | −36.574 | 0.510 | 1.00 | 11.26 | A | O |
| ATOM | 908 | ND2 | ASN | A | 62 | 72.404 | −37.432 | −0.639 | 1.00 | 14.47 | A | N |
| ATOM | 911 | C | ASN | A | 62 | 69.363 | −34.158 | −2.661 | 1.00 | 14.11 | A | C |
| ATOM | 912 | O | ASN | A | 62 | 69.476 | −33.005 | −2.240 | 1.00 | 14.02 | A | O |
| ATOM | 914 | N | VAL | A | 63 | 69.150 | −34.446 | −3.944 | 1.00 | 14.45 | A | N |
| ATOM | 915 | CA | VAL | A | 63 | 68.998 | −33.400 | −4.957 | 1.00 | 14.74 | A | C |
| ATOM | 917 | CB | VAL | A | 63 | 68.845 | −33.996 | −6.377 | 1.00 | 14.56 | A | C |
| ATOM | 919 | CG1 | VAL | A | 63 | 68.343 | −32.943 | −7.354 | 1.00 | 14.88 | A | C |
| ATOM | 923 | CG2 | VAL | A | 63 | 70.165 | −34.575 | −6.854 | 1.00 | 14.45 | A | C |

TABLE 8-2-continued

Coordinates for L494P Structure

| ATOM | 927 | C | VAL | A | 63 | 67.796 | −32.503 | −4.657 | 1.00 | 15.15 | A | C |
|---|---|---|---|---|---|---|---|---|---|---|---|---|
| ATOM | 928 | O | VAL | A | 63 | 67.890 | −31.278 | −4.762 | 1.00 | 15.47 | A | O |
| ATOM | 930 | N | GLN | A | 64 | 66.675 | −33.114 | −4.281 | 1.00 | 15.27 | A | N |
| ATOM | 931 | CA | GLN | A | 64 | 65.467 | −32.355 | −3.956 | 1.00 | 15.55 | A | C |
| ATOM | 933 | CB | GLN | A | 64 | 64.254 | −33.283 | −3.802 | 1.00 | 15.45 | A | C |
| ATOM | 936 | CG | GLN | A | 64 | 63.743 | −33.865 | −5.114 | 1.00 | 13.13 | A | C |
| ATOM | 939 | CD | GLN | A | 64 | 62.319 | −34.385 | −5.025 | 1.00 | 10.71 | A | C |
| ATOM | 940 | OE1 | GLN | A | 64 | 61.622 | −34.470 | −6.033 | 1.00 | 10.64 | A | O |
| ATOM | 941 | NE2 | GLN | A | 64 | 61.881 | −34.731 | −3.821 | 1.00 | 8.09 | A | N |
| ATOM | 944 | C | GLN | A | 64 | 65.650 | −31.519 | −2.688 | 1.00 | 15.86 | A | C |
| ATOM | 945 | O | GLN | A | 64 | 65.402 | −30.311 | −2.693 | 1.00 | 16.06 | A | O |
| ATOM | 947 | N | ARG | A | 65 | 66.089 | −32.167 | −1.612 | 1.00 | 15.84 | A | N |
| ATOM | 948 | CA | ARG | A | 65 | 66.241 | −31.506 | −0.313 | 1.00 | 15.98 | A | C |
| ATOM | 950 | CB | ARG | A | 65 | 66.627 | −32.523 | 0.764 | 1.00 | 16.31 | A | C |
| ATOM | 953 | CG | ARG | A | 65 | 65.505 | −33.496 | 1.113 | 1.00 | 18.72 | A | C |
| ATOM | 956 | CD | ARG | A | 65 | 65.879 | −34.400 | 2.279 | 1.00 | 20.75 | A | C |
| ATOM | 959 | NE | ARG | A | 65 | 66.068 | −33.641 | 3.514 | 1.00 | 22.71 | A | N |
| ATOM | 961 | CZ | ARG | A | 65 | 66.575 | −34.133 | 4.642 | 1.00 | 24.75 | A | C |
| ATOM | 962 | NH1 | ARG | A | 65 | 66.956 | −35.405 | 4.721 | 1.00 | 25.07 | A | N |
| ATOM | 965 | NH2 | ARG | A | 65 | 66.703 | −33.343 | 5.704 | 1.00 | 26.41 | A | N |
| ATOM | 968 | C | ARG | A | 65 | 67.253 | −30.361 | −0.342 | 1.00 | 15.53 | A | C |
| ATOM | 969 | O | ARG | A | 65 | 67.039 | −29.331 | 0.297 | 1.00 | 15.14 | A | O |
| ATOM | 971 | N | LEU | A | 66 | 68.338 | −30.536 | −1.099 | 1.00 | 15.13 | A | N |
| ATOM | 972 | CA | LEU | A | 66 | 69.343 | −29.481 | −1.287 | 1.00 | 14.45 | A | C |
| ATOM | 974 | CB | LEU | A | 66 | 70.588 | −30.046 | −1.979 | 1.00 | 14.24 | A | C |
| ATOM | 977 | CG | LEU | A | 66 | 71.505 | −30.909 | −1.108 | 1.00 | 13.57 | A | C |
| ATOM | 979 | CD1 | LEU | A | 66 | 72.413 | −31.781 | −1.961 | 1.00 | 13.45 | A | C |
| ATOM | 983 | CD2 | LEU | A | 66 | 72.329 | −30.036 | −0.178 | 1.00 | 12.36 | A | C |
| ATOM | 987 | C | LEU | A | 66 | 68.807 | −28.271 | −2.073 | 1.00 | 14.56 | A | C |
| ATOM | 988 | O | LEU | A | 66 | 69.544 | −27.313 | −2.332 | 1.00 | 14.45 | A | O |
| ATOM | 990 | N | GLY | A | 67 | 67.533 | −28.330 | −2.459 | 1.00 | 14.51 | A | N |
| ATOM | 991 | CA | GLY | A | 67 | 66.842 | −27.203 | −3.059 | 1.00 | 14.34 | A | C |
| ATOM | 994 | C | GLY | A | 67 | 66.968 | −27.115 | −4.564 | 1.00 | 14.63 | A | C |
| ATOM | 995 | O | GLY | A | 67 | 66.621 | −26.093 | −5.152 | 1.00 | 14.83 | A | O |
| ATOM | 997 | N | LEU | A | 68 | 67.448 | −28.191 | −5.189 | 1.00 | 15.09 | A | N |
| ATOM | 998 | CA | LEU | A | 68 | 67.656 | −28.234 | −6.638 | 1.00 | 15.36 | A | C |
| ATOM | 1000 | CB | LEU | A | 68 | 69.035 | −28.828 | −6.950 | 1.00 | 15.11 | A | C |
| ATOM | 1003 | CG | LEU | A | 68 | 70.243 | −28.122 | −6.332 | 1.00 | 14.67 | A | C |
| ATOM | 1005 | CD1 | LEU | A | 68 | 71.533 | −28.793 | −6.779 | 1.00 | 13.80 | A | C |
| ATOM | 1009 | CD2 | LEU | A | 68 | 70.256 | −26.651 | −6.699 | 1.00 | 12.27 | A | C |
| ATOM | 1013 | C | LEU | A | 68 | 66.577 | −29.042 | −7.371 | 1.00 | 15.95 | A | C |
| ATOM | 1014 | O | LEU | A | 68 | 66.679 | −29.258 | −8.578 | 1.00 | 16.42 | A | O |
| ATOM | 1016 | N | GLY | A | 69 | 65.543 | −29.473 | −6.653 | 1.00 | 16.33 | A | N |
| ATOM | 1017 | CA | GLY | A | 69 | 64.496 | −30.320 | −7.228 | 1.00 | 16.45 | A | C |
| ATOM | 1020 | C | GLY | A | 69 | 63.810 | −29.734 | −8.449 | 1.00 | 16.20 | A | C |
| ATOM | 1021 | O | GLY | A | 69 | 63.667 | −30.410 | −9.469 | 1.00 | 16.47 | A | O |
| ATOM | 1023 | N | TYR | A | 70 | 63.392 | −28.474 | −8.340 | 1.00 | 15.95 | A | N |
| ATOM | 1024 | CA | TYR | A | 70 | 62.726 | −27.760 | −9.440 | 1.00 | 15.71 | A | C |
| ATOM | 1026 | CB | TYR | A | 70 | 62.501 | −26.284 | −9.065 | 1.00 | 15.82 | A | C |
| ATOM | 1029 | CG | TYR | A | 70 | 63.755 | −25.424 | −9.114 | 1.00 | 14.12 | A | C |
| ATOM | 1030 | CD1 | TYR | A | 70 | 63.989 | −24.561 | −10.183 | 1.00 | 10.77 | A | C |
| ATOM | 1032 | CE1 | TYR | A | 70 | 65.133 | −23.781 | −10.237 | 1.00 | 10.89 | A | C |
| ATOM | 1034 | CZ | TYR | A | 70 | 66.066 | −23.856 | −9.216 | 1.00 | 11.24 | A | C |
| ATOM | 1035 | OH | TYR | A | 70 | 67.208 | −23.084 | −9.269 | 1.00 | 9.98 | A | O |
| ATOM | 1037 | CE2 | TYR | A | 70 | 65.859 | −24.705 | −8.145 | 1.00 | 11.41 | A | C |
| ATOM | 1039 | CD2 | TYR | A | 70 | 64.709 | −25.485 | −8.100 | 1.00 | 12.70 | A | C |
| ATOM | 1041 | C | TYR | A | 70 | 63.522 | −27.841 | −10.744 | 1.00 | 15.82 | A | C |
| ATOM | 1042 | O | TYR | A | 70 | 62.951 | −27.909 | −11.835 | 1.00 | 15.94 | A | O |
| ATOM | 1044 | N | ARG | A | 71 | 64.844 | −27.839 | −10.607 | 1.00 | 15.72 | A | N |
| ATOM | 1045 | CA | ARG | A | 71 | 65.757 | −27.824 | −11.737 | 1.00 | 15.71 | A | C |
| ATOM | 1047 | CB | ARG | A | 71 | 67.171 | −27.540 | −11.224 | 1.00 | 15.56 | A | C |
| ATOM | 1050 | CG | ARG | A | 71 | 68.175 | −27.150 | −12.286 | 1.00 | 16.84 | A | C |
| ATOM | 1053 | CD | ARG | A | 71 | 69.345 | −26.386 | −11.679 | 1.00 | 17.64 | A | C |
| ATOM | 1056 | NE | ARG | A | 71 | 69.076 | −24.951 | −11.600 | 1.00 | 18.02 | A | N |
| ATOM | 1058 | CZ | ARG | A | 71 | 69.124 | −24.113 | −12.633 | 1.00 | 18.91 | A | C |
| ATOM | 1059 | NH1 | ARG | A | 71 | 68.863 | −22.828 | −12.444 | 1.00 | 20.58 | A | N |
| ATOM | 1062 | NH2 | ARG | A | 71 | 69.428 | −24.546 | −13.856 | 1.00 | 18.44 | A | N |
| ATOM | 1065 | C | ARG | A | 71 | 65.729 | −29.131 | −12.535 | 1.00 | 15.68 | A | C |
| ATOM | 1066 | O | ARG | A | 71 | 65.790 | −29.111 | −13.764 | 1.00 | 15.69 | A | O |
| ATOM | 1068 | N | PHE | A | 72 | 65.625 | −30.260 | −11.838 | 1.00 | 15.70 | A | N |
| ATOM | 1069 | CA | PHE | A | 72 | 65.712 | −31.573 | −12.478 | 1.00 | 15.94 | A | C |
| ATOM | 1071 | CB | PHE | A | 72 | 66.838 | −32.393 | −11.835 | 1.00 | 15.86 | A | C |
| ATOM | 1074 | CG | PHE | A | 72 | 68.197 | −31.764 | −11.949 | 1.00 | 13.92 | A | C |
| ATOM | 1075 | CD1 | PHE | A | 72 | 68.891 | −31.797 | −13.151 | 1.00 | 13.93 | A | C |
| ATOM | 1077 | CE1 | PHE | A | 72 | 70.153 | −31.229 | −13.260 | 1.00 | 13.72 | A | C |
| ATOM | 1079 | CZ | PHE | A | 72 | 70.737 | −30.625 | −12.157 | 1.00 | 13.27 | A | C |
| ATOM | 1081 | CE2 | PHE | A | 72 | 70.057 | −30.590 | −10.951 | 1.00 | 12.76 | A | C |
| ATOM | 1083 | CD2 | PHE | A | 72 | 68.795 | −31.161 | −10.851 | 1.00 | 12.21 | A | C |

TABLE 8-2-continued

Coordinates for L494P Structure

| ATOM | 1085 | C | PHE | A | 72 | 64.407 | −32.371 | −12.404 | 1.00 | 16.42 A | C |
|---|---|---|---|---|---|---|---|---|---|---|---|
| ATOM | 1086 | O | PHE | A | 72 | 64.439 | −33.601 | −12.348 | 1.00 | 16.51 A | O |
| ATOM | 1088 | N | GLU | A | 73 | 63.265 | −31.686 | −12.425 | 1.00 | 16.94 A | N |
| ATOM | 1089 | CA | GLU | A | 73 | 61.967 | −32.365 | −12.315 | 1.00 | 17.43 A | C |
| ATOM | 1091 | CB | GLU | A | 73 | 60.812 | −31.361 | −12.397 | 1.00 | 17.65 A | C |
| ATOM | 1094 | CG | GLU | A | 73 | 59.425 | −31.997 | −12.254 | 1.00 | 19.25 A | C |
| ATOM | 1097 | CD | GLU | A | 73 | 58.291 | −30.983 | −12.251 | 1.00 | 21.29 A | C |
| ATOM | 1098 | OE1 | GLU | A | 73 | 58.563 | −29.769 | −12.127 | 1.00 | 22.11 A | O |
| ATOM | 1099 | OE2 | GLU | A | 73 | 57.121 | −31.410 | −12.370 | 1.00 | 21.96 A | O |
| ATOM | 1100 | C | GLU | A | 73 | 61.793 | −33.454 | −13.379 | 1.00 | 17.47 A | C |
| ATOM | 1101 | O | GLU | A | 73 | 61.625 | −34.628 | −13.047 | 1.00 | 17.51 A | O |
| ATOM | 1103 | N | SER | A | 74 | 61.841 | −33.062 | −14.649 | 1.00 | 17.73 A | N |
| ATOM | 1104 | CA | SER | A | 74 | 61.656 | −34.004 | −15.756 | 1.00 | 18.06 A | C |
| ATOM | 1106 | CB | SER | A | 74 | 61.792 | −33.293 | −17.103 | 1.00 | 18.17 A | C |
| ATOM | 1109 | OG | SER | A | 74 | 63.117 | −32.833 | −17.303 | 1.00 | 19.43 A | O |
| ATOM | 1111 | C | SER | A | 74 | 62.648 | −35.161 | −15.682 | 1.00 | 17.97 A | C |
| ATOM | 1112 | O | SER | A | 74 | 62.264 | −36.317 | −15.846 | 1.00 | 17.90 A | O |
| ATOM | 1114 | N | ASP | A | 75 | 63.915 | −34.842 | −15.425 | 1.00 | 18.18 A | N |
| ATOM | 1115 | CA | ASP | A | 75 | 64.961 | −35.862 | −15.295 | 1.00 | 18.40 A | C |
| ATOM | 1117 | CB | ASP | A | 75 | 66.344 | −35.224 | −15.112 | 1.00 | 18.40 A | C |
| ATOM | 1120 | CG | ASP | A | 75 | 66.754 | −34.365 | −16.292 | 1.00 | 18.51 A | C |
| ATOM | 1121 | OD1 | ASP | A | 75 | 67.526 | −34.847 | −17.144 | 1.00 | 15.74 A | O |
| ATOM | 1122 | OD2 | ASP | A | 75 | 66.294 | −33.207 | −16.370 | 1.00 | 20.28 A | O |
| ATOM | 1123 | C | ASP | A | 75 | 64.676 | −36.804 | −14.125 | 1.00 | 18.44 A | C |
| ATOM | 1124 | O | ASP | A | 75 | 64.923 | −38.008 | −14.221 | 1.00 | 18.88 A | O |
| ATOM | 1126 | N | ILE | A | 76 | 64.161 | −36.247 | −13.030 | 1.00 | 18.14 A | N |
| ATOM | 1127 | CA | ILE | A | 76 | 63.789 | −37.033 | −11.854 | 1.00 | 17.84 A | C |
| ATOM | 1129 | CB | ILE | A | 76 | 63.466 | −36.129 | −10.640 | 1.00 | 17.71 A | C |
| ATOM | 1131 | CG1 | ILE | A | 76 | 64.758 | −35.575 | −10.035 | 1.00 | 16.61 A | C |
| ATOM | 1134 | CD1 | ILE | A | 76 | 64.561 | −34.317 | −9.224 | 1.00 | 14.92 A | C |
| ATOM | 1138 | CG2 | ILE | A | 76 | 62.694 | −36.904 | −9.580 | 1.00 | 17.99 A | C |
| ATOM | 1142 | C | ILE | A | 76 | 62.594 | −37.930 | −12.160 | 1.00 | 17.97 A | C |
| ATOM | 1143 | O | ILE | A | 76 | 62.658 | −39.136 | −11.939 | 1.00 | 18.10 A | O |
| ATOM | 1145 | N | ARG | A | 77 | 61.515 | −37.341 | −12.674 | 1.00 | 18.15 A | N |
| ATOM | 1146 | CA | ARG | A | 77 | 60.331 | −38.107 | −13.077 | 1.00 | 18.64 A | C |
| ATOM | 1148 | CB | ARG | A | 77 | 59.350 | −37.225 | −13.851 | 1.00 | 18.82 A | C |
| ATOM | 1151 | CG | ARG | A | 77 | 58.565 | −36.253 | −12.988 | 1.00 | 20.98 A | C |
| ATOM | 1154 | CD | ARG | A | 77 | 57.624 | −35.398 | −13.835 | 1.00 | 23.38 A | C |
| ATOM | 1157 | NE | ARG | A | 77 | 56.595 | −36.205 | −14.492 | 1.00 | 24.73 A | N |
| ATOM | 1159 | CZ | ARG | A | 77 | 55.471 | −36.635 | −13.915 | 1.00 | 25.64 A | C |
| ATOM | 1160 | NH1 | ARG | A | 77 | 55.192 | −36.346 | −12.645 | 1.00 | 26.60 A | N |
| ATOM | 1163 | NH2 | ARG | A | 77 | 54.613 | −37.364 | −14.618 | 1.00 | 25.52 A | N |
| ATOM | 1166 | C | ARG | A | 77 | 60.711 | −39.312 | −13.938 | 1.00 | 18.58 A | C |
| ATOM | 1167 | O | ARG | A | 77 | 60.240 | −40.427 | −13.706 | 1.00 | 18.61 A | O |
| ATOM | 1169 | N | GLY | A | 78 | 61.568 | −39.075 | −14.928 | 1.00 | 18.28 A | N |
| ATOM | 1170 | CA | GLY | A | 78 | 62.057 | −40.134 | −15.802 | 1.00 | 18.20 A | C |
| ATOM | 1173 | C | GLY | A | 78 | 62.696 | −41.279 | −15.040 | 1.00 | 18.14 A | C |
| ATOM | 1174 | O | GLY | A | 78 | 62.502 | −42.445 | −15.386 | 1.00 | 18.30 A | O |
| ATOM | 1176 | N | ALA | A | 79 | 63.458 | −40.944 | −14.001 | 1.00 | 18.02 A | N |
| ATOM | 1177 | CA | ALA | A | 79 | 64.134 | −41.945 | −13.180 | 1.00 | 18.14 A | C |
| ATOM | 1179 | CB | ALA | A | 79 | 65.142 | −41.280 | −12.258 | 1.00 | 18.16 A | C |
| ATOM | 1183 | C | ALA | A | 79 | 63.134 | −42.763 | −12.369 | 1.00 | 18.13 A | C |
| ATOM | 1184 | O | ALA | A | 79 | 63.227 | −43.991 | −12.308 | 1.00 | 18.34 A | O |
| ATOM | 1186 | N | LEU | A | 80 | 62.179 | −42.073 | −11.754 | 1.00 | 18.13 A | N |
| ATOM | 1187 | CA | LEU | A | 80 | 61.136 | −42.727 | −10.969 | 1.00 | 18.20 A | C |
| ATOM | 1189 | CB | LEU | A | 80 | 60.348 | −41.693 | −10.161 | 1.00 | 17.90 A | C |
| ATOM | 1192 | CG | LEU | A | 80 | 61.135 | −41.067 | −9.009 | 1.00 | 16.44 A | C |
| ATOM | 1194 | CD1 | LEU | A | 80 | 60.478 | −39.790 | −8.526 | 1.00 | 15.42 A | C |
| ATOM | 1198 | CD2 | LEU | A | 80 | 61.285 | −42.059 | −7.871 | 1.00 | 15.55 A | C |
| ATOM | 1202 | C | LEU | A | 80 | 60.189 | −43.536 | −11.851 | 1.00 | 18.82 A | C |
| ATOM | 1203 | O | LEU | A | 80 | 59.655 | −44.556 | −11.418 | 1.00 | 18.88 A | O |
| ATOM | 1205 | N | ASP | A | 81 | 59.982 | −43.083 | −13.084 | 1.00 | 19.44 A | N |
| ATOM | 1206 | CA | ASP | A | 81 | 59.149 | −43.819 | −14.033 | 1.00 | 20.08 A | C |
| ATOM | 1208 | CB | ASP | A | 81 | 58.894 | −42.984 | −15.290 | 1.00 | 20.26 A | C |
| ATOM | 1211 | CG | ASP | A | 81 | 57.690 | −43.464 | −16.067 | 1.00 | 21.37 A | C |
| ATOM | 1212 | OD1 | ASP | A | 81 | 57.879 | −44.129 | −17.108 | 1.00 | 23.00 A | O |
| ATOM | 1213 | OD2 | ASP | A | 81 | 56.554 | −43.186 | −15.624 | 1.00 | 22.87 A | O |
| ATOM | 1214 | C | ASP | A | 81 | 59.810 | −45.149 | −14.406 | 1.00 | 20.30 A | C |
| ATOM | 1215 | O | ASP | A | 81 | 59.133 | −46.174 | −14.523 | 1.00 | 19.67 A | O |
| ATOM | 1217 | N | ARG | A | 82 | 61.131 | −45.116 | −14.583 | 1.00 | 20.83 A | N |
| ATOM | 1218 | CA | ARG | A | 82 | 61.920 | −46.322 | −14.853 | 1.00 | 21.36 A | C |
| ATOM | 1220 | CB | ARG | A | 82 | 63.315 | −45.951 | −15.375 | 1.00 | 21.67 A | C |
| ATOM | 1223 | CG | ARG | A | 82 | 63.351 | −45.688 | −16.878 | 1.00 | 23.80 A | C |
| ATOM | 1226 | CD | ARG | A | 82 | 64.738 | −45.280 | −17.376 | 1.00 | 25.75 A | C |
| ATOM | 1229 | NE | ARG | A | 82 | 64.961 | −43.834 | −17.262 | 1.00 | 27.68 A | N |
| ATOM | 1231 | CZ | ARG | A | 82 | 65.707 | −43.227 | −16.335 | 1.00 | 28.28 A | C |
| ATOM | 1232 | NH1 | ARG | A | 82 | 66.349 | −43.915 | −15.389 | 1.00 | 27.87 A | N |
| ATOM | 1235 | NH2 | ARG | A | 82 | 65.813 | −41.902 | −16.356 | 1.00 | 27.78 A | N |

TABLE 8-2-continued

Coordinates for L494P Structure

| ATOM | 1238 | C   | ARG | A | 82 | 62.038 | -47.229 | -13.623 | 1.00 | 21.47 | A | C |
|------|------|-----|-----|---|----|--------|---------|---------|------|-------|---|---|
| ATOM | 1239 | O   | ARG | A | 82 | 62.181 | -48.446 | -13.760 | 1.00 | 21.30 | A | O |
| ATOM | 1241 | N   | PHE | A | 83 | 61.981 | -46.633 | -12.432 | 1.00 | 21.68 | A | N |
| ATOM | 1242 | CA  | PHE | A | 83 | 61.970 | -47.385 | -11.171 | 1.00 | 21.75 | A | C |
| ATOM | 1244 | CB  | PHE | A | 83 | 62.026 | -46.418 | -9.981  | 1.00 | 21.95 | A | C |
| ATOM | 1247 | CG  | PHE | A | 83 | 62.097 | -47.097 | -8.637  | 1.00 | 21.67 | A | C |
| ATOM | 1248 | CD1 | PHE | A | 83 | 63.190 | -47.877 | -8.301  | 1.00 | 22.11 | A | C |
| ATOM | 1250 | CE1 | PHE | A | 83 | 63.268 | -48.500 | -7.064  | 1.00 | 21.50 | A | C |
| ATOM | 1252 | CZ  | PHE | A | 83 | 62.250 | -48.336 | -6.144  | 1.00 | 21.28 | A | C |
| ATOM | 1254 | CE2 | PHE | A | 83 | 61.155 | -47.554 | -6.464  | 1.00 | 21.20 | A | C |
| ATOM | 1256 | CD2 | PHE | A | 83 | 61.082 | -46.936 | -7.704  | 1.00 | 21.17 | A | C |
| ATOM | 1258 | C   | PHE | A | 83 | 60.733 | -48.277 | -11.059 | 1.00 | 21.71 | A | C |
| ATOM | 1259 | O   | PHE | A | 83 | 60.838 | -49.450 | -10.696 | 1.00 | 21.49 | A | O |
| ATOM | 1261 | N   | VAL | A | 84 | 59.567 | -47.708 | -11.365 | 1.00 | 21.86 | A | N |
| ATOM | 1262 | CA  | VAL | A | 84 | 58.309 | -48.454 | -11.376 | 1.00 | 21.92 | A | C |
| ATOM | 1264 | CB  | VAL | A | 84 | 57.087 | -47.509 | -11.496 | 1.00 | 21.73 | A | C |
| ATOM | 1266 | CG1 | VAL | A | 84 | 55.821 | -48.285 | -11.843 | 1.00 | 21.28 | A | C |
| ATOM | 1270 | CG2 | VAL | A | 84 | 56.898 | -46.731 | -10.209 | 1.00 | 20.78 | A | C |
| ATOM | 1274 | C   | VAL | A | 84 | 58.297 | -49.451 | -12.531 | 1.00 | 22.75 | A | C |
| ATOM | 1275 | O   | VAL | A | 84 | 58.070 | -50.646 | -12.323 | 1.00 | 22.96 | A | O |
| ATOM | 1277 | N   | SER | A | 85 | 58.560 | -48.953 | -13.740 | 1.00 | 23.25 | A | N |
| ATOM | 1278 | CA  | SER | A | 85 | 58.542 | -49.777 | -14.959 | 1.00 | 23.36 | A | C |
| ATOM | 1280 | CB  | SER | A | 85 | 59.043 | -48.969 | -16.160 | 1.00 | 23.36 | A | C |
| ATOM | 1283 | OG  | SER | A | 85 | 58.267 | -47.796 | -16.343 | 1.00 | 23.72 | A | O |
| ATOM | 1285 | C   | SER | A | 85 | 59.363 | -51.059 | -14.828 | 1.00 | 23.09 | A | C |
| ATOM | 1286 | O   | SER | A | 85 | 58.944 | -52.115 | -15.300 | 1.00 | 22.81 | A | O |
| ATOM | 1288 | N   | SER | A | 86 | 60.521 | -50.958 | -14.176 | 1.00 | 23.31 | A | N |
| ATOM | 1289 | CA  | SER | A | 86 | 61.421 | -52.099 | -13.992 | 1.00 | 23.83 | A | C |
| ATOM | 1291 | CB  | SER | A | 86 | 62.880 | -51.626 | -14.021 | 1.00 | 23.95 | A | C |
| ATOM | 1294 | OG  | SER | A | 86 | 63.188 | -50.822 | -12.894 | 1.00 | 24.38 | A | O |
| ATOM | 1296 | C   | SER | A | 86 | 61.157 | -52.885 | -12.698 | 1.00 | 24.08 | A | C |
| ATOM | 1297 | O   | SER | A | 86 | 61.966 | -53.729 | -12.312 | 1.00 | 24.00 | A | O |
| ATOM | 1299 | N   | GLY | A | 87 | 60.037 | -52.604 | -12.032 | 1.00 | 24.44 | A | N |
| ATOM | 1300 | CA  | GLY | A | 87 | 59.645 | -53.333 | -10.824 | 1.00 | 24.69 | A | C |
| ATOM | 1303 | C   | GLY | A | 87 | 60.534 | -53.124 | -9.607  | 1.00 | 24.77 | A | C |
| ATOM | 1304 | O   | GLY | A | 87 | 60.542 | -53.951 | -8.693  | 1.00 | 24.93 | A | O |
| ATOM | 1306 | N   | GLY | A | 88 | 61.283 | -52.024 | -9.585  | 1.00 | 24.83 | A | N |
| ATOM | 1307 | CA  | GLY | A | 88 | 62.142 | -51.701 | -8.449  | 1.00 | 24.84 | A | C |
| ATOM | 1310 | C   | GLY | A | 88 | 61.331 | -51.396 | -7.203  | 1.00 | 24.89 | A | C |
| ATOM | 1311 | O   | GLY | A | 88 | 61.688 | -51.824 | -6.104  | 1.00 | 24.71 | A | O |
| ATOM | 1313 | N   | PHE | A | 89 | 60.235 | -50.657 | -7.386  | 1.00 | 24.99 | A | N |
| ATOM | 1314 | CA  | PHE | A | 89 | 59.296 | -50.336 | -6.304  | 1.00 | 24.94 | A | C |
| ATOM | 1316 | CB  | PHE | A | 89 | 58.218 | -49.363 | -6.802  | 1.00 | 25.23 | A | C |
| ATOM | 1319 | CG  | PHE | A | 89 | 57.181 | -49.012 | -5.769  | 1.00 | 25.50 | A | C |
| ATOM | 1320 | CD1 | PHE | A | 89 | 57.546 | -48.380 | -4.588  | 1.00 | 25.76 | A | C |
| ATOM | 1322 | CE1 | PHE | A | 89 | 56.592 | -48.050 | -3.630  | 1.00 | 26.18 | A | C |
| ATOM | 1324 | CZ  | PHE | A | 89 | 55.253 | -48.346 | -3.855  | 1.00 | 27.09 | A | C |
| ATOM | 1326 | CE2 | PHE | A | 89 | 54.874 | -48.971 | -5.033  | 1.00 | 27.63 | A | C |
| ATOM | 1328 | CD2 | PHE | A | 89 | 55.838 | -49.300 | -5.984  | 1.00 | 27.27 | A | C |
| ATOM | 1330 | C   | PHE | A | 89 | 58.647 | -51.599 | -5.746  | 1.00 | 24.65 | A | C |
| ATOM | 1331 | O   | PHE | A | 89 | 58.438 | -51.709 | -4.538  | 1.00 | 24.51 | A | O |
| ATOM | 1333 | N   | ASP | A | 90 | 58.330 | -52.545 | -6.629  | 1.00 | 24.41 | A | N |
| ATOM | 1334 | CA  | ASP | A | 90 | 57.825 | -53.851 | -6.207  | 1.00 | 24.29 | A | C |
| ATOM | 1336 | CB  | ASP | A | 90 | 57.210 | -54.613 | -7.392  | 1.00 | 24.60 | A | C |
| ATOM | 1339 | CG  | ASP | A | 90 | 56.123 | -55.595 | -6.962  | 1.00 | 25.71 | A | C |
| ATOM | 1340 | OD1 | ASP | A | 90 | 55.046 | -55.135 | -6.518  | 1.00 | 24.61 | A | O |
| ATOM | 1341 | OD2 | ASP | A | 90 | 56.341 | -56.822 | -7.078  | 1.00 | 27.27 | A | O |
| ATOM | 1342 | C   | ASP | A | 90 | 58.946 | -54.677 | -5.563  | 1.00 | 23.50 | A | C |
| ATOM | 1343 | O   | ASP | A | 90 | 58.687 | -55.508 | -4.694  | 1.00 | 23.34 | A | O |
| ATOM | 1345 | N   | ALA | A | 91 | 60.185 | -54.439 | -5.992  | 1.00 | 22.93 | A | N |
| ATOM | 1346 | CA  | ALA | A | 91 | 61.356 | -55.122 | -5.434  | 1.00 | 22.68 | A | C |
| ATOM | 1348 | CB  | ALA | A | 91 | 62.574 | -54.900 | -6.326  | 1.00 | 22.43 | A | C |
| ATOM | 1352 | C   | ALA | A | 91 | 61.666 | -54.683 | -3.999  | 1.00 | 22.49 | A | C |
| ATOM | 1353 | O   | ALA | A | 91 | 61.957 | -55.520 | -3.142  | 1.00 | 22.56 | A | O |
| ATOM | 1355 | N   | VAL | A | 92 | 61.600 | -53.377 | -3.741  | 1.00 | 22.18 | A | N |
| ATOM | 1356 | CA  | VAL | A | 92 | 61.948 | -52.834 | -2.421  | 1.00 | 21.87 | A | C |
| ATOM | 1358 | CB  | VAL | A | 92 | 62.228 | -51.304 | -2.465  | 1.00 | 22.06 | A | C |
| ATOM | 1360 | CG1 | VAL | A | 92 | 63.296 | -50.983 | -3.507  | 1.00 | 21.68 | A | C |
| ATOM | 1364 | CG2 | VAL | A | 92 | 60.952 | -50.515 | -2.735  | 1.00 | 22.62 | A | C |
| ATOM | 1368 | C   | VAL | A | 92 | 60.890 | -53.133 | -1.351  | 1.00 | 21.46 | A | C |
| ATOM | 1369 | O   | VAL | A | 92 | 61.237 | -53.335 | -0.189  | 1.00 | 21.07 | A | O |
| ATOM | 1371 | N   | THR | A | 93 | 59.614 | -53.173 | -1.738  | 1.00 | 21.50 | A | N |
| ATOM | 1372 | CA  | THR | A | 93 | 58.538 | -53.555 | -0.809  | 1.00 | 21.48 | A | C |
| ATOM | 1374 | CB  | THR | A | 93 | 57.133 | -53.525 | -1.464  | 1.00 | 21.32 | A | C |
| ATOM | 1376 | OG1 | THR | A | 93 | 57.103 | -54.398 | -2.600  | 1.00 | 20.80 | A | O |
| ATOM | 1378 | CG2 | THR | A | 93 | 56.757 | -52.110 | -1.886  | 1.00 | 20.81 | A | C |
| ATOM | 1382 | C   | THR | A | 93 | 58.770 | -54.947 | -0.226  | 1.00 | 21.77 | A | C |
| ATOM | 1383 | O   | THR | A | 93 | 58.340 | -55.229 | 0.894   | 1.00 | 22.39 | A | O |

TABLE 8-2-continued

Coordinates for L494P Structure

| ATOM | 1385 | N   | LYS | A | 94  | 59.447 | −55.807 | −0.987 | 1.00 | 21.47 A | N |
|------|------|-----|-----|---|-----|--------|---------|--------|------|---------|---|
| ATOM | 1386 | CA  | LYS | A | 94  | 59.797 | −57.146 | −0.523 | 1.00 | 21.19 A | C |
| ATOM | 1388 | CB  | LYS | A | 94  | 60.015 | −58.087 | −1.715 | 1.00 | 21.47 A | C |
| ATOM | 1391 | CG  | LYS | A | 94  | 58.821 | −58.222 | −2.660 | 1.00 | 22.94 A | C |
| ATOM | 1394 | CD  | LYS | A | 94  | 57.596 | −58.829 | −1.978 | 1.00 | 24.09 A | C |
| ATOM | 1397 | CE  | LYS | A | 94  | 56.432 | −58.970 | −2.950 | 1.00 | 24.08 A | C |
| ATOM | 1400 | NZ  | LYS | A | 94  | 55.133 | −59.149 | −2.242 | 1.00 | 24.08 A | N |
| ATOM | 1404 | C   | LYS | A | 94  | 61.042 | −57.168 | 0.368  | 1.00 | 20.63 A | C |
| ATOM | 1405 | O   | LYS | A | 94  | 61.150 | −58.036 | 1.233  | 1.00 | 20.30 A | O |
| ATOM | 1407 | N   | THR | A | 95  | 61.969 | −56.225 | 0.167  | 1.00 | 20.41 A | N |
| ATOM | 1408 | CA  | THR | A | 95  | 63.302 | −56.301 | 0.795  | 1.00 | 20.29 A | C |
| ATOM | 1410 | CB  | THR | A | 95  | 64.398 | −56.575 | −0.269 | 1.00 | 20.32 A | C |
| ATOM | 1412 | OG1 | THR | A | 95  | 64.375 | −55.546 | −1.265 | 1.00 | 20.66 A | O |
| ATOM | 1414 | CG2 | THR | A | 95  | 64.186 | −57.931 | −0.931 | 1.00 | 20.65 A | C |
| ATOM | 1418 | C   | THR | A | 95  | 63.784 | −55.102 | 1.631  | 1.00 | 19.83 A | C |
| ATOM | 1419 | O   | THR | A | 95  | 64.777 | −55.238 | 2.345  | 1.00 | 19.98 A | O |
| ATOM | 1421 | N   | SER | A | 96  | 63.120 | −53.946 | 1.555  | 1.00 | 19.31 A | N |
| ATOM | 1422 | CA  | SER | A | 96  | 63.620 | −52.739 | 2.247  | 1.00 | 18.82 A | C |
| ATOM | 1424 | CB  | SER | A | 96  | 64.689 | −52.051 | 1.391  | 1.00 | 18.43 A | C |
| ATOM | 1427 | OG  | SER | A | 96  | 65.227 | −50.917 | 2.053  | 1.00 | 17.09 A | O |
| ATOM | 1429 | C   | SER | A | 96  | 62.536 | −51.716 | 2.614  | 1.00 | 18.93 A | C |
| ATOM | 1430 | O   | SER | A | 96  | 61.889 | −51.146 | 1.734  | 1.00 | 19.15 A | O |
| ATOM | 1432 | N   | LEU | A | 97  | 62.364 | −51.474 | 3.916  | 1.00 | 18.65 A | N |
| ATOM | 1433 | CA  | LEU | A | 97  | 61.415 | −50.467 | 4.405  | 1.00 | 18.06 A | C |
| ATOM | 1435 | CB  | LEU | A | 97  | 61.285 | −50.521 | 5.935  | 1.00 | 17.85 A | C |
| ATOM | 1438 | CG  | LEU | A | 97  | 60.459 | −49.416 | 6.612  | 1.00 | 16.18 A | C |
| ATOM | 1440 | CD1 | LEU | A | 97  | 59.070 | −49.303 | 6.001  | 1.00 | 15.61 A | C |
| ATOM | 1444 | CD2 | LEU | A | 97  | 60.358 | −49.662 | 8.105  | 1.00 | 13.42 A | C |
| ATOM | 1448 | C   | LEU | A | 97  | 61.852 | −49.076 | 3.982  | 1.00 | 18.03 A | C |
| ATOM | 1449 | O   | LEU | A | 97  | 61.048 | −48.303 | 3.461  | 1.00 | 18.07 A | O |
| ATOM | 1451 | N   | HIS | A | 98  | 63.126 | −48.767 | 4.217  | 1.00 | 18.04 A | N |
| ATOM | 1452 | CA  | HIS | A | 98  | 63.707 | −47.478 | 3.831  | 1.00 | 18.00 A | C |
| ATOM | 1454 | CB  | HIS | A | 98  | 65.214 | −47.475 | 4.101  | 1.00 | 18.04 A | C |
| ATOM | 1457 | CG  | HIS | A | 98  | 65.911 | −46.239 | 3.626  | 1.00 | 18.24 A | C |
| ATOM | 1458 | ND1 | HIS | A | 98  | 65.437 | −44.972 | 3.886  | 1.00 | 18.83 A | N |
| ATOM | 1460 | CE1 | HIS | A | 98  | 66.252 | −44.080 | 3.351  | 1.00 | 20.11 A | C |
| ATOM | 1462 | NE2 | HIS | A | 98  | 67.241 | −44.724 | 2.757  | 1.00 | 20.52 A | N |
| ATOM | 1464 | CD2 | HIS | A | 98  | 67.051 | −46.075 | 2.915  | 1.00 | 19.92 A | C |
| ATOM | 1466 | C   | HIS | A | 98  | 63.437 | −47.172 | 2.360  | 1.00 | 17.56 A | C |
| ATOM | 1467 | O   | HIS | A | 98  | 62.942 | −46.095 | 2.019  | 1.00 | 17.27 A | O |
| ATOM | 1469 | N   | GLY | A | 99  | 63.761 | −48.135 | 1.502  | 1.00 | 17.20 A | N |
| ATOM | 1470 | CA  | GLY | A | 99  | 63.515 | −48.016 | 0.071  | 1.00 | 16.81 A | C |
| ATOM | 1473 | C   | GLY | A | 99  | 62.044 | −47.848 | −0.254 | 1.00 | 16.25 A | C |
| ATOM | 1474 | O   | GLY | A | 99  | 61.689 | −47.056 | −1.122 | 1.00 | 16.14 A | O |
| ATOM | 1476 | N   | THR | A | 100 | 61.192 | −48.592 | 0.449  | 1.00 | 15.87 A | N |
| ATOM | 1477 | CA  | THR | A | 100 | 59.742 | −48.502 | 0.257  | 1.00 | 15.58 A | C |
| ATOM | 1479 | CB  | THR | A | 100 | 59.001 | −49.660 | 0.962  | 1.00 | 15.34 A | C |
| ATOM | 1481 | OG1 | THR | A | 100 | 59.592 | −50.906 | 0.583  | 1.00 | 14.29 A | O |
| ATOM | 1483 | CG2 | THR | A | 100 | 57.525 | −49.672 | 0.583  | 1.00 | 14.51 A | C |
| ATOM | 1487 | C   | THR | A | 100 | 59.184 | −47.172 | 0.767  | 1.00 | 15.52 A | C |
| ATOM | 1488 | O   | THR | A | 100 | 58.246 | −46.634 | 0.186  | 1.00 | 15.09 A | O |
| ATOM | 1490 | N   | ALA | A | 101 | 59.768 | −46.652 | 1.846  | 1.00 | 15.65 A | N |
| ATOM | 1491 | CA  | ALA | A | 101 | 59.332 | −45.388 | 2.444  | 1.00 | 15.65 A | C |
| ATOM | 1493 | CB  | ALA | A | 101 | 59.822 | −45.290 | 3.884  | 1.00 | 15.54 A | C |
| ATOM | 1497 | C   | ALA | A | 101 | 59.814 | −44.183 | 1.638  | 1.00 | 15.54 A | C |
| ATOM | 1498 | O   | ALA | A | 101 | 59.057 | −43.237 | 1.409  | 1.00 | 15.42 A | O |
| ATOM | 1500 | N   | LEU | A | 102 | 61.076 | −44.218 | 1.219  | 1.00 | 15.41 A | N |
| ATOM | 1501 | CA  | LEU | A | 102 | 61.648 | −43.146 | 0.408  | 1.00 | 15.42 A | C |
| ATOM | 1503 | CB  | LEU | A | 102 | 63.157 | −43.355 | 0.241  | 1.00 | 15.36 A | C |
| ATOM | 1506 | CG  | LEU | A | 102 | 63.945 | −42.270 | −0.501 | 1.00 | 14.98 A | C |
| ATOM | 1508 | CD1 | LEU | A | 102 | 63.702 | −40.900 | 0.116  | 1.00 | 15.72 A | C |
| ATOM | 1512 | CD2 | LEU | A | 102 | 65.430 | −42.604 | −0.499 | 1.00 | 13.41 A | C |
| ATOM | 1516 | C   | LEU | A | 102 | 60.971 | −43.076 | −0.961 | 1.00 | 15.48 A | C |
| ATOM | 1517 | O   | LEU | A | 102 | 60.618 | −41.993 | −1.434 | 1.00 | 15.70 A | O |
| ATOM | 1519 | N   | SER | A | 103 | 60.789 | −44.237 | −1.585 | 1.00 | 15.25 A | N |
| ATOM | 1520 | CA  | SER | A | 103 | 60.193 | −44.320 | −2.919 | 1.00 | 15.14 A | C |
| ATOM | 1522 | CB  | SER | A | 103 | 60.410 | −45.711 | −3.516 | 1.00 | 15.40 A | C |
| ATOM | 1525 | OG  | SER | A | 103 | 59.767 | −46.707 | −2.738 | 1.00 | 16.19 A | O |
| ATOM | 1527 | C   | SER | A | 103 | 58.702 | −44.001 | −2.923 | 1.00 | 14.61 A | C |
| ATOM | 1528 | O   | SER | A | 103 | 58.181 | −43.506 | −3.919 | 1.00 | 14.62 A | O |
| ATOM | 1530 | N   | PHE | A | 104 | 58.019 | −44.307 | −1.822 | 1.00 | 14.22 A | N |
| ATOM | 1531 | CA  | PHE | A | 104 | 56.601 | −43.979 | −1.673 | 1.00 | 13.75 A | C |
| ATOM | 1533 | CB  | PHE | A | 104 | 56.071 | −44.474 | −0.323 | 1.00 | 13.69 A | C |
| ATOM | 1536 | CG  | PHE | A | 104 | 54.603 | −44.227 | −0.113 | 1.00 | 13.93 A | C |
| ATOM | 1537 | CD1 | PHE | A | 104 | 53.687 | −45.255 | −0.272 | 1.00 | 14.16 A | C |
| ATOM | 1539 | CE1 | PHE | A | 104 | 52.332 | −45.031 | −0.075 | 1.00 | 15.68 A | C |
| ATOM | 1541 | CZ  | PHE | A | 104 | 51.878 | −43.770 | 0.287  | 1.00 | 15.52 A | C |
| ATOM | 1543 | CE2 | PHE | A | 104 | 52.780 | −42.737 | 0.450  | 1.00 | 15.16 A | C |

TABLE 8-2-continued

Coordinates for L494P Structure

| ATOM | 1545 | CD2 | PHE | A | 104 | 54.137 | −42.968 | 0.254 | 1.00 | 15.63 | A | C |
|---|---|---|---|---|---|---|---|---|---|---|---|---|
| ATOM | 1547 | C | PHE | A | 104 | 56.419 | −42.475 | −1.764 | 1.00 | 13.26 | A | C |
| ATOM | 1548 | O | PHE | A | 104 | 55.580 | −41.984 | −2.517 | 1.00 | 13.35 | A | O |
| ATOM | 1550 | N | ARG | A | 105 | 57.219 | −41.756 | −0.983 | 1.00 | 12.79 | A | N |
| ATOM | 1551 | CA | ARG | A | 105 | 57.129 | −40.305 | −0.889 | 1.00 | 12.24 | A | C |
| ATOM | 1553 | CB | ARG | A | 105 | 58.131 | −39.786 | 0.151 | 1.00 | 12.47 | A | C |
| ATOM | 1556 | CG | ARG | A | 105 | 58.043 | −38.289 | 0.429 | 1.00 | 12.65 | A | C |
| ATOM | 1559 | CD | ARG | A | 105 | 58.675 | −37.930 | 1.765 | 1.00 | 12.12 | A | C |
| ATOM | 1562 | NE | ARG | A | 105 | 60.085 | −38.315 | 1.836 | 1.00 | 12.56 | A | N |
| ATOM | 1564 | CZ | ARG | A | 105 | 61.099 | −37.626 | 1.307 | 1.00 | 12.59 | A | C |
| ATOM | 1565 | NH1 | ARG | A | 105 | 60.889 | −36.492 | 0.641 | 1.00 | 10.93 | A | N |
| ATOM | 1568 | NH2 | ARG | A | 105 | 62.342 | −38.081 | 1.442 | 1.00 | 13.27 | A | N |
| ATOM | 1571 | C | ARG | A | 105 | 57.377 | −39.646 | −2.240 | 1.00 | 11.50 | A | C |
| ATOM | 1572 | O | ARG | A | 105 | 56.522 | −38.911 | −2.739 | 1.00 | 11.41 | A | O |
| ATOM | 1574 | N | LEU | A | 106 | 58.538 | −39.929 | −2.828 | 1.00 | 10.65 | A | N |
| ATOM | 1575 | CA | LEU | A | 106 | 58.960 | −39.289 | −4.077 | 1.00 | 10.07 | A | C |
| ATOM | 1577 | CB | LEU | A | 106 | 60.342 | −39.797 | −4.503 | 1.00 | 9.65 | A | C |
| ATOM | 1580 | CG | LEU | A | 106 | 61.518 | −39.446 | −3.591 | 1.00 | 8.79 | A | C |
| ATOM | 1582 | CD1 | LEU | A | 106 | 62.798 | −40.057 | −4.123 | 1.00 | 7.06 | A | C |
| ATOM | 1586 | CD2 | LEU | A | 106 | 61.665 | −37.943 | −3.455 | 1.00 | 8.58 | A | C |
| ATOM | 1590 | C | LEU | A | 106 | 57.960 | −39.510 | −5.210 | 1.00 | 10.35 | A | C |
| ATOM | 1591 | O | LEU | A | 106 | 57.659 | −38.591 | −5.966 | 1.00 | 9.93 | A | O |
| ATOM | 1593 | N | LEU | A | 107 | 57.448 | −40.731 | −5.322 | 1.00 | 11.25 | A | N |
| ATOM | 1594 | CA | LEU | A | 107 | 56.482 | −41.059 | −6.364 | 1.00 | 11.96 | A | C |
| ATOM | 1596 | CB | LEU | A | 107 | 56.168 | −42.561 | −6.362 | 1.00 | 11.90 | A | C |
| ATOM | 1599 | CG | LEU | A | 107 | 57.282 | −43.462 | −6.910 | 1.00 | 10.93 | A | C |
| ATOM | 1601 | CD1 | LEU | A | 107 | 57.110 | −44.907 | −6.454 | 1.00 | 9.95 | A | C |
| ATOM | 1605 | CD2 | LEU | A | 107 | 57.338 | −43.384 | −8.426 | 1.00 | 9.78 | A | C |
| ATOM | 1609 | C | LEU | A | 107 | 55.211 | −40.227 | −6.190 | 1.00 | 12.95 | A | C |
| ATOM | 1610 | O | LEU | A | 107 | 54.855 | −39.443 | −7.073 | 1.00 | 13.19 | A | O |
| ATOM | 1612 | N | ARG | A | 108 | 54.552 | −40.368 | −5.041 | 1.00 | 13.67 | A | N |
| ATOM | 1613 | CA | ARG | A | 108 | 53.324 | −39.618 | −4.765 | 1.00 | 14.20 | A | C |
| ATOM | 1615 | CB | ARG | A | 108 | 52.790 | −39.925 | −3.364 | 1.00 | 14.17 | A | C |
| ATOM | 1618 | CG | ARG | A | 108 | 51.491 | −39.199 | −3.039 | 1.00 | 14.69 | A | C |
| ATOM | 1621 | CD | ARG | A | 108 | 50.825 | −39.745 | −1.794 | 1.00 | 15.20 | A | C |
| ATOM | 1624 | NE | ARG | A | 108 | 50.129 | −41.006 | −2.043 | 1.00 | 15.73 | A | N |
| ATOM | 1626 | CZ | ARG | A | 108 | 49.489 | −41.709 | −1.110 | 1.00 | 16.84 | A | C |
| ATOM | 1627 | NH1 | ARG | A | 108 | 49.452 | −41.284 | 0.152 | 1.00 | 18.23 | A | N |
| ATOM | 1630 | NH2 | ARG | A | 108 | 48.886 | −42.847 | −1.436 | 1.00 | 16.02 | A | N |
| ATOM | 1633 | C | ARG | A | 108 | 53.527 | −38.112 | −4.927 | 1.00 | 14.71 | A | C |
| ATOM | 1634 | O | ARG | A | 108 | 52.645 | −37.421 | −5.434 | 1.00 | 15.28 | A | O |
| ATOM | 1636 | N | GLN | A | 109 | 54.683 | −37.613 | −4.491 | 1.00 | 15.38 | A | N |
| ATOM | 1637 | CA | GLN | A | 109 | 55.061 | −36.209 | −4.704 | 1.00 | 15.97 | A | C |
| ATOM | 1639 | CB | GLN | A | 109 | 56.475 | −35.945 | −4.163 | 1.00 | 15.84 | A | C |
| ATOM | 1642 | CG | GLN | A | 109 | 57.029 | −34.541 | −4.425 | 1.00 | 14.14 | A | C |
| ATOM | 1645 | CD | GLN | A | 109 | 58.523 | −34.431 | −4.153 | 1.00 | 12.90 | A | C |
| ATOM | 1646 | OE1 | GLN | A | 109 | 59.146 | −35.355 | −3.631 | 1.00 | 11.02 | A | O |
| ATOM | 1647 | NE2 | GLN | A | 109 | 59.102 | −33.291 | −4.508 | 1.00 | 12.83 | A | N |
| ATOM | 1650 | C | GLN | A | 109 | 55.000 | −35.856 | −6.190 | 1.00 | 16.80 | A | C |
| ATOM | 1651 | O | GLN | A | 109 | 54.554 | −34.764 | −6.555 | 1.00 | 17.24 | A | O |
| ATOM | 1653 | N | HIS | A | 110 | 55.441 | −36.790 | −7.034 | 1.00 | 17.12 | A | N |
| ATOM | 1654 | CA | HIS | A | 110 | 55.471 | −36.593 | −8.484 | 1.00 | 17.38 | A | C |
| ATOM | 1656 | CB | HIS | A | 110 | 56.786 | −37.139 | −9.056 | 1.00 | 17.33 | A | C |
| ATOM | 1659 | CG | HIS | A | 110 | 57.991 | −36.346 | −8.656 | 1.00 | 16.17 | A | C |
| ATOM | 1660 | ND1 | HIS | A | 110 | 58.171 | −35.032 | −9.032 | 1.00 | 16.90 | A | N |
| ATOM | 1662 | CE1 | HIS | A | 110 | 59.317 | −34.590 | −8.545 | 1.00 | 16.88 | A | C |
| ATOM | 1664 | NE2 | HIS | A | 110 | 59.888 | −35.571 | −7.870 | 1.00 | 15.81 | A | N |
| ATOM | 1666 | CD2 | HIS | A | 110 | 59.080 | −36.681 | −7.926 | 1.00 | 14.86 | A | C |
| ATOM | 1668 | C | HIS | A | 110 | 54.264 | −37.210 | −9.211 | 1.00 | 17.87 | A | C |
| ATOM | 1669 | O | HIS | A | 110 | 54.390 | −37.690 | −10.344 | 1.00 | 17.97 | A | O |
| ATOM | 1671 | N | GLY | A | 111 | 53.101 | −37.208 | −8.557 | 1.00 | 18.23 | A | N |
| ATOM | 1672 | CA | GLY | A | 111 | 51.832 | −37.543 | −9.215 | 1.00 | 18.60 | A | C |
| ATOM | 1675 | C | GLY | A | 111 | 51.538 | −39.016 | −9.464 | 1.00 | 19.18 | A | C |
| ATOM | 1676 | O | GLY | A | 111 | 50.428 | −39.362 | −9.877 | 1.00 | 19.51 | A | O |
| ATOM | 1678 | N | PHE | A | 112 | 52.515 | −39.888 | −9.221 | 1.00 | 19.34 | A | N |
| ATOM | 1679 | CA | PHE | A | 112 | 52.326 | −41.326 | −9.398 | 1.00 | 19.07 | A | C |
| ATOM | 1681 | CB | PHE | A | 112 | 53.663 | −42.064 | −9.292 | 1.00 | 19.21 | A | C |
| ATOM | 1684 | CG | PHE | A | 112 | 54.544 | −41.904 | −10.495 | 1.00 | 20.15 | A | C |
| ATOM | 1685 | CD1 | PHE | A | 112 | 54.129 | −42.360 | −11.740 | 1.00 | 21.80 | A | C |
| ATOM | 1687 | CE1 | PHE | A | 112 | 54.945 | −42.227 | −12.855 | 1.00 | 22.75 | A | C |
| ATOM | 1689 | CZ | PHE | A | 112 | 56.195 | −41.642 | −12.730 | 1.00 | 23.18 | A | C |
| ATOM | 1691 | CE2 | PHE | A | 112 | 56.624 | −41.192 | −11.489 | 1.00 | 22.64 | A | C |
| ATOM | 1693 | CD2 | PHE | A | 112 | 55.800 | −41.326 | −10.380 | 1.00 | 21.27 | A | C |
| ATOM | 1695 | C | PHE | A | 112 | 51.369 | −41.887 | −8.357 | 1.00 | 18.69 | A | C |
| ATOM | 1696 | O | PHE | A | 112 | 51.144 | −41.275 | −7.313 | 1.00 | 18.60 | A | O |
| ATOM | 1698 | N | GLU | A | 113 | 50.817 | −43.060 | −8.645 | 1.00 | 18.61 | A | N |
| ATOM | 1699 | CA | GLU | A | 113 | 49.921 | −43.735 | −7.715 | 1.00 | 18.65 | A | C |
| ATOM | 1701 | CB | GLU | A | 113 | 48.699 | −44.292 | −8.447 | 1.00 | 18.82 | A | C |

TABLE 8-2-continued

Coordinates for L494P Structure

| ATOM | 1704 | CG | GLU | A | 113 | 47.633 | −43.241 | −8.709 | 1.00 | 21.49 | A | C |
|---|---|---|---|---|---|---|---|---|---|---|---|---|
| ATOM | 1707 | CD | GLU | A | 113 | 46.566 | −43.700 | −9.687 | 1.00 | 25.30 | A | C |
| ATOM | 1708 | OE1 | GLU | A | 113 | 45.849 | −42.829 | −10.227 | 1.00 | 27.79 | A | O |
| ATOM | 1709 | OE2 | GLU | A | 113 | 46.440 | −44.923 | −9.917 | 1.00 | 27.48 | A | O |
| ATOM | 1710 | C | GLU | A | 113 | 50.648 | −44.841 | −6.959 | 1.00 | 18.07 | A | C |
| ATOM | 1711 | O | GLU | A | 113 | 50.854 | −45.939 | −7.483 | 1.00 | 18.36 | A | O |
| ATOM | 1713 | N | VAL | A | 114 | 51.060 | −44.521 | −5.735 | 1.00 | 17.12 | A | N |
| ATOM | 1714 | CA | VAL | A | 114 | 51.481 | −45.524 | −4.765 | 1.00 | 16.39 | A | C |
| ATOM | 1716 | CB | VAL | A | 114 | 52.750 | −45.101 | −4.008 | 1.00 | 15.83 | A | C |
| ATOM | 1718 | CG1 | VAL | A | 114 | 53.919 | −45.005 | −4.964 | 1.00 | 15.16 | A | C |
| ATOM | 1722 | CG2 | VAL | A | 114 | 52.533 | −43.784 | −3.276 | 1.00 | 15.50 | A | C |
| ATOM | 1726 | C | VAL | A | 114 | 50.335 | −45.721 | −3.781 | 1.00 | 16.53 | A | C |
| ATOM | 1727 | O | VAL | A | 114 | 49.538 | −44.810 | −3.572 | 1.00 | 16.32 | A | O |
| ATOM | 1729 | N | SER | A | 115 | 50.247 | −46.912 | −3.194 | 1.00 | 17.04 | A | N |
| ATOM | 1730 | CA | SER | A | 115 | 49.195 | −47.223 | −2.228 | 1.00 | 17.55 | A | C |
| ATOM | 1732 | CB | SER | A | 115 | 48.308 | −48.355 | −2.743 | 1.00 | 17.82 | A | C |
| ATOM | 1735 | OG | SER | A | 115 | 47.197 | −48.552 | −1.884 | 1.00 | 18.67 | A | O |
| ATOM | 1737 | C | SER | A | 115 | 49.781 | −47.609 | −0.876 | 1.00 | 17.69 | A | C |
| ATOM | 1738 | O | SER | A | 115 | 50.899 | −48.124 | −0.795 | 1.00 | 17.50 | A | O |
| ATOM | 1740 | N | GLN | A | 116 | 49.006 | −47.374 | 0.181 | 1.00 | 17.82 | A | N |
| ATOM | 1741 | CA | GLN | A | 116 | 49.454 | −47.623 | 1.555 | 1.00 | 17.95 | A | C |
| ATOM | 1743 | CB | GLN | A | 116 | 48.420 | −47.101 | 2.559 | 1.00 | 17.90 | A | C |
| ATOM | 1746 | CG | GLN | A | 116 | 47.068 | −47.810 | 2.515 | 1.00 | 18.34 | A | C |
| ATOM | 1749 | CD | GLN | A | 116 | 46.133 | −47.374 | 3.628 | 1.00 | 18.56 | A | C |
| ATOM | 1750 | OE1 | GLN | A | 116 | 46.556 | −46.788 | 4.625 | 1.00 | 17.49 | A | O |
| ATOM | 1751 | NE2 | GLN | A | 116 | 44.849 | −47.667 | 3.464 | 1.00 | 20.40 | A | N |
| ATOM | 1754 | C | GLN | A | 116 | 49.769 | −49.092 | 1.862 | 1.00 | 18.13 | A | C |
| ATOM | 1755 | O | GLN | A | 116 | 50.414 | −49.388 | 2.869 | 1.00 | 18.57 | A | O |
| ATOM | 1757 | N | GLU | A | 117 | 49.310 | −50.003 | 1.004 | 1.00 | 17.94 | A | N |
| ATOM | 1758 | CA | GLU | A | 117 | 49.597 | −51.434 | 1.157 | 1.00 | 17.83 | A | C |
| ATOM | 1760 | CB | GLU | A | 117 | 48.454 | −52.279 | 0.566 | 1.00 | 17.98 | A | C |
| ATOM | 1763 | CG | GLU | A | 117 | 48.249 | −52.140 | −0.952 | 1.00 | 19.01 | A | C |
| ATOM | 1766 | CD | GLU | A | 117 | 46.780 | −52.207 | −1.378 | 1.00 | 20.24 | A | C |
| ATOM | 1767 | OE1 | GLU | A | 117 | 45.909 | −51.625 | −0.689 | 1.00 | 19.48 | A | O |
| ATOM | 1768 | OE2 | GLU | A | 117 | 46.500 | −52.832 | −2.424 | 1.00 | 20.64 | A | O |
| ATOM | 1769 | C | GLU | A | 117 | 50.956 | −51.847 | 0.566 | 1.00 | 17.49 | A | C |
| ATOM | 1770 | O | GLU | A | 117 | 51.215 | −53.034 | 0.373 | 1.00 | 17.44 | A | O |
| ATOM | 1772 | N | ALA | A | 118 | 51.817 | −50.870 | 0.282 | 1.00 | 17.38 | A | N |
| ATOM | 1773 | CA | ALA | A | 118 | 53.218 | −51.141 | −0.044 | 1.00 | 17.57 | A | C |
| ATOM | 1775 | CB | ALA | A | 118 | 53.836 | −49.962 | −0.770 | 1.00 | 17.88 | A | C |
| ATOM | 1779 | C | ALA | A | 118 | 54.002 | −51.431 | 1.228 | 1.00 | 17.50 | A | C |
| ATOM | 1780 | O | ALA | A | 118 | 55.040 | −52.090 | 1.184 | 1.00 | 17.67 | A | O |
| ATOM | 1782 | N | PHE | A | 119 | 53.498 | −50.929 | 2.354 | 1.00 | 17.52 | A | N |
| ATOM | 1783 | CA | PHE | A | 119 | 54.126 | −51.132 | 3.655 | 1.00 | 17.68 | A | C |
| ATOM | 1785 | CB | PHE | A | 119 | 53.830 | −49.945 | 4.578 | 1.00 | 17.42 | A | C |
| ATOM | 1788 | CG | PHE | A | 119 | 54.301 | −48.622 | 4.038 | 1.00 | 15.73 | A | C |
| ATOM | 1789 | CD1 | PHE | A | 119 | 53.399 | −47.701 | 3.526 | 1.00 | 14.47 | A | C |
| ATOM | 1791 | CE1 | PHE | A | 119 | 53.833 | −46.484 | 3.029 | 1.00 | 15.03 | A | C |
| ATOM | 1793 | CZ | PHE | A | 119 | 55.181 | −46.175 | 3.039 | 1.00 | 15.34 | A | C |
| ATOM | 1795 | CE2 | PHE | A | 119 | 56.091 | −47.088 | 3.544 | 1.00 | 14.74 | A | C |
| ATOM | 1797 | CD2 | PHE | A | 119 | 55.649 | −48.301 | 4.040 | 1.00 | 14.46 | A | C |
| ATOM | 1799 | C | PHE | A | 119 | 53.666 | −52.422 | 4.336 | 1.00 | 18.67 | A | C |
| ATOM | 1800 | O | PHE | A | 119 | 54.193 | −52.782 | 5.390 | 1.00 | 18.41 | A | O |
| ATOM | 1802 | N | SER | A | 120 | 52.693 | −53.112 | 3.735 | 1.00 | 20.10 | A | N |
| ATOM | 1803 | CA | SER | A | 120 | 52.070 | −54.302 | 4.342 | 1.00 | 20.78 | A | C |
| ATOM | 1805 | CB | SER | A | 120 | 50.966 | −54.859 | 3.433 | 1.00 | 20.80 | A | C |
| ATOM | 1808 | OG | SER | A | 120 | 51.505 | −55.402 | 2.240 | 1.00 | 21.10 | A | O |
| ATOM | 1810 | C | SER | A | 120 | 53.062 | −55.417 | 4.679 | 1.00 | 21.20 | A | C |
| ATOM | 1811 | O | SER | A | 120 | 52.863 | −56.152 | 5.645 | 1.00 | 21.27 | A | O |
| ATOM | 1813 | N | GLY | A | 121 | 54.121 | −55.542 | 3.884 | 1.00 | 22.05 | A | N |
| ATOM | 1814 | CA | GLY | A | 121 | 55.175 | −56.517 | 4.156 | 1.00 | 22.98 | A | C |
| ATOM | 1817 | C | GLY | A | 121 | 55.878 | −56.295 | 5.487 | 1.00 | 23.82 | A | C |
| ATOM | 1818 | O | GLY | A | 121 | 56.330 | −57.252 | 6.121 | 1.00 | 23.57 | A | O |
| ATOM | 1820 | N | PHE | A | 122 | 55.946 | −55.034 | 5.918 | 1.00 | 24.93 | A | N |
| ATOM | 1821 | CA | PHE | A | 122 | 56.665 | −54.646 | 7.137 | 1.00 | 25.54 | A | C |
| ATOM | 1823 | CB | PHE | A | 122 | 57.384 | −53.304 | 6.922 | 1.00 | 25.57 | A | C |
| ATOM | 1826 | CG | PHE | A | 122 | 58.118 | −53.209 | 5.610 | 1.00 | 25.40 | A | C |
| ATOM | 1827 | CD1 | PHE | A | 122 | 59.366 | −53.796 | 5.448 | 1.00 | 26.67 | A | C |
| ATOM | 1829 | CE1 | PHE | A | 122 | 60.042 | −53.710 | 4.235 | 1.00 | 26.81 | A | C |
| ATOM | 1831 | CZ | PHE | A | 122 | 59.467 | −53.034 | 3.170 | 1.00 | 26.20 | A | C |
| ATOM | 1833 | CE2 | PHE | A | 122 | 58.221 | −52.443 | 3.322 | 1.00 | 25.77 | A | C |
| ATOM | 1835 | CD2 | PHE | A | 122 | 57.554 | −52.534 | 4.536 | 1.00 | 24.71 | A | C |
| ATOM | 1837 | C | PHE | A | 122 | 55.734 | −54.560 | 8.358 | 1.00 | 26.09 | A | C |
| ATOM | 1838 | O | PHE | A | 122 | 55.717 | −53.553 | 9.074 | 1.00 | 26.28 | A | O |
| ATOM | 1840 | N | LYS | A | 123 | 54.964 | −55.622 | 8.587 | 1.00 | 26.57 | A | N |
| ATOM | 1841 | CA | LYS | A | 123 | 54.072 | −55.719 | 9.745 | 1.00 | 27.02 | A | C |
| ATOM | 1843 | CB | LYS | A | 123 | 52.632 | −55.359 | 9.349 | 1.00 | 27.12 | A | C |
| ATOM | 1846 | CG | LYS | A | 123 | 52.428 | −53.873 | 9.013 | 1.00 | 28.30 | A | C |

TABLE 8-2-continued

Coordinates for L494P Structure

| ATOM | 1849 | CD | LYS | A | 123 | 51.208 | −53.615 | 8.116 | 1.00 | 30.27 | A | C |
|------|------|-----|-----|---|-----|--------|--------|--------|------|-------|---|---|
| ATOM | 1852 | CE | LYS | A | 123 | 49.967 | −53.187 | 8.895 | 1.00 | 30.83 | A | C |
| ATOM | 1855 | NZ | LYS | A | 123 | 50.115 | −51.843 | 9.535 | 1.00 | 30.44 | A | N |
| ATOM | 1859 | C | LYS | A | 123 | 54.142 | −57.139 | 10.313 | 1.00 | 27.21 | A | C |
| ATOM | 1860 | O | LYS | A | 123 | 54.429 | −58.094 | 9.585 | 1.00 | 27.37 | A | O |
| ATOM | 1862 | N | ASP | A | 124 | 53.888 | −57.272 | 11.613 | 1.00 | 27.19 | A | N |
| ATOM | 1863 | CA | ASP | A | 124 | 53.936 | −58.576 | 12.282 | 1.00 | 26.97 | A | C |
| ATOM | 1865 | CB | ASP | A | 124 | 54.208 | −58.395 | 13.790 | 1.00 | 26.80 | A | C |
| ATOM | 1868 | CG | ASP | A | 124 | 53.015 | −57.829 | 14.555 | 1.00 | 26.01 | A | C |
| ATOM | 1869 | OD1 | ASP | A | 124 | 52.076 | −57.288 | 13.930 | 1.00 | 23.03 | A | O |
| ATOM | 1870 | OD2 | ASP | A | 124 | 53.020 | −57.930 | 15.800 | 1.00 | 25.54 | A | O |
| ATOM | 1871 | C | ASP | A | 124 | 52.647 | −59.374 | 12.014 | 1.00 | 27.07 | A | C |
| ATOM | 1872 | O | ASP | A | 124 | 51.904 | −59.059 | 11.079 | 1.00 | 26.95 | A | O |
| ATOM | 1874 | N | GLN | A | 125 | 52.393 | −60.409 | 12.816 | 1.00 | 27.04 | A | N |
| ATOM | 1875 | CA | GLN | A | 125 | 51.141 | −61.169 | 12.730 | 1.00 | 26.85 | A | C |
| ATOM | 1877 | CB | GLN | A | 125 | 51.124 | −62.297 | 13.761 | 1.00 | 26.80 | A | C |
| ATOM | 1880 | CG | GLN | A | 125 | 52.054 | −63.450 | 13.455 | 1.00 | 26.80 | A | C |
| ATOM | 1883 | CD | GLN | A | 125 | 51.830 | −64.626 | 14.386 | 1.00 | 26.65 | A | C |
| ATOM | 1884 | OE1 | GLN | A | 125 | 51.287 | −64.469 | 15.482 | 1.00 | 25.80 | A | O |
| ATOM | 1885 | NE2 | GLN | A | 125 | 52.242 | −65.812 | 13.952 | 1.00 | 26.55 | A | N |
| ATOM | 1888 | C | GLN | A | 125 | 49.908 | −60.293 | 12.956 | 1.00 | 26.80 | A | C |
| ATOM | 1889 | O | GLN | A | 125 | 48.889 | −60.462 | 12.283 | 1.00 | 26.98 | A | O |
| ATOM | 1891 | N | ASN | A | 126 | 50.012 | −59.369 | 13.910 | 1.00 | 26.46 | A | N |
| ATOM | 1892 | CA | ASN | A | 126 | 48.880 | −58.542 | 14.337 | 1.00 | 26.12 | A | C |
| ATOM | 1894 | CB | ASN | A | 126 | 49.113 | −58.030 | 15.762 | 1.00 | 25.97 | A | C |
| ATOM | 1897 | CG | ASN | A | 126 | 48.963 | −59.117 | 16.804 | 1.00 | 25.81 | A | C |
| ATOM | 1898 | OD1 | ASN | A | 126 | 48.186 | −58.979 | 17.748 | 1.00 | 26.53 | A | O |
| ATOM | 1899 | ND2 | ASN | A | 126 | 49.702 | −60.209 | 16.637 | 1.00 | 25.44 | A | N |
| ATOM | 1902 | C | ASN | A | 126 | 48.554 | −57.354 | 13.429 | 1.00 | 26.03 | A | C |
| ATOM | 1903 | O | ASN | A | 126 | 47.496 | −56.744 | 13.575 | 1.00 | 26.32 | A | O |
| ATOM | 1905 | N | GLY | A | 127 | 49.445 | −57.027 | 12.497 | 1.00 | 25.72 | A | N |
| ATOM | 1906 | CA | GLY | A | 127 | 49.262 | −55.850 | 11.646 | 1.00 | 25.62 | A | C |
| ATOM | 1909 | C | GLY | A | 127 | 49.743 | −54.571 | 12.316 | 1.00 | 25.62 | A | C |
| ATOM | 1910 | O | GLY | A | 127 | 49.235 | −53.481 | 12.040 | 1.00 | 25.98 | A | O |
| ATOM | 1912 | N | ASN | A | 128 | 50.712 | −54.716 | 13.216 | 1.00 | 25.32 | A | N |
| ATOM | 1913 | CA | ASN | A | 128 | 51.451 | −53.590 | 13.771 | 1.00 | 24.58 | A | C |
| ATOM | 1915 | CB | ASN | A | 128 | 51.410 | −53.617 | 15.298 | 1.00 | 24.48 | A | C |
| ATOM | 1918 | CG | ASN | A | 128 | 49.992 | −53.673 | 15.841 | 1.00 | 24.48 | A | C |
| ATOM | 1919 | OD1 | ASN | A | 128 | 49.100 | −52.975 | 15.355 | 1.00 | 24.27 | A | O |
| ATOM | 1920 | ND2 | ASN | A | 128 | 49.778 | −54.508 | 16.850 | 1.00 | 23.51 | A | N |
| ATOM | 1923 | C | ASN | A | 128 | 52.881 | −53.709 | 13.269 | 1.00 | 24.17 | A | C |
| ATOM | 1924 | O | ASN | A | 128 | 53.380 | −54.819 | 13.064 | 1.00 | 23.94 | A | O |
| ATOM | 1926 | N | PHE | A | 129 | 53.538 | −52.574 | 13.064 | 1.00 | 23.75 | A | N |
| ATOM | 1927 | CA | PHE | A | 129 | 54.868 | −52.567 | 12.453 | 1.00 | 23.39 | A | C |
| ATOM | 1929 | CB | PHE | A | 129 | 55.330 | −51.134 | 12.181 | 1.00 | 23.51 | A | C |
| ATOM | 1932 | CG | PHE | A | 129 | 54.571 | −50.461 | 11.073 | 1.00 | 23.75 | A | C |
| ATOM | 1933 | CD1 | PHE | A | 129 | 53.351 | −49.843 | 11.322 | 1.00 | 23.30 | A | C |
| ATOM | 1935 | CE1 | PHE | A | 129 | 52.645 | −49.226 | 10.300 | 1.00 | 23.78 | A | C |
| ATOM | 1937 | CZ | PHE | A | 129 | 53.157 | −49.223 | 9.011 | 1.00 | 24.34 | A | C |
| ATOM | 1939 | CE2 | PHE | A | 129 | 54.371 | −49.841 | 8.748 | 1.00 | 24.80 | A | C |
| ATOM | 1941 | CD2 | PHE | A | 129 | 55.071 | −50.456 | 9.777 | 1.00 | 24.15 | A | C |
| ATOM | 1943 | C | PHE | A | 129 | 55.881 | −53.315 | 13.320 | 1.00 | 22.72 | A | C |
| ATOM | 1944 | O | PHE | A | 129 | 55.797 | −53.289 | 14.549 | 1.00 | 22.69 | A | O |
| ATOM | 1946 | N | LEU | A | 130 | 56.821 | −53.997 | 12.674 | 1.00 | 21.98 | A | N |
| ATOM | 1947 | CA | LEU | A | 130 | 57.774 | −54.833 | 13.395 | 1.00 | 21.77 | A | C |
| ATOM | 1949 | CB | LEU | A | 130 | 58.741 | −55.532 | 12.430 | 1.00 | 21.51 | A | C |
| ATOM | 1952 | CG | LEU | A | 130 | 58.233 | −56.805 | 11.749 | 1.00 | 20.32 | A | C |
| ATOM | 1954 | CD1 | LEU | A | 130 | 59.185 | −57.238 | 10.642 | 1.00 | 18.63 | A | C |
| ATOM | 1958 | CD2 | LEU | A | 130 | 58.049 | −57.920 | 12.767 | 1.00 | 18.91 | A | C |
| ATOM | 1962 | C | LEU | A | 130 | 58.559 | −54.008 | 14.406 | 1.00 | 21.98 | A | C |
| ATOM | 1963 | O | LEU | A | 130 | 59.271 | −53.079 | 14.033 | 1.00 | 22.04 | A | O |
| ATOM | 1965 | N | GLU | A | 131 | 58.404 | −54.344 | 15.685 | 1.00 | 22.19 | A | N |
| ATOM | 1966 | CA | GLU | A | 131 | 59.208 | −53.755 | 16.756 | 1.00 | 22.55 | A | C |
| ATOM | 1968 | CB | GLU | A | 131 | 59.141 | −54.649 | 18.004 | 1.00 | 22.91 | A | C |
| ATOM | 1971 | CG | GLU | A | 131 | 60.010 | −54.215 | 19.194 | 1.00 | 23.48 | A | C |
| ATOM | 1974 | CD | GLU | A | 131 | 59.514 | −52.953 | 19.885 | 1.00 | 24.94 | A | C |
| ATOM | 1975 | OE1 | GLU | A | 131 | 58.423 | −52.451 | 19.536 | 1.00 | 26.88 | A | O |
| ATOM | 1976 | OE2 | GLU | A | 131 | 60.221 | −52.463 | 20.790 | 1.00 | 25.13 | A | O |
| ATOM | 1977 | C | GLU | A | 131 | 60.659 | −53.593 | 16.307 | 1.00 | 22.63 | A | C |
| ATOM | 1978 | O | GLU | A | 131 | 61.214 | −52.497 | 16.355 | 1.00 | 22.79 | A | O |
| ATOM | 1980 | N | ASN | A | 132 | 61.246 | −54.693 | 15.839 | 1.00 | 22.67 | A | N |
| ATOM | 1981 | CA | ASN | A | 132 | 62.659 | −54.740 | 15.447 | 1.00 | 22.65 | A | C |
| ATOM | 1983 | CB | ASN | A | 132 | 63.069 | −56.179 | 15.101 | 1.00 | 22.74 | A | C |
| ATOM | 1986 | CG | ASN | A | 132 | 62.220 | −56.785 | 13.992 | 1.00 | 24.12 | A | C |
| ATOM | 1987 | OD1 | ASN | A | 132 | 62.359 | −56.433 | 12.818 | 1.00 | 24.57 | A | O |
| ATOM | 1988 | ND2 | ASN | A | 132 | 61.339 | −57.710 | 14.362 | 1.00 | 25.30 | A | N |
| ATOM | 1991 | C | ASN | A | 132 | 63.074 | −53.793 | 14.313 | 1.00 | 22.61 | A | C |
| ATOM | 1992 | O | ASN | A | 132 | 64.266 | −53.662 | 14.034 | 1.00 | 23.15 | A | O |

TABLE 8-2-continued

Coordinates for L494P Structure

| ATOM | 1994 | N | LEU | A | 133 | 62.110 | −53.141 | 13.661 | 1.00 | 22.44 | A | N |
|---|---|---|---|---|---|---|---|---|---|---|---|---|
| ATOM | 1995 | CA | LEU | A | 133 | 62.421 | −52.087 | 12.682 | 1.00 | 22.59 | A | C |
| ATOM | 1997 | CB | LEU | A | 133 | 61.274 | −51.905 | 11.677 | 1.00 | 22.57 | A | C |
| ATOM | 2000 | CG | LEU | A | 133 | 61.086 | −53.023 | 10.646 | 1.00 | 22.37 | A | C |
| ATOM | 2002 | CD1 | LEU | A | 133 | 59.755 | −52.870 | 9.926 | 1.00 | 20.95 | A | C |
| ATOM | 2006 | CD2 | LEU | A | 133 | 62.236 | −53.049 | 9.647 | 1.00 | 21.48 | A | C |
| ATOM | 2010 | C | LEU | A | 133 | 62.755 | −50.743 | 13.347 | 1.00 | 22.64 | A | C |
| ATOM | 2011 | O | LEU | A | 133 | 63.043 | −49.766 | 12.656 | 1.00 | 22.50 | A | O |
| ATOM | 2013 | N | LYS | A | 134 | 62.710 | −50.695 | 14.679 | 1.00 | 22.83 | A | N |
| ATOM | 2014 | CA | LYS | A | 134 | 63.148 | −49.518 | 15.435 | 1.00 | 22.96 | A | C |
| ATOM | 2016 | CB | LYS | A | 134 | 62.736 | −49.645 | 16.909 | 1.00 | 22.77 | A | C |
| ATOM | 2019 | CG | LYS | A | 134 | 63.555 | −50.675 | 17.698 | 1.00 | 22.69 | A | C |
| ATOM | 2022 | CD | LYS | A | 134 | 62.959 | −50.982 | 19.064 | 1.00 | 21.51 | A | C |
| ATOM | 2025 | CE | LYS | A | 134 | 63.861 | −51.921 | 19.855 | 1.00 | 19.87 | A | C |
| ATOM | 2028 | NZ | LYS | A | 134 | 63.358 | −52.166 | 21.234 | 1.00 | 19.19 | A | N |
| ATOM | 2032 | C | LYS | A | 134 | 64.667 | −49.311 | 15.350 | 1.00 | 23.33 | A | C |
| ATOM | 2033 | O | LYS | A | 134 | 65.152 | −48.189 | 15.500 | 1.00 | 23.47 | A | O |
| ATOM | 2035 | N | GLU | A | 135 | 65.410 | −50.393 | 15.118 | 1.00 | 23.60 | A | N |
| ATOM | 2036 | CA | GLU | A | 135 | 66.874 | −50.347 | 15.129 | 1.00 | 23.76 | A | C |
| ATOM | 2038 | CB | GLU | A | 135 | 67.465 | −51.736 | 15.424 | 1.00 | 23.98 | A | C |
| ATOM | 2041 | CG | GLU | A | 135 | 66.893 | −52.454 | 16.662 | 1.00 | 24.91 | A | C |
| ATOM | 2044 | CD | GLU | A | 135 | 67.236 | −51.779 | 17.991 | 1.00 | 26.21 | A | C |
| ATOM | 2045 | OE1 | GLU | A | 135 | 67.594 | −50.581 | 18.003 | 1.00 | 25.91 | A | O |
| ATOM | 2046 | OE2 | GLU | A | 135 | 67.140 | −52.457 | 19.037 | 1.00 | 26.26 | A | O |
| ATOM | 2047 | C | GLU | A | 135 | 67.461 | −49.797 | 13.826 | 1.00 | 23.56 | A | C |
| ATOM | 2048 | O | GLU | A | 135 | 68.641 | −49.440 | 13.785 | 1.00 | 23.61 | A | O |
| ATOM | 2050 | N | ASP | A | 136 | 66.648 | −49.739 | 12.770 | 1.00 | 23.07 | A | N |
| ATOM | 2051 | CA | ASP | A | 136 | 67.043 | −49.103 | 11.511 | 1.00 | 22.73 | A | C |
| ATOM | 2053 | CB | ASP | A | 136 | 66.509 | −49.903 | 10.315 | 1.00 | 22.88 | A | C |
| ATOM | 2056 | CG | ASP | A | 136 | 67.141 | −49.489 | 8.990 | 1.00 | 23.31 | A | C |
| ATOM | 2057 | OD1 | ASP | A | 136 | 67.675 | −48.364 | 8.882 | 1.00 | 24.29 | A | O |
| ATOM | 2058 | OD2 | ASP | A | 136 | 67.096 | −50.301 | 8.043 | 1.00 | 24.88 | A | O |
| ATOM | 2059 | C | ASP | A | 136 | 66.509 | −47.671 | 11.503 | 1.00 | 22.28 | A | C |
| ATOM | 2060 | O | ASP | A | 136 | 65.448 | −47.392 | 10.943 | 1.00 | 22.30 | A | O |
| ATOM | 2062 | N | ILE | A | 137 | 67.263 | −46.765 | 12.119 | 1.00 | 21.98 | A | N |
| ATOM | 2063 | CA | ILE | A | 137 | 66.813 | −45.385 | 12.337 | 1.00 | 22.01 | A | C |
| ATOM | 2065 | CB | ILE | A | 137 | 67.780 | −44.618 | 13.279 | 1.00 | 21.91 | A | C |
| ATOM | 2067 | CG1 | ILE | A | 137 | 67.605 | −45.087 | 14.730 | 1.00 | 22.58 | A | C |
| ATOM | 2070 | CD1 | ILE | A | 137 | 68.188 | −46.460 | 15.030 | 1.00 | 22.59 | A | C |
| ATOM | 2074 | CG2 | ILE | A | 137 | 67.539 | −43.117 | 13.210 | 1.00 | 21.61 | A | C |
| ATOM | 2078 | C | ILE | A | 137 | 66.631 | −44.612 | 11.026 | 1.00 | 22.13 | A | C |
| ATOM | 2079 | O | ILE | A | 137 | 65.838 | −43.667 | 10.958 | 1.00 | 21.88 | A | O |
| ATOM | 2081 | N | LYS | A | 138 | 67.362 | −45.025 | 9.992 | 1.00 | 22.24 | A | N |
| ATOM | 2082 | CA | LYS | A | 138 | 67.242 | −44.431 | 8.659 | 1.00 | 21.88 | A | C |
| ATOM | 2084 | CB | LYS | A | 138 | 68.324 | −44.994 | 7.727 | 1.00 | 21.96 | A | C |
| ATOM | 2087 | CG | LYS | A | 138 | 68.724 | −44.056 | 6.601 | 1.00 | 23.45 | A | C |
| ATOM | 2090 | CD | LYS | A | 138 | 69.512 | −44.788 | 5.522 | 1.00 | 25.55 | A | C |
| ATOM | 2093 | CE | LYS | A | 138 | 70.339 | −43.831 | 4.674 | 1.00 | 26.38 | A | C |
| ATOM | 2096 | NZ | LYS | A | 138 | 71.460 | −43.222 | 5.449 | 1.00 | 28.11 | A | N |
| ATOM | 2100 | C | LYS | A | 138 | 65.854 | −44.689 | 8.062 | 1.00 | 21.05 | A | C |
| ATOM | 2101 | O | LYS | A | 138 | 65.277 | −43.812 | 7.416 | 1.00 | 20.86 | A | O |
| ATOM | 2103 | N | ALA | A | 139 | 65.327 | −45.890 | 8.292 | 1.00 | 20.37 | A | N |
| ATOM | 2104 | CA | ALA | A | 139 | 64.023 | −46.291 | 7.760 | 1.00 | 19.96 | A | C |
| ATOM | 2106 | CB | ALA | A | 139 | 63.890 | −47.811 | 7.792 | 1.00 | 19.84 | A | C |
| ATOM | 2110 | C | ALA | A | 139 | 62.856 | −45.639 | 8.510 | 1.00 | 19.48 | A | C |
| ATOM | 2111 | O | ALA | A | 139 | 61.856 | −45.256 | 7.897 | 1.00 | 19.09 | A | O |
| ATOM | 2113 | N | ILE | A | 140 | 62.987 | −45.518 | 9.830 | 1.00 | 18.99 | A | N |
| ATOM | 2114 | CA | ILE | A | 140 | 61.946 | −44.902 | 10.659 | 1.00 | 18.78 | A | C |
| ATOM | 2116 | CB | ILE | A | 140 | 62.266 | −45.017 | 12.166 | 1.00 | 18.67 | A | C |
| ATOM | 2118 | CG1 | ILE | A | 140 | 62.385 | −46.485 | 12.596 | 1.00 | 18.06 | A | C |
| ATOM | 2121 | CD1 | ILE | A | 140 | 61.112 | −47.284 | 12.435 | 1.00 | 18.60 | A | C |
| ATOM | 2125 | CG2 | ILE | A | 140 | 61.194 | −44.314 | 12.995 | 1.00 | 18.20 | A | C |
| ATOM | 2129 | C | ILE | A | 140 | 61.757 | −43.420 | 10.306 | 1.00 | 19.04 | A | C |
| ATOM | 2130 | O | ILE | A | 140 | 60.635 | −42.908 | 10.342 | 1.00 | 19.09 | A | O |
| ATOM | 2132 | N | LEU | A | 141 | 62.859 | −42.741 | 9.977 | 1.00 | 18.82 | A | N |
| ATOM | 2133 | CA | LEU | A | 141 | 62.812 | −41.358 | 9.492 | 1.00 | 18.09 | A | C |
| ATOM | 2135 | CB | LEU | A | 141 | 64.218 | −40.747 | 9.399 | 1.00 | 17.81 | A | C |
| ATOM | 2138 | CG | LEU | A | 141 | 64.684 | −39.929 | 10.604 | 1.00 | 17.40 | A | C |
| ATOM | 2140 | CD1 | LEU | A | 141 | 66.146 | −39.540 | 10.452 | 1.00 | 16.73 | A | C |
| ATOM | 2144 | CD2 | LEU | A | 141 | 63.817 | −38.692 | 10.781 | 1.00 | 16.04 | A | C |
| ATOM | 2148 | C | LEU | A | 141 | 62.129 | −41.282 | 8.132 | 1.00 | 17.94 | A | C |
| ATOM | 2149 | O | LEU | A | 141 | 61.260 | −40.440 | 7.917 | 1.00 | 18.26 | A | O |
| ATOM | 2151 | N | SER | A | 142 | 62.523 | −42.160 | 7.215 | 1.00 | 17.56 | A | N |
| ATOM | 2152 | CA | SER | A | 142 | 61.894 | −42.205 | 5.897 | 1.00 | 17.58 | A | C |
| ATOM | 2154 | CB | SER | A | 142 | 62.563 | −43.246 | 4.998 | 1.00 | 17.71 | A | C |
| ATOM | 2157 | OG | SER | A | 142 | 63.697 | −42.690 | 4.359 | 1.00 | 18.76 | A | O |
| ATOM | 2159 | C | SER | A | 142 | 60.401 | −42.488 | 6.016 | 1.00 | 17.20 | A | C |
| ATOM | 2160 | O | SER | A | 142 | 59.585 | −41.779 | 5.427 | 1.00 | 17.78 | A | O |

TABLE 8-2-continued

Coordinates for L494P Structure

| ATOM | 2162 | N | LEU | A | 143 | 60.052 | −43.516 | 6.787 | 1.00 | 16.32 | A | N |
|---|---|---|---|---|---|---|---|---|---|---|---|---|
| ATOM | 2163 | CA | LEU | A | 143 | 58.651 | −43.842 | 7.046 | 1.00 | 15.60 | A | C |
| ATOM | 2165 | CB | LEU | A | 143 | 58.534 | −45.084 | 7.940 | 1.00 | 15.48 | A | C |
| ATOM | 2168 | CG | LEU | A | 143 | 57.132 | −45.436 | 8.460 | 1.00 | 14.83 | A | C |
| ATOM | 2170 | CD1 | LEU | A | 143 | 56.099 | −45.438 | 7.342 | 1.00 | 14.92 | A | C |
| ATOM | 2174 | CD2 | LEU | A | 143 | 57.146 | −46.774 | 9.165 | 1.00 | 14.54 | A | C |
| ATOM | 2178 | C | LEU | A | 143 | 57.929 | −42.662 | 7.693 | 1.00 | 15.26 | A | C |
| ATOM | 2179 | O | LEU | A | 143 | 56.819 | −42.316 | 7.292 | 1.00 | 15.30 | A | O |
| ATOM | 2181 | N | TYR | A | 144 | 58.562 | −42.052 | 8.692 | 1.00 | 14.88 | A | N |
| ATOM | 2182 | CA | TYR | A | 144 | 57.996 | −40.882 | 9.359 | 1.00 | 14.72 | A | C |
| ATOM | 2184 | CB | TYR | A | 144 | 58.966 | −40.327 | 10.406 | 1.00 | 14.64 | A | C |
| ATOM | 2187 | CG | TYR | A | 144 | 58.555 | −38.994 | 10.994 | 1.00 | 14.77 | A | C |
| ATOM | 2188 | CD1 | TYR | A | 144 | 57.598 | −38.919 | 12.001 | 1.00 | 15.26 | A | C |
| ATOM | 2190 | CE1 | TYR | A | 144 | 57.220 | −37.698 | 12.548 | 1.00 | 15.65 | A | C |
| ATOM | 2192 | CZ | TYR | A | 144 | 57.807 | −36.534 | 12.091 | 1.00 | 17.33 | A | C |
| ATOM | 2193 | OH | TYR | A | 144 | 57.435 | −35.321 | 12.629 | 1.00 | 19.54 | A | O |
| ATOM | 2195 | CE2 | TYR | A | 144 | 58.761 | −36.583 | 11.090 | 1.00 | 17.47 | A | C |
| ATOM | 2197 | CD2 | TYR | A | 144 | 59.131 | −37.809 | 10.550 | 1.00 | 16.29 | A | C |
| ATOM | 2199 | C | TYR | A | 144 | 57.656 | −39.801 | 8.344 | 1.00 | 14.69 | A | C |
| ATOM | 2200 | O | TYR | A | 144 | 56.554 | −39.263 | 8.354 | 1.00 | 14.53 | A | O |
| ATOM | 2202 | N | GLU | A | 145 | 58.605 | −39.502 | 7.464 | 1.00 | 14.92 | A | N |
| ATOM | 2203 | CA | GLU | A | 145 | 58.428 | −38.457 | 6.458 | 1.00 | 15.34 | A | C |
| ATOM | 2205 | CB | GLU | A | 145 | 59.725 | −38.257 | 5.666 | 1.00 | 15.45 | A | C |
| ATOM | 2208 | CG | GLU | A | 145 | 60.888 | −37.694 | 6.479 | 1.00 | 16.03 | A | C |
| ATOM | 2211 | CD | GLU | A | 145 | 60.742 | −36.220 | 6.815 | 1.00 | 17.46 | A | C |
| ATOM | 2212 | OE1 | GLU | A | 145 | 59.672 | −35.627 | 6.537 | 1.00 | 18.49 | A | O |
| ATOM | 2213 | OE2 | GLU | A | 145 | 61.709 | −35.654 | 7.368 | 1.00 | 17.22 | A | O |
| ATOM | 2214 | C | GLU | A | 145 | 57.277 | −38.759 | 5.493 | 1.00 | 15.41 | A | C |
| ATOM | 2215 | O | GLU | A | 145 | 56.569 | −37.845 | 5.059 | 1.00 | 15.63 | A | O |
| ATOM | 2217 | N | ALA | A | 146 | 57.100 | −40.038 | 5.167 | 1.00 | 15.04 | A | N |
| ATOM | 2218 | CA | ALA | A | 146 | 56.073 | −40.475 | 4.221 | 1.00 | 14.82 | A | C |
| ATOM | 2220 | CB | ALA | A | 146 | 56.363 | −41.894 | 3.752 | 1.00 | 14.97 | A | C |
| ATOM | 2224 | C | ALA | A | 146 | 54.665 | −40.406 | 4.801 | 1.00 | 14.76 | A | C |
| ATOM | 2225 | O | ALA | A | 146 | 53.695 | −40.297 | 4.056 | 1.00 | 14.65 | A | O |
| ATOM | 2227 | N | SER | A | 147 | 54.551 | −40.470 | 6.124 | 1.00 | 14.98 | A | N |
| ATOM | 2228 | CA | SER | A | 147 | 53.245 | −40.507 | 6.778 | 1.00 | 15.23 | A | C |
| ATOM | 2230 | CB | SER | A | 147 | 53.401 | −40.795 | 8.271 | 1.00 | 15.04 | A | C |
| ATOM | 2233 | OG | SER | A | 147 | 53.997 | −39.704 | 8.942 | 1.00 | 14.18 | A | O |
| ATOM | 2235 | C | SER | A | 147 | 52.457 | −39.214 | 6.591 | 1.00 | 15.94 | A | C |
| ATOM | 2236 | O | SER | A | 147 | 51.231 | −39.204 | 6.738 | 1.00 | 16.57 | A | O |
| ATOM | 2238 | N | PHE | A | 148 | 53.165 | −38.133 | 6.271 | 1.00 | 16.28 | A | N |
| ATOM | 2239 | CA | PHE | A | 148 | 52.552 | −36.815 | 6.123 | 1.00 | 16.58 | A | C |
| ATOM | 2241 | CB | PHE | A | 148 | 53.581 | −35.727 | 6.416 | 1.00 | 16.42 | A | C |
| ATOM | 2244 | CG | PHE | A | 148 | 53.926 | −35.627 | 7.867 | 1.00 | 17.86 | A | C |
| ATOM | 2245 | CD1 | PHE | A | 148 | 53.239 | −34.753 | 8.694 | 1.00 | 19.24 | A | C |
| ATOM | 2247 | CE1 | PHE | A | 148 | 53.538 | −34.667 | 10.042 | 1.00 | 19.64 | A | C |
| ATOM | 2249 | CZ | PHE | A | 148 | 54.529 | −35.473 | 10.579 | 1.00 | 20.02 | A | C |
| ATOM | 2251 | CE2 | PHE | A | 148 | 55.214 | −36.358 | 9.763 | 1.00 | 19.24 | A | C |
| ATOM | 2253 | CD2 | PHE | A | 148 | 54.905 | −36.435 | 8.416 | 1.00 | 19.02 | A | C |
| ATOM | 2255 | C | PHE | A | 148 | 51.898 | −36.586 | 4.765 | 1.00 | 16.73 | A | C |
| ATOM | 2256 | O | PHE | A | 148 | 51.078 | −35.674 | 4.623 | 1.00 | 17.72 | A | O |
| ATOM | 2258 | N | LEU | A | 149 | 52.241 | −37.416 | 3.780 | 1.00 | 16.12 | A | N |
| ATOM | 2259 | CA | LEU | A | 149 | 51.605 | −37.353 | 2.461 | 1.00 | 15.65 | A | C |
| ATOM | 2261 | CB | LEU | A | 149 | 52.582 | −37.802 | 1.368 | 1.00 | 15.36 | A | C |
| ATOM | 2264 | CG | LEU | A | 149 | 53.836 | −36.939 | 1.206 | 1.00 | 14.18 | A | C |
| ATOM | 2266 | CD1 | LEU | A | 149 | 54.944 | −37.408 | 2.137 | 1.00 | 13.76 | A | C |
| ATOM | 2270 | CD2 | LEU | A | 149 | 54.315 | −36.957 | −0.235 | 1.00 | 14.24 | A | C |
| ATOM | 2274 | C | LEU | A | 149 | 50.328 | −38.200 | 2.405 | 1.00 | 15.63 | A | C |
| ATOM | 2275 | O | LEU | A | 149 | 49.735 | −38.366 | 1.337 | 1.00 | 15.57 | A | O |
| ATOM | 2277 | N | ALA | A | 150 | 49.909 | −38.723 | 3.557 | 1.00 | 15.70 | A | N |
| ATOM | 2278 | CA | ALA | A | 150 | 48.736 | −39.589 | 3.650 | 1.00 | 15.72 | A | C |
| ATOM | 2280 | CB | ALA | A | 150 | 48.563 | −40.070 | 5.086 | 1.00 | 15.67 | A | C |
| ATOM | 2284 | C | ALA | A | 150 | 47.456 | −38.899 | 3.170 | 1.00 | 15.65 | A | C |
| ATOM | 2285 | O | ALA | A | 150 | 47.255 | −37.706 | 3.404 | 1.00 | 15.79 | A | O |
| ATOM | 2287 | N | LEU | A | 151 | 46.606 | −39.665 | 2.491 | 1.00 | 15.19 | A | N |
| ATOM | 2288 | CA | LEU | A | 151 | 45.287 | −39.199 | 2.067 | 1.00 | 14.89 | A | C |
| ATOM | 2290 | CB | LEU | A | 151 | 44.936 | −39.778 | 0.698 | 1.00 | 14.68 | A | C |
| ATOM | 2293 | CG | LEU | A | 151 | 45.733 | −39.223 | −0.478 | 1.00 | 13.02 | A | C |
| ATOM | 2295 | CD1 | LEU | A | 151 | 45.541 | −40.087 | −1.715 | 1.00 | 12.24 | A | C |
| ATOM | 2299 | CD2 | LEU | A | 151 | 45.311 | −37.794 | −0.747 | 1.00 | 12.42 | A | C |
| ATOM | 2303 | C | LEU | A | 151 | 44.241 | −39.629 | 3.087 | 1.00 | 14.91 | A | C |
| ATOM | 2304 | O | LEU | A | 151 | 44.529 | −40.431 | 3.976 | 1.00 | 14.52 | A | O |
| ATOM | 2306 | N | GLU | A | 152 | 43.027 | −39.102 | 2.957 | 1.00 | 15.12 | A | N |
| ATOM | 2307 | CA | GLU | A | 152 | 41.949 | −39.471 | 3.870 | 1.00 | 15.70 | A | C |
| ATOM | 2309 | CB | GLU | A | 152 | 40.662 | −38.692 | 3.572 | 1.00 | 16.17 | A | C |
| ATOM | 2312 | CG | GLU | A | 152 | 40.577 | −37.350 | 4.299 | 1.00 | 18.12 | A | C |
| ATOM | 2315 | CD | GLU | A | 152 | 39.183 | −36.749 | 4.265 | 1.00 | 19.18 | A | C |
| ATOM | 2316 | OE1 | GLU | A | 152 | 38.686 | −36.455 | 3.157 | 1.00 | 20.47 | A | O |

TABLE 8-2-continued

Coordinates for L494P Structure

| ATOM | 2317 | OE2 | GLU | A | 152 | 38.589 | −36.566 | 5.349 | 1.00 | 19.32 A | O |
|---|---|---|---|---|---|---|---|---|---|---|---|
| ATOM | 2318 | C | GLU | A | 152 | 41.690 | −40.968 | 3.793 | 1.00 | 15.50 A | C |
| ATOM | 2319 | O | GLU | A | 152 | 41.623 | −41.535 | 2.704 | 1.00 | 15.88 A | O |
| ATOM | 2321 | N | GLY | A | 153 | 41.575 | −41.602 | 4.957 | 1.00 | 15.25 A | N |
| ATOM | 2322 | CA | GLY | A | 153 | 41.298 | −43.033 | 5.039 | 1.00 | 14.87 A | C |
| ATOM | 2325 | C | GLY | A | 153 | 42.512 | −43.935 | 5.003 | 1.00 | 14.62 A | C |
| ATOM | 2326 | O | GLY | A | 153 | 42.393 | −45.134 | 5.246 | 1.00 | 14.54 A | O |
| ATOM | 2328 | N | GLU | A | 154 | 43.680 | −43.372 | 4.705 | 1.00 | 14.82 A | N |
| ATOM | 2329 | CA | GLU | A | 154 | 44.907 | −44.157 | 4.660 | 1.00 | 14.90 A | C |
| ATOM | 2331 | CB | GLU | A | 154 | 45.957 | −43.488 | 3.769 | 1.00 | 14.85 A | C |
| ATOM | 2334 | CG | GLU | A | 154 | 45.527 | −43.403 | 2.305 | 1.00 | 15.01 A | C |
| ATOM | 2337 | CD | GLU | A | 154 | 46.681 | −43.160 | 1.350 | 1.00 | 15.65 A | C |
| ATOM | 2338 | OE1 | GLU | A | 154 | 46.559 | −43.530 | 0.164 | 1.00 | 13.73 A | O |
| ATOM | 2339 | OE2 | GLU | A | 154 | 47.712 | −42.599 | 1.779 | 1.00 | 18.73 A | O |
| ATOM | 2340 | C | GLU | A | 154 | 45.421 | −44.359 | 6.079 | 1.00 | 14.88 A | C |
| ATOM | 2341 | O | GLU | A | 154 | 46.302 | −43.638 | 6.548 | 1.00 | 15.13 A | O |
| ATOM | 2343 | N | ASN | A | 155 | 44.848 | −45.354 | 6.750 | 1.00 | 14.65 A | N |
| ATOM | 2344 | CA | ASN | A | 155 | 45.097 | −45.587 | 8.172 | 1.00 | 14.39 A | C |
| ATOM | 2346 | CB | ASN | A | 155 | 44.043 | −46.540 | 8.758 | 1.00 | 14.42 A | C |
| ATOM | 2349 | CG | ASN | A | 155 | 44.069 | −47.915 | 8.115 | 1.00 | 14.05 A | C |
| ATOM | 2350 | OD1 | ASN | A | 155 | 44.417 | −48.059 | 6.946 | 1.00 | 15.53 A | O |
| ATOM | 2351 | ND2 | ASN | A | 155 | 43.691 | −48.932 | 8.877 | 1.00 | 14.24 A | N |
| ATOM | 2354 | C | ASN | A | 155 | 46.499 | −46.101 | 8.492 | 1.00 | 14.15 A | C |
| ATOM | 2355 | O | ASN | A | 155 | 47.057 | −45.750 | 9.530 | 1.00 | 14.42 A | O |
| ATOM | 2357 | N | ILE | A | 156 | 47.066 | −46.923 | 7.607 | 1.00 | 13.81 A | N |
| ATOM | 2358 | CA | ILE | A | 156 | 48.394 | −47.515 | 7.836 | 1.00 | 13.39 A | C |
| ATOM | 2360 | CB | ILE | A | 156 | 48.774 | −48.549 | 6.731 | 1.00 | 13.45 A | C |
| ATOM | 2362 | CG1 | ILE | A | 156 | 47.886 | −49.794 | 6.827 | 1.00 | 13.17 A | C |
| ATOM | 2365 | CD1 | ILE | A | 156 | 48.364 | −50.961 | 5.977 | 1.00 | 12.86 A | C |
| ATOM | 2369 | CG2 | ILE | A | 156 | 50.234 | −48.965 | 6.847 | 1.00 | 12.55 A | C |
| ATOM | 2373 | C | ILE | A | 156 | 49.486 | −46.447 | 7.955 | 1.00 | 13.02 A | C |
| ATOM | 2374 | O | ILE | A | 156 | 50.471 | −46.643 | 8.665 | 1.00 | 12.85 A | O |
| ATOM | 2376 | N | LEU | A | 157 | 49.304 | −45.319 | 7.275 | 1.00 | 12.90 A | N |
| ATOM | 2377 | CA | LEU | A | 157 | 50.246 | −44.205 | 7.381 | 1.00 | 12.94 A | C |
| ATOM | 2379 | CB | LEU | A | 157 | 50.114 | −43.261 | 6.182 | 1.00 | 12.67 A | C |
| ATOM | 2382 | CG | LEU | A | 157 | 50.865 | −43.718 | 4.929 | 1.00 | 11.71 A | C |
| ATOM | 2384 | CD1 | LEU | A | 157 | 50.470 | −45.129 | 4.540 | 1.00 | 11.58 A | C |
| ATOM | 2388 | CD2 | LEU | A | 157 | 50.623 | −42.762 | 3.774 | 1.00 | 12.63 A | C |
| ATOM | 2392 | C | LEU | A | 157 | 50.078 | −43.444 | 8.701 | 1.00 | 13.44 A | C |
| ATOM | 2393 | O | LEU | A | 157 | 51.068 | −43.039 | 9.308 | 1.00 | 13.49 A | O |
| ATOM | 2395 | N | ASP | A | 158 | 48.833 | −43.260 | 9.144 | 1.00 | 14.10 A | N |
| ATOM | 2396 | CA | ASP | A | 158 | 48.551 | −42.626 | 10.442 | 1.00 | 14.43 A | C |
| ATOM | 2398 | CB | ASP | A | 158 | 47.043 | −42.417 | 10.635 | 1.00 | 14.42 A | C |
| ATOM | 2401 | CG | ASP | A | 158 | 46.488 | −41.307 | 9.759 | 1.00 | 15.28 A | C |
| ATOM | 2402 | OD1 | ASP | A | 158 | 47.035 | −40.184 | 9.789 | 1.00 | 14.96 A | O |
| ATOM | 2403 | OD2 | ASP | A | 158 | 45.494 | −41.555 | 9.045 | 1.00 | 17.78 A | O |
| ATOM | 2404 | C | ASP | A | 158 | 49.113 | −43.454 | 11.597 | 1.00 | 14.67 A | C |
| ATOM | 2405 | O | ASP | A | 158 | 49.622 | −42.899 | 12.573 | 1.00 | 14.25 A | O |
| ATOM | 2407 | N | GLU | A | 159 | 48.999 | −44.778 | 11.476 | 1.00 | 15.29 A | N |
| ATOM | 2408 | CA | GLU | A | 159 | 49.677 | −45.723 | 12.370 | 1.00 | 15.67 A | C |
| ATOM | 2410 | CB | GLU | A | 159 | 49.261 | −47.160 | 12.052 | 1.00 | 15.79 A | C |
| ATOM | 2413 | CG | GLU | A | 159 | 47.811 | −47.499 | 12.324 | 1.00 | 16.58 A | C |
| ATOM | 2416 | CD | GLU | A | 159 | 47.447 | −48.900 | 11.846 | 1.00 | 18.81 A | C |
| ATOM | 2417 | OE1 | GLU | A | 159 | 48.362 | −49.720 | 11.591 | 1.00 | 17.33 A | O |
| ATOM | 2418 | OE2 | GLU | A | 159 | 46.237 | −49.182 | 11.725 | 1.00 | 22.11 A | O |
| ATOM | 2419 | C | GLU | A | 159 | 51.198 | −45.631 | 12.218 | 1.00 | 15.73 A | C |
| ATOM | 2420 | O | GLU | A | 159 | 51.934 | −45.685 | 13.205 | 1.00 | 15.90 A | O |
| ATOM | 2422 | N | ALA | A | 160 | 51.656 | −45.525 | 10.971 | 1.00 | 15.58 A | N |
| ATOM | 2423 | CA | ALA | A | 160 | 53.082 | −45.445 | 10.660 | 1.00 | 15.31 A | C |
| ATOM | 2425 | CB | ALA | A | 160 | 53.297 | −45.451 | 9.153 | 1.00 | 15.15 A | C |
| ATOM | 2429 | C | ALA | A | 160 | 53.726 | −44.210 | 11.276 | 1.00 | 15.28 A | C |
| ATOM | 2430 | O | ALA | A | 160 | 54.895 | −44.244 | 11.651 | 1.00 | 15.24 A | O |
| ATOM | 2432 | N | LYS | A | 161 | 52.965 | −43.124 | 11.373 | 1.00 | 15.64 A | N |
| ATOM | 2433 | CA | LYS | A | 161 | 53.459 | −41.904 | 11.996 | 1.00 | 16.20 A | C |
| ATOM | 2435 | CB | LYS | A | 161 | 52.467 | −40.748 | 11.813 | 1.00 | 16.58 A | C |
| ATOM | 2438 | CG | LYS | A | 161 | 53.056 | −39.373 | 12.115 | 1.00 | 17.99 A | C |
| ATOM | 2441 | CD | LYS | A | 161 | 51.982 | −38.301 | 12.267 | 1.00 | 19.18 A | C |
| ATOM | 2444 | CE | LYS | A | 161 | 51.280 | −38.008 | 10.956 | 1.00 | 20.22 A | C |
| ATOM | 2447 | NZ | LYS | A | 161 | 50.469 | −36.762 | 11.043 | 1.00 | 22.18 A | N |
| ATOM | 2451 | C | LYS | A | 161 | 53.714 | −42.165 | 13.479 | 1.00 | 16.44 A | C |
| ATOM | 2452 | O | LYS | A | 161 | 54.843 | −42.022 | 13.951 | 1.00 | 16.58 A | O |
| ATOM | 2454 | N | VAL | A | 162 | 52.671 | −42.579 | 14.197 | 1.00 | 16.53 A | N |
| ATOM | 2455 | CA | VAL | A | 162 | 52.759 | −42.814 | 15.645 | 1.00 | 16.48 A | C |
| ATOM | 2457 | CB | VAL | A | 162 | 51.412 | −43.299 | 16.237 | 1.00 | 16.23 A | C |
| ATOM | 2459 | CG1 | VAL | A | 162 | 51.528 | −43.498 | 17.742 | 1.00 | 16.10 A | C |
| ATOM | 2463 | CG2 | VAL | A | 162 | 50.302 | −42.307 | 15.923 | 1.00 | 16.13 A | C |
| ATOM | 2467 | C | VAL | A | 162 | 53.861 | −43.822 | 15.995 | 1.00 | 16.54 A | C |
| ATOM | 2468 | O | VAL | A | 162 | 54.609 | −43.616 | 16.952 | 1.00 | 16.62 A | O |

TABLE 8-2-continued

Coordinates for L494P Structure

| ATOM | 2470 | N | PHE | A | 163 | 53.955 | −44.899 | 15.215 | 1.00 | 16.67 A | N |
|---|---|---|---|---|---|---|---|---|---|---|---|
| ATOM | 2471 | CA | PHE | A | 163 | 55.011 | −45.905 | 15.387 | 1.00 | 16.71 A | C |
| ATOM | 2473 | CB | PHE | A | 163 | 54.803 | −47.072 | 14.417 | 1.00 | 16.07 A | C |
| ATOM | 2476 | CG | PHE | A | 163 | 55.907 | −48.094 | 14.446 | 1.00 | 13.86 A | C |
| ATOM | 2477 | CD1 | PHE | A | 163 | 55.862 | −49.160 | 15.332 | 1.00 | 12.47 A | C |
| ATOM | 2479 | CE1 | PHE | A | 163 | 56.880 | −50.105 | 15.360 | 1.00 | 11.52 A | C |
| ATOM | 2481 | CZ | PHE | A | 163 | 57.957 | −49.986 | 14.497 | 1.00 | 10.81 A | C |
| ATOM | 2483 | CE2 | PHE | A | 163 | 58.014 | −48.928 | 13.610 | 1.00 | 11.67 A | C |
| ATOM | 2485 | CD2 | PHE | A | 163 | 56.992 | −47.988 | 13.587 | 1.00 | 12.64 A | C |
| ATOM | 2487 | C | PHE | A | 163 | 56.406 | −45.311 | 15.182 | 1.00 | 17.79 A | C |
| ATOM | 2488 | O | PHE | A | 163 | 57.368 | −45.724 | 15.838 | 1.00 | 17.93 A | O |
| ATOM | 2490 | N | ALA | A | 164 | 56.511 | −44.355 | 14.262 | 1.00 | 18.68 A | N |
| ATOM | 2491 | CA | ALA | A | 164 | 57.782 | −43.701 | 13.968 | 1.00 | 19.35 A | C |
| ATOM | 2493 | CB | ALA | A | 164 | 57.721 | −43.017 | 12.611 | 1.00 | 19.35 A | C |
| ATOM | 2497 | C | ALA | A | 164 | 58.149 | −42.697 | 15.060 | 1.00 | 19.82 A | C |
| ATOM | 2498 | O | ALA | A | 164 | 59.254 | −42.742 | 15.602 | 1.00 | 20.21 A | O |
| ATOM | 2500 | N | ILE | A | 165 | 57.217 | −41.803 | 15.383 | 1.00 | 20.14 A | N |
| ATOM | 2501 | CA | ILE | A | 165 | 57.441 | −40.775 | 16.404 | 1.00 | 20.35 A | C |
| ATOM | 2503 | CB | ILE | A | 165 | 56.150 | −39.959 | 16.698 | 1.00 | 20.49 A | C |
| ATOM | 2505 | CG1 | ILE | A | 165 | 55.797 | −39.062 | 15.508 | 1.00 | 20.83 A | C |
| ATOM | 2508 | CD1 | ILE | A | 165 | 54.500 | −38.292 | 15.676 | 1.00 | 21.96 A | C |
| ATOM | 2512 | CG2 | ILE | A | 165 | 56.325 | −39.092 | 17.939 | 1.00 | 20.43 A | C |
| ATOM | 2516 | C | ILE | A | 165 | 57.949 | −41.397 | 17.703 | 1.00 | 20.24 A | C |
| ATOM | 2517 | O | ILE | A | 165 | 59.035 | −41.062 | 18.173 | 1.00 | 19.62 A | O |
| ATOM | 2519 | N | SER | A | 166 | 57.167 | −42.320 | 18.258 | 1.00 | 20.69 A | N |
| ATOM | 2520 | CA | SER | A | 166 | 57.470 | −42.919 | 19.560 | 1.00 | 21.20 A | C |
| ATOM | 2522 | CB | SER | A | 166 | 56.381 | −43.923 | 19.958 | 1.00 | 21.36 A | C |
| ATOM | 2525 | OG | SER | A | 166 | 56.287 | −44.983 | 19.023 | 1.00 | 21.83 A | O |
| ATOM | 2527 | C | SER | A | 166 | 58.846 | −43.587 | 19.616 | 1.00 | 21.27 A | C |
| ATOM | 2528 | O | SER | A | 166 | 59.468 | −43.630 | 20.679 | 1.00 | 21.20 A | O |
| ATOM | 2530 | N | HIS | A | 167 | 59.314 | −44.102 | 18.480 | 1.00 | 21.52 A | N |
| ATOM | 2531 | CA | HIS | A | 167 | 60.649 | −44.703 | 18.398 | 1.00 | 21.98 A | C |
| ATOM | 2533 | CB | HIS | A | 167 | 60.677 | −45.836 | 17.366 | 1.00 | 22.19 A | C |
| ATOM | 2536 | CG | HIS | A | 167 | 60.128 | −47.131 | 17.881 | 1.00 | 23.11 A | C |
| ATOM | 2537 | ND1 | HIS | A | 167 | 58.969 | −47.696 | 17.395 | 1.00 | 23.65 A | N |
| ATOM | 2539 | CE1 | HIS | A | 167 | 58.730 | −48.826 | 18.038 | 1.00 | 24.10 A | C |
| ATOM | 2541 | NE2 | HIS | A | 167 | 59.690 | −49.012 | 18.926 | 1.00 | 23.55 A | N |
| ATOM | 2543 | CD2 | HIS | A | 167 | 60.575 | −47.964 | 18.851 | 1.00 | 23.42 A | C |
| ATOM | 2545 | C | HIS | A | 167 | 61.748 | −43.677 | 18.099 | 1.00 | 22.06 A | C |
| ATOM | 2546 | O | HIS | A | 167 | 62.900 | −43.884 | 18.480 | 1.00 | 21.93 A | O |
| ATOM | 2548 | N | LEU | A | 168 | 61.397 | −42.584 | 17.422 | 1.00 | 22.44 A | N |
| ATOM | 2549 | CA | LEU | A | 168 | 62.342 | −41.486 | 17.174 | 1.00 | 22.76 A | C |
| ATOM | 2551 | CB | LEU | A | 168 | 61.860 | −40.590 | 16.025 | 1.00 | 22.70 A | C |
| ATOM | 2554 | CG | LEU | A | 168 | 61.921 | −41.116 | 14.589 | 1.00 | 22.46 A | C |
| ATOM | 2556 | CD1 | LEU | A | 168 | 61.482 | −40.020 | 13.632 | 1.00 | 22.16 A | C |
| ATOM | 2560 | CD2 | LEU | A | 168 | 63.317 | −41.601 | 14.234 | 1.00 | 23.20 A | C |
| ATOM | 2564 | C | LEU | A | 168 | 62.542 | −40.614 | 18.412 | 1.00 | 23.43 A | C |
| ATOM | 2565 | O | LEU | A | 168 | 63.648 | −40.140 | 18.673 | 1.00 | 23.50 A | O |
| ATOM | 2567 | N | LYS | A | 169 | 61.465 | −40.408 | 19.165 | 1.00 | 24.25 A | N |
| ATOM | 2568 | CA | LYS | A | 169 | 61.446 | −39.435 | 20.259 | 1.00 | 24.95 A | C |
| ATOM | 2570 | CB | LYS | A | 169 | 60.007 | −39.234 | 20.749 | 1.00 | 24.99 A | C |
| ATOM | 2573 | CG | LYS | A | 169 | 59.788 | −37.951 | 21.533 | 1.00 | 26.38 A | C |
| ATOM | 2576 | CD | LYS | A | 169 | 58.329 | −37.522 | 21.493 | 1.00 | 27.59 A | C |
| ATOM | 2579 | CE | LYS | A | 169 | 58.115 | −36.206 | 22.217 | 1.00 | 28.00 A | C |
| ATOM | 2582 | NZ | LYS | A | 169 | 56.702 | −35.756 | 22.113 | 1.00 | 29.00 A | N |
| ATOM | 2586 | C | LYS | A | 169 | 62.353 | −39.802 | 21.438 | 1.00 | 25.45 A | C |
| ATOM | 2587 | O | LYS | A | 169 | 62.861 | −38.917 | 22.128 | 1.00 | 25.46 A | O |
| ATOM | 2589 | N | GLU | A | 170 | 62.560 | −41.097 | 21.661 | 1.00 | 26.28 A | N |
| ATOM | 2590 | CA | GLU | A | 170 | 63.351 | −41.570 | 22.798 | 1.00 | 27.20 A | C |
| ATOM | 2592 | CB | GLU | A | 170 | 62.625 | −42.725 | 23.502 | 1.00 | 27.52 A | C |
| ATOM | 2595 | CG | GLU | A | 170 | 61.178 | −42.416 | 23.892 | 1.00 | 29.00 A | C |
| ATOM | 2598 | CD | GLU | A | 170 | 61.051 | −41.184 | 24.776 | 1.00 | 30.77 A | C |
| ATOM | 2599 | OE1 | GLU | A | 170 | 61.736 | −41.127 | 25.821 | 1.00 | 30.80 A | O |
| ATOM | 2600 | OE2 | GLU | A | 170 | 60.266 | −40.274 | 24.426 | 1.00 | 31.83 A | O |
| ATOM | 2601 | C | GLU | A | 170 | 64.756 | −41.997 | 22.365 | 1.00 | 27.59 A | C |
| ATOM | 2602 | O | GLU | A | 170 | 65.223 | −43.086 | 22.715 | 1.00 | 27.53 A | O |
| ATOM | 2604 | N | LEU | A | 171 | 65.424 | −41.127 | 21.609 | 1.00 | 27.91 A | N |
| ATOM | 2605 | CA | LEU | A | 171 | 66.775 | −41.390 | 21.120 | 1.00 | 28.20 A | C |
| ATOM | 2607 | CB | LEU | A | 171 | 66.784 | −41.495 | 19.594 | 1.00 | 27.90 A | C |
| ATOM | 2610 | CG | LEU | A | 171 | 65.896 | −42.582 | 18.983 | 1.00 | 27.09 A | C |
| ATOM | 2612 | CD1 | LEU | A | 171 | 66.044 | −42.582 | 17.469 | 1.00 | 25.97 A | C |
| ATOM | 2616 | CD2 | LEU | A | 171 | 66.215 | −43.960 | 19.554 | 1.00 | 25.82 A | C |
| ATOM | 2620 | C | LEU | A | 171 | 67.720 | −40.283 | 21.570 | 1.00 | 28.93 A | C |
| ATOM | 2621 | O | LEU | A | 171 | 67.390 | −39.099 | 21.468 | 1.00 | 28.94 A | O |
| ATOM | 2623 | N | SER | A | 172 | 68.895 | −40.680 | 22.060 | 1.00 | 29.73 A | N |
| ATOM | 2624 | CA | SER | A | 172 | 69.882 | −39.745 | 22.605 | 1.00 | 30.12 A | C |
| ATOM | 2626 | CB | SER | A | 172 | 70.465 | −40.293 | 23.905 | 1.00 | 30.03 A | C |
| ATOM | 2629 | OG | SER | A | 172 | 69.435 | −40.707 | 24.783 | 1.00 | 30.49 A | O |

TABLE 8-2-continued

Coordinates for L494P Structure

| ATOM | 2631 | C | SER | A | 172 | 71.012 | −39.473 | 21.617 | 1.00 | 30.47 | A | C |
|---|---|---|---|---|---|---|---|---|---|---|---|---|
| ATOM | 2632 | O | SER | A | 172 | 71.235 | −40.241 | 20.678 | 1.00 | 30.80 | A | O |
| ATOM | 2634 | N | GLU | A | 173 | 71.733 | −38.381 | 21.855 | 1.00 | 30.63 | A | N |
| ATOM | 2635 | CA | GLU | A | 173 | 72.807 | −37.942 | 20.964 | 1.00 | 30.79 | A | C |
| ATOM | 2637 | CB | GLU | A | 173 | 73.199 | −36.492 | 21.287 | 1.00 | 30.90 | A | C |
| ATOM | 2640 | CG | GLU | A | 173 | 73.888 | −35.747 | 20.143 | 1.00 | 31.84 | A | C |
| ATOM | 2643 | CD | GLU | A | 173 | 73.898 | −34.232 | 20.335 | 1.00 | 33.26 | A | C |
| ATOM | 2644 | OE1 | GLU | A | 173 | 72.839 | −33.658 | 20.672 | 1.00 | 33.46 | A | O |
| ATOM | 2645 | OE2 | GLU | A | 173 | 74.964 | −33.611 | 20.136 | 1.00 | 34.47 | A | O |
| ATOM | 2646 | C | GLU | A | 173 | 74.038 | −38.862 | 21.017 | 1.00 | 30.75 | A | C |
| ATOM | 2647 | O | GLU | A | 173 | 74.807 | −38.913 | 20.057 | 1.00 | 30.90 | A | O |
| ATOM | 2649 | N | GLU | A | 174 | 74.221 | −39.585 | 22.125 | 1.00 | 30.65 | A | N |
| ATOM | 2650 | CA | GLU | A | 174 | 75.338 | −40.532 | 22.262 | 1.00 | 30.58 | A | C |
| ATOM | 2652 | CB | GLU | A | 174 | 75.627 | −40.857 | 23.733 | 1.00 | 30.55 | A | C |
| ATOM | 2655 | CG | GLU | A | 174 | 75.957 | −39.663 | 24.614 | 1.00 | 30.63 | A | C |
| ATOM | 2658 | CD | GLU | A | 174 | 74.768 | −39.198 | 25.430 | 1.00 | 30.50 | A | C |
| ATOM | 2659 | OE1 | GLU | A | 174 | 73.749 | −38.804 | 24.825 | 1.00 | 29.37 | A | O |
| ATOM | 2660 | OE2 | GLU | A | 174 | 74.852 | −39.230 | 26.675 | 1.00 | 30.66 | A | O |
| ATOM | 2661 | C | GLU | A | 174 | 75.073 | −41.847 | 21.530 | 1.00 | 30.62 | A | C |
| ATOM | 2662 | O | GLU | A | 174 | 75.991 | −42.432 | 20.948 | 1.00 | 30.96 | A | O |
| ATOM | 2664 | N | LYS | A | 175 | 73.822 | −42.308 | 21.575 | 1.00 | 30.19 | A | N |
| ATOM | 2665 | CA | LYS | A | 175 | 73.443 | −43.617 | 21.030 | 1.00 | 29.66 | A | C |
| ATOM | 2667 | CB | LYS | A | 175 | 71.983 | −43.959 | 21.363 | 1.00 | 29.85 | A | C |
| ATOM | 2670 | CG | LYS | A | 175 | 71.603 | −43.849 | 22.838 | 1.00 | 30.60 | A | C |
| ATOM | 2673 | CD | LYS | A | 175 | 72.325 | −44.864 | 23.703 | 1.00 | 30.80 | A | C |
| ATOM | 2676 | CE | LYS | A | 175 | 71.987 | −44.658 | 25.168 | 1.00 | 30.86 | A | C |
| ATOM | 2679 | NZ | LYS | A | 175 | 72.453 | −45.794 | 26.002 | 1.00 | 31.13 | A | N |
| ATOM | 2683 | C | LYS | A | 175 | 73.628 | −43.623 | 19.521 | 1.00 | 28.93 | A | C |
| ATOM | 2684 | O | LYS | A | 175 | 74.345 | −44.461 | 18.973 | 1.00 | 28.70 | A | O |
| ATOM | 2686 | N | ILE | A | 176 | 72.973 | −42.670 | 18.865 | 1.00 | 28.25 | A | N |
| ATOM | 2687 | CA | ILE | A | 176 | 73.092 | −42.490 | 17.424 | 1.00 | 27.93 | A | C |
| ATOM | 2689 | CB | ILE | A | 176 | 71.735 | −42.112 | 16.764 | 1.00 | 27.94 | A | C |
| ATOM | 2691 | CG1 | ILE | A | 176 | 71.039 | −40.966 | 17.514 | 1.00 | 28.01 | A | C |
| ATOM | 2694 | CD1 | ILE | A | 176 | 69.948 | −40.282 | 16.713 | 1.00 | 27.59 | A | C |
| ATOM | 2698 | CG2 | ILE | A | 176 | 70.822 | −43.325 | 16.716 | 1.00 | 27.61 | A | C |
| ATOM | 2702 | C | ILE | A | 176 | 74.144 | −41.421 | 17.143 | 1.00 | 27.68 | A | C |
| ATOM | 2703 | O | ILE | A | 176 | 74.655 | −40.788 | 18.067 | 1.00 | 27.18 | A | O |
| ATOM | 2705 | N | GLY | A | 177 | 74.473 | −41.237 | 15.868 | 1.00 | 27.66 | A | N |
| ATOM | 2706 | CA | GLY | A | 177 | 75.460 | −40.244 | 15.466 | 1.00 | 27.56 | A | C |
| ATOM | 2709 | C | GLY | A | 177 | 74.987 | −38.831 | 15.744 | 1.00 | 27.45 | A | C |
| ATOM | 2710 | O | GLY | A | 177 | 73.785 | −38.552 | 15.719 | 1.00 | 27.69 | A | O |
| ATOM | 2712 | N | LYS | A | 178 | 75.938 | −37.941 | 16.015 | 1.00 | 27.13 | A | N |
| ATOM | 2713 | CA | LYS | A | 178 | 75.639 | −36.526 | 16.218 | 1.00 | 26.85 | A | C |
| ATOM | 2715 | CB | LYS | A | 178 | 76.934 | −35.721 | 16.371 | 1.00 | 27.05 | A | C |
| ATOM | 2718 | CG | LYS | A | 178 | 76.737 | −34.303 | 16.900 | 1.00 | 27.43 | A | C |
| ATOM | 2721 | CD | LYS | A | 178 | 78.075 | −33.632 | 17.203 | 1.00 | 27.38 | A | C |
| ATOM | 2724 | CE | LYS | A | 178 | 77.917 | −32.490 | 18.197 | 1.00 | 27.26 | A | C |
| ATOM | 2727 | NZ | LYS | A | 178 | 79.230 | −31.954 | 18.642 | 1.00 | 27.88 | A | N |
| ATOM | 2731 | C | LYS | A | 178 | 74.822 | −35.984 | 15.048 | 1.00 | 26.49 | A | C |
| ATOM | 2732 | O | LYS | A | 178 | 73.928 | −35.161 | 15.238 | 1.00 | 26.01 | A | O |
| ATOM | 2734 | N | GLU | A | 179 | 75.130 | −36.465 | 13.843 | 1.00 | 26.38 | A | N |
| ATOM | 2735 | CA | GLU | A | 179 | 74.427 | −36.033 | 12.635 | 1.00 | 26.59 | A | C |
| ATOM | 2737 | CB | GLU | A | 179 | 75.284 | −36.264 | 11.379 | 1.00 | 26.76 | A | C |
| ATOM | 2740 | CG | GLU | A | 179 | 75.652 | −37.715 | 11.067 | 1.00 | 27.14 | A | C |
| ATOM | 2743 | CD | GLU | A | 179 | 76.355 | −37.860 | 9.721 | 1.00 | 27.77 | A | C |
| ATOM | 2744 | OE1 | GLU | A | 179 | 76.641 | −39.008 | 9.321 | 1.00 | 29.07 | A | O |
| ATOM | 2745 | OE2 | GLU | A | 179 | 76.623 | −36.833 | 9.060 | 1.00 | 27.01 | A | O |
| ATOM | 2746 | C | GLU | A | 179 | 73.033 | −36.657 | 12.469 | 1.00 | 26.24 | A | C |
| ATOM | 2747 | O | GLU | A | 179 | 72.139 | −36.021 | 11.903 | 1.00 | 26.60 | A | O |
| ATOM | 2749 | N | LEU | A | 180 | 72.846 | −37.887 | 12.949 | 1.00 | 25.43 | A | N |
| ATOM | 2750 | CA | LEU | A | 180 | 71.525 | −38.531 | 12.901 | 1.00 | 24.84 | A | C |
| ATOM | 2752 | CB | LEU | A | 180 | 71.613 | −40.033 | 13.201 | 1.00 | 24.93 | A | C |
| ATOM | 2755 | CG | LEU | A | 180 | 71.959 | −40.949 | 12.023 | 1.00 | 25.07 | A | C |
| ATOM | 2757 | CD1 | LEU | A | 180 | 72.178 | −42.374 | 12.519 | 1.00 | 24.77 | A | C |
| ATOM | 2761 | CD2 | LEU | A | 180 | 70.874 | −40.911 | 10.949 | 1.00 | 23.22 | A | C |
| ATOM | 2765 | C | LEU | A | 180 | 70.549 | −37.866 | 13.866 | 1.00 | 24.29 | A | C |
| ATOM | 2766 | O | LEU | A | 180 | 69.380 | −37.671 | 13.531 | 1.00 | 24.25 | A | O |
| ATOM | 2768 | N | ALA | A | 181 | 71.031 | −37.522 | 15.058 | 1.00 | 23.73 | A | N |
| ATOM | 2769 | CA | ALA | A | 181 | 70.229 | −36.777 | 16.031 | 1.00 | 23.30 | A | C |
| ATOM | 2771 | CB | ALA | A | 181 | 71.011 | −36.575 | 17.321 | 1.00 | 23.36 | A | C |
| ATOM | 2775 | C | ALA | A | 181 | 69.789 | −35.428 | 15.462 | 1.00 | 22.75 | A | C |
| ATOM | 2776 | O | ALA | A | 181 | 68.650 | −35.010 | 15.655 | 1.00 | 22.37 | A | O |
| ATOM | 2778 | N | GLU | A | 182 | 70.702 | −34.758 | 14.762 | 1.00 | 22.59 | A | N |
| ATOM | 2779 | CA | GLU | A | 182 | 70.399 | −33.493 | 14.088 | 1.00 | 22.35 | A | C |
| ATOM | 2781 | CB | GLU | A | 182 | 71.677 | −32.858 | 13.517 | 1.00 | 22.71 | A | C |
| ATOM | 2784 | CG | GLU | A | 182 | 72.564 | −32.200 | 14.578 | 1.00 | 24.48 | A | C |
| ATOM | 2787 | CD | GLU | A | 182 | 73.892 | −31.690 | 14.031 | 1.00 | 25.90 | A | C |
| ATOM | 2788 | OE1 | GLU | A | 182 | 74.533 | −32.407 | 13.229 | 1.00 | 26.63 | A | O |

TABLE 8-2-continued

Coordinates for L494P Structure

| ATOM | 2789 | OE2 | GLU | A | 182 | 74.302 | −30.573 | 14.418 | 1.00 | 25.24 | A | O |
|---|---|---|---|---|---|---|---|---|---|---|---|---|
| ATOM | 2790 | C | GLU | A | 182 | 69.371 | −33.694 | 12.980 | 1.00 | 21.48 | A | C |
| ATOM | 2791 | O | GLU | A | 182 | 68.562 | −32.806 | 12.712 | 1.00 | 21.64 | A | O |
| ATOM | 2793 | N | GLN | A | 183 | 69.408 | −34.862 | 12.345 | 1.00 | 20.42 | A | N |
| ATOM | 2794 | CA | GLN | A | 183 | 68.426 | −35.223 | 11.328 | 1.00 | 19.78 | A | C |
| ATOM | 2796 | CB | GLN | A | 183 | 68.890 | −36.458 | 10.548 | 1.00 | 19.69 | A | C |
| ATOM | 2799 | CG | GLN | A | 183 | 68.480 | −36.456 | 9.080 | 1.00 | 20.17 | A | C |
| ATOM | 2802 | CD | GLN | A | 183 | 69.261 | −35.455 | 8.240 | 1.00 | 19.79 | A | C |
| ATOM | 2803 | OE1 | GLN | A | 183 | 68.826 | −35.068 | 7.154 | 1.00 | 18.23 | A | O |
| ATOM | 2804 | NE2 | GLN | A | 183 | 70.419 | −35.035 | 8.737 | 1.00 | 21.56 | A | N |
| ATOM | 2807 | C | GLN | A | 183 | 67.065 | −35.499 | 11.973 | 1.00 | 19.19 | A | C |
| ATOM | 2808 | O | GLN | A | 183 | 66.025 | −35.090 | 11.450 | 1.00 | 18.90 | A | O |
| ATOM | 2810 | N | VAL | A | 184 | 67.084 | −36.194 | 13.108 | 1.00 | 18.65 | A | N |
| ATOM | 2811 | CA | VAL | A | 184 | 65.863 | −36.523 | 13.844 | 1.00 | 18.22 | A | C |
| ATOM | 2813 | CB | VAL | A | 184 | 66.131 | −37.581 | 14.940 | 1.00 | 18.01 | A | C |
| ATOM | 2815 | CG1 | VAL | A | 184 | 66.397 | −38.935 | 14.306 | 1.00 | 17.80 | A | C |
| ATOM | 2819 | CG2 | VAL | A | 184 | 64.960 | −37.673 | 15.903 | 1.00 | 17.60 | A | C |
| ATOM | 2823 | C | VAL | A | 184 | 65.237 | −35.280 | 14.471 | 1.00 | 18.09 | A | C |
| ATOM | 2824 | O | VAL | A | 184 | 64.024 | −35.091 | 14.389 | 1.00 | 18.22 | A | O |
| ATOM | 2826 | N | ASN | A | 185 | 66.066 | −34.443 | 15.094 | 1.00 | 18.01 | A | N |
| ATOM | 2827 | CA | ASN | A | 185 | 65.602 | −33.185 | 15.689 | 1.00 | 18.08 | A | C |
| ATOM | 2829 | CB | ASN | A | 185 | 66.741 | −32.481 | 16.437 | 1.00 | 18.30 | A | C |
| ATOM | 2832 | CG | ASN | A | 185 | 67.082 | −33.151 | 17.759 | 1.00 | 18.99 | A | C |
| ATOM | 2833 | OD1 | ASN | A | 185 | 66.855 | −34.347 | 17.947 | 1.00 | 20.86 | A | O |
| ATOM | 2834 | ND2 | ASN | A | 185 | 67.634 | −32.376 | 18.684 | 1.00 | 19.63 | A | N |
| ATOM | 2837 | C | ASN | A | 185 | 65.010 | −32.239 | 14.646 | 1.00 | 18.07 | A | C |
| ATOM | 2838 | O | ASN | A | 185 | 64.042 | −31.531 | 14.923 | 1.00 | 17.94 | A | O |
| ATOM | 2840 | N | HIS | A | 186 | 65.600 | −32.235 | 13.453 | 1.00 | 18.13 | A | N |
| ATOM | 2841 | CA | HIS | A | 186 | 65.084 | −31.459 | 12.322 | 1.00 | 18.18 | A | C |
| ATOM | 2843 | CB | HIS | A | 186 | 66.104 | −31.468 | 11.180 | 1.00 | 17.97 | A | C |
| ATOM | 2846 | CG | HIS | A | 186 | 65.745 | −30.580 | 10.028 | 1.00 | 16.43 | A | C |
| ATOM | 2847 | ND1 | HIS | A | 186 | 65.727 | −29.205 | 10.126 | 1.00 | 14.28 | A | N |
| ATOM | 2849 | CE1 | HIS | A | 186 | 65.396 | −28.688 | 8.956 | 1.00 | 13.38 | A | C |
| ATOM | 2851 | NE2 | HIS | A | 186 | 65.205 | −29.678 | 8.102 | 1.00 | 14.26 | A | N |
| ATOM | 2853 | CD2 | HIS | A | 186 | 65.423 | −30.871 | 8.746 | 1.00 | 14.62 | A | C |
| ATOM | 2855 | C | HIS | A | 186 | 63.741 | −32.012 | 11.834 | 1.00 | 18.27 | A | C |
| ATOM | 2856 | O | HIS | A | 186 | 62.784 | −31.261 | 11.657 | 1.00 | 18.39 | A | O |
| ATOM | 2858 | N | ALA | A | 187 | 63.679 | −33.325 | 11.625 | 1.00 | 18.10 | A | N |
| ATOM | 2859 | CA | ALA | A | 187 | 62.454 | −33.979 | 11.159 | 1.00 | 17.75 | A | C |
| ATOM | 2861 | CB | ALA | A | 187 | 62.726 | −35.439 | 10.848 | 1.00 | 17.93 | A | C |
| ATOM | 2865 | C | ALA | A | 187 | 61.315 | −33.859 | 12.173 | 1.00 | 17.45 | A | C |
| ATOM | 2866 | O | ALA | A | 187 | 60.161 | −33.643 | 11.797 | 1.00 | 17.00 | A | O |
| ATOM | 2868 | N | LEU | A | 188 | 61.646 | −33.998 | 13.456 | 1.00 | 17.36 | A | N |
| ATOM | 2869 | CA | LEU | A | 188 | 60.648 | −33.889 | 14.526 | 1.00 | 17.21 | A | C |
| ATOM | 2871 | CB | LEU | A | 188 | 61.154 | −34.531 | 15.826 | 1.00 | 16.89 | A | C |
| ATOM | 2874 | CG | LEU | A | 188 | 61.033 | −36.059 | 15.872 | 1.00 | 16.43 | A | C |
| ATOM | 2876 | CD1 | LEU | A | 188 | 61.936 | −36.663 | 16.933 | 1.00 | 15.33 | A | C |
| ATOM | 2880 | CD2 | LEU | A | 188 | 59.586 | −36.471 | 16.107 | 1.00 | 16.80 | A | C |
| ATOM | 2884 | C | LEU | A | 188 | 60.216 | −32.442 | 14.773 | 1.00 | 17.11 | A | C |
| ATOM | 2885 | O | LEU | A | 188 | 59.104 | −32.205 | 15.245 | 1.00 | 17.54 | A | O |
| ATOM | 2887 | N | GLU | A | 189 | 61.088 | −31.484 | 14.462 | 1.00 | 16.53 | A | N |
| ATOM | 2888 | CA | GLU | A | 189 | 60.711 | −30.071 | 14.493 | 1.00 | 16.03 | A | C |
| ATOM | 2890 | CB | GLU | A | 189 | 61.894 | −29.181 | 14.088 | 1.00 | 16.08 | A | C |
| ATOM | 2893 | CG | GLU | A | 189 | 61.639 | −27.679 | 14.221 | 1.00 | 17.05 | A | C |
| ATOM | 2896 | CD | GLU | A | 189 | 62.570 | −26.845 | 13.357 | 1.00 | 18.24 | A | C |
| ATOM | 2897 | OE1 | GLU | A | 189 | 62.631 | −27.099 | 12.136 | 1.00 | 18.22 | A | O |
| ATOM | 2898 | OE2 | GLU | A | 189 | 63.229 | −25.927 | 13.893 | 1.00 | 18.67 | A | O |
| ATOM | 2899 | C | GLU | A | 189 | 59.554 | −29.859 | 13.527 | 1.00 | 15.30 | A | C |
| ATOM | 2900 | O | GLU | A | 189 | 58.502 | −29.345 | 13.901 | 1.00 | 14.88 | A | O |
| ATOM | 2902 | N | LEU | A | 190 | 59.773 | −30.280 | 12.284 | 1.00 | 14.95 | A | N |
| ATOM | 2903 | CA | LEU | A | 190 | 58.806 | −30.145 | 11.203 | 1.00 | 14.48 | A | C |
| ATOM | 2905 | CB | LEU | A | 190 | 58.730 | −28.685 | 10.740 | 1.00 | 14.32 | A | C |
| ATOM | 2908 | CG | LEU | A | 190 | 57.637 | −28.308 | 9.735 | 1.00 | 13.70 | A | C |
| ATOM | 2910 | CD1 | LEU | A | 190 | 56.257 | −28.398 | 10.377 | 1.00 | 12.88 | A | C |
| ATOM | 2914 | CD2 | LEU | A | 190 | 57.885 | −26.909 | 9.175 | 1.00 | 9.41 | A | C |
| ATOM | 2918 | C | LEU | A | 190 | 59.281 | −31.037 | 10.057 | 1.00 | 14.33 | A | C |
| ATOM | 2919 | O | LEU | A | 190 | 60.460 | −31.011 | 9.711 | 1.00 | 14.00 | A | O |
| ATOM | 2921 | N | PRO | A | 191 | 58.379 | −31.839 | 9.468 | 1.00 | 14.65 | A | N |
| ATOM | 2922 | CA | PRO | A | 191 | 58.827 | −32.779 | 8.437 | 1.00 | 14.74 | A | C |
| ATOM | 2924 | CB | PRO | A | 191 | 57.674 | −33.777 | 8.358 | 1.00 | 14.70 | A | C |
| ATOM | 2927 | CG | PRO | A | 191 | 56.473 | −32.971 | 8.707 | 1.00 | 15.26 | A | C |
| ATOM | 2930 | CD | PRO | A | 191 | 56.918 | −31.887 | 9.655 | 1.00 | 14.91 | A | C |
| ATOM | 2933 | C | PRO | A | 191 | 59.059 | −32.111 | 7.082 | 1.00 | 14.61 | A | C |
| ATOM | 2934 | O | PRO | A | 191 | 58.725 | −30.941 | 6.903 | 1.00 | 15.11 | A | O |
| ATOM | 2935 | N | LEU | A | 192 | 59.624 | −32.860 | 6.142 | 1.00 | 14.26 | A | N |
| ATOM | 2936 | CA | LEU | A | 192 | 59.935 | −32.339 | 4.814 | 1.00 | 13.99 | A | C |
| ATOM | 2938 | CB | LEU | A | 192 | 60.580 | −33.424 | 3.950 | 1.00 | 14.19 | A | C |
| ATOM | 2941 | CG | LEU | A | 192 | 61.980 | −33.866 | 4.391 | 1.00 | 16.27 | A | C |

TABLE 8-2-continued

Coordinates for L494P Structure

| ATOM | 2943 | CD1 | LEU | A | 192 | 62.353 | −35.200 | 3.765 | 1.00 | 17.03 | A | C |
|---|---|---|---|---|---|---|---|---|---|---|---|---|
| ATOM | 2947 | CD2 | LEU | A | 192 | 63.019 | −32.803 | 4.053 | 1.00 | 17.29 | A | C |
| ATOM | 2951 | C | LEU | A | 192 | 58.688 | −31.817 | 4.122 | 1.00 | 13.36 | A | C |
| ATOM | 2952 | O | LEU | A | 192 | 58.662 | −30.679 | 3.661 | 1.00 | 13.23 | A | O |
| ATOM | 2954 | N | HIS | A | 193 | 57.651 | −32.649 | 4.086 | 1.00 | 13.28 | A | N |
| ATOM | 2955 | CA | HIS | A | 193 | 56.421 | −32.355 | 3.343 | 1.00 | 13.38 | A | C |
| ATOM | 2957 | CB | HIS | A | 193 | 55.449 | −33.537 | 3.458 | 1.00 | 13.14 | A | C |
| ATOM | 2960 | CG | HIS | A | 193 | 54.224 | −33.402 | 2.608 | 1.00 | 12.08 | A | C |
| ATOM | 2961 | ND1 | HIS | A | 193 | 54.279 | −33.279 | 1.237 | 1.00 | 11.82 | A | N |
| ATOM | 2963 | CE1 | HIS | A | 193 | 53.053 | −33.178 | 0.757 | 1.00 | 11.83 | A | C |
| ATOM | 2965 | NE2 | HIS | A | 193 | 52.204 | −33.235 | 1.767 | 1.00 | 9.95 | A | N |
| ATOM | 2967 | CD2 | HIS | A | 193 | 52.910 | −33.375 | 2.936 | 1.00 | 10.22 | A | C |
| ATOM | 2969 | C | HIS | A | 193 | 55.722 | −31.055 | 3.764 | 1.00 | 13.92 | A | C |
| ATOM | 2970 | O | HIS | A | 193 | 54.964 | −30.478 | 2.979 | 1.00 | 13.67 | A | O |
| ATOM | 2972 | N | ARG | A | 194 | 55.971 | −30.598 | 4.989 | 1.00 | 14.56 | A | N |
| ATOM | 2973 | CA | ARG | A | 194 | 55.393 | −29.343 | 5.475 | 1.00 | 15.25 | A | C |
| ATOM | 2975 | CB | ARG | A | 194 | 54.749 | −29.557 | 6.843 | 1.00 | 15.26 | A | C |
| ATOM | 2978 | CG | ARG | A | 194 | 53.625 | −30.571 | 6.824 | 1.00 | 16.11 | A | C |
| ATOM | 2981 | CD | ARG | A | 194 | 52.888 | −30.620 | 8.150 | 1.00 | 18.42 | A | C |
| ATOM | 2984 | NE | ARG | A | 194 | 51.885 | −31.684 | 8.170 | 1.00 | 19.85 | A | N |
| ATOM | 2986 | CZ | ARG | A | 194 | 51.170 | −32.042 | 9.236 | 1.00 | 20.13 | A | C |
| ATOM | 2987 | NH1 | ARG | A | 194 | 51.330 | −31.431 | 10.406 | 1.00 | 21.48 | A | N |
| ATOM | 2990 | NH2 | ARG | A | 194 | 50.288 | −33.028 | 9.132 | 1.00 | 20.98 | A | N |
| ATOM | 2993 | C | ARG | A | 194 | 56.392 | −28.180 | 5.542 | 1.00 | 15.65 | A | C |
| ATOM | 2994 | O | ARG | A | 194 | 55.981 | −27.029 | 5.629 | 1.00 | 16.13 | A | O |
| ATOM | 2996 | N | ARG | A | 195 | 57.691 | −28.468 | 5.501 | 1.00 | 15.83 | A | N |
| ATOM | 2997 | CA | ARG | A | 195 | 58.707 | −27.416 | 5.544 | 1.00 | 15.92 | A | C |
| ATOM | 2999 | CB | ARG | A | 195 | 60.047 | −27.994 | 5.992 | 1.00 | 16.22 | A | C |
| ATOM | 3002 | CG | ARG | A | 195 | 61.069 | −26.938 | 6.388 | 1.00 | 18.02 | A | C |
| ATOM | 3005 | CD | ARG | A | 195 | 62.434 | −27.540 | 6.681 | 1.00 | 18.19 | A | C |
| ATOM | 3008 | NE | ARG | A | 195 | 62.382 | −28.612 | 7.672 | 1.00 | 19.14 | A | N |
| ATOM | 3010 | CZ | ARG | A | 195 | 62.233 | −28.434 | 8.984 | 1.00 | 21.01 | A | C |
| ATOM | 3011 | NH1 | ARG | A | 195 | 62.104 | −27.216 | 9.507 | 1.00 | 20.62 | A | N |
| ATOM | 3014 | NH2 | ARG | A | 195 | 62.212 | −29.490 | 9.788 | 1.00 | 22.42 | A | N |
| ATOM | 3017 | C | ARG | A | 195 | 58.866 | −26.768 | 4.171 | 1.00 | 15.95 | A | C |
| ATOM | 3018 | O | ARG | A | 195 | 58.929 | −27.471 | 3.158 | 1.00 | 15.90 | A | O |
| ATOM | 3020 | N | THR | A | 196 | 58.946 | −25.436 | 4.133 | 1.00 | 15.87 | A | N |
| ATOM | 3021 | CA | THR | A | 196 | 59.146 | −24.725 | 2.866 | 1.00 | 15.91 | A | C |
| ATOM | 3023 | CB | THR | A | 196 | 59.126 | −23.183 | 3.019 | 1.00 | 15.61 | A | C |
| ATOM | 3025 | OG1 | THR | A | 196 | 60.106 | −22.770 | 3.979 | 1.00 | 15.28 | A | O |
| ATOM | 3027 | CG2 | THR | A | 196 | 57.757 | −22.700 | 3.452 | 1.00 | 15.63 | A | C |
| ATOM | 3031 | C | THR | A | 196 | 60.468 | −25.151 | 2.236 | 1.00 | 16.35 | A | C |
| ATOM | 3032 | O | THR | A | 196 | 61.379 | −25.611 | 2.928 | 1.00 | 16.39 | A | O |
| ATOM | 3034 | N | GLN | A | 197 | 60.562 | −24.986 | 0.922 | 1.00 | 16.60 | A | N |
| ATOM | 3035 | CA | GLN | A | 197 | 61.675 | −25.537 | 0.147 | 1.00 | 16.65 | A | C |
| ATOM | 3037 | CB | GLN | A | 197 | 61.292 | −25.578 | −1.344 | 1.00 | 16.83 | A | C |
| ATOM | 3040 | CG | GLN | A | 197 | 62.268 | −24.945 | −2.318 | 1.00 | 18.46 | A | C |
| ATOM | 3043 | CD | GLN | A | 197 | 63.359 | −25.875 | −2.795 | 1.00 | 19.11 | A | C |
| ATOM | 3044 | OE1 | GLN | A | 197 | 64.519 | −25.716 | −2.426 | 1.00 | 18.91 | A | O |
| ATOM | 3045 | NE2 | GLN | A | 197 | 62.997 | −26.839 | −3.639 | 1.00 | 19.88 | A | N |
| ATOM | 3048 | C | GLN | A | 197 | 63.023 | −24.834 | 0.399 | 1.00 | 16.45 | A | C |
| ATOM | 3049 | O | GLN | A | 197 | 64.073 | −25.476 | 0.344 | 1.00 | 16.57 | A | O |
| ATOM | 3051 | N | ARG | A | 198 | 62.990 | −23.535 | 0.692 | 1.00 | 16.22 | A | N |
| ATOM | 3052 | CA | ARG | A | 198 | 64.219 | −22.767 | 0.939 | 1.00 | 15.80 | A | C |
| ATOM | 3054 | CB | ARG | A | 198 | 63.960 | −21.270 | 0.758 | 1.00 | 15.86 | A | C |
| ATOM | 3057 | CG | ARG | A | 198 | 63.690 | −20.856 | −0.682 | 1.00 | 16.65 | A | C |
| ATOM | 3060 | CD | ARG | A | 198 | 64.967 | −20.804 | −1.526 | 1.00 | 16.78 | A | C |
| ATOM | 3063 | NE | ARG | A | 198 | 65.295 | −22.072 | −2.175 | 1.00 | 16.13 | A | N |
| ATOM | 3065 | CZ | ARG | A | 198 | 66.289 | −22.234 | −3.048 | 1.00 | 18.48 | A | C |
| ATOM | 3066 | NH1 | ARG | A | 198 | 67.067 | −21.209 | −3.393 | 1.00 | 17.78 | A | N |
| ATOM | 3069 | NH2 | ARG | A | 198 | 66.511 | −23.431 | −3.585 | 1.00 | 19.12 | A | N |
| ATOM | 3072 | C | ARG | A | 198 | 64.819 | −23.027 | 2.324 | 1.00 | 15.17 | A | C |
| ATOM | 3073 | O | ARG | A | 198 | 66.032 | −23.193 | 2.452 | 1.00 | 14.96 | A | O |
| ATOM | 3075 | N | LEU | A | 199 | 63.974 | −23.051 | 3.354 | 1.00 | 14.66 | A | N |
| ATOM | 3076 | CA | LEU | A | 199 | 64.425 | −23.342 | 4.719 | 1.00 | 14.28 | A | C |
| ATOM | 3078 | CB | LEU | A | 199 | 63.290 | −23.155 | 5.738 | 1.00 | 14.42 | A | C |
| ATOM | 3081 | CG | LEU | A | 199 | 62.996 | −21.723 | 6.198 | 1.00 | 13.58 | A | C |
| ATOM | 3083 | CD1 | LEU | A | 199 | 64.225 | −21.108 | 6.838 | 1.00 | 12.91 | A | C |
| ATOM | 3087 | CD2 | LEU | A | 199 | 61.823 | −21.698 | 7.166 | 1.00 | 11.52 | A | C |
| ATOM | 3091 | C | LEU | A | 199 | 64.973 | −24.760 | 4.820 | 1.00 | 13.99 | A | C |
| ATOM | 3092 | O | LEU | A | 199 | 65.941 | −25.007 | 5.542 | 1.00 | 13.43 | A | O |
| ATOM | 3094 | N | GLU | A | 200 | 64.338 | −25.686 | 4.105 | 1.00 | 13.99 | A | N |
| ATOM | 3095 | CA | GLU | A | 200 | 64.840 | −27.052 | 3.993 | 1.00 | 14.04 | A | C |
| ATOM | 3097 | CB | GLU | A | 200 | 63.833 | −27.945 | 3.254 | 1.00 | 14.26 | A | C |
| ATOM | 3100 | CG | GLU | A | 200 | 64.284 | −29.393 | 3.026 | 1.00 | 15.07 | A | C |
| ATOM | 3103 | CD | GLU | A | 200 | 64.864 | −30.053 | 4.267 | 1.00 | 16.59 | A | C |
| ATOM | 3104 | OE1 | GLU | A | 200 | 64.228 | −29.992 | 5.341 | 1.00 | 18.96 | A | O |
| ATOM | 3105 | OE2 | GLU | A | 200 | 65.957 | −30.646 | 4.165 | 1.00 | 16.21 | A | O |

TABLE 8-2-continued

Coordinates for L494P Structure

| ATOM | 3106 | C | GLU | A | 200 | 66.176 | −27.051 | 3.263 | 1.00 | 13.82 | A | C |
|---|---|---|---|---|---|---|---|---|---|---|---|---|
| ATOM | 3107 | O | GLU | A | 200 | 67.090 | −27.786 | 3.640 | 1.00 | 14.49 | A | O |
| ATOM | 3109 | N | ALA | A | 201 | 66.283 | −26.220 | 2.226 | 1.00 | 13.15 | A | N |
| ATOM | 3110 | CA | ALA | A | 201 | 67.510 | −26.108 | 1.437 | 1.00 | 12.65 | A | C |
| ATOM | 3112 | CB | ALA | A | 201 | 67.272 | −25.238 | 0.221 | 1.00 | 12.47 | A | C |
| ATOM | 3116 | C | ALA | A | 201 | 68.696 | −25.576 | 2.249 | 1.00 | 12.48 | A | C |
| ATOM | 3117 | O | ALA | A | 201 | 69.755 | −26.200 | 2.272 | 1.00 | 12.06 | A | O |
| ATOM | 3119 | N | VAL | A | 202 | 68.515 | −24.439 | 2.922 | 1.00 | 12.67 | A | N |
| ATOM | 3120 | CA | VAL | A | 202 | 69.609 | −23.801 | 3.673 | 1.00 | 12.57 | A | C |
| ATOM | 3122 | CB | VAL | A | 202 | 69.196 | −22.440 | 4.277 | 1.00 | 12.42 | A | C |
| ATOM | 3124 | CG1 | VAL | A | 202 | 68.324 | −22.635 | 5.506 | 1.00 | 12.80 | A | C |
| ATOM | 3128 | CG2 | VAL | A | 202 | 70.426 | −21.626 | 4.635 | 1.00 | 12.02 | A | C |
| ATOM | 3132 | C | VAL | A | 202 | 70.130 | −24.682 | 4.800 | 1.00 | 12.80 | A | C |
| ATOM | 3133 | O | VAL | A | 202 | 71.296 | −24.580 | 5.176 | 1.00 | 12.89 | A | O |
| ATOM | 3135 | N | TRP | A | 203 | 69.261 | −25.537 | 5.336 | 1.00 | 13.26 | A | N |
| ATOM | 3136 | CA | TRP | A | 203 | 69.638 | −26.478 | 6.385 | 1.00 | 13.35 | A | C |
| ATOM | 3138 | CB | TRP | A | 203 | 68.399 | −26.965 | 7.140 | 1.00 | 13.36 | A | C |
| ATOM | 3141 | CG | TRP | A | 203 | 68.720 | −27.817 | 8.329 | 1.00 | 12.25 | A | C |
| ATOM | 3142 | CD1 | TRP | A | 203 | 68.960 | −27.387 | 9.601 | 1.00 | 12.59 | A | C |
| ATOM | 3144 | NE1 | TRP | A | 203 | 69.219 | −28.456 | 10.421 | 1.00 | 11.51 | A | N |
| ATOM | 3146 | CE2 | TRP | A | 203 | 69.152 | −29.607 | 9.683 | 1.00 | 10.81 | A | C |
| ATOM | 3147 | CD2 | TRP | A | 203 | 68.837 | −29.242 | 8.358 | 1.00 | 11.23 | A | C |
| ATOM | 3148 | CE3 | TRP | A | 203 | 68.706 | −30.247 | 7.393 | 1.00 | 12.78 | A | C |
| ATOM | 3150 | CZ3 | TRP | A | 203 | 68.893 | −31.567 | 7.778 | 1.00 | 12.64 | A | C |
| ATOM | 3152 | CH2 | TRP | A | 203 | 69.205 | −31.897 | 9.107 | 1.00 | 11.26 | A | C |
| ATOM | 3154 | CZ2 | TRP | A | 203 | 69.339 | −30.934 | 10.069 | 1.00 | 10.95 | A | C |
| ATOM | 3156 | C | TRP | A | 203 | 70.379 | −27.670 | 5.795 | 1.00 | 13.47 | A | C |
| ATOM | 3157 | O | TRP | A | 203 | 71.515 | −27.954 | 6.183 | 1.00 | 13.39 | A | O |
| ATOM | 3159 | N | SER | A | 204 | 69.730 | −28.355 | 4.852 | 1.00 | 13.61 | A | N |
| ATOM | 3160 | CA | SER | A | 204 | 70.270 | −29.589 | 4.263 | 1.00 | 13.87 | A | C |
| ATOM | 3162 | CB | SER | A | 204 | 69.323 | −30.142 | 3.194 | 1.00 | 13.67 | A | C |
| ATOM | 3165 | OG | SER | A | 204 | 68.234 | −30.819 | 3.792 | 1.00 | 13.52 | A | O |
| ATOM | 3167 | C | SER | A | 204 | 71.666 | −29.407 | 3.674 | 1.00 | 14.22 | A | C |
| ATOM | 3168 | O | SER | A | 204 | 72.476 | −30.333 | 3.708 | 1.00 | 14.33 | A | O |
| ATOM | 3170 | N | ILE | A | 205 | 71.933 | −28.216 | 3.139 | 1.00 | 14.32 | A | N |
| ATOM | 3171 | CA | ILE | A | 205 | 73.259 | −27.852 | 2.639 | 1.00 | 14.23 | A | C |
| ATOM | 3173 | CB | ILE | A | 205 | 73.234 | −26.458 | 1.967 | 1.00 | 14.07 | A | C |
| ATOM | 3175 | CG1 | ILE | A | 205 | 72.473 | −26.517 | 0.643 | 1.00 | 13.44 | A | C |
| ATOM | 3178 | CD1 | ILE | A | 205 | 72.074 | −25.161 | 0.117 | 1.00 | 12.73 | A | C |
| ATOM | 3182 | CG2 | ILE | A | 205 | 74.647 | −25.947 | 1.718 | 1.00 | 15.49 | A | C |
| ATOM | 3186 | C | ILE | A | 205 | 74.292 | −27.845 | 3.769 | 1.00 | 14.47 | A | C |
| ATOM | 3187 | O | ILE | A | 205 | 75.347 | −28.479 | 3.663 | 1.00 | 14.24 | A | O |
| ATOM | 3189 | N | GLU | A | 206 | 73.975 | −27.126 | 4.846 | 1.00 | 14.66 | A | N |
| ATOM | 3190 | CA | GLU | A | 206 | 74.842 | −27.051 | 6.023 | 1.00 | 14.82 | A | C |
| ATOM | 3192 | CB | GLU | A | 206 | 74.219 | −26.131 | 7.082 | 1.00 | 15.15 | A | C |
| ATOM | 3195 | CG | GLU | A | 206 | 75.064 | −25.916 | 8.346 | 1.00 | 16.59 | A | C |
| ATOM | 3198 | CD | GLU | A | 206 | 76.420 | −25.279 | 8.071 | 1.00 | 17.90 | A | C |
| ATOM | 3199 | OE1 | GLU | A | 206 | 76.582 | −24.629 | 7.014 | 1.00 | 19.11 | A | O |
| ATOM | 3200 | OE2 | GLU | A | 206 | 77.325 | −25.424 | 8.922 | 1.00 | 18.61 | A | O |
| ATOM | 3201 | C | GLU | A | 206 | 75.094 | −28.436 | 6.616 | 1.00 | 14.53 | A | C |
| ATOM | 3202 | O | GLU | A | 206 | 76.197 | −28.730 | 7.072 | 1.00 | 14.36 | A | O |
| ATOM | 3204 | N | ALA | A | 207 | 74.063 | −29.277 | 6.604 | 1.00 | 14.37 | A | N |
| ATOM | 3205 | CA | ALA | A | 207 | 74.173 | −30.655 | 7.079 | 1.00 | 14.14 | A | C |
| ATOM | 3207 | CB | ALA | A | 207 | 72.785 | −31.266 | 7.234 | 1.00 | 14.13 | A | C |
| ATOM | 3211 | C | ALA | A | 207 | 75.015 | −31.514 | 6.141 | 1.00 | 13.78 | A | C |
| ATOM | 3212 | O | ALA | A | 207 | 75.898 | −32.248 | 6.585 | 1.00 | 13.22 | A | O |
| ATOM | 3214 | N | TYR | A | 208 | 74.733 | −31.410 | 4.845 | 1.00 | 13.95 | A | N |
| ATOM | 3215 | CA | TYR | A | 208 | 75.319 | −32.297 | 3.838 | 1.00 | 14.17 | A | C |
| ATOM | 3217 | CB | TYR | A | 208 | 74.531 | −32.189 | 2.525 | 1.00 | 14.20 | A | C |
| ATOM | 3220 | CG | TYR | A | 208 | 74.881 | −33.219 | 1.471 | 1.00 | 13.85 | A | C |
| ATOM | 3221 | CD1 | TYR | A | 208 | 74.401 | −34.523 | 1.557 | 1.00 | 15.48 | A | C |
| ATOM | 3223 | CE1 | TYR | A | 208 | 74.710 | −35.472 | 0.583 | 1.00 | 15.09 | A | C |
| ATOM | 3225 | CZ | TYR | A | 208 | 75.500 | −35.115 | −0.494 | 1.00 | 13.90 | A | C |
| ATOM | 3226 | OH | TYR | A | 208 | 75.811 | −36.045 | −1.458 | 1.00 | 11.21 | A | O |
| ATOM | 3228 | CE2 | TYR | A | 208 | 75.984 | −33.823 | −0.604 | 1.00 | 14.12 | A | C |
| ATOM | 3230 | CD2 | TYR | A | 208 | 75.670 | −32.882 | 0.375 | 1.00 | 13.38 | A | C |
| ATOM | 3232 | C | TYR | A | 208 | 76.804 | −32.031 | 3.588 | 1.00 | 14.31 | A | C |
| ATOM | 3233 | O | TYR | A | 208 | 77.515 | −32.918 | 3.120 | 1.00 | 14.93 | A | O |
| ATOM | 3235 | N | ARG | A | 209 | 77.276 | −30.825 | 3.892 | 1.00 | 14.14 | A | N |
| ATOM | 3236 | CA | ARG | A | 209 | 78.691 | −30.508 | 3.698 | 1.00 | 14.20 | A | C |
| ATOM | 3238 | CB | ARG | A | 209 | 78.912 | −28.994 | 3.580 | 1.00 | 14.05 | A | C |
| ATOM | 3241 | CG | ARG | A | 209 | 78.753 | −28.202 | 4.872 | 1.00 | 14.18 | A | C |
| ATOM | 3244 | CD | ARG | A | 209 | 79.424 | −26.841 | 4.766 | 1.00 | 14.24 | A | C |
| ATOM | 3247 | NE | ARG | A | 209 | 78.659 | −25.905 | 3.944 | 1.00 | 13.50 | A | N |
| ATOM | 3249 | CZ | ARG | A | 209 | 79.136 | −24.767 | 3.440 | 1.00 | 12.08 | A | C |
| ATOM | 3250 | NH1 | ARG | A | 209 | 80.397 | −24.399 | 3.650 | 1.00 | 10.79 | A | N |
| ATOM | 3253 | NH2 | ARG | A | 209 | 78.343 | −23.991 | 2.710 | 1.00 | 12.81 | A | N |
| ATOM | 3256 | C | ARG | A | 209 | 79.571 | −31.108 | 4.802 | 1.00 | 14.55 | A | C |

TABLE 8-2-continued

Coordinates for L494P Structure

| ATOM | 3257 | O | ARG | A | 209 | 80.767 | −31.309 | 4.600 | 1.00 | 14.80 | A | O |
|---|---|---|---|---|---|---|---|---|---|---|---|---|
| ATOM | 3259 | N | LYS | A | 210 | 78.977 | −31.388 | 5.960 | 1.00 | 15.15 | A | N |
| ATOM | 3260 | CA | LYS | A | 210 | 79.694 | −32.011 | 7.076 | 1.00 | 15.61 | A | C |
| ATOM | 3262 | CB | LYS | A | 210 | 79.018 | −31.669 | 8.406 | 1.00 | 15.61 | A | C |
| ATOM | 3265 | CG | LYS | A | 210 | 78.981 | −30.177 | 8.719 | 1.00 | 15.58 | A | C |
| ATOM | 3268 | CD | LYS | A | 210 | 78.026 | −29.867 | 9.865 | 1.00 | 15.71 | A | C |
| ATOM | 3271 | CE | LYS | A | 210 | 77.856 | −28.368 | 10.057 | 1.00 | 15.97 | A | C |
| ATOM | 3274 | NZ | LYS | A | 210 | 76.875 | −28.038 | 11.131 | 1.00 | 15.56 | A | N |
| ATOM | 3278 | C | LYS | A | 210 | 79.795 | −33.531 | 6.911 | 1.00 | 16.30 | A | C |
| ATOM | 3279 | O | LYS | A | 210 | 80.599 | −34.176 | 7.584 | 1.00 | 16.27 | A | O |
| ATOM | 3281 | N | LYS | A | 211 | 78.972 | −34.104 | 6.033 | 1.00 | 17.15 | A | N |
| ATOM | 3282 | CA | LYS | A | 211 | 79.141 | −35.496 | 5.628 | 1.00 | 17.96 | A | C |
| ATOM | 3284 | CB | LYS | A | 211 | 78.049 | −35.934 | 4.644 | 1.00 | 18.23 | A | C |
| ATOM | 3287 | CG | LYS | A | 211 | 76.694 | −36.253 | 5.260 | 1.00 | 19.44 | A | C |
| ATOM | 3290 | CD | LYS | A | 211 | 75.846 | −37.071 | 4.282 | 1.00 | 21.73 | A | C |
| ATOM | 3293 | CE | LYS | A | 211 | 74.424 | −37.282 | 4.784 | 1.00 | 23.25 | A | C |
| ATOM | 3296 | NZ | LYS | A | 211 | 74.388 | −38.036 | 6.071 | 1.00 | 24.71 | A | N |
| ATOM | 3300 | C | LYS | A | 211 | 80.499 | −35.635 | 4.952 | 1.00 | 18.46 | A | C |
| ATOM | 3301 | O | LYS | A | 211 | 80.739 | −35.015 | 3.915 | 1.00 | 18.58 | A | O |
| ATOM | 3303 | N | GLU | A | 212 | 81.383 | −36.442 | 5.534 | 1.00 | 19.08 | A | N |
| ATOM | 3304 | CA | GLU | A | 212 | 82.726 | −36.640 | 4.975 | 1.00 | 19.70 | A | C |
| ATOM | 3306 | CB | GLU | A | 212 | 83.607 | −37.453 | 5.936 | 1.00 | 20.07 | A | C |
| ATOM | 3309 | CG | GLU | A | 212 | 85.113 | −37.304 | 5.683 | 1.00 | 20.44 | A | C |
| ATOM | 3312 | CD | GLU | A | 212 | 85.953 | −38.339 | 6.423 | 1.00 | 20.22 | A | C |
| ATOM | 3313 | OE1 | GLU | A | 212 | 86.981 | −37.951 | 7.016 | 1.00 | 19.88 | A | O |
| ATOM | 3314 | OE2 | GLU | A | 212 | 85.595 | −39.538 | 6.407 | 1.00 | 18.93 | A | O |
| ATOM | 3315 | C | GLU | A | 212 | 82.667 | −37.328 | 3.606 | 1.00 | 19.59 | A | C |
| ATOM | 3316 | O | GLU | A | 212 | 83.540 | −37.119 | 2.763 | 1.00 | 19.49 | A | O |
| ATOM | 3318 | N | ASP | A | 213 | 81.627 | −38.133 | 3.393 | 1.00 | 19.59 | A | N |
| ATOM | 3319 | CA | ASP | A | 213 | 81.420 | −38.841 | 2.128 | 1.00 | 19.85 | A | C |
| ATOM | 3321 | CB | ASP | A | 213 | 80.904 | −40.262 | 2.404 | 1.00 | 20.37 | A | C |
| ATOM | 3324 | CG | ASP | A | 213 | 79.566 | −40.272 | 3.132 | 1.00 | 22.19 | A | C |
| ATOM | 3325 | OD1 | ASP | A | 213 | 79.448 | −39.595 | 4.178 | 1.00 | 23.92 | A | O |
| ATOM | 3326 | OD2 | ASP | A | 213 | 78.636 | −40.959 | 2.660 | 1.00 | 25.96 | A | O |
| ATOM | 3327 | C | ASP | A | 213 | 80.452 | −38.100 | 1.194 | 1.00 | 19.34 | A | C |
| ATOM | 3328 | O | ASP | A | 213 | 79.764 | −38.723 | 0.383 | 1.00 | 19.04 | A | O |
| ATOM | 3330 | N | ALA | A | 214 | 80.412 | −36.773 | 1.299 | 1.00 | 19.11 | A | N |
| ATOM | 3331 | CA | ALA | A | 214 | 79.501 | −35.959 | 0.496 | 1.00 | 19.01 | A | C |
| ATOM | 3333 | CB | ALA | A | 214 | 79.366 | −34.570 | 1.099 | 1.00 | 18.73 | A | C |
| ATOM | 3337 | C | ALA | A | 214 | 79.984 | −35.857 | −0.946 | 1.00 | 19.16 | A | C |
| ATOM | 3338 | O | ALA | A | 214 | 81.188 | −35.779 | −1.198 | 1.00 | 19.39 | A | O |
| ATOM | 3340 | N | ASN | A | 215 | 79.040 | −35.860 | −1.885 | 1.00 | 19.33 | A | N |
| ATOM | 3341 | CA | ASN | A | 215 | 79.354 | −35.675 | −3.302 | 1.00 | 19.51 | A | C |
| ATOM | 3343 | CB | ASN | A | 215 | 78.184 | −36.142 | −4.182 | 1.00 | 19.77 | A | C |
| ATOM | 3346 | CG | ASN | A | 215 | 78.595 | −36.396 | −5.628 | 1.00 | 20.67 | A | C |
| ATOM | 3347 | OD1 | ASN | A | 215 | 78.874 | −35.463 | −6.383 | 1.00 | 22.18 | A | O |
| ATOM | 3348 | ND2 | ASN | A | 215 | 78.623 | −37.666 | −6.019 | 1.00 | 20.55 | A | N |
| ATOM | 3351 | C | ASN | A | 215 | 79.683 | −34.202 | −3.564 | 1.00 | 19.05 | A | C |
| ATOM | 3352 | O | ASN | A | 215 | 78.819 | −33.333 | −3.428 | 1.00 | 19.14 | A | O |
| ATOM | 3354 | N | GLN | A | 216 | 80.934 | −33.932 | −3.932 | 1.00 | 18.33 | A | N |
| ATOM | 3355 | CA | GLN | A | 216 | 81.424 | −32.558 | −4.070 | 1.00 | 17.80 | A | C |
| ATOM | 3357 | CB | GLN | A | 216 | 82.943 | −32.536 | −4.292 | 1.00 | 17.98 | A | C |
| ATOM | 3360 | CG | GLN | A | 216 | 83.771 | −33.244 | −3.213 | 1.00 | 19.00 | A | C |
| ATOM | 3363 | CD | GLN | A | 216 | 83.465 | −32.763 | −1.804 | 1.00 | 19.26 | A | C |
| ATOM | 3364 | OE1 | GLN | A | 216 | 83.323 | −31.565 | −1.560 | 1.00 | 18.93 | A | O |
| ATOM | 3365 | NE2 | GLN | A | 216 | 83.369 | −33.701 | −0.868 | 1.00 | 19.47 | A | N |
| ATOM | 3368 | C | GLN | A | 216 | 80.735 | −31.814 | −5.208 | 1.00 | 17.08 | A | C |
| ATOM | 3369 | O | GLN | A | 216 | 80.432 | −30.627 | −5.080 | 1.00 | 17.09 | A | O |
| ATOM | 3371 | N | VAL | A | 217 | 80.490 | −32.511 | −6.315 | 1.00 | 16.33 | A | N |
| ATOM | 3372 | CA | VAL | A | 217 | 79.826 | −31.912 | −7.474 | 1.00 | 15.80 | A | C |
| ATOM | 3374 | CB | VAL | A | 217 | 79.755 | −32.894 | −8.668 | 1.00 | 15.84 | A | C |
| ATOM | 3376 | CG1 | VAL | A | 217 | 78.935 | −32.298 | −9.809 | 1.00 | 14.63 | A | C |
| ATOM | 3380 | CG2 | VAL | A | 217 | 81.155 | −33.254 | −9.147 | 1.00 | 16.01 | A | C |
| ATOM | 3384 | C | VAL | A | 217 | 78.411 | −31.454 | −7.123 | 1.00 | 15.46 | A | C |
| ATOM | 3385 | O | VAL | A | 217 | 77.999 | −30.355 | −7.500 | 1.00 | 15.60 | A | O |
| ATOM | 3387 | N | LEU | A | 218 | 77.680 | −32.296 | −6.395 | 1.00 | 14.90 | A | N |
| ATOM | 3388 | CA | LEU | A | 218 | 76.300 | −31.998 | −6.009 | 1.00 | 14.22 | A | C |
| ATOM | 3390 | CB | LEU | A | 218 | 75.629 | −33.247 | −5.428 | 1.00 | 13.96 | A | C |
| ATOM | 3393 | CG | LEU | A | 218 | 74.139 | −33.142 | −5.094 | 1.00 | 13.06 | A | C |
| ATOM | 3395 | CD1 | LEU | A | 218 | 73.337 | −32.809 | −6.334 | 1.00 | 12.25 | A | C |
| ATOM | 3399 | CD2 | LEU | A | 218 | 73.641 | −34.437 | −4.469 | 1.00 | 13.26 | A | C |
| ATOM | 3403 | C | LEU | A | 218 | 76.223 | −30.849 | −5.003 | 1.00 | 14.10 | A | C |
| ATOM | 3404 | O | LEU | A | 218 | 75.312 | −30.020 | −5.072 | 1.00 | 14.58 | A | O |
| ATOM | 3406 | N | LEU | A | 219 | 77.176 | −30.810 | −4.071 | 1.00 | 13.33 | A | N |
| ATOM | 3407 | CA | LEU | A | 219 | 77.232 | −29.759 | −3.054 | 1.00 | 12.42 | A | C |
| ATOM | 3409 | CB | LEU | A | 219 | 78.290 | −30.088 | −1.996 | 1.00 | 12.57 | A | C |
| ATOM | 3412 | CG | LEU | A | 219 | 78.579 | −29.028 | −0.926 | 1.00 | 12.20 | A | C |
| ATOM | 3414 | CD1 | LEU | A | 219 | 77.303 | −28.587 | −0.229 | 1.00 | 11.68 | A | C |

TABLE 8-2-continued

Coordinates for L494P Structure

| ATOM | 3418 | CD2 | LEU | A | 219 | 79.581 | −29.562 | 0.083 | 1.00 | 11.55 | A | C |
|---|---|---|---|---|---|---|---|---|---|---|---|---|
| ATOM | 3422 | C | LEU | A | 219 | 77.548 | −28.415 | −3.687 | 1.00 | 11.77 | A | C |
| ATOM | 3423 | O | LEU | A | 219 | 76.797 | −27.456 | −3.523 | 1.00 | 11.68 | A | O |
| ATOM | 3425 | N | GLU | A | 220 | 78.664 | −28.358 | −4.411 | 1.00 | 11.19 | A | N |
| ATOM | 3426 | CA | GLU | A | 220 | 79.099 | −27.132 | −5.084 | 1.00 | 10.73 | A | C |
| ATOM | 3428 | CB | GLU | A | 220 | 80.281 | −27.414 | −6.019 | 1.00 | 10.70 | A | C |
| ATOM | 3431 | CG | GLU | A | 220 | 80.927 | −26.162 | −6.616 | 1.00 | 11.19 | A | C |
| ATOM | 3434 | CD | GLU | A | 220 | 82.256 | −26.444 | −7.314 | 1.00 | 12.55 | A | C |
| ATOM | 3435 | OE1 | GLU | A | 220 | 82.631 | −27.630 | −7.453 | 1.00 | 13.13 | A | O |
| ATOM | 3436 | OE2 | GLU | A | 220 | 82.929 | −25.473 | −7.724 | 1.00 | 12.14 | A | O |
| ATOM | 3437 | C | GLU | A | 220 | 77.950 | −26.501 | −5.862 | 1.00 | 10.27 | A | C |
| ATOM | 3438 | O | GLU | A | 220 | 77.748 | −25.292 | −5.793 | 1.00 | 10.52 | A | O |
| ATOM | 3440 | N | LEU | A | 221 | 77.194 | −27.325 | −6.584 | 1.00 | 9.55 | A | N |
| ATOM | 3441 | CA | LEU | A | 221 | 76.018 | −26.851 | −7.310 | 1.00 | 9.02 | A | C |
| ATOM | 3443 | CB | LEU | A | 221 | 75.442 | −27.966 | −8.186 | 1.00 | 8.70 | A | C |
| ATOM | 3446 | CG | LEU | A | 221 | 74.258 | −27.599 | −9.086 | 1.00 | 7.05 | A | C |
| ATOM | 3448 | CD1 | LEU | A | 221 | 74.630 | −26.491 | −10.059 | 1.00 | 2.00 | A | C |
| ATOM | 3452 | CD2 | LEU | A | 221 | 73.772 | −28.833 | −9.831 | 1.00 | 6.26 | A | C |
| ATOM | 3456 | C | LEU | A | 221 | 74.948 | −26.343 | −6.347 | 1.00 | 9.08 | A | C |
| ATOM | 3457 | O | LEU | A | 221 | 74.395 | −25.262 | −6.544 | 1.00 | 8.80 | A | O |
| ATOM | 3459 | N | ALA | A | 222 | 74.669 | −27.124 | −5.305 | 1.00 | 9.46 | A | N |
| ATOM | 3460 | CA | ALA | A | 222 | 73.666 | −26.757 | −4.301 | 1.00 | 9.95 | A | C |
| ATOM | 3462 | CB | ALA | A | 222 | 73.633 | −27.794 | −3.181 | 1.00 | 9.71 | A | C |
| ATOM | 3466 | C | ALA | A | 222 | 73.913 | −25.358 | −3.728 | 1.00 | 10.24 | A | C |
| ATOM | 3467 | O | ALA | A | 222 | 72.979 | −24.572 | −3.572 | 1.00 | 10.55 | A | O |
| ATOM | 3469 | N | ILE | A | 223 | 75.173 | −25.055 | −3.430 | 1.00 | 10.52 | A | N |
| ATOM | 3470 | CA | ILE | A | 223 | 75.562 | −23.737 | −2.925 | 1.00 | 10.83 | A | C |
| ATOM | 3472 | CB | ILE | A | 223 | 77.049 | −23.711 | −2.476 | 1.00 | 10.98 | A | C |
| ATOM | 3474 | CG1 | ILE | A | 223 | 77.305 | −24.712 | −1.345 | 1.00 | 11.58 | A | C |
| ATOM | 3477 | CD1 | ILE | A | 223 | 78.778 | −24.910 | −1.045 | 1.00 | 12.62 | A | C |
| ATOM | 3481 | CG2 | ILE | A | 223 | 77.451 | −22.315 | −2.019 | 1.00 | 9.71 | A | C |
| ATOM | 3485 | C | ILE | A | 223 | 75.374 | −22.683 | −4.016 | 1.00 | 11.05 | A | C |
| ATOM | 3486 | O | ILE | A | 223 | 74.722 | −21.656 | −3.800 | 1.00 | 10.83 | A | O |
| ATOM | 3488 | N | LEU | A | 224 | 75.955 | −22.958 | −5.183 | 1.00 | 11.18 | A | N |
| ATOM | 3489 | CA | LEU | A | 224 | 75.918 | −22.044 | −6.328 | 1.00 | 11.07 | A | C |
| ATOM | 3491 | CB | LEU | A | 224 | 76.648 | −22.654 | −7.534 | 1.00 | 11.14 | A | C |
| ATOM | 3494 | CG | LEU | A | 224 | 78.143 | −22.340 | −7.658 | 1.00 | 11.66 | A | C |
| ATOM | 3496 | CD1 | LEU | A | 224 | 78.746 | −23.108 | −8.827 | 1.00 | 11.34 | A | C |
| ATOM | 3500 | CD2 | LEU | A | 224 | 78.905 | −22.632 | −6.369 | 1.00 | 11.95 | A | C |
| ATOM | 3504 | C | LEU | A | 224 | 74.500 | −21.660 | −6.730 | 1.00 | 10.85 | A | C |
| ATOM | 3505 | O | LEU | A | 224 | 74.239 | −20.497 | −7.035 | 1.00 | 10.84 | A | O |
| ATOM | 3507 | N | ASP | A | 225 | 73.593 | −22.635 | −6.727 | 1.00 | 10.80 | A | N |
| ATOM | 3508 | CA | ASP | A | 225 | 72.207 | −22.395 | −7.125 | 1.00 | 10.89 | A | C |
| ATOM | 3510 | CB | ASP | A | 225 | 71.505 | −23.705 | −7.481 | 1.00 | 10.48 | A | C |
| ATOM | 3513 | CG | ASP | A | 225 | 70.158 | −23.481 | −8.142 | 1.00 | 9.49 | A | C |
| ATOM | 3514 | OD1 | ASP | A | 225 | 69.184 | −23.189 | −7.422 | 1.00 | 10.17 | A | O |
| ATOM | 3515 | OD2 | ASP | A | 225 | 70.069 | −23.597 | −9.382 | 1.00 | 8.04 | A | O |
| ATOM | 3516 | C | ASP | A | 225 | 71.416 | −21.659 | −6.047 | 1.00 | 11.49 | A | C |
| ATOM | 3517 | O | ASP | A | 225 | 70.605 | −20.792 | −6.367 | 1.00 | 11.55 | A | O |
| ATOM | 3519 | N | TYR | A | 226 | 71.641 | −22.004 | −4.780 | 1.00 | 12.19 | A | N |
| ATOM | 3520 | CA | TYR | A | 226 | 70.963 | −21.320 | −3.676 | 1.00 | 12.94 | A | C |
| ATOM | 3522 | CB | TYR | A | 226 | 71.215 | −22.022 | −2.335 | 1.00 | 13.18 | A | C |
| ATOM | 3525 | CG | TYR | A | 226 | 70.495 | −21.360 | −1.178 | 1.00 | 13.58 | A | C |
| ATOM | 3526 | CD1 | TYR | A | 226 | 69.207 | −21.745 | −0.825 | 1.00 | 15.76 | A | C |
| ATOM | 3528 | CE1 | TYR | A | 226 | 68.536 | −21.133 | 0.227 | 1.00 | 17.41 | A | C |
| ATOM | 3530 | CZ | TYR | A | 226 | 69.154 | −20.117 | 0.932 | 1.00 | 18.41 | A | C |
| ATOM | 3531 | OH | TYR | A | 226 | 68.493 | −19.509 | 1.972 | 1.00 | 18.87 | A | O |
| ATOM | 3533 | CE2 | TYR | A | 226 | 70.434 | −19.712 | 0.595 | 1.00 | 16.75 | A | C |
| ATOM | 3535 | CD2 | TYR | A | 226 | 71.093 | −20.331 | −0.457 | 1.00 | 14.36 | A | C |
| ATOM | 3537 | C | TYR | A | 226 | 71.394 | −19.855 | −3.582 | 1.00 | 13.23 | A | C |
| ATOM | 3538 | O | TYR | A | 226 | 70.562 | −18.971 | −3.355 | 1.00 | 13.29 | A | O |
| ATOM | 3540 | N | ASN | A | 227 | 72.692 | −19.608 | −3.742 | 1.00 | 13.39 | A | N |
| ATOM | 3541 | CA | ASN | A | 227 | 73.221 | −18.246 | −3.718 | 1.00 | 14.03 | A | C |
| ATOM | 3543 | CB | ASN | A | 227 | 74.751 | −18.258 | −3.625 | 1.00 | 14.09 | A | C |
| ATOM | 3546 | CG | ASN | A | 227 | 75.255 | −18.679 | −2.250 | 1.00 | 14.19 | A | C |
| ATOM | 3547 | OD1 | ASN | A | 227 | 74.571 | −18.512 | −1.241 | 1.00 | 14.72 | A | O |
| ATOM | 3548 | ND2 | ASN | A | 227 | 76.467 | −19.217 | −2.208 | 1.00 | 15.25 | A | N |
| ATOM | 3551 | C | ASN | A | 227 | 72.768 | −17.429 | −4.929 | 1.00 | 14.55 | A | C |
| ATOM | 3552 | O | ASN | A | 227 | 72.560 | −16.219 | −4.819 | 1.00 | 14.82 | A | O |
| ATOM | 3554 | N | MET | A | 228 | 72.619 | −18.093 | −6.074 | 1.00 | 14.98 | A | N |
| ATOM | 3555 | CA | MET | A | 228 | 72.085 | −17.462 | −7.284 | 1.00 | 15.29 | A | C |
| ATOM | 3557 | CB | MET | A | 228 | 72.127 | −18.444 | −8.462 | 1.00 | 15.61 | A | C |
| ATOM | 3560 | CG | MET | A | 228 | 71.507 | −17.933 | −9.767 | 1.00 | 16.18 | A | C |
| ATOM | 3563 | SD | MET | A | 228 | 70.987 | −19.279 | −10.861 | 1.00 | 18.75 | A | S |
| ATOM | 3564 | CE | MET | A | 228 | 69.510 | −19.868 | −10.029 | 1.00 | 17.19 | A | C |
| ATOM | 3568 | C | MET | A | 228 | 70.650 | −17.009 | −7.049 | 1.00 | 15.29 | A | C |
| ATOM | 3569 | O | MET | A | 228 | 70.329 | −15.833 | −7.218 | 1.00 | 15.27 | A | O |
| ATOM | 3571 | N | ILE | A | 229 | 69.793 | −17.951 | −6.661 | 1.00 | 15.43 | A | N |

TABLE 8-2-continued

Coordinates for L494P Structure

| ATOM | 3572 | CA | ILE | A | 229 | 68.385 | −17.655 | −6.413 | 1.00 | 15.53 | A | C |
|---|---|---|---|---|---|---|---|---|---|---|---|---|
| ATOM | 3574 | CB | ILE | A | 229 | 67.605 | −18.896 | −5.916 | 1.00 | 15.48 | A | C |
| ATOM | 3576 | CG1 | ILE | A | 229 | 67.419 | −19.909 | −7.051 | 1.00 | 15.09 | A | C |
| ATOM | 3579 | CD1 | ILE | A | 229 | 66.660 | −21.167 | −6.643 | 1.00 | 11.04 | A | C |
| ATOM | 3583 | CG2 | ILE | A | 229 | 66.240 | −18.489 | −5.384 | 1.00 | 16.76 | A | C |
| ATOM | 3587 | C | ILE | A | 229 | 68.252 | −16.529 | −5.395 | 1.00 | 15.81 | A | C |
| ATOM | 3588 | O | ILE | A | 229 | 67.429 | −15.634 | −5.566 | 1.00 | 16.48 | A | O |
| ATOM | 3590 | N | GLN | A | 230 | 69.073 | −16.567 | −4.348 | 1.00 | 15.87 | A | N |
| ATOM | 3591 | CA | GLN | A | 230 | 69.059 | −15.514 | −3.332 | 1.00 | 15.81 | A | C |
| ATOM | 3593 | CB | GLN | A | 230 | 70.046 | −15.817 | −2.199 | 1.00 | 15.91 | A | C |
| ATOM | 3596 | CG | GLN | A | 230 | 69.925 | −14.855 | −1.019 | 1.00 | 15.74 | A | C |
| ATOM | 3599 | CD | GLN | A | 230 | 70.996 | −15.064 | 0.026 | 1.00 | 15.63 | A | C |
| ATOM | 3600 | OE1 | GLN | A | 230 | 71.920 | −14.261 | 0.147 | 1.00 | 17.47 | A | O |
| ATOM | 3601 | NE2 | GLN | A | 230 | 70.879 | −16.145 | 0.791 | 1.00 | 14.80 | A | N |
| ATOM | 3604 | C | GLN | A | 230 | 69.372 | −14.143 | −3.929 | 1.00 | 15.64 | A | C |
| ATOM | 3605 | O | GLN | A | 230 | 68.772 | −13.147 | −3.532 | 1.00 | 15.71 | A | O |
| ATOM | 3607 | N | SER | A | 231 | 70.305 | −14.091 | −4.878 | 1.00 | 15.55 | A | N |
| ATOM | 3608 | CA | SER | A | 231 | 70.678 | −12.819 | −5.504 | 1.00 | 15.35 | A | C |
| ATOM | 3610 | CB | SER | A | 231 | 71.927 | −12.962 | −6.385 | 1.00 | 15.10 | A | C |
| ATOM | 3613 | OG | SER | A | 231 | 71.603 | −13.433 | −7.681 | 1.00 | 15.04 | A | O |
| ATOM | 3615 | C | SER | A | 231 | 69.511 | −12.251 | −6.308 | 1.00 | 15.24 | A | C |
| ATOM | 3616 | O | SER | A | 231 | 69.441 | −11.041 | −6.525 | 1.00 | 15.43 | A | O |
| ATOM | 3618 | N | VAL | A | 232 | 68.605 | −13.126 | −6.747 | 1.00 | 15.03 | A | N |
| ATOM | 3619 | CA | VAL | A | 232 | 67.343 | −12.692 | −7.341 | 1.00 | 15.37 | A | C |
| ATOM | 3621 | CB | VAL | A | 232 | 66.631 | −13.837 | −8.091 | 1.00 | 15.43 | A | C |
| ATOM | 3623 | CG1 | VAL | A | 232 | 65.234 | −13.406 | −8.544 | 1.00 | 14.95 | A | C |
| ATOM | 3627 | CG2 | VAL | A | 232 | 67.468 | −14.282 | −9.277 | 1.00 | 15.59 | A | C |
| ATOM | 3631 | C | VAL | A | 232 | 66.427 | −12.130 | −6.256 | 1.00 | 15.65 | A | C |
| ATOM | 3632 | O | VAL | A | 232 | 65.897 | −11.027 | −6.401 | 1.00 | 15.40 | A | O |
| ATOM | 3634 | N | TYR | A | 233 | 66.259 | −12.882 | −5.168 | 1.00 | 16.13 | A | N |
| ATOM | 3635 | CA | TYR | A | 233 | 65.453 | −12.426 | −4.030 | 1.00 | 16.89 | A | C |
| ATOM | 3637 | CB | TYR | A | 233 | 65.588 | −13.370 | −2.825 | 1.00 | 16.70 | A | C |
| ATOM | 3640 | CG | TYR | A | 233 | 65.023 | −14.766 | −2.995 | 1.00 | 16.10 | A | C |
| ATOM | 3641 | CD1 | TYR | A | 233 | 64.102 | −15.068 | −4.001 | 1.00 | 17.42 | A | C |
| ATOM | 3643 | CE1 | TYR | A | 233 | 63.584 | −16.348 | −4.137 | 1.00 | 16.75 | A | C |
| ATOM | 3645 | CZ | TYR | A | 233 | 63.969 | −17.336 | −3.253 | 1.00 | 16.03 | A | C |
| ATOM | 3646 | OH | TYR | A | 233 | 63.452 | −18.601 | −3.388 | 1.00 | 17.62 | A | O |
| ATOM | 3648 | CE2 | TYR | A | 233 | 64.868 | −17.060 | −2.241 | 1.00 | 14.85 | A | C |
| ATOM | 3650 | CD2 | TYR | A | 233 | 65.385 | −15.782 | −2.115 | 1.00 | 14.89 | A | C |
| ATOM | 3652 | C | TYR | A | 233 | 65.841 | −11.016 | −3.591 | 1.00 | 17.81 | A | C |
| ATOM | 3653 | O | TYR | A | 233 | 64.977 | −10.199 | −3.267 | 1.00 | 17.90 | A | O |
| ATOM | 3655 | N | GLN | A | 234 | 67.142 | −10.743 | −3.577 | 1.00 | 19.03 | A | N |
| ATOM | 3656 | CA | GLN | A | 234 | 67.656 | −9.424 | −3.212 | 1.00 | 20.11 | A | C |
| ATOM | 3658 | CB | GLN | A | 234 | 69.178 | −9.474 | −3.026 | 1.00 | 20.14 | A | C |
| ATOM | 3661 | CG | GLN | A | 234 | 69.614 | −10.305 | −1.821 | 1.00 | 20.32 | A | C |
| ATOM | 3664 | CD | GLN | A | 234 | 71.113 | −10.522 | −1.755 | 1.00 | 20.42 | A | C |
| ATOM | 3665 | OE1 | GLN | A | 234 | 71.897 | −9.618 | −2.046 | 1.00 | 21.90 | A | O |
| ATOM | 3666 | NE2 | GLN | A | 234 | 71.519 | −11.725 | −1.359 | 1.00 | 19.04 | A | N |
| ATOM | 3669 | C | GLN | A | 234 | 67.273 | −8.370 | −4.251 | 1.00 | 20.93 | A | C |
| ATOM | 3670 | O | GLN | A | 234 | 66.878 | −7.258 | −3.890 | 1.00 | 20.70 | A | O |
| ATOM | 3672 | N | ARG | A | 235 | 67.380 | −8.728 | −5.533 | 1.00 | 21.91 | A | N |
| ATOM | 3673 | CA | ARG | A | 235 | 66.999 | −7.828 | −6.629 | 1.00 | 22.67 | A | C |
| ATOM | 3675 | CB | ARG | A | 235 | 67.476 | −8.369 | −7.989 | 1.00 | 23.14 | A | C |
| ATOM | 3678 | CG | ARG | A | 235 | 67.224 | −7.413 | −9.167 | 1.00 | 24.55 | A | C |
| ATOM | 3681 | CD | ARG | A | 235 | 68.367 | −7.390 | −10.199 | 1.00 | 27.72 | A | C |
| ATOM | 3684 | NE | ARG | A | 235 | 68.169 | −8.321 | −11.317 | 1.00 | 30.54 | A | N |
| ATOM | 3686 | CZ | ARG | A | 235 | 68.777 | −9.502 | −11.474 | 1.00 | 31.20 | A | C |
| ATOM | 3687 | NH1 | ARG | A | 235 | 69.652 | −9.961 | −10.582 | 1.00 | 31.84 | A | N |
| ATOM | 3690 | NH2 | ARG | A | 235 | 68.502 | −10.239 | −12.547 | 1.00 | 30.15 | A | N |
| ATOM | 3693 | C | ARG | A | 235 | 65.489 | −7.586 | −6.647 | 1.00 | 22.58 | A | C |
| ATOM | 3694 | O | ARG | A | 235 | 65.041 | −6.485 | −6.977 | 1.00 | 22.79 | A | O |
| ATOM | 3696 | N | ASP | A | 236 | 64.714 | −8.613 | −6.298 | 1.00 | 22.21 | A | N |
| ATOM | 3697 | CA | ASP | A | 236 | 63.264 | −8.470 | −6.137 | 1.00 | 22.10 | A | C |
| ATOM | 3699 | CB | ASP | A | 236 | 62.602 | −9.827 | −5.858 | 1.00 | 21.87 | A | C |
| ATOM | 3702 | CG | ASP | A | 236 | 62.525 | −10.721 | −7.087 | 1.00 | 21.53 | A | C |
| ATOM | 3703 | OD1 | ASP | A | 236 | 62.684 | −10.224 | −8.222 | 1.00 | 19.56 | A | O |
| ATOM | 3704 | OD2 | ASP | A | 236 | 62.293 | −11.936 | −6.907 | 1.00 | 20.26 | A | O |
| ATOM | 3705 | C | ASP | A | 236 | 62.926 | −7.513 | −4.995 | 1.00 | 22.23 | A | C |
| ATOM | 3706 | O | ASP | A | 236 | 61.997 | −6.712 | −5.107 | 1.00 | 22.26 | A | O |
| ATOM | 3708 | N | LEU | A | 237 | 63.686 | −7.598 | −3.902 | 1.00 | 22.39 | A | N |
| ATOM | 3709 | CA | LEU | A | 237 | 63.391 | −6.829 | −2.693 | 1.00 | 22.41 | A | C |
| ATOM | 3711 | CB | LEU | A | 237 | 64.157 | −7.387 | −1.489 | 1.00 | 22.11 | A | C |
| ATOM | 3714 | CG | LEU | A | 237 | 63.678 | −6.902 | −0.118 | 1.00 | 21.18 | A | C |
| ATOM | 3716 | CD1 | LEU | A | 237 | 62.211 | −7.251 | 0.103 | 1.00 | 20.99 | A | C |
| ATOM | 3720 | CD2 | LEU | A | 237 | 64.532 | −7.497 | 0.986 | 1.00 | 20.81 | A | C |
| ATOM | 3724 | C | LEU | A | 237 | 63.701 | −5.347 | −2.860 | 1.00 | 22.97 | A | C |
| ATOM | 3725 | O | LEU | A | 237 | 62.888 | −4.503 | −2.487 | 1.00 | 23.24 | A | O |
| ATOM | 3727 | N | ARG | A | 238 | 64.870 | −5.032 | −3.414 | 1.00 | 23.56 | A | N |

TABLE 8-2-continued

Coordinates for L494P Structure

| ATOM | 3728 | CA | ARG | A | 238 | 65.252 | −3.637 | −3.655 | 1.00 | 23.85 | A | C |
|---|---|---|---|---|---|---|---|---|---|---|---|---|
| ATOM | 3730 | CB | ARG | A | 238 | 66.594 | −3.544 | −4.391 | 1.00 | 23.60 | A | C |
| ATOM | 3733 | CG | ARG | A | 238 | 67.798 | −3.930 | −3.546 | 1.00 | 23.92 | A | C |
| ATOM | 3736 | CD | ARG | A | 238 | 69.109 | −3.464 | −4.176 | 1.00 | 25.61 | A | C |
| ATOM | 3739 | NE | ARG | A | 238 | 69.289 | −3.951 | −5.547 | 1.00 | 26.87 | A | N |
| ATOM | 3741 | CZ | ARG | A | 238 | 69.725 | −5.168 | −5.887 | 1.00 | 27.26 | A | C |
| ATOM | 3742 | NH1 | ARG | A | 238 | 70.036 | −6.073 | −4.961 | 1.00 | 27.13 | A | N |
| ATOM | 3745 | NH2 | ARG | A | 238 | 69.847 | −5.487 | −7.172 | 1.00 | 26.94 | A | N |
| ATOM | 3748 | C | ARG | A | 238 | 64.169 | −2.900 | −4.446 | 1.00 | 24.35 | A | C |
| ATOM | 3749 | O | ARG | A | 238 | 63.854 | −1.750 | −4.142 | 1.00 | 24.59 | A | O |
| ATOM | 3751 | N | GLU | A | 239 | 63.600 | −3.575 | −5.445 | 1.00 | 24.73 | A | N |
| ATOM | 3752 | CA | GLU | A | 239 | 62.514 | −3.020 | −6.259 | 1.00 | 25.20 | A | C |
| ATOM | 3754 | CB | GLU | A | 239 | 62.197 | −3.957 | −7.431 | 1.00 | 25.81 | A | C |
| ATOM | 3757 | CG | GLU | A | 239 | 61.161 | −3.414 | −8.425 | 1.00 | 28.50 | A | C |
| ATOM | 3760 | CD | GLU | A | 239 | 60.814 | −4.406 | −9.530 | 1.00 | 31.93 | A | C |
| ATOM | 3761 | OE1 | GLU | A | 239 | 61.344 | −5.542 | −9.512 | 1.00 | 33.54 | A | O |
| ATOM | 3762 | OE2 | GLU | A | 239 | 60.005 | −4.048 | −10.417 | 1.00 | 33.16 | A | O |
| ATOM | 3763 | C | GLU | A | 239 | 61.254 | −2.791 | −5.423 | 1.00 | 24.67 | A | C |
| ATOM | 3764 | O | GLU | A | 239 | 60.556 | −1.788 | −5.596 | 1.00 | 24.49 | A | O |
| ATOM | 3766 | N | THR | A | 240 | 60.966 | −3.730 | −4.528 | 1.00 | 24.08 | A | N |
| ATOM | 3767 | CA | THR | A | 240 | 59.829 | −3.610 | −3.624 | 1.00 | 23.83 | A | C |
| ATOM | 3769 | CB | THR | A | 240 | 59.535 | −4.946 | −2.915 | 1.00 | 23.90 | A | C |
| ATOM | 3771 | OG1 | THR | A | 240 | 59.679 | −6.026 | −3.845 | 1.00 | 24.05 | A | O |
| ATOM | 3773 | CG2 | THR | A | 240 | 58.121 | −4.953 | −2.344 | 1.00 | 24.20 | A | C |
| ATOM | 3777 | C | THR | A | 240 | 60.089 | −2.524 | −2.578 | 1.00 | 23.67 | A | C |
| ATOM | 3778 | O | THR | A | 240 | 59.225 | −1.686 | −2.318 | 1.00 | 23.85 | A | O |
| ATOM | 3780 | N | SER | A | 241 | 61.284 | −2.541 | −1.990 | 1.00 | 23.37 | A | N |
| ATOM | 3781 | CA | SER | A | 241 | 61.684 | −1.535 | −1.003 | 1.00 | 23.30 | A | C |
| ATOM | 3783 | CB | SER | A | 241 | 63.097 | −1.811 | −0.495 | 1.00 | 23.25 | A | C |
| ATOM | 3786 | OG | SER | A | 241 | 63.136 | −3.010 | 0.253 | 1.00 | 24.21 | A | O |
| ATOM | 3788 | C | SER | A | 241 | 61.612 | −0.117 | −1.561 | 1.00 | 23.34 | A | C |
| ATOM | 3789 | O | SER | A | 241 | 61.297 | 0.820 | −0.831 | 1.00 | 23.53 | A | O |
| ATOM | 3791 | N | ARG | A | 242 | 61.912 | 0.040 | −2.847 | 1.00 | 23.51 | A | N |
| ATOM | 3792 | CA | ARG | A | 242 | 61.754 | 1.334 | −3.509 | 1.00 | 23.66 | A | C |
| ATOM | 3794 | CB | ARG | A | 242 | 62.312 | 1.304 | −4.941 | 1.00 | 23.94 | A | C |
| ATOM | 3797 | CG | ARG | A | 242 | 63.841 | 1.370 | −5.019 | 1.00 | 24.87 | A | C |
| ATOM | 3800 | CD | ARG | A | 242 | 64.335 | 1.973 | −6.333 | 1.00 | 26.38 | A | C |
| ATOM | 3803 | NE | ARG | A | 242 | 64.074 | 1.116 | −7.492 | 1.00 | 28.02 | A | N |
| ATOM | 3805 | CZ | ARG | A | 242 | 64.802 | 0.054 | −7.848 | 1.00 | 27.68 | A | C |
| ATOM | 3806 | NH1 | ARG | A | 242 | 64.462 | −0.643 | −8.928 | 1.00 | 26.86 | A | N |
| ATOM | 3809 | NH2 | ARG | A | 242 | 65.861 | −0.324 | −7.135 | 1.00 | 27.49 | A | N |
| ATOM | 3812 | C | ARG | A | 242 | 60.286 | 1.757 | −3.514 | 1.00 | 23.31 | A | C |
| ATOM | 3813 | O | ARG | A | 242 | 59.976 | 2.920 | −3.264 | 1.00 | 23.30 | A | O |
| ATOM | 3815 | N | TRP | A | 243 | 59.393 | 0.809 | −3.788 | 1.00 | 23.18 | A | N |
| ATOM | 3816 | CA | TRP | A | 243 | 57.949 | 1.072 | −3.768 | 1.00 | 23.23 | A | C |
| ATOM | 3818 | CB | TRP | A | 243 | 57.177 | −0.111 | −4.369 | 1.00 | 23.16 | A | C |
| ATOM | 3821 | CG | TRP | A | 243 | 55.704 | −0.106 | −4.072 | 1.00 | 23.21 | A | C |
| ATOM | 3822 | CD1 | TRP | A | 243 | 54.729 | 0.555 | −4.762 | 1.00 | 23.71 | A | C |
| ATOM | 3824 | NE1 | TRP | A | 243 | 53.499 | 0.317 | −4.193 | 1.00 | 23.58 | A | N |
| ATOM | 3826 | CE2 | TRP | A | 243 | 53.662 | −0.514 | −3.116 | 1.00 | 23.23 | A | C |
| ATOM | 3827 | CD2 | TRP | A | 243 | 55.041 | −0.802 | −3.009 | 1.00 | 23.80 | A | C |
| ATOM | 3828 | CE3 | TRP | A | 243 | 55.478 | −1.639 | −1.973 | 1.00 | 23.02 | A | C |
| ATOM | 3830 | CZ3 | TRP | A | 243 | 54.535 | −2.156 | −1.091 | 1.00 | 22.08 | A | C |
| ATOM | 3832 | CH2 | TRP | A | 243 | 53.171 | −1.849 | −1.224 | 1.00 | 21.07 | A | C |
| ATOM | 3834 | CZ2 | TRP | A | 243 | 52.717 | −1.033 | −2.228 | 1.00 | 22.30 | A | C |
| ATOM | 3836 | C | TRP | A | 243 | 57.440 | 1.364 | −2.353 | 1.00 | 23.29 | A | C |
| ATOM | 3837 | O | TRP | A | 243 | 56.706 | 2.332 | −2.139 | 1.00 | 23.34 | A | O |
| ATOM | 3839 | N | TRP | A | 244 | 57.830 | 0.522 | −1.399 | 1.00 | 23.09 | A | N |
| ATOM | 3840 | CA | TRP | A | 244 | 57.355 | 0.641 | −0.019 | 1.00 | 22.81 | A | C |
| ATOM | 3842 | CB | TRP | A | 244 | 57.907 | −0.507 | 0.834 | 1.00 | 22.28 | A | C |
| ATOM | 3845 | CG | TRP | A | 244 | 57.373 | −0.551 | 2.242 | 1.00 | 21.81 | A | C |
| ATOM | 3846 | CD1 | TRP | A | 244 | 58.102 | −0.486 | 3.393 | 1.00 | 22.74 | A | C |
| ATOM | 3848 | NE1 | TRP | A | 244 | 57.271 | −0.556 | 4.486 | 1.00 | 22.22 | A | N |
| ATOM | 3850 | CE2 | TRP | A | 244 | 55.976 | −0.667 | 4.055 | 1.00 | 21.12 | A | C |
| ATOM | 3851 | CD2 | TRP | A | 244 | 56.000 | −0.666 | 2.645 | 1.00 | 20.57 | A | C |
| ATOM | 3852 | CE3 | TRP | A | 244 | 54.789 | −0.766 | 1.951 | 1.00 | 19.76 | A | C |
| ATOM | 3854 | CZ3 | TRP | A | 244 | 53.610 | −0.863 | 2.675 | 1.00 | 19.15 | A | C |
| ATOM | 3856 | CH2 | TRP | A | 244 | 53.619 | −0.863 | 4.076 | 1.00 | 20.39 | A | C |
| ATOM | 3858 | CZ2 | TRP | A | 244 | 54.789 | −0.764 | 4.784 | 1.00 | 21.06 | A | C |
| ATOM | 3860 | C | TRP | A | 244 | 57.699 | 1.996 | 0.608 | 1.00 | 23.07 | A | C |
| ATOM | 3861 | O | TRP | A | 244 | 56.851 | 2.609 | 1.256 | 1.00 | 23.27 | A | O |
| ATOM | 3863 | N | ARG | A | 245 | 58.930 | 2.467 | 0.408 | 1.00 | 23.23 | A | N |
| ATOM | 3864 | CA | ARG | A | 245 | 59.342 | 3.773 | 0.934 | 1.00 | 23.46 | A | C |
| ATOM | 3866 | CB | ARG | A | 245 | 60.839 | 4.028 | 0.708 | 1.00 | 23.77 | A | C |
| ATOM | 3869 | CG | ARG | A | 245 | 61.769 | 3.206 | 1.596 | 1.00 | 25.08 | A | C |
| ATOM | 3872 | CD | ARG | A | 245 | 63.090 | 3.929 | 1.866 | 1.00 | 28.31 | A | C |
| ATOM | 3875 | NE | ARG | A | 245 | 63.649 | 4.582 | 0.677 | 1.00 | 30.86 | A | N |
| ATOM | 3877 | CZ | ARG | A | 245 | 64.296 | 3.963 | −0.312 | 1.00 | 32.93 | A | C |

TABLE 8-2-continued

Coordinates for L494P Structure

| ATOM | 3878 | NH1 | ARG | A | 245 | 64.480 | 2.644 | −0.296 | 1.00 | 33.65 | A | N |
|---|---|---|---|---|---|---|---|---|---|---|---|---|
| ATOM | 3881 | NH2 | ARG | A | 245 | 64.760 | 4.671 | −1.338 | 1.00 | 33.03 | A | N |
| ATOM | 3884 | C | ARG | A | 245 | 58.532 | 4.898 | 0.295 | 1.00 | 23.19 | A | C |
| ATOM | 3885 | O | ARG | A | 245 | 58.020 | 5.776 | 0.994 | 1.00 | 23.26 | A | O |
| ATOM | 3887 | N | ARG | A | 246 | 58.426 | 4.860 | −1.032 | 1.00 | 22.85 | A | N |
| ATOM | 3888 | CA | ARG | A | 246 | 57.653 | 5.843 | −1.799 | 1.00 | 22.73 | A | C |
| ATOM | 3890 | CB | ARG | A | 246 | 57.613 | 5.451 | −3.282 | 1.00 | 23.21 | A | C |
| ATOM | 3893 | CG | ARG | A | 246 | 58.727 | 6.068 | −4.126 | 1.00 | 26.50 | A | C |
| ATOM | 3896 | CD | ARG | A | 246 | 58.216 | 7.252 | −4.944 | 1.00 | 30.69 | A | C |
| ATOM | 3899 | NE | ARG | A | 246 | 57.435 | 6.800 | −6.098 | 1.00 | 33.43 | A | N |
| ATOM | 3901 | CZ | ARG | A | 246 | 57.944 | 6.440 | −7.278 | 1.00 | 35.34 | A | C |
| ATOM | 3902 | NH1 | ARG | A | 246 | 59.257 | 6.479 | −7.505 | 1.00 | 35.77 | A | N |
| ATOM | 3905 | NH2 | ARG | A | 246 | 57.129 | 6.038 | −8.249 | 1.00 | 35.70 | A | N |
| ATOM | 3908 | C | ARG | A | 246 | 56.232 | 5.997 | −1.266 | 1.00 | 21.79 | A | C |
| ATOM | 3909 | O | ARG | A | 246 | 55.743 | 7.114 | −1.101 | 1.00 | 21.69 | A | O |
| ATOM | 3911 | N | VAL | A | 247 | 55.579 | 4.870 | −1.000 | 1.00 | 20.96 | A | N |
| ATOM | 3912 | CA | VAL | A | 247 | 54.252 | 4.871 | −0.393 | 1.00 | 20.37 | A | C |
| ATOM | 3914 | CB | VAL | A | 247 | 53.725 | 3.434 | −0.202 | 1.00 | 19.99 | A | C |
| ATOM | 3916 | CG1 | VAL | A | 247 | 53.571 | 2.751 | −1.549 | 1.00 | 19.77 | A | C |
| ATOM | 3920 | CG2 | VAL | A | 247 | 52.400 | 3.433 | 0.549 | 1.00 | 19.80 | A | C |
| ATOM | 3924 | C | VAL | A | 247 | 54.293 | 5.600 | 0.955 | 1.00 | 20.50 | A | C |
| ATOM | 3925 | O | VAL | A | 247 | 53.458 | 6.463 | 1.227 | 1.00 | 19.95 | A | O |
| ATOM | 3927 | N | GLY | A | 248 | 55.275 | 5.247 | 1.783 | 1.00 | 20.89 | A | N |
| ATOM | 3928 | CA | GLY | A | 248 | 55.515 | 5.921 | 3.059 | 1.00 | 21.19 | A | C |
| ATOM | 3931 | C | GLY | A | 248 | 54.386 | 5.801 | 4.067 | 1.00 | 21.62 | A | C |
| ATOM | 3932 | O | GLY | A | 248 | 54.129 | 6.736 | 4.827 | 1.00 | 21.37 | A | O |
| ATOM | 3934 | N | LEU | A | 249 | 53.726 | 4.645 | 4.090 | 1.00 | 22.43 | A | N |
| ATOM | 3935 | CA | LEU | A | 249 | 52.558 | 4.438 | 4.952 | 1.00 | 23.00 | A | C |
| ATOM | 3937 | CB | LEU | A | 249 | 51.685 | 3.290 | 4.421 | 1.00 | 22.92 | A | C |
| ATOM | 3940 | CG | LEU | A | 249 | 50.171 | 3.488 | 4.554 | 1.00 | 22.33 | A | C |
| ATOM | 3942 | CD1 | LEU | A | 249 | 49.692 | 4.615 | 3.649 | 1.00 | 21.36 | A | C |
| ATOM | 3946 | CD2 | LEU | A | 249 | 49.430 | 2.205 | 4.229 | 1.00 | 21.54 | A | C |
| ATOM | 3950 | C | LEU | A | 249 | 52.978 | 4.172 | 6.403 | 1.00 | 23.55 | A | C |
| ATOM | 3951 | O | LEU | A | 249 | 52.390 | 4.726 | 7.336 | 1.00 | 23.31 | A | O |
| ATOM | 3953 | N | ALA | A | 250 | 53.996 | 3.332 | 6.584 | 1.00 | 24.09 | A | N |
| ATOM | 3954 | CA | ALA | A | 250 | 54.538 | 3.034 | 7.913 | 1.00 | 24.42 | A | C |
| ATOM | 3956 | CB | ALA | A | 250 | 55.713 | 2.072 | 7.798 | 1.00 | 24.82 | A | C |
| ATOM | 3960 | C | ALA | A | 250 | 54.965 | 4.302 | 8.658 | 1.00 | 24.51 | A | C |
| ATOM | 3961 | O | ALA | A | 250 | 54.703 | 4.439 | 9.855 | 1.00 | 24.78 | A | O |
| ATOM | 3963 | N | THR | A | 251 | 55.620 | 5.218 | 7.944 | 1.00 | 24.26 | A | N |
| ATOM | 3964 | CA | THR | A | 251 | 56.070 | 6.486 | 8.520 | 1.00 | 23.84 | A | C |
| ATOM | 3966 | CB | THR | A | 251 | 56.889 | 7.311 | 7.504 | 1.00 | 23.73 | A | C |
| ATOM | 3968 | OG1 | THR | A | 251 | 57.988 | 6.530 | 7.022 | 1.00 | 23.21 | A | O |
| ATOM | 3970 | CG2 | THR | A | 251 | 57.413 | 8.596 | 8.146 | 1.00 | 23.03 | A | C |
| ATOM | 3974 | C | THR | A | 251 | 54.904 | 7.354 | 8.990 | 1.00 | 23.80 | A | C |
| ATOM | 3975 | O | THR | A | 251 | 54.852 | 7.748 | 10.154 | 1.00 | 24.05 | A | O |
| ATOM | 3977 | N | LYS | A | 252 | 53.973 | 7.638 | 8.082 | 1.00 | 23.59 | A | N |
| ATOM | 3978 | CA | LYS | A | 252 | 52.912 | 8.617 | 8.339 | 1.00 | 23.66 | A | C |
| ATOM | 3980 | CB | LYS | A | 252 | 52.238 | 9.041 | 7.025 | 1.00 | 23.72 | A | C |
| ATOM | 3983 | CG | LYS | A | 252 | 53.191 | 9.682 | 5.999 | 1.00 | 24.88 | A | C |
| ATOM | 3986 | CD | LYS | A | 252 | 53.744 | 11.038 | 6.465 | 1.00 | 25.58 | A | C |
| ATOM | 3989 | CE | LYS | A | 252 | 55.000 | 11.436 | 5.698 | 1.00 | 25.21 | A | C |
| ATOM | 3992 | NZ | LYS | A | 252 | 55.739 | 12.535 | 6.380 | 1.00 | 24.66 | A | N |
| ATOM | 3996 | C | LYS | A | 252 | 51.872 | 8.114 | 9.343 | 1.00 | 23.54 | A | C |
| ATOM | 3997 | O | LYS | A | 252 | 51.453 | 8.856 | 10.234 | 1.00 | 23.17 | A | O |
| ATOM | 3999 | N | LEU | A | 253 | 51.461 | 6.858 | 9.200 | 1.00 | 23.95 | A | N |
| ATOM | 4000 | CA | LEU | A | 253 | 50.579 | 6.226 | 10.181 | 1.00 | 24.13 | A | C |
| ATOM | 4002 | CB | LEU | A | 253 | 49.901 | 4.980 | 9.596 | 1.00 | 23.73 | A | C |
| ATOM | 4005 | CG | LEU | A | 253 | 48.663 | 5.213 | 8.724 | 1.00 | 22.61 | A | C |
| ATOM | 4007 | CD1 | LEU | A | 253 | 48.839 | 6.393 | 7.784 | 1.00 | 22.35 | A | C |
| ATOM | 4011 | CD2 | LEU | A | 253 | 48.328 | 3.954 | 7.943 | 1.00 | 23.69 | A | C |
| ATOM | 4015 | C | LEU | A | 253 | 51.404 | 5.863 | 11.414 | 1.00 | 24.78 | A | C |
| ATOM | 4016 | O | LEU | A | 253 | 52.176 | 4.901 | 11.389 | 1.00 | 25.30 | A | O |
| ATOM | 4018 | N | HIS | A | 254 | 51.238 | 6.638 | 12.486 | 1.00 | 24.95 | A | N |
| ATOM | 4019 | CA | HIS | A | 254 | 52.075 | 6.499 | 13.685 | 1.00 | 25.19 | A | C |
| ATOM | 4021 | CB | HIS | A | 254 | 51.757 | 7.594 | 14.714 | 1.00 | 25.53 | A | C |
| ATOM | 4024 | CG | HIS | A | 254 | 51.801 | 8.987 | 14.160 | 1.00 | 26.66 | A | C |
| ATOM | 4025 | ND1 | HIS | A | 254 | 52.813 | 9.434 | 13.337 | 1.00 | 26.59 | A | N |
| ATOM | 4027 | CE1 | HIS | A | 254 | 52.587 | 10.693 | 13.008 | 1.00 | 27.01 | A | C |
| ATOM | 4029 | NE2 | HIS | A | 254 | 51.468 | 11.082 | 13.593 | 1.00 | 27.77 | A | N |
| ATOM | 4031 | CD2 | HIS | A | 254 | 50.958 | 10.036 | 14.322 | 1.00 | 27.37 | A | C |
| ATOM | 4033 | C | HIS | A | 254 | 51.926 | 5.125 | 14.341 | 1.00 | 25.07 | A | C |
| ATOM | 4034 | O | HIS | A | 254 | 52.909 | 4.535 | 14.788 | 1.00 | 25.17 | A | O |
| ATOM | 4036 | N | PHE | A | 255 | 50.694 | 4.627 | 14.391 | 1.00 | 25.01 | A | N |
| ATOM | 4037 | CA | PHE | A | 255 | 50.392 | 3.332 | 15.013 | 1.00 | 25.06 | A | C |
| ATOM | 4039 | CB | PHE | A | 255 | 48.870 | 3.157 | 15.153 | 1.00 | 24.83 | A | C |
| ATOM | 4042 | CG | PHE | A | 255 | 48.151 | 2.999 | 13.837 | 1.00 | 24.67 | A | C |
| ATOM | 4043 | CD1 | PHE | A | 255 | 48.013 | 1.745 | 13.248 | 1.00 | 25.14 | A | C |

TABLE 8-2-continued

Coordinates for L494P Structure

| ATOM | 4045 | CE1 | PHE | A | 255 | 47.361 | 1.596 | 12.027 | 1.00 | 24.77 | A | C |
|------|------|-----|-----|---|-----|--------|-------|--------|------|-------|---|---|
| ATOM | 4047 | CZ | PHE | A | 255 | 46.838 | 2.708 | 11.386 | 1.00 | 25.06 | A | C |
| ATOM | 4049 | CE2 | PHE | A | 255 | 46.970 | 3.965 | 11.963 | 1.00 | 25.14 | A | C |
| ATOM | 4051 | CD2 | PHE | A | 255 | 47.624 | 4.105 | 13.182 | 1.00 | 24.68 | A | C |
| ATOM | 4053 | C | PHE | A | 255 | 50.962 | 2.125 | 14.256 | 1.00 | 25.30 | A | C |
| ATOM | 4054 | O | PHE | A | 255 | 51.288 | 1.106 | 14.869 | 1.00 | 25.15 | A | O |
| ATOM | 4056 | N | ALA | A | 256 | 51.078 | 2.245 | 12.934 | 1.00 | 25.66 | A | N |
| ATOM | 4057 | CA | ALA | A | 256 | 51.252 | 1.084 | 12.055 | 1.00 | 25.87 | A | C |
| ATOM | 4059 | CB | ALA | A | 256 | 50.884 | 1.454 | 10.622 | 1.00 | 25.83 | A | C |
| ATOM | 4063 | C | ALA | A | 256 | 52.651 | 0.468 | 12.095 | 1.00 | 26.20 | A | C |
| ATOM | 4064 | O | ALA | A | 256 | 53.654 | 1.177 | 12.226 | 1.00 | 26.11 | A | O |
| ATOM | 4066 | N | ARG | A | 257 | 52.696 | −0.857 | 11.962 | 1.00 | 26.63 | A | N |
| ATOM | 4067 | CA | ARG | A | 257 | 53.943 | −1.621 | 12.006 | 1.00 | 27.23 | A | C |
| ATOM | 4069 | CB | ARG | A | 257 | 53.705 | −2.990 | 12.643 | 1.00 | 27.59 | A | C |
| ATOM | 4072 | CG | ARG | A | 257 | 53.164 | −2.956 | 14.070 | 1.00 | 29.15 | A | C |
| ATOM | 4075 | CD | ARG | A | 257 | 52.777 | −4.360 | 14.518 | 1.00 | 30.54 | A | C |
| ATOM | 4078 | NE | ARG | A | 257 | 51.707 | −4.906 | 13.678 | 1.00 | 31.05 | A | N |
| ATOM | 4080 | CZ | ARG | A | 257 | 51.478 | −6.201 | 13.463 | 1.00 | 31.20 | A | C |
| ATOM | 4081 | NH1 | ARG | A | 257 | 52.242 | −7.139 | 14.018 | 1.00 | 31.74 | A | N |
| ATOM | 4084 | NH2 | ARG | A | 257 | 50.471 | −6.563 | 12.674 | 1.00 | 31.30 | A | N |
| ATOM | 4087 | C | ARG | A | 257 | 54.516 | −1.828 | 10.608 | 1.00 | 27.05 | A | C |
| ATOM | 4088 | O | ARG | A | 257 | 53.771 | −2.041 | 9.651 | 1.00 | 27.10 | A | O |
| ATOM | 4090 | N | ASP | A | 258 | 55.844 | −1.788 | 10.508 | 1.00 | 26.97 | A | N |
| ATOM | 4091 | CA | ASP | A | 258 | 56.548 | −1.937 | 9.236 | 1.00 | 26.68 | A | C |
| ATOM | 4093 | CB | ASP | A | 258 | 57.713 | −0.945 | 9.169 | 1.00 | 26.49 | A | C |
| ATOM | 4096 | CG | ASP | A | 258 | 58.241 | −0.759 | 7.764 | 1.00 | 26.72 | A | C |
| ATOM | 4097 | OD1 | ASP | A | 258 | 58.470 | −1.768 | 7.065 | 1.00 | 26.55 | A | O |
| ATOM | 4098 | OD2 | ASP | A | 258 | 58.428 | 0.405 | 7.351 | 1.00 | 28.47 | A | O |
| ATOM | 4099 | C | ASP | A | 258 | 57.049 | −3.373 | 9.073 | 1.00 | 26.57 | A | C |
| ATOM | 4100 | O | ASP | A | 258 | 58.058 | −3.759 | 9.667 | 1.00 | 26.72 | A | O |
| ATOM | 4102 | N | ARG | A | 259 | 56.342 | −4.157 | 8.262 | 1.00 | 26.49 | A | N |
| ATOM | 4103 | CA | ARG | A | 259 | 56.655 | −5.575 | 8.073 | 1.00 | 26.58 | A | C |
| ATOM | 4105 | CB | ARG | A | 259 | 55.578 | −6.447 | 8.738 | 1.00 | 27.25 | A | C |
| ATOM | 4108 | CG | ARG | A | 259 | 55.479 | −6.323 | 10.260 | 1.00 | 28.80 | A | C |
| ATOM | 4111 | CD | ARG | A | 259 | 56.423 | −7.277 | 10.983 | 1.00 | 30.14 | A | C |
| ATOM | 4114 | NE | ARG | A | 259 | 56.188 | −7.278 | 12.428 | 1.00 | 32.18 | A | N |
| ATOM | 4116 | CZ | ARG | A | 259 | 56.604 | −6.335 | 13.275 | 1.00 | 32.94 | A | C |
| ATOM | 4117 | NH1 | ARG | A | 259 | 57.290 | −5.280 | 12.842 | 1.00 | 34.19 | A | N |
| ATOM | 4120 | NH2 | ARG | A | 259 | 56.329 | −6.444 | 14.572 | 1.00 | 32.41 | A | N |
| ATOM | 4123 | C | ARG | A | 259 | 56.758 | −5.934 | 6.588 | 1.00 | 25.53 | A | C |
| ATOM | 4124 | O | ARG | A | 259 | 55.939 | −6.696 | 6.070 | 1.00 | 25.27 | A | O |
| ATOM | 4126 | N | LEU | A | 260 | 57.759 | −5.383 | 5.905 | 1.00 | 24.36 | A | N |
| ATOM | 4127 | CA | LEU | A | 260 | 57.987 | −5.709 | 4.496 | 1.00 | 23.56 | A | C |
| ATOM | 4129 | CB | LEU | A | 260 | 58.444 | −4.482 | 3.705 | 1.00 | 23.49 | A | C |
| ATOM | 4132 | CG | LEU | A | 260 | 58.738 | −4.732 | 2.220 | 1.00 | 22.82 | A | C |
| ATOM | 4134 | CD1 | LEU | A | 260 | 57.541 | −5.359 | 1.522 | 1.00 | 22.27 | A | C |
| ATOM | 4138 | CD2 | LEU | A | 260 | 59.145 | −3.448 | 1.530 | 1.00 | 23.21 | A | C |
| ATOM | 4142 | C | LEU | A | 260 | 59.024 | −6.812 | 4.382 | 1.00 | 22.93 | A | C |
| ATOM | 4143 | O | LEU | A | 260 | 58.782 | −7.834 | 3.736 | 1.00 | 23.24 | A | O |
| ATOM | 4145 | N | ILE | A | 261 | 60.175 | −6.592 | 5.013 | 1.00 | 22.02 | A | N |
| ATOM | 4146 | CA | ILE | A | 261 | 61.239 | −7.595 | 5.083 | 1.00 | 21.34 | A | C |
| ATOM | 4148 | CB | ILE | A | 261 | 62.309 | −7.215 | 6.131 | 1.00 | 21.16 | A | C |
| ATOM | 4150 | CG1 | ILE | A | 261 | 63.001 | −5.893 | 5.765 | 1.00 | 20.68 | A | C |
| ATOM | 4153 | CD1 | ILE | A | 261 | 63.318 | −5.016 | 6.972 | 1.00 | 19.12 | A | C |
| ATOM | 4157 | CG2 | ILE | A | 261 | 63.336 | −8.335 | 6.266 | 1.00 | 20.90 | A | C |
| ATOM | 4161 | C | ILE | A | 261 | 60.644 | −8.943 | 5.477 | 1.00 | 21.18 | A | C |
| ATOM | 4162 | O | ILE | A | 261 | 60.982 | −9.973 | 4.900 | 1.00 | 20.99 | A | O |
| ATOM | 4164 | N | GLU | A | 262 | 59.747 | −8.915 | 6.459 | 1.00 | 21.36 | A | N |
| ATOM | 4165 | CA | GLU | A | 262 | 59.060 | −10.112 | 6.927 | 1.00 | 21.68 | A | C |
| ATOM | 4167 | CB | GLU | A | 262 | 58.375 | −9.849 | 8.276 | 1.00 | 21.72 | A | C |
| ATOM | 4170 | CG | GLU | A | 262 | 59.332 | −9.744 | 9.477 | 1.00 | 21.84 | A | C |
| ATOM | 4173 | CD | GLU | A | 262 | 59.863 | −8.335 | 9.740 | 1.00 | 21.66 | A | C |
| ATOM | 4174 | OE1 | GLU | A | 262 | 59.610 | −7.413 | 8.933 | 1.00 | 21.94 | A | O |
| ATOM | 4175 | OE2 | GLU | A | 262 | 60.540 | −8.150 | 10.772 | 1.00 | 21.41 | A | O |
| ATOM | 4176 | C | GLU | A | 262 | 58.036 | −10.625 | 5.911 | 1.00 | 22.32 | A | C |
| ATOM | 4177 | O | GLU | A | 262 | 57.901 | −11.837 | 5.728 | 1.00 | 23.24 | A | O |
| ATOM | 4179 | N | SER | A | 263 | 57.313 | −9.712 | 5.262 | 1.00 | 22.49 | A | N |
| ATOM | 4180 | CA | SER | A | 263 | 56.288 | −10.094 | 4.277 | 1.00 | 22.31 | A | C |
| ATOM | 4182 | CB | SER | A | 263 | 55.386 | −8.909 | 3.919 | 1.00 | 22.29 | A | C |
| ATOM | 4185 | OG | SER | A | 263 | 54.431 | −8.678 | 4.939 | 1.00 | 22.39 | A | O |
| ATOM | 4187 | C | SER | A | 263 | 56.883 | −10.687 | 3.004 | 1.00 | 22.14 | A | C |
| ATOM | 4188 | O | SER | A | 263 | 56.274 | −11.555 | 2.382 | 1.00 | 22.58 | A | O |
| ATOM | 4190 | N | PHE | A | 264 | 58.059 | −10.214 | 2.606 | 1.00 | 22.01 | A | N |
| ATOM | 4191 | CA | PHE | A | 264 | 58.750 | −10.795 | 1.460 | 1.00 | 22.14 | A | C |
| ATOM | 4193 | CB | PHE | A | 264 | 59.942 | −9.933 | 1.038 | 1.00 | 22.16 | A | C |
| ATOM | 4196 | CG | PHE | A | 264 | 60.511 | −10.311 | −0.297 | 1.00 | 21.05 | A | C |
| ATOM | 4197 | CD1 | PHE | A | 264 | 59.905 | −9.880 | −1.467 | 1.00 | 20.84 | A | C |
| ATOM | 4199 | CE1 | PHE | A | 264 | 60.418 | −10.230 | −2.703 | 1.00 | 21.07 | A | C |

TABLE 8-2-continued

Coordinates for L494P Structure

| ATOM | 4201 | CZ | PHE | A | 264 | 61.552 | −11.021 | −2.778 | 1.00 | 22.11 | A | C |
|---|---|---|---|---|---|---|---|---|---|---|---|---|
| ATOM | 4203 | CE2 | PHE | A | 264 | 62.164 | −11.460 | −1.615 | 1.00 | 21.87 | A | C |
| ATOM | 4205 | CD2 | PHE | A | 264 | 61.641 | −11.108 | −0.384 | 1.00 | 20.79 | A | C |
| ATOM | 4207 | C | PHE | A | 264 | 59.212 | −12.211 | 1.800 | 1.00 | 22.40 | A | C |
| ATOM | 4208 | O | PHE | A | 264 | 58.950 | −13.149 | 1.042 | 1.00 | 22.39 | A | O |
| ATOM | 4210 | N | TYR | A | 265 | 59.885 | −12.349 | 2.946 | 1.00 | 22.32 | A | N |
| ATOM | 4211 | CA | TYR | A | 265 | 60.319 | −13.651 | 3.472 | 1.00 | 22.09 | A | C |
| ATOM | 4213 | CB | TYR | A | 265 | 60.930 | −13.489 | 4.872 | 1.00 | 22.28 | A | C |
| ATOM | 4216 | CG | TYR | A | 265 | 61.069 | −14.783 | 5.649 | 1.00 | 25.25 | A | C |
| ATOM | 4217 | CD1 | TYR | A | 265 | 62.150 | −15.636 | 5.438 | 1.00 | 27.20 | A | C |
| ATOM | 4219 | CE1 | TYR | A | 265 | 62.281 | −16.826 | 6.149 | 1.00 | 27.66 | A | C |
| ATOM | 4221 | CZ | TYR | A | 265 | 61.322 | −17.173 | 7.084 | 1.00 | 29.34 | A | C |
| ATOM | 4222 | OH | TYR | A | 265 | 61.447 | −18.349 | 7.791 | 1.00 | 32.52 | A | O |
| ATOM | 4224 | CE2 | TYR | A | 265 | 60.238 | −16.344 | 7.314 | 1.00 | 29.12 | A | C |
| ATOM | 4226 | CD2 | TYR | A | 265 | 60.117 | −15.156 | 6.598 | 1.00 | 28.54 | A | C |
| ATOM | 4228 | C | TYR | A | 265 | 59.163 | −14.649 | 3.513 | 1.00 | 21.42 | A | C |
| ATOM | 4229 | O | TYR | A | 265 | 59.334 | −15.821 | 3.175 | 1.00 | 21.62 | A | O |
| ATOM | 4231 | N | TRP | A | 266 | 57.992 | −14.180 | 3.935 | 1.00 | 20.65 | A | N |
| ATOM | 4232 | CA | TRP | A | 266 | 56.774 | −14.980 | 3.860 | 1.00 | 20.27 | A | C |
| ATOM | 4234 | CB | TRP | A | 266 | 55.576 | −14.189 | 4.407 | 1.00 | 20.42 | A | C |
| ATOM | 4237 | CG | TRP | A | 266 | 54.261 | −14.891 | 4.247 | 1.00 | 19.95 | A | C |
| ATOM | 4238 | CD1 | TRP | A | 266 | 53.460 | −14.889 | 3.143 | 1.00 | 19.27 | A | C |
| ATOM | 4240 | NE1 | TRP | A | 266 | 52.339 | −15.648 | 3.368 | 1.00 | 19.44 | A | N |
| ATOM | 4242 | CE2 | TRP | A | 266 | 52.394 | −16.154 | 4.639 | 1.00 | 19.32 | A | C |
| ATOM | 4243 | CD2 | TRP | A | 266 | 53.595 | −15.697 | 5.223 | 1.00 | 19.63 | A | C |
| ATOM | 4244 | CE3 | TRP | A | 266 | 53.895 | −16.075 | 6.537 | 1.00 | 20.02 | A | C |
| ATOM | 4246 | CZ3 | TRP | A | 266 | 53.000 | −16.890 | 7.215 | 1.00 | 20.91 | A | C |
| ATOM | 4248 | CH2 | TRP | A | 266 | 51.812 | −17.331 | 6.604 | 1.00 | 19.64 | A | C |
| ATOM | 4250 | CZ2 | TRP | A | 266 | 51.493 | −16.975 | 5.321 | 1.00 | 18.62 | A | C |
| ATOM | 4252 | C | TRP | A | 266 | 56.509 | −15.411 | 2.416 | 1.00 | 19.60 | A | C |
| ATOM | 4253 | O | TRP | A | 266 | 56.278 | −16.590 | 2.146 | 1.00 | 19.63 | A | O |
| ATOM | 4255 | N | ALA | A | 267 | 56.556 | −14.446 | 1.498 | 1.00 | 18.71 | A | N |
| ATOM | 4256 | CA | ALA | A | 267 | 56.272 | −14.687 | 0.081 | 1.00 | 18.06 | A | C |
| ATOM | 4258 | CB | ALA | A | 267 | 56.264 | −13.372 | −0.682 | 1.00 | 18.02 | A | C |
| ATOM | 4262 | C | ALA | A | 267 | 57.241 | −15.669 | −0.581 | 1.00 | 17.64 | A | C |
| ATOM | 4263 | O | ALA | A | 267 | 56.872 | −16.341 | −1.542 | 1.00 | 17.61 | A | O |
| ATOM | 4265 | N | VAL | A | 268 | 58.470 | −15.748 | −0.069 | 1.00 | 17.18 | A | N |
| ATOM | 4266 | CA | VAL | A | 268 | 59.479 | −16.690 | −0.579 | 1.00 | 16.54 | A | C |
| ATOM | 4268 | CB | VAL | A | 268 | 60.872 | −16.405 | 0.039 | 1.00 | 16.49 | A | C |
| ATOM | 4270 | CG1 | VAL | A | 268 | 61.390 | −15.062 | −0.451 | 1.00 | 16.73 | A | C |
| ATOM | 4274 | CG2 | VAL | A | 268 | 61.866 | −17.511 | −0.297 | 1.00 | 16.29 | A | C |
| ATOM | 4278 | C | VAL | A | 268 | 59.080 | −18.154 | −0.340 | 1.00 | 15.77 | A | C |
| ATOM | 4279 | O | VAL | A | 268 | 59.385 | −19.028 | −1.150 | 1.00 | 15.33 | A | O |
| ATOM | 4281 | N | GLY | A | 269 | 58.395 | −18.415 | 0.766 | 1.00 | 15.52 | A | N |
| ATOM | 4282 | CA | GLY | A | 269 | 57.832 | −19.737 | 1.016 | 1.00 | 15.52 | A | C |
| ATOM | 4285 | C | GLY | A | 269 | 56.673 | −20.066 | 0.090 | 1.00 | 15.20 | A | C |
| ATOM | 4286 | O | GLY | A | 269 | 56.391 | −21.237 | −0.160 | 1.00 | 14.64 | A | O |
| ATOM | 4288 | N | VAL | A | 270 | 56.007 | −19.032 | −0.419 | 1.00 | 14.97 | A | N |
| ATOM | 4289 | CA | VAL | A | 270 | 54.835 | −19.200 | −1.280 | 1.00 | 14.94 | A | C |
| ATOM | 4291 | CB | VAL | A | 270 | 53.887 | −17.979 | −1.178 | 1.00 | 14.38 | A | C |
| ATOM | 4293 | CG1 | VAL | A | 270 | 52.554 | −18.286 | −1.826 | 1.00 | 13.66 | A | C |
| ATOM | 4297 | CG2 | VAL | A | 270 | 53.677 | −17.584 | 0.272 | 1.00 | 12.55 | A | C |
| ATOM | 4301 | C | VAL | A | 270 | 55.230 | −19.429 | −2.747 | 1.00 | 15.75 | A | C |
| ATOM | 4302 | O | VAL | A | 270 | 54.475 | −20.036 | −3.508 | 1.00 | 16.17 | A | O |
| ATOM | 4304 | N | ALA | A | 271 | 56.410 | −18.948 | −3.140 | 1.00 | 16.28 | A | N |
| ATOM | 4305 | CA | ALA | A | 271 | 56.906 | −19.120 | −4.510 | 1.00 | 16.56 | A | C |
| ATOM | 4307 | CB | ALA | A | 271 | 56.190 | −18.161 | −5.450 | 1.00 | 16.49 | A | C |
| ATOM | 4311 | C | ALA | A | 271 | 58.429 | −18.926 | −4.586 | 1.00 | 16.90 | A | C |
| ATOM | 4312 | O | ALA | A | 271 | 58.925 | −17.849 | −4.925 | 1.00 | 16.39 | A | O |
| ATOM | 4314 | N | PHE | A | 272 | 59.155 | −19.993 | −4.273 | 1.00 | 17.53 | A | N |
| ATOM | 4315 | CA | PHE | A | 272 | 60.616 | −19.960 | −4.183 | 1.00 | 18.21 | A | C |
| ATOM | 4317 | CB | PHE | A | 272 | 61.119 | −21.181 | −3.416 | 1.00 | 18.52 | A | C |
| ATOM | 4320 | CG | PHE | A | 272 | 61.061 | −22.460 | −4.207 | 1.00 | 19.27 | A | C |
| ATOM | 4321 | CD1 | PHE | A | 272 | 62.180 | −22.915 | −4.894 | 1.00 | 19.23 | A | C |
| ATOM | 4323 | CE1 | PHE | A | 272 | 62.132 | −24.095 | −5.624 | 1.00 | 21.26 | A | C |
| ATOM | 4325 | CZ | PHE | A | 272 | 60.951 | −24.832 | −5.677 | 1.00 | 22.55 | A | C |
| ATOM | 4327 | CE2 | PHE | A | 272 | 59.825 | −24.383 | −4.999 | 1.00 | 21.20 | A | C |
| ATOM | 4329 | CD2 | PHE | A | 272 | 59.885 | −23.204 | −4.271 | 1.00 | 20.42 | A | C |
| ATOM | 4331 | C | PHE | A | 272 | 61.325 | −19.925 | −5.533 | 1.00 | 18.82 | A | C |
| ATOM | 4332 | O | PHE | A | 272 | 62.415 | −19.362 | −5.642 | 1.00 | 19.34 | A | O |
| ATOM | 4334 | N | GLU | A | 273 | 60.728 | −20.554 | −6.545 | 1.00 | 19.20 | A | N |
| ATOM | 4335 | CA | GLU | A | 273 | 61.364 | −20.679 | −7.859 | 1.00 | 19.20 | A | C |
| ATOM | 4337 | CB | GLU | A | 273 | 60.476 | −21.457 | −8.842 | 1.00 | 19.46 | A | C |
| ATOM | 4340 | CG | GLU | A | 273 | 60.093 | −22.880 | −8.399 | 1.00 | 20.71 | A | C |
| ATOM | 4343 | CD | GLU | A | 273 | 58.655 | −23.005 | −7.879 | 1.00 | 22.87 | A | C |
| ATOM | 4344 | OE1 | GLU | A | 273 | 58.171 | −22.086 | −7.178 | 1.00 | 22.37 | A | O |
| ATOM | 4345 | OE2 | GLU | A | 273 | 58.008 | −24.035 | −8.173 | 1.00 | 22.23 | A | O |
| ATOM | 4346 | C | GLU | A | 273 | 61.680 | −19.288 | −8.416 | 1.00 | 18.84 | A | C |

TABLE 8-2-continued

Coordinates for L494P Structure

| ATOM | 4347 | O   | GLU | A | 273 | 60.846 | −18.388 | −8.333  | 1.00 | 19.02 A | O |
|------|------|-----|-----|---|-----|--------|---------|---------|------|---------|---|
| ATOM | 4349 | N   | PRO | A | 274 | 62.887 | −19.108 | −8.984  | 1.00 | 18.67 A | N |
| ATOM | 4350 | CA  | PRO | A | 274 | 63.353 | −17.773 | −9.375  | 1.00 | 18.87 A | C |
| ATOM | 4352 | CB  | PRO | A | 274 | 64.762 | −18.034 | −9.924  | 1.00 | 18.89 A | C |
| ATOM | 4355 | CG  | PRO | A | 274 | 64.786 | −19.471 | −10.280 | 1.00 | 18.67 A | C |
| ATOM | 4358 | CD  | PRO | A | 274 | 63.861 | −20.157 | −9.335  | 1.00 | 18.65 A | C |
| ATOM | 4361 | C   | PRO | A | 274 | 62.487 | −17.066 | −10.422 | 1.00 | 19.21 A | C |
| ATOM | 4362 | O   | PRO | A | 274 | 62.470 | −15.837 | −10.467 | 1.00 | 19.76 A | O |
| ATOM | 4363 | N   | GLN | A | 275 | 61.771 | −17.829 | −11.243 | 1.00 | 19.37 A | N |
| ATOM | 4364 | CA  | GLN | A | 275 | 60.924 | −17.247 | −12.286 | 1.00 | 19.69 A | C |
| ATOM | 4366 | CB  | GLN | A | 275 | 60.631 | −18.272 | −13.395 | 1.00 | 19.95 A | C |
| ATOM | 4369 | CG  | GLN | A | 275 | 59.739 | −19.459 | −12.995 | 1.00 | 20.88 A | C |
| ATOM | 4372 | CD  | GLN | A | 275 | 60.526 | −20.705 | −12.614 | 1.00 | 21.94 A | C |
| ATOM | 4373 | OE1 | GLN | A | 275 | 61.655 | −20.620 | −12.130 | 1.00 | 24.29 A | O |
| ATOM | 4374 | NE2 | GLN | A | 275 | 59.924 | −21.870 | −12.826 | 1.00 | 22.72 A | N |
| ATOM | 4377 | C   | GLN | A | 275 | 59.607 | −16.633 | −11.782 | 1.00 | 19.72 A | C |
| ATOM | 4378 | O   | GLN | A | 275 | 58.905 | −15.991 | −12.562 | 1.00 | 20.27 A | O |
| ATOM | 4380 | N   | TYR | A | 276 | 59.270 | −16.819 | −10.504 | 1.00 | 19.68 A | N |
| ATOM | 4381 | CA  | TYR | A | 276 | 58.020 | −16.279 | −9.942  | 1.00 | 19.96 A | C |
| ATOM | 4383 | CB  | TYR | A | 276 | 57.339 | −17.321 | −9.044  | 1.00 | 20.06 A | C |
| ATOM | 4386 | CG  | TYR | A | 276 | 56.799 | −18.541 | −9.762  | 1.00 | 21.44 A | C |
| ATOM | 4387 | CD1 | TYR | A | 276 | 55.960 | −18.417 | −10.867 | 1.00 | 21.90 A | C |
| ATOM | 4389 | CE1 | TYR | A | 276 | 55.455 | −19.537 | −11.516 | 1.00 | 22.01 A | C |
| ATOM | 4391 | CZ  | TYR | A | 276 | 55.773 | −20.800 | −11.051 | 1.00 | 23.26 A | C |
| ATOM | 4392 | OH  | TYR | A | 276 | 55.276 | −21.917 | −11.683 | 1.00 | 24.08 A | O |
| ATOM | 4394 | CE2 | TYR | A | 276 | 56.592 | −20.949 | −9.946  | 1.00 | 23.34 A | C |
| ATOM | 4396 | CD2 | TYR | A | 276 | 57.095 | −19.824 | −9.306  | 1.00 | 22.64 A | C |
| ATOM | 4398 | C   | TYR | A | 276 | 58.219 | −14.977 | −9.147  | 1.00 | 19.98 A | C |
| ATOM | 4399 | O   | TYR | A | 276 | 57.639 | −14.802 | −8.072  | 1.00 | 19.72 A | O |
| ATOM | 4401 | N   | SER | A | 277 | 59.021 | −14.059 | −9.682  | 1.00 | 20.07 A | N |
| ATOM | 4402 | CA  | SER | A | 277 | 59.270 | −12.770 | −9.027  | 1.00 | 19.67 A | C |
| ATOM | 4404 | CB  | SER | A | 277 | 60.267 | −11.938 | −9.838  | 1.00 | 19.60 A | C |
| ATOM | 4407 | OG  | SER | A | 277 | 61.513 | −12.603 | −9.956  | 1.00 | 20.14 A | O |
| ATOM | 4409 | C   | SER | A | 277 | 57.984 | −11.973 | −8.822  | 1.00 | 19.33 A | C |
| ATOM | 4410 | O   | SER | A | 277 | 57.776 | −11.385 | −7.761  | 1.00 | 19.21 A | O |
| ATOM | 4412 | N   | ASP | A | 278 | 57.123 | −11.959 | −9.835  | 1.00 | 19.20 A | N |
| ATOM | 4413 | CA  | ASP | A | 278 | 55.859 | −11.226 | −9.754  | 1.00 | 19.25 A | C |
| ATOM | 4415 | CB  | ASP | A | 278 | 55.085 | −11.316 | −11.077 | 1.00 | 19.35 A | C |
| ATOM | 4418 | CG  | ASP | A | 278 | 55.629 | −10.380 | −12.143 | 1.00 | 18.93 A | C |
| ATOM | 4419 | OD1 | ASP | A | 278 | 56.348 | −9.419  | −11.796 | 1.00 | 18.90 A | O |
| ATOM | 4420 | OD2 | ASP | A | 278 | 55.327 | −10.600 | −13.333 | 1.00 | 18.56 A | O |
| ATOM | 4421 | C   | ASP | A | 278 | 54.979 | −11.716 | −8.606  | 1.00 | 19.13 A | C |
| ATOM | 4422 | O   | ASP | A | 278 | 54.356 | −10.908 | −7.916  | 1.00 | 19.10 A | O |
| ATOM | 4424 | N   | CYS | A | 279 | 54.930 | −13.031 | −8.403  | 1.00 | 18.93 A | N |
| ATOM | 4425 | CA  | CYS | A | 279 | 54.146 | −13.601 | −7.307  | 1.00 | 18.82 A | C |
| ATOM | 4427 | CB  | CYS | A | 279 | 54.090 | −15.129 | −7.401  | 1.00 | 18.89 A | C |
| ATOM | 4430 | SG  | CYS | A | 279 | 52.896 | −15.884 | −6.264  | 1.00 | 18.55 A | S |
| ATOM | 4432 | C   | CYS | A | 279 | 54.716 | −13.185 | −5.956  | 1.00 | 18.54 A | C |
| ATOM | 4433 | O   | CYS | A | 279 | 53.965 | −12.865 | −5.033  | 1.00 | 18.37 A | O |
| ATOM | 4435 | N   | ARG | A | 280 | 56.044 | −13.189 | −5.853  | 1.00 | 18.40 A | N |
| ATOM | 4436 | CA  | ARG | A | 280 | 56.730 | −12.759 | −4.635  | 1.00 | 18.00 A | C |
| ATOM | 4438 | CB  | ARG | A | 280 | 58.239 | −13.013 | −4.735  | 1.00 | 18.28 A | C |
| ATOM | 4441 | CG  | ARG | A | 280 | 58.634 | −14.477 | −4.592  | 1.00 | 18.99 A | C |
| ATOM | 4444 | CD  | ARG | A | 280 | 60.137 | −14.630 | −4.420  | 1.00 | 19.95 A | C |
| ATOM | 4447 | NE  | ARG | A | 280 | 60.867 | −14.212 | −5.615  | 1.00 | 21.16 A | N |
| ATOM | 4449 | CZ  | ARG | A | 280 | 61.053 | −14.964 | −6.700  | 1.00 | 23.15 A | C |
| ATOM | 4450 | NH1 | ARG | A | 280 | 60.562 | −16.198 | −6.772  | 1.00 | 24.11 A | N |
| ATOM | 4453 | NH2 | ARG | A | 280 | 61.736 | −14.475 | −7.728  | 1.00 | 24.44 A | N |
| ATOM | 4456 | C   | ARG | A | 280 | 56.464 | −11.285 | −4.344  | 1.00 | 17.11 A | C |
| ATOM | 4457 | O   | ARG | A | 280 | 56.147 | −10.923 | −3.210  | 1.00 | 16.85 A | O |
| ATOM | 4459 | N   | ASN | A | 281 | 56.586 | −10.443 | −5.369  | 1.00 | 16.30 A | N |
| ATOM | 4460 | CA  | ASN | A | 281 | 56.313 | −9.014  | −5.220  | 1.00 | 15.91 A | C |
| ATOM | 4462 | CB  | ASN | A | 281 | 56.684 | −8.244  | −6.493  | 1.00 | 16.20 A | C |
| ATOM | 4465 | CG  | ASN | A | 281 | 58.192 | −8.136  | −6.703  | 1.00 | 17.16 A | C |
| ATOM | 4466 | OD1 | ASN | A | 281 | 58.988 | −8.551  | −5.858  | 1.00 | 17.08 A | O |
| ATOM | 4467 | ND2 | ASN | A | 281 | 58.588 | −7.568  | −7.839  | 1.00 | 18.22 A | N |
| ATOM | 4470 | C   | ASN | A | 281 | 54.857 | −8.741  | −4.841  | 1.00 | 15.14 A | C |
| ATOM | 4471 | O   | ASN | A | 281 | 54.595 | −7.924  | −3.964  | 1.00 | 15.32 A | O |
| ATOM | 4473 | N   | SER | A | 282 | 53.920 | −9.432  | −5.491  | 1.00 | 14.30 A | N |
| ATOM | 4474 | CA  | SER | A | 282 | 52.494 | −9.294  | −5.173  | 1.00 | 13.39 A | C |
| ATOM | 4476 | CB  | SER | A | 282 | 51.631 | −10.127 | −6.124  | 1.00 | 13.27 A | C |
| ATOM | 4479 | OG  | SER | A | 282 | 51.539 | −9.524  | −7.400  | 1.00 | 13.30 A | O |
| ATOM | 4481 | C   | SER | A | 282 | 52.202 | −9.701  | −3.731  | 1.00 | 12.98 A | C |
| ATOM | 4482 | O   | SER | A | 282 | 51.743 | −8.880  | −2.933  | 1.00 | 12.94 A | O |
| ATOM | 4484 | N   | VAL | A | 283 | 52.471 | −10.963 | −3.402  | 1.00 | 12.45 A | N |
| ATOM | 4485 | CA  | VAL | A | 283 | 52.241 | −11.475 | −2.050  | 1.00 | 12.34 A | C |
| ATOM | 4487 | CB  | VAL | A | 283 | 52.831 | −12.895 | −1.858  | 1.00 | 12.07 A | C |
| ATOM | 4489 | CG1 | VAL | A | 283 | 52.867 | −13.272 | −0.387  | 1.00 | 11.16 A | C |

TABLE 8-2-continued

Coordinates for L494P Structure

| ATOM | 4493 | CG2 | VAL | A | 283 | 52.029 | −13.918 | −2.639 | 1.00 | 10.41 | A | C |
|---|---|---|---|---|---|---|---|---|---|---|---|---|
| ATOM | 4497 | C | VAL | A | 283 | 52.837 | −10.520 | −1.015 | 1.00 | 12.92 | A | C |
| ATOM | 4498 | O | VAL | A | 283 | 52.173 | −10.150 | −0.048 | 1.00 | 12.86 | A | O |
| ATOM | 4500 | N | ALA | A | 284 | 54.082 | −10.111 | −1.243 | 1.00 | 13.80 | A | N |
| ATOM | 4501 | CA | ALA | A | 284 | 54.772 | −9.179 | −0.351 | 1.00 | 14.74 | A | C |
| ATOM | 4503 | CB | ALA | A | 284 | 56.179 | −8.900 | −0.871 | 1.00 | 14.73 | A | C |
| ATOM | 4507 | C | ALA | A | 284 | 54.006 | −7.864 | −0.172 | 1.00 | 15.30 | A | C |
| ATOM | 4508 | O | ALA | A | 284 | 53.811 | −7.400 | 0.952 | 1.00 | 14.93 | A | O |
| ATOM | 4510 | N | LYS | A | 285 | 53.578 | −7.272 | −1.283 | 1.00 | 16.13 | A | N |
| ATOM | 4511 | CA | LYS | A | 285 | 52.841 | −6.012 | −1.248 | 1.00 | 17.03 | A | C |
| ATOM | 4513 | CB | LYS | A | 285 | 52.562 | −5.503 | −2.668 | 1.00 | 17.14 | A | C |
| ATOM | 4516 | CG | LYS | A | 285 | 53.756 | −4.834 | −3.335 | 1.00 | 18.60 | A | C |
| ATOM | 4519 | CD | LYS | A | 285 | 53.407 | −4.320 | −4.722 | 1.00 | 21.08 | A | C |
| ATOM | 4522 | CE | LYS | A | 285 | 54.618 | −3.718 | −5.417 | 1.00 | 22.65 | A | C |
| ATOM | 4525 | NZ | LYS | A | 285 | 54.341 | −3.399 | −6.848 | 1.00 | 24.04 | A | N |
| ATOM | 4529 | C | LYS | A | 285 | 51.529 | −6.160 | −0.481 | 1.00 | 17.73 | A | C |
| ATOM | 4530 | O | LYS | A | 285 | 51.239 | −5.379 | 0.431 | 1.00 | 17.94 | A | O |
| ATOM | 4532 | N | MET | A | 286 | 50.747 | −7.171 | −0.846 | 1.00 | 18.03 | A | N |
| ATOM | 4533 | CA | MET | A | 286 | 49.426 | −7.367 | −0.253 | 1.00 | 18.01 | A | C |
| ATOM | 4535 | CB | MET | A | 286 | 48.670 | −8.498 | −0.966 | 1.00 | 18.01 | A | C |
| ATOM | 4538 | CG | MET | A | 286 | 48.323 | −8.209 | −2.429 | 1.00 | 17.41 | A | C |
| ATOM | 4541 | SD | MET | A | 286 | 47.631 | −6.560 | −2.713 | 1.00 | 16.92 | A | S |
| ATOM | 4542 | CE | MET | A | 286 | 49.115 | −5.597 | −2.995 | 1.00 | 16.98 | A | C |
| ATOM | 4546 | C | MET | A | 286 | 49.524 | −7.651 | 1.240 | 1.00 | 17.81 | A | C |
| ATOM | 4547 | O | MET | A | 286 | 48.835 | −7.017 | 2.042 | 1.00 | 17.92 | A | O |
| ATOM | 4549 | N | PHE | A | 287 | 50.394 | −8.587 | 1.606 | 1.00 | 17.47 | A | N |
| ATOM | 4550 | CA | PHE | A | 287 | 50.575 | −8.976 | 3.007 | 1.00 | 17.44 | A | C |
| ATOM | 4552 | CB | PHE | A | 287 | 51.516 | −10.186 | 3.094 | 1.00 | 17.98 | A | C |
| ATOM | 4555 | CG | PHE | A | 287 | 51.463 | −10.925 | 4.409 | 1.00 | 20.17 | A | C |
| ATOM | 4556 | CD1 | PHE | A | 287 | 50.248 | −11.252 | 5.004 | 1.00 | 22.99 | A | C |
| ATOM | 4558 | CE1 | PHE | A | 287 | 50.204 | −11.947 | 6.205 | 1.00 | 23.48 | A | C |
| ATOM | 4560 | CZ | PHE | A | 287 | 51.380 | −12.337 | 6.820 | 1.00 | 25.00 | A | C |
| ATOM | 4562 | CE2 | PHE | A | 287 | 52.598 | −12.029 | 6.233 | 1.00 | 25.35 | A | C |
| ATOM | 4564 | CD2 | PHE | A | 287 | 52.634 | −11.332 | 5.032 | 1.00 | 23.16 | A | C |
| ATOM | 4566 | C | PHE | A | 287 | 51.096 | −7.818 | 3.871 | 1.00 | 16.40 | A | C |
| ATOM | 4567 | O | PHE | A | 287 | 50.848 | −7.781 | 5.076 | 1.00 | 15.60 | A | O |
| ATOM | 4569 | N | SER | A | 288 | 51.809 | −6.879 | 3.250 | 1.00 | 15.81 | A | N |
| ATOM | 4570 | CA | SER | A | 288 | 52.251 | −5.667 | 3.934 | 1.00 | 15.38 | A | C |
| ATOM | 4572 | CB | SER | A | 288 | 53.333 | −4.945 | 3.131 | 1.00 | 15.38 | A | C |
| ATOM | 4575 | OG | SER | A | 288 | 54.539 | −5.688 | 3.137 | 1.00 | 15.78 | A | O |
| ATOM | 4577 | C | SER | A | 288 | 51.081 | −4.728 | 4.202 | 1.00 | 15.29 | A | C |
| ATOM | 4578 | O | SER | A | 288 | 51.029 | −4.099 | 5.256 | 1.00 | 15.32 | A | O |
| ATOM | 4580 | N | PHE | A | 289 | 50.149 | −4.631 | 3.253 | 1.00 | 15.52 | A | N |
| ATOM | 4581 | CA | PHE | A | 289 | 48.899 | −3.885 | 3.480 | 1.00 | 15.49 | A | C |
| ATOM | 4583 | CB | PHE | A | 289 | 48.121 | −3.650 | 2.176 | 1.00 | 15.43 | A | C |
| ATOM | 4586 | CG | PHE | A | 289 | 48.484 | −2.367 | 1.479 | 1.00 | 15.12 | A | C |
| ATOM | 4587 | CD1 | PHE | A | 289 | 48.164 | −1.144 | 2.049 | 1.00 | 14.80 | A | C |
| ATOM | 4589 | CE1 | PHE | A | 289 | 48.499 | 0.040 | 1.420 | 1.00 | 16.15 | A | C |
| ATOM | 4591 | CZ | PHE | A | 289 | 49.159 | 0.011 | 0.206 | 1.00 | 17.05 | A | C |
| ATOM | 4593 | CE2 | PHE | A | 289 | 49.479 | −1.204 | −0.376 | 1.00 | 17.05 | A | C |
| ATOM | 4595 | CD2 | PHE | A | 289 | 49.144 | −2.383 | 0.261 | 1.00 | 16.16 | A | C |
| ATOM | 4597 | C | PHE | A | 289 | 48.002 | −4.582 | 4.503 | 1.00 | 15.27 | A | C |
| ATOM | 4598 | O | PHE | A | 289 | 47.393 | −3.923 | 5.345 | 1.00 | 15.17 | A | O |
| ATOM | 4600 | N | VAL | A | 290 | 47.935 | −5.910 | 4.431 | 1.00 | 15.14 | A | N |
| ATOM | 4601 | CA | VAL | A | 290 | 47.139 | −6.696 | 5.373 | 1.00 | 15.03 | A | C |
| ATOM | 4603 | CB | VAL | A | 290 | 47.224 | −8.201 | 5.068 | 1.00 | 14.64 | A | C |
| ATOM | 4605 | CG1 | VAL | A | 290 | 46.571 | −9.010 | 6.175 | 1.00 | 14.66 | A | C |
| ATOM | 4609 | CG2 | VAL | A | 290 | 46.562 | −8.497 | 3.739 | 1.00 | 14.94 | A | C |
| ATOM | 4613 | C | VAL | A | 290 | 47.551 | −6.445 | 6.827 | 1.00 | 15.27 | A | C |
| ATOM | 4614 | O | VAL | A | 290 | 46.698 | −6.185 | 7.673 | 1.00 | 15.36 | A | O |
| ATOM | 4616 | N | THR | A | 291 | 48.851 | −6.503 | 7.110 | 1.00 | 15.61 | A | N |
| ATOM | 4617 | CA | THR | A | 291 | 49.340 | −6.286 | 8.477 | 1.00 | 15.61 | A | C |
| ATOM | 4619 | CB | THR | A | 291 | 50.886 | −6.410 | 8.595 | 1.00 | 15.42 | A | C |
| ATOM | 4621 | OG1 | THR | A | 291 | 51.520 | −5.386 | 7.819 | 1.00 | 14.83 | A | O |
| ATOM | 4623 | CG2 | THR | A | 291 | 51.369 | −7.784 | 8.132 | 1.00 | 14.64 | A | C |
| ATOM | 4627 | C | THR | A | 291 | 48.911 | −4.916 | 9.001 | 1.00 | 15.68 | A | C |
| ATOM | 4628 | O | THR | A | 291 | 48.504 | −4.791 | 10.157 | 1.00 | 16.01 | A | O |
| ATOM | 4630 | N | ILE | A | 292 | 48.991 | −3.903 | 8.141 | 1.00 | 15.70 | A | N |
| ATOM | 4631 | CA | ILE | A | 292 | 48.639 | −2.533 | 8.516 | 1.00 | 15.64 | A | C |
| ATOM | 4633 | CB | ILE | A | 292 | 49.192 | −1.505 | 7.500 | 1.00 | 15.68 | A | C |
| ATOM | 4635 | CG1 | ILE | A | 292 | 50.722 | −1.490 | 7.557 | 1.00 | 15.54 | A | C |
| ATOM | 4638 | CD1 | ILE | A | 292 | 51.357 | −0.392 | 6.739 | 1.00 | 16.00 | A | C |
| ATOM | 4642 | CG2 | ILE | A | 292 | 48.639 | −0.108 | 7.780 | 1.00 | 15.12 | A | C |
| ATOM | 4646 | C | ILE | A | 292 | 47.131 | −2.359 | 8.661 | 1.00 | 15.48 | A | C |
| ATOM | 4647 | O | ILE | A | 292 | 46.669 | −1.760 | 9.631 | 1.00 | 15.61 | A | O |
| ATOM | 4649 | N | ILE | A | 293 | 46.367 | −2.885 | 7.708 | 1.00 | 15.26 | A | N |
| ATOM | 4650 | CA | ILE | A | 293 | 44.909 | −2.805 | 7.779 | 1.00 | 15.32 | A | C |
| ATOM | 4652 | CB | ILE | A | 293 | 44.231 | −3.333 | 6.495 | 1.00 | 15.16 | A | C |

TABLE 8-2-continued

Coordinates for L494P Structure

| ATOM | 4654 | CG1 | ILE | A | 293 | 44.602 | −2.472 | 5.282 | 1.00 | 15.39 | A | C |
|---|---|---|---|---|---|---|---|---|---|---|---|---|
| ATOM | 4657 | CD1 | ILE | A | 293 | 43.968 | −1.107 | 5.275 | 1.00 | 15.43 | A | C |
| ATOM | 4661 | CG2 | ILE | A | 293 | 42.719 | −3.348 | 6.658 | 1.00 | 15.54 | A | C |
| ATOM | 4665 | C | ILE | A | 293 | 44.394 | −3.586 | 8.991 | 1.00 | 15.79 | A | C |
| ATOM | 4666 | O | ILE | A | 293 | 43.465 | −3.144 | 9.664 | 1.00 | 15.61 | A | O |
| ATOM | 4668 | N | ASP | A | 294 | 45.012 | −4.733 | 9.273 | 1.00 | 16.58 | A | N |
| ATOM | 4669 | CA | ASP | A | 294 | 44.653 | −5.541 | 10.445 | 1.00 | 17.14 | A | C |
| ATOM | 4671 | CB | ASP | A | 294 | 45.511 | −6.814 | 10.521 | 1.00 | 17.55 | A | C |
| ATOM | 4674 | CG | ASP | A | 294 | 45.018 | −7.803 | 11.576 | 1.00 | 18.98 | A | C |
| ATOM | 4675 | OD1 | ASP | A | 294 | 43.790 | −7.884 | 11.806 | 1.00 | 20.79 | A | O |
| ATOM | 4676 | OD2 | ASP | A | 294 | 45.861 | −8.513 | 12.169 | 1.00 | 18.90 | A | O |
| ATOM | 4677 | C | ASP | A | 294 | 44.788 | −4.741 | 11.743 | 1.00 | 16.97 | A | C |
| ATOM | 4678 | O | ASP | A | 294 | 43.999 | −4.924 | 12.667 | 1.00 | 17.05 | A | O |
| ATOM | 4680 | N | ASP | A | 295 | 45.781 | −3.857 | 11.808 | 1.00 | 16.76 | A | N |
| ATOM | 4681 | CA | ASP | A | 295 | 45.937 | −2.965 | 12.958 | 1.00 | 16.73 | A | C |
| ATOM | 4683 | CB | ASP | A | 295 | 47.305 | −2.268 | 12.940 | 1.00 | 16.88 | A | C |
| ATOM | 4686 | CG | ASP | A | 295 | 48.461 | −3.220 | 13.210 | 1.00 | 17.30 | A | C |
| ATOM | 4687 | OD1 | ASP | A | 295 | 48.224 | −4.372 | 13.634 | 1.00 | 17.28 | A | O |
| ATOM | 4688 | OD2 | ASP | A | 295 | 49.620 | −2.806 | 12.998 | 1.00 | 18.54 | A | O |
| ATOM | 4689 | C | ASP | A | 295 | 44.825 | −1.915 | 13.018 | 1.00 | 16.43 | A | C |
| ATOM | 4690 | O | ASP | A | 295 | 44.347 | −1.589 | 14.105 | 1.00 | 16.59 | A | O |
| ATOM | 4692 | N | ILE | A | 296 | 44.420 | −1.390 | 11.859 | 1.00 | 15.90 | A | N |
| ATOM | 4693 | CA | ILE | A | 296 | 43.353 | −0.378 | 11.791 | 1.00 | 15.30 | A | C |
| ATOM | 4695 | CB | ILE | A | 296 | 43.100 | 0.114 | 10.346 | 1.00 | 14.79 | A | C |
| ATOM | 4697 | CG1 | ILE | A | 296 | 44.304 | 0.885 | 9.813 | 1.00 | 14.50 | A | C |
| ATOM | 4700 | CD1 | ILE | A | 296 | 44.210 | 1.200 | 8.336 | 1.00 | 13.16 | A | C |
| ATOM | 4704 | CG2 | ILE | A | 296 | 41.886 | 1.022 | 10.295 | 1.00 | 13.81 | A | C |
| ATOM | 4708 | C | ILE | A | 296 | 42.034 | −0.917 | 12.345 | 1.00 | 15.43 | A | C |
| ATOM | 4709 | O | ILE | A | 296 | 41.305 | −0.200 | 13.033 | 1.00 | 15.53 | A | O |
| ATOM | 4711 | N | TYR | A | 297 | 41.736 | −2.178 | 12.040 | 1.00 | 15.29 | A | N |
| ATOM | 4712 | CA | TYR | A | 297 | 40.501 | −2.820 | 12.495 | 1.00 | 15.11 | A | C |
| ATOM | 4714 | CB | TYR | A | 297 | 40.111 | −3.966 | 11.553 | 1.00 | 15.56 | A | C |
| ATOM | 4717 | CG | TYR | A | 297 | 39.399 | −3.528 | 10.288 | 1.00 | 16.05 | A | C |
| ATOM | 4718 | CD1 | TYR | A | 297 | 38.010 | −3.476 | 10.235 | 1.00 | 15.95 | A | C |
| ATOM | 4720 | CE1 | TYR | A | 297 | 37.348 | −3.086 | 9.081 | 1.00 | 15.39 | A | C |
| ATOM | 4722 | CZ | TYR | A | 297 | 38.074 | −2.746 | 7.959 | 1.00 | 16.60 | A | C |
| ATOM | 4723 | OH | TYR | A | 297 | 37.414 | −2.357 | 6.817 | 1.00 | 18.35 | A | O |
| ATOM | 4725 | CE2 | TYR | A | 297 | 39.456 | −2.794 | 7.982 | 1.00 | 16.80 | A | C |
| ATOM | 4727 | CD2 | TYR | A | 297 | 40.110 | −3.187 | 9.142 | 1.00 | 16.66 | A | C |
| ATOM | 4729 | C | TYR | A | 297 | 40.601 | −3.343 | 13.928 | 1.00 | 14.50 | A | C |
| ATOM | 4730 | O | TYR | A | 297 | 39.645 | −3.239 | 14.695 | 1.00 | 14.52 | A | O |
| ATOM | 4732 | N | ASP | A | 298 | 41.757 | −3.901 | 14.280 | 1.00 | 14.10 | A | N |
| ATOM | 4733 | CA | ASP | A | 298 | 41.949 | −4.561 | 15.575 | 1.00 | 13.63 | A | C |
| ATOM | 4735 | CB | ASP | A | 298 | 43.212 | −5.434 | 15.531 | 1.00 | 13.70 | A | C |
| ATOM | 4738 | CG | ASP | A | 298 | 43.478 | −6.162 | 16.835 | 1.00 | 13.63 | A | C |
| ATOM | 4739 | OD1 | ASP | A | 298 | 42.511 | −6.539 | 17.530 | 1.00 | 14.13 | A | O |
| ATOM | 4740 | OD2 | ASP | A | 298 | 44.666 | −6.368 | 17.156 | 1.00 | 13.89 | A | O |
| ATOM | 4741 | C | ASP | A | 298 | 42.044 | −3.573 | 16.741 | 1.00 | 13.00 | A | C |
| ATOM | 4742 | O | ASP | A | 298 | 41.295 | −3.681 | 17.710 | 1.00 | 12.88 | A | O |
| ATOM | 4744 | N | VAL | A | 299 | 42.959 | −2.614 | 16.637 | 1.00 | 12.31 | A | N |
| ATOM | 4745 | CA | VAL | A | 299 | 43.312 | −1.760 | 17.774 | 1.00 | 11.67 | A | C |
| ATOM | 4747 | CB | VAL | A | 299 | 44.805 | −1.930 | 18.142 | 1.00 | 11.42 | A | C |
| ATOM | 4749 | CG1 | VAL | A | 299 | 45.071 | −3.349 | 18.602 | 1.00 | 11.41 | A | C |
| ATOM | 4753 | CG2 | VAL | A | 299 | 45.703 | −1.574 | 16.965 | 1.00 | 10.40 | A | C |
| ATOM | 4757 | C | VAL | A | 299 | 43.020 | −0.267 | 17.587 | 1.00 | 11.59 | A | C |
| ATOM | 4758 | O | VAL | A | 299 | 42.551 | 0.385 | 18.524 | 1.00 | 11.49 | A | O |
| ATOM | 4760 | N | TYR | A | 300 | 43.289 | 0.268 | 16.394 | 1.00 | 11.13 | A | N |
| ATOM | 4761 | CA | TYR | A | 300 | 43.330 | 1.722 | 16.189 | 1.00 | 10.45 | A | C |
| ATOM | 4763 | CB | TYR | A | 300 | 44.389 | 2.094 | 15.139 | 1.00 | 9.99 | A | C |
| ATOM | 4766 | CG | TYR | A | 300 | 44.603 | 3.590 | 15.022 | 1.00 | 9.37 | A | C |
| ATOM | 4767 | CD1 | TYR | A | 300 | 45.202 | 4.309 | 16.055 | 1.00 | 9.54 | A | C |
| ATOM | 4769 | CE1 | TYR | A | 300 | 45.389 | 5.686 | 15.966 | 1.00 | 6.83 | A | C |
| ATOM | 4771 | CZ | TYR | A | 300 | 44.970 | 6.358 | 14.840 | 1.00 | 5.23 | A | C |
| ATOM | 4772 | OH | TYR | A | 300 | 45.155 | 7.715 | 14.752 | 1.00 | 3.12 | A | O |
| ATOM | 4774 | CE2 | TYR | A | 300 | 44.373 | 5.672 | 13.800 | 1.00 | 6.82 | A | C |
| ATOM | 4776 | CD2 | TYR | A | 300 | 44.188 | 4.292 | 13.896 | 1.00 | 8.25 | A | C |
| ATOM | 4778 | C | TYR | A | 300 | 41.989 | 2.370 | 15.821 | 1.00 | 10.48 | A | C |
| ATOM | 4779 | O | TYR | A | 300 | 41.675 | 3.448 | 16.317 | 1.00 | 10.25 | A | O |
| ATOM | 4781 | N | GLY | A | 301 | 41.209 | 1.729 | 14.956 | 1.00 | 11.04 | A | N |
| ATOM | 4782 | CA | GLY | A | 301 | 39.992 | 2.347 | 14.415 | 1.00 | 11.50 | A | C |
| ATOM | 4785 | C | GLY | A | 301 | 38.727 | 2.030 | 15.193 | 1.00 | 11.87 | A | C |
| ATOM | 4786 | O | GLY | A | 301 | 38.509 | 0.882 | 15.585 | 1.00 | 11.70 | A | O |
| ATOM | 4788 | N | THR | A | 302 | 37.887 | 3.045 | 15.411 | 1.00 | 12.42 | A | N |
| ATOM | 4789 | CA | THR | A | 302 | 36.572 | 2.829 | 16.024 | 1.00 | 13.04 | A | C |
| ATOM | 4791 | CB | THR | A | 302 | 35.913 | 4.137 | 16.546 | 1.00 | 13.14 | A | C |
| ATOM | 4793 | OG1 | THR | A | 302 | 35.606 | 5.009 | 15.452 | 1.00 | 14.40 | A | O |
| ATOM | 4795 | CG2 | THR | A | 302 | 36.826 | 4.852 | 17.535 | 1.00 | 12.53 | A | C |
| ATOM | 4799 | C | THR | A | 302 | 35.663 | 2.174 | 14.995 | 1.00 | 13.17 | A | C |

TABLE 8-2-continued

Coordinates for L494P Structure

| ATOM | 4800 | O   | THR | A | 302 | 35.965 | 2.180  | 13.803 | 1.00 | 12.57 | A | O |
| ATOM | 4802 | N   | LEU | A | 303 | 34.551 | 1.613  | 15.456 | 1.00 | 13.95 | A | N |
| ATOM | 4803 | CA  | LEU | A | 303 | 33.688 | 0.826  | 14.580 | 1.00 | 14.80 | A | C |
| ATOM | 4805 | CB  | LEU | A | 303 | 32.567 | 0.138  | 15.375 | 1.00 | 14.99 | A | C |
| ATOM | 4808 | CG  | LEU | A | 303 | 32.178 | −1.259 | 14.876 | 1.00 | 15.81 | A | C |
| ATOM | 4810 | CD1 | LEU | A | 303 | 33.326 | −2.239 | 15.080 | 1.00 | 16.28 | A | C |
| ATOM | 4814 | CD2 | LEU | A | 303 | 30.927 | −1.768 | 15.578 | 1.00 | 17.42 | A | C |
| ATOM | 4818 | C   | LEU | A | 303 | 33.114 | 1.690  | 13.456 | 1.00 | 15.44 | A | C |
| ATOM | 4819 | O   | LEU | A | 303 | 33.109 | 1.275  | 12.295 | 1.00 | 15.80 | A | O |
| ATOM | 4821 | N   | ASP | A | 304 | 32.659 | 2.896  | 13.803 | 1.00 | 15.85 | A | N |
| ATOM | 4822 | CA  | ASP | A | 304 | 32.105 | 3.840  | 12.823 | 1.00 | 15.89 | A | C |
| ATOM | 4824 | CB  | ASP | A | 304 | 31.645 | 5.137  | 13.509 | 1.00 | 16.11 | A | C |
| ATOM | 4827 | CG  | ASP | A | 304 | 30.370 | 4.957  | 14.326 | 1.00 | 15.63 | A | C |
| ATOM | 4828 | OD1 | ASP | A | 304 | 29.443 | 4.266  | 13.852 | 1.00 | 13.49 | A | O |
| ATOM | 4829 | OD2 | ASP | A | 304 | 30.291 | 5.522  | 15.439 | 1.00 | 14.30 | A | O |
| ATOM | 4830 | C   | ASP | A | 304 | 33.105 | 4.167  | 11.713 | 1.00 | 15.95 | A | C |
| ATOM | 4831 | O   | ASP | A | 304 | 32.728 | 4.260  | 10.544 | 1.00 | 16.02 | A | O |
| ATOM | 4833 | N   | GLU | A | 305 | 34.373 | 4.338  | 12.085 | 1.00 | 16.25 | A | N |
| ATOM | 4834 | CA  | GLU | A | 305 | 35.447 | 4.580  | 11.113 | 1.00 | 16.33 | A | C |
| ATOM | 4836 | CB  | GLU | A | 305 | 36.755 | 4.941  | 11.827 | 1.00 | 16.05 | A | C |
| ATOM | 4839 | CG  | GLU | A | 305 | 36.716 | 6.292  | 12.527 | 1.00 | 17.49 | A | C |
| ATOM | 4842 | CD  | GLU | A | 305 | 37.971 | 6.589  | 13.330 | 1.00 | 19.41 | A | C |
| ATOM | 4843 | OE1 | GLU | A | 305 | 38.649 | 5.636  | 13.773 | 1.00 | 21.25 | A | O |
| ATOM | 4844 | OE2 | GLU | A | 305 | 38.274 | 7.785  | 13.524 | 1.00 | 19.58 | A | O |
| ATOM | 4845 | C   | GLU | A | 305 | 35.667 | 3.364  | 10.215 | 1.00 | 16.21 | A | C |
| ATOM | 4846 | O   | GLU | A | 305 | 35.798 | 3.499  | 8.996  | 1.00 | 16.05 | A | O |
| ATOM | 4848 | N   | LEU | A | 306 | 35.699 | 2.183  | 10.829 | 1.00 | 16.16 | A | N |
| ATOM | 4849 | CA  | LEU | A | 306 | 35.911 | 0.930  | 10.107 | 1.00 | 15.88 | A | C |
| ATOM | 4851 | CB  | LEU | A | 306 | 36.033 | −0.235 | 11.089 | 1.00 | 15.78 | A | C |
| ATOM | 4854 | CG  | LEU | A | 306 | 37.274 | −0.232 | 11.976 | 1.00 | 15.34 | A | C |
| ATOM | 4856 | CD1 | LEU | A | 306 | 37.218 | −1.417 | 12.928 | 1.00 | 16.17 | A | C |
| ATOM | 4860 | CD2 | LEU | A | 306 | 38.541 | −0.256 | 11.134 | 1.00 | 14.22 | A | C |
| ATOM | 4864 | C   | LEU | A | 306 | 34.799 | 0.635  | 9.104  | 1.00 | 16.02 | A | C |
| ATOM | 4865 | O   | LEU | A | 306 | 35.065 | 0.112  | 8.019  | 1.00 | 15.90 | A | O |
| ATOM | 4867 | N   | GLU | A | 307 | 33.561 | 0.960  | 9.471  | 1.00 | 16.02 | A | N |
| ATOM | 4868 | CA  | GLU | A | 307 | 32.427 | 0.802  | 8.563  | 1.00 | 16.25 | A | C |
| ATOM | 4870 | CB  | GLU | A | 307 | 31.130 | 1.274  | 9.224  | 1.00 | 16.45 | A | C |
| ATOM | 4873 | CG  | GLU | A | 307 | 30.620 | 0.361  | 10.331 | 1.00 | 17.76 | A | C |
| ATOM | 4876 | CD  | GLU | A | 307 | 29.869 | −0.853 | 9.813  | 1.00 | 19.89 | A | C |
| ATOM | 4877 | OE1 | GLU | A | 307 | 29.047 | −1.399 | 10.580 | 1.00 | 22.93 | A | O |
| ATOM | 4878 | OE2 | GLU | A | 307 | 30.093 | −1.262 | 8.653  | 1.00 | 19.71 | A | O |
| ATOM | 4879 | C   | GLU | A | 307 | 32.654 | 1.572  | 7.264  | 1.00 | 16.17 | A | C |
| ATOM | 4880 | O   | GLU | A | 307 | 32.380 | 1.063  | 6.179  | 1.00 | 16.40 | A | O |
| ATOM | 4882 | N   | LEU | A | 308 | 33.163 | 2.795  | 7.383  | 1.00 | 16.07 | A | N |
| ATOM | 4883 | CA  | LEU | A | 308 | 33.456 | 3.620  | 6.213  | 1.00 | 15.87 | A | C |
| ATOM | 4885 | CB  | LEU | A | 308 | 33.850 | 5.038  | 6.634  | 1.00 | 15.51 | A | C |
| ATOM | 4888 | CG  | LEU | A | 308 | 32.759 | 5.841  | 7.341  | 1.00 | 14.36 | A | C |
| ATOM | 4890 | CD1 | LEU | A | 308 | 33.340 | 7.117  | 7.928  | 1.00 | 14.78 | A | C |
| ATOM | 4894 | CD2 | LEU | A | 308 | 31.618 | 6.151  | 6.386  | 1.00 | 12.42 | A | C |
| ATOM | 4898 | C   | LEU | A | 308 | 34.559 | 2.995  | 5.359  | 1.00 | 15.95 | A | C |
| ATOM | 4899 | O   | LEU | A | 308 | 34.422 | 2.896  | 4.140  | 1.00 | 16.08 | A | O |
| ATOM | 4901 | N   | PHE | A | 309 | 35.644 | 2.566  | 5.997  | 1.00 | 15.86 | A | N |
| ATOM | 4902 | CA  | PHE | A | 309 | 36.741 | 1.932  | 5.271  | 1.00 | 15.76 | A | C |
| ATOM | 4904 | CB  | PHE | A | 309 | 37.879 | 1.539  | 6.213  | 1.00 | 15.23 | A | C |
| ATOM | 4907 | CG  | PHE | A | 309 | 39.167 | 1.268  | 5.505  | 1.00 | 12.77 | A | C |
| ATOM | 4908 | CD1 | PHE | A | 309 | 40.023 | 2.308  | 5.187  | 1.00 | 11.18 | A | C |
| ATOM | 4910 | CE1 | PHE | A | 309 | 41.216 | 2.073  | 4.524  | 1.00 | 10.16 | A | C |
| ATOM | 4912 | CZ  | PHE | A | 309 | 41.558 | 0.788  | 4.165  | 1.00 | 11.94 | A | C |
| ATOM | 4914 | CE2 | PHE | A | 309 | 40.705 | −0.265 | 4.470  | 1.00 | 12.78 | A | C |
| ATOM | 4916 | CD2 | PHE | A | 309 | 39.515 | −0.019 | 5.136  | 1.00 | 12.55 | A | C |
| ATOM | 4918 | C   | PHE | A | 309 | 36.242 | 0.701  | 4.519  | 1.00 | 16.65 | A | C |
| ATOM | 4919 | O   | PHE | A | 309 | 36.509 | 0.545  | 3.326  | 1.00 | 16.66 | A | O |
| ATOM | 4921 | N   | THR | A | 310 | 35.515 | −0.162 | 5.227  | 1.00 | 17.62 | A | N |
| ATOM | 4922 | CA  | THR | A | 310 | 34.879 | −1.337 | 4.626  | 1.00 | 18.17 | A | C |
| ATOM | 4924 | CB  | THR | A | 310 | 33.943 | −2.053 | 5.630  | 1.00 | 18.21 | A | C |
| ATOM | 4926 | OG1 | THR | A | 310 | 34.678 | −2.429 | 6.802  | 1.00 | 18.07 | A | O |
| ATOM | 4928 | CG2 | THR | A | 310 | 33.321 | −3.292 | 4.999  | 1.00 | 18.32 | A | C |
| ATOM | 4932 | C   | THR | A | 310 | 34.057 | −0.931 | 3.407  | 1.00 | 18.50 | A | C |
| ATOM | 4933 | O   | THR | A | 310 | 34.199 | −1.514 | 2.330  | 1.00 | 18.52 | A | O |
| ATOM | 4935 | N   | ASP | A | 311 | 33.205 | 0.077  | 3.591  | 1.00 | 18.74 | A | N |
| ATOM | 4936 | CA  | ASP | A | 311 | 32.368 | 0.609  | 2.515  | 1.00 | 18.56 | A | C |
| ATOM | 4938 | CB  | ASP | A | 311 | 31.415 | 1.684  | 3.053  | 1.00 | 18.73 | A | C |
| ATOM | 4941 | CG  | ASP | A | 311 | 30.562 | 2.306  | 1.966  | 1.00 | 19.68 | A | C |
| ATOM | 4942 | OD1 | ASP | A | 311 | 29.867 | 1.552  | 1.252  | 1.00 | 21.03 | A | O |
| ATOM | 4943 | OD2 | ASP | A | 311 | 30.591 | 3.548  | 1.824  | 1.00 | 20.12 | A | O |
| ATOM | 4944 | C   | ASP | A | 311 | 33.221 | 1.186  | 1.389  | 1.00 | 17.98 | A | C |
| ATOM | 4945 | O   | ASP | A | 311 | 32.919 | 0.981  | 0.218  | 1.00 | 17.81 | A | O |
| ATOM | 4947 | N   | ALA | A | 312 | 34.288 | 1.895  | 1.754  | 1.00 | 17.60 | A | N |

TABLE 8-2-continued

Coordinates for L494P Structure

| ATOM | 4948 | CA | ALA | A | 312 | 35.207 | 2.487 | 0.779 | 1.00 | 17.18 | A | C |
|---|---|---|---|---|---|---|---|---|---|---|---|---|
| ATOM | 4950 | CB | ALA | A | 312 | 36.287 | 3.290 | 1.493 | 1.00 | 17.04 | A | C |
| ATOM | 4954 | C | ALA | A | 312 | 35.840 | 1.431 | −0.132 | 1.00 | 16.89 | A | C |
| ATOM | 4955 | O | ALA | A | 312 | 35.978 | 1.647 | −1.336 | 1.00 | 16.28 | A | O |
| ATOM | 4957 | N | VAL | A | 313 | 36.215 | 0.292 | 0.446 | 1.00 | 17.08 | A | N |
| ATOM | 4958 | CA | VAL | A | 313 | 36.777 | −0.819 | −0.326 | 1.00 | 17.48 | A | C |
| ATOM | 4960 | CB | VAL | A | 313 | 37.595 | −1.779 | 0.572 | 1.00 | 17.54 | A | C |
| ATOM | 4962 | CG1 | VAL | A | 313 | 38.729 | −1.027 | 1.260 | 1.00 | 17.32 | A | C |
| ATOM | 4966 | CG2 | VAL | A | 313 | 38.156 | −2.933 | −0.239 | 1.00 | 17.14 | A | C |
| ATOM | 4970 | C | VAL | A | 313 | 35.686 | −1.598 | −1.076 | 1.00 | 17.77 | A | C |
| ATOM | 4971 | O | VAL | A | 313 | 35.932 | −2.118 | −2.164 | 1.00 | 17.70 | A | O |
| ATOM | 4973 | N | GLU | A | 314 | 34.486 | −1.669 | −0.501 | 1.00 | 18.26 | A | N |
| ATOM | 4974 | CA | GLU | A | 314 | 33.347 | −2.332 | −1.155 | 1.00 | 18.61 | A | C |
| ATOM | 4976 | CB | GLU | A | 314 | 32.125 | −2.376 | −0.229 | 1.00 | 18.86 | A | C |
| ATOM | 4979 | CG | GLU | A | 314 | 32.105 | −3.539 | 0.747 | 1.00 | 20.58 | A | C |
| ATOM | 4982 | CD | GLU | A | 314 | 30.881 | −3.524 | 1.649 | 1.00 | 24.15 | A | C |
| ATOM | 4983 | OE1 | GLU | A | 314 | 30.876 | −4.268 | 2.652 | 1.00 | 28.09 | A | O |
| ATOM | 4984 | OE2 | GLU | A | 314 | 29.923 | −2.771 | 1.361 | 1.00 | 24.84 | A | O |
| ATOM | 4985 | C | GLU | A | 314 | 32.929 | −1.675 | −2.470 | 1.00 | 18.45 | A | C |
| ATOM | 4986 | O | GLU | A | 314 | 32.453 | −2.359 | −3.375 | 1.00 | 18.12 | A | O |
| ATOM | 4988 | N | ARG | A | 315 | 33.089 | −0.355 | −2.563 | 1.00 | 18.81 | A | N |
| ATOM | 4989 | CA | ARG | A | 315 | 32.614 | 0.405 | −3.724 | 1.00 | 19.28 | A | C |
| ATOM | 4991 | CB | ARG | A | 315 | 31.904 | 1.687 | −3.276 | 1.00 | 19.73 | A | C |
| ATOM | 4994 | CG | ARG | A | 315 | 30.876 | 1.469 | −2.149 | 1.00 | 22.35 | A | C |
| ATOM | 4997 | CD | ARG | A | 315 | 29.651 | 2.378 | −2.247 | 1.00 | 25.41 | A | C |
| ATOM | 5000 | NE | ARG | A | 315 | 29.952 | 3.667 | −2.867 | 1.00 | 29.17 | A | N |
| ATOM | 5002 | CZ | ARG | A | 315 | 30.616 | 4.665 | −2.284 | 1.00 | 32.10 | A | C |
| ATOM | 5003 | NH1 | ARG | A | 315 | 30.828 | 5.789 | −2.961 | 1.00 | 33.11 | A | N |
| ATOM | 5006 | NH2 | ARG | A | 315 | 31.072 | 4.555 | −1.038 | 1.00 | 33.08 | A | N |
| ATOM | 5009 | C | ARG | A | 315 | 33.730 | 0.733 | −4.717 | 1.00 | 18.91 | A | C |
| ATOM | 5010 | O | ARG | A | 315 | 33.484 | 0.805 | −5.921 | 1.00 | 18.78 | A | O |
| ATOM | 5012 | N | TRP | A | 316 | 34.944 | 0.936 | −4.209 | 1.00 | 18.94 | A | N |
| ATOM | 5013 | CA | TRP | A | 316 | 36.125 | 1.195 | −5.046 | 1.00 | 18.73 | A | C |
| ATOM | 5015 | CB | TRP | A | 316 | 36.366 | 0.014 | −6.002 | 1.00 | 18.53 | A | C |
| ATOM | 5018 | CG | TRP | A | 316 | 37.802 | −0.166 | −6.398 | 1.00 | 17.21 | A | C |
| ATOM | 5019 | CD1 | TRP | A | 316 | 38.330 | −0.036 | −7.649 | 1.00 | 16.88 | A | C |
| ATOM | 5021 | NE1 | TRP | A | 316 | 39.682 | −0.275 | −7.620 | 1.00 | 15.97 | A | N |
| ATOM | 5023 | CE2 | TRP | A | 316 | 40.051 | −0.566 | −6.334 | 1.00 | 15.80 | A | C |
| ATOM | 5024 | CD2 | TRP | A | 316 | 38.891 | −0.507 | −5.537 | 1.00 | 15.21 | A | C |
| ATOM | 5025 | CE3 | TRP | A | 316 | 38.999 | −0.766 | −4.167 | 1.00 | 16.69 | A | C |
| ATOM | 5027 | CZ3 | TRP | A | 316 | 40.245 | −1.073 | −3.643 | 1.00 | 17.30 | A | C |
| ATOM | 5029 | CH2 | TRP | A | 316 | 41.381 | −1.127 | −4.464 | 1.00 | 17.99 | A | C |
| ATOM | 5031 | CZ2 | TRP | A | 316 | 41.305 | −0.873 | −5.808 | 1.00 | 17.57 | A | C |
| ATOM | 5033 | C | TRP | A | 316 | 36.024 | 2.523 | −5.818 | 1.00 | 18.77 | A | C |
| ATOM | 5034 | O | TRP | A | 316 | 36.569 | 2.660 | −6.913 | 1.00 | 18.58 | A | O |
| ATOM | 5036 | N | ASP | A | 317 | 35.334 | 3.497 | −5.229 | 1.00 | 19.02 | A | N |
| ATOM | 5037 | CA | ASP | A | 317 | 35.161 | 4.811 | −5.835 | 1.00 | 19.48 | A | C |
| ATOM | 5039 | CB | ASP | A | 317 | 33.739 | 5.327 | −5.573 | 1.00 | 19.49 | A | C |
| ATOM | 5042 | CG | ASP | A | 317 | 33.471 | 6.694 | −6.199 | 1.00 | 19.09 | A | C |
| ATOM | 5043 | OD1 | ASP | A | 317 | 34.201 | 7.099 | −7.129 | 1.00 | 19.20 | A | O |
| ATOM | 5044 | OD2 | ASP | A | 317 | 32.512 | 7.365 | −5.758 | 1.00 | 17.19 | A | O |
| ATOM | 5045 | C | ASP | A | 317 | 36.202 | 5.767 | −5.253 | 1.00 | 20.22 | A | C |
| ATOM | 5046 | O | ASP | A | 317 | 36.110 | 6.161 | −4.088 | 1.00 | 20.57 | A | O |
| ATOM | 5048 | N | VAL | A | 318 | 37.188 | 6.135 | −6.070 | 1.00 | 20.71 | A | N |
| ATOM | 5049 | CA | VAL | A | 318 | 38.276 | 7.016 | −5.633 | 1.00 | 21.05 | A | C |
| ATOM | 5051 | CB | VAL | A | 318 | 39.423 | 7.038 | −6.666 | 1.00 | 20.76 | A | C |
| ATOM | 5053 | CG1 | VAL | A | 318 | 40.690 | 7.613 | −6.053 | 1.00 | 20.64 | A | C |
| ATOM | 5057 | CG2 | VAL | A | 318 | 39.017 | 7.812 | −7.911 | 1.00 | 20.38 | A | C |
| ATOM | 5061 | C | VAL | A | 318 | 37.818 | 8.456 | −5.370 | 1.00 | 21.99 | A | C |
| ATOM | 5062 | O | VAL | A | 318 | 38.528 | 9.222 | −4.719 | 1.00 | 22.30 | A | O |
| ATOM | 5064 | N | ASN | A | 319 | 36.644 | 8.821 | −5.885 | 1.00 | 22.84 | A | N |
| ATOM | 5065 | CA | ASN | A | 319 | 36.083 | 10.160 | −5.684 | 1.00 | 23.25 | A | C |
| ATOM | 5067 | CB | ASN | A | 319 | 35.177 | 10.539 | −6.862 | 1.00 | 23.24 | A | C |
| ATOM | 5070 | CG | ASN | A | 319 | 35.956 | 10.749 | −8.159 | 1.00 | 23.11 | A | C |
| ATOM | 5071 | OD1 | ASN | A | 319 | 36.802 | 11.643 | −8.255 | 1.00 | 22.22 | A | O |
| ATOM | 5072 | ND2 | ASN | A | 319 | 35.664 | 9.929 | −9.166 | 1.00 | 20.47 | A | N |
| ATOM | 5075 | C | ASN | A | 319 | 35.323 | 10.305 | −4.360 | 1.00 | 24.05 | A | C |
| ATOM | 5076 | O | ASN | A | 319 | 35.057 | 11.425 | −3.924 | 1.00 | 24.48 | A | O |
| ATOM | 5078 | N | ALA | A | 320 | 34.978 | 9.180 | −3.730 | 1.00 | 24.88 | A | N |
| ATOM | 5079 | CA | ALA | A | 320 | 34.347 | 9.180 | −2.399 | 1.00 | 25.38 | A | C |
| ATOM | 5081 | CB | ALA | A | 320 | 33.373 | 8.017 | −2.277 | 1.00 | 25.19 | A | C |
| ATOM | 5085 | C | ALA | A | 320 | 35.380 | 9.127 | −1.261 | 1.00 | 25.94 | A | C |
| ATOM | 5086 | O | ALA | A | 320 | 35.010 | 9.092 | −0.085 | 1.00 | 26.43 | A | O |
| ATOM | 5088 | N | ILE | A | 321 | 36.663 | 9.119 | −1.624 | 1.00 | 26.12 | A | N |
| ATOM | 5089 | CA | ILE | A | 321 | 37.785 | 9.144 | −0.674 | 1.00 | 26.16 | A | C |
| ATOM | 5091 | CB | ILE | A | 321 | 39.124 | 9.356 | −1.440 | 1.00 | 26.28 | A | C |
| ATOM | 5093 | CG1 | ILE | A | 321 | 40.336 | 9.088 | −0.551 | 1.00 | 25.99 | A | C |
| ATOM | 5096 | CD1 | ILE | A | 321 | 41.648 | 9.204 | −1.300 | 1.00 | 25.33 | A | C |

TABLE 8-2-continued

Coordinates for L494P Structure

| ATOM | 5100 | CG2 | ILE | A | 321 | 39.204 | 10.767 | −2.021 | 1.00 | 27.21 | A | C |
|---|---|---|---|---|---|---|---|---|---|---|---|---|
| ATOM | 5104 | C | ILE | A | 321 | 37.651 | 10.218 | 0.420 | 1.00 | 26.28 | A | C |
| ATOM | 5105 | O | ILE | A | 321 | 38.083 | 10.002 | 1.553 | 1.00 | 26.33 | A | O |
| ATOM | 5107 | N | ASN | A | 322 | 37.046 | 11.361 | 0.078 | 1.00 | 26.31 | A | N |
| ATOM | 5108 | CA | ASN | A | 322 | 36.870 | 12.485 | 1.019 | 1.00 | 26.01 | A | C |
| ATOM | 5110 | CB | ASN | A | 322 | 36.659 | 13.804 | 0.248 | 1.00 | 25.94 | A | C |
| ATOM | 5113 | CG | ASN | A | 322 | 37.960 | 14.409 | −0.261 | 1.00 | 26.56 | A | C |
| ATOM | 5114 | OD1 | ASN | A | 322 | 39.043 | 14.120 | 0.251 | 1.00 | 26.84 | A | O |
| ATOM | 5115 | ND2 | ASN | A | 322 | 37.854 | 15.266 | −1.268 | 1.00 | 27.80 | A | N |
| ATOM | 5118 | C | ASN | A | 322 | 35.751 | 12.310 | 2.062 | 1.00 | 25.35 | A | C |
| ATOM | 5119 | O | ASN | A | 322 | 35.438 | 13.253 | 2.796 | 1.00 | 25.20 | A | O |
| ATOM | 5121 | N | ASP | A | 323 | 35.153 | 11.120 | 2.126 | 1.00 | 24.45 | A | N |
| ATOM | 5122 | CA | ASP | A | 323 | 34.220 | 10.778 | 3.204 | 1.00 | 24.14 | A | C |
| ATOM | 5124 | CB | ASP | A | 323 | 33.119 | 9.836 | 2.692 | 1.00 | 24.89 | A | C |
| ATOM | 5127 | CG | ASP | A | 323 | 32.096 | 10.547 | 1.811 | 1.00 | 26.83 | A | C |
| ATOM | 5128 | OD1 | ASP | A | 323 | 31.426 | 11.480 | 2.306 | 1.00 | 27.88 | A | O |
| ATOM | 5129 | OD2 | ASP | A | 323 | 31.952 | 10.162 | 0.629 | 1.00 | 29.53 | A | O |
| ATOM | 5130 | C | ASP | A | 323 | 34.945 | 10.136 | 4.394 | 1.00 | 22.55 | A | C |
| ATOM | 5131 | O | ASP | A | 323 | 34.408 | 10.098 | 5.504 | 1.00 | 22.17 | A | O |
| ATOM | 5133 | N | LEU | A | 324 | 36.162 | 9.644 | 4.157 | 1.00 | 21.03 | A | N |
| ATOM | 5134 | CA | LEU | A | 324 | 36.939 | 8.936 | 5.178 | 1.00 | 20.05 | A | C |
| ATOM | 5136 | CB | LEU | A | 324 | 37.933 | 7.973 | 4.518 | 1.00 | 19.99 | A | C |
| ATOM | 5139 | CG | LEU | A | 324 | 37.351 | 6.752 | 3.803 | 1.00 | 20.17 | A | C |
| ATOM | 5141 | CD1 | LEU | A | 324 | 38.422 | 6.076 | 2.962 | 1.00 | 20.22 | A | C |
| ATOM | 5145 | CD2 | LEU | A | 324 | 36.747 | 5.771 | 4.797 | 1.00 | 19.25 | A | C |
| ATOM | 5149 | C | LEU | A | 324 | 37.707 | 9.901 | 6.075 | 1.00 | 19.03 | A | C |
| ATOM | 5150 | O | LEU | A | 324 | 37.918 | 11.052 | 5.702 | 1.00 | 18.72 | A | O |
| ATOM | 5152 | N | PRO | A | 325 | 38.130 | 9.429 | 7.263 | 1.00 | 18.44 | A | N |
| ATOM | 5153 | CA | PRO | A | 325 | 39.010 | 10.213 | 8.122 | 1.00 | 18.19 | A | C |
| ATOM | 5155 | CB | PRO | A | 325 | 38.874 | 9.527 | 9.482 | 1.00 | 18.12 | A | C |
| ATOM | 5158 | CG | PRO | A | 325 | 38.558 | 8.121 | 9.159 | 1.00 | 18.05 | A | C |
| ATOM | 5161 | CD | PRO | A | 325 | 37.746 | 8.152 | 7.896 | 1.00 | 18.53 | A | C |
| ATOM | 5164 | C | PRO | A | 325 | 40.458 | 10.173 | 7.630 | 1.00 | 18.23 | A | C |
| ATOM | 5165 | O | PRO | A | 325 | 40.863 | 9.215 | 6.973 | 1.00 | 17.90 | A | O |
| ATOM | 5166 | N | ASP | A | 326 | 41.223 | 11.206 | 7.971 | 1.00 | 18.42 | A | N |
| ATOM | 5167 | CA | ASP | A | 326 | 42.555 | 11.441 | 7.400 | 1.00 | 18.51 | A | C |
| ATOM | 5169 | CB | ASP | A | 326 | 43.261 | 12.572 | 8.161 | 1.00 | 18.74 | A | C |
| ATOM | 5172 | CG | ASP | A | 326 | 42.691 | 13.945 | 7.832 | 1.00 | 20.90 | A | C |
| ATOM | 5173 | OD1 | ASP | A | 326 | 42.044 | 14.087 | 6.772 | 1.00 | 23.65 | A | O |
| ATOM | 5174 | OD2 | ASP | A | 326 | 42.891 | 14.886 | 8.632 | 1.00 | 23.58 | A | O |
| ATOM | 5175 | C | ASP | A | 326 | 43.466 | 10.209 | 7.307 | 1.00 | 18.04 | A | C |
| ATOM | 5176 | O | ASP | A | 326 | 44.037 | 9.950 | 6.246 | 1.00 | 18.16 | A | O |
| ATOM | 5178 | N | TYR | A | 327 | 43.605 | 9.453 | 8.393 | 1.00 | 17.28 | A | N |
| ATOM | 5179 | CA | TYR | A | 327 | 44.502 | 8.291 | 8.389 | 1.00 | 16.66 | A | C |
| ATOM | 5181 | CB | TYR | A | 327 | 44.728 | 7.753 | 9.807 | 1.00 | 16.33 | A | C |
| ATOM | 5184 | CG | TYR | A | 327 | 43.607 | 6.900 | 10.353 | 1.00 | 14.83 | A | C |
| ATOM | 5185 | CD1 | TYR | A | 327 | 42.558 | 7.471 | 11.061 | 1.00 | 14.91 | A | C |
| ATOM | 5187 | CE1 | TYR | A | 327 | 41.528 | 6.692 | 11.572 | 1.00 | 15.33 | A | C |
| ATOM | 5189 | CZ | TYR | A | 327 | 41.546 | 5.323 | 11.382 | 1.00 | 15.64 | A | C |
| ATOM | 5190 | OH | TYR | A | 327 | 40.524 | 4.554 | 11.893 | 1.00 | 15.59 | A | O |
| ATOM | 5192 | CE2 | TYR | A | 327 | 42.585 | 4.729 | 10.683 | 1.00 | 14.60 | A | C |
| ATOM | 5194 | CD2 | TYR | A | 327 | 43.607 | 5.518 | 10.176 | 1.00 | 13.91 | A | C |
| ATOM | 5196 | C | TYR | A | 327 | 44.004 | 7.180 | 7.454 | 1.00 | 16.77 | A | C |
| ATOM | 5197 | O | TYR | A | 327 | 44.801 | 6.394 | 6.934 | 1.00 | 16.95 | A | O |
| ATOM | 5199 | N | MET | A | 328 | 42.690 | 7.122 | 7.246 | 1.00 | 16.36 | A | N |
| ATOM | 5200 | CA | MET | A | 328 | 42.100 | 6.171 | 6.307 | 1.00 | 16.03 | A | C |
| ATOM | 5202 | CB | MET | A | 328 | 40.650 | 5.876 | 6.684 | 1.00 | 15.85 | A | C |
| ATOM | 5205 | CG | MET | A | 328 | 40.515 | 5.126 | 7.990 | 1.00 | 15.27 | A | C |
| ATOM | 5208 | SD | MET | A | 328 | 38.824 | 4.621 | 8.325 | 1.00 | 14.96 | A | S |
| ATOM | 5209 | CE | MET | A | 328 | 39.096 | 3.214 | 9.397 | 1.00 | 11.58 | A | C |
| ATOM | 5213 | C | MET | A | 328 | 42.171 | 6.665 | 4.862 | 1.00 | 16.28 | A | C |
| ATOM | 5214 | O | MET | A | 328 | 42.190 | 5.857 | 3.938 | 1.00 | 16.32 | A | O |
| ATOM | 5216 | N | LYS | A | 329 | 42.199 | 7.982 | 4.662 | 1.00 | 16.61 | A | N |
| ATOM | 5217 | CA | LYS | A | 329 | 42.364 | 8.542 | 3.320 | 1.00 | 16.78 | A | C |
| ATOM | 5219 | CB | LYS | A | 329 | 42.319 | 10.076 | 3.338 | 1.00 | 16.88 | A | C |
| ATOM | 5222 | CG | LYS | A | 329 | 40.977 | 10.672 | 3.743 | 1.00 | 19.25 | A | C |
| ATOM | 5225 | CD | LYS | A | 329 | 41.066 | 12.184 | 3.989 | 1.00 | 22.20 | A | C |
| ATOM | 5228 | CE | LYS | A | 329 | 40.917 | 12.990 | 2.701 | 1.00 | 23.60 | A | C |
| ATOM | 5231 | NZ | LYS | A | 329 | 41.054 | 14.461 | 2.934 | 1.00 | 23.47 | A | N |
| ATOM | 5235 | C | LYS | A | 329 | 43.699 | 8.076 | 2.752 | 1.00 | 16.51 | A | C |
| ATOM | 5236 | O | LYS | A | 329 | 43.750 | 7.459 | 1.687 | 1.00 | 16.65 | A | O |
| ATOM | 5238 | N | LEU | A | 330 | 44.770 | 8.355 | 3.492 | 1.00 | 16.06 | A | N |
| ATOM | 5239 | CA | LEU | A | 330 | 46.125 | 7.989 | 3.088 | 1.00 | 15.49 | A | C |
| ATOM | 5241 | CB | LEU | A | 330 | 47.142 | 8.516 | 4.110 | 1.00 | 15.41 | A | C |
| ATOM | 5244 | CG | LEU | A | 330 | 48.628 | 8.299 | 3.810 | 1.00 | 14.76 | A | C |
| ATOM | 5246 | CD1 | LEU | A | 330 | 49.024 | 8.972 | 2.505 | 1.00 | 13.80 | A | C |
| ATOM | 5250 | CD2 | LEU | A | 330 | 49.481 | 8.812 | 4.960 | 1.00 | 13.92 | A | C |
| ATOM | 5254 | C | LEU | A | 330 | 46.283 | 6.478 | 2.927 | 1.00 | 15.10 | A | C |

TABLE 8-2-continued

Coordinates for L494P Structure

| ATOM | 5255 | O | LEU | A | 330 | 47.011 | 6.020 | 2.049 | 1.00 | 14.96 | A | O |
|---|---|---|---|---|---|---|---|---|---|---|---|---|
| ATOM | 5257 | N | CYS | A | 331 | 45.600 | 5.710 | 3.772 | 1.00 | 14.87 | A | N |
| ATOM | 5258 | CA | CYS | A | 331 | 45.696 | 4.248 | 3.732 | 1.00 | 14.79 | A | C |
| ATOM | 5260 | CB | CYS | A | 331 | 45.193 | 3.642 | 5.047 | 1.00 | 15.05 | A | C |
| ATOM | 5263 | SG | CYS | A | 331 | 45.475 | 1.867 | 5.196 | 1.00 | 16.22 | A | S |
| ATOM | 5265 | C | CYS | A | 331 | 44.919 | 3.661 | 2.552 | 1.00 | 13.61 | A | C |
| ATOM | 5266 | O | CYS | A | 331 | 45.455 | 2.861 | 1.787 | 1.00 | 13.77 | A | O |
| ATOM | 5268 | N | PHE | A | 332 | 43.661 | 4.067 | 2.415 | 1.00 | 12.37 | A | N |
| ATOM | 5269 | CA | PHE | A | 332 | 42.796 | 3.589 | 1.339 | 1.00 | 11.68 | A | C |
| ATOM | 5271 | CB | PHE | A | 332 | 41.430 | 4.282 | 1.415 | 1.00 | 11.85 | A | C |
| ATOM | 5274 | CG | PHE | A | 332 | 40.527 | 3.977 | 0.255 | 1.00 | 10.54 | A | C |
| ATOM | 5275 | CD1 | PHE | A | 332 | 39.892 | 2.752 | 0.163 | 1.00 | 9.36 | A | C |
| ATOM | 5277 | CE1 | PHE | A | 332 | 39.065 | 2.466 | −0.905 | 1.00 | 11.01 | A | C |
| ATOM | 5279 | CZ | PHE | A | 332 | 38.862 | 3.413 | −1.897 | 1.00 | 11.31 | A | C |
| ATOM | 5281 | CE2 | PHE | A | 332 | 39.489 | 4.639 | −1.815 | 1.00 | 9.89 | A | C |
| ATOM | 5283 | CD2 | PHE | A | 332 | 40.315 | 4.917 | −0.744 | 1.00 | 10.03 | A | C |
| ATOM | 5285 | C | PHE | A | 332 | 43.413 | 3.812 | −0.042 | 1.00 | 11.23 | A | C |
| ATOM | 5286 | O | PHE | A | 332 | 43.527 | 2.878 | −0.832 | 1.00 | 11.12 | A | O |
| ATOM | 5288 | N | LEU | A | 333 | 43.808 | 5.051 | −0.322 | 1.00 | 10.61 | A | N |
| ATOM | 5289 | CA | LEU | A | 333 | 44.354 | 5.417 | −1.632 | 1.00 | 10.12 | A | C |
| ATOM | 5291 | CB | LEU | A | 333 | 44.677 | 6.916 | −1.680 | 1.00 | 9.81 | A | C |
| ATOM | 5294 | CG | LEU | A | 333 | 45.111 | 7.515 | −3.022 | 1.00 | 8.38 | A | C |
| ATOM | 5296 | CD1 | LEU | A | 333 | 44.113 | 7.206 | −4.128 | 1.00 | 7.03 | A | C |
| ATOM | 5300 | CD2 | LEU | A | 333 | 45.299 | 9.017 | −2.881 | 1.00 | 5.80 | A | C |
| ATOM | 5304 | C | LEU | A | 333 | 45.598 | 4.605 | −1.978 | 1.00 | 10.21 | A | C |
| ATOM | 5305 | O | LEU | A | 333 | 45.791 | 4.229 | −3.133 | 1.00 | 9.84 | A | O |
| ATOM | 5307 | N | ALA | A | 334 | 46.432 | 4.342 | −0.972 | 1.00 | 10.86 | A | N |
| ATOM | 5308 | CA | ALA | A | 334 | 47.645 | 3.538 | −1.140 | 1.00 | 11.33 | A | C |
| ATOM | 5310 | CB | ALA | A | 334 | 48.442 | 3.504 | 0.155 | 1.00 | 11.25 | A | C |
| ATOM | 5314 | C | ALA | A | 334 | 47.302 | 2.120 | −1.582 | 1.00 | 11.86 | A | C |
| ATOM | 5315 | O | ALA | A | 334 | 47.965 | 1.552 | −2.453 | 1.00 | 11.99 | A | O |
| ATOM | 5317 | N | LEU | A | 335 | 46.273 | 1.552 | −0.961 | 1.00 | 12.36 | A | N |
| ATOM | 5318 | CA | LEU | A | 335 | 45.726 | 0.262 | −1.371 | 1.00 | 12.61 | A | C |
| ATOM | 5320 | CB | LEU | A | 335 | 44.651 | −0.193 | −0.375 | 1.00 | 12.56 | A | C |
| ATOM | 5323 | CG | LEU | A | 335 | 43.849 | −1.461 | −0.677 | 1.00 | 12.43 | A | C |
| ATOM | 5325 | CD1 | LEU | A | 335 | 44.764 | −2.659 | −0.871 | 1.00 | 13.39 | A | C |
| ATOM | 5329 | CD2 | LEU | A | 335 | 42.863 | −1.712 | 0.447 | 1.00 | 9.98 | A | C |
| ATOM | 5333 | C | LEU | A | 335 | 45.136 | 0.383 | −2.772 | 1.00 | 12.75 | A | C |
| ATOM | 5334 | O | LEU | A | 335 | 45.446 | −0.411 | −3.655 | 1.00 | 12.66 | A | O |
| ATOM | 5336 | N | TYR | A | 336 | 44.300 | 1.400 | −2.961 | 1.00 | 13.37 | A | N |
| ATOM | 5337 | CA | TYR | A | 336 | 43.602 | 1.636 | −4.225 | 1.00 | 13.86 | A | C |
| ATOM | 5339 | CB | TYR | A | 336 | 42.847 | 2.970 | −4.167 | 1.00 | 14.27 | A | C |
| ATOM | 5342 | CG | TYR | A | 336 | 41.953 | 3.234 | −5.357 | 1.00 | 14.40 | A | C |
| ATOM | 5343 | CD1 | TYR | A | 336 | 40.743 | 2.569 | −5.499 | 1.00 | 14.78 | A | C |
| ATOM | 5345 | CE1 | TYR | A | 336 | 39.916 | 2.810 | −6.586 | 1.00 | 13.90 | A | C |
| ATOM | 5347 | CZ | TYR | A | 336 | 40.293 | 3.725 | −7.545 | 1.00 | 11.73 | A | C |
| ATOM | 5348 | OH | TYR | A | 336 | 39.473 | 3.962 | −8.623 | 1.00 | 8.69 | A | O |
| ATOM | 5350 | CE2 | TYR | A | 336 | 41.488 | 4.405 | −7.423 | 1.00 | 13.24 | A | C |
| ATOM | 5352 | CD2 | TYR | A | 336 | 42.310 | 4.158 | −6.334 | 1.00 | 14.34 | A | C |
| ATOM | 5354 | C | TYR | A | 336 | 44.548 | 1.622 | −5.422 | 1.00 | 13.95 | A | C |
| ATOM | 5355 | O | TYR | A | 336 | 44.305 | 0.907 | −6.397 | 1.00 | 14.01 | A | O |
| ATOM | 5357 | N | ASN | A | 337 | 45.624 | 2.405 | −5.332 | 1.00 | 13.83 | A | N |
| ATOM | 5358 | CA | ASN | A | 337 | 46.605 | 2.519 | −6.416 | 1.00 | 13.77 | A | C |
| ATOM | 5360 | CB | ASN | A | 337 | 47.606 | 3.646 | −6.127 | 1.00 | 13.87 | A | C |
| ATOM | 5363 | CG | ASN | A | 337 | 47.035 | 5.023 | −6.408 | 1.00 | 15.61 | A | C |
| ATOM | 5364 | OD1 | ASN | A | 337 | 46.144 | 5.179 | −7.243 | 1.00 | 19.22 | A | O |
| ATOM | 5365 | ND2 | ASN | A | 337 | 47.557 | 6.035 | −5.719 | 1.00 | 16.23 | A | N |
| ATOM | 5368 | C | ASN | A | 337 | 47.362 | 1.221 | −6.689 | 1.00 | 13.58 | A | C |
| ATOM | 5369 | O | ASN | A | 337 | 47.512 | 0.822 | −7.841 | 1.00 | 13.59 | A | O |
| ATOM | 5371 | N | THR | A | 338 | 47.831 | 0.565 | −5.631 | 1.00 | 13.35 | A | N |
| ATOM | 5372 | CA | THR | A | 338 | 48.600 | −0.674 | −5.770 | 1.00 | 13.08 | A | C |
| ATOM | 5374 | CB | THR | A | 338 | 49.056 | −1.211 | −4.399 | 1.00 | 12.97 | A | C |
| ATOM | 5376 | OG1 | THR | A | 338 | 49.664 | −0.156 | −3.645 | 1.00 | 11.42 | A | O |
| ATOM | 5378 | CG2 | THR | A | 338 | 50.053 | −2.343 | −4.574 | 1.00 | 13.23 | A | C |
| ATOM | 5382 | C | THR | A | 338 | 47.803 | −1.766 | −6.487 | 1.00 | 13.11 | A | C |
| ATOM | 5383 | O | THR | A | 338 | 48.347 | −2.490 | −7.321 | 1.00 | 12.90 | A | O |
| ATOM | 5385 | N | ILE | A | 339 | 46.515 | −1.867 | −6.163 | 1.00 | 13.33 | A | N |
| ATOM | 5386 | CA | ILE | A | 339 | 45.632 | −2.852 | −6.786 | 1.00 | 13.78 | A | C |
| ATOM | 5388 | CB | ILE | A | 339 | 44.286 | −2.979 | −6.033 | 1.00 | 13.62 | A | C |
| ATOM | 5390 | CG1 | ILE | A | 339 | 44.507 | −3.429 | −4.585 | 1.00 | 13.37 | A | C |
| ATOM | 5393 | CD1 | ILE | A | 339 | 45.261 | −4.721 | −4.450 | 1.00 | 11.21 | A | C |
| ATOM | 5397 | CG2 | ILE | A | 339 | 43.364 | −3.962 | −6.740 | 1.00 | 13.25 | A | C |
| ATOM | 5401 | C | ILE | A | 339 | 45.356 | −2.486 | −8.242 | 1.00 | 14.51 | A | C |
| ATOM | 5402 | O | ILE | A | 339 | 45.444 | −3.338 | −9.127 | 1.00 | 14.76 | A | O |
| ATOM | 5404 | N | ASN | A | 340 | 45.025 | −1.220 | −8.485 | 1.00 | 15.03 | A | N |
| ATOM | 5405 | CA | ASN | A | 340 | 44.810 | −0.734 | −9.847 | 1.00 | 15.47 | A | C |
| ATOM | 5407 | CB | ASN | A | 340 | 44.412 | 0.741 | −9.843 | 1.00 | 15.26 | A | C |
| ATOM | 5410 | CG | ASN | A | 340 | 43.012 | 0.971 | −9.315 | 1.00 | 15.69 | A | C |

TABLE 8-2-continued

Coordinates for L494P Structure

| ATOM | 5411 | OD1 | ASN | A | 340 | 42.256 | 0.030 | −9.065 | 1.00 | 14.77 | A | O |
|---|---|---|---|---|---|---|---|---|---|---|---|---|
| ATOM | 5412 | ND2 | ASN | A | 340 | 42.656 | 2.236 | −9.149 | 1.00 | 17.78 | A | N |
| ATOM | 5415 | C | ASN | A | 340 | 46.030 | −0.918 | −10.745 | 1.00 | 16.40 | A | C |
| ATOM | 5416 | O | ASN | A | 340 | 45.882 | −1.126 | −11.950 | 1.00 | 17.11 | A | O |
| ATOM | 5418 | N | GLU | A | 341 | 47.227 | −0.839 | −10.161 | 1.00 | 16.74 | A | N |
| ATOM | 5419 | CA | GLU | A | 341 | 48.467 | −1.016 | −10.919 | 1.00 | 16.76 | A | C |
| ATOM | 5421 | CB | GLU | A | 341 | 49.645 | −0.371 | −10.193 | 1.00 | 17.38 | A | C |
| ATOM | 5424 | CG | GLU | A | 341 | 49.525 | 1.142 | −10.115 | 1.00 | 20.36 | A | C |
| ATOM | 5427 | CD | GLU | A | 341 | 50.747 | 1.812 | −9.519 | 1.00 | 25.20 | A | C |
| ATOM | 5428 | OE1 | GLU | A | 341 | 51.715 | 1.100 | −9.164 | 1.00 | 27.46 | A | O |
| ATOM | 5429 | OE2 | GLU | A | 341 | 50.731 | 3.061 | −9.411 | 1.00 | 26.48 | A | O |
| ATOM | 5430 | C | GLU | A | 341 | 48.765 | −2.480 | −11.232 | 1.00 | 15.62 | A | C |
| ATOM | 5431 | O | GLU | A | 341 | 49.288 | −2.782 | −12.305 | 1.00 | 15.57 | A | O |
| ATOM | 5433 | N | ILE | A | 342 | 48.439 | −3.390 | −10.316 | 1.00 | 14.59 | A | N |
| ATOM | 5434 | CA | ILE | A | 342 | 48.519 | −4.819 | −10.637 | 1.00 | 14.45 | A | C |
| ATOM | 5436 | CB | ILE | A | 342 | 48.289 | −5.731 | −9.410 | 1.00 | 14.11 | A | C |
| ATOM | 5438 | CG1 | ILE | A | 342 | 49.421 | −5.570 | −8.398 | 1.00 | 14.65 | A | C |
| ATOM | 5441 | CD1 | ILE | A | 342 | 49.239 | −6.395 | −7.145 | 1.00 | 14.72 | A | C |
| ATOM | 5445 | CG2 | ILE | A | 342 | 48.233 | −7.189 | −9.837 | 1.00 | 13.46 | A | C |
| ATOM | 5449 | C | ILE | A | 342 | 47.490 | −5.145 | −11.724 | 1.00 | 14.17 | A | C |
| ATOM | 5450 | O | ILE | A | 342 | 47.784 | −5.884 | −12.668 | 1.00 | 14.44 | A | O |
| ATOM | 5452 | N | ALA | A | 343 | 46.293 | −4.576 | −11.586 | 1.00 | 13.41 | A | N |
| ATOM | 5453 | CA | ALA | A | 343 | 45.229 | −4.730 | −12.577 | 1.00 | 12.37 | A | C |
| ATOM | 5455 | CB | ALA | A | 343 | 43.979 | −3.989 | −12.127 | 1.00 | 12.12 | A | C |
| ATOM | 5459 | C | ALA | A | 343 | 45.671 | −4.234 | −13.952 | 1.00 | 11.86 | A | C |
| ATOM | 5460 | O | ALA | A | 343 | 45.270 | −4.793 | −14.971 | 1.00 | 11.95 | A | O |
| ATOM | 5462 | N | TYR | A | 344 | 46.491 | −3.182 | −13.974 | 1.00 | 11.28 | A | N |
| ATOM | 5463 | CA | TYR | A | 344 | 47.076 | −2.685 | −15.219 | 1.00 | 10.66 | A | C |
| ATOM | 5465 | CB | TYR | A | 344 | 47.703 | −1.298 | −15.027 | 1.00 | 10.43 | A | C |
| ATOM | 5468 | CG | TYR | A | 344 | 48.443 | −0.803 | −16.250 | 1.00 | 8.34 | A | C |
| ATOM | 5469 | CD1 | TYR | A | 344 | 47.782 | −0.096 | −17.248 | 1.00 | 6.31 | A | C |
| ATOM | 5471 | CE1 | TYR | A | 344 | 48.453 | 0.350 | −18.377 | 1.00 | 5.53 | A | C |
| ATOM | 5473 | CZ | TYR | A | 344 | 49.802 | 0.088 | −18.520 | 1.00 | 6.31 | A | C |
| ATOM | 5474 | OH | TYR | A | 344 | 50.471 | 0.530 | −19.638 | 1.00 | 4.56 | A | O |
| ATOM | 5476 | CE2 | TYR | A | 344 | 50.482 | −0.614 | −17.542 | 1.00 | 7.74 | A | C |
| ATOM | 5478 | CD2 | TYR | A | 344 | 49.801 | −1.056 | −16.416 | 1.00 | 7.79 | A | C |
| ATOM | 5480 | C | TYR | A | 344 | 48.124 | −3.666 | −15.725 | 1.00 | 10.67 | A | C |
| ATOM | 5481 | O | TYR | A | 344 | 48.084 | −4.078 | −16.881 | 1.00 | 10.32 | A | O |
| ATOM | 5483 | N | ASP | A | 345 | 49.060 | −4.033 | −14.853 | 1.00 | 11.33 | A | N |
| ATOM | 5484 | CA | ASP | A | 345 | 50.108 | −5.004 | −15.192 | 1.00 | 11.99 | A | C |
| ATOM | 5486 | CB | ASP | A | 345 | 50.939 | −5.377 | −13.948 | 1.00 | 12.01 | A | C |
| ATOM | 5489 | CG | ASP | A | 345 | 51.945 | −4.297 | −13.553 | 1.00 | 12.59 | A | C |
| ATOM | 5490 | OD1 | ASP | A | 345 | 52.076 | −3.277 | −14.269 | 1.00 | 11.18 | A | O |
| ATOM | 5491 | OD2 | ASP | A | 345 | 52.615 | −4.483 | −12.513 | 1.00 | 12.55 | A | O |
| ATOM | 5492 | C | ASP | A | 345 | 49.530 | −6.275 | −15.829 | 1.00 | 11.93 | A | C |
| ATOM | 5493 | O | ASP | A | 345 | 50.123 | −6.833 | −16.758 | 1.00 | 11.83 | A | O |
| ATOM | 5495 | N | ASN | A | 346 | 48.378 | −6.722 | −15.329 | 1.00 | 11.62 | A | N |
| ATOM | 5496 | CA | ASN | A | 346 | 47.709 | −7.906 | −15.868 | 1.00 | 11.58 | A | C |
| ATOM | 5498 | CB | ASN | A | 346 | 46.774 | −8.521 | −14.825 | 1.00 | 11.15 | A | C |
| ATOM | 5501 | CG | ASN | A | 346 | 47.516 | −9.376 | −13.819 | 1.00 | 12.26 | A | C |
| ATOM | 5502 | OD1 | ASN | A | 346 | 48.097 | −10.404 | −14.173 | 1.00 | 14.81 | A | O |
| ATOM | 5503 | ND2 | ASN | A | 346 | 47.502 | −8.961 | −12.557 | 1.00 | 12.75 | A | N |
| ATOM | 5506 | C | ASN | A | 346 | 46.956 | −7.634 | −17.171 | 1.00 | 11.92 | A | C |
| ATOM | 5507 | O | ASN | A | 346 | 46.898 | −8.503 | −18.041 | 1.00 | 12.36 | A | O |
| ATOM | 5509 | N | LEU | A | 347 | 46.384 | −6.440 | −17.311 | 1.00 | 11.92 | A | N |
| ATOM | 5510 | CA | LEU | A | 347 | 45.734 | −6.057 | −18.566 | 1.00 | 11.64 | A | C |
| ATOM | 5512 | CB | LEU | A | 347 | 44.961 | −4.740 | −18.413 | 1.00 | 11.58 | A | C |
| ATOM | 5515 | CG | LEU | A | 347 | 44.059 | −4.336 | −19.588 | 1.00 | 10.95 | A | C |
| ATOM | 5517 | CD1 | LEU | A | 347 | 42.907 | −5.312 | −19.745 | 1.00 | 10.27 | A | C |
| ATOM | 5521 | CD2 | LEU | A | 347 | 43.533 | −2.919 | −19.413 | 1.00 | 9.70 | A | C |
| ATOM | 5525 | C | LEU | A | 347 | 46.772 | −5.936 | −19.680 | 1.00 | 11.59 | A | C |
| ATOM | 5526 | O | LEU | A | 347 | 46.514 | −6.330 | −20.814 | 1.00 | 11.64 | A | O |
| ATOM | 5528 | N | LYS | A | 348 | 47.946 | −5.405 | −19.348 | 1.00 | 11.60 | A | N |
| ATOM | 5529 | CA | LYS | A | 348 | 49.022 | −5.244 | −20.321 | 1.00 | 11.67 | A | C |
| ATOM | 5531 | CB | LYS | A | 348 | 50.169 | −4.411 | −19.731 | 1.00 | 11.61 | A | C |
| ATOM | 5534 | CG | LYS | A | 348 | 51.223 | −4.009 | −20.758 | 1.00 | 12.03 | A | C |
| ATOM | 5537 | CD | LYS | A | 348 | 52.290 | −3.072 | −20.194 | 1.00 | 12.25 | A | C |
| ATOM | 5540 | CE | LYS | A | 348 | 53.520 | −3.809 | −19.672 | 1.00 | 12.33 | A | C |
| ATOM | 5543 | NZ | LYS | A | 348 | 53.341 | −4.292 | −18.278 | 1.00 | 14.05 | A | N |
| ATOM | 5547 | C | LYS | A | 348 | 49.558 | −6.595 | −20.794 | 1.00 | 11.72 | A | C |
| ATOM | 5548 | O | LYS | A | 348 | 49.582 | −6.876 | −21.990 | 1.00 | 11.62 | A | O |
| ATOM | 5550 | N | ASP | A | 349 | 49.969 | −7.430 | −19.847 | 1.00 | 12.09 | A | N |
| ATOM | 5551 | CA | ASP | A | 349 | 50.714 | −8.650 | −20.162 | 1.00 | 12.80 | A | C |
| ATOM | 5553 | CB | ASP | A | 349 | 51.664 | −8.986 | −19.006 | 1.00 | 13.12 | A | C |
| ATOM | 5556 | CG | ASP | A | 349 | 52.656 | −7.862 | −18.717 | 1.00 | 14.20 | A | C |
| ATOM | 5557 | OD1 | ASP | A | 349 | 52.969 | −7.085 | −19.650 | 1.00 | 11.97 | A | O |
| ATOM | 5558 | OD2 | ASP | A | 349 | 53.120 | −7.756 | −17.558 | 1.00 | 15.26 | A | O |
| ATOM | 5559 | C | ASP | A | 349 | 49.851 | −9.873 | −20.506 | 1.00 | 12.85 | A | C |

TABLE 8-2-continued

Coordinates for L494P Structure

| ATOM | 5560 | O | ASP | A | 349 | 50.365 | −10.840 | −21.071 | 1.00 | 12.41 | A | O |
|---|---|---|---|---|---|---|---|---|---|---|---|---|
| ATOM | 5562 | N | LYS | A | 350 | 48.560 | −9.833 | −20.169 | 1.00 | 13.16 | A | N |
| ATOM | 5563 | CA | LYS | A | 350 | 47.635 | −10.942 | −20.471 | 1.00 | 13.31 | A | C |
| ATOM | 5565 | CB | LYS | A | 350 | 47.101 | −11.564 | −19.179 | 1.00 | 13.49 | A | C |
| ATOM | 5568 | CG | LYS | A | 350 | 48.180 | −12.050 | −18.233 | 1.00 | 15.19 | A | C |
| ATOM | 5571 | CD | LYS | A | 350 | 47.570 | −12.759 | −17.044 | 1.00 | 17.31 | A | C |
| ATOM | 5574 | CE | LYS | A | 350 | 48.620 | −13.131 | −16.015 | 1.00 | 17.74 | A | C |
| ATOM | 5577 | NZ | LYS | A | 350 | 47.980 | −13.734 | −14.818 | 1.00 | 17.79 | A | N |
| ATOM | 5581 | C | LYS | A | 350 | 46.451 | −10.554 | −21.358 | 1.00 | 12.84 | A | C |
| ATOM | 5582 | O | LYS | A | 350 | 45.896 | −11.406 | −22.048 | 1.00 | 12.55 | A | O |
| ATOM | 5584 | N | GLY | A | 351 | 46.056 | −9.285 | −21.331 | 1.00 | 13.03 | A | N |
| ATOM | 5585 | CA | GLY | A | 351 | 44.914 | −8.816 | −22.115 | 1.00 | 13.29 | A | C |
| ATOM | 5588 | C | GLY | A | 351 | 43.595 | −9.148 | −21.448 | 1.00 | 13.31 | A | C |
| ATOM | 5589 | O | GLY | A | 351 | 42.623 | −9.491 | −22.116 | 1.00 | 13.20 | A | O |
| ATOM | 5591 | N | GLU | A | 352 | 43.567 | −9.047 | −20.124 | 1.00 | 13.73 | A | N |
| ATOM | 5592 | CA | GLU | A | 352 | 42.388 | −9.384 | −19.342 | 1.00 | 14.52 | A | C |
| ATOM | 5594 | CB | GLU | A | 352 | 42.547 | −10.770 | −18.698 | 1.00 | 14.81 | A | C |
| ATOM | 5597 | CG | GLU | A | 352 | 42.906 | −11.923 | −19.656 | 1.00 | 15.61 | A | C |
| ATOM | 5600 | CD | GLU | A | 352 | 41.735 | −12.422 | −20.503 | 1.00 | 15.97 | A | C |
| ATOM | 5601 | OE1 | GLU | A | 352 | 40.627 | −11.845 | −20.425 | 1.00 | 15.33 | A | O |
| ATOM | 5602 | OE2 | GLU | A | 352 | 41.934 | −13.408 | −21.249 | 1.00 | 14.04 | A | O |
| ATOM | 5603 | C | GLU | A | 352 | 42.187 | −8.335 | −18.249 | 1.00 | 14.94 | A | C |
| ATOM | 5604 | O | GLU | A | 352 | 43.153 | −7.891 | −17.621 | 1.00 | 14.91 | A | O |
| ATOM | 5606 | N | ASN | A | 353 | 40.933 | −7.944 | −18.028 | 1.00 | 15.09 | A | N |
| ATOM | 5607 | CA | ASN | A | 353 | 40.579 | −7.054 | −16.924 | 1.00 | 15.05 | A | C |
| ATOM | 5609 | CB | ASN | A | 353 | 39.393 | −6.167 | −17.315 | 1.00 | 15.19 | A | C |
| ATOM | 5612 | CG | ASN | A | 353 | 39.132 | −5.055 | −16.314 | 1.00 | 14.51 | A | C |
| ATOM | 5613 | OD1 | ASN | A | 353 | 39.523 | −5.135 | −15.151 | 1.00 | 12.06 | A | O |
| ATOM | 5614 | ND2 | ASN | A | 353 | 38.459 | −4.007 | −16.769 | 1.00 | 16.67 | A | N |
| ATOM | 5617 | C | ASN | A | 353 | 40.238 | −7.895 | −15.696 | 1.00 | 14.95 | A | C |
| ATOM | 5618 | O | ASN | A | 353 | 39.198 | −8.554 | −15.662 | 1.00 | 15.14 | A | O |
| ATOM | 5620 | N | ILE | A | 354 | 41.118 | −7.863 | −14.695 | 1.00 | 14.71 | A | N |
| ATOM | 5621 | CA | ILE | A | 354 | 40.940 | −8.652 | −13.472 | 1.00 | 14.50 | A | C |
| ATOM | 5623 | CB | ILE | A | 354 | 42.138 | −9.614 | −13.238 | 1.00 | 14.70 | A | C |
| ATOM | 5625 | CG1 | ILE | A | 354 | 43.430 | −8.840 | −12.954 | 1.00 | 14.73 | A | C |
| ATOM | 5628 | CD1 | ILE | A | 354 | 44.527 | −9.706 | −12.397 | 1.00 | 13.59 | A | C |
| ATOM | 5632 | CG2 | ILE | A | 354 | 42.333 | −10.530 | −14.441 | 1.00 | 15.18 | A | C |
| ATOM | 5636 | C | ILE | A | 354 | 40.736 | −7.791 | −12.221 | 1.00 | 14.26 | A | C |
| ATOM | 5637 | O | ILE | A | 354 | 40.839 | −8.290 | −11.104 | 1.00 | 14.39 | A | O |
| ATOM | 5639 | N | LEU | A | 355 | 40.440 | −6.507 | −12.401 | 1.00 | 14.54 | A | N |
| ATOM | 5640 | CA | LEU | A | 355 | 40.244 | −5.601 | −11.266 | 1.00 | 14.48 | A | C |
| ATOM | 5642 | CB | LEU | A | 355 | 40.026 | −4.157 | −11.748 | 1.00 | 14.01 | A | C |
| ATOM | 5645 | CG | LEU | A | 355 | 39.868 | −3.068 | −10.679 | 1.00 | 13.56 | A | C |
| ATOM | 5647 | CD1 | LEU | A | 355 | 41.000 | −3.113 | −9.666 | 1.00 | 13.71 | A | C |
| ATOM | 5651 | CD2 | LEU | A | 355 | 39.786 | −1.687 | −11.320 | 1.00 | 12.08 | A | C |
| ATOM | 5655 | C | LEU | A | 355 | 39.103 | −6.042 | −10.335 | 1.00 | 14.97 | A | C |
| ATOM | 5656 | O | LEU | A | 355 | 39.248 | −5.951 | −9.116 | 1.00 | 15.16 | A | O |
| ATOM | 5658 | N | PRO | A | 356 | 37.976 | −6.532 | −10.899 | 1.00 | 15.42 | A | N |
| ATOM | 5659 | CA | PRO | A | 356 | 36.863 | −6.986 | −10.057 | 1.00 | 15.69 | A | C |
| ATOM | 5661 | CB | PRO | A | 356 | 35.785 | −7.372 | −11.079 | 1.00 | 15.69 | A | C |
| ATOM | 5664 | CG | PRO | A | 356 | 36.124 | −6.623 | −12.292 | 1.00 | 15.33 | A | C |
| ATOM | 5667 | CD | PRO | A | 356 | 37.610 | −6.580 | −12.326 | 1.00 | 15.51 | A | C |
| ATOM | 5670 | C | PRO | A | 356 | 37.177 | −8.185 | −9.154 | 1.00 | 15.96 | A | C |
| ATOM | 5671 | O | PRO | A | 356 | 36.545 | −8.342 | −8.107 | 1.00 | 16.29 | A | O |
| ATOM | 5672 | N | TYR | A | 357 | 38.130 | −9.023 | −9.556 | 1.00 | 15.86 | A | N |
| ATOM | 5673 | CA | TYR | A | 357 | 38.504 | −10.198 | −8.762 | 1.00 | 16.04 | A | C |
| ATOM | 5675 | CB | TYR | A | 357 | 39.099 | −11.298 | −9.651 | 1.00 | 16.10 | A | C |
| ATOM | 5678 | CG | TYR | A | 357 | 38.332 | −11.505 | −10.938 | 1.00 | 17.77 | A | C |
| ATOM | 5679 | CD1 | TYR | A | 357 | 36.958 | −11.732 | −10.921 | 1.00 | 18.41 | A | C |
| ATOM | 5681 | CE1 | TYR | A | 357 | 36.244 | −11.912 | −12.099 | 1.00 | 18.01 | A | C |
| ATOM | 5683 | CZ | TYR | A | 357 | 36.905 | −11.864 | −13.311 | 1.00 | 18.22 | A | C |
| ATOM | 5684 | OH | TYR | A | 357 | 36.207 | −12.043 | −14.479 | 1.00 | 19.76 | A | O |
| ATOM | 5686 | CE2 | TYR | A | 357 | 38.269 | −11.641 | −13.356 | 1.00 | 18.63 | A | C |
| ATOM | 5688 | CD2 | TYR | A | 357 | 38.975 | −11.460 | −12.173 | 1.00 | 18.68 | A | C |
| ATOM | 5690 | C | TYR | A | 357 | 39.489 | −9.810 | −7.661 | 1.00 | 15.60 | A | C |
| ATOM | 5691 | O | TYR | A | 357 | 39.448 | −10.361 | −6.562 | 1.00 | 15.71 | A | O |
| ATOM | 5693 | N | LEU | A | 358 | 40.371 | −8.861 | −7.965 | 1.00 | 15.17 | A | N |
| ATOM | 5694 | CA | LEU | A | 358 | 41.318 | −8.345 | −6.983 | 1.00 | 14.66 | A | C |
| ATOM | 5696 | CB | LEU | A | 358 | 42.383 | −7.471 | −7.655 | 1.00 | 14.49 | A | C |
| ATOM | 5699 | CG | LEU | A | 358 | 43.348 | −8.179 | −8.610 | 1.00 | 13.67 | A | C |
| ATOM | 5701 | CD1 | LEU | A | 358 | 44.231 | −7.165 | −9.319 | 1.00 | 13.09 | A | C |
| ATOM | 5705 | CD2 | LEU | A | 358 | 44.198 | −9.197 | −7.873 | 1.00 | 11.60 | A | C |
| ATOM | 5709 | C | LEU | A | 358 | 40.597 | −7.548 | −5.899 | 1.00 | 14.57 | A | C |
| ATOM | 5710 | O | LEU | A | 358 | 40.844 | −7.764 | −4.713 | 1.00 | 15.41 | A | O |
| ATOM | 5712 | N | THR | A | 359 | 39.703 | −6.644 | −6.304 | 1.00 | 13.71 | A | N |
| ATOM | 5713 | CA | THR | A | 359 | 39.002 | −5.768 | −5.354 | 1.00 | 13.19 | A | C |
| ATOM | 5715 | CB | THR | A | 359 | 38.347 | −4.560 | −6.058 | 1.00 | 13.29 | A | C |
| ATOM | 5717 | OG1 | THR | A | 359 | 37.390 | −5.020 | −7.020 | 1.00 | 15.24 | A | O |

TABLE 8-2-continued

Coordinates for L494P Structure

| ATOM | 5719 | CG2 | THR | A | 359 | 39.399 | −3.705 | −6.748 | 1.00 | 12.12 | A | C |
|------|------|-----|-----|---|-----|--------|--------|--------|------|-------|---|---|
| ATOM | 5723 | C | THR | A | 359 | 37.933 | −6.490 | −4.528 | 1.00 | 12.69 | A | C |
| ATOM | 5724 | O | THR | A | 359 | 37.545 | −6.008 | −3.464 | 1.00 | 12.15 | A | O |
| ATOM | 5726 | N | LYS | A | 360 | 37.456 | −7.634 | −5.019 | 1.00 | 12.46 | A | N |
| ATOM | 5727 | CA | LYS | A | 360 | 36.519 | −8.471 | −4.263 | 1.00 | 12.16 | A | C |
| ATOM | 5729 | CB | LYS | A | 360 | 35.845 | −9.498 | −5.180 | 1.00 | 12.44 | A | C |
| ATOM | 5732 | CG | LYS | A | 360 | 34.793 | −10.378 | −4.499 | 1.00 | 13.59 | A | C |
| ATOM | 5735 | CD | LYS | A | 360 | 33.591 | −9.569 | −4.027 | 1.00 | 14.74 | A | C |
| ATOM | 5738 | CE | LYS | A | 360 | 32.450 | −10.472 | −3.579 | 1.00 | 15.45 | A | C |
| ATOM | 5741 | NZ | LYS | A | 360 | 31.179 | −9.724 | −3.364 | 1.00 | 15.06 | A | N |
| ATOM | 5745 | C | LYS | A | 360 | 37.235 | −9.185 | −3.118 | 1.00 | 11.29 | A | C |
| ATOM | 5746 | O | LYS | A | 360 | 36.666 | −9.365 | −2.042 | 1.00 | 11.08 | A | O |
| ATOM | 5748 | N | ALA | A | 361 | 38.476 | −9.598 | −3.359 | 1.00 | 10.61 | A | N |
| ATOM | 5749 | CA | ALA | A | 361 | 39.304 | −10.206 | −2.318 | 1.00 | 10.70 | A | C |
| ATOM | 5751 | CB | ALA | A | 361 | 40.628 | −10.673 | −2.900 | 1.00 | 11.07 | A | C |
| ATOM | 5755 | C | ALA | A | 361 | 39.553 | −9.222 | −1.181 | 1.00 | 10.58 | A | C |
| ATOM | 5756 | O | ALA | A | 361 | 39.661 | −9.619 | −0.019 | 1.00 | 10.13 | A | O |
| ATOM | 5758 | N | TRP | A | 362 | 39.643 | −7.941 | −1.534 | 1.00 | 10.54 | A | N |
| ATOM | 5759 | CA | TRP | A | 362 | 39.859 | −6.868 | −0.568 | 1.00 | 10.37 | A | C |
| ATOM | 5761 | CB | TRP | A | 362 | 40.577 | −5.696 | −1.236 | 1.00 | 9.72 | A | C |
| ATOM | 5764 | CG | TRP | A | 362 | 42.045 | −5.882 | −1.233 | 1.00 | 9.03 | A | C |
| ATOM | 5765 | CD1 | TRP | A | 362 | 42.838 | −6.216 | −2.288 | 1.00 | 9.07 | A | C |
| ATOM | 5767 | NE1 | TRP | A | 362 | 44.147 | −6.312 | −1.883 | 1.00 | 8.13 | A | N |
| ATOM | 5769 | CE2 | TRP | A | 362 | 44.215 | −6.045 | −0.542 | 1.00 | 7.66 | A | C |
| ATOM | 5770 | CD2 | TRP | A | 362 | 42.907 | −5.775 | −0.099 | 1.00 | 7.66 | A | C |
| ATOM | 5771 | CE3 | TRP | A | 362 | 42.699 | −5.472 | 1.250 | 1.00 | 7.22 | A | C |
| ATOM | 5773 | CZ3 | TRP | A | 362 | 43.784 | −5.446 | 2.099 | 1.00 | 7.74 | A | C |
| ATOM | 5775 | CH2 | TRP | A | 362 | 45.076 | −5.718 | 1.629 | 1.00 | 9.54 | A | C |
| ATOM | 5777 | CZ2 | TRP | A | 362 | 45.310 | −6.018 | 0.314 | 1.00 | 9.02 | A | C |
| ATOM | 5779 | C | TRP | A | 362 | 38.570 | −6.394 | 0.099 | 1.00 | 11.16 | A | C |
| ATOM | 5780 | O | TRP | A | 362 | 38.588 | −6.007 | 1.267 | 1.00 | 11.42 | A | O |
| ATOM | 5782 | N | ALA | A | 363 | 37.462 | −6.416 | −0.639 | 1.00 | 11.67 | A | N |
| ATOM | 5783 | CA | ALA | A | 363 | 36.151 | −6.099 | −0.070 | 1.00 | 12.00 | A | C |
| ATOM | 5785 | CB | ALA | A | 363 | 35.103 | −5.985 | −1.169 | 1.00 | 11.90 | A | C |
| ATOM | 5789 | C | ALA | A | 363 | 35.738 | −7.162 | 0.941 | 1.00 | 12.69 | A | C |
| ATOM | 5790 | O | ALA | A | 363 | 35.096 | −6.857 | 1.944 | 1.00 | 12.73 | A | O |
| ATOM | 5792 | N | ASP | A | 364 | 36.112 | −8.409 | 0.670 | 1.00 | 13.63 | A | N |
| ATOM | 5793 | CA | ASP | A | 364 | 35.763 | −9.523 | 1.544 | 1.00 | 14.66 | A | C |
| ATOM | 5795 | CB | ASP | A | 364 | 35.734 | −10.838 | 0.754 | 1.00 | 15.17 | A | C |
| ATOM | 5798 | CG | ASP | A | 364 | 34.559 | −10.916 | −0.223 | 1.00 | 17.28 | A | C |
| ATOM | 5799 | OD1 | ASP | A | 364 | 33.578 | −10.155 | −0.061 | 1.00 | 17.21 | A | O |
| ATOM | 5800 | OD2 | ASP | A | 364 | 34.618 | −11.751 | −1.154 | 1.00 | 20.88 | A | O |
| ATOM | 5801 | C | ASP | A | 364 | 36.711 | −9.635 | 2.738 | 1.00 | 14.83 | A | C |
| ATOM | 5802 | O | ASP | A | 364 | 36.275 | −9.968 | 3.841 | 1.00 | 15.19 | A | O |
| ATOM | 5804 | N | LEU | A | 365 | 37.998 | −9.359 | 2.527 | 1.00 | 14.97 | A | N |
| ATOM | 5805 | CA | LEU | A | 365 | 38.978 | −9.400 | 3.620 | 1.00 | 14.98 | A | C |
| ATOM | 5807 | CB | LEU | A | 365 | 40.399 | −9.149 | 3.100 | 1.00 | 14.64 | A | C |
| ATOM | 5810 | CG | LEU | A | 365 | 41.521 | −9.152 | 4.146 | 1.00 | 13.12 | A | C |
| ATOM | 5812 | CD1 | LEU | A | 365 | 41.596 | −10.491 | 4.852 | 1.00 | 12.43 | A | C |
| ATOM | 5816 | CD2 | LEU | A | 365 | 42.861 | −8.812 | 3.514 | 1.00 | 13.28 | A | C |
| ATOM | 5820 | C | LEU | A | 365 | 38.632 | −8.367 | 4.685 | 1.00 | 15.67 | A | C |
| ATOM | 5821 | O | LEU | A | 365 | 38.742 | −8.637 | 5.884 | 1.00 | 16.08 | A | O |
| ATOM | 5823 | N | CYS | A | 366 | 38.216 | −7.187 | 4.234 | 1.00 | 16.03 | A | N |
| ATOM | 5824 | CA | CYS | A | 366 | 37.820 | −6.108 | 5.130 | 1.00 | 16.51 | A | C |
| ATOM | 5826 | CB | CYS | A | 366 | 37.723 | −4.784 | 4.363 | 1.00 | 16.60 | A | C |
| ATOM | 5829 | SG | CYS | A | 366 | 39.333 | −4.159 | 3.767 | 1.00 | 17.69 | A | S |
| ATOM | 5831 | C | CYS | A | 366 | 36.505 | −6.430 | 5.850 | 1.00 | 17.00 | A | C |
| ATOM | 5832 | O | CYS | A | 366 | 36.377 | −6.170 | 7.047 | 1.00 | 17.59 | A | O |
| ATOM | 5834 | N | ASN | A | 367 | 35.541 | −7.008 | 5.132 | 1.00 | 17.21 | A | N |
| ATOM | 5835 | CA | ASN | A | 367 | 34.291 | −7.476 | 5.757 | 1.00 | 17.08 | A | C |
| ATOM | 5837 | CB | ASN | A | 367 | 33.275 | −7.939 | 4.703 | 1.00 | 17.09 | A | C |
| ATOM | 5840 | CG | ASN | A | 367 | 32.260 | −6.863 | 4.354 | 1.00 | 17.63 | A | C |
| ATOM | 5841 | OD1 | ASN | A | 367 | 31.791 | −6.127 | 5.225 | 1.00 | 17.70 | A | O |
| ATOM | 5842 | ND2 | ASN | A | 367 | 31.903 | −6.778 | 3.076 | 1.00 | 17.33 | A | N |
| ATOM | 5845 | C | ASN | A | 367 | 34.514 | −8.590 | 6.782 | 1.00 | 17.07 | A | C |
| ATOM | 5846 | O | ASN | A | 367 | 33.684 | −8.793 | 7.670 | 1.00 | 17.00 | A | O |
| ATOM | 5848 | N | ALA | A | 368 | 35.627 | −9.311 | 6.646 | 1.00 | 16.97 | A | N |
| ATOM | 5849 | CA | ALA | A | 368 | 36.051 | −10.287 | 7.647 | 1.00 | 16.97 | A | C |
| ATOM | 5851 | CB | ALA | A | 368 | 37.167 | −11.156 | 7.093 | 1.00 | 16.96 | A | C |
| ATOM | 5855 | C | ALA | A | 368 | 36.505 | −9.598 | 8.937 | 1.00 | 17.11 | A | C |
| ATOM | 5856 | O | ALA | A | 368 | 36.112 | −10.006 | 10.034 | 1.00 | 16.89 | A | O |
| ATOM | 5858 | N | PHE | A | 369 | 37.332 | −8.559 | 8.798 | 1.00 | 17.06 | A | N |
| ATOM | 5859 | CA | PHE | A | 369 | 37.834 | −7.796 | 9.948 | 1.00 | 17.07 | A | C |
| ATOM | 5861 | CB | PHE | A | 369 | 38.876 | −6.756 | 9.517 | 1.00 | 17.09 | A | C |
| ATOM | 5864 | CG | PHE | A | 369 | 40.163 | −7.336 | 9.004 | 1.00 | 17.47 | A | C |
| ATOM | 5865 | CD1 | PHE | A | 369 | 40.847 | −8.307 | 9.722 | 1.00 | 19.16 | A | C |
| ATOM | 5867 | CE1 | PHE | A | 369 | 42.047 | −8.826 | 9.253 | 1.00 | 19.68 | A | C |
| ATOM | 5869 | CZ | PHE | A | 369 | 42.583 | −8.361 | 8.064 | 1.00 | 19.22 | A | C |

TABLE 8-2-continued

Coordinates for L494P Structure

| ATOM | 5871 | CE2 | PHE | A | 369 | 41.917 | −7.383 | 7.347 | 1.00 | 19.11 | A | C |
|---|---|---|---|---|---|---|---|---|---|---|---|---|
| ATOM | 5873 | CD2 | PHE | A | 369 | 40.717 | −6.872 | 7.820 | 1.00 | 17.84 | A | C |
| ATOM | 5875 | C | PHE | A | 369 | 36.721 | −7.061 | 10.694 | 1.00 | 17.02 | A | C |
| ATOM | 5876 | O | PHE | A | 369 | 36.748 | −6.961 | 11.924 | 1.00 | 17.17 | A | O |
| ATOM | 5878 | N | LEU | A | 370 | 35.763 | −6.521 | 9.945 | 1.00 | 16.86 | A | N |
| ATOM | 5879 | CA | LEU | A | 370 | 34.624 | −5.827 | 10.543 | 1.00 | 16.90 | A | C |
| ATOM | 5881 | CB | LEU | A | 370 | 33.710 | −5.241 | 9.462 | 1.00 | 17.00 | A | C |
| ATOM | 5884 | CG | LEU | A | 370 | 32.790 | −4.104 | 9.913 | 1.00 | 16.77 | A | C |
| ATOM | 5886 | CD1 | LEU | A | 370 | 33.545 | −2.782 | 9.908 | 1.00 | 17.03 | A | C |
| ATOM | 5890 | CD2 | LEU | A | 370 | 31.557 | −4.011 | 9.027 | 1.00 | 17.46 | A | C |
| ATOM | 5894 | C | LEU | A | 370 | 33.843 | −6.802 | 11.415 | 1.00 | 17.08 | A | C |
| ATOM | 5895 | O | LEU | A | 370 | 33.438 | −6.464 | 12.526 | 1.00 | 16.72 | A | O |
| ATOM | 5897 | N | GLN | A | 371 | 33.651 | −8.016 | 10.899 | 1.00 | 17.46 | A | N |
| ATOM | 5898 | CA | GLN | A | 371 | 32.961 | −9.077 | 11.626 | 1.00 | 17.49 | A | C |
| ATOM | 5900 | CB | GLN | A | 371 | 32.719 | −10.279 | 10.708 | 1.00 | 17.34 | A | C |
| ATOM | 5903 | CG | GLN | A | 371 | 31.916 | −11.410 | 11.344 | 1.00 | 17.48 | A | C |
| ATOM | 5906 | CD | GLN | A | 371 | 30.512 | −10.990 | 11.732 | 1.00 | 17.14 | A | C |
| ATOM | 5907 | OE1 | GLN | A | 371 | 30.267 | −10.572 | 12.863 | 1.00 | 17.53 | A | O |
| ATOM | 5908 | NE2 | GLN | A | 371 | 29.582 | −11.091 | 10.789 | 1.00 | 16.59 | A | N |
| ATOM | 5911 | C | GLN | A | 371 | 33.741 | −9.506 | 12.869 | 1.00 | 17.91 | A | C |
| ATOM | 5912 | O | GLN | A | 371 | 33.140 | −9.800 | 13.901 | 1.00 | 18.11 | A | O |
| ATOM | 5914 | N | GLU | A | 372 | 35.070 | −9.549 | 12.767 | 1.00 | 18.39 | A | N |
| ATOM | 5915 | CA | GLU | A | 372 | 35.926 | −9.854 | 13.921 | 1.00 | 18.81 | A | C |
| ATOM | 5917 | CB | GLU | A | 372 | 37.388 | −10.058 | 13.498 | 1.00 | 19.35 | A | C |
| ATOM | 5920 | CG | GLU | A | 372 | 37.707 | −11.451 | 12.961 | 1.00 | 22.59 | A | C |
| ATOM | 5923 | CD | GLU | A | 372 | 39.205 | −11.722 | 12.862 | 1.00 | 26.48 | A | C |
| ATOM | 5924 | OE1 | GLU | A | 372 | 39.992 | −10.748 | 12.800 | 1.00 | 29.10 | A | O |
| ATOM | 5925 | OE2 | GLU | A | 372 | 39.594 | −12.912 | 12.843 | 1.00 | 27.20 | A | O |
| ATOM | 5926 | C | GLU | A | 372 | 35.854 | −8.752 | 14.976 | 1.00 | 18.32 | A | C |
| ATOM | 5927 | O | GLU | A | 372 | 35.775 | −9.040 | 16.171 | 1.00 | 18.34 | A | O |
| ATOM | 5929 | N | ALA | A | 373 | 35.886 | −7.497 | 14.528 | 1.00 | 17.77 | A | N |
| ATOM | 5930 | CA | ALA | A | 373 | 35.846 | −6.347 | 15.429 | 1.00 | 17.52 | A | C |
| ATOM | 5932 | CB | ALA | A | 373 | 36.239 | −5.085 | 14.685 | 1.00 | 17.47 | A | C |
| ATOM | 5936 | C | ALA | A | 373 | 34.472 | −6.171 | 16.083 | 1.00 | 17.59 | A | C |
| ATOM | 5937 | O | ALA | A | 373 | 34.383 | −5.819 | 17.259 | 1.00 | 17.52 | A | O |
| ATOM | 5939 | N | LYS | A | 374 | 33.408 | −6.416 | 15.319 | 1.00 | 17.66 | A | N |
| ATOM | 5940 | CA | LYS | A | 374 | 32.037 | −6.287 | 15.827 | 1.00 | 17.69 | A | C |
| ATOM | 5942 | CB | LYS | A | 374 | 31.016 | −6.485 | 14.700 | 1.00 | 17.73 | A | C |
| ATOM | 5945 | CG | LYS | A | 374 | 30.781 | −5.244 | 13.848 | 1.00 | 18.61 | A | C |
| ATOM | 5948 | CD | LYS | A | 374 | 29.872 | −5.544 | 12.659 | 1.00 | 19.44 | A | C |
| ATOM | 5951 | CE | LYS | A | 374 | 29.505 | −4.277 | 11.898 | 1.00 | 18.81 | A | C |
| ATOM | 5954 | NZ | LYS | A | 374 | 28.710 | −4.565 | 10.673 | 1.00 | 18.02 | A | N |
| ATOM | 5958 | C | LYS | A | 374 | 31.735 | −7.250 | 16.977 | 1.00 | 17.82 | A | C |
| ATOM | 5959 | O | LYS | A | 374 | 31.028 | −6.884 | 17.917 | 1.00 | 17.93 | A | O |
| ATOM | 5961 | N | TRP | A | 375 | 32.260 | −8.473 | 16.896 | 1.00 | 18.05 | A | N |
| ATOM | 5962 | CA | TRP | A | 375 | 32.132 | −9.445 | 17.989 | 1.00 | 18.34 | A | C |
| ATOM | 5964 | CB | TRP | A | 375 | 32.660 | −10.824 | 17.575 | 1.00 | 18.28 | A | C |
| ATOM | 5967 | CG | TRP | A | 375 | 31.847 | −11.529 | 16.523 | 1.00 | 18.45 | A | C |
| ATOM | 5968 | CD1 | TRP | A | 375 | 30.498 | −11.446 | 16.328 | 1.00 | 19.67 | A | C |
| ATOM | 5970 | NE1 | TRP | A | 375 | 30.119 | −12.249 | 15.278 | 1.00 | 18.96 | A | N |
| ATOM | 5972 | CE2 | TRP | A | 375 | 31.228 | −12.882 | 14.782 | 1.00 | 17.60 | A | C |
| ATOM | 5973 | CD2 | TRP | A | 375 | 32.336 | −12.457 | 15.545 | 1.00 | 17.42 | A | C |
| ATOM | 5974 | CE3 | TRP | A | 375 | 33.604 | −12.962 | 15.235 | 1.00 | 17.04 | A | C |
| ATOM | 5976 | CZ3 | TRP | A | 375 | 33.724 | −13.861 | 14.186 | 1.00 | 17.20 | A | C |
| ATOM | 5978 | CH2 | TRP | A | 375 | 32.602 | −14.267 | 13.446 | 1.00 | 17.60 | A | C |
| ATOM | 5980 | CZ2 | TRP | A | 375 | 31.350 | −13.790 | 13.728 | 1.00 | 17.78 | A | C |
| ATOM | 5982 | C | TRP | A | 375 | 32.883 | −8.983 | 19.241 | 1.00 | 18.75 | A | C |
| ATOM | 5983 | O | TRP | A | 375 | 32.402 | −9.171 | 20.362 | 1.00 | 19.03 | A | O |
| ATOM | 5985 | N | LEU | A | 376 | 34.062 | −8.392 | 19.041 | 1.00 | 18.64 | A | N |
| ATOM | 5986 | CA | LEU | A | 376 | 34.890 | −7.907 | 20.147 | 1.00 | 18.48 | A | C |
| ATOM | 5988 | CB | LEU | A | 376 | 36.302 | −7.572 | 19.650 | 1.00 | 18.65 | A | C |
| ATOM | 5991 | CG | LEU | A | 376 | 37.413 | −7.399 | 20.697 | 1.00 | 20.28 | A | C |
| ATOM | 5993 | CD1 | LEU | A | 376 | 38.775 | −7.749 | 20.098 | 1.00 | 21.89 | A | C |
| ATOM | 5997 | CD2 | LEU | A | 376 | 37.437 | −5.986 | 21.285 | 1.00 | 20.91 | A | C |
| ATOM | 6001 | C | LEU | A | 376 | 34.257 | −6.693 | 20.834 | 1.00 | 18.28 | A | C |
| ATOM | 6002 | O | LEU | A | 376 | 34.401 | −6.525 | 22.046 | 1.00 | 18.58 | A | O |
| ATOM | 6004 | N | TYR | A | 377 | 33.559 | −5.857 | 20.065 | 1.00 | 17.92 | A | N |
| ATOM | 6005 | CA | TYR | A | 377 | 32.851 | −4.698 | 20.622 | 1.00 | 17.91 | A | C |
| ATOM | 6007 | CB | TYR | A | 377 | 32.456 | −3.710 | 19.513 | 1.00 | 18.04 | A | C |
| ATOM | 6010 | CG | TYR | A | 377 | 31.758 | −2.460 | 20.019 | 1.00 | 18.20 | A | C |
| ATOM | 6011 | CD1 | TYR | A | 377 | 32.450 | −1.505 | 20.762 | 1.00 | 19.47 | A | C |
| ATOM | 6013 | CE1 | TYR | A | 377 | 31.817 | −0.357 | 21.234 | 1.00 | 19.90 | A | C |
| ATOM | 6015 | CZ | TYR | A | 377 | 30.474 | −0.154 | 20.961 | 1.00 | 20.89 | A | C |
| ATOM | 6016 | OH | TYR | A | 377 | 29.846 | 0.980 | 21.429 | 1.00 | 19.22 | A | O |
| ATOM | 6018 | CE2 | TYR | A | 377 | 29.763 | −1.090 | 20.223 | 1.00 | 20.13 | A | C |
| ATOM | 6020 | CD2 | TYR | A | 377 | 30.409 | −2.234 | 19.756 | 1.00 | 18.66 | A | C |
| ATOM | 6022 | C | TYR | A | 377 | 31.607 | −5.126 | 21.408 | 1.00 | 17.54 | A | C |
| ATOM | 6023 | O | TYR | A | 377 | 31.403 | −4.696 | 22.546 | 1.00 | 17.43 | A | O |

TABLE 8-2-continued

Coordinates for L494P Structure

| ATOM | 6025 | N   | ASN | A | 378 | 30.792 | −5.984  | 20.797 | 1.00 | 17.04 | A | N |
|------|------|-----|-----|---|-----|--------|---------|--------|------|-------|---|---|
| ATOM | 6026 | CA  | ASN | A | 378 | 29.527 | −6.421  | 21.392 | 1.00 | 16.71 | A | C |
| ATOM | 6028 | CB  | ASN | A | 378 | 28.534 | −6.789  | 20.287 | 1.00 | 16.56 | A | C |
| ATOM | 6031 | CG  | ASN | A | 378 | 28.283 | −5.644  | 19.323 | 1.00 | 16.15 | A | C |
| ATOM | 6032 | OD1 | ASN | A | 378 | 27.985 | −4.526  | 19.735 | 1.00 | 15.51 | A | O |
| ATOM | 6033 | ND2 | ASN | A | 378 | 28.405 | −5.920  | 18.031 | 1.00 | 16.34 | A | N |
| ATOM | 6036 | C   | ASN | A | 378 | 29.675 | −7.599  | 22.356 | 1.00 | 16.69 | A | C |
| ATOM | 6037 | O   | ASN | A | 378 | 28.687 | −8.058  | 22.932 | 1.00 | 16.54 | A | O |
| ATOM | 6039 | N   | LYS | A | 379 | 30.905 | −8.083  | 22.528 | 1.00 | 16.67 | A | N |
| ATOM | 6040 | CA  | LYS | A | 379 | 31.188 | −9.241  | 23.375 | 1.00 | 16.55 | A | C |
| ATOM | 6042 | CB  | LYS | A | 379 | 31.047 | −8.874  | 24.859 | 1.00 | 16.40 | A | C |
| ATOM | 6045 | CG  | LYS | A | 379 | 32.158 | −7.964  | 25.348 | 1.00 | 17.12 | A | C |
| ATOM | 6048 | CD  | LYS | A | 379 | 31.853 | −7.352  | 26.702 | 1.00 | 17.89 | A | C |
| ATOM | 6051 | CE  | LYS | A | 379 | 33.029 | −6.523  | 27.198 | 1.00 | 18.11 | A | C |
| ATOM | 6054 | NZ  | LYS | A | 379 | 32.604 | −5.464  | 28.151 | 1.00 | 19.23 | A | N |
| ATOM | 6058 | C   | LYS | A | 379 | 30.305 | −10.432 | 22.997 | 1.00 | 16.36 | A | C |
| ATOM | 6059 | O   | LYS | A | 379 | 29.725 | −11.093 | 23.859 | 1.00 | 17.03 | A | O |
| ATOM | 6061 | N   | SER | A | 380 | 30.214 | −10.691 | 21.695 | 1.00 | 15.82 | A | N |
| ATOM | 6062 | CA  | SER | A | 380 | 29.447 | −11.818 | 21.179 | 1.00 | 15.44 | A | C |
| ATOM | 6064 | CB  | SER | A | 380 | 29.261 | −11.686 | 19.667 | 1.00 | 15.30 | A | C |
| ATOM | 6067 | OG  | SER | A | 380 | 28.738 | −10.414 | 19.326 | 1.00 | 14.16 | A | O |
| ATOM | 6069 | C   | SER | A | 380 | 30.171 | −13.118 | 21.503 | 1.00 | 15.54 | A | C |
| ATOM | 6070 | O   | SER | A | 380 | 31.377 | −13.115 | 21.747 | 1.00 | 15.63 | A | O |
| ATOM | 6072 | N   | THR | A | 381 | 29.433 | −14.226 | 21.504 | 1.00 | 15.71 | A | N |
| ATOM | 6073 | CA  | THR | A | 381 | 30.004 | −15.538 | 21.812 | 1.00 | 16.14 | A | C |
| ATOM | 6075 | CB  | THR | A | 381 | 29.483 | −16.076 | 23.173 | 1.00 | 16.44 | A | C |
| ATOM | 6077 | OG1 | THR | A | 381 | 28.057 | −16.215 | 23.133 | 1.00 | 17.09 | A | O |
| ATOM | 6079 | CG2 | THR | A | 381 | 29.863 | −15.133 | 24.309 | 1.00 | 17.19 | A | C |
| ATOM | 6083 | C   | THR | A | 381 | 29.694 | −16.539 | 20.696 | 1.00 | 16.10 | A | C |
| ATOM | 6084 | O   | THR | A | 381 | 29.099 | −17.591 | 20.947 | 1.00 | 16.34 | A | O |
| ATOM | 6086 | N   | PRO | A | 382 | 30.115 | −16.223 | 19.456 | 1.00 | 16.07 | A | N |
| ATOM | 6087 | CA  | PRO | A | 382 | 29.789 | −17.060 | 18.297 | 1.00 | 16.17 | A | C |
| ATOM | 6089 | CB  | PRO | A | 382 | 30.430 | −16.303 | 17.131 | 1.00 | 16.16 | A | C |
| ATOM | 6092 | CG  | PRO | A | 382 | 31.535 | −15.532 | 17.747 | 1.00 | 15.98 | A | C |
| ATOM | 6095 | CD  | PRO | A | 382 | 31.022 | −15.120 | 19.086 | 1.00 | 16.01 | A | C |
| ATOM | 6098 | C   | PRO | A | 382 | 30.369 | −18.470 | 18.385 | 1.00 | 16.25 | A | C |
| ATOM | 6099 | O   | PRO | A | 382 | 31.442 | −18.665 | 18.963 | 1.00 | 16.33 | A | O |
| ATOM | 6100 | N   | THR | A | 383 | 29.662 | −19.439 | 17.807 | 1.00 | 16.20 | A | N |
| ATOM | 6101 | CA  | THR | A | 383 | 30.120 | −20.828 | 17.800 | 1.00 | 15.92 | A | C |
| ATOM | 6103 | CB  | THR | A | 383 | 29.044 | −21.794 | 17.251 | 1.00 | 15.85 | A | C |
| ATOM | 6105 | OG1 | THR | A | 383 | 28.676 | −21.409 | 15.920 | 1.00 | 14.24 | A | O |
| ATOM | 6107 | CG2 | THR | A | 383 | 27.807 | −21.793 | 18.147 | 1.00 | 15.69 | A | C |
| ATOM | 6111 | C   | THR | A | 383 | 31.387 | −20.962 | 16.964 | 1.00 | 15.82 | A | C |
| ATOM | 6112 | O   | THR | A | 383 | 31.668 | −20.120 | 16.111 | 1.00 | 15.84 | A | O |
| ATOM | 6114 | N   | PHE | A | 384 | 32.148 | −22.021 | 17.219 | 1.00 | 15.86 | A | N |
| ATOM | 6115 | CA  | PHE | A | 384 | 33.401 | −22.274 | 16.508 | 1.00 | 15.78 | A | C |
| ATOM | 6117 | CB  | PHE | A | 384 | 33.909 | −23.687 | 16.812 | 1.00 | 15.96 | A | C |
| ATOM | 6120 | CG  | PHE | A | 384 | 35.097 | −24.097 | 15.987 | 1.00 | 15.25 | A | C |
| ATOM | 6121 | CD1 | PHE | A | 384 | 36.337 | −23.510 | 16.195 | 1.00 | 15.45 | A | C |
| ATOM | 6123 | CE1 | PHE | A | 384 | 37.439 | −23.887 | 15.438 | 1.00 | 15.15 | A | C |
| ATOM | 6125 | CZ  | PHE | A | 384 | 37.305 | −24.858 | 14.464 | 1.00 | 14.65 | A | C |
| ATOM | 6127 | CE2 | PHE | A | 384 | 36.072 | −25.450 | 14.247 | 1.00 | 14.59 | A | C |
| ATOM | 6129 | CD2 | PHE | A | 384 | 34.977 | −25.070 | 15.007 | 1.00 | 14.05 | A | C |
| ATOM | 6131 | C   | PHE | A | 384 | 33.251 | −22.101 | 15.002 | 1.00 | 15.75 | A | C |
| ATOM | 6132 | O   | PHE | A | 384 | 34.061 | −21.426 | 14.371 | 1.00 | 15.67 | A | O |
| ATOM | 6134 | N   | ASP | A | 385 | 32.206 | −22.704 | 14.439 | 1.00 | 15.83 | A | N |
| ATOM | 6135 | CA  | ASP | A | 385 | 31.997 | −22.699 | 12.990 | 1.00 | 15.78 | A | C |
| ATOM | 6137 | CB  | ASP | A | 385 | 30.956 | −23.755 | 12.593 | 1.00 | 15.57 | A | C |
| ATOM | 6140 | CG  | ASP | A | 385 | 31.473 | −25.179 | 12.750 | 1.00 | 14.28 | A | C |
| ATOM | 6141 | OD1 | ASP | A | 385 | 32.696 | −25.397 | 12.644 | 1.00 | 14.47 | A | O |
| ATOM | 6142 | OD2 | ASP | A | 385 | 30.656 | −26.092 | 12.971 | 1.00 | 13.30 | A | O |
| ATOM | 6143 | C   | ASP | A | 385 | 31.618 | −21.329 | 12.420 | 1.00 | 16.22 | A | C |
| ATOM | 6144 | O   | ASP | A | 385 | 31.727 | −21.121 | 11.215 | 1.00 | 16.29 | A | O |
| ATOM | 6146 | N   | ASP | A | 386 | 31.178 | −20.403 | 13.272 | 1.00 | 17.06 | A | N |
| ATOM | 6147 | CA  | ASP | A | 386 | 30.967 | −19.011 | 12.854 | 1.00 | 18.04 | A | C |
| ATOM | 6149 | CB  | ASP | A | 386 | 29.900 | −18.310 | 13.711 | 1.00 | 18.36 | A | C |
| ATOM | 6152 | CG  | ASP | A | 386 | 28.490 | −18.461 | 13.146 | 1.00 | 19.49 | A | C |
| ATOM | 6153 | OD1 | ASP | A | 386 | 28.242 | −19.410 | 12.369 | 1.00 | 21.38 | A | O |
| ATOM | 6154 | OD2 | ASP | A | 386 | 27.625 | −17.625 | 13.489 | 1.00 | 18.48 | A | O |
| ATOM | 6155 | C   | ASP | A | 386 | 32.271 | −18.223 | 12.910 | 1.00 | 18.63 | A | C |
| ATOM | 6156 | O   | ASP | A | 386 | 32.644 | −17.582 | 11.930 | 1.00 | 19.56 | A | O |
| ATOM | 6158 | N   | TYR | A | 387 | 32.962 | −18.265 | 14.048 | 1.00 | 19.03 | A | N |
| ATOM | 6159 | CA  | TYR | A | 387 | 34.237 | −17.556 | 14.182 | 1.00 | 19.44 | A | C |
| ATOM | 6161 | CB  | TYR | A | 387 | 34.793 | −17.629 | 15.614 | 1.00 | 19.51 | A | C |
| ATOM | 6164 | CG  | TYR | A | 387 | 36.142 | −16.950 | 15.762 | 1.00 | 21.18 | A | C |
| ATOM | 6165 | CD1 | TYR | A | 387 | 36.235 | −15.576 | 15.975 | 1.00 | 22.72 | A | C |
| ATOM | 6167 | CE1 | TYR | A | 387 | 37.476 | −14.945 | 16.095 | 1.00 | 24.66 | A | C |
| ATOM | 6169 | CZ  | TYR | A | 387 | 38.641 | −15.695 | 15.996 | 1.00 | 25.02 | A | C |

TABLE 8-2-continued

Coordinates for L494P Structure

| ATOM | 6170 | OH | TYR | A | 387 | 39.870 | −15.084 | 16.116 | 1.00 | 24.90 | A | O |
|------|------|-----|-----|---|-----|--------|---------|--------|------|-------|---|---|
| ATOM | 6172 | CE2 | TYR | A | 387 | 38.573 | −17.060 | 15.778 | 1.00 | 24.35 | A | C |
| ATOM | 6174 | CD2 | TYR | A | 387 | 37.328 | −17.680 | 15.661 | 1.00 | 23.39 | A | C |
| ATOM | 6176 | C | TYR | A | 387 | 35.273 | −18.089 | 13.188 | 1.00 | 19.48 | A | C |
| ATOM | 6177 | O | TYR | A | 387 | 35.892 | −17.311 | 12.462 | 1.00 | 19.69 | A | O |
| ATOM | 6179 | N | PHE | A | 388 | 35.451 | −19.409 | 13.155 | 1.00 | 19.44 | A | N |
| ATOM | 6180 | CA | PHE | A | 388 | 36.464 | −20.016 | 12.293 | 1.00 | 19.32 | A | C |
| ATOM | 6182 | CB | PHE | A | 388 | 36.682 | −21.490 | 12.626 | 1.00 | 19.39 | A | C |
| ATOM | 6185 | CG | PHE | A | 388 | 37.829 | −22.101 | 11.878 | 1.00 | 19.88 | A | C |
| ATOM | 6186 | CD1 | PHE | A | 388 | 39.135 | −21.824 | 12.251 | 1.00 | 19.14 | A | C |
| ATOM | 6188 | CE1 | PHE | A | 388 | 40.201 | −22.370 | 11.559 | 1.00 | 20.10 | A | C |
| ATOM | 6190 | CZ | PHE | A | 388 | 39.969 | −23.199 | 10.470 | 1.00 | 20.36 | A | C |
| ATOM | 6192 | CE2 | PHE | A | 388 | 38.669 | −23.476 | 10.080 | 1.00 | 20.47 | A | C |
| ATOM | 6194 | CD2 | PHE | A | 388 | 37.606 | −22.924 | 10.780 | 1.00 | 20.61 | A | C |
| ATOM | 6196 | C | PHE | A | 388 | 36.131 | −19.869 | 10.813 | 1.00 | 19.22 | A | C |
| ATOM | 6197 | O | PHE | A | 388 | 37.028 | −19.679 | 9.995 | 1.00 | 19.09 | A | O |
| ATOM | 6199 | N | GLY | A | 389 | 34.851 | −19.963 | 10.468 | 1.00 | 19.30 | A | N |
| ATOM | 6200 | CA | GLY | A | 389 | 34.411 | −19.671 | 9.106 | 1.00 | 19.45 | A | C |
| ATOM | 6203 | C | GLY | A | 389 | 34.924 | −18.310 | 8.665 | 1.00 | 19.46 | A | C |
| ATOM | 6204 | O | GLY | A | 389 | 35.561 | −18.186 | 7.616 | 1.00 | 19.53 | A | O |
| ATOM | 6206 | N | ASN | A | 390 | 34.662 | −17.297 | 9.491 | 1.00 | 19.12 | A | N |
| ATOM | 6207 | CA | ASN | A | 390 | 35.119 | −15.931 | 9.238 | 1.00 | 18.83 | A | C |
| ATOM | 6209 | CB | ASN | A | 390 | 34.388 | −14.955 | 10.163 | 1.00 | 18.64 | A | C |
| ATOM | 6212 | CG | ASN | A | 390 | 34.691 | −13.505 | 9.836 | 1.00 | 18.88 | A | C |
| ATOM | 6213 | OD1 | ASN | A | 390 | 34.151 | −12.949 | 8.882 | 1.00 | 20.54 | A | O |
| ATOM | 6214 | ND2 | ASN | A | 390 | 35.561 | −12.887 | 10.627 | 1.00 | 17.01 | A | N |
| ATOM | 6217 | C | ASN | A | 390 | 36.630 | −15.750 | 9.416 | 1.00 | 18.88 | A | C |
| ATOM | 6218 | O | ASN | A | 390 | 37.240 | −14.918 | 8.742 | 1.00 | 19.57 | A | O |
| ATOM | 6220 | N | ALA | A | 391 | 37.225 | −16.525 | 10.322 | 1.00 | 18.39 | A | N |
| ATOM | 6221 | CA | ALA | A | 391 | 38.636 | −16.365 | 10.688 | 1.00 | 17.65 | A | C |
| ATOM | 6223 | CB | ALA | A | 391 | 38.977 | −17.237 | 11.885 | 1.00 | 17.64 | A | C |
| ATOM | 6227 | C | ALA | A | 391 | 39.617 | −16.635 | 9.547 | 1.00 | 17.17 | A | C |
| ATOM | 6228 | O | ALA | A | 391 | 40.541 | −15.849 | 9.349 | 1.00 | 17.37 | A | O |
| ATOM | 6230 | N | TRP | A | 392 | 39.435 | −17.727 | 8.801 | 1.00 | 16.59 | A | N |
| ATOM | 6231 | CA | TRP | A | 392 | 40.381 | −18.048 | 7.718 | 1.00 | 16.35 | A | C |
| ATOM | 6233 | CB | TRP | A | 392 | 40.325 | −19.525 | 7.281 | 1.00 | 16.37 | A | C |
| ATOM | 6236 | CG | TRP | A | 392 | 39.029 | −20.021 | 6.712 | 1.00 | 17.82 | A | C |
| ATOM | 6237 | CD1 | TRP | A | 392 | 38.089 | −20.760 | 7.363 | 1.00 | 20.80 | A | C |
| ATOM | 6239 | NE1 | TRP | A | 392 | 37.044 | −21.053 | 6.522 | 1.00 | 21.26 | A | N |
| ATOM | 6241 | CE2 | TRP | A | 392 | 37.303 | −20.516 | 5.290 | 1.00 | 19.01 | A | C |
| ATOM | 6242 | CD2 | TRP | A | 392 | 38.552 | −19.864 | 5.369 | 1.00 | 18.29 | A | C |
| ATOM | 6243 | CE3 | TRP | A | 392 | 39.050 | −19.225 | 4.229 | 1.00 | 18.54 | A | C |
| ATOM | 6245 | CZ3 | TRP | A | 392 | 38.297 | −19.258 | 3.066 | 1.00 | 18.44 | A | C |
| ATOM | 6247 | CH2 | TRP | A | 392 | 37.060 | −19.914 | 3.021 | 1.00 | 18.84 | A | C |
| ATOM | 6249 | CZ2 | TRP | A | 392 | 36.547 | −20.547 | 4.120 | 1.00 | 18.75 | A | C |
| ATOM | 6251 | C | TRP | A | 392 | 40.272 | −17.093 | 6.521 | 1.00 | 15.96 | A | C |
| ATOM | 6252 | O | TRP | A | 392 | 41.223 | −16.957 | 5.754 | 1.00 | 15.58 | A | O |
| ATOM | 6254 | N | LYS | A | 393 | 39.131 | −16.427 | 6.367 | 1.00 | 16.07 | A | N |
| ATOM | 6255 | CA | LYS | A | 393 | 39.018 | −15.339 | 5.389 | 1.00 | 16.20 | A | C |
| ATOM | 6257 | CB | LYS | A | 393 | 37.556 | −15.051 | 5.034 | 1.00 | 16.58 | A | C |
| ATOM | 6260 | CG | LYS | A | 393 | 36.893 | −16.149 | 4.211 | 1.00 | 18.39 | A | C |
| ATOM | 6263 | CD | LYS | A | 393 | 35.609 | −15.652 | 3.561 | 1.00 | 21.72 | A | C |
| ATOM | 6266 | CE | LYS | A | 393 | 34.704 | −16.803 | 3.139 | 1.00 | 22.15 | A | C |
| ATOM | 6269 | NZ | LYS | A | 393 | 34.074 | −17.470 | 4.313 | 1.00 | 22.61 | A | N |
| ATOM | 6273 | C | LYS | A | 393 | 39.699 | −14.068 | 5.902 | 1.00 | 15.28 | A | C |
| ATOM | 6274 | O | LYS | A | 393 | 40.191 | −13.264 | 5.108 | 1.00 | 15.25 | A | O |
| ATOM | 6276 | N | SER | A | 394 | 39.725 | −13.891 | 7.223 | 1.00 | 14.19 | A | N |
| ATOM | 6277 | CA | SER | A | 394 | 40.438 | −12.768 | 7.836 | 1.00 | 13.88 | A | C |
| ATOM | 6279 | CB | SER | A | 394 | 39.829 | −12.405 | 9.194 | 1.00 | 13.76 | A | C |
| ATOM | 6282 | OG | SER | A | 394 | 40.198 | −13.331 | 10.198 | 1.00 | 14.47 | A | O |
| ATOM | 6284 | C | SER | A | 394 | 41.938 | −13.043 | 7.987 | 1.00 | 13.51 | A | C |
| ATOM | 6285 | O | SER | A | 394 | 42.696 | −12.149 | 8.359 | 1.00 | 13.98 | A | O |
| ATOM | 6287 | N | SER | A | 395 | 42.363 | −14.275 | 7.711 | 1.00 | 12.98 | A | N |
| ATOM | 6288 | CA | SER | A | 395 | 43.789 | −14.608 | 7.665 | 1.00 | 12.09 | A | C |
| ATOM | 6290 | CB | SER | A | 395 | 43.987 | −16.115 | 7.484 | 1.00 | 11.72 | A | C |
| ATOM | 6293 | OG | SER | A | 395 | 43.677 | −16.517 | 6.160 | 1.00 | 9.17 | A | O |
| ATOM | 6295 | C | SER | A | 395 | 44.479 | −13.873 | 6.520 | 1.00 | 11.88 | A | C |
| ATOM | 6296 | O | SER | A | 395 | 45.653 | −13.530 | 6.620 | 1.00 | 12.00 | A | O |
| ATOM | 6298 | N | SER | A | 396 | 43.721 | −13.637 | 5.446 | 1.00 | 11.56 | A | N |
| ATOM | 6299 | CA | SER | A | 396 | 44.212 | −13.063 | 4.189 | 1.00 | 11.42 | A | C |
| ATOM | 6301 | CB | SER | A | 396 | 45.143 | −11.858 | 4.416 | 1.00 | 11.41 | A | C |
| ATOM | 6304 | OG | SER | A | 396 | 46.494 | −12.252 | 4.580 | 1.00 | 10.83 | A | O |
| ATOM | 6306 | C | SER | A | 396 | 44.887 | −14.131 | 3.325 | 1.00 | 11.35 | A | C |
| ATOM | 6307 | O | SER | A | 396 | 45.498 | −13.814 | 2.300 | 1.00 | 11.18 | A | O |
| ATOM | 6309 | N | GLY | A | 397 | 44.761 | −15.392 | 3.740 | 1.00 | 11.18 | A | N |
| ATOM | 6310 | CA | GLY | A | 397 | 45.257 | −16.523 | 2.966 | 1.00 | 11.19 | A | C |
| ATOM | 6313 | C | GLY | A | 397 | 44.591 | −16.607 | 1.605 | 1.00 | 11.20 | A | C |
| ATOM | 6314 | O | GLY | A | 397 | 45.270 | −16.806 | 0.596 | 1.00 | 11.77 | A | O |

TABLE 8-2-continued

Coordinates for L494P Structure

| ATOM | 6316 | N | PRO | A | 398 | 43.254 | −16.458 | 1.565 | 1.00 | 10.58 | A | N |
|---|---|---|---|---|---|---|---|---|---|---|---|---|
| ATOM | 6317 | CA | PRO | A | 398 | 42.574 | −16.415 | 0.279 | 1.00 | 10.32 | A | C |
| ATOM | 6319 | CB | PRO | A | 398 | 41.095 | −16.282 | 0.665 | 1.00 | 10.50 | A | C |
| ATOM | 6322 | CG | PRO | A | 398 | 41.013 | −16.848 | 2.032 | 1.00 | 10.24 | A | C |
| ATOM | 6325 | CD | PRO | A | 398 | 42.295 | −16.448 | 2.683 | 1.00 | 10.64 | A | C |
| ATOM | 6328 | C | PRO | A | 398 | 43.024 | −15.235 | −0.571 | 1.00 | 9.73 | A | C |
| ATOM | 6329 | O | PRO | A | 398 | 43.301 | −15.405 | −1.755 | 1.00 | 9.10 | A | O |
| ATOM | 6330 | N | LEU | A | 399 | 43.113 | −14.054 | 0.030 | 1.00 | 9.90 | A | N |
| ATOM | 6331 | CA | LEU | A | 399 | 43.532 | −12.871 | −0.712 | 1.00 | 10.55 | A | C |
| ATOM | 6333 | CB | LEU | A | 399 | 43.538 | −11.626 | 0.179 | 1.00 | 10.41 | A | C |
| ATOM | 6336 | CG | LEU | A | 399 | 43.677 | −10.296 | −0.568 | 1.00 | 9.15 | A | C |
| ATOM | 6338 | CD1 | LEU | A | 399 | 43.004 | −9.192 | 0.209 | 1.00 | 10.37 | A | C |
| ATOM | 6342 | CD2 | LEU | A | 399 | 45.134 | −9.947 | −0.838 | 1.00 | 8.74 | A | C |
| ATOM | 6346 | C | LEU | A | 399 | 44.911 | −13.095 | −1.322 | 1.00 | 11.44 | A | C |
| ATOM | 6347 | O | LEU | A | 399 | 45.102 | −12.893 | −2.520 | 1.00 | 12.07 | A | O |
| ATOM | 6349 | N | GLN | A | 400 | 45.861 | −13.534 | −0.500 | 1.00 | 11.78 | A | N |
| ATOM | 6350 | CA | GLN | A | 400 | 47.230 | −13.779 | −0.966 | 1.00 | 12.03 | A | C |
| ATOM | 6352 | CB | GLN | A | 400 | 48.106 | −14.301 | 0.176 | 1.00 | 12.44 | A | C |
| ATOM | 6355 | CG | GLN | A | 400 | 48.616 | −13.216 | 1.117 | 1.00 | 12.64 | A | C |
| ATOM | 6358 | CD | GLN | A | 400 | 49.595 | −13.754 | 2.141 | 1.00 | 11.76 | A | C |
| ATOM | 6359 | OE1 | GLN | A | 400 | 50.554 | −14.442 | 1.799 | 1.00 | 11.16 | A | O |
| ATOM | 6360 | NE2 | GLN | A | 400 | 49.353 | −13.447 | 3.407 | 1.00 | 12.59 | A | N |
| ATOM | 6363 | C | GLN | A | 400 | 47.308 | −14.742 | −2.155 | 1.00 | 11.86 | A | C |
| ATOM | 6364 | O | GLN | A | 400 | 48.147 | −14.574 | −3.038 | 1.00 | 11.52 | A | O |
| ATOM | 6366 | N | LEU | A | 401 | 46.443 | −15.750 | −2.176 | 1.00 | 12.22 | A | N |
| ATOM | 6367 | CA | LEU | A | 401 | 46.442 | −16.721 | −3.269 | 1.00 | 12.76 | A | C |
| ATOM | 6369 | CB | LEU | A | 401 | 45.926 | −18.087 | −2.791 | 1.00 | 12.53 | A | C |
| ATOM | 6372 | CG | LEU | A | 401 | 46.818 | −18.811 | −1.772 | 1.00 | 11.90 | A | C |
| ATOM | 6374 | CD1 | LEU | A | 401 | 46.158 | −20.093 | −1.294 | 1.00 | 13.20 | A | C |
| ATOM | 6378 | CD2 | LEU | A | 401 | 48.195 | −19.111 | −2.346 | 1.00 | 9.64 | A | C |
| ATOM | 6382 | C | LEU | A | 401 | 45.649 | −16.225 | −4.485 | 1.00 | 13.27 | A | C |
| ATOM | 6383 | O | LEU | A | 401 | 45.910 | −16.662 | −5.609 | 1.00 | 13.80 | A | O |
| ATOM | 6385 | N | VAL | A | 402 | 44.693 | −15.320 | −4.272 | 1.00 | 13.43 | A | N |
| ATOM | 6386 | CA | VAL | A | 402 | 43.968 | −14.700 | −5.391 | 1.00 | 13.52 | A | C |
| ATOM | 6388 | CB | VAL | A | 402 | 42.791 | −13.811 | −4.915 | 1.00 | 13.58 | A | C |
| ATOM | 6390 | CG1 | VAL | A | 402 | 41.759 | −14.647 | −4.186 | 1.00 | 14.22 | A | C |
| ATOM | 6394 | CG2 | VAL | A | 402 | 42.146 | −13.090 | −6.093 | 1.00 | 11.75 | A | C |
| ATOM | 6398 | C | VAL | A | 402 | 44.924 | −13.864 | −6.244 | 1.00 | 13.38 | A | C |
| ATOM | 6399 | O | VAL | A | 402 | 44.798 | −13.827 | −7.463 | 1.00 | 13.04 | A | O |
| ATOM | 6401 | N | PHE | A | 403 | 45.880 | −13.207 | −5.594 | 1.00 | 13.34 | A | N |
| ATOM | 6402 | CA | PHE | A | 403 | 46.916 | −12.455 | −6.301 | 1.00 | 13.95 | A | C |
| ATOM | 6404 | CB | PHE | A | 403 | 47.544 | −11.410 | −5.376 | 1.00 | 14.44 | A | C |
| ATOM | 6407 | CG | PHE | A | 403 | 46.673 | −10.206 | −5.155 | 1.00 | 14.69 | A | C |
| ATOM | 6408 | CD1 | PHE | A | 403 | 46.949 | −9.004 | −5.795 | 1.00 | 13.14 | A | C |
| ATOM | 6410 | CE1 | PHE | A | 403 | 46.140 | −7.903 | −5.598 | 1.00 | 13.57 | A | C |
| ATOM | 6412 | CZ | PHE | A | 403 | 45.035 | −7.999 | −4.763 | 1.00 | 14.00 | A | C |
| ATOM | 6414 | CE2 | PHE | A | 403 | 44.749 | −9.191 | −4.128 | 1.00 | 12.73 | A | C |
| ATOM | 6416 | CD2 | PHE | A | 403 | 45.560 | −10.285 | −4.328 | 1.00 | 12.55 | A | C |
| ATOM | 6418 | C | PHE | A | 403 | 47.991 | −13.378 | −6.867 | 1.00 | 13.90 | A | C |
| ATOM | 6419 | O | PHE | A | 403 | 48.496 | −13.154 | −7.971 | 1.00 | 13.60 | A | O |
| ATOM | 6421 | N | ALA | A | 404 | 48.335 | −14.411 | −6.101 | 1.00 | 14.11 | A | N |
| ATOM | 6422 | CA | ALA | A | 404 | 49.301 | −15.419 | −6.533 | 1.00 | 14.01 | A | C |
| ATOM | 6424 | CB | ALA | A | 404 | 49.536 | −16.439 | −5.420 | 1.00 | 14.07 | A | C |
| ATOM | 6428 | C | ALA | A | 404 | 48.850 | −16.123 | −7.813 | 1.00 | 13.46 | A | C |
| ATOM | 6429 | O | ALA | A | 404 | 49.676 | −16.483 | −8.651 | 1.00 | 13.31 | A | O |
| ATOM | 6431 | N | TYR | A | 405 | 47.542 | −16.315 | −7.960 | 1.00 | 13.06 | A | N |
| ATOM | 6432 | CA | TYR | A | 405 | 46.990 | −16.912 | −9.172 | 1.00 | 13.33 | A | C |
| ATOM | 6434 | CB | TYR | A | 405 | 45.458 | −16.967 | −9.110 | 1.00 | 12.98 | A | C |
| ATOM | 6437 | CG | TYR | A | 405 | 44.842 | −17.457 | −10.398 | 1.00 | 11.28 | A | C |
| ATOM | 6438 | CD1 | TYR | A | 405 | 44.849 | −18.808 | −10.721 | 1.00 | 11.80 | A | C |
| ATOM | 6440 | CE1 | TYR | A | 405 | 44.297 | −19.269 | −11.914 | 1.00 | 11.52 | A | C |
| ATOM | 6442 | CZ | TYR | A | 405 | 43.741 | −18.369 | −12.801 | 1.00 | 10.95 | A | C |
| ATOM | 6443 | OH | TYR | A | 405 | 43.199 | −18.819 | −13.980 | 1.00 | 9.66 | A | O |
| ATOM | 6445 | CE2 | TYR | A | 405 | 43.729 | −17.016 | −12.505 | 1.00 | 11.40 | A | C |
| ATOM | 6447 | CD2 | TYR | A | 405 | 44.280 | −16.568 | −11.308 | 1.00 | 10.90 | A | C |
| ATOM | 6449 | C | TYR | A | 405 | 47.424 | −16.133 | −10.411 | 1.00 | 14.22 | A | C |
| ATOM | 6450 | O | TYR | A | 405 | 47.961 | −16.709 | −11.360 | 1.00 | 14.09 | A | O |
| ATOM | 6452 | N | PHE | A | 406 | 47.198 | −14.820 | −10.384 | 1.00 | 15.24 | A | N |
| ATOM | 6453 | CA | PHE | A | 406 | 47.442 | −13.958 | −11.546 | 1.00 | 15.22 | A | C |
| ATOM | 6455 | CB | PHE | A | 406 | 46.733 | −12.613 | −11.377 | 1.00 | 14.88 | A | C |
| ATOM | 6458 | CG | PHE | A | 406 | 45.237 | −12.722 | −11.317 | 1.00 | 13.53 | A | C |
| ATOM | 6459 | CD1 | PHE | A | 406 | 44.504 | −13.009 | −12.458 | 1.00 | 13.38 | A | C |
| ATOM | 6461 | CE1 | PHE | A | 406 | 43.126 | −13.107 | −12.408 | 1.00 | 12.53 | A | C |
| ATOM | 6463 | CZ | PHE | A | 406 | 42.465 | −12.913 | −11.210 | 1.00 | 12.19 | A | C |
| ATOM | 6465 | CE2 | PHE | A | 406 | 43.186 | −12.623 | −10.068 | 1.00 | 11.97 | A | C |
| ATOM | 6467 | CD2 | PHE | A | 406 | 44.563 | −12.528 | −10.126 | 1.00 | 11.83 | A | C |
| ATOM | 6469 | C | PHE | A | 406 | 48.922 | −13.717 | −11.831 | 1.00 | 15.89 | A | C |
| ATOM | 6470 | O | PHE | A | 406 | 49.267 | −13.239 | −12.912 | 1.00 | 16.18 | A | O |

TABLE 8-2-continued

Coordinates for L494P Structure

| ATOM | 6472 | N | ALA | A | 407 | 49.789 | −14.025 | −10.868 | 1.00 | 16.30 A | N |
|------|------|------|-----|---|-----|--------|---------|---------|------|---------|---|
| ATOM | 6473 | CA | ALA | A | 407 | 51.230 | −13.919 | −11.078 | 1.00 | 16.47 A | C |
| ATOM | 6475 | CB | ALA | A | 407 | 51.945 | −13.724 | −9.764 | 1.00 | 16.54 A | C |
| ATOM | 6479 | C | ALA | A | 407 | 51.764 | −15.156 | −11.785 | 1.00 | 17.01 A | C |
| ATOM | 6480 | O | ALA | A | 407 | 52.403 | −15.039 | −12.828 | 1.00 | 17.63 A | O |
| ATOM | 6482 | N | VAL | A | 408 | 51.479 | −16.333 | −11.227 | 1.00 | 17.52 A | N |
| ATOM | 6483 | CA | VAL | A | 408 | 52.125 | −17.582 | −11.661 | 1.00 | 18.18 A | C |
| ATOM | 6485 | CB | VAL | A | 408 | 52.196 | −18.620 | −10.509 | 1.00 | 18.02 A | C |
| ATOM | 6487 | CG1 | VAL | A | 408 | 52.962 | −18.048 | −9.323 | 1.00 | 17.51 A | C |
| ATOM | 6491 | CG2 | VAL | A | 408 | 50.808 | −19.070 | −10.091 | 1.00 | 17.56 A | C |
| ATOM | 6495 | C | VAL | A | 408 | 51.510 | −18.259 | −12.896 | 1.00 | 19.13 A | C |
| ATOM | 6496 | O | VAL | A | 408 | 52.226 | −18.899 | −13.665 | 1.00 | 19.26 A | O |
| ATOM | 6498 | N | VAL | A | 409 | 50.201 | −18.127 | −13.088 | 1.00 | 20.36 A | N |
| ATOM | 6499 | CA | VAL | A | 409 | 49.523 | −18.799 | −14.203 | 1.00 | 21.49 A | C |
| ATOM | 6501 | CB | VAL | A | 409 | 48.010 | −18.951 | −13.934 | 1.00 | 21.39 A | C |
| ATOM | 6503 | CG1 | VAL | A | 409 | 47.353 | −19.765 | −15.036 | 1.00 | 22.15 A | C |
| ATOM | 6507 | CG2 | VAL | A | 409 | 47.771 | −19.611 | −12.584 | 1.00 | 22.07 A | C |
| ATOM | 6511 | C | VAL | A | 409 | 49.722 | −18.038 | −15.521 | 1.00 | 22.53 A | C |
| ATOM | 6512 | O | VAL | A | 409 | 49.629 | −16.808 | −15.547 | 1.00 | 23.27 A | O |
| ATOM | 6514 | N | GLN | A | 410 | 49.994 | −18.768 | −16.607 | 1.00 | 23.04 A | N |
| ATOM | 6515 | CA | GLN | A | 410 | 50.117 | −18.159 | −17.940 | 1.00 | 23.44 A | C |
| ATOM | 6517 | CB | GLN | A | 410 | 50.609 | −19.176 | −18.988 | 1.00 | 23.94 A | C |
| ATOM | 6520 | CG | GLN | A | 410 | 52.109 | −19.114 | −19.307 | 1.00 | 25.78 A | C |
| ATOM | 6523 | CD | GLN | A | 410 | 52.465 | −19.825 | −20.619 | 1.00 | 27.06 A | C |
| ATOM | 6524 | OE1 | GLN | A | 410 | 52.543 | −21.055 | −20.676 | 1.00 | 27.24 A | O |
| ATOM | 6525 | NE2 | GLN | A | 410 | 52.688 | −19.047 | −21.675 | 1.00 | 25.76 A | N |
| ATOM | 6528 | C | GLN | A | 410 | 48.782 | −17.546 | −18.378 | 1.00 | 23.54 A | C |
| ATOM | 6529 | O | GLN | A | 410 | 48.589 | −16.335 | −18.271 | 1.00 | 23.64 A | O |
| ATOM | 6531 | N | ASN | A | 411 | 47.864 | −18.385 | −18.853 | 1.00 | 23.79 A | N |
| ATOM | 6532 | CA | ASN | A | 411 | 46.560 | −17.921 | −19.321 | 1.00 | 23.91 A | C |
| ATOM | 6534 | CB | ASN | A | 411 | 46.095 | −18.734 | −20.535 | 1.00 | 24.06 A | C |
| ATOM | 6537 | CG | ASN | A | 411 | 46.913 | −18.446 | −21.784 | 1.00 | 24.54 A | C |
| ATOM | 6538 | OD1 | ASN | A | 411 | 46.413 | −17.859 | −22.745 | 1.00 | 23.89 A | O |
| ATOM | 6539 | ND2 | ASN | A | 411 | 48.178 | −18.858 | −21.775 | 1.00 | 24.71 A | N |
| ATOM | 6542 | C | ASN | A | 411 | 45.514 | −18.009 | −18.219 | 1.00 | 23.88 A | C |
| ATOM | 6543 | O | ASN | A | 411 | 45.574 | −18.888 | −17.361 | 1.00 | 23.42 A | O |
| ATOM | 6545 | N | ILE | A | 412 | 44.547 | −17.098 | −18.267 | 1.00 | 24.33 A | N |
| ATOM | 6546 | CA | ILE | A | 412 | 43.466 | −17.042 | −17.285 | 1.00 | 24.54 A | C |
| ATOM | 6548 | CB | ILE | A | 412 | 43.018 | −15.583 | −17.036 | 1.00 | 24.66 A | C |
| ATOM | 6550 | CG1 | ILE | A | 412 | 44.224 | −14.686 | −16.727 | 1.00 | 24.61 A | C |
| ATOM | 6553 | CD1 | ILE | A | 412 | 45.133 | −15.218 | −15.646 | 1.00 | 24.33 A | C |
| ATOM | 6557 | CG2 | ILE | A | 412 | 41.997 | −15.516 | −15.910 | 1.00 | 25.28 A | C |
| ATOM | 6561 | C | ILE | A | 412 | 42.267 | −17.841 | −17.788 | 1.00 | 24.52 A | C |
| ATOM | 6562 | O | ILE | A | 412 | 41.795 | −17.612 | −18.901 | 1.00 | 24.75 A | O |
| ATOM | 6564 | N | LYS | A | 413 | 41.776 | −18.771 | −16.973 | 1.00 | 24.56 A | N |
| ATOM | 6565 | CA | LYS | A | 413 | 40.589 | −19.552 | −17.323 | 1.00 | 24.82 A | C |
| ATOM | 6567 | CB | LYS | A | 413 | 40.819 | −21.041 | −17.055 | 1.00 | 25.06 A | C |
| ATOM | 6570 | CG | LYS | A | 413 | 42.016 | −21.623 | −17.795 | 1.00 | 25.64 A | C |
| ATOM | 6573 | CD | LYS | A | 413 | 41.849 | −23.112 | −18.064 | 1.00 | 28.37 A | C |
| ATOM | 6576 | CE | LYS | A | 413 | 42.855 | −23.606 | −19.100 | 1.00 | 30.53 A | C |
| ATOM | 6579 | NZ | LYS | A | 413 | 42.618 | −25.028 | −19.493 | 1.00 | 30.83 A | N |
| ATOM | 6583 | C | LYS | A | 413 | 39.389 | −19.053 | −16.530 | 1.00 | 24.68 A | C |
| ATOM | 6584 | O | LYS | A | 413 | 39.521 | −18.714 | −15.352 | 1.00 | 23.95 A | O |
| ATOM | 6586 | N | LYS | A | 414 | 38.225 | −19.005 | −17.176 | 1.00 | 25.21 A | N |
| ATOM | 6587 | CA | LYS | A | 414 | 37.006 | −18.530 | −16.517 | 1.00 | 25.78 A | C |
| ATOM | 6589 | CB | LYS | A | 414 | 35.845 | −18.387 | −17.509 | 1.00 | 25.92 A | C |
| ATOM | 6592 | CG | LYS | A | 414 | 34.681 | −17.556 | −16.956 | 1.00 | 27.75 A | C |
| ATOM | 6595 | CD | LYS | A | 414 | 33.572 | −17.312 | −17.982 | 1.00 | 28.34 A | C |
| ATOM | 6598 | CE | LYS | A | 414 | 32.817 | −18.588 | −18.334 | 1.00 | 28.85 A | C |
| ATOM | 6601 | NZ | LYS | A | 414 | 32.295 | −19.301 | −17.133 | 1.00 | 28.73 A | N |
| ATOM | 6605 | C | LYS | A | 414 | 36.612 | −19.462 | −15.371 | 1.00 | 25.94 A | C |
| ATOM | 6606 | O | LYS | A | 414 | 36.215 | −18.997 | −14.301 | 1.00 | 26.04 A | O |
| ATOM | 6608 | N | GLU | A | 415 | 36.734 | −20.771 | −15.598 | 1.00 | 25.93 A | N |
| ATOM | 6609 | CA | GLU | A | 415 | 36.443 | −21.772 | −14.567 | 1.00 | 25.59 A | C |
| ATOM | 6611 | CB | GLU | A | 415 | 36.571 | −23.194 | −15.129 | 1.00 | 25.91 A | C |
| ATOM | 6614 | CG | GLU | A | 415 | 35.980 | −24.278 | −14.212 | 1.00 | 27.72 A | C |
| ATOM | 6617 | CD | GLU | A | 415 | 36.785 | −25.576 | −14.192 | 1.00 | 29.56 A | C |
| ATOM | 6618 | OE1 | GLU | A | 415 | 38.035 | −25.519 | −14.216 | 1.00 | 30.42 A | O |
| ATOM | 6619 | OE2 | GLU | A | 415 | 36.160 | −26.658 | −14.127 | 1.00 | 30.95 A | O |
| ATOM | 6620 | C | GLU | A | 415 | 37.375 | −21.614 | −13.367 | 1.00 | 24.71 A | C |
| ATOM | 6621 | O | GLU | A | 415 | 36.925 | −21.641 | −12.221 | 1.00 | 24.35 A | O |
| ATOM | 6623 | N | GLU | A | 416 | 38.668 | −21.455 | −13.635 | 1.00 | 24.19 A | N |
| ATOM | 6624 | CA | GLU | A | 416 | 39.653 | −21.259 | −12.574 | 1.00 | 24.24 A | C |
| ATOM | 6626 | CB | GLU | A | 416 | 41.062 | −21.074 | −13.151 | 1.00 | 24.41 A | C |
| ATOM | 6629 | CG | GLU | A | 416 | 41.712 | −22.376 | −13.612 | 1.00 | 25.81 A | C |
| ATOM | 6632 | CD | GLU | A | 416 | 43.177 | −22.214 | −13.985 | 1.00 | 26.72 A | C |
| ATOM | 6633 | OE1 | GLU | A | 416 | 43.547 | −21.142 | −14.507 | 1.00 | 27.38 A | O |
| ATOM | 6634 | OE2 | GLU | A | 416 | 43.958 | −23.166 | −13.764 | 1.00 | 26.58 A | O |

TABLE 8-2-continued

Coordinates for L494P Structure

| ATOM | 6635 | C | GLU | A | 416 | 39.291 | −20.077 | −11.673 | 1.00 | 23.98 | A | C |
|---|---|---|---|---|---|---|---|---|---|---|---|---|
| ATOM | 6636 | O | GLU | A | 416 | 39.215 | −20.232 | −10.454 | 1.00 | 23.87 | A | O |
| ATOM | 6638 | N | ILE | A | 417 | 39.052 | −18.910 | −12.269 | 1.00 | 23.83 | A | N |
| ATOM | 6639 | CA | ILE | A | 417 | 38.704 | −17.719 | −11.484 | 1.00 | 23.96 | A | C |
| ATOM | 6641 | CB | ILE | A | 417 | 38.800 | −16.395 | −12.301 | 1.00 | 24.26 | A | C |
| ATOM | 6643 | CG1 | ILE | A | 417 | 37.708 | −16.310 | −13.373 | 1.00 | 24.99 | A | C |
| ATOM | 6646 | CD1 | ILE | A | 417 | 37.647 | −14.966 | −14.065 | 1.00 | 24.44 | A | C |
| ATOM | 6650 | CG2 | ILE | A | 417 | 40.185 | −16.249 | −12.925 | 1.00 | 23.85 | A | C |
| ATOM | 6654 | C | ILE | A | 417 | 37.316 | −17.828 | −10.848 | 1.00 | 23.84 | A | C |
| ATOM | 6655 | O | ILE | A | 417 | 37.052 | −17.190 | −9.832 | 1.00 | 23.74 | A | O |
| ATOM | 6657 | N | GLU | A | 418 | 36.438 | −18.631 | −11.448 | 1.00 | 23.87 | A | N |
| ATOM | 6658 | CA | GLU | A | 418 | 35.107 | −18.886 | −10.882 | 1.00 | 24.02 | A | C |
| ATOM | 6660 | CB | GLU | A | 418 | 34.281 | −19.798 | −11.802 | 1.00 | 24.29 | A | C |
| ATOM | 6663 | CG | GLU | A | 418 | 32.821 | −19.382 | −11.980 | 1.00 | 25.56 | A | C |
| ATOM | 6666 | CD | GLU | A | 418 | 32.536 | −18.833 | −13.367 | 1.00 | 27.78 | A | C |
| ATOM | 6667 | OE1 | GLU | A | 418 | 32.836 | −19.536 | −14.358 | 1.00 | 29.63 | A | O |
| ATOM | 6668 | OE2 | GLU | A | 418 | 32.003 | −17.707 | −13.469 | 1.00 | 28.94 | A | O |
| ATOM | 6669 | C | GLU | A | 418 | 35.227 | −19.551 | −9.510 | 1.00 | 23.54 | A | C |
| ATOM | 6670 | O | GLU | A | 418 | 34.483 | −19.225 | −8.585 | 1.00 | 23.37 | A | O |
| ATOM | 6672 | N | ASN | A | 419 | 36.161 | −20.494 | −9.399 | 1.00 | 23.03 | A | N |
| ATOM | 6673 | CA | ASN | A | 419 | 36.414 | −21.200 | −8.144 | 1.00 | 22.72 | A | C |
| ATOM | 6675 | CB | ASN | A | 419 | 37.219 | −22.481 | −8.399 | 1.00 | 22.49 | A | C |
| ATOM | 6678 | CG | ASN | A | 419 | 36.353 | −23.621 | −8.901 | 1.00 | 21.26 | A | C |
| ATOM | 6679 | OD1 | ASN | A | 419 | 35.999 | −24.523 | −8.143 | 1.00 | 20.38 | A | O |
| ATOM | 6680 | ND2 | ASN | A | 419 | 35.994 | −23.577 | −10.176 | 1.00 | 18.71 | A | N |
| ATOM | 6683 | C | ASN | A | 419 | 37.110 | −20.332 | −7.094 | 1.00 | 22.76 | A | C |
| ATOM | 6684 | O | ASN | A | 419 | 36.831 | −20.460 | −5.901 | 1.00 | 22.68 | A | O |
| ATOM | 6686 | N | LEU | A | 420 | 38.007 | −19.450 | −7.535 | 1.00 | 23.02 | A | N |
| ATOM | 6687 | CA | LEU | A | 420 | 38.646 | −18.485 | −6.630 | 1.00 | 23.24 | A | C |
| ATOM | 6689 | CB | LEU | A | 420 | 39.740 | −17.689 | −7.352 | 1.00 | 23.12 | A | C |
| ATOM | 6692 | CG | LEU | A | 420 | 40.950 | −18.465 | −7.878 | 1.00 | 22.58 | A | C |
| ATOM | 6694 | CD1 | LEU | A | 420 | 41.884 | −17.542 | −8.649 | 1.00 | 23.76 | A | C |
| ATOM | 6698 | CD2 | LEU | A | 420 | 41.694 | −19.150 | −6.747 | 1.00 | 21.73 | A | C |
| ATOM | 6702 | C | LEU | A | 420 | 37.616 | −17.519 | −6.037 | 1.00 | 23.34 | A | C |
| ATOM | 6703 | O | LEU | A | 420 | 37.698 | −17.159 | −4.862 | 1.00 | 23.29 | A | O |
| ATOM | 6705 | N | GLN | A | 421 | 36.649 | −17.113 | −6.859 | 1.00 | 23.39 | A | N |
| ATOM | 6706 | CA | GLN | A | 421 | 35.555 | −16.240 | −6.426 | 1.00 | 23.61 | A | C |
| ATOM | 6708 | CB | GLN | A | 421 | 34.664 | −15.883 | −7.619 | 1.00 | 23.81 | A | C |
| ATOM | 6711 | CG | GLN | A | 421 | 35.317 | −14.977 | −8.655 | 1.00 | 25.57 | A | C |
| ATOM | 6714 | CD | GLN | A | 421 | 35.021 | −13.508 | −8.426 | 1.00 | 27.53 | A | C |
| ATOM | 6715 | OE1 | GLN | A | 421 | 34.355 | −12.867 | −9.241 | 1.00 | 27.80 | A | O |
| ATOM | 6716 | NE2 | GLN | A | 421 | 35.507 | −12.967 | −7.310 | 1.00 | 28.75 | A | N |
| ATOM | 6719 | C | GLN | A | 421 | 34.687 | −16.871 | −5.336 | 1.00 | 23.75 | A | C |
| ATOM | 6720 | O | GLN | A | 421 | 34.012 | −16.160 | −4.594 | 1.00 | 23.75 | A | O |
| ATOM | 6722 | N | LYS | A | 422 | 34.699 | −18.202 | −5.254 | 1.00 | 24.07 | A | N |
| ATOM | 6723 | CA | LYS | A | 422 | 33.875 | −18.944 | −4.301 | 1.00 | 24.27 | A | C |
| ATOM | 6725 | CB | LYS | A | 422 | 33.053 | −19.995 | −5.060 | 1.00 | 24.49 | A | C |
| ATOM | 6728 | CG | LYS | A | 422 | 32.059 | −19.388 | −6.053 | 1.00 | 26.08 | A | C |
| ATOM | 6731 | CD | LYS | A | 422 | 31.640 | −20.375 | −7.140 | 1.00 | 28.24 | A | C |
| ATOM | 6734 | CE | LYS | A | 422 | 30.776 | −19.693 | −8.205 | 1.00 | 28.90 | A | C |
| ATOM | 6737 | NZ | LYS | A | 422 | 30.279 | −20.642 | −9.246 | 1.00 | 28.82 | A | N |
| ATOM | 6741 | C | LYS | A | 422 | 34.716 | −19.603 | −3.196 | 1.00 | 23.98 | A | C |
| ATOM | 6742 | O | LYS | A | 422 | 34.248 | −20.524 | −2.519 | 1.00 | 23.87 | A | O |
| ATOM | 6744 | N | TYR | A | 423 | 35.942 | −19.107 | −3.005 | 1.00 | 23.57 | A | N |
| ATOM | 6745 | CA | TYR | A | 423 | 36.902 | −19.675 | −2.046 | 1.00 | 23.15 | A | C |
| ATOM | 6747 | CB | TYR | A | 423 | 36.697 | −19.077 | −0.643 | 1.00 | 22.87 | A | C |
| ATOM | 6750 | CG | TYR | A | 423 | 36.761 | −17.559 | −0.637 | 1.00 | 23.55 | A | C |
| ATOM | 6751 | CD1 | TYR | A | 423 | 37.857 | −16.888 | −1.182 | 1.00 | 24.97 | A | C |
| ATOM | 6753 | CE1 | TYR | A | 423 | 37.919 | −15.497 | −1.197 | 1.00 | 24.81 | A | C |
| ATOM | 6755 | CZ | TYR | A | 423 | 36.880 | −14.761 | −0.660 | 1.00 | 24.32 | A | C |
| ATOM | 6756 | OH | TYR | A | 423 | 36.945 | −13.388 | −0.673 | 1.00 | 23.63 | A | O |
| ATOM | 6758 | CE2 | TYR | A | 423 | 35.782 | −15.400 | −0.110 | 1.00 | 23.79 | A | C |
| ATOM | 6760 | CD2 | TYR | A | 423 | 35.726 | −16.794 | −0.102 | 1.00 | 24.22 | A | C |
| ATOM | 6762 | C | TYR | A | 423 | 36.847 | −21.206 | −2.046 | 1.00 | 22.87 | A | C |
| ATOM | 6763 | O | TYR | A | 423 | 36.540 | −21.849 | −1.038 | 1.00 | 23.25 | A | O |
| ATOM | 6765 | N | HIS | A | 424 | 37.144 | −21.765 | −3.214 | 1.00 | 22.22 | A | N |
| ATOM | 6766 | CA | HIS | A | 424 | 37.125 | −23.205 | −3.449 | 1.00 | 21.90 | A | C |
| ATOM | 6768 | CB | HIS | A | 424 | 37.276 | −23.465 | −4.956 | 1.00 | 22.14 | A | C |
| ATOM | 6771 | CG | HIS | A | 424 | 37.467 | −24.904 | −5.320 | 1.00 | 23.25 | A | C |
| ATOM | 6772 | ND1 | HIS | A | 424 | 38.681 | −25.408 | −5.734 | 1.00 | 23.32 | A | N |
| ATOM | 6774 | CE1 | HIS | A | 424 | 38.555 | −26.698 | −5.989 | 1.00 | 23.99 | A | C |
| ATOM | 6776 | NE2 | HIS | A | 424 | 37.303 | −27.049 | −5.758 | 1.00 | 24.51 | A | N |
| ATOM | 6778 | CD2 | HIS | A | 424 | 36.600 | −25.944 | −5.341 | 1.00 | 24.99 | A | C |
| ATOM | 6780 | C | HIS | A | 424 | 38.232 | −23.894 | −2.652 | 1.00 | 21.23 | A | C |
| ATOM | 6781 | O | HIS | A | 424 | 39.226 | −23.266 | −2.293 | 1.00 | 21.22 | A | O |
| ATOM | 6783 | N | ASP | A | 425 | 38.042 | −25.184 | −2.383 | 1.00 | 20.88 | A | N |
| ATOM | 6784 | CA | ASP | A | 425 | 38.963 | −25.991 | −1.561 | 1.00 | 20.94 | A | C |
| ATOM | 6786 | CB | ASP | A | 425 | 38.655 | −27.491 | −1.731 | 1.00 | 21.19 | A | C |

TABLE 8-2-continued

Coordinates for L494P Structure

| ATOM | 6789 | CG | ASP | A | 425 | 37.337 | −27.908 | −1.083 | 1.00 | 22.84 | A | C |
| ATOM | 6790 | OD1 | ASP | A | 425 | 36.714 | −27.086 | −0.374 | 1.00 | 27.02 | A | O |
| ATOM | 6791 | OD2 | ASP | A | 425 | 36.923 | −29.070 | −1.284 | 1.00 | 23.18 | A | O |
| ATOM | 6792 | C | ASP | A | 425 | 40.467 | −25.759 | −1.800 | 1.00 | 20.30 | A | C |
| ATOM | 6793 | O | ASP | A | 425 | 41.253 | −25.806 | −0.851 | 1.00 | 20.33 | A | O |
| ATOM | 6795 | N | THR | A | 426 | 40.870 | −25.519 | −3.046 | 1.00 | 19.20 | A | N |
| ATOM | 6796 | CA | THR | A | 426 | 42.295 | −25.401 | −3.366 | 1.00 | 18.17 | A | C |
| ATOM | 6798 | CB | THR | A | 426 | 42.546 | −25.212 | −4.878 | 1.00 | 17.95 | A | C |
| ATOM | 6800 | OG1 | THR | A | 426 | 41.842 | −26.219 | −5.612 | 1.00 | 17.41 | A | O |
| ATOM | 6802 | CG2 | THR | A | 426 | 44.033 | −25.315 | −5.196 | 1.00 | 15.99 | A | C |
| ATOM | 6806 | C | THR | A | 426 | 42.960 | −24.263 | −2.597 | 1.00 | 17.94 | A | C |
| ATOM | 6807 | O | THR | A | 426 | 44.085 | −24.424 | −2.127 | 1.00 | 18.23 | A | O |
| ATOM | 6809 | N | ILE | A | 427 | 42.270 | −23.127 | −2.471 | 1.00 | 17.76 | A | N |
| ATOM | 6810 | CA | ILE | A | 427 | 42.795 | −21.979 | −1.711 | 1.00 | 17.88 | A | C |
| ATOM | 6812 | CB | ILE | A | 427 | 42.699 | −20.642 | −2.499 | 1.00 | 17.38 | A | C |
| ATOM | 6814 | CG1 | ILE | A | 427 | 41.246 | −20.209 | −2.701 | 1.00 | 16.70 | A | C |
| ATOM | 6817 | CD1 | ILE | A | 427 | 41.119 | −18.858 | −3.365 | 1.00 | 16.78 | A | C |
| ATOM | 6821 | CG2 | ILE | A | 427 | 43.415 | −20.755 | −3.836 | 1.00 | 16.09 | A | C |
| ATOM | 6825 | C | ILE | A | 427 | 42.137 | −21.803 | −0.339 | 1.00 | 18.62 | A | C |
| ATOM | 6826 | O | ILE | A | 427 | 42.602 | −20.996 | 0.471 | 1.00 | 19.27 | A | O |
| ATOM | 6828 | N | SER | A | 428 | 41.065 | −22.550 | −0.082 | 1.00 | 18.85 | A | N |
| ATOM | 6829 | CA | SER | A | 428 | 40.426 | −22.561 | 1.233 | 1.00 | 19.03 | A | C |
| ATOM | 6831 | CB | SER | A | 428 | 39.035 | −23.200 | 1.145 | 1.00 | 18.90 | A | C |
| ATOM | 6834 | OG | SER | A | 428 | 38.499 | −23.466 | 2.429 | 1.00 | 19.43 | A | O |
| ATOM | 6836 | C | SER | A | 428 | 41.291 | −23.317 | 2.241 | 1.00 | 19.40 | A | C |
| ATOM | 6837 | O | SER | A | 428 | 41.671 | −22.772 | 3.274 | 1.00 | 19.21 | A | O |
| ATOM | 6839 | N | ARG | A | 429 | 41.614 | −24.566 | 1.914 | 1.00 | 20.31 | A | N |
| ATOM | 6840 | CA | ARG | A | 429 | 42.331 | −25.465 | 2.833 | 1.00 | 20.92 | A | C |
| ATOM | 6842 | CB | ARG | A | 429 | 42.587 | −26.839 | 2.185 | 1.00 | 21.25 | A | C |
| ATOM | 6845 | CG | ARG | A | 429 | 41.326 | −27.586 | 1.733 | 1.00 | 23.47 | A | C |
| ATOM | 6848 | CD | ARG | A | 429 | 40.833 | −28.594 | 2.762 | 1.00 | 26.54 | A | C |
| ATOM | 6851 | NE | ARG | A | 429 | 39.381 | −28.778 | 2.710 | 1.00 | 28.25 | A | N |
| ATOM | 6853 | CZ | ARG | A | 429 | 38.719 | −29.394 | 1.730 | 1.00 | 29.99 | A | C |
| ATOM | 6854 | NH1 | ARG | A | 429 | 39.359 | −29.903 | 0.676 | 1.00 | 29.63 | A | N |
| ATOM | 6857 | NH2 | ARG | A | 429 | 37.396 | −29.497 | 1.801 | 1.00 | 30.83 | A | N |
| ATOM | 6860 | C | ARG | A | 429 | 43.649 | −24.871 | 3.347 | 1.00 | 20.52 | A | C |
| ATOM | 6861 | O | ARG | A | 429 | 43.869 | −24.835 | 4.555 | 1.00 | 20.89 | A | O |
| ATOM | 6863 | N | PRO | A | 430 | 44.524 | −24.388 | 2.442 | 1.00 | 19.92 | A | N |
| ATOM | 6864 | CA | PRO | A | 430 | 45.782 | −23.822 | 2.933 | 1.00 | 19.69 | A | C |
| ATOM | 6866 | CB | PRO | A | 430 | 46.451 | −23.278 | 1.664 | 1.00 | 19.80 | A | C |
| ATOM | 6869 | CG | PRO | A | 430 | 45.801 | −23.986 | 0.541 | 1.00 | 19.77 | A | C |
| ATOM | 6872 | CD | PRO | A | 430 | 44.400 | −24.245 | 0.982 | 1.00 | 20.08 | A | C |
| ATOM | 6875 | C | PRO | A | 430 | 45.558 | −22.695 | 3.934 | 1.00 | 19.44 | A | C |
| ATOM | 6876 | O | PRO | A | 430 | 46.314 | −22.573 | 4.898 | 1.00 | 19.69 | A | O |
| ATOM | 6877 | N | SER | A | 431 | 44.520 | −21.891 | 3.701 | 1.00 | 19.05 | A | N |
| ATOM | 6878 | CA | SER | A | 431 | 44.171 | −20.780 | 4.591 | 1.00 | 18.38 | A | C |
| ATOM | 6880 | CB | SER | A | 431 | 43.173 | −19.843 | 3.910 | 1.00 | 18.34 | A | C |
| ATOM | 6883 | OG | SER | A | 431 | 43.653 | −19.431 | 2.639 | 1.00 | 18.28 | A | O |
| ATOM | 6885 | C | SER | A | 431 | 43.610 | −21.273 | 5.925 | 1.00 | 17.67 | A | C |
| ATOM | 6886 | O | SER | A | 431 | 43.797 | −20.621 | 6.954 | 1.00 | 16.78 | A | O |
| ATOM | 6888 | N | HIS | A | 432 | 42.922 | −22.417 | 5.896 | 1.00 | 17.38 | A | N |
| ATOM | 6889 | CA | HIS | A | 432 | 42.501 | −23.105 | 7.121 | 1.00 | 17.22 | A | C |
| ATOM | 6891 | CB | HIS | A | 432 | 41.774 | −24.426 | 6.803 | 1.00 | 17.35 | A | C |
| ATOM | 6894 | CG | HIS | A | 432 | 40.354 | −24.255 | 6.353 | 1.00 | 16.88 | A | C |
| ATOM | 6895 | ND1 | HIS | A | 432 | 39.389 | −25.215 | 6.569 | 1.00 | 16.42 | A | N |
| ATOM | 6897 | CE1 | HIS | A | 432 | 38.237 | −24.799 | 6.074 | 1.00 | 16.45 | A | C |
| ATOM | 6899 | NE2 | HIS | A | 432 | 38.418 | −23.601 | 5.548 | 1.00 | 14.80 | A | N |
| ATOM | 6901 | CD2 | HIS | A | 432 | 39.733 | −23.236 | 5.712 | 1.00 | 16.06 | A | C |
| ATOM | 6903 | C | HIS | A | 432 | 43.723 | −23.383 | 8.002 | 1.00 | 16.93 | A | C |
| ATOM | 6904 | O | HIS | A | 432 | 43.687 | −23.163 | 9.215 | 1.00 | 16.68 | A | O |
| ATOM | 6906 | N | ILE | A | 433 | 44.800 | −23.862 | 7.378 | 1.00 | 16.43 | A | N |
| ATOM | 6907 | CA | ILE | A | 433 | 46.064 | −24.108 | 8.078 | 1.00 | 16.05 | A | C |
| ATOM | 6909 | CB | ILE | A | 433 | 47.080 | −24.877 | 7.189 | 1.00 | 16.29 | A | C |
| ATOM | 6911 | CG1 | ILE | A | 433 | 46.752 | −26.374 | 7.152 | 1.00 | 16.71 | A | C |
| ATOM | 6914 | CD1 | ILE | A | 433 | 45.604 | −26.727 | 6.261 | 1.00 | 15.49 | A | C |
| ATOM | 6918 | CG2 | ILE | A | 433 | 48.505 | −24.683 | 7.704 | 1.00 | 17.15 | A | C |
| ATOM | 6922 | C | ILE | A | 433 | 46.710 | −22.804 | 8.553 | 1.00 | 15.22 | A | C |
| ATOM | 6923 | O | ILE | A | 433 | 47.267 | −22.751 | 9.648 | 1.00 | 15.08 | A | O |
| ATOM | 6925 | N | PHE | A | 434 | 46.631 | −21.765 | 7.725 | 1.00 | 14.47 | A | N |
| ATOM | 6926 | CA | PHE | A | 434 | 47.211 | −20.455 | 8.034 | 1.00 | 14.05 | A | C |
| ATOM | 6928 | CB | PHE | A | 434 | 47.038 | −19.527 | 6.814 | 1.00 | 13.92 | A | C |
| ATOM | 6931 | CG | PHE | A | 434 | 47.583 | −18.117 | 6.985 | 1.00 | 13.80 | A | C |
| ATOM | 6932 | CD1 | PHE | A | 434 | 48.512 | −17.785 | 7.967 | 1.00 | 14.68 | A | C |
| ATOM | 6934 | CE1 | PHE | A | 434 | 48.987 | −16.482 | 8.081 | 1.00 | 13.77 | A | C |
| ATOM | 6936 | CZ | PHE | A | 434 | 48.558 | −15.508 | 7.200 | 1.00 | 12.50 | A | C |
| ATOM | 6938 | CE2 | PHE | A | 434 | 47.654 | −15.829 | 6.213 | 1.00 | 11.41 | A | C |
| ATOM | 6940 | CD2 | PHE | A | 434 | 47.177 | −17.122 | 6.104 | 1.00 | 13.10 | A | C |
| ATOM | 6942 | C | PHE | A | 434 | 46.599 | −19.864 | 9.311 | 1.00 | 13.97 | A | C |

TABLE 8-2-continued

Coordinates for L494P Structure

| ATOM | 6943 | O | PHE | A | 434 | 47.325 | −19.429 | 10.208 | 1.00 | 13.34 | A | O |
|---|---|---|---|---|---|---|---|---|---|---|---|---|
| ATOM | 6945 | N | ARG | A | 435 | 45.273 | −19.878 | 9.407 | 1.00 | 14.22 | A | N |
| ATOM | 6946 | CA | ARG | A | 435 | 44.594 | −19.371 | 10.603 | 1.00 | 14.37 | A | C |
| ATOM | 6948 | CB | ARG | A | 435 | 43.086 | −19.241 | 10.359 | 1.00 | 14.35 | A | C |
| ATOM | 6951 | CG | ARG | A | 435 | 42.252 | −18.907 | 11.593 | 1.00 | 15.10 | A | C |
| ATOM | 6954 | CD | ARG | A | 435 | 42.754 | −17.675 | 12.337 | 1.00 | 16.05 | A | C |
| ATOM | 6957 | NE | ARG | A | 435 | 42.700 | −16.464 | 11.524 | 1.00 | 17.00 | A | N |
| ATOM | 6959 | CZ | ARG | A | 435 | 43.235 | −15.293 | 11.870 | 1.00 | 18.01 | A | C |
| ATOM | 6960 | NH1 | ARG | A | 435 | 43.888 | −15.153 | 13.020 | 1.00 | 18.43 | A | N |
| ATOM | 6963 | NH2 | ARG | A | 435 | 43.121 | −14.253 | 11.054 | 1.00 | 18.41 | A | N |
| ATOM | 6966 | C | ARG | A | 435 | 44.864 | −20.264 | 11.813 | 1.00 | 14.63 | A | C |
| ATOM | 6967 | O | ARG | A | 435 | 45.259 | −19.774 | 12.870 | 1.00 | 14.88 | A | O |
| ATOM | 6969 | N | LEU | A | 436 | 44.650 | −21.569 | 11.651 | 1.00 | 14.88 | A | N |
| ATOM | 6970 | CA | LEU | A | 436 | 44.874 | −22.531 | 12.735 | 1.00 | 14.69 | A | C |
| ATOM | 6972 | CB | LEU | A | 436 | 44.567 | −23.964 | 12.274 | 1.00 | 14.43 | A | C |
| ATOM | 6975 | CG | LEU | A | 436 | 43.095 | −24.373 | 12.141 | 1.00 | 12.91 | A | C |
| ATOM | 6977 | CD1 | LEU | A | 436 | 42.975 | −25.815 | 11.667 | 1.00 | 9.69 | A | C |
| ATOM | 6981 | CD2 | LEU | A | 436 | 42.353 | −24.194 | 13.454 | 1.00 | 11.60 | A | C |
| ATOM | 6985 | C | LEU | A | 436 | 46.300 | −22.450 | 13.302 | 1.00 | 15.09 | A | C |
| ATOM | 6986 | O | LEU | A | 436 | 46.480 | −22.448 | 14.519 | 1.00 | 15.32 | A | O |
| ATOM | 6988 | N | CYS | A | 437 | 47.303 | −22.375 | 12.429 | 1.00 | 15.32 | A | N |
| ATOM | 6989 | CA | CYS | A | 437 | 48.692 | −22.223 | 12.877 | 1.00 | 15.91 | A | C |
| ATOM | 6991 | CB | CYS | A | 437 | 49.663 | −22.121 | 11.693 | 1.00 | 16.11 | A | C |
| ATOM | 6994 | SG | CYS | A | 437 | 50.204 | −23.702 | 11.009 | 1.00 | 15.22 | A | S |
| ATOM | 6996 | C | CYS | A | 437 | 48.848 | −20.989 | 13.763 | 1.00 | 16.70 | A | C |
| ATOM | 6997 | O | CYS | A | 437 | 49.285 | −21.100 | 14.910 | 1.00 | 17.68 | A | O |
| ATOM | 6999 | N | ASN | A | 438 | 48.485 | −19.825 | 13.224 | 1.00 | 16.73 | A | N |
| ATOM | 7000 | CA | ASN | A | 438 | 48.591 | −18.548 | 13.946 | 1.00 | 16.68 | A | C |
| ATOM | 7002 | CB | ASN | A | 438 | 47.902 | −17.428 | 13.148 | 1.00 | 16.72 | A | C |
| ATOM | 7005 | CG | ASN | A | 438 | 48.141 | −16.036 | 13.733 | 1.00 | 16.65 | A | C |
| ATOM | 7006 | OD1 | ASN | A | 438 | 48.240 | −15.855 | 14.947 | 1.00 | 18.65 | A | O |
| ATOM | 7007 | ND2 | ASN | A | 438 | 48.214 | −15.042 | 12.858 | 1.00 | 16.47 | A | N |
| ATOM | 7010 | C | ASN | A | 438 | 47.993 | −18.634 | 15.349 | 1.00 | 16.53 | A | C |
| ATOM | 7011 | O | ASN | A | 438 | 48.666 | −18.340 | 16.343 | 1.00 | 16.47 | A | O |
| ATOM | 7013 | N | ASP | A | 439 | 46.735 | −19.055 | 15.417 | 1.00 | 16.27 | A | N |
| ATOM | 7014 | CA | ASP | A | 439 | 45.992 | −19.076 | 16.672 | 1.00 | 16.30 | A | C |
| ATOM | 7016 | CB | ASP | A | 439 | 44.503 | −19.296 | 16.400 | 1.00 | 16.10 | A | C |
| ATOM | 7019 | CG | ASP | A | 439 | 43.872 | −18.134 | 15.650 | 1.00 | 15.85 | A | C |
| ATOM | 7020 | OD1 | ASP | A | 439 | 44.623 | −17.292 | 15.112 | 1.00 | 14.52 | A | O |
| ATOM | 7021 | OD2 | ASP | A | 439 | 42.626 | −18.059 | 15.598 | 1.00 | 16.49 | A | O |
| ATOM | 7022 | C | ASP | A | 439 | 46.527 | −20.115 | 17.660 | 1.00 | 16.83 | A | C |
| ATOM | 7023 | O | ASP | A | 439 | 46.451 | −19.911 | 18.874 | 1.00 | 17.09 | A | O |
| ATOM | 7025 | N | LEU | A | 440 | 47.067 | −21.219 | 17.145 | 1.00 | 17.06 | A | N |
| ATOM | 7026 | CA | LEU | A | 440 | 47.742 | −22.215 | 17.987 | 1.00 | 17.22 | A | C |
| ATOM | 7028 | CB | LEU | A | 440 | 48.155 | −23.442 | 17.166 | 1.00 | 17.05 | A | C |
| ATOM | 7031 | CG | LEU | A | 440 | 47.100 | −24.537 | 17.019 | 1.00 | 15.68 | A | C |
| ATOM | 7033 | CD1 | LEU | A | 440 | 47.460 | −25.487 | 15.894 | 1.00 | 15.98 | A | C |
| ATOM | 7037 | CD2 | LEU | A | 440 | 46.955 | −25.288 | 18.321 | 1.00 | 15.39 | A | C |
| ATOM | 7041 | C | LEU | A | 440 | 48.972 | −21.625 | 18.680 | 1.00 | 18.01 | A | C |
| ATOM | 7042 | O | LEU | A | 440 | 49.261 | −21.965 | 19.830 | 1.00 | 17.74 | A | O |
| ATOM | 7044 | N | ALA | A | 441 | 49.685 | −20.747 | 17.972 | 1.00 | 18.91 | A | N |
| ATOM | 7045 | CA | ALA | A | 441 | 50.883 | −20.083 | 18.502 | 1.00 | 19.53 | A | C |
| ATOM | 7047 | CB | ALA | A | 441 | 51.622 | −19.360 | 17.384 | 1.00 | 19.65 | A | C |
| ATOM | 7051 | C | ALA | A | 441 | 50.542 | −19.101 | 19.616 | 1.00 | 19.96 | A | C |
| ATOM | 7052 | O | ALA | A | 441 | 51.224 | −19.050 | 20.639 | 1.00 | 19.83 | A | O |
| ATOM | 7054 | N | SER | A | 442 | 49.480 | −18.328 | 19.407 | 1.00 | 20.77 | A | N |
| ATOM | 7055 | CA | SER | A | 442 | 49.015 | −17.350 | 20.387 | 1.00 | 21.70 | A | C |
| ATOM | 7057 | CB | SER | A | 442 | 48.473 | −16.122 | 19.653 | 1.00 | 22.02 | A | C |
| ATOM | 7060 | OG | SER | A | 442 | 47.282 | −16.440 | 18.950 | 1.00 | 22.89 | A | O |
| ATOM | 7062 | C | SER | A | 442 | 47.926 | −17.911 | 21.312 | 1.00 | 22.14 | A | C |
| ATOM | 7063 | O | SER | A | 442 | 47.178 | −17.149 | 21.924 | 1.00 | 22.10 | A | O |
| ATOM | 7065 | N | ALA | A | 443 | 47.845 | −19.236 | 21.422 | 1.00 | 22.95 | A | N |
| ATOM | 7066 | CA | ALA | A | 443 | 46.762 | −19.886 | 22.161 | 1.00 | 23.60 | A | C |
| ATOM | 7068 | CB | ALA | A | 443 | 46.779 | −21.396 | 21.915 | 1.00 | 23.77 | A | C |
| ATOM | 7072 | C | ALA | A | 443 | 46.816 | −19.592 | 23.660 | 1.00 | 24.06 | A | C |
| ATOM | 7073 | O | ALA | A | 443 | 45.974 | −18.857 | 24.177 | 1.00 | 24.06 | A | O |
| ATOM | 7075 | N | SER | A | 444 | 47.813 | −20.151 | 24.344 | 1.00 | 24.55 | A | N |
| ATOM | 7076 | CA | SER | A | 444 | 47.912 | −20.054 | 25.806 | 1.00 | 24.88 | A | C |
| ATOM | 7078 | CB | SER | A | 444 | 49.039 | −20.954 | 26.324 | 1.00 | 24.85 | A | C |
| ATOM | 7081 | OG | SER | A | 444 | 50.274 | −20.624 | 25.714 | 1.00 | 25.18 | A | O |
| ATOM | 7083 | C | SER | A | 444 | 48.119 | −18.625 | 26.320 | 1.00 | 25.16 | A | C |
| ATOM | 7084 | O | SER | A | 444 | 47.749 | −18.315 | 27.456 | 1.00 | 25.37 | A | O |
| ATOM | 7086 | N | ALA | A | 445 | 48.709 | −17.764 | 25.490 | 1.00 | 25.22 | A | N |
| ATOM | 7087 | CA | ALA | A | 445 | 48.924 | −16.363 | 25.854 | 1.00 | 25.09 | A | C |
| ATOM | 7089 | CB | ALA | A | 445 | 49.820 | −15.675 | 24.832 | 1.00 | 25.06 | A | C |
| ATOM | 7093 | C | ALA | A | 445 | 47.598 | −15.622 | 25.971 | 1.00 | 25.09 | A | C |
| ATOM | 7094 | O | ALA | A | 445 | 47.333 | −14.971 | 26.980 | 1.00 | 25.23 | A | O |
| ATOM | 7096 | N | GLU | A | 446 | 46.766 | −15.738 | 24.939 | 1.00 | 25.16 | A | N |

TABLE 8-2-continued

Coordinates for L494P Structure

| ATOM | 7097 | CA | GLU | A | 446 | 45.496 | −15.009 | 24.873 | 1.00 | 25.34 | A | C |
|------|------|-----|-----|---|-----|--------|---------|--------|------|-------|---|---|
| ATOM | 7099 | CB | GLU | A | 446 | 44.976 | −14.984 | 23.430 | 1.00 | 25.42 | A | C |
| ATOM | 7102 | CG | GLU | A | 446 | 45.884 | −14.210 | 22.473 | 1.00 | 26.40 | A | C |
| ATOM | 7105 | CD | GLU | A | 446 | 45.477 | −14.336 | 21.012 | 1.00 | 27.93 | A | C |
| ATOM | 7106 | OE1 | GLU | A | 446 | 44.450 | −14.988 | 20.718 | 1.00 | 28.81 | A | O |
| ATOM | 7107 | OE2 | GLU | A | 446 | 46.191 | −13.776 | 20.153 | 1.00 | 27.41 | A | O |
| ATOM | 7108 | C | GLU | A | 446 | 44.421 | −15.561 | 25.819 | 1.00 | 25.11 | A | C |
| ATOM | 7109 | O | GLU | A | 446 | 43.555 | −14.812 | 26.273 | 1.00 | 24.91 | A | O |
| ATOM | 7111 | N | ILE | A | 447 | 44.482 | −16.859 | 26.115 | 1.00 | 25.06 | A | N |
| ATOM | 7112 | CA | ILE | A | 447 | 43.524 | −17.497 | 27.026 | 1.00 | 25.06 | A | C |
| ATOM | 7114 | CB | ILE | A | 447 | 43.578 | −19.041 | 26.936 | 1.00 | 25.18 | A | C |
| ATOM | 7116 | CG1 | ILE | A | 447 | 43.192 | −19.522 | 25.535 | 1.00 | 25.37 | A | C |
| ATOM | 7119 | CD1 | ILE | A | 447 | 43.705 | −20.915 | 25.217 | 1.00 | 24.89 | A | C |
| ATOM | 7123 | CG2 | ILE | A | 447 | 42.642 | −19.672 | 27.963 | 1.00 | 24.79 | A | C |
| ATOM | 7127 | C | ILE | A | 447 | 43.793 | −17.081 | 28.473 | 1.00 | 25.00 | A | C |
| ATOM | 7128 | O | ILE | A | 447 | 42.862 | −16.762 | 29.216 | 1.00 | 25.06 | A | O |
| ATOM | 7130 | N | ALA | A | 448 | 45.066 | −17.095 | 28.864 | 1.00 | 24.78 | A | N |
| ATOM | 7131 | CA | ALA | A | 448 | 45.479 | −16.656 | 30.198 | 1.00 | 24.75 | A | C |
| ATOM | 7133 | CB | ALA | A | 448 | 46.968 | −16.911 | 30.399 | 1.00 | 24.58 | A | C |
| ATOM | 7137 | C | ALA | A | 448 | 45.156 | −15.177 | 30.439 | 1.00 | 24.85 | A | C |
| ATOM | 7138 | O | ALA | A | 448 | 44.840 | −14.782 | 31.562 | 1.00 | 24.72 | A | O |
| ATOM | 7140 | N | ARG | A | 449 | 45.235 | −14.370 | 29.381 | 1.00 | 25.19 | A | N |
| ATOM | 7141 | CA | ARG | A | 449 | 44.895 | −12.944 | 29.453 | 1.00 | 25.36 | A | C |
| ATOM | 7143 | CB | ARG | A | 449 | 45.514 | −12.181 | 28.272 | 1.00 | 25.38 | A | C |
| ATOM | 7146 | CG | ARG | A | 449 | 47.002 | −11.884 | 28.451 | 1.00 | 25.01 | A | C |
| ATOM | 7149 | CD | ARG | A | 449 | 47.559 | −10.951 | 27.375 | 1.00 | 23.90 | A | C |
| ATOM | 7152 | NE | ARG | A | 449 | 48.127 | −11.685 | 26.242 | 1.00 | 22.76 | A | N |
| ATOM | 7154 | CZ | ARG | A | 449 | 47.765 | −11.558 | 24.963 | 1.00 | 23.10 | A | C |
| ATOM | 7155 | NH1 | ARG | A | 449 | 46.817 | −10.705 | 24.588 | 1.00 | 22.37 | A | N |
| ATOM | 7158 | NH2 | ARG | A | 449 | 48.374 | −12.295 | 24.037 | 1.00 | 24.00 | A | N |
| ATOM | 7161 | C | ARG | A | 449 | 43.382 | −12.686 | 29.517 | 1.00 | 25.70 | A | C |
| ATOM | 7162 | O | ARG | A | 449 | 42.958 | −11.579 | 29.853 | 1.00 | 25.66 | A | O |
| ATOM | 7164 | N | GLY | A | 450 | 42.579 | −13.699 | 29.190 | 1.00 | 26.09 | A | N |
| ATOM | 7165 | CA | GLY | A | 450 | 41.121 | −13.619 | 29.310 | 1.00 | 26.27 | A | C |
| ATOM | 7168 | C | GLY | A | 450 | 40.432 | −13.118 | 28.054 | 1.00 | 26.55 | A | C |
| ATOM | 7169 | O | GLY | A | 450 | 39.447 | −12.383 | 28.132 | 1.00 | 26.90 | A | O |
| ATOM | 7171 | N | GLU | A | 451 | 40.949 | −13.523 | 26.895 | 1.00 | 26.64 | A | N |
| ATOM | 7172 | CA | GLU | A | 451 | 40.382 | −13.141 | 25.602 | 1.00 | 26.67 | A | C |
| ATOM | 7174 | CB | GLU | A | 451 | 41.475 | −12.562 | 24.701 | 1.00 | 27.07 | A | C |
| ATOM | 7177 | CG | GLU | A | 451 | 42.137 | −11.307 | 25.255 | 1.00 | 27.64 | A | C |
| ATOM | 7180 | CD | GLU | A | 451 | 43.464 | −11.004 | 24.583 | 1.00 | 29.26 | A | C |
| ATOM | 7181 | OE1 | GLU | A | 451 | 43.516 | −10.980 | 23.333 | 1.00 | 28.51 | A | O |
| ATOM | 7182 | OE2 | GLU | A | 451 | 44.455 | −10.789 | 25.312 | 1.00 | 30.56 | A | O |
| ATOM | 7183 | C | GLU | A | 451 | 39.731 | −14.348 | 24.925 | 1.00 | 26.15 | A | C |
| ATOM | 7184 | O | GLU | A | 451 | 39.901 | −15.485 | 25.369 | 1.00 | 26.18 | A | O |
| ATOM | 7186 | N | THR | A | 452 | 38.986 | −14.089 | 23.853 | 1.00 | 25.51 | A | N |
| ATOM | 7187 | CA | THR | A | 452 | 38.273 | −15.142 | 23.119 | 1.00 | 24.90 | A | C |
| ATOM | 7189 | CB | THR | A | 452 | 36.752 | −15.015 | 23.327 | 1.00 | 24.75 | A | C |
| ATOM | 7191 | OG1 | THR | A | 452 | 36.470 | −14.915 | 24.727 | 1.00 | 24.32 | A | O |
| ATOM | 7193 | CG2 | THR | A | 452 | 36.021 | −16.222 | 22.756 | 1.00 | 24.68 | A | C |
| ATOM | 7197 | C | THR | A | 452 | 38.560 | −15.175 | 21.609 | 1.00 | 24.60 | A | C |
| ATOM | 7198 | O | THR | A | 452 | 38.318 | −16.200 | 20.964 | 1.00 | 24.57 | A | O |
| ATOM | 7200 | N | ALA | A | 453 | 39.066 | −14.073 | 21.049 | 1.00 | 23.97 | A | N |
| ATOM | 7201 | CA | ALA | A | 453 | 39.372 | −13.991 | 19.613 | 1.00 | 23.32 | A | C |
| ATOM | 7203 | CB | ALA | A | 453 | 39.710 | −12.550 | 19.216 | 1.00 | 23.40 | A | C |
| ATOM | 7207 | C | ALA | A | 453 | 40.515 | −14.935 | 19.237 | 1.00 | 22.48 | A | C |
| ATOM | 7208 | O | ALA | A | 453 | 41.639 | −14.504 | 18.962 | 1.00 | 22.66 | A | O |
| ATOM | 7210 | N | ASN | A | 454 | 40.201 | −16.228 | 19.220 | 1.00 | 21.33 | A | N |
| ATOM | 7211 | CA | ASN | A | 454 | 41.191 | −17.281 | 19.038 | 1.00 | 20.43 | A | C |
| ATOM | 7213 | CB | ASN | A | 454 | 42.047 | −17.415 | 20.297 | 1.00 | 20.27 | A | C |
| ATOM | 7216 | CG | ASN | A | 454 | 43.269 | −18.277 | 20.082 | 1.00 | 20.86 | A | C |
| ATOM | 7217 | OD1 | ASN | A | 454 | 43.160 | −19.454 | 19.740 | 1.00 | 22.12 | A | O |
| ATOM | 7218 | ND2 | ASN | A | 454 | 44.445 | −17.697 | 20.294 | 1.00 | 22.69 | A | N |
| ATOM | 7221 | C | ASN | A | 454 | 40.488 | −18.602 | 18.733 | 1.00 | 19.67 | A | C |
| ATOM | 7222 | O | ASN | A | 454 | 39.513 | −18.957 | 19.396 | 1.00 | 19.58 | A | O |
| ATOM | 7224 | N | SER | A | 455 | 40.986 | −19.320 | 17.731 | 1.00 | 18.91 | A | N |
| ATOM | 7225 | CA | SER | A | 455 | 40.347 | −20.549 | 17.264 | 1.00 | 18.58 | A | C |
| ATOM | 7227 | CB | SER | A | 455 | 41.080 | −21.092 | 16.040 | 1.00 | 18.57 | A | C |
| ATOM | 7230 | OG | SER | A | 455 | 41.081 | −20.136 | 14.995 | 1.00 | 18.90 | A | O |
| ATOM | 7232 | C | SER | A | 455 | 40.294 | −21.619 | 18.348 | 1.00 | 18.43 | A | C |
| ATOM | 7233 | O | SER | A | 455 | 39.274 | −22.289 | 18.517 | 1.00 | 18.43 | A | O |
| ATOM | 7235 | N | VAL | A | 456 | 41.395 | −21.765 | 19.081 | 1.00 | 18.24 | A | N |
| ATOM | 7236 | CA | VAL | A | 456 | 41.476 | −22.719 | 20.189 | 1.00 | 17.99 | A | C |
| ATOM | 7238 | CB | VAL | A | 456 | 42.896 | −22.755 | 20.804 | 1.00 | 17.68 | A | C |
| ATOM | 7240 | CG1 | VAL | A | 456 | 43.002 | −23.866 | 21.837 | 1.00 | 17.09 | A | C |
| ATOM | 7244 | CG2 | VAL | A | 456 | 43.950 | −22.931 | 19.720 | 1.00 | 17.17 | A | C |
| ATOM | 7248 | C | VAL | A | 456 | 40.472 | −22.360 | 21.290 | 1.00 | 18.30 | A | C |
| ATOM | 7249 | O | VAL | A | 456 | 39.855 | −23.240 | 21.891 | 1.00 | 18.13 | A | O |

TABLE 8-2-continued

| | | | | | | | | | | | | |
|---|---|---|---|---|---|---|---|---|---|---|---|---|
| \multicolumn{13}{|c|}{Coordinates for L494P Structure} |

| ATOM | 7251 | N | SER | A | 457 | 40.314 | −21.062 | 21.537 | 1.00 | 18.70 | A | N |
|---|---|---|---|---|---|---|---|---|---|---|---|---|
| ATOM | 7252 | CA | SER | A | 457 | 39.420 | −20.564 | 22.579 | 1.00 | 18.75 | A | C |
| ATOM | 7254 | CB | SER | A | 457 | 39.593 | −19.050 | 22.748 | 1.00 | 18.60 | A | C |
| ATOM | 7257 | OG | SER | A | 457 | 38.845 | −18.568 | 23.849 | 1.00 | 19.53 | A | O |
| ATOM | 7259 | C | SER | A | 457 | 37.961 | −20.887 | 22.276 | 1.00 | 18.84 | A | C |
| ATOM | 7260 | O | SER | A | 457 | 37.233 | −21.352 | 23.151 | 1.00 | 19.03 | A | O |
| ATOM | 7262 | N | CYS | A | 458 | 37.540 | −20.641 | 21.038 | 1.00 | 19.02 | A | N |
| ATOM | 7263 | CA | CYS | A | 458 | 36.150 | −20.883 | 20.639 | 1.00 | 19.32 | A | C |
| ATOM | 7265 | CB | CYS | A | 458 | 35.820 | −20.159 | 19.328 | 1.00 | 19.42 | A | C |
| ATOM | 7268 | SG | CYS | A | 458 | 35.508 | −18.389 | 19.544 | 1.00 | 20.53 | A | S |
| ATOM | 7270 | C | CYS | A | 458 | 35.811 | −22.373 | 20.530 | 1.00 | 19.33 | A | C |
| ATOM | 7271 | O | CYS | A | 458 | 34.639 | −22.746 | 20.610 | 1.00 | 19.60 | A | O |
| ATOM | 7273 | N | TYR | A | 459 | 36.827 | −23.218 | 20.355 | 1.00 | 19.09 | A | N |
| ATOM | 7274 | CA | TYR | A | 459 | 36.622 | −24.666 | 20.365 | 1.00 | 18.87 | A | C |
| ATOM | 7276 | CB | TYR | A | 459 | 37.841 | −25.402 | 19.805 | 1.00 | 18.80 | A | C |
| ATOM | 7279 | CG | TYR | A | 459 | 37.543 | −26.809 | 19.320 | 1.00 | 17.90 | A | C |
| ATOM | 7280 | CD1 | TYR | A | 459 | 37.163 | −27.044 | 17.999 | 1.00 | 15.79 | A | C |
| ATOM | 7282 | CE1 | TYR | A | 459 | 36.890 | −28.327 | 17.546 | 1.00 | 15.20 | A | C |
| ATOM | 7284 | CZ | TYR | A | 459 | 36.998 | −29.398 | 18.415 | 1.00 | 16.33 | A | C |
| ATOM | 7285 | OH | TYR | A | 459 | 36.728 | −30.670 | 17.962 | 1.00 | 17.00 | A | O |
| ATOM | 7287 | CE2 | TYR | A | 459 | 37.375 | −29.194 | 19.734 | 1.00 | 16.42 | A | C |
| ATOM | 7289 | CD2 | TYR | A | 459 | 37.646 | −27.903 | 20.179 | 1.00 | 17.05 | A | C |
| ATOM | 7291 | C | TYR | A | 459 | 36.332 | −25.124 | 21.792 | 1.00 | 19.29 | A | C |
| ATOM | 7292 | O | TYR | A | 459 | 35.353 | −25.834 | 22.029 | 1.00 | 19.45 | A | O |
| ATOM | 7294 | N | MET | A | 460 | 37.182 | −24.704 | 22.733 | 1.00 | 19.66 | A | N |
| ATOM | 7295 | CA | MET | A | 460 | 36.959 | −24.942 | 24.166 | 1.00 | 20.09 | A | C |
| ATOM | 7297 | CB | MET | A | 460 | 37.907 | −24.088 | 25.020 | 1.00 | 20.44 | A | C |
| ATOM | 7300 | CG | MET | A | 460 | 39.363 | −24.535 | 25.035 | 1.00 | 21.37 | A | C |
| ATOM | 7303 | SD | MET | A | 460 | 40.403 | −23.446 | 26.040 | 1.00 | 20.41 | A | S |
| ATOM | 7304 | CE | MET | A | 460 | 39.710 | −23.720 | 27.672 | 1.00 | 20.51 | A | C |
| ATOM | 7308 | C | MET | A | 460 | 35.526 | −24.602 | 24.568 | 1.00 | 20.02 | A | C |
| ATOM | 7309 | O | MET | A | 460 | 34.881 | −25.354 | 25.299 | 1.00 | 20.55 | A | O |
| ATOM | 7311 | N | ARG | A | 461 | 35.044 | −23.460 | 24.087 | 1.00 | 19.56 | A | N |
| ATOM | 7312 | CA | ARG | A | 461 | 33.701 | −22.985 | 24.402 | 1.00 | 19.46 | A | C |
| ATOM | 7314 | CB | ARG | A | 461 | 33.576 | −21.506 | 24.032 | 1.00 | 19.44 | A | C |
| ATOM | 7317 | CG | ARG | A | 461 | 32.316 | −20.828 | 24.545 | 1.00 | 19.32 | A | C |
| ATOM | 7320 | CD | ARG | A | 461 | 32.420 | −19.311 | 24.446 | 1.00 | 20.04 | A | C |
| ATOM | 7323 | NE | ARG | A | 461 | 32.757 | −18.860 | 23.095 | 1.00 | 20.53 | A | N |
| ATOM | 7325 | CZ | ARG | A | 461 | 32.925 | −17.587 | 22.743 | 1.00 | 21.06 | A | C |
| ATOM | 7326 | NH1 | ARG | A | 461 | 32.781 | −16.609 | 23.634 | 1.00 | 20.57 | A | N |
| ATOM | 7329 | NH2 | ARG | A | 461 | 33.238 | −17.287 | 21.486 | 1.00 | 22.20 | A | N |
| ATOM | 7332 | C | ARG | A | 461 | 32.622 | −23.797 | 23.685 | 1.00 | 19.27 | A | C |
| ATOM | 7333 | O | ARG | A | 461 | 31.605 | −24.142 | 24.283 | 1.00 | 19.05 | A | O |
| ATOM | 7335 | N | THR | A | 462 | 32.852 | −24.099 | 22.409 | 1.00 | 19.32 | A | N |
| ATOM | 7336 | CA | THR | A | 462 | 31.871 | −24.814 | 21.585 | 1.00 | 19.62 | A | C |
| ATOM | 7338 | CB | THR | A | 462 | 32.292 | −24.821 | 20.095 | 1.00 | 19.63 | A | C |
| ATOM | 7340 | OG1 | THR | A | 462 | 32.065 | −23.524 | 19.532 | 1.00 | 20.66 | A | O |
| ATOM | 7342 | CG2 | THR | A | 462 | 31.503 | −25.854 | 19.296 | 1.00 | 20.05 | A | C |
| ATOM | 7346 | C | THR | A | 462 | 31.632 | −26.253 | 22.052 | 1.00 | 19.82 | A | C |
| ATOM | 7347 | O | THR | A | 462 | 30.487 | −26.719 | 22.084 | 1.00 | 20.00 | A | O |
| ATOM | 7349 | N | LYS | A | 463 | 32.710 | −26.948 | 22.413 | 1.00 | 19.62 | A | N |
| ATOM | 7350 | CA | LYS | A | 463 | 32.622 | −28.345 | 22.846 | 1.00 | 19.23 | A | C |
| ATOM | 7352 | CB | LYS | A | 463 | 33.772 | −29.162 | 22.243 | 1.00 | 19.10 | A | C |
| ATOM | 7355 | CG | LYS | A | 463 | 34.023 | −28.923 | 20.754 | 1.00 | 17.85 | A | C |
| ATOM | 7358 | CD | LYS | A | 463 | 32.791 | −29.169 | 19.891 | 1.00 | 17.09 | A | C |
| ATOM | 7361 | CE | LYS | A | 463 | 33.108 | −28.934 | 18.419 | 1.00 | 17.67 | A | C |
| ATOM | 7364 | NZ | LYS | A | 463 | 31.897 | −28.942 | 17.554 | 1.00 | 18.35 | A | N |
| ATOM | 7368 | C | LYS | A | 463 | 32.618 | −28.499 | 24.374 | 1.00 | 19.01 | A | C |
| ATOM | 7369 | O | LYS | A | 463 | 32.385 | −29.597 | 24.883 | 1.00 | 18.88 | A | O |
| ATOM | 7371 | N | GLY | A | 464 | 32.875 | −27.407 | 25.095 | 1.00 | 18.78 | A | N |
| ATOM | 7372 | CA | GLY | A | 464 | 32.929 | −27.434 | 26.557 | 1.00 | 18.68 | A | C |
| ATOM | 7375 | C | GLY | A | 464 | 34.040 | −28.331 | 27.067 | 1.00 | 18.63 | A | C |
| ATOM | 7376 | O | GLY | A | 464 | 33.780 | −29.294 | 27.790 | 1.00 | 18.57 | A | O |
| ATOM | 7378 | N | ILE | A | 465 | 35.278 | −28.015 | 26.685 | 1.00 | 18.68 | A | N |
| ATOM | 7379 | CA | ILE | A | 465 | 36.439 | −28.853 | 27.006 | 1.00 | 18.82 | A | C |
| ATOM | 7381 | CB | ILE | A | 465 | 36.788 | −29.812 | 25.838 | 1.00 | 18.83 | A | C |
| ATOM | 7383 | CG1 | ILE | A | 465 | 37.004 | −29.035 | 24.534 | 1.00 | 18.84 | A | C |
| ATOM | 7386 | CD1 | ILE | A | 465 | 37.345 | −29.915 | 23.345 | 1.00 | 18.16 | A | C |
| ATOM | 7390 | CG2 | ILE | A | 465 | 35.689 | −30.848 | 25.660 | 1.00 | 19.72 | A | C |
| ATOM | 7394 | C | ILE | A | 465 | 37.682 | −28.039 | 27.370 | 1.00 | 18.85 | A | C |
| ATOM | 7395 | O | ILE | A | 465 | 37.736 | −26.826 | 27.153 | 1.00 | 18.44 | A | O |
| ATOM | 7397 | N | SER | A | 466 | 38.676 | −28.731 | 27.920 | 1.00 | 19.23 | A | N |
| ATOM | 7398 | CA | SER | A | 466 | 39.912 | −28.108 | 28.384 | 1.00 | 19.68 | A | C |
| ATOM | 7400 | CB | SER | A | 466 | 40.667 | −29.071 | 29.304 | 1.00 | 19.87 | A | C |
| ATOM | 7403 | OG | SER | A | 466 | 40.980 | −30.278 | 28.628 | 1.00 | 19.96 | A | O |
| ATOM | 7405 | C | SER | A | 466 | 40.811 | −27.707 | 27.221 | 1.00 | 20.03 | A | C |
| ATOM | 7406 | O | SER | A | 466 | 40.670 | −28.225 | 26.114 | 1.00 | 19.89 | A | O |
| ATOM | 7408 | N | GLU | A | 467 | 41.746 | −26.797 | 27.491 | 1.00 | 20.78 | A | N |

TABLE 8-2-continued

Coordinates for L494P Structure

| ATOM | 7409 | CA | GLU | A | 467 | 42.673 | −26.283 | 26.472 | 1.00 | 21.37 | A | C |
|---|---|---|---|---|---|---|---|---|---|---|---|---|
| ATOM | 7411 | CB | GLU | A | 467 | 43.576 | −25.189 | 27.062 | 1.00 | 21.42 | A | C |
| ATOM | 7414 | CG | GLU | A | 467 | 44.408 | −24.433 | 26.022 | 1.00 | 21.87 | A | C |
| ATOM | 7417 | CD | GLU | A | 467 | 45.487 | −23.565 | 26.640 | 1.00 | 22.82 | A | C |
| ATOM | 7418 | OE1 | GLU | A | 467 | 45.207 | −22.883 | 27.647 | 1.00 | 23.89 | A | O |
| ATOM | 7419 | OE2 | GLU | A | 467 | 46.618 | −23.560 | 26.109 | 1.00 | 23.99 | A | O |
| ATOM | 7420 | C | GLU | A | 467 | 43.542 | −27.377 | 25.843 | 1.00 | 21.81 | A | C |
| ATOM | 7421 | O | GLU | A | 467 | 43.856 | −27.309 | 24.651 | 1.00 | 22.00 | A | O |
| ATOM | 7423 | N | GLU | A | 468 | 43.932 | −28.373 | 26.639 | 1.00 | 21.90 | A | N |
| ATOM | 7424 | CA | GLU | A | 468 | 44.772 | −29.466 | 26.142 | 1.00 | 21.88 | A | C |
| ATOM | 7426 | CB | GLU | A | 468 | 45.304 | −30.320 | 27.298 | 1.00 | 22.13 | A | C |
| ATOM | 7429 | CG | GLU | A | 468 | 46.361 | −31.336 | 26.869 | 1.00 | 23.30 | A | C |
| ATOM | 7432 | CD | GLU | A | 468 | 46.846 | −32.207 | 28.012 | 1.00 | 24.29 | A | C |
| ATOM | 7433 | OE1 | GLU | A | 468 | 47.560 | −31.688 | 28.898 | 1.00 | 25.02 | A | O |
| ATOM | 7434 | OE2 | GLU | A | 468 | 46.526 | −33.416 | 28.015 | 1.00 | 24.63 | A | O |
| ATOM | 7435 | C | GLU | A | 468 | 44.022 | −30.345 | 25.137 | 1.00 | 21.46 | A | C |
| ATOM | 7436 | O | GLU | A | 468 | 44.577 | −30.710 | 24.099 | 1.00 | 21.21 | A | O |
| ATOM | 7438 | N | LEU | A | 469 | 42.771 | −30.685 | 25.450 | 1.00 | 21.18 | A | N |
| ATOM | 7439 | CA | LEU | A | 469 | 41.919 | −31.458 | 24.531 | 1.00 | 20.84 | A | C |
| ATOM | 7441 | CB | LEU | A | 469 | 40.692 | −32.042 | 25.253 | 1.00 | 21.05 | A | C |
| ATOM | 7444 | CG | LEU | A | 469 | 40.856 | −33.409 | 25.932 | 1.00 | 20.32 | A | C |
| ATOM | 7446 | CD1 | LEU | A | 469 | 41.842 | −33.328 | 27.086 | 1.00 | 20.20 | A | C |
| ATOM | 7450 | CD2 | LEU | A | 469 | 39.508 | −33.940 | 26.415 | 1.00 | 18.12 | A | C |
| ATOM | 7454 | C | LEU | A | 469 | 41.463 | −30.616 | 23.335 | 1.00 | 20.25 | A | C |
| ATOM | 7455 | O | LEU | A | 469 | 41.262 | −31.149 | 22.243 | 1.00 | 20.27 | A | O |
| ATOM | 7457 | N | ALA | A | 470 | 41.295 | −29.312 | 23.550 | 1.00 | 19.59 | A | N |
| ATOM | 7458 | CA | ALA | A | 470 | 40.901 | −28.386 | 22.484 | 1.00 | 19.19 | A | C |
| ATOM | 7460 | CB | ALA | A | 470 | 40.517 | −27.037 | 23.069 | 1.00 | 18.89 | A | C |
| ATOM | 7464 | C | ALA | A | 470 | 42.013 | −28.213 | 21.452 | 1.00 | 19.15 | A | C |
| ATOM | 7465 | O | ALA | A | 470 | 41.746 | −28.143 | 20.249 | 1.00 | 19.34 | A | O |
| ATOM | 7467 | N | THR | A | 471 | 43.254 | −28.135 | 21.931 | 1.00 | 18.89 | A | N |
| ATOM | 7468 | CA | THR | A | 471 | 44.426 | −28.064 | 21.059 | 1.00 | 18.62 | A | C |
| ATOM | 7470 | CB | THR | A | 471 | 45.732 | −27.906 | 21.884 | 1.00 | 18.76 | A | C |
| ATOM | 7472 | OG1 | THR | A | 471 | 45.777 | −26.597 | 22.467 | 1.00 | 19.40 | A | O |
| ATOM | 7474 | CG2 | THR | A | 471 | 46.968 | −28.103 | 21.012 | 1.00 | 18.57 | A | C |
| ATOM | 7478 | C | THR | A | 471 | 44.515 | −29.311 | 20.179 | 1.00 | 18.43 | A | C |
| ATOM | 7479 | O | THR | A | 471 | 44.622 | −29.205 | 18.959 | 1.00 | 18.22 | A | O |
| ATOM | 7481 | N | GLU | A | 472 | 44.446 | −30.484 | 20.807 | 1.00 | 18.49 | A | N |
| ATOM | 7482 | CA | GLU | A | 472 | 44.564 | −31.770 | 20.107 | 1.00 | 18.66 | A | C |
| ATOM | 7484 | CB | GLU | A | 472 | 44.382 | −32.928 | 21.094 | 1.00 | 18.91 | A | C |
| ATOM | 7487 | CG | GLU | A | 472 | 44.713 | −34.306 | 20.517 | 1.00 | 20.49 | A | C |
| ATOM | 7490 | CD | GLU | A | 472 | 44.356 | −35.452 | 21.450 | 1.00 | 21.71 | A | C |
| ATOM | 7491 | OE1 | GLU | A | 472 | 44.795 | −36.589 | 21.175 | 1.00 | 22.68 | A | O |
| ATOM | 7492 | OE2 | GLU | A | 472 | 43.637 | −35.225 | 22.448 | 1.00 | 22.86 | A | O |
| ATOM | 7493 | C | GLU | A | 472 | 43.569 | −31.924 | 18.951 | 1.00 | 18.52 | A | C |
| ATOM | 7494 | O | GLU | A | 472 | 43.896 | −32.510 | 17.917 | 1.00 | 17.98 | A | O |
| ATOM | 7496 | N | SER | A | 473 | 42.356 | −31.410 | 19.133 | 1.00 | 18.86 | A | N |
| ATOM | 7497 | CA | SER | A | 473 | 41.343 | −31.440 | 18.077 | 1.00 | 19.17 | A | C |
| ATOM | 7499 | CB | SER | A | 473 | 39.978 | −31.041 | 18.633 | 1.00 | 18.98 | A | C |
| ATOM | 7502 | OG | SER | A | 473 | 39.616 | −31.871 | 19.723 | 1.00 | 18.35 | A | O |
| ATOM | 7504 | C | SER | A | 473 | 41.727 | −30.519 | 16.917 | 1.00 | 19.64 | A | C |
| ATOM | 7505 | O | SER | A | 473 | 41.518 | −30.862 | 15.749 | 1.00 | 20.03 | A | O |
| ATOM | 7507 | N | VAL | A | 474 | 42.287 | −29.355 | 17.248 | 1.00 | 19.48 | A | N |
| ATOM | 7508 | CA | VAL | A | 474 | 42.797 | −28.424 | 16.240 | 1.00 | 19.38 | A | C |
| ATOM | 7510 | CB | VAL | A | 474 | 43.148 | −27.054 | 16.862 | 1.00 | 19.33 | A | C |
| ATOM | 7512 | CG1 | VAL | A | 474 | 43.833 | −26.152 | 15.844 | 1.00 | 18.11 | A | C |
| ATOM | 7516 | CG2 | VAL | A | 474 | 41.892 | −26.389 | 17.412 | 1.00 | 19.60 | A | C |
| ATOM | 7520 | C | VAL | A | 474 | 44.020 | −29.008 | 15.525 | 1.00 | 19.69 | A | C |
| ATOM | 7521 | O | VAL | A | 474 | 44.175 | −28.829 | 14.315 | 1.00 | 20.15 | A | O |
| ATOM | 7523 | N | MET | A | 475 | 44.873 | −29.714 | 16.268 | 1.00 | 19.66 | A | N |
| ATOM | 7524 | CA | MET | A | 475 | 46.005 | −30.444 | 15.680 | 1.00 | 19.70 | A | C |
| ATOM | 7526 | CB | MET | A | 475 | 46.889 | −31.053 | 16.772 | 1.00 | 20.05 | A | C |
| ATOM | 7529 | CG | MET | A | 475 | 47.604 | −30.045 | 17.650 | 1.00 | 20.04 | A | C |
| ATOM | 7532 | SD | MET | A | 475 | 48.893 | −29.161 | 16.773 | 1.00 | 21.08 | A | S |
| ATOM | 7533 | CE | MET | A | 475 | 50.090 | −28.966 | 18.096 | 1.00 | 21.33 | A | C |
| ATOM | 7537 | C | MET | A | 475 | 45.528 | −31.562 | 14.751 | 1.00 | 19.35 | A | C |
| ATOM | 7538 | O | MET | A | 475 | 46.147 | −31.822 | 13.718 | 1.00 | 19.12 | A | O |
| ATOM | 7540 | N | ASN | A | 476 | 44.441 | −32.230 | 15.136 | 1.00 | 19.22 | A | N |
| ATOM | 7541 | CA | ASN | A | 476 | 43.791 | −33.215 | 14.270 | 1.00 | 19.31 | A | C |
| ATOM | 7543 | CB | ASN | A | 476 | 42.729 | −34.021 | 15.036 | 1.00 | 19.59 | A | C |
| ATOM | 7546 | CG | ASN | A | 476 | 43.330 | −35.106 | 15.920 | 1.00 | 20.46 | A | C |
| ATOM | 7547 | OD1 | ASN | A | 476 | 44.375 | −35.682 | 15.605 | 1.00 | 21.67 | A | O |
| ATOM | 7548 | ND2 | ASN | A | 476 | 42.659 | −35.397 | 17.029 | 1.00 | 19.15 | A | N |
| ATOM | 7551 | C | ASN | A | 476 | 43.147 | −32.565 | 13.050 | 1.00 | 18.81 | A | C |
| ATOM | 7552 | O | ASN | A | 476 | 43.056 | −33.193 | 11.996 | 1.00 | 19.00 | A | O |
| ATOM | 7554 | N | LEU | A | 477 | 42.699 | −31.318 | 13.195 | 1.00 | 18.29 | A | N |
| ATOM | 7555 | CA | LEU | A | 477 | 42.084 | −30.588 | 12.083 | 1.00 | 18.10 | A | C |
| ATOM | 7557 | CB | LEU | A | 477 | 41.349 | −29.331 | 12.568 | 1.00 | 18.33 | A | C |

TABLE 8-2-continued

Coordinates for L494P Structure

| ATOM | 7560 | CG | LEU | A | 477 | 40.013 | −29.097 | 11.847 | 1.00 | 19.37 A | C |
|---|---|---|---|---|---|---|---|---|---|---|---|
| ATOM | 7562 | CD1 | LEU | A | 477 | 38.911 | −29.923 | 12.515 | 1.00 | 19.86 A | C |
| ATOM | 7566 | CD2 | LEU | A | 477 | 39.627 | −27.623 | 11.809 | 1.00 | 19.63 A | C |
| ATOM | 7570 | C | LEU | A | 477 | 43.115 | −30.208 | 11.022 | 1.00 | 17.36 A | C |
| ATOM | 7571 | O | LEU | A | 477 | 42.808 | −30.206 | 9.834 | 1.00 | 16.65 A | O |
| ATOM | 7573 | N | ILE | A | 478 | 44.328 | −29.876 | 11.459 | 1.00 | 17.33 A | N |
| ATOM | 7574 | CA | ILE | A | 478 | 45.438 | −29.615 | 10.540 | 1.00 | 17.10 A | C |
| ATOM | 7576 | CB | ILE | A | 478 | 46.684 | −29.070 | 11.278 | 1.00 | 16.99 A | C |
| ATOM | 7578 | CG1 | ILE | A | 478 | 46.479 | −27.597 | 11.646 | 1.00 | 15.91 A | C |
| ATOM | 7581 | CD1 | ILE | A | 478 | 47.583 | −27.015 | 12.513 | 1.00 | 14.00 A | C |
| ATOM | 7585 | CG2 | ILE | A | 478 | 47.928 | −29.216 | 10.418 | 1.00 | 16.35 A | C |
| ATOM | 7589 | C | ILE | A | 478 | 45.797 | −30.895 | 9.796 | 1.00 | 17.29 A | C |
| ATOM | 7590 | O | ILE | A | 478 | 45.765 | −30.928 | 8.566 | 1.00 | 16.88 A | O |
| ATOM | 7592 | N | ASP | A | 479 | 46.124 | −31.946 | 10.547 | 1.00 | 17.99 A | N |
| ATOM | 7593 | CA | ASP | A | 479 | 46.388 | −33.264 | 9.962 | 1.00 | 18.84 A | C |
| ATOM | 7595 | CB | ASP | A | 479 | 46.434 | −34.355 | 11.047 | 1.00 | 19.10 A | C |
| ATOM | 7598 | CG | ASP | A | 479 | 47.715 | −34.320 | 11.885 | 1.00 | 20.09 A | C |
| ATOM | 7599 | OD1 | ASP | A | 479 | 48.759 | −33.837 | 11.398 | 1.00 | 23.06 A | O |
| ATOM | 7600 | OD2 | ASP | A | 479 | 47.678 | −34.799 | 13.039 | 1.00 | 20.40 A | O |
| ATOM | 7601 | C | ASP | A | 479 | 45.316 | −33.616 | 8.926 | 1.00 | 19.15 A | C |
| ATOM | 7602 | O | ASP | A | 479 | 45.633 | −34.020 | 7.807 | 1.00 | 19.09 A | O |
| ATOM | 7604 | N | GLU | A | 480 | 44.052 | −33.439 | 9.307 | 1.00 | 19.60 A | N |
| ATOM | 7605 | CA | GLU | A | 480 | 42.914 | −33.728 | 8.431 | 1.00 | 19.98 A | C |
| ATOM | 7607 | CB | GLU | A | 480 | 41.602 | −33.582 | 9.207 | 1.00 | 19.86 A | C |
| ATOM | 7610 | CG | GLU | A | 480 | 40.347 | −33.858 | 8.393 | 1.00 | 20.57 A | C |
| ATOM | 7613 | CD | GLU | A | 480 | 39.126 | −34.088 | 9.268 | 1.00 | 22.39 A | C |
| ATOM | 7614 | OE1 | GLU | A | 480 | 39.083 | −35.116 | 9.982 | 1.00 | 22.35 A | O |
| ATOM | 7615 | OE2 | GLU | A | 480 | 38.205 | −33.244 | 9.233 | 1.00 | 22.18 A | O |
| ATOM | 7616 | C | GLU | A | 480 | 42.885 | −32.835 | 7.190 | 1.00 | 20.39 A | C |
| ATOM | 7617 | O | GLU | A | 480 | 42.571 | −33.303 | 6.095 | 1.00 | 20.59 A | O |
| ATOM | 7619 | N | THR | A | 481 | 43.202 | −31.553 | 7.364 | 1.00 | 20.68 A | N |
| ATOM | 7620 | CA | THR | A | 481 | 43.218 | −30.604 | 6.249 | 1.00 | 20.31 A | C |
| ATOM | 7622 | CB | THR | A | 481 | 43.298 | −29.143 | 6.737 | 1.00 | 20.04 A | C |
| ATOM | 7624 | OG1 | THR | A | 481 | 42.259 | −28.899 | 7.690 | 1.00 | 20.12 A | O |
| ATOM | 7626 | CG2 | THR | A | 481 | 43.131 | −28.179 | 5.577 | 1.00 | 19.56 A | C |
| ATOM | 7630 | C | THR | A | 481 | 44.378 | −30.897 | 5.297 | 1.00 | 20.57 A | C |
| ATOM | 7631 | O | THR | A | 481 | 44.217 | −30.791 | 4.080 | 1.00 | 21.43 A | O |
| ATOM | 7633 | N | TRP | A | 482 | 45.537 | −31.268 | 5.846 | 1.00 | 19.91 A | N |
| ATOM | 7634 | CA | TRP | A | 482 | 46.673 | −31.698 | 5.020 | 1.00 | 19.35 A | C |
| ATOM | 7636 | CB | TRP | A | 482 | 47.922 | −31.978 | 5.873 | 1.00 | 19.46 A | C |
| ATOM | 7639 | CG | TRP | A | 482 | 48.839 | −30.798 | 5.995 | 1.00 | 19.49 A | C |
| ATOM | 7640 | CD1 | TRP | A | 482 | 48.961 | −29.963 | 7.064 | 1.00 | 19.76 A | C |
| ATOM | 7642 | NE1 | TRP | A | 482 | 49.900 | −28.996 | 6.805 | 1.00 | 18.99 A | N |
| ATOM | 7644 | CE2 | TRP | A | 482 | 50.403 | −29.191 | 5.547 | 1.00 | 19.41 A | C |
| ATOM | 7645 | CD2 | TRP | A | 482 | 49.757 | −30.320 | 5.005 | 1.00 | 18.58 A | C |
| ATOM | 7646 | CE3 | TRP | A | 482 | 50.095 | −30.737 | 3.714 | 1.00 | 18.27 A | C |
| ATOM | 7648 | CZ3 | TRP | A | 482 | 51.055 | −30.024 | 3.014 | 1.00 | 19.21 A | C |
| ATOM | 7650 | CH2 | TRP | A | 482 | 51.681 | −28.902 | 3.581 | 1.00 | 20.66 A | C |
| ATOM | 7652 | CZ2 | TRP | A | 482 | 51.369 | −28.470 | 4.842 | 1.00 | 19.87 A | C |
| ATOM | 7654 | C | TRP | A | 482 | 46.333 | −32.933 | 4.186 | 1.00 | 18.89 A | C |
| ATOM | 7655 | O | TRP | A | 482 | 46.780 | −33.055 | 3.048 | 1.00 | 18.56 A | O |
| ATOM | 7657 | N | LYS | A | 483 | 45.544 | −33.842 | 4.753 | 1.00 | 18.60 A | N |
| ATOM | 7658 | CA | LYS | A | 483 | 45.126 | −35.045 | 4.034 | 1.00 | 18.61 A | C |
| ATOM | 7660 | CB | LYS | A | 483 | 44.344 | −35.996 | 4.953 | 1.00 | 18.82 A | C |
| ATOM | 7663 | CG | LYS | A | 483 | 45.198 | −36.750 | 5.972 | 1.00 | 17.67 A | C |
| ATOM | 7666 | CD | LYS | A | 483 | 44.331 | −37.423 | 7.032 | 1.00 | 15.32 A | C |
| ATOM | 7669 | CE | LYS | A | 483 | 45.158 | −38.283 | 7.970 | 1.00 | 13.29 A | C |
| ATOM | 7672 | NZ | LYS | A | 483 | 44.317 | −38.976 | 8.975 | 1.00 | 11.47 A | N |
| ATOM | 7676 | C | LYS | A | 483 | 44.288 | −34.699 | 2.803 | 1.00 | 18.60 A | C |
| ATOM | 7677 | O | LYS | A | 483 | 44.480 | −35.279 | 1.737 | 1.00 | 19.08 A | O |
| ATOM | 7679 | N | LYS | A | 484 | 43.365 | −33.755 | 2.953 | 1.00 | 18.44 A | N |
| ATOM | 7680 | CA | LYS | A | 484 | 42.497 | −33.350 | 1.848 | 1.00 | 18.75 A | C |
| ATOM | 7682 | CB | LYS | A | 484 | 41.273 | −32.596 | 2.375 | 1.00 | 19.23 A | C |
| ATOM | 7685 | CG | LYS | A | 484 | 40.298 | −33.472 | 3.160 | 1.00 | 20.08 A | C |
| ATOM | 7688 | CD | LYS | A | 484 | 39.154 | −32.644 | 3.749 | 1.00 | 21.14 A | C |
| ATOM | 7691 | CE | LYS | A | 484 | 38.400 | −33.410 | 4.825 | 1.00 | 21.14 A | C |
| ATOM | 7694 | NZ | LYS | A | 484 | 37.453 | −32.542 | 5.575 | 1.00 | 21.03 A | N |
| ATOM | 7698 | C | LYS | A | 484 | 43.229 | −32.506 | 0.799 | 1.00 | 18.54 A | C |
| ATOM | 7699 | O | LYS | A | 484 | 42.816 | −32.464 | −0.362 | 1.00 | 18.32 A | O |
| ATOM | 7701 | N | MET | A | 485 | 44.303 | −31.832 | 1.206 | 1.00 | 18.57 A | N |
| ATOM | 7702 | CA | MET | A | 485 | 45.123 | −31.055 | 0.271 | 1.00 | 18.64 A | C |
| ATOM | 7704 | CB | MET | A | 485 | 45.980 | −30.024 | 1.012 | 1.00 | 18.40 A | C |
| ATOM | 7707 | CG | MET | A | 485 | 45.227 | −28.776 | 1.434 | 1.00 | 18.70 A | C |
| ATOM | 7710 | SD | MET | A | 485 | 46.323 | −27.453 | 1.994 | 1.00 | 20.00 A | S |
| ATOM | 7711 | CE | MET | A | 485 | 47.030 | −28.185 | 3.470 | 1.00 | 21.42 A | C |
| ATOM | 7715 | C | MET | A | 485 | 46.018 | −31.957 | −0.579 | 1.00 | 18.87 A | C |
| ATOM | 7716 | O | MET | A | 485 | 46.335 | −31.620 | −1.718 | 1.00 | 19.09 A | O |
| ATOM | 7718 | N | ASN | A | 486 | 46.423 | −33.097 | −0.024 | 1.00 | 19.18 A | N |

TABLE 8-2-continued

Coordinates for L494P Structure

| ATOM | 7719 | CA | ASN | A | 486 | 47.263 | −34.055 | −0.747 | 1.00 | 19.51 | A | C |
| ATOM | 7721 | CB | ASN | A | 486 | 47.949 | −35.011 | 0.234 | 1.00 | 19.57 | A | C |
| ATOM | 7724 | CG | ASN | A | 486 | 48.863 | −34.291 | 1.215 | 1.00 | 18.76 | A | C |
| ATOM | 7725 | OD1 | ASN | A | 486 | 49.319 | −33.176 | 0.955 | 1.00 | 16.76 | A | O |
| ATOM | 7726 | ND2 | ASN | A | 486 | 49.129 | −34.926 | 2.353 | 1.00 | 15.82 | A | N |
| ATOM | 7729 | C | ASN | A | 486 | 46.484 | −34.844 | −1.805 | 1.00 | 19.93 | A | C |
| ATOM | 7730 | O | ASN | A | 486 | 47.079 | −35.465 | −2.686 | 1.00 | 19.71 | A | O |
| ATOM | 7732 | N | LYS | A | 487 | 45.157 | −34.825 | −1.699 | 1.00 | 20.76 | A | N |
| ATOM | 7733 | CA | LYS | A | 487 | 44.270 | −35.350 | −2.740 | 1.00 | 21.38 | A | C |
| ATOM | 7735 | CB | LYS | A | 487 | 42.876 | −35.618 | −2.155 | 1.00 | 21.37 | A | C |
| ATOM | 7738 | CG | LYS | A | 487 | 41.863 | −36.168 | −3.146 | 1.00 | 22.41 | A | C |
| ATOM | 7741 | CD | LYS | A | 487 | 40.657 | −36.762 | −2.429 | 1.00 | 24.55 | A | C |
| ATOM | 7744 | CE | LYS | A | 487 | 39.699 | −37.429 | −3.406 | 1.00 | 25.58 | A | C |
| ATOM | 7747 | NZ | LYS | A | 487 | 38.641 | −38.214 | −2.712 | 1.00 | 25.77 | A | N |
| ATOM | 7751 | C | LYS | A | 487 | 44.173 | −34.357 | −3.902 | 1.00 | 21.61 | A | C |
| ATOM | 7752 | O | LYS | A | 487 | 44.198 | −34.750 | −5.069 | 1.00 | 21.31 | A | O |
| ATOM | 7754 | N | GLU | A | 488 | 44.066 | −33.073 | −3.563 | 1.00 | 22.02 | A | N |
| ATOM | 7755 | CA | GLU | A | 488 | 43.961 | −31.991 | −4.548 | 1.00 | 22.50 | A | C |
| ATOM | 7757 | CB | GLU | A | 488 | 43.814 | −30.642 | −3.829 | 1.00 | 22.80 | A | C |
| ATOM | 7760 | CG | GLU | A | 488 | 43.213 | −29.533 | −4.676 | 1.00 | 23.18 | A | C |
| ATOM | 7763 | CD | GLU | A | 488 | 41.700 | −29.614 | −4.749 | 1.00 | 24.54 | A | C |
| ATOM | 7764 | OE1 | GLU | A | 488 | 41.174 | −30.005 | −5.813 | 1.00 | 26.04 | A | O |
| ATOM | 7765 | OE2 | GLU | A | 488 | 41.037 | −29.300 | −3.736 | 1.00 | 23.72 | A | O |
| ATOM | 7766 | C | GLU | A | 488 | 45.175 | −31.939 | −5.484 | 1.00 | 22.62 | A | C |
| ATOM | 7767 | O | GLU | A | 488 | 45.030 | −31.728 | −6.692 | 1.00 | 22.91 | A | O |
| ATOM | 7769 | N | LYS | A | 489 | 46.364 | −32.126 | −4.914 | 1.00 | 22.30 | A | N |
| ATOM | 7770 | CA | LYS | A | 489 | 47.612 | −32.113 | −5.679 | 1.00 | 22.00 | A | C |
| ATOM | 7772 | CB | LYS | A | 489 | 48.811 | −32.096 | −4.722 | 1.00 | 21.67 | A | C |
| ATOM | 7775 | CG | LYS | A | 489 | 50.184 | −32.043 | −5.393 | 1.00 | 21.43 | A | C |
| ATOM | 7778 | CD | LYS | A | 489 | 50.461 | −30.695 | −6.050 | 1.00 | 20.14 | A | C |
| ATOM | 7781 | CE | LYS | A | 489 | 51.730 | −30.743 | −6.890 | 1.00 | 19.82 | A | C |
| ATOM | 7784 | NZ | LYS | A | 489 | 52.931 | −31.125 | −6.095 | 1.00 | 17.92 | A | N |
| ATOM | 7788 | C | LYS | A | 489 | 47.701 | −33.322 | −6.611 | 1.00 | 22.11 | A | C |
| ATOM | 7789 | O | LYS | A | 489 | 48.096 | −33.198 | −7.773 | 1.00 | 21.65 | A | O |
| ATOM | 7791 | N | LEU | A | 490 | 47.327 | −34.488 | −6.093 | 1.00 | 22.42 | A | N |
| ATOM | 7792 | CA | LEU | A | 490 | 47.446 | −35.738 | −6.839 | 1.00 | 22.44 | A | C |
| ATOM | 7794 | CB | LEU | A | 490 | 47.168 | −36.947 | −5.931 | 1.00 | 22.44 | A | C |
| ATOM | 7797 | CG | LEU | A | 490 | 47.979 | −38.212 | −6.227 | 1.00 | 21.83 | A | C |
| ATOM | 7799 | CD1 | LEU | A | 490 | 49.430 | −38.021 | −5.803 | 1.00 | 20.81 | A | C |
| ATOM | 7803 | CD2 | LEU | A | 490 | 47.375 | −39.425 | −5.528 | 1.00 | 22.00 | A | C |
| ATOM | 7807 | C | LEU | A | 490 | 46.513 | −35.751 | −8.049 | 1.00 | 22.61 | A | C |
| ATOM | 7808 | O | LEU | A | 490 | 46.851 | −36.327 | −9.084 | 1.00 | 22.97 | A | O |
| ATOM | 7810 | N | GLY | A | 491 | 45.347 | −35.118 | −7.919 | 1.00 | 22.59 | A | N |
| ATOM | 7811 | CA | GLY | A | 491 | 44.416 | −35.003 | −9.038 | 1.00 | 22.92 | A | C |
| ATOM | 7814 | C | GLY | A | 491 | 43.025 | −34.538 | −8.654 | 1.00 | 23.38 | A | C |
| ATOM | 7815 | O | GLY | A | 491 | 42.667 | −34.519 | −7.479 | 1.00 | 23.58 | A | O |
| ATOM | 7817 | N | GLY | A | 492 | 42.242 | −34.164 | −9.662 | 1.00 | 24.00 | A | N |
| ATOM | 7818 | CA | GLY | A | 492 | 40.868 | −33.719 | −9.464 | 1.00 | 24.68 | A | C |
| ATOM | 7821 | C | GLY | A | 492 | 40.714 | −32.217 | −9.284 | 1.00 | 25.47 | A | C |
| ATOM | 7822 | O | GLY | A | 492 | 39.590 | −31.710 | −9.219 | 1.00 | 26.12 | A | O |
| ATOM | 7824 | N | SER | A | 493 | 41.829 | −31.495 | −9.204 | 1.00 | 25.71 | A | N |
| ATOM | 7825 | CA | SER | A | 493 | 41.777 | −30.049 | −9.019 | 1.00 | 25.75 | A | C |
| ATOM | 7827 | CB | SER | A | 493 | 43.159 | −29.494 | −8.656 | 1.00 | 26.12 | A | C |
| ATOM | 7830 | OG | SER | A | 493 | 43.108 | −28.096 | −8.407 | 1.00 | 25.68 | A | O |
| ATOM | 7832 | C | SER | A | 493 | 41.268 | −29.373 | −10.287 | 1.00 | 25.36 | A | C |
| ATOM | 7833 | O | SER | A | 493 | 41.558 | −29.836 | −11.390 | 1.00 | 25.36 | A | O |
| ATOM | 7835 | N | PRO | A | 494 | 40.493 | −28.285 | −10.134 | 1.00 | 25.03 | A | N |
| ATOM | 7836 | CA | PRO | A | 494 | 40.128 | −27.456 | −11.280 | 1.00 | 24.84 | A | C |
| ATOM | 7838 | CB | PRO | A | 494 | 38.930 | −26.657 | −10.766 | 1.00 | 24.98 | A | C |
| ATOM | 7841 | CG | PRO | A | 494 | 39.143 | −26.559 | −9.306 | 1.00 | 25.14 | A | C |
| ATOM | 7844 | CD | PRO | A | 494 | 39.871 | −27.804 | −8.887 | 1.00 | 25.07 | A | C |
| ATOM | 7847 | C | PRO | A | 494 | 41.269 | −26.525 | −11.699 | 1.00 | 24.33 | A | C |
| ATOM | 7848 | O | PRO | A | 494 | 41.251 | −25.992 | −12.809 | 1.00 | 24.46 | A | O |
| ATOM | 7849 | N | PHE | A | 495 | 42.242 | −26.332 | −10.809 | 1.00 | 23.65 | A | N |
| ATOM | 7850 | CA | PHE | A | 495 | 43.440 | −25.554 | −11.110 | 1.00 | 23.36 | A | C |
| ATOM | 7852 | CB | PHE | A | 495 | 43.903 | −24.783 | −9.872 | 1.00 | 23.58 | A | C |
| ATOM | 7855 | CG | PHE | A | 495 | 42.904 | −23.784 | −9.374 | 1.00 | 23.05 | A | C |
| ATOM | 7856 | CD1 | PHE | A | 495 | 42.977 | −22.457 | −9.760 | 1.00 | 21.76 | A | C |
| ATOM | 7858 | CE1 | PHE | A | 495 | 42.052 | −21.539 | −9.302 | 1.00 | 22.61 | A | C |
| ATOM | 7860 | CZ | PHE | A | 495 | 41.036 | −21.946 | −8.454 | 1.00 | 22.69 | A | C |
| ATOM | 7862 | CE2 | PHE | A | 495 | 40.953 | −23.264 | −8.068 | 1.00 | 23.16 | A | C |
| ATOM | 7864 | CD2 | PHE | A | 495 | 41.883 | −24.175 | −8.525 | 1.00 | 23.51 | A | C |
| ATOM | 7866 | C | PHE | A | 495 | 44.561 | −26.470 | −11.576 | 1.00 | 23.05 | A | C |
| ATOM | 7867 | O | PHE | A | 495 | 44.538 | −27.676 | −11.325 | 1.00 | 22.76 | A | O |
| ATOM | 7869 | N | ALA | A | 496 | 45.545 | −25.886 | −12.253 | 1.00 | 22.91 | A | N |
| ATOM | 7870 | CA | ALA | A | 496 | 46.730 | −26.622 | −12.677 | 1.00 | 22.83 | A | C |
| ATOM | 7872 | CB | ALA | A | 496 | 47.528 | −25.806 | −13.681 | 1.00 | 23.00 | A | C |
| ATOM | 7876 | C | ALA | A | 496 | 47.586 | −26.957 | −11.461 | 1.00 | 22.74 | A | C |

TABLE 8-2-continued

Coordinates for L494P Structure

| ATOM | 7877 | O | ALA | A | 496 | 47.573 | −26.229 | −10.469 | 1.00 | 23.03 | A | O |
|---|---|---|---|---|---|---|---|---|---|---|---|---|
| ATOM | 7879 | N | LYS | A | 497 | 48.331 | −28.056 | −11.544 | 1.00 | 22.67 | A | N |
| ATOM | 7880 | CA | LYS | A | 497 | 49.160 | −28.523 | −10.424 | 1.00 | 22.50 | A | C |
| ATOM | 7882 | CB | LYS | A | 497 | 49.887 | −29.828 | −10.785 | 1.00 | 22.80 | A | C |
| ATOM | 7885 | CG | LYS | A | 497 | 48.946 | −31.004 | −11.042 | 1.00 | 24.08 | A | C |
| ATOM | 7888 | CD | LYS | A | 497 | 49.679 | −32.344 | −11.050 | 1.00 | 24.82 | A | C |
| ATOM | 7891 | CE | LYS | A | 497 | 48.703 | −33.508 | −11.215 | 1.00 | 24.18 | A | C |
| ATOM | 7894 | NZ | LYS | A | 497 | 49.301 | −34.815 | −10.828 | 1.00 | 23.44 | A | N |
| ATOM | 7898 | C | LYS | A | 497 | 50.161 | −27.474 | −9.917 | 1.00 | 21.54 | A | C |
| ATOM | 7899 | O | LYS | A | 497 | 50.391 | −27.385 | −8.712 | 1.00 | 21.63 | A | O |
| ATOM | 7901 | N | PRO | A | 498 | 50.763 | −26.684 | −10.828 | 1.00 | 20.42 | A | N |
| ATOM | 7902 | CA | PRO | A | 498 | 51.606 | −25.575 | −10.392 | 1.00 | 19.81 | A | C |
| ATOM | 7904 | CB | PRO | A | 498 | 51.853 | −24.807 | −11.689 | 1.00 | 20.02 | A | C |
| ATOM | 7907 | CG | PRO | A | 498 | 51.868 | −25.858 | −12.730 | 1.00 | 20.71 | A | C |
| ATOM | 7910 | CD | PRO | A | 498 | 50.921 | −26.940 | −12.272 | 1.00 | 20.44 | A | C |
| ATOM | 7913 | C | PRO | A | 498 | 50.954 | −24.665 | −9.353 | 1.00 | 19.16 | A | C |
| ATOM | 7914 | O | PRO | A | 498 | 51.549 | −24.416 | −8.304 | 1.00 | 19.10 | A | O |
| ATOM | 7915 | N | PHE | A | 499 | 49.745 | −24.184 | −9.636 | 1.00 | 18.41 | A | N |
| ATOM | 7916 | CA | PHE | A | 499 | 49.067 | −23.259 | −8.725 | 1.00 | 17.71 | A | C |
| ATOM | 7918 | CB | PHE | A | 499 | 47.876 | −22.577 | −9.394 | 1.00 | 17.65 | A | C |
| ATOM | 7921 | CG | PHE | A | 499 | 47.125 | −21.666 | −8.469 | 1.00 | 17.11 | A | C |
| ATOM | 7922 | CD1 | PHE | A | 499 | 47.733 | −20.525 | −7.964 | 1.00 | 15.75 | A | C |
| ATOM | 7924 | CE1 | PHE | A | 499 | 47.059 | −19.686 | −7.097 | 1.00 | 16.82 | A | C |
| ATOM | 7926 | CZ | PHE | A | 499 | 45.760 | −19.985 | −6.715 | 1.00 | 18.26 | A | C |
| ATOM | 7928 | CE2 | PHE | A | 499 | 45.146 | −21.128 | −7.203 | 1.00 | 19.35 | A | C |
| ATOM | 7930 | CD2 | PHE | A | 499 | 45.833 | −21.966 | −8.071 | 1.00 | 18.48 | A | C |
| ATOM | 7932 | C | PHE | A | 499 | 48.594 | −23.918 | −7.432 | 1.00 | 17.27 | A | C |
| ATOM | 7933 | O | PHE | A | 499 | 48.608 | −23.283 | −6.377 | 1.00 | 18.04 | A | O |
| ATOM | 7935 | N | VAL | A | 500 | 48.156 | −25.173 | −7.520 | 1.00 | 16.13 | A | N |
| ATOM | 7936 | CA | VAL | A | 500 | 47.787 | −25.947 | −6.334 | 1.00 | 15.18 | A | C |
| ATOM | 7938 | CB | VAL | A | 500 | 47.344 | −27.381 | −6.710 | 1.00 | 15.13 | A | C |
| ATOM | 7940 | CG1 | VAL | A | 500 | 46.049 | −27.346 | −7.503 | 1.00 | 15.59 | A | C |
| ATOM | 7944 | CG2 | VAL | A | 500 | 47.181 | −28.247 | −5.466 | 1.00 | 15.76 | A | C |
| ATOM | 7948 | C | VAL | A | 500 | 48.972 | −26.003 | −5.367 | 1.00 | 14.53 | A | C |
| ATOM | 7949 | O | VAL | A | 500 | 48.834 | −25.683 | −4.184 | 1.00 | 14.32 | A | O |
| ATOM | 7951 | N | GLU | A | 501 | 50.134 | −26.391 | −5.893 | 1.00 | 13.78 | A | N |
| ATOM | 7952 | CA | GLU | A | 501 | 51.380 | −26.469 | −5.126 | 1.00 | 13.17 | A | C |
| ATOM | 7954 | CB | GLU | A | 501 | 52.516 | −26.953 | −6.033 | 1.00 | 13.27 | A | C |
| ATOM | 7957 | CG | GLU | A | 501 | 53.883 | −27.124 | −5.355 | 1.00 | 12.99 | A | C |
| ATOM | 7960 | CD | GLU | A | 501 | 53.936 | −28.270 | −4.360 | 1.00 | 10.75 | A | C |
| ATOM | 7961 | OE1 | GLU | A | 501 | 53.035 | −29.135 | −4.365 | 1.00 | 9.48 | A | O |
| ATOM | 7962 | OE2 | GLU | A | 501 | 54.899 | −28.308 | −3.571 | 1.00 | 9.39 | A | O |
| ATOM | 7963 | C | GLU | A | 501 | 51.759 | −25.126 | −4.505 | 1.00 | 13.02 | A | C |
| ATOM | 7964 | O | GLU | A | 501 | 52.309 | −25.083 | −3.403 | 1.00 | 12.70 | A | O |
| ATOM | 7966 | N | THR | A | 502 | 51.479 | −24.037 | −5.218 | 1.00 | 13.13 | A | N |
| ATOM | 7967 | CA | THR | A | 502 | 51.715 | −22.696 | −4.689 | 1.00 | 12.94 | A | C |
| ATOM | 7969 | CB | THR | A | 502 | 51.408 | −21.597 | −5.724 | 1.00 | 12.49 | A | C |
| ATOM | 7971 | OG1 | THR | A | 502 | 51.913 | −21.986 | −7.007 | 1.00 | 12.30 | A | O |
| ATOM | 7973 | CG2 | THR | A | 502 | 52.045 | −20.281 | −5.314 | 1.00 | 11.05 | A | C |
| ATOM | 7977 | C | THR | A | 502 | 50.849 | −22.481 | −3.453 | 1.00 | 13.75 | A | C |
| ATOM | 7978 | O | THR | A | 502 | 51.323 | −21.947 | −2.451 | 1.00 | 14.63 | A | O |
| ATOM | 7980 | N | ALA | A | 503 | 49.587 | −22.912 | −3.526 | 1.00 | 13.85 | A | N |
| ATOM | 7981 | CA | ALA | A | 503 | 48.671 | −22.838 | −2.386 | 1.00 | 13.85 | A | C |
| ATOM | 7983 | CB | ALA | A | 503 | 47.298 | −23.367 | −2.766 | 1.00 | 13.55 | A | C |
| ATOM | 7987 | C | ALA | A | 503 | 49.229 | −23.619 | −1.202 | 1.00 | 14.25 | A | C |
| ATOM | 7988 | O | ALA | A | 503 | 49.414 | −23.068 | −0.115 | 1.00 | 14.42 | A | O |
| ATOM | 7990 | N | ILE | A | 504 | 49.517 | −24.899 | −1.426 | 1.00 | 14.43 | A | N |
| ATOM | 7991 | CA | ILE | A | 504 | 50.082 | −25.762 | −0.385 | 1.00 | 14.49 | A | C |
| ATOM | 7993 | CB | ILE | A | 504 | 50.462 | −27.159 | −0.950 | 1.00 | 14.26 | A | C |
| ATOM | 7995 | CG1 | ILE | A | 504 | 49.197 | −27.968 | −1.258 | 1.00 | 13.75 | A | C |
| ATOM | 7998 | CD1 | ILE | A | 504 | 49.450 | −29.249 | −2.022 | 1.00 | 11.62 | A | C |
| ATOM | 8002 | CG2 | ILE | A | 504 | 51.333 | −27.928 | 0.032 | 1.00 | 13.71 | A | C |
| ATOM | 8006 | C | ILE | A | 504 | 51.293 | −25.097 | 0.278 | 1.00 | 15.04 | A | C |
| ATOM | 8007 | O | ILE | A | 504 | 51.449 | −25.159 | 1.498 | 1.00 | 15.26 | A | O |
| ATOM | 8009 | N | ASN | A | 505 | 52.125 | −24.438 | −0.526 | 1.00 | 15.57 | A | N |
| ATOM | 8010 | CA | ASN | A | 505 | 53.295 | −23.716 | −0.014 | 1.00 | 16.27 | A | C |
| ATOM | 8012 | CB | ASN | A | 505 | 54.117 | −23.135 | −1.175 | 1.00 | 16.20 | A | C |
| ATOM | 8015 | CG | ASN | A | 505 | 54.937 | −24.191 | −1.910 | 1.00 | 16.68 | A | C |
| ATOM | 8016 | OD1 | ASN | A | 505 | 55.408 | −25.164 | −1.317 | 1.00 | 14.13 | A | O |
| ATOM | 8017 | ND2 | ASN | A | 505 | 55.122 | −23.989 | −3.213 | 1.00 | 16.63 | A | N |
| ATOM | 8020 | C | ASN | A | 505 | 52.973 | −22.607 | 1.014 | 1.00 | 16.76 | A | C |
| ATOM | 8021 | O | ASN | A | 505 | 53.840 | −22.239 | 1.811 | 1.00 | 17.12 | A | O |
| ATOM | 8023 | N | LEU | A | 506 | 51.749 | −22.074 | 0.995 | 1.00 | 16.63 | A | N |
| ATOM | 8024 | CA | LEU | A | 506 | 51.303 | −21.135 | 2.034 | 1.00 | 16.26 | A | C |
| ATOM | 8026 | CB | LEU | A | 506 | 49.936 | −20.530 | 1.694 | 1.00 | 16.36 | A | C |
| ATOM | 8029 | CG | LEU | A | 506 | 49.433 | −19.409 | 2.615 | 1.00 | 15.61 | A | C |
| ATOM | 8031 | CD1 | LEU | A | 506 | 50.134 | −18.100 | 2.305 | 1.00 | 16.15 | A | C |
| ATOM | 8035 | CD2 | LEU | A | 506 | 47.930 | −19.241 | 2.488 | 1.00 | 15.78 | A | C |

TABLE 8-2-continued

Coordinates for L494P Structure

| ATOM | 8039 | C | LEU | A | 506 | 51.220 | −21.858 | 3.373 | 1.00 | 16.06 | A | C |
|------|------|-----|-----|---|-----|--------|---------|--------|------|-------|---|---|
| ATOM | 8040 | O | LEU | A | 506 | 51.719 | −21.363 | 4.387 | 1.00 | 15.94 | A | O |
| ATOM | 8042 | N | ALA | A | 507 | 50.582 | −23.028 | 3.367 | 1.00 | 15.76 | A | N |
| ATOM | 8043 | CA | ALA | A | 507 | 50.483 | −23.862 | 4.563 | 1.00 | 15.58 | A | C |
| ATOM | 8045 | CB | ALA | A | 507 | 49.733 | −25.148 | 4.257 | 1.00 | 15.54 | A | C |
| ATOM | 8049 | C | ALA | A | 507 | 51.867 | −24.178 | 5.109 | 1.00 | 15.59 | A | C |
| ATOM | 8050 | O | ALA | A | 507 | 52.095 | −24.098 | 6.316 | 1.00 | 14.90 | A | O |
| ATOM | 8052 | N | ARG | A | 508 | 52.787 | −24.531 | 4.210 | 1.00 | 16.16 | A | N |
| ATOM | 8053 | CA | ARG | A | 508 | 54.174 | −24.806 | 4.585 | 1.00 | 16.29 | A | C |
| ATOM | 8055 | CB | ARG | A | 508 | 55.026 | −25.165 | 3.364 | 1.00 | 16.26 | A | C |
| ATOM | 8058 | CG | ARG | A | 508 | 54.660 | −26.473 | 2.679 | 1.00 | 17.94 | A | C |
| ATOM | 8061 | CD | ARG | A | 508 | 55.608 | −26.763 | 1.521 | 1.00 | 19.98 | A | C |
| ATOM | 8064 | NE | ARG | A | 508 | 54.905 | −27.288 | 0.346 | 1.00 | 21.98 | A | N |
| ATOM | 8066 | CZ | ARG | A | 508 | 54.787 | −28.577 | 0.019 | 1.00 | 22.61 | A | C |
| ATOM | 8067 | NH1 | ARG | A | 508 | 55.324 | −29.538 | 0.767 | 1.00 | 22.88 | A | N |
| ATOM | 8070 | NH2 | ARG | A | 508 | 54.120 | −28.910 | −1.080 | 1.00 | 22.72 | A | N |
| ATOM | 8073 | C | ARG | A | 508 | 54.783 | −23.598 | 5.274 | 1.00 | 16.50 | A | C |
| ATOM | 8074 | O | ARG | A | 508 | 55.366 | −23.724 | 6.347 | 1.00 | 16.45 | A | O |
| ATOM | 8076 | N | GLN | A | 509 | 54.634 | −22.430 | 4.652 | 1.00 | 17.01 | A | N |
| ATOM | 8077 | CA | GLN | A | 509 | 55.139 | −21.180 | 5.218 | 1.00 | 17.44 | A | C |
| ATOM | 8079 | CB | GLN | A | 509 | 54.932 | −20.022 | 4.233 | 1.00 | 17.64 | A | C |
| ATOM | 8082 | CG | GLN | A | 509 | 55.378 | −18.640 | 4.743 | 1.00 | 18.86 | A | C |
| ATOM | 8085 | CD | GLN | A | 509 | 56.866 | −18.559 | 5.059 | 1.00 | 19.80 | A | C |
| ATOM | 8086 | OE1 | GLN | A | 509 | 57.698 | −19.142 | 4.364 | 1.00 | 21.40 | A | O |
| ATOM | 8087 | NE2 | GLN | A | 509 | 57.205 | −17.824 | 6.109 | 1.00 | 20.43 | A | N |
| ATOM | 8090 | C | GLN | A | 509 | 54.489 | −20.856 | 6.566 | 1.00 | 17.62 | A | C |
| ATOM | 8091 | O | GLN | A | 509 | 55.147 | −20.310 | 7.452 | 1.00 | 17.58 | A | O |
| ATOM | 8093 | N | SER | A | 510 | 53.208 | −21.190 | 6.722 | 1.00 | 18.00 | A | N |
| ATOM | 8094 | CA | SER | A | 510 | 52.519 | −20.976 | 7.995 | 1.00 | 18.54 | A | C |
| ATOM | 8096 | CB | SER | A | 510 | 51.036 | −21.331 | 7.892 | 1.00 | 18.47 | A | C |
| ATOM | 8099 | OG | SER | A | 510 | 50.356 | −20.392 | 7.083 | 1.00 | 18.50 | A | O |
| ATOM | 8101 | C | SER | A | 510 | 53.182 | −21.778 | 9.109 | 1.00 | 19.15 | A | C |
| ATOM | 8102 | O | SER | A | 510 | 53.583 | −21.212 | 10.124 | 1.00 | 19.12 | A | O |
| ATOM | 8104 | N | HIS | A | 511 | 53.307 | −23.088 | 8.907 | 1.00 | 20.18 | A | N |
| ATOM | 8105 | CA | HIS | A | 511 | 54.032 | −23.956 | 9.844 | 1.00 | 21.08 | A | C |
| ATOM | 8107 | CB | HIS | A | 511 | 54.180 | −25.378 | 9.276 | 1.00 | 20.92 | A | C |
| ATOM | 8110 | CG | HIS | A | 511 | 52.976 | −26.246 | 9.480 | 1.00 | 21.15 | A | C |
| ATOM | 8111 | ND1 | HIS | A | 511 | 52.496 | −26.574 | 10.731 | 1.00 | 23.07 | A | N |
| ATOM | 8113 | CE1 | HIS | A | 511 | 51.438 | −27.355 | 10.605 | 1.00 | 21.16 | A | C |
| ATOM | 8115 | NE2 | HIS | A | 511 | 51.220 | −27.555 | 9.318 | 1.00 | 20.02 | A | N |
| ATOM | 8117 | CD2 | HIS | A | 511 | 52.171 | −26.877 | 8.593 | 1.00 | 20.33 | A | C |
| ATOM | 8119 | C | HIS | A | 511 | 55.422 | −23.394 | 10.176 | 1.00 | 22.01 | A | C |
| ATOM | 8120 | O | HIS | A | 511 | 55.836 | −23.382 | 11.340 | 1.00 | 22.10 | A | O |
| ATOM | 8122 | N | CYS | A | 512 | 56.127 | −22.928 | 9.145 | 1.00 | 22.75 | A | N |
| ATOM | 8123 | CA | CYS | A | 512 | 57.489 | −22.410 | 9.291 | 1.00 | 23.31 | A | C |
| ATOM | 8125 | CB | CYS | A | 512 | 58.162 | −22.308 | 7.918 | 1.00 | 23.29 | A | C |
| ATOM | 8128 | SG | CYS | A | 512 | 58.272 | −23.878 | 7.018 | 1.00 | 23.12 | A | S |
| ATOM | 8130 | C | CYS | A | 512 | 57.560 | −21.048 | 9.997 | 1.00 | 24.05 | A | C |
| ATOM | 8131 | O | CYS | A | 512 | 58.612 | −20.683 | 10.522 | 1.00 | 24.32 | A | O |
| ATOM | 8133 | N | THR | A | 513 | 56.455 | −20.303 | 10.006 | 1.00 | 24.74 | A | N |
| ATOM | 8134 | CA | THR | A | 513 | 56.424 | −18.975 | 10.627 | 1.00 | 25.50 | A | C |
| ATOM | 8136 | CB | THR | A | 513 | 55.556 | −17.982 | 9.806 | 1.00 | 25.40 | A | C |
| ATOM | 8138 | OG1 | THR | A | 513 | 56.349 | −17.410 | 8.760 | 1.00 | 24.78 | A | O |
| ATOM | 8140 | CG2 | THR | A | 513 | 55.027 | −16.856 | 10.681 | 1.00 | 25.88 | A | C |
| ATOM | 8144 | C | THR | A | 513 | 55.948 | −19.012 | 12.082 | 1.00 | 26.41 | A | C |
| ATOM | 8145 | O | THR | A | 513 | 56.535 | −18.347 | 12.940 | 1.00 | 26.85 | A | O |
| ATOM | 8147 | N | TYR | A | 514 | 54.899 | −19.786 | 12.361 | 1.00 | 27.13 | A | N |
| ATOM | 8148 | CA | TYR | A | 514 | 54.304 | −19.828 | 13.703 | 1.00 | 27.65 | A | C |
| ATOM | 8150 | CB | TYR | A | 514 | 52.780 | −19.915 | 13.608 | 1.00 | 27.23 | A | C |
| ATOM | 8153 | CG | TYR | A | 514 | 52.205 | −18.699 | 12.929 | 1.00 | 25.40 | A | C |
| ATOM | 8154 | CD1 | TYR | A | 514 | 52.107 | −17.486 | 13.607 | 1.00 | 24.39 | A | C |
| ATOM | 8156 | CE1 | TYR | A | 514 | 51.598 | −16.355 | 12.985 | 1.00 | 22.46 | A | C |
| ATOM | 8158 | CZ | TYR | A | 514 | 51.196 | −16.428 | 11.667 | 1.00 | 21.99 | A | C |
| ATOM | 8159 | OH | TYR | A | 514 | 50.694 | −15.313 | 11.041 | 1.00 | 21.78 | A | O |
| ATOM | 8161 | CE2 | TYR | A | 514 | 51.297 | −17.618 | 10.969 | 1.00 | 22.62 | A | C |
| ATOM | 8163 | CD2 | TYR | A | 514 | 51.804 | −18.743 | 11.600 | 1.00 | 22.78 | A | C |
| ATOM | 8165 | C | TYR | A | 514 | 54.883 | −20.942 | 14.571 | 1.00 | 29.02 | A | C |
| ATOM | 8166 | O | TYR | A | 514 | 54.290 | −22.013 | 14.724 | 1.00 | 28.90 | A | O |
| ATOM | 8168 | N | HIS | A | 515 | 56.057 | −20.655 | 15.129 | 1.00 | 30.73 | A | N |
| ATOM | 8169 | CA | HIS | A | 515 | 56.761 | −21.538 | 16.063 | 1.00 | 32.06 | A | C |
| ATOM | 8171 | CB | HIS | A | 515 | 58.121 | −21.948 | 15.484 | 1.00 | 32.40 | A | C |
| ATOM | 8174 | CG | HIS | A | 515 | 59.036 | −20.791 | 15.217 | 1.00 | 33.80 | A | C |
| ATOM | 8175 | ND1 | HIS | A | 515 | 59.022 | −20.090 | 14.030 | 1.00 | 34.76 | A | N |
| ATOM | 8177 | CE1 | HIS | A | 515 | 59.920 | −19.122 | 14.081 | 1.00 | 35.38 | A | C |
| ATOM | 8179 | NE2 | HIS | A | 515 | 60.513 | −19.166 | 15.261 | 1.00 | 35.75 | A | N |
| ATOM | 8181 | CD2 | HIS | A | 515 | 59.977 | −20.200 | 15.991 | 1.00 | 34.95 | A | C |
| ATOM | 8183 | C | HIS | A | 515 | 56.966 | −20.796 | 17.389 | 1.00 | 32.51 | A | C |
| ATOM | 8184 | O | HIS | A | 515 | 56.694 | −19.593 | 17.484 | 1.00 | 32.74 | A | O |

TABLE 8-2-continued

Coordinates for L494P Structure

| ATOM | 8186 | N | ASN | A | 516 | 57.448 | −21.517 | 18.401 | 1.00 | 32.73 | A | N |
|---|---|---|---|---|---|---|---|---|---|---|---|---|
| ATOM | 8187 | CA | ASN | A | 516 | 57.747 | −20.931 | 19.713 | 1.00 | 32.96 | A | C |
| ATOM | 8189 | CB | ASN | A | 516 | 56.625 | −21.237 | 20.715 | 1.00 | 33.20 | A | C |
| ATOM | 8192 | CG | ASN | A | 516 | 55.351 | −20.436 | 20.446 | 1.00 | 33.85 | A | C |
| ATOM | 8193 | OD1 | ASN | A | 516 | 54.596 | −20.730 | 19.512 | 1.00 | 31.44 | A | O |
| ATOM | 8194 | ND2 | ASN | A | 516 | 55.097 | −19.430 | 21.283 | 1.00 | 33.00 | A | N |
| ATOM | 8197 | C | ASN | A | 516 | 59.081 | −21.436 | 20.261 | 1.00 | 32.91 | A | C |
| ATOM | 8198 | O | ASN | A | 516 | 60.121 | −21.308 | 19.611 | 1.00 | 33.04 | A | O |
| ATOM | 8200 | N | THR | A | 521 | 66.548 | −21.132 | 21.796 | 1.00 | 40.70 | A | N |
| ATOM | 8201 | CA | THR | A | 521 | 66.207 | −20.050 | 20.874 | 1.00 | 40.78 | A | C |
| ATOM | 8203 | CB | THR | A | 521 | 66.436 | −20.476 | 19.406 | 1.00 | 40.62 | A | C |
| ATOM | 8205 | OG1 | THR | A | 521 | 67.703 | −21.134 | 19.285 | 1.00 | 39.94 | A | O |
| ATOM | 8207 | CG2 | THR | A | 521 | 66.402 | −19.267 | 18.478 | 1.00 | 40.21 | A | C |
| ATOM | 8211 | C | THR | A | 521 | 64.746 | −19.619 | 21.056 | 1.00 | 41.19 | A | C |
| ATOM | 8212 | O | THR | A | 521 | 63.841 | −20.460 | 21.049 | 1.00 | 41.68 | A | O |
| ATOM | 8214 | N | SER | A | 522 | 64.523 | −18.313 | 21.209 | 1.00 | 41.01 | A | N |
| ATOM | 8215 | CA | SER | A | 522 | 63.182 | −17.767 | 21.453 | 1.00 | 40.95 | A | C |
| ATOM | 8217 | CB | SER | A | 522 | 63.294 | −16.355 | 22.049 | 1.00 | 40.91 | A | C |
| ATOM | 8220 | OG | SER | A | 522 | 63.552 | −15.382 | 21.052 | 1.00 | 40.15 | A | O |
| ATOM | 8222 | C | SER | A | 522 | 62.329 | −17.754 | 20.168 | 1.00 | 41.29 | A | C |
| ATOM | 8223 | O | SER | A | 522 | 62.835 | −18.071 | 19.089 | 1.00 | 41.26 | A | O |
| ATOM | 8225 | N | PRO | A | 523 | 61.026 | −17.409 | 20.282 | 1.00 | 41.67 | A | N |
| ATOM | 8226 | CA | PRO | A | 523 | 60.172 | −17.283 | 19.088 | 1.00 | 41.68 | A | C |
| ATOM | 8228 | CB | PRO | A | 523 | 58.815 | −16.856 | 19.666 | 1.00 | 41.63 | A | C |
| ATOM | 8231 | CG | PRO | A | 523 | 58.807 | −17.408 | 21.044 | 1.00 | 41.77 | A | C |
| ATOM | 8234 | CD | PRO | A | 523 | 60.230 | −17.359 | 21.526 | 1.00 | 41.83 | A | C |
| ATOM | 8237 | C | PRO | A | 523 | 60.679 | −16.274 | 18.041 | 1.00 | 41.69 | A | C |
| ATOM | 8238 | O | PRO | A | 523 | 60.935 | −16.665 | 16.900 | 1.00 | 41.96 | A | O |
| ATOM | 8239 | N | ASP | A | 524 | 60.820 | −15.003 | 18.422 | 1.00 | 41.43 | A | N |
| ATOM | 8240 | CA | ASP | A | 524 | 61.364 | −13.979 | 17.522 | 1.00 | 41.02 | A | C |
| ATOM | 8242 | CB | ASP | A | 524 | 60.602 | −12.652 | 17.664 | 1.00 | 41.31 | A | C |
| ATOM | 8245 | CG | ASP | A | 524 | 60.708 | −11.774 | 16.417 | 1.00 | 42.01 | A | C |
| ATOM | 8246 | OD1 | ASP | A | 524 | 61.842 | −11.469 | 15.989 | 1.00 | 42.29 | A | O |
| ATOM | 8247 | OD2 | ASP | A | 524 | 59.655 | −11.387 | 15.865 | 1.00 | 42.57 | A | O |
| ATOM | 8248 | C | ASP | A | 524 | 62.854 | −13.803 | 17.824 | 1.00 | 40.28 | A | C |
| ATOM | 8249 | O | ASP | A | 524 | 63.228 | −13.154 | 18.802 | 1.00 | 40.11 | A | O |
| ATOM | 8251 | N | GLU | A | 525 | 63.681 | −14.371 | 16.946 | 1.00 | 39.60 | A | N |
| ATOM | 8252 | CA | GLU | A | 525 | 65.126 | −14.597 | 17.159 | 1.00 | 39.35 | A | C |
| ATOM | 8254 | CB | GLU | A | 525 | 65.483 | −14.783 | 18.645 | 1.00 | 39.51 | A | C |
| ATOM | 8257 | CG | GLU | A | 525 | 66.978 | −14.944 | 18.955 | 1.00 | 40.12 | A | C |
| ATOM | 8260 | CD | GLU | A | 525 | 67.789 | −13.676 | 18.721 | 1.00 | 41.52 | A | C |
| ATOM | 8261 | OE1 | GLU | A | 525 | 69.013 | −13.799 | 18.496 | 1.00 | 41.73 | A | O |
| ATOM | 8262 | OE2 | GLU | A | 525 | 67.217 | −12.562 | 18.760 | 1.00 | 41.99 | A | O |
| ATOM | 8263 | C | GLU | A | 525 | 65.554 | −15.835 | 16.352 | 1.00 | 38.94 | A | C |
| ATOM | 8264 | O | GLU | A | 525 | 66.736 | −15.994 | 16.020 | 1.00 | 39.49 | A | O |
| ATOM | 8266 | N | LEU | A | 526 | 64.589 | −16.716 | 16.072 | 1.00 | 37.92 | A | N |
| ATOM | 8267 | CA | LEU | A | 526 | 64.740 | −17.769 | 15.068 | 1.00 | 36.89 | A | C |
| ATOM | 8269 | CB | LEU | A | 526 | 64.024 | −19.049 | 15.516 | 1.00 | 36.77 | A | C |
| ATOM | 8272 | CG | LEU | A | 526 | 64.013 | −20.253 | 14.565 | 1.00 | 36.82 | A | C |
| ATOM | 8274 | CD1 | LEU | A | 526 | 63.540 | −21.504 | 15.302 | 1.00 | 35.24 | A | C |
| ATOM | 8278 | CD2 | LEU | A | 526 | 65.382 | −20.492 | 13.935 | 1.00 | 36.63 | A | C |
| ATOM | 8282 | C | LEU | A | 526 | 64.185 | −17.262 | 13.735 | 1.00 | 36.23 | A | C |
| ATOM | 8283 | O | LEU | A | 526 | 64.661 | −17.654 | 12.671 | 1.00 | 36.06 | A | O |
| ATOM | 8285 | N | THR | A | 527 | 63.177 | −16.391 | 13.805 | 1.00 | 35.70 | A | N |
| ATOM | 8286 | CA | THR | A | 527 | 62.713 | −15.630 | 12.643 | 1.00 | 35.26 | A | C |
| ATOM | 8288 | CB | THR | A | 527 | 61.469 | −14.766 | 12.981 | 1.00 | 35.09 | A | C |
| ATOM | 8290 | OG1 | THR | A | 527 | 60.448 | −15.587 | 13.560 | 1.00 | 35.42 | A | O |
| ATOM | 8292 | CG2 | THR | A | 527 | 60.918 | −14.084 | 11.730 | 1.00 | 33.75 | A | C |
| ATOM | 8296 | C | THR | A | 527 | 63.817 | −14.705 | 12.121 | 1.00 | 35.05 | A | C |
| ATOM | 8297 | O | THR | A | 527 | 63.915 | −14.473 | 10.914 | 1.00 | 35.33 | A | O |
| ATOM | 8299 | N | ARG | A | 528 | 64.645 | −14.185 | 13.029 | 1.00 | 34.45 | A | N |
| ATOM | 8300 | CA | ARG | A | 528 | 65.746 | −13.295 | 12.654 | 1.00 | 34.07 | A | C |
| ATOM | 8302 | CB | ARG | A | 528 | 66.399 | −12.684 | 13.897 | 1.00 | 34.21 | A | C |
| ATOM | 8305 | CG | ARG | A | 528 | 67.430 | −11.597 | 13.577 | 1.00 | 35.79 | A | C |
| ATOM | 8308 | CD | ARG | A | 528 | 68.237 | −11.153 | 14.802 | 1.00 | 37.39 | A | C |
| ATOM | 8311 | NE | ARG | A | 528 | 68.738 | −12.271 | 15.607 | 1.00 | 38.17 | A | N |
| ATOM | 8313 | CZ | ARG | A | 528 | 69.715 | −13.105 | 15.245 | 1.00 | 37.53 | A | C |
| ATOM | 8314 | NH1 | ARG | A | 528 | 70.333 | −12.981 | 14.072 | 1.00 | 36.61 | A | N |
| ATOM | 8317 | NH2 | ARG | A | 528 | 70.079 | −14.085 | 16.066 | 1.00 | 37.93 | A | N |
| ATOM | 8320 | C | ARG | A | 528 | 66.801 | −14.024 | 11.819 | 1.00 | 33.31 | A | C |
| ATOM | 8321 | O | ARG | A | 528 | 67.225 | −13.525 | 10.774 | 1.00 | 33.25 | A | O |
| ATOM | 8323 | N | LYS | A | 529 | 67.221 | −15.198 | 12.287 | 1.00 | 32.35 | A | N |
| ATOM | 8324 | CA | LYS | A | 529 | 68.219 | −16.003 | 11.579 | 1.00 | 31.60 | A | C |
| ATOM | 8326 | CB | LYS | A | 529 | 68.676 | −17.186 | 12.439 | 1.00 | 31.66 | A | C |
| ATOM | 8329 | CG | LYS | A | 529 | 69.437 | −16.800 | 13.696 | 1.00 | 31.41 | A | C |
| ATOM | 8332 | CD | LYS | A | 529 | 69.959 | −18.035 | 14.408 | 1.00 | 31.32 | A | C |
| ATOM | 8335 | CE | LYS | A | 529 | 70.798 | −17.669 | 15.617 | 1.00 | 32.31 | A | C |
| ATOM | 8338 | NZ | LYS | A | 529 | 71.369 | −18.876 | 16.276 | 1.00 | 33.65 | A | N |

TABLE 8-2-continued

Coordinates for L494P Structure

| ATOM | 8342 | C | LYS | A | 529 | 67.670 | −16.531 | 10.260 | 1.00 | 30.95 | A | C |
| ATOM | 8343 | O | LYS | A | 529 | 68.297 | −16.364 | 9.213 | 1.00 | 30.56 | A | O |
| ATOM | 8345 | N | ARG | A | 530 | 66.501 | −17.170 | 10.329 | 1.00 | 30.64 | A | N |
| ATOM | 8346 | CA | ARG | A | 530 | 65.846 | −17.760 | 9.153 | 1.00 | 30.15 | A | C |
| ATOM | 8348 | CB | ARG | A | 530 | 64.482 | −18.362 | 9.525 | 1.00 | 29.94 | A | C |
| ATOM | 8351 | CG | ARG | A | 530 | 64.561 | −19.726 | 10.225 | 1.00 | 29.01 | A | C |
| ATOM | 8354 | CD | ARG | A | 530 | 63.171 | −20.281 | 10.550 | 1.00 | 27.64 | A | C |
| ATOM | 8357 | NE | ARG | A | 530 | 63.220 | −21.609 | 11.172 | 1.00 | 25.77 | A | N |
| ATOM | 8359 | CZ | ARG | A | 530 | 62.150 | −22.322 | 11.537 | 1.00 | 23.97 | A | C |
| ATOM | 8360 | NH1 | ARG | A | 530 | 60.921 | −21.851 | 11.352 | 1.00 | 22.79 | A | N |
| ATOM | 8363 | NH2 | ARG | A | 530 | 62.307 | −23.518 | 12.092 | 1.00 | 23.31 | A | N |
| ATOM | 8366 | C | ARG | A | 530 | 65.689 | −16.746 | 8.017 | 1.00 | 30.16 | A | C |
| ATOM | 8367 | O | ARG | A | 530 | 65.923 | −17.075 | 6.853 | 1.00 | 30.17 | A | O |
| ATOM | 8369 | N | VAL | A | 531 | 65.304 | −15.518 | 8.360 | 1.00 | 30.09 | A | N |
| ATOM | 8370 | CA | VAL | A | 531 | 65.249 | −14.423 | 7.384 | 1.00 | 29.85 | A | C |
| ATOM | 8372 | CB | VAL | A | 531 | 64.687 | −13.116 | 8.009 | 1.00 | 29.92 | A | C |
| ATOM | 8374 | CG1 | VAL | A | 531 | 65.130 | −11.891 | 7.212 | 1.00 | 29.47 | A | C |
| ATOM | 8378 | CG2 | VAL | A | 531 | 63.166 | −13.183 | 8.090 | 1.00 | 30.50 | A | C |
| ATOM | 8382 | C | VAL | A | 531 | 66.628 | −14.151 | 6.781 | 1.00 | 29.24 | A | C |
| ATOM | 8383 | O | VAL | A | 531 | 66.781 | −14.158 | 5.559 | 1.00 | 29.23 | A | O |
| ATOM | 8385 | N | LEU | A | 532 | 67.623 | −13.925 | 7.639 | 1.00 | 28.50 | A | N |
| ATOM | 8386 | CA | LEU | A | 532 | 68.994 | −13.652 | 7.186 | 1.00 | 28.01 | A | C |
| ATOM | 8388 | CB | LEU | A | 532 | 69.944 | −13.450 | 8.378 | 1.00 | 28.09 | A | C |
| ATOM | 8391 | CG | LEU | A | 532 | 70.095 | −12.013 | 8.894 | 1.00 | 28.78 | A | C |
| ATOM | 8393 | CD1 | LEU | A | 532 | 68.741 | −11.373 | 9.211 | 1.00 | 28.04 | A | C |
| ATOM | 8397 | CD2 | LEU | A | 532 | 71.014 | −11.979 | 10.112 | 1.00 | 28.59 | A | C |
| ATOM | 8401 | C | LEU | A | 532 | 69.533 | −14.754 | 6.272 | 1.00 | 27.20 | A | C |
| ATOM | 8402 | O | LEU | A | 532 | 70.151 | −14.470 | 5.243 | 1.00 | 26.80 | A | O |
| ATOM | 8404 | N | SER | A | 533 | 69.283 | −16.004 | 6.652 | 1.00 | 26.36 | A | N |
| ATOM | 8405 | CA | SER | A | 533 | 69.742 | −17.159 | 5.883 | 1.00 | 25.65 | A | C |
| ATOM | 8407 | CB | SER | A | 533 | 69.573 | −18.437 | 6.705 | 1.00 | 25.79 | A | C |
| ATOM | 8410 | OG | SER | A | 533 | 68.231 | −18.588 | 7.127 | 1.00 | 26.13 | A | O |
| ATOM | 8412 | C | SER | A | 533 | 69.009 | −17.306 | 4.549 | 1.00 | 24.80 | A | C |
| ATOM | 8413 | O | SER | A | 533 | 69.589 | −17.786 | 3.573 | 1.00 | 24.87 | A | O |
| ATOM | 8415 | N | VAL | A | 534 | 67.742 | −16.897 | 4.514 | 1.00 | 23.73 | A | N |
| ATOM | 8416 | CA | VAL | A | 534 | 66.930 | −16.993 | 3.299 | 1.00 | 22.78 | A | C |
| ATOM | 8418 | CB | VAL | A | 534 | 65.442 | −17.279 | 3.634 | 1.00 | 22.62 | A | C |
| ATOM | 8420 | CG1 | VAL | A | 534 | 64.574 | −17.176 | 2.393 | 1.00 | 22.83 | A | C |
| ATOM | 8424 | CG2 | VAL | A | 534 | 65.299 | −18.661 | 4.247 | 1.00 | 20.75 | A | C |
| ATOM | 8428 | C | VAL | A | 534 | 67.063 | −15.751 | 2.407 | 1.00 | 22.04 | A | C |
| ATOM | 8429 | O | VAL | A | 534 | 67.186 | −15.880 | 1.188 | 1.00 | 21.64 | A | O |
| ATOM | 8431 | N | ILE | A | 535 | 67.058 | −14.562 | 3.010 | 1.00 | 21.46 | A | N |
| ATOM | 8432 | CA | ILE | A | 535 | 67.090 | −13.304 | 2.249 | 1.00 | 21.12 | A | C |
| ATOM | 8434 | CB | ILE | A | 535 | 66.130 | −12.241 | 2.845 | 1.00 | 21.03 | A | C |
| ATOM | 8436 | CG1 | ILE | A | 535 | 64.702 | −12.782 | 2.954 | 1.00 | 19.56 | A | C |
| ATOM | 8439 | CD1 | ILE | A | 535 | 64.055 | −13.076 | 1.628 | 1.00 | 18.99 | A | C |
| ATOM | 8443 | CG2 | ILE | A | 535 | 66.138 | −10.979 | 1.990 | 1.00 | 20.45 | A | C |
| ATOM | 8447 | C | ILE | A | 535 | 68.488 | −12.678 | 2.122 | 1.00 | 21.08 | A | C |
| ATOM | 8448 | O | ILE | A | 535 | 69.043 | −12.638 | 1.025 | 1.00 | 21.16 | A | O |
| ATOM | 8450 | N | THR | A | 536 | 69.049 | −12.188 | 3.229 | 1.00 | 21.05 | A | N |
| ATOM | 8451 | CA | THR | A | 536 | 70.220 | −11.290 | 3.167 | 1.00 | 21.47 | A | C |
| ATOM | 8453 | CB | THR | A | 536 | 70.259 | −10.315 | 4.373 | 1.00 | 21.61 | A | C |
| ATOM | 8455 | OG1 | THR | A | 536 | 70.381 | −11.053 | 5.593 | 1.00 | 23.10 | A | O |
| ATOM | 8457 | CG2 | THR | A | 536 | 68.993 | −9.465 | 4.422 | 1.00 | 22.21 | A | C |
| ATOM | 8461 | C | THR | A | 536 | 71.587 | −11.983 | 3.039 | 1.00 | 20.97 | A | C |
| ATOM | 8462 | O | THR | A | 536 | 72.308 | −11.747 | 2.069 | 1.00 | 20.73 | A | O |
| ATOM | 8464 | N | GLU | A | 537 | 71.947 | −12.817 | 4.013 | 1.00 | 20.65 | A | N |
| ATOM | 8465 | CA | GLU | A | 537 | 73.259 | −13.474 | 4.017 | 1.00 | 20.51 | A | C |
| ATOM | 8467 | CB | GLU | A | 537 | 73.649 | −13.911 | 5.432 | 1.00 | 20.64 | A | C |
| ATOM | 8470 | CG | GLU | A | 537 | 73.824 | −12.751 | 6.409 | 1.00 | 21.25 | A | C |
| ATOM | 8473 | CD | GLU | A | 537 | 74.728 | −13.076 | 7.590 | 1.00 | 20.98 | A | C |
| ATOM | 8474 | OE1 | GLU | A | 537 | 74.910 | −12.186 | 8.448 | 1.00 | 19.76 | A | O |
| ATOM | 8475 | OE2 | GLU | A | 537 | 75.261 | −14.205 | 7.663 | 1.00 | 20.90 | A | O |
| ATOM | 8476 | C | GLU | A | 537 | 73.294 | −14.689 | 3.088 | 1.00 | 20.36 | A | C |
| ATOM | 8477 | O | GLU | A | 537 | 72.475 | −15.599 | 3.235 | 1.00 | 20.54 | A | O |
| ATOM | 8479 | N | PRO | A | 538 | 74.244 | −14.718 | 2.130 | 1.00 | 20.10 | A | N |
| ATOM | 8480 | CA | PRO | A | 538 | 74.398 | −15.928 | 1.321 | 1.00 | 19.67 | A | C |
| ATOM | 8482 | CB | PRO | A | 538 | 75.354 | −15.495 | 0.198 | 1.00 | 19.39 | A | C |
| ATOM | 8485 | CG | PRO | A | 538 | 75.435 | −14.010 | 0.274 | 1.00 | 19.88 | A | C |
| ATOM | 8488 | CD | PRO | A | 538 | 75.155 | −13.647 | 1.688 | 1.00 | 20.22 | A | C |
| ATOM | 8491 | C | PRO | A | 538 | 75.009 | −17.071 | 2.123 | 1.00 | 19.62 | A | C |
| ATOM | 8492 | O | PRO | A | 538 | 75.449 | −16.868 | 3.256 | 1.00 | 19.61 | A | O |
| ATOM | 8493 | N | ILE | A | 539 | 75.027 | −18.263 | 1.534 | 1.00 | 19.52 | A | N |
| ATOM | 8494 | CA | ILE | A | 539 | 75.661 | −19.422 | 2.154 | 1.00 | 19.35 | A | C |
| ATOM | 8496 | CB | ILE | A | 539 | 75.149 | −20.739 | 1.535 | 1.00 | 19.15 | A | C |
| ATOM | 8498 | CG1 | ILE | A | 539 | 73.656 | −20.902 | 1.813 | 1.00 | 19.17 | A | C |
| ATOM | 8501 | CD1 | ILE | A | 539 | 73.079 | −22.205 | 1.311 | 1.00 | 19.79 | A | C |
| ATOM | 8505 | CG2 | ILE | A | 539 | 75.913 | −21.934 | 2.090 | 1.00 | 19.34 | A | C |

TABLE 8-2-continued

Coordinates for L494P Structure

| ATOM | 8509 | C | ILE | A | 539 | 77.173 | −19.326 | 1.977 | 1.00 | 19.38 | A | C |
|---|---|---|---|---|---|---|---|---|---|---|---|---|
| ATOM | 8510 | O | ILE | A | 539 | 77.652 | −18.812 | 0.963 | 1.00 | 18.71 | A | O |
| ATOM | 8512 | N | LEU | A | 540 | 77.920 | −19.810 | 2.969 | 1.00 | 19.89 | A | N |
| ATOM | 8513 | CA | LEU | A | 540 | 79.379 | −19.852 | 2.876 | 1.00 | 20.47 | A | C |
| ATOM | 8515 | CB | LEU | A | 540 | 80.001 | −20.467 | 4.139 | 1.00 | 20.46 | A | C |
| ATOM | 8518 | CG | LEU | A | 540 | 79.948 | −19.634 | 5.427 | 1.00 | 20.08 | A | C |
| ATOM | 8520 | CD1 | LEU | A | 540 | 80.419 | −20.457 | 6.618 | 1.00 | 18.44 | A | C |
| ATOM | 8524 | CD2 | LEU | A | 540 | 80.775 | −18.359 | 5.296 | 1.00 | 17.67 | A | C |
| ATOM | 8528 | C | LEU | A | 540 | 79.765 | −20.664 | 1.638 | 1.00 | 20.82 | A | C |
| ATOM | 8529 | O | LEU | A | 540 | 79.241 | −21.761 | 1.438 | 1.00 | 20.93 | A | O |
| ATOM | 8531 | N | PRO | A | 541 | 80.669 | −20.123 | 0.797 | 1.00 | 21.10 | A | N |
| ATOM | 8532 | CA | PRO | A | 541 | 80.960 | −20.737 | −0.501 | 1.00 | 21.17 | A | C |
| ATOM | 8534 | CB | PRO | A | 541 | 81.831 | −19.687 | −1.197 | 1.00 | 20.94 | A | C |
| ATOM | 8537 | CG | PRO | A | 541 | 82.477 | −18.951 | −0.096 | 1.00 | 21.31 | A | C |
| ATOM | 8540 | CD | PRO | A | 541 | 81.484 | −18.917 | 1.024 | 1.00 | 21.15 | A | C |
| ATOM | 8543 | C | PRO | A | 541 | 81.692 | −22.071 | −0.401 | 1.00 | 21.47 | A | C |
| ATOM | 8544 | O | PRO | A | 541 | 82.045 | −22.508 | 0.693 | 1.00 | 21.43 | A | O |
| ATOM | 8545 | N | PHE | A | 542 | 81.915 | −22.701 | −1.550 | 1.00 | 22.16 | A | N |
| ATOM | 8546 | CA | PHE | A | 542 | 82.488 | −24.043 | −1.607 | 1.00 | 22.83 | A | C |
| ATOM | 8548 | CB | PHE | A | 542 | 82.148 | −24.685 | −2.953 | 1.00 | 22.75 | A | C |
| ATOM | 8551 | CG | PHE | A | 542 | 82.651 | −26.095 | −3.102 | 1.00 | 22.87 | A | C |
| ATOM | 8552 | CD1 | PHE | A | 542 | 83.477 | −26.446 | −4.163 | 1.00 | 22.56 | A | C |
| ATOM | 8554 | CE1 | PHE | A | 542 | 83.938 | −27.747 | −4.306 | 1.00 | 21.48 | A | C |
| ATOM | 8556 | CZ | PHE | A | 542 | 83.581 | −28.712 | −3.382 | 1.00 | 21.47 | A | C |
| ATOM | 8558 | CE2 | PHE | A | 542 | 82.760 | −28.376 | −2.316 | 1.00 | 22.09 | A | C |
| ATOM | 8560 | CD2 | PHE | A | 542 | 82.301 | −27.073 | −2.180 | 1.00 | 22.60 | A | C |
| ATOM | 8562 | C | PHE | A | 542 | 84.007 | −24.066 | −1.386 | 1.00 | 23.60 | A | C |
| ATOM | 8563 | O | PHE | A | 542 | 84.750 | −23.309 | −2.017 | 1.00 | 23.24 | A | O |
| ATOM | 8565 | N | GLU | A | 543 | 84.447 | −24.940 | −0.480 | 1.00 | 24.65 | A | N |
| ATOM | 8566 | CA | GLU | A | 543 | 85.867 | −25.238 | −0.264 | 1.00 | 25.63 | A | C |
| ATOM | 8568 | CB | GLU | A | 543 | 86.242 | −25.032 | 1.209 | 1.00 | 25.64 | A | C |
| ATOM | 8571 | CG | GLU | A | 543 | 86.531 | −23.587 | 1.593 | 1.00 | 25.04 | A | C |
| ATOM | 8574 | CD | GLU | A | 543 | 87.219 | −23.462 | 2.945 | 1.00 | 24.31 | A | C |
| ATOM | 8575 | OE1 | GLU | A | 543 | 87.195 | −24.433 | 3.733 | 1.00 | 23.03 | A | O |
| ATOM | 8576 | OE2 | GLU | A | 543 | 87.787 | −22.385 | 3.219 | 1.00 | 23.80 | A | O |
| ATOM | 8577 | C | GLU | A | 543 | 86.149 | −26.685 | −0.685 | 1.00 | 26.60 | A | C |
| ATOM | 8578 | O | GLU | A | 543 | 85.244 | −27.387 | −1.132 | 1.00 | 26.93 | A | O |
| ATOM | 8580 | N | ARG | A | 544 | 87.398 | −27.128 | −0.543 | 1.00 | 27.49 | A | N |
| ATOM | 8581 | CA | ARG | A | 544 | 87.790 | −28.496 | −0.904 | 1.00 | 28.18 | A | C |
| ATOM | 8583 | CB | ARG | A | 544 | 88.462 | −28.503 | −2.283 | 1.00 | 28.70 | A | C |
| ATOM | 8586 | CG | ARG | A | 544 | 87.480 | −28.538 | −3.454 | 1.00 | 30.13 | A | C |
| ATOM | 8589 | CD | ARG | A | 544 | 87.958 | −27.689 | −4.627 | 1.00 | 32.27 | A | C |
| ATOM | 8592 | NE | ARG | A | 544 | 87.029 | −27.745 | −5.758 | 1.00 | 34.04 | A | N |
| ATOM | 8594 | CZ | ARG | A | 544 | 86.969 | −26.853 | −6.749 | 1.00 | 35.15 | A | C |
| ATOM | 8595 | NH1 | ARG | A | 544 | 87.785 | −25.801 | −6.780 | 1.00 | 35.93 | A | N |
| ATOM | 8598 | NH2 | ARG | A | 544 | 86.078 | −27.010 | −7.722 | 1.00 | 35.60 | A | N |
| ATOM | 8601 | C | ARG | A | 544 | 88.718 | −29.113 | 0.148 | 1.00 | 28.07 | A | C |
| ATOM | 8602 | O | ARG | A | 544 | 89.936 | −28.927 | 0.113 | 1.00 | 27.79 | A | O |
| ATOM | 8604 | N | SER | B | 6 | 65.194 | 37.534 | 11.490 | 1.00 | 30.93 | B | N |
| ATOM | 8605 | CA | SER | B | 6 | 66.501 | 38.213 | 11.258 | 1.00 | 31.10 | B | C |
| ATOM | 8607 | CB | SER | B | 6 | 67.126 | 38.622 | 12.599 | 1.00 | 31.12 | B | C |
| ATOM | 8610 | OG | SER | B | 6 | 68.384 | 39.251 | 12.418 | 1.00 | 30.48 | B | O |
| ATOM | 8612 | C | SER | B | 6 | 67.433 | 37.305 | 10.437 | 1.00 | 31.29 | B | C |
| ATOM | 8613 | O | SER | B | 6 | 67.056 | 36.867 | 9.347 | 1.00 | 31.44 | B | O |
| ATOM | 8617 | N | ALA | B | 7 | 68.634 | 37.031 | 10.954 | 1.00 | 31.29 | B | N |
| ATOM | 8618 | CA | ALA | B | 7 | 69.633 | 36.190 | 10.276 | 1.00 | 31.27 | B | C |
| ATOM | 8620 | CB | ALA | B | 7 | 70.875 | 36.063 | 11.153 | 1.00 | 31.07 | B | C |
| ATOM | 8624 | C | ALA | B | 7 | 69.128 | 34.792 | 9.894 | 1.00 | 31.29 | B | C |
| ATOM | 8625 | O | ALA | B | 7 | 68.262 | 34.227 | 10.566 | 1.00 | 31.47 | B | O |
| ATOM | 8627 | N | ASN | B | 8 | 69.690 | 34.242 | 8.817 | 1.00 | 31.13 | B | N |
| ATOM | 8628 | CA | ASN | B | 8 | 69.342 | 32.903 | 8.333 | 1.00 | 30.87 | B | C |
| ATOM | 8630 | CB | ASN | B | 8 | 68.536 | 33.009 | 7.033 | 1.00 | 30.78 | B | C |
| ATOM | 8633 | CG | ASN | B | 8 | 68.152 | 31.652 | 6.460 | 1.00 | 30.33 | B | C |
| ATOM | 8634 | OD1 | ASN | B | 8 | 67.997 | 30.671 | 7.187 | 1.00 | 30.31 | B | O |
| ATOM | 8635 | ND2 | ASN | B | 8 | 67.988 | 31.597 | 5.144 | 1.00 | 29.92 | B | N |
| ATOM | 8638 | C | ASN | B | 8 | 70.591 | 32.048 | 8.110 | 1.00 | 30.77 | B | C |
| ATOM | 8639 | O | ASN | B | 8 | 71.467 | 32.411 | 7.324 | 1.00 | 30.68 | B | O |
| ATOM | 8641 | N | TYR | B | 9 | 70.659 | 30.915 | 8.808 | 1.00 | 30.85 | B | N |
| ATOM | 8642 | CA | TYR | B | 9 | 71.782 | 29.980 | 8.700 | 1.00 | 30.90 | B | C |
| ATOM | 8644 | CB | TYR | B | 9 | 72.394 | 29.745 | 10.081 | 1.00 | 30.91 | B | C |
| ATOM | 8647 | CG | TYR | B | 9 | 72.941 | 30.996 | 10.724 | 1.00 | 31.38 | B | C |
| ATOM | 8648 | CD1 | TYR | B | 9 | 74.066 | 31.627 | 10.207 | 1.00 | 31.49 | B | C |
| ATOM | 8650 | CE1 | TYR | B | 9 | 74.577 | 32.772 | 10.792 | 1.00 | 31.53 | B | C |
| ATOM | 8652 | CZ | TYR | B | 9 | 73.963 | 33.302 | 11.915 | 1.00 | 31.18 | B | C |
| ATOM | 8653 | OH | TYR | B | 9 | 74.464 | 34.440 | 12.505 | 1.00 | 31.64 | B | O |
| ATOM | 8655 | CE2 | TYR | B | 9 | 72.845 | 32.694 | 12.449 | 1.00 | 30.98 | B | C |
| ATOM | 8657 | CD2 | TYR | B | 9 | 72.340 | 31.545 | 11.853 | 1.00 | 31.50 | B | C |
| ATOM | 8659 | C | TYR | B | 9 | 71.392 | 28.628 | 8.099 | 1.00 | 30.89 | B | C |

TABLE 8-2-continued

Coordinates for L494P Structure

| ATOM | 8660 | O | TYR | B | 9 | 72.244 | 27.749 | 7.954 | 1.00 | 30.84 | B | O |
|---|---|---|---|---|---|---|---|---|---|---|---|---|
| ATOM | 8662 | N | GLU | B | 10 | 70.118 | 28.461 | 7.748 | 1.00 | 30.91 | B | N |
| ATOM | 8663 | CA | GLU | B | 10 | 69.619 | 27.177 | 7.254 | 1.00 | 30.96 | B | C |
| ATOM | 8665 | CB | GLU | B | 10 | 68.090 | 27.193 | 7.135 | 1.00 | 31.16 | B | C |
| ATOM | 8668 | CG | GLU | B | 10 | 67.357 | 27.168 | 8.477 | 1.00 | 32.67 | B | C |
| ATOM | 8671 | CD | GLU | B | 10 | 65.997 | 26.478 | 8.404 | 1.00 | 34.80 | B | C |
| ATOM | 8672 | OE1 | GLU | B | 10 | 65.359 | 26.497 | 7.327 | 1.00 | 35.78 | B | O |
| ATOM | 8673 | OE2 | GLU | B | 10 | 65.564 | 25.914 | 9.433 | 1.00 | 34.93 | B | O |
| ATOM | 8674 | C | GLU | B | 10 | 70.237 | 26.801 | 5.905 | 1.00 | 30.57 | B | C |
| ATOM | 8675 | O | GLU | B | 10 | 70.673 | 27.678 | 5.156 | 1.00 | 30.27 | B | O |
| ATOM | 8677 | N | PRO | B | 11 | 70.281 | 25.490 | 5.596 | 1.00 | 30.23 | B | N |
| ATOM | 8678 | CA | PRO | B | 11 | 70.814 | 25.038 | 4.314 | 1.00 | 29.93 | B | C |
| ATOM | 8680 | CB | PRO | B | 11 | 70.985 | 23.528 | 4.519 | 1.00 | 29.85 | B | C |
| ATOM | 8683 | CG | PRO | B | 11 | 69.977 | 23.171 | 5.533 | 1.00 | 29.86 | B | C |
| ATOM | 8686 | CD | PRO | B | 11 | 69.874 | 24.357 | 6.448 | 1.00 | 30.23 | B | C |
| ATOM | 8689 | C | PRO | B | 11 | 69.862 | 25.312 | 3.154 | 1.00 | 29.66 | B | C |
| ATOM | 8690 | O | PRO | B | 11 | 68.641 | 25.250 | 3.325 | 1.00 | 29.68 | B | O |
| ATOM | 8691 | N | ASN | B | 12 | 70.428 | 25.631 | 1.993 | 1.00 | 29.25 | B | N |
| ATOM | 8692 | CA | ASN | B | 12 | 69.672 | 25.660 | 0.747 | 1.00 | 28.94 | B | C |
| ATOM | 8694 | CB | ASN | B | 12 | 70.298 | 26.638 | −0.252 | 1.00 | 29.10 | B | C |
| ATOM | 8697 | CG | ASN | B | 12 | 70.210 | 28.086 | 0.208 | 1.00 | 29.53 | B | C |
| ATOM | 8698 | OD1 | ASN | B | 12 | 69.136 | 28.575 | 0.559 | 1.00 | 31.39 | B | O |
| ATOM | 8699 | ND2 | ASN | B | 12 | 71.342 | 28.782 | 0.196 | 1.00 | 28.62 | B | N |
| ATOM | 8702 | C | ASN | B | 12 | 69.646 | 24.253 | 0.162 | 1.00 | 28.62 | B | C |
| ATOM | 8703 | O | ASN | B | 12 | 70.554 | 23.458 | 0.409 | 1.00 | 28.75 | B | O |
| ATOM | 8705 | N | SER | B | 13 | 68.600 | 23.943 | −0.600 | 1.00 | 28.28 | B | N |
| ATOM | 8706 | CA | SER | B | 13 | 68.467 | 22.629 | −1.238 | 1.00 | 27.84 | B | C |
| ATOM | 8708 | CB | SER | B | 13 | 67.066 | 22.466 | −1.842 | 1.00 | 27.87 | B | C |
| ATOM | 8711 | OG | SER | B | 13 | 66.698 | 23.594 | −2.621 | 1.00 | 27.68 | B | O |
| ATOM | 8713 | C | SER | B | 13 | 69.540 | 22.403 | −2.312 | 1.00 | 27.33 | B | C |
| ATOM | 8714 | O | SER | B | 13 | 69.999 | 21.280 | −2.514 | 1.00 | 27.15 | B | O |
| ATOM | 8716 | N | TRP | B | 14 | 69.941 | 23.480 | −2.982 | 1.00 | 26.98 | B | N |
| ATOM | 8717 | CA | TRP | B | 14 | 70.947 | 23.410 | −4.047 | 1.00 | 27.01 | B | C |
| ATOM | 8719 | CB | TRP | B | 14 | 70.801 | 24.595 | −5.025 | 1.00 | 27.03 | B | C |
| ATOM | 8722 | CG | TRP | B | 14 | 70.521 | 25.947 | −4.396 | 1.00 | 27.01 | B | C |
| ATOM | 8723 | CD1 | TRP | B | 14 | 69.295 | 26.521 | −4.199 | 1.00 | 27.14 | B | C |
| ATOM | 8725 | NE1 | TRP | B | 14 | 69.435 | 27.754 | −3.612 | 1.00 | 26.54 | B | N |
| ATOM | 8727 | CE2 | TRP | B | 14 | 70.768 | 28.009 | −3.426 | 1.00 | 27.41 | B | C |
| ATOM | 8728 | CD2 | TRP | B | 14 | 71.485 | 26.892 | −3.911 | 1.00 | 27.68 | B | C |
| ATOM | 8729 | CE3 | TRP | B | 14 | 72.884 | 26.902 | −3.834 | 1.00 | 29.36 | B | C |
| ATOM | 8731 | CZ3 | TRP | B | 14 | 73.516 | 28.014 | −3.281 | 1.00 | 30.23 | B | C |
| ATOM | 8733 | CH2 | TRP | B | 14 | 72.773 | 29.109 | −2.808 | 1.00 | 29.91 | B | C |
| ATOM | 8735 | CZ2 | TRP | B | 14 | 71.402 | 29.125 | −2.873 | 1.00 | 28.79 | B | C |
| ATOM | 8737 | C | TRP | B | 14 | 72.402 | 23.306 | −3.548 | 1.00 | 27.02 | B | C |
| ATOM | 8738 | O | TRP | B | 14 | 73.290 | 22.935 | −4.320 | 1.00 | 26.74 | B | O |
| ATOM | 8740 | N | ASP | B | 15 | 72.638 | 23.614 | −2.270 | 1.00 | 26.93 | B | N |
| ATOM | 8741 | CA | ASP | B | 15 | 73.999 | 23.688 | −1.705 | 1.00 | 26.86 | B | C |
| ATOM | 8743 | CB | ASP | B | 15 | 73.944 | 23.887 | −0.182 | 1.00 | 26.86 | B | C |
| ATOM | 8746 | CG | ASP | B | 15 | 73.721 | 25.336 | 0.219 | 1.00 | 26.99 | B | C |
| ATOM | 8747 | OD1 | ASP | B | 15 | 73.870 | 26.238 | −0.637 | 1.00 | 24.43 | B | O |
| ATOM | 8748 | OD2 | ASP | B | 15 | 73.406 | 25.571 | 1.408 | 1.00 | 27.44 | B | O |
| ATOM | 8749 | C | ASP | B | 15 | 74.894 | 22.484 | −2.010 | 1.00 | 26.90 | B | C |
| ATOM | 8750 | O | ASP | B | 15 | 74.415 | 21.365 | −2.191 | 1.00 | 26.83 | B | O |
| ATOM | 8752 | N | TYR | B | 16 | 76.202 | 22.739 | −2.039 | 1.00 | 27.18 | B | N |
| ATOM | 8753 | CA | TYR | B | 16 | 77.202 | 21.717 | −2.361 | 1.00 | 27.47 | B | C |
| ATOM | 8755 | CB | TYR | B | 16 | 78.530 | 22.369 | −2.767 | 1.00 | 27.32 | B | C |
| ATOM | 8758 | CG | TYR | B | 16 | 78.492 | 23.077 | −4.106 | 1.00 | 25.78 | B | C |
| ATOM | 8759 | CD1 | TYR | B | 16 | 78.255 | 22.372 | −5.283 | 1.00 | 24.46 | B | C |
| ATOM | 8761 | CE1 | TYR | B | 16 | 78.223 | 23.015 | −6.512 | 1.00 | 23.58 | B | C |
| ATOM | 8763 | CZ | TYR | B | 16 | 78.436 | 24.378 | −6.576 | 1.00 | 23.84 | B | C |
| ATOM | 8764 | OH | TYR | B | 16 | 78.405 | 25.020 | −7.792 | 1.00 | 23.45 | B | O |
| ATOM | 8766 | CE2 | TYR | B | 16 | 78.679 | 25.100 | −5.422 | 1.00 | 24.10 | B | C |
| ATOM | 8768 | CD2 | TYR | B | 16 | 78.707 | 24.446 | −4.197 | 1.00 | 24.90 | B | C |
| ATOM | 8770 | C | TYR | B | 16 | 77.449 | 20.724 | −1.219 | 1.00 | 28.17 | B | C |
| ATOM | 8771 | O | TYR | B | 16 | 77.971 | 19.635 | −1.455 | 1.00 | 28.00 | B | O |
| ATOM | 8773 | N | ASP | B | 17 | 77.100 | 21.103 | 0.009 | 1.00 | 28.94 | B | N |
| ATOM | 8774 | CA | ASP | B | 17 | 77.182 | 20.189 | 1.153 | 1.00 | 29.33 | B | C |
| ATOM | 8776 | CB | ASP | B | 17 | 77.135 | 20.960 | 2.479 | 1.00 | 29.08 | B | C |
| ATOM | 8779 | CG | ASP | B | 17 | 78.279 | 21.954 | 2.627 | 1.00 | 28.02 | B | C |
| ATOM | 8780 | OD1 | ASP | B | 17 | 78.883 | 22.334 | 1.602 | 1.00 | 26.84 | B | O |
| ATOM | 8781 | OD2 | ASP | B | 17 | 78.570 | 22.364 | 3.770 | 1.00 | 26.76 | B | O |
| ATOM | 8782 | C | ASP | B | 17 | 76.026 | 19.188 | 1.087 | 1.00 | 30.23 | B | C |
| ATOM | 8783 | O | ASP | B | 17 | 76.202 | 17.997 | 1.355 | 1.00 | 30.34 | B | O |
| ATOM | 8785 | N | TYR | B | 18 | 74.847 | 19.697 | 0.728 | 1.00 | 31.12 | B | N |
| ATOM | 8786 | CA | TYR | B | 18 | 73.640 | 18.888 | 0.552 | 1.00 | 32.00 | B | C |
| ATOM | 8788 | CB | TYR | B | 18 | 72.432 | 19.814 | 0.349 | 1.00 | 32.50 | B | C |
| ATOM | 8791 | CG | TYR | B | 18 | 71.072 | 19.146 | 0.372 | 1.00 | 34.76 | B | C |
| ATOM | 8792 | CD1 | TYR | B | 18 | 70.211 | 19.321 | 1.455 | 1.00 | 37.40 | B | C |

TABLE 8-2-continued

Coordinates for L494P Structure

| ATOM | 8794 | CE1 | TYR | B | 18 | 68.955 | 18.727 | 1.479 | 1.00 | 38.40 | B | C |
|---|---|---|---|---|---|---|---|---|---|---|---|---|
| ATOM | 8796 | CZ | TYR | B | 18 | 68.545 | 17.952 | 0.408 | 1.00 | 38.58 | B | C |
| ATOM | 8797 | OH | TYR | B | 18 | 67.302 | 17.361 | 0.428 | 1.00 | 39.64 | B | O |
| ATOM | 8799 | CE2 | TYR | B | 18 | 69.378 | 17.770 | −0.683 | 1.00 | 37.47 | B | C |
| ATOM | 8801 | CD2 | TYR | B | 18 | 70.631 | 18.369 | −0.698 | 1.00 | 35.94 | B | C |
| ATOM | 8803 | C | TYR | B | 18 | 73.821 | 17.938 | −0.634 | 1.00 | 32.06 | B | C |
| ATOM | 8804 | O | TYR | B | 18 | 73.879 | 16.722 | −0.447 | 1.00 | 32.28 | B | O |
| ATOM | 8806 | N | LEU | B | 19 | 73.916 | 18.495 | −1.844 | 1.00 | 31.97 | B | N |
| ATOM | 8807 | CA | LEU | B | 19 | 74.291 | 17.725 | −3.033 | 1.00 | 31.81 | B | C |
| ATOM | 8809 | CB | LEU | B | 19 | 74.101 | 18.552 | −4.310 | 1.00 | 31.61 | B | C |
| ATOM | 8812 | CG | LEU | B | 19 | 72.673 | 18.884 | −4.747 | 1.00 | 31.60 | B | C |
| ATOM | 8814 | CD1 | LEU | B | 19 | 72.676 | 20.011 | −5.771 | 1.00 | 29.70 | B | C |
| ATOM | 8818 | CD2 | LEU | B | 19 | 71.975 | 17.650 | −5.307 | 1.00 | 32.90 | B | C |
| ATOM | 8822 | C | LEU | B | 19 | 75.755 | 17.334 | −2.900 | 1.00 | 32.11 | B | C |
| ATOM | 8823 | O | LEU | B | 19 | 76.478 | 17.920 | −2.100 | 1.00 | 32.07 | B | O |
| ATOM | 8825 | N | LEU | B | 20 | 76.188 | 16.346 | −3.679 | 1.00 | 32.38 | B | N |
| ATOM | 8826 | CA | LEU | B | 20 | 77.580 | 15.881 | −3.655 | 1.00 | 32.60 | B | C |
| ATOM | 8828 | CB | LEU | B | 20 | 78.543 | 17.016 | −4.048 | 1.00 | 32.67 | B | C |
| ATOM | 8831 | CG | LEU | B | 20 | 78.184 | 17.857 | −5.275 | 1.00 | 32.36 | B | C |
| ATOM | 8833 | CD1 | LEU | B | 20 | 79.247 | 18.915 | −5.510 | 1.00 | 31.31 | B | C |
| ATOM | 8837 | CD2 | LEU | B | 20 | 78.023 | 16.976 | −6.502 | 1.00 | 32.73 | B | C |
| ATOM | 8841 | C | LEU | B | 20 | 77.976 | 15.298 | −2.289 | 1.00 | 32.78 | B | C |
| ATOM | 8842 | O | LEU | B | 20 | 78.727 | 15.917 | −1.531 | 1.00 | 32.45 | B | O |
| ATOM | 8844 | N | SER | B | 21 | 77.462 | 14.108 | −1.984 | 1.00 | 33.27 | B | N |
| ATOM | 8845 | CA | SER | B | 21 | 77.803 | 13.407 | −0.740 | 1.00 | 33.68 | B | C |
| ATOM | 8847 | CB | SER | B | 21 | 76.696 | 13.592 | 0.307 | 1.00 | 33.73 | B | C |
| ATOM | 8850 | OG | SER | B | 21 | 75.453 | 13.090 | −0.153 | 1.00 | 33.56 | B | O |
| ATOM | 8852 | C | SER | B | 21 | 78.067 | 11.916 | −0.981 | 1.00 | 33.90 | B | C |
| ATOM | 8853 | O | SER | B | 21 | 77.611 | 11.344 | −1.976 | 1.00 | 33.89 | B | O |
| ATOM | 8855 | N | SER | B | 22 | 78.813 | 11.303 | −0.063 | 1.00 | 34.06 | B | N |
| ATOM | 8856 | CA | SER | B | 22 | 79.177 | 9.888 | −0.163 | 1.00 | 34.19 | B | C |
| ATOM | 8858 | CB | SER | B | 22 | 80.431 | 9.720 | −1.026 | 1.00 | 34.22 | B | C |
| ATOM | 8861 | OG | SER | B | 22 | 81.500 | 10.512 | −0.537 | 1.00 | 34.16 | B | O |
| ATOM | 8863 | C | SER | B | 22 | 79.417 | 9.282 | 1.218 | 1.00 | 34.24 | B | C |
| ATOM | 8864 | O | SER | B | 22 | 78.552 | 8.598 | 1.766 | 1.00 | 34.40 | B | O |
| ATOM | 8866 | N | ILE | B | 28 | 83.096 | 12.126 | −5.219 | 1.00 | 33.03 | B | N |
| ATOM | 8867 | CA | ILE | B | 28 | 82.293 | 13.341 | −5.130 | 1.00 | 33.17 | B | C |
| ATOM | 8869 | CB | ILE | B | 28 | 80.768 | 13.019 | −5.067 | 1.00 | 33.49 | B | C |
| ATOM | 8871 | CG1 | ILE | B | 28 | 80.431 | 11.736 | −5.840 | 1.00 | 33.77 | B | C |
| ATOM | 8874 | CD1 | ILE | B | 28 | 78.942 | 11.415 | −5.876 | 1.00 | 33.05 | B | C |
| ATOM | 8878 | CG2 | ILE | B | 28 | 79.953 | 14.191 | −5.610 | 1.00 | 33.81 | B | C |
| ATOM | 8882 | C | ILE | B | 28 | 82.693 | 14.165 | −3.897 | 1.00 | 33.01 | B | C |
| ATOM | 8883 | O | ILE | B | 28 | 81.856 | 14.845 | −3.299 | 1.00 | 33.03 | B | O |
| ATOM | 8885 | N | GLU | B | 29 | 83.977 | 14.116 | −3.537 | 1.00 | 32.83 | B | N |
| ATOM | 8886 | CA | GLU | B | 29 | 84.462 | 14.714 | −2.288 | 1.00 | 32.67 | B | C |
| ATOM | 8888 | CB | GLU | B | 29 | 85.136 | 13.647 | −1.429 | 1.00 | 32.76 | B | C |
| ATOM | 8891 | CG | GLU | B | 29 | 84.198 | 12.510 | −1.051 | 1.00 | 33.72 | B | C |
| ATOM | 8894 | CD | GLU | B | 29 | 84.786 | 11.574 | −0.012 | 1.00 | 35.62 | B | C |
| ATOM | 8895 | OE1 | GLU | B | 29 | 85.447 | 12.061 | 0.932 | 1.00 | 37.99 | B | O |
| ATOM | 8896 | OE2 | GLU | B | 29 | 84.579 | 10.348 | −0.136 | 1.00 | 35.42 | B | O |
| ATOM | 8897 | C | GLU | B | 29 | 85.407 | 15.895 | −2.516 | 1.00 | 32.29 | B | C |
| ATOM | 8898 | O | GLU | B | 29 | 85.093 | 17.019 | −2.125 | 1.00 | 32.51 | B | O |
| ATOM | 8900 | N | VAL | B | 30 | 86.559 | 15.650 | −3.138 | 1.00 | 31.62 | B | N |
| ATOM | 8901 | CA | VAL | B | 30 | 87.465 | 16.741 | −3.525 | 1.00 | 30.85 | B | C |
| ATOM | 8903 | CB | VAL | B | 30 | 88.830 | 16.207 | −4.027 | 1.00 | 30.72 | B | C |
| ATOM | 8905 | CG1 | VAL | B | 30 | 89.708 | 17.345 | −4.528 | 1.00 | 30.15 | B | C |
| ATOM | 8909 | CG2 | VAL | B | 30 | 89.538 | 15.439 | −2.917 | 1.00 | 30.01 | B | C |
| ATOM | 8913 | C | VAL | B | 30 | 86.787 | 17.605 | −4.600 | 1.00 | 30.37 | B | C |
| ATOM | 8914 | O | VAL | B | 30 | 87.082 | 18.791 | −4.739 | 1.00 | 30.28 | B | O |
| ATOM | 8916 | N | TYR | B | 31 | 85.877 | 16.984 | −5.346 | 1.00 | 29.78 | B | N |
| ATOM | 8917 | CA | TYR | B | 31 | 84.969 | 17.674 | −6.262 | 1.00 | 29.51 | B | C |
| ATOM | 8919 | CB | TYR | B | 31 | 84.111 | 16.625 | −6.984 | 1.00 | 29.72 | B | C |
| ATOM | 8922 | CG | TYR | B | 31 | 83.435 | 17.063 | −8.268 | 1.00 | 30.61 | B | C |
| ATOM | 8923 | CD1 | TYR | B | 31 | 84.175 | 17.308 | −9.424 | 1.00 | 30.75 | B | C |
| ATOM | 8925 | CE1 | TYR | B | 31 | 83.548 | 17.683 | −10.614 | 1.00 | 31.57 | B | C |
| ATOM | 8927 | CZ | TYR | B | 31 | 82.163 | 17.800 | −10.655 | 1.00 | 31.88 | B | C |
| ATOM | 8928 | OH | TYR | B | 31 | 81.530 | 18.173 | −11.822 | 1.00 | 30.54 | B | O |
| ATOM | 8930 | CE2 | TYR | B | 31 | 81.409 | 17.546 | −9.524 | 1.00 | 31.66 | B | C |
| ATOM | 8932 | CD2 | TYR | B | 31 | 82.045 | 17.173 | −8.342 | 1.00 | 32.07 | B | C |
| ATOM | 8934 | C | TYR | B | 31 | 84.076 | 18.654 | −5.490 | 1.00 | 28.96 | B | C |
| ATOM | 8935 | O | TYR | B | 31 | 83.852 | 19.780 | −5.933 | 1.00 | 29.21 | B | O |
| ATOM | 8937 | N | LYS | B | 32 | 83.574 | 18.211 | −4.336 | 1.00 | 28.11 | B | N |
| ATOM | 8938 | CA | LYS | B | 32 | 82.742 | 19.037 | −3.446 | 1.00 | 27.18 | B | C |
| ATOM | 8940 | CB | LYS | B | 32 | 82.091 | 18.152 | −2.368 | 1.00 | 27.40 | B | C |
| ATOM | 8943 | CG | LYS | B | 32 | 81.289 | 18.888 | −1.291 | 1.00 | 27.70 | B | C |
| ATOM | 8946 | CD | LYS | B | 32 | 81.011 | 17.982 | −0.088 | 1.00 | 28.13 | B | C |
| ATOM | 8949 | CE | LYS | B | 32 | 82.214 | 17.904 | 0.859 | 1.00 | 27.91 | B | C |
| ATOM | 8952 | NZ | LYS | B | 32 | 82.132 | 16.766 | 1.823 | 1.00 | 26.03 | B | N |

TABLE 8-2-continued

Coordinates for L494P Structure

| ATOM | 8956 | C | LYS | B | 32 | 83.549 | 20.159 | −2.788 | 1.00 | 26.03 | B | C |
| ATOM | 8957 | O | LYS | B | 32 | 83.099 | 21.305 | −2.740 | 1.00 | 25.99 | B | O |
| ATOM | 8959 | N | ASP | B | 33 | 84.731 | 19.820 | −2.274 | 1.00 | 24.80 | B | N |
| ATOM | 8960 | CA | ASP | B | 33 | 85.635 | 20.807 | −1.666 | 1.00 | 23.80 | B | C |
| ATOM | 8962 | CB | ASP | B | 33 | 86.882 | 20.123 | −1.073 | 1.00 | 23.97 | B | C |
| ATOM | 8965 | CG | ASP | B | 33 | 86.603 | 19.412 | 0.252 | 1.00 | 23.84 | B | C |
| ATOM | 8966 | OD1 | ASP | B | 33 | 85.444 | 19.021 | 0.506 | 1.00 | 24.89 | B | O |
| ATOM | 8967 | OD2 | ASP | B | 33 | 87.557 | 19.238 | 1.041 | 1.00 | 21.93 | B | O |
| ATOM | 8968 | C | ASP | B | 33 | 86.074 | 21.887 | −2.664 | 1.00 | 22.53 | B | C |
| ATOM | 8969 | O | ASP | B | 33 | 86.377 | 23.012 | −2.270 | 1.00 | 22.50 | B | O |
| ATOM | 8971 | N | LYS | B | 34 | 86.111 | 21.537 | −3.949 | 1.00 | 21.23 | B | N |
| ATOM | 8972 | CA | LYS | B | 34 | 86.498 | 22.479 | −4.999 | 1.00 | 20.16 | B | C |
| ATOM | 8974 | CB | LYS | B | 34 | 86.832 | 21.737 | −6.302 | 1.00 | 20.17 | B | C |
| ATOM | 8977 | CG | LYS | B | 34 | 88.013 | 22.319 | −7.068 | 1.00 | 21.10 | B | C |
| ATOM | 8980 | CD | LYS | B | 34 | 89.338 | 21.743 | −6.567 | 1.00 | 22.05 | B | C |
| ATOM | 8983 | CE | LYS | B | 34 | 90.538 | 22.487 | −7.142 | 1.00 | 22.40 | B | C |
| ATOM | 8986 | NZ | LYS | B | 34 | 90.519 | 22.547 | −8.633 | 1.00 | 22.69 | B | N |
| ATOM | 8990 | C | LYS | B | 34 | 85.379 | 23.488 | −5.250 | 1.00 | 19.08 | B | C |
| ATOM | 8991 | O | LYS | B | 34 | 85.622 | 24.695 | −5.277 | 1.00 | 19.11 | B | O |
| ATOM | 8993 | N | ALA | B | 35 | 84.158 | 22.979 | −5.424 | 1.00 | 17.76 | B | N |
| ATOM | 8994 | CA | ALA | B | 35 | 82.980 | 23.805 | −5.718 | 1.00 | 16.41 | B | C |
| ATOM | 8996 | CB | ALA | B | 35 | 81.743 | 22.927 | −5.847 | 1.00 | 16.25 | B | C |
| ATOM | 9000 | C | ALA | B | 35 | 82.745 | 24.878 | −4.663 | 1.00 | 15.50 | B | C |
| ATOM | 9001 | O | ALA | B | 35 | 82.464 | 26.028 | −4.996 | 1.00 | 15.11 | B | O |
| ATOM | 9003 | N | LYS | B | 36 | 82.857 | 24.491 | −3.395 | 1.00 | 14.95 | B | N |
| ATOM | 9004 | CA | LYS | B | 36 | 82.725 | 25.426 | −2.277 | 1.00 | 14.49 | B | C |
| ATOM | 9006 | CB | LYS | B | 36 | 82.866 | 24.686 | −0.941 | 1.00 | 14.64 | B | C |
| ATOM | 9009 | CG | LYS | B | 36 | 81.721 | 23.724 | −0.624 | 1.00 | 14.95 | B | C |
| ATOM | 9012 | CD | LYS | B | 36 | 82.093 | 22.732 | 0.482 | 1.00 | 14.25 | B | C |
| ATOM | 9015 | CE | LYS | B | 36 | 82.334 | 23.418 | 1.820 | 1.00 | 12.69 | B | C |
| ATOM | 9018 | NZ | LYS | B | 36 | 82.523 | 22.434 | 2.916 | 1.00 | 10.99 | B | N |
| ATOM | 9022 | C | LYS | B | 36 | 83.768 | 26.541 | −2.352 | 1.00 | 13.97 | B | C |
| ATOM | 9023 | O | LYS | B | 36 | 83.450 | 27.709 | −2.129 | 1.00 | 13.72 | B | O |
| ATOM | 9025 | N | LYS | B | 37 | 85.007 | 26.169 | −2.673 | 1.00 | 13.59 | B | N |
| ATOM | 9026 | CA | LYS | B | 37 | 86.120 | 27.119 | −2.735 | 1.00 | 13.44 | B | C |
| ATOM | 9028 | CB | LYS | B | 37 | 87.457 | 26.374 | −2.816 | 1.00 | 13.67 | B | C |
| ATOM | 9031 | CG | LYS | B | 37 | 88.681 | 27.282 | −2.729 | 1.00 | 15.27 | B | C |
| ATOM | 9034 | CD | LYS | B | 37 | 89.950 | 26.502 | −2.393 | 1.00 | 17.27 | B | C |
| ATOM | 9037 | CE | LYS | B | 37 | 91.135 | 27.436 | −2.137 | 1.00 | 17.81 | B | C |
| ATOM | 9040 | NZ | LYS | B | 37 | 91.454 | 28.302 | −3.312 | 1.00 | 17.07 | B | N |
| ATOM | 9044 | C | LYS | B | 37 | 86.000 | 28.100 | −3.902 | 1.00 | 12.83 | B | C |
| ATOM | 9045 | O | LYS | B | 37 | 86.455 | 29.241 | −3.800 | 1.00 | 12.97 | B | O |
| ATOM | 9047 | N | LEU | B | 38 | 85.398 | 27.655 | −5.003 | 1.00 | 12.14 | B | N |
| ATOM | 9048 | CA | LEU | B | 38 | 85.198 | 28.508 | −6.176 | 1.00 | 11.43 | B | C |
| ATOM | 9050 | CB | LEU | B | 38 | 85.176 | 27.669 | −7.458 | 1.00 | 11.06 | B | C |
| ATOM | 9053 | CG | LEU | B | 38 | 86.459 | 26.883 | −7.758 | 1.00 | 9.62 | B | C |
| ATOM | 9055 | CD1 | LEU | B | 38 | 86.310 | 26.057 | −9.026 | 1.00 | 6.76 | B | C |
| ATOM | 9059 | CD2 | LEU | B | 38 | 87.657 | 27.812 | −7.867 | 1.00 | 9.21 | B | C |
| ATOM | 9063 | C | LEU | B | 38 | 83.922 | 29.348 | −6.052 | 1.00 | 11.28 | B | C |
| ATOM | 9064 | O | LEU | B | 38 | 83.926 | 30.532 | −6.388 | 1.00 | 11.03 | B | O |
| ATOM | 9066 | N | GLU | B | 39 | 82.839 | 28.738 | −5.570 | 1.00 | 11.37 | B | N |
| ATOM | 9067 | CA | GLU | B | 39 | 81.605 | 29.472 | −5.271 | 1.00 | 11.49 | B | C |
| ATOM | 9069 | CB | GLU | B | 39 | 80.544 | 28.551 | −4.657 | 1.00 | 11.84 | B | C |
| ATOM | 9072 | CG | GLU | B | 39 | 79.181 | 29.229 | −4.440 | 1.00 | 12.44 | B | C |
| ATOM | 9075 | CD | GLU | B | 39 | 78.197 | 28.388 | −3.639 | 1.00 | 13.61 | B | C |
| ATOM | 9076 | OE1 | GLU | B | 39 | 78.576 | 27.309 | −3.140 | 1.00 | 14.31 | B | O |
| ATOM | 9077 | OE2 | GLU | B | 39 | 77.033 | 28.818 | −3.504 | 1.00 | 13.97 | B | O |
| ATOM | 9078 | C | GLU | B | 39 | 81.891 | 30.611 | −4.305 | 1.00 | 11.45 | B | C |
| ATOM | 9079 | O | GLU | B | 39 | 81.370 | 31.716 | −4.466 | 1.00 | 11.54 | B | O |
| ATOM | 9081 | N | ALA | B | 40 | 82.714 | 30.325 | −3.298 | 1.00 | 11.50 | B | N |
| ATOM | 9082 | CA | ALA | B | 40 | 83.120 | 31.321 | −2.312 | 1.00 | 11.48 | B | C |
| ATOM | 9084 | CB | ALA | B | 40 | 84.038 | 30.689 | −1.278 | 1.00 | 11.52 | B | C |
| ATOM | 9088 | C | ALA | B | 40 | 83.815 | 32.506 | −2.972 | 1.00 | 11.57 | B | C |
| ATOM | 9089 | O | ALA | B | 40 | 83.515 | 33.661 | −2.665 | 1.00 | 11.32 | B | O |
| ATOM | 9091 | N | GLU | B | 41 | 84.734 | 32.210 | −3.886 | 1.00 | 11.81 | B | N |
| ATOM | 9092 | CA | GLU | B | 41 | 85.501 | 33.244 | −4.580 | 1.00 | 12.06 | B | C |
| ATOM | 9094 | CB | GLU | B | 41 | 86.602 | 32.610 | −5.437 | 1.00 | 12.41 | B | C |
| ATOM | 9097 | CG | GLU | B | 41 | 87.698 | 33.583 | −5.862 | 1.00 | 13.10 | B | C |
| ATOM | 9100 | CD | GLU | B | 41 | 88.924 | 32.889 | −6.430 | 1.00 | 13.35 | B | C |
| ATOM | 9101 | OE1 | GLU | B | 41 | 89.231 | 31.755 | −6.004 | 1.00 | 13.61 | B | O |
| ATOM | 9102 | OE2 | GLU | B | 41 | 89.589 | 33.486 | −7.301 | 1.00 | 13.54 | B | O |
| ATOM | 9103 | C | GLU | B | 41 | 84.596 | 34.128 | −5.436 | 1.00 | 11.69 | B | C |
| ATOM | 9104 | O | GLU | B | 41 | 84.749 | 35.346 | −5.452 | 1.00 | 11.44 | B | O |
| ATOM | 9106 | N | VAL | B | 42 | 83.651 | 33.509 | −6.135 | 1.00 | 11.70 | B | N |
| ATOM | 9107 | CA | VAL | B | 42 | 82.672 | 34.251 | −6.922 | 1.00 | 11.83 | B | C |
| ATOM | 9109 | CB | VAL | B | 42 | 81.728 | 33.305 | −7.695 | 1.00 | 11.85 | B | C |
| ATOM | 9111 | CG1 | VAL | B | 42 | 80.650 | 34.095 | −8.419 | 1.00 | 12.24 | B | C |
| ATOM | 9115 | CG2 | VAL | B | 42 | 82.513 | 32.460 | −8.682 | 1.00 | 11.42 | B | C |

TABLE 8-2-continued

Coordinates for L494P Structure

| ATOM | 9119 | C | VAL | B | 42 | 81.849 | 35.162 | −6.015 | 1.00 | 12.05 | B | C |
|---|---|---|---|---|---|---|---|---|---|---|---|---|
| ATOM | 9120 | O | VAL | B | 42 | 81.692 | 36.348 | −6.299 | 1.00 | 11.93 | B | O |
| ATOM | 9122 | N | ARG | B | 43 | 81.343 | 34.602 | −4.918 | 1.00 | 12.55 | B | N |
| ATOM | 9123 | CA | ARG | B | 43 | 80.539 | 35.356 | −3.949 | 1.00 | 13.01 | B | C |
| ATOM | 9125 | CB | ARG | B | 43 | 80.173 | 34.467 | −2.748 | 1.00 | 13.46 | B | C |
| ATOM | 9128 | CG | ARG | B | 43 | 79.342 | 35.153 | −1.654 | 1.00 | 14.25 | B | C |
| ATOM | 9131 | CD | ARG | B | 43 | 80.220 | 35.887 | −0.635 | 1.00 | 14.13 | B | C |
| ATOM | 9134 | NE | ARG | B | 43 | 79.457 | 36.448 | 0.477 | 1.00 | 13.56 | B | N |
| ATOM | 9136 | CZ | ARG | B | 43 | 79.951 | 37.291 | 1.382 | 1.00 | 13.26 | B | C |
| ATOM | 9137 | NH1 | ARG | B | 43 | 79.172 | 37.747 | 2.356 | 1.00 | 13.32 | B | N |
| ATOM | 9140 | NH2 | ARG | B | 43 | 81.218 | 37.687 | 1.319 | 1.00 | 13.61 | B | N |
| ATOM | 9143 | C | ARG | B | 43 | 81.251 | 36.623 | −3.474 | 1.00 | 12.51 | B | C |
| ATOM | 9144 | O | ARG | B | 43 | 80.632 | 37.683 | −3.361 | 1.00 | 12.05 | B | O |
| ATOM | 9146 | N | ARG | B | 44 | 82.545 | 36.504 | −3.187 | 1.00 | 12.38 | B | N |
| ATOM | 9147 | CA | ARG | B | 44 | 83.347 | 37.648 | −2.750 | 1.00 | 12.46 | B | C |
| ATOM | 9149 | CB | ARG | B | 44 | 84.807 | 37.236 | −2.537 | 1.00 | 12.38 | B | C |
| ATOM | 9152 | CG | ARG | B | 44 | 85.734 | 38.380 | −2.138 | 1.00 | 11.90 | B | C |
| ATOM | 9155 | CD | ARG | B | 44 | 87.112 | 37.874 | −1.750 | 1.00 | 10.93 | B | C |
| ATOM | 9158 | NE | ARG | B | 44 | 87.798 | 37.229 | −2.866 | 1.00 | 10.06 | B | N |
| ATOM | 9160 | CZ | ARG | B | 44 | 89.003 | 36.667 | −2.788 | 1.00 | 10.80 | B | C |
| ATOM | 9161 | NH1 | ARG | B | 44 | 89.679 | 36.664 | −1.643 | 1.00 | 12.55 | B | N |
| ATOM | 9164 | NH2 | ARG | B | 44 | 89.539 | 36.103 | −3.863 | 1.00 | 10.95 | B | N |
| ATOM | 9167 | C | ARG | B | 44 | 83.278 | 38.788 | −3.758 | 1.00 | 12.62 | B | C |
| ATOM | 9168 | O | ARG | B | 44 | 83.176 | 39.953 | −3.375 | 1.00 | 12.54 | B | O |
| ATOM | 9170 | N | GLU | B | 45 | 83.332 | 38.446 | −5.042 | 1.00 | 12.86 | B | N |
| ATOM | 9171 | CA | GLU | B | 45 | 83.303 | 39.448 | −6.102 | 1.00 | 13.14 | B | C |
| ATOM | 9173 | CB | GLU | B | 45 | 83.716 | 38.840 | −7.449 | 1.00 | 13.40 | B | C |
| ATOM | 9176 | CG | GLU | B | 45 | 85.094 | 38.176 | −7.467 | 1.00 | 13.15 | B | C |
| ATOM | 9179 | CD | GLU | B | 45 | 86.197 | 39.066 | −6.930 | 1.00 | 12.52 | B | C |
| ATOM | 9180 | OE1 | GLU | B | 45 | 86.171 | 40.286 | −7.197 | 1.00 | 11.65 | B | O |
| ATOM | 9181 | OE2 | GLU | B | 45 | 87.094 | 38.542 | −6.239 | 1.00 | 13.46 | B | O |
| ATOM | 9182 | C | GLU | B | 45 | 81.930 | 40.100 | −6.227 | 1.00 | 13.07 | B | C |
| ATOM | 9183 | O | GLU | B | 45 | 81.837 | 41.308 | −6.424 | 1.00 | 13.24 | B | O |
| ATOM | 9185 | N | ILE | B | 46 | 80.870 | 39.308 | −6.100 | 1.00 | 13.28 | B | N |
| ATOM | 9186 | CA | ILE | B | 46 | 79.505 | 39.831 | −6.217 | 1.00 | 13.40 | B | C |
| ATOM | 9188 | CB | ILE | B | 46 | 78.450 | 38.696 | −6.262 | 1.00 | 13.25 | B | C |
| ATOM | 9190 | CG1 | ILE | B | 46 | 78.670 | 37.801 | −7.485 | 1.00 | 12.31 | B | C |
| ATOM | 9193 | CD1 | ILE | B | 46 | 77.743 | 36.617 | −7.546 | 1.00 | 11.98 | B | C |
| ATOM | 9197 | CG2 | ILE | B | 46 | 77.044 | 39.270 | −6.318 | 1.00 | 12.44 | B | C |
| ATOM | 9201 | C | ILE | B | 46 | 79.179 | 40.805 | −5.078 | 1.00 | 13.95 | B | C |
| ATOM | 9202 | O | ILE | B | 46 | 78.401 | 41.740 | −5.269 | 1.00 | 13.95 | B | O |
| ATOM | 9204 | N | ASN | B | 47 | 79.788 | 40.589 | −3.910 | 1.00 | 14.71 | B | N |
| ATOM | 9205 | CA | ASN | B | 47 | 79.621 | 41.476 | −2.750 | 1.00 | 15.06 | B | C |
| ATOM | 9207 | CB | ASN | B | 47 | 79.428 | 40.644 | −1.485 | 1.00 | 14.81 | B | C |
| ATOM | 9210 | CG | ASN | B | 47 | 78.236 | 39.728 | −1.579 | 1.00 | 15.52 | B | C |
| ATOM | 9211 | OD1 | ASN | B | 47 | 77.091 | 40.181 | −1.600 | 1.00 | 15.77 | B | O |
| ATOM | 9212 | ND2 | ASN | B | 47 | 78.495 | 38.429 | −1.650 | 1.00 | 17.54 | B | N |
| ATOM | 9215 | C | ASN | B | 47 | 80.779 | 42.460 | −2.552 | 1.00 | 15.58 | B | C |
| ATOM | 9216 | O | ASN | B | 47 | 80.888 | 43.093 | −1.498 | 1.00 | 16.00 | B | O |
| ATOM | 9218 | N | ASN | B | 48 | 81.637 | 42.584 | −3.563 | 1.00 | 15.89 | B | N |
| ATOM | 9219 | CA | ASN | B | 48 | 82.745 | 43.532 | −3.535 | 1.00 | 16.06 | B | C |
| ATOM | 9221 | CB | ASN | B | 48 | 83.744 | 43.202 | −4.650 | 1.00 | 15.90 | B | C |
| ATOM | 9224 | CG | ASN | B | 48 | 84.925 | 44.150 | −4.685 | 1.00 | 15.28 | B | C |
| ATOM | 9225 | OD1 | ASN | B | 48 | 85.262 | 44.783 | −3.686 | 1.00 | 15.43 | B | O |
| ATOM | 9226 | ND2 | ASN | B | 48 | 85.566 | 44.248 | −5.843 | 1.00 | 15.13 | B | N |
| ATOM | 9229 | C | ASN | B | 48 | 82.214 | 44.951 | −3.701 | 1.00 | 16.79 | B | C |
| ATOM | 9230 | O | ASN | B | 48 | 81.838 | 45.349 | −4.806 | 1.00 | 17.02 | B | O |
| ATOM | 9232 | N | GLU | B | 49 | 82.188 | 45.710 | −2.606 | 1.00 | 17.49 | B | N |
| ATOM | 9233 | CA | GLU | B | 49 | 81.592 | 47.053 | −2.612 | 1.00 | 18.37 | B | C |
| ATOM | 9235 | CB | GLU | B | 49 | 81.183 | 47.467 | −1.191 | 1.00 | 18.78 | B | C |
| ATOM | 9238 | CG | GLU | B | 49 | 80.125 | 46.546 | −0.564 | 1.00 | 20.96 | B | C |
| ATOM | 9241 | CD | GLU | B | 49 | 79.341 | 47.187 | 0.583 | 1.00 | 23.15 | B | C |
| ATOM | 9242 | OE1 | GLU | B | 49 | 78.832 | 46.437 | 1.443 | 1.00 | 23.41 | B | O |
| ATOM | 9243 | OE2 | GLU | B | 49 | 79.220 | 48.432 | 0.626 | 1.00 | 25.12 | B | O |
| ATOM | 9244 | C | GLU | B | 49 | 82.484 | 48.132 | −3.245 | 1.00 | 18.48 | B | C |
| ATOM | 9245 | O | GLU | B | 49 | 82.045 | 49.270 | −3.411 | 1.00 | 18.18 | B | O |
| ATOM | 9247 | N | LYS | B | 50 | 83.721 | 47.776 | −3.598 | 1.00 | 18.96 | B | N |
| ATOM | 9248 | CA | LYS | B | 50 | 84.643 | 48.694 | −4.277 | 1.00 | 19.36 | B | C |
| ATOM | 9250 | CB | LYS | B | 50 | 86.002 | 48.704 | −3.569 | 1.00 | 19.39 | B | C |
| ATOM | 9253 | CG | LYS | B | 50 | 85.938 | 48.749 | −2.054 | 1.00 | 19.24 | B | C |
| ATOM | 9256 | CD | LYS | B | 50 | 87.314 | 49.008 | −1.455 | 1.00 | 19.55 | B | C |
| ATOM | 9259 | CE | LYS | B | 50 | 87.442 | 48.400 | −0.069 | 1.00 | 19.73 | B | C |
| ATOM | 9262 | NZ | LYS | B | 50 | 86.280 | 48.740 | 0.792 | 1.00 | 18.94 | B | N |
| ATOM | 9266 | C | LYS | B | 50 | 84.855 | 48.325 | −5.751 | 1.00 | 19.85 | B | C |
| ATOM | 9267 | O | LYS | B | 50 | 85.860 | 48.711 | −6.350 | 1.00 | 19.64 | B | O |
| ATOM | 9269 | N | ALA | B | 51 | 83.914 | 47.585 | −6.335 | 1.00 | 20.78 | B | N |
| ATOM | 9270 | CA | ALA | B | 51 | 84.036 | 47.130 | −7.721 | 1.00 | 21.39 | B | C |
| ATOM | 9272 | CB | ALA | B | 51 | 83.225 | 45.860 | −7.932 | 1.00 | 21.43 | B | C |

TABLE 8-2-continued

Coordinates for L494P Structure

| ATOM | 9276 | C | ALA | B | 51 | 83.580 | 48.213 | −8.693 | 1.00 | 21.95 | B | C |
|---|---|---|---|---|---|---|---|---|---|---|---|---|
| ATOM | 9277 | O | ALA | B | 51 | 82.643 | 48.956 | −8.402 | 1.00 | 21.95 | B | O |
| ATOM | 9279 | N | GLU | B | 52 | 84.248 | 48.298 | −9.842 | 1.00 | 22.93 | B | N |
| ATOM | 9280 | CA | GLU | B | 52 | 83.864 | 49.240 | −10.899 | 1.00 | 23.64 | B | C |
| ATOM | 9282 | CB | GLU | B | 52 | 84.892 | 49.243 | −12.037 | 1.00 | 23.82 | B | C |
| ATOM | 9285 | CG | GLU | B | 52 | 86.280 | 49.747 | −11.642 | 1.00 | 24.65 | B | C |
| ATOM | 9288 | CD | GLU | B | 52 | 86.415 | 51.257 | −11.745 | 1.00 | 26.37 | B | C |
| ATOM | 9289 | OE1 | GLU | B | 52 | 86.465 | 51.778 | −12.880 | 1.00 | 27.93 | B | O |
| ATOM | 9290 | OE2 | GLU | B | 52 | 86.486 | 51.924 | −10.691 | 1.00 | 27.36 | B | O |
| ATOM | 9291 | C | GLU | B | 52 | 82.498 | 48.824 | −11.427 | 1.00 | 23.98 | B | C |
| ATOM | 9292 | O | GLU | B | 52 | 82.289 | 47.653 | −11.752 | 1.00 | 24.25 | B | O |
| ATOM | 9294 | N | PHE | B | 53 | 81.575 | 49.780 | −11.505 | 1.00 | 24.11 | B | N |
| ATOM | 9295 | CA | PHE | B | 53 | 80.165 | 49.475 | −11.772 | 1.00 | 24.15 | B | C |
| ATOM | 9297 | CB | PHE | B | 53 | 79.315 | 50.749 | −11.715 | 1.00 | 24.51 | B | C |
| ATOM | 9300 | CG | PHE | B | 53 | 79.155 | 51.313 | −10.324 | 1.00 | 27.60 | B | C |
| ATOM | 9301 | CD1 | PHE | B | 53 | 78.559 | 50.556 | −9.315 | 1.00 | 29.48 | B | C |
| ATOM | 9303 | CE1 | PHE | B | 53 | 78.400 | 51.071 | −8.028 | 1.00 | 30.36 | B | C |
| ATOM | 9305 | CZ | PHE | B | 53 | 78.838 | 52.361 | −7.739 | 1.00 | 31.69 | B | C |
| ATOM | 9307 | CE2 | PHE | B | 53 | 79.433 | 53.131 | −8.739 | 1.00 | 31.11 | B | C |
| ATOM | 9309 | CD2 | PHE | B | 53 | 79.586 | 52.606 | −10.024 | 1.00 | 30.30 | B | C |
| ATOM | 9311 | C | PHE | B | 53 | 79.933 | 48.739 | −13.095 | 1.00 | 23.44 | B | C |
| ATOM | 9312 | O | PHE | B | 53 | 79.059 | 47.874 | −13.177 | 1.00 | 23.35 | B | O |
| ATOM | 9314 | N | LEU | B | 54 | 80.715 | 49.073 | −14.120 | 1.00 | 22.51 | B | N |
| ATOM | 9315 | CA | LEU | B | 54 | 80.622 | 48.377 | −15.403 | 1.00 | 21.75 | B | C |
| ATOM | 9317 | CB | LEU | B | 54 | 81.416 | 49.117 | −16.487 | 1.00 | 21.53 | B | C |
| ATOM | 9320 | CG | LEU | B | 54 | 81.023 | 48.812 | −17.936 | 1.00 | 21.05 | B | C |
| ATOM | 9322 | CD1 | LEU | B | 54 | 79.602 | 49.279 | −18.218 | 1.00 | 20.70 | B | C |
| ATOM | 9326 | CD2 | LEU | B | 54 | 81.997 | 49.461 | −18.908 | 1.00 | 19.68 | B | C |
| ATOM | 9330 | C | LEU | B | 54 | 81.110 | 46.928 | −15.267 | 1.00 | 21.34 | B | C |
| ATOM | 9331 | O | LEU | B | 54 | 80.503 | 46.011 | −15.821 | 1.00 | 21.37 | B | O |
| ATOM | 9333 | N | THR | B | 55 | 82.195 | 46.731 | −14.517 | 1.00 | 20.71 | B | N |
| ATOM | 9334 | CA | THR | B | 55 | 82.723 | 45.391 | −14.241 | 1.00 | 20.02 | B | C |
| ATOM | 9336 | CB | THR | B | 55 | 84.090 | 45.459 | −13.528 | 1.00 | 19.67 | B | C |
| ATOM | 9338 | OG1 | THR | B | 55 | 84.974 | 46.311 | −14.264 | 1.00 | 18.17 | B | O |
| ATOM | 9340 | CG2 | THR | B | 55 | 84.706 | 44.071 | −13.409 | 1.00 | 19.26 | B | C |
| ATOM | 9344 | C | THR | B | 55 | 81.763 | 44.569 | −13.379 | 1.00 | 19.89 | B | C |
| ATOM | 9345 | O | THR | B | 55 | 81.651 | 43.353 | −13.550 | 1.00 | 19.81 | B | O |
| ATOM | 9347 | N | LEU | B | 56 | 81.077 | 45.242 | −12.456 | 1.00 | 19.76 | B | N |
| ATOM | 9348 | CA | LEU | B | 56 | 80.128 | 44.592 | −11.552 | 1.00 | 19.79 | B | C |
| ATOM | 9350 | CB | LEU | B | 56 | 79.630 | 45.591 | −10.500 | 1.00 | 19.92 | B | C |
| ATOM | 9353 | CG | LEU | B | 56 | 78.637 | 45.086 | −9.449 | 1.00 | 20.73 | B | C |
| ATOM | 9355 | CD1 | LEU | B | 56 | 79.195 | 43.878 | −8.703 | 1.00 | 21.48 | B | C |
| ATOM | 9359 | CD2 | LEU | B | 56 | 78.277 | 46.207 | −8.476 | 1.00 | 21.77 | B | C |
| ATOM | 9363 | C | LEU | B | 56 | 78.941 | 44.014 | −12.316 | 1.00 | 19.43 | B | C |
| ATOM | 9364 | O | LEU | B | 56 | 78.580 | 42.850 | −12.136 | 1.00 | 19.59 | B | O |
| ATOM | 9366 | N | LEU | B | 57 | 78.341 | 44.840 | −13.167 | 1.00 | 18.85 | B | N |
| ATOM | 9367 | CA | LEU | B | 57 | 77.219 | 44.412 | −13.997 | 1.00 | 18.27 | B | C |
| ATOM | 9369 | CB | LEU | B | 57 | 76.672 | 45.590 | −14.808 | 1.00 | 18.24 | B | C |
| ATOM | 9372 | CG | LEU | B | 57 | 76.112 | 46.770 | −14.008 | 1.00 | 18.19 | B | C |
| ATOM | 9374 | CD1 | LEU | B | 57 | 75.894 | 47.973 | −14.912 | 1.00 | 17.75 | B | C |
| ATOM | 9378 | CD2 | LEU | B | 57 | 74.824 | 46.382 | −13.297 | 1.00 | 18.37 | B | C |
| ATOM | 9382 | C | LEU | B | 57 | 77.649 | 43.289 | −14.938 | 1.00 | 17.71 | B | C |
| ATOM | 9383 | O | LEU | B | 57 | 76.922 | 42.311 | −15.114 | 1.00 | 17.47 | B | O |
| ATOM | 9385 | N | GLU | B | 58 | 78.836 | 43.435 | −15.527 | 1.00 | 17.20 | B | N |
| ATOM | 9386 | CA | GLU | B | 58 | 79.386 | 42.429 | −16.440 | 1.00 | 16.77 | B | C |
| ATOM | 9388 | CB | GLU | B | 58 | 80.668 | 42.942 | −17.110 | 1.00 | 16.93 | B | C |
| ATOM | 9391 | CG | GLU | B | 58 | 80.413 | 43.906 | −18.269 | 1.00 | 18.82 | B | C |
| ATOM | 9394 | CD | GLU | B | 58 | 81.688 | 44.351 | −18.983 | 1.00 | 20.53 | B | C |
| ATOM | 9395 | OE1 | GLU | B | 58 | 82.721 | 43.653 | −18.876 | 1.00 | 22.18 | B | O |
| ATOM | 9396 | OE2 | GLU | B | 58 | 81.652 | 45.400 | −19.662 | 1.00 | 20.87 | B | O |
| ATOM | 9397 | C | GLU | B | 58 | 79.655 | 41.080 | −15.764 | 1.00 | 16.01 | B | C |
| ATOM | 9398 | O | GLU | B | 58 | 79.540 | 40.038 | −16.409 | 1.00 | 16.08 | B | O |
| ATOM | 9400 | N | LEU | B | 59 | 80.011 | 41.095 | −14.479 | 1.00 | 14.97 | B | N |
| ATOM | 9401 | CA | LEU | B | 59 | 80.244 | 39.849 | −13.740 | 1.00 | 13.89 | B | C |
| ATOM | 9403 | CB | LEU | B | 59 | 80.915 | 40.117 | −12.387 | 1.00 | 13.50 | B | C |
| ATOM | 9406 | CG | LEU | B | 59 | 81.070 | 38.917 | −11.439 | 1.00 | 11.95 | B | C |
| ATOM | 9408 | CD1 | LEU | B | 59 | 81.657 | 37.699 | −12.142 | 1.00 | 8.96 | B | C |
| ATOM | 9412 | CD2 | LEU | B | 59 | 81.921 | 39.295 | −10.243 | 1.00 | 10.77 | B | C |
| ATOM | 9416 | C | LEU | B | 59 | 78.936 | 39.085 | −13.541 | 1.00 | 13.42 | B | C |
| ATOM | 9417 | O | LEU | B | 59 | 78.852 | 37.904 | −13.877 | 1.00 | 13.89 | B | O |
| ATOM | 9419 | N | ILE | B | 60 | 77.924 | 39.761 | −12.999 | 1.00 | 12.45 | B | N |
| ATOM | 9420 | CA | ILE | B | 60 | 76.607 | 39.148 | −12.804 | 1.00 | 11.69 | B | C |
| ATOM | 9422 | CB | ILE | B | 60 | 75.533 | 40.169 | −12.356 | 1.00 | 11.55 | B | C |
| ATOM | 9424 | CG1 | ILE | B | 60 | 75.861 | 40.758 | −10.982 | 1.00 | 11.14 | B | C |
| ATOM | 9427 | CD1 | ILE | B | 60 | 74.840 | 41.771 | −10.494 | 1.00 | 9.21 | B | C |
| ATOM | 9431 | CG2 | ILE | B | 60 | 74.161 | 39.507 | −12.311 | 1.00 | 10.73 | B | C |
| ATOM | 9435 | C | ILE | B | 60 | 76.139 | 38.535 | −14.114 | 1.00 | 11.60 | B | C |
| ATOM | 9436 | O | ILE | B | 60 | 75.774 | 37.362 | −14.167 | 1.00 | 11.32 | B | O |

TABLE 8-2-continued

Coordinates for L494P Structure

| ATOM | 9438 | N | ASP | B | 61 | 76.168 | 39.348 | −15.168 | 1.00 | 11.70 | B | N |
|---|---|---|---|---|---|---|---|---|---|---|---|---|
| ATOM | 9439 | CA | ASP | B | 61 | 75.739 | 38.927 | −16.496 | 1.00 | 11.67 | B | C |
| ATOM | 9441 | CB | ASP | B | 61 | 75.996 | 40.041 | −17.517 | 1.00 | 11.58 | B | C |
| ATOM | 9444 | CG | ASP | B | 61 | 75.344 | 39.772 | −18.866 | 1.00 | 11.78 | B | C |
| ATOM | 9445 | OD1 | ASP | B | 61 | 74.350 | 39.015 | −18.922 | 1.00 | 9.94 | B | O |
| ATOM | 9446 | OD2 | ASP | B | 61 | 75.826 | 40.332 | −19.874 | 1.00 | 11.86 | B | O |
| ATOM | 9447 | C | ASP | B | 61 | 76.452 | 37.647 | −16.914 | 1.00 | 11.90 | B | C |
| ATOM | 9448 | O | ASP | B | 61 | 75.823 | 36.740 | −17.444 | 1.00 | 11.79 | B | O |
| ATOM | 9450 | N | ASN | B | 62 | 77.756 | 37.572 | −16.660 | 1.00 | 12.59 | B | N |
| ATOM | 9451 | CA | ASN | B | 62 | 78.515 | 36.345 | −16.917 | 1.00 | 13.39 | B | C |
| ATOM | 9453 | CB | ASN | B | 62 | 80.020 | 36.574 | −16.725 | 1.00 | 13.48 | B | C |
| ATOM | 9456 | CG | ASN | B | 62 | 80.590 | 37.589 | −17.699 | 1.00 | 13.93 | B | C |
| ATOM | 9457 | OD1 | ASN | B | 62 | 80.077 | 37.768 | −18.803 | 1.00 | 13.75 | B | O |
| ATOM | 9458 | ND2 | ASN | B | 62 | 81.660 | 38.263 | −17.290 | 1.00 | 16.15 | B | N |
| ATOM | 9461 | C | ASN | B | 62 | 78.049 | 35.192 | −16.024 | 1.00 | 13.60 | B | C |
| ATOM | 9462 | O | ASN | B | 62 | 77.842 | 34.076 | −16.500 | 1.00 | 13.11 | B | O |
| ATOM | 9464 | N | VAL | B | 63 | 77.873 | 35.473 | −14.735 | 1.00 | 13.89 | B | N |
| ATOM | 9465 | CA | VAL | B | 63 | 77.447 | 34.458 | −13.773 | 1.00 | 14.49 | B | C |
| ATOM | 9467 | CB | VAL | B | 63 | 77.327 | 35.041 | −12.349 | 1.00 | 14.33 | B | C |
| ATOM | 9469 | CG1 | VAL | B | 63 | 76.681 | 34.034 | −11.410 | 1.00 | 14.92 | B | C |
| ATOM | 9473 | CG2 | VAL | B | 63 | 78.693 | 35.452 | −11.829 | 1.00 | 14.73 | B | C |
| ATOM | 9477 | C | VAL | B | 63 | 76.113 | 33.822 | −14.170 | 1.00 | 15.20 | B | C |
| ATOM | 9478 | O | VAL | B | 63 | 75.986 | 32.596 | −14.188 | 1.00 | 15.27 | B | O |
| ATOM | 9480 | N | GLN | B | 64 | 75.129 | 34.658 | −14.490 | 1.00 | 15.80 | B | N |
| ATOM | 9481 | CA | GLN | B | 64 | 73.799 | 34.178 | −14.875 | 1.00 | 16.00 | B | C |
| ATOM | 9483 | CB | GLN | B | 64 | 72.811 | 35.340 | −14.962 | 1.00 | 16.04 | B | C |
| ATOM | 9486 | CG | GLN | B | 64 | 72.518 | 36.000 | −13.630 | 1.00 | 16.27 | B | C |
| ATOM | 9489 | CD | GLN | B | 64 | 71.616 | 37.209 | −13.762 | 1.00 | 16.56 | B | C |
| ATOM | 9490 | OE1 | GLN | B | 64 | 70.631 | 37.339 | −13.035 | 1.00 | 19.83 | B | O |
| ATOM | 9491 | NE2 | GLN | B | 64 | 71.946 | 38.102 | −14.693 | 1.00 | 12.79 | B | N |
| ATOM | 9494 | C | GLN | B | 64 | 73.825 | 33.441 | −16.207 | 1.00 | 16.02 | B | C |
| ATOM | 9495 | O | GLN | B | 64 | 73.141 | 32.434 | −16.375 | 1.00 | 16.54 | B | O |
| ATOM | 9497 | N | ARG | B | 65 | 74.612 | 33.950 | −17.150 | 1.00 | 16.05 | B | N |
| ATOM | 9498 | CA | ARG | B | 65 | 74.721 | 33.338 | −18.473 | 1.00 | 16.17 | B | C |
| ATOM | 9500 | CB | ARG | B | 65 | 75.346 | 34.315 | −19.473 | 1.00 | 16.27 | B | C |
| ATOM | 9503 | CG | ARG | B | 65 | 74.403 | 35.458 | −19.834 | 1.00 | 18.62 | B | C |
| ATOM | 9506 | CD | ARG | B | 65 | 74.945 | 36.347 | −20.935 | 1.00 | 19.52 | B | C |
| ATOM | 9509 | NE | ARG | B | 65 | 74.972 | 35.651 | −22.219 | 1.00 | 21.90 | B | N |
| ATOM | 9511 | CZ | ARG | B | 65 | 75.080 | 36.245 | −23.405 | 1.00 | 25.25 | B | C |
| ATOM | 9512 | NH1 | ARG | B | 65 | 75.161 | 37.571 | −23.503 | 1.00 | 26.87 | B | N |
| ATOM | 9515 | NH2 | ARG | B | 65 | 75.099 | 35.504 | −24.509 | 1.00 | 26.60 | B | N |
| ATOM | 9518 | C | ARG | B | 65 | 75.494 | 32.020 | −18.451 | 1.00 | 15.57 | B | C |
| ATOM | 9519 | O | ARG | B | 65 | 75.292 | 31.179 | −19.322 | 1.00 | 16.17 | B | O |
| ATOM | 9521 | N | LEU | B | 66 | 76.361 | 31.838 | −17.454 | 1.00 | 14.50 | B | N |
| ATOM | 9522 | CA | LEU | B | 66 | 77.091 | 30.575 | −17.275 | 1.00 | 13.62 | B | C |
| ATOM | 9524 | CB | LEU | B | 66 | 78.445 | 30.836 | −16.606 | 1.00 | 13.45 | B | C |
| ATOM | 9527 | CG | LEU | B | 66 | 79.441 | 31.662 | −17.429 | 1.00 | 12.05 | B | C |
| ATOM | 9529 | CD1 | LEU | B | 66 | 80.499 | 32.279 | −16.532 | 1.00 | 11.23 | B | C |
| ATOM | 9533 | CD2 | LEU | B | 66 | 80.081 | 30.824 | −18.518 | 1.00 | 9.81 | B | C |
| ATOM | 9537 | C | LEU | B | 66 | 76.283 | 29.546 | −16.468 | 1.00 | 13.36 | B | C |
| ATOM | 9538 | O | LEU | B | 66 | 76.797 | 28.480 | −16.116 | 1.00 | 12.46 | B | O |
| ATOM | 9540 | N | GLY | B | 67 | 75.024 | 29.880 | −16.175 | 1.00 | 13.57 | B | N |
| ATOM | 9541 | CA | GLY | B | 67 | 74.089 | 28.970 | −15.518 | 1.00 | 13.40 | B | C |
| ATOM | 9544 | C | GLY | B | 67 | 74.004 | 29.124 | −14.009 | 1.00 | 13.53 | B | C |
| ATOM | 9545 | O | GLY | B | 67 | 73.192 | 28.456 | −13.367 | 1.00 | 13.68 | B | O |
| ATOM | 9547 | N | LEU | B | 68 | 74.812 | 30.020 | −13.442 | 1.00 | 13.50 | B | N |
| ATOM | 9548 | CA | LEU | B | 68 | 75.000 | 30.092 | −11.988 | 1.00 | 13.46 | B | C |
| ATOM | 9550 | CB | LEU | B | 68 | 76.484 | 30.330 | −11.678 | 1.00 | 13.16 | B | C |
| ATOM | 9553 | CG | LEU | B | 68 | 77.467 | 29.318 | −12.274 | 1.00 | 12.36 | B | C |
| ATOM | 9555 | CD1 | LEU | B | 68 | 78.899 | 29.699 | −11.919 | 1.00 | 11.43 | B | C |
| ATOM | 9559 | CD2 | LEU | B | 68 | 77.152 | 27.905 | −11.803 | 1.00 | 9.64 | B | C |
| ATOM | 9563 | C | LEU | B | 68 | 74.149 | 31.150 | −11.266 | 1.00 | 13.59 | B | C |
| ATOM | 9564 | O | LEU | B | 68 | 74.430 | 31.485 | −10.117 | 1.00 | 13.36 | B | O |
| ATOM | 9566 | N | GLY | B | 69 | 73.105 | 31.658 | −11.916 | 1.00 | 13.93 | B | N |
| ATOM | 9567 | CA | GLY | B | 69 | 72.275 | 32.714 | −11.327 | 1.00 | 14.33 | B | C |
| ATOM | 9570 | C | GLY | B | 69 | 71.461 | 32.277 | −10.117 | 1.00 | 14.49 | B | C |
| ATOM | 9571 | O | GLY | B | 69 | 71.331 | 33.023 | −9.142 | 1.00 | 14.33 | B | O |
| ATOM | 9573 | N | TYR | B | 70 | 70.910 | 31.067 | −10.184 | 1.00 | 14.76 | B | N |
| ATOM | 9574 | CA | TYR | B | 70 | 70.127 | 30.493 | −9.080 | 1.00 | 14.94 | B | C |
| ATOM | 9576 | CB | TYR | B | 70 | 69.535 | 29.136 | −9.493 | 1.00 | 14.57 | B | C |
| ATOM | 9579 | CG | TYR | B | 70 | 70.532 | 27.992 | −9.554 | 1.00 | 12.18 | B | C |
| ATOM | 9580 | CD1 | TYR | B | 70 | 70.607 | 27.053 | −8.530 | 1.00 | 9.68 | B | C |
| ATOM | 9582 | CE1 | TYR | B | 70 | 71.511 | 25.999 | −8.585 | 1.00 | 8.46 | B | C |
| ATOM | 9584 | CZ | TYR | B | 70 | 72.353 | 25.874 | −9.673 | 1.00 | 8.09 | B | C |
| ATOM | 9585 | OH | TYR | B | 70 | 73.251 | 24.837 | −9.733 | 1.00 | 2.16 | B | O |
| ATOM | 9587 | CE2 | TYR | B | 70 | 72.300 | 26.789 | −10.701 | 1.00 | 10.87 | B | C |
| ATOM | 9589 | CD2 | TYR | B | 70 | 71.390 | 27.841 | −10.640 | 1.00 | 12.42 | B | C |
| ATOM | 9591 | C | TYR | B | 70 | 70.929 | 30.328 | −7.783 | 1.00 | 15.65 | B | C |

TABLE 8-2-continued

Coordinates for L494P Structure

| ATOM | 9592 | O | TYR | B | 70 | 70.354 | 30.256 | −6.696 | 1.00 | 15.92 | B | O |
|------|------|-----|-----|---|----|--------|--------|--------|------|-------|---|---|
| ATOM | 9594 | N | ARG | B | 71 | 72.251 | 30.270 | −7.911 | 1.00 | 16.20 | B | N |
| ATOM | 9595 | CA | ARG | B | 71 | 73.144 | 30.017 | −6.785 | 1.00 | 16.52 | B | C |
| ATOM | 9597 | CB | ARG | B | 71 | 74.387 | 29.275 | −7.292 | 1.00 | 16.53 | B | C |
| ATOM | 9600 | CG | ARG | B | 71 | 75.487 | 29.079 | −6.269 | 1.00 | 18.42 | B | C |
| ATOM | 9603 | CD | ARG | B | 71 | 76.353 | 27.866 | −6.587 | 1.00 | 20.45 | B | C |
| ATOM | 9606 | NE | ARG | B | 71 | 75.889 | 26.669 | −5.880 | 1.00 | 20.38 | B | N |
| ATOM | 9608 | CZ | ARG | B | 71 | 75.159 | 25.689 | −6.412 | 1.00 | 18.95 | B | C |
| ATOM | 9609 | NH1 | ARG | B | 71 | 74.803 | 24.658 | −5.656 | 1.00 | 19.37 | B | N |
| ATOM | 9612 | NH2 | ARG | B | 71 | 74.783 | 25.719 | −7.686 | 1.00 | 18.08 | B | N |
| ATOM | 9615 | C | ARG | B | 71 | 73.536 | 31.290 | −6.029 | 1.00 | 16.71 | B | C |
| ATOM | 9616 | O | ARG | B | 71 | 73.904 | 31.216 | −4.856 | 1.00 | 17.32 | B | O |
| ATOM | 9618 | N | PHE | B | 72 | 73.446 | 32.448 | −6.686 | 1.00 | 16.77 | B | N |
| ATOM | 9619 | CA | PHE | B | 72 | 73.869 | 33.722 | −6.084 | 1.00 | 16.64 | B | C |
| ATOM | 9621 | CB | PHE | B | 72 | 75.080 | 34.285 | −6.839 | 1.00 | 16.18 | B | C |
| ATOM | 9624 | CG | PHE | B | 72 | 76.285 | 33.396 | −6.807 | 1.00 | 14.45 | B | C |
| ATOM | 9625 | CD1 | PHE | B | 72 | 77.151 | 33.422 | −5.726 | 1.00 | 14.72 | B | C |
| ATOM | 9627 | CE1 | PHE | B | 72 | 78.270 | 32.602 | −5.696 | 1.00 | 15.49 | B | C |
| ATOM | 9629 | CZ | PHE | B | 72 | 78.529 | 31.748 | −6.758 | 1.00 | 14.51 | B | C |
| ATOM | 9631 | CE2 | PHE | B | 72 | 77.672 | 31.718 | −7.840 | 1.00 | 12.96 | B | C |
| ATOM | 9633 | CD2 | PHE | B | 72 | 76.559 | 32.540 | −7.861 | 1.00 | 12.86 | B | C |
| ATOM | 9635 | C | PHE | B | 72 | 72.771 | 34.789 | −6.055 | 1.00 | 17.23 | B | C |
| ATOM | 9636 | O | PHE | B | 72 | 73.070 | 35.966 | −5.846 | 1.00 | 17.54 | B | O |
| ATOM | 9638 | N | GLU | B | 73 | 71.511 | 34.392 | −6.241 | 1.00 | 17.68 | B | N |
| ATOM | 9639 | CA | GLU | B | 73 | 70.417 | 35.362 | −6.381 | 1.00 | 17.82 | B | C |
| ATOM | 9641 | CB | GLU | B | 73 | 69.044 | 34.677 | −6.330 | 1.00 | 17.51 | B | C |
| ATOM | 9644 | CG | GLU | B | 73 | 67.872 | 35.639 | −6.556 | 1.00 | 17.32 | B | C |
| ATOM | 9647 | CD | GLU | B | 73 | 66.574 | 34.938 | −6.923 | 1.00 | 18.12 | B | C |
| ATOM | 9648 | OE1 | GLU | B | 73 | 66.536 | 34.246 | −7.964 | 1.00 | 17.38 | B | O |
| ATOM | 9649 | OE2 | GLU | B | 73 | 65.582 | 35.097 | −6.181 | 1.00 | 18.22 | B | O |
| ATOM | 9650 | C | GLU | B | 73 | 70.492 | 36.495 | −5.347 | 1.00 | 18.27 | B | C |
| ATOM | 9651 | O | GLU | B | 73 | 70.561 | 37.666 | −5.720 | 1.00 | 18.56 | B | O |
| ATOM | 9653 | N | SER | B | 74 | 70.503 | 36.156 | −4.061 | 1.00 | 18.44 | B | N |
| ATOM | 9654 | CA | SER | B | 74 | 70.518 | 37.184 | −3.016 | 1.00 | 19.13 | B | C |
| ATOM | 9656 | CB | SER | B | 74 | 70.471 | 36.564 | −1.617 | 1.00 | 19.31 | B | C |
| ATOM | 9659 | OG | SER | B | 74 | 71.749 | 36.099 | −1.218 | 1.00 | 20.88 | B | O |
| ATOM | 9661 | C | SER | B | 74 | 71.751 | 38.075 | −3.137 | 1.00 | 19.37 | B | C |
| ATOM | 9662 | O | SER | B | 74 | 71.649 | 39.304 | −3.058 | 1.00 | 19.55 | B | O |
| ATOM | 9664 | N | ASP | B | 75 | 72.910 | 37.448 | −3.330 | 1.00 | 19.39 | B | N |
| ATOM | 9665 | CA | ASP | B | 75 | 74.168 | 38.181 | −3.468 | 1.00 | 19.25 | B | C |
| ATOM | 9667 | CB | ASP | B | 75 | 75.355 | 37.219 | −3.618 | 1.00 | 18.87 | B | C |
| ATOM | 9670 | CG | ASP | B | 75 | 75.559 | 36.340 | −2.387 | 1.00 | 18.85 | B | C |
| ATOM | 9671 | OD1 | ASP | B | 75 | 76.370 | 36.708 | −1.510 | 1.00 | 15.51 | B | O |
| ATOM | 9672 | OD2 | ASP | B | 75 | 74.897 | 35.284 | −2.293 | 1.00 | 19.53 | B | O |
| ATOM | 9673 | C | ASP | B | 75 | 74.090 | 39.139 | −4.656 | 1.00 | 19.33 | B | C |
| ATOM | 9674 | O | ASP | B | 75 | 74.564 | 40.274 | −4.579 | 1.00 | 19.40 | B | O |
| ATOM | 9676 | N | ILE | B | 76 | 73.466 | 38.682 | −5.739 | 1.00 | 19.53 | B | N |
| ATOM | 9677 | CA | ILE | B | 76 | 73.258 | 39.509 | −6.927 | 1.00 | 19.92 | B | C |
| ATOM | 9679 | CB | ILE | B | 76 | 72.762 | 38.664 | −8.128 | 1.00 | 19.83 | B | C |
| ATOM | 9681 | CG1 | ILE | B | 76 | 73.868 | 37.717 | −8.599 | 1.00 | 19.94 | B | C |
| ATOM | 9684 | CD1 | ILE | B | 76 | 73.384 | 36.631 | −9.528 | 1.00 | 21.34 | B | C |
| ATOM | 9688 | CG2 | ILE | B | 76 | 72.335 | 39.560 | −9.283 | 1.00 | 19.40 | B | C |
| ATOM | 9692 | C | ILE | B | 76 | 72.277 | 40.652 | −6.647 | 1.00 | 20.43 | B | C |
| ATOM | 9693 | O | ILE | B | 76 | 72.535 | 41.796 | −7.028 | 1.00 | 20.62 | B | O |
| ATOM | 9695 | N | ARG | B | 77 | 71.165 | 40.342 | −5.977 | 1.00 | 20.78 | B | N |
| ATOM | 9696 | CA | ARG | B | 77 | 70.175 | 41.360 | −5.595 | 1.00 | 21.05 | B | C |
| ATOM | 9698 | CB | ARG | B | 77 | 68.985 | 40.722 | −4.877 | 1.00 | 21.27 | B | C |
| ATOM | 9701 | CG | ARG | B | 77 | 68.098 | 39.864 | −5.760 | 1.00 | 23.04 | B | C |
| ATOM | 9704 | CD | ARG | B | 77 | 67.085 | 39.093 | −4.924 | 1.00 | 25.79 | B | C |
| ATOM | 9707 | NE | ARG | B | 77 | 66.125 | 39.989 | −4.281 | 1.00 | 27.15 | B | N |
| ATOM | 9709 | CZ | ARG | B | 77 | 65.054 | 40.514 | −4.878 | 1.00 | 28.90 | B | C |
| ATOM | 9710 | NH1 | ARG | B | 77 | 64.777 | 40.244 | −6.152 | 1.00 | 29.24 | B | N |
| ATOM | 9713 | NH2 | ARG | B | 77 | 64.251 | 41.320 | −4.193 | 1.00 | 30.29 | B | N |
| ATOM | 9716 | C | ARG | B | 77 | 70.785 | 42.436 | −4.697 | 1.00 | 20.82 | B | C |
| ATOM | 9717 | O | ARG | B | 77 | 70.469 | 43.618 | −4.833 | 1.00 | 20.93 | B | O |
| ATOM | 9719 | N | GLY | B | 78 | 71.653 | 42.016 | −3.780 | 1.00 | 20.58 | B | N |
| ATOM | 9720 | CA | GLY | B | 78 | 72.387 | 42.943 | −2.924 | 1.00 | 20.53 | B | C |
| ATOM | 9723 | C | GLY | B | 78 | 73.409 | 43.788 | −3.670 | 1.00 | 20.38 | B | C |
| ATOM | 9724 | O | GLY | B | 78 | 73.801 | 44.851 | −3.193 | 1.00 | 20.60 | B | O |
| ATOM | 9726 | N | ALA | B | 79 | 73.847 | 43.313 | −4.835 | 1.00 | 20.03 | B | N |
| ATOM | 9727 | CA | ALA | B | 79 | 74.777 | 44.060 | −5.680 | 1.00 | 20.01 | B | C |
| ATOM | 9729 | CB | ALA | B | 79 | 75.425 | 43.132 | −6.694 | 1.00 | 20.01 | B | C |
| ATOM | 9733 | C | ALA | B | 79 | 74.077 | 45.210 | −6.396 | 1.00 | 20.07 | B | C |
| ATOM | 9734 | O | ALA | B | 79 | 74.580 | 46.333 | −6.424 | 1.00 | 19.81 | B | O |
| ATOM | 9736 | N | LEU | B | 80 | 72.918 | 44.921 | −6.981 | 1.00 | 20.65 | B | N |
| ATOM | 9737 | CA | LEU | B | 80 | 72.145 | 45.928 | −7.706 | 1.00 | 21.23 | B | C |
| ATOM | 9739 | CB | LEU | B | 80 | 71.039 | 45.265 | −8.533 | 1.00 | 21.22 | B | C |
| ATOM | 9742 | CG | LEU | B | 80 | 71.509 | 44.313 | −9.637 | 1.00 | 22.04 | B | C |

TABLE 8-2-continued

Coordinates for L494P Structure

| ATOM | 9744 | CD1 | LEU | B | 80 | 70.315 | 43.623 | −10.295 | 1.00 | 22.93 | B | C |
|---|---|---|---|---|---|---|---|---|---|---|---|---|
| ATOM | 9748 | CD2 | LEU | B | 80 | 72.349 | 45.047 | −10.677 | 1.00 | 21.09 | B | C |
| ATOM | 9752 | C | LEU | B | 80 | 71.538 | 46.967 | −6.764 | 1.00 | 21.81 | B | C |
| ATOM | 9753 | O | LEU | B | 80 | 71.402 | 48.135 | −7.129 | 1.00 | 22.20 | B | O |
| ATOM | 9755 | N | ASP | B | 81 | 71.178 | 46.544 | −5.555 | 1.00 | 22.17 | B | N |
| ATOM | 9756 | CA | ASP | B | 81 | 70.651 | 47.463 | −4.543 | 1.00 | 22.35 | B | C |
| ATOM | 9758 | CB | ASP | B | 81 | 70.188 | 46.692 | −3.303 | 1.00 | 22.43 | B | C |
| ATOM | 9761 | CG | ASP | B | 81 | 69.122 | 47.433 | −2.521 | 1.00 | 23.43 | B | C |
| ATOM | 9762 | OD1 | ASP | B | 81 | 69.403 | 47.854 | −1.377 | 1.00 | 24.99 | B | O |
| ATOM | 9763 | OD2 | ASP | B | 81 | 68.004 | 47.598 | −3.055 | 1.00 | 23.01 | B | O |
| ATOM | 9764 | C | ASP | B | 81 | 71.705 | 48.509 | −4.158 | 1.00 | 22.33 | B | C |
| ATOM | 9765 | O | ASP | B | 81 | 71.374 | 49.658 | −3.862 | 1.00 | 22.00 | B | O |
| ATOM | 9767 | N | ARG | B | 82 | 72.970 | 48.091 | −4.160 | 1.00 | 22.64 | B | N |
| ATOM | 9768 | CA | ARG | B | 82 | 74.110 | 48.997 | −3.992 | 1.00 | 23.00 | B | C |
| ATOM | 9770 | CB | ARG | B | 82 | 75.429 | 48.207 | −3.977 | 1.00 | 23.31 | B | C |
| ATOM | 9773 | CG | ARG | B | 82 | 76.436 | 48.600 | −2.894 | 1.00 | 23.85 | B | C |
| ATOM | 9776 | CD | ARG | B | 82 | 76.608 | 47.462 | −1.902 | 1.00 | 25.49 | B | C |
| ATOM | 9779 | NE | ARG | B | 82 | 77.031 | 46.237 | −2.588 | 1.00 | 27.67 | B | N |
| ATOM | 9781 | CZ | ARG | B | 82 | 76.736 | 44.993 | −2.208 | 1.00 | 28.92 | B | C |
| ATOM | 9782 | NH1 | ARG | B | 82 | 75.999 | 44.755 | −1.125 | 1.00 | 29.74 | B | N |
| ATOM | 9785 | NH2 | ARG | B | 82 | 77.175 | 43.967 | −2.929 | 1.00 | 28.09 | B | N |
| ATOM | 9788 | C | ARG | B | 82 | 74.150 | 49.964 | −5.168 | 1.00 | 22.98 | B | C |
| ATOM | 9789 | O | ARG | B | 82 | 74.309 | 51.174 | −4.997 | 1.00 | 23.04 | B | O |
| ATOM | 9791 | N | PHE | B | 83 | 74.012 | 49.394 | −6.363 | 1.00 | 22.90 | B | N |
| ATOM | 9792 | CA | PHE | B | 83 | 74.097 | 50.131 | −7.620 | 1.00 | 22.96 | B | C |
| ATOM | 9794 | CB | PHE | B | 83 | 73.907 | 49.159 | −8.788 | 1.00 | 22.83 | B | C |
| ATOM | 9797 | CG | PHE | B | 83 | 74.055 | 49.790 | −10.137 | 1.00 | 22.79 | B | C |
| ATOM | 9798 | CD1 | PHE | B | 83 | 75.264 | 50.338 | −10.527 | 1.00 | 22.61 | B | C |
| ATOM | 9800 | CE1 | PHE | B | 83 | 75.411 | 50.916 | −11.776 | 1.00 | 23.30 | B | C |
| ATOM | 9802 | CZ | PHE | B | 83 | 74.340 | 50.941 | −12.656 | 1.00 | 23.91 | B | C |
| ATOM | 9804 | CE2 | PHE | B | 83 | 73.126 | 50.391 | −12.281 | 1.00 | 23.32 | B | C |
| ATOM | 9806 | CD2 | PHE | B | 83 | 72.989 | 49.816 | −11.029 | 1.00 | 23.33 | B | C |
| ATOM | 9808 | C | PHE | B | 83 | 73.081 | 51.269 | −7.701 | 1.00 | 23.09 | B | C |
| ATOM | 9809 | O | PHE | B | 83 | 73.424 | 52.381 | −8.102 | 1.00 | 23.19 | B | O |
| ATOM | 9811 | N | VAL | B | 84 | 71.840 | 50.989 | −7.312 | 1.00 | 23.08 | B | N |
| ATOM | 9812 | CA | VAL | B | 84 | 70.778 | 51.996 | −7.336 | 1.00 | 23.11 | B | C |
| ATOM | 9814 | CB | VAL | B | 84 | 69.379 | 51.347 | −7.184 | 1.00 | 23.15 | B | C |
| ATOM | 9816 | CG1 | VAL | B | 84 | 68.319 | 52.402 | −6.884 | 1.00 | 22.64 | B | C |
| ATOM | 9820 | CG2 | VAL | B | 84 | 69.019 | 50.564 | −8.441 | 1.00 | 22.66 | B | C |
| ATOM | 9824 | C | VAL | B | 84 | 70.969 | 53.048 | −6.244 | 1.00 | 23.28 | B | C |
| ATOM | 9825 | O | VAL | B | 84 | 70.892 | 54.248 | −6.513 | 1.00 | 23.33 | B | O |
| ATOM | 9827 | N | SER | B | 85 | 71.223 | 52.590 | −5.020 | 1.00 | 23.59 | B | N |
| ATOM | 9828 | CA | SER | B | 85 | 71.289 | 53.472 | −3.848 | 1.00 | 23.83 | B | C |
| ATOM | 9830 | CB | SER | B | 85 | 71.287 | 52.643 | −2.559 | 1.00 | 24.07 | B | C |
| ATOM | 9833 | OG | SER | B | 85 | 72.375 | 51.733 | −2.529 | 1.00 | 25.24 | B | O |
| ATOM | 9835 | C | SER | B | 85 | 72.493 | 54.417 | −3.851 | 1.00 | 23.55 | B | C |
| ATOM | 9836 | O | SER | B | 85 | 72.401 | 55.534 | −3.342 | 1.00 | 23.23 | B | O |
| ATOM | 9838 | N | SER | B | 86 | 73.612 | 53.973 | −4.425 | 1.00 | 23.60 | B | N |
| ATOM | 9839 | CA | SER | B | 86 | 74.814 | 54.810 | −4.524 | 1.00 | 23.71 | B | C |
| ATOM | 9841 | CB | SER | B | 86 | 76.076 | 53.937 | −4.571 | 1.00 | 23.57 | B | C |
| ATOM | 9844 | OG | SER | B | 86 | 76.163 | 53.204 | −5.781 | 1.00 | 23.18 | B | O |
| ATOM | 9846 | C | SER | B | 86 | 74.784 | 55.748 | −5.738 | 1.00 | 23.94 | B | C |
| ATOM | 9847 | O | SER | B | 86 | 75.764 | 56.444 | −6.007 | 1.00 | 23.67 | B | O |
| ATOM | 9849 | N | GLY | B | 87 | 73.664 | 55.764 | −6.462 | 1.00 | 24.30 | B | N |
| ATOM | 9850 | CA | GLY | B | 87 | 73.511 | 56.602 | −7.648 | 1.00 | 24.62 | B | C |
| ATOM | 9853 | C | GLY | B | 87 | 74.240 | 56.061 | −8.866 | 1.00 | 24.97 | B | C |
| ATOM | 9854 | O | GLY | B | 87 | 74.698 | 56.832 | −9.711 | 1.00 | 25.27 | B | O |
| ATOM | 9856 | N | GLY | B | 88 | 74.350 | 54.737 | −8.960 | 1.00 | 25.14 | B | N |
| ATOM | 9857 | CA | GLY | B | 88 | 75.008 | 54.090 | −10.096 | 1.00 | 25.27 | B | C |
| ATOM | 9860 | C | GLY | B | 88 | 74.123 | 54.077 | −11.330 | 1.00 | 25.47 | B | C |
| ATOM | 9861 | O | GLY | B | 88 | 74.598 | 54.303 | −12.446 | 1.00 | 25.09 | B | O |
| ATOM | 9863 | N | PHE | B | 89 | 72.834 | 53.811 | −11.123 | 1.00 | 25.86 | B | N |
| ATOM | 9864 | CA | PHE | B | 89 | 71.847 | 53.814 | −12.206 | 1.00 | 26.07 | B | C |
| ATOM | 9866 | CB | PHE | B | 89 | 70.486 | 53.334 | −11.688 | 1.00 | 26.21 | B | C |
| ATOM | 9869 | CG | PHE | B | 89 | 69.389 | 53.363 | −12.723 | 1.00 | 26.68 | B | C |
| ATOM | 9870 | CD1 | PHE | B | 89 | 69.523 | 52.660 | −13.915 | 1.00 | 26.40 | B | C |
| ATOM | 9872 | CE1 | PHE | B | 89 | 68.513 | 52.681 | −14.871 | 1.00 | 26.69 | B | C |
| ATOM | 9874 | CZ | PHE | B | 89 | 67.350 | 53.404 | −14.636 | 1.00 | 27.08 | B | C |
| ATOM | 9876 | CE2 | PHE | B | 89 | 67.202 | 54.104 | −13.448 | 1.00 | 27.35 | B | C |
| ATOM | 9878 | CD2 | PHE | B | 89 | 68.217 | 54.080 | −12.498 | 1.00 | 27.23 | B | C |
| ATOM | 9880 | C | PHE | B | 89 | 71.714 | 55.204 | −12.818 | 1.00 | 26.15 | B | C |
| ATOM | 9881 | O | PHE | B | 89 | 71.593 | 55.344 | −14.035 | 1.00 | 26.29 | B | O |
| ATOM | 9883 | N | ASP | B | 90 | 71.741 | 56.224 | −11.964 | 1.00 | 26.08 | B | N |
| ATOM | 9884 | CA | ASP | B | 90 | 71.678 | 57.612 | −12.411 | 1.00 | 26.14 | B | C |
| ATOM | 9886 | CB | ASP | B | 90 | 71.389 | 58.536 | −11.222 | 1.00 | 26.54 | B | C |
| ATOM | 9889 | CG | ASP | B | 90 | 70.904 | 59.914 | −11.651 | 1.00 | 28.73 | B | C |
| ATOM | 9890 | OD1 | ASP | B | 90 | 71.751 | 60.801 | −11.913 | 1.00 | 29.84 | B | O |
| ATOM | 9891 | OD2 | ASP | B | 90 | 69.671 | 60.112 | −11.709 | 1.00 | 31.49 | B | O |

TABLE 8-2-continued

Coordinates for L494P Structure

| ATOM | 9892 | C | ASP | B | 90 | 72.971 | 58.042 | −13.113 | 1.00 | 25.74 | B | C |
|---|---|---|---|---|---|---|---|---|---|---|---|---|
| ATOM | 9893 | O | ASP | B | 90 | 72.949 | 58.939 | −13.955 | 1.00 | 26.14 | B | O |
| ATOM | 9895 | N | ALA | B | 91 | 74.089 | 57.400 | −12.770 | 1.00 | 25.04 | B | N |
| ATOM | 9896 | CA | ALA | B | 91 | 75.395 | 57.742 | −13.343 | 1.00 | 24.47 | B | C |
| ATOM | 9898 | CB | ALA | B | 91 | 76.517 | 57.190 | −12.470 | 1.00 | 24.49 | B | C |
| ATOM | 9902 | C | ALA | B | 91 | 75.555 | 57.246 | −14.780 | 1.00 | 23.98 | B | C |
| ATOM | 9903 | O | ALA | B | 91 | 75.966 | 58.005 | −15.657 | 1.00 | 23.86 | B | O |
| ATOM | 9905 | N | VAL | B | 92 | 75.231 | 55.976 | −15.016 | 1.00 | 23.68 | B | N |
| ATOM | 9906 | CA | VAL | B | 92 | 75.405 | 55.365 | −16.341 | 1.00 | 23.29 | B | C |
| ATOM | 9908 | CB | VAL | B | 92 | 75.211 | 53.832 | −16.307 | 1.00 | 23.10 | B | C |
| ATOM | 9910 | CG1 | VAL | B | 92 | 76.248 | 53.187 | −15.399 | 1.00 | 22.67 | B | C |
| ATOM | 9914 | CG2 | VAL | B | 92 | 73.795 | 53.473 | −15.868 | 1.00 | 23.29 | B | C |
| ATOM | 9918 | C | VAL | B | 92 | 74.474 | 55.949 | −17.406 | 1.00 | 23.09 | B | C |
| ATOM | 9919 | O | VAL | B | 92 | 74.862 | 56.059 | −18.569 | 1.00 | 23.06 | B | O |
| ATOM | 9921 | N | THR | B | 93 | 73.260 | 56.333 | −17.009 | 1.00 | 22.98 | B | N |
| ATOM | 9922 | CA | THR | B | 93 | 72.277 | 56.894 | −17.948 | 1.00 | 22.80 | B | C |
| ATOM | 9924 | CB | THR | B | 93 | 70.887 | 57.094 | −17.293 | 1.00 | 22.75 | B | C |
| ATOM | 9926 | OG1 | THR | B | 93 | 71.002 | 57.966 | −16.161 | 1.00 | 21.89 | B | O |
| ATOM | 9928 | CG2 | THR | B | 93 | 70.299 | 55.756 | −16.859 | 1.00 | 22.59 | B | C |
| ATOM | 9932 | C | THR | B | 93 | 72.721 | 58.224 | −18.567 | 1.00 | 22.54 | B | C |
| ATOM | 9933 | O | THR | B | 93 | 72.142 | 58.664 | −19.562 | 1.00 | 22.69 | B | O |
| ATOM | 9935 | N | LYS | B | 94 | 73.734 | 58.857 | −17.974 | 1.00 | 22.08 | B | N |
| ATOM | 9936 | CA | LYS | B | 94 | 74.346 | 60.061 | −18.539 | 1.00 | 21.85 | B | C |
| ATOM | 9938 | CB | LYS | B | 94 | 74.849 | 60.989 | −17.422 | 1.00 | 21.89 | B | C |
| ATOM | 9941 | CG | LYS | B | 94 | 73.825 | 61.316 | −16.333 | 1.00 | 22.60 | B | C |
| ATOM | 9944 | CD | LYS | B | 94 | 72.573 | 61.989 | −16.885 | 1.00 | 23.74 | B | C |
| ATOM | 9947 | CE | LYS | B | 94 | 71.570 | 62.282 | −15.779 | 1.00 | 24.01 | B | C |
| ATOM | 9950 | NZ | LYS | B | 94 | 70.262 | 62.747 | −16.319 | 1.00 | 23.58 | B | N |
| ATOM | 9954 | C | LYS | B | 94 | 75.509 | 59.724 | −19.479 | 1.00 | 21.38 | B | C |
| ATOM | 9955 | O | LYS | B | 94 | 75.748 | 60.447 | −20.450 | 1.00 | 21.29 | B | O |
| ATOM | 9957 | N | THR | B | 95 | 76.219 | 58.629 | −19.193 | 1.00 | 20.80 | B | N |
| ATOM | 9958 | CA | THR | B | 95 | 77.463 | 58.288 | −19.898 | 1.00 | 20.16 | B | C |
| ATOM | 9960 | CB | THR | B | 95 | 78.598 | 57.987 | −18.892 | 1.00 | 20.05 | B | C |
| ATOM | 9962 | OG1 | THR | B | 95 | 78.226 | 56.884 | −18.054 | 1.00 | 19.86 | B | O |
| ATOM | 9964 | CG2 | THR | B | 95 | 78.882 | 59.208 | −18.027 | 1.00 | 19.17 | B | C |
| ATOM | 9968 | C | THR | B | 95 | 77.337 | 57.110 | −20.880 | 1.00 | 19.76 | B | C |
| ATOM | 9969 | O | THR | B | 95 | 77.331 | 57.315 | −22.097 | 1.00 | 19.67 | B | O |
| ATOM | 9971 | N | SER | B | 96 | 77.238 | 55.889 | −20.352 | 1.00 | 19.17 | B | N |
| ATOM | 9972 | CA | SER | B | 96 | 77.321 | 54.673 | −21.172 | 1.00 | 18.55 | B | C |
| ATOM | 9974 | CB | SER | B | 96 | 78.197 | 53.631 | −20.474 | 1.00 | 18.28 | B | C |
| ATOM | 9977 | OG | SER | B | 96 | 78.356 | 52.478 | −21.284 | 1.00 | 16.95 | B | O |
| ATOM | 9979 | C | SER | B | 96 | 75.957 | 54.055 | −21.474 | 1.00 | 18.37 | B | C |
| ATOM | 9980 | O | SER | B | 96 | 75.124 | 53.907 | −20.581 | 1.00 | 18.51 | B | O |
| ATOM | 9982 | N | LEU | B | 97 | 75.749 | 53.681 | −22.737 | 1.00 | 18.03 | B | N |
| ATOM | 9983 | CA | LEU | B | 97 | 74.538 | 52.970 | −23.156 | 1.00 | 17.63 | B | C |
| ATOM | 9985 | CB | LEU | B | 97 | 74.358 | 53.060 | −24.676 | 1.00 | 17.43 | B | C |
| ATOM | 9988 | CG | LEU | B | 97 | 73.200 | 52.279 | −25.308 | 1.00 | 16.33 | B | C |
| ATOM | 9990 | CD1 | LEU | B | 97 | 71.862 | 52.622 | −24.663 | 1.00 | 14.88 | B | C |
| ATOM | 9994 | CD2 | LEU | B | 97 | 73.158 | 52.544 | −26.799 | 1.00 | 15.23 | B | C |
| ATOM | 9998 | C | LEU | B | 97 | 74.616 | 51.509 | −22.721 | 1.00 | 17.57 | B | C |
| ATOM | 9999 | O | LEU | B | 97 | 73.726 | 51.012 | −22.031 | 1.00 | 17.48 | B | O |
| ATOM | 10001 | N | HIS | B | 98 | 75.685 | 50.833 | −23.135 | 1.00 | 17.59 | B | N |
| ATOM | 10002 | CA | HIS | B | 98 | 75.953 | 49.450 | −22.732 | 1.00 | 17.51 | B | C |
| ATOM | 10004 | CB | HIS | B | 98 | 77.430 | 49.107 | −22.981 | 1.00 | 17.79 | B | C |
| ATOM | 10007 | CG | HIS | B | 98 | 77.888 | 47.849 | −22.309 | 1.00 | 18.71 | B | C |
| ATOM | 10008 | ND1 | HIS | B | 98 | 77.360 | 46.610 | −22.602 | 1.00 | 20.03 | B | N |
| ATOM | 10010 | CE1 | HIS | B | 98 | 77.959 | 45.693 | −21.863 | 1.00 | 20.85 | B | C |
| ATOM | 10012 | NE2 | HIS | B | 98 | 78.861 | 46.291 | −21.106 | 1.00 | 20.28 | B | N |
| ATOM | 10014 | CD2 | HIS | B | 98 | 78.839 | 47.639 | −21.367 | 1.00 | 19.98 | B | C |
| ATOM | 10016 | C | HIS | B | 98 | 75.606 | 49.243 | −21.265 | 1.00 | 17.07 | B | C |
| ATOM | 10017 | O | HIS | B | 98 | 74.733 | 48.441 | −20.934 | 1.00 | 17.09 | B | O |
| ATOM | 10019 | N | GLY | B | 99 | 76.280 | 49.994 | −20.399 | 1.00 | 16.69 | B | N |
| ATOM | 10020 | CA | GLY | B | 99 | 76.080 | 49.903 | −18.956 | 1.00 | 16.27 | B | C |
| ATOM | 10023 | C | GLY | B | 99 | 74.644 | 50.107 | −18.510 | 1.00 | 15.82 | B | C |
| ATOM | 10024 | O | GLY | B | 99 | 74.218 | 49.516 | −17.518 | 1.00 | 15.84 | B | O |
| ATOM | 10026 | N | THR | B | 100 | 73.902 | 50.946 | −19.233 | 1.00 | 15.36 | B | N |
| ATOM | 10027 | CA | THR | B | 100 | 72.492 | 51.200 | −18.928 | 1.00 | 15.12 | B | |
| ATOM | 10029 | CB | THR | B | 100 | 71.989 | 52.511 | −19.582 | 1.00 | 15.04 | B | C |
| ATOM | 10031 | OG1 | THR | B | 100 | 72.701 | 53.626 | −19.034 | 1.00 | 14.95 | B | O |
| ATOM | 10033 | CG2 | THR | B | 100 | 70.500 | 52.706 | −19.336 | 1.00 | 14.68 | B | C |
| ATOM | 10037 | C | THR | B | 100 | 71.612 | 50.036 | −19.380 | 1.00 | 14.98 | B | C |
| ATOM | 10038 | O | THR | B | 100 | 70.745 | 49.587 | −18.636 | 1.00 | 14.55 | B | O |
| ATOM | 10040 | N | ALA | B | 101 | 71.846 | 49.552 | −20.596 | 1.00 | 15.35 | B | N |
| ATOM | 10041 | CA | ALA | B | 101 | 71.059 | 48.452 | −21.162 | 1.00 | 15.58 | B | C |
| ATOM | 10043 | CB | ALA | B | 101 | 71.386 | 48.281 | −22.637 | 1.00 | 15.49 | B | C |
| ATOM | 10047 | C | ALA | B | 101 | 71.281 | 47.135 | −20.413 | 1.00 | 15.71 | B | C |
| ATOM | 10048 | O | ALA | B | 101 | 70.392 | 46.278 | −20.369 | 1.00 | 16.00 | B | O |
| ATOM | 10050 | N | LEU | B | 102 | 72.470 | 46.978 | −19.838 | 1.00 | 15.43 | B | N |

TABLE 8-2-continued

Coordinates for L494P Structure

| ATOM | 10051 | CA | LEU | B | 102 | 72.788 | 45.817 | −19.011 | 1.00 | 15.11 | B | C |
|---|---|---|---|---|---|---|---|---|---|---|---|---|
| ATOM | 10053 | CB | LEU | B | 102 | 74.306 | 45.698 | −18.828 | 1.00 | 14.88 | B | C |
| ATOM | 10056 | CG | LEU | B | 102 | 74.848 | 44.512 | −18.029 | 1.00 | 13.96 | B | C |
| ATOM | 10058 | CD1 | LEU | B | 102 | 74.261 | 43.198 | −18.515 | 1.00 | 13.62 | B | C |
| ATOM | 10062 | CD2 | LEU | B | 102 | 76.369 | 44.488 | −18.109 | 1.00 | 13.07 | B | C |
| ATOM | 10066 | C | LEU | B | 102 | 72.096 | 45.934 | −17.654 | 1.00 | 15.05 | B | C |
| ATOM | 10067 | O | LEU | B | 102 | 71.425 | 45.000 | −17.210 | 1.00 | 15.13 | B | O |
| ATOM | 10069 | N | SER | B | 103 | 72.254 | 47.089 | −17.010 | 1.00 | 14.64 | B | N |
| ATOM | 10070 | CA | SER | B | 103 | 71.667 | 47.325 | −15.695 | 1.00 | 14.21 | B | C |
| ATOM | 10072 | CB | SER | B | 103 | 72.208 | 48.613 | −15.068 | 1.00 | 14.05 | B | C |
| ATOM | 10075 | OG | SER | B | 103 | 71.690 | 49.766 | −15.705 | 1.00 | 13.39 | B | O |
| ATOM | 10077 | C | SER | B | 103 | 70.148 | 47.383 | −15.764 | 1.00 | 14.45 | B | C |
| ATOM | 10078 | O | SER | B | 103 | 69.471 | 46.896 | −14.862 | 1.00 | 15.34 | B | O |
| ATOM | 10080 | N | PHE | B | 104 | 69.611 | 47.976 | −16.827 | 1.00 | 14.20 | B | N |
| ATOM | 10081 | CA | PHE | B | 104 | 68.163 | 48.010 | −17.017 | 1.00 | 13.83 | B | C |
| ATOM | 10083 | CB | PHE | B | 104 | 67.792 | 48.649 | −18.356 | 1.00 | 14.07 | B | C |
| ATOM | 10086 | CG | PHE | B | 104 | 66.311 | 48.706 | −18.608 | 1.00 | 14.64 | B | C |
| ATOM | 10087 | CD1 | PHE | B | 104 | 65.589 | 49.850 | −18.309 | 1.00 | 15.83 | B | C |
| ATOM | 10089 | CE1 | PHE | B | 104 | 64.220 | 49.905 | −18.538 | 1.00 | 16.59 | B | C |
| ATOM | 10091 | CZ | PHE | B | 104 | 63.562 | 48.807 | −19.068 | 1.00 | 16.05 | B | C |
| ATOM | 10093 | CE2 | PHE | B | 104 | 64.272 | 47.660 | −19.368 | 1.00 | 15.67 | B | C |
| ATOM | 10095 | CD2 | PHE | B | 104 | 65.639 | 47.612 | −19.140 | 1.00 | 15.20 | B | C |
| ATOM | 10097 | C | PHE | B | 104 | 67.627 | 46.594 | −16.966 | 1.00 | 13.24 | B | C |
| ATOM | 10098 | O | PHE | B | 104 | 66.718 | 46.295 | −16.194 | 1.00 | 13.15 | B | O |
| ATOM | 10100 | N | ARG | B | 105 | 68.211 | 45.731 | −17.794 | 1.00 | 13.05 | B | N |
| ATOM | 10101 | CA | ARG | B | 105 | 67.795 | 44.334 | −17.904 | 1.00 | 13.08 | B | C |
| ATOM | 10103 | CB | ARG | B | 105 | 68.620 | 43.617 | −18.977 | 1.00 | 13.37 | B | C |
| ATOM | 10106 | CG | ARG | B | 105 | 68.162 | 42.196 | −19.273 | 1.00 | 13.35 | B | C |
| ATOM | 10109 | CD | ARG | B | 105 | 68.759 | 41.681 | −20.576 | 1.00 | 12.99 | B | C |
| ATOM | 10112 | NE | ARG | B | 105 | 70.219 | 41.615 | −20.518 | 1.00 | 12.68 | B | N |
| ATOM | 10114 | CZ | ARG | B | 105 | 70.918 | 40.672 | −19.885 | 1.00 | 10.95 | B | C |
| ATOM | 10115 | NH1 | ARG | B | 105 | 70.309 | 39.686 | −19.231 | 1.00 | 9.34 | B | N |
| ATOM | 10118 | NH2 | ARG | B | 105 | 72.246 | 40.718 | −19.902 | 1.00 | 10.70 | B | N |
| ATOM | 10121 | C | ARG | B | 105 | 67.936 | 43.602 | −16.578 | 1.00 | 12.52 | B | C |
| ATOM | 10122 | O | ARG | B | 105 | 66.992 | 42.967 | −16.106 | 1.00 | 12.65 | B | O |
| ATOM | 10124 | N | LEU | B | 106 | 69.119 | 43.697 | −15.983 | 1.00 | 11.82 | B | N |
| ATOM | 10125 | CA | LEU | B | 106 | 69.380 | 43.060 | −14.699 | 1.00 | 11.23 | B | C |
| ATOM | 10127 | CB | LEU | B | 106 | 70.827 | 43.314 | −14.255 | 1.00 | 10.81 | B | C |
| ATOM | 10130 | CG | LEU | B | 106 | 71.911 | 42.650 | −15.109 | 1.00 | 8.27 | B | C |
| ATOM | 10132 | CD1 | LEU | B | 106 | 73.282 | 43.156 | −14.714 | 1.00 | 6.17 | B | C |
| ATOM | 10136 | CD2 | LEU | B | 106 | 71.845 | 41.141 | −14.993 | 1.00 | 6.13 | B | C |
| ATOM | 10140 | C | LEU | B | 106 | 68.395 | 43.548 | −13.635 | 1.00 | 11.04 | B | C |
| ATOM | 10141 | O | LEU | B | 106 | 67.783 | 42.745 | −12.939 | 1.00 | 10.80 | B | O |
| ATOM | 10143 | N | LEU | B | 107 | 68.229 | 44.862 | −13.528 | 1.00 | 11.29 | B | N |
| ATOM | 10144 | CA | LEU | B | 107 | 67.332 | 45.436 | −12.525 | 1.00 | 11.68 | B | C |
| ATOM | 10146 | CB | LEU | B | 107 | 67.324 | 46.967 | −12.603 | 1.00 | 11.63 | B | C |
| ATOM | 10149 | CG | LEU | B | 107 | 68.511 | 47.671 | −11.943 | 1.00 | 10.96 | B | C |
| ATOM | 10151 | CD1 | LEU | B | 107 | 68.589 | 49.129 | −12.377 | 1.00 | 9.53 | B | C |
| ATOM | 10155 | CD2 | LEU | B | 107 | 68.414 | 47.555 | −10.424 | 1.00 | 11.26 | B | C |
| ATOM | 10159 | C | LEU | B | 107 | 65.912 | 44.901 | −12.671 | 1.00 | 11.95 | B | C |
| ATOM | 10160 | O | LEU | B | 107 | 65.323 | 44.423 | −11.700 | 1.00 | 12.00 | B | O |
| ATOM | 10162 | N | ARG | B | 108 | 65.370 | 44.972 | −13.882 | 1.00 | 12.17 | B | N |
| ATOM | 10163 | CA | ARG | B | 108 | 64.004 | 44.516 | −14.122 | 1.00 | 12.61 | B | C |
| ATOM | 10165 | CB | ARG | B | 108 | 63.535 | 44.888 | −15.526 | 1.00 | 12.46 | B | C |
| ATOM | 10168 | CG | ARG | B | 108 | 62.082 | 44.523 | −15.779 | 1.00 | 11.97 | B | C |
| ATOM | 10171 | CD | ARG | B | 108 | 61.486 | 45.308 | −16.924 | 1.00 | 11.34 | B | C |
| ATOM | 10174 | NE | ARG | B | 108 | 61.210 | 46.693 | −16.555 | 1.00 | 10.21 | B | N |
| ATOM | 10176 | CZ | ARG | B | 108 | 60.650 | 47.590 | −17.362 | 1.00 | 10.94 | B | C |
| ATOM | 10177 | NH1 | ARG | B | 108 | 60.296 | 47.265 | −18.603 | 1.00 | 10.42 | B | N |
| ATOM | 10180 | NH2 | ARG | B | 108 | 60.443 | 48.825 | −16.924 | 1.00 | 11.87 | B | N |
| ATOM | 10183 | C | ARG | B | 108 | 63.867 | 43.011 | −13.905 | 1.00 | 13.23 | B | C |
| ATOM | 10184 | O | ARG | B | 108 | 62.876 | 42.554 | −13.338 | 1.00 | 13.51 | B | O |
| ATOM | 10186 | N | GLN | B | 109 | 64.861 | 42.252 | −14.359 | 1.00 | 13.93 | B | N |
| ATOM | 10187 | CA | GLN | B | 109 | 64.893 | 40.802 | −14.148 | 1.00 | 14.40 | B | C |
| ATOM | 10189 | CB | GLN | B | 109 | 66.224 | 40.225 | −14.650 | 1.00 | 14.43 | B | C |
| ATOM | 10192 | CG | GLN | B | 109 | 66.353 | 38.709 | −14.555 | 1.00 | 13.91 | B | C |
| ATOM | 10195 | CD | GLN | B | 109 | 67.800 | 38.247 | −14.560 | 1.00 | 12.71 | B | C |
| ATOM | 10196 | OE1 | GLN | B | 109 | 68.652 | 38.840 | −15.222 | 1.00 | 12.98 | B | O |
| ATOM | 10197 | NE2 | GLN | B | 109 | 68.083 | 37.183 | −13.819 | 1.00 | 12.06 | B | N |
| ATOM | 10200 | C | GLN | B | 109 | 64.695 | 40.461 | −12.670 | 1.00 | 14.82 | B | C |
| ATOM | 10201 | O | GLN | B | 109 | 63.935 | 39.551 | −12.336 | 1.00 | 15.14 | B | O |
| ATOM | 10203 | N | HIS | B | 110 | 65.369 | 41.208 | −11.795 | 1.00 | 15.02 | B | N |
| ATOM | 10204 | CA | HIS | B | 110 | 65.307 | 40.977 | −10.351 | 1.00 | 15.34 | B | C |
| ATOM | 10206 | CB | HIS | B | 110 | 66.702 | 41.147 | −9.732 | 1.00 | 15.49 | B | C |
| ATOM | 10209 | CG | HIS | B | 110 | 67.692 | 40.110 | −10.168 | 1.00 | 14.40 | B | C |
| ATOM | 10210 | ND1 | HIS | B | 110 | 67.790 | 38.876 | −9.563 | 1.00 | 13.44 | B | N |
| ATOM | 10212 | CE1 | HIS | B | 110 | 68.749 | 38.178 | −10.145 | 1.00 | 13.56 | B | C |
| ATOM | 10214 | NE2 | HIS | B | 110 | 69.280 | 38.917 | −11.101 | 1.00 | 11.71 | B | N |

TABLE 8-2-continued

Coordinates for L494P Structure

| ATOM | 10216 | CD2 | HIS | B | 110 | 68.639 | 40.130 | −11.135 | 1.00 | 12.93 | B | C |
|---|---|---|---|---|---|---|---|---|---|---|---|---|
| ATOM | 10218 | C | HIS | B | 110 | 64.300 | 41.899 | −9.644 | 1.00 | 15.77 | B | C |
| ATOM | 10219 | O | HIS | B | 110 | 64.591 | 42.451 | −8.578 | 1.00 | 15.94 | B | O |
| ATOM | 10221 | N | GLY | B | 111 | 63.127 | 42.075 | −10.248 | 1.00 | 16.02 | B | N |
| ATOM | 10222 | CA | GLY | B | 111 | 61.992 | 42.729 | −9.590 | 1.00 | 16.43 | B | C |
| ATOM | 10225 | C | GLY | B | 111 | 62.109 | 44.199 | −9.205 | 1.00 | 16.88 | B | C |
| ATOM | 10226 | O | GLY | B | 111 | 61.257 | 44.708 | −8.474 | 1.00 | 16.73 | B | O |
| ATOM | 10228 | N | PHE | B | 112 | 63.143 | 44.890 | −9.683 | 1.00 | 17.42 | B | N |
| ATOM | 10229 | CA | PHE | B | 112 | 63.274 | 46.328 | −9.438 | 1.00 | 17.67 | B | C |
| ATOM | 10231 | CB | PHE | B | 112 | 64.722 | 46.798 | −9.597 | 1.00 | 17.98 | B | C |
| ATOM | 10234 | CG | PHE | B | 112 | 65.615 | 46.412 | −8.460 | 1.00 | 19.28 | B | C |
| ATOM | 10235 | CD1 | PHE | B | 112 | 65.605 | 47.143 | −7.281 | 1.00 | 20.60 | B | C |
| ATOM | 10237 | CE1 | PHE | B | 112 | 66.431 | 46.796 | −6.222 | 1.00 | 22.44 | B | C |
| ATOM | 10239 | CZ | PHE | B | 112 | 67.287 | 45.710 | −6.339 | 1.00 | 22.18 | B | C |
| ATOM | 10241 | CE2 | PHE | B | 112 | 67.309 | 44.976 | −7.515 | 1.00 | 21.88 | B | C |
| ATOM | 10243 | CD2 | PHE | B | 112 | 66.477 | 45.329 | −8.569 | 1.00 | 20.40 | B | C |
| ATOM | 10245 | C | PHE | B | 112 | 62.397 | 47.100 | −10.406 | 1.00 | 17.64 | B | C |
| ATOM | 10246 | O | PHE | B | 112 | 62.039 | 46.594 | −11.470 | 1.00 | 17.30 | B | O |
| ATOM | 10248 | N | GLU | B | 113 | 62.053 | 48.329 | −10.036 | 1.00 | 18.13 | B | N |
| ATOM | 10249 | CA | GLU | B | 113 | 61.356 | 49.217 | −10.952 | 1.00 | 18.59 | B | C |
| ATOM | 10251 | CB | GLU | B | 113 | 60.339 | 50.108 | −10.227 | 1.00 | 18.94 | B | C |
| ATOM | 10254 | CG | GLU | B | 113 | 59.591 | 51.062 | −11.178 | 1.00 | 20.95 | B | C |
| ATOM | 10257 | CD | GLU | B | 113 | 58.188 | 51.435 | −10.710 | 1.00 | 22.45 | B | C |
| ATOM | 10258 | OE1 | GLU | B | 113 | 57.949 | 51.484 | −9.485 | 1.00 | 25.01 | B | O |
| ATOM | 10259 | OE2 | GLU | B | 113 | 57.324 | 51.691 | −11.577 | 1.00 | 21.27 | B | O |
| ATOM | 10260 | C | GLU | B | 113 | 62.375 | 50.068 | −11.697 | 1.00 | 18.18 | B | C |
| ATOM | 10261 | O | GLU | B | 113 | 63.150 | 50.806 | −11.085 | 1.00 | 17.81 | B | O |
| ATOM | 10263 | N | VAL | B | 114 | 62.378 | 49.924 | −13.020 | 1.00 | 17.96 | B | N |
| ATOM | 10264 | CA | VAL | B | 114 | 63.109 | 50.814 | −13.915 | 1.00 | 17.72 | B | C |
| ATOM | 10266 | CB | VAL | B | 114 | 64.338 | 50.121 | −14.540 | 1.00 | 17.40 | B | C |
| ATOM | 10268 | CG1 | VAL | B | 114 | 65.341 | 49.766 | −13.458 | 1.00 | 16.56 | B | C |
| ATOM | 10272 | CG2 | VAL | B | 114 | 63.925 | 48.880 | −15.324 | 1.00 | 17.16 | B | C |
| ATOM | 10276 | C | VAL | B | 114 | 62.152 | 51.303 | −15.005 | 1.00 | 17.86 | B | C |
| ATOM | 10277 | O | VAL | B | 114 | 61.067 | 50.746 | −15.183 | 1.00 | 17.45 | B | O |
| ATOM | 10279 | N | SER | B | 115 | 62.554 | 52.351 | −15.719 | 1.00 | 18.11 | B | N |
| ATOM | 10280 | CA | SER | B | 115 | 61.695 | 52.993 | −16.713 | 1.00 | 17.98 | B | C |
| ATOM | 10282 | CB | SER | B | 115 | 61.151 | 54.311 | −16.155 | 1.00 | 17.76 | B | C |
| ATOM | 10285 | OG | SER | B | 115 | 60.269 | 54.934 | −17.070 | 1.00 | 17.43 | B | O |
| ATOM | 10287 | C | SER | B | 115 | 62.451 | 53.247 | −18.016 | 1.00 | 18.09 | B | C |
| ATOM | 10288 | O | SER | B | 115 | 63.661 | 53.487 | −18.006 | 1.00 | 18.38 | B | O |
| ATOM | 10290 | N | GLN | B | 116 | 61.724 | 53.199 | −19.132 | 1.00 | 17.77 | B | N |
| ATOM | 10291 | CA | GLN | B | 116 | 62.300 | 53.431 | −20.460 | 1.00 | 17.40 | B | C |
| ATOM | 10293 | CB | GLN | B | 116 | 61.235 | 53.251 | −21.548 | 1.00 | 17.53 | B | C |
| ATOM | 10296 | CG | GLN | B | 116 | 60.133 | 54.317 | −21.543 | 1.00 | 18.28 | B | C |
| ATOM | 10299 | CD | GLN | B | 116 | 58.938 | 53.944 | −22.404 | 1.00 | 17.36 | B | C |
| ATOM | 10300 | OE1 | GLN | B | 116 | 59.065 | 53.210 | −23.385 | 1.00 | 17.59 | B | O |
| ATOM | 10301 | NE2 | GLN | B | 116 | 57.770 | 54.456 | −22.041 | 1.00 | 15.98 | B | N |
| ATOM | 10304 | C | GLN | B | 116 | 62.944 | 54.812 | −20.589 | 1.00 | 17.28 | B | C |
| ATOM | 10305 | O | GLN | B | 116 | 63.751 | 55.035 | −21.488 | 1.00 | 17.66 | B | O |
| ATOM | 10307 | N | GLU | B | 117 | 62.586 | 55.731 | −19.693 | 1.00 | 17.24 | B | N |
| ATOM | 10308 | CA | GLU | B | 117 | 63.225 | 57.050 | −19.625 | 1.00 | 17.35 | B | C |
| ATOM | 10310 | CB | GLU | B | 117 | 62.455 | 57.969 | −18.666 | 1.00 | 17.33 | B | C |
| ATOM | 10313 | CG | GLU | B | 117 | 61.062 | 58.369 | −19.160 | 1.00 | 16.64 | B | C |
| ATOM | 10316 | CD | GLU | B | 117 | 61.092 | 59.306 | −20.364 | 1.00 | 15.94 | B | C |
| ATOM | 10317 | OE1 | GLU | B | 117 | 62.165 | 59.872 | −20.667 | 1.00 | 13.31 | B | O |
| ATOM | 10318 | OE2 | GLU | B | 117 | 60.034 | 59.479 | −21.008 | 1.00 | 15.83 | B | O |
| ATOM | 10319 | C | GLU | B | 117 | 64.706 | 56.987 | −19.218 | 1.00 | 17.41 | B | C |
| ATOM | 10320 | O | GLU | B | 117 | 65.398 | 58.005 | −19.230 | 1.00 | 17.10 | B | O |
| ATOM | 10322 | N | ALA | B | 118 | 65.184 | 55.799 | −18.848 | 1.00 | 17.79 | B | N |
| ATOM | 10323 | CA | ALA | B | 118 | 66.614 | 55.563 | −18.667 | 1.00 | 18.07 | B | C |
| ATOM | 10325 | CB | ALA | B | 118 | 66.852 | 54.162 | −18.121 | 1.00 | 17.97 | B | C |
| ATOM | 10329 | C | ALA | B | 118 | 67.360 | 55.748 | −19.986 | 1.00 | 18.33 | B | C |
| ATOM | 10330 | O | ALA | B | 118 | 68.491 | 56.234 | −20.004 | 1.00 | 18.49 | B | O |
| ATOM | 10332 | N | PHE | B | 119 | 66.711 | 55.369 | −21.085 | 1.00 | 18.76 | B | N |
| ATOM | 10333 | CA | PHE | B | 119 | 67.313 | 55.448 | −22.414 | 1.00 | 19.32 | B | C |
| ATOM | 10335 | CB | PHE | B | 119 | 66.785 | 54.310 | −23.300 | 1.00 | 19.27 | B | C |
| ATOM | 10338 | CG | PHE | B | 119 | 67.039 | 52.933 | −22.742 | 1.00 | 18.34 | B | C |
| ATOM | 10339 | CD1 | PHE | B | 119 | 65.987 | 52.138 | −22.305 | 1.00 | 17.02 | B | C |
| ATOM | 10341 | CE1 | PHE | B | 119 | 66.219 | 50.871 | −21.791 | 1.00 | 17.25 | B | C |
| ATOM | 10343 | CZ | PHE | B | 119 | 67.514 | 50.384 | −21.706 | 1.00 | 17.67 | B | C |
| ATOM | 10345 | CE2 | PHE | B | 119 | 68.574 | 51.166 | −22.137 | 1.00 | 17.65 | B | C |
| ATOM | 10347 | CD2 | PHE | B | 119 | 68.333 | 52.433 | −22.653 | 1.00 | 18.36 | B | C |
| ATOM | 10349 | C | PHE | B | 119 | 67.075 | 56.794 | −23.114 | 1.00 | 20.18 | B | C |
| ATOM | 10350 | O | PHE | B | 119 | 67.387 | 56.933 | −24.298 | 1.00 | 20.87 | B | O |
| ATOM | 10352 | N | SER | B | 120 | 66.537 | 57.781 | −22.396 | 1.00 | 20.76 | B | N |
| ATOM | 10353 | CA | SER | B | 120 | 66.253 | 59.099 | −22.982 | 1.00 | 20.91 | B | C |
| ATOM | 10355 | CB | SER | B | 120 | 65.240 | 59.870 | −22.129 | 1.00 | 20.93 | B | C |
| ATOM | 10358 | OG | SER | B | 120 | 65.837 | 60.372 | −20.944 | 1.00 | 21.26 | B | O |

TABLE 8-2-continued

Coordinates for L494P Structure

| ATOM | 10360 | C | SER | B | 120 | 67.515 | 59.945 | −23.177 | 1.00 | 20.98 | B | C |
|---|---|---|---|---|---|---|---|---|---|---|---|---|
| ATOM | 10361 | O | SER | B | 120 | 67.497 | 60.912 | −23.937 | 1.00 | 21.13 | B | O |
| ATOM | 10363 | N | GLY | B | 121 | 68.601 | 59.584 | −22.496 | 1.00 | 21.23 | B | N |
| ATOM | 10364 | CA | GLY | B | 121 | 69.884 | 60.267 | −22.667 | 1.00 | 21.73 | B | C |
| ATOM | 10367 | C | GLY | B | 121 | 70.734 | 59.725 | −23.808 | 1.00 | 22.23 | B | C |
| ATOM | 10368 | O | GLY | B | 121 | 71.951 | 59.924 | −23.821 | 1.00 | 21.96 | B | O |
| ATOM | 10370 | N | PHE | B | 122 | 70.098 | 59.038 | −24.762 | 1.00 | 22.81 | B | N |
| ATOM | 10371 | CA | PHE | B | 122 | 70.789 | 58.447 | −25.913 | 1.00 | 23.32 | B | C |
| ATOM | 10373 | CB | PHE | B | 122 | 71.029 | 56.945 | −25.680 | 1.00 | 23.17 | B | C |
| ATOM | 10376 | CG | PHE | B | 122 | 71.721 | 56.627 | −24.382 | 1.00 | 22.98 | B | C |
| ATOM | 10377 | CD1 | PHE | B | 122 | 73.108 | 56.588 | −24.308 | 1.00 | 22.49 | B | C |
| ATOM | 10379 | CE1 | PHE | B | 122 | 73.750 | 56.293 | −23.107 | 1.00 | 22.39 | B | C |
| ATOM | 10381 | CZ | PHE | B | 122 | 73.002 | 56.034 | −21.968 | 1.00 | 22.47 | B | C |
| ATOM | 10383 | CE2 | PHE | B | 122 | 71.617 | 56.067 | −22.030 | 1.00 | 23.14 | B | C |
| ATOM | 10385 | CD2 | PHE | B | 122 | 70.984 | 56.361 | −23.234 | 1.00 | 23.30 | B | C |
| ATOM | 10387 | C | PHE | B | 122 | 69.984 | 58.640 | −27.204 | 1.00 | 23.76 | B | C |
| ATOM | 10388 | O | PHE | B | 122 | 69.948 | 57.751 | −28.056 | 1.00 | 23.82 | B | O |
| ATOM | 10390 | N | LYS | B | 123 | 69.348 | 59.803 | −27.349 | 1.00 | 24.39 | B | N |
| ATOM | 10391 | CA | LYS | B | 123 | 68.464 | 60.075 | −28.490 | 1.00 | 24.99 | B | C |
| ATOM | 10393 | CB | LYS | B | 123 | 66.996 | 59.960 | −28.061 | 1.00 | 25.11 | B | C |
| ATOM | 10396 | CG | LYS | B | 123 | 66.579 | 58.554 | −27.623 | 1.00 | 26.36 | B | C |
| ATOM | 10399 | CD | LYS | B | 123 | 65.256 | 58.547 | −26.858 | 1.00 | 27.49 | B | C |
| ATOM | 10402 | CE | LYS | B | 123 | 64.056 | 58.691 | −27.782 | 1.00 | 28.01 | B | C |
| ATOM | 10405 | NZ | LYS | B | 123 | 63.822 | 57.472 | −28.611 | 1.00 | 28.15 | B | N |
| ATOM | 10409 | C | LYS | B | 123 | 68.728 | 61.456 | −29.106 | 1.00 | 25.23 | B | C |
| ATOM | 10410 | O | LYS | B | 123 | 68.984 | 62.428 | −28.391 | 1.00 | 25.22 | B | O |
| ATOM | 10412 | N | ASP | B | 124 | 68.647 | 61.529 | −30.435 | 1.00 | 25.37 | B | N |
| ATOM | 10413 | CA | ASP | B | 124 | 68.960 | 62.755 | −31.185 | 1.00 | 25.33 | B | C |
| ATOM | 10415 | CB | ASP | B | 124 | 69.203 | 62.423 | −32.673 | 1.00 | 25.38 | B | C |
| ATOM | 10418 | CG | ASP | B | 124 | 67.946 | 61.934 | −33.398 | 1.00 | 24.90 | B | C |
| ATOM | 10419 | OD1 | ASP | B | 124 | 66.838 | 61.988 | −32.824 | 1.00 | 23.59 | B | O |
| ATOM | 10420 | OD2 | ASP | B | 124 | 68.072 | 61.489 | −34.558 | 1.00 | 23.99 | B | O |
| ATOM | 10421 | C | ASP | B | 124 | 67.882 | 63.840 | −31.028 | 1.00 | 25.30 | B | C |
| ATOM | 10422 | O | ASP | B | 124 | 66.943 | 63.683 | −30.243 | 1.00 | 25.33 | B | O |
| ATOM | 10424 | N | GLN | B | 125 | 68.032 | 64.938 | −31.770 | 1.00 | 25.13 | B | N |
| ATOM | 10425 | CA | GLN | B | 125 | 67.047 | 66.026 | −31.767 | 1.00 | 25.14 | B | C |
| ATOM | 10427 | CB | GLN | B | 125 | 67.458 | 67.128 | −32.750 | 1.00 | 25.16 | B | C |
| ATOM | 10430 | CG | GLN | B | 125 | 68.471 | 68.123 | −32.187 | 1.00 | 25.92 | B | C |
| ATOM | 10433 | CD | GLN | B | 125 | 67.855 | 69.137 | −31.228 | 1.00 | 25.99 | B | C |
| ATOM | 10434 | OE1 | GLN | B | 125 | 66.688 | 69.032 | −30.849 | 1.00 | 26.31 | B | O |
| ATOM | 10435 | NE2 | GLN | B | 125 | 68.646 | 70.126 | −30.832 | 1.00 | 25.52 | B | N |
| ATOM | 10438 | C | GLN | B | 125 | 65.633 | 65.545 | −32.098 | 1.00 | 25.09 | B | C |
| ATOM | 10439 | O | GLN | B | 125 | 64.675 | 65.901 | −31.409 | 1.00 | 25.17 | B | O |
| ATOM | 10441 | N | ASN | B | 126 | 65.511 | 64.738 | −33.149 | 1.00 | 24.90 | B | N |
| ATOM | 10442 | CA | ASN | B | 126 | 64.213 | 64.199 | −33.567 | 1.00 | 24.53 | B | C |
| ATOM | 10444 | CB | ASN | B | 126 | 64.337 | 63.471 | −34.911 | 1.00 | 24.47 | B | C |
| ATOM | 10447 | CG | ASN | B | 126 | 64.510 | 64.422 | −36.078 | 1.00 | 24.13 | B | C |
| ATOM | 10448 | OD1 | ASN | B | 126 | 65.064 | 65.511 | −35.930 | 1.00 | 23.55 | B | O |
| ATOM | 10449 | ND2 | ASN | B | 126 | 64.033 | 64.015 | −37.249 | 1.00 | 23.27 | B | N |
| ATOM | 10452 | C | ASN | B | 126 | 63.578 | 63.257 | −32.545 | 1.00 | 24.35 | B | C |
| ATOM | 10453 | O | ASN | B | 126 | 62.352 | 63.204 | −32.430 | 1.00 | 24.38 | B | O |
| ATOM | 10455 | N | GLY | B | 127 | 64.411 | 62.524 | −31.808 | 1.00 | 23.98 | B | N |
| ATOM | 10456 | CA | GLY | B | 127 | 63.938 | 61.494 | −30.881 | 1.00 | 23.80 | B | C |
| ATOM | 10459 | C | GLY | B | 127 | 64.216 | 60.076 | −31.357 | 1.00 | 23.59 | B | C |
| ATOM | 10460 | O | GLY | B | 127 | 63.608 | 59.124 | −30.865 | 1.00 | 23.44 | B | O |
| ATOM | 10462 | N | ASN | B | 128 | 65.117 | 59.939 | −32.330 | 1.00 | 23.46 | B | N |
| ATOM | 10463 | CA | ASN | B | 128 | 65.661 | 58.641 | −32.721 | 1.00 | 23.17 | B | C |
| ATOM | 10465 | CB | ASN | B | 128 | 65.918 | 58.577 | −34.232 | 1.00 | 23.19 | B | C |
| ATOM | 10468 | CG | ASN | B | 128 | 64.713 | 59.001 | −35.056 | 1.00 | 22.48 | B | C |
| ATOM | 10469 | OD1 | ASN | B | 128 | 64.149 | 60.075 | −34.846 | 1.00 | 20.86 | B | O |
| ATOM | 10470 | ND2 | ASN | B | 128 | 64.323 | 58.162 | −36.010 | 1.00 | 21.21 | B | N |
| ATOM | 10473 | C | ASN | B | 128 | 66.972 | 58.432 | −31.980 | 1.00 | 22.97 | B | C |
| ATOM | 10474 | O | ASN | B | 128 | 67.583 | 59.394 | −31.515 | 1.00 | 22.71 | B | O |
| ATOM | 10476 | N | PHE | B | 129 | 67.408 | 57.182 | −31.870 | 1.00 | 22.94 | B | N |
| ATOM | 10477 | CA | PHE | B | 129 | 68.691 | 56.885 | −31.234 | 1.00 | 22.94 | B | C |
| ATOM | 10479 | CB | PHE | B | 129 | 68.859 | 55.380 | −31.017 | 1.00 | 23.04 | B | C |
| ATOM | 10482 | CG | PHE | B | 129 | 68.061 | 54.844 | −29.863 | 1.00 | 24.12 | B | C |
| ATOM | 10483 | CD1 | PHE | B | 129 | 66.708 | 54.559 | −30.011 | 1.00 | 25.06 | B | C |
| ATOM | 10485 | CE1 | PHE | B | 129 | 65.965 | 54.066 | −28.946 | 1.00 | 25.61 | B | C |
| ATOM | 10487 | CZ | PHE | B | 129 | 66.575 | 53.850 | −27.718 | 1.00 | 25.88 | B | C |
| ATOM | 10489 | CE2 | PHE | B | 129 | 67.926 | 54.130 | −27.559 | 1.00 | 25.30 | B | C |
| ATOM | 10491 | CD2 | PHE | B | 129 | 68.661 | 54.625 | −28.628 | 1.00 | 24.47 | B | C |
| ATOM | 10493 | C | PHE | B | 129 | 69.827 | 57.432 | −32.091 | 1.00 | 22.78 | B | C |
| ATOM | 10494 | O | PHE | B | 129 | 69.719 | 57.474 | −33.320 | 1.00 | 22.90 | B | O |
| ATOM | 10496 | N | LEU | B | 130 | 70.907 | 57.862 | −31.441 | 1.00 | 22.49 | B | N |
| ATOM | 10497 | CA | LEU | B | 130 | 72.045 | 58.435 | −32.154 | 1.00 | 22.33 | B | C |
| ATOM | 10499 | CB | LEU | B | 130 | 73.095 | 58.980 | −31.178 | 1.00 | 22.14 | B | C |
| ATOM | 10502 | CG | LEU | B | 130 | 72.731 | 60.262 | −30.422 | 1.00 | 21.49 | B | C |

TABLE 8-2-continued

Coordinates for L494P Structure

| ATOM | 10504 | CD1 | LEU | B | 130 | 73.833 | 60.628 | −29.442 | 1.00 | 20.84 | B | C |
|---|---|---|---|---|---|---|---|---|---|---|---|---|
| ATOM | 10508 | CD2 | LEU | B | 130 | 72.469 | 61.414 | −31.383 | 1.00 | 20.96 | B | C |
| ATOM | 10512 | C | LEU | B | 130 | 72.672 | 57.393 | −33.075 | 1.00 | 22.54 | B | C |
| ATOM | 10513 | O | LEU | B | 130 | 73.072 | 56.320 | −32.626 | 1.00 | 22.34 | B | O |
| ATOM | 10515 | N | GLU | B | 131 | 72.730 | 57.721 | −34.365 | 1.00 | 23.02 | B | N |
| ATOM | 10516 | CA | GLU | B | 131 | 73.337 | 56.863 | −35.387 | 1.00 | 23.37 | B | C |
| ATOM | 10518 | CB | GLU | B | 131 | 73.410 | 57.629 | −36.718 | 1.00 | 23.40 | B | C |
| ATOM | 10521 | CG | GLU | B | 131 | 74.128 | 56.913 | −37.870 | 1.00 | 24.01 | B | C |
| ATOM | 10524 | CD | GLU | B | 131 | 73.300 | 55.813 | −38.517 | 1.00 | 25.54 | B | C |
| ATOM | 10525 | OE1 | GLU | B | 131 | 72.271 | 55.395 | −37.939 | 1.00 | 26.84 | B | O |
| ATOM | 10526 | OE2 | GLU | B | 131 | 73.688 | 55.362 | −39.616 | 1.00 | 26.70 | B | O |
| ATOM | 10527 | C | GLU | B | 131 | 74.732 | 56.388 | −34.976 | 1.00 | 23.61 | B | C |
| ATOM | 10528 | O | GLU | B | 131 | 75.065 | 55.213 | −35.130 | 1.00 | 23.84 | B | O |
| ATOM | 10530 | N | ASN | B | 132 | 75.531 | 57.306 | −34.438 | 1.00 | 23.67 | B | N |
| ATOM | 10531 | CA | ASN | B | 132 | 76.923 | 57.024 | −34.060 | 1.00 | 23.74 | B | C |
| ATOM | 10533 | CB | ASN | B | 132 | 77.674 | 58.343 | −33.806 | 1.00 | 23.96 | B | C |
| ATOM | 10536 | CG | ASN | B | 132 | 76.916 | 59.285 | −32.884 | 1.00 | 24.66 | B | C |
| ATOM | 10537 | OD1 | ASN | B | 132 | 76.613 | 58.945 | −31.739 | 1.00 | 25.44 | B | O |
| ATOM | 10538 | ND2 | ASN | B | 132 | 76.604 | 60.477 | −33.384 | 1.00 | 24.88 | B | N |
| ATOM | 10541 | C | ASN | B | 132 | 77.118 | 56.056 | −32.873 | 1.00 | 23.55 | B | C |
| ATOM | 10542 | O | ASN | B | 132 | 78.253 | 55.791 | −32.469 | 1.00 | 23.42 | B | O |
| ATOM | 10544 | N | LEU | B | 133 | 76.022 | 55.535 | −32.322 | 1.00 | 23.55 | B | N |
| ATOM | 10545 | CA | LEU | B | 133 | 76.087 | 54.480 | −31.303 | 1.00 | 23.52 | B | C |
| ATOM | 10547 | CB | LEU | B | 133 | 74.870 | 54.555 | −30.370 | 1.00 | 23.31 | B | C |
| ATOM | 10550 | CG | LEU | B | 133 | 74.750 | 55.823 | −29.521 | 1.00 | 22.53 | B | C |
| ATOM | 10552 | CD1 | LEU | B | 133 | 73.383 | 55.904 | −28.862 | 1.00 | 20.74 | B | C |
| ATOM | 10556 | CD2 | LEU | B | 133 | 75.857 | 55.886 | −28.477 | 1.00 | 22.10 | B | C |
| ATOM | 10560 | C | LEU | B | 133 | 76.180 | 53.075 | −31.916 | 1.00 | 23.65 | B | C |
| ATOM | 10561 | O | LEU | B | 133 | 76.404 | 52.102 | −31.193 | 1.00 | 23.81 | B | O |
| ATOM | 10563 | N | LYS | B | 134 | 76.011 | 52.970 | −33.237 | 1.00 | 23.51 | B | N |
| ATOM | 10564 | CA | LYS | B | 134 | 76.111 | 51.681 | −33.931 | 1.00 | 23.40 | B | C |
| ATOM | 10566 | CB | LYS | B | 134 | 75.613 | 51.790 | −35.382 | 1.00 | 23.26 | B | C |
| ATOM | 10569 | CG | LYS | B | 134 | 76.593 | 52.452 | −36.356 | 1.00 | 23.29 | B | C |
| ATOM | 10572 | CD | LYS | B | 134 | 76.009 | 52.566 | −37.761 | 1.00 | 22.10 | B | C |
| ATOM | 10575 | CE | LYS | B | 134 | 77.047 | 53.064 | −38.759 | 1.00 | 20.46 | B | C |
| ATOM | 10578 | NZ | LYS | B | 134 | 76.503 | 53.139 | −40.141 | 1.00 | 18.74 | B | N |
| ATOM | 10582 | C | LYS | B | 134 | 77.539 | 51.126 | −33.907 | 1.00 | 23.60 | B | C |
| ATOM | 10583 | O | LYS | B | 134 | 77.736 | 49.915 | −34.006 | 1.00 | 23.60 | B | O |
| ATOM | 10585 | N | GLU | B | 135 | 78.525 | 52.014 | −33.780 | 1.00 | 23.90 | B | N |
| ATOM | 10586 | CA | GLU | B | 135 | 79.934 | 51.615 | −33.743 | 1.00 | 24.13 | B | C |
| ATOM | 10588 | CB | GLU | B | 135 | 80.853 | 52.842 | −33.837 | 1.00 | 24.42 | B | C |
| ATOM | 10591 | CG | GLU | B | 135 | 80.740 | 53.633 | −35.149 | 1.00 | 25.24 | B | C |
| ATOM | 10594 | CD | GLU | B | 135 | 81.137 | 52.832 | −36.384 | 1.00 | 25.99 | B | C |
| ATOM | 10595 | OE1 | GLU | B | 135 | 81.957 | 51.895 | −36.266 | 1.00 | 25.85 | B | O |
| ATOM | 10596 | OE2 | GLU | B | 135 | 80.629 | 53.148 | −37.482 | 1.00 | 26.38 | B | O |
| ATOM | 10597 | C | GLU | B | 135 | 80.275 | 50.800 | −32.493 | 1.00 | 23.93 | B | C |
| ATOM | 10598 | O | GLU | B | 135 | 81.150 | 49.934 | −32.542 | 1.00 | 24.05 | B | O |
| ATOM | 10600 | N | ASP | B | 136 | 79.596 | 51.078 | −31.382 | 1.00 | 23.74 | B | N |
| ATOM | 10601 | CA | ASP | B | 136 | 79.752 | 50.270 | −30.172 | 1.00 | 23.80 | B | C |
| ATOM | 10603 | CB | ASP | B | 136 | 79.424 | 51.090 | −28.914 | 1.00 | 23.79 | B | C |
| ATOM | 10606 | CG | ASP | B | 136 | 80.046 | 50.506 | −27.647 | 1.00 | 23.69 | B | C |
| ATOM | 10607 | OD1 | ASP | B | 136 | 80.288 | 49.280 | −27.589 | 1.00 | 22.19 | B | O |
| ATOM | 10608 | OD2 | ASP | B | 136 | 80.295 | 51.282 | −26.701 | 1.00 | 24.10 | B | O |
| ATOM | 10609 | C | ASP | B | 136 | 78.855 | 49.031 | −30.280 | 1.00 | 23.77 | B | C |
| ATOM | 10610 | O | ASP | B | 136 | 77.667 | 49.080 | −29.957 | 1.00 | 23.85 | B | O |
| ATOM | 10612 | N | ILE | B | 137 | 79.438 | 47.927 | −30.743 | 1.00 | 23.58 | B | N |
| ATOM | 10613 | CA | ILE | B | 137 | 78.701 | 46.674 | −30.945 | 1.00 | 23.48 | B | C |
| ATOM | 10615 | CB | ILE | B | 137 | 79.553 | 45.638 | −31.734 | 1.00 | 23.47 | B | C |
| ATOM | 10617 | CG1 | ILE | B | 137 | 79.750 | 46.086 | −33.189 | 1.00 | 23.86 | B | C |
| ATOM | 10620 | CD1 | ILE | B | 137 | 80.947 | 46.990 | −33.413 | 1.00 | 23.96 | B | C |
| ATOM | 10624 | CG2 | ILE | B | 137 | 78.900 | 44.261 | −31.712 | 1.00 | 23.85 | B | C |
| ATOM | 10628 | C | ILE | B | 137 | 78.242 | 46.065 | −29.612 | 1.00 | 23.33 | B | C |
| ATOM | 10629 | O | ILE | B | 137 | 77.241 | 45.344 | −29.559 | 1.00 | 23.33 | B | O |
| ATOM | 10631 | N | LYS | B | 138 | 78.974 | 46.368 | −28.543 | 1.00 | 22.92 | B | N |
| ATOM | 10632 | CA | LYS | B | 138 | 78.647 | 45.884 | −27.202 | 1.00 | 22.45 | B | C |
| ATOM | 10634 | CB | LYS | B | 138 | 79.815 | 46.177 | −26.252 | 1.00 | 22.66 | B | C |
| ATOM | 10637 | CG | LYS | B | 138 | 80.011 | 45.168 | −25.136 | 1.00 | 23.58 | B | C |
| ATOM | 10640 | CD | LYS | B | 138 | 80.951 | 45.726 | −24.063 | 1.00 | 25.04 | B | C |
| ATOM | 10643 | CE | LYS | B | 138 | 81.815 | 44.644 | −23.430 | 1.00 | 25.73 | B | C |
| ATOM | 10646 | NZ | LYS | B | 138 | 82.936 | 44.235 | −24.324 | 1.00 | 25.22 | B | N |
| ATOM | 10650 | C | LYS | B | 138 | 77.364 | 46.542 | −26.673 | 1.00 | 21.59 | B | C |
| ATOM | 10651 | O | LYS | B | 138 | 76.492 | 45.864 | −26.123 | 1.00 | 21.40 | B | O |
| ATOM | 10653 | N | ALA | B | 139 | 77.258 | 47.860 | −26.853 | 1.00 | 20.48 | B | N |
| ATOM | 10654 | CA | ALA | B | 139 | 76.130 | 48.643 | −26.335 | 1.00 | 19.64 | B | C |
| ATOM | 10656 | CB | ALA | B | 139 | 76.479 | 50.125 | −26.324 | 1.00 | 19.54 | B | C |
| ATOM | 10660 | C | ALA | B | 139 | 74.841 | 48.416 | −27.118 | 1.00 | 19.12 | B | C |
| ATOM | 10661 | O | ALA | B | 139 | 73.756 | 48.368 | −26.535 | 1.00 | 19.04 | B | O |
| ATOM | 10663 | N | ILE | B | 140 | 74.961 | 48.292 | −28.437 | 1.00 | 18.59 | B | N |

TABLE 8-2-continued

Coordinates for L494P Structure

| ATOM | 10664 | CA | ILE | B | 140 | 73.814 | 47.982 | −29.291 | 1.00 | 18.11 | B | C |
| ATOM | 10666 | CB | ILE | B | 140 | 74.197 | 47.979 | −30.791 | 1.00 | 18.07 | B | C |
| ATOM | 10668 | CG1 | ILE | B | 140 | 74.613 | 49.380 | −31.254 | 1.00 | 18.28 | B | C |
| ATOM | 10671 | CD1 | ILE | B | 140 | 73.475 | 50.378 | −31.350 | 1.00 | 18.35 | B | C |
| ATOM | 10675 | CG2 | ILE | B | 140 | 73.040 | 47.471 | −31.646 | 1.00 | 17.81 | B | C |
| ATOM | 10679 | C | ILE | B | 140 | 73.234 | 46.614 | −28.928 | 1.00 | 17.72 | B | C |
| ATOM | 10680 | O | ILE | B | 140 | 72.017 | 46.443 | −28.889 | 1.00 | 18.01 | B | O |
| ATOM | 10682 | N | LEU | B | 141 | 74.108 | 45.648 | −28.657 | 1.00 | 17.08 | B | N |
| ATOM | 10683 | CA | LEU | B | 141 | 73.674 | 44.295 | −28.331 | 1.00 | 16.61 | B | C |
| ATOM | 10685 | CB | LEU | B | 141 | 74.854 | 43.324 | −28.386 | 1.00 | 16.26 | B | C |
| ATOM | 10688 | CG | LEU | B | 141 | 74.528 | 41.828 | −28.324 | 1.00 | 15.01 | B | C |
| ATOM | 10690 | CD1 | LEU | B | 141 | 73.243 | 41.487 | −29.069 | 1.00 | 13.84 | B | C |
| ATOM | 10694 | CD2 | LEU | B | 141 | 75.696 | 41.020 | −28.873 | 1.00 | 14.21 | B | C |
| ATOM | 10698 | C | LEU | B | 141 | 73.003 | 44.233 | −26.963 | 1.00 | 16.78 | B | C |
| ATOM | 10699 | O | LEU | B | 141 | 71.933 | 43.640 | −26.820 | 1.00 | 17.29 | B | O |
| ATOM | 10701 | N | SER | B | 142 | 73.624 | 44.843 | −25.958 | 1.00 | 16.60 | B | N |
| ATOM | 10702 | CA | SER | B | 142 | 73.015 | 44.911 | −24.627 | 1.00 | 16.64 | B | C |
| ATOM | 10704 | CB | SER | B | 142 | 73.944 | 45.607 | −23.625 | 1.00 | 16.83 | B | C |
| ATOM | 10707 | OG | SER | B | 142 | 74.964 | 44.727 | −23.179 | 1.00 | 16.19 | B | O |
| ATOM | 10709 | C | SER | B | 142 | 71.659 | 45.621 | −24.692 | 1.00 | 16.43 | B | C |
| ATOM | 10710 | O | SER | B | 142 | 70.700 | 45.194 | −24.048 | 1.00 | 16.17 | B | O |
| ATOM | 10712 | N | LEU | B | 143 | 71.589 | 46.697 | −25.474 | 1.00 | 16.32 | B | N |
| ATOM | 10713 | CA | LEU | B | 143 | 70.322 | 47.380 | −25.743 | 1.00 | 16.29 | B | C |
| ATOM | 10715 | CB | LEU | B | 143 | 70.539 | 48.590 | −26.664 | 1.00 | 15.94 | B | C |
| ATOM | 10718 | CG | LEU | B | 143 | 69.296 | 49.191 | −27.331 | 1.00 | 15.20 | B | C |
| ATOM | 10720 | CD1 | LEU | B | 143 | 68.240 | 49.558 | −26.301 | 1.00 | 13.55 | B | C |
| ATOM | 10724 | CD2 | LEU | B | 143 | 69.678 | 50.402 | −28.160 | 1.00 | 15.26 | B | C |
| ATOM | 10728 | C | LEU | B | 143 | 69.312 | 46.415 | −26.365 | 1.00 | 16.70 | B | C |
| ATOM | 10729 | O | LEU | B | 143 | 68.150 | 46.375 | −25.957 | 1.00 | 17.42 | B | O |
| ATOM | 10731 | N | TYR | B | 144 | 69.765 | 45.644 | −27.350 | 1.00 | 16.53 | B | N |
| ATOM | 10732 | CA | TYR | B | 144 | 68.921 | 44.657 | −28.024 | 1.00 | 16.27 | B | C |
| ATOM | 10734 | CB | TYR | B | 144 | 69.718 | 43.942 | −29.118 | 1.00 | 16.16 | B | C |
| ATOM | 10737 | CG | TYR | B | 144 | 69.051 | 42.714 | −29.692 | 1.00 | 15.78 | B | C |
| ATOM | 10738 | CD1 | TYR | B | 144 | 67.955 | 42.822 | −30.541 | 1.00 | 15.10 | B | C |
| ATOM | 10740 | CE1 | TYR | B | 144 | 67.349 | 41.697 | −31.077 | 1.00 | 14.61 | B | C |
| ATOM | 10742 | CZ | TYR | B | 144 | 67.844 | 40.447 | −30.769 | 1.00 | 15.60 | B | C |
| ATOM | 10743 | OH | TYR | B | 144 | 67.251 | 39.325 | −31.297 | 1.00 | 19.22 | B | O |
| ATOM | 10745 | CE2 | TYR | B | 144 | 68.933 | 40.314 | −29.932 | 1.00 | 16.86 | B | C |
| ATOM | 10747 | CD2 | TYR | B | 144 | 69.531 | 41.444 | −29.401 | 1.00 | 16.55 | B | C |
| ATOM | 10749 | C | TYR | B | 144 | 68.336 | 43.641 | −27.046 | 1.00 | 16.32 | B | C |
| ATOM | 10750 | O | TYR | B | 144 | 67.143 | 43.348 | −27.094 | 1.00 | 16.33 | B | O |
| ATOM | 10752 | N | GLU | B | 145 | 69.178 | 43.116 | −26.159 | 1.00 | 16.42 | B | N |
| ATOM | 10753 | CA | GLU | B | 145 | 68.738 | 42.136 | −25.162 | 1.00 | 16.72 | B | C |
| ATOM | 10755 | CB | GLU | B | 145 | 69.940 | 41.586 | −24.382 | 1.00 | 16.57 | B | C |
| ATOM | 10758 | CG | GLU | B | 145 | 70.940 | 40.787 | −25.221 | 1.00 | 16.50 | B | C |
| ATOM | 10761 | CD | GLU | B | 145 | 70.436 | 39.406 | −25.610 | 1.00 | 16.57 | B | C |
| ATOM | 10762 | OE1 | GLU | B | 145 | 69.275 | 39.069 | −25.290 | 1.00 | 17.83 | B | O |
| ATOM | 10763 | OE2 | GLU | B | 145 | 71.208 | 38.652 | −26.240 | 1.00 | 16.22 | B | O |
| ATOM | 10764 | C | GLU | B | 145 | 67.718 | 42.732 | −24.184 | 1.00 | 16.86 | B | C |
| ATOM | 10765 | O | GLU | B | 145 | 66.768 | 42.055 | −23.773 | 1.00 | 16.50 | B | O |
| ATOM | 10767 | N | ALA | B | 146 | 67.918 | 44.004 | −23.832 | 1.00 | 16.74 | B | N |
| ATOM | 10768 | CA | ALA | B | 146 | 67.088 | 44.687 | −22.838 | 1.00 | 16.36 | B | C |
| ATOM | 10770 | CB | ALA | B | 146 | 67.859 | 45.847 | −22.219 | 1.00 | 15.89 | B | C |
| ATOM | 10774 | C | ALA | B | 146 | 65.760 | 45.187 | −23.402 | 1.00 | 16.26 | B | C |
| ATOM | 10775 | O | ALA | B | 146 | 64.922 | 45.683 | −22.650 | 1.00 | 16.44 | B | O |
| ATOM | 10777 | N | SER | B | 147 | 65.568 | 45.064 | −24.713 | 1.00 | 16.21 | B | N |
| ATOM | 10778 | CA | SER | B | 147 | 64.326 | 45.496 | −25.354 | 1.00 | 16.38 | B | C |
| ATOM | 10780 | CB | SER | B | 147 | 64.536 | 45.662 | −26.862 | 1.00 | 16.51 | B | C |
| ATOM | 10783 | OG | SER | B | 147 | 64.814 | 44.420 | −27.489 | 1.00 | 17.36 | B | O |
| ATOM | 10785 | C | SER | B | 147 | 63.163 | 44.531 | −25.096 | 1.00 | 16.24 | B | C |
| ATOM | 10786 | O | SER | B | 147 | 62.015 | 44.959 | −24.969 | 1.00 | 15.95 | B | O |
| ATOM | 10788 | N | PHE | B | 148 | 63.467 | 43.237 | −25.009 | 1.00 | 16.34 | B | N |
| ATOM | 10789 | CA | PHE | B | 148 | 62.435 | 42.198 | −24.890 | 1.00 | 16.34 | B | C |
| ATOM | 10791 | CB | PHE | B | 148 | 63.026 | 40.816 | −25.190 | 1.00 | 16.30 | B | C |
| ATOM | 10794 | CG | PHE | B | 148 | 63.444 | 40.640 | −26.620 | 1.00 | 17.03 | B | C |
| ATOM | 10795 | CD1 | PHE | B | 148 | 62.570 | 40.093 | −27.548 | 1.00 | 18.20 | B | C |
| ATOM | 10797 | CE1 | PHE | B | 148 | 62.948 | 39.938 | −28.877 | 1.00 | 19.13 | B | C |
| ATOM | 10799 | CZ | PHE | B | 148 | 64.213 | 40.335 | −29.287 | 1.00 | 18.33 | B | C |
| ATOM | 10801 | CE2 | PHE | B | 148 | 65.093 | 40.887 | −28.369 | 1.00 | 17.95 | B | C |
| ATOM | 10803 | CD2 | PHE | B | 148 | 64.705 | 41.039 | −27.044 | 1.00 | 17.59 | B | C |
| ATOM | 10805 | C | PHE | B | 148 | 61.738 | 42.187 | −23.530 | 1.00 | 16.13 | B | C |
| ATOM | 10806 | O | PHE | B | 148 | 60.615 | 41.695 | −23.415 | 1.00 | 15.72 | B | O |
| ATOM | 10808 | N | LEU | B | 149 | 62.391 | 42.750 | −22.514 | 1.00 | 16.32 | B | N |
| ATOM | 10809 | CA | LEU | B | 149 | 61.811 | 42.840 | −21.171 | 1.00 | 16.28 | B | C |
| ATOM | 10811 | CB | LEU | B | 149 | 62.910 | 43.001 | −20.117 | 1.00 | 15.75 | B | C |
| ATOM | 10814 | CG | LEU | B | 149 | 63.883 | 41.829 | −20.010 | 1.00 | 15.12 | B | C |
| ATOM | 10816 | CD1 | LEU | B | 149 | 65.018 | 41.960 | −21.017 | 1.00 | 14.29 | B | C |
| ATOM | 10820 | CD2 | LEU | B | 149 | 64.430 | 41.725 | −18.598 | 1.00 | 15.76 | B | C |

TABLE 8-2-continued

Coordinates for L494P Structure

| ATOM | 10824 | C | LEU | B | 149 | 60.816 | 43.995 | −21.049 | 1.00 | 16.79 | B | C |
|---|---|---|---|---|---|---|---|---|---|---|---|---|
| ATOM | 10825 | O | LEU | B | 149 | 60.382 | 44.327 | −19.943 | 1.00 | 17.29 | B | O |
| ATOM | 10827 | N | ALA | B | 150 | 60.451 | 44.597 | −22.182 | 1.00 | 16.76 | B | N |
| ATOM | 10828 | CA | ALA | B | 150 | 59.538 | 45.736 | −22.205 | 1.00 | 16.50 | B | C |
| ATOM | 10830 | CB | ALA | B | 150 | 59.404 | 46.271 | −23.627 | 1.00 | 16.43 | B | C |
| ATOM | 10834 | C | ALA | B | 150 | 58.163 | 45.397 | −21.646 | 1.00 | 16.20 | B | C |
| ATOM | 10835 | O | ALA | B | 150 | 57.838 | 44.230 | −21.406 | 1.00 | 15.98 | B | O |
| ATOM | 10837 | N | LEU | B | 151 | 57.368 | 46.440 | −21.437 | 1.00 | 16.11 | B | N |
| ATOM | 10838 | CA | LEU | B | 151 | 55.992 | 46.298 | −20.982 | 1.00 | 16.14 | B | C |
| ATOM | 10840 | CB | LEU | B | 151 | 55.809 | 46.980 | −19.625 | 1.00 | 16.21 | B | C |
| ATOM | 10843 | CG | LEU | B | 151 | 56.718 | 46.502 | −18.488 | 1.00 | 15.32 | B | C |
| ATOM | 10845 | CD1 | LEU | B | 151 | 56.599 | 47.436 | −17.293 | 1.00 | 13.46 | B | C |
| ATOM | 10849 | CD2 | LEU | B | 151 | 56.397 | 45.066 | −18.088 | 1.00 | 13.69 | B | C |
| ATOM | 10853 | C | LEU | B | 151 | 55.044 | 46.910 | −22.008 | 1.00 | 16.00 | B | C |
| ATOM | 10854 | O | LEU | B | 151 | 55.475 | 47.599 | −22.936 | 1.00 | 15.95 | B | O |
| ATOM | 10856 | N | GLU | B | 152 | 53.752 | 46.651 | −21.830 | 1.00 | 15.76 | B | N |
| ATOM | 10857 | CA | GLU | B | 152 | 52.730 | 47.163 | −22.734 | 1.00 | 15.95 | B | C |
| ATOM | 10859 | CB | GLU | B | 152 | 51.356 | 46.595 | −22.363 | 1.00 | 16.09 | B | C |
| ATOM | 10862 | CG | GLU | B | 152 | 50.504 | 46.178 | −23.560 | 1.00 | 17.01 | B | C |
| ATOM | 10865 | CD | GLU | B | 152 | 49.009 | 46.229 | −23.277 | 1.00 | 17.41 | B | C |
| ATOM | 10866 | OE1 | GLU | B | 152 | 48.623 | 46.417 | −22.103 | 1.00 | 17.43 | B | O |
| ATOM | 10867 | OE2 | GLU | B | 152 | 48.216 | 46.086 | −24.233 | 1.00 | 17.21 | B | O |
| ATOM | 10868 | C | GLU | B | 152 | 52.700 | 48.689 | −22.649 | 1.00 | 16.18 | B | C |
| ATOM | 10869 | O | GLU | B | 152 | 52.615 | 49.243 | −21.554 | 1.00 | 16.81 | B | O |
| ATOM | 10871 | N | GLY | B | 153 | 52.789 | 49.362 | −23.795 | 1.00 | 16.13 | B | N |
| ATOM | 10872 | CA | GLY | B | 153 | 52.784 | 50.828 | −23.839 | 1.00 | 15.84 | B | C |
| ATOM | 10875 | C | GLY | B | 153 | 54.164 | 51.469 | −23.884 | 1.00 | 15.69 | B | C |
| ATOM | 10876 | O | GLY | B | 153 | 54.307 | 52.590 | −24.373 | 1.00 | 15.81 | B | O |
| ATOM | 10878 | N | GLU | B | 154 | 55.178 | 50.771 | −23.374 | 1.00 | 15.51 | B | N |
| ATOM | 10879 | CA | GLU | B | 154 | 56.550 | 51.282 | −23.382 | 1.00 | 15.70 | B | C |
| ATOM | 10881 | CB | GLU | B | 154 | 57.448 | 50.439 | −22.467 | 1.00 | 15.97 | B | C |
| ATOM | 10884 | CG | GLU | B | 154 | 57.054 | 50.515 | −20.994 | 1.00 | 16.22 | B | C |
| ATOM | 10887 | CD | GLU | B | 154 | 58.095 | 49.917 | −20.062 | 1.00 | 15.63 | B | C |
| ATOM | 10888 | OE1 | GLU | B | 154 | 58.417 | 50.567 | −19.046 | 1.00 | 12.92 | B | O |
| ATOM | 10889 | OE2 | GLU | B | 154 | 58.590 | 48.802 | −20.341 | 1.00 | 16.00 | B | O |
| ATOM | 10890 | C | GLU | B | 154 | 57.105 | 51.317 | −24.807 | 1.00 | 15.67 | B | C |
| ATOM | 10891 | O | GLU | B | 154 | 57.757 | 50.375 | −25.262 | 1.00 | 15.68 | B | O |
| ATOM | 10893 | N | ASN | B | 155 | 56.843 | 52.423 | −25.498 | 1.00 | 15.69 | B | N |
| ATOM | 10894 | CA | ASN | B | 155 | 57.164 | 52.547 | −26.924 | 1.00 | 15.77 | B | C |
| ATOM | 10896 | CB | ASN | B | 155 | 56.417 | 53.741 | −27.552 | 1.00 | 15.68 | B | C |
| ATOM | 10899 | CG | ASN | B | 155 | 56.741 | 55.074 | −26.883 | 1.00 | 15.48 | B | C |
| ATOM | 10900 | OD1 | ASN | B | 155 | 57.898 | 55.377 | −26.591 | 1.00 | 15.65 | B | O |
| ATOM | 10901 | ND2 | ASN | B | 155 | 55.711 | 55.882 | −26.655 | 1.00 | 14.42 | B | N |
| ATOM | 10904 | C | ASN | B | 155 | 58.661 | 52.613 | −27.260 | 1.00 | 15.85 | B | C |
| ATOM | 10905 | O | ASN | B | 155 | 59.062 | 52.208 | −28.351 | 1.00 | 16.36 | B | O |
| ATOM | 10907 | N | ILE | B | 156 | 59.478 | 53.117 | −26.335 | 1.00 | 15.40 | B | N |
| ATOM | 10908 | CA | ILE | B | 156 | 60.903 | 53.345 | −26.610 | 1.00 | 14.84 | B | C |
| ATOM | 10910 | CB | ILE | B | 156 | 61.565 | 54.261 | −25.548 | 1.00 | 14.77 | B | C |
| ATOM | 10912 | CG1 | ILE | B | 156 | 60.846 | 55.612 | −25.479 | 1.00 | 14.33 | B | C |
| ATOM | 10915 | CD1 | ILE | B | 156 | 61.588 | 56.669 | −24.686 | 1.00 | 13.21 | B | C |
| ATOM | 10919 | CG2 | ILE | B | 156 | 63.038 | 54.486 | −25.870 | 1.00 | 14.12 | B | C |
| ATOM | 10923 | C | ILE | B | 156 | 61.690 | 52.037 | −26.718 | 1.00 | 14.66 | B | C |
| ATOM | 10924 | O | ILE | B | 156 | 62.621 | 51.939 | −27.516 | 1.00 | 14.69 | B | O |
| ATOM | 10926 | N | LEU | B | 157 | 61.319 | 51.038 | −25.922 | 1.00 | 14.65 | B | N |
| ATOM | 10927 | CA | LEU | B | 157 | 61.992 | 49.735 | −25.974 | 1.00 | 14.75 | B | C |
| ATOM | 10929 | CB | LEU | B | 157 | 61.576 | 48.846 | −24.796 | 1.00 | 14.48 | B | C |
| ATOM | 10932 | CG | LEU | B | 157 | 62.394 | 49.043 | −23.516 | 1.00 | 13.97 | B | C |
| ATOM | 10934 | CD1 | LEU | B | 157 | 62.541 | 50.515 | −23.164 | 1.00 | 15.30 | B | C |
| ATOM | 10938 | CD2 | LEU | B | 157 | 61.766 | 48.288 | −22.364 | 1.00 | 13.93 | B | C |
| ATOM | 10942 | C | LEU | B | 157 | 61.744 | 49.022 | −27.306 | 1.00 | 15.28 | B | C |
| ATOM | 10943 | O | LEU | B | 157 | 62.644 | 48.368 | −27.832 | 1.00 | 15.56 | B | O |
| ATOM | 10945 | N | ASP | B | 158 | 60.536 | 49.158 | −27.849 | 1.00 | 15.69 | B | N |
| ATOM | 10946 | CA | ASP | B | 158 | 60.230 | 48.641 | −29.184 | 1.00 | 16.04 | B | C |
| ATOM | 10948 | CB | ASP | B | 158 | 58.766 | 48.888 | −29.546 | 1.00 | 16.00 | B | C |
| ATOM | 10951 | CG | ASP | B | 158 | 57.807 | 48.095 | −28.682 | 1.00 | 17.24 | B | C |
| ATOM | 10952 | OD1 | ASP | B | 158 | 58.224 | 47.607 | −27.609 | 1.00 | 19.56 | B | O |
| ATOM | 10953 | OD2 | ASP | B | 158 | 56.630 | 47.963 | −29.081 | 1.00 | 17.24 | B | O |
| ATOM | 10954 | C | ASP | B | 158 | 61.127 | 49.307 | −30.222 | 1.00 | 16.55 | B | C |
| ATOM | 10955 | O | ASP | B | 158 | 61.746 | 48.625 | −31.041 | 1.00 | 16.41 | B | O |
| ATOM | 10957 | N | GLU | B | 159 | 61.192 | 50.640 | −30.171 | 1.00 | 17.24 | B | N |
| ATOM | 10958 | CA | GLU | B | 159 | 62.070 | 51.427 | −31.045 | 1.00 | 17.47 | B | C |
| ATOM | 10960 | CB | GLU | B | 159 | 61.967 | 52.923 | −30.728 | 1.00 | 17.55 | B | C |
| ATOM | 10963 | CG | GLU | B | 159 | 60.630 | 53.563 | −31.057 | 1.00 | 19.36 | B | C |
| ATOM | 10966 | CD | GLU | B | 159 | 60.517 | 54.982 | −30.511 | 1.00 | 22.03 | B | C |
| ATOM | 10967 | OE1 | GLU | B | 159 | 61.422 | 55.804 | −30.782 | 1.00 | 21.37 | B | O |
| ATOM | 10968 | OE2 | GLU | B | 159 | 59.522 | 55.273 | −29.812 | 1.00 | 23.93 | B | O |
| ATOM | 10969 | C | GLU | B | 159 | 63.522 | 50.995 | −30.887 | 1.00 | 17.46 | B | C |
| ATOM | 10970 | O | GLU | B | 159 | 64.280 | 50.984 | −31.856 | 1.00 | 17.74 | B | O |

TABLE 8-2-continued

Coordinates for L494P Structure

| ATOM | 10972 | N | ALA | B | 160 | 63.900 | 50.651 | −29.656 | 1.00 | 17.33 | B | N |
|---|---|---|---|---|---|---|---|---|---|---|---|---|
| ATOM | 10973 | CA | ALA | B | 160 | 65.238 | 50.152 | −29.361 | 1.00 | 17.26 | B | C |
| ATOM | 10975 | CB | ALA | B | 160 | 65.405 | 49.946 | −27.866 | 1.00 | 17.19 | B | C |
| ATOM | 10979 | C | ALA | B | 160 | 65.517 | 48.852 | −30.105 | 1.00 | 17.27 | B | C |
| ATOM | 10980 | O | ALA | B | 160 | 66.602 | 48.671 | −30.658 | 1.00 | 17.36 | B | O |
| ATOM | 10982 | N | LYS | B | 161 | 64.534 | 47.955 | −30.121 | 1.00 | 17.28 | B | N |
| ATOM | 10983 | CA | LYS | B | 161 | 64.679 | 46.673 | −30.806 | 1.00 | 17.64 | B | C |
| ATOM | 10985 | CB | LYS | B | 161 | 63.488 | 45.756 | −30.499 | 1.00 | 17.92 | B | C |
| ATOM | 10988 | CG | LYS | B | 161 | 63.630 | 44.332 | −31.034 | 1.00 | 18.60 | B | C |
| ATOM | 10991 | CD | LYS | B | 161 | 62.821 | 43.311 | −30.222 | 1.00 | 19.37 | B | C |
| ATOM | 10994 | CE | LYS | B | 161 | 61.331 | 43.648 | −30.151 | 1.00 | 19.94 | B | C |
| ATOM | 10997 | NZ | LYS | B | 161 | 60.535 | 42.535 | −29.550 | 1.00 | 19.72 | B | N |
| ATOM | 11001 | C | LYS | B | 161 | 64.827 | 46.884 | −32.311 | 1.00 | 17.64 | B | C |
| ATOM | 11002 | O | LYS | B | 161 | 65.773 | 46.387 | −32.921 | 1.00 | 17.55 | B | O |
| ATOM | 11004 | N | VAL | B | 162 | 63.904 | 47.644 | −32.897 | 1.00 | 17.74 | B | N |
| ATOM | 11005 | CA | VAL | B | 162 | 63.945 | 47.954 | −34.331 | 1.00 | 17.76 | B | C |
| ATOM | 11007 | CB | VAL | B | 162 | 62.713 | 48.788 | −34.770 | 1.00 | 17.61 | B | C |
| ATOM | 11009 | CG1 | VAL | B | 162 | 62.847 | 49.240 | −36.220 | 1.00 | 16.32 | B | C |
| ATOM | 11013 | CG2 | VAL | B | 162 | 61.435 | 47.983 | −34.579 | 1.00 | 17.55 | B | C |
| ATOM | 11017 | C | VAL | B | 162 | 65.231 | 48.697 | −34.713 | 1.00 | 17.95 | B | C |
| ATOM | 11018 | O | VAL | B | 162 | 65.733 | 48.540 | −35.829 | 1.00 | 18.42 | B | O |
| ATOM | 11020 | N | PHE | B | 163 | 65.760 | 49.491 | −33.783 | 1.00 | 17.79 | B | N |
| ATOM | 11021 | CA | PHE | B | 163 | 66.995 | 50.244 | −34.008 | 1.00 | 17.65 | B | C |
| ATOM | 11023 | CB | PHE | B | 163 | 67.121 | 51.380 | −32.985 | 1.00 | 17.30 | B | C |
| ATOM | 11026 | CG | PHE | B | 163 | 68.412 | 52.132 | −33.073 | 1.00 | 15.04 | B | C |
| ATOM | 11027 | CD1 | PHE | B | 163 | 68.578 | 53.138 | −34.008 | 1.00 | 14.91 | B | C |
| ATOM | 11029 | CE1 | PHE | B | 163 | 69.773 | 53.832 | −34.095 | 1.00 | 15.53 | B | C |
| ATOM | 11031 | CZ | PHE | B | 163 | 70.819 | 53.520 | −33.238 | 1.00 | 14.60 | B | C |
| ATOM | 11033 | CE2 | PHE | B | 163 | 70.664 | 52.517 | −32.305 | 1.00 | 13.99 | B | C |
| ATOM | 11035 | CD2 | PHE | B | 163 | 69.467 | 51.827 | −32.227 | 1.00 | 13.98 | B | C |
| ATOM | 11037 | C | PHE | B | 163 | 68.245 | 49.360 | −33.958 | 1.00 | 18.10 | B | C |
| ATOM | 11038 | O | PHE | B | 163 | 69.188 | 49.574 | −34.722 | 1.00 | 18.08 | B | O |
| ATOM | 11040 | N | ALA | B | 164 | 68.256 | 48.381 | −33.055 | 1.00 | 18.58 | B | N |
| ATOM | 11041 | CA | ALA | B | 164 | 69.415 | 47.502 | −32.882 | 1.00 | 18.87 | B | C |
| ATOM | 11043 | CB | ALA | B | 164 | 69.362 | 46.814 | −31.532 | 1.00 | 18.67 | B | C |
| ATOM | 11047 | C | ALA | B | 164 | 69.499 | 46.467 | −33.999 | 1.00 | 19.36 | B | C |
| ATOM | 11048 | O | ALA | B | 164 | 70.548 | 46.304 | −34.616 | 1.00 | 19.42 | B | O |
| ATOM | 11050 | N | ILE | B | 165 | 68.386 | 45.783 | −34.258 | 1.00 | 20.22 | B | N |
| ATOM | 11051 | CA | ILE | B | 165 | 68.322 | 44.739 | −35.290 | 1.00 | 20.91 | B | C |
| ATOM | 11053 | CB | ILE | B | 165 | 66.900 | 44.120 | −35.396 | 1.00 | 21.06 | B | C |
| ATOM | 11055 | CG1 | ILE | B | 165 | 66.529 | 43.370 | −34.114 | 1.00 | 20.91 | B | C |
| ATOM | 11058 | CD1 | ILE | B | 165 | 65.107 | 42.851 | −34.110 | 1.00 | 21.56 | B | C |
| ATOM | 11062 | CG2 | ILE | B | 165 | 66.810 | 43.158 | −36.577 | 1.00 | 21.26 | B | C |
| ATOM | 11066 | C | ILE | B | 165 | 68.732 | 45.267 | −36.668 | 1.00 | 21.49 | B | C |
| ATOM | 11067 | O | ILE | B | 165 | 69.319 | 44.533 | −37.466 | 1.00 | 21.69 | B | O |
| ATOM | 11069 | N | SER | B | 166 | 68.419 | 46.533 | −36.941 | 1.00 | 22.01 | B | N |
| ATOM | 11070 | CA | SER | B | 166 | 68.784 | 47.169 | −38.210 | 1.00 | 22.52 | B | C |
| ATOM | 11072 | CB | SER | B | 166 | 68.144 | 48.560 | −38.322 | 1.00 | 22.55 | B | C |
| ATOM | 11075 | OG | SER | B | 166 | 68.720 | 49.477 | −37.407 | 1.00 | 22.35 | B | O |
| ATOM | 11077 | C | SER | B | 166 | 70.302 | 47.274 | −38.410 | 1.00 | 23.00 | B | C |
| ATOM | 11078 | O | SER | B | 166 | 70.782 | 47.188 | −39.542 | 1.00 | 23.31 | B | O |
| ATOM | 11080 | N | HIS | B | 167 | 71.044 | 47.460 | −37.317 | 1.00 | 23.34 | B | N |
| ATOM | 11081 | CA | HIS | B | 167 | 72.509 | 47.582 | −37.372 | 1.00 | 23.44 | B | C |
| ATOM | 11083 | CB | HIS | B | 167 | 73.004 | 48.652 | −36.387 | 1.00 | 23.48 | B | C |
| ATOM | 11086 | CG | HIS | B | 167 | 72.718 | 50.058 | −36.822 | 1.00 | 24.37 | B | C |
| ATOM | 11087 | ND1 | HIS | B | 167 | 72.058 | 50.966 | −36.022 | 1.00 | 24.84 | B | N |
| ATOM | 11089 | CE1 | HIS | B | 167 | 71.949 | 52.117 | −36.661 | 1.00 | 24.23 | B | C |
| ATOM | 11091 | NE2 | HIS | B | 167 | 72.513 | 51.988 | −37.849 | 1.00 | 24.82 | B | N |
| ATOM | 11093 | CD2 | HIS | B | 167 | 73.001 | 50.710 | −37.974 | 1.00 | 25.08 | B | C |
| ATOM | 11095 | C | HIS | B | 167 | 73.244 | 46.264 | −37.103 | 1.00 | 23.24 | B | C |
| ATOM | 11096 | O | HIS | B | 167 | 74.377 | 46.095 | −37.546 | 1.00 | 23.60 | B | O |
| ATOM | 11098 | N | LEU | B | 168 | 72.605 | 45.340 | −36.387 | 1.00 | 22.97 | B | N |
| ATOM | 11099 | CA | LEU | B | 168 | 73.255 | 44.091 | −35.967 | 1.00 | 22.95 | B | C |
| ATOM | 11101 | CB | LEU | B | 168 | 72.449 | 43.412 | −34.852 | 1.00 | 22.93 | B | C |
| ATOM | 11104 | CG | LEU | B | 168 | 72.509 | 44.048 | −33.460 | 1.00 | 22.05 | B | C |
| ATOM | 11106 | CD1 | LEU | B | 168 | 71.330 | 43.587 | −32.619 | 1.00 | 20.71 | B | C |
| ATOM | 11110 | CD2 | LEU | B | 168 | 73.827 | 43.733 | −32.766 | 1.00 | 20.14 | B | C |
| ATOM | 11114 | C | LEU | B | 168 | 73.462 | 43.089 | −37.103 | 1.00 | 23.36 | B | C |
| ATOM | 11115 | O | LEU | B | 168 | 74.549 | 42.531 | −37.249 | 1.00 | 23.26 | B | O |
| ATOM | 11117 | N | LYS | B | 169 | 72.418 | 42.855 | −37.893 | 1.00 | 24.10 | B | N |
| ATOM | 11118 | CA | LYS | B | 169 | 72.433 | 41.778 | −38.892 | 1.00 | 24.87 | B | C |
| ATOM | 11120 | CB | LYS | B | 169 | 71.002 | 41.350 | −39.249 | 1.00 | 24.93 | B | C |
| ATOM | 11123 | CG | LYS | B | 169 | 70.192 | 42.360 | −40.059 | 1.00 | 25.82 | B | C |
| ATOM | 11126 | CD | LYS | B | 169 | 68.686 | 42.102 | −39.943 | 1.00 | 27.02 | B | C |
| ATOM | 11129 | CE | LYS | B | 169 | 68.291 | 40.714 | −40.452 | 1.00 | 27.94 | B | C |
| ATOM | 11132 | NZ | LYS | B | 169 | 66.823 | 40.466 | −40.352 | 1.00 | 27.64 | B | N |
| ATOM | 11136 | C | LYS | B | 169 | 73.231 | 42.100 | −40.161 | 1.00 | 25.51 | B | C |
| ATOM | 11137 | O | LYS | B | 169 | 73.547 | 41.195 | −40.937 | 1.00 | 25.25 | B | O |

TABLE 8-2-continued

Coordinates for L494P Structure

| ATOM | 11139 | N | GLU | B | 170 | 73.564 | 43.376 | −40.361 | 1.00 | 26.58 | B | N |
|---|---|---|---|---|---|---|---|---|---|---|---|---|
| ATOM | 11140 | CA | GLU | B | 170 | 74.350 | 43.809 | −41.523 | 1.00 | 27.53 | B | C |
| ATOM | 11142 | CB | GLU | B | 170 | 73.806 | 45.137 | −42.080 | 1.00 | 27.70 | B | C |
| ATOM | 11145 | CG | GLU | B | 170 | 72.272 | 45.219 | −42.233 | 1.00 | 29.32 | B | C |
| ATOM | 11148 | CD | GLU | B | 170 | 71.704 | 44.349 | −43.355 | 1.00 | 30.04 | B | C |
| ATOM | 11149 | OE1 | GLU | B | 170 | 72.480 | 43.674 | −44.065 | 1.00 | 31.89 | B | O |
| ATOM | 11150 | OE2 | GLU | B | 170 | 70.467 | 44.347 | −43.530 | 1.00 | 28.58 | B | O |
| ATOM | 11151 | C | GLU | B | 170 | 75.843 | 43.964 | −41.181 | 1.00 | 27.95 | B | C |
| ATOM | 11152 | O | GLU | B | 170 | 76.540 | 44.784 | −41.792 | 1.00 | 28.24 | B | O |
| ATOM | 11154 | N | LEU | B | 171 | 76.326 | 43.173 | −40.217 | 1.00 | 27.99 | B | N |
| ATOM | 11155 | CA | LEU | B | 171 | 77.729 | 43.208 | −39.791 | 1.00 | 27.86 | B | C |
| ATOM | 11157 | CB | LEU | B | 171 | 77.830 | 43.290 | −38.264 | 1.00 | 27.64 | B | C |
| ATOM | 11160 | CG | LEU | B | 171 | 77.203 | 44.514 | −37.588 | 1.00 | 26.91 | B | C |
| ATOM | 11162 | CD1 | LEU | B | 171 | 77.470 | 44.483 | −36.088 | 1.00 | 24.62 | B | C |
| ATOM | 11166 | CD2 | LEU | B | 171 | 77.709 | 45.818 | −38.197 | 1.00 | 25.86 | B | C |
| ATOM | 11170 | C | LEU | B | 171 | 78.485 | 41.976 | −40.283 | 1.00 | 28.06 | B | C |
| ATOM | 11171 | O | LEU | B | 171 | 77.922 | 40.882 | −40.362 | 1.00 | 27.83 | B | O |
| ATOM | 11173 | N | SER | B | 172 | 79.766 | 42.166 | −40.595 | 1.00 | 28.45 | B | N |
| ATOM | 11174 | CA | SER | B | 172 | 80.616 | 41.104 | −41.136 | 1.00 | 28.64 | B | C |
| ATOM | 11176 | CB | SER | B | 172 | 81.520 | 41.664 | −42.237 | 1.00 | 28.62 | B | C |
| ATOM | 11179 | OG | SER | B | 172 | 82.445 | 40.690 | −42.689 | 1.00 | 28.34 | B | O |
| ATOM | 11181 | C | SER | B | 172 | 81.476 | 40.461 | −40.051 | 1.00 | 28.97 | B | C |
| ATOM | 11182 | O | SER | B | 172 | 81.869 | 41.120 | −39.084 | 1.00 | 28.98 | B | O |
| ATOM | 11184 | N | GLU | B | 173 | 81.778 | 39.176 | −40.232 | 1.00 | 29.33 | B | N |
| ATOM | 11185 | CA | GLU | B | 173 | 82.661 | 38.439 | −39.323 | 1.00 | 29.65 | B | C |
| ATOM | 11187 | CB | GLU | B | 173 | 82.531 | 36.925 | −39.553 | 1.00 | 29.65 | B | C |
| ATOM | 11190 | CG | GLU | B | 173 | 83.188 | 36.059 | −38.471 | 1.00 | 30.47 | B | C |
| ATOM | 11193 | CD | GLU | B | 173 | 82.816 | 34.585 | −38.567 | 1.00 | 31.62 | B | C |
| ATOM | 11194 | OE1 | GLU | B | 173 | 81.610 | 34.271 | −38.670 | 1.00 | 31.50 | B | O |
| ATOM | 11195 | OE2 | GLU | B | 173 | 83.732 | 33.735 | −38.523 | 1.00 | 31.84 | B | O |
| ATOM | 11196 | C | GLU | B | 173 | 84.126 | 38.882 | −39.464 | 1.00 | 29.86 | B | C |
| ATOM | 11197 | O | GLU | B | 173 | 84.962 | 38.534 | −38.630 | 1.00 | 30.01 | B | O |
| ATOM | 11199 | N | GLU | B | 174 | 84.435 | 39.639 | −40.518 | 1.00 | 29.81 | B | N |
| ATOM | 11200 | CA | GLU | B | 174 | 85.760 | 40.244 | −40.676 | 1.00 | 29.91 | B | C |
| ATOM | 11202 | CB | GLU | B | 174 | 86.107 | 40.423 | −42.160 | 1.00 | 30.15 | B | C |
| ATOM | 11205 | CG | GLU | B | 174 | 86.698 | 39.179 | −42.809 | 1.00 | 30.29 | B | C |
| ATOM | 11208 | CD | GLU | B | 174 | 86.767 | 39.283 | −44.321 | 1.00 | 29.90 | B | C |
| ATOM | 11209 | OE1 | GLU | B | 174 | 87.889 | 39.316 | −44.868 | 1.00 | 29.26 | B | O |
| ATOM | 11210 | OE2 | GLU | B | 174 | 85.697 | 39.339 | −44.962 | 1.00 | 29.35 | B | O |
| ATOM | 11211 | C | GLU | B | 174 | 85.855 | 41.587 | −39.950 | 1.00 | 29.71 | B | C |
| ATOM | 11212 | O | GLU | B | 174 | 86.787 | 41.810 | −39.175 | 1.00 | 29.67 | B | O |
| ATOM | 11214 | N | LYS | B | 175 | 84.891 | 42.473 | −40.205 | 1.00 | 29.47 | B | N |
| ATOM | 11215 | CA | LYS | B | 175 | 84.867 | 43.811 | −39.595 | 1.00 | 29.30 | B | C |
| ATOM | 11217 | CB | LYS | B | 175 | 83.570 | 44.546 | −39.944 | 1.00 | 29.60 | B | C |
| ATOM | 11220 | CG | LYS | B | 175 | 83.454 | 44.992 | −41.390 | 1.00 | 30.58 | B | C |
| ATOM | 11223 | CD | LYS | B | 175 | 82.079 | 45.598 | −41.651 | 1.00 | 31.84 | B | C |
| ATOM | 11226 | CE | LYS | B | 175 | 81.816 | 45.781 | −43.136 | 1.00 | 32.09 | B | C |
| ATOM | 11229 | NZ | LYS | B | 175 | 80.394 | 46.124 | −43.416 | 1.00 | 32.12 | B | N |
| ATOM | 11233 | C | LYS | B | 175 | 85.001 | 43.754 | −38.076 | 1.00 | 28.77 | B | C |
| ATOM | 11234 | O | LYS | B | 175 | 85.642 | 44.612 | −37.470 | 1.00 | 28.82 | B | O |
| ATOM | 11236 | N | ILE | B | 176 | 84.375 | 42.745 | −37.476 | 1.00 | 28.19 | B | N |
| ATOM | 11237 | CA | ILE | B | 176 | 84.444 | 42.513 | −36.034 | 1.00 | 27.82 | B | C |
| ATOM | 11239 | CB | ILE | B | 176 | 83.105 | 42.841 | −35.331 | 1.00 | 27.95 | B | C |
| ATOM | 11241 | CG1 | ILE | B | 176 | 81.911 | 42.300 | −36.132 | 1.00 | 27.44 | B | C |
| ATOM | 11244 | CD1 | ILE | B | 176 | 80.584 | 42.443 | −35.424 | 1.00 | 26.82 | B | C |
| ATOM | 11248 | CG2 | ILE | B | 176 | 82.971 | 44.346 | −35.137 | 1.00 | 28.50 | B | C |
| ATOM | 11252 | C | ILE | B | 176 | 84.834 | 41.061 | −35.777 | 1.00 | 27.40 | B | C |
| ATOM | 11253 | O | ILE | B | 176 | 84.754 | 40.227 | −36.675 | 1.00 | 27.29 | B | O |
| ATOM | 11255 | N | GLY | B | 177 | 85.249 | 40.767 | −34.548 | 1.00 | 26.94 | B | N |
| ATOM | 11256 | CA | GLY | B | 177 | 85.791 | 39.452 | −34.203 | 1.00 | 26.74 | B | C |
| ATOM | 11259 | C | GLY | B | 177 | 84.867 | 38.276 | −34.467 | 1.00 | 26.46 | B | C |
| ATOM | 11260 | O | GLY | B | 177 | 83.648 | 38.434 | −34.540 | 1.00 | 26.73 | B | O |
| ATOM | 11262 | N | LYS | B | 178 | 85.461 | 37.094 | −34.618 | 1.00 | 26.15 | B | N |
| ATOM | 11263 | CA | LYS | B | 178 | 84.706 | 35.851 | −34.767 | 1.00 | 25.92 | B | C |
| ATOM | 11265 | CB | LYS | B | 178 | 85.657 | 34.667 | −34.967 | 1.00 | 25.77 | B | C |
| ATOM | 11268 | CG | LYS | B | 178 | 84.967 | 33.322 | −35.183 | 1.00 | 25.80 | B | C |
| ATOM | 11271 | CD | LYS | B | 178 | 85.979 | 32.189 | −35.296 | 1.00 | 25.76 | B | C |
| ATOM | 11274 | CE | LYS | B | 178 | 85.347 | 30.924 | −35.863 | 1.00 | 25.07 | B | C |
| ATOM | 11277 | NZ | LYS | B | 178 | 86.333 | 29.818 | −35.998 | 1.00 | 23.38 | B | N |
| ATOM | 11281 | C | LYS | B | 178 | 83.832 | 35.609 | −33.538 | 1.00 | 26.02 | B | C |
| ATOM | 11282 | O | LYS | B | 178 | 82.671 | 35.214 | −33.667 | 1.00 | 26.16 | B | O |
| ATOM | 11284 | N | GLU | B | 179 | 84.393 | 35.850 | −32.353 | 1.00 | 25.87 | B | N |
| ATOM | 11285 | CA | GLU | B | 179 | 83.658 | 35.649 | −31.099 | 1.00 | 25.72 | B | C |
| ATOM | 11287 | CB | GLU | B | 179 | 84.603 | 35.673 | −29.881 | 1.00 | 25.81 | B | C |
| ATOM | 11290 | CG | GLU | B | 179 | 85.277 | 37.014 | −29.571 | 1.00 | 26.23 | B | C |
| ATOM | 11293 | CD | GLU | B | 179 | 86.166 | 36.951 | −28.330 | 1.00 | 26.14 | B | C |
| ATOM | 11294 | OE1 | GLU | B | 179 | 86.250 | 37.961 | −27.601 | 1.00 | 25.98 | B | O |
| ATOM | 11295 | OE2 | GLU | B | 179 | 86.780 | 35.892 | −28.077 | 1.00 | 25.53 | B | O |

TABLE 8-2-continued

Coordinates for L494P Structure

| ATOM | 11296 | C | GLU | B | 179 | 82.509 | 36.649 | −30.932 | 1.00 | 25.07 | B | C |
|---|---|---|---|---|---|---|---|---|---|---|---|---|
| ATOM | 11297 | O | GLU | B | 179 | 81.457 | 36.298 | −30.397 | 1.00 | 24.79 | B | O |
| ATOM | 11299 | N | LEU | B | 180 | 82.712 | 37.881 | −31.401 | 1.00 | 24.36 | B | N |
| ATOM | 11300 | CA | LEU | B | 180 | 81.663 | 38.904 | −31.370 | 1.00 | 23.69 | B | C |
| ATOM | 11302 | CB | LEU | B | 180 | 82.253 | 40.300 | −31.611 | 1.00 | 23.71 | B | C |
| ATOM | 11305 | CG | LEU | B | 180 | 81.387 | 41.489 | −31.175 | 1.00 | 23.25 | B | C |
| ATOM | 11307 | CD1 | LEU | B | 180 | 81.356 | 41.608 | −29.657 | 1.00 | 22.05 | B | C |
| ATOM | 11311 | CD2 | LEU | B | 180 | 81.892 | 42.785 | −31.800 | 1.00 | 22.07 | B | C |
| ATOM | 11315 | C | LEU | B | 180 | 80.578 | 38.604 | −32.407 | 1.00 | 23.13 | B | C |
| ATOM | 11316 | O | LEU | B | 180 | 79.404 | 38.903 | −32.187 | 1.00 | 22.94 | B | O |
| ATOM | 11318 | N | ALA | B | 181 | 80.980 | 38.015 | −33.533 | 1.00 | 22.63 | B | N |
| ATOM | 11319 | CA | ALA | B | 181 | 80.039 | 37.593 | −34.573 | 1.00 | 22.38 | B | C |
| ATOM | 11321 | CB | ALA | B | 181 | 80.792 | 37.158 | −35.819 | 1.00 | 22.13 | B | C |
| ATOM | 11325 | C | ALA | B | 181 | 79.138 | 36.459 | −34.083 | 1.00 | 22.21 | B | C |
| ATOM | 11326 | O | ALA | B | 181 | 77.935 | 36.451 | −34.347 | 1.00 | 22.14 | B | O |
| ATOM | 11328 | N | GLU | B | 182 | 79.732 | 35.506 | −33.371 | 1.00 | 21.95 | B | N |
| ATOM | 11329 | CA | GLU | B | 182 | 79.000 | 34.349 | −32.857 | 1.00 | 21.66 | B | C |
| ATOM | 11331 | CB | GLU | B | 182 | 79.979 | 33.284 | −32.350 | 1.00 | 21.93 | B | C |
| ATOM | 11334 | CG | GLU | B | 182 | 80.709 | 32.557 | −33.481 | 1.00 | 22.98 | B | C |
| ATOM | 11337 | CD | GLU | B | 182 | 81.913 | 31.751 | −33.016 | 1.00 | 23.56 | B | C |
| ATOM | 11338 | OE1 | GLU | B | 182 | 82.298 | 31.861 | −31.831 | 1.00 | 23.87 | B | O |
| ATOM | 11339 | OE2 | GLU | B | 182 | 82.477 | 31.005 | −33.847 | 1.00 | 22.99 | B | O |
| ATOM | 11340 | C | GLU | B | 182 | 78.003 | 34.731 | −31.762 | 1.00 | 20.94 | B | C |
| ATOM | 11341 | O | GLU | B | 182 | 76.949 | 34.107 | −31.643 | 1.00 | 20.76 | B | O |
| ATOM | 11343 | N | GLN | B | 183 | 78.334 | 35.750 | −30.972 | 1.00 | 20.28 | B | N |
| ATOM | 11344 | CA | GLN | B | 183 | 77.412 | 36.262 | −29.957 | 1.00 | 20.01 | B | C |
| ATOM | 11346 | CB | GLN | B | 183 | 78.130 | 37.187 | −28.968 | 1.00 | 19.95 | B | C |
| ATOM | 11349 | CG | GLN | B | 183 | 79.140 | 36.483 | −28.068 | 1.00 | 20.86 | B | C |
| ATOM | 11352 | CD | GLN | B | 183 | 79.118 | 37.001 | −26.638 | 1.00 | 22.16 | B | C |
| ATOM | 11353 | OE1 | GLN | B | 183 | 79.484 | 38.147 | −26.375 | 1.00 | 22.85 | B | O |
| ATOM | 11354 | NE2 | GLN | B | 183 | 78.689 | 36.153 | −25.707 | 1.00 | 21.77 | B | N |
| ATOM | 11357 | C | GLN | B | 183 | 76.234 | 36.999 | −30.591 | 1.00 | 19.93 | B | C |
| ATOM | 11358 | O | GLN | B | 183 | 75.125 | 36.978 | −30.052 | 1.00 | 19.93 | B | O |
| ATOM | 11360 | N | VAL | B | 184 | 76.477 | 37.651 | −31.727 | 1.00 | 19.67 | B | N |
| ATOM | 11361 | CA | VAL | B | 184 | 75.416 | 38.334 | −32.469 | 1.00 | 19.49 | B | C |
| ATOM | 11363 | CB | VAL | B | 184 | 75.991 | 39.266 | −33.553 | 1.00 | 19.50 | B | C |
| ATOM | 11365 | CG1 | VAL | B | 184 | 76.767 | 40.403 | −32.906 | 1.00 | 19.63 | B | C |
| ATOM | 11369 | CG2 | VAL | B | 184 | 74.880 | 39.815 | −34.440 | 1.00 | 19.00 | B | C |
| ATOM | 11373 | C | VAL | B | 184 | 74.464 | 37.325 | −33.111 | 1.00 | 19.48 | B | C |
| ATOM | 11374 | O | VAL | B | 184 | 73.246 | 37.484 | −33.036 | 1.00 | 19.34 | B | O |
| ATOM | 11376 | N | ASN | B | 185 | 75.027 | 36.289 | −33.732 | 1.00 | 19.56 | B | N |
| ATOM | 11377 | CA | ASN | B | 185 | 74.230 | 35.210 | −34.323 | 1.00 | 19.71 | B | C |
| ATOM | 11379 | CB | ASN | B | 185 | 75.115 | 34.272 | −35.153 | 1.00 | 19.76 | B | C |
| ATOM | 11382 | CG | ASN | B | 185 | 75.756 | 34.965 | −36.348 | 1.00 | 20.50 | B | C |
| ATOM | 11383 | OD1 | ASN | B | 185 | 75.392 | 36.085 | −36.706 | 1.00 | 22.61 | B | O |
| ATOM | 11384 | ND2 | ASN | B | 185 | 76.719 | 34.295 | −36.971 | 1.00 | 21.21 | B | N |
| ATOM | 11387 | C | ASN | B | 185 | 73.473 | 34.402 | −33.266 | 1.00 | 19.77 | B | C |
| ATOM | 11388 | O | ASN | B | 185 | 72.386 | 33.891 | −33.533 | 1.00 | 20.02 | B | O |
| ATOM | 11390 | N | HIS | B | 186 | 74.057 | 34.287 | −32.075 | 1.00 | 19.72 | B | N |
| ATOM | 11391 | CA | HIS | B | 186 | 73.404 | 33.628 | −30.942 | 1.00 | 19.80 | B | C |
| ATOM | 11393 | CB | HIS | B | 186 | 74.414 | 33.411 | −29.808 | 1.00 | 19.92 | B | C |
| ATOM | 11396 | CG | HIS | B | 186 | 73.854 | 32.703 | −28.611 | 1.00 | 19.22 | B | C |
| ATOM | 11397 | ND1 | HIS | B | 186 | 73.549 | 31.358 | −28.615 | 1.00 | 19.55 | B | N |
| ATOM | 11399 | CE1 | HIS | B | 186 | 73.091 | 31.010 | −27.426 | 1.00 | 18.27 | B | C |
| ATOM | 11401 | NE2 | HIS | B | 186 | 73.093 | 32.077 | −26.649 | 1.00 | 18.30 | B | N |
| ATOM | 11403 | CD2 | HIS | B | 186 | 73.571 | 33.149 | −27.364 | 1.00 | 18.39 | B | C |
| ATOM | 11405 | C | HIS | B | 186 | 72.225 | 34.464 | −30.448 | 1.00 | 19.84 | B | C |
| ATOM | 11406 | O | HIS | B | 186 | 71.124 | 33.943 | −30.269 | 1.00 | 19.69 | B | O |
| ATOM | 11408 | N | ALA | B | 187 | 72.463 | 35.758 | −30.240 | 1.00 | 19.89 | B | N |
| ATOM | 11409 | CA | ALA | B | 187 | 71.419 | 36.682 | −29.780 | 1.00 | 19.70 | B | C |
| ATOM | 11411 | CB | ALA | B | 187 | 72.029 | 38.022 | −29.387 | 1.00 | 19.58 | B | C |
| ATOM | 11415 | C | ALA | B | 187 | 70.320 | 36.886 | −30.829 | 1.00 | 19.42 | B | C |
| ATOM | 11416 | O | ALA | B | 187 | 69.152 | 37.071 | −30.477 | 1.00 | 19.51 | B | O |
| ATOM | 11418 | N | LEU | B | 188 | 70.693 | 36.853 | −32.109 | 1.00 | 18.76 | B | N |
| ATOM | 11419 | CA | LEU | B | 188 | 69.721 | 36.993 | −33.200 | 1.00 | 18.16 | B | C |
| ATOM | 11421 | CB | LEU | B | 188 | 70.409 | 37.449 | −34.492 | 1.00 | 17.88 | B | C |
| ATOM | 11424 | CG | LEU | B | 188 | 70.820 | 38.925 | −34.496 | 1.00 | 17.28 | B | C |
| ATOM | 11426 | CD1 | LEU | B | 188 | 71.831 | 39.217 | −35.593 | 1.00 | 16.54 | B | C |
| ATOM | 11430 | CD2 | LEU | B | 188 | 69.600 | 39.820 | −34.640 | 1.00 | 15.64 | B | C |
| ATOM | 11434 | C | LEU | B | 188 | 68.916 | 35.711 | −33.436 | 1.00 | 17.88 | B | C |
| ATOM | 11435 | O | LEU | B | 188 | 67.764 | 35.775 | −33.863 | 1.00 | 18.07 | B | O |
| ATOM | 11437 | N | GLU | B | 189 | 69.518 | 34.554 | −33.164 | 1.00 | 17.45 | B | N |
| ATOM | 11438 | CA | GLU | B | 189 | 68.783 | 33.286 | −33.161 | 1.00 | 17.00 | B | C |
| ATOM | 11440 | CB | GLU | B | 189 | 69.717 | 32.116 | −32.830 | 1.00 | 16.79 | B | C |
| ATOM | 11443 | CG | GLU | B | 189 | 69.039 | 30.745 | −32.807 | 1.00 | 16.46 | B | C |
| ATOM | 11446 | CD | GLU | B | 189 | 70.001 | 29.608 | −32.506 | 1.00 | 16.49 | B | C |
| ATOM | 11447 | OE1 | GLU | B | 189 | 70.952 | 29.810 | −31.720 | 1.00 | 17.45 | B | O |
| ATOM | 11448 | OE2 | GLU | B | 189 | 69.802 | 28.502 | −33.051 | 1.00 | 16.29 | B | O |

TABLE 8-2-continued

| | | | | | | | | | | | |
|---|---|---|---|---|---|---|---|---|---|---|---|
| ATOM | 11449 | C | GLU | B | 189 | 67.647 | 33.354 | −32.141 | 1.00 | 16.85 B | C |
| ATOM | 11450 | O | GLU | B | 189 | 66.513 | 32.963 | −32.430 | 1.00 | 16.54 B | O |
| ATOM | 11452 | N | LEU | B | 190 | 67.973 | 33.852 | −30.949 | 1.00 | 16.84 B | N |
| ATOM | 11453 | CA | LEU | B | 190 | 67.008 | 34.033 | −29.864 | 1.00 | 16.87 B | C |
| ATOM | 11455 | CB | LEU | B | 190 | 66.646 | 32.680 | −29.242 | 1.00 | 16.90 B | C |
| ATOM | 11458 | CG | LEU | B | 190 | 65.420 | 32.614 | −28.326 | 1.00 | 16.89 B | C |
| ATOM | 11460 | CD1 | LEU | B | 190 | 64.144 | 32.781 | −29.127 | 1.00 | 16.28 B | C |
| ATOM | 11464 | CD2 | LEU | B | 190 | 65.395 | 31.296 | −27.566 | 1.00 | 17.45 B | C |
| ATOM | 11468 | C | LEU | B | 190 | 67.637 | 34.940 | −28.801 | 1.00 | 16.77 B | C |
| ATOM | 11469 | O | LEU | B | 190 | 68.826 | 34.803 | −28.509 | 1.00 | 17.14 B | O |
| ATOM | 11471 | N | PRO | B | 191 | 66.857 | 35.873 | −28.222 | 1.00 | 16.38 B | N |
| ATOM | 11472 | CA | PRO | B | 191 | 67.420 | 36.724 | −27.166 | 1.00 | 16.04 B | C |
| ATOM | 11474 | CB | PRO | B | 191 | 66.391 | 37.848 | −27.040 | 1.00 | 15.95 B | C |
| ATOM | 11477 | CG | PRO | B | 191 | 65.114 | 37.221 | −27.453 | 1.00 | 16.28 B | C |
| ATOM | 11480 | CD | PRO | B | 191 | 65.460 | 36.231 | −28.527 | 1.00 | 16.22 B | C |
| ATOM | 11483 | C | PRO | B | 191 | 67.576 | 35.981 | −25.838 | 1.00 | 15.62 B | C |
| ATOM | 11484 | O | PRO | B | 191 | 67.046 | 34.884 | −25.682 | 1.00 | 15.70 B | O |
| ATOM | 11485 | N | LEU | B | 192 | 68.303 | 36.578 | −24.896 | 1.00 | 15.37 B | N |
| ATOM | 11486 | CA | LEU | B | 192 | 68.515 | 35.973 | −23.578 | 1.00 | 14.71 B | C |
| ATOM | 11488 | CB | LEU | B | 192 | 69.477 | 36.810 | −22.735 | 1.00 | 14.48 B | C |
| ATOM | 11491 | CG | LEU | B | 192 | 70.931 | 36.828 | −23.194 | 1.00 | 14.76 B | C |
| ATOM | 11493 | CD1 | LEU | B | 192 | 71.650 | 38.005 | −22.575 | 1.00 | 16.74 B | C |
| ATOM | 11497 | CD2 | LEU | B | 192 | 71.627 | 35.526 | −22.840 | 1.00 | 14.51 B | C |
| ATOM | 11501 | C | LEU | B | 192 | 67.203 | 35.839 | −22.833 | 1.00 | 14.18 B | C |
| ATOM | 11502 | O | LEU | B | 192 | 66.930 | 34.801 | −22.234 | 1.00 | 14.39 B | O |
| ATOM | 11504 | N | HIS | B | 193 | 66.388 | 36.889 | −22.891 | 1.00 | 13.57 B | N |
| ATOM | 11505 | CA | HIS | B | 193 | 65.119 | 36.926 | −22.170 | 1.00 | 13.63 B | C |
| ATOM | 11507 | CB | HIS | B | 193 | 64.446 | 38.292 | −22.363 | 1.00 | 13.58 B | C |
| ATOM | 11510 | CG | HIS | B | 193 | 63.202 | 38.477 | −21.548 | 1.00 | 13.03 B | C |
| ATOM | 11511 | ND1 | HIS | B | 193 | 63.208 | 38.485 | −20.170 | 1.00 | 13.37 B | N |
| ATOM | 11513 | CE1 | HIS | B | 193 | 61.976 | 38.662 | −19.727 | 1.00 | 13.22 B | C |
| ATOM | 11515 | NE2 | HIS | B | 193 | 61.171 | 38.773 | −20.769 | 1.00 | 11.40 B | N |
| ATOM | 11517 | CD2 | HIS | B | 193 | 61.913 | 38.661 | −21.920 | 1.00 | 11.23 B | C |
| ATOM | 11519 | C | HIS | B | 193 | 64.160 | 35.795 | −22.570 | 1.00 | 13.78 B | C |
| ATOM | 11520 | O | HIS | B | 193 | 63.257 | 35.440 | −21.802 | 1.00 | 13.38 B | O |
| ATOM | 11522 | N | ARG | B | 194 | 64.365 | 35.224 | −23.756 | 1.00 | 14.17 B | N |
| ATOM | 11523 | CA | ARG | B | 194 | 63.487 | 34.175 | −24.273 | 1.00 | 14.88 B | C |
| ATOM | 11525 | CB | ARG | B | 194 | 62.992 | 34.567 | −25.663 | 1.00 | 15.05 B | C |
| ATOM | 11528 | CG | ARG | B | 194 | 62.208 | 35.872 | −25.689 | 1.00 | 16.31 B | C |
| ATOM | 11531 | CD | ARG | B | 194 | 61.684 | 36.153 | −27.083 | 1.00 | 18.23 B | C |
| ATOM | 11534 | NE | ARG | B | 194 | 60.754 | 37.277 | −27.116 | 1.00 | 18.82 B | N |
| ATOM | 11536 | CZ | ARG | B | 194 | 60.060 | 37.648 | −28.190 | 1.00 | 18.69 B | C |
| ATOM | 11537 | NH1 | ARG | B | 194 | 60.186 | 36.987 | −29.338 | 1.00 | 19.08 B | N |
| ATOM | 11540 | NH2 | ARG | B | 194 | 59.235 | 38.687 | −28.117 | 1.00 | 19.19 B | N |
| ATOM | 11543 | C | ARG | B | 194 | 64.126 | 32.785 | −24.336 | 1.00 | 14.83 B | C |
| ATOM | 11544 | O | ARG | B | 194 | 63.439 | 31.814 | −24.648 | 1.00 | 15.42 B | O |
| ATOM | 11546 | N | ARG | B | 195 | 65.421 | 32.681 | −24.042 | 1.00 | 14.50 B | N |
| ATOM | 11547 | CA | ARG | B | 195 | 66.118 | 31.398 | −24.116 | 1.00 | 14.49 B | C |
| ATOM | 11549 | CB | ARG | B | 195 | 67.545 | 31.588 | −24.627 | 1.00 | 14.69 B | C |
| ATOM | 11552 | CG | ARG | B | 195 | 68.145 | 30.336 | −25.240 | 1.00 | 15.98 B | C |
| ATOM | 11555 | CD | ARG | B | 195 | 69.649 | 30.461 | −25.417 | 1.00 | 17.88 B | C |
| ATOM | 11558 | NE | ARG | B | 195 | 70.028 | 31.579 | −26.279 | 1.00 | 18.66 B | N |
| ATOM | 11560 | CZ | ARG | B | 195 | 69.963 | 31.572 | −27.610 | 1.00 | 20.86 B | C |
| ATOM | 11561 | NH1 | ARG | B | 195 | 69.522 | 30.505 | −28.274 | 1.00 | 21.51 B | N |
| ATOM | 11564 | NH2 | ARG | B | 195 | 70.344 | 32.646 | −28.289 | 1.00 | 22.00 B | N |
| ATOM | 11567 | C | ARG | B | 195 | 66.141 | 30.733 | −22.747 | 1.00 | 14.49 B | C |
| ATOM | 11568 | O | ARG | B | 195 | 66.247 | 31.412 | −21.723 | 1.00 | 14.49 B | O |
| ATOM | 11570 | N | THR | B | 196 | 66.047 | 29.404 | −22.736 | 1.00 | 14.52 B | N |
| ATOM | 11571 | CA | THR | B | 196 | 66.036 | 28.641 | −21.490 | 1.00 | 14.61 B | C |
| ATOM | 11573 | CB | THR | B | 196 | 65.535 | 27.199 | −21.701 | 1.00 | 14.72 B | C |
| ATOM | 11575 | OG1 | THR | B | 196 | 66.358 | 26.536 | −22.668 | 1.00 | 14.27 B | O |
| ATOM | 11577 | CG2 | THR | B | 196 | 64.090 | 27.198 | −22.178 | 1.00 | 15.09 B | C |
| ATOM | 11581 | C | THR | B | 196 | 67.427 | 28.599 | −20.868 | 1.00 | 14.74 B | C |
| ATOM | 11582 | O | THR | B | 196 | 68.431 | 28.613 | −21.577 | 1.00 | 14.94 B | O |
| ATOM | 11584 | N | GLN | B | 197 | 67.464 | 28.529 | −19.540 | 1.00 | 14.94 B | N |
| ATOM | 11585 | CA | GLN | B | 197 | 68.707 | 28.631 | −18.768 | 1.00 | 14.89 B | C |
| ATOM | 11587 | CB | GLN | B | 197 | 68.415 | 28.398 | −17.273 | 1.00 | 14.86 B | C |
| ATOM | 11590 | CG | GLN | B | 197 | 69.335 | 29.146 | −16.312 | 1.00 | 13.67 B | C |
| ATOM | 11593 | CD | GLN | B | 197 | 70.536 | 28.336 | −15.866 | 1.00 | 11.84 B | C |
| ATOM | 11594 | OE1 | GLN | B | 197 | 71.150 | 27.618 | −16.653 | 1.00 | 11.73 B | O |
| ATOM | 11595 | NE2 | GLN | B | 197 | 70.885 | 28.460 | −14.596 | 1.00 | 10.93 B | N |
| ATOM | 11598 | C | GLN | B | 197 | 69.785 | 27.656 | −19.250 | 1.00 | 15.04 B | C |
| ATOM | 11599 | O | GLN | B | 197 | 70.916 | 28.058 | −19.533 | 1.00 | 14.84 B | O |
| ATOM | 11601 | N | ARG | B | 198 | 69.421 | 26.380 | −19.353 | 1.00 | 15.25 B | N |
| ATOM | 11602 | CA | ARG | B | 198 | 70.382 | 25.316 | −19.657 | 1.00 | 15.00 B | C |
| ATOM | 11604 | CB | ARG | B | 198 | 69.755 | 23.946 | −19.396 | 1.00 | 14.97 B | C |
| ATOM | 11607 | CG | ARG | B | 198 | 69.439 | 23.673 | −17.932 | 1.00 | 15.36 B | C |
| ATOM | 11610 | CD | ARG | B | 198 | 70.675 | 23.289 | −17.132 | 1.00 | 15.24 B | C |

TABLE 8-2-continued

Coordinates for L494P Structure

| ATOM | 11613 | NE | ARG | B | 198 | 71.376 | 24.438 | −16.564 | 1.00 | 15.04 | B | N |
|---|---|---|---|---|---|---|---|---|---|---|---|---|
| ATOM | 11615 | CZ | ARG | B | 198 | 72.401 | 24.347 | −15.717 | 1.00 | 15.93 | B | C |
| ATOM | 11616 | NH1 | ARG | B | 198 | 72.855 | 23.160 | −15.334 | 1.00 | 16.51 | B | N |
| ATOM | 11619 | NH2 | ARG | B | 198 | 72.977 | 25.447 | −15.248 | 1.00 | 16.24 | B | N |
| ATOM | 11622 | C | ARG | B | 198 | 70.916 | 25.373 | −21.086 | 1.00 | 14.67 | B | C |
| ATOM | 11623 | O | ARG | B | 198 | 72.093 | 25.083 | −21.320 | 1.00 | 14.37 | B | O |
| ATOM | 11625 | N | LEU | B | 199 | 70.055 | 25.726 | −22.038 | 1.00 | 14.51 | B | N |
| ATOM | 11626 | CA | LEU | B | 199 | 70.490 | 25.910 | −23.427 | 1.00 | 14.52 | B | C |
| ATOM | 11628 | CB | LEU | B | 199 | 69.297 | 26.133 | −24.378 | 1.00 | 14.65 | B | C |
| ATOM | 11631 | CG | LEU | B | 199 | 68.606 | 24.925 | −25.037 | 1.00 | 14.01 | B | C |
| ATOM | 11633 | CD1 | LEU | B | 199 | 67.687 | 24.176 | −24.064 | 1.00 | 13.56 | B | C |
| ATOM | 11637 | CD2 | LEU | B | 199 | 69.625 | 23.978 | −25.659 | 1.00 | 12.13 | B | C |
| ATOM | 11641 | C | LEU | B | 199 | 71.458 | 27.091 | −23.512 | 1.00 | 14.39 | B | C |
| ATOM | 11642 | O | LEU | B | 199 | 72.476 | 27.022 | −24.207 | 1.00 | 14.42 | B | O |
| ATOM | 11644 | N | GLU | B | 200 | 71.132 | 28.168 | −22.800 | 1.00 | 13.72 | B | N |
| ATOM | 11645 | CA | GLU | B | 200 | 71.998 | 29.335 | −22.737 | 1.00 | 13.37 | B | C |
| ATOM | 11647 | CB | GLU | B | 200 | 71.312 | 30.473 | −21.969 | 1.00 | 13.42 | B | C |
| ATOM | 11650 | CG | GLU | B | 200 | 72.160 | 31.723 | −21.776 | 1.00 | 13.45 | B | C |
| ATOM | 11653 | CD | GLU | B | 200 | 72.875 | 32.157 | −23.042 | 1.00 | 14.44 | B | C |
| ATOM | 11654 | OE1 | GLU | B | 200 | 72.268 | 32.095 | −24.133 | 1.00 | 14.98 | B | O |
| ATOM | 11655 | OE2 | GLU | B | 200 | 74.049 | 32.561 | −22.945 | 1.00 | 15.44 | B | O |
| ATOM | 11656 | C | GLU | B | 200 | 73.317 | 28.968 | −22.071 | 1.00 | 13.44 | B | C |
| ATOM | 11657 | O | GLU | B | 200 | 74.389 | 29.324 | −22.561 | 1.00 | 13.42 | B | O |
| ATOM | 11659 | N | ALA | B | 201 | 73.229 | 28.248 | −20.959 | 1.00 | 13.64 | B | N |
| ATOM | 11660 | CA | ALA | B | 201 | 74.414 | 27.828 | −20.222 | 1.00 | 14.07 | B | C |
| ATOM | 11662 | CB | ALA | B | 201 | 74.017 | 27.028 | −18.991 | 1.00 | 14.39 | B | C |
| ATOM | 11666 | C | ALA | B | 201 | 75.371 | 27.018 | −21.094 | 1.00 | 14.43 | B | C |
| ATOM | 11667 | O | ALA | B | 201 | 76.564 | 27.319 | −21.144 | 1.00 | 14.77 | B | O |
| ATOM | 11669 | N | VAL | B | 202 | 74.849 | 26.008 | −21.791 | 1.00 | 14.63 | B | N |
| ATOM | 11670 | CA | VAL | B | 202 | 75.691 | 25.119 | −22.602 | 1.00 | 14.73 | B | C |
| ATOM | 11672 | CB | VAL | B | 202 | 74.885 | 23.939 | −23.206 | 1.00 | 14.72 | B | C |
| ATOM | 11674 | CG1 | VAL | B | 202 | 73.980 | 24.415 | −24.333 | 1.00 | 15.60 | B | C |
| ATOM | 11678 | CG2 | VAL | B | 202 | 75.828 | 22.852 | −23.706 | 1.00 | 13.72 | B | C |
| ATOM | 11682 | C | VAL | B | 202 | 76.425 | 25.865 | −23.723 | 1.00 | 14.67 | B | C |
| ATOM | 11683 | O | VAL | B | 202 | 77.535 | 25.484 | −24.101 | 1.00 | 14.54 | B | O |
| ATOM | 11685 | N | TRP | B | 203 | 75.809 | 26.926 | −24.238 | 1.00 | 14.66 | B | N |
| ATOM | 11686 | CA | TRP | B | 203 | 76.417 | 27.728 | −25.295 | 1.00 | 14.84 | B | C |
| ATOM | 11688 | CB | TRP | B | 203 | 75.344 | 28.484 | −26.083 | 1.00 | 14.97 | B | C |
| ATOM | 11691 | CG | TRP | B | 203 | 75.916 | 29.258 | −27.217 | 1.00 | 14.08 | B | C |
| ATOM | 11692 | CD1 | TRP | B | 203 | 76.114 | 28.818 | −28.491 | 1.00 | 13.97 | B | C |
| ATOM | 11694 | NE1 | TRP | B | 203 | 76.677 | 29.812 | −29.251 | 1.00 | 14.19 | B | N |
| ATOM | 11696 | CE2 | TRP | B | 203 | 76.860 | 30.919 | −28.465 | 1.00 | 13.10 | B | C |
| ATOM | 11697 | CD2 | TRP | B | 203 | 76.393 | 30.603 | −27.176 | 1.00 | 12.77 | B | C |
| ATOM | 11698 | CE3 | TRP | B | 203 | 76.465 | 31.575 | −26.173 | 1.00 | 13.68 | B | C |
| ATOM | 11700 | CZ3 | TRP | B | 203 | 76.993 | 32.812 | −26.486 | 1.00 | 14.21 | B | C |
| ATOM | 11702 | CH2 | TRP | B | 203 | 77.449 | 33.096 | −27.778 | 1.00 | 14.39 | B | C |
| ATOM | 11704 | CZ2 | TRP | B | 203 | 77.393 | 32.165 | −28.779 | 1.00 | 13.69 | B | C |
| ATOM | 11706 | C | TRP | B | 203 | 77.438 | 28.722 | −24.739 | 1.00 | 15.07 | B | C |
| ATOM | 11707 | O | TRP | B | 203 | 78.578 | 28.779 | −25.211 | 1.00 | 15.56 | B | O |
| ATOM | 11709 | N | SER | B | 204 | 77.018 | 29.507 | −23.749 | 1.00 | 14.73 | B | N |
| ATOM | 11710 | CA | SER | B | 204 | 77.861 | 30.563 | −23.179 | 1.00 | 14.32 | B | C |
| ATOM | 11712 | CB | SER | B | 204 | 77.084 | 31.382 | −22.146 | 1.00 | 14.36 | B | C |
| ATOM | 11715 | OG | SER | B | 204 | 76.240 | 32.322 | −22.781 | 1.00 | 13.68 | B | O |
| ATOM | 11717 | C | SER | B | 204 | 79.149 | 30.044 | −22.549 | 1.00 | 14.07 | B | C |
| ATOM | 11718 | O | SER | B | 204 | 80.164 | 30.735 | −22.583 | 1.00 | 14.22 | B | O |
| ATOM | 11720 | N | ILE | B | 205 | 79.103 | 28.840 | −21.976 | 1.00 | 13.65 | B | N |
| ATOM | 11721 | CA | ILE | B | 205 | 80.286 | 28.223 | −21.365 | 1.00 | 13.54 | B | C |
| ATOM | 11723 | CB | ILE | B | 205 | 79.918 | 26.963 | −20.542 | 1.00 | 13.39 | B | C |
| ATOM | 11725 | CG1 | ILE | B | 205 | 79.225 | 27.367 | −19.241 | 1.00 | 13.19 | B | C |
| ATOM | 11728 | CD1 | ILE | B | 205 | 78.813 | 26.197 | −18.372 | 1.00 | 13.69 | B | C |
| ATOM | 11732 | CG2 | ILE | B | 205 | 81.162 | 26.151 | −20.208 | 1.00 | 13.60 | B | C |
| ATOM | 11736 | C | ILE | B | 205 | 81.352 | 27.870 | −22.410 | 1.00 | 13.51 | B | C |
| ATOM | 11737 | O | ILE | B | 205 | 82.542 | 28.105 | −22.193 | 1.00 | 12.96 | B | O |
| ATOM | 11739 | N | GLU | B | 206 | 80.918 | 27.309 | −23.536 | 1.00 | 13.71 | B | N |
| ATOM | 11740 | CA | GLU | B | 206 | 81.822 | 26.989 | −24.640 | 1.00 | 13.71 | B | C |
| ATOM | 11742 | CB | GLU | B | 206 | 81.084 | 26.164 | −25.706 | 1.00 | 13.88 | B | C |
| ATOM | 11745 | CG | GLU | B | 206 | 81.888 | 25.840 | −26.973 | 1.00 | 15.04 | B | C |
| ATOM | 11748 | CD | GLU | B | 206 | 83.222 | 25.163 | −26.693 | 1.00 | 15.38 | B | C |
| ATOM | 11749 | OE1 | GLU | B | 206 | 83.322 | 24.405 | −25.704 | 1.00 | 15.76 | B | O |
| ATOM | 11750 | OE2 | GLU | B | 206 | 84.172 | 25.387 | −27.474 | 1.00 | 15.99 | B | O |
| ATOM | 11751 | C | GLU | B | 206 | 82.418 | 28.263 | −25.253 | 1.00 | 13.41 | B | C |
| ATOM | 11752 | O | GLU | B | 206 | 83.603 | 28.303 | −25.581 | 1.00 | 12.99 | B | O |
| ATOM | 11754 | N | ALA | B | 207 | 81.592 | 29.297 | −25.397 | 1.00 | 13.13 | B | N |
| ATOM | 11755 | CA | ALA | B | 207 | 82.037 | 30.583 | −25.938 | 1.00 | 12.74 | B | C |
| ATOM | 11757 | CB | ALA | B | 207 | 80.834 | 31.472 | −26.228 | 1.00 | 12.73 | B | C |
| ATOM | 11761 | C | ALA | B | 207 | 83.008 | 31.300 | −24.997 | 1.00 | 12.41 | B | C |
| ATOM | 11762 | O | ALA | B | 207 | 84.012 | 31.856 | −25.441 | 1.00 | 11.95 | B | O |
| ATOM | 11764 | N | TYR | B | 208 | 82.695 | 31.283 | −23.702 | 1.00 | 12.40 | B | N |

TABLE 8-2-continued

Coordinates for L494P Structure

| ATOM | 11765 | CA | TYR | B | 208 | 83.506 | 31.947 | −22.674 | 1.00 | 12.38 | B | C |
|---|---|---|---|---|---|---|---|---|---|---|---|---|
| ATOM | 11767 | CB | TYR | B | 208 | 82.719 | 32.017 | −21.359 | 1.00 | 12.14 | B | C |
| ATOM | 11770 | CG | TYR | B | 208 | 83.307 | 32.930 | −20.307 | 1.00 | 11.69 | B | C |
| ATOM | 11771 | CD1 | TYR | B | 208 | 83.112 | 34.307 | −20.366 | 1.00 | 12.57 | B | C |
| ATOM | 11773 | CE1 | TYR | B | 208 | 83.640 | 35.152 | −19.398 | 1.00 | 13.17 | B | C |
| ATOM | 11775 | CZ | TYR | B | 208 | 84.367 | 34.620 | −18.349 | 1.00 | 13.50 | B | C |
| ATOM | 11776 | OH | TYR | B | 208 | 84.891 | 35.454 | −17.388 | 1.00 | 14.79 | B | O |
| ATOM | 11778 | CE2 | TYR | B | 208 | 84.568 | 33.254 | −18.262 | 1.00 | 12.55 | B | C |
| ATOM | 11780 | CD2 | TYR | B | 208 | 84.035 | 32.417 | −19.238 | 1.00 | 11.68 | B | C |
| ATOM | 11782 | C | TYR | B | 208 | 84.834 | 31.221 | −22.450 | 1.00 | 12.66 | B | C |
| ATOM | 11783 | O | TYR | B | 208 | 85.840 | 31.841 | −22.109 | 1.00 | 12.19 | B | O |
| ATOM | 11785 | N | ARG | B | 209 | 84.818 | 29.904 | −22.637 | 1.00 | 13.27 | B | N |
| ATOM | 11786 | CA | ARG | B | 209 | 86.020 | 29.073 | −22.563 | 1.00 | 13.72 | B | C |
| ATOM | 11788 | CB | ARG | B | 209 | 85.627 | 27.607 | −22.794 | 1.00 | 13.38 | B | C |
| ATOM | 11791 | CG | ARG | B | 209 | 86.776 | 26.618 | −22.939 | 1.00 | 13.64 | B | C |
| ATOM | 11794 | CD | ARG | B | 209 | 86.308 | 25.339 | −23.618 | 1.00 | 12.76 | B | C |
| ATOM | 11797 | NE | ARG | B | 209 | 85.380 | 24.576 | −22.789 | 1.00 | 8.75 | B | N |
| ATOM | 11799 | CZ | ARG | B | 209 | 85.737 | 23.800 | −21.769 | 1.00 | 7.83 | B | C |
| ATOM | 11800 | NH1 | ARG | B | 209 | 87.014 | 23.671 | −21.418 | 1.00 | 7.53 | B | N |
| ATOM | 11803 | NH2 | ARG | B | 209 | 84.805 | 23.149 | −21.088 | 1.00 | 9.72 | B | N |
| ATOM | 11806 | C | ARG | B | 209 | 87.091 | 29.520 | −23.574 | 1.00 | 14.74 | B | C |
| ATOM | 11807 | O | ARG | B | 209 | 88.291 | 29.385 | −23.317 | 1.00 | 14.87 | B | O |
| ATOM | 11809 | N | LYS | B | 210 | 86.653 | 30.052 | −24.715 | 1.00 | 15.63 | B | N |
| ATOM | 11810 | CA | LYS | B | 210 | 87.566 | 30.517 | −25.763 | 1.00 | 16.08 | B | C |
| ATOM | 11812 | CB | LYS | B | 210 | 86.837 | 30.620 | −27.106 | 1.00 | 16.07 | B | C |
| ATOM | 11815 | CG | LYS | B | 210 | 86.325 | 29.290 | −27.644 | 1.00 | 16.25 | B | C |
| ATOM | 11818 | CD | LYS | B | 210 | 85.403 | 29.498 | −28.838 | 1.00 | 15.92 | B | C |
| ATOM | 11821 | CE | LYS | B | 210 | 84.773 | 28.196 | −29.298 | 1.00 | 15.10 | B | C |
| ATOM | 11824 | NZ | LYS | B | 210 | 83.951 | 28.393 | −30.523 | 1.00 | 14.52 | B | N |
| ATOM | 11828 | C | LYS | B | 210 | 88.218 | 31.861 | −25.437 | 1.00 | 16.75 | B | C |
| ATOM | 11829 | O | LYS | B | 210 | 89.311 | 32.145 | −25.928 | 1.00 | 17.30 | B | O |
| ATOM | 11831 | N | LYS | B | 211 | 87.555 | 32.687 | −24.627 | 1.00 | 17.35 | B | N |
| ATOM | 11832 | CA | LYS | B | 211 | 88.104 | 33.994 | −24.247 | 1.00 | 17.95 | B | C |
| ATOM | 11834 | CB | LYS | B | 211 | 87.083 | 34.814 | −23.445 | 1.00 | 18.18 | B | C |
| ATOM | 11837 | CG | LYS | B | 211 | 85.851 | 35.242 | −24.233 | 1.00 | 18.73 | B | C |
| ATOM | 11840 | CD | LYS | B | 211 | 85.015 | 36.254 | −23.458 | 1.00 | 19.41 | B | C |
| ATOM | 11843 | CE | LYS | B | 211 | 83.593 | 36.355 | −24.010 | 1.00 | 20.51 | B | C |
| ATOM | 11846 | NZ | LYS | B | 211 | 83.552 | 36.703 | −25.461 | 1.00 | 20.75 | B | N |
| ATOM | 11850 | C | LYS | B | 211 | 89.388 | 33.830 | −23.431 | 1.00 | 18.28 | B | C |
| ATOM | 11851 | O | LYS | B | 211 | 89.364 | 33.281 | −22.329 | 1.00 | 18.16 | B | O |
| ATOM | 11853 | N | GLU | B | 212 | 90.503 | 34.311 | −23.978 | 1.00 | 18.88 | B | N |
| ATOM | 11854 | CA | GLU | B | 212 | 91.801 | 34.227 | −23.300 | 1.00 | 19.31 | B | C |
| ATOM | 11856 | CB | GLU | B | 212 | 92.933 | 34.639 | −24.248 | 1.00 | 19.39 | B | C |
| ATOM | 11859 | CG | GLU | B | 212 | 94.323 | 34.194 | −23.793 | 1.00 | 19.97 | B | C |
| ATOM | 11862 | CD | GLU | B | 212 | 95.445 | 34.816 | −24.608 | 1.00 | 20.72 | B | C |
| ATOM | 11863 | OE1 | GLU | B | 212 | 95.377 | 36.028 | −24.905 | 1.00 | 21.30 | B | O |
| ATOM | 11864 | OE2 | GLU | B | 212 | 96.407 | 34.093 | −24.941 | 1.00 | 20.66 | B | O |
| ATOM | 11865 | C | GLU | B | 212 | 91.831 | 35.098 | −22.040 | 1.00 | 19.46 | B | C |
| ATOM | 11866 | O | GLU | B | 212 | 92.651 | 34.880 | −21.146 | 1.00 | 19.79 | B | O |
| ATOM | 11868 | N | ASP | B | 213 | 90.932 | 36.078 | −21.979 | 1.00 | 19.22 | B | N |
| ATOM | 11869 | CA | ASP | B | 213 | 90.816 | 36.973 | −20.830 | 1.00 | 19.09 | B | C |
| ATOM | 11871 | CB | ASP | B | 213 | 90.503 | 38.398 | −21.309 | 1.00 | 19.27 | B | C |
| ATOM | 11874 | CG | ASP | B | 213 | 89.263 | 38.464 | −22.186 | 1.00 | 19.40 | B | C |
| ATOM | 11875 | OD1 | ASP | B | 213 | 89.198 | 37.713 | −23.183 | 1.00 | 19.36 | B | O |
| ATOM | 11876 | OD2 | ASP | B | 213 | 88.360 | 39.271 | −21.884 | 1.00 | 21.12 | B | O |
| ATOM | 11877 | C | ASP | B | 213 | 89.750 | 36.516 | −19.828 | 1.00 | 18.88 | B | C |
| ATOM | 11878 | O | ASP | B | 213 | 89.341 | 37.294 | −18.966 | 1.00 | 19.17 | B | O |
| ATOM | 11880 | N | ALA | B | 214 | 89.316 | 35.260 | −19.926 | 1.00 | 18.57 | B | N |
| ATOM | 11881 | CA | ALA | B | 214 | 88.229 | 34.750 | −19.084 | 1.00 | 18.24 | B | C |
| ATOM | 11883 | CB | ALA | B | 214 | 87.574 | 33.549 | −19.740 | 1.00 | 18.18 | B | C |
| ATOM | 11887 | C | ALA | B | 214 | 88.712 | 34.383 | −17.683 | 1.00 | 18.02 | B | C |
| ATOM | 11888 | O | ALA | B | 214 | 89.828 | 33.891 | −17.511 | 1.00 | 17.90 | B | O |
| ATOM | 11890 | N | ASN | B | 215 | 87.857 | 34.627 | −16.690 | 1.00 | 17.91 | B | N |
| ATOM | 11891 | CA | ASN | B | 215 | 88.151 | 34.300 | −15.297 | 1.00 | 17.91 | B | C |
| ATOM | 11893 | CB | ASN | B | 215 | 87.225 | 35.079 | −14.353 | 1.00 | 17.98 | B | C |
| ATOM | 11896 | CG | ASN | B | 215 | 87.530 | 34.835 | −12.882 | 1.00 | 18.96 | B | C |
| ATOM | 11897 | OD1 | ASN | B | 215 | 88.546 | 34.235 | −12.531 | 1.00 | 20.95 | B | O |
| ATOM | 11898 | ND2 | ASN | B | 215 | 86.646 | 35.311 | −12.012 | 1.00 | 20.55 | B | N |
| ATOM | 11901 | C | ASN | B | 215 | 87.989 | 32.801 | −15.079 | 1.00 | 17.88 | B | C |
| ATOM | 11902 | O | ASN | B | 215 | 86.871 | 32.288 | −15.067 | 1.00 | 18.40 | B | O |
| ATOM | 11904 | N | GLN | B | 216 | 89.110 | 32.109 | −14.897 | 1.00 | 17.67 | B | N |
| ATOM | 11905 | CA | GLN | B | 216 | 89.123 | 30.648 | −14.814 | 1.00 | 17.28 | B | C |
| ATOM | 11907 | CB | GLN | B | 216 | 90.559 | 30.125 | −14.732 | 1.00 | 17.40 | B | C |
| ATOM | 11910 | CG | GLN | B | 216 | 91.454 | 30.489 | −15.919 | 1.00 | 18.55 | B | C |
| ATOM | 11913 | CD | GLN | B | 216 | 91.101 | 29.741 | −17.193 | 1.00 | 19.04 | B | C |
| ATOM | 11914 | OE1 | GLN | B | 216 | 90.043 | 29.961 | −17.788 | 1.00 | 19.21 | B | O |
| ATOM | 11915 | NE2 | GLN | B | 216 | 91.999 | 28.863 | −17.628 | 1.00 | 20.05 | B | N |
| ATOM | 11918 | C | GLN | B | 216 | 88.334 | 30.149 | −13.610 | 1.00 | 16.63 | B | C |

TABLE 8-2-continued

Coordinates for L494P Structure

| ATOM | 11919 | O | GLN | B | 216 | 87.517 | 29.234 | −13.733 | 1.00 | 16.72 | B | O |
|---|---|---|---|---|---|---|---|---|---|---|---|---|
| ATOM | 11921 | N | VAL | B | 217 | 88.583 | 30.759 | −12.453 | 1.00 | 15.82 | B | N |
| ATOM | 11922 | CA | VAL | B | 217 | 87.865 | 30.422 | −11.224 | 1.00 | 15.08 | B | C |
| ATOM | 11924 | CB | VAL | B | 217 | 88.187 | 31.414 | −10.079 | 1.00 | 15.07 | B | C |
| ATOM | 11926 | CG1 | VAL | B | 217 | 87.308 | 31.142 | −8.868 | 1.00 | 14.72 | B | C |
| ATOM | 11930 | CG2 | VAL | B | 217 | 89.660 | 31.324 | −9.694 | 1.00 | 15.15 | B | C |
| ATOM | 11934 | C | VAL | B | 217 | 86.360 | 30.394 | −11.481 | 1.00 | 14.47 | B | C |
| ATOM | 11935 | O | VAL | B | 217 | 85.678 | 29.458 | −11.067 | 1.00 | 14.91 | B | O |
| ATOM | 11937 | N | LEU | B | 218 | 85.852 | 31.405 | −12.180 | 1.00 | 13.50 | B | N |
| ATOM | 11938 | CA | LEU | B | 218 | 84.441 | 31.437 | −12.553 | 1.00 | 12.95 | B | C |
| ATOM | 11940 | CB | LEU | B | 218 | 84.069 | 32.789 | −13.179 | 1.00 | 12.79 | B | C |
| ATOM | 11943 | CG | LEU | B | 218 | 82.617 | 32.980 | −13.641 | 1.00 | 11.49 | B | C |
| ATOM | 11945 | CD1 | LEU | B | 218 | 81.627 | 32.691 | −12.524 | 1.00 | 8.68 | B | C |
| ATOM | 11949 | CD2 | LEU | B | 218 | 82.416 | 34.384 | −14.174 | 1.00 | 10.75 | B | C |
| ATOM | 11953 | C | LEU | B | 218 | 84.110 | 30.301 | −13.517 | 1.00 | 12.90 | B | C |
| ATOM | 11954 | O | LEU | B | 218 | 83.134 | 29.579 | −13.311 | 1.00 | 13.48 | B | O |
| ATOM | 11956 | N | LEU | B | 219 | 84.930 | 30.144 | −14.555 | 1.00 | 12.44 | B | N |
| ATOM | 11957 | CA | LEU | B | 219 | 84.683 | 29.154 | −15.609 | 1.00 | 12.25 | B | C |
| ATOM | 11959 | CB | LEU | B | 219 | 85.739 | 29.272 | −16.715 | 1.00 | 12.47 | B | C |
| ATOM | 11962 | CG | LEU | B | 219 | 85.676 | 28.253 | −17.864 | 1.00 | 13.40 | B | C |
| ATOM | 11964 | CD1 | LEU | B | 219 | 84.303 | 28.247 | −18.520 | 1.00 | 12.39 | B | C |
| ATOM | 11968 | CD2 | LEU | B | 219 | 86.761 | 28.534 | −18.896 | 1.00 | 13.97 | B | C |
| ATOM | 11972 | C | LEU | B | 219 | 84.649 | 27.720 | −15.079 | 1.00 | 11.89 | B | C |
| ATOM | 11973 | O | LEU | B | 219 | 83.772 | 26.938 | −15.451 | 1.00 | 12.23 | B | O |
| ATOM | 11975 | N | GLU | B | 220 | 85.607 | 27.379 | −14.222 | 1.00 | 11.04 | B | N |
| ATOM | 11976 | CA | GLU | B | 220 | 85.691 | 26.034 | −13.648 | 1.00 | 10.39 | B | C |
| ATOM | 11978 | CB | GLU | B | 220 | 86.885 | 25.938 | −12.694 | 1.00 | 10.57 | B | C |
| ATOM | 11981 | CG | GLU | B | 220 | 87.164 | 24.540 | −12.157 | 1.00 | 10.41 | B | C |
| ATOM | 11984 | CD | GLU | B | 220 | 88.415 | 24.484 | −11.300 | 1.00 | 11.88 | B | C |
| ATOM | 11985 | OE1 | GLU | B | 220 | 89.036 | 25.544 | −11.076 | 1.00 | 13.40 | B | O |
| ATOM | 11986 | OE2 | GLU | B | 220 | 88.779 | 23.380 | −10.846 | 1.00 | 13.69 | B | O |
| ATOM | 11987 | C | GLU | B | 220 | 84.401 | 25.682 | −12.913 | 1.00 | 9.41 | B | C |
| ATOM | 11988 | O | GLU | B | 220 | 83.838 | 24.607 | −13.110 | 1.00 | 9.34 | B | O |
| ATOM | 11990 | N | LEU | B | 221 | 83.944 | 26.604 | −12.072 | 1.00 | 8.59 | B | N |
| ATOM | 11991 | CA | LEU | B | 221 | 82.689 | 26.452 | −11.338 | 1.00 | 7.91 | B | C |
| ATOM | 11993 | CB | LEU | B | 221 | 82.470 | 27.675 | −10.445 | 1.00 | 7.25 | B | C |
| ATOM | 11996 | CG | LEU | B | 221 | 81.299 | 27.637 | −9.470 | 1.00 | 5.48 | B | C |
| ATOM | 11998 | CD1 | LEU | B | 221 | 81.473 | 26.510 | −8.472 | 1.00 | 2.94 | B | C |
| ATOM | 12002 | CD2 | LEU | B | 221 | 81.180 | 28.974 | −8.765 | 1.00 | 3.79 | B | C |
| ATOM | 12006 | C | LEU | B | 221 | 81.507 | 26.285 | −12.298 | 1.00 | 8.00 | B | C |
| ATOM | 12007 | O | LEU | B | 221 | 80.662 | 25.402 | −12.116 | 1.00 | 7.50 | B | O |
| ATOM | 12009 | N | ALA | B | 222 | 81.464 | 27.141 | −13.316 | 1.00 | 7.90 | B | N |
| ATOM | 12010 | CA | ALA | B | 222 | 80.434 | 27.087 | −14.348 | 1.00 | 8.12 | B | C |
| ATOM | 12012 | CB | ALA | B | 222 | 80.752 | 28.080 | −15.451 | 1.00 | 8.09 | B | C |
| ATOM | 12016 | C | ALA | B | 222 | 80.287 | 25.684 | −14.933 | 1.00 | 8.56 | B | C |
| ATOM | 12017 | O | ALA | B | 222 | 79.171 | 25.191 | −15.104 | 1.00 | 8.85 | B | O |
| ATOM | 12019 | N | ILE | B | 223 | 81.418 | 25.048 | −15.230 | 1.00 | 8.90 | B | N |
| ATOM | 12020 | CA | ILE | B | 223 | 81.428 | 23.699 | −15.793 | 1.00 | 9.10 | B | C |
| ATOM | 12022 | CB | ILE | B | 223 | 82.812 | 23.336 | −16.366 | 1.00 | 9.15 | B | C |
| ATOM | 12024 | CG1 | ILE | B | 223 | 83.153 | 24.241 | −17.550 | 1.00 | 9.69 | B | C |
| ATOM | 12027 | CD1 | ILE | B | 223 | 84.570 | 24.078 | −18.041 | 1.00 | 11.92 | B | C |
| ATOM | 12031 | CG2 | ILE | B | 223 | 82.845 | 21.881 | −16.816 | 1.00 | 8.99 | B | C |
| ATOM | 12035 | C | ILE | B | 223 | 81.030 | 22.657 | −14.750 | 1.00 | 9.24 | B | C |
| ATOM | 12036 | O | ILE | B | 223 | 80.215 | 21.777 | −15.028 | 1.00 | 9.09 | B | O |
| ATOM | 12038 | N | LEU | B | 224 | 81.612 | 22.756 | −13.557 | 1.00 | 9.68 | B | N |
| ATOM | 12039 | CA | LEU | B | 224 | 81.306 | 21.822 | −12.468 | 1.00 | 10.03 | B | C |
| ATOM | 12041 | CB | LEU | B | 224 | 82.114 | 22.156 | −11.208 | 1.00 | 9.46 | B | C |
| ATOM | 12044 | CG | LEU | B | 224 | 83.367 | 21.311 | −10.988 | 1.00 | 9.22 | B | C |
| ATOM | 12046 | CD1 | LEU | B | 224 | 84.199 | 21.177 | −12.262 | 1.00 | 8.16 | B | C |
| ATOM | 12050 | CD2 | LEU | B | 224 | 84.193 | 21.895 | −9.856 | 1.00 | 10.80 | B | C |
| ATOM | 12054 | C | LEU | B | 224 | 79.821 | 21.809 | −12.130 | 1.00 | 10.73 | B | C |
| ATOM | 12055 | O | LEU | B | 224 | 79.209 | 20.742 | −12.032 | 1.00 | 10.93 | B | O |
| ATOM | 12057 | N | ASP | B | 225 | 79.252 | 22.999 | −11.959 | 1.00 | 11.11 | B | N |
| ATOM | 12058 | CA | ASP | B | 225 | 77.860 | 23.124 | −11.556 | 1.00 | 11.25 | B | C |
| ATOM | 12060 | CB | ASP | B | 225 | 77.505 | 24.585 | −11.282 | 1.00 | 11.10 | B | C |
| ATOM | 12063 | CG | ASP | B | 225 | 76.227 | 24.727 | −10.487 | 1.00 | 11.83 | B | C |
| ATOM | 12064 | OD1 | ASP | B | 225 | 75.198 | 25.135 | −11.071 | 1.00 | 10.54 | B | O |
| ATOM | 12065 | OD2 | ASP | B | 225 | 76.248 | 24.405 | −9.280 | 1.00 | 11.82 | B | O |
| ATOM | 12066 | C | ASP | B | 225 | 76.939 | 22.549 | −12.627 | 1.00 | 11.77 | B | C |
| ATOM | 12067 | O | ASP | B | 225 | 76.014 | 21.798 | −12.316 | 1.00 | 11.63 | B | O |
| ATOM | 12069 | N | TYR | B | 226 | 77.209 | 22.891 | −13.885 | 1.00 | 12.20 | B | N |
| ATOM | 12070 | CA | TYR | B | 226 | 76.415 | 22.393 | −15.005 | 1.00 | 12.70 | B | C |
| ATOM | 12072 | CB | TYR | B | 226 | 76.962 | 22.925 | −16.332 | 1.00 | 12.61 | B | C |
| ATOM | 12075 | CG | TYR | B | 226 | 76.133 | 22.538 | −17.541 | 1.00 | 12.38 | B | C |
| ATOM | 12076 | CD1 | TYR | B | 226 | 75.212 | 23.421 | −18.090 | 1.00 | 12.61 | B | C |
| ATOM | 12078 | CE1 | TYR | B | 226 | 74.455 | 23.069 | −19.199 | 1.00 | 13.81 | B | C |
| ATOM | 12080 | CZ | TYR | B | 226 | 74.615 | 21.818 | −19.768 | 1.00 | 13.32 | B | C |
| ATOM | 12081 | OH | TYR | B | 226 | 73.869 | 21.457 | −20.866 | 1.00 | 14.04 | B | O |

TABLE 8-2-continued

Coordinates for L494P Structure

| ATOM | 12083 | CE2 | TYR | B | 226 | 75.522 | 20.926 | −19.239 | 1.00 | 11.80 | B | C |
|---|---|---|---|---|---|---|---|---|---|---|---|---|
| ATOM | 12085 | CD2 | TYR | B | 226 | 76.274 | 21.287 | −18.135 | 1.00 | 11.70 | B | C |
| ATOM | 12087 | C | TYR | B | 226 | 76.365 | 20.861 | −15.025 | 1.00 | 13.36 | B | C |
| ATOM | 12088 | O | TYR | B | 226 | 75.290 | 20.273 | −15.170 | 1.00 | 14.07 | B | O |
| ATOM | 12090 | N | ASN | B | 227 | 77.527 | 20.225 | −14.882 | 1.00 | 13.50 | B | N |
| ATOM | 12091 | CA | ASN | B | 227 | 77.611 | 18.764 | −14.862 | 1.00 | 13.63 | B | C |
| ATOM | 12093 | CB | ASN | B | 227 | 79.074 | 18.302 | −14.837 | 1.00 | 13.86 | B | C |
| ATOM | 12096 | CG | ASN | B | 227 | 79.789 | 18.524 | −16.161 | 1.00 | 14.25 | B | C |
| ATOM | 12097 | OD1 | ASN | B | 227 | 79.172 | 18.516 | −17.230 | 1.00 | 13.18 | B | O |
| ATOM | 12098 | ND2 | ASN | B | 227 | 81.104 | 18.712 | −16.094 | 1.00 | 12.89 | B | N |
| ATOM | 12101 | C | ASN | B | 227 | 76.866 | 18.166 | −13.673 | 1.00 | 13.81 | B | C |
| ATOM | 12102 | O | ASN | B | 227 | 76.139 | 17.186 | −13.824 | 1.00 | 13.98 | B | O |
| ATOM | 12104 | N | MET | B | 228 | 77.053 | 18.757 | −12.495 | 1.00 | 14.03 | B | N |
| ATOM | 12105 | CA | MET | B | 228 | 76.345 | 18.325 | −11.288 | 1.00 | 14.59 | B | C |
| ATOM | 12107 | CB | MET | B | 228 | 76.698 | 19.234 | −10.107 | 1.00 | 15.31 | B | C |
| ATOM | 12110 | CG | MET | B | 228 | 75.985 | 18.894 | −8.792 | 1.00 | 16.38 | B | C |
| ATOM | 12113 | SD | MET | B | 228 | 75.944 | 20.288 | −7.645 | 1.00 | 18.68 | B | S |
| ATOM | 12114 | CE | MET | B | 228 | 74.714 | 21.327 | −8.435 | 1.00 | 17.56 | B | C |
| ATOM | 12118 | C | MET | B | 228 | 74.835 | 18.345 | −11.507 | 1.00 | 14.50 | B | C |
| ATOM | 12119 | O | MET | B | 228 | 74.136 | 17.402 | −11.138 | 1.00 | 14.64 | B | O |
| ATOM | 12121 | N | ILE | B | 229 | 74.337 | 19.427 | −12.097 | 1.00 | 14.25 | B | N |
| ATOM | 12122 | CA | ILE | B | 229 | 72.916 | 19.538 | −12.398 | 1.00 | 14.20 | B | C |
| ATOM | 12124 | CB | ILE | B | 229 | 72.537 | 20.957 | −12.857 | 1.00 | 14.37 | B | C |
| ATOM | 12126 | CG1 | ILE | B | 229 | 72.802 | 21.973 | −11.741 | 1.00 | 14.47 | B | C |
| ATOM | 12129 | CD1 | ILE | B | 229 | 72.024 | 23.268 | −11.891 | 1.00 | 13.51 | B | C |
| ATOM | 12133 | CG2 | ILE | B | 229 | 71.074 | 21.011 | −13.262 | 1.00 | 15.42 | B | C |
| ATOM | 12137 | C | ILE | B | 229 | 72.528 | 18.523 | −13.470 | 1.00 | 13.75 | B | C |
| ATOM | 12138 | O | ILE | B | 229 | 71.558 | 17.789 | −13.310 | 1.00 | 13.08 | B | O |
| ATOM | 12140 | N | GLN | B | 230 | 73.297 | 18.476 | −14.554 | 1.00 | 14.01 | B | N |
| ATOM | 12141 | CA | GLN | B | 230 | 73.092 | 17.472 | −15.599 | 1.00 | 14.55 | B | C |
| ATOM | 12143 | CB | GLN | B | 230 | 74.216 | 17.535 | −16.640 | 1.00 | 14.49 | B | C |
| ATOM | 12146 | CG | GLN | B | 230 | 74.086 | 16.503 | −17.757 | 1.00 | 13.89 | B | C |
| ATOM | 12149 | CD | GLN | B | 230 | 75.223 | 16.564 | −18.755 | 1.00 | 12.94 | B | C |
| ATOM | 12150 | OE1 | GLN | B | 230 | 76.100 | 15.701 | −18.761 | 1.00 | 12.13 | B | O |
| ATOM | 12151 | NE2 | GLN | B | 230 | 75.213 | 17.582 | −19.608 | 1.00 | 10.57 | B | N |
| ATOM | 12154 | C | GLN | B | 230 | 72.996 | 16.052 | −15.026 | 1.00 | 15.29 | B | C |
| ATOM | 12155 | O | GLN | B | 230 | 72.177 | 15.255 | −15.481 | 1.00 | 15.71 | B | O |
| ATOM | 12157 | N | SER | B | 231 | 73.832 | 15.739 | −14.037 | 1.00 | 15.66 | B | N |
| ATOM | 12158 | CA | SER | B | 231 | 73.793 | 14.425 | −13.387 | 1.00 | 15.81 | B | C |
| ATOM | 12160 | CB | SER | B | 231 | 75.004 | 14.227 | −12.468 | 1.00 | 15.73 | B | C |
| ATOM | 12163 | OG | SER | B | 231 | 74.848 | 14.926 | −11.246 | 1.00 | 16.09 | B | O |
| ATOM | 12165 | C | SER | B | 231 | 72.492 | 14.223 | −12.600 | 1.00 | 16.06 | B | C |
| ATOM | 12166 | O | SER | B | 231 | 71.989 | 13.102 | −12.511 | 1.00 | 15.88 | B | O |
| ATOM | 12168 | N | VAL | B | 232 | 71.959 | 15.306 | −12.034 | 1.00 | 16.47 | B | N |
| ATOM | 12169 | CA | VAL | B | 232 | 70.661 | 15.266 | −11.355 | 1.00 | 16.95 | B | C |
| ATOM | 12171 | CB | VAL | B | 232 | 70.343 | 16.593 | −10.607 | 1.00 | 17.13 | B | C |
| ATOM | 12173 | CG1 | VAL | B | 232 | 68.971 | 16.529 | −9.941 | 1.00 | 16.99 | B | C |
| ATOM | 12177 | CG2 | VAL | B | 232 | 71.412 | 16.892 | −9.570 | 1.00 | 18.25 | B | C |
| ATOM | 12181 | C | VAL | B | 232 | 69.543 | 14.957 | −12.355 | 1.00 | 17.08 | B | C |
| ATOM | 12182 | O | VAL | B | 232 | 68.608 | 14.229 | −12.032 | 1.00 | 17.31 | B | O |
| ATOM | 12184 | N | TYR | B | 233 | 69.646 | 15.502 | −13.566 | 1.00 | 17.20 | B | N |
| ATOM | 12185 | CA | TYR | B | 233 | 68.679 | 15.203 | −14.624 | 1.00 | 17.30 | B | C |
| ATOM | 12187 | CB | TYR | B | 233 | 68.880 | 16.109 | −15.842 | 1.00 | 17.15 | B | C |
| ATOM | 12190 | CG | TYR | B | 233 | 68.763 | 17.600 | −15.593 | 1.00 | 16.58 | B | C |
| ATOM | 12191 | CD1 | TYR | B | 233 | 68.056 | 18.113 | −14.502 | 1.00 | 14.97 | B | C |
| ATOM | 12193 | CE1 | TYR | B | 233 | 67.957 | 19.481 | −14.296 | 1.00 | 14.04 | B | C |
| ATOM | 12195 | CZ | TYR | B | 233 | 68.549 | 20.349 | −15.194 | 1.00 | 14.25 | B | C |
| ATOM | 12196 | OH | TYR | B | 233 | 68.461 | 21.706 | −15.012 | 1.00 | 13.90 | B | O |
| ATOM | 12198 | CE2 | TYR | B | 233 | 69.240 | 19.866 | −16.283 | 1.00 | 15.45 | B | C |
| ATOM | 12200 | CD2 | TYR | B | 233 | 69.341 | 18.503 | −16.479 | 1.00 | 16.33 | B | C |
| ATOM | 12202 | C | TYR | B | 233 | 68.782 | 13.750 | −15.077 | 1.00 | 17.89 | B | C |
| ATOM | 12203 | O | TYR | B | 233 | 67.772 | 13.135 | −15.421 | 1.00 | 18.00 | B | O |
| ATOM | 12205 | N | GLN | B | 234 | 70.003 | 13.215 | −15.093 | 1.00 | 18.54 | B | N |
| ATOM | 12206 | CA | GLN | B | 234 | 70.234 | 11.817 | −15.465 | 1.00 | 18.95 | B | C |
| ATOM | 12208 | CB | GLN | B | 234 | 71.730 | 11.535 | −15.644 | 1.00 | 18.86 | B | C |
| ATOM | 12211 | CG | GLN | B | 234 | 72.324 | 12.116 | −16.920 | 1.00 | 18.09 | B | C |
| ATOM | 12214 | CD | GLN | B | 234 | 73.816 | 11.854 | −17.051 | 1.00 | 17.24 | B | C |
| ATOM | 12215 | OE1 | GLN | B | 234 | 74.324 | 10.830 | −16.593 | 1.00 | 17.14 | B | O |
| ATOM | 12216 | NE2 | GLN | B | 234 | 74.524 | 12.779 | −17.686 | 1.00 | 15.08 | B | N |
| ATOM | 12219 | C | GLN | B | 234 | 69.638 | 10.858 | −14.434 | 1.00 | 19.60 | B | C |
| ATOM | 12220 | O | GLN | B | 234 | 69.011 | 9.865 | −14.802 | 1.00 | 19.31 | B | O |
| ATOM | 12222 | N | ARG | B | 235 | 69.837 | 11.156 | −13.151 | 1.00 | 20.61 | B | N |
| ATOM | 12223 | CA | ARG | B | 235 | 69.232 | 10.365 | −12.074 | 1.00 | 21.86 | B | C |
| ATOM | 12225 | CB | ARG | B | 235 | 69.842 | 10.722 | −10.712 | 1.00 | 22.48 | B | C |
| ATOM | 12228 | CG | ARG | B | 235 | 69.357 | 9.837 | −9.562 | 1.00 | 24.72 | B | C |
| ATOM | 12231 | CD | ARG | B | 235 | 70.130 | 10.088 | −8.272 | 1.00 | 28.63 | B | C |
| ATOM | 12234 | NE | ARG | B | 235 | 70.043 | 11.485 | −7.828 | 1.00 | 32.42 | B | N |
| ATOM | 12236 | CZ | ARG | B | 235 | 71.016 | 12.398 | −7.918 | 1.00 | 33.76 | B | C |

TABLE 8-2-continued

Coordinates for L494P Structure

| ATOM | 12237 | NH1 | ARG | B | 235 | 72.205 | 12.098 | −8.440 | 1.00 | 34.56 | B | N |
|---|---|---|---|---|---|---|---|---|---|---|---|---|
| ATOM | 12240 | NH2 | ARG | B | 235 | 70.799 | 13.633 | −7.472 | 1.00 | 33.57 | B | N |
| ATOM | 12243 | C | ARG | B | 235 | 67.710 | 10.550 | −12.039 | 1.00 | 21.94 | B | C |
| ATOM | 12244 | O | ARG | B | 235 | 66.976 | 9.623 | −11.687 | 1.00 | 22.34 | B | O |
| ATOM | 12246 | N | ASP | B | 236 | 67.244 | 11.745 | −12.393 | 1.00 | 21.69 | B | N |
| ATOM | 12247 | CA | ASP | B | 236 | 65.818 | 11.975 | −12.584 | 1.00 | 21.55 | B | C |
| ATOM | 12249 | CB | ASP | B | 236 | 65.530 | 13.445 | −12.920 | 1.00 | 21.49 | B | C |
| ATOM | 12252 | CG | ASP | B | 236 | 65.742 | 14.384 | −11.737 | 1.00 | 21.70 | B | C |
| ATOM | 12253 | OD1 | ASP | B | 236 | 65.961 | 13.915 | −10.601 | 1.00 | 22.53 | B | O |
| ATOM | 12254 | OD2 | ASP | B | 236 | 65.694 | 15.611 | −11.951 | 1.00 | 20.61 | B | O |
| ATOM | 12255 | C | ASP | B | 236 | 65.324 | 11.086 | −13.719 | 1.00 | 21.53 | B | C |
| ATOM | 12256 | O | ASP | B | 236 | 64.440 | 10.255 | −13.520 | 1.00 | 21.51 | B | O |
| ATOM | 12258 | N | LEU | B | 237 | 65.929 | 11.247 | −14.895 | 1.00 | 21.85 | B | N |
| ATOM | 12259 | CA | LEU | B | 237 | 65.483 | 10.568 | −16.117 | 1.00 | 22.44 | B | C |
| ATOM | 12261 | CB | LEU | B | 237 | 66.369 | 10.963 | −17.307 | 1.00 | 22.59 | B | C |
| ATOM | 12264 | CG | LEU | B | 237 | 65.987 | 10.394 | −18.683 | 1.00 | 22.86 | B | C |
| ATOM | 12266 | CD1 | LEU | B | 237 | 64.591 | 10.840 | −19.099 | 1.00 | 22.39 | B | C |
| ATOM | 12270 | CD2 | LEU | B | 237 | 67.011 | 10.801 | −19.734 | 1.00 | 23.22 | B | C |
| ATOM | 12274 | C | LEU | B | 237 | 65.435 | 9.043 | −16.002 | 1.00 | 22.87 | B | C |
| ATOM | 12275 | O | LEU | B | 237 | 64.508 | 8.421 | −16.518 | 1.00 | 23.17 | B | O |
| ATOM | 12277 | N | ARG | B | 238 | 66.429 | 8.445 | −15.347 | 1.00 | 23.22 | B | N |
| ATOM | 12278 | CA | ARG | B | 238 | 66.465 | 6.986 | −15.167 | 1.00 | 23.20 | B | C |
| ATOM | 12280 | CB | ARG | B | 238 | 67.747 | 6.544 | −14.453 | 1.00 | 23.33 | B | C |
| ATOM | 12283 | CG | ARG | B | 238 | 68.977 | 6.488 | −15.348 | 1.00 | 24.49 | B | C |
| ATOM | 12286 | CD | ARG | B | 238 | 70.111 | 5.717 | −14.683 | 1.00 | 25.92 | B | C |
| ATOM | 12289 | NE | ARG | B | 238 | 70.498 | 6.303 | −13.397 | 1.00 | 27.40 | B | N |
| ATOM | 12291 | CZ | ARG | B | 238 | 71.452 | 7.219 | −13.216 | 1.00 | 27.20 | B | C |
| ATOM | 12292 | NH1 | ARG | B | 238 | 72.161 | 7.693 | −14.239 | 1.00 | 26.98 | B | N |
| ATOM | 12295 | NH2 | ARG | B | 238 | 71.701 | 7.669 | −11.991 | 1.00 | 27.09 | B | N |
| ATOM | 12298 | C | ARG | B | 238 | 65.253 | 6.480 | −14.393 | 1.00 | 23.04 | B | C |
| ATOM | 12299 | O | ARG | B | 238 | 64.725 | 5.416 | −14.697 | 1.00 | 22.74 | B | O |
| ATOM | 12301 | N | GLU | B | 239 | 64.822 | 7.252 | −13.397 | 1.00 | 23.57 | B | N |
| ATOM | 12302 | CA | GLU | B | 239 | 63.645 | 6.916 | −12.592 | 1.00 | 24.22 | B | C |
| ATOM | 12304 | CB | GLU | B | 239 | 63.617 | 7.774 | −11.322 | 1.00 | 24.77 | B | C |
| ATOM | 12307 | CG | GLU | B | 239 | 62.618 | 7.317 | −10.265 | 1.00 | 26.77 | B | C |
| ATOM | 12310 | CD | GLU | B | 239 | 62.813 | 8.028 | −8.934 | 1.00 | 29.81 | B | C |
| ATOM | 12311 | OE1 | GLU | B | 239 | 63.910 | 7.911 | −8.348 | 1.00 | 30.83 | B | O |
| ATOM | 12312 | OE2 | GLU | B | 239 | 61.867 | 8.702 | −8.469 | 1.00 | 32.55 | B | O |
| ATOM | 12313 | C | GLU | B | 239 | 62.338 | 7.085 | −13.382 | 1.00 | 23.78 | B | C |
| ATOM | 12314 | O | GLU | B | 239 | 61.406 | 6.293 | −13.224 | 1.00 | 23.75 | B | O |
| ATOM | 12316 | N | THR | B | 240 | 62.271 | 8.115 | −14.222 | 1.00 | 23.31 | B | N |
| ATOM | 12317 | CA | THR | B | 240 | 61.130 | 8.298 | −15.122 | 1.00 | 23.25 | B | C |
| ATOM | 12319 | CB | THR | B | 240 | 61.132 | 9.703 | −15.767 | 1.00 | 23.05 | B | C |
| ATOM | 12321 | OG1 | THR | B | 240 | 61.223 | 10.703 | −14.746 | 1.00 | 22.86 | B | O |
| ATOM | 12323 | CG2 | THR | B | 240 | 59.862 | 9.932 | −16.574 | 1.00 | 22.22 | B | C |
| ATOM | 12327 | C | THR | B | 240 | 61.135 | 7.236 | −16.227 | 1.00 | 23.58 | B | C |
| ATOM | 12328 | O | THR | B | 240 | 60.076 | 6.746 | −16.630 | 1.00 | 23.36 | B | O |
| ATOM | 12330 | N | SER | B | 241 | 62.330 | 6.888 | −16.707 | 1.00 | 23.85 | B | N |
| ATOM | 12331 | CA | SER | B | 241 | 62.500 | 5.878 | −17.758 | 1.00 | 24.00 | B | C |
| ATOM | 12333 | CB | SER | B | 241 | 63.943 | 5.868 | −18.271 | 1.00 | 24.23 | B | C |
| ATOM | 12336 | OG | SER | B | 241 | 64.304 | 7.126 | −18.813 | 1.00 | 25.12 | B | O |
| ATOM | 12338 | C | SER | B | 241 | 62.124 | 4.479 | −17.280 | 1.00 | 24.04 | B | C |
| ATOM | 12339 | O | SER | B | 241 | 61.531 | 3.705 | −18.032 | 1.00 | 23.92 | B | O |
| ATOM | 12341 | N | ARG | B | 242 | 62.483 | 4.151 | −16.039 | 1.00 | 24.20 | B | N |
| ATOM | 12342 | CA | ARG | B | 242 | 62.037 | 2.900 | −15.427 | 1.00 | 24.47 | B | C |
| ATOM | 12344 | CB | ARG | B | 242 | 62.565 | 2.741 | −13.992 | 1.00 | 24.64 | B | C |
| ATOM | 12347 | CG | ARG | B | 242 | 63.977 | 2.149 | −13.889 | 1.00 | 25.62 | B | C |
| ATOM | 12350 | CD | ARG | B | 242 | 64.220 | 1.493 | −12.525 | 1.00 | 25.82 | B | C |
| ATOM | 12353 | NE | ARG | B | 242 | 63.800 | 2.347 | −11.411 | 1.00 | 26.44 | B | N |
| ATOM | 12355 | CZ | ARG | B | 242 | 64.518 | 3.342 | −10.885 | 1.00 | 26.48 | B | C |
| ATOM | 12356 | NH1 | ARG | B | 242 | 64.020 | 4.045 | −9.874 | 1.00 | 25.75 | B | N |
| ATOM | 12359 | NH2 | ARG | B | 242 | 65.725 | 3.644 | −11.356 | 1.00 | 27.75 | B | N |
| ATOM | 12362 | C | ARG | B | 242 | 60.512 | 2.851 | −15.429 | 1.00 | 24.30 | B | C |
| ATOM | 12363 | O | ARG | B | 242 | 59.919 | 1.885 | −15.909 | 1.00 | 24.90 | B | O |
| ATOM | 12365 | N | TRP | B | 243 | 59.887 | 3.903 | −14.906 | 1.00 | 23.61 | B | N |
| ATOM | 12366 | CA | TRP | B | 243 | 58.429 | 4.000 | −14.888 | 1.00 | 22.97 | B | C |
| ATOM | 12368 | CB | TRP | B | 243 | 57.982 | 5.318 | −14.237 | 1.00 | 22.79 | B | C |
| ATOM | 12371 | CG | TRP | B | 243 | 56.531 | 5.655 | −14.463 | 1.00 | 21.51 | B | C |
| ATOM | 12372 | CD1 | TRP | B | 243 | 55.465 | 5.256 | −13.708 | 1.00 | 20.30 | B | C |
| ATOM | 12374 | NE1 | TRP | B | 243 | 54.301 | 5.768 | −14.228 | 1.00 | 19.74 | B | N |
| ATOM | 12376 | CE2 | TRP | B | 243 | 54.599 | 6.513 | −15.339 | 1.00 | 19.29 | B | C |
| ATOM | 12377 | CD2 | TRP | B | 243 | 55.995 | 6.466 | −15.517 | 1.00 | 19.30 | B | C |
| ATOM | 12378 | CE3 | TRP | B | 243 | 56.561 | 7.151 | −16.597 | 1.00 | 18.07 | B | C |
| ATOM | 12380 | CZ3 | TRP | B | 243 | 55.728 | 7.850 | −17.453 | 1.00 | 17.55 | B | C |
| ATOM | 12382 | CH2 | TRP | B | 243 | 54.344 | 7.880 | −17.252 | 1.00 | 17.66 | B | C |
| ATOM | 12384 | CZ2 | TRP | B | 243 | 53.759 | 7.218 | −16.205 | 1.00 | 19.44 | B | C |
| ATOM | 12386 | C | TRP | B | 243 | 57.852 | 3.879 | −16.299 | 1.00 | 22.95 | B | C |
| ATOM | 12387 | O | TRP | B | 243 | 56.882 | 3.151 | −16.515 | 1.00 | 23.06 | B | O |

TABLE 8-2-continued

Coordinates for L494P Structure

| ATOM | 12389 | N | TRP | B | 244 | 58.457 | 4.585 | −17.252 | 1.00 | 22.77 | B | N |
|------|-------|------|-----|---|-----|--------|-------|---------|------|-------|---|---|
| ATOM | 12390 | CA | TRP | B | 244 | 57.944 | 4.624 | −18.624 | 1.00 | 22.56 | B | C |
| ATOM | 12392 | CB | TRP | B | 244 | 58.743 | 5.624 | −19.473 | 1.00 | 22.41 | B | C |
| ATOM | 12395 | CG | TRP | B | 244 | 58.196 | 5.866 | −20.872 | 1.00 | 21.79 | B | C |
| ATOM | 12396 | CD1 | TRP | B | 244 | 58.907 | 5.853 | −22.041 | 1.00 | 21.43 | B | C |
| ATOM | 12398 | NE1 | TRP | B | 244 | 58.078 | 6.124 | −23.105 | 1.00 | 20.15 | B | N |
| ATOM | 12400 | CE2 | TRP | B | 244 | 56.804 | 6.314 | −22.641 | 1.00 | 18.38 | B | C |
| ATOM | 12401 | CD2 | TRP | B | 244 | 56.836 | 6.162 | −21.238 | 1.00 | 19.68 | B | C |
| ATOM | 12402 | CE3 | TRP | B | 244 | 55.644 | 6.312 | −20.517 | 1.00 | 17.93 | B | C |
| ATOM | 12404 | CZ3 | TRP | B | 244 | 54.482 | 6.602 | −21.206 | 1.00 | 16.17 | B | C |
| ATOM | 12406 | CH2 | TRP | B | 244 | 54.483 | 6.745 | −22.599 | 1.00 | 16.40 | B | C |
| ATOM | 12408 | CZ2 | TRP | B | 244 | 55.631 | 6.605 | −23.333 | 1.00 | 16.86 | B | C |
| ATOM | 12410 | C | TRP | B | 244 | 57.951 | 3.241 | −19.268 | 1.00 | 22.60 | B | C |
| ATOM | 12411 | O | TRP | B | 244 | 57.038 | 2.906 | −20.023 | 1.00 | 23.08 | B | O |
| ATOM | 12413 | N | ARG | B | 245 | 58.967 | 2.443 | −18.951 | 1.00 | 22.59 | B | N |
| ATOM | 12414 | CA | ARG | B | 245 | 59.086 | 1.083 | −19.483 | 1.00 | 22.68 | B | C |
| ATOM | 12416 | CB | ARG | B | 245 | 60.484 | 0.511 | −19.208 | 1.00 | 22.97 | B | C |
| ATOM | 12419 | CG | ARG | B | 245 | 61.171 | −0.073 | −20.439 | 1.00 | 24.49 | B | C |
| ATOM | 12422 | CD | ARG | B | 245 | 62.637 | −0.418 | −20.184 | 1.00 | 26.62 | B | C |
| ATOM | 12425 | NE | ARG | B | 245 | 63.364 | 0.675 | −19.532 | 1.00 | 29.64 | B | N |
| ATOM | 12427 | CZ | ARG | B | 245 | 63.829 | 0.665 | −18.278 | 1.00 | 32.38 | B | C |
| ATOM | 12428 | NH1 | ARG | B | 245 | 64.468 | 1.734 | −17.808 | 1.00 | 32.81 | B | N |
| ATOM | 12431 | NH2 | ARG | B | 245 | 63.675 | −0.395 | −17.485 | 1.00 | 32.73 | B | N |
| ATOM | 12434 | C | ARG | B | 245 | 58.011 | 0.172 | −18.885 | 1.00 | 22.31 | B | C |
| ATOM | 12435 | O | ARG | B | 245 | 57.367 | −0.580 | −19.610 | 1.00 | 22.44 | B | O |
| ATOM | 12437 | N | ARG | B | 246 | 57.825 | 0.255 | −17.567 | 1.00 | 22.29 | B | N |
| ATOM | 12438 | CA | ARG | B | 246 | 56.787 | −0.507 | −16.850 | 1.00 | 22.34 | B | C |
| ATOM | 12440 | CB | ARG | B | 246 | 56.771 | −0.127 | −15.363 | 1.00 | 22.79 | B | C |
| ATOM | 12443 | CG | ARG | B | 246 | 57.920 | −0.713 | −14.543 | 1.00 | 25.55 | B | C |
| ATOM | 12446 | CD | ARG | B | 246 | 57.440 | −1.710 | −13.486 | 1.00 | 28.55 | B | C |
| ATOM | 12449 | NE | ARG | B | 246 | 56.772 | −2.885 | −14.050 | 1.00 | 30.25 | B | N |
| ATOM | 12451 | CZ | ARG | B | 246 | 56.294 | −3.902 | −13.330 | 1.00 | 31.54 | B | C |
| ATOM | 12452 | NH1 | ARG | B | 246 | 55.701 | −4.922 | −13.939 | 1.00 | 31.77 | B | N |
| ATOM | 12455 | NH2 | ARG | B | 246 | 56.406 | −3.910 | −12.004 | 1.00 | 32.68 | B | N |
| ATOM | 12458 | C | ARG | B | 246 | 55.395 | −0.282 | −17.433 | 1.00 | 21.44 | B | C |
| ATOM | 12459 | O | ARG | B | 246 | 54.664 | −1.236 | −17.698 | 1.00 | 21.29 | B | O |
| ATOM | 12461 | N | VAL | B | 247 | 55.031 | 0.985 | −17.612 | 1.00 | 20.80 | B | N |
| ATOM | 12462 | CA | VAL | B | 247 | 53.776 | 1.340 | −18.268 | 1.00 | 20.16 | B | C |
| ATOM | 12464 | CB | VAL | B | 247 | 53.602 | 2.872 | −18.404 | 1.00 | 19.88 | B | C |
| ATOM | 12466 | CG1 | VAL | B | 247 | 53.749 | 3.555 | −17.056 | 1.00 | 18.27 | B | C |
| ATOM | 12470 | CG2 | VAL | B | 247 | 52.252 | 3.203 | −19.016 | 1.00 | 19.22 | B | C |
| ATOM | 12474 | C | VAL | B | 247 | 53.777 | 0.705 | −19.653 | 1.00 | 20.35 | B | C |
| ATOM | 12475 | O | VAL | B | 247 | 52.834 | 0.012 | −20.024 | 1.00 | 19.91 | B | O |
| ATOM | 12477 | N | GLY | B | 248 | 54.856 | 0.941 | −20.398 | 1.00 | 20.85 | B | N |
| ATOM | 12478 | CA | GLY | B | 248 | 55.099 | 0.287 | −21.684 | 1.00 | 21.09 | B | C |
| ATOM | 12481 | C | GLY | B | 248 | 54.039 | 0.561 | −22.731 | 1.00 | 21.48 | B | C |
| ATOM | 12482 | O | GLY | B | 248 | 53.686 | −0.327 | −23.509 | 1.00 | 21.44 | B | O |
| ATOM | 12484 | N | LEU | B | 249 | 53.539 | 1.792 | −22.763 | 1.00 | 21.90 | B | N |
| ATOM | 12485 | CA | LEU | B | 249 | 52.414 | 2.128 | −23.633 | 1.00 | 22.39 | B | C |
| ATOM | 12487 | CB | LEU | B | 249 | 51.736 | 3.423 | −23.164 | 1.00 | 22.22 | B | C |
| ATOM | 12490 | CG | LEU | B | 249 | 50.264 | 3.619 | −23.549 | 1.00 | 21.67 | B | C |
| ATOM | 12492 | CD1 | LEU | B | 249 | 49.396 | 2.466 | −23.060 | 1.00 | 19.27 | B | C |
| ATOM | 12496 | CD2 | LEU | B | 249 | 49.741 | 4.948 | −23.007 | 1.00 | 21.26 | B | C |
| ATOM | 12500 | C | LEU | B | 249 | 52.844 | 2.229 | −25.102 | 1.00 | 23.09 | B | C |
| ATOM | 12501 | O | LEU | B | 249 | 52.140 | 1.744 | −25.989 | 1.00 | 23.40 | B | O |
| ATOM | 12503 | N | ALA | B | 250 | 54.004 | 2.837 | −25.351 | 1.00 | 23.56 | B | N |
| ATOM | 12504 | CA | ALA | B | 250 | 54.523 | 2.999 | −26.717 | 1.00 | 23.56 | B | C |
| ATOM | 12506 | CB | ALA | B | 250 | 55.778 | 3.867 | −26.708 | 1.00 | 23.75 | B | C |
| ATOM | 12510 | C | ALA | B | 250 | 54.812 | 1.661 | −27.406 | 1.00 | 23.27 | B | C |
| ATOM | 12511 | O | ALA | B | 250 | 54.632 | 1.533 | −28.621 | 1.00 | 22.94 | B | O |
| ATOM | 12513 | N | THR | B | 251 | 55.261 | 0.677 | −26.630 | 1.00 | 23.12 | B | N |
| ATOM | 12514 | CA | THR | B | 251 | 55.528 | −0.665 | −27.151 | 1.00 | 23.11 | B | C |
| ATOM | 12516 | CB | THR | B | 251 | 56.313 | −1.525 | −26.133 | 1.00 | 23.00 | B | C |
| ATOM | 12518 | OG1 | THR | B | 251 | 57.569 | −0.903 | −25.843 | 1.00 | 23.41 | B | O |
| ATOM | 12520 | CG2 | THR | B | 251 | 56.567 | −2.922 | −26.682 | 1.00 | 23.17 | B | C |
| ATOM | 12524 | C | THR | B | 251 | 54.240 | −1.402 | −27.518 | 1.00 | 22.91 | B | C |
| ATOM | 12525 | O | THR | B | 251 | 54.183 | −2.081 | −28.544 | 1.00 | 23.01 | B | O |
| ATOM | 12527 | N | LYS | B | 252 | 53.213 | −1.259 | −26.683 | 1.00 | 22.75 | B | N |
| ATOM | 12528 | CA | LYS | B | 252 | 51.970 | −2.019 | −26.843 | 1.00 | 22.97 | B | C |
| ATOM | 12530 | CB | LYS | B | 252 | 51.347 | −2.303 | −25.473 | 1.00 | 23.14 | B | C |
| ATOM | 12533 | CG | LYS | B | 252 | 52.249 | −3.107 | −24.525 | 1.00 | 23.20 | B | C |
| ATOM | 12536 | CD | LYS | B | 252 | 52.403 | −4.563 | −24.963 | 1.00 | 24.47 | B | C |
| ATOM | 12539 | CE | LYS | B | 252 | 53.339 | −5.338 | −24.041 | 1.00 | 24.49 | B | C |
| ATOM | 12542 | NZ | LYS | B | 252 | 53.670 | −6.689 | −24.576 | 1.00 | 23.12 | B | N |
| ATOM | 12546 | C | LYS | B | 252 | 50.949 | −1.350 | −27.781 | 1.00 | 23.11 | B | C |
| ATOM | 12547 | O | LYS | B | 252 | 50.186 | −2.046 | −28.457 | 1.00 | 23.06 | B | O |
| ATOM | 12549 | N | LEU | B | 253 | 50.931 | −0.017 | −27.821 | 1.00 | 23.21 | B | N |
| ATOM | 12550 | CA | LEU | B | 253 | 50.141 | 0.714 | −28.822 | 1.00 | 23.39 | B | C |

TABLE 8-2-continued

Coordinates for L494P Structure

| ATOM | 12552 | CB | LEU | B | 253 | 49.629 | 2.053 | −28.276 | 1.00 | 23.12 | B | C |
|---|---|---|---|---|---|---|---|---|---|---|---|---|
| ATOM | 12555 | CG | LEU | B | 253 | 48.187 | 2.044 | −27.757 | 1.00 | 22.22 | B | C |
| ATOM | 12557 | CD1 | LEU | B | 253 | 47.973 | 0.942 | −26.728 | 1.00 | 21.08 | B | C |
| ATOM | 12561 | CD2 | LEU | B | 253 | 47.816 | 3.406 | −27.182 | 1.00 | 19.92 | B | C |
| ATOM | 12565 | C | LEU | B | 253 | 50.979 | 0.927 | −30.085 | 1.00 | 24.12 | B | C |
| ATOM | 12566 | O | LEU | B | 253 | 52.037 | 1.561 | −30.041 | 1.00 | 24.39 | B | O |
| ATOM | 12568 | N | HIS | B | 254 | 50.482 | 0.411 | −31.208 | 1.00 | 24.48 | B | N |
| ATOM | 12569 | CA | HIS | B | 254 | 51.277 | 0.288 | −32.438 | 1.00 | 24.66 | B | C |
| ATOM | 12571 | CB | HIS | B | 254 | 50.733 | −0.854 | −33.312 | 1.00 | 24.99 | B | C |
| ATOM | 12574 | CG | HIS | B | 254 | 50.385 | −2.093 | −32.542 | 1.00 | 26.11 | B | C |
| ATOM | 12575 | ND1 | HIS | B | 254 | 51.328 | −3.020 | −32.152 | 1.00 | 26.40 | B | N |
| ATOM | 12577 | CE1 | HIS | B | 254 | 50.734 | −3.993 | −31.484 | 1.00 | 26.76 | B | C |
| ATOM | 12579 | NE2 | HIS | B | 254 | 49.441 | −3.731 | −31.425 | 1.00 | 27.08 | B | N |
| ATOM | 12581 | CD2 | HIS | B | 254 | 49.196 | −2.548 | −32.079 | 1.00 | 26.88 | B | C |
| ATOM | 12583 | C | HIS | B | 254 | 51.339 | 1.587 | −33.248 | 1.00 | 24.42 | B | C |
| ATOM | 12584 | O | HIS | B | 254 | 52.154 | 1.712 | −34.159 | 1.00 | 24.54 | B | O |
| ATOM | 12586 | N | PHE | B | 255 | 50.478 | 2.543 | −32.911 | 1.00 | 24.49 | B | N |
| ATOM | 12587 | CA | PHE | B | 255 | 50.439 | 3.853 | −33.573 | 1.00 | 24.65 | B | C |
| ATOM | 12589 | CB | PHE | B | 255 | 48.984 | 4.303 | −33.758 | 1.00 | 24.74 | B | C |
| ATOM | 12592 | CG | PHE | B | 255 | 48.292 | 4.626 | −32.464 | 1.00 | 24.93 | B | C |
| ATOM | 12593 | CD1 | PHE | B | 255 | 48.365 | 5.903 | −31.919 | 1.00 | 24.68 | B | C |
| ATOM | 12595 | CE1 | PHE | B | 255 | 47.749 | 6.196 | −30.714 | 1.00 | 25.25 | B | C |
| ATOM | 12597 | CZ | PHE | B | 255 | 47.058 | 5.204 | −30.036 | 1.00 | 25.88 | B | C |
| ATOM | 12599 | CE2 | PHE | B | 255 | 46.985 | 3.925 | −30.566 | 1.00 | 25.92 | B | C |
| ATOM | 12601 | CD2 | PHE | B | 255 | 47.602 | 3.641 | −31.771 | 1.00 | 24.96 | B | C |
| ATOM | 12603 | C | PHE | B | 255 | 51.179 | 4.931 | −32.772 | 1.00 | 24.72 | B | C |
| ATOM | 12604 | O | PHE | B | 255 | 51.506 | 5.988 | −33.312 | 1.00 | 24.47 | B | O |
| ATOM | 12606 | N | ALA | B | 256 | 51.416 | 4.665 | −31.485 | 1.00 | 24.97 | B | N |
| ATOM | 12607 | CA | ALA | B | 256 | 51.924 | 5.675 | −30.551 | 1.00 | 25.20 | B | C |
| ATOM | 12609 | CB | ALA | B | 256 | 51.462 | 5.355 | −29.132 | 1.00 | 24.99 | B | C |
| ATOM | 12613 | C | ALA | B | 256 | 53.451 | 5.822 | −30.590 | 1.00 | 25.60 | B | C |
| ATOM | 12614 | O | ALA | B | 256 | 54.180 | 4.845 | −30.776 | 1.00 | 25.02 | B | O |
| ATOM | 12616 | N | ARG | B | 257 | 53.911 | 7.058 | −30.389 | 1.00 | 26.40 | B | N |
| ATOM | 12617 | CA | ARG | B | 257 | 55.329 | 7.410 | −30.453 | 1.00 | 27.04 | B | C |
| ATOM | 12619 | CB | ARG | B | 257 | 55.511 | 8.768 | −31.132 | 1.00 | 27.31 | B | C |
| ATOM | 12622 | CG | ARG | B | 257 | 54.920 | 8.884 | −32.530 | 1.00 | 28.68 | B | C |
| ATOM | 12625 | CD | ARG | B | 257 | 54.737 | 10.347 | −32.907 | 1.00 | 30.49 | B | C |
| ATOM | 12628 | NE | ARG | B | 257 | 53.733 | 10.999 | −32.065 | 1.00 | 31.91 | B | N |
| ATOM | 12630 | CZ | ARG | B | 257 | 53.468 | 12.304 | −32.062 | 1.00 | 31.98 | B | C |
| ATOM | 12631 | NH1 | ARG | B | 257 | 54.132 | 13.134 | −32.860 | 1.00 | 32.59 | B | N |
| ATOM | 12634 | NH2 | ARG | B | 257 | 52.526 | 12.785 | −31.253 | 1.00 | 30.73 | B | N |
| ATOM | 12637 | C | ARG | B | 257 | 55.952 | 7.496 | −29.063 | 1.00 | 27.27 | B | C |
| ATOM | 12638 | O | ARG | B | 257 | 55.380 | 8.103 | −28.153 | 1.00 | 26.70 | B | O |
| ATOM | 12640 | N | ASP | B | 258 | 57.140 | 6.910 | −28.922 | 1.00 | 27.82 | B | N |
| ATOM | 12641 | CA | ASP | B | 258 | 57.907 | 6.973 | −27.680 | 1.00 | 28.09 | B | C |
| ATOM | 12643 | CB | ASP | B | 258 | 58.926 | 5.822 | −27.637 | 1.00 | 28.30 | B | C |
| ATOM | 12646 | CG | ASP | B | 258 | 59.647 | 5.710 | −26.296 | 1.00 | 29.74 | B | C |
| ATOM | 12647 | OD1 | ASP | B | 258 | 59.515 | 6.623 | −25.449 | 1.00 | 31.58 | B | O |
| ATOM | 12648 | OD2 | ASP | B | 258 | 60.350 | 4.696 | −26.088 | 1.00 | 30.24 | B | O |
| ATOM | 12649 | C | ASP | B | 258 | 58.609 | 8.335 | −27.570 | 1.00 | 27.79 | B | C |
| ATOM | 12650 | O | ASP | B | 258 | 59.694 | 8.529 | −28.122 | 1.00 | 27.75 | B | O |
| ATOM | 12652 | N | ARG | B | 259 | 57.977 | 9.269 | −26.859 | 1.00 | 27.57 | B | N |
| ATOM | 12653 | CA | ARG | B | 259 | 58.547 | 10.597 | −26.621 | 1.00 | 27.44 | B | C |
| ATOM | 12655 | CB | ARG | B | 259 | 57.645 | 11.691 | −27.212 | 1.00 | 27.68 | B | C |
| ATOM | 12658 | CG | ARG | B | 259 | 57.598 | 11.737 | −28.736 | 1.00 | 29.41 | B | C |
| ATOM | 12661 | CD | ARG | B | 259 | 58.884 | 12.297 | −29.341 | 1.00 | 30.97 | B | C |
| ATOM | 12664 | NE | ARG | B | 259 | 58.754 | 12.551 | −30.778 | 1.00 | 32.99 | B | N |
| ATOM | 12666 | CZ | ARG | B | 259 | 58.787 | 11.616 | −31.732 | 1.00 | 33.88 | B | C |
| ATOM | 12667 | NH1 | ARG | B | 259 | 58.943 | 10.329 | −31.431 | 1.00 | 34.50 | B | N |
| ATOM | 12670 | NH2 | ARG | B | 259 | 58.657 | 11.972 | −33.008 | 1.00 | 33.20 | B | N |
| ATOM | 12673 | C | ARG | B | 259 | 58.728 | 10.835 | −25.124 | 1.00 | 26.73 | B | C |
| ATOM | 12674 | O | ARG | B | 259 | 57.907 | 11.509 | −24.496 | 1.00 | 27.01 | B | O |
| ATOM | 12676 | N | LEU | B | 260 | 59.792 | 10.270 | −24.553 | 1.00 | 25.66 | B | N |
| ATOM | 12677 | CA | LEU | B | 260 | 60.147 | 10.523 | −23.152 | 1.00 | 24.71 | B | C |
| ATOM | 12679 | CB | LEU | B | 260 | 60.396 | 9.216 | −22.388 | 1.00 | 24.82 | B | C |
| ATOM | 12682 | CG | LEU | B | 260 | 60.711 | 9.346 | −20.887 | 1.00 | 23.56 | B | C |
| ATOM | 12684 | CD1 | LEU | B | 260 | 59.596 | 10.059 | −20.139 | 1.00 | 22.57 | B | C |
| ATOM | 12688 | CD2 | LEU | B | 260 | 60.956 | 7.982 | −20.276 | 1.00 | 22.94 | B | C |
| ATOM | 12692 | C | LEU | B | 260 | 61.381 | 11.411 | −23.075 | 1.00 | 23.72 | B | C |
| ATOM | 12693 | O | LEU | B | 260 | 61.347 | 12.468 | −22.445 | 1.00 | 23.35 | B | O |
| ATOM | 12695 | N | ILE | B | 261 | 62.462 | 10.979 | −23.721 | 1.00 | 22.88 | B | N |
| ATOM | 12696 | CA | ILE | B | 261 | 63.712 | 11.743 | −23.722 | 1.00 | 22.59 | B | C |
| ATOM | 12698 | CB | ILE | B | 261 | 64.773 | 11.162 | −24.691 | 1.00 | 22.38 | B | C |
| ATOM | 12700 | CG1 | ILE | B | 261 | 65.102 | 9.705 | −24.357 | 1.00 | 22.05 | B | C |
| ATOM | 12703 | CD1 | ILE | B | 261 | 66.110 | 9.080 | −25.307 | 1.00 | 21.88 | B | C |
| ATOM | 12707 | CG2 | ILE | B | 261 | 66.056 | 11.987 | −24.628 | 1.00 | 21.66 | B | C |
| ATOM | 12711 | C | ILE | B | 261 | 63.419 | 13.187 | −24.125 | 1.00 | 22.69 | B | C |
| ATOM | 12712 | O | ILE | B | 261 | 63.873 | 14.128 | −23.469 | 1.00 | 22.64 | B | O |

TABLE 8-2-continued

Coordinates for L494P Structure

| ATOM | 12714 | N | GLU | B | 262 | 62.641 | 13.341 | −25.196 | 1.00 | 22.88 | B | N |
|---|---|---|---|---|---|---|---|---|---|---|---|---|
| ATOM | 12715 | CA | GLU | B | 262 | 62.215 | 14.655 | −25.692 | 1.00 | 22.71 | B | C |
| ATOM | 12717 | CB | GLU | B | 262 | 61.384 | 14.518 | −26.981 | 1.00 | 22.85 | B | C |
| ATOM | 12720 | CG | GLU | B | 262 | 62.176 | 14.081 | −28.228 | 1.00 | 23.29 | B | C |
| ATOM | 12723 | CD | GLU | B | 262 | 62.377 | 12.568 | −28.339 | 1.00 | 23.18 | B | C |
| ATOM | 12724 | OE1 | GLU | B | 262 | 62.069 | 11.832 | −27.375 | 1.00 | 22.88 | B | O |
| ATOM | 12725 | OE2 | GLU | B | 262 | 62.852 | 12.113 | −29.401 | 1.00 | 22.83 | B | O |
| ATOM | 12726 | C | GLU | B | 262 | 61.397 | 15.397 | −24.639 | 1.00 | 22.14 | B | C |
| ATOM | 12727 | O | GLU | B | 262 | 61.659 | 16.565 | −24.346 | 1.00 | 22.04 | B | O |
| ATOM | 12729 | N | SER | B | 263 | 60.408 | 14.709 | −24.073 | 1.00 | 21.51 | B | N |
| ATOM | 12730 | CA | SER | B | 263 | 59.561 | 15.292 | −23.035 | 1.00 | 21.01 | B | C |
| ATOM | 12732 | CB | SER | B | 263 | 58.448 | 14.321 | −22.627 | 1.00 | 20.92 | B | C |
| ATOM | 12735 | OG | SER | B | 263 | 57.396 | 14.332 | −23.577 | 1.00 | 20.64 | B | O |
| ATOM | 12737 | C | SER | B | 263 | 60.356 | 15.721 | −21.806 | 1.00 | 20.77 | B | C |
| ATOM | 12738 | O | SER | B | 263 | 59.996 | 16.691 | −21.146 | 1.00 | 20.59 | B | O |
| ATOM | 12740 | N | PHE | B | 264 | 61.434 | 15.008 | −21.493 | 1.00 | 21.04 | B | N |
| ATOM | 12741 | CA | PHE | B | 264 | 62.253 | 15.380 | −20.346 | 1.00 | 21.42 | B | C |
| ATOM | 12743 | CB | PHE | B | 264 | 63.143 | 14.232 | −19.886 | 1.00 | 21.45 | B | C |
| ATOM | 12746 | CG | PHE | B | 264 | 63.662 | 14.426 | −18.502 | 1.00 | 21.91 | B | C |
| ATOM | 12747 | CD1 | PHE | B | 264 | 62.912 | 14.019 | −17.408 | 1.00 | 22.62 | B | C |
| ATOM | 12749 | CE1 | PHE | B | 264 | 63.373 | 14.220 | −16.122 | 1.00 | 23.76 | B | C |
| ATOM | 12751 | CZ | PHE | B | 264 | 64.591 | 14.848 | −15.920 | 1.00 | 24.45 | B | C |
| ATOM | 12753 | CE2 | PHE | B | 264 | 65.337 | 15.273 | −17.006 | 1.00 | 23.47 | B | C |
| ATOM | 12755 | CD2 | PHE | B | 264 | 64.869 | 15.068 | −18.286 | 1.00 | 22.37 | B | C |
| ATOM | 12757 | C | PHE | B | 264 | 63.107 | 16.609 | −20.639 | 1.00 | 21.80 | B | C |
| ATOM | 12758 | O | PHE | B | 264 | 63.236 | 17.496 | −19.791 | 1.00 | 22.35 | B | O |
| ATOM | 12760 | N | TYR | B | 265 | 63.694 | 16.649 | −21.833 | 1.00 | 21.65 | B | N |
| ATOM | 12761 | CA | TYR | B | 265 | 64.396 | 17.839 | −22.327 | 1.00 | 21.35 | B | C |
| ATOM | 12763 | CB | TYR | B | 265 | 64.916 | 17.585 | −23.747 | 1.00 | 21.73 | B | C |
| ATOM | 12766 | CG | TYR | B | 265 | 65.364 | 18.817 | −24.494 | 1.00 | 22.81 | B | C |
| ATOM | 12767 | CD1 | TYR | B | 265 | 66.617 | 19.372 | −24.267 | 1.00 | 24.34 | B | C |
| ATOM | 12769 | CE1 | TYR | B | 265 | 67.033 | 20.501 | −24.954 | 1.00 | 26.45 | B | C |
| ATOM | 12771 | CZ | TYR | B | 265 | 66.192 | 21.083 | −25.886 | 1.00 | 27.60 | B | C |
| ATOM | 12772 | OH | TYR | B | 265 | 66.601 | 22.202 | −26.573 | 1.00 | 30.92 | B | O |
| ATOM | 12774 | CE2 | TYR | B | 265 | 64.944 | 20.544 | −26.133 | 1.00 | 26.49 | B | C |
| ATOM | 12776 | CD2 | TYR | B | 265 | 64.539 | 19.417 | −25.440 | 1.00 | 24.55 | B | C |
| ATOM | 12778 | C | TYR | B | 265 | 63.481 | 19.070 | −22.292 | 1.00 | 20.55 | B | C |
| ATOM | 12779 | O | TYR | B | 265 | 63.923 | 20.176 | −21.983 | 1.00 | 20.24 | B | O |
| ATOM | 12781 | N | TRP | B | 266 | 62.207 | 18.859 | −22.610 | 1.00 | 20.01 | B | N |
| ATOM | 12782 | CA | TRP | B | 266 | 61.183 | 19.894 | −22.484 | 1.00 | 19.27 | B | C |
| ATOM | 12784 | CB | TRP | B | 266 | 59.834 | 19.354 | −22.972 | 1.00 | 19.17 | B | C |
| ATOM | 12787 | CG | TRP | B | 266 | 58.709 | 20.327 | −22.879 | 1.00 | 19.53 | B | C |
| ATOM | 12788 | CD1 | TRP | B | 266 | 57.867 | 20.512 | −21.820 | 1.00 | 19.29 | B | C |
| ATOM | 12790 | NE1 | TRP | B | 266 | 56.955 | 21.496 | −22.107 | 1.00 | 18.94 | B | N |
| ATOM | 12792 | CE2 | TRP | B | 266 | 57.190 | 21.963 | −23.373 | 1.00 | 20.47 | B | C |
| ATOM | 12793 | CD2 | TRP | B | 266 | 58.291 | 21.246 | −23.891 | 1.00 | 21.23 | B | C |
| ATOM | 12794 | CE3 | TRP | B | 266 | 58.742 | 21.537 | −25.184 | 1.00 | 22.28 | B | C |
| ATOM | 12796 | CZ3 | TRP | B | 266 | 58.087 | 22.520 | −25.911 | 1.00 | 22.69 | B | C |
| ATOM | 12798 | CH2 | TRP | B | 266 | 56.996 | 23.218 | −25.367 | 1.00 | 22.30 | B | C |
| ATOM | 12800 | CZ2 | TRP | B | 266 | 56.532 | 22.953 | −24.105 | 1.00 | 20.82 | B | C |
| ATOM | 12802 | C | TRP | B | 266 | 61.069 | 20.374 | −21.039 | 1.00 | 18.58 | B | C |
| ATOM | 12803 | O | TRP | B | 266 | 61.049 | 21.579 | −20.779 | 1.00 | 18.53 | B | O |
| ATOM | 12805 | N | ALA | B | 267 | 61.003 | 19.422 | −20.109 | 1.00 | 18.04 | B | N |
| ATOM | 12806 | CA | ALA | B | 267 | 60.846 | 19.721 | −18.680 | 1.00 | 17.48 | B | C |
| ATOM | 12808 | CB | ALA | B | 267 | 60.644 | 18.432 | −17.888 | 1.00 | 17.29 | B | C |
| ATOM | 12812 | C | ALA | B | 267 | 62.024 | 20.507 | −18.111 | 1.00 | 16.68 | B | C |
| ATOM | 12813 | O | ALA | B | 267 | 61.834 | 21.408 | −17.294 | 1.00 | 16.12 | B | O |
| ATOM | 12815 | N | VAL | B | 268 | 63.233 | 20.169 | −18.556 | 1.00 | 16.04 | B | N |
| ATOM | 12816 | CA | VAL | B | 268 | 64.451 | 20.840 | −18.094 | 1.00 | 15.90 | B | C |
| ATOM | 12818 | CB | VAL | B | 268 | 65.713 | 20.172 | −18.685 | 1.00 | 15.88 | B | C |
| ATOM | 12820 | CG1 | VAL | B | 268 | 65.880 | 18.777 | −18.105 | 1.00 | 16.89 | B | C |
| ATOM | 12824 | CG2 | VAL | B | 268 | 66.954 | 21.001 | −18.414 | 1.00 | 14.94 | B | C |
| ATOM | 12828 | C | VAL | B | 268 | 64.444 | 22.339 | −18.411 | 1.00 | 15.83 | B | C |
| ATOM | 12829 | O | VAL | B | 268 | 65.068 | 23.131 | −17.707 | 1.00 | 15.84 | B | O |
| ATOM | 12831 | N | GLY | B | 269 | 63.736 | 22.725 | −19.467 | 1.00 | 16.01 | B | N |
| ATOM | 12832 | CA | GLY | B | 269 | 63.520 | 24.136 | −19.768 | 1.00 | 16.02 | B | C |
| ATOM | 12835 | C | GLY | B | 269 | 62.558 | 24.781 | −18.788 | 1.00 | 15.89 | B | C |
| ATOM | 12836 | O | GLY | B | 269 | 62.710 | 25.952 | −18.440 | 1.00 | 15.72 | B | O |
| ATOM | 12838 | N | VAL | B | 270 | 61.570 | 24.009 | −18.341 | 1.00 | 15.89 | B | N |
| ATOM | 12839 | CA | VAL | B | 270 | 60.537 | 24.512 | −17.439 | 1.00 | 15.75 | B | C |
| ATOM | 12841 | CB | VAL | B | 270 | 59.329 | 23.550 | −17.364 | 1.00 | 15.72 | B | C |
| ATOM | 12843 | CG1 | VAL | B | 270 | 58.227 | 24.145 | −16.505 | 1.00 | 15.52 | B | C |
| ATOM | 12847 | CG2 | VAL | B | 270 | 58.806 | 23.239 | −18.759 | 1.00 | 15.42 | B | C |
| ATOM | 12851 | C | VAL | B | 270 | 61.098 | 24.728 | −16.039 | 1.00 | 15.62 | B | C |
| ATOM | 12852 | O | VAL | B | 270 | 60.970 | 25.815 | −15.481 | 1.00 | 15.95 | B | O |
| ATOM | 12854 | N | ALA | B | 271 | 61.724 | 23.692 | −15.485 | 1.00 | 15.73 | B | N |
| ATOM | 12855 | CA | ALA | B | 271 | 62.301 | 23.756 | −14.140 | 1.00 | 16.08 | B | C |
| ATOM | 12857 | CB | ALA | B | 271 | 61.403 | 23.033 | −13.156 | 1.00 | 15.92 | B | C |

TABLE 8-2-continued

Coordinates for L494P Structure

| ATOM | 12861 | C | ALA | B | 271 | 63.712 | 23.166 | −14.108 | 1.00 | 16.48 | B | C |
|---|---|---|---|---|---|---|---|---|---|---|---|---|
| ATOM | 12862 | O | ALA | B | 271 | 63.898 | 21.987 | −13.792 | 1.00 | 16.03 | B | O |
| ATOM | 12864 | N | PHE | B | 272 | 64.701 | 23.996 | −14.435 | 1.00 | 17.15 | B | N |
| ATOM | 12865 | CA | PHE | B | 272 | 66.098 | 23.560 | −14.476 | 1.00 | 17.81 | B | C |
| ATOM | 12867 | CB | PHE | B | 272 | 66.968 | 24.549 | −15.268 | 1.00 | 18.10 | B | C |
| ATOM | 12870 | CG | PHE | B | 272 | 67.219 | 25.853 | −14.557 | 1.00 | 19.12 | B | C |
| ATOM | 12871 | CD1 | PHE | B | 272 | 68.266 | 25.978 | −13.654 | 1.00 | 18.88 | B | C |
| ATOM | 12873 | CE1 | PHE | B | 272 | 68.498 | 27.177 | −12.995 | 1.00 | 20.29 | B | C |
| ATOM | 12875 | CZ | PHE | B | 272 | 67.688 | 28.273 | −13.242 | 1.00 | 20.78 | B | C |
| ATOM | 12877 | CE2 | PHE | B | 272 | 66.645 | 28.166 | −14.146 | 1.00 | 21.63 | B | C |
| ATOM | 12879 | CD2 | PHE | B | 272 | 66.414 | 26.960 | −14.799 | 1.00 | 21.22 | B | C |
| ATOM | 12881 | C | PHE | B | 272 | 66.681 | 23.371 | −13.082 | 1.00 | 18.23 | B | C |
| ATOM | 12882 | O | PHE | B | 272 | 67.510 | 22.486 | −12.871 | 1.00 | 18.10 | B | O |
| ATOM | 12884 | N | GLU | B | 273 | 66.246 | 24.206 | −12.138 | 1.00 | 18.89 | B | N |
| ATOM | 12885 | CA | GLU | B | 273 | 66.821 | 24.230 | −10.792 | 1.00 | 19.04 | B | C |
| ATOM | 12887 | CB | GLU | B | 273 | 66.053 | 25.189 | −9.870 | 1.00 | 19.05 | B | C |
| ATOM | 12890 | CG | GLU | B | 273 | 66.068 | 26.665 | −10.295 | 1.00 | 19.59 | B | C |
| ATOM | 12893 | CD | GLU | B | 273 | 64.917 | 27.047 | −11.222 | 1.00 | 22.44 | B | C |
| ATOM | 12894 | OE1 | GLU | B | 273 | 64.464 | 28.210 | −11.163 | 1.00 | 24.11 | B | O |
| ATOM | 12895 | OE2 | GLU | B | 273 | 64.460 | 26.190 | −12.009 | 1.00 | 24.79 | B | O |
| ATOM | 12896 | C | GLU | B | 273 | 66.826 | 22.809 | −10.215 | 1.00 | 18.87 | B | C |
| ATOM | 12897 | O | GLU | B | 273 | 65.801 | 22.129 | −10.257 | 1.00 | 19.19 | B | O |
| ATOM | 12899 | N | PRO | B | 274 | 67.985 | 22.349 | −9.701 | 1.00 | 18.78 | B | N |
| ATOM | 12900 | CA | PRO | B | 274 | 68.155 | 20.957 | −9.253 | 1.00 | 18.78 | B | C |
| ATOM | 12902 | CB | PRO | B | 274 | 69.478 | 20.999 | −8.479 | 1.00 | 18.81 | B | C |
| ATOM | 12905 | CG | PRO | B | 274 | 70.229 | 22.113 | −9.082 | 1.00 | 18.95 | B | C |
| ATOM | 12908 | CD | PRO | B | 274 | 69.231 | 23.127 | −9.550 | 1.00 | 18.65 | B | C |
| ATOM | 12911 | C | PRO | B | 274 | 67.037 | 20.428 | −8.351 | 1.00 | 18.44 | B | C |
| ATOM | 12912 | O | PRO | B | 274 | 66.501 | 19.347 | −8.599 | 1.00 | 18.00 | B | O |
| ATOM | 12913 | N | GLN | B | 275 | 66.704 | 21.197 | −7.320 | 1.00 | 18.53 | B | N |
| ATOM | 12914 | CA | GLN | B | 275 | 65.679 | 20.831 | −6.339 | 1.00 | 18.90 | B | C |
| ATOM | 12916 | CB | GLN | B | 275 | 65.475 | 21.976 | −5.332 | 1.00 | 19.10 | B | C |
| ATOM | 12919 | CG | GLN | B | 275 | 65.092 | 23.339 | −5.936 | 1.00 | 19.30 | B | C |
| ATOM | 12922 | CD | GLN | B | 275 | 66.298 | 24.200 | −6.290 | 1.00 | 19.15 | B | C |
| ATOM | 12923 | OE1 | GLN | B | 275 | 67.237 | 23.734 | −6.933 | 1.00 | 19.04 | B | O |
| ATOM | 12924 | NE2 | GLN | B | 275 | 66.270 | 25.462 | −5.877 | 1.00 | 19.96 | B | N |
| ATOM | 12927 | C | GLN | B | 275 | 64.318 | 20.404 | −6.925 | 1.00 | 19.09 | B | C |
| ATOM | 12928 | O | GLN | B | 275 | 63.643 | 19.549 | −6.347 | 1.00 | 19.14 | B | O |
| ATOM | 12930 | N | TYR | B | 276 | 63.924 | 20.979 | −8.062 | 1.00 | 19.13 | B | N |
| ATOM | 12931 | CA | TYR | B | 276 | 62.625 | 20.672 | −8.679 | 1.00 | 18.93 | B | C |
| ATOM | 12933 | CB | TYR | B | 276 | 62.170 | 21.817 | −9.598 | 1.00 | 18.94 | B | C |
| ATOM | 12936 | CG | TYR | B | 276 | 62.067 | 23.177 | −8.941 | 1.00 | 19.74 | B | C |
| ATOM | 12937 | CD1 | TYR | B | 276 | 61.362 | 23.352 | −7.755 | 1.00 | 20.43 | B | C |
| ATOM | 12939 | CE1 | TYR | B | 276 | 61.263 | 24.600 | −7.159 | 1.00 | 20.81 | B | C |
| ATOM | 12941 | CZ | TYR | B | 276 | 61.858 | 25.692 | −7.759 | 1.00 | 20.24 | B | C |
| ATOM | 12942 | OH | TYR | B | 276 | 61.757 | 26.929 | −7.173 | 1.00 | 23.88 | B | O |
| ATOM | 12944 | CE2 | TYR | B | 276 | 62.551 | 25.550 | −8.942 | 1.00 | 18.69 | B | C |
| ATOM | 12946 | CD2 | TYR | B | 276 | 62.647 | 24.299 | −9.529 | 1.00 | 19.51 | B | C |
| ATOM | 12948 | C | TYR | B | 276 | 62.646 | 19.371 | −9.489 | 1.00 | 18.68 | B | C |
| ATOM | 12949 | O | TYR | B | 276 | 62.344 | 19.376 | −10.681 | 1.00 | 18.82 | B | O |
| ATOM | 12951 | N | SER | B | 277 | 62.983 | 18.256 | −8.848 | 1.00 | 18.35 | B | N |
| ATOM | 12952 | CA | SER | B | 277 | 62.984 | 16.961 | −9.534 | 1.00 | 17.80 | B | C |
| ATOM | 12954 | CB | SER | B | 277 | 63.829 | 15.938 | −8.774 | 1.00 | 17.69 | B | C |
| ATOM | 12957 | OG | SER | B | 277 | 65.212 | 16.219 | −8.923 | 1.00 | 16.37 | B | O |
| ATOM | 12959 | C | SER | B | 277 | 61.558 | 16.449 | −9.743 | 1.00 | 17.75 | B | C |
| ATOM | 12960 | O | SER | B | 277 | 61.257 | 15.869 | −10.783 | 1.00 | 17.82 | B | O |
| ATOM | 12962 | N | ASP | B | 278 | 60.687 | 16.675 | −8.761 | 1.00 | 17.90 | B | N |
| ATOM | 12963 | CA | ASP | B | 278 | 59.267 | 16.323 | −8.881 | 1.00 | 17.97 | B | C |
| ATOM | 12965 | CB | ASP | B | 278 | 58.493 | 16.711 | −7.618 | 1.00 | 18.01 | B | C |
| ATOM | 12968 | CG | ASP | B | 278 | 58.951 | 15.960 | −6.390 | 1.00 | 18.66 | B | C |
| ATOM | 12969 | OD1 | ASP | B | 278 | 59.518 | 14.860 | −6.537 | 1.00 | 22.13 | B | O |
| ATOM | 12970 | OD2 | ASP | B | 278 | 58.740 | 16.473 | −5.271 | 1.00 | 20.36 | B | O |
| ATOM | 12971 | C | ASP | B | 278 | 58.620 | 17.019 | −10.073 | 1.00 | 18.09 | B | C |
| ATOM | 12972 | O | ASP | B | 278 | 57.855 | 16.404 | −10.813 | 1.00 | 18.35 | B | O |
| ATOM | 12974 | N | CYS | B | 279 | 58.919 | 18.303 | −10.246 | 1.00 | 18.18 | B | N |
| ATOM | 12975 | CA | CYS | B | 279 | 58.366 | 19.077 | −11.356 | 1.00 | 18.27 | B | C |
| ATOM | 12977 | CB | CYS | B | 279 | 58.847 | 20.538 | −11.302 | 1.00 | 18.30 | B | C |
| ATOM | 12980 | SG | CYS | B | 279 | 57.937 | 21.699 | −12.374 | 1.00 | 16.99 | B | S |
| ATOM | 12982 | C | CYS | B | 279 | 58.758 | 18.423 | −12.676 | 1.00 | 18.44 | B | C |
| ATOM | 12983 | O | CYS | B | 279 | 57.897 | 18.121 | −13.503 | 1.00 | 18.24 | B | O |
| ATOM | 12985 | N | ARG | B | 280 | 60.055 | 18.178 | −12.846 | 1.00 | 18.78 | B | N |
| ATOM | 12986 | CA | ARG | B | 280 | 60.576 | 17.556 | −14.063 | 1.00 | 18.99 | B | C |
| ATOM | 12988 | CB | ARG | B | 280 | 62.096 | 17.386 | −13.978 | 1.00 | 19.18 | B | C |
| ATOM | 12991 | CG | ARG | B | 280 | 62.866 | 18.702 | −14.057 | 1.00 | 20.22 | B | C |
| ATOM | 12994 | CD | ARG | B | 280 | 64.364 | 18.482 | −14.244 | 1.00 | 20.99 | B | C |
| ATOM | 12997 | NE | ARG | B | 280 | 65.004 | 17.940 | −13.047 | 1.00 | 20.45 | B | N |
| ATOM | 12999 | CZ | ARG | B | 280 | 65.341 | 18.652 | −11.972 | 1.00 | 22.60 | B | C |
| ATOM | 13000 | NH1 | ARG | B | 280 | 65.098 | 19.959 | −11.908 | 1.00 | 22.84 | B | N |

TABLE 8-2-continued

Coordinates for L494P Structure

| ATOM | 13003 | NH2 | ARG | B | 280 | 65.923 | 18.046 | −10.942 | 1.00 | 24.41 | B | N |
|---|---|---|---|---|---|---|---|---|---|---|---|---|
| ATOM | 13006 | C | ARG | B | 280 | 59.906 | 16.212 | −14.339 | 1.00 | 18.84 | B | C |
| ATOM | 13007 | O | ARG | B | 280 | 59.427 | 15.973 | −15.447 | 1.00 | 19.34 | B | O |
| ATOM | 13009 | N | ASN | B | 281 | 59.852 | 15.352 | −13.326 | 1.00 | 18.40 | B | N |
| ATOM | 13010 | CA | ASN | B | 281 | 59.227 | 14.034 | −13.468 | 1.00 | 18.38 | B | C |
| ATOM | 13012 | CB | ASN | B | 281 | 59.559 | 13.146 | −12.266 | 1.00 | 18.31 | B | C |
| ATOM | 13015 | CG | ASN | B | 281 | 61.055 | 12.921 | −12.103 | 1.00 | 19.38 | B | C |
| ATOM | 13016 | OD1 | ASN | B | 281 | 61.851 | 13.291 | −12.969 | 1.00 | 18.81 | B | O |
| ATOM | 13017 | ND2 | ASN | B | 281 | 61.445 | 12.317 | −10.985 | 1.00 | 21.51 | B | N |
| ATOM | 13020 | C | ASN | B | 281 | 57.710 | 14.109 | −13.672 | 1.00 | 18.30 | B | C |
| ATOM | 13021 | O | ASN | B | 281 | 57.126 | 13.240 | −14.317 | 1.00 | 18.27 | B | O |
| ATOM | 13023 | N | SER | B | 282 | 57.078 | 15.150 | −13.132 | 1.00 | 17.93 | B | N |
| ATOM | 13024 | CA | SER | B | 282 | 55.651 | 15.378 | −13.352 | 1.00 | 17.39 | B | C |
| ATOM | 13026 | CB | SER | B | 282 | 55.106 | 16.395 | −12.340 | 1.00 | 17.68 | B | C |
| ATOM | 13029 | OG | SER | B | 282 | 53.687 | 16.431 | −12.343 | 1.00 | 18.53 | B | O |
| ATOM | 13031 | C | SER | B | 282 | 55.410 | 15.861 | −14.786 | 1.00 | 16.41 | B | C |
| ATOM | 13032 | O | SER | B | 282 | 54.649 | 15.251 | −15.535 | 1.00 | 15.72 | B | O |
| ATOM | 13034 | N | VAL | B | 283 | 56.083 | 16.944 | −15.167 | 1.00 | 15.82 | B | N |
| ATOM | 13035 | CA | VAL | B | 283 | 55.893 | 17.546 | −16.489 | 1.00 | 15.38 | B | C |
| ATOM | 13037 | CB | VAL | B | 283 | 56.678 | 18.871 | −16.635 | 1.00 | 15.03 | B | C |
| ATOM | 13039 | CG1 | VAL | B | 283 | 56.610 | 19.388 | −18.066 | 1.00 | 13.71 | B | C |
| ATOM | 13043 | CG2 | VAL | B | 283 | 56.136 | 19.912 | −15.669 | 1.00 | 13.54 | B | C |
| ATOM | 13047 | C | VAL | B | 283 | 56.289 | 16.584 | −17.607 | 1.00 | 15.75 | B | C |
| ATOM | 13048 | O | VAL | B | 283 | 55.608 | 16.504 | −18.627 | 1.00 | 15.73 | B | O |
| ATOM | 13050 | N | ALA | B | 284 | 57.381 | 15.852 | −17.410 | 1.00 | 16.23 | B | N |
| ATOM | 13051 | CA | ALA | B | 284 | 57.811 | 14.857 | −18.387 | 1.00 | 16.83 | B | C |
| ATOM | 13053 | CB | ALA | B | 284 | 59.098 | 14.185 | −17.939 | 1.00 | 16.69 | B | C |
| ATOM | 13057 | C | ALA | B | 284 | 56.713 | 13.818 | −18.592 | 1.00 | 17.70 | B | C |
| ATOM | 13058 | O | ALA | B | 284 | 56.235 | 13.629 | −19.712 | 1.00 | 17.70 | B | O |
| ATOM | 13060 | N | LYS | B | 285 | 56.311 | 13.170 | −17.497 | 1.00 | 18.64 | B | N |
| ATOM | 13061 | CA | LYS | B | 285 | 55.259 | 12.146 | −17.518 | 1.00 | 18.83 | B | C |
| ATOM | 13063 | CB | LYS | B | 285 | 54.860 | 11.750 | −16.089 | 1.00 | 18.82 | B | C |
| ATOM | 13066 | CG | LYS | B | 285 | 55.795 | 10.749 | −15.431 | 1.00 | 20.25 | B | C |
| ATOM | 13069 | CD | LYS | B | 285 | 55.419 | 10.498 | −13.974 | 1.00 | 22.25 | B | C |
| ATOM | 13072 | CE | LYS | B | 285 | 56.438 | 9.597 | −13.279 | 1.00 | 23.50 | B | C |
| ATOM | 13075 | NZ | LYS | B | 285 | 56.327 | 9.653 | −11.792 | 1.00 | 23.56 | B | N |
| ATOM | 13079 | C | LYS | B | 285 | 54.015 | 12.604 | −18.274 | 1.00 | 18.88 | B | C |
| ATOM | 13080 | O | LYS | B | 285 | 53.524 | 11.895 | −19.151 | 1.00 | 18.86 | B | O |
| ATOM | 13082 | N | MET | B | 286 | 53.518 | 13.790 | −17.932 | 1.00 | 19.06 | B | N |
| ATOM | 13083 | CA | MET | B | 286 | 52.272 | 14.299 | −18.506 | 1.00 | 19.32 | B | C |
| ATOM | 13085 | CB | MET | B | 286 | 51.853 | 15.601 | −17.818 | 1.00 | 19.40 | B | C |
| ATOM | 13088 | CG | MET | B | 286 | 51.483 | 15.460 | −16.350 | 1.00 | 19.99 | B | C |
| ATOM | 13091 | SD | MET | B | 286 | 50.219 | 14.220 | −16.032 | 1.00 | 21.41 | B | S |
| ATOM | 13092 | CE | MET | B | 286 | 51.231 | 12.784 | −15.666 | 1.00 | 21.45 | B | C |
| ATOM | 13096 | C | MET | B | 286 | 52.379 | 14.535 | −20.010 | 1.00 | 19.39 | B | C |
| ATOM | 13097 | O | MET | B | 286 | 51.486 | 14.152 | −20.769 | 1.00 | 19.62 | B | O |
| ATOM | 13099 | N | PHE | B | 287 | 53.474 | 15.163 | −20.429 | 1.00 | 19.05 | B | N |
| ATOM | 13100 | CA | PHE | B | 287 | 53.684 | 15.501 | −21.835 | 1.00 | 18.49 | B | C |
| ATOM | 13102 | CB | PHE | B | 287 | 54.845 | 16.499 | −21.969 | 1.00 | 18.88 | B | C |
| ATOM | 13105 | CG | PHE | B | 287 | 54.942 | 17.161 | −23.320 | 1.00 | 19.92 | B | C |
| ATOM | 13106 | CD1 | PHE | B | 287 | 53.805 | 17.632 | −23.977 | 1.00 | 20.75 | B | C |
| ATOM | 13108 | CE1 | PHE | B | 287 | 53.899 | 18.243 | −25.217 | 1.00 | 20.58 | B | C |
| ATOM | 13110 | CZ | PHE | B | 287 | 55.136 | 18.405 | −25.812 | 1.00 | 23.37 | B | C |
| ATOM | 13112 | CE2 | PHE | B | 287 | 56.280 | 17.952 | −25.165 | 1.00 | 23.28 | B | C |
| ATOM | 13114 | CD2 | PHE | B | 287 | 56.178 | 17.338 | −23.925 | 1.00 | 21.35 | B | C |
| ATOM | 13116 | C | PHE | B | 287 | 53.919 | 14.250 | −22.690 | 1.00 | 17.56 | B | C |
| ATOM | 13117 | O | PHE | B | 287 | 53.564 | 14.231 | −23.869 | 1.00 | 17.16 | B | O |
| ATOM | 13119 | N | SER | B | 288 | 54.503 | 13.209 | −22.096 | 1.00 | 16.87 | B | N |
| ATOM | 13120 | CA | SER | B | 288 | 54.594 | 11.903 | −22.757 | 1.00 | 16.53 | B | C |
| ATOM | 13122 | CB | SER | B | 288 | 55.368 | 10.891 | −21.904 | 1.00 | 16.55 | B | C |
| ATOM | 13125 | OG | SER | B | 288 | 56.768 | 11.116 | −21.970 | 1.00 | 16.74 | B | O |
| ATOM | 13127 | C | SER | B | 288 | 53.195 | 11.374 | −23.045 | 1.00 | 16.36 | B | C |
| ATOM | 13128 | O | SER | B | 288 | 52.902 | 10.956 | −24.165 | 1.00 | 16.74 | B | O |
| ATOM | 13130 | N | PHE | B | 289 | 52.331 | 11.406 | −22.034 | 1.00 | 16.08 | B | N |
| ATOM | 13131 | CA | PHE | B | 289 | 50.930 | 11.029 | −22.214 | 1.00 | 15.77 | B | C |
| ATOM | 13133 | CB | PHE | B | 289 | 50.171 | 11.038 | −20.878 | 1.00 | 15.73 | B | C |
| ATOM | 13136 | CG | PHE | B | 289 | 50.321 | 9.767 | −20.087 | 1.00 | 16.79 | B | C |
| ATOM | 13137 | CD1 | PHE | B | 289 | 49.832 | 8.564 | −20.585 | 1.00 | 18.35 | B | C |
| ATOM | 13139 | CE1 | PHE | B | 289 | 49.966 | 7.384 | −19.864 | 1.00 | 17.92 | B | C |
| ATOM | 13141 | CZ | PHE | B | 289 | 50.591 | 7.399 | −18.628 | 1.00 | 18.05 | B | C |
| ATOM | 13143 | CE2 | PHE | B | 289 | 51.081 | 8.591 | −18.119 | 1.00 | 18.22 | B | C |
| ATOM | 13145 | CD2 | PHE | B | 289 | 50.943 | 9.768 | −18.846 | 1.00 | 17.63 | B | C |
| ATOM | 13147 | C | PHE | B | 289 | 50.225 | 11.930 | −23.229 | 1.00 | 15.42 | B | C |
| ATOM | 13148 | O | PHE | B | 289 | 49.437 | 11.445 | −24.039 | 1.00 | 15.46 | B | O |
| ATOM | 13150 | N | VAL | B | 290 | 50.517 | 13.230 | −23.193 | 1.00 | 15.19 | B | N |
| ATOM | 13151 | CA | VAL | B | 290 | 49.908 | 14.179 | −24.133 | 1.00 | 14.81 | B | C |
| ATOM | 13153 | CB | VAL | B | 290 | 50.383 | 15.639 | −23.905 | 1.00 | 14.27 | B | C |
| ATOM | 13155 | CG1 | VAL | B | 290 | 49.790 | 16.565 | −24.954 | 1.00 | 11.43 | B | C |

TABLE 8-2-continued

Coordinates for L494P Structure

| ATOM | 13159 | CG2 | VAL | B | 290 | 50.002 | 16.118 | −22.521 | 1.00 | 13.72 | B | C |
|---|---|---|---|---|---|---|---|---|---|---|---|---|
| ATOM | 13163 | C | VAL | B | 290 | 50.194 | 13.784 | −25.583 | 1.00 | 15.49 | B | C |
| ATOM | 13164 | O | VAL | B | 290 | 49.276 | 13.740 | −26.402 | 1.00 | 15.62 | B | O |
| ATOM | 13166 | N | THR | B | 291 | 51.455 | 13.476 | −25.893 | 1.00 | 15.62 | B | N |
| ATOM | 13167 | CA | THR | B | 291 | 51.838 | 13.155 | −27.273 | 1.00 | 15.90 | B | C |
| ATOM | 13169 | CB | THR | B | 291 | 53.367 | 12.948 | −27.445 | 1.00 | 15.92 | B | C |
| ATOM | 13171 | OG1 | THR | B | 291 | 53.781 | 11.762 | −26.759 | 1.00 | 17.87 | B | O |
| ATOM | 13173 | CG2 | THR | B | 291 | 54.150 | 14.145 | −26.917 | 1.00 | 16.50 | B | C |
| ATOM | 13177 | C | THR | B | 291 | 51.109 | 11.914 | −27.786 | 1.00 | 15.66 | B | C |
| ATOM | 13178 | O | THR | B | 291 | 50.809 | 11.818 | −28.977 | 1.00 | 15.78 | B | O |
| ATOM | 13180 | N | ILE | B | 292 | 50.824 | 10.977 | −26.882 | 1.00 | 15.54 | B | N |
| ATOM | 13181 | CA | ILE | B | 292 | 50.114 | 9.743 | −27.228 | 1.00 | 15.38 | B | C |
| ATOM | 13183 | CB | ILE | B | 292 | 50.331 | 8.650 | −26.160 | 1.00 | 15.32 | B | C |
| ATOM | 13185 | CG1 | ILE | B | 292 | 51.803 | 8.234 | −26.129 | 1.00 | 13.86 | B | C |
| ATOM | 13188 | CD1 | ILE | B | 292 | 52.103 | 7.171 | −25.111 | 1.00 | 13.47 | B | C |
| ATOM | 13192 | CG2 | ILE | B | 292 | 49.446 | 7.434 | −26.437 | 1.00 | 15.16 | B | C |
| ATOM | 13196 | C | ILE | B | 292 | 48.612 | 9.978 | −27.426 | 1.00 | 15.28 | B | C |
| ATOM | 13197 | O | ILE | B | 292 | 48.023 | 9.462 | −28.379 | 1.00 | 15.27 | B | O |
| ATOM | 13199 | N | ILE | B | 293 | 47.997 | 10.749 | −26.531 | 1.00 | 14.89 | B | N |
| ATOM | 13200 | CA | ILE | B | 293 | 46.580 | 11.079 | −26.672 | 1.00 | 14.80 | B | C |
| ATOM | 13202 | CB | ILE | B | 293 | 46.012 | 11.832 | −25.453 | 1.00 | 14.64 | B | C |
| ATOM | 13204 | CG1 | ILE | B | 293 | 46.094 | 10.979 | −24.184 | 1.00 | 14.55 | B | C |
| ATOM | 13207 | CD1 | ILE | B | 293 | 45.101 | 9.846 | −24.144 | 1.00 | 14.32 | B | C |
| ATOM | 13211 | CG2 | ILE | B | 293 | 44.558 | 12.203 | −25.700 | 1.00 | 14.22 | B | C |
| ATOM | 13215 | C | ILE | B | 293 | 46.394 | 11.938 | −27.916 | 1.00 | 15.23 | B | C |
| ATOM | 13216 | O | ILE | B | 293 | 45.466 | 11.724 | −28.691 | 1.00 | 15.35 | B | O |
| ATOM | 13218 | N | ASP | B | 294 | 47.291 | 12.901 | −28.110 | 1.00 | 15.94 | B | N |
| ATOM | 13219 | CA | ASP | B | 294 | 47.273 | 13.739 | −29.313 | 1.00 | 16.55 | B | C |
| ATOM | 13221 | CB | ASP | B | 294 | 48.491 | 14.682 | −29.346 | 1.00 | 17.12 | B | C |
| ATOM | 13224 | CG | ASP | B | 294 | 48.314 | 15.858 | −30.307 | 1.00 | 17.49 | B | C |
| ATOM | 13225 | OD1 | ASP | B | 294 | 47.164 | 16.220 | −30.634 | 1.00 | 17.71 | B | O |
| ATOM | 13226 | OD2 | ASP | B | 294 | 49.342 | 16.437 | −30.720 | 1.00 | 18.55 | B | O |
| ATOM | 13227 | C | ASP | B | 294 | 47.239 | 12.861 | −30.564 | 1.00 | 16.11 | B | C |
| ATOM | 13228 | O | ASP | B | 294 | 46.495 | 13.144 | −31.495 | 1.00 | 16.16 | B | O |
| ATOM | 13230 | N | ASP | B | 295 | 48.029 | 11.788 | −30.567 | 1.00 | 15.75 | B | N |
| ATOM | 13231 | CA | ASP | B | 295 | 48.006 | 10.816 | −31.663 | 1.00 | 15.80 | B | C |
| ATOM | 13233 | CB | ASP | B | 295 | 49.092 | 9.750 | −31.481 | 1.00 | 15.85 | B | C |
| ATOM | 13236 | CG | ASP | B | 295 | 50.462 | 10.218 | −31.932 | 1.00 | 15.72 | B | C |
| ATOM | 13237 | OD1 | ASP | B | 295 | 50.570 | 11.306 | −32.536 | 1.00 | 16.90 | B | O |
| ATOM | 13238 | OD2 | ASP | B | 295 | 51.440 | 9.486 | −31.684 | 1.00 | 13.67 | B | O |
| ATOM | 13239 | C | ASP | B | 295 | 46.650 | 10.132 | −31.797 | 1.00 | 15.95 | B | C |
| ATOM | 13240 | O | ASP | B | 295 | 46.149 | 9.960 | −32.911 | 1.00 | 16.24 | B | O |
| ATOM | 13242 | N | ILE | B | 296 | 46.063 | 9.738 | −30.668 | 1.00 | 15.64 | B | N |
| ATOM | 13243 | CA | ILE | B | 296 | 44.754 | 9.080 | −30.674 | 1.00 | 15.06 | B | C |
| ATOM | 13245 | CB | ILE | B | 296 | 44.270 | 8.738 | −29.251 | 1.00 | 14.85 | B | C |
| ATOM | 13247 | CG1 | ILE | B | 296 | 45.067 | 7.558 | −28.699 | 1.00 | 14.95 | B | C |
| ATOM | 13250 | CD1 | ILE | B | 296 | 44.747 | 7.211 | −27.266 | 1.00 | 15.45 | B | C |
| ATOM | 13254 | CG2 | ILE | B | 296 | 42.795 | 8.378 | −29.263 | 1.00 | 15.55 | B | C |
| ATOM | 13258 | C | ILE | B | 296 | 43.696 | 9.932 | −31.365 | 1.00 | 14.52 | B | C |
| ATOM | 13259 | O | ILE | B | 296 | 43.010 | 9.462 | −32.269 | 1.00 | 14.11 | B | O |
| ATOM | 13261 | N | TYR | B | 297 | 43.579 | 11.185 | −30.941 | 1.00 | 14.55 | B | N |
| ATOM | 13262 | CA | TYR | B | 297 | 42.557 | 12.089 | −31.471 | 1.00 | 14.75 | B | C |
| ATOM | 13264 | CB | TYR | B | 297 | 42.392 | 13.311 | −30.558 | 1.00 | 14.65 | B | C |
| ATOM | 13267 | CG | TYR | B | 297 | 41.605 | 13.051 | −29.288 | 1.00 | 13.97 | B | C |
| ATOM | 13268 | CD1 | TYR | B | 297 | 40.311 | 13.543 | −29.132 | 1.00 | 15.04 | B | C |
| ATOM | 13270 | CE1 | TYR | B | 297 | 39.586 | 13.315 | −27.963 | 1.00 | 15.12 | B | C |
| ATOM | 13272 | CZ | TYR | B | 297 | 40.157 | 12.584 | −26.938 | 1.00 | 16.10 | B | C |
| ATOM | 13273 | OH | TYR | B | 297 | 39.452 | 12.349 | −25.781 | 1.00 | 17.13 | B | O |
| ATOM | 13275 | CE2 | TYR | B | 297 | 41.439 | 12.086 | −27.070 | 1.00 | 16.03 | B | C |
| ATOM | 13277 | CD2 | TYR | B | 297 | 42.156 | 12.322 | −28.240 | 1.00 | 15.06 | B | C |
| ATOM | 13279 | C | TYR | B | 297 | 42.869 | 12.545 | −32.898 | 1.00 | 14.81 | B | C |
| ATOM | 13280 | O | TYR | B | 297 | 41.995 | 12.524 | −33.770 | 1.00 | 14.70 | B | O |
| ATOM | 13282 | N | ASP | B | 298 | 44.117 | 12.946 | −33.125 | 1.00 | 14.76 | B | N |
| ATOM | 13283 | CA | ASP | B | 298 | 44.529 | 13.551 | −34.391 | 1.00 | 14.85 | B | C |
| ATOM | 13285 | CB | ASP | B | 298 | 46.011 | 13.965 | −34.327 | 1.00 | 15.56 | B | C |
| ATOM | 13288 | CG | ASP | B | 298 | 46.436 | 14.845 | −35.495 | 1.00 | 16.94 | B | C |
| ATOM | 13289 | OD1 | ASP | B | 298 | 45.717 | 15.822 | −35.798 | 1.00 | 19.66 | B | O |
| ATOM | 13290 | OD2 | ASP | B | 298 | 47.500 | 14.571 | −36.096 | 1.00 | 16.83 | B | O |
| ATOM | 13291 | C | ASP | B | 298 | 44.298 | 12.621 | −35.579 | 1.00 | 13.99 | B | C |
| ATOM | 13292 | O | ASP | B | 298 | 43.653 | 13.011 | −36.552 | 1.00 | 13.35 | B | O |
| ATOM | 13294 | N | VAL | B | 299 | 44.813 | 11.395 | −35.487 | 1.00 | 13.69 | B | N |
| ATOM | 13295 | CA | VAL | B | 299 | 44.819 | 10.467 | −36.629 | 1.00 | 13.50 | B | C |
| ATOM | 13297 | CB | VAL | B | 299 | 46.263 | 10.201 | −37.129 | 1.00 | 13.48 | B | C |
| ATOM | 13299 | CG1 | VAL | B | 299 | 46.901 | 11.491 | −37.614 | 1.00 | 14.14 | B | C |
| ATOM | 13303 | CG2 | VAL | B | 299 | 47.111 | 9.556 | −36.038 | 1.00 | 13.60 | B | C |
| ATOM | 13307 | C | VAL | B | 299 | 44.139 | 9.112 | −36.404 | 1.00 | 12.90 | B | C |
| ATOM | 13308 | O | VAL | B | 299 | 43.543 | 8.574 | −37.336 | 1.00 | 12.78 | B | O |
| ATOM | 13310 | N | TYR | B | 300 | 44.217 | 8.563 | −35.192 | 1.00 | 12.41 | B | N |

TABLE 8-2-continued

Coordinates for L494P Structure

| ATOM | 13311 | CA  | TYR | B | 300 | 43.884 | 7.149  | −34.976 | 1.00 | 12.41 B | C |
|------|-------|-----|-----|---|-----|--------|--------|---------|------|---------|---|
| ATOM | 13313 | CB  | TYR | B | 300 | 44.802 | 6.549  | −33.911 | 1.00 | 12.27 B | C |
| ATOM | 13316 | CG  | TYR | B | 300 | 44.709 | 5.041  | −33.826 | 1.00 | 12.47 B | C |
| ATOM | 13317 | CD1 | TYR | B | 300 | 45.090 | 4.241  | −34.898 | 1.00 | 11.58 B | C |
| ATOM | 13319 | CE1 | TYR | B | 300 | 45.005 | 2.858  | −34.831 | 1.00 | 10.77 B | C |
| ATOM | 13321 | CZ  | TYR | B | 300 | 44.535 | 2.258  | −33.681 | 1.00 | 10.71 B | C |
| ATOM | 13322 | OH  | TYR | B | 300 | 44.451 | 0.888  | −33.608 | 1.00 | 11.57 B | O |
| ATOM | 13324 | CE2 | TYR | B | 300 | 44.150 | 3.027  | −32.602 | 1.00 | 13.01 B | C |
| ATOM | 13326 | CD2 | TYR | B | 300 | 44.237 | 4.415  | −32.679 | 1.00 | 13.92 B | C |
| ATOM | 13328 | C   | TYR | B | 300 | 42.420 | 6.833  | −34.624 | 1.00 | 12.63 B | C |
| ATOM | 13329 | O   | TYR | B | 300 | 41.804 | 5.979  | −35.259 | 1.00 | 12.91 B | O |
| ATOM | 13331 | N   | GLY | B | 301 | 41.869 | 7.496  | −33.614 | 1.00 | 12.74 B | N |
| ATOM | 13332 | CA  | GLY | B | 301 | 40.531 | 7.156  | −33.118 | 1.00 | 12.64 B | C |
| ATOM | 13335 | C   | GLY | B | 301 | 39.382 | 7.678  | −33.966 | 1.00 | 12.49 B | C |
| ATOM | 13336 | O   | GLY | B | 301 | 39.498 | 8.719  | −34.613 | 1.00 | 12.57 B | O |
| ATOM | 13338 | N   | THR | B | 302 | 38.265 | 6.951  | −33.957 | 1.00 | 12.36 B | N |
| ATOM | 13339 | CA  | THR | B | 302 | 37.033 | 7.433  | −34.579 | 1.00 | 12.60 B | C |
| ATOM | 13341 | CB  | THR | B | 302 | 36.010 | 6.307  | −34.834 | 1.00 | 12.31 B | C |
| ATOM | 13343 | OG1 | THR | B | 302 | 35.511 | 5.810  | −33.587 | 1.00 | 11.75 B | O |
| ATOM | 13345 | CG2 | THR | B | 302 | 36.631 | 5.171  | −35.624 | 1.00 | 12.44 B | C |
| ATOM | 13349 | C   | THR | B | 302 | 36.391 | 8.449  | −33.653 | 1.00 | 13.44 B | C |
| ATOM | 13350 | O   | THR | B | 302 | 36.764 | 8.556  | −32.487 | 1.00 | 13.63 B | O |
| ATOM | 13352 | N   | LEU | B | 303 | 35.408 | 9.181  | −34.166 | 1.00 | 14.23 B | N |
| ATOM | 13353 | CA  | LEU | B | 303 | 34.732 | 10.205 | −33.373 | 1.00 | 14.47 B | C |
| ATOM | 13355 | CB  | LEU | B | 303 | 33.758 | 11.004 | −34.239 | 1.00 | 14.69 B | C |
| ATOM | 13358 | CG  | LEU | B | 303 | 33.460 | 12.428 | −33.775 | 1.00 | 14.65 B | C |
| ATOM | 13360 | CD1 | LEU | B | 303 | 34.684 | 13.310 | −33.959 | 1.00 | 13.80 B | C |
| ATOM | 13364 | CD2 | LEU | B | 303 | 32.268 | 12.988 | −34.544 | 1.00 | 16.81 B | C |
| ATOM | 13368 | C   | LEU | B | 303 | 33.998 | 9.573  | −32.192 | 1.00 | 14.67 B | C |
| ATOM | 13369 | O   | LEU | B | 303 | 34.065 | 10.082 | −31.075 | 1.00 | 14.67 B | O |
| ATOM | 13371 | N   | ASP | B | 304 | 33.311 | 8.460  | −32.449 | 1.00 | 15.27 B | N |
| ATOM | 13372 | CA  | ASP | B | 304 | 32.630 | 7.694  | −31.395 | 1.00 | 15.80 B | C |
| ATOM | 13374 | CB  | ASP | B | 304 | 31.828 | 6.523  | −31.991 | 1.00 | 16.12 B | C |
| ATOM | 13377 | CG  | ASP | B | 304 | 30.537 | 6.966  | −32.668 | 1.00 | 16.23 B | C |
| ATOM | 13378 | OD1 | ASP | B | 304 | 30.252 | 8.183  | −32.707 | 1.00 | 17.00 B | O |
| ATOM | 13379 | OD2 | ASP | B | 304 | 29.803 | 6.086  | −33.165 | 1.00 | 15.17 B | O |
| ATOM | 13380 | C   | ASP | B | 304 | 33.617 | 7.155  | −30.356 | 1.00 | 15.75 B | C |
| ATOM | 13381 | O   | ASP | B | 304 | 33.332 | 7.168  | −29.154 | 1.00 | 15.68 B | O |
| ATOM | 13383 | N   | GLU | B | 305 | 34.765 | 6.669  | −30.823 | 1.00 | 15.44 B | N |
| ATOM | 13384 | CA  | GLU | B | 305 | 35.823 | 6.207  | −29.926 | 1.00 | 15.31 B | C |
| ATOM | 13386 | CB  | GLU | B | 305 | 36.965 | 5.564  | −30.713 | 1.00 | 15.57 B | C |
| ATOM | 13389 | CG  | GLU | B | 305 | 36.689 | 4.138  | −31.162 | 1.00 | 15.98 B | C |
| ATOM | 13392 | CD  | GLU | B | 305 | 37.800 | 3.581  | −32.027 | 1.00 | 16.46 B | C |
| ATOM | 13393 | OE1 | GLU | B | 305 | 38.399 | 4.350  | −32.807 | 1.00 | 17.84 B | O |
| ATOM | 13394 | OE2 | GLU | B | 305 | 38.076 | 2.369  | −31.936 | 1.00 | 17.97 B | O |
| ATOM | 13395 | C   | GLU | B | 305 | 36.366 | 7.357  | −29.088 | 1.00 | 15.04 B | C |
| ATOM | 13396 | O   | GLU | B | 305 | 36.621 | 7.190  | −27.895 | 1.00 | 15.15 B | O |
| ATOM | 13398 | N   | LEU | B | 306 | 36.536 | 8.518  | −29.720 | 1.00 | 14.77 B | N |
| ATOM | 13399 | CA  | LEU | B | 306 | 37.040 | 9.715  | −29.040 | 1.00 | 13.94 B | C |
| ATOM | 13401 | CB  | LEU | B | 306 | 37.447 | 10.778 | −30.064 | 1.00 | 13.32 B | C |
| ATOM | 13404 | CG  | LEU | B | 306 | 38.667 | 10.392 | −30.903 | 1.00 | 11.95 B | C |
| ATOM | 13406 | CD1 | LEU | B | 306 | 38.892 | 11.372 | −32.041 | 1.00 | 9.49 B  | C |
| ATOM | 13410 | CD2 | LEU | B | 306 | 39.897 | 10.287 | −30.018 | 1.00 | 12.30 B | C |
| ATOM | 13414 | C   | LEU | B | 306 | 36.024 | 10.283 | −28.050 | 1.00 | 14.05 B | C |
| ATOM | 13415 | O   | LEU | B | 306 | 36.405 | 10.817 | −27.007 | 1.00 | 13.84 B | O |
| ATOM | 13417 | N   | GLU | B | 307 | 34.739 | 10.159 | −28.374 | 1.00 | 14.32 B | N |
| ATOM | 13418 | CA  | GLU | B | 307 | 33.672 | 10.542 | −27.448 | 1.00 | 14.91 B | C |
| ATOM | 13420 | CB  | GLU | B | 307 | 32.296 | 10.437 | −28.119 | 1.00 | 15.01 B | C |
| ATOM | 13423 | CG  | GLU | B | 307 | 31.885 | 11.687 | −28.890 | 1.00 | 16.39 B | C |
| ATOM | 13426 | CD  | GLU | B | 307 | 31.587 | 12.875 | −27.985 | 1.00 | 18.17 B | C |
| ATOM | 13427 | OE1 | GLU | B | 307 | 31.715 | 14.025 | −28.455 | 1.00 | 18.84 B | O |
| ATOM | 13428 | OE2 | GLU | B | 307 | 31.227 | 12.662 | −26.805 | 1.00 | 19.10 B | O |
| ATOM | 13429 | C   | GLU | B | 307 | 33.695 | 9.709  | −26.164 | 1.00 | 15.05 B | C |
| ATOM | 13430 | O   | GLU | B | 307 | 33.545 | 10.256 | −25.070 | 1.00 | 15.50 B | O |
| ATOM | 13432 | N   | LEU | B | 308 | 33.883 | 8.395  | −26.299 | 1.00 | 14.90 B | N |
| ATOM | 13433 | CA  | LEU | B | 308 | 33.941 | 7.501  | −25.136 | 1.00 | 14.90 B | C |
| ATOM | 13435 | CB  | LEU | B | 308 | 33.975 | 6.027  | −25.562 | 1.00 | 15.03 B | C |
| ATOM | 13438 | CG  | LEU | B | 308 | 32.705 | 5.409  | −26.151 | 1.00 | 15.09 B | C |
| ATOM | 13440 | CD1 | LEU | B | 308 | 32.922 | 3.918  | −26.391 | 1.00 | 12.37 B | C |
| ATOM | 13444 | CD2 | LEU | B | 308 | 31.503 | 5.640  | −25.244 | 1.00 | 14.58 B | C |
| ATOM | 13448 | C   | LEU | B | 308 | 35.144 | 7.794  | −24.244 | 1.00 | 14.76 B | C |
| ATOM | 13449 | O   | LEU | B | 308 | 35.047 | 7.693  | −23.023 | 1.00 | 14.83 B | O |
| ATOM | 13451 | N   | PHE | B | 309 | 36.272 | 8.148  | −24.854 | 1.00 | 14.97 B | N |
| ATOM | 13452 | CA  | PHE | B | 309 | 37.482 | 8.481  | −24.102 | 1.00 | 15.23 B | C |
| ATOM | 13454 | CB  | PHE | B | 309 | 38.701 | 8.540  | −25.030 | 1.00 | 14.93 B | C |
| ATOM | 13457 | CG  | PHE | B | 309 | 40.014 | 8.476  | −24.303 | 1.00 | 12.81 B | C |
| ATOM | 13458 | CD1 | PHE | B | 309 | 40.712 | 7.280  | −24.213 | 1.00 | 10.56 B | C |
| ATOM | 13460 | CE1 | PHE | B | 309 | 41.919 | 7.212  | −23.537 | 1.00 | 9.68 B  | C |

TABLE 8-2-continued

Coordinates for L494P Structure

| ATOM | 13462 | CZ | PHE | B | 309 | 42.440 | 8.345 | −22.941 | 1.00 | 10.55 | B | C |
|---|---|---|---|---|---|---|---|---|---|---|---|---|
| ATOM | 13464 | CE2 | PHE | B | 309 | 41.752 | 9.550 | −23.020 | 1.00 | 11.50 | B | C |
| ATOM | 13466 | CD2 | PHE | B | 309 | 40.547 | 9.610 | −23.698 | 1.00 | 11.86 | B | C |
| ATOM | 13468 | C | PHE | B | 309 | 37.318 | 9.815 | −23.361 | 1.00 | 16.02 | B | C |
| ATOM | 13469 | O | PHE | B | 309 | 37.597 | 9.905 | −22.162 | 1.00 | 16.16 | B | O |
| ATOM | 13471 | N | THR | B | 310 | 36.876 | 10.843 | −24.083 | 1.00 | 16.42 | B | N |
| ATOM | 13472 | CA | THR | B | 310 | 36.594 | 12.144 | −23.484 | 1.00 | 16.93 | B | C |
| ATOM | 13474 | CB | THR | B | 310 | 35.941 | 13.101 | −24.499 | 1.00 | 17.11 | B | C |
| ATOM | 13476 | OG1 | THR | B | 310 | 36.753 | 13.182 | −25.676 | 1.00 | 18.04 | B | O |
| ATOM | 13478 | CG2 | THR | B | 310 | 35.775 | 14.490 | −23.898 | 1.00 | 17.27 | B | C |
| ATOM | 13482 | C | THR | B | 310 | 35.645 | 11.970 | −22.306 | 1.00 | 17.22 | B | C |
| ATOM | 13483 | O | THR | B | 310 | 35.893 | 12.475 | −21.213 | 1.00 | 17.31 | B | O |
| ATOM | 13485 | N | ASP | B | 311 | 34.560 | 11.242 | −22.549 | 1.00 | 17.64 | B | N |
| ATOM | 13486 | CA | ASP | B | 311 | 33.559 | 10.957 | −21.529 | 1.00 | 18.02 | B | C |
| ATOM | 13488 | CB | ASP | B | 311 | 32.432 | 10.119 | −22.136 | 1.00 | 17.98 | B | C |
| ATOM | 13491 | CG | ASP | B | 311 | 31.441 | 9.638 | −21.103 | 1.00 | 18.70 | B | C |
| ATOM | 13492 | OD1 | ASP | B | 311 | 30.851 | 10.486 | −20.399 | 1.00 | 19.29 | B | O |
| ATOM | 13493 | OD2 | ASP | B | 311 | 31.251 | 8.407 | −20.997 | 1.00 | 21.03 | B | O |
| ATOM | 13494 | C | ASP | B | 311 | 34.160 | 10.228 | −20.326 | 1.00 | 18.33 | B | C |
| ATOM | 13495 | O | ASP | B | 311 | 33.934 | 10.624 | −19.182 | 1.00 | 18.39 | B | O |
| ATOM | 13497 | N | ALA | B | 312 | 34.925 | 9.170 | −20.597 | 1.00 | 18.50 | B | N |
| ATOM | 13498 | CA | ALA | B | 312 | 35.524 | 8.335 | −19.548 | 1.00 | 18.23 | B | C |
| ATOM | 13500 | CB | ALA | B | 312 | 36.268 | 7.159 | −20.168 | 1.00 | 18.14 | B | C |
| ATOM | 13504 | C | ALA | B | 312 | 36.456 | 9.117 | −18.625 | 1.00 | 18.16 | B | C |
| ATOM | 13505 | O | ALA | B | 312 | 36.513 | 8.845 | −17.426 | 1.00 | 18.48 | B | O |
| ATOM | 13507 | N | VAL | B | 313 | 37.183 | 10.079 | −19.189 | 1.00 | 18.03 | B | N |
| ATOM | 13508 | CA | VAL | B | 313 | 38.050 | 10.960 | −18.405 | 1.00 | 18.31 | B | C |
| ATOM | 13510 | CB | VAL | B | 313 | 38.965 | 11.805 | −19.326 | 1.00 | 18.52 | B | C |
| ATOM | 13512 | CG1 | VAL | B | 313 | 40.105 | 10.946 | −19.870 | 1.00 | 18.57 | B | C |
| ATOM | 13516 | CG2 | VAL | B | 313 | 39.515 | 13.021 | −18.588 | 1.00 | 18.51 | B | C |
| ATOM | 13520 | C | VAL | B | 313 | 37.240 | 11.882 | −17.486 | 1.00 | 18.58 | B | C |
| ATOM | 13521 | O | VAL | B | 313 | 37.553 | 12.016 | −16.303 | 1.00 | 18.04 | B | O |
| ATOM | 13523 | N | GLU | B | 314 | 36.198 | 12.504 | −18.033 | 1.00 | 19.37 | B | N |
| ATOM | 13524 | CA | GLU | B | 314 | 35.321 | 13.395 | −17.258 | 1.00 | 20.06 | B | C |
| ATOM | 13526 | CB | GLU | B | 314 | 34.224 | 13.987 | −18.154 | 1.00 | 20.50 | B | C |
| ATOM | 13529 | CG | GLU | B | 314 | 34.697 | 15.089 | −19.102 | 1.00 | 21.76 | B | C |
| ATOM | 13532 | CD | GLU | B | 314 | 33.609 | 15.550 | −20.064 | 1.00 | 23.96 | B | C |
| ATOM | 13533 | OE1 | GLU | B | 314 | 33.914 | 16.363 | −20.962 | 1.00 | 23.97 | B | O |
| ATOM | 13534 | OE2 | GLU | B | 314 | 32.449 | 15.100 | −19.929 | 1.00 | 25.34 | B | O |
| ATOM | 13535 | C | GLU | B | 314 | 34.667 | 12.709 | −16.053 | 1.00 | 19.90 | B | C |
| ATOM | 13536 | O | GLU | B | 314 | 34.342 | 13.369 | −15.068 | 1.00 | 20.36 | B | O |
| ATOM | 13538 | N | ARG | B | 315 | 34.463 | 11.398 | −16.141 | 1.00 | 19.78 | B | N |
| ATOM | 13539 | CA | ARG | B | 315 | 33.863 | 10.626 | −15.054 | 1.00 | 20.09 | B | C |
| ATOM | 13541 | CB | ARG | B | 315 | 33.116 | 9.420 | −15.616 | 1.00 | 20.83 | B | C |
| ATOM | 13544 | CG | ARG | B | 315 | 31.940 | 9.789 | −16.488 | 1.00 | 23.42 | B | C |
| ATOM | 13547 | CD | ARG | B | 315 | 31.282 | 8.560 | −17.080 | 1.00 | 27.26 | B | C |
| ATOM | 13550 | NE | ARG | B | 315 | 30.102 | 8.922 | −17.863 | 1.00 | 32.39 | B | N |
| ATOM | 13552 | CZ | ARG | B | 315 | 28.915 | 9.250 | −17.351 | 1.00 | 35.04 | B | C |
| ATOM | 13553 | NH1 | ARG | B | 315 | 28.712 | 9.262 | −16.035 | 1.00 | 36.54 | B | N |
| ATOM | 13556 | NH2 | ARG | B | 315 | 27.914 | 9.567 | −18.168 | 1.00 | 34.69 | B | N |
| ATOM | 13559 | C | ARG | B | 315 | 34.901 | 10.145 | −14.049 | 1.00 | 19.51 | B | C |
| ATOM | 13560 | O | ARG | B | 315 | 34.642 | 10.126 | −12.845 | 1.00 | 19.73 | B | O |
| ATOM | 13562 | N | TRP | B | 316 | 36.065 | 9.741 | −14.553 | 1.00 | 18.77 | B | N |
| ATOM | 13563 | CA | TRP | B | 316 | 37.150 | 9.218 | −13.725 | 1.00 | 17.72 | B | C |
| ATOM | 13565 | CB | TRP | B | 316 | 37.694 | 10.308 | −12.794 | 1.00 | 17.03 | B | C |
| ATOM | 13568 | CG | TRP | B | 316 | 39.112 | 10.081 | −12.398 | 1.00 | 14.29 | B | C |
| ATOM | 13569 | CD1 | TRP | B | 316 | 39.566 | 9.639 | −11.195 | 1.00 | 13.02 | B | C |
| ATOM | 13571 | NE1 | TRP | B | 316 | 40.934 | 9.547 | −11.211 | 1.00 | 12.01 | B | N |
| ATOM | 13573 | CE2 | TRP | B | 316 | 41.389 | 9.930 | −12.443 | 1.00 | 11.63 | B | C |
| ATOM | 13574 | CD2 | TRP | B | 316 | 40.267 | 10.271 | −13.218 | 1.00 | 12.10 | B | C |
| ATOM | 13575 | CE3 | TRP | B | 316 | 40.462 | 10.702 | −14.533 | 1.00 | 13.74 | B | C |
| ATOM | 13577 | CZ3 | TRP | B | 316 | 41.752 | 10.778 | −15.024 | 1.00 | 13.08 | B | C |
| ATOM | 13579 | CH2 | TRP | B | 316 | 42.848 | 10.432 | −14.228 | 1.00 | 13.51 | B | C |
| ATOM | 13581 | CZ2 | TRP | B | 316 | 42.688 | 10.004 | −12.937 | 1.00 | 13.12 | B | C |
| ATOM | 13583 | C | TRP | B | 316 | 36.678 | 7.995 | −12.940 | 1.00 | 17.90 | B | C |
| ATOM | 13584 | O | TRP | B | 316 | 36.859 | 7.909 | −11.727 | 1.00 | 17.86 | B | O |
| ATOM | 13586 | N | ASP | B | 317 | 36.073 | 7.053 | −13.658 | 1.00 | 18.19 | B | N |
| ATOM | 13587 | CA | ASP | B | 317 | 35.487 | 5.863 | −13.057 | 1.00 | 18.63 | B | C |
| ATOM | 13589 | CB | ASP | B | 317 | 33.983 | 5.825 | −13.354 | 1.00 | 18.49 | B | C |
| ATOM | 13592 | CG | ASP | B | 317 | 33.270 | 4.671 | −12.664 | 1.00 | 18.45 | B | C |
| ATOM | 13593 | OD1 | ASP | B | 317 | 33.789 | 4.140 | −11.659 | 1.00 | 17.90 | B | O |
| ATOM | 13594 | OD2 | ASP | B | 317 | 32.173 | 4.298 | −13.129 | 1.00 | 19.26 | B | O |
| ATOM | 13595 | C | ASP | B | 317 | 36.177 | 4.618 | −13.605 | 1.00 | 19.33 | B | C |
| ATOM | 13596 | O | ASP | B | 317 | 35.899 | 4.186 | −14.723 | 1.00 | 19.83 | B | O |
| ATOM | 13598 | N | VAL | B | 318 | 37.072 | 4.040 | −12.808 | 1.00 | 20.11 | B | N |
| ATOM | 13599 | CA | VAL | B | 318 | 37.836 | 2.857 | −13.222 | 1.00 | 20.65 | B | C |
| ATOM | 13601 | CB | VAL | B | 318 | 38.983 | 2.555 | −12.231 | 1.00 | 20.75 | B | C |
| ATOM | 13603 | CG1 | VAL | B | 318 | 40.006 | 1.618 | −12.859 | 1.00 | 20.37 | B | C |

TABLE 8-2-continued

Coordinates for L494P Structure

| ATOM | 13607 | CG2 | VAL | B | 318 | 38.434 | 1.984 | −10.929 | 1.00 | 21.89 | B | C |
|---|---|---|---|---|---|---|---|---|---|---|---|---|
| ATOM | 13611 | C | VAL | B | 318 | 36.973 | 1.601 | −13.381 | 1.00 | 21.11 | B | C |
| ATOM | 13612 | O | VAL | B | 318 | 37.433 | 0.607 | −13.938 | 1.00 | 21.49 | B | O |
| ATOM | 13614 | N | ASN | B | 319 | 35.739 | 1.640 | −12.879 | 1.00 | 21.87 | B | N |
| ATOM | 13615 | CA | ASN | B | 319 | 34.769 | 0.561 | −13.103 | 1.00 | 22.19 | B | C |
| ATOM | 13617 | CB | ASN | B | 319 | 33.661 | 0.605 | −12.049 | 1.00 | 22.01 | B | C |
| ATOM | 13620 | CG | ASN | B | 319 | 34.184 | 0.354 | −10.645 | 1.00 | 23.10 | B | C |
| ATOM | 13621 | OD1 | ASN | B | 319 | 34.633 | −0.747 | −10.323 | 1.00 | 24.06 | B | O |
| ATOM | 13622 | ND2 | ASN | B | 319 | 34.126 | 1.379 | −9.801 | 1.00 | 22.91 | B | N |
| ATOM | 13625 | C | ASN | B | 319 | 34.157 | 0.624 | −14.503 | 1.00 | 22.52 | B | C |
| ATOM | 13626 | O | ASN | B | 319 | 33.797 | −0.407 | −15.071 | 1.00 | 22.62 | B | O |
| ATOM | 13628 | N | ALA | B | 320 | 34.057 | 1.833 | −15.057 | 1.00 | 22.93 | B | N |
| ATOM | 13629 | CA | ALA | B | 320 | 33.528 | 2.040 | −16.411 | 1.00 | 23.46 | B | C |
| ATOM | 13631 | CB | ALA | B | 320 | 32.801 | 3.381 | −16.485 | 1.00 | 23.82 | B | C |
| ATOM | 13635 | C | ALA | B | 320 | 34.615 | 1.966 | −17.495 | 1.00 | 23.78 | B | C |
| ATOM | 13636 | O | ALA | B | 320 | 34.456 | 2.528 | −18.579 | 1.00 | 23.85 | B | O |
| ATOM | 13638 | N | ILE | B | 321 | 35.714 | 1.275 | −17.197 | 1.00 | 24.14 | B | N |
| ATOM | 13639 | CA | ILE | B | 321 | 36.796 | 1.063 | −18.159 | 1.00 | 23.92 | B | C |
| ATOM | 13641 | CB | ILE | B | 321 | 38.086 | 0.529 | −17.457 | 1.00 | 24.05 | B | C |
| ATOM | 13643 | CG1 | ILE | B | 321 | 39.279 | 0.540 | −18.416 | 1.00 | 23.88 | B | C |
| ATOM | 13646 | CD1 | ILE | B | 321 | 40.563 | 0.038 | −17.785 | 1.00 | 24.06 | B | C |
| ATOM | 13650 | CG2 | ILE | B | 321 | 37.873 | −0.878 | −16.884 | 1.00 | 23.28 | B | C |
| ATOM | 13654 | C | ILE | B | 321 | 36.356 | 0.103 | −19.267 | 1.00 | 23.68 | B | C |
| ATOM | 13655 | O | ILE | B | 321 | 36.578 | 0.379 | −20.445 | 1.00 | 23.41 | B | O |
| ATOM | 13657 | N | ASN | B | 322 | 35.706 | −0.999 | −18.882 | 1.00 | 23.66 | B | N |
| ATOM | 13658 | CA | ASN | B | 322 | 35.280 | −2.050 | −19.823 | 1.00 | 23.61 | B | C |
| ATOM | 13660 | CB | ASN | B | 322 | 34.503 | −3.165 | −19.093 | 1.00 | 23.73 | B | C |
| ATOM | 13663 | CG | ASN | B | 322 | 35.413 | −4.227 | −18.468 | 1.00 | 23.75 | B | C |
| ATOM | 13664 | OD1 | ASN | B | 322 | 36.561 | −4.414 | −18.877 | 1.00 | 23.33 | B | O |
| ATOM | 13665 | ND2 | ASN | B | 322 | 34.885 | −4.939 | −17.479 | 1.00 | 22.49 | B | N |
| ATOM | 13668 | C | ASN | B | 322 | 34.434 | −1.539 | −20.992 | 1.00 | 23.44 | B | C |
| ATOM | 13669 | O | ASN | B | 322 | 34.330 | −2.207 | −22.021 | 1.00 | 23.62 | B | O |
| ATOM | 13671 | N | ASP | B | 323 | 33.828 | −0.365 | −20.826 | 1.00 | 23.09 | B | N |
| ATOM | 13672 | CA | ASP | B | 323 | 33.050 | 0.269 | −21.889 | 1.00 | 22.51 | B | C |
| ATOM | 13674 | CB | ASP | B | 323 | 32.249 | 1.458 | −21.328 | 1.00 | 23.08 | B | C |
| ATOM | 13677 | CG | ASP | B | 323 | 31.293 | 1.056 | −20.201 | 1.00 | 23.77 | B | C |
| ATOM | 13678 | OD1 | ASP | B | 323 | 30.528 | 0.081 | −20.377 | 1.00 | 23.68 | B | O |
| ATOM | 13679 | OD2 | ASP | B | 323 | 31.302 | 1.725 | −19.143 | 1.00 | 23.10 | B | O |
| ATOM | 13680 | C | ASP | B | 323 | 33.937 | 0.740 | −23.051 | 1.00 | 21.15 | B | C |
| ATOM | 13681 | O | ASP | B | 323 | 33.467 | 0.856 | −24.182 | 1.00 | 20.67 | B | O |
| ATOM | 13683 | N | LEU | B | 324 | 35.214 | 1.001 | −22.767 | 1.00 | 20.28 | B | N |
| ATOM | 13684 | CA | LEU | B | 324 | 36.155 | 1.517 | −23.766 | 1.00 | 19.81 | B | C |
| ATOM | 13686 | CB | LEU | B | 324 | 37.278 | 2.299 | −23.075 | 1.00 | 19.75 | B | C |
| ATOM | 13689 | CG | LEU | B | 324 | 36.855 | 3.536 | −22.280 | 1.00 | 19.79 | B | C |
| ATOM | 13691 | CD1 | LEU | B | 324 | 38.033 | 4.107 | −21.504 | 1.00 | 18.72 | B | C |
| ATOM | 13695 | CD2 | LEU | B | 324 | 36.257 | 4.590 | −23.200 | 1.00 | 19.38 | B | C |
| ATOM | 13699 | C | LEU | B | 324 | 36.775 | 0.408 | −24.620 | 1.00 | 19.40 | B | C |
| ATOM | 13700 | O | LEU | B | 324 | 36.895 | −0.731 | −24.164 | 1.00 | 19.28 | B | O |
| ATOM | 13702 | N | PRO | B | 325 | 37.186 | 0.743 | −25.860 | 1.00 | 18.93 | B | N |
| ATOM | 13703 | CA | PRO | B | 325 | 37.864 | −0.226 | −26.720 | 1.00 | 18.63 | B | C |
| ATOM | 13705 | CB | PRO | B | 325 | 37.910 | 0.480 | −28.077 | 1.00 | 18.57 | B | C |
| ATOM | 13708 | CG | PRO | B | 325 | 37.894 | 1.915 | −27.751 | 1.00 | 18.71 | B | C |
| ATOM | 13711 | CD | PRO | B | 325 | 37.036 | 2.048 | −26.528 | 1.00 | 18.93 | B | C |
| ATOM | 13714 | C | PRO | B | 325 | 39.274 | −0.545 | −26.227 | 1.00 | 18.43 | B | C |
| ATOM | 13715 | O | PRO | B | 325 | 39.858 | 0.231 | −25.468 | 1.00 | 17.77 | B | O |
| ATOM | 13716 | N | ASP | B | 326 | 39.808 | −1.676 | −26.678 | 1.00 | 18.61 | B | N |
| ATOM | 13717 | CA | ASP | B | 326 | 41.035 | −2.248 | −26.113 | 1.00 | 18.76 | B | C |
| ATOM | 13719 | CB | ASP | B | 326 | 41.455 | −3.501 | −26.894 | 1.00 | 19.31 | B | C |
| ATOM | 13722 | CG | ASP | B | 326 | 40.570 | −4.708 | −26.599 | 1.00 | 20.22 | B | C |
| ATOM | 13723 | OD1 | ASP | B | 326 | 39.894 | −4.730 | −25.545 | 1.00 | 21.20 | B | O |
| ATOM | 13724 | OD2 | ASP | B | 326 | 40.565 | −5.649 | −27.422 | 1.00 | 21.66 | B | O |
| ATOM | 13725 | C | ASP | B | 326 | 42.211 | −1.277 | −26.015 | 1.00 | 18.24 | B | C |
| ATOM | 13726 | O | ASP | B | 326 | 42.806 | −1.145 | −24.948 | 1.00 | 18.18 | B | O |
| ATOM | 13728 | N | TYR | B | 327 | 42.547 | −0.599 | −27.109 | 1.00 | 17.94 | B | N |
| ATOM | 13729 | CA | TYR | B | 327 | 43.695 | 0.316 | −27.094 | 1.00 | 17.68 | B | C |
| ATOM | 13731 | CB | TYR | B | 327 | 44.061 | 0.800 | −28.506 | 1.00 | 17.63 | B | C |
| ATOM | 13734 | CG | TYR | B | 327 | 43.152 | 1.858 | −29.101 | 1.00 | 17.30 | B | C |
| ATOM | 13735 | CD1 | TYR | B | 327 | 41.980 | 1.506 | −29.768 | 1.00 | 17.77 | B | C |
| ATOM | 13737 | CE1 | TYR | B | 327 | 41.151 | 2.475 | −30.328 | 1.00 | 17.15 | B | C |
| ATOM | 13739 | CZ | TYR | B | 327 | 41.497 | 3.811 | −30.233 | 1.00 | 17.82 | B | C |
| ATOM | 13740 | OH | TYR | B | 327 | 40.684 | 4.774 | −30.783 | 1.00 | 19.10 | B | O |
| ATOM | 13742 | CE2 | TYR | B | 327 | 42.659 | 4.185 | −29.584 | 1.00 | 17.85 | B | C |
| ATOM | 13744 | CD2 | TYR | B | 327 | 43.482 | 3.208 | −29.027 | 1.00 | 17.88 | B | C |
| ATOM | 13746 | C | TYR | B | 327 | 43.474 | 1.497 | −26.149 | 1.00 | 17.55 | B | C |
| ATOM | 13747 | O | TYR | B | 327 | 44.435 | 2.025 | −25.587 | 1.00 | 17.97 | B | O |
| ATOM | 13749 | N | MET | B | 328 | 42.215 | 1.894 | −25.966 | 1.00 | 17.24 | B | N |
| ATOM | 13750 | CA | MET | B | 328 | 41.866 | 2.972 | −25.033 | 1.00 | 16.88 | B | C |
| ATOM | 13752 | CB | MET | B | 328 | 40.511 | 3.582 | −25.390 | 1.00 | 16.72 | B | C |

TABLE 8-2-continued

Coordinates for L494P Structure

| ATOM | 13755 | CG | MET | B | 328 | 40.549 | 4.380 | −26.674 | 1.00 | 16.24 | B | C |
|---|---|---|---|---|---|---|---|---|---|---|---|---|
| ATOM | 13758 | SD | MET | B | 328 | 39.002 | 5.199 | −27.066 | 1.00 | 13.82 | B | S |
| ATOM | 13759 | CE | MET | B | 328 | 39.582 | 6.357 | −28.303 | 1.00 | 13.73 | B | C |
| ATOM | 13763 | C | MET | B | 328 | 41.865 | 2.507 | −23.578 | 1.00 | 16.65 | B | C |
| ATOM | 13764 | O | MET | B | 328 | 42.227 | 3.274 | −22.688 | 1.00 | 16.22 | B | O |
| ATOM | 13766 | N | LYS | B | 329 | 41.449 | 1.262 | −23.342 | 1.00 | 16.55 | B | N |
| ATOM | 13767 | CA | LYS | B | 329 | 41.524 | 0.661 | −22.008 | 1.00 | 16.67 | B | C |
| ATOM | 13769 | CB | LYS | B | 329 | 41.107 | −0.813 | −22.045 | 1.00 | 17.17 | B | C |
| ATOM | 13772 | CG | LYS | B | 329 | 39.614 | −1.076 | −22.199 | 1.00 | 19.24 | B | C |
| ATOM | 13775 | CD | LYS | B | 329 | 39.370 | −2.516 | −22.662 | 1.00 | 21.98 | B | C |
| ATOM | 13778 | CE | LYS | B | 329 | 38.095 | −3.116 | −22.093 | 1.00 | 23.19 | B | C |
| ATOM | 13781 | NZ | LYS | B | 329 | 37.911 | −4.532 | −22.538 | 1.00 | 24.02 | B | N |
| ATOM | 13785 | C | LYS | B | 329 | 42.946 | 0.754 | −21.469 | 1.00 | 16.07 | B | C |
| ATOM | 13786 | O | LYS | B | 329 | 43.177 | 1.281 | −20.381 | 1.00 | 16.02 | B | O |
| ATOM | 13788 | N | LEU | B | 330 | 43.891 | 0.238 | −22.248 | 1.00 | 15.71 | B | N |
| ATOM | 13789 | CA | LEU | B | 330 | 45.300 | 0.211 | −21.859 | 1.00 | 15.48 | B | C |
| ATOM | 13791 | CB | LEU | B | 330 | 46.118 | −0.574 | −22.889 | 1.00 | 15.59 | B | C |
| ATOM | 13794 | CG | LEU | B | 330 | 47.578 | −0.875 | −22.540 | 1.00 | 15.37 | B | C |
| ATOM | 13796 | CD1 | LEU | B | 330 | 47.655 | −1.862 | −21.387 | 1.00 | 15.91 | B | C |
| ATOM | 13800 | CD2 | LEU | B | 330 | 48.314 | −1.411 | −23.758 | 1.00 | 14.02 | B | C |
| ATOM | 13804 | C | LEU | B | 330 | 45.868 | 1.622 | −21.710 | 1.00 | 15.18 | B | C |
| ATOM | 13805 | O | LEU | B | 330 | 46.670 | 1.876 | −20.812 | 1.00 | 15.28 | B | O |
| ATOM | 13807 | N | CYS | B | 331 | 45.453 | 2.529 | −22.592 | 1.00 | 14.49 | B | N |
| ATOM | 13808 | CA | CYS | B | 331 | 45.875 | 3.929 | −22.525 | 1.00 | 13.98 | B | C |
| ATOM | 13810 | CB | CYS | B | 331 | 45.494 | 4.665 | −23.814 | 1.00 | 14.01 | B | C |
| ATOM | 13813 | SG | CYS | B | 331 | 45.852 | 6.448 | −23.790 | 1.00 | 16.06 | B | S |
| ATOM | 13815 | C | CYS | B | 331 | 45.265 | 4.652 | −21.321 | 1.00 | 13.11 | B | C |
| ATOM | 13816 | O | CYS | B | 331 | 45.969 | 5.344 | −20.581 | 1.00 | 12.31 | B | O |
| ATOM | 13818 | N | PHE | B | 332 | 43.956 | 4.485 | −21.137 | 1.00 | 12.49 | B | N |
| ATOM | 13819 | CA | PHE | B | 332 | 43.220 | 5.171 | −20.074 | 1.00 | 12.12 | B | C |
| ATOM | 13821 | CB | PHE | B | 332 | 41.712 | 4.935 | −20.229 | 1.00 | 11.94 | B | C |
| ATOM | 13824 | CG | PHE | B | 332 | 40.889 | 5.500 | −19.105 | 1.00 | 11.71 | B | C |
| ATOM | 13825 | CD1 | PHE | B | 332 | 40.586 | 6.852 | −19.062 | 1.00 | 11.58 | B | C |
| ATOM | 13827 | CE1 | PHE | B | 332 | 39.831 | 7.379 | −18.023 | 1.00 | 12.01 | B | C |
| ATOM | 13829 | CZ | PHE | B | 332 | 39.369 | 6.550 | −17.013 | 1.00 | 11.84 | B | C |
| ATOM | 13831 | CE2 | PHE | B | 332 | 39.665 | 5.199 | −17.044 | 1.00 | 12.39 | B | C |
| ATOM | 13833 | CD2 | PHE | B | 332 | 40.423 | 4.680 | −18.087 | 1.00 | 12.36 | B | C |
| ATOM | 13835 | C | PHE | B | 332 | 43.673 | 4.745 | −18.674 | 1.00 | 12.03 | B | C |
| ATOM | 13836 | O | PHE | B | 332 | 43.919 | 5.593 | −17.812 | 1.00 | 11.73 | B | O |
| ATOM | 13838 | N | LEU | B | 333 | 43.778 | 3.435 | −18.455 | 1.00 | 11.78 | B | N |
| ATOM | 13839 | CA | LEU | B | 333 | 44.160 | 2.893 | −17.144 | 1.00 | 11.25 | B | C |
| ATOM | 13841 | CB | LEU | B | 333 | 43.998 | 1.365 | −17.122 | 1.00 | 10.70 | B | C |
| ATOM | 13844 | CG | LEU | B | 333 | 44.058 | 0.648 | −15.767 | 1.00 | 8.41 | B | C |
| ATOM | 13846 | CD1 | LEU | B | 333 | 43.018 | 1.170 | −14.793 | 1.00 | 5.66 | B | C |
| ATOM | 13850 | CD2 | LEU | B | 333 | 43.874 | −0.840 | −15.966 | 1.00 | 6.27 | B | C |
| ATOM | 13854 | C | LEU | B | 333 | 45.588 | 3.282 | −16.761 | 1.00 | 11.55 | B | C |
| ATOM | 13855 | O | LEU | B | 333 | 45.898 | 3.420 | −15.577 | 1.00 | 11.81 | B | O |
| ATOM | 13857 | N | ALA | B | 334 | 46.449 | 3.462 | −17.762 | 1.00 | 11.79 | B | N |
| ATOM | 13858 | CA | ALA | B | 334 | 47.815 | 3.935 | −17.539 | 1.00 | 11.84 | B | C |
| ATOM | 13860 | CB | ALA | B | 334 | 48.625 | 3.847 | −18.825 | 1.00 | 11.68 | B | C |
| ATOM | 13864 | C | ALA | B | 334 | 47.809 | 5.369 | −17.013 | 1.00 | 12.02 | B | C |
| ATOM | 13865 | O | ALA | B | 334 | 48.401 | 5.660 | −15.975 | 1.00 | 11.95 | B | O |
| ATOM | 13867 | N | LEU | B | 335 | 47.135 | 6.258 | −17.736 | 1.00 | 12.45 | B | N |
| ATOM | 13868 | CA | LEU | B | 335 | 46.991 | 7.648 | −17.311 | 1.00 | 12.66 | B | C |
| ATOM | 13870 | CB | LEU | B | 335 | 46.194 | 8.447 | −18.352 | 1.00 | 12.71 | B | C |
| ATOM | 13873 | CG | LEU | B | 335 | 46.041 | 9.954 | −18.117 | 1.00 | 12.97 | B | C |
| ATOM | 13875 | CD1 | LEU | B | 335 | 47.397 | 10.642 | −18.055 | 1.00 | 13.00 | B | C |
| ATOM | 13879 | CD2 | LEU | B | 335 | 45.178 | 10.572 | −19.202 | 1.00 | 11.60 | B | C |
| ATOM | 13883 | C | LEU | B | 335 | 46.299 | 7.714 | −15.950 | 1.00 | 12.72 | B | C |
| ATOM | 13884 | O | LEU | B | 335 | 46.785 | 8.372 | −15.035 | 1.00 | 12.67 | B | O |
| ATOM | 13886 | N | TYR | B | 336 | 45.176 | 7.013 | −15.826 | 1.00 | 13.04 | B | N |
| ATOM | 13887 | CA | TYR | B | 336 | 44.394 | 6.979 | −14.584 | 1.00 | 13.37 | B | C |
| ATOM | 13889 | CB | TYR | B | 336 | 43.346 | 5.865 | −14.661 | 1.00 | 13.50 | B | C |
| ATOM | 13892 | CG | TYR | B | 336 | 42.316 | 5.877 | −13.556 | 1.00 | 13.69 | B | C |
| ATOM | 13893 | CD1 | TYR | B | 336 | 41.167 | 6.654 | −13.662 | 1.00 | 15.39 | B | C |
| ATOM | 13895 | CE1 | TYR | B | 336 | 40.205 | 6.659 | −12.659 | 1.00 | 15.19 | B | C |
| ATOM | 13897 | CZ | TYR | B | 336 | 40.386 | 5.879 | −11.536 | 1.00 | 13.61 | B | C |
| ATOM | 13898 | OH | TYR | B | 336 | 39.433 | 5.885 | −10.545 | 1.00 | 12.30 | B | O |
| ATOM | 13900 | CE2 | TYR | B | 336 | 41.517 | 5.091 | −11.410 | 1.00 | 13.99 | B | C |
| ATOM | 13902 | CD2 | TYR | B | 336 | 42.472 | 5.091 | −12.420 | 1.00 | 13.11 | B | C |
| ATOM | 13904 | C | TYR | B | 336 | 45.276 | 6.778 | −13.351 | 1.00 | 13.42 | B | C |
| ATOM | 13905 | O | TYR | B | 336 | 45.282 | 7.612 | −12.446 | 1.00 | 13.88 | B | O |
| ATOM | 13907 | N | ASN | B | 337 | 46.026 | 5.678 | −13.336 | 1.00 | 13.13 | B | N |
| ATOM | 13908 | CA | ASN | B | 337 | 46.914 | 5.349 | −12.221 | 1.00 | 12.80 | B | C |
| ATOM | 13910 | CB | ASN | B | 337 | 47.573 | 3.985 | −12.443 | 1.00 | 12.62 | B | C |
| ATOM | 13913 | CG | ASN | B | 337 | 46.576 | 2.842 | −12.446 | 1.00 | 12.42 | B | C |
| ATOM | 13914 | OD1 | ASN | B | 337 | 45.386 | 3.036 | −12.200 | 1.00 | 11.43 | B | O |
| ATOM | 13915 | ND2 | ASN | B | 337 | 47.062 | 1.639 | −12.726 | 1.00 | 12.41 | B | N |

TABLE 8-2-continued

Coordinates for L494P Structure

| ATOM | 13918 | C | ASN | B | 337 | 47.997 | 6.404 | −12.020 | 1.00 | 13.00 | B | C |
|---|---|---|---|---|---|---|---|---|---|---|---|---|
| ATOM | 13919 | O | ASN | B | 337 | 48.274 | 6.810 | −10.891 | 1.00 | 13.85 | B | O |
| ATOM | 13921 | N | THR | B | 338 | 48.606 | 6.838 | −13.120 | 1.00 | 12.67 | B | N |
| ATOM | 13922 | CA | THR | B | 338 | 49.656 | 7.852 | −13.079 | 1.00 | 12.12 | B | C |
| ATOM | 13924 | CB | THR | B | 338 | 50.137 | 8.222 | −14.498 | 1.00 | 11.99 | B | C |
| ATOM | 13926 | OG1 | THR | B | 338 | 50.664 | 7.057 | −15.145 | 1.00 | 9.18 | B | O |
| ATOM | 13928 | CG2 | THR | B | 338 | 51.207 | 9.303 | −14.444 | 1.00 | 11.84 | B | C |
| ATOM | 13932 | C | THR | B | 338 | 49.161 | 9.111 | −12.384 | 1.00 | 12.48 | B | C |
| ATOM | 13933 | O | THR | B | 338 | 49.859 | 9.671 | −11.540 | 1.00 | 12.39 | B | O |
| ATOM | 13935 | N | ILE | B | 339 | 47.950 | 9.540 | −12.734 | 1.00 | 13.07 | B | N |
| ATOM | 13936 | CA | ILE | B | 339 | 47.373 | 10.759 | −12.172 | 1.00 | 13.52 | B | C |
| ATOM | 13938 | CB | ILE | B | 339 | 46.123 | 11.241 | −12.956 | 1.00 | 13.22 | B | C |
| ATOM | 13940 | CG1 | ILE | B | 339 | 46.443 | 11.474 | −14.438 | 1.00 | 12.90 | B | C |
| ATOM | 13943 | CD1 | ILE | B | 339 | 47.622 | 12.375 | −14.683 | 1.00 | 11.77 | B | C |
| ATOM | 13947 | CG2 | ILE | B | 339 | 45.587 | 12.534 | −12.362 | 1.00 | 12.97 | B | C |
| ATOM | 13951 | C | ILE | B | 339 | 47.018 | 10.561 | −10.697 | 1.00 | 14.03 | B | C |
| ATOM | 13952 | O | ILE | B | 339 | 47.294 | 11.430 | −9.870 | 1.00 | 15.15 | B | O |
| ATOM | 13954 | N | ASN | B | 340 | 46.419 | 9.422 | −10.364 | 1.00 | 13.83 | B | N |
| ATOM | 13955 | CA | ASN | B | 340 | 46.116 | 9.116 | −8.967 | 1.00 | 13.79 | B | C |
| ATOM | 13957 | CB | ASN | B | 340 | 45.287 | 7.837 | −8.852 | 1.00 | 13.39 | B | C |
| ATOM | 13960 | CG | ASN | B | 340 | 43.876 | 8.015 | −9.360 | 1.00 | 12.83 | B | C |
| ATOM | 13961 | OD1 | ASN | B | 340 | 43.552 | 9.024 | −9.987 | 1.00 | 11.69 | B | O |
| ATOM | 13962 | ND2 | ASN | B | 340 | 43.024 | 7.035 | −9.092 | 1.00 | 12.15 | B | N |
| ATOM | 13965 | C | ASN | B | 340 | 47.375 | 8.995 | −8.115 | 1.00 | 14.39 | B | C |
| ATOM | 13966 | O | ASN | B | 340 | 47.356 | 9.331 | −6.933 | 1.00 | 14.92 | B | O |
| ATOM | 13968 | N | GLU | B | 341 | 48.465 | 8.527 | −8.720 | 1.00 | 14.80 | B | N |
| ATOM | 13969 | CA | GLU | B | 341 | 49.731 | 8.361 | −8.006 | 1.00 | 15.19 | B | C |
| ATOM | 13971 | CB | GLU | B | 341 | 50.702 | 7.500 | −8.819 | 1.00 | 15.65 | B | C |
| ATOM | 13974 | CG | GLU | B | 341 | 52.057 | 7.297 | −8.150 | 1.00 | 17.64 | B | C |
| ATOM | 13977 | CD | GLU | B | 341 | 52.785 | 6.076 | −8.668 | 1.00 | 21.06 | B | C |
| ATOM | 13978 | OE1 | GLU | B | 341 | 53.791 | 6.243 | −9.394 | 1.00 | 22.18 | B | O |
| ATOM | 13979 | OE2 | GLU | B | 341 | 52.343 | 4.951 | −8.353 | 1.00 | 23.01 | B | O |
| ATOM | 13980 | C | GLU | B | 341 | 50.376 | 9.704 | −7.652 | 1.00 | 14.68 | B | C |
| ATOM | 13981 | O | GLU | B | 341 | 50.952 | 9.848 | −6.573 | 1.00 | 14.72 | B | O |
| ATOM | 13983 | N | ILE | B | 342 | 50.288 | 10.679 | −8.555 | 1.00 | 14.12 | B | N |
| ATOM | 13984 | CA | ILE | B | 342 | 50.753 | 12.035 | −8.253 | 1.00 | 13.72 | B | C |
| ATOM | 13986 | CB | ILE | B | 342 | 50.765 | 12.945 | −9.498 | 1.00 | 13.57 | B | C |
| ATOM | 13988 | CG1 | ILE | B | 342 | 51.775 | 12.434 | −10.526 | 1.00 | 14.64 | B | C |
| ATOM | 13991 | CD1 | ILE | B | 342 | 51.843 | 13.277 | −11.792 | 1.00 | 15.37 | B | C |
| ATOM | 13995 | CG2 | ILE | B | 342 | 51.123 | 14.376 | −9.111 | 1.00 | 13.73 | B | C |
| ATOM | 13999 | C | ILE | B | 342 | 49.858 | 12.654 | −7.179 | 1.00 | 13.24 | B | C |
| ATOM | 14000 | O | ILE | B | 342 | 50.340 | 13.359 | −6.290 | 1.00 | 13.44 | B | O |
| ATOM | 14002 | N | ALA | B | 343 | 48.557 | 12.379 | −7.270 | 1.00 | 12.34 | B | N |
| ATOM | 14003 | CA | ALA | B | 343 | 47.592 | 12.806 | −6.261 | 1.00 | 11.40 | B | C |
| ATOM | 14005 | CB | ALA | B | 343 | 46.197 | 12.362 | −6.654 | 1.00 | 11.24 | B | C |
| ATOM | 14009 | C | ALA | B | 343 | 47.956 | 12.253 | −4.883 | 1.00 | 10.91 | B | C |
| ATOM | 14010 | O | ALA | B | 343 | 47.833 | 12.953 | −3.876 | 1.00 | 10.88 | B | O |
| ATOM | 14012 | N | TYR | B | 344 | 48.409 | 11.001 | −4.851 | 1.00 | 10.38 | B | N |
| ATOM | 14013 | CA | TYR | B | 344 | 48.833 | 10.355 | −3.607 | 1.00 | 10.04 | B | C |
| ATOM | 14015 | CB | TYR | B | 344 | 49.023 | 8.845 | −3.814 | 1.00 | 9.93 | B | C |
| ATOM | 14018 | CG | TYR | B | 344 | 49.475 | 8.118 | −2.569 | 1.00 | 8.21 | B | C |
| ATOM | 14019 | CD1 | TYR | B | 344 | 48.553 | 7.639 | −1.648 | 1.00 | 6.65 | B | C |
| ATOM | 14021 | CE1 | TYR | B | 344 | 48.963 | 6.982 | −0.497 | 1.00 | 6.47 | B | C |
| ATOM | 14023 | CZ | TYR | B | 344 | 50.309 | 6.799 | −0.254 | 1.00 | 6.00 | B | C |
| ATOM | 14024 | OH | TYR | B | 344 | 50.715 | 6.147 | 0.888 | 1.00 | 4.30 | B | O |
| ATOM | 14026 | CE2 | TYR | B | 344 | 51.247 | 7.268 | −1.154 | 1.00 | 7.46 | B | C |
| ATOM | 14028 | CD2 | TYR | B | 344 | 50.827 | 7.924 | −2.304 | 1.00 | 8.03 | B | C |
| ATOM | 14030 | C | TYR | B | 344 | 50.119 | 10.977 | −3.064 | 1.00 | 10.06 | B | C |
| ATOM | 14031 | O | TYR | B | 344 | 50.269 | 11.142 | −1.856 | 1.00 | 10.03 | B | O |
| ATOM | 14033 | N | ASP | B | 345 | 51.047 | 11.310 | −3.957 | 1.00 | 10.36 | B | N |
| ATOM | 14034 | CA | ASP | B | 345 | 52.284 | 11.982 | −3.559 | 1.00 | 10.78 | B | C |
| ATOM | 14036 | CB | ASP | B | 345 | 53.256 | 12.088 | −4.740 | 1.00 | 10.82 | B | C |
| ATOM | 14039 | CG | ASP | B | 345 | 53.868 | 10.755 | −5.123 | 1.00 | 10.93 | B | C |
| ATOM | 14040 | OD1 | ASP | B | 345 | 53.973 | 9.858 | −4.256 | 1.00 | 11.03 | B | O |
| ATOM | 14041 | OD2 | ASP | B | 345 | 54.258 | 10.610 | −6.300 | 1.00 | 12.06 | B | O |
| ATOM | 14042 | C | ASP | B | 345 | 52.011 | 13.377 | −2.999 | 1.00 | 11.16 | B | C |
| ATOM | 14043 | O | ASP | B | 345 | 52.830 | 13.919 | −2.259 | 1.00 | 11.52 | B | O |
| ATOM | 14045 | N | ASN | B | 346 | 50.873 | 13.959 | −3.366 | 1.00 | 11.44 | B | N |
| ATOM | 14046 | CA | ASN | B | 346 | 50.468 | 15.260 | −2.843 | 1.00 | 11.76 | B | C |
| ATOM | 14048 | CB | ASN | B | 346 | 49.615 | 16.005 | −3.872 | 1.00 | 11.96 | B | C |
| ATOM | 14051 | CG | ASN | B | 346 | 50.458 | 16.711 | −4.910 | 1.00 | 13.27 | B | C |
| ATOM | 14052 | OD1 | ASN | B | 346 | 51.086 | 17.729 | −4.618 | 1.00 | 18.45 | B | O |
| ATOM | 14053 | ND2 | ASN | B | 346 | 50.485 | 16.174 | −6.128 | 1.00 | 12.71 | B | N |
| ATOM | 14056 | C | ASN | B | 346 | 49.733 | 15.140 | −1.514 | 1.00 | 11.65 | B | C |
| ATOM | 14057 | O | ASN | B | 346 | 49.944 | 15.953 | −0.612 | 1.00 | 11.65 | B | O |
| ATOM | 14059 | N | LEU | B | 347 | 48.876 | 14.126 | −1.399 | 1.00 | 11.52 | B | N |
| ATOM | 14060 | CA | LEU | B | 347 | 48.164 | 13.847 | −0.150 | 1.00 | 11.25 | B | C |
| ATOM | 14062 | CB | LEU | B | 347 | 47.136 | 12.728 | −0.350 | 1.00 | 10.95 | B | C |

TABLE 8-2-continued

Coordinates for L494P Structure

| ATOM | 14065 | CG | LEU | B | 347 | 46.235 | 12.390 | 0.843 | 1.00 | 9.89 | B | C |
|---|---|---|---|---|---|---|---|---|---|---|---|---|
| ATOM | 14067 | CD1 | LEU | B | 347 | 45.291 | 13.541 | 1.145 | 1.00 | 9.37 | B | C |
| ATOM | 14071 | CD2 | LEU | B | 347 | 45.457 | 11.109 | 0.585 | 1.00 | 8.58 | B | C |
| ATOM | 14075 | C | LEU | B | 347 | 49.123 | 13.460 | 0.973 | 1.00 | 11.48 | B | C |
| ATOM | 14076 | O | LEU | B | 347 | 48.844 | 13.722 | 2.138 | 1.00 | 11.80 | B | O |
| ATOM | 14078 | N | LYS | B | 348 | 50.245 | 12.833 | 0.628 | 1.00 | 11.67 | B | N |
| ATOM | 14079 | CA | LYS | B | 348 | 51.230 | 12.424 | 1.627 | 1.00 | 11.74 | B | C |
| ATOM | 14081 | CB | LYS | B | 348 | 52.176 | 11.361 | 1.053 | 1.00 | 11.69 | B | C |
| ATOM | 14084 | CG | LYS | B | 348 | 53.032 | 10.658 | 2.104 | 1.00 | 10.78 | B | C |
| ATOM | 14087 | CD | LYS | B | 348 | 53.948 | 9.598 | 1.497 | 1.00 | 9.66 | B | C |
| ATOM | 14090 | CE | LYS | B | 348 | 55.189 | 10.191 | 0.836 | 1.00 | 8.44 | B | C |
| ATOM | 14093 | NZ | LYS | B | 348 | 54.959 | 10.572 | −0.583 | 1.00 | 7.87 | B | N |
| ATOM | 14097 | C | LYS | B | 348 | 52.033 | 13.625 | 2.125 | 1.00 | 11.88 | B | C |
| ATOM | 14098 | O | LYS | B | 348 | 52.147 | 13.851 | 3.330 | 1.00 | 11.65 | B | O |
| ATOM | 14100 | N | ASP | B | 349 | 52.574 | 14.398 | 1.192 | 1.00 | 12.38 | B | N |
| ATOM | 14101 | CA | ASP | B | 349 | 53.508 | 15.469 | 1.532 | 1.00 | 13.33 | B | C |
| ATOM | 14103 | CB | ASP | B | 349 | 54.425 | 15.775 | 0.342 | 1.00 | 13.19 | B | C |
| ATOM | 14106 | CG | ASP | B | 349 | 55.170 | 14.546 | −0.155 | 1.00 | 11.88 | B | C |
| ATOM | 14107 | OD1 | ASP | B | 349 | 55.312 | 13.572 | 0.616 | 1.00 | 7.56 | B | O |
| ATOM | 14108 | OD2 | ASP | B | 349 | 55.610 | 14.556 | −1.324 | 1.00 | 11.49 | B | O |
| ATOM | 14109 | C | ASP | B | 349 | 52.808 | 16.745 | 1.996 | 1.00 | 14.12 | B | C |
| ATOM | 14110 | O | ASP | B | 349 | 53.261 | 17.387 | 2.944 | 1.00 | 14.75 | B | O |
| ATOM | 14112 | N | LYS | B | 350 | 51.711 | 17.107 | 1.335 | 1.00 | 14.58 | B | N |
| ATOM | 14113 | CA | LYS | B | 350 | 51.003 | 18.357 | 1.634 | 1.00 | 15.29 | B | C |
| ATOM | 14115 | CB | LYS | B | 350 | 50.751 | 19.137 | 0.339 | 1.00 | 15.87 | B | C |
| ATOM | 14118 | CG | LYS | B | 350 | 52.035 | 19.487 | −0.411 | 1.00 | 18.40 | B | C |
| ATOM | 14121 | CD | LYS | B | 350 | 51.775 | 20.337 | −1.651 | 1.00 | 20.21 | B | C |
| ATOM | 14124 | CE | LYS | B | 350 | 52.936 | 20.246 | −2.646 | 1.00 | 20.06 | B | C |
| ATOM | 14127 | NZ | LYS | B | 350 | 54.271 | 20.455 | −2.007 | 1.00 | 19.09 | B | N |
| ATOM | 14131 | C | LYS | B | 350 | 49.691 | 18.156 | 2.407 | 1.00 | 14.89 | B | C |
| ATOM | 14132 | O | LYS | B | 350 | 49.227 | 19.073 | 3.088 | 1.00 | 14.72 | B | O |
| ATOM | 14134 | N | GLY | B | 351 | 49.098 | 16.970 | 2.304 | 1.00 | 14.61 | B | N |
| ATOM | 14135 | CA | GLY | B | 351 | 47.889 | 16.645 | 3.060 | 1.00 | 14.57 | B | C |
| ATOM | 14138 | C | GLY | B | 351 | 46.615 | 17.209 | 2.463 | 1.00 | 14.52 | B | C |
| ATOM | 14139 | O | GLY | B | 351 | 45.688 | 17.560 | 3.193 | 1.00 | 14.37 | B | O |
| ATOM | 14141 | N | GLU | B | 352 | 46.568 | 17.286 | 1.134 | 1.00 | 14.82 | B | N |
| ATOM | 14142 | CA | GLU | B | 352 | 45.429 | 17.859 | 0.416 | 1.00 | 15.23 | B | C |
| ATOM | 14144 | CB | GLU | B | 352 | 45.789 | 19.240 | −0.144 | 1.00 | 15.22 | B | C |
| ATOM | 14147 | CG | GLU | B | 352 | 46.260 | 20.271 | 0.894 | 1.00 | 15.93 | B | C |
| ATOM | 14150 | CD | GLU | B | 352 | 45.126 | 21.048 | 1.543 | 1.00 | 16.01 | B | C |
| ATOM | 14151 | OE1 | GLU | B | 352 | 43.998 | 20.519 | 1.642 | 1.00 | 17.82 | B | O |
| ATOM | 14152 | OE2 | GLU | B | 352 | 45.372 | 22.198 | 1.962 | 1.00 | 15.28 | B | O |
| ATOM | 14153 | C | GLU | B | 352 | 45.033 | 16.946 | −0.738 | 1.00 | 15.54 | B | C |
| ATOM | 14154 | O | GLU | B | 352 | 45.897 | 16.437 | −1.456 | 1.00 | 15.74 | B | O |
| ATOM | 14156 | N | ASN | B | 353 | 43.730 | 16.738 | −0.914 | 1.00 | 15.72 | B | N |
| ATOM | 14157 | CA | ASN | B | 353 | 43.228 | 15.980 | −2.058 | 1.00 | 15.71 | B | C |
| ATOM | 14159 | CB | ASN | B | 353 | 41.856 | 15.361 | −1.762 | 1.00 | 15.94 | B | C |
| ATOM | 14162 | CG | ASN | B | 353 | 41.403 | 14.388 | −2.847 | 1.00 | 16.62 | B | C |
| ATOM | 14163 | OD1 | ASN | B | 353 | 41.769 | 14.521 | −4.016 | 1.00 | 16.74 | B | O |
| ATOM | 14164 | ND2 | ASN | B | 353 | 40.602 | 13.403 | −2.459 | 1.00 | 17.81 | B | N |
| ATOM | 14167 | C | ASN | B | 353 | 43.148 | 16.888 | −3.277 | 1.00 | 15.38 | B | C |
| ATOM | 14168 | O | ASN | B | 353 | 42.204 | 17.666 | −3.424 | 1.00 | 15.14 | B | O |
| ATOM | 14170 | N | ILE | B | 354 | 44.145 | 16.775 | −4.149 | 1.00 | 15.29 | B | N |
| ATOM | 14171 | CA | ILE | B | 354 | 44.202 | 17.576 | −5.369 | 1.00 | 15.35 | B | C |
| ATOM | 14173 | CB | ILE | B | 354 | 45.608 | 18.197 | −5.558 | 1.00 | 15.18 | B | C |
| ATOM | 14175 | CG1 | ILE | B | 354 | 46.670 | 17.121 | −5.797 | 1.00 | 14.74 | B | C |
| ATOM | 14178 | CD1 | ILE | B | 354 | 47.872 | 17.644 | −6.528 | 1.00 | 14.74 | B | C |
| ATOM | 14182 | CG2 | ILE | B | 354 | 45.982 | 19.020 | −4.343 | 1.00 | 15.14 | B | C |
| ATOM | 14186 | C | ILE | B | 354 | 43.801 | 16.778 | −6.623 | 1.00 | 15.64 | B | C |
| ATOM | 14187 | O | ILE | B | 354 | 44.136 | 17.163 | −7.743 | 1.00 | 15.61 | B | O |
| ATOM | 14189 | N | LEU | B | 355 | 43.077 | 15.676 | −6.437 | 1.00 | 15.92 | B | N |
| ATOM | 14190 | CA | LEU | B | 355 | 42.667 | 14.836 | −7.564 | 1.00 | 15.93 | B | C |
| ATOM | 14192 | CB | LEU | B | 355 | 42.060 | 13.514 | −7.073 | 1.00 | 15.64 | B | C |
| ATOM | 14195 | CG | LEU | B | 355 | 41.802 | 12.439 | −8.136 | 1.00 | 14.69 | B | C |
| ATOM | 14197 | CD1 | LEU | B | 355 | 43.070 | 12.105 | −8.906 | 1.00 | 13.49 | B | C |
| ATOM | 14201 | CD2 | LEU | B | 355 | 41.222 | 11.184 | −7.499 | 1.00 | 14.54 | B | C |
| ATOM | 14205 | C | LEU | B | 355 | 41.698 | 15.550 | −8.517 | 1.00 | 16.22 | B | C |
| ATOM | 14206 | O | LEU | B | 355 | 41.836 | 15.418 | −9.735 | 1.00 | 16.22 | B | O |
| ATOM | 14208 | N | PRO | B | 356 | 40.724 | 16.311 | −7.975 | 1.00 | 16.49 | B | N |
| ATOM | 14209 | CA | PRO | B | 356 | 39.781 | 16.987 | −8.869 | 1.00 | 16.94 | B | C |
| ATOM | 14211 | CB | PRO | B | 356 | 38.843 | 17.727 | −7.906 | 1.00 | 16.89 | B | C |
| ATOM | 14214 | CG | PRO | B | 356 | 38.992 | 17.035 | −6.615 | 1.00 | 16.92 | B | C |
| ATOM | 14217 | CD | PRO | B | 356 | 40.410 | 16.581 | −6.562 | 1.00 | 16.28 | B | C |
| ATOM | 14220 | C | PRO | B | 356 | 40.460 | 17.974 | −9.817 | 1.00 | 17.52 | B | C |
| ATOM | 14221 | O | PRO | B | 356 | 40.087 | 18.046 | −10.987 | 1.00 | 18.27 | B | O |
| ATOM | 14222 | N | TYR | B | 357 | 41.452 | 18.712 | −9.318 | 1.00 | 17.33 | B | N |
| ATOM | 14223 | CA | TYR | B | 357 | 42.179 | 19.690 | −10.138 | 1.00 | 17.07 | B | C |
| ATOM | 14225 | CB | TYR | B | 357 | 43.048 | 20.621 | −9.276 | 1.00 | 16.94 | B | C |

TABLE 8-2-continued

Coordinates for L494P Structure

| ATOM | 14228 | CG | TYR | B | 357 | 42.411 | 21.040 | −7.969 | 1.00 | 17.63 | B | C |
|---|---|---|---|---|---|---|---|---|---|---|---|---|
| ATOM | 14229 | CD1 | TYR | B | 357 | 41.167 | 21.663 | −7.945 | 1.00 | 19.45 | B | C |
| ATOM | 14231 | CE1 | TYR | B | 357 | 40.575 | 22.042 | −6.742 | 1.00 | 19.39 | B | C |
| ATOM | 14233 | CZ | TYR | B | 357 | 41.234 | 21.798 | −5.551 | 1.00 | 18.35 | B | C |
| ATOM | 14234 | OH | TYR | B | 357 | 40.661 | 22.171 | −4.360 | 1.00 | 19.17 | B | O |
| ATOM | 14236 | CE2 | TYR | B | 357 | 42.470 | 21.183 | −5.550 | 1.00 | 17.99 | B | C |
| ATOM | 14238 | CD2 | TYR | B | 357 | 43.051 | 20.807 | −6.755 | 1.00 | 18.02 | B | C |
| ATOM | 14240 | C | TYR | B | 357 | 43.052 | 18.987 | −11.180 | 1.00 | 16.70 | B | C |
| ATOM | 14241 | O | TYR | B | 357 | 43.176 | 19.463 | −12.308 | 1.00 | 17.02 | B | O |
| ATOM | 14243 | N | LEU | B | 358 | 43.649 | 17.858 | −10.797 | 1.00 | 16.01 | B | N |
| ATOM | 14244 | CA | LEU | B | 358 | 44.510 | 17.088 | −11.699 | 1.00 | 15.44 | B | C |
| ATOM | 14246 | CB | LEU | B | 358 | 45.321 | 16.046 | −10.922 | 1.00 | 15.39 | B | C |
| ATOM | 14249 | CG | LEU | B | 358 | 46.418 | 16.579 | −9.998 | 1.00 | 15.39 | B | C |
| ATOM | 14251 | CD1 | LEU | B | 358 | 46.969 | 15.455 | −9.137 | 1.00 | 16.30 | B | C |
| ATOM | 14255 | CD2 | LEU | B | 358 | 47.531 | 17.241 | −10.791 | 1.00 | 15.02 | B | C |
| ATOM | 14259 | C | LEU | B | 358 | 43.720 | 16.397 | −12.810 | 1.00 | 15.07 | B | C |
| ATOM | 14260 | O | LEU | B | 358 | 44.217 | 16.259 | −13.928 | 1.00 | 14.92 | B | O |
| ATOM | 14262 | N | THR | B | 359 | 42.502 | 15.956 | −12.501 | 1.00 | 14.50 | B | N |
| ATOM | 14263 | CA | THR | B | 359 | 41.643 | 15.320 | −13.501 | 1.00 | 14.14 | B | C |
| ATOM | 14265 | CB | THR | B | 359 | 40.620 | 14.372 | −12.857 | 1.00 | 14.08 | B | C |
| ATOM | 14267 | OG1 | THR | B | 359 | 39.832 | 15.087 | −11.896 | 1.00 | 13.76 | B | O |
| ATOM | 14269 | CG2 | THR | B | 359 | 41.334 | 13.219 | −12.179 | 1.00 | 13.80 | B | C |
| ATOM | 14273 | C | THR | B | 359 | 40.904 | 16.350 | −14.349 | 1.00 | 13.91 | B | C |
| ATOM | 14274 | O | THR | B | 359 | 40.619 | 16.097 | −15.519 | 1.00 | 13.91 | B | O |
| ATOM | 14276 | N | LYS | B | 360 | 40.595 | 17.505 | −13.761 | 1.00 | 13.68 | B | N |
| ATOM | 14277 | CA | LYS | B | 360 | 39.919 | 18.583 | −14.487 | 1.00 | 13.73 | B | C |
| ATOM | 14279 | CB | LYS | B | 360 | 39.565 | 19.742 | −13.541 | 1.00 | 14.11 | B | C |
| ATOM | 14282 | CG | LYS | B | 360 | 38.670 | 20.824 | −14.147 | 1.00 | 15.76 | B | C |
| ATOM | 14285 | CD | LYS | B | 360 | 37.240 | 20.337 | −14.337 | 1.00 | 17.92 | B | C |
| ATOM | 14288 | CE | LYS | B | 360 | 36.414 | 21.340 | −15.130 | 1.00 | 19.80 | B | C |
| ATOM | 14291 | NZ | LYS | B | 360 | 35.031 | 20.844 | −15.397 | 1.00 | 21.13 | B | N |
| ATOM | 14295 | C | LYS | B | 360 | 40.785 | 19.080 | −15.646 | 1.00 | 13.04 | B | C |
| ATOM | 14296 | O | LYS | B | 360 | 40.277 | 19.341 | −16.738 | 1.00 | 12.64 | B | O |
| ATOM | 14298 | N | ALA | B | 361 | 42.089 | 19.200 | −15.400 | 1.00 | 12.50 | B | N |
| ATOM | 14299 | CA | ALA | B | 361 | 43.043 | 19.582 | −16.436 | 1.00 | 12.11 | B | C |
| ATOM | 14301 | CB | ALA | B | 361 | 44.430 | 19.730 | −15.850 | 1.00 | 11.80 | B | C |
| ATOM | 14305 | C | ALA | B | 361 | 43.056 | 18.556 | −17.562 | 1.00 | 12.30 | B | C |
| ATOM | 14306 | O | ALA | B | 361 | 43.047 | 18.925 | −18.738 | 1.00 | 12.61 | B | O |
| ATOM | 14308 | N | TRP | B | 362 | 43.066 | 17.274 | −17.198 | 1.00 | 12.41 | B | N |
| ATOM | 14309 | CA | TRP | B | 362 | 43.062 | 16.187 | −18.184 | 1.00 | 12.60 | B | C |
| ATOM | 14311 | CB | TRP | B | 362 | 43.484 | 14.860 | −17.545 | 1.00 | 12.31 | B | C |
| ATOM | 14314 | CG | TRP | B | 362 | 44.957 | 14.676 | −17.578 | 1.00 | 12.74 | B | C |
| ATOM | 14315 | CD1 | TRP | B | 362 | 45.823 | 14.737 | −16.524 | 1.00 | 13.49 | B | C |
| ATOM | 14317 | NE1 | TRP | B | 362 | 47.110 | 14.535 | −16.958 | 1.00 | 12.06 | B | N |
| ATOM | 14319 | CE2 | TRP | B | 362 | 47.093 | 14.347 | −18.315 | 1.00 | 11.96 | B | C |
| ATOM | 14320 | CD2 | TRP | B | 362 | 45.751 | 14.432 | −18.737 | 1.00 | 11.61 | B | C |
| ATOM | 14321 | CE3 | TRP | B | 362 | 45.459 | 14.278 | −20.094 | 1.00 | 11.70 | B | C |
| ATOM | 14323 | CZ3 | TRP | B | 362 | 46.499 | 14.042 | −20.975 | 1.00 | 12.47 | B | C |
| ATOM | 14325 | CH2 | TRP | B | 362 | 47.824 | 13.960 | −20.525 | 1.00 | 12.99 | B | C |
| ATOM | 14327 | CZ2 | TRP | B | 362 | 48.140 | 14.110 | −19.201 | 1.00 | 12.91 | B | C |
| ATOM | 14329 | C | TRP | B | 362 | 41.725 | 16.024 | −18.904 | 1.00 | 13.17 | B | C |
| ATOM | 14330 | O | TRP | B | 362 | 41.682 | 15.459 | −19.997 | 1.00 | 13.14 | B | O |
| ATOM | 14332 | N | ALA | B | 363 | 40.646 | 16.510 | −18.289 | 1.00 | 13.48 | B | N |
| ATOM | 14333 | CA | ALA | B | 363 | 39.325 | 16.500 | −18.915 | 1.00 | 13.34 | B | C |
| ATOM | 14335 | CB | ALA | B | 363 | 38.235 | 16.626 | −17.862 | 1.00 | 13.16 | B | C |
| ATOM | 14339 | C | ALA | B | 363 | 39.214 | 17.625 | −19.940 | 1.00 | 13.54 | B | C |
| ATOM | 14340 | O | ALA | B | 363 | 38.772 | 17.398 | −21.066 | 1.00 | 13.89 | B | O |
| ATOM | 14342 | N | ASP | B | 364 | 39.626 | 18.831 | −19.553 | 1.00 | 13.59 | B | N |
| ATOM | 14343 | CA | ASP | B | 364 | 39.577 | 19.995 | −20.447 | 1.00 | 13.61 | B | C |
| ATOM | 14345 | CB | ASP | B | 364 | 39.922 | 21.277 | −19.683 | 1.00 | 13.78 | B | C |
| ATOM | 14348 | CG | ASP | B | 364 | 38.894 | 21.626 | −18.616 | 1.00 | 16.18 | B | C |
| ATOM | 14349 | OD1 | ASP | B | 364 | 38.028 | 20.775 | −18.311 | 1.00 | 19.21 | B | O |
| ATOM | 14350 | OD2 | ASP | B | 364 | 38.957 | 22.753 | −18.077 | 1.00 | 17.35 | B | O |
| ATOM | 14351 | C | ASP | B | 364 | 40.503 | 19.861 | −21.666 | 1.00 | 13.27 | B | C |
| ATOM | 14352 | O | ASP | B | 364 | 40.219 | 20.435 | −22.721 | 1.00 | 12.94 | B | O |
| ATOM | 14354 | N | LEU | B | 365 | 41.601 | 19.116 | −21.521 | 1.00 | 12.55 | B | N |
| ATOM | 14355 | CA | LEU | B | 365 | 42.537 | 18.901 | −22.627 | 1.00 | 11.93 | B | C |
| ATOM | 14357 | CB | LEU | B | 365 | 43.893 | 18.407 | −22.108 | 1.00 | 11.48 | B | C |
| ATOM | 14360 | CG | LEU | B | 365 | 44.991 | 18.096 | −23.139 | 1.00 | 9.74 | B | C |
| ATOM | 14362 | CD1 | LEU | B | 365 | 45.213 | 19.237 | −24.114 | 1.00 | 7.44 | B | C |
| ATOM | 14366 | CD2 | LEU | B | 365 | 46.293 | 17.754 | −22.438 | 1.00 | 7.19 | B | C |
| ATOM | 14370 | C | LEU | B | 365 | 41.968 | 17.917 | −23.643 | 1.00 | 12.31 | B | C |
| ATOM | 14371 | O | LEU | B | 365 | 42.123 | 18.103 | −24.848 | 1.00 | 12.10 | B | O |
| ATOM | 14373 | N | CYS | B | 366 | 41.312 | 16.870 | −23.156 | 1.00 | 13.31 | B | N |
| ATOM | 14374 | CA | CYS | B | 366 | 40.674 | 15.889 | −24.034 | 1.00 | 14.41 | B | C |
| ATOM | 14376 | CB | CYS | B | 366 | 40.246 | 14.655 | −23.240 | 1.00 | 14.50 | B | C |
| ATOM | 14379 | SG | CYS | B | 366 | 41.629 | 13.759 | −22.500 | 1.00 | 14.66 | B | S |
| ATOM | 14381 | C | CYS | B | 366 | 39.475 | 16.505 | −24.756 | 1.00 | 15.14 | B | C |

TABLE 8-2-continued

Coordinates for L494P Structure

| ATOM | 14382 | O | CYS | B | 366 | 39.314 | 16.319 | −25.966 | 1.00 | 15.49 | B | O |
|---|---|---|---|---|---|---|---|---|---|---|---|---|
| ATOM | 14384 | N | ASN | B | 367 | 38.641 | 17.229 | −24.005 | 1.00 | 15.16 | B | N |
| ATOM | 14385 | CA | ASN | B | 367 | 37.579 | 18.057 | −24.585 | 1.00 | 14.89 | B | C |
| ATOM | 14387 | CB | ASN | B | 367 | 36.875 | 18.893 | −23.502 | 1.00 | 14.96 | B | C |
| ATOM | 14390 | CG | ASN | B | 367 | 35.727 | 18.155 | −22.831 | 1.00 | 14.43 | B | C |
| ATOM | 14391 | OD1 | ASN | B | 367 | 34.815 | 17.660 | −23.495 | 1.00 | 13.51 | B | O |
| ATOM | 14392 | ND2 | ASN | B | 367 | 35.751 | 18.110 | −21.503 | 1.00 | 13.11 | B | N |
| ATOM | 14395 | C | ASN | B | 367 | 38.139 | 19.000 | −25.648 | 1.00 | 15.02 | B | C |
| ATOM | 14396 | O | ASN | B | 367 | 37.520 | 19.203 | −26.691 | 1.00 | 14.98 | B | O |
| ATOM | 14398 | N | ALA | B | 368 | 39.309 | 19.574 | −25.368 | 1.00 | 15.27 | B | N |
| ATOM | 14399 | CA | ALA | B | 368 | 39.981 | 20.480 | −26.303 | 1.00 | 15.42 | B | C |
| ATOM | 14401 | CB | ALA | B | 368 | 41.197 | 21.126 | −25.646 | 1.00 | 15.49 | B | C |
| ATOM | 14405 | C | ALA | B | 368 | 40.394 | 19.763 | −27.583 | 1.00 | 15.38 | B | C |
| ATOM | 14406 | O | ALA | B | 368 | 40.305 | 20.335 | −28.672 | 1.00 | 14.84 | B | O |
| ATOM | 14408 | N | PHE | B | 369 | 40.850 | 18.517 | −27.444 | 1.00 | 15.74 | B | N |
| ATOM | 14409 | CA | PHE | B | 369 | 41.198 | 17.689 | −28.600 | 1.00 | 15.84 | B | C |
| ATOM | 14411 | CB | PHE | B | 369 | 41.926 | 16.405 | −28.175 | 1.00 | 15.87 | B | C |
| ATOM | 14414 | CG | PHE | B | 369 | 43.362 | 16.608 | −27.751 | 1.00 | 16.19 | B | C |
| ATOM | 14415 | CD1 | PHE | B | 369 | 44.261 | 17.284 | −28.565 | 1.00 | 17.44 | B | C |
| ATOM | 14417 | CE1 | PHE | B | 369 | 45.589 | 17.449 | −28.175 | 1.00 | 17.59 | B | C |
| ATOM | 14419 | CZ | PHE | B | 369 | 46.031 | 16.919 | −26.978 | 1.00 | 14.90 | B | C |
| ATOM | 14421 | CE2 | PHE | B | 369 | 45.152 | 16.230 | −26.169 | 1.00 | 14.93 | B | C |
| ATOM | 14423 | CD2 | PHE | B | 369 | 43.828 | 16.069 | −26.558 | 1.00 | 16.05 | B | C |
| ATOM | 14425 | C | PHE | B | 369 | 39.953 | 17.313 | −29.402 | 1.00 | 15.56 | B | C |
| ATOM | 14426 | O | PHE | B | 369 | 39.951 | 17.391 | −30.628 | 1.00 | 15.57 | B | O |
| ATOM | 14428 | N | LEU | B | 370 | 38.898 | 16.904 | −28.705 | 1.00 | 15.73 | B | N |
| ATOM | 14429 | CA | LEU | B | 370 | 37.660 | 16.472 | −29.358 | 1.00 | 16.24 | B | C |
| ATOM | 14431 | CB | LEU | B | 370 | 36.587 | 16.157 | −28.302 | 1.00 | 16.24 | B | C |
| ATOM | 14434 | CG | LEU | B | 370 | 35.468 | 15.179 | −28.670 | 1.00 | 15.94 | B | C |
| ATOM | 14436 | CD1 | LEU | B | 370 | 36.027 | 13.860 | −29.180 | 1.00 | 15.36 | B | C |
| ATOM | 14440 | CD2 | LEU | B | 370 | 34.569 | 14.943 | −27.466 | 1.00 | 15.13 | B | C |
| ATOM | 14444 | C | LEU | B | 370 | 37.167 | 17.547 | −30.328 | 1.00 | 16.58 | B | C |
| ATOM | 14445 | O | LEU | B | 370 | 36.894 | 17.269 | −31.496 | 1.00 | 16.08 | B | O |
| ATOM | 14447 | N | GLN | B | 371 | 37.087 | 18.776 | −29.828 | 1.00 | 17.63 | B | N |
| ATOM | 14448 | CA | GLN | B | 371 | 36.713 | 19.947 | −30.624 | 1.00 | 18.39 | B | C |
| ATOM | 14450 | CB | GLN | B | 371 | 36.835 | 21.212 | −29.761 | 1.00 | 18.47 | B | C |
| ATOM | 14453 | CG | GLN | B | 371 | 36.465 | 22.509 | −30.455 | 1.00 | 18.40 | B | C |
| ATOM | 14456 | CD | GLN | B | 371 | 35.014 | 22.546 | −30.854 | 1.00 | 19.71 | B | C |
| ATOM | 14457 | OE1 | GLN | B | 371 | 34.657 | 22.160 | −31.965 | 1.00 | 21.51 | B | O |
| ATOM | 14458 | NE2 | GLN | B | 371 | 34.161 | 22.995 | −29.942 | 1.00 | 21.78 | B | N |
| ATOM | 14461 | C | GLN | B | 371 | 37.557 | 20.098 | −31.899 | 1.00 | 19.05 | B | C |
| ATOM | 14462 | O | GLN | B | 371 | 37.033 | 20.494 | −32.943 | 1.00 | 19.37 | B | O |
| ATOM | 14464 | N | GLU | B | 372 | 38.857 | 19.803 | −31.804 | 1.00 | 19.25 | B | N |
| ATOM | 14465 | CA | GLU | B | 372 | 39.748 | 19.811 | −32.974 | 1.00 | 19.20 | B | C |
| ATOM | 14467 | CB | GLU | B | 372 | 41.226 | 19.689 | −32.562 | 1.00 | 19.45 | B | C |
| ATOM | 14470 | CG | GLU | B | 372 | 41.877 | 20.997 | −32.107 | 1.00 | 21.69 | B | C |
| ATOM | 14473 | CD | GLU | B | 372 | 43.356 | 20.840 | −31.747 | 1.00 | 24.43 | B | C |
| ATOM | 14474 | OE1 | GLU | B | 372 | 43.861 | 19.695 | −31.711 | 1.00 | 25.03 | B | O |
| ATOM | 14475 | OE2 | GLU | B | 372 | 44.017 | 21.870 | −31.498 | 1.00 | 25.72 | B | O |
| ATOM | 14476 | C | GLU | B | 372 | 39.391 | 18.682 | −33.941 | 1.00 | 18.59 | B | C |
| ATOM | 14477 | O | GLU | B | 372 | 39.372 | 18.883 | −35.158 | 1.00 | 18.34 | B | O |
| ATOM | 14479 | N | ALA | B | 373 | 39.108 | 17.502 | −33.391 | 1.00 | 18.19 | B | N |
| ATOM | 14480 | CA | ALA | B | 373 | 38.762 | 16.331 | −34.195 | 1.00 | 17.99 | B | C |
| ATOM | 14482 | CB | ALA | B | 373 | 38.816 | 15.070 | −33.345 | 1.00 | 17.85 | B | C |
| ATOM | 14486 | C | ALA | B | 373 | 37.386 | 16.472 | −34.844 | 1.00 | 17.94 | B | C |
| ATOM | 14487 | O | ALA | B | 373 | 37.146 | 15.920 | −35.916 | 1.00 | 18.34 | B | O |
| ATOM | 14489 | N | LYS | B | 374 | 36.486 | 17.205 | −34.193 | 1.00 | 17.70 | B | N |
| ATOM | 14490 | CA | LYS | B | 374 | 35.146 | 17.438 | −34.736 | 1.00 | 17.42 | B | C |
| ATOM | 14492 | CB | LYS | B | 374 | 34.195 | 17.945 | −33.647 | 1.00 | 17.54 | B | C |
| ATOM | 14495 | CG | LYS | B | 374 | 33.700 | 16.869 | −32.696 | 1.00 | 16.57 | B | C |
| ATOM | 14498 | CD | LYS | B | 374 | 32.755 | 17.459 | −31.667 | 1.00 | 16.38 | B | C |
| ATOM | 14501 | CE | LYS | B | 374 | 32.149 | 16.392 | −30.780 | 1.00 | 16.46 | B | C |
| ATOM | 14504 | NZ | LYS | B | 374 | 31.306 | 16.977 | −29.704 | 1.00 | 15.25 | B | N |
| ATOM | 14508 | C | LYS | B | 374 | 35.174 | 18.425 | −35.900 | 1.00 | 17.26 | B | C |
| ATOM | 14509 | O | LYS | B | 374 | 34.513 | 18.208 | −36.915 | 1.00 | 17.43 | B | O |
| ATOM | 14511 | N | TRP | B | 375 | 35.934 | 19.509 | −35.750 | 1.00 | 17.18 | B | N |
| ATOM | 14512 | CA | TRP | B | 375 | 36.105 | 20.483 | −36.832 | 1.00 | 17.31 | B | C |
| ATOM | 14514 | CB | TRP | B | 375 | 36.949 | 21.681 | −36.372 | 1.00 | 17.16 | B | C |
| ATOM | 14517 | CG | TRP | B | 375 | 36.259 | 22.614 | −35.404 | 1.00 | 17.13 | B | C |
| ATOM | 14518 | CD1 | TRP | B | 375 | 34.916 | 22.857 | −35.304 | 1.00 | 17.41 | B | C |
| ATOM | 14520 | NE1 | TRP | B | 375 | 34.674 | 23.782 | −34.315 | 1.00 | 17.36 | B | N |
| ATOM | 14522 | CE2 | TRP | B | 375 | 35.868 | 24.171 | −33.767 | 1.00 | 17.07 | B | C |
| ATOM | 14523 | CD2 | TRP | B | 375 | 36.891 | 23.458 | −34.429 | 1.00 | 16.95 | B | C |
| ATOM | 14524 | CE3 | TRP | B | 375 | 38.221 | 23.677 | −34.049 | 1.00 | 15.71 | B | C |
| ATOM | 14526 | CZ3 | TRP | B | 375 | 38.484 | 24.587 | −33.029 | 1.00 | 15.41 | B | C |
| ATOM | 14528 | CH2 | TRP | B | 375 | 37.444 | 25.278 | −32.389 | 1.00 | 16.22 | B | C |
| ATOM | 14530 | CZ2 | TRP | B | 375 | 36.133 | 25.084 | −32.741 | 1.00 | 16.57 | B | C |
| ATOM | 14532 | C | TRP | B | 375 | 36.750 | 19.842 | −38.066 | 1.00 | 17.41 | B | C |

TABLE 8-2-continued

Coordinates for L494P Structure

| ATOM | 14533 | O | TRP | B | 375 | 36.502 | 20.269 | −39.198 | 1.00 | 17.35 | B | O |
|---|---|---|---|---|---|---|---|---|---|---|---|---|
| ATOM | 14535 | N | LEU | B | 376 | 37.570 | 18.818 | −37.840 | 1.00 | 17.35 | B | N |
| ATOM | 14536 | CA | LEU | B | 376 | 38.231 | 18.100 | −38.923 | 1.00 | 17.23 | B | C |
| ATOM | 14538 | CB | LEU | B | 376 | 39.425 | 17.302 | −38.391 | 1.00 | 17.49 | B | C |
| ATOM | 14541 | CG | LEU | B | 376 | 40.555 | 17.070 | −39.395 | 1.00 | 18.22 | B | C |
| ATOM | 14543 | CD1 | LEU | B | 376 | 41.433 | 18.312 | −39.485 | 1.00 | 19.63 | B | C |
| ATOM | 14547 | CD2 | LEU | B | 376 | 41.383 | 15.849 | −39.012 | 1.00 | 19.32 | B | C |
| ATOM | 14551 | C | LEU | B | 376 | 37.248 | 17.167 | −39.627 | 1.00 | 16.88 | B | C |
| ATOM | 14552 | O | LEU | B | 376 | 37.183 | 17.143 | −40.854 | 1.00 | 17.11 | B | O |
| ATOM | 14554 | N | TYR | B | 377 | 36.486 | 16.402 | −38.849 | 1.00 | 16.77 | B | N |
| ATOM | 14555 | CA | TYR | B | 377 | 35.499 | 15.476 | −39.412 | 1.00 | 17.06 | B | C |
| ATOM | 14557 | CB | TYR | B | 377 | 34.930 | 14.547 | −38.327 | 1.00 | 17.15 | B | C |
| ATOM | 14560 | CG | TYR | B | 377 | 33.854 | 13.587 | −38.814 | 1.00 | 17.58 | B | C |
| ATOM | 14561 | CD1 | TYR | B | 377 | 34.187 | 12.403 | −39.475 | 1.00 | 17.98 | B | C |
| ATOM | 14563 | CE1 | TYR | B | 377 | 33.200 | 11.520 | −39.920 | 1.00 | 17.11 | B | C |
| ATOM | 14565 | CZ | TYR | B | 377 | 31.865 | 11.820 | −39.701 | 1.00 | 17.79 | B | C |
| ATOM | 14566 | OH | TYR | B | 377 | 30.880 | 10.962 | −40.133 | 1.00 | 15.15 | B | O |
| ATOM | 14568 | CE2 | TYR | B | 377 | 31.511 | 12.987 | −39.047 | 1.00 | 19.01 | B | C |
| ATOM | 14570 | CD2 | TYR | B | 377 | 32.504 | 13.862 | −38.608 | 1.00 | 18.51 | B | C |
| ATOM | 14572 | C | TYR | B | 377 | 34.365 | 16.223 | −40.116 | 1.00 | 16.88 | B | C |
| ATOM | 14573 | O | TYR | B | 377 | 33.846 | 15.748 | −41.126 | 1.00 | 17.51 | B | O |
| ATOM | 14575 | N | ASN | B | 378 | 33.996 | 17.390 | −39.590 | 1.00 | 16.33 | B | N |
| ATOM | 14576 | CA | ASN | B | 378 | 32.891 | 18.178 | −40.140 | 1.00 | 16.09 | B | C |
| ATOM | 14578 | CB | ASN | B | 378 | 32.095 | 18.824 | −38.999 | 1.00 | 16.18 | B | C |
| ATOM | 14581 | CG | ASN | B | 378 | 31.487 | 17.797 | −38.053 | 1.00 | 15.67 | B | C |
| ATOM | 14582 | OD1 | ASN | B | 378 | 30.872 | 16.821 | −38.486 | 1.00 | 14.58 | B | O |
| ATOM | 14583 | ND2 | ASN | B | 378 | 31.651 | 18.021 | −36.755 | 1.00 | 13.56 | B | N |
| ATOM | 14586 | C | ASN | B | 378 | 33.333 | 19.252 | −41.141 | 1.00 | 15.94 | B | C |
| ATOM | 14587 | O | ASN | B | 378 | 32.503 | 20.019 | −41.630 | 1.00 | 15.56 | B | O |
| ATOM | 14589 | N | LYS | B | 379 | 34.632 | 19.300 | −41.444 | 1.00 | 16.13 | B | N |
| ATOM | 14590 | CA | LYS | B | 379 | 35.208 | 20.300 | −42.358 | 1.00 | 16.30 | B | C |
| ATOM | 14592 | CB | LYS | B | 379 | 34.699 | 20.087 | −43.797 | 1.00 | 16.31 | B | C |
| ATOM | 14595 | CG | LYS | B | 379 | 35.509 | 19.101 | −44.626 | 1.00 | 17.12 | B | C |
| ATOM | 14598 | CD | LYS | B | 379 | 35.221 | 19.295 | −46.113 | 1.00 | 18.17 | B | C |
| ATOM | 14601 | CE | LYS | B | 379 | 35.889 | 18.233 | −46.973 | 1.00 | 20.00 | B | C |
| ATOM | 14604 | NZ | LYS | B | 379 | 35.188 | 16.917 | −46.903 | 1.00 | 20.73 | B | N |
| ATOM | 14608 | C | LYS | B | 379 | 34.963 | 21.756 | −41.922 | 1.00 | 16.29 | B | C |
| ATOM | 14609 | O | LYS | B | 379 | 34.987 | 22.669 | −42.751 | 1.00 | 16.86 | B | O |
| ATOM | 14611 | N | SER | B | 380 | 34.755 | 21.978 | −40.625 | 1.00 | 15.76 | B | N |
| ATOM | 14612 | CA | SER | B | 380 | 34.443 | 23.312 | −40.119 | 1.00 | 15.29 | B | C |
| ATOM | 14614 | CB | SER | B | 380 | 34.179 | 23.266 | −38.614 | 1.00 | 15.44 | B | C |
| ATOM | 14617 | OG | SER | B | 380 | 33.129 | 22.367 | −38.305 | 1.00 | 15.59 | B | O |
| ATOM | 14619 | C | SER | B | 380 | 35.580 | 24.284 | −40.417 | 1.00 | 14.99 | B | C |
| ATOM | 14620 | O | SER | B | 380 | 36.743 | 23.885 | −40.479 | 1.00 | 14.56 | B | O |
| ATOM | 14622 | N | THR | B | 381 | 35.231 | 25.557 | −40.600 | 1.00 | 14.97 | B | N |
| ATOM | 14623 | CA | THR | B | 381 | 36.196 | 26.607 | −40.939 | 1.00 | 14.59 | B | C |
| ATOM | 14625 | CB | THR | B | 381 | 35.976 | 27.102 | −42.383 | 1.00 | 14.34 | B | C |
| ATOM | 14627 | OG1 | THR | B | 381 | 34.623 | 27.544 | −42.533 | 1.00 | 13.29 | B | O |
| ATOM | 14629 | CG2 | THR | B | 381 | 36.243 | 25.984 | −43.376 | 1.00 | 14.48 | B | C |
| ATOM | 14633 | C | THR | B | 381 | 36.079 | 27.788 | −39.969 | 1.00 | 14.43 | B | C |
| ATOM | 14634 | O | THR | B | 381 | 35.732 | 28.900 | −40.379 | 1.00 | 14.36 | B | O |
| ATOM | 14636 | N | PRO | B | 382 | 36.379 | 27.551 | −38.676 | 1.00 | 14.16 | B | N |
| ATOM | 14637 | CA | PRO | B | 382 | 36.183 | 28.563 | −37.635 | 1.00 | 14.13 | B | C |
| ATOM | 14639 | CB | PRO | B | 382 | 36.455 | 27.790 | −36.336 | 1.00 | 14.03 | B | C |
| ATOM | 14642 | CG | PRO | B | 382 | 37.313 | 26.672 | −36.731 | 1.00 | 13.70 | B | C |
| ATOM | 14645 | CD | PRO | B | 382 | 36.876 | 26.285 | −38.107 | 1.00 | 13.99 | B | C |
| ATOM | 14648 | C | PRO | B | 382 | 37.114 | 29.768 | −37.731 | 1.00 | 13.68 | B | C |
| ATOM | 14649 | O | PRO | B | 382 | 38.166 | 29.702 | −38.368 | 1.00 | 13.57 | B | O |
| ATOM | 14650 | N | THR | B | 383 | 36.709 | 30.857 | −37.082 | 1.00 | 13.56 | B | N |
| ATOM | 14651 | CA | THR | B | 383 | 37.507 | 32.075 | −37.022 | 1.00 | 13.70 | B | C |
| ATOM | 14653 | CB | THR | B | 383 | 36.758 | 33.208 | −36.285 | 1.00 | 13.82 | B | C |
| ATOM | 14655 | OG1 | THR | B | 383 | 36.295 | 32.735 | −35.013 | 1.00 | 13.66 | B | O |
| ATOM | 14657 | CG2 | THR | B | 383 | 35.571 | 33.691 | −37.103 | 1.00 | 13.85 | B | C |
| ATOM | 14661 | C | THR | B | 383 | 38.809 | 31.809 | −36.289 | 1.00 | 13.73 | B | C |
| ATOM | 14662 | O | THR | B | 383 | 38.962 | 30.774 | −35.645 | 1.00 | 14.13 | B | O |
| ATOM | 14664 | N | PHE | B | 384 | 39.744 | 32.747 | −36.387 | 1.00 | 13.93 | B | N |
| ATOM | 14665 | CA | PHE | B | 384 | 41.013 | 32.645 | −35.668 | 1.00 | 13.87 | B | C |
| ATOM | 14667 | CB | PHE | B | 384 | 41.974 | 33.752 | −36.117 | 1.00 | 13.82 | B | C |
| ATOM | 14670 | CG | PHE | B | 384 | 43.181 | 33.906 | −35.237 | 1.00 | 14.42 | B | C |
| ATOM | 14671 | CD1 | PHE | B | 384 | 44.302 | 33.112 | −35.428 | 1.00 | 15.39 | B | C |
| ATOM | 14673 | CE1 | PHE | B | 384 | 45.421 | 33.253 | −34.613 | 1.00 | 15.72 | B | C |
| ATOM | 14675 | CZ | PHE | B | 384 | 45.423 | 34.201 | −33.597 | 1.00 | 16.47 | B | C |
| ATOM | 14677 | CE2 | PHE | B | 384 | 44.307 | 35.002 | −33.398 | 1.00 | 15.83 | B | C |
| ATOM | 14679 | CD2 | PHE | B | 384 | 43.195 | 34.851 | −34.215 | 1.00 | 15.61 | B | C |
| ATOM | 14681 | C | PHE | B | 384 | 40.803 | 32.697 | −34.155 | 1.00 | 13.83 | B | C |
| ATOM | 14682 | O | PHE | B | 384 | 41.562 | 32.086 | −33.407 | 1.00 | 13.69 | B | O |
| ATOM | 14684 | N | ASP | B | 385 | 39.773 | 33.419 | −33.714 | 1.00 | 14.28 | B | N |
| ATOM | 14685 | CA | ASP | B | 385 | 39.461 | 33.546 | −32.286 | 1.00 | 14.69 | B | C |

TABLE 8-2-continued

Coordinates for L494P Structure

| ATOM | 14687 | CB | ASP | B | 385 | 38.335 | 34.564 | −32.067 | 1.00 | 14.68 | B | C |
|---|---|---|---|---|---|---|---|---|---|---|---|---|
| ATOM | 14690 | CG | ASP | B | 385 | 38.758 | 35.989 | −32.377 | 1.00 | 14.29 | B | C |
| ATOM | 14691 | OD1 | ASP | B | 385 | 39.916 | 36.198 | −32.801 | 1.00 | 12.29 | B | O |
| ATOM | 14692 | OD2 | ASP | B | 385 | 37.922 | 36.901 | −32.194 | 1.00 | 13.65 | B | O |
| ATOM | 14693 | C | ASP | B | 385 | 39.072 | 32.212 | −31.647 | 1.00 | 14.95 | B | C |
| ATOM | 14694 | O | ASP | B | 385 | 39.558 | 31.872 | −30.565 | 1.00 | 15.03 | B | O |
| ATOM | 14696 | N | ASP | B | 386 | 38.199 | 31.463 | −32.315 | 1.00 | 15.10 | B | N |
| ATOM | 14697 | CA | ASP | B | 386 | 37.756 | 30.164 | −31.807 | 1.00 | 15.21 | B | C |
| ATOM | 14699 | CB | ASP | B | 386 | 36.562 | 29.635 | −32.608 | 1.00 | 14.89 | B | C |
| ATOM | 14702 | CG | ASP | B | 386 | 35.352 | 30.537 | −32.518 | 1.00 | 13.79 | B | C |
| ATOM | 14703 | OD1 | ASP | B | 386 | 35.359 | 31.469 | −31.688 | 1.00 | 11.65 | B | O |
| ATOM | 14704 | OD2 | ASP | B | 386 | 34.395 | 30.312 | −33.284 | 1.00 | 13.99 | B | O |
| ATOM | 14705 | C | ASP | B | 386 | 38.881 | 29.141 | −31.845 | 1.00 | 15.56 | B | C |
| ATOM | 14706 | O | ASP | B | 386 | 39.175 | 28.506 | −30.831 | 1.00 | 15.59 | B | O |
| ATOM | 14708 | N | TYR | B | 387 | 39.509 | 28.987 | −33.010 | 1.00 | 16.18 | B | N |
| ATOM | 14709 | CA | TYR | B | 387 | 40.535 | 27.961 | −33.190 | 1.00 | 17.16 | B | C |
| ATOM | 14711 | CB | TYR | B | 387 | 41.021 | 27.871 | −34.639 | 1.00 | 17.34 | B | C |
| ATOM | 14714 | CG | TYR | B | 387 | 42.013 | 26.745 | −34.840 | 1.00 | 19.17 | B | C |
| ATOM | 14715 | CD1 | TYR | B | 387 | 41.602 | 25.419 | −34.781 | 1.00 | 22.10 | B | C |
| ATOM | 14717 | CE1 | TYR | B | 387 | 42.503 | 24.374 | −34.945 | 1.00 | 25.04 | B | C |
| ATOM | 14719 | CZ | TYR | B | 387 | 43.839 | 24.650 | −35.170 | 1.00 | 26.53 | B | C |
| ATOM | 14720 | OH | TYR | B | 387 | 44.731 | 23.609 | −35.338 | 1.00 | 27.53 | B | O |
| ATOM | 14722 | CE2 | TYR | B | 387 | 44.278 | 25.965 | −35.225 | 1.00 | 25.30 | B | C |
| ATOM | 14724 | CD2 | TYR | B | 387 | 43.363 | 27.004 | −35.055 | 1.00 | 22.56 | B | C |
| ATOM | 14726 | C | TYR | B | 387 | 41.729 | 28.180 | −32.272 | 1.00 | 17.41 | B | C |
| ATOM | 14727 | O | TYR | B | 387 | 42.241 | 27.224 | −31.689 | 1.00 | 18.04 | B | O |
| ATOM | 14729 | N | PHE | B | 388 | 42.177 | 29.426 | −32.147 | 1.00 | 17.25 | B | N |
| ATOM | 14730 | CA | PHE | B | 388 | 43.255 | 29.726 | −31.218 | 1.00 | 17.19 | B | C |
| ATOM | 14732 | CB | PHE | B | 388 | 43.803 | 31.135 | −31.406 | 1.00 | 16.75 | B | C |
| ATOM | 14735 | CG | PHE | B | 388 | 45.047 | 31.387 | −30.617 | 1.00 | 16.33 | B | C |
| ATOM | 14736 | CD1 | PHE | B | 388 | 46.244 | 30.796 | −30.994 | 1.00 | 16.78 | B | C |
| ATOM | 14738 | CE1 | PHE | B | 388 | 47.401 | 31.006 | −30.265 | 1.00 | 16.25 | B | C |
| ATOM | 14740 | CZ | PHE | B | 388 | 47.369 | 31.808 | −29.137 | 1.00 | 16.41 | B | C |
| ATOM | 14742 | CE2 | PHE | B | 388 | 46.175 | 32.396 | −28.742 | 1.00 | 16.15 | B | C |
| ATOM | 14744 | CD2 | PHE | B | 388 | 45.021 | 32.179 | −29.479 | 1.00 | 16.35 | B | C |
| ATOM | 14746 | C | PHE | B | 388 | 42.778 | 29.539 | −29.783 | 1.00 | 17.91 | B | C |
| ATOM | 14747 | O | PHE | B | 388 | 43.468 | 28.913 | −28.979 | 1.00 | 18.31 | B | O |
| ATOM | 14749 | N | GLY | B | 389 | 41.590 | 30.062 | −29.475 | 1.00 | 18.30 | B | N |
| ATOM | 14750 | CA | GLY | B | 389 | 40.982 | 29.902 | −28.151 | 1.00 | 18.22 | B | C |
| ATOM | 14753 | C | GLY | B | 389 | 41.074 | 28.480 | −27.625 | 1.00 | 18.15 | B | C |
| ATOM | 14754 | O | GLY | B | 389 | 41.426 | 28.262 | −26.465 | 1.00 | 18.35 | B | O |
| ATOM | 14756 | N | ASN | B | 390 | 40.760 | 27.516 | −28.487 | 1.00 | 17.78 | B | N |
| ATOM | 14757 | CA | ASN | B | 390 | 40.865 | 26.097 | −28.154 | 1.00 | 17.52 | B | C |
| ATOM | 14759 | CB | ASN | B | 390 | 39.912 | 25.286 | −29.037 | 1.00 | 17.50 | B | C |
| ATOM | 14762 | CG | ASN | B | 390 | 39.703 | 23.875 | −28.529 | 1.00 | 17.13 | B | C |
| ATOM | 14763 | OD1 | ASN | B | 390 | 39.294 | 23.673 | −27.386 | 1.00 | 16.19 | B | O |
| ATOM | 14764 | ND2 | ASN | B | 390 | 39.977 | 22.890 | −29.377 | 1.00 | 16.14 | B | N |
| ATOM | 14767 | C | ASN | B | 390 | 42.289 | 25.559 | −28.324 | 1.00 | 17.35 | B | C |
| ATOM | 14768 | O | ASN | B | 390 | 42.689 | 24.616 | −27.637 | 1.00 | 16.87 | B | O |
| ATOM | 14770 | N | ALA | B | 391 | 43.041 | 26.160 | −29.246 | 1.00 | 17.15 | B | N |
| ATOM | 14771 | CA | ALA | B | 391 | 44.367 | 25.670 | −29.628 | 1.00 | 16.79 | B | C |
| ATOM | 14773 | CB | ALA | B | 391 | 44.874 | 26.414 | −30.850 | 1.00 | 16.54 | B | C |
| ATOM | 14777 | C | ALA | B | 391 | 45.402 | 25.737 | −28.507 | 1.00 | 16.67 | B | C |
| ATOM | 14778 | O | ALA | B | 391 | 46.229 | 24.834 | −28.386 | 1.00 | 17.01 | B | O |
| ATOM | 14780 | N | TRP | B | 392 | 45.378 | 26.795 | −27.700 | 1.00 | 16.56 | B | N |
| ATOM | 14781 | CA | TRP | B | 392 | 46.324 | 26.891 | −26.585 | 1.00 | 16.79 | B | C |
| ATOM | 14783 | CB | TRP | B | 392 | 46.551 | 28.339 | −26.114 | 1.00 | 16.90 | B | C |
| ATOM | 14786 | CG | TRP | B | 392 | 45.347 | 29.101 | −25.644 | 1.00 | 16.82 | B | C |
| ATOM | 14787 | CD1 | TRP | B | 392 | 44.616 | 29.993 | −26.368 | 1.00 | 17.86 | B | C |
| ATOM | 14789 | NE1 | TRP | B | 392 | 43.604 | 30.516 | −25.601 | 1.00 | 19.26 | B | N |
| ATOM | 14791 | CE2 | TRP | B | 392 | 43.675 | 29.974 | −24.346 | 1.00 | 19.44 | B | C |
| ATOM | 14792 | CD2 | TRP | B | 392 | 44.770 | 29.082 | −24.333 | 1.00 | 18.34 | B | C |
| ATOM | 14793 | CE3 | TRP | B | 392 | 45.061 | 28.389 | −23.152 | 1.00 | 20.35 | B | C |
| ATOM | 14795 | CZ3 | TRP | B | 392 | 44.259 | 28.606 | −22.035 | 1.00 | 20.88 | B | C |
| ATOM | 14797 | CH2 | TRP | B | 392 | 43.177 | 29.500 | −22.082 | 1.00 | 20.79 | B | C |
| ATOM | 14799 | CZ2 | TRP | B | 392 | 42.870 | 30.192 | −23.224 | 1.00 | 20.30 | B | C |
| ATOM | 14801 | C | TRP | B | 392 | 45.952 | 25.973 | −25.420 | 1.00 | 17.05 | B | C |
| ATOM | 14802 | O | TRP | B | 392 | 46.818 | 25.598 | −24.635 | 1.00 | 17.62 | B | O |
| ATOM | 14804 | N | LYS | B | 393 | 44.682 | 25.596 | −25.310 | 1.00 | 17.13 | B | N |
| ATOM | 14805 | CA | LYS | B | 393 | 44.297 | 24.524 | −24.390 | 1.00 | 17.62 | B | C |
| ATOM | 14807 | CB | LYS | B | 393 | 42.771 | 24.422 | −24.242 | 1.00 | 18.17 | B | C |
| ATOM | 14810 | CG | LYS | B | 393 | 42.149 | 25.470 | −23.336 | 1.00 | 19.49 | B | C |
| ATOM | 14813 | CD | LYS | B | 393 | 40.637 | 25.300 | −23.251 | 1.00 | 20.92 | B | C |
| ATOM | 14816 | CE | LYS | B | 393 | 39.987 | 26.436 | −22.472 | 1.00 | 22.85 | B | C |
| ATOM | 14819 | NZ | LYS | B | 393 | 40.242 | 27.775 | −23.089 | 1.00 | 23.75 | B | N |
| ATOM | 14823 | C | LYS | B | 393 | 44.855 | 23.190 | −24.891 | 1.00 | 17.26 | B | C |
| ATOM | 14824 | O | LYS | B | 393 | 45.466 | 22.438 | −24.130 | 1.00 | 17.57 | B | O |
| ATOM | 14826 | N | SER | B | 394 | 44.655 | 22.917 | −26.181 | 1.00 | 16.47 | B | N |

TABLE 8-2-continued

Coordinates for L494P Structure

| ATOM | 14827 | CA | SER | B | 394 | 45.061 | 21.644 | −26.782 | 1.00 | 15.87 | B | C |
|---|---|---|---|---|---|---|---|---|---|---|---|---|
| ATOM | 14829 | CB | SER | B | 394 | 44.438 | 21.474 | −28.173 | 1.00 | 16.34 | B | C |
| ATOM | 14832 | OG | SER | B | 394 | 45.053 | 22.324 | −29.128 | 1.00 | 17.96 | B | O |
| ATOM | 14834 | C | SER | B | 394 | 46.573 | 21.488 | −26.882 | 1.00 | 14.74 | B | C |
| ATOM | 14835 | O | SER | B | 394 | 47.064 | 20.395 | −27.163 | 1.00 | 14.87 | B | O |
| ATOM | 14837 | N | SER | B | 395 | 47.306 | 22.581 | −26.674 | 1.00 | 13.73 | B | N |
| ATOM | 14838 | CA | SER | B | 395 | 48.768 | 22.536 | −26.627 | 1.00 | 12.86 | B | C |
| ATOM | 14840 | CB | SER | B | 395 | 49.347 | 23.953 | −26.514 | 1.00 | 12.97 | B | C |
| ATOM | 14843 | OG | SER | B | 395 | 49.165 | 24.500 | −25.216 | 1.00 | 10.58 | B | O |
| ATOM | 14845 | C | SER | B | 395 | 49.263 | 21.677 | −25.460 | 1.00 | 12.10 | B | C |
| ATOM | 14846 | O | SER | B | 395 | 50.306 | 21.037 | −25.563 | 1.00 | 12.00 | B | O |
| ATOM | 14848 | N | SER | B | 396 | 48.478 | 21.661 | −24.379 | 1.00 | 11.22 | B | N |
| ATOM | 14849 | CA | SER | B | 396 | 48.812 | 21.023 | −23.096 | 1.00 | 10.50 | B | C |
| ATOM | 14851 | CB | SER | B | 396 | 49.589 | 19.704 | −23.259 | 1.00 | 10.20 | B | C |
| ATOM | 14854 | OG | SER | B | 396 | 50.988 | 19.921 | −23.297 | 1.00 | 8.38 | B | O |
| ATOM | 14856 | C | SER | B | 396 | 49.576 | 21.997 | −22.197 | 1.00 | 10.26 | B | C |
| ATOM | 14857 | O | SER | B | 396 | 50.076 | 21.611 | −21.138 | 1.00 | 9.66 | B | O |
| ATOM | 14859 | N | GLY | B | 397 | 49.637 | 23.260 | −22.623 | 1.00 | 9.98 | B | N |
| ATOM | 14860 | CA | GLY | B | 397 | 50.327 | 24.315 | −21.889 | 1.00 | 9.92 | B | C |
| ATOM | 14863 | C | GLY | B | 397 | 49.710 | 24.631 | −20.538 | 1.00 | 9.97 | B | C |
| ATOM | 14864 | O | GLY | B | 397 | 50.433 | 24.872 | −19.576 | 1.00 | 10.10 | B | O |
| ATOM | 14866 | N | PRO | B | 398 | 48.368 | 24.665 | −20.462 | 1.00 | 10.22 | B | N |
| ATOM | 14867 | CA | PRO | B | 398 | 47.702 | 24.796 | −19.167 | 1.00 | 10.28 | B | C |
| ATOM | 14869 | CB | PRO | B | 398 | 46.239 | 25.041 | −19.547 | 1.00 | 10.17 | B | C |
| ATOM | 14872 | CG | PRO | B | 398 | 46.294 | 25.597 | −20.918 | 1.00 | 10.28 | B | C |
| ATOM | 14875 | CD | PRO | B | 398 | 47.428 | 24.886 | −21.573 | 1.00 | 10.52 | B | C |
| ATOM | 14878 | C | PRO | B | 398 | 47.834 | 23.548 | −18.292 | 1.00 | 10.37 | B | C |
| ATOM | 14879 | O | PRO | B | 398 | 48.153 | 23.664 | −17.105 | 1.00 | 9.87 | B | O |
| ATOM | 14880 | N | LEU | B | 399 | 47.594 | 22.372 | −18.872 | 1.00 | 10.74 | B | N |
| ATOM | 14881 | CA | LEU | B | 399 | 47.682 | 21.120 | −18.118 | 1.00 | 10.74 | B | C |
| ATOM | 14883 | CB | LEU | B | 399 | 47.255 | 19.920 | −18.965 | 1.00 | 10.40 | B | C |
| ATOM | 14886 | CG | LEU | B | 399 | 47.118 | 18.589 | −18.212 | 1.00 | 8.78 | B | C |
| ATOM | 14888 | CD1 | LEU | B | 399 | 46.277 | 17.619 | −19.010 | 1.00 | 9.68 | B | C |
| ATOM | 14892 | CD2 | LEU | B | 399 | 48.466 | 17.965 | −17.903 | 1.00 | 8.42 | B | C |
| ATOM | 14896 | C | LEU | B | 399 | 49.093 | 20.911 | −17.587 | 1.00 | 11.26 | B | C |
| ATOM | 14897 | O | LEU | B | 399 | 49.267 | 20.586 | −16.411 | 1.00 | 12.26 | B | O |
| ATOM | 14899 | N | GLN | B | 400 | 50.095 | 21.095 | −18.443 | 1.00 | 10.88 | B | N |
| ATOM | 14900 | CA | GLN | B | 400 | 51.482 | 20.980 | −18.000 | 1.00 | 10.85 | B | C |
| ATOM | 14902 | CB | GLN | B | 400 | 52.459 | 21.371 | −19.109 | 1.00 | 10.68 | B | C |
| ATOM | 14905 | CG | GLN | B | 400 | 52.718 | 20.268 | −20.118 | 1.00 | 10.94 | B | C |
| ATOM | 14908 | CD | GLN | B | 400 | 53.840 | 20.605 | −21.075 | 1.00 | 10.14 | B | C |
| ATOM | 14909 | OE1 | GLN | B | 400 | 54.874 | 21.143 | −20.674 | 1.00 | 8.70 | B | O |
| ATOM | 14910 | NE2 | GLN | B | 400 | 53.650 | 20.279 | −22.347 | 1.00 | 10.31 | B | N |
| ATOM | 14913 | C | GLN | B | 400 | 51.726 | 21.844 | −16.768 | 1.00 | 11.14 | B | C |
| ATOM | 14914 | O | GLN | B | 400 | 52.241 | 21.358 | −15.761 | 1.00 | 11.47 | B | O |
| ATOM | 14916 | N | LEU | B | 401 | 51.329 | 23.114 | −16.845 | 1.00 | 11.14 | B | N |
| ATOM | 14917 | CA | LEU | B | 401 | 51.568 | 24.065 | −15.759 | 1.00 | 11.06 | B | C |
| ATOM | 14919 | CB | LEU | B | 401 | 51.299 | 25.498 | −16.221 | 1.00 | 10.61 | B | C |
| ATOM | 14922 | CG | LEU | B | 401 | 52.308 | 26.063 | −17.224 | 1.00 | 11.73 | B | C |
| ATOM | 14924 | CD1 | LEU | B | 401 | 52.040 | 27.539 | −17.482 | 1.00 | 12.66 | B | C |
| ATOM | 14928 | CD2 | LEU | B | 401 | 53.736 | 25.867 | −16.738 | 1.00 | 15.02 | B | C |
| ATOM | 14932 | C | LEU | B | 401 | 50.761 | 23.747 | −14.499 | 1.00 | 11.70 | B | C |
| ATOM | 14933 | O | LEU | B | 401 | 51.333 | 23.653 | −13.412 | 1.00 | 12.09 | B | O |
| ATOM | 14935 | N | VAL | B | 402 | 49.448 | 23.559 | −14.633 | 1.00 | 12.08 | B | N |
| ATOM | 14936 | CA | VAL | B | 402 | 48.625 | 23.148 | −13.485 | 1.00 | 12.19 | B | C |
| ATOM | 14938 | CB | VAL | B | 402 | 47.230 | 22.621 | −13.907 | 1.00 | 12.09 | B | C |
| ATOM | 14940 | CG1 | VAL | B | 402 | 46.393 | 23.736 | −14.500 | 1.00 | 11.45 | B | C |
| ATOM | 14944 | CG2 | VAL | B | 402 | 46.508 | 21.992 | −12.715 | 1.00 | 10.48 | B | C |
| ATOM | 14948 | C | VAL | B | 402 | 49.343 | 22.055 | −12.691 | 1.00 | 12.73 | B | C |
| ATOM | 14949 | O | VAL | B | 402 | 49.364 | 22.090 | −11.463 | 1.00 | 13.03 | B | O |
| ATOM | 14951 | N | PHE | B | 403 | 49.931 | 21.096 | −13.406 | 1.00 | 12.77 | B | N |
| ATOM | 14952 | CA | PHE | B | 403 | 50.689 | 20.009 | −12.789 | 1.00 | 12.83 | B | C |
| ATOM | 14954 | CB | PHE | B | 403 | 51.004 | 18.918 | −13.818 | 1.00 | 13.10 | B | C |
| ATOM | 14957 | CG | PHE | B | 403 | 50.038 | 17.776 | −13.798 | 1.00 | 13.23 | B | C |
| ATOM | 14958 | CD1 | PHE | B | 403 | 50.267 | 16.676 | −12.985 | 1.00 | 12.90 | B | C |
| ATOM | 14960 | CE1 | PHE | B | 403 | 49.379 | 15.618 | −12.959 | 1.00 | 14.26 | B | C |
| ATOM | 14962 | CZ | PHE | B | 403 | 48.241 | 15.653 | −13.749 | 1.00 | 15.62 | B | C |
| ATOM | 14964 | CE2 | PHE | B | 403 | 48.004 | 16.745 | −14.567 | 1.00 | 15.30 | B | C |
| ATOM | 14966 | CD2 | PHE | B | 403 | 48.899 | 17.800 | −14.586 | 1.00 | 14.00 | B | C |
| ATOM | 14968 | C | PHE | B | 403 | 51.985 | 20.487 | −12.142 | 1.00 | 12.73 | B | C |
| ATOM | 14969 | O | PHE | B | 403 | 52.337 | 20.036 | −11.051 | 1.00 | 12.37 | B | O |
| ATOM | 14971 | N | ALA | B | 404 | 52.695 | 21.383 | −12.824 | 1.00 | 12.86 | B | N |
| ATOM | 14972 | CA | ALA | B | 404 | 53.958 | 21.925 | −12.317 | 1.00 | 12.97 | B | C |
| ATOM | 14974 | CB | ALA | B | 404 | 54.659 | 22.744 | −13.395 | 1.00 | 12.54 | B | C |
| ATOM | 14978 | C | ALA | B | 404 | 53.750 | 22.771 | −11.062 | 1.00 | 13.43 | B | C |
| ATOM | 14979 | O | ALA | B | 404 | 54.665 | 22.906 | −10.247 | 1.00 | 13.75 | B | O |
| ATOM | 14981 | N | TYR | B | 405 | 52.549 | 23.332 | −10.915 | 1.00 | 13.71 | B | N |
| ATOM | 14982 | CA | TYR | B | 405 | 52.200 | 24.148 | −9.750 | 1.00 | 13.86 | B | C |

TABLE 8-2-continued

Coordinates for L494P Structure

| ATOM | 14984 | CB | TYR | B | 405 | 50.762 | 24.667 | −9.872 | 1.00 | 13.79 | B | C |
|---|---|---|---|---|---|---|---|---|---|---|---|---|
| ATOM | 14987 | CG | TYR | B | 405 | 50.254 | 25.335 | −8.618 | 1.00 | 13.21 | B | C |
| ATOM | 14988 | CD1 | TYR | B | 405 | 50.594 | 26.652 | −8.323 | 1.00 | 12.79 | B | C |
| ATOM | 14990 | CE1 | TYR | B | 405 | 50.136 | 27.270 | −7.170 | 1.00 | 11.81 | B | C |
| ATOM | 14992 | CZ | TYR | B | 405 | 49.332 | 26.565 | −6.298 | 1.00 | 12.37 | B | C |
| ATOM | 14993 | OH | TYR | B | 405 | 48.878 | 27.167 | −5.154 | 1.00 | 12.04 | B | O |
| ATOM | 14995 | CE2 | TYR | B | 405 | 48.983 | 25.251 | −6.566 | 1.00 | 12.72 | B | C |
| ATOM | 14997 | CD2 | TYR | B | 405 | 49.444 | 24.645 | −7.720 | 1.00 | 12.42 | B | C |
| ATOM | 14999 | C | TYR | B | 405 | 52.357 | 23.371 | −8.446 | 1.00 | 14.17 | B | C |
| ATOM | 15000 | O | TYR | B | 405 | 53.016 | 23.836 | −7.515 | 1.00 | 14.28 | B | O |
| ATOM | 15002 | N | PHE | B | 406 | 51.753 | 22.186 | −8.391 | 1.00 | 14.49 | B | N |
| ATOM | 15003 | CA | PHE | B | 406 | 51.802 | 21.342 | −7.193 | 1.00 | 14.68 | B | C |
| ATOM | 15005 | CB | PHE | B | 406 | 50.791 | 20.197 | −7.298 | 1.00 | 14.37 | B | C |
| ATOM | 15008 | CG | PHE | B | 406 | 49.360 | 20.654 | −7.391 | 1.00 | 13.87 | B | C |
| ATOM | 15009 | CD1 | PHE | B | 406 | 48.612 | 20.883 | −6.246 | 1.00 | 13.63 | B | C |
| ATOM | 15011 | CE1 | PHE | B | 406 | 47.290 | 21.297 | −6.334 | 1.00 | 12.80 | B | C |
| ATOM | 15013 | CZ | PHE | B | 406 | 46.705 | 21.484 | −7.573 | 1.00 | 11.76 | B | C |
| ATOM | 15015 | CE2 | PHE | B | 406 | 47.440 | 21.257 | −8.720 | 1.00 | 12.46 | B | C |
| ATOM | 15017 | CD2 | PHE | B | 406 | 48.758 | 20.843 | −8.626 | 1.00 | 13.06 | B | C |
| ATOM | 15019 | C | PHE | B | 406 | 53.202 | 20.774 | −6.955 | 1.00 | 15.00 | B | C |
| ATOM | 15020 | O | PHE | B | 406 | 53.542 | 20.387 | −5.837 | 1.00 | 14.79 | B | O |
| ATOM | 15022 | N | ALA | B | 407 | 54.001 | 20.725 | −8.015 | 1.00 | 15.76 | B | N |
| ATOM | 15023 | CA | ALA | B | 407 | 55.372 | 20.243 | −7.940 | 1.00 | 16.63 | B | C |
| ATOM | 15025 | CB | ALA | B | 407 | 55.849 | 19.847 | −9.323 | 1.00 | 16.82 | B | C |
| ATOM | 15029 | C | ALA | B | 407 | 56.327 | 21.270 | −7.338 | 1.00 | 17.61 | B | C |
| ATOM | 15030 | O | ALA | B | 407 | 57.348 | 20.889 | −6.761 | 1.00 | 17.54 | B | O |
| ATOM | 15032 | N | VAL | B | 408 | 56.005 | 22.558 | −7.485 | 1.00 | 18.76 | B | N |
| ATOM | 15033 | CA | VAL | B | 408 | 56.896 | 23.644 | −7.041 | 1.00 | 19.68 | B | C |
| ATOM | 15035 | CB | VAL | B | 408 | 57.122 | 24.709 | −8.151 | 1.00 | 19.56 | B | C |
| ATOM | 15037 | CG1 | VAL | B | 408 | 57.867 | 24.099 | −9.326 | 1.00 | 20.05 | B | C |
| ATOM | 15041 | CG2 | VAL | B | 408 | 55.809 | 25.326 | −8.608 | 1.00 | 19.46 | B | C |
| ATOM | 15045 | C | VAL | B | 408 | 56.422 | 24.343 | −5.765 | 1.00 | 20.58 | B | C |
| ATOM | 15046 | O | VAL | B | 408 | 57.217 | 24.560 | −4.850 | 1.00 | 20.87 | B | O |
| ATOM | 15048 | N | VAL | B | 409 | 55.137 | 24.686 | −5.700 | 1.00 | 21.60 | B | N |
| ATOM | 15049 | CA | VAL | B | 409 | 54.589 | 25.416 | −4.556 | 1.00 | 22.34 | B | C |
| ATOM | 15051 | CB | VAL | B | 409 | 53.202 | 26.016 | −4.877 | 1.00 | 22.39 | B | C |
| ATOM | 15053 | CG1 | VAL | B | 409 | 52.600 | 26.674 | −3.640 | 1.00 | 23.44 | B | C |
| ATOM | 15057 | CG2 | VAL | B | 409 | 53.306 | 27.019 | −6.015 | 1.00 | 22.32 | B | C |
| ATOM | 15061 | C | VAL | B | 409 | 54.464 | 24.492 | −3.346 | 1.00 | 22.94 | B | C |
| ATOM | 15062 | O | VAL | B | 409 | 53.760 | 23.483 | −3.411 | 1.00 | 23.20 | B | O |
| ATOM | 15064 | N | GLN | B | 410 | 55.146 | 24.841 | −2.254 | 1.00 | 23.53 | B | N |
| ATOM | 15065 | CA | GLN | B | 410 | 55.110 | 24.046 | −1.021 | 1.00 | 24.19 | B | C |
| ATOM | 15067 | CB | GLN | B | 410 | 56.199 | 24.501 | −0.038 | 1.00 | 24.35 | B | C |
| ATOM | 15070 | CG | GLN | B | 410 | 57.580 | 23.913 | −0.322 | 1.00 | 25.13 | B | C |
| ATOM | 15073 | CD | GLN | B | 410 | 58.700 | 24.597 | 0.458 | 1.00 | 26.32 | B | C |
| ATOM | 15074 | OE1 | GLN | B | 410 | 58.471 | 25.217 | 1.500 | 1.00 | 26.11 | B | O |
| ATOM | 15075 | NE2 | GLN | B | 410 | 59.923 | 24.479 | −0.047 | 1.00 | 26.55 | B | N |
| ATOM | 15078 | C | GLN | B | 410 | 53.736 | 24.119 | −0.354 | 1.00 | 24.67 | B | C |
| ATOM | 15079 | O | GLN | B | 410 | 53.107 | 23.087 | −0.098 | 1.00 | 24.94 | B | O |
| ATOM | 15081 | N | ASN | B | 411 | 53.282 | 25.340 | −0.077 | 1.00 | 24.76 | B | N |
| ATOM | 15082 | CA | ASN | B | 411 | 51.964 | 25.568 | 0.515 | 1.00 | 24.87 | B | C |
| ATOM | 15084 | CB | ASN | B | 411 | 52.044 | 26.607 | 1.639 | 1.00 | 24.93 | B | C |
| ATOM | 15087 | CG | ASN | B | 411 | 52.557 | 26.022 | 2.944 | 1.00 | 25.27 | B | C |
| ATOM | 15088 | OD1 | ASN | B | 411 | 52.140 | 26.439 | 4.027 | 1.00 | 25.02 | B | O |
| ATOM | 15089 | ND2 | ASN | B | 411 | 53.458 | 25.050 | 2.850 | 1.00 | 24.79 | B | N |
| ATOM | 15092 | C | ASN | B | 411 | 50.967 | 26.024 | −0.543 | 1.00 | 24.92 | B | C |
| ATOM | 15093 | O | ASN | B | 411 | 50.950 | 27.198 | −0.924 | 1.00 | 25.20 | B | O |
| ATOM | 15095 | N | ILE | B | 412 | 50.145 | 25.091 | −1.017 | 1.00 | 24.78 | B | N |
| ATOM | 15096 | CA | ILE | B | 412 | 49.102 | 25.407 | −1.996 | 1.00 | 24.69 | B | C |
| ATOM | 15098 | CB | ILE | B | 412 | 48.471 | 24.130 | −2.625 | 1.00 | 24.72 | B | C |
| ATOM | 15100 | CG1 | ILE | B | 412 | 47.696 | 23.311 | −1.585 | 1.00 | 24.16 | B | C |
| ATOM | 15103 | CD1 | ILE | B | 412 | 47.342 | 21.919 | −2.059 | 1.00 | 23.73 | B | C |
| ATOM | 15107 | CG2 | ILE | B | 412 | 49.546 | 23.272 | −3.289 | 1.00 | 25.19 | B | C |
| ATOM | 15111 | C | ILE | B | 412 | 48.015 | 26.260 | −1.350 | 1.00 | 24.62 | B | C |
| ATOM | 15112 | O | ILE | B | 412 | 47.701 | 26.086 | −0.176 | 1.00 | 24.66 | B | O |
| ATOM | 15114 | N | LYS | B | 413 | 47.457 | 27.187 | −2.121 | 1.00 | 24.99 | B | N |
| ATOM | 15115 | CA | LYS | B | 413 | 46.396 | 28.065 | −1.635 | 1.00 | 25.75 | B | C |
| ATOM | 15117 | CB | LYS | B | 413 | 46.871 | 29.520 | −1.653 | 1.00 | 25.95 | B | C |
| ATOM | 15120 | CG | LYS | B | 413 | 48.243 | 29.716 | −1.015 | 1.00 | 28.01 | B | C |
| ATOM | 15123 | CD | LYS | B | 413 | 48.538 | 31.179 | −0.705 | 1.00 | 30.48 | B | C |
| ATOM | 15126 | CE | LYS | B | 413 | 49.825 | 31.320 | 0.103 | 1.00 | 31.81 | B | C |
| ATOM | 15129 | NZ | LYS | B | 413 | 50.059 | 32.715 | 0.570 | 1.00 | 32.42 | B | N |
| ATOM | 15133 | C | LYS | B | 413 | 45.152 | 27.892 | −2.505 | 1.00 | 25.95 | B | C |
| ATOM | 15134 | O | LYS | B | 413 | 45.254 | 27.868 | −3.735 | 1.00 | 26.19 | B | O |
| ATOM | 15136 | N | LYS | B | 414 | 43.983 | 27.762 | −1.874 | 1.00 | 25.87 | B | N |
| ATOM | 15137 | CA | LYS | B | 414 | 42.731 | 27.596 | −2.619 | 1.00 | 25.83 | B | C |
| ATOM | 15139 | CB | LYS | B | 414 | 41.512 | 27.515 | −1.691 | 1.00 | 26.36 | B | C |
| ATOM | 15142 | CG | LYS | B | 414 | 40.168 | 27.499 | −2.450 | 1.00 | 27.62 | B | C |

TABLE 8-2-continued

Coordinates for L494P Structure

| ATOM | 15145 | CD | LYS | B | 414 | 38.978 | 27.133 | -1.562 | 1.00 | 28.07 | B | C |
|---|---|---|---|---|---|---|---|---|---|---|---|---|
| ATOM | 15148 | CE | LYS | B | 414 | 38.690 | 28.200 | -0.508 | 1.00 | 28.15 | B | C |
| ATOM | 15151 | NZ | LYS | B | 414 | 38.573 | 29.575 | -1.081 | 1.00 | 27.51 | B | N |
| ATOM | 15155 | C | LYS | B | 414 | 42.547 | 28.730 | -3.622 | 1.00 | 25.45 | B | C |
| ATOM | 15156 | O | LYS | B | 414 | 42.039 | 28.512 | -4.721 | 1.00 | 25.62 | B | O |
| ATOM | 15158 | N | GLU | B | 415 | 42.958 | 29.936 | -3.235 | 1.00 | 24.98 | B | N |
| ATOM | 15159 | CA | GLU | B | 415 | 42.926 | 31.092 | -4.133 | 1.00 | 24.62 | B | C |
| ATOM | 15161 | CB | GLU | B | 415 | 43.333 | 32.377 | -3.388 | 1.00 | 24.74 | B | C |
| ATOM | 15164 | CG | GLU | B | 415 | 44.180 | 33.364 | -4.212 | 1.00 | 25.93 | B | C |
| ATOM | 15167 | CD | GLU | B | 415 | 43.994 | 34.813 | -3.804 | 1.00 | 26.17 | B | C |
| ATOM | 15168 | OE1 | GLU | B | 415 | 43.609 | 35.076 | -2.646 | 1.00 | 28.18 | B | O |
| ATOM | 15169 | OE2 | GLU | B | 415 | 44.241 | 35.695 | -4.655 | 1.00 | 26.04 | B | O |
| ATOM | 15170 | C | GLU | B | 415 | 43.788 | 30.877 | -5.386 | 1.00 | 23.90 | B | C |
| ATOM | 15171 | O | GLU | B | 415 | 43.367 | 31.210 | -6.495 | 1.00 | 23.91 | B | O |
| ATOM | 15173 | N | GLU | B | 416 | 44.986 | 30.326 | -5.209 | 1.00 | 23.17 | B | N |
| ATOM | 15174 | CA | GLU | B | 416 | 45.878 | 30.058 | -6.338 | 1.00 | 22.78 | B | C |
| ATOM | 15176 | CB | GLU | B | 416 | 47.261 | 29.608 | -5.855 | 1.00 | 23.14 | B | C |
| ATOM | 15179 | CG | GLU | B | 416 | 48.181 | 30.755 | -5.454 | 1.00 | 23.54 | B | C |
| ATOM | 15182 | CD | GLU | B | 416 | 49.543 | 30.288 | -4.962 | 1.00 | 24.77 | B | C |
| ATOM | 15183 | OE1 | GLU | B | 416 | 49.646 | 29.171 | -4.411 | 1.00 | 24.46 | B | O |
| ATOM | 15184 | OE2 | GLU | B | 416 | 50.518 | 31.050 | -5.120 | 1.00 | 26.91 | B | O |
| ATOM | 15185 | C | GLU | B | 416 | 45.285 | 29.017 | -7.284 | 1.00 | 22.07 | B | C |
| ATOM | 15186 | O | GLU | B | 416 | 45.196 | 29.253 | -8.490 | 1.00 | 21.50 | B | O |
| ATOM | 15188 | N | ILE | B | 417 | 44.874 | 27.875 | -6.737 | 1.00 | 21.72 | B | N |
| ATOM | 15189 | CA | ILE | B | 417 | 44.253 | 26.822 | -7.551 | 1.00 | 22.01 | B | C |
| ATOM | 15191 | CB | ILE | B | 417 | 44.108 | 25.472 | -6.790 | 1.00 | 22.11 | B | C |
| ATOM | 15193 | CG1 | ILE | B | 417 | 43.194 | 25.610 | -5.576 | 1.00 | 22.41 | B | C |
| ATOM | 15196 | CD1 | ILE | B | 417 | 43.202 | 24.395 | -4.674 | 1.00 | 23.93 | B | C |
| ATOM | 15200 | CG2 | ILE | B | 417 | 45.473 | 24.951 | -6.362 | 1.00 | 22.61 | B | C |
| ATOM | 15204 | C | ILE | B | 417 | 42.898 | 27.249 | -8.132 | 1.00 | 22.01 | B | C |
| ATOM | 15205 | O | ILE | B | 417 | 42.449 | 26.680 | -9.127 | 1.00 | 21.57 | B | O |
| ATOM | 15207 | N | GLU | B | 418 | 42.256 | 28.241 | -7.512 | 1.00 | 22.40 | B | N |
| ATOM | 15208 | CA | GLU | B | 418 | 41.029 | 28.841 | -8.064 | 1.00 | 22.66 | B | C |
| ATOM | 15210 | CB | GLU | B | 418 | 40.379 | 29.814 | -7.068 | 1.00 | 22.95 | B | C |
| ATOM | 15213 | CG | GLU | B | 418 | 39.241 | 29.216 | -6.250 | 1.00 | 24.26 | B | C |
| ATOM | 15216 | CD | GLU | B | 418 | 38.507 | 30.261 | -5.428 | 1.00 | 26.39 | B | C |
| ATOM | 15217 | OE1 | GLU | B | 418 | 39.152 | 31.244 | -5.003 | 1.00 | 26.91 | B | O |
| ATOM | 15218 | OE2 | GLU | B | 418 | 37.287 | 30.099 | -5.207 | 1.00 | 27.64 | B | O |
| ATOM | 15219 | C | GLU | B | 418 | 41.288 | 29.568 | -9.384 | 1.00 | 22.19 | B | C |
| ATOM | 15220 | O | GLU | B | 418 | 40.467 | 29.507 | -10.302 | 1.00 | 22.03 | B | O |
| ATOM | 15222 | N | ASN | B | 419 | 42.419 | 30.263 | -9.468 | 1.00 | 21.74 | B | N |
| ATOM | 15223 | CA | ASN | B | 419 | 42.819 | 30.931 | -10.704 | 1.00 | 21.85 | B | C |
| ATOM | 15225 | CB | ASN | B | 419 | 43.803 | 32.069 | -10.409 | 1.00 | 21.97 | B | C |
| ATOM | 15228 | CG | ASN | B | 419 | 43.112 | 33.305 | -9.840 | 1.00 | 22.96 | B | C |
| ATOM | 15229 | OD1 | ASN | B | 419 | 42.276 | 33.922 | -10.503 | 1.00 | 24.59 | B | O |
| ATOM | 15230 | ND2 | ASN | B | 419 | 43.462 | 33.670 | -8.609 | 1.00 | 22.29 | B | N |
| ATOM | 15233 | C | ASN | B | 419 | 43.392 | 29.954 | -11.739 | 1.00 | 21.82 | B | C |
| ATOM | 15234 | O | ASN | B | 419 | 43.309 | 30.208 | -12.942 | 1.00 | 21.68 | B | O |
| ATOM | 15236 | N | LEU | B | 420 | 43.961 | 28.840 | -11.271 | 1.00 | 21.94 | B | N |
| ATOM | 15237 | CA | LEU | B | 420 | 44.408 | 27.760 | -12.166 | 1.00 | 21.70 | B | C |
| ATOM | 15239 | CB | LEU | B | 420 | 45.147 | 26.654 | -11.400 | 1.00 | 21.08 | B | C |
| ATOM | 15242 | CG | LEU | B | 420 | 46.618 | 26.901 | -11.057 | 1.00 | 20.18 | B | C |
| ATOM | 15244 | CD1 | LEU | B | 420 | 47.124 | 25.869 | -10.057 | 1.00 | 18.62 | B | C |
| ATOM | 15248 | CD2 | LEU | B | 420 | 47.477 | 26.901 | -12.313 | 1.00 | 17.37 | B | C |
| ATOM | 15252 | C | LEU | B | 420 | 43.228 | 27.145 | -12.903 | 1.00 | 22.21 | B | C |
| ATOM | 15253 | O | LEU | B | 420 | 43.283 | 26.956 | -14.118 | 1.00 | 22.19 | B | O |
| ATOM | 15255 | N | GLN | B | 421 | 42.166 | 26.832 | -12.160 | 1.00 | 22.92 | B | N |
| ATOM | 15256 | CA | GLN | B | 421 | 40.958 | 26.240 | -12.739 | 1.00 | 23.57 | B | C |
| ATOM | 15258 | CB | GLN | B | 421 | 39.911 | 25.943 | -11.656 | 1.00 | 24.09 | B | C |
| ATOM | 15261 | CG | GLN | B | 421 | 40.296 | 24.803 | -10.706 | 1.00 | 26.83 | B | C |
| ATOM | 15264 | CD | GLN | B | 421 | 39.112 | 23.933 | -10.302 | 1.00 | 29.79 | B | C |
| ATOM | 15265 | OE1 | GLN | B | 421 | 39.061 | 22.742 | -10.627 | 1.00 | 31.64 | B | O |
| ATOM | 15266 | NE2 | GLN | B | 421 | 38.151 | 24.525 | -9.597 | 1.00 | 29.87 | B | N |
| ATOM | 15269 | C | GLN | B | 421 | 40.351 | 27.135 | -13.812 | 1.00 | 23.57 | B | C |
| ATOM | 15270 | O | GLN | B | 421 | 39.842 | 26.637 | -14.815 | 1.00 | 23.53 | B | O |
| ATOM | 15272 | N | LYS | B | 422 | 40.430 | 28.451 | -13.605 | 1.00 | 24.03 | B | N |
| ATOM | 15273 | CA | LYS | B | 422 | 39.860 | 29.436 | -14.534 | 1.00 | 24.54 | B | C |
| ATOM | 15275 | CB | LYS | B | 422 | 39.330 | 30.643 | -13.747 | 1.00 | 24.69 | B | C |
| ATOM | 15278 | CG | LYS | B | 422 | 38.068 | 30.312 | -12.950 | 1.00 | 27.40 | B | C |
| ATOM | 15281 | CD | LYS | B | 422 | 37.853 | 31.231 | -11.748 | 1.00 | 30.16 | B | C |
| ATOM | 15284 | CE | LYS | B | 422 | 36.737 | 30.695 | -10.844 | 1.00 | 30.51 | B | C |
| ATOM | 15287 | NZ | LYS | B | 422 | 36.523 | 31.525 | -9.621 | 1.00 | 30.84 | B | N |
| ATOM | 15291 | C | LYS | B | 422 | 40.832 | 29.882 | -15.638 | 1.00 | 24.42 | B | C |
| ATOM | 15292 | O | LYS | B | 422 | 40.546 | 30.833 | -16.366 | 1.00 | 24.81 | B | O |
| ATOM | 15294 | N | TYR | B | 423 | 41.960 | 29.182 | -15.770 | 1.00 | 24.16 | B | N |
| ATOM | 15295 | CA | TYR | B | 423 | 42.965 | 29.458 | -16.803 | 1.00 | 23.64 | B | C |
| ATOM | 15297 | CB | TYR | B | 423 | 42.480 | 28.982 | -18.182 | 1.00 | 23.69 | B | C |
| ATOM | 15300 | CG | TYR | B | 423 | 42.338 | 27.472 | -18.292 | 1.00 | 24.59 | B | C |

TABLE 8-2-continued

Coordinates for L494P Structure

| ATOM | 15301 | CD1 | TYR | B | 423 | 43.353 | 26.622 | −17.849 | 1.00 | 25.56 | B | C |
|---|---|---|---|---|---|---|---|---|---|---|---|---|
| ATOM | 15303 | CE1 | TYR | B | 423 | 43.233 | 25.243 | −17.942 | 1.00 | 25.98 | B | C |
| ATOM | 15305 | CZ | TYR | B | 423 | 42.096 | 24.691 | −18.492 | 1.00 | 26.45 | B | C |
| ATOM | 15306 | OH | TYR | B | 423 | 41.994 | 23.323 | −18.576 | 1.00 | 26.60 | B | O |
| ATOM | 15308 | CE2 | TYR | B | 423 | 41.073 | 25.506 | −18.948 | 1.00 | 26.05 | B | C |
| ATOM | 15310 | CD2 | TYR | B | 423 | 41.200 | 26.892 | −18.848 | 1.00 | 25.18 | B | C |
| ATOM | 15312 | C | TYR | B | 423 | 43.372 | 30.927 | −16.826 | 1.00 | 23.30 | B | C |
| ATOM | 15313 | O | TYR | B | 423 | 43.079 | 31.657 | −17.773 | 1.00 | 23.79 | B | O |
| ATOM | 15315 | N | HIS | B | 424 | 44.058 | 31.333 | −15.762 | 1.00 | 22.79 | B | N |
| ATOM | 15316 | CA | HIS | B | 424 | 44.483 | 32.715 | −15.553 | 1.00 | 22.25 | B | C |
| ATOM | 15318 | CB | HIS | B | 424 | 44.798 | 32.915 | −14.065 | 1.00 | 22.47 | B | C |
| ATOM | 15321 | CG | HIS | B | 424 | 45.182 | 34.313 | −13.699 | 1.00 | 23.17 | B | C |
| ATOM | 15322 | ND1 | HIS | B | 424 | 46.491 | 34.738 | −13.664 | 1.00 | 22.23 | B | N |
| ATOM | 15324 | CE1 | HIS | B | 424 | 46.531 | 36.009 | −13.308 | 1.00 | 22.45 | B | C |
| ATOM | 15326 | NE2 | HIS | B | 424 | 45.294 | 36.424 | −13.106 | 1.00 | 23.39 | B | N |
| ATOM | 15328 | CD2 | HIS | B | 424 | 44.430 | 35.381 | −13.342 | 1.00 | 23.99 | B | C |
| ATOM | 15330 | C | HIS | B | 424 | 45.701 | 33.058 | −16.415 | 1.00 | 21.56 | B | C |
| ATOM | 15331 | O | HIS | B | 424 | 46.434 | 32.167 | −16.845 | 1.00 | 21.55 | B | O |
| ATOM | 15333 | N | ASP | B | 425 | 45.898 | 34.354 | −16.659 | 1.00 | 21.01 | B | N |
| ATOM | 15334 | CA | ASP | B | 425 | 47.006 | 34.875 | −17.482 | 1.00 | 20.76 | B | C |
| ATOM | 15336 | CB | ASP | B | 425 | 47.157 | 36.385 | −17.267 | 1.00 | 20.81 | B | C |
| ATOM | 15339 | CG | ASP | B | 425 | 45.982 | 37.171 | −17.801 | 1.00 | 21.95 | B | C |
| ATOM | 15340 | OD1 | ASP | B | 425 | 45.764 | 37.140 | −19.030 | 1.00 | 23.03 | B | O |
| ATOM | 15341 | OD2 | ASP | B | 425 | 45.281 | 37.822 | −16.994 | 1.00 | 22.61 | B | O |
| ATOM | 15342 | C | ASP | B | 425 | 48.365 | 34.217 | −17.228 | 1.00 | 20.21 | B | C |
| ATOM | 15343 | O | ASP | B | 425 | 49.082 | 33.880 | −18.172 | 1.00 | 20.00 | B | O |
| ATOM | 15345 | N | THR | B | 426 | 48.711 | 34.052 | −15.952 | 1.00 | 19.50 | B | N |
| ATOM | 15346 | CA | THR | B | 426 | 50.011 | 33.510 | −15.545 | 1.00 | 18.64 | B | C |
| ATOM | 15348 | CB | THR | B | 426 | 50.061 | 33.267 | −14.021 | 1.00 | 18.27 | B | C |
| ATOM | 15350 | OG1 | THR | B | 426 | 50.051 | 34.525 | −13.335 | 1.00 | 17.93 | B | O |
| ATOM | 15352 | CG2 | THR | B | 426 | 51.313 | 32.502 | −13.632 | 1.00 | 17.94 | B | C |
| ATOM | 15356 | C | THR | B | 426 | 50.362 | 32.216 | −16.278 | 1.00 | 18.30 | B | C |
| ATOM | 15357 | O | THR | B | 426 | 51.519 | 32.012 | −16.657 | 1.00 | 18.29 | B | O |
| ATOM | 15359 | N | ILE | B | 427 | 49.364 | 31.355 | −16.479 | 1.00 | 17.83 | B | N |
| ATOM | 15360 | CA | ILE | B | 427 | 49.556 | 30.106 | −17.222 | 1.00 | 17.71 | B | C |
| ATOM | 15362 | CB | ILE | B | 427 | 48.948 | 28.885 | −16.472 | 1.00 | 17.30 | B | C |
| ATOM | 15364 | CG1 | ILE | B | 427 | 47.417 | 28.906 | −16.489 | 1.00 | 16.67 | B | C |
| ATOM | 15367 | CD1 | ILE | B | 427 | 46.803 | 27.717 | −15.792 | 1.00 | 15.11 | B | C |
| ATOM | 15371 | CG2 | ILE | B | 427 | 49.449 | 28.846 | −15.039 | 1.00 | 16.16 | B | C |
| ATOM | 15375 | C | ILE | B | 427 | 49.025 | 30.172 | −18.663 | 1.00 | 18.09 | B | C |
| ATOM | 15376 | O | ILE | B | 427 | 49.557 | 29.498 | −19.547 | 1.00 | 17.89 | B | O |
| ATOM | 15378 | N | SER | B | 428 | 47.997 | 30.985 | −18.904 | 1.00 | 18.49 | B | N |
| ATOM | 15379 | CA | SER | B | 428 | 47.379 | 31.056 | −20.232 | 1.00 | 18.89 | B | C |
| ATOM | 15381 | CB | SER | B | 428 | 46.036 | 31.794 | −20.180 | 1.00 | 19.00 | B | C |
| ATOM | 15384 | OG | SER | B | 428 | 46.211 | 33.200 | −20.223 | 1.00 | 19.67 | B | O |
| ATOM | 15386 | C | SER | B | 428 | 48.296 | 31.721 | −21.255 | 1.00 | 19.28 | B | C |
| ATOM | 15387 | O | SER | B | 428 | 48.416 | 31.245 | −22.382 | 1.00 | 19.91 | B | O |
| ATOM | 15389 | N | ARG | B | 429 | 48.940 | 32.818 | −20.858 | 1.00 | 19.47 | B | N |
| ATOM | 15390 | CA | ARG | B | 429 | 49.798 | 33.597 | −21.763 | 1.00 | 19.36 | B | C |
| ATOM | 15392 | CB | ARG | B | 429 | 50.349 | 34.838 | −21.056 | 1.00 | 19.70 | B | C |
| ATOM | 15395 | CG | ARG | B | 429 | 49.283 | 35.843 | −20.642 | 1.00 | 22.63 | B | C |
| ATOM | 15398 | CD | ARG | B | 429 | 49.315 | 37.104 | −21.490 | 1.00 | 25.32 | B | C |
| ATOM | 15401 | NE | ARG | B | 429 | 48.208 | 38.001 | −21.157 | 1.00 | 26.37 | B | N |
| ATOM | 15403 | CZ | ARG | B | 429 | 47.010 | 37.998 | −21.745 | 1.00 | 27.17 | B | C |
| ATOM | 15404 | NH1 | ARG | B | 429 | 46.725 | 37.144 | −22.725 | 1.00 | 26.90 | B | N |
| ATOM | 15407 | NH2 | ARG | B | 429 | 46.084 | 38.865 | −21.349 | 1.00 | 28.32 | B | N |
| ATOM | 15410 | C | ARG | B | 429 | 50.948 | 32.784 | −22.364 | 1.00 | 18.47 | B | C |
| ATOM | 15411 | O | ARG | B | 429 | 51.117 | 32.783 | −23.577 | 1.00 | 17.94 | B | O |
| ATOM | 15413 | N | PRO | B | 430 | 51.742 | 32.087 | −21.528 | 1.00 | 18.01 | B | N |
| ATOM | 15414 | CA | PRO | B | 430 | 52.794 | 31.255 | −22.123 | 1.00 | 17.76 | B | C |
| ATOM | 15416 | CB | PRO | B | 430 | 53.597 | 30.774 | −20.909 | 1.00 | 17.79 | B | C |
| ATOM | 15419 | CG | PRO | B | 430 | 52.661 | 30.880 | −19.766 | 1.00 | 18.19 | B | C |
| ATOM | 15422 | CD | PRO | B | 430 | 51.791 | 32.058 | −20.056 | 1.00 | 17.89 | B | C |
| ATOM | 15425 | C | PRO | B | 430 | 52.255 | 30.068 | −22.933 | 1.00 | 17.32 | B | C |
| ATOM | 15426 | O | PRO | B | 430 | 52.989 | 29.504 | −23.746 | 1.00 | 17.56 | B | O |
| ATOM | 15427 | N | SER | B | 431 | 50.996 | 29.693 | −22.710 | 1.00 | 16.49 | B | N |
| ATOM | 15428 | CA | SER | B | 431 | 50.328 | 28.702 | −23.554 | 1.00 | 16.00 | B | C |
| ATOM | 15430 | CB | SER | B | 431 | 49.131 | 28.086 | −22.830 | 1.00 | 15.98 | B | C |
| ATOM | 15433 | OG | SER | B | 431 | 49.521 | 27.553 | −21.578 | 1.00 | 15.79 | B | O |
| ATOM | 15435 | C | SER | B | 431 | 49.896 | 29.310 | −24.895 | 1.00 | 15.50 | B | C |
| ATOM | 15436 | O | SER | B | 431 | 49.769 | 28.595 | −25.890 | 1.00 | 15.19 | B | O |
| ATOM | 15438 | N | HIS | B | 432 | 49.662 | 30.623 | −24.919 | 1.00 | 15.14 | B | N |
| ATOM | 15439 | CA | HIS | B | 432 | 49.510 | 31.350 | −26.183 | 1.00 | 14.91 | B | C |
| ATOM | 15441 | CB | HIS | B | 432 | 49.203 | 32.841 | −25.952 | 1.00 | 14.78 | B | C |
| ATOM | 15444 | CG | HIS | B | 432 | 47.812 | 33.122 | −25.471 | 1.00 | 14.57 | B | C |
| ATOM | 15445 | ND1 | HIS | B | 432 | 47.099 | 32.248 | −24.679 | 1.00 | 15.65 | B | N |
| ATOM | 15447 | CE1 | HIS | B | 432 | 45.914 | 32.766 | −24.408 | 1.00 | 14.74 | B | C |
| ATOM | 15449 | NE2 | HIS | B | 432 | 45.836 | 33.951 | −24.985 | 1.00 | 13.39 | B | N |

TABLE 8-2-continued

| | | | | | Coordinates for L494P Structure | | | | | | |
|---|---|---|---|---|---|---|---|---|---|---|---|
| ATOM | 15451 | CD2 | HIS | B | 432 | 47.013 | 34.200 | −25.650 | 1.00 | 14.77 B | C |
| ATOM | 15453 | C | HIS | B | 432 | 50.807 | 31.224 | −26.984 | 1.00 | 14.58 B | C |
| ATOM | 15454 | O | HIS | B | 432 | 50.786 | 30.909 | −28.172 | 1.00 | 14.38 B | O |
| ATOM | 15456 | N | ILE | B | 433 | 51.931 | 31.455 | −26.307 | 1.00 | 14.30 B | N |
| ATOM | 15457 | CA | ILE | B | 433 | 53.258 | 31.391 | −26.919 | 1.00 | 13.69 B | C |
| ATOM | 15459 | CB | ILE | B | 433 | 54.357 | 31.939 | −25.968 | 1.00 | 13.55 B | C |
| ATOM | 15461 | CG1 | ILE | B | 433 | 54.064 | 33.386 | −25.550 | 1.00 | 13.14 B | C |
| ATOM | 15464 | CD1 | ILE | B | 433 | 54.088 | 34.380 | −26.682 | 1.00 | 11.73 B | C |
| ATOM | 15468 | CG2 | ILE | B | 433 | 55.734 | 31.857 | −26.623 | 1.00 | 13.05 B | C |
| ATOM | 15472 | C | ILE | B | 433 | 53.627 | 29.958 | −27.303 | 1.00 | 13.75 B | C |
| ATOM | 15473 | O | ILE | B | 433 | 54.393 | 29.743 | −28.240 | 1.00 | 14.58 B | O |
| ATOM | 15475 | N | PHE | B | 434 | 53.088 | 28.982 | −26.578 | 1.00 | 13.11 B | N |
| ATOM | 15476 | CA | PHE | B | 434 | 53.363 | 27.570 | −26.851 | 1.00 | 12.79 B | C |
| ATOM | 15478 | CB | PHE | B | 434 | 52.916 | 26.726 | −25.648 | 1.00 | 12.75 B | C |
| ATOM | 15481 | CG | PHE | B | 434 | 53.066 | 25.231 | −25.822 | 1.00 | 13.16 B | C |
| ATOM | 15482 | CD1 | PHE | B | 434 | 53.915 | 24.668 | −26.771 | 1.00 | 13.37 B | C |
| ATOM | 15484 | CE1 | PHE | B | 434 | 54.026 | 23.285 | −26.894 | 1.00 | 13.68 B | C |
| ATOM | 15486 | CZ | PHE | B | 434 | 53.311 | 22.454 | −26.049 | 1.00 | 12.83 B | C |
| ATOM | 15488 | CE2 | PHE | B | 434 | 52.482 | 23.002 | −25.092 | 1.00 | 13.60 B | C |
| ATOM | 15490 | CD2 | PHE | B | 434 | 52.367 | 24.379 | −24.978 | 1.00 | 14.39 B | C |
| ATOM | 15492 | C | PHE | B | 434 | 52.689 | 27.132 | −28.153 | 1.00 | 12.75 B | C |
| ATOM | 15493 | O | PHE | B | 434 | 53.341 | 26.578 | −29.036 | 1.00 | 12.94 B | O |
| ATOM | 15495 | N | ARG | B | 435 | 51.397 | 27.409 | −28.278 | 1.00 | 12.65 B | N |
| ATOM | 15496 | CA | ARG | B | 435 | 50.647 | 27.077 | −29.490 | 1.00 | 12.43 B | C |
| ATOM | 15498 | CB | ARG | B | 435 | 49.146 | 27.269 | −29.238 | 1.00 | 12.62 B | C |
| ATOM | 15501 | CG | ARG | B | 435 | 48.244 | 27.150 | −30.463 | 1.00 | 13.62 B | C |
| ATOM | 15504 | CD | ARG | B | 435 | 48.426 | 25.839 | −31.211 | 1.00 | 15.01 B | C |
| ATOM | 15507 | NE | ARG | B | 435 | 48.056 | 24.675 | −30.411 | 1.00 | 15.74 B | N |
| ATOM | 15509 | CZ | ARG | B | 435 | 48.332 | 23.415 | −30.739 | 1.00 | 17.48 B | C |
| ATOM | 15510 | NH1 | ARG | B | 435 | 48.997 | 23.124 | −31.856 | 1.00 | 18.48 B | N |
| ATOM | 15513 | NH2 | ARG | B | 435 | 47.948 | 22.434 | −29.936 | 1.00 | 18.57 B | N |
| ATOM | 15516 | C | ARG | B | 435 | 51.098 | 27.898 | −30.708 | 1.00 | 12.48 B | C |
| ATOM | 15517 | O | ARG | B | 435 | 51.168 | 27.370 | −31.817 | 1.00 | 12.61 B | O |
| ATOM | 15519 | N | LEU | B | 436 | 51.401 | 29.180 | −30.504 | 1.00 | 12.45 B | N |
| ATOM | 15520 | CA | LEU | B | 436 | 51.812 | 30.060 | −31.606 | 1.00 | 12.32 B | C |
| ATOM | 15522 | CB | LEU | B | 436 | 51.884 | 31.521 | −31.153 | 1.00 | 12.22 B | C |
| ATOM | 15525 | CG | LEU | B | 436 | 50.576 | 32.303 | −31.063 | 1.00 | 11.85 B | C |
| ATOM | 15527 | CD1 | LEU | B | 436 | 50.876 | 33.761 | −30.737 | 1.00 | 12.49 B | C |
| ATOM | 15531 | CD2 | LEU | B | 436 | 49.782 | 32.196 | −32.351 | 1.00 | 11.29 B | C |
| ATOM | 15535 | C | LEU | B | 436 | 53.153 | 29.669 | −32.225 | 1.00 | 12.83 B | C |
| ATOM | 15536 | O | LEU | B | 436 | 53.335 | 29.800 | −33.433 | 1.00 | 12.98 B | O |
| ATOM | 15538 | N | CYS | B | 437 | 54.093 | 29.214 | −31.402 | 1.00 | 13.39 B | N |
| ATOM | 15539 | CA | CYS | B | 437 | 55.387 | 28.759 | −31.903 | 1.00 | 13.88 B | C |
| ATOM | 15541 | CB | CYS | B | 437 | 56.381 | 28.581 | −30.753 | 1.00 | 13.94 B | C |
| ATOM | 15544 | SG | CYS | B | 437 | 56.826 | 30.125 | −29.910 | 1.00 | 15.60 B | S |
| ATOM | 15546 | C | CYS | B | 437 | 55.219 | 27.449 | −32.668 | 1.00 | 14.16 B | C |
| ATOM | 15547 | O | CYS | B | 437 | 55.625 | 27.343 | −33.825 | 1.00 | 14.34 B | O |
| ATOM | 15549 | N | ASN | B | 438 | 54.602 | 26.466 | −32.014 | 1.00 | 14.40 B | N |
| ATOM | 15550 | CA | ASN | B | 438 | 54.336 | 25.156 | −32.612 | 1.00 | 14.88 B | C |
| ATOM | 15552 | CB | ASN | B | 438 | 53.450 | 24.324 | −31.674 | 1.00 | 15.18 B | C |
| ATOM | 15555 | CG | ASN | B | 438 | 52.919 | 23.050 | −32.324 | 1.00 | 16.21 B | C |
| ATOM | 15556 | OD1 | ASN | B | 438 | 51.766 | 22.669 | −32.104 | 1.00 | 17.51 B | O |
| ATOM | 15557 | ND2 | ASN | B | 438 | 53.754 | 22.387 | −33.122 | 1.00 | 16.34 B | N |
| ATOM | 15560 | C | ASN | B | 438 | 53.687 | 25.252 | −33.991 | 1.00 | 14.99 B | C |
| ATOM | 15561 | O | ASN | B | 438 | 54.140 | 24.613 | −34.941 | 1.00 | 15.21 B | O |
| ATOM | 15563 | N | ASP | B | 439 | 52.623 | 26.042 | −34.091 | 1.00 | 15.13 B | N |
| ATOM | 15564 | CA | ASP | B | 439 | 51.912 | 26.202 | −35.358 | 1.00 | 15.33 B | C |
| ATOM | 15566 | CB | ASP | B | 439 | 50.546 | 26.880 | −35.147 | 1.00 | 15.20 B | C |
| ATOM | 15569 | CG | ASP | B | 439 | 49.512 | 25.946 | −34.501 | 1.00 | 14.78 B | C |
| ATOM | 15570 | OD1 | ASP | B | 439 | 49.909 | 24.940 | −33.876 | 1.00 | 13.59 B | O |
| ATOM | 15571 | OD2 | ASP | B | 439 | 48.295 | 26.218 | −34.619 | 1.00 | 13.26 B | O |
| ATOM | 15572 | C | ASP | B | 439 | 52.767 | 26.968 | −36.374 | 1.00 | 15.73 B | C |
| ATOM | 15573 | O | ASP | B | 439 | 52.689 | 26.698 | −37.574 | 1.00 | 15.79 B | O |
| ATOM | 15575 | N | LEU | B | 440 | 53.587 | 27.904 | −35.892 | 1.00 | 16.14 B | N |
| ATOM | 15576 | CA | LEU | B | 440 | 54.514 | 28.640 | −36.761 | 1.00 | 16.51 B | C |
| ATOM | 15578 | CB | LEU | B | 440 | 55.158 | 29.824 | −36.031 | 1.00 | 16.13 B | C |
| ATOM | 15581 | CG | LEU | B | 440 | 54.414 | 31.156 | −36.092 | 1.00 | 15.62 B | C |
| ATOM | 15583 | CD1 | LEU | B | 440 | 55.083 | 32.170 | −35.174 | 1.00 | 15.61 B | C |
| ATOM | 15587 | CD2 | LEU | B | 440 | 54.358 | 31.676 | −37.520 | 1.00 | 14.42 B | C |
| ATOM | 15591 | C | LEU | B | 440 | 55.611 | 27.737 | −37.316 | 1.00 | 17.37 B | C |
| ATOM | 15592 | O | LEU | B | 440 | 56.085 | 27.949 | −38.432 | 1.00 | 18.00 B | O |
| ATOM | 15594 | N | ALA | B | 441 | 56.017 | 26.742 | −36.534 | 1.00 | 18.07 B | N |
| ATOM | 15595 | CA | ALA | B | 441 | 57.053 | 25.804 | −36.962 | 1.00 | 18.79 B | C |
| ATOM | 15597 | CB | ALA | B | 441 | 57.436 | 24.880 | −35.814 | 1.00 | 18.94 B | C |
| ATOM | 15601 | C | ALA | B | 441 | 56.608 | 24.984 | −38.173 | 1.00 | 19.39 B | C |
| ATOM | 15602 | O | ALA | B | 441 | 57.367 | 24.821 | −39.130 | 1.00 | 19.34 B | O |
| ATOM | 15604 | N | SER | B | 442 | 55.372 | 24.488 | −38.129 | 1.00 | 20.04 B | N |
| ATOM | 15605 | CA | SER | B | 442 | 54.835 | 23.620 | −39.178 | 1.00 | 20.72 B | C |

TABLE 8-2-continued

Coordinates for L494P Structure

| ATOM | 15607 | CB | SER | B | 442 | 54.010 | 22.503 | −38.537 | 1.00 | 20.68 | B | C |
|---|---|---|---|---|---|---|---|---|---|---|---|---|
| ATOM | 15610 | OG | SER | B | 442 | 52.872 | 23.030 | −37.876 | 1.00 | 21.27 | B | O |
| ATOM | 15612 | C | SER | B | 442 | 53.970 | 24.359 | −40.208 | 1.00 | 21.39 | B | C |
| ATOM | 15613 | O | SER | B | 442 | 53.341 | 23.722 | −41.055 | 1.00 | 21.51 | B | O |
| ATOM | 15615 | N | ALA | B | 443 | 53.953 | 25.690 | −40.147 | 1.00 | 22.14 | B | N |
| ATOM | 15616 | CA | ALA | B | 443 | 53.036 | 26.503 | −40.957 | 1.00 | 22.64 | B | C |
| ATOM | 15618 | CB | ALA | B | 443 | 53.249 | 27.988 | −40.666 | 1.00 | 22.67 | B | C |
| ATOM | 15622 | C | ALA | B | 443 | 53.139 | 26.241 | −42.463 | 1.00 | 22.85 | B | C |
| ATOM | 15623 | O | ALA | B | 443 | 52.206 | 25.712 | −43.068 | 1.00 | 22.40 | B | O |
| ATOM | 15625 | N | SER | B | 444 | 54.274 | 26.603 | −43.056 | 1.00 | 23.46 | B | N |
| ATOM | 15626 | CA | SER | B | 444 | 54.460 | 26.513 | −44.509 | 1.00 | 24.13 | B | C |
| ATOM | 15628 | CB | SER | B | 444 | 55.851 | 27.015 | −44.903 | 1.00 | 24.32 | B | C |
| ATOM | 15631 | OG | SER | B | 444 | 56.864 | 26.161 | −44.398 | 1.00 | 25.37 | B | O |
| ATOM | 15633 | C | SER | B | 444 | 54.251 | 25.097 | −45.053 | 1.00 | 24.33 | B | C |
| ATOM | 15634 | O | SER | B | 444 | 53.795 | 24.925 | −46.184 | 1.00 | 24.33 | B | O |
| ATOM | 15636 | N | ALA | B | 445 | 54.595 | 24.093 | −44.249 | 1.00 | 24.60 | B | N |
| ATOM | 15637 | CA | ALA | B | 445 | 54.375 | 22.696 | −44.615 | 1.00 | 24.55 | B | C |
| ATOM | 15639 | CB | ALA | B | 445 | 55.038 | 21.770 | −43.601 | 1.00 | 24.40 | B | C |
| ATOM | 15643 | C | ALA | B | 445 | 52.881 | 22.400 | −44.706 | 1.00 | 24.64 | B | C |
| ATOM | 15644 | O | ALA | B | 445 | 52.380 | 22.032 | −45.767 | 1.00 | 24.53 | B | O |
| ATOM | 15646 | N | GLU | B | 446 | 52.176 | 22.587 | −43.593 | 1.00 | 24.83 | B | N |
| ATOM | 15647 | CA | GLU | B | 446 | 50.743 | 22.289 | −43.516 | 1.00 | 25.12 | B | C |
| ATOM | 15649 | CB | GLU | B | 446 | 50.230 | 22.457 | −42.075 | 1.00 | 25.24 | B | C |
| ATOM | 15652 | CG | GLU | B | 446 | 50.805 | 21.427 | −41.088 | 1.00 | 26.42 | B | C |
| ATOM | 15655 | CD | GLU | B | 446 | 50.271 | 21.565 | −39.660 | 1.00 | 27.29 | B | C |
| ATOM | 15656 | OE1 | GLU | B | 446 | 49.633 | 22.589 | −39.336 | 1.00 | 29.11 | B | O |
| ATOM | 15657 | OE2 | GLU | B | 446 | 50.500 | 20.638 | −38.853 | 1.00 | 26.37 | B | O |
| ATOM | 15658 | C | GLU | B | 446 | 49.912 | 23.137 | −44.488 | 1.00 | 25.03 | B | C |
| ATOM | 15659 | O | GLU | B | 446 | 48.903 | 22.667 | −45.013 | 1.00 | 25.21 | B | O |
| ATOM | 15661 | N | ILE | B | 447 | 50.343 | 24.373 | −44.734 | 1.00 | 24.84 | B | N |
| ATOM | 15662 | CA | ILE | B | 447 | 49.633 | 25.274 | −45.647 | 1.00 | 24.77 | B | C |
| ATOM | 15664 | CB | ILE | B | 447 | 50.218 | 26.709 | −45.600 | 1.00 | 24.76 | B | C |
| ATOM | 15666 | CG1 | ILE | B | 447 | 49.850 | 27.386 | −44.276 | 1.00 | 24.75 | B | C |
| ATOM | 15669 | CD1 | ILE | B | 447 | 50.783 | 28.510 | −43.879 | 1.00 | 24.00 | B | C |
| ATOM | 15673 | CG2 | ILE | B | 447 | 49.706 | 27.547 | −46.771 | 1.00 | 23.20 | B | C |
| ATOM | 15677 | C | ILE | B | 447 | 49.653 | 24.752 | −47.085 | 1.00 | 25.09 | B | C |
| ATOM | 15678 | O | ILE | B | 447 | 48.612 | 24.699 | −47.742 | 1.00 | 25.20 | B | O |
| ATOM | 15680 | N | ALA | B | 448 | 50.835 | 24.358 | −47.560 | 1.00 | 25.30 | B | N |
| ATOM | 15681 | CA | ALA | B | 448 | 51.005 | 23.871 | −48.935 | 1.00 | 25.10 | B | C |
| ATOM | 15683 | CB | ALA | B | 448 | 52.485 | 23.792 | −49.294 | 1.00 | 24.84 | B | C |
| ATOM | 15687 | C | ALA | B | 448 | 50.323 | 22.521 | −49.183 | 1.00 | 25.08 | B | C |
| ATOM | 15688 | O | ALA | B | 448 | 50.005 | 22.192 | −50.324 | 1.00 | 25.19 | B | O |
| ATOM | 15690 | N | ARG | B | 449 | 50.106 | 21.745 | −48.121 | 1.00 | 25.21 | B | N |
| ATOM | 15691 | CA | ARG | B | 449 | 49.342 | 20.495 | −48.214 | 1.00 | 25.32 | B | C |
| ATOM | 15693 | CB | ARG | B | 449 | 49.540 | 19.636 | −46.964 | 1.00 | 25.46 | B | C |
| ATOM | 15696 | CG | ARG | B | 449 | 50.959 | 19.185 | −46.680 | 1.00 | 25.13 | B | C |
| ATOM | 15699 | CD | ARG | B | 449 | 50.986 | 18.373 | −45.391 | 1.00 | 24.41 | B | C |
| ATOM | 15702 | NE | ARG | B | 449 | 52.221 | 18.551 | −44.632 | 1.00 | 24.69 | B | N |
| ATOM | 15704 | CZ | ARG | B | 449 | 52.395 | 18.161 | −43.368 | 1.00 | 24.86 | B | C |
| ATOM | 15705 | NH1 | ARG | B | 449 | 51.412 | 17.563 | −42.698 | 1.00 | 25.32 | B | N |
| ATOM | 15708 | NH2 | ARG | B | 449 | 53.561 | 18.372 | −42.765 | 1.00 | 24.17 | B | N |
| ATOM | 15711 | C | ARG | B | 449 | 47.843 | 20.749 | −48.357 | 1.00 | 25.44 | B | C |
| ATOM | 15712 | O | ARG | B | 449 | 47.103 | 19.868 | −48.793 | 1.00 | 25.60 | B | O |
| ATOM | 15714 | N | GLY | B | 450 | 47.399 | 21.940 | −47.961 | 1.00 | 25.52 | B | N |
| ATOM | 15715 | CA | GLY | B | 450 | 45.978 | 22.269 | −47.919 | 1.00 | 25.45 | B | C |
| ATOM | 15718 | C | GLY | B | 450 | 45.347 | 21.972 | −46.568 | 1.00 | 25.40 | B | C |
| ATOM | 15719 | O | GLY | B | 450 | 44.125 | 21.849 | −46.471 | 1.00 | 25.56 | B | O |
| ATOM | 15721 | N | GLU | B | 451 | 46.171 | 21.852 | −45.525 | 1.00 | 25.17 | B | N |
| ATOM | 15722 | CA | GLU | B | 451 | 45.666 | 21.675 | −44.162 | 1.00 | 25.18 | B | C |
| ATOM | 15724 | CB | GLU | B | 451 | 46.685 | 20.956 | −43.271 | 1.00 | 25.44 | B | C |
| ATOM | 15727 | CG | GLU | B | 451 | 46.811 | 19.460 | −43.546 | 1.00 | 26.78 | B | C |
| ATOM | 15730 | CD | GLU | B | 451 | 47.637 | 18.724 | −42.496 | 1.00 | 28.97 | B | C |
| ATOM | 15731 | OE1 | GLU | B | 451 | 47.800 | 19.244 | −41.368 | 1.00 | 30.01 | B | O |
| ATOM | 15732 | OE2 | GLU | B | 451 | 48.122 | 17.613 | −42.799 | 1.00 | 30.31 | B | O |
| ATOM | 15733 | C | GLU | B | 451 | 45.308 | 23.029 | −43.551 | 1.00 | 24.68 | B | C |
| ATOM | 15734 | O | GLU | B | 451 | 46.039 | 24.007 | −43.716 | 1.00 | 24.69 | B | O |
| ATOM | 15736 | N | THR | B | 452 | 44.179 | 23.069 | −42.845 | 1.00 | 24.05 | B | N |
| ATOM | 15737 | CA | THR | B | 452 | 43.680 | 24.299 | −42.223 | 1.00 | 23.13 | B | C |
| ATOM | 15739 | CB | THR | B | 452 | 42.176 | 24.536 | −42.552 | 1.00 | 23.21 | B | C |
| ATOM | 15741 | OG1 | THR | B | 452 | 41.494 | 23.281 | −42.679 | 1.00 | 22.65 | B | O |
| ATOM | 15743 | CG2 | THR | B | 452 | 42.023 | 25.322 | −43.850 | 1.00 | 22.06 | B | C |
| ATOM | 15747 | C | THR | B | 452 | 43.878 | 24.338 | −40.702 | 1.00 | 22.26 | B | C |
| ATOM | 15748 | O | THR | B | 452 | 43.816 | 25.416 | −40.107 | 1.00 | 22.08 | B | O |
| ATOM | 15750 | N | ALA | B | 453 | 44.119 | 23.182 | −40.078 | 1.00 | 21.27 | B | N |
| ATOM | 15751 | CA | ALA | B | 453 | 44.318 | 23.105 | −38.624 | 1.00 | 20.51 | B | C |
| ATOM | 15753 | CB | ALA | B | 453 | 44.174 | 21.670 | −38.137 | 1.00 | 20.50 | B | C |
| ATOM | 15757 | C | ALA | B | 453 | 45.680 | 23.674 | −38.222 | 1.00 | 20.10 | B | C |
| ATOM | 15758 | O | ALA | B | 453 | 46.590 | 22.946 | −37.816 | 1.00 | 20.31 | B | O |

TABLE 8-2-continued

Coordinates for L494P Structure

| ATOM | 15760 | N | ASN | B | 454 | 45.793 | 24.992 | −38.343 | 1.00 | 19.21 | B | N |
|---|---|---|---|---|---|---|---|---|---|---|---|---|
| ATOM | 15761 | CA | ASN | B | 454 | 46.991 | 25.736 | −37.982 | 1.00 | 17.99 | B | C |
| ATOM | 15763 | CB | ASN | B | 454 | 48.020 | 25.682 | −39.117 | 1.00 | 17.83 | B | C |
| ATOM | 15766 | CG | ASN | B | 454 | 49.386 | 26.230 | −38.709 | 1.00 | 17.61 | B | C |
| ATOM | 15767 | OD1 | ASN | B | 454 | 49.581 | 27.442 | −38.617 | 1.00 | 17.15 | B | O |
| ATOM | 15768 | ND2 | ASN | B | 454 | 50.341 | 25.334 | −38.485 | 1.00 | 16.02 | B | N |
| ATOM | 15771 | C | ASN | B | 454 | 46.555 | 27.168 | −37.705 | 1.00 | 17.02 | B | C |
| ATOM | 15772 | O | ASN | B | 454 | 45.631 | 27.671 | −38.343 | 1.00 | 16.92 | B | O |
| ATOM | 15774 | N | SER | B | 455 | 47.198 | 27.816 | −36.743 | 1.00 | 16.17 | B | N |
| ATOM | 15775 | CA | SER | B | 455 | 46.830 | 29.178 | −36.373 | 1.00 | 15.49 | B | C |
| ATOM | 15777 | CB | SER | B | 455 | 47.504 | 29.571 | −35.061 | 1.00 | 15.49 | B | C |
| ATOM | 15780 | OG | SER | B | 455 | 47.026 | 28.759 | −34.002 | 1.00 | 15.01 | B | O |
| ATOM | 15782 | C | SER | B | 455 | 47.165 | 30.177 | −37.482 | 1.00 | 15.01 | B | C |
| ATOM | 15783 | O | SER | B | 455 | 46.369 | 31.068 | −37.780 | 1.00 | 14.87 | B | O |
| ATOM | 15785 | N | VAL | B | 456 | 48.331 | 30.015 | −38.104 | 1.00 | 14.62 | B | N |
| ATOM | 15786 | CA | VAL | B | 456 | 48.729 | 30.885 | −39.214 | 1.00 | 14.23 | B | C |
| ATOM | 15788 | CB | VAL | B | 456 | 50.186 | 30.623 | −39.660 | 1.00 | 13.71 | B | C |
| ATOM | 15790 | CG1 | VAL | B | 456 | 50.564 | 31.530 | −40.820 | 1.00 | 12.75 | B | C |
| ATOM | 15794 | CG2 | VAL | B | 456 | 51.140 | 30.836 | −38.498 | 1.00 | 12.43 | B | C |
| ATOM | 15798 | C | VAL | B | 456 | 47.769 | 30.725 | −40.399 | 1.00 | 14.74 | B | C |
| ATOM | 15799 | O | VAL | B | 456 | 47.520 | 31.682 | −41.133 | 1.00 | 15.01 | B | O |
| ATOM | 15801 | N | SER | B | 457 | 47.228 | 29.521 | −40.573 | 1.00 | 15.08 | B | N |
| ATOM | 15802 | CA | SER | B | 457 | 46.194 | 29.275 | −41.579 | 1.00 | 15.28 | B | C |
| ATOM | 15804 | CB | SER | B | 457 | 45.918 | 27.775 | −41.728 | 1.00 | 15.22 | B | C |
| ATOM | 15807 | OG | SER | B | 457 | 44.712 | 27.543 | −42.437 | 1.00 | 15.09 | B | O |
| ATOM | 15809 | C | SER | B | 457 | 44.902 | 30.009 | −41.227 | 1.00 | 15.53 | B | C |
| ATOM | 15810 | O | SER | B | 457 | 44.311 | 30.663 | −42.082 | 1.00 | 15.71 | B | O |
| ATOM | 15812 | N | CYS | B | 458 | 44.469 | 29.893 | −39.973 | 1.00 | 15.80 | B | N |
| ATOM | 15813 | CA | CYS | B | 458 | 43.245 | 30.559 | −39.515 | 1.00 | 16.11 | B | C |
| ATOM | 15815 | CB | CYS | B | 458 | 42.912 | 30.183 | −38.070 | 1.00 | 15.87 | B | C |
| ATOM | 15818 | SG | CYS | B | 458 | 42.128 | 28.572 | −37.880 | 1.00 | 18.08 | B | S |
| ATOM | 15820 | C | CYS | B | 458 | 43.354 | 32.072 | −39.628 | 1.00 | 16.21 | B | C |
| ATOM | 15821 | O | CYS | B | 458 | 42.379 | 32.744 | −39.968 | 1.00 | 17.07 | B | O |
| ATOM | 15823 | N | TYR | B | 459 | 44.539 | 32.602 | −39.342 | 1.00 | 15.90 | B | N |
| ATOM | 15824 | CA | TYR | B | 459 | 44.771 | 34.039 | −39.424 | 1.00 | 15.53 | B | C |
| ATOM | 15826 | CB | TYR | B | 459 | 46.084 | 34.420 | −38.727 | 1.00 | 15.20 | B | C |
| ATOM | 15829 | CG | TYR | B | 459 | 46.116 | 35.848 | −38.221 | 1.00 | 13.77 | B | C |
| ATOM | 15830 | CD1 | TYR | B | 459 | 45.880 | 36.142 | −36.880 | 1.00 | 11.99 | B | C |
| ATOM | 15832 | CE1 | TYR | B | 459 | 45.906 | 37.452 | −36.416 | 1.00 | 10.67 | B | C |
| ATOM | 15834 | CZ | TYR | B | 459 | 46.170 | 38.483 | −37.298 | 1.00 | 10.73 | B | C |
| ATOM | 15835 | OH | TYR | B | 459 | 46.202 | 39.785 | −36.855 | 1.00 | 12.04 | B | O |
| ATOM | 15837 | CE2 | TYR | B | 459 | 46.406 | 38.216 | −38.630 | 1.00 | 11.92 | B | C |
| ATOM | 15839 | CD2 | TYR | B | 459 | 46.376 | 36.906 | −39.086 | 1.00 | 13.04 | B | C |
| ATOM | 15841 | C | TYR | B | 459 | 44.765 | 34.507 | −40.884 | 1.00 | 15.64 | B | C |
| ATOM | 15842 | O | TYR | B | 459 | 44.354 | 35.630 | −41.171 | 1.00 | 15.37 | B | O |
| ATOM | 15844 | N | MET | B | 460 | 45.209 | 33.646 | −41.798 | 1.00 | 16.17 | B | N |
| ATOM | 15845 | CA | MET | B | 460 | 45.137 | 33.935 | −43.234 | 1.00 | 17.10 | B | C |
| ATOM | 15847 | CB | MET | B | 460 | 45.871 | 32.865 | −44.049 | 1.00 | 17.68 | B | C |
| ATOM | 15850 | CG | MET | B | 460 | 47.381 | 33.004 | −44.070 | 1.00 | 20.00 | B | C |
| ATOM | 15853 | SD | MET | B | 460 | 48.194 | 31.536 | −44.746 | 1.00 | 24.41 | B | S |
| ATOM | 15854 | CE | MET | B | 460 | 47.441 | 31.432 | −46.371 | 1.00 | 21.79 | B | C |
| ATOM | 15858 | C | MET | B | 460 | 43.690 | 34.021 | −43.726 | 1.00 | 17.18 | B | C |
| ATOM | 15859 | O | MET | B | 460 | 43.328 | 34.962 | −44.434 | 1.00 | 17.43 | B | O |
| ATOM | 15861 | N | ARG | B | 461 | 42.877 | 33.031 | −43.359 | 1.00 | 17.00 | B | N |
| ATOM | 15862 | CA | ARG | B | 461 | 41.472 | 32.966 | −43.784 | 1.00 | 16.70 | B | C |
| ATOM | 15864 | CB | ARG | B | 461 | 40.848 | 31.623 | −43.399 | 1.00 | 16.92 | B | C |
| ATOM | 15867 | CG | ARG | B | 461 | 41.012 | 30.525 | −44.433 | 1.00 | 17.73 | B | C |
| ATOM | 15870 | CD | ARG | B | 461 | 40.488 | 29.211 | −43.879 | 1.00 | 19.18 | B | C |
| ATOM | 15873 | NE | ARG | B | 461 | 41.337 | 28.716 | −42.794 | 1.00 | 19.69 | B | N |
| ATOM | 15875 | CZ | ARG | B | 461 | 40.942 | 27.907 | −41.810 | 1.00 | 20.75 | B | C |
| ATOM | 15876 | NH1 | ARG | B | 461 | 39.687 | 27.474 | −41.729 | 1.00 | 20.89 | B | N |
| ATOM | 15879 | NH2 | ARG | B | 461 | 41.819 | 27.534 | −40.886 | 1.00 | 22.40 | B | N |
| ATOM | 15882 | C | ARG | B | 461 | 40.621 | 34.079 | −43.186 | 1.00 | 16.22 | B | C |
| ATOM | 15883 | O | ARG | B | 461 | 39.803 | 34.683 | −43.879 | 1.00 | 16.34 | B | O |
| ATOM | 15885 | N | THR | B | 462 | 40.807 | 34.330 | −41.895 | 1.00 | 15.74 | B | N |
| ATOM | 15886 | CA | THR | B | 462 | 40.008 | 35.317 | −41.181 | 1.00 | 15.73 | B | C |
| ATOM | 15888 | CB | THR | B | 462 | 40.255 | 35.228 | −39.672 | 1.00 | 15.53 | B | C |
| ATOM | 15890 | OG1 | THR | B | 462 | 39.962 | 33.900 | −39.224 | 1.00 | 15.96 | B | O |
| ATOM | 15892 | CG2 | THR | B | 462 | 39.379 | 36.217 | −38.924 | 1.00 | 16.51 | B | C |
| ATOM | 15896 | C | THR | B | 462 | 40.261 | 36.749 | −41.649 | 1.00 | 15.94 | B | C |
| ATOM | 15897 | O | THR | B | 462 | 39.322 | 37.532 | −41.801 | 1.00 | 16.24 | B | O |
| ATOM | 15899 | N | LYS | B | 463 | 41.527 | 37.084 | −41.876 | 1.00 | 15.98 | B | N |
| ATOM | 15900 | CA | LYS | B | 463 | 41.906 | 38.423 | −42.316 | 1.00 | 16.21 | B | C |
| ATOM | 15902 | CB | LYS | B | 463 | 43.232 | 38.827 | −41.672 | 1.00 | 16.41 | B | C |
| ATOM | 15905 | CG | LYS | B | 463 | 43.165 | 38.978 | −40.152 | 1.00 | 16.93 | B | C |
| ATOM | 15908 | CD | LYS | B | 463 | 42.539 | 40.306 | −39.738 | 1.00 | 16.56 | B | C |
| ATOM | 15911 | CE | LYS | B | 463 | 42.716 | 40.567 | −38.251 | 1.00 | 16.16 | B | C |
| ATOM | 15914 | NZ | LYS | B | 463 | 42.453 | 41.992 | −37.910 | 1.00 | 15.98 | B | N |

TABLE 8-2-continued

Coordinates for L494P Structure

| ATOM | 15918 | C | LYS | B | 463 | 42.010 | 38.525 | −43.838 | 1.00 | 16.35 | B | C |
|---|---|---|---|---|---|---|---|---|---|---|---|---|
| ATOM | 15919 | O | LYS | B | 463 | 42.119 | 39.628 | −44.379 | 1.00 | 16.35 | B | O |
| ATOM | 15921 | N | GLY | B | 464 | 41.977 | 37.381 | −44.520 | 1.00 | 16.54 | B | N |
| ATOM | 15922 | CA | GLY | B | 464 | 42.063 | 37.340 | −45.978 | 1.00 | 16.78 | B | C |
| ATOM | 15925 | C | GLY | B | 464 | 43.348 | 37.955 | −46.500 | 1.00 | 17.14 | B | C |
| ATOM | 15926 | O | GLY | B | 464 | 43.316 | 38.779 | −47.415 | 1.00 | 17.35 | B | O |
| ATOM | 15928 | N | ILE | B | 465 | 44.477 | 37.550 | −45.917 | 1.00 | 17.39 | B | N |
| ATOM | 15929 | CA | ILE | B | 465 | 45.789 | 38.112 | −46.265 | 1.00 | 17.68 | B | C |
| ATOM | 15931 | CB | ILE | B | 465 | 46.356 | 39.000 | −45.122 | 1.00 | 17.52 | B | C |
| ATOM | 15933 | CG1 | ILE | B | 465 | 46.503 | 38.208 | −43.818 | 1.00 | 16.22 | B | C |
| ATOM | 15936 | CD1 | ILE | B | 465 | 47.122 | 39.001 | −42.698 | 1.00 | 13.96 | B | C |
| ATOM | 15940 | CG2 | ILE | B | 465 | 45.457 | 40.206 | −44.901 | 1.00 | 18.60 | B | C |
| ATOM | 15944 | C | ILE | B | 465 | 46.802 | 37.022 | −46.626 | 1.00 | 18.16 | B | C |
| ATOM | 15945 | O | ILE | B | 465 | 46.529 | 35.831 | −46.464 | 1.00 | 18.09 | B | O |
| ATOM | 15947 | N | SER | B | 466 | 47.966 | 37.448 | −47.118 | 1.00 | 18.79 | B | N |
| ATOM | 15948 | CA | SER | B | 466 | 49.035 | 36.535 | −47.538 | 1.00 | 19.13 | B | C |
| ATOM | 15950 | CB | SER | B | 466 | 50.103 | 37.303 | −48.318 | 1.00 | 19.18 | B | C |
| ATOM | 15953 | OG | SER | B | 466 | 50.799 | 38.203 | −47.471 | 1.00 | 18.23 | B | O |
| ATOM | 15955 | C | SER | B | 466 | 49.694 | 35.843 | −46.349 | 1.00 | 19.60 | B | C |
| ATOM | 15956 | O | SER | B | 466 | 49.741 | 36.401 | −45.251 | 1.00 | 19.64 | B | O |
| ATOM | 15958 | N | GLU | B | 467 | 50.216 | 34.637 | −46.581 | 1.00 | 20.01 | B | N |
| ATOM | 15959 | CA | GLU | B | 467 | 50.903 | 33.862 | −45.535 | 1.00 | 20.44 | B | C |
| ATOM | 15961 | CB | GLU | B | 467 | 51.440 | 32.541 | −46.106 | 1.00 | 20.58 | B | C |
| ATOM | 15964 | CG | GLU | B | 467 | 52.180 | 31.664 | −45.086 | 1.00 | 20.96 | B | C |
| ATOM | 15967 | CD | GLU | B | 467 | 52.735 | 30.383 | −45.685 | 1.00 | 21.70 | B | C |
| ATOM | 15968 | OE1 | GLU | B | 467 | 52.053 | 29.765 | −46.530 | 1.00 | 22.54 | B | O |
| ATOM | 15969 | OE2 | GLU | B | 467 | 53.854 | 29.984 | −45.296 | 1.00 | 22.39 | B | O |
| ATOM | 15970 | C | GLU | B | 467 | 52.047 | 34.650 | −44.895 | 1.00 | 20.53 | B | C |
| ATOM | 15971 | O | GLU | B | 467 | 52.293 | 34.541 | −43.692 | 1.00 | 20.25 | B | O |
| ATOM | 15973 | N | GLU | B | 468 | 52.744 | 35.432 | −45.714 | 1.00 | 20.89 | B | N |
| ATOM | 15974 | CA | GLU | B | 468 | 53.826 | 36.295 | −45.253 | 1.00 | 21.16 | B | C |
| ATOM | 15976 | CB | GLU | B | 468 | 54.438 | 37.025 | −46.451 | 1.00 | 21.39 | B | C |
| ATOM | 15979 | CG | GLU | B | 468 | 55.709 | 37.807 | −46.150 | 1.00 | 22.77 | B | C |
| ATOM | 15982 | CD | GLU | B | 468 | 56.147 | 38.680 | −47.317 | 1.00 | 25.04 | B | C |
| ATOM | 15983 | OE1 | GLU | B | 468 | 55.474 | 38.657 | −48.373 | 1.00 | 26.20 | B | O |
| ATOM | 15984 | OE2 | GLU | B | 468 | 57.164 | 39.393 | −47.179 | 1.00 | 26.28 | B | O |
| ATOM | 15985 | C | GLU | B | 468 | 53.330 | 37.316 | −44.225 | 1.00 | 20.91 | B | C |
| ATOM | 15986 | O | GLU | B | 468 | 53.981 | 37.540 | −43.203 | 1.00 | 21.14 | B | O |
| ATOM | 15988 | N | LEU | B | 469 | 52.179 | 37.925 | −44.507 | 1.00 | 20.46 | B | N |
| ATOM | 15989 | CA | LEU | B | 469 | 51.607 | 38.964 | −43.642 | 1.00 | 19.85 | B | C |
| ATOM | 15991 | CB | LEU | B | 469 | 50.616 | 39.833 | −44.433 | 1.00 | 19.93 | B | C |
| ATOM | 15994 | CG | LEU | B | 469 | 50.541 | 41.325 | −44.088 | 1.00 | 19.46 | B | C |
| ATOM | 15996 | CD1 | LEU | B | 469 | 49.630 | 42.035 | −45.081 | 1.00 | 19.01 | B | C |
| ATOM | 16000 | CD2 | LEU | B | 469 | 50.071 | 41.572 | −42.657 | 1.00 | 18.30 | B | C |
| ATOM | 16004 | C | LEU | B | 469 | 50.923 | 38.353 | −42.412 | 1.00 | 19.10 | B | C |
| ATOM | 16005 | O | LEU | B | 469 | 50.888 | 38.969 | −41.349 | 1.00 | 18.73 | B | O |
| ATOM | 16007 | N | ALA | B | 470 | 50.374 | 37.149 | −42.565 | 1.00 | 18.69 | B | N |
| ATOM | 16008 | CA | ALA | B | 470 | 49.770 | 36.427 | −41.443 | 1.00 | 18.30 | B | C |
| ATOM | 16010 | CB | ALA | B | 470 | 48.984 | 35.221 | −41.945 | 1.00 | 18.19 | B | C |
| ATOM | 16014 | C | ALA | B | 470 | 50.835 | 35.987 | −40.441 | 1.00 | 17.77 | B | C |
| ATOM | 16015 | O | ALA | B | 470 | 50.624 | 36.070 | −39.230 | 1.00 | 17.14 | B | O |
| ATOM | 16017 | N | THR | B | 471 | 51.970 | 35.517 | −40.961 | 1.00 | 17.77 | B | N |
| ATOM | 16018 | CA | THR | B | 471 | 53.128 | 35.137 | −40.141 | 1.00 | 17.92 | B | C |
| ATOM | 16020 | CB | THR | B | 471 | 54.264 | 34.553 | −41.009 | 1.00 | 17.78 | B | C |
| ATOM | 16022 | OG1 | THR | B | 471 | 53.940 | 33.208 | −41.381 | 1.00 | 18.24 | B | O |
| ATOM | 16024 | CG2 | THR | B | 471 | 55.586 | 34.559 | −40.261 | 1.00 | 17.26 | B | C |
| ATOM | 16028 | C | THR | B | 471 | 53.670 | 36.319 | −39.337 | 1.00 | 18.26 | B | C |
| ATOM | 16029 | O | THR | B | 471 | 54.011 | 36.171 | −38.164 | 1.00 | 18.51 | B | O |
| ATOM | 16031 | N | GLU | B | 472 | 53.747 | 37.483 | −39.979 | 1.00 | 18.50 | B | N |
| ATOM | 16032 | CA | GLU | B | 472 | 54.144 | 38.730 | −39.322 | 1.00 | 18.54 | B | C |
| ATOM | 16034 | CB | GLU | B | 472 | 54.078 | 39.882 | −40.333 | 1.00 | 18.66 | B | C |
| ATOM | 16037 | CG | GLU | B | 472 | 54.483 | 41.252 | −39.797 | 1.00 | 19.75 | B | C |
| ATOM | 16040 | CD | GLU | B | 472 | 54.306 | 42.361 | −40.825 | 1.00 | 20.71 | B | C |
| ATOM | 16041 | OE1 | GLU | B | 472 | 53.611 | 42.146 | −41.843 | 1.00 | 18.97 | B | O |
| ATOM | 16042 | OE2 | GLU | B | 472 | 54.864 | 43.457 | −40.610 | 1.00 | 22.53 | B | O |
| ATOM | 16043 | C | GLU | B | 472 | 53.255 | 39.043 | −38.112 | 1.00 | 18.37 | B | C |
| ATOM | 16044 | O | GLU | B | 472 | 53.753 | 39.376 | −37.036 | 1.00 | 18.21 | B | O |
| ATOM | 16046 | N | SER | B | 473 | 51.941 | 38.931 | −38.299 | 1.00 | 18.41 | B | N |
| ATOM | 16047 | CA | SER | B | 473 | 50.970 | 39.247 | −37.248 | 1.00 | 18.17 | B | C |
| ATOM | 16049 | CB | SER | B | 473 | 49.548 | 39.246 | −37.813 | 1.00 | 17.98 | B | C |
| ATOM | 16052 | OG | SER | B | 473 | 49.382 | 40.280 | −38.766 | 1.00 | 17.49 | B | O |
| ATOM | 16054 | C | SER | B | 473 | 51.058 | 38.289 | −36.061 | 1.00 | 18.17 | B | C |
| ATOM | 16055 | O | SER | B | 473 | 50.892 | 38.704 | −34.913 | 1.00 | 18.49 | B | O |
| ATOM | 16057 | N | VAL | B | 474 | 51.314 | 37.013 | −36.339 | 1.00 | 17.87 | B | N |
| ATOM | 16058 | CA | VAL | B | 474 | 51.508 | 36.026 | −35.278 | 1.00 | 17.81 | B | C |
| ATOM | 16060 | CB | VAL | B | 474 | 51.578 | 34.583 | −35.835 | 1.00 | 17.80 | B | C |
| ATOM | 16062 | CG1 | VAL | B | 474 | 51.912 | 33.591 | −34.727 | 1.00 | 16.61 | B | C |
| ATOM | 16066 | CG2 | VAL | B | 474 | 50.261 | 34.205 | −36.504 | 1.00 | 16.90 | B | C |

TABLE 8-2-continued

Coordinates for L494P Structure

| ATOM | 16070 | C | VAL | B | 474 | 52.769 | 36.341 | −34.469 | 1.00 | 18.13 | B | C |
|---|---|---|---|---|---|---|---|---|---|---|---|---|
| ATOM | 16071 | O | VAL | B | 474 | 52.783 | 36.165 | −33.253 | 1.00 | 18.18 | B | O |
| ATOM | 16073 | N | MET | B | 475 | 53.817 | 36.817 | −35.139 | 1.00 | 18.76 | B | N |
| ATOM | 16074 | CA | MET | B | 475 | 55.033 | 37.248 | −34.443 | 1.00 | 19.47 | B | C |
| ATOM | 16076 | CB | MET | B | 475 | 56.131 | 37.658 | −35.433 | 1.00 | 19.73 | B | C |
| ATOM | 16079 | CG | MET | B | 475 | 56.654 | 36.537 | −36.319 | 1.00 | 20.45 | B | C |
| ATOM | 16082 | SD | MET | B | 475 | 57.699 | 35.349 | −35.460 | 1.00 | 23.17 | B | S |
| ATOM | 16083 | CE | MET | B | 475 | 58.311 | 34.392 | −36.849 | 1.00 | 21.35 | B | C |
| ATOM | 16087 | C | MET | B | 475 | 54.718 | 38.423 | −33.517 | 1.00 | 19.81 | B | C |
| ATOM | 16088 | O | MET | B | 475 | 55.195 | 38.471 | −32.383 | 1.00 | 19.66 | B | O |
| ATOM | 16090 | N | ASN | B | 476 | 53.912 | 39.363 | −34.009 | 1.00 | 20.14 | B | N |
| ATOM | 16091 | CA | ASN | B | 476 | 53.483 | 40.518 | −33.216 | 1.00 | 20.47 | B | C |
| ATOM | 16093 | CB | ASN | B | 476 | 52.766 | 41.543 | −34.102 | 1.00 | 20.65 | B | C |
| ATOM | 16096 | CG | ASN | B | 476 | 53.699 | 42.205 | −35.101 | 1.00 | 21.93 | B | C |
| ATOM | 16097 | OD1 | ASN | B | 476 | 54.734 | 42.757 | −34.726 | 1.00 | 24.56 | B | O |
| ATOM | 16098 | ND2 | ASN | B | 476 | 53.333 | 42.160 | −36.379 | 1.00 | 22.45 | B | N |
| ATOM | 16101 | C | ASN | B | 476 | 52.581 | 40.123 | −32.044 | 1.00 | 20.49 | B | C |
| ATOM | 16102 | O | ASN | B | 476 | 52.541 | 40.815 | −31.025 | 1.00 | 20.89 | B | O |
| ATOM | 16104 | N | LEU | B | 477 | 51.862 | 39.014 | −32.195 | 1.00 | 20.27 | B | N |
| ATOM | 16105 | CA | LEU | B | 477 | 51.019 | 38.481 | −31.123 | 1.00 | 19.90 | B | C |
| ATOM | 16107 | CB | LEU | B | 477 | 50.030 | 37.446 | −31.674 | 1.00 | 19.84 | B | C |
| ATOM | 16110 | CG | LEU | B | 477 | 48.636 | 37.462 | −31.046 | 1.00 | 19.42 | B | C |
| ATOM | 16112 | CD1 | LEU | B | 477 | 47.908 | 38.751 | −31.411 | 1.00 | 18.74 | B | C |
| ATOM | 16116 | CD2 | LEU | B | 477 | 47.841 | 36.247 | −31.494 | 1.00 | 18.32 | B | C |
| ATOM | 16120 | C | LEU | B | 477 | 51.877 | 37.863 | −30.013 | 1.00 | 19.60 | B | C |
| ATOM | 16121 | O | LEU | B | 477 | 51.480 | 37.864 | −28.845 | 1.00 | 19.36 | B | O |
| ATOM | 16123 | N | ILE | B | 478 | 53.045 | 37.335 | −30.386 | 1.00 | 19.33 | B | N |
| ATOM | 16124 | CA | ILE | B | 478 | 54.028 | 36.846 | −29.414 | 1.00 | 18.77 | B | C |
| ATOM | 16126 | CB | ILE | B | 478 | 55.159 | 36.038 | −30.092 | 1.00 | 18.25 | B | C |
| ATOM | 16128 | CG1 | ILE | B | 478 | 54.626 | 34.686 | −30.568 | 1.00 | 17.56 | B | C |
| ATOM | 16131 | CD1 | ILE | B | 478 | 55.694 | 33.767 | −31.126 | 1.00 | 17.90 | B | C |
| ATOM | 16135 | CG2 | ILE | B | 478 | 56.321 | 35.832 | −29.135 | 1.00 | 16.88 | B | C |
| ATOM | 16139 | C | ILE | B | 478 | 54.631 | 38.007 | −28.622 | 1.00 | 19.04 | B | C |
| ATOM | 16140 | O | ILE | B | 478 | 54.677 | 37.962 | −27.393 | 1.00 | 19.14 | B | O |
| ATOM | 16142 | N | ASP | B | 479 | 55.088 | 39.040 | −29.331 | 1.00 | 19.19 | B | N |
| ATOM | 16143 | CA | ASP | B | 479 | 55.605 | 40.255 | −28.694 | 1.00 | 19.30 | B | C |
| ATOM | 16145 | CB | ASP | B | 479 | 55.884 | 41.345 | −29.739 | 1.00 | 19.38 | B | C |
| ATOM | 16148 | CG | ASP | B | 479 | 57.121 | 41.061 | −30.580 | 1.00 | 19.94 | B | C |
| ATOM | 16149 | OD1 | ASP | B | 479 | 57.589 | 39.903 | −30.603 | 1.00 | 22.59 | B | O |
| ATOM | 16150 | OD2 | ASP | B | 479 | 57.625 | 42.004 | −31.228 | 1.00 | 19.87 | B | O |
| ATOM | 16151 | C | ASP | B | 479 | 54.625 | 40.792 | −27.649 | 1.00 | 19.52 | B | C |
| ATOM | 16152 | O | ASP | B | 479 | 55.007 | 41.051 | −26.506 | 1.00 | 19.57 | B | O |
| ATOM | 16154 | N | GLU | B | 480 | 53.362 | 40.940 | −28.044 | 1.00 | 19.62 | B | N |
| ATOM | 16155 | CA | GLU | B | 480 | 52.332 | 41.489 | −27.156 | 1.00 | 19.69 | B | C |
| ATOM | 16157 | CB | GLU | B | 480 | 51.053 | 41.813 | −27.939 | 1.00 | 19.64 | B | C |
| ATOM | 16160 | CG | GLU | B | 480 | 51.154 | 43.076 | −28.785 | 1.00 | 20.42 | B | C |
| ATOM | 16163 | CD | GLU | B | 480 | 51.566 | 44.302 | −27.976 | 1.00 | 21.42 | B | C |
| ATOM | 16164 | OE1 | GLU | B | 480 | 52.363 | 45.113 | −28.490 | 1.00 | 21.49 | B | O |
| ATOM | 16165 | OE2 | GLU | B | 480 | 51.104 | 44.448 | −26.823 | 1.00 | 21.89 | B | O |
| ATOM | 16166 | C | GLU | B | 480 | 52.004 | 40.588 | −25.966 | 1.00 | 19.49 | B | C |
| ATOM | 16167 | O | GLU | B | 480 | 51.663 | 41.085 | −24.889 | 1.00 | 19.09 | B | O |
| ATOM | 16169 | N | THR | B | 481 | 52.102 | 39.274 | −26.165 | 1.00 | 19.48 | B | N |
| ATOM | 16170 | CA | THR | B | 481 | 51.921 | 38.308 | −25.077 | 1.00 | 19.19 | B | C |
| ATOM | 16172 | CB | THR | B | 481 | 51.751 | 36.871 | −25.609 | 1.00 | 18.82 | B | C |
| ATOM | 16174 | OG1 | THR | B | 481 | 50.430 | 36.713 | −26.142 | 1.00 | 17.25 | B | O |
| ATOM | 16176 | CG2 | THR | B | 481 | 51.964 | 35.856 | −24.497 | 1.00 | 18.35 | B | C |
| ATOM | 16180 | C | THR | B | 481 | 53.093 | 38.359 | −24.092 | 1.00 | 19.61 | B | C |
| ATOM | 16181 | O | THR | B | 481 | 52.883 | 38.329 | −22.877 | 1.00 | 20.16 | B | O |
| ATOM | 16183 | N | TRP | B | 482 | 54.318 | 38.438 | −24.613 | 1.00 | 19.27 | B | N |
| ATOM | 16184 | CA | TRP | B | 482 | 55.503 | 38.600 | −23.763 | 1.00 | 19.03 | B | C |
| ATOM | 16186 | CB | TRP | B | 482 | 56.805 | 38.542 | −24.581 | 1.00 | 19.10 | B | C |
| ATOM | 16189 | CG | TRP | B | 482 | 57.389 | 37.164 | −24.652 | 1.00 | 19.78 | B | C |
| ATOM | 16190 | CD1 | TRP | B | 482 | 57.235 | 36.257 | −25.660 | 1.00 | 20.32 | B | C |
| ATOM | 16192 | NE1 | TRP | B | 482 | 57.906 | 35.097 | −25.360 | 1.00 | 20.19 | B | N |
| ATOM | 16194 | CE2 | TRP | B | 482 | 58.509 | 35.235 | −24.137 | 1.00 | 20.96 | B | C |
| ATOM | 16195 | CD2 | TRP | B | 482 | 58.203 | 36.526 | −23.660 | 1.00 | 20.92 | B | C |
| ATOM | 16196 | CE3 | TRP | B | 482 | 58.704 | 36.921 | −22.413 | 1.00 | 20.54 | B | C |
| ATOM | 16198 | CZ3 | TRP | B | 482 | 59.485 | 36.024 | −21.694 | 1.00 | 19.83 | B | C |
| ATOM | 16200 | CH2 | TRP | B | 482 | 59.775 | 34.750 | −22.197 | 1.00 | 18.86 | B | C |
| ATOM | 16202 | CZ2 | TRP | B | 482 | 59.300 | 34.336 | −23.413 | 1.00 | 19.97 | B | C |
| ATOM | 16204 | C | TRP | B | 482 | 55.439 | 39.896 | −22.960 | 1.00 | 18.96 | B | C |
| ATOM | 16205 | O | TRP | B | 482 | 55.892 | 39.935 | −21.818 | 1.00 | 18.99 | B | O |
| ATOM | 16207 | N | LYS | B | 483 | 54.871 | 40.945 | −23.553 | 1.00 | 18.84 | B | N |
| ATOM | 16208 | CA | LYS | B | 483 | 54.711 | 42.228 | −22.860 | 1.00 | 18.72 | B | C |
| ATOM | 16210 | CB | LYS | B | 483 | 54.188 | 43.306 | −23.818 | 1.00 | 18.58 | B | C |
| ATOM | 16213 | CG | LYS | B | 483 | 55.251 | 43.895 | −24.728 | 1.00 | 16.71 | B | C |
| ATOM | 16216 | CD | LYS | B | 483 | 54.670 | 44.960 | −25.639 | 1.00 | 14.83 | B | C |
| ATOM | 16219 | CE | LYS | B | 483 | 55.692 | 45.441 | −26.649 | 1.00 | 13.58 | B | C |

TABLE 8-2-continued

Coordinates for L494P Structure

| ATOM | 16222 | NZ | LYS | B | 483 | 55.245 | 46.679 | −27.324 | 1.00 | 11.34 | B | N |
|---|---|---|---|---|---|---|---|---|---|---|---|---|
| ATOM | 16226 | C | LYS | B | 483 | 53.790 | 42.123 | −21.640 | 1.00 | 18.92 | B | C |
| ATOM | 16227 | O | LYS | B | 483 | 53.982 | 42.829 | −20.648 | 1.00 | 19.09 | B | O |
| ATOM | 16229 | N | LYS | B | 484 | 52.799 | 41.241 | −21.717 | 1.00 | 18.99 | B | N |
| ATOM | 16230 | CA | LYS | B | 484 | 51.861 | 41.039 | −20.615 | 1.00 | 19.49 | B | C |
| ATOM | 16232 | CB | LYS | B | 484 | 50.477 | 40.674 | −21.160 | 1.00 | 19.74 | B | C |
| ATOM | 16235 | CG | LYS | B | 484 | 49.839 | 41.803 | −21.979 | 1.00 | 20.77 | B | C |
| ATOM | 16238 | CD | LYS | B | 484 | 48.609 | 41.336 | −22.749 | 1.00 | 21.69 | B | C |
| ATOM | 16241 | CE | LYS | B | 484 | 48.153 | 42.369 | −23.775 | 1.00 | 21.40 | B | C |
| ATOM | 16244 | NZ | LYS | B | 484 | 47.244 | 41.774 | −24.798 | 1.00 | 21.11 | B | N |
| ATOM | 16248 | C | LYS | B | 484 | 52.368 | 39.992 | −19.614 | 1.00 | 19.34 | B | C |
| ATOM | 16249 | O | LYS | B | 484 | 52.050 | 40.061 | −18.427 | 1.00 | 19.45 | B | O |
| ATOM | 16251 | N | MET | B | 485 | 53.157 | 39.031 | −20.089 | 1.00 | 19.18 | B | N |
| ATOM | 16252 | CA | MET | B | 485 | 53.822 | 38.075 | −19.199 | 1.00 | 19.15 | B | C |
| ATOM | 16254 | CB | MET | B | 485 | 54.469 | 36.941 | −19.992 | 1.00 | 18.98 | B | C |
| ATOM | 16257 | CG | MET | B | 485 | 53.499 | 35.902 | −20.500 | 1.00 | 18.28 | B | C |
| ATOM | 16260 | SD | MET | B | 485 | 54.363 | 34.436 | −21.072 | 1.00 | 16.65 | B | S |
| ATOM | 16261 | CE | MET | B | 485 | 55.425 | 35.132 | −22.337 | 1.00 | 16.32 | B | C |
| ATOM | 16265 | C | MET | B | 485 | 54.897 | 38.750 | −18.353 | 1.00 | 19.51 | B | C |
| ATOM | 16266 | O | MET | B | 485 | 55.082 | 38.397 | −17.190 | 1.00 | 19.86 | B | O |
| ATOM | 16268 | N | ASN | B | 486 | 55.615 | 39.700 | −18.949 | 1.00 | 19.82 | B | N |
| ATOM | 16269 | CA | ASN | B | 486 | 56.642 | 40.457 | −18.234 | 1.00 | 20.17 | B | C |
| ATOM | 16271 | CB | ASN | B | 486 | 57.353 | 41.434 | −19.175 | 1.00 | 20.23 | B | C |
| ATOM | 16274 | CG | ASN | B | 486 | 58.260 | 40.739 | −20.174 | 1.00 | 20.22 | B | C |
| ATOM | 16275 | OD1 | ASN | B | 486 | 58.679 | 39.597 | −19.968 | 1.00 | 18.04 | B | O |
| ATOM | 16276 | ND2 | ASN | B | 486 | 58.570 | 41.432 | −21.267 | 1.00 | 18.35 | B | N |
| ATOM | 16279 | C | ASN | B | 486 | 56.073 | 41.225 | −17.046 | 1.00 | 20.79 | B | C |
| ATOM | 16280 | O | ASN | B | 486 | 56.712 | 41.302 | −15.994 | 1.00 | 20.97 | B | O |
| ATOM | 16282 | N | LYS | B | 487 | 54.878 | 41.792 | −17.221 | 1.00 | 21.29 | B | N |
| ATOM | 16283 | CA | LYS | B | 487 | 54.199 | 42.524 | −16.147 | 1.00 | 21.50 | B | C |
| ATOM | 16285 | CB | LYS | B | 487 | 52.967 | 43.266 | −16.678 | 1.00 | 21.48 | B | C |
| ATOM | 16288 | CG | LYS | B | 487 | 52.281 | 44.137 | −15.630 | 1.00 | 22.59 | B | C |
| ATOM | 16291 | CD | LYS | B | 487 | 51.063 | 44.853 | −16.184 | 1.00 | 25.14 | B | C |
| ATOM | 16294 | CE | LYS | B | 487 | 50.218 | 45.453 | −15.064 | 1.00 | 26.24 | B | C |
| ATOM | 16297 | NZ | LYS | B | 487 | 48.974 | 46.098 | −15.571 | 1.00 | 27.02 | B | N |
| ATOM | 16301 | C | LYS | B | 487 | 53.789 | 41.596 | −15.005 | 1.00 | 21.42 | B | C |
| ATOM | 16302 | O | LYS | B | 487 | 53.830 | 41.990 | −13.841 | 1.00 | 21.42 | B | O |
| ATOM | 16304 | N | GLU | B | 488 | 53.397 | 40.371 | −15.346 | 1.00 | 21.59 | B | N |
| ATOM | 16305 | CA | GLU | B | 488 | 52.999 | 39.373 | −14.350 | 1.00 | 21.83 | B | C |
| ATOM | 16307 | CB | GLU | B | 488 | 52.583 | 38.064 | −15.035 | 1.00 | 21.81 | B | C |
| ATOM | 16310 | CG | GLU | B | 488 | 51.557 | 37.253 | −14.256 | 1.00 | 21.26 | B | C |
| ATOM | 16313 | CD | GLU | B | 488 | 50.179 | 37.886 | −14.273 | 1.00 | 19.11 | B | C |
| ATOM | 16314 | OE1 | GLU | B | 488 | 49.566 | 38.007 | −13.191 | 1.00 | 20.01 | B | O |
| ATOM | 16315 | OE2 | GLU | B | 488 | 49.713 | 38.270 | −15.365 | 1.00 | 14.89 | B | O |
| ATOM | 16316 | C | GLU | B | 488 | 54.134 | 39.104 | −13.359 | 1.00 | 22.01 | B | C |
| ATOM | 16317 | O | GLU | B | 488 | 53.948 | 39.212 | −12.145 | 1.00 | 22.27 | B | O |
| ATOM | 16319 | N | LYS | B | 489 | 55.308 | 38.772 | −13.894 | 1.00 | 21.89 | B | N |
| ATOM | 16320 | CA | LYS | B | 489 | 56.502 | 38.503 | −13.087 | 1.00 | 21.65 | B | C |
| ATOM | 16322 | CB | LYS | B | 489 | 57.658 | 38.066 | −13.995 | 1.00 | 21.41 | B | C |
| ATOM | 16325 | CG | LYS | B | 489 | 58.974 | 37.757 | −13.282 | 1.00 | 20.79 | B | C |
| ATOM | 16328 | CD | LYS | B | 489 | 58.858 | 36.558 | −12.349 | 1.00 | 19.77 | B | C |
| ATOM | 16331 | CE | LYS | B | 489 | 60.160 | 36.303 | −11.605 | 1.00 | 19.39 | B | C |
| ATOM | 16334 | NZ | LYS | B | 489 | 61.314 | 36.125 | −12.527 | 1.00 | 18.60 | B | N |
| ATOM | 16338 | C | LYS | B | 489 | 56.932 | 39.715 | −12.260 | 1.00 | 21.80 | B | C |
| ATOM | 16339 | O | LYS | B | 489 | 57.425 | 39.566 | −11.140 | 1.00 | 21.96 | B | O |
| ATOM | 16341 | N | LEU | B | 490 | 56.749 | 40.908 | −12.820 | 1.00 | 21.81 | B | N |
| ATOM | 16342 | CA | LEU | B | 490 | 57.145 | 42.143 | −12.149 | 1.00 | 21.84 | B | C |
| ATOM | 16344 | CB | LEU | B | 490 | 56.972 | 43.349 | −13.084 | 1.00 | 21.72 | B | C |
| ATOM | 16347 | CG | LEU | B | 490 | 58.111 | 44.369 | −13.049 | 1.00 | 21.17 | B | C |
| ATOM | 16349 | CD1 | LEU | B | 490 | 59.318 | 43.812 | −13.782 | 1.00 | 20.00 | B | C |
| ATOM | 16353 | CD2 | LEU | B | 490 | 57.681 | 45.699 | −13.651 | 1.00 | 20.57 | B | C |
| ATOM | 16357 | C | LEU | B | 490 | 56.322 | 42.338 | −10.878 | 1.00 | 22.21 | B | C |
| ATOM | 16358 | O | LEU | B | 490 | 56.868 | 42.627 | −9.812 | 1.00 | 22.30 | B | O |
| ATOM | 16360 | N | GLY | B | 491 | 55.009 | 42.163 | −11.001 | 1.00 | 22.57 | B | N |
| ATOM | 16361 | CA | GLY | B | 491 | 54.092 | 42.349 | −9.881 | 1.00 | 22.97 | B | C |
| ATOM | 16364 | C | GLY | B | 491 | 52.644 | 42.326 | −10.332 | 1.00 | 23.45 | B | C |
| ATOM | 16365 | O | GLY | B | 491 | 52.356 | 42.365 | −11.528 | 1.00 | 23.60 | B | O |
| ATOM | 16367 | N | GLY | B | 492 | 51.727 | 42.281 | −9.372 | 1.00 | 23.88 | B | N |
| ATOM | 16368 | CA | GLY | B | 492 | 50.315 | 42.067 | −9.672 | 1.00 | 24.35 | B | C |
| ATOM | 16371 | C | GLY | B | 492 | 50.083 | 40.618 | −10.053 | 1.00 | 24.84 | B | C |
| ATOM | 16372 | O | GLY | B | 492 | 49.210 | 40.308 | −10.867 | 1.00 | 24.78 | B | O |
| ATOM | 16374 | N | SER | B | 493 | 50.882 | 39.734 | −9.456 | 1.00 | 25.52 | B | N |
| ATOM | 16375 | CA | SER | B | 493 | 50.805 | 38.298 | −9.698 | 1.00 | 25.67 | B | C |
| ATOM | 16377 | CB | SER | B | 493 | 52.214 | 37.695 | −9.775 | 1.00 | 25.87 | B | C |
| ATOM | 16380 | OG | SER | B | 493 | 53.048 | 38.173 | −8.728 | 1.00 | 24.83 | B | O |
| ATOM | 16382 | C | SER | B | 493 | 50.030 | 37.628 | −8.569 | 1.00 | 25.46 | B | C |
| ATOM | 16383 | O | SER | B | 493 | 50.479 | 37.651 | −7.421 | 1.00 | 25.26 | B | O |
| ATOM | 16385 | N | PRO | B | 494 | 48.869 | 37.023 | −8.886 | 1.00 | 25.33 | B | N |

TABLE 8-2-continued

Coordinates for L494P Structure

| ATOM | 16386 | CA | PRO | B | 494 | 48.148 | 36.286 | −7.852 | 1.00 | 25.35 | B | C |
|------|-------|-----|-----|---|-----|--------|--------|--------|------|-------|---|---|
| ATOM | 16388 | CB | PRO | B | 494 | 46.819 | 35.943 | −8.526 | 1.00 | 25.40 | B | C |
| ATOM | 16391 | CG | PRO | B | 494 | 47.149 | 35.847 | −9.962 | 1.00 | 25.73 | B | C |
| ATOM | 16394 | CD | PRO | B | 494 | 48.261 | 36.834 | −10.216 | 1.00 | 25.52 | B | C |
| ATOM | 16397 | C | PRO | B | 494 | 48.903 | 35.017 | −7.446 | 1.00 | 25.19 | B | C |
| ATOM | 16398 | O | PRO | B | 494 | 48.708 | 34.513 | −6.337 | 1.00 | 25.71 | B | O |
| ATOM | 16399 | N | PHE | B | 495 | 49.754 | 34.518 | −8.345 | 1.00 | 24.45 | B | N |
| ATOM | 16400 | CA | PHE | B | 495 | 50.663 | 33.413 | −8.048 | 1.00 | 23.68 | B | C |
| ATOM | 16402 | CB | PHE | B | 495 | 50.894 | 32.569 | −9.303 | 1.00 | 23.86 | B | C |
| ATOM | 16405 | CG | PHE | B | 495 | 49.660 | 31.879 | −9.802 | 1.00 | 23.56 | B | C |
| ATOM | 16406 | CD1 | PHE | B | 495 | 49.294 | 30.640 | −9.296 | 1.00 | 23.17 | B | C |
| ATOM | 16408 | CE1 | PHE | B | 495 | 48.154 | 29.998 | −9.745 | 1.00 | 22.12 | B | C |
| ATOM | 16410 | CZ | PHE | B | 495 | 47.361 | 30.592 | −10.713 | 1.00 | 21.69 | B | C |
| ATOM | 16412 | CE2 | PHE | B | 495 | 47.715 | 31.829 | −11.227 | 1.00 | 22.40 | B | C |
| ATOM | 16414 | CD2 | PHE | B | 495 | 48.860 | 32.466 | −10.770 | 1.00 | 22.45 | B | C |
| ATOM | 16416 | C | PHE | B | 495 | 52.005 | 33.919 | −7.523 | 1.00 | 22.88 | B | C |
| ATOM | 16417 | O | PHE | B | 495 | 52.295 | 35.118 | −7.564 | 1.00 | 22.31 | B | O |
| ATOM | 16419 | N | ALA | B | 496 | 52.816 | 32.988 | −7.031 | 1.00 | 22.48 | B | N |
| ATOM | 16420 | CA | ALA | B | 496 | 54.155 | 33.297 | −6.542 | 1.00 | 22.48 | B | C |
| ATOM | 16422 | CB | ALA | B | 496 | 54.680 | 32.144 | −5.697 | 1.00 | 22.42 | B | C |
| ATOM | 16426 | C | ALA | B | 496 | 55.093 | 33.563 | −7.716 | 1.00 | 22.53 | B | C |
| ATOM | 16427 | O | ALA | B | 496 | 54.948 | 32.954 | −8.778 | 1.00 | 22.92 | B | O |
| ATOM | 16429 | N | LYS | B | 497 | 56.056 | 34.463 | −7.521 | 1.00 | 22.29 | B | N |
| ATOM | 16430 | CA | LYS | B | 497 | 57.052 | 34.778 | −8.557 | 1.00 | 21.94 | B | C |
| ATOM | 16432 | CB | LYS | B | 497 | 58.007 | 35.884 | −8.084 | 1.00 | 22.07 | B | C |
| ATOM | 16435 | CG | LYS | B | 497 | 57.334 | 37.237 | −7.920 | 1.00 | 23.65 | B | C |
| ATOM | 16438 | CD | LYS | B | 497 | 58.343 | 38.366 | −7.815 | 1.00 | 24.78 | B | C |
| ATOM | 16441 | CE | LYS | B | 497 | 57.645 | 39.702 | −7.616 | 1.00 | 25.70 | B | C |
| ATOM | 16444 | NZ | LYS | B | 497 | 58.598 | 40.846 | −7.649 | 1.00 | 26.30 | B | N |
| ATOM | 16448 | C | LYS | B | 497 | 57.849 | 33.552 | −9.035 | 1.00 | 21.17 | B | C |
| ATOM | 16449 | O | LYS | B | 497 | 58.182 | 33.465 | −10.220 | 1.00 | 20.85 | B | O |
| ATOM | 16451 | N | PRO | B | 498 | 58.169 | 32.613 | −8.120 | 1.00 | 20.40 | B | N |
| ATOM | 16452 | CA | PRO | B | 498 | 58.746 | 31.335 | −8.539 | 1.00 | 19.76 | B | C |
| ATOM | 16454 | CB | PRO | B | 498 | 58.843 | 30.555 | −7.228 | 1.00 | 20.02 | B | C |
| ATOM | 16457 | CG | PRO | B | 498 | 59.067 | 31.596 | −6.208 | 1.00 | 20.28 | B | C |
| ATOM | 16460 | CD | PRO | B | 498 | 58.282 | 32.797 | −6.659 | 1.00 | 20.41 | B | C |
| ATOM | 16463 | C | PRO | B | 498 | 57.892 | 30.572 | −9.551 | 1.00 | 19.04 | B | C |
| ATOM | 16464 | O | PRO | B | 498 | 58.429 | 30.080 | −10.543 | 1.00 | 18.97 | B | O |
| ATOM | 16465 | N | PHE | B | 499 | 56.584 | 30.478 | −9.308 | 1.00 | 18.00 | B | N |
| ATOM | 16466 | CA | PHE | B | 499 | 55.679 | 29.806 | −10.247 | 1.00 | 17.28 | B | C |
| ATOM | 16468 | CB | PHE | B | 499 | 54.339 | 29.476 | −9.595 | 1.00 | 17.32 | B | C |
| ATOM | 16471 | CG | PHE | B | 499 | 53.370 | 28.806 | −10.530 | 1.00 | 17.69 | B | C |
| ATOM | 16472 | CD1 | PHE | B | 499 | 53.589 | 27.497 | −10.951 | 1.00 | 17.29 | B | C |
| ATOM | 16474 | CE1 | PHE | B | 499 | 52.705 | 26.871 | −11.823 | 1.00 | 16.85 | B | C |
| ATOM | 16476 | CZ | PHE | B | 499 | 51.587 | 27.557 | −12.288 | 1.00 | 16.84 | B | C |
| ATOM | 16478 | CE2 | PHE | B | 499 | 51.362 | 28.868 | −11.880 | 1.00 | 17.65 | B | C |
| ATOM | 16480 | CD2 | PHE | B | 499 | 52.252 | 29.486 | −11.006 | 1.00 | 17.32 | B | C |
| ATOM | 16482 | C | PHE | B | 499 | 55.432 | 30.634 | −11.505 | 1.00 | 16.84 | B | C |
| ATOM | 16483 | O | PHE | B | 499 | 55.363 | 30.086 | −12.605 | 1.00 | 16.87 | B | O |
| ATOM | 16485 | N | VAL | B | 500 | 55.287 | 31.947 | −11.338 | 1.00 | 16.41 | B | N |
| ATOM | 16486 | CA | VAL | B | 500 | 55.142 | 32.861 | −12.474 | 1.00 | 16.20 | B | C |
| ATOM | 16488 | CB | VAL | B | 500 | 54.925 | 34.317 | −12.010 | 1.00 | 16.36 | B | C |
| ATOM | 16490 | CG1 | VAL | B | 500 | 53.606 | 34.442 | −11.264 | 1.00 | 17.18 | B | C |
| ATOM | 16494 | CG2 | VAL | B | 500 | 54.957 | 35.280 | −13.191 | 1.00 | 16.91 | B | C |
| ATOM | 16498 | C | VAL | B | 500 | 56.363 | 32.793 | −13.394 | 1.00 | 15.82 | B | C |
| ATOM | 16499 | O | VAL | B | 500 | 56.243 | 32.992 | −14.600 | 1.00 | 15.97 | B | O |
| ATOM | 16501 | N | GLU | B | 501 | 57.531 | 32.509 | −12.822 | 1.00 | 15.50 | B | N |
| ATOM | 16502 | CA | GLU | B | 501 | 58.734 | 32.258 | −13.615 | 1.00 | 15.59 | B | C |
| ATOM | 16504 | CB | GLU | B | 501 | 60.003 | 32.453 | −12.769 | 1.00 | 15.69 | B | C |
| ATOM | 16507 | CG | GLU | B | 501 | 61.332 | 32.376 | −13.545 | 1.00 | 15.01 | B | C |
| ATOM | 16510 | CD | GLU | B | 501 | 61.554 | 33.531 | −14.526 | 1.00 | 16.71 | B | C |
| ATOM | 16511 | OE1 | GLU | B | 501 | 60.739 | 34.482 | −14.571 | 1.00 | 14.60 | B | O |
| ATOM | 16512 | OE2 | GLU | B | 501 | 62.564 | 33.485 | −15.261 | 1.00 | 18.19 | B | O |
| ATOM | 16513 | C | GLU | B | 501 | 58.704 | 30.854 | −14.231 | 1.00 | 15.47 | B | C |
| ATOM | 16514 | O | GLU | B | 501 | 59.123 | 30.677 | −15.375 | 1.00 | 16.14 | B | O |
| ATOM | 16516 | N | THR | B | 502 | 58.217 | 29.862 | −13.484 | 1.00 | 14.76 | B | N |
| ATOM | 16517 | CA | THR | B | 502 | 58.104 | 28.497 | −14.010 | 1.00 | 14.28 | B | C |
| ATOM | 16519 | CB | THR | B | 502 | 57.531 | 27.499 | −12.973 | 1.00 | 14.03 | B | C |
| ATOM | 16521 | OG1 | THR | B | 502 | 58.190 | 27.660 | −11.715 | 1.00 | 13.78 | B | O |
| ATOM | 16523 | CG2 | THR | B | 502 | 57.721 | 26.070 | −13.449 | 1.00 | 12.78 | B | C |
| ATOM | 16527 | C | THR | B | 502 | 57.210 | 28.464 | −15.246 | 1.00 | 14.49 | B | C |
| ATOM | 16528 | O | THR | B | 502 | 57.505 | 27.760 | −16.207 | 1.00 | 14.67 | B | O |
| ATOM | 16530 | N | ALA | B | 503 | 56.119 | 29.227 | −15.215 | 1.00 | 14.64 | B | N |
| ATOM | 16531 | CA | ALA | B | 503 | 55.206 | 29.306 | −16.354 | 1.00 | 14.82 | B | C |
| ATOM | 16533 | CB | ALA | B | 503 | 53.932 | 30.048 | −15.973 | 1.00 | 14.76 | B | C |
| ATOM | 16537 | C | ALA | B | 503 | 55.890 | 29.989 | −17.534 | 1.00 | 14.83 | B | C |
| ATOM | 16538 | O | ALA | B | 503 | 55.970 | 29.425 | −18.623 | 1.00 | 14.59 | B | O |
| ATOM | 16540 | N | ILE | B | 504 | 56.404 | 31.194 | −17.307 | 1.00 | 14.79 | B | N |

TABLE 8-2-continued

Coordinates for L494P Structure

| ATOM | 16541 | CA | ILE | B | 504 | 57.111 | 31.936 | −18.350 | 1.00 | 15.23 | B | C |
|------|-------|-----|-----|---|-----|--------|--------|---------|------|-------|---|---|
| ATOM | 16543 | CB | ILE | B | 504 | 57.747 | 33.233 | −17.790 | 1.00 | 15.36 | B | C |
| ATOM | 16545 | CG1 | ILE | B | 504 | 56.654 | 34.265 | −17.483 | 1.00 | 15.16 | B | C |
| ATOM | 16548 | CD1 | ILE | B | 504 | 57.127 | 35.440 | −16.656 | 1.00 | 12.30 | B | C |
| ATOM | 16552 | CG2 | ILE | B | 504 | 58.740 | 33.834 | −18.782 | 1.00 | 15.13 | B | C |
| ATOM | 16556 | C | ILE | B | 504 | 58.174 | 31.065 | −19.032 | 1.00 | 15.91 | B | C |
| ATOM | 16557 | O | ILE | B | 504 | 58.417 | 31.207 | −20.231 | 1.00 | 16.25 | B | O |
| ATOM | 16559 | N | ASN | B | 505 | 58.787 | 30.155 | −18.273 | 1.00 | 16.36 | B | N |
| ATOM | 16560 | CA | ASN | B | 505 | 59.760 | 29.208 | −18.829 | 1.00 | 16.52 | B | C |
| ATOM | 16562 | CB | ASN | B | 505 | 60.447 | 28.408 | −17.710 | 1.00 | 16.46 | B | C |
| ATOM | 16565 | CG | ASN | B | 505 | 61.425 | 29.249 | −16.892 | 1.00 | 16.04 | B | C |
| ATOM | 16566 | OD1 | ASN | B | 505 | 62.149 | 30.091 | −17.427 | 1.00 | 13.66 | B | O |
| ATOM | 16567 | ND2 | ASN | B | 505 | 61.456 | 29.008 | −15.586 | 1.00 | 16.62 | B | N |
| ATOM | 16570 | C | ASN | B | 505 | 59.169 | 28.251 | −19.876 | 1.00 | 16.61 | B | C |
| ATOM | 16571 | O | ASN | B | 505 | 59.891 | 27.786 | −20.761 | 1.00 | 16.48 | B | O |
| ATOM | 16573 | N | LEU | B | 506 | 57.872 | 27.955 | −19.774 | 1.00 | 16.86 | B | N |
| ATOM | 16574 | CA | LEU | B | 506 | 57.171 | 27.184 | −20.810 | 1.00 | 17.30 | B | C |
| ATOM | 16576 | CB | LEU | B | 506 | 55.726 | 26.888 | −20.401 | 1.00 | 17.57 | B | C |
| ATOM | 16579 | CG | LEU | B | 506 | 54.836 | 26.191 | −21.440 | 1.00 | 18.47 | B | C |
| ATOM | 16581 | CD1 | LEU | B | 506 | 55.184 | 24.719 | −21.542 | 1.00 | 19.77 | B | C |
| ATOM | 16585 | CD2 | LEU | B | 506 | 53.370 | 26.364 | −21.073 | 1.00 | 20.68 | B | C |
| ATOM | 16589 | C | LEU | B | 506 | 57.177 | 27.946 | −22.130 | 1.00 | 17.50 | B | C |
| ATOM | 16590 | O | LEU | B | 506 | 57.340 | 27.351 | −23.195 | 1.00 | 17.72 | B | O |
| ATOM | 16592 | N | ALA | B | 507 | 56.985 | 29.261 | −22.054 | 1.00 | 17.77 | B | N |
| ATOM | 16593 | CA | ALA | B | 507 | 57.067 | 30.120 | −23.233 | 1.00 | 17.80 | B | C |
| ATOM | 16595 | CB | ALA | B | 507 | 56.635 | 31.536 | −22.893 | 1.00 | 17.84 | B | C |
| ATOM | 16599 | C | ALA | B | 507 | 58.483 | 30.117 | −23.796 | 1.00 | 17.61 | B | C |
| ATOM | 16600 | O | ALA | B | 507 | 58.671 | 29.989 | −25.003 | 1.00 | 17.76 | B | O |
| ATOM | 16602 | N | ARG | B | 508 | 59.472 | 30.246 | −22.913 | 1.00 | 17.60 | B | N |
| ATOM | 16603 | CA | ARG | B | 508 | 60.880 | 30.193 | −23.309 | 1.00 | 17.71 | B | C |
| ATOM | 16605 | CB | ARG | B | 508 | 61.803 | 30.386 | −22.100 | 1.00 | 17.79 | B | C |
| ATOM | 16608 | CG | ARG | B | 508 | 61.746 | 31.773 | −21.487 | 1.00 | 18.73 | B | C |
| ATOM | 16611 | CD | ARG | B | 508 | 62.939 | 32.043 | −20.582 | 1.00 | 19.55 | B | C |
| ATOM | 16614 | NE | ARG | B | 508 | 62.905 | 33.398 | −20.024 | 1.00 | 19.83 | B | N |
| ATOM | 16616 | CZ | ARG | B | 508 | 62.358 | 33.739 | −18.857 | 1.00 | 19.59 | B | C |
| ATOM | 16617 | NH1 | ARG | B | 508 | 61.781 | 32.831 | −18.073 | 1.00 | 19.68 | B | N |
| ATOM | 16620 | NH2 | ARG | B | 508 | 62.391 | 35.009 | −18.468 | 1.00 | 19.69 | B | N |
| ATOM | 16623 | C | ARG | B | 508 | 61.212 | 28.870 | −23.984 | 1.00 | 17.74 | B | C |
| ATOM | 16624 | O | ARG | B | 508 | 61.822 | 28.855 | −25.052 | 1.00 | 17.57 | B | O |
| ATOM | 16626 | N | GLN | B | 509 | 60.806 | 27.767 | −23.355 | 1.00 | 17.87 | B | N |
| ATOM | 16627 | CA | GLN | B | 509 | 61.065 | 26.428 | −23.889 | 1.00 | 18.05 | B | C |
| ATOM | 16629 | CB | GLN | B | 509 | 60.600 | 25.353 | −22.901 | 1.00 | 17.84 | B | C |
| ATOM | 16632 | CG | GLN | B | 509 | 60.772 | 23.904 | −23.383 | 1.00 | 17.66 | B | C |
| ATOM | 16635 | CD | GLN | B | 509 | 62.217 | 23.521 | −23.658 | 1.00 | 16.78 | B | C |
| ATOM | 16636 | OE1 | GLN | B | 509 | 63.150 | 24.156 | −23.170 | 1.00 | 17.45 | B | O |
| ATOM | 16637 | NE2 | GLN | B | 509 | 62.404 | 22.471 | −24.442 | 1.00 | 16.89 | B | N |
| ATOM | 16640 | C | GLN | B | 509 | 60.396 | 26.220 | −25.248 | 1.00 | 18.61 | B | C |
| ATOM | 16641 | O | GLN | B | 509 | 60.959 | 25.561 | −26.124 | 1.00 | 18.92 | B | O |
| ATOM | 16643 | N | SER | B | 510 | 59.202 | 26.782 | −25.423 | 1.00 | 18.83 | B | N |
| ATOM | 16644 | CA | SER | B | 510 | 58.498 | 26.692 | −26.700 | 1.00 | 18.95 | B | C |
| ATOM | 16646 | CB | SER | B | 510 | 57.109 | 27.323 | −26.603 | 1.00 | 18.82 | B | C |
| ATOM | 16649 | OG | SER | B | 510 | 56.264 | 26.533 | −25.788 | 1.00 | 19.00 | B | O |
| ATOM | 16651 | C | SER | B | 510 | 59.292 | 27.337 | −27.832 | 1.00 | 19.16 | B | C |
| ATOM | 16652 | O | SER | B | 510 | 59.232 | 26.882 | −28.968 | 1.00 | 19.43 | B | O |
| ATOM | 16654 | N | HIS | B | 511 | 60.041 | 28.390 | −27.526 | 1.00 | 19.42 | B | N |
| ATOM | 16655 | CA | HIS | B | 511 | 60.889 | 29.022 | −28.531 | 1.00 | 20.02 | B | C |
| ATOM | 16657 | CB | HIS | B | 511 | 61.405 | 30.380 | −28.041 | 1.00 | 20.11 | B | C |
| ATOM | 16660 | CG | HIS | B | 511 | 60.395 | 31.479 | −28.143 | 1.00 | 17.99 | B | C |
| ATOM | 16661 | ND1 | HIS | B | 511 | 60.065 | 32.074 | −29.341 | 1.00 | 17.74 | B | N |
| ATOM | 16663 | CE1 | HIS | B | 511 | 59.155 | 33.006 | −29.131 | 1.00 | 18.27 | B | C |
| ATOM | 16665 | NE2 | HIS | B | 511 | 58.883 | 33.038 | −27.839 | 1.00 | 17.55 | B | N |
| ATOM | 16667 | CD2 | HIS | B | 511 | 59.645 | 32.092 | −27.199 | 1.00 | 16.35 | B | C |
| ATOM | 16669 | C | HIS | B | 511 | 62.058 | 28.118 | −28.933 | 1.00 | 20.72 | B | C |
| ATOM | 16670 | O | HIS | B | 511 | 62.345 | 27.955 | −30.121 | 1.00 | 20.84 | B | O |
| ATOM | 16672 | N | CYS | B | 512 | 62.712 | 27.519 | −27.943 | 1.00 | 21.38 | B | N |
| ATOM | 16673 | CA | CYS | B | 512 | 63.904 | 26.704 | −28.187 | 1.00 | 22.20 | B | C |
| ATOM | 16675 | CB | CYS | B | 512 | 64.715 | 26.569 | −26.894 | 1.00 | 22.42 | B | C |
| ATOM | 16678 | SG | CYS | B | 512 | 65.118 | 28.158 | −26.116 | 1.00 | 23.55 | B | S |
| ATOM | 16680 | C | CYS | B | 512 | 63.604 | 25.313 | −28.765 | 1.00 | 22.44 | B | C |
| ATOM | 16681 | O | CYS | B | 512 | 64.520 | 24.628 | −29.223 | 1.00 | 22.16 | B | O |
| ATOM | 16683 | N | THR | B | 513 | 62.337 | 24.898 | −28.740 | 1.00 | 23.12 | B | N |
| ATOM | 16684 | CA | THR | B | 513 | 61.931 | 23.599 | −29.287 | 1.00 | 24.06 | B | C |
| ATOM | 16686 | CB | THR | B | 513 | 60.899 | 22.897 | −28.371 | 1.00 | 24.30 | B | C |
| ATOM | 16688 | OG1 | THR | B | 513 | 61.262 | 23.083 | −26.999 | 1.00 | 25.60 | B | O |
| ATOM | 16690 | CG2 | THR | B | 513 | 60.832 | 21.401 | −28.671 | 1.00 | 24.35 | B | C |
| ATOM | 16694 | C | THR | B | 513 | 61.340 | 23.706 | −30.700 | 1.00 | 24.58 | B | C |
| ATOM | 16695 | O | THR | B | 513 | 61.194 | 22.695 | −31.386 | 1.00 | 24.46 | B | O |
| ATOM | 16697 | N | TYR | B | 514 | 61.003 | 24.921 | −31.132 | 1.00 | 25.51 | B | N |

TABLE 8-2-continued

Coordinates for L494P Structure

| ATOM | 16698 | CA | TYR | B | 514 | 60.432 | 25.139 | −32.463 | 1.00 | 26.21 B | C |
|---|---|---|---|---|---|---|---|---|---|---|---|
| ATOM | 16700 | CB | TYR | B | 514 | 58.968 | 25.573 | −32.348 | 1.00 | 25.89 B | C |
| ATOM | 16703 | CG | TYR | B | 514 | 58.098 | 24.497 | −31.729 | 1.00 | 24.88 B | C |
| ATOM | 16704 | CD1 | TYR | B | 514 | 57.783 | 23.342 | −32.437 | 1.00 | 25.24 B | C |
| ATOM | 16706 | CE1 | TYR | B | 514 | 56.994 | 22.346 | −31.874 | 1.00 | 24.68 B | C |
| ATOM | 16708 | CZ | TYR | B | 514 | 56.514 | 22.499 | −30.589 | 1.00 | 23.33 B | C |
| ATOM | 16709 | OH | TYR | B | 514 | 55.733 | 21.511 | −30.037 | 1.00 | 24.82 B | O |
| ATOM | 16711 | CE2 | TYR | B | 514 | 56.816 | 23.634 | −29.863 | 1.00 | 22.23 B | C |
| ATOM | 16713 | CD2 | TYR | B | 514 | 57.606 | 24.622 | −30.432 | 1.00 | 23.14 B | C |
| ATOM | 16715 | C | TYR | B | 514 | 61.268 | 26.142 | −33.264 | 1.00 | 27.31 B | C |
| ATOM | 16716 | O | TYR | B | 514 | 61.143 | 27.358 | −33.107 | 1.00 | 27.40 B | O |
| ATOM | 16718 | N | HIS | B | 515 | 62.124 | 25.595 | −34.122 | 1.00 | 28.61 B | N |
| ATOM | 16719 | CA | HIS | B | 515 | 63.102 | 26.361 | −34.893 | 1.00 | 30.06 B | C |
| ATOM | 16721 | CB | HIS | B | 515 | 64.492 | 26.228 | −34.242 | 1.00 | 30.62 B | C |
| ATOM | 16724 | CG | HIS | B | 515 | 64.870 | 24.815 | −33.904 | 1.00 | 32.08 B | C |
| ATOM | 16725 | ND1 | HIS | B | 515 | 64.776 | 24.306 | −32.626 | 1.00 | 31.97 B | N |
| ATOM | 16727 | CE1 | HIS | B | 515 | 65.159 | 23.042 | −32.629 | 1.00 | 32.68 B | C |
| ATOM | 16729 | NE2 | HIS | B | 515 | 65.492 | 22.710 | −33.863 | 1.00 | 34.16 B | N |
| ATOM | 16731 | CD2 | HIS | B | 515 | 65.320 | 23.801 | −34.681 | 1.00 | 33.51 B | C |
| ATOM | 16733 | C | HIS | B | 515 | 63.106 | 25.831 | −36.333 | 1.00 | 30.55 B | C |
| ATOM | 16734 | O | HIS | B | 515 | 62.201 | 25.084 | −36.717 | 1.00 | 30.83 B | O |
| ATOM | 16736 | N | ASN | B | 516 | 64.098 | 26.233 | −37.129 | 1.00 | 30.79 B | N |
| ATOM | 16737 | CA | ASN | B | 516 | 64.294 | 25.687 | −38.474 | 1.00 | 30.94 B | C |
| ATOM | 16739 | CB | ASN | B | 516 | 63.524 | 26.513 | −39.512 | 1.00 | 31.24 B | C |
| ATOM | 16742 | CG | ASN | B | 516 | 62.034 | 26.182 | −39.546 | 1.00 | 32.16 B | C |
| ATOM | 16743 | OD1 | ASN | B | 516 | 61.642 | 25.024 | −39.703 | 1.00 | 31.94 B | O |
| ATOM | 16744 | ND2 | ASN | B | 516 | 61.198 | 27.207 | −39.410 | 1.00 | 33.17 B | N |
| ATOM | 16747 | C | ASN | B | 516 | 65.774 | 25.639 | −38.839 | 1.00 | 30.76 B | C |
| ATOM | 16748 | O | ASN | B | 516 | 66.617 | 25.303 | −38.007 | 1.00 | 30.70 B | O |
| ATOM | 16750 | N | THR | B | 521 | 72.475 | 22.115 | −40.233 | 1.00 | 39.09 B | N |
| ATOM | 16751 | CA | THR | B | 521 | 71.640 | 21.708 | −39.109 | 1.00 | 39.22 B | C |
| ATOM | 16753 | CB | THR | B | 521 | 71.978 | 22.514 | −37.832 | 1.00 | 39.15 B | C |
| ATOM | 16755 | OG1 | THR | B | 521 | 73.375 | 22.401 | −37.542 | 1.00 | 39.43 B | O |
| ATOM | 16757 | CG2 | THR | B | 521 | 71.181 | 22.001 | −36.647 | 1.00 | 38.86 B | C |
| ATOM | 16761 | C | THR | B | 521 | 70.152 | 21.875 | −39.426 | 1.00 | 39.42 B | C |
| ATOM | 16762 | O | THR | B | 521 | 69.595 | 22.965 | −39.281 | 1.00 | 39.63 B | O |
| ATOM | 16764 | N | SER | B | 522 | 69.519 | 20.787 | −39.860 | 1.00 | 39.51 B | N |
| ATOM | 16765 | CA | SER | B | 522 | 68.067 | 20.756 | −40.065 | 1.00 | 39.64 B | C |
| ATOM | 16767 | CB | SER | B | 522 | 67.675 | 19.512 | −40.881 | 1.00 | 39.62 B | C |
| ATOM | 16770 | OG | SER | B | 522 | 68.247 | 18.334 | −40.340 | 1.00 | 39.80 B | O |
| ATOM | 16772 | C | SER | B | 522 | 67.354 | 20.780 | −38.702 | 1.00 | 39.74 B | C |
| ATOM | 16773 | O | SER | B | 522 | 68.014 | 20.665 | −37.666 | 1.00 | 39.55 B | O |
| ATOM | 16775 | N | PRO | B | 523 | 66.013 | 20.952 | −38.691 | 1.00 | 40.10 B | N |
| ATOM | 16776 | CA | PRO | B | 523 | 65.277 | 20.965 | −37.414 | 1.00 | 40.09 B | C |
| ATOM | 16778 | CB | PRO | B | 523 | 63.811 | 21.075 | −37.849 | 1.00 | 40.16 B | C |
| ATOM | 16781 | CG | PRO | B | 523 | 63.856 | 21.703 | −39.192 | 1.00 | 40.42 B | C |
| ATOM | 16784 | CD | PRO | B | 523 | 65.125 | 21.234 | −39.836 | 1.00 | 40.33 B | C |
| ATOM | 16787 | C | PRO | B | 523 | 65.498 | 19.703 | −36.572 | 1.00 | 40.04 B | C |
| ATOM | 16788 | O | PRO | B | 523 | 65.670 | 19.800 | −35.353 | 1.00 | 39.93 B | O |
| ATOM | 16789 | N | ASP | B | 524 | 65.479 | 18.538 | −37.222 | 1.00 | 39.90 B | N |
| ATOM | 16790 | CA | ASP | B | 524 | 65.886 | 17.277 | −36.593 | 1.00 | 39.64 B | C |
| ATOM | 16792 | CB | ASP | B | 524 | 65.136 | 16.081 | −37.198 | 1.00 | 39.95 B | C |
| ATOM | 16795 | CG | ASP | B | 524 | 63.726 | 15.926 | −36.655 | 1.00 | 40.66 B | C |
| ATOM | 16796 | OD1 | ASP | B | 524 | 63.491 | 16.229 | −35.465 | 1.00 | 40.38 B | O |
| ATOM | 16797 | OD2 | ASP | B | 524 | 62.851 | 15.477 | −37.425 | 1.00 | 42.77 B | O |
| ATOM | 16798 | C | ASP | B | 524 | 67.386 | 17.083 | −36.782 | 1.00 | 38.91 B | C |
| ATOM | 16799 | O | ASP | B | 524 | 67.812 | 16.471 | −37.759 | 1.00 | 39.00 B | O |
| ATOM | 16801 | N | GLU | B | 525 | 68.159 | 17.608 | −35.830 | 1.00 | 38.15 B | N |
| ATOM | 16802 | CA | GLU | B | 525 | 69.642 | 17.592 | −35.810 | 1.00 | 37.66 B | C |
| ATOM | 16804 | CB | GLU | B | 525 | 70.297 | 17.569 | −37.206 | 1.00 | 37.71 B | C |
| ATOM | 16807 | CG | GLU | B | 525 | 70.620 | 16.153 | −37.724 | 1.00 | 37.79 B | C |
| ATOM | 16810 | CD | GLU | B | 525 | 71.981 | 16.048 | −38.386 | 1.00 | 38.25 B | C |
| ATOM | 16811 | OE1 | GLU | B | 525 | 72.955 | 16.625 | −37.857 | 1.00 | 39.00 B | O |
| ATOM | 16812 | OE2 | GLU | B | 525 | 72.080 | 15.370 | −39.430 | 1.00 | 38.77 B | O |
| ATOM | 16813 | C | GLU | B | 525 | 70.191 | 18.771 | −34.994 | 1.00 | 36.95 B | C |
| ATOM | 16814 | O | GLU | B | 525 | 71.317 | 18.714 | −34.499 | 1.00 | 37.04 B | O |
| ATOM | 16816 | N | LEU | B | 526 | 69.407 | 19.842 | −34.880 | 1.00 | 36.09 B | N |
| ATOM | 16817 | CA | LEU | B | 526 | 69.625 | 20.840 | −33.837 | 1.00 | 35.33 B | C |
| ATOM | 16819 | CB | LEU | B | 526 | 68.900 | 22.150 | −34.161 | 1.00 | 35.12 B | C |
| ATOM | 16822 | CG | LEU | B | 526 | 69.334 | 23.384 | −33.364 | 1.00 | 34.90 B | C |
| ATOM | 16824 | CD1 | LEU | B | 526 | 68.442 | 24.568 | −33.694 | 1.00 | 34.94 B | C |
| ATOM | 16828 | CD2 | LEU | B | 526 | 70.793 | 23.730 | −33.630 | 1.00 | 36.14 B | C |
| ATOM | 16832 | C | LEU | B | 526 | 69.105 | 20.252 | −32.527 | 1.00 | 34.83 B | C |
| ATOM | 16833 | O | LEU | B | 526 | 69.770 | 20.327 | −31.496 | 1.00 | 34.87 B | O |
| ATOM | 16835 | N | THR | B | 527 | 67.913 | 19.660 | −32.586 | 1.00 | 34.52 B | N |
| ATOM | 16836 | CA | THR | B | 527 | 67.303 | 18.996 | −31.434 | 1.00 | 34.28 B | C |
| ATOM | 16838 | CB | THR | B | 527 | 65.908 | 18.433 | −31.788 | 1.00 | 34.07 B | C |
| ATOM | 16840 | OG1 | THR | B | 527 | 65.038 | 19.509 | −32.164 | 1.00 | 33.57 B | O |

TABLE 8-2-continued

Coordinates for L494P Structure

| ATOM | 16842 | CG2 | THR | B | 527 | 65.306 | 17.682 | −30.606 | 1.00 | 33.37 | B | C |
|---|---|---|---|---|---|---|---|---|---|---|---|---|
| ATOM | 16846 | C | THR | B | 527 | 68.179 | 17.857 | −30.916 | 1.00 | 34.29 | B | C |
| ATOM | 16847 | O | THR | B | 527 | 68.451 | 17.771 | −29.716 | 1.00 | 34.38 | B | O |
| ATOM | 16849 | N | ARG | B | 528 | 68.617 | 16.992 | −31.829 | 1.00 | 34.09 | B | N |
| ATOM | 16850 | CA | ARG | B | 528 | 69.465 | 15.850 | −31.485 | 1.00 | 34.07 | B | C |
| ATOM | 16852 | CB | ARG | B | 528 | 69.933 | 15.138 | −32.760 | 1.00 | 34.30 | B | C |
| ATOM | 16855 | CG | ARG | B | 528 | 70.746 | 13.869 | −32.528 | 1.00 | 35.25 | B | C |
| ATOM | 16858 | CD | ARG | B | 528 | 71.215 | 13.264 | −33.849 | 1.00 | 36.66 | B | C |
| ATOM | 16861 | NE | ARG | B | 528 | 72.244 | 14.073 | −34.513 | 1.00 | 37.15 | B | N |
| ATOM | 16863 | CZ | ARG | B | 528 | 73.534 | 14.113 | −34.169 | 1.00 | 36.44 | B | C |
| ATOM | 16864 | NH1 | ARG | B | 528 | 73.996 | 13.397 | −33.146 | 1.00 | 35.92 | B | N |
| ATOM | 16867 | NH2 | ARG | B | 528 | 74.373 | 14.884 | −34.854 | 1.00 | 35.81 | B | N |
| ATOM | 16870 | C | ARG | B | 528 | 70.673 | 16.287 | −30.655 | 1.00 | 33.89 | B | C |
| ATOM | 16871 | O | ARG | B | 528 | 70.950 | 15.705 | −29.606 | 1.00 | 34.34 | B | O |
| ATOM | 16873 | N | LYS | B | 529 | 71.378 | 17.313 | −31.127 | 1.00 | 33.28 | B | N |
| ATOM | 16874 | CA | LYS | B | 529 | 72.566 | 17.824 | −30.436 | 1.00 | 32.69 | B | C |
| ATOM | 16876 | CB | LYS | B | 529 | 73.298 | 18.863 | −31.294 | 1.00 | 32.75 | B | C |
| ATOM | 16879 | CG | LYS | B | 529 | 74.085 | 18.275 | −32.452 | 1.00 | 32.66 | B | C |
| ATOM | 16882 | CD | LYS | B | 529 | 74.956 | 19.327 | −33.120 | 1.00 | 32.31 | B | C |
| ATOM | 16885 | CE | LYS | B | 529 | 75.829 | 18.711 | −34.200 | 1.00 | 32.91 | B | C |
| ATOM | 16888 | NZ | LYS | B | 529 | 76.857 | 19.660 | −34.708 | 1.00 | 33.59 | B | N |
| ATOM | 16892 | C | LYS | B | 529 | 72.225 | 18.436 | −29.079 | 1.00 | 32.13 | B | C |
| ATOM | 16893 | O | LYS | B | 529 | 72.916 | 18.182 | −28.091 | 1.00 | 32.37 | B | O |
| ATOM | 16895 | N | ARG | B | 530 | 71.165 | 19.241 | −29.037 | 1.00 | 31.27 | B | N |
| ATOM | 16896 | CA | ARG | B | 530 | 70.759 | 19.913 | −27.800 | 1.00 | 30.74 | B | C |
| ATOM | 16898 | CB | ARG | B | 530 | 69.629 | 20.912 | −28.070 | 1.00 | 30.66 | B | C |
| ATOM | 16901 | CG | ARG | B | 530 | 70.095 | 22.182 | −28.768 | 1.00 | 30.10 | B | C |
| ATOM | 16904 | CD | ARG | B | 530 | 68.926 | 23.081 | −29.131 | 1.00 | 28.52 | B | C |
| ATOM | 16907 | NE | ARG | B | 530 | 69.370 | 24.383 | −29.626 | 1.00 | 26.96 | B | N |
| ATOM | 16909 | CZ | ARG | B | 530 | 68.554 | 25.374 | −29.982 | 1.00 | 26.60 | B | C |
| ATOM | 16910 | NH1 | ARG | B | 530 | 67.234 | 25.224 | −29.904 | 1.00 | 26.51 | B | N |
| ATOM | 16913 | NH2 | ARG | B | 530 | 69.059 | 26.524 | −30.420 | 1.00 | 26.25 | B | N |
| ATOM | 16916 | C | ARG | B | 530 | 70.346 | 18.918 | −26.716 | 1.00 | 30.41 | B | C |
| ATOM | 16917 | O | ARG | B | 530 | 70.684 | 19.097 | −25.546 | 1.00 | 30.43 | B | O |
| ATOM | 16919 | N | VAL | B | 531 | 69.626 | 17.871 | −27.110 | 1.00 | 30.03 | B | N |
| ATOM | 16920 | CA | VAL | B | 531 | 69.278 | 16.784 | −26.191 | 1.00 | 29.78 | B | C |
| ATOM | 16922 | CB | VAL | B | 531 | 68.275 | 15.782 | −26.834 | 1.00 | 30.01 | B | C |
| ATOM | 16924 | CG1 | VAL | B | 531 | 68.603 | 14.335 | −26.458 | 1.00 | 30.16 | B | C |
| ATOM | 16928 | CG2 | VAL | B | 531 | 66.841 | 16.141 | −26.447 | 1.00 | 29.98 | B | C |
| ATOM | 16932 | C | VAL | B | 531 | 70.530 | 16.052 | −25.694 | 1.00 | 29.45 | B | C |
| ATOM | 16933 | O | VAL | B | 531 | 70.578 | 15.616 | −24.543 | 1.00 | 29.37 | B | O |
| ATOM | 16935 | N | LEU | B | 532 | 71.536 | 15.927 | −26.559 | 1.00 | 29.15 | B | N |
| ATOM | 16936 | CA | LEU | B | 532 | 72.822 | 15.331 | −26.167 | 1.00 | 28.66 | B | C |
| ATOM | 16938 | CB | LEU | B | 532 | 73.687 | 14.993 | −27.391 | 1.00 | 28.54 | B | C |
| ATOM | 16941 | CG | LEU | B | 532 | 73.627 | 13.537 | −27.858 | 1.00 | 29.13 | B | C |
| ATOM | 16943 | CD1 | LEU | B | 532 | 72.216 | 13.153 | −28.293 | 1.00 | 29.00 | B | C |
| ATOM | 16947 | CD2 | LEU | B | 532 | 74.630 | 13.293 | −28.983 | 1.00 | 29.97 | B | C |
| ATOM | 16951 | C | LEU | B | 532 | 73.602 | 16.232 | −25.208 | 1.00 | 28.00 | B | C |
| ATOM | 16952 | O | LEU | B | 532 | 74.158 | 15.751 | −24.220 | 1.00 | 28.07 | B | O |
| ATOM | 16954 | N | SER | B | 533 | 73.632 | 17.532 | −25.500 | 1.00 | 26.92 | B | N |
| ATOM | 16955 | CA | SER | B | 533 | 74.369 | 18.495 | −24.679 | 1.00 | 26.09 | B | C |
| ATOM | 16957 | CB | SER | B | 533 | 74.469 | 19.844 | −25.392 | 1.00 | 26.14 | B | C |
| ATOM | 16960 | OG | SER | B | 533 | 73.243 | 20.553 | −25.320 | 1.00 | 26.63 | B | O |
| ATOM | 16962 | C | SER | B | 533 | 73.722 | 18.697 | −23.311 | 1.00 | 25.29 | B | C |
| ATOM | 16963 | O | SER | B | 533 | 74.420 | 18.822 | −22.303 | 1.00 | 25.77 | B | O |
| ATOM | 16965 | N | VAL | B | 534 | 72.392 | 18.729 | −23.284 | 1.00 | 24.07 | B | N |
| ATOM | 16966 | CA | VAL | B | 534 | 71.643 | 19.035 | −22.065 | 1.00 | 23.05 | B | C |
| ATOM | 16968 | CB | VAL | B | 534 | 70.265 | 19.652 | −22.401 | 1.00 | 22.97 | B | C |
| ATOM | 16970 | CG1 | VAL | B | 534 | 69.412 | 19.793 | −21.152 | 1.00 | 23.85 | B | C |
| ATOM | 16974 | CG2 | VAL | B | 534 | 70.448 | 21.003 | −23.069 | 1.00 | 21.88 | B | C |
| ATOM | 16978 | C | VAL | B | 534 | 71.462 | 17.820 | −21.153 | 1.00 | 22.17 | B | C |
| ATOM | 16979 | O | VAL | B | 534 | 71.657 | 17.926 | −19.942 | 1.00 | 21.94 | B | O |
| ATOM | 16981 | N | ILE | B | 535 | 71.098 | 16.674 | −21.728 | 1.00 | 21.59 | B | N |
| ATOM | 16982 | CA | ILE | B | 535 | 70.783 | 15.471 | −20.938 | 1.00 | 20.91 | B | C |
| ATOM | 16984 | CB | ILE | B | 535 | 69.589 | 14.673 | −21.539 | 1.00 | 20.66 | B | C |
| ATOM | 16986 | CG1 | ILE | B | 535 | 68.343 | 15.558 | −21.675 | 1.00 | 19.60 | B | C |
| ATOM | 16989 | CD1 | ILE | B | 535 | 67.826 | 16.119 | −20.364 | 1.00 | 17.67 | B | C |
| ATOM | 16993 | CG2 | ILE | B | 535 | 69.271 | 13.457 | −20.680 | 1.00 | 19.45 | B | C |
| ATOM | 16997 | C | ILE | B | 535 | 71.972 | 14.519 | −20.762 | 1.00 | 20.28 | B | C |
| ATOM | 16998 | O | ILE | B | 535 | 72.342 | 14.203 | −19.633 | 1.00 | 19.52 | B | O |
| ATOM | 17000 | N | THR | B | 536 | 72.561 | 14.061 | −21.866 | 1.00 | 20.21 | B | N |
| ATOM | 17001 | CA | THR | B | 536 | 73.580 | 13.003 | −21.806 | 1.00 | 20.57 | B | C |
| ATOM | 17003 | CB | THR | B | 536 | 73.444 | 12.009 | −22.988 | 1.00 | 20.61 | B | C |
| ATOM | 17005 | OG1 | THR | B | 536 | 73.670 | 12.688 | −24.229 | 1.00 | 21.12 | B | O |
| ATOM | 17007 | CG2 | THR | B | 536 | 72.058 | 11.372 | −22.996 | 1.00 | 20.40 | B | C |
| ATOM | 17011 | C | THR | B | 536 | 75.025 | 13.520 | −21.730 | 1.00 | 20.49 | B | C |
| ATOM | 17012 | O | THR | B | 536 | 75.658 | 13.438 | −20.677 | 1.00 | 20.27 | B | O |
| ATOM | 17014 | N | GLU | B | 537 | 75.541 | 14.045 | −22.838 | 1.00 | 20.64 | B | N |

TABLE 8-2-continued

Coordinates for L494P Structure

| ATOM | 17015 | CA | GLU | B | 537 | 76.956 | 14.423 | −22.932 | 1.00 | 21.04 | B | C |
|---|---|---|---|---|---|---|---|---|---|---|---|---|
| ATOM | 17017 | CB | GLU | B | 537 | 77.330 | 14.745 | −24.384 | 1.00 | 21.51 | B | C |
| ATOM | 17020 | CG | GLU | B | 537 | 77.292 | 13.537 | −25.324 | 1.00 | 22.54 | B | C |
| ATOM | 17023 | CD | GLU | B | 537 | 77.568 | 13.898 | −26.780 | 1.00 | 23.27 | B | C |
| ATOM | 17024 | OE1 | GLU | B | 537 | 78.095 | 13.035 | −27.516 | 1.00 | 21.98 | B | O |
| ATOM | 17025 | OE2 | GLU | B | 537 | 77.257 | 15.038 | −27.189 | 1.00 | 24.15 | B | O |
| ATOM | 17026 | C | GLU | B | 537 | 77.311 | 15.617 | −22.031 | 1.00 | 20.83 | B | C |
| ATOM | 17027 | O | GLU | B | 537 | 76.737 | 16.700 | −22.187 | 1.00 | 20.87 | B | O |
| ATOM | 17029 | N | PRO | B | 538 | 78.272 | 15.433 | −21.099 | 1.00 | 20.36 | B | N |
| ATOM | 17030 | CA | PRO | B | 538 | 78.649 | 16.551 | −20.233 | 1.00 | 19.96 | B | C |
| ATOM | 17032 | CB | PRO | B | 538 | 79.456 | 15.883 | −19.104 | 1.00 | 19.93 | B | C |
| ATOM | 17035 | CG | PRO | B | 538 | 79.623 | 14.441 | −19.482 | 1.00 | 19.71 | B | C |
| ATOM | 17038 | CD | PRO | B | 538 | 79.135 | 14.258 | −20.878 | 1.00 | 20.30 | B | C |
| ATOM | 17041 | C | PRO | B | 538 | 79.501 | 17.592 | −20.943 | 1.00 | 19.59 | B | C |
| ATOM | 17042 | O | PRO | B | 538 | 79.934 | 17.380 | −22.077 | 1.00 | 19.30 | B | O |
| ATOM | 17043 | N | ILE | B | 539 | 79.728 | 18.715 | −20.272 | 1.00 | 19.52 | B | N |
| ATOM | 17044 | CA | ILE | B | 539 | 80.663 | 19.715 | −20.763 | 1.00 | 20.00 | B | C |
| ATOM | 17046 | CB | ILE | B | 539 | 80.524 | 21.056 | −20.008 | 1.00 | 20.22 | B | C |
| ATOM | 17048 | CG1 | ILE | B | 539 | 79.134 | 21.656 | −20.230 | 1.00 | 19.71 | B | C |
| ATOM | 17051 | CD1 | ILE | B | 539 | 78.919 | 22.967 | −19.510 | 1.00 | 19.23 | B | C |
| ATOM | 17055 | CG2 | ILE | B | 539 | 81.594 | 22.051 | −20.464 | 1.00 | 19.98 | B | C |
| ATOM | 17059 | C | ILE | B | 539 | 82.072 | 19.168 | −20.569 | 1.00 | 20.32 | B | C |
| ATOM | 17060 | O | ILE | B | 539 | 82.372 | 18.577 | −19.530 | 1.00 | 20.46 | B | O |
| ATOM | 17062 | N | LEU | B | 540 | 82.928 | 19.353 | −21.569 | 1.00 | 20.70 | B | N |
| ATOM | 17063 | CA | LEU | B | 540 | 84.317 | 18.904 | −21.480 | 1.00 | 21.15 | B | C |
| ATOM | 17065 | CB | LEU | B | 540 | 85.103 | 19.328 | −22.725 | 1.00 | 21.14 | B | C |
| ATOM | 17068 | CG | LEU | B | 540 | 84.665 | 18.725 | −24.065 | 1.00 | 20.69 | B | C |
| ATOM | 17070 | CD1 | LEU | B | 540 | 85.271 | 19.506 | −25.229 | 1.00 | 19.34 | B | C |
| ATOM | 17074 | CD2 | LEU | B | 540 | 85.032 | 17.246 | −24.140 | 1.00 | 17.98 | B | C |
| ATOM | 17078 | C | LEU | B | 540 | 84.957 | 19.510 | −20.230 | 1.00 | 21.63 | B | C |
| ATOM | 17079 | O | LEU | B | 540 | 84.734 | 20.687 | −19.939 | 1.00 | 22.38 | B | O |
| ATOM | 17081 | N | PRO | B | 541 | 85.746 | 18.716 | −19.481 | 1.00 | 21.69 | B | N |
| ATOM | 17082 | CA | PRO | B | 541 | 86.321 | 19.215 | −18.224 | 1.00 | 21.85 | B | C |
| ATOM | 17084 | CB | PRO | B | 541 | 87.149 | 18.027 | −17.712 | 1.00 | 21.79 | B | C |
| ATOM | 17087 | CG | PRO | B | 541 | 87.361 | 17.154 | −18.895 | 1.00 | 22.13 | B | C |
| ATOM | 17090 | CD | PRO | B | 541 | 86.153 | 17.327 | −19.754 | 1.00 | 21.68 | B | C |
| ATOM | 17093 | C | PRO | B | 541 | 87.205 | 20.452 | −18.389 | 1.00 | 22.14 | B | C |
| ATOM | 17094 | O | PRO | B | 541 | 87.704 | 20.723 | −19.480 | 1.00 | 22.12 | B | O |
| ATOM | 17095 | N | PHE | B | 542 | 87.385 | 21.191 | −17.298 | 1.00 | 22.72 | B | N |
| ATOM | 17096 | CA | PHE | B | 542 | 88.184 | 22.414 | −17.305 | 1.00 | 23.32 | B | C |
| ATOM | 17098 | CB | PHE | B | 542 | 87.783 | 23.298 | −16.120 | 1.00 | 23.32 | B | C |
| ATOM | 17101 | CG | PHE | B | 542 | 88.756 | 24.402 | −15.833 | 1.00 | 24.16 | B | C |
| ATOM | 17102 | CD1 | PHE | B | 542 | 89.494 | 24.409 | −14.654 | 1.00 | 24.68 | B | C |
| ATOM | 17104 | CE1 | PHE | B | 542 | 90.398 | 25.425 | −14.389 | 1.00 | 24.06 | B | C |
| ATOM | 17106 | CZ | PHE | B | 542 | 90.580 | 26.443 | −15.309 | 1.00 | 24.14 | B | C |
| ATOM | 17108 | CE2 | PHE | B | 542 | 89.853 | 26.444 | −16.491 | 1.00 | 24.52 | B | C |
| ATOM | 17110 | CD2 | PHE | B | 542 | 88.949 | 25.426 | −16.748 | 1.00 | 24.49 | B | C |
| ATOM | 17112 | C | PHE | B | 542 | 89.688 | 22.104 | −17.261 | 1.00 | 23.94 | B | C |
| ATOM | 17113 | O | PHE | B | 542 | 90.167 | 21.469 | −16.320 | 1.00 | 23.65 | B | O |
| ATOM | 17115 | N | GLU | B | 543 | 90.421 | 22.563 | −18.279 | 1.00 | 24.84 | B | N |
| ATOM | 17116 | CA | GLU | B | 543 | 91.874 | 22.344 | −18.380 | 1.00 | 25.76 | B | C |
| ATOM | 17118 | CB | GLU | B | 543 | 92.235 | 21.696 | −19.728 | 1.00 | 25.79 | B | C |
| ATOM | 17121 | CG | GLU | B | 543 | 92.464 | 20.182 | −19.672 | 1.00 | 25.69 | B | C |
| ATOM | 17124 | CD | GLU | B | 543 | 93.330 | 19.661 | −20.818 | 1.00 | 25.14 | B | C |
| ATOM | 17125 | OE1 | GLU | B | 543 | 93.398 | 20.313 | −21.883 | 1.00 | 24.79 | B | O |
| ATOM | 17126 | OE2 | GLU | B | 543 | 93.945 | 18.587 | −20.650 | 1.00 | 23.90 | B | O |
| ATOM | 17127 | C | GLU | B | 543 | 92.683 | 23.634 | −18.213 | 1.00 | 26.66 | B | C |
| ATOM | 17128 | O | GLU | B | 543 | 92.137 | 24.738 | −18.259 | 1.00 | 26.93 | B | O |
| ATOM | 17130 | N | ARG | B | 544 | 93.992 | 23.470 | −18.017 | 1.00 | 27.44 | B | N |
| ATOM | 17131 | CA | ARG | B | 544 | 94.937 | 24.585 | −17.945 | 1.00 | 28.02 | B | C |
| ATOM | 17133 | CB | ARG | B | 544 | 95.430 | 24.787 | −16.509 | 1.00 | 28.24 | B | C |
| ATOM | 17136 | CG | ARG | B | 544 | 94.332 | 25.114 | −15.508 | 1.00 | 29.37 | B | C |
| ATOM | 17139 | CD | ARG | B | 544 | 94.881 | 25.278 | −14.094 | 1.00 | 31.23 | B | C |
| ATOM | 17142 | NE | ARG | B | 544 | 93.858 | 25.011 | −13.080 | 1.00 | 33.21 | B | N |
| ATOM | 17144 | CZ | ARG | B | 544 | 93.577 | 23.811 | −12.563 | 1.00 | 34.35 | B | C |
| ATOM | 17145 | NH1 | ARG | B | 544 | 94.242 | 22.720 | −12.943 | 1.00 | 34.25 | B | N |
| ATOM | 17148 | NH2 | ARG | B | 544 | 92.616 | 23.700 | −11.649 | 1.00 | 34.18 | B | N |
| ATOM | 17151 | C | ARG | B | 544 | 96.124 | 24.303 | −18.862 | 1.00 | 28.26 | B | C |
| ATOM | 17152 | O | ARG | B | 544 | 96.881 | 25.207 | −19.220 | 1.00 | 28.64 | B | O |
| ATOM | 17154 | O | HOH | C | 1 | 49.400 | −35.729 | 6.838 | 1.00 | 2.00 | | O |
| ATOM | 17157 | O | HOH | C | 2 | 77.843 | −36.939 | −9.130 | 1.00 | 2.00 | | O |
| ATOM | 17160 | O | HOH | C | 3 | 55.726 | −22.590 | −6.230 | 1.00 | 19.51 | | O |
| ATOM | 17163 | O | HOH | C | 4 | 37.476 | −22.187 | −17.999 | 1.00 | 2.00 | | O |

Example 9

Expression and Purification of IspS-T536F

Expression of 6×His-Tagged IspS-T536F

N-terminally 6×His-tagged IspS-T536F was expressed and purified from strain DW363. The growth procedure is suitable for histidine tagged enzymes expressed in BL21 (λDE3)pLysS cells. A 10 ml overnight culture was prepared for each 1 L of planned growth. The appropriate antibiotics (50 mg/ml kanamycin, 50 mg/ml chloramphenicol) were added to 10 ml of LB medium in a 25 ml flask which was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1L day culture was inoculated with 10 ml of overnight culture and grown at 30-37° C. with shaking at ~220 rpm until the $OD_{600}$ reached ~0.4-0.6. Day cultures were then induced with 400 μM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process.

Purification of 6×His-Tagged IspS-T536F

For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 40-50 ml of lysis buffer was used per 1L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 μl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 μl).

The clarified lysate was run over HisTrap HP columns (GE healthcare) using a gradient from 0-100% Ni buffer B. Following loading of the lysate on the column, the column was washed with Ni wash buffer (50 mM $NaH_2PO_4$, 300 mm NaCl, 20 mM imidazole, ph 8.0). The his-tagged IspS was then eluted from the column using a gradient from 0-100% Ni elution buffer (50 mM $NaH_2PO_4$, 300 mM NaCl, 500 mM imidazole, ph 8.0) and fractions containing the his-tagged IspS were collected. The column was then washed with Ni stripping buffer (20 mM NaH2PO4, 0.5 m NaCl, 50 mM EDTA, ph 7.4). Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a Hi Prep 26/10 Desalting column (GE heathcare) packed with Sephadex G25 resin. The G-25 buffer consisted of 50 mM HEPES, 50 mM NaCl, and 1 mM DTT, pH 7.4. Fractions were then analyzed and concentrated. The samples were then stored at −80° C.

TEV Cleavage (IspS-T536F from Strains DW363)

Strain DW363 is described in Example 6. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (which is also tagged), and impurities. The Ni column pass though and washes were analyzed using SDS-PAGE gel (NUPAGE, Invitrogen; FIG. 54) and DMAPP activity assays. Samples containing pure enzyme were pooled and desalted into 50 mM NaCl pH 7.4 buffer containing 1 mM DTT and stored at −80° C.

Expression Levels of IspS Variants

Small Scale Expression of 6×His-Tagged IspS Variants

N-terminally 6×His-tagged wild type IspS, IspS-L494P, and IspS-T536F were expressed and purified from strains MD09-167, DW399, and DW363, respectively. The growth procedure is suitable for histidine tagged enzymes expressed in BL21(λDE3)pLysS cells. A 3 ml of overnight culture was prepared for each 100 mL of planned growth. The appropriate antibiotics (50 mg/ml kanamycin, 25 mg/ml chloramphenicol) were added to 3 ml of LB medium in a 10 ml glass tube and was inoculated with 1 colony from a fresh plate of cells or directly from glycerol frozen cell stock. Cultures were grown at 30° C. overnight with shaking at ~220 rpm. Day cultures were prepared in 100 mL of LB medium with appropriate antibiotics for each culture. Each 100 mL day culture was inoculated with 50 μl of overnight culture and grown at 37° C. with shaking at ~220 rpm until the $OD_{600}$ reached ~0.4-0.6. Day cultures were then induced with 400 μM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process.

Purification of 6×His-Tagged IspS Variants Expressed in Small Scale

For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 3 ml of lysis buffer was used per 5 mL of cell pellet. Cells were then incubated on ice for approximately 30 min. The cell suspension was then lysed fully by passing 2-3 times through a french pressure cell (small french press cell at 850 psi/Low setting) until lysate started to look clear. A sample of the lysate was saved for activity assay and gel analysis (~100 μl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 μl).

A 20 mL disposable column containing 0.5 mL Ni Sepharose 6 Fast Flow resin (Amersham) was pre equilibrated with 10 mL of Ni wash buffer. Protein in the clarified lysate was added to the column and shaken gently for 60 min at 4° C. in order to bind the tagged protein. The protein was then eluted with 2.5 mL Ni elution buffer. A sample of the eluate was saved for activity assay and gel analysis (~100 μl).

To buffer exchange the protein into a buffer suitable for protein assays and storage, a PD-10 column (GE Healthcare) was equilibrated with 25 mL PD-10 buffer (50 mM HEPES, 0.05 M NaCl, pH 7.4). Protein was loaded onto the PD-10 column and eluted with 3.5 mL of PD-10 buffer. The eluate was then analyzed by absorbance at 280 nm and SDS-PAGE gel and the samples were stored at −80° C.

Analysis of the yield of purified wild type IspS compared to IspS-L494P, and IspS-T536F suggests that both IspS-L494P and IspS-T536F are expressed at higher levels than the wild type protein (Table 9, FIG. 55).

Differential Scanning Calorimetry

Excessive heat capacity curves were measured using an ultrasensitive scanning high-throughput microcalorimeter, VP-Cap DSC (MicroCal, Inc., Northampton, Mass.). The standard procedure for Differential Scanning calorimetry (DSC) measurements and the theory of the technique is previously published (Freire, E. (1995) Differential Scanning calorimetry Methods. Mol. Biol. 41, 191-218). Approximately 500 μL of 0.5 mg/ml IspS (from strain MD09-167) or variant IspS-L494P (from strain DW399) and IspS-T536F (from strain DW363) (in the absence or presence of 5 mM sodium pyrophosphate) were scanned over a 30-100° C. temperature range. The same sample was then re-scanned to check the reversibility of the process. For IspS the thermal unfolding process was irreversible. The buffer used was 50 mM HEPES, 5 mM $MgCl_2$, pH 7.4, with and without 5 mM sodium pyrophosphate. Sodium pyrophosphate was included for its ability to function as a substrate analog. A 200° C./hr scan rate was used to minimize any artifacts that may result from aggregation. The thermal midpoint (Tm) of the DSC curves was used as an indicator of the thermal stability. The thermal melting curves and the melting points for the wild type IspS and variants are shown in FIG. 56 (buffer only) and 57 (with 5 mM sodium pyrophosphate).

The thermal unfolding for the IspS variants IspS-L494P and IspS-T536F in buffer demonstrates a considerable increase in the melting points for the variants when compared to that for the wild type. In buffer alone, the wild type IspS has a thermal melting point of 58.3° C. while the Tm's for IspS-L494P and IspS-T536F are 60.4° C. and 62.1° C., respectively. Thus, the substitution of L494 with P results in an increase in the Tm of 2.1° C., and the substitution of T536 with F results in an increase in the Tm of 3.8° C.

In the presence of sodium pyrophosphate, the wild type IspS and IspS variants all exhibit a decrease in melting point compared to analysis in buffer alone. When wild type IspS and the variants were thermally-unfolded in the presence of 5 mM sodium pyrophosphate, wild type IspS has a thermal melting point of 54.7° C., while the Tm's for IspS-L494P and IspS-T536F are 57.0° C. and 59.4° C., respectively. Thus, the substitution of L494 with P results in an increase in the Tm of 2.3° C., and the substitution of T536 with F results in an increase in the Tm of 4.7° C. The change in the shape of the DSC traces in the presence of substrate analog and the decrease in the Tm for the proteins could be the result of aggregation or represent a structure or conformational change of the protein upon complexation of the substrate analog. In addition, there is an exothermic peak. Nonetheless, the changes in the Tm's are fairly consistent with those for buffer alone.

Isoprene Synthase Activity vs Temperature

The activity of wild type IspS and variants IspS-L494P and IspS-T536F was measured across a spectrum of temperatures. Individual DMAPP assays were performed at 5° C. intervals from 25° C. to 80° C. by incubating the vials in a pre-heated water bath.

Isoprene Synthase DMAPP Assay

The following reaction mixture was used for the DMAPP assay: 25 μL purified protein, 5 μL MgCl2 (1 M), 5 μL DMAPP (100 mM), and 65 μL 100 mM Tris pH 8, 100 mM NaCl for a total volume of 100 μL. The reaction is performed at the specified temperature for 15 minutes in a gas tight 1.8 mL GC tube. Reactions are terminated by the addition of 100 μL 500 mM EDTA (pH 8). The amount of isoprene produced was measured by GC/MS.

The analysis was performed using an Agilent 6890 GC/MS system interfaced with a CTC Analytics CombiPAL autosampler operating in headspace mode. An Agilent HP-5MS GC/MS column (30 m×0.25 mm; 0.25 μm film thickness) was used for separation of analytes. The sampler was set up to inject 500 μL of headspace gas. The GC/MS method utilized helium as the carrier gas at a flow of 1 ml/min. The injection port was held at 250° C. with a split ratio of 50:1. The oven temperature was held at 37° C. for the 2 mM duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 200 μg/L. The limit of detection was estimated to be 50-100 ng/L using this method.

The temperature activity ratios for wild type IspS and variants IspS-L494P and IspS-T536F are plotted in FIG. 58. The IspS-T536F variant shifts the curve both upwards and to the right, suggesting that it has increased activity and thermostability as compared to wild type IspS and IspS-L494P. The activity and thermostability benefits of the T536F variant may be attributable to the replacement of a polar amino acid residue (threonine) with a large, hydrophobic residue (phenylalanine). FIG. 59 shows that at the 536 position, hydrophobic residues such as isoleucine, valine, and phenylalanine are common to many terpene synthase enzymes. It is therefore possible that the T536F mutation serves to remove polarity and introduce a more hydrophobic local region, and this change leads to the observed benefits in catalytic efficiency.

TABLE 9

Relative yield of purified IspS-L494P and IspS-T536F compared to wild type IspS

| Protein | Relative Yield |
| --- | --- |
| Wild type IspS | 1 |
| IspS-L494P | 1.3 |
| IspS-T536F | 1.9 |

We claim:

1. An isolated host cell comprising an isoprene synthase variant, wherein the isoprene synthase variant is produced by:
   a) identifying amino acid residues in the flexible loops of isoprene synthase based on the three dimensional structure of P. alba isoprene synthase;
   b) introducing one or more amino acid substitutions in the flexible loop amino acids of said isoprene synthase to produce an isoprene synthase variant; and
   c) identifying said isoprene synthase variant with substitutions that improve activity, expression or stability of the isoprene synthase,
wherein said isoprene synthase variant comprises one or more amino acid substitution(s) in the flexible loops corresponding to an amino acid position of SEQ ID NO:45 selected from the group consisting of A443, A453, N454, H515 and A519; and
   wherein said isoprene synthase variant has improved activity, expression or stability as compared to an isoprene synthase without said one or more amino acid substitutions.

2. An isolated host cell comprising an isoprene synthase variant, wherein the variant comprises one or more substitution(s) in the flexible loops corresponding to an amino acid position of SEQ ID NO:45 selected from the group consisting of A443, A453, N454, H515 and A519, wherein said isoprene synthase variant has improved activity, expression or stability as compared to an isoprene synthase without said one or more amino acid substitutions.

3. The isolated host cell of claim 1, wherein the variant comprises one or more substitutions selected from the group consisting of A443S, A443G, A443R, A443Q, A453L, A453N, A453I, A453V, H515M, H515Q, A519H, A519S, A519G, A519W and A519T.

4. The isolated host cell of claim 2, wherein the variant comprises one or more substitutions selected from the group consisting of A443S, A443G, A443R, A443Q, A453L, A453N, A453I, A453V, H515M, H515Q, A519H, A519S, A519G, A519W and A519T.

5. The isolated host cell of claim 2, wherein the cell is a gram-positive bacterial cell, gram-negative bacterial cell, filamentous fungal cell, or yeast cell.

6. The isolated host cell of claim 5, wherein the bacterial cell is selected from the group consisting of E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas sp., and P. alcaligenes cells.

7. The isolated host cell of claim 5, wherein the cell is selected from the group consisting of Escherichia spp., Saccharomyces spp., Panteoa spp., Bacillus spp., Yarrowia spp., and Trichoderma spp.

8. The isolated host cell of claim 7, wherein the cell is selected from the group consisting E. coli, S. cerevisiae, P. citrea, B. subtilis, Y. lipolytica, and T. reesei.

9. The isolated host cell of claim 2, wherein the host cell further comprises one or more heterologous nucleic acid(s) encoding one or more mevalonate (MVA) pathway polypeptides.

10. The isolated host cell of claim 9, wherein the one or more MVA pathway polypeptides is selected from: (i) an acetyl-CoA acetyltransferase (AA-CoA thiolase) polypeptide; (ii) a 3-hydroxy-3-methylglutaryl-CoA synthase (HMG-CoA synthase) polypeptide; (iii) a 3-hydroxy-3-methylglutaryl-CoA reductase (HMG-CoA reductase), (iv) mevalonate kinase (MVK); (v) phosphomevalonate kinase (PMK); or (vi) diphosphomevalonate decarboxylase (MVD).

11. The isolated host cell of claim 2, wherein the host cell further comprises a heterologous or native nucleic acid encoding an isopentenyl-diphosphate delta-isomerase (IDI) polypeptide and/or a heterologous or native nucleic acid encoding a 1-Deoxyxylulose-5-phosphate synthase (DXS) polypeptide, optionally in combination with the native 1-deoxy-D-xylulose-5-phosphate (DXP) pathway.

12. The isolated host cell of claim 2, wherein the host cell further comprises one or more nucleic acids encoding an IDI polypeptide and a DXS polypeptide.

13. The isolated host cell of claim 12, wherein the host cell comprises one vector encoding the isoprene synthase variant, the IDI polypeptide, and the DXS polypeptide.

14. The isolated host cell of claim 13, wherein the host cell further comprises a heterologous nucleic acid encoding a mevalonate (MVA) pathway polypeptide selected from the group consisting of an MVA pathway polypeptide from Saccharomyces cerevisiae and Enterococcus faecalis.

15. The isolated host cell of claim 2, wherein the host cell further comprises one or more nucleic acids encoding an MVA pathway polypeptide and a DXS polypeptide and wherein one vector encodes the isoprene synthase variant, the MVA pathway polypeptide, and the DXS polypeptide.

16. The isolated host cell of claim 2, wherein the host cell further comprises one or more nucleic acids encoding a DXS polypeptide, an IDI polypeptide, or one or more of the rest of the DXP pathway polypeptides, and a MVA pathway polypeptide.

17. The isolated host cell of claim 9, wherein the host cell further comprises one or more nucleic acids encoding an IDI polypeptide.

18. A method of producing isoprene, comprising: (a) providing a host cell of claim 1; and (b) culturing the host cell under conditions suitable for producing isoprene.

\* \* \* \* \*